(12) United States Patent
Masse et al.

(10) Patent No.: US 12,043,632 B2
(45) Date of Patent: Jul. 23, 2024

(54) 6-HETEROARYLOXY BENZIMIDAZOLES AND AZABENZIMIDAZOLES AS JAK2 INHIBITORS

(71) Applicant: Ajax Therapeutics, Inc., New York, NY (US)

(72) Inventors: Craig E. Masse, Cambridge, MA (US); Jeremy R. Greenwood, Brooklyn, NY (US); Sayan Mondal, New York, NY (US); Jiayi Xu, Marlboro, NJ (US); Phani Ghanakota, Edison, NJ (US); Fiona Michelle McRobb, Brooklyn, NY (US); Nicholas Boyles, Hillsboro, OR (US)

(73) Assignee: Ajax Therapeutics, Inc., New York, NY (US)

( * ) Notice: Subject to any disclaimer, the term of this patent is extended or adjusted under 35 U.S.C. 154(b) by 26 days.

(21) Appl. No.: 17/559,051

(22) Filed: Dec. 22, 2021

(65) Prior Publication Data

US 2023/0099203 A1 Mar. 30, 2023

Related U.S. Application Data

(60) Provisional application No. 63/277,337, filed on Nov. 9, 2021, provisional application No. 63/218,097, filed on Jul. 2, 2021, provisional application No. 63/130,251, filed on Dec. 23, 2020.

(51) Int. Cl.
C07D 519/00 (2006.01)

(52) U.S. Cl.
CPC .................................. C07D 519/00 (2013.01)

(58) Field of Classification Search
CPC .................................................. C07D 519/00
See application file for complete search history.

(56) References Cited

U.S. PATENT DOCUMENTS

| | | |
|---|---|---|
| 5,270,148 A | 12/1993 | Morigaki et al. |
| 5,512,590 A | 4/1996 | George et al. |
| 5,616,537 A | 4/1997 | Yokota et al. |
| 5,702,877 A | 12/1997 | Odenwalder et al. |
| 5,814,633 A | 9/1998 | Muller et al. |
| 5,852,046 A | 12/1998 | Lang et al. |
| 5,994,629 A | 11/1999 | Bojsen et al. |
| 6,329,383 B1 | 12/2001 | Hedgecock et al. |
| 6,346,531 B1 | 2/2002 | Luengo et al. |
| 6,444,816 B1 | 9/2002 | Das et al. |
| 6,552,192 B1 | 4/2003 | Hanus et al. |
| 6,566,372 B1 | 5/2003 | Zhi et al. |
| 6,630,470 B1 | 10/2003 | Luengo et al. |
| 6,743,800 B1 | 6/2004 | Peyman et al. |
| 6,747,016 B1 | 6/2004 | Peyman et al. |
| 7,256,196 B1 | 8/2007 | Sabat et al. |
| 7,531,553 B2 * | 5/2009 | Di Pietro ............. C07D 403/12 514/312 |
| 8,114,874 B2 | 2/2012 | Zou et al. |
| 8,293,923 B2 | 10/2012 | Guckian et al. |
| 8,614,330 B2 | 12/2013 | Amiri et al. |
| 8,846,697 B2 | 9/2014 | Carson et al. |
| 9,145,438 B2 | 9/2015 | Chesworth et al. |
| 9,200,020 B2 | 12/2015 | De Jersey et al. |
| 9,284,299 B2 | 3/2016 | Ji et al. |
| 10,766,888 B1 | 9/2020 | Biddle et al. |
| 11,691,963 B2 | 7/2023 | Masse et al. |
| 2001/0056090 A1 | 12/2001 | Aquila et al. |
| 2002/0010159 A1 | 1/2002 | Weigele et al. |
| 2002/0052368 A1 | 5/2002 | Marlowe et al. |
| 2002/0058677 A1 | 5/2002 | Marlowe et al. |
| 2002/0068721 A1 | 6/2002 | Weigele et al. |
| 2002/0094994 A1 | 7/2002 | Bourzat et al. |
| 2002/0120144 A1 | 8/2002 | Akama et al. |
| 2002/0165261 A1 | 11/2002 | Borisy et al. |
| 2002/0173506 A1 | 11/2002 | Clark et al. |
| 2003/0109714 A1 | 6/2003 | Wishart et al. |
| 2003/0187261 A1 | 10/2003 | Havlicek et al. |
| 2003/0199564 A1 | 10/2003 | Fenton et al. |
| 2004/0006117 A1 | 1/2004 | Blume et al. |
| 2004/0034224 A1 | 2/2004 | Hammarstrom et al. |
| 2004/0077633 A1 | 4/2004 | Watson et al. |
| 2004/0082583 A1 | 4/2004 | Cheung et al. |
| 2004/0087626 A1 | 5/2004 | Renhowe et al. |
| 2004/0122237 A1 | 6/2004 | Amiri et al. |
| 2004/0171630 A1 | 9/2004 | Kim et al. |
| 2004/0198725 A1 | 10/2004 | Sun et al. |
| 2005/0049263 A1 | 3/2005 | Kasibhatla et al. |
| 2005/0101647 A1 | 5/2005 | Oda et al. |
| 2005/0137234 A1 | 6/2005 | Bressi et al. |
| 2005/0192287 A1 | 9/2005 | Costales et al. |

(Continued)

FOREIGN PATENT DOCUMENTS

| | | |
|---|---|---|
| CN | 1148043 A | 4/1997 |
| CN | 101239980 A | 8/2008 |

(Continued)

OTHER PUBLICATIONS

Registry/ZRegistry (CAS RegistrySM) Sep. 2016 2 pages.*
Bartlett "Exploiting Chemical Diversity for Drug Discovery" Edited by Paul A Bartlett and Michael Entzeroth, the Royal Society of Chemistry, 2006, pp. 113-118.*
Kim "PubChem in 2021: new data content and improved web interfaces" Nucleic Acids Research, 2021, vol. 49, Database issue Published online Nov. 5, 2020.*
Irwin "Zinc—A Free Database of Commercially Available Compounds for Virtual Screening" J. Chem. Inf. Model. 2005, 45, 177-182.*
"Find ETDs Home » Thesis Resources » Find ETDs" Online: "https://ndltd.org/thesis-resources/find-etds/" Accessed Jan. 31, 2023.*
Schonherr "Profound Methyl Effects in Drug Discovery and a Call for New C—H Methylation Reactions" Angew. Chem. Int. Ed. 2013, 52, 12256-12267.*

(Continued)

*Primary Examiner* — David K O'Dell

(74) *Attorney, Agent, or Firm* — Choate, Hall & Stewart LLP; Charles E. Lyon; Michael A. Shinall

(57) ABSTRACT

The present disclosure provides 6-heteroaryloxy benzimidazole and azabenzimidazole compounds and compositions thereof useful for inhibiting JAK2.

35 Claims, No Drawings

(56) References Cited

U.S. PATENT DOCUMENTS

| | | |
|---|---|---|
| 2005/0209176 A1 | 9/2005 | Meutermans et al. |
| 2005/0239821 A1 | 10/2005 | Neyts et al. |
| 2005/0272765 A1 | 12/2005 | Feng et al. |
| 2005/0282802 A1 | 12/2005 | Kostik et al. |
| 2006/0042026 A1 | 3/2006 | Glenn et al. |
| 2006/0052331 A1 | 3/2006 | Koch et al. |
| 2006/0111362 A1 | 5/2006 | Kira et al. |
| 2006/0116383 A1 | 6/2006 | Bloxham et al. |
| 2006/0148830 A1 | 7/2006 | Terakado et al. |
| 2006/0154977 A1 | 7/2006 | Morand et al. |
| 2006/0160872 A1 | 7/2006 | Norman et al. |
| 2007/0032493 A1 | 2/2007 | Foley et al. |
| 2007/0043043 A1 | 2/2007 | Chen et al. |
| 2007/0049622 A1 | 3/2007 | Dimitroff et al. |
| 2007/0093544 A1 | 4/2007 | Parmee et al. |
| 2007/0105930 A1 | 5/2007 | Parmee et al. |
| 2007/0112048 A1 | 5/2007 | Bavari et al. |
| 2007/0173527 A1 | 7/2007 | Bressi et al. |
| 2007/0197450 A1 | 8/2007 | Fushimi et al. |
| 2007/0219235 A1 | 9/2007 | Mjalli et al. |
| 2007/0249637 A1 | 10/2007 | Collins et al. |
| 2007/0275984 A1 | 11/2007 | Imogai et al. |
| 2008/0008682 A1 | 1/2008 | Chong et al. |
| 2008/0009488 A1 | 1/2008 | Anand et al. |
| 2008/0032936 A1 | 2/2008 | Gai et al. |
| 2008/0058297 A1 | 3/2008 | Ono et al. |
| 2008/0096903 A1 | 4/2008 | Chen et al. |
| 2008/0132501 A1 | 6/2008 | Sun et al. |
| 2008/0161254 A1 | 7/2008 | Green et al. |
| 2008/0194803 A1 | 8/2008 | Sinclair et al. |
| 2008/0221148 A1 | 9/2008 | Ibrahim et al. |
| 2008/0284322 A1 | 11/2008 | Hosokawa et al. |
| 2009/0047249 A1 | 2/2009 | Graupe et al. |
| 2009/0118200 A1 | 5/2009 | Bergman et al. |
| 2009/0140637 A1 | 6/2009 | Hosokawa et al. |
| 2009/0176778 A1 | 7/2009 | Schmitz et al. |
| 2009/0232844 A1 | 9/2009 | Sutton et al. |
| 2009/0233946 A1 | 9/2009 | Krasinski et al. |
| 2009/0278115 A1 | 11/2009 | Hosokawa et al. |
| 2010/0010217 A1 | 1/2010 | Valiante et al. |
| 2010/0029709 A1 | 2/2010 | Menet et al. |
| 2010/0093747 A1 | 4/2010 | Goodhew |
| 2010/0197688 A1 | 8/2010 | Nantermet et al. |
| 2010/0204265 A1 | 8/2010 | Baskaran et al. |
| 2010/0210598 A1 | 8/2010 | Carson et al. |
| 2010/0216810 A1 | 8/2010 | Okaniwa et al. |
| 2010/0249119 A1 | 9/2010 | Hirose et al. |
| 2010/0256188 A1 | 10/2010 | Pfau et al. |
| 2010/0261679 A1 | 10/2010 | Sutton et al. |
| 2010/0267714 A1 | 10/2010 | Jorgensen et al. |
| 2011/0021518 A1 | 1/2011 | Magnuson et al. |
| 2011/0039895 A1 | 2/2011 | Chai et al. |
| 2011/0059962 A1 | 3/2011 | Alekshun et al. |
| 2011/0105498 A1 | 5/2011 | Pettus et al. |
| 2011/0117073 A1 | 5/2011 | Singh et al. |
| 2011/0172186 A1 | 7/2011 | Behnke et al. |
| 2011/0201605 A1 | 8/2011 | Baumann et al. |
| 2011/0237620 A1 | 9/2011 | Okaniwa |
| 2011/0263598 A1 | 10/2011 | Sampson et al. |
| 2011/0281865 A1 | 11/2011 | Muthuppalaniappan et al. |
| 2011/0312935 A1 | 12/2011 | Pfau et al. |
| 2012/0028969 A1 | 2/2012 | Barnes et al. |
| 2012/0115902 A1 | 5/2012 | Pfau et al. |
| 2012/0122930 A1 | 5/2012 | Pfau et al. |
| 2012/0172351 A1 | 7/2012 | Negoro et al. |
| 2012/0202287 A1 | 8/2012 | Adams et al. |
| 2012/0208839 A1 | 8/2012 | Priepke et al. |
| 2012/0214786 A1 | 8/2012 | Priepke et al. |
| 2012/0258967 A1 | 10/2012 | Qiao et al. |
| 2013/0059851 A1 | 3/2013 | Garraway et al. |
| 2013/0079342 A1 | 3/2013 | Dransfield et al. |
| 2013/0084346 A1 | 4/2013 | Wolkenberg et al. |
| 2013/0090327 A1 | 4/2013 | Hata et al. |
| 2013/0096136 A1 | 4/2013 | Hata et al. |
| 2013/0136782 A1 | 5/2013 | Blackwell et al. |
| 2013/0149717 A1 | 6/2013 | Krause et al. |
| 2013/0165446 A1 | 6/2013 | Fujita et al. |
| 2013/0184240 A1 | 7/2013 | Tonogaki et al. |
| 2013/0184248 A1 | 7/2013 | Grauert et al. |
| 2013/0190320 A1 | 7/2013 | Xu et al. |
| 2013/0224195 A1 | 8/2013 | Costales et al. |
| 2013/0225596 A1 | 8/2013 | Kai et al. |
| 2013/0261125 A1 | 10/2013 | Shipps, Jr. et al. |
| 2013/0310333 A1 | 11/2013 | Chesworth et al. |
| 2013/0345261 A1 | 12/2013 | Waters et al. |
| 2014/0011763 A1 | 1/2014 | Lakshman |
| 2014/0031339 A1 | 1/2014 | Abeywardane et al. |
| 2014/0155379 A1 | 6/2014 | Ho et al. |
| 2014/0194420 A1 | 7/2014 | Kojima et al. |
| 2014/0303102 A1 | 10/2014 | Choe et al. |
| 2014/0303360 A1 | 10/2014 | Schroeder et al. |
| 2014/0364386 A1 | 12/2014 | Choe et al. |
| 2015/0018291 A1 | 1/2015 | Choe et al. |
| 2015/0057309 A1 | 2/2015 | Vakkalanka et al. |
| 2015/0126436 A1 | 5/2015 | Phillips et al. |
| 2015/0133500 A1 | 5/2015 | Tafesse et al. |
| 2015/0152065 A1 | 6/2015 | Brookings et al. |
| 2015/0197497 A1 | 7/2015 | Abeywickrama et al. |
| 2015/0216168 A1 | 8/2015 | Frackenpohl et al. |
| 2015/0243903 A1 | 8/2015 | Zeng et al. |
| 2015/0249221 A1 | 9/2015 | Zeng et al. |
| 2016/0024072 A1 | 1/2016 | Kai et al. |
| 2016/0052922 A1 | 2/2016 | Chesworth et al. |
| 2016/0096804 A1 | 4/2016 | Shuttleworth et al. |
| 2016/0168165 A1 | 6/2016 | Koehler et al. |
| 2016/0176825 A1 | 6/2016 | Gray et al. |
| 2016/0229837 A1 | 8/2016 | Xi et al. |
| 2016/0257641 A1 | 9/2016 | Kobayashi et al. |
| 2016/0297795 A1 | 10/2016 | Heer et al. |
| 2016/0304511 A1 | 10/2016 | Jackson et al. |
| 2016/0304513 A1 | 10/2016 | Deligny et al. |
| 2017/0114078 A1 | 4/2017 | McGowan et al. |
| 2017/0121349 A1 | 5/2017 | Kim et al. |
| 2017/0129883 A1 | 5/2017 | Jackson et al. |
| 2017/0158688 A1 | 6/2017 | Jackson et al. |
| 2017/0222157 A1 | 8/2017 | Jatsch et al. |
| 2017/0333398 A1 | 11/2017 | Kojima et al. |
| 2018/0030453 A1 | 2/2018 | Zakharenko et al. |
| 2018/0072688 A1 | 3/2018 | Qian et al. |
| 2018/0079727 A1 | 3/2018 | Ohyabu et al. |
| 2018/0086725 A1 | 3/2018 | Kumar et al. |
| 2018/0153877 A1 | 6/2018 | Azam |
| 2018/0273511 A1 | 9/2018 | Long |
| 2019/0002442 A1 | 1/2019 | Zhao et al. |
| 2019/0022074 A1 | 1/2019 | Hadari et al. |
| 2019/0038603 A1 | 2/2019 | Jakobsson |
| 2019/0119217 A1 | 4/2019 | Long et al. |
| 2019/0134042 A1 | 5/2019 | Miao et al. |
| 2019/0135834 A1 | 5/2019 | Tamura et al. |
| 2019/0183866 A1 | 6/2019 | Tamura et al. |
| 2019/0382377 A1 | 12/2019 | Li et al. |
| 2019/0388426 A1 | 12/2019 | Nguyen et al. |
| 2020/0039933 A1 | 2/2020 | Gaisina et al. |
| 2020/0039961 A1 | 2/2020 | Campbell et al. |
| 2020/0039998 A1 | 2/2020 | Campbell et al. |
| 2020/0054635 A1 | 2/2020 | Campbell et al. |
| 2020/0062758 A1 | 2/2020 | Liu et al. |
| 2020/0101091 A1 | 4/2020 | Peyrottes et al. |
| 2020/0113901 A1 | 4/2020 | Campbell et al. |
| 2020/0113907 A1 | 4/2020 | Hagiwara et al. |
| 2020/0237717 A1 | 7/2020 | Jensen et al. |
| 2020/0268753 A1 | 8/2020 | Nguyen et al. |
| 2020/0274072 A1 | 8/2020 | Kugler |
| 2020/0317642 A1 | 10/2020 | Campbell et al. |
| 2021/0008046 A1 | 1/2021 | Bravo et al. |
| 2022/0127260 A1 | 4/2022 | Gray et al. |
| 2022/0127284 A1 | 4/2022 | Gray et al. |
| 2022/0411403 A1 | 12/2022 | Masse et al. |
| 2023/0146125 A1 | 5/2023 | Masse et al. |

(56) References Cited

U.S. PATENT DOCUMENTS

| | | | |
|---|---|---|---|
| 2023/0167110 A1 | 6/2023 | Masse et al. | |
| 2023/0265075 A1 | 8/2023 | Masse et al. | |

FOREIGN PATENT DOCUMENTS

| | | | |
|---|---|---|---|
| CN | 107383014 A | 11/2017 | |
| CN | 108689942 A | 10/2018 | |
| CN | 110092798 A | 8/2019 | |
| EP | 639573 A1 | 2/1995 | |
| EP | 3059225 A1 | 8/2016 | |
| EP | 3279187 A1 | 2/2018 | |
| EP | 3450435 A1 | 3/2019 | |
| JP | H11-283746 A | 10/1999 | |
| JP | 2000299186 A | 10/2000 | |
| JP | 2004067629 A | 3/2004 | |
| JP | 2005289921 A | 10/2005 | |
| JP | 2009149589 A | 7/2009 | |
| JP | 2016132649 A | 7/2016 | |
| KR | 10-2019-0064508 A | 6/2019 | |
| WO | WO-93/05163 A1 | 3/1993 | |
| WO | WO-97/11065 A1 | 3/1997 | |
| WO | WO-99/26932 A1 | 6/1999 | |
| WO | WO-2001/044259 A1 | 6/2001 | |
| WO | WO-2002/076960 A1 | 10/2002 | |
| WO | WO-2003/082272 A1 | 10/2003 | |
| WO | WO-2004/006849 A2 | 1/2004 | |
| WO | WO-2004/085425 A1 | 10/2004 | |
| WO | WO-2004/087153 A2 | 10/2004 | |
| WO | WO-2005/032548 A1 | 4/2005 | |
| WO | WO-2005/035526 A1 | 4/2005 | |
| WO | WO-2005/037273 A1 | 4/2005 | |
| WO | WO-2006/027365 A1 | 3/2006 | |
| WO | WO-2006/128129 A2 | 11/2006 | |
| WO | WO-2006/130469 A1 | 12/2006 | |
| WO | WO-2007/091950 A1 | 8/2007 | |
| WO | WO-2007/121484 A2 | 10/2007 | |
| WO | WO-2008/016666 A2 | 2/2008 | |
| WO | WO-2008/124145 A1 | 10/2008 | |
| WO | WO-2008/144062 A1 | 11/2008 | |
| WO | WO-2008/150015 A1 | 12/2008 | |
| WO | WO-2009/011775 A1 | 1/2009 | |
| WO | WO-2009/017954 A1 | 2/2009 | |
| WO | WO-2009/034386 A1 | 3/2009 | |
| WO | WO-2009/050228 A2 | 4/2009 | |
| WO | WO-2009/155565 A1 | 12/2009 | |
| WO | WO-2010/002492 A1 | 1/2010 | |
| WO | WO-2010/141796 A2 | 12/2010 | |
| WO | WO-2010/144909 A1 | 12/2010 | |
| WO | WO-2011/063908 A1 | 6/2011 | |
| WO | WO-2011/127833 A1 | 10/2011 | |
| WO | WO-2012/016133 A2 | 2/2012 | |
| WO | WO-2013/024078 A1 | 2/2013 | |
| WO | WO-2014/069426 A1 | 5/2014 | |
| WO | WO-2014/072435 A1 | 5/2014 | |
| WO | WO-2014/175330 A1 | 10/2014 | |
| WO | WO-2015/008861 A1 | 1/2015 | |
| WO | WO-2016/014576 A1 | 1/2016 | |
| WO | WO-2016/119700 A1 | 8/2016 | |
| WO | WO-2017/143014 A1 | 8/2017 | |
| WO | WO-2017/175068 A1 | 10/2017 | |
| WO | WO-2018/039557 A1 | 3/2018 | |
| WO | WO-2018/064498 A1 | 4/2018 | |
| WO | WO-2018/066545 A1 | 4/2018 | |
| WO | WO-2018/191146 A1 | 10/2018 | |
| WO | WO-2018/200786 A1 | 11/2018 | |
| WO | WO-2018/203099 A1 | 11/2018 | |
| WO | WO-2018/204765 A1 | 11/2018 | |
| WO | WO-2019/000683 A1 | 1/2019 | |
| WO | WO-2019/018119 A1 | 1/2019 | |
| WO | WO-2019/038683 A1 | 2/2019 | |
| WO | WO-2019/079596 A1 | 4/2019 | |
| WO | WO-2019/079607 A1 | 4/2019 | |
| WO | WO-2019/088159 A1 | 5/2019 | |
| WO | WO-2019/217838 A1 | 11/2019 | |
| WO | WO-2020/014599 A1 | 1/2020 | |
| WO | WO-2020/081450 A1 | 4/2020 | |
| WO | WO-2020/089455 A1 | 5/2020 | |
| WO | WO-2020/093905 A1 | 5/2020 | |
| WO | WO-2020/097396 A1 | 5/2020 | |
| WO | WO-2020/097398 A1 | 5/2020 | |
| WO | WO-2020/097400 A1 | 5/2020 | |
| WO | WO-2020/118045 A1 | 6/2020 | |
| WO | WO-2020/165907 A1 | 8/2020 | |
| WO | WO-2020/176597 A1 | 9/2020 | |
| WO | WO-2020/180768 A1 | 9/2020 | |
| WO | WO-2020/181050 A1 | 9/2020 | |
| WO | WO-2020/210481 A1 | 10/2020 | |
| WO | WO-2020/243457 A1 | 12/2020 | |
| WO | WO-2021/067682 A1 | 4/2021 | |
| WO | WO-2021/091575 A1 | 5/2021 | |
| WO | WO-2021/113557 A1 | 6/2021 | |
| WO | WO-2021/226261 A1 | 11/2021 | |
| WO | WO-2022/140527 A1 | 6/2022 | |
| WO | WO-2023/086319 A1 | 5/2023 | |

OTHER PUBLICATIONS

Bain "The selectivity of protein kinase inhibitors: a further update" Biochem. J. (2007) 408, 297-315.*
Fabian et. al. Nature Biotechnology 2005, 23, 329-336.*
Akhtar, W. et al., Therapeutic evolution of benzimidazole derivatives in the last quinquennial period, European Journal of Medicinal Chemistry, 126:705-753 (2017).
Choi, H.G. et al., Development of 'DFG-out' inhibitors of gatekeeper mutant kinases, Bioorganic & Medicinal Chemistry Letters, 22:5297-5302 (2012).
Clark, J. et al., Discovery and Development of Janus Kinase (JAK) Inhibitors for Inflammatory Diseases, Journal of Medicinal Chemistry, J. Med. Chem., 57:5023-5038 (2014).
International Search Report for PCT/US2021/030926, 7 pages (Sep. 8, 2021).
Jaffer, T. and Ma, D., The emerging role of chemokine receptor CXCR2 in cancer progression, Transl. Cancer Res., 5(Suppl 4):S616-S628 (2016).
Jutzi, J. et al., LSD1 Inhibition Prolongs Survival in Mouse Models of MPN by Selectivity Targeting the Disease Clone, HemaSphere, 2:3, 13 pages (2018).
Leroy, E. et al., Rethinking JAK2 inhibition: towards novel strategies of more specific and versatile janus kinase inhibition, Leukemia, 31(5):1023-1038 (2017).
Meyer, S. and Levine, R., Molecular Pathways: Molecular Basis for Sensitivity and Resistance to JAK Kinase Inhibitors, Clin. Cancer Res., 20(8):2051-2059 (2014).
O'Hare, T. et al., AP24534, a Pan-BCR-ABL Inhibitor for Chronic Myeloid Leukemia, Potently Inhibits the T3151 Mutant and Overcomes Mutation-Based Resistance, Cancer Cell, 16(5):401-412 (2009).
O'Shea, J. et al., Janus kinase Inhibitors in autoimmune diseases, Ann Rheum. Dis., 72, 11 pages (2013).
Ramurthy, S. et al., Design and Synthesis of Orally Bioavailable Benzimidazoles as Raf Kinase Inhibitors, J. Med. Chem., 51:7049-7052 (2008).
Ramurthy, S. et al., Supporting Information Design and Synthesis of Benzimidazoles Amides as Raf Kinase Inibitors, Novartis Institutes of Biomedical Research, 38 pages (2008).
Rodrigues, M.A. and Torres, T., JAK/STAT inhibitors for the treatment of atopic dermatitis, Journal of Dermatological Treatment, 31(1):33-40 (2020).
Rzymski, T. et al., SEL120-34A is a novel CDK8 inhibitor active in AML cells with high levels of serine phosphorylation of STAT1 and STAT5 transactivation domains, Oncotarget, 8(20):33779-33795 (2017).
Subramanian, S. et al., Design and Synthesis of Orally Bioavailable Benzimidazole Reverse Amides as Pan RAF Kinase Inhibitors, ACS Med. Chem. Lett., 5:989-992 (2014).
Vainchenker, W. et al., JAK inhibitors for the treatment of myeloproliferative neoplasms and other disorders, F1000 Research, 7(F1000 Faculty Rev), 19 pages (last updated Jan. 17, 2018).
Wu, S. et al., Activity of the Type II JAK2 Inhibitor CHZ868 in B Cell Acute Lymphoblastic Leukemia, Cancer Cell, 28:29-41 (2015).

(56) References Cited

OTHER PUBLICATIONS

Yumeen, S. et al., JAK inhibition synergistically potentiates BCL2, BET, HDAC, and proteasome inhibition in advanced CTCL, Blood Advances, 4(10):2213-2226 (2020).
Bundgard, Design of Prodrugs, Amsterdam, New York, Oxford, Elsevier, pp. 7-9, 21-24 (1985).
Dymock et al., Inhibitors of JAK2 and JAK3: an update on the patent literature 2010-2012, Expert Opin Ther Pat., 23(4):449-501 (2013).
Extended European Search Report for Application No. EP19882411.2, mailed Jun. 21, 2022.
Extended European Search Report for EP 19882880.8 mailed Jul. 11, 2022.
Extended European Search Report for EP19881035.0 mailed Jun. 29, 2022.
Li, et al., AutoT&T v.2: An Efficient and Versatile Tool for Lead Structure Generation and Optimization, J. Chem. Inf. Model, 56(2):435-453 (2016).
Okaniwa, et al., Design and synthesis of novel DFG-out RAF/vascular endothelial growth factor receptor 2 (VEGF2) inhibitors. 1. Exploration of [5,6]-fused bicyclic scaffolds, J Med Chem., 55(7):3452-78 (2012).
Williams et al., Discovery of RAF265: A Potent mut-B-RAF Inhibitor for the Treatment of Metastatic Melanoma, ACS Med. Chem Lett., 6(9):961-965 (2015).
Zhao, et al., Exploration of type II binding mode: A privileged approach for kinase inhibitor focused drug discovery?, ACS Chem Biol., 9(6):1230-41 (2014).
International Search Report for PCT/US2022/049220, 4 pages (mailed Feb. 6, 2023).
Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), 64th American Society of Hematology Annual Meeting, 1-4 (2022).
Rai, S. et al., The Second Generation Type II JAK2 inhibitor, AJ1-10502, Demonstrates Enhanced Selectivity Improved Therapeutic Efficacy and Reduced Mutant Cell Fraction Compared to Type I JAK2 inhibitors in Models of Myeloproliferative Neoplasms (MPNs), Poster (1 page), Presented at the 64th American Society of Hematology Annual Meeting from Dec. 10-13, 2022.
Steelman, L. S. et al., JAK/STAT, Raf/MEK/ERK, PI3K/Akt and BCR-ABL in cell cycle progression and leukemogenesis, Leukemia, 18:189-218 (2004).
Aaronson, D. S. and Horvath, C. M., A Road Map for Those Who Don't Know JAK-STAT, Science, 296(5573):1653-1655 (2002).
Andraos, R. et al., Modulation of activation-loop phosphorylation by JAK inhibitors is binding mode dependent, Cancer Discovery, 2(6):512-523 (2012).
Elf, S. et al., Mutant calreticulin requires both its mutant C-terminus and the thrombopoietin receptor for oncogenic transformation, Science Discovery, 6(4):368-381 (2016).
Harrison, C. et al., JAK Inhibition with Ruxolitinib versus Best Available Therapy for Myelofibrosis, the New England Journal of Medicine, 366(9):787-798 (2012).
International Search Report for PCT/US2019/060358, mailed on Mar. 3, 2020.
International Search Report for PCT/US2019/060360, mailed on Mar. 3, 2020.
International Search Report for PCT/US2019/060363, mailed on Mar. 9, 2020.
International Search Report for PCT/US2020/053922, mailed on Mar. 8, 2021.
International Search Report for PCT/US2021/064830, 4 pages (Mar. 25, 2022).
Koppikar, P. et al., Heterodimeric JAK-STAT Activation as a Mechanism of Persistence to JAK2 Inhibitor Therapy, Nature, 489(7414):155-159 (2012).
Levine, R. L., JAK-mutant Myeloproliferative Neoplasms, Current Topics in Microbiology and Immunology, 355:119-133 (2011).
Pandey, A. et al., Cloning of a receptor subunit required for signaling by thymic stromal lymphopoietin, Nature Immunology, 1(1):59-64 (2000).
Roberts, K. G. et al., Targetable Kinase-Activating Lesions in Ph-like Acute Lymphoblastic Leukemia, New England Journal of Medicine, 371(11):1005-1015 (2014).
Rui, L. et al., Cooperative Epigenetic Modulation by Cancer Amplicon Genes, Cancer Cell., 18(6):590-605 (2010).
Shiels, M. S. et al., Cancer Burden in the HIV-Infected Population in the United States, J Natl Cancer Inst., 103(9):753-762 (2011).
Smith, A. et al., Imidazo[1,2-a]pyridin-6-yl-benzamide analogs as potent RAF inhibitors, Bioorg Med Chem Lett., 27(23):5221-5224 (2017).
Verstovsek, S. et al., A Double-Blind Placebo-Controlled Trial of Ruxolitinib for Myelofibrosis, N Engl J Med., 366(9):799-807 (2012).
Yuanyuan, W. et al., Design, synthesis, biological evaluation and molecular modeling of novel 1H-pyrazolo [3,4-d] pyrimidine derivatives as BRAFV600Eand VEGFR-2 dual inhibitors, European Journal of Medicinal Chemistry, 155:210-228 (2018).
U.S. Appl. No. 17/308,740, Ajax Therapeutics, Inc.
U.S. Appl. No. 17/982,663, Masse et al.
International Preliminary Report on Patentability for PCT/US22/49220, 6 pages (mailed Jan. 3, 2024).

* cited by examiner

6-HETEROARYLOXY BENZIMIDAZOLES AND AZABENZIMIDAZOLES AS JAK2 INHIBITORS

RELATED APPLICATIONS

This application claims priority to and benefit of U.S. Application No. 63/130,251 filed Dec. 23, 2020, U.S. Application No. 63/218,097 filed Jul. 2, 2021, and U.S. Application No. 63/277,337 filed Nov. 9, 2021, the entire contents of each of which are hereby incorporated by reference.

BACKGROUND

Janus kinase 2 (JAK2) is a non-receptor tyrosine kinase involved in the JAK-STAT signaling pathway, which plays a role in cell processes such as immunity, cell division, and cell death. Dysfunction of the JAK-STAT pathway is implicated in various diseases, including cancer and other proliferative diseases, as well as diseases of the immune system. For example, essentially all BCR-ABL1-negative myeloproliferative neoplasms are associated with mutations that activate JAK2. In particular, JAK2V617F is the most prevalent mutation in myeloproliferative neoplasms, occurring in approx. 70% of all patients, and in up to 95% of patients with polycythemia vera. (Vainchenker, W., Kralovics, R. Blood 2017, 129(6):667-79). Even less common mutations, such as in MPL and CALR, have been shown to effect activation of JAK2, thereby initiating and/or driving disease progression. (Vainchenker, W. et al., F1000 Research 2018, 7 (F1000 Faculty Rev): 82). Furthermore, polymorphisms in JAK2 have been linked to various autoimmune diseases and inflammatory conditions, such as psoriasis and inflammatory bowel disease. (O'Shea, J. J. et al., Ann. Rheum. Dis. 2013 April, 72:ii111-ii115). Increased signaling through JAK2, as well as other members of the JAK family, is also associated with atopic dermatitis. (Rodrigues, M. A. and Torres, T. J. Derm. Treat. 2019, 31(1):33-40).

Inhibitors of JAKs (e.g., JAK2) are classified based on their binding mode. All currently approved JAK inhibitors are Type I inhibitors, which are those that bind the ATP-binding site in the active conformation of the kinase domain, thereby blocking catalysis (Vainchenker, W. et al.). However, increased phosphorylation of the JAK2 activation loop is observed with Type I inhibitors and may lead to acquired resistance in certain patients (Meyer S. C., Levine, R. L. Clin. Cancer Res. 2014, 20(8):2051-9). Type II inhibitors, on the other hand, bind the ATP-binding site of the kinase domain in the inactive conformation and, therefore, may avoid hyperphosphorylation observed with Type I inhibitors (Wu, S. C. et al. Cancer Cell 2015 Jul. 13, 28(1):29-41).

SUMMARY

The present disclosure provides compounds useful for inhibiting JAK2. In some embodiments, provided compounds are useful for, among other things, treating and/or preventing diseases, disorders, or conditions associated with JAK2.

In some embodiments, the present disclosure provides a compound of Formula I:

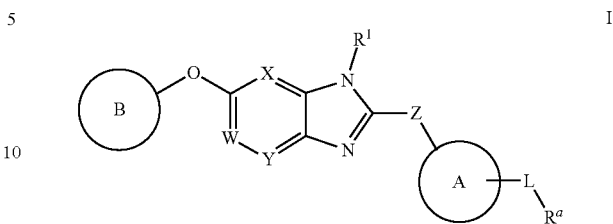

or a pharmaceutically acceptable salt thereof, wherein Ring A, Ring B, L, W, X, Y, Z, $R^1$, and $R^a$ are as defined herein.

DETAILED DESCRIPTION

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Unless otherwise stated, structures depicted herein are meant to include all stereoisomeric (e.g., enantiomeric or diastereomeric) forms of the structure, as well as all geometric or conformational isomeric forms of the structure. For example, the R and S configurations of each stereocenter are contemplated as part of the disclosure. Therefore, single stereochemical isomers, as well as enantiomeric, diastereomic, and geometric (or conformational) mixtures of provided compounds are within the scope of the disclosure. For example, in some case, Table 1 shows one or more stereoisomers of a compound, and unless otherwise indicated, represents each stereoisomer alone and/or as a mixture. Unless otherwise stated, all tautomeric forms of provided compounds are within the scope of the disclosure.

Unless otherwise indicated, structures depicted herein are meant to include compounds that differ only in the presence of one or more isotopically enriched atoms. For example, compounds having the present structures including replacement of hydrogen by deuterium or tritium, or replacement of a carbon by $^{13}$C- or $^{14}$C-enriched carbon are within the scope of this disclosure.

Aliphatic: The term "aliphatic" refers to a straight-chain (i.e., unbranched) or branched, optionally substituted hydrocarbon chain that is completely saturated or that contains one or more units of unsaturation, or a monocyclic or bicyclic hydrocarbon that is completely saturated or that contains one or more units of unsaturation but which is not aromatic (also referred to herein as "carbocyclic" or "cycloaliphatic"), that has a single point of attachment to the rest of the molecule. Unless otherwise specified, aliphatic groups contain 1-12 aliphatic carbon atoms. In some embodiments, aliphatic groups contain 1-6 aliphatic carbon atoms (e.g., $C_{1-6}$). In some embodiments, aliphatic groups contain 1-5 aliphatic carbon atoms (e.g., $C_{1-5}$). In other embodiments, aliphatic groups contain 1-4 aliphatic carbon atoms (e.g., $C_{1-4}$). In still other embodiments, aliphatic groups contain 1-3 aliphatic carbon atoms (e.g., $C_{1-3}$), and in yet other embodiments, aliphatic groups contain 1-2 aliphatic carbon atoms (e.g., $C_{1-2}$). Suitable aliphatic groups include, but are not limited to, linear or branched, substituted or unsubstituted alkyl, alkenyl, alkynyl groups and hybrids thereof. In some embodiments, "aliphatic" refers to a straight-chain (i.e., unbranched) or branched, optionally substituted hydrocarbon chain that is completely saturated or that contains one or more units of unsaturation that has a single point of attachment to the rest of the molecule.

Alkyl: The term "alkyl", used alone or as part of a larger moiety, refers to a saturated, optionally substituted straight or branched hydrocarbon group having (unless otherwise specified) 1-12, 1-10, 1-8, 1-6, 1-4, 1-3, or 1-2 carbon atoms (e.g., $C_{1-12}$, $C_{1-10}$, $C_{1-8}$, $C_{1-6}$, $C_{1-4}$, $C_{1-3}$, or $C_{1-2}$). Exemplary alkyl groups include methyl, ethyl, propyl, butyl, pentyl, hexyl, and heptyl.

Carbocyclyl: The terms "carbocyclyl," "carbocycle," and "carbocyclic ring" as used herein, refer to saturated or partially unsaturated cyclic aliphatic monocyclic, bicyclic, or polycyclic ring systems, as described herein, having from 3 to 14 members, wherein the aliphatic ring system is optionally substituted as described herein. Carbocyclic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, "carbocyclyl" (or "cycloaliphatic") refers to an optionally substituted monocyclic $C_3$-$C_8$ hydrocarbon, or an optionally substituted $C_7$-$C_{10}$ bicyclic hydrocarbon that is completely saturated or that contains one or more units of unsaturation, but which is not aromatic, that has a single point of attachment to the rest of the molecule. The term "cycloalkyl" refers to an optionally substituted saturated ring system of about 3 to about 10 ring carbon atoms. In some embodiments, cycloalkyl groups have 3-6 carbons. Exemplary monocyclic cycloalkyl rings include cyclopropyl, cyclobutyl, cyclopentyl, cyclohexyl, and cycloheptyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Alkenyl: The term "alkenyl", used alone or as part of a larger moiety, refers to an optionally substituted straight or branched hydrocarbon chain having at least one double bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl.

Alkynyl: The term "alkynyl", used alone or as part of a larger moiety, refers to an optionally substituted straight or branched chain hydrocarbon group having at least one triple bond and having (unless otherwise specified) 2-12, 2-10, 2-8, 2-6, 2-4, or 2-3 carbon atoms (e.g., $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Aryl: The term "aryl" refers to monocyclic and bicyclic ring systems having a total of six to fourteen ring members (e.g., $C_{6-14}$), wherein at least one ring in the system is aromatic and wherein each ring in the system contains three to seven ring members. The term "aryl" may be used interchangeably with the term "aryl ring". In some embodiments, "aryl" refers to an aromatic ring system which includes, but not limited to, phenyl, naphthyl, anthracyl and the like, which may bear one or more substituents. Unless otherwise specified, "aryl" groups are hydrocarbons.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 10 ring atoms (e.g., 5- to 6-membered monocyclic heteroaryl or 9- to 10-membered bicyclic heteroaryl); having 6, 10, or 14 $\pi$ electrons shared in a cyclic array; and having, in addition to carbon atoms, from one to five heteroatoms. Exemplary heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridonyl, pyridazinyl, pyrimidinyl, pyrazinyl, indolizinyl, purinyl, naphthyridinyl, pteridinyl, imidazo[1,2-a]pyrimidinyl, imidazo[1,2-a]pyridinyl, thienopyrimidinyl, triazolopyridinyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Nonlimiting examples include indolyl, isoindolyl, benzothienyl, benzofuranyl, dibenzofuranyl, indazolyl, benzimidazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, and benzoisoxazolyl. The term "heteroaryl" may be used interchangeably with the terms "heteroaryl ring", "heteroaryl group", or "heteroaromatic", any of which terms include rings that are optionally substituted.

Heteroatom: The term "heteroatom" as used herein refers to nitrogen, oxygen, or sulfur, and includes any oxidized form of nitrogen or sulfur, and any quaternized form of a basic nitrogen.

Heterocycle: As used herein, the terms "heterocycle", "heterocyclyl", and "heterocyclic ring" are used interchangeably and refer to a stable 3- to 8-membered monocyclic or 7- to 10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. A bicyclic heterocyclic ring also includes groups in which the heterocyclic ring is fused to one or more aryl, heteroaryl, or cycloaliphatic rings. Exemplary bicyclic heterocyclic groups include indolinyl, isoindolinyl, benzodioxolyl, 1,3-dihydroisobenzofuranyl, 2,3-dihydrobenzofuranyl, and tetrahydroquinolinyl. A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)).

Partially Unsaturated: As used herein, the term "partially unsaturated", when referring to a ring moiety, means a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient or subject: As used herein, the term "patient" or "subject" refers to any organism to which a provided composition is or may be administered, e.g., for experimental, diagnostic, prophylactic, cosmetic, and/or therapeutic purposes. Typical patients or subjects include animals (e.g., mammals such as mice, rats, rabbits, non-human primates, and/or humans). In some embodiments, a patient is a human. In some embodiments, a patient or a subject is suffering from or susceptible to one or more disorders or conditions. In some embodiments, a patient or subject displays one or more symptoms of a disorder or condition. In some embodiments, a patient or subject has been diagnosed with one or more disorders or conditions. In some embodiments, a patient or a subject is receiving or has received certain therapy to diagnose and/or to treat a disease, disorder, or condition.

Substituted or optionally substituted: As described herein, compounds of this disclosure may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

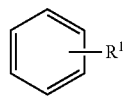

refers to at least

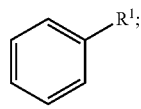

and

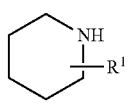

refers to at least

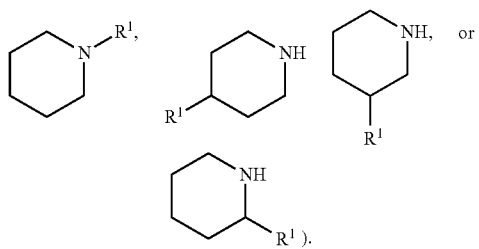

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes provided herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5- to 6-membered heteroaryl ring), or a 3- to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH₂)₀₋₂R●, -(haloR●), —(CH₂)₀₋₂OH, —(CH₂)₀₋₂OR●, —(CH₂)₀₋₂CH(OR●)₂, —O(haloR●), —CN, —N₃, —(CH₂)₀₋₂C(O)R●, —(CH₂)₀₋₂C(O)OH, —(CH₂)₀₋₂C(O)OR●, —(CH₂)₀₋₂SR●, —(CH₂)₀₋₂SH, —(CH₂)₀₋₂NH₂, —(CH₂)₀₋₂NHR●, —(CH₂)₀₋₂NR●₂, —NO₂, —SiR●₃, —OSiR●₃, —C(O)SR●, —(C₁₋₄ straight or branched alkylene)C(O)OR●, or —SSR● wherein each R● is unsubstituted or where preceded by "halo" is substituted only with one or more halogens, and is independently selected from C₁₋₄ aliphatic, —CH₂Ph, —O(CH₂)₀₋₁Ph, or a 3- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O ("oxo"), =S, =NNR*₂, =NNHC(O)R*, =NNHC(O)OR*, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆ aliphatic which may be substituted as defined below, or an unsubstituted 3- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃O—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 3- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, or an unsubstituted 3- to 6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 3- to 6-membered saturated, partially unsaturated, or aryl ring having 0-4 heteroatoms independently selected from nitrogen, oxygen, or sulfur.

Treat: As used herein, the term "treat" (also "treatment" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition.

Provided Compounds

The present disclosure provides a compound of Formula I:

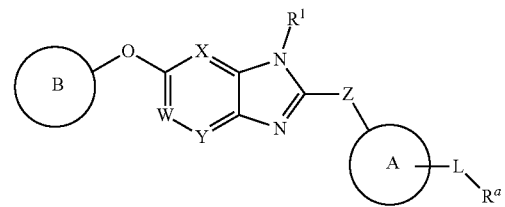

or a pharmaceutically acceptable salt thereof, wherein:
W is CR$^w$ or N;
X is CR$^x$ or N;
Y is CR$^y$ or N;
Z is —O— or —NR$^z$—;
R$^w$, R$^x$ and R$^y$ are each independently hydrogen, halogen, —OR$^2$, —N(R$^2$)₂, —SR$^2$, optionally substituted C$_{1-6}$ aliphatic, or —CN;
R$^z$ is hydrogen or optionally substituted C$_{1-6}$ aliphatic;
R$^1$ is optionally substituted C$_{1-6}$ aliphatic;
each R$^2$ is independently hydrogen or optionally substituted C$_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
Ring B is optionally substituted 9- to 16-membered bicyclic or tricyclic aryl, optionally substituted optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur;

L is a covalent bond or a bivalent $C_{1-3}$ straight or branched hydrocarbon chain; and $R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

In some embodiments, the present disclosure provides a compound of Formula II:

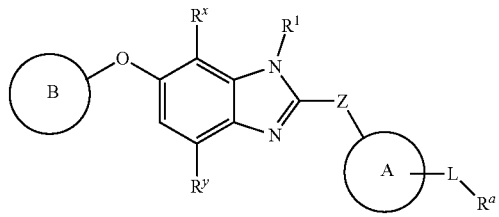

II or a pharmaceutically acceptable salt thereof, wherein Ring A, Ring B, L, Z, $R^1$, $R^a$, $R^x$, and $R^y$ are as defined above for Formula I and described in classes and subclasses herein, both singly and in combination.

In some embodiments, the present disclosure provides a compound of Formula III:

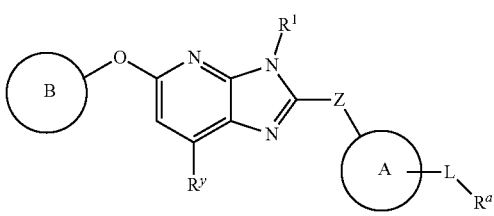

III or a pharmaceutically acceptable salt thereof, wherein Ring A, Ring B, L, Z, $R^1$, $R^a$, and $R^y$ are as defined above for Formula I and described in classes and subclasses herein, both singly and in combination.

In some embodiments, the present disclosure provides a compound of Formula IV:

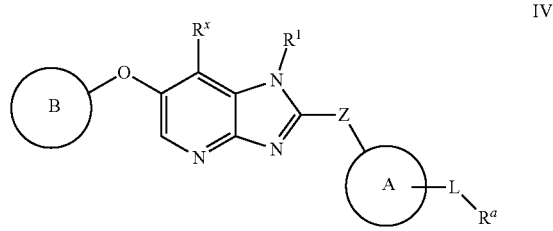

IV or a pharmaceutically acceptable salt thereof, wherein Ring A, Ring B, L, Z, $R^1$, $R^a$, and $R^x$ are as defined above for Formula I and described in classes and subclasses herein, both singly and in combination.

In some embodiments, the present disclosure provides a compound of Formula I-A:

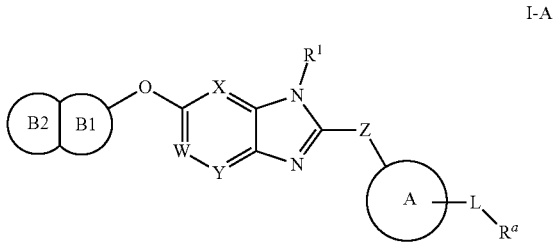

I-A or a pharmaceutically acceptable salt thereof, wherein Ring A, L, W, X, Y, Z, $R^1$, and $R^a$ are as defined above for Formula I and described in classes and subclasses herein, both singly and in combination; and:

Ring B1 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur; wherein Ring B1 is fused to Ring B2;

Ring B2 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur;

wherein Ring B2 is optionally (i) further fused to Ring B3, or (ii) Ring B2 and Ring B3 combine to form a spirocycle; and Ring B3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

In some embodiments, the present disclosure provides a compound of Formula II-A:

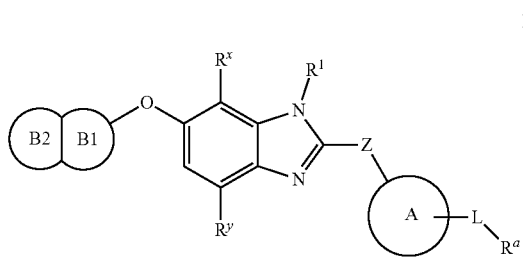

II-A or a pharmaceutically acceptable salt thereof, wherein Ring A, Ring B1, Ring B2, L, Z, $R^1$, $R^a$, $R^x$, and $R^y$ are as defined above for Formula I-A and described in classes and subclasses herein, both singly and in combination.

In some embodiments, the present disclosure provides a compound of Formula III-A:

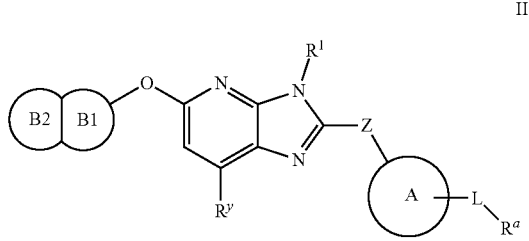

III-A or a pharmaceutically acceptable salt thereof, wherein Ring A, Ring B1, Ring B2, L, Z, $R^1$, $R^a$, and $R^y$ are as defined above for Formula I-A and described in classes and subclasses herein, both singly and in combination.

In some embodiments, the present disclosure provides a compound of Formula IV-A:

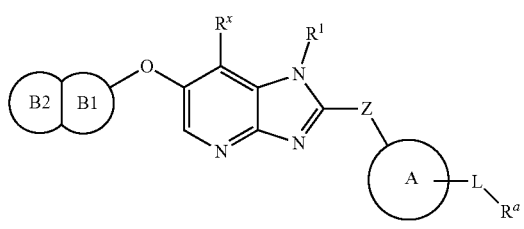

IV-A or a pharmaceutically acceptable salt thereof, wherein Ring A, Ring B1, Ring B2, L, Z, $R^1$, $R^a$, and $R^x$ are as defined above for Formula I-A and described in classes and subclasses herein, both singly and in combination.

In some embodiments, the present disclosure provides a compound of Formula I-B:

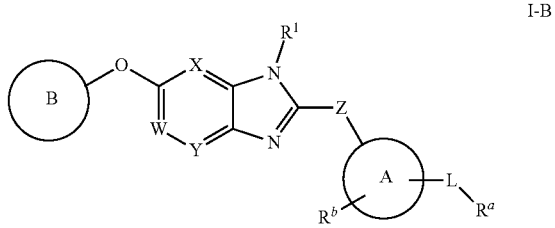

I-B or a pharmaceutically acceptable salt thereof, wherein Ring A, Ring B, L, W, X, Y, Z, $R^1$, and $R^a$ are as defined above for Formula I and described in classes and subclasses herein, both singly and in combination; and:

$R^b$ is hydrogen, halogen, —CN, —OR, —O(CH$_2$)$_n$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur;

each R is independently hydrogen, optionally substituted $C_{1-6}$ aliphatic, optionally substituted phenyl, optionally substituted 5- to 6-membered monocyclic heteroaryl having 1-3 heteroatoms independently selected from nitrogen, oxygen, and sulfur, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur;

each R' is independently optionally substituted $C_{1-6}$ aliphatic or optionally substituted 3- to 7-membered saturated or partially unsaturated carbocyclyl; and n is 1, 2, or 3.

In some embodiments, the present disclosure provides a compound of Formula I-B, wherein Ring A, Ring B, L, W, X, Y, Z, $R^1$, and $R^a$ are as defined above for Formula I and described in classes and subclasses herein, both singly and in combination; and:

$R^b$ is hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur;

each R is independently hydrogen, optionally substituted $C_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted $C_{1-6}$ aliphatic or optionally substituted 3- to 7-membered saturated or partially unsaturated carbocyclyl.

In some embodiments, the present disclosure provides a compound of Formula II-B:

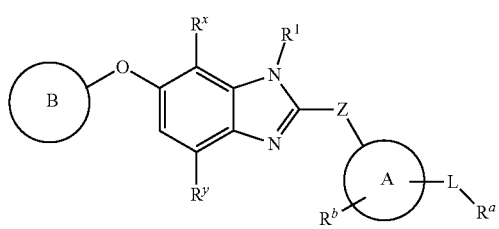

II-B or a pharmaceutically acceptable salt thereof, wherein Ring A, Ring B, L, Z, $R^1$, $R^a$, $R^b$, $R^x$, and R are as defined above for Formula I-B and described in classes and subclasses herein, both singly and in combination.

In some embodiments, the present disclosure provides a compound of Formula III-B:

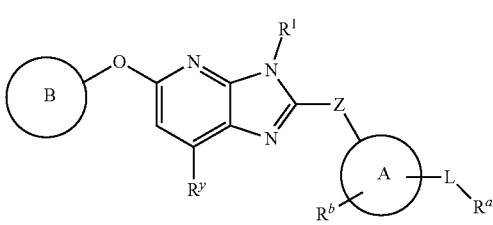

III-B or a pharmaceutically acceptable salt thereof, wherein Ring A, Ring B, L, Z, $R^1$, $R^a$, $R^b$, and $R^y$ are as defined above for Formula I-B and described in classes and subclasses herein, both singly and in combination.

In some embodiments, the present disclosure provides a compound of Formula IV-B:

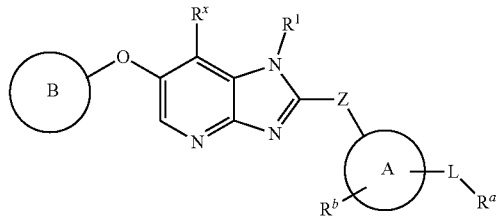

IV-B or a pharmaceutically acceptable salt thereof, wherein Ring A, Ring B, L, Z, $R^1$, $R^a$, $R^b$, and $R^x$ are as defined above for Formula I-B and described in classes and subclasses herein, both singly and in combination.

In some embodiments, the present disclosure provides a compound of Formula I-C:

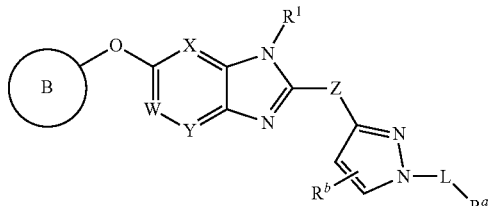

I-C or a pharmaceutically acceptable salt thereof, wherein Ring B, L, W, X, Y, Z, $R^1$, $R^a$, and $R^b$ are as defined above for Formula I-B and described in classes and subclasses herein, both singly and in combination.

In some embodiments, the present disclosure provides a compound of Formula II-C:

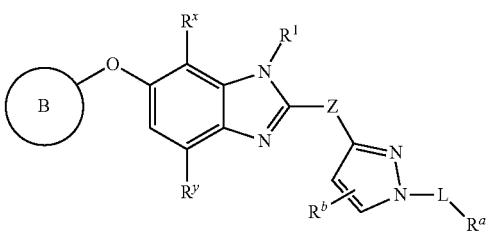

II-C or a pharmaceutically acceptable salt thereof, wherein Ring B, L, Z, $R^1$, $R^a$, $R^b$, $R^x$, and $R^y$ are as defined above for Formula I-B and described in classes and subclasses herein, both singly and in combination.

In some embodiments, the present disclosure provides a compound of Formula III-C:

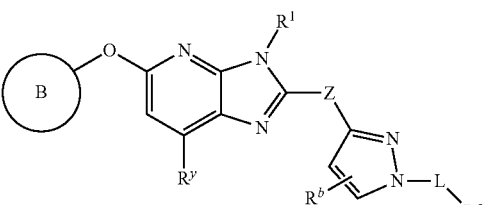

III-C or a pharmaceutically acceptable salt thereof, wherein Ring B, L, Z, R¹, R$^a$, R$^b$, and R$^y$ are as defined above for Formula I-B and described in classes and subclasses herein, both singly and in combination.

In some embodiments, the present disclosure provides a compound of Formula IV-C:

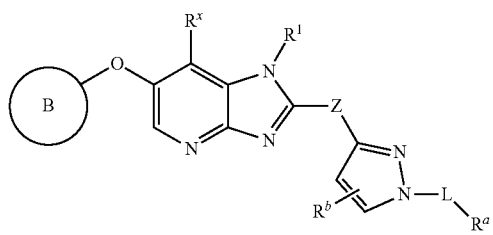

IV-C or a pharmaceutically acceptable salt thereof, wherein Ring B, L, Z, R¹, R$^a$, R$^b$, and R$^x$ are as defined above for Formula I-B and described in classes and subclasses herein, both singly and in combination.

In some embodiments, the present disclosure provides a compound of Formula I-D:

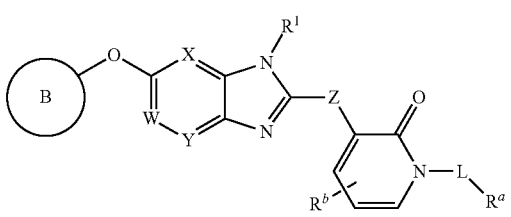

I-D or a pharmaceutically acceptable salt thereof, wherein Ring B, L, W, X, Y, Z, R¹, R$^a$, and R$^b$ are as defined above for Formula I-B and described in classes and subclasses herein, both singly and in combination.

In some embodiments, the present disclosure provides a compound of Formula II-D:

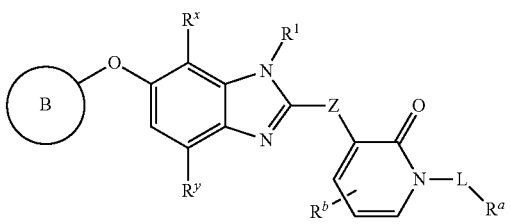

II-D or a pharmaceutically acceptable salt thereof, wherein Ring B, L, Z, R¹, R$^a$, R$^b$, R$^x$, and R$^y$ are as defined above for Formula I-B and described in classes and subclasses herein, both singly and in combination.

In some embodiments, the present disclosure provides a compound of Formula III-D:

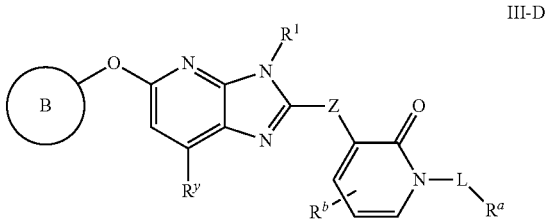

III-D or a pharmaceutically acceptable salt thereof, wherein Ring B, L, Z, R¹, R$^a$, R$^b$, and R$^y$ are as defined above for Formula I-B and described in classes and subclasses herein, both singly and in combination.

In some embodiments, the present disclosure provides a compound of Formula IV-D:

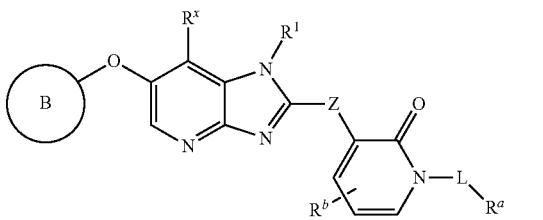

IV-D or a pharmaceutically acceptable salt thereof, wherein Ring B, L, Z, R¹, R$^a$, R$^b$, and R$^x$ are as defined above for Formula I-B and described in classes and subclasses herein, both singly and in combination.

In some embodiments, the present disclosure provides a compound of Formula I-E:

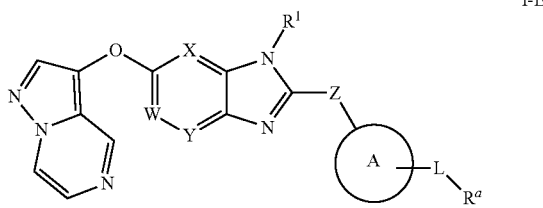

I-E or a pharmaceutically acceptable salt thereof, wherein Ring A, L, W, X, Y, Z, R¹, and R$^a$ are as defined above for Formula I and described in classes and subclasses herein, both singly and in combination.

In some embodiments, the present disclosure provides a compound of Formula II-E:

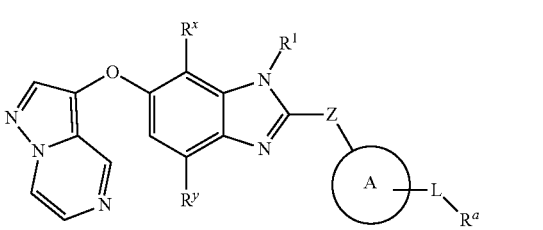

II-E or a pharmaceutically acceptable salt thereof, wherein Ring A, L, Z, $R^1$, $R^a$, $R^x$, and $R^y$ are as defined above for Formula I and described in classes and subclasses herein, both singly and in combination.

In some embodiments, the present disclosure provides a compound of Formula III-E:

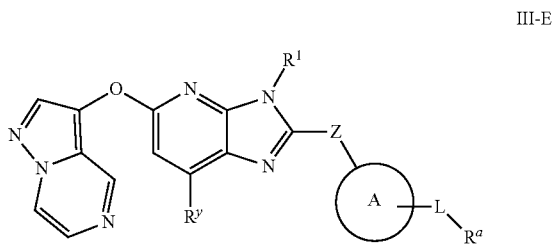

III-E or a pharmaceutically acceptable salt thereof, wherein Ring A, L, Z, $R^1$, $R^a$, and $R^y$ are as defined above for Formula I and described in classes and subclasses herein, both singly and in combination.

In some embodiments, the present disclosure provides a compound of Formula IV-E:

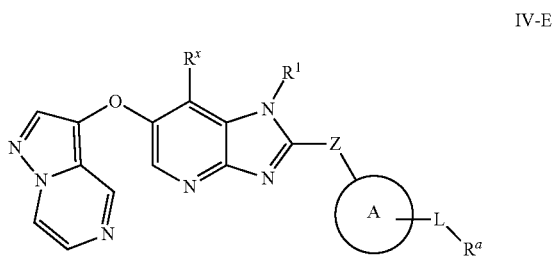

IV-E or a pharmaceutically acceptable salt thereof, wherein Ring A, L, Z, $R^1$, $R^a$, and $R^x$ are as defined above for Formula I and described in classes and subclasses herein, both singly and in combination.

In some embodiments of any of Formulae I, I-A, I-B, I-C, I-D, and I-E, W is $CR^w$. In some embodiments, W is N.

In some embodiments of any of Formulae I, I-A, I-B, I-C, I-D, and I-E, X is $CR^x$. In some embodiments, X is N.

In some embodiments of any of Formulae I, I-A, I-B, I-C, I-D, and I-E, Y is $CR^y$. In some embodiments, Y is N.

In some embodiments of any of Formulae I, I-A, I-B, I-C, I-D, and I-E, W is $CR^w$ or N, X is $CR^x$ or N, and Y is $CR^y$ or N, and no more than one of W, X, and Y is N. In some embodiments, W is $CR^w$ or N, X is $CR^x$ or N, and Y is $CR^y$ or N, and no more than two of W, X, and Y is N.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, Z is —O—. In some embodiments, Z is —$NR^z$—. In some embodiments, Z is —NH—.

In some embodiments of any of Formulae I, I-A, I-B, I-C, I-D, and I-E, $R^w$ is hydrogen, halogen, or optionally substituted $C_{1-6}$ aliphatic. In some embodiments, $R^w$ is hydrogen. In some embodiments, $R^w$ is halogen. In some embodiments, $R^w$ is fluoro. In some embodiments, $R^w$ is chloro. In some embodiments, $R^w$ is —$OR^2$. In some embodiments, $R^w$ is —$OR^2$, wherein $R^2$ is optionally substituted $C_{1-6}$ aliphatic. In some embodiments, Y is N, W is $CR^w$, and $R^w$ is —$OR^2$ wherein $R^2$ is optionally substituted $C_{1-6}$ aliphatic. In some embodiments, $R^w$ is —$N(R^2)_2$. In some embodiments, $R^w$ is —$SR^2$. In some embodiments, $R^w$ is —$SR^2$, wherein $R^2$ is optionally substituted $C_{1-6}$ aliphatic. In some embodiments, Y is N, W is $CR^w$, and $R^w$ is —$SR^2$ wherein $R^2$ is optionally substituted $C_{1-6}$ aliphatic. In some embodiments, $R^w$ is optionally substituted $C_{1-6}$ aliphatic. In some embodiments, $R^w$ is optionally substituted straight-chain or branched $C_{1-6}$ aliphatic (i.e., optionally substituted acyclic $C_{1-6}$ aliphatic). In some embodiments, $R^w$ is optionally substituted $C_{1-6}$ alkyl. In some embodiments, $R^w$ is optionally substituted $C_{1-4}$ alkyl. In some embodiments, $R^w$ is optionally substituted $C_{1-2}$ alkyl. In some embodiments, $R^w$ is optionally substituted methyl (e.g., methyl optionally substituted with one or more fluoro). In some embodiments, $R^w$ is —CN.

In some embodiments of any of Formulae I, II, IV, I-A, II-A, IV-A, I-B, II-B, IV-B, I-C, II-C, IV-C, I-D, II-D, IV-D, I-E, II-E, and IV-E, $R^x$ is hydrogen, halogen, —CN, —$OR^2$, or optionally substituted $C_{1-6}$ aliphatic. In some embodiments, $R^x$ is hydrogen, halogen, —CN, —O($C_{1-4}$ alkyl), or $C_{1-4}$ alkyl optionally substituted with one or more halogen. In some embodiments, $R^x$ is hydrogen, halogen, —$OR^2$, or optionally substituted $C_{1-6}$ aliphatic. In some embodiments, $R^x$ is hydrogen, halogen, —O($C_{1-4}$ alkyl), or $C_{1-4}$ alkyl optionally substituted with one or more halogen. In some embodiments, $R^x$ is hydrogen, halogen, or optionally substituted $C_{1-6}$ aliphatic. In some embodiments, $R^x$ is hydrogen. In some embodiments, $R^x$ is halogen. In some embodiments, $R^x$ is fluoro. In some embodiments, $R^x$ is chloro. In some embodiments, $R^x$ is —$OR^2$. In some embodiments, $R^x$ is —$OR^2$, wherein $R^2$ is optionally substituted $C_{1-6}$ aliphatic (e.g., optionally substituted $C_{1-6}$ alkyl). In some embodiments, $R^x$ is —O($C_{1-4}$ alkyl). In some embodiments, $R^x$ is —$OCH_3$. In some embodiments, $R^x$ is —$N(R^2)_2$. In some embodiments, $R^x$ is —$SR^2$. In some embodiments, $R^x$ is —$SR^2$, wherein $R^2$ is optionally substituted $C_{1-6}$ aliphatic. In some embodiments, $R^x$ is optionally substituted $C_{1-6}$ aliphatic. In some embodiments, $R^x$ is optionally substituted straight-chain or branched $C_{1-6}$ aliphatic (i.e., optionally substituted acyclic $C_{1-6}$ aliphatic). In some embodiments, $R^x$ is optionally substituted $C_{1-6}$ alkyl (e.g., $C_{1-6}$ alkyl optionally substituted with one or more fluoro). In some embodiments, $R^x$ is optionally substituted $C_{1-4}$ alkyl (e.g., $C_{1-4}$ alkyl optionally substituted with one or more fluoro). In some embodiments, $R^x$ is optionally substituted $C_{1-2}$ alkyl (e.g., $C_{1-2}$ alkyl optionally substituted with one or more fluoro). In some embodiments, $R^x$ is optionally substituted methyl (e.g., methyl optionally substituted with one or more fluoro, e.g., —$CHF_2$). In some embodiments, $R^x$ is —CN.

In some embodiments of any of Formulae I, II, III, I-A, II-A, III-A, I-B, II-B, III-B, I-C, II-C, III-C, I-D, II-D, III-D, I-E, II-E, and III-E, $R^y$ is hydrogen, halogen, or optionally substituted $C_{1-6}$ aliphatic. In some embodiments, $R^y$ is hydrogen. In some embodiments, $R^y$ is halogen. In some embodiments, $R^y$ is fluoro. In some embodiments, $R^y$ is chloro. In some embodiments, $R^y$ is —$OR^2$. In some embodiments, $R^y$ is —$OR^2$, wherein $R^2$ is optionally substituted $C_{1-6}$ aliphatic. In some embodiments, W is N, Y is $CR^y$, and $R^y$ is —$OR^2$ wherein $R^2$ is optionally substituted $C_{1-6}$ aliphatic. In some embodiments, $R^y$ is —$N(R^2)_2$. In some embodiments, $R^y$ is —$SR^2$. In some embodiments, $R^y$ is —$SR^2$, wherein $R^2$ is optionally substituted $C_{1-6}$ aliphatic. In some embodiments, W is N, Y is $CR^y$, and $R^y$ is —$SR^2$ wherein $R^2$ is optionally substituted $C_{1-6}$ aliphatic. In some embodiments, $R^y$ is optionally substituted $C_{1-6}$ aliphatic. In some embodiments, $R^y$ is optionally substituted straight-chain or branched $C_{1-6}$ aliphatic (i.e., optionally substituted acyclic $C_{1-6}$ aliphatic). In some embodiments, $R^y$ is optionally substituted $C_{1-6}$ alkyl. In some embodiments, $R^y$ is optionally substituted $C_{1-4}$ alkyl. In some embodiments, $R^y$ is optionally substituted $C_{1-2}$ alkyl. In some embodiments, $R^y$ is optionally substituted methyl (e.g., methyl optionally substituted with one or more fluoro). In some embodiments, $R^y$ is —CN.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, $R^z$ is hydrogen. In some embodiments, $R^z$ is optionally substituted $C_{1-6}$ aliphatic. In some embodiments, $R^z$ is optionally substituted straight-chain or branched $C_{1-6}$ aliphatic (i.e., optionally substituted acyclic $C_{1-6}$ aliphatic). In some embodiments, $R^z$ is optionally substituted $C_{1-6}$ alkyl. In some embodiments, $R^z$ is optionally substituted $C_{1-4}$ alkyl. In some embodiments, $R^z$ is unsubstituted $C_{1-4}$ alkyl. In some embodiments, $R^z$ is optionally substituted $C_{1-2}$ alkyl. In some embodiments, $R^z$ is unsubstituted $C_{1-2}$ alkyl.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, $R^1$ is optionally substituted straight-chain or branched $C_{1-6}$ aliphatic (i.e., optionally substituted acyclic $C_{1-6}$ aliphatic). In some embodiments, $R^1$ is optionally substituted $C_{1-6}$ alkyl. In some embodiments, $R^1$ is optionally substituted $C_{1-4}$ alkyl. In some embodiments, $R^1$ is unsubstituted $C_{1-4}$ alkyl. In some embodiments, $R^1$ is optionally substituted $C_{1-2}$ alkyl. In some embodiments, $R^1$ is unsubstituted $C_{1-2}$ alkyl. In some embodiments, $R^1$ is methyl.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, each $R^2$ is independently hydrogen or optionally substituted $C_{1-4}$ aliphatic. In some embodiments, each $R^2$ is independently hydrogen or optionally substituted $C_{1-2}$ aliphatic. In some embodiments, each $R^2$ is hydrogen. In some embodiments, each $R^2$ is independently optionally substituted $C_{1-6}$ aliphatic. In some embodiments, each $R^2$ is independently optionally substituted straight-chain or branched $C_{1-6}$ aliphatic (i.e., optionally substituted acyclic $C_{1-6}$ aliphatic). In some embodiments, each $R^2$ is independently optionally substituted $C_{1-4}$ aliphatic. In some embodiments, each $R^2$ is independently optionally substituted straight-chain or branched $C_{1-4}$ aliphatic (i.e., optionally substituted acyclic $C_{1-4}$ aliphatic). In some embodiments, each $R^2$ is independently optionally substituted $C_{1-2}$ aliphatic. In some embodiments, each $R^2$ is independently hydrogen or $C_{1-6}$ alkyl. In some embodiments, each $R^2$ is independently hydrogen or $C_{1-4}$ alkyl. In some embodiments, each $R^2$ is independently hydrogen or $C_{1-2}$ alkyl.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, Ring A is (i) optionally substituted on a substitutable carbon atom with one or more groups independently selected from oxo, halogen, $R^o$, —CN, —$OR^o$, —$O(CH_2)_{1-4}R^o$, —$SR^o$, —$N(R^o)_2$, —$NO_2$, —$C(O)R^o$, —$C(O)OR^o$, —$C(O)NR^o_2$, —$OC(O)R^o$, —$OC(O)NR^o_2$, —$OC(O)OR^o$, —$OS(O)_2R^o$, —$OS(O)_2NR^o_2$, —$N(R^o)C(O)R^o$, —$N(R^o)S(O)_2R^o$, —$S(O)_2R^o$, —$SO_2NR^o_2$, and —$S(O)_2OR^o$, and (ii) optionally substituted on a substitutable nitrogen atom with one or more groups selected from —$R^†$, —$NR^†_2$, —$C(O)R^†$, —$C(O)OR^†$, —$S(O)_2R^†$, and —$S(O)_2NR^†_2$. In some embodiments, Ring A is (i) optionally substituted on a substitutable carbon atom with one or more groups independently selected from oxo, halogen, $R^o$, —CN, —$OR^o$, —$O(CH_2)_{1-4}R^o$, —$SR^o$, —$N(R^o)_2$, —$NO_2$, —$C(O)R^o$, —$C(O)OR^o$, —$C(O)NR^o_2$, —$OC(O)R^o$, —$OC(O)NR^o_2$, —$OC(O)OR^o$, —$OS(O)_2R^o$, —$OS(O)_2NR^o_2$, —$N(R^o)C(O)R^o$, —$N(R^o)S(O)_2R^o$, —$S(O)_2R^o$, —$SO_2NR^o_2$, and —$S(O)_2OR^o$, and (ii) optionally substituted on a substitutable nitrogen atom with one or more groups selected from —$R^†$, —$NR^†_2$, —$C(O)R^†$, —$C(O)OR^†$, —$S(O)_2R^†$, and —$S(O)_2NR^†_2$. In some embodiments, Ring A is (i) optionally substituted on a substitutable carbon atom with one or more groups independently selected from oxo, halogen, $R^o$, —CN, —$OR^o$, —$O(CH_2)_{1-4}R^o$, —$N(R^o)_2$, and —$C(O)NR^o_2$, and (ii) optionally substituted on a substitutable nitrogen atom with one or more groups selected from —$R^†$. In some embodiments, Ring A is (i) optionally substituted on a substitutable carbon atom with one or more groups independently selected from oxo, halogen, and $R^o$, and (ii) optionally substituted on a substitutable nitrogen atom with one or more groups selected from —$R^†$. In some embodiments, Ring A is (i) optionally substituted on a substitutable carbon atom with one or more groups independently selected from halogen and $R^o$, and (ii) optionally substituted on a substitutable nitrogen atom with one or more groups selected from —$R^†$.

In some embodiments, Ring A is optionally substituted with one or more $R^b$ (i.e., in addition to being substituted with -L-$R^a$), wherein $R^b$ is as defined in Formula I-B above and described in classes and subclasses herein. In some embodiments, Ring A is substituted with zero, one, two, three, four, or five $R^b$, as valency allows.

In some embodiments, Ring A is optionally substituted phenyl, optionally substituted 5- to 6-membered monocyclic heteroaryl having 1-4 heteroatoms independently selected from nitrogen, oxygen, and sulfur, or optionally substituted 8- to 10-membered bicyclic heteroaryl having 1-4 heteroatoms independently selected from nitrogen, oxygen, and sulfur.

In some embodiments, Ring A is optionally substituted 5- to 6-membered monocyclic heteroaryl having 1-4 heteroatoms independently selected from nitrogen, oxygen, and sulfur or optionally substituted 8- to 10-membered bicyclic heteroaryl having 1-4 heteroatoms independently selected from nitrogen, oxygen, and sulfur.

In some embodiments, Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, or optionally substituted 3- to 7-membered saturated or partially unsaturated monocyclic heterocyclyl having 1-3 heteroatoms independently selected from nitrogen, oxygen, and sulfur.

In some embodiments, Ring A is optionally substituted phenyl. In some embodiments, Ring A is not optionally substituted phenyl.

In some embodiments, Ring A is optionally substituted 5- to 6-membered monocyclic heteroaryl having 1-4 heteroatoms independently selected from nitrogen, oxygen, and sulfur. In some embodiments, Ring A is optionally substituted 5- to 6-membered monocyclic heteroaryl having 1-2 heteroatoms independently selected from nitrogen, oxygen, and sulfur. In some embodiments, Ring A is optionally substituted 5-membered monocyclic heteroaryl having 1-4 heteroatoms independently selected from nitrogen, oxygen, and sulfur. In some embodiments, Ring A is optionally substituted pyrazolyl or thiazolyl. In some embodiments, Ring A is optionally substituted pyrazolyl. In some embodiments, Ring A is optionally substituted 6-membered monocyclic heteroaryl having 1-4 heteroatoms independently selected from nitrogen, oxygen, and sulfur. In some embodiments, Ring A is optionally substituted pyridyl, pyridonyl, pyridazinonyl, pyrimidyl, pyrimidonyl, or pyrimidinedionyl. In some embodiments, Ring A is optionally substituted pyridonyl or pyridazinonyl. In some embodiments, Ring A is optionally substituted pyridonyl.

In some embodiments, Ring A is optionally substituted 8- to 10-membered bicyclic heteroaryl having 1-4 heteroatoms independently selected from nitrogen, oxygen, and sulfur. In some embodiments, Ring A is optionally substituted 8-membered bicyclic heteroaryl having 1-4 heteroatoms independently selected from nitrogen, oxygen, and sulfur. In some embodiments, Ring A is optionally substituted 9-membered bicyclic heteroaryl having 1-4 heteroatoms independently selected from nitrogen, oxygen, and sulfur. In some embodiments, Ring A is optionally substituted 10-membered bicyclic heteroaryl having 1-4 heteroatoms independently selected from nitrogen, oxygen, and sulfur.

In some embodiments, Ring A is optionally substituted 3- to 7-membered saturated or partially unsaturated monocyclic carbocyclyl. In some embodiments, Ring A is optionally substituted 3-membered saturated or partially unsaturated monocyclic carbocyclyl. In some embodiments, Ring A is optionally substituted 4-membered saturated or partially unsaturated monocyclic carbocyclyl. In some embodiments, Ring A is optionally substituted 5-membered saturated or partially unsaturated monocyclic carbocyclyl. In some embodiments, Ring A is optionally substituted 6-membered saturated or partially unsaturated monocyclic carbocyclyl. In some embodiments, Ring A is not optionally substituted 6-membered saturated or partially unsaturated monocyclic carbocyclyl. In some embodiments, Ring A is optionally substituted 7-membered saturated or partially unsaturated monocyclic carbocyclyl.

In some embodiments, Ring A is optionally substituted 3- to 7-membered saturated or partially unsaturated monocyclic heterocyclyl having 1-3 heteroatoms independently selected from nitrogen, oxygen, and sulfur. In some embodiments, Ring A is optionally substituted 3-membered saturated or partially unsaturated monocyclic heterocyclyl having 1-2 heteroatoms independently selected from nitrogen, oxygen, and sulfur. In some embodiments, Ring A is optionally substituted 4-membered saturated or partially unsaturated monocyclic heterocyclyl having 1-3 heteroatoms independently selected from nitrogen, oxygen, and sulfur. In some embodiments, Ring A is optionally substituted 5-membered saturated or partially unsaturated monocyclic heterocyclyl having 1-3 heteroatoms independently selected from nitrogen, oxygen, and sulfur. In some embodiments, Ring A is optionally substituted 6-membered saturated or partially unsaturated monocyclic heterocyclyl having 1-3 heteroatoms independently selected from nitrogen, oxygen, and sulfur. In some embodiments, Ring A is optionally substituted 7-membered saturated or partially unsaturated monocyclic heterocyclyl having 1-3 heteroatoms independently selected from nitrogen, oxygen, and sulfur.

In some embodiments, Ring A is optionally substituted 7- to 10-membered saturated or partially unsaturated bicyclic heterocyclyl having 1-4 heteroatoms independently selected from nitrogen, oxygen, and sulfur. In some embodiments, Ring A is optionally substituted 7-membered saturated or partially unsaturated bicyclic heterocyclyl having 1-4 heteroatoms independently selected from nitrogen, oxygen, and sulfur. In some embodiments, Ring A is optionally substituted 8-membered saturated or partially unsaturated bicyclic heterocyclyl having 1-4 heteroatoms independently selected from nitrogen, oxygen, and sulfur. In some embodiments, Ring A is not optionally substituted 8-membered saturated or partially unsaturated bicyclic heterocyclyl having 1-4 heteroatoms independently selected from nitrogen, oxygen, and sulfur (e.g., optionally substituted hexahydrofuro[3,2-b]furan). In some embodiments, Ring A is optionally substituted 9-membered saturated or partially unsaturated bicyclic heterocyclyl having 1-4 heteroatoms independently selected from nitrogen, oxygen, and sulfur. In some embodiments, Ring A is optionally substituted 10-membered saturated or partially unsaturated bicyclic heterocyclyl having 1-4 heteroatoms independently selected from nitrogen, oxygen, and sulfur.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, L is a covalent bond. In some embodiments, L is a bivalent $C_{1-3}$ straight or branched hydrocarbon chain. In some embodiments, L is a bivalent $C_{1-2}$ straight or branched hydrocarbon chain. In some embodiments, L is methylene (i.e., —$CH_2$—). In some embodiments, L is —$CH_2CH_2$—. In some embodiments, L is —$CH_2CH_2CH_2$—. In some embodiments, L is a covalent bond or —$CH_2$—.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, $R^a$ is hydrogen, halogen, optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, $R^a$ is optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur. In some embodiments, $R^a$ is hydrogen, halogen, or an optionally substituted group selected from $C_{1-4}$ alkyl, 5- to 6-membered monocyclic heteroaryl having 1-2 heteroatoms independently selected from nitrogen, oxygen, and sulfur, 3- to 6-membered cycloalkyl, 3- to 7-membered saturated monocyclic heterocyclyl having 1-2 heteroatoms independently selected from nitrogen, oxygen, and sulfur, or optionally substituted 7- to 8-membered saturated, spirocyclic, bicyclic heterocyclyl having 1-2 heteroatoms independently selected from nitrogen, oxygen, and sulfur. In some embodiments, $R^a$ is an optionally substituted group selected from $C_{1-4}$ alkyl, 5- to 6-membered monocyclic heteroaryl having 1-2 heteroatoms independently selected from nitrogen, oxygen, and sulfur, 3- to 6-membered cycloalkyl, 3- to 6-membered saturated monocyclic heterocyclyl having 1-2 heteroatoms independently selected from nitrogen, oxygen, and sulfur, or optionally substituted 7- to 8-membered saturated, spirocyclic, bicyclic heterocyclyl having 1-2 heteroatoms independently selected from nitrogen, oxygen, and sulfur. In some embodiments, $R^a$ is an optionally substituted group selected from $C_{1-4}$ alkyl, 5- to 6-membered monocyclic heteroaryl having 1-2 heteroatoms independently selected from nitrogen, oxygen, and sulfur, 3- to 6-membered cycloalkyl, 3- to 6-membered saturated monocyclic heterocyclyl having 1-2 heteroatoms independently selected from nitrogen, oxygen, and sulfur, or optionally substituted 7- to 10-membered saturated, spirocyclic, bicyclic heterocyclyl having 1-2 heteroatoms independently selected from nitrogen, oxygen, and sulfur. In some embodiments, $R^a$ is optionally substituted $C_{1-6}$ aliphatic, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

In some embodiments, $R^a$ is hydrogen. In some embodiments, $R^a$ is not hydrogen.

In some embodiments, $R^a$ is halogen. In some embodiments, $R^a$ is fluoro, chloro, bromo, or iodo. In some embodiments, $R^a$ is fluoro. In some embodiments, $R^a$ is chloro. In some embodiments, $R^a$ is not halogen. In some embodiments, $R^a$ is not fluoro. In some embodiments, $R^a$ is not chloro. In some embodiments, when L is a covalent bond, $R^a$ is not halogen. In some embodiments, when L is a covalent bond, $R^a$ is not fluoro. In some embodiments, when L is a covalent bond, $R^a$ is not chloro.

In some embodiments, $R^a$ is optionally substituted $C_{1-6}$ aliphatic. In some embodiments, $R^a$ is optionally substituted straight-chain or branched $C_{1-6}$ aliphatic (i.e., optionally substituted acyclic $C_{1-6}$ aliphatic). In some embodiments, $R^a$ is $C_{1-6}$ aliphatic optionally substituted with one or more halogen, —CN, —O($C_{1-6}$ alkyl), or —OH. In some embodiments, $R^a$ is optionally substituted $C_{1-6}$ alkyl. In some embodiments, $R^a$ is $C_{1-6}$ alkyl optionally substituted with one or more halogen, —CN, —O($C_{1-6}$ alkyl), or —OH. In some embodiments, $R^a$ is optionally substituted $C_{1-4}$ alkyl. In some embodiments, $R^a$ is $C_{1-4}$ alkyl optionally substituted with one or more halogen, —CN, —O($C_{1-6}$ alkyl), or —OH. In some embodiments, $R^a$ is —$CH_3$, —$CH_2CN$, —$CH_2CH_2OCH_3$, —$CH_2CH_2OH$, —$CH_2CHF_2$, —$CH_2CH(OH)CH_3$, —$CH(CH_3)CH_2CN$, —$CH_2C(CH_3)_2OCH_3$, or —$CH_2CH(CH_3)CH_2OH$. In some embodiments, $R^a$ is —$CH_3$, —$CH_2CN$, —$CH_2CH_2CN$, —$CH_2CH_2OCH_3$, —$CH_2CH_2OH$, —$CH_2CHF_2$, —$CH_2CH(OH)CH_3$, —$CH(CH_3)CH_2CN$, —$CH_2C(CH_3)_2OCH_3$, or —$CH_2CH(CH_3)CH_2OH$. In some embodiments, $R^a$ is —$CH_3$, —$CD_3$, —$CF_3$, —$CH_2CN$, —$CH_2CH_3$, —$CH_2CH_2CN$, —$CH_2CH_2OCH_3$, —$CH_2CH_2OH$, —$CH_2CHF_2$, —$CH(CH_3)_2$, —$CH_2CH(OH)CH_3$, —$CH(CH_3)CH_2CN$, —$CH_2C(CH_3)_2OCH_3$, or —$CH_2CH(CH_3)CH_2OH$. In some embodiments, when L is a covalent bond, $R^a$ is not —$CF_3$.

In some embodiments, $R^a$ is optionally substituted phenyl.

In some embodiments, $R^a$ is optionally substituted 5- to 6-membered monocyclic heteroaryl having 1-4 heteroatoms independently selected from nitrogen, oxygen, and sulfur. In some embodiments, $R^a$ is optionally substituted 5- to 6-membered monocyclic heteroaryl having 1-2 heteroatoms independently selected from nitrogen, oxygen, and sulfur. In some embodiments, $R^a$ is optionally substituted 5-membered monocyclic heteroaryl having 1-4 heteroatoms independently selected from nitrogen, oxygen, and sulfur. In some embodiments, $R^a$ is a 5-membered monocyclic heteroaryl having 1-4 heteroatoms independently selected from nitrogen, oxygen, and sulfur optionally substituted with one or more $C_{1-6}$ alkyl (e.g., methyl). In some embodiments, $R^a$ is optionally substituted pyrazolyl or imidazolyl. In some embodiments, $R^a$ is optionally substituted pyrazolyl. In some embodiments, $R^a$ is pyrazolyl or imidazolyl optionally substituted with one or more $C_{1-6}$ alkyl (e.g., methyl). In some embodiments, $R^a$ is pyrazolyl optionally substituted with one or more $C_{1-6}$ alkyl (e.g., methyl). In some embodiments, $R^a$ is

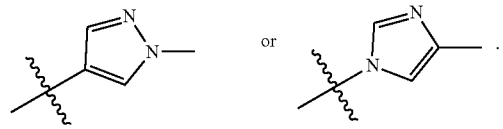

In some embodiments, $R^a$ is optionally substituted 6-membered monocyclic heteroaryl having 1-4 heteroatoms independently selected from nitrogen, oxygen, and sulfur. In some embodiments, $R^a$ is optionally substituted pyridinyl. In some embodiments, $R^a$ is pyridinyl. In some embodiments, $R^a$ is

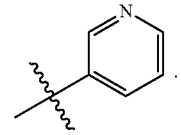 [SMILES: *c1cccnc1]

In some embodiments, $R^a$ is optionally substituted 3- to 7-membered saturated or partially unsaturated monocyclic carbocyclyl. In some embodiments, $R^a$ is 3- to 7-membered saturated or partially unsaturated monocyclic carbocyclyl optionally substituted with one or more —CN or —OH. In some embodiments, $R^a$ is optionally substituted 3- to 6-membered saturated monocyclic carbocyclyl. In some embodiments, $R^a$ is optionally substituted 4- to 6-membered saturated monocyclic carbocyclyl. In some embodiments, $R^a$ is 3- to 6-membered saturated monocyclic carbocyclyl optionally substituted with one or more —CN or —OH. In some embodiments, $R^a$ is 4- to 6-membered saturated monocyclic carbocyclyl optionally substituted with one or more —CN or —OH. In some embodiments, $R^a$ is optionally substituted 3-membered saturated monocyclic carbocyclyl. In some embodiments, $R^a$ is optionally substituted 4-membered saturated monocyclic carbocyclyl. In some embodiments, $R^a$ is optionally substituted 5-membered saturated monocyclic carbocyclyl. In some embodiments, $R^a$ is optionally substituted 6-membered saturated monocyclic carbocyclyl. In some embodiments, $R^a$ is optionally substituted 7-membered saturated monocyclic carbocyclyl. In some embodiments, $R^a$ is

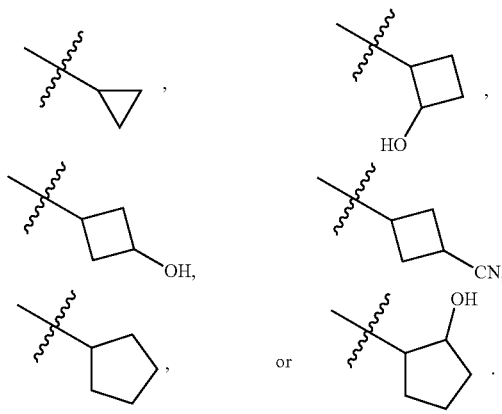

In some embodiments, $R^a$ is optionally substituted 3- to 7-membered saturated or partially unsaturated monocyclic heterocyclyl having 1-3 heteroatoms independently selected from nitrogen, oxygen, and sulfur. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more optionally substituted $C_{1-6}$ alkyl or —OH. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more halogen, optionally substituted $C_{1-6}$ alkyl, —C(O)($C_{1-6}$ alkyl), or —OH. In some embodiments, $R^a$ is 3- to 7-membered saturated or partially unsaturated monocyclic heterocyclyl having 1-3 heteroatoms independently selected from nitrogen, oxygen, and sulfur optionally substituted with one or more halogen, —OH, —O($C_{1-4}$ alkyl), —N($C_{1-4}$ alkyl)$_2$, —C(O)($C_{1-6}$ alkyl), —CN, or optionally substituted $C_{1-6}$ alkyl. In some embodiments, $R^a$ is optionally substituted 4- to 7-membered saturated monocyclic heterocyclyl having 1-2 heteroatoms independently selected from nitrogen, oxygen, and sulfur. In some embodiments, $R^a$ is optionally substituted 4- to 6-membered saturated monocyclic heterocyclyl having 1-2 heteroatoms independently selected from nitrogen, oxygen, and sulfur. In some embodiments, $R^a$ is 4- to 6-membered saturated monocyclic heterocyclyl having 1-2 heteroatoms independently selected from nitrogen, oxygen, and sulfur optionally substituted with one or more optionally substituted $C_{1-6}$ alkyl or —OH. In some embodiments, $R^a$ is 4- to 6-membered saturated monocyclic heterocyclyl having 1-2 heteroatoms independently selected from nitrogen, oxygen, and sulfur optionally substituted with one or more halogen, optionally substituted $C_{1-6}$ alkyl, —C(O)($C_{1-6}$ alkyl), or —OH. In some embodiments, $R^a$ is 4- to 7-membered saturated or partially unsaturated monocyclic heterocyclyl having 1-2 heteroatoms independently selected from nitrogen, oxygen, and sulfur optionally substituted with one or more halogen, —OH, —O($C_{1-4}$ alkyl), —N($C_{1-4}$ alkyl)$_2$, —C(O)($C_{1-6}$ alkyl), —CN, or optionally substituted $C_{1-6}$ alkyl. In some embodiments, $R^a$ is optionally substituted 3-membered saturated monocyclic heterocyclyl having 1 heteroatom independently selected from nitrogen, oxygen, and sulfur. In some embodiments, $R^a$ is optionally substituted 4-membered saturated monocyclic heterocyclyl having 1-2 heteroatoms independently selected from nitrogen, oxygen, and sulfur. In some embodiments, $R^a$ is optionally substituted azetidinyl or oxetanyl. In some embodiments, $R^a$ is

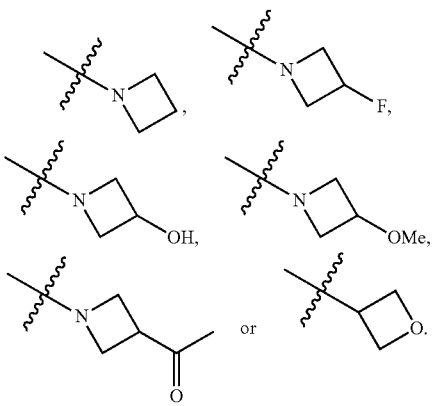

In some embodiments, $R^a$ is optionally substituted 5-membered saturated monocyclic heterocyclyl having 1-3 heteroatoms independently selected from nitrogen, oxygen, and sulfur. In some embodiments, $R^a$ is optionally substituted pyrrolidinyl or tetrahydrofuranyl. In some embodiments, $R^a$ is pyrrolidinyl or tetrahydrofuranyl optionally substituted with one or more optionally substituted $C_{1-6}$ alkyl or —OH. In some embodiments, $R^a$ is pyrrolidinyl or tetrahydrofuranyl optionally substituted with one or more halogen, —OH, or optionally substituted $C_{1-6}$ alkyl. In some embodiments, $R^a$ is pyrrolidinyl or tetrahydrofuranyl optionally substituted with one or more halogen, —OH, —O($C_{1-4}$ alkyl), —N($C_{1-4}$ alkyl)$_2$, —CN, or optionally substituted $C_{1-6}$ alkyl. In some embodiments, $R^a$ is

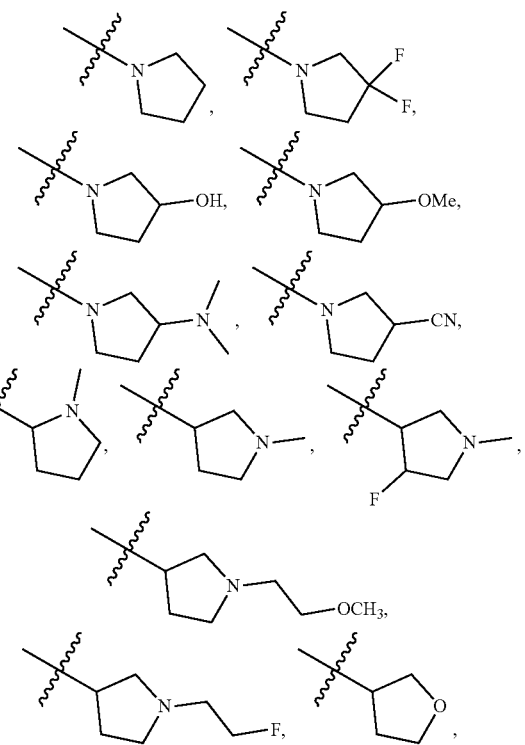

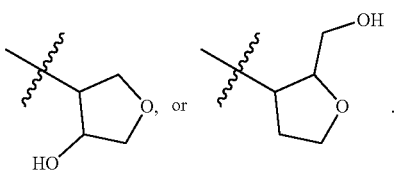

In some embodiments, $R^a$ is optionally substituted 6-membered saturated monocyclic heterocyclyl having 1-3 heteroatoms independently selected from nitrogen, oxygen, and sulfur. In some embodiments, $R^a$ is optionally substituted tetrahydropyranyl, piperidinyl, morpholinyl, or piperazinyl. In some embodiments, $R^a$ is tetrahydropyranyl, piperidinyl, morpholinyl, or piperazinyl optionally substituted with one or more halogen, —OH, —O($C_{1-4}$ alkyl), or optionally substituted $C_{1-6}$ alkyl. In some embodiments, $R^a$ is optionally substituted tetrahydropyranyl, morpholinyl, or piperazinyl. In some embodiments, $R^a$ is optionally substituted tetrahydropyranyl. In some embodiments, $R^a$ is

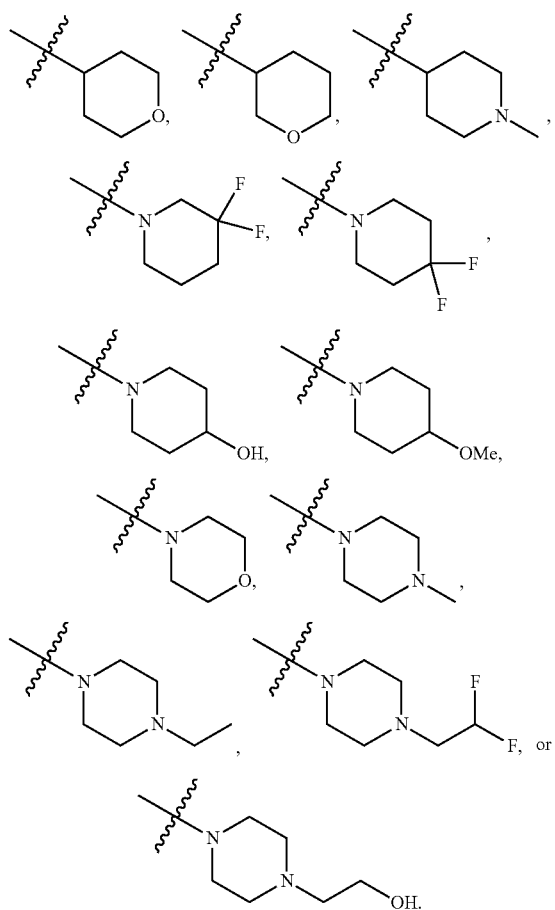

In some embodiments, when L is —$CH_2$—, $R^a$ is not optionally substituted 6-membered saturated monocyclic heterocyclyl having 1-3 heteroatoms independently selected from nitrogen, oxygen, and sulfur. In some embodiments, when L is —$CH_2$—, $R^a$ is not

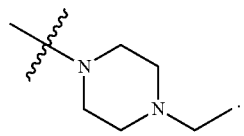 [SMILES: *N1CCN(CC)CC1]

In some embodiments, $R^a$ is optionally substituted 7-membered saturated monocyclic heterocyclyl having 1-3 heteroatoms independently selected from nitrogen, oxygen, and sulfur. In some embodiments, $R^a$ is optionally substituted oxazepanyl or diazepanyl. In some embodiments, $R^a$ is

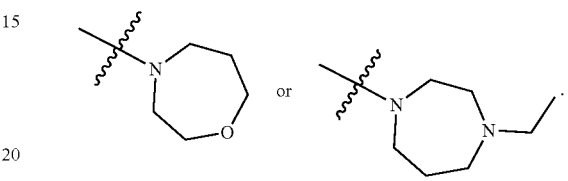

In some embodiments, $R^a$ is optionally substituted 7- to 10-membered saturated or partially unsaturated bicyclic heterocyclyl having 1-4 heteroatoms independently selected from nitrogen, oxygen, and sulfur. In some embodiments, $R^a$ is unsubstituted 7- to 10-membered saturated or partially unsaturated bicyclic heterocyclyl having 1-4 heteroatoms independently selected from nitrogen, oxygen, and sulfur. In some embodiments, $R^a$ is optionally substituted 7- to 10-membered saturated, spirocyclic, bicyclic heterocyclyl having 1-4 heteroatoms independently selected from nitrogen, oxygen, and sulfur. In some embodiments, $R^a$ is optionally substituted 7- to 8-membered saturated, spirocyclic, bicyclic heterocyclyl having 1-2 heteroatoms independently selected from nitrogen, oxygen, and sulfur. In some embodiments $R^a$ is optionally substituted 7-membered saturated, spirocyclic, bicyclic heterocyclyl having 1-4 heteroatoms independently selected from nitrogen, oxygen, and sulfur. In some embodiments, $R^a$ is optionally substituted 2-oxaspiro[3.3]heptanyl or 4-oxaspiro[2.4]heptanyl. In some embodiments $R^a$ is optionally substituted 8-membered saturated, spirocyclic, bicyclic heterocyclyl having 1-4 heteroatoms independently selected from nitrogen, oxygen, and sulfur. In some embodiments $R^a$ is optionally substituted 9-membered saturated, spirocyclic, bicyclic heterocyclyl having 1-4 heteroatoms independently selected from nitrogen, oxygen, and sulfur. In some embodiments $R^a$ is optionally substituted 10-membered saturated, spirocyclic, bicyclic heterocyclyl having 1-4 heteroatoms independently selected from nitrogen, oxygen, and sulfur. In some embodiments, $R^a$ is

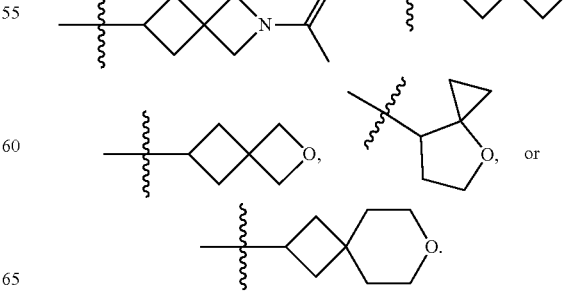

In some embodiments, $R^a$ is selected from the group consisting of:
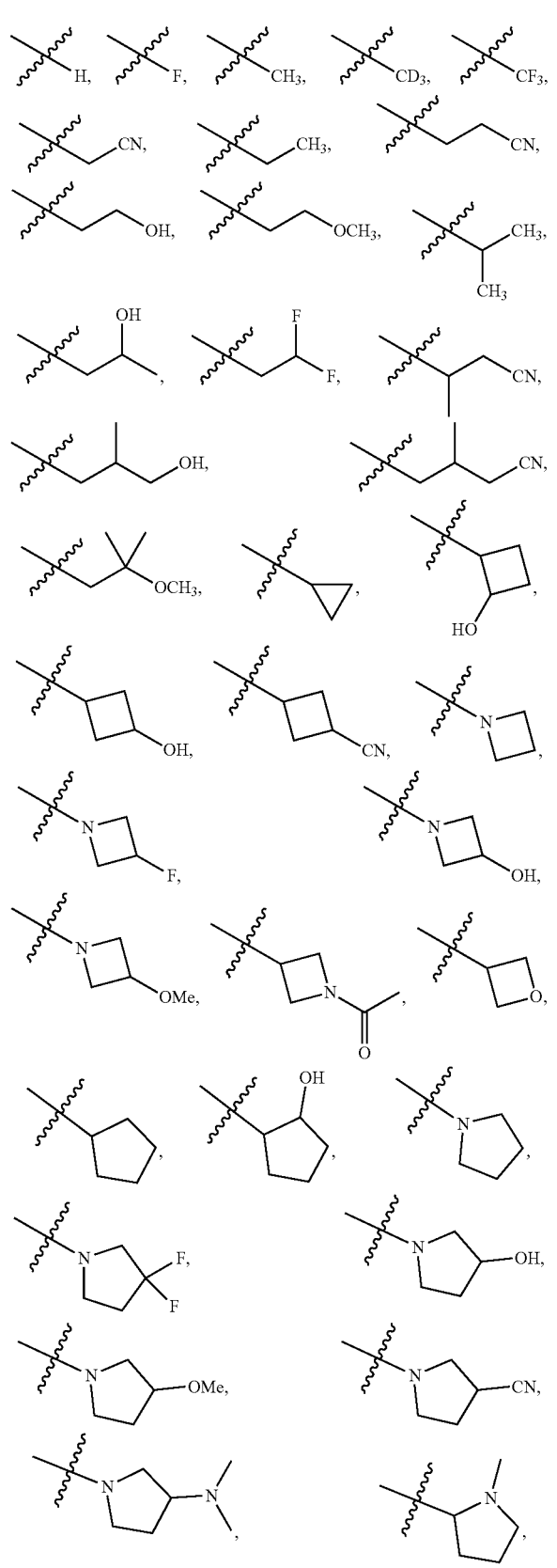
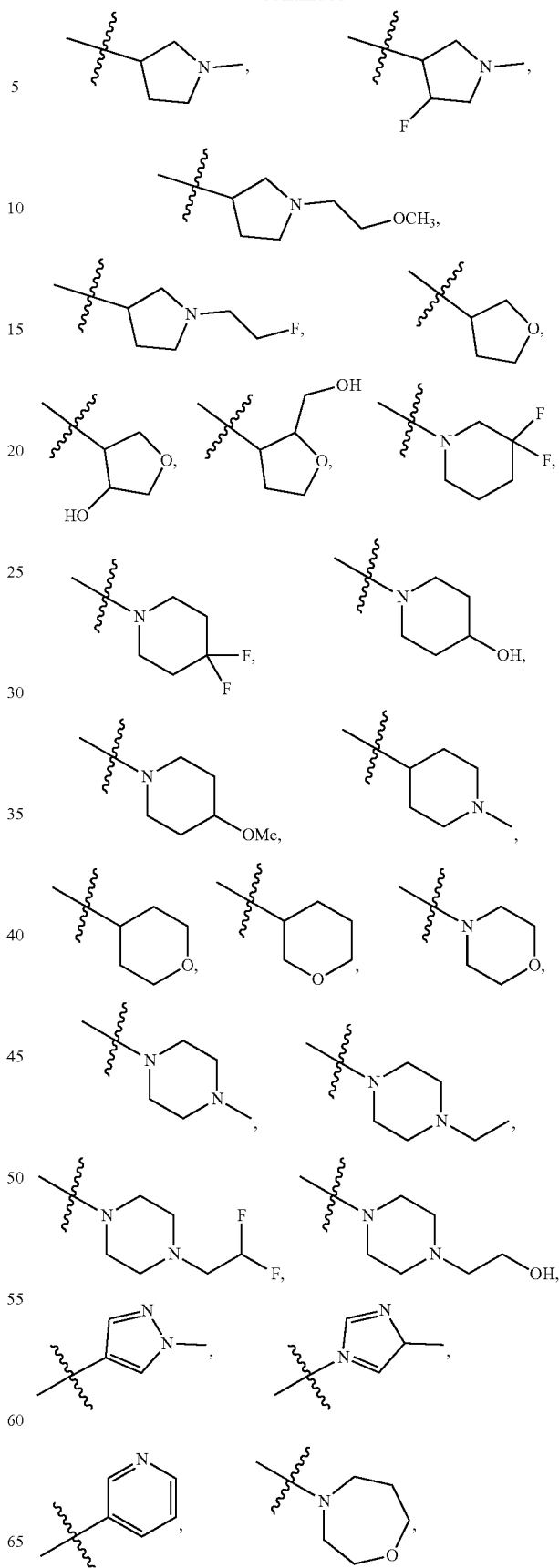

-continued

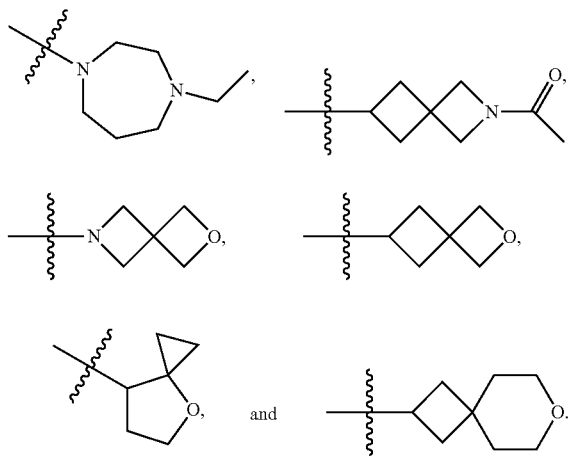

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E,

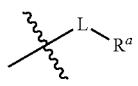

is —$R^a$ (i.e., L is a covalent bond). In some embodiments,

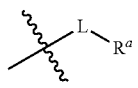

is —($C_{1-3}$ alkylene)-$R^a$ (i.e., L is a $C_{1-3}$ straight or branched hydrocarbon chain). In some embodiments,

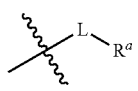

is —($C_{1-2}$ alkylene)-$R^a$ (i.e., L is a $C_{1-2}$ straight or branched hydrocarbon chain). In some embodiments,

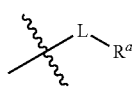

is —$CH_2$—$R^a$ (i.e., L is a $C_1$ hydrocarbon chain). In some embodiments,

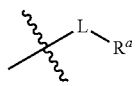

is —$CH_2CH_2$—$R^a$ (i.e., L is a $C_2$ straight hydrocarbon chain). In some embodiments,

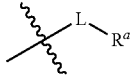

is —$CH_2CH_2CH_2$—$R^a$ (i.e., L is a $C_3$ straight hydrocarbon chain).

In some embodiments of any of Formulae I-B, II-B, III-B, IV-B, I-C, II-C, III-C, IV-C, I-D, II-D, III-D, and IV-D, up to five occurrences of $R^b$ may be present, as allowed by valency rules, and is each independently halogen, —CN, —OR, —O($CH_2$)$_n$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur. In some embodiments, up to five occurrences of $R^b$ may be present, as allowed by valency rules, and is each independently halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur. In some embodiments, each occurrence of $R^b$ is independently hydrogen, halogen, —CN, —OR, —O($CH_2$)$_n$R, —N(R)$_2$, —C(O)N(R)$_2$, optionally substituted $C_{1-6}$ aliphatic, or optionally substituted 3- to 6-membered saturated or partially unsaturated monocyclic carbocyclyl. In some embodiments, each occurrence of $R^b$ is independently hydrogen, optionally substituted $C_{1-6}$ aliphatic, or optionally substituted 3- to 6-membered saturated or partially unsaturated monocyclic carbocyclyl. In some embodiments, each occurrence of $R^b$ is independently halogen, —CN, —OR, —O($CH_2$)$_n$R, —N(R)$_2$, —C(O)N(R)$_2$, optionally substituted $C_{1-6}$ aliphatic, or optionally substituted 3- to 6-membered saturated or partially unsaturated monocyclic carbocyclyl. In some embodiments, each occurrence of $R^b$ is independently optionally substituted $C_{1-6}$ aliphatic or optionally substituted 3- to 6-membered saturated or partially unsaturated monocyclic carbocyclyl. In some embodiments, each occurrence of $R^b$ is independently hydrogen, halogen, —CN, —OR, —OCH$_2$R, —N(R)$_2$, —C(O)N(R)$_2$, optionally substituted $C_{1-4}$ alkyl, or optionally substituted $C_3$-$C_4$ cycloalkyl. In some embodiments, each occurrence of $R^b$ is independently hydrogen, optionally substituted $C_{1-4}$ alkyl, or optionally substituted $C_3$-$C_4$ cycloalkyl. In some embodiments, each occurrence of $R^b$ is independently optionally substituted $C_{1-4}$ alkyl or optionally substituted $C_3$-$C_4$ cycloalkyl. In some embodiments, each occurrence of $R^b$ is independently halogen, —CN, —OR, —OCH$_2$R, —N(R)$_2$, —C(O)N(R)$_2$, optionally substituted $C_{1-4}$ alkyl, or optionally substituted $C_3$-$C_4$ cycloalkyl. In some embodiments, each occurrence of $R^b$ is independently $C_{3-4}$ cycloalkyl or $C_{1-4}$ alkyl optionally substituted with one or more halogen or —CN. In some embodiments, each occurrence of $R^b$ is independently $C_{3-4}$ cycloalkyl or $C_{1-4}$ alkyl optionally substituted with one or more halogen.

In some embodiments, $R^b$ is hydrogen.

In some embodiments, $R^b$ is halogen. In some embodiments, $R^b$ is fluoro, chloro, bromo, or iodo. In some embodiments, $R^b$ is fluoro. In some embodiments, $R^b$ is chloro. In some embodiments, $R^b$ is not halogen. In some embodiments, $R^b$ is not fluoro. In some embodiments, $R^b$ is not chloro.

In some embodiments, $R^b$ is —CN, —OR, —O(CH$_2$)$_n$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, $R^b$ is —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, $R^b$ is —CN, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R, —SO$_2$N(R)$_2$, or —SO$_3$R'. In some embodiments, $R^b$ is not —OR. In some embodiments, $R^b$ is not —OSi(tBu)(Me)$_2$,

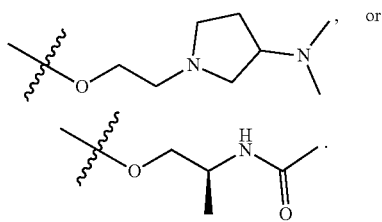, or

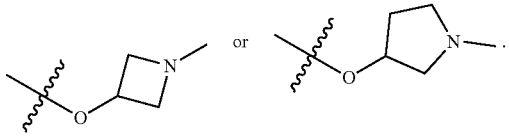.

In some embodiments, $R^b$ is —CN.

In some embodiments, $R^b$ is —OR. In some embodiments, $R^b$ is —OR, wherein R is optionally substituted 3- to 7-membered saturated or partially unsaturated monocyclic heterocyclyl having 1-3 heteroatoms independently selected from nitrogen, oxygen, and sulfur. In some embodiments, $R^b$ is —OR, wherein R is optionally substituted 4- to 6-membered saturated monocyclic heterocyclyl having 1-2 heteroatoms independently selected from nitrogen, oxygen, and sulfur. In some embodiments, $R^b$ is —OR, wherein R is 4- to 6-membered saturated monocyclic heterocyclyl having 1-2 heteroatoms independently selected from nitrogen, oxygen, and sulfur and optionally substituted with one or more $C_{1-6}$ alkyl (e.g., methyl). In some embodiments, $R^b$ is —OR, wherein R is optionally substituted azetidinyl or pyrrolidinyl. In some embodiments, $R^b$ is —OR, wherein R is azetidinyl or pyrrolidinyl optionally substituted with one or more $C_{1-6}$ alkyl (e.g., methyl). In some embodiments, $R^b$ is In some embodiments, $R^b$ is —O(CH$_2$)$_n$R. In some embodiments, $R^b$ is —OCH$_2$R. In some embodiments, $R^b$ is —O(CH$_2$)$_n$R, wherein R is optionally substituted 3- to 7-membered saturated or partially unsaturated monocyclic heterocyclyl having 1-3 heteroatoms independently selected from nitrogen, oxygen, and sulfur. In some embodiments, $R^b$ is —O(CH$_2$)$_n$R, wherein R is optionally substituted 4- to 6-membered saturated monocyclic heterocyclyl having 1-2 heteroatoms independently selected from nitrogen, oxygen, and sulfur. In some embodiments, $R^b$ is —O(CH$_2$)$_n$R, wherein R is 4- to 6-membered saturated monocyclic heterocyclyl having 1-2 heteroatoms independently selected from nitrogen, oxygen, and sulfur and optionally substituted with one or more $C_{1-6}$ alkyl (e.g., methyl). In some embodiments, $R^b$ is —O(CH$_2$)$_n$R, wherein R is optionally substituted azetidinyl, pyrrolidinyl, or piperidinyl. In some embodiments, $R^b$ is —O(CH$_2$)$_n$R, wherein R is azetidinyl, pyrrolidinyl, or piperidinyl optionally substituted with one or more $C_{1-6}$ alkyl (e.g., methyl). In some embodiments, $R^b$ is

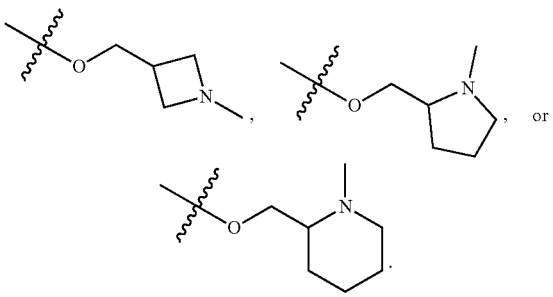

In some embodiments, $R^b$ is —N(R)$_2$. In some embodiments, $R^b$ is —N($C_{1-6}$ aliphatic)$_2$. In some embodiments, $R^b$ is —N($C_{1-6}$ alkyl)$_2$. In some embodiments, $R^b$ is —N($C_{1-4}$ alkyl)$_2$. In some embodiments, $R^b$ is —N($C_{1-2}$ alkyl)$_2$. In some embodiments, $R^b$ is —N(CH$_3$)$_2$.

In some embodiments, $R^b$ is —C(O)N(R)$_2$. In some embodiments, $R^b$ is —C(O)N(R)$_2$, wherein each R is independently hydrogen or optionally substituted $C_{1-6}$ aliphatic, or two R are taken together to form an optionally substituted 3- to 7-membered saturated or partially unsaturated monocyclic heterocyclyl having 0-2 additional heteroatoms independently selected from nitrogen, oxygen, and sulfur. In some embodiments, $R^b$ is —C(O)N(R)$_2$, wherein each R is independently hydrogen or optionally substituted $C_{1-6}$ alkyl, or two R are taken together to form an optionally substituted 4- to 6-membered saturated monocyclic heterocyclyl having 0-1 additional heteroatoms independently selected from nitrogen, oxygen, and sulfur. In some embodiments, $R^b$ is

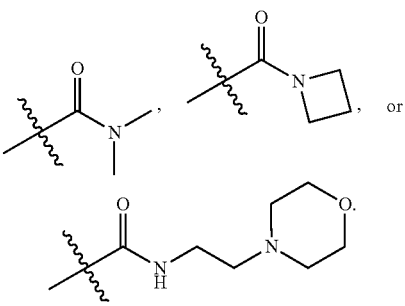

In some embodiments, $R^b$ is optionally substituted $C_{1-6}$ aliphatic. In some embodiments, $R^b$ is optionally substituted straight-chain or branched $C_{1-6}$ aliphatic (i.e., optionally substituted acyclic $C_{1-6}$ aliphatic). In some embodiments, $R^b$ is optionally substituted $C_{1-6}$ alkyl. In some embodiments, $R^b$ is optionally substituted $C_{1-4}$ alkyl. In some embodiments, $R^b$ is $C_{1-4}$ alkyl optionally substituted with one or more of halogen, —CN, and —N($C_{1-4}$ alkyl)$_2$. In some embodiments, $R^b$ is $C_{1-4}$ alkyl optionally substituted with one or more of halogen and —CN. In some embodiments, $R^b$ is $C_{1-4}$ alkyl optionally substituted with one or more halogen. In some embodiments, each $R^b$ is independently selected from the group consisting of —CF$_3$, —C(CH$_3$)$_3$, —C(CH$_3$)$_2$CN, and —CF$_2$CF$_3$. In some embodiments, each $R^b$ is independently selected from the group consisting of —CH$_3$, —CF$_3$, —CH$_2$N(CH$_3$)$_2$, —C(CH$_3$)$_3$, —C(CH$_3$)$_2$CN, and —CF$_2$CF$_3$. In some embodiments, when Ring A is phenyl, $R^b$ is not —CF$_3$. In some embodiments, when Ring A is phenyl, $R^b$ is not

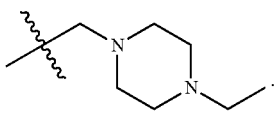

In some embodiments, $R^b$ is optionally substituted 3- to 6-membered saturated or partially unsaturated monocyclic carbocyclyl. In some embodiments, $R^b$ is optionally substituted $C_3$-$C_6$ cycloalkyl. In some embodiments, $R^b$ is optionally substituted 3-membered saturated or partially unsaturated monocyclic carbocyclyl. In some embodiments, $R^b$ is cyclopropyl. In some embodiments, $R^b$ is optionally substituted 4-membered saturated or partially unsaturated monocyclic carbocyclyl. In some embodiments, $R^b$ is optionally substituted 5-membered saturated or partially unsaturated monocyclic carbocyclyl. In some embodiments, $R^b$ is optionally substituted 6-membered saturated or partially unsaturated monocyclic carbocyclyl.

In some embodiments, $R^b$ is optionally substituted 3- to 6-membered saturated or partially unsaturated monocyclic heterocyclyl having 1-3 heteroatoms independently selected from nitrogen, oxygen, and sulfur.

In some embodiments, $R^b$ is optionally substituted 5- to 6-membered monocyclic heteroaryl having 1-4 heteroatoms independently selected from nitrogen, oxygen, and sulfur.

In some embodiments, $R^b$ is not fluoro, —OR, or —CF$_3$. In some embodiments, $R^b$ is not fluoro, —CF$_3$, —OSi(tBu)(Me)$_2$,

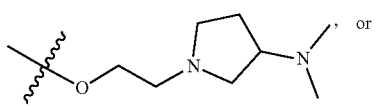, or

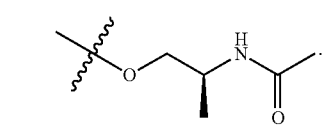.

In some embodiments of any of Formulae I, II, III, IV, I-A, II-A, III-A, IV-A, I-E, II-E, III-E, and IV-E, optionally substituted

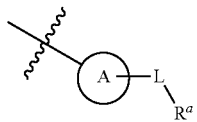

is

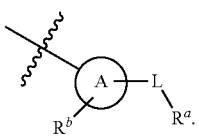

In some embodiments, optionally substituted

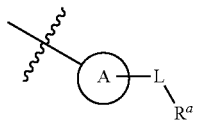

is optionally substituted

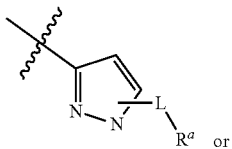 or

In some embodiments optionally substituted

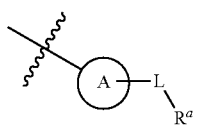

is optionally substituted

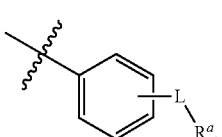
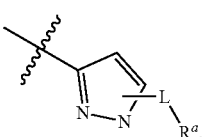
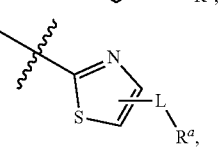
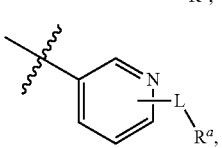

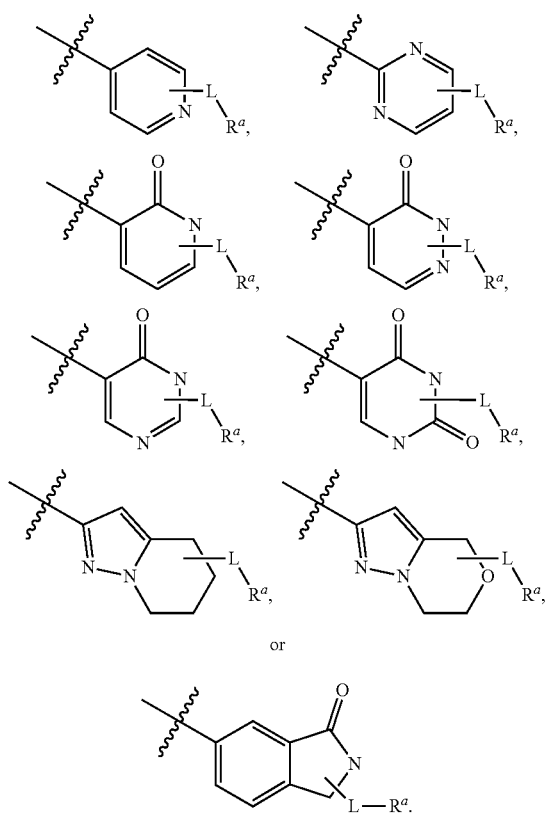
In some embodiments,
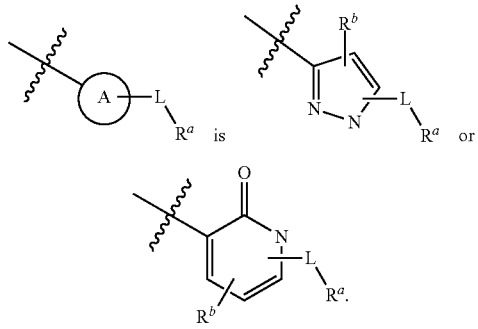
In some embodiments,
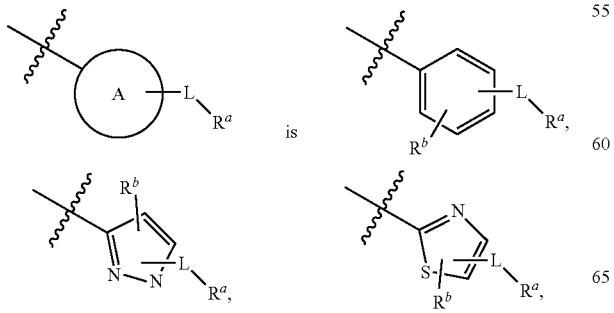
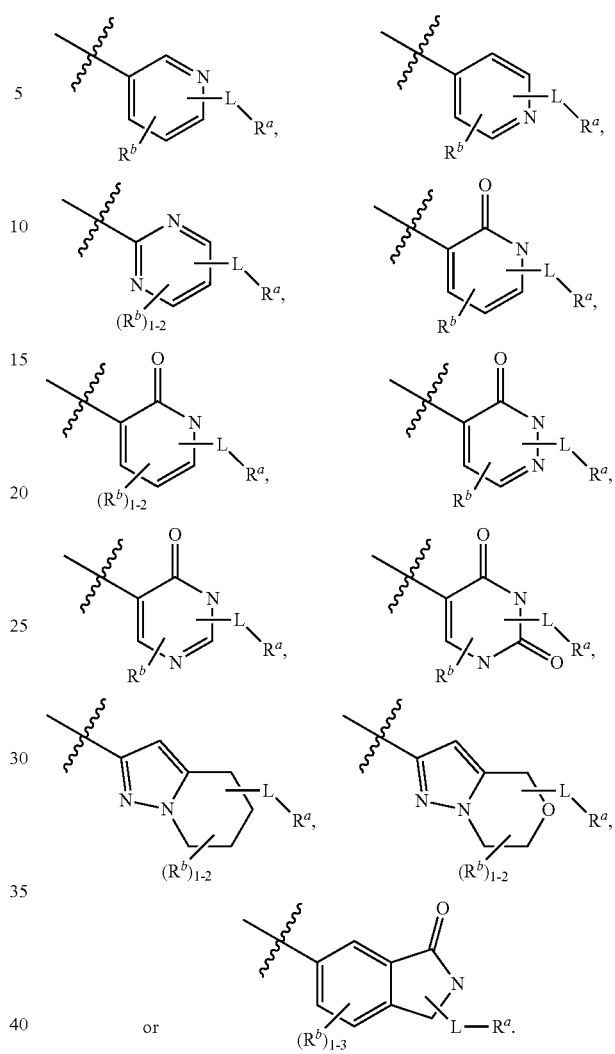
In some embodiments,
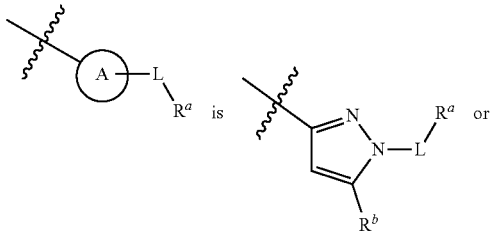
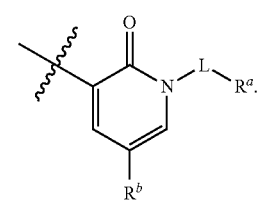

In some embodiments,
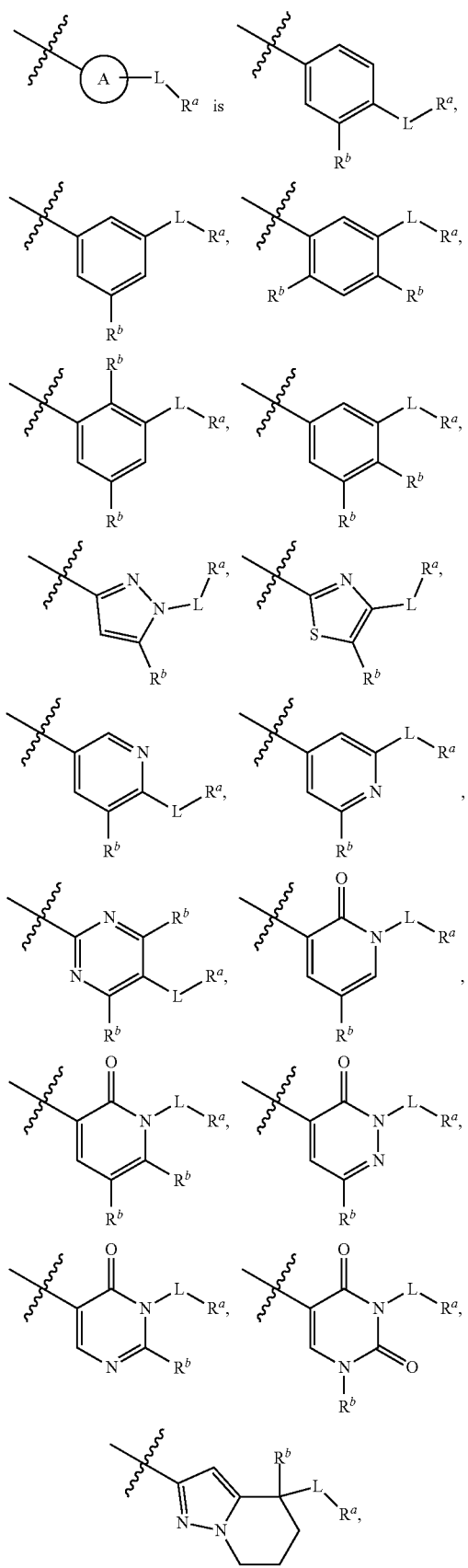
-continued
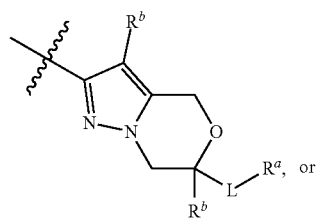
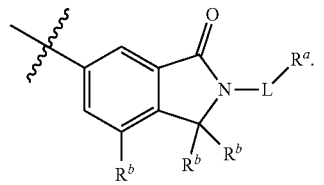
In some embodiments,
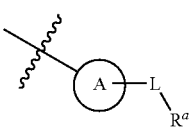
is selected from the group consisting of:
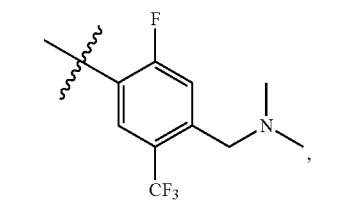
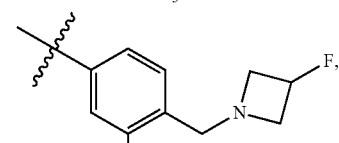
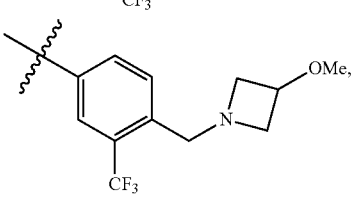
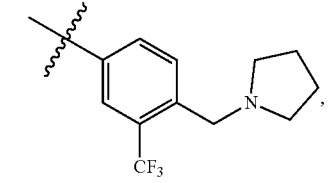
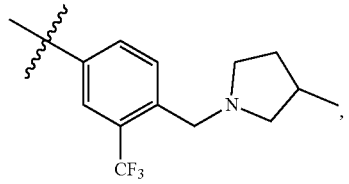

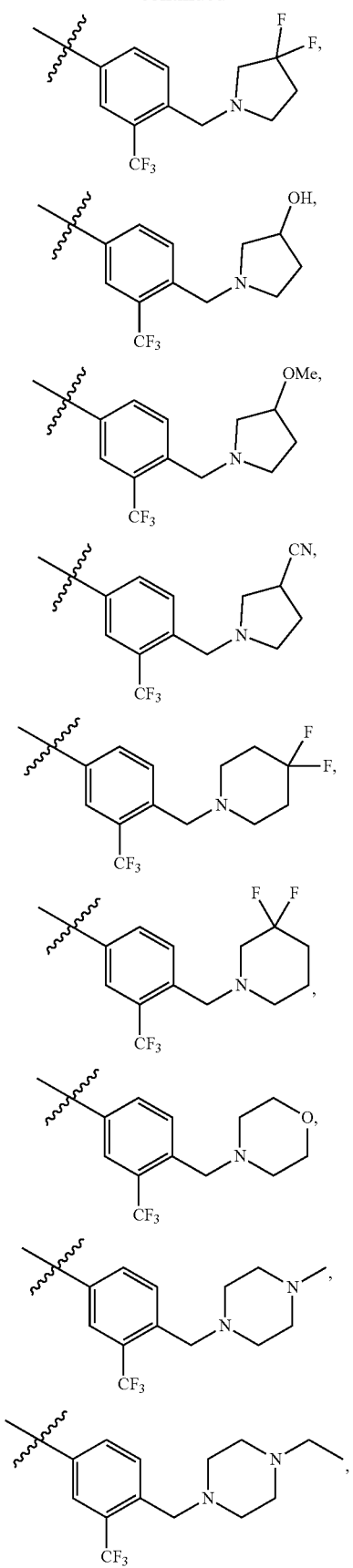
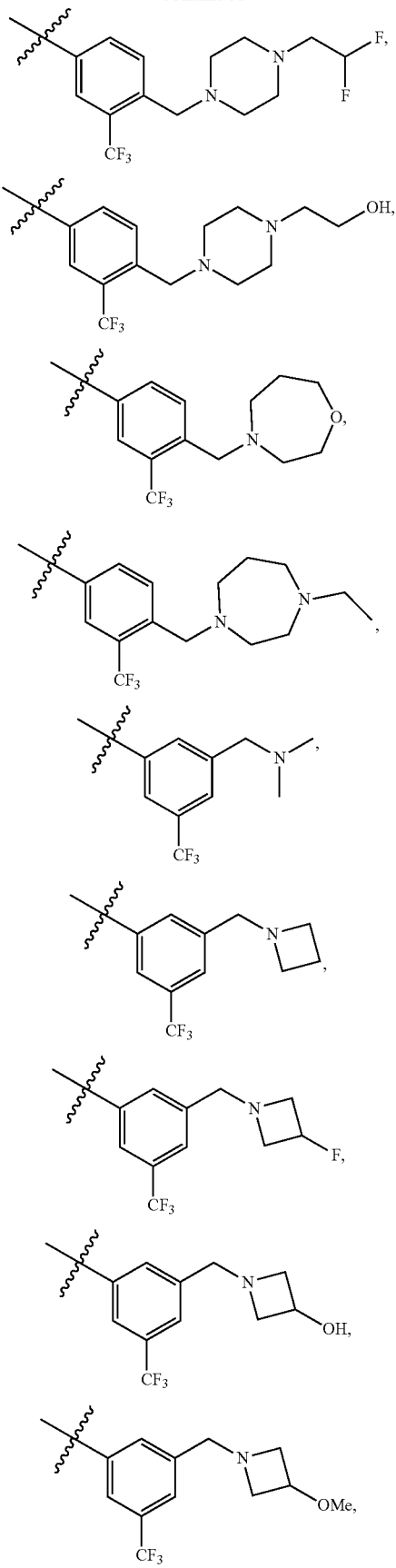

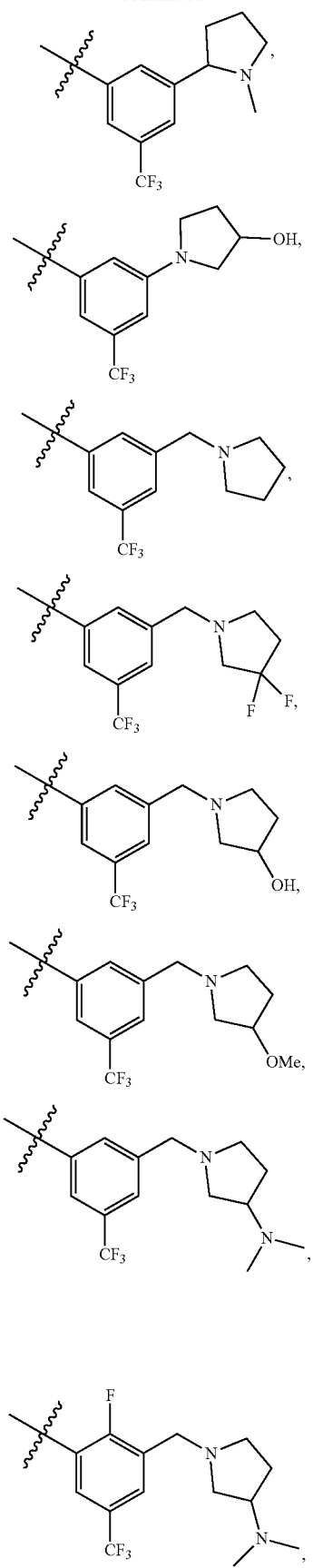
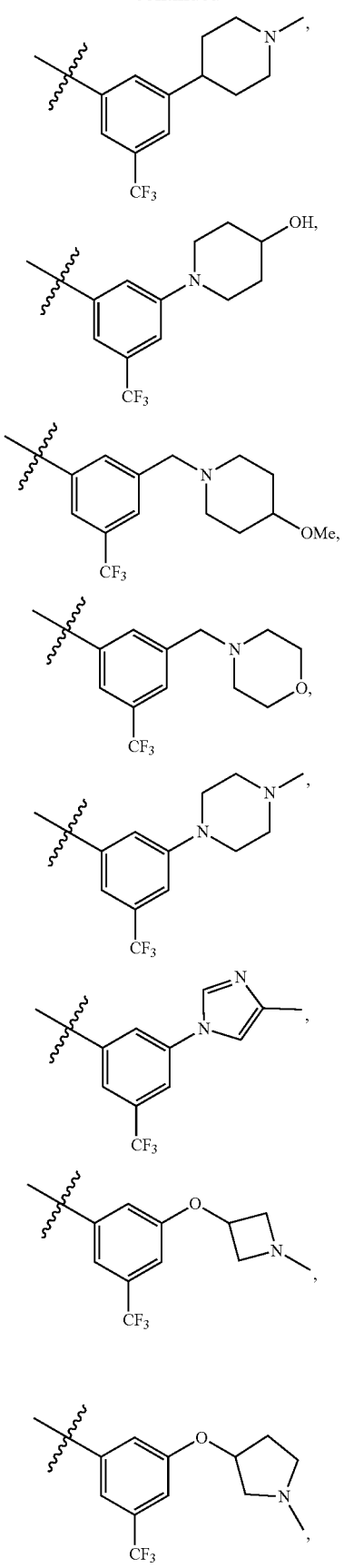

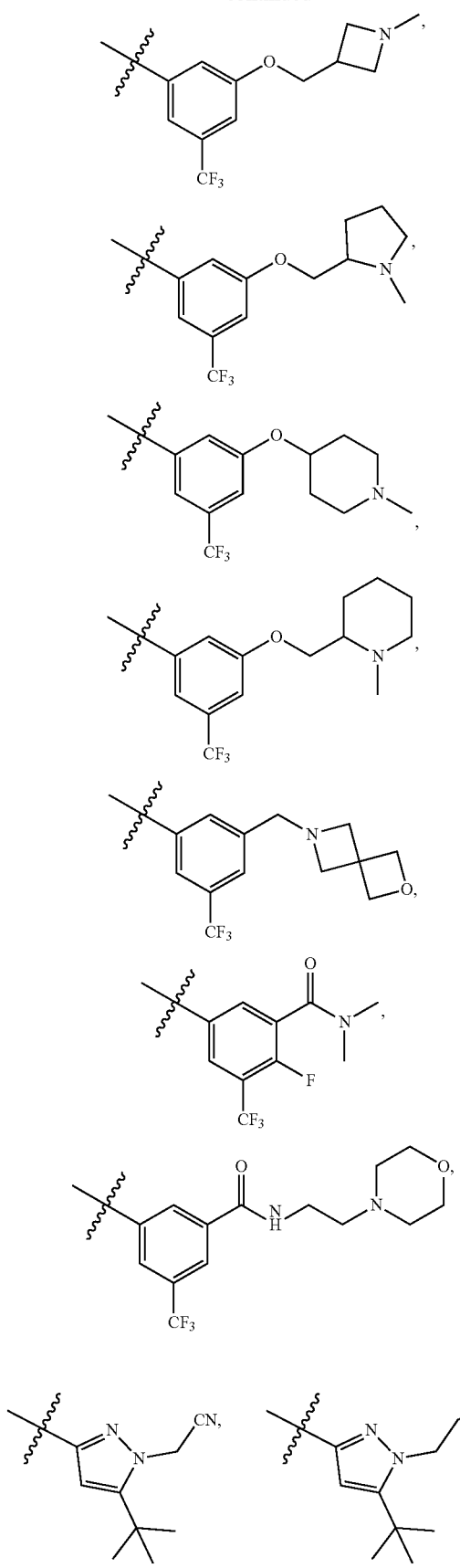
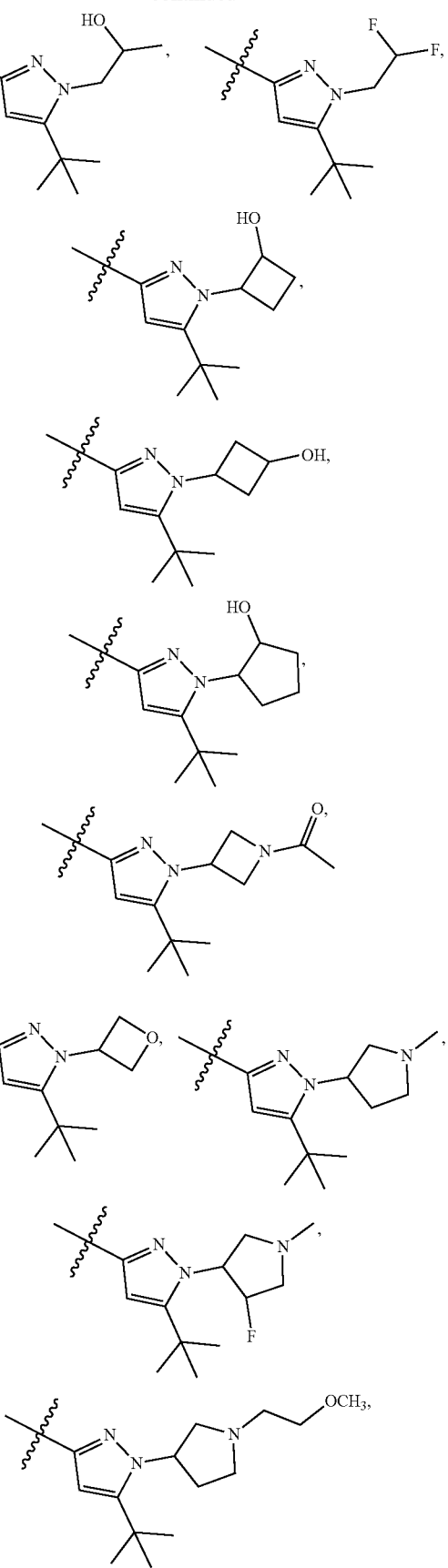

-continued
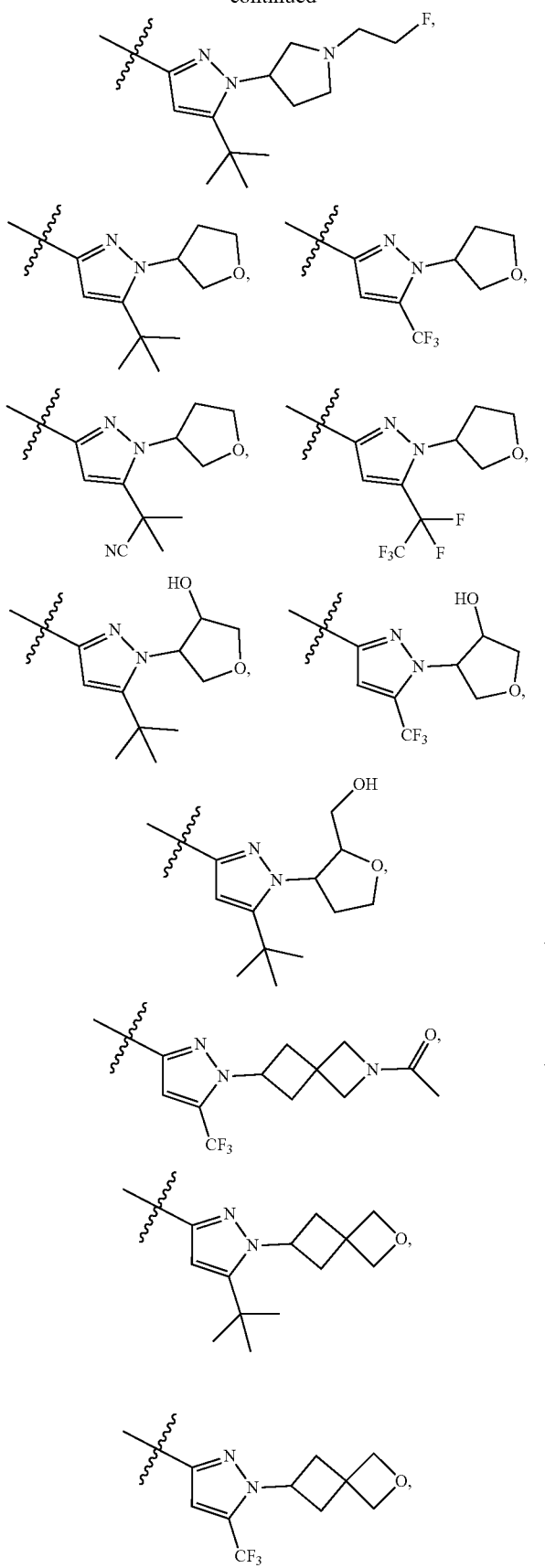
-continued
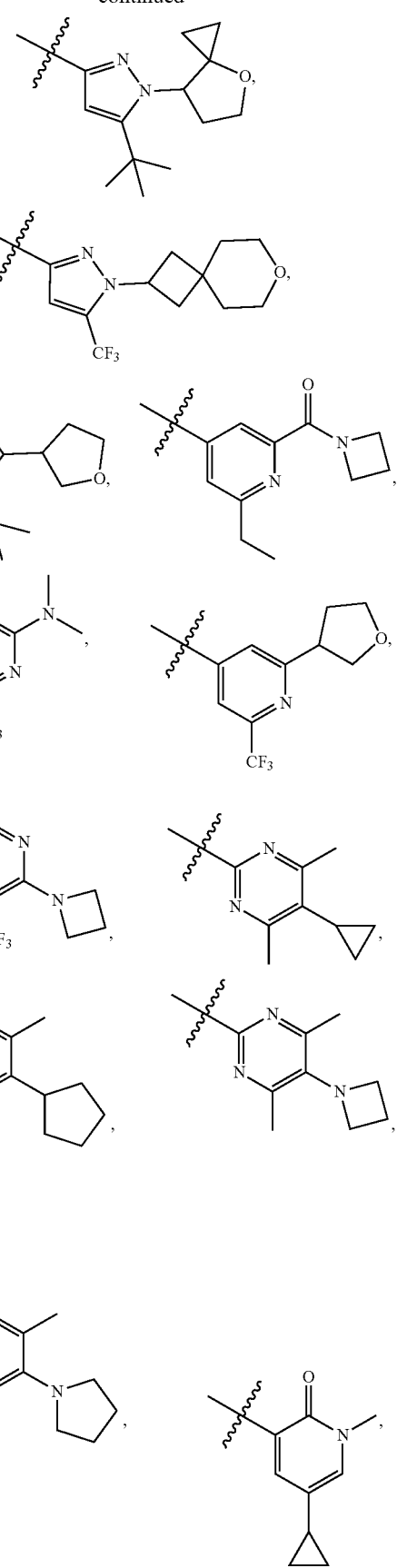

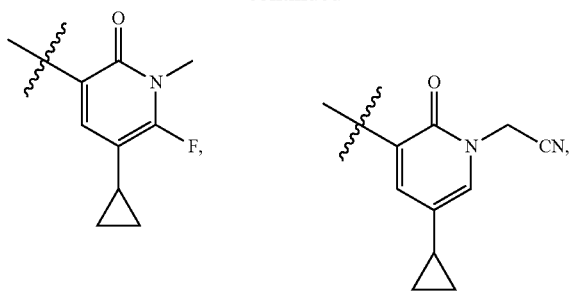
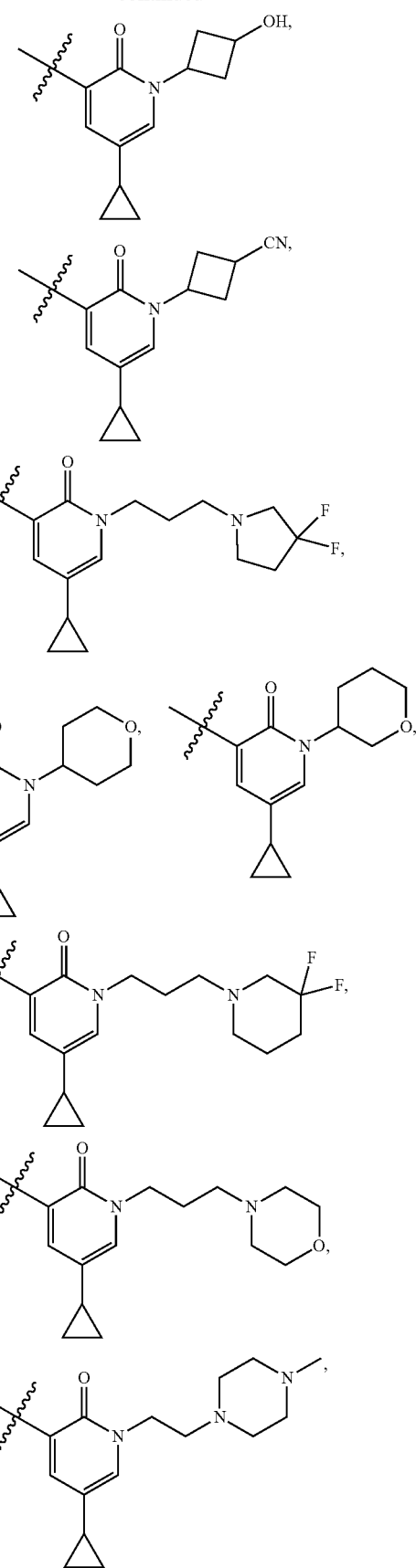

-continued
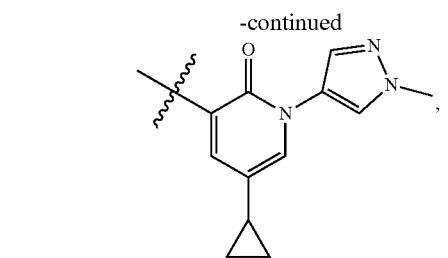
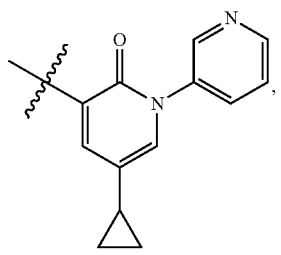
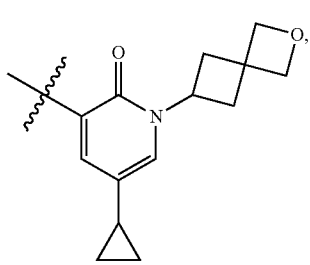
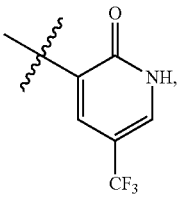
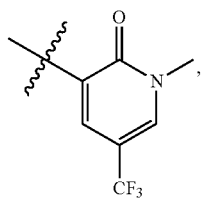
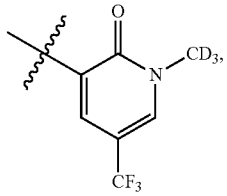
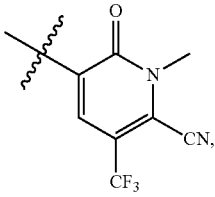
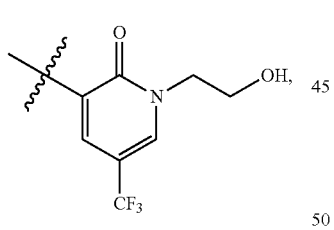
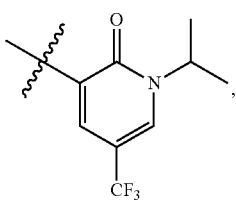
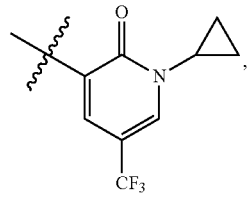
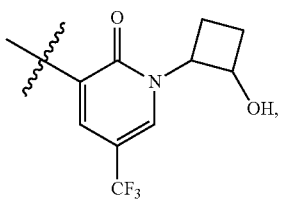
-continued
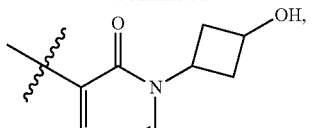
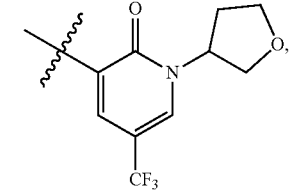
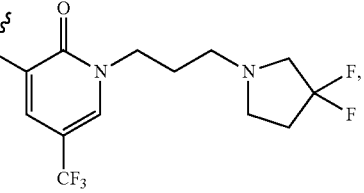
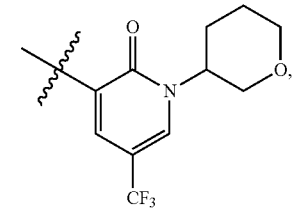
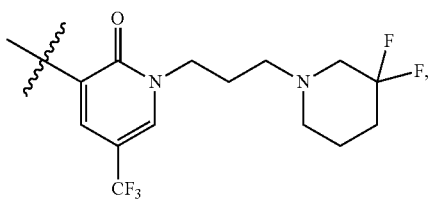
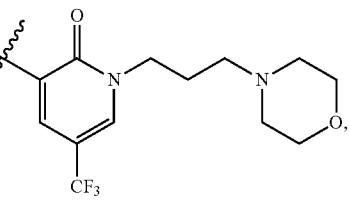
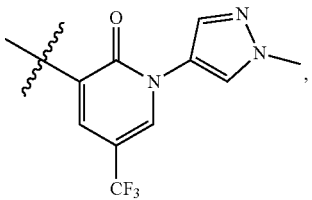
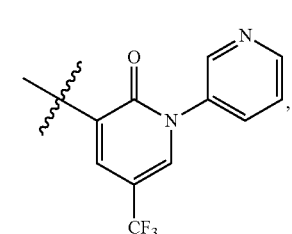

-continued

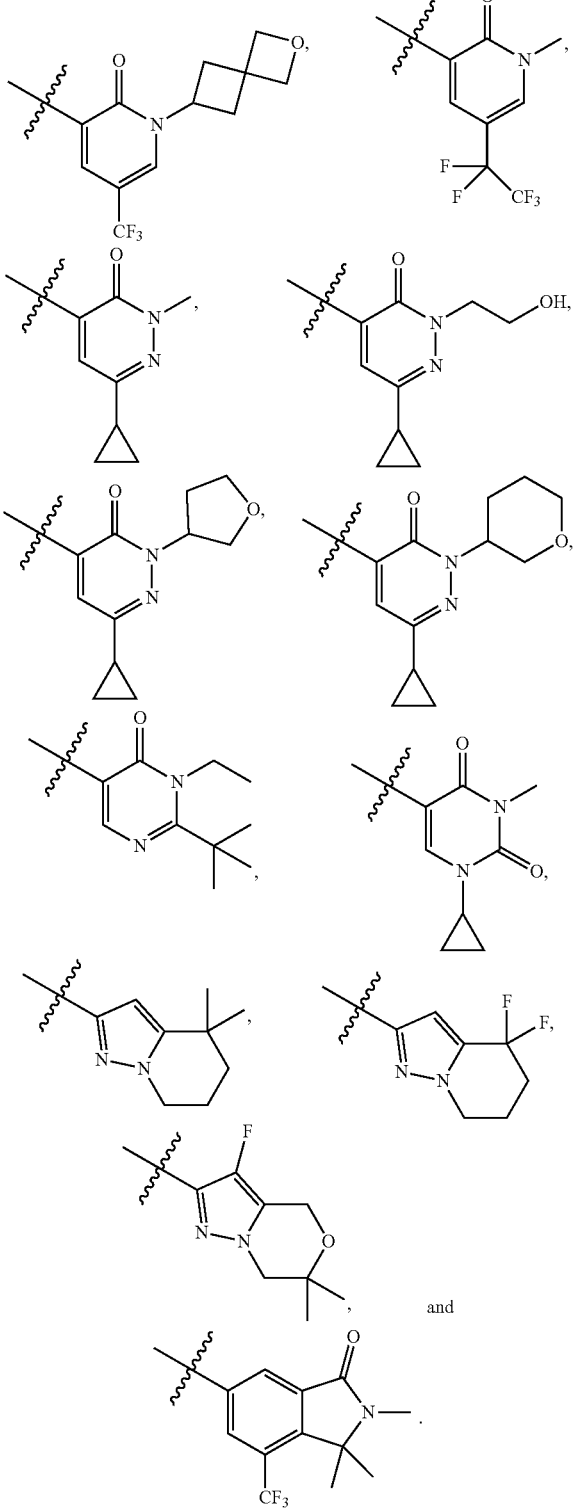

In some embodiments of any of Formulae I, II, III, IV, I-B, II-B, III-B, IV-B, I-C, II-C, III-C, IV-C, I-D, II-D, III-D, and IV-D, Ring B is (i) optionally substituted on a substitutable carbon atom with one or more groups independently selected from oxo, halogen, R°, —CN, —OR°, —SR°, —N(R°)$_2$, —NO$_2$, —C(O)R°, —C(O)OR°, —C(O)NR°$_2$, —OC(O)R°, —OC(O)NR°$_2$, —OC(O)OR°, —OS(O)$_2$R°, —OS(O)$_2$NR°$_2$, —N(R°)C(O)R°, —N(R°)S(O)$_2$R°, —S(O)$_2$R°, —SO$_2$NR°$_2$, and —S(O)$_2$OR°, and (ii) optionally substituted on a substitutable nitrogen atom with one or more groups selected from —R†, —NR†$_2$, —C(O)R†, —C(O)OR†, —S(O)$_2$R†, and —S(O)$_2$NR†$_2$. In some embodiments, Ring B is (i) optionally substituted on a substitutable carbon atom with one or more groups independently selected from oxo, halogen, R°, —CN, —OR°, and —N(R°)$_2$, and (ii) optionally substituted on a substitutable nitrogen with —R†. In some embodiments, Ring B is optionally substituted on a substitutable carbon atom with one or more groups independently selected from —CN and R°.

In some embodiments, each ring in a bicyclic or polycyclic ring system of Ring B contains at least one heteroatom. In some embodiments, one and only one ring of a bicyclic or polycyclic ring system of Ring B contains no heteroatoms.

In some embodiments, each ring in a bicyclic or polycyclic ring system of Ring B is aromatic. In some embodiments, one and only one ring of a bicyclic or polycyclic ring system of Ring B is aromatic. In some embodiments, no ring in a bicyclic or polycyclic ring system of Ring B is aromatic.

In some embodiments, Ring B is optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur. In some embodiments, Ring B is optionally substituted 8- to 10-membered bicyclic heteroaryl having 1-4 heteroatoms independently selected from nitrogen, oxygen, and sulfur or optionally substituted 10- to 16-membered polycyclic heteroaryl having 1-5 heteroatoms independently selected from nitrogen, oxygen, and sulfur.

In some embodiments, Ring B is optionally substituted 9- to 16-membered bicyclic or tricyclic aryl. In some embodiments, Ring B is optionally substituted 9- to 10-membered bicyclic aryl. In some embodiments, Ring B is optionally substituted 9-membered bicyclic aryl (e.g., a 5-membered carbocycle fused to a phenyl ring). In some embodiments, Ring B is not substituted indanyl (e.g., indanyl substituted with one or more halogens). In some embodiments, Ring B is optionally substituted 10-membered bicyclic aryl (e.g., naphthyl or a 6-membered carbocycle fused to a phenyl ring).

In some embodiments, Ring B is optionally substituted 8- to 10-membered bicyclic heteroaryl having 1-4 heteroatoms independently selected from nitrogen, oxygen, and sulfur. In some embodiments, Ring B is 8- to 10-membered bicyclic heteroaryl having 1-4 heteroatoms independently selected from nitrogen, oxygen, and sulfur optionally substituted with one or more oxo, halogen, —O(optionally substituted C$_{1-6}$ alkyl), —O(optionally substituted C$_{3-6}$ carbocyclyl), —NH (optionally substituted C$_{1-6}$ alkyl), —NH (optionally substituted 3- to 6-membered saturated heterocyclyl), —N(optionally substituted C$_{1-6}$ alkyl)$_2$, —CN, optionally substituted C$_{1-6}$ aliphatic (e.g., optionally substituted C$_{1-6}$ alkyl), optionally substituted C$_{3-6}$ carbocyclyl (e.g., optionally substituted C$_{3-6}$ cycloalkyl), and optionally substituted 3- to 6-membered saturated or partially unsaturated heterocyclyl having 1-2 heteroatoms selected from nitrogen, oxygen, and sulfur (e.g., optionally substituted 3- to 6-membered saturated heterocyclyl having 1-2 heteroatoms selected from nitrogen, oxygen, and sulfur). In some embodiments, Ring B is 8- to 10-membered bicyclic heteroaryl having 1-4 heteroatoms independently selected from nitrogen, oxygen, and sulfur optionally substituted with one or more —O(C$_{1-6}$ alkyl), —CN, optionally substituted C$_{1-6}$ aliphatic (e.g., optionally substituted C$_{1-6}$ alkyl) and optionally substituted C$_{3-6}$ carbocyclyl (e.g., optionally substituted C$_{3-6}$ cycloalkyl). In some embodiments, Ring B is 8- to 10-membered bicyclic heteroaryl having 1-4 heteroatoms independently selected from nitrogen, oxygen, and sulfur optionally substituted with one or more halogen, —O(C$_{1-6}$ alkyl), —CN, optionally substituted C$_{1-6}$ aliphatic (e.g., optionally substituted C$_{1-6}$ alkyl) and optionally substituted C$_{3-6}$ carbocyclyl (e.g., optionally substituted C$_{3-6}$ cycloalkyl). In some embodiments, Ring B is 8- to 10-membered bicyclic heteroaryl having 1-4 heteroatoms independently selected from nitrogen, oxygen, and sulfur optionally substituted with one or more selected from the group consisting of —O(C$_{1-4}$ alkyl), —CN, C$_{1-4}$ alkyl optionally substituted with one or more —O(C$_{1-4}$ alkyl), and C$_{3-4}$ cycloalkyl. In some embodiments, Ring B is 8- to 10-membered bicyclic heteroaryl having 1-4 heteroatoms independently selected from nitrogen, oxygen, and sulfur optionally substituted with one or more selected from the group consisting of halogen, —O(C$_{1-4}$ alkyl), —CN, C$_{1-4}$ alkyl optionally substituted with one or more halogen or —O(C$_{1-4}$ alkyl), and C$_{3-4}$ cycloalkyl. In some embodiments, Ring B is 8- to 10-membered bicyclic heteroaryl having 1-4 heteroatoms independently selected from nitrogen, oxygen, and sulfur optionally substituted with one or more selected from the group consisting of halogen, —O(C$_{1-4}$ alkyl), —NH(C$_{1-4}$ alkyl), —CN, C$_{1-4}$ alkyl optionally substituted with one or more halogen or —O(C$_{1-4}$ alkyl), and C$_{3-4}$ cycloalkyl. In some embodiments, Ring B is 8- to 10-membered bicyclic heteroaryl having 1-4 heteroatoms independently selected from nitrogen, oxygen, and sulfur optionally substituted with one or more groups selected from:

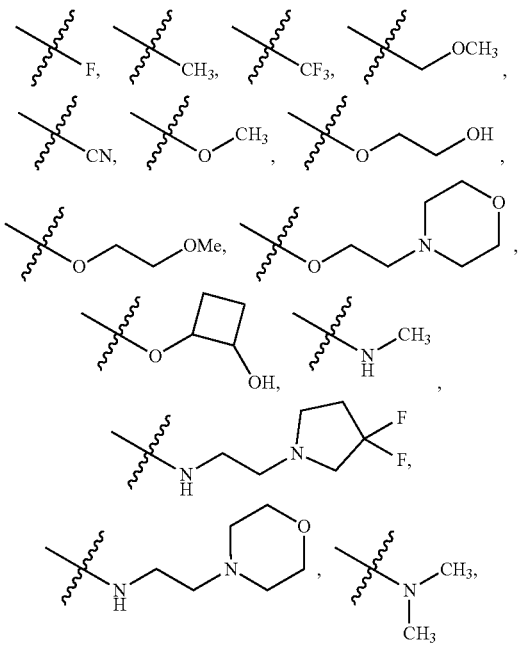

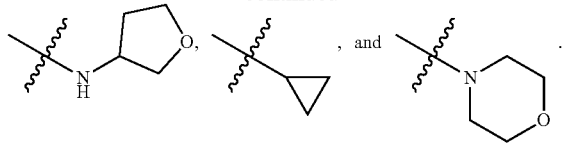

In some embodiments, Ring B is optionally substituted 8-membered bicyclic heteroaryl having 1-4 heteroatoms independently selected from nitrogen, oxygen, and sulfur. In some embodiments, Ring B is optionally substituted 9-membered bicyclic heteroaryl having 1-4 heteroatoms independently selected from nitrogen, oxygen, and sulfur. In some embodiments, Ring B is a 9-membered bicyclic heteroaryl having 1-4 heteroatoms independently selected from nitrogen, oxygen, and sulfur optionally substituted with one or more oxo, halogen, —O(optionally substituted C$_{1-6}$ alkyl), —O(optionally substituted C$_{3-6}$ carbocyclyl), —NH (optionally substituted C$_{1-6}$ alkyl), —NH (optionally substituted 3- to 6-membered saturated heterocyclyl), —N(optionally substituted C$_{1-6}$ alkyl)$_2$, —CN, optionally substituted C$_{1-6}$ aliphatic (e.g., optionally substituted C$_{1-6}$ alkyl), optionally substituted C$_{3-6}$ carbocyclyl (e.g., optionally substituted C$_{3-6}$ cycloalkyl), and optionally substituted 3- to 6-membered saturated or partially unsaturated heterocyclyl having 1-2 heteroatoms selected from nitrogen, oxygen, and sulfur (e.g., optionally substituted 3- to 6-membered saturated heterocyclyl having 1-2 heteroatoms selected from nitrogen, oxygen, and sulfur). In some embodiments, Ring B is 9-membered bicyclic heteroaryl having 1-4 heteroatoms independently selected from nitrogen, oxygen, and sulfur optionally substituted with one or more —O(C$_{1-6}$ alkyl), —CN, optionally substituted C$_{1-6}$ aliphatic (e.g., optionally substituted C$_{1-6}$ alkyl) and optionally substituted C$_{3-6}$ carbocyclyl (e.g., optionally substituted C$_{3-6}$ cycloalkyl). In some embodiments, Ring B is 9-membered bicyclic heteroaryl having 1-4 heteroatoms independently selected from nitrogen, oxygen, and sulfur optionally substituted with one or more halogen, —O(C$_{1-6}$ alkyl), —CN, optionally substituted C$_{1-6}$ aliphatic (e.g., optionally substituted C$_{1-6}$ alkyl) and optionally substituted C$_{3-6}$ carbocyclyl (e.g., optionally substituted C$_{3-6}$ cycloalkyl). In some embodiments, Ring B is 9-membered bicyclic heteroaryl having 1-4 heteroatoms independently selected from nitrogen, oxygen, and sulfur optionally substituted with one or more selected from the group consisting of —O(C$_{1-4}$ alkyl), —CN, C$_{1-4}$ alkyl optionally substituted with one or more —O(C$_{1-4}$ alkyl), and C$_{3-4}$ cycloalkyl. In some embodiments, Ring B is 9-membered bicyclic heteroaryl having 1-4 heteroatoms independently selected from nitrogen, oxygen, and sulfur optionally substituted with one or more selected from the group consisting of halogen, —O(C$_{1-4}$ alkyl), —CN, C$_{1-4}$ alkyl optionally substituted with one or more halogen or —O(C$_{1-4}$ alkyl), and C$_{3-4}$ cycloalkyl. In some embodiments, Ring B is a 9-membered bicyclic heteroaryl having 1-4 heteroatoms independently selected from nitrogen, oxygen, and sulfur optionally substituted with one or more selected from the group consisting of halogen, —O(C$_{1-4}$ alkyl), —NH(C$_{1-4}$ alkyl), —CN, C$_{1-4}$ alkyl optionally substituted with one or more halogen or —O(C$_{1-4}$ alkyl), and C$_{3-4}$ cycloalkyl. In some embodiments, Ring B is optionally substituted pyrazol[1,5-a]pyridyl, 1H-pyrrolo[2,3-b]pyridinyl, 1H-pyrazolo[3,4-b]pyridinyl, pyrazolo[1,5-a]pyrazinyl, pyrazolo[1,5-a]pyrimidinyl, imidazo[1,2-b]pyridazinyl, imidazo[1,5-a]pyrimidinyl, [1,2,4]triazolo[4,3-b]pyridazinyl, thieno[2,3-b]pyridinyl, or thiazolo[5,4-b]pyridinyl. In some embodiments, Ring B is optionally substituted pyrazol[1,5-a]pyridyl, 1H-pyrrolo[2,3-b]pyridinyl, 1H-pyrazolo[3,4-b]pyridinyl, pyrazolo[1,5-a]pyrazinyl, pyrazolo[1,5-a]pyrimidinyl, imidazo[1,2-b]pyridazinyl, imidazo[1,5-a]pyrimidinyl, 3H-imidazo[4,5-b]pyridyl, imidazo[1,5-b]pyridazinyl, [1,2,4]triazolo[4,3-b]pyridazinyl, thieno[2,3-b]pyridinyl, or thiazolo[5,4-b]pyridinyl. In some embodiments, Ring B is not optionally substituted thiazolo[5,4-b]pyridinyl (e.g., thiazolo[5,4-b]pyridinyl substituted with —NHC(O)(C₃ cycloalkyl)). In some embodiments, Ring B is optionally substituted 10-membered bicyclic heteroaryl having 1-4 heteroatoms independently selected from nitrogen, oxygen, and sulfur. In some embodiments, Ring B is not optionally substituted 10-membered bicyclic heteroaryl having 1-4 heteroatoms independently selected from nitrogen, oxygen, and sulfur (e.g., quinazolinyl).

In some embodiments, Ring B is optionally substituted 10- to 16-membered polycyclic heteroaryl having 1-5 heteroatoms independently selected from nitrogen, oxygen, and sulfur. In some embodiments, Ring B is optionally substituted 5,6,7,8-tetrahydrocyclopenta[4,5]pyrrolo[2,3-b]pyridyl.

In some embodiments, Ring B is optionally substituted 7- to 10-membered bicyclic heterocyclyl having 1-4 heteroatoms independently selected from nitrogen, oxygen, and sulfur. In some embodiments, Ring B is optionally substituted 7- to 10-membered fused bicyclic heterocyclyl having 1-4 heteroatoms independently selected from nitrogen, oxygen, and sulfur.

In some embodiments, Ring B is optionally substituted 7-membered bicyclic heterocyclyl having 1-3 heteroatoms independently selected from nitrogen, oxygen, and sulfur. In some embodiments, Ring B is optionally substituted 7-membered fused bicyclic heterocyclyl having 1-3 heteroatoms independently selected from nitrogen, oxygen, and sulfur. In some embodiments, Ring B is not 7-membered spirocyclic bicyclic heterocyclyl having 1-4 heteroatoms independently selected from nitrogen, oxygen, and sulfur (e.g., 2-oxaspiro[3.3]heptanyl). In some embodiments, Ring B is optionally substituted 8-membered bicyclic heterocyclyl having 1-3 heteroatoms independently selected from nitrogen, oxygen, and sulfur. In some embodiments, Ring B is optionally substituted 9-membered bicyclic heterocyclyl having 1-3 heteroatoms independently selected from nitrogen, oxygen, and sulfur. In some embodiments, Ring B is not a 9-membered bicyclic heterocyclyl having 1 nitrogen (e.g., 6,7-dihydro-5H-cyclopenta[b]pyridyl). In some embodiments, Ring B is optionally substituted 10-membered bicyclic heterocyclyl having 1-3 heteroatoms independently selected from nitrogen, oxygen, and sulfur.

In some embodiments, Ring B is optionally substituted 10- to 16-membered polycyclic heterocyclyl having 1-5 heteroatoms independently selected from nitrogen, oxygen, and sulfur.

In some embodiments, Ring B is selected from the group consisting of:

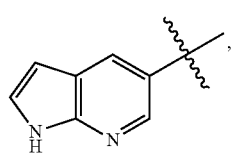, 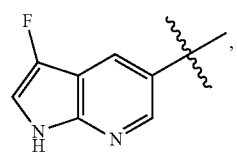,

-continued

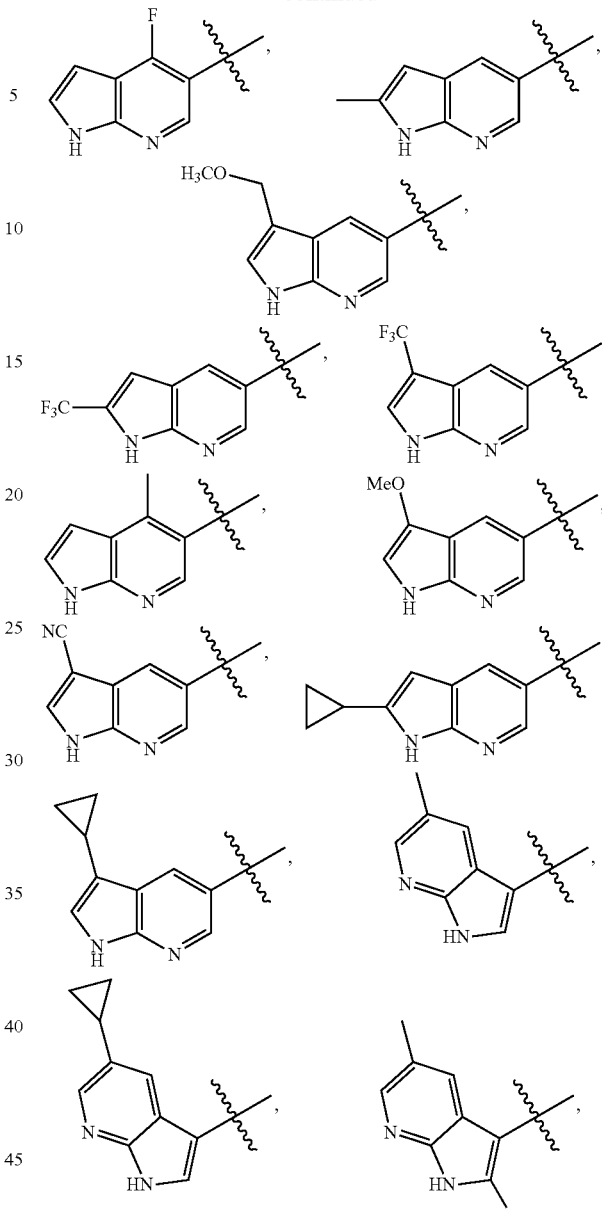

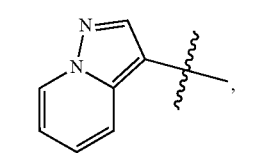, 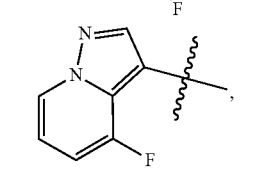,

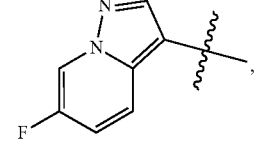, 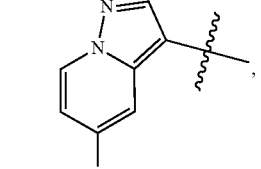,

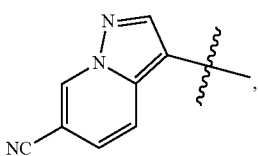, 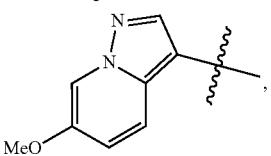

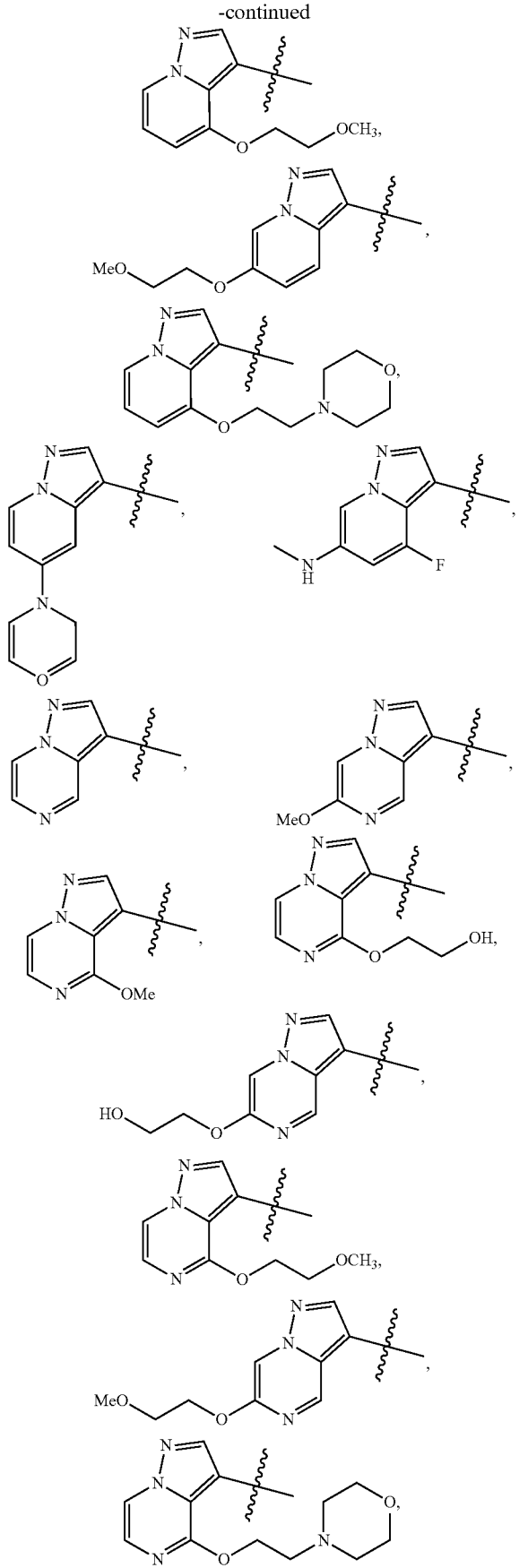
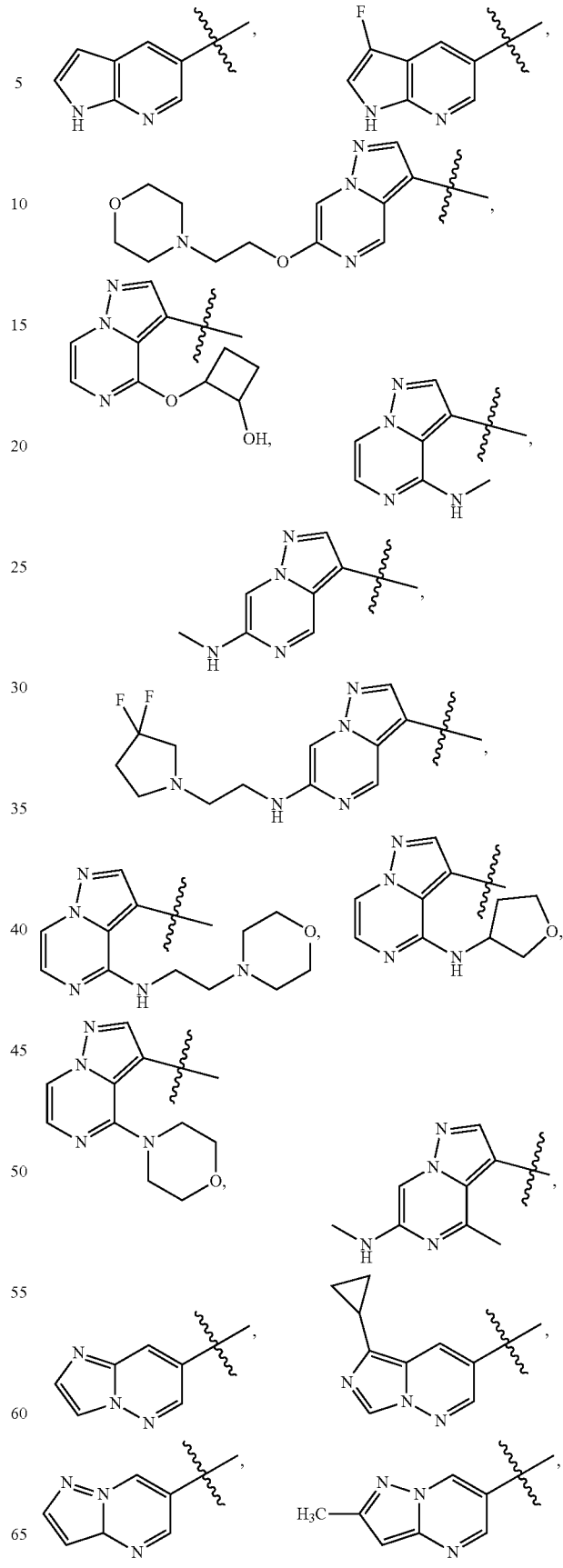

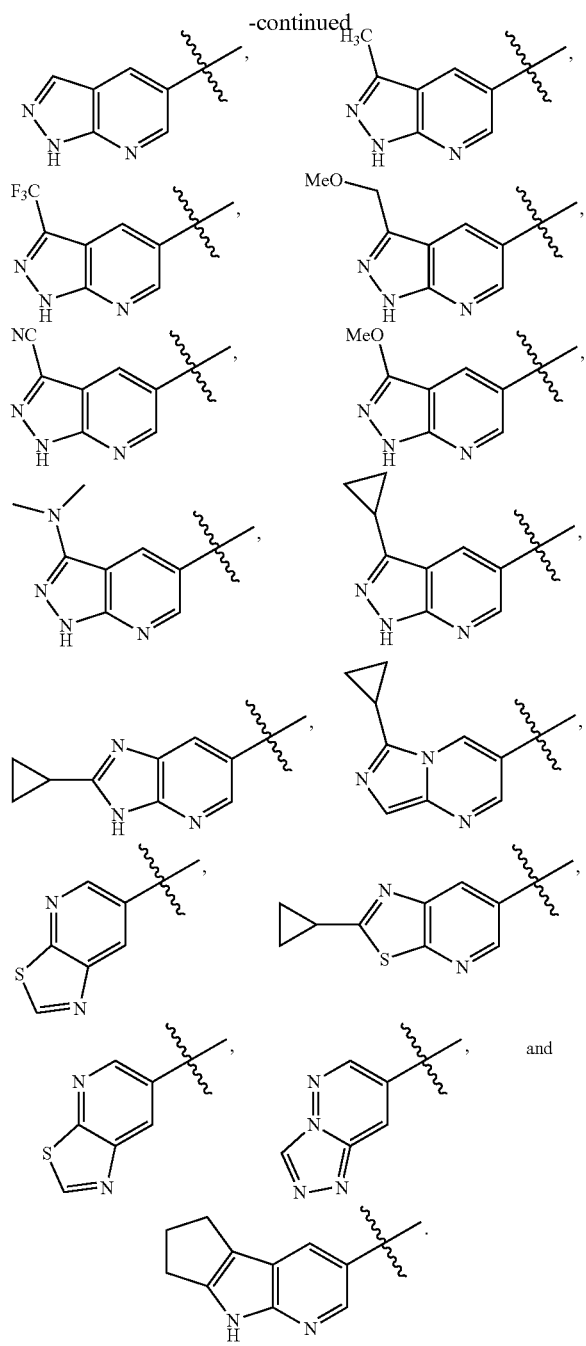

In some embodiments, Ring B is

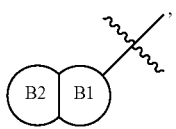

wherein Ring B1 and Ring B2 are defined as in Formula I-A and described in classes and subclasses herein, both singly and in combination; and Ring B1 is fused to Ring B2; and Ring B2 is optionally (i) further fused to Ring B3 or (ii) Ring B2 and Ring B3 combine to form a spirocycle.

In some embodiments, Ring B1 is an optionally substituted ring selected from 5- to 6-membered monocyclic heteroaryl having 1-3 heteroatoms independently selected from nitrogen, oxygen, and sulfur and 5- to 6-membered saturated or partially unsaturated monocyclic heterocyclyl having 1-3 heteroatoms independently selected from nitrogen, oxygen, and sulfur.

In some embodiments, Ring B1 is optionally substituted phenyl. In some embodiments, when Ring B1 is phenyl, Ring B2 contains at least one heteroatom.

In some embodiments, Ring B1 is optionally substituted 5- to 6-membered monocyclic heteroaryl having 1-3 heteroatoms independently selected from nitrogen, oxygen, and sulfur. In some embodiments, Ring B1 is 5- to 6-membered monocyclic heteroaryl having 1-3 heteroatoms independently selected from nitrogen, oxygen, and sulfur optionally substituted with one or more halogen or $C_{1-6}$ alkyl. In some embodiments, Ring B1 is unsubstituted 5- to 6-membered monocyclic heteroaryl having 1-3 heteroatoms independently selected from nitrogen, oxygen, and sulfur. In some embodiments, Ring B1 is optionally substituted 5-membered monocyclic heteroaryl having 1-3 heteroatoms independently selected from nitrogen, oxygen, and sulfur. In some embodiments, Ring B1 is optionally substituted pyrazole. In some embodiments, Ring B1 is optionally substituted pyrrole or pyrazole. In some embodiments, Ring B1 is optionally substituted 6-membered monocyclic heteroaryl having 1-3 heteroatoms independently selected from nitrogen, oxygen, and sulfur. In some embodiments, Ring B1 is optionally substituted pyridine, pyridazine, or pyrimidine (e.g., pyridine, pyridazine, or pyrimidine optionally substituted with one or more halogen or $C_{1-6}$ alkyl).

In some embodiments, Ring B1 is optionally substituted 5- to 6-membered saturated or partially unsaturated monocyclic carbocyclyl. In some embodiments, when Ring B1 is optionally substituted 5- to 6-membered saturated or partially unsaturated monocyclic carbocyclyl, Ring B2 contains at least one heteroatom. In some embodiments, when Ring B2 is not aromatic, Ring B1 is optionally substituted 5- to 6-membered saturated monocyclic carbocyclyl. In some embodiments, Ring B1 is optionally substituted 5- to 6-membered partially saturated monocyclic carbocyclyl.

In some embodiments, Ring B1 is optionally substituted 5- to 6-membered saturated or partially unsaturated monocyclic heterocyclyl having 1-3 heteroatoms independently selected from nitrogen, oxygen, and sulfur. In some embodiments, when Ring B2 is not aromatic, Ring B1 is optionally substituted 5- to 6-membered saturated monocyclic heterocyclyl having 1-3 heteroatoms independently selected from nitrogen, oxygen, and sulfur. In some embodiments, Ring B1 is optionally substituted 5- to 6-membered partially saturated monocyclic heterocyclyl having 1-3 heteroatoms independently selected from nitrogen, oxygen, and sulfur.

In some embodiments, optionally substituted Ring B1 fused to Ring B2 is selected from the group consisting of:

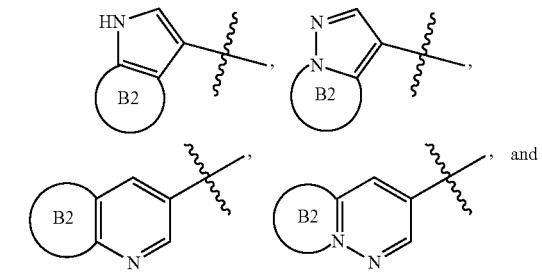

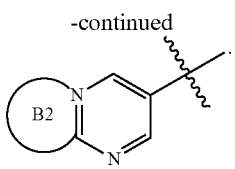

In some embodiments, Ring B2 is an optionally substituted ring selected from 5- to 6-membered monocyclic heteroaryl having 1-3 heteroatoms independently selected from nitrogen, oxygen, and sulfur and 5- to 6-membered saturated or partially unsaturated monocyclic heterocyclyl having 1-3 heteroatoms independently selected from nitrogen, oxygen, and sulfur.

In some embodiments, Ring B2 is optionally substituted phenyl. In some embodiments, when Ring B2 is phenyl, Ring B1 contains at least one heteroatom.

In some embodiments, Ring B2 is optionally substituted 5- to 6-membered monocyclic heteroaryl having 1-3 heteroatoms independently selected from nitrogen, oxygen, and sulfur. In some embodiments, Ring B2 is 5- to 6-membered monocyclic heteroaryl having 1-3 heteroatoms independently selected from nitrogen, oxygen, and sulfur optionally substituted with one or more with one or more oxo, halogen, —O(optionally substituted $C_{1-6}$ alkyl), —O(optionally substituted $C_{3-6}$ carbocyclyl), —NH (optionally substituted $C_{1-6}$ alkyl), —NH (optionally substituted 3- to 6-membered saturated heterocyclyl), —N(optionally substituted $C_{1-6}$ alkyl)$_2$, —CN, optionally substituted $C_{1-6}$ aliphatic (e.g., optionally substituted $C_{1-6}$ alkyl), optionally substituted $C_{3-6}$ carbocyclyl (e.g., optionally substituted $C_{3-6}$ cycloalkyl), and optionally substituted 3- to 6-membered saturated or partially unsaturated heterocyclyl having 1-2 heteroatoms selected from nitrogen, oxygen, and sulfur (e.g., optionally substituted 3- to 6-membered saturated heterocyclyl having 1-2 heteroatoms selected from nitrogen, oxygen, and sulfur). In some embodiments, Ring B2 is 5- to 6-membered monocyclic heteroaryl having 1-3 heteroatoms independently selected from nitrogen, oxygen, and sulfur optionally substituted with one or more —O($C_{1-6}$ alkyl), —CN, optionally substituted $C_{1-6}$ aliphatic (e.g., optionally substituted $C_{1-6}$ alkyl) and optionally substituted $C_{3-6}$ carbocyclyl (e.g., optionally substituted $C_{3-6}$ cycloalkyl). In some embodiments, Ring B2 is 5- to 6-membered monocyclic heteroaryl having 1-3 heteroatoms independently selected from nitrogen, oxygen, and sulfur optionally substituted with one or more —O($C_{1-4}$ alkyl), —CN, $C_{1-4}$ alkyl optionally substituted with one or more —O($C_{1-4}$ alkyl), and $C_{3-4}$ cycloalkyl. In some embodiments, Ring B2 is 5- to 6-membered monocyclic heteroaryl having 1-3 heteroatoms independently selected from nitrogen, oxygen, and sulfur optionally substituted with one or more —O($C_{1-4}$ alkyl), —CN, $C_{1-4}$ alkyl optionally substituted with one or more halogen or —O($C_{1-4}$ alkyl), and $C_{3-4}$ cycloalkyl. In some embodiments, Ring B2 is 5- to 6-membered monocyclic heteroaryl having 1-3 heteroatoms independently selected from nitrogen, oxygen, and sulfur optionally substituted with one or more halogen, —O($C_{1-4}$ alkyl), —NH($C_{1-4}$ alkyl), —CN, $C_{1-4}$ alkyl optionally substituted with one or more halogen or —O($C_{1-4}$ alkyl), and $C_{3-4}$ cycloalkyl. In some embodiments, Ring B2 is optionally substituted 5-membered monocyclic heteroaryl having 1-3 heteroatoms independently selected from nitrogen, oxygen, and sulfur. In some embodiments, Ring B2 is optionally substituted pyrrole, pyrazole, imidazole, triazole, thiophene, or thiazole. In some embodiments, Ring B2 is optionally substituted 6-membered monocyclic heteroaryl having 1-3 heteroatoms independently selected from nitrogen, oxygen, and sulfur. In some embodiments, Ring B2 is unsubstituted 6-membered monocyclic heteroaryl having 1-3 heteroatoms independently selected from nitrogen, oxygen, and sulfur. In some embodiments, Ring B2 is optionally substituted pyridine or pyrazine. In some embodiments, Ring B2 is pyridine or pyrazine. In some embodiments, Ring B2 is not pyridine.

In some embodiments, Ring B2 is optionally substituted 5- to 6-membered saturated or partially unsaturated monocyclic carbocyclyl. In some embodiments, when Ring B2 is optionally substituted 5- to 6-membered saturated or partially unsaturated monocyclic carbocyclyl, Ring B1 contains at least one heteroatom. In some embodiments, when Ring B1 is not aromatic, Ring B2 is optionally substituted 5- to 6-membered saturated monocyclic carbocyclyl. In some embodiments, Ring B2 is optionally substituted 5- to 6-membered partially saturated monocyclic carbocyclyl.

In some embodiments, Ring B2 is optionally substituted 5- to 6-membered saturated or partially unsaturated monocyclic heterocyclyl having 1-3 heteroatoms independently selected from nitrogen, oxygen, and sulfur. In some embodiments, when Ring B1 (and Ring B3, if present) is not aromatic, Ring B2 is optionally substituted 5- to 6-membered saturated monocyclic heterocyclyl having 1-3 heteroatoms independently selected from nitrogen, oxygen, and sulfur. In some embodiments, Ring B2 is optionally substituted 5- to 6-membered partially saturated monocyclic heterocyclyl having 1-3 heteroatoms independently selected from nitrogen, oxygen, and sulfur.

In some embodiments, optionally substituted Ring B2 fused to Ring B1 is selected from the group consisting of:

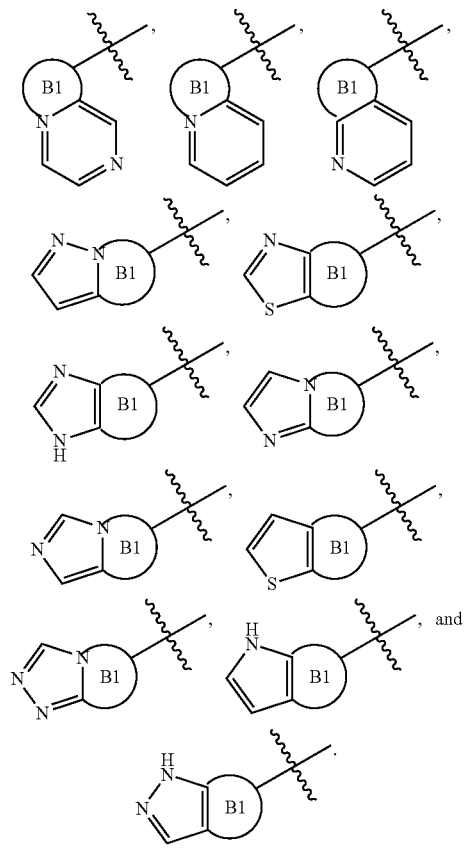

In some embodiments, Ring B1 and Ring B2 are both optionally substituted 5- to 6-membered monocyclic heteroaryl having 1-3 heteroatoms independently selected from nitrogen, oxygen, and sulfur. In some embodiments, Ring B1 is optionally substituted 5-membered monocyclic heteroaryl having 1-3 heteroatoms independently selected from nitrogen, oxygen, and sulfur, and Ring B2 is optionally substituted 6-membered monocyclic heteroaryl having 1-3 heteroatoms independently selected from nitrogen, oxygen, and sulfur. In some embodiments, Ring B1 is optionally substituted 6-membered monocyclic heteroaryl having 1-3 heteroatoms independently selected from nitrogen, oxygen, and sulfur, and Ring B2 is optionally substituted 5-membered monocyclic heteroaryl having 1-3 heteroatoms independently selected from nitrogen, oxygen, and sulfur.

In some embodiments, Ring B2 is further fused to Ring B3. In some embodiments, Ring B2 and Ring B3 combine to form a spirocycle.

In some embodiments, Ring B3, when present, is optionally substituted phenyl. In some embodiments, Ring B3 is 5- to 6-membered monocyclic heteroaryl having 1-3 heteroatoms independently selected from nitrogen, oxygen, and sulfur. In some embodiments, Ring B3 is 3- to 7-membered saturated or partially unsaturated monocyclic carbocyclyl. In some embodiments, Ring B3, when not fused to an aromatic Ring B2, is 3- to 7-membered saturated monocyclic carbocyclyl. In some embodiments, Ring B3 is 3- to 7-membered partially saturated monocyclic carbocyclyl. In some embodiments, Ring B3 is 3- to 7-membered saturated or partially unsaturated monocyclic heterocyclyl having 1-3 heteroatoms independently selected from nitrogen, oxygen, and sulfur. In some embodiments, Ring B3, when not fused to an aromatic Ring B2, is 3- to 7-membered saturated monocyclic heterocyclyl having 1-3 heteroatoms independently selected from nitrogen, oxygen, and sulfur. In some embodiments, Ring B3 is 3- to 7-membered partially saturated monocyclic heterocyclyl having 1-3 heteroatoms independently selected from nitrogen, oxygen, and sulfur.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, each R is independently hydrogen or optionally substituted $C_{1-6}$ aliphatic. In some embodiments, R is hydrogen. In some embodiments, R is optionally substituted $C_{1-6}$ aliphatic (e.g., $C_{1-6}$ aliphatic optionally substituted with one or more 3- to 7-membered saturated or partially unsaturated monocyclic heterocyclyl having 1-3 heteroatoms independently selected from nitrogen, oxygen, and sulfur). In some embodiments, R is optionally substituted straight-chain or branched $C_{1-6}$ aliphatic (i.e., optionally substituted acyclic $C_{1-6}$ aliphatic). In some embodiments, R is optionally substituted $C_{1-6}$ alkyl (e.g., $C_{1-6}$ alkyl optionally substituted with one or more 3- to 7-membered saturated or partially unsaturated monocyclic heterocyclyl having 1-3 heteroatoms independently selected from nitrogen, oxygen, and sulfur). In some embodiments, R is optionally substituted 3- to 7-membered saturated or partially unsaturated carbocyclyl. In some embodiments, R is optionally substituted 3- to 7-membered saturated or partially unsaturated monocyclic heterocyclyl having 1-3 heteroatoms independently selected from nitrogen, oxygen, and sulfur. In some embodiments, R is 3- to 7-membered saturated or partially unsaturated monocyclic heterocyclyl having 1-3 heteroatoms independently selected from nitrogen, oxygen, and sulfur and optionally substituted with one or more $C_{1-6}$ alkyl. In some embodiments, R is optionally substituted 4- to 6-membered saturated monocyclic heterocyclyl having 1-2 heteroatoms independently selected from nitrogen, oxygen, and sulfur. In some embodiments, R is 4- to 6-membered saturated monocyclic heterocyclyl having 1-2 heteroatoms independently selected from nitrogen, oxygen, and sulfur and optionally substituted with one or more $C_{1-6}$ alkyl. In some embodiments, R is optionally substituted phenyl. In some embodiments, R is optionally substituted 5- to 6-membered monocyclic heteroaryl having 1-3 heteroatoms independently selected from nitrogen, oxygen, and sulfur. In some embodiments, two R when attached to the same nitrogen atom are taken together form a 3- to 7-membered saturated or partially unsaturated monocyclic heterocyclyl having 0-2 additional heteroatoms independently selected from nitrogen, oxygen, and sulfur. In some embodiments, two R when attached to the same nitrogen atom are taken together form a 4- to 6-membered saturated monocyclic heterocyclyl having 0-1 additional heteroatoms independently selected from nitrogen, oxygen, and sulfur.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, R' is optionally substituted $C_{1-6}$ aliphatic. In some embodiments, R' is optionally substituted straight-chain or branched $C_{1-6}$ aliphatic (i.e., optionally substituted acyclic $C_{1-6}$ aliphatic). In some embodiments, R' is optionally substituted $C_{1-6}$ alkyl. In some embodiments, R' is 3- to 7-membered saturated or partially unsaturated carbocyclyl.

In some embodiments of any of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, n is 1 or 2. In some embodiments, n is 1. In some embodiments, n is 2. In some embodiments, n is 3.

In some embodiments of any of Formulae I, II, III, IV, I-A, II-A, III-A, IV-A, I-B, II-B, III-B, and IV-B, the compound is not:

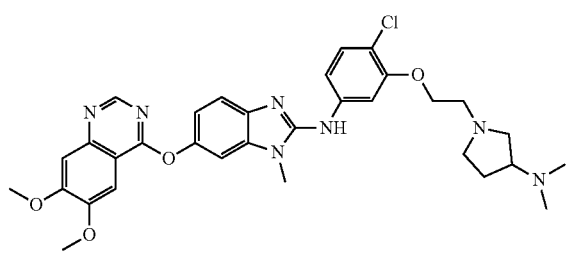

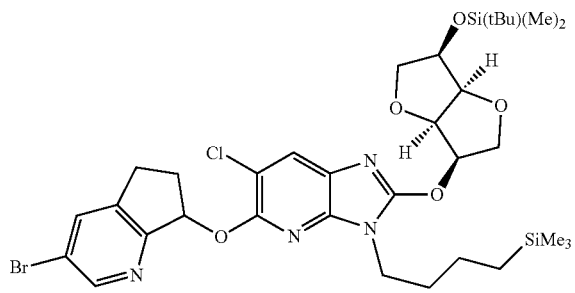

67
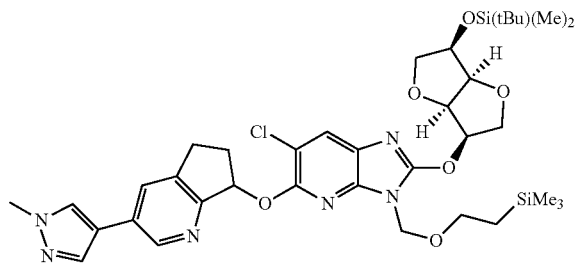
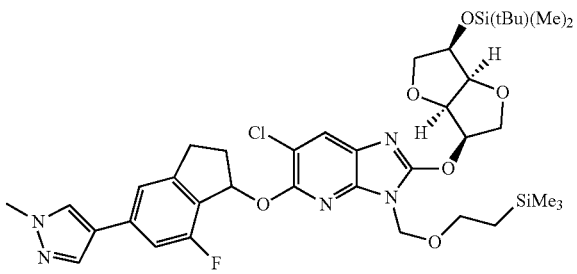
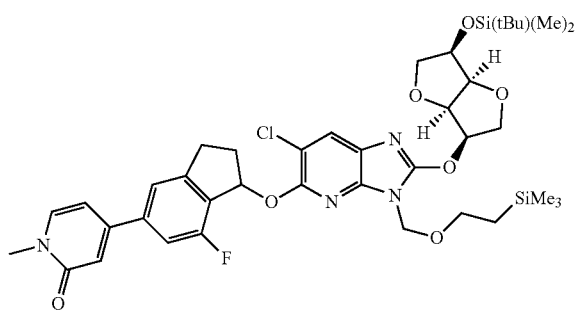
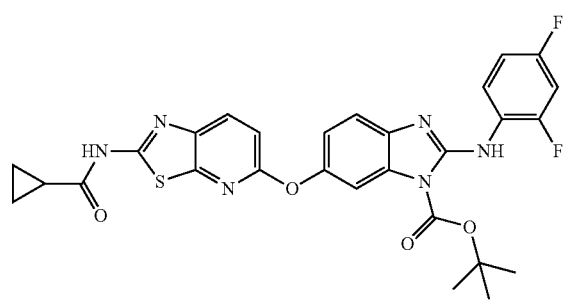
68
-continued
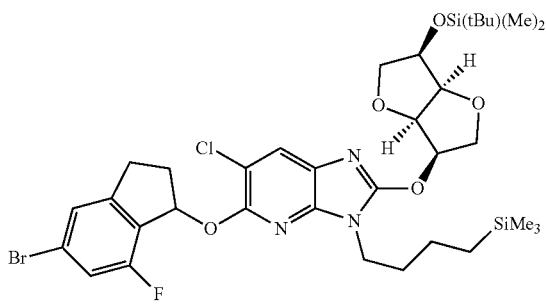
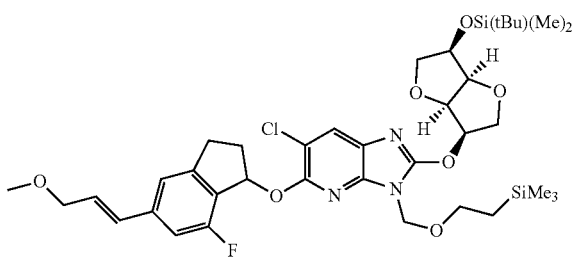
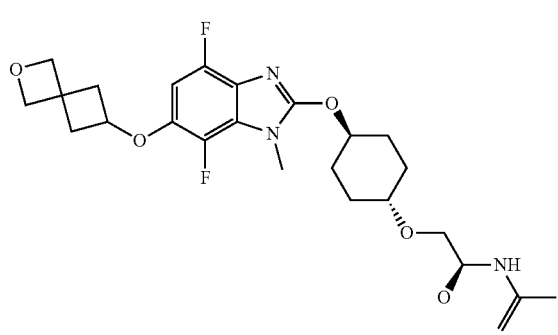
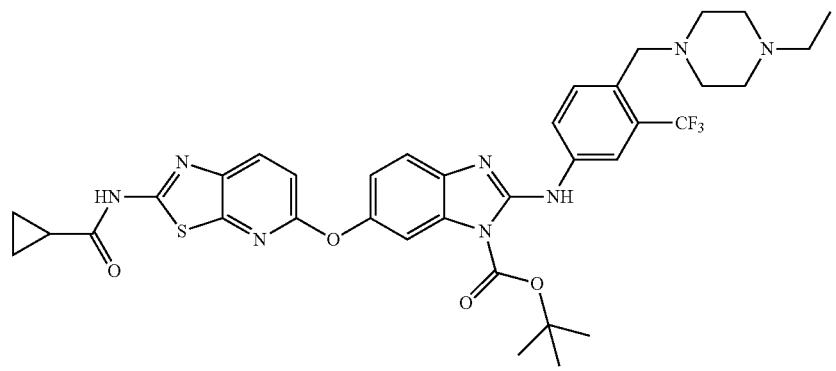

In some embodiments, when Ring A is phenyl, $R^a$ is not fluoro, chloro, —CF$_3$, or

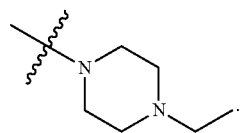 [SMILES: *N1CCN(CC)CC1]

In some embodiments, when Ring A is phenyl and L is a covalent bond, $R^a$ is not fluoro, chloro, —CF$_3$, or

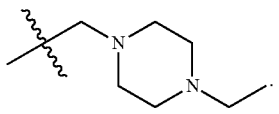 [SMILES: *CN1CCN(CC)CC1]

In some embodiments, when Ring A is phenyl, $R^b$ is not fluoro, —OR, —CF$_3$, or

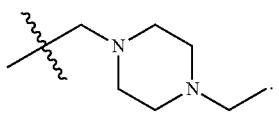

In some embodiments, when Ring A is phenyl, $R^1$ is unsubstituted C$_{1-6}$ alkyl (e.g., unsubstituted C$_{1-4}$ alkyl, e.g., unsubstituted C$_{1-2}$ alkyl). In some embodiments, when Ring A is phenyl, $R^1$ is not —C(O)OC(CH$_3$)$_3$.

In some embodiments, when Ring A is phenyl, Ring B is not

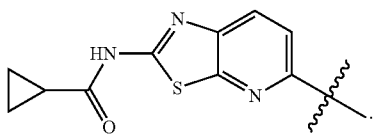 [SMILES: *c1ccc2nc(NC(=O)C3CC3)sc2n1]

In some embodiments, when Ring A is phenyl, Ring B is not optionally substituted 10-membered bicyclic heteroaryl having 1-4 heteroatoms independently selected from nitrogen, oxygen, and sulfur (e.g., quinazolinyl).

In some embodiments, when Ring A is phenyl, Ring B is unsubstituted.

In some embodiments, when Ring A is 3- to 7-membered saturated or partially unsaturated monocyclic carbocyclyl (e.g., cyclohexyl), then $R^b$ is not —OR.

In some embodiments, when Ring A is 3- to 7-membered saturated or partially unsaturated monocyclic carbocyclyl (e.g., cyclohexyl), then $R^a$ is not hydrogen.

In some embodiments, when Ring A is 8-membered saturated bicyclic heterocyclyl having 1-4 heteroatoms independently selected from nitrogen, oxygen, and sulfur (e.g., hexahydrofuro[3,2-b]furan), then $R^b$ is not —OR.

In some embodiments, when Ring A is 8-membered saturated bicyclic heterocyclyl having 1-4 heteroatoms independently selected from nitrogen, oxygen, and sulfur (e.g., hexahydrofuro[3,2-b]furan), then $R^a$ is not hydrogen.

In some embodiments, the present disclosure provides compounds selected from Table 1:

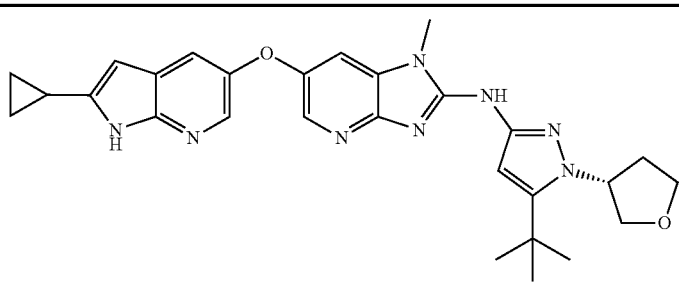

I-1

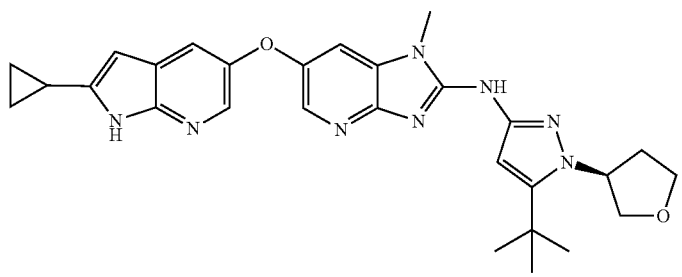

I-2

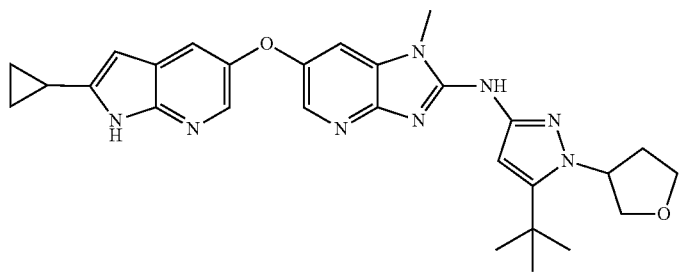 [SMILES: Cn1c(Nc2cc(C(C)(C)C)n([C@@H]3CCOC3)n2)nc2ncc(Oc3cnc4[nH]c(C5CC5)cc4c3)cc21]

I-1'

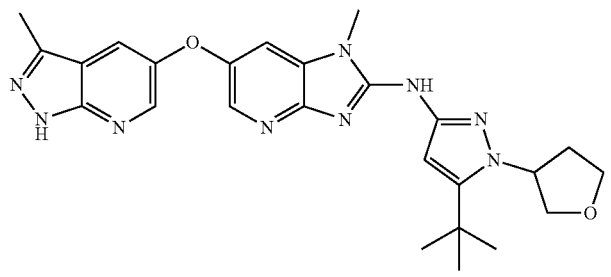 [SMILES: Cc1n[nH]c2ncc(Oc3cnc4nc(Nc5cc(C(C)(C)C)n(C6CCOC6)n5)n(C)c4c3)cc12]
I-3'
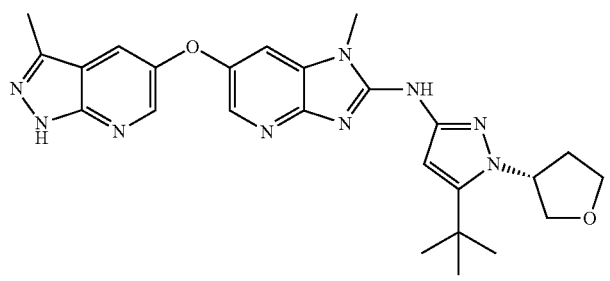 [SMILES: Cc1n[nH]c2ncc(Oc3cnc4nc(Nc5cc(C(C)(C)C)n([C@@H]6CCOC6)n5)n(C)c4c3)cc12]
I-3
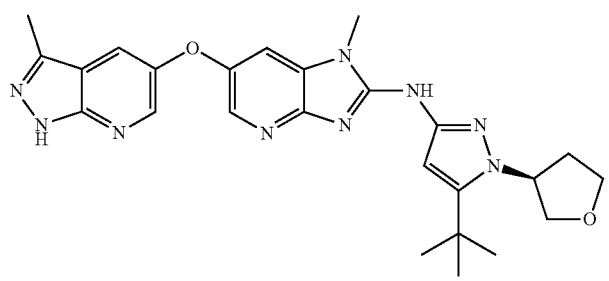
I-4
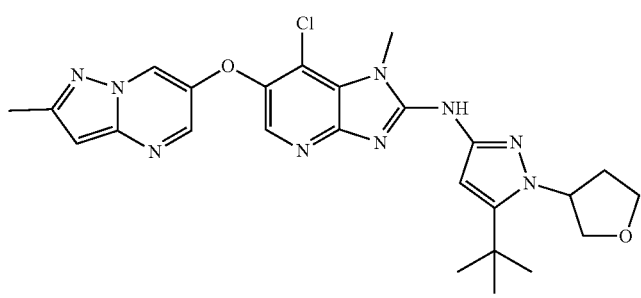 [SMILES: Cc1cc2ncc(Oc3cnc4nc(Nc5cc(C(C)(C)C)n(C6CCOC6)n5)n(C)c4c3Cl)cn2n1]
I-5'
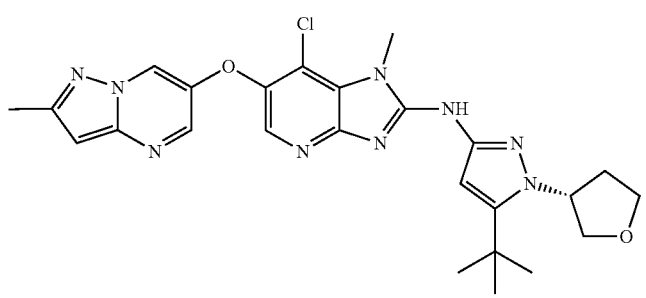 [SMILES: Cc1cc2ncc(Oc3cnc4nc(Nc5cc(C(C)(C)C)n([C@@H]6CCOC6)n5)n(C)c4c3Cl)cn2n1]
I-5

-continued
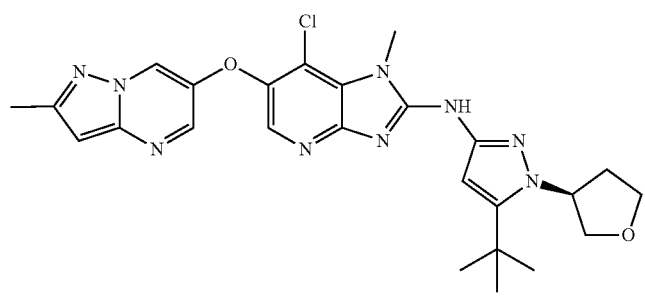 [SMILES: Cc1cc2ncc(Oc3cnc4nc(Nc5cc(C(C)(C)C)n([C@H]6CCOC6)n5)n(C)c4c3Cl)cn2n1]
I-6
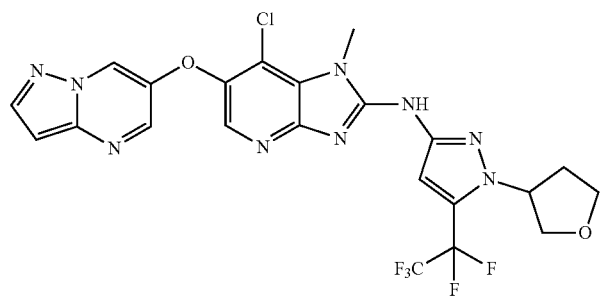 [SMILES: Cn1c(Nc2cc(C(F)(F)C(F)(F)F)n(C3CCOC3)n2)nc2ncc(Oc3cnc4ccnn4c3)c(Cl)c21]
I-7'
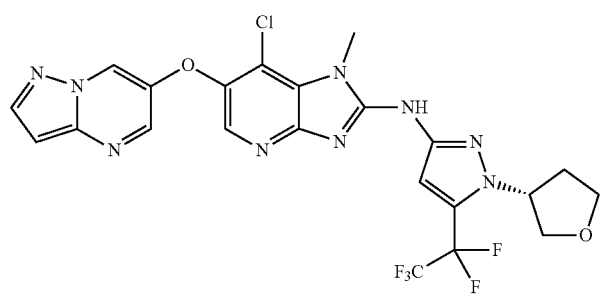 [SMILES: Cn1c(Nc2cc(C(F)(F)C(F)(F)F)n([C@@H]3CCOC3)n2)nc2ncc(Oc3cnc4ccnn4c3)c(Cl)c21]
I-7
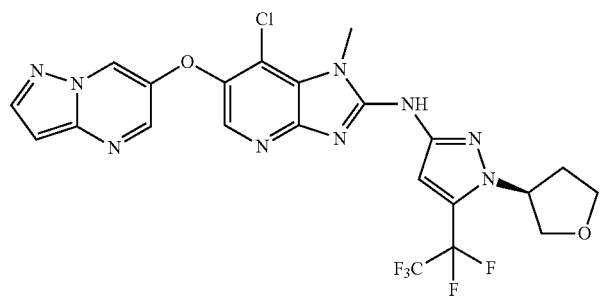 [SMILES: Cn1c(Nc2cc(C(F)(F)C(F)(F)F)n([C@H]3CCOC3)n2)nc2ncc(Oc3cnc4ccnn4c3)c(Cl)c21]
I-8
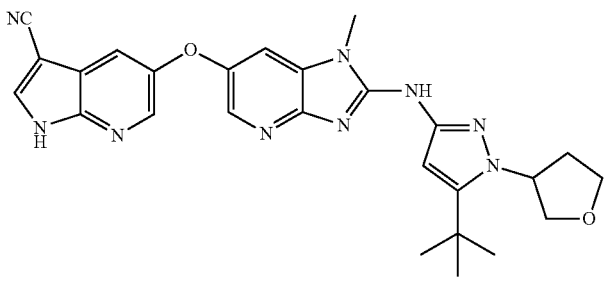 [SMILES: Cn1c(Nc2cc(C(C)(C)C)n(C3CCOC3)n2)nc2ncc(Oc3cnc4[nH]cc(C#N)c4c3)cc21]
I-9'

-continued
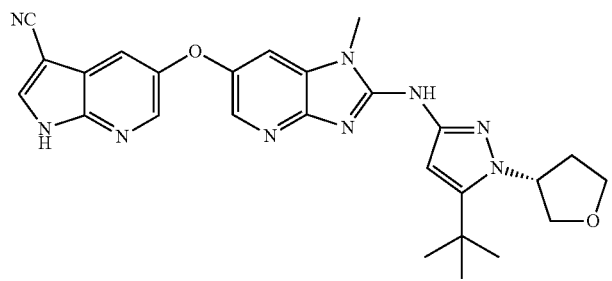 [SMILES: Cn1c(Nc2cc(C(C)(C)C)n([C@@H]3CCOC3)n2)nc2ncc(Oc3cnc4[nH]cc(C#N)c4c3)cc21]
I-9
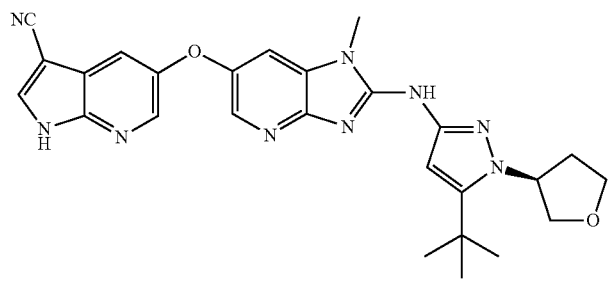 [SMILES: Cn1c(Nc2cc(C(C)(C)C)n([C@H]3CCOC3)n2)nc2ncc(Oc3cnc4[nH]cc(C#N)c4c3)cc21]
I-10
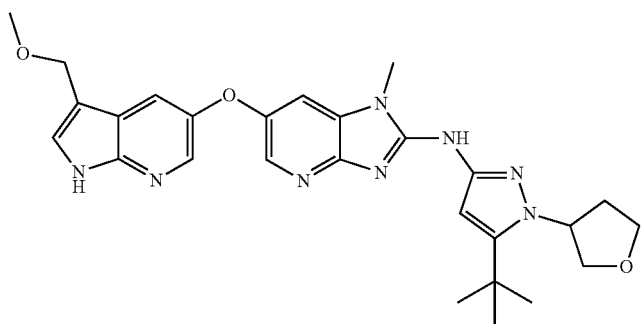
I-11'
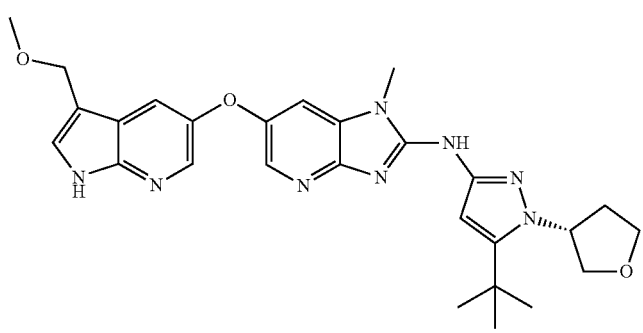 [SMILES: COCc1c[nH]c2ncc(Oc3cnc4nc(Nc5cc(C(C)(C)C)n([C@@H]6CCOC6)n5)n(C)c4c3)cc12]
I-11
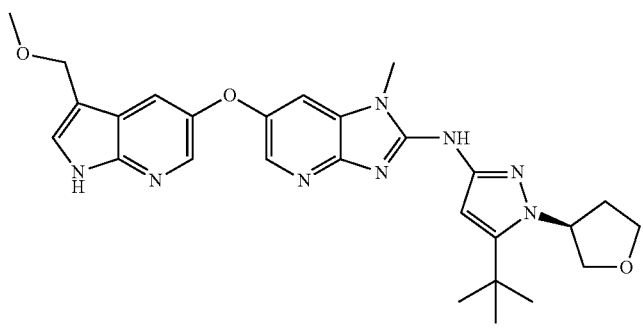 [SMILES: COCc1c[nH]c2ncc(Oc3cnc4nc(Nc5cc(C(C)(C)C)n([C@H]6CCOC6)n5)n(C)c4c3)cc12]
I-12

-continued
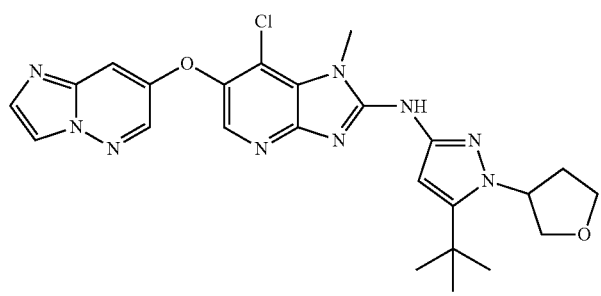 [SMILES: Cn1c(Nc2cc(C(C)(C)C)n(C3CCOC3)n2)nc2ncc(Oc3cnn4ccnc4c3)c(Cl)c21]
I-13'
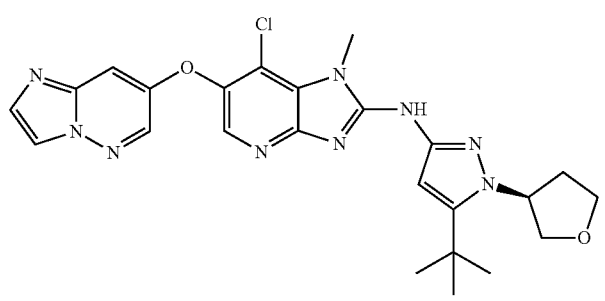 [SMILES: Cn1c(Nc2cc(C(C)(C)C)n([C@H]3CCOC3)n2)nc2ncc(Oc3cnn4ccnc4c3)c(Cl)c21]
I-13
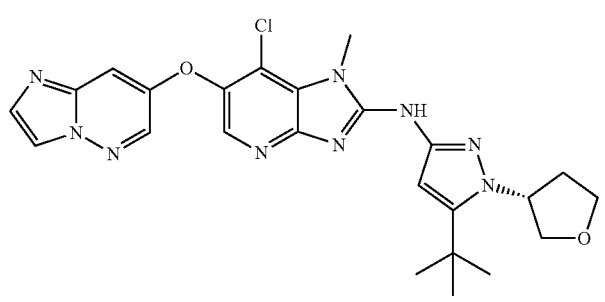
I-14
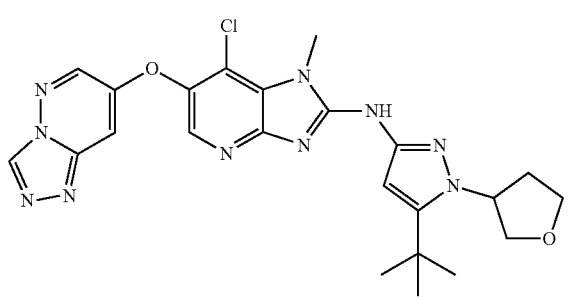 [SMILES: Cn1c(Nc2cc(C(C)(C)C)n(C3CCOC3)n2)nc2ncc(Oc3cnn4cnnc4c3)c(Cl)c21]
I-15'
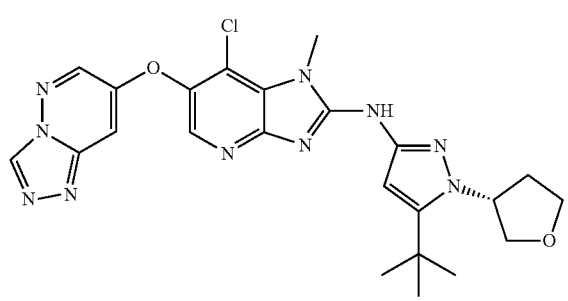 [SMILES: Cn1c(Nc2cc(C(C)(C)C)n([C@@H]3CCOC3)n2)nc2ncc(Oc3cnn4cnnc4c3)c(Cl)c21]
I-15

-continued
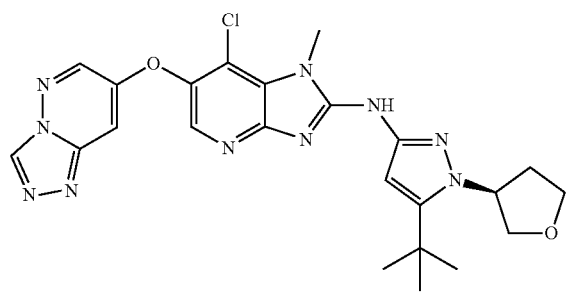 [SMILES: Cn1c(Nc2cc(C(C)(C)C)n([C@H]3CCOC3)n2)nc2ncc(Oc3cnn4cnnc4c3)c(Cl)c21]
I-16
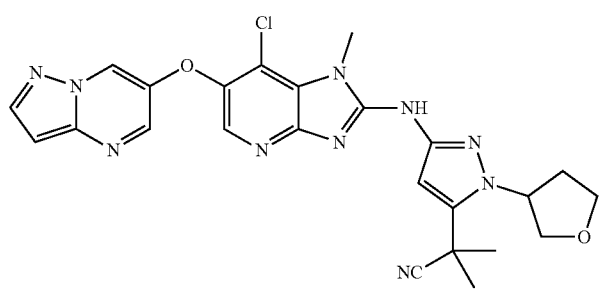 [SMILES: Cn1c(Nc2cc(C(C)(C)C#N)n(C3CCOC3)n2)nc2ncc(Oc3cnc4ccnn4c3)c(Cl)c21]
I-17'
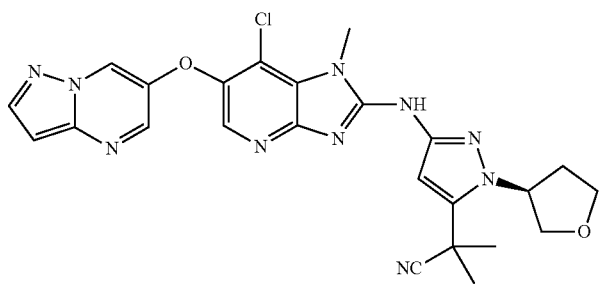 [SMILES: Cn1c(Nc2cc(C(C)(C)C#N)n([C@H]3CCOC3)n2)nc2ncc(Oc3cnc4ccnn4c3)c(Cl)c21]
I-17
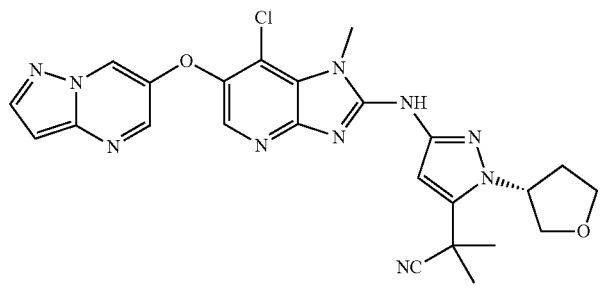 [SMILES: Cn1c(Nc2cc(C(C)(C)C#N)n([C@@H]3CCOC3)n2)nc2ncc(Oc3cnc4ccnn4c3)c(Cl)c21]
I-18
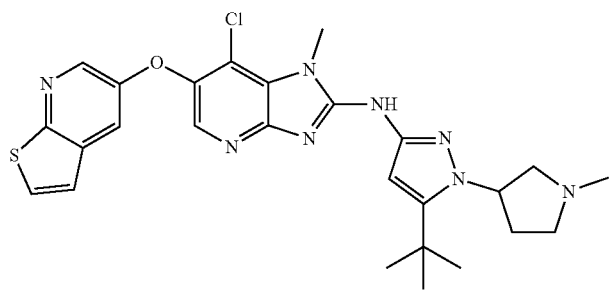 [SMILES: CN1CCC(n2nc(Nc3nc4ncc(Oc5cnc6sccc6c5)c(Cl)c4n3C)cc2C(C)(C)C)C1]
I-19'

-continued
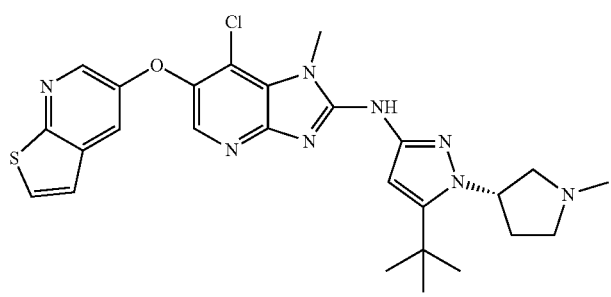 [SMILES: CN1CC[C@H](n2nc(Nc3nc4ncc(Oc5cnc6sccc6c5)c(Cl)c4n3C)cc2C(C)(C)C)C1]
I-19
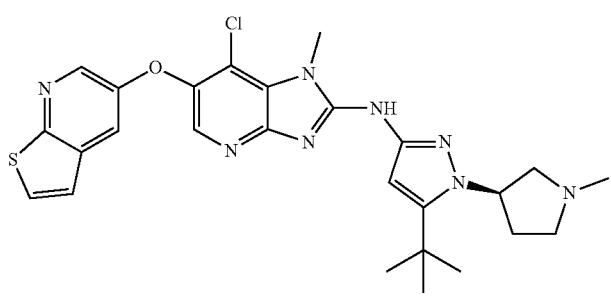 [SMILES: CN1CC[C@@H](n2nc(Nc3nc4ncc(Oc5cnc6sccc6c5)c(Cl)c4n3C)cc2C(C)(C)C)C1]
I-20
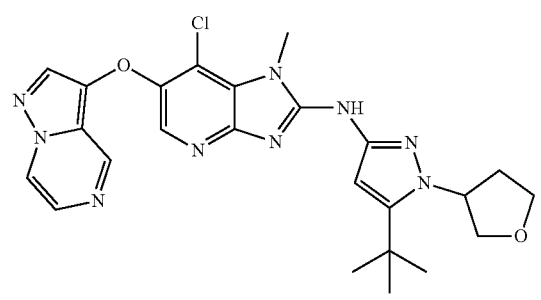 [SMILES: Cn1c(Nc2cc(C(C)(C)C)n(C3CCOC3)n2)nc2ncc(Oc3cnn4ccncc34)c(Cl)c21]
I-21'
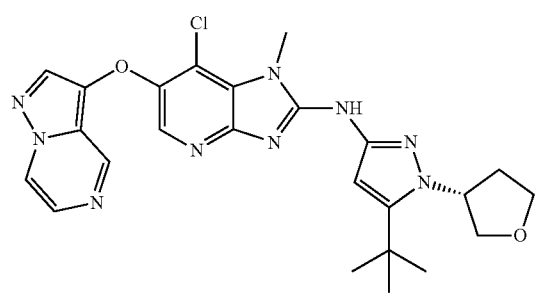 [SMILES: Cn1c(Nc2cc(C(C)(C)C)n([C@@H]3CCOC3)n2)nc2ncc(Oc3cnn4ccncc34)c(Cl)c21]
I-21
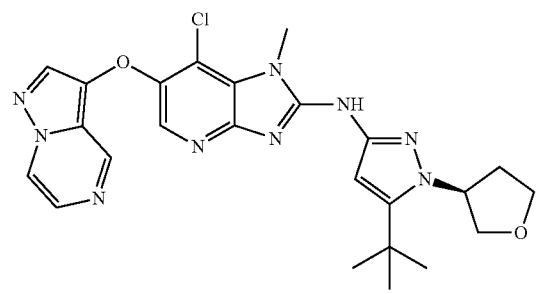 [SMILES: Cn1c(Nc2cc(C(C)(C)C)n([C@H]3CCOC3)n2)nc2ncc(Oc3cnn4ccncc34)c(Cl)c21]
I-22

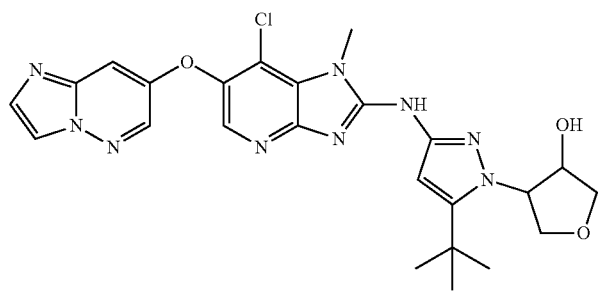 [SMILES: Cn1c(Nc2cc(C(C)(C)C)n(C3COCC3O)n2)nc2ncc(Oc3cnn4ccnc4c3)c(Cl)c21]
I-23'
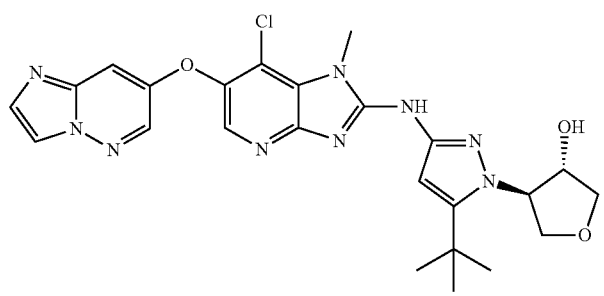 [SMILES: Cn1c(Nc2cc(C(C)(C)C)n([C@@H]3COC[C@H]3O)n2)nc2ncc(Oc3cnn4ccnc4c3)c(Cl)c21]
I-23-i
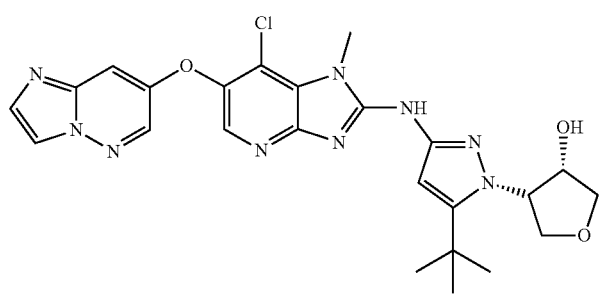
I-23-ii
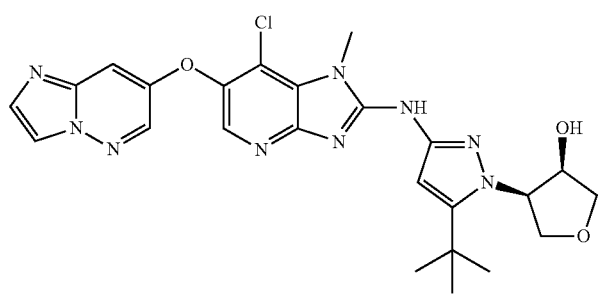 [SMILES: Cn1c(Nc2cc(C(C)(C)C)n([C@@H]3COC[C@@H]3O)n2)nc2ncc(Oc3cnn4ccnc4c3)c(Cl)c21]
I-23-iii
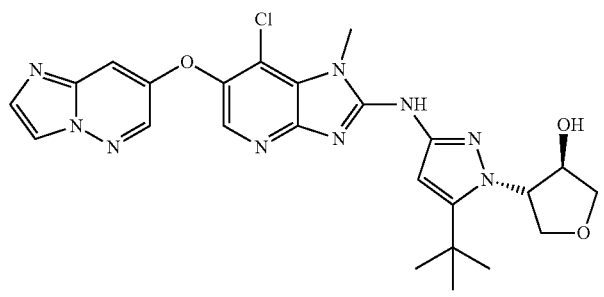
I-23-iv

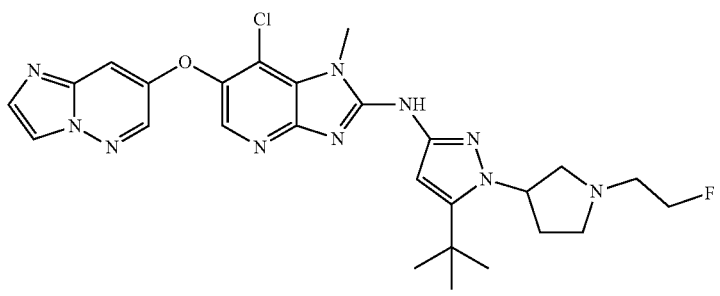 [SMILES: Cn1c(Nc2cc(C(C)(C)C)n(C3CCN(CCF)C3)n2)nc2ncc(Oc3cnn4ccnc4c3)c(Cl)c21]
I-25'
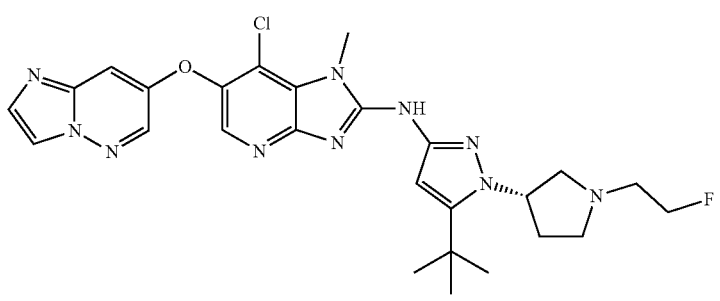 [SMILES: Cn1c(Nc2cc(C(C)(C)C)n([C@H]3CCN(CCF)C3)n2)nc2ncc(Oc3cnn4ccnc4c3)c(Cl)c21]
I-25
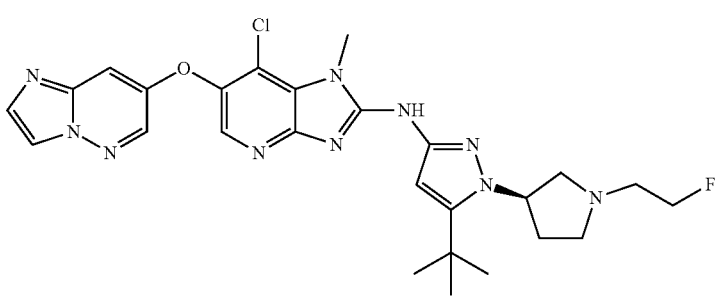 [SMILES: Cn1c(Nc2cc(C(C)(C)C)n([C@@H]3CCN(CCF)C3)n2)nc2ncc(Oc3cnn4ccnc4c3)c(Cl)c21]
I-26
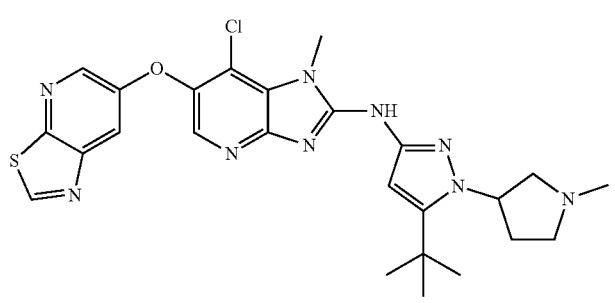 [SMILES: CN1CCC(n2nc(Nc3nc4ncc(Oc5cnc6scnc6c5)c(Cl)c4n3C)cc2C(C)(C)C)C1]
I-27'
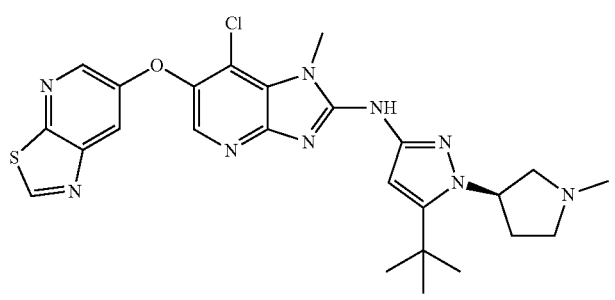 [SMILES: CN1CC[C@@H](n2nc(Nc3nc4ncc(Oc5cnc6scnc6c5)c(Cl)c4n3C)cc2C(C)(C)C)C1]
I-27

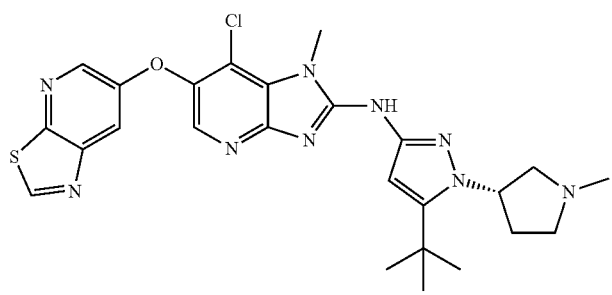 [SMILES: CN1CC[C@H](n2nc(Nc3nc4ncc(Oc5cnc6scnc6c5)c(Cl)c4n3C)cc2C(C)(C)C)C1]
I-28
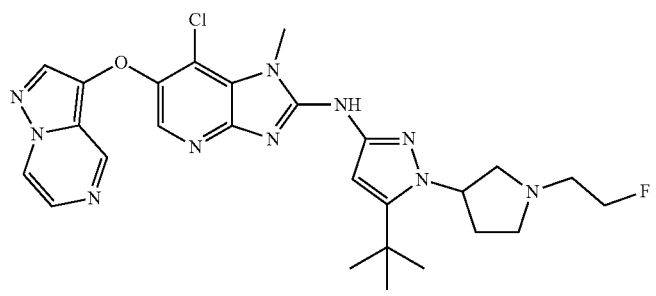 [SMILES: Cn1c(Nc2cc(C(C)(C)C)n(C3CCN(CCF)C3)n2)nc2ncc(Oc3cnn4ccncc34)c(Cl)c21]
I-29'
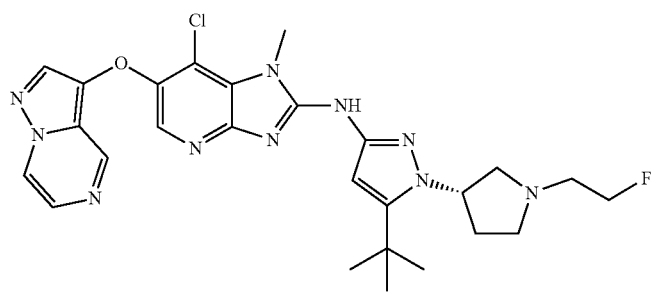 [SMILES: Cn1c(Nc2cc(C(C)(C)C)n([C@H]3CCN(CCF)C3)n2)nc2ncc(Oc3cnn4ccncc34)c(Cl)c21]
I-29
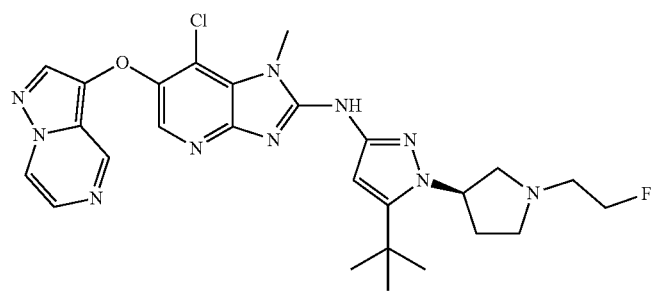 [SMILES: Cn1c(Nc2cc(C(C)(C)C)n([C@@H]3CCN(CCF)C3)n2)nc2ncc(Oc3cnn4ccncc34)c(Cl)c21]
I-30
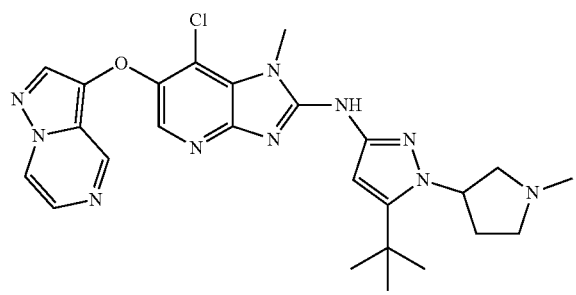 [SMILES: CN1CCC(n2nc(Nc3nc4ncc(Oc5cnn6ccncc56)c(Cl)c4n3C)cc2C(C)(C)C)C1]
I-31'

-continued
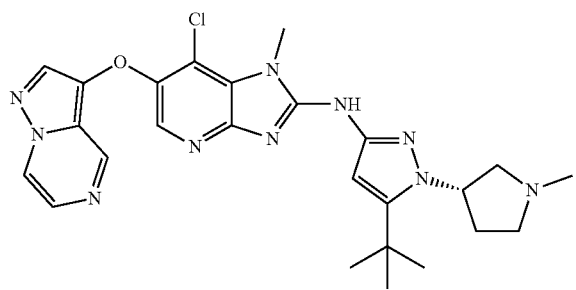 [SMILES: CN1CC[C@H](n2nc(Nc3nc4ncc(Oc5cnn6ccncc56)c(Cl)c4n3C)cc2C(C)(C)C)C1]
I-31
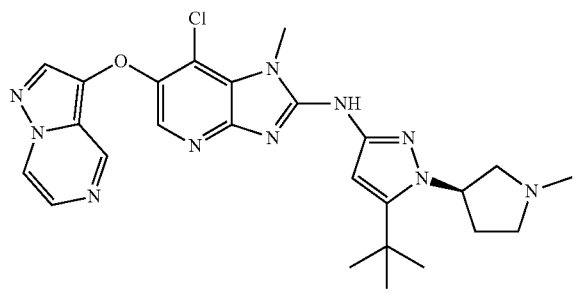 [SMILES: CN1CC[C@@H](n2nc(Nc3nc4ncc(Oc5cnn6ccncc56)c(Cl)c4n3C)cc2C(C)(C)C)C1]
I-32
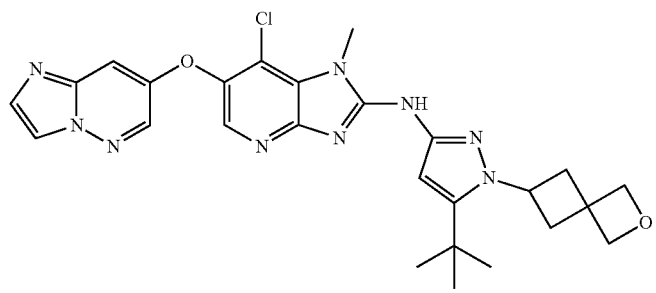 [SMILES: Cn1c(Nc2cc(C(C)(C)C)n(C3CC4(COC4)C3)n2)nc2ncc(Oc3cnn4ccnc4c3)c(Cl)c21]
I-33
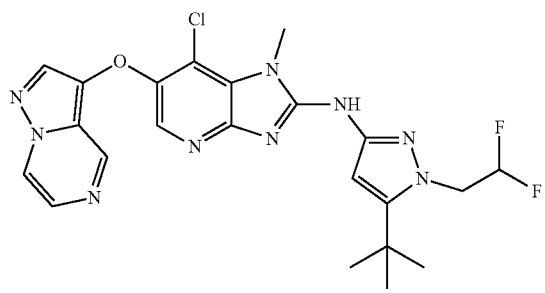 [SMILES: Cn1c(Nc2cc(C(C)(C)C)n(CC(F)F)n2)nc2ncc(Oc3cnn4ccncc34)c(Cl)c21]
I-34
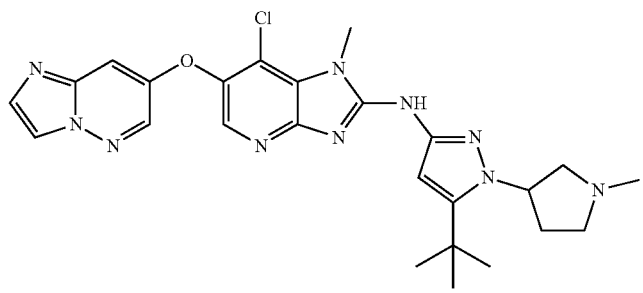 [SMILES: CN1CCC(n2nc(Nc3nc4ncc(Oc5cnn6ccnc6c5)c(Cl)c4n3C)cc2C(C)(C)C)C1]
I-35'

-continued
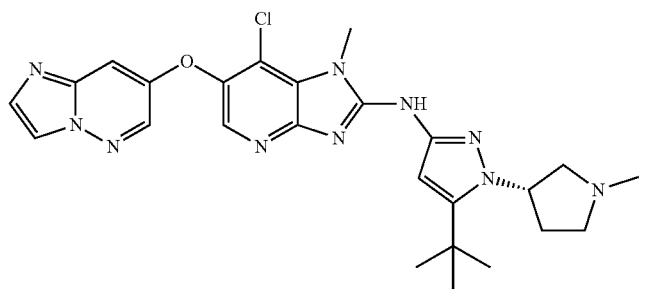 [SMILES: CN1CC[C@H](n2nc(Nc3nc4ncc(Oc5cnn6ccnc6c5)c(Cl)c4n3C)cc2C(C)(C)C)C1]
I-35
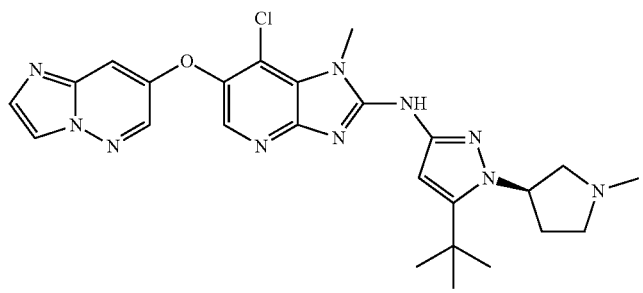 [SMILES: CN1CC[C@@H](n2nc(Nc3nc4ncc(Oc5cnn6ccnc6c5)c(Cl)c4n3C)cc2C(C)(C)C)C1]
I-36
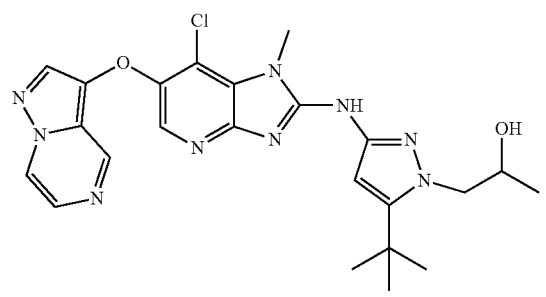 [SMILES: CC(O)Cn1nc(Nc2nc3ncc(Oc4cnn5ccncc45)c(Cl)c3n2C)cc1C(C)(C)C]
I-37
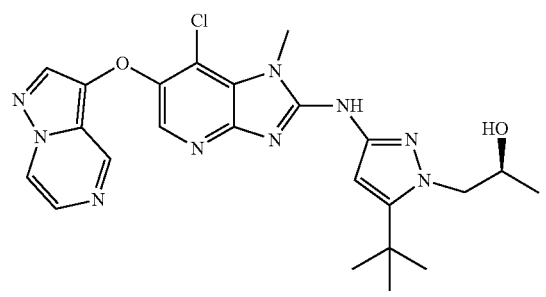 [SMILES: C[C@H](O)Cn1nc(Nc2nc3ncc(Oc4cnn5ccncc45)c(Cl)c3n2C)cc1C(C)(C)C]
I-37-i
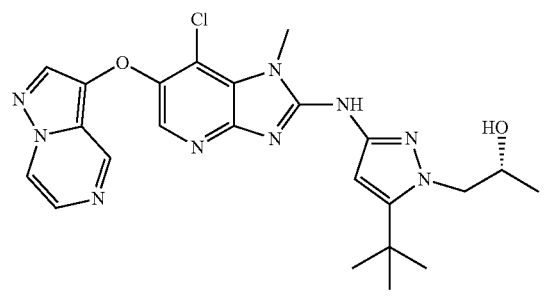 [SMILES: C[C@@H](O)Cn1nc(Nc2nc3ncc(Oc4cnn5ccncc45)c(Cl)c3n2C)cc1C(C)(C)C]
I-37-ii -continued
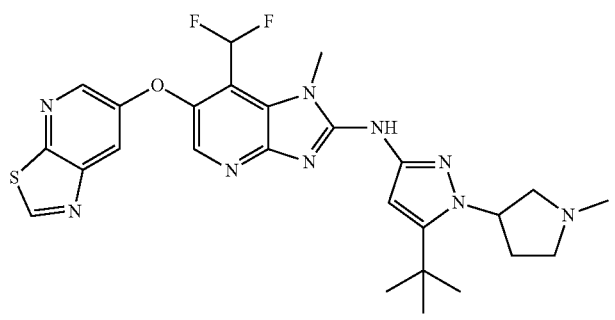 [SMILES: CN1CCC(n2nc(Nc3nc4ncc(Oc5cnc6scnc6c5)c(C(F)F)c4n3C)cc2C(C)(C)C)C1] I-39'
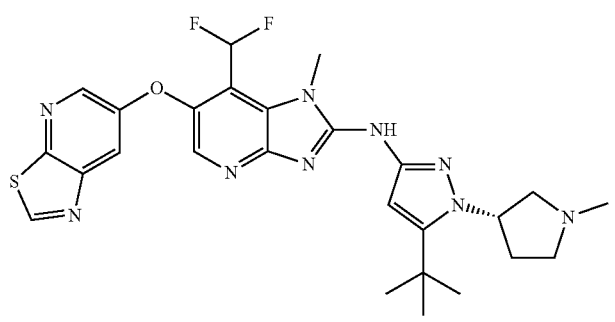 [SMILES: CN1CC[C@H](n2nc(Nc3nc4ncc(Oc5cnc6scnc6c5)c(C(F)F)c4n3C)cc2C(C)(C)C)C1] I-39
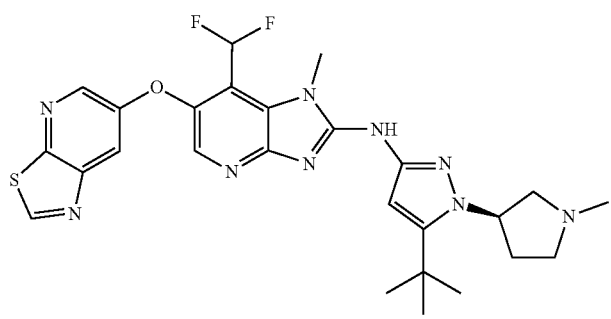 [SMILES: CN1CC[C@@H](n2nc(Nc3nc4ncc(Oc5cnc6scnc6c5)c(C(F)F)c4n3C)cc2C(C)(C)C)C1] I-40
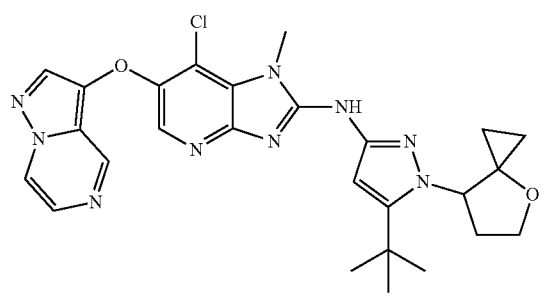 [SMILES: Cn1c(Nc2cc(C(C)(C)C)n(C3CCOC34CC4)n2)nc2ncc(Oc3cnn4ccncc34)c(Cl)c21] I-41
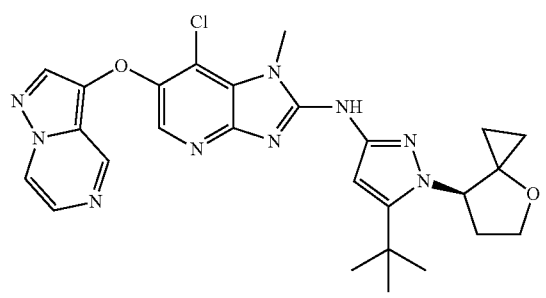 [SMILES: Cn1c(Nc2cc(C(C)(C)C)n([C@@H]3CCOC34CC4)n2)nc2ncc(Oc3cnn4ccncc34)c(Cl)c21] I-41-i -continued
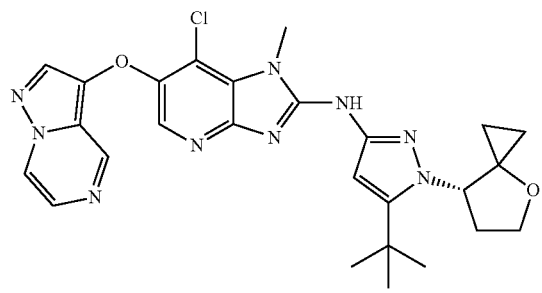 [SMILES: Cn1c(Nc2cc(C(C)(C)C)n([C@H]3CCOC34CC4)n2)nc2ncc(Oc3cnn4ccncc34)c(Cl)c21]
I-41-ii
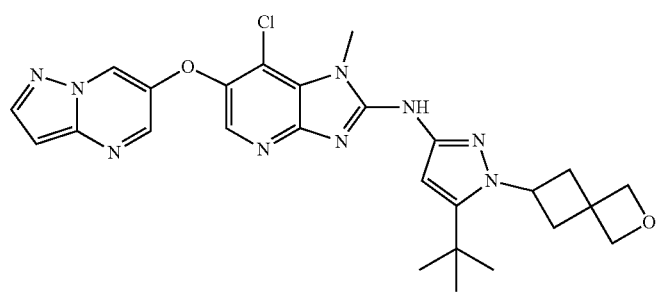 [SMILES: Cn1c(Nc2cc(C(C)(C)C)n(C3CC4(COC4)C3)n2)nc2ncc(Oc3cnc4ccnn4c3)c(Cl)c21]
I-42
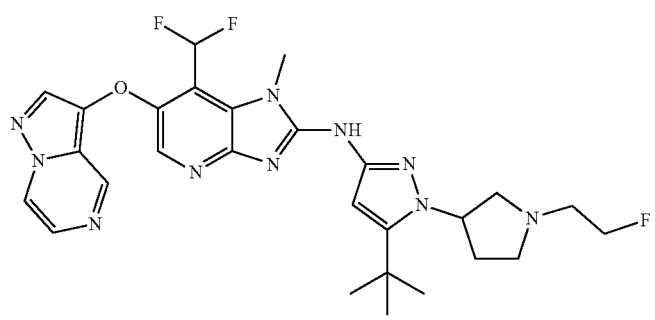 [SMILES: Cn1c(Nc2cc(C(C)(C)C)n(C3CCN(CCF)C3)n2)nc2ncc(Oc3cnn4ccncc34)c(C(F)F)c21]
I-43'
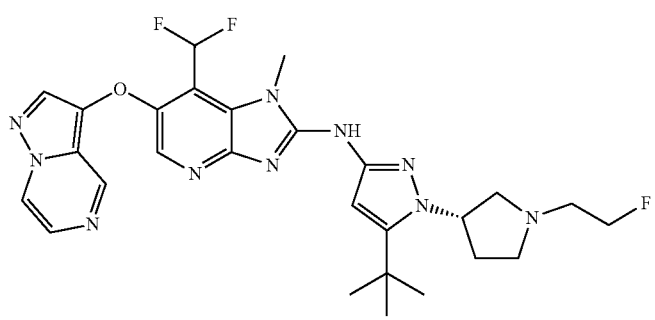 [SMILES: Cn1c(Nc2cc(C(C)(C)C)n([C@H]3CCN(CCF)C3)n2)nc2ncc(Oc3cnn4ccncc34)c(C(F)F)c21]
I-43
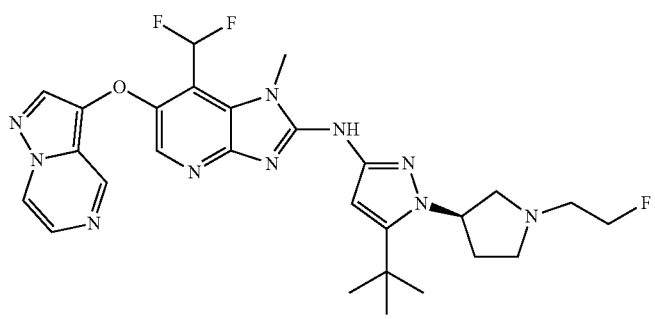 [SMILES: Cn1c(Nc2cc(C(C)(C)C)n([C@@H]3CCN(CCF)C3)n2)nc2ncc(Oc3cnn4ccncc34)c(C(F)F)c21]
I-44

-continued
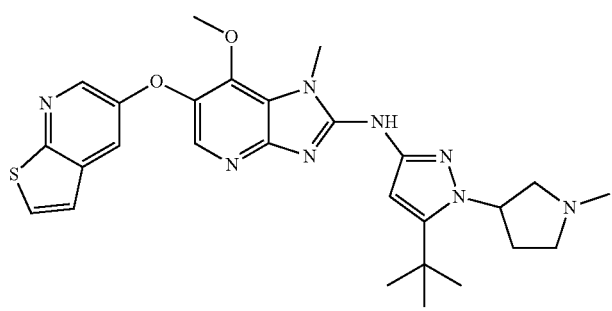 [SMILES: COc1c(Oc2cnc3sccc3c2)cnc2nc(Nc3cc(C(C)(C)C)n(C4CCN(C)C4)n3)n(C)c12]
I-45'
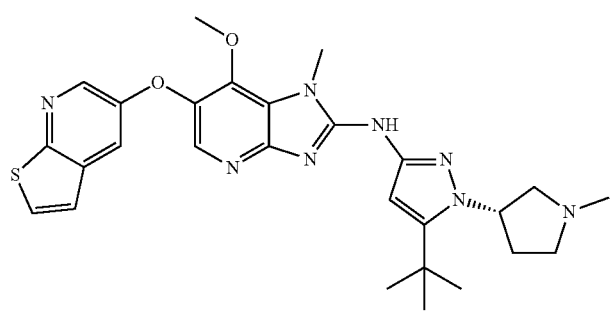 [SMILES: COc1c(Oc2cnc3sccc3c2)cnc2nc(Nc3cc(C(C)(C)C)n([C@H]4CCN(C)C4)n3)n(C)c12]
I-45
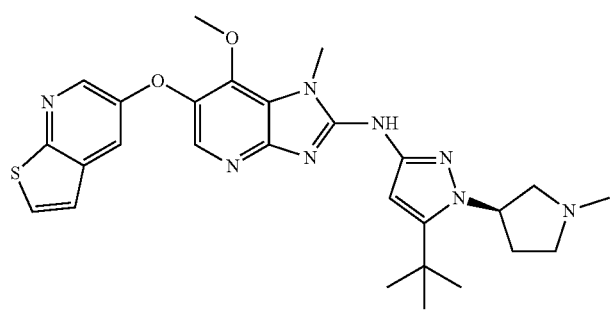 [SMILES: COc1c(Oc2cnc3sccc3c2)cnc2nc(Nc3cc(C(C)(C)C)n([C@@H]4CCN(C)C4)n3)n(C)c12]
I-46
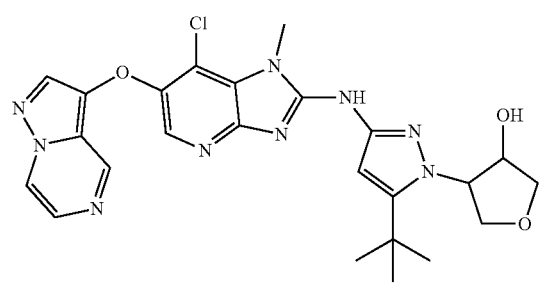 [SMILES: Cn1c(Nc2cc(C(C)(C)C)n(C3COCC3O)n2)nc2ncc(Oc3cnn4ccncc34)c(Cl)c21]
I-47
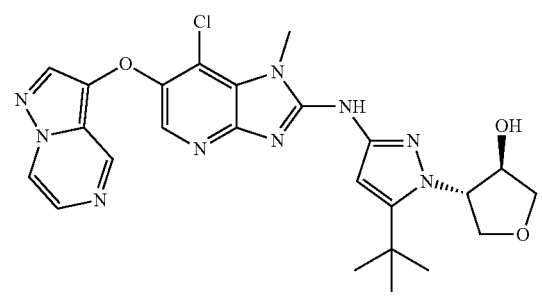 [SMILES: Cn1c(Nc2cc(C(C)(C)C)n([C@H]3COC[C@@H]3O)n2)nc2ncc(Oc3cnn4ccncc34)c(Cl)c21]
I-47-i -continued
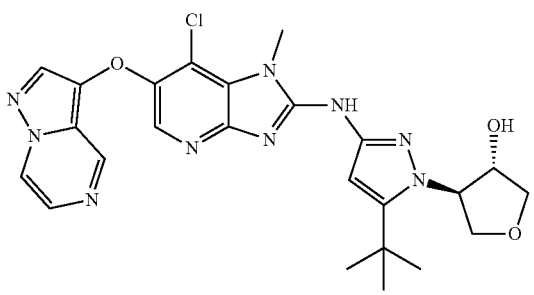 [SMILES: Cn1c(Nc2cc(C(C)(C)C)n([C@@H]3COC[C@H]3O)n2)nc2ncc(Oc3cnn4ccncc34)c(Cl)c21]
I-47-ii
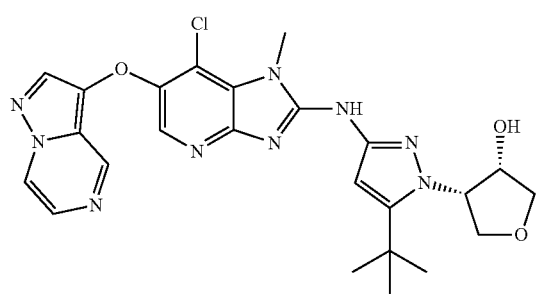 [SMILES: Cn1c(Nc2cc(C(C)(C)C)n([C@H]3COC[C@H]3O)n2)nc2ncc(Oc3cnn4ccncc34)c(Cl)c21]
I-47-iii
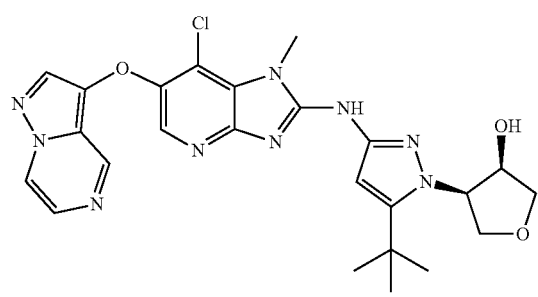 [SMILES: Cn1c(Nc2cc(C(C)(C)C)n([C@@H]3COC[C@@H]3O)n2)nc2ncc(Oc3cnn4ccncc34)c(Cl)c21]
I-47-iv
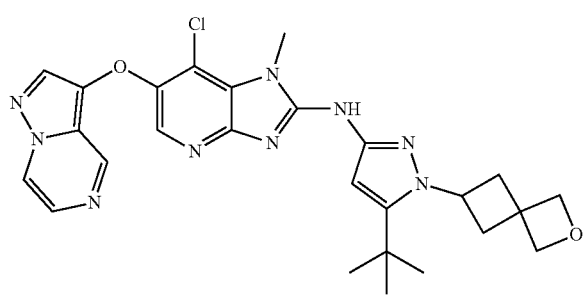 [SMILES: Cn1c(Nc2cc(C(C)(C)C)n(C3CC4(COC4)C3)n2)nc2ncc(Oc3cnn4ccncc34)c(Cl)c21]
I-49
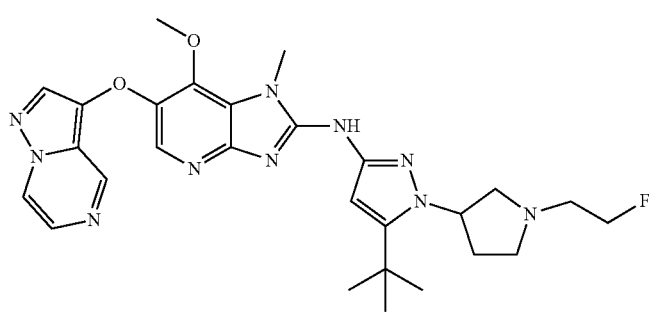 [SMILES: COc1c(Oc2cnn3ccncc23)cnc2nc(Nc3cc(C(C)(C)C)n(C4CCN(CCF)C4)n3)n(C)c12]
I-50'

-continued
I-50
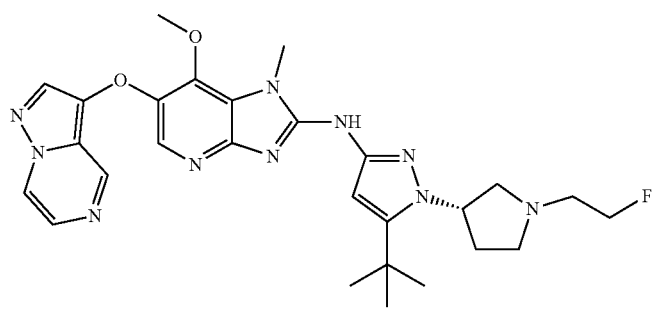
I-50-ii
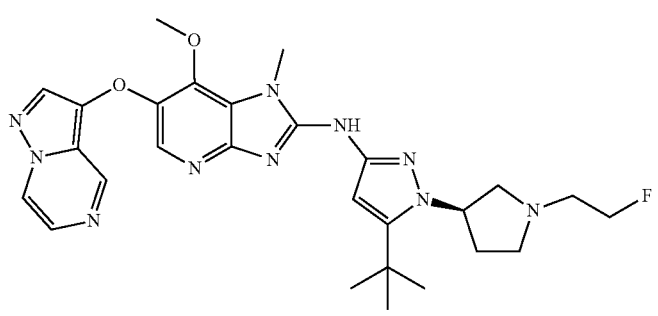 [SMILES: COc1c(Oc2cnn3ccncc23)cnc2nc(Nc3cc(C(C)(C)C)n([C@@H]4CCN(CCF)C4)n3)n(C)c12]
I-51'
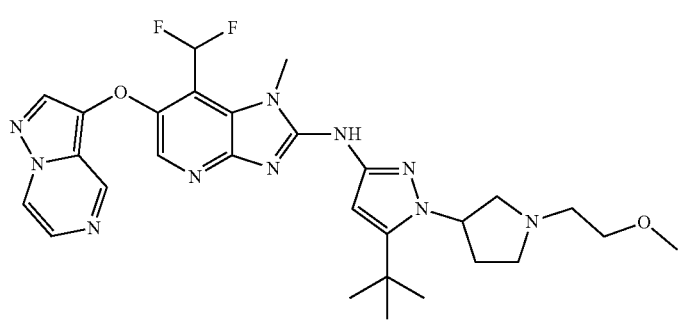 [SMILES: COCCN1CCC(n2nc(Nc3nc4ncc(Oc5cnn6ccncc56)c(C(F)F)c4n3C)cc2C(C)(C)C)C1]
I-51
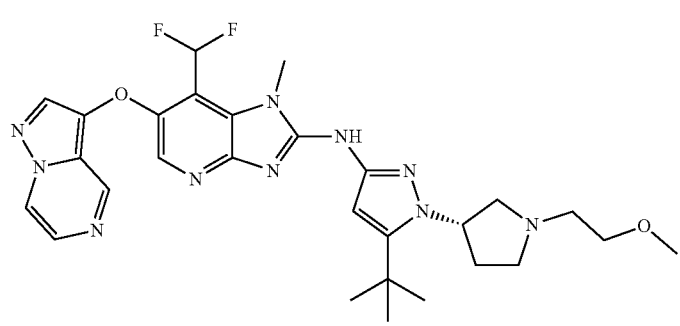 [SMILES: COCCN1CC[C@H](n2nc(Nc3nc4ncc(Oc5cnn6ccncc56)c(C(F)F)c4n3C)cc2C(C)(C)C)C1]
I-52
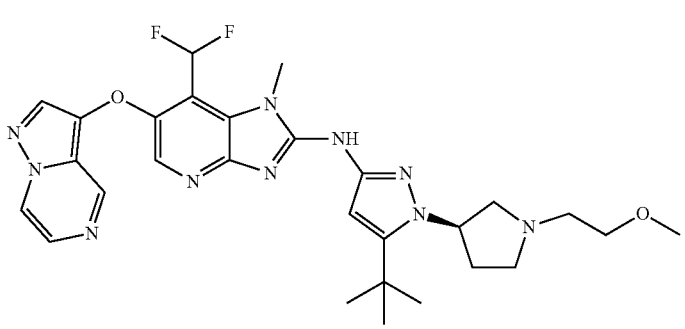 [SMILES: COCCN1CC[C@@H](n2nc(Nc3nc4ncc(Oc5cnn6ccncc56)c(C(F)F)c4n3C)cc2C(C)(C)C)C1]

-continued
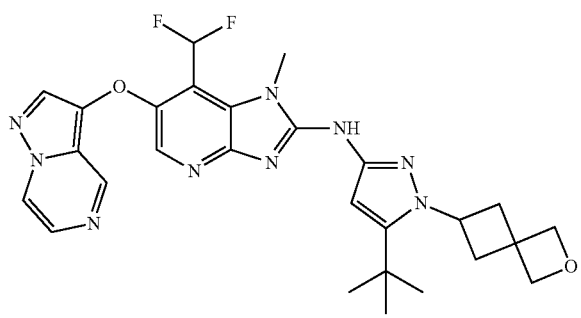 [SMILES: Cn1c(Nc2cc(C(C)(C)C)n(C3CC4(COC4)C3)n2)nc2ncc(Oc3cnn4ccncc34)c(C(F)F)c21]
I-53
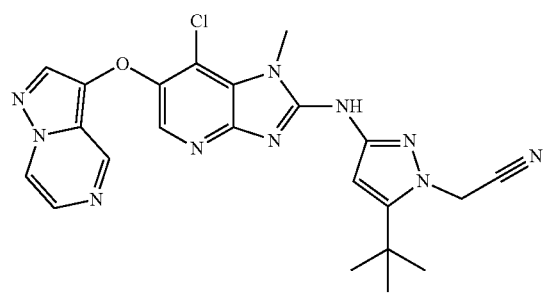 [SMILES: Cn1c(Nc2cc(C(C)(C)C)n(CC#N)n2)nc2ncc(Oc3cnn4ccncc34)c(Cl)c21]
I-54
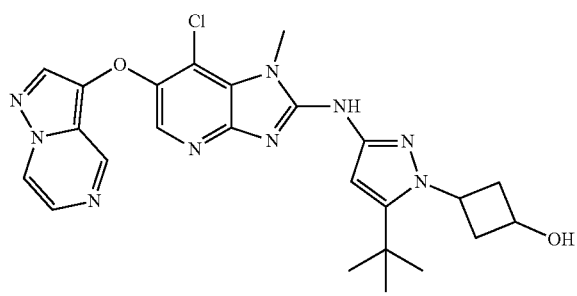 [SMILES: Cn1c(Nc2cc(C(C)(C)C)n(C3CC(O)C3)n2)nc2ncc(Oc3cnn4ccncc34)c(Cl)c21]
I-55'
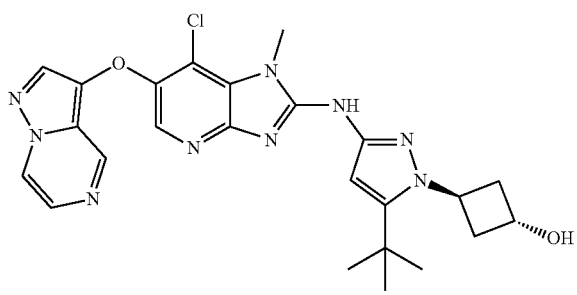 [SMILES: Cn1c(Nc2cc(C(C)(C)C)n([C@H]3C[C@H](O)C3)n2)nc2ncc(Oc3cnn4ccncc34)c(Cl)c21]
I-55
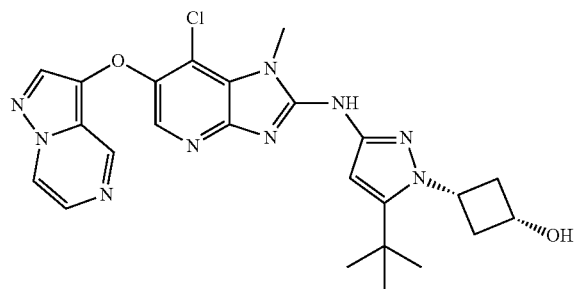 [SMILES: Cn1c(Nc2cc(C(C)(C)C)n([C@H]3C[C@@H](O)C3)n2)nc2ncc(Oc3cnn4ccncc34)c(Cl)c21]
I-55-ii -continued
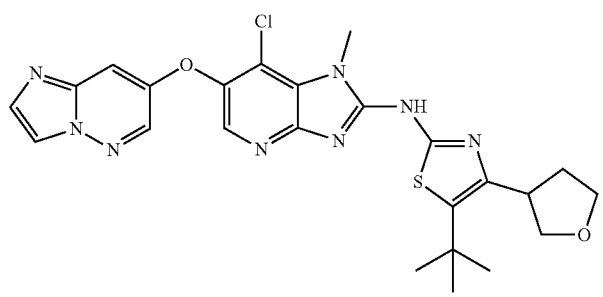 [SMILES: Cn1c(Nc2nc(C3CCOC3)c(C(C)(C)C)s2)nc2ncc(Oc3cnn4ccnc4c3)c(Cl)c21]
I-56
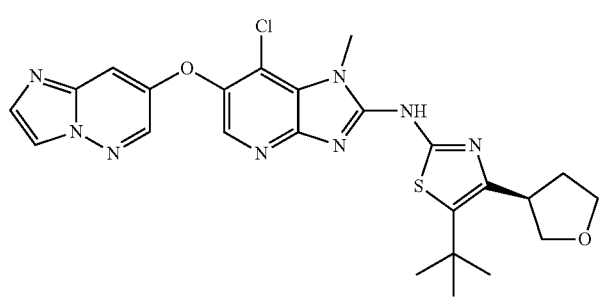 [SMILES: Cn1c(Nc2nc([C@H]3CCOC3)c(C(C)(C)C)s2)nc2ncc(Oc3cnn4ccnc4c3)c(Cl)c21]
I-56-i
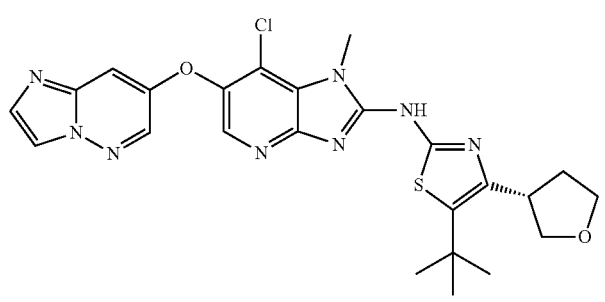 [SMILES: Cn1c(Nc2nc([C@@H]3CCOC3)c(C(C)(C)C)s2)nc2ncc(Oc3cnn4ccnc4c3)c(Cl)c21]
I-56-ii
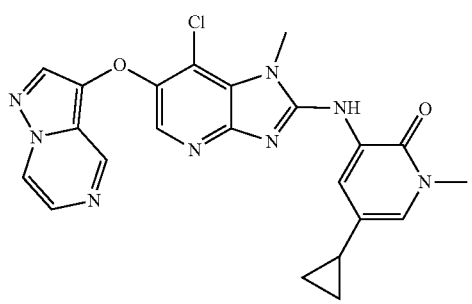 [SMILES: Cn1cc(C2CC2)cc(Nc2nc3ncc(Oc4cnn5ccncc45)c(Cl)c3n2C)c1=O]
I-57
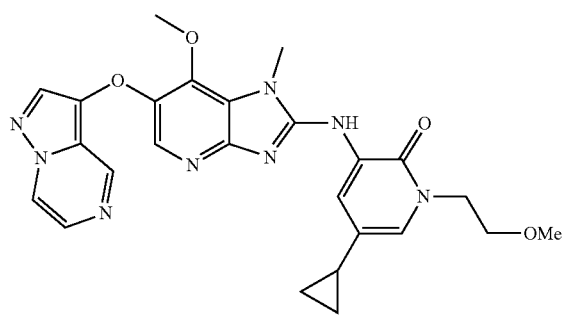
I-58

I-59
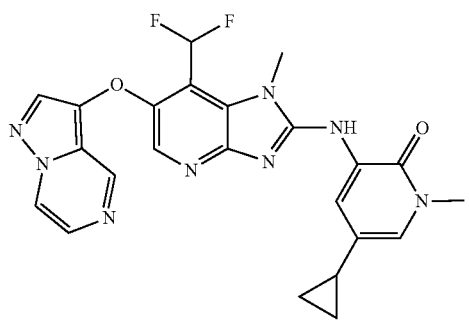
I-60
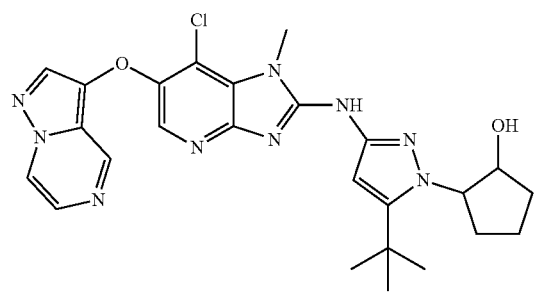 [SMILES: Cn1c(Nc2cc(C(C)(C)C)n(C3CCCC3O)n2)nc2ncc(Oc3cnn4ccncc34)c(Cl)c21]
I-60-i
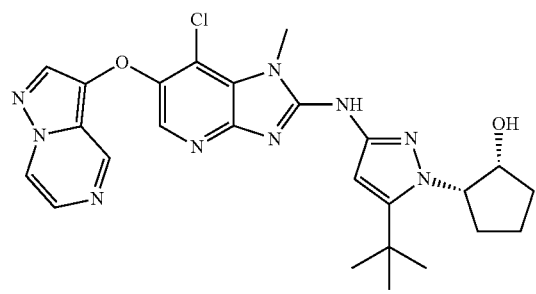 [SMILES: Cn1c(Nc2cc(C(C)(C)C)n([C@H]3CCC[C@H]3O)n2)nc2ncc(Oc3cnn4ccncc34)c(Cl)c21]
I-60-ii
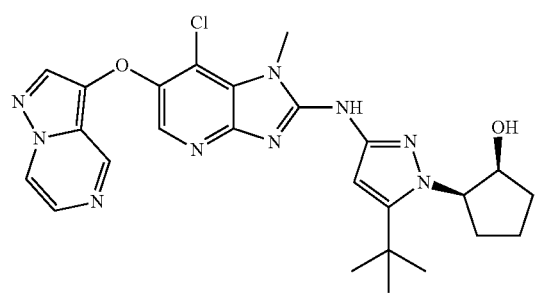
I-60-iii
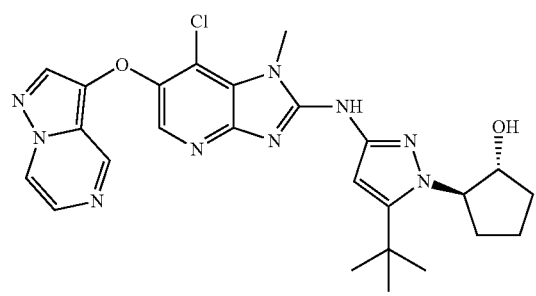 [SMILES: Cn1c(Nc2cc(C(C)(C)C)n([C@@H]3CCC[C@H]3O)n2)nc2ncc(Oc3cnn4ccncc34)c(Cl)c21]

-continued
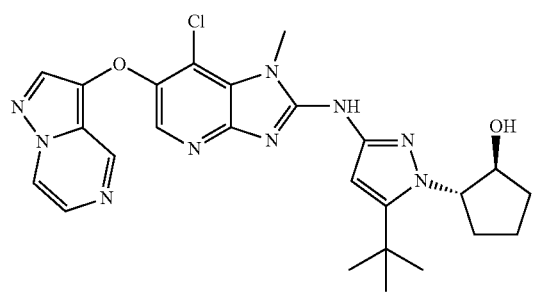
I-60-iv
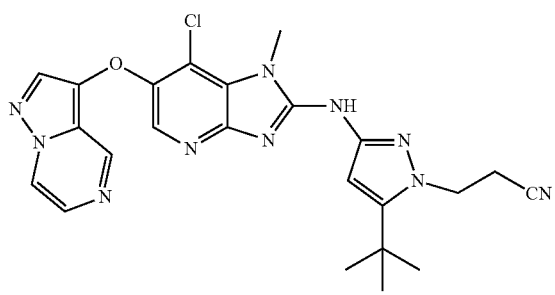
I-61
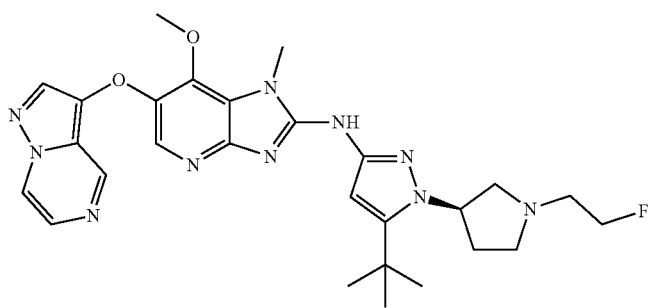 [SMILES: COc1c(Oc2cnn3ccncc23)cnc2nc(Nc3cc(C(C)(C)C)n([C@@H]4CCN(CCF)C4)n3)n(C)c12]
I-62
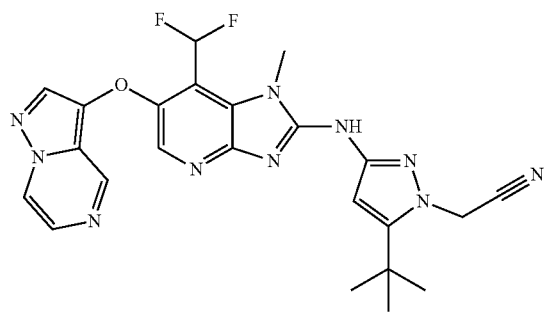 [SMILES: Cn1c(Nc2cc(C(C)(C)C)n(CC#N)n2)nc2ncc(Oc3cnn4ccncc34)c(C(F)F)c21]
I-63
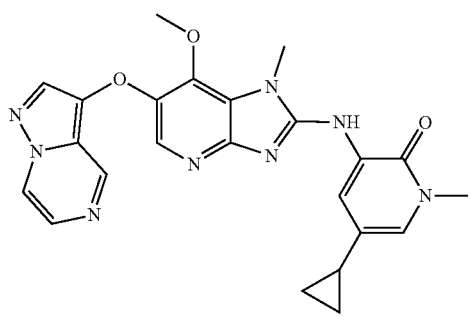 [SMILES: COc1c(Oc2cnn3ccncc23)cnc2nc(Nc3cc(C4CC4)cn(C)c3=O)n(C)c12]
I-64

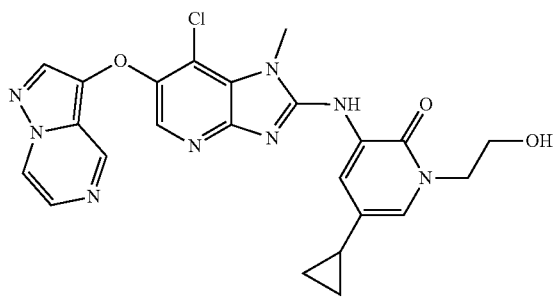 [SMILES: Cn1c(Nc2cc(C3CC3)cn(CCO)c2=O)nc2ncc(Oc3cnn4ccncc34)c(Cl)c21]
I-65
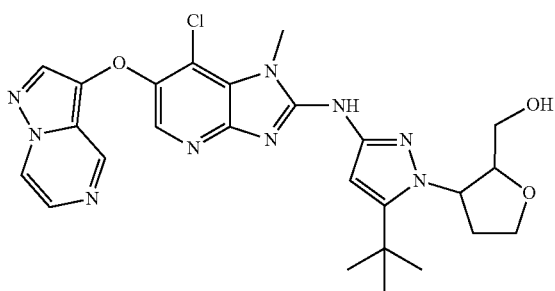 [SMILES: Cn1c(Nc2cc(C(C)(C)C)n(C3CCOC3CO)n2)nc2ncc(Oc3cnn4ccncc34)c(Cl)c21]
I-66'
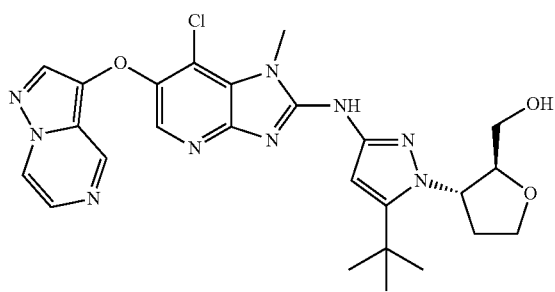 [SMILES: Cn1c(Nc2cc(C(C)(C)C)n([C@H]3CCO[C@@H]3CO)n2)nc2ncc(Oc3cnn4ccncc34)c(Cl)c21]
I-66
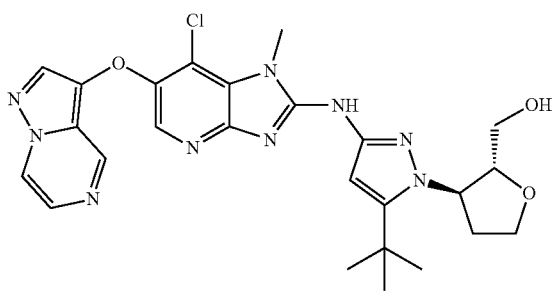 [SMILES: Cn1c(Nc2cc(C(C)(C)C)n([C@@H]3CCO[C@H]3CO)n2)nc2ncc(Oc3cnn4ccncc34)c(Cl)c21]
I-66-ii
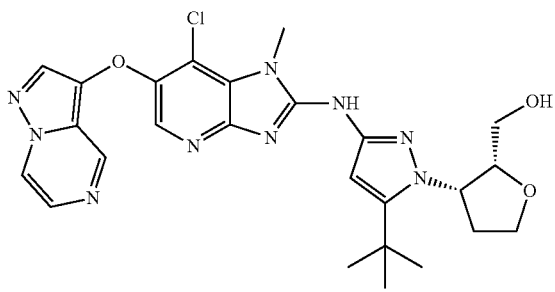 [SMILES: Cn1c(Nc2cc(C(C)(C)C)n([C@H]3CCO[C@H]3CO)n2)nc2ncc(Oc3cnn4ccncc34)c(Cl)c21]
I-66-iii

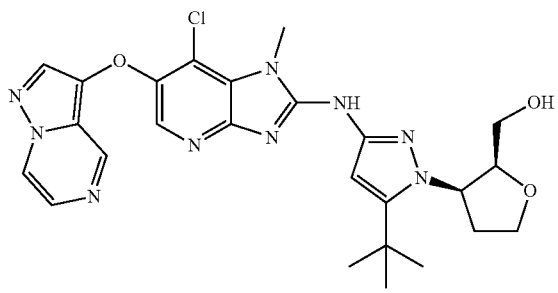 [SMILES: Cn1c(Nc2cc(C(C)(C)C)n([C@@H]3CCO[C@@H]3CO)n2)nc2ncc(Oc3cnn4ccncc34)c(Cl)c21]
I-66-iv
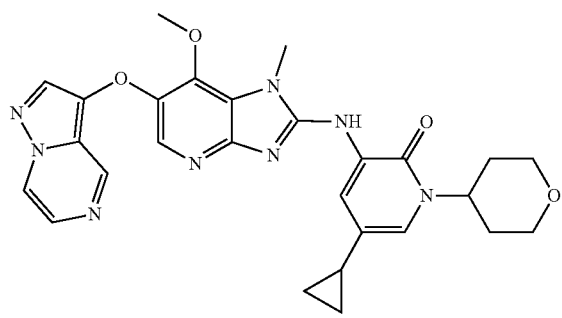 [SMILES: COc1c(Oc2cnn3ccncc23)cnc2nc(Nc3cc(C4CC4)cn(C4CCOCC4)c3=O)n(C)c12]
I-67
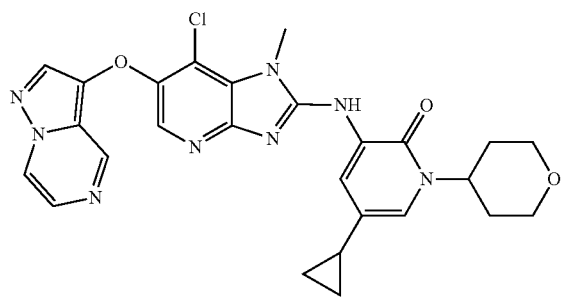 [SMILES: Cn1c(Nc2cc(C3CC3)cn(C3CCOCC3)c2=O)nc2ncc(Oc3cnn4ccncc34)c(Cl)c21]
I-68
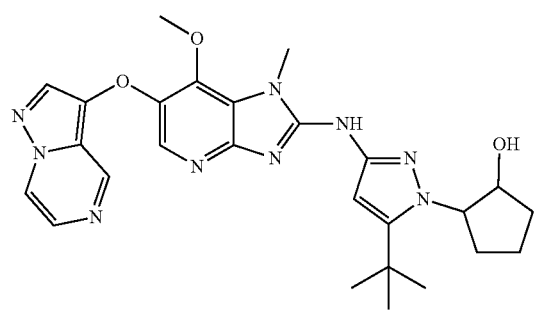 [SMILES: COc1c(Oc2cnn3ccncc23)cnc2nc(Nc3cc(C(C)(C)C)n(C4CCCC4O)n3)n(C)c12]
I-69
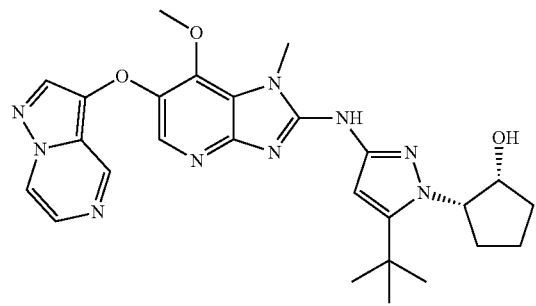 [SMILES: COc1c(Oc2cnn3ccncc23)cnc2nc(Nc3cc(C(C)(C)C)n([C@H]4CCC[C@H]4O)n3)n(C)c12]
I-69-i

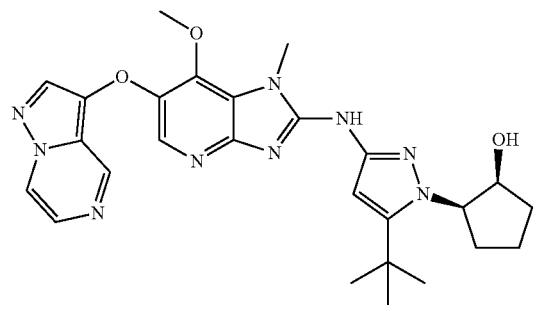
I-69-ii
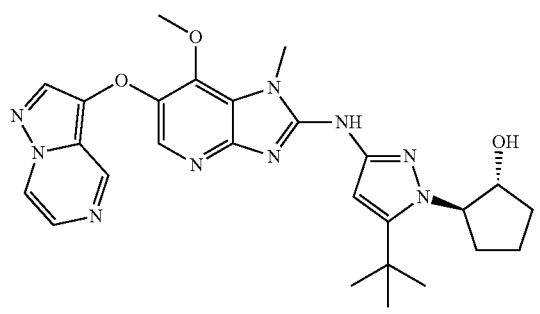 [SMILES: COc1c(Oc2cnn3ccncc23)cnc2nc(Nc3cc(C(C)(C)C)n([C@@H]4CCC[C@H]4O)n3)n(C)c12]
I-69-iii
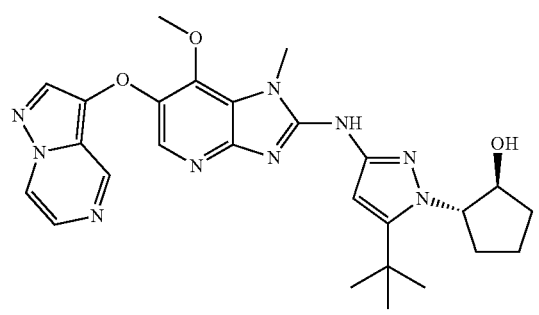 [SMILES: COc1c(Oc2cnn3ccncc23)cnc2nc(Nc3cc(C(C)(C)C)n([C@H]4CCC[C@@H]4O)n3)n(C)c12]
I-69-iv
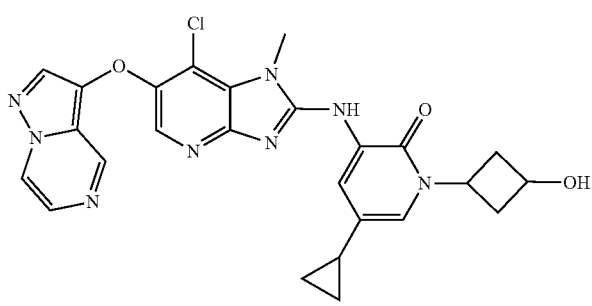
I-70'
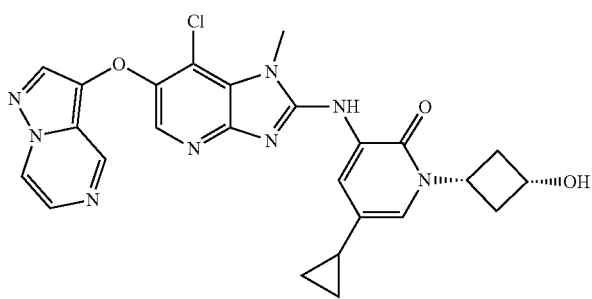 [SMILES: Cn1c(Nc2cc(C3CC3)cn([C@H]3C[C@@H](O)C3)c2=O)nc2ncc(Oc3cnn4ccncc34)c(Cl)c21]
I-70

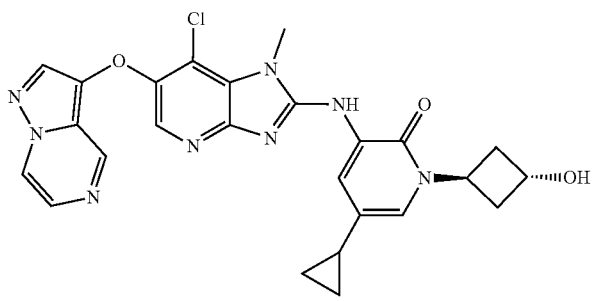 [SMILES: Cn1c(Nc2cc(C3CC3)cn([C@H]3C[C@H](O)C3)c2=O)nc2ncc(Oc3cnn4ccncc34)c(Cl)c21]
I-70-ii
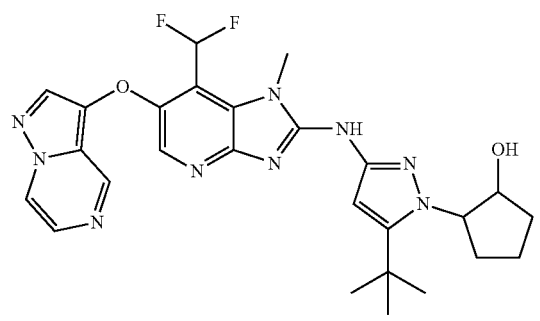 [SMILES: Cn1c(Nc2cc(C(C)(C)C)n(C3CCCC3O)n2)nc2ncc(Oc3cnn4ccncc34)c(C(F)F)c21]
I-71
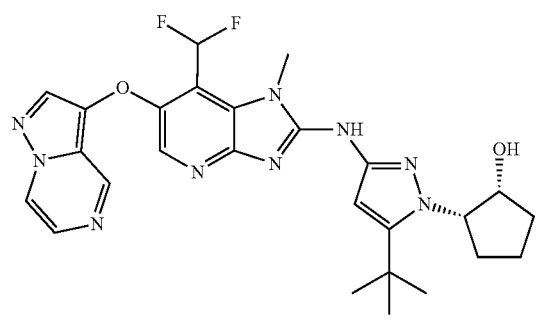 [SMILES: Cn1c(Nc2cc(C(C)(C)C)n([C@H]3CCC[C@H]3O)n2)nc2ncc(Oc3cnn4ccncc34)c(C(F)F)c21]
I-71-i
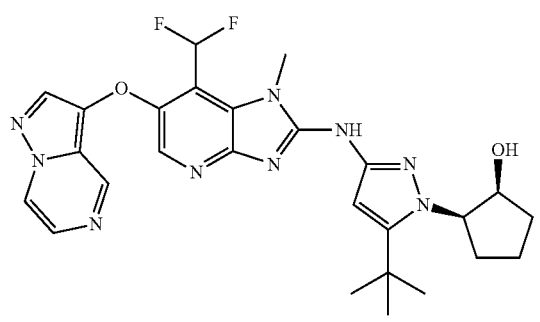 [SMILES: Cn1c(Nc2cc(C(C)(C)C)n([C@@H]3CCC[C@@H]3O)n2)nc2ncc(Oc3cnn4ccncc34)c(C(F)F)c21]
I-71-ii
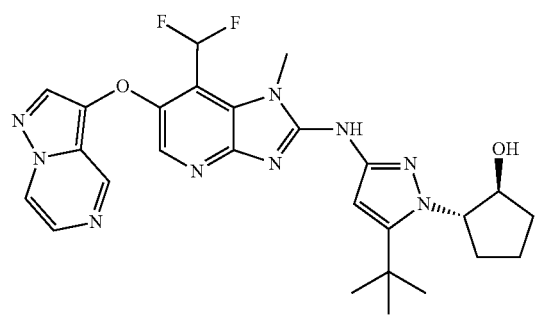 [SMILES: Cn1c(Nc2cc(C(C)(C)C)n([C@H]3CCC[C@@H]3O)n2)nc2ncc(Oc3cnn4ccncc34)c(C(F)F)c21]
I-71-iii -continued
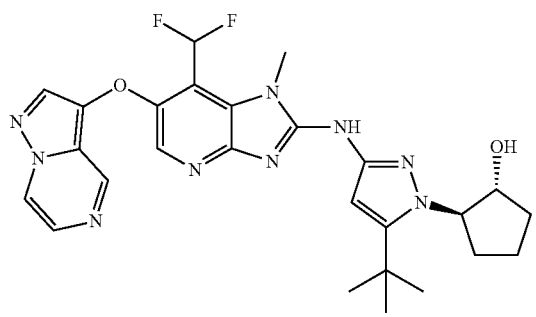 [SMILES: Cn1c(Nc2cc(C(C)(C)C)n([C@@H]3CCC[C@H]3O)n2)nc2ncc(Oc3cnn4ccncc34)c(C(F)F)c21]
I-71-iv
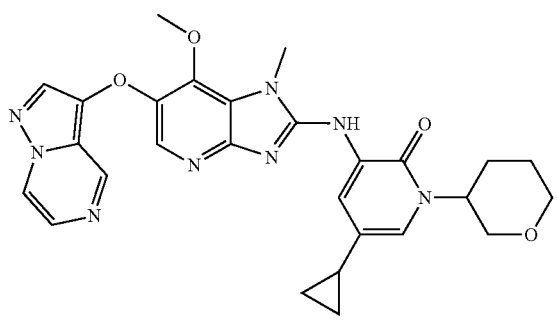 [SMILES: COc1c(Oc2cnn3ccncc23)cnc2nc(Nc3cc(C4CC4)cn([C@@H]4CCCOC4)c3=O)n(C)c12]
I-72
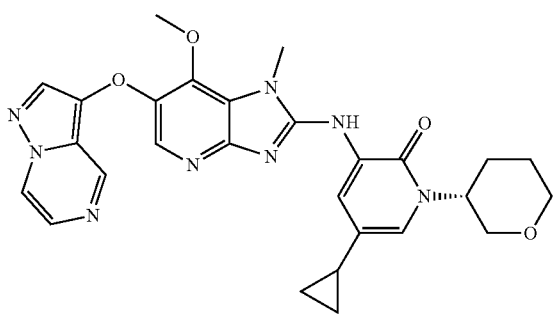
I-72-i
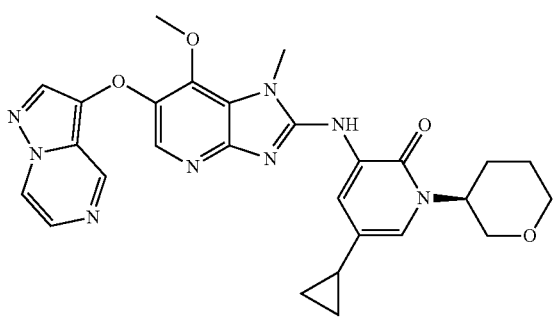 [SMILES: COc1c(Oc2cnn3ccncc23)cnc2nc(Nc3cc(C4CC4)cn([C@H]4CCCOC4)c3=O)n(C)c12]
I-72-ii
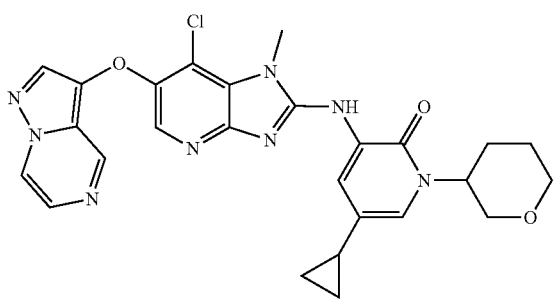
I-73

I-73-i
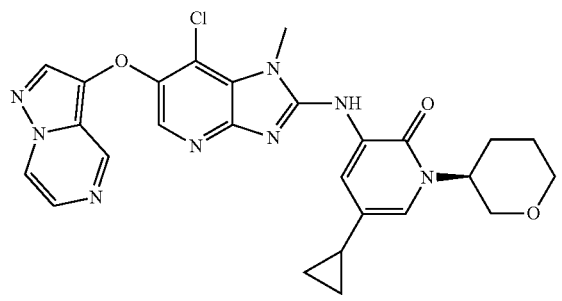 [SMILES: Cn1c(Nc2cc(C3CC3)cn([C@H]3CCCOC3)c2=O)nc2ncc(Oc3cnn4ccncc34)c(Cl)c21]
I-73-ii
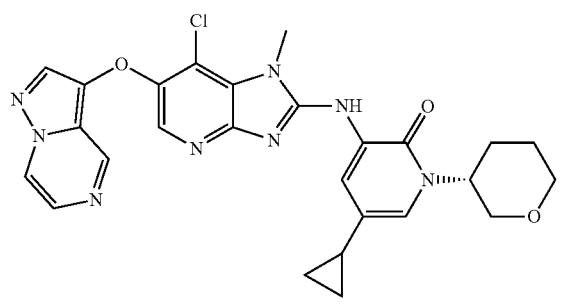 [SMILES: Cn1c(Nc2cc(C3CC3)cn([C@@H]3CCCOC3)c2=O)nc2ncc(Oc3cnn4ccncc34)c(Cl)c21]
I-74'
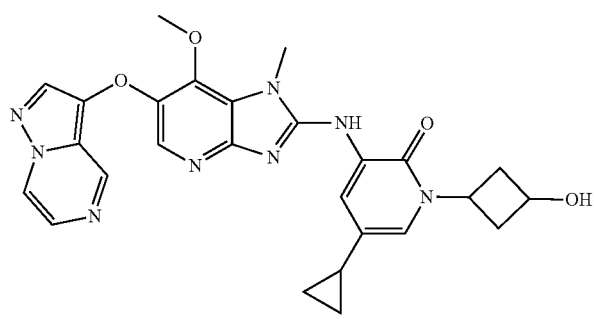 [SMILES: COc1c(Oc2cnn3ccncc23)cnc2nc(Nc3cc(C4CC4)cn(C4CC(O)C4)c3=O)n(C)c12]
I-74
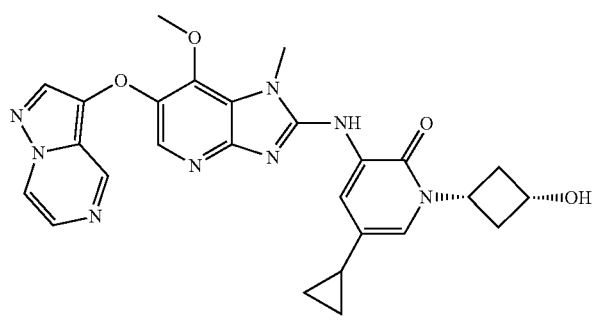 [SMILES: COc1c(Oc2cnn3ccncc23)cnc2nc(Nc3cc(C4CC4)cn([C@H]4C[C@@H](O)C4)c3=O)n(C)c12]
I-75
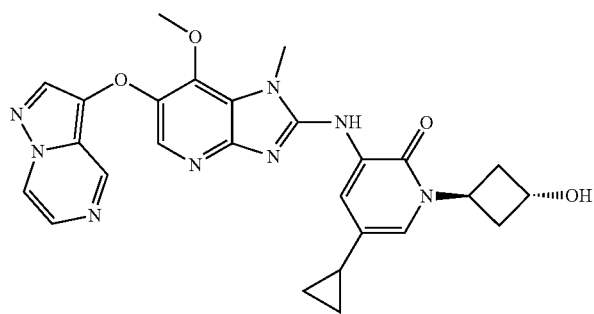 [SMILES: COc1c(Oc2cnn3ccncc23)cnc2nc(Nc3cc(C4CC4)cn([C@H]4C[C@H](O)C4)c3=O)n(C)c12]

I-76
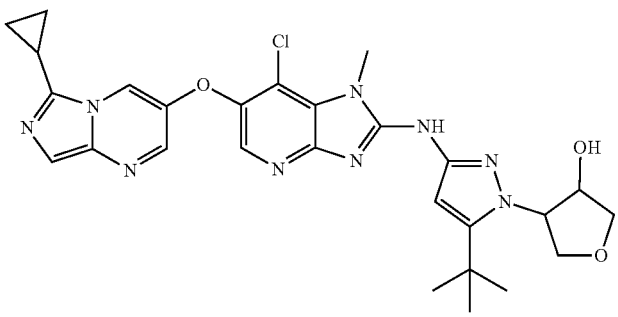 [SMILES: Cn1c(Nc2cc(C(C)(C)C)n(C3COCC3O)n2)nc2ncc(Oc3cnc4cnc(C5CC5)n4c3)c(Cl)c21]
I-76-i
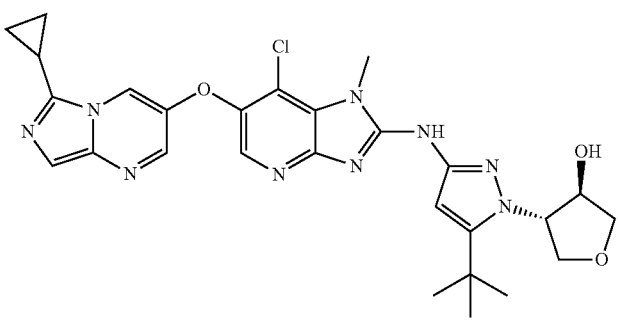 [SMILES: Cn1c(Nc2cc(C(C)(C)C)n([C@H]3COC[C@@H]3O)n2)nc2ncc(Oc3cnc4cnc(C5CC5)n4c3)c(Cl)c21]
I-76-ii
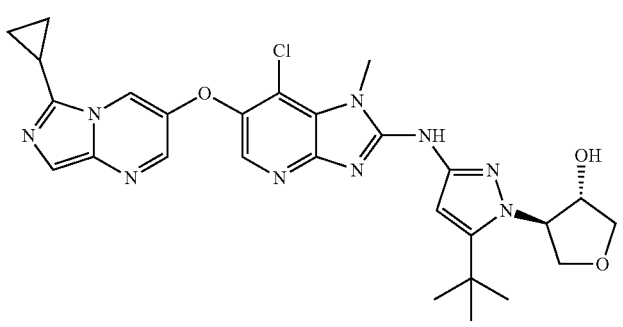 [SMILES: Cn1c(Nc2cc(C(C)(C)C)n([C@@H]3COC[C@H]3O)n2)nc2ncc(Oc3cnc4cnc(C5CC5)n4c3)c(Cl)c21]
I-76-iii
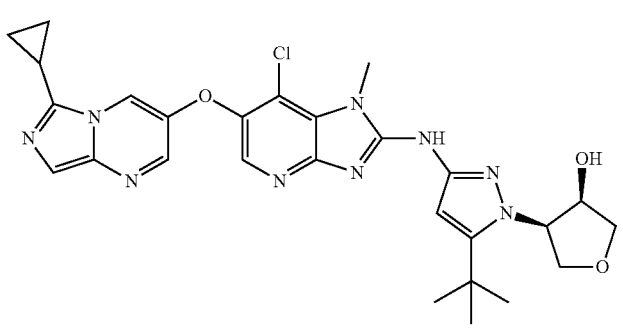 [SMILES: Cn1c(Nc2cc(C(C)(C)C)n([C@@H]3COC[C@@H]3O)n2)nc2ncc(Oc3cnc4cnc(C5CC5)n4c3)c(Cl)c21]
I-76-iv
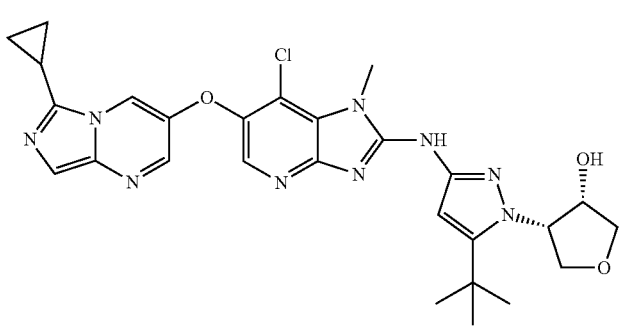 [SMILES: Cn1c(Nc2cc(C(C)(C)C)n([C@H]3COC[C@H]3O)n2)nc2ncc(Oc3cnc4cnc(C5CC5)n4c3)c(Cl)c21]

-continued
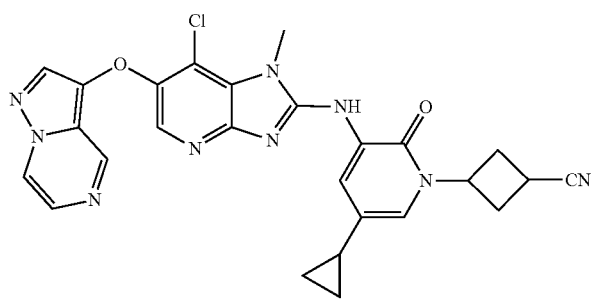
I-77'
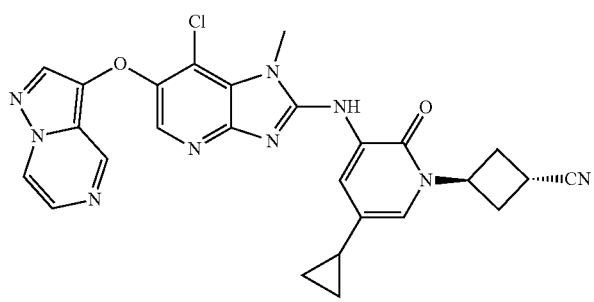
I-77
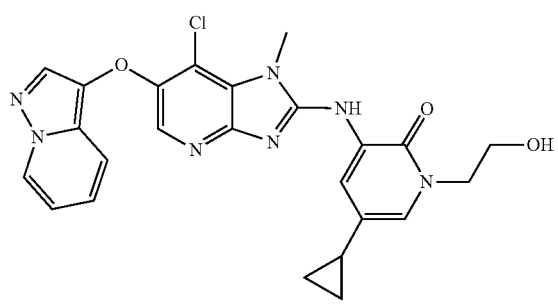 [SMILES: Cn1c(Nc2cc(C3CC3)cn(CCO)c2=O)nc2ncc(Oc3cnn4ccccc34)c(Cl)c21]
I-78
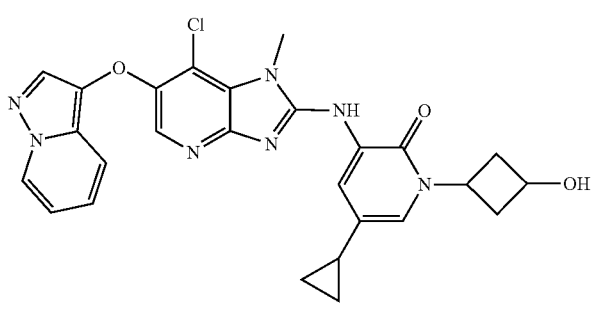 [SMILES: Cn1c(Nc2cc(C3CC3)cn(C3CC(O)C3)c2=O)nc2ncc(Oc3cnn4ccccc34)c(Cl)c21]
I-79'
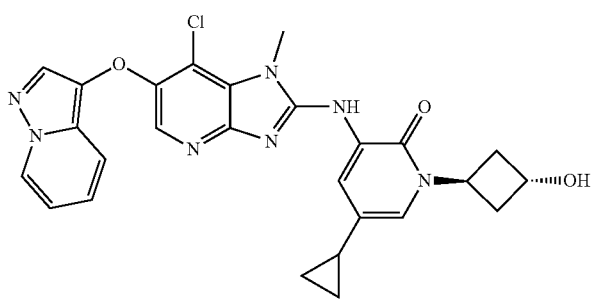
I-79

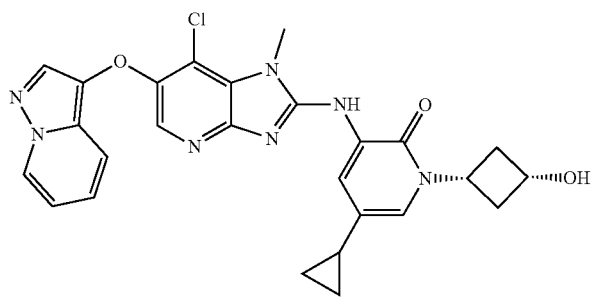 [SMILES: Cn1c(Nc2cc(C3CC3)cn([C@H]3C[C@@H](O)C3)c2=O)nc2ncc(Oc3cnn4ccccc34)c(Cl)c21]
I-79-ii
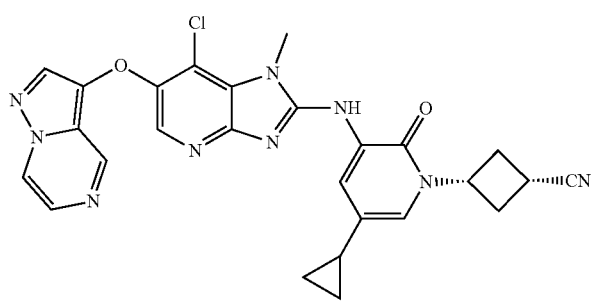 [SMILES: Cn1c(Nc2cc(C3CC3)cn([C@H]3C[C@@H](C#N)C3)c2=O)nc2ncc(Oc3cnn4ccncc34)c(Cl)c21]
I-80
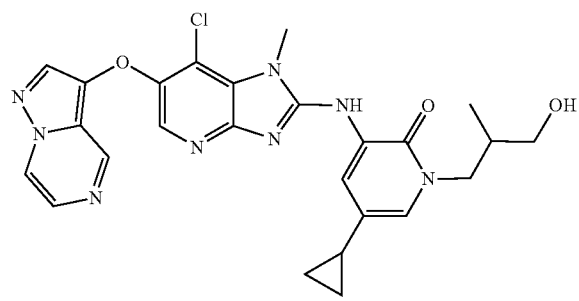 [SMILES: CC(CO)Cn1cc(C2CC2)cc(Nc2nc3ncc(Oc4cnn5ccncc45)c(Cl)c3n2C)c1=O]
I-81
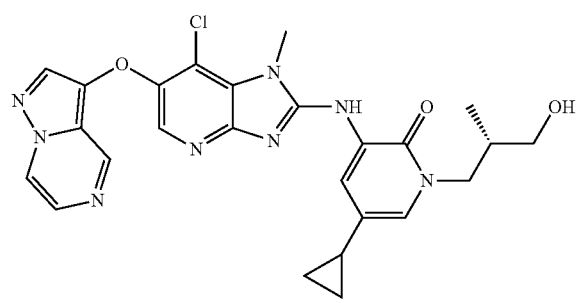 [SMILES: C[C@H](CO)Cn1cc(C2CC2)cc(Nc2nc3ncc(Oc4cnn5ccncc45)c(Cl)c3n2C)c1=O]
I-81-i
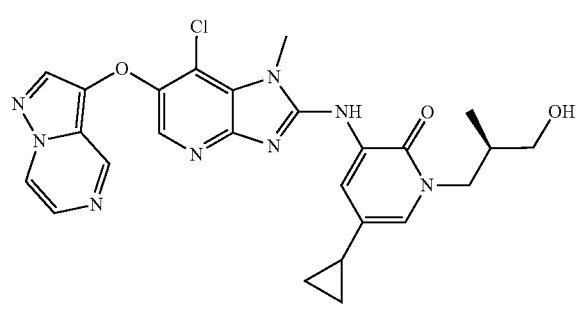 [SMILES: C[C@@H](CO)Cn1cc(C2CC2)cc(Nc2nc3ncc(Oc4cnn5ccncc45)c(Cl)c3n2C)c1=O]
I-81-ii

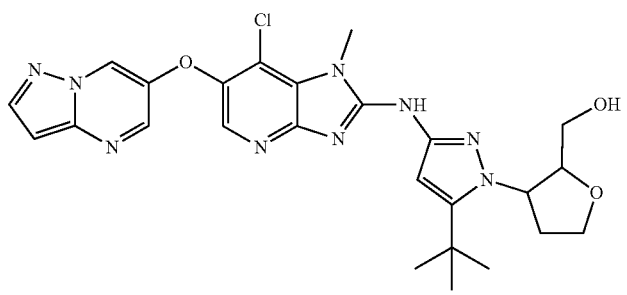 [SMILES: Cn1c(Nc2cc(C(C)(C)C)n(C3CCOC3CO)n2)nc2ncc(Oc3cnc4ccnn4c3)c(Cl)c21]
I-82'
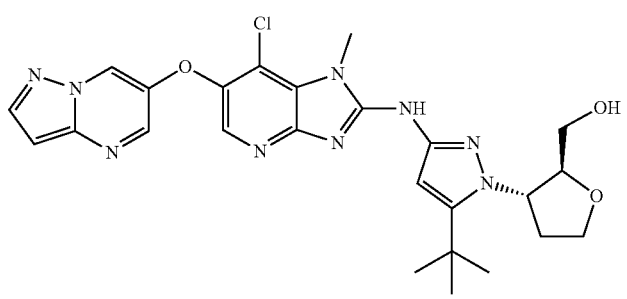 [SMILES: Cn1c(Nc2cc(C(C)(C)C)n([C@H]3CCO[C@@H]3CO)n2)nc2ncc(Oc3cnc4ccnn4c3)c(Cl)c21]
I-82
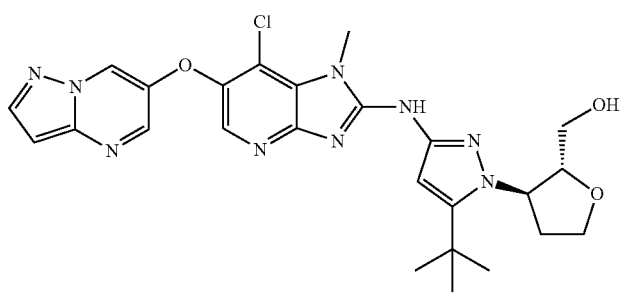 [SMILES: Cn1c(Nc2cc(C(C)(C)C)n([C@@H]3CCO[C@H]3CO)n2)nc2ncc(Oc3cnc4ccnn4c3)c(Cl)c21]
I-82-ii
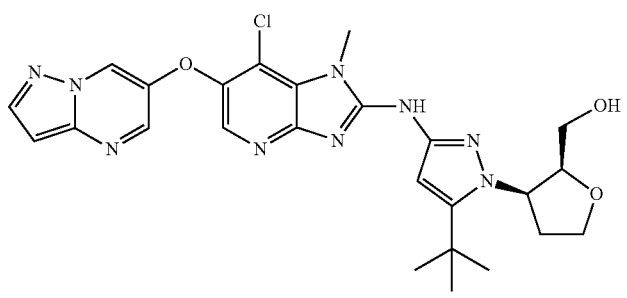
I-82-iii
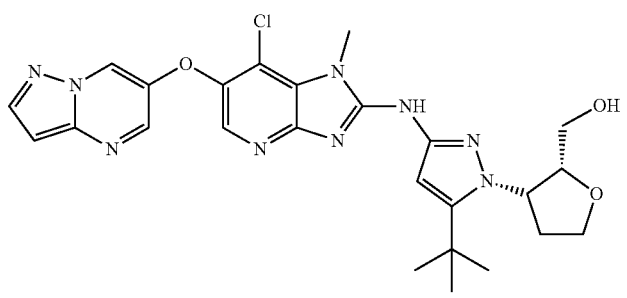
I-82-iv I-83'
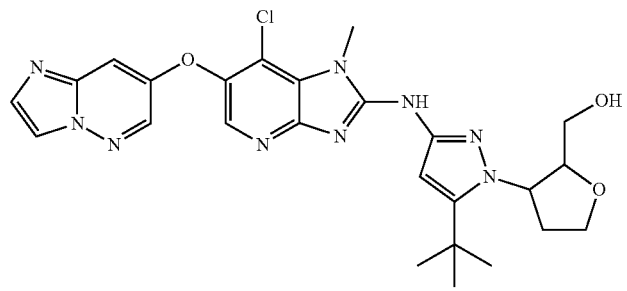 [SMILES: Cn1c(Nc2cc(C(C)(C)C)n(C3CCOC3CO)n2)nc2ncc(Oc3cnn4ccnc4c3)c(Cl)c21]
I-83
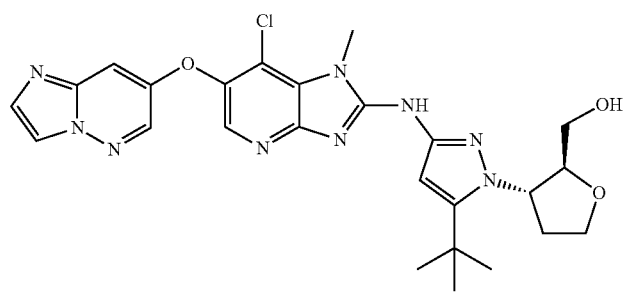 [SMILES: Cn1c(Nc2cc(C(C)(C)C)n([C@H]3CCO[C@@H]3CO)n2)nc2ncc(Oc3cnn4ccnc4c3)c(Cl)c21]
I-83-ii
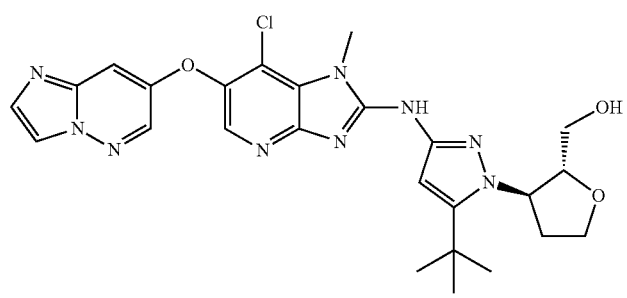 [SMILES: Cn1c(Nc2cc(C(C)(C)C)n([C@@H]3CCO[C@H]3CO)n2)nc2ncc(Oc3cnn4ccnc4c3)c(Cl)c21]
I-83-iii
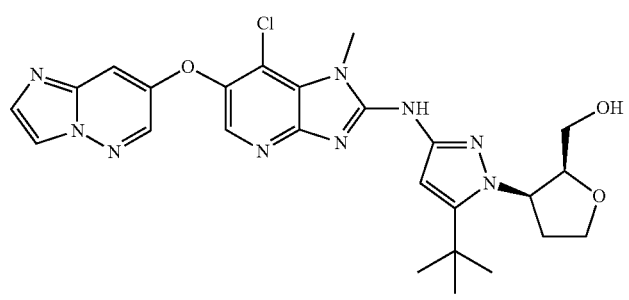
I-83-iv
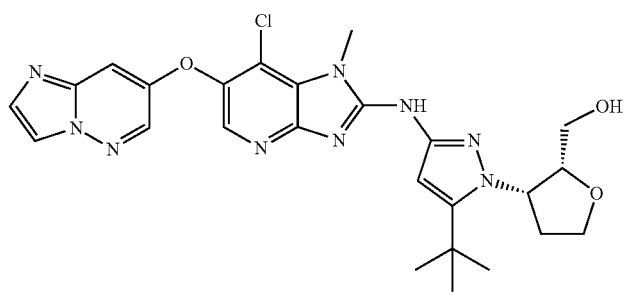 [SMILES: Cn1c(Nc2cc(C(C)(C)C)n([C@H]3CCO[C@H]3CO)n2)nc2ncc(Oc3cnn4ccnc4c3)c(Cl)c21]

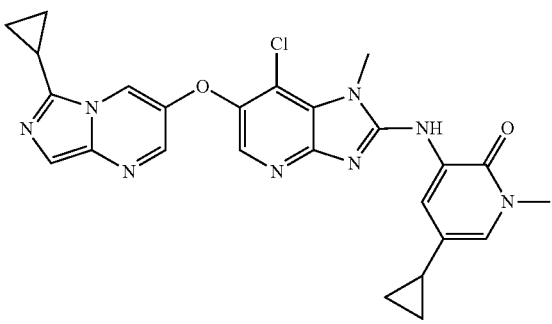 [SMILES: Cn1cc(C2CC2)cc(Nc2nc3ncc(Oc4cnc5cnc(C6CC6)n5c4)c(Cl)c3n2C)c1=O]
I-84
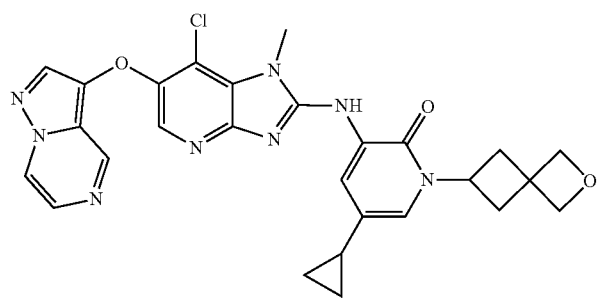 [SMILES: Cn1c(Nc2cc(C3CC3)cn(C3CC4(COC4)C3)c2=O)nc2ncc(Oc3cnn4ccncc34)c(Cl)c21]
I-85
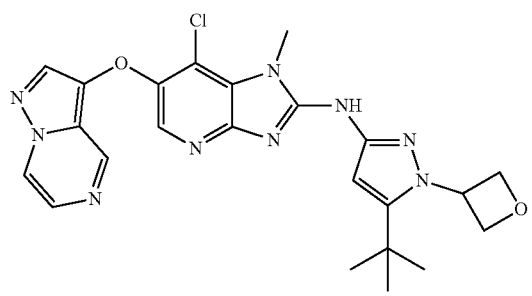 [SMILES: Cn1c(Nc2cc(C(C)(C)C)n(C3COC3)n2)nc2ncc(Oc3cnn4ccncc34)c(Cl)c21]
I-86
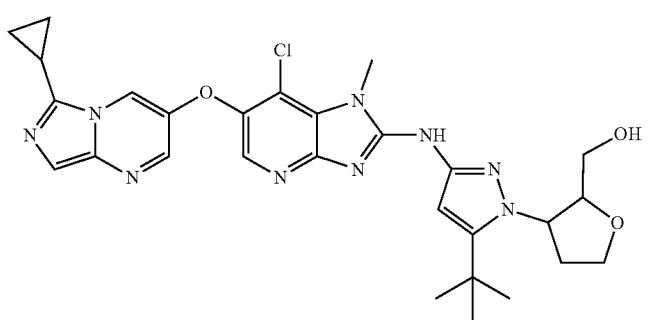 [SMILES: Cn1c(Nc2cc(C(C)(C)C)n(C3CCOC3CO)n2)nc2ncc(Oc3cnc4cnc(C5CC5)n4c3)c(Cl)c21]
I-87'
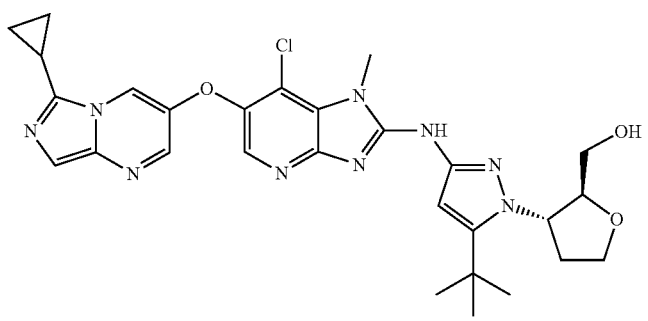 [SMILES: Cn1c(Nc2cc(C(C)(C)C)n([C@H]3CCO[C@@H]3CO)n2)nc2ncc(Oc3cnc4cnc(C5CC5)n4c3)c(Cl)c21]
I-87

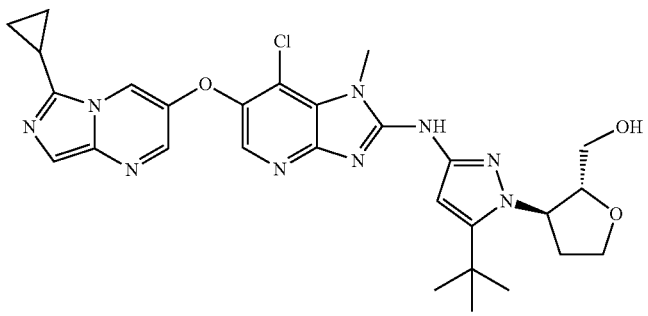 [SMILES: Cn1c(Nc2cc(C(C)(C)C)n([C@@H]3CCO[C@H]3CO)n2)nc2ncc(Oc3cnc4cnc(C5CC5)n4c3)c(Cl)c21]
I-87-ii
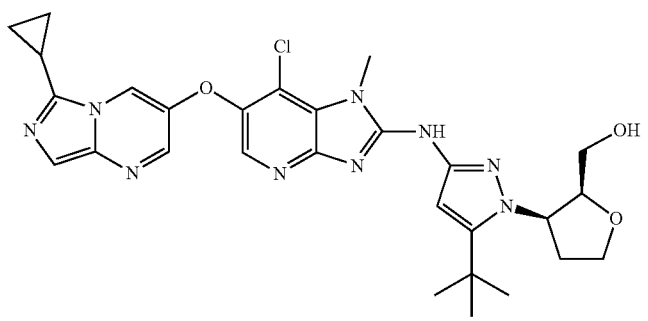 [SMILES: Cn1c(Nc2cc(C(C)(C)C)n([C@@H]3CCO[C@@H]3CO)n2)nc2ncc(Oc3cnc4cnc(C5CC5)n4c3)c(Cl)c21]
I-87-iii
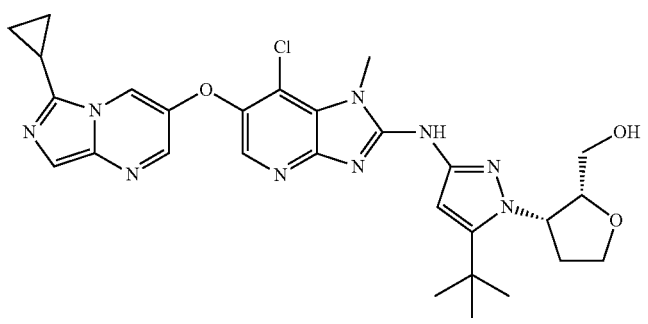
I-87-iv
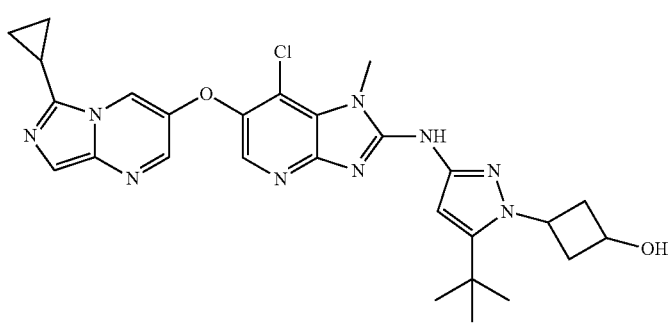 [SMILES: Cn1c(Nc2cc(C(C)(C)C)n(C3CC(O)C3)n2)nc2ncc(Oc3cnc4cnc(C5CC5)n4c3)c(Cl)c21]
I-88'
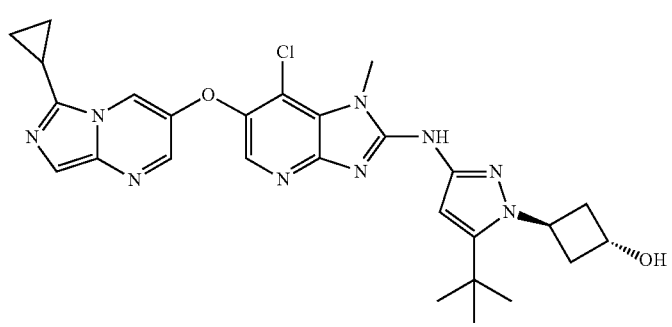 [SMILES: Cn1c(Nc2cc(C(C)(C)C)n([C@H]3C[C@H](O)C3)n2)nc2ncc(Oc3cnc4cnc(C5CC5)n4c3)c(Cl)c21]
I-88

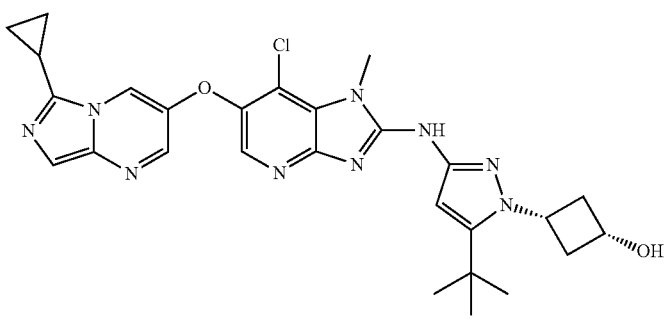 [SMILES: Cn1c(Nc2cc(C(C)(C)C)n([C@H]3C[C@@H](O)C3)n2)nc2ncc(Oc3cnc4cnc(C5CC5)n4c3)c(Cl)c21]
I-88-ii
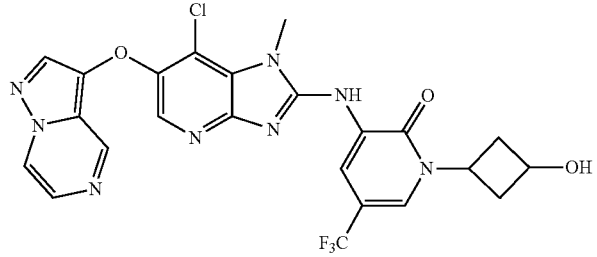 [SMILES: Cn1c(Nc2cc(C(F)(F)F)cn(C3CC(O)C3)c2=O)nc2ncc(Oc3cnn4ccncc34)c(Cl)c21]
I-89'
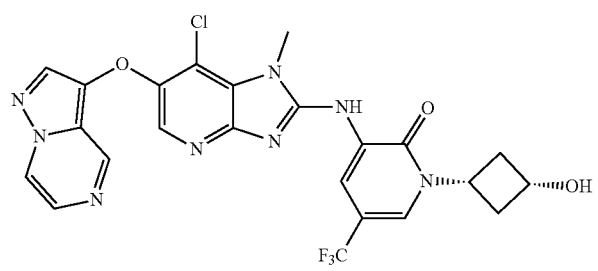 [SMILES: Cn1c(Nc2cc(C(F)(F)F)cn([C@H]3C[C@@H](O)C3)c2=O)nc2ncc(Oc3cnn4ccncc34)c(Cl)c21]
I-89
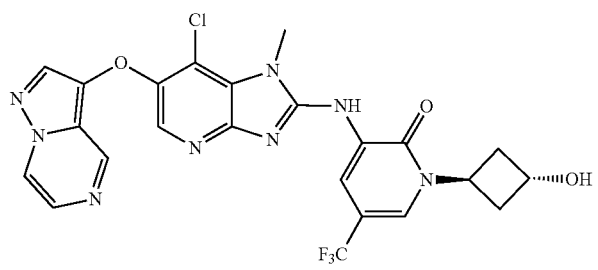 [SMILES: Cn1c(Nc2cc(C(F)(F)F)cn([C@H]3C[C@H](O)C3)c2=O)nc2ncc(Oc3cnn4ccncc34)c(Cl)c21]
I-89-ii
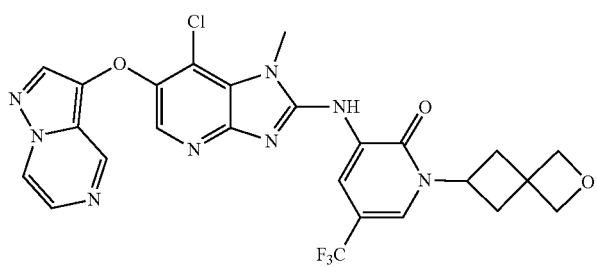 [SMILES: Cn1c(Nc2cc(C(F)(F)F)cn(C3CC4(COC4)C3)c2=O)nc2ncc(Oc3cnn4ccncc34)c(Cl)c21]
I-90

-continued
I-91
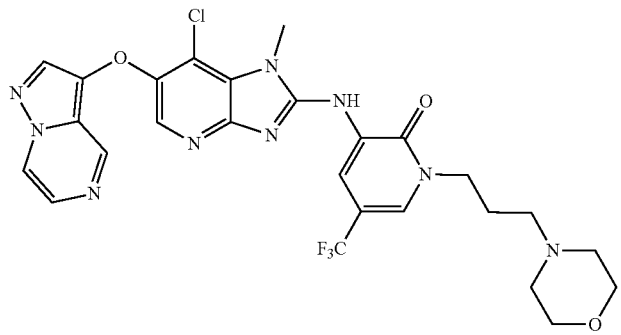 [SMILES: Cn1c(Nc2cc(C(F)(F)F)cn(CCCN3CCOCC3)c2=O)nc2ncc(Oc3cnn4ccncc34)c(Cl)c21]
I-92
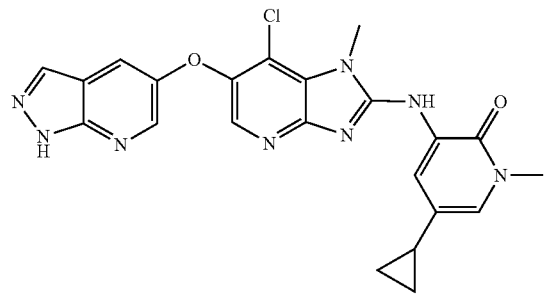 [SMILES: Cn1cc(C2CC2)cc(Nc2nc3ncc(Oc4cnc5[nH]ncc5c4)c(Cl)c3n2C)c1=O]
I-93
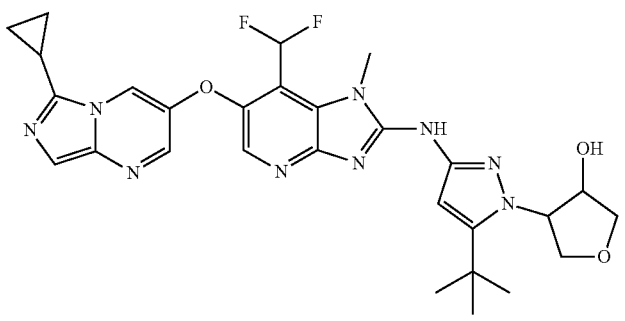 [SMILES: Cn1c(Nc2cc(C(C)(C)C)n(C3COCC3O)n2)nc2ncc(Oc3cnc4cnc(C5CC5)n4c3)c(C(F)F)c21]
I-93-i
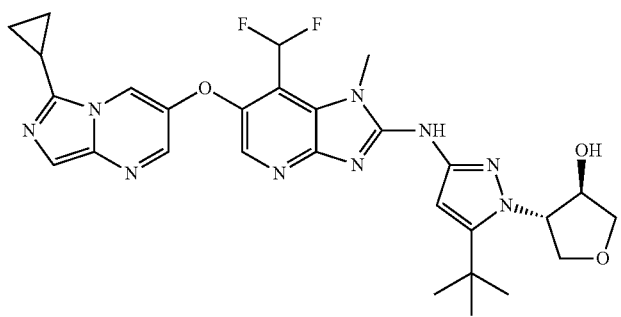 [SMILES: Cn1c(Nc2cc(C(C)(C)C)n([C@H]3COC[C@@H]3O)n2)nc2ncc(Oc3cnc4cnc(C5CC5)n4c3)c(C(F)F)c21]
I-93-ii
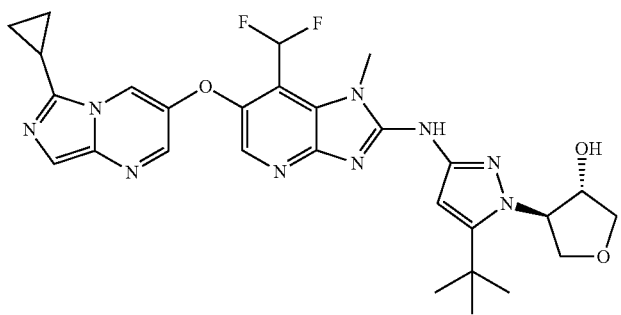 [SMILES: Cn1c(Nc2cc(C(C)(C)C)n([C@@H]3COC[C@H]3O)n2)nc2ncc(Oc3cnc4cnc(C5CC5)n4c3)c(C(F)F)c21]

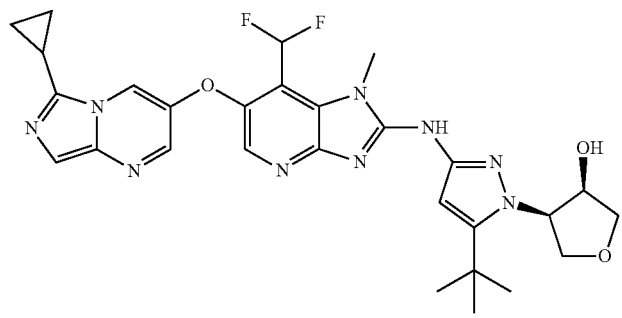 [SMILES: Cn1c(Nc2cc(C(C)(C)C)n([C@@H]3COC[C@@H]3O)n2)nc2ncc(Oc3cnc4cnc(C5CC5)n4c3)c(C(F)F)c21]
I-93-iii
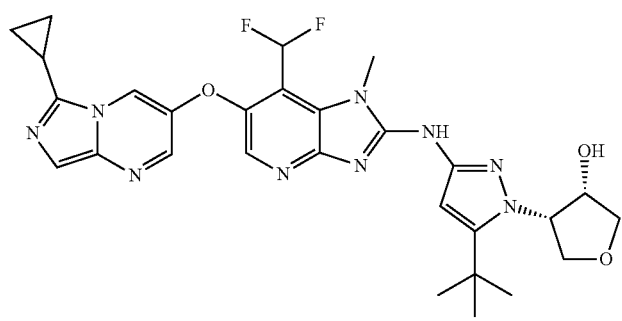 [SMILES: Cn1c(Nc2cc(C(C)(C)C)n([C@H]3COC[C@H]3O)n2)nc2ncc(Oc3cnc4cnc(C5CC5)n4c3)c(C(F)F)c21]
I-93-iv
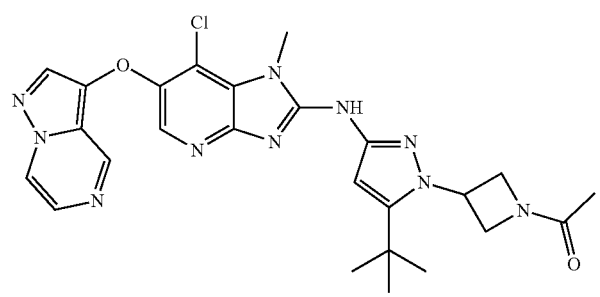 [SMILES: CC(=O)N1CC(n2nc(Nc3nc4ncc(Oc5cnn6ccncc56)c(Cl)c4n3C)cc2C(C)(C)C)C1]
I-94
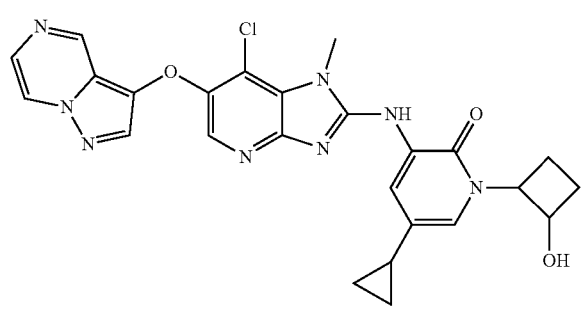 [SMILES: Cn1c(Nc2cc(C3CC3)cn(C3CCC3O)c2=O)nc2ncc(Oc3cnn4ccncc34)c(Cl)c21]
I-95
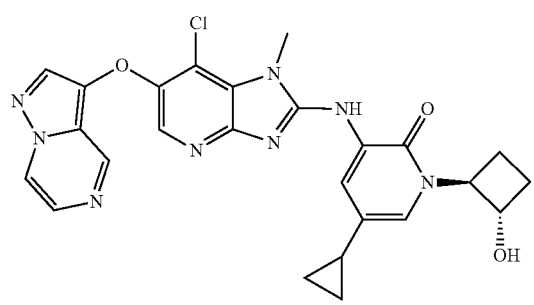 [SMILES: Cn1c(Nc2cc(C3CC3)cn([C@H]3CC[C@@H]3O)c2=O)nc2ncc(Oc3cnn4ccncc34)c(Cl)c21]
I-95-i

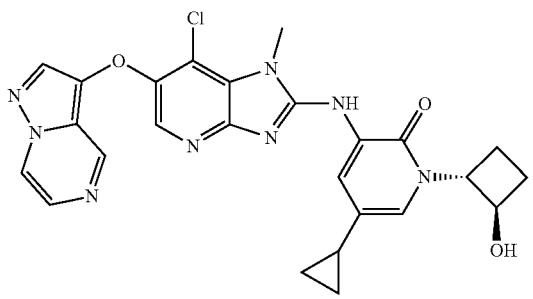 [SMILES: Cn1c(Nc2cc(C3CC3)cn([C@@H]3CC[C@H]3O)c2=O)nc2ncc(Oc3cnn4ccncc34)c(Cl)c21]
I-95-ii
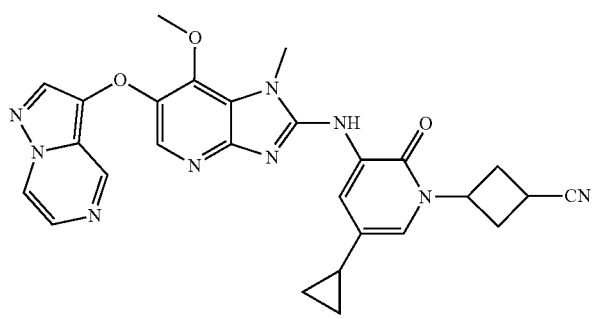 [SMILES: COc1c(Oc2cnn3ccncc23)cnc2nc(Nc3cc(C4CC4)cn(C4CC(C#N)C4)c3=O)n(C)c12]
I-96'
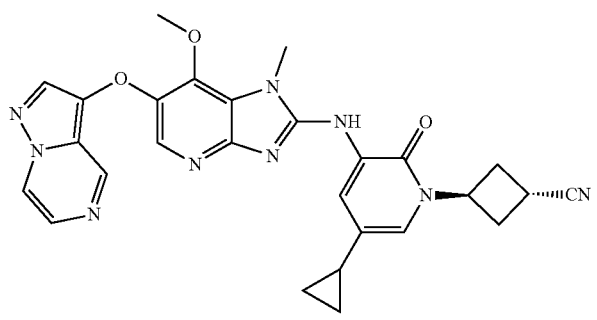 [SMILES: COc1c(Oc2cnn3ccncc23)cnc2nc(Nc3cc(C4CC4)cn([C@H]4C[C@H](C#N)C4)c3=O)n(C)c12]
I-96
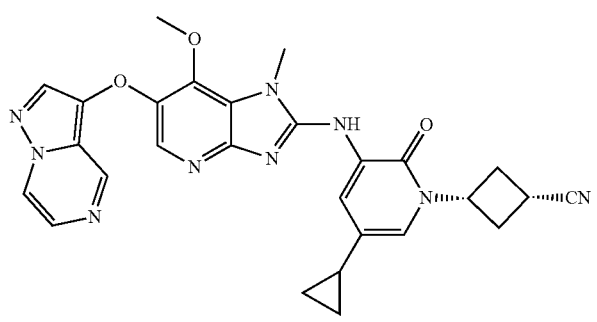 [SMILES: COc1c(Oc2cnn3ccncc23)cnc2nc(Nc3cc(C4CC4)cn([C@H]4C[C@@H](C#N)C4)c3=O)n(C)c12]
I-96-ii
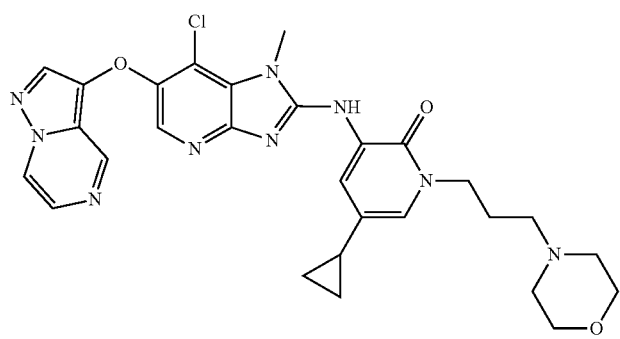 [SMILES: Cn1c(Nc2cc(C3CC3)cn(CCCN3CCOCC3)c2=O)nc2ncc(Oc3cnn4ccncc34)c(Cl)c21]
I-97

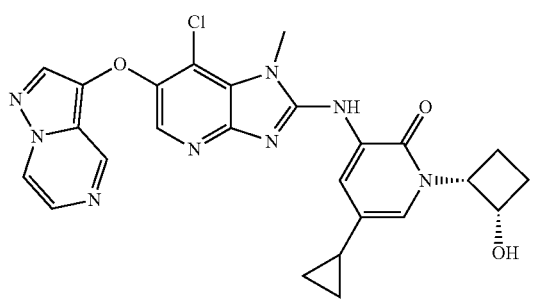
I-98-i
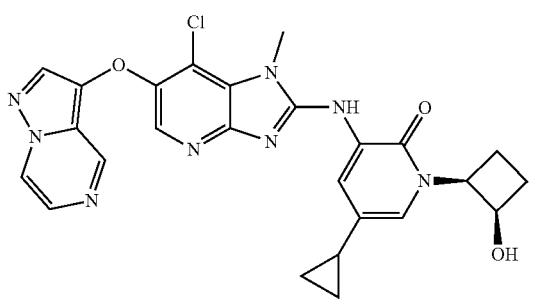 [SMILES: Cn1c(Nc2cc(C3CC3)cn([C@H]3CC[C@H]3O)c2=O)nc2ncc(Oc3cnn4ccncc34)c(Cl)c21]
I-98-ii
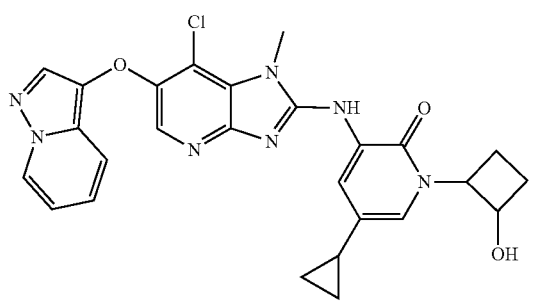 [SMILES: Cn1c(Nc2cc(C3CC3)cn(C3CCC3O)c2=O)nc2ncc(Oc3cnn4ccccc34)c(Cl)c21]
I-99
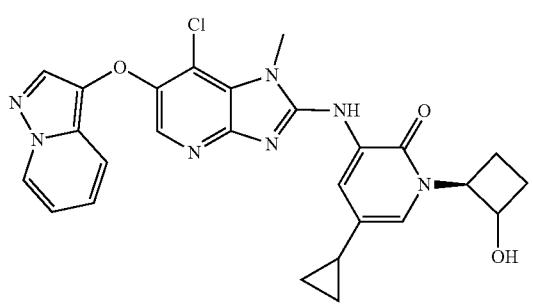 [SMILES: Cn1c(Nc2cc(C3CC3)cn([C@H]3CCC3O)c2=O)nc2ncc(Oc3cnn4ccccc34)c(Cl)c21]
I-99-i
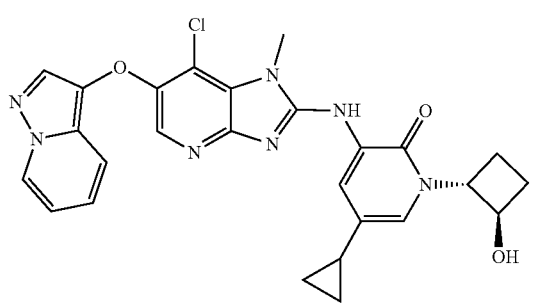 [SMILES: Cn1c(Nc2cc(C3CC3)cn([C@@H]3CC[C@H]3O)c2=O)nc2ncc(Oc3cnn4ccccc34)c(Cl)c21]
I-99-ii -continued
I-100
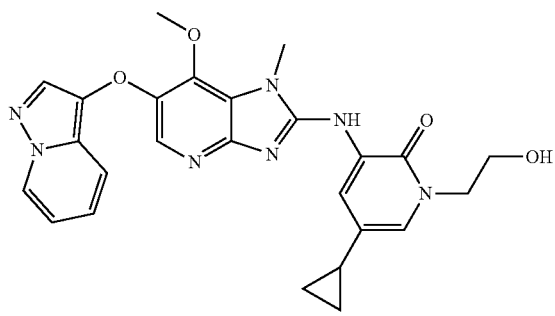 [SMILES: COc1c(Oc2cnn3ccccc23)cnc2nc(Nc3cc(C4CC4)cn(CCO)c3=O)n(C)c12]
I-101
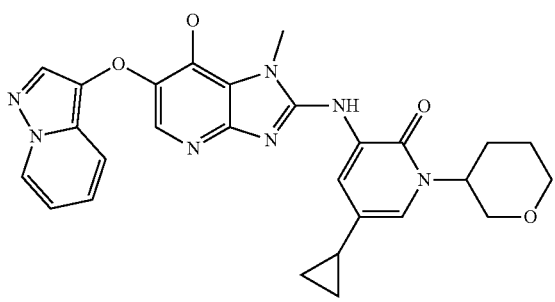 [SMILES: Cn1c(Nc2cc(C3CC3)cn(C3CCCOC3)c2=O)nc2ncc(Oc3cnn4ccccc34)c(O)c21]
I-101-i
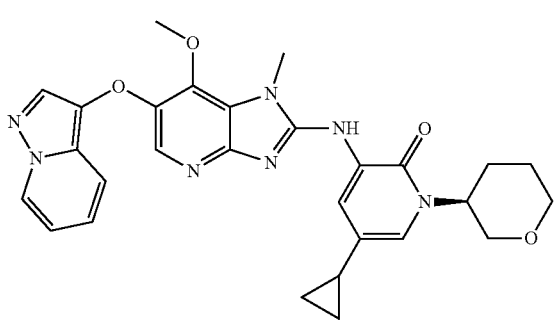 [SMILES: COc1c(Oc2cnn3ccccc23)cnc2nc(Nc3cc(C4CC4)cn([C@H]4CCCOC4)c3=O)n(C)c12]
I-101-ii
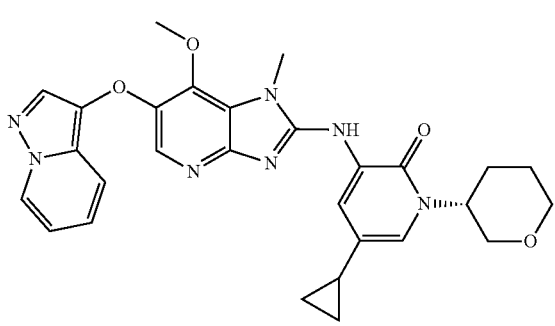
I-102
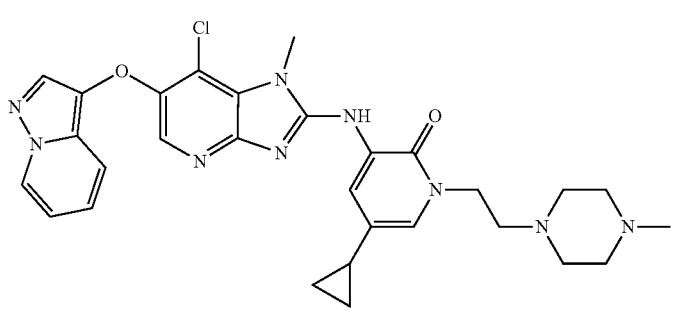 [SMILES: CN1CCN(CCn2cc(C3CC3)cc(Nc3nc4ncc(Oc5cnn6ccccc56)c(Cl)c4n3C)c2=O)CC1]

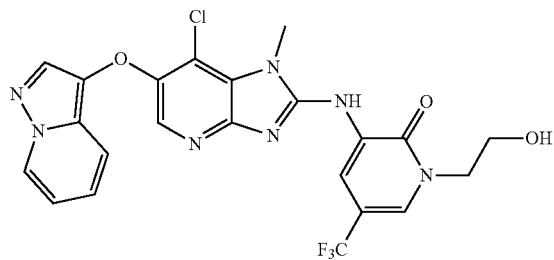 [SMILES: Cn1c(Nc2cc(C(F)(F)F)cn(CCO)c2=O)nc2ncc(Oc3cnn4ccccc34)c(Cl)c21]
I-103
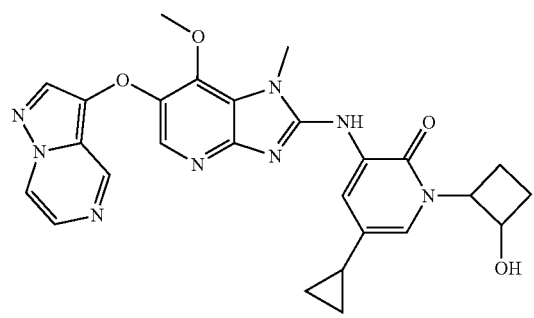 [SMILES: COc1c(Oc2cnn3ccncc23)cnc2nc(Nc3cc(C4CC4)cn(C4CCC4O)c3=O)n(C)c12]
I-104
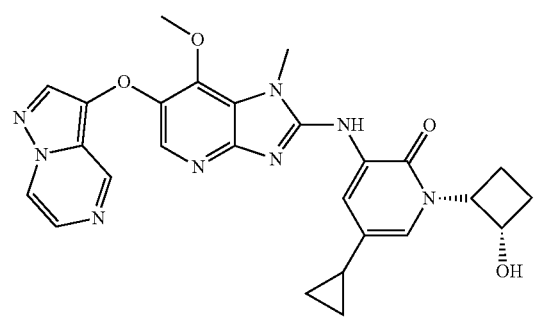
I-104-i
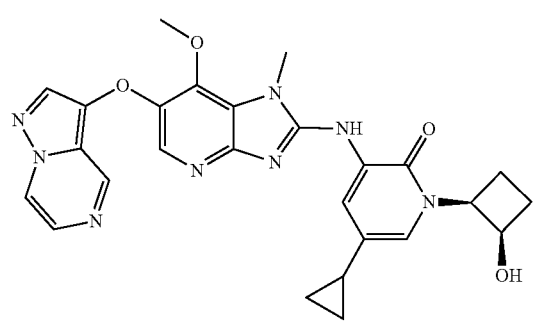 [SMILES: COc1c(Oc2cnn3ccncc23)cnc2nc(Nc3cc(C4CC4)cn([C@H]4CC[C@H]4O)c3=O)n(C)c12]
I-104-ii
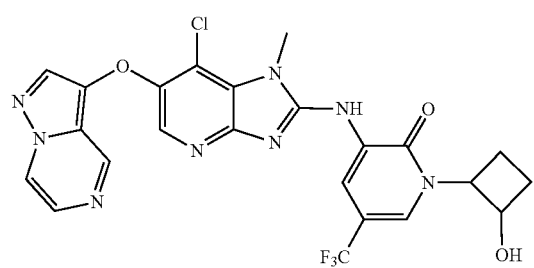 [SMILES: Cn1c(Nc2cc(C(F)(F)F)cn(C3CCC3O)c2=O)nc2ncc(Oc3cnn4ccncc34)c(Cl)c21]
I-105

-continued
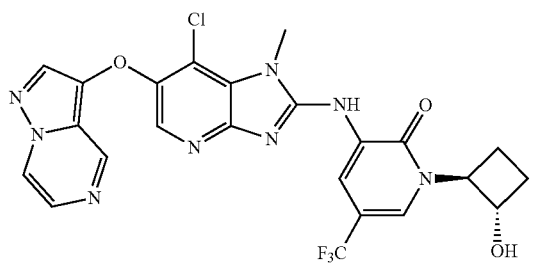
I-105-i
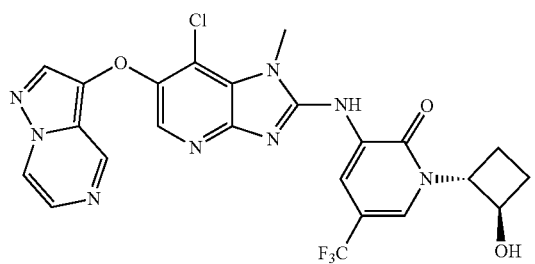 [SMILES: Cn1c(Nc2cc(C(F)(F)F)cn([C@@H]3CC[C@H]3O)c2=O)nc2ncc(Oc3cnn4ccncc34)c(Cl)c21]
I-105-ii
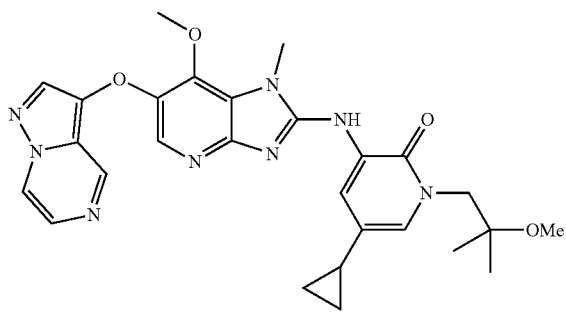 [SMILES: COc1c(Oc2cnn3ccncc23)cnc2nc(Nc3cc(C4CC4)cn(CC(C)(C)OC)c3=O)n(C)c12]
I-106
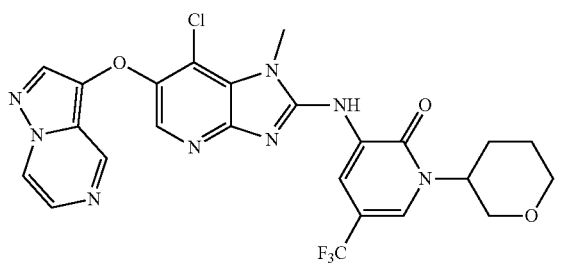 [SMILES: Cn1c(Nc2cc(C(F)(F)F)cn(C3CCCOC3)c2=O)nc2ncc(Oc3cnn4ccncc34)c(Cl)c21]
I-107
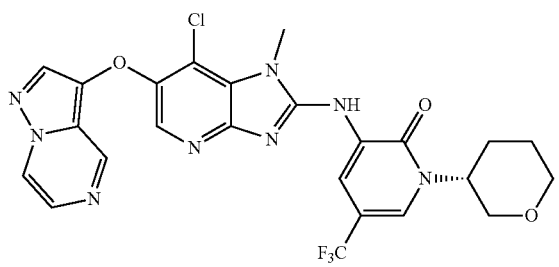 [SMILES: Cn1c(Nc2cc(C(F)(F)F)cn([C@@H]3CCCOC3)c2=O)nc2ncc(Oc3cnn4ccncc34)c(Cl)c21]
I-107-i

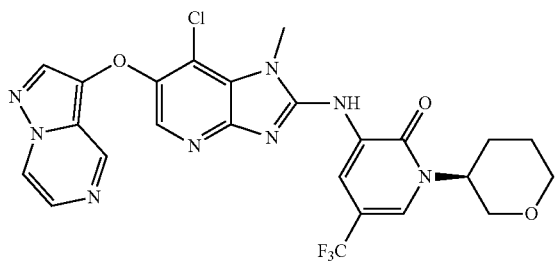 [SMILES: Cn1c(Nc2cc(C(F)(F)F)cn([C@H]3CCCOC3)c2=O)nc2ncc(Oc3cnn4ccncc34)c(Cl)c21]
I-107-ii
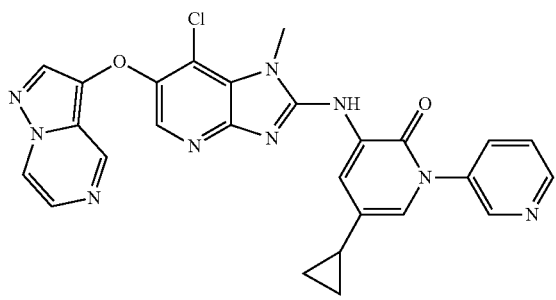 [SMILES: Cn1c(Nc2cc(C3CC3)cn(-c3cccnc3)c2=O)nc2ncc(Oc3cnn4ccncc34)c(Cl)c21]
I-108
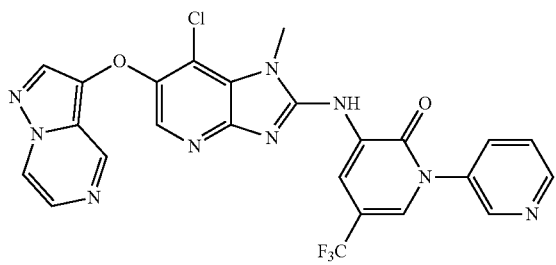 [SMILES: Cn1c(Nc2cc(C(F)(F)F)cn(-c3cccnc3)c2=O)nc2ncc(Oc3cnn4ccncc34)c(Cl)c21]
I-109
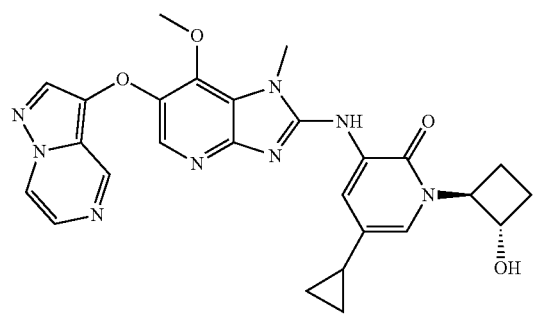 [SMILES: COc1c(Oc2cnn3ccncc23)cnc2nc(Nc3cc(C4CC4)cn([C@H]4CC[C@@H]4O)c3=O)n(C)c12]
I-110-i
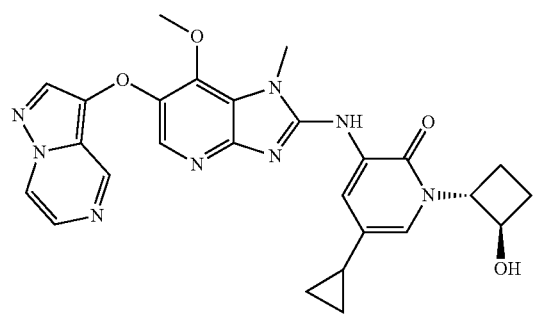 [SMILES: COc1c(Oc2cnn3ccncc23)cnc2nc(Nc3cc(C4CC4)cn([C@@H]4CC[C@H]4O)c3=O)n(C)c12]
I-110-ii I-111'
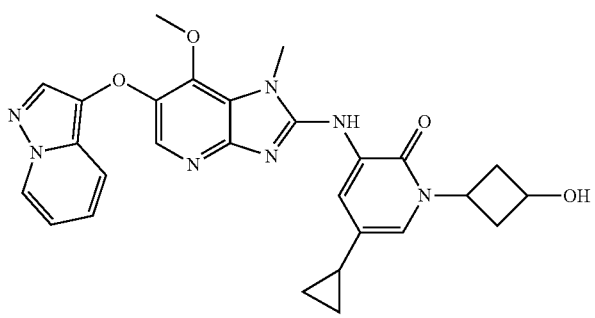 [SMILES: COc1c(Oc2cnn3ccccc23)cnc2nc(Nc3cc(C4CC4)cn(C4CC(O)C4)c3=O)n(C)c12]
I-111
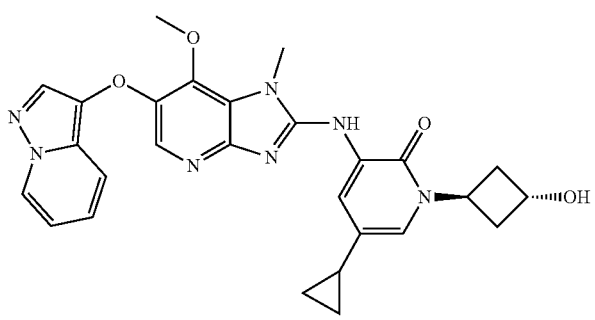 [SMILES: COc1c(Oc2cnn3ccccc23)cnc2nc(Nc3cc(C4CC4)cn([C@H]4C[C@H](O)C4)c3=O)n(C)c12]
I-112
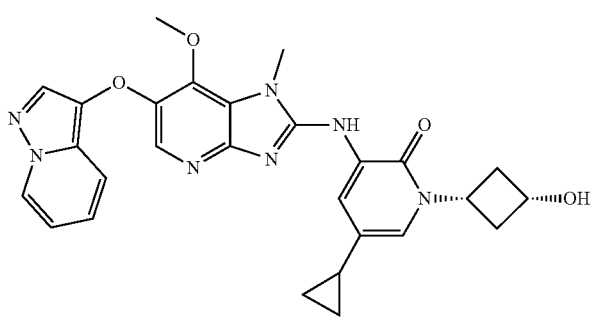 [SMILES: COc1c(Oc2cnn3ccccc23)cnc2nc(Nc3cc(C4CC4)cn([C@H]4C[C@@H](O)C4)c3=O)n(C)c12]
I-113
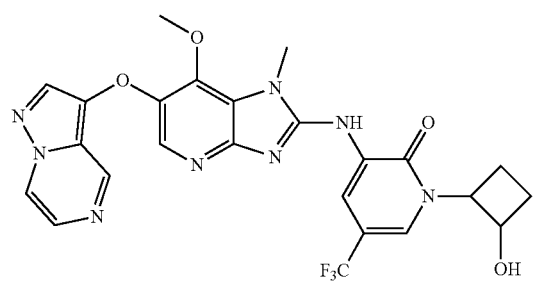 [SMILES: COc1c(Oc2cnn3ccncc23)cnc2nc(Nc3cc(C(F)(F)F)cn(C4CCC4O)c3=O)n(C)c12]
I-113-i
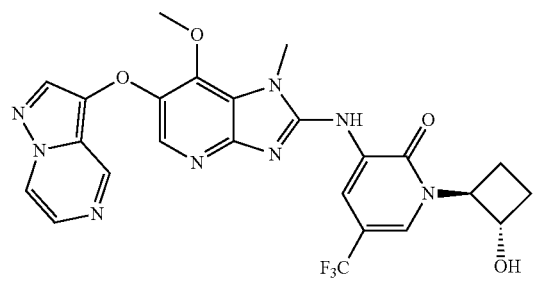

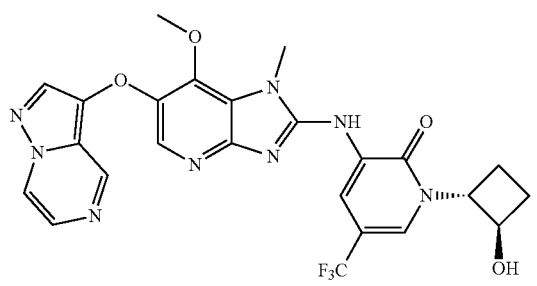 [SMILES: COc1c(Oc2cnn3ccncc23)cnc2nc(Nc3cc(C(F)(F)F)cn([C@@H]4CC[C@H]4O)c3=O)n(C)c12]
I-113-ii
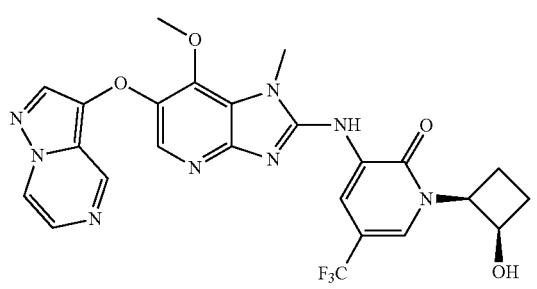 [SMILES: COc1c(Oc2cnn3ccncc23)cnc2nc(Nc3cc(C(F)(F)F)cn([C@H]4CC[C@H]4O)c3=O)n(C)c12]
I-113-iii
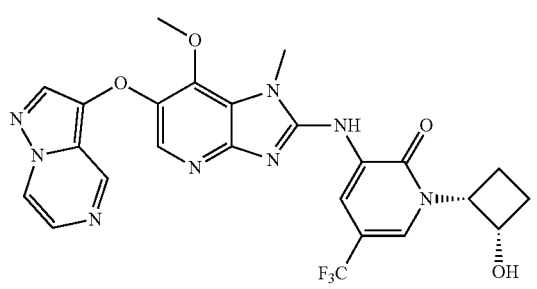
I-113-iv
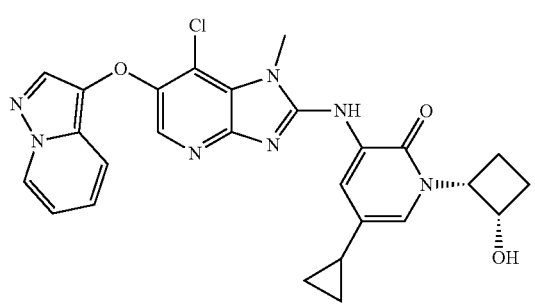
I-114-i
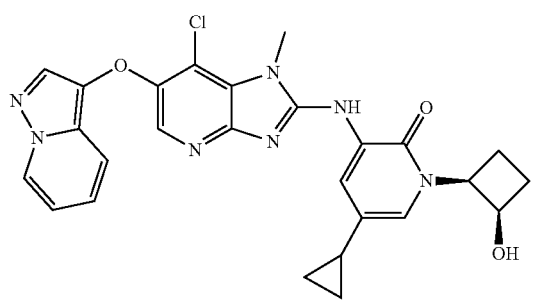 [SMILES: Cn1c(Nc2cc(C3CC3)cn([C@H]3CC[C@H]3O)c2=O)nc2ncc(Oc3cnn4ccccc34)c(Cl)c21]
I-114-ii I-115
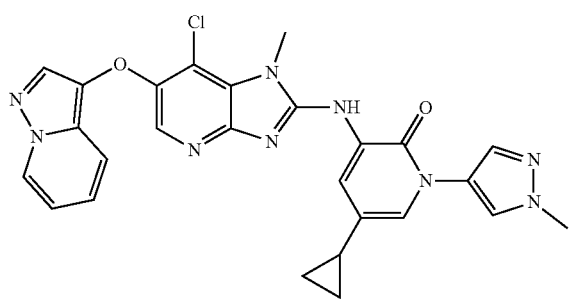 [SMILES: Cn1cc(-n2cc(C3CC3)cc(Nc3nc4ncc(Oc5cnn6ccccc56)c(Cl)c4n3C)c2=O)cn1]
I-116
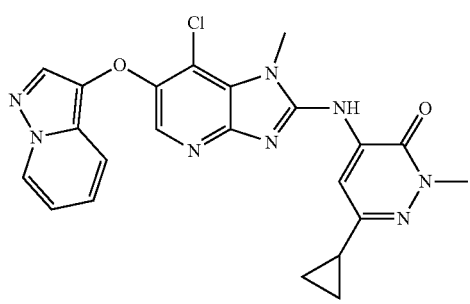 [SMILES: Cn1nc(C2CC2)cc(Nc2nc3ncc(Oc4cnn5ccccc45)c(Cl)c3n2C)c1=O]
I-117
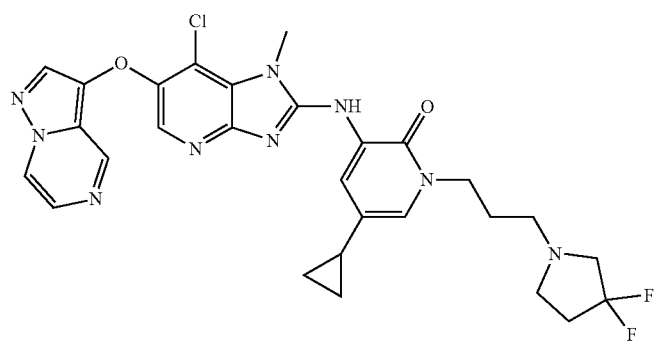 [SMILES: Cn1c(Nc2cc(C3CC3)cn(CCCN3CCC(F)(F)C3)c2=O)nc2ncc(Oc3cnn4ccncc34)c(Cl)c21]
I-118
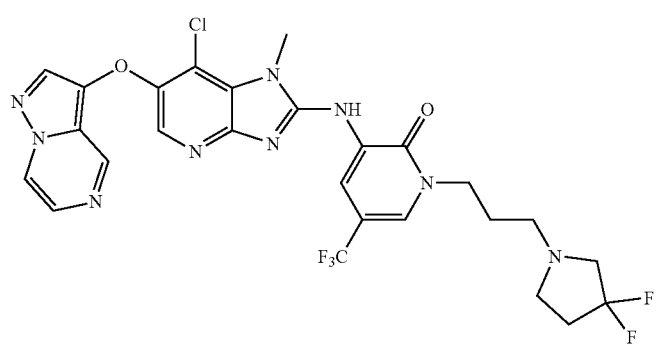 [SMILES: Cn1c(Nc2cc(C(F)(F)F)cn(CCCN3CCC(F)(F)C3)c2=O)nc2ncc(Oc3cnn4ccncc34)c(Cl)c21]
I-119-i
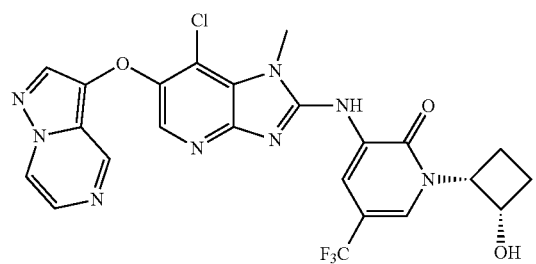 [SMILES: Cn1c(Nc2cc(C(F)(F)F)cn([C@@H]3CC[C@@H]3O)c2=O)nc2ncc(Oc3cnn4ccncc34)c(Cl)c21]

-continued
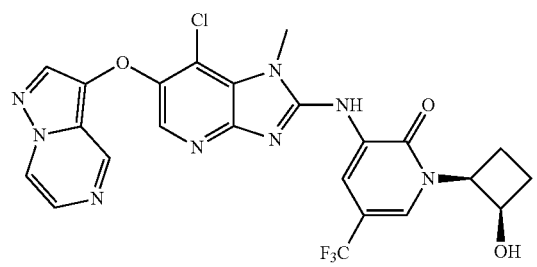 [SMILES: Cn1c(Nc2cc(C(F)(F)F)cn([C@H]3CC[C@H]3O)c2=O)nc2ncc(Oc3cnn4ccncc34)c(Cl)c21]
I-119-ii
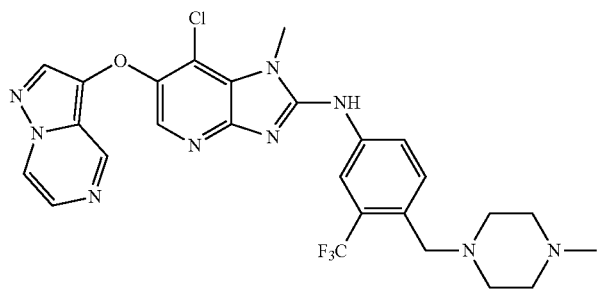 [SMILES: CN1CCN(Cc2ccc(Nc3nc4ncc(Oc5cnn6ccncc56)c(Cl)c4n3C)cc2C(F)(F)F)CC1]
I-120
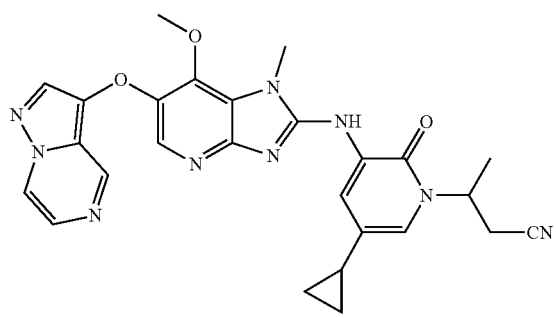
I-121
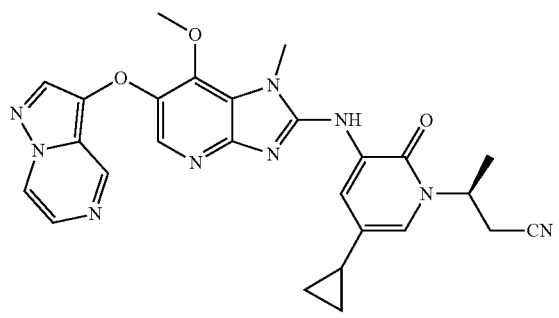
I-121-i
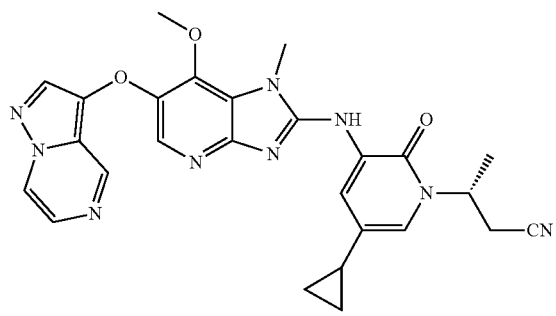 [SMILES: COc1c(Oc2cnn3ccncc23)cnc2nc(Nc3cc(C4CC4)cn(C(C)CC#N)c3=O)n(C)c12]
I-121-ii -continued
I-122
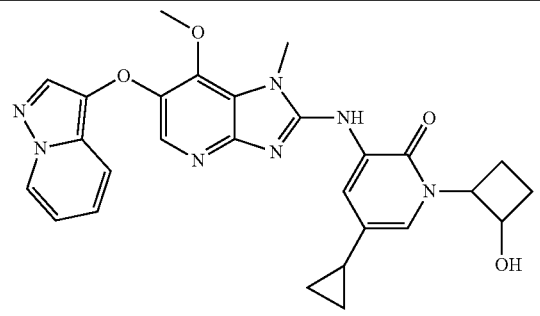
I-122-i
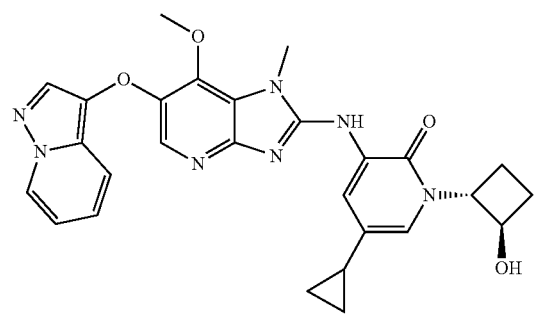 [SMILES: COc1c(Oc2cnn3ccccc23)cnc2nc(Nc3cc(C4CC4)cn([C@@H]4CC[C@H]4O)c3=O)n(C)c12]
I-122-ii
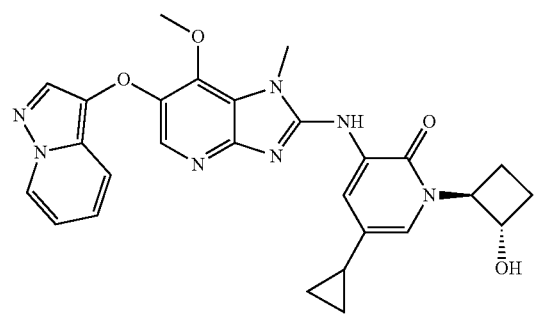 [SMILES: COc1c(Oc2cnn3ccccc23)cnc2nc(Nc3cc(C4CC4)cn([C@H]4CC[C@@H]4O)c3=O)n(C)c12]
I-123
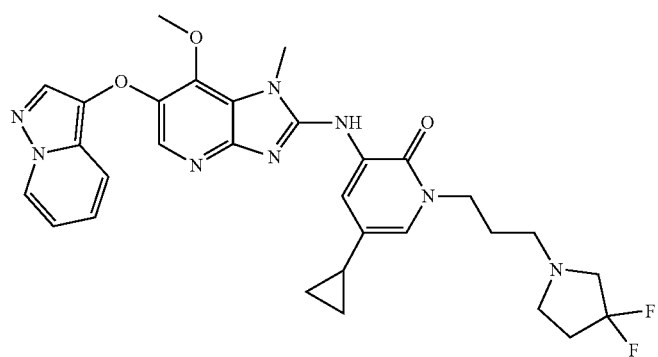 [SMILES: COc1c(Oc2cnn3ccccc23)cnc2nc(Nc3cc(C4CC4)cn(CCCN4CCC(F)(F)C4)c3=O)n(C)c12]
I-124
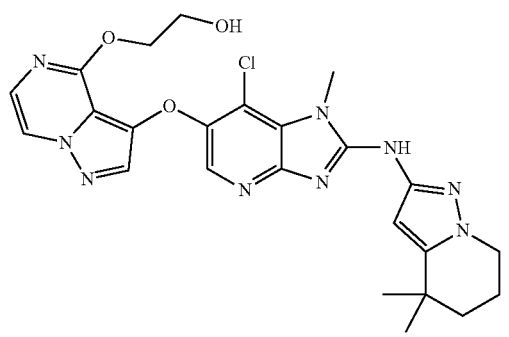 [SMILES: Cn1c(Nc2cc3n(n2)CCCC3(C)C)nc2ncc(Oc3cnn4ccnc(OCCO)c34)c(Cl)c21]

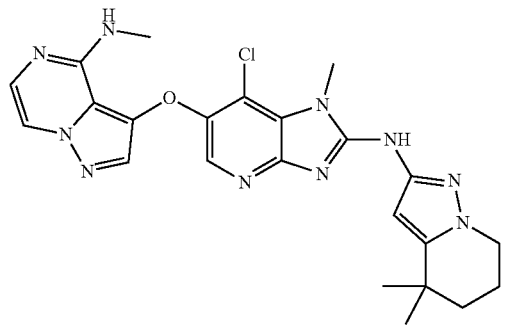 [SMILES: CNc1nccn2ncc(Oc3cnc4nc(Nc5cc6n(n5)CCCC6(C)C)n(C)c4c3Cl)c12]
I-125
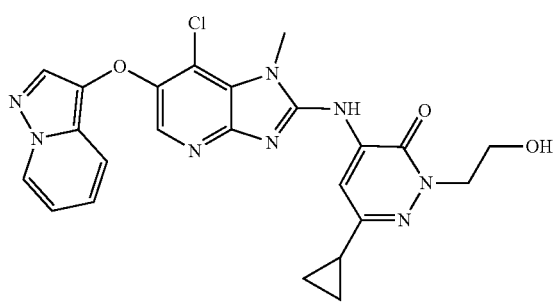 [SMILES: Cn1c(Nc2cc(C3CC3)nn(CCO)c2=O)nc2ncc(Oc3cnn4ccccc34)c(Cl)c21]
I-126
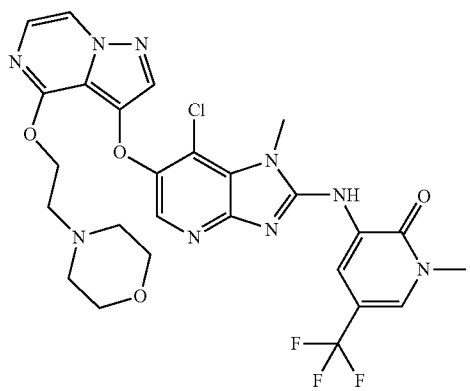 [SMILES: Cn1cc(C(F)(F)F)cc(Nc2nc3ncc(Oc4cnn5ccnc(OCCN6CCOCC6)c45)c(Cl)c3n2C)c1=O]
I-127
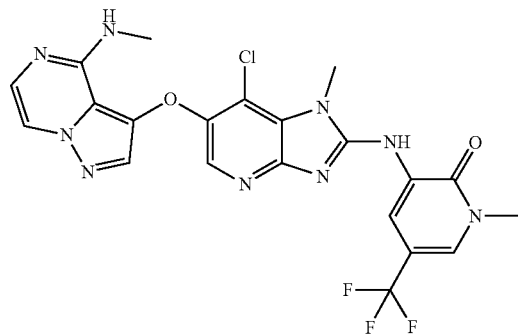 [SMILES: CNc1nccn2ncc(Oc3cnc4nc(Nc5cc(C(F)(F)F)cn(C)c5=O)n(C)c4c3Cl)c12]
I-128

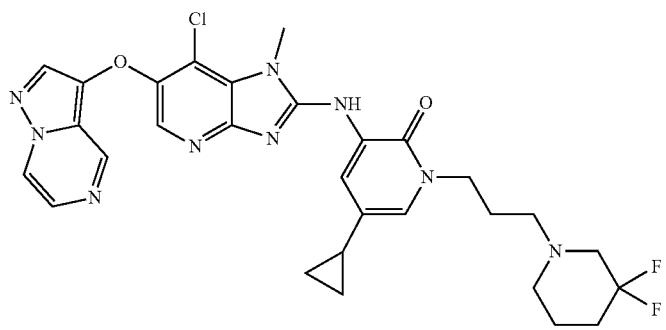 [SMILES: Cn1c(Nc2cc(C3CC3)cn(CCCN3CCCC(F)(F)C3)c2=O)nc2ncc(Oc3cnn4ccncc34)c(Cl)c21]
I-129
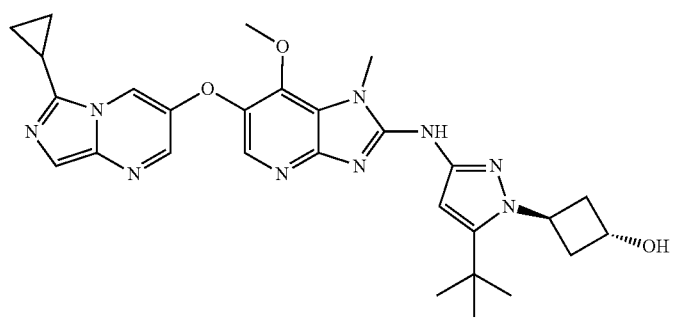 [SMILES: COc1c(Oc2cnc3cnc(C4CC4)n3c2)cnc2nc(Nc3cc(C(C)(C)C)n([C@H]4C[C@H](O)C4)n3)n(C)c12]
I-130
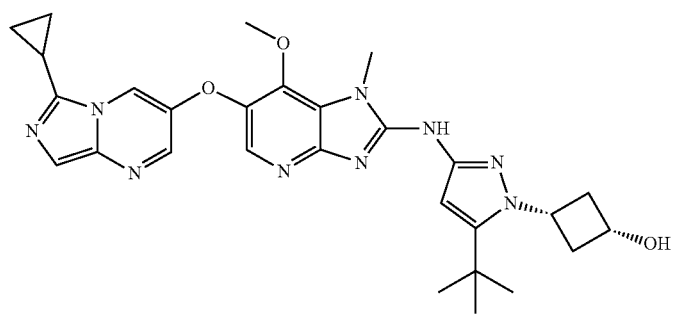 [SMILES: COc1c(Oc2cnc3cnc(C4CC4)n3c2)cnc2nc(Nc3cc(C(C)(C)C)n([C@H]4C[C@@H](O)C4)n3)n(C)c12]
I-130-ii
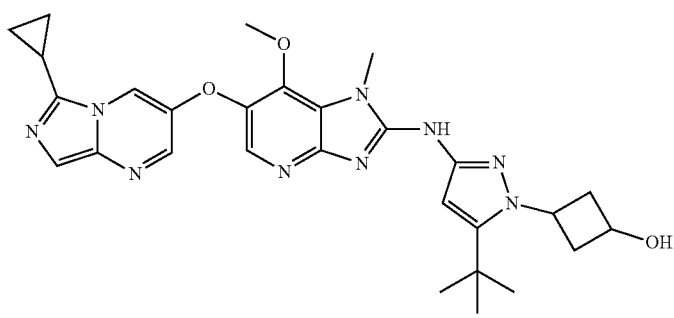 [SMILES: COc1c(Oc2cnc3cnc(C4CC4)n3c2)cnc2nc(Nc3cc(C(C)(C)C)n(C4CC(O)C4)n3)n(C)c12]
I-130'
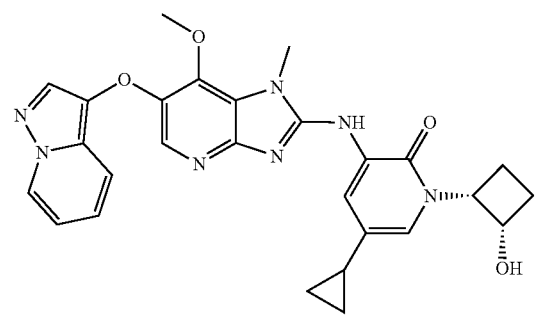 [SMILES: COc1c(Oc2cnn3ccccc23)cnc2nc(Nc3cc(C4CC4)cn([C@@H]4CC[C@@H]4O)c3=O)n(C)c12]
I-131-i

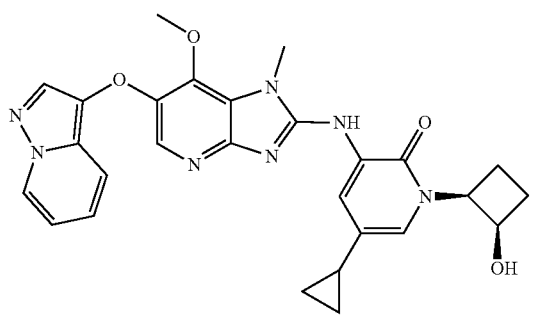 [SMILES: COc1c(Oc2cnn3ccccc23)cnc2nc(Nc3cc(C4CC4)cn([C@H]4CC[C@H]4O)c3=O)n(C)c12]
I-131-ii
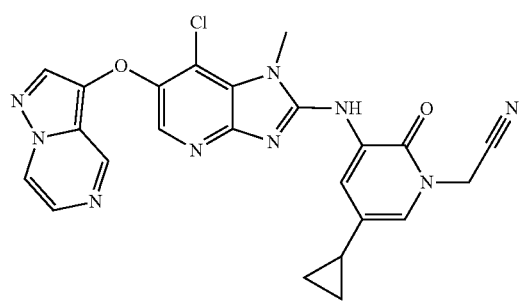 [SMILES: Cn1c(Nc2cc(C3CC3)cn(CC#N)c2=O)nc2ncc(Oc3cnn4ccncc34)c(Cl)c21]
I-132
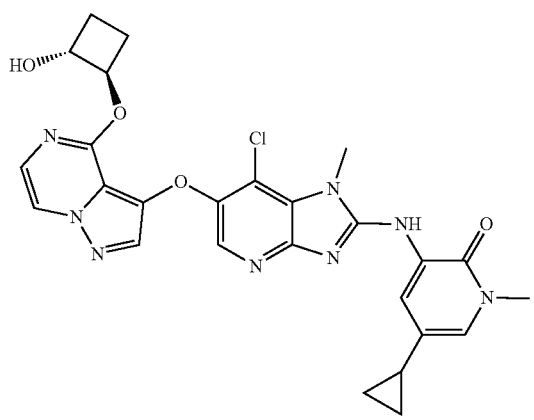 [SMILES: Cn1cc(C2CC2)cc(Nc2nc3ncc(Oc4cnn5ccnc(O[C@@H]6CC[C@H]6O)c45)c(Cl)c3n2C)c1=O]
I-133-i
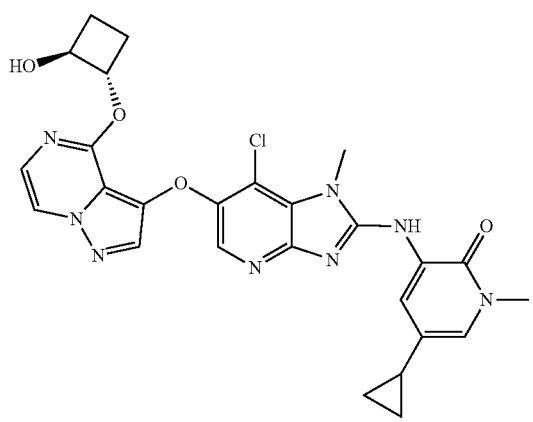 [SMILES: Cn1cc(C2CC2)cc(Nc2nc3ncc(Oc4cnn5ccnc(O[C@H]6CC[C@@H]6O)c45)c(Cl)c3n2C)c1=O]
I-133-ii

-continued
I-133-iii
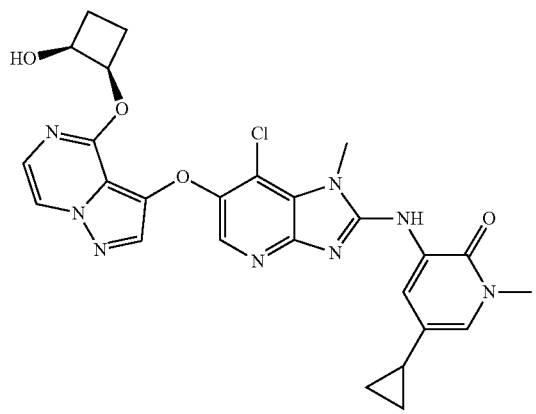 [SMILES: Cn1cc(C2CC2)cc(Nc2nc3ncc(Oc4cnn5ccnc(O[C@@H]6CC[C@@H]6O)c45)c(Cl)c3n2C)c1=O]
I-133-iv
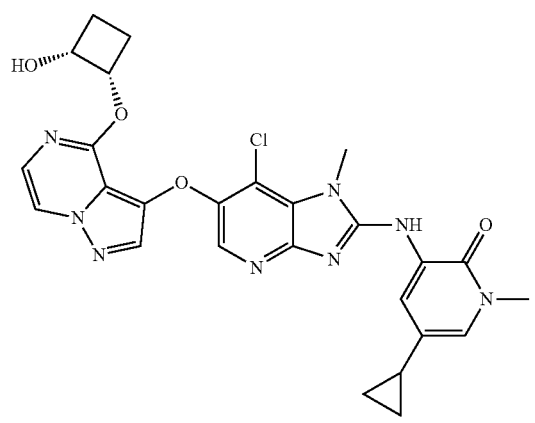 [SMILES: Cn1cc(C2CC2)cc(Nc2nc3ncc(Oc4cnn5ccnc(O[C@H]6CC[C@H]6O)c45)c(Cl)c3n2C)c1=O]
I-133
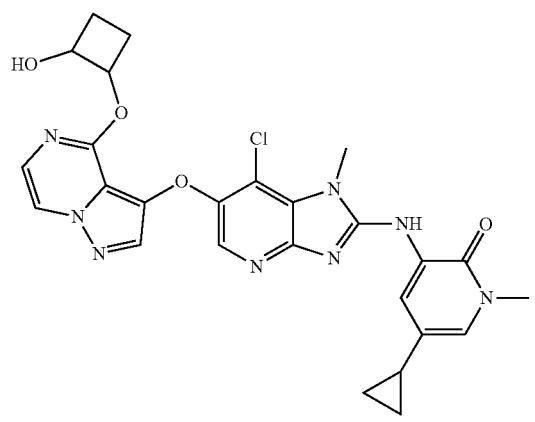 [SMILES: Cn1cc(C2CC2)cc(Nc2nc3ncc(Oc4cnn5ccnc(OC6CCC6O)c45)c(Cl)c3n2C)c1=O]
I-134
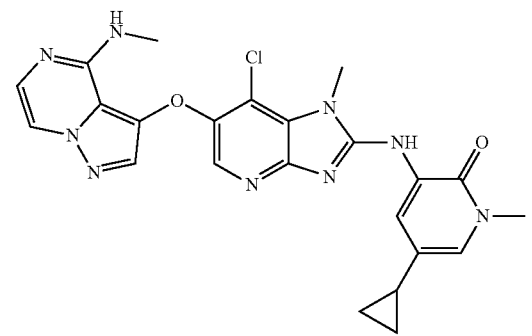 [SMILES: CNc1nccn2ncc(Oc3cnc4nc(Nc5cc(C6CC6)cn(C)c5=O)n(C)c4c3Cl)c12]

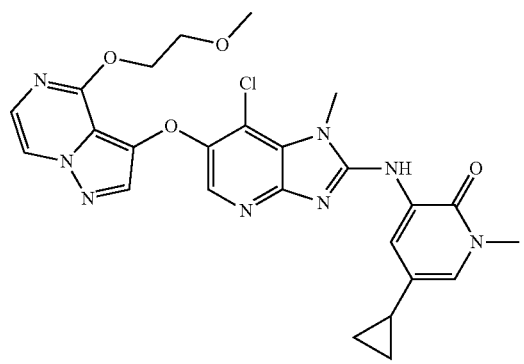 [SMILES: COCCOc1nccn2ncc(Oc3cnc4nc(Nc5cc(C6CC6)cn(C)c5=O)n(C)c4c3Cl)c12]
I-135
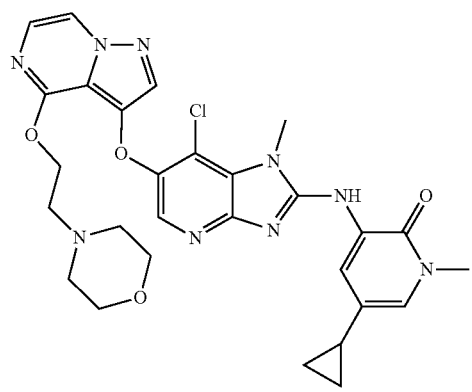 [SMILES: Cn1cc(C2CC2)cc(Nc2nc3ncc(Oc4cnn5ccnc(OCCN6CCOCC6)c45)c(Cl)c3n2C)c1=O]
I-136
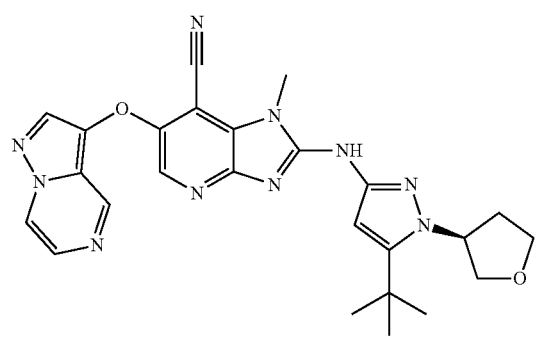 [SMILES: Cn1c(Nc2cc(C(C)(C)C)n([C@H]3CCOC3)n2)nc2ncc(Oc3cnn4ccncc34)c(C#N)c21]
I-137
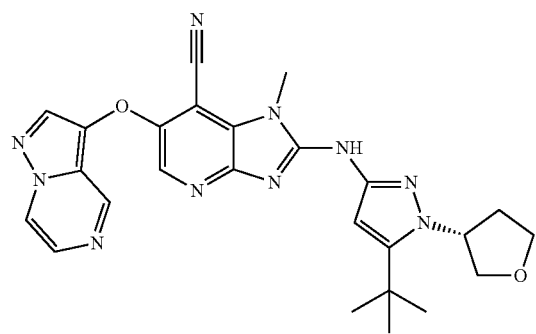 [SMILES: Cn1c(Nc2cc(C(C)(C)C)n([C@@H]3CCOC3)n2)nc2ncc(Oc3cnn4ccncc34)c(C#N)c21]
I-137-ii

-continued
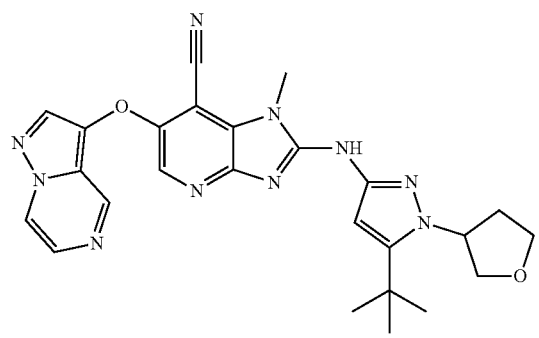 [SMILES: Cn1c(Nc2cc(C(C)(C)C)n(C3CCOC3)n2)nc2ncc(Oc3cnn4ccncc34)c(C#N)c21]
I-137'
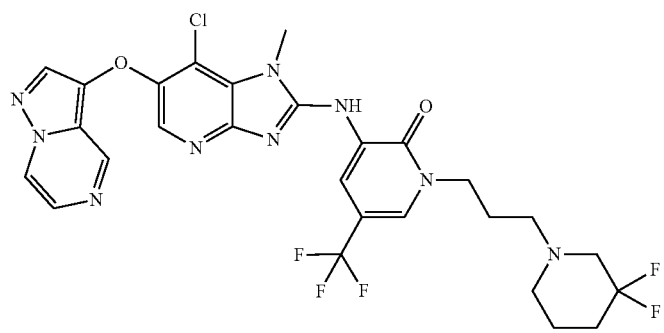 [SMILES: Cn1c(Nc2cc(C(F)(F)F)cn(CCCN3CCCC(F)(F)C3)c2=O)nc2ncc(Oc3cnn4ccncc34)c(Cl)c21]
I-138
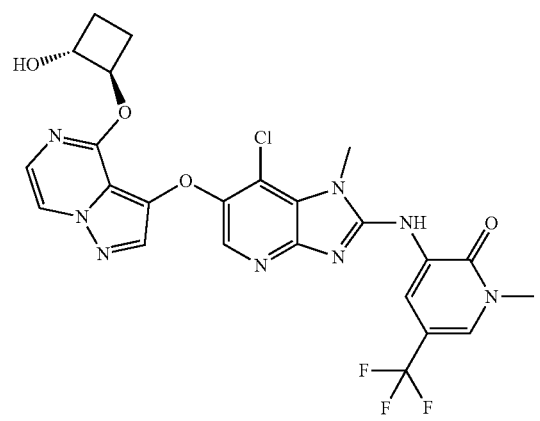 [SMILES: Cn1cc(C(F)(F)F)cc(Nc2nc3ncc(Oc4cnn5ccnc(O[C@@H]6CC[C@H]6O)c45)c(Cl)c3n2C)c1=O]
I-139-i
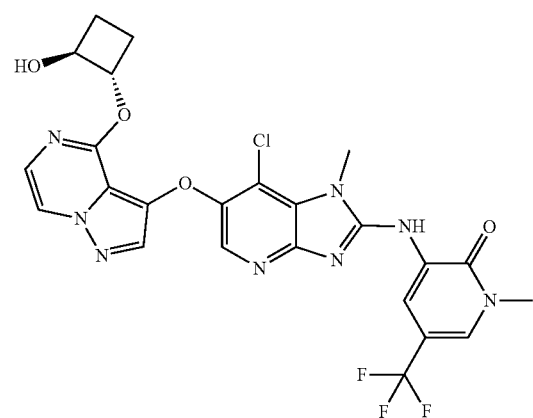 [SMILES: Cn1cc(C(F)(F)F)cc(Nc2nc3ncc(Oc4cnn5ccnc(O[C@H]6CC[C@@H]6O)c45)c(Cl)c3n2C)c1=O]
I-139-ii I-139-iii
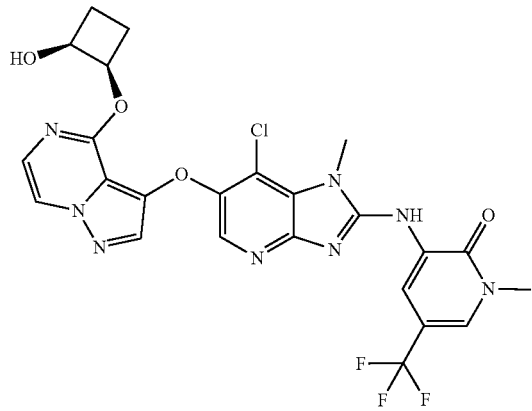 [SMILES: Cn1cc(C(F)(F)F)cc(Nc2nc3ncc(Oc4cnn5ccnc(O[C@@H]6CC[C@@H]6O)c45)c(Cl)c3n2C)c1=O]
I-139-iv
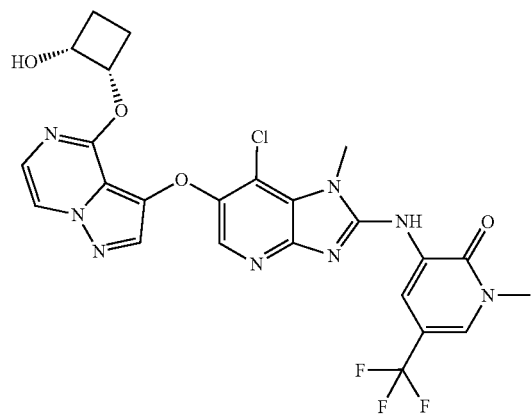
I-139
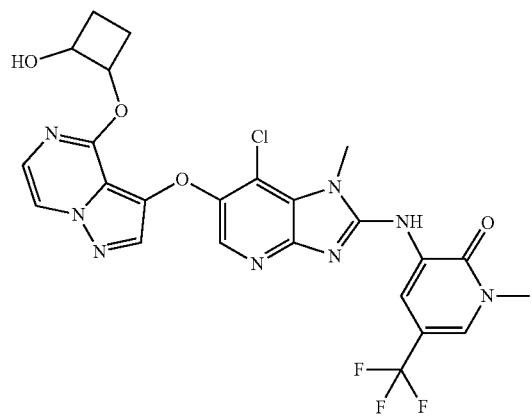 [SMILES: Cn1cc(C(F)(F)F)cc(Nc2nc3ncc(Oc4cnn5ccnc(O[C@H]6CC[C@H]6O)c45)c(Cl)c3n2C)c1=O]
I-140
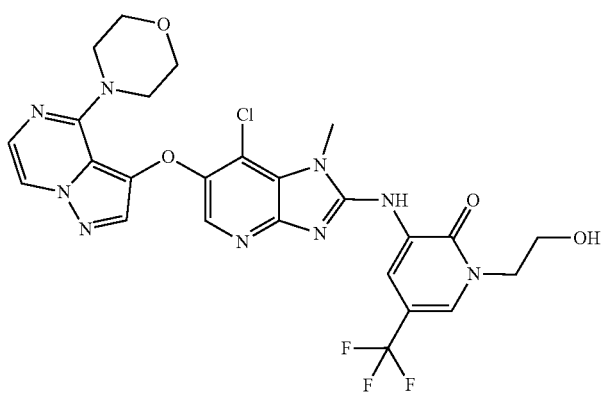 [SMILES: Cn1c(Nc2cc(C(F)(F)F)cn(CCO)c2=O)nc2ncc(Oc3cnn4ccnc(N5CCOCC5)c34)c(Cl)c21]

-continued
I-141
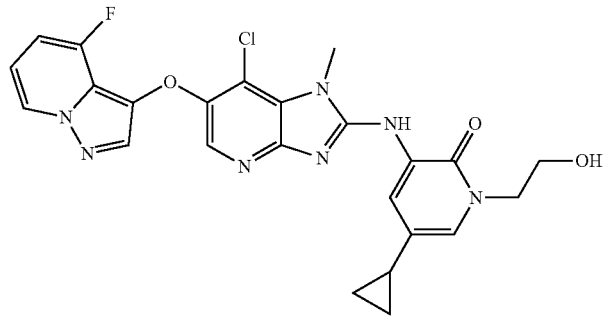 [SMILES: Cn1c(Nc2cc(C3CC3)cn(CCO)c2=O)nc2ncc(Oc3cnn4cccc(F)c34)c(Cl)c21]
I-142
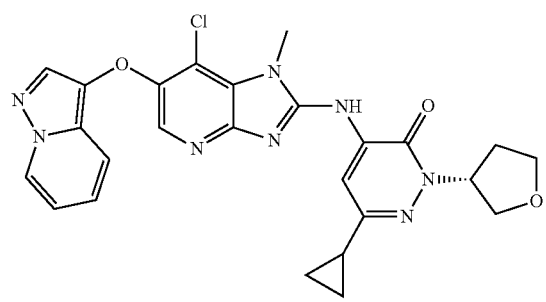
I-143
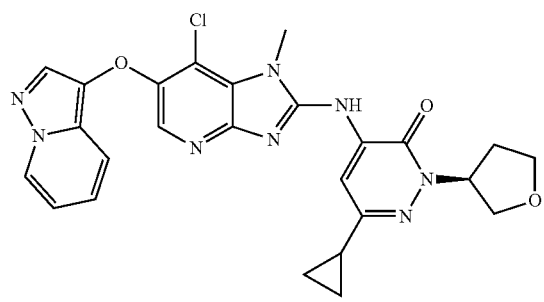 [SMILES: Cn1c(Nc2cc(C3CC3)nn([C@H]3CCOC3)c2=O)nc2ncc(Oc3cnn4ccccc34)c(Cl)c21]
I-142'
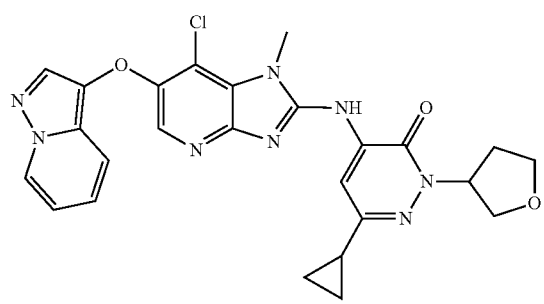 [SMILES: Cn1c(Nc2cc(C3CC3)nn(C3CCOC3)c2=O)nc2ncc(Oc3cnn4ccccc34)c(Cl)c21]
I-144
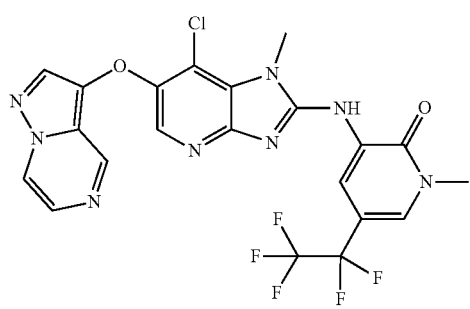 [SMILES: Cn1cc(C(F)(F)C(F)(F)F)cc(Nc2nc3ncc(Oc4cnn5ccncc45)c(Cl)c3n2C)c1=O]

-continued
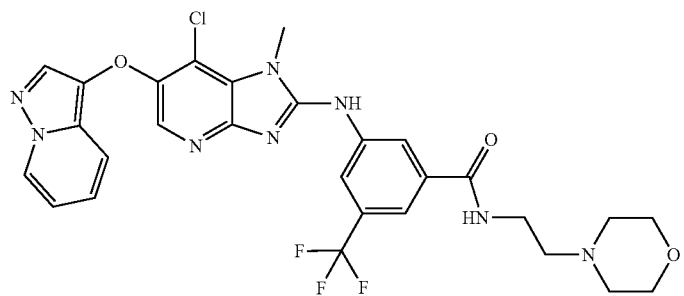 [SMILES: Cn1c(Nc2cc(C(=O)NCCN3CCOCC3)cc(C(F)(F)F)c2)nc2ncc(Oc3cnn4ccccc34)c(Cl)c21]
I-145
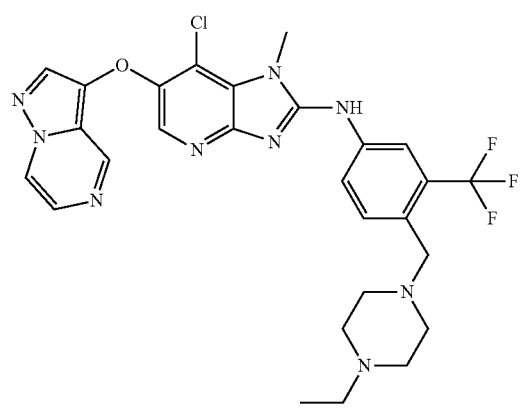 [SMILES: CCN1CCN(Cc2ccc(Nc3nc4ncc(Oc5cnn6ccncc56)c(Cl)c4n3C)cc2C(F)(F)F)CC1]
I-146
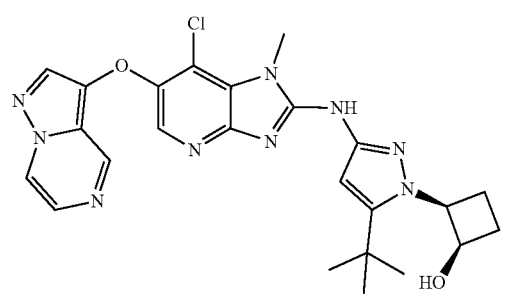 [SMILES: Cn1c(Nc2cc(C(C)(C)C)n([C@H]3CC[C@H]3O)n2)nc2ncc(Oc3cnn4ccncc34)c(Cl)c21]
I-147-i
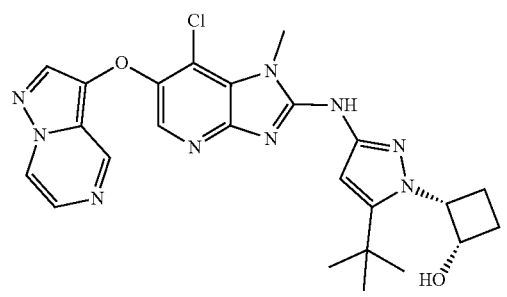 [SMILES: Cn1c(Nc2cc(C(C)(C)C)n([C@@H]3CC[C@@H]3O)n2)nc2ncc(Oc3cnn4ccncc34)c(Cl)c21]
I-147-ii
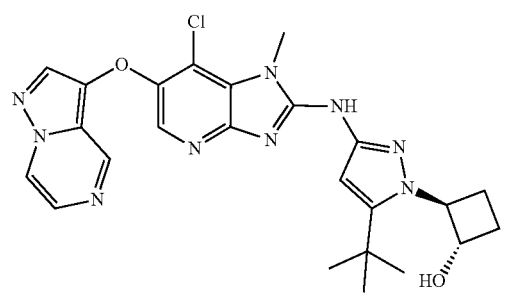 [SMILES: Cn1c(Nc2cc(C(C)(C)C)n([C@H]3CC[C@@H]3O)n2)nc2ncc(Oc3cnn4ccncc34)c(Cl)c21]
I-147-iii

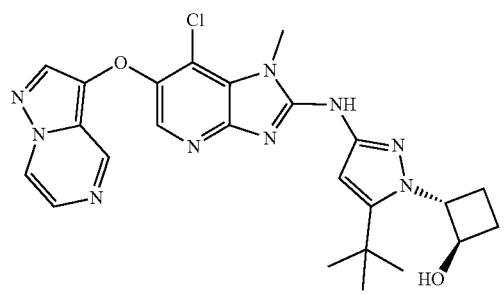 [SMILES: Cn1c(Nc2cc(C(C)(C)C)n([C@@H]3CC[C@H]3O)n2)nc2ncc(Oc3cnn4ccncc34)c(Cl)c21]
I-147-iv
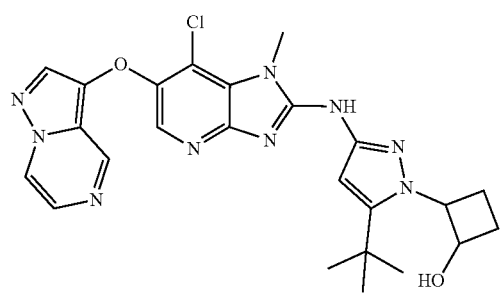 [SMILES: Cn1c(Nc2cc(C(C)(C)C)n(C3CCC3O)n2)nc2ncc(Oc3cnn4ccncc34)c(Cl)c21]
I-147
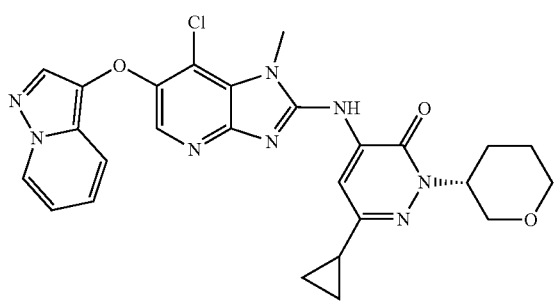
I-148-i
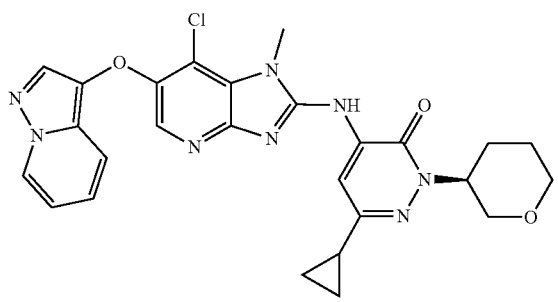 [SMILES: Cn1c(Nc2cc(C3CC3)nn([C@H]3CCCOC3)c2=O)nc2ncc(Oc3cnn4ccccc34)c(Cl)c21]
I-148-ii
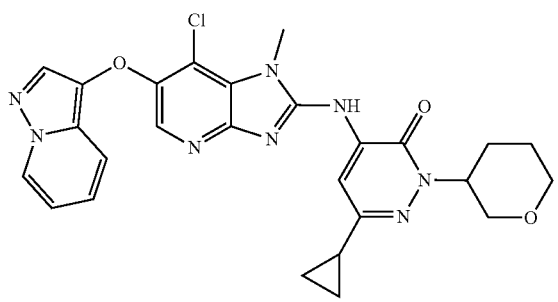 [SMILES: Cn1c(Nc2cc(C3CC3)nn(C3CCCOC3)c2=O)nc2ncc(Oc3cnn4ccccc34)c(Cl)c21]
I-148

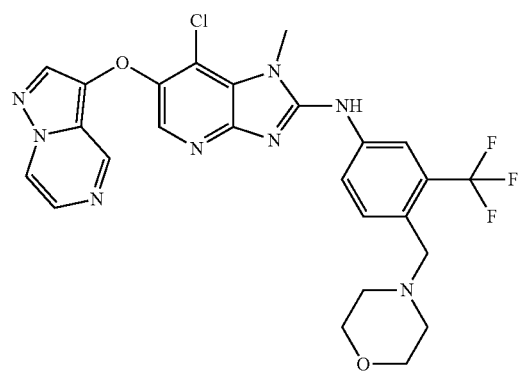 [SMILES: Cn1c(Nc2ccc(CN3CCOCC3)c(C(F)(F)F)c2)nc2ncc(Oc3cnn4ccncc34)c(Cl)c21]
I-149
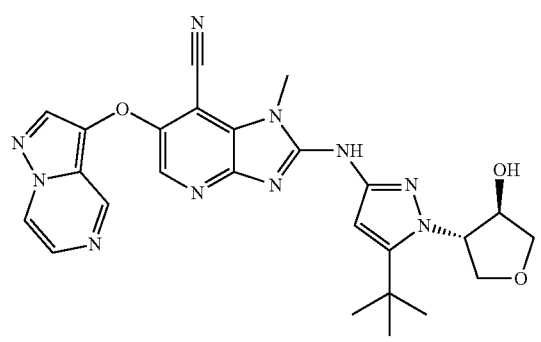 [SMILES: Cn1c(Nc2cc(C(C)(C)C)n([C@H]3COC[C@@H]3O)n2)nc2ncc(Oc3cnn4ccncc34)c(C#N)c21]
I-150-i
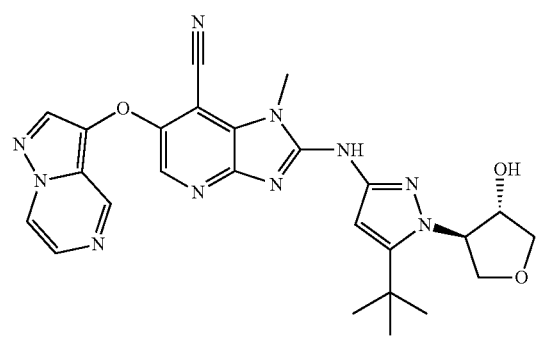
I-150-ii
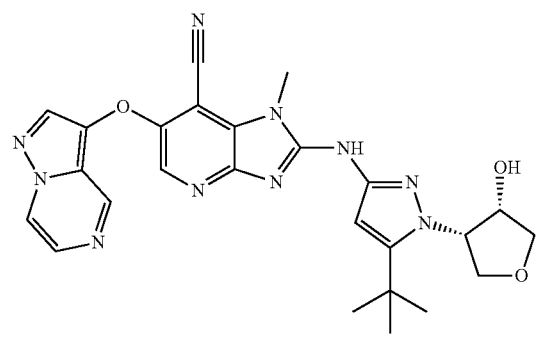 [SMILES: Cn1c(Nc2cc(C(C)(C)C)n([C@H]3COC[C@H]3O)n2)nc2ncc(Oc3cnn4ccncc34)c(C#N)c21]
I-150-iii

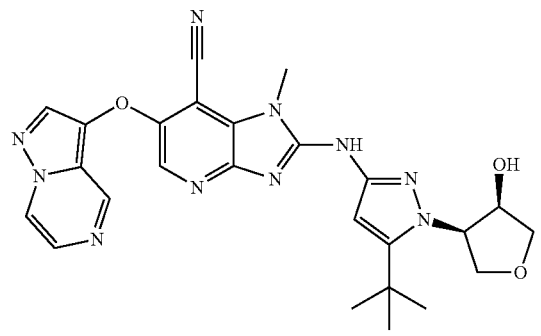 [SMILES: Cn1c(Nc2cc(C(C)(C)C)n([C@@H]3COC[C@@H]3O)n2)nc2ncc(Oc3cnn4ccncc34)c(C#N)c21]
I-150-iv
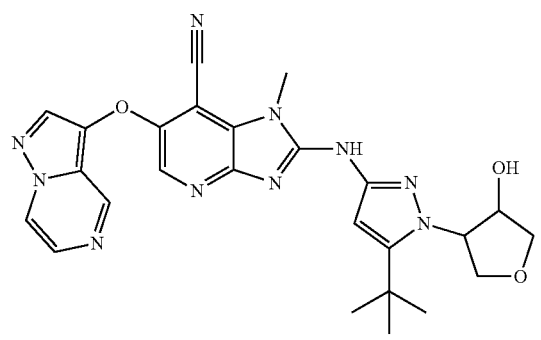 [SMILES: Cn1c(Nc2cc(C(C)(C)C)n(C3COCC3O)n2)nc2ncc(Oc3cnn4ccncc34)c(C#N)c21]
I-150
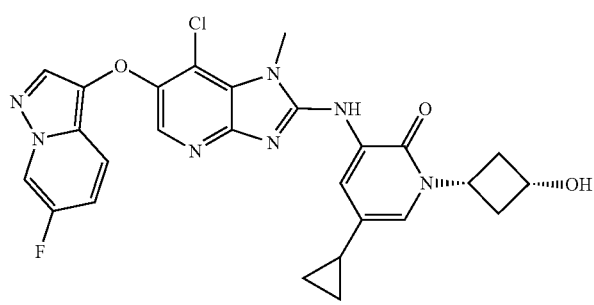 [SMILES: Cn1c(Nc2cc(C3CC3)cn([C@H]3C[C@@H](O)C3)c2=O)nc2ncc(Oc3cnn4cc(F)ccc34)c(Cl)c21]
I-151
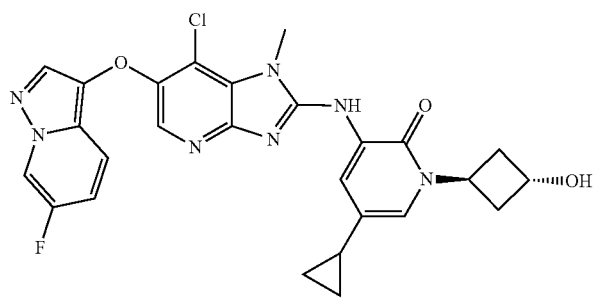 [SMILES: Cn1c(Nc2cc(C3CC3)cn([C@H]3C[C@H](O)C3)c2=O)nc2ncc(Oc3cnn4cc(F)ccc34)c(Cl)c21]
I-152
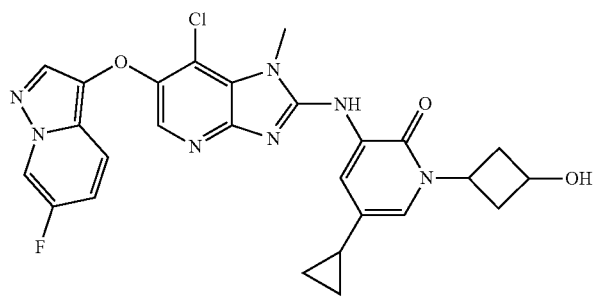 [SMILES: Cn1c(Nc2cc(C3CC3)cn(C3CC(O)C3)c2=O)nc2ncc(Oc3cnn4cc(F)ccc34)c(Cl)c21]
I-151'

-continued
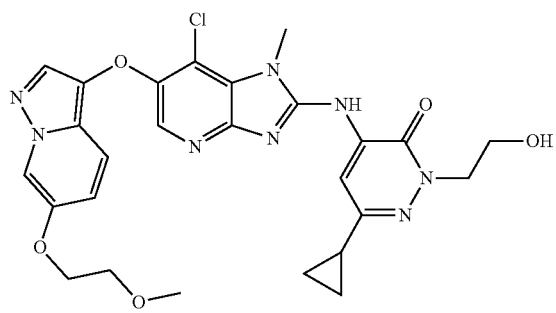 [SMILES: COCCOc1ccc2c(Oc3cnc4nc(Nc5cc(C6CC6)nn(CCO)c5=O)n(C)c4c3Cl)cnn2c1]
I-153
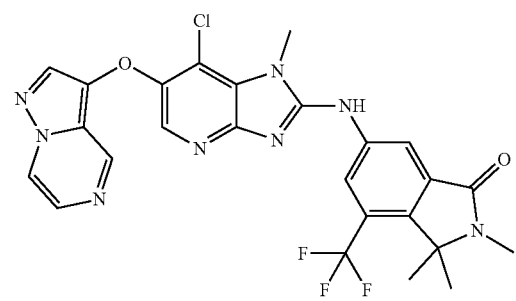 [SMILES: CN1C(=O)c2cc(Nc3nc4ncc(Oc5cnn6ccncc56)c(Cl)c4n3C)cc(C(F)(F)F)c2C1(C)C]
I-154
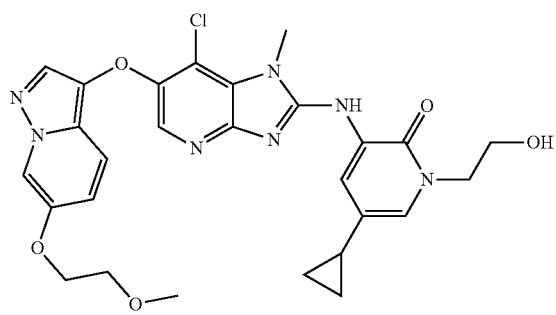 [SMILES: COCCOc1ccc2c(Oc3cnc4nc(Nc5cc(C6CC6)cn(CCO)c5=O)n(C)c4c3Cl)cnn2c1]
I-155
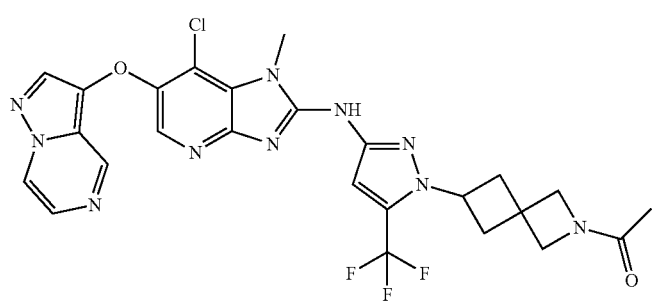 [SMILES: CC(=O)N1CC2(CC(n3nc(Nc4nc5ncc(Oc6cnn7ccncc67)c(Cl)c5n4C)cc3C(F)(F)F)C2)C1]
I-156
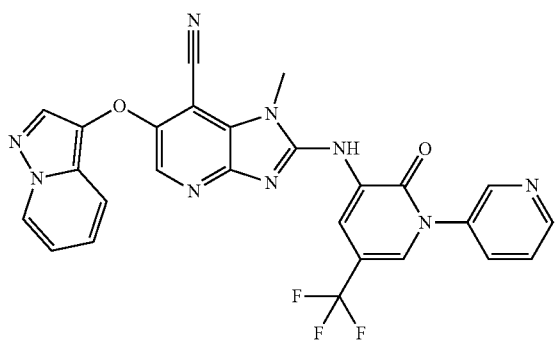 [SMILES: Cn1c(Nc2cc(C(F)(F)F)cn(-c3cccnc3)c2=O)nc2ncc(Oc3cnn4ccccc34)c(C#N)c21]
I-157

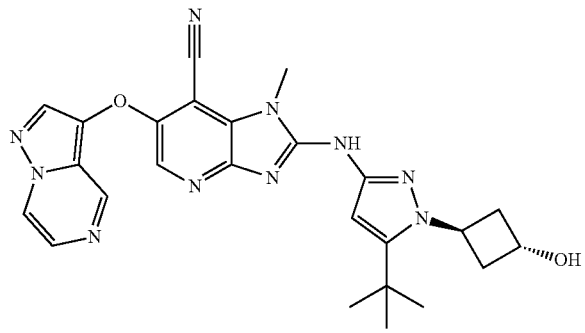 [SMILES: Cn1c(Nc2cc(C(C)(C)C)n([C@H]3C[C@H](O)C3)n2)nc2ncc(Oc3cnn4ccncc34)c(C#N)c21]
I-158
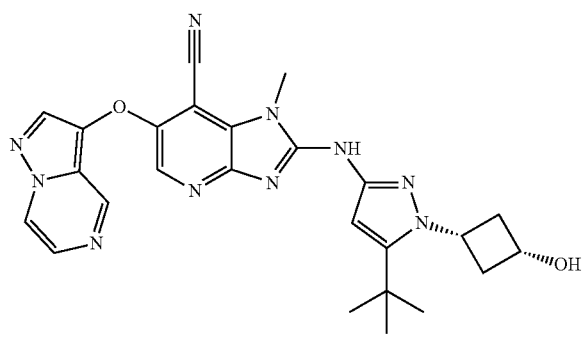 [SMILES: Cn1c(Nc2cc(C(C)(C)C)n([C@H]3C[C@@H](O)C3)n2)nc2ncc(Oc3cnn4ccncc34)c(C#N)c21]
I-158-ii
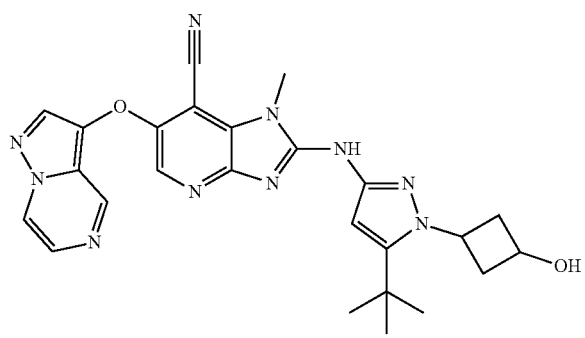 [SMILES: Cn1c(Nc2cc(C(C)(C)C)n(C3CC(O)C3)n2)nc2ncc(Oc3cnn4ccncc34)c(C#N)c21]
I-158'
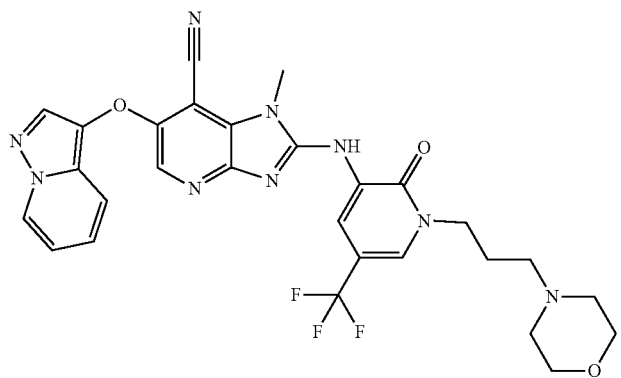 [SMILES: Cn1c(Nc2cc(C(F)(F)F)cn(CCCN3CCOCC3)c2=O)nc2ncc(Oc3cnn4ccccc34)c(C#N)c21]
I-159

I-160
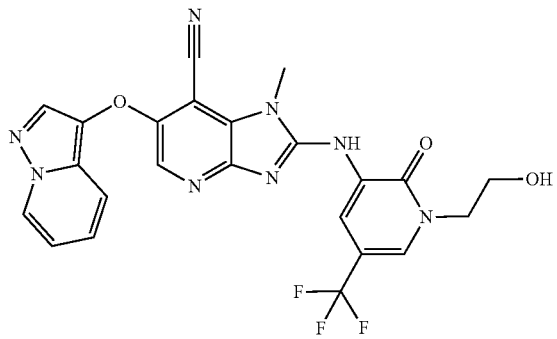 [SMILES: Cn1c(Nc2cc(C(F)(F)F)cn(CCO)c2=O)nc2ncc(Oc3cnn4ccccc34)c(C#N)c21]
I-161
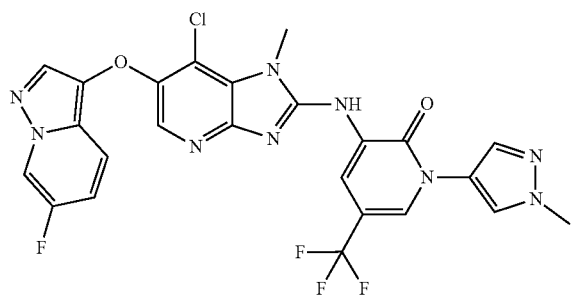 [SMILES: Cn1cc(-n2cc(C(F)(F)F)cc(Nc3nc4ncc(Oc5cnn6cc(F)ccc56)c(Cl)c4n3C)c2=O)cn1]
I-162
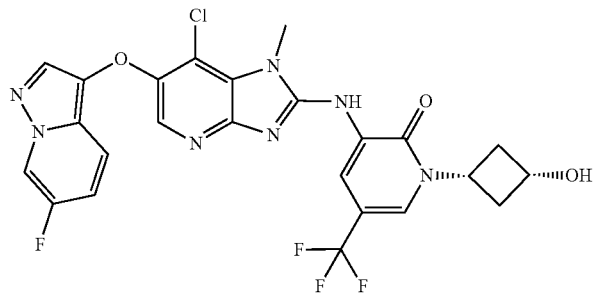 [SMILES: Cn1c(Nc2cc(C(F)(F)F)cn([C@H]3C[C@@H](O)C3)c2=O)nc2ncc(Oc3cnn4cc(F)ccc34)c(Cl)c21]
I-162-ii
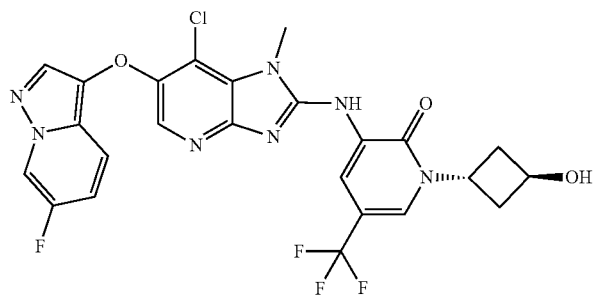 [SMILES: Cn1c(Nc2cc(C(F)(F)F)cn([C@H]3C[C@H](O)C3)c2=O)nc2ncc(Oc3cnn4cc(F)ccc34)c(Cl)c21]
I-162'
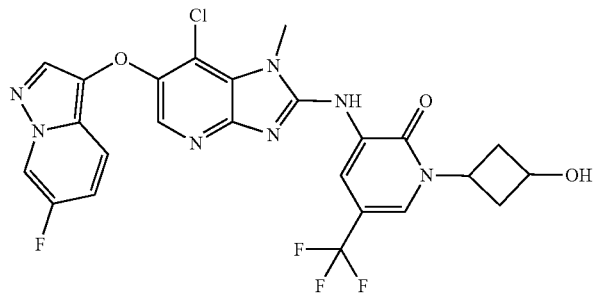 [SMILES: Cn1c(Nc2cc(C(F)(F)F)cn(C3CC(O)C3)c2=O)nc2ncc(Oc3cnn4cc(F)ccc34)c(Cl)c21]

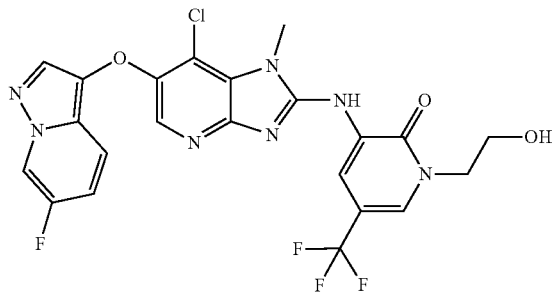
I-163
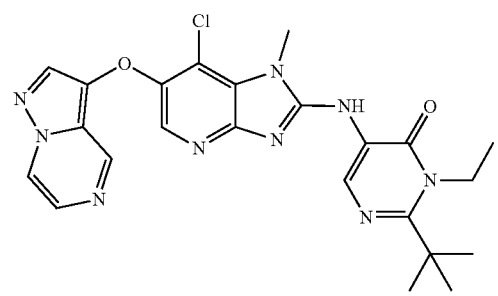 [SMILES: CCn1c(C(C)(C)C)ncc(Nc2nc3ncc(Oc4cnn5ccncc45)c(Cl)c3n2C)c1=O]
I-164
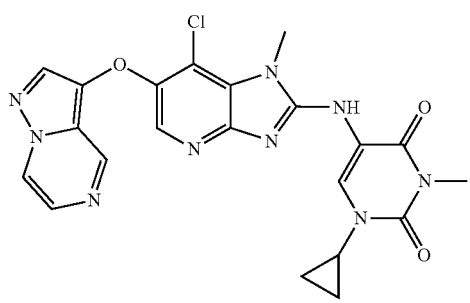 [SMILES: Cn1c(=O)c(Nc2nc3ncc(Oc4cnn5ccncc45)c(Cl)c3n2C)cn(C2CC2)c1=O]
I-165
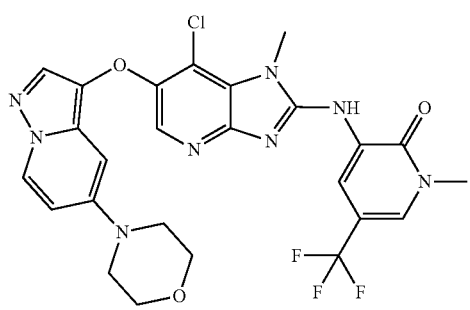 [SMILES: Cn1cc(C(F)(F)F)cc(Nc2nc3ncc(Oc4cnn5ccc(N6CCOCC6)cc45)c(Cl)c3n2C)c1=O]
I-166
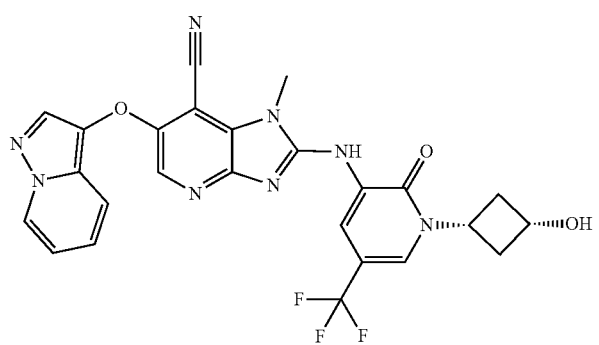 [SMILES: Cn1c(Nc2cc(C(F)(F)F)cn([C@H]3C[C@@H](O)C3)c2=O)nc2ncc(Oc3cnn4ccccc34)c(C#N)c21]
I-167

-continued
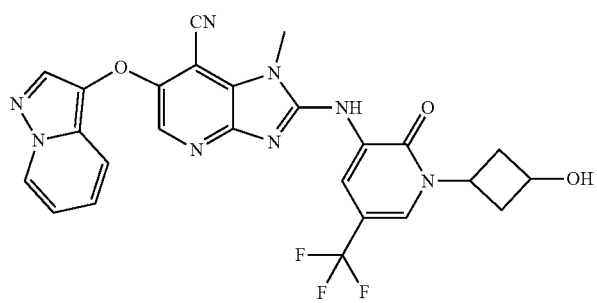 [SMILES: Cn1c(Nc2cc(C(F)(F)F)cn(C3CC(O)C3)c2=O)nc2ncc(Oc3cnn4ccccc34)c(C#N)c21]
I-167'
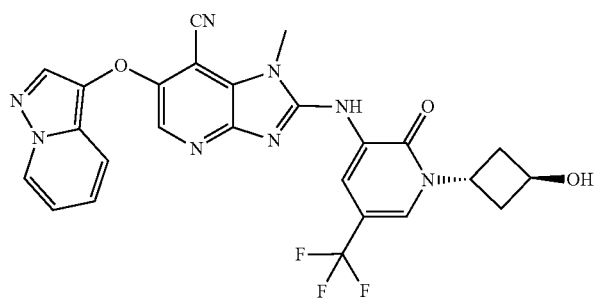 [SMILES: Cn1c(Nc2cc(C(F)(F)F)cn([C@H]3C[C@H](O)C3)c2=O)nc2ncc(Oc3cnn4ccccc34)c(C#N)c21]
I-167-ii
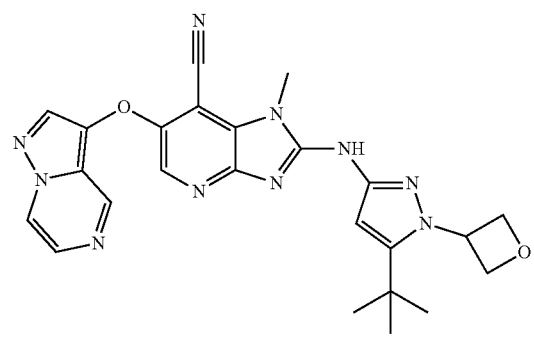 [SMILES: Cn1c(Nc2cc(C(C)(C)C)n(C3COC3)n2)nc2ncc(Oc3cnn4ccncc34)c(C#N)c21]
I-168
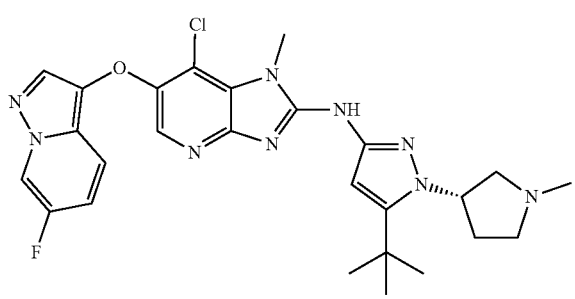 [SMILES: CN1CC[C@H](n2nc(Nc3nc4ncc(Oc5cnn6cc(F)ccc56)c(Cl)c4n3C)cc2C(C)(C)C)C1]
I-169
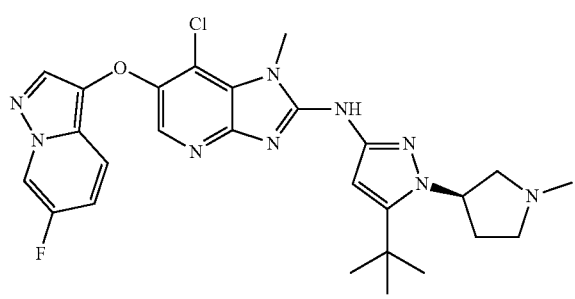 [SMILES: CN1CC[C@@H](n2nc(Nc3nc4ncc(Oc5cnn6cc(F)ccc56)c(Cl)c4n3C)cc2C(C)(C)C)C1]
I-170

I-169'
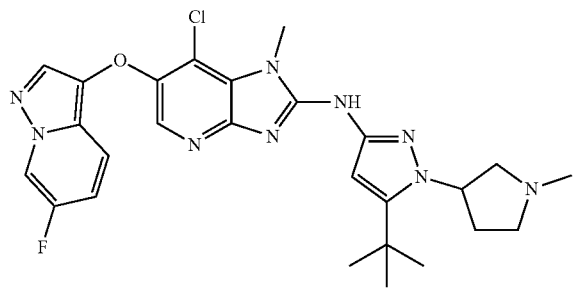 [SMILES: CN1CCC(n2nc(Nc3nc4ncc(Oc5cnn6cc(F)ccc56)c(Cl)c4n3C)cc2C(C)(C)C)C1]
I-171
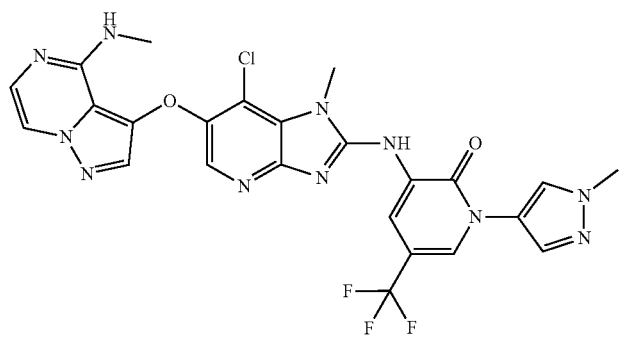 [SMILES: CNc1nccn2ncc(Oc3cnc4nc(Nc5cc(C(F)(F)F)cn(-c6cnn(C)c6)c5=O)n(C)c4c3Cl)c12]
I-172
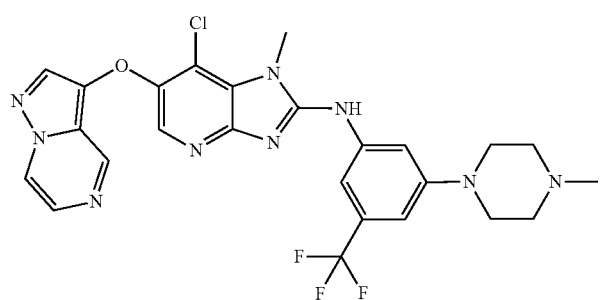 [SMILES: CN1CCN(c2cc(Nc3nc4ncc(Oc5cnn6ccncc56)c(Cl)c4n3C)cc(C(F)(F)F)c2)CC1]
I-173
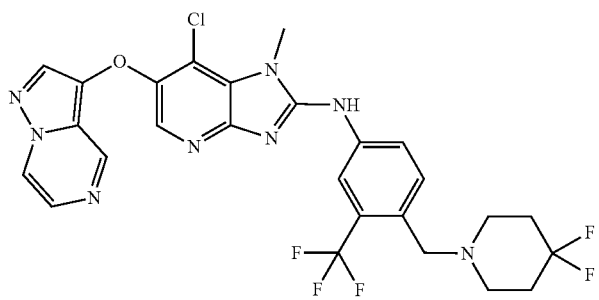 [SMILES: Cn1c(Nc2ccc(CN3CCC(F)(F)CC3)c(C(F)(F)F)c2)nc2ncc(Oc3cnn4ccncc34)c(Cl)c21]
I-174
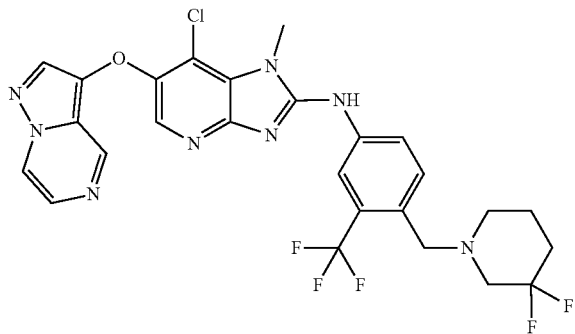 [SMILES: Cn1c(Nc2ccc(CN3CCCC(F)(F)C3)c(C(F)(F)F)c2)nc2ncc(Oc3cnn4ccncc34)c(Cl)c21]

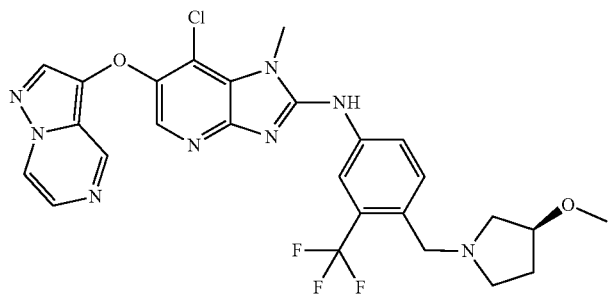 [SMILES: CO[C@H]1CCN(Cc2ccc(Nc3nc4ncc(Oc5cnn6ccncc56)c(Cl)c4n3C)cc2C(F)(F)F)C1]
I-175
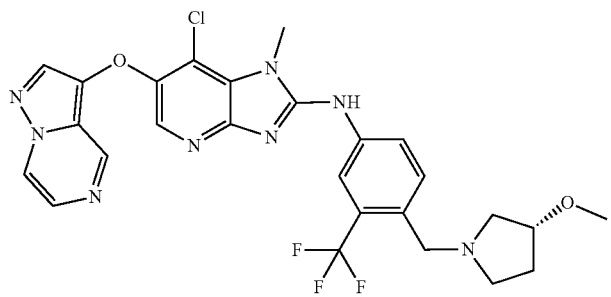 [SMILES: CO[C@@H]1CCN(Cc2ccc(Nc3nc4ncc(Oc5cnn6ccncc56)c(Cl)c4n3C)cc2C(F)(F)F)C1]
I-176
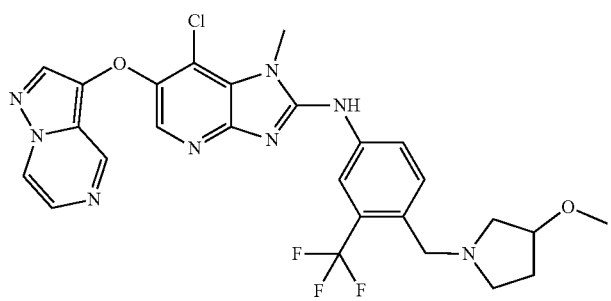 [SMILES: COC1CCN(Cc2ccc(Nc3nc4ncc(Oc5cnn6ccncc56)c(Cl)c4n3C)cc2C(F)(F)F)C1]
I-175'
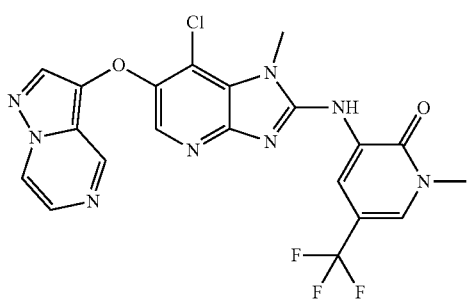 [SMILES: Cn1cc(C(F)(F)F)cc(Nc2nc3ncc(Oc4cnn5ccncc45)c(Cl)c3n2C)c1=O]
I-177
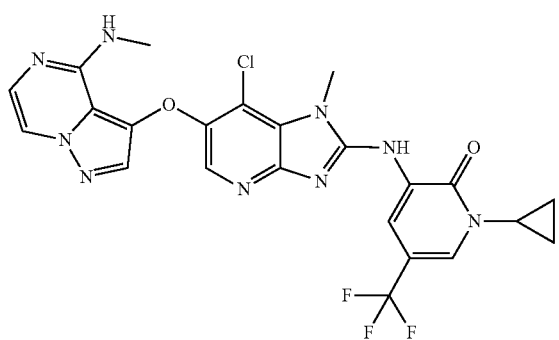 [SMILES: CNc1nccn2ncc(Oc3cnc4nc(Nc5cc(C(F)(F)F)cn(C6CC6)c5=O)n(C)c4c3Cl)c12]
I-178

-continued

I-179

I-180

I-181

I-182

I-181'

-continued
I-183
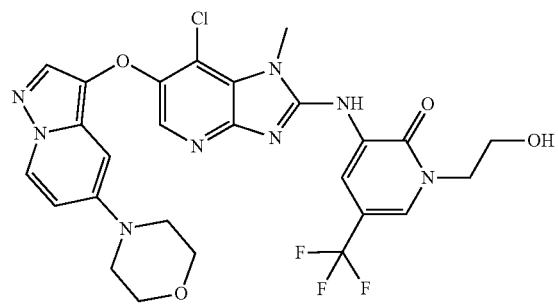 [SMILES: Cn1c(Nc2cc(C(F)(F)F)cn(CCO)c2=O)nc2ncc(Oc3cnn4ccc(N5CCOCC5)cc34)c(Cl)c21]
I-184
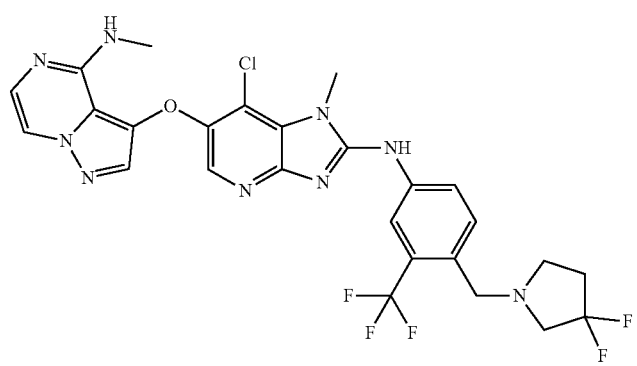 [SMILES: CNc1nccn2ncc(Oc3cnc4nc(Nc5ccc(CN6CCC(F)(F)C6)c(C(F)(F)F)c5)n(C)c4c3Cl)c12]
I-185
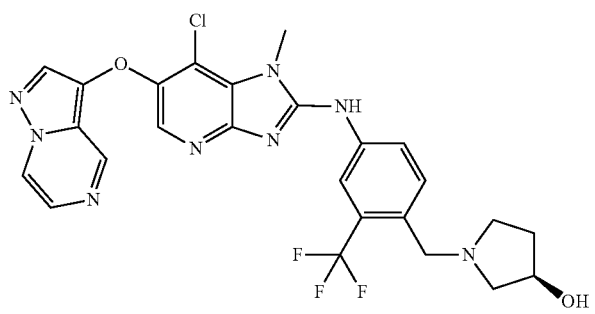 [SMILES: Cn1c(Nc2ccc(CN3CC[C@@H](O)C3)c(C(F)(F)F)c2)nc2ncc(Oc3cnn4ccncc34)c(Cl)c21]
I-186
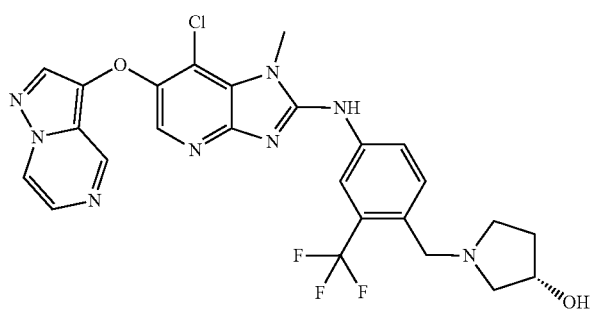 [SMILES: Cn1c(Nc2ccc(CN3CC[C@H](O)C3)c(C(F)(F)F)c2)nc2ncc(Oc3cnn4ccncc34)c(Cl)c21]
I-185'
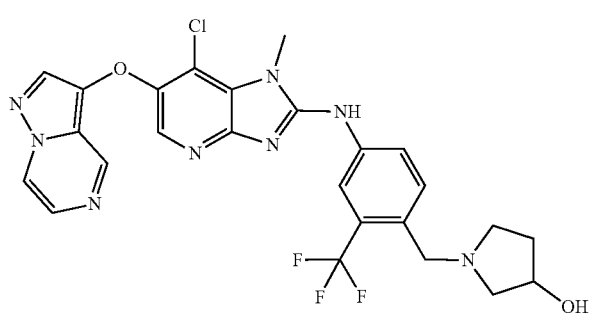 [SMILES: Cn1c(Nc2ccc(CN3CCC(O)C3)c(C(F)(F)F)c2)nc2ncc(Oc3cnn4ccncc34)c(Cl)c21]

I-187
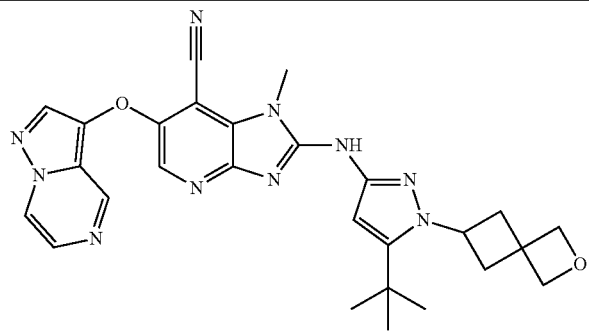
I-188
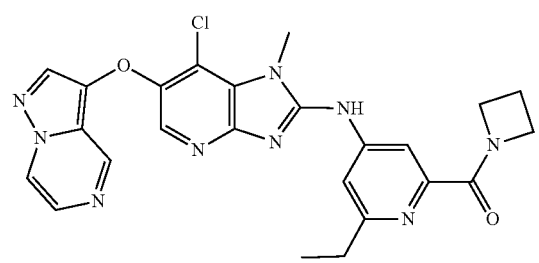 [SMILES: CCc1cc(Nc2nc3ncc(Oc4cnn5ccncc45)c(Cl)c3n2C)cc(C(=O)N2CCC2)n1]
I-189
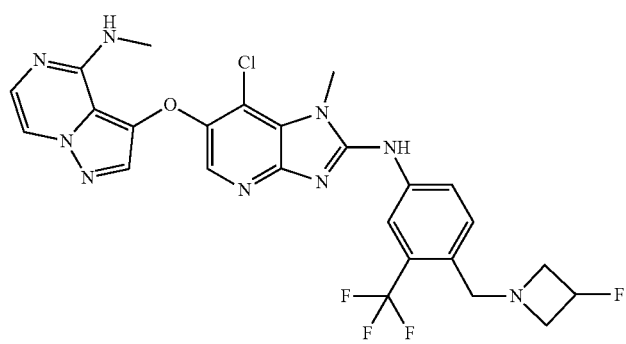 [SMILES: CNc1nccn2ncc(Oc3cnc4nc(Nc5ccc(CN6CC(F)C6)c(C(F)(F)F)c5)n(C)c4c3Cl)c12]
I-190
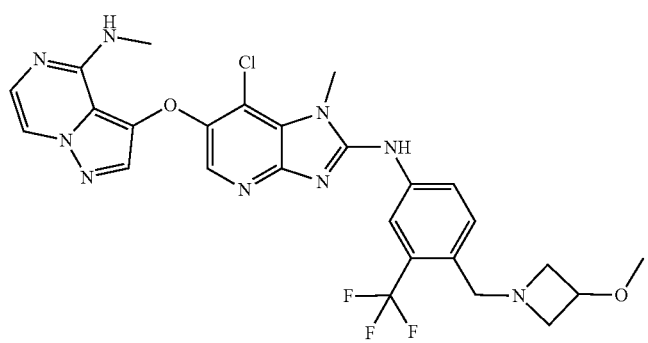 [SMILES: CNc1nccn2ncc(Oc3cnc4nc(Nc5ccc(CN6CC(OC)C6)c(C(F)(F)F)c5)n(C)c4c3Cl)c12]
I-191
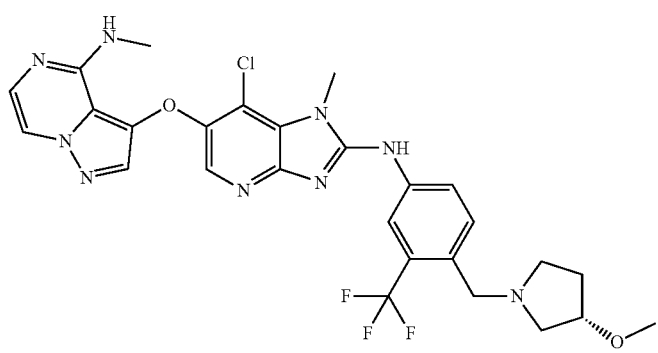

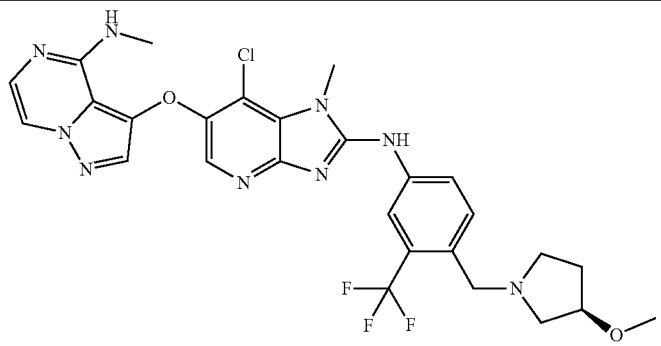
I-192
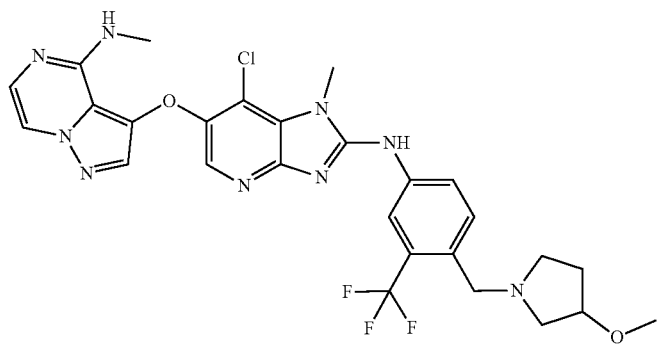 [SMILES: CNc1nccn2ncc(Oc3cnc4nc(Nc5ccc(CN6CCC(OC)C6)c(C(F)(F)F)c5)n(C)c4c3Cl)c12]
I-192'
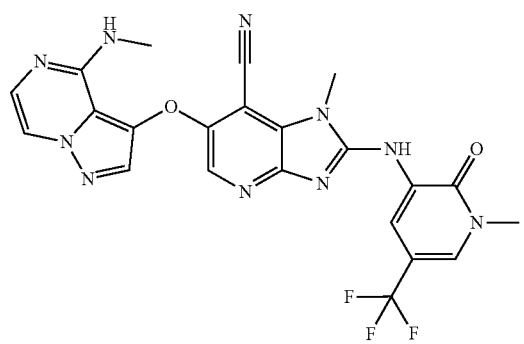 [SMILES: CNc1nccn2ncc(Oc3cnc4nc(Nc5cc(C(F)(F)F)cn(C)c5=O)n(C)c4c3C#N)c12]
I-193
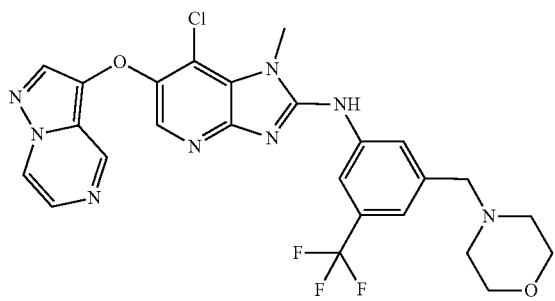 [SMILES: Cn1c(Nc2cc(CN3CCOCC3)cc(C(F)(F)F)c2)nc2ncc(Oc3cnn4ccncc34)c(Cl)c21]
I-194
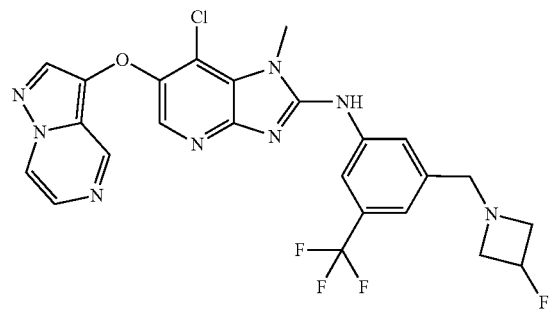 [SMILES: Cn1c(Nc2cc(CN3CC(F)C3)cc(C(F)(F)F)c2)nc2ncc(Oc3cnn4ccncc34)c(Cl)c21]
I-195

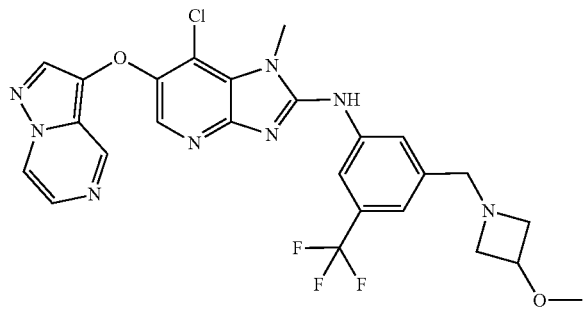 [SMILES: COC1CN(Cc2cc(Nc3nc4ncc(Oc5cnn6ccncc56)c(Cl)c4n3C)cc(C(F)(F)F)c2)C1]
I-196
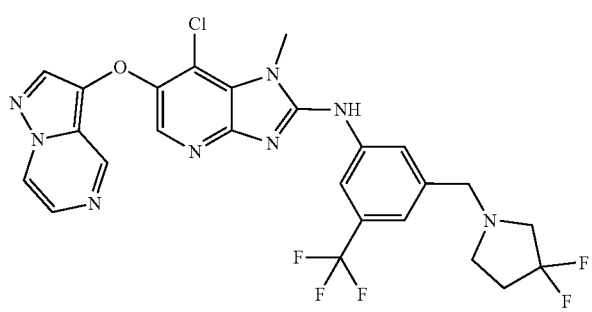 [SMILES: Cn1c(Nc2cc(CN3CCC(F)(F)C3)cc(C(F)(F)F)c2)nc2ncc(Oc3cnn4ccncc34)c(Cl)c21]
I-197
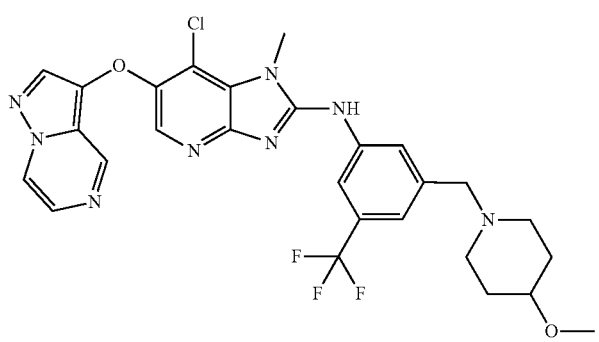 [SMILES: COC1CCN(Cc2cc(Nc3nc4ncc(Oc5cnn6ccncc56)c(Cl)c4n3C)cc(C(F)(F)F)c2)CC1]
I-198
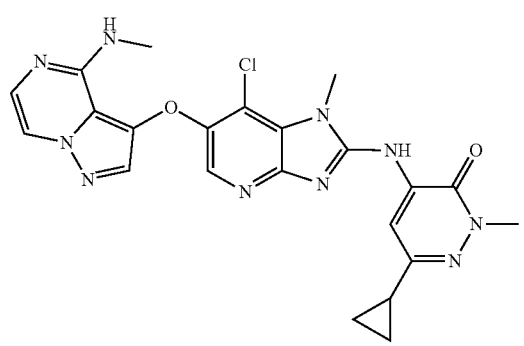
I-199
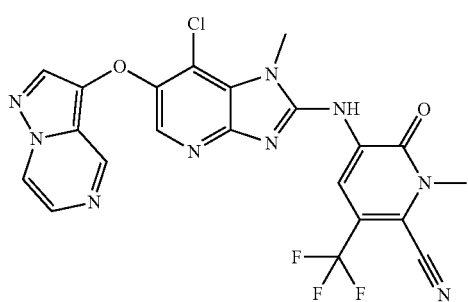 [SMILES: Cn1c(C#N)c(C(F)(F)F)cc(Nc2nc3ncc(Oc4cnn5ccncc45)c(Cl)c3n2C)c1=O]
I-200

-continued
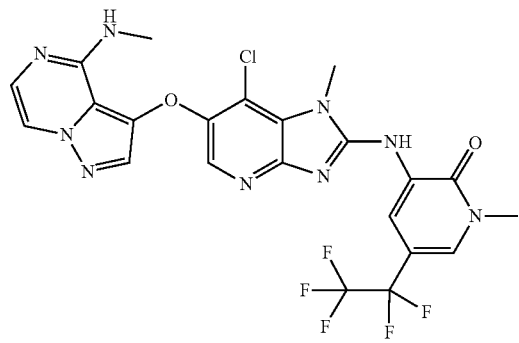 [SMILES: CNc1nccn2ncc(Oc3cnc4nc(Nc5cc(C(F)(F)C(F)(F)F)cn(C)c5=O)n(C)c4c3Cl)c12]
I-201
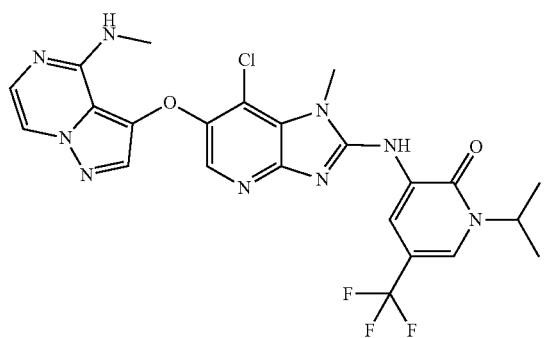 [SMILES: CNc1nccn2ncc(Oc3cnc4nc(Nc5cc(C(F)(F)F)cn(C(C)C)c5=O)n(C)c4c3Cl)c12]
I-202
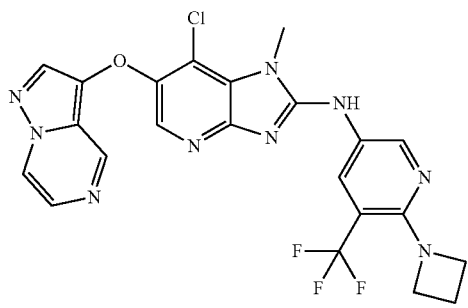 [SMILES: Cn1c(Nc2cnc(N3CCC3)c(C(F)(F)F)c2)nc2ncc(Oc3cnn4ccncc34)c(Cl)c21]
I-203
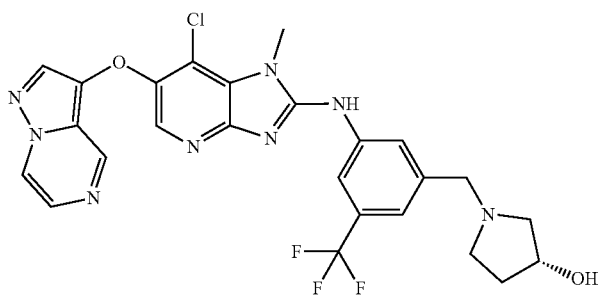 [SMILES: Cn1c(Nc2cc(CN3CC[C@@H](O)C3)cc(C(F)(F)F)c2)nc2ncc(Oc3cnn4ccncc34)c(Cl)c21]
I-204
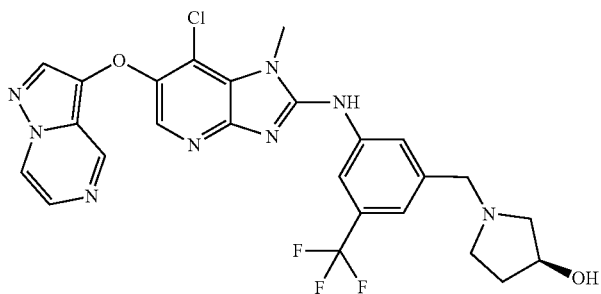 [SMILES: Cn1c(Nc2cc(CN3CC[C@H](O)C3)cc(C(F)(F)F)c2)nc2ncc(Oc3cnn4ccncc34)c(Cl)c21]
I-205

-continued
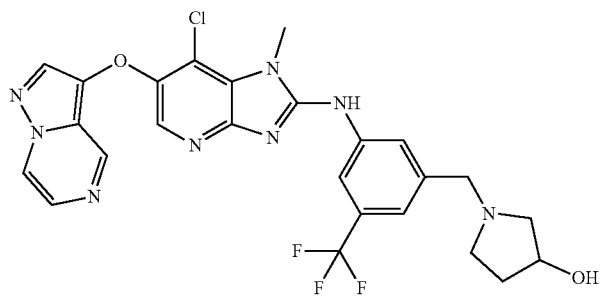
I-204'
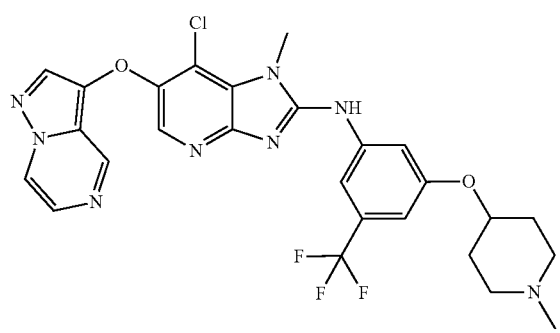 [SMILES: CN1CCC(Oc2cc(Nc3nc4ncc(Oc5cnn6ccncc56)c(Cl)c4n3C)cc(C(F)(F)F)c2)CC1]
I-206
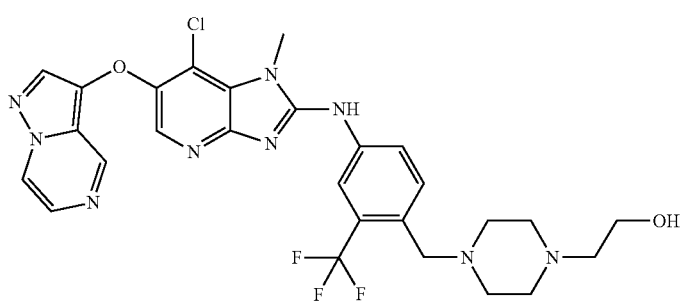 [SMILES: Cn1c(Nc2ccc(CN3CCN(CCO)CC3)c(C(F)(F)F)c2)nc2ncc(Oc3cnn4ccncc34)c(Cl)c21]
I-207
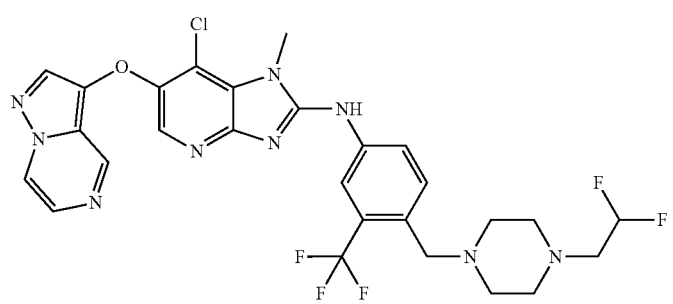 [SMILES: Cn1c(Nc2ccc(CN3CCN(CC(F)F)CC3)c(C(F)(F)F)c2)nc2ncc(Oc3cnn4ccncc34)c(Cl)c21]
I-208
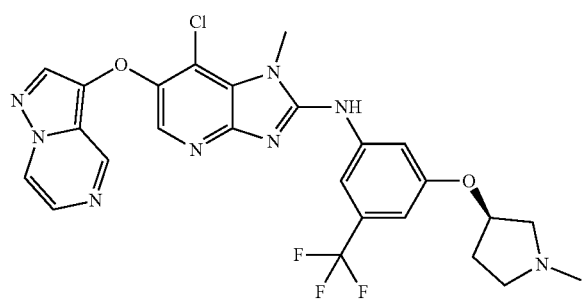 [SMILES: CN1CC[C@@H](Oc2cc(Nc3nc4ncc(Oc5cnn6ccncc56)c(Cl)c4n3C)cc(C(F)(F)F)c2)C1]
I-209

-continued
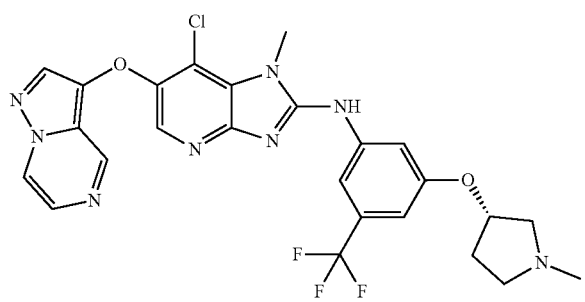
I-210
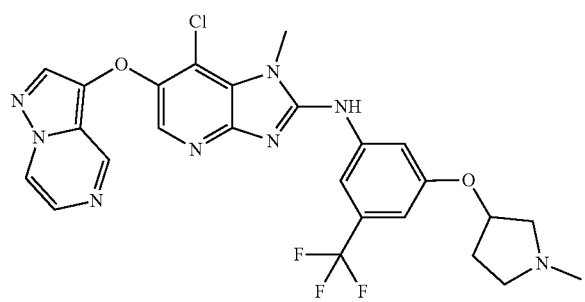 [SMILES: CN1CC[C@H](Oc2cc(Nc3nc4ncc(Oc5cnn6ccncc56)c(Cl)c4n3C)cc(C(F)(F)F)c2)C1]
I-209'
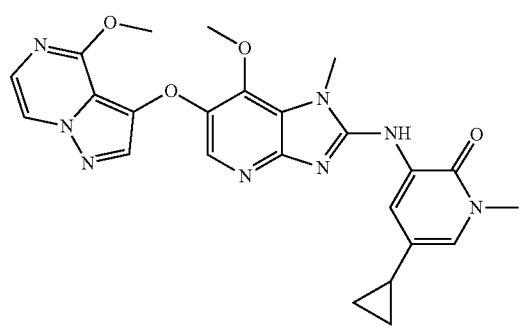 [SMILES: COc1c(Oc2cnn3ccnc(OC)c23)cnc2nc(Nc3cc(C4CC4)cn(C)c3=O)n(C)c12]
I-211
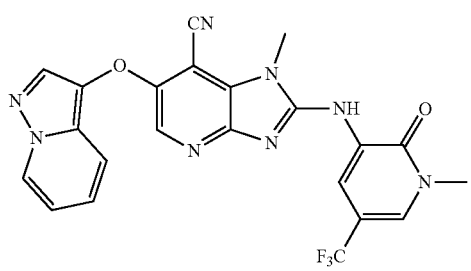 [SMILES: Cn1cc(C(F)(F)F)cc(Nc2nc3ncc(Oc4cnn5ccccc45)c(C#N)c3n2C)c1=O]
I-212
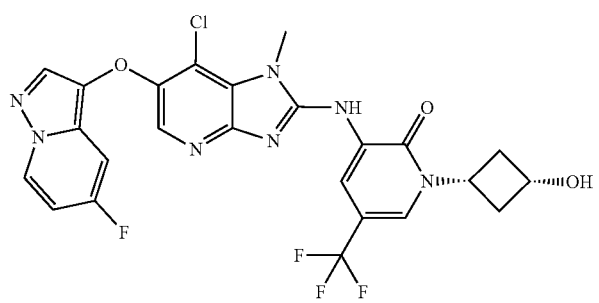 [SMILES: Cn1c(Nc2cc(C(F)(F)F)cn([C@H]3C[C@@H](O)C3)c2=O)nc2ncc(Oc3cnn4ccc(F)cc34)c(Cl)c21]
I-213

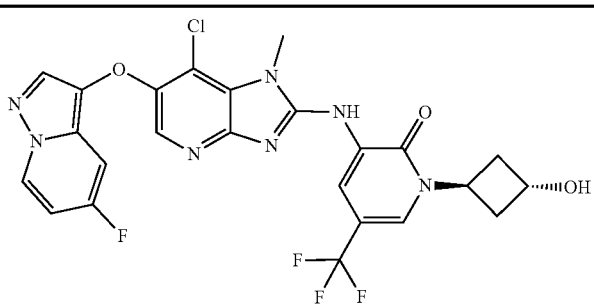
I-213-ii
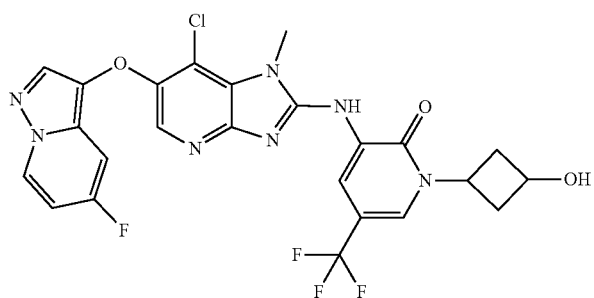 [SMILES: Cn1c(Nc2cc(C(F)(F)F)cn(C3CC(O)C3)c2=O)nc2ncc(Oc3cnn4ccc(F)cc34)c(Cl)c21]
I-213'
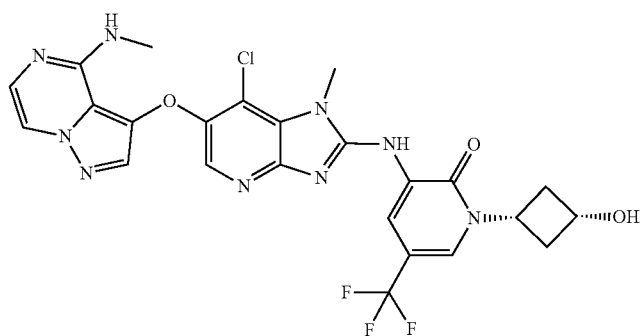 [SMILES: CNc1nccn2ncc(Oc3cnc4nc(Nc5cc(C(F)(F)F)cn([C@H]6C[C@@H](O)C6)c5=O)n(C)c4c3Cl)c12]
I-214
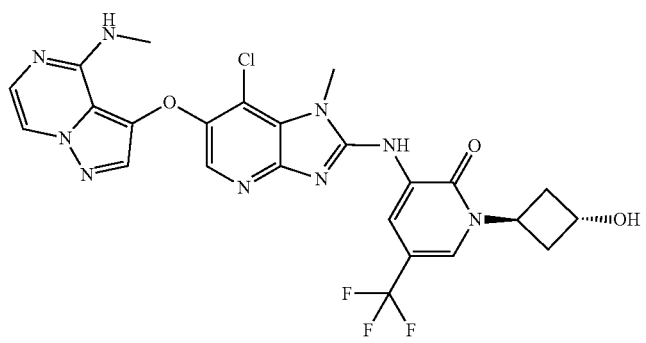 [SMILES: CNc1nccn2ncc(Oc3cnc4nc(Nc5cc(C(F)(F)F)cn([C@H]6C[C@H](O)C6)c5=O)n(C)c4c3Cl)c12]
I-214-ii
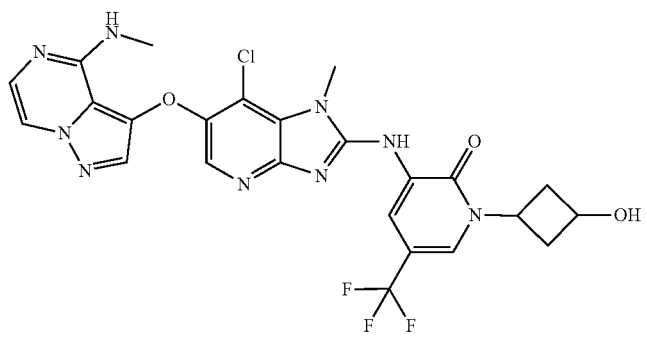 [SMILES: CNc1nccn2ncc(Oc3cnc4nc(Nc5cc(C(F)(F)F)cn(C6CC(O)C6)c5=O)n(C)c4c3Cl)c12]
I-214'

I-215
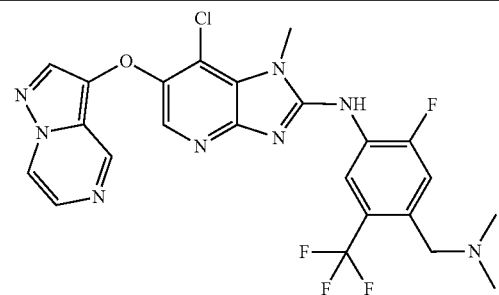
I-216
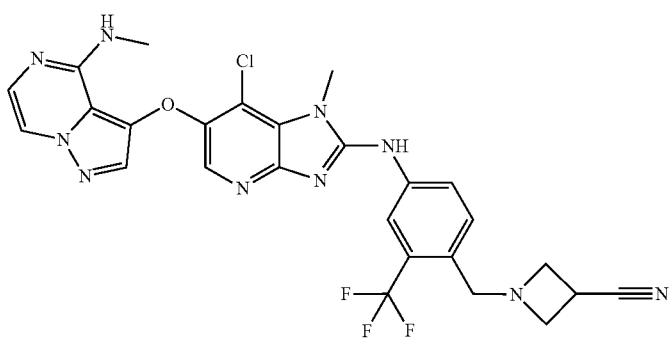 [SMILES: CNc1nccn2ncc(Oc3cnc4nc(Nc5ccc(CN6CC(C#N)C6)c(C(F)(F)F)c5)n(C)c4c3Cl)c12]
I-217
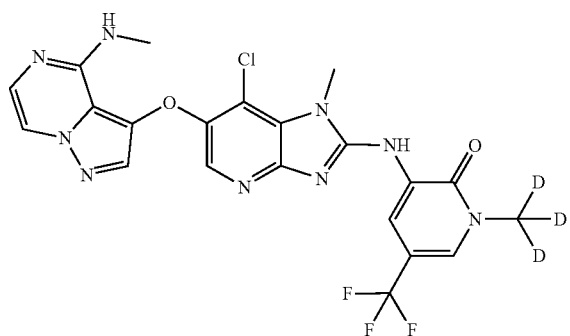 [SMILES: [2H]C([2H])([2H])n1cc(C(F)(F)F)cc(Nc2nc3ncc(Oc4cnn5ccnc(NC)c45)c(Cl)c3n2C)c1=O]
I-218
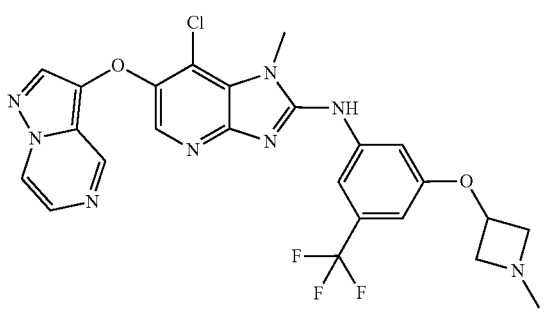 [SMILES: CN1CC(Oc2cc(Nc3nc4ncc(Oc5cnn6ccncc56)c(Cl)c4n3C)cc(C(F)(F)F)c2)C1]
I-219
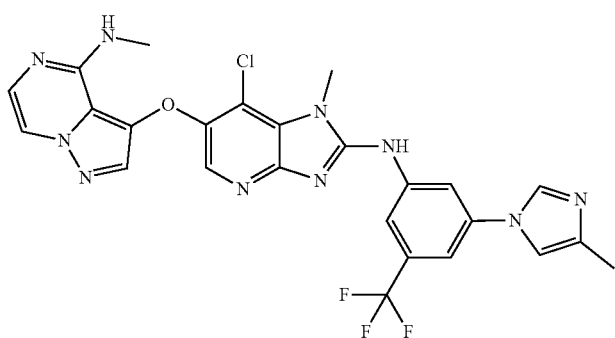 [SMILES: CNc1nccn2ncc(Oc3cnc4nc(Nc5cc(-n6cnc(C)c6)cc(C(F)(F)F)c5)n(C)c4c3Cl)c12]

-continued
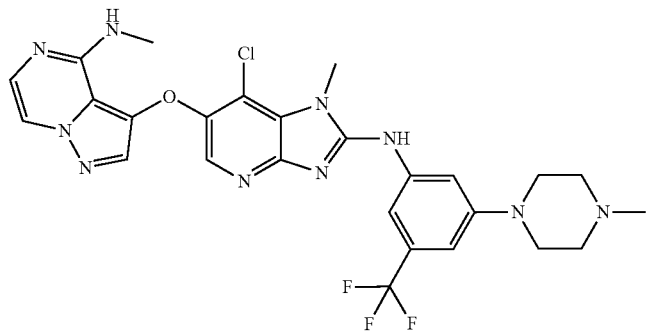 [SMILES: CNc1nccn2ncc(Oc3cnc4nc(Nc5cc(N6CCN(C)CC6)cc(C(F)(F)F)c5)n(C)c4c3Cl)c12]
I-220
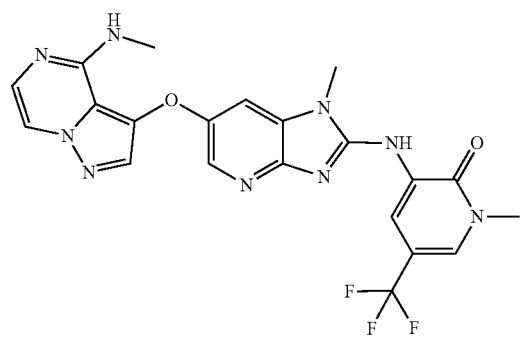 [SMILES: CNc1nccn2ncc(Oc3cnc4nc(Nc5cc(C(F)(F)F)cn(C)c5=O)n(C)c4c3)c12]
I-221
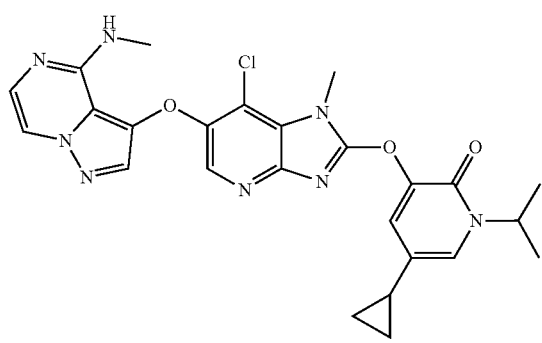 [SMILES: CNc1nccn2ncc(Oc3cnc4nc(Oc5cc(C6CC6)cn(C(C)C)c5=O)n(C)c4c3Cl)c12]
I-222
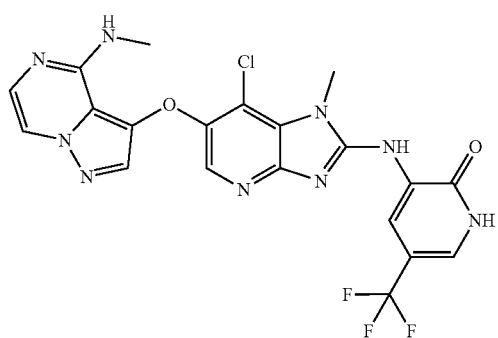 [SMILES: CNc1nccn2ncc(Oc3cnc4nc(Nc5cc(C(F)(F)F)c[nH]c5=O)n(C)c4c3Cl)c12]
I-223

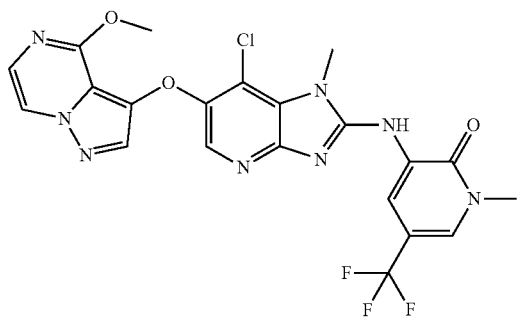 [SMILES: COc1nccn2ncc(Oc3cnc4nc(Nc5cc(C(F)(F)F)cn(C)c5=O)n(C)c4c3Cl)c12]
I-224
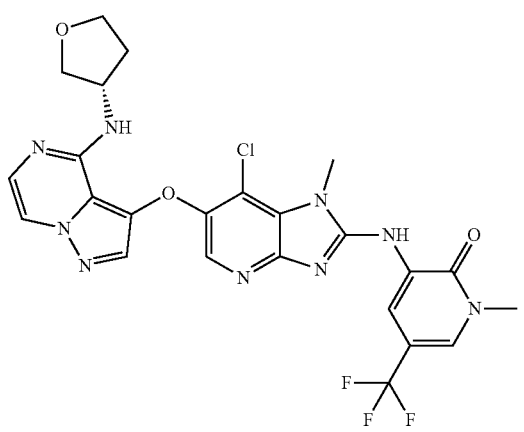 [SMILES: Cn1cc(C(F)(F)F)cc(Nc2nc3ncc(Oc4cnn5ccnc(N[C@H]6CCOC6)c45)c(Cl)c3n2C)c1=O]
I-225
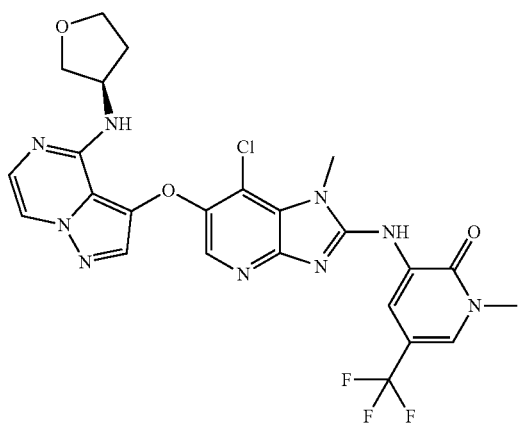 [SMILES: Cn1cc(C(F)(F)F)cc(Nc2nc3ncc(Oc4cnn5ccnc(N[C@@H]6CCOC6)c45)c(Cl)c3n2C)c1=O]
I-225-ii
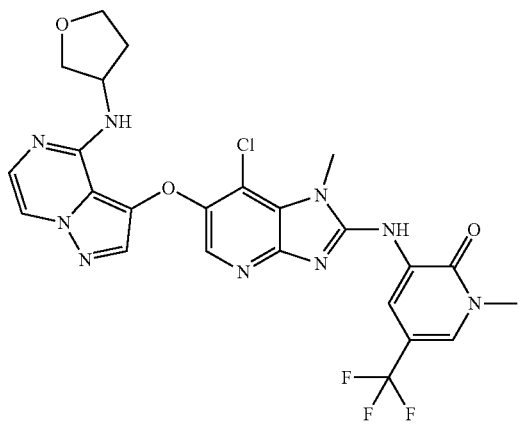 [SMILES: Cn1cc(C(F)(F)F)cc(Nc2nc3ncc(Oc4cnn5ccnc(NC6CCOC6)c45)c(Cl)c3n2C)c1=O]
I-225'

-continued
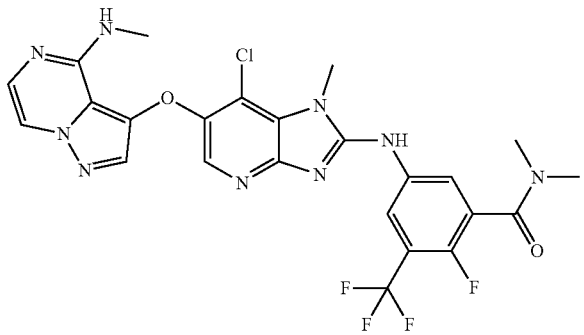 [SMILES: CNc1nccn2ncc(Oc3cnc4nc(Nc5cc(C(=O)N(C)C)c(F)c(C(F)(F)F)c5)n(C)c4c3Cl)c12]
I-226
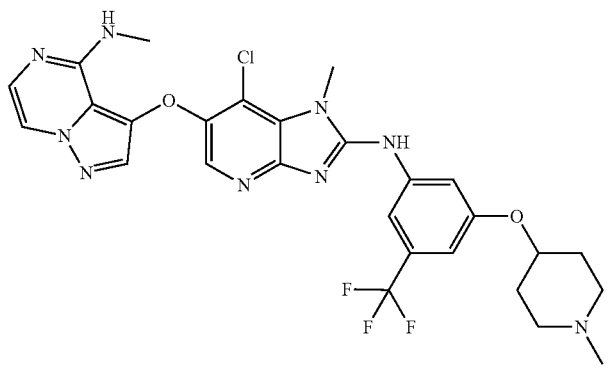 [SMILES: CNc1nccn2ncc(Oc3cnc4nc(Nc5cc(OC6CCN(C)CC6)cc(C(F)(F)F)c5)n(C)c4c3Cl)c12]
I-227
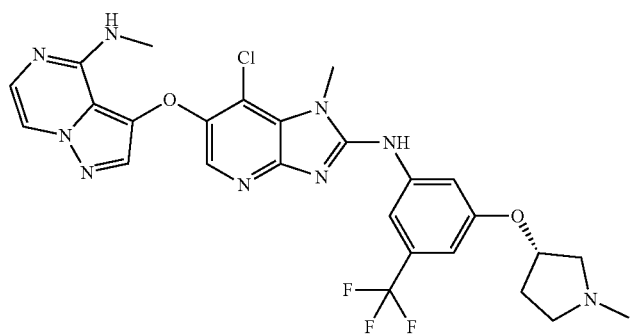 [SMILES: CNc1nccn2ncc(Oc3cnc4nc(Nc5cc(O[C@H]6CCN(C)C6)cc(C(F)(F)F)c5)n(C)c4c3Cl)c12]
I-228
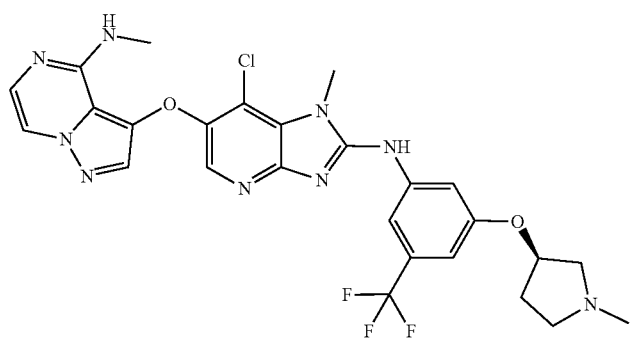 [SMILES: CNc1nccn2ncc(Oc3cnc4nc(Nc5cc(O[C@@H]6CCN(C)C6)cc(C(F)(F)F)c5)n(C)c4c3Cl)c12]
I-229

-continued
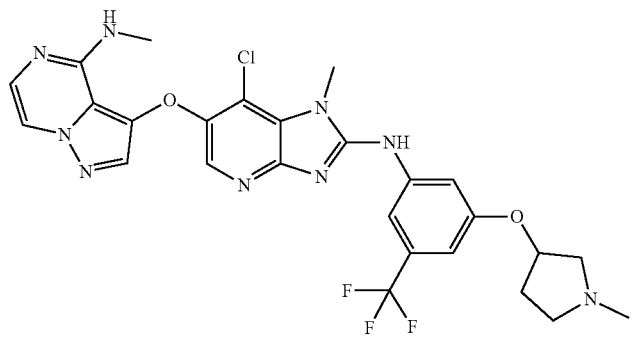 [SMILES: CNc1nccn2ncc(Oc3cnc4nc(Nc5cc(OC6CCN(C)C6)cc(C(F)(F)F)c5)n(C)c4c3Cl)c12]
I-228'
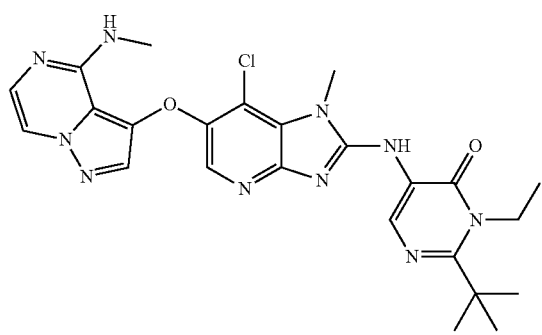 [SMILES: CCn1c(C(C)(C)C)ncc(Nc2nc3ncc(Oc4cnn5ccnc(NC)c45)c(Cl)c3n2C)c1=O]
I-230
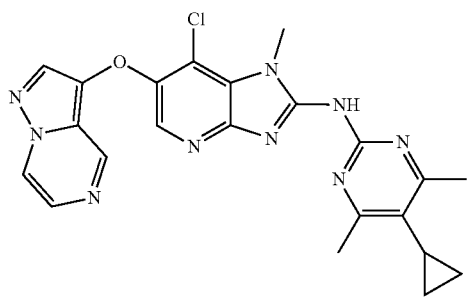 [SMILES: Cc1nc(Nc2nc3ncc(Oc4cnn5ccncc45)c(Cl)c3n2C)nc(C)c1C1CC1]
I-231
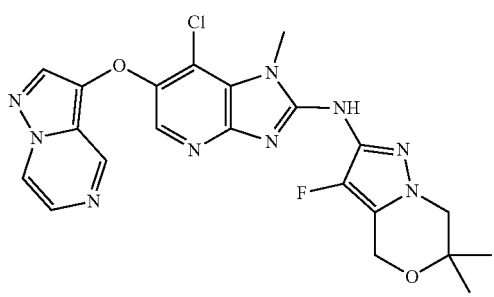 [SMILES: Cn1c(Nc2nn3c(c2F)COC(C)(C)C3)nc2ncc(Oc3cnn4ccncc34)c(Cl)c21]
I-232
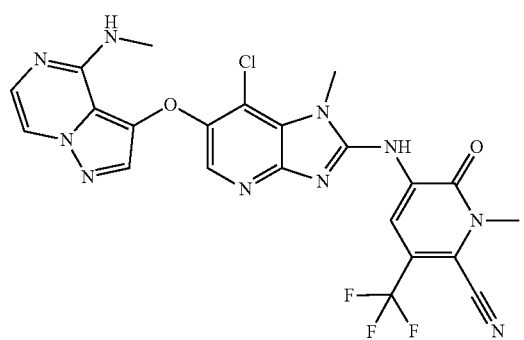 [SMILES: CNc1nccn2ncc(Oc3cnc4nc(Nc5cc(C(F)(F)F)c(C#N)n(C)c5=O)n(C)c4c3Cl)c12]
I-233

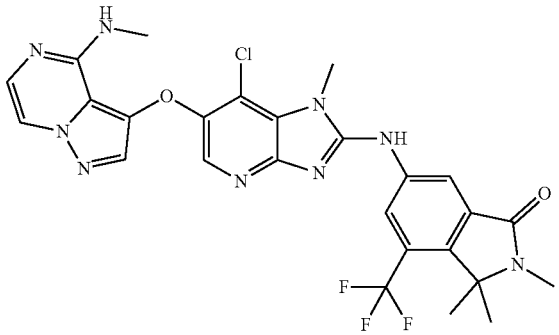 [SMILES: CNc1nccn2ncc(Oc3cnc4nc(Nc5cc6c(c(C(F)(F)F)c5)C(C)(C)N(C)C6=O)n(C)c4c3Cl)c12]
I-234
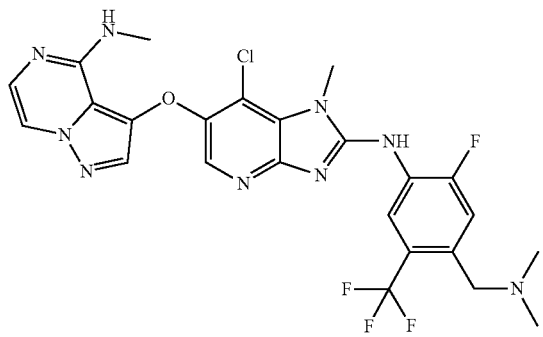 [SMILES: CNc1nccn2ncc(Oc3cnc4nc(Nc5cc(C(F)(F)F)c(CN(C)C)cc5F)n(C)c4c3Cl)c12]
I-235
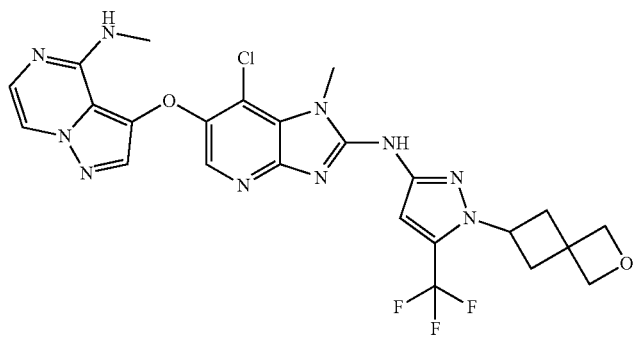 [SMILES: CNc1nccn2ncc(Oc3cnc4nc(Nc5cc(C(F)(F)F)n(C6CC7(COC7)C6)n5)n(C)c4c3Cl)c12]
I-236
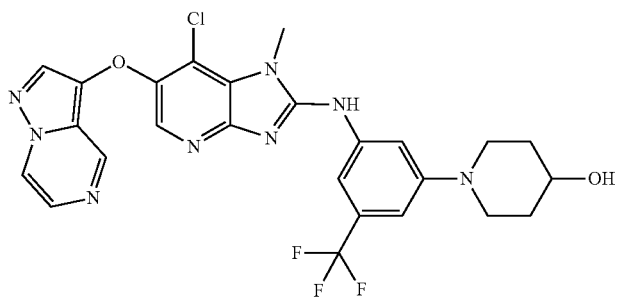 [SMILES: Cn1c(Nc2cc(N3CCC(O)CC3)cc(C(F)(F)F)c2)nc2ncc(Oc3cnn4ccncc34)c(Cl)c21]
I-237
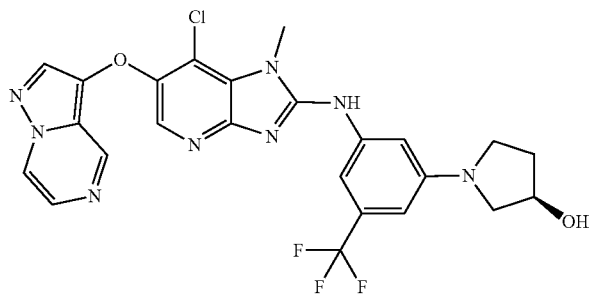 [SMILES: Cn1c(Nc2cc(N3CC[C@@H](O)C3)cc(C(F)(F)F)c2)nc2ncc(Oc3cnn4ccncc34)c(Cl)c21]
I-238

I-239
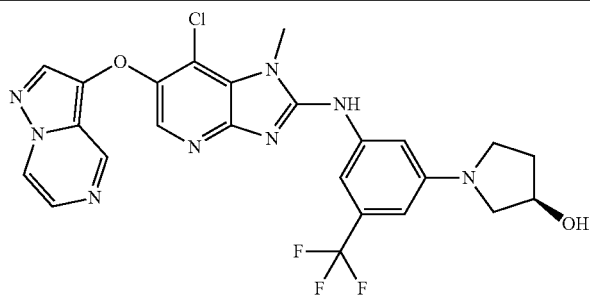
I-238'
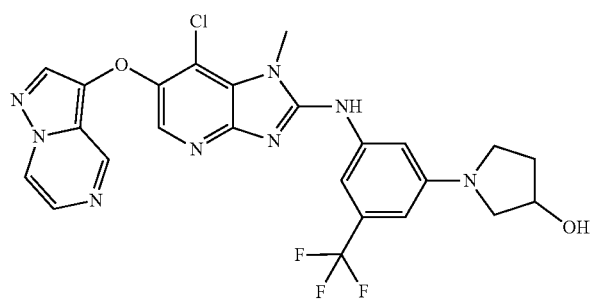 [SMILES: Cn1c(Nc2cc(N3CCC(O)C3)cc(C(F)(F)F)c2)nc2ncc(Oc3cnn4ccncc34)c(Cl)c21]
I-240
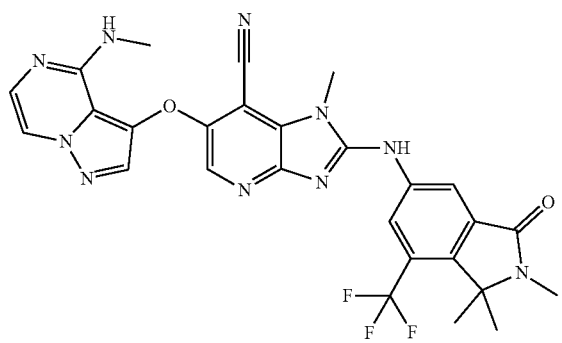 [SMILES: CNc1nccn2ncc(Oc3cnc4nc(Nc5cc6c(c(C(F)(F)F)c5)C(C)(C)N(C)C6=O)n(C)c4c3C#N)c12]
I-241
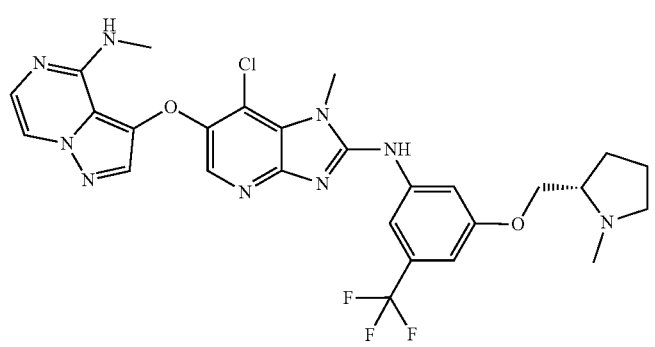 [SMILES: CNc1nccn2ncc(Oc3cnc4nc(Nc5cc(OC[C@@H]6CCCN6C)cc(C(F)(F)F)c5)n(C)c4c3Cl)c12]
I-242
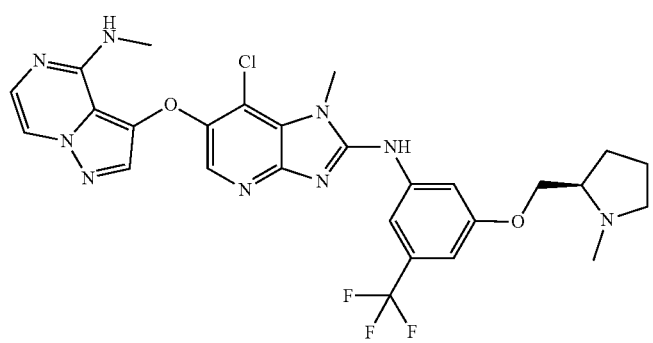 [SMILES: CNc1nccn2ncc(Oc3cnc4nc(Nc5cc(OC[C@H]6CCCN6C)cc(C(F)(F)F)c5)n(C)c4c3Cl)c12]

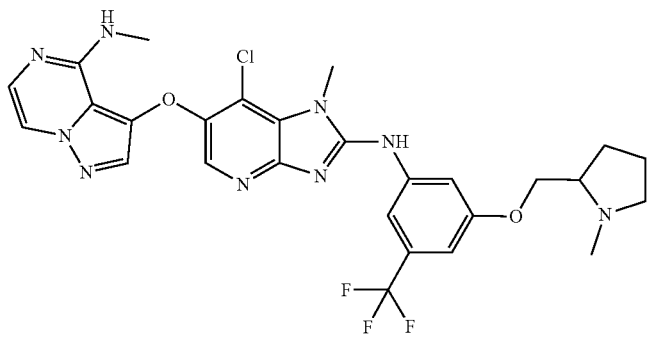 [SMILES: CNc1nccn2ncc(Oc3cnc4nc(Nc5cc(OCC6CCCN6C)cc(C(F)(F)F)c5)n(C)c4c3Cl)c12]
I-241'
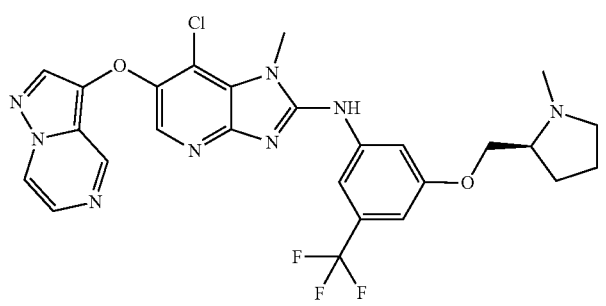 [SMILES: CN1CCC[C@H]1COc1cc(Nc2nc3ncc(Oc4cnn5ccncc45)c(Cl)c3n2C)cc(C(F)(F)F)c1]
I-243
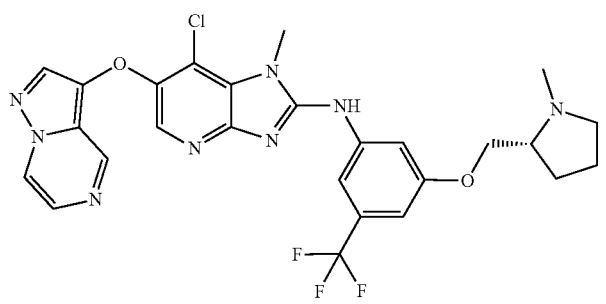 [SMILES: CN1CCCC1COc1cc(Nc2nc3ncc(Oc4cnn5ccncc45)c(Cl)c3n2C)cc(C(F)(F)F)c1]
I-244
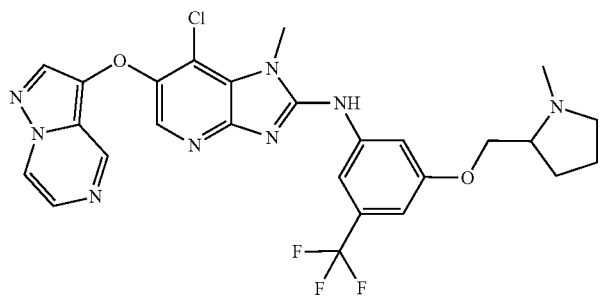
I-243'
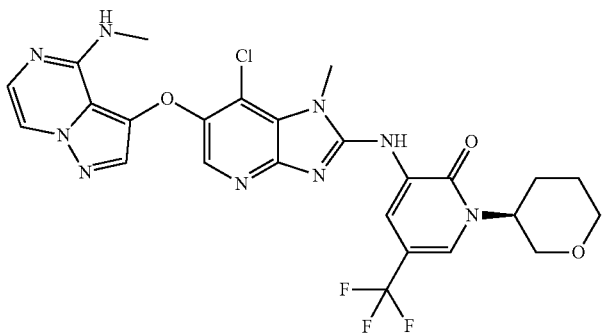 [SMILES: CNc1nccn2ncc(Oc3cnc4nc(Nc5cc(C(F)(F)F)cn([C@H]6CCCOC6)c5=O)n(C)c4c3Cl)c12]
I-245-i -continued
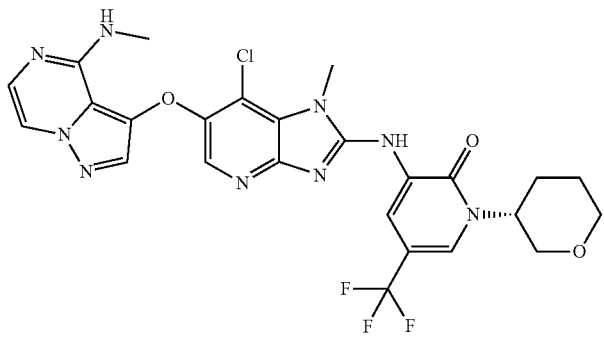 [SMILES: CNc1nccn2ncc(Oc3cnc4nc(Nc5cc(C(F)(F)F)cn([C@@H]6CCCOC6)c5=O)n(C)c4c3Cl)c12]
I-245-ii
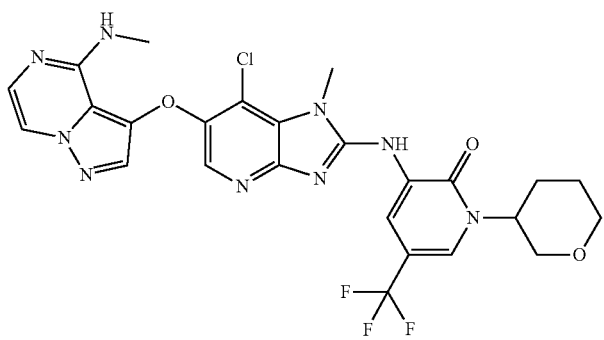 [SMILES: CNc1nccn2ncc(Oc3cnc4nc(Nc5cc(C(F)(F)F)cn(C6CCCOC6)c5=O)n(C)c4c3Cl)c12]
I-245
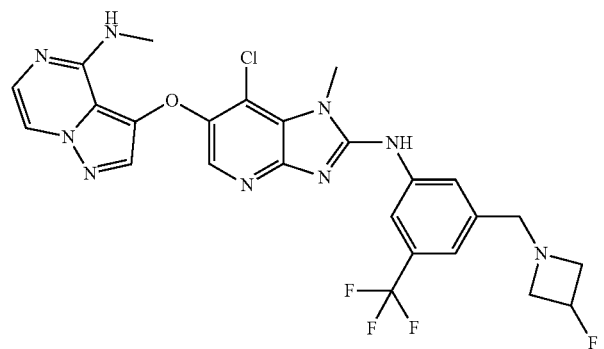 [SMILES: CNc1nccn2ncc(Oc3cnc4nc(Nc5cc(CN6CC(F)C6)cc(C(F)(F)F)c5)n(C)c4c3Cl)c12]
I-246
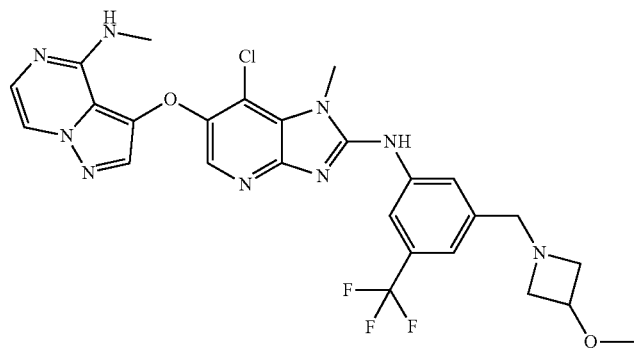 [SMILES: CNc1nccn2ncc(Oc3cnc4nc(Nc5cc(CN6CC(OC)C6)cc(C(F)(F)F)c5)n(C)c4c3Cl)c12]
I-247

I-248
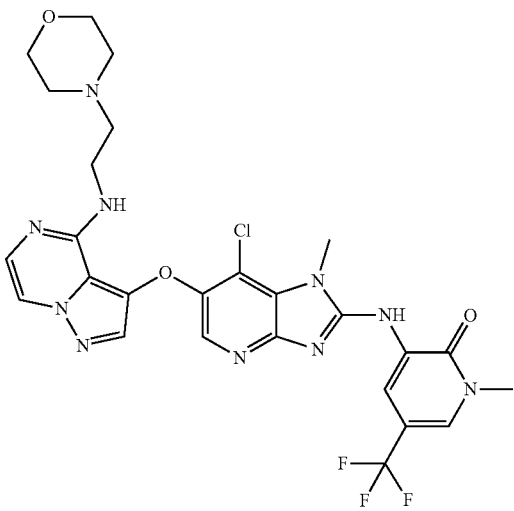 [SMILES: Cn1cc(C(F)(F)F)cc(Nc2nc3ncc(Oc4cnn5ccnc(NCCN6CCOCC6)c45)c(Cl)c3n2C)c1=O]
I-249
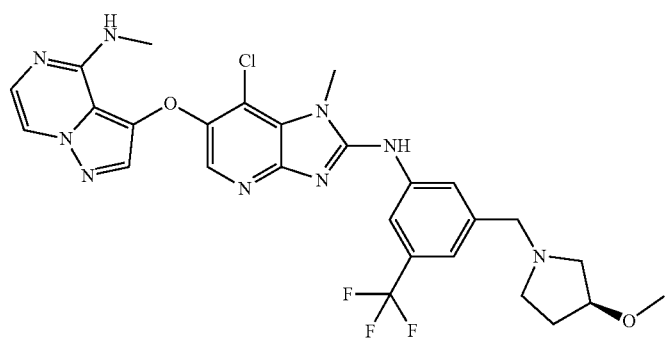 [SMILES: CNc1nccn2ncc(Oc3cnc4nc(Nc5cc(CN6CC[C@H](OC)C6)cc(C(F)(F)F)c5)n(C)c4c3Cl)c12]
I-250
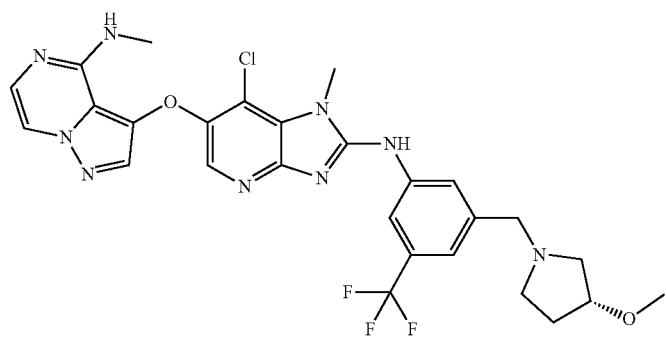
I-249'
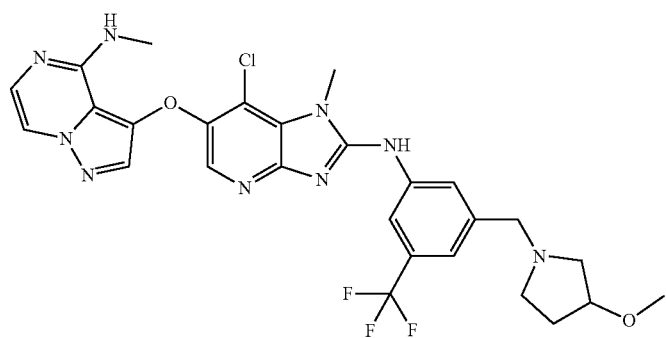 [SMILES: CNc1nccn2ncc(Oc3cnc4nc(Nc5cc(CN6CC[C@@H](OC)C6)cc(C(F)(F)F)c5)n(C)c4c3Cl)c12]

-continued
I-251
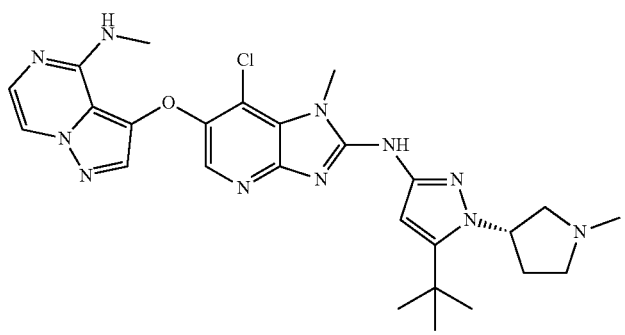 [SMILES: CNc1nccn2ncc(Oc3cnc4nc(Nc5cc(C(C)(C)C)n([C@H]6CCN(C)C6)n5)n(C)c4c3Cl)c12]
I-252
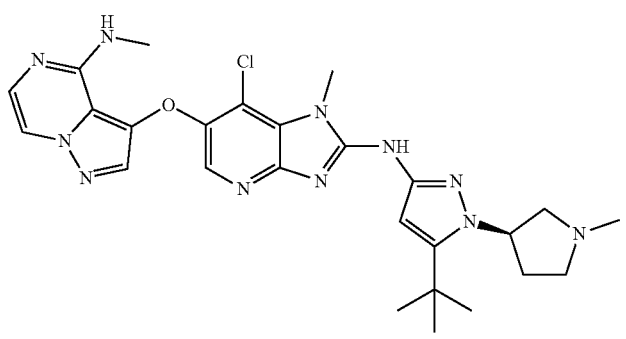 [SMILES: CNc1nccn2ncc(Oc3cnc4nc(Nc5cc(C(C)(C)C)n([C@@H]6CCN(C)C6)n5)n(C)c4c3Cl)c12]
I-251'
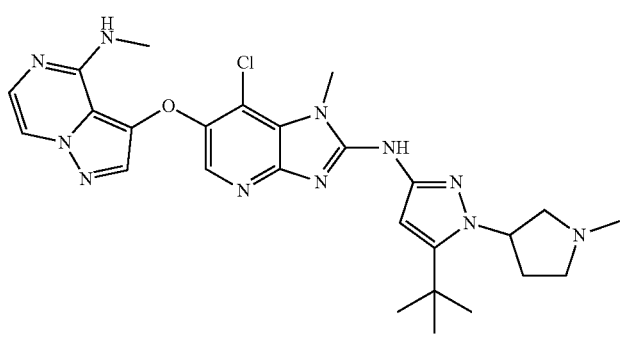 [SMILES: CNc1nccn2ncc(Oc3cnc4nc(Nc5cc(C(C)(C)C)n(C6CCN(C)C6)n5)n(C)c4c3Cl)c12]
I-253
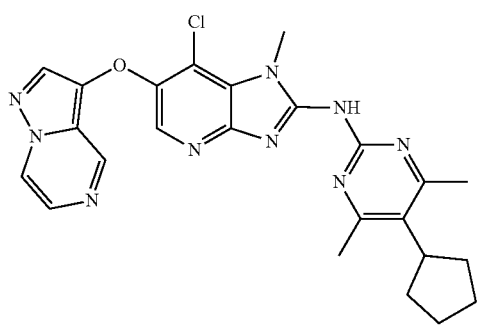 [SMILES: Cc1nc(Nc2nc3ncc(Oc4cnn5ccncc45)c(Cl)c3n2C)nc(C)c1C1CCCC1]

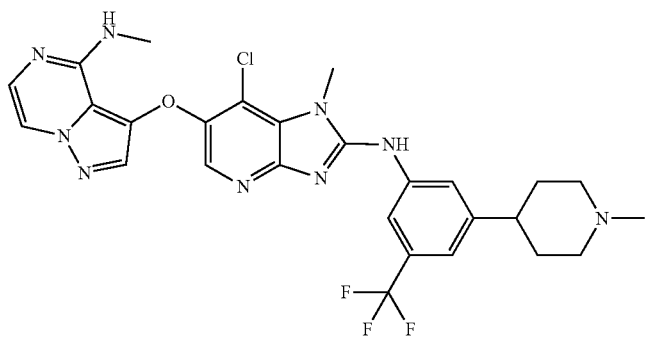 [SMILES: CNc1nccn2ncc(Oc3cnc4nc(Nc5cc(C6CCN(C)CC6)cc(C(F)(F)F)c5)n(C)c4c3Cl)c12]
I-254
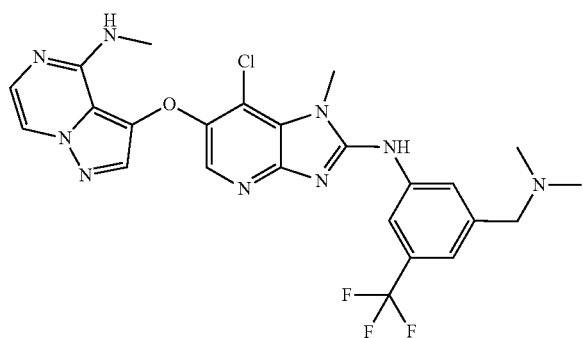 [SMILES: CNc1nccn2ncc(Oc3cnc4nc(Nc5cc(CN(C)C)cc(C(F)(F)F)c5)n(C)c4c3Cl)c12]
I-255
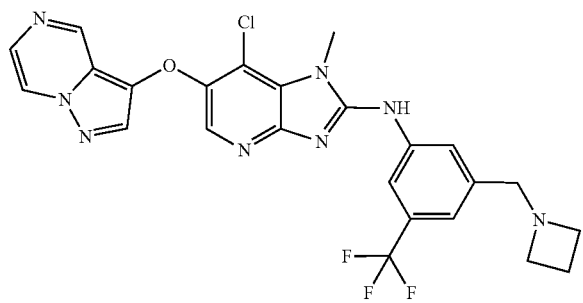 [SMILES: Cn1c(Nc2cc(CN3CCC3)cc(C(F)(F)F)c2)nc2ncc(Oc3cnn4ccncc34)c(Cl)c21]
I-256
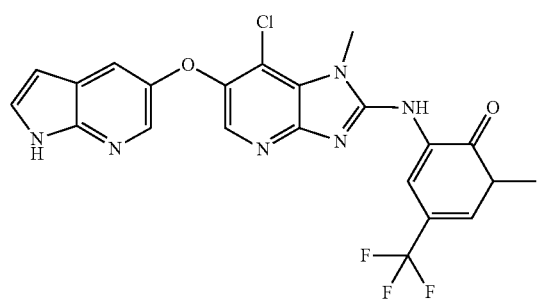 [SMILES: CC1C=C(C(F)(F)F)C=C(Nc2nc3ncc(Oc4cnc5[nH]ccc5c4)c(Cl)c3n2C)C1=O]
I-257
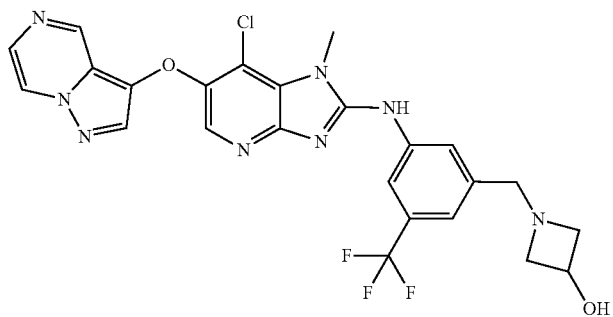 [SMILES: Cn1c(Nc2cc(CN3CC(O)C3)cc(C(F)(F)F)c2)nc2ncc(Oc3cnn4ccncc34)c(Cl)c21]
I-258

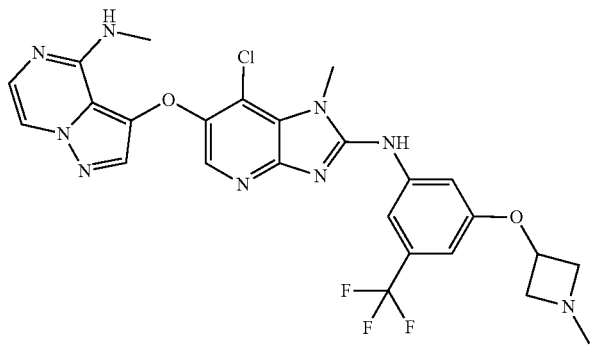 [SMILES: CNc1nccn2ncc(Oc3cnc4nc(Nc5cc(OC6CN(C)C6)cc(C(F)(F)F)c5)n(C)c4c3Cl)c12]
I-259
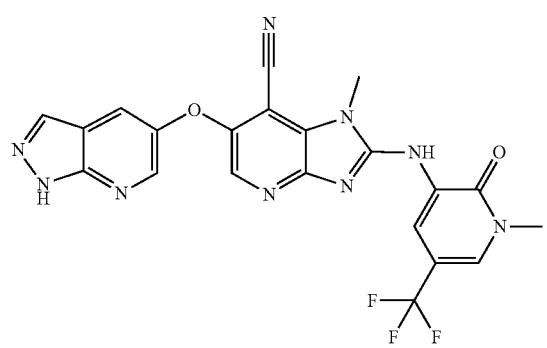 [SMILES: Cn1cc(C(F)(F)F)cc(Nc2nc3ncc(Oc4cnc5[nH]ncc5c4)c(C#N)c3n2C)c1=O]
I-260
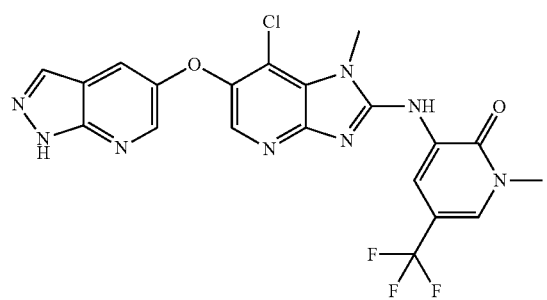 [SMILES: Cn1cc(C(F)(F)F)cc(Nc2nc3ncc(Oc4cnc5[nH]ncc5c4)c(Cl)c3n2C)c1=O]
I-261
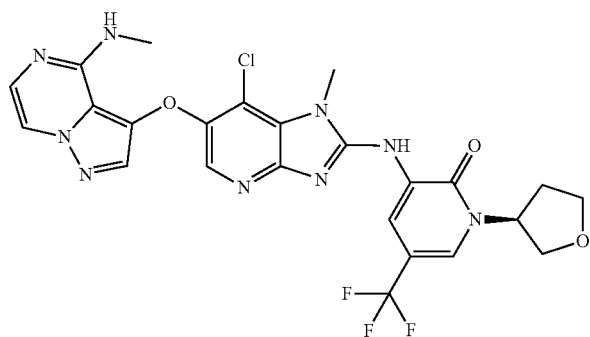 [SMILES: CNc1nccn2ncc(Oc3cnc4nc(Nc5cc(C(F)(F)F)cn([C@H]6CCOC6)c5=O)n(C)c4c3Cl)c12]
I-262-i

-continued
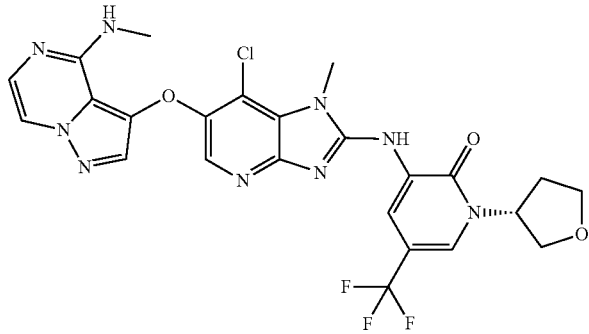
I-262-ii
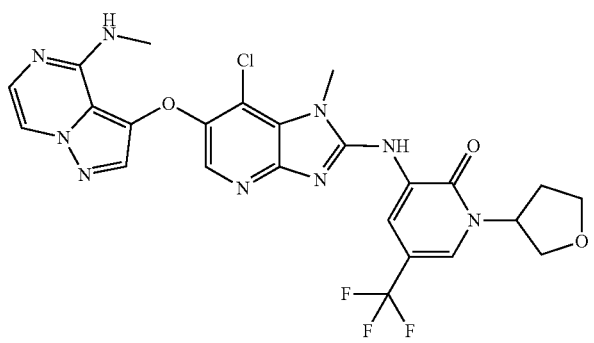 [SMILES: CNc1nccn2ncc(Oc3cnc4nc(Nc5cc(C(F)(F)F)cn(C6CCOC6)c5=O)n(C)c4c3Cl)c12]
I-262
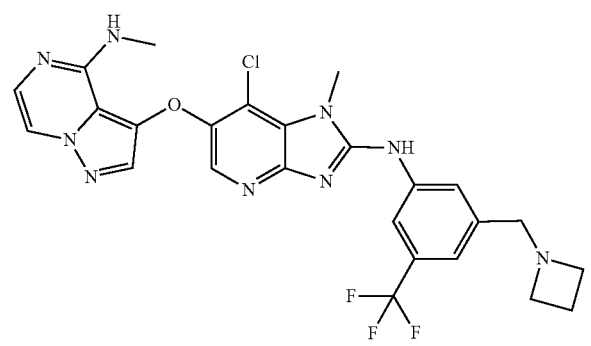 [SMILES: CNc1nccn2ncc(Oc3cnc4nc(Nc5cc(CN6CCC6)cc(C(F)(F)F)c5)n(C)c4c3Cl)c12]
I-263
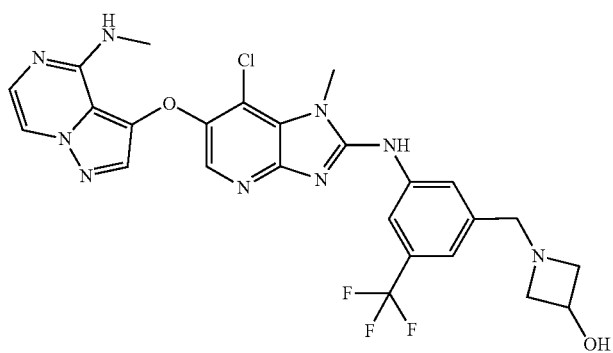 [SMILES: CNc1nccn2ncc(Oc3cnc4nc(Nc5cc(CN6CC(O)C6)cc(C(F)(F)F)c5)n(C)c4c3Cl)c12]
I-264

-continued
I-265
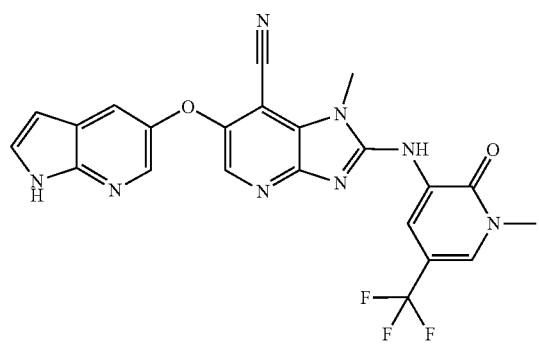 [SMILES: Cn1cc(C(F)(F)F)cc(Nc2nc3ncc(Oc4cnc5[nH]ccc5c4)c(C#N)c3n2C)c1=O]
I-266
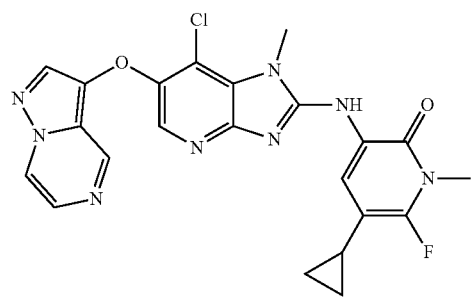 [SMILES: Cn1c(F)c(C2CC2)cc(Nc2nc3ncc(Oc4cnn5ccncc45)c(Cl)c3n2C)c1=O]
I-267-i
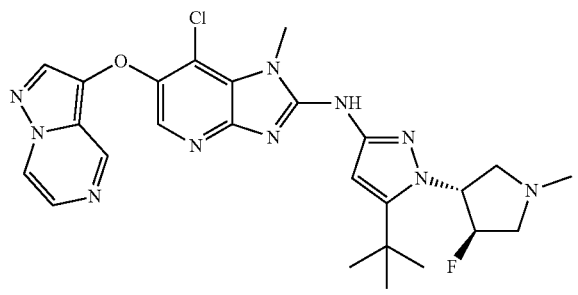 [SMILES: CN1C[C@@H](F)[C@H](n2nc(Nc3nc4ncc(Oc5cnn6ccncc56)c(Cl)c4n3C)cc2C(C)(C)C)C1]
I-267-ii
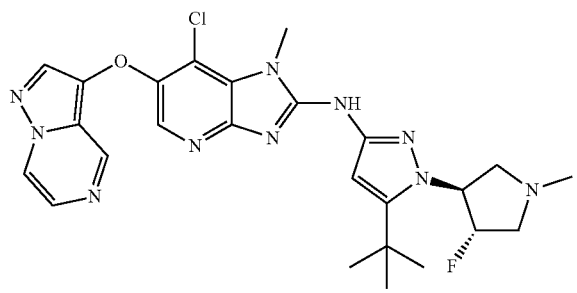 [SMILES: CN1C[C@H](F)[C@@H](n2nc(Nc3nc4ncc(Oc5cnn6ccncc56)c(Cl)c4n3C)cc2C(C)(C)C)C1]
I-267-iii
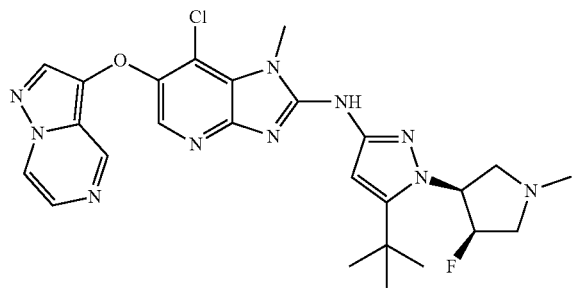 [SMILES: CN1C[C@@H](F)[C@@H](n2nc(Nc3nc4ncc(Oc5cnn6ccncc56)c(Cl)c4n3C)cc2C(C)(C)C)C1]

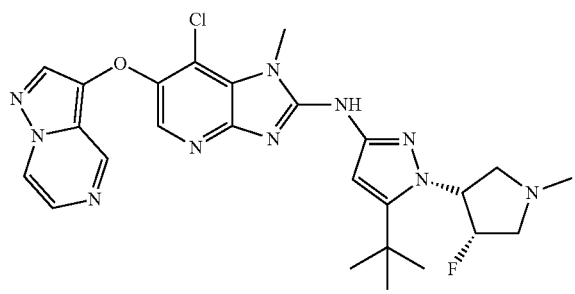
I-267-iv
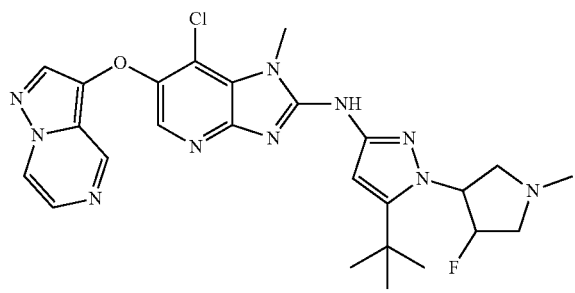 [SMILES: CN1CC(F)C(n2nc(Nc3nc4ncc(Oc5cnn6ccncc56)c(Cl)c4n3C)cc2C(C)(C)C)C1]
I-267
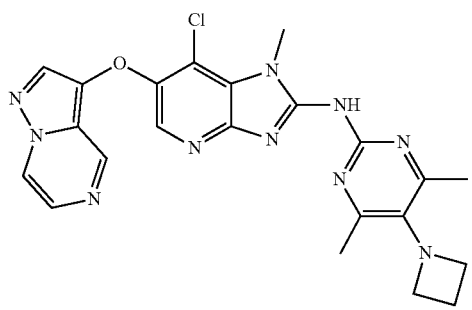 [SMILES: Cc1nc(Nc2nc3ncc(Oc4cnn5ccncc45)c(Cl)c3n2C)nc(C)c1N1CCC1]
I-268
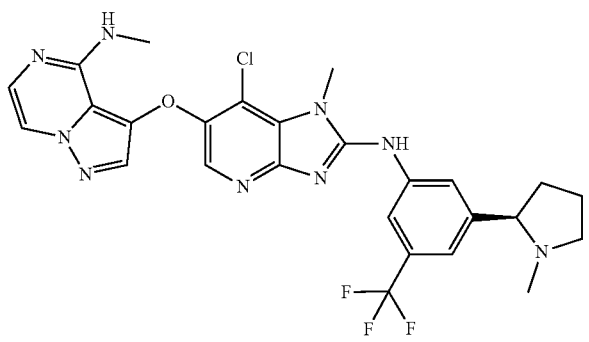 [SMILES: CNc1nccn2ncc(Oc3cnc4nc(Nc5cc([C@H]6CCCN6C)cc(C(F)(F)F)c5)n(C)c4c3Cl)c12]
I-269-i
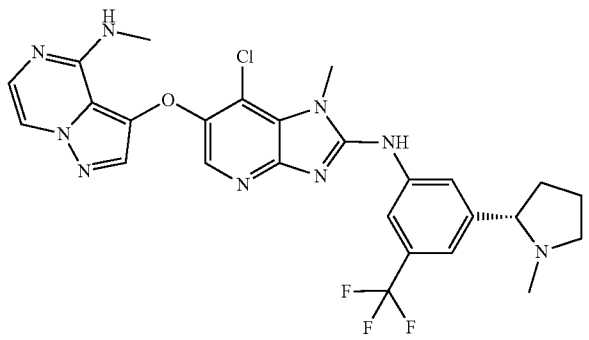
I-269-ii -continued
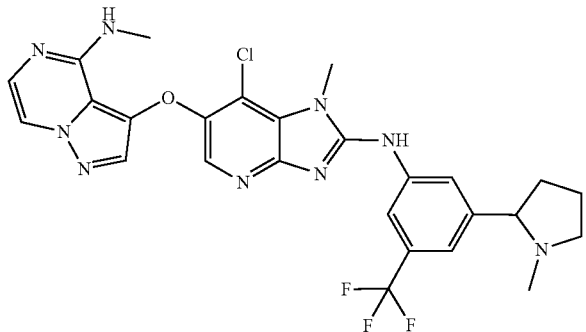 [SMILES: CNc1nccn2ncc(Oc3cnc4nc(Nc5cc([C@@H]6CCCN6C)cc(C(F)(F)F)c5)n(C)c4c3Cl)c12]
I-269
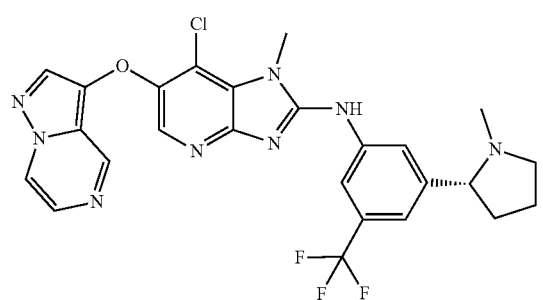 [SMILES: CN1CCC[C@@H]1c1cc(Nc2nc3ncc(Oc4cnn5ccncc45)c(Cl)c3n2C)cc(C(F)(F)F)c1]
I-270-i
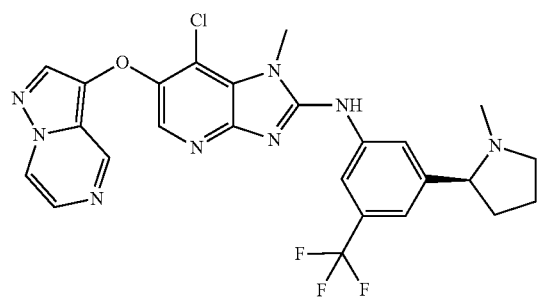 [SMILES: CN1CCC[C@H]1c1cc(Nc2nc3ncc(Oc4cnn5ccncc45)c(Cl)c3n2C)cc(C(F)(F)F)c1]
I-270-ii
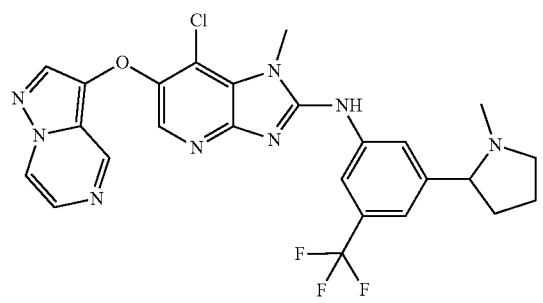 [SMILES: CN1CCCC1c1cc(Nc2nc3ncc(Oc4cnn5ccncc45)c(Cl)c3n2C)cc(C(F)(F)F)c1]
I-270
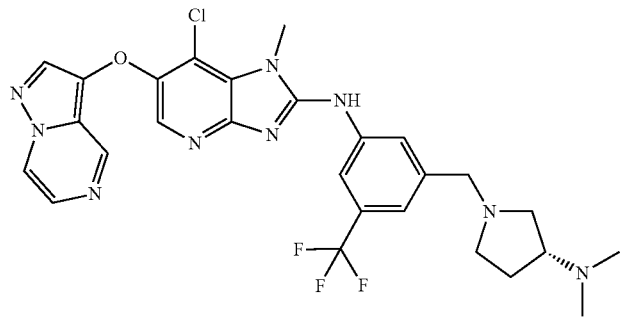 [SMILES: CN(C)[C@@H]1CCN(Cc2cc(Nc3nc4ncc(Oc5cnn6ccncc56)c(Cl)c4n3C)cc(C(F)(F)F)c2)C1]
I-271

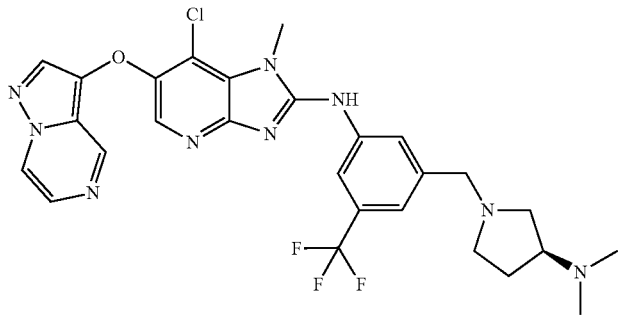 [SMILES: CN(C)[C@H]1CCN(Cc2cc(Nc3nc4ncc(Oc5cnn6ccncc56)c(Cl)c4n3C)cc(C(F)(F)F)c2)C1]
I-272
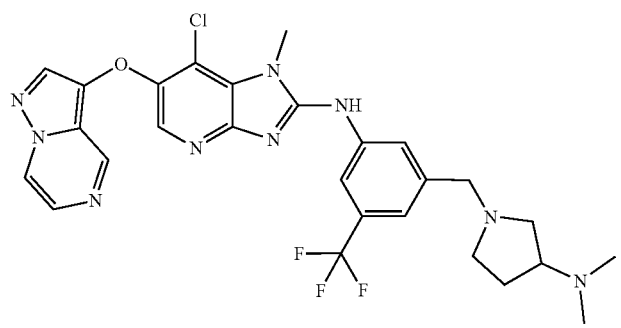 [SMILES: CN(C)C1CCN(Cc2cc(Nc3nc4ncc(Oc5cnn6ccncc56)c(Cl)c4n3C)cc(C(F)(F)F)c2)C1]
I-271'
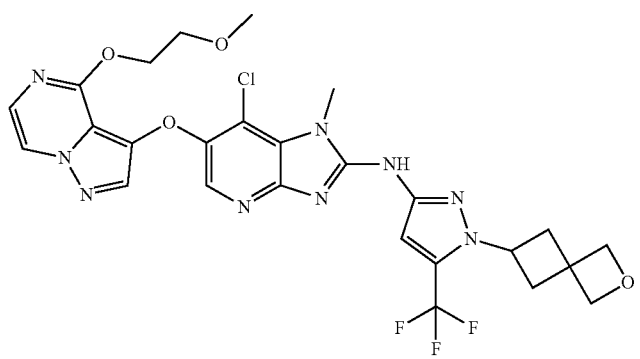 [SMILES: COCCOc1nccn2ncc(Oc3cnc4nc(Nc5cc(C(F)(F)F)n(C6CC7(COC7)C6)n5)n(C)c4c3Cl)c12]
I-273
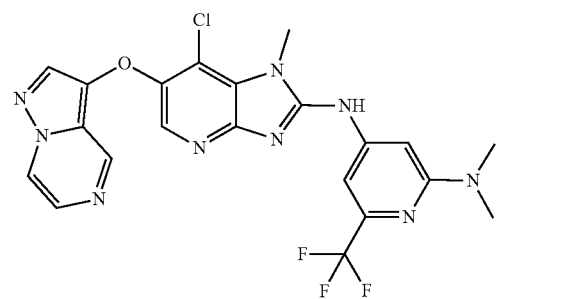 [SMILES: CN(C)c1cc(Nc2nc3ncc(Oc4cnn5ccncc45)c(Cl)c3n2C)cc(C(F)(F)F)n1]
I-274
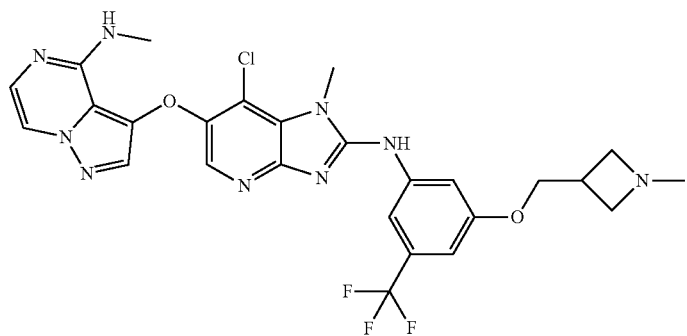 [SMILES: CNc1nccn2ncc(Oc3cnc4nc(Nc5cc(OCC6CN(C)C6)cc(C(F)(F)F)c5)n(C)c4c3Cl)c12]
I-275

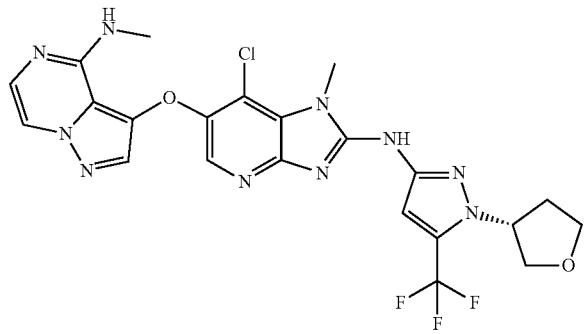 [SMILES: CNc1nccn2ncc(Oc3cnc4nc(Nc5cc(C(F)(F)F)n([C@@H]6CCOC6)n5)n(C)c4c3Cl)c12]
I-276
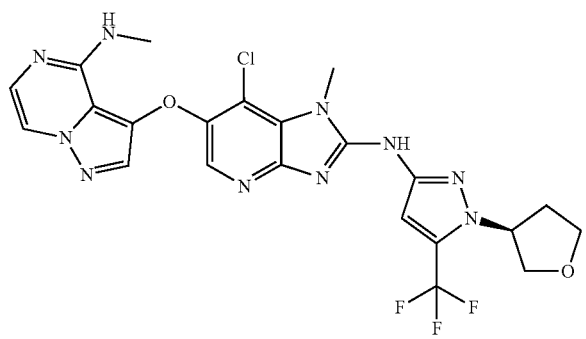 [SMILES: CNc1nccn2ncc(Oc3cnc4nc(Nc5cc(C(F)(F)F)n([C@H]6CCOC6)n5)n(C)c4c3Cl)c12]
I-276-ii
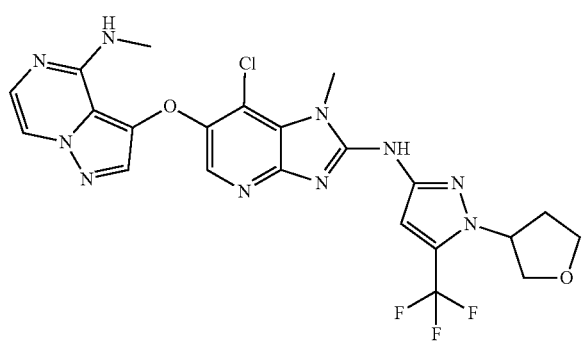 [SMILES: CNc1nccn2ncc(Oc3cnc4nc(Nc5cc(C(F)(F)F)n(C6CCOC6)n5)n(C)c4c3Cl)c12]
I-276'
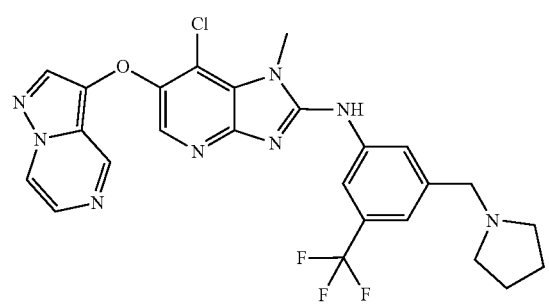 [SMILES: Cn1c(Nc2cc(CN3CCCC3)cc(C(F)(F)F)c2)nc2ncc(Oc3cnn4ccncc34)c(Cl)c21]
I-277
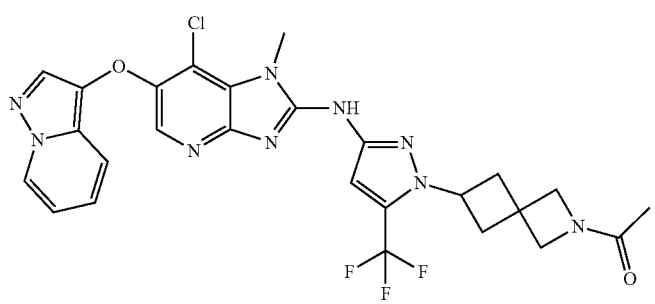 [SMILES: CC(=O)N1CC2(CC(n3nc(Nc4nc5ncc(Oc6cnn7ccccc67)c(Cl)c5n4C)cc3C(F)(F)F)C2)C1]
I-278

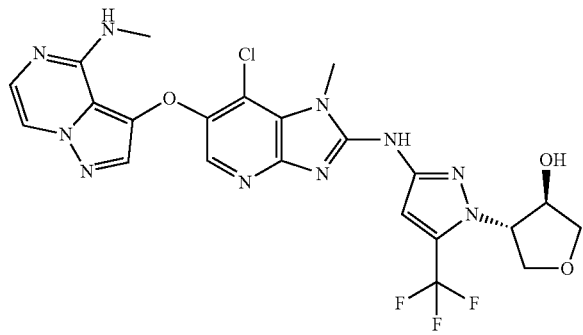 [SMILES: CNc1nccn2ncc(Oc3cnc4nc(Nc5cc(C(F)(F)F)n([C@H]6COC[C@@H]6O)n5)n(C)c4c3Cl)c12]
I-279-i
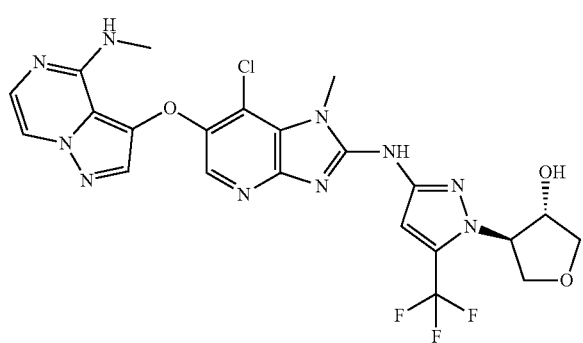 [SMILES: CNc1nccn2ncc(Oc3cnc4nc(Nc5cc(C(F)(F)F)n([C@@H]6COC[C@H]6O)n5)n(C)c4c3Cl)c12]
I-279-ii
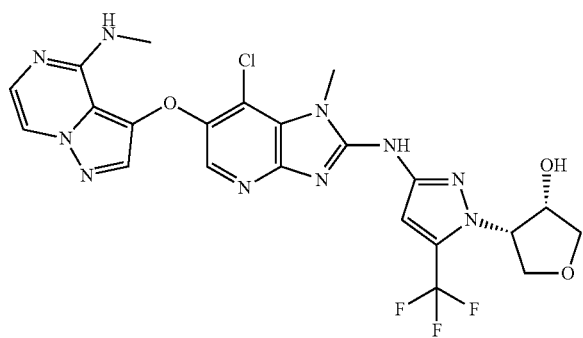 [SMILES: CNc1nccn2ncc(Oc3cnc4nc(Nc5cc(C(F)(F)F)n([C@H]6COC[C@H]6O)n5)n(C)c4c3Cl)c12]
I-279-iii
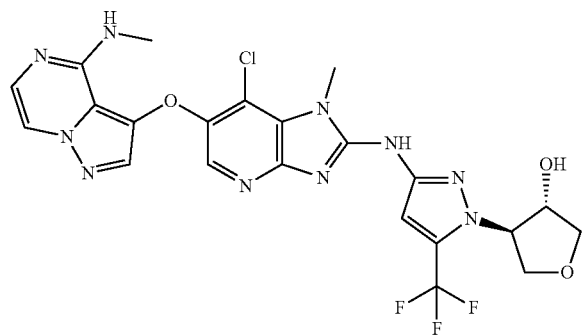 [SMILES: CNc1nccn2ncc(Oc3cnc4nc(Nc5cc(C(F)(F)F)n([C@@H]6COC[C@H]6O)n5)n(C)c4c3Cl)c12]
I-279-iv

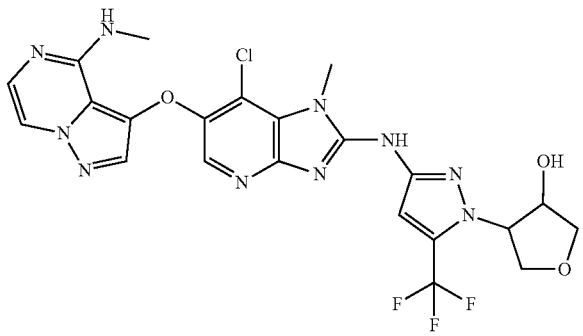 [SMILES: CNc1nccn2ncc(Oc3cnc4nc(Nc5cc(C(F)(F)F)n(C6COCC6O)n5)n(C)c4c3Cl)c12]
I-279
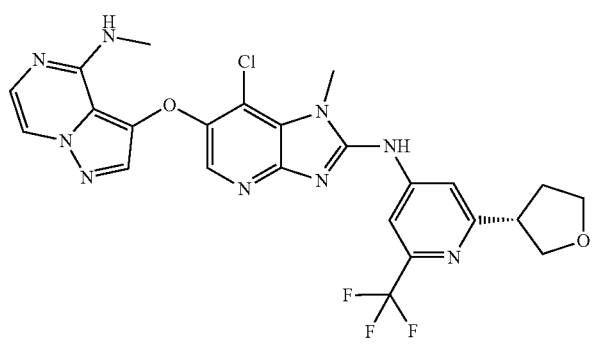 [SMILES: CNc1nccn2ncc(Oc3cnc4nc(Nc5cc([C@@H]6CCOC6)nc(C(F)(F)F)c5)n(C)c4c3Cl)c12]
I-280-i
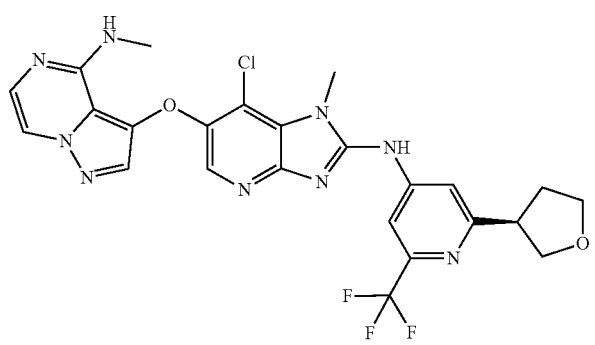 [SMILES: CNc1nccn2ncc(Oc3cnc4nc(Nc5cc([C@H]6CCOC6)nc(C(F)(F)F)c5)n(C)c4c3Cl)c12]
I-280-ii
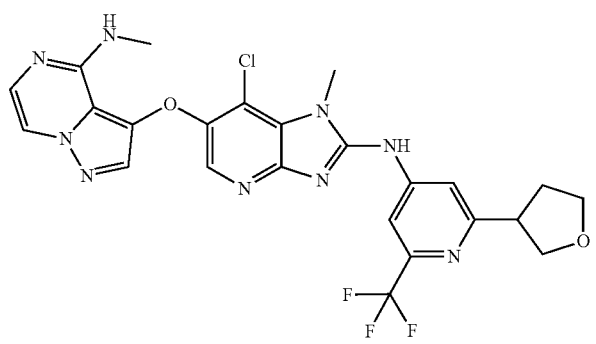
I-280

-continued
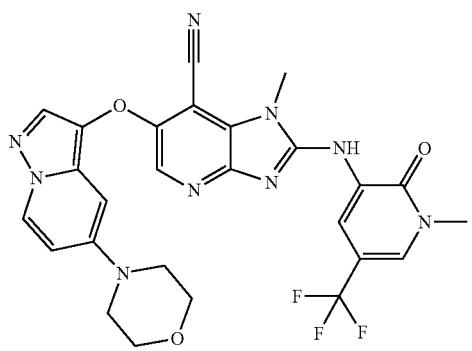 [SMILES: Cn1cc(C(F)(F)F)cc(Nc2nc3ncc(Oc4cnn5ccc(N6CCOCC6)cc45)c(C#N)c3n2C)c1=O]
I-281
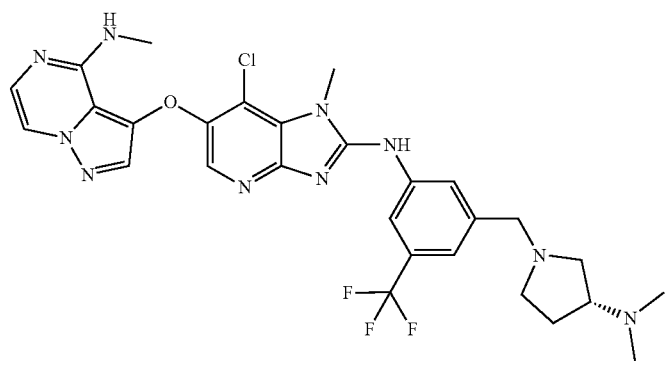 [SMILES: CNc1nccn2ncc(Oc3cnc4nc(Nc5cc(CN6CC[C@@H](N(C)C)C6)cc(C(F)(F)F)c5)n(C)c4c3Cl)c12]
I-282
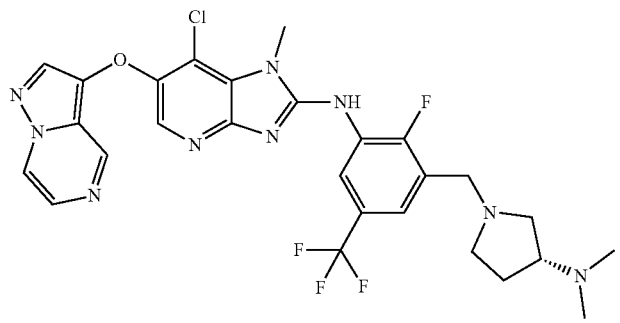 [SMILES: CN(C)[C@@H]1CCN(Cc2cc(C(F)(F)F)cc(Nc3nc4ncc(Oc5cnn6ccncc56)c(Cl)c4n3C)c2F)C1]
I-283
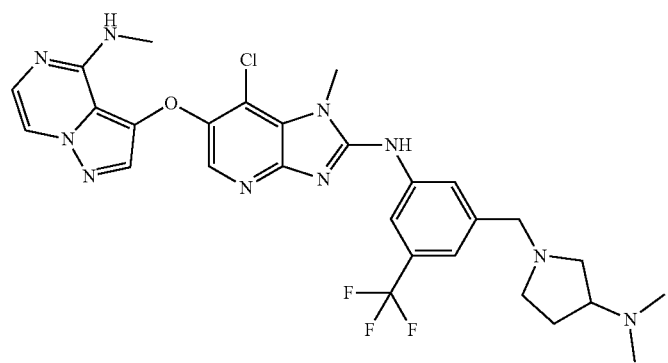 [SMILES: CNc1nccn2ncc(Oc3cnc4nc(Nc5cc(CN6CCC(N(C)C)C6)cc(C(F)(F)F)c5)n(C)c4c3Cl)c12]
I-282'

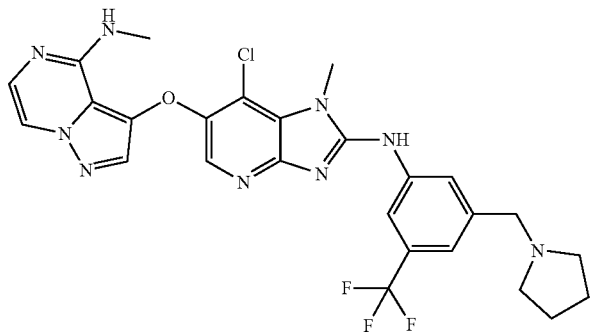 [SMILES: CNc1nccn2ncc(Oc3cnc4nc(Nc5cc(CN6CCCC6)cc(C(F)(F)F)c5)n(C)c4c3Cl)c12]
I-284
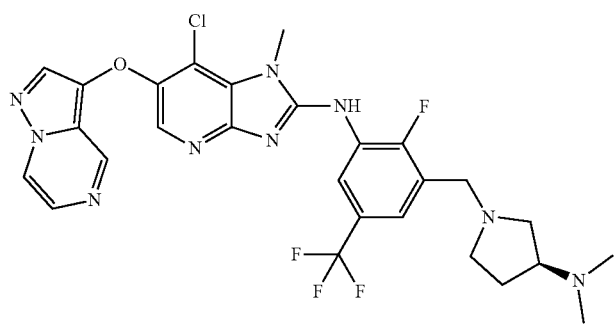 [SMILES: CN(C)[C@H]1CCN(Cc2cc(C(F)(F)F)cc(Nc3nc4ncc(Oc5cnn6ccncc56)c(Cl)c4n3C)c2F)C1]
I-285
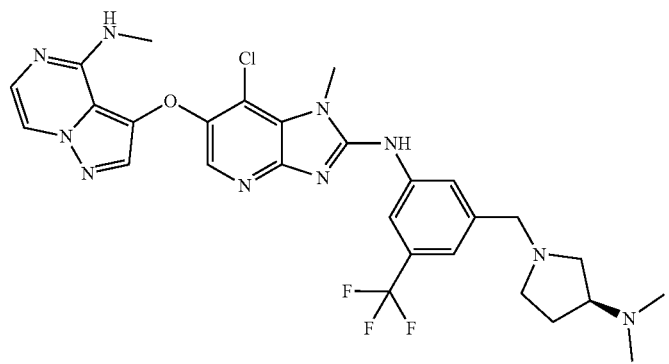 [SMILES: CNc1nccn2ncc(Oc3cnc4nc(Nc5cc(CN6CC[C@H](N(C)C)C6)cc(C(F)(F)F)c5)n(C)c4c3Cl)c12]
I-286
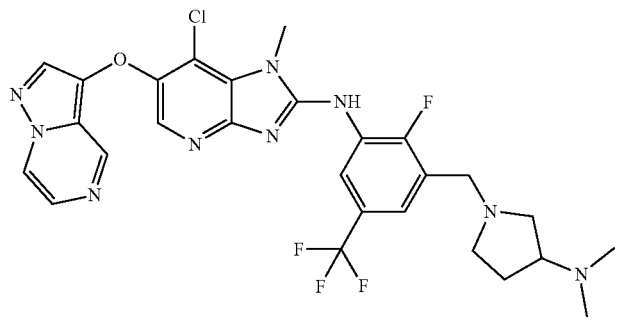 [SMILES: CN(C)C1CCN(Cc2cc(C(F)(F)F)cc(Nc3nc4ncc(Oc5cnn6ccncc56)c(Cl)c4n3C)c2F)C1]
I-285'

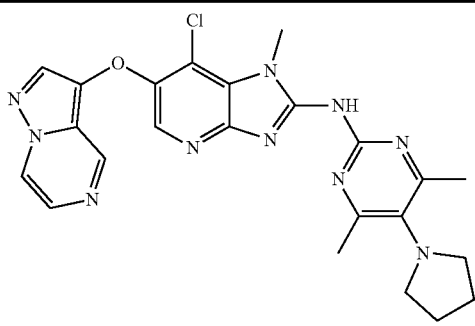
I-287
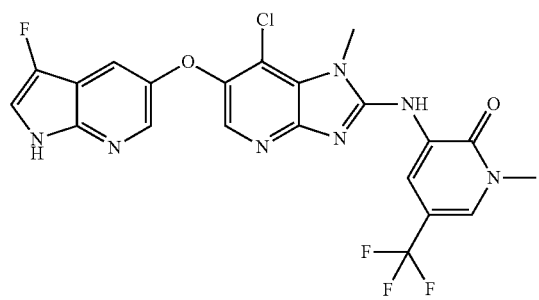 [SMILES: Cn1cc(C(F)(F)F)cc(Nc2nc3ncc(Oc4cnc5[nH]cc(F)c5c4)c(Cl)c3n2C)c1=O]
I-288
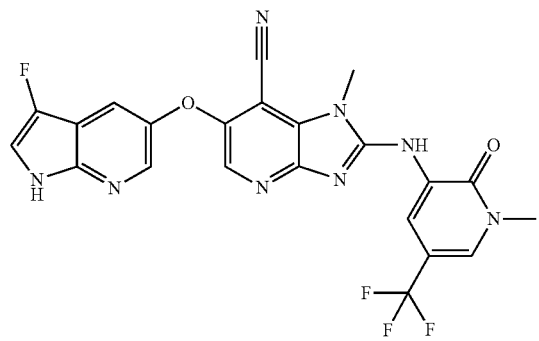
I-289
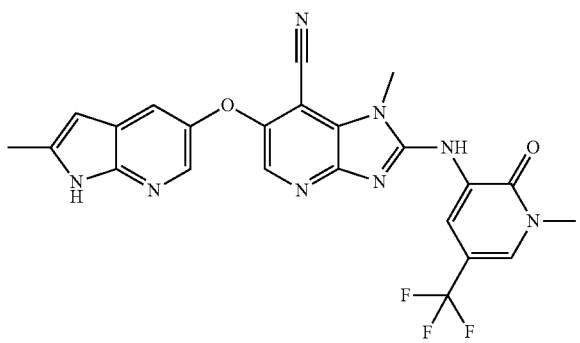
I-290
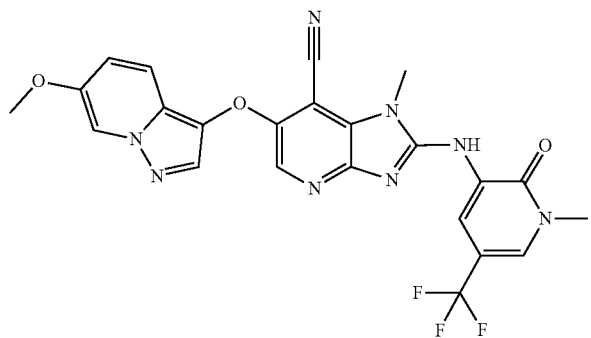
I-291

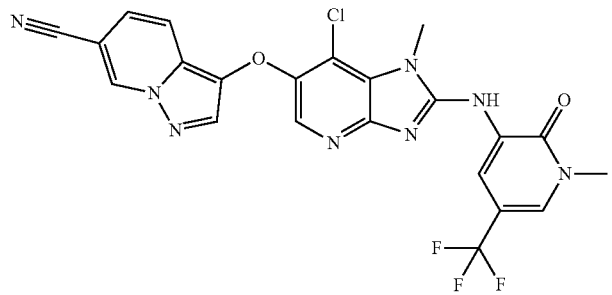 [SMILES: Cn1cc(C(F)(F)F)cc(Nc2nc3ncc(Oc4cnn5cc(C#N)ccc45)c(Cl)c3n2C)c1=O]
I-292
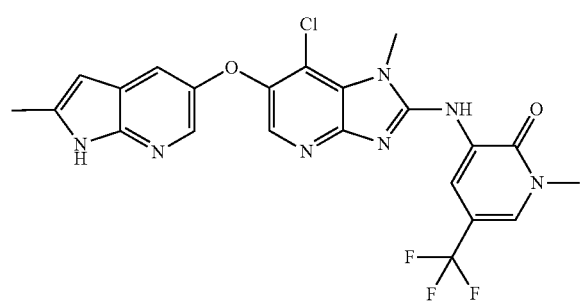
I-293
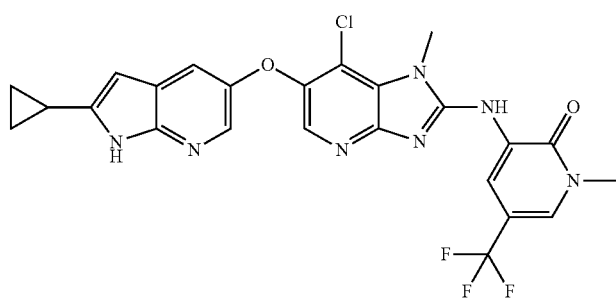 [SMILES: Cn1cc(C(F)(F)F)cc(Nc2nc3ncc(Oc4cnc5[nH]c(C6CC6)cc5c4)c(Cl)c3n2C)c1=O]
I-294
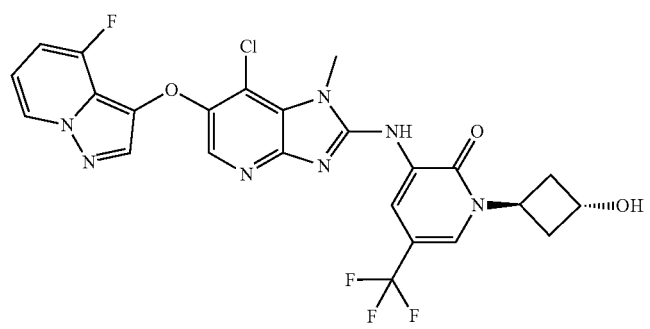 [SMILES: Cn1c(Nc2cc(C(F)(F)F)cn([C@H]3C[C@H](O)C3)c2=O)nc2ncc(Oc3cnn4cccc(F)c34)c(Cl)c21]
I-295
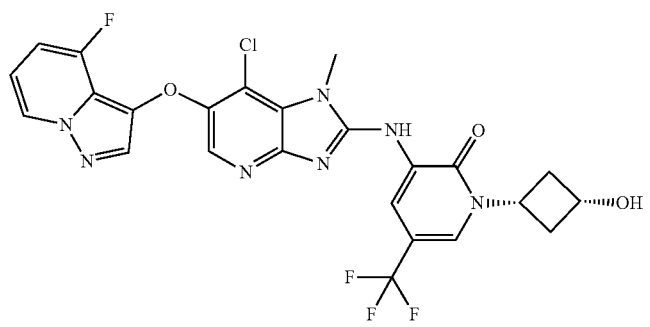 [SMILES: Cn1c(Nc2cc(C(F)(F)F)cn([C@H]3C[C@@H](O)C3)c2=O)nc2ncc(Oc3cnn4cccc(F)c34)c(Cl)c21]
I-295-ii -continued
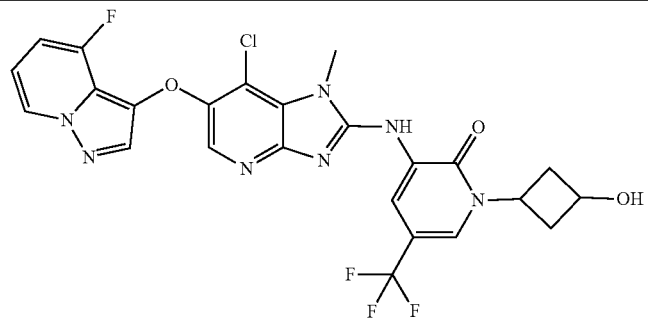
I-295'
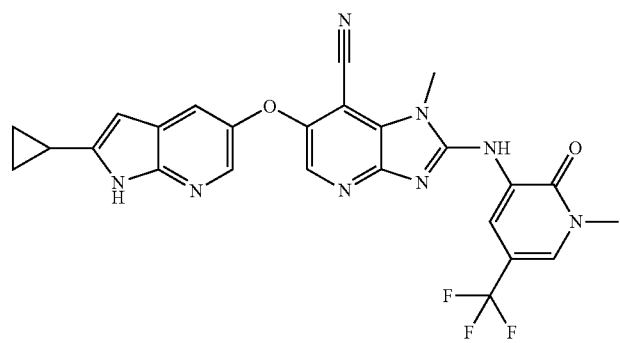 [SMILES: Cn1cc(C(F)(F)F)cc(Nc2nc3ncc(Oc4cnc5[nH]c(C6CC6)cc5c4)c(C#N)c3n2C)c1=O]
I-296
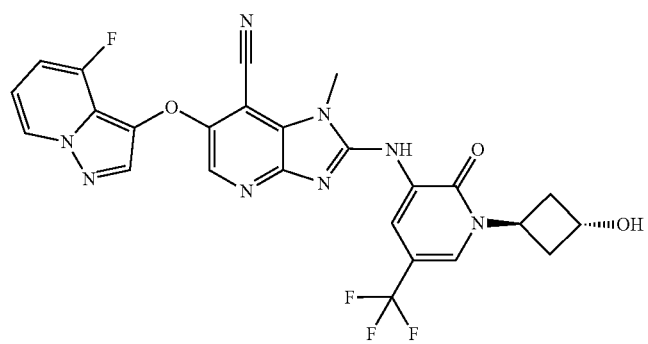 [SMILES: Cn1c(Nc2cc(C(F)(F)F)cn([C@H]3C[C@H](O)C3)c2=O)nc2ncc(Oc3cnn4cccc(F)c34)c(C#N)c21]
I-297
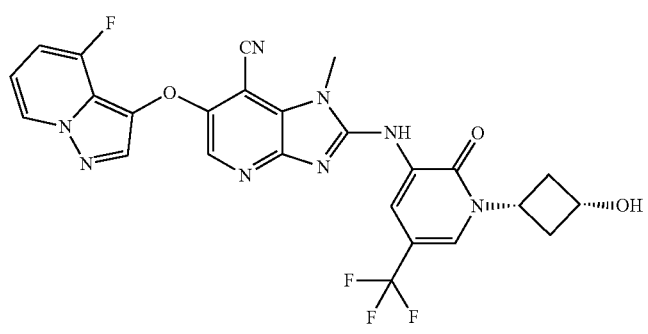 [SMILES: Cn1c(Nc2cc(C(F)(F)F)cn([C@H]3C[C@@H](O)C3)c2=O)nc2ncc(Oc3cnn4cccc(F)c34)c(C#N)c21]
I-297-ii
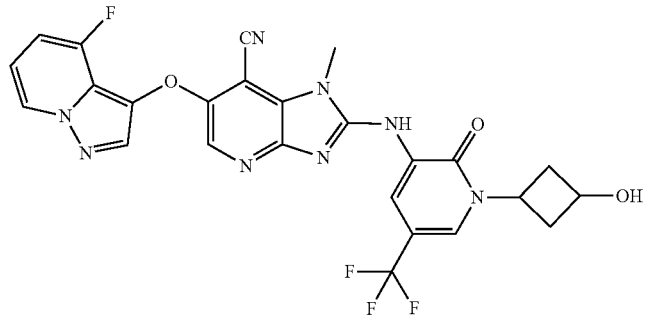 [SMILES: Cn1c(Nc2cc(C(F)(F)F)cn(C3CC(O)C3)c2=O)nc2ncc(Oc3cnn4cccc(F)c34)c(C#N)c21]
I-297'

-continued
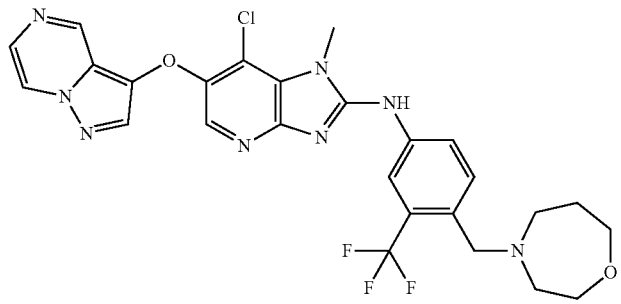 [SMILES: Cn1c(Nc2ccc(CN3CCCOCC3)c(C(F)(F)F)c2)nc2ncc(Oc3cnn4ccncc34)c(Cl)c21]
I-298
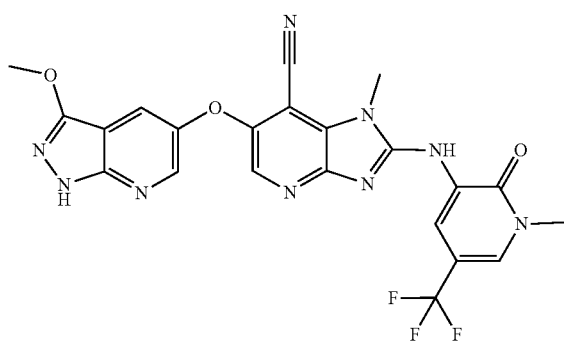
I-299
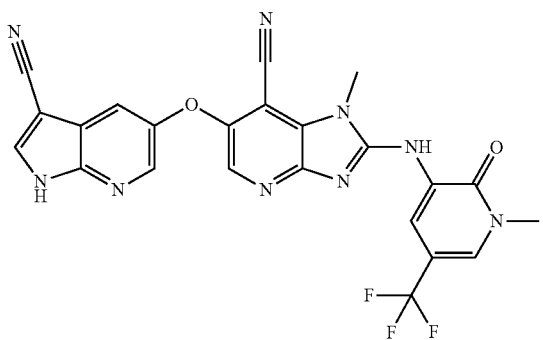 [SMILES: Cn1cc(C(F)(F)F)cc(Nc2nc3ncc(Oc4cnc5[nH]cc(C#N)c5c4)c(C#N)c3n2C)c1=O]
I-300
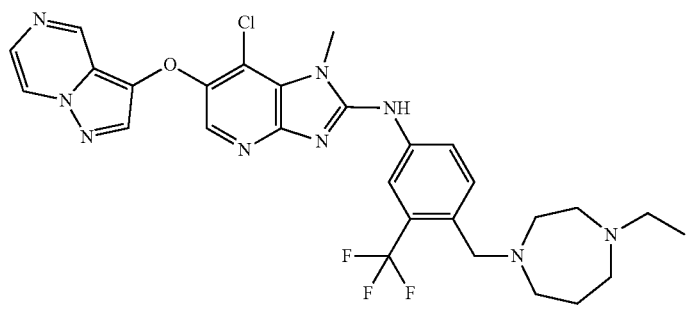 [SMILES: CCN1CCCN(Cc2ccc(Nc3nc4ncc(Oc5cnn6ccncc56)c(Cl)c4n3C)cc2C(F)(F)F)CC1]
I-301
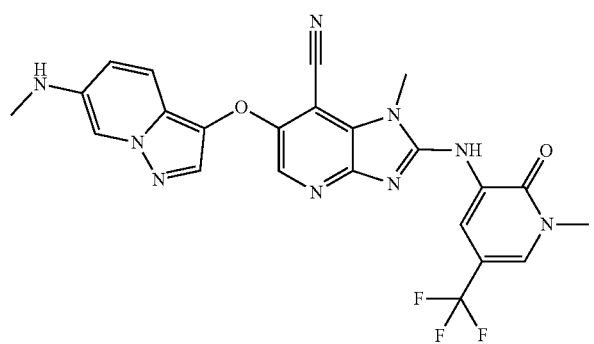
I-302

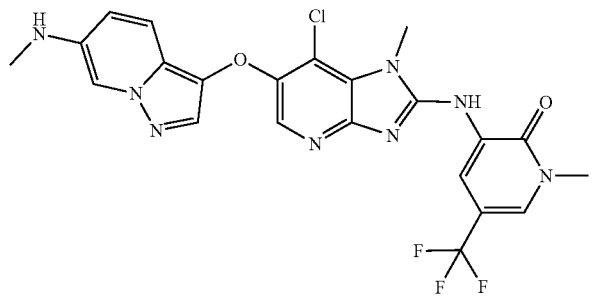
I-303
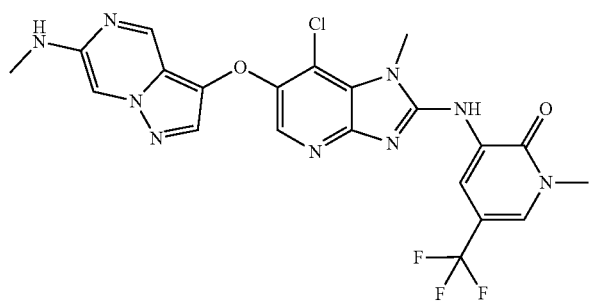
I-304
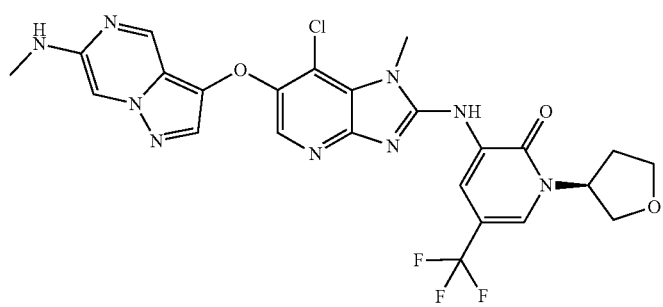 [SMILES: CNc1cn2ncc(Oc3cnc4nc(Nc5cc(C(F)(F)F)cn([C@H]6CCOC6)c5=O)n(C)c4c3Cl)c2cn1]
I-305
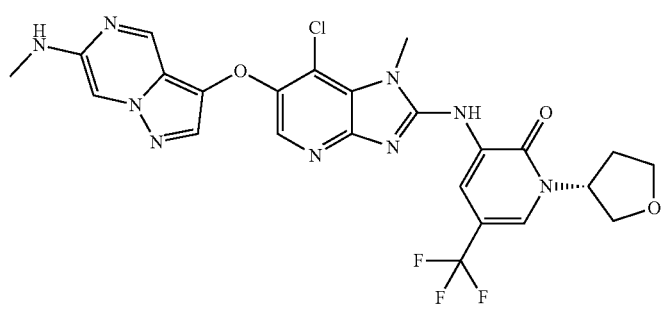 [SMILES: CNc1cn2ncc(Oc3cnc4nc(Nc5cc(C(F)(F)F)cn([C@@H]6CCOC6)c5=O)n(C)c4c3Cl)c2cn1]
I-306
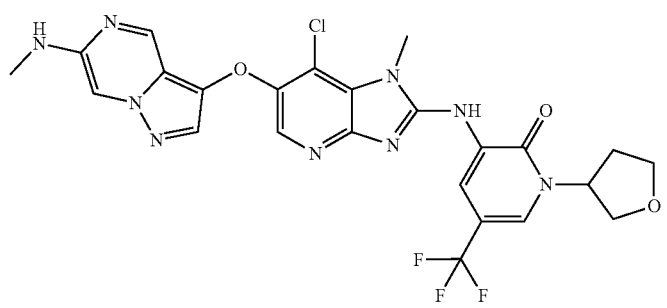 [SMILES: CNc1cn2ncc(Oc3cnc4nc(Nc5cc(C(F)(F)F)cn(C6CCOC6)c5=O)n(C)c4c3Cl)c2cn1]
I-305'

-continued
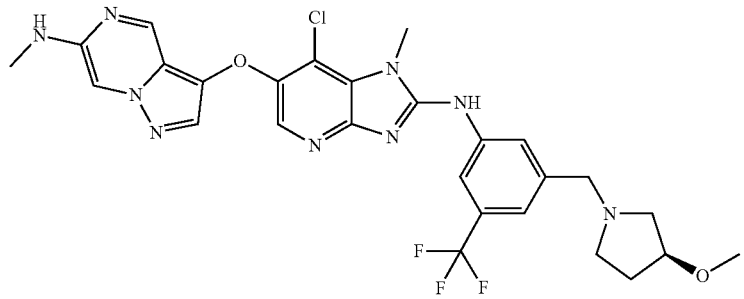
I-307
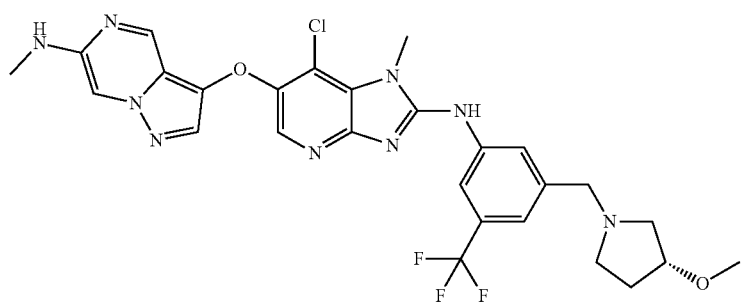
I-308
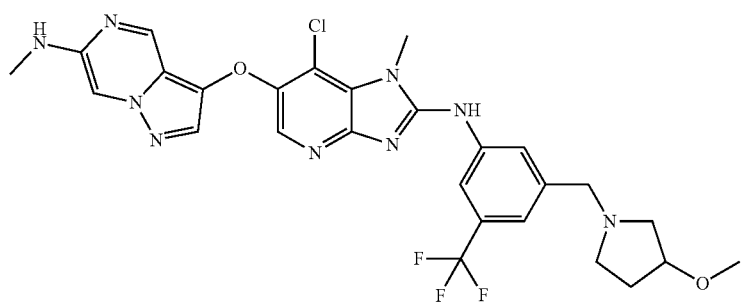
I-307'
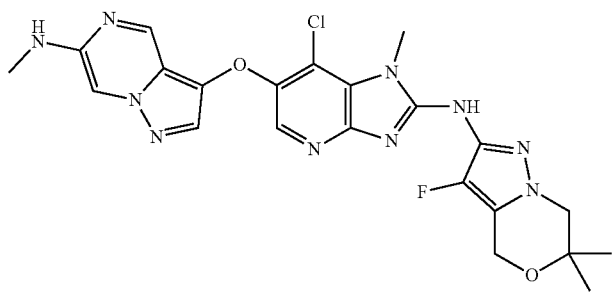
I-309
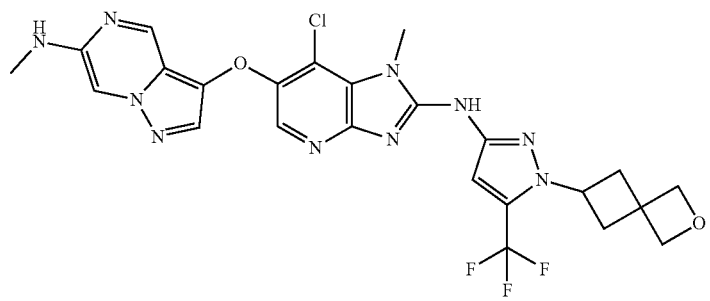 [SMILES: CNc1cn2ncc(Oc3cnc4nc(Nc5cc(C(F)(F)F)n(C6CC7(COC7)C6)n5)n(C)c4c3Cl)c2cn1]
I-310

-continued
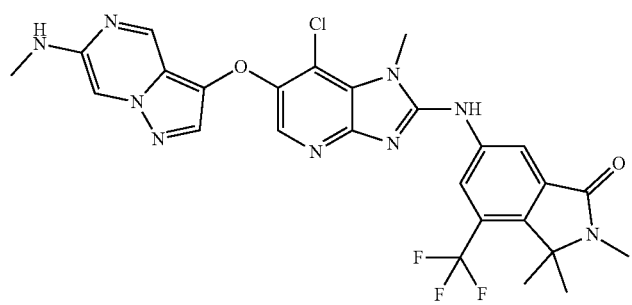
I-311
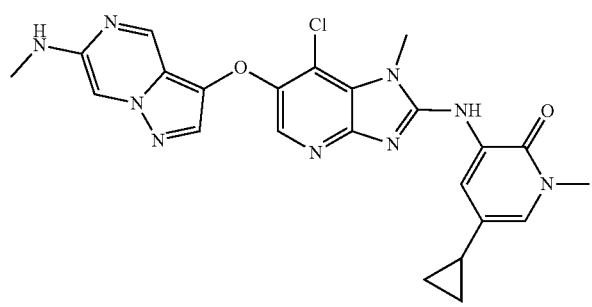
I-312
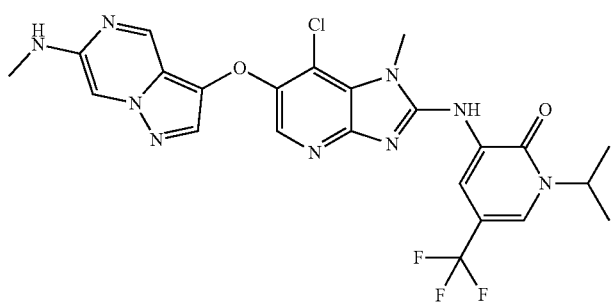 [SMILES: CNc1cn2ncc(Oc3cnc4nc(Nc5cc(C(F)(F)F)cn(C(C)C)c5=O)n(C)c4c3Cl)c2cn1]
I-313
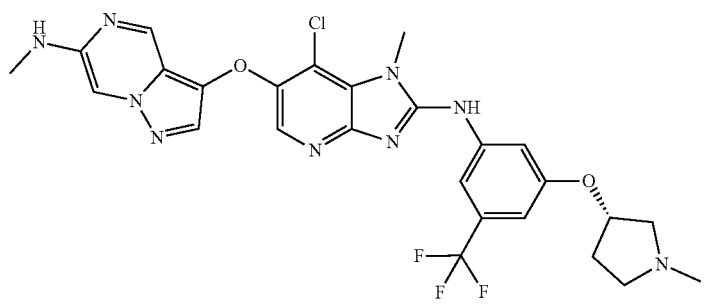
I-314
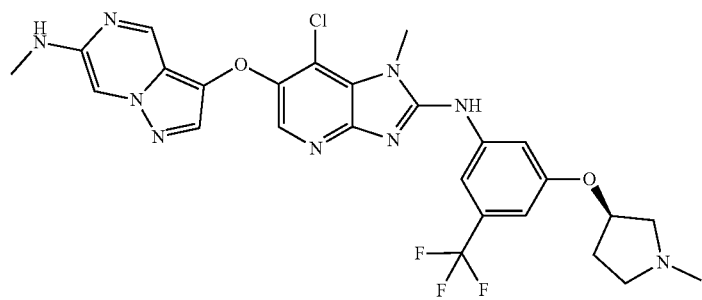
I-315

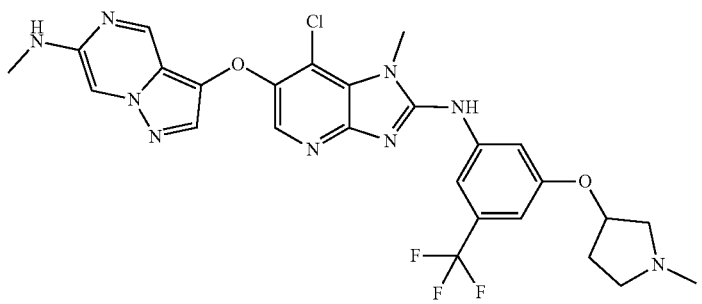
I-314'
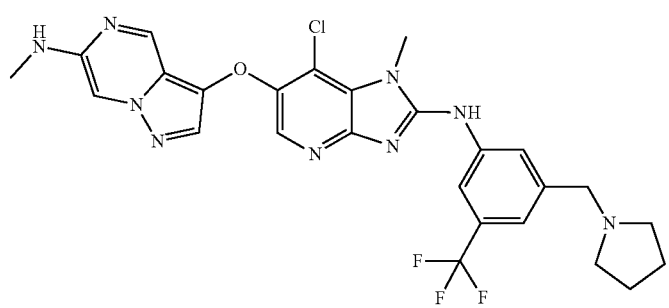 [SMILES: CNc1cn2ncc(Oc3cnc4nc(Nc5cc(CN6CCCC6)cc(C(F)(F)F)c5)n(C)c4c3Cl)c2cn1]
I-316
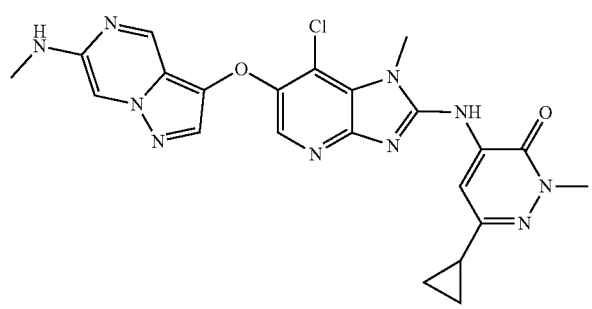
I-317
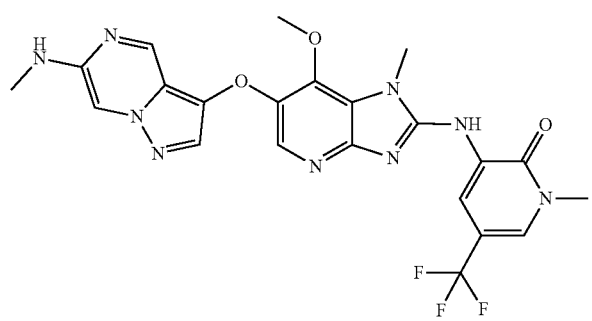
I-318
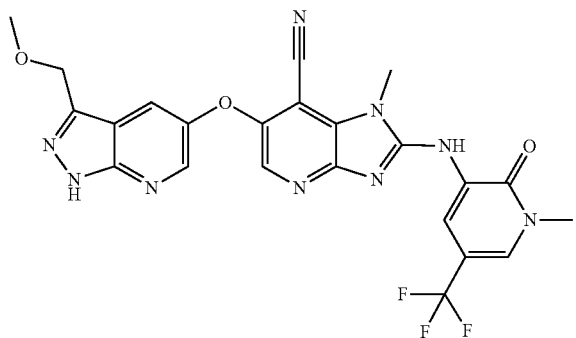
I-319

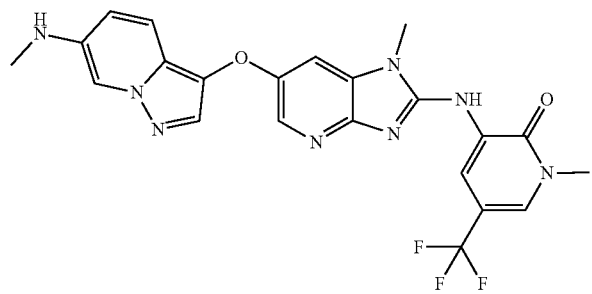
I-320
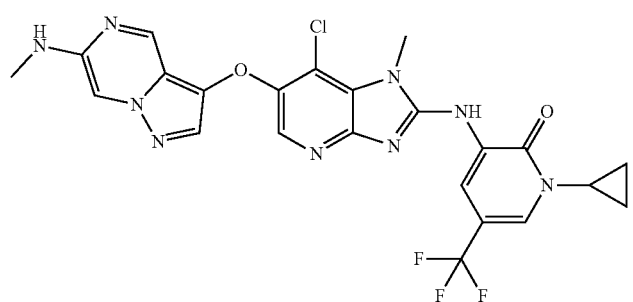 [SMILES: CNc1cn2ncc(Oc3cnc4nc(Nc5cc(C(F)(F)F)cn(C6CC6)c5=O)n(C)c4c3Cl)c2cn1]
I-321
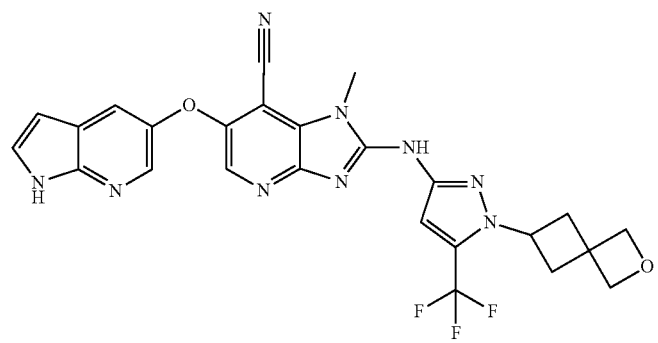 [SMILES: Cn1c(Nc2cc(C(F)(F)F)n(C3CC4(COC4)C3)n2)nc2ncc(Oc3cnc4[nH]ccc4c3)c(C#N)c21]
I-322
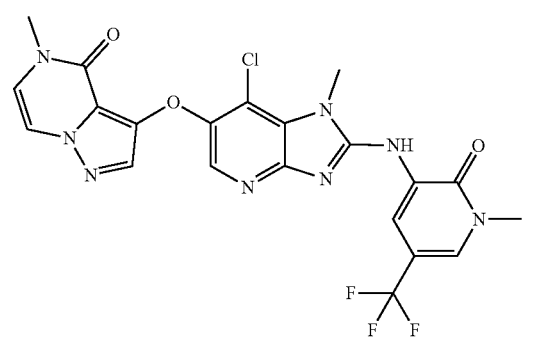 [SMILES: Cn1cc(C(F)(F)F)cc(Nc2nc3ncc(Oc4cnn5ccn(C)c(=O)c45)c(Cl)c3n2C)c1=O]
I-323
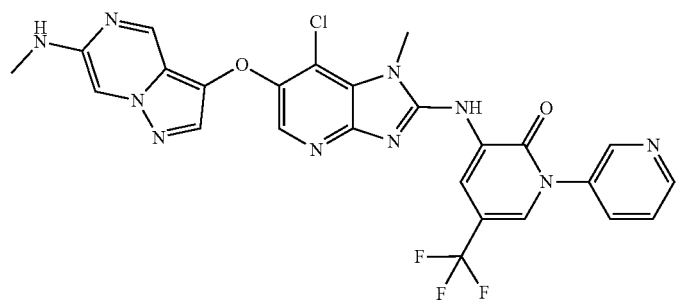 [SMILES: CNc1cn2ncc(Oc3cnc4nc(Nc5cc(C(F)(F)F)cn(-c6cccnc6)c5=O)n(C)c4c3Cl)c2cn1]
I-324

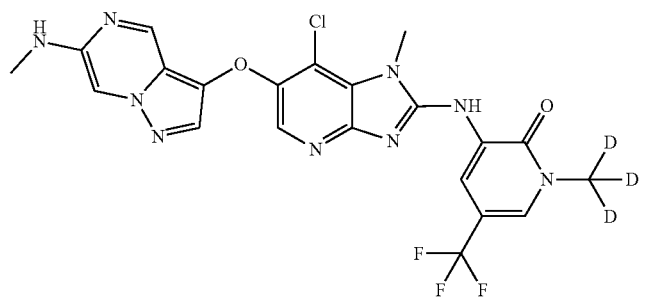 [SMILES: [2H]C([2H])([2H])n1cc(C(F)(F)F)cc(Nc2nc3ncc(Oc4cnn5cc(NC)ncc45)c(Cl)c3n2C)c1=O]
I-325
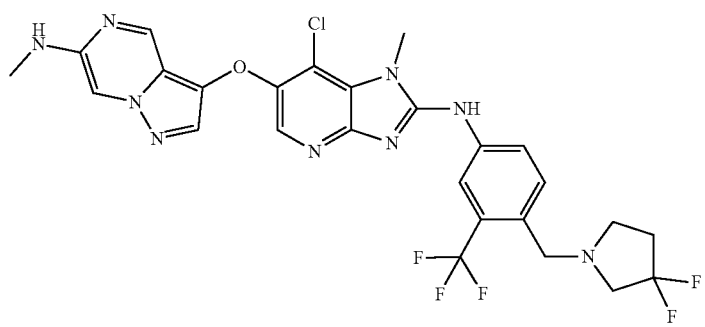 [SMILES: CNc1cn2ncc(Oc3cnc4nc(Nc5ccc(CN6CCC(F)(F)C6)c(C(F)(F)F)c5)n(C)c4c3Cl)c2cn1]
I-326
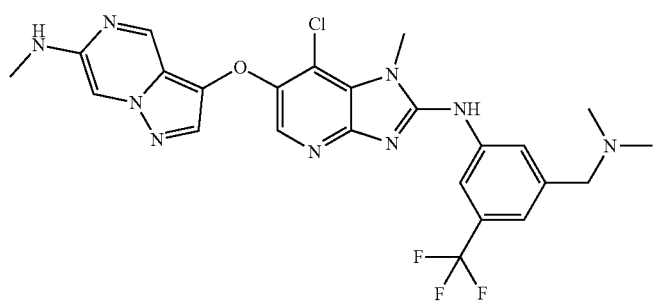
I-327
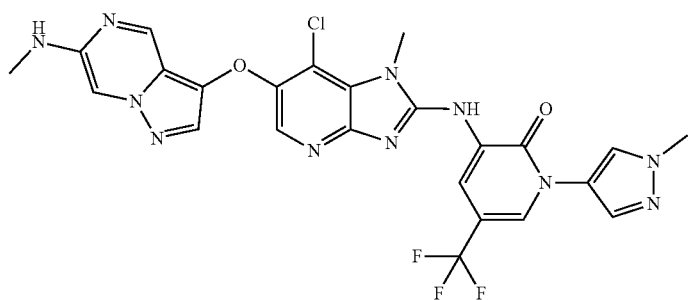
I-328
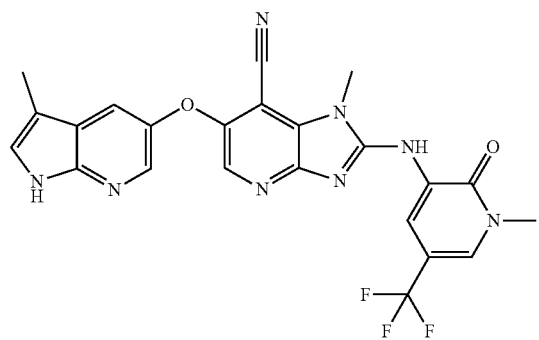 [SMILES: Cc1c[nH]c2ncc(Oc3cnc4nc(Nc5cc(C(F)(F)F)cn(C)c5=O)n(C)c4c3C#N)cc12]
I-329

-continued
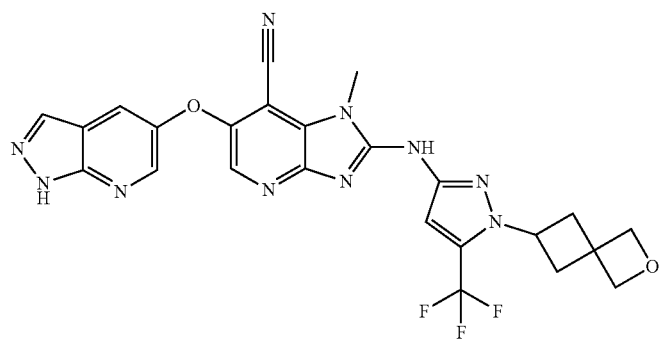 [SMILES: Cn1c(Nc2cc(C(F)(F)F)n(C3CC4(COC4)C3)n2)nc2ncc(Oc3cnc4[nH]ncc4c3)c(C#N)c21]
I-330
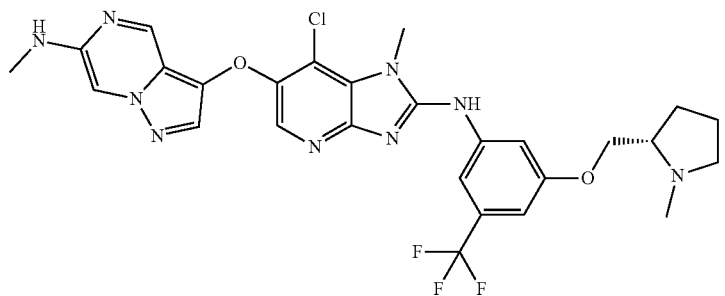 [SMILES: CNc1cn2ncc(Oc3cnc4nc(Nc5cc(OC[C@@H]6CCCN6C)cc(C(F)(F)F)c5)n(C)c4c3Cl)c2cn1]
I-331
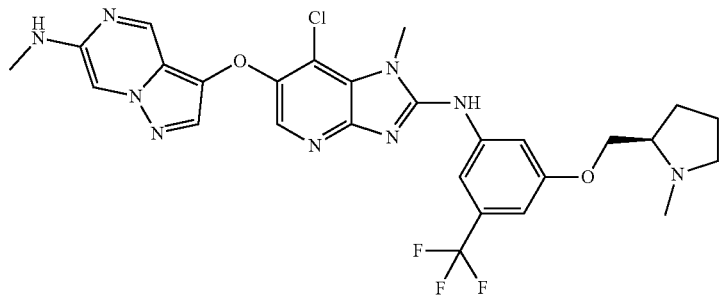 [SMILES: CNc1cn2ncc(Oc3cnc4nc(Nc5cc(OC[C@H]6CCCN6C)cc(C(F)(F)F)c5)n(C)c4c3Cl)c2cn1]
I-332
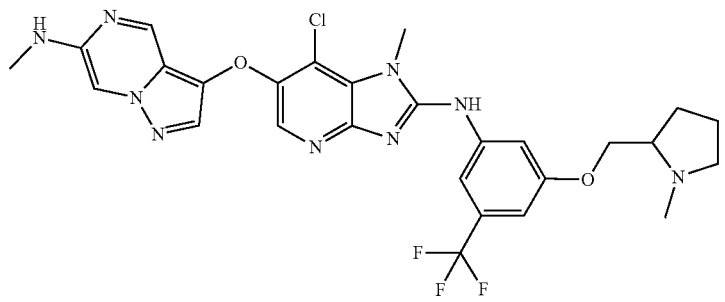 [SMILES: CNc1cn2ncc(Oc3cnc4nc(Nc5cc(OCC6CCCN6C)cc(C(F)(F)F)c5)n(C)c4c3Cl)c2cn1]
I-331'
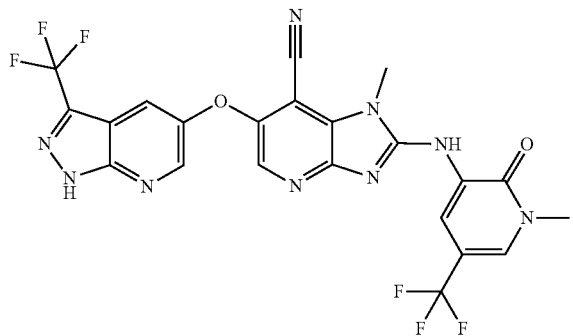 [SMILES: Cn1cc(C(F)(F)F)cc(Nc2nc3ncc(Oc4cnc5[nH]nc(C(F)(F)F)c5c4)c(C#N)c3n2C)c1=O]
I-333

I-334
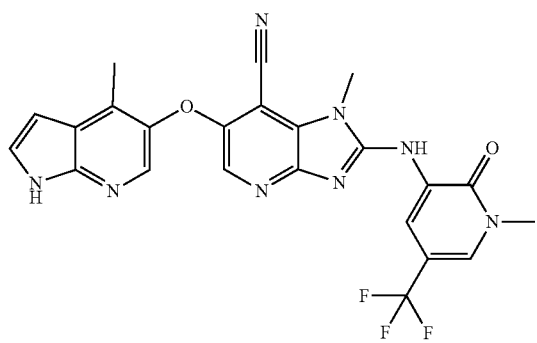 [SMILES: Cc1c(Oc2cnc3nc(Nc4cc(C(F)(F)F)cn(C)c4=O)n(C)c3c2C#N)cnc2[nH]ccc12]
I-335
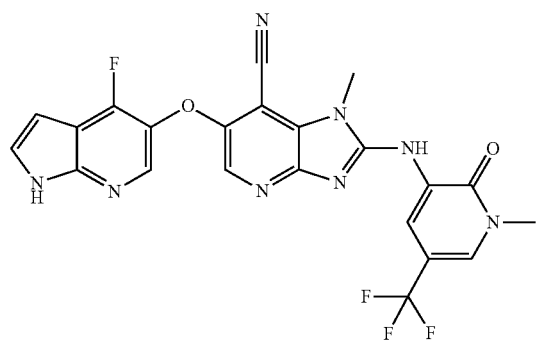 [SMILES: Cn1cc(C(F)(F)F)cc(Nc2nc3ncc(Oc4cnc5[nH]ccc5c4F)c(C#N)c3n2C)c1=O]
I-336
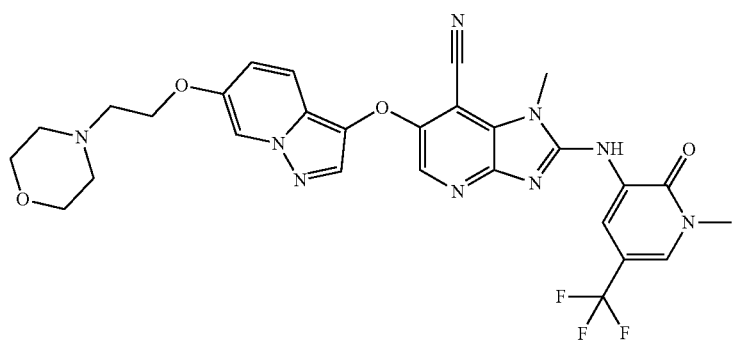 [SMILES: Cn1cc(C(F)(F)F)cc(Nc2nc3ncc(Oc4cnn5cc(OCCN6CCOCC6)ccc45)c(C#N)c3n2C)c1=O]
I-337
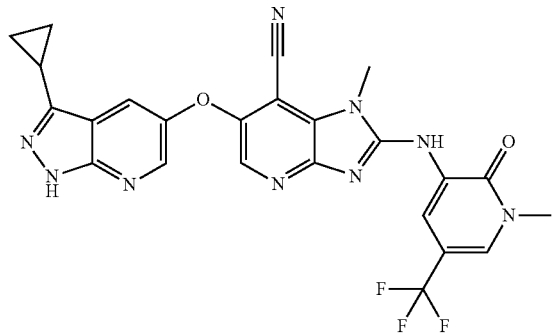 [SMILES: Cn1cc(C(F)(F)F)cc(Nc2nc3ncc(Oc4cnc5[nH]nc(C6CC6)c5c4)c(C#N)c3n2C)c1=O]

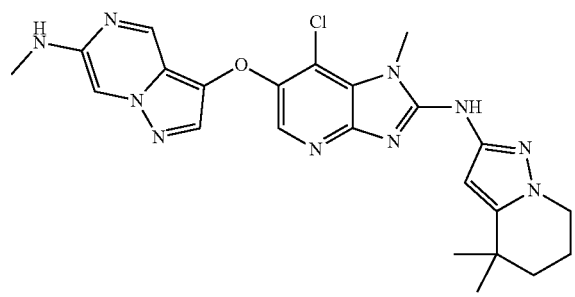 [SMILES: CNc1cn2ncc(Oc3cnc4nc(Nc5cc6n(n5)CCCC6(C)C)n(C)c4c3Cl)c2cn1]
I-338
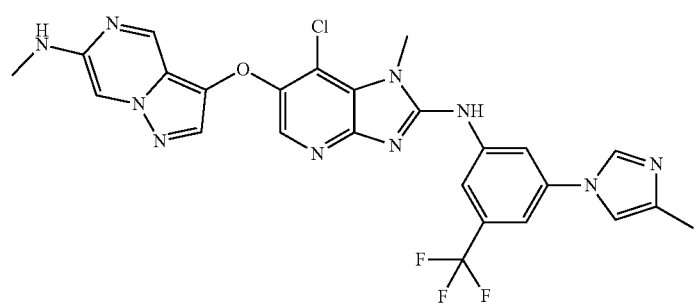
I-339
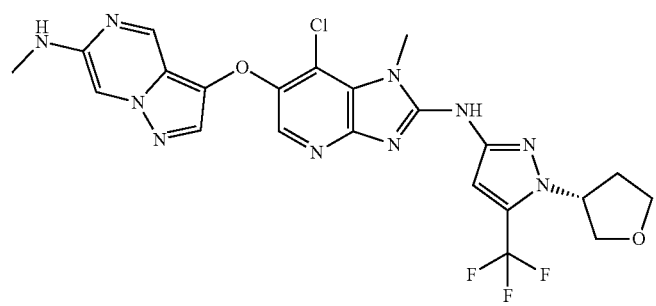
I-340
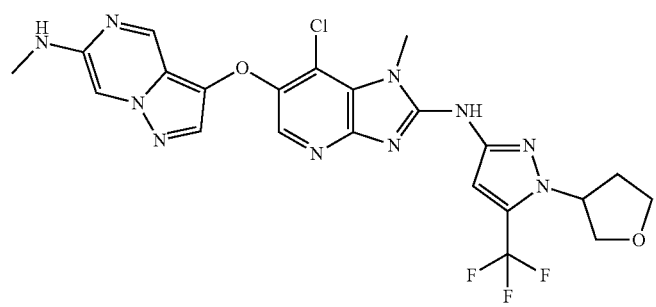 [SMILES: CNc1cn2ncc(Oc3cnc4nc(Nc5cc(C(F)(F)F)n([C@@H]6CCOC6)n5)n(C)c4c3Cl)c2cn1]
I-340'
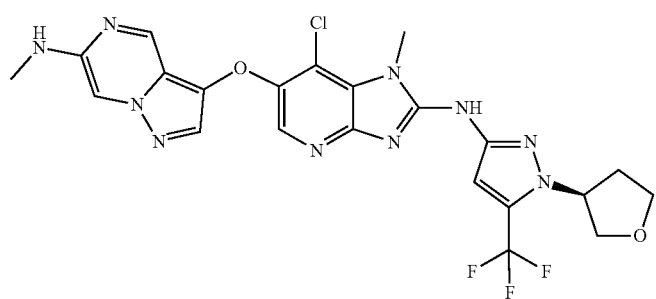 [SMILES: CNc1cn2ncc(Oc3cnc4nc(Nc5cc(C(F)(F)F)n([C@H]6CCOC6)n5)n(C)c4c3Cl)c2cn1]
I-340-ii -continued
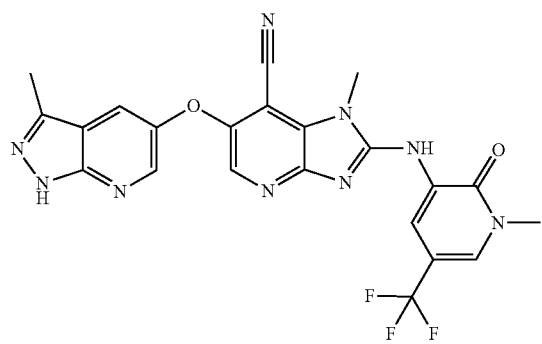 [SMILES: Cc1n[nH]c2ncc(Oc3cnc4nc(Nc5cc(C(F)(F)F)cn(C)c5=O)n(C)c4c3C#N)cc12]
I-341
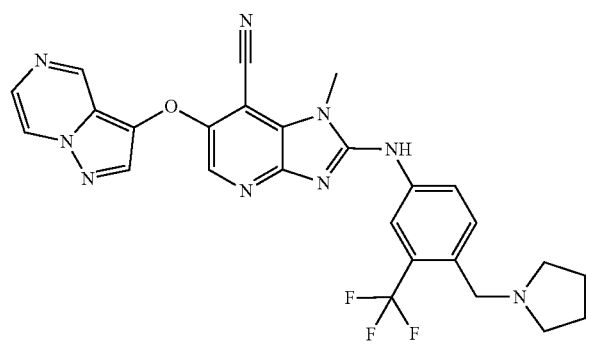 [SMILES: Cn1c(Nc2ccc(CN3CCCC3)c(C(F)(F)F)c2)nc2ncc(Oc3cnn4ccncc34)c(C#N)c21]
I-342
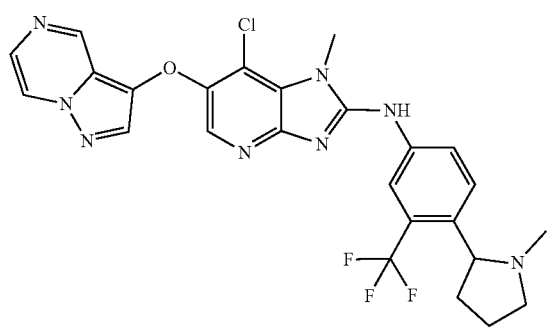 [SMILES: CN1CCCC1c1ccc(Nc2nc3ncc(Oc4cnn5ccncc45)c(Cl)c3n2C)cc1C(F)(F)F]
I-343'
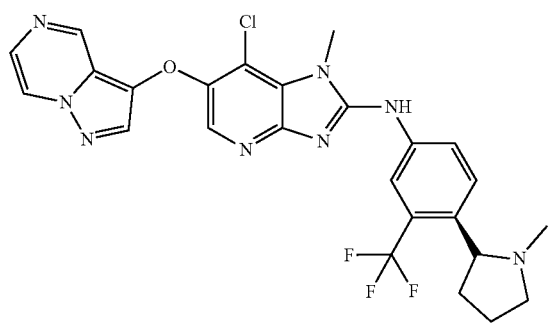
I-343

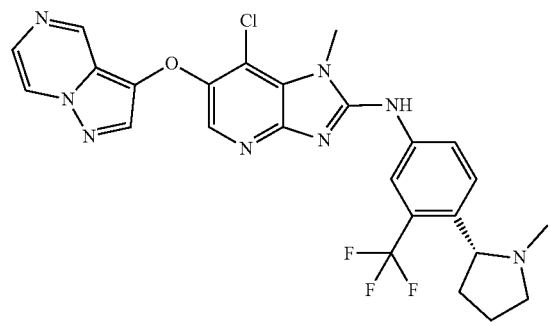 [SMILES: CN1CCC[C@@H]1c1ccc(Nc2nc3ncc(Oc4cnn5ccncc45)c(Cl)c3n2C)cc1C(F)(F)F]
I-344
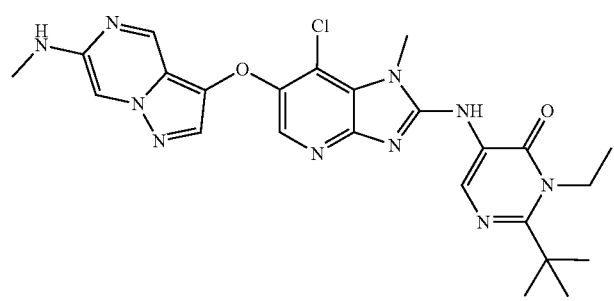 [SMILES: CCn1c(C(C)(C)C)ncc(Nc2nc3ncc(Oc4cnn5cc(NC)ncc45)c(Cl)c3n2C)c1=O]
I-345
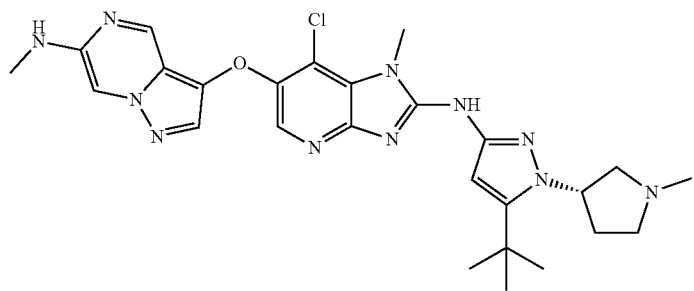
I-346
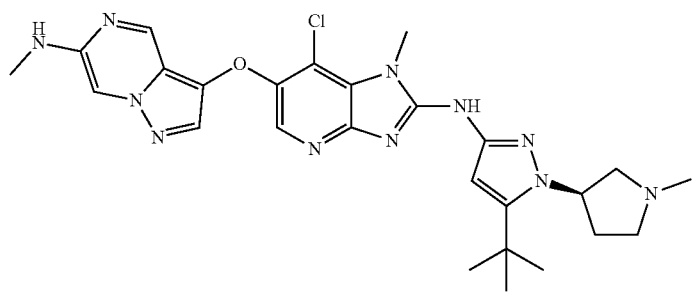
I-347
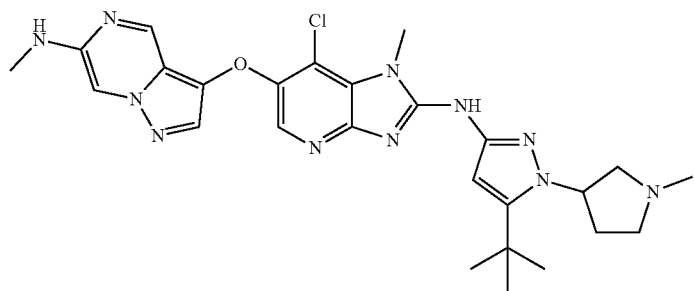
I-346'

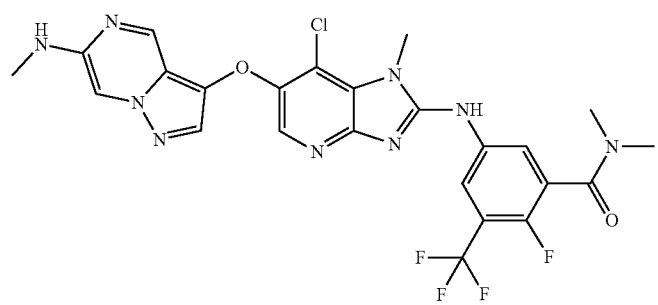
I-348
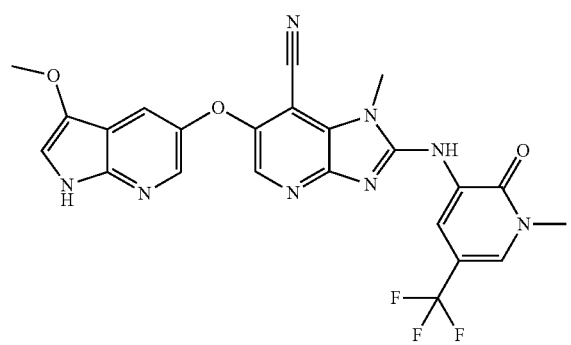
I-349
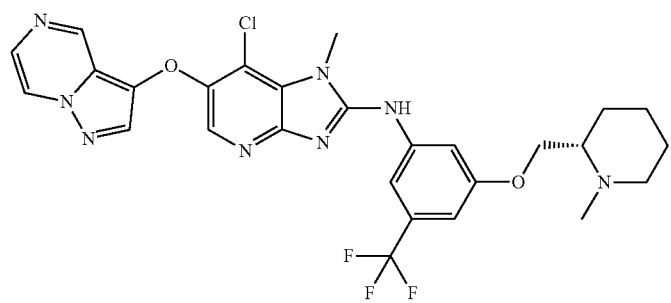 [SMILES: CN1CCCC[C@H]1COc1cc(Nc2nc3ncc(Oc4cnn5ccncc45)c(Cl)c3n2C)cc(C(F)(F)F)c1]
I-350-i
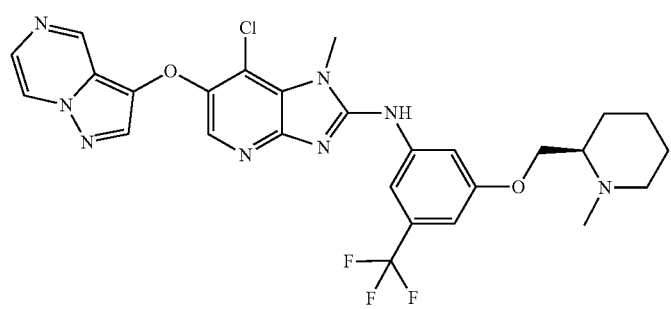 [SMILES: CN1CCCC[C@@H]1COc1cc(Nc2nc3ncc(Oc4cnn5ccncc45)c(Cl)c3n2C)cc(C(F)(F)F)c1]
I-350-ii
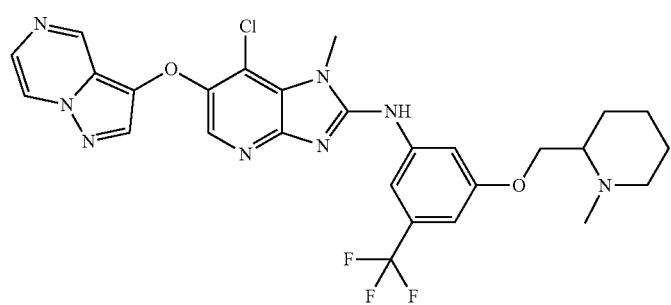
I-350'

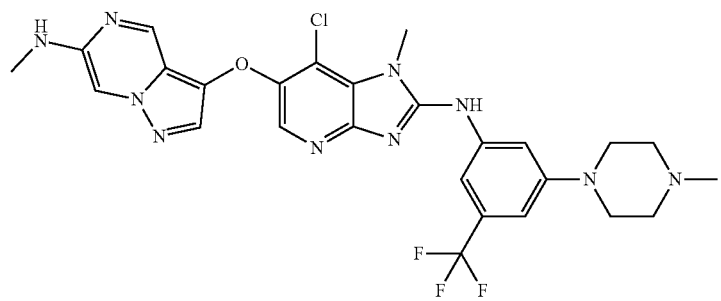
I-351
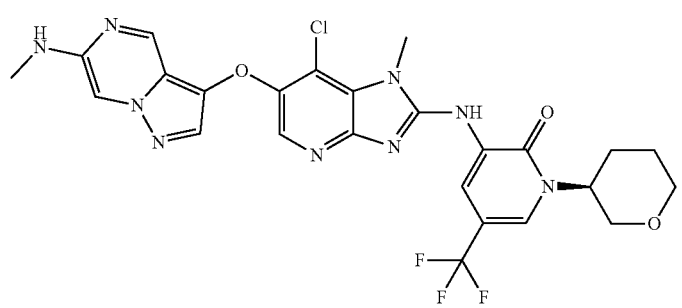
I-352-i
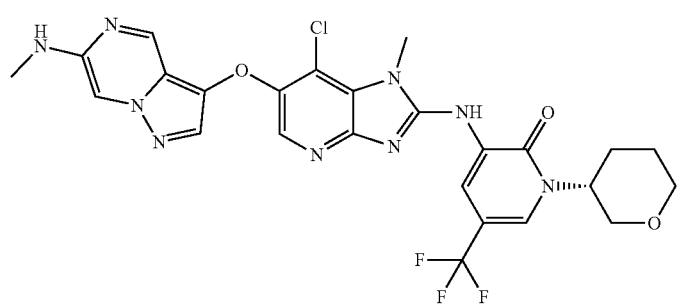 [SMILES: CNc1cn2ncc(Oc3cnc4nc(Nc5cc(C(F)(F)F)cn([C@@H]6CCCOC6)c5=O)n(C)c4c3Cl)c2cn1]
I-352-ii
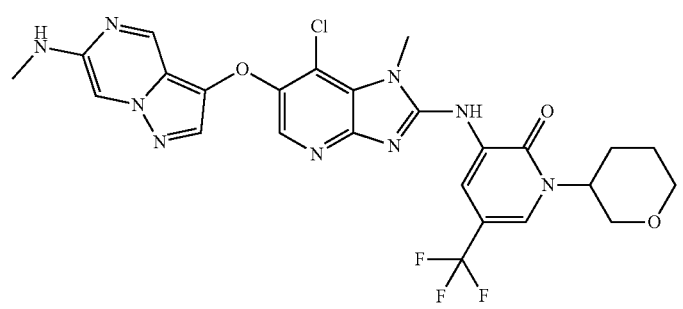 [SMILES: CNc1cn2ncc(Oc3cnc4nc(Nc5cc(C(F)(F)F)cn(C6CCCOC6)c5=O)n(C)c4c3Cl)c2cn1]
I-352'
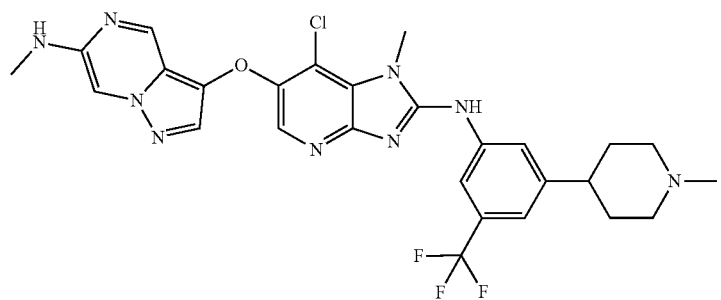
I-353

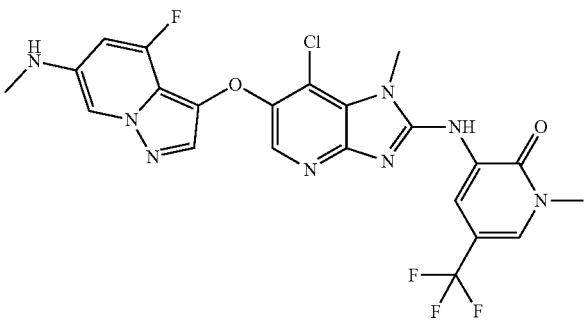
I-354
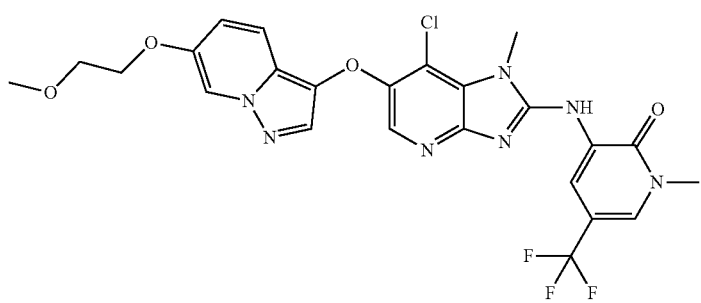
I-355
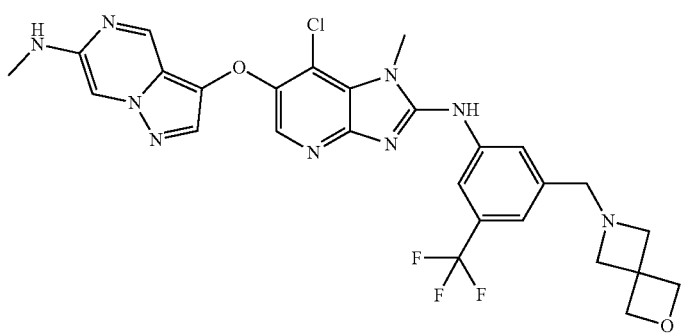 [SMILES: CNc1cn2ncc(Oc3cnc4nc(Nc5cc(CN6CC7(COC7)C6)cc(C(F)(F)F)c5)n(C)c4c3Cl)c2cn1]
I-356
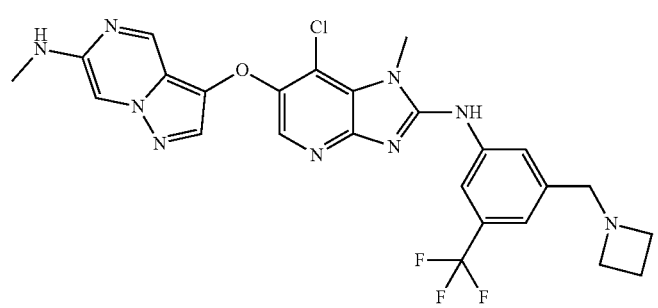 [SMILES: CNc1cn2ncc(Oc3cnc4nc(Nc5cc(CN6CCC6)cc(C(F)(F)F)c5)n(C)c4c3Cl)c2cn1]
I-357
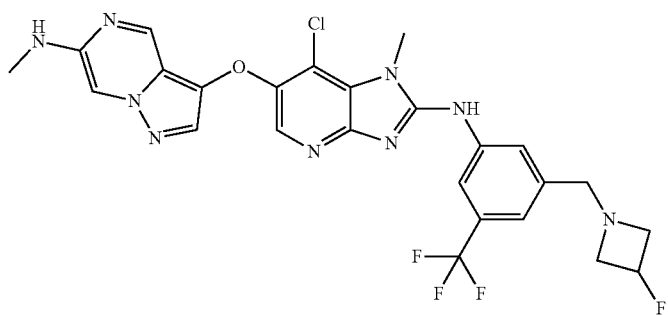 [SMILES: CNc1cn2ncc(Oc3cnc4nc(Nc5cc(CN6CC(F)C6)cc(C(F)(F)F)c5)n(C)c4c3Cl)c2cn1]
I-358

-continued
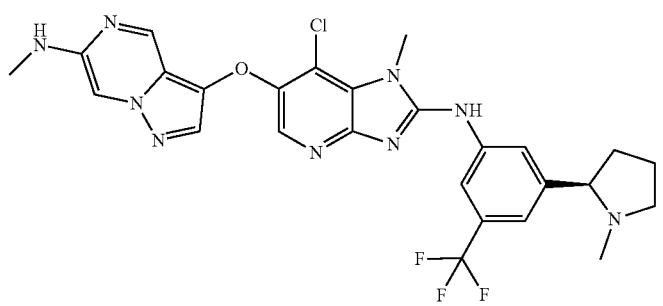 [SMILES: CNc1cn2ncc(Oc3cnc4nc(Nc5cc([C@H]6CCCN6C)cc(C(F)(F)F)c5)n(C)c4c3Cl)c2cn1]
I-359-i
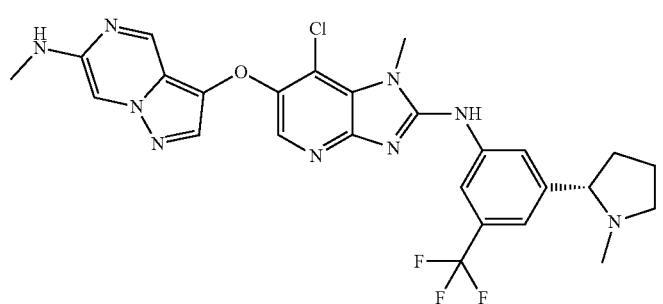 [SMILES: CNc1cn2ncc(Oc3cnc4nc(Nc5cc([C@@H]6CCCN6C)cc(C(F)(F)F)c5)n(C)c4c3Cl)c2cn1]
I-359-ii
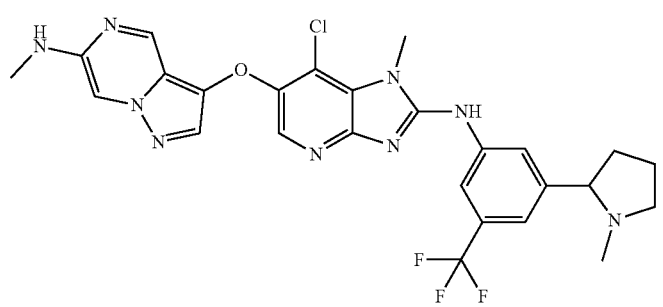 [SMILES: CNc1cn2ncc(Oc3cnc4nc(Nc5cc(C6CCCN6C)cc(C(F)(F)F)c5)n(C)c4c3Cl)c2cn1]
I-359'
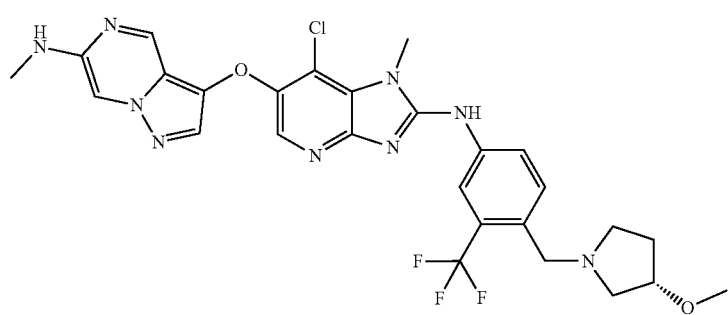
I-360
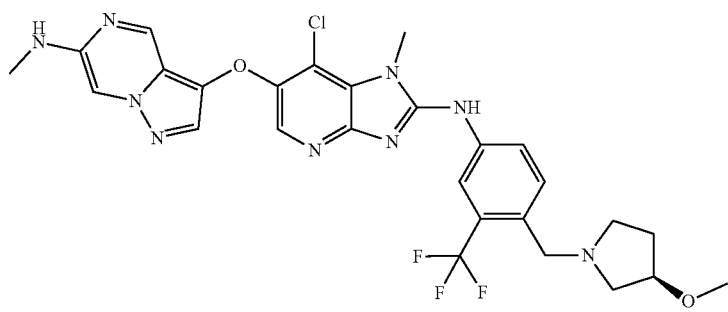
I-361

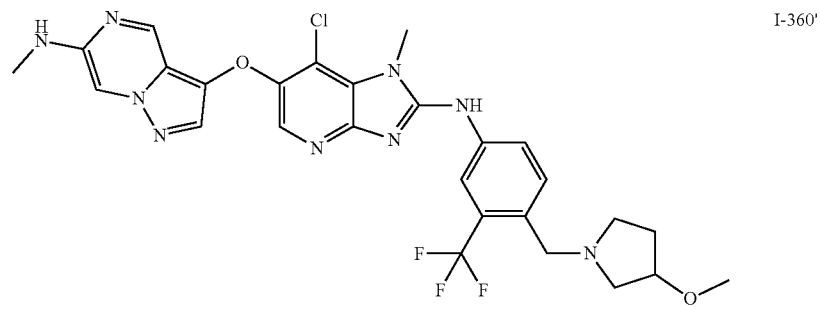
I-360'
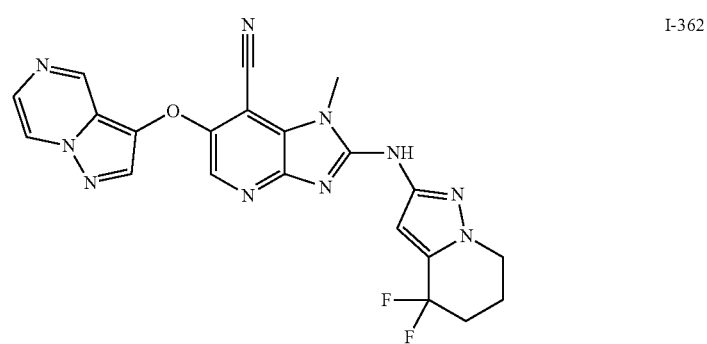
I-362
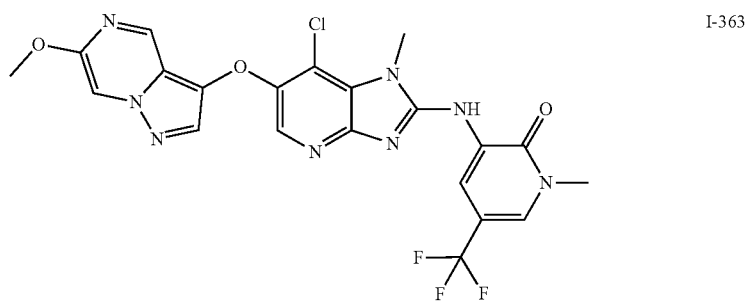
I-363
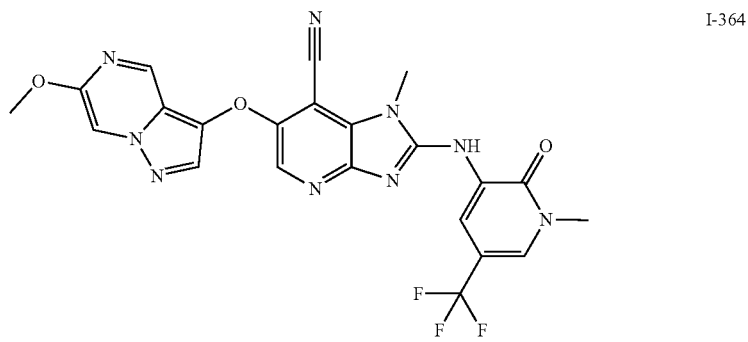
I-364
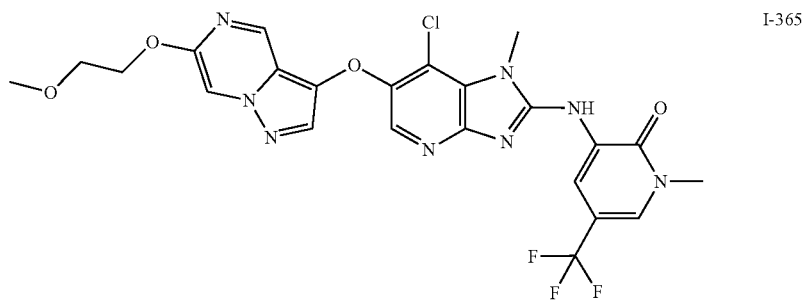
I-365

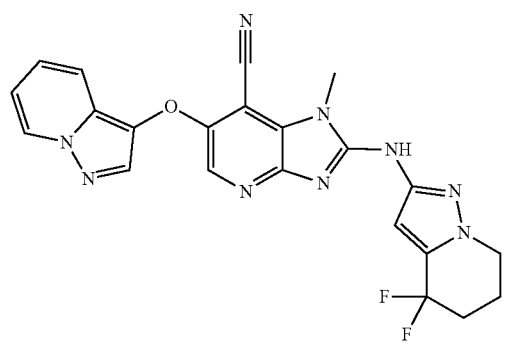 [SMILES: Cn1c(Nc2cc3n(n2)CCCC3(F)F)nc2ncc(Oc3cnn4ccccc34)c(C#N)c21]
I-366
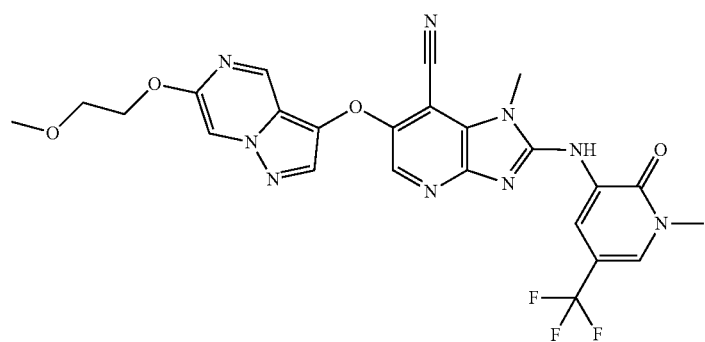
I-367
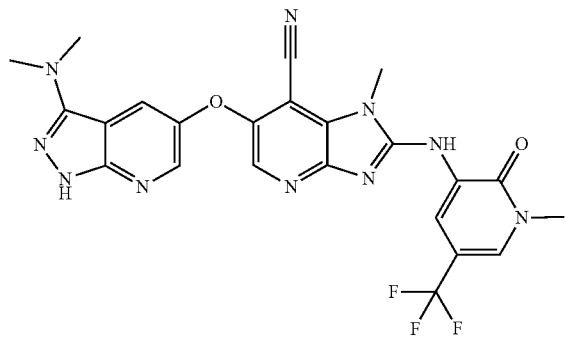
I-368
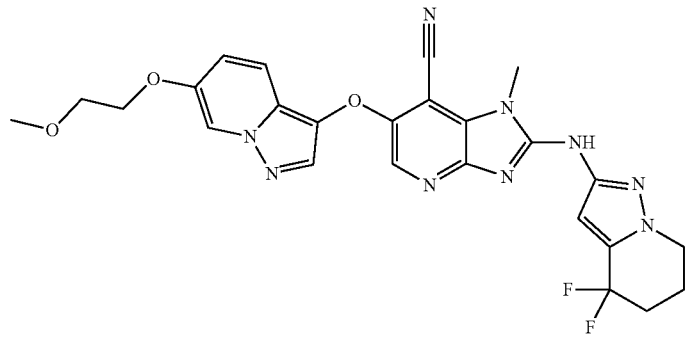 [SMILES: COCCOc1ccc2c(Oc3cnc4nc(Nc5cc6n(n5)CCCC6(F)F)n(C)c4c3C#N)cnn2c1]
I-369

-continued
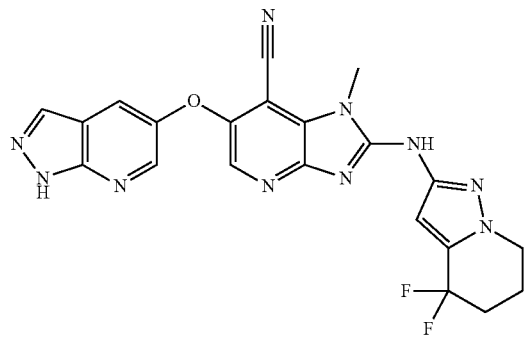 [SMILES: Cn1c(Nc2cc3n(n2)CCCC3(F)F)nc2ncc(Oc3cnc4[nH]ncc4c3)c(C#N)c21]
I-370
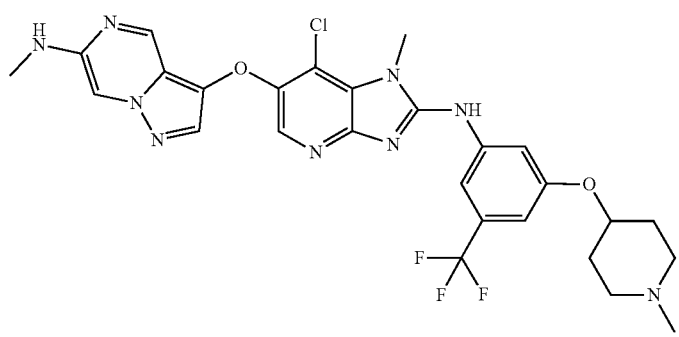 [SMILES: CNc1cn2ncc(Oc3cnc4nc(Nc5cc(OC6CCN(C)CC6)cc(C(F)(F)F)c5)n(C)c4c3Cl)c2cn1]
I-371
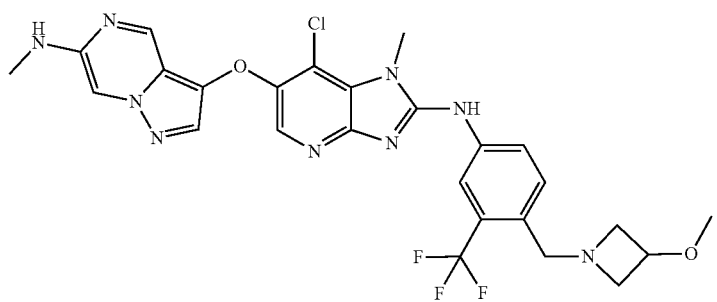
I-372
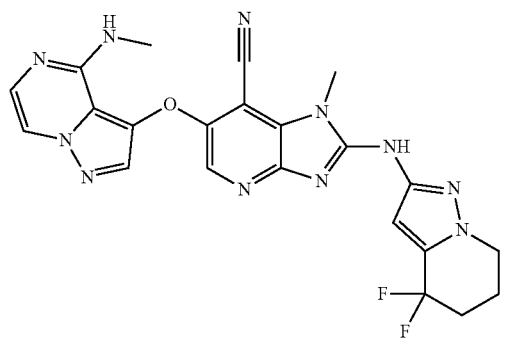 [SMILES: CNc1nccn2ncc(Oc3cnc4nc(Nc5cc6n(n5)CCCC6(F)F)n(C)c4c3C#N)c12]
I-373
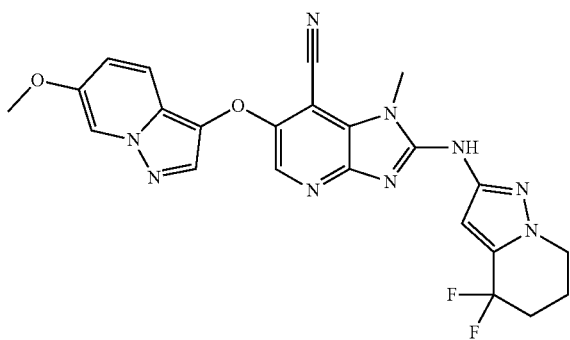 [SMILES: COc1ccc2c(Oc3cnc4nc(Nc5cc6n(n5)CCCC6(F)F)n(C)c4c3C#N)cnn2c1]
I-374

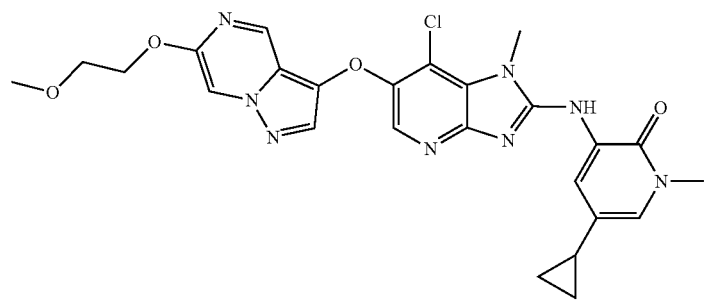
I-375
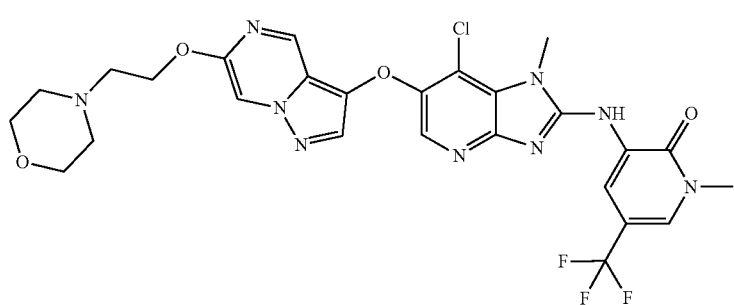 [SMILES: Cn1cc(C(F)(F)F)cc(Nc2nc3ncc(Oc4cnn5cc(OCCN6CCOCC6)ncc45)c(Cl)c3n2C)c1=O]
I-376
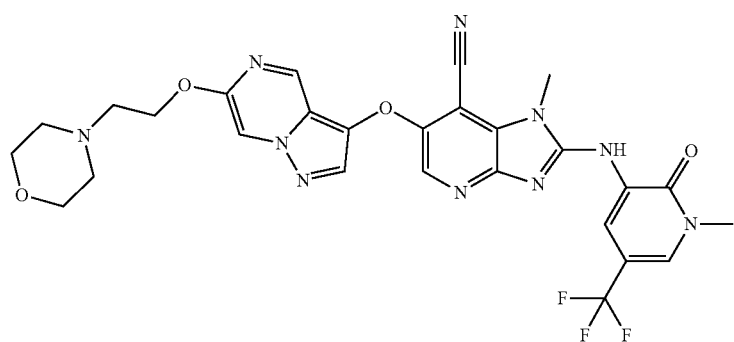 [SMILES: Cn1cc(C(F)(F)F)cc(Nc2nc3ncc(Oc4cnn5cc(OCCN6CCOCC6)ncc45)c(C#N)c3n2C)c1=O]
I-377
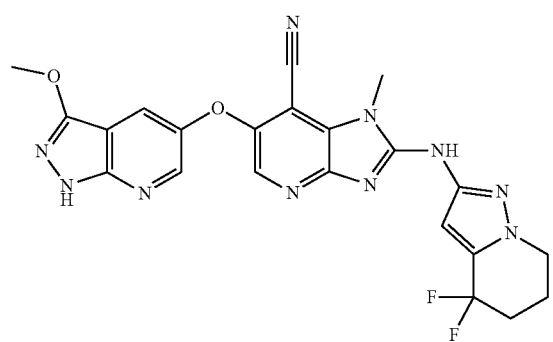 [SMILES: COc1n[nH]c2ncc(Oc3cnc4nc(Nc5cc6n(n5)CCCC6(F)F)n(C)c4c3C#N)cc12]
I-378
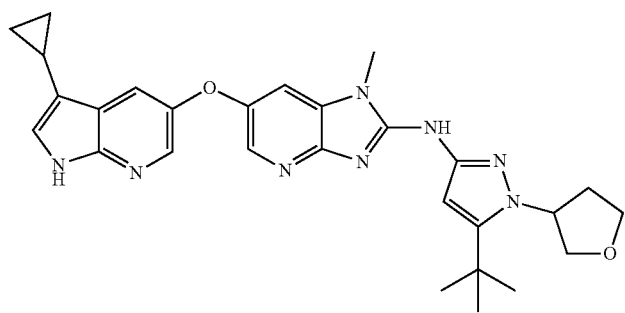 [SMILES: Cn1c(Nc2cc(C(C)(C)C)n(C3CCOC3)n2)nc2ncc(Oc3cnc4[nH]cc(C5CC5)c4c3)cc21]
I-379

-continued
I-379-i
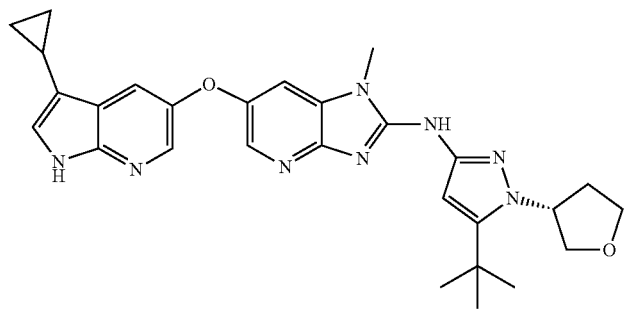 [SMILES: Cn1c(Nc2cc(C(C)(C)C)n([C@@H]3CCOC3)n2)nc2ncc(Oc3cnc4[nH]cc(C5CC5)c4c3)cc21]
I-379-ii
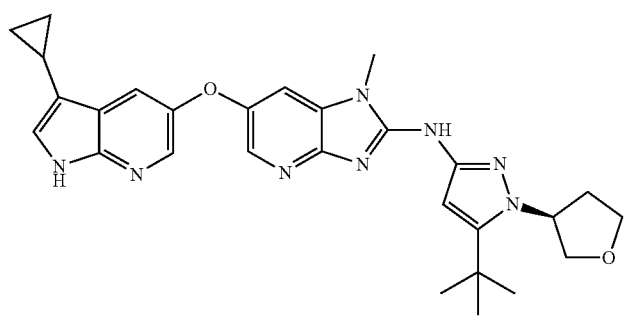 [SMILES: Cn1c(Nc2cc(C(C)(C)C)n([C@H]3CCOC3)n2)nc2ncc(Oc3cnc4[nH]cc(C5CC5)c4c3)cc21]
I-380
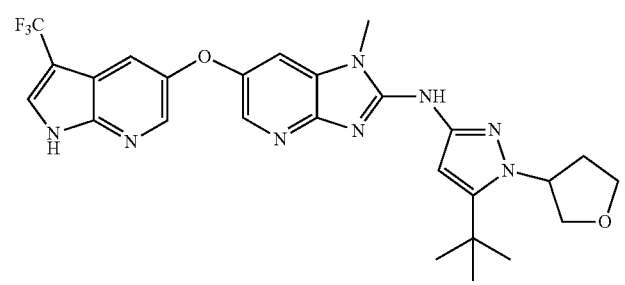 [SMILES: Cn1c(Nc2cc(C(C)(C)C)n(C3CCOC3)n2)nc2ncc(Oc3cnc4[nH]cc(C(F)(F)F)c4c3)cc21]
I-380-i
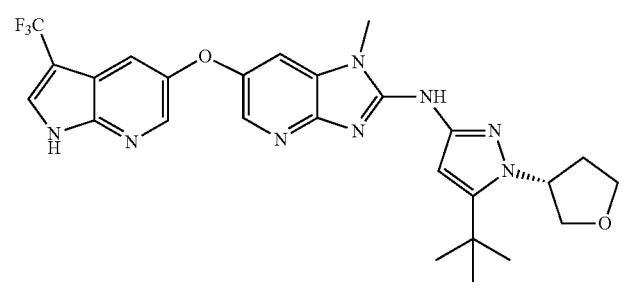
I-380-ii
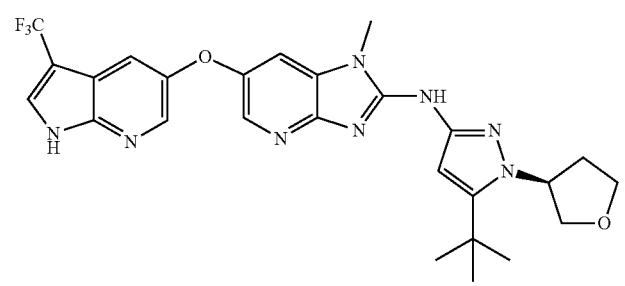 [SMILES: Cn1c(Nc2cc(C(C)(C)C)n([C@H]3CCOC3)n2)nc2ncc(Oc3cnc4[nH]cc(C(F)(F)F)c4c3)cc21]

-continued
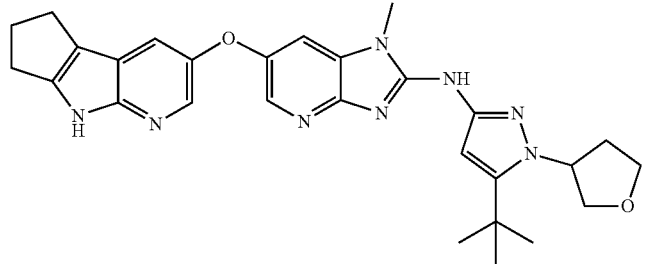 [SMILES: Cn1c(Nc2cc(C(C)(C)C)n(C3CCOC3)n2)nc2ncc(Oc3cnc4[nH]c5c(c4c3)CCC5)cc21]
I-381
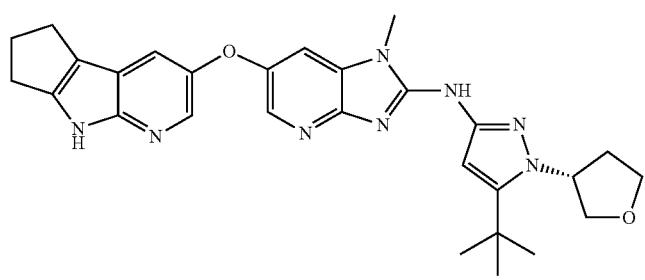 [SMILES: Cn1c(Nc2cc(C(C)(C)C)n([C@@H]3CCOC3)n2)nc2ncc(Oc3cnc4[nH]c5c(c4c3)CCC5)cc21]
I-381-i
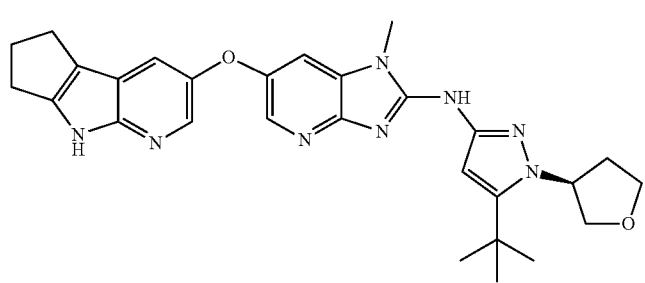 [SMILES: Cn1c(Nc2cc(C(C)(C)C)n([C@H]3CCOC3)n2)nc2ncc(Oc3cnc4[nH]c5c(c4c3)CCC5)cc21]
I-381-ii
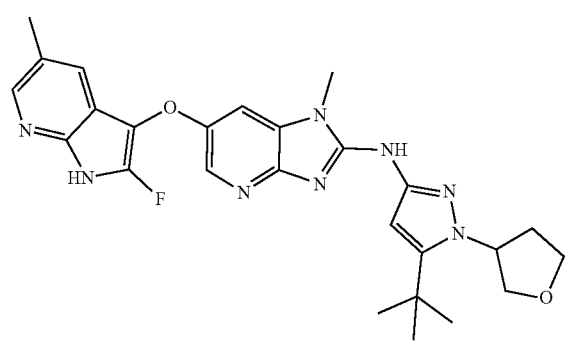 [SMILES: Cc1cnc2[nH]c(F)c(Oc3cnc4nc(Nc5cc(C(C)(C)C)n(C6CCOC6)n5)n(C)c4c3)c2c1]
I-382
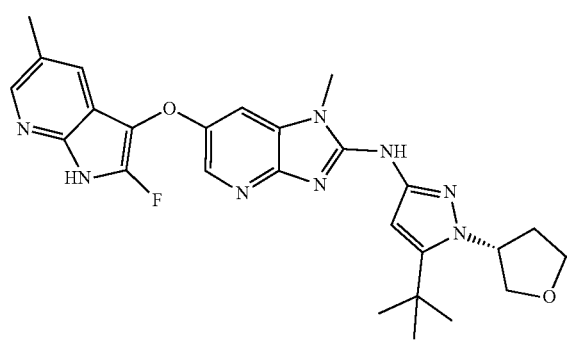 [SMILES: Cc1cnc2[nH]c(F)c(Oc3cnc4nc(Nc5cc(C(C)(C)C)n([C@@H]6CCOC6)n5)n(C)c4c3)c2c1]
I-382-i

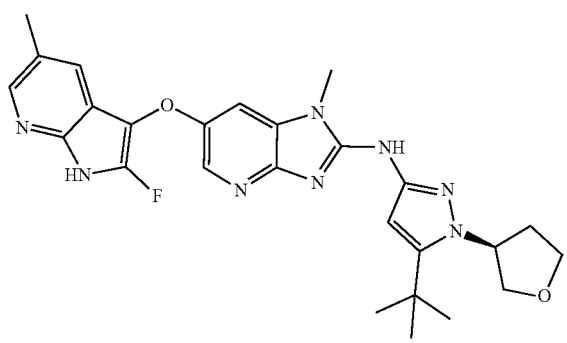 [SMILES: Cc1cnc2[nH]c(F)c(Oc3cnc4nc(Nc5cc(C(C)(C)C)n([C@H]6CCOC6)n5)n(C)c4c3)c2c1]
I-382-ii
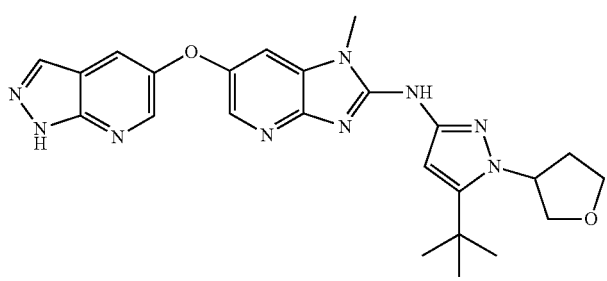 [SMILES: Cn1c(Nc2cc(C(C)(C)C)n(C3CCOC3)n2)nc2ncc(Oc3cnc4[nH]ncc4c3)cc21]
I-383
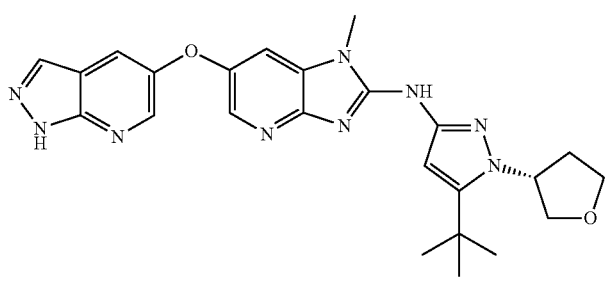 [SMILES: Cn1c(Nc2cc(C(C)(C)C)n([C@@H]3CCOC3)n2)nc2ncc(Oc3cnc4[nH]ncc4c3)cc21]
I-383-i
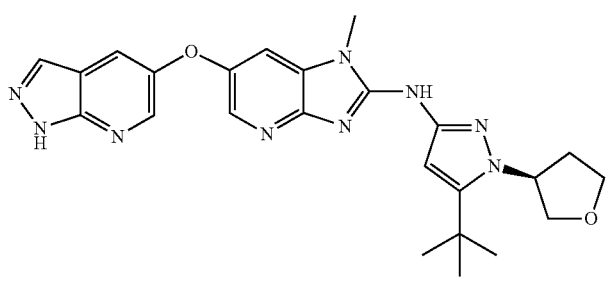 [SMILES: Cn1c(Nc2cc(C(C)(C)C)n([C@H]3CCOC3)n2)nc2ncc(Oc3cnc4[nH]ncc4c3)cc21]
I-383-ii
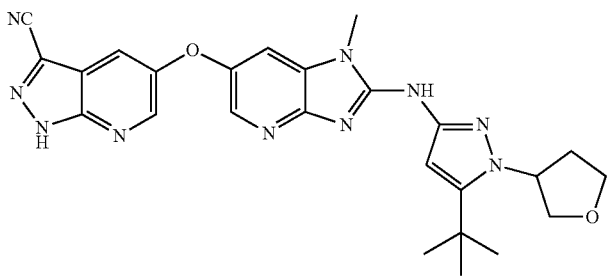 [SMILES: Cn1c(Nc2cc(C(C)(C)C)n(C3CCOC3)n2)nc2ncc(Oc3cnc4[nH]nc(C#N)c4c3)cc21]
I-384

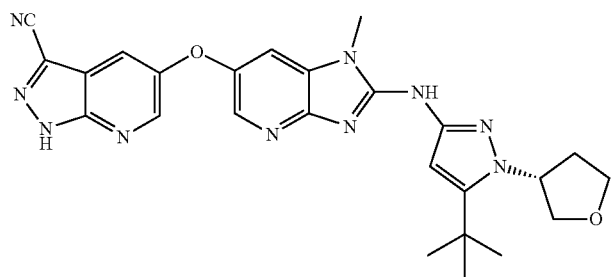 [SMILES: Cn1c(Nc2cc(C(C)(C)C)n([C@@H]3CCOC3)n2)nc2ncc(Oc3cnc4[nH]nc(C#N)c4c3)cc21]
I-384-i
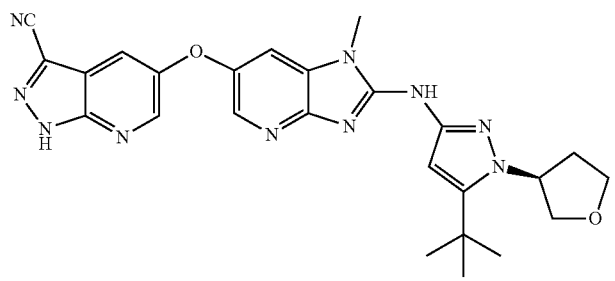 [SMILES: Cn1c(Nc2cc(C(C)(C)C)n([C@H]3CCOC3)n2)nc2ncc(Oc3cnc4[nH]nc(C#N)c4c3)cc21]
I-384-ii
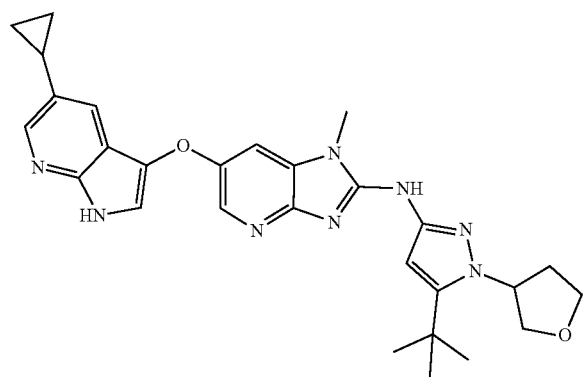 [SMILES: Cn1c(Nc2cc(C(C)(C)C)n(C3CCOC3)n2)nc2ncc(Oc3c[nH]c4ncc(C5CC5)cc34)cc21]
I-385
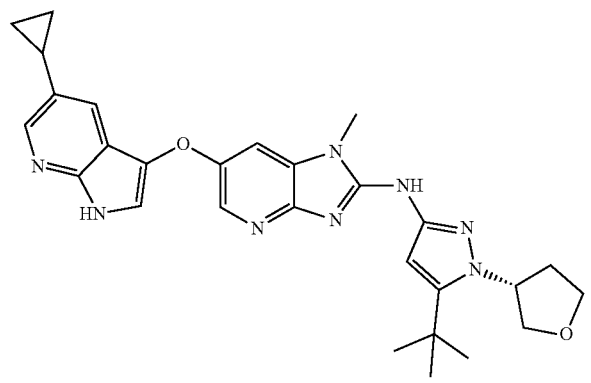 [SMILES: Cn1c(Nc2cc(C(C)(C)C)n([C@@H]3CCOC3)n2)nc2ncc(Oc3c[nH]c4ncc(C5CC5)cc34)cc21]
I-385-i

-continued
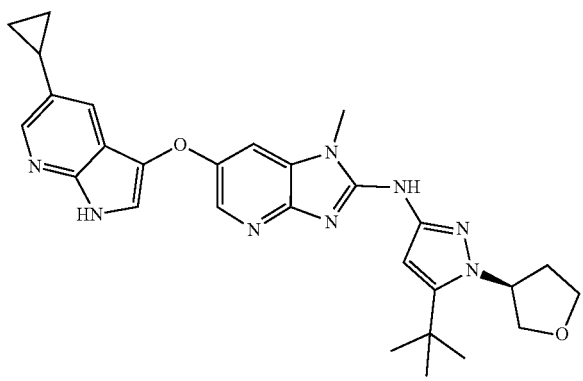 [SMILES: Cn1c(Nc2cc(C(C)(C)C)n([C@H]3CCOC3)n2)nc2ncc(Oc3c[nH]c4ncc(C5CC5)cc34)cc21]
I-385-ii
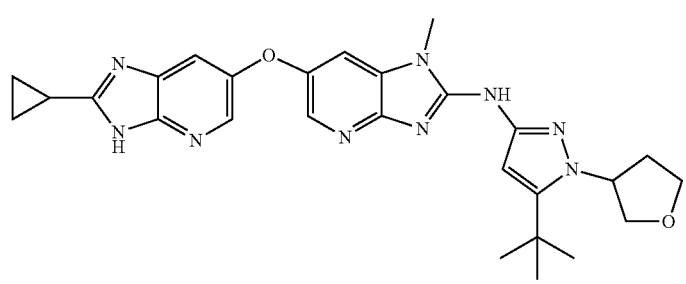 [SMILES: Cn1c(Nc2cc(C(C)(C)C)n(C3CCOC3)n2)nc2ncc(Oc3cnc4[nH]c(C5CC5)nc4c3)cc21]
I-386
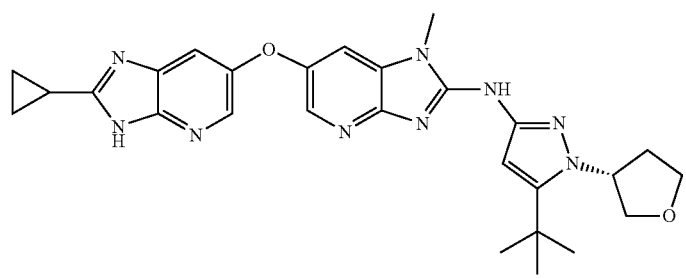 [SMILES: Cn1c(Nc2cc(C(C)(C)C)n([C@@H]3CCOC3)n2)nc2ncc(Oc3cnc4[nH]c(C5CC5)nc4c3)cc21]
I-386-i
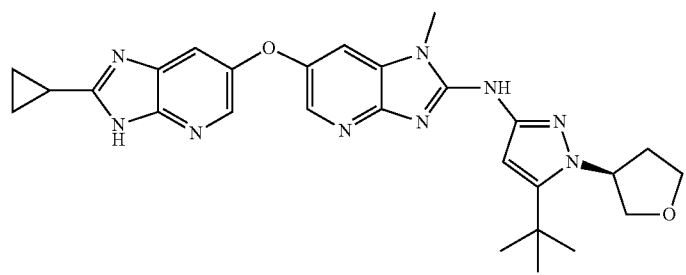
I-386-ii
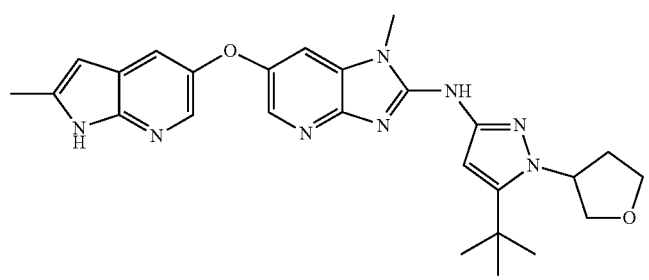 [SMILES: Cc1cc2cc(Oc3cnc4nc(Nc5cc(C(C)(C)C)n(C6CCOC6)n5)n(C)c4c3)cnc2[nH]1]
I-387

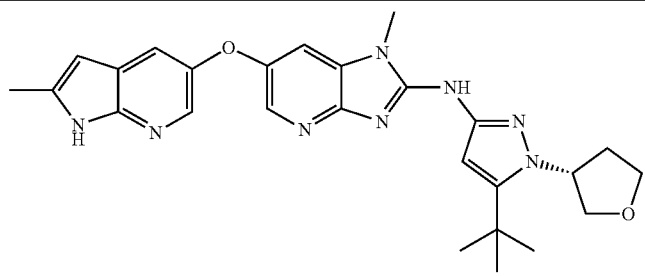
I-387-i
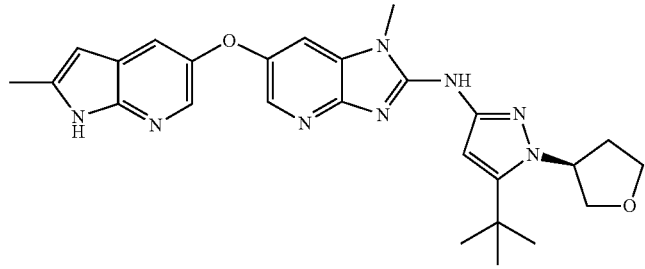 [SMILES: Cc1cc2cc(Oc3cnc4nc(Nc5cc(C(C)(C)C)n([C@H]6CCOC6)n5)n(C)c4c3)cnc2[nH]1]
I-387-ii
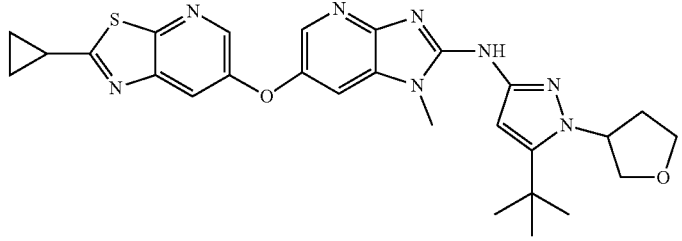 [SMILES: Cn1c(Nc2cc(C(C)(C)C)n(C3CCOC3)n2)nc2ncc(Oc3cnc4sc(C5CC5)nc4c3)cc21]
I-388
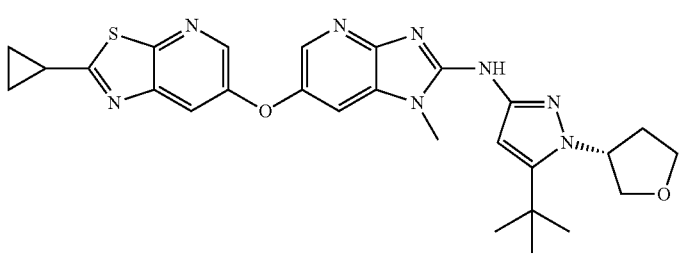 [SMILES: Cn1c(Nc2cc(C(C)(C)C)n([C@@H]3CCOC3)n2)nc2ncc(Oc3cnc4sc(C5CC5)nc4c3)cc21]
I-388-i
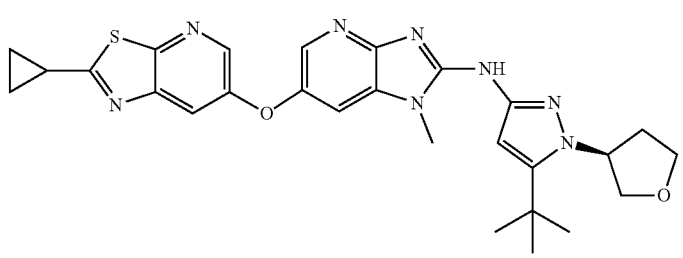 [SMILES: Cn1c(Nc2cc(C(C)(C)C)n([C@H]3CCOC3)n2)nc2ncc(Oc3cnc4sc(C5CC5)nc4c3)cc21]
I-388-ii
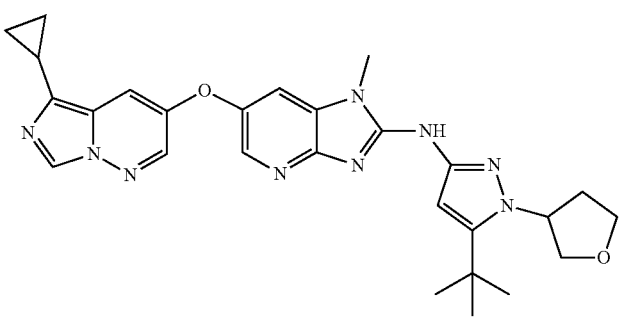 [SMILES: Cn1c(Nc2cc(C(C)(C)C)n(C3CCOC3)n2)nc2ncc(Oc3cnn4cnc(C5CC5)c4c3)cc21]
I-389

-continued
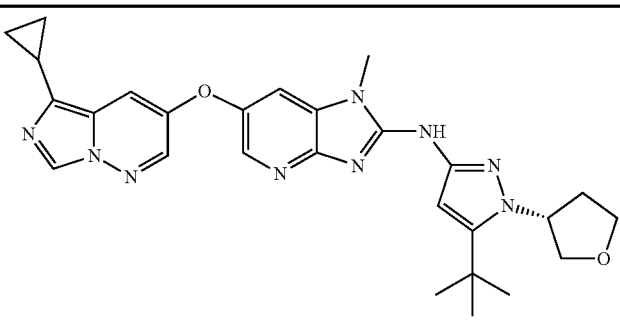
I-389-i
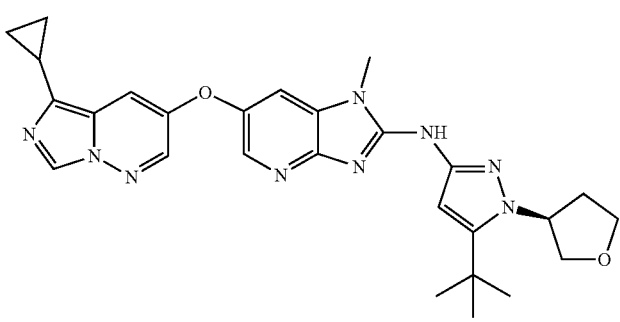 [SMILES: Cn1c(Nc2cc(C(C)(C)C)n([C@H]3CCOC3)n2)nc2ncc(Oc3cnn4cnc(C5CC5)c4c3)cc21]
I-389-ii
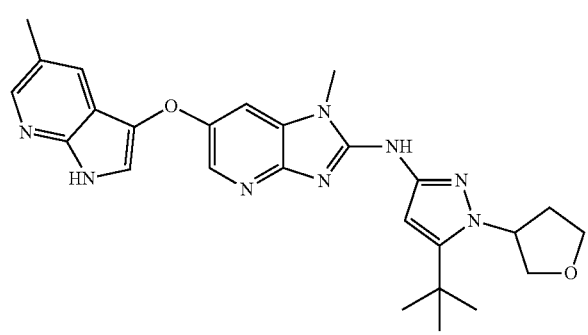 [SMILES: Cc1cnc2[nH]cc(Oc3cnc4nc(Nc5cc(C(C)(C)C)n(C6CCOC6)n5)n(C)c4c3)c2c1]
I-390
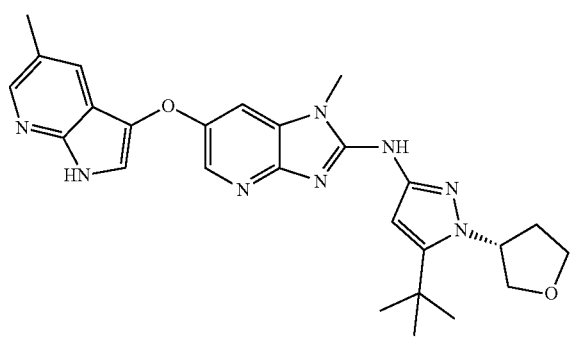 [SMILES: Cc1cnc2[nH]cc(Oc3cnc4nc(Nc5cc(C(C)(C)C)n([C@@H]6CCOC6)n5)n(C)c4c3)c2c1]
I-390-i
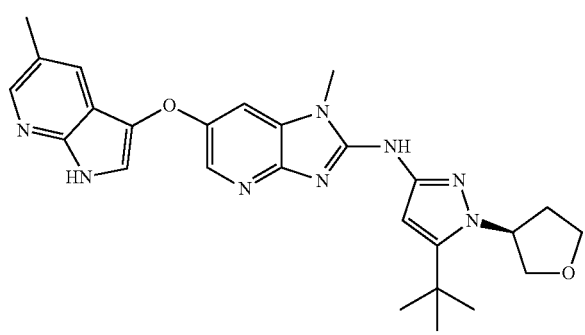 [SMILES: Cc1cnc2[nH]cc(Oc3cnc4nc(Nc5cc(C(C)(C)C)n([C@H]6CCOC6)n5)n(C)c4c3)c2c1]
I-390-ii I-391
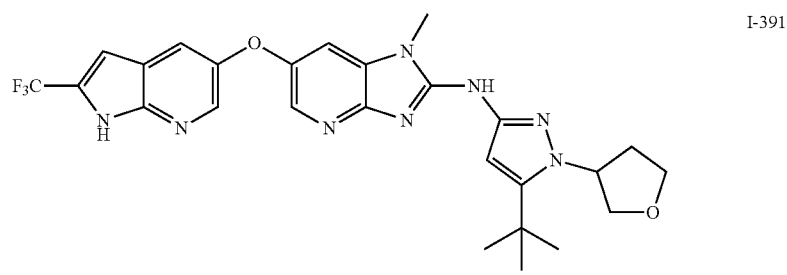
I-391-i
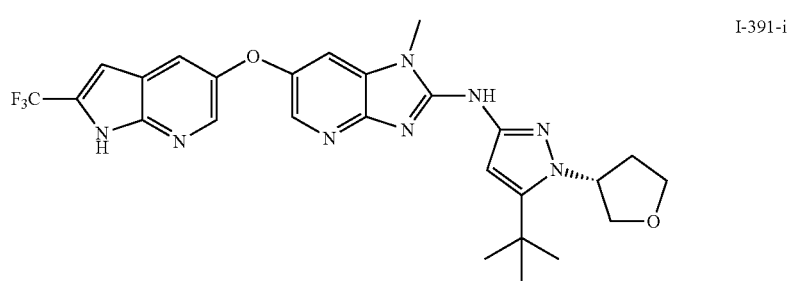
I-391-ii
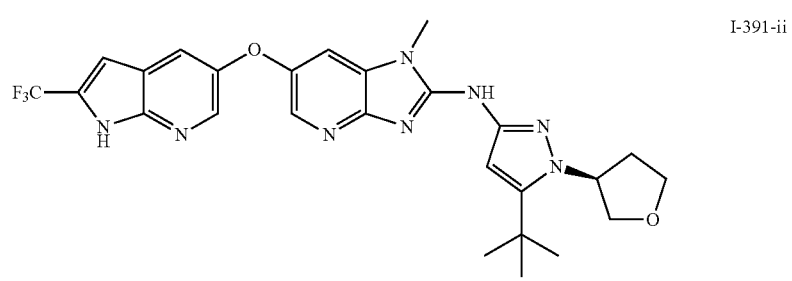
I-392
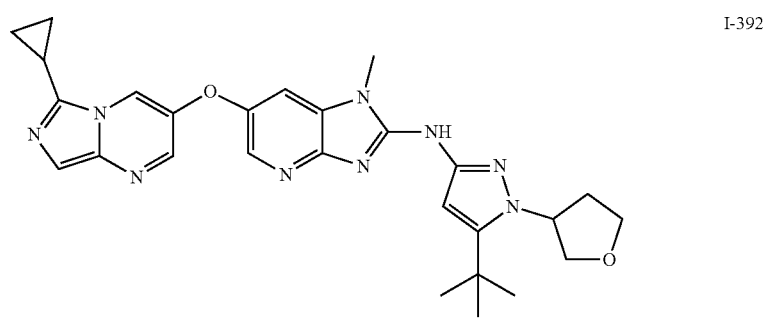
I-392-i
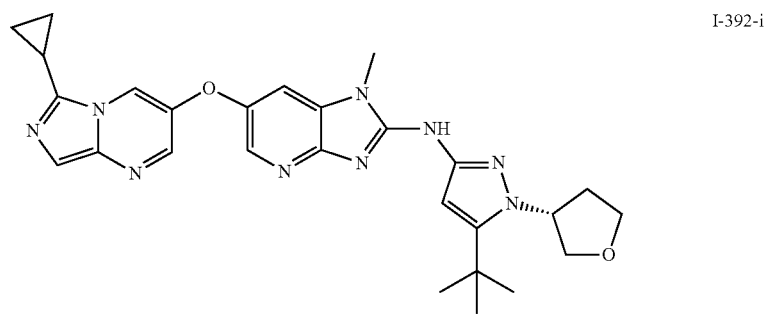

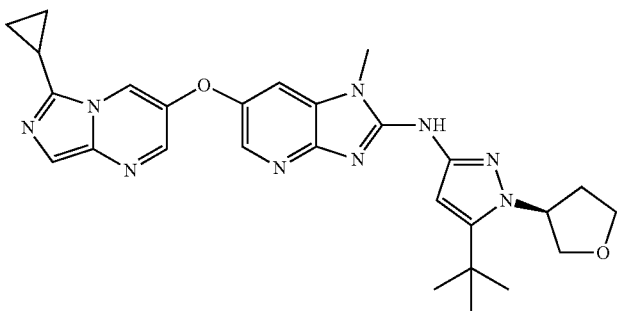 [SMILES: Cn1c(Nc2cc(C(C)(C)C)n([C@H]3CCOC3)n2)nc2ncc(Oc3cnc4cnc(C5CC5)n4c3)cc21]
I-392-ii
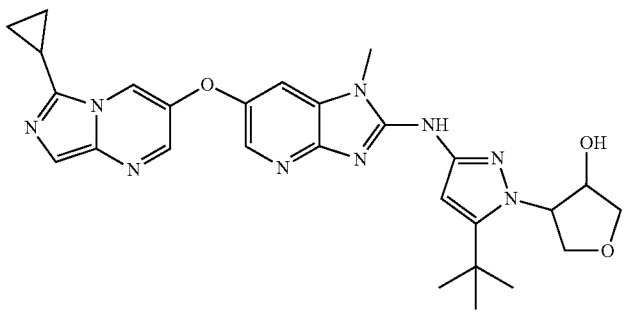 [SMILES: Cn1c(Nc2cc(C(C)(C)C)n(C3COCC3O)n2)nc2ncc(Oc3cnc4cnc(C5CC5)n4c3)cc21]
I-393
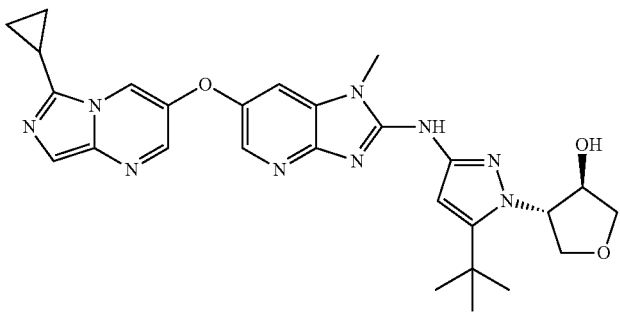 [SMILES: Cn1c(Nc2cc(C(C)(C)C)n([C@H]3COC[C@@H]3O)n2)nc2ncc(Oc3cnc4cnc(C5CC5)n4c3)cc21]
I-393-i
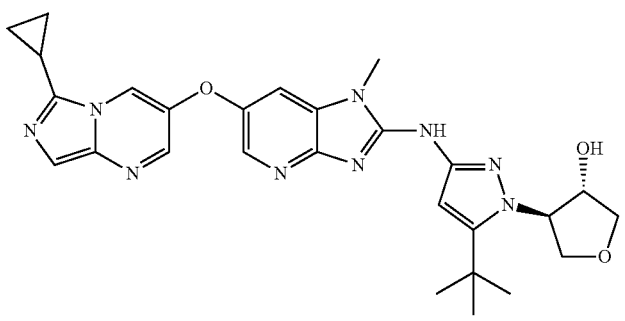 [SMILES: Cn1c(Nc2cc(C(C)(C)C)n([C@@H]3COC[C@H]3O)n2)nc2ncc(Oc3cnc4cnc(C5CC5)n4c3)cc21]
I-393-ii
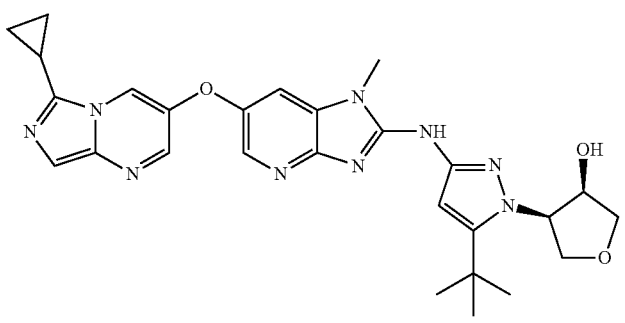 [SMILES: Cn1c(Nc2cc(C(C)(C)C)n([C@@H]3COC[C@@H]3O)n2)nc2ncc(Oc3cnc4cnc(C5CC5)n4c3)cc21]
I-393-iii

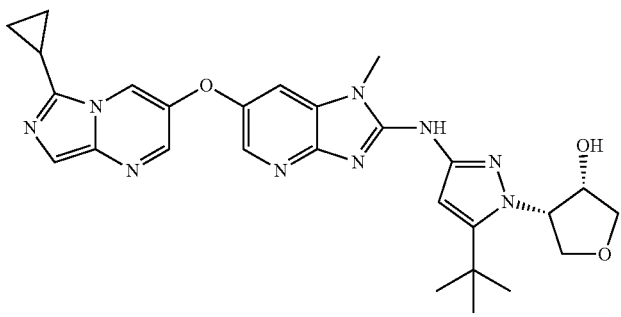 [SMILES: Cn1c(Nc2cc(C(C)(C)C)n([C@H]3COC[C@H]3O)n2)nc2ncc(Oc3cnc4cnc(C5CC5)n4c3)cc21]
I-393-iv
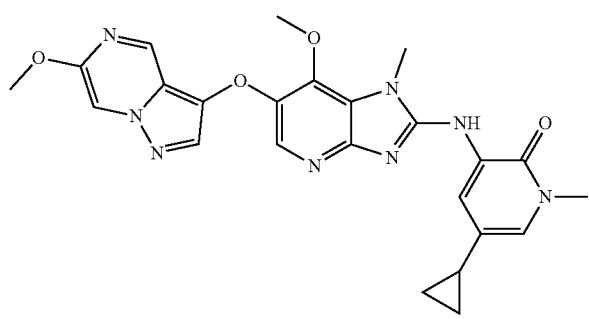
I-394
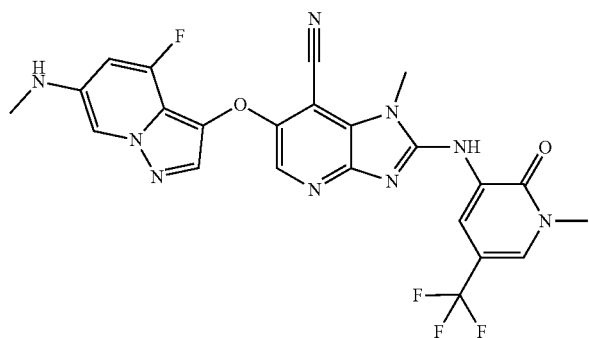
I-395
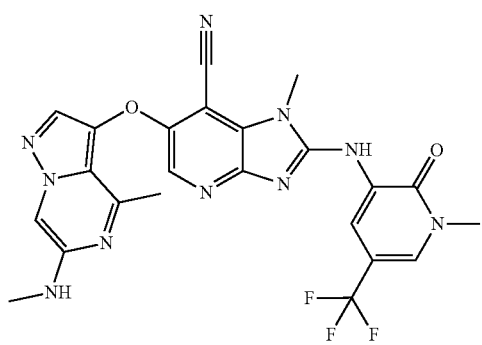
I-396
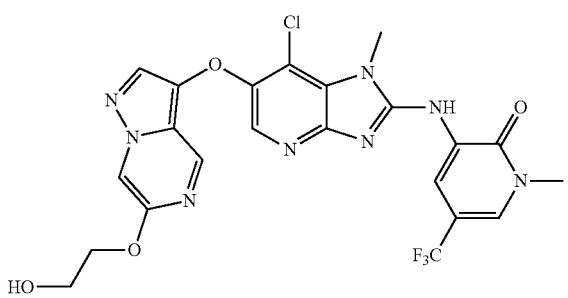 [SMILES: Cn1cc(C(F)(F)F)cc(Nc2nc3ncc(Oc4cnn5cc(OCCO)ncc45)c(Cl)c3n2C)c1=O]
I-397

I-398
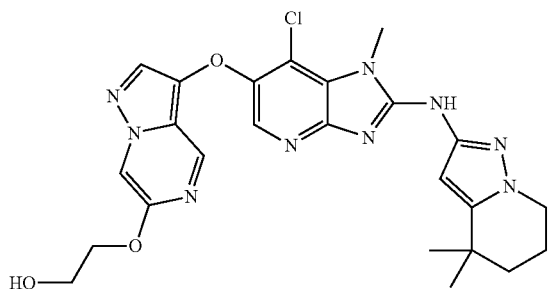 [SMILES: Cn1c(Nc2cc3n(n2)CCCC3(C)C)nc2ncc(Oc3cnn4cc(OCCO)ncc34)c(Cl)c21]
I-399
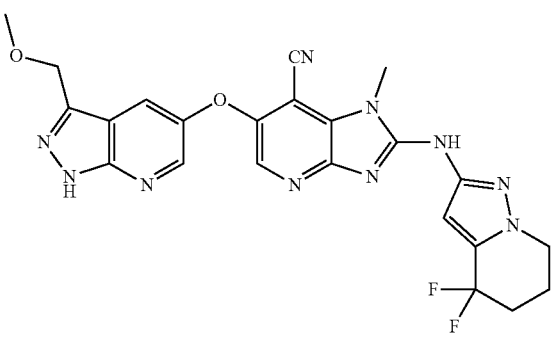 [SMILES: COCc1n[nH]c2ncc(Oc3cnc4nc(Nc5cc6n(n5)CCCC6(F)F)n(C)c4c3C#N)cc12]
I-400
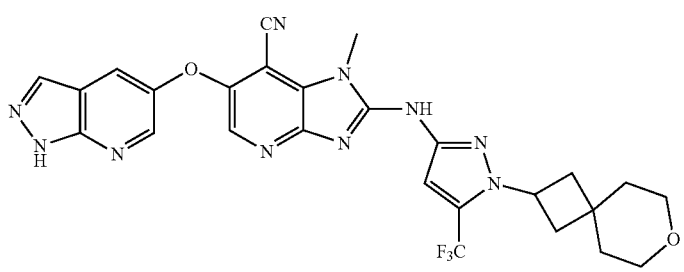 [SMILES: Cn1c(Nc2cc(C(F)(F)F)n(C3CC4(CCOCC4)C3)n2)nc2ncc(Oc3cnc4[nH]ncc4c3)c(C#N)c21]
I-401
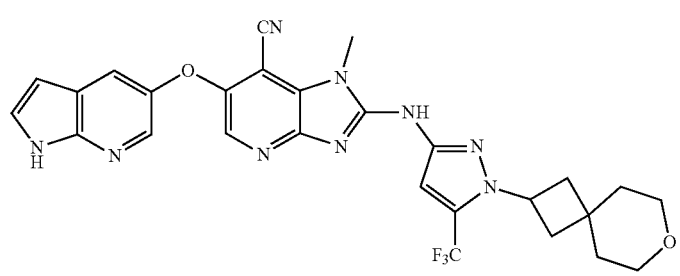 [SMILES: Cn1c(Nc2cc(C(F)(F)F)n(C3CC4(CCOCC4)C3)n2)nc2ncc(Oc3cnc4[nH]ccc4c3)c(C#N)c21]
I-402'
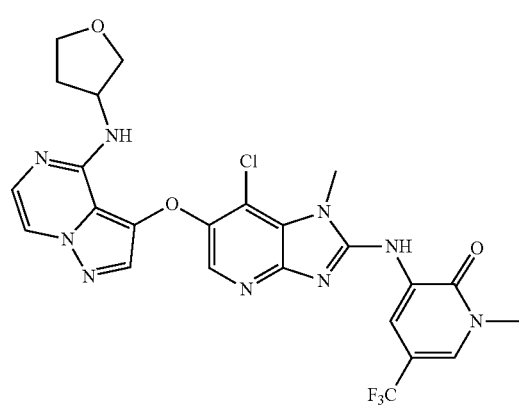 [SMILES: Cn1cc(C(F)(F)F)cc(Nc2nc3ncc(Oc4cnn5ccnc(NC6CCOC6)c45)c(Cl)c3n2C)c1=O]

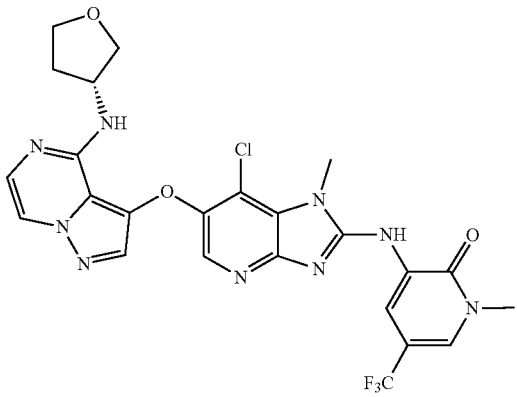 [SMILES: Cn1cc(C(F)(F)F)cc(Nc2nc3ncc(Oc4cnn5ccnc(N[C@@H]6CCOC6)c45)c(Cl)c3n2C)c1=O]

I-402

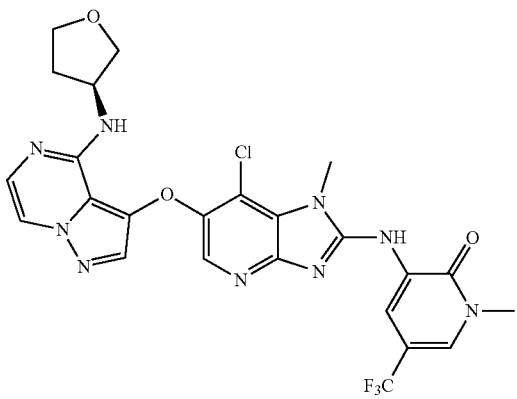 [SMILES: Cn1cc(C(F)(F)F)cc(Nc2nc3ncc(Oc4cnn5ccnc(N[C@H]6CCOC6)c45)c(Cl)c3n2C)c1=O]

I-402-ii

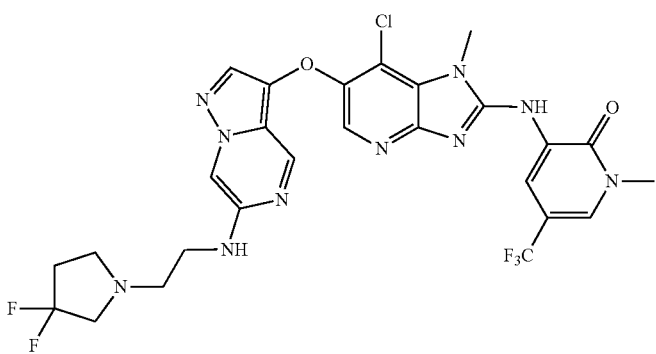 [SMILES: Cn1cc(C(F)(F)F)cc(Nc2nc3ncc(Oc4cnn5cc(NCCN6CCC(F)(F)C6)ncc45)c(Cl)c3n2C)c1=O]

I-403

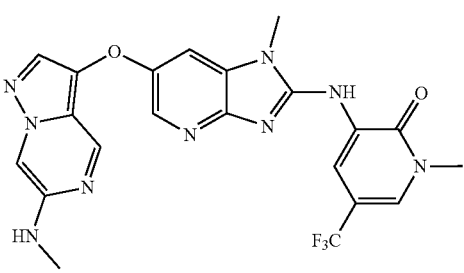 [SMILES: CNc1cn2ncc(Oc3cnc4nc(Nc5cc(C(F)(F)F)cn(C)c5=O)n(C)c4c3)c2cn1]

I-404 or a pharmaceutically acceptable salt thereof.

In some embodiments, the present disclosure encompasses the recognition that provided compounds display certain desirable characteristics, e.g., as compared to other known compounds. For example, in some embodiments, provided compounds are more potent in one or more biochemical or cellular assays (e.g., the JAK2 Binding Assay or SET2-pSTAT5 Cellular Assay described herein) and/or have one or more other characteristics that make them more suitable for drug development, such as better selectivity over other kinases and/or better ADME (absorption, distribution, metabolism, and excretion) properties including but not limited to better permeability, cytotoxicity, hepatocyte stability, solubility, and/or plasma protein binding profiles (e.g., based on assays described in the ensuing examples), than other known compounds. In some embodiments, provided compounds display certain desirable characteristics in one or more assays described herein, e.g., compared to other known compounds. Without wishing to be bound by any particular theory, the present disclosure encompasses the recognition that 6-heteroaryloxy benzimidazoles and azabenzimidazoles can display certain more desirable characteristics (such as better properties in one or more assays described herein) than corresponding 5-heteroaryloxy benzimidazoles and azabenzimidazoles.

In some embodiments, provided compounds are provided and/or utilized in a salt form (e.g., a pharmaceutically acceptable salt form). Reference to a compound provided herein is understood to include reference to salts thereof, unless otherwise indicated. Pharmaceutically acceptable salt forms are known in the art. For example, S. M. Berge, et al. describes pharmaceutically acceptable salts in detail in J. Pharmaceutical Sciences, 66:1-19(1977).

It will be appreciated that throughout the present disclosure, unless otherwise indicated, reference to a compound of Formula I is intended to also include Formulae II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E, and compound species of such formulas disclosed herein.

Preparing Provided Compounds

Provided compounds may generally be made by the processes described in the ensuing schemes and examples. In some embodiments, provided compounds (e.g., compounds of Formula I wherein Z is —NH—) are prepared according to the following Scheme:

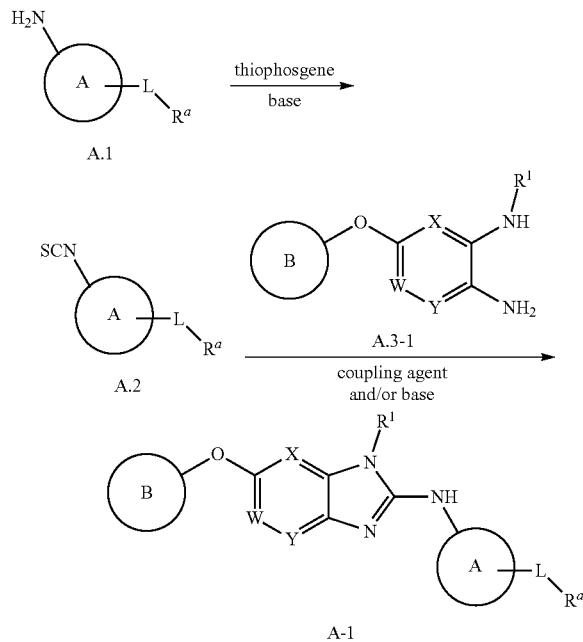

wherein Ring A, Ring B, L, W, X, Y, $R^1$, and $R^a$ are as defined above for Formula I and described in classes and subclasses herein, both singly and in combination. Accordingly, in some embodiments, intermediate A.2 is prepared by a process comprising contacting intermediate A.1 with thiophosgene in the presence of a suitable base (e.g., $NaHCO_3$). In some embodiments, compound A-1 is prepared by a process comprising contacting intermediate A.2 with intermediate A.3-1 in the presence of a suitable coupling agent (e.g., 1-ethyl-3-(3-dimethylaminopropyl)carbodiimide hydrochloride) and/or a suitable base (e.g., potassium tert-butoxide). In some embodiments, a process for preparing compound A-1 further comprises a deprotection step under suitable conditions. In some embodiments, a process for preparing compound A-1 further comprises a functionalization step (e.g., cyanation, methylation, or acetylation) under suitable conditions.

In some embodiments, provided compounds (e.g., compounds of Formula I wherein Z is —$NR^z$— or —O—) are prepared according to the following Scheme:

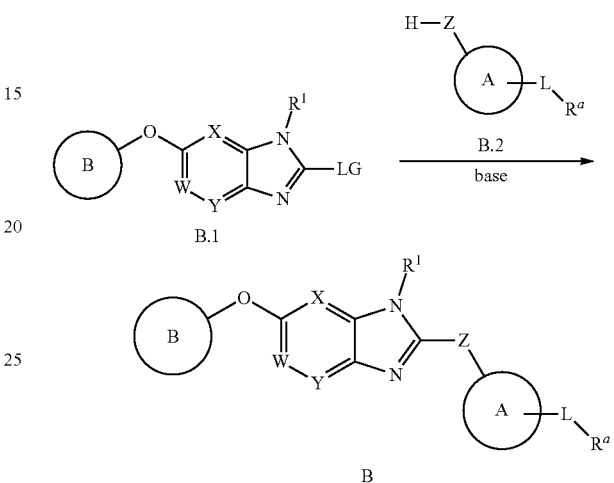

wherein LG is a suitable leaving group (e.g., halogen, e.g., chloro or bromo) and Ring A, Ring B L, W, X, Y, Z, $R^1$, and $R^a$ are as defined above for Formula I and described in classes and subclasses herein, both singly and in combination. Accordingly, in some embodiments, compound B is prepared by a process comprising contacting intermediate B.1 with intermediate B.2 in the presence of a suitable base (e.g., $K_3PO_4$, $K_2CO_3$, or $Cs_2CO_3$). In some embodiments, compound B is prepared by a process comprising contacting intermediate B.1 with intermediate B.2 in the presence of a suitable base (e.g., $K_3PO_4$, $K_2CO_3$, or $Cs_2CO_3$), a suitable metal complex (e.g., a palladium complex such as tris (dibenzylideneacetone)dipalladium(0) or [(2-di-tert-butylphosphino-2',4',6'-triisopropyl-1,1'-biphenyl)-2-(2'-amino-1,1'-biphenyl)]palladium(II) methanesulfonate), and, optionally, a suitable ligand (e.g., 4,5-bis(diphenylphosphino)-9,9-dimethylxanthene). In some embodiments, a process for preparing compound B further comprises a deprotection step under suitable conditions. In some embodiments, a process for preparing compound B further comprises a funtionalization step (e.g., cyanation, methylation, or acetylation) under suitable conditions.

In some embodiments, provided compounds (e.g., compounds of Formula I, wherein Ring B is substituted with a —OR or —$N(R)_2$ moiety) are prepared according to the following Scheme:

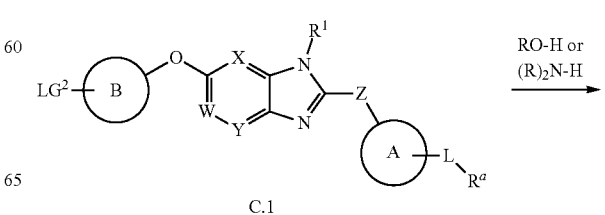

-continued

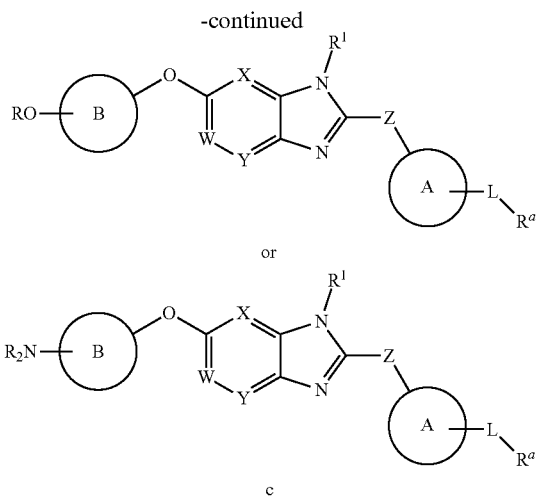

c wherein $LG^2$ is a suitable leaving group (e.g., halogen, e.g., fluoro or chloro) and Ring A, Ring B, L, W, X, Y, Z, R, $R^1$, and $R^a$ are as defined above for Formula I and described in classes and subclasses herein, both singly and in combination. Accordingly, in some embodiments, compound C is prepared by a process comprising contacting intermediate C.1 with a suitable RO—H or $(R)_2N$—H compound, optionally in the presence of a suitable base (e.g., tBuOK). In some embodiments, intermediate C.1 can be prepared by a process described herein, such as that described in the Schemes above for the synthesis of compound A-1 or compound B.

In some embodiments, a provided compound is obtained by a process comprising a purification method described in the Examples section. In some such embodiments, a compound is the $1^{st}$ eluting isomer. In some such embodiments, a compound is the $2^{nd}$ eluting isomer. In some embodiments, a compound is the $3^{rd}$ eluting isomer. In some embodiments, a compound is the $4^{th}$ eluting isomer. In some embodiments, a compound is the $5^{th}$, $6^{th}$, $7^{th}$, $8^{th}$, or more eluting isomer.

Compositions

The present disclosure also provides compositions comprising a compound provided herein with one or more other components. In some embodiments, provided compositions comprise and/or deliver a compound described herein (e.g., compounds of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E).

In some embodiments, a provided composition is a pharmaceutical composition that comprises and/or delivers a compound provided herein (e.g., compounds of Formulae I, II, III, IV, I-A, II-A, III-A, IV-A, I-B, II-B, III-B, IV-B, I-C, II-C, III-C, IV-C, I-D, II-D, III-D, IV-D, I-E, II-E, III-E, and IV-E) and further comprises a pharmaceutically acceptable carrier. Pharmaceutical compositions typically contain an active agent (e.g., a compound described herein) in an amount effective to achieve a desired therapeutic effect while avoiding or minimizing adverse side effects. In some embodiments, provided pharmaceutical compositions comprise a compound described herein and one or more fillers, disintegrants, lubricants, glidants, anti-adherents, and/or anti-statics, etc. Provided pharmaceutical compositions can be in a variety of forms including oral dosage forms, topical creams, topical patches, iontophoresis forms, suppository, nasal spray and/or inhaler, eye drops, intraocular injection forms, depot forms, as well as injectable and infusible solutions. Methods of preparing pharmaceutical compositions are well known in the art.

In some embodiments, provided compounds are formulated in a unit dosage form for ease of administration and uniformity of dosage. The expression "unit dosage form" as used herein refers to a physically discrete unit of an active agent (e.g., a compound described herein) for administration to a subject. Typically, each such unit contains a predetermined quantity of active agent. In some embodiments, a unit dosage form contains an entire single dose of the agent. In some embodiments, more than one unit dosage form is administered to achieve a total single dose. In some embodiments, administration of multiple unit dosage forms is required, or expected to be required, in order to achieve an intended effect. A unit dosage form may be, for example, a liquid pharmaceutical composition containing a predetermined quantity of one or more active agents, a solid pharmaceutical composition (e.g., a tablet, a capsule, or the like) containing a predetermined amount of one or more active agents, a sustained release formulation containing a predetermined quantity of one or more active agents, or a drug delivery device containing a predetermined amount of one or more active agents, etc.

Provided compositions may be administered using any amount and any route of administration effective for treating or lessening the severity of any disease or disorder described herein.

Uses

The present disclosure provides uses for compounds and compositions described herein. In some embodiments, provided compounds and compositions are useful in medicine (e.g., as therapy). In some embodiments, provided compounds and compositions are useful in research as, for example, analytical tools and/or control compounds in biological assays.

In some embodiments, the present disclosure provides methods of administering provided compounds or compositions to a subject in need thereof. In some embodiments, the present disclosure provides methods of administering provided compounds or compositions to a subject suffering from or susceptible to a disease, disorder, or condition associated with JAK2.

In some embodiments, provided compounds are useful as JAK2 inhibitors. In some embodiments, provided compounds are useful as Type II JAK2 inhibitors. In some embodiments, the present disclosure provides methods of inhibiting JAK2 in a subject comprising administering a provided compound or composition. In some embodiments, the present disclosure provides methods of inhibiting JAK2 in a biological sample comprising contacting the sample with a provided compound or composition.

JAK (e.g., JAK2) has been implicated in various diseases, disorders, and conditions, such as myeloproliferative neoplasms (Vainchenker, W. et al., F1000 Research 2018, 7 (F1000 Faculty Rev): 82), atopic dermatitis (Rodrigues, M. A. and Torres, T. J. Derm. Treat. 2019, 31(1), 33-40) and acute respiratory syndrome, hyperinflammation, and/or cytokine storm syndrome (The Lancet. doi:10.1016/S0140-6736(20)30628-0). Accordingly, in some embodiments, the present disclosure provides methods of treating a disease, disorder or condition associated with JAK2 in a subject in need thereof comprising administering to the subject a provided compound or composition. In some embodiments, a disease, disorder or condition is associated with overexpression of JAK2.

In some embodiments, the present disclosure provides methods of treating cancer, comprising administering a provided compound or composition to a subject in need thereof. In some embodiments, the present disclosure provides methods of treating proliferative diseases, comprising administering a provided compound or composition to a subject in need thereof.

In some embodiments, the present disclosure provides methods of treating a hematological malignancy, comprising administering a provided compound or composition to a subject in need thereof. In some embodiments, a hematological malignancy is leukemia (e.g., chronic lymphocytic leukemia, acute lymphoblastic leukemia, T-cell acute lymphoblastic leukemia, chronic myelogenous leukemia, acute myelogenous leukemia, or acute monocytic leukemia). In some embodiments, a hematological malignancy is lymphoma (e.g., Burkitt's lymphoma, Hodgkin's lymphoma, or non-Hodgkin's lymphoma). In some embodiments, a non-Hodgkin's lymphoma is a B-cell lymphoma. In some embodiments, a non-Hodgkin's lymphoma is a NK/T-cell lymphoma (e.g., cutaneous T-cell lymphoma). In some embodiments, a hematological malignancy is myeloma (e.g., multiple myeloma). In some embodiments, a hematological malignancy is myeloproliferative neoplasm (e.g., polycythemia vera, essential thrombocytopenia, or myelofibrosis). In some embodiments, a hematological malignancy is myelodysplastic syndrome.

In some embodiments, the present disclosure provides methods of treating an inflammatory disease, disorder, or condition (e.g., acute respiratory syndrome, hyperinflammation, and/or cytokine storm syndrome (including those associated with COVID-19) or atopic dermatitis), comprising administering a provided compound or composition to a subject in need thereof.

In some embodiments, a provided compound or composition is administered as part of a combination therapy. As used herein, the term "combination therapy" refers to those situations in which a subject is simultaneously exposed to two or more therapeutic or prophylactic regimens (e.g., two or more therapeutic or prophylactic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition.

For example, in some embodiments, a provided compound or composition is administered to a subject who is receiving or has received one or more additional therapies (e.g., an anti-cancer therapy and/or therapy to address one or more side effects of such anti-cancer therapy, or otherwise to provide palliative care). Exemplary additional therapies include BCL2 inhibitors (e.g., venetoclax), HDAC inhibitors (e.g., vorinostat), BET inhibitors (e.g., mivebresib), proteasome inhibitors (e.g., bortezomib), LSD1 inhibitors (e.g., IMG-7289), and CXCR2 inhibitors. Useful combinations of a JAK2 inhibitor with BCL2, HDAC, BET, and proteasome inhibitors have been demonstrated in cells derived from cutaneous T-cell lymphoma patients (Yumeen, S., et al., Blood Adv. 2020, 4(10), 2213-2226). A combination of a JAK2 inhibitor with a LSD1 inhibitor demonstrated good efficacy in a mouse model of myeloproliferative neoplasms (Jutzi, J. S., et al., HemaSphere 2018, 2(3), http://dx.doi.org/10.1097/HS9.0000000000000054). CXCR2 activity has been shown to modulate signaling pathways involved in tumor growth, angiogenesis, and/or metastasis, including the JAK-STAT3 pathway (Jaffer, T., Ma, D. Transl. Cancer Res. 2016, 5 (Suppl. 4), S616-S628).

Exemplary Embodiments

The following numbered embodiments, while non-limiting, are exemplary of certain aspects of the present disclosure:

1. A compound of Formula I:

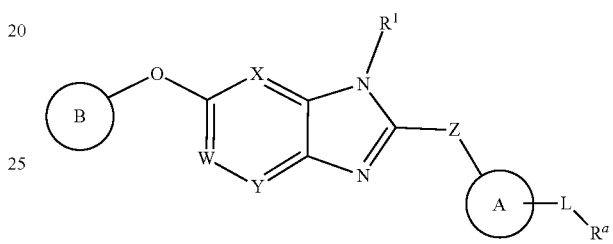

or a pharmaceutically acceptable salt thereof, wherein:
W is $CR^w$ or N;
X is $CR^x$ or N;
Y is $CR^y$ or N;
Z is —O— or —$NR^z$—;
$R^w$, $R^x$ and $R^y$ are each independently hydrogen, halogen, —$OR^2$, —$N(R^2)_2$, —$SR^2$, optionally substituted $C_{1-6}$ aliphatic, or —CN;
$R^z$ is hydrogen or optionally substituted $C_{1-6}$ aliphatic;
$R^1$ is optionally substituted $C_{1-6}$ aliphatic;
each $R^2$ is independently hydrogen or optionally substituted $C_{1-6}$ aliphatic;
Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;
Ring B is optionally substituted 9- to 16-membered bicyclic or tricyclic aryl, optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur;

L is a covalent bond or a bivalent $C_{1-3}$ straight or branched hydrocarbon chain; and $R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

2. The compound of embodiment 1, wherein the compound is not:

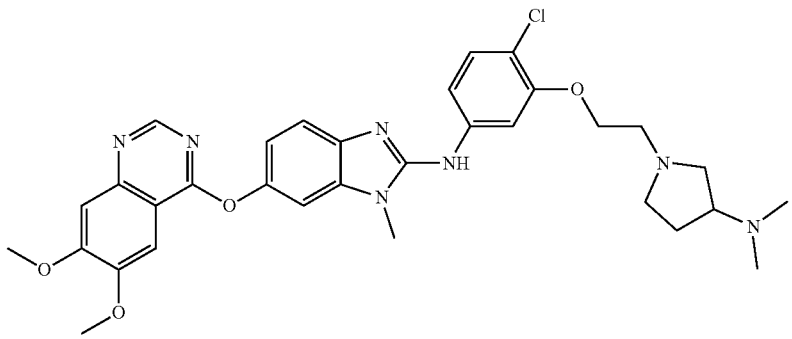

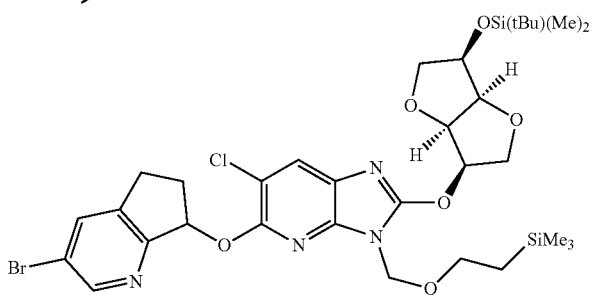

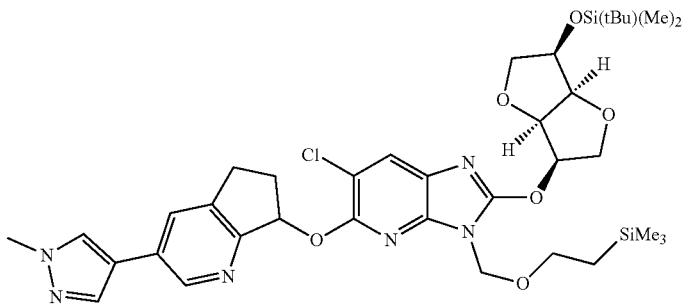

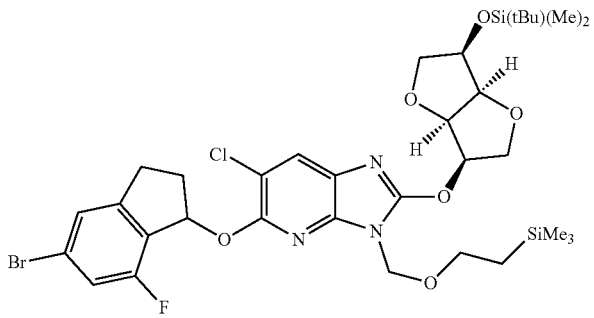

-continued
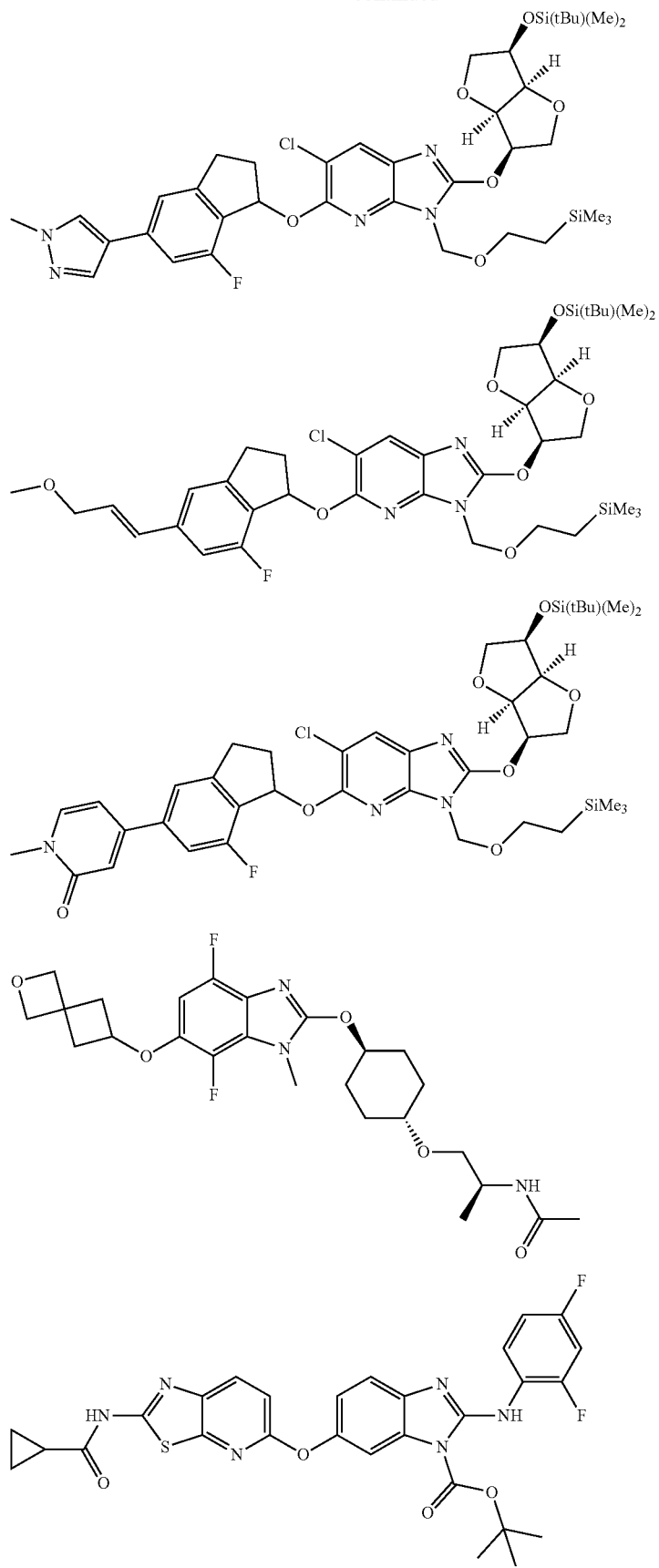

-continued

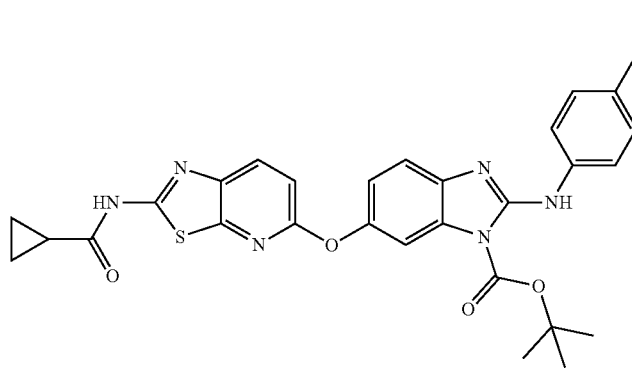

3. The compound of any one of the preceding embodiments, wherein Ring A is optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

4. The compound of embodiment 1 or 2, wherein Ring A is optionally substituted phenyl, optionally substituted 5- to 6-membered monocyclic heteroaryl having 1-4 heteroatoms independently selected from nitrogen, oxygen, and sulfur, or optionally substituted 8- to 10-membered bicyclic heteroaryl having 1-4 heteroatoms independently selected from nitrogen, oxygen, and sulfur.

5. The compound of any one of the preceding embodiments, wherein Ring A is optionally substituted 5- to 6-membered monocyclic heteroaryl having 1-4 heteroatoms independently selected from nitrogen, oxygen, and sulfur.

6. The compound of any one of embodiments 1-4, wherein Ring A is optionally substituted phenyl.

7. The compound of any one of the preceding embodiments, wherein $R^a$ is halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

8. The compound of any one of embodiments 1-6, wherein $R^a$ is hydrogen, halogen, optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

9. The compound of any one of the preceding embodiments, wherein $R^a$ is optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

10. The compound of any one of the preceding embodiments, wherein $R^a$ is optionally substituted $C_{1-6}$ aliphatic, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

11. The compound of any one of the preceding embodiments, wherein:

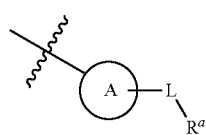

is substituted with 1-5 $R^b$, as valency allows; and
each $R^b$ is independently hydrogen, halogen, —CN, —OR, —O(CH$_2$)$_n$R, —SR, —N(R)$_2$, —NO$_2$, —C(O)

R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur;

each R is independently hydrogen, optionally substituted C$_{1-6}$ aliphatic, optionally substituted phenyl, optionally substituted 5- to 6-membered monocyclic heteroaryl having 1-3 heteroatoms independently selected from nitrogen, oxygen, and sulfur, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur;

each R' is independently optionally substituted C$_{1-6}$ aliphatic or optionally substituted 3- to 7-membered saturated or partially unsaturated carbocyclyl; and n is 1, 2, or 3.

12. The compound of any one of the preceding embodiments, wherein:

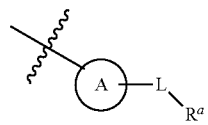

is

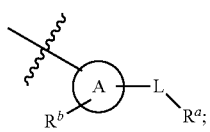

and

R$^b$ is hydrogen, halogen, —CN, —OR, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted C$_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, optionally substituted 5- to 6-membered monocyclic heteroaryl having 1-4 heteroatoms independently selected from nitrogen, oxygen, and sulfur;

each R is independently hydrogen, optionally substituted C$_{1-6}$ aliphatic, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur; and each R' is independently optionally substituted C$_{1-6}$ aliphatic or optionally substituted 3- to 7-membered saturated or partially unsaturated carbocyclyl.

13. The compound of embodiment 11, wherein each R$^b$ is independently hydrogen, halogen, —CN, —OR, —O(CH$_2$)$_n$R, —N(R)$_2$, —C(O)N(R)$_2$, optionally substituted C$_{1-6}$ aliphatic, or optionally substituted 3- to 6-membered saturated or partially unsaturated monocyclic carbocyclyl.

14. The compound of any one of embodiments 11-13, wherein R$^b$ is hydrogen, optionally substituted C$_{1-6}$ aliphatic or optionally substituted 3- to 6-membered saturated or partially unsaturated monocyclic carbocyclyl.

15. The compound of any one of embodiments 11-14, wherein R$^b$ is optionally substituted C$_{1-4}$ alkyl or optionally substituted C$_3$-C$_4$ cycloalkyl.

16. The compound of any one of embodiments 11-15, wherein

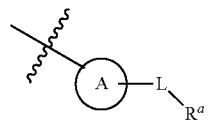

is

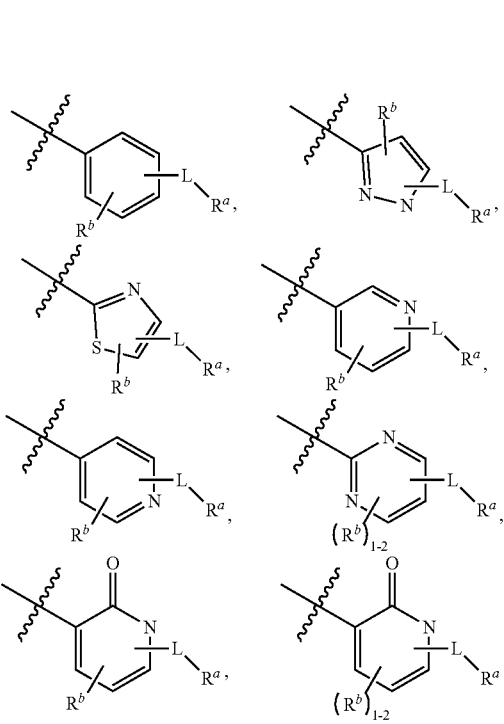

-continued

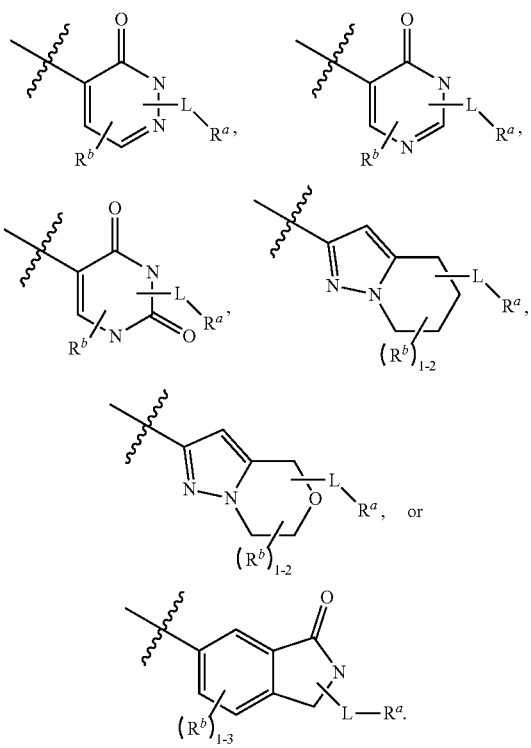

17. The compound of any one of embodiments 11-16, wherein

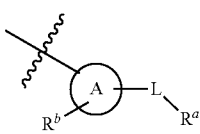

is

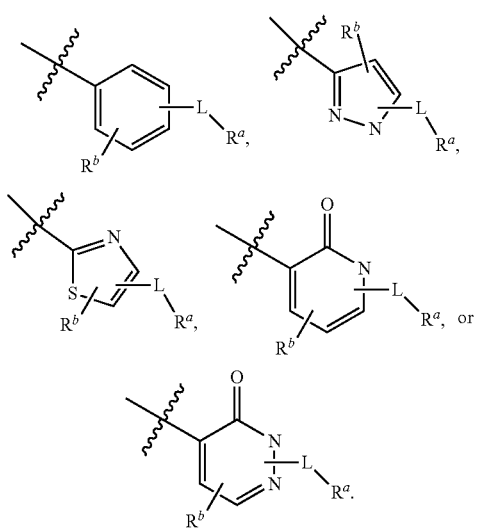

18. The compound of any one of embodiments 11-17, wherein

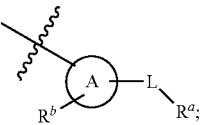

is

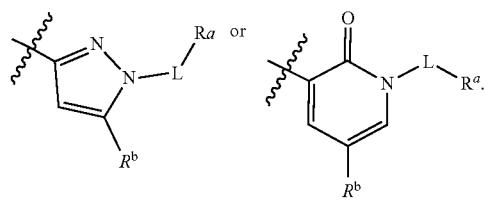

19. The compound of any one of the preceding embodiments, wherein L is a covalent bond.
20. The compound of any one of the preceding embodiments, wherein L is —CH$_2$—.
21. The compound of any one of the preceding embodiments, wherein Ring B is optionally substituted 8- to 10-membered bicyclic heteroaryl having 1-4 heteroatoms independently selected from nitrogen, oxygen, and sulfur or optionally substituted 10- to 16-membered polycyclic heteroaryl having 1-5 heteroatoms independently selected from nitrogen, oxygen, and sulfur.
22. The compound of any one of the preceding embodiments, wherein Ring B is optionally substituted 8- to 10-membered bicyclic heteroaryl having 1-4 heteroatoms independently selected from nitrogen, oxygen, and sulfur.
23. The compound of any one of the preceding embodiments, wherein Ring B is 8- to 10-membered bicyclic heteroaryl having 1-4 heteroatoms independently selected from nitrogen, oxygen, and sulfur, and is optionally substituted with one or more oxo, halogen, —O(optionally substituted C$_{1-6}$ alkyl), —O(optionally substituted C$_{3-6}$ carbocyclyl), —NH (optionally substituted C$_{1-6}$ alkyl), —NH (optionally substituted 3- to 6-membered saturated heterocyclyl), —N(optionally substituted C$_{1-6}$ alkyl)$_2$, —CN, optionally substituted C$_{1-6}$ aliphatic, optionally substituted C$_{3-6}$ carbocyclyl, or optionally substituted 3- to 6-membered saturated or partially unsaturated heterocyclyl having 1-2 heteroatoms selected from nitrogen, oxygen, and sulfur.
24. The compound of any one of the preceding embodiments, wherein Ring B is 8- to 10-membered bicyclic heteroaryl having 1-4 heteroatoms independently selected from nitrogen, oxygen, and sulfur, and is optionally substituted with one or more —O(C$_{1-6}$ alkyl), —CN, optionally substituted C$_{1-6}$ aliphatic, or optionally substituted C$_{3-6}$ carbocyclyl.
25. The compound of any one of the preceding embodiments, wherein:
Ring B is

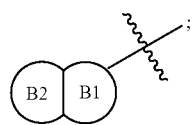

Ring B1 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur;

wherein Ring B1 is fused to Ring B2;

Ring B2 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur;

wherein Ring B2 is optionally (i) further fused to Ring B3, or (ii) Ring B2 and Ring B3 combine to form a spirocycle; and Ring B3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

26. The compound of embodiment 25, wherein Ring B1 is optionally substituted 5- to 6-membered monocyclic heteroaryl having 1-3 heteroatoms independently selected from nitrogen, oxygen, and sulfur.

27. The compound of embodiment 25 or 26, wherein Ring B is selected from the group consisting of:

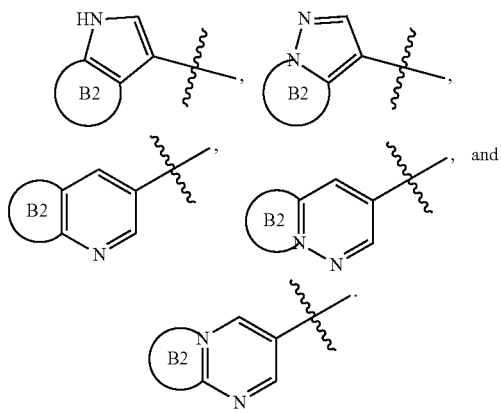

28. The compound of any one of embodiments 25-27, wherein Ring B2 is optionally substituted 5- to 6-membered monocyclic heteroaryl having 1-3 heteroatoms independently selected from nitrogen, oxygen, and sulfur.

29. The compound of any one of embodiments 25-28, wherein Ring B is selected from the group consisting of:

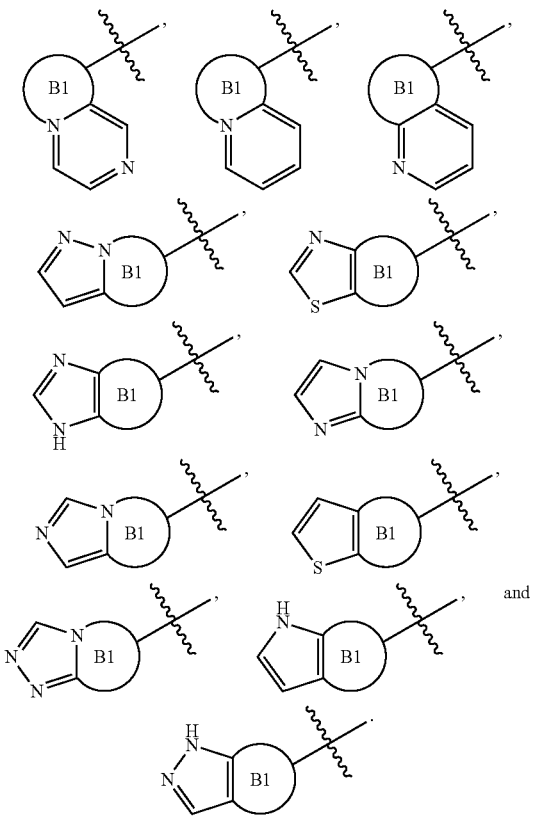

30. The compound of any one of the preceding embodiments, wherein $R^1$ is $C_{1-4}$ alkyl.

31. The compound of any one of the preceding embodiments, wherein W is $CR^w$.

32. The compound of embodiment 31, wherein $R^w$ is hydrogen.

33. The compound of any one of embodiments 1-30, wherein W is N.

34. The compound of any one of the preceding embodiments, wherein X is $CR^x$.

35. The compound of embodiment 34, wherein $R^x$ is hydrogen, halogen, —CN, —$OR^2$, or optionally substituted $C_{1-6}$ aliphatic.

36. The compound of embodiment 34, wherein $R^x$ is hydrogen, halogen, —$OR^2$, or optionally substituted $C_{1-6}$ aliphatic.

37. The compound of any one of embodiments 1-33, wherein X is N.

38. The compound of any one of the preceding embodiments, wherein Y is $CR^y$.

39. The compound of embodiment 38, wherein $R^y$ is hydrogen.

40. The compound of any one of embodiments 1-37, wherein Y is N.

41. The compound of any one of the preceding embodiments, wherein Z is —O—.

42. The compound of any one of embodiments 1-40, wherein Z is —$NR^z$—.

43. The compound of embodiment 42, wherein $R^z$ is hydrogen.-

44. The compound of any one of the preceding embodiments, wherein the compound is of Formula I-A:

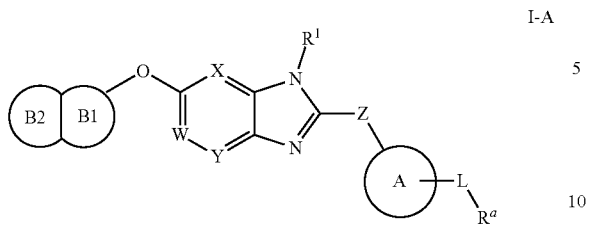

I-A or a pharmaceutically acceptable salt thereof.

45. The compound of any one of the preceding embodiments, wherein the compound is of Formula I-B:

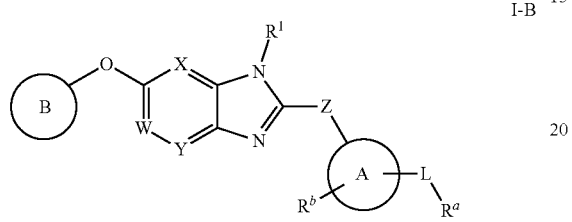

I-B or a pharmaceutically acceptable salt thereof.

46. The compound of any one of the preceding embodiments, wherein the compound is of Formula I-C:

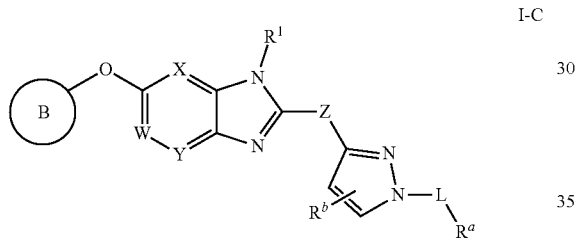

I-C or a pharmaceutically acceptable salt thereof.

47. The compound of any one of the preceding embodiments, wherein the compound is of Formula I-D:

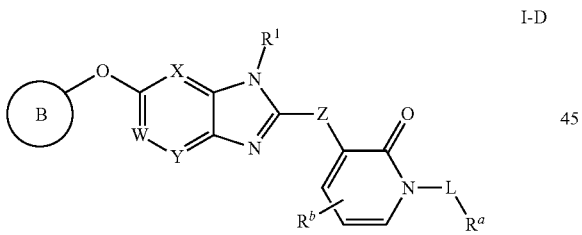

I-D or a pharmaceutically acceptable salt thereof.

48. The compound of any one of the preceding embodiments, wherein the compound is of Formula I-E:

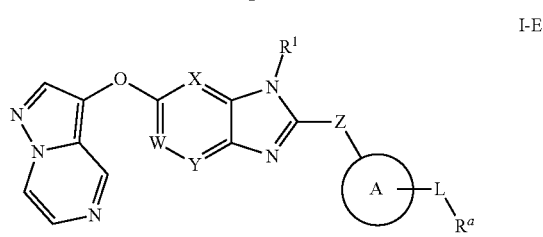

I-E or a pharmaceutically acceptable salt thereof.

49. A compound selected from Table 1, or a pharmaceutically acceptable salt thereof.

50. A pharmaceutical composition comprising a compound of any one of the preceding embodiments, or a pharmaceutically acceptable salt thereof, and a pharmaceutically acceptable carrier.

51. A method of inhibiting JAK2 in a subject comprising administering the compound of any one of embodiments 1-49 or the composition of embodiment 50.

52. A method of treating a disease, disorder, or condition associated with JAK2, comprising administering to a subject in need thereof the compound of any one of embodiments 1-49 or the composition of embodiment 50.

53. A method of treating cancer, comprising administering to a subject in need thereof the compound of any one of embodiments 1-49 or the composition of embodiment 50.

54. A method of treating a hematological malignancy, comprising administering to a subject in need thereof the compound of any one of embodiments 1-49 or the composition of embodiment 50.

55. The method of embodiment 54, wherein the hematological malignancy is leukemia or lymphoma.

56. A method of treating a myeloproliferative neoplasm, comprising administering to a subject in need thereof the compound of any one of embodiments 1-49 or the composition of embodiment 50.

57. The method of embodiment 56, wherein the myeloproliferative neoplasm is polycythemia vera, essential thrombocytopenia or myelofibrosis.

58. The method of any one of embodiments 53-57, wherein the compound is not:

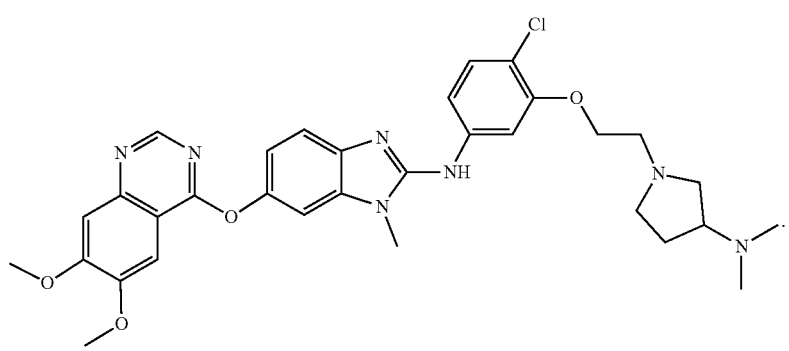

EXAMPLES

As described in the Examples below, in certain exemplary embodiments, compounds are prepared according to the following general procedures. It will be appreciated that, although the general methods depict the synthesis of certain compounds of the present disclosure, the following general methods and other methods known to one of ordinary skill in the art can be applied to all compounds and subclasses and species of each of these compounds, as described herein.

Preparation of Intermediates

Preparation of Intermediate Int-1: (S)-5-(tert-butyl)-3-isothiocyanato-1-(tetrahydrofuran-3-yl)-1H-pyrazole

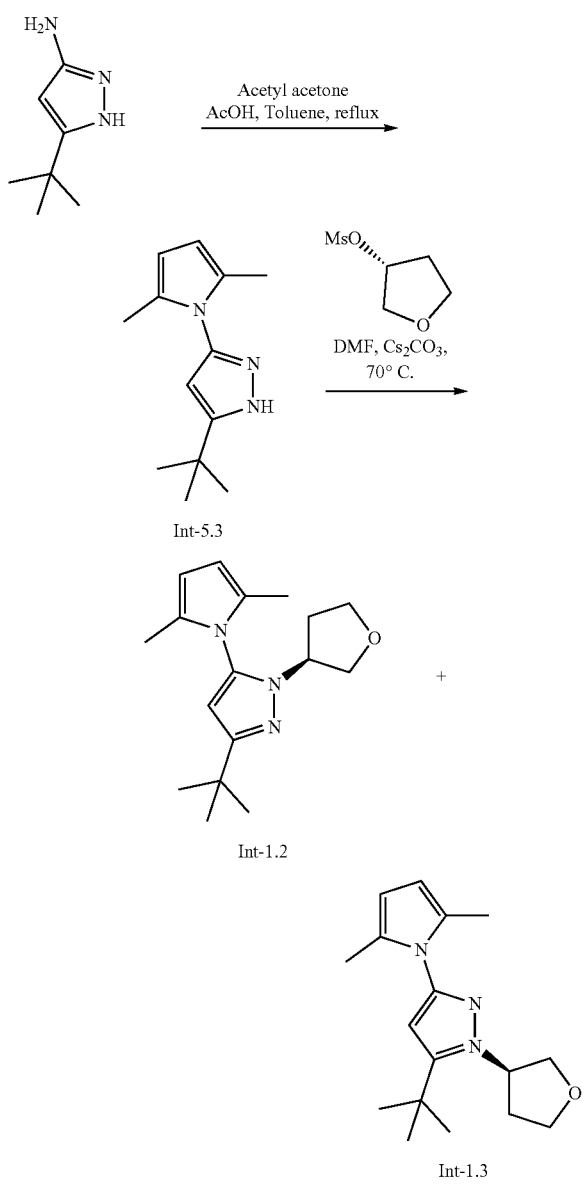

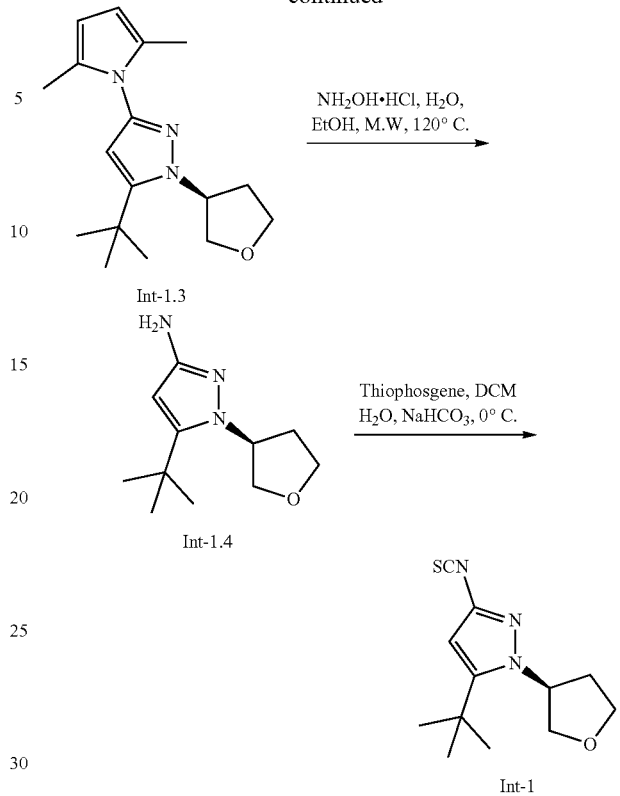

Synthesis of compound Int-1.1. To a round-bottom flask equipped with a Dean-Stark apparatus and a condenser was charged with 5-(tert-butyl)-1H-pyrazol-3-amine (5.0 g, 35.92 mmol, 1.0 equiv), 2, 5-hexanedione (4.09 g, 35.92 mmol, 1.0 equiv), toluene (100 mL) and a few drops of acetic acid (catalytic). The reaction mixture was heated to reflux for 3 hours. It was cooled rt and concentrated under reduced pressure. The residue was purified by flash column chromatography on silica gel (CombiFlash®, 12% ethyl acetate in hexane as eluant) to afford Int-1.1. MS (ES): m/z 218.3 [M+H]$^+$.

Synthesis of compound Int-1.2 and Int-1.3. A mixture of Int-1.1 (2.5 g, 11.50 mmol, 1.0 equiv), (R)-tetrahydrofuran-3-yl methanesulfonate (1.91 g, 11.50 mmol, 1.0 equiv) and cesium carbonate (7.49 g, 23 mmol, 2.0 equiv) in DMF (15 mL) was stirred at 70° C. for 12 h under nitrogen. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi-Flash®, 2% ethyl acetate in hexane as eluant) to afford Int-1.2. MS (ES): m/z 287.4 [M+H]$^+$ and Int-1.3. MS (ES): m/z 248.3 [M+H]$^+$.

Synthesis of compound Int-1.4. To a solution of Int-1.3 (0.120 g, 0.417 mmol, 1.0 equiv) in ethanol-water (2:1, 2 mL) was added hydroxylamine hydrochloride (0.287 g, 4.17 mmol, 10 equiv). The reaction mixture was stirred at 120° C. in a microwave reactor for 1 h. It was poured over ice-water, basified by 2 N sodium hydroxide and extracted with dichloromethane. The combined organic layers were washed with brine, dried over anhydrous sodium sulfate, filtered and concentrated under reduced pressure to afford Int-1.4. MS (ES): m/z 210.3 [M+H]$^+$.

Synthesis of compound Int-1. To a solution of Int-1.4 (0.070 g, 0.334 mmol, 1.0 equiv) in dichloromethane (2 mL) was added a solution of sodium bicarbonate (0.140 g, 1.67 mmol, 5.0 equiv) in water (1 mL) followed by thiophosgene (0.096 g, 0.835 mmol, 2.5 equiv) at 0° C. The reaction mixture was stirred at room temperature for 2 h. It was poured over ice-water and extracted with dichloromethane. The combined organic layers were washed with brine, dried over anhydrous sodium sulfate, filtered and concentrated under reduced pressure to afford Int-1. MS (ES): m/z 252.3 [M+H]$^+$.

Preparation of Intermediate Int-2: (R)-5-(tert-butyl)-3-isothiocyanato-1-(tetrahydrofuran-3-yl)-1H-pyrazole

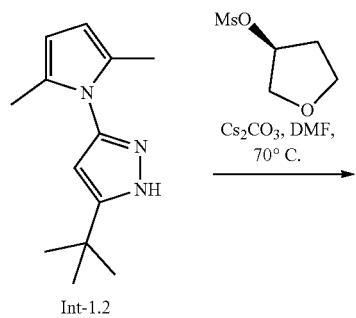

Int-1.2

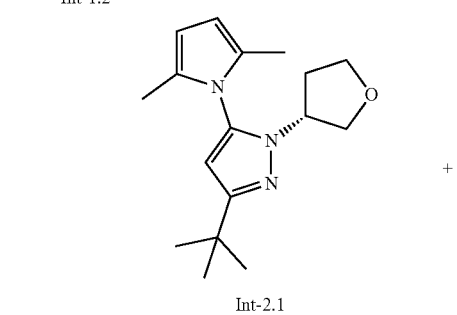

Int-2.1

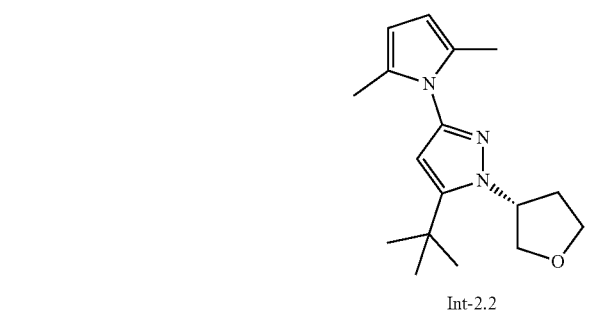

Int-2.2

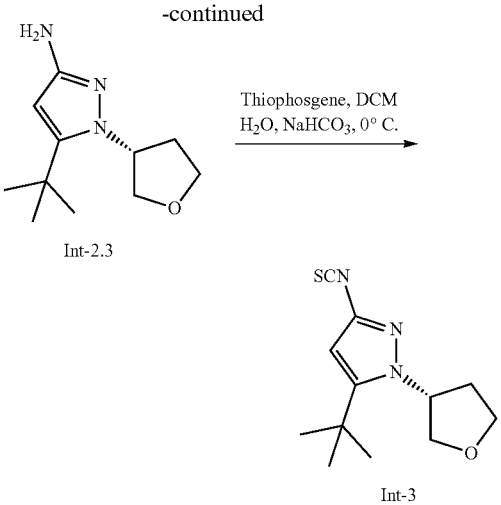

Int-2.3

Synthesis of compound Int-2. Compound Int-2 was prepared from Int-1.2, following the procedures described in the synthesis of Int-1. MS (ES): m/z 252.3 [M+H]$^+$.

Preparation of Intermediate Int-3: 5-fluoro-N-methyl-2-nitropyridin-3-amine

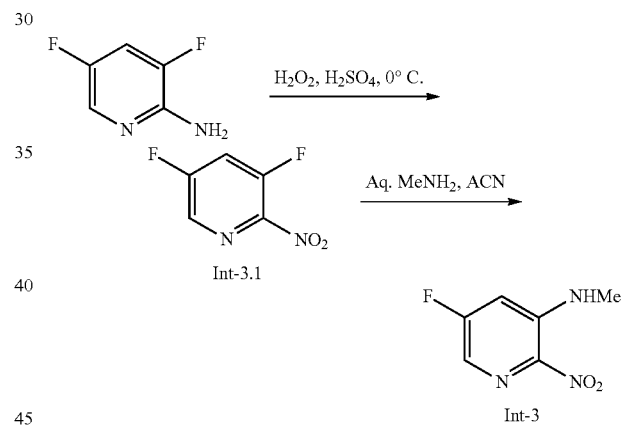

Synthesis of compound Int-3.1 Hydrogen peroxide (30 wt %, 31 mL) was added dropwise to concentrated sulfuric acid (60 mL) at 0° C. To the solution was added a solution of 3,5-difluoropyridin-2-amine (5.0 g, 38.43 mmol, 1.0 equiv) in concentrated sulfuric acid (60 mL) dropwise at 0° C. The reaction mixture was stirred at room temperature for 48 h. It was carefully poured over crushed ice and stirred. The aqueous mixture was basified with saturated aqueous sodium bicarbonate. Precipitates were removed by filtration and the filtrate was extracted with ethyl acetate. The combined organic layers were washed with brine, dried over anhydrous sodium sulfate, filtered and concentrated under reduced pressure to afford Int-3.1. $^1$H NMR (CDCl$_3$, 400 MHz): δ 8.35 (bs, 1H), 7.62-7.58 (m, 1H).

Synthesis of compound Int-3. To a solution of Int-3.1 (2.3 g, 14.37 mmol, 1.0 equiv) in acetonitrile (20 mL) was added aqueous methylamine solution (40%, 1.1 mL, 14.37 mmol, 1.0 equiv) dropwise at 0° C. The reaction mixture was stirred at room temperature for 1 h. It was poured over ice-water and extracted with ethyl acetate. The combined organic layers were washed with brine, dried over anhydrous sodium sulfate, filtered and concentrated under reduced pressure to afford Int-3. $^1$H NMR (CDCl$_3$, 400 MHz): δ 7.93 (bs, 1H), 7.78-7.75 (d, 1H), 7.02-6.99 (m, 1H), 3.06 (s, 3H).

Preparation of Intermediate Int-4:
4-chloro-5-fluoro-N-methyl-2-nitropyridin-3-amine

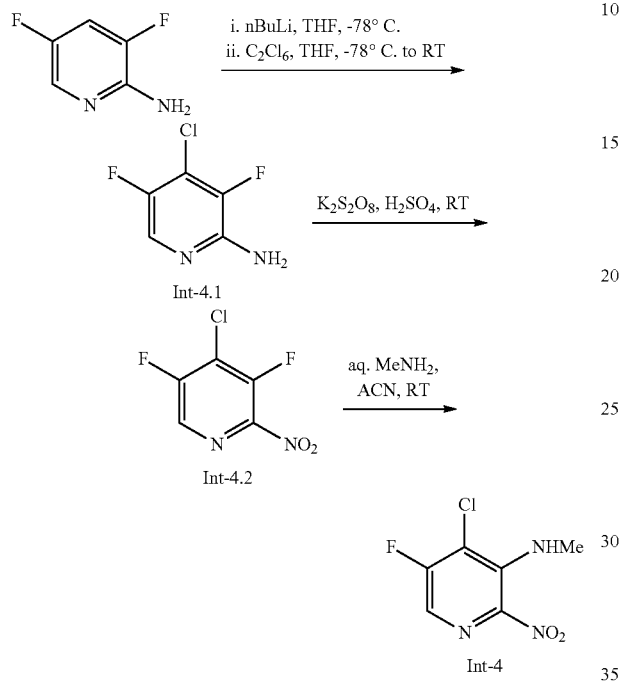

Synthesis of compound Int-4.1. To a solution of 3,5-difluoropyridin-2-amine (10 g, 76.87 mmol, 1.0 equiv) in THF (200 mL), was added n-butyllithium (2.5 M in hexane, 61.4 mL, 153.7 mmol, 2.0 equiv). The reaction mixture was stirred at −78° C. for 40 min. Hexachloroethane (36.3 g, 153.7 mmol, 2.0 equiv) was added and the reaction mixture was stirred at −78° C. for 30-40 min. A saturated ammonium chloride solution was added carefully to quench the reaction. The mixture was warmed to room temperature and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-4.1. $^1$H NMR (DMSO-d$_6$, 400 MHz): δ 7.98-7.94 (m, 1H), 6.48 (bs, 2H).

Synthesis of compound Int-4.2. Concentrated sulfuric acid (3 mL, 6 vol) was added dropwise to potassium persulfate (2.05 g, 7.6 mmol, 2.5 equiv) at room temperature and stirred for 15 min. To the mixture was added Int-4.1 (0.5 g, 3.04 mmol, 1.0 equiv) in small portions maintaining temperature at 30-40° C. The reaction mixture was stirred at room temperature for 3-4 h. It was poured over crushed ice, stirred, basified with saturated sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 2-3% ethyl acetate in hexane) to afford Int-4.2. $^1$H NMR (DMSO-d$_6$, 400 MHz): δ 8.78 (s, 1H).

Synthesis of compound Int-4. To a solution of Int-4.2 (0.970 g, 4.99 mmol, 1.0 equiv) in acetonitrile (10 mL) was added aqueous methylamine solution (40%, 0.8 mL, 9.98 mmol, 2.0 equiv) dropwise at 0° C. The reaction mixture was stirred at room temperature for 10-20 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-4. $^1$H NMR (DMSO-d$_6$, 400 MHz): δ 7.98 (s, 1H), 7.05 (bs, 1H), 2.79 (d, 3H).

Preparation of Intermediate Int-5: (R)-3-isothiocyanato-5-(perfluoroethyl)-1-(tetrahydrofuran-3-yl)-1H-pyrazole

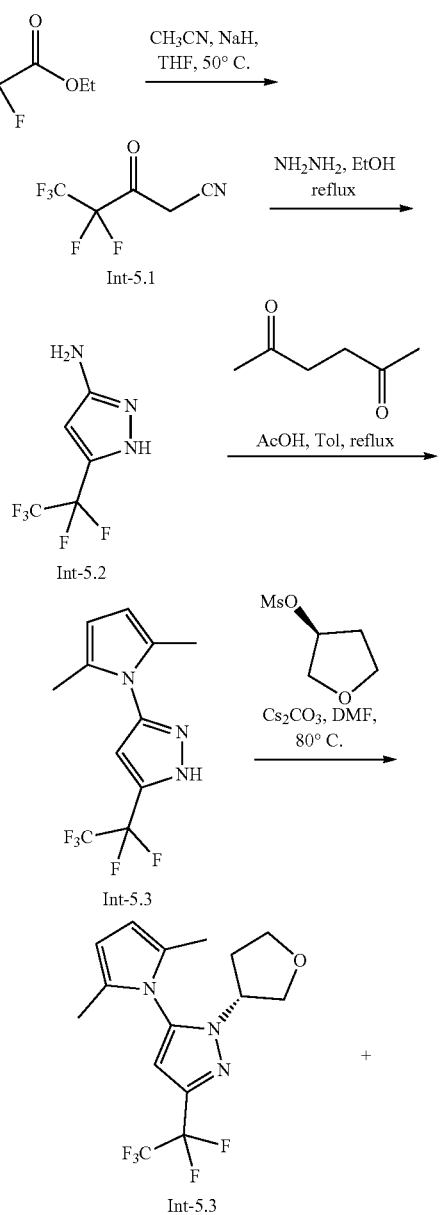

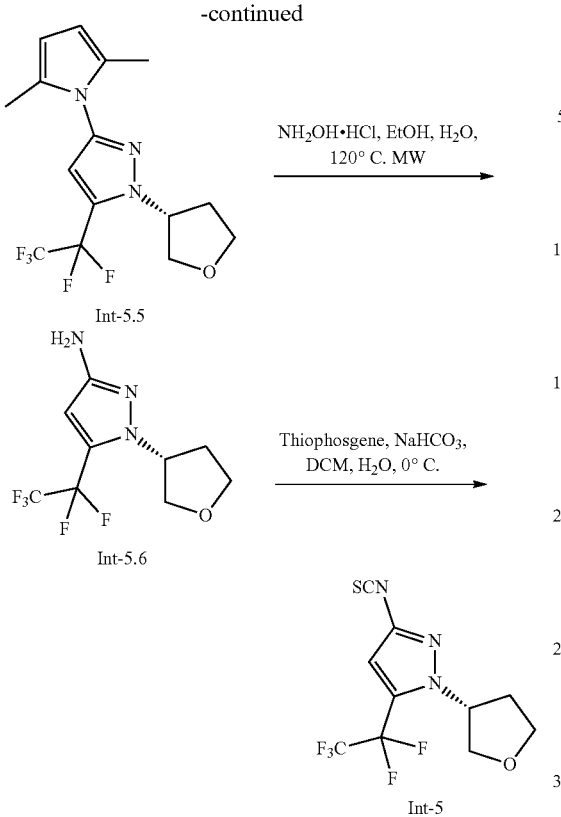

Synthesis of compound Int-5.1. To a suspension of sodium hydride (6.2 g, 156.18 mmol, 3.0 equiv) in THF (100 mL) was added ethyl 2,2,3,3,3-pentafluoropropanoate (10 g, 52.06 mmol, 1.0 equiv) and acetonitrile (1.68 mL, 52.06 mmol, 1.0 equiv) at 50° C. and the reaction mixture was stirred at same temperature for 4 h. It was concentrated under reduced pressure. To the mixture was added 4 N hydrochloric acid and it was extracted with diethyl ether. The combined organic layers were washed with brine, dried over anhydrous sodium sulfate, filtered and concentrated under reduced pressure to afford Int-5.1. The crude product was used in the next step without further purification.

Synthesis of compound Int-5.1. A mixture of Int-5.1 (6.0 g, 32.07 mmol, 1.0 equiv) and hydrazine hydrate (98%, 3.14 mL, 64.14 mmol, 2.0 equiv) in ethanol (60 mL) was heated to reflux for 12 h. It was poured over ice-water, stirred and extracted with ethyl acetate. The combined organic layers were washed with brine, dried over anhydrous sodium sulfate, filtered and concentrated under reduced pressure to afford Int-5.2. MS (ES): m/z 202.1 [M+H]$^+$.

Synthesis of compound Int-5.3. A mixture of Int-5.2 (3.0 g, 14.92 mmol, 1.0 equiv), hexane-2,5-dione (1.87 g, 16.41 mmol, 1.1 equiv) and acetic acid (0.2 mL, catalytic) in toluene (30 mL) was heated to reflux for 4-5 h. It was poured into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford Int-5.3. MS (ES): m/z 280.2 [M+H]$^+$.

Synthesis of compound Int-5.5. A mixture of Int-5.3 (0.700 g, 2.51 mmol, 1.0 equiv), (S)-tetrahydrofuran-3-yl methanesulfonate (0.416 g, 2.51 mmol, 1.0 equiv) and cesium carbonate (2.44 g, 7.53 mmol, 3.0 equiv) in DMF (10 mL) was stirred at 80-90° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5-6% ethyl acetate in hexane) to afford Int-5.5. MS (ES): m/z 350.3 [M+H]$^+$ and 1.7b (0.100 g, yield: 11.42%). MS (ES): m/z 350.3 [M+H]$^+$.

Synthesis of compound Int-5.6. Compound Int-5.6 was prepared from Int-5.5, following the procedure described in the synthesis of Int-1.4. The product was purified by flash column chromatography on silica gel (CombiFlash®, 3-4% methanol in dichloromethane). MS (ES): m/z 272.2 [M+H]$^+$.

Synthesis of compound Int-5. Compound Int-5 was prepared from Int-5.6, following the procedure described in the synthesis of Int-1. The product was purified by flash column chromatography on silica gel (CombiFlash®, 6% ethyl acetate in hexane). MS (ES): m/z 314.1 [M+H]$^+$.

Preparation of Intermediate Int-6: (S)-3-isothiocyanato-5-(perfluoroethyl)-1-(tetrahydrofuran-3-yl)-1H-pyrazole

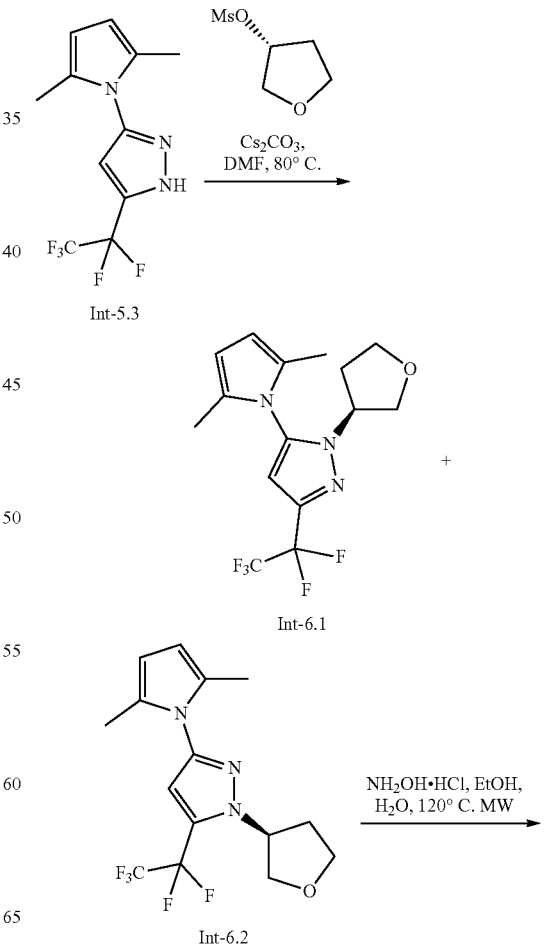

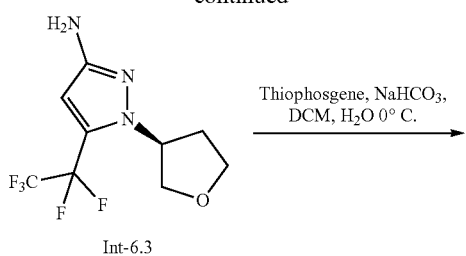

Int-6.3

Thiophosgene, NaHCO₃,
DCM, H₂O 0° C.

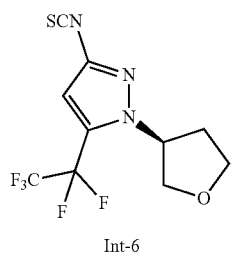

Int-6

Synthesis of compound Int-6. Compound Int-6 was prepared from Int-5.3 and (R)-tetrahydrofuran-3-yl methanesulfonate, following the procedures described in the synthesis of Int-5. MS (ES): m/z 314.1 [M+H]⁺.

Preparation of Intermediate Int-7: (S)-2-(3-isothiocyanato-1-(tetrahydrofuran-3-yl)-1H-pyrazol-5-yl)-2-methylpropanenitrile

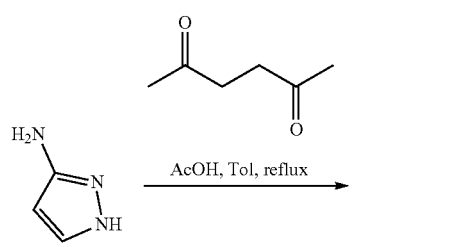

AcOH, Tol, reflux

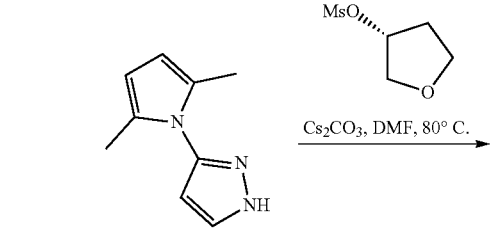

Int-7.1

Cs₂CO₃, DMF, 80° C.

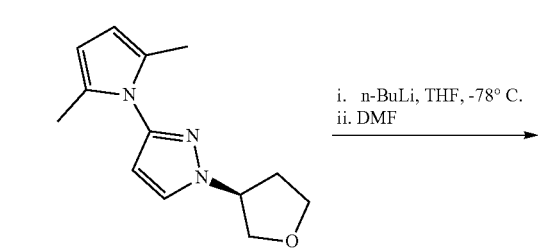

Int-7.2 i. n-BuLi, THF, -78° C.
ii. DMF

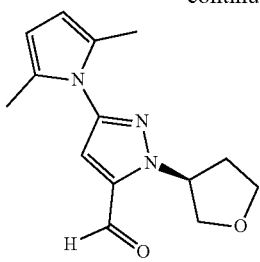

Int-7.3

NaBH₄, THF, 0° C.

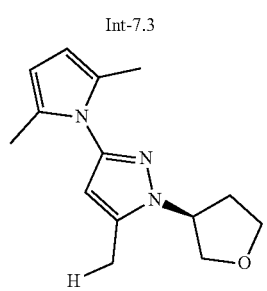

Int-7.4

TEA, MsCl, DCM

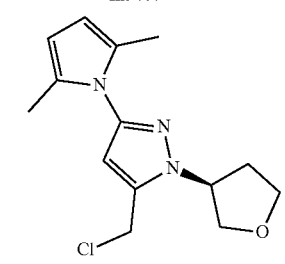

Int-7.5

TMSCN, K₂CO₃, ACN

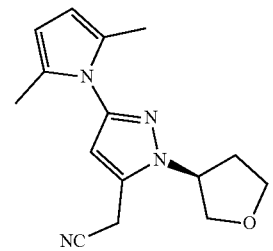

Int-7.6

NaH, MeI, DMF

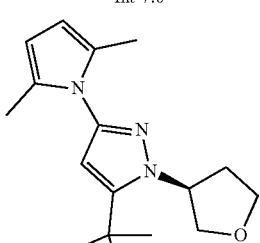

Int-7.7

TFA, H₂O, 120° C.

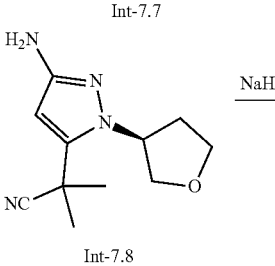

Int-7.8

Thiophosgene
NaHCO₃, DCM, H₂O 0° C.

-continued

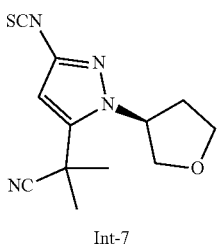

Int-7

Synthesis of compound Int-7.1. To a solution of 1H-pyrazol-3-amine (10.0 g, 120.35 mmol, 1.0 equiv) and hexane-2,5-dione (13.74 g, 120.35 mmol, 1.0 equiv) in toluene (100 mL) was added acetic acid (catalytic). The reaction mixture was heated to reflux with a Dean-Stark trap to remove water. The reaction mixture was cooled to room temperature and concentrated under reduced pressure. The residue was purified by flash column chromatography on silica gel (CombiFlash®, 25% ethyl acetate in hexane) to afford Int-7.1. MS (ES): m/z 162.2 [M+H]$^+$.

Synthesis of compound Int-7.2. A mixture of Int-7.1 (15 g, 93.05 mmol, 1.0 equiv), (R)-tetrahydrofuran-3-yl methanesulfonate (18.56 g, 111.66 mmol, 1.2 equiv) and cesium carbonate (60.48 g, 186.01 mmol, 2.0 equiv) in DMF (150 mL) was stirred at 80-90° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 17% ethyl acetate in hexane) to afford Int-7.2. MS (ES): m/z 232.3 [M+H]$^+$.

Synthesis of compound Int-7.3. To a solution of Int-7.2 (10 g, 43.23 mmol, 1.0 equiv) in THF (100 mL) was added n-butyllithium (2.5 M in hexane, 22.5 mL, 56.19 mmol, 1.3 equiv) dropwise at −78° C. and stirred for 1 h. To the solution was added DMF (7.3 mL, 95.10 mmol, 2.2 equiv) and the reaction mixture was stirred at −78° C. for 30-40 min. A saturated aqueous solution of ammonium chloride was added carefully to quench the reaction. The mixture was warmed to room temperature and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford Int-7.3.

Synthesis of compound Int-7.4. To a solution of Int-7.3 (3.5 g, 13.50 mmol, 1.0 equiv) in THF (50 mL), was added sodium borohydride (0.62 g, 16.2 mmol, 1.2 equiv) at 0° C. The reaction mixture was stirred at 0° C. for 1 h. It was poured over ice-water, stirred and extracted with ethyl acetate. The combined organic layers were washed with brine, dried over anhydrous sodium sulfate, filtered and concentrated under reduced pressure to afford Int-7.4.

Synthesis of compound Int-7.5. To a solution of Int-7.4 (2.5 g, 9.57 mmol, 1.0 equiv) and triethylamine (4.0 mL, 28.71 mmol, 3.0 equiv) in dichloromethane (40 mL) at 0° C. was added MsCl (1.1 mL, 14.35 mmol, 1.5 equiv). The reaction mixture was allowed to warm to rt and stirred for 1 h. It was poured over ice-water, stirred and extracted with dichloromethane. The combined organic layers were washed with saturated aqueous sodium bicarbonate followed by brine, dried over anhydrous sodium sulfate, filtered and concentrated under reduced pressure. The residue was purified by flash column chromatography on silica gel (CombiFlash®, 15% ethyl acetate in hexane) to afford Int-7.5. MS (ES): m/z 280.7 [M+H]$^+$.

Synthesis of compound Int-7.6. To a solution of Int-7.5 (2.0 g, 7.15 mmol, 1.0 equiv) in acetonitrile (40 mL) was added potassium carbonate (1.97 g, 14.3 mmol, 2.0 equiv) followed by addition of trimethylsilyl cyanide (1.415 g, 14.3 mmol, 2.0 equiv). The reaction mixture was stirred at 80° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford Int-7.6. MS (ES): m/z 271.3 [M+H]$^+$.

Synthesis of compound Int-7.7. To a solution of Int-7.6 (1.0 g, 3.70 mmol, 1.0 equiv) in DMF (15 mL), was added sodium hydride (0.592 g, 14.8 mmol, 4.0 equiv) at 0° C. and stirred for 20 min. To the mixture was added methyl iodide (2.1 g, 14.8 mmol, 4.0 equiv) and it was allowed to warm to rt stirring for 30 min. It was poured into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 22% ethyl acetate in hexane) to afford Int-7.7. MS (ES): m/z 299.4 [M+H]$^+$.

Synthesis of compound Int-7.8. To a suspension of Int-7.7 (0.3 g, 1.01 mmol, 1.0 equiv) in water (10 mL) was added trifluoroacetic acid (3 mL) and stirred at 120° C. for 30 min. The reaction mixture was poured into a mixture of ice-saturated aqueous solution of sodium bicarbonate, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 2.4% methanol in dichloromethane) to afford Int-7.8. MS (ES): m/z 221.3 [M+H]$^+$.

Synthesis of compound Int-7. Compound Int-7 was prepared from Int-7.8, following the procedure described in the synthesis of Int-1. The residue was purified by flash column chromatography on silica gel (CombiFlash®, 8% ethyl acetate in hexane) to afford Int-7. MS (ES): m/z 263.3 [M+H]$^+$.

Preparation of Intermediate Int-8: (R)-2-(3-isothiocyanato-1-(tetrahydrofuran-3-yl)-1H-pyrazol-5-yl)-2-methylpropanenitrile

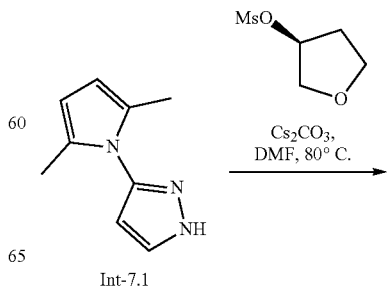

Int-7.1

-continued

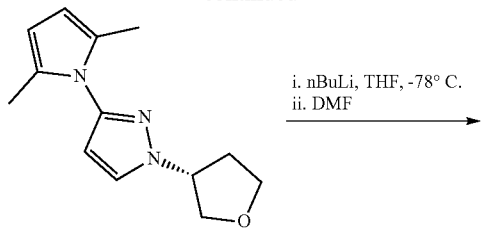

Int-8.1 i. nBuLi, THF, -78° C.
ii. DMF


Int-8.2

NaBH₄
THF, 0° C.


Int-8.3

MsCl,
TEA, DCM

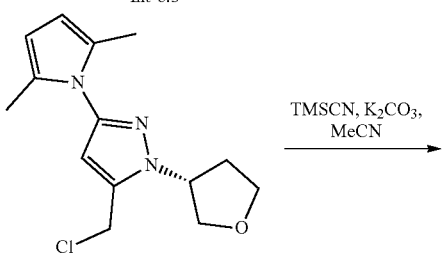

Int-8.4

TMSCN, K₂CO₃,
MeCN

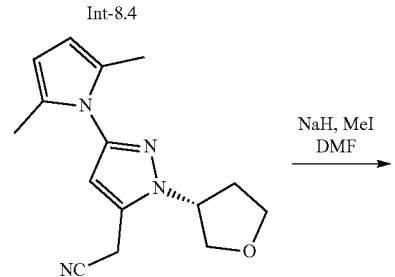

Int-8.5

NaH, MeI
DMF

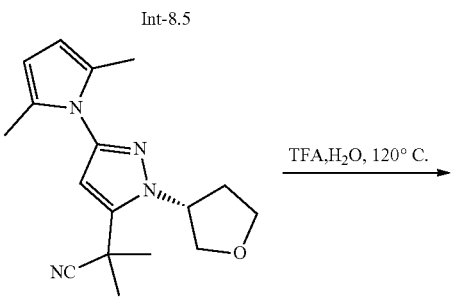

Int-8.6

TFA, H₂O, 120° C.

-continued

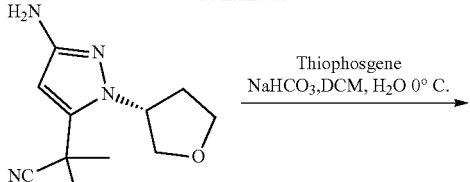

Int-8.7

Thiophosgene
NaHCO₃, DCM, H₂O 0° C.

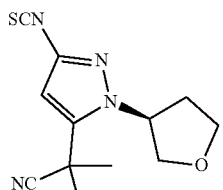

Int-8

Synthesis of compound Int-8. Compound Int-8 was prepared following the procedures described in the synthesis of Int-7. The residue was purified by flash column chromatography on silica gel (CombiFlash®, 8% ethyl acetate in hexane). MS (ES): m/z 263.3 [M+H]⁺.

Preparation of Intermediate Int-9: (S)-5-(tert-butyl)-3-isothiocyanato-1-(1-methylpyrrolidin-3-yl)-1H-pyrazole

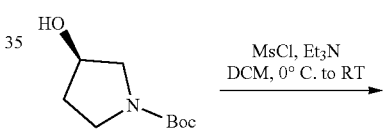

MsCl, Et₃N
DCM, 0° C. to RT

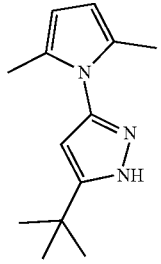

Int-1.1

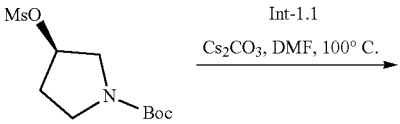

Int-9.1

Cs₂CO₃, DMF, 100° C.

Int-9.2

+

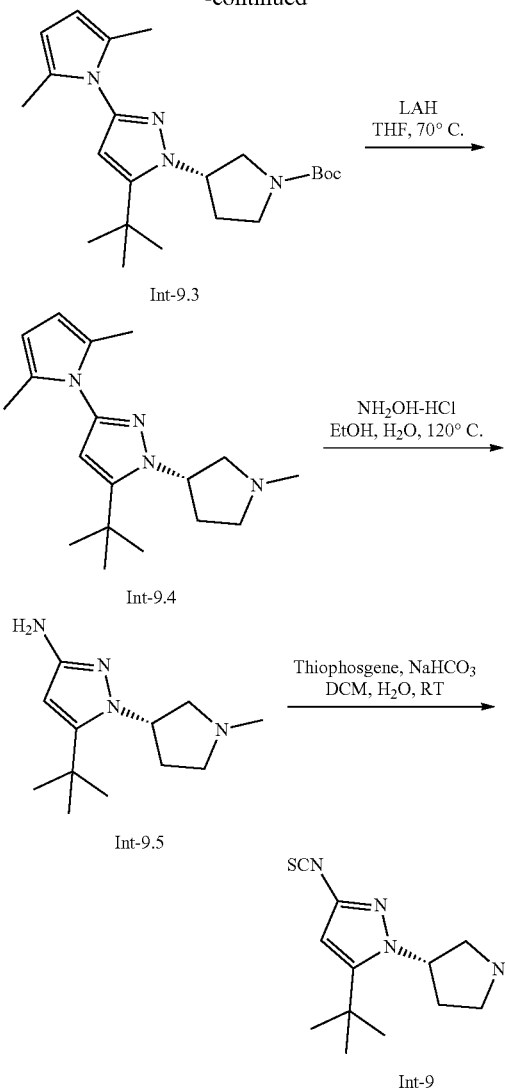

Flash®, 10-12% ethyl acetate in hexane) to afford Int-9.3. MS (ES): m/z 387.5 [M+H]⁺.

Synthesis of compound Int-9.4. To a solution of Int-9.3 (4.5 g, 11.64 mmol, 1.0 equiv) in THF (45 mL) was added lithium aluminum hydride solution (1 M in THF, 69.8 mL, 69.84 mmol, 6.0 equiv) at 0° C. and the reaction mixture was stirred at 70° C. for 2 h. It was cooled to rt and quenched by the addition of saturated aqueous anhydrous sodium sulfate. The reaction mixture was filtered through a pad of Celite® and rinsed with diethyl ether. The organic layer was separated, dried over anhydrous sodium sulfate, filtered and concentrated under reduced pressure. The residue was purified by flash column chromatography on silica gel (Combi-Flash®, 60% ethyl acetate in hexane) to afford Int-9.4. MS (ES): m/z 301.5 [M+H]⁺.

Synthesis of compound Int-9.5. Compound Int-9.5 was prepared from Int-9.4, following the procedure described in the synthesis of Int-1.4. The product was purified by flash column chromatography on silica gel (CombiFlash®, 7-8% methanol in dichloromethane) to afford Int-9.5. MS (ES): m/z 223.3 [M+H]⁺.

Synthesis of compound Int-9. Compound Int-9 was prepared from Int-9.5, following the procedure described in the synthesis of Int-1. The product was purified by flash column chromatography on silica gel (CombiFlash®, 6% ethyl acetate in hexane). MS (ES): m/z 265.3 [M+H]⁺.

Preparation of intermediate Int-10: (R)-5-(tert-butyl)-3-isothiocyanato-1-(1-methylpyrrolidin-3-yl)-1H-pyrazole

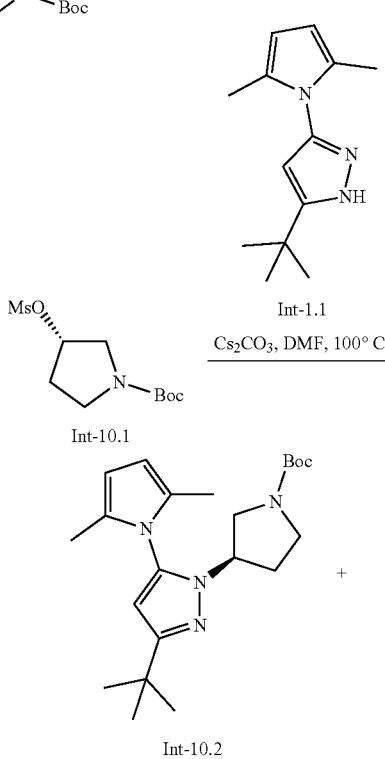

Synthesis of compound Int-9.1. To a solution of tert-butyl (R)-3-hydroxypyrrolidine-1-carboxylate (25 g, 133.52 mmol, 1.0 equiv) in dichloromethane (250 mL) was added triethylamine (46.5 mL, 333.8 mmol, 2.5 equiv) at 0° C. followed by addition of mesyl chloride (15.56 mL, 200.28 mmol, 1.5 equiv). The reaction mixture was stirred at room temperature for 1 h. It was poured over ice-water, stirred and extracted with dichloromethane. The combined organic layers were washed with saturated sodium bicarbonate followed by brine, dried over anhydrous sodium sulfate, filtered and concentrated under reduced pressure to afford Int-9.1. ¹H NMR (DMSO-d₆, 400 MHz): δ 5.24 (bs, 1H), 3.55-3.51 (m, 2H), 3.48-3.39 (m, 2H), 3.24 (s, 3H), 2.12 (bs, 2H), 1.41 (s, 9H).

Synthesis of compound Int-9.3. A mixture of Int-1.1 (15 g, 69.02 mmol, 1.0 equiv), Int-9.1 (27 g, 103.5 mmol, 1.5 equiv) and cesium carbonate (56 g, 172.5 mmol, 2.5 equiv) in DMF (150 mL) was stirred at 100° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi-

373
-continued

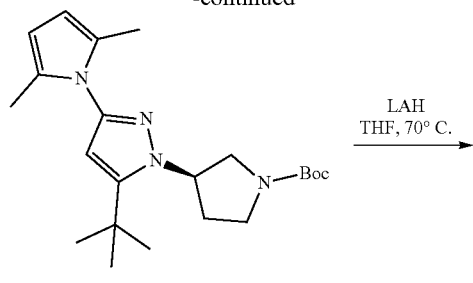
Int-10.3

LAH
THF, 70° C.

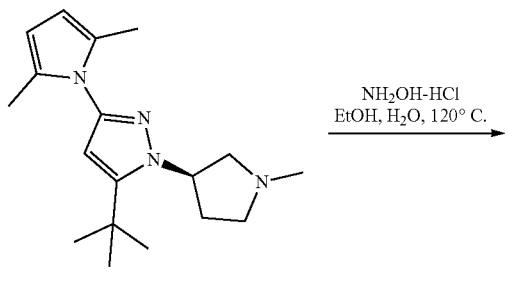
Int-10.4

NH₂OH-HCl
EtOH, H₂O, 120° C.

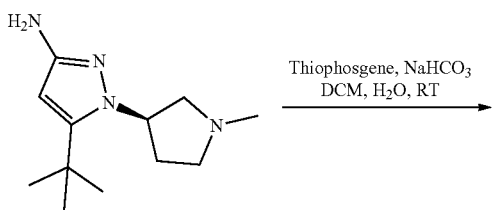
Int-10.5

Thiophosgene, NaHCO₃
DCM, H₂O, RT

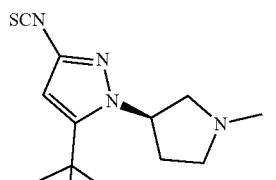
Int-10

Synthesis of compound Int-10. Compound Int-10 was prepared following the procedures described in the synthesis of Int-9.

Preparation of Intermediates Int-11a and Int-11b: 1-((3S,4R)-4-(benzyloxy)tetrahydrofuran-3-yl)-5-(tert-butyl)-3-isothiocyanato-1H-pyrazole and 1-((3S,4R)-4-(benzyloxy)tetrahydrofuran-3-yl)-5-(tert-butyl)-3-isothiocyanato-1H-pyrazole

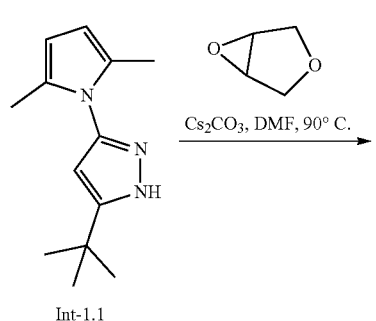
Int-1.1

Cs₂CO₃, DMF, 90° C.

374
-continued

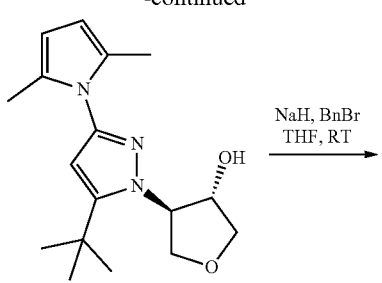
trans-(±)-Int-11.1

NaH, BnBr
THF, RT

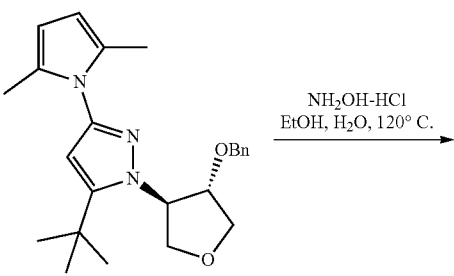
trans-(±)-Int-11.2

NH₂OH-HCl
EtOH, H₂O, 120° C.

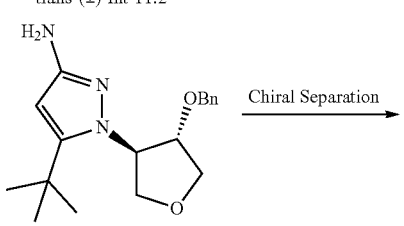
trans-(±)-Int-11.3

Chiral Separation

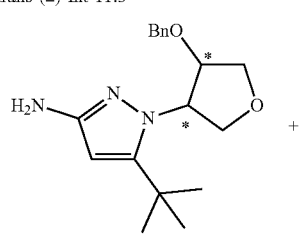
trans-Int-11.4a
+

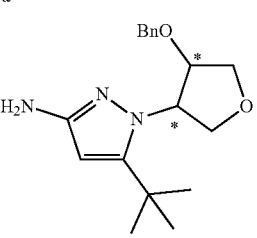
trans-Int-11.4b

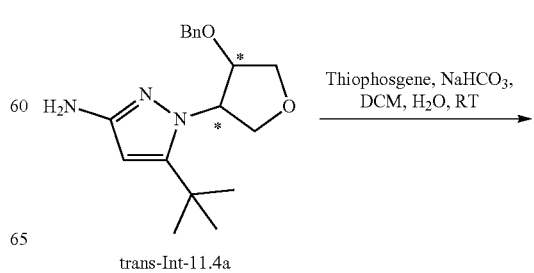
trans-Int-11.4a

Thiophosgene, NaHCO₃,
DCM, H₂O, RT

-continued

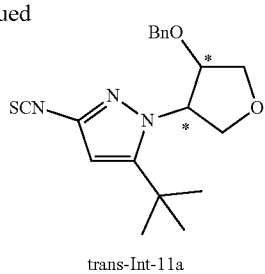

trans-Int-11a

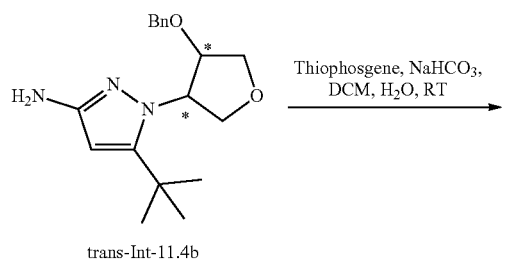

trans-Int-11.4b

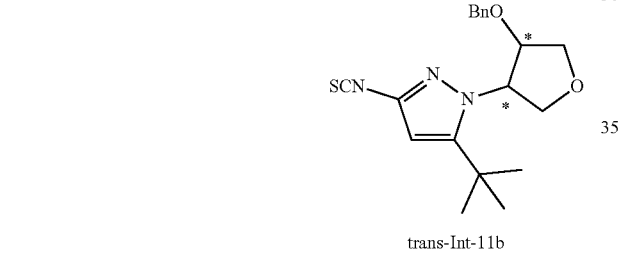

trans-Int-11b

Synthesis of compound trans-(±)-Int-11.1. A mixture of compound Int-1.1 (40 g, 184 mmol, 1.0 equiv), 3,6-dioxabicyclo[3.1.0]hexane (23.77 g, 276 mmol, 1.5 equiv) and cesium carbonate (239 g, 736 mmol, 4.0 equiv) in DMF (400 mL) was stirred at 90° C. for 6 h. It was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford trans-(±)-Int-11.1. MS (ES): m/z 304.3 [M+H]$^+$.

Synthesis of compound trans-(±)-Int-11.2. To a suspension of sodium hydride (0.514 g, 12.85 mmol, 1.5 equiv) in THF (10 mL) was added a solution of trans-(±)-Int-11.1 (2.6 g, 8.57 mmol, 1.0 equiv) in THF (15 mL) and stirred at 70° C. for 1 h followed by addition of benzyl bromide (1.22 mL, 10.28 mmol, 1.2 equiv) and the reaction mixture was stirred at room temperature for 7 h. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford trans-(±)-Int-11.2. MS (ES): m/z 394.4 [M+H]$^+$.

Synthesis of compound trans-(±)-Int-11.3. Compound trans-(±)-Int-11.3 was prepared from trans-(±)-Int-11.2, following the procedure described in the synthesis of Int-1.4. The product was purified by flash column chromatography on silica gel (CombiFlash®, 80% ethyl acetate in hexane). MS (ES): m/z 316.3 [M+H]$^+$.

Separation of compound trans-Int-11.4a and trans-Int-11.4b. Enantiomers of trans-(±)-Int-11.3 (0.970 g) were separated by HPLC (column: CHIRALCAL OX-H (250 mm×21 mm, 5 µm); mobile phase: (A) 0.1% DEA in n-hexane, (B) 0.1% DEA in 2-propanol; flow rate=20 mL/min) to afford first eluting fraction (trans-Int-11.4a, MS (ES): m/z: 316.3 [M+H]$^+$) and second eluting fraction (trans-Int-11.4b, MS (ES): m/z: 316.3 [M+H]$^+$). (*Absolute stereochemistry not confirmed.)

Synthesis of compound trans-Int-11a. Compound trans-Int-11a was prepared from trans-Int-11.4a, following the procedure described in the synthesis of Int-1. The product was purified by flash column chromatography on silica gel (CombiFlash®, 20% ethyl acetate in hexane). MS (ES): m/z 358.4 [M+H]$^+$.

Synthesis of compound trans-Int-11b. Compound trans-Int-11b was prepared from trans-Int-11.4b, following the procedure described in the synthesis of Int-1. The product was purified by flash column chromatography on silica gel (CombiFlash®, 20% ethyl acetate in hexane). MS (ES): m/z 358.4 [M+H]$^+$.

Preparation of Intermediate Int-12: (S)-5-(tert-butyl)-1-(1-(2-fluoroethyl)pyrrolidin-3-yl)-3-isothiocyanato-1H-pyrazole

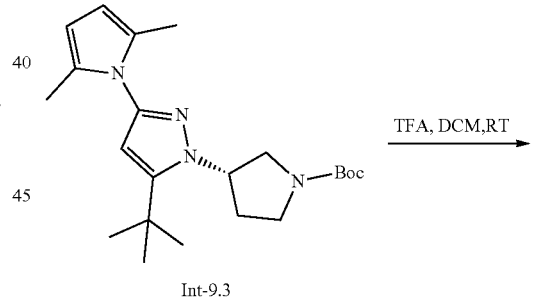

Int-9.3

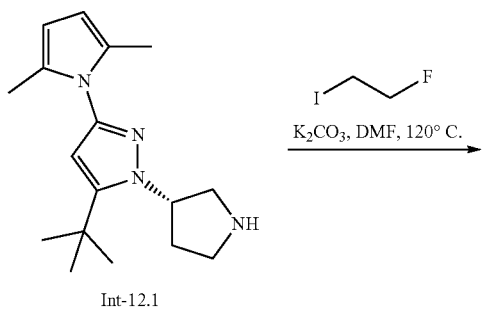

Int-12.1

-continued

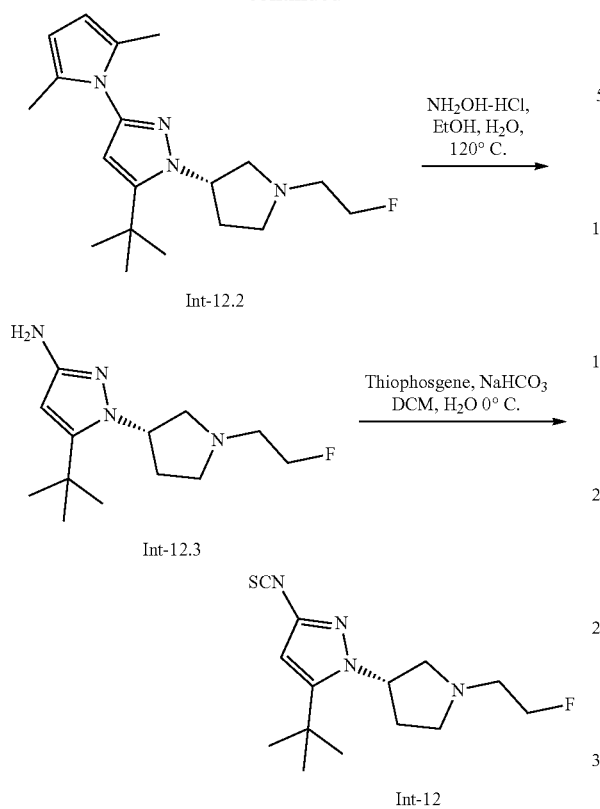

Preparation of Intermediate Int-13: (R)-5-(tert-butyl)-1-(1-(2-fluoroethyl)pyrrolidin-3-yl)-3-isothiocyanato-1H-pyrazole

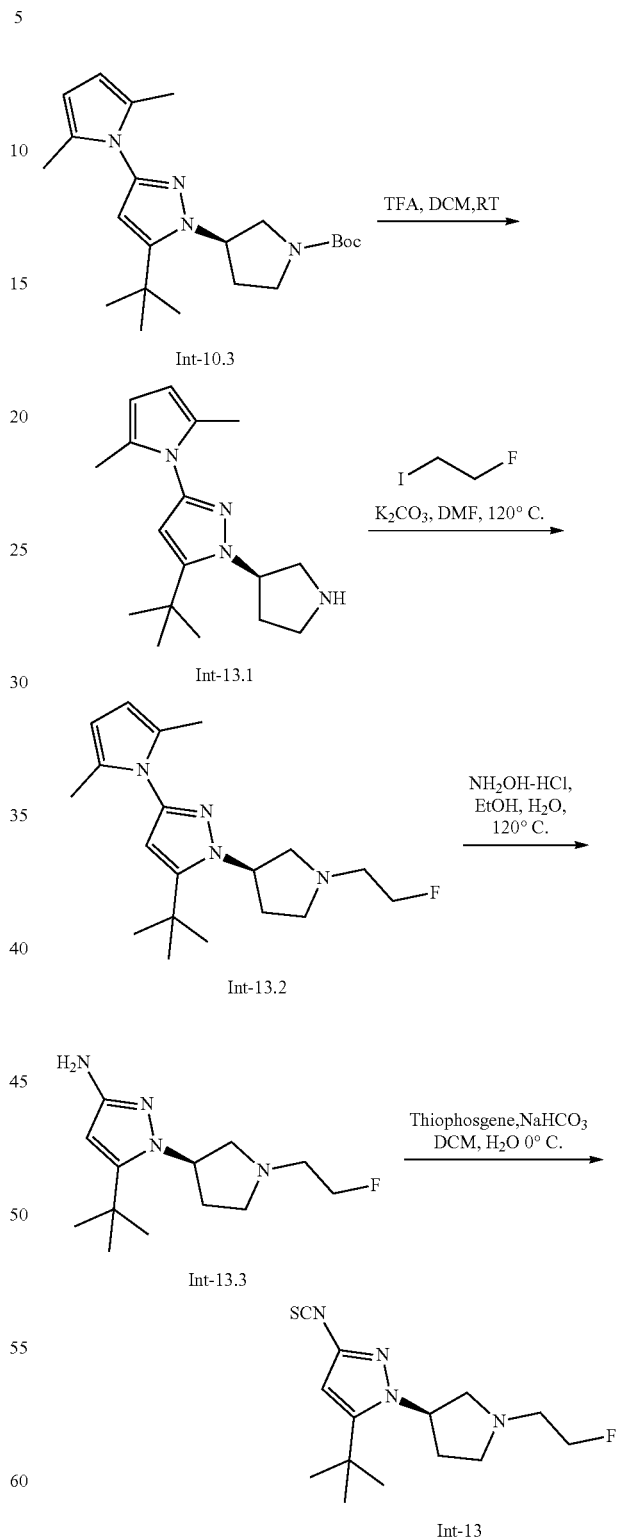

Synthesis of compound Int-12.1. To a solution of Int-9.3 (4.1 g, 10.61 mmol, 1.0 equiv) in dichloromethane (40 mL) was added trifluoroacetic acid (10 mL) at 0° C. The reaction mixture was stirred at room temperature for 3 h. It was poured over ice-water, followed by addition of saturated sodium bicarbonate solution and extracted with ethyl acetate. The combined organic layers were washed with brine, dried over anhydrous sodium sulfate, filtered and concentrated under reduced pressure to afford Int-12.1. MS (ES): m/z 287.4 [M+H]$^+$.

Synthesis of compound Int-12.2. A mixture of Int-12.1 (2.0 g, 6.98 mmol, 1.0 equiv), 1-fluoro-2-iodoethane (1.82 g, 10.47 mmol, 1.5 equiv) and potassium carbonate (2.89 g, 20.94 mmol, 3.0 equiv) in DMF (20 mL) was stirred at 120° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford Int-12.2. MS (ES): m/z 333.4 [M+H]$^+$.

Synthesis of compound Int-12.3. Compound Int-12.3 was prepared from Int-12.2, following the procedure described in the synthesis of Int-1.4. The product was purified by flash column chromatography on silica gel (CombiFlash®, 4-5% methanol in dichloromethane). MS (ES): m/z 255.3 [M+H]$^+$.

Synthesis of compound Int-12. Compound Int-12 was prepared from Int-12.3, following the procedure described in the synthesis of Int-1.

Synthesis of compound Int-13. Compound Int-13 was prepared following the procedures described in the synthesis of Int-12.

Preparation of Intermediate Int-14: 5-(tert-butyl)-3-isothiocyanato-1-(2-oxaspiro[3.3]heptan-6-yl)-1H-pyrazole

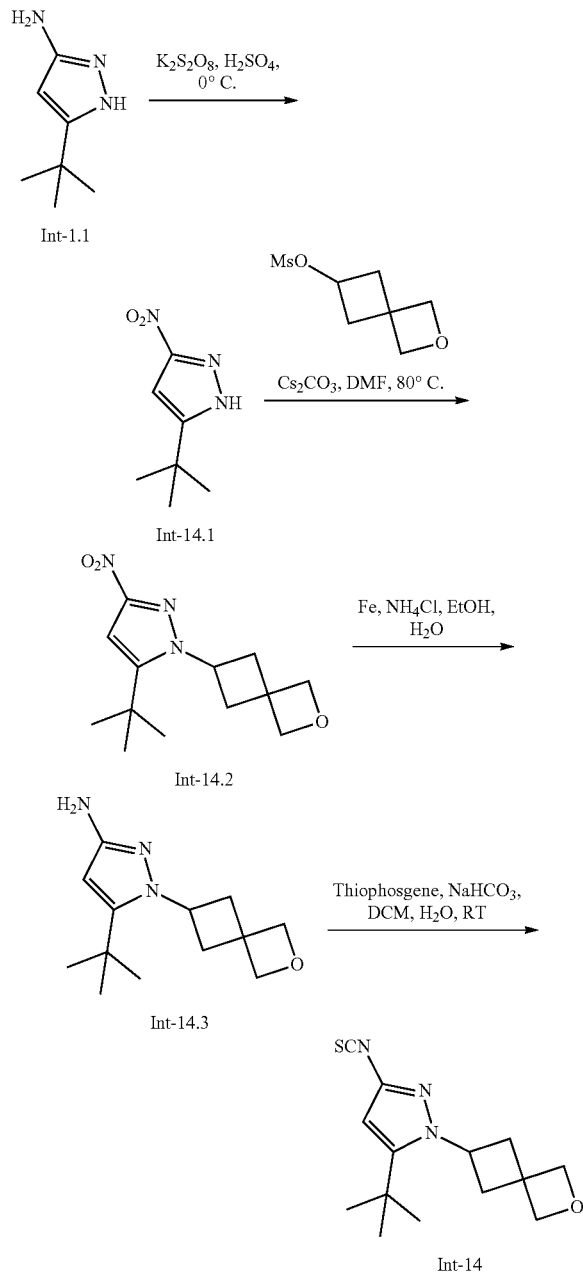

Synthesis of compound Int-14.1. Concentrated sulfuric acid (60 mL, 6 fvol) was added dropwise to potassium persulfate (54.31 g, 201.15 mmol, 2.8 equiv) at room temperature and stirred for 15 min. To the mixture was added Int-1.1 (10 g, 71.84 mmol, 1.0 equiv) in small portions maintaining temperature at 30-40° C. The reaction mixture was stirred at room temperature for 30 min. It was poured over crushed ice, stirred and basified with saturated sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford Int-14.1. $^1$H NMR (DMSO-$d_6$, 400 MHz): δ 11.20 (s, 1H), 6.26 (s, 1H), 1.29 (s, 9H).

Synthesis of compound Int-14.2. To a solution of Int-14.1 (1.2 g, 7.09 mmol, 1.0 equiv) and 2-oxaspiro[3.3]heptan-6-yl methanesulfonate (2.05 g, 10.64 mmol, 1.5 equiv) in DMF (10 mL) was added cesium carbonate (6.91 g, 21.27 mmol, 3.0 equiv) and the reaction mixture was stirred at 80-90° C. for 12 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15-20% ethyl acetate in hexane) to afford Int-14.2. MS (ES): m/z 266.3 [M+H]$^+$.

Synthesis of compound Int-14.3. To a solution of Int-14.2 (0.200 g, 0.753 mmol, 1.0 equiv) in ethanol-water (2:1, 5 mL) was added iron powder (0.210 g, 3.765 mmol, 5 equiv) followed by ammonium chloride (0.203 g, 3.765 mmol, 5 equiv). The reaction mixture was stirred at 50° C. for 30 min. It was poured over ice-water, filtered and extracted with ethyl acetate. The combined organic layers were washed with brine, dried over anhydrous sodium sulfate, filtered and concentrated under reduced pressure to afford Int-14.3. MS (ES): m/z 236.3 [M+H]$^+$. The crude product was used in the next step without further purification.

Synthesis of compound Int-14. Compound Int-14 was prepared following the procedures described in the synthesis of Int-7.

Preparation of Intermediate Int-15: 5-(tert-butyl)-1-(2,2-difluoroethyl)-3-isothiocyanato-1H-pyrazole

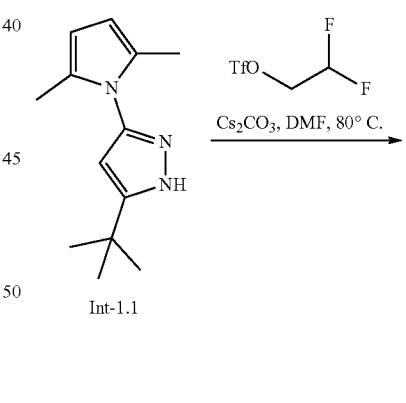

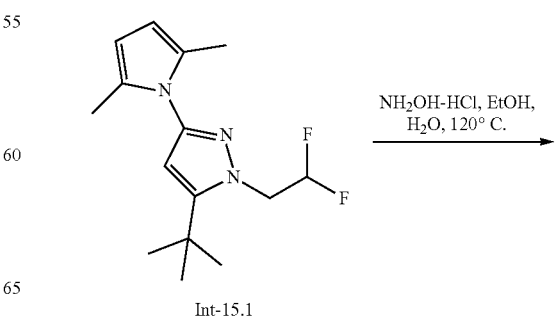

-continued

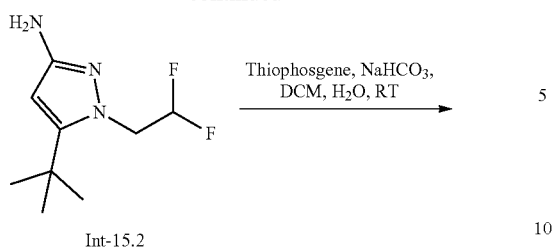

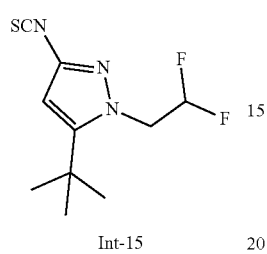

Synthesis of compound Int-15.1. To a solution of Int-1.1 (2.5 g, 11.50 mmol, 1.0 equiv) and 2,2-difluoroethyl trifluoromethanesulfonate (3.69 g, 17.26 mmol, 1.5 equiv) in DMF (25 mL) was added cesium carbonate (11.2 g, 34.5 mmol, 3.0 equiv) and the reaction mixture was stirred at 80-90° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8-10% ethyl acetate in hexane) to afford Int-15.1. MS (ES): m/z 282.4 [M+H]$^+$.

Synthesis of compound Int-15.2. Compound Int-15.2 was prepared from Int-15.1, following the procedure described in the synthesis of Int-1.4. The product was purified by flash column chromatography on silica gel (CombiFlash®, 40% ethyl acetate in hexane). MS (ES): m/z 204.2 [M+H]$^+$.

Synthesis of compound Int-15. Compound Int-15 was prepared from Int-15.2, following the procedure described in the synthesis of Int-1.

Preparation of Intermediates Int-16a and Int-16b
(S)-1-(2-(benzyloxy)propyl)-5-(tert-butyl)-3-isothiocyanato-1H-pyrazole and (R)-1-(2-(benzyloxy)propyl)-5-(tert-butyl)-3-isothiocyanato-1H-pyrazole

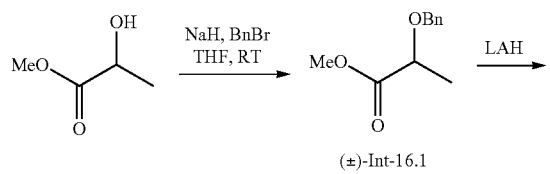

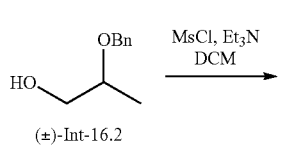

-continued

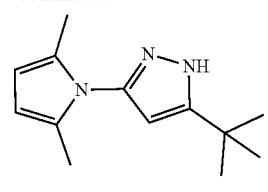

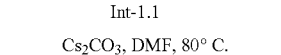

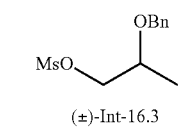

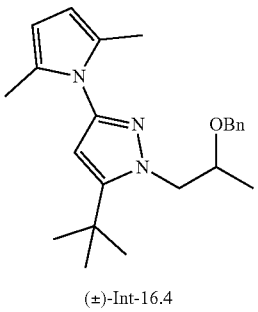

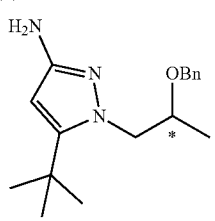 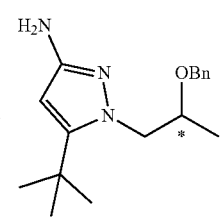

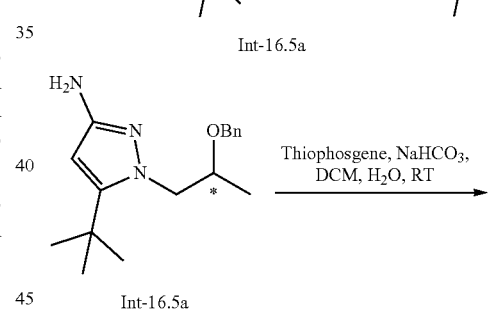

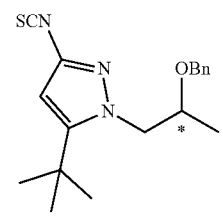

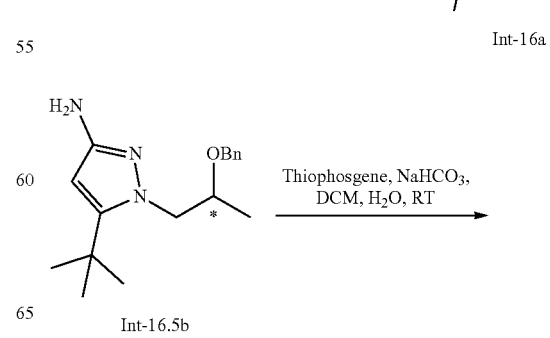

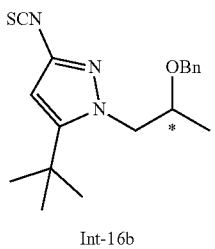

Int-16b

Synthesis of compound (±)-Int-16.1. To a suspension of sodium hydride (2.88 g, 72.04 mmol, 1.5 equiv) in THF (25 mL) was added a solution of methyl 2-hydroxypropanoate (5.0 g, 48.03 mmol, 1.0 equiv) in THF (25 mL) at 0° C. and stirred for 1 h followed by addition of benzyl bromide (6.85 mL, 57.63 mmol, 1.2 equiv) and the reaction mixture was stirred at room temperature for 2 h. It was poured over ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% ethyl acetate in hexane) to afford (±)-Int-16.1. $^1$H NMR (DMSO-$d_6$, 400 MHz): δ 7.39-7.30 (m, 5H), 4.59-4.56 (d, 1H), 4.46-4.43 (d, 1H), 4.16-4.11 (q, 1H), 3.69 (s, 3H), 1.34 (s, 3H).

Synthesis of compound (±)-Int-16.2. To a solution of (±)-Int-16.1 (3.0 g, 15.45 mmol, 1.0 equiv) in THF (30 mL), was added lithium aluminum hydride solution (1 M in THF, 39 mL, 38.62 mmol, 2.5 equiv) at 0° C. The reaction mixture was stirred for 1 h and quenched by the addition of saturated aqueous anhydrous sodium. Precipitates were removed by filtering through a pad of Celite® and rinsed with ethyl acetate. The organic layer was separated and dried over anhydrous sodium sulfate, filtered and concentrated under reduced pressure to afford (±)-Int-16.2. $^1$H NMR (DMSO-$d_6$, 400 MHz): δ 7.35-7.25 (m, 5H), 4.65-4.62 (t, 1H), 4.50 (s, 2H), 3.52-3.42 (m, 2H), 3.33 (bs, 1H), 1.10 (s, 3H).

Synthesis of compound (±)-Int-16.3. To a solution of (±)-Int-16.2 (2.5 g, 15.04 mmol, 1.0 equiv) in dichloromethane (25 mL) was added triethylamine (6.3 mL, 45.12 mmol, 3.0 equiv) at 0° C. followed by addition of mesyl chloride (2.3 mL, 30.08 mmol, 2.0 equiv). The reaction mixture was stirred at 0° C. for 30 min. It was poured over ice-water, stirred and extracted with dichloromethane. The combined organic layers were washed with saturated sodium bicarbonate followed by brine, dried over anhydrous sodium sulfate, filtered and concentrated under reduced pressure to afford (±)-Int-16.3. The crude product was used without further purification.

Synthesis of compound (±)-Int-16.4. A mixture of Int-1.1 (1.9 g, 8.74 mmol, 1.0 equiv), (±)-Int-16.3 (2.9 g, 12.24 mmol, 1.4 equiv) and cesium carbonate (8.54 g, 26.22 mmol, 3.0 equiv) in DMF (20 mL) was added stirred at 80° C. for 4 h. It was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1-2% ethyl acetate in hexane) to afford (±)-Int-16.4. MS (ES): m/z 366.45 [M+H]$^+$.

Synthesis of compound (±)-Int-16.5. Compound (±)-Int-16.5 was prepared from (±)-Int-16.4, following the procedure described in the synthesis of Int-1.4. The product was purified by flash column chromatography on silica gel (CombiFlash®, 25% ethyl acetate in hexane). MS (ES): m/z 288.4 [M+H]$^+$.

Separation of compounds Int-16.5a and Int-16.5b. Enantiomers of (±)-Int-16.5 were separated by HPLC (column: CHIRALPAK IG (250 mm×21 mm, 5 μm), mobile phase: (A) 0.1% DEA in n-hexane, (B) 0.1% DEA in 2-propanol; flow rate=20 mL/min) to afford first eluting fraction (Int-16.5a, MS (ES): m/z 288.4 [M+H]$^+$) and second eluting fraction (Int-16.5b, MS (ES): m/z 288.4 [M+H]$^+$). (*Absolute stereochemistry not confirmed.)

Preparation of Intermediate Int-17: 5-(tert-butyl)-3-isothiocyanato-1-(4-oxaspiro[2.4]heptan-7-yl)-1H-pyrazole

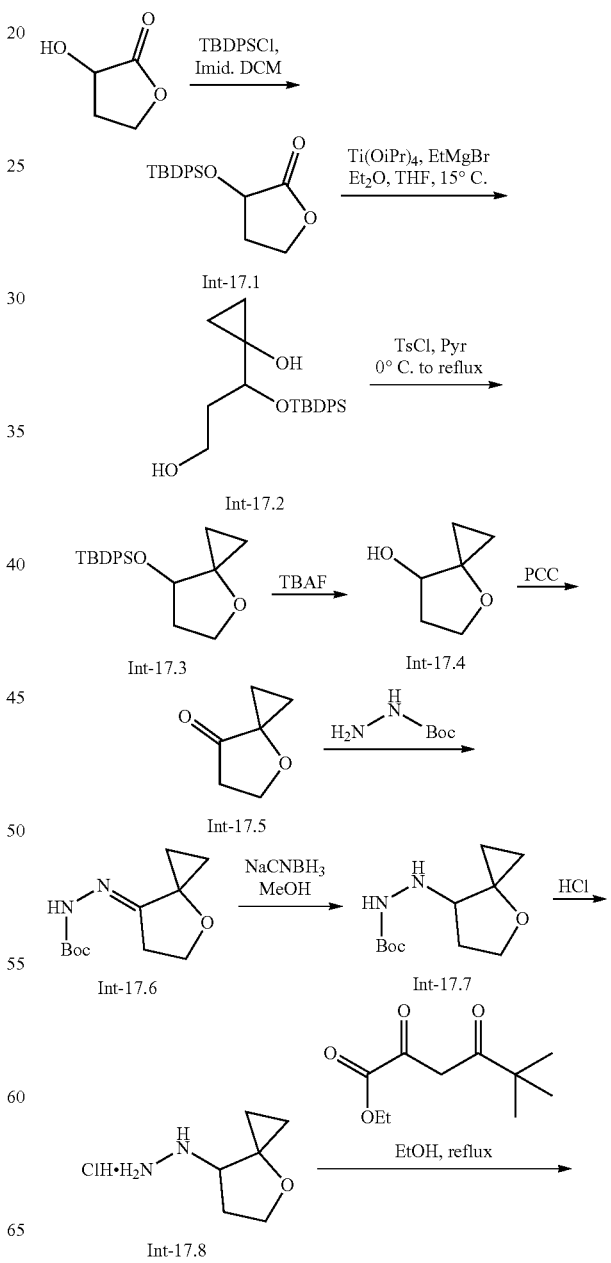

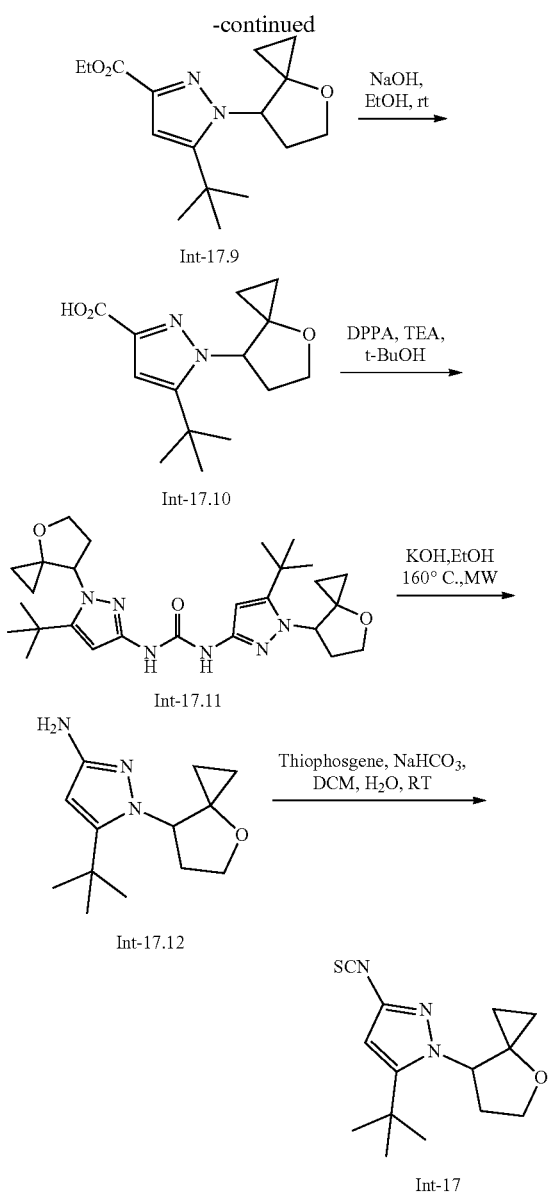

Synthesis of compound Int-17.1. To a solution of 3-hydroxydihydrofuran-2(3H)-one (25 g, 244.8 mmol, 1.0 equiv) and imidazole (38.3 g, 563.04 mmol, 2.3 equiv) in dichloromethane (400 mL) at 0° C. was added tert-butyldiphenylchlorosilane (80.7 g, 293.76 mmol, 1.2 equiv). The reaction mixture was stirred at room temperature for 2 h. It was poured into ice-water and extracted with dichloromethane. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford 17.1. $^1$H NMR (DMSO-d$_6$, 400 MHz): δ 7.74-7.65 (m, 4H), 7.51-7.39 (m, 6H), 4.61-4.56 (m, 1H), 4.28-4.24 (m, 1H), 4.10-4.04 (m, 1H), 2.29-2.14 (m, 2H), 1.03 (s, 9H).

Synthesis of compound Int-17.2. To a solution of Int-17.1 (40 g, 117.48 mmol, 1.0 equiv) in THF (120 mL) and diethyl ether (120 mL) at 15° C. was added titanium isopropoxide (16.69 g, 58.74 mmol, 0.5 equiv) followed by the addition of ethyl magnesium bromide (3.0 M in diethyl ether, 117.5 mL, 352.4 mmol, 3.0 equiv). It was stirred for 1 h at 15° C. and room temperature for 1 h. It was poured into a saturated solution of ammonium chloride and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-17.2. $^1$H NMR (CDCl$_3$, 400 MHz): δ 7.73-7.67 (m, 4H), 7.47-7.39 (m, 6H), 3.93-3.88 (m, 1H), 3.67-3.61 (m, 1H), 3.51 (s, 2H), 3.35-3.32 (m, 1H), 1.93-1.87 (m, 2H), 1.11 (s, 9H), 0.82-0.76 (m, 1H), 0.61-0.56 (m, 1H), 0.40-0.34 (m, 1H), 0.18-0.17 (m, 1H).

Synthesis of compound Int-17.3. To a solution of Int-17.2 (32 g, 86.35 mmol, 1.0 equiv) in pyridine (320 mL) was added p-toluenesulfonyl chloride (32.81 g, 172.7 mmol, 2.0 equiv) in portions at 0° C. The reaction mixture was stirred at room temperature for 2 h and it was heated to reflux for 2 h. After completion of reaction, reaction mixture was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane) to afford Int-17.3. $^1$H NMR (CDCl$_3$, 400 MHz): δ 7.67-7.64 (m, 4H), 7.47-7.38 (m, 6H), 4.19-4.16 (m, 1H), 4.07-4.01 (m, 1H), 3.82-3.77 (m, 1H), 2.15-2.08 (m, 1H), 2.06-1.95 (m, 1H), 1.08 (s, 9H), 0.79-0.66 (m, 3H), 0.31-0.22 (m, 1H).

Synthesis of compound Int-17.4. To a solution of Int-17.3 (25 g, 70.91 mmol, 1.0 equiv) in THF (250 mL) was added tetra-n-butyl ammonium fluoride (1 M in THF, 142 mL, 141.82 mmol, 2.0 equiv) at 0° C. and stir for 30 min. The reaction mixture was allowed to warm to rt and stirred for 16 h. It was poured over crushed ice, stirred, neutralized with saturated aqueous sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford Int-17.4. $^1$H NMR (CDCl$_3$, 400 MHz): δ 4.12-3.99 (m, 1H), 3.98-3.90 (m, 2H), 2.45-2.36 (m, 1H), 2.12-2.05 (m, 1H), 1.09-0.94 (m, 1H), 0.88-0.80 (m, 2H), 0.65-0.59 (m, 1H).

Synthesis of compound Int-17.5. To a solution of Int-17.4 (4.9 g, 42.93 mmol, 1.0 equiv) in dichloromethane (50 mL) was added pyridinium chlorochromate (27.68 g, 128.79 mmol, 3.0 equiv) at 0° C. The reaction mixture was stirred at room temperature for 12 h. After completion of reaction, diethyl ether was added, and the precipitates were removed by filtration. The filtrate was concentrated under reduced pressure to obtain Int-17.5. It was used in the next step without further purification.

Synthesis of compound Int-17.6. To a solution of Int-17.5 (2.5 g, 22.3 mmol, 1.0 equiv) in ethanol (25 mL) was added tert-butyl hydrazinecarboxylate (3.24 g, 24.53 mmol, 1.1 equiv). The reaction mixture was heated to reflux for 12 h. It was concentrated under reduced pressure. The residue was purified by flash column chromatography on silica gel (CombiFlash®, 17% ethyl acetate in hexane) to afford Int-17.6. $^1$H NMR (DMSO-d$_6$, 400 MHz): δ 9.60 (s, 1H), 3.98-3.95 (m, 2H), 2.73-2.70 (m, 2H), 1.43 (s, 9H), 1.02-0.99 (m, 2H), 0.84-0.81 (m, 2H).

Synthesis of compound Int-17.7. To a solution of Int-17.6 (1.1 g, 4.86 mmol, 1.0 equiv) in acetic acid (10 mL) was added sodium cyanoborohydride (0.301 g, 4.86 mmol, 1.0 equiv) in portions. The reaction mixture was stirred at room temperature for 1 h. It was poured into ice-water, stirred, neutralized with 1 N sodium hydroxide solution and extracted with dichloromethane. The combined organic layers were washed with brine, dried over anhydrous sodium sulfate, filtered and concentrated under reduced pressure to afford Int-17.7. $^1$H NMR (CDCl$_3$, 400 MHz): δ 6.59 (s, 1H), 5.33 (s, 1H), 4.18-4.07 (m, 2H), 3.93-3.90 (m, 1H), 3.44 (bs, 1H), 2.34-2.31 (m, 1H), 1.50 (s, 9H), 1.09-1.06 (m, 2H), 0.75-0.73 (m, 1H), 0.56 (bs, 1H).

Synthesis of compound Int-17.8. To a solution of Int-17.8 (1.0 g, 4.38 mmol, 1.0 equiv) in 1,4-dioxane (10 mL) was added 4 M hydrogen chloride in dioxane (11 mL, 43.8 mmol, 10 equiv) at 0° C. The reaction mixture was allowed to warm to rt and stirred for 12 h. After completion of reaction, reaction mixture was concentrated under reduced pressure to obtain Int-17.8. $^1$H NMR (DMSO-d$_6$, 400 MHz): δ 9.12 (bs, 1H), 3.92-3.90 (m, 2H), 3.75-3.70 (m, 2H), 2.29 (bs, 4H), 0.66-0.54 (m, 4H).

Synthesis of compound Int-17.9. To a solution of Int-17.8 (0.700 g, 4.25 mmol, 1.0 equiv) in ethanol (10 mL) was added ethyl 5,5-dimethyl-2,4-dioxohexanoate (0.851 g, 4.25 mmol, 1.0 equiv). The reaction mixture was heated to reflux for 12 h. It was concentrated under reduced pressure. The residue was purified by flash column chromatography on silica gel (CombiFlash®, 20% ethyl acetate in hexane) to afford Int-17.9. MS (ES): m/z 293.4 [M+H]$^+$.

Synthesis of compound Int-17.10. To a solution of Int-17.9 (0.610 g, 2.09 mmol, 1.0 equiv) in ethanol-water (8:2, 10 mL) was added powdered sodium hydroxide (0.334 g, 8.36 mmol, 4.0 equiv) at 0° C. The reaction mixture was stirred at room temperature for 12 h. It was transferred into ice-water. The pH was adjusted with 1N HCl solution to 2 and the mixture was extracted with ethyl acetate. The combined organic layers were washed with brine, dried over anhydrous sodium sulfate, filtered and concentrated under reduced pressure. The crude product was triturated with diethyl ether to obtain Int-17.10. MS (ES): m/z 265.3 [M+H]$^+$.

Synthesis of compound Int-17.11. To a solution of Int-17.10 (0.4 g, 1.51 mmol, 1.0 equiv) and triethyl amine (0.42 mL, 3.02 mmol, 2.0 equiv) in tert-butanol (6 mL) was added diphenylphosphoryl azide (0.622 g, 2.26 mmol, 1.5 equiv). The reaction mixture was stirred at 90° C. for 12 h. It was transferred into ice-cold water, stirred and extracted with ethyl acetate. The combined organic layers were washed with brine, dried over anhydrous sodium sulfate, filtered and concentrated under reduced pressure to afford Int-17.11. MS (ES): m/z 497.6 [M+H]$^+$.

Synthesis of compound Int-17.12. To a solution of Int-17.11 (0.4 g, 0.805 mmol, 1.0 equiv) in ethanol-water (2:0.4, 10 mL) was added 20% aqueous solution of potassium hydroxide (2.0 mL) and the reaction mixture was stirred at 160° C. in microwave reactor for 1 h. It was concentrated under reduced pressure. The residue was purified by flash column chromatography on silica gel (CombiFlash®, 1.5% methanol in dichloromethane) to afford (f)-Int-17.12. MS (ES): m/z 236.4 [M+H]$^+$.

Synthesis of compound Int-17. Compound Int-17 was prepared from Int-17.12, following the procedure described in the synthesis of Int-1. MS (ES): m/z 278.1 [M+H]$^+$.

Preparation of Intermediate Int-18: (S)-5-(tert-butyl)-3-isothiocyanato-1-(1-(2-methoxyethyl)pyrrolidin-3-yl)-1H-pyrazole

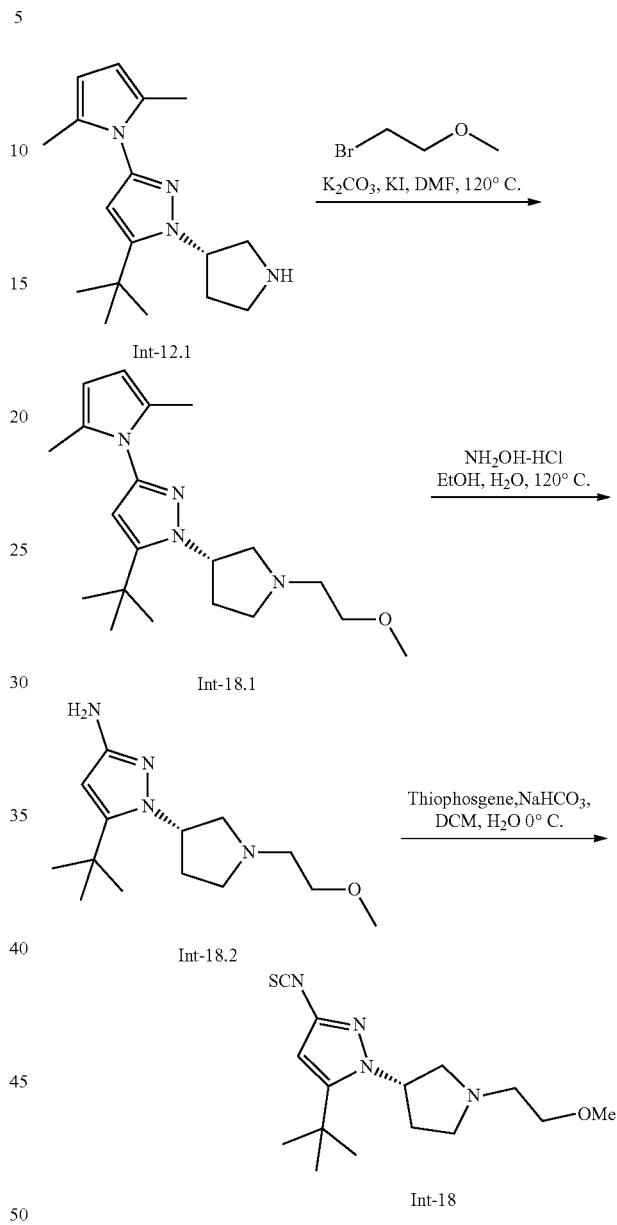

Synthesis of compound Int-18.1. A mixture of Int-12.1 (1.0 g, 3.49 mmol, 1.0 equiv), 1-bromo-2-methoxyethane (0.582 g, 4.19 mmol, 1.2 equiv), potassium carbonate (1.44 g, 10.47 mmol, 3.0 equiv) and potassium iodide (0.028 g, 0.174 mmol, 0.05 equiv) in DMF (10 mL) was stirred at 120° C. for 5 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% ethyl acetate in hexane) to afford Int-18.1. MS (ES): m/z 345.5 [M+H]$^+$.

Synthesis of compound Int-18.2. Compound Int-18.2 was prepared from Int-18.1 following the procedure described in the synthesis of compound Int-1.4. The product was purified by flash column chromatography on silica gel (Combi-Flash®, 4-5% methanol in DCM). MS (ES): m/z 223.3 [M+H]+.

Synthesis of Int-18. Compound Int-18 was prepared from Int-18.2 following the procedure described in the synthesis of compound Int-1. The product was purified by flash column chromatography on silica gel (CombiFlash®, 3.2% methanol in DCM). MS (ES): m/z 309.4 [M+H]+.

Preparation of Intermediate Int-19: (R)-5-(tert-butyl)-3-isothiocyanato-1-(1-(2-methoxyethyl)pyrrolidin-3-yl)-1H-pyrazole

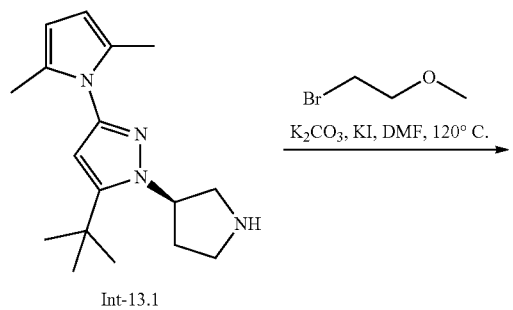

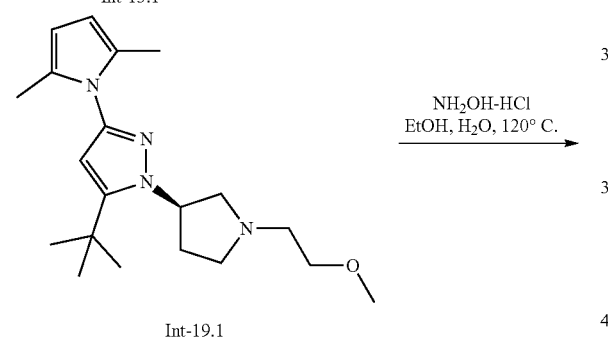

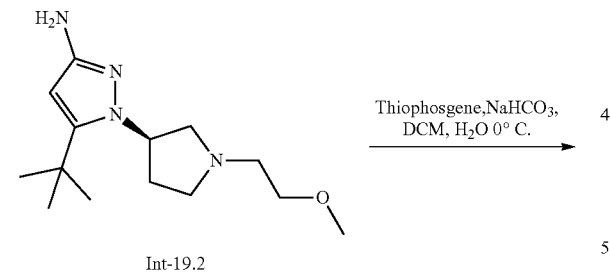

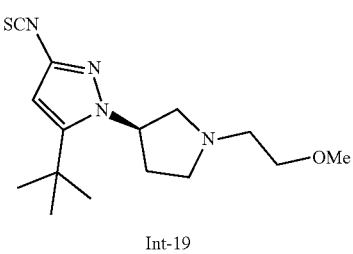

Synthesis of Int-19. Compound Int-19 was prepared following the procedures described in the synthesis of compound Int-18. The product was purified by flash column chromatography on silica gel (CombiFlash®, 3.2% methanol in DCM). MS (ES): m/z 309.4 [M+H]+.

Preparation of Intermediate Int-20: 2-(5-(tert-butyl)-3-isothiocyanato-1H-pyrazol-1-yl)acetonitrile

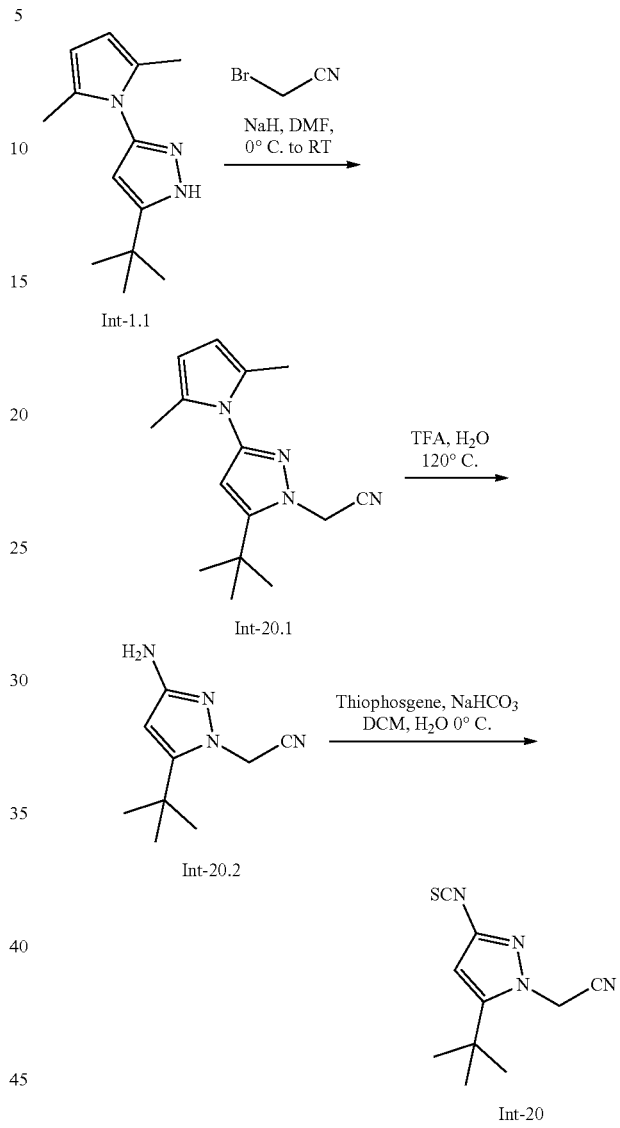

Synthesis of compound Int-20.1. To a solution of Int-1.1 (5.0 g, 23.01 mmol, 1.0 equiv) in DMF (25 mL) was added sodium hydride (3.6 g, 92.04 mmol, 4.0 equiv) in portions at 0° C. The reaction mixture was stirred at 0° C. for 2 h followed by addition of bromoacetonitrile (13.7 g, 115.08 mmol, 5.0 equiv) dropwise. The reaction mixture was stirred at room temperature for 16 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6-8% ethyl acetate in hexane) to afford Int-20.1. MS (ES): m/z 257.3 [M+H]+.

Synthesis of compound Int-20.2. To a suspension of Int-20.1 (0.465 g, 1.82 mmol, 1.0 equiv) in water (20 mL) was added trifluoroacetic acid (10 mL). The reaction mixture was stirred at 120° C. for 10 min. It was poured into ice-water, followed by addition of saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 70% ethyl acetate in hexane) to afford Int-20.2. MS (ES): m/z 179.2 [M+H]$^+$.

Synthesis of compound Int-20. Compound Int-20 was prepared from Int-20.2 following the procedure described in the synthesis of compound Int-1. The product was purified by flash column chromatography on silica gel (Combi-Flash®, 30% ethyl acetate in hexane). MS (ES): m/z 221.2 [M+H]$^+$.

Preparation of Intermediate Int-21: 1-((1r,3r)-3-(benzyloxy)cyclobutyl)-5-(tert-butyl)-3-isothiocya-nato-1H-pyrazole

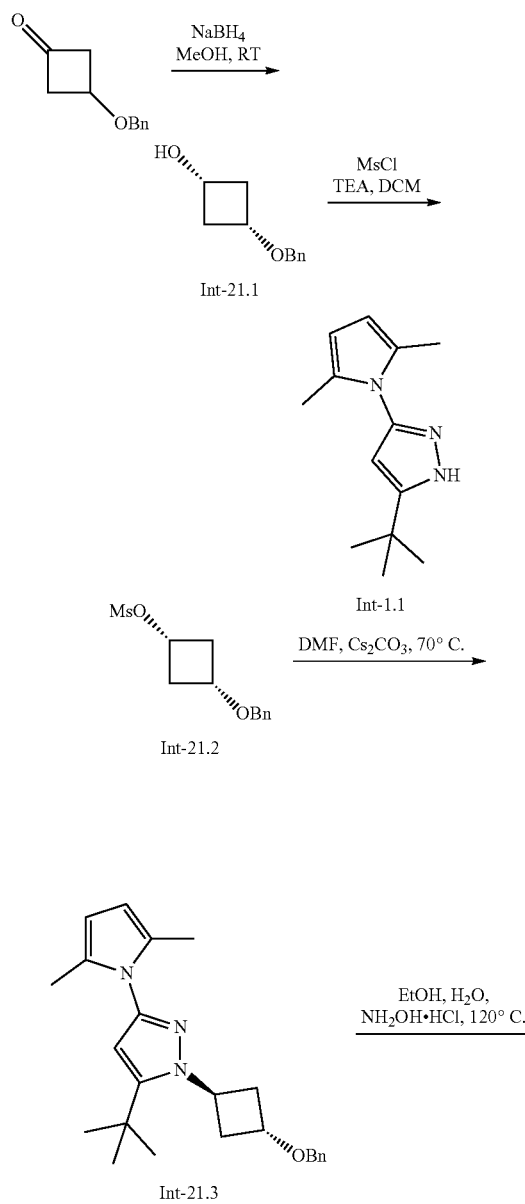

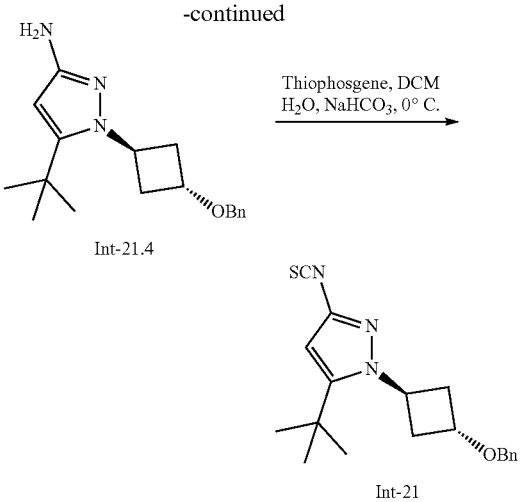

Synthesis of compound Int-21.1. To a solution of 3-(ben-zyloxy)cyclobutan-1-one (10 g, 56.75 mmol, 1.0 equiv) in methanol (100 mL) was added sodium borohydride (6.4 g, 170.2 mmol, 3.0 equiv) in small portions at 0° C. The reaction mixture was stirred at room temperature for 3 h. It was poured over ice-water, stirred and extracted with ethyl acetate. The combined organic layers were washed with brine, dried over anhydrous sodium sulfate, filtered and concentrated under reduced pressure to afford Int-21.1. MS (ES): m/z 179.3 [M+H]$^+$.

Synthesis of compound Int-21.2 To a solution of Int-21.1 (3.0 g, 16.83 mmol, 1.0 equiv) in DCM (30 mL) was added triethylamine (3.0 mL, 21.87 mmol, 1.3 equiv) at 0° C. followed by addition of methanesulfonyl chloride (1.7 mL, 21.87 mmol, 1.3 equiv). The reaction mixture was stirred at room temperature for 12 h. It was poured into ice-water, stirred and extracted with DCM. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-21.2. MS (ES): m/z 257.3 [M+H]$^+$.

Synthesis of compound Int-21.3. A mixture of Int-1.1 (3.2 g, 12.48 mmol, 1.0 equiv), Int-21.2 (2.71 g, 12.48 mmol, 1.0 equiv) and cesium carbonate (8.13 g, 24.96 mmol, 2.0 equiv) in DMF (30 mL) was stirred at 80-90° C. for 12 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi-Flash®, 8-12% ethyl acetate in hexane) to afford Int-21.3. MS (ES): m/z 378.5 [M+H]$^+$.

Synthesis of compound Int-21.4. Compound Int-21.4 was prepared from Int-21.3 following the procedure described in the synthesis of compound Int-1.4. The product was purified by flash column chromatography on silica gel (Combi-Flash®, 24-28% ethyl acetate in hexane). MS (ES): m/z 300.4 [M+H]$^+$.

Synthesis of compound Int-21. Compound Int-21 was prepared from Int-21.4 following the procedure described in the synthesis of compound Int-1. The product was used without purification. MS (ES): m/z 342.5 [M+H]$^+$.

Preparation of Intermediate (±)-Int-22: 5-(tert-butyl)-4-(tetrahydrofuran-3-yl)thiazol-2-amine

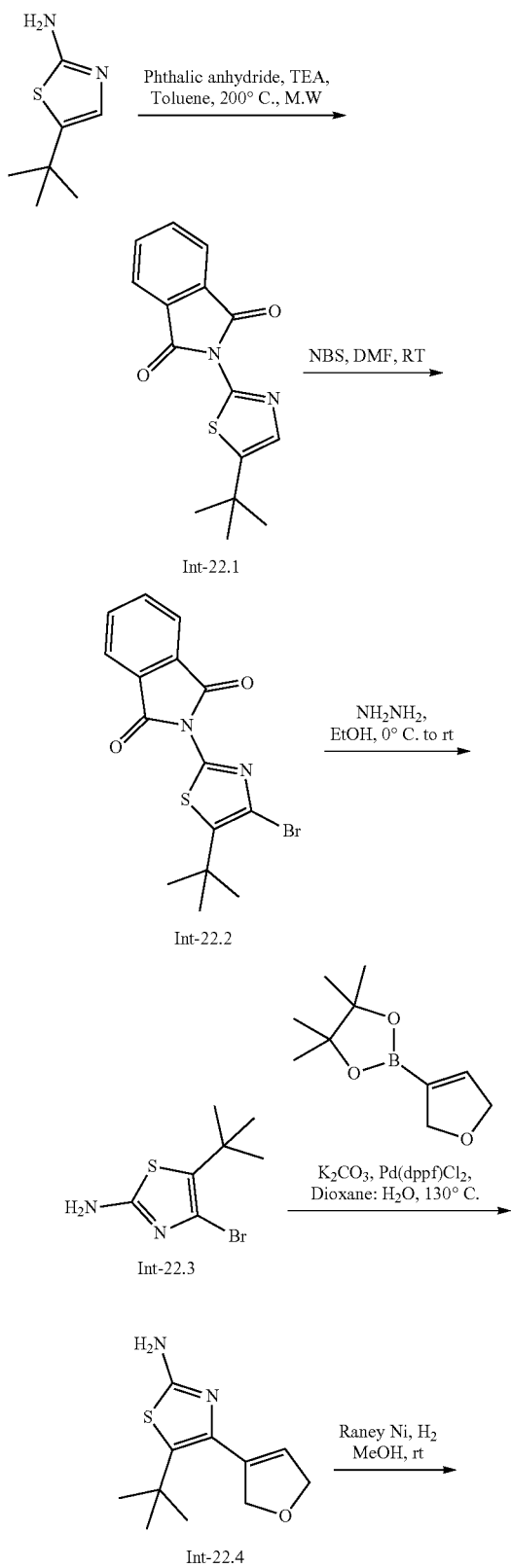

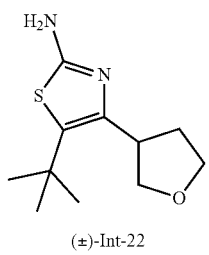

(±)-Int-22

Synthesis of compound Int-22.1. A solution of 5-(tert-butyl)thiazol-2-amine (2.0 g, 12.80 mmol, 1.0 equiv), phthalic anhydride (3.79 g, 25.60 mmol, 2.0 equiv), triethylamine (5.4 mL, 38.4 mmol, 3.0 equiv) in toluene (20 mL) was stirred at 200° C. in a microwave reactor for 2 h. It was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 11% ethyl acetate in hexane) to afford Int-22.1. MS (ES): m/z 287.3 [M+H]$^+$.

Synthesis of compound Int-22.2. To a solution of Int-22.1 (2.1 g, 7.33 mmol, 1.0 equiv) in DMF (20 mL) was added NBS (6.5 g, 36.6 mmol, 5.0 equiv). The reaction mixture was stirred at room temperature for 1 h. It was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford Int-22.2. MS (ES): m/z 366.2 [M+H]$^+$.

Synthesis of compound Int-22.3. A solution of Int-22.2 (1.9 g, 5.2 mmol, 1.0 equiv) in ethanol (20 mL) was added hydrazine (0.34 mL, 10.4 mmol, 2.0 equiv) at 0° C. The reaction mixture was stirred at room temperature for 12 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 70% ethyl acetate in hexane) to afford Int-22.3. MS (ES): m/z 236.1 [M+H]$^+$.

Synthesis of compound Int-22.4. A mixture of Int-22.3 (1.0 g, 4.25 mmol, 1.0 equiv), 2-(2,5-dihydrofuran-3-yl)-4,4,5,5-tetramethyl-1,3,2-dioxaborolane (2.5 g, 12.76 mmol, 3.0 equiv) and potassium carbonate (1.76 g, 12.76 mmol, 3.0 equiv) in 1,4-dioxane (10 mL) and water (1 mL) was degassed by bubbling through a stream of argon for 10 min. Under argon atmosphere, [1,1'-bis(diphenylphosphino)ferrocene]dichloropalladium(II)-DCM complex (0.173 g, 0.212 mmol, 0.05 equiv) was added, and the mixture was degassed for another 5 min. The reaction mixture was stirred at 130° C. for 3 h. It was cooled to room temperature and filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 1% methanol in DCM) to afford Int-22.4. MS (ES): m/z 225.3 [M+H]$^+$.

Synthesis of compound (±)-Int-22. A mixture of Raney nickel (0.2 g) and compound Int-22.4 (0.250 g, 1.11 mmol, 1.0 equiv) in methanol (10 mL) was stirred under hydrogen atmosphere for 12 h. It was filtered through a pad of Celite® and rinsed with methanol. The filtrate was concentrated under reduced pressure to afford (±)-Int-22. The product was used without purification. MS (ES): m/z 227.3 [M+H]+.

Preparation of Intermediate Int-23: 5-cyclopropyl-3-isothiocyanato-1-methylpyridin-2(1H)-one

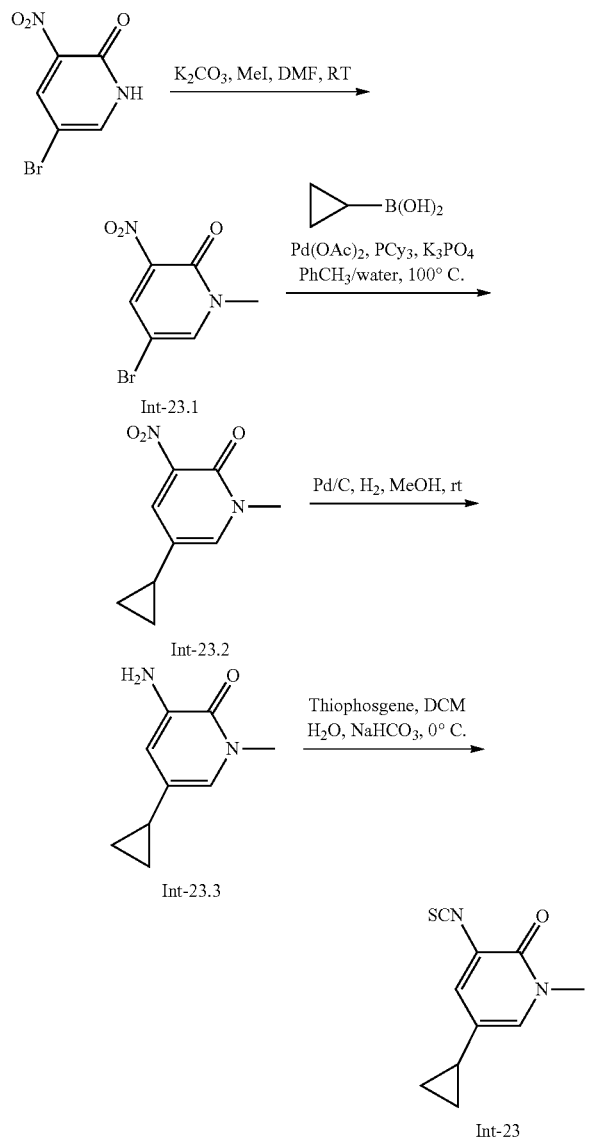

Synthesis of compound Int-23.1. A mixture of 5-bromo-3-nitropyridin-2(1H)-one (5.0 g, 22.83 mmol, 1.0 equiv) and potassium carbonate (6.6 g, 47.94 mmol, 2.1 equiv) in DMF (50 mL) was stirred for 15 min before the addition of methyl iodide (3.56 g, 25.11 mmol, 1.1 equiv). The reaction mixture was stirred at room temperature for 1 h. It was poured into ice-water and extracted with ethyl acetate. The combined organic layers were washed with brine, dried over anhydrous sodium sulfate, filtered and concentrated under reduced pressure to afford Int-23.1. MS (ES): m/z 234.02 [M+H]+.

Synthesis of compound Int-23.2. A mixture of Int-23.1 (0.7 g, 3.0 mmol, 1.0 equiv), cyclopropylboronic acid (0.774 g, 9.0 mmol, 3.0 equiv), potassium phosphate (1.9 g, 9.0 mmol, 3.0 equiv) and tricyclohexylphosphine (0.168 g, 0.6 mmol, 0.2 equiv) in toluene (10 mL) and water (1 mL) was degassed by bubbling through a stream of argon for 10 min. Under argon atmosphere palladium(II) acetate (0.336 g, 1.5 mmol, 0.5 equiv) was added, and the mixture was degassed for additional 5 min. The reaction mixture was stirred at 100° C. for 2 h. It was cooled to room temperature and filtered through a pad of Celite®. The filtrate was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-23.2. MS (ES): m/z 195.2 [M+H]+.

Synthesis of compound Int-23.3. A mixture of compound Int-23.2 (0.182 g, 0.93 mmol, 1.0 equiv) and 10% palladium on carbon (0.1 g) in methanol (5 mL) was stirred under hydrogen atmosphere (1 atm) at rt for 2 h. The mixture was filtered through a pad of Celite® and rinsed with methanol. The filtrate was concentrated under reduced pressure to afford Int-23.3. MS (ES): m/z 165.21 [M+H]+.

Synthesis of compound Int-23. Compound Int-23 was prepared from Int-23.3 following the procedure described in the synthesis of compound Int-1. The product was used without purification. MS (ES): m/z 207.3 [M+H]+.

Preparation of Intermediate Int-24: 5-cyclopropyl-3-isothiocyanato-1-(2-methoxyethyl)pyridin-2(1H)-one

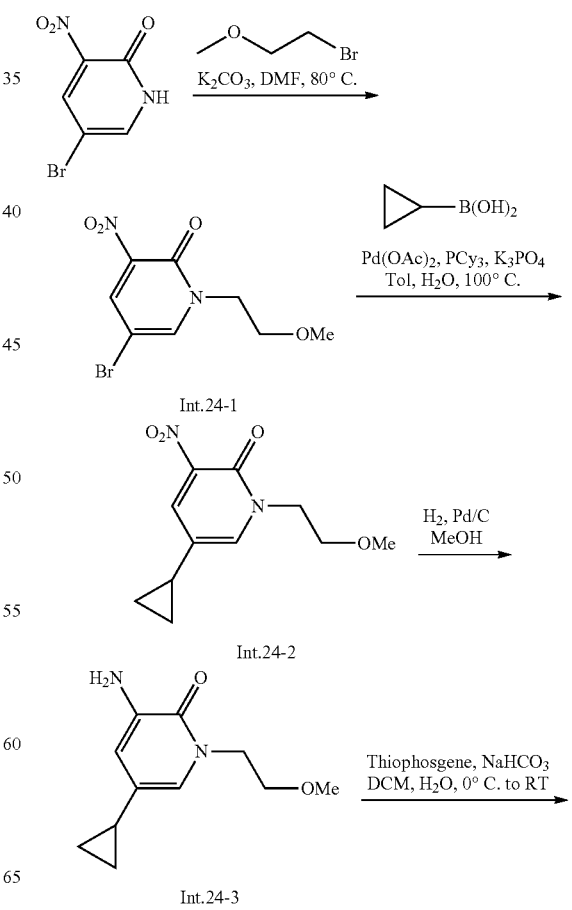

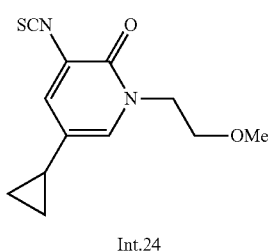

Int.24

Synthesis of compound Int-24.1. A mixture of 5-bromo-3-nitropyridin-2(1H)-one (1.0 g, 4.57 mmol, 1.0 equiv) and potassium carbonate (1.57 g, 11.42 mmol, 2.5 equiv) in DMF (10 mL) was stirred for 15 min before the addition of 1-bromo-2-methoxyethane (0.698 g, 5.02 mmol, 1.1 equiv). The reaction mixture was stirred at 80° C. for 30 min. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 7-8% ethyl acetate in hexane) to afford Int-24.1. MS (ES): m/z 278.1 [M+H]$^+$.

Synthesis of compound Int-24.2. Compound Int-24.2 was prepared from Int-24.1, following the procedure described in the synthesis of Int-23.2. The product was purified by flash column chromatography on silica gel (CombiFlash®, 30% ethyl acetate in hexane). MS (ES): m/z 239.2 [M+H]$^+$.

Synthesis of compound Int-24.3. Compound Int-24.3 was prepared from Int-24.2 following the procedure described in the synthesis of compound Int-23.3. The product was used without purification. MS (ES): m/z 209.3 [M+H]$^+$.

Synthesis of compound Int-24. Compound Int-24 was prepared from Int-24.3 following the procedure described in the synthesis of compound Int-1. The product was used without purification. MS (ES): m/z 251.3 [M+H]$^+$.

Preparation of Intermediate cis-(±)-Int-25: 1-(2-(benzyloxy)cyclopentyl)-5-(tert-butyl)-3-isothiocyanato-1H-pyrazole

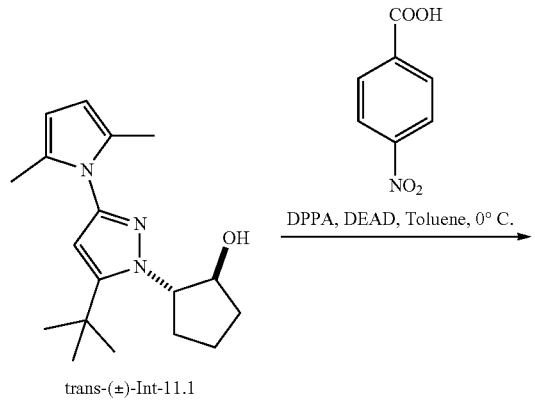

trans-(±)-Int-11.1

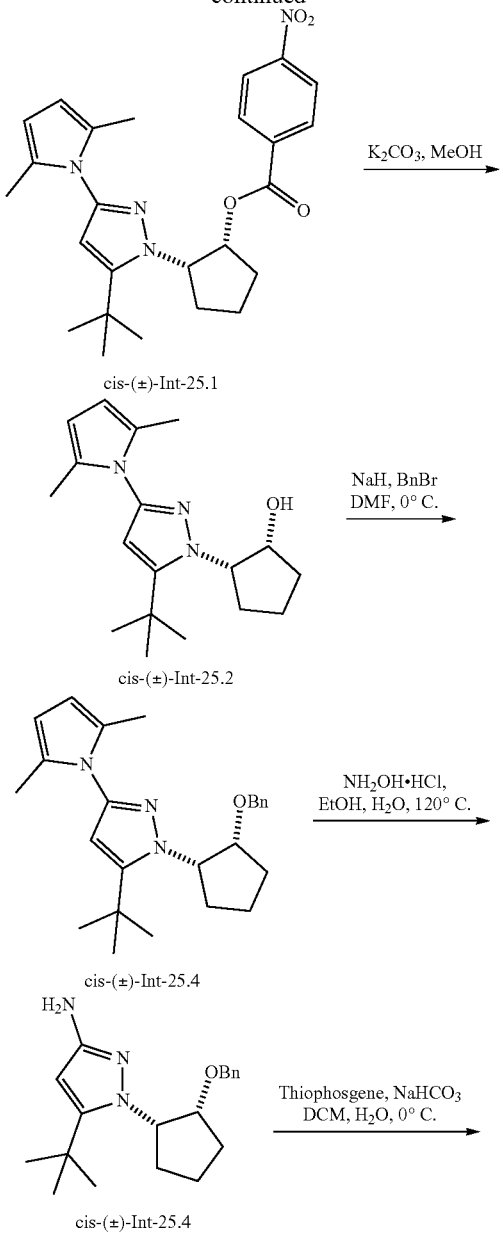

Synthesis of compound cis-(±)-Int-25.1. To a mixture of compound trans-(±)-Int-11.1 (1.6 g, 5.31 mmol, 1.0 equiv), 4-nitrobenzoic acid (1.77 g, 10.62 mmol, 2.0 equiv) and diphenylphosphoryl azide (3.17 g, 7.96 mmol, 1.5 equiv) in toluene (35 mL) at 0° C. was added diethylazodicarboxylate (1.38 g, 7.96 mmol, 1.5 equiv). The reaction mixture was stirred at room temperature for 2 h. It poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford cis-(±)-Int-25.1. MS (ES): m/z 451.4 [M+H]$^+$.

Synthesis of compound cis-(±)-Int-25.2. To a solution of cis-(±)-Int-25.1 (0.8 g, 1.78 mmol, 1.0 equiv) in methanol (20 mL) was added potassium carbonate (1.96 g, 14.24 mmol, 8.0 equiv). The reaction mixture was stirred at room temperature for 1 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford cis-(±)-Int-25.2. MS (ES): m/z 302.4 [M+H]$^+$.

Synthesis of compound cis-(±)-Int-25.3. To a solution of cis-(±)-Int-25.2 (0.5 g, 1.66 mmol, 1.0 equiv) in DMF (10 mL) was added sodium hydride (0.132 g, 3.32 mmol, 2.0 equiv) at 0° C. and stirred for 20 min followed by addition of benzyl bromide (0.3 mL, 2.49 mmol, 1.5 equiv). The reaction mixture was stirred at room temperature for 30 min. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane) to afford cis-(±)-Int-25.3. MS (ES): m/z 392.5 [M+H]$^+$.

Synthesis of compound cis-(±)-Int-25.4. Compound cis-(±)-Int-25.4 was prepared from cis-(±)-Int-25.3 following the procedure described in the synthesis of compound Int-1.4. The product was purified by flash column chromatography on silica gel (CombiFlash®, 28-30% ethyl acetate in hexane). MS (ES): m/z 314.4 [M+H]$^+$.

Synthesis of compound cis-(±)-Int-25. Compound cis-(±)-Int-25 was prepared from cis-(±)-Int-25.4 following the procedure described in the synthesis of compound Int-1. The product was used without purification. MS (ES): m/z 356.5 [M+H]$^+$.

Preparation of Intermediate Int-26: 3-(3-amino-5-(tert-butyl)-1H-pyrazol-1-yl)propanenitrile

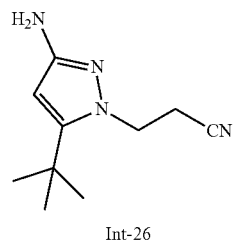

Synthesis of compound Int-26.1. To a solution of Int-1.1 (15 g, 69.02 mmol, 1.0 equiv) in acetonitrile (150 mL) was added acrylonitrile (5.4 mL, 82.8 mmol, 1.2 equiv). The reaction mixture was stirred at room temperature for 16 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 12-15% ethyl acetate in hexane) to afford Int-26.1. MS (ES): m/z 271.3 [M+H]$^+$.

Synthesis of compound Int-26. To a suspension of Int-26.1 (1.9 g, 7.03 mmol, 1.0 equiv) in water (20 mL) was added trifluoroacetic acid (7 mL). The reaction mixture was stirred at 120° C. for 10 min. It was poured into ice-water, followed by addition of saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in DCM) to afford Int-26. MS (ES): m/z 193.2 [M+H]$^+$.

Preparation of Intermediate Int-27: 1-(2-(benzyloxy)ethyl)-5-cyclopropyl-3-isothiocyanatopyridin-2(1H)-one

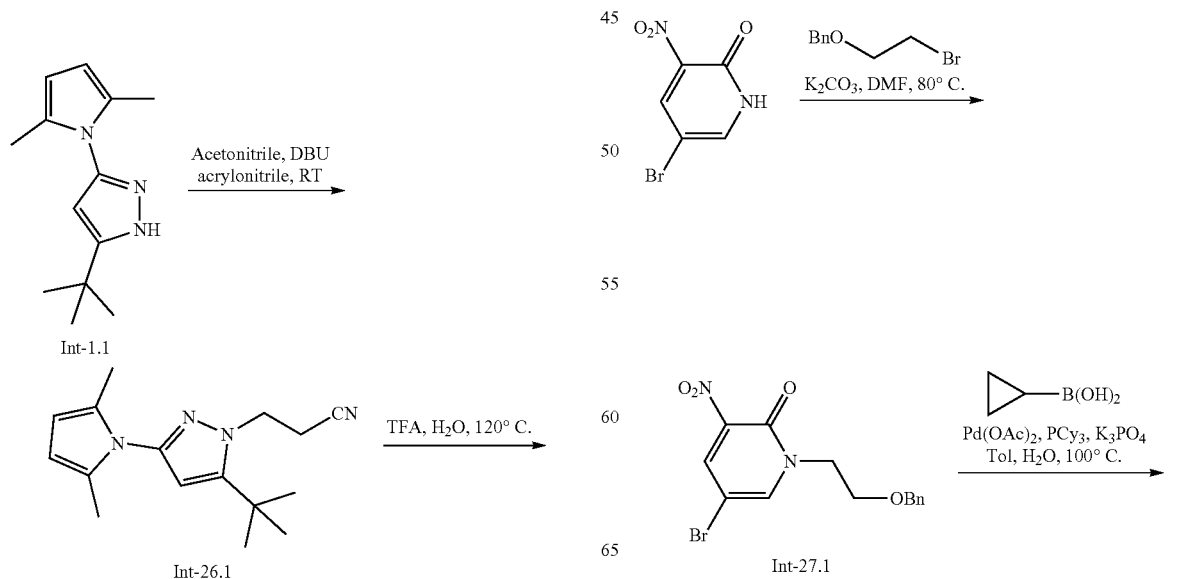

401

-continued

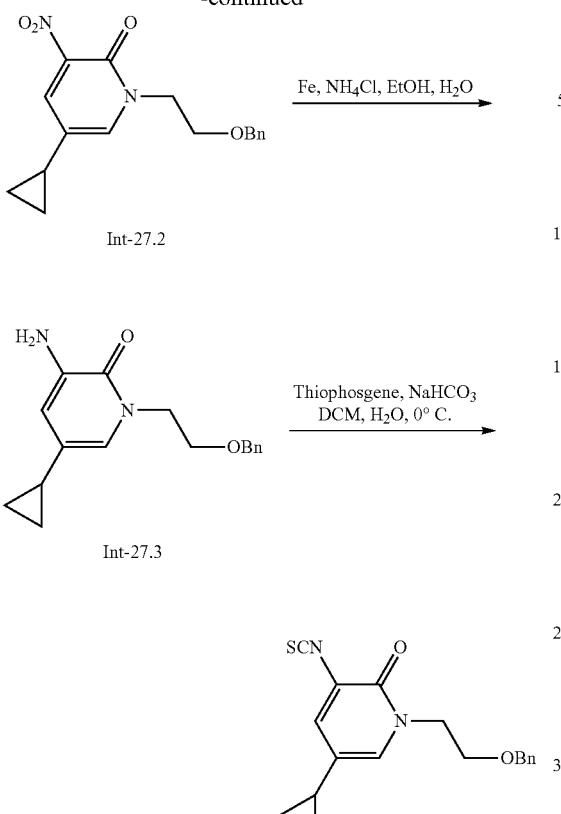

Synthesis of compound Int-27.1. Compound Int-27.1 was prepared from 5-bromo-3-nitropyridin-2(1H)-one, following the procedure described in the synthesis of Int-24.1. The product was purified by flash column chromatography on silica gel (CombiFlash®, 17% ethyl acetate in hexane). MS (ES): m/z 354.2 [M+H]+.

Synthesis of compound Int-27.2. Compound Int-27.2 was prepared from Int-27.1, following the procedure described in the synthesis of Int-23.2. The product was purified by flash column chromatography on silica gel (CombiFlash®, 37% ethyl acetate in hexane). MS (ES): m/z 315.2 [M+H]+.

Synthesis of compound Int-27.3. To a solution of Int-27.2 (0.400 g, 1.27 mmol, 1.0 equiv) in ethanol:water (2:1, 10 mL) was added iron powder (0.355 g, 6.35 mmol, 5.0 equiv) followed by ammonium chloride (0.342 g, 6.35 mmol, 5.0 equiv). The reaction mixture was stirred at 80° C. for 1 h. It was poured into ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-27.3. MS (ES): m/z 285.3 [M+H]+.

Synthesis of compound Int-27. Compound Int-27 was prepared from Int-27.3 following the procedure described in the synthesis of compound Int-1. The product was purified by flash column chromatography on silica gel (CombiFlash®, 2.0% methanol in DCM). MS (ES): m/z 326.3 [M+H]+.

402

Preparation of Intermediate Int-28: 1-((2S,3S)-2-((benzyloxy)methyl)tetrahydrofuran-3-yl)-5-(tert-butyl)-3-isothiocyanato-1H-pyrazole

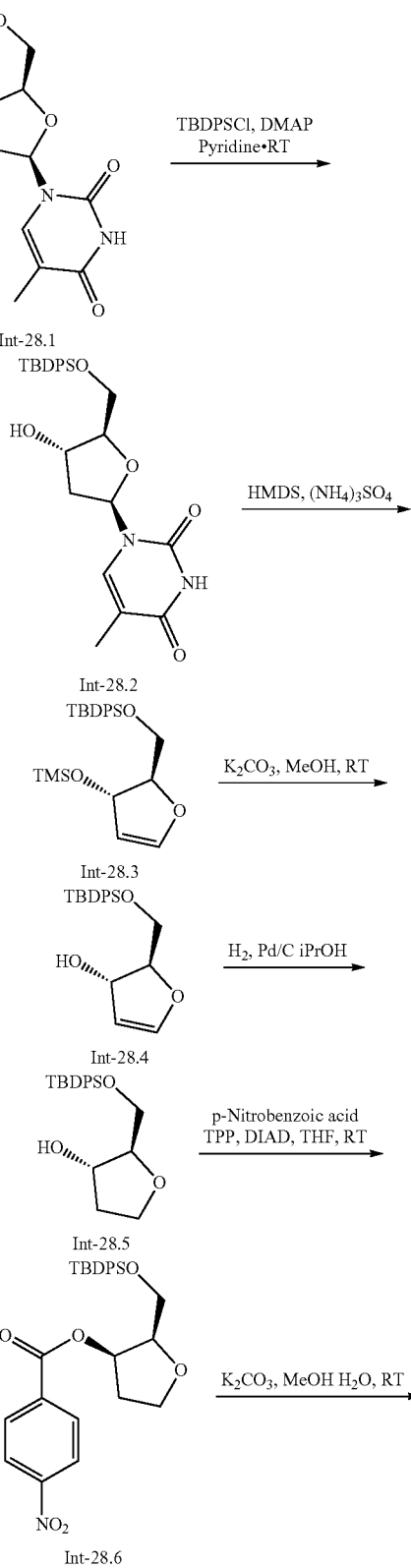

-continued

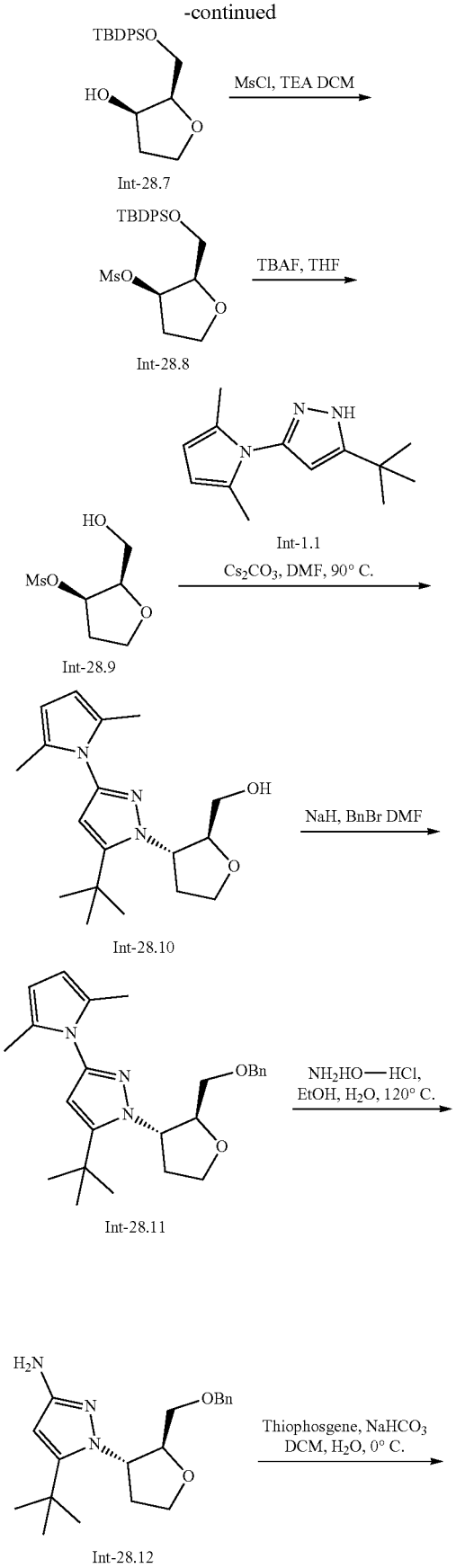

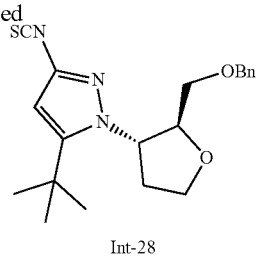

Synthesis of compound Int-28.2. To a solution of Int-28.1 (150 g, 619 mmol, 1.0 equiv) in pyridine (3000 mL) was added 4-dimethylaminopyridine (15.124, 123.8 mmol, 0.2 equiv) followed by tert-butyldiphenylchlorosilane (189.7 mL, 742.8 mmol, 1.2 equiv), and the mixture was stirred at room temperature for 15 h. It was transferred into ice-water, stirred and extracted with ethyl acetate. The organic layer was separated, washed with brine, dried over anhydrous sodium sulfate, filtered and concentrated under reduced pressure. The residue was purified by flash column chromatography on silica gel (CombiFlash®, 2.0% methanol in DCM) to afford Int-28.2. MS (ES): m/z 481.5 [M+H]$^+$.

Synthesis of compound Int-28.3. To a solution of Int-28.2 (140 g, 291 mmol, 1.0 equiv) in bis(trimethylsilyl)amine (2100 mL) was added ammonium sulfate (76.8 g, 582 mmol, 2.0 equiv), and the reaction mixture was heated to reflux for 3 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford Int-28.3. $^1$H NMR (CDCl$_3$, 400 MHz): δ 7.71-7.69 (m, 4H), 7.52-7.42 (m, 6H), 6.42-6.39 (m, 1H), 4.51-4.49 (d, 1H), 4.01-3.98 (m, 2H), 3.83-3.81 (m, 1H), 2.35-2.30 (m, 1H), 1.10 (s, 9H), 0.14 (s, 9H).

Synthesis of compound Int-28.4. To a solution of Int-28.3 (90 g, 210 mmol, 1.0 equiv) in methanol (900 mL) was added potassium carbonate (57.9 g, 420 mmol, 2.0 equiv) and stirred at room temperature for 3 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 18% ethyl acetate in hexane) to afford Int-28.4. $^1$H NMR (CDCl$_3$, 400 MHz): δ 7.70-7.68 (m, 4H), 7.47-7.38 (m, 6H), 6.57-6.56 (m, 1H), 5.19-5.17 (m, 1H), 4.92-4.89 (m, 1H), 4.42-4.39 (m, 1H), 3.80-3.76 (m, 1H), 3.68-3.64 (m, 1H), 1.53-1.51 (d, 1H), 1.07 (s, 9H).

Synthesis of compound Int-28.5. A mixture of palladium on charcoal (10 g) and Int-28.4 (36 g, 101 mmol, 1.0 equiv) in isopropyl alcohol (350 mL) was stirred under hydrogen (1 atm) for 16 h at room temperature. It was filtered through a pad of Celite® and washed with ethyl acetate. The filtrate was concentrated under reduced pressure. The residue was purified by flash column chromatography on silica gel (CombiFlash®, 20% ethyl acetate in hexane) to afford Int-28.5. $^1$H NMR (CDCl$_3$, 400 MHz): δ 7.70-7.67 (m, 4H), 7.47-7.38 (m, 6H), 4.45-4.43 (m, 1H), 4.00-3.97 (m, 2H), 3.86-3.84 (m, 1H), 3.81-3.77 (m, 1H), 3.63-3.58 (m, 1H), 2.20-2.13 (m, 1H), 1.95-1.89 (m, 1H), 1.75-7.74 (d, 1H), 1.08 (s, 9H).

Synthesis of compound Int-28.6. To a solution of compound Int-28.5 (25 g, 70.12 mmol, 1.0 equiv) in THF (250 mL) was added 4-nitrobenzoic acid (35.13 g, 210.36 mmol, 3.0 equiv) followed by triphenyl phosphine (55.11 g, 210.36 mmol, 3.0 equiv), and the reaction mixture was cooled to 0° C. To the mixture was added diisopropylazodicarboxylate (42.49 g, 210.36 mmol, 3.0 equiv) and it was stirred at room temperature for 4 h. It poured into ice-water and extracted with DCM. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-28.6. $^1$H NMR (CDCl$_3$, 400 MHz): δ 8.27-8.25 (d, J=8.8 Hz, 2H), 8.11-8.09 (d, J=8.8 Hz, 2H), 7.65-7.63 (m, 2H), 7.56-7.54 (d, J=6.8 Hz, 2H), 7.44-7.35 (m, 4H), 7.30-7.23 (m, 2H), 5.80-5.78 (m, 1H), 4.20-4.16 (m, 1H), 4.14-4.10 (m, 1H), 4.02-3.91 (m, 3H), 2.49-2.44 (m, 1H), 2.23-2.17 (m, 1H), 1.09 (s, 9H).

Synthesis of compound Int-28.7. To a solution of Int-28.6 (16 g, 31.64 mmol, 1.0 equiv) in methanol (320 mL) and water (160 mL) was added potassium carbonate (13.09 g, 94.92 mmol, 3.0 equiv), and the mixture was stirred at room temperature for 5 h. It was transferred into water and extracted with ethyl acetate. The combined organic layers were washed with brine, dried over anhydrous sodium sulfate, filtered and concentrated under reduced pressure to afford Int-28.7. $^1$H NMR (CDCl$_3$, 400 MHz): δ 7.72-7.68 (m, 4H), 7.47-7.40 (m, 6H), 4.60-4.57 (m, 1H), 4.12-4.03 (m, 1H), 4.00-3.96 (m, 2H), 3.89-3.84 (m, 2H), 2.20-2.11 (m, 1H), 2.07-2.00 (m, 1H), 1.28 (bs, 1H), 1.08 (s, 9H).

Synthesis of compound Int-28.8. To a solution of Int-28.7 (5.7 g, 15.99 mmol, 1.0 equiv) and triethylamine (6.7 mL, 47.97 mmol, 3.0 equiv) in DCM (50 mL) at 0° C. was added methanesulfonyl chloride (2.5 mL, 31.98 mmol, 2.0 equiv). The reaction mixture was stirred at 0° C. for 30 min. It was poured into ice-water, stirred and extracted with DCM. The combined organic layers were washed with brine, dried over anhydrous sodium sulfate, filtered and concentrated under reduced pressure to afford Int-28.8. $^1$H NMR (CDCl$_3$, 400 MHz): δ 7.71-7.68 (m, 4H), 7.49-7.41 (m, 6H), 5.36-5.34 (m, 1H), 4.12-4.06 (m, 1H), 4.02-3.91 (m, 4H), 3.18 (bs, 1H), 2.97 (s, 3H), 2.47-2.42 (m, 1H), 2.37-2.32 (m, 1H), 1.11 (s, 9H).

Synthesis of compound Int-28.9. To a solution of Int-28.8 (5.4 g, 12.42 mmol, 1.0 equiv) in THF (50 mL), was added tetrabutylammonium fluoride (1 M in THF, 18.6 mL, 18.63 mmol, 1.5 equiv) at 0° C. and stirred at room temperature for 30 min. It was transferred into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.7% methanol in DCM) to afford Int-28.9. $^1$H NMR (CDCl$_3$, 400 MHz): δ 5.39-5.36 (m, 1H), 4.15-4.03 (m, 1H), 4.02-3.83 (m, 4H), 3.13 (s, 3H), 2.44-2.33 (m, 2H).

Synthesis of compound Int-28.10 and Int-28.11. To a solution of Int-1.1 (1.1 g, 5.06 mmol, 1.0 equiv) and Int-28.9 (1.5 g, 7.59 mmol, 1.5 equiv) in DMF (15 mL) was added cesium carbonate (8.2 g, 25.3 mmol, 5.0 equiv). The reaction mixture was stirred at 80-90° C. for 12 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford Int-28.10. MS (ES): m/z 318.4 [M+H]$^+$.

Synthesis of compound Int-28.11. To a solution of Int-28.10 (0.380 g, 1.2 mmol, 1.0 equiv) in DMF (4 mL) was added sodium hydride (0.072 g, 1.8 mmol, 1.5 equiv) at 0° C. and stirred for 10 min. To the mixture was added benzyl bromide (0.246 g, 1.44 mmol, 1.2 equiv). The reaction mixture was stirred at room temperature for 30 min. It was transferred into ice, stirred and extracted with ethyl acetate. The combined organic layers were washed with brine, dried over anhydrous sodium sulfate, filtered and concentrated under reduced pressure to afford Int-28.11. MS (ES): m/z 408.5 [M+H]$^+$.

Synthesis of compound Int-28.12. Compound Int-28.12 was prepared from Int-28.11, following the procedure described in the synthesis of Int-1.4. The product was purified by flash column chromatography on silica gel (CombiFlash®, 2.0% methanol in DCM). MS (ES): m/z 330.4 [M+H]$^+$.

Synthesis of compound Int-28. Compound Int-28 was prepared from Int-28.12, following the procedure described in the synthesis of Int-1. The product was used without purification. MS (ES): m/z 372.5 [M+H]$^+$.

Preparation of Intermediate Int-29: 5-cyclopropyl-3-isothiocyanato-1-(tetrahydro-2H-pyran-4-yl)pyridin-2(1H)-one

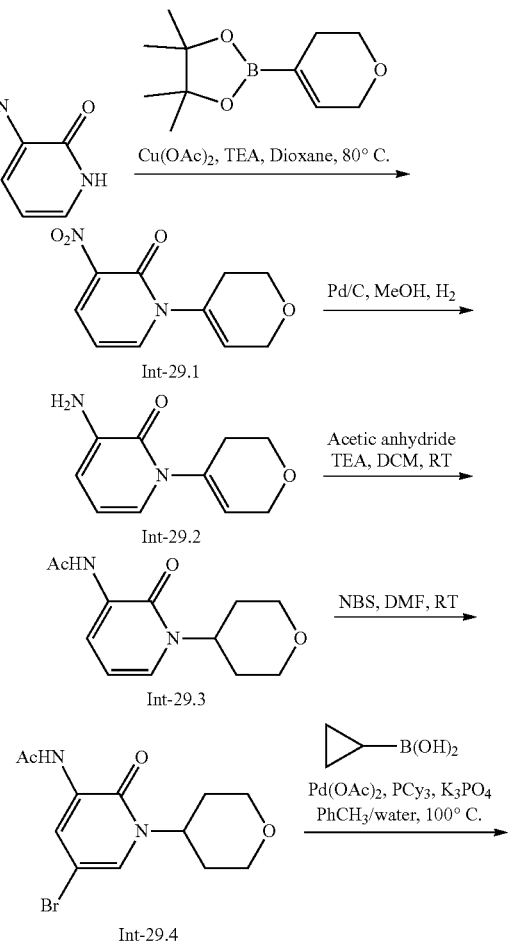

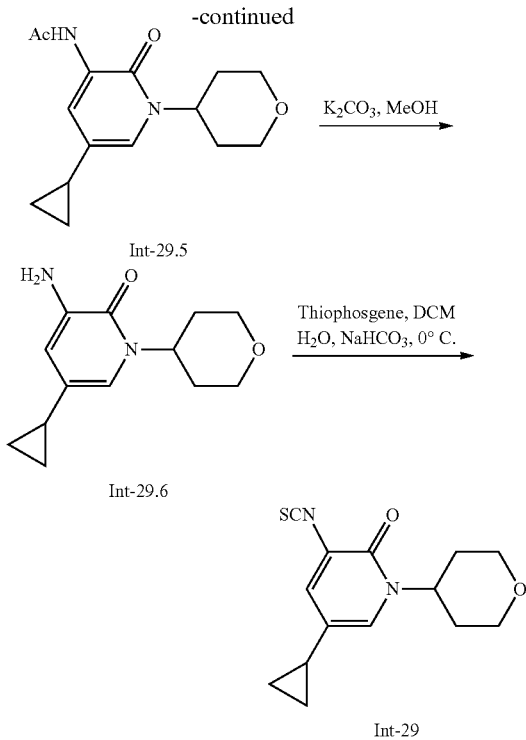

Synthesis of compound Int-29.1. To a solution of 3-nitropyridin-2(1H)-one (3 g, 14.28 mmol, 1.0 equiv) and 2-(3,6-dihydro-2H-pyran-4-yl)-4,4,5,5-tetramethyl-1,3,2-dioxaborolane (2.4 g, 17.14 mmol, 1.2 equiv) in dioxane (30 mL) was added copper acetate (2.60 g, 14.28 mmol, 1.0 equiv) and triethylamine (5.0 mL, 35.7 mmol, 2.5 equiv) under nitrogen. The reaction was stirred at 80° C. for 5 h. It was transferred into ice-water and extracted with ethyl acetate. The combined organic layers were dried over anhydrous sodium sulfate, filtered and concentrated under reduced pressure. The residue was purified by flash column chromatography on silica gel (CombiFlash®, 10% ethyl acetate in hexane) to afford Int-29.1. MS (ES): m/z 222.20 [M+H]$^+$.

Synthesis of compound Int-29.2. To a mixture of Int-29.1 (1.2 g, 5.40 mmol, 1.0 equiv) and 10% palladium on charcoal (0.5 g) in methanol (15 mL) was stirred under hydrogen (1 atm) for 3 h at room temperature. It was filtered through a pad of Celite® and rinsed with methanol. The filtrate was concentrated under reduced pressure. The residue was purified by flash column chromatography on silica gel (CombiFlash®, 1.8% methanol in DCM) to afford Int-29.2. MS (ES): m/z 195.23 [M+H]$^+$.

Synthesis of compound Int-29.3. To a solution of Int-29.2 (0.500 g, 2.57 mmol, 1.0 equiv) and triethylamine (1.07 mL, 7.71 mmol, 3.0 equiv) in DCM (5 mL) at 0° C. was added acetic anhydride (0.51 mL, 5.14 mmol, 2.0 equiv) dropwise. The reaction mixture was stirred at room temperature for 2 h. It was poured into ice-water, stirred and extracted with DCM. The combined organic layers were washed with brine, dried over anhydrous sodium sulfate, filtered and concentrated under reduced pressure. The residue was purified by flash column chromatography on silica gel (CombiFlash®, 1.4% methanol in DCM) to afford Int-29.3. MS (ES): m/z 237.3 [M+H]$^+$.

Synthesis of compound Int-29.4. To a solution of Int-29.3 (0.4 g, 1.69 mmol, 1.0 equiv) in DMF (5 mL) was added NBS (0.448 g, 2.53 mmol, 1.5 equiv) and stirred at room temperature for 1 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 80% ethyl acetate in hexane) to afford Int-29.4. MS (ES): m/z 316.2 [M+H]$^+$.

Synthesis of compound Int-29.5. Compound Int-29.5 was prepared from Int-29.4, following the procedure described in the synthesis of Int-27.2. The product was purified by flash column chromatography on silica gel (CombiFlash®, 1.4% methanol in DCM). MS (ES): m/z 277.3 [M+H]$^+$.

Synthesis of compound Int-29.6. To a solution of compound Int-29.5 (0.185 g, 0.669 mmol, 1.0 equiv) in methanol (5 mL) was added potassium carbonate (1.846 g, 13.38 mmol, 20.0 equiv). The reaction mixture was heated to reflux for 16 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in DCM) to afford Int-29.6. MS (ES): m/z 235.3 [M+H]$^+$.

Synthesis of compound Int-29. Compound Int-29 was prepared from Int-29.6, following the procedure described in the synthesis of Int-1. The product was used without purification. MS (ES): m/z 277.4 [M+H]$^+$.

Preparation of Intermediate Int-30: cis-5-Cyclopropyl-1-((3-hydroxycyclobutyl)-3-isothiocyanatopyridin-2(1H)-one

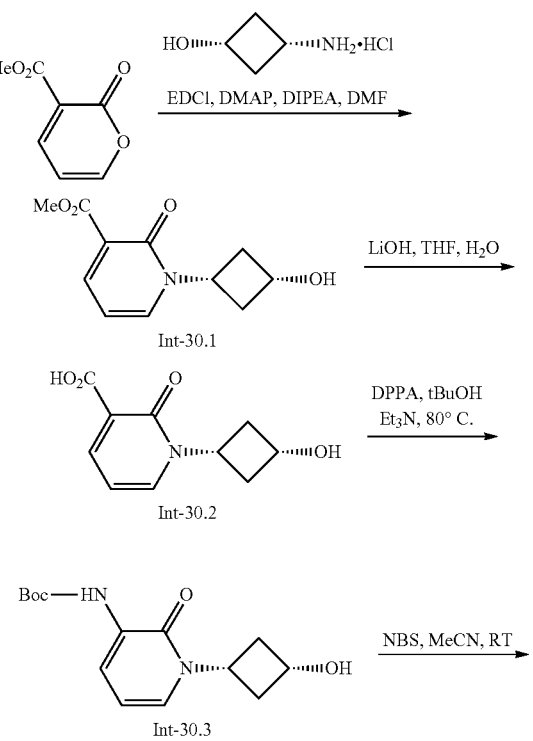

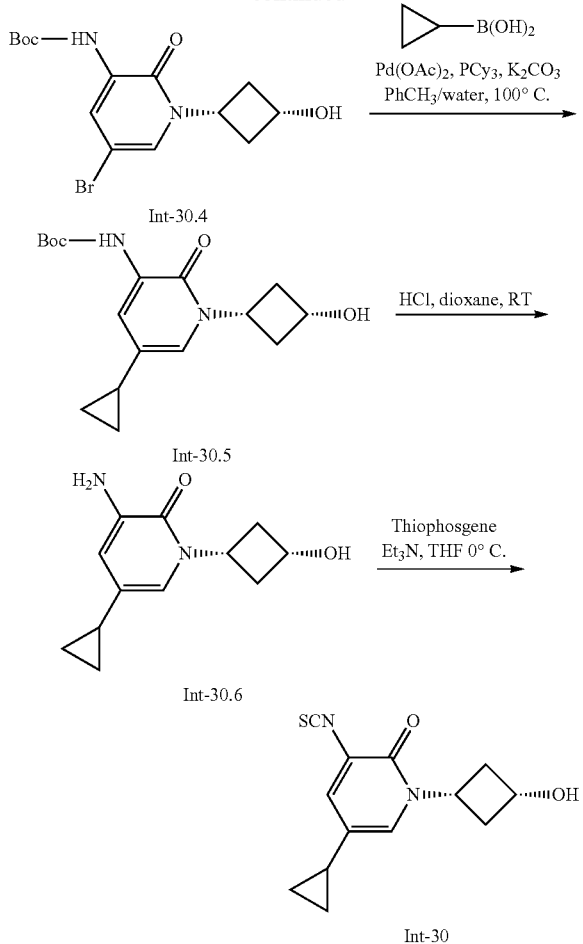

Synthesis of compound Int-30.1. To a cooled solution of methyl 2-oxo-2H-pyran-3-carboxylate (5.0 g, 32.44 mmol, 1.0 equiv) in DMF (50 mL) was added cis-3-aminocyclobutan-1-ol hydrochloride (5.21 g, 42.17 mmol, 1.3 equiv), followed by diisopropylethylamine (11.1 mL, 64.88 mmol, 2.0 equiv). The reaction mixture was stirred at 0° C. for 2 h. N-Ethyl-N-(3-dimethylaminopropyl)carbodiimide hydrochloride (8.7 g, 45.36 mmol, 1.4 equiv) and 4-dimethylaminopyridine (0.989 g, 8.11 mmol, 0.25 equiv) were added. The reaction mixture was stirred at room temperature for 16 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-30.1. MS (ES): m/z 224.09 [M+H]$^+$.

Synthesis of compound Int-30.2. To a solution of Int-30.1 (1.3 g, 5.82 mmol, 1.0 equiv), in THF:water (15 mL, 2:1) was added lithium hydroxide (1.22 g, 29.1 mmol, 5.0 equiv), and the mixture was stirred at room temperature for 24 h. It was concentrated under reduced pressure. To the residue was added water, and the mixture was acidified with 1 N hydrochloric acid to adjust pH-6-6.5 at 10° C. The product was extracted with 10% methanol in DCM. The combined organic layers were washed with brine, dried over anhydrous sodium sulfate, filtered and concentrated under reduced pressure to afford Int-30.2. MS (ES): m/z 210.2 [M+H]$^+$.

Synthesis of compound Int-30.3. A solution of Int-30.2 (0.8 g, 3.82 mmol, 1.0 equiv), triethylamine (0.91 mL, 6.49 mmol, 1.7 equiv) and diphenylphosphoryl azide (1.36 g, 4.96 mmol, 1.3 equiv) in tert-butanol (15 mL) under nitrogen was stirred at 80° C. for 16 h. It cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in DCM) to afford Int-30.3. MS (ES): m/z 281.3 [M+H]$^+$.

Synthesis of compound Int-30.4. To a cooled solution of Int-30.3 (0.4 g, 1.43 mmol, 1.0 equiv) in acetonitrile (10 mL) at 0° C. was added NBS (0.354 g, 2.00 mmol, 1.4 equiv) in portions. The reaction mixture was stirred at 0° C. for 15 min. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-30.4. MS (ES): m/z 360.2 [M+H]$^+$.

Synthesis of compound Int-30.5. Compound Int-24.2 was prepared from Int-24.1, following the procedure described in the synthesis of Int-23.2. The product was purified by flash column chromatography on silica gel (CombiFlash®, 70% ethyl acetate in hexane). MS (ES): m/z 321.4 [M+H]$^+$.

Synthesis of compound Int-30.6. To a cooled solution of Int-30.5 (0.059 g, 0.184 mmol, 1 equiv) in dioxane (2 mL) was added 4 N hydrochloric acid in dioxane (1 mL) dropwise at 0° C. The reaction mixture was stirred at room temperature for 30 min. It was transferred into saturated aqueous solution of sodium bicarbonate and extracted with DCM. The combined organic layers were washed with brine, dried over anhydrous sodium sulfate, filtered and concentrated under reduced pressure to afford Int-30.6. MS (ES): m/z 221.3 [M+H]$^+$.

Synthesis of compound Int-30. Compound Int-30 was prepared from Int-30.6, following the procedure described in the synthesis of Int-1. The product was used without purification. MS (ES): m/z 263.3 [M+H]$^+$.

Preparation of Intermediate (±)-Int-31. (1)-5-cyclopropyl-3-isothiocyanato-1-(tetrahydro-2H-pyran-3-yl)pyridin-2(1H)-one

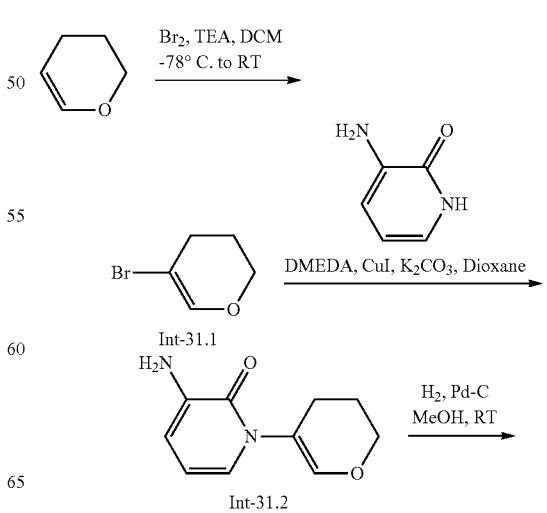

-continued

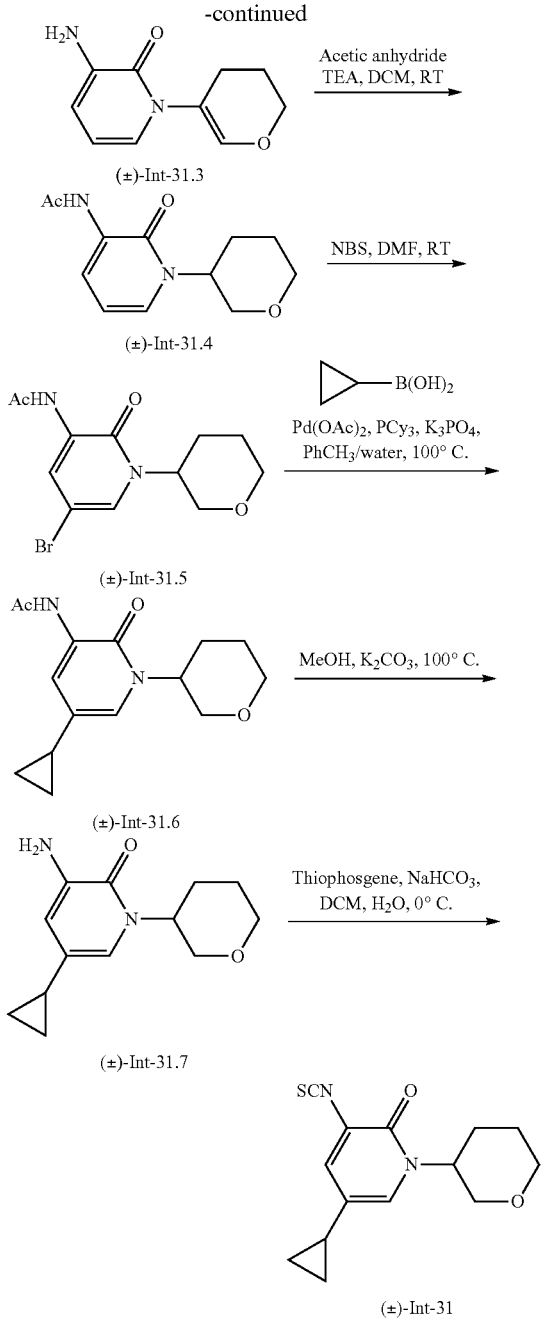

Synthesis of compound Int-31.1. To a solution of 3,4-dihydro-2H-pyran (20 g, 238 mmol, 1.0 equiv) in DCM (200 mL) was added bromine (12.2 mL, 238 mmol, 1.0 equiv) in DCM (100 mL) at −78° C. dropwise. The reaction mixture was stirred at −78° C. for 2 h, and it was allowed to warm to room temperature stirring for 16 h. Triethylamine (66 mL, 476 mmol, 2.0 equiv) in DCM (100 mL) was added dropwise at room temperature and then stirred for 5 h. The reaction mixture was concentrated under reduced pressure to afford a residue, to which diethyl ether was added and the solid was removed by filtration. The filtrate was concentrated under reduced pressure to afford a residue which was purified by vacuum distillation (80° C., 0.02 mmHg) to afford Int-31.1. $^1$H NMR (400 MHz, CDCl$_3$): 6.68 (s, 1H), 4.02-4.00 (t, J=4 Hz, 2H), 2.45-2.42 (m, 2H), 2.06-2.00 (m, 2H).

Synthesis of compound Int-31.2. A mixture of Int-31.1 (8 g, 49.08 mmol, 1.0 equiv), 3-aminopyridin-2(1H)-one (6.48 g, 58.89 mmol, 1.2 equiv) and potassium carbonate (13.6 g, 98.16 mmol, 2.0 equiv) in 1,4-dioxane (100 mL) was degassed by bubbling through a stream of argon for 15 min. Copper iodide (1.4 g, 7.40 mmol, 0.15 equiv) and 1,2-dimethylethylenediamine (1.60 mL, 14.72 mmol, 0.30 equiv) were added. The reaction mixture was degassed for 5 min and stirred at 110° C. for 12 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (Combi-Flash®, 1.2% methanol in DCM) to afford Int-31.2. MS (ES): m/z 193.09 [M+H]$^+$.

Synthesis of compound (±)-Int-31.3. A mixture of Int-31.2 (8 g, 41.62 mmol, 1.0 equiv) and palladium on charcoal (4 g) in methanol (100 mL) was stirred under hydrogen (1 atm) for 16 h at room temperature. It was filtered through a pad of Celite® and rinsed with methanol. The filtrate was concentrated under reduced pressure. The residue was purified by trituration with n-pentane to afford (±)-Int-31.3. MS (ES): m/z 195.11 [M+H]$^+$.

Synthesis of compound (±)-Int-31.4. To a solution of (±)-Int-31.3 (2 g, 10.30 mmol, 1.0 equiv) in DCM (20 mL) at 0° C. was added triethylamine (4.33 mL, 30.9 mmol, 3.0 equiv) and acetic anhydride (1.55 mL, 16.49 mmol, 1.6 equiv). The reaction mixture was stirred at room temperature for 2 h. It was transferred into water and extracted with DCM. The combined organic layers were dried over anhydrous sodium sulfate, filtered and concentrated under reduced pressure. The residue was purified by flash column chromatography on silica gel (CombiFlash®, 0-5% methanol in DCM) to afford (±)-Int-31.4. MS (ES): m/z 237.12 [M+H]$^+$.

Synthesis of compound (±)-Int-31.5. To a solution of (±)-Int-31.4 (0.9 g, 3.81 mmol, 1.0 equiv) in DMF (10 mL) was added NBS (1.017 g, 5.71 mmol, 1.5 equiv), and the mixture was stirred at room temperature for 1 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 60% ethyl acetate in hexane) to afford (±)-Int-31.5. MS (ES): m/z 316.2 [M+H]$^+$.

Synthesis of compound (±)-Int-31.6. Compound (±)-Int-31.6 was prepared from (±)-Int-31.5, following the procedure described in the synthesis of Int-23.2. The product was purified by flash column chromatography on silica gel (CombiFlash®, 100% ethyl acetate). MS (ES): m/z 277.3 [M+H]$^+$.

Synthesis of compound (±)-Int-31.7. Compound (±)-Int-31.7 was prepared from (±)-Int-31.6, following the procedure described in the synthesis of Int-29.6. The product was purified by flash column chromatography on silica gel (CombiFlash®, 2.0% methanol in DCM). MS (ES): m/z 235.3 [M+H]$^+$.

Synthesis of compound (±)-Int-31. Compound (±)-Int-31 was prepared from (f)-Int-31.7, following the procedure described in the synthesis of Int-1. The product was used without purification. MS (ES): m/z 277.4 [M+H]$^+$.

413
Preparation of Intermediate Int-32. cis-3-Amino-1-(−3-(benzyloxy)cyclobutyl)-5-cyclopropylpyridin-2(1H)-one

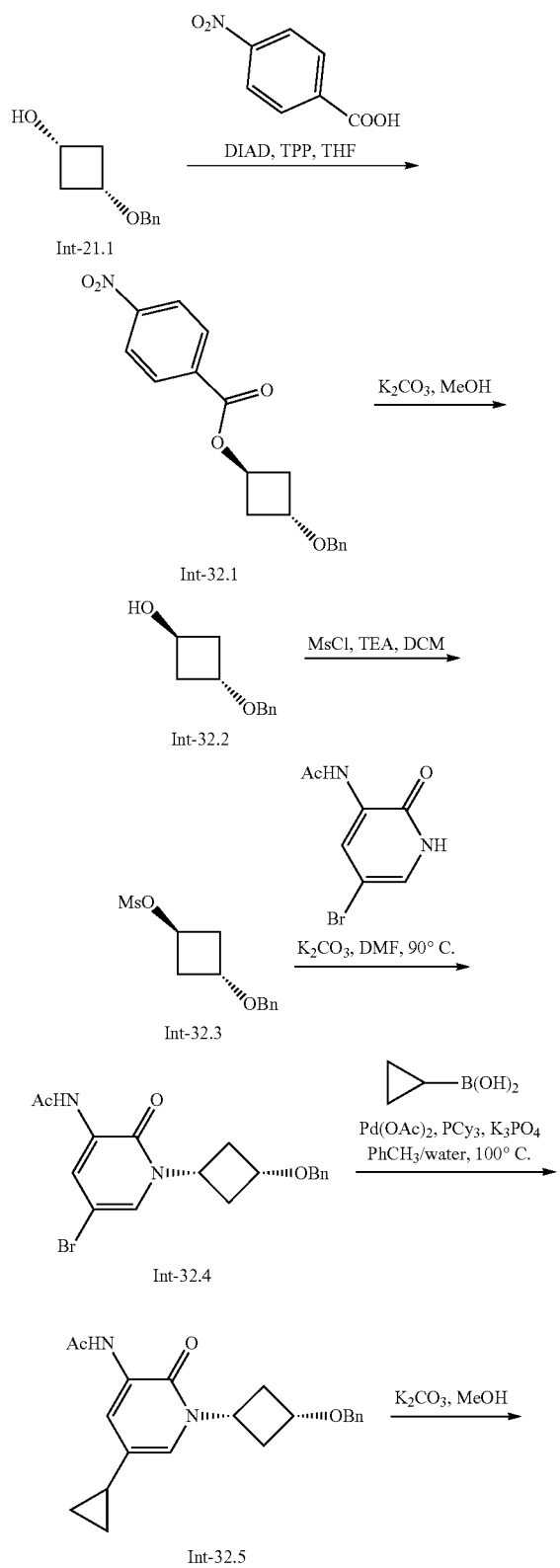

414
-continued

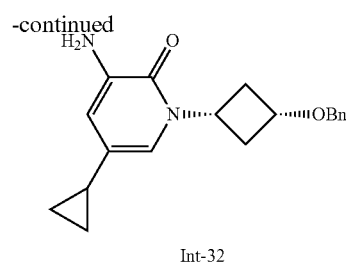

Int-32

Synthesis of compound Int-32.1. To a solution of compound Int-21.1 (8.9 g, 49.94 mmol, 1.0 equiv) in THF (200 mL) was added 4-nitrobenzoic acid (10.01 g, 59.92 mmol, 1.2 equiv) followed by triphenylphosphine (26.16 g, 99.88 mmol, 2.0 equiv) and the reaction mixture was cooled to 0° C. To the mixture was added diisopropylazodicarboxylate (20.17 g, 99.88 mmol, 2.0 equiv). The reaction mixture was stirred at room temperature for 2 h. It was poured into ice-water and extracted with DCM. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-32.1. MS (ES): m/z 328.3 [M+H]$^+$.

Synthesis of compound Int-32.2. A mixture of Int-32.1 (9.2 g, 28.11 mmol, 1.0 equiv) and potassium carbonate (11.63 g, 84.33 mmol, 3.0 equiv) in methanol (100 mL) was stirred at room temperature for 3 h. It was poured into ice-water, stirred and extracted with ethyl acetate. The combined organic layers were washed with brine, dried over anhydrous sodium sulfate, filtered and concentrated under reduced pressure to afford Int-32.2. MS (ES): m/z 179.2 [M+H]$^+$.

Synthesis of compound Int-32.3. To a solution of Int-32.2 (4.2 g, 23.56 mmol, 1.0 equiv) and triethylamine (4.9 mL, 35.34 mmol, 1.5 equiv) in DCM (40 mL) at 0° C. was added methanesulfonyl chloride (2.36 mL, 30.62 mmol, 1.3 equiv). The reaction mixture was stirred at room temperature for 3 h. It was poured into ice-water, stirred and extracted with DCM. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-32.3. MS (ES): m/z 257.3 [M+H]$^+$.

Synthesis of compound Int-32.4. A mixture of Int-32.3 (3.5 g, 15.15 mmol, 1.0 equiv), potassium carbonate (4.18 g, 30.3 mmol, 2.0 equiv) and N-(5-bromo-2-oxo-1,2-dihydropyridin-3-yl)acetamide (3.88 g, 15.15 mmol, 1.0 equiv) in DMF (30 mL) was stirred at 90° C. for 2 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-32.4. MS (ES): m/z 392.2 [M+H]$^+$.

Synthesis of compound Int-32.5. Compound Int-32.5 was prepared from Int-32.4, following the procedure described in the synthesis of Int-23.2. The product was purified by flash column chromatography on silica gel (CombiFlash®, 60% ethyl acetate in hexane). MS (ES): m/z 353.2 [M+H]$^+$.

Synthesis of compound Int-32. Compound Int-32 was prepared from Int-32.5, following the procedure described in the synthesis of Int-29.6. The product was purified by flash column chromatography on silica gel (CombiFlash®, 1.5% methanol in DCM). MS (ES): m/z 311.4 [M+H]$^+$.

Preparation of Intermediate Int-33. trans-3-(benzyloxy)cyclobutyl)-5-cyclopropyl-3-isothiocyanato-pyridin-2(1H)-one

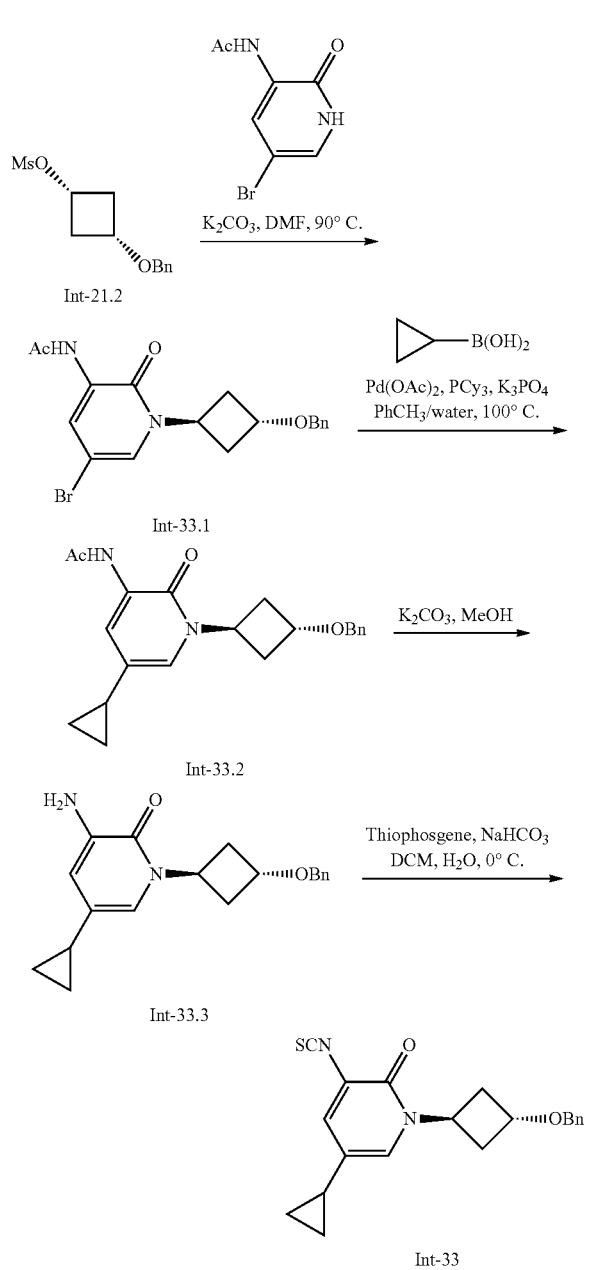

Preparation of Intermediates Int-34 and Int-35: trans-3-(5-cyclopropyl-3-isothiocyanato-2-oxopyridin-1(2H)-yl)cyclobutane-1-carbonitrile and cis-3-(5-cyclopropyl-3-isothiocyanato-2-oxopyridin-1(2H)-yl)cyclobutane-1-carbonitrile

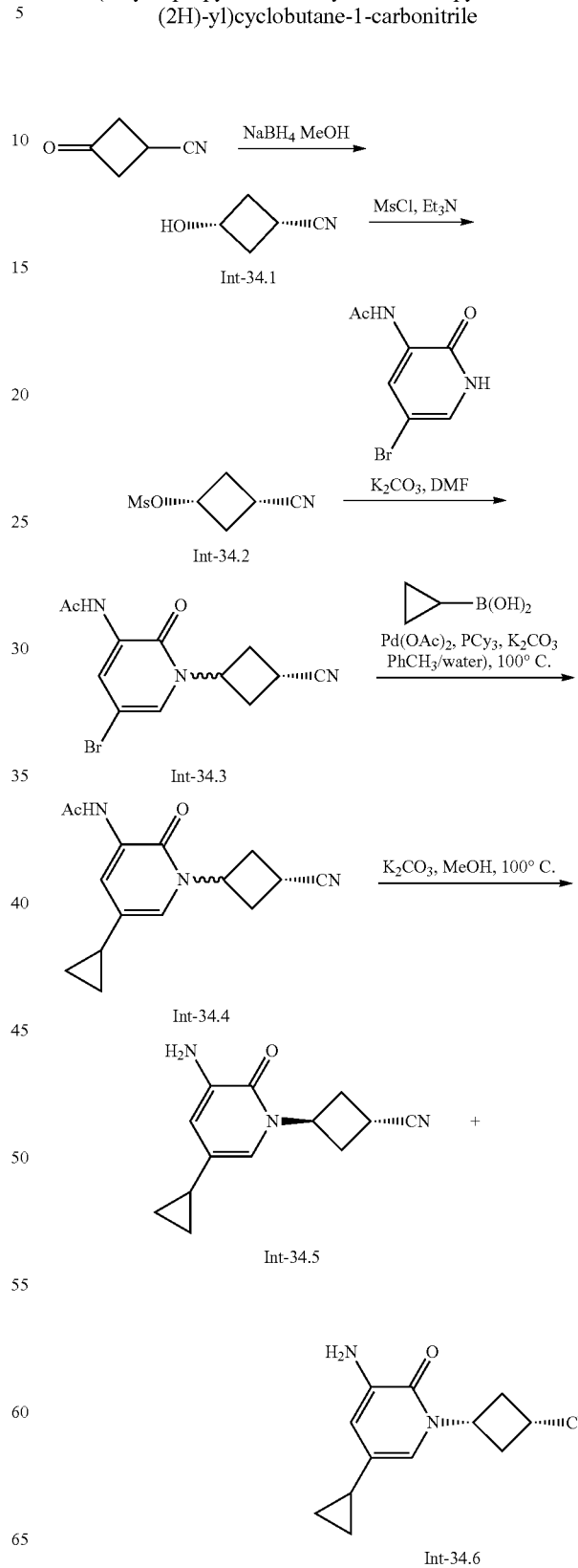

Synthesis of compound Int-33.3. Compound Int-33.3 was prepared from Int-21.2, following the procedures described in the synthesis of Int-29.6.

Synthesis of compound Int-33. Compound Int-33 was prepared from Int-33.3, following the procedure described in the synthesis of Int-1. The product was purified by flash column chromatography on silica gel (CombiFlash®, 1.2% methanol in DCM). MS (ES): m/z 381.3 [M+H]$^+$.

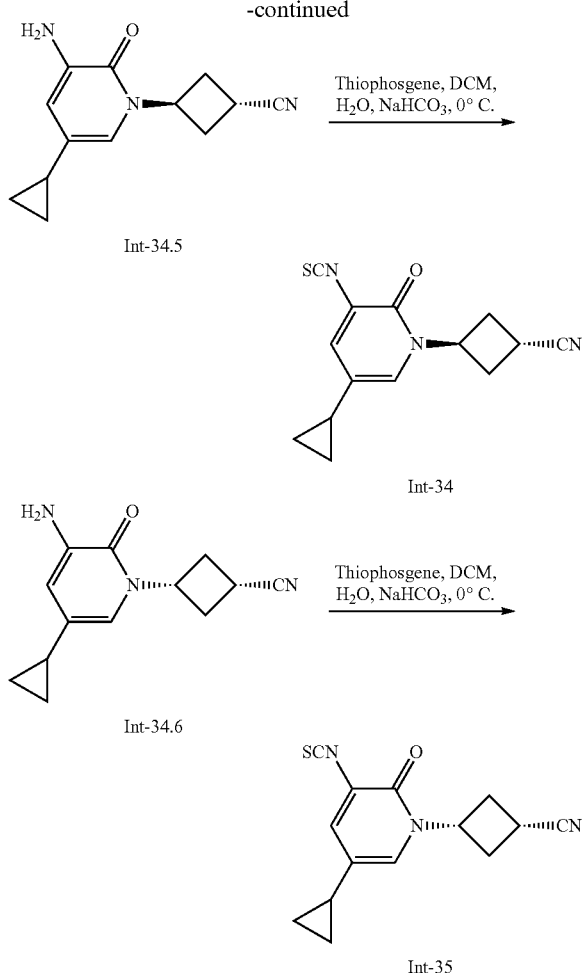

Synthesis of compounds Int-34.5 and Int-34.6. A mixture of Int-34.4 (0.150 g, 0.552 mmol, 1.0 equiv) and potassium carbonate (1.52 g, 11.04 mmol, 20 equiv) in methanol (5 mL) was stirred at 100° C. for 16 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane), followed by SFC to afford Int-34.5, MS (ES): m/z 230.3 [M+H]+ and Int-34.6, MS (ES): m/z 230.3 [M+H]+.

Synthesis of compound Int-34. Compound Int-34 was prepared from Int-34.5, following the procedure described in the synthesis of Int-1. The product was used without purification. MS (ES): m/z 272.3 [M+H]+.

Synthesis of compound Int-35. Compound Int-35 was prepared from Int-34.6, following the procedure described in the synthesis of Int-1. The product was used without purification. MS (ES): m/z 272.3 [M+H]+.

Preparation of Intermediate Int-36: 1-(3-(benzyloxy)-2-methylpropyl)-5-cyclopropyl-3-isothiocyanatopyridin-2(1H)-one

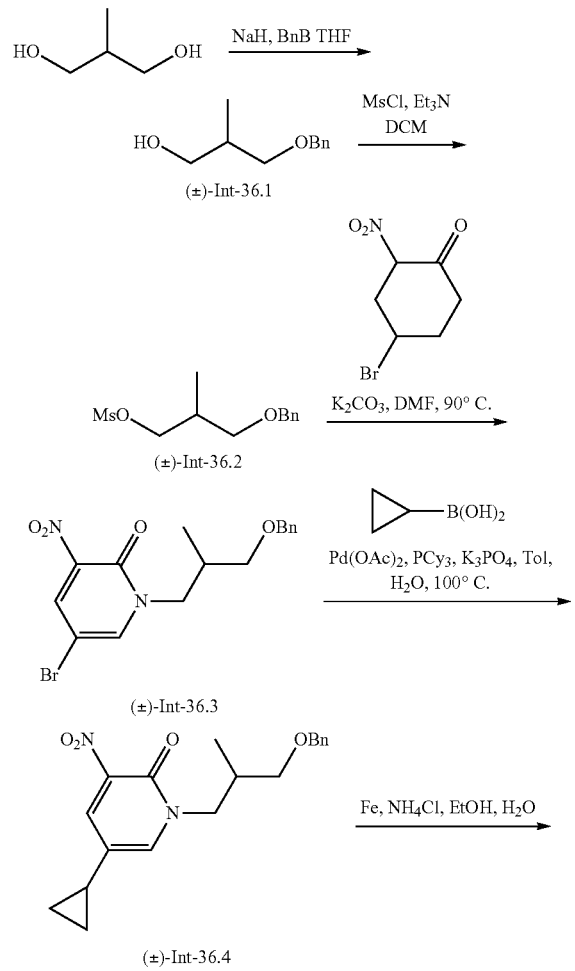

Synthesis of compound Int-34.1. To a solution of 3-oxo-cyclobutane-1-carbonitrile (1.0 g, 10.52 mmol, 1.0 equiv) in methanol (10 mL) was added sodium borohydride (0.778 g, 21.04 mmol, 2.0 equiv) in portions at 0° C. The reaction mixture was stirred at room temperature for 3 h. It was poured into ice-water, stirred and extracted with ethyl acetate. The combined organic layers were washed with brine, dried over anhydrous sodium sulfate, filtered and concentrated under reduced pressure to afford Int-34.1. $^1$H NMR (CDCl$_3$, 400 MHz): 4.35-4.27 (m, 1H), 2.83-2.79 (m, 2H), 2.69-2.58 (m, 1H), 2.41-2.34 (m, 2H), 2.00 (bs, 1H).

Synthesis of compound Int-34.2. Compound Int-34.2 was prepared from Int-34.1, following the procedure described in the synthesis of Int-32.3. The product was purified by flash column chromatography on silica gel (CombiFlash®, 15% ethyl acetate in hexane). $^1$H NMR (CDCl$_3$, 400 MHz): 5.03-4.96 (m, 1H), 3.18-3.12 (m, 1H), 3.07 (s, 3H), 2.98-2.94 (m, 2H), 2.87-2.61 (m, 2H).

Synthesis of compound Int-34.3. Compound Int-34.3 was prepared from Int-34.2, following the procedure described in the synthesis of Int-32.4. The product was purified by flash column chromatography on silica gel (CombiFlash®, 25% ethyl acetate in hexane). MS (ES): m/z 311.2 [M+H]+.

Synthesis of compound Int-34.4. Compound Int-34.4 was prepared from Int-34.3, following the procedure described in the synthesis of Int-23.2. The product was purified by flash column chromatography on silica gel (CombiFlash®, 25% ethyl acetate in hexane). MS (ES): m/z 272.3 [M+H]+.

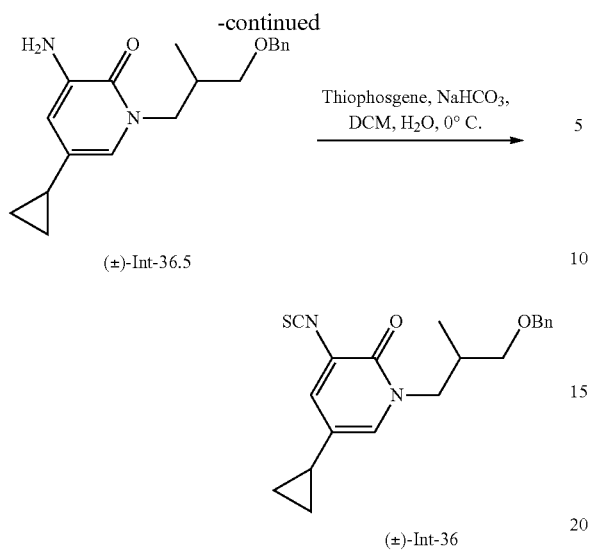

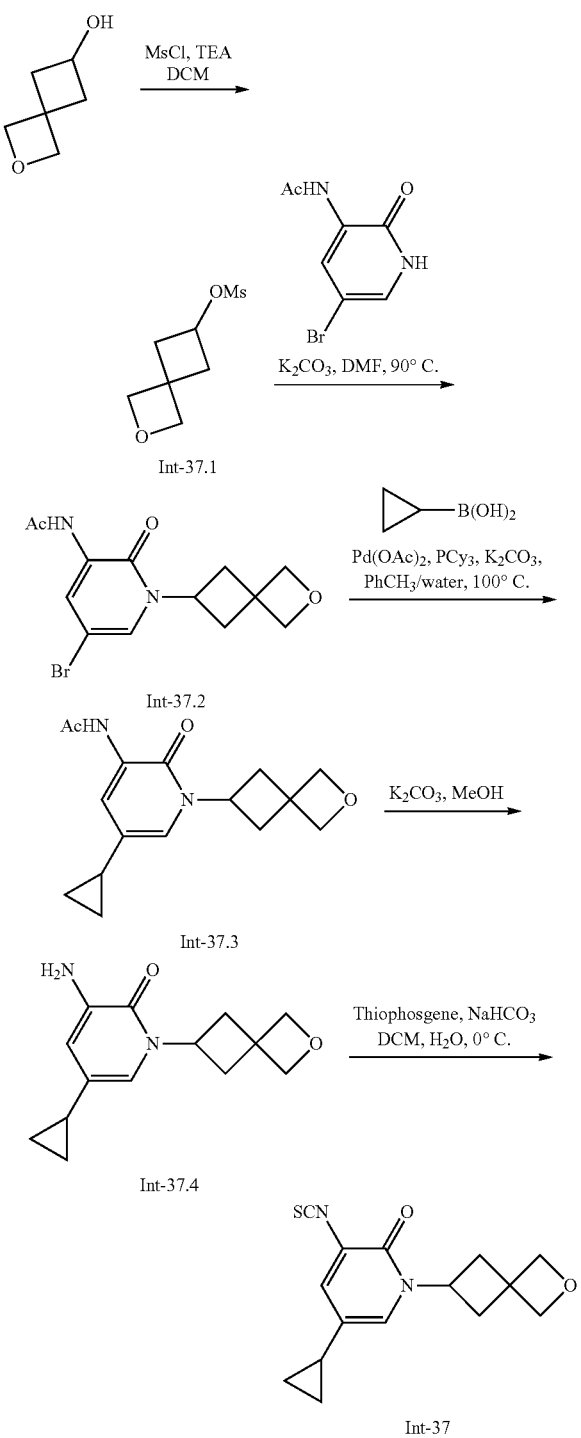

Preparation of Intermediate Int-37: 5-cyclopropyl-3-isothiocyanato-1-(2-oxaspiro[3.3]heptan-6-yl)pyridin-2(1H)-one Synthesis of compound (±)-Int-36.1. To a suspension of sodium hydride (5.32 g, 133.15 mmol, 1.2 equiv) in THF (50 mL) was added a solution of 2-methylpropane-1,3-diol (10 g, 110.96 mmol, 1.0 equiv) in THF (100 mL) and stirred at 50° C. for 2 h. To the mixture was added benzyl bromide (13.2 mL, 110.96 mmol, 1.0 equiv), and the mixture was stirred at 60° C. for 12 h. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford (±)-Int-36.1. MS (ES): m/z 181.2 [M+H]$^+$.

Synthesis of compound (±)-Int-36.2. Compound (±)-Int-36.2 was prepared from (±)-Int-36.1, following the procedure described in the synthesis of Int-32.3. The product was used in the next step without purification.

Synthesis of compound (±)-Int-36.3. Compound (±)-Int-36.3 was prepared from (±)-Int-36.2 and 5-bromo-3-nitropyridin-2(1H)-one following the procedure described in the synthesis of Int-32.4. The product was purified by flash column chromatography on silica gel (CombiFlash®, 25% ethyl acetate in hexane) to afford (±)-Int-36.3. MS (ES): m/z 382.2 [M+H]$^+$.

Synthesis of compound (±)-Int-36.4. Compound (±)-Int-36.4 was prepared from (±)-Int-36.3, following the procedure described in the synthesis of Int-23.2. The product was purified by flash column chromatography on silica gel (CombiFlash®, 40% ethyl acetate in hexane). MS (ES): m/z 343.2 [M+H]$^+$.

Synthesis of compound (±)-Int-36.5. Compound (±)-Int-36.5 was prepared from (±)-Int-36.4, following the procedure described in the synthesis of Int-27.3. The product was used in the next step without purification. MS (ES): m/z 313.4 [M+H]$^+$.

Synthesis of compound (±)-Int-36. Compound (±)-Int-36 was prepared from (f)-Int-36.5, following the procedure described in the synthesis of Int-1. The product was purified by flash column chromatography on silica gel (CombiFlash®, 25% ethyl acetate in hexane). MS (ES): m/z 355.4 [M+H]$^+$.

Synthesis of compound Int-37.1. Compound Int-37.1 was prepared from 2-oxaspiro[3.3]heptan-6-ol, following the procedure described in the synthesis of Int-32.3. The product was used in the next step without purification. MS (ES): m/z 193.3 [M+H]$^+$.

Synthesis of compound Int-37.2. Compound Int-37.2 was prepared from Int-37.1 and N-(5-bromo-2-oxo-1,2-dihydropyridin-3-yl)acetamide, following the procedure described in the synthesis of Int-32.4. The product was purified by flash column chromatography on silica gel (CombiFlash®, 60% ethyl acetate in hexane). MS (ES): m/z 328.2 [M+H]$^+$.

Synthesis of compound Int-37.3. Compound Int-37.3 was prepared from Int-37.2, following the procedure described in the synthesis of Int-23.2. The product was purified by flash column chromatography on silica gel (CombiFlash®, 2% methanol in DCM). MS (ES): m/z 289.1 [M+H]$^+$.

Synthesis of compound Int-37.4. Compound Int-37.4 was prepared following the procedures described in the synthesis of Int-29.6. The product was purified by flash column chromatography on silica gel (CombiFlash®, 2.5% methanol in DCM). MS (ES): m/z 247.2 [M+H]$^+$.

Synthesis of compound Int-37. Compound Int-37 was prepared from Int-37.4, following the procedure described in the synthesis of Int-1. The product was used without purification. MS (ES): m/z: 289.2 [M+H]$^+$.

Preparation of Intermediate Int-38: 5-(tert-butyl)-3-isothiocyanato-1-(oxetan-3-yl)-1H-pyrazole

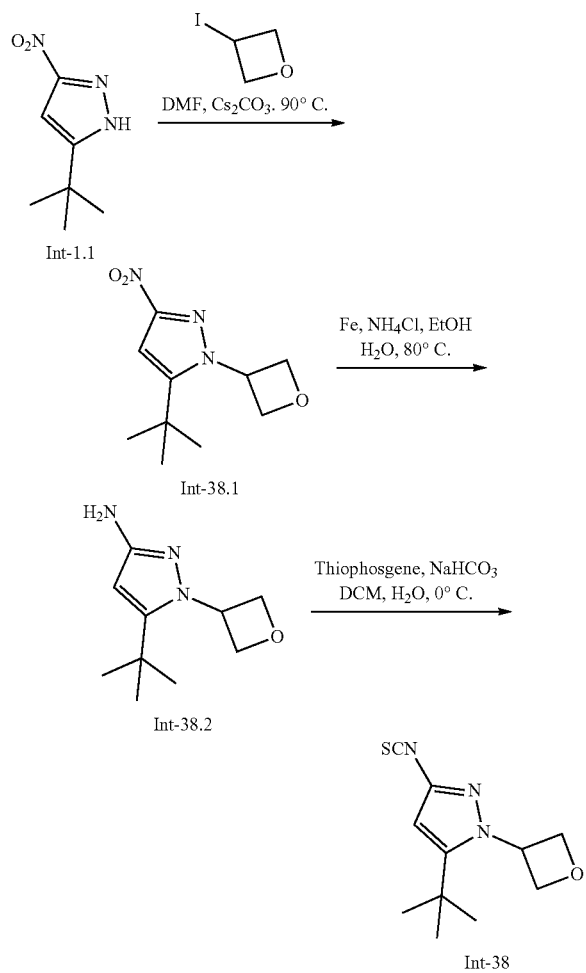

Synthesis of compound Int-38.1. A mixture of compound Int-1.1 (2.0 g, 11.82 mmol, 1.0 equiv), 3-iodooxetane (4.35 g, 23.64 mmol, 2.0 equiv) and cesium carbonate (7.68 g, 23.64 mmol, 2.0 equiv) in DMF (20 mL) was stirred at 90° C. for 48 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford Int-38.1. MS (ES): m/z 226.2 [M+H]$^+$.

Synthesis of compound Int-38.2. To a solution of Int-38.1 (0.360 g, 1.6 mmol, 1.0 equiv) in ethanol:water (2:1, 10 mL) was added iron powder (0.448 g, 8.0 mmol, 5.0 equiv) followed by ammonium chloride (0.432 g, 8.0 mmol, 5.0 equiv). The reaction mixture was stirred at 80° C. for 1 h. It was poured into ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-38.2. MS (ES): m/z 196.2 [M+H]$^+$.

Synthesis of compound Int-38. Compound Int-38 was prepared from Int-38.2, following the procedure described in the synthesis of Int-1. The product was purified by flash column chromatography on silica gel (CombiFlash®, 1.2% methanol in DCM). MS (ES): m/z 238.3 [M+H]$^+$.

Preparation of Intermediate (±)-Int-39: 3-(3-amino-5-cyclopropyl-2-oxopyridin-1(2H)-yl)butanenitrile

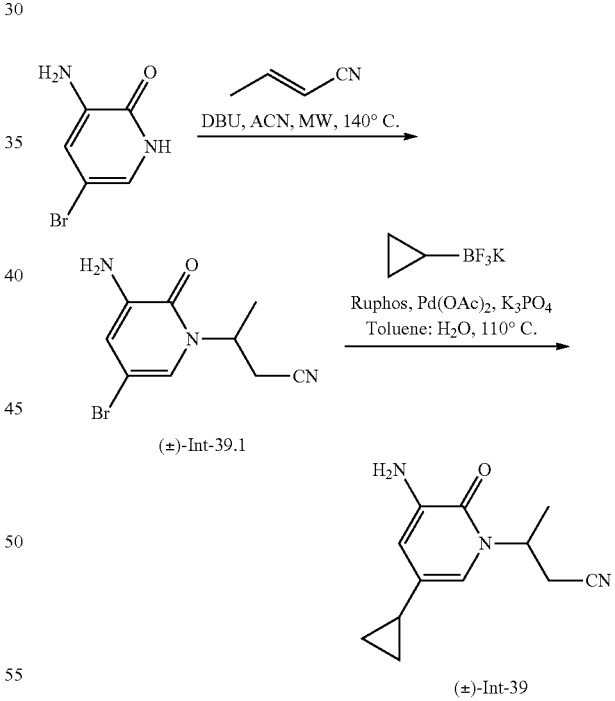

Synthesis of compound (±)-Int-39.1. To a solution of 3-amino-5-bromopyridin-2(1H)-one (1 g, 5.29 mmol, 1.0 equiv) in acetonitrile (10 mL) was added (E)-but-2-enenitrile (2.13 g, 31.74 mmol, 6.0 equiv) followed by addition of 1,8-diazabicyclo[5.4.0]undec-7-ene (0.64 g, 4.23 mmol, 0.8 equiv). The reaction mixture was stirred at 140° C. in MW for 2 h. It transferred into water and extracted with ethyl acetate. The combined organic layers were washed with brine, dried over anhydrous sodium sulfate, filtered and concentrated under reduced pressure. The residue was purified by flash column chromatography on silica gel (Combi-Flash®, 15% ethyl acetate in hexane) to afford (±)-Int-39.1. MS (ES): m/z 257.1 [M+H]⁺.

Synthesis of compound (±)-Int-39. A mixture of (±)-Int-39.1 (0.510 g, 1.99 mmol, 1.0 equiv), potassium cyclopropyltrifluoroborate (0.530 g, 3.58 mmol, 1.8 equiv) and tripotassium phosphate (0.843 g, 3.98 mmol, 2.0 equiv) in toluene (9 mL) and water (1 mL) was degassed by bubbling through a stream of argon for 10 min. Under argon atmosphere was added palladium(II) acetate (0.222 g, 0.995 mmol, 0.5 equiv) and 2-dicyclohexylphosphino-2',6'-diisopropoxybiphenyl (0.278 g, 0.597 mmol, 0.3 equiv), and the mixture again degassed for 5 min. The reaction mixture was stirred at 110° C. for 12 h. It was cooled to room temperature and filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 30-35% ethyl acetate in hexane) to afford (±)-Int-39. MS (ES): m/z 218.2 [M+H]⁺.

Preparation of Intermediate Int-40: 1-((1s,3s)-3-(benzyloxy)cyclobutyl)-3-isothiocyanato-5-(trifluoromethyl)pyridin-2(1H)-one

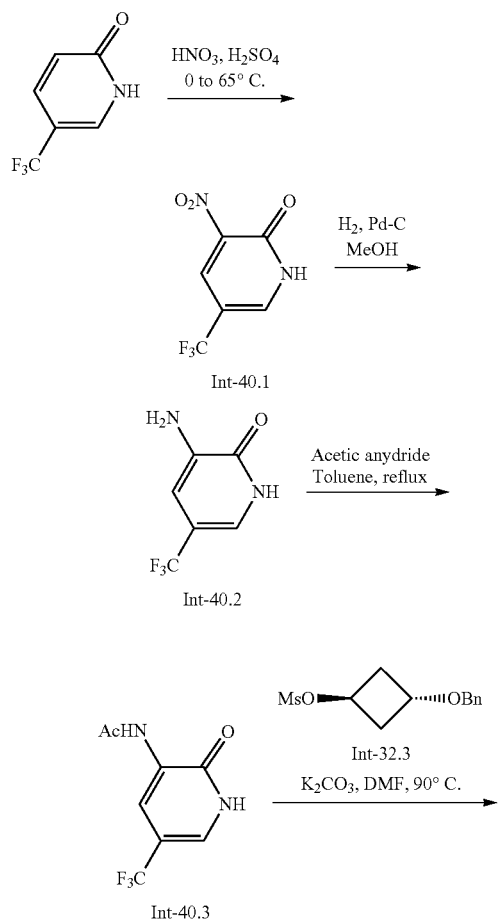

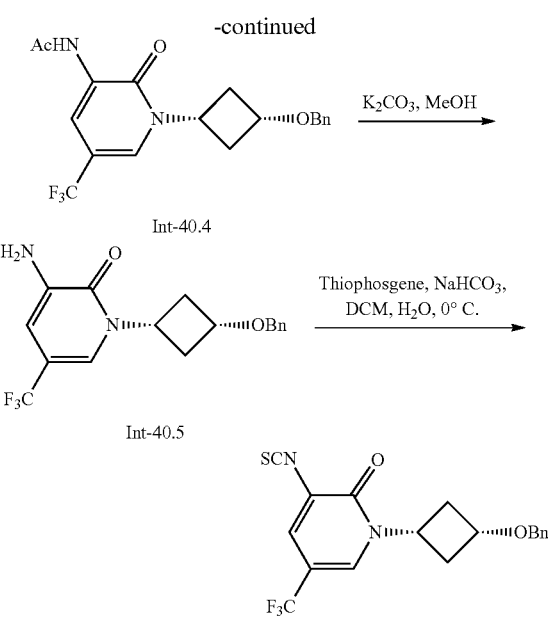

Synthesis of compound Int-40.1. To a solution of 5-(trifluoromethyl)pyridin-2(1H)-one (5.0 g, 30.66 mmol, 1.0 equiv) in concentrated sulfuric acid (25 mL) was added fuming nitric acid (8 mL) at 0° C. The reaction mixture was stirred at 65° C. for 6 h. It was transferred into crushed ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-40.1. MS (ES): m/z 209.10 [M+H]⁺.

Synthesis of compound Int-40.2. A mixture of Int-40.1 (8.0 g, 38.44 mmol, 1.0 equiv) and 10% palladium on carbon (3.0 g) in methanol (30 mL) was stirred under hydrogen (1 atm) for 2 h. It was filtered through a pad of Celite® and rinsed with methanol. The filtrate was concentrated under reduced pressure to afford Int-40.2. MS (ES): m/z 179.1 [M+H]⁺.

Synthesis of compound Int-40.3. A solution of Int-40.2 (6.5 g, 36.49 mmol, 1.0 equiv) and acetic anhydride (17 mL, 182.45 mmol, 5.0 equiv) in toluene (25 mL) was heated to reflux for 2 h. It was concentrated under reduced pressure to afford crude material, which was purified by trituration with diethyl ether to afford Int-40.3. MS (ES): m/z 221.3 [M+H]⁺.

Synthesis of compound Int-40.4. Compound Int-40.4 was prepared from Int-40.3 and Int-32.3, following the procedure described in the synthesis of Int-32.4. The product was purified by flash column chromatography on silica gel (CombiFlash®, 40% ethyl acetate in hexane). MS (ES): m/z 381.3 [M+H]⁺.

Synthesis of compound Int-40.5. Compound Int-40.5 was prepared from Int-40.4, following the procedure described in the synthesis of Int-29.6. The product was purified by flash column chromatography on silica gel (CombiFlash®, 1.5% methanol in DCM). MS (ES): m/z 339.3 [M+H]⁺.

Synthesis of compound Int-40. Compound Int-40 was prepared from Int-40.5, following the procedure described in the synthesis of Int-1. The product was used without purification.

Preparation of Intermediate Int-41: 3-isothiocyanato-1-(2-oxaspiro[3.3]heptan-6-yl)-5-(trifluoromethyl)pyridin-2(1H)-one

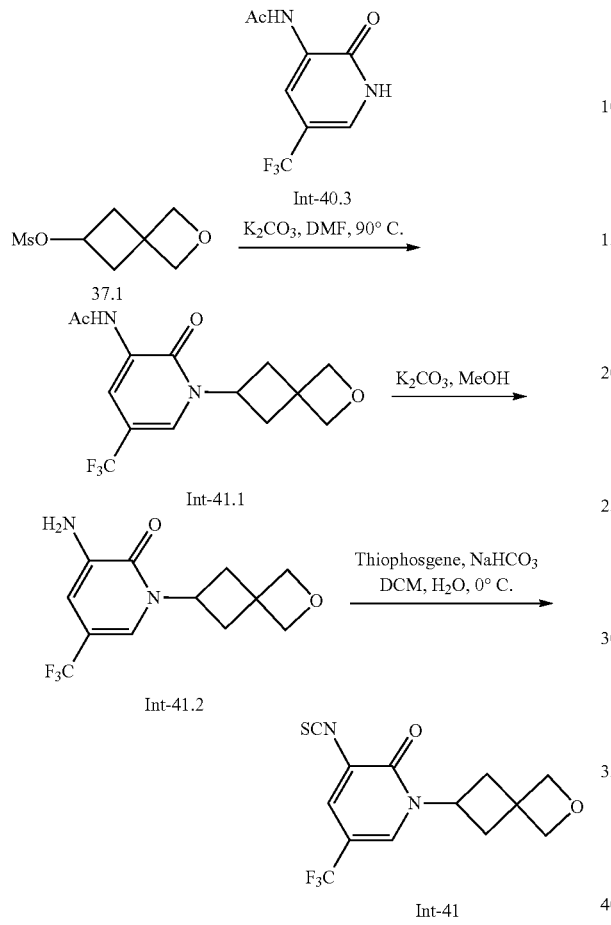

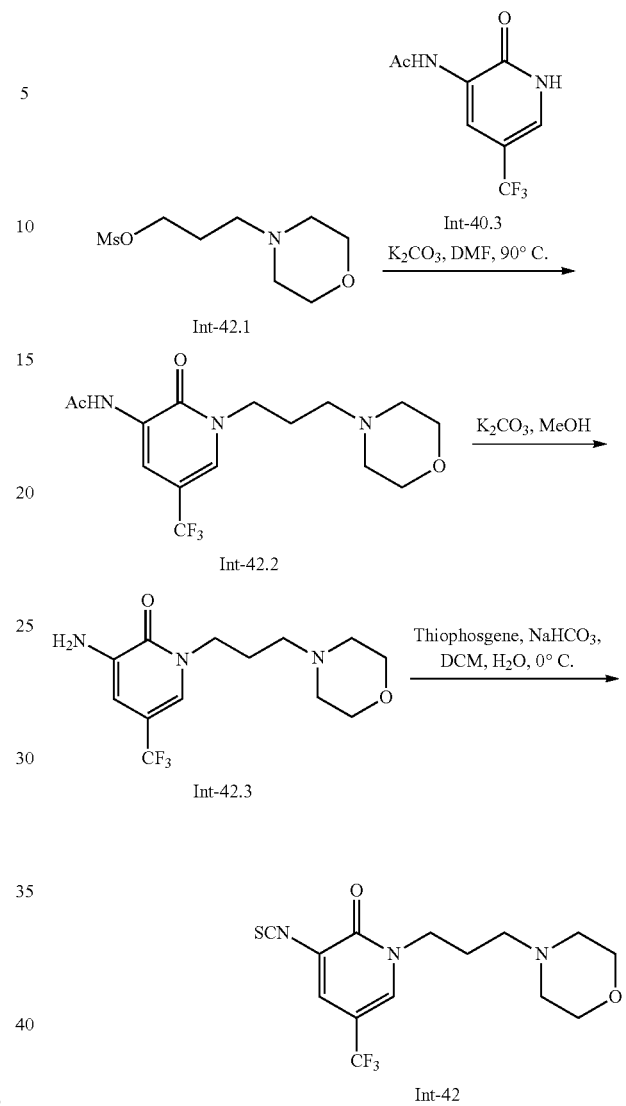

Synthesis of compound Int-41.1. Compound Int-41.1 was prepared from Int-40.3 and Int-37.1, following the procedure described in the synthesis of Int-32.4. The product was purified by flash column chromatography on silica gel (CombiFlash®, 1.3% methanol in DCM). MS (ES): m/z 317.2 [M+H]$^+$.

Synthesis of compound Int-41.2. Compound Int-41.2 was prepared from Int-41.1 following the procedure described in the synthesis of Int-29.6. The product was purified by flash column chromatography on silica gel (CombiFlash®, 2.5% methanol in DCM). MS (ES): m/z 275.2 [M+H]$^+$.

Synthesis of compound Int-41. Compound Int-41 was prepared from Int-41.2, following the procedure described in the synthesis of Int-1. The product was used without purification. MS (ES): m/z: 317.3 [M+H]$^+$.

Preparation of Intermediate Int-42: 3-isothiocyanato-1-(3-morpholinopropyl)-5-(trifluoromethyl)pyridin-2(1H)-one

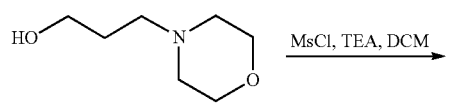

Synthesis of compound Int-42.1. Compound Int-42.1 was prepared from 3-morpholinopropan-1-ol, following the procedure described in the synthesis of Int-32.3. The product was used in the next step without purification. MS (ES): m/z 224.2 [M+H]$^+$.

Synthesis of compound Int-42.2. Compound Int-42.2 was prepared from Int-42.1 and Int-40.3, following the procedure described in the synthesis of Int-32.4. The product was purified by flash column chromatography on silica gel (CombiFlash®, 1.4% methanol in DCM). MS (ES): m/z 348.2 [M+H]$^+$.

Synthesis of compound Int-42.3. Compound Int-42.3 was prepared from Int-42.2 following the procedure described in the synthesis of Int-29.6. The product was purified by flash column chromatography on silica gel (CombiFlash®, 2.6% methanol in DCM). MS (ES): m/z 306.3 [M+H]$^+$.

Synthesis of compound Int-42. Compound Int-42 was prepared from Int-42.3, following the procedure described in the synthesis of Int-1. The product was used without purification. MS (ES): m/z: 348.3 [M+H]$^+$.

Preparation of Intermediate Int-43: 1-(3-(5-(tert-butyl)-3-isothiocyanato-1H-pyrazol-1-yl)azetidin-1-yl)ethan-1-one

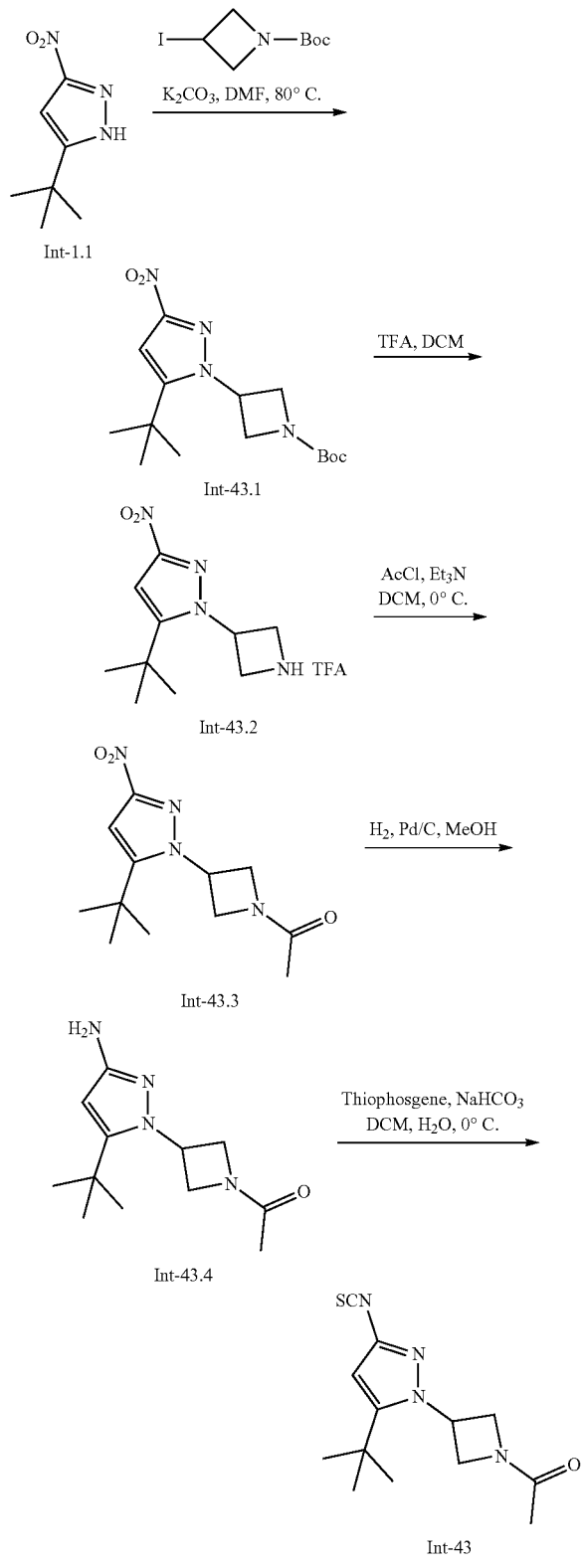

Synthesis of compound Int-43.1. A mixture of Int-1.1 (1.0 g, 5.91 mmol, 1.0 equiv), tert-butyl 3-iodoazetidine-1-carboxylate (3.68 g, 13 mmol, 2.2 equiv) and potassium carbonate (2.44 g, 17.73 mmol, 3.0 equiv) in DMF (10 mL) was stirred at 80° C. for 2 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 23% ethyl acetate in hexane) to afford Int-43.1. MS (ES): m/z 325.3 [M+H]$^+$.

Synthesis of compound Int-43.2. To a solution of Int-43.1 (0.300 g, 0.924 mmol, 1.0 equiv) in DCM (4 mL) was added trifluoroacetic acid (0.3 mL) at 0° C. and stirred for 30 min. It was concentrated under reduced pressure to afford Int-43.2. MS (ES): m/z: 225.1 [M+H]$^+$.

Synthesis of compound Int-43.3. To a solution of Int-43.2 (0.3 g, 0.886 mmol, 1.0 equiv) and triethylamine (0.37 mL, 2.658 mmol, 3.0 equiv) in DCM (2 mL) at 0° C. was added acetyl chloride (0.13 mL, 1.772 mmol, 2.0 equiv). The reaction mixture was stirred at room temperature for 30 min. It was poured into ice-water, stirred and extracted with DCM. The combined organic layers were washed with brine, dried over anhydrous sodium sulfate, filtered and concentrated under reduced pressure to afford crude material. This was purified by flash column chromatography on silica gel (CombiFlash®, 2.0% methanol in DCM) to afford Int-43.3. MS (ES): m/z 267.3 [M+H]$^+$.

Synthesis of compound Int-43.4. A mixture of Int-43.3 (0.150 g, 0.563 mmol, 1.0 equiv) and 10% palladium on carbon (0.075 g) in methanol (2 mL) was stirred under hydrogen (1 atm) for 1 h. It was filtered through a pad of Celite® and rinsed with methanol. The filtrate was concentrated under reduced pressure to afford Int-43.4. MS (ES): m/z 237.3 [M+H]$^+$.

Synthesis of compound Int-43. Compound Int-43 was prepared from Int-43.4, following the procedure described in the synthesis of Int-1. The product was purified by flash column chromatography on silica gel (CombiFlash®, 1.5% methanol in DCM). MS (ES): m/z 279.3 [M+H]$^+$.

Preparation of Intermediate trans-(±)-Int-44: trans-1-(2-(benzyloxy)cyclobutyl)-5-cyclopropyl-3-isothiocyanatopyridin-2(1H)-one

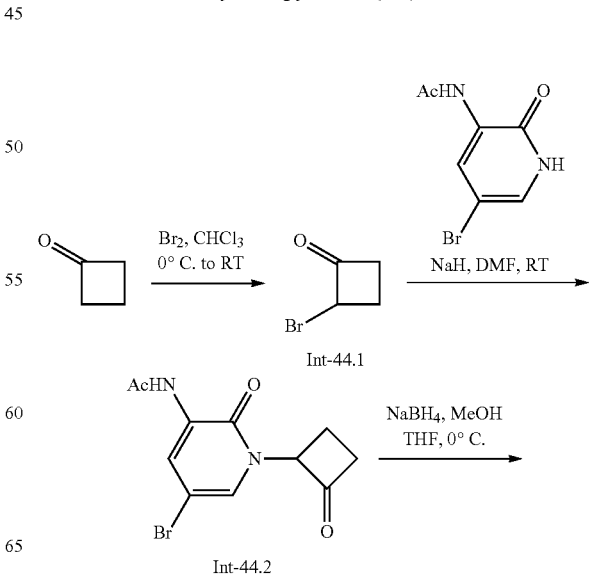

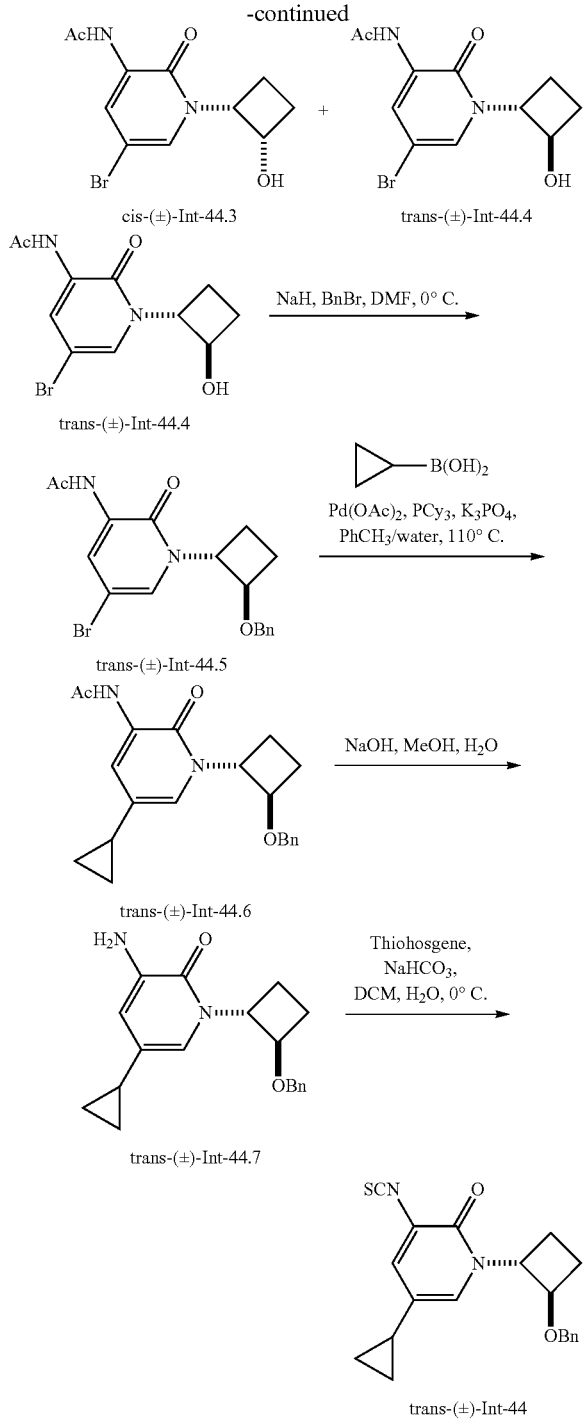

Synthesis of compound Int-44.2. To a solution of N-(5-bromo-2-oxo-1,2-dihydropyridin-3-yl)acetamide (10 g, 43.28 mmol, 1.0 equiv) in DMF (100 mL) was added sodium hydride (3.46 g, 86.56 mmol, 2.0 equiv) in portions at 0° C. and stirred for 30 min followed by addition of Int-44.1 (9.67 g, 64.92 mmol, 1.5 equiv). The reaction mixture was stirred at room temperature for 16 h. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-44.2. $^1$H NMR (DMSO-$d_6$, 400 MHz): 9.62 (s, 1H), 8.36-8.35 (d, J=2.4 Hz, 1H), 7.71-7.70 (d, J=2.4 Hz, 1H), 5.51-5.47 (m, 1H), 3.12-3.10 (m, 2H), 2.44-2.37 (m, 2H), 2.14 (s, 3H).

Synthesis of compound Int-44.3. To a solution of Int-44.2 (1.8 g, 6.02 mmol, 1.0 equiv) in methanol (20 mL) and THF (5 mL) was added sodium borohydride (0.445 g, 12.04 mmol, 2.0 equiv) slowly. The reaction mixture was stirred at 0° C. for 10 min. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in DCM) to afford cis-(±)-Int-44.3 MS (ES): m/z 302.1 [M+H]$^+$ and trans-(±)-Int-44.4. MS (ES): m/z 302.1 [M+H]$^+$.

Synthesis of compound trans-(±)-Int-44.5. To a solution of trans-(±)-Int-44.4 (0.250 g, 0.830 mmol, 1.0 equiv) in DMF (5 mL) was added sodium hydride (0.066 g, 1.66 mmol, 2.0 equiv) at 0° C. and stirred for 30 min, followed by addition of benzyl bromide (0.30 mL, 2.49 mmol, 3.0 equiv). The reaction mixture was stirred at 0° C. for 30 min. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15-20% ethyl acetate in hexane) to afford trans-(±)-Int-44.5. MS (ES): m/z 392.2 [M+H]$^+$.

Synthesis of compound trans-(±)-Int-44.6. Compound trans-(±)-Int-44.6 was prepared from trans-(±)-Int-44.5, following the procedure described in the synthesis of Int-23.2. The product was purified by flash column chromatography on silica gel (CombiFlash®, 30-35% ethyl acetate in hexane). MS (ES): m/z 353.2 [M+H]$^+$.

Synthesis of compound trans-(±)-Int-44.7 To a solution of trans-(±)-Int-44.6 (0.100 g, 0.283 mmol, 1.0 equiv) in methanol (2 mL) was added a solution of sodium hydroxide (0.339 g, 8.49 mmol, 30 equiv) in water (0.5 mL). The reaction mixture was stirred at 55-60° C. for 30 min. It concentrated under reduced pressure to afford a residue which was taken up in water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in DCM) to afford trans-(±)-Int-44.6. MS (ES): m/z 311.4 [M+H]$^+$.

Synthesis of compound trans-(±)-Int-44. Compound trans-(±)-Int-44 was prepared from trans-(±)-Int-44.7, following the procedure described in the synthesis of Int-1. The product was used without purification. MS (ES): m/z 353.3 [M+H]$^+$.

Synthesis of compound Int-44.1. To a solution of cyclobutanone (12 g, 171 mmol, 1.0 equiv) in chloroform (120 mL) was added bromine (27.3 g, 171 mmol, 1.0 equiv) dropwise at 0° C. The reaction mixture was stirred at room temperature for 16 h. It was transferred into ice/saturated sodium bicarbonate solution, stirred and extracted with ethyl acetate. The combined organic layers were washed with aqueous sodium bisulfite, brine, dried over anhydrous sodium sulfate, filtered and concentrated under reduced pressure to afford Int-44.1. $^1$H NMR (CDCl$_3$, 400 MHz): 5.18-4.99 (m, 1H), 3.31-3.22 (m, 2H), 2.83-2.73 (m, 1H), 2.33-2.29 (m, 1H).

Preparation of Intermediate cis-(±)-Int-45: cis-1-(2-(benzyloxy)cyclobutyl)-5-cyclopropyl-3-isothiocyanatopyridin-2(1H)-one

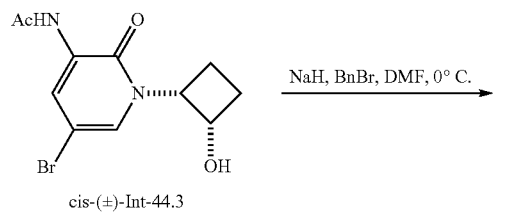

cis-(±)-Int-44.3

NaH, BnBr, DMF, 0° C.

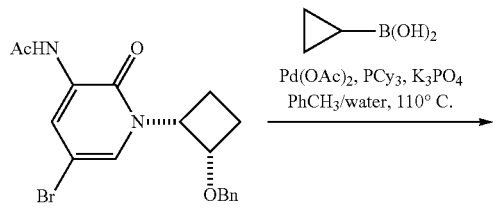

cis-(±)-Int-45.1

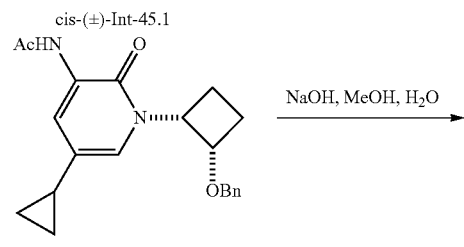

cis-(±)-Int-45.2

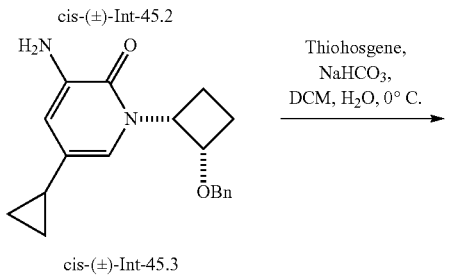

cis-(±)-Int-45.3

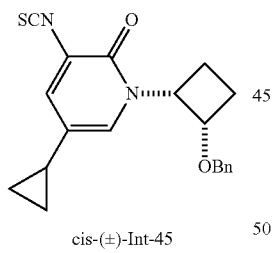

cis-(±)-Int-45

Synthesis of compound cis-(±)-Int-45.1. Compound cis-(±)-Int-45.1 was prepared from cis-(±)-Int-44.3, following the procedure described in the synthesis of trans-(±)-Int-44.5. The product was purified by flash column chromatography on silica gel (CombiFlash®, 15-20% ethyl acetate in hexane). MS (ES): m/z 392.2 [M+H]⁺.

Synthesis of compound cis-(±)-Int-45.2. Compound cis-(±)-Int-45.2 was prepared from cis-(±)-Int-45.1, following the procedure described in the synthesis of Int-23.2. The product was purified by flash column chromatography on silica gel (CombiFlash®, 30-35% ethyl acetate in hexane). MS (ES): m/z 353.2 [M+H]⁺.

Synthesis of compound cis-(±)-Int-45.3. Compound cis-(±)-Int-45.3 was prepared from cis-(±)-Int-45.2, following the procedure described in the synthesis of trans-(±)-Int-44.7. The product was purified by flash column chromatography on silica gel (CombiFlash®, 1.2% methanol in DCM). MS (ES): m/z 311.4 [M+H]⁺.

Synthesis of compound cis-(±)-Int-45. Compound cis-(±)-Int-45 was prepared from cis-(±)-Int-45.3, following the procedure described in the synthesis of Int-1. The product was used without purification. MS (ES): m/z 353.3 [M+H]⁺.

Preparation of Intermediate Int-46: 5-cyclopropyl-3-isothiocyanato-1-(3-morpholinopropyl)pyridin-2(1H)-one

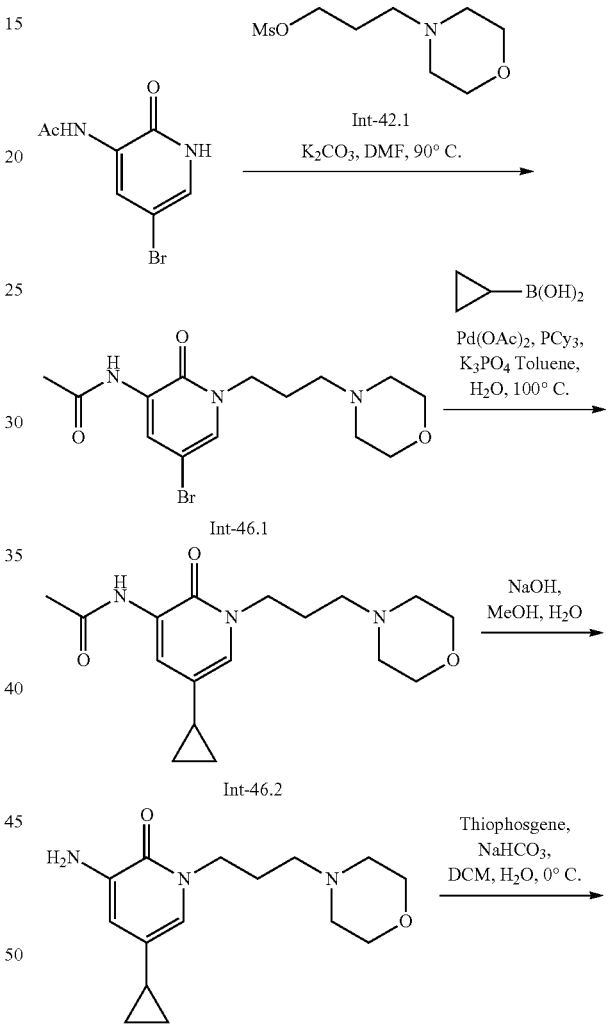

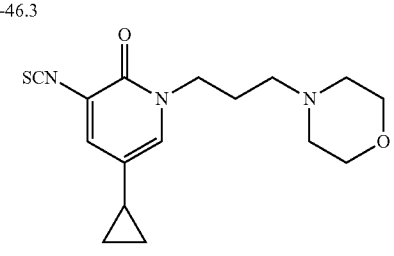

Int-46

Synthesis of compound Int-46.1. Compound Int-46.1 was prepared from N-(5-bromo-2-oxo-1,2-dihydropyridin-3-yl)

acetamide and Int-42.1, following the procedure described in the synthesis of Int-32.4. The product was purified by flash column chromatography on silica gel (CombiFlash®, 1.3% methanol in DCM). MS (ES): m/z 359.2 [M+H]⁺.

Synthesis of compound Int-46.2. Compound Int-46.2 was prepared from Int-46.1, following the procedure described in the synthesis of Int-23.2. The product was purified by flash column chromatography on silica gel (CombiFlash®, 40% ethyl acetate in hexane). MS (ES): m/z 320.2 [M+H]⁺.

Synthesis of compound Int-46.3. Compound Int-46.3 was prepared from Int-46.2, following the procedure described in the synthesis of trans-(±)-Int-44.7. The product was used without purification. MS (ES): m/z 278.3 [M+H]⁺.

Synthesis of compound Int-46. Compound Int-46 was prepared from Int-46.3, following the procedure described in the synthesis of Int-1. The product was used without purification. MS (ES): m/z: 320.4 [M+H]⁺.

Preparation of Intermediate Int-47: tert-butyl 4-(2-(5-cyclopropyl-3-isothiocyanato-2-oxopyridin-1(2H)-yl)ethyl)piperazine-1-carboxylate

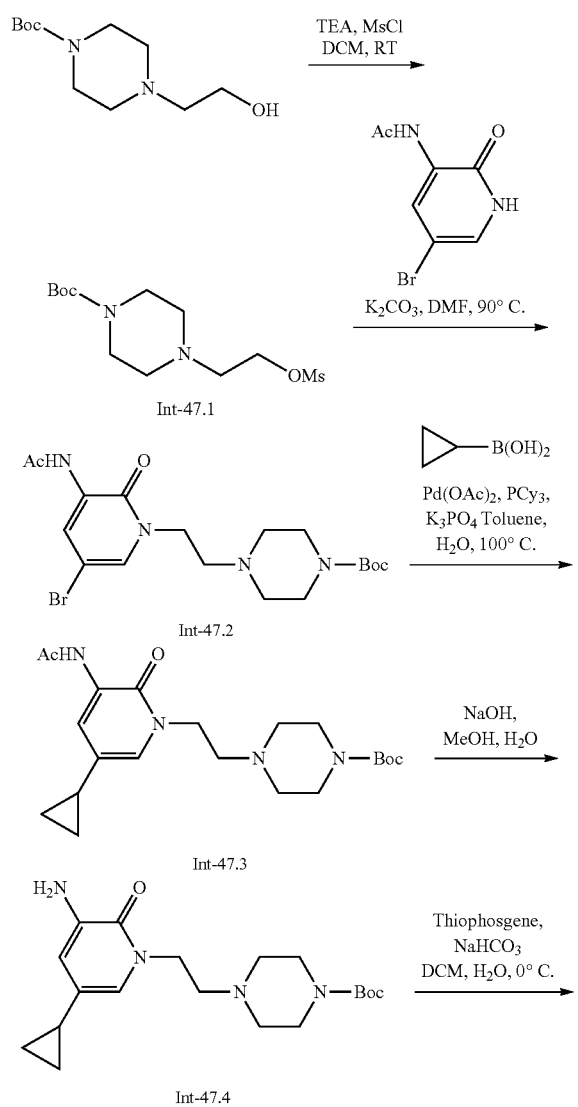

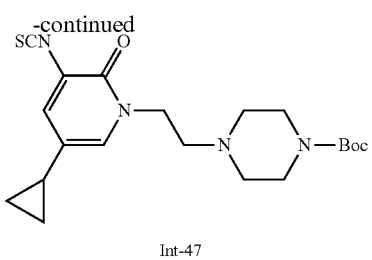

Synthesis of compound Int-47.1. To a solution of tert-butyl 4-(2-hydroxyethyl)piperazine-1-carboxylate (2.0 g, 8.68 mmol, 1.0 equiv) and triethylamine (3.0 mL, 21.7 mmol, 2.5 equiv) at 0° C. in DCM (20 mL) was added methanesulfonyl chloride (0.94 mL, 12.15 mmol, 1.4 equiv). The reaction mixture was stirred at 0° C. for 1 h. It was poured into ice-water, stirred and extracted with DCM. The combined organic layers were washed with brine, dried over anhydrous sodium sulfate, filtered and concentrated under reduced pressure to afford Int-47.1. It was used without purification. ¹H NMR (DMSO-d₆, 400 MHz): δ 4.03 (s, 3H), 3.76-3.72 (m, 8H), 2.33 (bs, 4H), 1.43 (s, 9H).

Synthesis of compound Int-47.2. Compound Int-47.2 was prepared from Int-47.1, following the procedure described in the synthesis of Int-32.4. The product was purified by flash column chromatography on silica gel (CombiFlash®, 50% ethyl acetate in hexane). MS (ES): m/z 444.5 [M+H]⁺.

Synthesis of compound Int-47.3. Compound Int-47.3 was prepared from Int-47.2, following the procedure described in the synthesis of Int-23.2. The product was purified by flash column chromatography on silica gel (CombiFlash®, 55% ethyl acetate in hexane). MS (ES): m/z 405.5 [M+H]⁺.

Synthesis of compound Int-47.4. Compound Int-47.4 was prepared from Int-47.3, following the procedure described in the synthesis of trans-(±)-Int-44.7. The product was used without purification. MS (ES): m/z 363.3 [M+H]⁺.

Synthesis of compound Int-47. Compound Int-47 was prepared from Int-47.4, following the procedure described in the synthesis of Int-1. The product was used without purification. MS (ES): m/z: 405.4 [M+H]⁺.

Preparation of Intermediate Int-48: 1-(2-(benzyloxy)ethyl)-3-isothiocyanato-5-(trifluoromethyl)pyridin-2(1H)-one

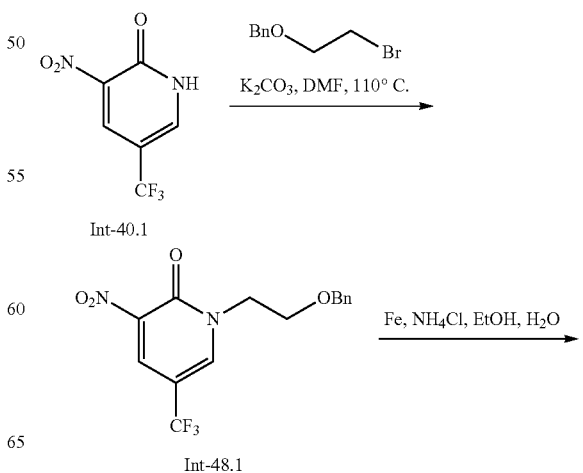

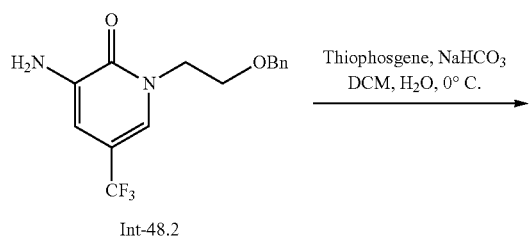

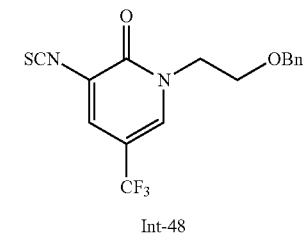

Synthesis of compound Int-48.1. To a mixture of Int-40.1 (0.5 g, 2.4 mmol, 1.0 equiv) and potassium carbonate (0.662 g, 4.8 mmol, 2.0 equiv) in DMF (7 mL) was added ((2-bromoethoxy)methyl)benzene (0.775 g, 3.6 mmol, 1.5 equiv). The reaction mixture was stirred at 110° C. for 2 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-48.1. MS (ES): m/z 343.2 [M+H]$^+$.

Synthesis of compound Int-48.2. Compound Int-48.2 was prepared from Int-48.1, following the procedure described in the synthesis of Int-27.3. The product was purified by flash column chromatography on silica gel (CombiFlash®, 2.5% methanol in DCM). MS (ES): m/z 313.3 [M+H]$^+$.

Synthesis of compound Int-48. Compound Int-48 was prepared from Int-48.2, following the procedure described in the synthesis of Int-1. The product was purified by flash column chromatography on silica gel (CombiFlash®, 1.5% methanol in DCM). MS (ES): m/z 355.3 [M+H]$^+$.

Preparation of Intermediate trans-(±)-Int-49: trans-1-(-2-(benzyloxy)cyclobutyl)-3-isothiocyanato-5-(trifluoromethyl)pyridin-2(1H)-one

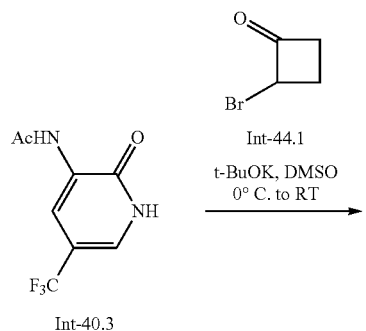

Synthesis of compound Int-49.1. To a solution of Int-40.3 (10 g, 45.42 mmol, 1.0 equiv) and Int-44.1 (10.15 g, 68.13 mmol, 1.5 equiv) in DMSO (100 mL) was added potassium tert-butoxide (1 M in THF, 0.62 mL, 0.62 mmol, 3.0 equiv) at 0° C. The reaction mixture was stirred at room temperature for 16 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-49.1. MS (ES): m/z 289.2[M+H]$^+$.

Synthesis of compound cis-(±)-Int-49.2 and trans-(±)-Int-49.3. To a solution of Int-49.1 (0.640 g, 2.22 mmol, 1.0 equiv) in methanol (10 mL) was added sodium borohydride (0.164 g, 4.44 mmol, 2.0 equiv) slowly. The reaction mixture was stirred at 0° C. for 10 min. It was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in DCM) to afford cis-(±)-Int-49.2. MS (ES): m/z 291.1 [M+H]+ and trans-(±)-Int-49.3. MS (ES): m/z 291.1 [M+H]+.

Synthesis of compound trans-(±)-Int-49.3. Compound trans-(±)-Int-49.3 was prepared from trans-(±)-Int-49.2, following the procedure described in the synthesis of trans-(±)-Int-44.5. The product was purified by flash column chromatography on silica gel (CombiFlash®, 15-20% ethyl acetate in hexane). MS (ES): m/z 381.2 [M+H]+.

Synthesis of compound trans-(±)-Int-49.4. Compound trans-(±)-Int-49.4 was prepared from trans-(±)-Int-49.3, following the procedure described in the synthesis of trans-(±)-Int-44.7. The product was purified by flash column chromatography on silica gel (CombiFlash®, 1.6% methanol in DCM). MS (ES): m/z 339.3 [M+H]+.

Synthesis of compound trans-(±)-Int-49. Compound trans-(±)-Int-49 was prepared from trans-(±)-Int-49.4, following the procedure described in the synthesis of Int-1. The product was purified by flash column chromatography on silica gel (CombiFlash®, 15% ethyl acetate in hexane). MS (ES): m/z 381.3 [M+H]+.

Preparation of Intermediate Int-50: 3-amino-5-cyclopropyl-1-(2-methoxy-2-methylpropyl)pyridin-2(1H)-one

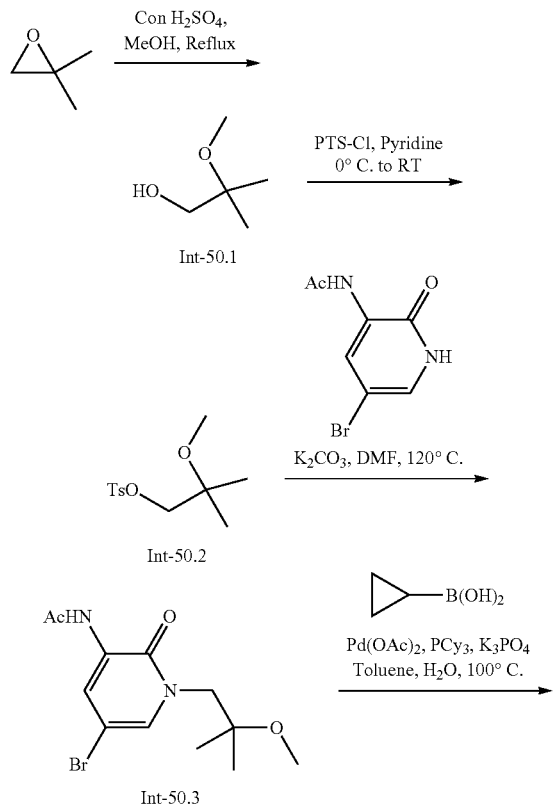

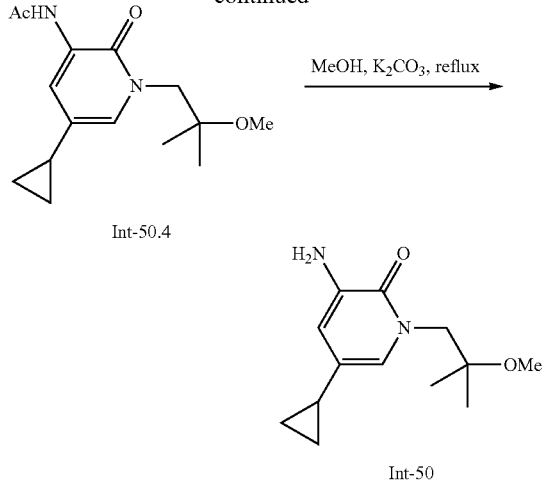

Synthesis of compound Int-50.1. To a solution of 2,2-dimethyloxirane (60 g, 832 mmol, 1.0 equiv) in methanol (300 mL) was added concentrated sulfuric acid. The reaction mixture was heated to reflux for 5 h. It neutralized with methanolic potassium hydroxide to pH=7. The reaction mixture was concentrated under reduced pressure. The residue was purified by fractional distillation to afford Int-50.1 (boiling point: 136-140° C.). $^1$H NMR (CDCl$_3$, 400 MHz): δ 3.51 (s, 2H), 3.46 (bs, 1H), 3.26 (s, 3H), 1.19 (s, 6H).

Synthesis of compound Int-50.2. To a solution of Int-50.1 (4.5 g, 43.21 mmol, 1.0 equiv) in pyridine (37 mL) was added p-toluenesulfonyl chloride (3.011 g, 15.85 mmol, 1.2 equiv) at 0° C. The reaction mixture was stirred at room temperature for 16 h. It was transferred into ice-cold aqueous hydrochloric acid, stirred and extracted with ethyl acetate. The combined organic layers were washed with brine, dried over anhydrous sodium sulfate, filtered and concentrated under reduced pressure to afford Int-50.2. $^1$H NMR (CDCl$_3$, 400 MHz): δ 7.83-7.81 (d, J=6.8 Hz, 2H), 7.37-7.35 (J=7.2 Hz, 2H), 3.87 (s, 2H), 2.99 (s, 3H), 2.47 (s, 3H), 1.17 (s, 6H).

Synthesis of compound Int-50.3. To a solution of N-(5-bromo-2-oxo-1,2-dihydropyridin-3-yl)acetamide (2.0 g, 8.66 mmol, 1.0 equiv) in DMF (20 mL) was added potassium carbonate (3.585 g, 25.98 mmol, 3.0 equiv) followed by Int-50.2 (2.68 g, 10.39 mmol, 1.2 equiv). The reaction mixture stirred at 120° C. for 16 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-50.3. MS (ES): m/z 318.1 [M+H]+.

Synthesis of compound Int-50.4. Compound Int-50.4 was prepared from Int-50.3, following the procedure described in the synthesis of Int-23.2. The product was purified by flash column chromatography on silica gel (CombiFlash®, 2.0% methanol in DCM). MS (ES): m/z 279.3 [M+H]+.

Synthesis of compound Int-50. Compound Int-50 was prepared from Int-50.4, following the procedure described in the synthesis of Int-29.6. The product was purified by flash column chromatography on silica gel (CombiFlash®, 2.5% methanol in DCM). MS (ES): m/z 237.3 [M+H]+.

Preparation of Intermediate (±)-Int-51: 3-isothiocyanato-1-(tetrahydro-2H-pyran-3-yl)-5-(trifluoromethyl)pyridin-2(1H)-one

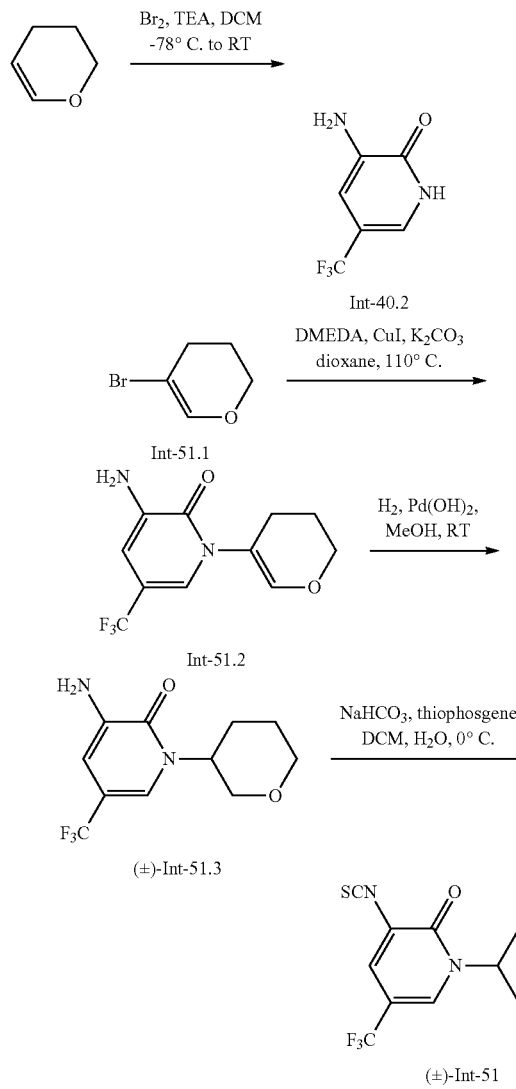

(±)-Int-51

Synthesis of compound Int-51.1. To a solution of 3,4-dihydro-2H-pyran (20 g, 238 mmol, 1.0 equiv) in DCM (200 mL) was added bromine (12.2 mL, 238 mmol, 1.0 equiv) in DCM (100 mL) at −78° C. dropwise. The reaction mixture was stirred at −78° C. for 2 h. It was allowed to warm to room temperature and stirred for 16 h. To the reaction mixture was added triethylamine (66 mL, 476 mmol, 2.0 equiv) in DCM (100 mL) dropwise and it was stirred for 5 h. The reaction mixture was concentrated under reduced pressure. To the residue was added diethyl ether. The precipitations were removed by filtration. The filtrate was concentrated under reduced pressure. The residue was purified by vacuum distillation (80° C., 0.02 mmHg), to afford Int-51.1. $^1$H NMR (400 M Hz, CDCl$_3$): 6.68 (s, 1H), 4.02-4.00 (t, J=4 Hz, 2H), 2.45-2.42 (m, 2H), 2.06-2.00 (m, 2H).

Synthesis of compound Int-51.2. To a solution of Int-40.2 (0.7 g, 3.93 mmol, 1.0 equiv) and Int-51.1 (0.960 g, 5.90 mmol, 1.5 equiv) in 1,4-dioxane (10 mL) was added potassium carbonate (1.084 g, 7.86 mmol, 2.0 equiv), and the mixture was degassed by bubbling through a stream of argon for 15 min. Copper iodide (0.149 g, 0.786 mmol, 0.2 equiv) and 1,2-dimethylethylenediamine (0.138 g, 1.572 mmol, 0.4 equiv) were added. The reaction mixture was degassed for another 5 min and stirred at 110° C. for 12 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.1% methanol in DCM) to afford Int-51.1. MS (ES): m/z 261.2 [M+H]$^+$.

Synthesis of compound (±)-Int-51.3. A mixture of Int-51.2 (0.472 g, 1.81 mmol, 1.0 equiv) and 20% palladium hydroxide (0.4 g) in methanol (5 mL) was stirred under hydrogen (1 atm) for 16 h at room temperature. It was filtered through a pad of Celite® and rinsed with methanol. The filtrate was concentrated under reduced pressure. The residue was purified by trituration with n-pentane to afford (±)-Int-51.3. MS (ES): m/z 263.2 [M+H]$^+$.

Synthesis of compound (±)-Int-51. Compound (±)-Int-51 was prepared from (f)-Int-51.3, following the procedure described in the synthesis of Int-1. The product was purified by flash column chromatography on silica gel (CombiFlash®, 20% ethyl acetate in hexane). MS (ES): m/z 305.2 [M+H]$^+$.

Preparation of Intermediate Int-52: 5-cyclopropyl-3-isothiocyanato-2H-[1,3'-bipyridin]-2-one

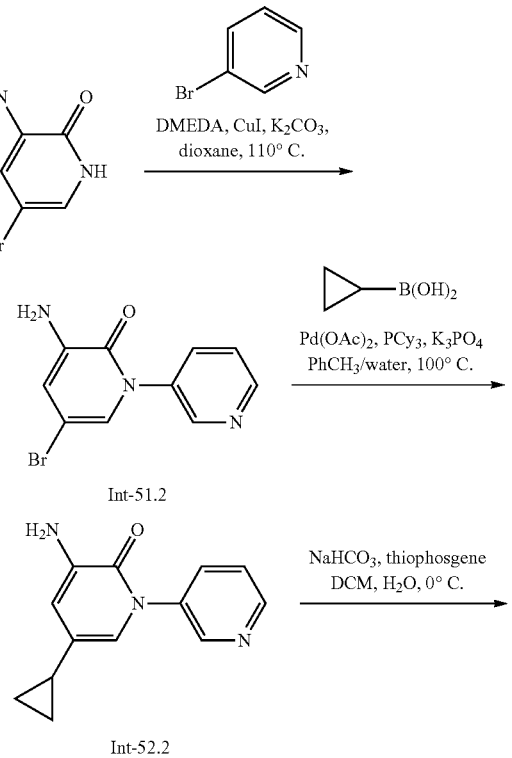

Int-52.2

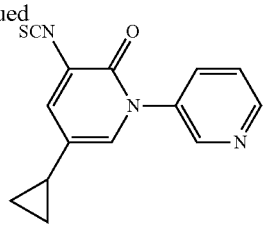

Int-52

Synthesis of compound Int-52.1. Compound Int-52.1 was prepared from 3-amino-5-bromopyridin-2(1H)-one and 3-bromopyridine, following the procedure described in the synthesis of Int-51.2. The product was purified by flash column chromatography on silica gel (CombiFlash®, 2.5% methanol in DCM). MS (ES): m/z 267.1 [M+H]$^+$.

Synthesis of compound Int-52.2. Compound Int-52.2 was prepared from Int-52.1, following the procedure described in the synthesis of Int-23.2. The product was purified by flash column chromatography on silica gel (CombiFlash®, 4.0% methanol in DCM). MS (ES): m/z 228.2 [M+H]$^+$.

Synthesis of compound Int-52.3. Compound Int-52.3 was prepared from Int-52.2, following the procedure described in the synthesis of Int-1. The product was purified by flash column chromatography on silica gel (CombiFlash®, 1.5% methanol in DCM). MS (ES): m/z 270.3 [M+H]$^+$.

Preparation of Intermediate Int-53: 3-isothiocyanato-5-(trifluoromethyl)-2H-[1,3'-bipyridin]-2-one

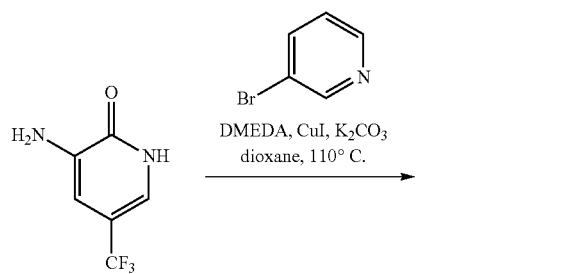

Int-40.2

Int-53.1

Int-53

Synthesis of compound Int-53.1. Compound Int-53.1 was prepared from Int-40.2 and 3-bromopyridine, following the procedure described in the synthesis of Int-51.2. The product was purified by flash column chromatography on silica gel (CombiFlash®, 2.7% methanol in DCM). MS (ES): m/z 256.2 [M+H]$^+$.

Synthesis of compound Int-53. Compound Int-53 was prepared from Int-53.1, following the procedure described in the synthesis of Int-1. The product was purified by flash column chromatography on silica gel (CombiFlash®, 1.7% methanol in DCM). MS (ES): m/z 298.2 [M+H]$^+$.

Preparation of Intermediate Int-54: 5-cyclopropyl-3-isothiocyanato-1-(1-methyl-1H-pyrazol-4-yl)pyridin-2(1H)-one

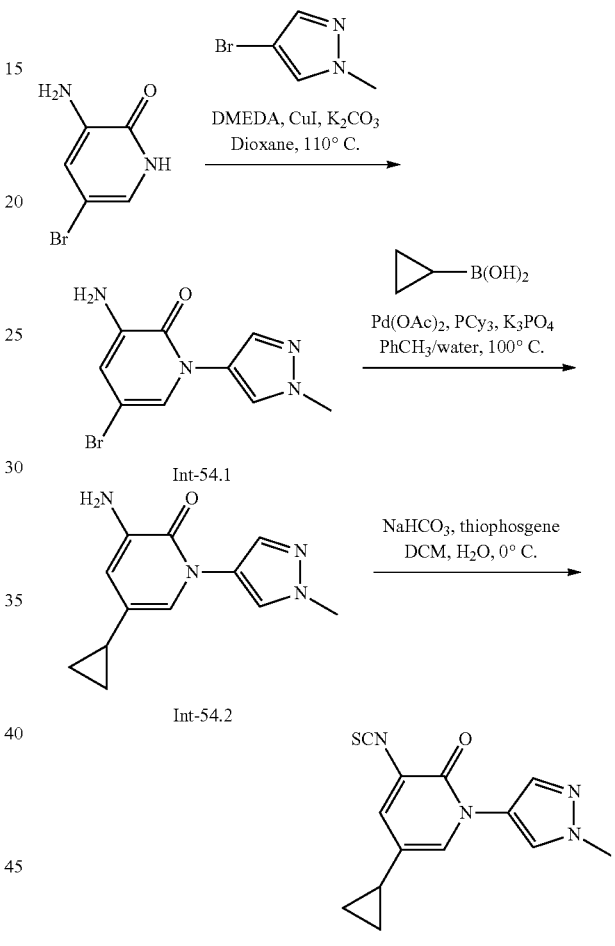

Int-54.1

Int-54.2

Int-54

Synthesis of compound Int-54.1. Compound Int-54.1 was prepared from 3-amino-5-bromopyridin-2(1H)-one and 4-bromo-1-methyl-1H-pyrazole, following the procedure described in the synthesis of Int-51.2. The product was purified by flash column chromatography on silica gel (CombiFlash®, 2.1% methanol in DCM). MS (ES): m/z 270.1 [M+H]$^+$.

Synthesis of compound Int-54.2. Compound Int-54.2 was prepared from Int-54.1, following the procedure described in the synthesis of Int-23.2. The product was purified by flash column chromatography on silica gel (CombiFlash®, 2.4% methanol in DCM). MS (ES): m/z 231.2 [M+H]$^+$.

Synthesis of compound Int-54. Compound Int-54 was prepared from Int-54.2, following the procedure described in the synthesis of Int-1. The product was purified by flash column chromatography on silica gel (CombiFlash®, 1.4% methanol in DCM). MS (ES): m/z 273.3 [M+H]$^+$.

Preparation of Intermediate Int-55: 6-cyclopropyl-4-isothiocyanato-2-methylpyridazin-3(2H)-one

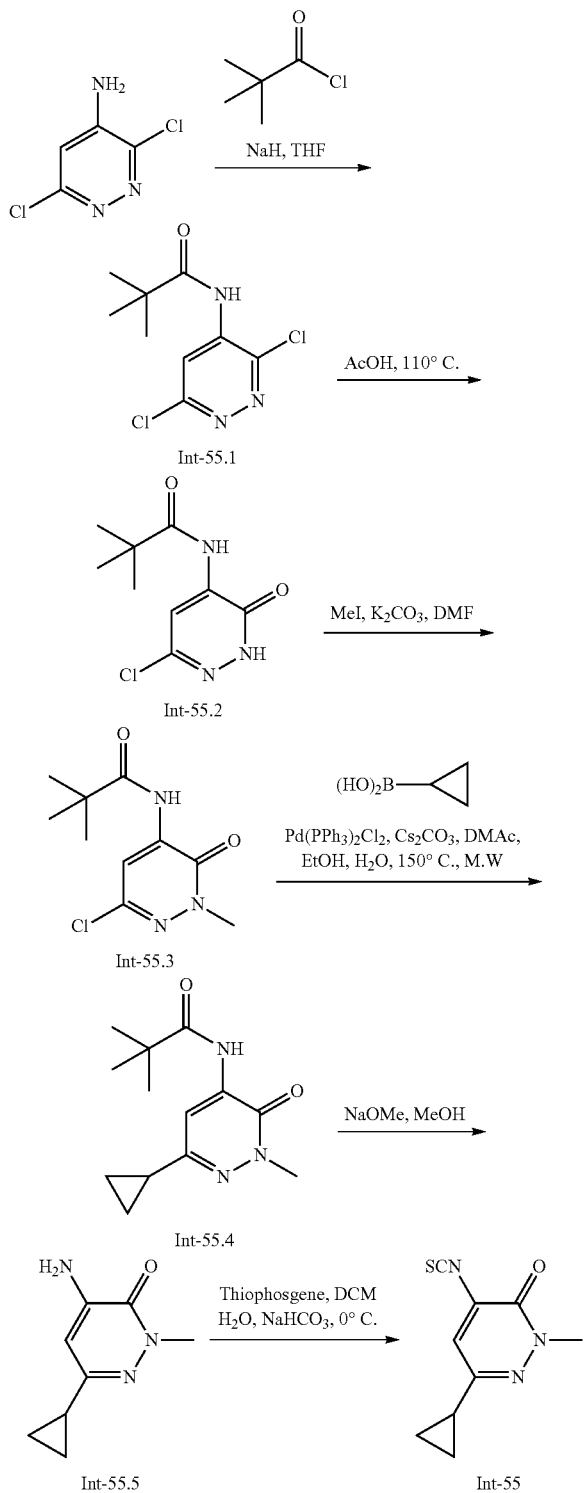

Synthesis of compound Int-55.1. To a solution of 3,6-dichloropyridazin-4-amine (0.9 g, 5.49 mmol, 1.0 equiv) in THF (20 mL) was added sodium hydride (0.579 g, 12.07 mmol, 2.2 equiv) at 0° C. and stirred for 10 min. Pivaloyl chloride (0.7 mL, 5.76 mmol, 1.05 equiv) was added dropwise. The reaction mixture was stirred at room temperature for 15 min. It was transferred into ice-water, stirred and extracted with ethyl acetate. The combined organic layers were washed with brine, dried over anhydrous sodium sulfate, filtered and concentrated under reduced pressure to afford Int-55.1. MS (ES): m/z 230.6 [M+H]$^+$.

Synthesis of compound Int-55.2. A solution of Int-55.1 (1.1 g, 4.43 mmol, 1.0 equiv) in acetic acid (10 mL) was stirred at 110° C. for 3 h. It was transferred into ice, stirred and neutralized with saturated sodium bicarbonate solution. Precipitated solid was filtered out and dried well to afford Int-55.2. MS (ES): m/z 271.3 [M+H]$^+$.

Synthesis of compound Int-55.3. To a solution of Int-55.2 (0.7 g, 3.05 mmol, 1.0 equiv) in DMF (7 mL) was added potassium carbonate (0.841 g, 6.1 mmol, 2.0 equiv) at room temperature and stirred for 15 min followed by addition of methyl iodide (0.519 g, 3.66 mmol, 1.2 equiv). The reaction mixture was stirred at room temperature for 16 h. It was poured into ice-water and extracted with ethyl acetate. The combined organic layers were washed with brine, dried over anhydrous sodium sulfate, filtered and concentrated under reduced pressure. The residue was purified by trituration with n-pentane to afford Int-55.3. MS (ES): m/z 244.6 [M+H]$^+$.

Synthesis of compound Int-55.4. To a solution of Int-55.3 (0.350 g, 1.44 mmol, 1.0 equiv) in dimethylacetamide (2 mL), water (1 mL) and ethanol (0.7 mL) was added cyclopropylboronic acid (0.27 g, 3.16 mmol, 2.2 equiv), cesium carbonate (0.938 g, 2.88 mmol, 2.0 equiv) and dichlorobis(triphenylphosphine)palladium(II) (0.090 g, 0.129 mmol, 0.09 equiv). The reaction mixture was heated in a microwave reactor at 150° C. for 30 min. It was cooled to room temperature and filtered through a pad of Celite®. The filtrate was transferred into water and extracted with DCM. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-55.4. MS (ES): m/z 250.3 [M+H]$^+$.

Synthesis of compound Int-55.5. To a solution of Int-55.4 (0.155 g, 0.621 mmol, 1.0 equiv) in methanol (2.5 mL) was added sodium methoxide solution (25% in methanol, 0.4 mL, 1.86 mmol, 3.0 equiv). The reaction mixture was stirred at 65° C. for 2 h. It was concentrated under reduced pressure. The residue was transferred into water and extracted with ethyl acetate. The combined organic layers were washed with brine, dried over anhydrous sodium sulfate, filtered and concentrated under reduced pressure to afford Int-55.5. MS (ES): m/z 166.2 [M+H]$^+$.

Synthesis of compound Int-55. Compound Int-55 was prepared from Int-55.5, following the procedure described in the synthesis of Int-1. The product was used without purification. MS (ES): m/z 208.3 [M+H]$^+$.

Preparation of Intermediate Int-56: 5-cyclopropyl-1-(3-(3,3-difluoropyrrolidin-1-yl)propyl)-3-isothiocyanatopyridin-2(1H)-one

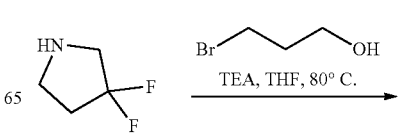

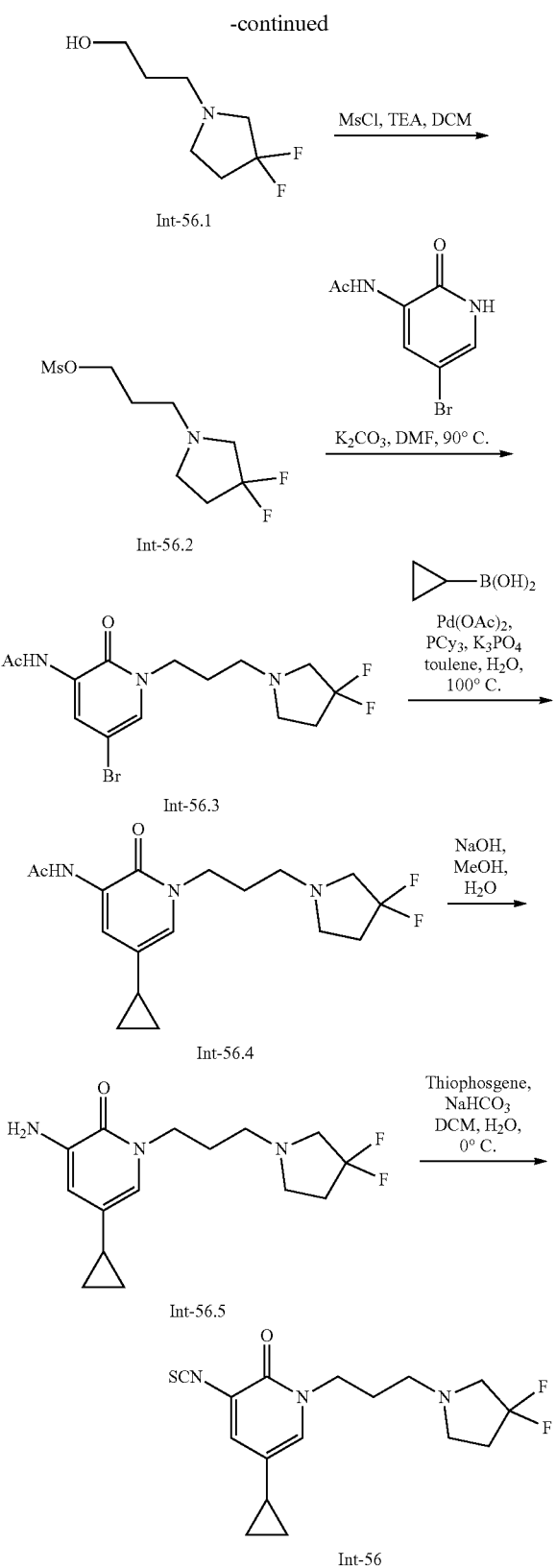

was stirred at 80° C. for 12 h. It was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-56.1. $^1$H NMR (DMSO-$d_6$, 400 MHz): δ 4.43 (bs, 1H), 3.39-3.36 (m, 2H), 2.87-2.80 (m, 2H), 2.67-2.64 (m, 2H), 2.47-2.44 (m, 2H), 2.28-2.17 (m, 2H), 1.60-1.55 (m, 2H).

Synthesis of compound Int-56.2. Compound Int-56.2 was prepared from Int-56.1, following the procedure described in the synthesis of Int-32.3. The product was used without purification. $^1$H NMR (DMSO-$d_6$, 400 MHz): δ 4.26-4.22 (m, 2H), 3.17 (s, 3H), 2.91-2.84 (m, 2H), 2.71-2.67 (m, 2H), 2.53-2.47 (m, 2H), 2.29-2.18 (m, 2H), 1.86-1.80 (m, 2H).

Synthesis of compound Int-56.3. Compound Int-56.3 was prepared from Int-56.2, following the procedure described in the synthesis of Int-32.4. The product was purified by preparative HPLC. MS (ES): m/z 379.2 [M+H]$^+$.

Synthesis of compound Int-56.4. Compound Int-56.4 was prepared from Int-56.3, following the procedure described in the synthesis of Int-23.2. The product was purified by flash column chromatography on silica gel (CombiFlash®, 2.0% methanol in DCM). MS (ES): m/z 340.2 [M+H]$^+$.

Synthesis of compound Int-56.5. Compound Int-56.5 was prepared from Int-56.4, following the procedure described in the synthesis of trans-(±)-Int-44.7. The product was purified by flash column chromatography on silica gel (CombiFlash®, 2.5% methanol in DCM). MS (ES): m/z 298.3 [M+H$^+$.

Synthesis of compound Int-56. Compound Int-56 was prepared from Int-56.5, following the procedure described in the synthesis of Int-1. The product was purified by flash column chromatography on silica gel (CombiFlash®, 1.5% methanol in DCM). MS (ES): m/z: 340.4 [M+H]$^+$.

Preparation of Intermediate Int-57: 1-(3-(3,3-difluoropyrrolidin-1-yl)propyl)-3-isothiocyanato-5-(trifluoromethyl)pyridin-2(1H)-one

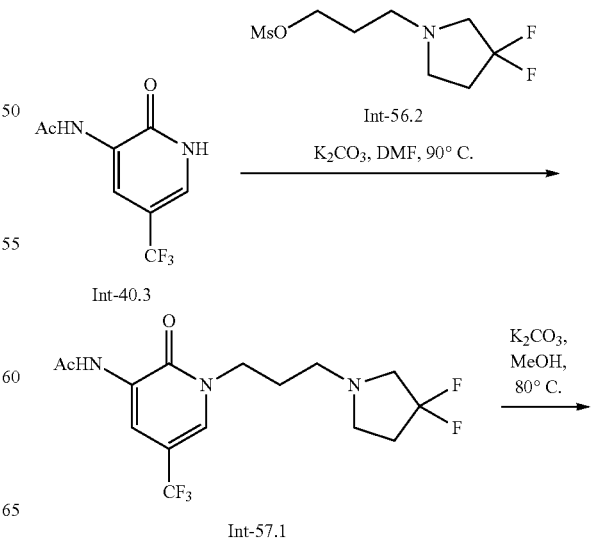

Synthesis of compound Int-56.1. To a solution of 3,3-difluoropyrrolidine (10.0 g, 93.37 mmol, 1.0 equiv), triethylamine (3.0 mL, 21.7 mmol, 3.0 equiv) and 3-bromopropan-1-ol (25.95 g, 186.7 mmol, 2.0 equiv) in THF (10 mL)

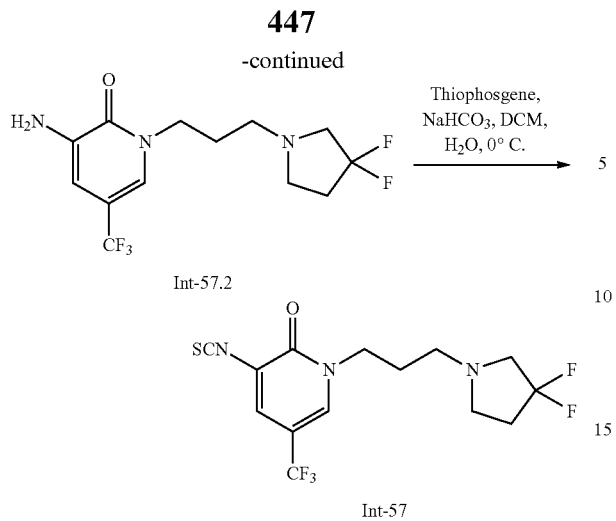

Int-57.2

Int-57

Synthesis of compound Int-57.1. Compound Int-57.1 was prepared from Int-40.3 and Int-56.2, following the procedure described in the synthesis of Int-32.4. The product was purified by flash column chromatography on silica gel (CombiFlash®, 45% ethyl acetate in hexane). MS (ES): m/z 368.3 [M+H]$^+$.

Synthesis of compound Int-57.2. Compound Int-57.2 was prepared from Int-57.1, following the procedure described in the synthesis of Int-29.6. The product was purified by flash column chromatography on silica gel (CombiFlash®, 28% ethyl acetate in hexane). MS (ES): m/z 326.2 [M+H]$^+$.

Synthesis of compound Int-57. Compound Int-57 was prepared from Int-57.2 following the procedure described in the synthesis of Int-1. The product was purified by flash column chromatography on silica gel (CombiFlash®, 1.0% methanol in DCM). MS (ES): m/z: 368.3 [M+H]$^+$.

Preparation of Intermediate cis-(±)-Int-58: cis-1-(2-(benzyloxy)cyclobutyl)-3-isothiocyanato-5-(trifluoromethyl)pyridin-2(1H)-one

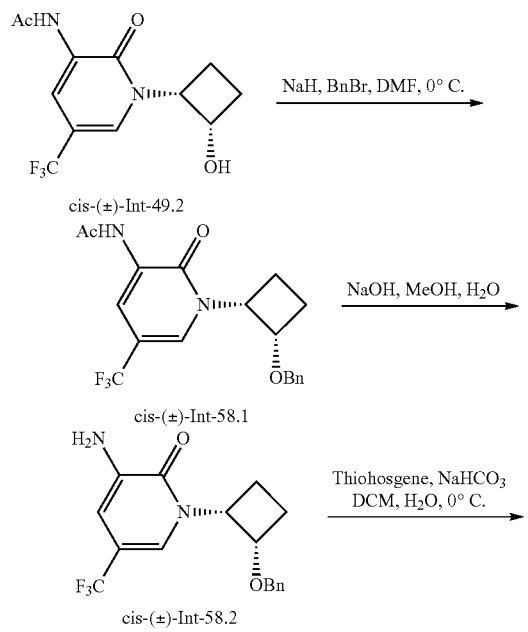

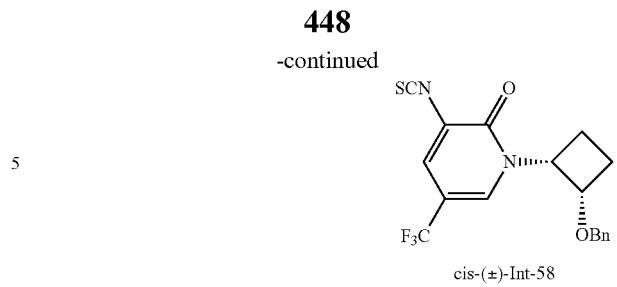

cis-(±)-Int-58

Synthesis of compound cis-(±)-Int-58.1. Compound cis-(±)-Int-58.1 was prepared from cis-(±)-Int-49.2 following the procedure described in the synthesis of trans-(±)-Int-49.3. The product was purified by flash column chromatography on silica gel (CombiFlash®, 15-20% ethyl acetate in hexane). MS (ES): m/z 381.2 [M+H]$^+$.

Synthesis of compound cis-(±)-Int-58.2. Compound cis-(±)-Int-58.2 was prepared from cis-(±)-Int-58.1, following the procedure described in the synthesis of trans-(±)-Int-44.7. The product was purified by flash column chromatography on silica gel (CombiFlash®, 1.6% methanol in DCM). MS (ES): m/z 339.3 [M+H]$^+$.

Synthesis of compound cis-(±)-Int-58. Compound cis-(±)-Int-58 was prepared from cis-(±)-Int-58.2 following the procedure described in the synthesis of Int-1. The product was purified by flash column chromatography on silica gel (CombiFlash®, 15% ethyl acetate in hexane). MS (ES): m/z 381.3 [M+H]$^+$.

Preparation of Intermediate Int-59: 1-ethyl-4-(4-isothiocyanato-2-(trifluoromethyl)benzyl)piperazine

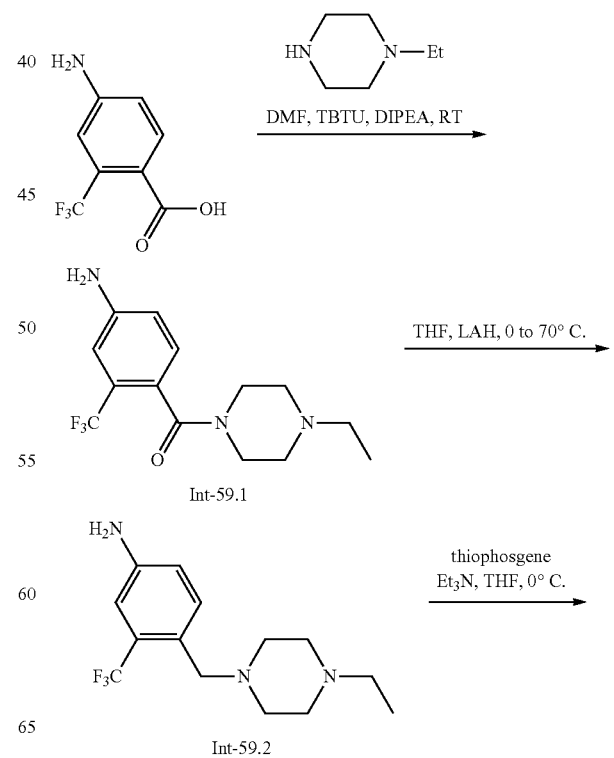

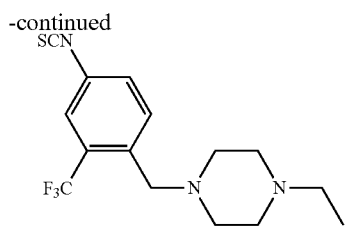

Int-59

Synthesis of compound Int-59.1. To a solution of 4-amino-2-(trifluoromethyl)benzoic acid (10 g, 48.75 mmol, 1.0 equiv) in DMF (30 mL) was added 0-(benzotriazol-1-yl)-N,N,N',N'-tetramethyluronium tetrafluoroborate (18.4 g, 58.5 mmol, 1.2 equiv) at 0° C. The reaction mixture was stirred for 30 min. To the mixture was added 1-ethylpiperazine (6.67, 58.5 mmol, 1.2 equiv) followed by N,N-diisopropylethylamine (24 mL, 146.25 mmol, 3.0 equiv) and stirred at room temperature for 3 h. It was transferred into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in DCM) to afford Int-59.1. MS (ES): m/z 302.3 [M+H]$^+$.

Synthesis of compound Int-59.2. To a solution of Int-59.1 (2 g, 6.64 mmol, 1.0 equiv) in THF (20 mL) was added lithium aluminum hydride solution (1 M in THF) (19.9 mL, 19.92 mmol, 3.0 equiv) at 0° C. The reaction mixture was heated to reflux for 3 h. It was cooled to room temperature, transferred into ice-water and extracted with ethyl acetate. The combined organic layers were washed with brine, dried over anhydrous sodium sulfate, filtered and concentrated under reduced pressure to afford Int-59.2. MS (ES): m/z 288.3 [M+H]$^+$.

Synthesis of compound Int-59. Compound Int-59 was prepared from Int-59.2 following the procedure described in the synthesis of Int-1. The product was purified by flash column chromatography on silica gel (CombiFlash®, 3.0% methanol in DCM). MS (ES): m/z 330.3 [M+H]$^+$.

Preparation of Intermediate Int-60: 1-(4-isothiocyanato-2-(trifluoromethyl)benzyl)-4-methylpiperazine

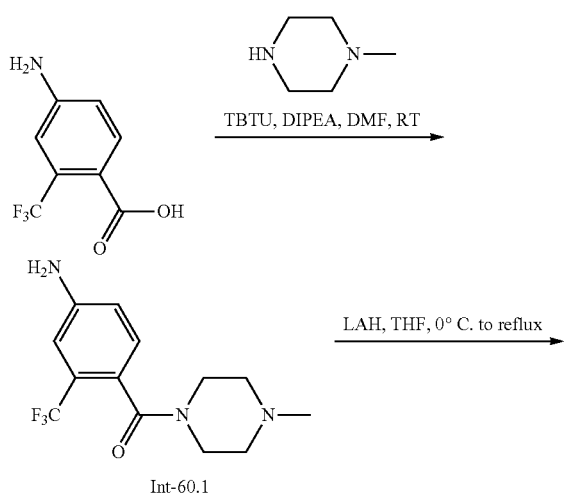

Int-60.1

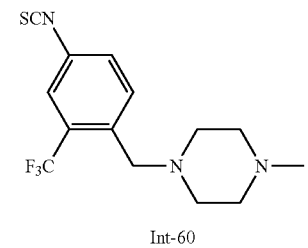

Int-60.2

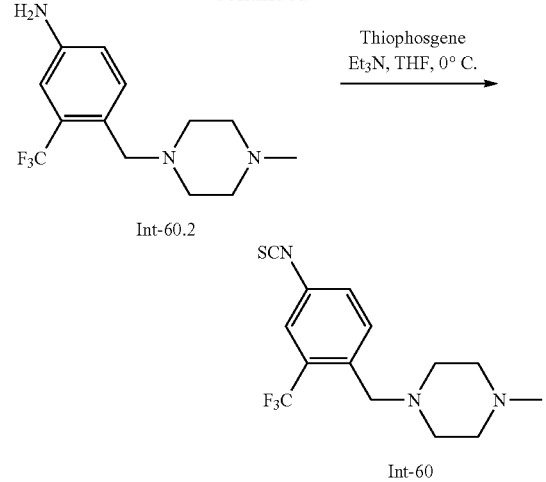

Int-60

Synthesis of compound Int-60. Compound Int-60 was prepared following the procedures described in the synthesis of Int-59. The product was purified by flash column chromatography on silica gel (CombiFlash®, 2.0% methanol in dichloromethane). MS (ES): m/z 316.2 [M+H]$^+$.

Preparation of Intermediate Int-61: 2-isothiocyanato-4,4-dimethyl-4,5,6,7-tetrahydropyrazolo[1,5-a]pyridine

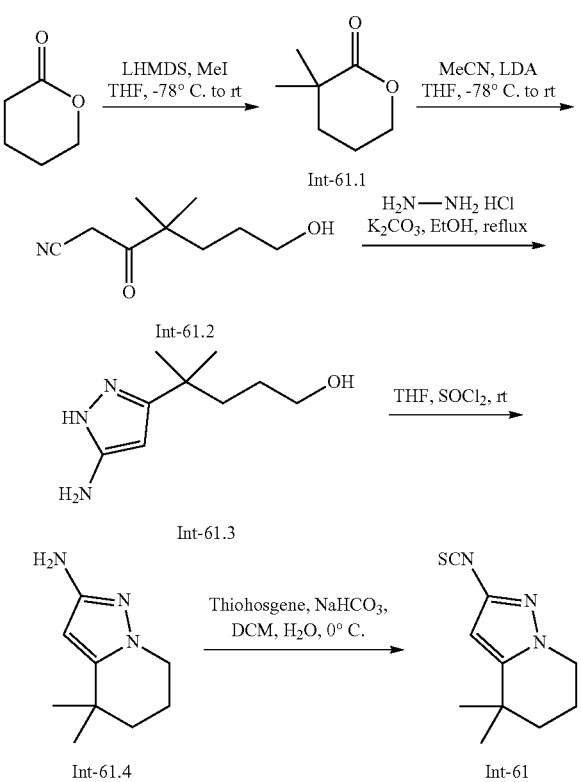

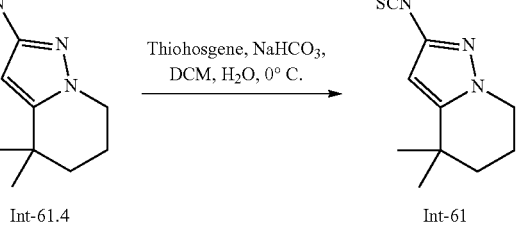

Synthesis of compound Int-61.1. To a solution of δ-valerolactone (10 g, 99.88 mmol, 1.0 equiv) and methyl iodide (24.8 mL, 399.52 mmol, 4.0 equiv) in THF (200 mL) was added lithium bis(trimethylsilyl)amide (1 M in THF, 219 mL, 219.7 mmol, 2.2 equiv) at −78° C. The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford Int-61.1. MS (ES): m/z 129.2 [M+H]$^+$.

Synthesis of compound Int-61.2. To a solution of diisopropylamine (4.88 g, 48.37 mmol, 1.0 equiv) in THF (100 mL) at −78° C. was slowly added a solution of n-butyl lithium (2.5 M in hexane, 24.2 mL, 60.46 mmol, 1.25 equiv). The reaction mixture was stirred for 5 min followed by addition of acetonitrile (2.5 mL, 48.37 mmol, 1.0 equiv). The reaction mixture stirred for 10 min and compound Int-61.1 (6.20 g, 48.37 mmol, 1.0 equiv) in THF (30 mL) was added to it. The reaction mixture was stirred at 5° C. for 6 h. It was poured over cold saturated ammonium chloride solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford Int-61.2. MS (ES): m/z 170.2 [M+H]$^+$.

Synthesis of compound Int-61.3. To a solution of Int-61.2 (3.9 g, 23.05 mmol, 1.0 equiv) in ethanol (40 mL) was added hydrazine hydrochloride (2.35 g, 34.57 mmol, 1.5 equiv) followed by addition of potassium carbonate (4.77 g, 34.57 mmol, 1.5 equiv). The reaction mixture was heated to reflux for 16 h. It was concentrated under reduced pressure. The residue was purified by flash column chromatography on silica gel (CombiFlash®, 3-4% methanol in DCM as eluant) to afford Int-61.3. MS (ES): m/z 184.26 [M+H]$^+$.

Synthesis of compound Int-61.4. To a solution of Int-61.3 (1.1 g, 6.0 mmol, 1.0 equiv) in THF (20 mL) was added thionyl chloride (2.15 mL, 30 mmol, 5.0 equiv). The reaction mixture was stirred at room temperature for 2 h. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% methanol in DCM as eluant) to afford Int-61.4. MS (ES): m/z 166.24 [M+H]$^+$.

Synthesis of compound Int-61. Compound Int-61 was prepared from Int-61.4 following the procedure described in the synthesis of Int-1. The crude product was used in the next step without further purification. MS (ES): m/z 208.3 [M+H]$^+$.

Preparation of Intermediate Int-62: 2-(2-(benzyloxy)ethyl)-6-cyclopropyl-4-isothiocyanatopyridazin-3(2H)-one

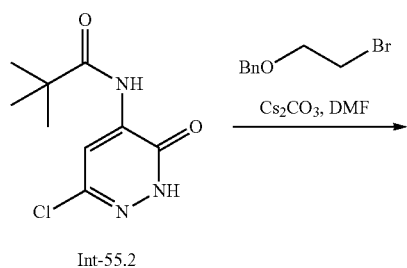

Int-55.2

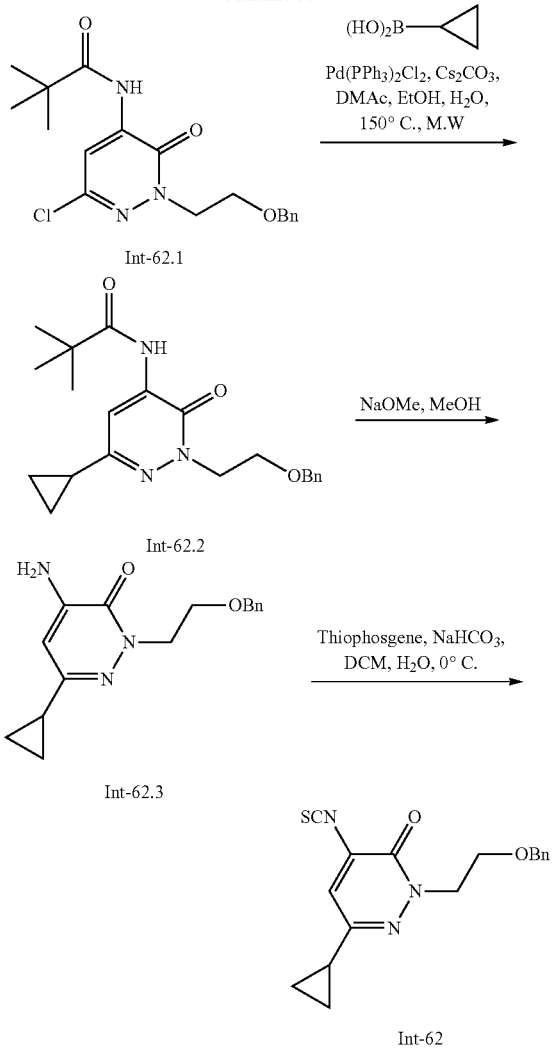

Synthesis of compound Int-62.1. To a suspension of Int-55.2 (3.5 g, 15.24 mmol, 1.0 equiv) and cesium carbonate (9.9 g, 30.48 mmol, 2.0 equiv) in DMF (35 mL) was added ((2-bromoethoxy)methyl)benzene (3.28 g, 15.24 mmol, 1.0 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by trituration with n-pentane to afford Int-62.1. MS (ES): m/z 364.5 [M+H]$^+$.

Synthesis of compound Int-62.2. Compound Int-62.2 was prepared from Int-62.1, following the procedure described in the synthesis of Int-55.4. The product was purified by flash column chromatography on silica gel (CombiFlash®, 15% ethyl acetate in hexane). MS (ES): m/z 370.4 [M+H]$^+$.

Synthesis of compound Int-62.3. Compound Int-62.3 was prepared from Int-62.2, following the procedure described in the synthesis of Int-55.5. The product was purified by flash column chromatography on silica gel (CombiFlash®, 30% ethyl acetate in hexane). MS (ES): m/z 286.2 [M+H]$^+$.

Synthesis of compound Int-62. Compound Int-62 was prepared from Int-62.3, following the procedure described in the synthesis of Int-1. The product was purified by flash Preparation of Intermediate Int-63: 3-isothiocyanato-1-methyl-5-(trifluoromethyl)pyridin-2(1H)-one

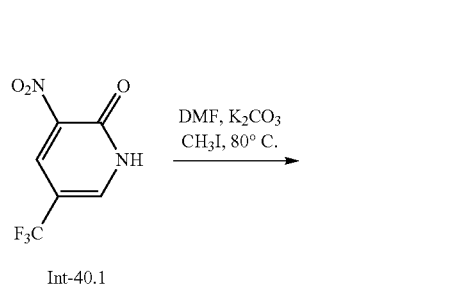

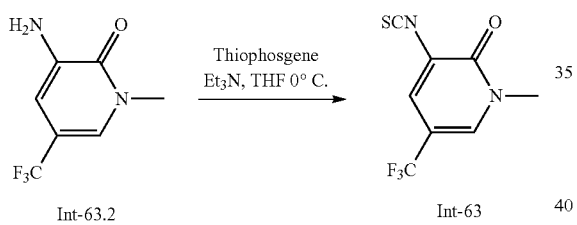

Synthesis of compound Int-63.1. A mixture of Int-40.1 (1.0 g, 4.81 mmol, 1.0 equiv), potassium carbonate (1.3 g, 9.62 mmol, 2.0 equiv) and methyl iodide (1.0 g, 7.21 mmol, 1.5 equiv) in DMF (15 mL) was stirred at 80° C. for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford Int-63.1. MS (ES): m/z 223.12 [M+H]+.

Synthesis of compound Int-63.2. A mixture of compound Int-63.1 (0.57 g, 2.57 mmol, 1.0 equiv) in methanol (18 mL) and 10% palladium on carbon (0.3 g) were stirred under hydrogen (1 atm) for 1 h. The reaction mixture was filtered through a pad of Celite® and rinsed with methanol. The filtrate was concentrated under reduced pressure to obtain Int-63.2. MS (ES): m/z 193.14 [M+H]+.

Synthesis of compound Int-63. Compound Int-63 was prepared from 63.2 following the procedure described in the synthesis of Int-59. The crude product was used in the next step without further purification. MS (ES): m/z 192.15 [M+H]+.

Preparation of Intermediate Int-64: 5-cyclopropyl-1-(3-(3,3-difluoropiperidin-1-yl)propyl)-3-isothiocyanatopyridin-2(1H)-one

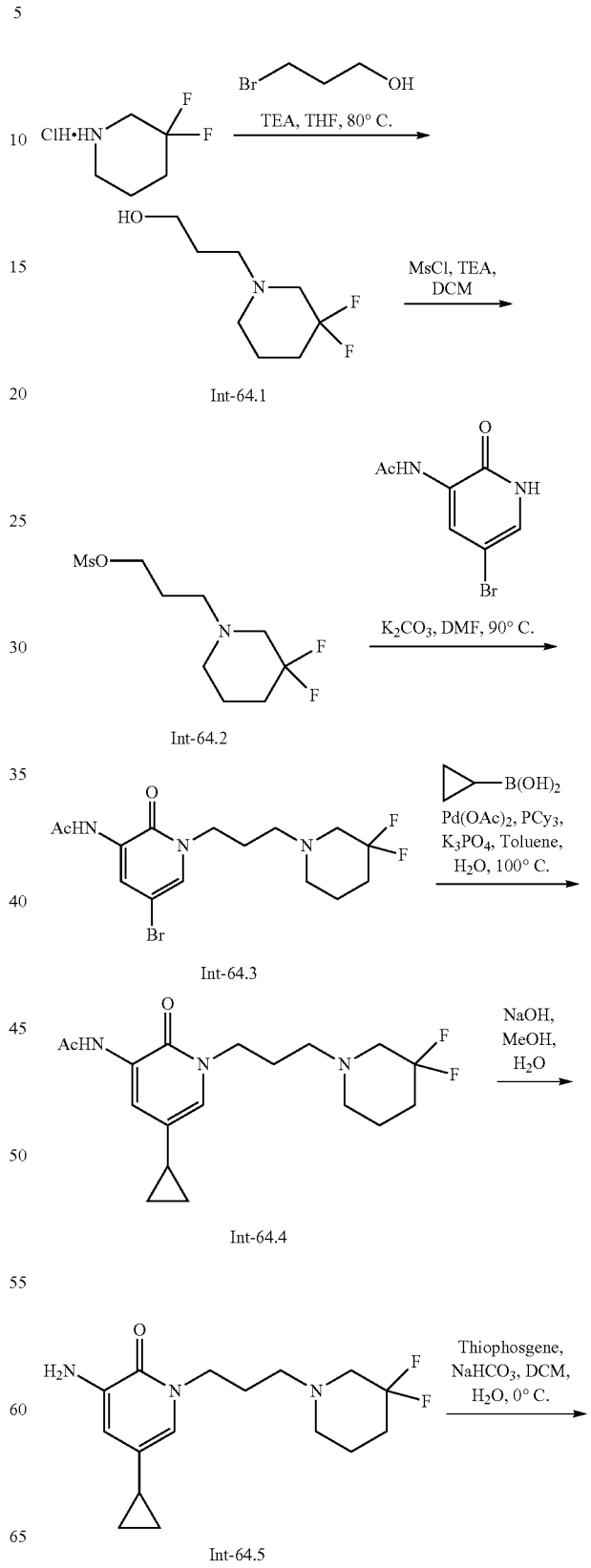

-continued

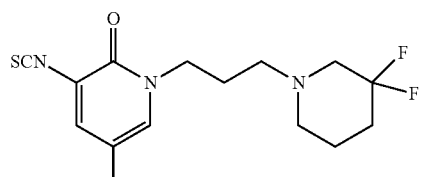

Int-64

Synthesis of compound Int-64.1. To a solution of 3,3-difluoropiperidine hydrochloride (1.0 g, 6.35 mmol, 1.0 equiv) in THF (10 mL) was added triethylamine (4.42 mL, 31.75 mmol, 5.0 equiv) at room temperature followed by addition of 3-bromopropan-1-ol (1.76 g, 12.7 mmol, 2.0 equiv). The reaction mixture was stirred at 80° C. for 12 h. It was poured over water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-64.1. $^1$H NMR (DMSO-d$_6$, 400 MHz): δ 4.43 (bs, 1H), 3.43-3.42 (m, 2H), 2.63-2.52 (m, 2H), 2.43-2.38 (m, 4H), 1.91-1.81 (m, 2H), 1.66-1.54 (m, 4H).

Synthesis of compound Int-64.2. Compound Int-64.2 was prepared from Int-64.1, following the procedure described in the synthesis of Int-32.3. The product was used in the next step without purification. $^1$H NMR (DMSO-d$_6$, 400 MHz): δ 4.28-4.27 (m, 2H), 3.36 (s, 3H), 3.22-3.17 (m, 4H), 3.13-3.07 (m, 2H), 2.06-2.04 (m, 4H), 1.82 (bs, 2H).

Synthesis of compound Int-64.3. Compound Int-64.3 was prepared from Int-64.1 and N-(5-bromo-2-oxo-1,2-dihydropyridin-3-yl)acetamide, following the procedure described in the synthesis of Int-32.4. The product was purified by preparative HPLC. MS (ES): m/z 393.2 [M+H]$^+$.

Synthesis of compound Int-64.4. Compound Int-64.4 was prepared from Int-64.3, following the procedure described in the synthesis of Int-23.2. The product was purified by flash column chromatography on silica gel (CombiFlash®, 2.0% methanol in DCM). MS (ES): m/z 354.4 [M+H]$^+$.

Synthesis of compound Int-64.5. To a solution of Int-64.4 (0.180 g, 0.509 mmol, 1.0 equiv) in methanol (5 mL) was added a solution of sodium hydroxide (0.814 g, 20.36 mmol, 40 equiv) in water (2 mL). The reaction mixture was heated at 55-60° C. for 3 h. It was concentrated under reduced pressure. The residue was added to water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-64.5. MS (ES): m/z 312.3 [M+H]$^+$.

Synthesis of compound Int-64. Compound Int-64 was prepared from Int-64.5, following the procedure described in the synthesis of Int-1. The product was purified by flash column chromatography on silica gel (CombiFlash®, 1.5% methanol in DCM). MS (ES): m/z 354.4 [M+H]$^+$.

Preparation of Intermediate Int-65: 2-(3-amino-5-cyclopropyl-2-oxopyridin-1(2H)-yl)acetonitrile

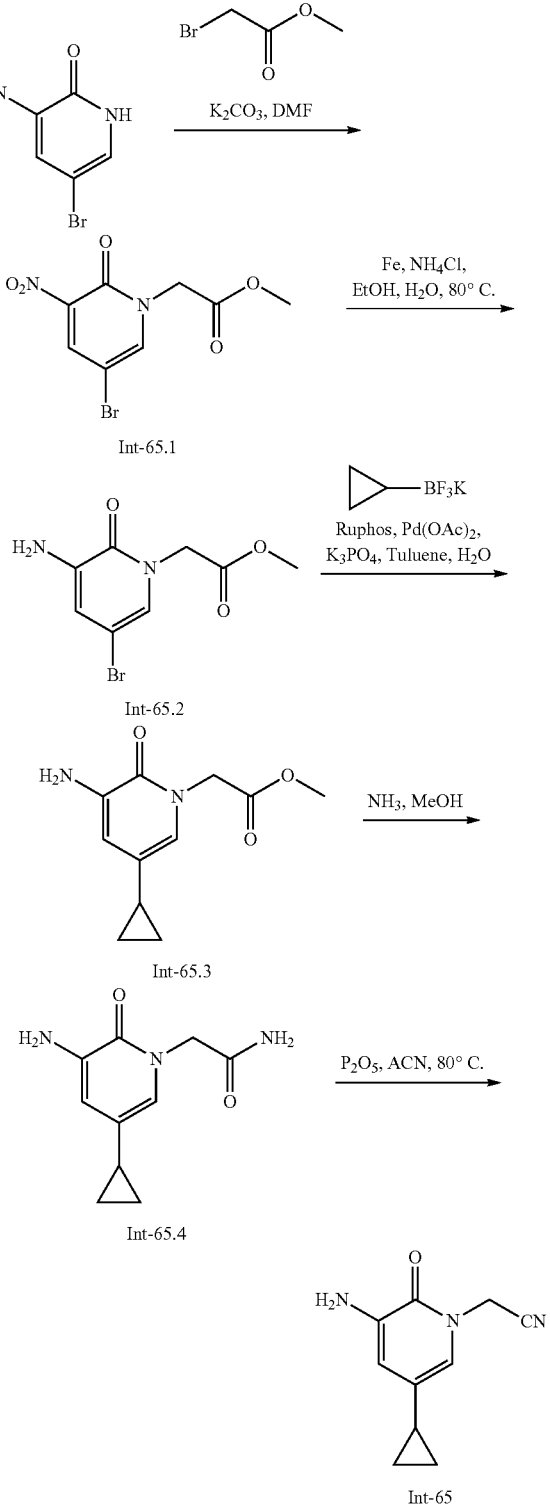

Synthesis of compound Int-65.1. To a mixture of 5-bromo-3-nitropyridin-2(1H)-one (5.0 g, 45.66 mmol, 1.0 equiv) and potassium carbonate (18.9 g, 136.98 mmol, 3.0 equiv) in DMF (50 mL) was added methyl 2-bromoacetate (10.48 g, 68.50 mmol, 1.5 equiv). The reaction mixture was stirred at room temperature for 5 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-65.1. MS (ES): m/z 292.0 [M+H]⁺.

Synthesis of compound Int-65.2 Compound Int-65.2 was prepared from Int-65.1, following the procedure described in the synthesis of Int-27.3. The product was purified by flash column chromatography on silica gel (CombiFlash®, 2.0% methanol in DCM). MS (ES): m/z 262.1 [M+H]⁺.

Synthesis of compound Int-65.3. Compound Int-65.3 was prepared from Int-65.2, following the procedure described in the synthesis of Int-23.2. The product was purified by flash column chromatography on silica gel (CombiFlash®, 2.3% methanol in DCM). MS (ES): m/z 223.2 [M+H]⁺.

Synthesis of compound Int-65.4. A solution of Int-65.3 (1.0 g, 4.59 mmol, 1.0 equiv) and ammonia (7 N in methanol, 50 mL) was stirred at room temperature for 12 h. It was concentrated under reduced pressure to afford crude compound which was triturated with diethyl ether to afford Int-65.4. MS (ES): m/z 208.1 [M+H]⁺.

Synthesis of compound Int-65. To a solution of Int-65.4 (0.640 g, 3.09 mmol, 1.0 equiv) in acetonitrile (10 mL) was added phosphorus pentoxide (0.877 g, 6.18 mmol, 2.0 equiv) and stirred at 80° C. for 12 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in DCM) to afford Int-65. MS (ES): m/z 190.0 [M+H]⁺.

Preparation of Intermediate Int-66: 1-(3-(3,3-difluoropiperidin-1-yl)propyl)-3-isothiocyanato-5-(trifluoromethyl)pyridin-2(1H)-one

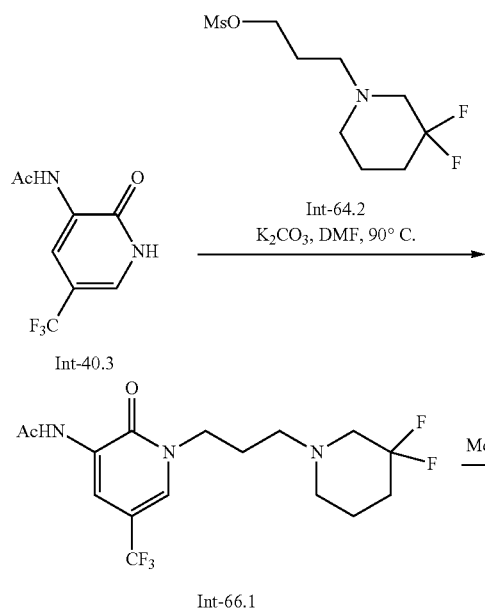

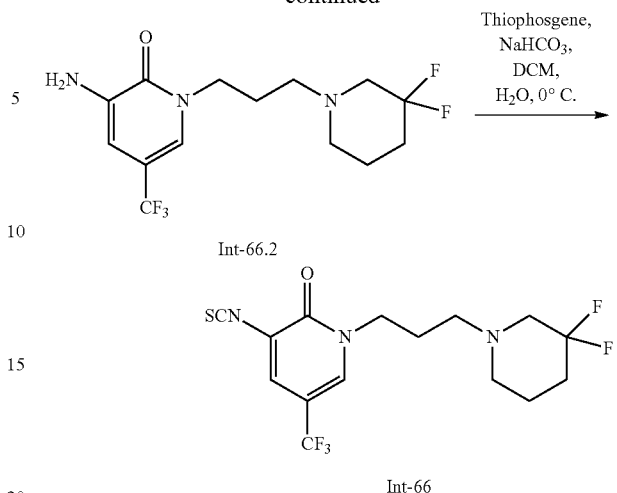

Synthesis of compound Int-66.1. Compound Int-66.1 was prepared from Int-40.3 and Int-64.2, following the procedure described in the synthesis of Int-32.4. The product was purified by preparative HPLC. MS (ES): m/z 382.3 [M+H]⁺.

Synthesis of compound Int-66.2. Compound Int-66.2 was prepared from Int-66.1, following the procedure described in the synthesis of trans-(±)-Int-44.7. The product was purified by flash column chromatography on silica gel (CombiFlash®, 2.3% methanol in DCM). MS (ES): m/z 340.3 [M+H]⁺.

Synthesis of compound Int-66. Compound Int-66 was prepared from Int-66.2, following the procedure described in the synthesis of Int-1. The product was purified by flash column chromatography on silica gel (CombiFlash®, 1.4% methanol in DCM). MS (ES): m/z 382.2 [M+H]⁺.

Preparation of Intermediate Int-67: (R)-6-cyclopropyl-4-isothiocyanato-2-(tetrahydrofuran-3-yl)pyridazin-3(2H)-one

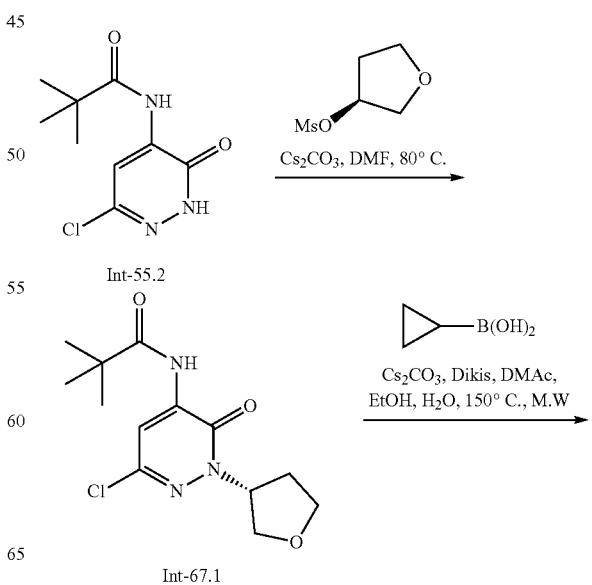

-continued

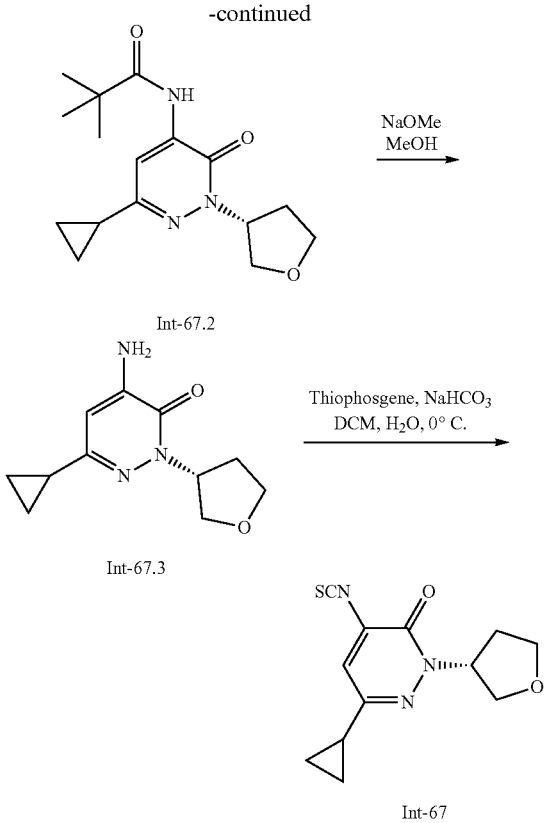

Int-67.2

Int-67.3

Int-67

Synthesis of compound Int-67.1. A mixture of Int-55.3 (10 g, 43.54 mmol, 1.0 equiv), cesium carbonate (35.4 g, 108.85 mmol, 2.5 equiv) and (S)-tetrahydrofuran-3-yl methanesulfonate (14.47 g, 87.08 mmol, 2.0 equiv) in DMF (100 mL) was stirred at 80° C. for 16 h. The reaction mixture was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 7.0% ethyl acetate in hexane) to afford Int-67.1. MS (ES): m/z 300.1 $[M+H]^+$.

Synthesis of compound Int-67.2. To a solution of Int-67.1 (1.3 g, 4.34 mmol, 1.0 equiv) in dimethylacetamide (10 mL), water (5 mL) and ethanol (2 mL) was added cyclopropylboronic acid (1.12 g, 13.01 mmol, 3.0 equiv), cesium carbonate (2.82 g, 8.68 mmol, 2.0 equiv) and dichlorobis (triphenylphosphine)palladium(II) (0.304 g, 0.434 mmol, 0.1 equiv). The reaction mixture was heated in a microwave reactor at 150° C. for 15 min. It was cooled to room temperature and filtered through a pad of Celite®. The filtrate was transferred into water and extracted with dichloromethane. The combined organic layers were washed with brine, dried over anhydrous sodium sulfate and concentrated under reduced pressure. The residue was purified by flash column chromatography on silica gel (CombiFlash®, 30% ethyl acetate in hexane) to afford Int-67.2. MS (ES): m/z 306.3 $[M+H]^+$.

Synthesis of compound Int-67.3. To a solution of Int-67.2 (0.345 g, 1.13 mmol, 1.0 equiv) in methanol (4 mL) was added sodium methoxide solution (25% in methanol, 0.4 mL, 1.695 mmol, 1.5 equiv). The reaction mixture was heated at 65° C. for 1 h. It was concentrated under reduced pressure. The residue was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford Int-67.3. MS (ES): m/z 222.1 $[M+H]^+$.

Synthesis of compound Int-67. Compound Int-67 was prepared from Int-67.3, following the procedure described in the synthesis of Int-1. The product was purified by flash column chromatography on silica gel (CombiFlash®, 20% ethyl acetate in hexane. MS (ES): m/z 264.1 $[M+H]^+$.

Preparation of Intermediate Int-68: (S)-6-cyclopropyl-4-isothiocyanato-2-(tetrahydrofuran-3-yl)pyridazin-3(2H)-one

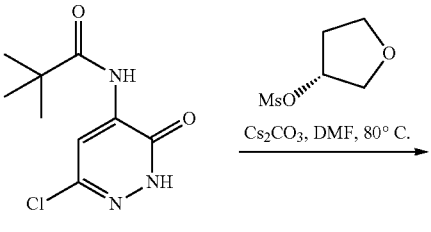

Int-55.2

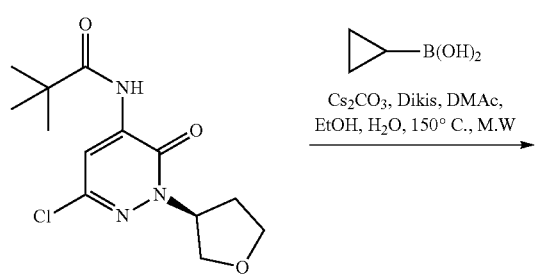

Int-68.1

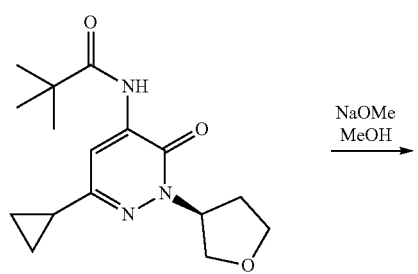

Int-68.2

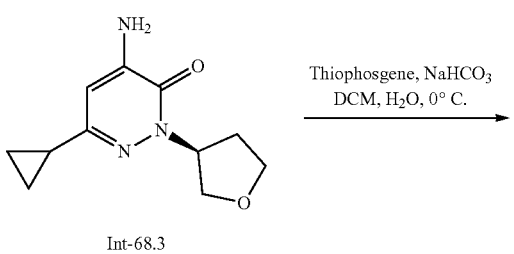

Int-68.3

-continued

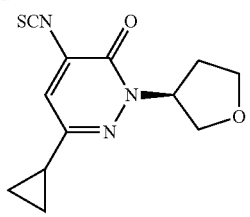

Int-68

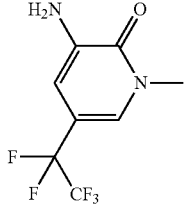

Int-69.4

TCDI, Imidazole, ACN, 0° C.

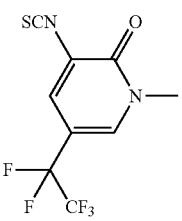

Int-69

Synthesis of compound Int-68. Compound Int-68 was prepared from Int-55.3, following the procedures described in the synthesis of Int-67. The product was purified by flash column chromatography on silica gel (CombiFlash®, 20% ethyl acetate in hexane. MS (ES): m/z 264.1 [M+H]$^+$.

Preparation of Intermediate Int-69: 3-isothiocyanato-1-methyl-5-(perfluoroethyl)pyridin-2(1H)-one

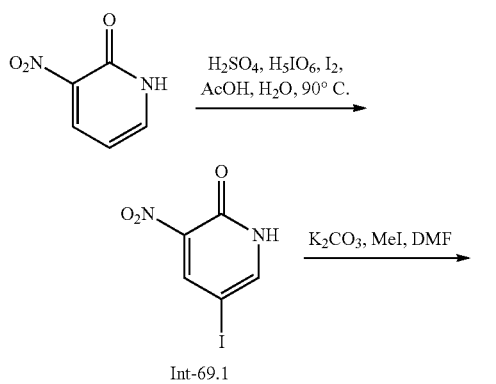

H$_2$SO$_4$, H$_5$IO$_6$, I$_2$, AcOH, H$_2$O, 90° C.

Int-69.1

K$_2$CO$_3$, MeI, DMF

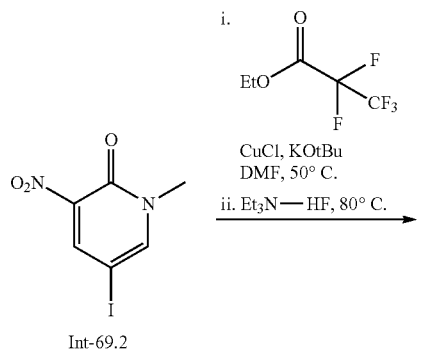

Int-69.2 i. <chemical structure: EtO-C(=O)-CF(F)-CF$_3$>
CuCl, KOtBu
DMF, 50° C.
ii. Et$_3$N—HF, 80° C.

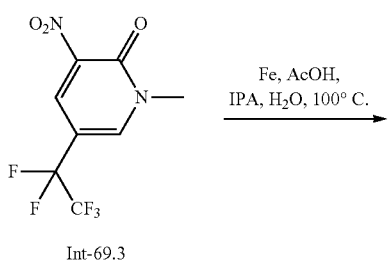

Int-69.3

Fe, AcOH, IPA, H$_2$O, 100° C.

Synthesis of compound Int-69.1. To a solution of 3-nitropyridin-2(1H)-one (5.0 g, 35.69 mmol, 1.0 equiv) in acetic acid (23 mL) and water (5 mL) was added conc. sulfuric acid (0.7 mL) and periodic acid (2.03 g, 8.92 mmol, 0.25 equiv). The reaction mixture was stirred at 90° C. for 15 min followed by addition of iodine (3.6 g, 14.27 mmol, 0.4 equiv) in portions. The reaction mixture was stirred for 20 min. It was cooled and saturated aqueous sodium thiosulphate solution (25 mL) was added. The precipitated solids were collected by filtration and rinsed with sodium thiosulphate (25 mL) then water. The solids were dried under vacuum to afford Int-69.1. MS (ES): m/z 266.5 [M+H]$^+$.

Synthesis of compound Int-69.2. To a mixture of Int-69.1 (4.5 g, 16.92 mmol, 1.0 equiv) in DMF (45 mL) was added potassium carbonate (5.83 g, 42.3 mmol, 2.5 equiv) and stirred for 30 min before the addition of methyl iodide (2.86 g, 20.30 mmol, 1.2 equiv). The reaction mixture was stirred at room temperature for 3 h. It was poured over ice-water and stirred. The precipitated solids were collected by filtration and dried under vacuum to afford Int-69.2. MS (ES): m/z 280.9 [M+H]$^+$.

Synthesis of compound Int-69.3. To a suspension of copper(I) chloride (0.706 g, 7.14 mmol, 2.0 equiv) in DMF (12 mL) was added potassium tert-butoxide (1.6 g, 14.28 mmol, 4.0 equiv) and stirred at room temperature for 1 h. Ethyl 2,2,3,3,3-pentafluoropropanoate (1.37 g, 7.14 mmol, 2.0 equiv) was added dropwise at 50° C. and stirred for 30 min. The reaction mixture was cooled to 0° C. and triethylamine trihydrofluoride (0.574 g, 3.57 mmol, 1.0 equiv) was added slowly. The reaction mixture was allowed to warm to room temperature, Int-69.2 (1.0 g, 3.57 mmol, 1.0 equiv) was added and stirred at 80° C. for 20 h. It was cooled to room temperature, transferred into dilute hydrochloric acid and extracted with ethyl acetate. The combined organic layers were washed with brine, dried over anhydrous sodium sulfate, filtered and concentrated under reduced pressure. The residue was purified by flash column chromatography on silica gel (CombiFlash®, 35% ethyl acetate in hexane) to afford Int-69.3. MS (ES): m/z 273.1 [M+H]$^+$.

Synthesis of compound Int-69.4. To a solution of Int-69.3 (0.180 g, 0.661 mmol, 1.0 equiv) in 2-propanol:water (2:1, 6 mL) was added iron powder (0.185 g, 3.305 mmol, 5.0 equiv) followed by acetic acid (0.198 g, 3.305 mmol, 5.0 equiv). The reaction mixture was heated at 100° C. for 3 h. It was poured over ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 45% ethyl acetate in hexane) to afford Int-69.4. MS (ES): m/z 243.1 [M+H]+.

Synthesis of compound Int-69. To a solution of Int-69.4 (0.125 g, 0.516 mmol, 1.0 equiv) in acetonitrile (5 mL) was added thiocarbonyldiimidazole (0.182 g, 1.032 mmol, 2.0 equiv) followed by imidazole (0.010 g, 0.154 mmol, 0.3 equiv). The reaction mixture was stirred at room temperature for 1 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-69. MS (ES): m/z 285.2 [M+H]+.

Preparation of Intermediate Int-70: 3-isothiocyanato-N-(2-morpholinoethyl)-5-(trifluoromethyl)benzamide

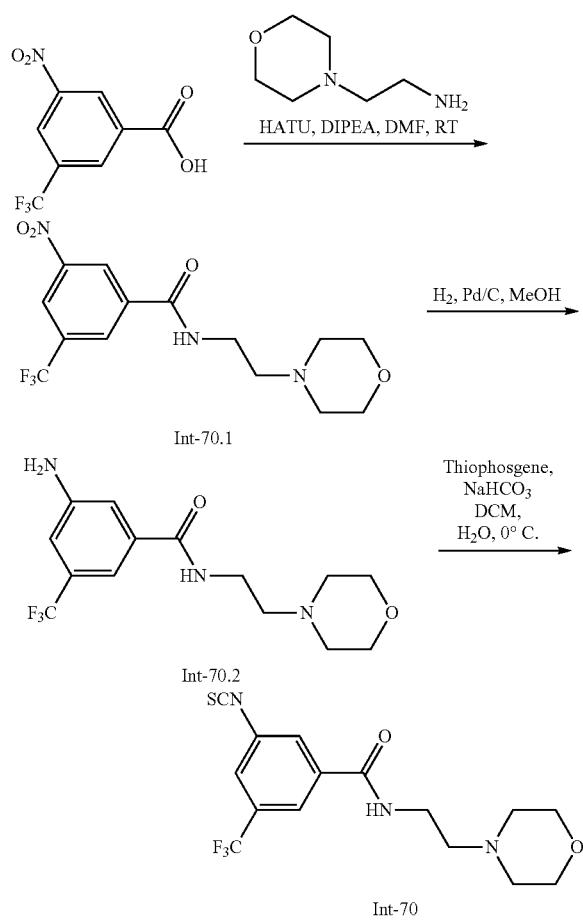

Synthesis of compound Int-70.1. To a solution of 3-nitro-5-(trifluoromethyl)benzoic acid (0.5 g, 2.13 mmol, 1.0 equiv) and 2-morpholinoethan-1-amine (0.359 g, 2.76 mmol, 1.3 equiv) in DMF (5 mL) was added 1-[bis(dimethylamino)methylene]-1H-1,2,3-triazolo[4,5-b]pyridinium-3-oxide (1.214 g, 3.195 mmol, 1.5 equiv). The reaction mixture was stirred at room temperature for 30 min. N,N-Diisopropylethylamine (1.1 mL, 6.39 mmol, 3.0 equiv) was added and stirred at for 16 h. The reaction mixture was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in DCM) to afford Int-70.1. MS (ES): m/z 348.0 [M+H]+.

Synthesis of compound Int-70.2. A mixture of compound Int-70.1 (0.300 g, 0.863 mmol, 1.0 equiv) and 10% palladium on carbon (0.200 g) in methanol (10 mL) was stirred under hydrogen (1 atm) for 1 h. The reaction mixture was filtered through a pad of Celite® and rinsed with methanol. The filtrate was concentrated under reduced pressure to afford Int-70.2. MS (ES): m/z 318.2 [M+H]+.

Synthesis of compound Int-70. Compound Int-70 was prepared from Int-70.2, following the procedures described in the synthesis of Int-1. The product was purified by flash column chromatography on silica gel (CombiFlash®, 1.0% methanol in DCM) t. MS (ES): m/z 359.9 [M+H]+.

Preparation of Intermediate cis-(±)-Int-71: cis-2-(3-amino-5-(tert-butyl)-1H-pyrazol-1-yl)cyclobutan-1-ol

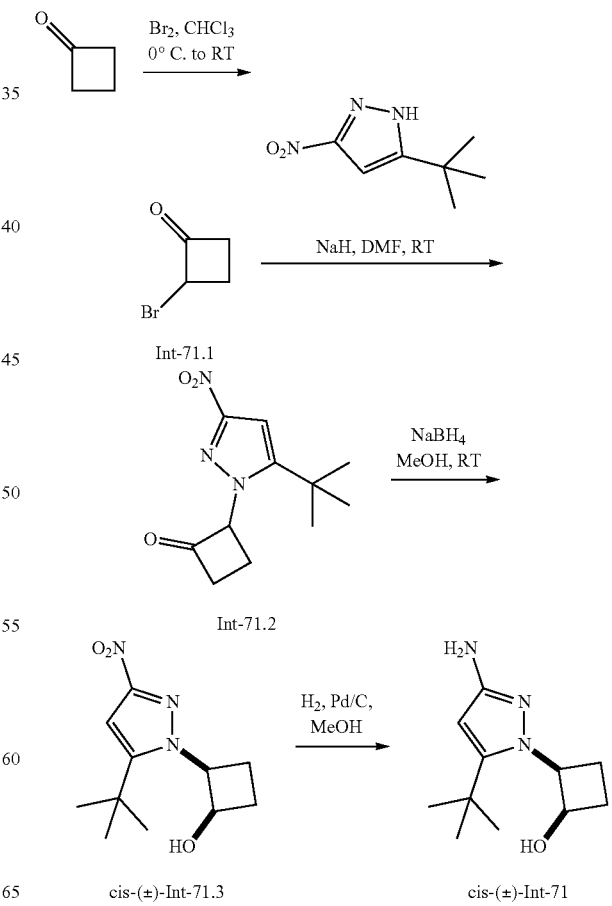

465

Synthesis of compound Int-71.1. To a solution of cyclobutanone (20 g, 285 mmol, 1.0 equiv) in chloroform (120 mL) was added solution of bromine (14.7 mL, 285 mmol, 1.0 equiv) in chloroform (80 mL) dropwise at 0° C. The reaction mixture was stirred at room temperature for 16 h. It was poured over ice-cold saturated sodium bicarbonate solution and stirred. The organic layer was separated washed with aqueous sodium bisulfite, brine, dried over anhydrous sodium sulfate and used for next step without purification.

Synthesis of compound Int-71.2. To a solution of 5-(tert-butyl)-3-nitro-1H-pyrazole (4.0 g, 23.64 mmol, 1.0 equiv) in DMF (100 mL) was added sodium hydride (1.89 g, 47.28 mmol, 2.0 equiv) in portions at 0° C. and stirred for 30 min followed by addition of Int-71.1 (chloroform solution from the previous step). The reaction mixture was stirred at room temperature for 1 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-71.2. MS (ES): m/z 238.3[M+H]$^+$.

Synthesis of compound cis-(±)-Int-71.3. To a solution of Int-71.2 (1.9 g, 8.01 mmol, 1.0 equiv) in methanol (20 mL) was added sodium borohydride (0.608 g, 16.02 mmol, 2.0 equiv) slowly and the reaction mixture was stirred at room temperature for 1 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford cis-(±)-Int-71.3. MS (ES): m/z 240.1 [M+H]$^+$.

Synthesis of compound cis-(±)-Int-71. A mixture of compound cis-(±)-Int-71.3 (0.300 g, 1.25 mmol, 1.0 equiv) and 10% palladium on carbon (0.150 g) in methanol (10 mL) was stirred under hydrogen (1 atm) for 3 h. The reaction mixture was filtered through a pad of Celite® and rinsed with methanol. The filtrate was concentrated under reduced pressure to afford cis-(f)-Int-71. MS (ES): m/z 210.1 [M+H]$^+$.

Preparation of Intermediate (±)-Int-72: 6-cyclopropyl-4-isothiocyanato-2-(tetrahydro-2H-pyran-3-yl)pyridazin-3(2H)-one

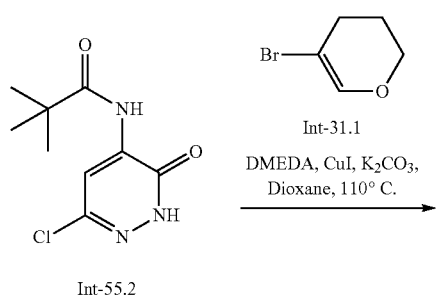

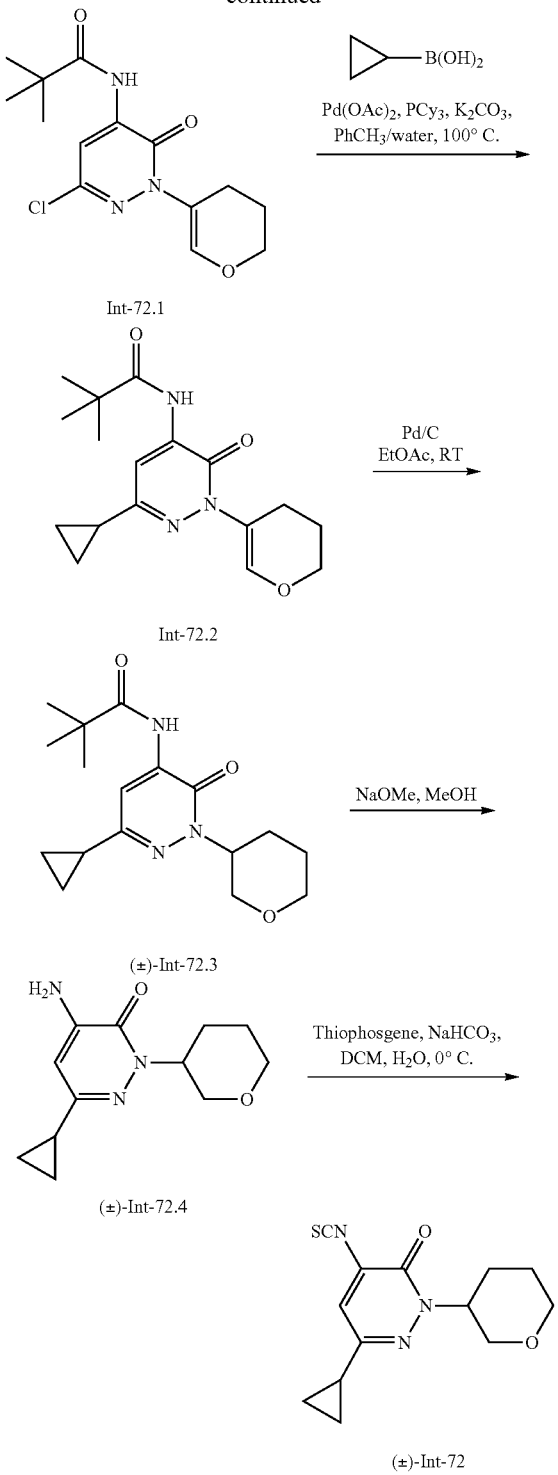

Synthesis of compound Int-72.1. A mixture of Int-55.3 (2 g, 8.71 mmol, 1.0 equiv), Int-31.1 (2.13 g, 13.06 mmol, 1.5 equiv) and potassium carbonate (2.40 g, 17.42 mmol, 2.0 equiv) in 1,4-dioxane (20 mL) was degassed by bubbling through a stream of argon for 15 min. Copper iodide (0.330 g, 1.74 mmol, 0.2 equiv) and 1,2-dimethylethylenediamine (0.306 g, 3.48 mmol, 0.4 equiv) were added and degassed for another 5 min. The reaction mixture was stirred at 110° C. for 16 h. It was cooled to room temperature, transferred into water and extracted with ethyl acetate. The combined organic layers were washed with brine, dried over anhydrous sodium sulfate, filtered and concentrated under reduced pressure. The residue was purified by column chromatography and compound was eluted in 20% ethyl acetate in hexane to afford Int-72.1. MS (ES): m/z 312.5 [M+H]+.

Synthesis of compound Int-72.2. Compound Int-72.2 was prepared from Int-72.1, following the procedure described in the synthesis of Int-23.2. The product was purified by flash column chromatography on silica gel (CombiFlash®, 30% ethyl acetate). MS (ES): m/z 318.3 [M+H]+.

Synthesis of compound (±)-Int-72.3. A mixture of Int-72.2 (0.610 g, 1.92 mmol, 1.0 equiv) and 10% palladium on charcoal (0.300 g) in ethyl acetate (20 mL) was stirred under hydrogen (1 atm) at room temperature for 2 h. It was filtered through a pad of Celite® and rinsed with ethyl acetate. The filtrate was concentrated under reduced pressure to afford (±)-Int-72.3. MS (ES): m/z 320.4 [M+H]+.

Synthesis of compound (±)-Int-72.4. To a solution of (±)-Int-72.3 (0.310 g, 0.970 mmol, 1.0 equiv) in methanol (10 mL) was added sodium methoxide solution (25% in methanol, 0.42 mL, 1.94 mmol, 2.0 equiv). The reaction mixture was heated at 65° C. for 1 h. It was concentrated under reduced pressure. The residue was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 45% ethyl acetate in hexane) to afford (f)-Int-72.4. MS (ES): m/z 236.2 [M+H]+.

Synthesis of compound (±)-Int-72. Compound (±)-Int-72 was prepared from (f)-Int-72.4, following the procedures described in the synthesis of Int-1. The product was purified by flash column chromatography on silica gel (CombiFlash®, 20% ethyl acetate in hexane) to afford 1.7 (0.149 g, 56.43%). MS (ES): m/z 278.3 [M+H]+.

Preparation of Intermediate Int-73: 4-(4-isothiocyanato-2-(trifluoromethyl)benzyl)morpholine

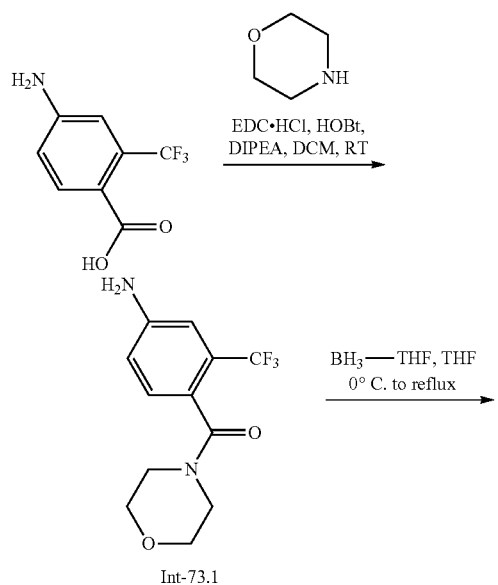

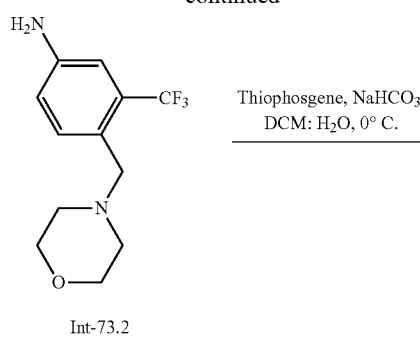

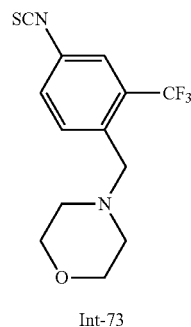

Int-73

Synthesis of compound Int-73.1. To a solution of 4-amino-2-(trifluoromethyl)benzoic acid (3.0 g, 14.62 mmol, 1.0 equiv) and morpholine (1.91 g, 21.93 mmol, 1.5 equiv) in DCM (60 mL) was added 1-hydroxybenzotriazole (2.96 g, 21.93 mmol, 1.5 equiv), 1-ethyl-3-(3-dimethylaminopropyl)carbodiimide hydrochloride (4.18 g, 21.93 mmol, 1.5 equiv), N,N-diisopropylethylamine (5.65 g, 43.86 mmol, 3.0 equiv) and stirred at room temperature for 3 h. The reaction mixture was poured over ice-water, stirred and extracted with ethyl acetate. The combined organic layers were washed with brine, dried over sodium sulfate, filtered and concentrated under reduced pressure. The residue was purified by flash column chromatography on silica gel (CombiFlash®, 1.2% methanol in DCM) to afford Int-73.1. MS (ES): m/z 275.2 [M+H]+.

Synthesis of compound Int-73.2. To a solution of Int-73.1 (1 g, 3.65 mmol, 1.0 equiv) in THF (10 mL) was added borane-THF (1.04 mL, 10.95 mmol, 3.0 equiv) at 0° C. The reaction mixture was heated to reflux for 3 h. it was cooled to room temperature and added a solution of 6 N hydrochloric acid (5 mL). It was heated to reflux for another 2 h, cooled to room temperature, poured over ice-water and extracted with ethyl acetate. The combined organic layers were washed with brine, dried over sodium sulfate, filtered and concentrated under reduced pressure. The residue was purified by flash column chromatography on silica gel (CombiFlash®, 1.0% methanol in DCM) to afford Int-73.2. MS (ES): m/z 261.3 [M+H]+.

Synthesis of compound Int-73. Compound Int-73 was prepared from Int-73.2 following the procedure described in the synthesis of Int-1. The crude product was purified by flash column chromatography on silica gel (CombiFlash®, 40% ethyl acetate in hexane). MS (ES): m/z 303.3 [M+H]+.

Preparation of Intermediate Int-74: 6-isothiocyanato-2,3,3-trimethyl-4-(trifluoromethyl)isoindolin-1-one

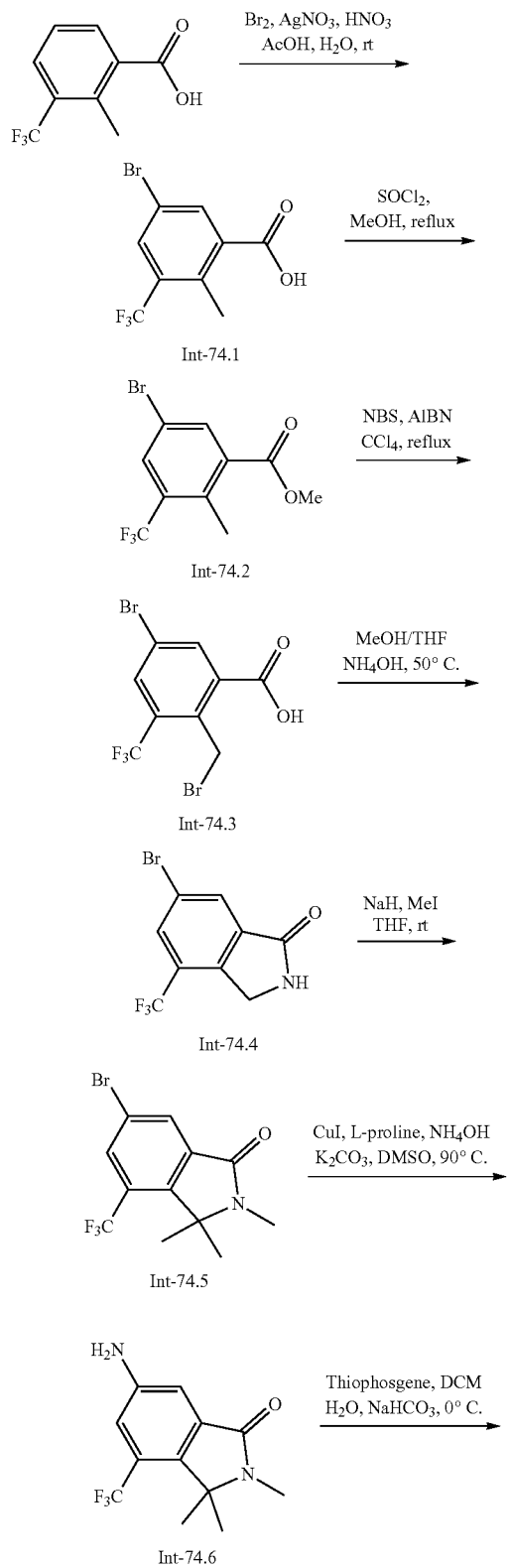

Synthesis of compound Int-47.1. To a solution of 2-methyl-3-(trifluoromethyl)benzoic acid (1.0 g, 4.90 mmol, 1.0 equiv) in 0.2 M aqueous acetic acid (20 mL) was added nitric acid (2.08 mL, 49 mmol, 10 equiv), bromine (0.86 g, 5.39 mmol, 1.1 equiv) followed by addition of 2.5 M aqueous silver nitrate solution (2.5 mL, 6.37 mmol, 1.3 equiv) over a period of 30 min. The reaction mixture was stirred at room temperature for 48 h. It was poured over ice-water, stirred and extracted with ethyl acetate. The combined organic layers were washed with brine, dried over anhydrous sodium sulfate, filtered and concentrated under reduced pressure to obtain Int-74.1. MS (ES): m/z 284.1 [M+H]+.

Synthesis of compound Int-74.2. To a solution of Int-74.1 (1.6 g, 5.65 mmol, 1.0 equiv) in methanol (20 mL) was added thionyl chloride (0.82 mL, 11.3 mmol, 2.0 equiv) at 0° C. The reaction mixture was heated to reflux for 4-5 h. It was poured over ice-water, stirred and extracted with ethyl acetate. The combined organic layers were washed with brine, dried over anhydrous sodium sulfate, filtered and concentrated under reduced pressure to obtain Int-74.2. MS (ES): m/z 298.1 [M+H]+.

Synthesis of compound Int-74.3. To a solution of Int-74.2 (0.710 g, 2.39 mmol, 1.0 equiv) in carbon tetrachloride (10 mL) was added N-bromosuccinimide (0.425 g, 2.39 mmol, 1.0 equiv) followed by azobisisobutyronitrile (0.078 g, 0.478 mmol, 0.2 equiv). The reaction mixture was heated to reflux for 1 h. It was poured over ice-water, stirred and extracted with dichloromethane. The combined organic layers were washed with brine, dried over anhydrous sodium sulfate, filtered and concentrated under reduced pressure to afford Int-74.3. MS (ES): m/z 362.9 [M+H]+.

Synthesis of compound Int-74.4. To a solution of Int-74.3 (0.480 g, 1.33 mmol, 1.0 equiv) in methanol (5 mL) and THF (5 mL) was added aqueous ammonium hydroxide solution (2.5 mL). The reaction mixture was stirred at 50° C. and heated to reflux for 4 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane as eluant) to afford Int-74.4. MS (ES): m/z 281.1 [M+H]+.

Synthesis of compound Int-74.5. To a solution of Int-74.4 (0.205 g, 0.732 mmol, 1.0 equiv) in THF (3 mL) was added sodium hydride (0.175 g, 3.66 mmol, 5.0 equiv) in small portions at 0° C. and stirred for 20 min. To the mixture was added methyl iodide (0.620 g, 4.39 mmol, 6.0 equiv). The reaction mixture was stirred at room temperature for 24 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (Combi- Flash®, 17% ethyl acetate in hexane as eluant) to afford Int-74.5. MS (ES): m/z 323.2 [M+H]+.

Synthesis of compound Int-74.6. To a solution of Int-74.5 (0.135 g, 0.419 mmol, 1.0 equiv) in dimethyl sulfoxide (5 mL) was added L-proline (0.019 g, 0.167 mmol, 0.4 equiv), copper iodide (0.046 g, 0.251 mmol, 0.6 equiv), potassium carbonate (0.289 g, 2.095 mmol, 5.0 equiv) followed by ammonium hydroxide solution (2 mL). The reaction mixture was stirred at 90-100° C. for 16 h. It was cooled to room temperature, transferred into water and extracted with ethyl acetate. The combined organic layers were washed with brine, dried over sodium sulfate and concentrated under reduced pressure. The residue was purified by flash column chromatography on silica gel (CombiFlash®, 30% methanol in DCM) to afford Int-74.6. MS (ES): m/z 259.3 [M+H]+.

Synthesis of compound Int-74. Compound Int-74 was prepared from Int-74.6 following the procedure described in the synthesis of Int-1. The crude product was used in the next step without further purification. MS (ES): m/z 301.3 [M+H]+.

Preparation of Intermediate Int-75: tert-butyl 6-(3-isothiocyanato-5-(trifluoromethyl)-1H-pyrazol-1-yl)-2-azaspiro[3.3]heptane-2-carboxylate

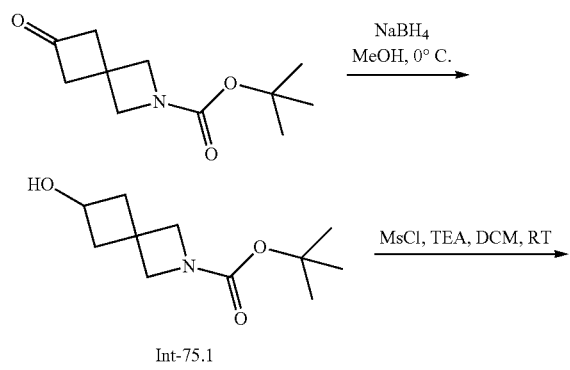

Int-75.1

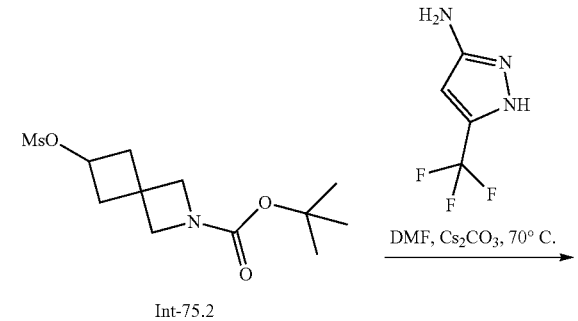

Int-75.2

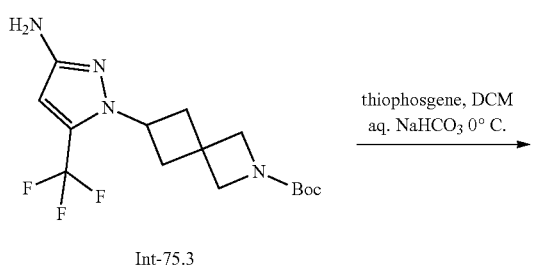

Int-75.3

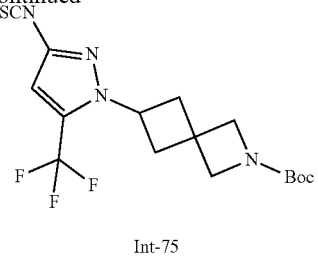

Int-75

Synthesis of compound Int-75.1. To a solution of tert-butyl 6-oxo-2-azaspiro[3.3]heptane-2-carboxylate (2.0 g, 9.47 mmol, 1.0 equiv) in methanol (20 mL) was added sodium borohydride (1.439 g, 37.88 mmol, 4.0 equiv) in small portions at 0° C. The reaction mixture was stirred at 0° C. for 2 h. It was poured over ice-water, stirred and extracted with ethyl acetate. The combined organic layers were washed with brine, dried over anhydrous sodium sulfate, filtered and concentrated under reduced pressure to obtain Int-75.1. MS (ES): m/z 214.3 [M+H]+.

Synthesis of compound Int-75.2. Compound Int-75.2 was prepared from Int-75.1, following the procedure described in the synthesis of Int-32.3. The product was used without purification. MS (ES): m/z 292.3 [M+H]+.

Synthesis of compound Int-75.3. Compound Int-75.3 was prepared from Int-75.2 and 5-(trifluoromethyl)-1H-pyrazol-3-amine, following the procedure described in the synthesis of Int-1.3. The isomers were isolated by preparative HPLC. MS (ES): m/z 347.3 [M+H]+.

Synthesis of compound Int-75. Compound Int-75 was prepared from Int-75.3 following the procedure described in the synthesis of Int-1. The crude product was used in the next step without further purification. MS (ES): m/z 389.4 [M+H]+.

Preparation of Intermediate Int-76: 3-isothiocyanato-1-(1-methyl-1H-pyrazol-4-yl)-5-(trifluoromethyl)pyridin-2(1H)-one

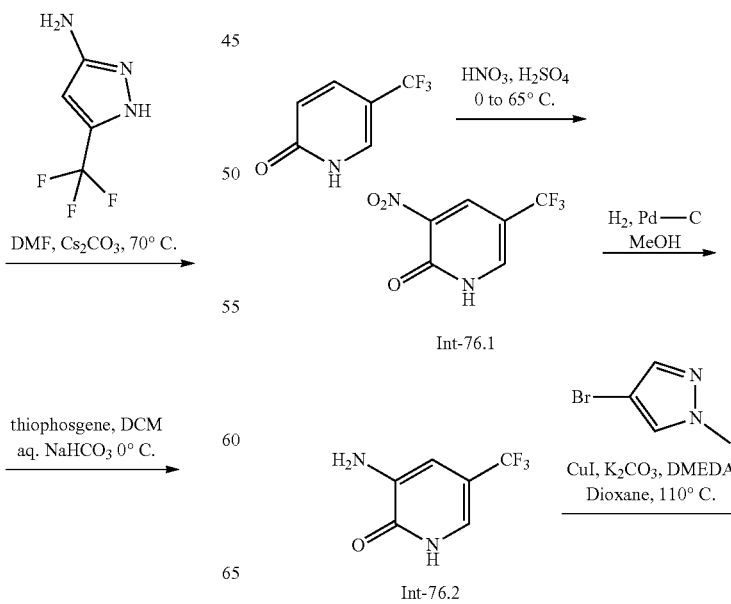

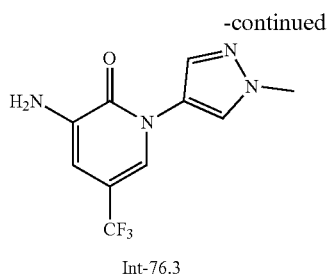

Int-76.3

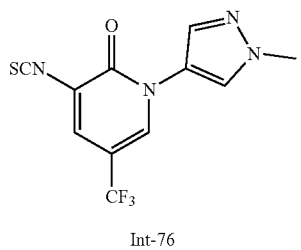

Int-76

Synthesis of compound Int-76.1 To a solution of 5-(trifluoromethyl)pyridin-2(1H)-one (5.0 g, 30.66 mmol, 1.0 equiv) in conc. sulfuric acid (25 mL) was added fuming nitric acid (8 mL) at 0° C. The reaction mixture was stirred at 65° C. for 6 h. It was poured over crushed ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-76.1. MS (ES): m/z 209.10 [M+H]$^+$.

Synthesis of compound Int-76.2. A mixture of compound Int-76.1 (8.0 g, 38.44 mmol, 1.0 equiv) and 10% palladium on carbon (3.0 g) in methanol (30 mL) was stirred under hydrogen (1 atm) for 2 h. The reaction mixture was filtered through a pad of Celite® and washed with methanol. The filtrate was concentrated under reduced pressure to afford Int-76.2 MS (ES): m/z 179.1 [M+H]$^+$.

Synthesis of compound Int-76.3. To a mixture of Int-76.2 (0.3 g, 2.81 mmol, 1.0 equiv), 4-bromo-1-methyl-1H-pyrazole (0.451 g, 2.81 mmol, 1.0 equiv) and potassium carbonate (0.775 g, 5.6 mmol, 2.0 equiv) in 1,4-dioxane (5 mL) was degassed for 15 min. Copper iodide (0.106 g, 0.56 mmol, 0.2 equiv) and N,N-dimethylethylenediamine (0.098 g, 1.12 mmol, 0.4 equiv) were added. The reaction mixture heated at 110° C. for 16 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.6% methanol in DCM) to afford Int-76.3. MS (ES): m/z 259.1 [M]$^+$.

Synthesis of compound Int-76. Compound Int-76 was prepared from Int-76.3 following the procedure described in the synthesis of Int-1. The product was purified by flash column chromatography on silica gel (CombiFlash®, 2% methanol in DCM). MS (ES): m/z 301.2 [M+H]$^+$.

Preparation of Intermediate Int-77: 2-(tert-butyl)-3-ethyl-5-isothiocyanatopyrimidin-4(3H)-one

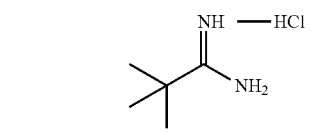


Int-77.1

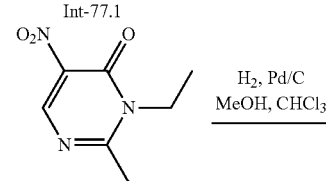

Int-77.2

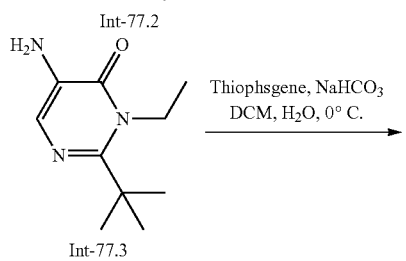

Int-77.3

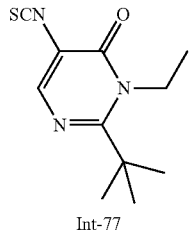

Int-77

Synthesis of compound Int-77.1. A mixture of ethyl 2-nitroacetate (4.0 g, 30.05 mmol, 1.0 equiv) and N,N-dimethylformamide dimethyl acetal (6.25 g, 52.58 mmol, 1.75 equiv) was stirred at room temperature for 1 h. To the mixture was added ethanol (80 mL), pivalimidamide hydrochloride (4.52 g, 33.06 mmol, 1.1 equiv) and triethylamine (8.3 mL, 60.1 mmol, 2.0 equiv). It was heated to reflux for 8 h. It was cooled to room temperature and concentrated under reduced pressure. The residue was purified by flash column chromatography on silica gel (CombiFlash®, 3.0% methanol in DCM) to afford Int-77.1. MS (ES): m/z 198.1 [M+H]$^+$.

Synthesis of compound Int-77.2. To a solution of compound Int-77.1 (0.200 g, 1.01 mmol, 1.0 equiv) in dimethylformamide (5 mL) was added potassium carbonate (0.209 g, 1.51 mmol, 1.5 equiv) and ethyl iodide (0.173 g, 1.11 mmol, 1.1 equiv). The mixture was stirred at room temperature for 3 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-77.2. MS (ES): m/z 226.2 [M+H]+.

Synthesis of compound Int-77.3. A mixture of compound Int-77.2 (0.120 g, 0.532 mmol, 1.0 equiv) and 10% palladium on carbon (0.060 g) in methanol (3 mL) and chloroform (3 mL) was stirred under hydrogen (1 atm) for 1 h. The reaction mixture was filtered through a pad of Celite® and washed with methanol. The filtrate was concentrated under reduced pressure to afford Int-77.3. MS (ES): m/z 196.0 [M+H]+.

Synthesis of compound Int-77. Compound Int-77 was prepared from Int-77.3 following the procedure described in the synthesis of Int-1. The product was purified by flash column chromatography on silica gel (CombiFlash®, 1.8% methanol in DCM). MS (ES): m/z 238.2 [M+H]+.

Preparation of Intermediate Int-78: 1-(3-isothiocyanato-5-(trifluoromethyl)phenyl)-4-methylpiperazine

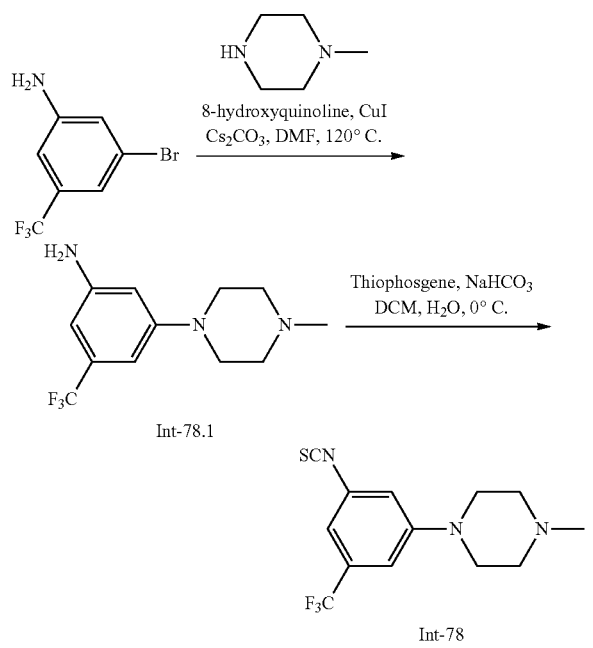

Synthesis of compound Int-78.1. A mixture of 3-bromo-5-(trifluoromethyl)aniline (0.500 g, 2.08 mmol, 1.0 equiv), 1-methylpiperazine (0.834 g, 8.33 mmol, 4.0 equiv) and cesium carbonate (1.35 g, 4.16 mmol, 2.0 equiv) in DMF (5 mL) was degassed by bubbling argon through for 10 min. Under argon atmosphere copper iodide (0.197 g, 1.04 mmol, 0.5 equiv) and 8-hydroxyquinoline (0.090 g, 0.624 mmol, 0.3 equiv) were added and degassed for another 5 min. The reaction mixture was stirred at 120° C. for 16 h. It was cooled to room temperature, filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 7% methanol in DCM) to afford Int-78.1. MS (ES): m/z 260.1 [M+H]+.

Synthesis of compound Int-78. Compound Int-78 was prepared from Int-78.1 following the procedure described in the synthesis of Int-1. The product was purified by flash column chromatography on silica gel (CombiFlash®, 3.0% methanol in DCM). MS (ES): m/z 302.3 [M+H]+.

Preparation of Intermediate Int-79: 4,4-difluoro-1-(4-isothiocyanato-2-(trifluoromethyl)benzyl)piperidine

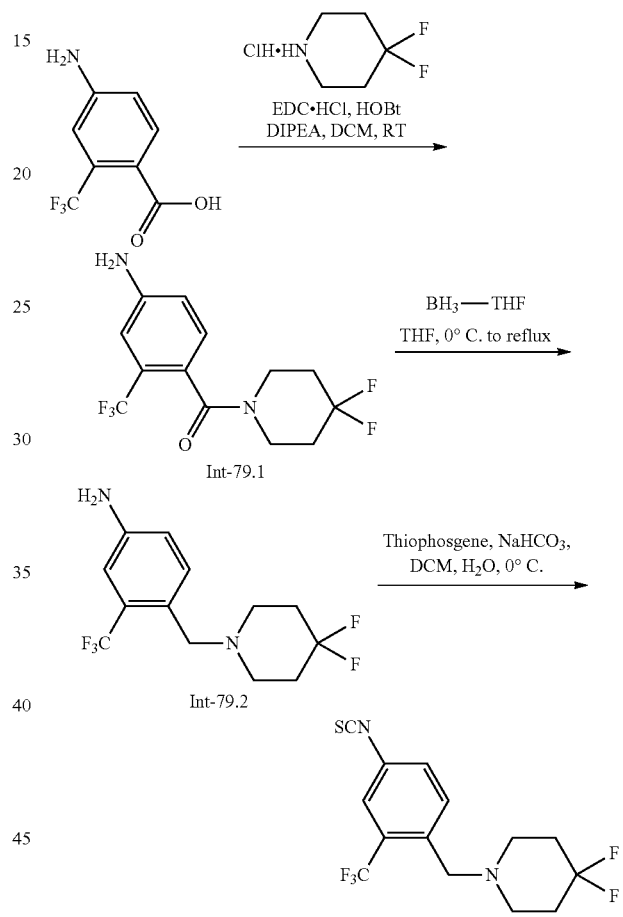

Synthesis of compound Int-79.1. A mixture of 4-amino-2-(trifluoromethyl)benzoic acid (1.0 g, 4.87 mmol, 1.0 equiv), 4,4-difluoropiperidine hydrochloride (1.15 g, 7.31 mmol, 1.5 equiv), 1-hydroxybenzotriazole (0.986 g, 7.30 mmol, 1.5 equiv), 1-ethyl-3-(3-dimethylaminopropyl)carbodiimide hydrochloride (1.39 g, 7.30 mmol, 1.5 equiv) and N,N-diisopropylethylamine (2.5 mL, 14.61 mmol, 3.0 equiv) in DCM (20 mL) was stirred at room temperature for 3 h. It was poured over ice cold water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.4% methanol in DCM) to afford Int-79.1. MS (ES): m/z 309.2 [M+H]+.

Synthesis of compound Int-79.2. To a solution of Int-79.1 (0.680 g, 2.21 mmol, 1.0 equiv) in THF (10 mL) was added borane dimethylsulfide (0.63 mL, 6.63 mmol, 3.0 equiv) at 0° C. The reaction mixture was heated to reflux for 3 h. It was cooled to room temperature and added 6 N hydrochloric acid (5 mL). The reaction mixture was heated to reflux for another 2 h. It was cooled to room temperature, transferred into ice cold 8 N sodium hydroxide solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in DCM) to afford Int-79.2. MS (ES): m/z 295.3 [M+H]+.

Synthesis of compound Int-79. Compound Int-79 was prepared from Int-79.2 following the procedure described in the synthesis of Int-1. The product was purified by flash column chromatography on silica gel (CombiFlash®, 35% ethyl acetate in hexane). MS (ES): m/z 337.3 [M+H]+.

Preparation of Intermediate Int-80: 3,3-difluoro-1-(4-isothiocyanato-2-(trifluoromethyl)benzyl)piperidine

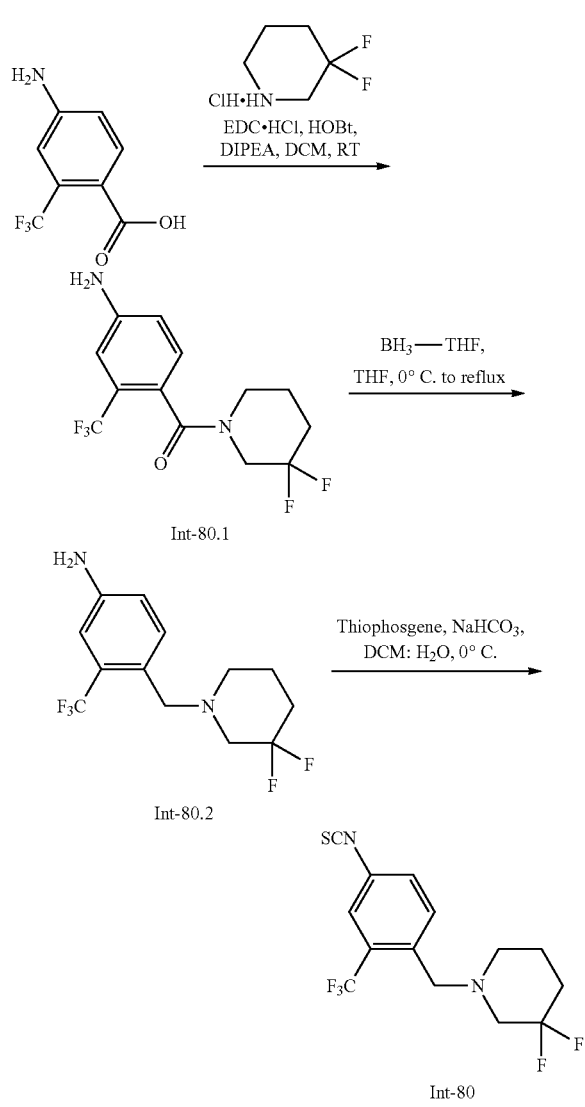

Synthesis of compound Int-80. Compound Int-80 was prepared by following the procedures described in the synthesis of Int-79. The final product was purified by flash column chromatography on silica gel (CombiFlash®, 35% ethyl acetate in hexane). MS (ES): m/z 337.3 [M+H]+.

Preparation of Intermediate Int-81: (S)-1-(4-isothiocyanato-2-(trifluoromethyl)benzyl)-3-methoxypyrrolidine

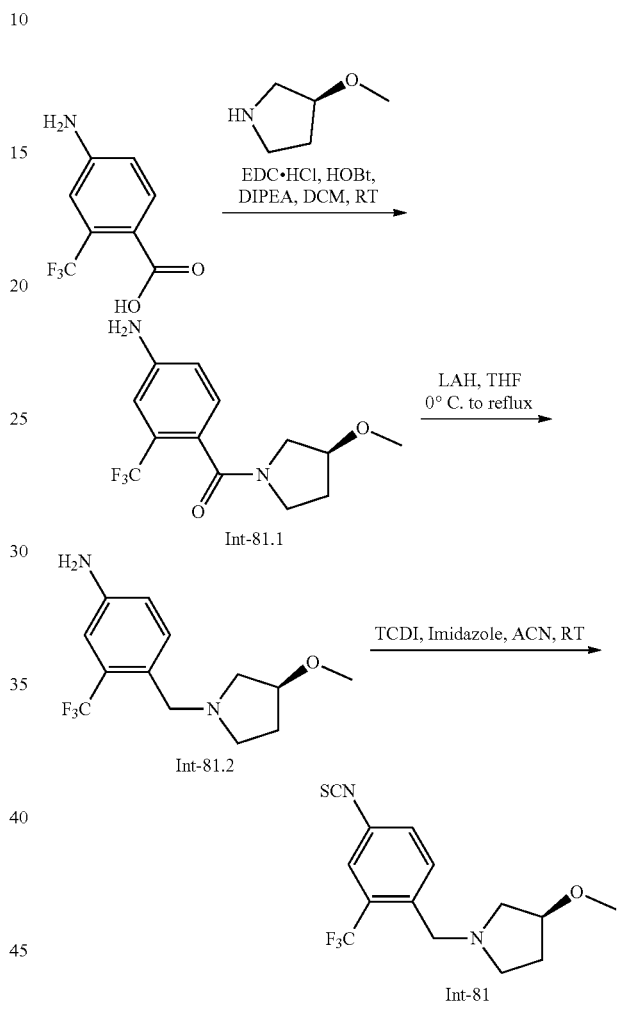

Synthesis of compound Int-81.1. Compound Int-81.1 was prepared from 4-amino-2-(trifluoromethyl)benzoic acid and (S)-3-methoxypyrrolidine, following the procedures described in the synthesis of Int-79.1. The product was purified by flash column chromatography on silica gel (CombiFlash®, 5.3% methanol in DCM). MS (ES): m/z 289.2 [M+H]+.

Synthesis of compound Int-81.2. To a solution of Int-81.1 (0.270 g, 0.936 mmol, 1.0 equiv) in THF (10 mL) was added lithium aluminum hydride (1 M in THF, 2.8 mL, 2.808 mmol, 3.0 equiv) at 0° C. The reaction mixture was heated to reflux for 30 min. It was cooled to room temperature, transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 6.2% methanol in DCM) to afford Int-81.2. MS (ES): m/z 275.3 [M+H]+.

Synthesis of compound Int-81. Compound Int-81 was prepared from Int-81.2, following the procedures described in the synthesis of Int-69. The product was purified by flash column chromatography on silica gel (CombiFlash®, 35% ethyl acetate in hexane). MS (ES): m/z 317.2 [M+H]$^+$.

Preparation of Intermediate Int-82: (R)-1-(4-isothiocyanato-2-(trifluoromethyl)benzyl)-3-methoxypyrrolidine

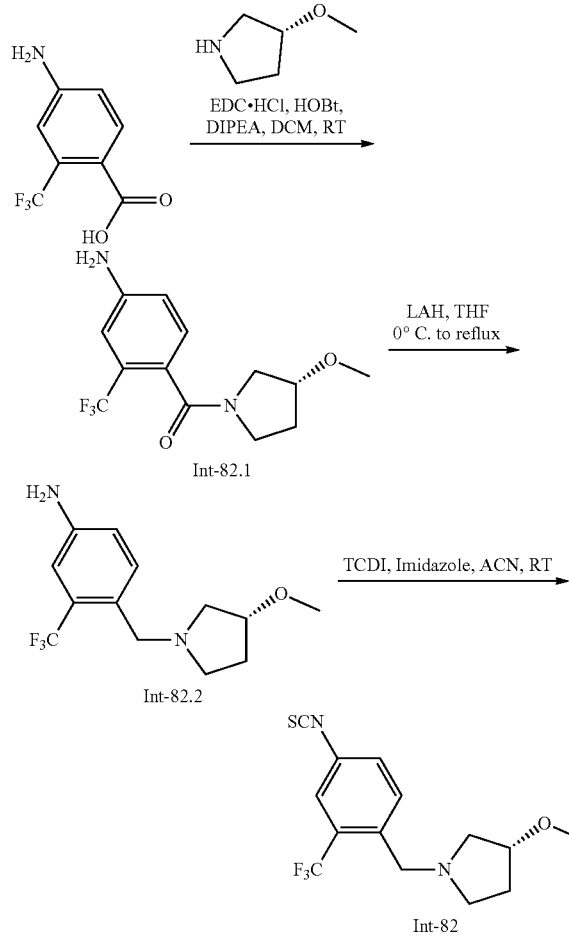

Synthesis of compound Int-82.1. Compound Int-82.1 was prepared from 4-amino-2-(trifluoromethyl)benzoic acid and (R)-3-methoxypyrrolidine, following the procedures described in the synthesis of Int-79.1. The product was purified by flash column chromatography on silica gel (CombiFlash®, 5.3% methanol in DCM). MS (ES): m/z 289.2 [M+H]$^+$.

Synthesis of compound Int-82.2. Compound Int-82.2 was prepared from Int-82.1, following the procedures described in the synthesis of Int-81.2. The product was purified by flash column chromatography on silica gel (CombiFlash®, 6.2% methanol in DCM). MS (ES): m/z 275.3 [M+H]$^+$.

Synthesis of compound Int-82. Compound Int-82 was prepared from Int-82.2, following the procedures described in the synthesis of Int-69. The product was purified by flash column chromatography on silica gel (CombiFlash®, 35% ethyl acetate in hexane). MS (ES): m/z 317.1 [M+H]$^+$.

Preparation of Intermediate Int-83: 1-cyclopropyl-3-isothiocyanato-5-(trifluoromethyl)pyridin-2(1H)-one

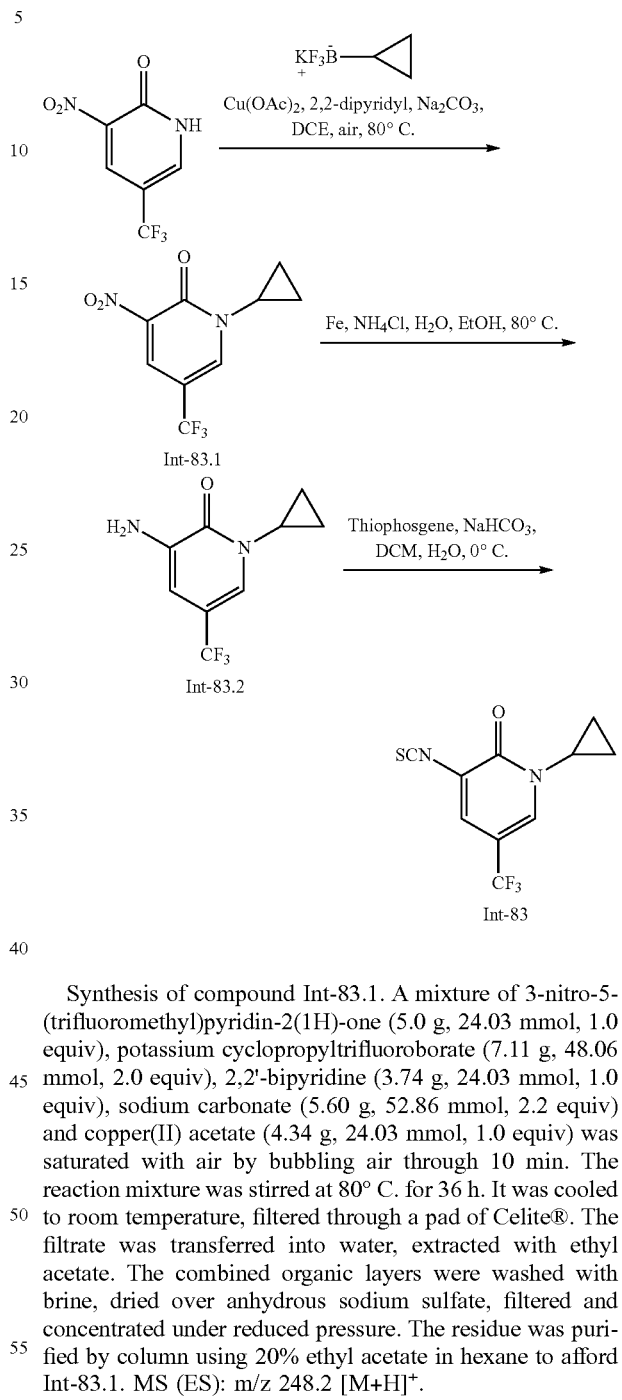

Synthesis of compound Int-83.1. A mixture of 3-nitro-5-(trifluoromethyl)pyridin-2(1H)-one (5.0 g, 24.03 mmol, 1.0 equiv), potassium cyclopropyltrifluoroborate (7.11 g, 48.06 mmol, 2.0 equiv), 2,2'-bipyridine (3.74 g, 24.03 mmol, 1.0 equiv), sodium carbonate (5.60 g, 52.86 mmol, 2.2 equiv) and copper(II) acetate (4.34 g, 24.03 mmol, 1.0 equiv) was saturated with air by bubbling air through 10 min. The reaction mixture was stirred at 80° C. for 36 h. It was cooled to room temperature, filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by column using 20% ethyl acetate in hexane to afford Int-83.1. MS (ES): m/z 248.2 [M+H]$^+$.

Synthesis of compound Int-83.2. Compound Int-83.2 was prepared from Int-83.1, following the procedure described in the synthesis of 3.7. The product was purified by flash column chromatography on silica gel (CombiFlash®, 2.4% methanol in DCM). MS (ES): m/z 219.1 [M+H]$^+$.

Synthesis of compound Int-83. Compound Int-83 was prepared from Int-83.2 following the procedure described in the synthesis of Int-1. The product was purified by column using 50% ethyl acetate in hexane). MS (ES): m/z 261.2 [M+H]$^+$.

Preparation of Intermediate Int-84: 1-(3-isothiocyanato-5-(trifluoromethyl)phenyl)-4-methyl-1H-imidazole

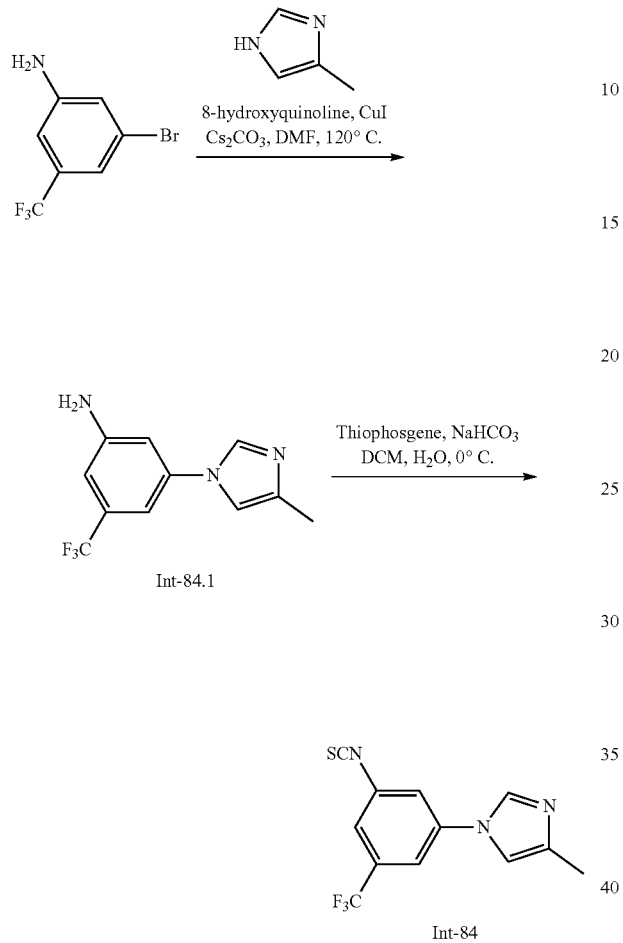

Int-84.1

Int-84

Synthesis of compound Int-84.1 A mixture of 3-bromo-5-(trifluoromethyl)aniline (0.500 g, 2.08 mmol, 1.0 equiv), 4-methyl-1H-imidazole (0.205 g, 2.5 mmol, 1.2 equiv) and cesium carbonate (1.35 g, 4.16 mmol, 2.0 equiv) in dimethyl sulfoxide (5 mL) was degassed by bubbling argon through for 10 min. Under argon atmosphere copper iodide (0.055 g, 0.291 mmol, 0.14 equiv) and 8-hydroxyquinoline (0.042 g, 0.291 mmol, 0.14 equiv) were added and degassed for another 5 min. The reaction mixture was stirred at 120° C. for 6 h. It was cooled to room temperature, filtered through a pad of Celite®. The filtrate was transferred into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 3% methanol in DCM) to afford Int-84.1. MS (ES): m/z 242.1 [M+H]+.

Synthesis of compound Int-84. Compound Int-84 was prepared from Int-84.1 following the procedure described in the synthesis of Int-1. The product was purified by flash column chromatography on silica gel (CombiFlash®, 1.2% methanol in DCM). MS (ES): m/z 291.5 [M+H]+.

Preparation of Intermediate Int-85: (S)-3-((3-methoxypyrrolidin-1-yl)methyl)-5-(trifluoromethyl)aniline

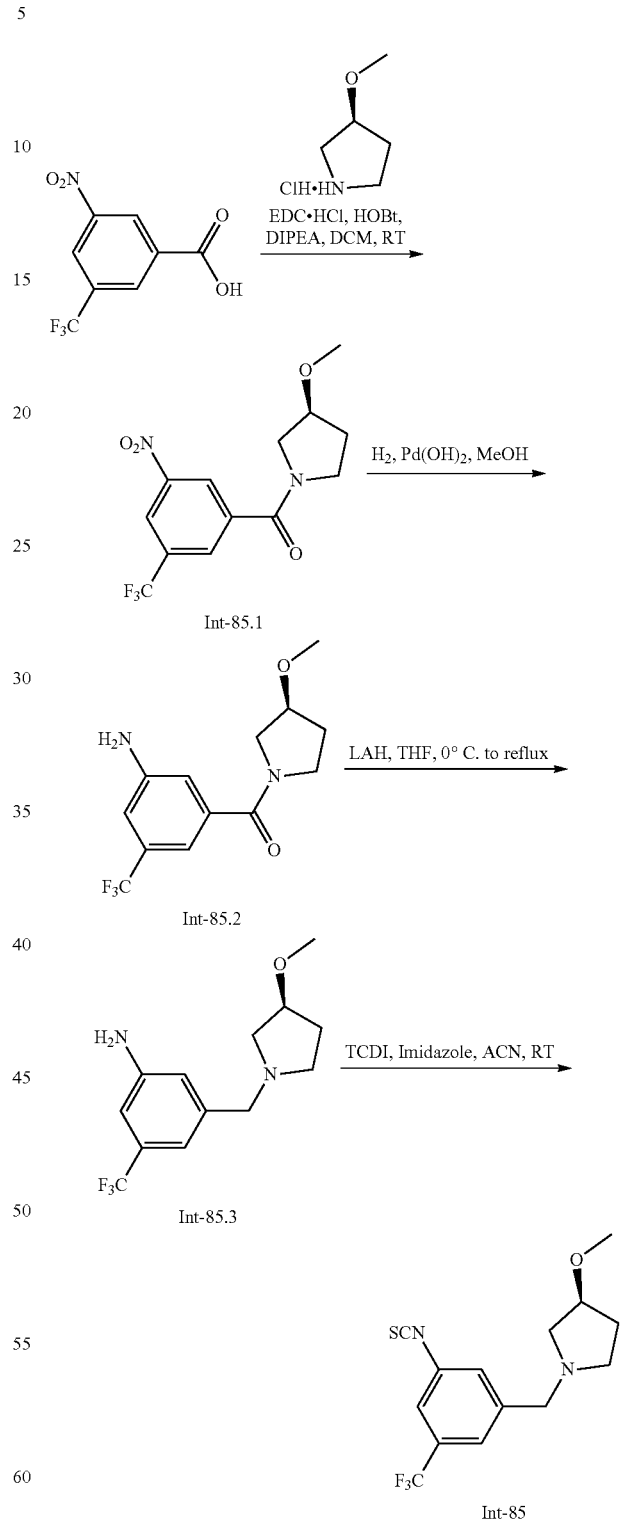

Int-85.1

Int-85.2

Int-85.3

Int-85

Synthesis of compound Int-85.1. Compound Int-85.1 was prepared from 3-nitro-5-(trifluoromethyl)benzoic acid and (S)-3-methoxypyrrolidine hydrochloride, following the procedures described in the synthesis of Int-79.1. The product was purified by flash column chromatography on silica gel (CombiFlash®, 40% ethyl acetate in hexane). MS (ES): m/z 319.1 [M+H]+.

Synthesis of compound Int-85.2. A mixture of compound Int-85.1 (0.810 g, 2.55 mmol, 1.0 equiv) and 20% palladium hydroxide (0.400 g) in methanol (10 mL) was stirred under hydrogen (1 atm) for 2 h. The reaction mixture was filtered through a pad of Celite® and rinsed with methanol. The filtrate was concentrated under reduced pressure to afford Int-85.2. MS (ES): m/z 289.1 [M+H]+.

Synthesis of compound Int-85.3. Compound Int-85.3 was prepared from Int-85.2 following the procedure described in the synthesis of Int-81.2. The product was purified by flash column chromatography on silica gel (CombiFlash®, 3.0% methanol in DCM). MS (ES): m/z 275.3 [M+H]+.

Synthesis of compound Int-85. Compound Int-85 was prepared from Int-85.3, following the procedures described in the synthesis of Int-69. The product was purified by flash column chromatography on silica gel (CombiFlash®, 40% ethyl acetate in hexane). MS (ES): m/z 317.2 [M+H]+.

Preparation of Intermediate Int-86: (R)-3-((3-methoxypyrrolidin-1-yl)methyl)-5-(trifluoromethyl)aniline

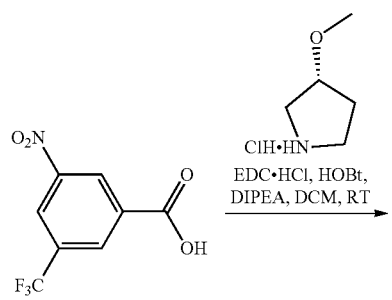

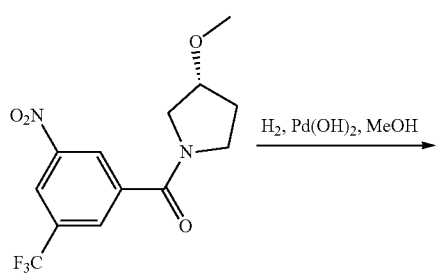

Int-86.2

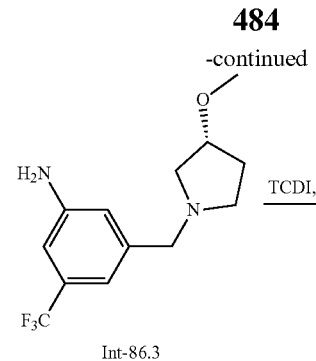

Int-86.3

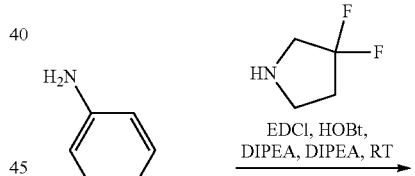

Int-86

Synthesis of compound Int-86. Compound Int-86 was prepared following the procedure described in the synthesis of Int-85. The product was purified by flash column chromatography on silica gel (CombiFlash®, 3.0% methanol in DCM). MS (ES): m/z 317.2 [M+H]+.

Preparation of Intermediate Int-87: 3,3-difluoro-1-(4-isothiocyanato-2-(trifluoromethyl)benzyl)pyrrolidine

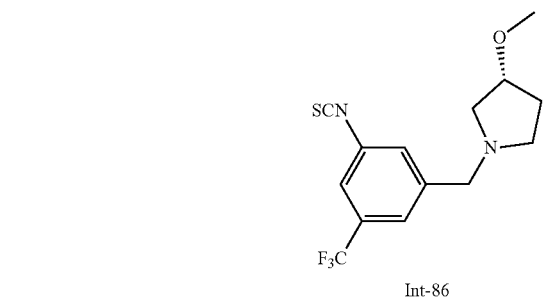

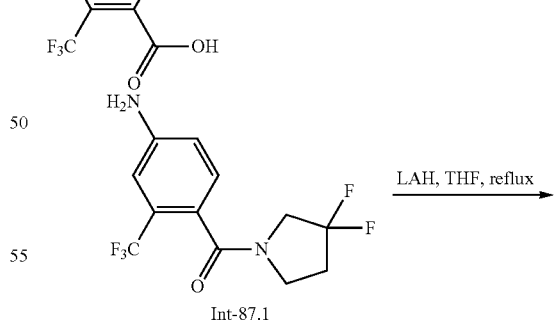

Int-87.1

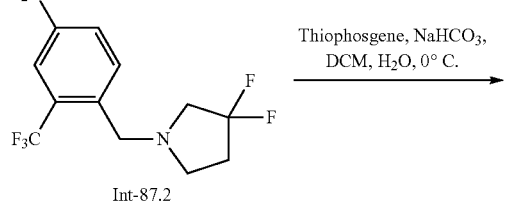

Int-87.2

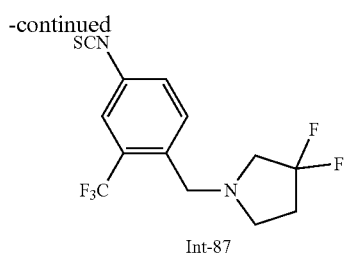

Int-87

Synthesis of compound Int-87.1. Compound Int-87.1 was prepared from 4-amino-2-(trifluoromethyl)benzoic acid and 3,3-difluoropyrrolidine, following the procedure described in the synthesis of Int-79.1. The product was purified by flash column chromatography on silica gel (CombiFlash®, 2.6% methanol in DCM). MS (ES): m/z 295.2 [M+H]$^+$.

Synthesis of compound Int-87.2. Compound Int-87.2 was prepared from Int-87.1, following the procedures described in the synthesis of Int-81.2. The product was purified by flash column chromatography on silica gel (CombiFlash®, 25% ethyl acetate in hexane). MS (ES): m/z 281.2 [M+H]$^+$.

Synthesis of compound I-87. Compound Int-87 was prepared from Int-87.2 following the procedure described in the synthesis of Int-1. The product was purified by column chromatography 20% ethyl acetate in hexane). MS (ES): m/z 323.3 [M+H]$^+$.

Preparation of Intermediate Int-88: (S)-3-(benzyloxy)-1-(4-isothiocyanato-2-(trifluoromethyl)benzyl)pyrrolidine

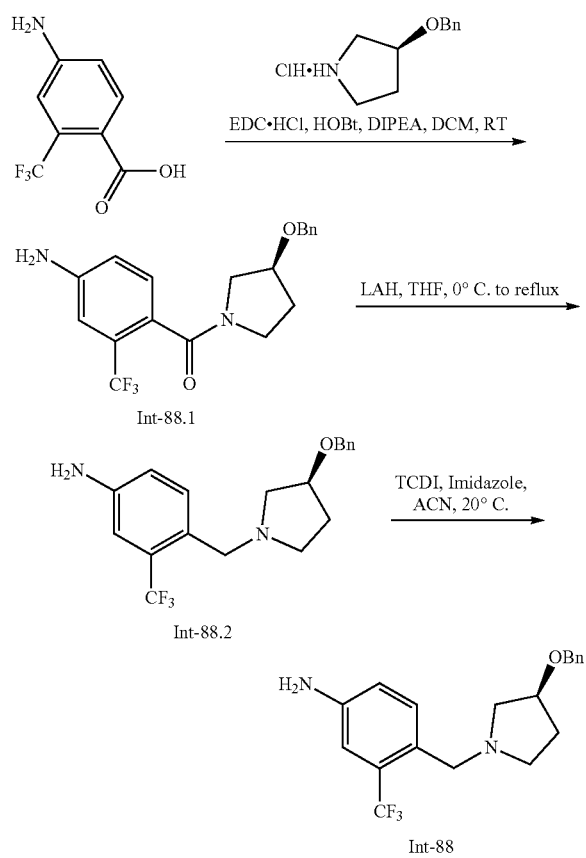

Synthesis of compound Int-88.1. Compound Int-88.1 was prepared from 4-amino-2-(trifluoromethyl)benzoic acid and (S)-3-(benzyloxy)pyrrolidine hydrochloride, following the procedure described in the synthesis of Int-79.1. The product was purified by flash column chromatography on silica gel (CombiFlash®, 30% ethyl acetate in hexane). MS (ES): m/z 365.2 [M+H]$^+$.

Synthesis of compound Int-88.2. Compound Int-88.2 was prepared from Int-88.1, following the procedures described in the synthesis of Int-81.2. The product was purified by flash column chromatography on silica gel (CombiFlash®, 1.5% methanol in DCM). MS (ES): m/z 351.2 [M+H]$^+$.

Synthesis of compound Int-88. Compound Int-88 was prepared from Int-88.2, following the procedures described in the synthesis of Int-69. The product was purified by flash column chromatography on silica gel (CombiFlash®, 15% ethyl acetate in hexane). MS (ES): m/z 393.4 [M+H]$^+$.

Preparation of Intermediate Int-89: (R)-3-(benzyloxy)-1-(4-isothiocyanato-2-(trifluoromethyl)benzyl)pyrrolidine

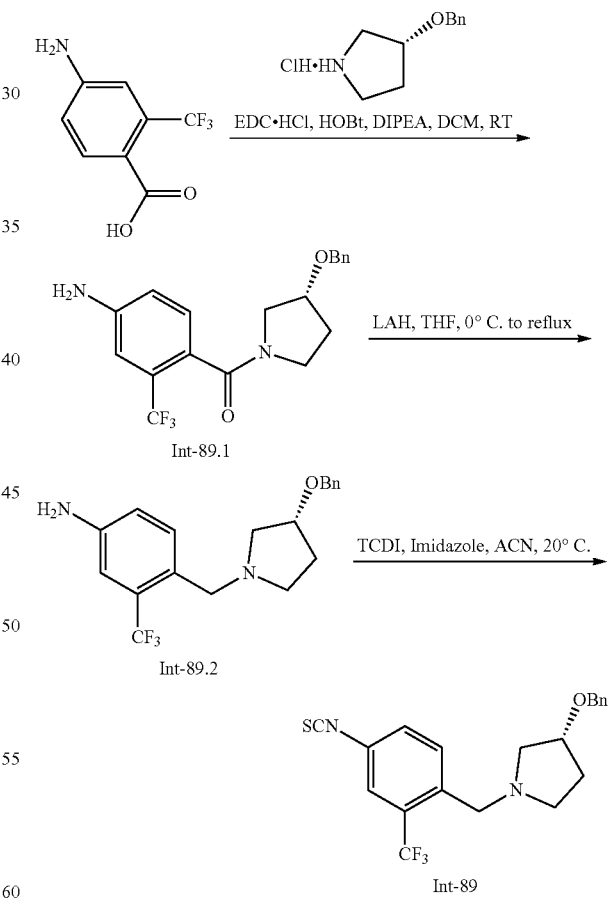

Synthesis of compound Int-89. Compound Int-89 was prepared following the procedures described in the synthesis of Int-88. The product was purified by flash column chromatography on silica gel (CombiFlash®, 15% ethyl acetate in hexane). MS (ES): m/z 393.4 [M+H]$^+$.

487

Preparation of Intermediate Int-90: 3-fluoro-1-(4-isothiocyanato-2-(trifluoromethyl)benzyl)azetidine

488

Preparation of Intermediate Int-91: 1-(4-isothiocyanato-2-(trifluoromethyl)benzyl)-3-methoxyazetidine

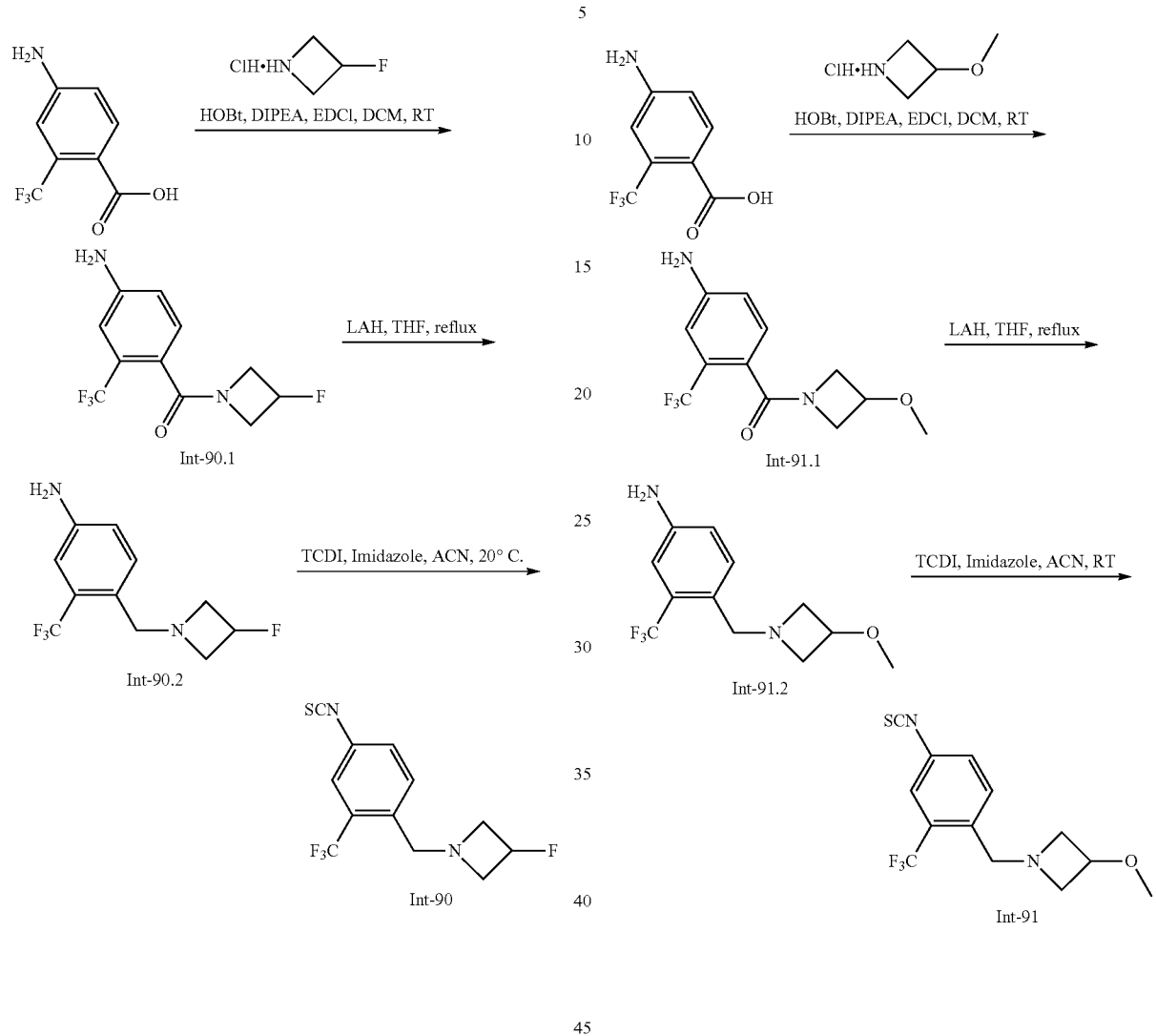

Synthesis of compound Int-90.1. Compound Int-90.1 was prepared from 4-amino-2-(trifluoromethyl)benzoic acid and 3-fluoroazetidine hydrochloride, following the procedure described in the synthesis of Int-79.1. The product was purified by flash column chromatography on silica gel (CombiFlash®, 3.0% methanol in DCM) to afford Int-90.1. MS (ES): m/z 263.2 [M+H]$^+$.

Synthesis of compound Int-90.2. Compound Int-90.2 was prepared from Int-90.1, following the procedures described in the synthesis of Int-81.2. The product was purified by flash column chromatography on silica gel (CombiFlash®, 2.0% methanol in DCM) to afford Int-90.2. MS (ES): m/z 249.2 [M+H]$^+$.

Synthesis of compound Int-90. Compound Int-90 was prepared from Int-90.2, following the procedures described in the synthesis of Int-69. The product was purified by flash column chromatography on silica gel (CombiFlash®, 35% ethyl acetate in hexane). MS (ES): m/z 291.1 [M+H]$^+$.

Synthesis of compound Int-91.1. Compound Int-91.1 was prepared from 4-amino-2-(trifluoromethyl)benzoic acid and 3-methoxyazetidine hydrochloride, following the procedure described in the synthesis of Int-79.1. The product was purified by flash column chromatography on silica gel (CombiFlash®, 2.5% methanol in DCM). MS (ES): m/z 275.1 [M+H]$^+$.

Synthesis of compound Int-91.2. Compound Int-91.2 was prepared from Int-91.1, following the procedures described in the synthesis of Int-81.2. The product was purified by flash column chromatography on silica gel (CombiFlash®, 2.0% methanol in DCM). MS (ES): m/z 260.9 [M+H]$^+$.

Synthesis of compound Int-91. Compound Int-91 was prepared following the procedures described in the synthesis of Int-69. The product was purified by flash column chromatography on silica gel (CombiFlash®, 3.5% methanol in DCM). MS (ES): m/z 303.2 [M+H]$^+$.

Preparation of Intermediate Int-92: 4-(3-isothiocyanato-5-(trifluoromethyl)benzyl)morpholine

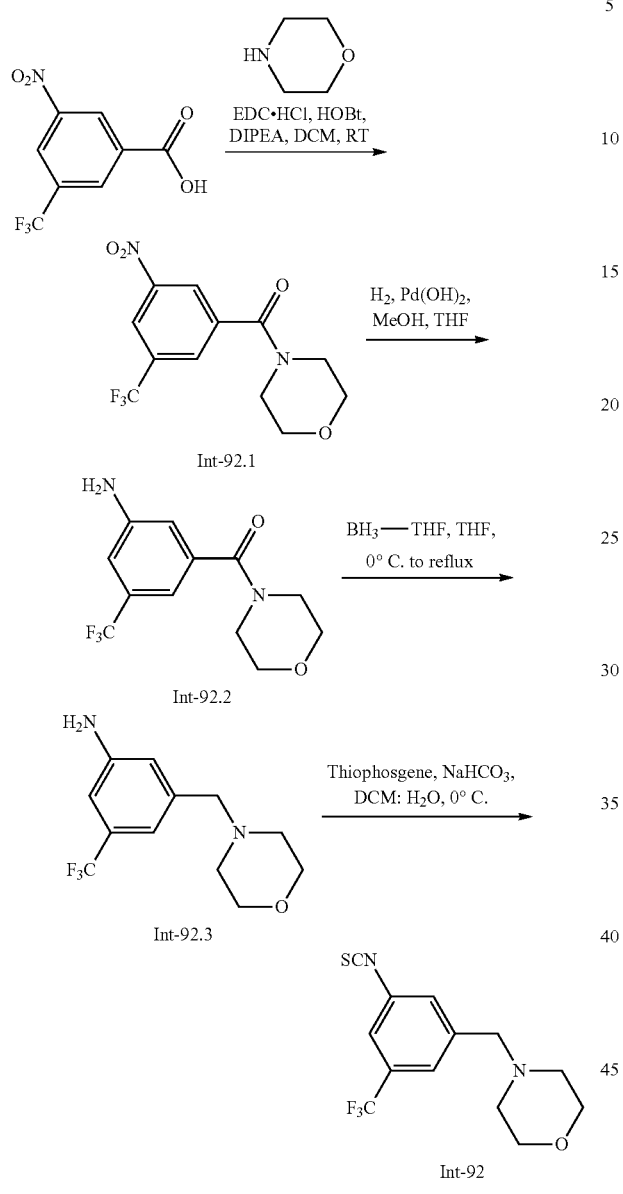

Synthesis of compound Int-92.1.
Compound Int-92.1 was prepared from 3-nitro-5-(trifluoromethyl)benzoic acid and morpholine, following the procedure described in the synthesis of Int-79.1. The product was purified by flash column chromatography on silica gel (CombiFlash®, 33% ethyl acetate in hexane). MS (ES): m/z 305.2 [M+H]$^+$.

Synthesis of compound Int-92.2. Compound Int-92.2 was prepared from Int-92.1, following the procedures described in the synthesis of Int-85.2. The product was used without purification. MS (ES): m/z 275.1 [M+H]$^+$.

Synthesis of compound Int-92.3. Compound Int-92.3 was prepared from Int-92.2, following the procedures described in the synthesis of Int-79.2. The product was purified by flash column chromatography on silica gel (CombiFlash®, 1.6% methanol in DCM). MS (ES): m/z 261.2 [M+H]$^+$.

Synthesis of compound Int-92. Compound Int-92 was prepared from Int-92.3 following the procedure described in the synthesis of Int-1. The product was purified by flash column chromatography on silica gel (CombiFlash®, 1.8% methanol in DCM). MS (ES): m/z 303.1 [M+H]$^+$.

Preparation of Intermediate Int-93: 3-fluoro-1-(3-isothiocyanato-5-(trifluoromethyl)benzyl)azetidine

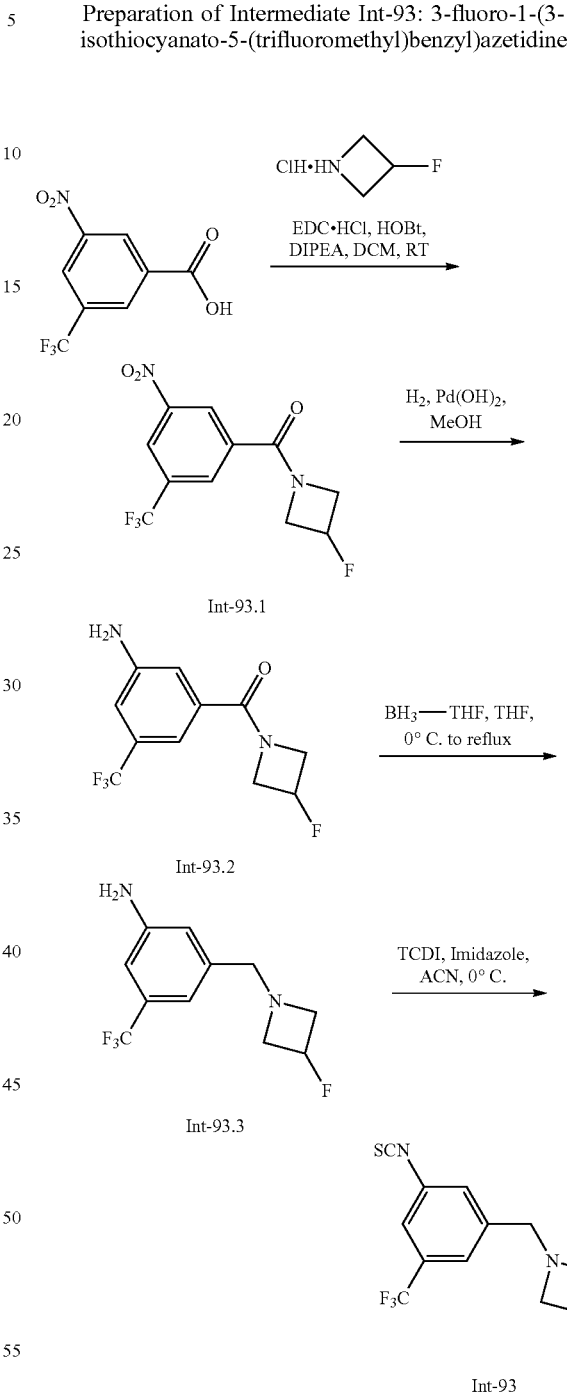

Synthesis of compound Int-93.1. Compound Int-93.1 was prepared from 3-nitro-5-(trifluoromethyl)benzoic acid and 3-fluoroazetidine hydrochloride, following the procedure described in the synthesis of Int-79.1. The product was purified by flash column chromatography on silica gel (CombiFlash®, 26% ethyl acetate in hexane). MS (ES): m/z 293.1 [M+H]$^+$.

Synthesis of compound Int-93.2. Compound Int-93.2 was prepared from Int-93.1, following the procedures described in the synthesis of Int-85.2. The product was used without purification. MS (ES): m/z 263.2 [M+H]$^+$.

Synthesis of compound Int-93.3. Compound Int-93.3 was prepared from Int-93.2, following the procedures described in the synthesis of Int-79.2. The product was purified by flash column chromatography on silica gel (CombiFlash®, 1.5% methanol in DCM). MS (ES): m/z 249.2 [M+H]$^+$.

Synthesis of compound Int-93. Compound Int-93 was prepared from Int-93.3 following the procedure described in the synthesis of Int-69. The product was purified by flash column chromatography on silica gel (CombiFlash®, 15% ethyl acetate in hexane). MS (ES): m/z 249.2 [M+H]$^+$.

Preparation of Intermediate Int-94: 1-(3-isothiocyanato-5-(trifluoromethyl)benzyl)-3-methoxyazetidine

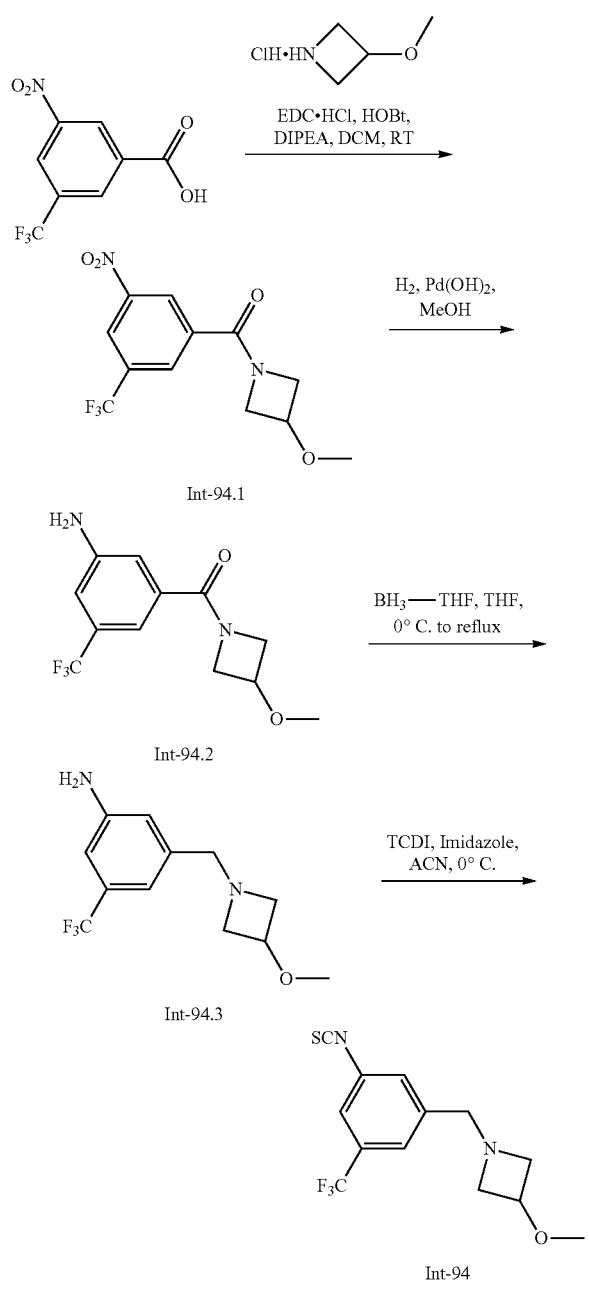

Synthesis of compound Int-94.1. Compound Int-94.1 was prepared from 3-nitro-5-(trifluoromethyl)benzoic acid and 3-methoxyazetidine hydrochloride, following the procedure described in the synthesis of Int-79.1. The product was purified by flash column chromatography on silica gel (CombiFlash®, 27% ethyl acetate in hexane). MS (ES): m/z 305.1 [M+H]$^+$.

Synthesis of compound Int-94.2. Compound Int-94.2 was prepared from Int-94.1, following the procedures described in the synthesis of Int-85.2. The product was used without purification. MS (ES): m/z 275.2 [M+H]$^+$.

Synthesis of compound Int-94.3. Compound Int-94.3 was prepared from Int-94.2, following the procedures described in the synthesis of Int-79.2. The product was purified by flash column chromatography on silica gel (CombiFlash®, 1.7% methanol in DCM). MS (ES): m/z 261.2 [M+H]$^+$.

Synthesis of compound Int-94. Compound Int-94 was prepared from Int-94.3 following the procedure described in the synthesis of Int-69. The product was purified by flash column chromatography on silica gel (CombiFlash®, DCM). MS (ES): m/z 303.2 [M+H]$^+$.

Preparation of Intermediate Int-95: 3,3-difluoro-1-(3-isothiocyanato-5-(trifluoromethyl)benzyl)pyrrolidine

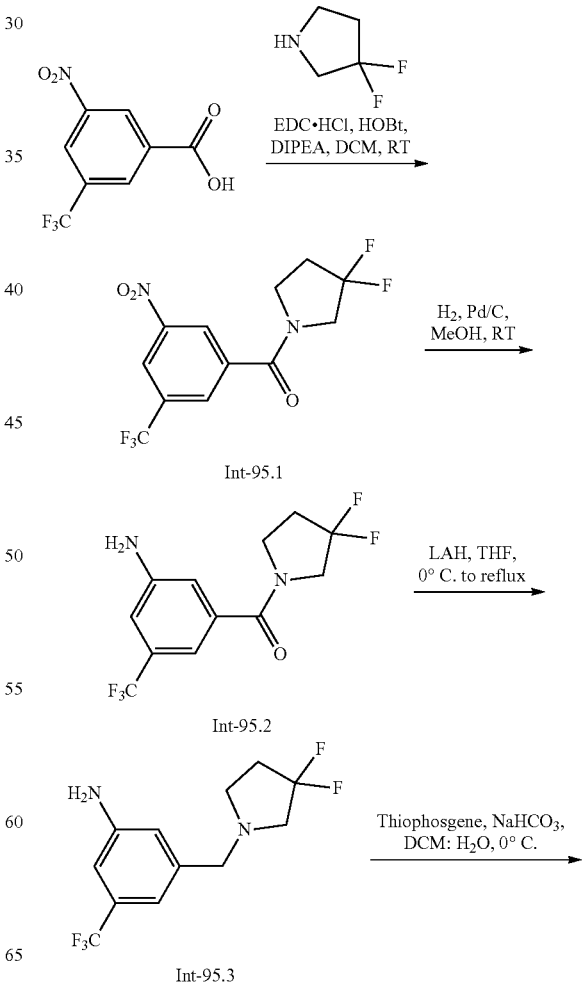

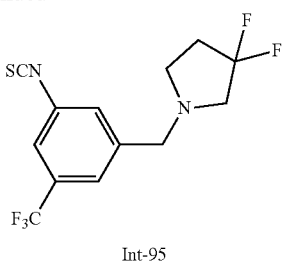

Int-95

Synthesis of compound Int-95.1. Compound Int-95.1 was prepared from 3-nitro-5-(trifluoromethyl)benzoic acid and 3,3-difluoropyrrolidine, following the procedure described in the synthesis of Int-79.1. The product was purified by flash column chromatography on silica gel (CombiFlash®, 15% ethyl acetate in hexane). MS (ES): m/z 325.1 [M+H]$^+$.

Synthesis of compound Int-95.2. Compound Int-95.2 was prepared from Int-95.1, following the procedures described in the synthesis of Int-23.3. The product was used without purification. MS (ES): m/z 295.2 [M+H]$^+$.

Synthesis of compound Int-95.3. Compound Int-95.3 was prepared from Int-95.2, following the procedures described in the synthesis of Int-81.2. The product was purified by flash column chromatography on silica gel (CombiFlash®, 25% ethyl acetate in hexane). MS (ES): m/z 281.0 [M+H]$^+$.

Synthesis of compound Int-95. Compound Int-95 was prepared from Int-95.3 following the procedure described in the synthesis of Int-1. The product was purified by flash column chromatography on silica gel (CombiFlash®, 1.0% methanol in DCM). MS (ES): m/z 323.1 [M+H]$^+$.

Preparation of Intermediate Int-96: 1-(3-isothiocyanato-5-(trifluoromethyl)benzyl)-4-methoxypiperidine

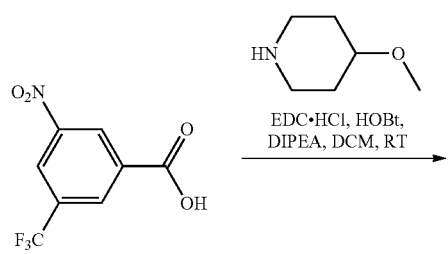

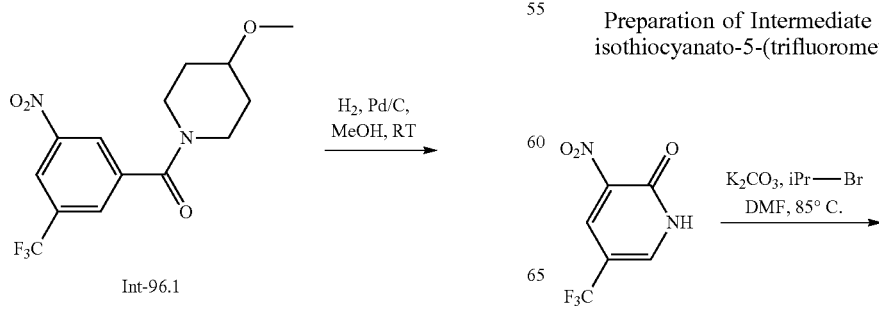

Synthesis of compound Int-96.1. Compound Int-96.1 was prepared from 3-nitro-5-(trifluoromethyl)benzoic acid and 4-methoxypiperidine, following the procedure described in the synthesis of Int-79.1. The product was purified by flash column chromatography on silica gel (CombiFlash®, 13% ethyl acetate in hexane). MS (ES): m/z 333.0 [M+H]$^+$.

Synthesis of compound Int-96.2. Compound Int-96.2 was prepared from Int-96.1, following the procedures described in the synthesis of Int-23.3. The product was used without purification. MS (ES): m/z 303.1 [M+H]$^+$.

Synthesis of compound Int-96.3. Compound Int-96.3 was prepared from Int-96.2, following the procedures described in the synthesis of Int-81.2. The product was purified by flash column chromatography on silica gel (CombiFlash®, 23% ethyl acetate in hexane). MS (ES): m/z 289.2 [M+H]$^+$.

Synthesis of compound Int-96. Compound Int-96 was prepared from Int-96.3 following the procedure described in the synthesis of Int-69. The product was purified by flash column chromatography on silica gel (CombiFlash®, 10% ethyl acetate in hexane). MS (ES): m/z 331.3 [M+H]$^+$.

Preparation of Intermediate Int-97: 1-isopropyl-3-isothiocyanato-5-(trifluoromethyl)pyridin-2(1H)-one

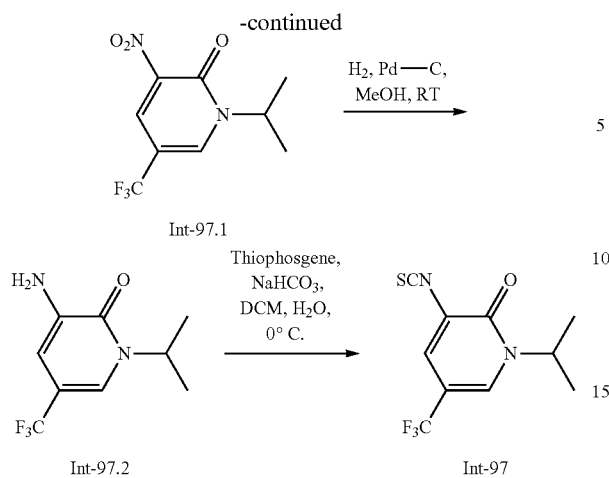
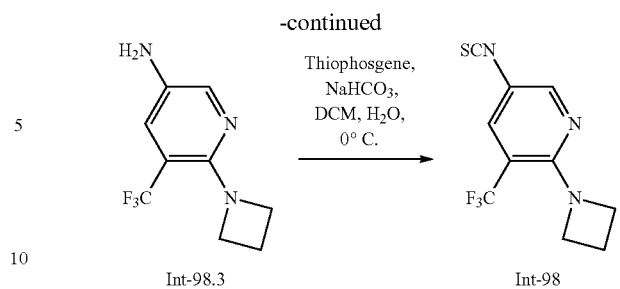

Synthesis of compound Int-97.1. Compound Int-97.1 was prepared from 3-nitro-5-(trifluoromethyl)benzoic acid and 2-propyl bromide, following the procedure described in the synthesis of Int-79.1. The product was purified by flash column chromatography on silica gel (CombiFlash®, 20% ethyl acetate in hexane). MS (ES): m/z 251.1 [M+H]$^+$.

Synthesis of compound Int-97.2. Compound Int-97.2 was prepared from Int-97.1, following the procedures described in the synthesis of Int-23.3. The product was used without purification. MS (ES): m/z 221.2 [M+H]$^+$.

Synthesis of compound Int-97. Compound Int-97 was prepared from Int-97.3 following the procedure described in the synthesis of Int-1. The product was purified by flash column chromatography on silica gel (CombiFlash®, 2.5% methanol in DCM). MS (ES): m/z 263.0 [M+H]$^+$.

Preparation of Intermediate Int-98: 2-(azetidin-1-yl)-5-isothiocyanato-3-(trifluoromethyl)pyridine

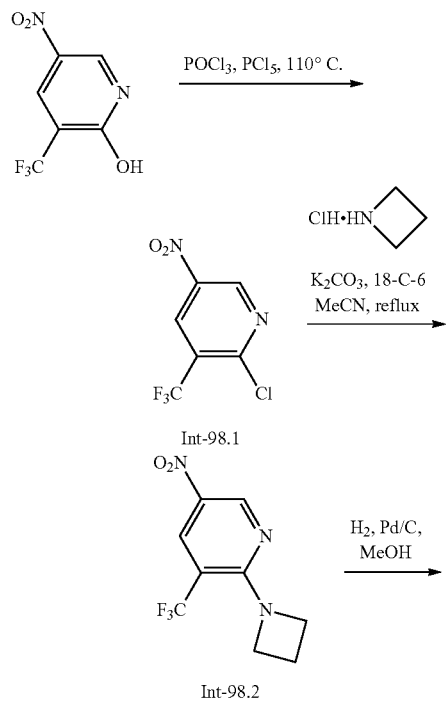

Synthesis of compound Int-98.1. To 5-nitro-3-(trifluoromethyl)pyridin-2-ol (2.0 g, 9.61 mmol, 1.0 equiv) was added phosphorus pentachloride (2.79 g, 13.45 mmol, 1.4 equiv) followed by phosphoryl chloride (2.2 mL, 24.02 mmol, 2.5 equiv). The reaction mixture was stirred at 110° C. for 8 h. It was concentrated under reduced pressure to afford a residue which was dissolved in DCM and washed with 2 N sodium hydroxide. The combined organic layers were washed with brine, dried over anhydrous sodium sulfate, filtered and concentrated under reduced pressure to afford Int-98.1. MS (ES): m/z 227.54 [M+H]$^+$.

Synthesis of compound Int-98.2. A mixture of Int-98.1 (1.5 g, 6.62 mmol, 1.0 equiv), azetidine hydrochloride (0.756 g, 8.08 mmol, 1.22 equiv), potassium carbonate (3.19 g, 23.17 mmol, 3.5 equiv) and 18-crown-6 (150 mg, 10% w/w) in acetonitrile (40 mL) was heated to reflux for 8 h. It was cooled to room temperature, poured over ice-water and extracted with ethyl acetate. The combined organic layers were, dried over anhydrous sodium sulfate, filtered and concentrated under reduced pressure. The residue was purified by flash column chromatography on silica gel (CombiFlash®, 28% ethyl acetate in hexane) to afford Int-98.2. MS (ES): m/z 248.1 [M+H]$^+$.

Synthesis of Compound Int-98.3. Compound Int-98.3 was prepared from Int-98.2, following the procedures described in the synthesis of Int-23.3. The product was used without purification. MS (ES): m/z 218.2 [M+H]$^+$.

Synthesis of compound Int-98. Compound Int-98 was prepared from Int-98.3 following the procedure described in the synthesis of Int-1. The product was purified by flash column chromatography on silica gel (CombiFlash®, 2.0% methanol in DCM). MS (ES): m/z 260.1 [M+H]$^+$.

Preparation of Intermediate Int-99: (R)-3-(benzyloxy)-1-(3-isothiocyanato-5-(trifluoromethyl)benzyl)pyrrolidine

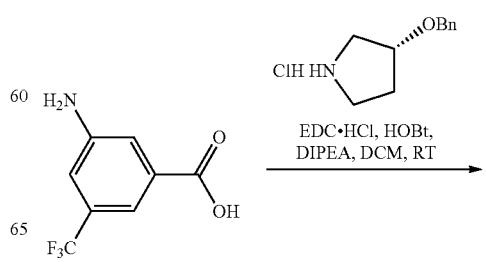

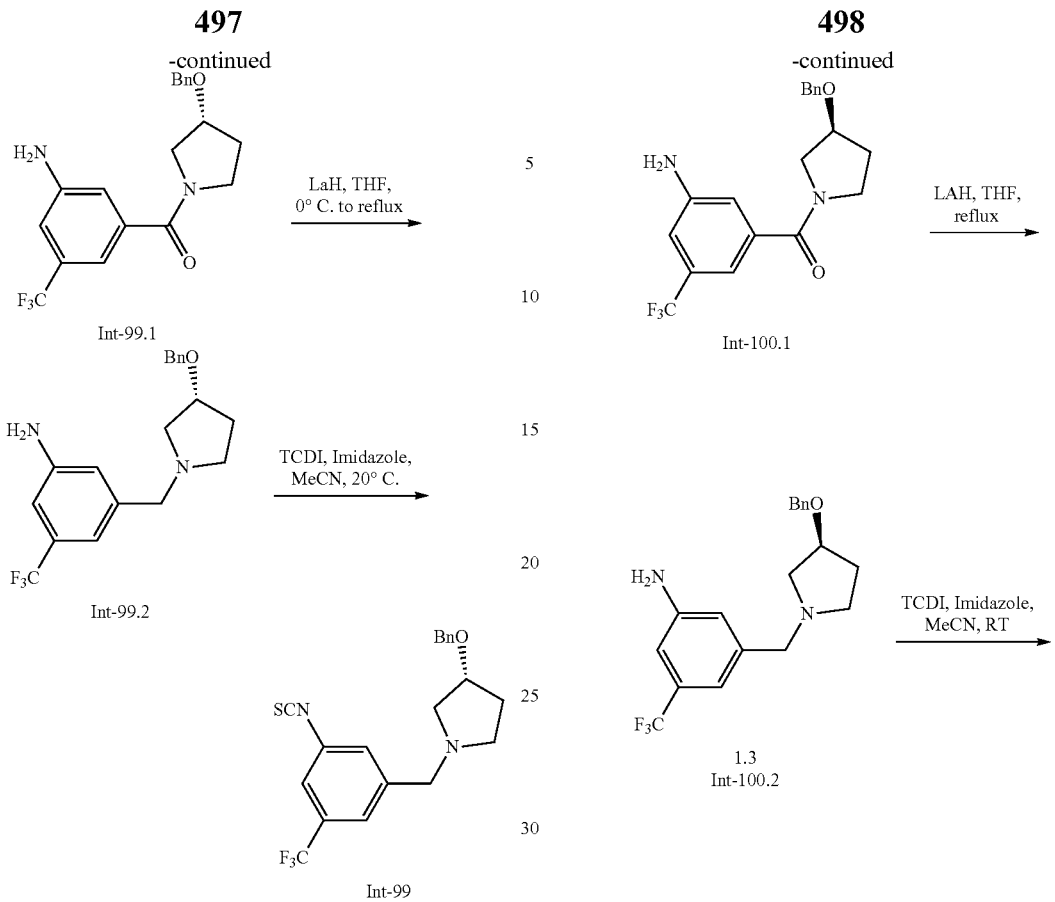

Synthesis of compound Int-99.1. Compound Int-99.1 was prepared from 3-amino-5-(trifluoromethyl)benzoic acid and (R)-3-(benzyloxy)pyrrolidine hydrochloride, following the procedure described in the synthesis of Int-79.1. The product was purified by flash column chromatography on silica gel (CombiFlash®, 30% ethyl acetate in hexane). MS (ES): m/z 365.2 [M+H]$^+$.

Synthesis of compound Int-99.2. Compound Int-99.2 was prepared from Int-99.1, following the procedures described in the synthesis of Int-81.2. The product was purified by flash column chromatography on silica gel (CombiFlash®, 1.5% methanol in DCM). MS (ES): m/z 351.39 [M+H]$^+$.

Synthesis of compound Int-99. Compound Int-99 was prepared from Int-99.2 following the procedure described in the synthesis of Int-69. The product was purified by flash column chromatography on silica gel (CombiFlash®, 15% ethyl acetate in hexane). MS (ES): m/z 393.4 [M+H]$^+$.

Preparation of Intermediate Int-100: (S)-3-(benzyloxy)-1-(3-isothiocyanato-5-(trifluoromethyl)benzyl)pyrrolidine

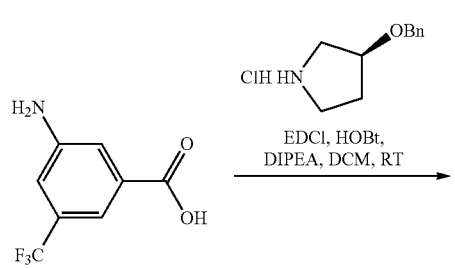

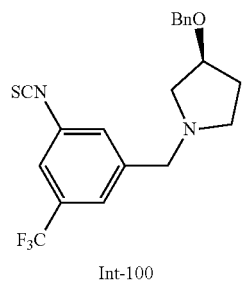

Synthesis of compound Int-100.1. Compound Int-100.1 was prepared from 3-amino-5-(trifluoromethyl)benzoic acid and (S)-3-(benzyloxy)pyrrolidine hydrochloride, following the procedure described in the synthesis of Int-79.1. The product was purified by flash column chromatography on silica gel (CombiFlash®, 30% ethyl acetate in hexane). MS (ES): m/z 365.1 [M+H]$^+$.

Synthesis of compound Int-100.2. Compound Int-100.2 was prepared from Int-100.1, following the procedures described in the synthesis of Int-81.2. The product was purified by flash column chromatography on silica gel (CombiFlash®, 1.5% methanol in DCM). MS (ES): m/z 351.39 [M+H]$^+$.

Synthesis of compound Int-100. Compound Int-100 was prepared from Int-100.2 following the procedure described in the synthesis of Int-69. The product was purified by flash column chromatography on silica gel (CombiFlash®, 15% ethyl acetate in hexane). MS (ES): m/z 393.5 [M+H]$^+$.

Preparation of Intermediate Int-101: (4-(3-isothiocyanato-5-(trifluoromethyl)phenoxy)-1-methylpiperidine

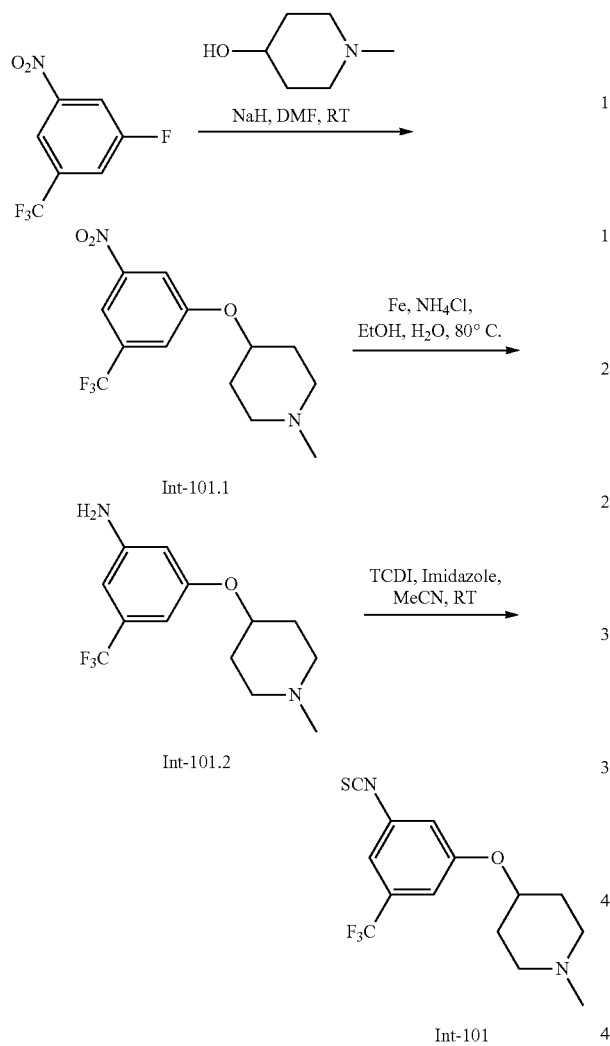

Synthesis of compound Int-101.1. To a solution of 1-fluoro-3-nitro-5-(trifluoromethyl)benzene (0.500 g, 2.39 mmol, 1.0 equiv) in DMF (10 mL) was added sodium hydride (0.143 g, 3.58 mmol, 1.5 equiv) in portions at 0° C. and stirred for 30 min followed by addition of 1-methylpiperidin-4-ol (0.33 g, 2.87 mmol, 1.2 equiv). The reaction mixture was stirred at room temperature for 1 h. It was poured over water, stirred and extracted with ethyl acetate. The combined organic layers were, dried over anhydrous sodium sulfate, filtered and concentrated under reduced pressure. The residue was purified by flash column chromatography on silica gel (CombiFlash®, 2.8% methanol in DCM) to afford Int-101.1. MS (ES): m/z 305.2 [M+H]$^+$.

Synthesis of compound Int-101.2. Compound Int-101.2 was prepared from Int-101.1, following the procedure described in the synthesis of 3.7. The product was purified by column using 3.5% methanol in DCM). MS (ES): m/z 275.2 [M+H]$^+$.

Synthesis of compound Int-101. Compound Int-101 was prepared from Int-101.2 following the procedure described in the synthesis of Int-69. The product was purified by flash column chromatography on silica gel (CombiFlash®, 25% ethyl acetate in hexane). MS (ES): m/z 317.1 [M+H]$^+$.

Preparation of Intermediate Int-102: (1-(2-(benzyloxy)ethyl)-4-(4-isothiocyanato-2-(trifluoromethyl)benzyl)piperazine

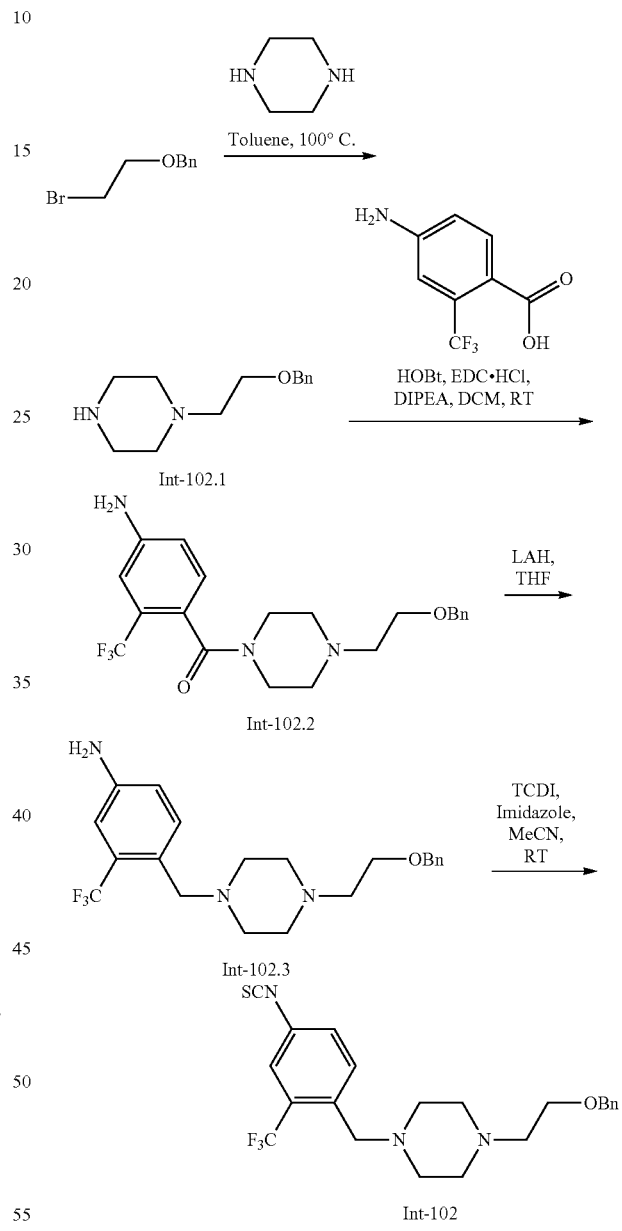

Synthesis of compound Int-102.1. A solution of ((2-bromoethoxy)methyl)benzene (2 g, 9.30 mmol, 1.0 equiv) and piperazine (1.2 g, 13.95 mmol, 1.5 equiv) in toluene (10 mL) was stirred at 100° C. for 2 h. It was cooled to room temperature, filtered and the filtrate was concentrated under reduced pressure. This residue was acidified with 2 M hydrochloric acid and extracted with DCM. Aqueous layer separated and basified with solid sodium hydroxide and extracted with DCM. The combined organic layers were washed with brine, dried over anhydrous sodium sulfate, filtered and concentrated under reduced pressure to afford Int-102.1. MS (ES): m/z 221.2 [M+H]$^+$.

Synthesis of compound Int-102.2. Compound Int-102.2 was prepared from 3-amino-5-(trifluoromethyl)benzoic acid and Int-102.1, following the procedure described in the synthesis of Int-79.1. The product was purified by flash column chromatography on silica gel (CombiFlash®, 1.6% methanol in DCM). MS (ES): m/z 408.1 [M+H]$^+$.

Synthesis of compound Int-102.3. Compound Int-102.3 was prepared from Int-102.2, following the procedures described in the synthesis of Int-81.2. The product was purified by flash column chromatography on silica gel (CombiFlash®, 1.8% methanol in DCM). MS (ES): m/z 394.2 [M+H]$^+$.

Synthesis of compound Int-102. Compound Int-102 was prepared from Int-102.3 following the procedure described in the synthesis of Int-69. The product was purified by flash column chromatography on silica gel (CombiFlash®, DCM). MS (ES): m/z 436.4 [M+H]$^+$.

Preparation of Intermediate Int-103: 1-(2,2-difluoroethyl)-4-(4-isothiocyanato-2-(trifluoromethyl)benzyl)piperazine

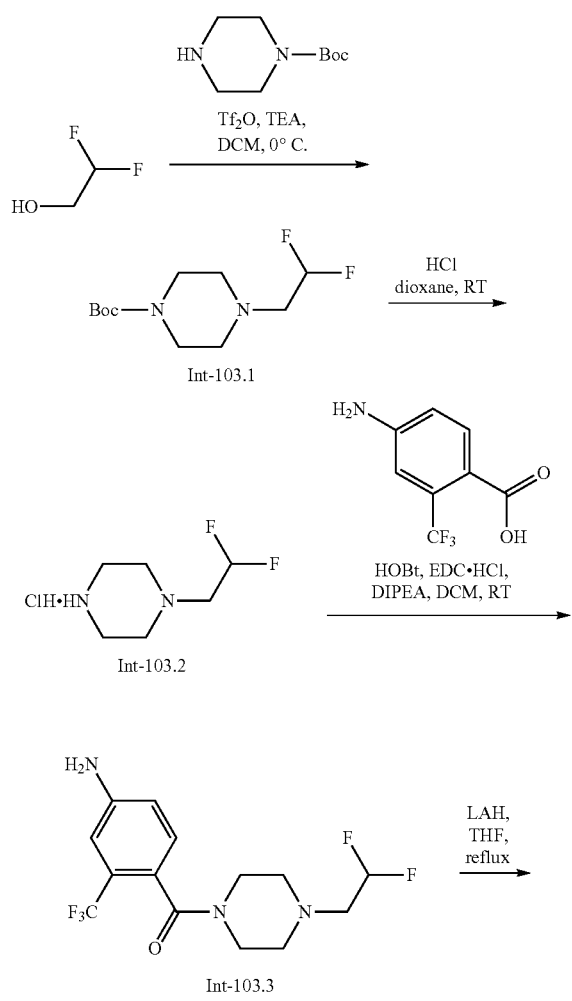

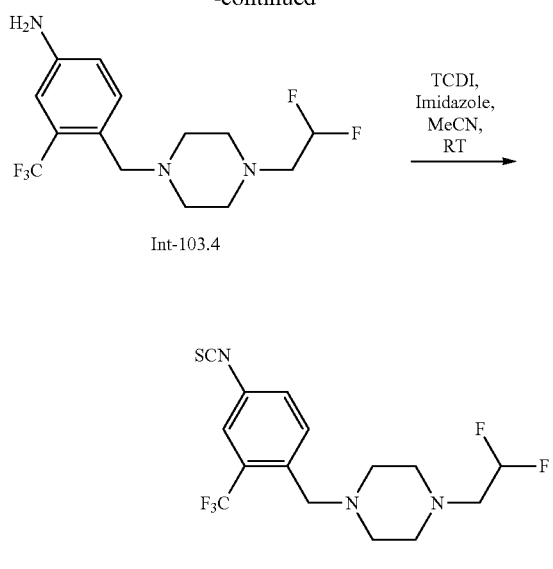

Synthesis of compound Int-103.1. To a solution of 2,2-difluoroethan-1-ol (0.500 g, 6.09 mmol, 1.0 equiv) in DCM (10 mL) was added trifluoromethanesulfonic anhydride (1.53 mL, 9.14 mmol, 1.5 equiv) and triethylamine (1.7 mL, 12.18 mmol, 2.0 equiv) and stirred at 0° C. for 30 min. To the solution was added tert-butyl piperazine-1-carboxylate (0.908 g, 4.88 mmol, 0.8 equiv). It was stirred at room temperature for 9 h, poured over water, stirred and extracted with ethyl acetate. The combined organic layers were washed with saturated sodium bicarbonate followed by brine, dried over anhydrous sodium sulfate, filtered and concentrated under reduced pressure. The residue was purified by flash column chromatography on silica gel (CombiFlash®, 5% ethyl in hexane) to afford Int-103.1. MS (ES): m/z 251.1 [M+H]$^+$.

Synthesis of compound Int-103.2. To a solution of Int-103.1 (0.410 g, 1.64 mmol, 1.0 equiv) in 1,4-dioxane (10 mL) was added hydrogen chloride in dioxane (3 mL) stirred at room temperature for 3 h. It was concentrated under reduced pressure. The residue was purified by trituration in diethyl ether to afford Int-103.2. MS (ES): m/z 151.2 [M−HCl]$^+$.

Synthesis of compound Int-103.3. Compound Int-103.3 was prepared from 3-amino-5-(trifluoromethyl)benzoic acid and Int-103.2, following the procedure described in the synthesis of Int-79.1. The product was purified by flash column chromatography on silica gel (CombiFlash®, 5.1% methanol in DCM). MS (ES): m/z 338.1 [M+H]$^+$.

Synthesis of compound Int-103.4. Compound Int-103.4 was prepared from Int-103.3, following the procedures described in the synthesis of Int-81.2. The product was purified by flash column chromatography on silica gel (CombiFlash®, 3.1% methanol in DCM). MS (ES): m/z 324.1 [M+H]$^+$.

Synthesis of compound Int-103. Compound Int-103 was prepared from Int-103.4 following the procedure described in the synthesis of Int-69. The product was purified by flash column chromatography on silica gel (CombiFlash®, 1.2% methanol in DCM). MS (ES): m/z 366.3 [M+H]$^+$.

Preparation of Intermediate Int-104: tert-butyl (R)-3-(3-isothiocyanato-5-(trifluoromethyl)phenoxy)pyrrolidine-1-carboxylate

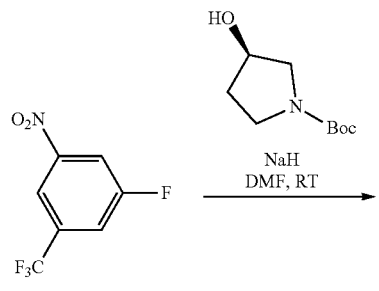

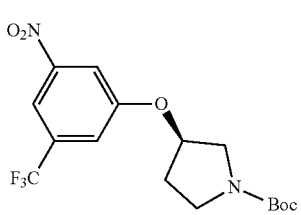

Int-104.1

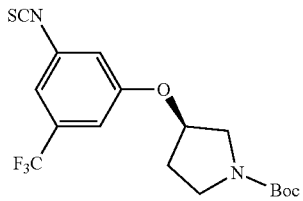

Int-104.2

Int-104

Preparation of Intermediate Int-105: tert-butyl (S)-3-(3-isothiocyanato-5-(trifluoromethyl)phenoxy)pyrrolidine-1-carboxylate

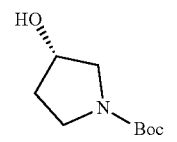

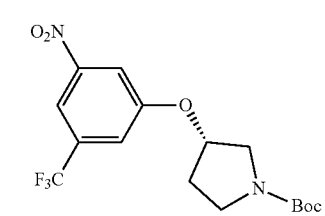

Int-105.1

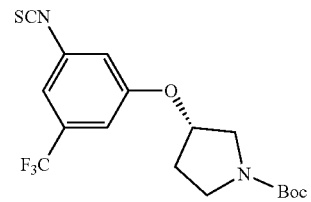

Int-105.2

Int-105

Synthesis of compound Int-104.1. Compound Int-104.1 was prepared from 1-fluoro-3-nitro-5-(trifluoromethyl)benzene and tert-butyl (R)-3-hydroxypyrrolidine-1-carboxylate, following the procedures described in the synthesis of Int-101.1. The product was purified by flash column chromatography on silica gel (CombiFlash®, 16% ethyl acetate in hexane). MS (ES): m/z 377.3 $[M+H]^+$.

Synthesis of compound Int-104.2. Compound Int-104.2 was prepared from Int-104.1, following the procedures described in the synthesis of Int-23.3. The product was used without purification. MS (ES): m/z 347.1 $[M+H]^+$.

Synthesis of compound Int-104. Compound Int-104 was prepared from Int-104.2 following the procedure described in the synthesis of Int-69. The product was purified by flash column chromatography on silica gel (CombiFlash®, 2.7% ethyl methanol in DCM). MS (ES): m/z 389.2 $[M+H]^+$.

Synthesis of compound Int-105.1. Compound Int-105.1 was prepared from 1-fluoro-3-nitro-5-(trifluoromethyl)benzene and tert-butyl (S)-3-hydroxypyrrolidine-1-carboxylate, following the procedures described in the synthesis of Int-101.1. The product was purified by flash column chromatography on silica gel (CombiFlash®, 16% ethyl acetate in hexane) to afford Int-105.1, MS (ES): m/z 377.3 $[M+H]^+$.

Synthesis of compound Int-105.2. Compound Int-105.2 was prepared from Int-105.1, following the procedures described in the synthesis of Int-23.3. The product was used without purification. MS (ES): m/z 347.1 $[M+H]^+$.

Synthesis of compound Int-105. Compound Int-105 was prepared from Int-105.2 following the procedure described in the synthesis of Int-69. The product was purified by flash column chromatography on silica gel (CombiFlash®, 2.7% ethyl methanol in DCM). MS (ES): m/z 389.2 $[M+H]^+$.

Preparation of Intermediate Int-106: 1-(5-fluoro-4-isothiocyanato-2-(trifluoromethyl)phenyl)-N,N-dimethylmethanamine

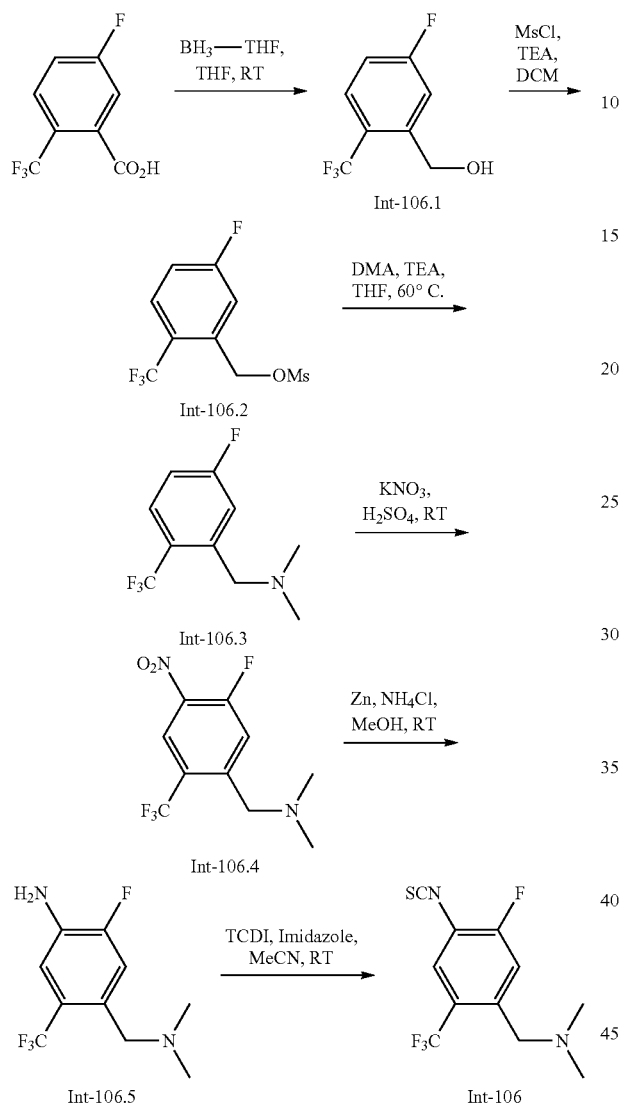

Synthesis of compound Int-106.1. To a solution of 5-fluoro-2-(trifluoromethyl)benzoic acid (3 g, 14.42 mmol, 1.0 equiv) in THF (150 mL) was added borane-THF complex (1 M in THF, 72.1 mL, 72.1 mmol, 5.0 equiv) at 0° C. The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl in hexane) to afford Int-106.1 MS (ES): m/z 195.1 [M+H]$^+$.

Synthesis of compound Int-106.2. To a solution of Int-106.1 (1.2 g, 6.18 mmol, 1.0 equiv) and triethylamine (2.58 mL, 18.54 mmol, 3.0 equiv) in DCM (15 mL) was added methane sulfonyl chloride (0.71 mL, 9.27 mmol, 1.5 equiv) at 0° C. The reaction mixture was stirred at room temperature for 3 h. It was poured over ice-water, stirred and extracted with DCM. The combined organic layers were washed with brine, dried over anhydrous sodium sulfate, filtered and concentrated under reduced pressure to afford Int-106.2. MS (ES): m/z 273.2 [M+H]$^+$.

Synthesis of compound Int-106.3. To a solution of Int-106.2 (1.3 g, 4.78 mmol, 1.0 equiv) and triethylamine (1.7 mL, 11.95 mmol, 2.5 equiv) in THF (20 mL) was added N,N dimethylamine (2 M in THF, 4.78 mL, 9.56 mmol, 2.0 equiv). The reaction mixture was stirred at 60° C. for 4 h. It was poured over ice cold water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl in hexane) to afford Int-106.3. MS (ES): m/z 221.9 [M+H]$^+$.

Synthesis of compound Int-106.4. To a solution of Int-106.3 (0.700 g, 3.16 mmol, 1.0 equiv) in sulfuric acid (7 mL) was added potassium nitrate (0.478 g, 4.74 mmol, 1.5 equiv) in portions at 0° C. The reaction mixture was stirred at room temperature for 16 h. It was poured over ice-water and neutralized with sodium bicarbonate and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl in hexane) to afford Int-106.4. MS (ES): m/z 267.1 [M+H]$^+$.

Synthesis of compound Int-106.5. To a solution of Int-106.4 (0.400 g, 1.50 mmol, 1.0 equiv) in methanol (15 mL) was added zinc powder (0.975 g, 15.0 mmol, 10.0 equiv) and ammonium chloride (0.810 g, 1.50 mmol, 10.0 equiv). The reaction mixture was stirred at room temperature for 16 h. It was filtered through a pad of Celite® and rinsed with methanol. The filtrate was concentrated under reduced pressure. The residue was purified by flash column chromatography on silica gel (CombiFlash®, 20% ethyl in hexane) to afford Int-106.5. MS (ES): m/z 237 [M+H]$^+$.

Synthesis of compound Int-106. Compound Int-106 was prepared from Int-106.5 following the procedure described in the synthesis of Int-69. The product was purified by flash column chromatography on silica gel (CombiFlash®, 5% ethyl in hexane). MS (ES): m/z 279.1 [M+H]$^+$.

Preparation of Intermediate Int-107: 1-(4-isothiocyanato-2-(trifluoromethyl)benzyl)azetidine-3-carbonitrile

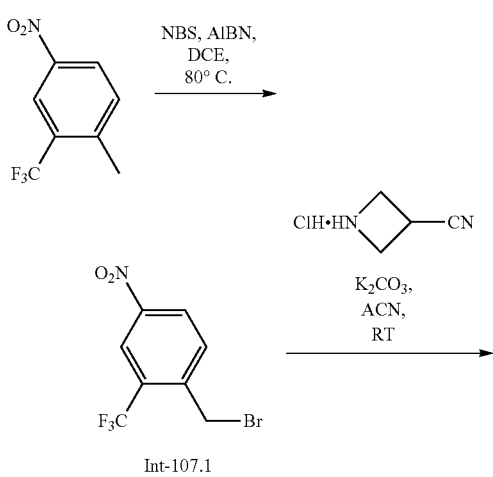

507

-continued

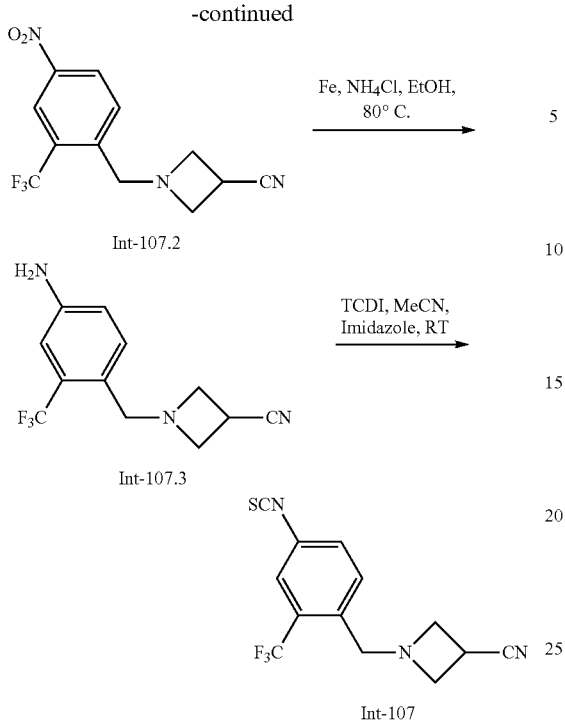

508

Preparation of Intermediate Int-108: 3-isothiocyanato-1-(methyl-d₃)-5-(trifluoromethyl)pyridin-2(1H)-one

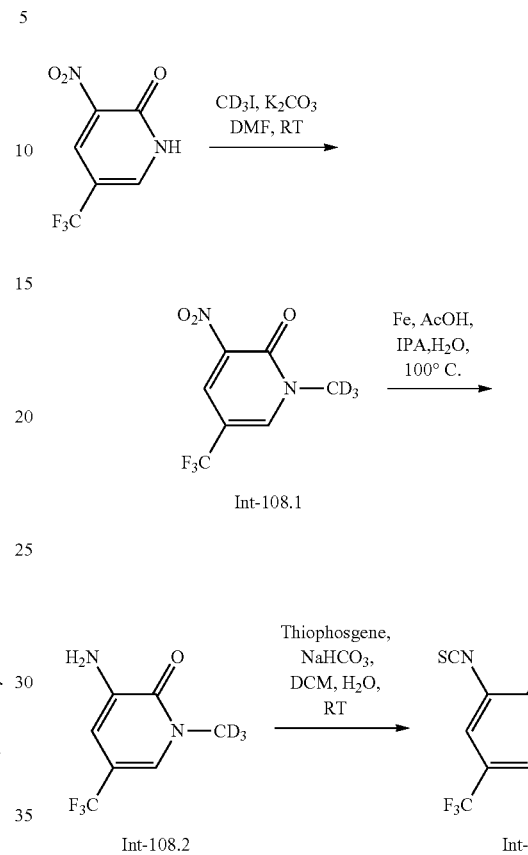

Synthesis of compound Int-107.1. To a solution of 1-methyl-4-nitro-2-(trifluoromethyl)benzene (2.0 g, 9.75 mmol, 1.0 equiv) in 1,2-dichloroethane (30 mL) was added N-bromosuccinimide (1.73 g, 9.75 mmol, 1.0 equiv) followed by azobisisobutyronitrile (0.159 g, 0.975 mmol, 0.1 equiv). The reaction mixture was stirred at 80° C. for 5 h. It was poured over ice cold water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.0% ethyl acetate in hexane) to afford Int-107.1. MS (ES): m/z 284.9 [M+H]⁺.

Synthesis of compound Int-107.2. To a solution of Int-107.2 (1.5 g, 5.28 mmol, 1.0 equiv) and azetidine-3-carbonitrile hydrochloride (0.751 g, 6.34 mmol, 1.2 equiv) in acetonitrile (30 mL) was added potassium carbonate (2.18 g, 15.84 mmol, 3.0 equiv) and stirred at room temperature for 4 h. It was poured over ice cold water and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-107.2. MS (ES): m/z 286.1 [M+H]⁺.

Synthesis of compound Int-107.3. Compound Int-107.3 was prepared from Int-107.2, following the procedure described in the synthesis of 3.7. The product was used in the next step without purification. MS (ES): m/z 256.2 [M+H]⁺.

Synthesis of compound Int-107. Compound Int-107 was prepared from Int-107.3 following the procedure described in the synthesis of Int-69. The product was purified by flash column chromatography on silica gel (CombiFlash®, 20% ethyl acetate in hexane). MS (ES): m/z 298 [M+H]⁺.

Synthesis of compound Int-108.1. A mixture of compound 3-nitro-5-(trifluoromethyl)pyridin-2(1H)-one (0.300 g, 1.44 mmol, 1.0 equiv) and potassium carbonate (0.596 g, 4.32 mmol, 3.0 equiv) in DMF (6 mL) was added deuterated iodomethane (0.271 g, 1.87 mmol, 1.3 equiv). The reaction mixture was stirred at room temperature for 3 h. The reaction mixture was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.0% methanol in DCM) to afford Int-108.1. MS (ES): m/z 226.1 [M+H]⁺.

Synthesis of compound Int-108.2. To a solution of Int-108.1 (0.160 g, 0.710 mmol, 1.0 equiv) in 2-propanol:water (2:1) (3 mL) was added iron powder (0.199 g, 3.55 mmol, 5.0 equiv) followed by acetic acid (0.213 g, 3.55 mmol, 5.0 equiv). The reaction mixture was heated at 100° C. for 2 h. It was filtered through a pad of Celite® and the filtrate was concentrated under reduced pressure. The residue was purified by column using 5% Methanol in DCM) to afford Int-108.2. MS (ES): m/z 196.1 [M+H]⁺.

Synthesis of compound Int-108. Compound Int-108 was prepared from Int-108.2 following the procedure described in the synthesis of Int-1. The product was purified by flash column chromatography on silica gel (CombiFlash®, 20% ethyl acetate in hexane). MS (ES): m/z 237.8 [M+H]⁺.

Preparation of Intermediate Int-109: tert-butyl 3-(3-isothiocyanato-5-(trifluoromethyl)phenoxy)azetidine-1-carboxylate

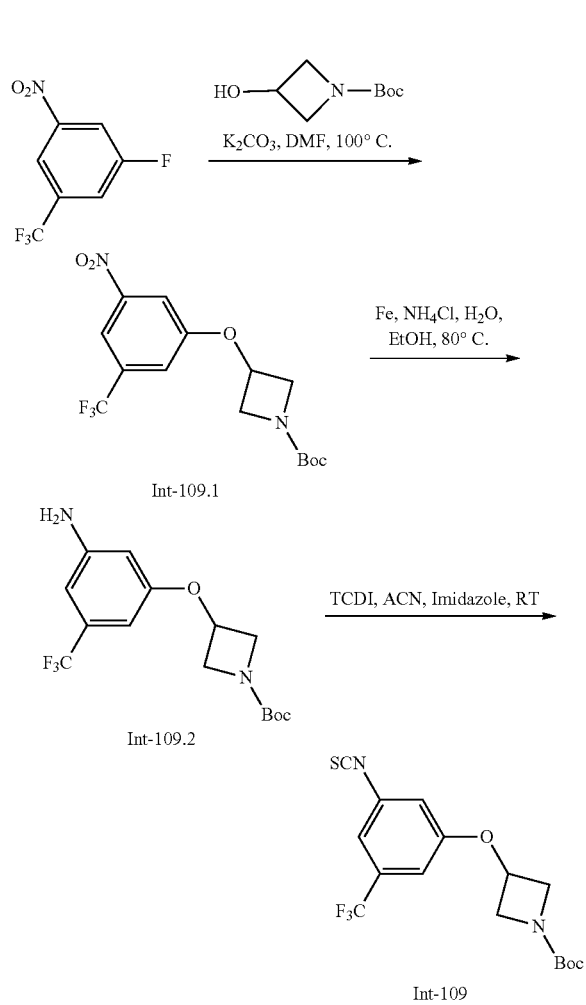

Synthesis of compound Int-109.1. A mixture of 1-fluoro-3-nitro-5-(trifluoromethyl)benzene (0.600 g, 2.87 mmol, 1.0 equiv) and potassium carbonate (1.18 g, mmol, 3.0 equiv) in DMF (5 mL) was stirred at 0° C. for 30 min and was added tert-butyl 3-hydroxyazetidine-1-carboxylate (0.595 g, 3.44 mmol, 1.2 equiv). The reaction mixture was stirred at 100° C. for 16 h. It was poured over water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 7% ethyl acetate in hexane) to afford Int-109.1. MS (ES): m/z 363.3 [M+H]+.

Synthesis of compound Int-109.2. Compound Int-109.2 was prepared from Int-109.1, following the procedure described in the synthesis of 3.7. The product was purified by column using 15% ethyl acetate in hexane). MS (ES): m/z 333.1 [M+H]+.

Synthesis of compound Int-109. Compound Int-109 was prepared from Int-109.2 following the procedure described in the synthesis of Int-69. The product was purified by flash column chromatography on silica gel (CombiFlash®, 10% ethyl acetate in hexane). MS (ES): m/z 375.2 [M+H]+.

Preparation of Intermediate Int-110: 1-benzyl-3-isothiocyanato-5-(trifluoromethyl)pyridin-2(1H)-one

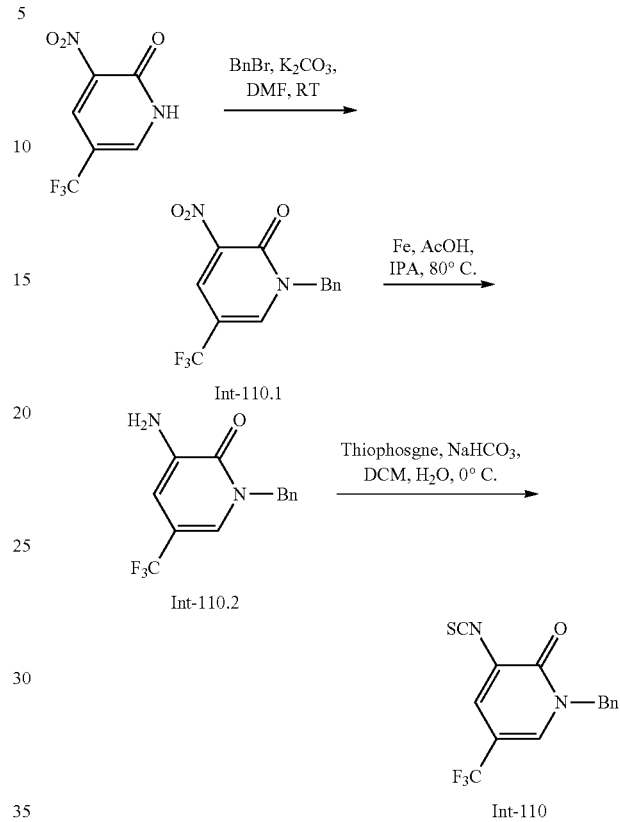

Synthesis of compound Int-110.1. To a mixture of 3-nitro-5-(trifluoromethyl)pyridin-2(1H)-one (1.0 g, 4.81 mmol, 1.0 equiv) and potassium carbonate (1.33 g, 9.62 mmol, 2.0 equiv) in DMF (10 mL) was added benzyl bromide (1.23 g, 7.21 mmol, 1.5 equiv) and was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-110.1. MS (ES): m/z 299.1 [M+H]+.

Synthesis of compound Int-110.2. To a mixture of Int-110.1 (0.800 g, 2.68 mmol 1.0 equiv), iron powder (0.750 g, 13.4 mmol, 5.0 equiv) and acetic acid (0.804 g, 13.4 mmol, 5.0 equiv) in 2-propanol (10 mL) was stirred at 80° C. for 2 h. It was filtered through a pad of Celite®, transferred into ice-cold saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford Int-110.2. MS (ES): m/z 269.2 [M+H]+.

Synthesis of compound Int-110. Compound Int-110 was prepared from Int-110.2 following the procedure described in the synthesis of Int-1. The product was purified by flash column chromatography on silica gel (CombiFlash®, 1.0% methanol in DCM). MS (ES): m/z 311.1 [M+H]+.

Preparation of Intermediate Int-111: 2-fluoro-5-isothiocyanato-N,N-dimethyl-3-(trifluoromethyl)benzamide

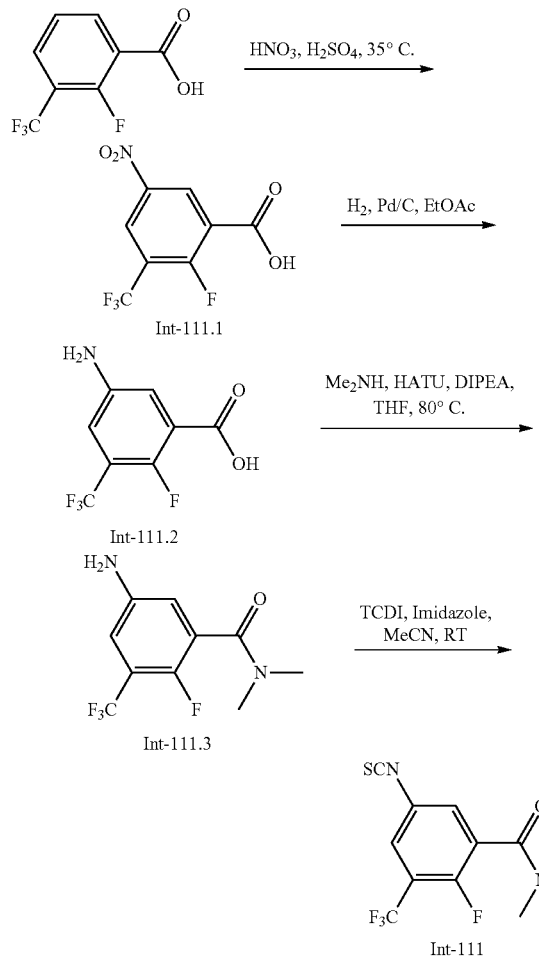

Preparation of Intermediate Int-112: (S)-3-(3-isothiocyanato-5-(trifluoromethyl)phenoxy)-1-methylpyrrolidine

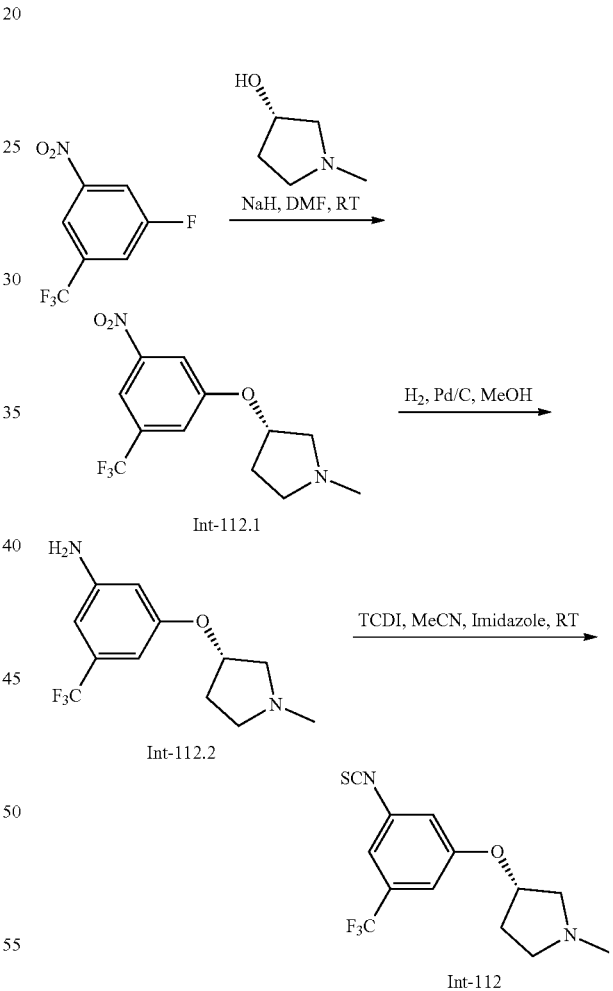

Synthesis of compound Int-111.1. To a solution of 2-fluoro-3-(trifluoromethyl)benzoic acid (1.0 g, 4.81 mmol, 1.0 equiv) in conc. sulfuric acid (5 mL) was added fuming nitric acid (1 mL) at 0° C. The reaction mixture was stirred at 55° C. for 2 h. It was poured over crushed ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford Int-111.1. MS (ES): m/z 254.1 [M+H]$^+$.

Synthesis of compound Int-111.2. A mixture of Int-111.1 (0.900 g, 3.56 mmol, 1.0 equiv) and 10% palladium on carbon (0.450 g) in ethyl acetate (20 mL) was stirred under hydrogen (1 atm) for 2 h. The reaction mixture was filtered through a pad of Celite® and rinsed with methanol. The filtrate was concentrated under reduced pressure to afford Int-111.2. MS (ES): m/z 224 [M+H]$^+$.

Synthesis of compound Int-111.3. To a solution of Int-111.2 (0.600 g, 2.69 mmol, 1.0 equiv) in THF (10 mL) was added dimethylamine (2 M in THF, 1.6 mL, 3.22 mmol, 1.2 equiv) followed by 1-[bis(dimethylamino)methylene]-1H-1,2,3-triazolo[4,5-b]pyridinium-3-oxide (1.53 g, 4.03 mmol, 1.5 equiv) and reaction mixture stirred at room temperature for 30 min. To this N,N-diisopropylethylamine (1.04 g, 8.07 mmol, 3.0 equiv) was added, The reaction mixture was stirred at 80° C. for 3 h. It was poured over ice-water and extracted with ethyl acetate. The combined organic layers were washed with brine, dried over anhydrous sodium sulfate, filtered and concentrated under reduced pressure. The residue was purified flash column chromatography on silica gel (CombiFlash®, 30% ethyl acetate in hexane) to afford Int-111.3. MS (ES): m/z 251.20 [M+H]$^+$.

Synthesis of compound Int-111. Compound Int-111 was prepared from Int-111.3 following the procedure described in the synthesis of Int-69. The product was purified by flash column chromatography on silica gel (CombiFlash®, DCM). MS (ES): m/z 293.2 [M+H]$^+$.

Synthesis of compound Int-112.1. Compound Int-112.1 was prepared from 1-fluoro-3-nitro-5-(trifluoromethyl)benzene and (S)-1-methylpyrrolidin-3-ol, following the procedures described in the synthesis of Int-101.1. The product was purified by flash column chromatography on silica gel (CombiFlash®, 3.0% methanol in DCM). MS (ES): m/z 291.2 [M+H]$^+$.

Synthesis of compound Int-112.2. Compound Int-105.2 was prepared from Int-105.1, following the procedures described in the synthesis of Int-23.3. The product was used without purification. MS (ES): m/z 261.1 [M+H]$^+$.

Synthesis of compound Int-112. Compound Int-112 was prepared from Int-112.2 following the procedure described in the synthesis of Int-69. The product was purified by flash column chromatography on silica gel (CombiFlash®, 2.0% methanol in DCM). MS (ES): m/z 303.2 [M+H]$^+$.

Preparation of Intermediate Int-113: (R)-3-(3-isothiocyanato-5-(trifluoromethyl)phenoxy)-1-methylpyrrolidine

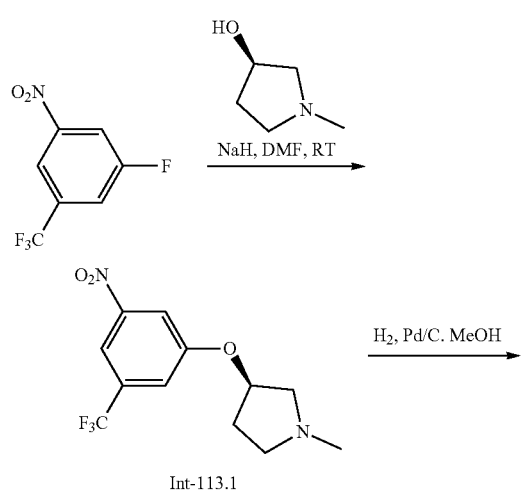

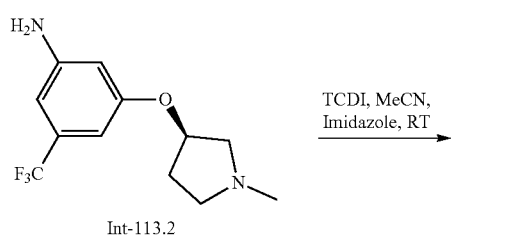

Synthesis of compound Int-113. Compound Int-113 was prepared following the procedures described in the synthesis of Int-112. The final product was purified by flash column chromatography on silica gel (CombiFlash®, 2.0% methanol in DCM). MS (ES): m/z 303.2 [M+H]$^+$.

Preparation of Intermediate Int-114: 5-cyclopropyl-2-isothiocyanato-4,6-dimethylpyrimidine

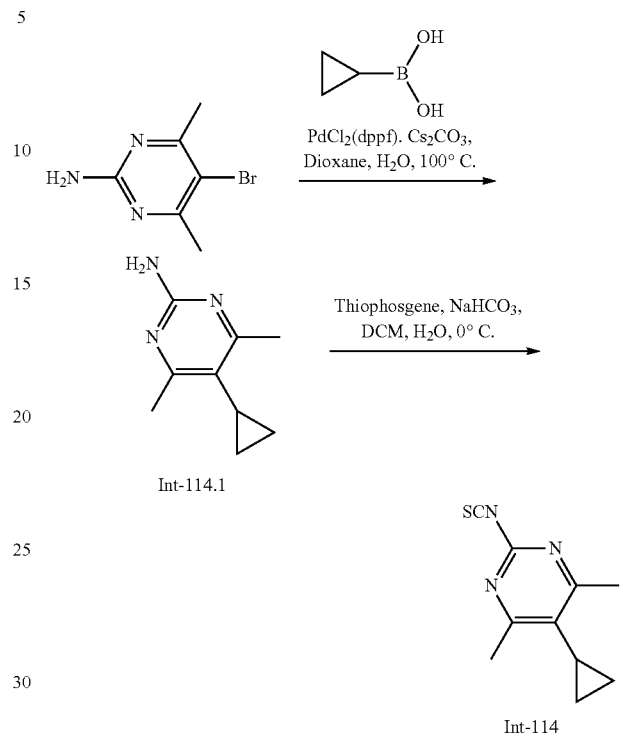

Synthesis of compound Int-114.1 A mixture of 5-bromo-4,6-dimethylpyrimidin-2-amine (0.5 g, 2.47 mmol, 1.0 equiv) in 1,4-dioxane (5 mL), cyclopropylboronic acid (0.619 g, 7.4 mmol, 3 equiv) and cesium carbonate (2.41 g, 7.4 mmol, 3.0 equiv) was degassed by bubbling argon through for 10 min. 1,1-Bis(diphenylphosphino)ferrocenepalladium(II) dichloride DCM complex (0.060 g, 0.074 mmol, 0.03 equiv) was added, again degassed for 5 min. The reaction mixture was stirred at 100° C. for 1 h. It was poured over water and extracted with ethyl acetate. The combined organic layers were washed with brine, dried over anhydrous sodium sulfate, filtered and concentrated under reduced pressure. This residue was purified by flash column chromatography on silica gel (CombiFlash®, 2.5% methanol in DCM) to afford Int-114.1. MS (ES): m/z 164.2 [M+H]$^+$.

Synthesis of compound Int-114. Compound Int-114 was prepared from Int-114.1 following the procedure described in the synthesis of Int-1. The product was purified by flash column chromatography on silica gel (CombiFlash®, 20% ethyl acetate in hexane). MS (ES): m/z 206.28 [M+H]$^+$.

Preparation of Intermediate Int-115: 3-fluoro-2-isothiocyanato-6,6-dimethyl-6,7-dihydro-4H-pyrazolo[5,1-c][1,4]oxazine

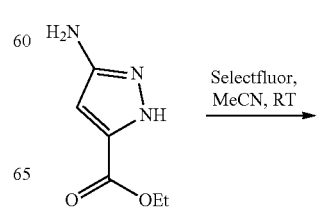

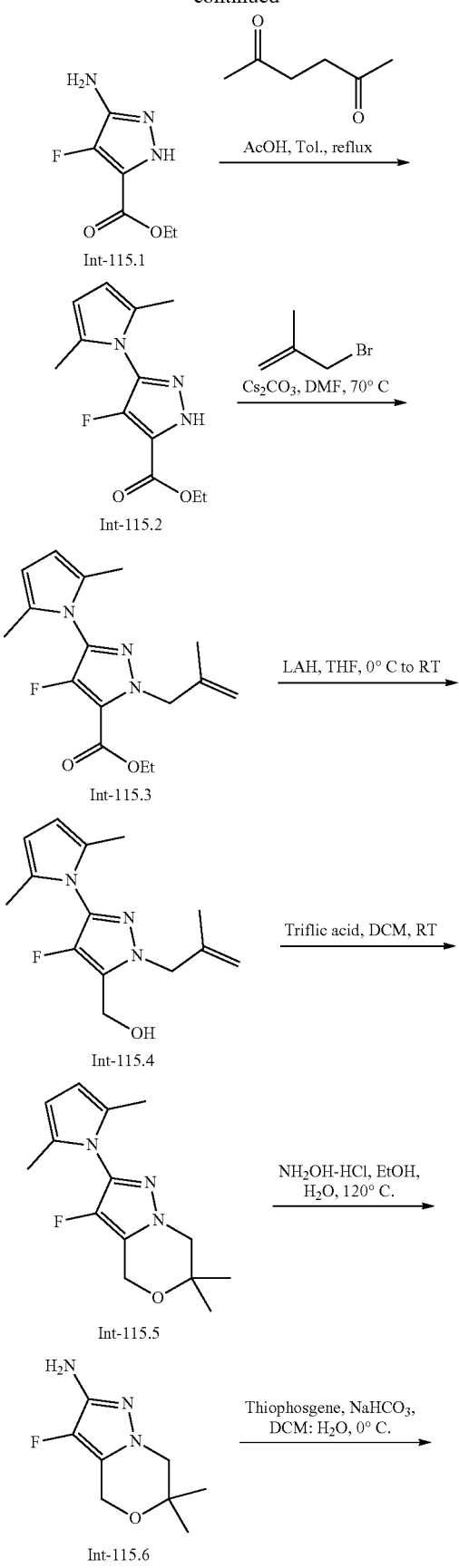

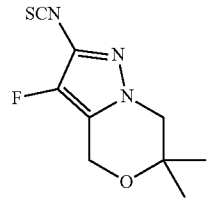

Int-115

Synthesis of compound Int-115.1. To solution of ethyl 3-amino-1H-pyrazole-5-carboxylate (10 g, 64.45 mmol, 1.0 equiv) in acetonitrile (200 mL) was added 1-chloromethyl-4-fluoro-1,4-diazoniabicyclo[2.2.2]octane-bis(tetrafluoroborate) (10 g, 28.22 mmol, 0.4 equiv) and stirred at room temperature for 16 h. It was poured over water and extracted with ethyl acetate. The combined organic layers were washed with brine, dried over anhydrous sodium sulfate, filtered and concentrated under reduced pressure to afford crude. This was purified by flash column chromatography on silica gel (CombiFlash®, 25% ethyl acetate in hexane) to afford Int-115.1. MS (ES): m/z 174.1 [M+H]⁺.

Synthesis of compound Int-115.2. To a solution of Int-115.1 (3.8 g, 21.95 mmol, 1.0 equiv) in toluene (100 mL) was added 2,5-hexanedione (2.51 g, 21.95 mmol, 1.0 equiv) and acetic acid (catalytic). The reaction mixture was refluxed with a Dean-Stark trap to remove water for 72 h. It cooled to rt, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford Int-115.2. MS (ES): m/z 252.2 [M+H]⁺.

Synthesis of compound Int-115.3. A mixture of Int-115.2 (1.9 g, 7.56 mmol, 1.0 equiv), 3-bromo-2-methylprop-1-ene (1.02 g, 7.56 mmol, 1.0 equiv) and cesium carbonate (4.91 g, 15.12 mmol, 2.0 equiv) in DMF (20 mL) was stirred at 70° C. for 5 h. The reaction mixture was poured over ice-water and extracted with ethyl acetate. The combined organic layers were washed with brine, dried over anhydrous sodium sulfate, filtered and concentrated under reduced pressure to afford crude. This was purified by flash column chromatography on silica gel (CombiFlash®, 15% ethyl acetate in hexane) to afford Int-115.3. MS (ES): m/z 306.1 [M+H]⁺.

Synthesis of compound Int-115.4. To a solution of Int-115.3 (0.5 g, 1.64 mmol, 1.0 equiv) in THF (5 mL) was added lithium aluminum hydride (1 M in THF, 2.5 mL, 2.46 mmol, 1.5 equiv) dropwise at 0° C. and stirred for 4 h. It was poured over ice-water and extracted with ethyl acetate. The combined organic layers were washed with brine, dried over anhydrous sodium sulfate, filtered and concentrated under reduced pressure to afford crude. This was purified by flash column chromatography on silica gel (CombiFlash®, 26% ethyl acetate in hexane) to afford Int-115.4. MS (ES): m/z 263.2 [M+H]⁺.

Synthesis of compound Int-115.5. To a solution of Int-115.4 (0.200 g, 0.759 mmol, 1.0 equiv) in DCM (10 mL) was added triflic acid (2.0 mL) and stirred at room temperature for 30 min. It was poured over saturated sodium bicarbonate solution and extracted with ethyl acetate. The combined organic layers were washed with brine, dried over anhydrous sodium sulfate, filtered and concentrated under reduced pressure to afford Int-115.5. MS (ES): m/z 264.3 [M+H]⁺.

Synthesis of compound Int-115.6. To a solution of Int-115.5 (0.149 g, 0.565 mmol, 1.0 equiv) in ethanol:water (2:1) (8 mL) was added hydroxylamine hydrochloride (1.95 g, 28.25 mmol, 50 equiv) and the reaction mixture was stirred at 120° C. for 3-4 h. It was cooled to room temperature, transferred into 2 N aqueous sodium hydroxide solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford Int-115.6. MS (ES): m/z 186.0 [M+H]$^+$.

Synthesis of compound Int-115. Compound Int-115 was prepared from Int-115.6 following the procedure described in the synthesis of Int-1. The product was purified by flash column chromatography on silica gel (CombiFlash®, 45% ethyl acetate in hexane). MS (ES): m/z 228.1 [M+H]$^+$.

Preparation of Intermediate Int-116: 5-isothiocyanato-1-methyl-6-oxo-3-(trifluoromethyl)-1,6-dihydropyridine-2-carbonitrile

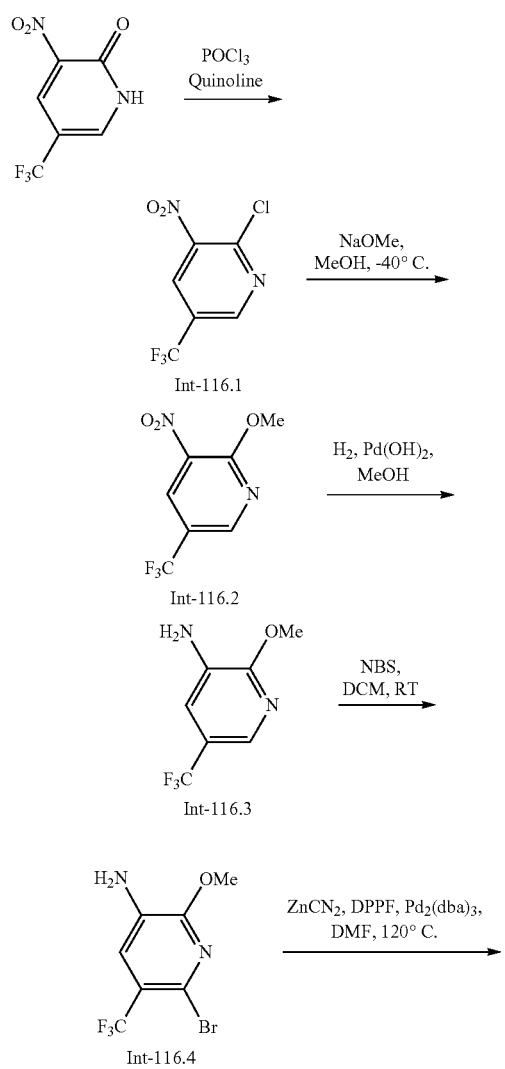

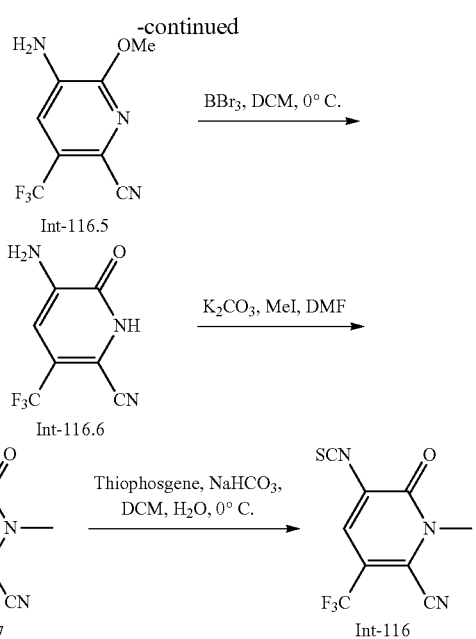

Synthesis of compound Int-116.1. To a mixture of 3-nitro-5-(trifluoromethyl)pyridin-2(1H)-one (5 g, 24.3 mmol, 1.0 equiv) and quinoline (2.0 g, 15.55 mmol, 0.64 equiv) was added phosphorus oxychloride (15 mL) dropwise. The reaction mixture was stirred at 120° C. for 2 h. The reaction mixture cooled to room temperature and diluted with ethyl acetate followed by addition of dilute hydrochloric acid (2 N). The combined organic layers were washed with saturated sodium bicarbonate solution followed by brine, dried over anhydrous sodium sulfate, filtered and concentrated under reduced pressure. The residue was purified by flash column chromatography on silica gel (CombiFlash®, 5% ethyl acetate in hexane) to afford Int-116.1, MS (ES): m/z 227.4 [M+H]$^+$.

Synthesis of compound Int-116.2. To a solution of Int-116.1 (4.0 g, 17.66 mmol, 1.0 equiv) in methanol (20 mL) was added sodium methoxide (25% in methanol, 4.2 mL, 19.42 mmol, 1.1 equiv) drop wise at −40° C. The reaction mixture was stirred at same temperature for 20 min. It was poured over ice cold 1 N hydrochloric acid and extracted with ethyl acetate. The combined organic layers were washed with brine, dried over anhydrous sodium sulfate, filtered and concentrated under reduced pressure to afford Int-116.1, MS (ES): m/z 223.1 [M+H]$^+$.

Synthesis of compound Int-116.3. A mixture of compound Int-116.2 (3.6 g, 16.21 mmol, 1.0 equiv) and 20% palladium hydroxide (1.30 g) in methanol (20 mL) was stirred under hydrogen for 3 h. The reaction mixture was filtered through a pad of Celite® and rinsed with methanol. The filtrate was concentrated under reduced pressure to afford Int-116.3. MS (ES): m/z 192.9 [M+H]$^+$.

Synthesis of compound Int-116.4. To a solution of Int-116.3 (2.9 g, 15.09 mmol, 1.0 equiv) in DMF (48 mL) was added N-bromosuccinimide (2.68 g, 15.09 mmol, 1.0 equiv) at −40° C. and stirred for 1.5 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-116.4. MS (ES): m/z 271.8 [M+H]$^+$.

Synthesis of compound Int-116.5. A mixture of Int-116.4 (1.8 g, 6.64 mmol, 1.0 equiv), zinc cyanide (0.388 g, 3.32 mmol, 0.5 equiv) and zinc powder (0.043 g, 0.66 mmol, 0.1 equiv) in DMF (15 mL) was degassed by bubbling argon through for 10 min. Under argon atmosphere 4,5-bis(diphenylphosphino)-9,9-dimethylxanthene (1.15 g, 1.99 mmol, 0.3 equiv) and tris(dibenzylideneacetone)dipalladium(0) (1.82 g, 1.99 mmol, 0.3 equiv) were added and degassed for 5 min. The reaction mixture was stirred at 120° C. for 5 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 23% ethyl acetate in hexane) to afford Int-116.5. MS (ES): m/z 218.1 [M+H]⁺.

Synthesis of compound Int-116.6. To a solution of Int-116.5 (0.270 g, 1.24 mmol, 1.0 equiv) in DCM (10 mL) was added boron tribromide (1 M in dichloromethane, 3.7 mL, 3.72 mmol, 3.0 equiv) slowly at 0° C. and stirred at room temperature for 16 h. It was poured over ice-cold saturated solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 3.5% methanol in DCM) to afford Int-116.6. MS (ES): m/z 203.9 [M+H]⁺.

Synthesis of compound Int-116.7. To a solution of Int-116.6 (0.2 g, 0.984 mmol, 1.0 equiv) in DMF (5 mL) was added potassium carbonate (0.176 g, 1.28 mmol, 1.3 equiv) and stirred for 30 min. To the mixture was added methyl iodide (0.153 g, 1.082 mmol, 1.1 equiv). It was stirred at room temperature for 3 h, poured over ice-water and stirred. The precipitated solids were collected by filtration and further purified by flash column chromatography on silica gel (CombiFlash®, 23% ethyl acetate in hexane) to afford Int-116.7. MS (ES): m/z 218.2 [M+H]⁺.

Synthesis of compound Int-116. Compound Int-116 was prepared from Int-116.7 following the procedure described in the synthesis of Int-1. The product was purified by flash column chromatography on silica gel (CombiFlash®, 25% ethyl acetate in hexane). MS (ES): m/z 260.1 [M+H]⁺.

Preparation of Intermediate Int-117: 3-isothiocyanato-1-(2-oxaspiro[3.3]heptan-6-yl)-5-(trifluoromethyl)-1H-pyrazole

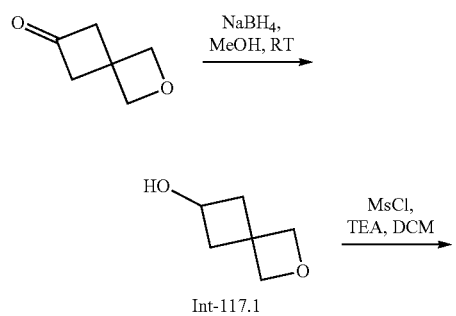

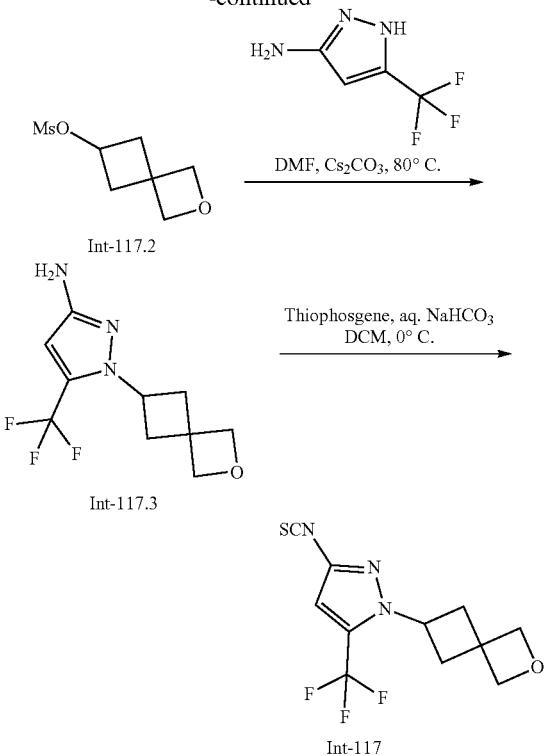

Synthesis of compound Int-117.1. To a solution of 2-oxaspiro[3.3]heptan-6-one (0.600 g, 5.35 mmol, 1.0 equiv) in methanol (10 mL) was added sodium borohydride (0.203 g, 5.35 mmol, 1.0 equiv) in small portions at 0° C. The reaction mixture was stirred at 0° C. for 2 h. It was poured over ice-water, stirred and extracted with ethyl acetate. The combined organic layers were washed with brine, dried over anhydrous sodium sulfate, filtered and concentrated under reduced pressure to obtain Int-117.1. MS (ES): m/z 115.2 [M+H]⁺.

Synthesis of compound Int-117.2. To a solution of Int-117.1 (0.540 g, 4.73 mmol, 1.0 equiv) and triethylamine (1.64 mL, 11.82 mmol, 2.5 equiv) in dichloromethane (10 mL) was added methanesulfonyl chloride (0.71 mL, 9.46 mmol, 2.0 equiv) at 0° C. The reaction mixture was stirred at room temperature for 12 h. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 40% ethyl acetate in hexane as eluant) to afford Int-117.2. MS (ES): m/z 193.2 [M+H]⁺.

Synthesis of compound Int-117.3. To a solution of Int-117.2 (0.4 g, 2.08 mmol, 1.0 equiv) and 5-(trifluoromethyl)-1H-pyrazol-3-amine (0.314 g, 2.08 mmol, 1.0 equiv) in DMF (7 mL) was added cesium carbonate (1.352 g, 4.16 mmol, 2.0 equiv), and the reaction mixture was stirred at 80° C. for 5 h. It was poured over ice-water, stirred and extracted with ethyl acetate. The combined organic layers were washed with brine, dried over anhydrous sodium sulfate, filtered and concentrated under reduced pressure. The residue was purified by preparative HPLC to obtain Int-117.3. MS (ES): m/z 248.2 [M+H]⁺.

Synthesis of compound Int-117. Compound Int-117 was prepared from Int-117.3 following the procedure described in the synthesis of Int-1. The crude product was used in the next step without further purification. MS (ES): m/z 290.2 [M+H]⁺.

Preparation of Intermediate Int-118: 4-(benzyloxy)-1-(3-isothiocyanato-5-(trifluoromethyl)phenyl)piperidine

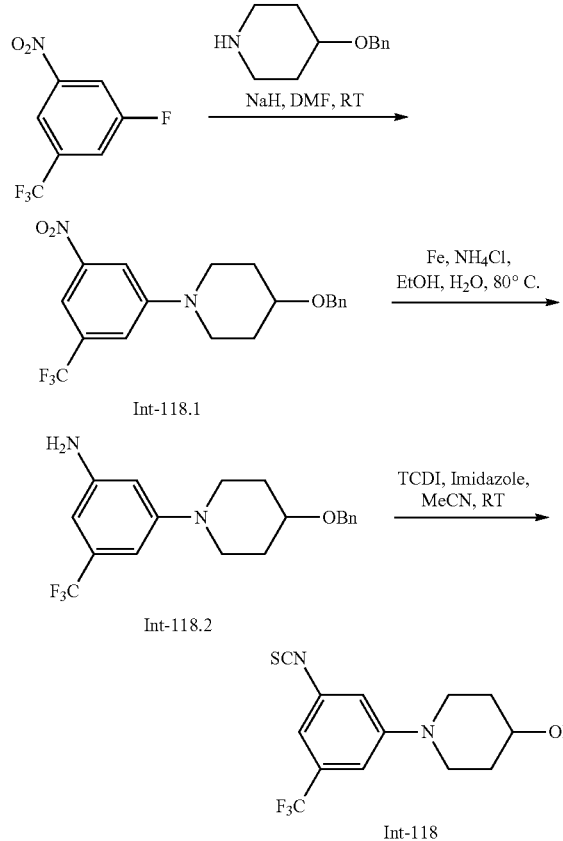

Synthesis of compound Int-118.1. Compound Int-118.1 was prepared from 1-fluoro-3-nitro-5-(trifluoromethyl)benzene and 4-(benzyloxy)piperidine, following the procedures described in the synthesis of Int-101.1. The product purified by flash column chromatography on silica gel (CombiFlash®, 15% ethyl acetate in hexane). MS (ES): m/z 381.1 [M+H]⁺.

Synthesis of compound Int-118.2. Compound Int-118.2 was prepared from Int-118.1, following the procedure described in the synthesis of 3.7. The product was purified by flash column chromatography on silica gel (CombiFlash®, 25% ethyl acetate in hexane). MS (ES): m/z 351.3 [M+H]⁺.

Synthesis of compound Int-118. Compound Int-118 was prepared from Int-118.2 following the procedure described in the synthesis of Int-69. The product was purified by flash column chromatography on silica gel (CombiFlash®, 25% ethyl acetate in hexane). MS (ES): m/z 393.4 [M+H]⁺.

Preparation of Intermediate Int-119: (R)-3-(benzyloxy)-1-(3-isothiocyanato-5-(trifluoromethyl)phenyl)pyrrolidine

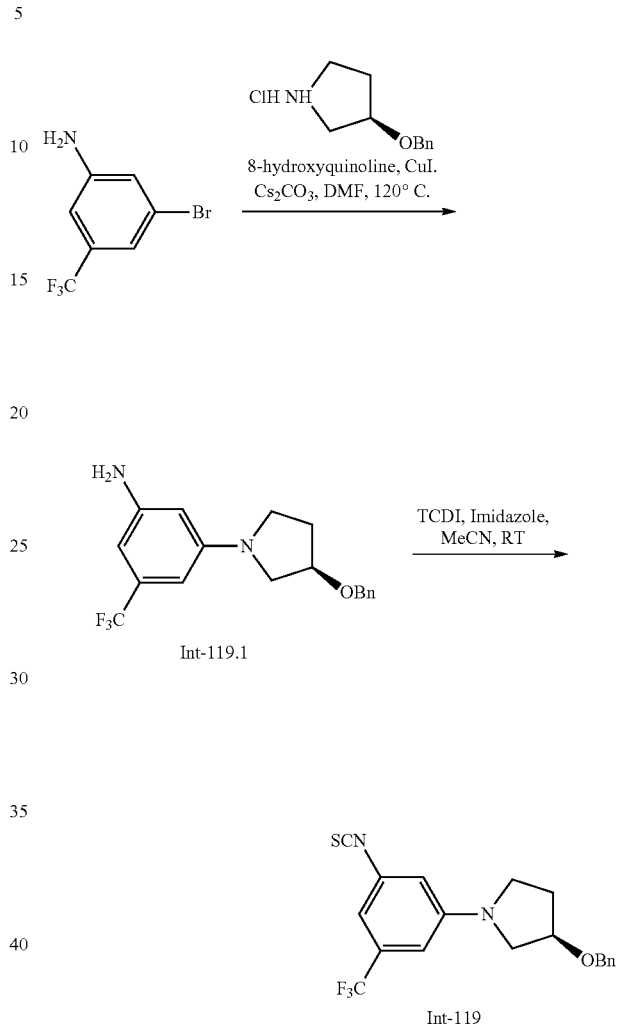

Synthesis of compound Int-119.1. A mixture of 3-bromo-5-(trifluoromethyl)aniline (0.9 g, 3.75 mmol, 1.0 equiv), (R)-3-(benzyloxy)pyrrolidine hydrochloride (1.2 g, 5.62 mmol, 1.5 equiv) and cesium carbonate (4.89 g, 15.0 mmol, 4.0 equiv) in DMF (9 mL) was degassed by bubbling argon through for 10 min. Under argon atmosphere copper iodide (0.213 g, 1.125 mmol, 0.3 equiv) and 8-hydroxyquinoline (0.163 g, 1.125 mmol, 0.3 equiv) was then added, again degassed for 5 min. The reaction mixture was stirred at 120° C. for 16 h. The reaction mixture was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-119.1. MS (ES): m/z 337.3 [M+H]⁺.

Synthesis of compound Int-119. Compound Int-119 was prepared from Int-119.1 following the procedure described in the synthesis of Int-69. The product was purified by flash column chromatography on silica gel (CombiFlash®, 30% ethyl acetate in hexane). MS (ES): m/z 379.2 [M+H]⁺.

Preparation of Intermediate Int-120: (S)-3-(benzyloxy)-1-(3-isothiocyanato-5-(trifluoromethyl)phenyl)pyrrolidine

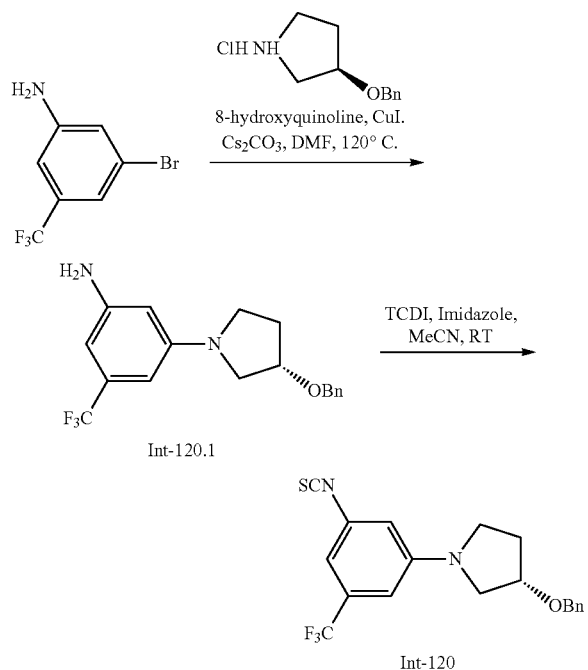

Synthesis of compound Int-120. Compound Int-120 was prepared following the procedures described in the synthesis of Int-119. The product was purified by flash column chromatography on silica gel (CombiFlash®, 30% ethyl acetate in hexane). MS (ES): m/z 379.2 [M+H]$^+$.

Preparation of Intermediate Int-121: ((S)-2-((3-isothiocyanato-5-(trifluoromethyl)phenoxy)methyl)-1-methylpyrrolidine

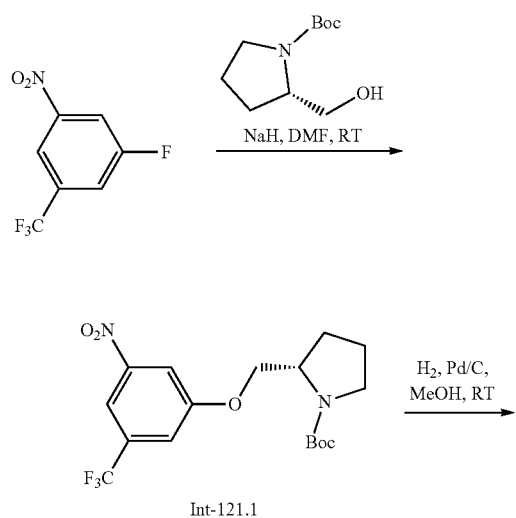

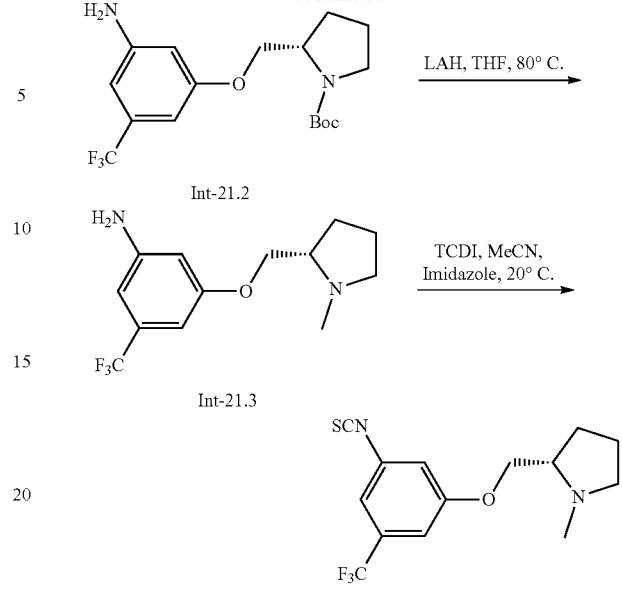

Synthesis of compound Int-121.1. Compound Int-121.1 was prepared from 1-fluoro-3-nitro-5-(trifluoromethyl)benzene and tert-butyl (S)-2-(hydroxymethyl)pyrrolidine-1-carboxylate, following the procedures described in the synthesis of Int-101.1. The product was purified by flash column chromatography on silica gel (CombiFlash®, 15-17% ethyl acetate in hexane). MS (ES): m/z 391.0 [M+H]$^+$.

Synthesis of compound Int-121.2. Compound Int-121.2 was prepared from Int-121.1, following the procedures described in the synthesis of Int-23.3. The product was purified by flash column chromatography on silica gel (CombiFlash®, 20-23% ethyl acetate in hexane). MS (ES): m/z 361.2 [M+H]$^+$.

Synthesis of compound Int-121.3. Compound Int-121.3 was prepared from Int-121.2, following the procedures described in the synthesis of Int-81.2. The product was purified by flash column chromatography on silica gel (CombiFlash®, 60-65% ethyl acetate in hexane). MS (ES): m/z 275.1 [M+H]$^+$.

Synthesis of compound Int-121. Compound Int-121 was prepared from Int-121.3 following the procedure described in the synthesis of Int-69. The product was purified by flash column chromatography on silica gel (CombiFlash®, 1.5% methanol in DCM). MS (ES): m/z 317.2 [M+H]$^+$.

Preparation of Intermediate Int-122: ((R)-2-((3-isothiocyanato-5-(trifluoromethyl)phenoxy)methyl)-1-methylpyrrolidine

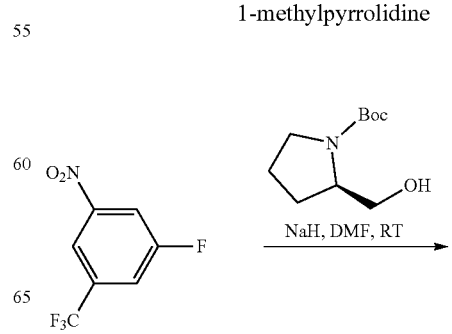

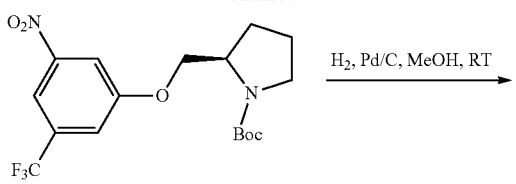



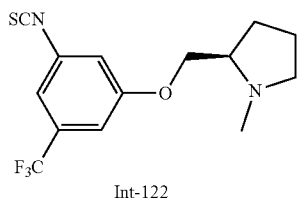

Synthesis of compound Int-122. Compound Int-122 was prepared following the procedures described in the synthesis of Int-121. The product was purified by flash column chromatography on silica gel (CombiFlash®, 1.5% methanol in DCM). MS (ES): m/z 317.2 [M+H]$^+$.

Preparation of Intermediate Int-123: 5-cyclopentyl-2-isothiocyanato-4,6-dimethylpyrimidine

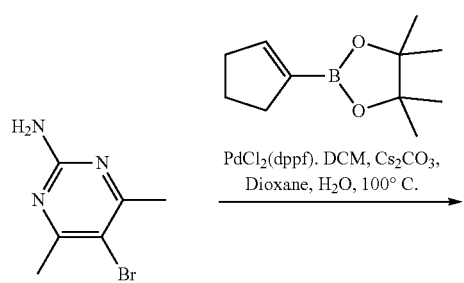

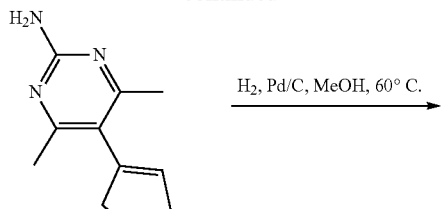

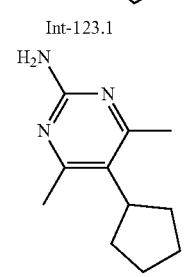

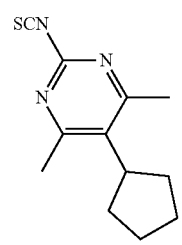

Synthesis of compound Int-123.1. A mixture of 5-bromo-4,6-dimethylpyrimidin-2-amine (0.500 g, 2.47 mmol, 1.0 equiv), 2-(cyclopent-1-en-1-yl)-4,4,5,5-tetramethyl-1,3,2-dioxaborolane (1.44 g, 7.42 mmol, 3.0 equiv) and cesium carbonate (2.41 g, 7.42 mmol, 3.0 equiv) in 1,4-dioxane (5 mL) was degassed by bubbling argon through for 10 min. To the mixture was added 1,1-bis(diphenylphosphino)ferrocene-palladium(II) dichloride DCM complex (0.060 g, 0.074 mmol, 0.03 equiv) and degassed for another 5 min. The reaction mixture was stirred at 100° C. for 1 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% methanol in DCM) to afford Int-123.1. MS (ES): m/z 190.3 [M+H]$^+$.

Synthesis of compound Int-123.2. A mixture of Int-123.1 (0.350 g, 1.85 mmol, 1.0 equiv) and 10% palladium on charcoal (0.200 g) in methanol in an autoclave was stirred under hydrogen (100 psi) at 60° C. for 16 h. It was cooled to room temperature and filtered through a pad of Celite®, rinsed with methanol. The filtrate was concentrated under reduced pressure to afford Int-123.2. MS (ES): m/z 192.2 [M+H]$^+$.

Synthesis of compound Int-123. Compound Int-123 was prepared from Int-123.2 following the procedure described in the synthesis of Int-1. The product was purified by flash column chromatography on silica gel (CombiFlash®, 20% ethyl acetate in hexane) to afford Int-123. MS (ES): m/z 234.3 [M+H]$^+$.

Preparation of Intermediate Int-124: 4-(3-isothiocyanato-5-(trifluoromethyl)phenyl)-1-methylpiperidine

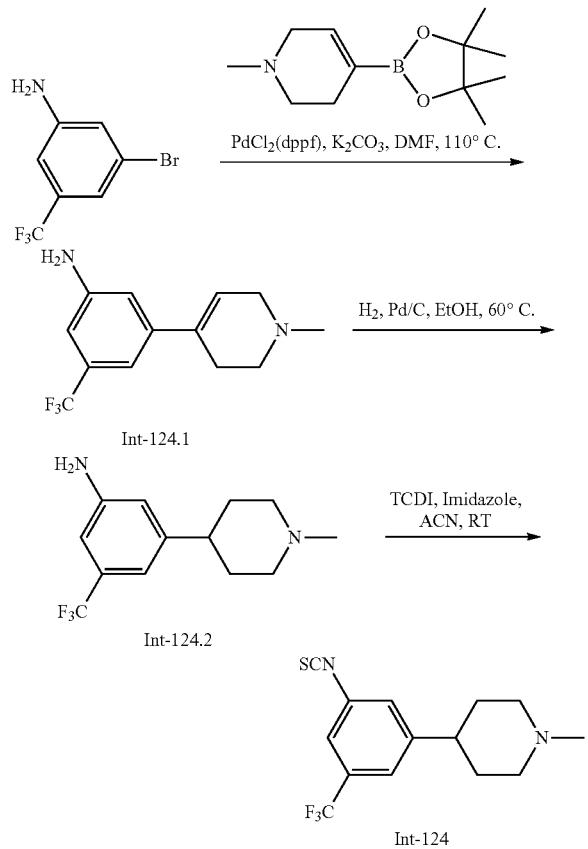

Int-124

Synthesis of compound Int-124.1. A mixture of 3-bromo-5-(trifluoromethyl)aniline (1.0 g, 4.17 mmol, 1.0 equiv), 1-methyl-4-(4,4,5,5-tetramethyl-1,3,2-dioxaborolan-2-yl)-1,2,3,6-tetrahydropyridine (2.79 g, 12.50 mmol, 3.0 equiv) and potassium carbonate (1.72 g, 12.50 mmol, 3.0 equiv) in DMF (25 mL) was degassed by bubbling argon through for 10 min. To the mixture was added 1,1-bis(diphenylphosphino)ferrocene-palladium(II) dichloride (0.304 g, 0.417 mmol, 0.1 equiv) and degassed for another 5 min. The reaction mixture was stirred at 110° C. for 16 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5.0% methanol in DCM) to afford Int-124.1. MS (ES): m/z 257.2 [M+H]$^+$.

Synthesis of compound Int-124.2. A mixture of Int-124.1 (0.600 g, 2.34 mmol, 1.0 equiv) and 10% palladium on charcoal (0.300 g) in ethanol was stirred in an autoclave under hydrogen pressure (100 psi) at 60° C. for 16 h. It was cooled to room temperature, filtered through a pad of Celite®, rinsed with methanol. The filtrate was concentrated under reduced pressure to afford Int-124.2. MS (ES): m/z 259.1 [M+H]$^+$.

Synthesis of compound Int-124. Compound Int-124 was prepared from Int-124.2 following the procedure described in the synthesis of Int-69. The product was purified by flash column chromatography on silica gel (CombiFlash®, 2.0% methanol in DCM). MS (ES): m/z 300.9 [M+H]$^+$.

Preparation of Intermediate Int-125: 1-(3-isothiocyanato-5-(trifluoromethyl)phenyl)-N,N-dimethylmethanamine

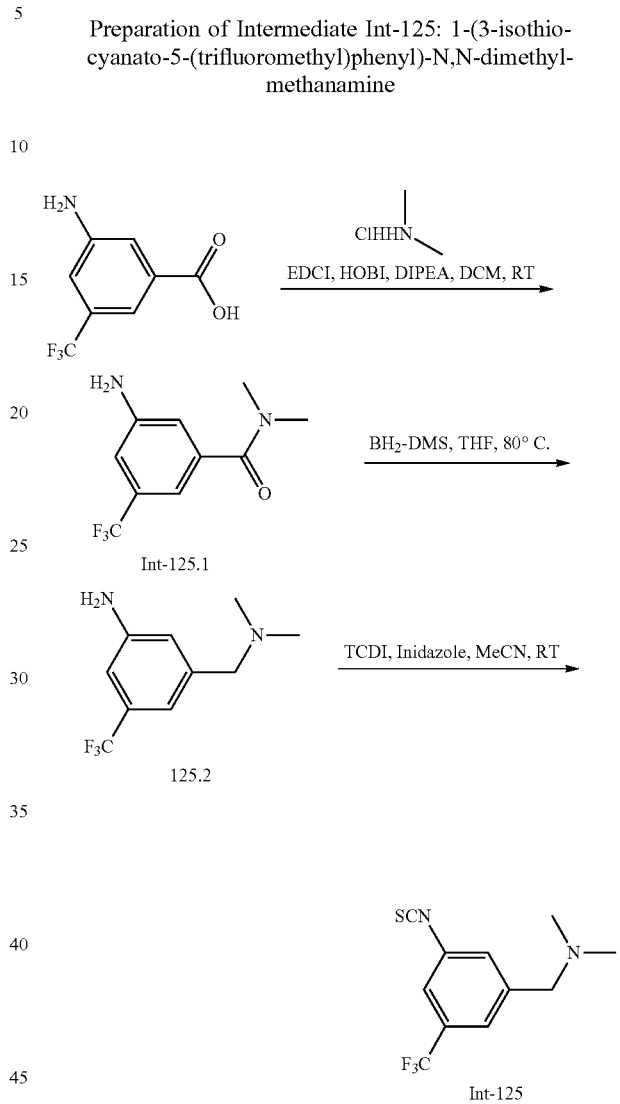

Int-125

Synthesis of compound Int-125.1. Compound Int-125.1 was prepared from 3-amino-5-(trifluoromethyl)benzoic acid and dimethylamine hydrochloride, following the procedure described in the synthesis of Int-79.1. The product was purified by flash column chromatography on silica gel (CombiFlash®, 2.2% methanol in DCM). MS (ES): m/z 233.1 [M+H]$^+$.

Synthesis of compound Int-125.2. Compound Int-125.2 was prepared from Int-125.1, following the procedures described in the synthesis of Int-79.2. The product was purified by flash column chromatography on silica gel (CombiFlash®, 2.7% methanol in DCM). MS (ES): m/z 219.0 [M+H]$^+$.

Synthesis of compound Int-125. Compound Int-125 was prepared from Int-125.2 following the procedure described in the synthesis of Int-69. The product was purified by flash column chromatography on silica gel (CombiFlash®, 1.0% methanol in DCM). MS (ES): m/z 260.9 [M+H]$^+$.

Preparation of Intermediate Int-126: 1-(3-isothiocyanato-5-(trifluoromethyl)benzyl)azetidine

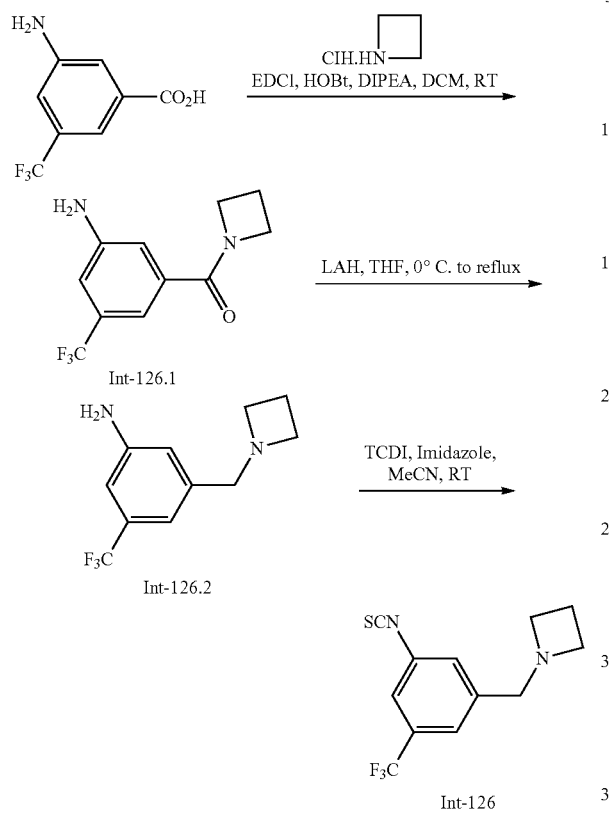

Synthesis of compound Int-126.1. Compound Int-126.1 was prepared from 3-amino-5-(trifluoromethyl)benzoic acid and azetidine hydrochloride, following the procedure described in the synthesis of Int-79.1. The product was purified by flash column chromatography on silica gel (CombiFlash®, 2.5% methanol in DCM). MS (ES): m/z 245.1 [M+H]$^+$.

Synthesis of compound Int-126.2. Compound Int-126.2 was prepared from Int-126.1, following the procedures described in the synthesis of Int-81.2. The product was purified by flash column chromatography on silica gel (CombiFlash®, 4.8% methanol in DCM). MS (ES): m/z 231.0 [M+H]$^+$.

Synthesis of compound Int-126. Compound Int-126 was prepared from Int-126.2 following the procedure described in the synthesis of Int-69. The product was purified by flash column chromatography on silica gel (CombiFlash®, 2.0% methanol in DCM). MS (ES): m/z 272.9 [M+H]$^+$.

Preparation of Intermediate Int-127: 3-(benzyloxy)-1-(3-isothiocyanato-5-(trifluoromethyl)benzyl)azetidine

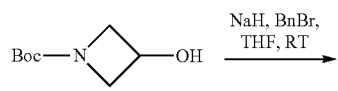

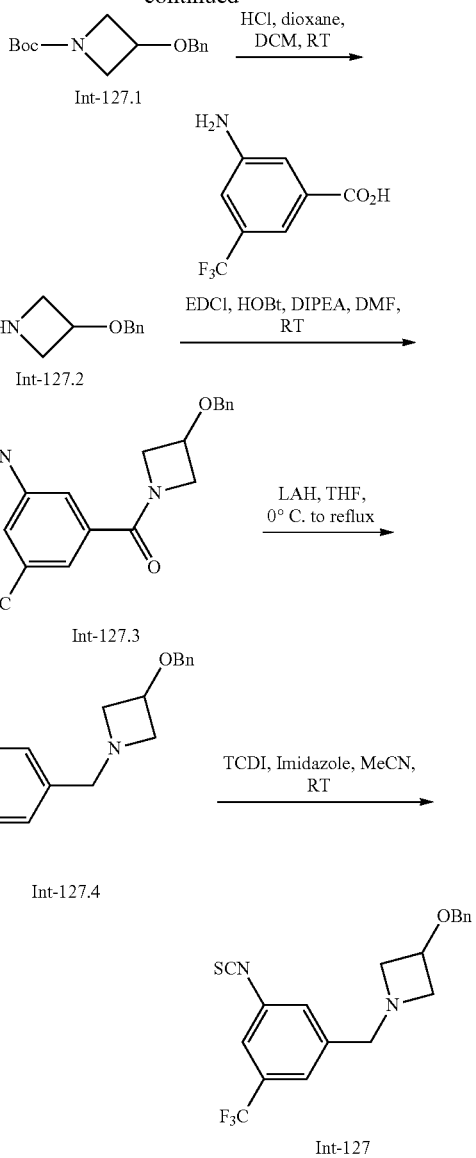

Synthesis of compound Int-127.1. To a solution of tert-butyl 3-hydroxyazetidine-1-carboxylate (1.0 g, 5.77 mmol, 1.0 equiv) in THF (15 mL) was added sodium hydride (0.346 g, 8.66 mmol, 1.5 equiv) at 0° C. and stirred for 30 min followed by addition of benzyl bromide (1.18 g, 6.92 mmol, 1.2 equiv) and reaction mixture was stirred at room temperature for 30 min. It was poured over water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford Int-127.1. MS (ES): m/z 264.1 [M+H]$^+$.

Synthesis of compound Int-127.2. To a solution of Int-127.1 (1.05 g, 3.99 mmol, 1.0 equiv) in DCM (20 mL) was added 4 M hydrogen chloride in dioxane (7 mL) at 0° C. The reaction mixture was stirred at room temperature for 1 h. It was concentrated under reduced pressure. The residue was purified by trituration in diethyl ether to afford Int-127.2. MS (ES): m/z 164.2 [M−HCl]$^+$.

Synthesis of compound Int-127.3. Compound Int-127.3 was prepared from 3-amino-5-(trifluoromethyl)benzoic acid and Int-127.2, following the procedure described in the synthesis of Int-79.1. The product was purified by flash column chromatography on silica gel (CombiFlash®, 2.3% methanol in DCM). MS (ES): m/z 351.1 [M+H]$^+$.

Synthesis of compound Int-127.4. Compound Int-127.4 was prepared from Int-127.3, following the procedures described in the synthesis of Int-81.2. The product was purified by flash column chromatography on silica gel (CombiFlash®, 25% ethyl acetate in hexane) elu. MS (ES): m/z 337.2 [M+H]$^+$.

Synthesis of compound Int-127. Compound Int-127 was prepared from Int-127.4 following the procedure described in the synthesis of Int-69. The product was purified by flash column chromatography on silica gel (CombiFlash®, 1.0% methanol in DCM). MS (ES): m/z 379.3 [M+H]$^+$.

Preparation of Intermediate Int-128: 3-isothiocyanato-1-(tetrahydrofuran-3-yl)-5-(trifluoromethyl)pyridin-2(1H)-one

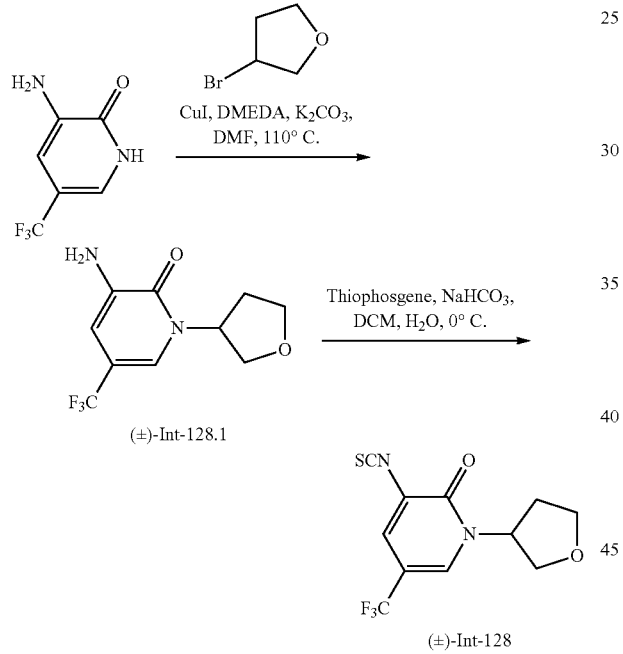

Synthesis of compound (±)-Int-128.1. A mixture of 3-amino-5-(trifluoromethyl)pyridin-2(1H)-one (2.0 g, 11.23 mmol, 1.0 equiv), (±)-3-bromotetrahydrofuran (3.39 g, 22.46 mmol, 2.0 equiv) and potassium carbonate (4.64 g, 33.69 mmol, 3.0 equiv) in DMF (20 mL) was degassed by bubbling through a stream of argon for 15 min. Copper iodide (0.428 g, 2.24 mmol, 0.2 equiv) and 1,2-dimethylethylenediamine (0.395 g, 4.49 mmol, 0.4 equiv) were added and degassed for another 5 min. The mixture was stirred at 110° C. for 16 h. It was cooled to room temperature, transferred into water and extracted with ethyl acetate. The combined organic layers were washed with brine, dried over anhydrous sodium sulfate, filtered and concentrated under reduced pressure. The residue was purified by column chromatography and compound was eluted in 25% ethyl acetate in hexane) to afford (±)-Int-128.1. MS (ES): m/z 249.2 [M+H]$^+$.

Synthesis of compound (±)-Int-128. Compound (±)-Int-128 was prepared from (±)-Int-128.1 following the procedure described in the synthesis of Int-1. The product was purified by flash column chromatography on silica gel (CombiFlash®, 1% methanol in DCM). MS (ES): m/z 290.8 [M+H]$^+$.

Preparation of Intermediate Int-129: 3-amino-5-cyclopropyl-6-fluoro-1-methylpyridin-2(1H)-one

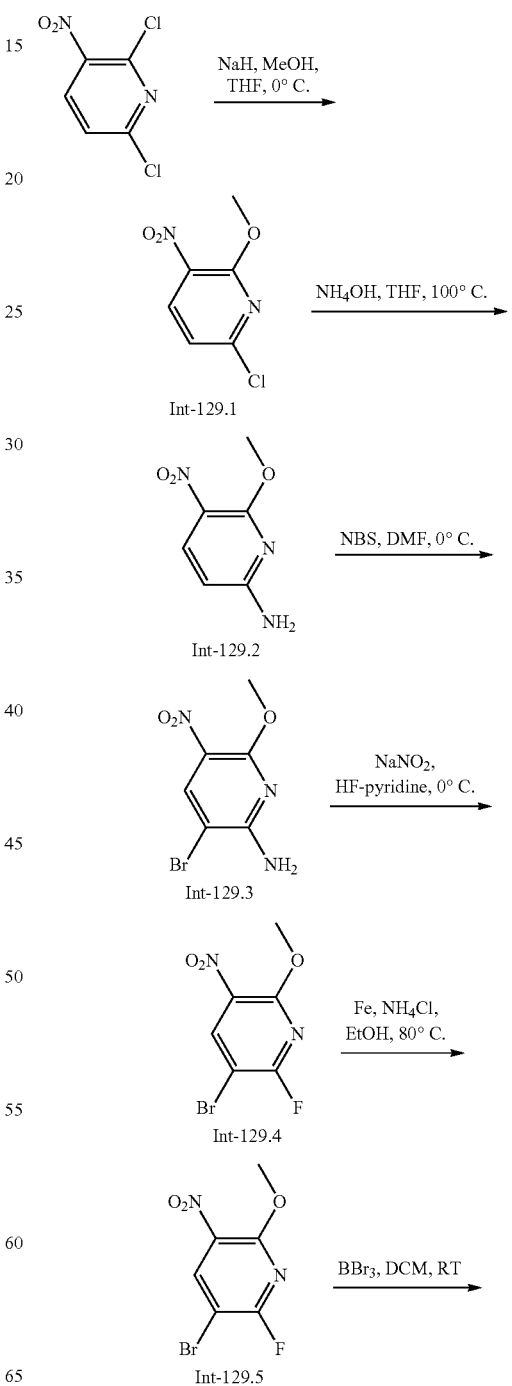

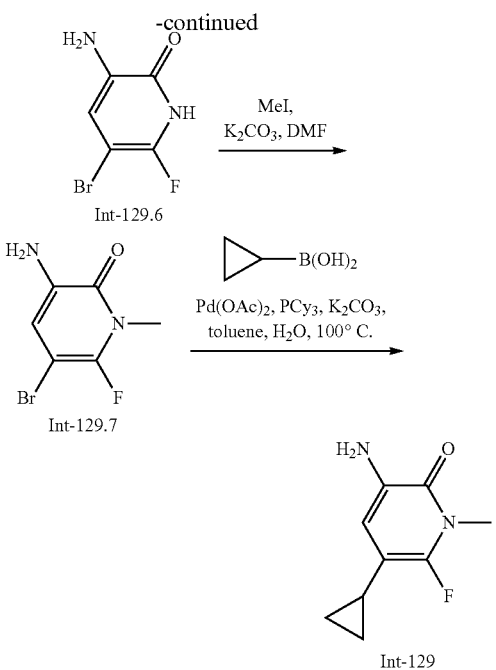

Synthesis of compound Int-129.1. To solution of 2,6-dichloro-3-nitropyridine (50 g, 259 mmol, 1.0 equiv) in THF (500 mL) and methanol (9.4 mL, 233 mmol, 0.9 equiv) at 0° C. was added sodium hydride (10.3 g, 259 mmol, 1.0 equiv) in portions. After the addition, the reaction mixture was allowed to warm to room temperature and stirred for 16 h. It was poured over ice cold water and extracted with ethyl acetate. The combined organic layers were washed with brine, dried over anhydrous sodium sulfate, filtered and concentrated under reduced pressure. The residue was purified by flash column chromatography on silica gel (CombiFlash®, 8.0% ethyl acetate in hexane) to afford Int-129.1. MS (ES): m/z 189.3 [M+H]$^+$.

Synthesis of compound Int-129.2. A solution of Int-129.1 (27 g, 143 mmol, 1.0 equiv) and ammonia (7 N in water, 11 mL) in THF (270 mL) was stirred at 100° C. for 5 h in an autoclave. It cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford Int-129.2. MS (ES): m/z 170.1 [M+H]$^+$.

Synthesis of compound Int-129.3. To a solution of Int-129.2 (6.0 g, 35.47 mmol, 1.0 equiv) in DMF (60 mL) was added N-bromosuccinimide (12.62 g, 70.94 mmol, 2.0 equiv) in portions at 0° C. and the reaction mixture was stirred for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford Int-129.2. MS (ES): m/z 248.9 [M+H]$^+$.

Synthesis of compound Int-129.4. To a solution of hydrogen fluoride pyridine (60 mL) at 0° C. was added Int-129.3 (5.3 g, 21.37 mmol, 1.0 equiv) in portions followed by the addition of sodium nitrite (2.90 g, 42.74 mmol, 2.0 equiv). The reaction mixture was stirred 0° C. for 2 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford Int-129.4. MS (ES): m/z 252.01 [M+H]$^+$.

Synthesis of compound Int-129.5. Compound Int-129.5 was prepared from Int-129.4, following the procedure described in the synthesis of 3.7. The product was purified by flash column chromatography on silica gel (CombiFlash®, 49% ethyl acetate in hexane). MS (ES): m/z 222.1 [M+H]$^+$.

Synthesis of compound Int-129.6. To a solution of Int-129.5 (1.3 g, 5.88 mmol, 1.0 equiv) in DCM (30 mL) was added boron tribromide (18 mL, 14 v/w) slowly and stirred at room temperature for 3 h. It was poured over ice, neutralized with sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 18% ethyl acetate in hexane) to afford 1 nt-129.6. MS (ES): m/z 208.0 [M+H]$^+$.

Synthesis of compound Int-129.7. A mixture of Int-129.6 (0.380 g, 1.84 mmol, 1.0 equiv) and potassium carbonate (0.507 g, 3.68 mmol, 2.0 equiv) in DMF (3 mL) was stirred for 30 min at 0° C. Methyl iodide (0.261 g, 1.84 mmol, 1.0 equiv) was added and the reaction mixture was stirred at 0° C. for 1 h. It was poured over ice-water and precipitated product was filtered out, dried well. The residue was purified by flash column chromatography on silica gel (CombiFlash®, 20% ethyl acetate in hexane) to afford Int-129.7. MS (ES): m/z 222.1 [M+H]$^+$.

Synthesis of compound Int-129. Compound Int-129 was prepared from Int-129.7, following the procedure described in the synthesis of Int-23.2. The product was purified by flash column chromatography on silica gel (CombiFlash®, 42% ethyl acetate in hexane). MS (ES): m/z 183.2 [M+H]$^+$.

Preparation of Intermediate (±)-trans-Int-130: trans-tert-butyl-3-(5-(tert-butyl)-3-isothiocyanato-1H-pyrazol-1-yl)-4-fluoropyrrolidine-1-carboxylate

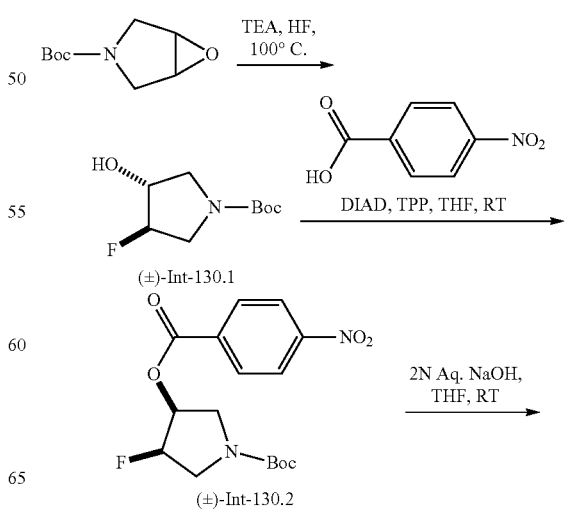

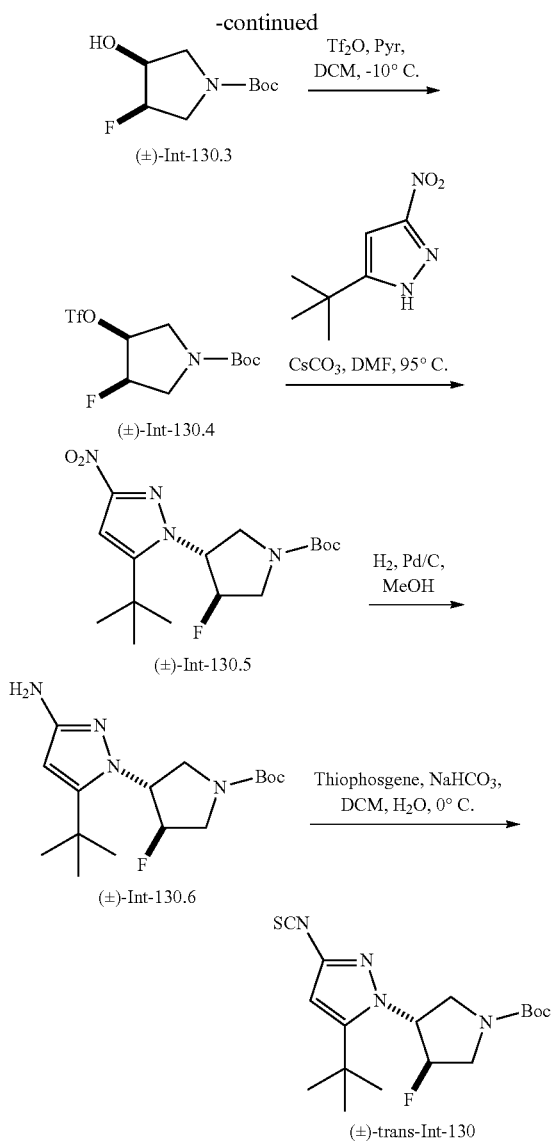

over anhydrous sodium sulfate, filtered, and concentrated under reduced pressure. The residue was purified by flash column chromatography on silica gel (CombiFlash®, 6% ethyl acetate in hexane) to afford (±)-Int-130.2. $^1$H NMR (DMSO-$d_6$, 400 MHz): δ 8.43-8.40 (d, J=9.2 Hz, 2H), 8.35-8.33 (d, J=8.8 Hz, 2H), 4.92-4.75 (m, 6H), 1.19 (s, 9H).

Synthesis of compound (±)-Int-130.3. To a solution of (±)-Int-130.2 (25 g, 70.55 mmol, 1.0 equiv) in THF (125 mL) was added aq. sodium hydroxide (2 N in water, 150 mL) and stirred at room temperature for 2 h. The reaction mixture was concentrated under reduced pressure. The residue was purified by flash column chromatography on silica gel (CombiFlash®, 20% ethyl acetate in hexane) to afford (±)-Int-130.3. $^1$H NMR (DMSO-$d_6$, 400 MHz): δ 5.53-5.52 (m, 1H), 4.98-4.85 (m, 1H), 4.19 (bs, 1H), 3.60-3.25 (m, 4H), 1.42 (s, 9H).

Synthesis of compound (±)-Int-130.4. To a solution of (±)-Int-130.3 (10 g, 48.73 mmol, 1.0 equiv) and pyridine (19.2 g, 243.65 mmol, 5.0 equiv) in DCM (200 mL) at −10° C. was added triflic anhydride (27.48 g, 97.46 mmol, 2.0 equiv) and stirred for 2 h. It was transferred into ice-saturated citric acid solution and pH was adjusted to 5 by addition of sodium bicarbonate. The mixture was extracted with DCM. The combined organic layers were washed with brine, dried over anhydrous sodium sulfate, filtered, and concentrated under reduced pressure to afford (±)-Int-130.4. $^1$H NMR (DMSO-$d_6$, 400 MHz): δ 5.51-5.36 (m, 1H), 5.21-5.17 (m, 1H), 3.83-3.35 (m, 4H), 1.42 (s, 9H).

Synthesis of compound (±)-Int-130.5. A mixture of (±)-Int-130.4 (4.0 g, 23.64 mmol, 1.0 equiv), 5-(tert-butyl)-3-nitro-1H-pyrazole (4.8 g, 28.37 mmol, 1.2 equiv), and cesium carbonate (23 g, 70.92 mmol, 3.0 equiv) in DMF (100 mL) was stirred at 95° C. for 16 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.0% ethyl acetate in hexane) to afford (±)-Int-130.5. MS (ES): m/z 357.2 [M+H]$^+$.

Synthesis of compound (±)-Int-130.6. A mixture of compound (±)-Int-130.5 (0.500 g, 1.40 mmol, 1.0 equiv) and 10% palladium on carbon (0.250 g) in methanol (10 mL) was stirred under hydrogen atmosphere for 30 min. The reaction mixture was filtered through a pad of Celite® and rinsed with methanol. The filtrate was concentrated under reduced pressure to afford (±)-Int-130.6. MS (ES): m/z 327.1 [M+H]$^+$.

Synthesis of compound (±)-Int-130. Compound (±)-Int-130 was prepared from (f)-Int-130.6, following the procedure described in the synthesis of Int-1. The product was purified by flash column chromatography on silica gel (CombiFlash®, DCM). MS (ES): m/z 369.2 [M+H]$^+$.

Preparation of Intermediate Int-131: 5-(azetidin-1-yl)-2-isothiocyanato-4,6-dimethylpyrimidine Synthesis of compound (±)-Int-130.1. A solution of tert-butyl 6-oxa-3-azabicyclo[3.1.0]hexane-3-carboxylate (50 g, 269 mmol, 1.0 equiv) in triethylamine hydrofluoride (51.9 g, 322.8 mmol, 1.2 equiv) was stirred at 100° C. for 16 h. It was transferred into ice-saturated sodium bicarbonate solution, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford (±)-Int-130.1. $^1$H NMR (CDCl$_3$, 400 MHz): δ 5.02-4.90 (m, 1H), 4.43-4.41 (m, 1H), 3.85-3.50 (m, 4H), 2.70 (bs, 1H), 1.47 (s, 9H).

Synthesis of compound (±)-Int-130.2. To a solution of compound (±)-Int-130.1 (27 g, 131.56 mmol, 1.0 equiv), 4-nitrobenzoic acid (43.97 g, 263.12 mmol, 2.0 equiv), and triphenyl phosphine (68.93 g, 263.12 mmol, 2.0 equiv) in THF (540 mL) at 0° C. was added diisopropyl azodicarboxylate (53.15 g, 263.12 mmol, 2.0 equiv), and reaction mixture was stirred at room temperature for 16 h. It was transferred into ice-water and extracted with ethyl acetate. The combined organic layers were washed with brine, dried

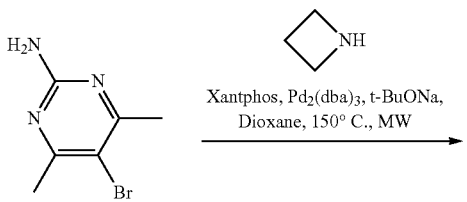

-continued

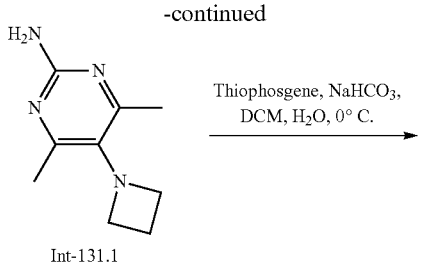

Synthesis of compound Int-131.1. A solution of 5-bromo-4,6-dimethylpyrimidin-2-amine (0.500 g, 2.47 mmol, 1.0 equiv), azetidine (0.706 g, 12.37 mmol, 5.0 equiv), and sodium tert-butoxide (0.711 g, 7.41 mmol, 3.0 equiv) in 1,4-dioxane (10 mL) was degassed by bubbling argon through for 10 min. Under argon atmosphere, 4,5-bis(diphenylphosphino)-9,9-dimethylxanthene (0.071 g, 0.123 mmol, 0.05 equiv) and tris(dibenzylideneacetone)dipalladium(0) (0.045 g, 0.049 mmol, 0.02 equiv) were added, and degassed for 5 min. The reaction mixture was stirred in a microwave reactor at 150° C. for 30 min. The reaction mixture was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-131.1. MS (ES): m/z 179.1 [M+H]$^+$.

Synthesis of compound Int-131. Compound Int-131 was prepared from Int-131.1, following the procedure described in the synthesis of Int-1. The product was purified by flash column chromatography on silica gel (CombiFlash®, DCM). MS (ES): m/z 221.2 [M+H]$^+$.

Preparation of Intermediate Int-132-a and Int-132-b: (R)-2-(3-isothiocyanato-5-(trifluoromethyl)phenyl)-1-methylpyrrolidine and (S)-2-(3-isothiocyanato-5-(trifluoromethyl)phenyl)-1-methylpyrrolidine

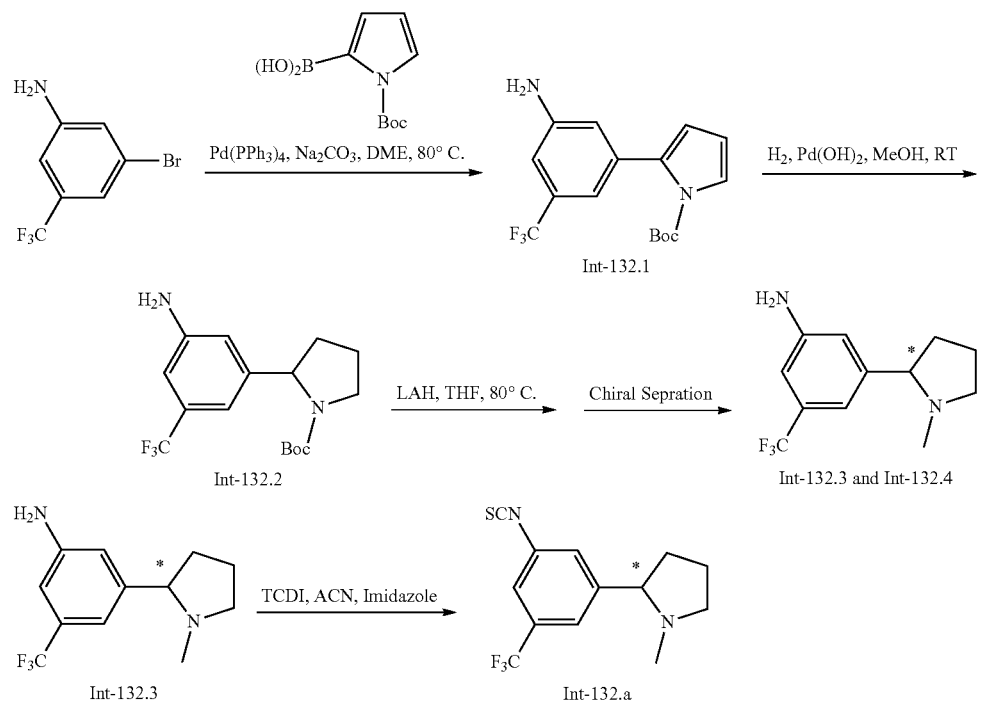

Synthesis of compound Int-132.1. A mixture of 3-bromo-5-(trifluoromethyl)aniline (2.5 g, 10.42 mmol, 1.0 equiv), (1-(tert-butoxycarbonyl)-1H-pyrrol-2-yl)boronic acid (4.4 g, 20.83 mmol, 2.0 equiv) and sodium carbonate (3.31 g, 31.26 mmol, 3.0 equiv) in dimethoxyethane (25 mL) was degassed by bubbling argon through for 10 min. Tetrakis(triphenylphosphine)palladium(0) (1.2 g, 1.042 mmol, 0.1 equiv) was added, and degassed for 5 min. The reaction mixture was stirred at 80° C. for 5 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-132.1. MS (ES): m/z 327.2 [M+H]$^+$.

Synthesis of compound Int-132.2. A mixture of compound Int-132.1 (2.1 g, 6.44 mmol, 1.0 equiv) and 20% palladium hydroxide (1.0 g) in methanol (20 mL) was stirred under hydrogen (1 atm) for 1 h. The reaction mixture was filtered through a pad of Celite® and rinsed with methanol. The filtrate was concentrated under reduced pressure to afford Int-132.2. MS (ES): m/z 331.1 [M+H]$^+$.

Synthesis of compound Int-132.3 and Int-132.4. To a solution of Int-132.2 (1.37 g, 4.15 mmol, 1.0 equiv) in THF (10 mL) was added lithium aluminum hydride (1 M in THF, 29 mL, 29.05 mmol, 7.0 equiv) at 0° C. The reaction mixture was stirred to reflux for 30 min. The reaction mixture was cooled to room temperature, transferred into ice, stirred, and extracted with ethyl acetate. The combined organic layers were washed with brine, dried over anhydrous sodium sulfate, filtered, and concentrated under reduced pressure. The racemate was separated by HPLC (column: CHIRALPAK AD-H (250 mm×21 mm, 5 µm); mobile phases: (A) 0.1% DEA in n-hexane, (B) 0.1% DEA in propan-2-ol; flow rate: 30 mL/min) to afford first eluting fraction (Int-132.3) and second eluting fraction (Int-132.4). MS (ES): m/z: 245.1 [M+H]$^+$. (*Absolute stereochemistry not determined.)

Synthesis of compound Int-132-a. To a solution of Int-132.3 (0.100 g, 0.409 mmol, 1.0 equiv) and imidazole (0.008 g, 0.122 mmol, 0.3 equiv) in acetonitrile (5 mL) was added thiocarbonyldiimidazole (0.241 g, 1.354 mmol, 2.0 equiv) and stirred at room temperature for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford Int-132-a. MS (ES): m/z 287.2 [M+H]$^+$.

Synthesis of compound Int-132-b. Compound Int-132-b was prepared from Int-132.4, following the synthesis of Int-132-a. The product was purified by flash column chromatography on silica gel (CombiFlash®, 12% ethyl acetate in hexane). MS (ES): m/z 287.2 [M+H]$^+$.

Preparation of Intermediate Int-133: (R)-1-(3-isothiocyanato-5-(trifluoromethyl)benzyl)-N,N-dimethylpyrrolidin-3-amine

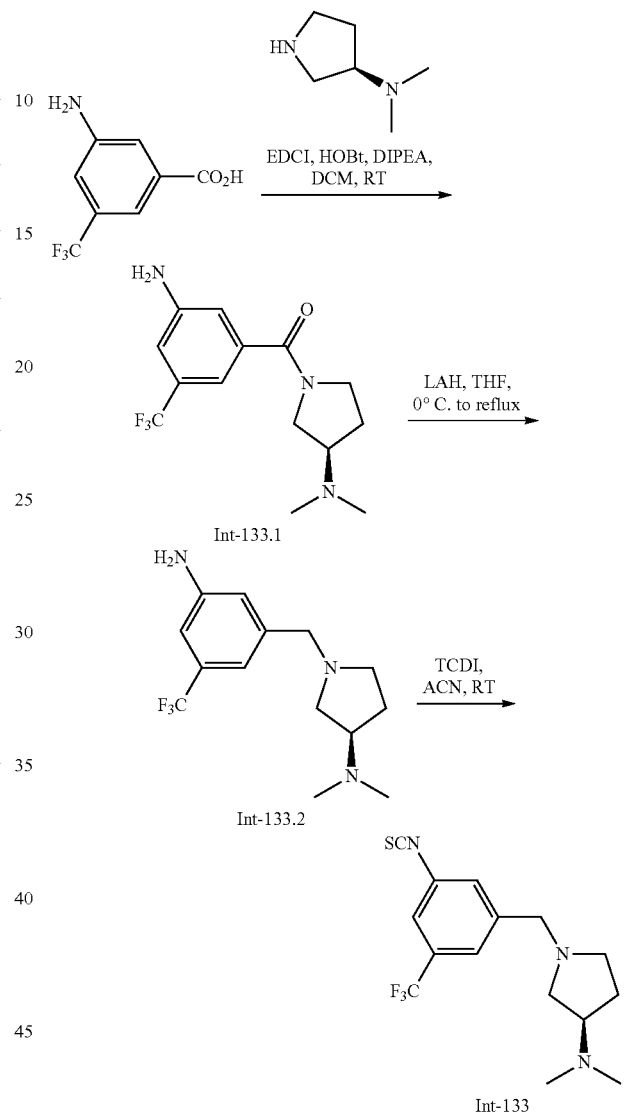

Synthesis of compound Int-133.1. To a solution of 3-amino-5-(trifluoromethyl)benzoic acid (1 g, 4.87 mmol, 1.0 equiv) in DCM (15 mL) was added 1-hydroxybenzotriazole (0.986 g, 7.30 mmol, 1.5 equiv), 1-ethyl-3-(3-dimethylaminopropyl)carbodiimide hydrochloride (1.39 g, 7.30 mmol, 1.5 equiv) and N,N-diisopropylethylamine (4.25 mL, 24.35 mmol, 5.0 equiv) and stirred at room temperature for 30 min. To the mixture was added (R)—N,N-dimethylpyrrolidin-3-amine (0.723 g, 6.34 mmol, 1.3 equiv) and stirred at room temperature for 4 h. It was transferred into ice-water, stirred, and extracted with DCM. The combined organic layers were washed with brine, dried over anhydrous sodium sulfate, filtered, and concentrated under reduced pressure. The residue was purified by preparative HPLC to afford Int-133.1. MS (ES): m/z 302.1 [M+H]$^+$.

Synthesis of compound Int-133.2. To a solution of Int-133.1 (0.400 g, 1.33 mmol, 1.0 equiv) in THF (10 mL) was added lithium aluminum hydride (1 M in THF, 4.0 mL, 3.99 mmol, 3.0 equiv) at 0° C. The reaction mixture was stirred to reflux for 2 h. The reaction mixture was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 11% methanol in DCM) to afford Int-133.2. MS (ES): m/z 288.2 [M+H]$^+$.

Synthesis of compound Int-133. Compound Int-133 was prepared from Int-133.2, following the synthesis of Int-69. The product was purified by flash column chromatography on silica gel (CombiFlash®, 3.5% methanol in DCM). MS (ES): m/z 330.2 [M+H]$^+$.

Preparation of Intermediate Int-134: (S)-1-(3-isothiocyanato-5-(trifluoromethyl)benzyl)-N,N-dimethylpyrrolidin-3-amine

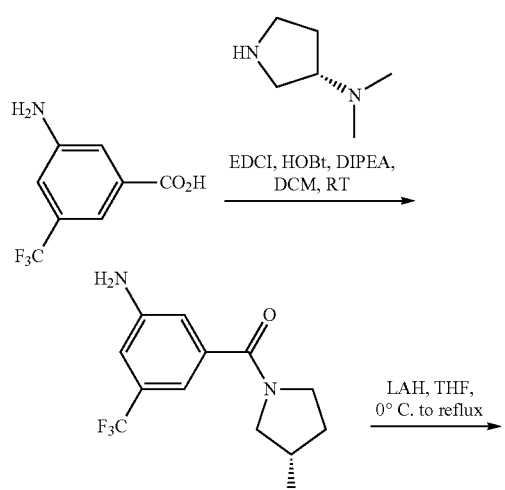

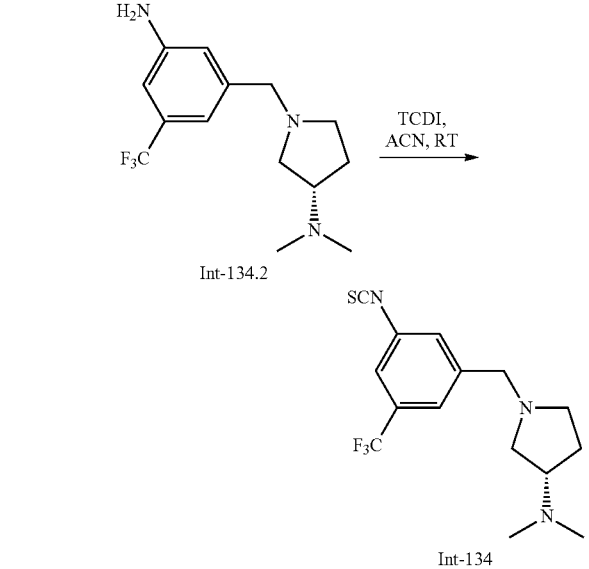

Synthesis of compound Int-134. Compound Int-134 was prepared following the procedures described in the synthesis of Int-133. The final product was purified by flash column chromatography on silica gel (CombiFlash®, 3.4% methanol in DCM). MS (ES): m/z 330.1 [M+H]$^+$.

Preparation of Intermediate Int-135: 4-isothiocyanato-N,N-dimethyl-6-(trifluoromethyl)pyridin-2-amine

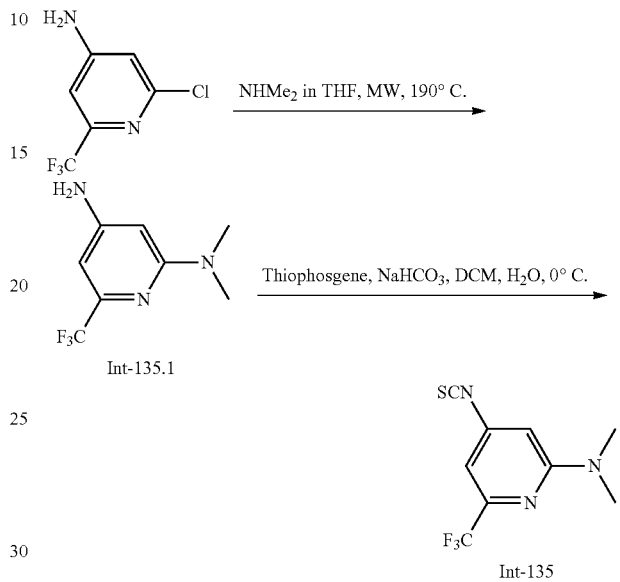

Synthesis of compound Int-135.1. A solution of 2-chloro-6-(trifluoromethyl)pyridin-4-amine (0.500 g, 2.54 mmol, 1.0 equiv) in dimethylamine (2 M in THF, 5 mL) was stirred in a microwave reactor at 190° C. for 12 h. The reaction mixture was cooled to room temperature and purified by flash column chromatography on silica gel (CombiFlash®, 1.2% methanol in DCM) to afford Int-135.1. MS (ES): m/z 206.1 [M+H]$^+$.

Synthesis of compound Int-135. Compound Int-135 was prepared from Int-135.1, following the procedure described in the synthesis of Int-1. The product was purified by flash column chromatography on silica gel (CombiFlash®, hexane). MS (ES): m/z 248.2 [M+H]$^+$.

Preparation of Intermediate Int-136: tert-butyl 3-((3-isothiocyanato-5-(trifluoromethyl)phenoxy)methyl)azetidine-1-carboxylate

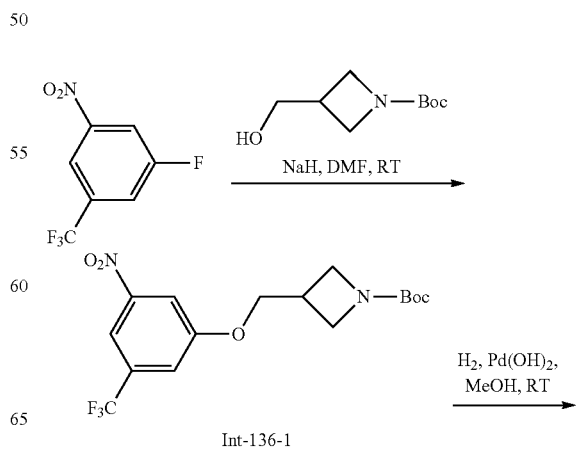

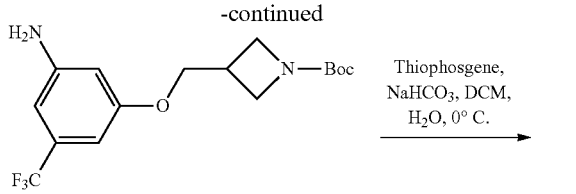

Int-136-2

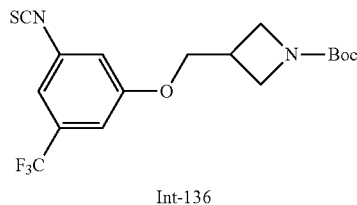

Int-136

Synthesis of compound Int-136.1. To a solution of tert-butyl 3-(hydroxymethyl)azetidine-1-carboxylate (1.0 g, 4.78 mmol, 1.0 equiv) in DMF (15 mL) was added sodium hydride (0.286 g, 7.17 mmol, 1.5 equiv) at 0° C. and stirred for 30 min. To the reaction mixture was added 1-fluoro-3-nitro-5-(trifluoromethyl)benzene (1.07 g, 5.74 mmol, 1.2 equiv) and stirred at 0° C. for 1 h. It was transferred into ice-water and precipitated solid was filtered out, washed with water, and dried to afford Int-136.1. MS (ES): m/z: 377.2 [M+H]$^+$.

Synthesis of compound Int-136.2. To a mixture of Int-136.1 (0.700 g, 1.86 mmol, 1.0 equiv) and 20% palladium hydroxide (0.700 g) in methanol was stirred under hydrogen (1 atm) for 1 h. The mixture was filtered through a pad of Celite® and rinsed with methanol. The filtrate was concentrated under reduced pressure. The residue was purified by flash column chromatography on silica gel (CombiFlash®, 30% ethyl acetate in hexane) to afford Int-136.2. MS (ES): m/z 347.1 [M+H]$^+$.

Synthesis of compound Int-136. Compound Int-136 was prepared from Int-136.2, following the procedure described in the synthesis of Int-1. The product was purified by flash column chromatography on silica gel (CombiFlash®, 20% ethyl acetate in hexane). MS (ES): m/z 389.2 [M+H]$^+$.

Preparation of Intermediate Int-137: (R)-3-isothiocyanato-1-(tetrahydrofuran-3-yl)-5-(trifluoromethyl)-1H-pyrazole

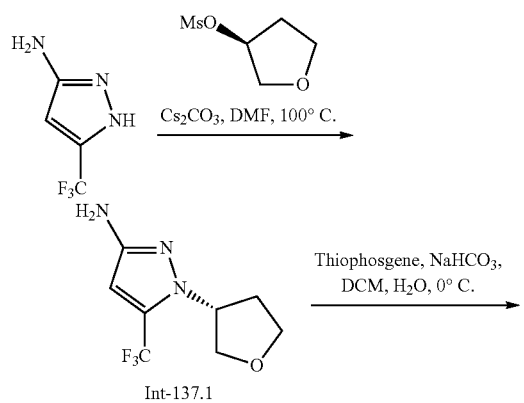

Int-137.1

Int-137

Synthesis of compound Int-137.1. A mixture of 5-(trifluoromethyl)-1H-pyrazol-3-amine (1.0 g, 6.62 mmol, 1.0 equiv), (S)-tetrahydrofuran-3-yl methanesulfonate (2.20 g, 13.24 mmol, 2.0 equiv) and cesium carbonate (6.45 g, 19.86 mmol, 3.0 equiv) in DMF (10 mL) was stirred at 100° C. for 12 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford Int-137.1. MS (ES): m/z 222.1 [M+H]$^+$.

Synthesis of compound Int-137. Compound Int-137 was prepared from Int-137.1, following the procedure described in the synthesis of Int-1. The product was purified by flash column chromatography on silica gel (CombiFlash®, 12% ethyl acetate in hexane). MS (ES): m/z 264.3 [M+H]$^+$.

Preparation of Intermediate Int-138: 1-(3-isothiocyanato-5-(trifluoromethyl)benzyl)pyrrolidine

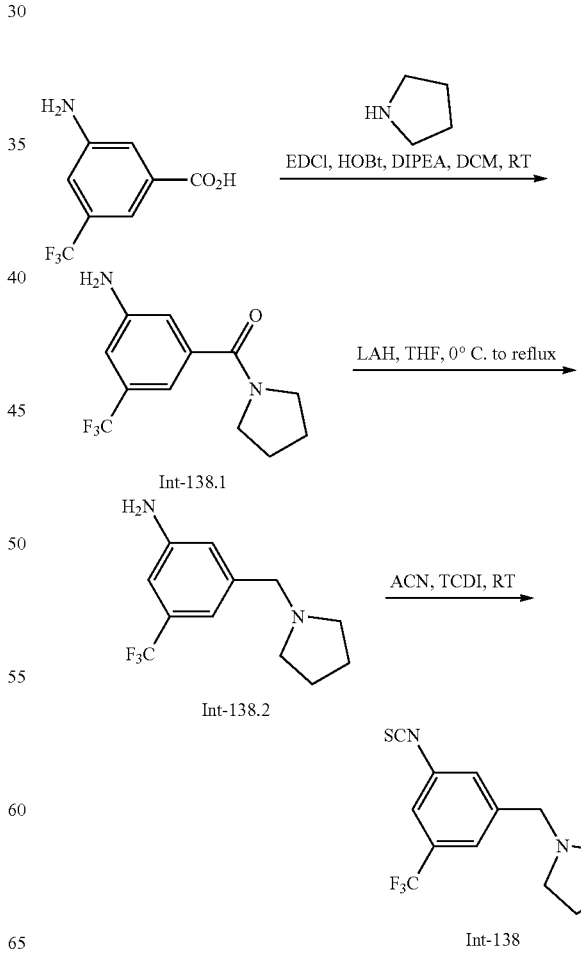

Synthesis of compound Int-138.1. A solution of 3-amino-5-(trifluoromethyl)benzoic acid (1 g, 4.87 mmol, 1.0 equiv), 1-hydroxybenzotriazole (0.723 g, 6.34 mmol, 1.3 equiv), 1-ethyl-3-(3-dimethylaminopropyl)carbodiimide hydrochloride (1.39 g, 7.30 mmol, 1.5 equiv), and N,N-diisopropylethylamine (4.25 mL, 24.35 mmol, 5.0 equiv) in DCM (15 mL) was stirred at room temperature for 30 min. To the reaction mixture was added pyrrolidine (0.0.450 g, 6.34 mmol, 1.3 equiv) and stirred for 4 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 3.8% methanol in DCM) to afford Int-138.1. MS (ES): m/z 259.2 [M+H]$^+$.

Synthesis of compound Int-138.2. To a solution of Int-138.1 (0.700 g, 2.71 mmol, 1.0 equiv) in THF (10 mL) was added lithium aluminum hydride (1 M in THF, 8.1 mL, 8.13 mmol, 3.0 equiv) at 0° C. The reaction mixture was stirred to reflux for 2 h. It was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7.8% methanol in DCM) to afford Int-138.2. MS (ES): m/z 245.0 [M+H]$^+$.

Synthesis of compound Int-138. To a solution of Int-138.2 (0.450 g, 1.84 mmol, 1.0 equiv) and imidazole (0.037 g, 0.552 mmol, 0.3 equiv) in acetonitrile (10 mL) was added thiocarbonyldiimidazole (0.651 g, 3.68 mmol, 2.0 equiv) and stirred at room temperature for 2 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1% methanol in DCM) to afford Int-138. MS (ES): m/z 287.2 [M+H]$^+$.

Preparation of Intermediate (±)-Int-139: trans-1-(4-(benzyloxy)tetrahydrofuran-3-yl)-3-isothiocyanato-5-(trifluoromethyl)-1H-pyrazole

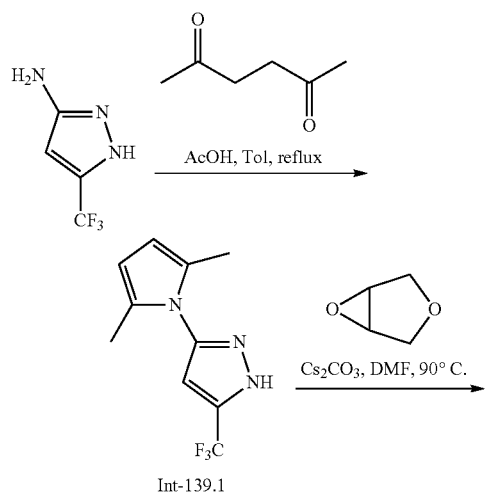

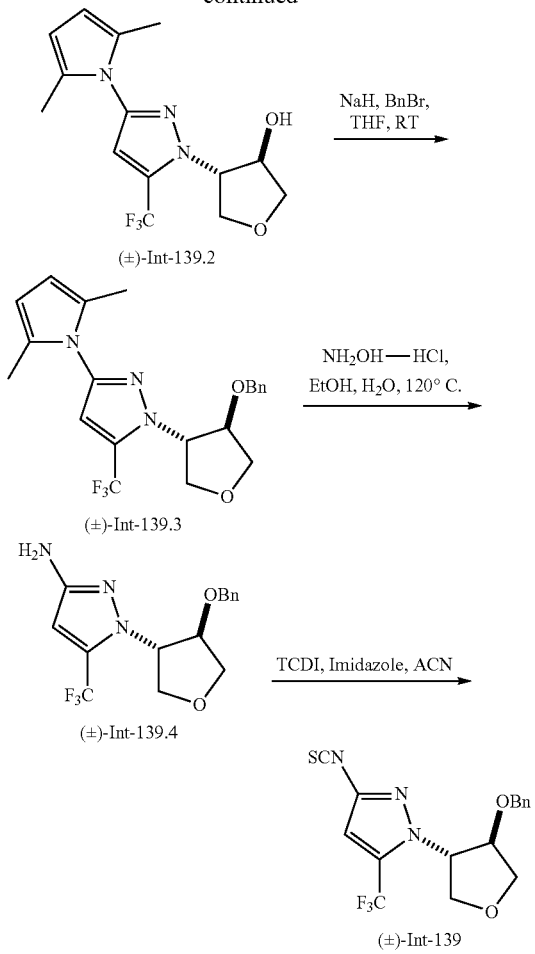

Synthesis of compound Int-139.1. A solution of 5-(trifluoromethyl)-1H-pyrazol-3-amine (10.0 g, 66.18 mmol, 1.0 equiv), hexane-2,5-dione (7.55 g, 66.18 mmol, 1.0 equiv) and acetic acid (catalytic) in toluene (100 mL) was stirred to reflux in a round bottom flask equipped with a Dean-Stark trap to remove water. The reaction mixture was cooled to room temperature and concentrated under reduced pressure. The residue was purified by flash column chromatography on silica gel (CombiFlash®, 15% ethyl acetate in hexane) to afford Int-139.1. MS (ES): m/z 230.3 [M+H]$^+$.

Synthesis of compound (±)-Int-139.2. A mixture of compound Int-139.1 (6 g, 26.18 mmol, 1.0 equiv), 3,6-dioxabicyclo[3.1.0]hexane (3.38 g, 39.27 mmol, 1.5 equiv) and cesium carbonate (25.52 g, 78.54 mmol, 3.0 equiv) in DMF (60 mL) was stirred at 80° C. for 16 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford (±)-Int-139.2. MS (ES): m/z 316.4 [M+H]$^+$.

Synthesis of compound (±)-Int-139.3. To a solution of (±)-Int-139.2 (0.460 g, 1.46 mmol, 1.0 equiv) in DMF (10 mL) was added sodium hydride (0.052 g, 2.19 mmol, 1.5 equiv) at room temperature and stirred for 30 min. To the reaction mixture was added benzyl bromide (0.27 g, 1.60 mmol, 1.1 equiv) and stirred at room temperature for 12 hr.

It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford (±)-Int-139.3. MS (ES): m/z 406.5 [M+H]⁺.

Synthesis of compound (±)-Int-139.4. To a solution of (±)-Int-139.3 (0.200 g, 0.493 mmol, 1.0 equiv) in ethanol: water (2:1, 10 mL) was added hydroxylamine hydrochloride (1.5 g, 24.65 mmol, 50 equiv). The reaction mixture was stirred at 100° C. for 9 h. It was transferred into ice-water, followed by 6 N sodium hydroxide, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.5-2.0% methanol in DCM) to afford (±)-Int-139.4. MS (ES): m/z 328.4 [M+H]⁺.

Synthesis of compound (±)-Int-139. Compound (±)-Int-139 was prepared from (f)-Int-139.4 following the procedure for the synthesis of I-69. The product was purified by flash column chromatography on silica gel (CombiFlash®, 2.5-3.0% methanol in DCM). MS (ES): m/z 370.2 [M+H]⁺.

Preparation of Intermediate (±)-Int-140: 4-isothiocyanato-2-(tetrahydrofuran-3-yl)-6-(trifluoromethyl)pyridine equiv), 2-(4,5-dihydrofuran-3-yl)-4,4,5,5-tetramethyl-1,3,2-dioxaborolane (2.99 g, 15.26 mmol, 3.0 equiv) and potassium carbonate (2.10 g, 15.26 mmol, 3.0 equiv) in 1,4-dioxane (7 mL) and water (3 mL) was degassed by bubbling argon through for 10 min. [1,1'-bis(diphenylphosphino)ferrocene] dichloropalladium(II), complex with DCM (0.207 g, 0.254 mmol, 0.05 equiv) was added, and degassed for 5 min. The reaction mixture was stirred at 120° C. for 3 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 38% ethyl acetate in hexane) to afford Int-140.1. MS (ES): m/z 231.0 [M+H]⁺.

Synthesis of compound (±)-Int-140.2. A mixture of compound Int-140.1 (0.409 g, 1.78 mmol, 1.0 equiv) and 20% palladium hydroxide (0.4 g) in methanol (10 mL) was stirred under hydrogen (1 atm) for 1 h. The reaction mixture was filtered through a pad of Celite® and rinsed with methanol. The filtrate was concentrated under reduced pressure to afford (±)-Int-140.2. MS (ES): m/z 233.1 [M+H]⁺.

Synthesis of compound (±)-Int-140. Compound (±)-Int-140 was prepared from (f)-Int-140.2, following the procedure described in the synthesis of Int-1. The product was purified by flash column chromatography on silica gel (CombiFlash®, 8% ethyl acetate in hexane). MS (ES): m/z 275.1 [M+H]⁺.

Preparation of Intermediate Int-141: (R)-1-(3-amino-2-fluoro-5-(trifluoromethyl)benzyl)-N,N-dimethylpyrrolidin-3-amine

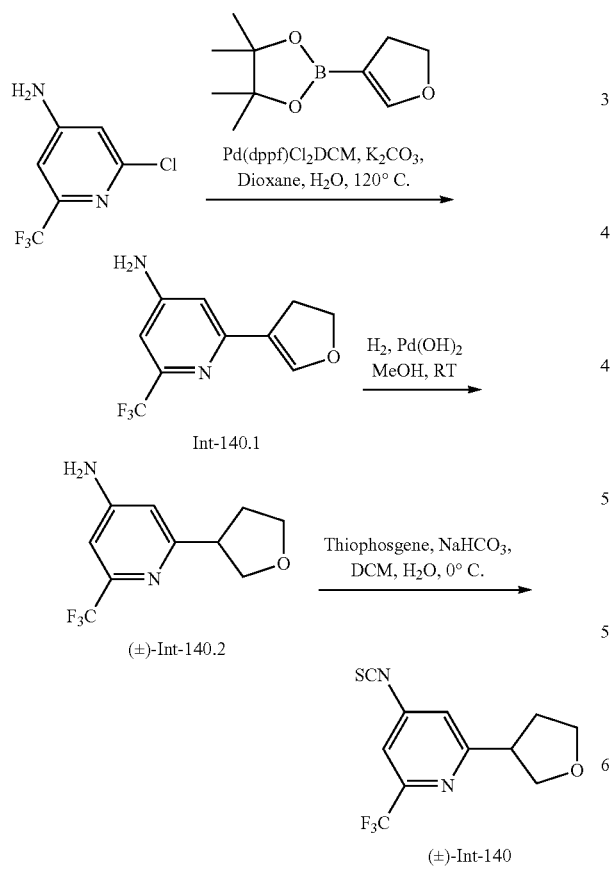

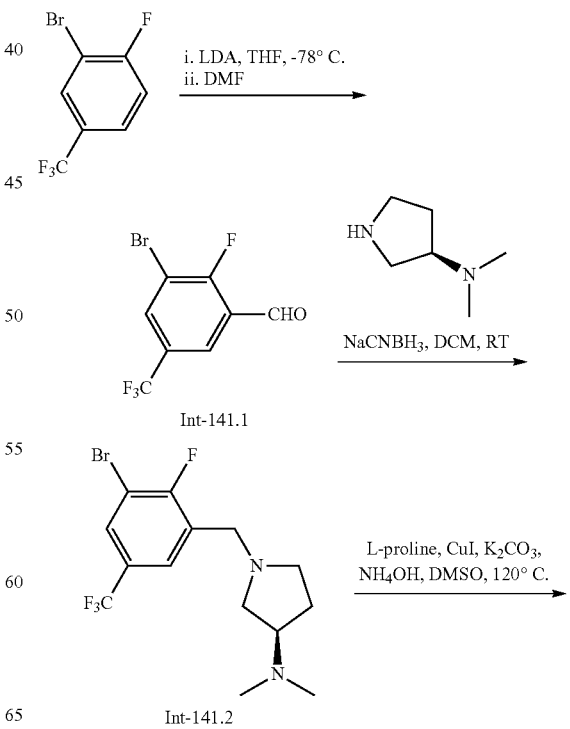

Synthesis of compound Int-140.1. A mixture of 2-chloro-6-(trifluoromethyl)pyridin-4-amine (1.0 g, 5.09 mmol, 1.0

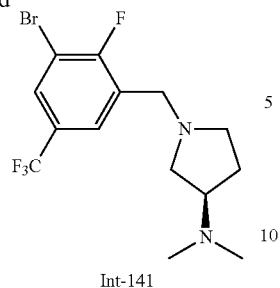

Int-141

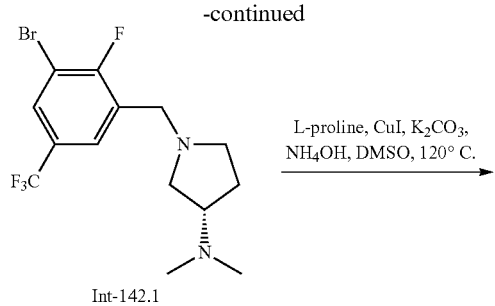

Int-142.1

Synthesis of compound Int-141.1. To a solution of 2-bromo-1-fluoro-4-(trifluoromethyl)benzene (1 g, 4.12 mmol, 1.0 equiv) in THF (15 mL) was added lithium diisopropylamide solution (2.0 M in THF, 3.09 mL, 6.18 mmol, 1.5 equiv) at −78° C. and stirred for 30 min. To the solution was added DMF (0.361 g, 4.94 mmol, 1.2 equiv) and stirred for 15 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5% ethyl acetate in hexane) to afford Int-141.1. MS (ES): m/z 272.0 [M+H]+.

Synthesis of compound Int-141.2. To a solution of Int-141.1 (0.570 g, 2.10 mmol, 1.0 equiv) and (R)—N,N-dimethylpyrrolidin-3-amine (0.480 g, 4.21 mmol, 2.0 equiv) in anhydrous DCM (25 mL) was stirred at room temperature for 2 h. To the solution was added sodium cyanoborohydride (0.396 g, 6.3 mmol, 3.0 equiv) and stirred for 12 h. The reaction mixture was concentrated under reduced pressure. The residue was purified by flash column chromatography on silica gel (CombiFlash®, 8% methanol in DCM) to afford Int-141.2. MS (ES): m/z 370.1 [M+H]+.

Synthesis of compound Int-141. To a mixture of Int-141.2 (0.245 g, 0.663 mmol, 1.0 equiv), L-proline (0.030 g, 0.265 mmol, 0.4 equiv), potassium carbonate (0.457 g, 3.315 mmol, 5.0 equiv) in dimethyl sulfoxide (5 mL) were added aq. ammonium hydroxide (1 mL) and copper iodide (0.075 g, 0.397 mmol, 0.6 equiv). The reaction mixture was stirred at 120° C. for 16 h. The reaction mixture was cooled to room temperature, transferred into water, and extracted with ethyl acetate. The combined organic layers were washed with brine, dried over anhydrous sodium sulfate, filtered, and concentrated under reduced pressure to afford Int-141. MS (ES): m/z 306.2 [M+H]+.

Preparation of Intermediate Int-142: ((S)-1-(3-amino-2-fluoro-5-(trifluoromethyl)benzyl)-N,N-dimethylpyrrolidin-3-amine

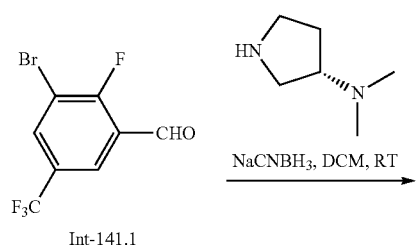

Int-141.1

Synthesis of compound Int-142. Compound Int-142 was prepared following the procedures described in the synthesis of Int-141. The final product was purified by flash column chromatography on silica gel (CombiFlash®, 8% methanol in DCM). MS (ES): m/z 370.1 [M+H]+.

Preparation of Intermediate Int-143: trans-1-(3-(benzyloxy)cyclobutyl)-3-isothiocyanato-5-(trifluoromethyl)pyridin-2(1H)-one

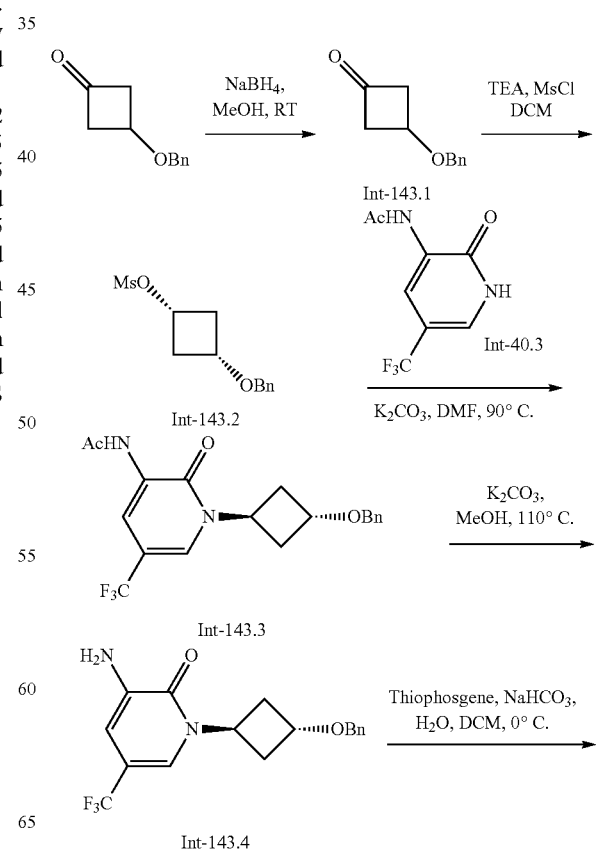

-continued

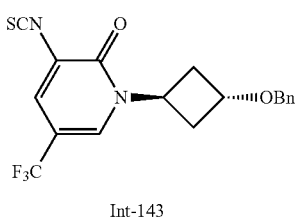

Int-143

Synthesis of compound Int-143.1. To a solution of 3-(benzyloxy)cyclobutan-1-one (10 g, 56.75 mmol, 1.0 equiv) in methanol (60 mL) was added sodium borohydride (4.2 g, 113.63 mmol, 2.0 equiv) in portions at 0° C. and stirred for 2 h. It was transferred into ice-water, stirred, and extracted with ethyl acetate. The combined organic layers were washed with brine, dried over anhydrous sodium sulfate, filtered, and concentrated under reduced pressure to afford Int-143.1. MS (ES): m/z 179.1 [M+H]$^+$.

Synthesis of compound Int-143.2. To a solution of Int-143.1 (9.1 g, 51.06 mmol, 1.0 equiv) and triethylamine (17.5 mL, 127.8 mmol, 2.5 equiv) in DCM (45 mL) was added methanesulfonyl chloride (4.7 mL, 61.34 mmol, 1.2 equiv) at 0° C. The reaction mixture was allowed to warm to room temperature and stirred for 30 min. It was transferred into ice-water, stirred, and extracted with DCM. The combined organic layers were washed with saturated sodium bicarbonate, followed by brine, dried over anhydrous sodium sulfate, filtered, and concentrated under reduced pressure to afford Int-143.2. MS (ES): m/z 257.2 [M+H]$^+$.

Synthesis of compound Int-143.3. A mixture of Int-143.2 (1.94 g, 7.57 mmol, 1.0 equiv), cesium carbonate (6.15 g, 18.94 mmol, 2.5 equiv) and Int-40.3 (3.0 g, 13.63 mmol, 1.8 equiv) in DMF (20 mL) was stirred at 90° C. for 16 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford Int-143.3. MS (ES): m/z 381.1 [M+H]$^+$.

Synthesis of compound Int-143.4. A mixture of Int-143.3 (1.5 g, 3.94 mmol, 1.0 equiv) and potassium carbonate (10.89 g, 78.94 mmol, 20 equiv) in methanol (5 mL) was stirred at 110° C. for 16 h. It was cooled to room temperature, poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford Int-143.4. MS (ES): m/z 339.4 [M+H]$^+$.

Synthesis of compound Int-143. Compound Int-143 was prepared from Int-143.4, following the procedure described in the synthesis of Int-1. The product was purified by flash column chromatography on silica gel (CombiFlash®, 1% methanol in DCM). MS (ES): m/z 381.4 [M+H]$^+$.

Preparation of Intermediate Int-144: 4-(4-isothiocyanato-2-(trifluoromethyl)benzyl)-1,4-oxazepane

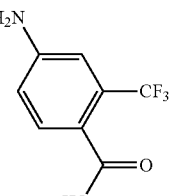 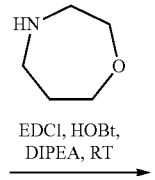

EDCl, HOBt, DIPEA, RT

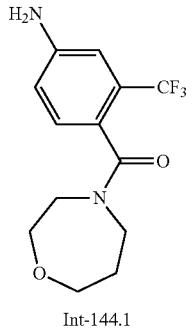

Int-144.1

BH$_3$-DMS, THF, 0° C. to reflux

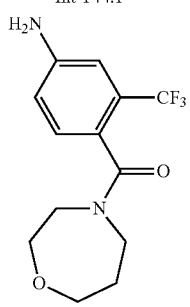

Int-144.2

Thiophosgene, NaHCO$_3$, DCM, H$_2$O, 0° C.

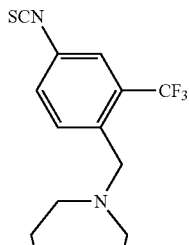

Int-144

Synthesis of compound Int-144.1. A solution of 4-amino-2-(trifluoromethyl)benzoic acid (0.400 g, 1.95 mmol, 1.0 equiv), 1-hydroxybenzotriazole (0.395 g, 2.90 mmol, 1.5 equiv), 1-ethyl-3-(3-dimethylaminopropyl)carbodiimide hydrochloride (0.559 g, 2.9 mmol, 1.5 equiv) and N,N-diisopropylethylamine (1.0 g, 7.8 mmol, 4.0 equiv) in DCM (8 mL) was stirred at room temperature for 15 min before the addition of 1,4-oxazepane (0.295 g, 2.92 mmol, 1.0 equiv) and stirred at room temperature for 16 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.4% methanol in DCM) to afford Int-144.1 MS (ES): m/z 289.2 [M+H]⁺.

Synthesis of compound Int-144.2. To a solution of Int-144.1 (0.320 g, 1.11 mmol, 1.0 equiv) in THF (5 mL) was added borane dimethylsulfide (1 M in THF, 3.0 mL, 3.0 mmol, 3.0 equiv) at 0° C. The reaction mixture was stirred to reflux for 2 h. It was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford Int-144.2. MS (ES): m/z 275.1 [M+H]⁺.

Synthesis of compound Int-144. Compound Int-144 was prepared from Int-144.2, following the procedure described in the synthesis of Int-1. The product was purified by flash column chromatography on silica gel (CombiFlash®, 2.0% methanol in DCM). MS (ES): m/z 317.1 [M+H]⁺.

Preparation of Intermediate Int-145: 4-((4-ethyl-1,4-diazepan-1-yl)methyl)-3-(trifluoromethyl)aniline

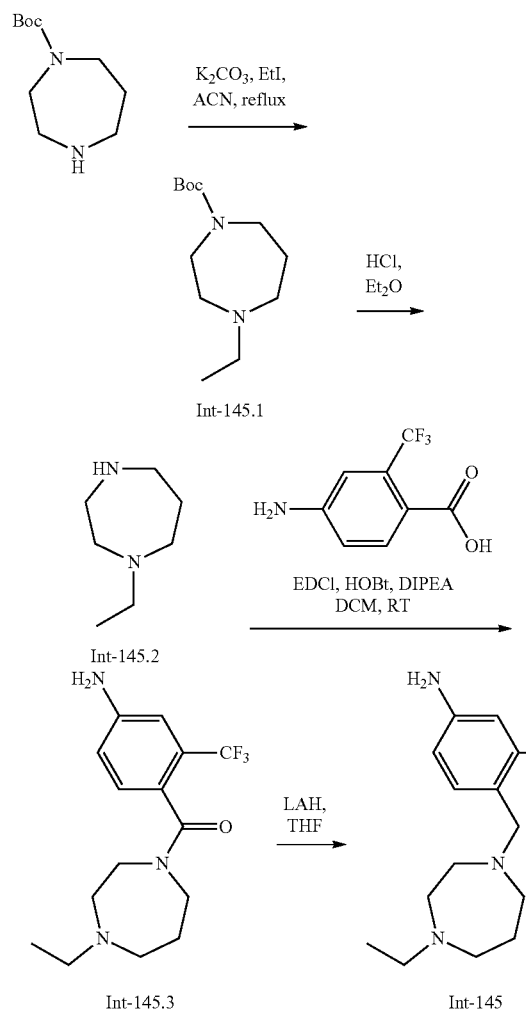

Synthesis of compound Int-145.1. A mixture of tert-butyl 1,4-diazepane-1-carboxylate (5 g, 24.96 mmol, 1.0 equiv), iodoethane (5.8 g, 37.44 mmol, 1.5 equiv) and potassium carbonate (6.8 g, 49.92 mmol, 2.0 equiv) in acetonitrile (25 mL) was stirred to reflux for 20 h. The reaction mixture was filtered through a pad of Celite® and rinsed with methanol. The filtrate was concentrated under reduced pressure. The residue was purified by flash column chromatography on silica gel (CombiFlash®, 3.8% methanol in DCM eluant) to afford Int-145.1. MS (ES): m/z 229.1 [M+H]⁺.

Synthesis of compound Int-145.2. A solution of Int-145.1 (1.0 g, 4.38 mmol, 1 equiv) in solution of hydrochloric acid in diethyl ether (2 M, 10 mL) was stirred at room temperature for 2 h. The reaction mixture was filtered to afford crude product, which was further purified by trituration with diethyl ether to afford Int-145.2. MS (ES): m/z 129.2 [M+H]⁺.

Synthesis of compound Int-145.3. A solution of 4-amino-2-(trifluoromethyl)benzoic acid (0.639 g, 3.12 mmol, 1.0 equiv), 1-hydroxybenzotriazole (0.893 g, 4.68 mmol, 1.5 equiv) and 1-ethyl-3-(3-dimethylaminopropyl)carbodiimide hydrochloride (0.631 g, 4.68 mmol, 1.5 equiv) in DCM (12 mL) was stirred at 0° C. for 15 min. To the solution was added Int-145.2 (0.400 g, 3.12 mmol, 1.0 equiv) and N,N-diisopropylethylamine (2.01 g, 15.6 mmol, 5.0 equiv) and stirred at 0° C. for 3 h. It was transferred into ice-water, stirred, and extracted with DCM. The combined organic layers were washed with brine, dried over anhydrous sodium sulfate, filtered, and concentrated under reduced pressure. The residue was purified by trituration using diethyl ether to afford Int-145.3. MS (ES): m/z 316.5 [M+H]⁺.

Synthesis of compound Int-145. To a solution of Int-145.3 (0.450 g, 1.43 mmol, 1.0 equiv) in THF (10 mL) was added lithium aluminum hydride (2 M in THF, 3.5 mL, 7.14 mmol, 5.0 equiv) at 0° C. The reaction mixture was stirred to reflux for 1 h. It was cooled to room temperature, transferred into ice, stirred, and extracted with ethyl acetate. The combined organic layers were washed with brine, dried over anhydrous sodium sulfate, filtered, and concentrated under reduced pressure to afford Int-145. MS (ES): m/z 302.5 [M+H]⁺.

Preparation of Intermediate Int-146: 4-((4-ethyl-1,4-diazepan-1-yl)methyl)-3-(trifluoromethyl)aniline

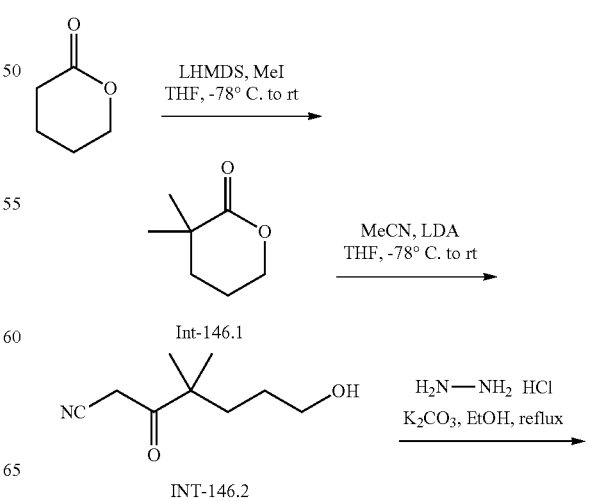

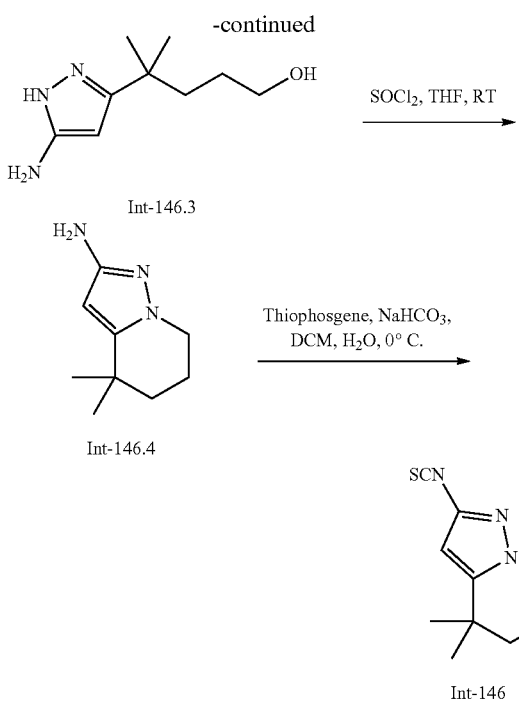

Synthesis of compound Int-146.1. To a solution of δ-valerolactone (10 g, 99.88 mmol, 1.0 equiv) and methyl iodide (24.8 mL, 399.52 mmol, 4.0 equiv) in THF (200 mL) was added lithium bis(trimethylsilyl)amide (1 M in THF, 219 mL, 219.7 mmol, 2.2 equiv) at −78° C. The reaction mixture was stirred at room temperature for 16 h. It was poured over ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 10% ethyl acetate in hexane as eluant) to afford Int-146.1. MS (ES): m/z 129.2 [M+H]$^+$.

Synthesis of compound Int-146.2. To a solution of diisopropylamine (4.88 g, 48.37 mmol, 1.0 equiv) in THF (100 mL) at −78° C. was slowly added a solution of n-butyl lithium (2.5 M in hexane, 24.2 mL, 60.46 mmol, 1.25 equiv). The reaction mixture was stirred for 5 min followed by addition of acetonitrile (2.5 mL, 48.37 mmol, 1.0 equiv). The reaction mixture stirred for 10 min and compound Int-146.1 (6.20 g, 48.37 mmol, 1.0 equiv) in THF (30 mL) was added to it. The reaction mixture was stirred at 5° C. for 6 h. It was poured over cold saturated ammonium chloride solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane as eluant) to afford Int-146.2. MS (ES): m/z 170.2 [M+H]$^+$.

Synthesis of compound Int-146.3. To a solution of Int-146.2 (3.9 g, 23.05 mmol, 1.0 equiv) in ethanol (40 mL) was added hydrazine hydrochloride (2.35 g, 34.57 mmol, 1.5 equiv) followed by addition of potassium carbonate (4.77 g, 34.57 mmol, 1.5 equiv). The reaction mixture was stirred to reflux for 16 h. It was concentrated under reduced pressure. The residue was purified by flash column chromatography on silica gel (CombiFlash®, 3-4% methanol in dichloromethane as eluant) to afford Int-146.3. MS (ES): m/z 184.26 [M+H]$^+$.

Synthesis of compound Int-146.4. To a solution of Int-146.3 (1.1 g, 6.0 mmol, 1.0 equiv) in THF (20 mL) was added thionyl chloride (2.15 mL, 30 mmol, 5.0 equiv). The reaction mixture was stirred at room temperature for 2 h. It was poured over saturated sodium bicarbonate solution, stirred, and extracted with ethyl acetate. The combined organic layers were washed with brine, dried over anhydrous sodium sulfate, filtered and concentrated under reduced pressure. The residue was purified by flash column chromatography on silica gel (CombiFlash®, 2% methanol in dichloromethane as eluant) to afford Int-146.4. MS (ES): m/z 166.24 [M+H]$^+$.

Synthesis of compound Int-146. Compound Int-146 was prepared from Int-146.4 following the procedure described in the synthesis of Int-1. The crude product was used in the next step without further purification. MS (ES): m/z 208.3 [M+H]$^+$.

Preparation of Intermediate Int-147: 1-(4-isothiocyanato-2-(trifluoromethyl)benzyl)pyrrolidine

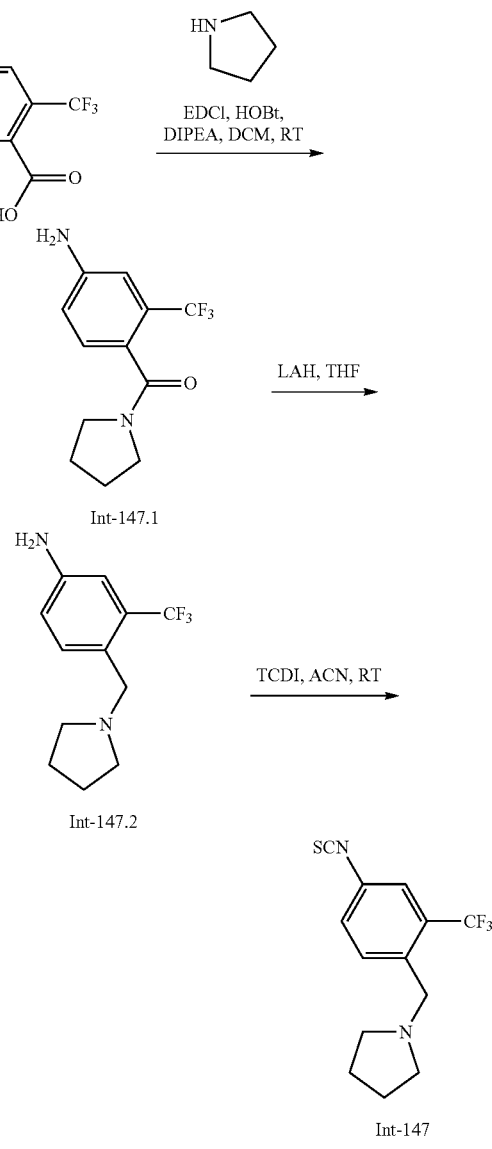

Synthesis of compound Int-147.1. To a solution of 4-amino-2-(trifluoromethyl)benzoic acid (0.500 g, 2.44 mmol, 1.0 equiv), 1-hydroxybenzotriazole (0.362 g, 2.68 mmol, 1.1 equiv) and 1-ethyl-3-(3-dimethylaminopropyl) carbodiimide hydrochloride (0.699 g, 3.66 mmol, 1.5 equiv) in DCM (15 mL) was added pyrrolidine (0.260 g, 3.66 mmol, 1.5 equiv) and N,N-diisopropylethylamine (1.57 g, 12.2 mmol, 5.0 equiv) at 0° C. and stirred at room temperature for 3 h. It was transferred into ice-water, stirred, and extracted with DCM. The combined organic layers were washed with brine, dried over anhydrous sodium sulfate, filtered, and concentrated under reduced pressure. The residue was purified by trituration using diethyl ether) to afford Int-147.1. MS (ES): m/z 259.5 $[M+H]^+$.

Synthesis of compound Int-147.2. To a solution of Int-147.1 (0.500 g, 1.94 mmol, 1.0 equiv) in THE (10 mL) was added lithium aluminum hydride (2 M in THF) (2.9 mL, 5.82 mmol, 3.0 equiv) at 0° C. Reaction mixture refluxed for 1 h. It was cooled to room temperature, transferred into ice, stirred, and extracted with ethyl acetate. The combined organic layers were washed with brine, dried over anhydrous sodium sulfate, filtered, and concentrated under reduced pressure to afford Int-147.2. MS (ES): m/z 245.5 $[M+H]^+$.

Synthesis of compound Int-147. Compound Int-147 was synthesized following the procedure described in the synthesis of I-138. MS (ES): m/z 287.2 $[M+H]^+$.

Preparation of Intermediate (±)-Int-148: 2-(4-isothiocyanato-2-(trifluoromethyl)phenyl)-1-methylpyrrolidine

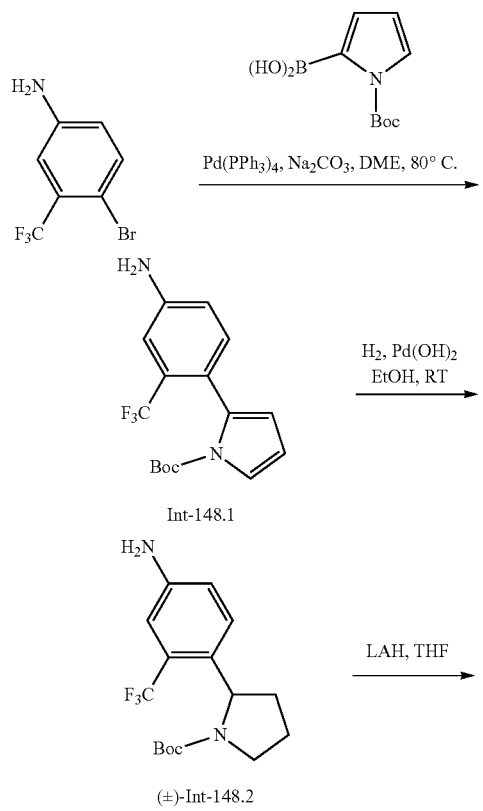

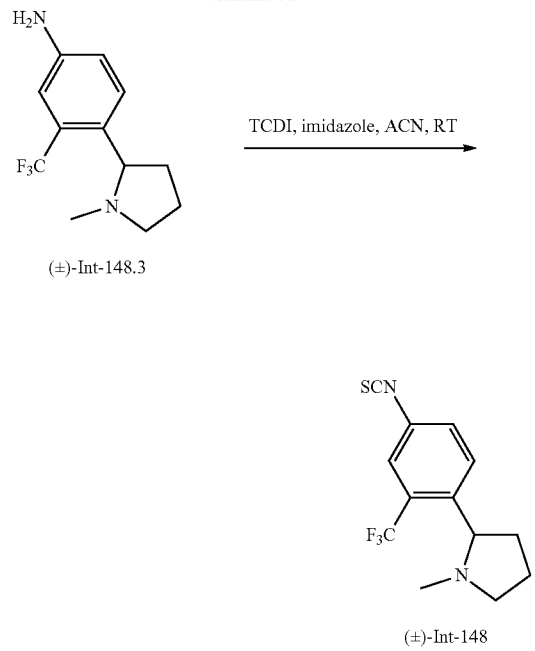

Synthesis of compound Int-148.1. A mixture of 4-bromo-3-(trifluoromethyl)aniline (3.0 g, 12.5 mmol, 1.0 equiv), (1-(tert-butoxycarbonyl)-1H-pyrrol-2-yl)boronic acid (3.9 g, 18.7 mmol, 1.5 equiv) and sodium carbonate (5.2 g, 50.02 mmol, 4.0 equiv) in dimethoxyethane (40 mL) was degassed by bubbling argon through for 10 min. Tetrakis(triphenylphosphine) palladium(0) (1.2 g, 1.3 mmol, 0.9 equiv) was added, and degassed for 5 min. The reaction mixture was stirred at 80° C. for 5 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 8.0% methanol in DCM) to afford Int-148.1. MS (ES): m/z 327.32 $[M+H]^+$.

Synthesis of compound (±)-Int-148.2. A mixture of compound Int-148.1 (1.4 g, 4.29 mmol, 1.0 equiv) and 20% palladium hydroxide (1.0 g) in methanol (38 mL) was stirred under hydrogen (1 atm) for 7 h. The reaction mixture was filtered through a pad of Celite® and rinsed with methanol. The filtrate was concentrated under reduced pressure to afford (±)-Int-148.2. MS (ES): m/z 331.35 $[M+H]^+$.

Synthesis of compound (±)-Int-148.3. To a solution of (±)-Int-148.2 (1.2 g, 3.63 mmol, 1.0 equiv) in THE (14 mL) was added lithium aluminum hydride (1 M in THF, 25 mL, 25.41 mmol, 7.0 equiv) at 0° C. The reaction mixture was stirred to reflux for 30 min. It was cooled to room temperature, transferred into ice, stirred, and extracted with ethyl acetate. The combined organic layers were washed with brine, dried over anhydrous sodium sulfate, filtered, and concentrated under reduced pressure to afford (±)-Int-148.3. MS (ES): m/z 245.26$[M+H]^+$.

Synthesis of compound (±)-Int-148. Compound (±)-Int-148 was prepared from (±)-Int-148.3 following the procedure for the synthesis of I-69. The product was purified by flash column chromatography on silica gel (CombiFlash®, 2.5-3.0% methanol in DCM). MS (ES): m/z 287.32$[M+H]^+$.

Preparation of Intermediate Int-149-a and Int-149-b: (S)-2-((3-isothiocyanato-5-(trifluoromethyl)phenoxy)methyl)-1-methylpiperidine and (R)-2-((3-isothiocyanato-5-(trifluoromethyl)phenoxy)methyl)-1-methylpiperidine

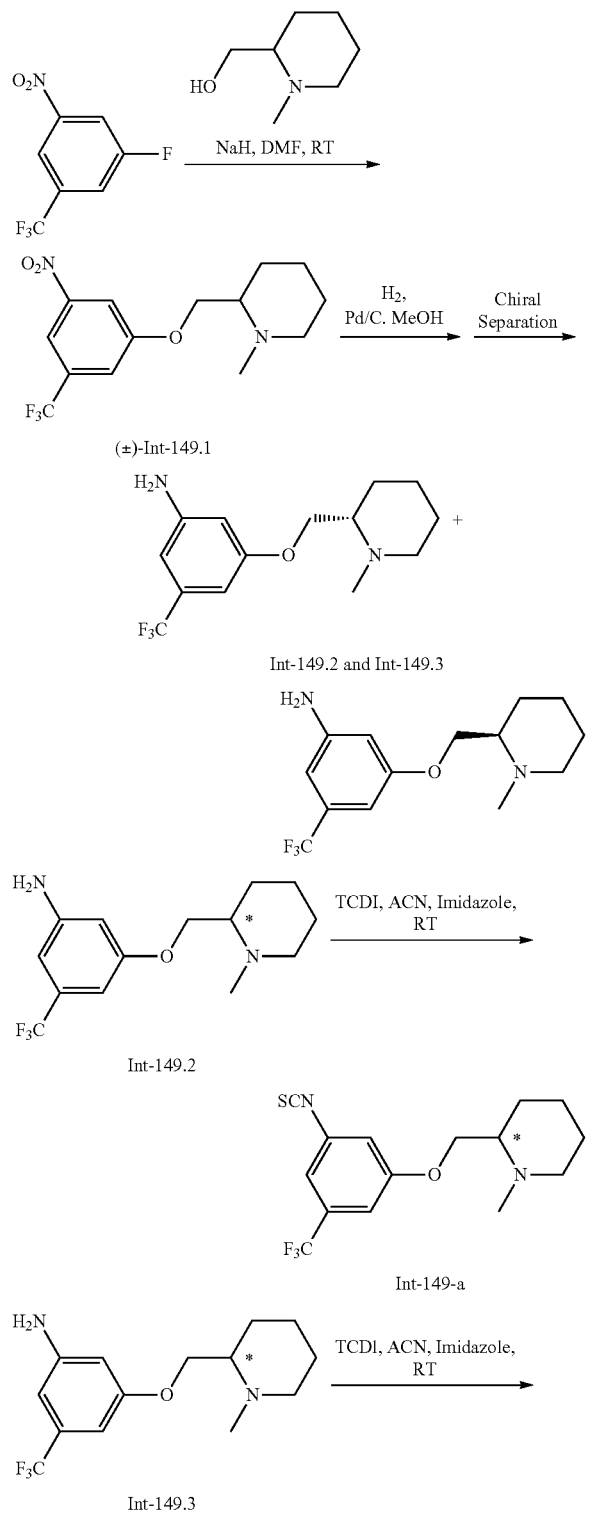

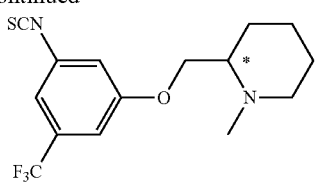

Synthesis of compound (±)-Int-149.1. To solution of (1-methylpiperidin-2-yl)methanol (1.0 g, 4.78 mmol, 1.0 equiv) in DMF (20 mL) was added sodium hydride (0.286 g, 11.95 mmol, 2.5 equiv) at 0° C. and stirred for 30 min. To the mixture was added 1-fluoro-3-nitro-5-(trifluoromethyl)benzene (0.617 g, 4.78 mmol, 1.0 equiv) and stirred at 0° C. for 1 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 50% ethyl acetate in hexane to afford (±)-Int-149.1. MS (ES): m/z 319.30 [M+H]$^+$.

Synthesis of compound Int-149.2 and Int-149.3. A mixture of compound (±)-Int-149.1 (0.900 g, 2.83 mmol, 1.0 equiv) and 10% palladium on carbon (0.450 g) in methanol (5 mL) was stirred under hydrogen (1 atm) for 4 h. The reaction mixture was filtered through a pad of Celite® and the filtrate was concentrated under reduced pressure. The residue was purified by flash column chromatography on silica gel (CombiFlash®, 5.0% methanol in DCM). The enantiomers were separated by HPLC (column: CHIRALPAK IG (250 mm×4.6 mm, 5 μm); mobile phases: 0.1% DEA in methanol; flow rate: 10 mL/min) to afford first eluting fraction (Int-149.2) and second eluting fraction (Int-149.3). MS (ES): m/z 289.1. (*Absolute stereochemistry not determined.)

Synthesis of compound Int-149-a. Compound Int-149-a was prepared from Int-149.2 following the procedure for the synthesis of I-69. The product was purified by flash column chromatography on silica gel (CombiFlash®, 2.5-3.0% methanol in DCM). MS (ES): m/z 331.2 [M+H]$^+$.

Synthesis of compound Int-149-b. Compound Int-149-b was prepared from Int-149.3 following the procedure for the synthesis of I-69. The product was purified by flash column chromatography on silica gel (CombiFlash®, 2.5% methanol in DCM). MS (ES): m/z 331.2 [M+H]$^+$.

Preparation of Intermediate Int-150: 6-(3-isothiocyanato-5-(trifluoromethyl)benzyl)-2-oxa-6-azaspiro[3.3]heptane

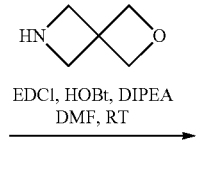

561

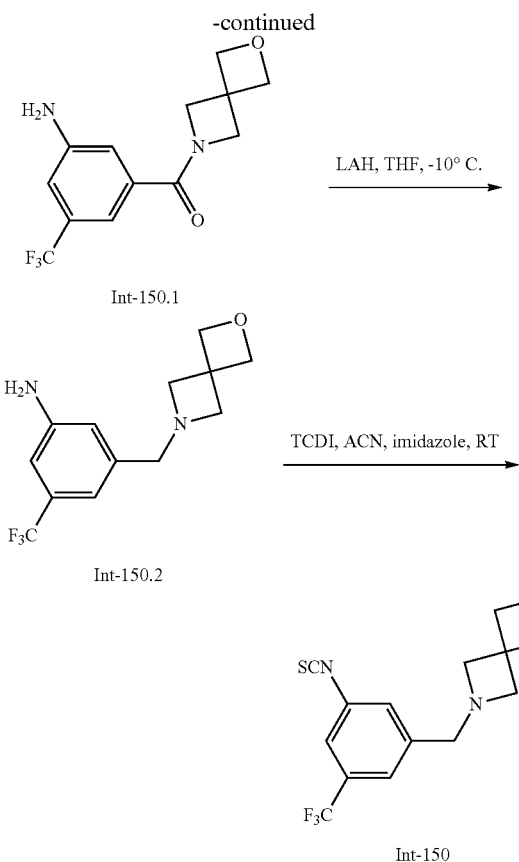

Synthesis of compound Int-150.1. A solution of 3-amino-5-(trifluoromethyl)benzoic acid (2.0 g, 9.75 mmol, 1.0 equiv), 1-hydroxybenzotriazole (0.682 g, 4.8 mmol, 0.5 equiv), 1-ethyl-3-(3-dimethylaminopropyl)carbodiimide hydrochloride (5.59 g, 29.3 mmol, 3.0 equiv) and N,N-diisopropylethylamine (6.78 mL, 39.0 mmol, 4.0 equiv) in DMF (15 mL) was stirred at room temperature for 30 min. To the solution was added 2-oxa-6-azaspiro[3.3]heptane (1.16 g, 11.70 mmol, 1.2 equiv) and stirred at room temperature for 12 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.4 methanol in DCM) to afford Int-150.1. MS (ES): m/z 287.2 [M+H]$^+$.

Synthesis of compound Int-150.2. To a solution of Int-150.1 (0.800 g, 0.346 mmol, 1.0 equiv) in THF (8 mL) was added lithium aluminum hydride (1 M in THF, 2.7 mL, 2.7 mmol, 3.0 equiv) at −10° C. and stirred for 30 min. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.0% methanol in DCM) to afford Int-150.2. MS (ES): m/z 273.1 [M+H]$^+$.

Synthesis of compound Int-150. Compound Int-150 was prepared from Int-150.2 following the procedure for the synthesis of I-69. The product was purified by flash column chromatography on silica gel (CombiFlash®, 2.0% methanol in DCM). MS (ES): m/z 315.0 [M+H]$^+$.

562

Preparation of Intermediate Int-151: 4,4-difluoro-2-isothiocyanato-4,5,6,7-tetrahydropyrazolo[1,5-a]pyridine

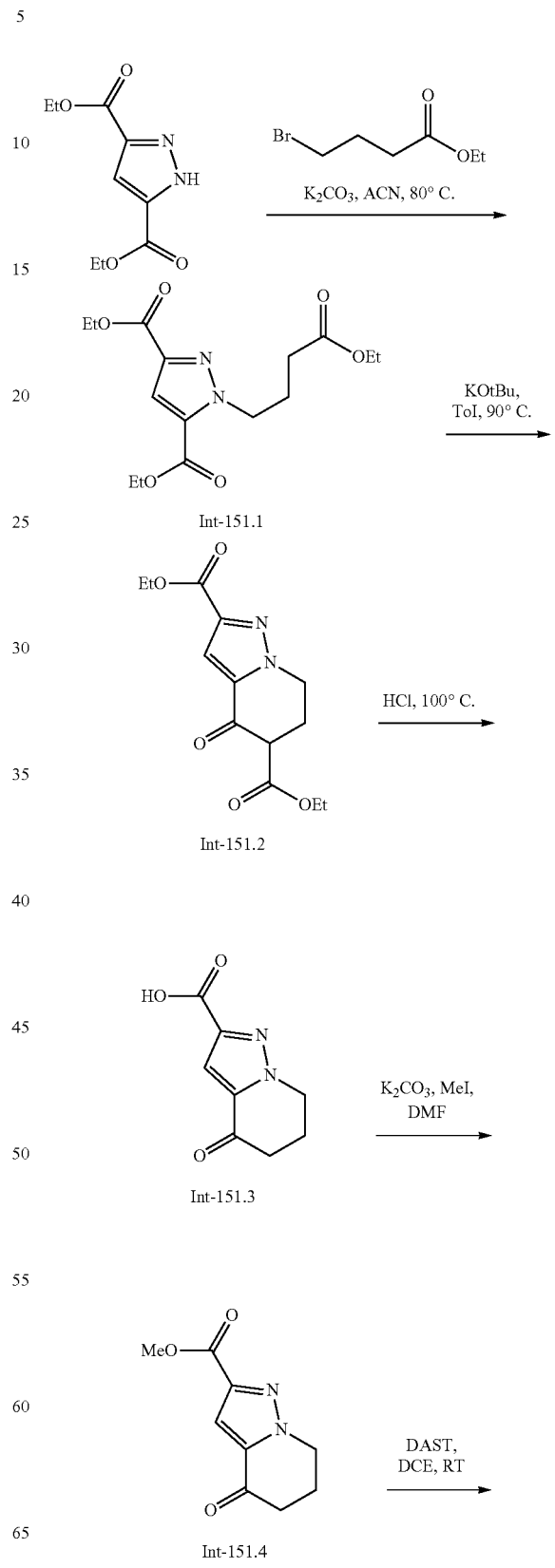

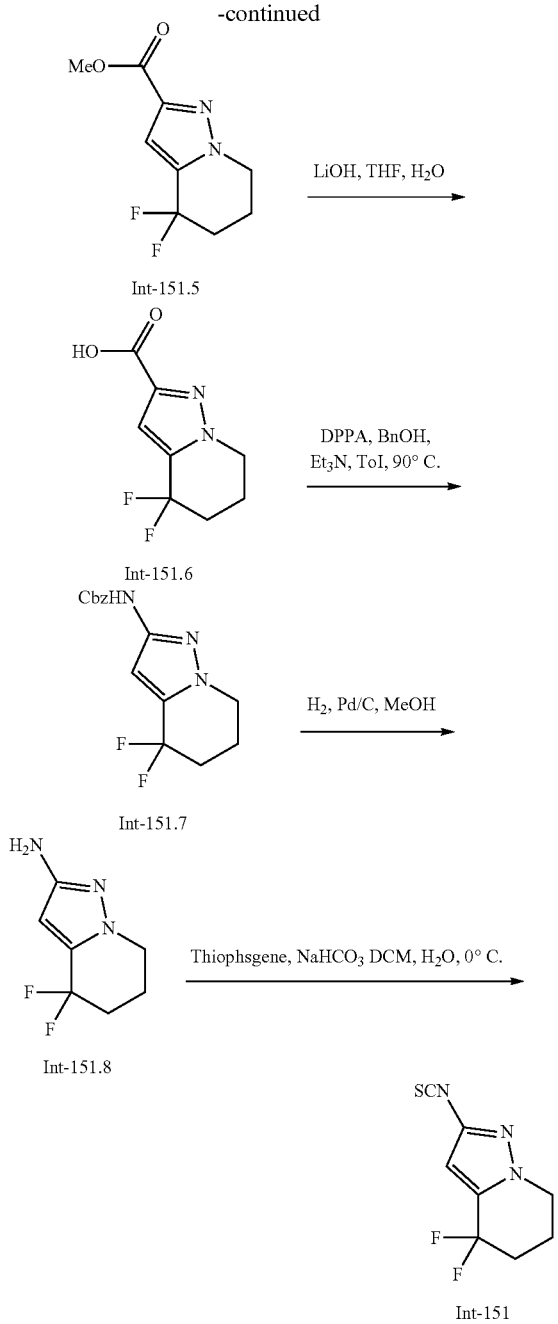

Synthesis of compound Int-151.1. To a solution of diethyl 1H-pyrazole-3,5-dicarboxylate (100 g, 471 mmol, 1.0 equiv) and ethyl 4-bromobutanoate (91.92 g, 471 mmol, 1.0 equiv) in acetonitrile (1000 mL) was added potassium carbonate (64.99 g, 471 mmol, 1.0 equiv) and reaction mixture was stirred at 80° C. for 4 h. It was poured into ice-water and extracted with ethyl acetate. The combined organic layers were washed with brine, dried over anhydrous sodium sulfate, filtered, and concentrated under reduced pressure. The residue was purified by trituration with diethyl ether to afford Int-151.1. MS (ES): m/z 327.2 [M+H]$^+$.

Synthesis of compound Int-151.2. To a solution of Int-151.1 (120 g, 367 mmol, 1.0 equiv) in toluene (1000 mL) was added potassium tert-butoxide (1 M in THF) (403 mL, 403.7 mmol, 1.1 equiv) at room temperature. The reaction mixture was stirred at 90° C. for 3 h. The reaction mixture was poured into ice-water, and product extracted with ethyl acetate. The combined organic layers were washed with brine, dried over anhydrous sodium sulfate, filtered, and concentrated under reduced pressure. The residue was purified by trituration with diethyl ether to afford Int-151.2. m/z: 281.2 [M+H]$^+$.

Synthesis of compound Int-151.3. To Int-151.2 (65 g, 231 mmol 1.0 equiv) was added hydrochloric acid:water (2:1, 600 mL) and the reaction mixture heated 100° C. for 6 h. It was concentrated under reduced pressure. The residue was dissolved in acetonitrile-THF (1:4, 250 mL) and the solution was concentrated under reduced pressure to afford Int-151.3. MS (ES): m/z 181.1 [M+H]$^+$.

Synthesis of compound Int-151.4. To a solution of Int-151.3 (38 g, 210 mmol, 1.0 equiv) in DMF (4000 mL) was added potassium carbonate (57.96 g, 420 mmol, 2.0 equiv) followed by methyl iodide (15.7 mL, 252 mmol, 1.2 equiv) and reaction mixture was stirred at room temperature for 4 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (Combi-Flash®, 25% ethyl acetate in hexane) to afford Int-151.4. MS (ES): m/z 195.0 [M+H]$^+$.

Synthesis of compound Int-151.5. To a solution of Int-151.4 (22 g, 113.29 mmol, 1.0 equiv) in 1,2-dichloroethane (130 mL) was added diethylaminosulfur trifluoride (150 mL, 1132.9 mmol, 10.0 equiv) and reaction mixture was stirred at room temperature for 5 days. It was transferred into ice-cold saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (Combi-Flash®, 20% ethyl acetate in hexane) to afford Int-151.5. MS (ES): m/z 217.1 [M+H]$^+$.

Synthesis of compound Int-151.6. To a solution of Int-151.5 (11.2 g, 51.81 mmol, 1.0 equiv) in THF (110 mL) was added lithium hydroxide (4.35 g, 103.62 mmol, 2.0 equiv) and water (11 mL). The reaction mixture was stirred at room temperature for 16 h. It was poured into ice-water, and adjusted to pH 5 by adding 2 M hydrochloric acid. Product was extracted with ethyl acetate. The combined organic layers were washed with brine, dried over anhydrous sodium sulfate, filtered, and concentrated under reduced pressure to afford Int-151.6. MS (ES): m/z 203.0 [M+H]$^+$.

Synthesis of compound Int-151.7. To a suspension of Int-151.6 (8.0 g, 39.57 mmol, 1.0 equiv) in toluene (100 mL) was added triethyl amine (11 mL, 79.14 mmol, 2.0 equiv), followed by benzyl alcohol (21.4 g, 197.85 mmol, 5.0 equiv) and diphenylphosphoryl azide (21.77 g, 79.14 mmol, 2.0 equiv). The reaction mixture was stirred at 90° C. for 16 h. It was poured into ice-water and extracted with ethyl acetate. The combined organic layers were washed with brine, dried over anhydrous sodium sulfate, filtered, and concentrated under reduced pressure to afford to afford crude material. This was further purified by flash column chromatography on silica gel (CombiFlash®, 15% ethyl acetate in hexane) to afford Int-151.7. MS (ES): m/z 308.2 [M+H]$^+$.

Synthesis of compound Int-151.8. A mixture of Int-151.7 (5.4 g, 17.57 mmol, 1.0 equiv) and 10% palladium on charcoal (2.0 g) in methanol (100 mL) was stirred under hydrogen (1 atm) for 2 h. It was filtered through a pad of Celite®, rinsed with methanol. The filtrate was concentrated under reduced pressure to afford Int-151.8. MS (ES): m/z 174.1 [M+H]⁺.

Synthesis of compound Int-151. Compound Int-151 was prepared from Int-151.8 following the procedure described in the synthesis of Int-1. It was used without purification. MS (ES): m/z 216.2 [M+H]⁺.

Preparation of Intermediate Int-152: 3-isothiocyanato-1-(7-oxaspiro[3.5]nonan-2-yl)-5-(trifluoromethyl)-1H-pyrazole

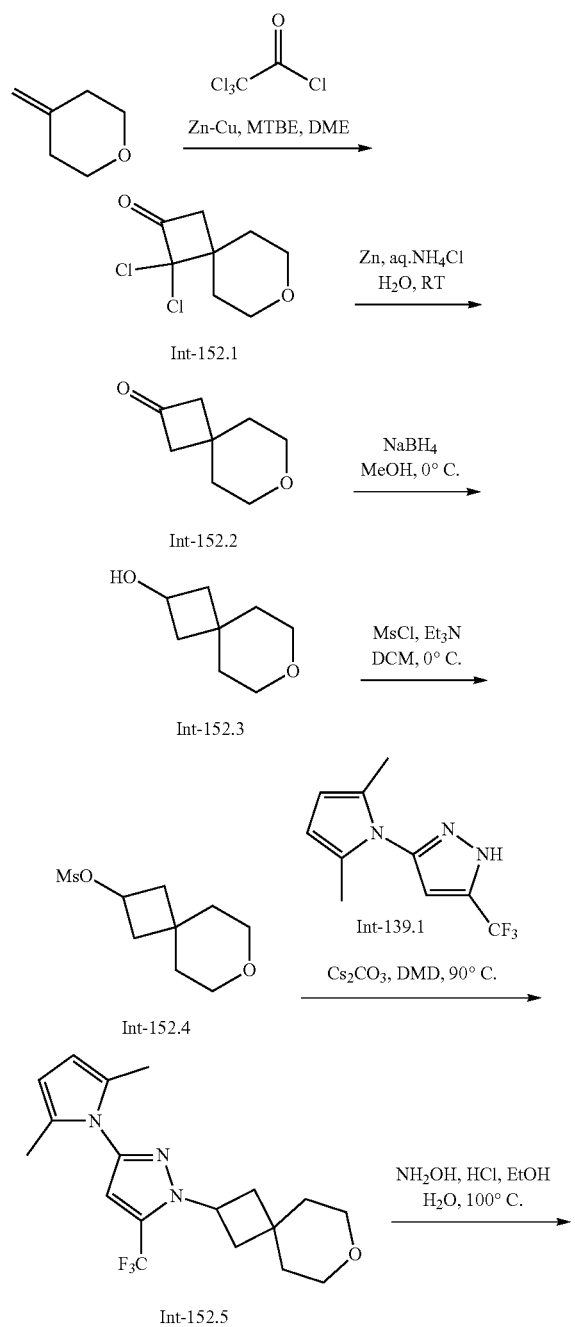

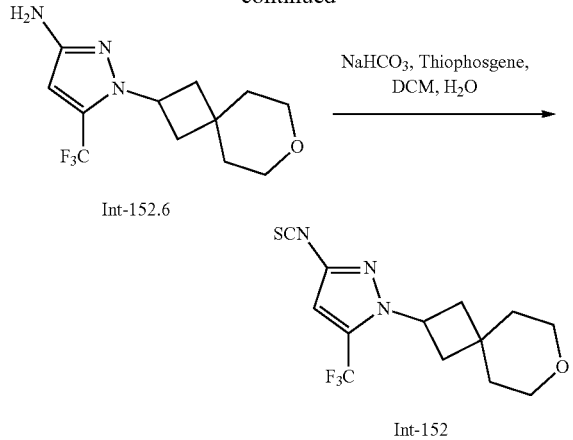

Synthesis of compound Int-152.1. To a mixture of 4-methylenetetrahydro-2H-pyran (5.0 g, 50.95 mmol, 1.0 equiv) and zinc-copper couple (71.73 g, 560.45 mmol, 11.0 equiv) in tert-butyl methyl ether (100 mL) was added a solution of diphosgene (37.10 g, 204.08 mmol, 4.0 equiv) in dimethoxyethane (40 mL) at 0° C. and stirred at room temperature for 18 h. It was filtered through a pad of Celite® and the filtrate was washed with aqueous sodium bicarbonate and brine. The organic layer was separated, dried over sodium sulfate, filtered, and concentrated under reduced pressure to afford Int-152.1. MS (ES): m/z: 210.0 [M+H]⁺.

Synthesis of compound Int-152.2. A mixture of Int-152.1 (8.9 g, 42.58 mmol, 1.0 equiv), saturated ammonium chloride solution in methanol (200 mL) and zinc (27.67 g, 425.8 mmol, 10.0 equiv) was stirred at room temperature for 16 h. It was filtered through a pad of Celite® and rinsed with diethyl ether. The filtrate was concentrated under reduced pressure. The residue was purified by flash column chromatography on silica gel (CombiFlash®, 30% ethyl acetate in hexane) to afford Int-152.2. MS (ES): m/z: 141.1 [M+H]⁺.

Synthesis of compound Int-152.3. To a solution of Int-152.2 (3.9 g, 27.82 mmol, 1.0 equiv) in methanol (40 mL) was added sodium borohydride (0.308 g, 8.34 mmol, 0.3 equiv) at 0° C. and stirred at room temperature for 16 h. It was transferred into ice-water and extracted with ethyl acetate. The combined organic layers were washed with brine, dried over anhydrous sodium sulfate, filtered, and concentrated under reduced pressure to afford Int-152.3. MS (ES): m/z: 143.1 [M+H]⁺.

Synthesis of compound Int-152.4. To a solution of Int-152.3 (3.0 g, 21.1 mmol, 1.0 equiv) and triethylamine (8.8 mL, 63.3 mmol, 3.0 equiv) in DCM (30 mL) was added methanesulfonyl chloride (2.4 mL, 31.65 mmol, 1.5 equiv) at 0° C. The reaction mixture was stirred at room temperature for 30 min. It was transferred into ice-water, stirred, and extracted with DCM. The combined organic layers were washed with saturated sodium bicarbonate followed by brine, dried over anhydrous sodium sulfate, filtered, and concentrated under reduced pressure to afford Int-152.4. MS (ES): m/z: 221.0 [M+H]⁺.

Synthesis of compound Int-152.5. To a mixture of Int-139.1 (2.8 g, 12.22 mmol, 1.0 equiv), Int-152.4 (4.04 g, 18.32 mmol, 1.3 equiv), and cesium carbonate (7.94 g, 24.44 mmol, 2.0 equiv) in DMF (15 mL) was stirred at 90° C. for 4 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.0% ethyl acetate in hexane) to afford Int-152.5. MS (ES): m/z 354.2 [M+H]+.

Synthesis of compound Int-152.6. To a solution of Int-152.5 (1.5 g, 4.24 mmol, 1.0 equiv) in ethanol:water (2:1, 50 mL) was added hydroxylamine hydrochloride (11.4 g, 169.6 mmol, 40 equiv). The reaction mixture was stirred at 100° C. for 3 h. It was transferred into ice-water and neutralized by the addition of 2 N sodium hydroxide. The mixture was extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford Int-152.6. MS (ES): m/z 276.0 [M+H]+.

Synthesis of compound Int-152. Compound Int-152 was prepared from Int-152.6 following the procedure described in the synthesis of Int-1. The product was purified by flash column chromatography on silica gel (CombiFlash®, DCM). MS (ES): m/z 318.2 [M+H]+.

Preparation of Provided Compounds

Example 1: (R)—N-(5-(tert-butyl)-1-(tetrahydrofuran-3-yl)-1H-pyrazol-3-yl)-6-((2-cyclopropyl-1H-pyrrolo[2,3-b]pyridin-5-yl)oxy)-1-methyl-1H-imidazo[4,5-b]pyridin-2-amine

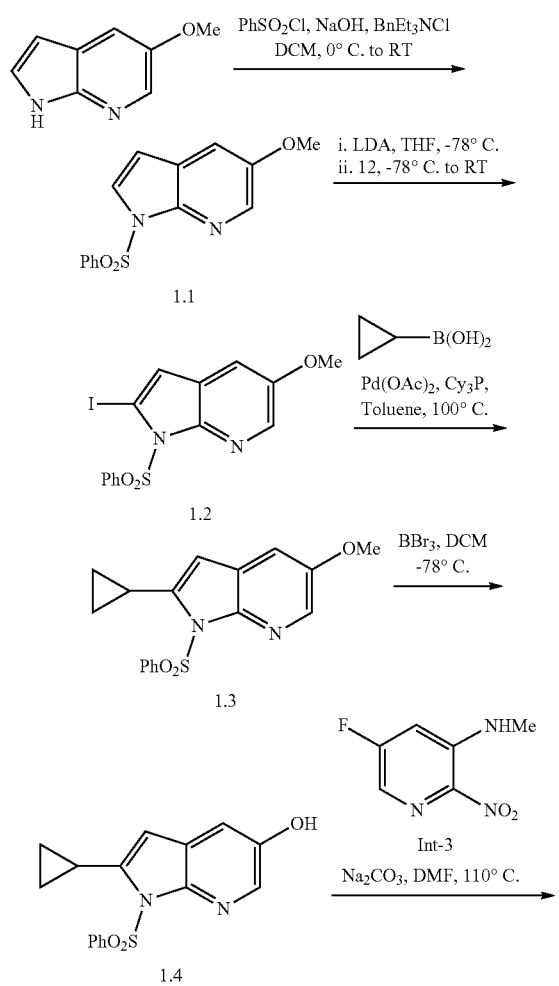

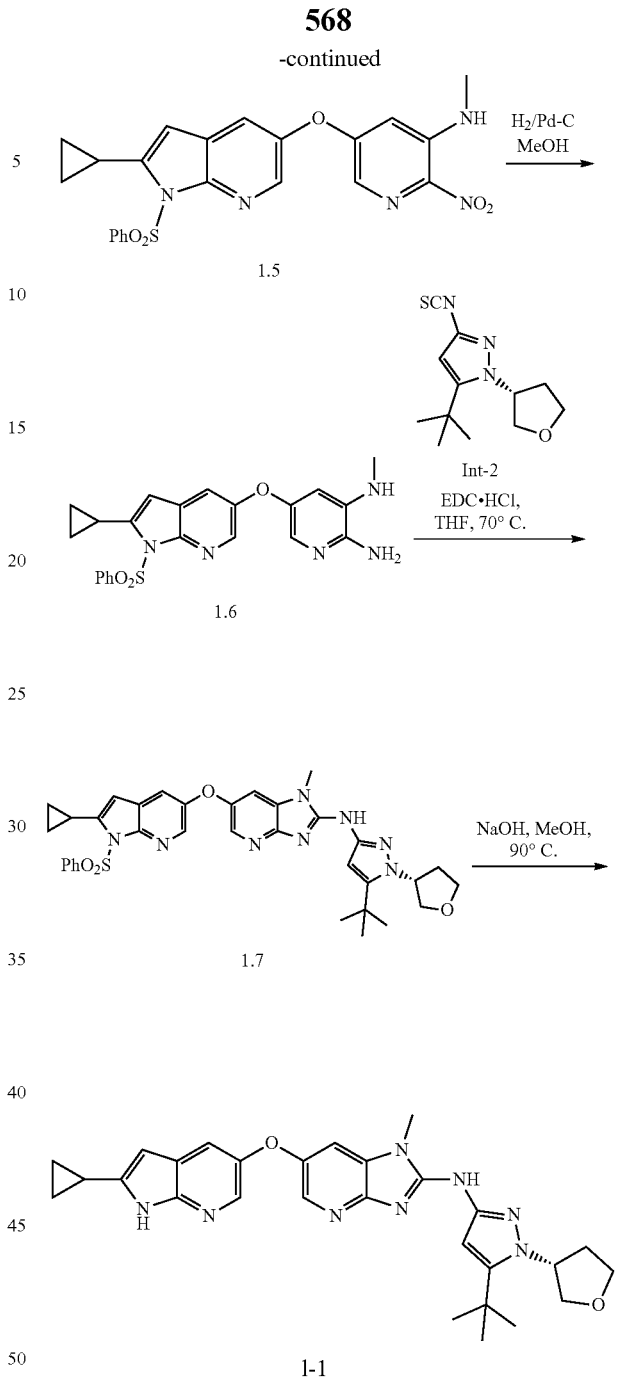

Synthesis of compound 1.1. To a solution of 5-methoxy-1H-pyrrolo[2,3-b]pyridine (18 g, 121 mmol, 1.0 equiv) in dichloromethane (180 mL) was added benzyltriethylammonium chloride (0.711 g, 3.12 mmol, 0.025 equiv) followed by addition of sodium hydroxide powder (14.5 g, 363 mmol, 3.0 equiv). The reaction mixture was cooled to 0° C. and benzyl sulfonyl chloride (26.62 g, 151.25 mmol, 1.25 equiv) and the reaction mixture was stirred at room temperature for 2-3 h. It filtered through a pad of Celite® and the solids were rinsed with dichloromethane. The filtrate was concentrated under reduced pressure. The residue was purified by flash column chromatography on silica gel (CombiFlash®, 20% ethyl acetate in hexane) to afford 1.1. MS (ES): m/z 289.3 [M+H]+.

Synthesis of compound 1.2. A solution of 1.1 (22 g, 76.30 mmol, 1.0 equiv) and diisopropylamine (17.2 mL, 122.08 mmol, 1.6 equiv) in THF (200 mL) at −78° C. was added n-butyllithium (2.5 M in hexane, 48.8 mL, 122.08 mmol, 1.6 equiv) and stirred for 1 h. To the mixture was added a solution of iodine (38.72 g, 152.6 mmol, 2.0 equiv) in THF (200 mL) and the reaction mixture was stirred at −78° C. for 1 h. It was quenched by addition of a saturated ammonium chloride solution. The mixture was extracted with ethyl acetate. The combined organic layers was dried over anhydrous sodium sulfate, filtered and concentrated under reduced pressure. The residue was purified by flash column chromatography on silica gel (CombiFlash®, 20% ethyl acetate in hexane) to afford 1.2. MS (ES): m/z 415.2 $[M+H]^+$.

Synthesis of compound 1.3. A mixture of 1.2 (15 g, 36.21 mmol, 1.0 equiv), cyclopropylboronic acid (4.14 g, 48.16 mmol, 1.33 equiv), potassium phosphate (28.13 g, 132.5 mmol, 3.66 equiv) and tricyclohexylphosphine (2.23 g, 7.96 mmol, 0.22 equiv) in toluene (150 mL) was degassed by bubbling through a stream of argon for 10 min by bubbling through a stream of argon. Palladium(II) acetate (0.894 g, 3.98 mmol, 0.11 equiv) was added to the mixture, and degassed by bubbling through a stream of argon for 5 min. The reaction mixture was stirred at 110° C. for 4 h. It was cooled to room temperature and filtered through a pad of Celite®. The filtrate was poured into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 50% dichloromethane in hexane) to afford 1.3. MS (ES): m/z 329.4 $[M+H]^+$.

Synthesis of compound 1.4. To a solution of 1.3 (6.0 g, 18.27 mmol, 1.0 equiv) in dichloromethane (60 mL) was added boron tribromide solution (1 M in dichloromethane, 40 mL, 40.19 mmol, 2.2 equiv) at −30° C. and stirred for 2 h. It was transferred into ice-cold saturated sodium bicarbonate solution and extracted with dichloromethane. The combined organic layers were washed with brine, dried over anhydrous sodium sulfate, filtered and concentrated under reduced pressure to afford 1.4. MS (ES): m/z 315.3 $[M+H]^+$.

Synthesis of compound 1.5. A mixture of 1.4 (3.1 g, 9.86 mmol, 1.0 equiv), Int-3 (1.69 g, 9.86 mmol, 1.0 equiv) and sodium carbonate (2.09 g, 19.72 mmol, 2.0 equiv) in DMF (30 mL) was stirred at 110° C. for 12 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane to afford 1.5. MS (ES): m/z 466.5 $[M+H]^+$.

Synthesis of compound 1.6. A mixture of compound 1.5 (1.7 g, 3.65 mmol, 1.0 equiv) and 10 wt % palladium on carbon (0.800 g) in methanol (20 mL) was stirred under hydrogen (1 atm) for 1 h. It was filtered through a pad of Celite® and rinsed with methanol. The filtrate was concentrated under reduced pressure. The residue was purified by flash column chromatography on silica gel (CombiFlash®, 2% methanol in dichloromethane) to afford 1.6. MS (ES): m/z 436.5 $[M+H]^+$.

Synthesis of compound 1.7. To a solution of 1.6 (0.100 g, 0.229 mmol, 1.0 equiv) in 1,4-dioxane (2 mL) was added Int-2 (0.057 g, 0.229 mmol, 1.0 equiv) followed by N-(3-dimethylaminopropyl)-N′-ethylcarbodiimide hydrochloride (0.131 g, 0.687 mmol, 3.0 equiv). The reaction mixture was stirred at 70° C. for 2 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.5% methanol in dichloromethane) to afford 1.7. MS (ES): m/z: 653.7 $[M+H]^+$.

Synthesis of I-1. To a solution of 1.7 (0.046 g, 0.070 mmol, 1.0 equiv) in methanol (2 mL) was added 40% aqueous sodium hydroxide (0.4 mL). The mixture was stirred at 100° C. for 1 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 7.0% methanol in dichloromethane) to afford I-1. MS (ES): m/z: 513.69 $[M+H]^+$, $^1$H NMR (DMSO-$d_6$, 400 MHz): δ 11.47 (s, 1H), 9.74 (s, 1H), 7.95-7.90 (m, 2H), 7.40-7.36 (m, 2H), 6.57 (s, 1H), 6.05 (s, 1H), 5.23 (bs, 1H), 4.07 (bs, 2H), 3.85-3.81 (m, 2H), 3.60 (s, 3H), 2.33 (bs, 1H), 2.25-2.22 (m, 1H), 2.02-1.99 (m, 1H), 1.40 (s, 9H), 0.99-0.98 (m, 2H), 0.84-0.83 (m, 2H).

Example 2: (S)—N-(5-(tert-butyl)-1-(tetrahydrofuran-3-yl)-1H-pyrazol-3-yl)-6-((2-cyclopropyl-1H-pyrrolo[2,3-b]pyridin-5-yl)oxy)-1-methyl-1H-imidazo[4,5-b]pyridin-2-amine

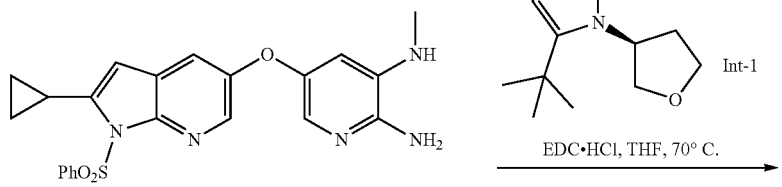

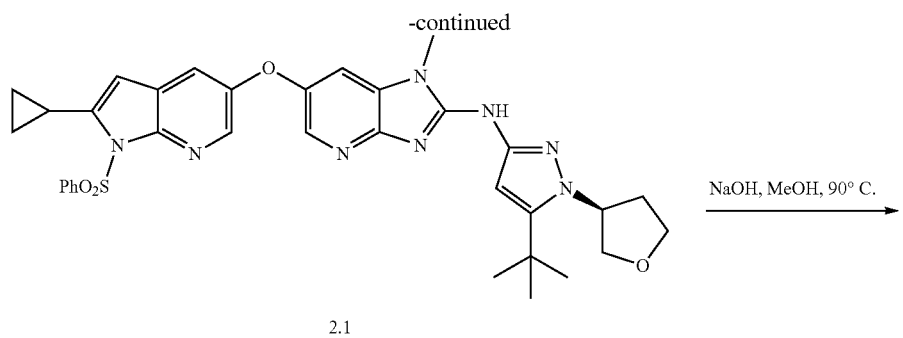

2.1

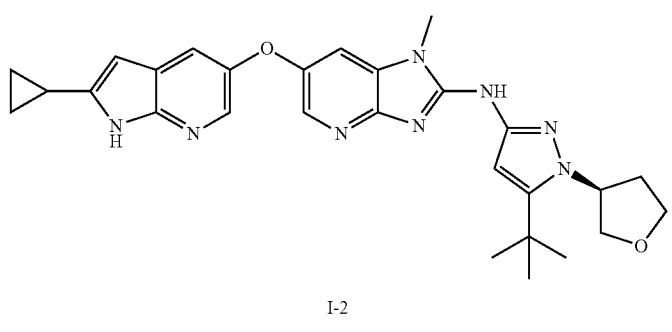

I-2

Synthesis of compound 2.1. Compound 2.1 was prepared from 1.6 and Int-1, following the procedure described in the synthesis of 1.7. The product was purified by flash column chromatography on silica gel (CombiFlash®, 4.4% methanol in dichloromethane). MS (ES): m/z: 653.7 [M+H]$^+$.

Synthesis of I-2. Compound I-2 was prepared from 2.1, following the procedure described in the synthesis of I-1. The product was purified by flash column chromatography on silica gel (CombiFlash®, 6.8% methanol in dichloromethane). MS (ES): m/z: 513.75 [M+H]$^+$, $^1$H NMR (DMSO-d$_6$, 400 MHz): δ 11.49 (s, 1H), 9.77 (s, 1H), 7.96-7.91 (m, 2H), 7.41-7.38 (m, 2H), 6.58 (s, 1H), 6.05 (s, 1H), 5.25 (bs, 1H), 4.08 (bs, 2H), 3.85-3.82 (m, 2H), 3.61 (s, 3H), 2.34 (bs, 1H), 2.26-2.23 (m, 1H), 2.03 (bs, 1H), 1.40 (s, 9H), 1.01-0.99 (m, 2H), 0.84 (bs, 2H).

Example 3: ((R)—N-(5-(tert-butyl)-1-(tetrahydrofuran-3-yl)-1H-pyrazol-3-yl)-1-methyl-6-((3-methyl-1H-pyrazolo[3,4-b]pyridin-5-yl)oxy)-1H-imidazo[4,5-b]pyridin-2-amine

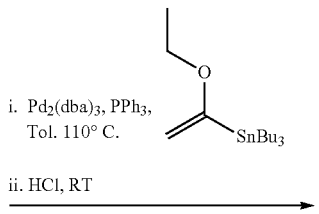

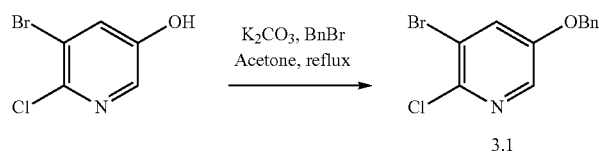

3.1

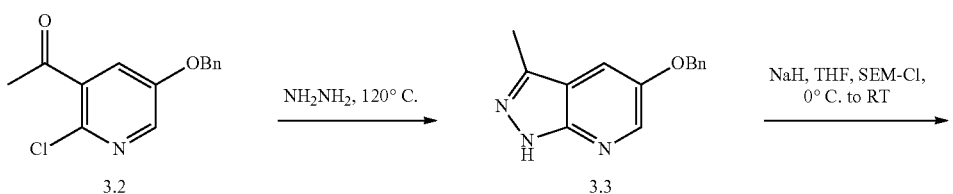

-continued
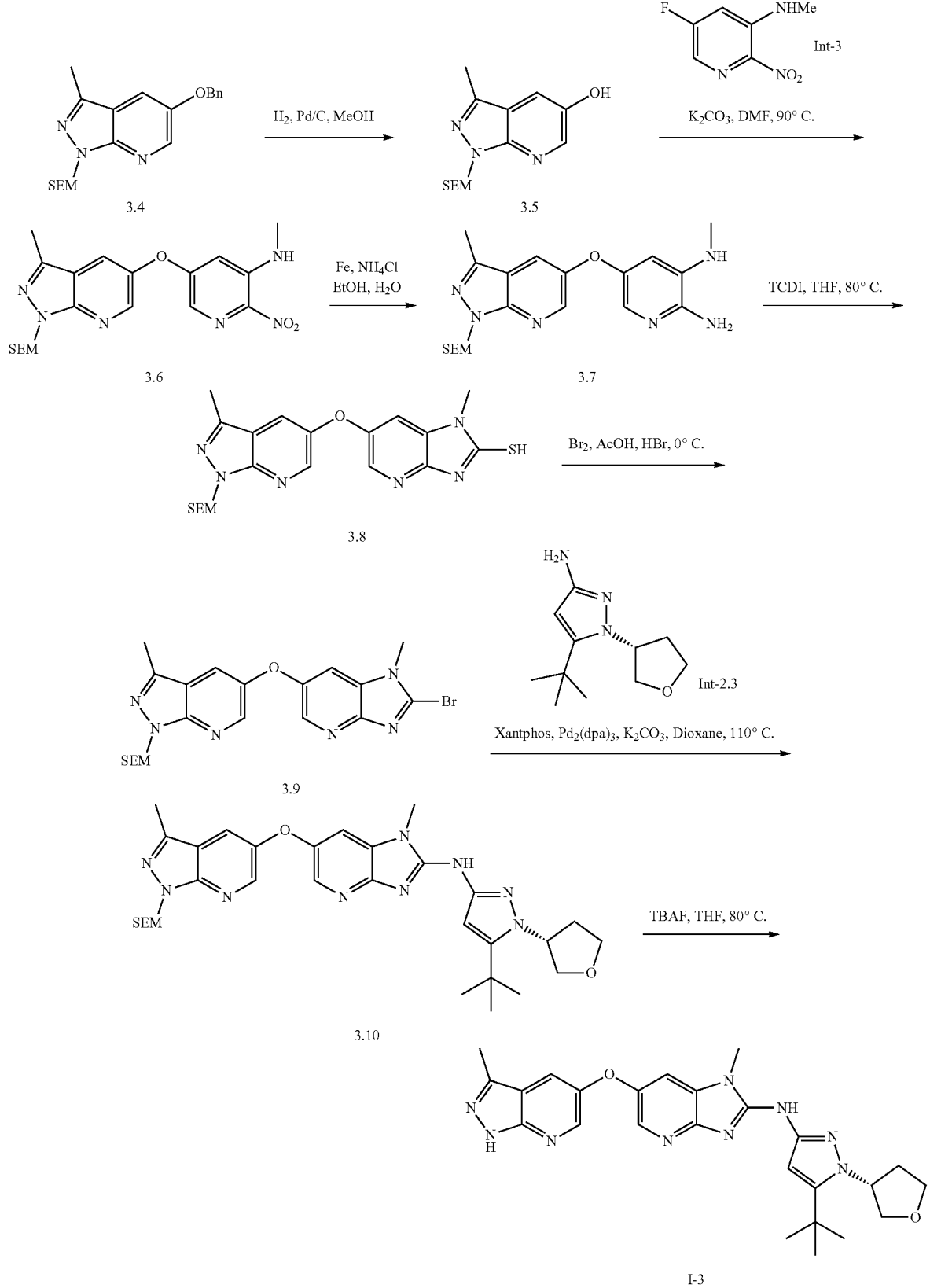
Synthesis of compound 3.1. To a solution of 5-bromo-6-chloropyridin-3-ol (10 g, 47.98 mmol, 1.0 equiv) in acetone (100 mL), was added potassium carbonate (7.94 g, 57.57 mmol, 1.2 equiv) followed by addition of benzyl bromide (9.02 g, 52.77 mmol, 1.1 equiv). The reaction mixture was heated to reflux for 3 h. It cooled to room temperature, poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford 3.1.

Synthesis of compound 3.2. A mixture of 3.1 (10.8 g, 36.17 mmol, 1.0 equiv), triphenylphosphine (0.758 g, 2.89 mmol, 0.08 equiv) in toluene (100 mL) was degassed by bubbling through a stream of argon for 15 min. To the mixture was added tributyl(1-ethoxyvinyl)stannane (13.05 g, 36.17 mmol, 1.0 equiv) and tris(dibenzylideneacetone)dipalladium (1.65 g, 1.80 mmol, 0.05 equiv). The reaction mixture was stirred at 110° C. under argon for 4 h. It was cooled to room temperature, poured over ice-water and extracted with ethyl acetate. The organic layer was dried over anhydrous sodium sulfate, filtered and concentrated under reduced pressure to afford 3.2. MS (ES): m/z 262.3 [M+H]$^+$.

Synthesis of compound 3.3. A mixture of 3.2 (4.1 g, 15.67 mmol, 1.0 equiv) and hydrazine (98%, 16 mL, 4.0 equiv) was stirred at 120° C. for 5 h. It was poured over ice-water, stirred and extracted with ethyl acetate. The combined organic layers were washed with brine, dried over anhydrous sodium sulfate, filtered and concentrated under reduced pressure to afford 3.3. MS (ES): m/z 240.14 [M+H]$^+$.

Synthesis of compound 3.4. To a suspension of sodium hydride (0.301 g, 7.53 mmol, 1.5 equiv) in THF (10 mL) was added a solution of 3.3 (1.2 g, 5.02 mmol, 1.0 equiv) in THF (10 mL) at 0° C. It was stirred for 30 min and (2-chloromethoxyethyl)trimethylsilane (1.0 g, 6.02 mmol, 1.2 equiv) was added. The reaction mixture was allowed to warm to room temperature stirring for 30 min. It was poured into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford 3.4. MS (ES): m/z 370.56 [M+H]$^+$.

Synthesis of compound 3.5. A mixture of compound 3.4 (0.690 g, 1.87 mmol, 1.0 equiv), 10% palladium on carbon (0.350 g) and in methanol (10 mL) was stirred under hydrogen (1 atm) for 5 h. It was filtered through a pad of Celite® and rinsed with methanol. The filtrate was concentrated under reduced pressure to afford 3.5. MS (ES): m/z 280.37 [M+H]$^+$.

Synthesis of compound 3.6. A mixture of 3.5 (0.450 g, 1.61 mmol, 1.0 equiv), Int-3 (0.33 g, 1.93 mmol, 1.0 equiv) and potassium carbonate (0.555 g, 4.02 mmol, 2.5 equiv) in DMF (10 mL) was stirred at 80° C. for 2 h. It was cooled to room temperature, filtered through a pad of Celite®, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford 3.6. MS (ES): m/z 431.6 [M+H]$^+$.

Synthesis of compound 3.7. To a solution of 3.6 (0.450 g, 1.05 mmol, 1.0 equiv) in ethanol-water (2:1, 10 mL) was added iron powder (0.323 g, 5.77 mmol, 5.5 equiv) followed by ammonium chloride (0.283 g, 5.25 mmol, 5.0 equiv). The reaction mixture was stirred at 90° C. for 3 h. It was poured over ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane) to afford 3.7. MS (ES): m/z 401.4 [M+H]$^+$.

Synthesis of compound 3.8. To a solution of 3.7 (0.320 g, 0.798 mmol, 1.0 equiv) in THF (5 mL) was added 1,1'-thiocarbonyldiimidazole (0.710 g, 3.99 mmol, 5.0 equiv). The reaction mixture was stirred at 80° C. for 2 h. It was cooled to room temperature and poured over ice-water. The solids were collected by filtration and triturated in hexane to afford 3.8. MS (ES): m/z: 443.6 [M+H]$^+$.

Synthesis of compound 3.9. To a solution of 3.8 (0.300 g, 0.677 mmol, 1.0 equiv) in acetic acid (4 mL) was added aqueous hydrobromic acid (0.082 g, 1.015 mmol, 1.5 equiv) at 0° C. followed by bromine (0.378 g, 2.36 mmol, 3.5 equiv) and the reaction mixture was stirred for 10 min. It was transferred into saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.2% methanol in dichloromethane) to afford 3.9. MS (ES): m/z 490.4 [M+H]$^+$.

Synthesis of compound 3.10. A mixture of 3.9 (0.060 g, 0.122 mmol, 1.0 equiv), Int-2.3 (0.031 g, 0.147 mmol, 1.2 equiv) and potassium carbonate (0.050 g, 0.366 mmol, 3.0 equiv) in 1,4-dioxane (1.5 mL) was degassed by bubbling through a stream of argon for 10 min. To the mixture were added 4,5-bis(diphenylphosphino)-9,9-dimethylxanthene (0.014 g, 0.024 mmol, 0.2 equiv) and tris(dibenzylideneacetone)dipalladium (0.011 g, 0.012 mmol, 0.1 equiv). It was degassed for another 5 min. The reaction mixture was stirred at 110° C. under argon for 2 h. It was cooled to room temperature, poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 3.10. MS (ES): m/z: 618.5 [M+H]$^+$.

Synthesis of I-3. To a solution of 3.10 (0.036 g, 0.058 mmol, 1.0 equiv) in THF (2 mL) was added TBAF (1 M in THF, 0.46 mL, 0.464 mmol, 8.0 equiv) and stirred at 80° C. for 2 h. It was poured into ice-cold saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 6.0% methanol in dichloromethane) to afford I-3. MS (ES): m/z: 488.49 [M+H; $^1$H NMR (DMSO-d$_6$, 400 MHz): δ 13.24 (s, 1H), 9.80 (s, 1H), 8.45-8.44 (d, J=2.4 Hz, 1H), 7.99-7.98 (d, J=2.4 Hz, 1H), 7.79-7.78 (d, J=2.0 Hz, 1H), 7.50-7.49 (d, J=2.4 Hz, 1H), 6.59 (s, 1H), 5.25 (s, 1H), 4.11-4.07 (m, 2H), 3.88-3.83 (m, 2H), 3.64 (s, 3H), 2.44 (s, 3H), 2.36-2.32 (m, 1H), 2.28-2.20 (m, 1H), 1.41 (s, 9H).

Example 4: (S)—N-(5-(tert-butyl)-1-(tetrahydro-furan-3-yl)-1H-pyrazol-3-yl)-1-methyl-6-((3-methyl-1H-pyrazolo[3,4-b]pyridin-5-yl)oxy)-1H-imidazo[4,5-b]pyridin-2-amine

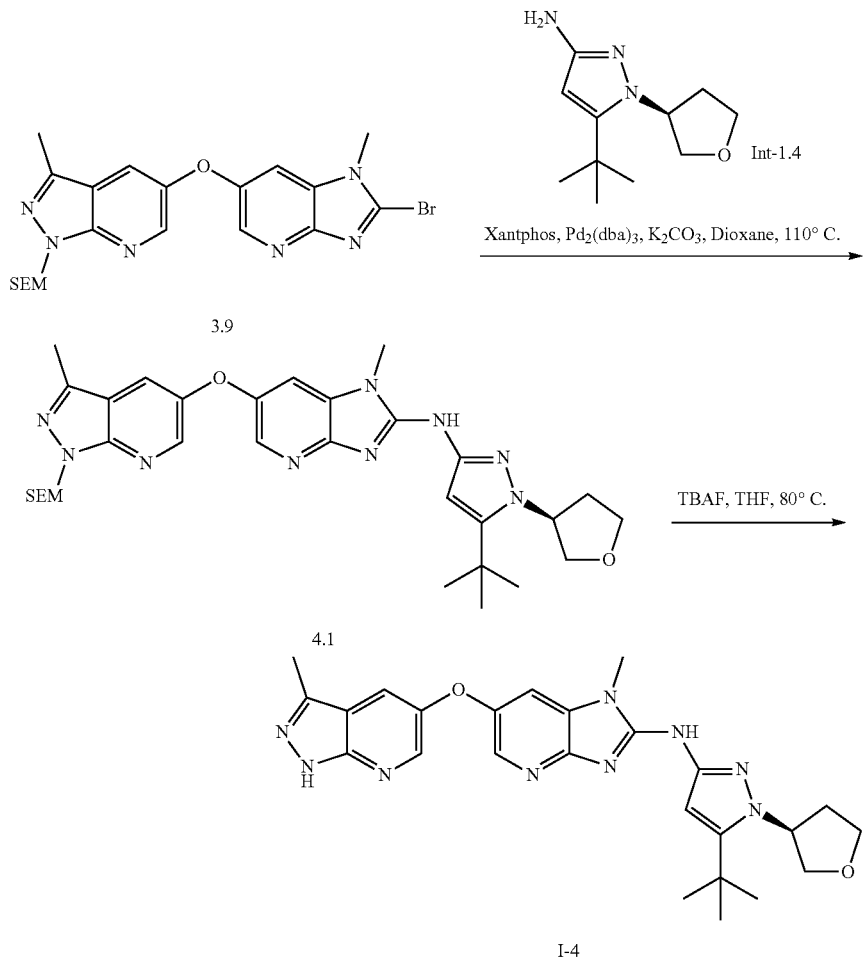

Synthesis of compound 4.1. Compound 4.1 was prepared from 3.9 and Int-1.4, following the procedure described in the synthesis of 3.10. The product was purified by flash column chromatography on silica gel (CombiFlash®, 2.6% methanol in dichloromethane). MS (ES): m/z: 618.5 [M+H]⁺.

Synthesis of I-4. Compound I-4 was prepared from 4.1, following the procedure described in the synthesis of I-3. The product was purified by flash column chromatography on silica gel (CombiFlash®, 6.2% methanol in dichloromethane). MS (ES): m/z: 488.77 [M+H]⁺, ¹H NMR (DMSO-$d_6$, 400 MHz): δ 13.24 (s, 1H), 9.80 (s, 1H), 8.44-8.43 (d, J=2.4 Hz, 1H), 7.98-7.97 (d, J=2.4 Hz, 1H), 7.78-7.77 (d, J=2.0 Hz, 1H), 7.49-7.48 (d, J=2.4 Hz, 1H), 6.58 (s, 1H), 5.24 (s, 1H), 4.10-4.06 (m, 2H), 3.87-3.81 (m, 2H), 3.63 (s, 3H), 2.43 (s, 3H), 2.37-2.30 (m, 1H), 2.27-2.20 (m, 1H), 1.40 (s, 9H).

Example 5: (R)—N-(5-(tert-butyl)-1-(tetrahydro-furan-3-yl)-1H-pyrazol-3-yl)-7-chloro-1-methyl-6-((2-methylpyrazolo[1,5-a]pyrimidin-6-yl)oxy)-1H-imidazo[4,5-b]pyridin-2-amine

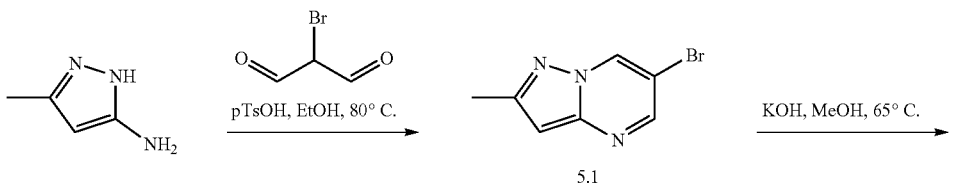

-continued

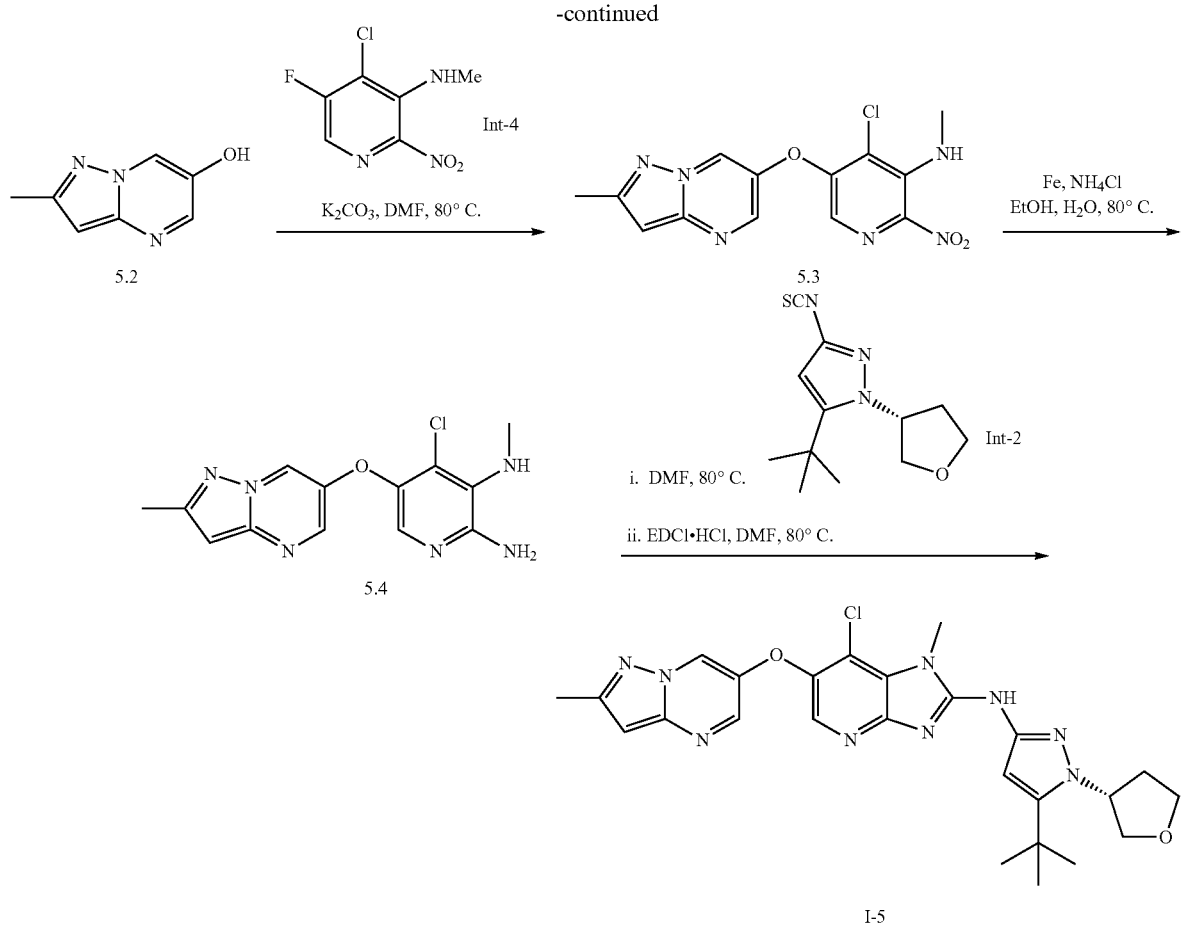

Synthesis of compound 5.1. To a solution of 3-methyl-1H-pyrazol-5-amine (5 g, 51.48 mmol, 1.0 equiv) in ethanol (50 mL) was added 2-bromomalonaldehyde (7.77 g, 51.48 mmol, 1.0 equiv) followed by addition of p-toluenesulfonic acid (0.548 g, 2.88 mmol, 0.056 equiv). The reaction mixture was stirred at 80° C. for 2 h. It was cooled to room temperature and concentrated under reduced pressure. The crude product was triturated with ethanol to afford 5.1. MS (ES): m/z 211.8 [M−H]$^+$.

Synthesis of compound 5.2. To a solution of 5.1 (3.5 g, 16.51 mmol, 1.0 equiv) in methanol (70 mL), was added potassium hydroxide (5.54 g, 99.06 mmol, 6.0 equiv). The reaction mixture was stirred at 65° C. for 2 h. It was cooled to room temperature and concentrated under reduced pressure. The reaction mixture was then neutralized with 1N hydrochloric acid and extracted with ethyl acetate. The organic layer was dried over anhydrous sodium sulfate, filtered and concentrated under reduced pressure to afford 5.2. MS (ES): m/z 149.95 [M+H]$^+$.

Synthesis of compound 5.3. A mixture of 5.2 (1.4 g, 9.39 mmol, 1.0 equiv), Int-4 (1.93 g, 9.39 mmol, 1.0 equiv) and potassium carbonate (3.23 g, 23.47 mmol, 2.5 equiv) in DMF (15 mL) was stirred at 80° C. for 1 h. It was cooled to room temperature, filtered through a pad of Celite, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.8% methanol in dichloromethane) to afford 5.3. MS (ES): m/z 335.2 [M+H]$^+$.

Synthesis of compound 5.4. To a solution of 5.3 (0.400 g, 1.2 mmol, 1.0 equiv) in ethanol-water (2:1, 10 mL) was added iron powder (0.336 g, 6.0 mmol, 5.0 equiv) followed by ammonium chloride (0.324 g, 6.0 mmol, 5.0 equiv). The reaction mixture was stirred at 80° C. for 2 h. It was poured over ice-water, filtered and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 5.4. MS (ES): m/z 305.2 [M+H]$^+$.

Synthesis of I-5. A solution of 5.4 (0.200 g, 0.656 mmol, 1.0 equiv) and Int-2 (0.164 g, 0.656 mmol, 1.0 equiv) in DMF (2 mL) was stirred at 80° C. for 2 h. It was cooled to room temperature, poured over ice-water and extracted with ethyl acetate. The combined organic layers were washed with brine, dried over anhydrous sodium sulfate, filtered and concentrated under reduced pressure. The residue was dissolved in DMF (2 mL) and N-(3-dimethylaminopropyl)-N'-ethylcarbodiimide hydrochloride (0.187 g, 0.984 mmol, 1.5 equiv) was added. The reaction mixture was stirred at 80° C. for 12 h. It cooled to room temperature, poured over ice-water and extracted with ethyl acetate. The combined organic layers were washed with brine, dried over anhydrous sodium sulfate, filtered and concentrated under reduced pressure. The residue was purified by preparative HPLC to afford I-5. MS (ES): m/z: 522.4 [M+H]$^+$, $^1$H NMR (DMSO-d$_6$, 400 MHz): δ 10.01 (s, 1H), 8.82-8.81 (d, J=2.4 Hz, 1H), 8.60-8.59 (d, J=2.8 Hz, 1H), 8.11 (s, 1H), 6.57-6.55 (m, 2H), 5.27 (bs, 1H), 4.12-4.08 (m, 2H), 3.94 (s, 3H), 3.89-3.83 (m, 2H), 2.41 (s, 3H), 2.34 (bs, 1H), 2.27-2.22 (m, 1H), 1.41 (s, 9H).

Example 6: (S)—N-(5-(tert-butyl)-1-(tetrahydrofuran-3-yl)-1H-pyrazol-3-yl)-7-chloro-1-methyl-6-((2-methylpyrazolo[1,5-a]pyrimidin-6-yl)oxy)-1H-imidazo[4,5-b]pyridin-2-amine

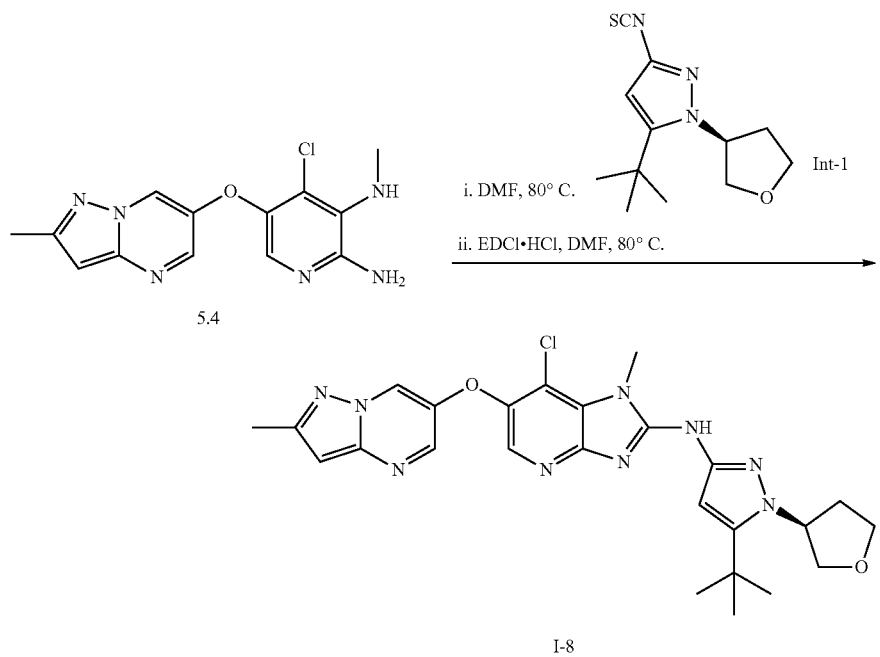

Synthesis of I-6. Compound I-6 was prepared from 5.4 and Int-1, following the procedure described in the synthesis of I-5. The product was purified by preparative HPLC. MS (ES): m/z: 522.4 [M+H]$^+$; $^1$H NMR (DMSO-d$_6$, 400 MHz): δ 10.00 (s, 1H), 8.80-8.79 (d, J=2.4 Hz, 1H), 8.59-8.58 (d, J=2.8 Hz, 1H), 8.10 (s, 1H), 6.55-6.54 (m, 2H), 5.26 (bs, 1H), 4.11-4.07 (m, 2H), 3.94 (s, 3H), 3.87-3.82 (m, 2H), 2.39 (s, 3H), 2.33 (bs, 1H), 2.27-2.21 (m, 1H), 1.40 (s, 9H).

Example 7: (R)-7-chloro-1-methyl-N-(5-(perfluoroethyl)-1-(tetrahydrofuran-3-yl)-1H-pyrazol-3-yl)-6-(pyrazolo[1,5-a]pyrimidin-6-yloxy)-1H-imidazo[4,5-b]pyridin-2-amine

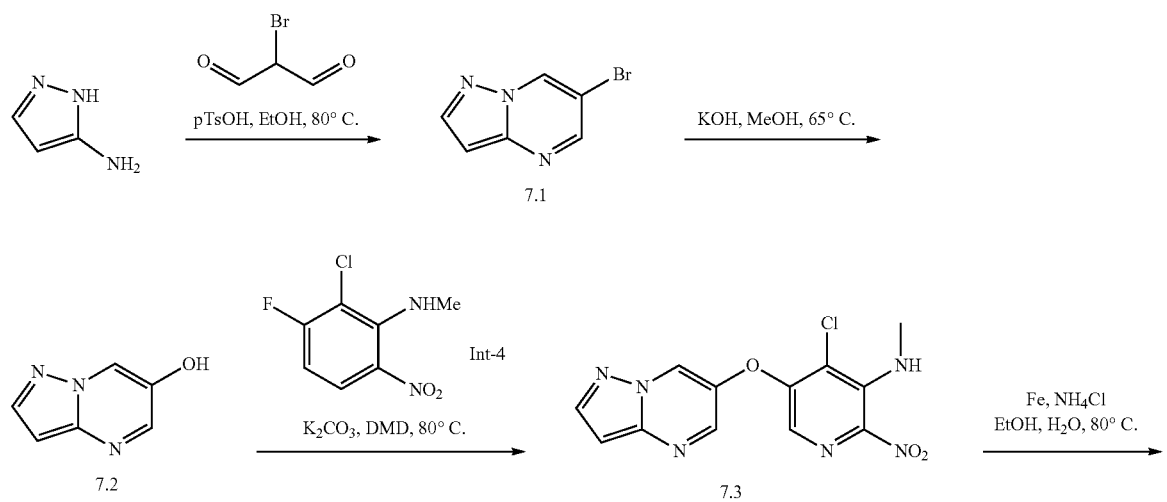

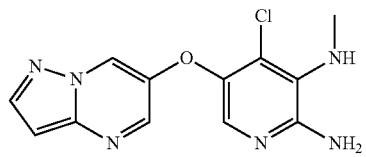 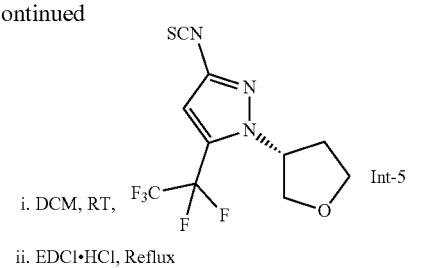

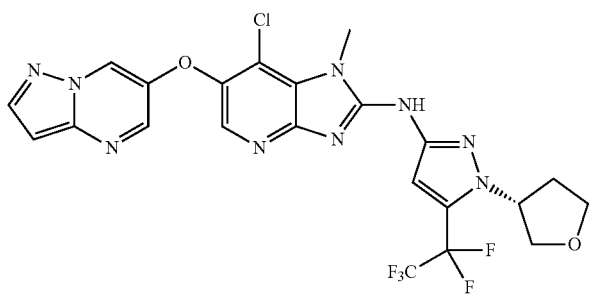

Synthesis of compound 7.1. Compound 7.1 was prepared following the procedure described in the synthesis of 5.1. The product was triturated in ethanol. MS (ES): m/z 197.8 [M+H]+.

Synthesis of compound 7.2. Compound 7.2 was prepared following the procedure described in the synthesis of 5.2. The product was used in the next step without purification. MS (ES): m/z 135.94 [M+H]+.

Synthesis of compound 7.3. Compound 7.3 was prepared following the procedure described in the synthesis of 5.3. The product was purified by flash column chromatography on silica gel (CombiFlash®, 24% ethyl acetate in hexane). MS (ES): m/z 321.1 [M+H]+.

Synthesis of compound 7.4. Compound 7.4 was prepared following the procedure described in the synthesis of 5.4. The product was purified by flash column chromatography on silica gel (CombiFlash®, 3.0% methanol in dichloromethane). MS (ES): m/z 291.1 [M+H]+.

Synthesis of I-7. A solution of 7.4 (0.085 g, 0.292 mmol, 1.0 equiv) and Int-5 (0.091 g, 0.292 mmol, 1.0 equiv) in dichloromethane (6 mL) was stirred at room temperature for 6 h. To the mixture was added N-(3-dimethylaminopropyl)-N'-ethylcarbodiimide hydrochloride (0.167 g, 0.876 mmol, 3.0 equiv) and it was heated to reflux for 24 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.9% methanol in dichloromethane) to afford I-7. MS (ES): m/z: 570.4 [M+H]+, $^1$H NMR (DMSO-d$_6$, 400 MHz): δ 10.63 (s, 1H), 8.90-8.89 (d, J=2.4 Hz, 1H), 8.70-8.69 (d, J=2.8 Hz, 1H), 8.20-8.18 (m, 2H), 7.37 (s, 1H), 6.80-6.79 (m, 1H), 5.18 (bs, 1H), 4.15-4.06 (m, 2H), 3.99 (s, 3H), 3.95-3.93 (m, 1H), 3.88-3.83 (m, 1H), 2.47-2.42 (m, 1H), 2.34-2.31 (m, 1H).

Example 8: (S)-7-chloro-1-methyl-N-(5-(perfluoroethyl)-1-(tetrahydrofuran-3-yl)-1H-pyrazol-3-yl)-6-(pyrazolo[1,5-a]pyrimidin-6-yloxy)-1H-imidazo[4,5-b]pyridin-2-amine

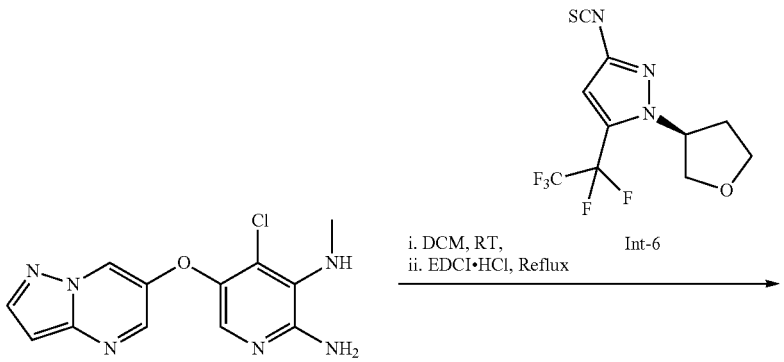

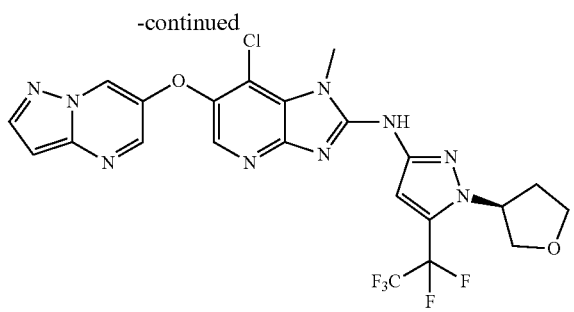

I-8

Synthesis of compound I-8. Compound I-8 was prepared from 7.4 and Int-6, following the procedure described in the synthesis of I-7. The product was purified by flash column chromatography on silica gel (CombiFlash®, 1.9% methanol in dichloromethane). MS (ES): m/z: 570.4 [M+H]+, 1H NMR (DMSO-d6, 400 MHz): δ 10.63 (s, 1H), 8.90-8.89 (d, J=2.4 Hz, 1H), 8.71-8.70 (d, J=2.8 Hz, 1H), 8.20-8.18 (m, 2H), 7.37 (s, 1H), 6.80-6.79 (m, 1H), 5.18 (bs, 1H), 4.13-4.06 (m, 2H), 3.99 (s, 3H), 3.96-3.92 (m, 1H), 3.89-3.83 (m, 1H), 2.47-2.42 (m, 1H), 2.34-2.31 (m, 1H).

Example 9: ((R)-5-((2-((5-(tert-butyl)-1-(tetrahydrofuran-3-yl)-1H-pyrazol-3-yl)amino)-1-methyl-1H-imidazo[4,5-b]pyridin-6-yl)oxy)-1H-pyrrolo[2,3-b]pyridine-3-carbonitrile

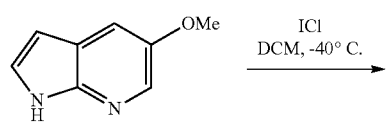

9.1

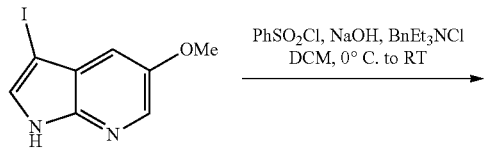

9.2

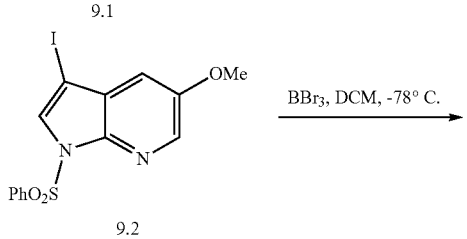

9.3

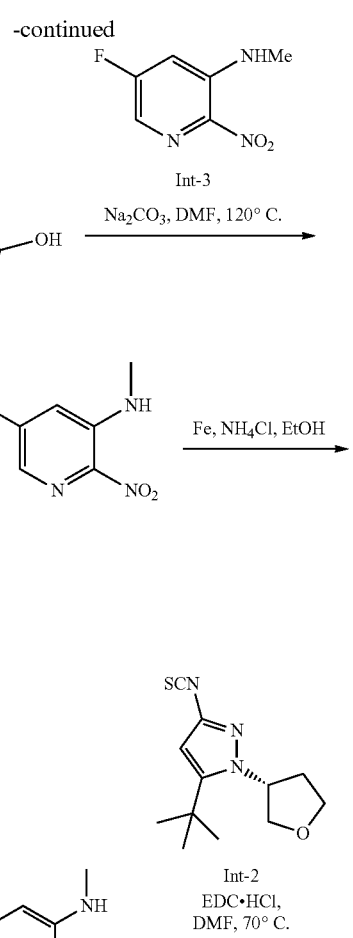

9.4

9.5

9.6

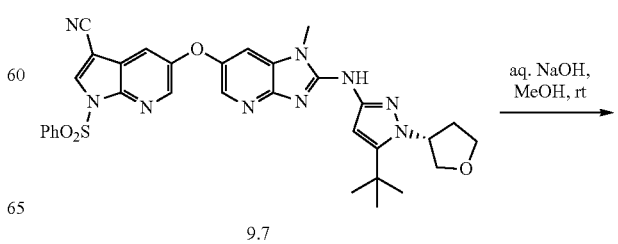

9.7

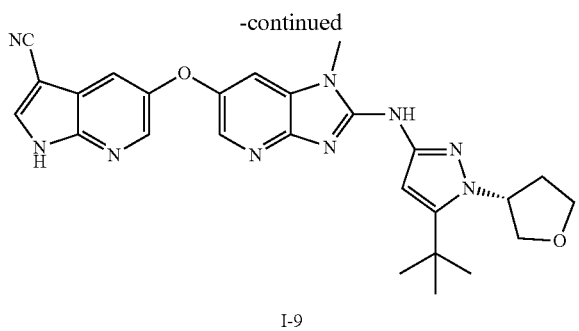

I-9

Synthesis of compound 9.1. To a solution of 5-methoxy-1H-pyrrolo[2,3-b]pyridine (5 g, 33.75 mmol, 1.0 equiv) in dichloromethane (200 mL), was added iodine monochloride (1 M in dichloromethane, 50 mL, 50.62 mmol, 1.5 equiv) at −40° C. The reaction mixture was stirred at room temperature for 1 h. It was poured over ice-water and extracted with dichloromethane. The organic layer was washed with sodium thiosulfate solution, dried over anhydrous sodium sulfate, filtered and concentrated under reduced pressure to afford 9.1. MS (ES): m/z 275.1 [M+H]$^+$.

Synthesis of compound 9.2. To a solution of 9.1 (5.5 g, 20.07 mmol, 1.0 equiv) in dichloromethane (55 mL) was added benzyltriethylammonium chloride (1.138 g, 5.01 mmol, 0.25 equiv) followed by addition of sodium hydroxide powder (2.4 g, 60.21 mmol, 3.0 equiv). The reaction mixture was cooled to 0° C. and benzyl sulfonyl chloride (4.41 g, 25.08 mmol, 1.25 equiv) was added. The reaction mixture was stirred at room temperature for 1 h. It was filtered through a pad of Celite® and washed with dichloromethane. The filtrate was concentrated under reduced pressure. The residue was purified by flash column chromatography on silica gel (CombiFlash®, 15% ethyl acetate in hexane) to afford 9.2. MS (ES): m/z 415.3 [M+H]$^+$.

Synthesis of compound 9.3. To a solution of 9.2 (6.3 g, 15.21 mmol, 1.0 equiv) in dichloromethane (60 mL) was added boron tribromide solution (1 M in dichloromethane, 114 mL, 114 mmol, 7.5 equiv) at −78° C. The reaction mixture was allowed to warm to room temperature stirring for 2 h. It was poured into ice-cold saturated sodium bicarbonate solution and extracted with dichloromethane. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 9.3. MS (ES): m/z 401.1 [M+H]$^+$.

Synthesis of compound 9.4. A solution of 9.3 (4.2 g, 10.50 mmol, 1.0 equiv) and zinc cyanide (0.859 g, 7.35 mmol, 0.7 equiv) in DMF (20 mL) and water (20 mL) was degassed by bubbling through a stream of argon for 10 min. Tris(dibenzylideneacetone)dipalladium (0.480 g, 0.525 mmol, 0.05 equiv) and 1,1'-bis(diphenylphosphino)ferrocene (0.581 g, 1.05 mmol, 0.1 equiv) were added and the reaction mixture heated at 120° C. under argon for 1 h. It was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 22% ethyl acetate in hexane) to afford 9.4. MS (ES): m/z 300.3 [M+H]$^+$.

Synthesis of compound 9.5. A mixture of 9.4 (2.7 g, 9.02 mmol, 1.0 equiv), Int-3 (1.54 g, 9.02 mmol, 1.0 equiv) and sodium carbonate (1.91 g, 18.04 mmol, 2.0 equiv) in DMF (30 mL) was stirred at 120° C. for 12 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane) to afford 9.5. MS (ES): m/z 451.2 [M+H]$^+$.

Synthesis of compound 9.6. Compound 9.6 was prepared from 9.5, following the procedure described in the synthesis of 5.4. The product was purified by flash column chromatography on silica gel (CombiFlash®, 3.5% methanol in dichloromethane). MS (ES): m/z 421.2 [M+H]$^+$.

Synthesis of compound 9.7. Compound 9.7 was prepared from 9.6 and Int-2 following the procedure described in the synthesis of 1.7. The product was purified by flash column chromatography on silica gel (CombiFlash®, 2.6% methanol in dichloromethane). MS (ES): m/z: 638.5 [M+H]$^+$.

Synthesis of I-9. To a solution of 9.7 (0.060 g, 0.094 mmol, 1.0 equiv) in methanol (2 mL) was added 40% aqueous sodium hydroxide (0.5 mL) and stirred at room temperature for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane) to afford I-9. MS (ES): m/z: 498.5 [M+H]$^+$; $^1$H NMR (DMSO-d$_6$, 400 MHz): δ 10.01 (s, 1H), 9.99 (s, 1H), 8.73-8.72 (d, J=5.2 Hz, 1H), 8.42-8.41 (d, J=2.4 Hz, 1H), 8.09-8.08 (d, J=2.8 Hz, 1H), 8.04-8.03 (d, J=2.4 Hz, 1H), 7.48-7.47 (d, J=2.4 Hz, 1H), 6.63 (s, 1H), 5.27 (bs, 1H), 4.11-4.07 (m, 2H), 3.88-3.83 (m, 2H), 3.73 (s, 3H), 2.41-2.36 (m, 1H), 2.26-2.21 (m, 1H), 1.41 (s, 9H).

Example 10: (S)-5-((2-((5-(tert-butyl)-1-(tetrahydrofuran-3-yl)-1H-pyrazol-3-yl)amino)-1-methyl-1H-imidazo[4,5-b]pyridin-6-yl)oxy)-1H-pyrrolo[2,3-b]pyridine-3-carbonitrile

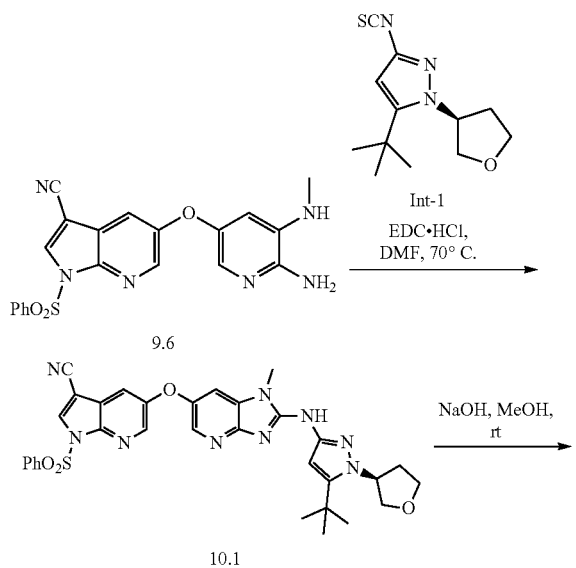

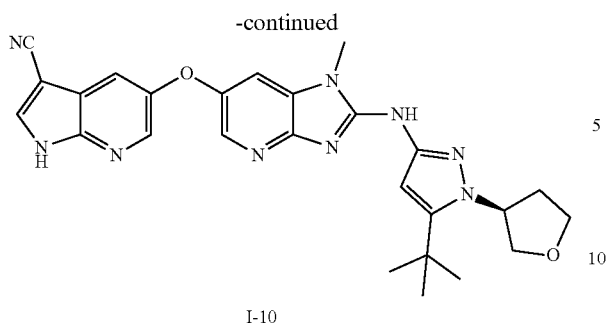

I-10

Synthesis of compound 10.1. Compound 10.1 was prepared from 9.6 and Int-1 following the procedure described in the synthesis of 1.7. The product was purified by flash column chromatography on silica gel (CombiFlash®, 2.6% methanol in dichloromethane). MS (ES): m/z: 638.5 [M+H]$^+$.

Synthesis of I-10. Compound I-10 was prepared from 10.1 following the procedure described in the synthesis of I-9. The product was purified by flash column chromatography on silica gel (CombiFlash®, 3.5% methanol in dichloromethane). MS (ES): m/z: 498.5 [M+H]$^+$, $^1$H NMR (DMSO-d$_6$, 400 MHz): δ 10.02 (s, 1H), 10.00 (s, 1H), 8.73-8.72 (d, J=5.2 Hz, 1H), 8.42-8.41 (d, J=2.4 Hz, 1H), 8.09-8.08 (d, J=2.8 Hz, 1H), 8.04-8.03 (d, J=2.4 Hz, 1H), 7.48-7.47 (d, J=2.4 Hz, 1H), 6.63 (s, 1H), 5.27 (bs, 1H), 4.10-4.08 (m, 2H), 3.86-3.82 (m, 2H), 3.73 (s, 3H), 2.38-2.36 (m, 1H), 2.28-2.21 (m, 1H), 1.41 (s, 9H).

Example 11: ((R)—N-(5-(tert-butyl)-1-(tetrahydrofuran-3-yl)-1H-pyrazol-3-yl)-6-((3-(methoxymethyl)-1H-pyrrolo[2,3-b]pyridin-5-yl)oxy)-1-methyl-1H-imidazo[4,5-b]pyridin-2-amine

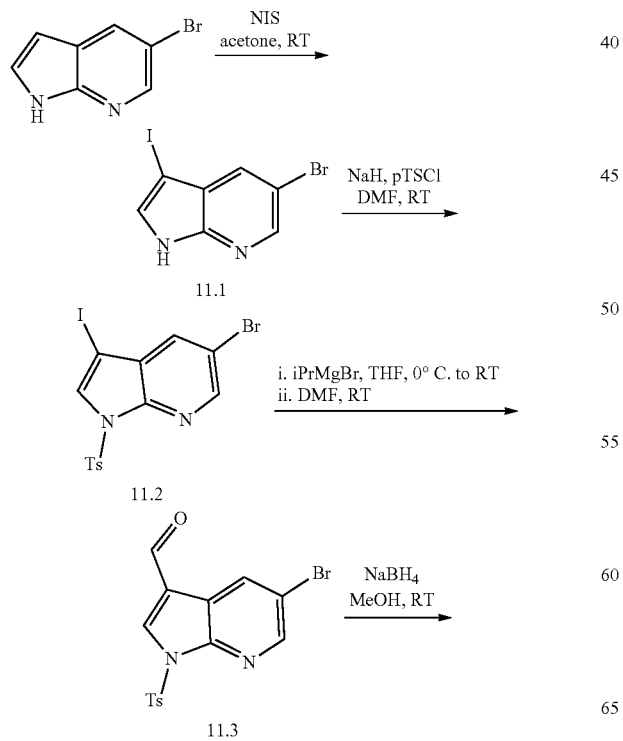

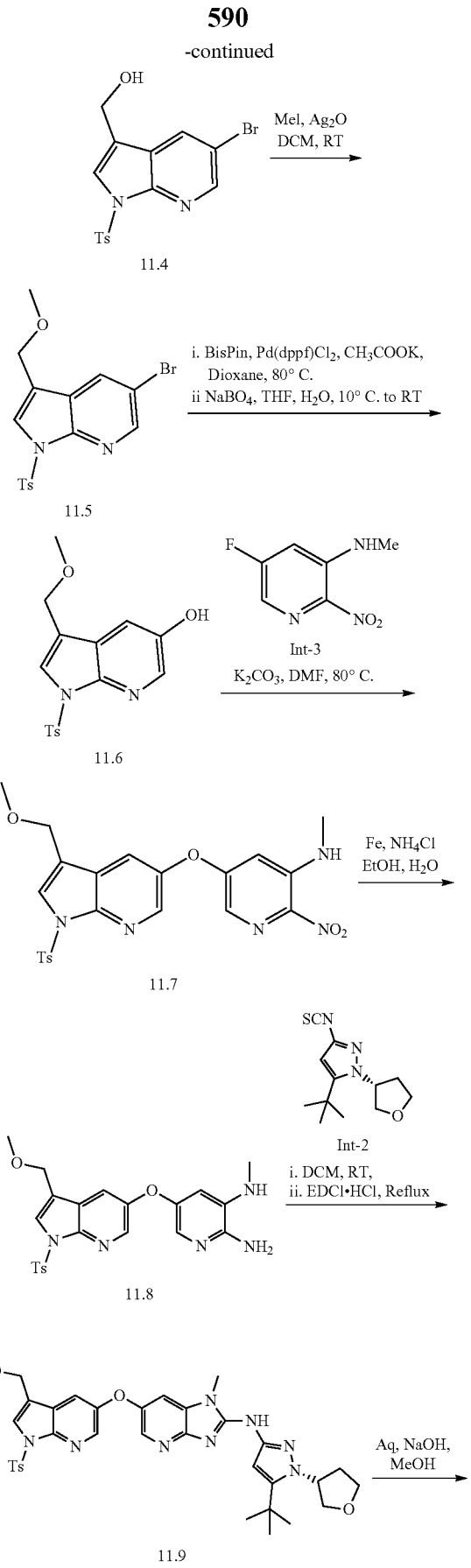

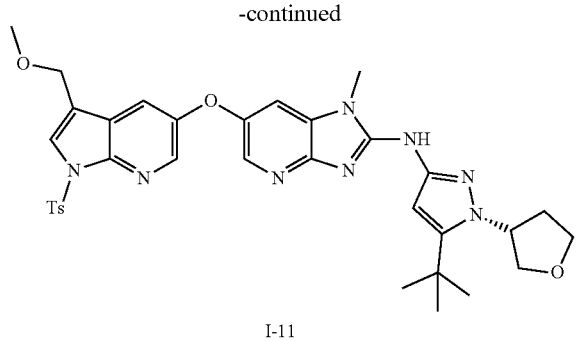

I-11

Synthesis of compound 11.1. To a solution of 5-bromo-1H-pyrrolo[2,3-b]pyridine (20 g, 101.5 mmol, 1.0 equiv) in acetone (400 mL) was added N-iodosuccinimide (25 g, 111.65 mmol, 1.1 equiv) at 0° C. in portions. The reaction mixture was stirred at room temperature for 2 h. It was poured over ice-water and product precipitated out was filtered and dried well to obtain 11.1. MS (ES): m/z 323.1 [M+H]$^+$.

Synthesis of compound 11.2. To a solution of 11.1 (21.0 g, 65.03 mmol, 1.0 equiv) in DMF (200 mL) was added sodium hydride (3.9 g, 97.54 mmol, 1.5 equiv) in small portions at 0° C. It was stirred for 1 h and then 4-toluenesulfonyl chloride was added (13.59 g, 71.53 mmol, 1.1 equiv). The reaction mixture was stirred at room temperature for 2 h. It was poured over ice-water, and the precipitated product was filtered and dried to obtain 11.2. MS (ES): m/z 477.4 [M+H]$^+$.

Synthesis of compound 11.3. To a solution of 11.2 (26 g, 54.49 mmol, 1.0 equiv) in THF (260 mL) at 0° C. was added isopropylmagnesium bromide (1 M in THF, 59.9 mL, 59.93 mmol, 1.1 equiv). It was stirred for 30 min and DMF (8.3 mL, 108.98 mmol, 2.0 equiv) was added. The mixture was allowed to warm to rt and stirred for 2 h. It was transferred into saturated ammonium chloride and extracted with ethyl acetate. The combined organic layers were washed with brine, dried over anhydrous sodium sulfate, filtered and concentrated under reduced pressure to afford crude product. The residue was purified by flash column chromatography on silica gel (CombiFlash®, 30% ethyl acetate in hexane) to afford 11.3. MS (ES): m/z 379.3 [M+H]$^+$.

Synthesis of compound 11.4. To a solution of 11.3 (12 g, 31.64 mmol, 1.0 equiv) in methanol (120 mL) was added sodium borohydride (1.75 g, 47.46 mmol, 1.5 equiv) in small portions at 0° C. The reaction mixture was stirred at room temperature for 16 h. It was poured over ice-water, and product precipitated out was filtered, dried well to obtain 11.4. MS (ES): m/z 381.3 [M+H]$^+$.

Synthesis of compound 11.5. To a solution of 11.4 (9 g, 23.61 mmol, 1.0 equiv) in dichloromethane (90 mL) was added silver oxide (27.26 g, 118.05 mmol, 5.0 equiv) followed by methyl iodide (7.3 mL, 118.05 mmol, 5.0 equiv). The reaction mixture was stirred at room temperature for 24 h. It was poured over ice-water, extracted with ethyl acetate. The combined organic layers were washed with brine, dried over anhydrous sodium sulfate, filtered and concentrated under reduced pressure to afford crude. The residue was purified by flash column chromatography on silica gel (CombiFlash®, 15% ethyl acetate in hexane) to afford 11.5. MS (ES): m/z 395.5 [M+H]$^+$.

Synthesis of compound 11.6. A mixture of 11.5 (5.1 g, 12.90 mmol, 1.0 equiv), bis(pinacolato)diboron (4.24 g, 16.77 mmol, 1.3 equiv) and potassium acetate (4.24 g, 38.7 mmol, 3.0 equiv) in 1,4-dioxane (50 mL) was degassed by bubbling through a stream of argon for 10 min. [1,1'-Bis(diphenylphosphino)-ferrocene]palladium(II) dichloride (0.471 g, 0.645 mmol, 0.05 equiv) was added and the reaction mixture was heated at 80° C. under argon for 24 h. It was filtered through a pad of Celite® and rinsed with dichloromethane. The filtrate was concentrated under reduced pressure. The residue was dissolved in THF (50 mL) and water (10 mL), followed by addition of sodium perborate (3.94 g, 25.8 mmol, 2.0 equiv) at 10° C. The reaction mixture was stirred at room temperature for 3 h. It was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane) to afford 11.6 (2.3 g, 53.63%). MS (ES): m/z 333.4 [M+H]$^+$.

Synthesis of compound 11.7. A mixture of 11.6 (2.3 g, 6.92 mmol, 1.0 equiv), Int-3 (1.18 g, 6.92 mmol, 1.0 equiv) and potassium carbonate (2.38 g, 17.3 mmol, 2.5 equiv) in DMF (25 mL) was stirred at 80° C. for 2 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in dichloromethane) to afford 11.7. MS (ES): m/z 484.4 [M+H]$^+$.

Synthesis of compound 11.8. Compound 11.8 was prepared from 11.7, following the procedure described in the synthesis of 5.4. The product was purified by flash column chromatography on silica gel (CombiFlash®, 3.3% methanol in dichloromethane). MS (ES): m/z 454.6 [M+H]$^+$.

Synthesis of compound 11.9. Compound 11.9 was prepared from 11.8 and Int-2, following the procedure described in the synthesis of I-7. The product was purified by flash column chromatography on silica gel (CombiFlash®, 2.5% methanol in dichloromethane). MS (ES): m/z: 671.6 [M+H]$^+$.

Synthesis of I-11. To a solution of 11.9 (0.095 g, 0.141 mmol, 1.0 equiv) in methanol (10 mL) was added 20% aqueous sodium hydroxide (15 mL), and the reaction mixture was stirred at room temperature for 30 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in dichloromethane) to afford I-11. MS (ES): m/z: 517.4 [M+H]$^+$; $^1$H NMR (DMSO-d$_6$, 400 MHz): δ 11.65 (s, 1H), 9.79 (s, 1H), 8.13-8.12 (d, J=2.4 Hz, 1H), 7.94-7.93 (d, J=2.4 Hz, 1H), 7.58-7.57 (d, J=2.8 Hz, 1H), 7.53-7.52 (d, J=2.4 Hz, 1H), 7.44-7.43 (d, J=2.4 Hz, 1H), 6.58 (s, 1H), 5.24 (bs, 1H), 4.48 (s, 2H), 4.10-4.06 (m, 2H), 3.85-3.81 (m, 2H), 3.62 (s, 3H), 3.19 (s, 3H), 2.33 (bs, 1H), 2.28-2.23 (m, 1H), 1.40 (s, 9H).

Example 12: ((S)—N-(5-(tert-butyl)-1-(tetrahydro-furan-3-yl)-1H-pyrazol-3-yl)-6-((3-(methoxymethyl)-1H-pyrrolo[2,3-b]pyridin-5-yl)oxy)-1-methyl-1H-imidazo[4,5-b]pyridin-2-amine 8.13-8.12 (d, J=2.4 Hz, 1H), 7.94-7.93 (d, J=2.4 Hz, 1H), 7.58-7.57 (d, J=2.8 Hz, 1H), 7.53-7.52 (d, J=2.4 Hz, 1H), 7.44-7.43 (d, J=2.4 Hz, 1H), 6.58 (s, 1H), 5.24 (bs, 1H), 4.48 (s, 2H), 4.10-4.06 (m, 2H), 3.87-3.81 (m, 2H), 3.62 (s, 3H), 3.19 (s, 3H), 2.33 (bs, 1H), 2.25-2.20 (m, 1H), 1.40 (s, 9H).

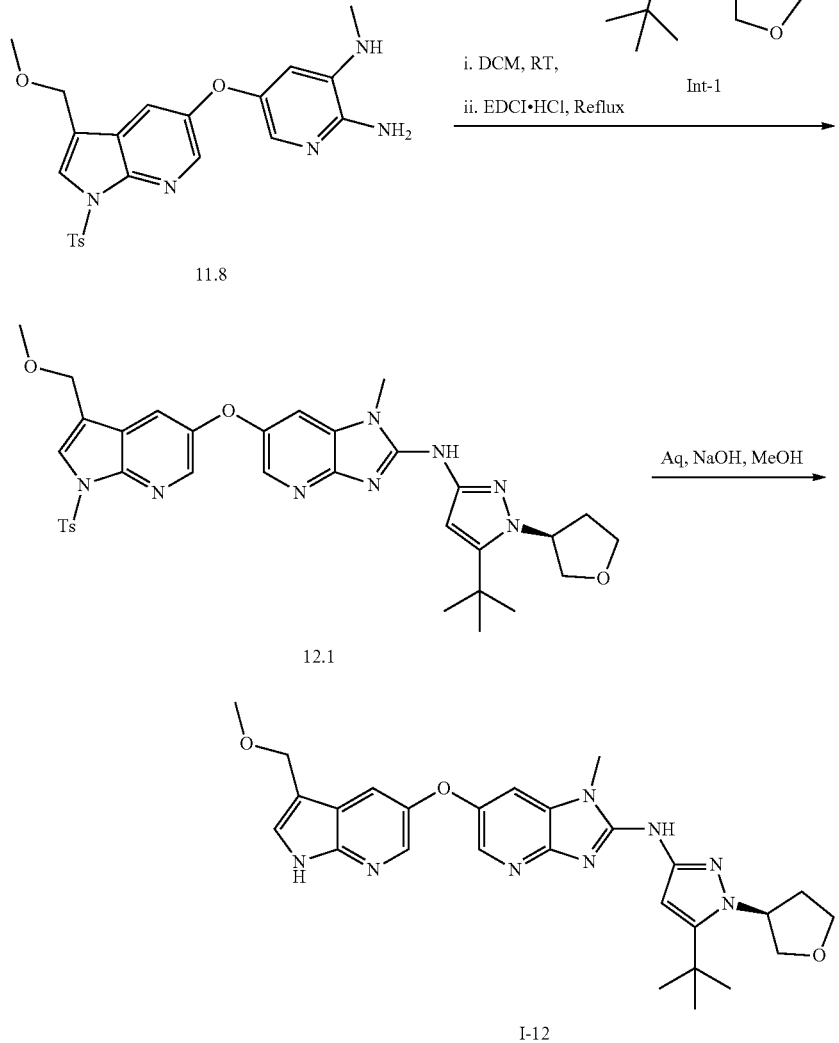

Synthesis of compound 12.1. Compound 12.1 was prepared from 11.8 and Int-1 following the procedure described in the synthesis of I-7. The product was purified by flash column chromatography on silica gel (CombiFlash®, 2.5% methanol in dichloromethane). MS (ES): m/z: 671.6 [M+H]⁺.

Synthesis of I-12. Compound I-12 was prepared from 12.1 following the procedure described in the synthesis of I-11. The product was purified by flash column chromatography on silica gel (CombiFlash®, 3.5% methanol in dichloromethane). MS (ES): m/z: 517.4 [M+H]⁺; ¹H NMR (DMSO-d₆, 400 MHz): δ 11.65 (s, 1H), 9.79 (s, 1H), Example 13: (S)—N-(5-(tert-butyl)-1-(tetrahydro-furan-3-yl)-1H-pyrazol-3-yl)-7-chloro-6-(imidazo[1,2-b]pyridazin-7-yloxy)-1-methyl-1H-imidazo[4,5-b]pyridin-2-amine

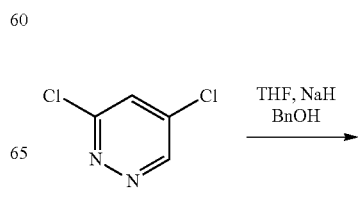

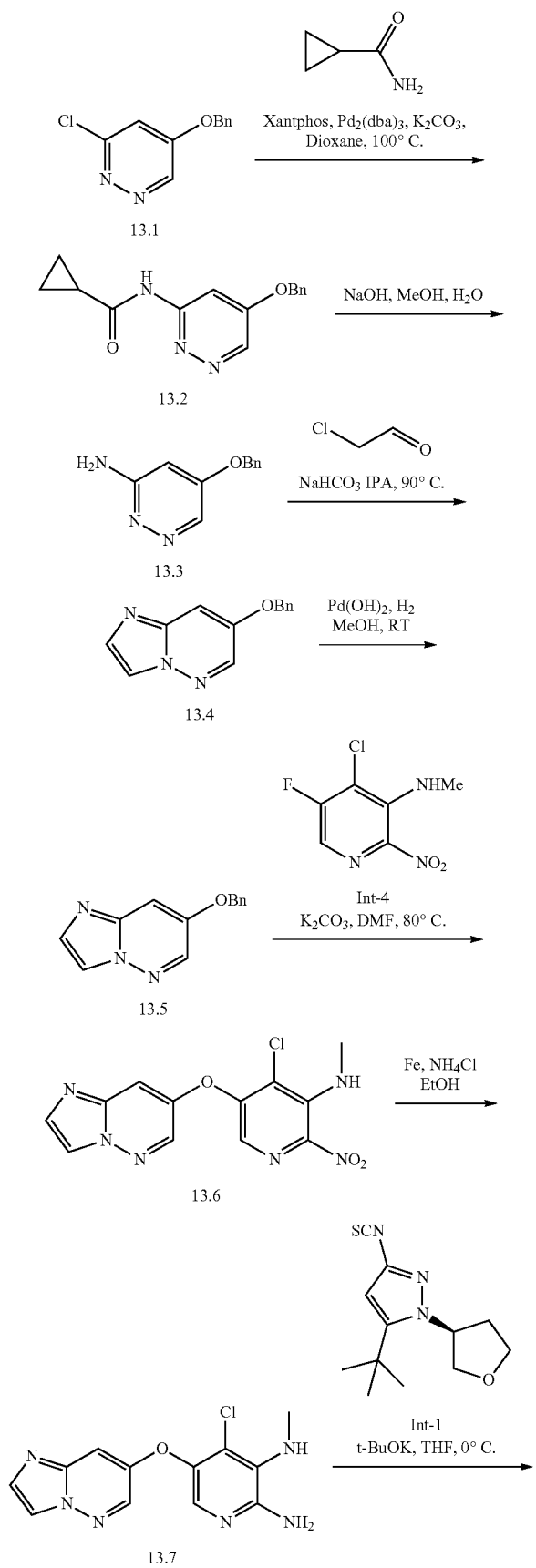
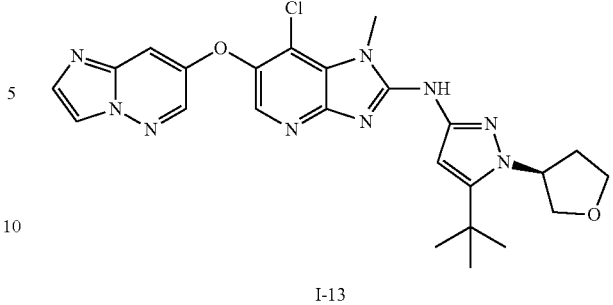

Synthesis of compound 13.1. To a suspension of sodium hydride (3.2 g, 80.55 mmol, 1.2 equiv) in dry THF (100 mL) was added benzyl alcohol (7.97 g, 73.84 mmol, 1.1 equiv) at 0° C. and stirred for 15 min. To the mixture was added 3,5-dichloropyridazine (10 g, 67.13 mmol, 1.0 equiv) in small portions and the reaction mixture was stirred at room temperature for 2 h. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford 13.1. MS (ES): m/z 221.2 [M+H]$^+$.

Synthesis of compound 13.2. A mixture of 13.1 (6.8 g, 30.82 mmol, 1.0 equiv), cyclopropanecarboxamide (7.87 g, 92.45 mmol, 3.0 equiv) and potassium carbonate (12.75 g, 92.45 mmol, 3.0 equiv) in 1,4-dioxane (70 mL) was degassed by bubbling through a stream of argon for 10 min. 4,5-Bis(diphenylphosphino)-9,9-dimethylxanthene (3.56 g, 6.16 mmol, 0.2 equiv) and tris(dibenzylideneacetone)dipalladium (2.82 g, 3.082 mmol, 0.1 equiv) was added, and degassed for 5 min. The reaction mixture was stirred at 100° C. under argon for 1 h. It was cooled to room temperature, poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in dichloromethane) to afford 13.2. MS (ES): m/z: 270.3 [M+H]$^+$.

Synthesis of compound 13.3. To a solution of 13.2 (5.7 g, 21.17 mmol, 1.0 equiv) in methanol (100 mL) was added water (50 mL) followed by sodium hydroxide (8.46 g, 211.7 mmol, 10 equiv). The reaction mixture was heated to reflux for 1 h. It was poured over ice-water and extracted with ethyl acetate. The combined organic layers were washed with brine, dried over anhydrous sodium sulfate, filtered and concentrated under reduced pressure to afford 13.3. MS (ES): m/z: 202.1 [M+H]$^+$.

Synthesis of compound 13.4. To a solution of 13.3 (3.6 g, 17.89 mmol, 1.0 equiv) in isopropyl alcohol (70 mL) was added chloroacetaldehyde (22.7 mL, 178.9 mmol, 10 equiv) followed by sodium bicarbonate (3.00 g, 35.78 mmol, 2.0 equiv). The reaction mixture was stirred at 90° C. for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 35% ethyl acetate in hexane) to afford 13.4. MS (ES): m/z: 226.2 [M+H]$^+$.

Synthesis of compound 13.5. A mixture of compound 13.4 (3.1 g, 13.76 mmol, 1.0 equiv) and palladium hydroxide (20 wt % on carbon, 1.5 g) in methanol (30 mL) was stirred under hydrogen (1 atm) for 1 h. It was filtered through a pad of Celite® and rinsed with methanol. The filtrate was concentrated under reduced pressure to afford 13.5. MS (ES): m/z 136.2 [M+H]$^+$.

Synthesis of compound 13.6. Compound 13.6 was prepared following the procedure described in the synthesis of 5.3. The product was purified by flash column chromatography on silica gel (CombiFlash®, 3.5% methanol in dichloromethane). MS (ES): m/z 321.5 [M+H]$^+$.

Synthesis of compound 13.7. Compound 13.7 was prepared from 13.6, following the procedure described in the synthesis of 5.4. The product was purified by flash column chromatography on silica gel (CombiFlash®, 4.4% methanol in dichloromethane). MS (ES): m/z 291.3 [M+H]$^+$.

Synthesis of I-13. To a solution of 13.7 (0.150 g, 0.515 mmol, 1.0 equiv) and Int-1 (0.155 g, 0.619 mmol, 1.2 equiv) in THF (4 mL) was added potassium tert-butoxide (1 M in THF, 1.54 mL, 1.545 mmol, 3.0 equiv) at 0° C. The reaction mixture was stirred at 0° C. for 30 min and allowed to warm to rt with stirring for 14 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.6% methanol in dichloromethane) to afford I-13. MS (ES): m/z: 508.6 [M+H]$^+$, $^1$H NMR (DMSO-d$_6$, 400 MHz): δ 10.04 (s, 1H), 8.72 (s, 1H), 8.22 (s, 1H), 8.15 (s, 1H), 7.65 (bs, 1H), 7.22 (s, 1H), 6.56 (bs, 1H), 5.26 (bs, 1H), 4.09 (bs, 2H), 3.93 (s, 3H), 3.86-3.83 (m, 2H), 2.36-2.34 (m, 1H), 2.24 (bs, 1H), 1.40 (s, 9H).

Example 14: (R)—N-(5-(tert-butyl)-1-(tetrahydrofuran-3-yl)-1H-pyrazol-3-yl)-7-chloro-6-(imidazo[1,2-b]pyridazin-7-yloxy)-1-methyl-1H-imidazo[4,5-b]pyridin-2-amine Synthesis of I-14. Compound I-14 was prepared from 13.7 and Int-2, following the procedure described in the synthesis of I-13. The product was purified by flash column chromatography on silica gel (CombiFlash®, 2.6% methanol in dichloromethane). MS (ES): m/z: 508.7 [M+H]$^+$, $^1$H NMR (DMSO-d$_6$, 400 MHz): δ 10.04 (s, 1H), 8.73-8.72 (d, J=2.8 Hz, 1H), 8.22 (s, 1H), 8.15 (s, 1H), 7.66-7.65 (d, J=1.2 Hz, 1H), 7.23-7.22 (d, J=2.4 Hz, 1H), 6.56 (bs, 1H), 5.28-5.24 (m, 1H), 4.11-4.06 (m, 2H), 3.93 (s, 3H), 3.86-3.82 (m, 2H), 2.40-2.35 (m, 1H), 2.26-2.20 (m, 1H), 1.40 (s, 9H).

Example 15: (R)-6-([1,2,4]triazolo[4,3-b]pyridazin-7-yloxy)-N-(5-(tert-butyl)-1-(tetrahydrofuran-3-yl)-1H-pyrazol-3-yl)-7-chloro-1-methyl-1H-imidazo[4,5-b]pyridin-2-amine

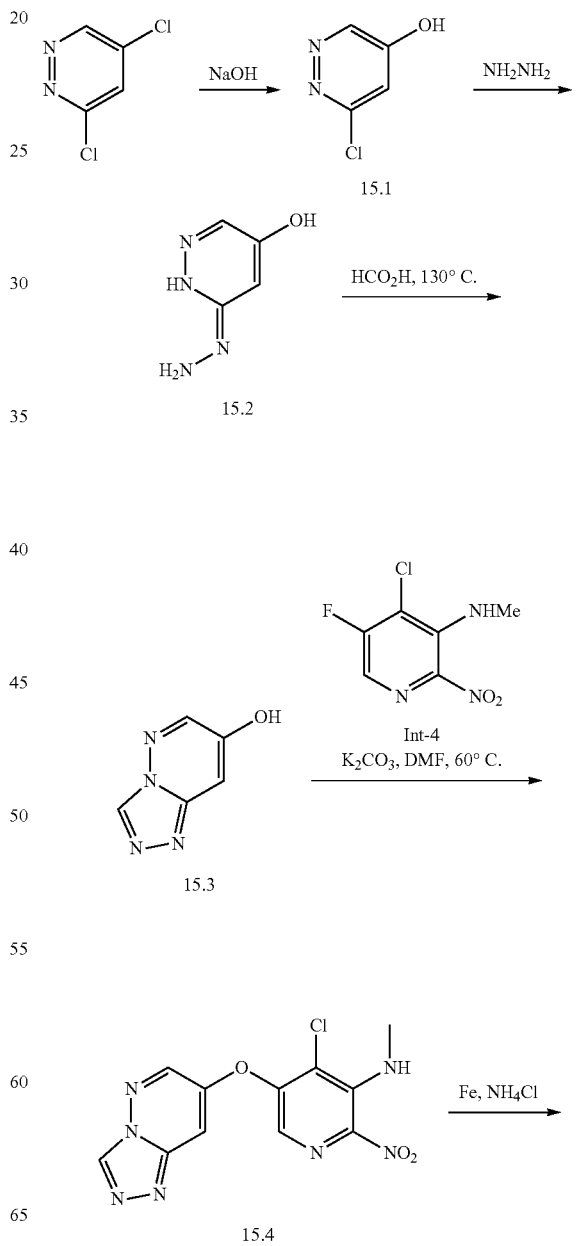

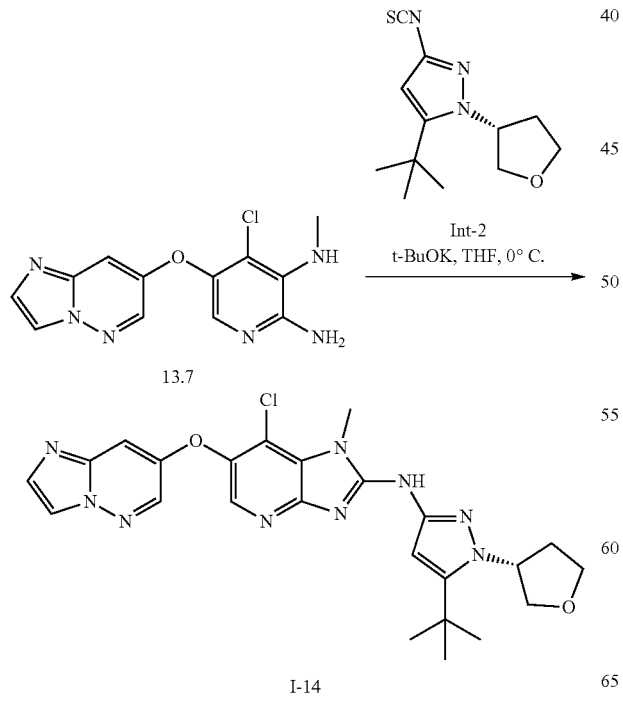

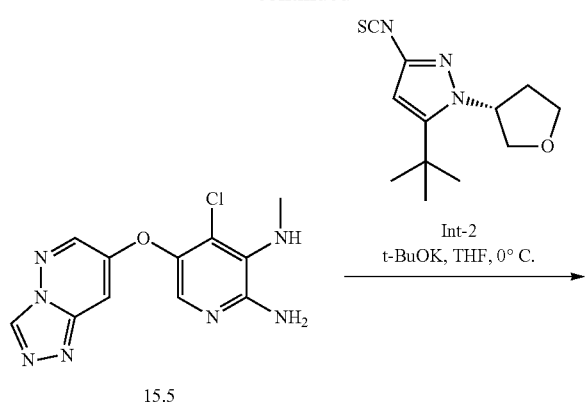

synthesis of 5.4. The product was purified by flash column chromatography on silica gel (CombiFlash®, 3.4% methanol in dichloromethane). MS (ES): m/z 292.3 [M+H]⁺.

Synthesis of I-15. Compound I-15 was prepared from 15.5 and Int-2, following the procedure described in the synthesis of I-13. The product was purified by flash column chromatography on silica gel (CombiFlash®, 3.0% methanol in dichloromethane). MS (ES): m/z: 509.7 [M+H]⁺, $^1$H NMR (DMSO-d$_6$, 400 MHz): δ 10.07 (s, 1H), 9.59-9.57 (d, J=8 Hz, 1H), 8.89-8.88 (d, J=2.4 Hz, 1H), 8.17 (s, 1H), 7.41-7.40 (d, d, J=2.4 Hz, 1H), 6.56 (s, 1H), 5.28-5.23 (m, 1H), 4.11-4.06 (m, 2H), 3.99 (s, 3H), 3.88-3.86 (m, 3H), 2.40-2.33 (m, 1H), 2.27-2.20 (m, 1H), 1.40 (s, 9H).

Example 16: (S)-6-([1,2,4]triazolo[4,3-b]pyridazin-7-yloxy)-N-(5-(tert-butyl)-1-(tetrahydrofuran-3-yl)-1H-pyrazol-3-yl)-7-chloro-1-methyl-1H-imidazo[4,5-b]pyridin-2-amine

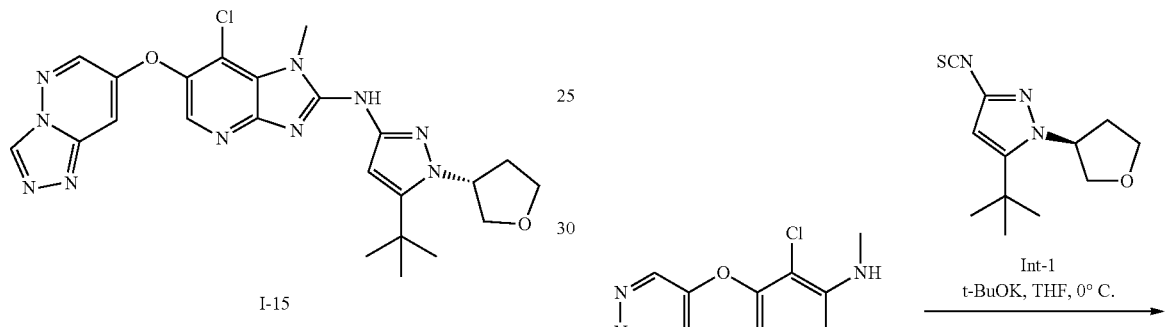

Synthesis of compound 15.1. To a solution of 3,5-dichloropyridazine (5.0 g, 33.56 mmol, 1.0 equiv) in 1,4-dioxane (20 mL) was added 2 N sodium hydroxide solution (50 mL, 10 v/w) and stirred at 100° C. for 4 h. It was transferred into ice-cold 1 N hydrochloric acid, stirred and extracted with ethyl acetate. The combined organic layers were washed with brine, dried over anhydrous sodium sulfate, filtered and concentrated under reduced pressure to afford 15.1. MS (ES): m/z 130.96 [M+H]⁺.

Synthesis of compound 15.2. To a solution of 15.1 (3.0 g, 22.98 mmol, 1.0 equiv) in 1,4-dioxane (30 mL) was added hydrazine hydrate (60 mL, 20 v/w) and stirred at 130° C. for 16 h. It was concentrated under reduced pressure to afford 15.2. MS (ES): m/z 127.2 [M+H]⁺.

Synthesis of compound 15.3. A solution of 15.2 (2.1 g, 16.65 mmol, 1.0 equiv) in formic acid (21 mL, 10 v/w) was stirred at 130° C. for 16 h. It was concentrated under reduced pressure. The residue was purified by preparative HPLC to afford 15.3. MS (ES): m/z 137.2 [M+H]⁺.

Synthesis of compound 15.4. To a solution of 15.3 (0.810 g, 5.95 mmol, 1.0 equiv) in DMF (8 mL) was added Int-4 (1.22 g, 5.95 mmol, 1.0 equiv) followed by potassium carbonate (2.463 g, 17.85 mmol, 3.0 equiv). The reaction mixture was stirred at 60° C. for 3 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in dichloromethane) to afford 15.4. MS (ES): m/z 322.2 [M+H]⁺.

Synthesis of compound 15.5. Compound 15.5 was prepared from 15.4, following the procedure described in the

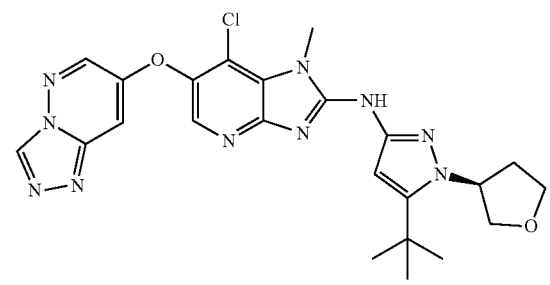

Synthesis of I-16. Compound I-16 was prepared from 15.5 and Int-1, following the procedure described in the synthesis of I-13. The product was purified by flash column chromatography on silica gel (CombiFlash®, 2.9% methanol in dichloromethane). MS (ES): m/z: 509.6 [M+H]⁺, $^1$H NMR (DMSO-d$_6$, 400 MHz): δ 10.06 (s, 1H), 9.60 (bs, 1H), 8.90-8.89 (d, J=2.4 Hz, 1H), 8.18 (s, 1H), 7.41-7.40 (d, d, J=2.4 Hz, 1H), 6.57 (s, 1H), 5.28 (bs, 1H), 4.12-4.09 (m, 2H), 3.99 (s, 3H), 3.89-3.84 (m, 2H), 2.37-2.34 (m, 1H), 2.27-2.24 (m, 1H), 1.40 (s, 9H).

Example 17: (S)-2-(3-((7-chloro-1-methyl-6-(pyrazolo[1,5-a]pyrimidin-6-yloxy)-1H-imidazo[4,5-b]pyridin-2-yl)amino)-1-(tetrahydrofuran-3-yl)-1H-pyrazol-5-yl)-2-methylpropanenitrile

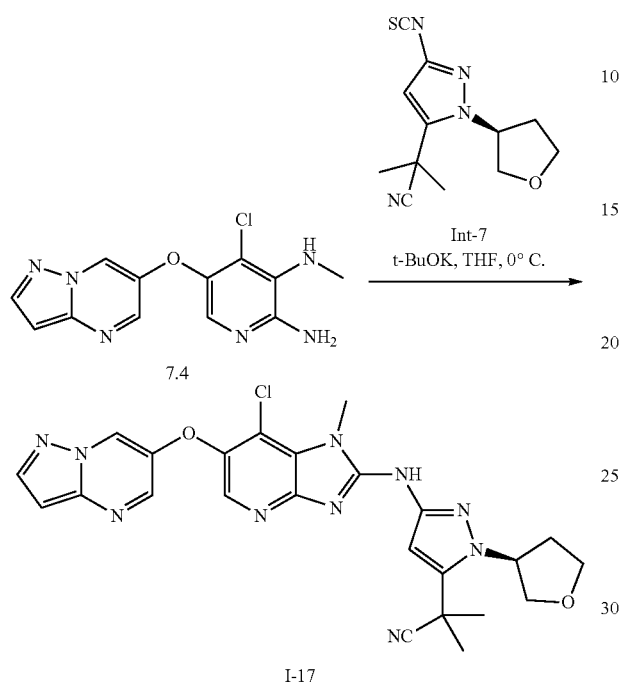

I-17

Synthesis I-17. Compound I-17 was prepared from 7.4 and Int-7, following the procedure described in the synthesis of I-13. The product was purified by flash column chromatography on silica gel (CombiFlash®, 2.9% methanol in dichloromethane). MS (ES): m/z: 519.39 [M+H]$^+$, $^1$H NMR (DMSO-d$_6$, 400 MHz): δ 10.27 (s, 1H), 8.90-8.89 (d, J=2.4 Hz, 1H), 8.71-8.70 (d, J=2.8 Hz, 1H), 8.19-8.17 (m, 2H), 6.80 (bs, 2H), 5.34-5.31 (m, 1H), 4.19-4.09 (m, 2H), 3.97 (s, 3H), 3.89-3.85 (m, 2H), 2.34 (bs, 1H), 2.30-2.22 (m, 1H), 1.82 (s, 6H).

Example 18: (R)-2-(3-((7-chloro-1-methyl-6-(pyrazolo[1,5-a]pyrimidin-6-yloxy)-1H-imidazo[4,5-b]pyridin-2-yl)amino)-1-(tetrahydrofuran-3-yl)-1H-pyrazol-5-yl)-2-methylpropanenitrile

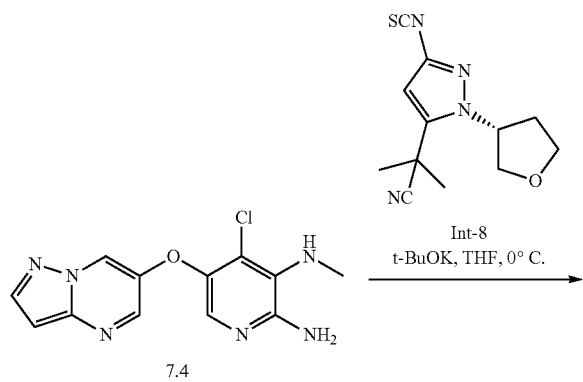

-continued

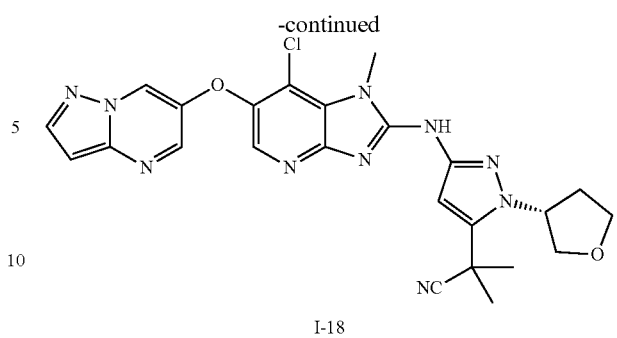

I-18

Synthesis of I-18. Compound I-18 was prepared from 7.4 and Int-8, following the procedure described in the synthesis of I-13. The product was purified by flash column chromatography on silica gel (CombiFlash®, 3.0% methanol in dichloromethane. MS (ES): m/z: 519.75 [M+H]$^+$, $^1$H NMR (DMSO-d$_6$, 400 MHz): δ 10.26 (s, 1H), 8.89-8.88 (d, J=2.4 Hz, 1H), 8.69-8.68 (d, J=2.8 Hz, 1H), 8.16-8.16 (m, 2H), 6.79 (bs, 2H), 5.29 (bs, 1H), 4.18-4.08 (m, 2H), 3.96 (s, 3H), 3.87-3.84 (m, 2H), 2.33 (bs, 1H), 2.27-2.23 (m, 1H), 1.82 (s, 6H).

Example 19: (S)—N-(5-(tert-butyl)-1-(1-methylpyrrolidin-3-yl)-1H-pyrazol-3-yl)-7-chloro-1-methyl-6-(thieno[2,3-b]pyridin-5-yloxy)-1H-imidazo[4,5-b]pyridin-2-amine

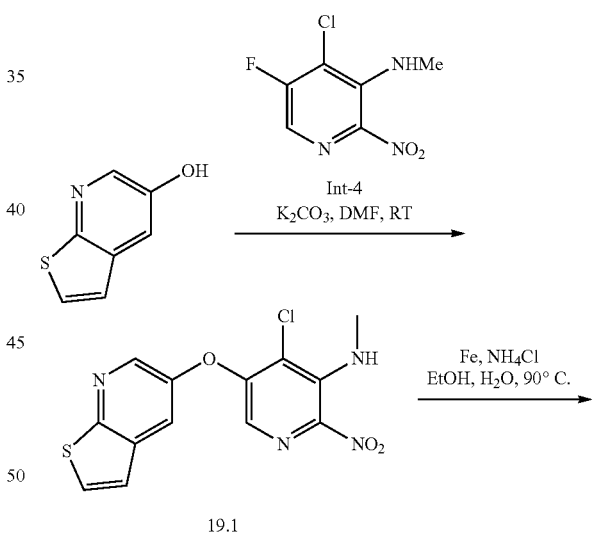

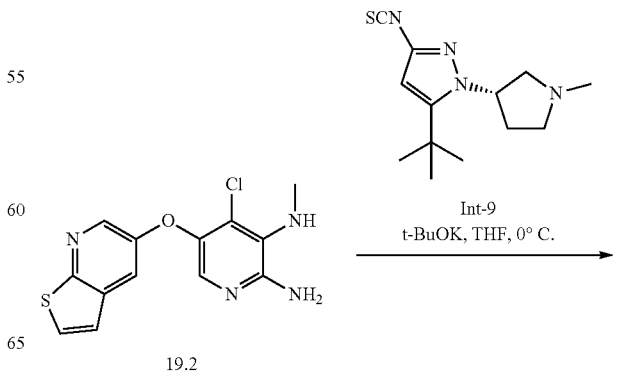

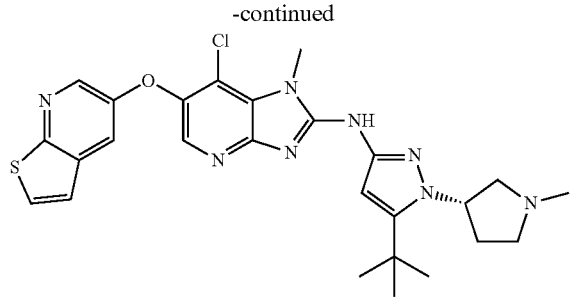

I-19

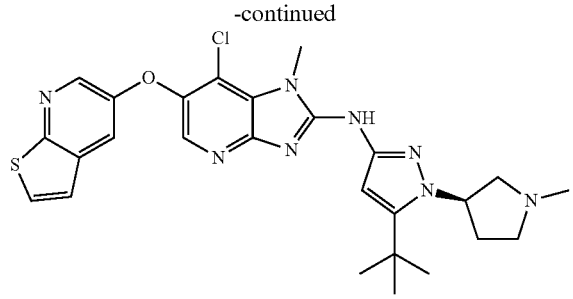

I-20

Synthesis of compound 19.1. To a solution of thieno[2,3-b]pyridin-5-ol (1.0 g, 6.61 mmol, 1.0 equiv) in DMF (10 mL) was added Int-4 (1.36 g, 6.61 mmol, 1.0 equiv), followed by potassium carbonate (2.28 g, 16.52 mmol, 2.5 equiv). The reaction mixture was stirred at room temperature for 1 h. It was poured over ice-water, and the precipitated product was filtered and dried to obtain 19.1. MS (ES): m/z 337.5 [M+H]+.

Synthesis of compound 19.2. Compound 19.2 was prepared from 19.1, following the procedure described in the synthesis of 5.4. The product was purified by flash column chromatography on silica gel (CombiFlash®, 3.5% methanol in dichloromethane). MS (ES): m/z 307.6 [M+H]+.

Synthesis of I-19. Compound I-19 was prepared from 19.2 and Int-9, following the procedure described in the synthesis of I-13. The product was purified by flash column chromatography on silica gel (CombiFlash®, 11% methanol in dichloromethane). MS (ES): m/z: 537.7 [M+H]+, $^1$H NMR (DMSO-d$_6$, 400 MHz): δ 10.02 (s, 1H), 8.52-8.51 (d, J=2.8 Hz, 1H), 8.10 (s, 1H), 7.92-7.90 (d, J=6.0 Hz, 1H), 7.68-7.67 (d, J=2.8 Hz, 1H), 7.34-7.32 (d, J=6.0 Hz, 1H), 6.51 (s, 1H), 5.08 (bs, 1H), 3.94 (s, 3H), 3.01-2.97 (m, 1H), 2.72-2.62 (m, 3H), 2.33 (bs, 1H), 2.30 (s, 3H), 2.18-2.17 (m, 1H), 1.39 (s, 9H).

Example 20: (R)—N-(5-(tert-butyl)-1-(1-methylpyrrolidin-3-yl)-1H-pyrazol-3-yl)-7-chloro-1-methyl-6-(thieno[2,3-b]pyridin-5-yloxy)-1H-imidazo[4,5-b]pyridin-2-amine Synthesis of I-20. Compound I-20 was prepared from 19.2 and Int-10, following the procedure described in the synthesis of I-13. The product was purified by flash column chromatography on silica gel (CombiFlash®, 11% methanol in dichloromethane). MS (ES): m/z: 537.7 [M+H]+, $^1$H NMR (DMSO-d$_6$, 400 MHz): δ 10.02 (s, 1H), 8.52-8.51 (d, J=2.8 Hz, 1H), 8.10 (s, 1H), 7.92-7.90 (d, J=6.0 Hz, 1H), 7.68-7.67 (d, J=2.8 Hz, 1H), 7.34-7.32 (d, J=6.0 Hz, 1H), 6.51 (s, 1H), 5.08-5.06 (m, 1H), 3.94 (s, 3H), 3.01-2.97 (m, 1H), 2.73-2.62 (m, 3H), 2.33 (bs, 1H), 2.30 (s, 3H), 2.18-2.17 (m, 1H), 1.39 (s, 9H).

Example 21: (R)—N-(5-(tert-butyl)-1-(tetrahydrofuran-3-yl)-1H-pyrazol-3-yl)-7-chloro-1-methyl-6-(pyrazolo[1,5-a]pyrazin-3-yloxy)-1H-imidazo[4,5-b]pyridin-2-amine

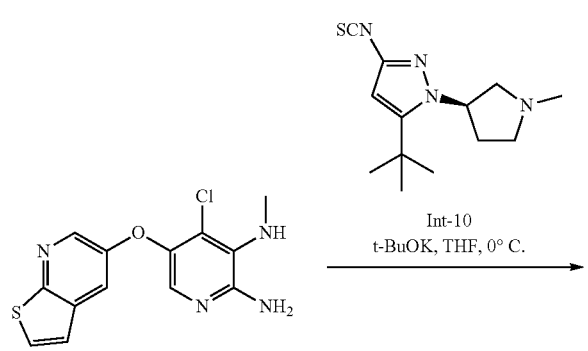

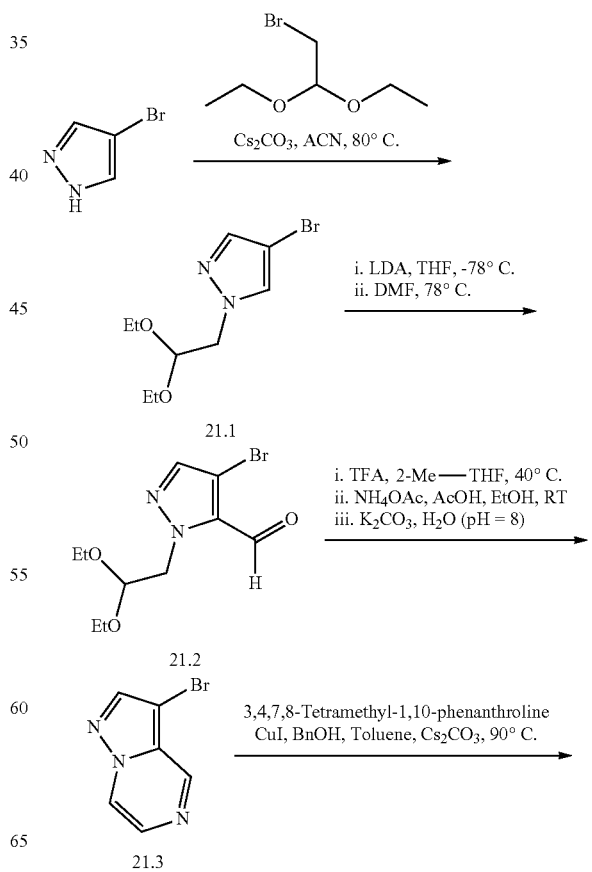

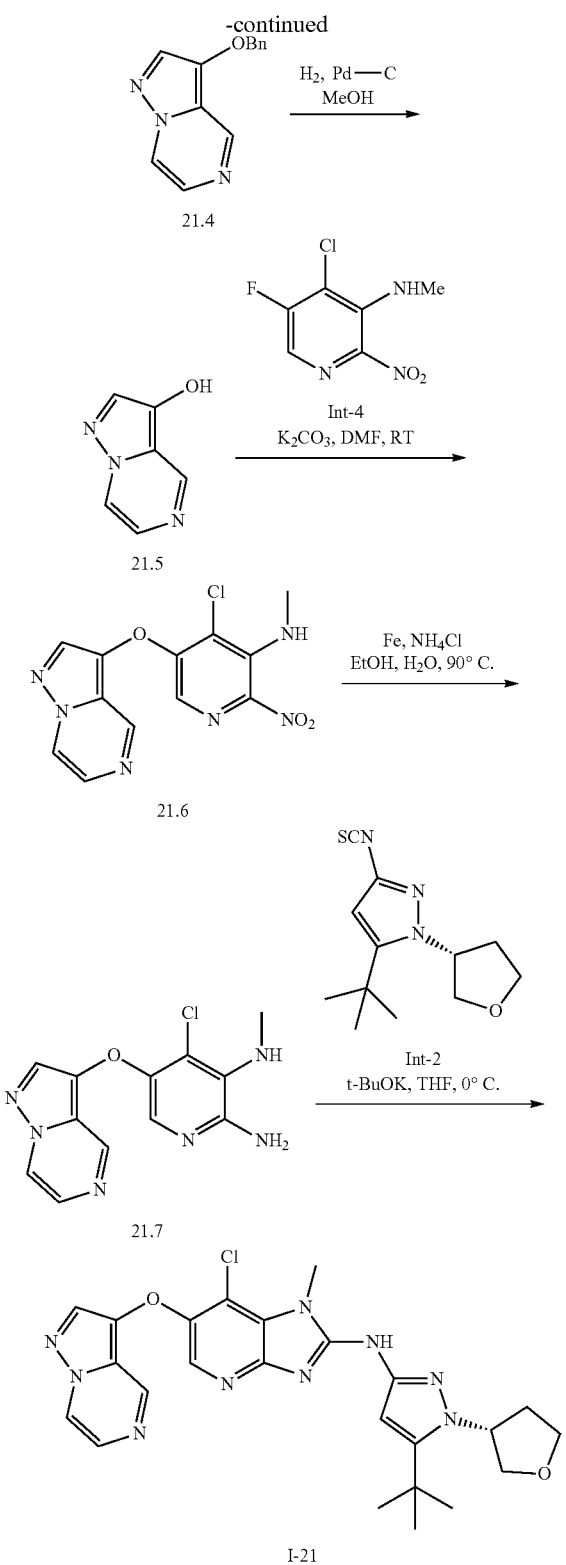

extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford 21.1. MS (ES): m/z 263.3 [M+H]+.

Synthesis of compound 21.2. To a solution of diisopropylamine (30.7 mL, 212.8 mmol, 1.6 equiv) in THF (200 mL) was added n-butyllithium (2.5 M in hexane, 85 mL, 212.8 mmol, 1.6 equiv) at −78° C. and stirred for 30 min. To the mixture was added a solution of 21.1 (35 g, 133 mmol, 1.0 equiv) in THF (70 mL), followed by addition of DMF (18 mL, 239.4, 1.8 equiv), and the reaction mixture was stirred for 1 h. It was quenched by addition of a saturated ammonium chloride solution and extracted with ethyl acetate. The organic layer was dried over anhydrous sodium sulfate, filtered and concentrated under reduced pressure. The residue was purified by flash column chromatography on silica gel (CombiFlash®, 4% ethyl acetate in hexane) to afford 21.2. $^1$H NMR (CDCl$_3$, 400 MHz): δ 9.91 (s, 1H), 7.57 (s, 1H), 4.84-4.81 (m, 1H), 4.67-4.66 (d, 2H), 3.75-3.68 (m, 2H), 3.53-3.45 (m, 2H), 1.16-1.13 (t, 6H).

Synthesis of compound 21.3. To a solution of 21.2 (22 g, 75.56 mmol, 1.0 equiv) in 2-methyl-THF (44 mL) was added trifluoroacetic acid (88 mL) and water (44 mL). The mixture was stirred at 40° C. for 3 h. It was cooled to room temperature and most solvent was removed under reduced pressure. The residue was dissolved in ethanol (120 mL), and acetic acid (12.9 mL, 226.68 mmol, 3.0 equiv) and ammonium acetate (17.45, 226.68 mmol, 3.0 equiv) were added. The reaction mixture was stirred at room temperature for 1 h. It was concentrated under reduced pressure. The residue was dissolved in 2-methyl-THF (400 mL) and water (400 mL). To it was added potassium carbonate in small portions to adjust pH=8. The mixture was extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 21.3. MS (ES): m/z 199.8 [M+H]+.

Synthesis of compound 21.4. A mixture of 21.3 (12 g, 60.6 mmol, 1.0 equiv) and benzyl alcohol (13 g, 121.2 mmol, 2.0 equiv) in toluene (120 mL) was degassed by bubbling through a stream of argon for 10 min. To the mixture was added cesium carbonate (59.08 g, 181.8 mmol, 3.0 equiv), 3,4,7,8-tetramethyl-1,10-phenanthroline (4.29 g, 18.18 mmol, 0.3 equiv) and copper iodide (1.72 g, 9.09 mmol, 0.15 equiv). It was degassed for 5 min and stirred at 90° C. under argon for 16 h. It was cooled to room temperature and filtered through a pad of Celite®. The filtrate was poured into water, extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford 21.4. MS (ES): m/z 226.3 [M+H]+.

Synthesis of compound 21.5. A mixture of compound 21.4 (1.3 g, 5.77 mmol, 1.0 equiv) and palladium on carbon (10 wt %, 0.650 g) in methanol (15 mL) was stirred under hydrogen for 1 h. It was filtered through a pad of Celite® and rinsed with methanol. The filtrate was concentrated under reduced pressure to afford 21.5. MS (ES): m/z 136.2 [M+H]+.

Synthesis of compound 21.6. To a solution of 21.5 (0.450 g, 3.33 mmol, 1.0 equiv) in DMF (10 mL) was added Int-4

Synthesis of compound 21.1. A mixture of 4-bromo-1H-pyrazole (30 g, 204.12 mmol, 1.0 equiv), cesium carbonate (99.5 g, 306.18 mmol, 1.5 equiv) and 2-bromo-1,1-diethoxyethane (44.23 g, 224.5 mmol, 1.1 equiv) in acetonitrile (200 mL) was stirred at 80° C. for 16 h. It was cooled to room temperature, and most solvent was removed under reduced pressure. The residue was added to water and (0.684 g, 3.33 mmol, 1.0 equiv), followed by potassium carbonate (0.919 g, 6.66 mmol, 2.0 equiv). The reaction mixture was stirred at room temperature for 30 min. It was cooled to room temperature, filtered through a pad of Celite, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 25% ethyl acetate in hexane to afford 21.6. MS (ES): m/z 321.2 [M+H]$^+$.

Synthesis of compound 21.7. Compound 21.7 was prepared from 21.6, following the procedure described in the synthesis of 5.4. The product was purified by flash column chromatography on silica gel (CombiFlash®, 3.2% methanol in dichloromethane). MS (ES): m/z 291.3 [M+H]$^+$.

Synthesis of I-21. Compound I-21 was prepared from 21.7 and Int-2, following the procedure described in the synthesis of I-13. The product was purified by flash column chromatography on silica gel (CombiFlash®, 3.5% methanol in dichloromethane). MS (ES): m/z: 508.3 [M+H]$^+$, $^1$H NMR (DMSO-d$_6$, 400 MHz): δ 10.02 (s, 1H), 9.02-9.01 (d, J=1.2 Hz, 1H), 8.69-8.67 (m, 1H), 8.12 (s, 1H), 8.02 (s, 1H), 7.87-7.86 (d, J=5.2 Hz, 1H), 6.55 (s, 1H), 5.28-5.24 (m, 1H), 4.11-4.07 (m, 2H), 3.96 (s, 3H), 3.86-3.83 (m, 2H), 2.41-2.34 (m, 1H), 2.28-2.22 (m, 1H), 1.40 (s, 9H).

Example 22: (S)—N-(5-(tert-butyl)-1-(tetrahydrofuran-3-yl)-1H-pyrazol-3-yl)-7-chloro-1-methyl-6-(pyrazolo[1,5-a]pyrazin-3-yloxy)-1H-imidazo[4,5-b]pyridin-2-amine

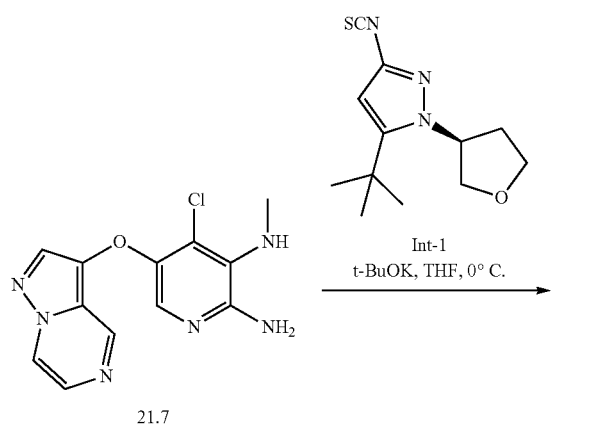

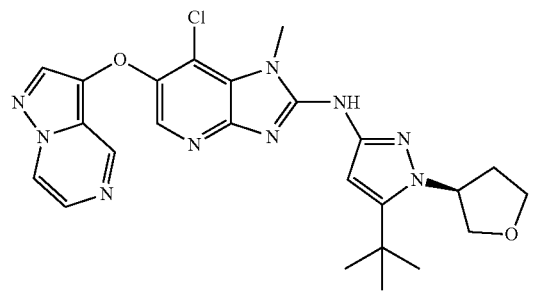

I-22

Synthesis of I-22. Compound I-22 was prepared from 21.7 and Int-1, following the procedure described in the synthesis of I-13. The product was purified by flash column chromatography on silica gel (CombiFlash®, 3.5% methanol in dichloromethane). MS (ES): m/z: 508.3 [M+H]$^+$, $^1$H NMR (DMSO-d$_6$, 400 MHz): δ 9.99 (s, 1H), 9.01 (s, 1H), 8.68-8.67 (d, J=3.6 Hz, 1H), 8.11 (s, 1H), 8.01 (s, 1H), 7.86-7.85 (d, J=5.2 Hz, 1H), 6.53 (s, 1H), 5.25 (bs, 1H), 4.10-4.06 (m, 2H), 3.94 (s, 3H), 3.85-3.81 (m, 2H), 2.39-2.31 (m, 1H), 2.26-2.19 (m, 1H), 1.39 (s, 9H).

Example 23: (3R,4S)-4-(5-(tert-butyl)-3-((7-chloro-6-(imidazo[1,2-b]pyridazin-7-yloxy)-1-methyl-1H-imidazo[4,5-b]pyridin-2-yl)amino)-1H-pyrazol-1-yl)tetrahydrofuran-3-ol and (3S,4R)-4-(5-(tert-butyl)-3-((7-chloro-6-(imidazo[1,2-b]pyridazin-7-yloxy)-1-methyl-1H-imidazo[4,5-b]pyridin-2-yl)amino)-1H-pyrazol-1-yl)tetrahydrofuran-3-ol

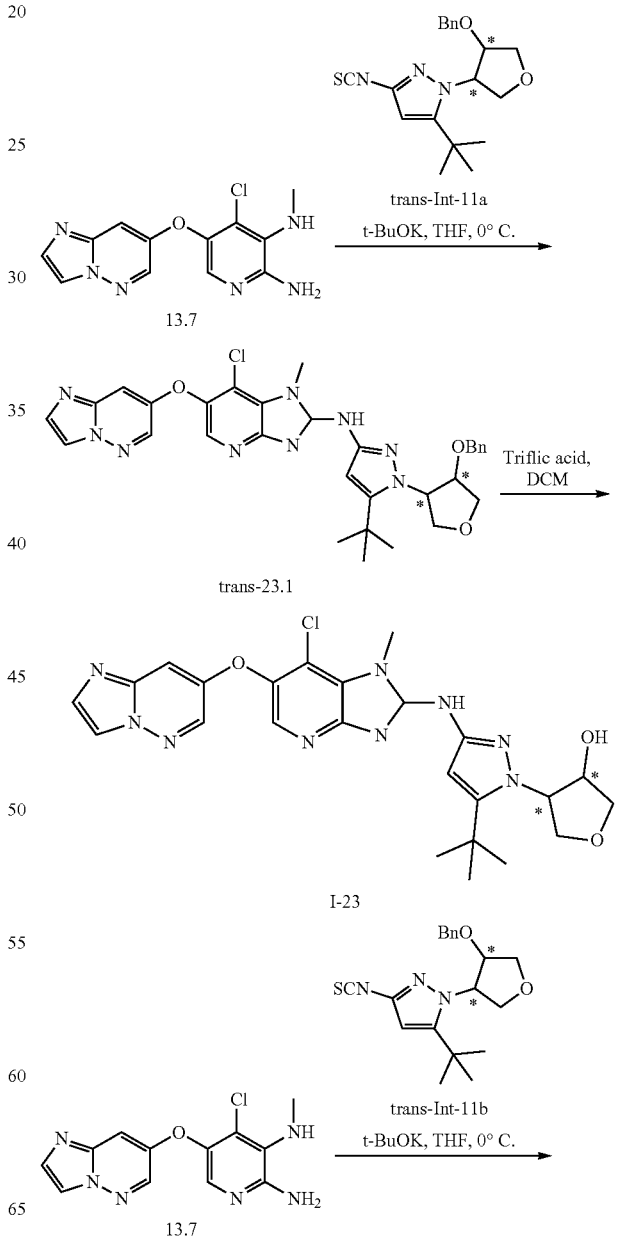

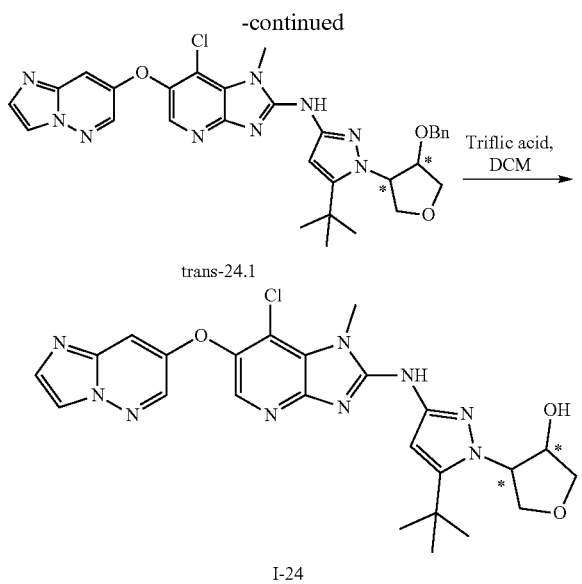

Synthesis of compound trans-23.1. Compound trans-23.1 was prepared from 13.7 and trans-Int-11a, following the procedure described in the synthesis of I-13. The product was purified by flash column chromatography on silica gel (CombiFlash®, 3% methanol in dichloromethane). MS (ES): m/z: 614.5 [M+H]$^+$.

Synthesis of I-23. To a solution of trans-23.1 (0.045 g, 0.073 mmol, 1.0 equiv) in dichloromethane (2 mL) was added triflic acid (0.1 mL) at 0° C. and stirred for 5 min. It was transferred into ice-cold saturated sodium bicarbonate solution and extracted with dichloromethane. The combined organic layers were washed with brine, dried over anhydrous sodium sulfate, filtered and concentrated under reduced pressure. The residue was purified by flash column chromatography on silica gel (CombiFlash®, 6.0% methanol in dichloromethane) to afford I-23. MS (ES): m/z: 524.8 [M+H]$^+$, $^1$H NMR (DMSO-d$_6$, 400 MHz): δ 10.06 (s, 1H), 8.74-8.73 (d, J=2.8 Hz, 1H), 8.23 (s, 1H), 8.17 (s, 1H), 7.66 (s, 1H), 7.24-7.23 (d, J=3.2 Hz, 1H), 6.56 (s, 1H), 5.56-5.55 (m, 1H), 4.93-4.91 (m, 1H), 4.57 (bs, 1H), 4.31-4.27 (m, 1H), 4.16-4.12 (m, 1H), 3.95 (s, 3H), 3.84-3.80 (m, 1H), 3.71-3.68 (m, 1H), 1.43 (s, 9H). (*Absolute stereochemistry not determined.)

Synthesis of compound trans-24.1. Compound trans-24.1 was prepared from 13.7 and trans-Int-11b, following the procedure described in the synthesis of I-13. The product was purified by flash column chromatography on silica gel (CombiFlash®, 3% methanol in dichloromethane) to afford trans-24.1. MS (ES): m/z: 614.5 [M+H]$^+$.

Synthesis of I-24. Compound I-24 was prepared from trans-24.1, following the procedure described in the synthesis of I-23. The product was purified by flash column chromatography on silica gel (CombiFlash®, 6.0% methanol in dichloromethane). MS (ES): m/z: 524.8 [M+H]$^+$, $^1$H NMR (DMSO-d$_6$, 400 MHz): δ 10.06 (s, 1H), 8.74-8.73 (d, J=2.8 Hz, 1H), 8.23 (s, 1H), 8.17 (s, 1H), 7.66 (s, 1H), 7.24-7.23 (d, J=3.2 Hz, 1H), 6.60 (s, 1H), 5.56-5.55 (m, 1H), 4.93-4.91 (m, 1H), 4.58-4.56 (m, 1H), 4.31-4.27 (m, 1H), 4.16-4.12 (m, 1H), 3.95 (s, 3H), 3.84-3.80 (m, 1H), 3.71-3.68 (m, 1H), 1.43 (s, 9H). (*Absolute stereochemistry not determined.)

Example 25: (S)—N-(5-(tert-butyl)-1-(1-(2-fluoroethyl)pyrrolidin-3-yl)-1H-pyrazol-3-yl)-7-chloro-6-(imidazo[1,2-b]pyridazin-7-yloxy)-1-methyl-1H-imidazo[4,5-b]pyridin-2-amine

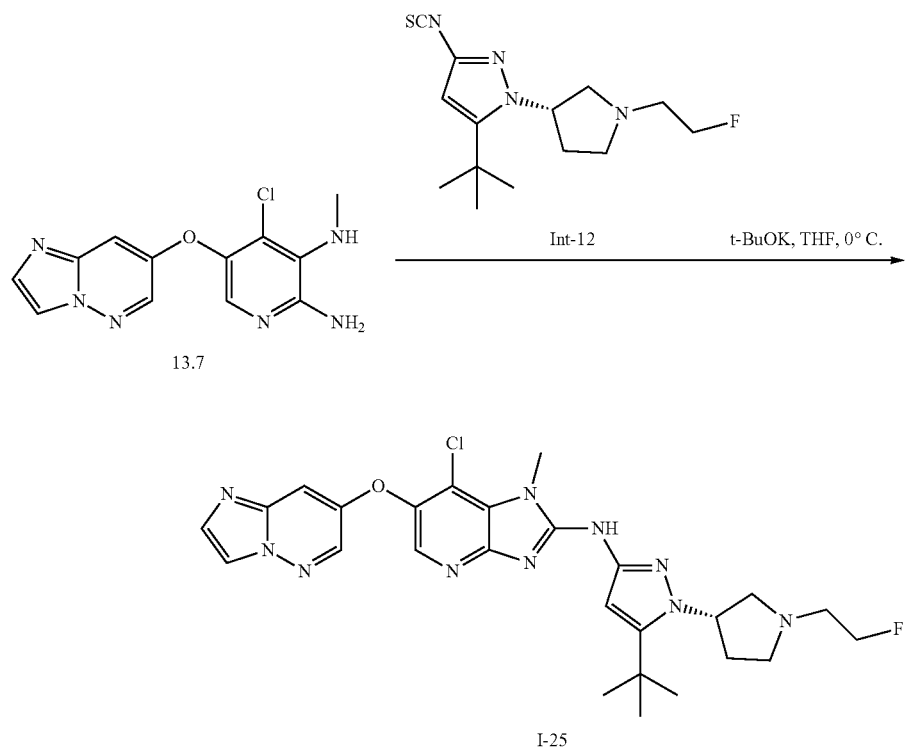

Synthesis of I-25. Compound I-25 was prepared from 13.7 and Int-12, following the procedure described in the synthesis of I-13. The product was purified by flash column chromatography on silica gel (CombiFlash®, 6.5% methanol in dichloromethane). MS (ES): m/z: 554.8 [M+H]⁺, ¹H NMR (DMSO-d$_6$, 400 MHz): δ 10.05 (s, 1H), 8.73-8.72 (d, J=2.4 Hz, 1H), 8.22 (s, 1H), 8.15 (s, 1H), 7.65 (s, 1H), 7.23-7.22 (d, J=2.4 Hz, 1H), 6.53 (s, 1H), 5.10 (s, 1H), 4.61 (bs, 1H), 4.49 (bs, 1H), 3.90 (s, 3H), 3.13 (bs, 1H), 2.83-2.77 (m, 4H), 2.33-2.27 (m, 2H), 2.22-2.19 (m, 1H), 1.40 (s, 9H).

Example 26: (R)—N-(5-(tert-butyl)-1-(1-(2-fluoroethyl)pyrrolidin-3-yl)-1H-pyrazol-3-yl)-7-chloro-6-(imidazo[1,2-b]pyridazin-7-yloxy)-1-methyl-1H-imidazo[4,5-b]pyridin-2-amine Example 27: (R)—N-(5-(tert-butyl)-1-(1-methylpyrrolidin-3-yl)-1H-pyrazol-3-yl)-7-chloro-1-methyl-6-(thiazolo[5,4-b]pyridin-6-yloxy)-1H-imidazo[4,5-b]pyridin-2-amine

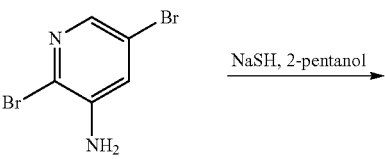

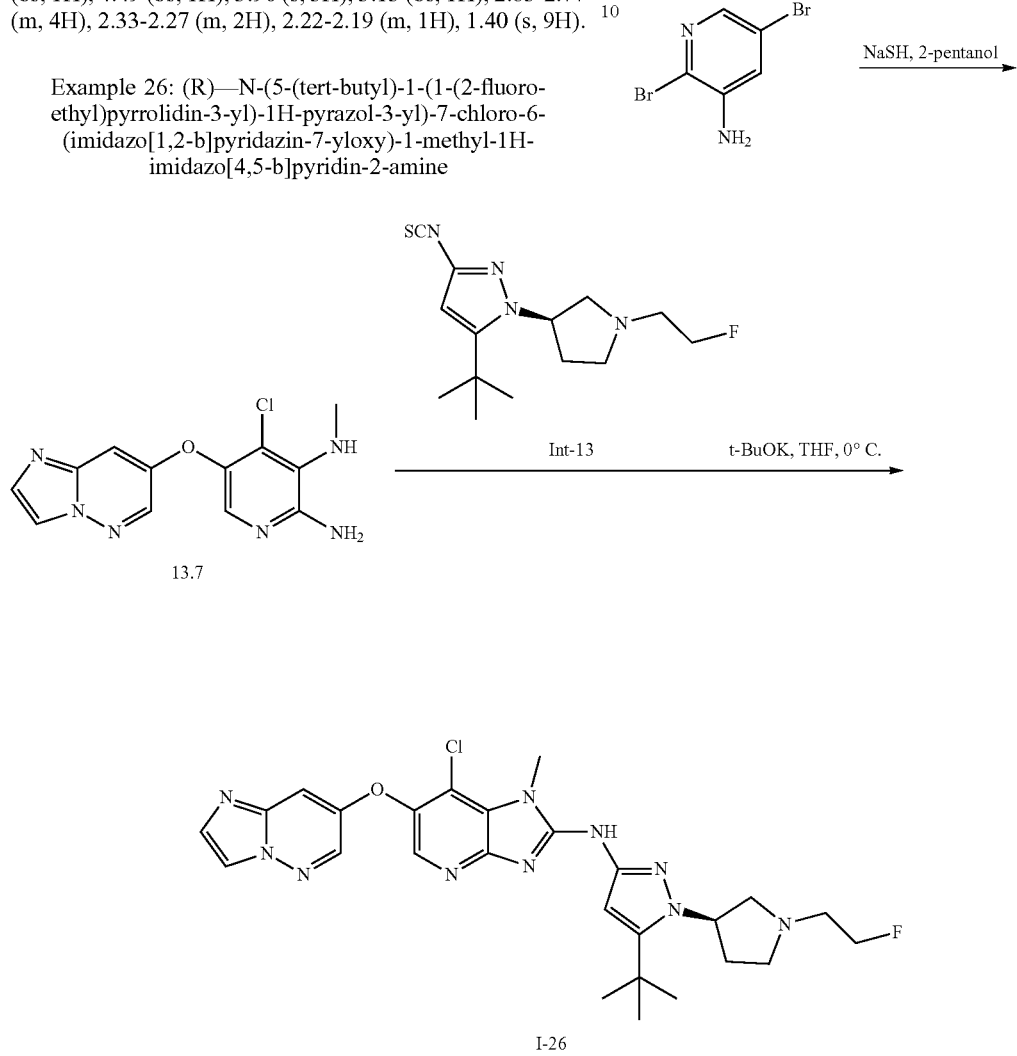

Synthesis of I-26. Compound I-26 was prepared from 13.7 and Int-13, following the procedure described in the synthesis of I-13. The product was purified by flash column chromatography on silica gel (CombiFlash®, 6.4% methanol in dichloromethane). MS (ES): m/z: 553.04 [M+H]⁺, ¹H NMR (DMSO-d$_6$, 400 MHz): δ 10.05 (s, 1H), 8.73-8.72 (d, J=2.4 Hz, 1H), 8.22 (s, 1H), 8.15 (s, 1H), 7.65 (s, 1H), 7.23-7.22 (d, J=2.4 Hz, 1H), 6.53 (s, 1H), 5.10-08 (m, 1H), 4.61 (bs, 1H), 4.49 (bs, 1H), 3.90 (s, 3H), 3.13 (bs, 1H), 2.83-2.77 (m, 4H), 2.33-2.27 (m, 2H), 2.22-2.19 (m, 1H), 1.40 (s, 9H).

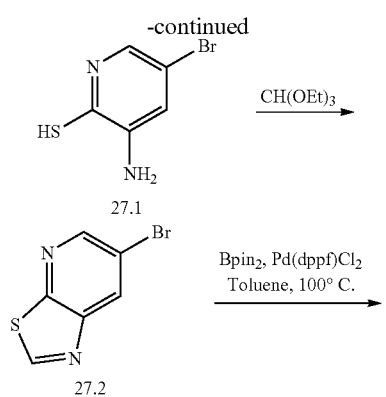

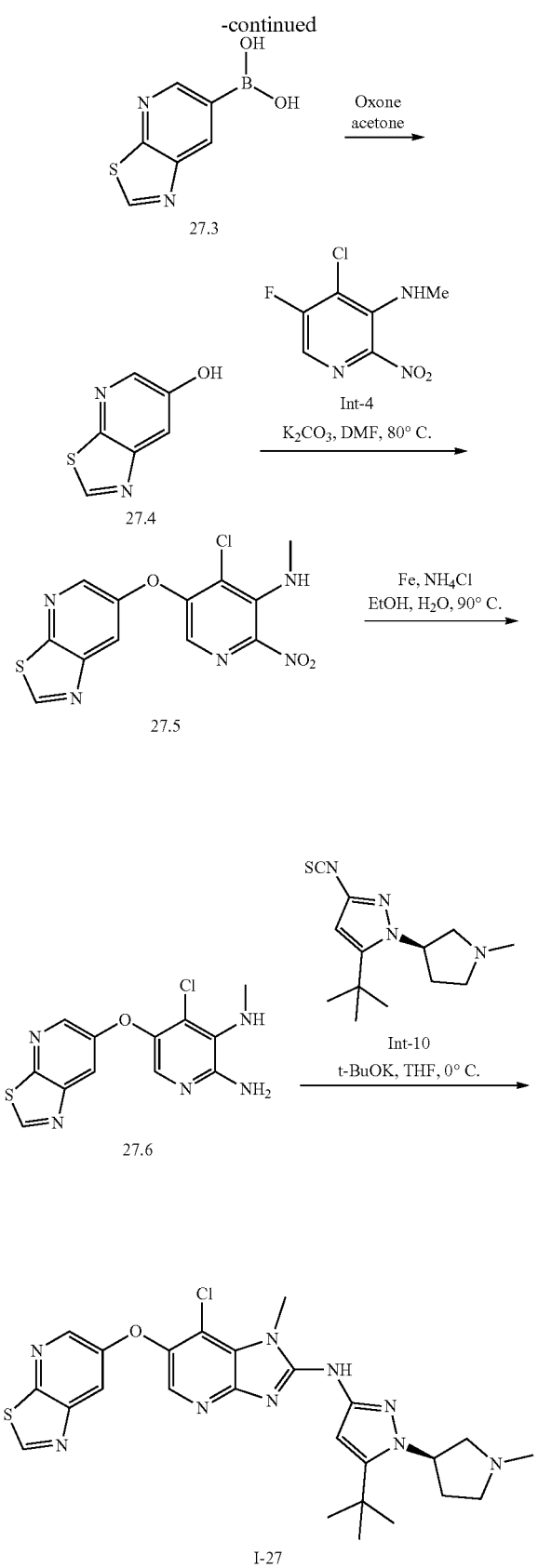

sodium hydrosulfide (13.35 g, 238.17 mmol, 3.0 equiv) in 2-pentanol (200 mL) was stirred at 120° C. for 16 h. It was cooled to room temperature, poured into water, stirred and extracted with ethyl acetate. The combined organic layers were washed with brine, dried over anhydrous sodium sulfate, filtered and concentrated under reduced pressure. The residue was triturated in hexane to afford 27.1. MS (ES): m/z 206.4[M+H]$^+$.

Synthesis of compound 27.2. A mixture of 27.1 (5.2 g, 25.36 mmol, 1.0 equiv) and triethyl orthoformate (50 mL) was stirred at 120° C. for 1 h. It was cooled to room temperature, poured into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 4-6% ethyl acetate in hexane) to afford 27.2. MS (ES): m/z 215.1[M+H]$^+$.

Synthesis of compound 27.3. A mixture of 27.2 (2.4 g, 11.16 mmol, 1.0 equiv), bis(pinacolato)diboron (3.68 g, 14.50 mmol, 1.3 equiv) and potassium acetate (2.18 g, 22.32 mmol, 2.0 equiv) in toluene (25 mL) was degassed by bubbling through a stream of argon for 10 min. To the mixture was added [1,1'-bis(diphenylphosphino)-ferrocene] palladium(II) dichloride (0.407 g, 0.558 mmol, 0.05 equiv), and it was heated at 100° C. under argon for 1.5 h. It was poured into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 30% ethyl acetate in hexane) to afford 27.3. MS (ES): m/z 181.1 [M+H]$^+$.

Synthesis of compound 27.4. To a solution of 27.3 (2.0 g, 11.11 mmol, 1.0 equiv) in acetone (20 mL) was added a solution of oxone (3.41 g, 11.11 mmol, 1.0 equiv) in water (10 mL). The reaction mixture was stirred at room temperature for 2 h. It was transferred into 1 N hydrochloric acid and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.1% methanol in dichloromethane) to afford 27.4. MS (ES): m/z 153.1 [M+H]$^+$.

Synthesis of compound 27.5. Compound 27.5 was prepared from 27.4 and Int-4 following the procedures described in the synthesis of 7.3. The residue was purified by flash column chromatography on silica gel (CombiFlash®, 2.4% methanol in dichloromethane). MS (ES): m/z 338.2 [M+H]$^+$.

Synthesis of compound 27.6. Compound 27.6 was prepared from 27.5, following the procedure described in the synthesis of 5.4. The product was purified by flash column chromatography on silica gel (CombiFlash®, 3.5% methanol in dichloromethane). MS (ES): m/z 308.3 [M+H]$^+$.

Synthesis of I-27. Compound I-27 was prepared from 27.6 and Int-10, following the procedure described in the synthesis of I-13. The product was purified by preparative HPLC. MS (ES): m/z: 538.4 [M+H]$^+$, $^1$H NMR (DMSO-d$_6$, 400 MHz): δ 10.02 (s, 1H), 9.58 (s, 1H), 8.64-8.63 (d, J=2.4 Hz, 1H), 8.15 (s, 1H), 7.89-7.88 (d, J=2.8 Hz, 1H), 6.52 (s, 1H), 5.12 (bs, 1H), 3.94 (s, 3H), 2.81-2.74 (m, 4H), 2.45 (s, 3H), 2.37-2.33 (m, 1H), 2.20-2.18 (m, 1H), 1.39 (s, 9H).

Synthesis of compound 27.1. A solution of 2,5-dibromopyridin-3-amine (20 g, 79.39 mmol, 1.0 equiv) and

Example 28: (S)—N-(5-(tert-butyl)-1-(1-methylpyrrolidin-3-yl)-1H-pyrazol-3-yl)-7-chloro-1-methyl-6-(thiazolo[5,4-b]pyridin-6-yloxy)-1H-imidazo[4,5-b]pyridin-2-amine

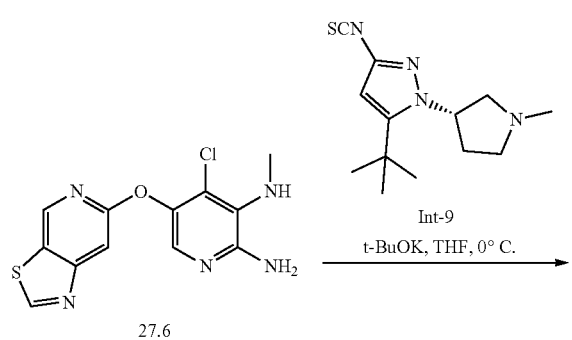

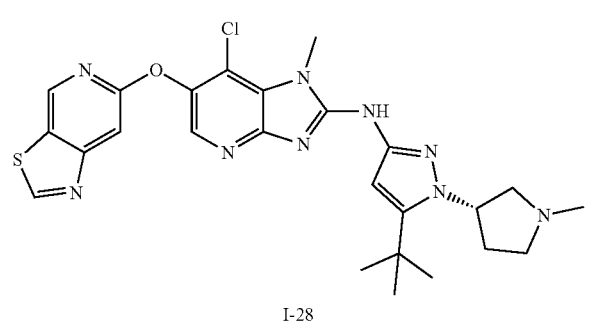

Synthesis of I-28. Compound I-28 was prepared from 27.6 and Int-9, following the procedure described in the synthesis of I-13. The product was purified by preparative HPLC. MS (ES): m/z: 538.4 [M+H]$^+$, $^1$H NMR (DMSO-d$_6$, 400 MHz): δ 10.02 (s, 1H), 9.58 (s, 1H), 8.64-8.63 (d, J=2.4 Hz, 1H), 8.15 (s, 1H), 7.89-7.88 (d, J=2.8 Hz, 1H), 6.52 (s, 1H), 5.12 (bs, 1H), 3.94 (s, 3H), 2.81-2.74 (m, 4H), 2.45 (s, 3H), 2.36-2.33 (m, 1H), 2.20-2.18 (m, 1H), 1.39 (s, 9H).

Example 29: (S)—N-(5-(tert-butyl)-1-(1-(2-fluoroethyl)pyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine

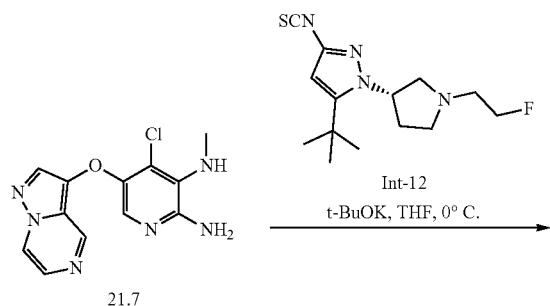

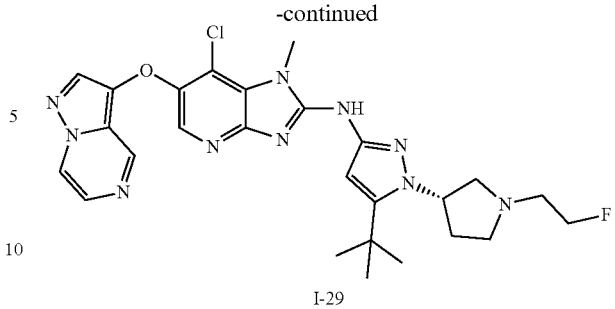

Synthesis of I-29. Compound I-29 was prepared from 21.7 and Int-12, following the procedure described in the synthesis of I-13. The product was purified by flash column chromatography on silica gel (CombiFlash®, 6.0% methanol in dichloromethane. MS (ES): m/z: 553.5 [M+H]$^+$, $^1$H NMR (DMSO-d$_6$, 400 MHz): δ 10.00 (s, 1H), 9.01-9.00 (d, J=1.2 Hz, 1H), 8.68-8.67 (m, 1H), 8.11 (s, 1H), 8.01 (s, 1H), 7.86-7.85 (d, J=4.8 Hz, 1H), 6.51 (s, 1H), 5.10-5.06 (m, 1H), 4.61-4.59 (t, 1H), 4.49-4.47 (t, 1H), 3.95 (s, 3H), 3.13-3.09 (m, 1H), 2.85-2.67 (m, 5H), 2.33-2.26 (m, 1H), 2.23-2.18 (m, 1H), 1.38 (s, 9H).

Example 30: (R)—N-(5-(tert-butyl)-1-(1-(2-fluoroethyl)pyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine

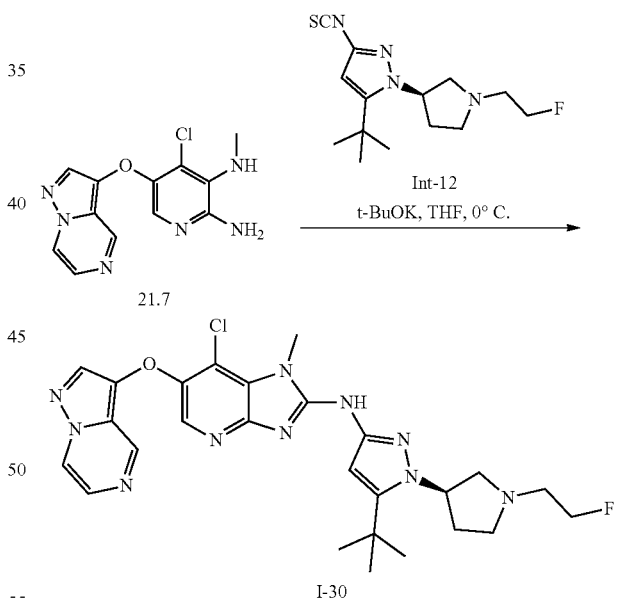

Synthesis of I-30. Compound I-29 was prepared from 21.7 and Int-13, following the procedure described in the synthesis of I-13. The product was purified by flash column chromatography on silica gel (CombiFlash®, 6.0% methanol in dichloromethane). MS (ES): m/z: 553.5 [M+H]$^+$, $^1$H NMR (DMSO-d$_6$, 400 MHz): δ 10.00 (s, 1H), 9.02-9.01 (d, J=1.2 Hz, 1H), 8.69-8.68 (m, 1H), 8.12 (s, 1H), 8.02 (s, 1H), 7.87-7.86 (d, J=4.8 Hz, 1H), 6.52 (s, 1H), 5.11-5.07 (m, 1H), 4.62-4.60 (t, 1H), 4.50-4.48 (t, 1H), 3.96 (s, 3H), 3.14-3.10 (m, 1H), 2.86-2.68 (m, 5H), 2.34-2.27 (m, 1H), 2.24-2.17 (m, 1H), 1.39 (s, 9H).

Example 31: (S)—N-(5-(tert-butyl)-1-(1-methylpyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine

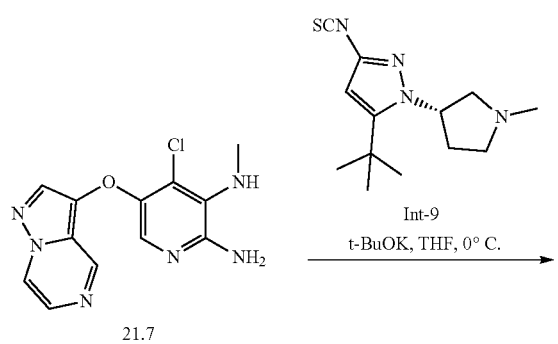

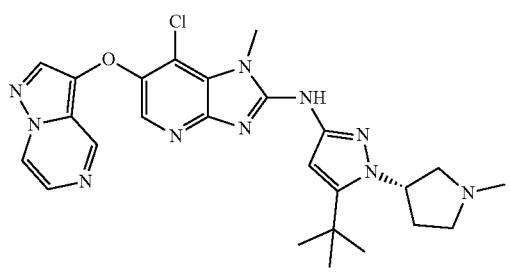

Synthesis of I-31. Compound I-31 was prepared from 21.7 and Int-9, following the procedure described in the synthesis of I-13. The product was purified by flash column chromatography on silica gel (CombiFlash®, 8.0% methanol in dichloromethane). MS (ES): m/z: 521.7 [M+H]+, 1H NMR (DMSO-d6, 400 MHz): δ 9.99 (s, 1H), 9.00 (s, 1H), 8.68-8.67 (d, J=4.0 Hz, 1H), 8.19 (s, 1H), 8.01 (s, 1H), 7.86-7.85 (d, J=4.8 Hz, 1H), 6.50 (s, 1H), 5.08 (bs, 1H), 3.94 (s, 3H), 2.75-2.63 (m, 4H), 2.30 (bs, 4H), 2.17-2.16 (m, 1H), 1.37 (s, 9H).

Example 32: (R)—N-(5-(tert-butyl)-1-(1-methylpyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine

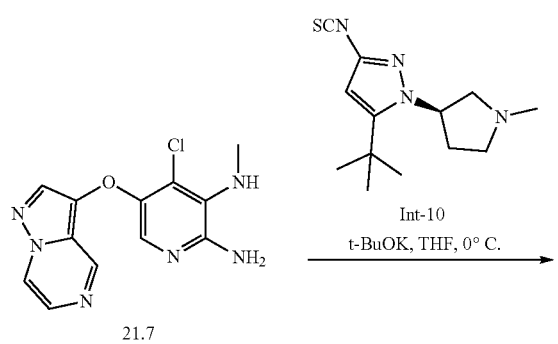

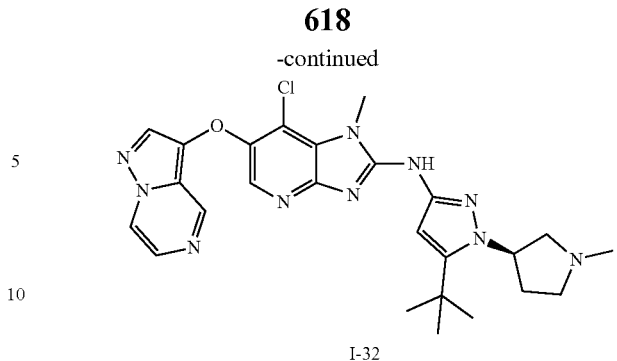

Synthesis of I-32. Compound I-32 was prepared from 21.7 and Int-10, following the procedure described in the synthesis of I-13. The product was purified by flash column chromatography on silica gel (CombiFlash®, 8.1% methanol in dichloromethane). MS (ES): m/z: 521.7 [M+H]+, 1H NMR (DMSO-d6, 400 MHz): δ 9.99 (s, 1H), 9.02-9.01 (d, J=0.8 Hz, 1H), 8.69-8.68 (m, 1H), 8.12 (s, 1H), 8.02 (s, 1H), 7.87-7.86 (d, J=4.8 Hz, 1H), 6.51 (s, 1H), 5.12-5.07 (m, 1H), 3.96 (s, 3H), 2.78-2.64 (m, 4H), 2.32 (bs, 4H), 2.20-2.15 (m, 1H), 1.39 (s, 9H).

Example 33: N-(5-(tert-butyl)-1-(2-oxaspiro[3.3]heptan-6-yl)-1H-pyrazol-3-yl)-7-chloro-6-(imidazo[1,2-b]pyridazin-7-yloxy)-1-methyl-1H-imidazo[4,5-b]pyridin-2-amine

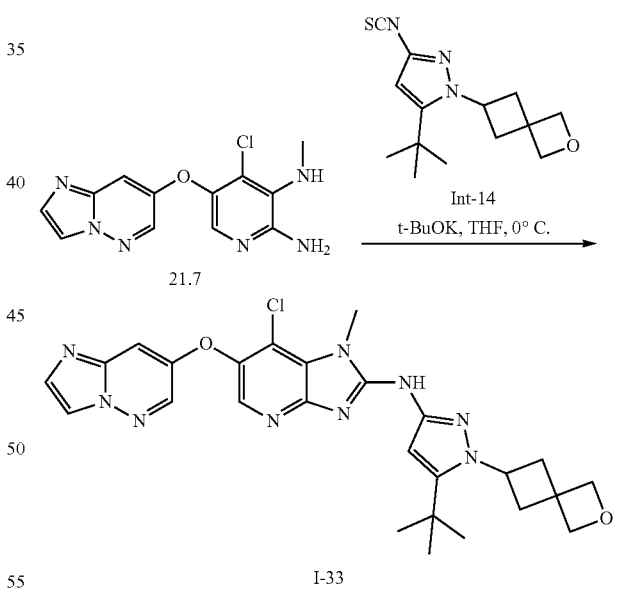

Synthesis of I-33. Compound I-33 was prepared from 13.7 and Int-14, following the procedure described in the synthesis of I-13. The product was purified by flash column chromatography on silica gel (CombiFlash®, 5% methanol in dichloromethane). MS (ES): m/z: 534.3 [M+H]+, 1H NMR (DMSO-d6, 400 MHz): δ 10.04 (s, 1H), 8.74-8.73 (d, J=2.4 Hz, 1H), 8.23 (s, 1H), 8.16 (s, 1H), 7.66 (s, 1H), 7.24-7.23 (d, J=2.8 Hz, 1H), 6.54 (s, 1H), 4.98-4.93 (m, 1H), 4.72 (s, 2H), 4.58 (s, 2H), 3.94 (s, 3H), 2.81-2.74 (m, 4H), 1.36 (s, 9H).

Example 34: N-(5-(tert-butyl)-1-(2,2-difluoroethyl)-1H-pyrazol-3-yl)-7-chloro-1-methyl-6-(pyrazolo[1,5-a]pyrazin-3-yloxy)-1H-imidazo[4,5-b]pyridin-2-amine

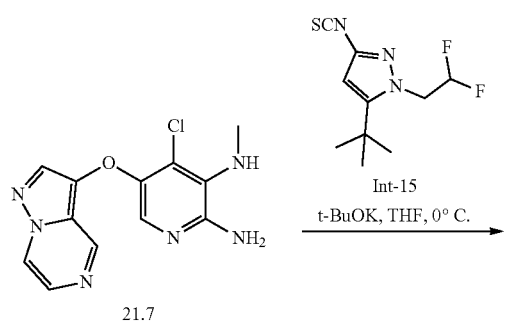

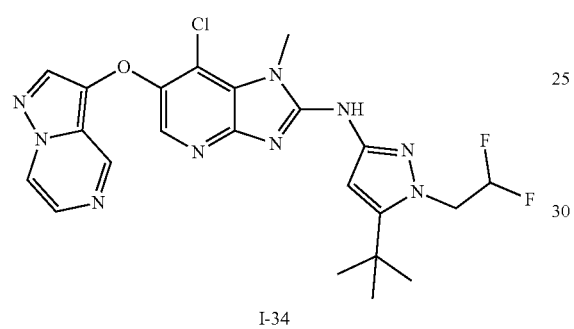

Synthesis of I-34. Compound I-34 was prepared from 21.7 and Int-15, following the procedure described in the synthesis of I-13. The product was purified by flash column chromatography on silica gel (CombiFlash®, 2.5% methanol in dichloromethane). MS (ES): m/z: 502.4 [M+H]$^+$, $^1$H NMR (DMSO-d$_6$, 400 MHz): δ 10.08 (s, 1H), 9.01 (s, 1H), 8.69-8.68 (d, J=4 Hz, 1H), 8.13 (s, 1H), 8.03 (s, 1H), 7.87-7.86 (d, J=4.8 Hz, 1H), 6.64 (s, 1H), 6.59-6.31 (m, 1H), 4.65-4.57 (m, 2H), 3.95 (s, 3H), 1.39 (s, 9H).

Example 35: (S)—N-(5-(tert-butyl)-1-(1-methylpyrrolidin-3-yl)-1H-pyrazol-3-yl)-7-chloro-6-(imidazo[1,2-b]pyridazin-7-yloxy)-1-methyl-1H-imidazo[4,5-b]pyridin-2-amine

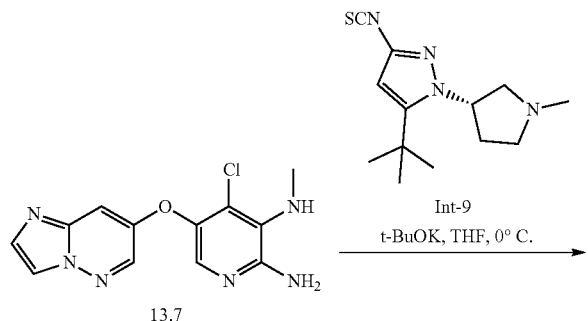

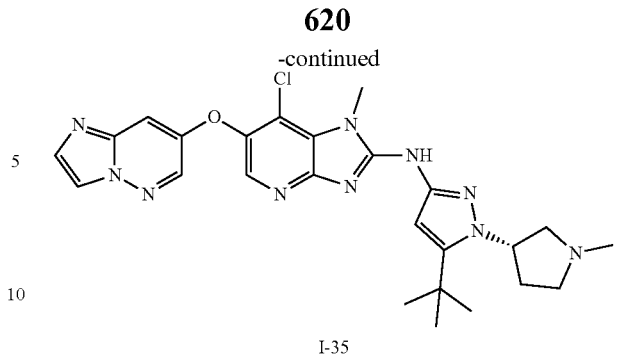

Synthesis of I-35. Compound I-35 was prepared from 13.7 and Int-9, following the procedure described in the synthesis of I-13. The product was purified by flash column chromatography on silica gel (CombiFlash®, 10% methanol in dichloromethane). MS (ES): m/z: 521.5 [M+H]$^+$, $^1$H NMR (DMSO-d$_6$, 400 MHz): δ 10.04 (s, 1H), 8.74-8.73 (d, J=2.4 Hz, 1H), 8.23 (s, 1H), 8.18 (s, 1H), 7.66 (s, 1H), 7.24-7.23 (d, J=2.4 Hz, 1H), 6.56 (s, 1H), 5.27 (s, 1H), 3.96 (s, 3H), 3.10 (bs, 2H), 2.62 (bs, 2H), 2.45 (bs, 3H), 2.34 (bs, 1H), 2.23 (bs, 1H), 1.40 (s, 9H).

Example 36: (R)—N-(5-(tert-butyl)-1-(1-methylpyrrolidin-3-yl)-1H-pyrazol-3-yl)-7-chloro-6-(imidazo[1,2-b]pyridazin-7-yloxy)-1-methyl-1H-imidazo[4,5-b]pyridin-2-amine

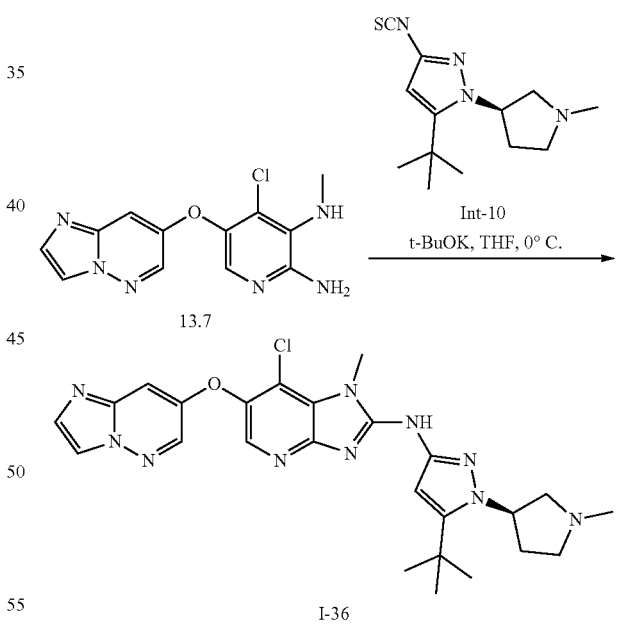

Synthesis of I-36. Compound I-36 was prepared from 13.7 and Int-10, following the procedure described in the synthesis of I-13. The product was purified by flash column chromatography on silica gel (CombiFlash®, 11% methanol in dichloromethane). MS (ES): m/z: 521.03 [M+H]$^+$, $^1$H NMR (DMSO-d$_6$, 400 MHz): δ 10.03 (s, 1H), 8.74-8.73 (d, J=2.4 Hz, 1H), 8.18 (s, 1H), 7.66 (s, 1H), 7.24-7.23 (d, J=2.4 Hz, 1H), 6.54 (s, 1H), 5.27 (s, 1H), 3.96 (s, 3H), 3.10 (bs, 2H), 2.61 (bs, 2H), 2.45 (s, 3H), 2.34 (bs, 1H), 2.24-2.22 (m, 1H), 1.40 (s, 9H).

Example 37: (S)-1-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)propan-2-ol and (R)-1-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)propan-2-ol

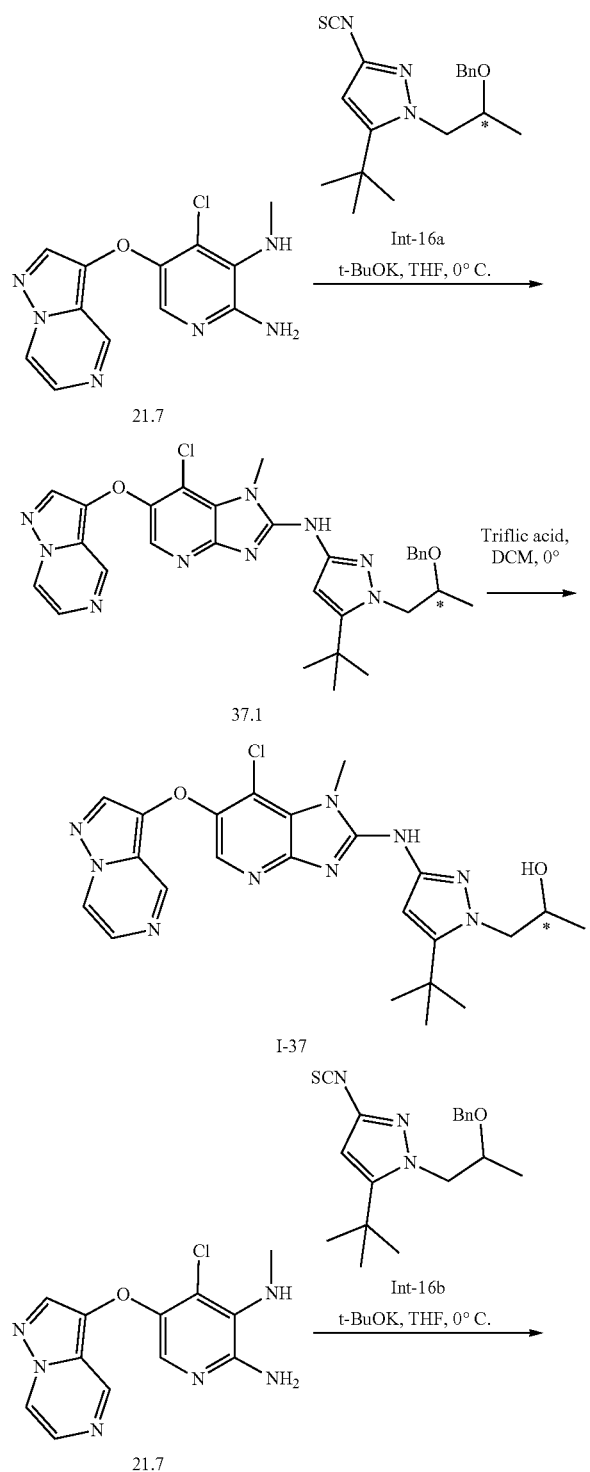

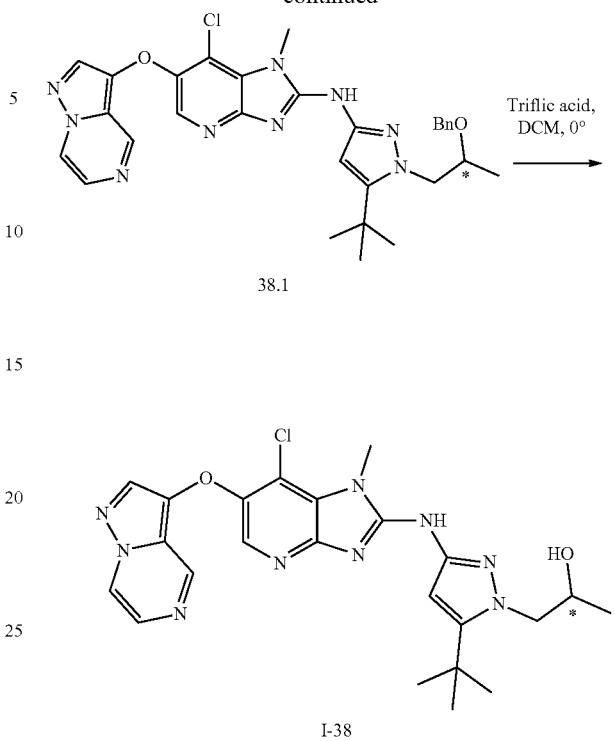

Synthesis of compound 37.1. Compound 37.1 was prepared from 21.7 and Int-16a, following the procedure described in the synthesis of I-13. The product was purified by flash column chromatography on silica gel (CombiFlash®, 3.5% methanol in dichloromethane). MS (ES): m/z: 587.5 [M+H]+.

Synthesis of I-37. Compound I-37 was prepared from 37.1, following the procedure described in the synthesis of I-23. The product was purified by flash column chromatography on silica gel (CombiFlash®, 4.5% methanol in dichloromethane). MS (ES): m/z: 496.41 [M+H]+, H NMR (DMSO-$d_6$, 400 MHz): δ 9.97 (s, 1H), 9.01 (s, 1H), 8.69-8.68 (d, J=4.0 Hz, 1H), 8.12 (s, 1H), 8.02 (s, 1H), 7.87-7.86 (d, J=4.8 Hz, 1H), 6.56 (s, 1H), 4.98-4.97 (d, 1H), 4.25-4.22 (m, 1H), 4.11-4.06 (m, 1H), 3.95 (bs, 4H), 1.39 (s, 9H), 1.15-1.14 (d, 3H). (*Absolute stereochemistry not determined).

Synthesis of compound 38.1. Compound 38.1 was prepared from 21.7 and Int-16b, following the procedure described in the synthesis of I-13. The product was purified by flash column chromatography on silica gel (CombiFlash®, 3.5% methanol in dichloromethane). MS (ES): m/z: 587.4 [M+H]+.

Synthesis of I-38. Compound I-38 was prepared from 38.1, following the procedure described in the synthesis of I-23. The product was purified by flash column chromatography on silica gel (CombiFlash®, 4.5% methanol in dichloromethane). MS (ES): m/z: 496.41 [M+H]+, $^1$H NMR (DMSO-$d_6$, 400 MHz): δ 9.97 (s, 1H), 9.01 (s, 1H), 8.69-8.68 (d, J=4.0 Hz, 1H), 8.12 (s, 1H), 8.02 (s, 1H), 7.87-7.86 (d, J=4.8 Hz, 1H), 6.56 (s, 1H), 4.98-4.97 (d, 1H), 4.25-4.21 (m, 1H), 4.11-4.05 (m, 1H), 3.95 (bs, 4H), 1.39 (s, 9H), 1.15-1.14 (d, 3H). (*Absolute stereochemistry not determined.)

Example 39: (S)—N-(5-(tert-butyl)-1-(1-methylpyrrolidin-3-yl)-1H-pyrazol-3-yl)-7-(difluoromethyl)-1-methyl-6-(thiazolo[5,4-b]pyridin-6-yloxy)-1H-imidazo[4,5-b]pyridin-2-amine

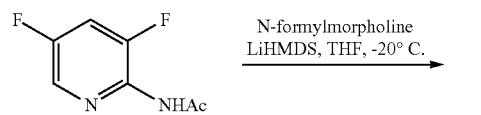

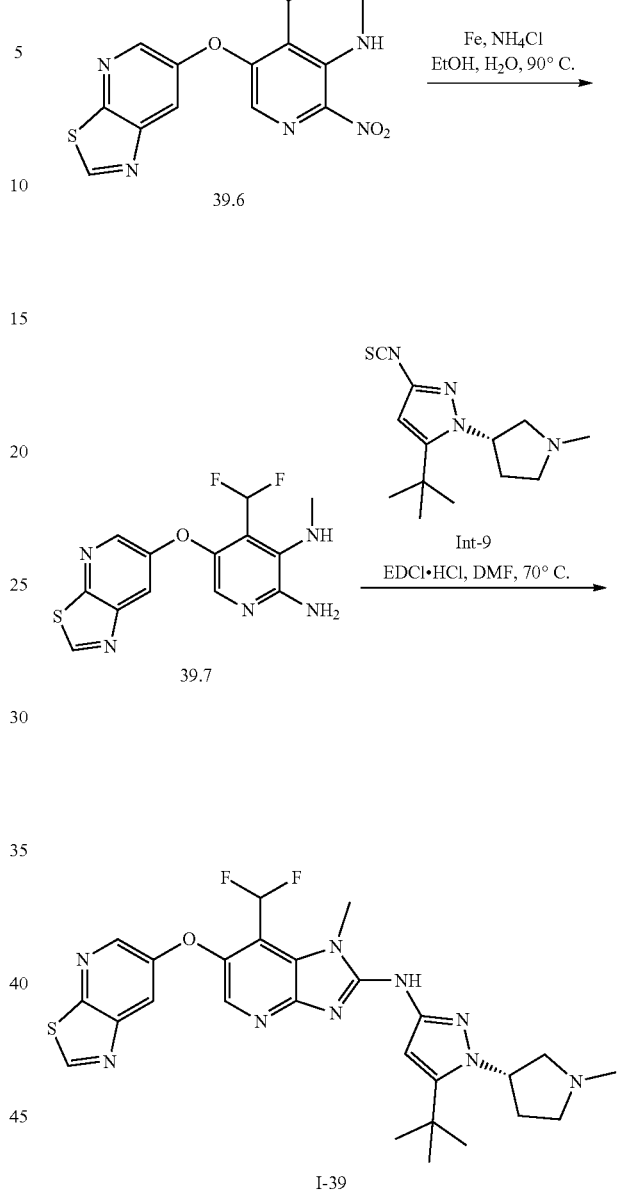

Synthesis of compound 39.1. To a solution of N-(3,5-difluoropyridin-2-yl)acetamide (15 g, 87.14 mmol, 1.0 equiv) and N-formylmorpholine (26.1 mL, 261.4 mmol, 3.0 equiv) in THF (150 mL) was added lithium bis(trimethylsilyl)amide (1.0 M in THF, 200 mL, 200.4 mmol, 2.3 equiv) at −20° C. dropwise. After the addition, the reaction mixture was stirred at same temperature for 2 h. It was poured into a cold aqueous solution of citric acid monohydrate (60.4 g) and sodium chloride (15 g), and the mixture was stirred at 0° C. for 15 min. The organic layer was separated, washed with 50% dipotassium hydrogen phosphate aqueous solution followed by brine. It was dried over sodium sulfate, filtered and concentrated under reduced pressure. The residue was purified by flash column chromatography on silica gel (CombiFlash®, 70% ethyl acetate in hexane) to afford 39.1. $^1$H NMR (DMSO-$d_6$, 400 MHz): δ 10.46 (s, 1H), 10.22 (s, 1H), 8.53 (s, 1H), 2.09 (s, 3H).

Synthesis of compound 39.2. To a solution of 39.1 (1.0 g, 5.0 mmol, 1.0 equiv) in dichloromethane (10 mL) was added diethylaminosulfur trifluoride (0.65 mL, 5.0 mmol, 1.0 equiv) dropwise at 0° C. The reaction mixture was stirred at same temperature for 30 min. It was transferred into saturated sodium bicarbonate solution and extracted with ethyl acetate. The combined organic layers were washed with brine, dried over sodium sulfate, filtered and concentrated under reduced pressure. The residue was purified by flash column chromatography on silica gel (CombiFlash®, 35-40% ethyl acetate in hexane) to afford 39.2. $^1$H NMR (CDCl$_3$, 400 MHz): δ 8.27 (s, 1H), 7.63 (s, 1H), 7.12-6.86 (m, 1H), 2.38 (s, 3H).

Synthesis of compound 39.3. To a solution of 39.2 (1.8 g, 8.10 mmol, 1.0 equiv) in methanol (10 mL) was added concentrated hydrochloric acid (3 mL). The reaction mixture was heated to reflux for 1 h. It was concentrated under reduced pressure. To the residue was added ice-water and it was neutralized by saturated sodium bicarbonate solution and extracted with ethyl acetate. The combined organic layers were washed with brine, dried over sodium sulfate, filtered and concentrated under reduced pressure. The residue was purified by flash column chromatography on silica gel (CombiFlash®, 15-20% ethyl acetate in hexane) to afford 39.3. $^1$H NMR (DMSO-d$_6$, 400 MHz): δ 7.99 (s, 1H), 7.44-7.18 (m, 1H), 6.54 (s, 2H).

Synthesis of compound 39.4. Concentrated sulfuric acid (5 mL, 6 vol) was added dropwise to potassium persulfate (3.56 g, 13.21 mmol, 2.8 equiv) at room temperature and stirred for 15 min. To the mixture was added 39.3 (0.850 g, 4.72 mmol, 1.0 equiv) in portions, maintaining temperature at 30-40° C. The reaction mixture was stirred at room temperature for 3-4 h. It was poured into crushed ice, stirred and basified with saturated sodium bicarbonate. The aqueous mixture was extracted with ethyl acetate. The combined organic layers were washed with brine, dried over sodium sulfate, filtered and concentrated under reduced pressure. The residue was purified by flash column chromatography on silica gel (CombiFlash®, 8-10% ethyl acetate in hexane) to afford 39.4. $^1$H NMR (CDCl$_3$, 400 MHz): δ 8.69 (s, 1H), 7.28-6.91 (m, 1H).

Synthesis of compound 39.5. To a solution of 39.4 (0.155 g, 0.737 mmol, 1.0 equiv) in acetonitrile (3 mL) was added aqueous methylamine solution (40%, 0.06 mL, 0.737 mmol, 1.0 equiv) dropwise at 0° C. The reaction mixture was stirred at room temperature for 2-3 h. It was poured over ice-water and extracted with ethyl acetate. The combined organic layers were washed with brine, dried over sodium sulfate, filtered and concentrated under reduced pressure to afford 39.5. $^1$H NMR (DMSO-d$_6$, 400 MHz): δ 7.96 (s, 1H), 7.54-7.41 (m, 1H), 2.86 (d, 3H).

Synthesis of compound 39.6. To a solution of 39.5 (0.300 g, 1.36 mmol, 1.0 equiv) in DMF (10 mL) was added 27.4 (0.309 g, 2.03 mmol, 1.5 equiv) followed by potassium carbonate (0.469 g, 3.4 mmol, 2.5 equiv). The reaction mixture was stirred at room temperature for 1 h. It was poured over ice-water and extracted with ethyl acetate. The combined organic layers were washed with brine, dried over anhydrous sodium sulfate, filtered and concentrated under reduced pressure. The residue was purified by trituration with diethyl ether to afford 39.6. (0.295 g, 61.55%). MS (ES): m/z 354.2 [M+H]$^+$.

Synthesis of compound 39.7. Compound 39.7 was prepared from 39.6, following the procedure described in the synthesis of 5.4. The product was purified by flash column chromatography on silica gel (CombiFlash®, 3.0% methanol in dichloromethane). MS (ES): m/z 324.3 [M+H]$^+$.

Synthesis of I-39. Compound I-39 was prepared from 39.7 and Int-9 following the procedure described in the synthesis of 1.7. The product was purified by flash column chromatography on silica gel (CombiFlash®, 4.0% methanol in dichloromethane). MS (ES): m/z: 554.5 [M+H]$^+$, $^1$H NMR (DMSO-d$_6$, 400 MHz): δ 10.09 (s, 1H), 9.59 (s, 1H), 8.63-8.62 (d, J=2.4 Hz, 1H), 8.07 (s, 1H), 7.95-7.94 (d, J=2.8 Hz, 1H), 7.66-7.40 (m, 1H), 6.53 (s, 1H), 5.10-5.06 (m, 1H), 3.80 (s, 3H), 3.02-2.98 (m, 1H), 2.74-2.63 (m, 3H), 2.30 (bs, 4H), 2.18-2.17 (m, 1H), 1.38 (s, 9H).

Example 40: (R)—N-(5-(tert-butyl)-1-(1-methylpyrrolidin-3-yl)-1H-pyrazol-3-yl)-7-(difluoromethyl)-1-methyl-6-(thiazolo[5,4-b]pyridin-6-yloxy)-1H-imidazo[4,5-b]pyridin-2-amine

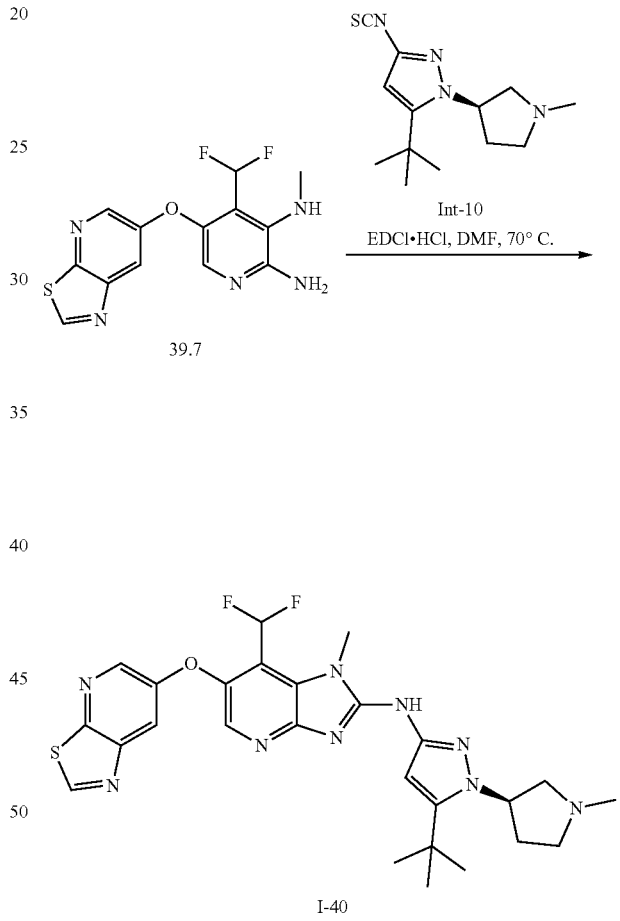

Synthesis of I-40. Compound I-40 was prepared from 39.7 and Int-10 following the procedure described in the synthesis of 1.7. The product was purified by flash column chromatography on silica gel (CombiFlash®, 4.0% methanol in dichloromethane). MS (ES): m/z: 554.4 [M+H]$^+$, $^1$H NMR (DMSO-d$_6$, 400 MHz): δ 10.10 (s, 1H), 9.60 (s, 1H), 8.64-8.63 (d, J=2.4 Hz, 1H), 8.09 (s, 1H), 7.96-7.95 (d, J=2.8 Hz, 1H), 7.67-7.41 (m, 1H), 6.54 (s, 1H), 5.11-5.07 (m, 1H), 3.82 (s, 3H), 3.01-2.99 (m, 1H), 2.75-2.63 (m, 3H), 2.31 (bs, 4H), 2.19-2.18 (m, 1H), 1.40 (s, 9H).

Example 41: (R)—N-(5-(tert-butyl)-1-(4-oxaspiro[2.4]heptan-7-yl)-1H-pyrazol-3-yl)-7-chloro-1-methyl-6-(pyrazolo[1,5-a]pyrazin-3-yloxy)-1H-imidazo[4,5-b]pyridin-2-amine and (R)—N-(5-(tert-butyl)-1-(4-oxaspiro[2.4]heptan-7-yl)-1H-pyrazol-3-yl)-7-chloro-1-methyl-6-(pyrazolo[1,5-a]pyrazin-3-yloxy)-1H-imidazo[4,5-b]pyridin-2-amine

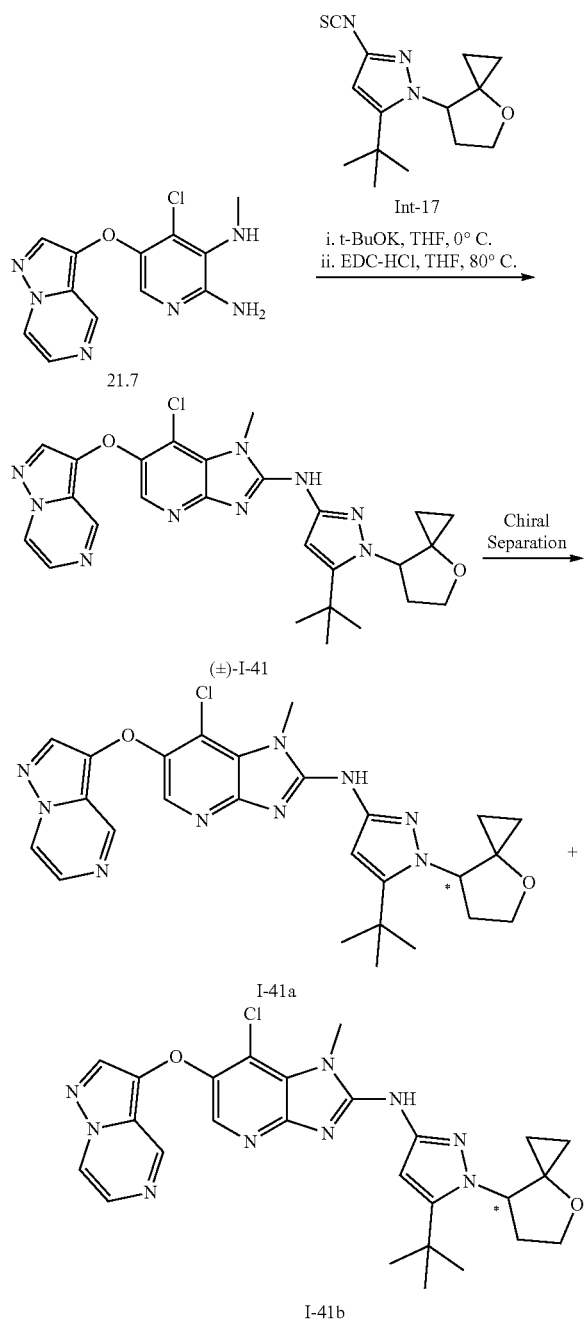

Synthesis of compound (±)-I-41. To a solution of 21.7 (0.100 g, 0.343 mmol, 1.0 equiv) in THF (5 mL) was added Int-17 (0.095 g, 0.343 mmol, 1.0 equiv) followed by addition of potassium tert-butoxide (1 M in THF, 1.0 mL, 1.029 mmol, 3.0 equiv) at 0° C. The reaction mixture was stirred for 30 min. It poured over ice-water and extracted with ethyl acetate. The combined organic layers were washed with brine, dried over anhydrous sodium sulfate, filtered and concentrated under reduced pressure. The residue was dissolved in THF (5 mL) and N-(3-dimethylaminopropyl)-N'-ethylcarbodiimide hydrochloride (0.131 g, 0.686 mmol, 2.0 equiv) was added. The reaction mixture was stirred at 80° C. for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in dichloromethane) to afford (±)-I-41. MS (ES): m/z: 534.9 [M+H]+.

Separation of I-41a and I-41b. Enantiomers of (±)-I-41 were separated by HPLC (column: CHIRALPAK IC (250 mm×21 mm, 5 μm); mobile phase: 0.1% DEA in methanol; flow rate=20 mL/min) to afford first eluting fraction (I-41a) and second eluting fraction (I-41b).

I-41a: MS (ES): m/z: 534.4 [M+H]+, 1H NMR (DMSO-$d_6$, 400 MHz): δ 9.99 (s, 1H), 8.97 (s, 1H), 8.68-8.66 (m, 1H), 8.02-8.00 (d, J=8 Hz, 2H), 7.86-7.84 (d, J=4.8 Hz, 1H), 6.51 (s, 1H), 5.01-4.98 (m, 1H), 4.25-4.19 (m, 1H), 3.91 (s, 3H), 3.85-3.80 (m, 1H), 2.39-2.31 (m, 2H), 1.33 (s, 9H), 0.9-0.84 (m, 2H), 0.79-0.75 (m, 2H).

I-41b: MS (ES): m/z: 534.4 [M+H]+, 1H NMR (DMSO-$d_6$, 400 MHz): δ 9.97 (s, 1H), 8.97 (s, 1H), 8.68-8.66 (m, 1H), 8.02-8.00 (d, J=8 Hz, 2H), 7.86-7.84 (d, J=4.8 Hz, 1H), 6.51 (s, 1H), 5.01-4.97 (m, 1H), 4.24-4.19 (m, 1H), 3.91 (s, 3H), 3.85-3.79 (m, 1H), 2.39-2.31 (m, 2H), 1.33 (s, 9H), 0.9-0.84 (m, 2H), 0.79-0.75 (m, 2H).

Example 42: N-(5-(tert-butyl)-1-(2-oxaspiro[3.3]heptan-6-yl)-1H-pyrazol-3-yl)-7-chloro-1-methyl-6-(pyrazolo[1,5-a]pyrimidin-6-yloxy)-1H-imidazo[4,5-b]pyridin-2-amine

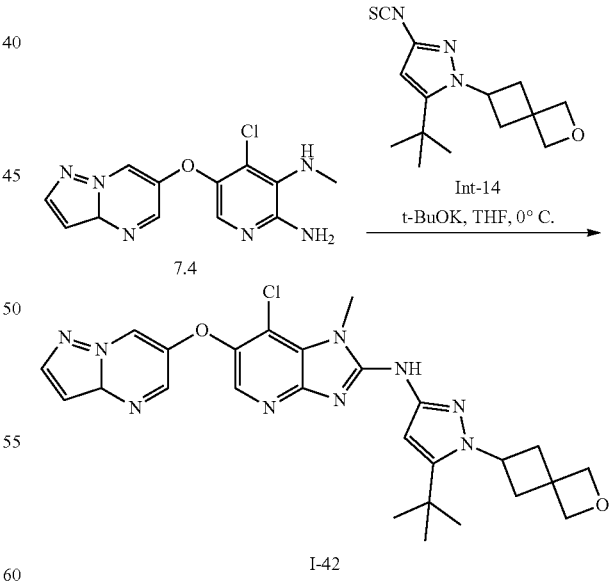

Synthesis of I-42. Compound I-42 was prepared from 7.4 and Int-14, following the procedure described in the synthesis of I-13. The product was purified by flash column chromatography on silica gel (CombiFlash®, 3% methanol in dichloromethane). MS (ES): m/z: 535.7 [M+H]+, 1H NMR (DMSO-$d_6$, 400 MHz): δ 9.99 (s, 1H), 8.87-8.86 (d, J=2.4 Hz, 1H), 8.69-8.68 (d, J=2.8 Hz, 1H), 8.18-8.17 (d, J=2.0 Hz, 1H), 8.14 (s, 1H), 6.78 (s, 1H), 6.52 (s, 1H), 4.96-4.92 (m, 1H), 4.71 (s, 2H), 4.57 (s, 2H), 3.94 (s, 3H), 2.80-2.67 (m, 4H), 1.35 (s, 9H).

Example 43: (S)—N-(5-(tert-butyl)-1-(1-(2-fluoroethyl)pyrrolidin-3-yl)-1H-pyrazol-3-yl)-7-(difluoromethyl)-1-methyl-6-(pyrazolo[1,5-a]pyrazin-3-yloxy)-1H-imidazo[4,5-b]pyridin-2-amine

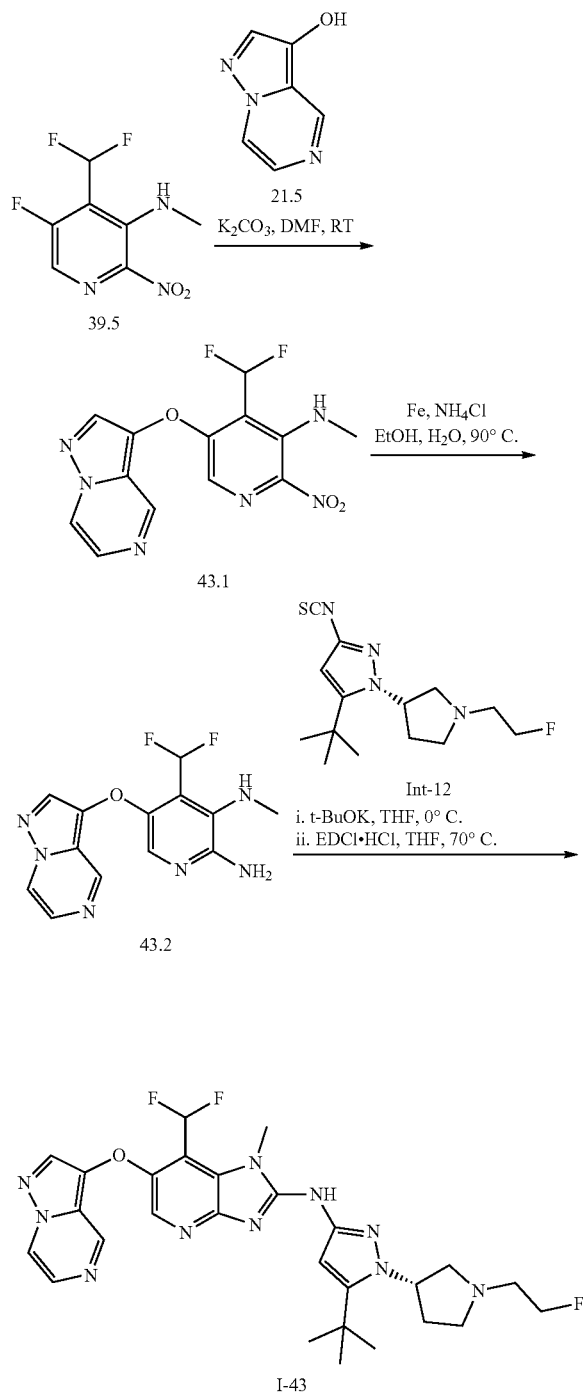

Synthesis of compound 43.1. Compound 43.1 was prepared from 39.5 and 21.5, following the procedure described in the synthesis of 39.6. The product was purified by trituration with diethyl ether. MS (ES): m/z 337.5 [M+H]$^+$.

Synthesis of compound 43.2. Compound 43.2 was prepared from 43.1, following the procedure described in the synthesis of 5.4. The product was purified by flash column chromatography on silica gel (CombiFlash®, 3.0% methanol in dichloromethane). MS (ES): m/z 307.3 [M+H]$^+$.

Synthesis of I-43. Compound I-43 was prepared from 43.2 and Int-12, following the procedure described in the synthesis of I-41. The product was purified by flash column chromatography on silica gel (CombiFlash®, 4.0% methanol in dichloromethane). MS (ES): m/z: 569.8 [M+H]$^+$, $^1$H NMR (DMSO-d$_6$, 400 MHz): δ 10.08 (s, 1H), 9.02 (s, 1H), 8.71-8.70 (d, J=4.0 Hz, 1H), 8.65-8.64 (d, J=4.0 Hz, 1H), 8.07-8.05 (d, J=7.6 Hz, 1H), 7.81-7.58 (m, 1H), 6.53 (s, 1H), 6.26 (s, 1H), 5.11-5.07 (m, 1H), 4.62-4.60 (t, 2H), 4.50-4.48 (t, 2H), 3.82 (s, 3H), 3.40-3.38 (m, 2H), 3.17-3.11 (m, 2H), 2.85-2.81 (m, 1H), 2.79-2.74 (m, 1H), 1.39 (s, 9H).

Example 44: (R)—N-(5-(tert-butyl)-1-(1-(2-fluoroethyl)pyrrolidin-3-yl)-1H-pyrazol-3-yl)-7-(difluoromethyl)-1-methyl-6-(pyrazolo[1,5-a]pyrazin-3-yloxy)-1H-imidazo[4,5-b]pyridin-2-amine

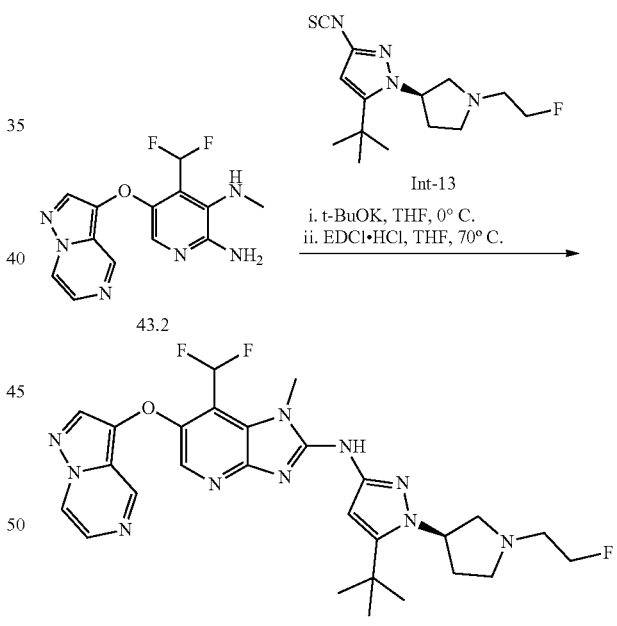

Synthesis of I-44. Compound I-43 was prepared from 43.2 and Int-13, following the procedure described in the synthesis of I-41. The product was purified by flash column chromatography on silica gel (CombiFlash®, 4.0% methanol in dichloromethane). MS (ES): m/z: 569.8 [M+H]$^+$, $^1$H NMR (DMSO-d$_6$, 400 MHz): δ 10.08 (s, 1H), 9.02 (s, 1H), 8.71-8.70 (d, J=4.0 Hz, 1H), 8.65-8.64 (d, J=4.0 Hz, 1H), 8.07-8.05 (d, J=7.6 Hz, 1H), 7.81-7.58 (m, 1H), 6.53 (s, 1H), 6.26 (s, 1H), 5.11-5.07 (m, 1H), 4.62-4.60 (t, 2H), 4.50-4.48 (t, 2H), 3.82 (s, 3H), 3.40-3.38 (m, 2H), 3.17-3.11 (m, 2H), 2.85-2.81 (m, 1H), 2.79-2.74 (m, 1H), 1.39 (s, 9H).

Example 45: (S)—N-(5-(tert-butyl)-1-(1-methylpyrrolidin-3-yl)-1H-pyrazol-3-yl)-7-methoxy-1-methyl-6-(thieno[2,3-b]pyridin-5-yloxy)-1H-imidazo[4,5-b]pyridin-2-amine

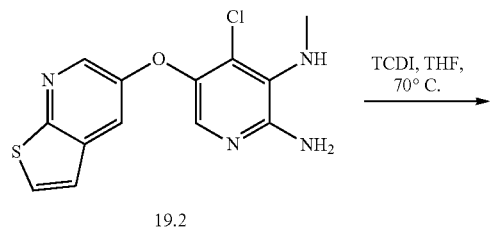

19.2

TCDI, THF,
70° C.

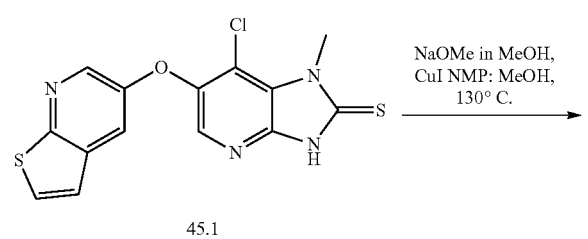

45.1

NaOMe in MeOH,
CuI NMP: MeOH,
130° C.

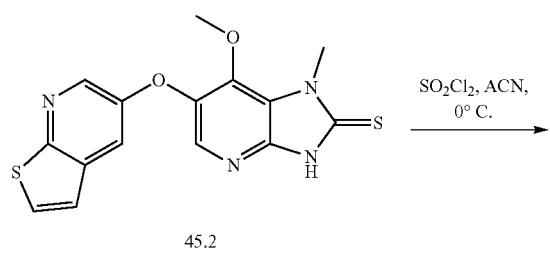

45.2

SO$_2$Cl$_2$, ACN,
0° C.

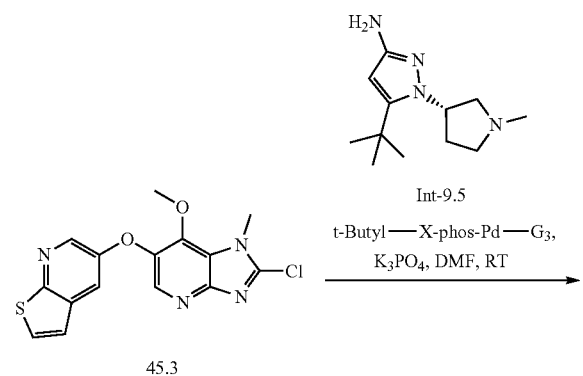

45.3

Int-9.5 t-Butyl—X-phos-Pd—G$_3$,
K$_3$PO$_4$, DMF, RT

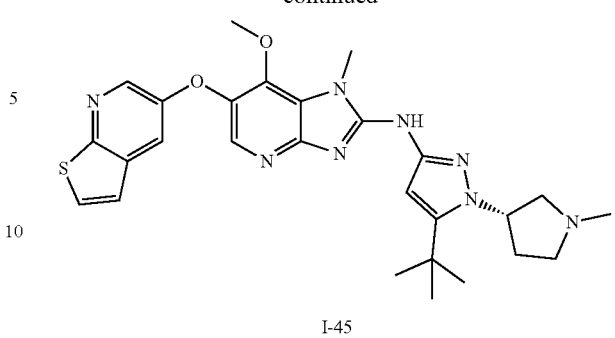

I-45

Synthesis of compound 45.1. To a solution of 19.2 (0.642 g, 2.09 mmol, 1.0 equiv) in THF (15 mL) was added 1,1'-thiocarbonyldiimidazole (1.86 g, 10.45 mmol, 5.0 equiv). The reaction mixture was stirred at 70° C. for 1 h. It was cooled to room temperature and poured into ice-water. The precipitated solids were collected by filtration and triturated with hexane to afford 45.1. MS (ES): m/z: 349.5 [M+H]$^+$.

Synthesis of compound 45.2. To a solution of 45.1 (0.545 g, 1.56 mmol, 1.0 equiv) in methanol (2 mL) and N-methylpyrrolidine (5 mL) was added a solution of sodium methoxide (0.5 M in methanol, 7.8 mL, 3.9 mmol, 2.5 equiv) and copper iodide (0.059 g, 0.312 mmol, 0.2 equiv). The reaction mixture was stirred at 130° C. under argon for 2 h. It was cooled to room temperature, poured into ice-water, and extracted with DCM. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford 45.2. MS (ES): m/z: 345.1 [M+H]$^+$.

Synthesis of compound 45.3. To a solution of 45.2 (0.135 g, 0.391 mmol, 1.0 equiv) in acetonitrile (5 mL) was added sulfuryl chloride (0.4 mL, 4.995 mmol, 37 equiv) at 0° C. The reaction mixture was stirred for 30 min. It was transferred into saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.8% methanol in DCM) to afford 45.3. MS (ES): m/z 347.1 [M+H]$^+$.

Synthesis of I-45. A mixture of 45.3 (0.050 g, 0.144 mmol, 1.0 equiv), Int-9.5 (0.032 g, 0.144 mmol, 1.2 equiv) and tripotassium phosphate (0.091 g, 0.432 mmol, 3.0 equiv) in DMF (3 mL) was degassed by bubbling through a stream of argon for 10 min. Under argon atmosphere [(2-di-tert-butylphosphino-2',4',6'-triisopropyl-1,1'-biphenyl)-2-(2'-amino-1,1'-biphenyl)]palladium(II) methanesulfonate (0.034 g, 0.043 mmol, 0.3 equiv) was added, and the mixture was degassed for an additional 5 min. The reaction mixture was stirred at room temperature for 24 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% methanol in DCM) to afford I-45. MS (ES): m/z: 533.2 [M+H]$^+$, $^1$H NMR (DMSO-d$_6$, 400 MHz): δ 9.80 (s, 1H), 8.54-8.53 (d, J=2.4 Hz, 1H), 8.00 (s, 1H), 7.92-7.91 (d, J=6.0 Hz, 1H), 7.69-7.68 (d, J=2.8 Hz, 1H), 7.36-7.34 (d, J=6.0 Hz, 1H), 6.51 (s, 1H), 5.20 (bs, 1H), 3.96 (s, 3H), 3.86 (s, 3H), 3.35 (s, 3H), 2.98 (bs, 2H), 2.21-2.19 (m, 2H), 1.39 (s, 9H), 1.28-1.20 (m, 2H).

Example 46: (R)—N-(5-(tert-butyl)-1-(1-methylpyrrolidin-3-yl)-1H-pyrazol-3-yl)-7-methoxy-1-methyl-6-(thieno[2,3-b]pyridin-5-yloxy)-1H-imidazo[4,5-b]pyridin-2-amine

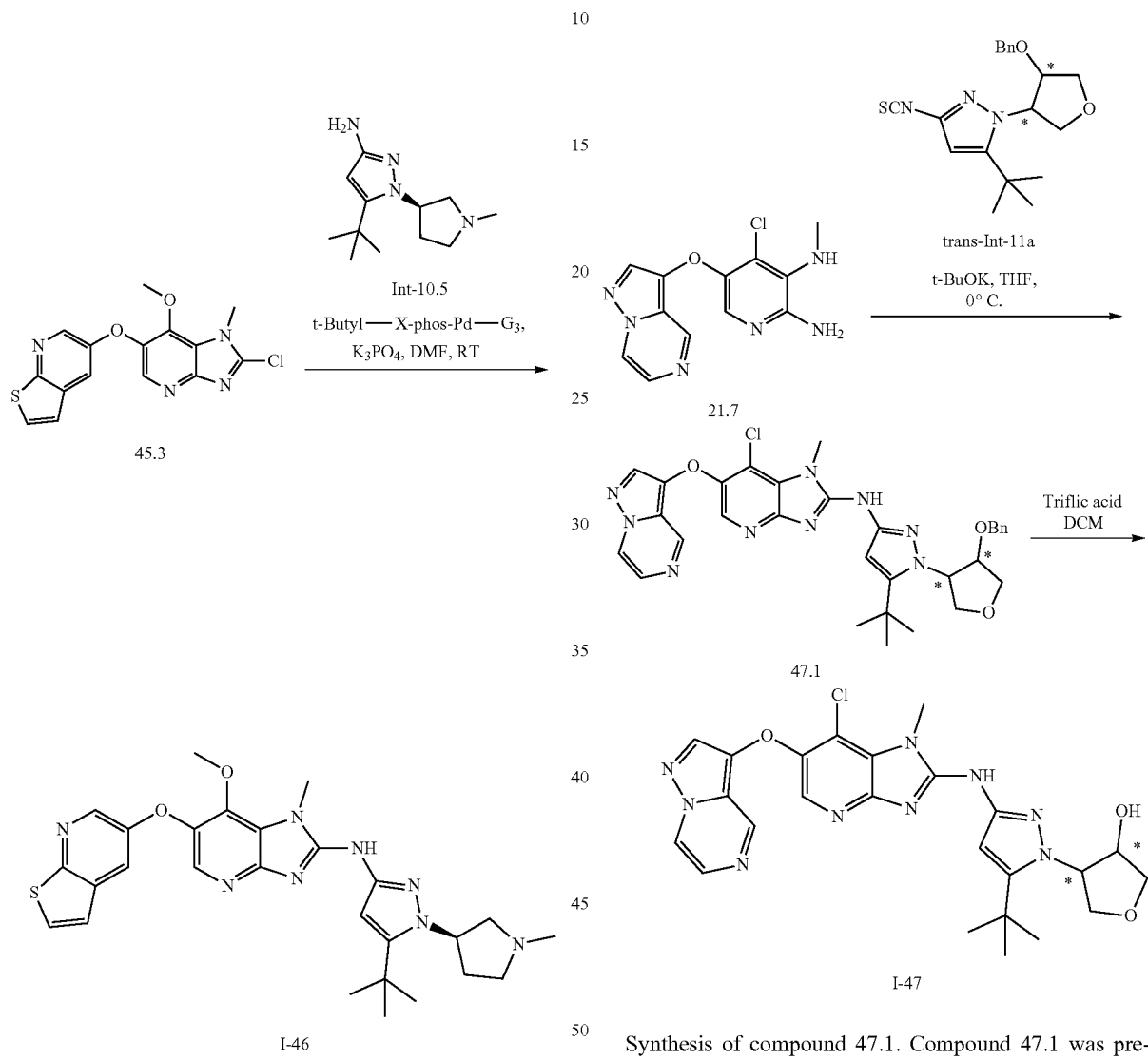

Synthesis of I-46. Compound I-46 was prepared from 45.3 following the procedure described in the synthesis of I-45. The product was purified by flash column chromatography on silica gel (CombiFlash®, 10% methanol in DCM) to afford I-46. MS (ES): m/z: 533.2 [M+H]⁺, ¹H NMR (DMSO-d₆, 400 MHz): δ 9.81 (s, 1H), 8.53 (bs, 1H), 7.99 (bs, 1H), 7.92 (bs, 1H), 7.68 (bs, 1H), 7.35 (bs, 1H), 6.51 (s, 1H), 5.19 (bs, 1H), 3.95 (s, 3H), 3.84 (s, 3H), 3.35 (s, 3H), 2.96 (bs, 2H), 2.19 (bs, 2H), 1.39 (s, 9H), 1.28-1.20 (m, 2H).

Example 47: (3R,4S)-4-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)tetrahydrofuran-3-ol and (3S,4R)-4-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)tetrahydrofuran-3-ol

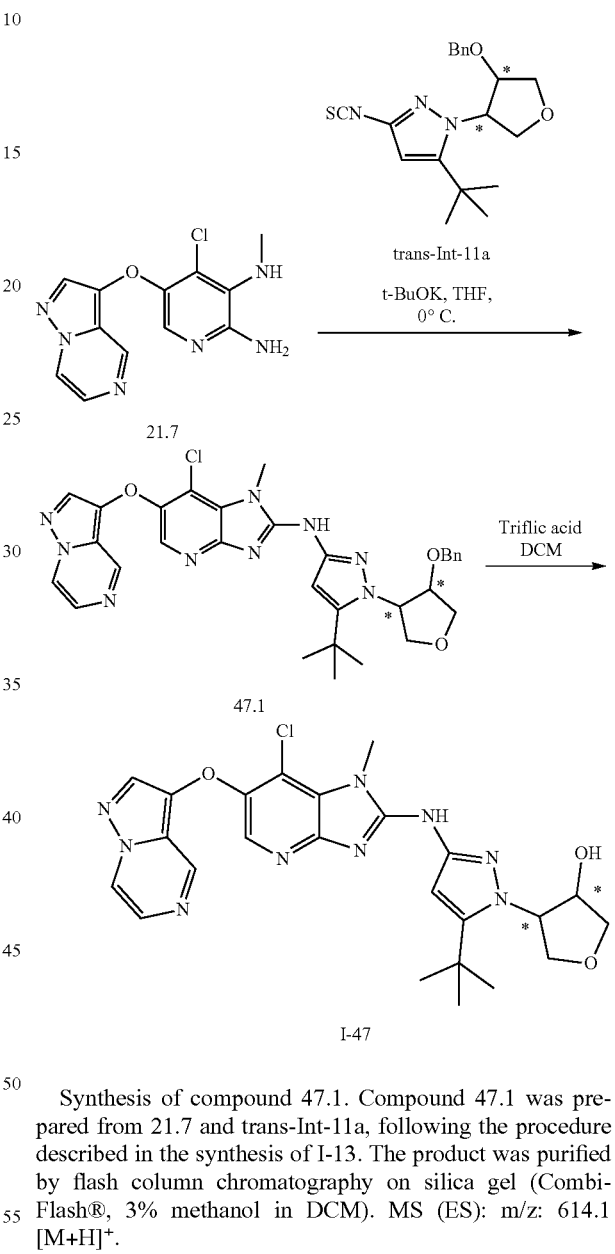

Synthesis of compound 47.1. Compound 47.1 was prepared from 21.7 and trans-Int-11a, following the procedure described in the synthesis of I-13. The product was purified by flash column chromatography on silica gel (CombiFlash®, 3% methanol in DCM). MS (ES): m/z: 614.1 [M+H]⁺.

Synthesis of I-47. Compound I-47 was prepared from 47.1, following the procedure described in the synthesis of I-23. The product was purified by flash column chromatography on silica gel (CombiFlash®, 7.0% methanol in DCM). MS (ES): m/z: 524.3 [M+H]⁺, LCMS purity: 100%, ¹H NMR (DMSO-d₆, 400 MHz): δ 10.00 (s, 1H), 9.01-9.00 (d, J=1.6 Hz, 1H), 8.68-8.67 (m, 1H), 8.12 (s, 1H), 8.01 (s, 1H), 7.86-7.85 (d, J=4.8 Hz, 1H), 6.56 (s, 1H), 5.55-5.53 (m, 1H), 4.91 (bs, 1H), 4.55 (bs, 1H), 4.29-4.27 (m, 1H), 4.14-4.11 (m, 1H), 3.95 (s, 3H), 3.80-3.79 (m, 1H), 3.70-3.66 (m, 1H), 1.40 (s, 9H). (*Absolute stereochemistry not determined.)

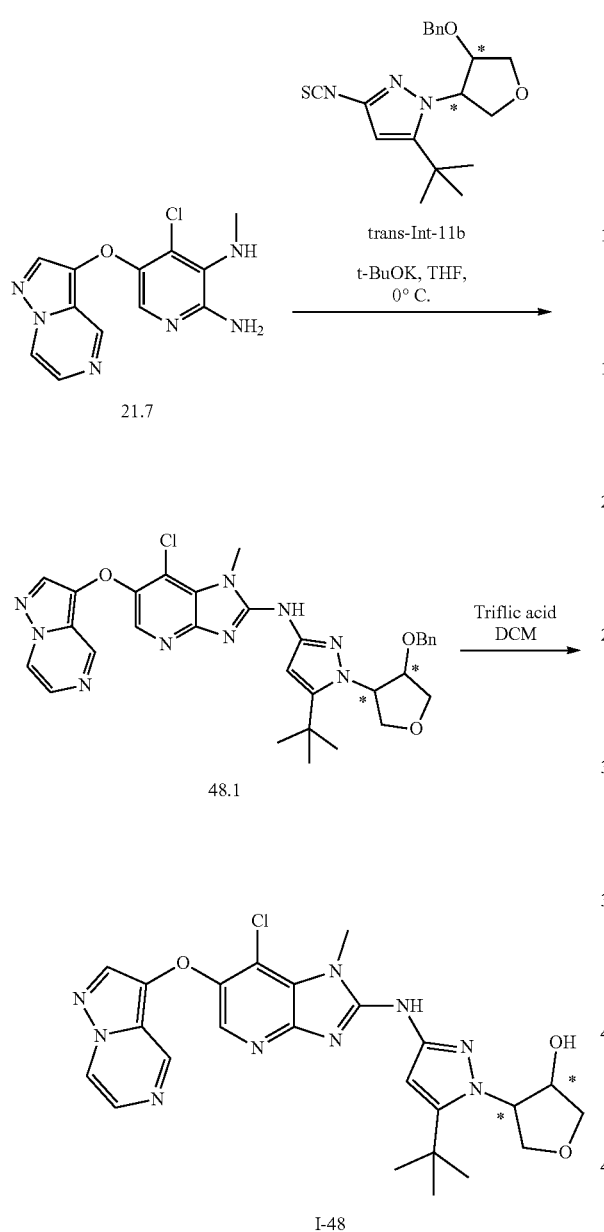

Synthesis of compound 48.1. Compound 48.1 was prepared from 21.7 and trans-Int-11b, following the procedure described in the synthesis of I-13. The product was purified by flash column chromatography on silica gel (Combi-Flash®, 3% methanol in DCM). MS (ES): m/z: 614.1 [M+H]+.

Synthesis of I-48. Compound I-48 was prepared from 48.1, following the procedure described in the synthesis of I-23. The product was purified by flash column chromatography on silica gel (CombiFlash®, 7.0% methanol in DCM. MS (ES): m/z: 524.3 [M+H]+, LCMS purity: 100%, $^1$H NMR (DMSO-d$_6$, 400 MHz): δ 10.03 (s, 1H), 9.02-9.01 (d, J=1.6 Hz, 1H), 8.70-8.68 (m, 1H), 8.13 (s, 1H), 8.03 (s, 1H), 7.87-7.86 (d, J=4.8 Hz, 1H), 6.57 (s, 1H), 5.55-5.53 (m, 1H), 4.92 (bs, 1H), 4.57 (bs, 1H), 4.30-4.26 (m, 1H), 4.15-4.12 (m, 1H), 3.96 (s, 3H), 3.82-3.79 (m, 1H), 3.71-3.67 (m, 1H), 1.41 (s, 9H). (*Absolute stereochemistry not determined.)

Example 49: N-(5-(tert-butyl)-1-(2-oxaspiro[3.3]heptan-6-yl)-1H-pyrazol-3-yl)-7-chloro-1-methyl-6-(pyrazolo[1,5-a]pyrazin-3-yloxy)-1H-imidazo[4,5-b]pyridin-2-amine

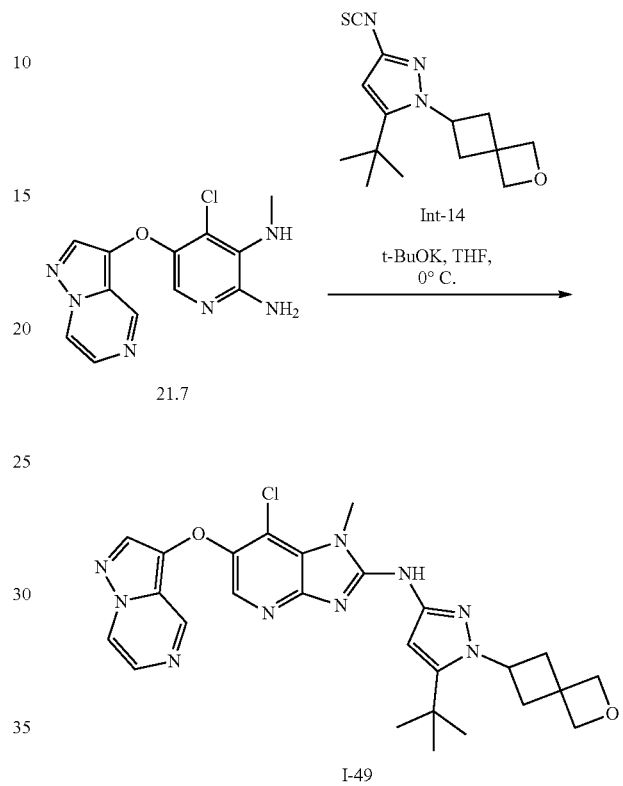

Synthesis of I-49. Compound I-49 was prepared from 21.7 and Int-14, following the procedure described in the synthesis of I-13. The product was purified by flash column chromatography on silica gel (CombiFlash®, 5% methanol in DCM). MS (ES): m/z: 534.4 [M]+, $^1$H NMR (DMSO-d$_6$, 400 MHz): δ 9.97 (s, 1H), 9.01 (s, 1H), 8.68-8.67 (d, J=4.4 Hz, 1H), 8.12 (s, 1H), 8.02 (s, 1H), 7.87-7.86 (d, J=4.8 Hz, 1H), 6.52 (s, 1H), 4.96-4.92 (m, 1H), 4.71 (s, 2H), 4.58 (s, 2H), 3.95 (s, 3H), 2.77-2.73 (m, 4H), 1.35 (s, 9H).

Example 50: (S)—N-(5-(tert-butyl)-1-(1-(2-fluoroethyl)pyrrolidin-3-yl)-1H-pyrazol-3-yl)-7-methoxy-1-methyl-6-(pyrazolo[1,5-a]pyrazin-3-yloxy)-1H-imidazo[4,5-b]pyridin-2-amine

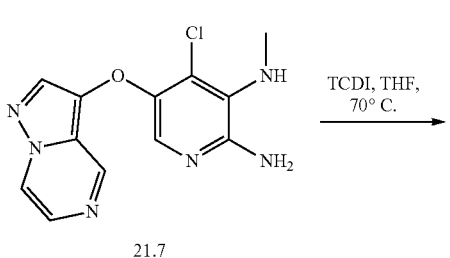

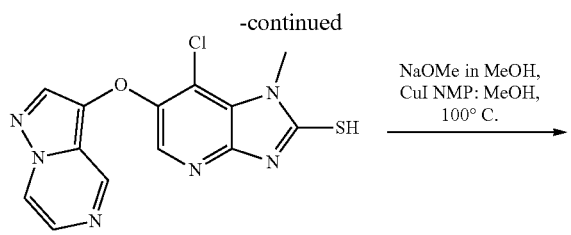

50.1

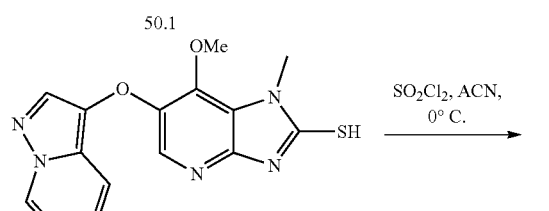

50.2

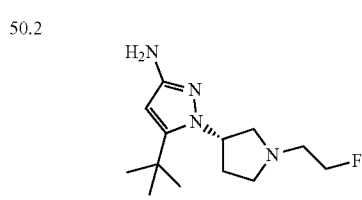

Int-12

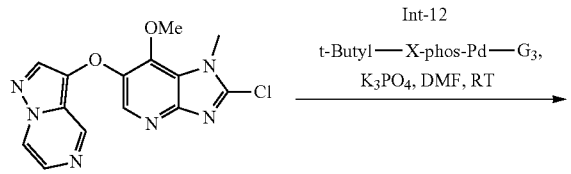

50.3

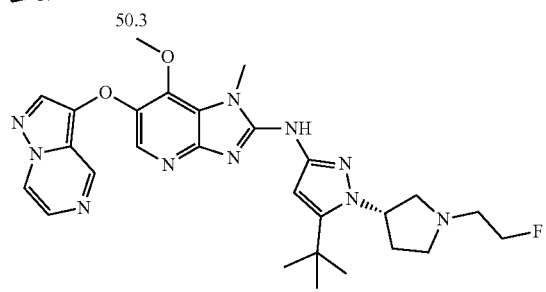

I-50

Synthesis of compound 50.1. Compound 50.1 was prepared from 21.7, following the procedure described in the synthesis of 45.1. The product was used without purification. MS (ES): m/z: 333.5 [M+H]⁺.

Synthesis of compound 50.2. Compound 50.2 was prepared from 50.1, following the procedure described in the synthesis of 45.2. The product was purified by flash column chromatography on silica gel (CombiFlash®, 3.0% methanol in DCM). MS (ES): m/z: 329.3 [M+H]⁺.

Synthesis of compound 50.3. Compound 50.3 was prepared from 50.2, following the procedure described in the synthesis of 45.3. The product was purified by flash column chromatography on silica gel (CombiFlash®, 3.2% methanol in DCM). MS (ES): m/z 306.7 [M+H]⁺.

Synthesis of I-50. Compound I-50 was prepared from 50.3 following the procedure described in the synthesis of Int-45. The product was purified by preparative HPLC. MS (ES): m/z: 549.8 [M+H]⁺, ¹H NMR (DMSO-d₆, 400 MHz): δ 9.79 (s, 1H), 8.96 (s, 1H), 8.66-8.65 (d, J=4.8 Hz, 1H), 8.00 (s, 1H), 7.96 (s, 1H), 7.84-7.83 (d, J=4.8 Hz, 1H), 6.51 (s, 1H), 5.07 (bs, 1H), 4.63-4.60 (m, 1H), 4.51-4.48 (m, 1H), 4.05 (s, 3H), 3.82 (s, 3H), 3.14-3.10 (m, 1H), 2.86-2.80 (m, 3H), 2.77-2.74 (m, 2H), 2.28-2.20 (m, 2H), 1.39 (s, 9H).

Example 51: (S)—N-(5-(tert-butyl)-1-(1-(2-methoxyethyl)pyrrolidin-3-yl)-1H-pyrazol-3-yl)-7-(difluoromethyl)-1-methyl-6-(pyrazolo[1,5-a]pyrazin-3-yloxy)-1H-imidazo[4,5-b]pyridin-2-amine

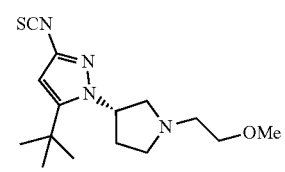

Int-18

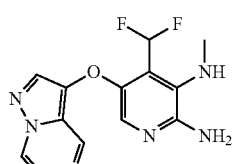

43.2

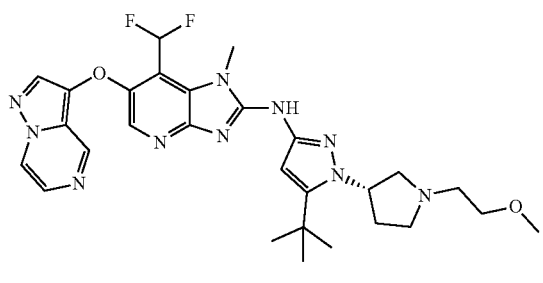

I-51

Synthesis of I-51. To a solution of 43.2 (0.025 g, 0.081 mmol, 1.0 equiv) and Int-18 (0.038 g, 0.122 mmol, 1.5 equiv) in THF (3 mL) was added potassium tert-butoxide (1 M in THF) (0.36 mL, mmol, 2.2 equiv) at −78° C. The reaction mixture was stirred at −78° C. for 30 min. It was poured into ice-water and extracted with ethyl acetate. The combined organic layers were washed with brine, dried over anhydrous sodium sulfate, filtered and concentrated under reduced pressure. The residue was dissolved in THF (5 mL) and N-(3-dimethylaminopropyl)-N-ethylcarbodiimide hydrochloride (0.093 g, 0.489 mmol, 3.0 equiv) was added. The reaction mixture was stirred at 70° C. for 3 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford I-51. MS (ES): m/z: 581.5 [M+H]⁺, ¹H NMR (MeOD, 400 MHz): δ 8.99 (s, 1H), 8.55-8.53 (m, 1H), 8.02 (s, 1H), 7.94 (s, 1H), 7.87-7.86 (d, J=4.8 Hz, 1H), 7.77-7.50 (m, 1H), 6.50 (s, 1H), 5.25 (bs, 1H), 3.91 (s, 3H), 3.63-3.61 (m, 2H), 3.39 (s, 3H), 3.08-2.89 (m, 6H), 2.39-2.29 (m, 2H), 1.46 (s, 9H).

Example 52: (S)—N-(5-(tert-butyl)-1-(1-(2-methoxyethyl)pyrrolidin-3-yl)-1H-pyrazol-3-yl)-7-(difluoromethyl)-1-methyl-6-(pyrazolo[1,5-a]pyrazin-3-yloxy)-1H-imidazo[4,5-b]pyridin-2-amine

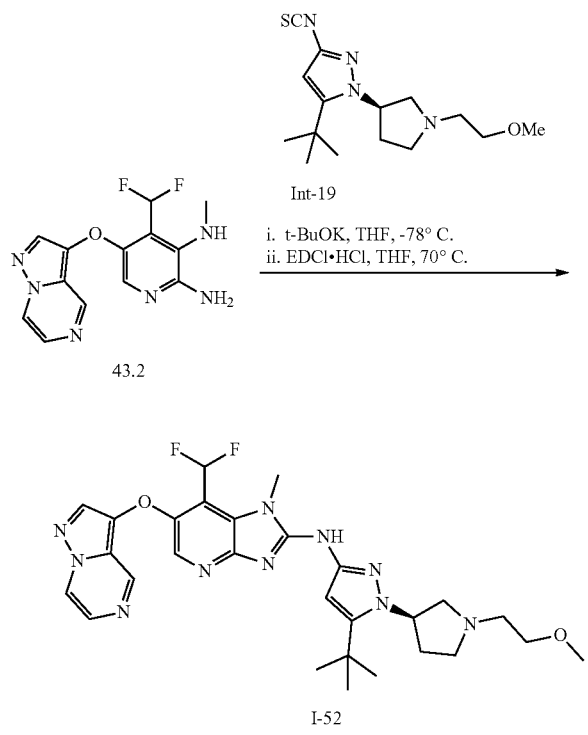

Synthesis of I-52. Compound I-52 was prepared from 43.2 and Int-19 following the procedure described in the synthesis of Int-51. The product was purified by flash column chromatography on silica gel (CombiFlash®, 2.5% methanol in DCM). MS (ES): m/z: 581.4 [M+H]⁺, ¹H NMR (MeOD, 400 MHz): δ 8.99 (s, 1H), 8.55-8.54 (d, J=4.4 Hz, 1H), 8.02 (s, 1H), 7.94 (s, 1H), 7.87-7.86 (d, J=4.8 Hz, 1H), 7.77-7.50 (m, 1H), 6.50 (s, 1H), 5.25 (bs, 1H), 3.91 (s, 3H), 3.63-3.61 (m, 2H), 3.39 (s, 3H), 3.08-2.90 (m, 6H), 2.39-2.29 (m, 2H), 1.46 (s, 9H).

Example 53: N-(5-(tert-butyl)-1-(2-oxaspiro[3.3]heptan-6-yl)-1H-pyrazol-3-yl)-7-(difluoromethyl)-1-methyl-6-(pyrazolo[1,5-a]pyrazin-3-yloxy)-1H-imidazo[4,5-b]pyridin-2-amine

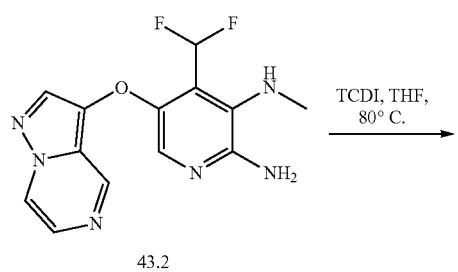

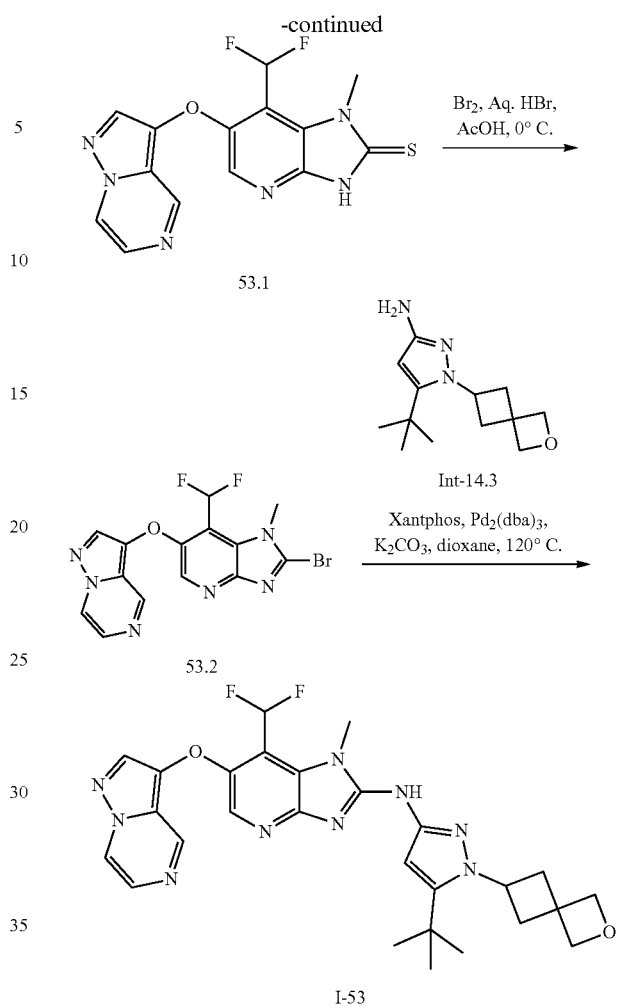

Synthesis of compound 53.1. To a solution of 43.2 (0.280 g, 0.914 mmol, 1.0 equiv) in THF (5 mL) was added 1,1'-thiocarbonyldiimidazole (0.813 g, 4.57 mmol, 5.0 equiv). The reaction mixture was stirred at 80° C. for 1 h. It was cooled to room temperature and poured into ice-water. The precipitated solids were collected by filtration and triturated with hexane to afford 53.1. MS (ES): m/z: 349.0 [M+H]⁺.

Synthesis of compound 53.2. To a solution of 53.1 (0.230 g, 0.660 mmol, 1.0 equiv) in acetic acid (5 mL) was added aqueous hydrobromic acid (0.160 g, 1.98 mmol, 3.0 equiv) at 0° C. followed by bromine (0.528 g, 3.3 mmol, 5.0 equiv). The reaction mixture was stirred for 10 min. It was transferred into saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.0% methanol in DCM) to afford 53.2. MS (ES): m/z 396.1 [M+H]⁺.

Synthesis of I-53. A mixture of 53.2 (0.025 g, 0.063 mmol, 1.0 equiv), Int-14.3 (0.018 g, 0.075 mmol, 1.2 equiv) and potassium carbonate (0.021 g, 0.157 mmol, 2.5 equiv) in 1,4-dioxane (2 mL) was degassed by bubbling through a stream of argon for 10 min. Under argon atmosphere, 4,5-bis(diphenylphosphino)-9,9-dimethylxanthene (0.007 g, 0.012 mmol, 0.2 equiv) and tris(dibenzylideneacetone)dipalladium(0) (0.006 g, 0.0063 mmol, 0.1 equiv) were added, and the mixture was degassed for an additional 5 min. The reaction mixture was stirred at 120° C. for 3 h. It was cooled to room temperature, transferred into water and extracted with ethyl acetate. The combined organic layers were washed with brine, dried over anhydrous sodium sulfate, filtered and concentrated under reduced pressure. The residue was purified by preparative HPLC to afford I-53. MS (ES): m/z: 550.1 [M]$^+$, $^1$H NMR (DMSO-d$_6$, 400 MHz): δ 9.97 (s, 1H), 9.01 (s, 1H), 8.68-8.67 (d, J=4.4 Hz, 1H), 8.12 (s, 1H), 8.02 (s, 1H), 7.87-7.86 (d, J=4.8 Hz, 1H), 7.77-7.50 (m, 1H), 6.52 (s, 1H), 4.96-4.92 (m, 1H), 4.71 (s, 2H), 4.58 (s, 2H), 3.95 (s, 3H), 2.77-2.73 (m, 4H), 1.35 (s, 9H).

Example 54: 2-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl) acetonitrile Example 55: trans-3-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl) cyclobutan-1-ol

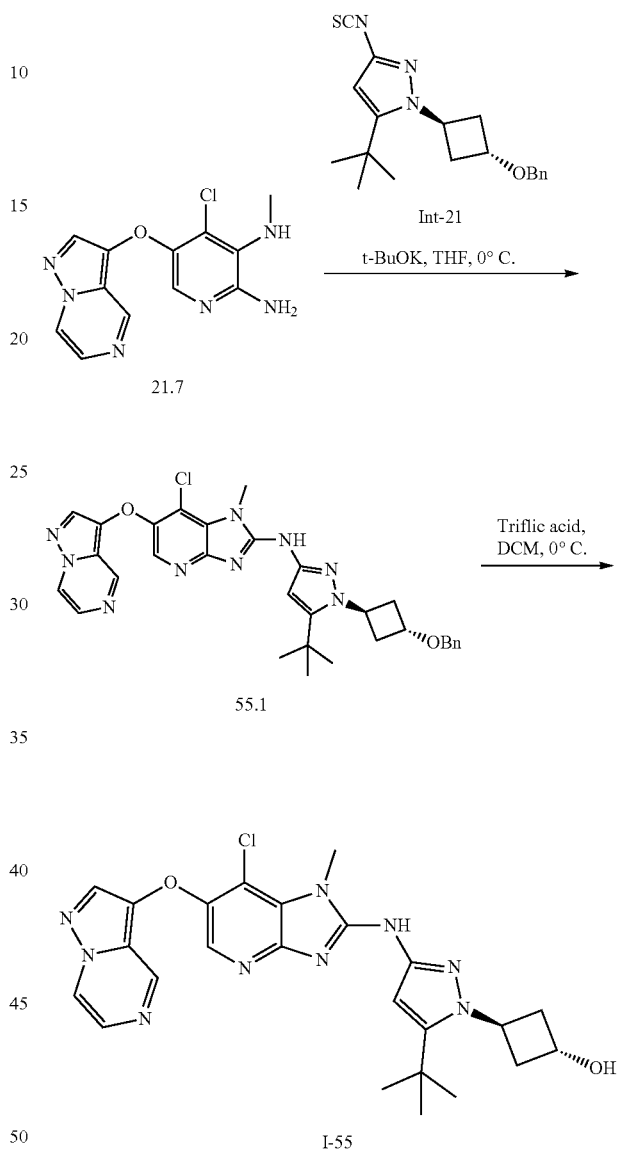

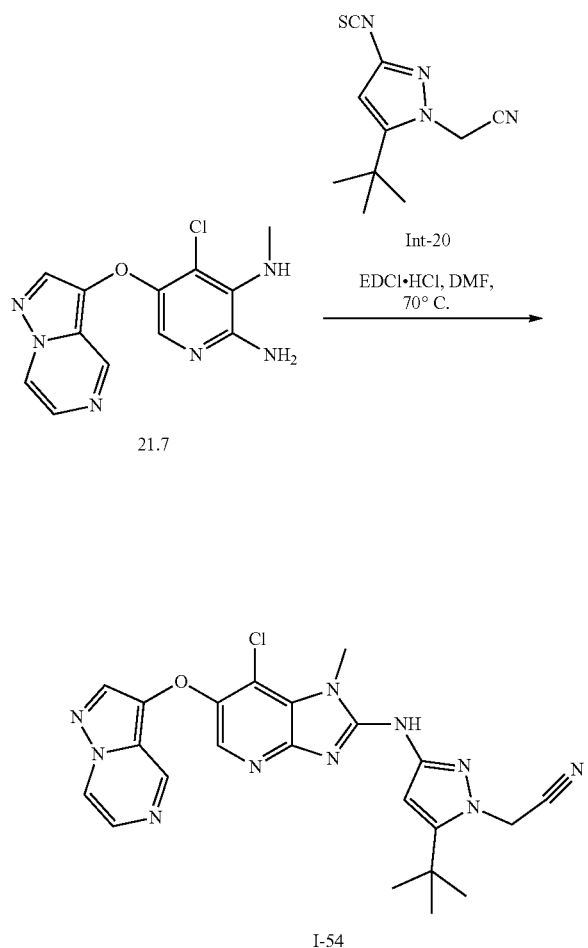

Synthesis of I-54. Compound I-54 was prepared from 21.7 and Int-20 following the procedure described in the synthesis of 1.7. The product was purified by prep HPLC. MS (ES): m/z: 477.6 [M+H]$^+$, $^1$H NMR (DMSO-d$_6$, 400 MHz): δ 10.24 (s, 1H), 8.73-8.72 (d, J=2.8 Hz, 1H), 8.22 (s, 1H), 8.18 (s, 1H), 7.65 (s, 1H), 7.24-7.23 (d, J=2.8 Hz, 1H), 6.69 (s, 1H), 5.49 (s, 2H), 3.94 (s, 3H), 1.40 (s, 9H).

Synthesis of compound 55.1. Compound 55.1 was prepared from 21.7 and Int-21, following the procedure described in the synthesis of I-13. The product was purified by flash column chromatography on silica gel (CombiFlash®, 3% methanol in DCM). MS (ES): m/z: 598.2 [M]$^+$.

Synthesis of I-55. Compound I-55 was prepared from 55.1, following the procedure described in the synthesis of I-23. The product was purified by flash column chromatography on silica gel (CombiFlash®, 5.0% methanol in DCM). MS (ES): m/z: 508.2 [M+H]$^+$, $^1$H NMR (DMSO-d$_6$, 400 MHz): δ 9.96 (s, 1H), 9.00 (s, 1H), 8.68-8.67 (d, J=4.4 Hz, 1H), 8.11 (s, 1H), 8.01 (s, 1H), 7.86-7.85 (d, J=4.8 Hz, 1H), 6.53 (s, 1H), 5.23-5.17 (m, 2H), 4.47 (bs, 1H), 3.95 (s, 3H), 2.75-2.67 (m, 2H), 2.35-2.31 (m, 2H), 1.35 (s, 9H).

Example 56: (R)-5-(tert-butyl)-N-(7-chloro-6-(imidazo[1,2-b]pyridazin-7-yloxy)-1-methyl-1H-imidazo[4,5-b]pyridin-2-yl)-4-(tetrahydrofuran-3-yl)thiazol-2-amine and (S)-5-(tert-butyl)-N-(7-chloro-6-(imidazo[1,2-b]pyridazin-7-yloxy)-1-methyl-1H-imidazo[4,5-b]pyridin-2-yl)-4-(tetrahydrofuran-3-yl)thiazol-2-amine

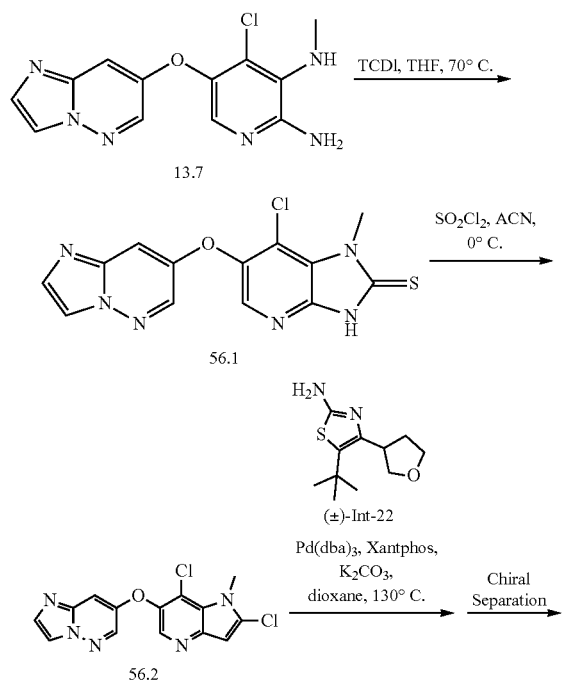

Synthesis of compound 56.1. Compound 56.1 was prepared from 13.7, following the procedure described in the synthesis of 45.1. The product was used without purification. MS (ES): m/z: 333.5 [M+H]$^+$.

Synthesis of compound 56.2. Compound 56.2 was prepared from 56.1, following the procedure described in the synthesis of 45.3. The product was purified by flash column chromatography on silica gel (CombiFlash®, 3.5% methanol in DCM). MS (ES): m/z 336.1 [M+H]$^+$.

Synthesis of compound I-56-a and I-56-b. A mixture of 56.2 (0.097 g, 0.289 mmol, 1.0 equiv), (±)-Int-22 (0.066 g, 0.289 mmol, 1.0 equiv) and potassium carbonate (0.099 g, 0.722 mmol, 2.5 equiv) in 1,4-dioxane (5 mL) was degassed by bubbling through a stream of argon for 10 min. Under argon atmosphere, 4,5-bis(diphenylphosphino)-9,9-dimethylxanthene (0.033 g, 0.057 mmol, 0.2 equiv) and tris(dibenzylideneacetone)dipalladium(0) (0.025 g, 0.028 mmol, 0.1 equiv) were added, and the mixture was degassed for an additional 5 min. The reaction mixture was stirred at 130° C. for 3 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford the racemate I-56. It was subjected to HPLC separation (column: CHIRALPAK IB-N (250 mm×21 mm, 5 μm); mobile phase: (A) 0.1% DEA in n-hexane (B) 0.1% DEA in isopropanol:acetonitrile (70:30); flow rate: 20 mL/min) to afford first eluting fraction (I-56-a) and second eluting fraction (I-56-b). (*Absolute stereochemistry not determined.)

I-56-a: MS (ES): m/z: 525.4 [M+H]$^+$, $^1$H NMR (DMSO-d$_6$, 400 MHz): δ 10.04 (s, 1H), 8.72 (bs, 1H), 8.22 (s, 1H), 8.15 (s, 1H), 7.65 (bs, 1H), 7.22 (s, 1H), 5.26 (bs, 1H), 4.09 (bs, 2H), 3.93 (s, 3H), 3.86-3.83 (m, 2H), 2.36-2.34 (m, 1H), 2.24 (bs, 1H), 1.40 (s, 9H).

I-56-b: MS (ES): m/z: 525.4 [M+H]$^+$, $^1$H NMR (DMSO-d$_6$, 400 MHz): δ 10.04 (s, 1H), 8.73-8.72 (d, J=2.8 Hz, 1H), 8.22 (s, 1H), 8.15 (s, 1H), 7.66-7.65 (d, J=1.2 Hz, 1H), 7.23-7.22 (d, J=2.4 Hz, 1H), 5.28-5.24 (m, 1H), 4.11-4.06 (m, 2H), 3.93 (s, 3H), 3.86-3.82 (m, 2H), 2.40-2.35 (m, 1H), 2.26-2.20 (m, 1H), 1.40 (s, 9H).

Example 57: 3-((7-chloro-1-methyl-6-(pyrazolo[1,5-a]pyrazin-3-yloxy)-1H-imidazo[4,5-b]pyridin-2-yl)amino)-5-cyclopropyl-1-methylpyridin-2(1H)-one

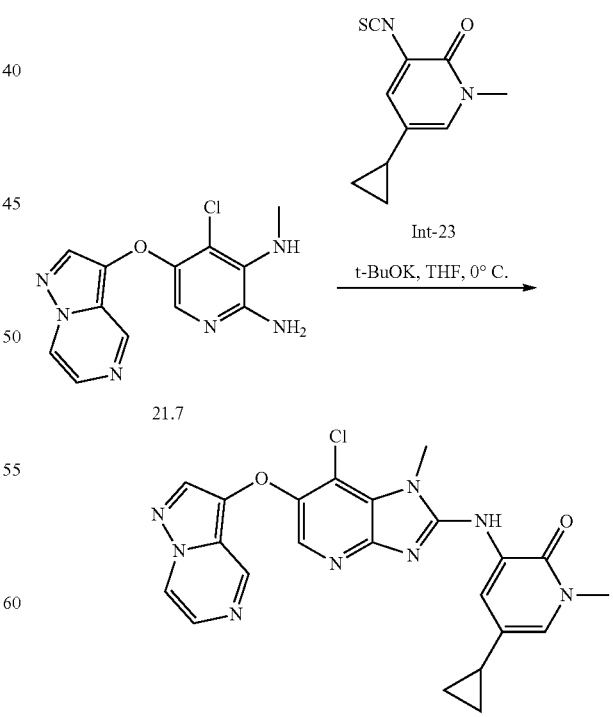

Synthesis of I-57. Compound I-57 was prepared from 21.7 and Int-23, following the procedure described in the synthesis of I-13. The product was purified by flash column chromatography on silica gel (CombiFlash®, 2.5% methanol in DCM). MS (ES): m/z: 463.5 [M]+, 1H NMR (DMSO-d6, 400 MHz): δ 9.04 (s, 1H), 8.70-8.69 (d, J=3.6 Hz, 1H), 8.53 (s, 1H), 8.30-8.29 (d, J=2.0 Hz, 1H), 8.21 (s, 1H), 8.05 (s, 1H), 7.88-7.87 (d, J=4.8 Hz, 1H), 7.25-7.24 (d, J=2.0 Hz, 1H), 3.99 (s, 3H), 3.56 (s, 3H), 1.83-1.79 (m, 1H), 0.90-0.85 (m, 2H), 0.61-0.58 (m, 2H).

Example 58: 5-cyclopropyl-3-((7-methoxy-1-methyl-6-(pyrazolo[1,5-a]pyrazin-3-yloxy)-1H-imidazo[4,5-b]pyridin-2-yl)amino)-1-(2-methoxyethyl)pyridin-2(1H)-one Example 59: 5-cyclopropyl-3-((7-(difluoromethyl)-1-methyl-6-(pyrazolo[1,5-a]pyrazin-3-yloxy)-1H-imidazo[4,5-b]pyridin-2-yl)amino)-1-methylpyridin-2(1H)-one

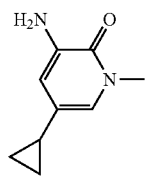

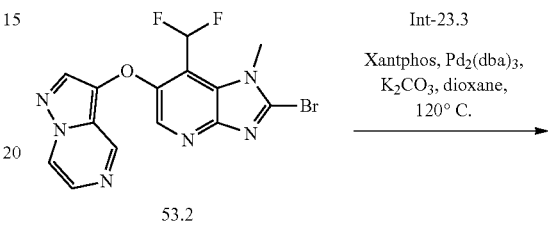

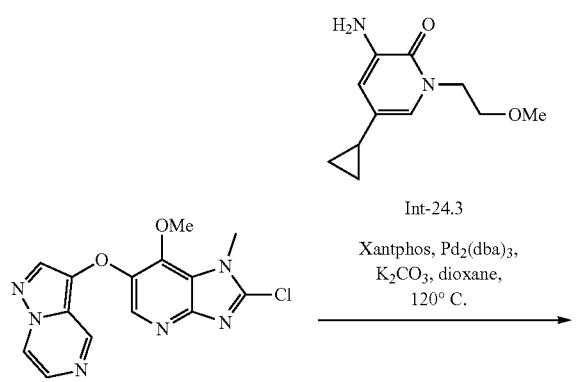

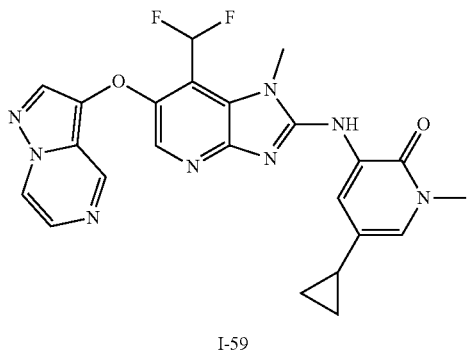

Synthesis of I-58. Compound I-58 was prepared from 51.3 and Int-24.3, following the procedure described in the synthesis of I-53. The product was purified by flash column chromatography on silica gel (CombiFlash®, 3.6% methanol in DCM). MS (ES): m/z: 503.1 [M+H]+, 1H NMR (DMSO-d6, 400 MHz): δ 9.00 (s, 1H), 8.68-8.67 (d, J=4.0 Hz, 1H), 8.35 (s, 1H), 8.29 (s, 1H), 8.13 (s, 1H), 7.99 (s, 1H), 7.86-7.85 (d, J=3.6 Hz, 1H), 7.16 (s, 1H), 4.18 (bs, 2H), 4.11 (s, 3H), 3.90 (s, 3H), 3.67 (bs, 2H), 3.28 (s, 3H), 1.83 (bs, 1H), 0.89-0.88 (m, 2H), 0.59 (bs, 2H).

Synthesis of I-59. Compound I-59 was prepared from 53.2 and Int-23.3, following the procedure described in the synthesis of I-53. The product was purified by flash column chromatography on silica gel (CombiFlash®, 3.6% methanol in DCM). MS (ES): m/z: 479.6 [M]+, 1H NMR (DMSO-d6, 400 MHz): δ 9.03 (s, 1H), 8.71-8.70 (d, J=4.0 Hz, 1H), 8.60 (s, 1H), 8.31-8.30 (d, J=2.0 Hz, 1H), 8.16 (s, 1H), 8.07 (s, 1H), 7.89 (s, 1H), 7.88-7.62 (m, 1H), 7.24-7.23 (d, J=1.6 Hz, 1H), 3.18 (s, 3H), 3.55 (s, 3H), 1.84-1.78 (m, 1H), 0.88-0.84 (m, 2H), 0.60-0.56 (m, 2H).

Example 60: (1R,2S)-2-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol and (1S,2R)-2-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol

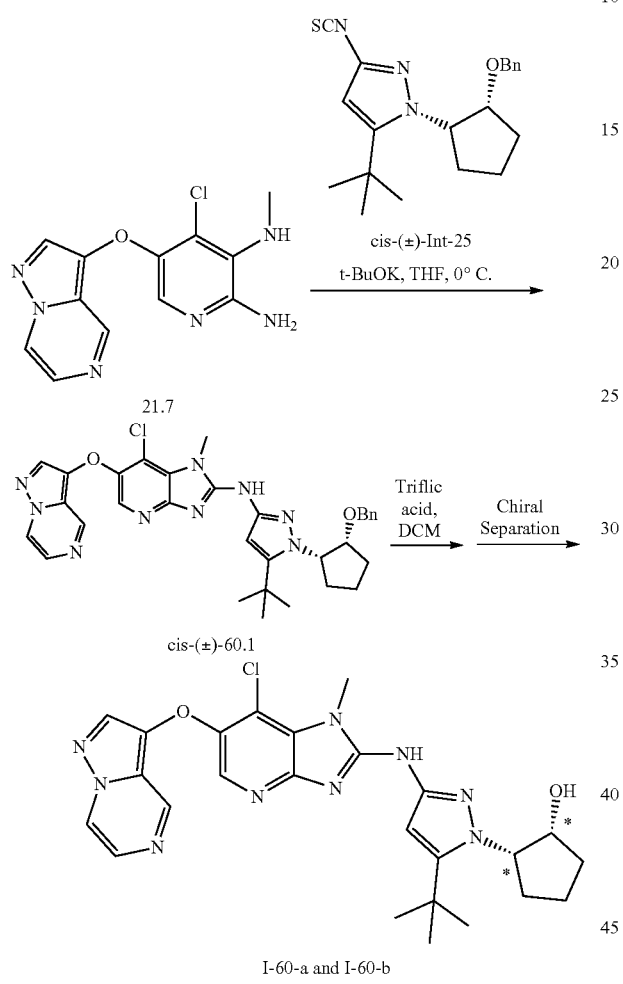

cis-(±)-60.1

I-60-a and I-60-b

Synthesis of compound cis-(±)-60.1. Compound cis-(±)-60.1 was prepared from 21.7 and cis-(±)-Int-25, following the procedure described in the synthesis of I-13. The product was purified by flash column chromatography on silica gel (CombiFlash®, 3% methanol in DCM). MS (ES): m/z: 613.1 [M+H]$^+$.

Synthesis of I-60-a and I-60-b. The racemate I-60 was prepared from cis-(±)-60.1, following the procedure described in the synthesis of I-23. The product was purified by flash column chromatography on silica gel (CombiFlash®, 7.0% methanol in DCM). MS (ES): m/z: 522.4 [M+H]$^+$. The racemate was subjected to HPLC separation (column: CHIRALPAK IB-N (250 mm×21 mm, 5 μm); mobile phase: (A) 0.1% DEA in n-hexane (B) 0.1% DEA in isopropanol:acetonitrile (70:30); flow rate: 22 mL/min) to afford first eluting fraction (I-60-a) and second eluting fraction (I-60-b). (*Absolute stereochemistry not determined.)

I-60-a: MS (ES): m/z: 522.4 [M+H]$^+$, $^1$H NMR (DMSO-d$_6$, 400 MHz): δ 9.90 (s, 1H), 9.01 (s, 1H), 8.68-8.67 (m, 1H), 8.12 (s, 1H), 8.02 (s, 1H), 7.87-7.86 (d, J=4.8 Hz, 1H), 6.51 (s, 1H), 5.00 (bs, 1H), 4.60-4.56 (m, 1H), 4.48 (bs, 1H), 3.96 (s, 3H), 2.16-2.00 (m, 2H), 1.90-1.75 (m, 3H), 1.67-1.60 (m, 1H), 1.41 (s, 9H).

I-60-b: MS (ES): m/z: 522.4 [M+H]$^+$, $^1$H NMR (DMSO-d$_6$, 400 MHz): δ 9.92 (s, 1H), 9.00 (s, 1H), 8.67-8.66 (m, 1H), 8.11 (s, 1H), 8.01 (s, 1H), 7.86-7.85 (d, J=4.8 Hz, 1H), 6.50 (s, 1H), 5.01 (bs, 1H), 4.60-4.54 (m, 1H), 4.47 (bs, 1H), 3.95 (s, 3H), 2.14-2.00 (m, 2H), 1.88-1.75 (m, 3H), 1.65-1.60 (m, 1H), 1.40 (s, 9H).

Example 61: 3-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)propanenitrile

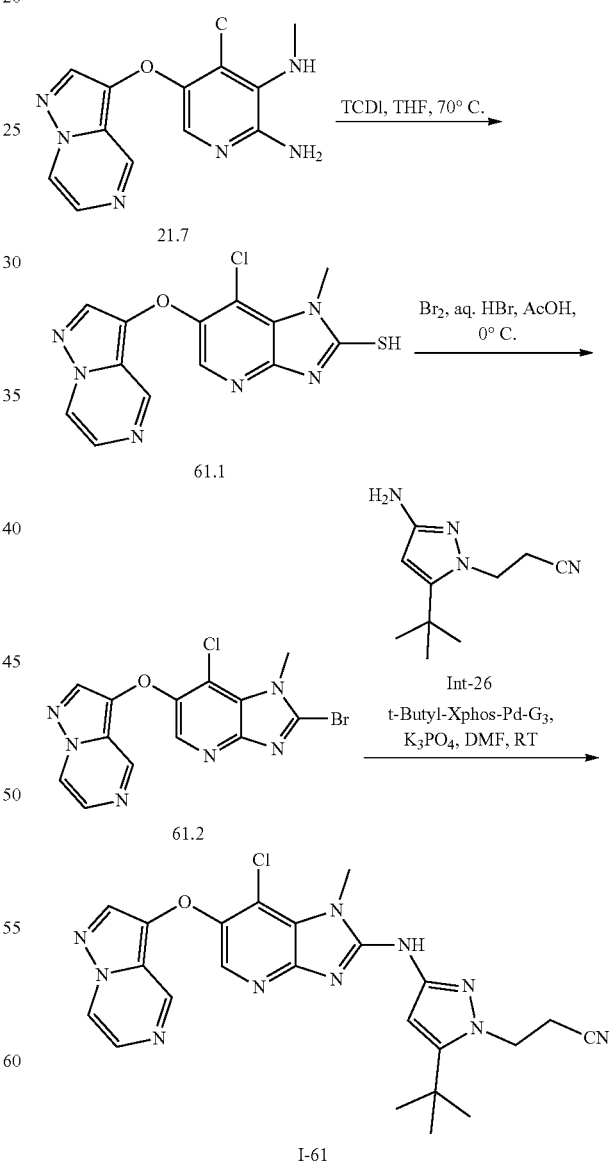

Synthesis of compound 61.1. Compound 61.1 was prepared from 21.7, following the procedure described in the synthesis of 45.1. The product was used without purification. MS (ES): m/z: 333.2 [M+H]⁺.

Synthesis of compound 61.2. Compound 61.2 was prepared from 61.1, following the procedure described in the synthesis of 53.2. The product was purified by flash column chromatography on silica gel (CombiFlash®, 2.8% methanol in DCM). MS (ES): m/z 380.2 [M+H]⁺.

Synthesis of I-61. Compound I-61 was prepared from 61.2 and Int-26, following the procedure described in the synthesis of Int-45. The product was purified by preparative HPLC. MS (ES): m/z: 491.5 [M]⁺, $^1$H NMR (DMSO-$d_6$, 400 MHz): δ 9.02-9.01 (d, J=1.2 Hz, 1H), 8.69-8.68 (m, 1H), 8.49 (s, 1H), 8.12 (s, 1H), 8.03 (s, 1H), 7.87-8.86 (d, J=4.8 Hz, 1H), 6.58 (s, 1H), 4.42-4.39 (t, 2H), 3.95 (s, 3H), 3.14-3.10 (t, 2H), 1.40 (s, 9H).

Example 62: (R)—N-(5-(tert-butyl)-1-(1-(2-fluoroethyl)pyrrolidin-3-yl)-1H-pyrazol-3-yl)-7-methoxy-1-methyl-6-(pyrazolo[1,5-a]pyrazin-3-yloxy)-1H-imidazo[4,5-b]pyridin-2-amine

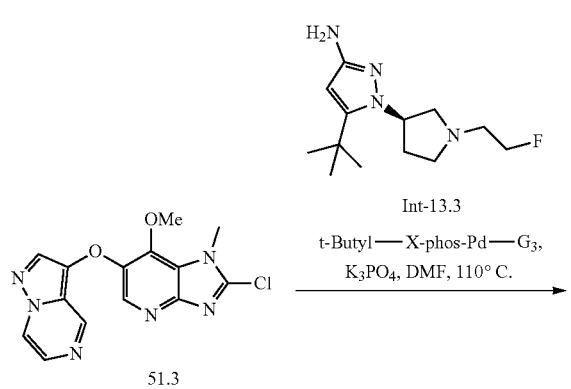

Synthesis of I-62. A mixture of 51.3 (0.050 g, 0.151 mmol, 1.0 equiv), Int-13.3 (0.046 g, 0.181 mmol, 1.2 equiv) and tripotassium phosphate (0.096 g, 0.453 mmol, 3.0 equiv) in DMF (2 mL) was degassed by bubbling through a stream of argon for 10 min. Under argon atmosphere, [(2-di-tert-butylphosphino-2',4',6'-triisopropyl-1,1'-biphenyl)-2-(2'-amino-1,1'-biphenyl)] palladium(II) methanesulfonate (0.035 g, 0.045 mmol, 0.3 equiv) was added, and the mixture was degassed for additional 5 min. The reaction mixture was stirred at 110° C. for 2 h. It was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.8% methanol in DCM) to afford I-62. MS (ES): m/z: 549.6 [M+H]⁺, $^1$H NMR (DMSO-$d_6$, 400 MHz): δ 9.79 (s, 1H), 8.96 (s, 1H), 8.66-8.65 (d, J=4.8 Hz, 1H), 8.00 (s, 1H), 7.96 (s, 1H), 7.84-7.83 (d, J=4.8 Hz, 1H), 6.51 (s, 1H), 5.07 (bs, 1H), 4.63-4.60 (m, 1H), 4.51-4.48 (m, 1H), 4.05 (s, 3H), 3.82 (s, 3H), 3.14-3.10 (m, 1H), 2.86-2.80 (m, 3H), 2.77-2.74 (m, 2H), 2.28-2.20 (m, 2H), 1.39 (s, 9H).

Example 63: 2-(5-(tert-butyl)-3-((7-(difluoromethyl)-1-methyl-6-(pyrazolo[1,5-a]pyrazin-3-yloxy)-1H-imidazo[4,5-b]pyridin-2-yl)amino)-1H-pyrazol-1-yl)acetonitrile

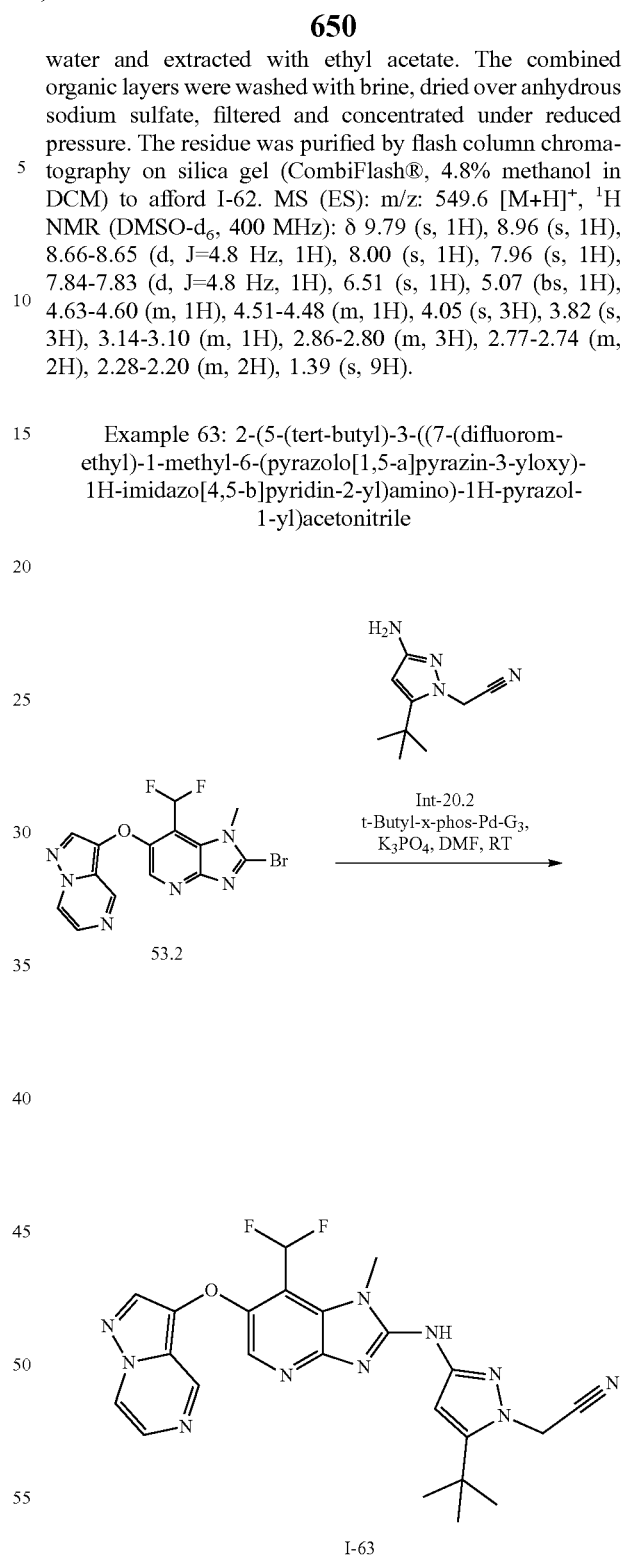

Synthesis of I-63. Compound I-63 was prepared from 53.2 and Int-20.2, following the procedure described in the synthesis of Int-45. The product was purified by preparative HPLC. MS (ES): m/z: 493.03 [M+H]⁺, $^1$H NMR (DMSO-$d_6$, 400 MHz): δ 10.21 (s, 1H), 9.01 (s, 1H), 8.70-8.69 (s, 1H), 8.07 (s, 1H), 8.04 (s, 1H), 7.88-7.87 (d, J=4.8 Hz, 1H), 7.84-7.58 (m, 1H), 6.67 (s, 1H), 5.48 (s, 2H), 3.81 (s, 3H), 1.39 (s, 9H).

Example 64: 5-cyclopropyl-3-((7-methoxy-1-methyl-6-(pyrazolo[1,5-a]pyrazin-3-yloxy)-1H-imidazo[4,5-b]pyridin-2-yl)amino)-1-methylpyridin-2(1H)-one

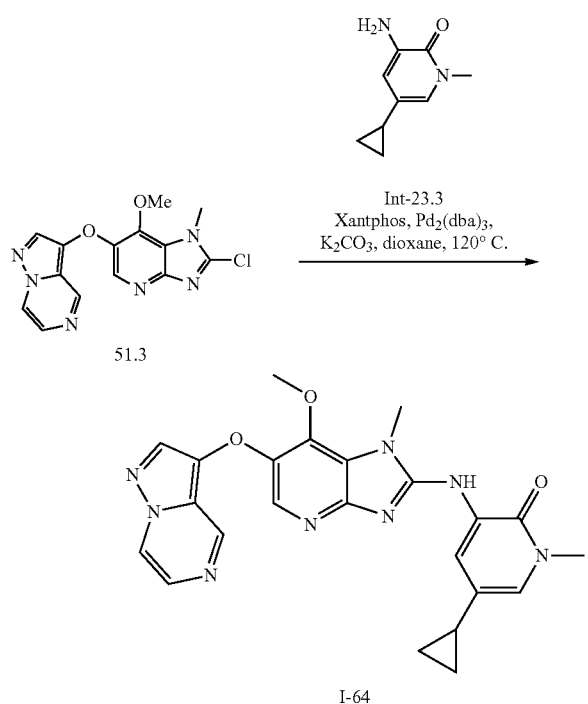

Synthesis of I-64. Compound I-64 was prepared from 51.3 and Int-23.3, following the procedure described in the synthesis of I-53. The product was purified by flash column chromatography on silica gel (CombiFlash®, 4.0% methanol in DCM). MS (ES): m/z: 459.4 [M+H]$^+$, $^1$H NMR (DMSO-d$_6$, 400 MHz): δ 9.00-8.99 (d, J=1.2 Hz, 1H), 8.68-8.67 (m, 1H), 8.34 (s, 1H), 8.32-8.31 (d, J=1.2 Hz, 1H), 8.13 (s, 1H), 7.99 (s, 1H), 7.86-7.85 (d, J=4.8 Hz, 1H), 7.22-7.21 (d, J=2.0 Hz, 1H), 4.11 (s, 3H), 3.90 (s, 3H), 3.56 (s, 3H), 1.84-1.80 (m, 1H), 0.90-0.85 (m, 2H), 0.61-0.57 (m, 2H).

Example 65: 3-((7-chloro-1-methyl-6-(pyrazolo[1,5-a]pyrazin-3-yloxy)-1H-imidazo[4,5-b]pyridin-2-yl)amino)-5-cyclopropyl-1-(2-hydroxyethyl)pyridin-2(1H)-one

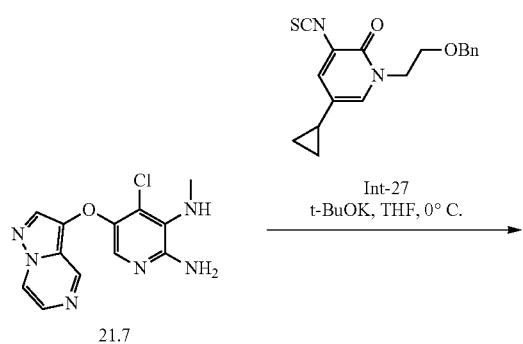

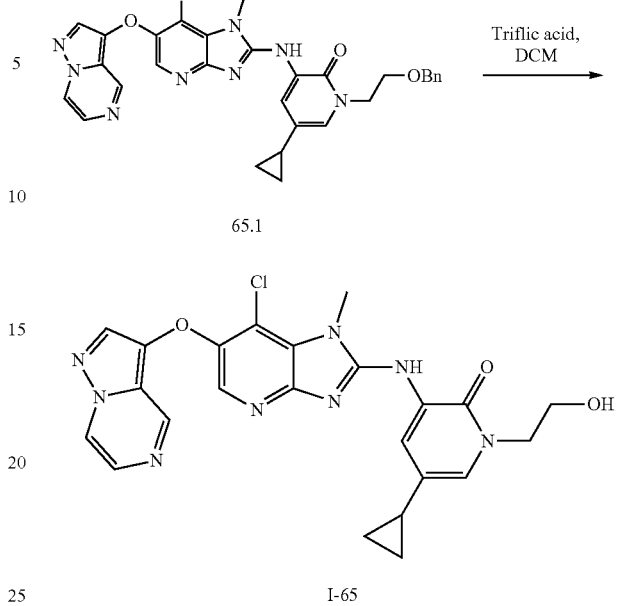

Synthesis of compound 65.1. Compound 65.1 was prepared from 21.7 and Int-27, following the procedure described in the synthesis of I-13. The product was purified by flash column chromatography on silica gel (CombiFlash®, 1.5% methanol in DCM). MS (ES): m/z: 584.0 [M+H]$^+$.

Synthesis of I-65. Compound I-65 was prepared from 65.1, following the procedure described in the synthesis of I-23. The product was purified by flash column chromatography on silica gel (CombiFlash®, 3.0% methanol in DCM). MS (ES): m/z: 493.6 [M+H]$^+$, $^1$H NMR (DMSO-d$_6$, 400 MHz): δ 9.03 (s, 1H), 8.68-8.67 (d, J=4.4 Hz, 1H), 8.56 (s, 1H), 8.21 (s, 1H), 8.05 (s, 1H), 7.87-7.86 (d, J=4.8 Hz, 1H), 7.32 (s, 1H), 6.02-6.00 (d, J=6.8 Hz, 1H), 4.97-4.94 (m, 2H), 4.08-4.05 (m, 2H), 4.00 (s, 3H), 3.72-3.69 (m, 1H), 1.86-1.85 (m, 1H), 1.23 (bs, 4H).

Example 66: ((2S,3S)-3-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)tetrahydrofuran-2-yl)methanol

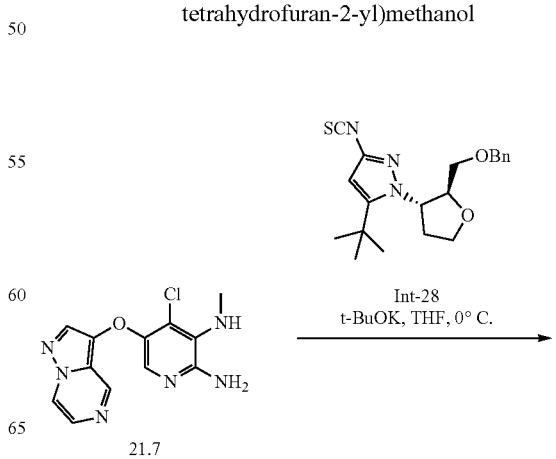

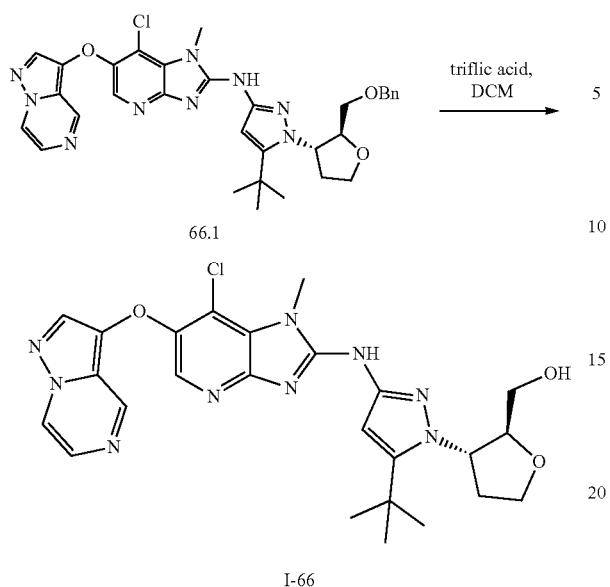

66.1

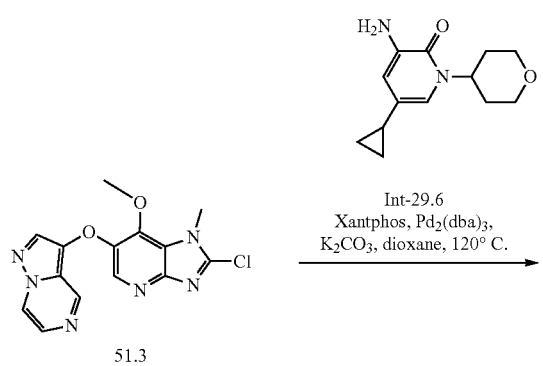

I-66

Synthesis of compound 66.1. Compound 66.1 was prepared from 21.7 and Int-28, following the procedure described in the synthesis of I-13. The product was purified by flash column chromatography on silica gel (CombiFlash®, 3.0% methanol in DCM). MS (ES): m/z: 629.1 [M+H]+.

Synthesis of I-66. Compound I-66 was prepared from 66.1, following the procedure described in the synthesis of I-23. The product was purified by flash column chromatography on silica gel (CombiFlash®, 4.6% methanol in DCM). MS (ES): m/z: 538.4 [M+H]+, LCMS purity: 98.54%, $^1$H NMR (DMSO-$d_6$, 400 MHz): δ 9.99 (s, 1H), 9.00 (s, 1H), 8.68-8.67 (d, J=4.0 Hz, 1H), 8.11 (s, 1H), 8.01 (s, 1H), 7.86-7.85 (d, J=5.2 Hz, 1H), 6.54 (s, 1H), 5.06-5.01 (m, 1H), 4.93-4.90 (m, 1H), 4.37-4.36 (m, 1H), 4.11-4.06 (m, 1H), 3.95 (s, 3H), 3.59-3.54 (m, 1H), 3.49-3.43 (m, 1H), 2.39 (bs, 2H), 2.09-2.01 (m, 1H), 1.40 (s, 9H).

Example 67: 5-cyclopropyl-3-((7-methoxy-1-methyl-6-(pyrazolo[1,5-a]pyrazin-3-yloxy)-1H-imidazo[4,5-b]pyridin-2-yl)amino)-1-(tetrahydro-2H-pyran-4-yl)pyridin-2(1H)-one

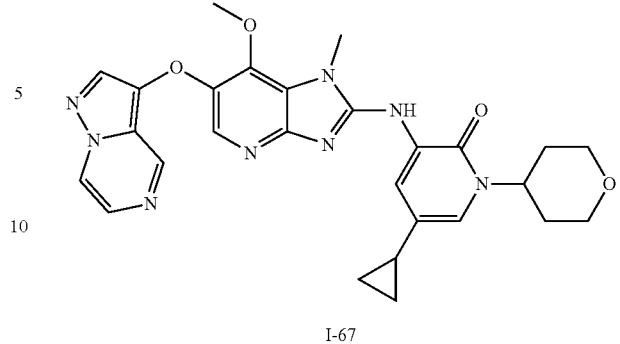

I-67

Synthesis of I-67. Compound I-67 was prepared from 51.3 and Int-29.6, following the procedure described in the synthesis of I-53. The product was purified by flash column chromatography on silica gel (CombiFlash®, 3.0% methanol in DCM). MS (ES): m/z: 529.1 [M+H]+, $^1$H NMR (DMSO-$d_6$, 400 MHz): δ 9.00-8.99 (d, J=1.2 Hz, 1H), 8.68-8.67 (m, 1H), 8.37 (s, 1H), 8.23-8.22 (d, J=2.4 Hz, 1H), 8.13 (s, 1H), 7.98 (s, 1H), 7.86-7.84 (d, J=5.2 Hz, 1H), 7.27-7.26 (d, J=2.0 Hz, 1H), 5.05-4.99 (m, 1H), 4.11 (s, 3H), 4.07-4.01 (m, 2H), 3.90 (s, 3H), 3.54-3.48 (m, 2H), 2.13-2.03 (m, 2H), 1.92-1.87 (m, 1H), 1.75-1.74 (m, 2H), 0.91-0.85 (m, 2H), 0.65-0.61 (m, 2H).

Example 68: 3-((7-chloro-1-methyl-6-(pyrazolo[1,5-a]pyrazin-3-yloxy)-1H-imidazo[4,5-b]pyridin-2-yl)amino)-5-cyclopropyl-1-(tetrahydro-2H-pyran-4-yl)pyridin-2(1H)-one

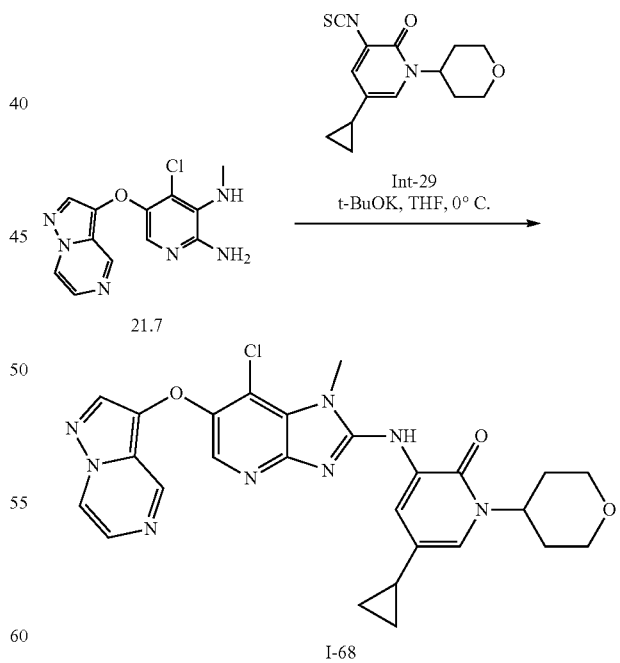

I-68

Synthesis of I-68. Compound I-68 was prepared from 21.7 and Int-29, following the procedure described in the synthesis of I-13. The product was purified by flash column chromatography on silica gel (CombiFlash®, 2.5% methanol in DCM). MS (ES): m/z: 533.7 [M+H], $^1$H NMR (DMSO-d$_6$, 400 MHz): δ 9.02 (s, 1H), 8.69-8.68 (d, J=4 Hz 1H), 8.55 (s, 1H), 8.20-8.19 (m, 2H), 8.04 (s, 1H), 7.87-7.86 (d, J=5.2 Hz, 1H), 7.29 (s, 1H), 5.01 (bs, 1H), 4.03-4.00 (m, 2H), 3.98 (s, 3H), 3.53-3.47 (m, 2H), 2.09-2.05 (m, 2H), 1.91-1.88 (m, 1H), 1.74-1.70 (m, 2H), 0.88-0.86 (m, 2H), 0.63-0.61 (m, 2H).

Example 69: (1R,2S)-2-(5-(tert-butyl)-3-((7-methoxy-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol and (1S,2R)-2-(5-(tert-butyl)-3-((7-methoxy-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol

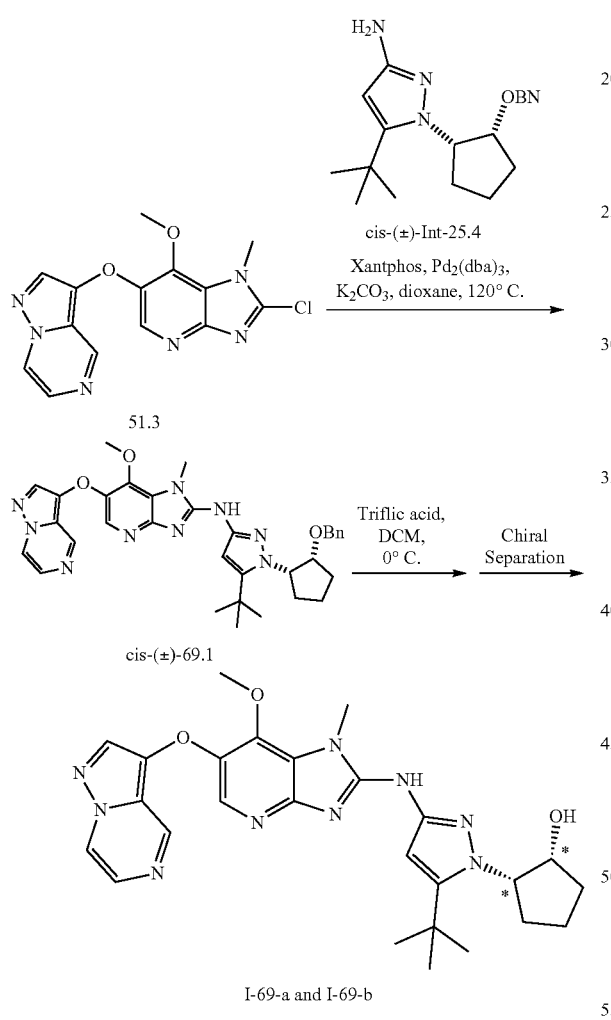

Synthesis of compound cis-(±)-69.1. Compound cis-(±)-69.1 was prepared from 51.3 and cis-(±)-Int-25.4, following the procedure described in the synthesis of I-53. The product was purified by flash column chromatography on silica gel (CombiFlash®, 3.5% methanol in DCM). MS (ES): m/z: 608.5 [M+H]$^+$.

Synthesis of compound I-69-a and I-69-b. The racemate I-69 was prepared from cis-(±)-69.1, following the procedure described in the synthesis of I-23. The product was purified by flash column chromatography on silica gel (CombiFlash®, 5.0% methanol in DCM). It was subjected to HPLC separation: (column: CHIRALPAK IH (250 mm×21 mm, 5 μm); mobile phase: (A) 0.1% DEA in n-hexane, (B) 0.1% DEA in isopropanol:methanol (50:50); flow rate: 20 mL/min) to afford first eluting fraction (I-69-a) and second eluting fraction (I-69-b). (*Absolute stereochemistry not determined.)

I-69-a: MS (ES): m/z: 518.4 [M+H]$^+$, $^1$H NMR (DMSO-d$_6$, 400 MHz): δ 9.73 (s, 1H), 8.98-8.97 (d, J=1.6 Hz, 1H), 8.67-8.66 (m, 1H), 8.03 (s, 1H), 7.97 (s, 1H), 7.84-7.83 (d, J=4.8 Hz, 1H), 6.50 (s, 1H), 5.04-5.02 (d, 1H), 4.58-4.57 (m, 1H), 4.49-4.48 (m, 1H), 4.06 (s, 3H), 3.84 (s, 3H), 2.05-2.01 (m, 2H), 1.79-1.76 (m, 2H), 1.67-1.61 (m, 2H), 1.41 (s, 9H).

I-69-b: MS (ES): m/z: 518.4 [M+H]$^+$, $^1$H NMR (DMSO-d$_6$, 400 MHz): δ 9.72 (s, 1H), 8.96 (bs, 1H), 8.66-8.65 (m, 1H), 8.02 (s, 1H), 7.95 (s, 1H), 7.83-7.82 (d, J=4.8 Hz, 1H), 6.49 (s, 1H), 5.03-5.02 (d, 1H), 4.57-4.56 (m, 1H), 4.48-4.47 (m, 1H), 4.05 (s, 3H), 3.83 (s, 3H), 2.03-1.99 (m, 2H), 1.78-1.74 (m, 2H), 1.65-1.60 (m, 2H), 1.39 (s, 9H).

Example 70: 3-((7-chloro-1-methyl-6-(pyrazolo[1,5-a]pyrazin-3-yloxy)-1H-imidazo[4,5-b]pyridin-2-yl)amino)-5-cyclopropyl-1-((1s,3s)-3-hydroxycyclobutyl)pyridin-2(1H)-one

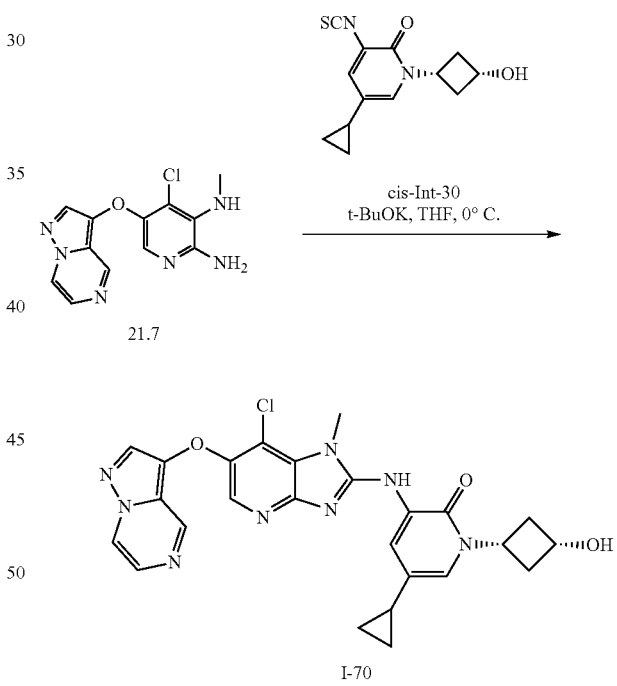

Synthesis of I-70. Compound I-70 was prepared from 21.7 and cis-Int-30, following the procedure described in the synthesis of I-13. The product was purified by flash column chromatography on silica gel (CombiFlash®, 4.5% methanol in DCM). MS (ES): m/z: 519.6 [M+H]$^+$, $^1$H NMR (DMSO-d$_6$, 400 MHz): δ 8.98 (s, 1H), 8.67-8.66 (d, J=4.4 Hz 1H), 8.34 (s, 1H), 8.23 (s, 1H), 8.11 (s, 1H), 7.97 (s, 1H), 7.84-7.83 (d, J=4.8 Hz 1H), 7.24 (s, 1H), 5.30 (bs, 1H), 4.68-4.64 (m, 1H), 4.00 (bs, 1H), 3.88 (s, 3H), 2.77-2.76 (m, 2H), 2.16-2.14 (m, 2H), 1.91 (bs, 1H), 0.90-0.87 (m, 2H), 0.62-0.61 (m, 2H).

Example 72: (1R,2S)-2-(5-(tert-butyl)-3-((7-(difluoromethyl)-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol and (1S,2R)-2-(5-(tert-butyl)-3-((7-(difluoromethyl)-1-methyl-6-(pyrazolo[1,5-a]pyrazin-3-yloxy)-1H-imidazo[4,5-b]pyridin-2-yl)amino)-1H-pyrazol-1-yl)cyclopentan-1-ol

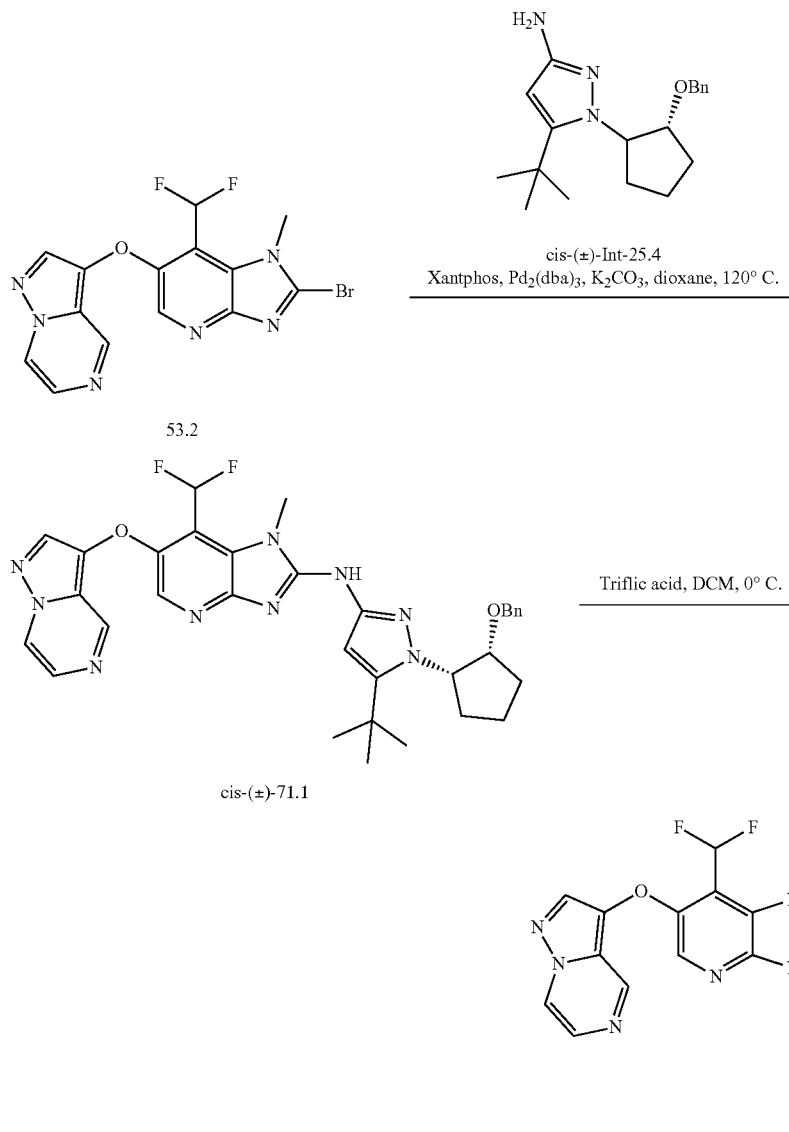

I-71-a and I-71-b

Synthesis of compound cis-(±)-71.1. Compound cis-(±)-71.1 was prepared from 53.2 and cis-(±)-Int-25.4, following the procedure described in the synthesis of I-53. The product was purified by flash column chromatography on silica gel (CombiFlash®, 3.5% methanol in DCM). MS (ES): m/z: 628.5 [M+H]$^+$.

Synthesis of compounds I-71-a and I-71-b. The racemate I-71 was prepared from cis-(±)-71.1, following the procedure described in the synthesis of I-23. The product was purified by flash column chromatography on silica gel (CombiFlash®, 5.0% methanol in DCM). MS (ES): m/z: 538.1 [M+H]$^+$. It was subjected to SFC separation (column: CHIRALPAK IH (250 mm×21 mm, 5 μm); mobile phase: (A) liquid carbon dioxide, (B) 0.1% DEA in methanol; flow rate: 80 mL/min) to afford first eluting fraction (I-71-a) and second eluting fraction (I-71-b). (*Absolute stereochemistry not determined.)

I-71-a: MS (ES): m/z: 538.4 [M+H]$^+$, $^1$H NMR (MeOD, 400 MHz): δ 8.98 (s, 1H), 8.53-8.52 (d, J=4.8 Hz, 1H), 7.99 (s, 1H), 7.92 (s, 1H), 7.82 (bs, 1H), 7.75-7.48 (m, 1H), 6.44 (s, 1H), 4.71-4.65 (m, 2H), 3.89 (s, 3H), 2.20-2.16 (m, 2H), 1.91-1.86 (m, 2H), 1.72-1.62 (m, 2H), 1.46 (s, 9H).

I-71-b: MS (ES): m/z: 538.4 [M+H]$^+$, $^1$H NMR (MeOD, 400 MHz): δ 8.99 (s, 1H), 8.54-8.53 (d, J=4.8 Hz, 1H), 8.02 (s, 1H), 7.93 (s, 1H), 7.87-7.85 (m, 1H), 7.76-7.49 (m, 1H), 6.47 (s, 1H), 4.72-4.68 (m, 2H), 3.91 (s, 3H), 2.22-2.18 (m, 2H), 1.90-1.87 (m, 2H), 1.72-1.63 (m, 2H), 1.48 (s, 9H).

Example 72: (R)-5-cyclopropyl-3-((7-methoxy-1-methyl-6-(pyrazolo[1,5-a]pyrazin-3-yloxy)-1H-imidazo[4,5-b]pyridin-2-yl)amino)-1-(tetrahydro-2H-pyran-3-yl)pyridin-2(1H)-one and (S)-5-cyclopropyl-3-((7-methoxy-1-methyl-6-(pyrazolo[1,5-a]pyrazin-3-yloxy)-1H-imidazo[4,5-b]pyridin-2-yl)amino)-1-(tetrahydro-2H-pyran-3-yl)pyridin-2(1H)-one (I-72-a) and second eluting fraction (I-72-b). (*Absolute stereochemistry not determined.)

I-72-a: MS (ES): m/z: 529.4 [M+H]$^+$, $^1$H NMR (DMSO-d$_6$, 400 MHz): δ 8.99 (s, 1H), 8.67-8.65 (m, 1H), 8.36 (s, 1H), 8.23 (s, 1H), 8.11 (s, 1H), 7.97 (s, 1H), 7.84-7.83 (m, 1H), 7.28 (s, 1H), 4.86 (s, 1H), 4.09 (s, 3H), 3.88 (s, 3H), 3.85-3.82 (m, 2H), 3.68-3.63 (m, 1H), 3.50-3.45 (m, 1H), 2.15-2.13 (m, 1H), 1.94-1.85 (m, 2H), 1.77-1.70 (m, 2H), 0.89-0.87 (m, 2H), 0.61-0.60 (m, 2H).

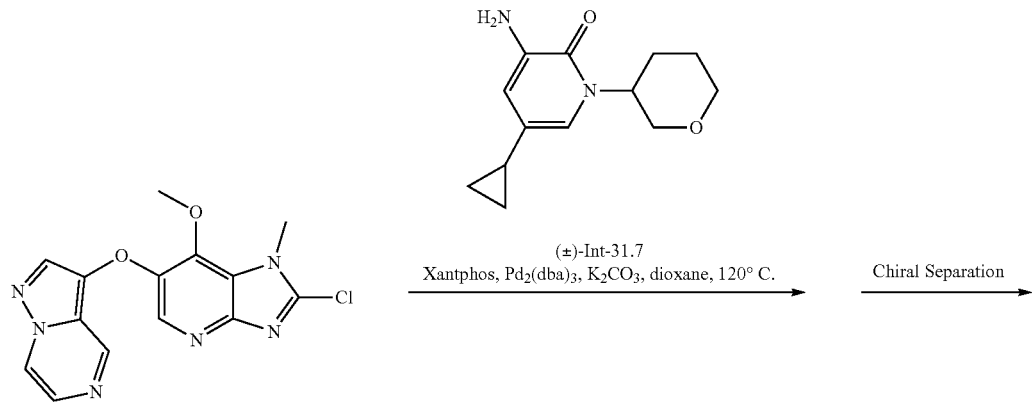

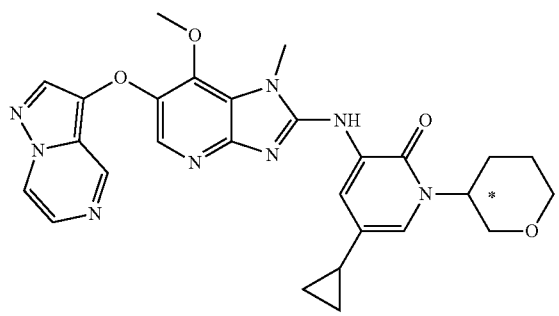

I-72-a and I-72-b

Synthesis of compound I-72-a and I-72-b. Racemate I-72 was prepared from 51.3 and (±)-Int-31.7, following the procedure described in the synthesis of I-53. The product was purified by flash column chromatography on silica gel (CombiFlash®, 3.1% methanol in DCM). It was subjected to HPLC separation (column: CHIRALPAK IB-N (250 mm×21 mm, 5 μm); mobile phase: (A) 0.1% DEA in n-hexane, (B) 0.1% DEA in isopropanol:acetonitrile (70:30); flow rate: 20 mL/min) to afford first eluting fraction I-72-b: MS (ES): m/z: 529.4 [M+H]$^+$, $^1$H NMR (DMSO-d$_6$, 400 MHz): δ 8.99 (s, 1H), 8.67-8.65 (m, 1H), 8.37 (s, 1H), 8.23 (s, 1H), 8.12-8.11 (d, J=1.6 Hz, 1H), 7.98-7.97 (d, J=1.6 Hz, 1H), 7.84-7.83 (m, 1H), 7.28 (s, 1H), 4.86 (s, 1H), 4.09 (s, 3H), 3.88 (s, 3H), 3.82-3.80 (m, 2H), 3.68-3.63 (m, 1H), 3.50-3.45 (m, 1H), 2.15-2.13 (m, 1H), 1.94-1.82 (m, 2H), 1.77-1.70 (m, 2H), 0.89-0.87 (m, 2H), 0.61-0.60 (m, 2H).

Example 73: (S)-3-((7-chloro-1-methyl-6-(pyrazolo[1,5-a]pyrazin-3-yloxy)-1H-imidazo[4,5-b]pyridin-2-yl)amino)-5-cyclopropyl-1-(tetrahydro-2H-pyran-3-yl)pyridin-2(1H)-one and (R)-3-((7-chloro-1-methyl-6-(pyrazolo[1,5-a]pyrazin-3-yloxy)-1H-imidazo[4,5-b]pyridin-2-yl)amino)-5-cyclopropyl-1-(tetrahydro-2H-pyran-3-yl)pyridin-2(1H)-one (I-72-a) and second eluting fraction (I-72-b). (*Absolute stereochemistry not determined.)

I-72-a: MS (ES): m/z: 533.3 [M+H]$^+$, $^1$H NMR (DMSO-d$_6$, 400 MHz): δ 9.03 (s, 1H), 8.69-8.68 (d, J=4.8 Hz, 1H), 8.55 (s, 1H), 8.23-8.22 (d, J=4.4 Hz, 1H), 8.20 (s, 1H), 8.04 (s, 1H), 7.87-7.86 (d, J=4.8 Hz, 1H), 7.31 (s, 1H), 4.86-4.83 (m, 1H), 3.98 (s, 3H), 3.82-3.80 (m, 2H), 3.68-3.63 (m, 1H),

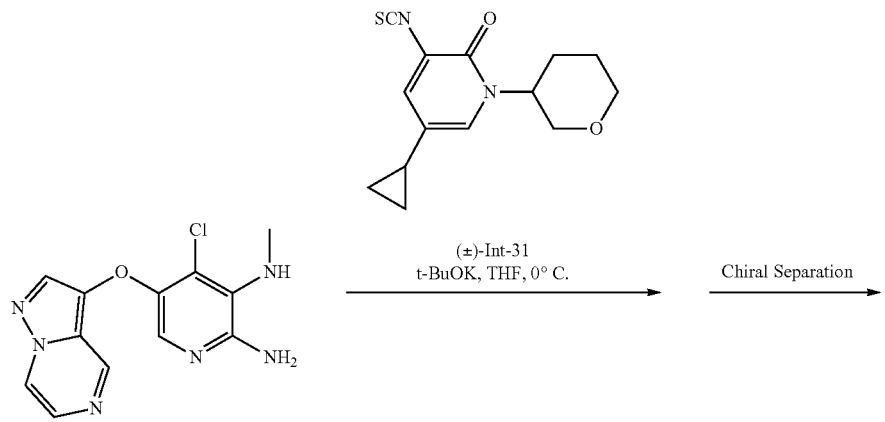

21.7

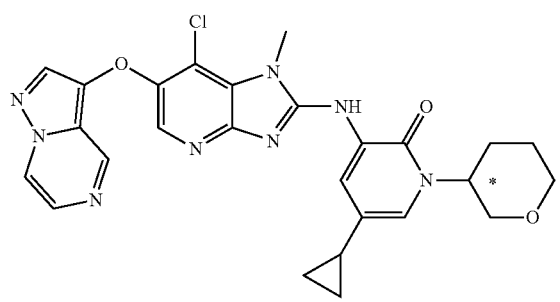

I-73-a and I-73-b

Synthesis of compounds I-73-a and I-73-b. Racemate I-73 was prepared from 21.7 and (±)-Int-31, following the procedure described in the synthesis of I-13. The product was purified by flash column chromatography on silica gel (CombiFlash®, 2.1% methanol in DCM). It was subjected to HPLC separation (column: CHIRALPAK IB-N (250 mm×21 mm, 5 μm); mobile phase: (A) 0.1% DEA in n-hexane, (B) 0.1% DEA in isopropanol:acetonitrile (70:30); flow rate: 20 mL/min) to afford first eluting fraction 3.51-3.46 (m, 1H), 2.18-2.10 (m, 1H), 1.94-1.88 (m, 2H), 1.77-1.70 (m, 2H), 0.89-0.87 (m, 2H), 0.61-0.60 (m, 2H).

I-72-b: MS (ES): m/z: 533.3 [M+H]$^+$, $^1$H NMR (DMSO-d$_6$, 400 MHz): δ 9.03 (s, 1H), 8.69-8.68 (d, J=4.8 Hz, 1H), 8.55 (s, 1H), 8.23-8.22 (d, J=4.4 Hz, 1H), 8.20 (s, 1H), 8.04 (s, 1H), 7.87-7.86 (d, J=4.8 Hz, 1H), 7.31 (s, 1H), 4.88-4.83 (m, 1H), 3.98 (s, 3H), 3.84-3.81 (m, 2H), 3.68-3.63 (m, 1H), 3.51-3.46 (m, 1H), 2.18-2.13 (m, 1H), 1.94-1.88 (m, 2H), 1.77-1.70 (m, 2H), 0.89-0.86 (m, 2H), 0.61-0.60 (m, 2H).

Example 74: cis-5-cyclopropyl-1-(3-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one Synthesis of I-74. Compound I-74 was prepared from 74.1, following the procedure described in the synthesis of I-23. The product was purified by flash column chromatography on silica gel (CombiFlash®, 5.0% methanol in DCM). MS (ES): m/z: 515.7 [M+H]$^+$, $^1$H NMR (DMSO-d$_6$, 400

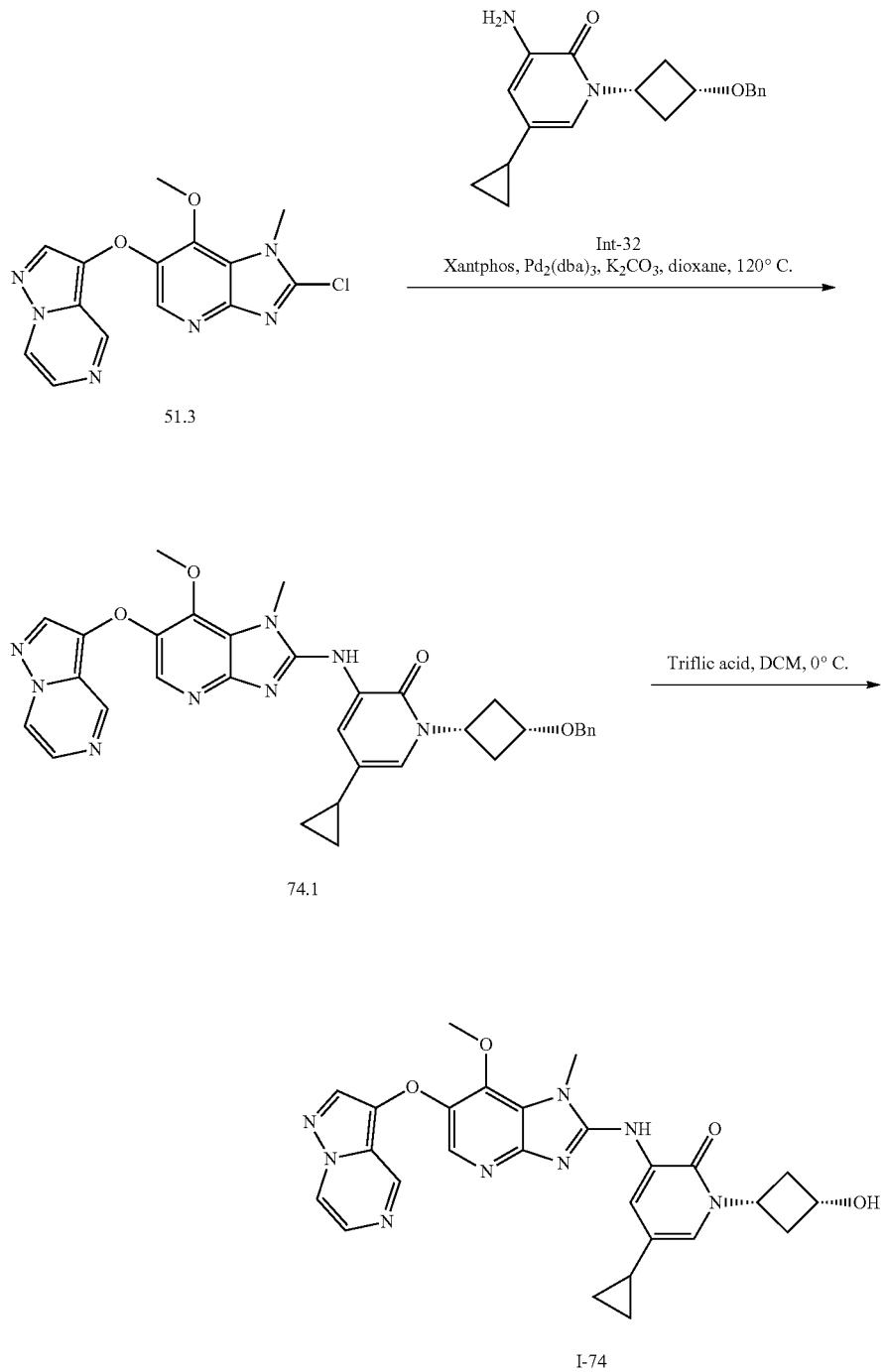

Synthesis of compound 74.1. Compound 74.1 was prepared from 51.3 and Int-32, following the procedure described in the synthesis of I-53. The product was purified by flash column chromatography on silica gel (CombiFlash®, 3.2% methanol in DCM). MS (ES): m/z: 605.5 [M+H]$^+$.

MHz): δ 8.98 (s, 1H), 8.67-8.66 (d, J=4.4 Hz, 1H), 8.34 (s, 1H), 8.23 (s, 1H), 8.11 (s, 1H), 7.97 (s, 1H), 7.84-7.83 (d, J=4.8 Hz, 1H), 7.24 (s, 1H), 5.30-5.28 (m, 1H), 4.68-4.64 (m, 1H), 4.09 (s, 3H), 4.00 (bs, 1H), 3.88 (s, 3H), 2.77-2.76 (m, 2H), 2.16-2.14 (m, 2H), 1.91 (bs, 1H), 0.90-0.87 (m, 2H), 0.62-0.61 (m, 2H).

Example 75: trans-5-cyclopropyl-1-(3-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one Synthesis of I-75. Compound I-75 was prepared from 75.1, following the procedure described in the synthesis of I-23. The product was purified by flash column chromatography on silica gel (CombiFlash®, 4.5% methanol in DCM). MS (ES): m/z: 515.7 [M+H]$^+$, $^1$H NMR (DMSO-d$_6$, 400

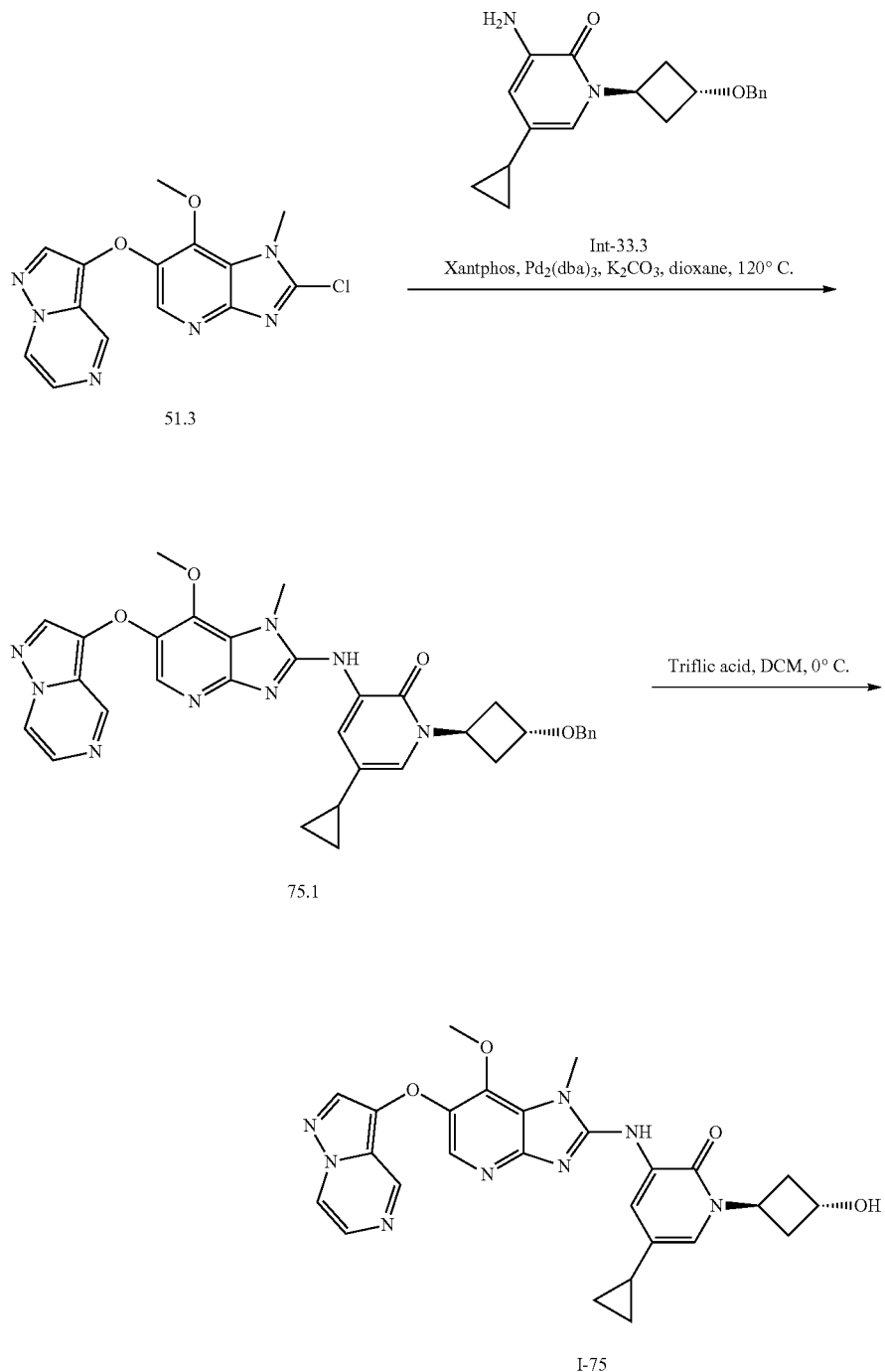

Synthesis of compound 75.1. Compound 75.1 was prepared from 51.3 and Int-33.3, following the procedure described in the synthesis of I-53. The product was purified by flash column chromatography on silica gel (CombiFlash®, 3.2% methanol in DCM). MS (ES): m/z: 605.5 [M+H]$^+$.

MHz): δ 8.99 (s, 1H), 8.67-8.66 (d, J=4.4 Hz, 1H), 8.35 (s, 1H), 8.23 (s, 1H), 8.11 (s, 1H), 7.97 (s, 1H), 7.84-7.83 (d, J=4.8 Hz, 1H), 7.25 (bs, 1H), 5.42-5.38 (m, 1H), 5.24-5.23 (d, 1H), 4.39-4.38 (m, 1H), 4.09 (s, 3H), 3.88 (s, 3H), 2.67-2.61 (m, 4H), 1.91-1.86 (m, 1H), 0.90-0.85 (m, 2H), 0.63-0.61 (m, 2H).

Example 76: (3R,4S)-4-(5-(tert-butyl)-3-((7-chloro-6-((6-cyclopropylimidazo[1,5-a]pyrimidin-3-yl)oxy)-1-methyl-1H-imidazo[4,5-b]pyridin-2-yl)amino)-1H-pyrazol-1-yl)tetrahydrofuran-3-ol and (3S,4R)-4-(5-(tert-butyl)-3-((7-chloro-6-((6-cyclopropylimidazo[1,5-a]pyrimidin-3-yl)oxy)-1-methyl-1H-imidazo[4,5-b]pyridin-2-yl)amino)-1H-pyrazol-1-yl)tetrahydrofuran-3-ol
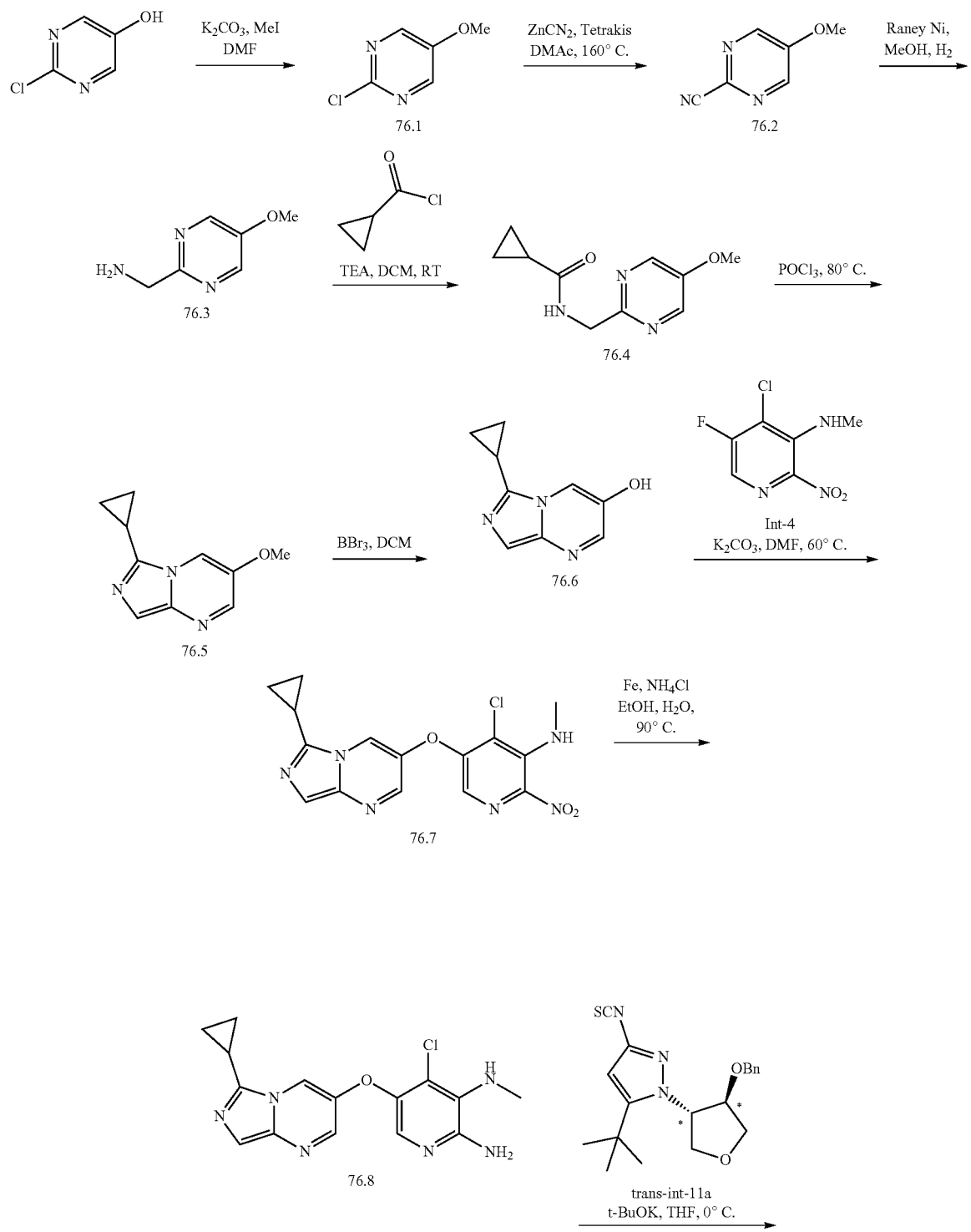

-continued
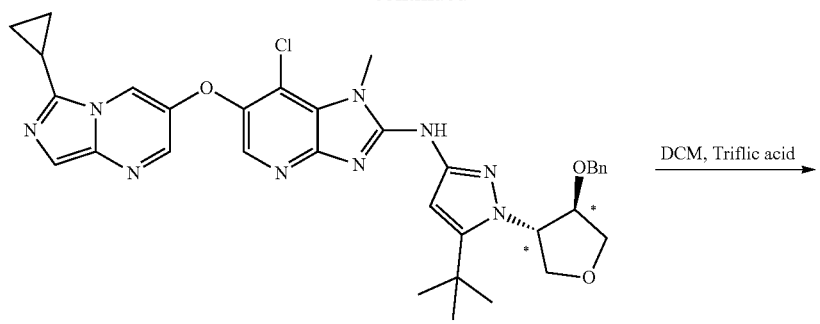
trans-76.9-a
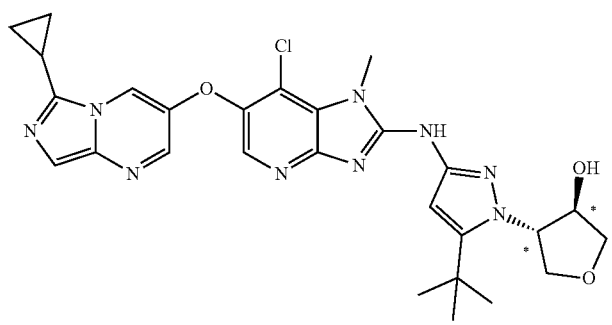
I-76-a
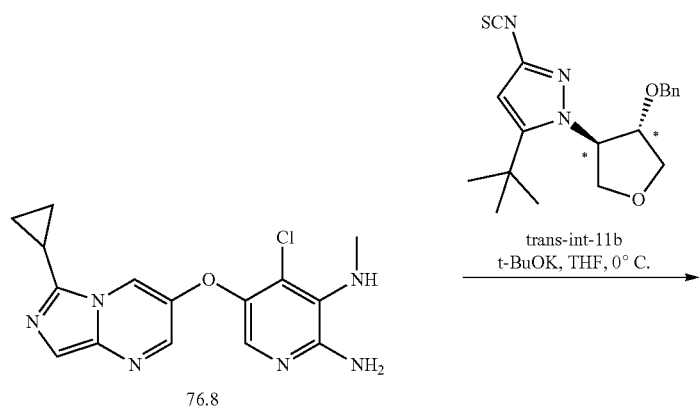
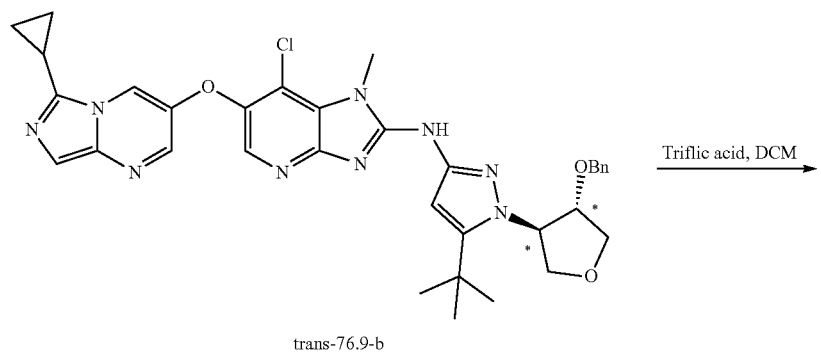
trans-76.9-b

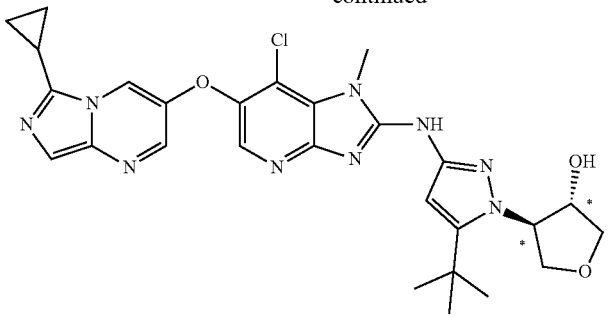

I-76-b

Synthesis of compound 76.1. To a solution of 2-chloropyrimidin-5-ol (25 g, 191.5 mmol, 1.0 equiv) in DMF (250 mL) was added potassium carbonate (79.3 g, 574.5 mmol, 3.0 equiv) followed by methyl iodide (32.63 g, 229.8 mmol, 1.2 equiv). The reaction mixture was stirred at 60° C. for 30 min. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford 76.1. MS (ES): m/z 145.5 [M+H]$^+$.

Synthesis of compound 76.2. A solution of 76.1 (21 g, 145.2 mmol, 1.0 equiv) in dimethylacetamide (200 mL) was degassed by bubbling through a stream of argon for 10 min. Under argon atmosphere, zinc cyanide (18.68 g, 159.7 mmol, 1.1 equiv) was added, and the mixture was degassed for 5 min. To the mixture was added tetrakis(triphenylphosphine)palladium(0) (8.38 g, 7.26 mmol, 0.05 equiv), and the reaction mixture was stirred at 160° C. for 1 h. It was cooled to room temperature, poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane as eluant) to afford 76.2. $^1$H NMR (DMSO-d$_6$, 400 MHz): δ 8.78-8.75 (m, 2H), 4.03 (s, 3H).

Synthesis of compound 76.3. A mixture of compound 76.2 (2.6 g, 19.24 mmol, 1.0 equiv) and Raney nickel (1.3 g) in methanol (25 mL) was stirred under hydrogen (1 atm) at room temperature for 12 h. It was filtered through a pad of Celite® and rinsed with methanol. The filtrate was concentrated under reduced pressure to afford 76.3. MS (ES): m/z 140.2 [M+H]$^+$.

Synthesis of compound 76.4. To a solution of 76.3 (2.3 g, 16.53 mmol, 1.0 equiv) and triethylamine (6.9 mL, 49.59 mmol, 3.0 equiv) in DCM (20 mL) was added cyclopropyl carbonyl chloride (1.81 g, 17.35 mmol, 1.05 equiv) at room temperature, and the mixture was stirred for 1 h. It was transferred into ice, stirred and extracted with DCM. The combined organic layers were washed with brine, dried over anhydrous sodium sulfate, filtered and concentrated under reduced pressure. The residue was purified by flash column chromatography on silica gel (CombiFlash®, 2.1% methanol in DCM) to afford 76.4. MS (ES): m/z 208.2 [M+H]$^+$.

Synthesis of compound 76.5. A solution of 76.4 (0.910 g, 4.39 mmol, 1.0 equiv) in phosphorous oxychloride (9 mL) was stirred at 80° C. for 1 h. It was transferred into ice-water, neutralized by saturated sodium bicarbonate stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in DCM) to afford 76.5. MS (ES): m/z 190.2 [M+H]$^+$.

Synthesis of compound 76.6. To a solution of 76.5 (0.385 g, 2.03 mmol, 1.0 equiv) in DCM (5 mL) was added boron tribromide (5.8 mL, 60.9 mmol, 30 equiv) at 0° C. The reaction mixture was stirred at room temperature for 16 h. It was transferred into ice cold saturated sodium bicarbonate solution and extracted with ethyl acetate. The combined organic layers were washed with brine, dried over anhydrous sodium sulfate, filtered and concentrated under reduced pressure to afford 76.6. MS (ES): m/z 176.1 [M+H]$^+$.

Synthesis of compound 76.7. A mixture of 76.6 (0.285 g, 1.63 mmol, 1.0 equiv), Int-4 (0.334 g, 1.63 mmol, 1.0 equiv) and potassium carbonate (0.674 g, 4.89 mmol, 3.0 equiv) in DMF (3 mL) was stirred at 60° C. for 2 h. It was cooled to room temperature, filtered through a pad of Celite®, poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.3% methanol in DCM) to afford 76.7. MS (ES): m/z 361.5 [M+H]$^+$.

Synthesis of compound 76.8. Compound 76.8 was prepared from 76.7, following the procedure described in the synthesis of 3.7. The product was purified by flash column chromatography on silica gel (CombiFlash®, 1.8% methanol in DCM). MS (ES): m/z 331.5 [M+H]$^+$.

Synthesis of compound trans-76.9-a. Compound trans-76.9-a was prepared from 76.8 and trans-Int-11a, following the procedure described in the synthesis of I-13. The product was purified by flash column chromatography on silica gel (CombiFlash®, 2.5% methanol in DCM). MS (ES): m/z: 655.1 [M+H]$^+$. (*Absolute stereochemistry not determined.)

Synthesis of I-76-a. Compound I-76-a was prepared from trans-76.9-a, following the procedure described in the synthesis of I-23. The product was purified by flash column chromatography on silica gel (CombiFlash®, 4.5% methanol in DCM). MS (ES): m/z: 565.7 [M+H]$^+$, $^1$H NMR (DMSO-d$_6$, 400 MHz): δ 10.03 (s, 1H), 8.35 (s, 1H), 8.22-8.21 (d, J=2.8 Hz, 1H), 8.15 (s, 1H), 7.41 (s, 1H), 6.58 (s, 1H), 5.55-5.54 (m, 1H), 4.92 (bs, 1H), 4.56 (bs, 1H), 4.31-4.26 (m, 1H), 4.16-4.12 (m, 1H), 3.96 (s, 3H), 3.83-3.79 (m, 1H), 3.72-3.68 (m, 1H), 2.38-2.34 (m, 1H), 1.41 (s, 9H), 0.95-0.87 (m, 4H). (*Absolute stereochemistry not determined.)

Synthesis of compound trans-76.9-b. Compound trans-76.9-b was prepared from 76.8 and trans-Int-11b, following the procedure described in the synthesis of I-13. The product was purified by flash column chromatography on silica gel (CombiFlash®, 2.5% methanol in DCM). MS (ES): m/z: 655.1 [M+H]$^+$.

Synthesis of I-76-b. Compound I-76-b was prepared from trans-76.9-b, following the procedure described in the synthesis of I-23. The product was purified by flash column chromatography on silica gel (CombiFlash®, 4.5% methanol in DCM). MS (ES): m/z: 564.7 [M+H]$^+$, $^1$H NMR (DMSO-d$_6$, 400 MHz): δ 10.02 (s, 1H), 8.35 (bs, 1H), 8.21-8.20 (d, J=2.8 Hz, 1H), 8.13 (s, 1H), 7.39 (s, 1H), 6.56 (s, 1H), 5.54-5.53 (d, 1H), 4.91 (bs, 1H), 4.55 (bs, 1H), 4.29-4.25 (m, 1H), 4.14-4.11 (m, 1H), 3.94 (s, 3H), 3.81-3.78 (m, 1H), 3.70-3.66 (m, 1H), 2.39-2.34 (m, 1H), 1.39 (s, 9H), 0.93-0.83 (m, 4H).

Example 77: trans-3-(3-((7-chloro-1-methyl-6-(pyrazolo[1,5-a]pyrazin-3-yloxy)-1H-imidazo[4,5-b]pyridin-2-yl)amino)-5-cyclopropyl-2-oxopyridin-1(2H)-yl)cyclobutane-1-carbonitrile Example 78: 3-((7-chloro-1-methyl-6-(pyrazolo[1,5-a]pyridin-3-yloxy)-1H-imidazo[4,5-b]pyridin-2-yl)amino)-5-cyclopropyl-1-(2-hydroxyethyl)pyridin-2(1H)-one

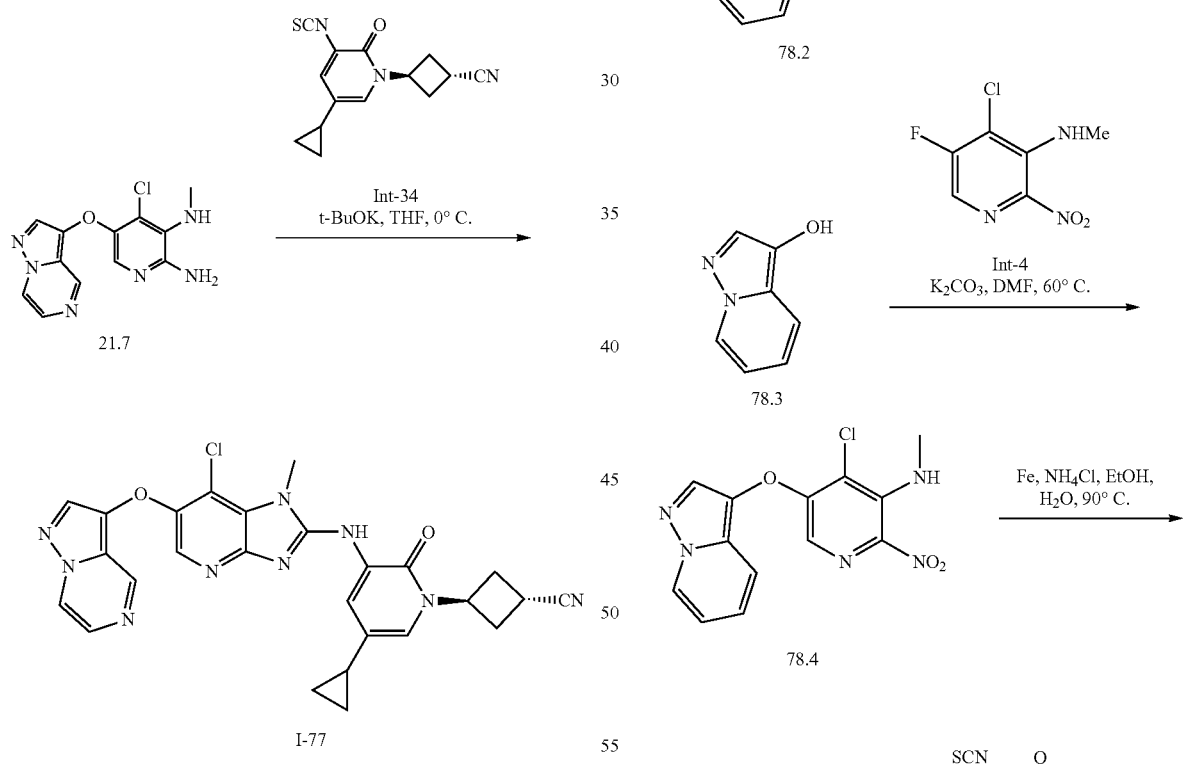

Synthesis of I-77. Compound I-77 was prepared from 21.7 and Int-34, following the procedure described in the synthesis of I-13. The product was purified by flash column chromatography on silica gel (CombiFlash®, 3.1% methanol in DCM). MS (ES): m/z: 528.2 [M+H]$^+$, $^1$H NMR (CDCl$_3$, 400 MHz): δ 9.02 (s, 1H), 8.78 (s, 1H), 8.27 (bs, 2H), 7.87-7.86 (d, J=4.4 Hz 1H), 7.76 (s, 1H), 7.61 (s, 1H), 7.05 (s, 1H), 5.40-5.37 (m, 1H), 4.12 (s, 3H), 3.12-3.08 (m, 2H), 3.00-2.94 (m, 1H), 2.65-2.61 (m, 2H), 1.99-1.94 (m, 1H), 1.03-0.98 (m, 2H), 0.78-0.76 (m, 2H).

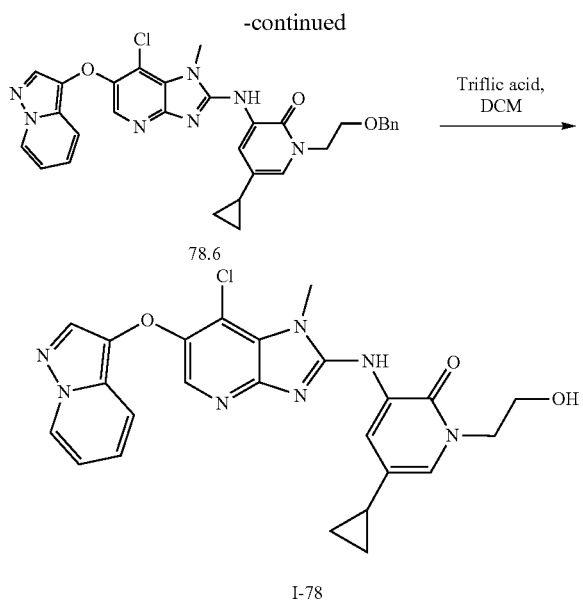

Synthesis of compound 78.6. Compound 78.6 was prepared from 78.5 and Int-27, following the procedure described in the synthesis of I-13. The product was purified by flash column chromatography on silica gel (CombiFlash®, 1.4% methanol in DCM). MS (ES): m/z: 583.0 [M+H]+.

Synthesis of I-78. Compound I-78 was prepared from 78.6, following the procedure described in the synthesis of I-23. The product was purified by flash column chromatography on silica gel (CombiFlash®, 2.8% methanol in DCM). MS (ES): m/z: 492.6 [M+H]+; $^1$H NMR (DMSO-$d_6$, 400 MHz): δ 8.63-8.61 (d, J=7.2 Hz, 1H), 8.49 (s, 1H), 8.02-8.00 (d, J=8.0 Hz, 2H), 8.27-8.26 (d, J=2.4 Hz, 1H), 7.52-7.50 (d, J=8.8 Hz, 1H), 7.20-7.15 (m, 2H), 6.91-6.88 (m, 1H), 4.93-4.90 (m, 1H), 4.06-4.03 (m, 2H), 3.99 (s, 3H), 3.71-3.67 (m, 2H), 1.83-1.79 (m, 1H), 0.88-0.84 (m, 2H), 0.58-0.54 (m, 2H).

Example 79: trans-3-((7-chloro-1-methyl-6-(pyrazolo[1,5-a]pyridin-3-yloxy)-1H-imidazo[4,5-b]pyridin-2-yl)amino)-5-cyclopropyl-1-(3-hydroxycyclobutyl)pyridin-2(1H)-one

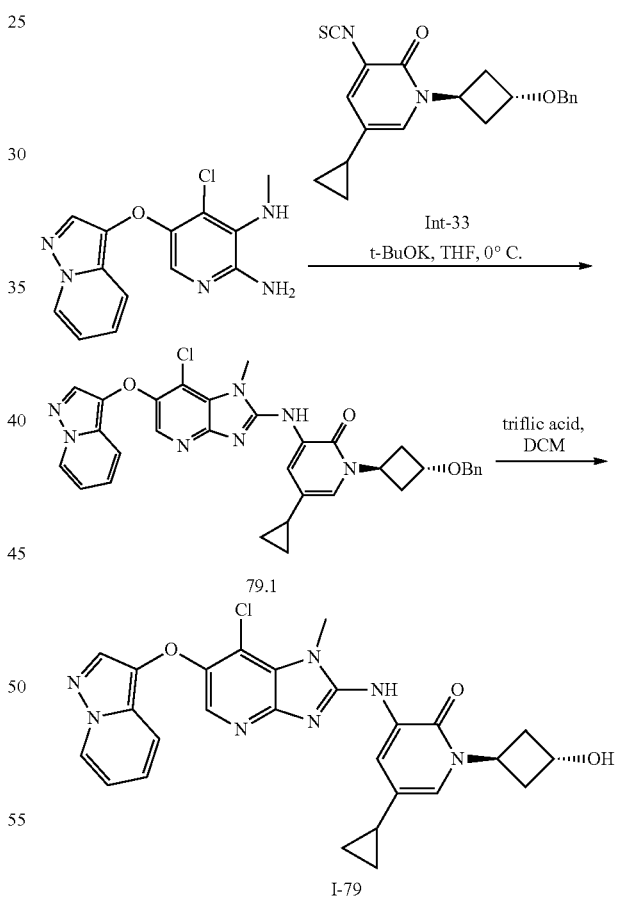

Synthesis of compound 78.1. To a solution of pyrazolo[1,5-a]pyridine (2.0 g, 16.93 mmol, 1.0 equiv) in DMF (20 mL) was added phosphoryl chloride (4.75 mL, 50.79 mmol, 3.0 equiv). The reaction mixture was stirred at room temperature for 1 h. It was concentrated under reduced pressure to afford a residue, which was dissolved in DCM and washed with 2N sodium hydroxide. The organic layer was washed with brine, dried over anhydrous sodium sulfate, filtered and concentrated under reduced pressure to afford 78.1. MS (ES): m/z 147.1 [M+H]+.

Synthesis of compound 78.2. To a solution of 78.1 (2.2 g, 15.05 mmol, 1.0 equiv) in DCM (50 mL) was added potassium fluoride (1.30 g, 22.57 mmol, 1.5 equiv) at 0° C. followed by addition of meta-chloroperoxybenzoic acid (3.88 g, 22.57 mmol, 1.5 equiv). The reaction mixture was stirred at room temperature for 2 h. It was cooled to 0° C. and saturated sodium bicarbonate solution was added, and the mixture was stirred for 30 min. The organic layer was separated, washed with aq. sodium bisulfite, dried over anhydrous sodium sulfate, filtered and concentrated under reduced pressure. The residue was purified by flash column chromatography on silica gel (CombiFlash®, 2.2% methanol in DCM) to afford 78.2. MS (ES): m/z 163.2 [M+H]+.

Synthesis of compound 78.3. To a solution of 78.2 (1.6 g, 9.87 mmol, 1.0 equiv) in methanol (20 mL) was added potassium carbonate (6.81 g, 49.35 mmol, 5.0 equiv), and the reaction mixture was stirred at room temperature for 30 min. It was filtered and the filtrate was concentrated under reduced pressure. The residue was purified by flash column chromatography on silica gel (CombiFlash®, 2.5% methanol in DCM) to afford 78.3. MS (ES): m/z 135.1 [M+H]+.

Synthesis of compound 78.4. Compound 78.4 was prepared from 78.3 and Int-4, following the procedure described in the synthesis of 76.7. The product was purified by flash column chromatography on silica gel (CombiFlash®, 25% ethyl acetate in hexane). MS (ES): m/z 320.5 [M+H]+.

Synthesis of compound 78.5. Compound 78.5 was prepared from 78.4, following the procedure described in the synthesis of 3.7. The product was purified by flash column chromatography on silica gel (CombiFlash®, 3.5% methanol in DCM). MS (ES): m/z 290.7 [M+H]+.

Synthesis of compound 79.1. Compound 79.1 was prepared from 78.5 and Int-33, following the procedure described in the synthesis of I-13. The product was purified by flash column chromatography on silica gel (CombiFlash®, 3.0% methanol in DCM). MS (ES): m/z: 609.1 [M+H]+.

Synthesis of I-79. Compound I-79 was prepared from 79.1, following the procedure described in the synthesis of I-23. The product was purified by flash column chromatography on silica gel (CombiFlash®, 3.5% methanol in DCM). MS (ES): m/z: 518.5 [M]+, ¹H NMR (DMSO-d₆, 400 MHz): δ 8.63-8.61 (d, J=7.2 Hz, 1H), 8.50 (s, 1H), 8.20 (s, 1H), 8.02-7.99 (d, J=7.2 Hz, 2H), 7.51-7.49 (d, J=9.2 Hz, 1H), 7.27 (s, 1H), 7.20-7.16 (t, J=6.8 Hz, 8.8 Hz, 1H), 6.91-6.88 (J=6.4 Hz, 7.2 Hz, 1H), 5.42-5.38 (m, 1H), 5.24-5.23 (m, 1H), 4.38 (bs, 1H), 3.98 (s, 3H), 2.60-2.55 (m, 2H), 2.34-2.29 (m, 2H), 1.91-1.87 (m, 1H), 0.88-0.86 (m, 2H), 0.61-0.60 (m, 2H).

Example 80: cis-3-(3-((7-chloro-1-methyl-6-(pyrazolo[1,5-a]pyrazin-3-yloxy)-1H-imidazo[4,5-b]pyridin-2-yl)amino)-5-cyclopropyl-2-oxopyridin-1(2H)-yl)cyclobutane-1-carbonitrile

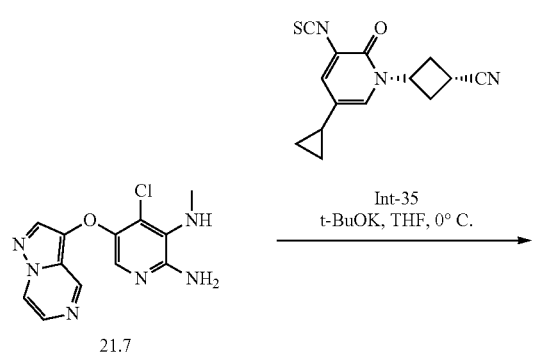

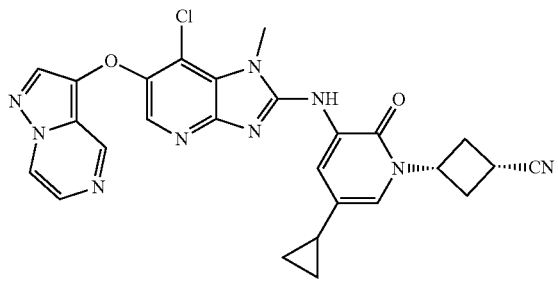

Synthesis of I-80. Compound I-80 was prepared from 21.7 and Int-35, following the procedure described in the synthesis of I-13. The product was purified by flash column chromatography on silica gel (CombiFlash®, 3.1% methanol in DCM). MS (ES): m/z: 528.3 [M+H]+, ¹H NMR (DMSO-d₆, 400 MHz): δ 9.02 (s, 1H), 8.69-8.68 (d, J=4.0 Hz 1H), 8.50 (s, 1H), 8.18 (s, 1H), 8.16-8.15 (d, J=2.0 Hz, 1H), 8.03 (s, 1H), 7.87-7.86 (d, J=4.8 Hz 1H), 7.68-7.67 (d, J=2.0 Hz 1H), 5.21-5.17 (m, 1H), 4.02 (s, 3H), 3.16-3.12 (m, 1H), 2.91-2.85 (m, 2H), 1.96-1.92 (m, 1H), 1.23 (bs, 2H), 0.98-0.93 (m, 2H), 0.67-0.64 (m, 2H).

Example 81: (S)-3-((7-chloro-1-methyl-6-(pyrazolo[1,5-a]pyrazin-3-yloxy)-1H-imidazo[4,5-b]pyridin-2-yl)amino)-5-cyclopropyl-1-(3-hydroxy-2-methylpropyl)pyridin-2(1H)-one and (R)-3-((7-chloro-1-methyl-6-(pyrazolo[1,5-a]pyrazin-3-yloxy)-1H-imidazo[4,5-b]pyridin-2-yl)amino)-5-cyclopropyl-1-(3-hydroxy-2-methylpropyl)pyridin-2(1H)-one

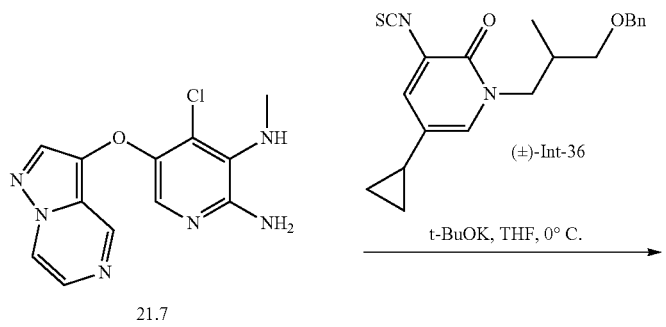

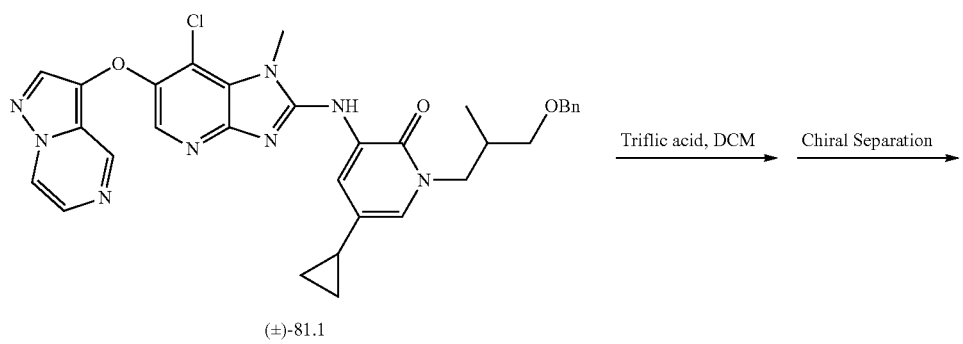

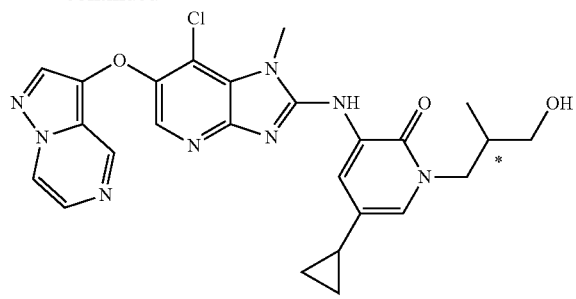

I-81-a and I-81-b

Synthesis of compound (±)-81.1. Compound (±)-81.1 was prepared from 21.7 and (±)-Int-36, following the procedure described in the synthesis of I-13. The product was purified by flash column chromatography on silica gel (CombiFlash®, 2.5% methanol in DCM). MS (ES): m/z: 612.1 [M+H]+.

Synthesis of I-81-a and I-81-b. Racemate I-81 was prepared from (±)-81.1, following the procedure described in the synthesis of I-23. The product was purified by flash column chromatography on silica gel (CombiFlash®, 3.8% methanol in DCM). MS (ES): m/z 521.2 [M+H]+. It was subjected to HPLC purification (column: CHIRALPAK IH (250 mm×21 mm, 5 μm); mobile phase: (A) 0.1% DEA in hexane, (B) 0.1% DEA in isopropanol:methanol (30:70); flow rate: 18 mL/min) to afford first eluting fraction (I-81-a) and second eluting fraction (I-81-b). (*Absolute stereochemistry not determined.)

I-81-a: MS (ES): m/z: 521.2 [M+H]+, $^1$H NMR (DMSO-d$_6$, 400 MHz): δ 9.04 (s, 1H), 8.71-8.69 (d, J=4.8 Hz, 1H), 8.53 (bs, 1H), 8.30 (s, 1H), 8.22 (s, 1H), 8.06 (s, 1H), 7.89-7.87 (d, J=4.8 Hz, 1H), 7.18 (s, 1H), 4.67-4.64 (m, 1H), 4.00 (bs, 3H), 3.89-3.86 (m, 2H), 2.12-2.11 (m, 1H), 1.85-1.83 (m, 1H), 1.25 (bs, 3H), 1.06-1.04 (m, 2H), 0.88-0.87 (m, 4H).

I-81-b: MS (ES): m/z: 521.2 [M+H]+, $^1$H NMR (DMSO-d$_6$, 400 MHz): δ 9.04 (s, 1H), 8.71-8.69 (d, J=4.8 Hz, 1H), 8.53 (bs, 1H), 8.29 (s, 1H), 8.22 (s, 1H), 8.06 (s, 1H), 7.89-7.87 (d, J=4.8 Hz, 1H), 7.18 (s, 1H), 4.67-4.64 (m, 1H), 4.00 (bs, 3H), 3.89-3.84 (m, 2H), 2.12-2.11 (m, 1H), 1.84-1.83 (m, 1H), 1.25 (bs, 3H), 1.06-1.04 (m, 2H), 0.88-0.87 (m, 4H).

Example 82: ((2S,3S)-3-(5-(tert-butyl)-3-((7-chloro-1-methyl-6-(pyrazolo[1,5-a]pyrimidin-6-yloxy)-1H-imidazo[4,5-b]pyridin-2-yl)amino)-1H-pyrazol-1-yl)tetrahydrofuran-2-yl)methanol

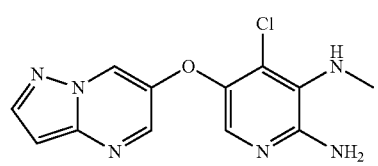

7.4

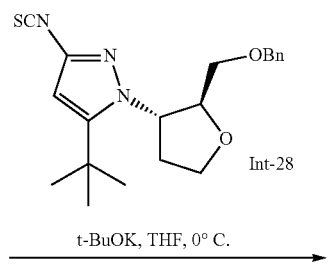

Int-28 t-BuOK, THF, 0° C.

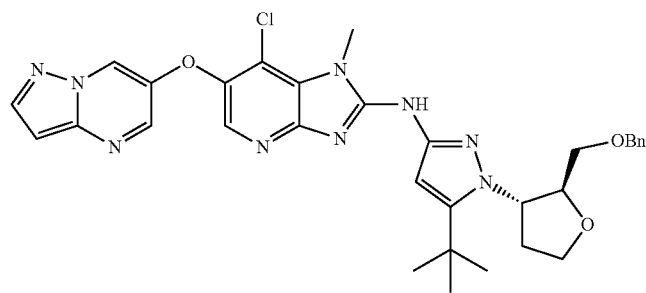

82.1 triflic acid, DCM,

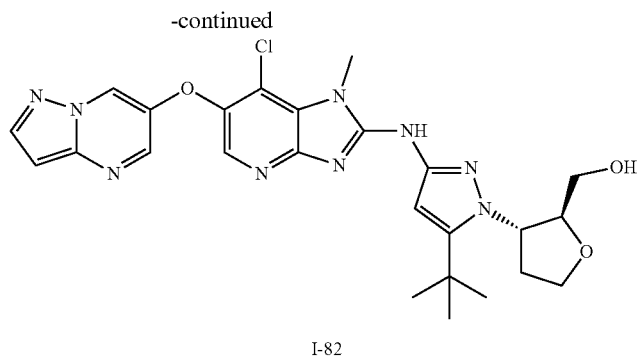

I-82

Synthesis of compound 82.1. Compound 82.1 was prepared from 7.4 and Int-28, following the procedure described in the synthesis of I-13. The product was purified by flash column chromatography on silica gel (CombiFlash®, 3.0% methanol in DCM). MS (ES): m/z: 629.2 [M+H]+.

Synthesis of I-82. Racemate I-82 was prepared from 82.1, following the procedure described in the synthesis of I-23. The product was purified by flash column chromatography on silica gel (CombiFlash®, 4.2% methanol in DCM). MS (ES): m/z: 538.7 [M+H]+, LCMS purity: 100%, HPLC purity: 100%, Chiral HPLC: 99.17%, $^1$H NMR (DMSO-$d_6$, 400 MHz): δ 10.00 (s, 1H), 8.88 (s, 1H), 8.69 (s, 1H), 8.18-8.16 (d, J=9.6 Hz, 2H), 6.79 (s, 1H), 6.56 (s, 1H), 5.04 (bs, 1H), 4.93-4.90 (m, 1H), 4.39-4.38 (m, 1H), 4.13-4.08 (m, 1H), 3.96 (s, 3H), 3.60-3.47 (m, 2H), 2.40-2.35 (m, 2H), 2.07-2.05 (m, 1H), 1.43 (s, 9H).

Example 83: ((2S,3S)-3-(5-(tert-butyl)-3-((7-chloro-6-(imidazo[1,2-b]pyridazin-7-yloxy)-1-methyl-1H-imidazo[4,5-b]pyridin-2-yl)amino)-1H-pyrazol-1-yl)tetrahydrofuran-2-yl)methanol

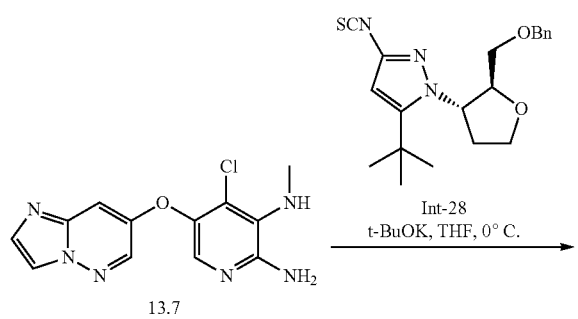

I-83

Synthesis of compound 83.1. Compound 83.1 was prepared from 13.7 and Int-28, following the procedure described in the synthesis of I-13. The product was purified by flash column chromatography on silica gel (CombiFlash®, 2.9% methanol in DCM). MS (ES): m/z: 629.2 [M+H]+.

Synthesis of I-83. Compound I-83 was prepared from 83.1, following the procedure described in the synthesis of I-23. The product was purified by flash column chromatography on silica gel (CombiFlash®, 4.5% methanol in DCM). MS (ES): m/z: 538.2 [M]+, $^1$H NMR (DMSO-$d_6$, 400 MHz): δ 10.04 (s, 1H), 8.72 (s, 1H), 8.21 (s, 1H), 8.16 (s, 1H), 7.65 (s, 1H), 7.22 (s, 1H), 6.56 (s, 1H), 5.05 (bs, 1H), 4.92 (bs, 1H), 4.38 (bs, 1H), 4.10-4.08 (m, 1H), 3.94 (s, 3H), 3.55-3.50 (m, 2H), 2.37-2.33 (m, 2H), 2.05-2.04 (m, 1H), 1.42 (s, 9H).

Example 84: 3-((7-chloro-6-((6-cyclopropylimidazo[1,5-a]pyrimidin-3-yl)oxy)-1-methyl-1H-imidazo[4,5-b]pyridin-2-yl)amino)-5-cyclopropyl-1-methylpyridin-2(1H)-one

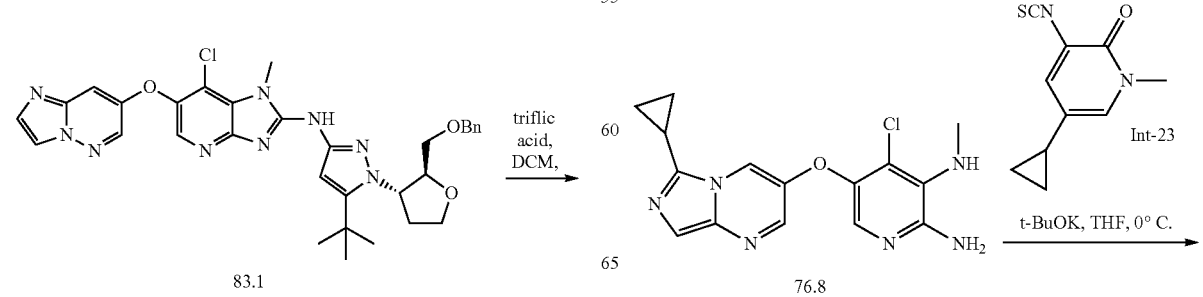

-continued

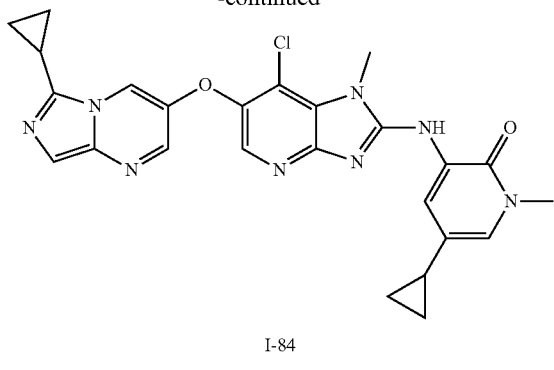

I-84

Synthesis of I-84. Compound I-84 was prepared from 76.8 and Int-23, following the procedure described in the synthesis of I-13. The product was purified by flash column chromatography on silica gel (CombiFlash®, 2.8% methanol in DCM). MS (ES): m/z: 503.6 [M+H]$^+$, $^1$H NMR (DMSO-d$_6$, 400 MHz): δ 8.56 (s, 1H), 8.38-8.37 (d, J=2.4 Hz, 1H), 8.30-8.29 (d, J=2.0 Hz, 1H), 8.24 (s, 1H), 8.23-8.22 (d, J=2.4 Hz, 1H), 7.40 (s, 1H), 7.24-7.23 (d, J=2.0 Hz, 1H), 3.98 (s, 3H), 3.55 (s, 3H), 2.38-2.33 (m, 1H), 1.79 (bs, 1H), 0.94-0.89 (m, 4H), 0.87-0.83 (m, 2H), 0.59-0.56 (m, 2H).

Example 85: 3-((7-chloro-1-methyl-6-(pyrazolo[1,5-a]pyrazin-3-yloxy)-1H-imidazo[4,5-b]pyridin-2-yl)amino)-5-cyclopropyl-1-(2-oxaspiro[3.3]heptan-6-yl)pyridin-2(1H)-one

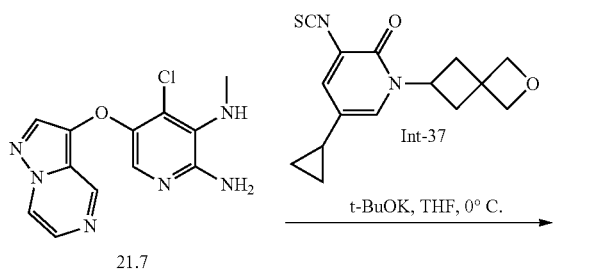

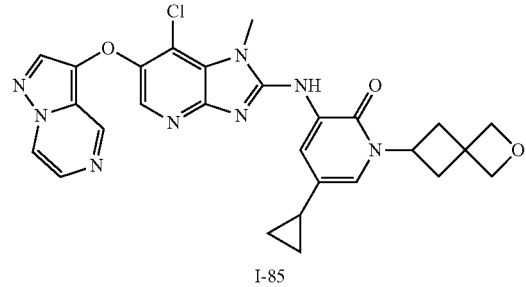

I-85

Synthesis of I-85. Compound I-85 was prepared from 21.7 and Int-37, following the procedure described in the synthesis of I-13. The product was purified by flash column chromatography on silica gel (CombiFlash®, 2.6% methanol in DCM). MS (ES): m/z: 545.14 [M]$^+$, $^1$H NMR (DMSO-d$_6$, 400 MHz): δ 9.03 (s, 1H), 8.70-8.69 (d, J=4.8 Hz, 1H), 8.53 (s, 1H), 8.22-8.21 (m, 2H), 8.05 (s, 1H), 7.88-7.87 (d, J=4.8 Hz, 1H), 7.24 (bs, 1H), 4.97-4.93 (m, 1H), 4.72 (bs, 2H), 4.60 (bs, 2H), 3.99 (s, 3H), 1.90 (bs, 2H), 1.58 (bs, 2H), 1.25 (bs, 1H), 0.90-0.88 (m, 2H), 0.63-0.61 (m, 2H).

Example 86: N-(5-(tert-butyl)-1-(oxetan-3-yl)-1H-pyrazol-3-yl)-7-chloro-1-methyl-6-(pyrazolo[1,5-a]pyrazin-3-yloxy)-1H-imidazo[4,5-b]pyridin-2-amine

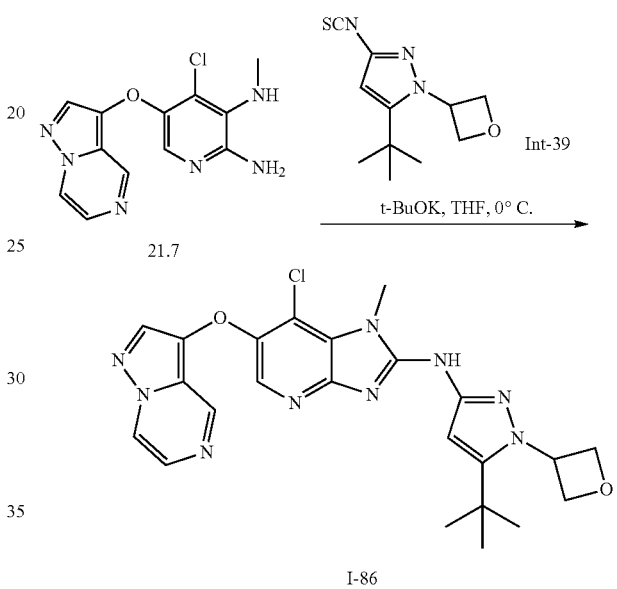

I-86

Synthesis of I-86. Compound I-86 was prepared from 21.7 and Int-39, following the procedure described in the synthesis of I-13. The product was purified by flash column chromatography on silica gel (CombiFlash®, 4.0% methanol in DCM). MS (ES): m/z: 494.5 [M]$^+$, $^1$H NMR (DMSO-d$_6$, 400 MHz): δ 10.20 (s, 1H), 9.02 (s, 1H), 8.69-8.68 (d, J=3.6 Hz, 1H), 8.14 (s, 1H), 8.03 (s, 1H), 7.87-7.86 (d, J=4.4 Hz, 1H), 6.63 (s, 1H), 5.82 (bs, 1H), 5.0-4.95 (m, 4H), 3.99 (s, 3H), 1.34 (s, 9H).

Example 87: ((2S,3S)-3-(5-(tert-butyl)-3-((7-chloro-6-((6-cyclopropylimidazo[1,5-a]pyrimidin-3-yl)oxy)-1-methyl-1H-imidazo[4,5-b]pyridin-2-yl)amino)-1H-pyrazol-1-yl)tetrahydrofuran-2-yl)methanol

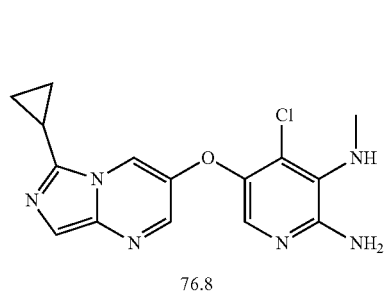

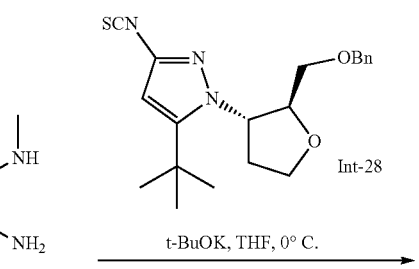

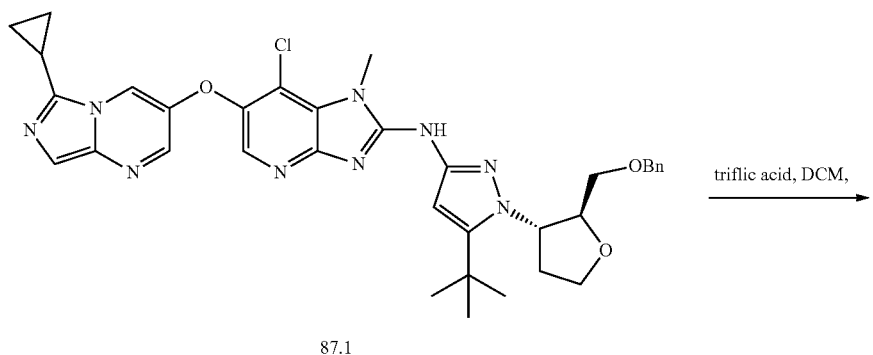

87.1

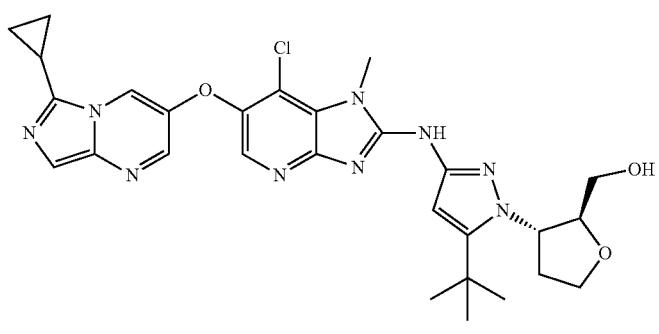

I-87

Synthesis of compound 87.1. Compound 87.1 was prepared from 76.8 and Int-28, following the procedure described in the synthesis of I-13. The product was purified by flash column chromatography on silica gel (CombiFlash®, 2.6% methanol in DCM). MS (ES): m/z: 668.8 [M+H]⁺.

Synthesis of I-87. Compound I-87 was prepared from 87.1, following the procedure described in the synthesis of I-23. The product was purified by flash column chromatography on silica gel (CombiFlash®, 3.6% methanol in DCM). MS (ES): m/z: 578.6 [M]⁺, ¹H NMR (DMSO-d₆, 400 MHz):

δ 9.98 (s, 1H), 8.33 (s, 1H), 8.20 (s, 1H), 8.14 (s, 1H), 7.39 (s, 1H), 6.54 (s, 1H), 5.05 (bs, 1H), 4.89-4.88 (d, 1H), 4.38-4.37 (d, 1H), 4.10-4.08 (m, 1H), 3.95 (s, 3H), 3.58-3.46 (m, 2H), 2.39-2.34 (m, 2H), 2.05-2.04 (m, 1H), 1.40 (s, 9H), 1.24 (bs, 1H), 0.94-0.89 (m, 4H).

Example 88: trans-3-(5-(tert-butyl)-3-((7-chloro-6-((6-cyclopropylimidazo[1,5-a]pyrimidin-3-yl)oxy)-1-methyl-1H-imidazo[4,5-b]pyridin-2-yl)amino)-1H-pyrazol-1-yl)cyclobutan-1-ol

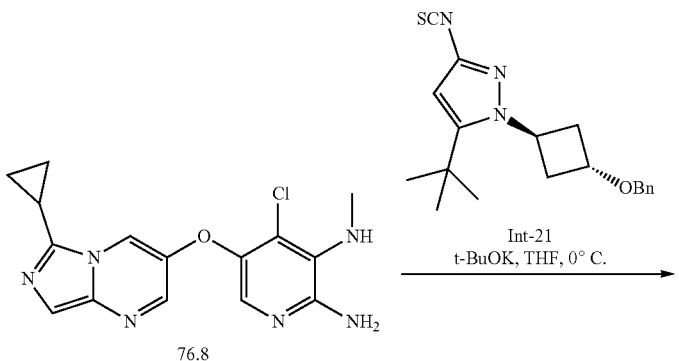

76.8

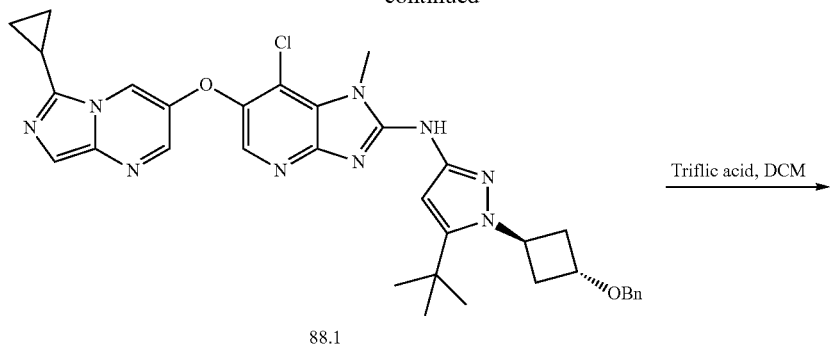

Synthesis of compound 88.1. Compound 88.1 was prepared from 76.8 and Int-21, following the procedure described in the synthesis of I-13. The product was purified by flash column chromatography on silica gel (CombiFlash®, 2.5% methanol in DCM). MS (ES): m/z: 639.1 [M+H]⁺.

Synthesis of I-88. Compound I-88 was prepared from 88.1, following the procedure described in the synthesis of I-23. The product was purified by flash column chromatography on silica gel (CombiFlash®, 4.8% methanol in DCM). MS (ES): m/z: 548.7 [M+H]⁺, $^1$H NMR (DMSO-d$_6$, 400 MHz): δ 9.99 (s, 1H), 8.36 (bs, 1H), 8.23-8.22 (d, J=2.0 Hz, 1H), 8.15 (s, 1H), 7.41 (s, 1H), 6.54 (s, 1H), 5.23-5.19 (m, 2H), 4.18 (bs, 1H), 3.96 (s, 3H), 2.75-2.74 (m, 2H), 2.37-2.35 (m, 3H), 1.35 (s, 9H), 0.95-0.91 (m, 4H).

Example 89: trans-3-((7-chloro-1-methyl-6-(pyrazolo[1,5-a]pyrazin-3-yloxy)-1H-imidazo[4,5-b]pyridin-2-yl)amino)-1-(3-hydroxycyclobutyl)-5-(trifluoromethyl)pyridin-2(1H)-one

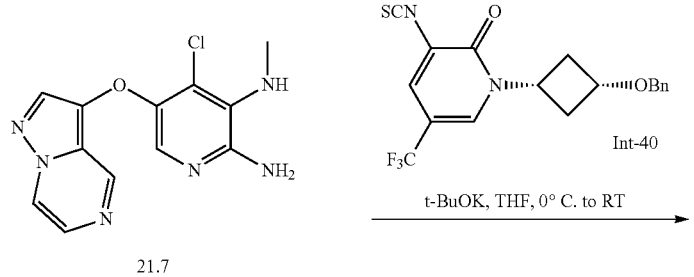

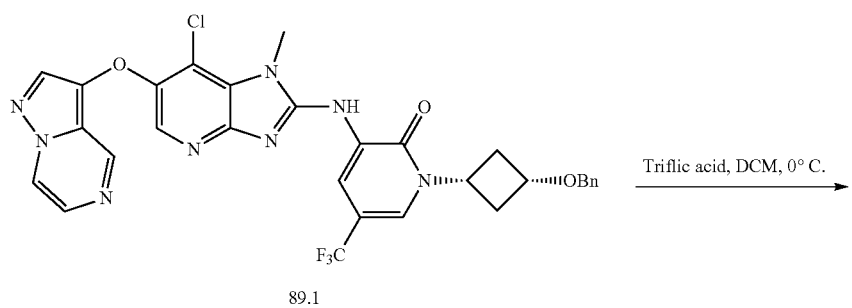

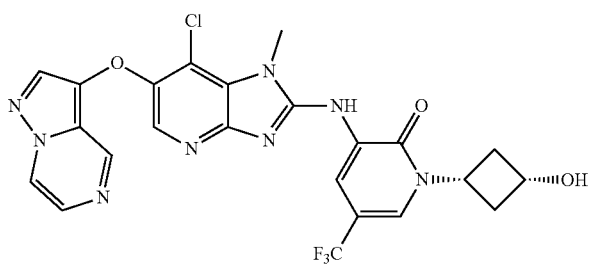

I-89

Synthesis of compound 89.1. Compound 89.1 was prepared from 21.7 and Int-40, following the procedure described in the synthesis of I-13. The product was purified by flash column chromatography on silica gel (CombiFlash®, 3.2% methanol in DCM). MS (ES): m/z: 637.7 [M+H]+.

Synthesis of I-89. Compound I-89 was prepared from 89.1, following the procedure described in the synthesis of I-23. The product was purified by flash column chromatography on silica gel (CombiFlash®, 4.5% methanol in DCM). MS (ES): m/z: 547.7 [M+H]+, $^1$H NMR (DMSO-d$_6$, 400 MHz): δ 9.05 (s, 1H), 8.85 (s, 1H), 8.70-8.69 (d, J=4.8 Hz, 1H), 8.63 (s, 1H), 8.26 (s, 1H), 8.06 (s, 1H), 7.91 (s, 1H), 7.89-7.88 (d, J=4.8 Hz, 1H), 5.77 (bs, 1H), 5.30-5.28 (m, 1H), 4.67-4.63 (m, 1H), 4.02 (s, 3H), 2.85-2.84 (m, 2H), 2.24-2.19 (m, 2H).

Example 90: 3-((7-chloro-1-methyl-6-(pyrazolo[1,5-a]pyrazin-3-yloxy)-1H-imidazo[4,5-b]pyridin-2-yl)amino)-1-(2-oxaspiro[3.3]heptan-6-yl)-5-(trifluoromethyl)pyridin-2(1H)-one

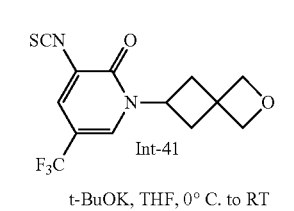

21.7

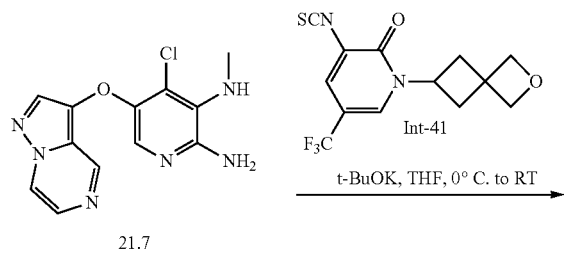

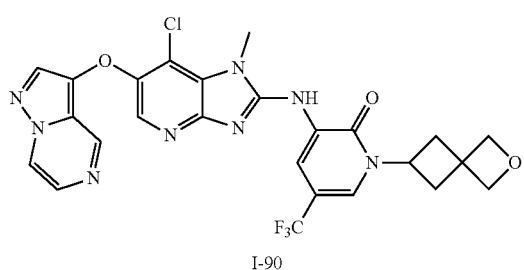

I-90

Synthesis of I-90. Compound I-90 was prepared from 21.7 and Int-41, following the procedure described in the synthesis of I-13. The product was purified by flash column chromatography on silica gel (CombiFlash®, 3.6% methanol in DCM). MS (ES): m/z: 573.6 [M+H]+, $^1$H NMR (DMSO-d$_6$, 400 MHz): δ 9.05 (s, 1H), 8.84 (s, 1H), 8.71-8.70 (d, J=4.4 z, 1H), 8.62 (s, 1H), 8.25 (s, 1H), 8.06 (s, 1H), 7.94 (s, 1H), 7.89-7.88 (d, J=4.8 Hz, 1H), 4.98-4.94 (m, 1H), 4.73 (bs, 2H), 4.58 (bs, 2H), 4.02 (s, 3H), 2.80-2.69 (m, 4H).

Example 91: 3-((7-chloro-1-methyl-6-(pyrazolo[1,5-a]pyrazin-3-yloxy)-1H-imidazo[4,5-b]pyridin-2-yl)amino)-1-(3-morpholinopropyl)-5-(trifluoromethyl)pyridin-2(1H)-one

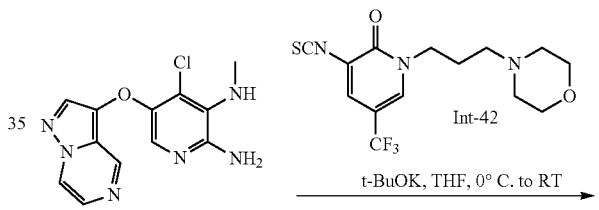

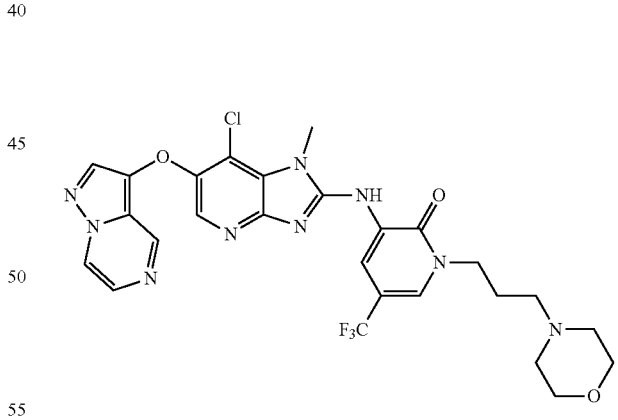

I-91

Synthesis of I-91. Compound I-91 was prepared from 21.7 and Int-42, following the procedure described in the synthesis of I-13. The product was purified by flash column chromatography on silica gel (CombiFlash®, 4.5% methanol in DCM). MS (ES): m/z: 604.7 [M+H]+, $^1$H NMR (DMSO-d$_6$, 400 MHz): δ 9.05 (s, 1H), 8.84 (s, 1H), 8.71-8.70 (d, J=4.4 z, 1H), 8.63 (s, 1H), 8.25 (s, 1H), 8.13 (s, 1H), 8.07 (s, 1H), 7.89-7.88 (d, J=4.8 Hz, 1H), 4.18-4.17 (m, 2H), 3.98 (s, 3H), 3.56 (bs, 4H), 2.34 (bs, 6H), 1.95-1.94 (m, 2H).

Example 92: 3-((6-((1H-pyrazolo[3,4-b]pyridin-5-yl)oxy)-7-chloro-1-methyl-1H-imidazo[4,5-b]pyridin-2-yl)amino)-5-cyclopropyl-1-methylpyridin-2(1H)-one

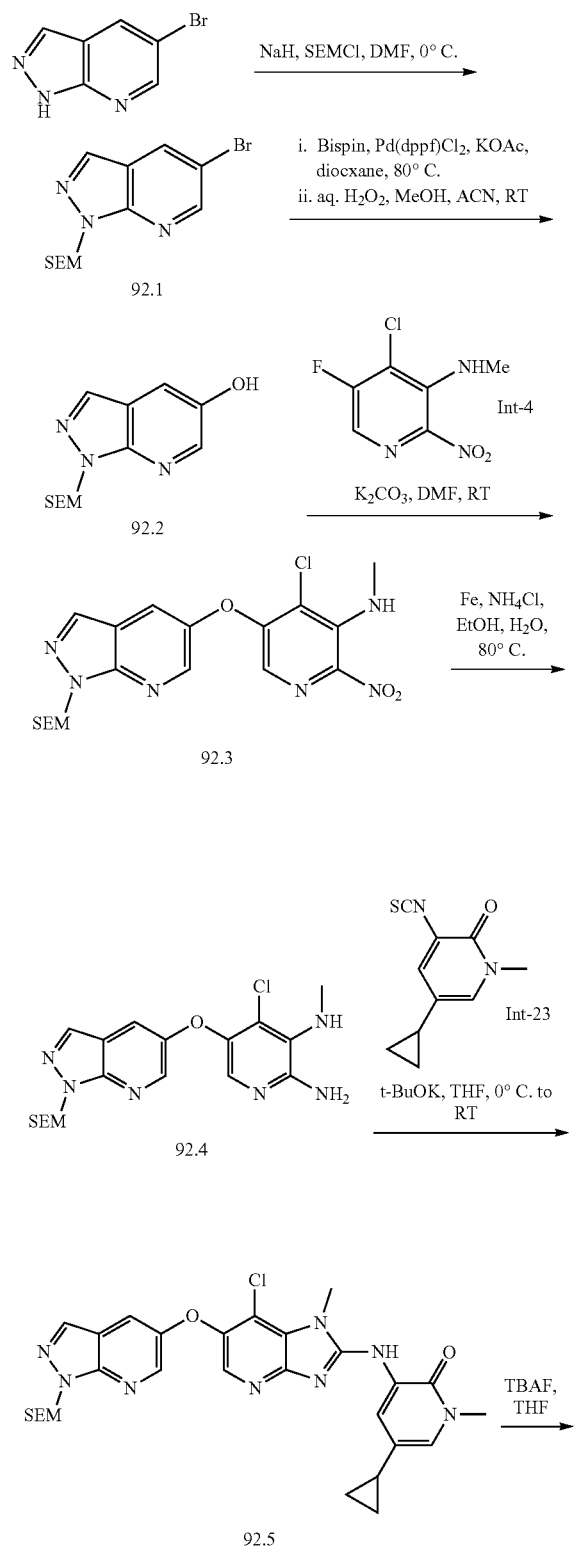

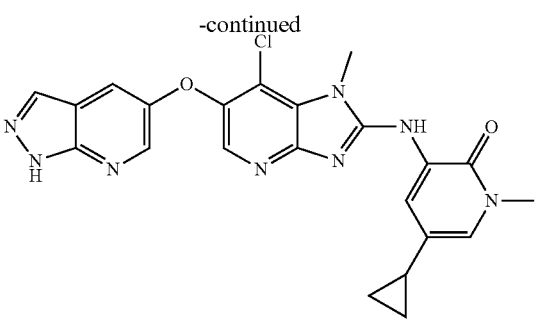

I-92

Synthesis of compound 92.1. To a suspension of sodium hydride (0.060 g, 1.51 mmol, 1.5 equiv) in DMF (2 mL) was added a solution of 5-bromo-1H-pyrazolo[3,4-b]pyridine (0.2 g, 1.01 mmol, 1.0 equiv) in THF (3 mL) at 0° C., and the mixture was stirred for 30 min, followed by addition of (2-chloromethoxyethyl)trimethylsilane (0.250 g, 1.51 mmol, 1.5 equiv). The reaction mixture was stirred at room temperature for 30 min. It was transferred into ice, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane) to afford 92.1. MS (ES): m/z 328.3 [M]$^+$.

Synthesis of compound 92.2. A mixture of 92.1 (0.250 g, 0.761 mmol, 1.0 equiv), bis(pinacolato)diboron (0.386 g, 1.52 mmol, 2.0 equiv) and potassium acetate (0.148 g, 1.52 mmol, 2.0 equiv) in 1,4-dioxane (5 mL) was degassed by bubbling through a stream of argon for min. Under argon atmosphere, [1,1'-bis(diphenylphosphino)ferrocene]palladium(II) dichloride (0.111 g, 0.152 mmol, 0.2 equiv) was added and, the mixture was degassed for an additional 5 min. The reaction mixture was stirred at 80° C. for 3 h. It was cooled to room temperature and filtered through a pad of Celite®. The filtrate was transferred into water and extracted with ethyl acetate. The combined organic layers were washed with brine, dried over anhydrous sodium sulfate, filtered and concentrated under reduced pressure. The residue was dissolved in methanol (7 mL) and acetonitrile (7 mL), followed by the addition of aq. hydrogen peroxide (1 mL). The reaction mixture was stirred at room temperature for 16 h. It was poured into ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.0% methanol in DCM) to afford 92.2. MS (ES): m/z 266.3 [M+H]$^+$.

Synthesis of compound 92.3. Compound 92.3 was prepared from 92.2 and Int-4, following the procedure described in the synthesis of 19.1. The product was purified by flash column chromatography on silica gel (CombiFlash®, 25% ethyl acetate in hexane). MS (ES): m/z 451.6 [M+H]$^+$.

Synthesis of compound 92.4 Compound 92.4 was prepared from 92.3, following the procedure described in the synthesis of 5.4. The product was purified by flash column chromatography on silica gel (CombiFlash®, 1.5% methanol in DCM). MS (ES): m/z 421.4 [M+H]$^+$.

Synthesis of compound 92.5. Compound 92.5 was prepared from 92.4 and Int-23, following the procedure described in the synthesis of I-13. The product was purified by flash column chromatography on silica gel (Combi-Flash®, 2.5% methanol in DCM). MS (ES): m/z: 594.1 [M+H]+.

Synthesis of I-92. To a solution of 92.5 (0.030 g, 0.051 mmol, 1.0 equiv) in THF (2 mL) was added tetra-n-butylammonium fluoride (1 M in THF, 0.5 mL, 0.51 mmol, 10 equiv) and stirred at 80° C. for 8 h. It was transferred into ice-cold saturated sodium bicarbonate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in DCM) to afford I-92: m/z: 463.0 [M+H]+, $^1$H NMR (DMSO-$d_6$, 400 MHz): δ 13.71 (s, 1H), 8.54 (bs, 2H), 8.31 (s, 1H), 8.16 (s, 1H), 8.02 (s, 1H), 7.64 (s, 1H), 7.25 (s, 1H), 3.99 (s, 3H), 3.57 (s, 3H), 1.84 (bs, 1H), 0.95-0.88 (m, 2H), 0.61 (bs, 2H).

Example 93: (3R,4S)-4-(5-(tert-butyl)-3-((6-((6-cyclopropylimidazo[1,5-a]pyrimidin-3-yl)oxy)-7-(difluoromethyl)-1-methyl-1H-imidazo[4,5-b]pyridin-2-yl)amino)-1H-pyrazol-1-yl)tetrahydrofuran-3-ol and (3S,4R)-4-(5-(tert-butyl)-3-((6-((6-cyclopropylimidazo[1,5-a]pyrimidin-3-yl)oxy)-7-(difluoromethyl)-1-methyl-1H-imidazo[4,5-b]pyridin-2-yl)amino)-1H-pyrazol-1-yl)tetrahydrofuran-3-ol

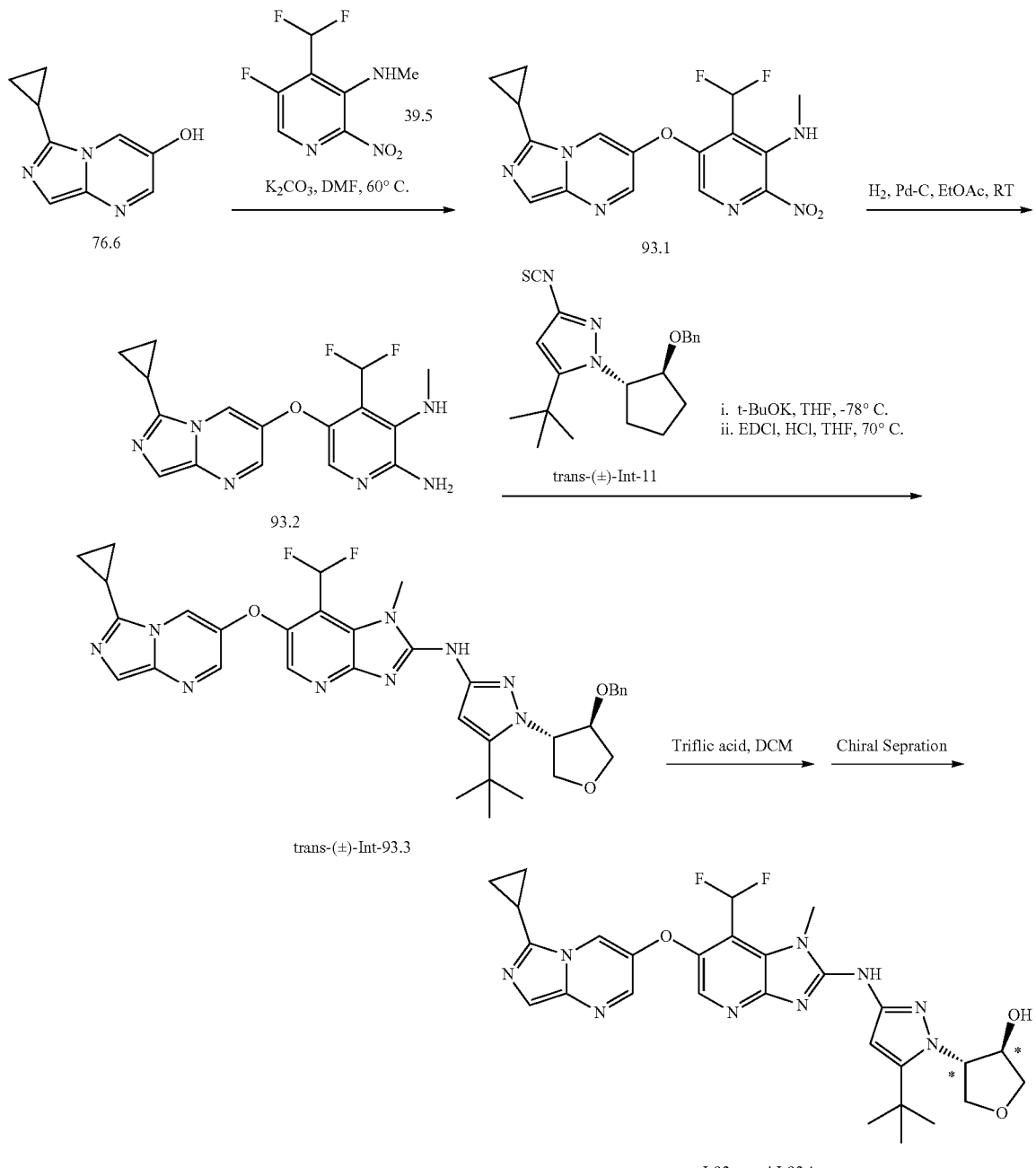

Synthesis of compound 93.1. Compound 93.1 was prepared from 76.6 and 39.5, following the procedure described in the synthesis of 76.7. The product was purified by flash column chromatography on silica gel (CombiFlash®, 2.0% methanol in DCM). MS (ES): m/z 377.5 [M+H]⁺.

Synthesis of compound 93.2. A mixture of 93.1 (0.500 g, 1.33 mmol, 1.0 equiv) and palladium on charcoal (0.25 g) in ethyl acetate (10 mL) was stirred under hydrogen (1 atm) at room temperature for 16 h. It was filtered through a pad of Celite® and washed with ethyl acetate. The filtrate was concentrated under reduced pressure. The residue was purified by trituration with n-pentane to afford 93.2. MS (ES): m/z 347.2 [M+H]⁺.

Synthesis of compound trans-(±)-Int-93.3. Compound trans-(±)-Int-93.3 was prepared from 93.2 and trans-(±)-Int-11, following the procedure described in the synthesis of I-51. The product was purified by flash column chromatography on silica gel (CombiFlash®, 2.5% methanol in DCM). MS (ES): m/z: 670.1 [M+H]⁺.

Synthesis of I-93-a and I-93-b. Racemate I-93 was prepared from trans-(±)-Int-93.3, following the procedure described in the synthesis of I-23. The product was purified by flash column chromatography on silica gel (CombiFlash®, 3.5% methanol in DCM. MS (ES): m/z: 580.6 [M+H]⁺. It was subjected to HPLC separation (column: CHIRALPAK IB-N (250 mm×21 mm, 5 μm); mobile phase: (A) 0.1% DEA in hexane, (B) 0.1% DEA in isopropanol:methanol (50:50); flow rate: 20 mL/min) to afford first eluting fraction (I-93-a) and second eluting fraction (I-93-b). (*Absolute stereochemistry not determined.)

I-93-a: MS (ES): m/z: 580.6 [M+H]⁺, ¹H NMR (MeOD, 400 MHz): δ 8.32-8.31 (d, J=6.8 Hz, 2H), 8.09 (s, 1H), 7.63-7.36 (m, 1H), 7.56 (s, 1H), 6.84-6.83 (d, J=2.0 Hz, 1H), 6.57 (s, 1H), 5.05 (bs, 1H), 4.64 (bs, 1H), 4.38-4.29 (m, 2H), 4.00-3.97 (m, 1H), 3.89 (s, 3H), 3.85-3.82 (m, 1H), 3.38 (bs, 1H), 2.23-2.16 (m, 1H), 1.47 (s, 9H), 1.10-1.00 (m, 4H).

I-93-b: MS (ES): m/z: 580.6 [M+H]⁺, ¹H NMR (MeOD, 400 MHz): δ 8.33-8.29 (d, J=6.8 Hz, 2H), 8.10 (s, 1H), 7.65-7.38 (m, 1H), 7.53 (s, 1H), 6.85-6.84 (d, J=2.0 Hz, 1H), 6.59 (s, 1H), 5.06 (bs, 1H), 4.66 (bs, 1H), 4.40-4.30 (m, 2H), 4.02-3.98 (m, 1H), 3.90 (s, 3H), 3.86-3.84 (m, 1H), 3.38 (bs, 1H), 2.20-2.19 (m, 1H), 1.49 (s, 9H), 1.10-1.01 (m, 4H).

Example 94: 1-(3-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)azetidin-1-yl)ethan-1-one

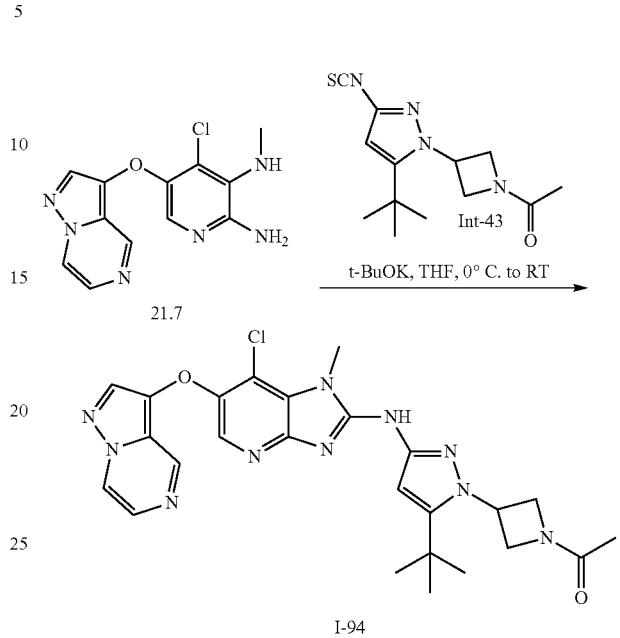

Synthesis of I-94. Compound I-94 was prepared from 21.7 and Int-43, following the procedure described in the synthesis of I-13. The product was purified by flash column chromatography on silica gel (CombiFlash®, 2.7% methanol in DCM). MS (ES): m/z: 535.7 [M]⁺, ¹H NMR (DMSO-d₆, 400 MHz): δ 10.17 (s, 1H), 9.02 (s, 1H), 8.69 (bs, 1H), 8.14 (s, 1H), 8.03 (s, 1H), 7.88 (bs, 1H), 6.64 (s, 1H), 5.50 (bs, 1H), 4.59 (bs, 1H), 4.43 (bs, 1H), 4.32-4.26 (m, 2H), 3.98 (s, 3H), 1.83 (s, 3H), 1.37 (s, 9H).

Example 95: 3-((7-chloro-1-methyl-6-(pyrazolo[1,5-a]pyrazin-3-yloxy)-1H-imidazo[4,5-b]pyridin-2-yl)amino)-5-cyclopropyl-1-((1S,2S)-2-hydroxycyclobutyl)pyridin-2(1H)-one and 3-((7-chloro-1-methyl-6-(pyrazolo[1,5-a]pyrazin-3-yloxy)-1H-imidazo[4,5-b]pyridin-2-yl)amino)-5-cyclopropyl-1-((1R,2R)-2-hydroxycyclobutyl)pyridin-2(1H)-one

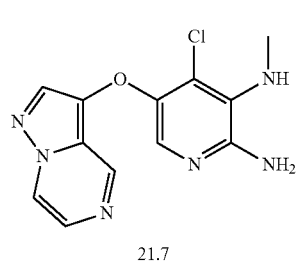

21.7

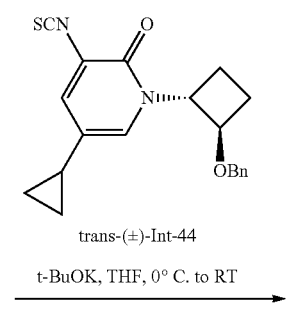

trans-(±)-Int-44 t-BuOK, THF, 0° C. to RT

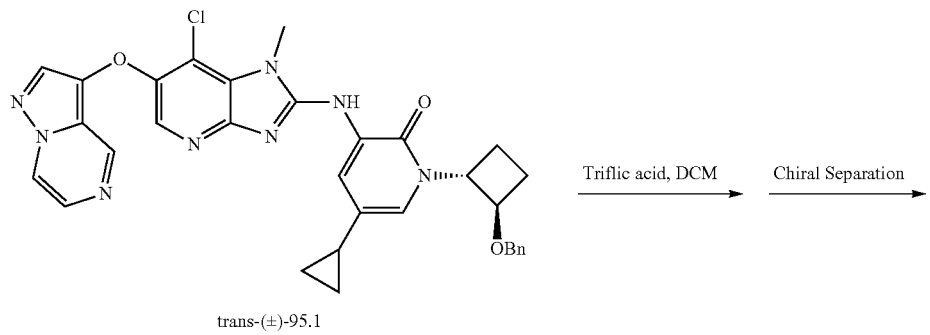

trans-(±)-95.1

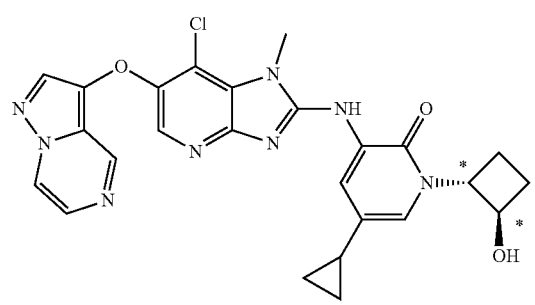

I-95-a and I-95-b

Synthesis of compound trans-(±)-95.1. Compound trans-(±)-95.1 was prepared from 21.7 and trans-(±)-Int-44, following the procedure described in the synthesis of I-13. The product was purified by flash column chromatography on silica gel (CombiFlash®, 1.6% methanol in DCM). MS (ES): m/z: 610.1 [M+H]$^+$.

Synthesis of compound I-95-a and I-95-b. Racemate I-95 was prepared from trans-(±)-95.1, following the procedure described in the synthesis of I-23. The product was purified by flash column chromatography on silica gel (CombiFlash®, 2.4% methanol in DCM). It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-95-a) and second eluting fraction (I-95-b). (*Absolute stereochemistry not determined.)

I-95-a: MS (ES): m/z: 519.3 [M+H]$^+$, $^1$H NMR (DMSO-d$_6$, 400 MHz): δ 9.02 (s, 1H), 8.69-8.68 (d, J=4.8 Hz, 1H), 8.54 (bs, 1H), 8.23-8.21 (d, J=8.4 Hz, 2H), 8.04 (s, 1H), 7.87-7.86 (d, J=4.8 Hz, 1H), 7.29 (s, 1H), 5.62-5.60 (d, J=6.4 Hz, 1H), 4.92-4.87 (m, 1H), 4.45-4.41 (m, 1H), 3.99 (s, 3H), 2.14-2.09 (m, 2H), 1.88 (bs, 1H), 1.71-1.59 (m, 2H), 0.89-0.87 (m, 2H), 0.63-0.62 (m, 2H).

I-95-b: MS (ES): m/z: 519.3 [M+H]$^+$, $^1$H NMR (DMSO-d$_6$, 400 MHz): δ 9.03 (s, 1H), 8.70-8.69 (d, J=4.8 Hz, 1H), 8.55 (bs, 1H), 8.24-8.21 (d, J=8.8 Hz, 2H), 8.04 (s, 1H), 7.88-7.87 (d, J=4.4 Hz, 1H), 7.29 (s, 1H), 5.63-5.61 (d, J=6.4 Hz, 1H), 4.92-4.90 (m, 1H), 4.46-4.44 (m, 1H), 3.99 (s, 3H), 2.15-2.10 (m, 2H), 1.89 (bs, 1H), 1.70-1.62 (m, 2H), 0.90-0.88 (m, 2H), 0.64-0.63 (m, 2H).

Example 96: trans-3-(5-cyclopropyl-3-((7-methoxy-1-methyl-6-(pyrazolo[1,5-a]pyrazin-3-yloxy)-1H-imidazo[4,5-b]pyridin-2-yl)amino)-2-oxopyridin-1(2H)-yl)cyclobutane-1-carbonitrile

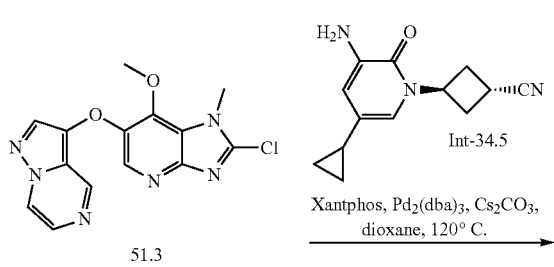

51.3

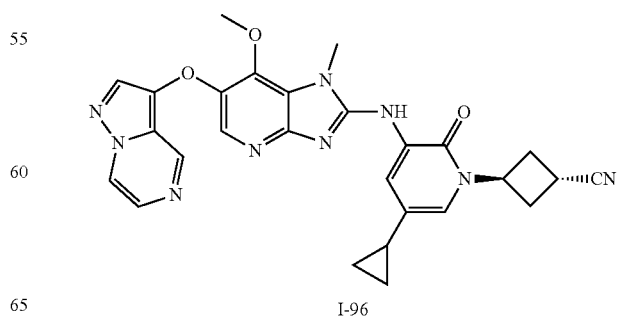

I-96

Synthesis of I-96. Compound I-96 was prepared from 51.3 and Int-34.5, following the procedure described in the synthesis of I-53. The product was purified by flash column chromatography on silica gel (CombiFlash®, 3.0% methanol in DCM). MS (ES): m/z: 524.4 [M+H]+, $^1$H NMR (CDCl$_3$, 400 MHz): δ 9.01 (s, 1H), 8.68-8.66 (m, 1H), 8.25 (bs, 1H), 8.21 (bs, 1H), 8.11 (s, 1H), 7.99 (s, 1H), 7.85-7.84 (d, J=4.4 Hz 1H), 7.68-7.67 (d, J=2.0 Hz 1H), 5.46-5.42 (m, 1H), 4.10 (s, 3H), 3.89 (s, 3H), 3.47-3.46 (m, 1H), 2.80-2.77 (m, 2H), 2.64-2.57 (m, 2H), 1.95-1.94 (m, 1H), 0.98-0.95 (m, 2H), 0.67-0.66 (m, 2H).

Example 97: 3-((7-chloro-1-methyl-6-(pyrazolo[1,5-a]pyrazin-3-yloxy)-1H-imidazo[4,5-b]pyridin-2-yl)amino)-5-cyclopropyl-1-(3-morpholinopropyl)pyridin-2(1H)-one

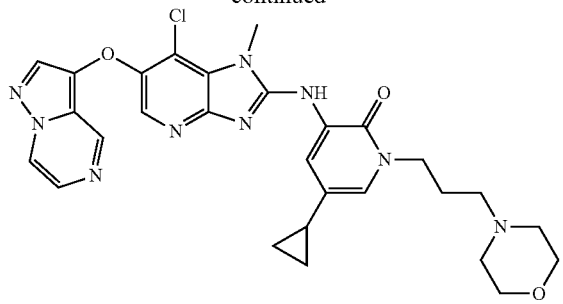

I-97

Synthesis of I-97. Compound I-97 was prepared from 21.7 and Int-42, following the procedure described in the synthesis of I-13. The product was purified by preparative HPLC. MS (ES): m/z: 576.3 [M+H]+, $^1$H NMR (DMSO-d$_6$, 400 MHz): δ 9.03 (s, 1H), 8.69 (bs, 1H), 8.53 (s, 1H), 8.28 (s, 1H), 8.20 (s, 1H), 8.04 (s, 1H), 7.87-7.86 (d, J=3.6 Hz, 1H), 7.22 (s, 1H), 4.02-3.98 (m, 5H), 3.58 (bs, 4H), 2.34-2.31 (m, 6H), 1.87-1.82 (m, 3H), 0.88-0.86 (m, 2H), 0.58-0.56 (m, 2H).

Example 98: 3-((7-chloro-1-methyl-6-(pyrazolo[1,5-a]pyrazin-3-yloxy)-1H-imidazo[4,5-b]pyridin-2-yl)amino)-5-cyclopropyl-1-((1R,2S)-2-hydroxycyclobutyl)pyridin-2(1H)-one and 3-((7-chloro-1-methyl-6-(pyrazolo[1,5-a]pyrazin-3-yloxy)-1H-imidazo[4,5-b]pyridin-2-yl)amino)-5-cyclopropyl-1-((1S,2R)-2-hydroxycyclobutyl)pyridin-2(1H)-one

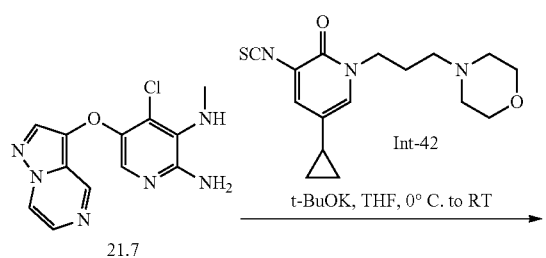

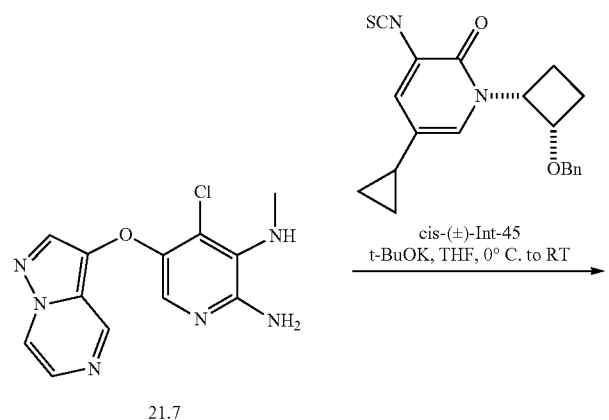

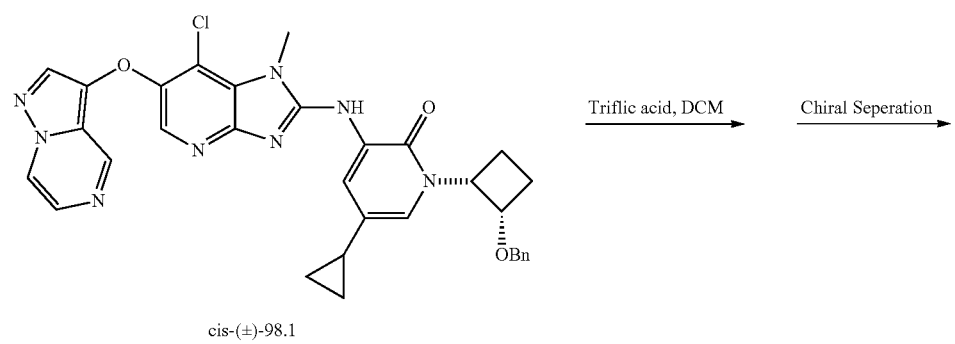

cis-(±)-98.1

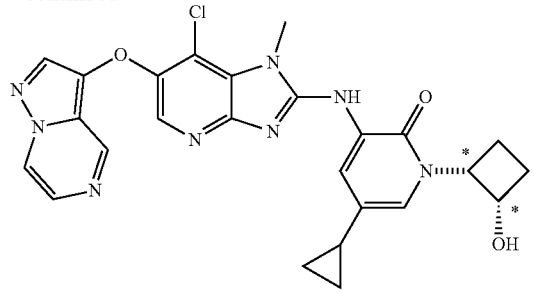

I-98-a and I-98-b

Synthesis of compound cis-(±)-98.1. Compound cis-(±)-98.1 was prepared from 21.7 and cis-(±)-Int-45, following the procedure described in the synthesis of I-13. The product was purified by flash column chromatography on silica gel (CombiFlash®, 1.6% methanol in DCM). MS (ES): m/z: 610.1 [M+H]+.

Synthesis of compound I-98-a and I-98-b. Racemate I-98 was prepared from cis-(±)-98.1, following the procedure described in the synthesis of I-23. The product was purified by flash column chromatography on silica gel (CombiFlash®, 2.4% methanol in DCM). It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-98-a) and second eluting fraction (I-98-b). (*Absolute stereochemistry not determined.)

I-98-a: MS (ES): m/z: 519.2 [M+H]+, 1H NMR (DMSO-d6, 400 MHz): δ 9.02 (s, 1H), 8.69-8.68 (d, J=4.8 Hz, 1H), 8.54 (bs, 1H), 8.23-8.21 (d, J=8.4 Hz, 2H), 8.04 (s, 1H), 7.87-7.86 (d, J=4.8 Hz, 1H), 7.29 (s, 1H), 5.62-5.60 (d, J=6.4 Hz, 1H), 4.94-4.90 (m, 1H), 4.45-4.43 (m, 1H), 3.98 (s, 3H), 2.14-2.12 (m, 2H), 1.89 (bs, 1H), 1.71-1.59 (m, 2H), 0.89-0.87 (m, 2H), 0.63-0.62 (m, 2H).

I-98-b: MS (ES): m/z: 519.2 [M+H]+, 1H NMR (DMSO-d6, 400 MHz): δ 9.02 (s, 1H), 8.69-8.68 (d, J=4.4 Hz, 1H), 8.54 (bs, 1H), 8.22 (bs, 1H), 8.20 (s, 1H), 8.04 (s, 1H), 7.87-7.86 (d, J=4.8 Hz, 1H), 7.29 (s, 1H), 5.63-5.62 (d, J=6.4 Hz, 1H), 4.92-4.90 (m, 1H), 4.45-4.41 (m, 1H), 3.98 (s, 3H), 2.14-2.09 (m, 2H), 1.88 (bs, 1H), 1.71-1.61 (m, 2H), 0.90-0.88 (m, 2H), 0.64-0.63 (m, 2H).

Example 99: 3-((7-chloro-1-methyl-6-(pyrazolo[1,5-a]pyridin-3-yloxy)-1H-imidazo[4,5-b]pyridin-2-yl)amino)-5-cyclopropyl-1-((1S,2S)-2-hydroxycyclobutyl)pyridin-2(1H)-one and 3-((7-chloro-1-methyl-6-(pyrazolo[1,5-a]pyridin-3-yloxy)-1H-imidazo[4,5-b]pyridin-2-yl)amino)-5-cyclopropyl-1-((1R,2R)-2-hydroxycyclobutyl)pyridin-2(1H)-one

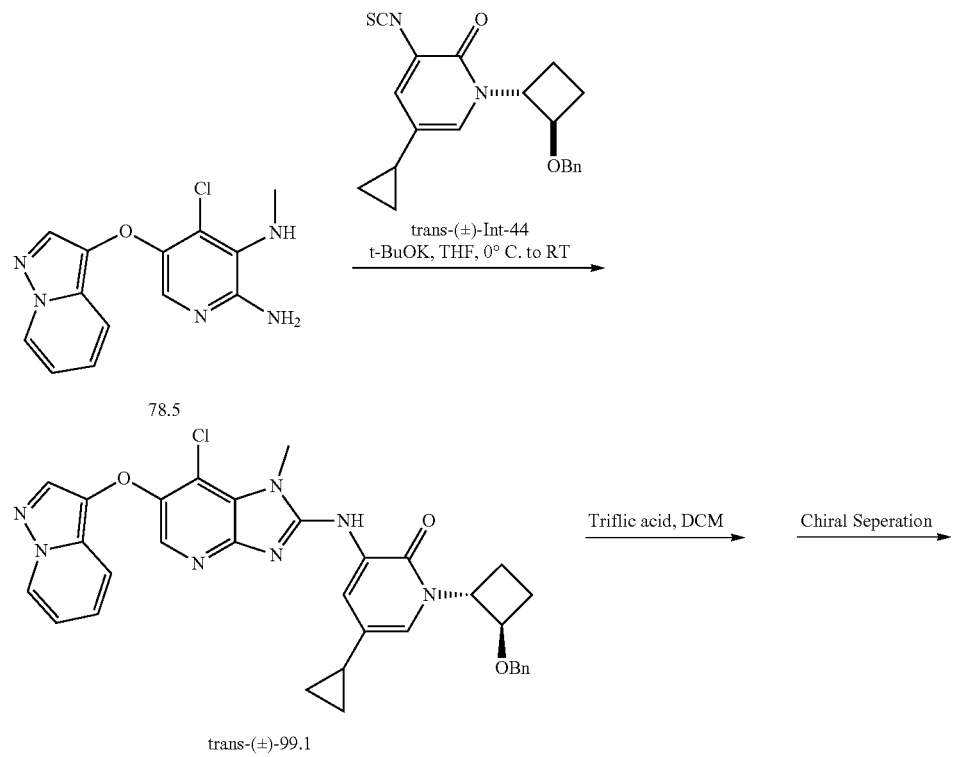

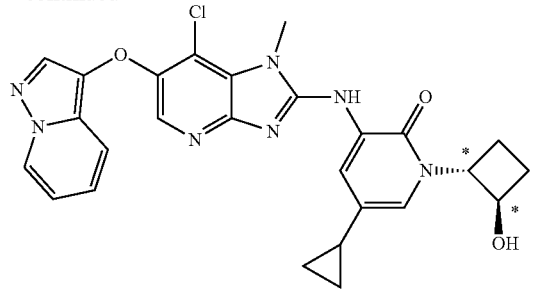

I-99-a and I-99-b

Synthesis of compound trans-(±)-99.1. Compound trans-(±)-99.1 was prepared from 78.5 and trans-(±)-Int-44, following the procedure described in the synthesis of I-13. The product was purified by flash column chromatography on silica gel (CombiFlash®, 1.6% methanol in DCM). MS (ES): m/z: 609.1 [M+H]+.

Synthesis of compound I-99-a and I-99-b. Racemate I-99 was prepared from trans-(±)-99.1, following the procedure described in the synthesis of I-23. The product was purified by flash column chromatography on silica gel (Combi-Flash®, 2.4% methanol in DCM). MS (ES): m/z 518.2 [M+H]+. It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-99-a) and second eluting fraction (I-99-b). (*Absolute stereochemistry not determined.)

I-99-a: MS (ES): m/z: 518.2 [M+H]+, 1H NMR (DMSO-d6, 400 MHz): δ 8.62-8.61 (d, J=6.4 Hz, 1H), 8.51 (bs, 1H), 8.22 (bs, 1H), 8.01-8.00 (d, J=5.2 Hz, 2H), 7.51-7.47 (d, J=7.6 Hz, 1H), 7.28 (s, 1H), 7.18 (bs, 1H), 6.89 (bs, 1H), 5.61-5.60 (d, J=6.4 Hz, 1H), 4.91-4.89 (m, 1H), 4.43 (bs, 1H), 3.99 (s, 3H), 2.12-2.04 (m, 2H), 1.91-1.87 (bs, 1H), 1.68-1.61 (m, 2H), 0.87 (bs, 2H), 0.62 (bs, 2H).

I-99-b: MS (ES): m/z: 518.2 [M+H]+, 1H NMR (DMSO-d6, 400 MHz): δ 8.63-8.61 (d, J=7.2 Hz, 1H), 8.51 (bs, 1H), 8.22 (bs, 1H), 8.01-8.00 (d, J=5.2 Hz, 2H), 7.51-7.49 (d, J=7.6 Hz, 1H), 7.28 (s, 1H), 7.20-7.16 (t, J=7.6 Hz, 8.4 Hz, 1H), 6.91-6.88 (t, J=6.8 Hz, 6.8 Hz, 1H), 5.62-5.60 (d, J=6.8 Hz, 1H), 4.91-4.89 (m, 1H), 4.43 (bs, 1H), 3.99 (s, 3H), 2.13-2.06 (m, 2H), 1.91-1.87 (bs, 1H), 1.68-1.61 (m, 2H), 0.89-0.86 (m, 2H), 0.62-0.61 (m, 2H).

Example 100: 5-cyclopropyl-1-(2-hydroxyethyl)-3-((7-methoxy-1-methyl-6-(pyrazolo[1,5-a]pyridin-3-yloxy)-1H-imidazo[4,5-b]pyridin-2-yl)amino)pyridin-2(1H)-one

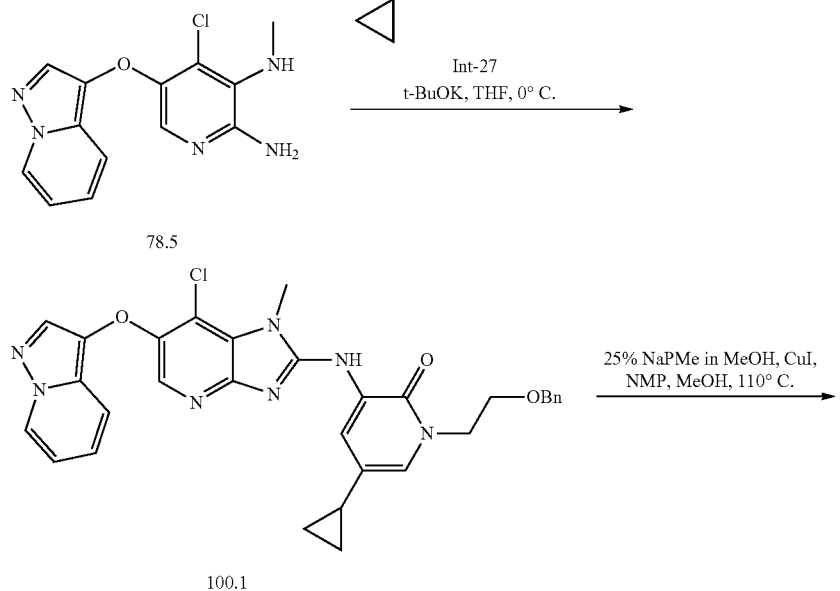

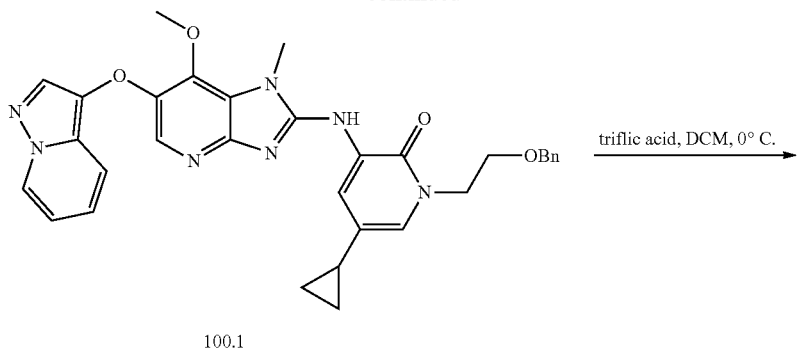

100.1

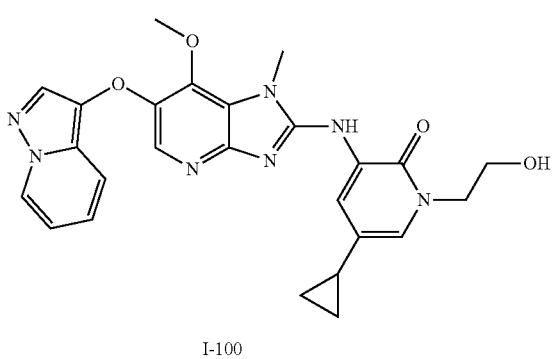

I-100

Synthesis of compound 100.1. Compound 100.1 was prepared from 78.5 and Int-27, following the procedure described in the synthesis of I-13. The product was purified by flash column chromatography on silica gel (Combi-Flash®, 1.6% methanol in DCM). MS (ES): m/z: 582.1 [M+H]$^+$.

Synthesis of compound 100.2. To a solution of 100.1 (0.110 g, 0.188 mmol, 1.0 equiv) in methanol (1.1 mL) and N-methylpyrrolidine (6 mL) were added sodium methoxide solution (25%, 0.4 mL, 1.88 mmol, 10.0 equiv) and copper iodide (0.010 g, 0.056 mmol, 0.3 equiv). The reaction mixture was stirred at 110° C. for 16 h. It was cooled to room temperature, poured into ice-water, and extracted with DCM. The combined organic layers were washed with brine, dried over anhydrous sodium sulfate, filtered and concentrated under reduced pressure. The residue was purified by preparative HPLC to afford 100.2. MS (ES): m/z: 578.5 [M+H]$^+$.

Synthesis of I-100. Compound I-100 was prepared from 100.1, following the procedure described in the synthesis of I-23. The product was purified by trituration with diethyl ether. MS (ES): m/z: 488.5 [M+H]$^+$. $^1$H NMR (DMSO-d$_6$, 400 MHz): δ 8.60-8.58 (d, J=6.8 Hz, 1H), 8.31 (s, 1H), 8.28-8.27 (d, J=8.0 Hz, 1H), 7.95-7.93 (d, J=6.4 Hz, 2H), 7.53-7.50 (d, J=9.2 Hz, 1H), 7.17-7.12 (m, 2H), 6.88-6.85 (m, 1H), 4.92-4.89 (m, 1H), 4.13 (s, 3H), 4.06-4.03 (m, 2H), 3.89 (s, 3H), 3.71-3.67 (m, 2H), 1.84-1.79 (m, 1H), 0.88-0.84 (m, 2H), 0.58-0.54 (m, 2H).

Example 101: (S)-5-cyclopropyl-3-((7-methoxy-1-methyl-6-(pyrazolo[1,5-a]pyridin-3-yloxy)-1H-imidazo[4,5-b]pyridin-2-yl)amino)-1-(tetrahydro-2H-pyran-3-yl)pyridin-2(1H)-one and (R)-5-cyclopropyl-3-((7-methoxy-1-methyl-6-(pyrazolo[1,5-a]pyridin-3-yloxy)-1H-imidazo[4,5-b]pyridin-2-yl)amino)-1-(tetrahydro-2H-pyran-3-yl)pyridin-2(1H)-one

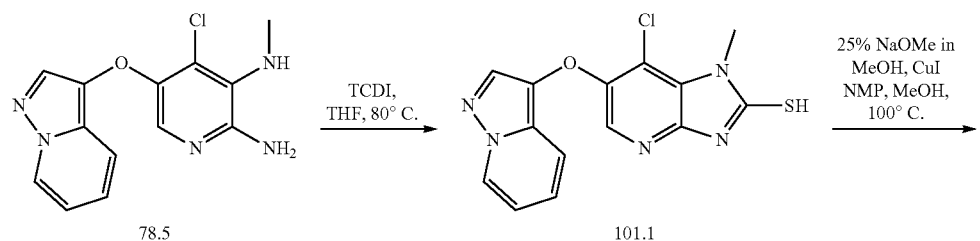

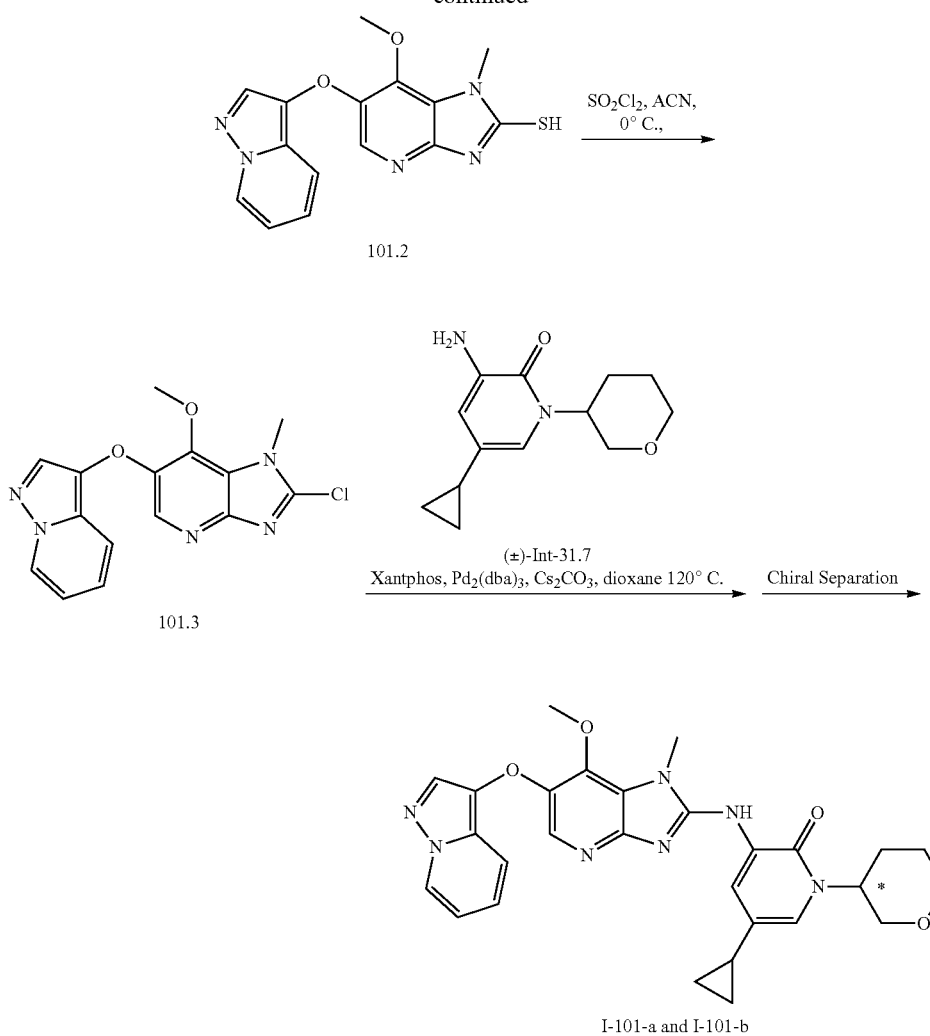

Synthesis of compound 101.1. To a solution of 78.5 (4.5 g, 15.53 mmol, 1.0 equiv) in THF (135 mL) was added 1,1'-thiocarbonyldiimidazole (16.58 g, 93.18 mmol, 6.0 equiv). The reaction mixture was stirred at 80° C. for 4 h. It was cooled to room temperature and poured into ice-water. The solids were collected by filtration and triturated with hexane to afford 101.1. MS (ES): m/z: 332.5 [M+H]+.

Synthesis of compound 101.2. Compound 101.2 was prepared from 101.1, following the procedure described in the synthesis of 100.2. The product was purified by flash column chromatography on silica gel (CombiFlash®, 2.0% methanol in DCM). MS (ES): m/z: 328.3 [M+H]+.

Synthesis of compound 101.3. Compound 101.3 was prepared from 101.2, following the procedure described in the synthesis of 45.3. The product was purified by flash column chromatography on silica gel (CombiFlash®, 2.2% methanol in DCM). MS (ES): m/z 330.7 [M+H]+.

Synthesis of compound I-101-a and I-101-b. Racemate I-101 was prepared from 101.3 and (±)-Int-31.7, following the procedure described in the synthesis of I-53. The product was purified by flash column chromatography on silica gel (CombiFlash®, 3.0% methanol in DCM). MS (ES): m/z 528.3 [M+H]+. It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-101-a) and second eluting fraction (I-101-b). (*Absolute stereochemistry not determined.)

I-101-a: MS (ES): m/z: 528.3 [M+H]+, $^1$H NMR (DMSO-$d_6$, 400 MHz): δ 8.60-8.58 (d, J=6.8 Hz, 1H), 8.34 (bs, 1H), 8.22 (bs, 1H), 7.94-7.93 (d, J=4.0 Hz, 2H), 7.53-7.51 (d, J=8.8 Hz, 1H), 7.27 (s, 1H), 7.17-7.14 (t, J=7.2 Hz, 8.4 Hz, 1H), 6.89-6.85 (t, J=6.4 Hz, 6.8 Hz, 1H), 4.86 (bs, 1H), 4.13 (s, 3H), 3.89 (s, 3H), 3.85-3.80 (m, 2H), 3.67-6.62 (m, 1H), 3.50-3.45 (m, 1H), 2.14-2.12 (m, 1H), 1.93 (bs, 1H), 1.84-1.83 (m, 1H), 1.77-1.72 (m, 2H), 0.88-0.86 (m, 2H), 0.60-0.59 (m, 2H).

I-101-b: MS (ES): m/z: 528.3 [M+H]+, $^1$H NMR (DMSO-$d_6$, 400 MHz): δ 8.60-8.58 (d, J=6.8 Hz, 1H), 8.34 (bs, 1H), 8.22 (bs, 1H), 7.95-7.93 (d, J=6.4 Hz, 2H), 7.53-7.51 (d, J=8.8 Hz, 1H), 7.27 (s, 1H), 7.18-7.14 (t, J=7.2 Hz, 8.4 Hz, 1H), 6.89-6.85 (t, J=6.4 Hz, 6.8 Hz, 1H), 4.86 (bs, 1H), 4.13 (s, 3H), 3.89 (s, 3H), 3.85-3.80 (m, 2H), 3.68-6.62 (m, 1H), 3.50-3.45 (m, 1H), 2.15-2.12 (m, 1H), 1.94-1.91 (m, 1H), 1.87-1.83 (m, 1H), 1.77-1.73 (m, 2H), 0.90-0.85 (m, 2H), 0.61-0.58 (m, 2H).

Example 102: 3-((7-chloro-1-methyl-6-(pyrazolo[1,5-a]pyridin-3-yloxy)-1H-imidazo[4,5-b]pyridin-2-yl)amino)-5-cyclopropyl-1-(2-(4-methylpiperazin-1-yl)ethyl)pyridin-2(1H)-one

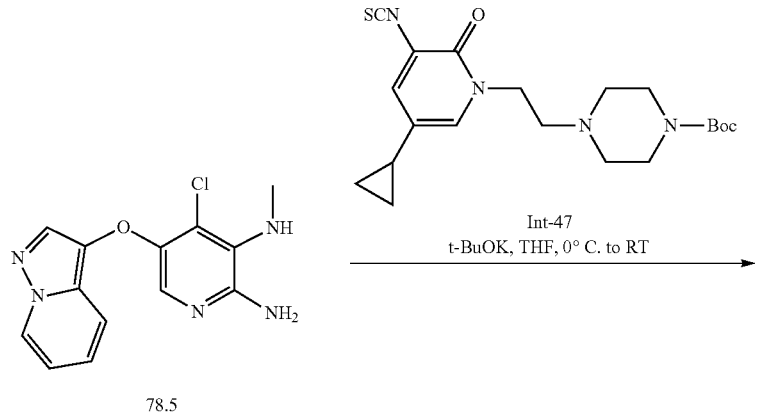

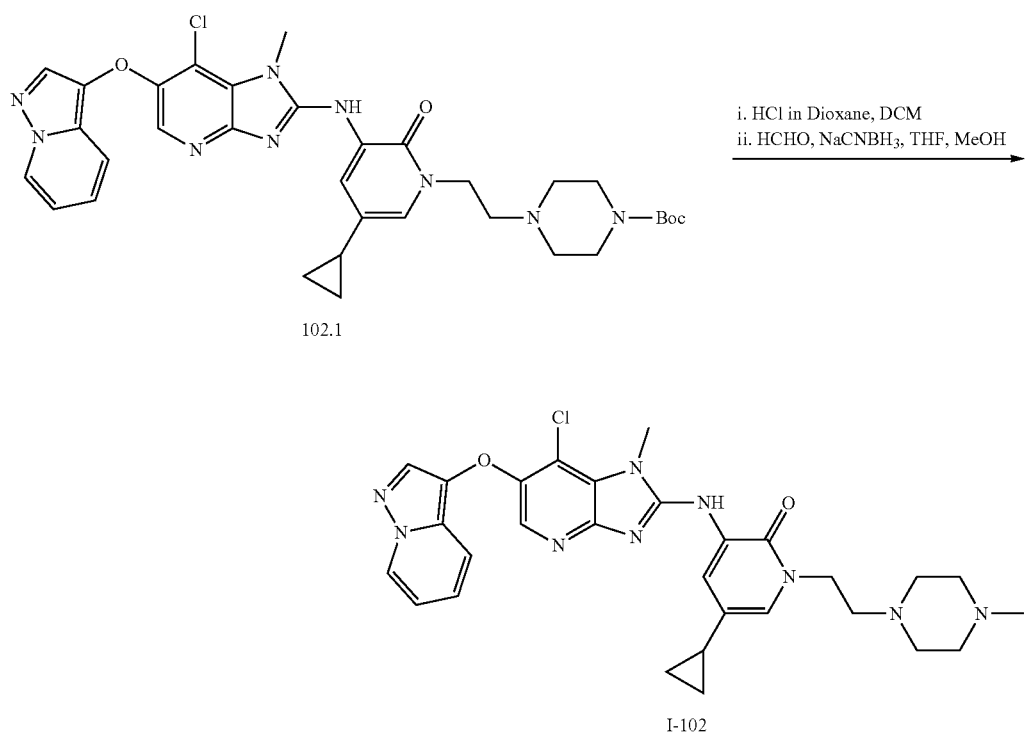

Synthesis of compound 102.1. Compound 102.1 was prepared from 78.5 and Int-47, following the procedure described in the synthesis of I-13. The product was purified by flash column chromatography on silica gel (CombiFlash®, 3.0% methanol in DCM). MS (ES): m/z 661.1 [M+H]$^+$.

Synthesis of I-102. To a solution of 102.1 (0.090 g, 0.136 mmol, 1.0 equiv) in DCM (5 mL) was added 4 M HCl in dioxane at 0° C. and stirred for 1 h. It was transferred into ice-cold aqueous sodium bicarbonate and was extracted with DCM. The combined organic layers were washed with brine, dried over anhydrous sodium sulfate, filtered and concentrated under reduced pressure. The residue was dissolved in THF-methanol (2:1, 5 mL) followed by addition of formaldehyde (0.010 g, 0.34 mmol, 2.5 equiv). The reaction mixture was stirred at room temperature for 10 min, and sodium cyanoborohydride (0.018 g, 0.272 mmol, 2.0 equiv) was added at 0° C. It was stirred at room temperature for 30 min before it was poured into ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.5% methanol in DCM) to afford I-102. MS (ES): m/z 574.4 [M+H]$^+$, $^1$H NMR (DMSO-d$_6$, 400 MHz): δ 8.64-8.62 (d, J=6.8 Hz, 1H), 8.50 (s, 1H), 8.28 (s, 1H), 8.03-8.01 (d, J=8.4 Hz, 1H), 7.53-7.51 (d, J=8.8 Hz, 1H), 7.20 (s, 1H), 7.09-7.08 (d, J=6.4 Hz, 1H), 6.84-6.82 (d, J=6.8 Hz, 1H), 4.10 (bs, 2H), 4.00 (s, 4H), 2.00 (bs, 1H), 1.82 (bs, 1H), 1.56 (bs. 4H), 1.40 (s, 2H), 1.24 (bs, 6H), 0.88-0.86 (m, 2H), 0.59-0.58 (m, 2H).

Example 103: 3-((7-chloro-1-methyl-6-(pyrazolo[1,5-a]pyridin-3-yloxy)-1H-imidazo[4,5-b]pyridin-2-yl)amino)-1-(2-hydroxyethyl)-5-(trifluoromethyl)pyridin-2(1H)-one

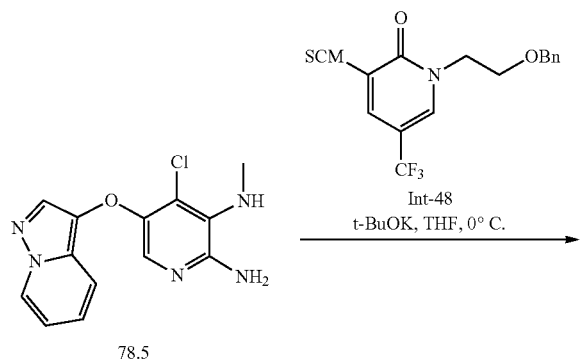

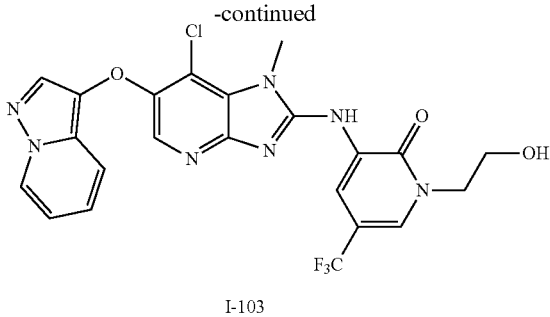

Synthesis of compound 103.1. Compound 103.1 was prepared from 78.5 and Int-48, following the procedure described in the synthesis of I-13. The product was purified by flash column chromatography on silica gel (Combi-Flash®, 1.7% methanol in DCM). MS (ES): m/z: 610.5 [M+H]$^+$.

Synthesis of I-103. Compound I-103 was prepared from 103.1, following the procedure described in the synthesis of I-23. The product was purified by flash column chromatography on silica gel (CombiFlash®, 4.0% methanol in DCM). MS (ES): m/z: 520.3 [M+H]$^+$, $^1$H NMR (DMSO-d$_6$, 400 MHz): δ 8.80 (s, 1H), 8.63 (s, 1H), 8.62-8.61 (d, J=2.0 Hz, 1H), 8.04-8.03 (d, J=2.8 Hz, 2H), 7.96 (s, 1H), 7.52-7.50 (d, J=9.2 Hz, 1H), 7.20-7.17 (m, 1H), 6.92-6.88 (m, 1H), 5.00-4.97 (m, 1H), 4.19-4.16 (m, 2H), 4.02 (s, 3H), 3.75-3.71 (m, 2H).

Example 104: 5-cyclopropyl-1-((1R,2S)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one and 5-cyclopropyl-1-((1S,2R)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one

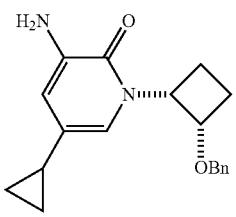

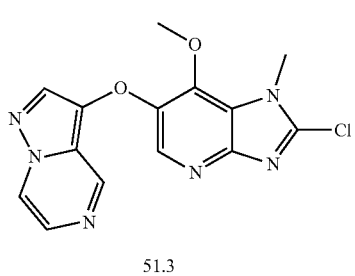

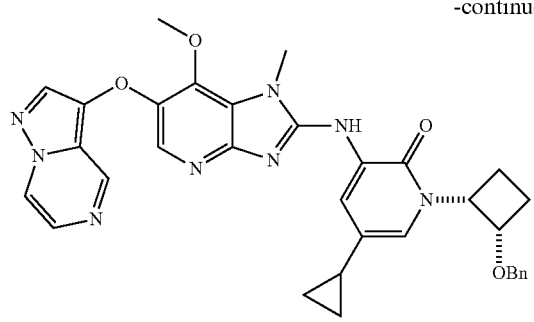

cis-(±)-104.1

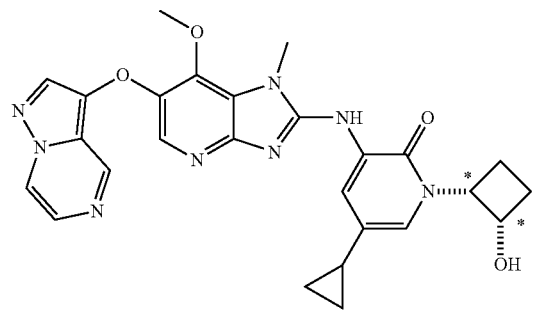

I-104-a and I-104-b

Synthesis of compound cis-(±)-104.1. Compound cis-(±)-104.1 was prepared from 51.3 and cis-(±)-Int-45.3, following the procedure described in the synthesis of I-53. The product was purified by flash column chromatography on silica gel (CombiFlash®, 2.0% methanol in DCM). MS (ES): m/z: 605.5 [M+H]⁺.

Synthesis of compound I-104-a and I-104-b. Racemate I-104 was prepared from 104.1, following the procedure described in the synthesis of I-23. The product was purified by flash column chromatography on silica gel (CombiFlash®, 5.0% methanol in DCM). MS (ES): m/z: 515.3 [M+H]⁺. It was subjected to HPLC separation (column: CHIRALPAK IB-N (250 mm×21 mm, 5 μm); mobile phase: (A) 0.1% DEA in hexane, (B) 0.1% DEA in isopropanol: acetonitrile (70:30); flow rate: 20 mL/min) to afford first eluting fraction (I-104-a) and second eluting fraction (I-104-b). (*Absolute stereochemistry not determined.)

I-104-a: MS (ES): m/z: 515.3 [M+H]⁺, ¹H NMR (DMSO-$d_6$, 400 MHz): δ 8.98 (s, 1H), 8.66-8.65 (d, J=3.6 Hz, 1H), 8.35 (s, 1H), 8.24 (s, 1H), 8.12 (bs, 1H), 7.97 (s, 1H), 7.84-7.83 (d, J=5.2 Hz, 1H), 7.25 (s, 1H), 5.60-5.58 (m, 1H), 4.91-4.89 (m, 1H), 4.45-4.41 (m, 1H), 4.10 (s, 3H), 3.89 (s, 3H), 2.12-2.09 (m, 2H), 1.91-1.88 (m, 1H), 1.71-1.61 (m, 2H), 0.89-0.87 (m, 2H), 0.63-0.62 (m, 2H).

I-104-b: MS (ES): m/z: 515.3 [M+H]⁺, ¹H NMR (DMSO-$d_6$, 400 MHz): δ 8.97 (s, 1H), 8.65-8.64 (d, J=3.6 Hz, 1H), 8.34 (s, 1H), 8.24 (s, 1H), 8.11 (bs, 1H), 7.97 (s, 1H), 7.84-7.83 (d, J=5.2 Hz, 1H), 7.24 (s, 1H), 5.59-5.57 (m, 1H), 4.90-4.86 (m, 1H), 4.45-4.41 (m, 1H), 4.10 (s, 3H), 3.89 (s, 3H), 2.14-2.09 (m, 2H), 1.91-1.88 (m, 1H), 1.71-1.56 (m, 2H), 0.89-0.87 (m, 2H), 0.63-0.62 (m, 2H).

Example 105: 3-((7-chloro-1-methyl-6-(pyrazolo[1,5-a]pyrazin-3-yloxy)-1H-imidazo[4,5-b]pyridin-2-yl)amino)-1-((1S,2S)-2-hydroxycyclobutyl)-5-(trifluoromethyl)pyridin-2(1H)-one and 3-((7-chloro-1-methyl-6-(pyrazolo[1,5-a]pyrazin-3-yloxy)-1H-imidazo[4,5-b]pyridin-2-yl)amino)-1-((1R,2R)-2-hydroxycyclobutyl)-5-(trifluoromethyl)pyridin-2(1H)-one

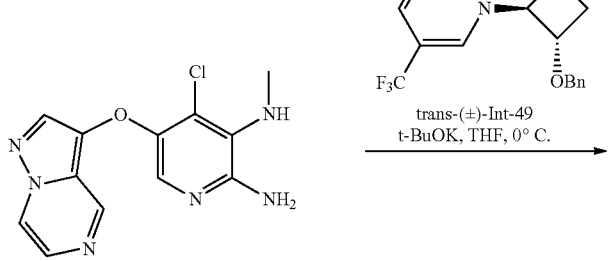

21.7

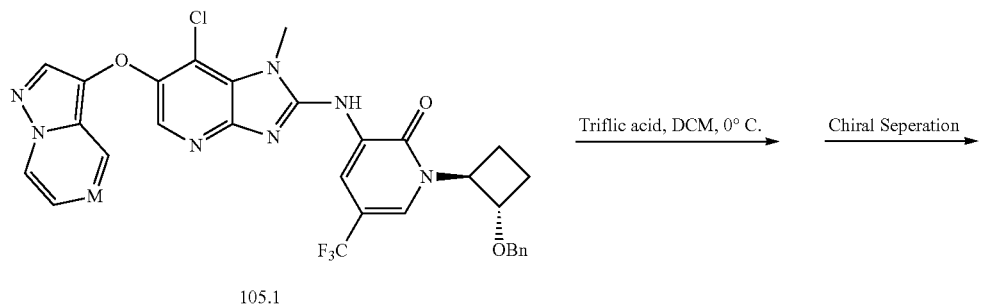

105.1

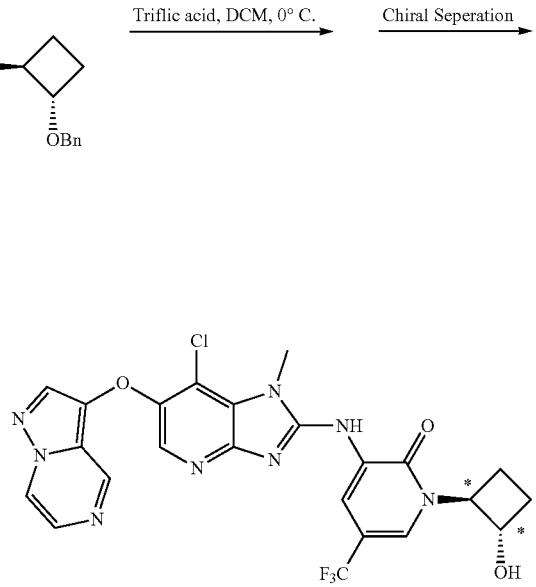

I-105-a and I-105-b

Synthesis of compound 105.1. Compound 105.1 was prepared from 21.7 and trans-(±)-Int-49, following the procedure described in the synthesis of I-13. The product was purified by flash column chromatography on silica gel (CombiFlash®, 1.6% methanol in DCM). MS (ES): m/z: 638.0 [M+H]$^+$.

Synthesis of compound I-105-a and I-105-b. Racemate I-105 was prepared from 105.1, following the procedure described in the synthesis of I-23. The product was purified by flash column chromatography on silica gel (CombiFlash®, 2.4% methanol in DCM). MS (ES): m/z 547.9 [M+H]$^+$. It was subjected to HPLC separation (column: CHIRALPAK IB-N (250 mm×21 mm, 5 μm); mobile phase: (A) 0.1% DEA in hexane, (B) 0.1% DEA in isopropanol: acetonitrile (70:30); flow rate: 20 mL/min) to afford first eluting fraction (I-105-a) and second eluting fraction (I-105-b). (*Absolute stereochemistry not determined.)

I-105-a: MS (ES): m/z: 547.4 [M+H]$^+$, $^1$H NMR (DMSO-d$_6$, 400 MHz): δ 9.07 (s, 1H), 8.95 (s, 1H), 8.72-8.71 (d, J=4.4 Hz, 1H), 8.58 (bs, 1H), 8.26 (s, 1H), 8.07 (s, 1H), 8.04 (s, 1H), 7.89-7.88 (d, J=4.8 Hz, 1H), 4.92-4.90 (m, 1H), 4.52-4.50 (m, 1H), 4.02 (s, 3H), 3.17 (s, 1H), 2.16-2.14 (m, 2H), 1.76-1.64 (m, 2H).

I-105-b: MS (ES): m/z: 547.4 [M+H]$^+$, $^1$H NMR (DMSO-d$_6$, 400 MHz): δ 9.08 (s, 1H), 8.95 (s, 1H), 8.73-8.72 (d, J=4.4 Hz, 1H), 8.60 (bs, 1H), 8.27 (s, 1H), 8.08 (s, 1H), 8.04 (s, 1H), 7.90-7.89 (d, J=4.8 Hz, 1H), 7.29 (s, 1H), 4.93-4.91 (m, 1H), 4.53-4.51 (m, 1H), 4.03 (s, 3H), 3.18 (s, 1H), 2.18-2.15 (m, 2H), 1.79-1.65 (m, 2H).

Example 106: 5-cyclopropyl-3-((7-methoxy-1-methyl-6-(pyrazolo[1,5-a]pyrazin-3-yloxy)-1H-imidazo[4,5-b]pyridin-2-yl)amino)-1-(2-methoxy-2-methylpropyl)pyridin-2(1H)-one

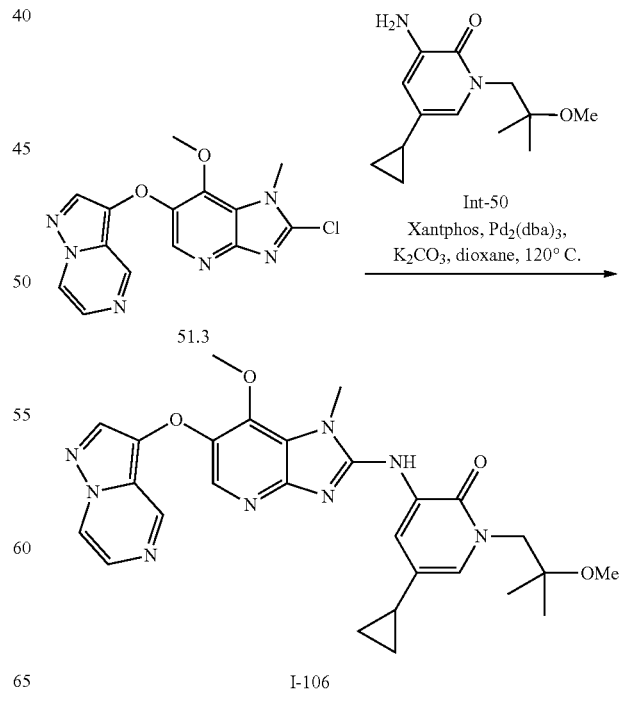

I-106

Synthesis of I-106. Compound I-106 was prepared from 51.3 and Int-50, following the procedure described in the synthesis of I-53. The product was purified by flash column chromatography on silica gel (CombiFlash®, 3.2% methanol in DCM). MS (ES): m/z: 531.5 [M+H]$^+$, $^1$H NMR (DMSO-d$_6$, 400 MHz): δ 8.98 (s, 1H), 8.66-8.65 (d, J=4.0 Hz, 1H), 8.32 (s, 1H), 8.28 (s, 1H), 8.11 (s, 1H), 7.97 (s, 1H), 7.84-7.83 (d, J=4.4 Hz, 1H), 6.99 (s, 1H), 4.09 (s, 5H), 3.88 (s, 3H), 3.20 (s, 3H), 1.82 (bs, 1H), 1.12 (s, 6H), 0.88-0.87 (m, 2H), 0.55-0.54 (m, 2H).

Example 107: (R)-3-((7-chloro-1-methyl-6-(pyrazolo[1,5-a]pyrazin-3-yloxy)-1H-imidazo[4,5-b]pyridin-2-yl)amino)-1-(tetrahydro-2H-pyran-3-yl)-5-(trifluoromethyl)pyridin-2(1H)-one and (S)-3-((7-chloro-1-methyl-6-(pyrazolo[1,5-a]pyrazin-3-yloxy)-1H-imidazo[4,5-b]pyridin-2-yl)amino)-1-(tetrahydro-2H-pyran-3-yl)-5-(trifluoromethyl)pyridin-2(1H)-one 8.11 (s, 1H), 8.05 (s, 1H), 7.88-7.86 (d, J=4.8 Hz, 1H), 4.88 (bs, 1H), 4.01 (s, 3H), 3.89-3.87 (m, 1H), 3.82-3.77 (m, 2H), 3.58-3.55 (m, 1H), 2.25-2.16 (m, 2H), 2.00 (bs, 2H).

I-107-b: MS (ES): m/z: 561.2 [M+H]$^+$, $^1$H NMR (DMSO-d$_6$, 400 MHz): δ 9.04 (s, 1H), 8.88 (s, 1H), 8.70-8.69 (d, J=3.6 Hz, 1H), 8.61 (bs, 1H), 8.24 (s, 1H), 8.11 (s, 1H), 8.05 (s, 1H), 7.88-7.86 (d, J=4.8 Hz, 1H), 4.88 (bs, 1H), 4.08 (s, 3H), 3.89-3.87 (m, 1H), 3.82-3.77 (m, 2H), 3.58-3.53 (m, 1H), 2.21-2.19 (m, 2H), 2.00 (bs, 2H).

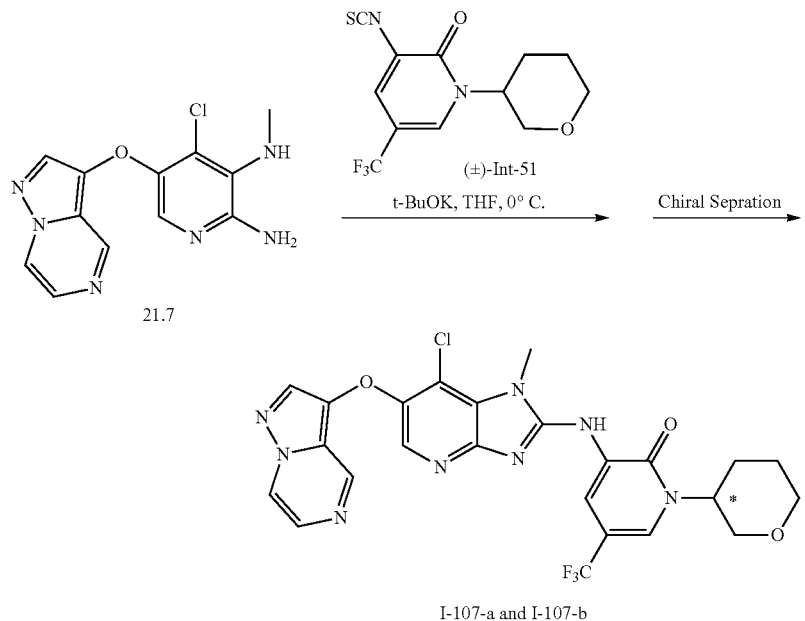

Synthesis of compound I-107-a and I-107-b. Racemate I-107 was prepared from 21.7 and (±)-Int-51, following the procedure described in the synthesis of I-13. The product was purified by flash column chromatography on silica gel (CombiFlash®, 2.0% methanol in DCM). It was subjected to HPLC separation (column: CHIRALPAK IC (250 mm×21 mm, 5 µm); mobile phase: (A) 0.1% DEA in methanol, (B) 0.1% DEA in acetonitrile; flow rate: 20 mL/min) to afford first eluting fraction (I-107-a) and second eluting fraction (I-107-b). (*Absolute stereochemistry not determined.)

I-107-a: MS (ES): m/z: 561.4 [M+H]$^+$, $^1$H NMR (DMSO-d$_6$, 400 MHz): δ 9.04 (s, 1H), 8.88 (s, 1H), 8.70-8.69 (d, J=3.6 Hz, 1H), 8.62-8.61 (d, J=2.0 Hz, 1H), 8.24 (s, 1H),

Example 108: 3-((7-chloro-1-methyl-6-(pyrazolo[1,5-a]pyrazin-3-yloxy)-1H-imidazo[4,5-b]pyridin-2-yl)amino)-5-cyclopropyl-2H-[1,3'-bipyridin]-2-one

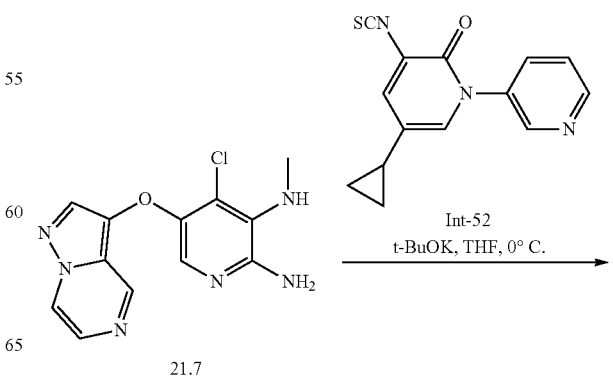

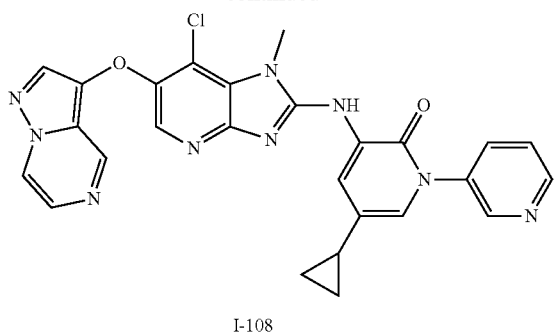

I-108

Synthesis of I-108. Compound I-108 was prepared from 21.7 and Int-52, following the procedure described in the synthesis of I-13. The product was purified by flash column chromatography on silica gel (CombiFlash®, 4.0% methanol in DCM). MS (ES): m/z: 526.2 [M+H]$^+$, $^1$H NMR (DMSO-d$_6$, 400 MHz): δ 9.04 (s, 1H), 8.75 (s, 1H), 8.69 (s, 1H), 8.63 (s, 1H), 8.37 (s, 1H), 8.24 (s, 1H), 8.05 (bs, 1H), 8.00 (bs, 1H), 7.87 (s, 1H), 7.62 (bs, 2H), 7.27 (s, 1H), 3.99 (s, 3H), 1.55 (bs, 1H), 0.88 (bs, 2H), 0.66 (bs, 2H).

Example 109: 3-((7-chloro-1-methyl-6-(pyrazolo[1,5-a]pyrazin-3-yloxy)-1H-imidazo[4,5-b]pyridin-2-yl)amino)-5-(trifluoromethyl)-2H-[1,3'-bipyridin]-2-one

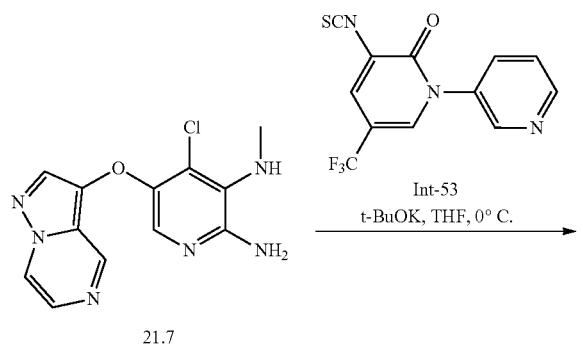

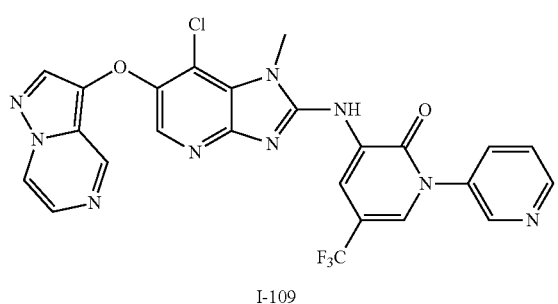

I-109

Synthesis of I-109. Compound I-109 was prepared from 21.7 and Int-53, following the procedure described in the synthesis of I-13. The product was purified by flash column chromatography on silica gel (CombiFlash®, 4.2% methanol in DCM). MS (ES): m/z: 554.2 [M+H]$^+$, $^1$H NMR (DMSO-d$_6$, 400 MHz): δ 9.05 (s, 1H), 8.98 (s, 1H), 8.81 (s, 1H), 8.73-8.69 (m, 3H), 8.27 (s, 1H), 8.14 (s, 1H), 8.09 (s, 1H), 8.06 (s, 1H), 7.88-7.87 (d, J=4.8 Hz, 1H), 7.66-7.63 (m, 1H), 4.01 (s, 3H).

Example 110: 5-cyclopropyl-1-((1S,2S)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one and 5-cyclopropyl-1-((1R,2R)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)pyridin-2(1H)-one

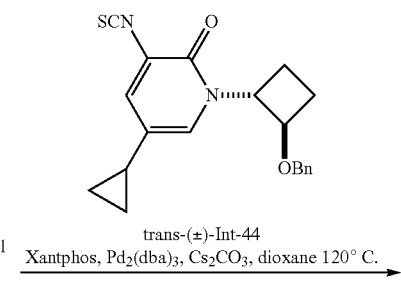

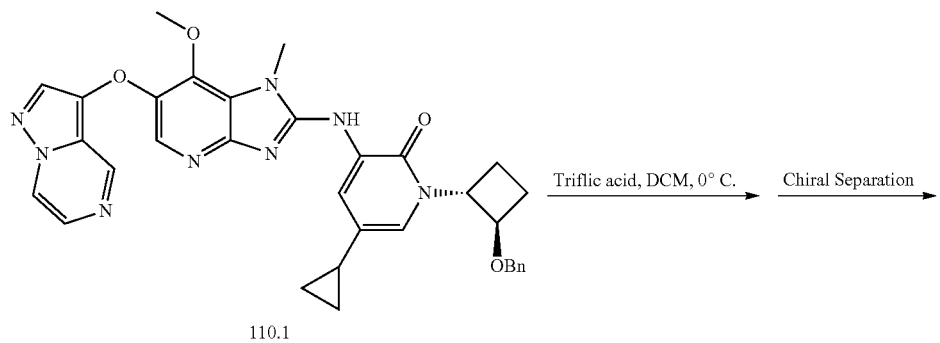

110.1

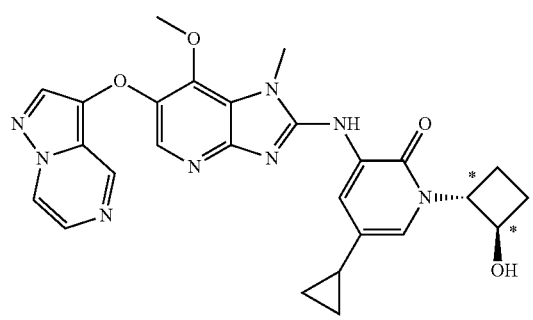

I-110-a and I-110-b

Synthesis of compound 110.1. Compound 110.1 was prepared from 51.3 and trans-(±)-Int-44, following the procedure described in the synthesis of I-53. The product was purified by flash column chromatography on silica gel (CombiFlash®, 2.1% methanol in DCM). MS (ES): m/z: 605.5 [M+H]+.

Synthesis of compound I-110-a and I-110-b. Racemate I-110 was prepared from 110.1, following the procedure described in the synthesis of I-23. The product was purified by flash column chromatography on silica gel (CombiFlash®, 5.0% methanol in DCM). MS (ES): m/z: 515.3 [M+H]+. It was subjected to HPLC separation (column: CHIRALPAK IB-N (250 mm×21 mm, 5 μm); mobile phase: (A) 0.1% DEA in hexane, (B) 0.1% DEA in isopropanol: acetonitrile (70:30); flow rate: 20 mL/min) to afford first eluting fraction (I-110-a) and second eluting fraction (I-110-b). (*Absolute stereochemistry not determined.)

I-110-a: MS (ES): m/z: 515.5 [M+H]+, 1H NMR (DMSO-d6, 400 MHz): δ 8.98 (s, 1H), 8.67-8.65 (d, J=4.0 Hz, 1H), 8.35 (s, 1H), 8.24 (s, 1H), 8.11 (bs, 1H), 7.97 (s, 1H), 7.84-7.83 (d, J=5.2 Hz, 1H), 7.26 (s, 1H), 5.61-5.60 (m, 1H), 4.92-4.89 (m, 1H), 4.47-4.39 (m, 1H), 4.09 (s, 3H), 3.89 (s, 3H), 2.14-2.07 (m, 2H), 1.91-1.86 (m, 1H), 1.71-1.61 (m, 2H), 0.89-0.87 (m, 2H), 0.63-0.62 (m, 2H).

I-110-b: MS (ES): m/z: 515.5 [M+H]+, 1H NMR (DMSO-d6, 400 MHz): δ 8.99 (s, 1H), 8.68-8.67 (d, J=4.8 Hz, 1H), 8.36 (s, 1H), 8.26 (s, 1H), 8.13 (bs, 1H), 7.98 (s, 1H), 7.86-7.84 (d, J=4.8 Hz, 1H), 7.27 (s, 1H), 5.62-5.60 (m, 1H), 4.93-4.90 (m, 1H), 4.47-4.39 (m, 1H), 4.11 (s, 3H), 3.90 (s, 3H), 2.15-2.08 (m, 2H), 1.92-1.88 (m, 1H), 1.73-1.62 (m, 2H), 0.89-0.85 (m, 2H), 0.63-0.62 (m, 2H).

Example 111: trans-5-cyclopropyl-1-(3-hydroxycyclobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one

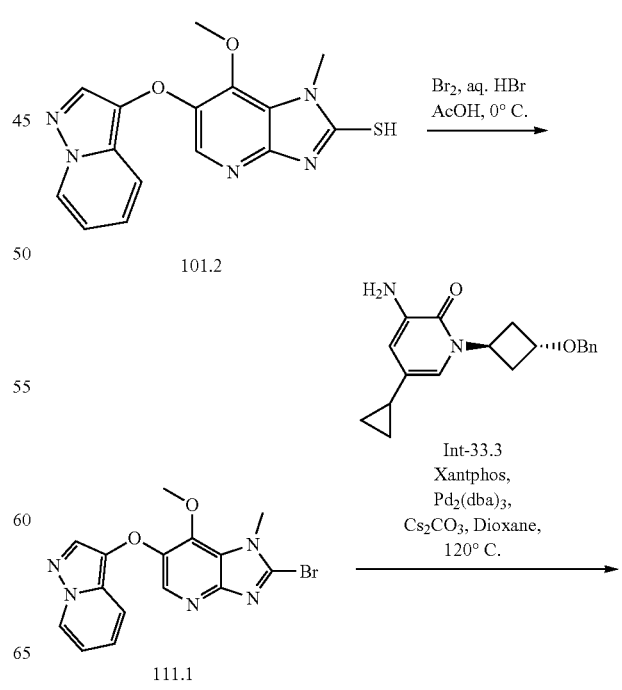

723
-continued

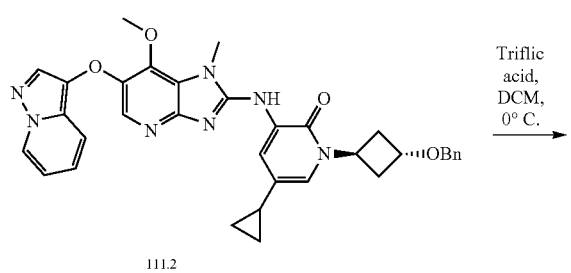

111.2

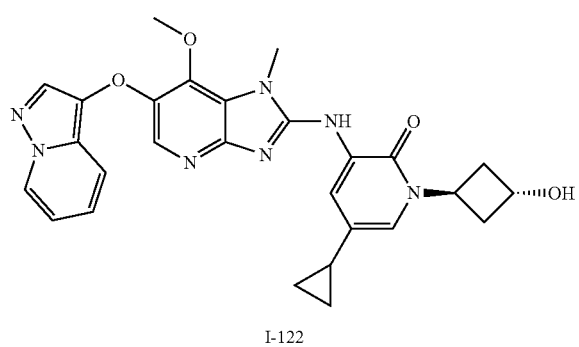

I-122

Synthesis of compound 111.1. Compound 111.1 was prepared from 101.2, following the procedure described in the synthesis of 53.2. The product was purified by flash column chromatography on silica gel (CombiFlash®, 2.2% methanol in DCM). MS (ES): m/z 375.2 [M+H]+.

Synthesis of compound 111.2. Compound 111.2 was prepared from 111.1 and Int-33.3, following the procedure described in the synthesis of I-53. The product was purified by flash column chromatography on silica gel (Combi-Flash®, 2.5% methanol in DCM). MS (ES): m/z: 604.5 [M+H]+.

Synthesis of I-111. Compound I-111 was prepared from 111.2, following the procedure described in the synthesis of I-23. The product was purified by flash column chromatography on silica gel (CombiFlash®, 3.5% methanol in DCM). MS (ES): m/z: 514.5 [M+H]+, $^1$H NMR (DMSO-$d_6$, 400 MHz): δ 8.61-8.59 (d, J=7.2 Hz, 1H), 8.33 (s, 1H), 8.22 (s, 1H), 7.96-7.94 (d, J=5.6 Hz, 2H), 7.53-7.51 (d, J=8.8 Hz, 1H), 7.25 (s, 1H), 7.18-7.15 (t, J=7.2 Hz, 8.0 Hz, 1H), 6.90-6.86 (t, J=6.8 Hz, 6.8 Hz, 1H), 5.43-5.37 (m, 1H), 5.25-5.24 (m, 1H), 4.39 (bs, 1H), 4.14 (s, 3H), 3.90 (s, 3H), 3.42-3.35 (m, 2H), 2.35-2.31 (m, 2H), 1.93-1.86 (m, 1H), 0.91-0.87 (m, 2H), 0.63-0.61 (m, 2H).

724

Example 112: cis-5-cyclopropyl-1-(3-hydroxycy-clobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one

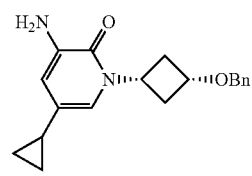

Int-32
Xantphos,
Pd$_2$(dba)$_3$,
Cs$_2$CO$_3$, Dioxane,
120° C.

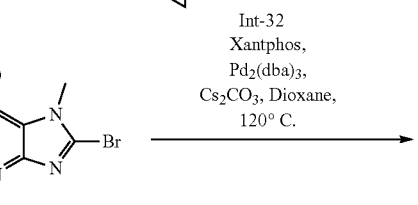

111.1

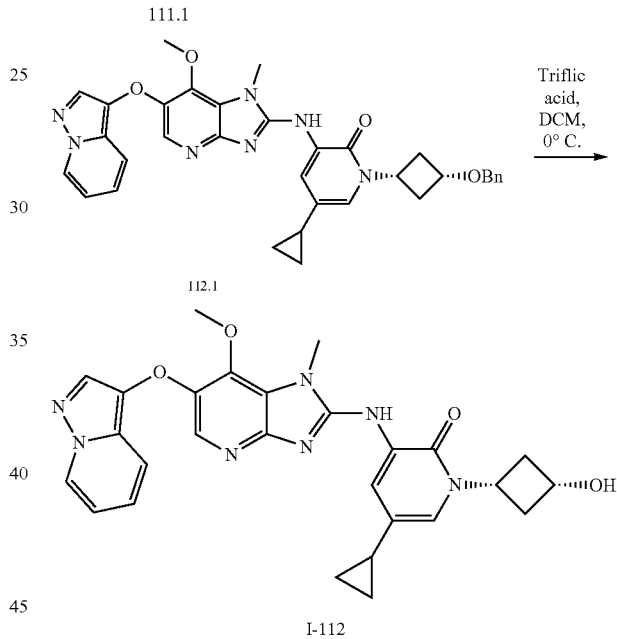

I-112

Synthesis of compound 112.1. Compound 112.1 was prepared from 111.1 and Int-32, following the procedure described in the synthesis of I-53. The product was purified by flash column chromatography on silica gel (Combi-Flash®, 2.6% methanol in DCM). MS (ES): m/z: 604.5 [M+H]+.

Synthesis of I-112. Compound I-112 was prepared from 112.1, following the procedure described in the synthesis of I-23. The product was purified by flash column chromatography on silica gel (CombiFlash®, 3.5% methanol in DCM). MS (ES): m/z: 514.5 [M+H]+, $^1$H NMR (DMSO-$d_6$, 400 MHz): δ 8.61-8.59 (d, J=7.2 Hz, 1H), 8.33 (s, 1H), 8.23 (s, 1H), 7.96-7.94 (d, J=5.6 Hz, 2H), 7.54-7.52 (d, J=8.8 Hz, 1H), 7.25 (s, 1H), 7.19-7.15 (t, J=7.2 Hz, 8.0 Hz, 1H), 6.90-6.87 (t, J=6.8 Hz, 6.8 Hz, 1H), 5.30-5.28 (m, 1H), 4.71-4.63 (m, 1H), 4.14 (s, 3H), 4.01 (bs, 1H), 3.90 (s, 3H), 2.78-2.77 (m, 2H), 2.17-2.15 (m, 2H), 1.95-1.88 (m, 1H), 0.91-0.89 (m, 2H), 0.63-0.61 (m, 2H).

Example 113: 1-((1S,2S)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)-5-(trifluoromethyl)pyridin-2(1H)-one and 1-((1R,2R)-2-hydroxycyclobutyl)-3-((7-methoxy-1-methyl-6-(pyrazolo[1,5-a]pyrazin-3-yloxy)-1H-imidazo[4,5-b]pyridin-2-yl)amino)-5-(trifluoromethyl)pyridin-2(1H)-one separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-113-a) and second eluting fraction (I-113-b). (*Absolute stereochemistry not determined.)

I-113-a: MS (ES): m/z: 543.4 [M+H]$^+$, $^1$H NMR (DMSO-d$_6$, 400 MHz): δ 9.01 (s, 1H), 8.68-8.67 (d, J=4.0 Hz, 2H), 8.64-8.63 (d, J=2.0 Hz, 1H), 8.16 (s, 1H), 8.00 (s, 1H), 7.99

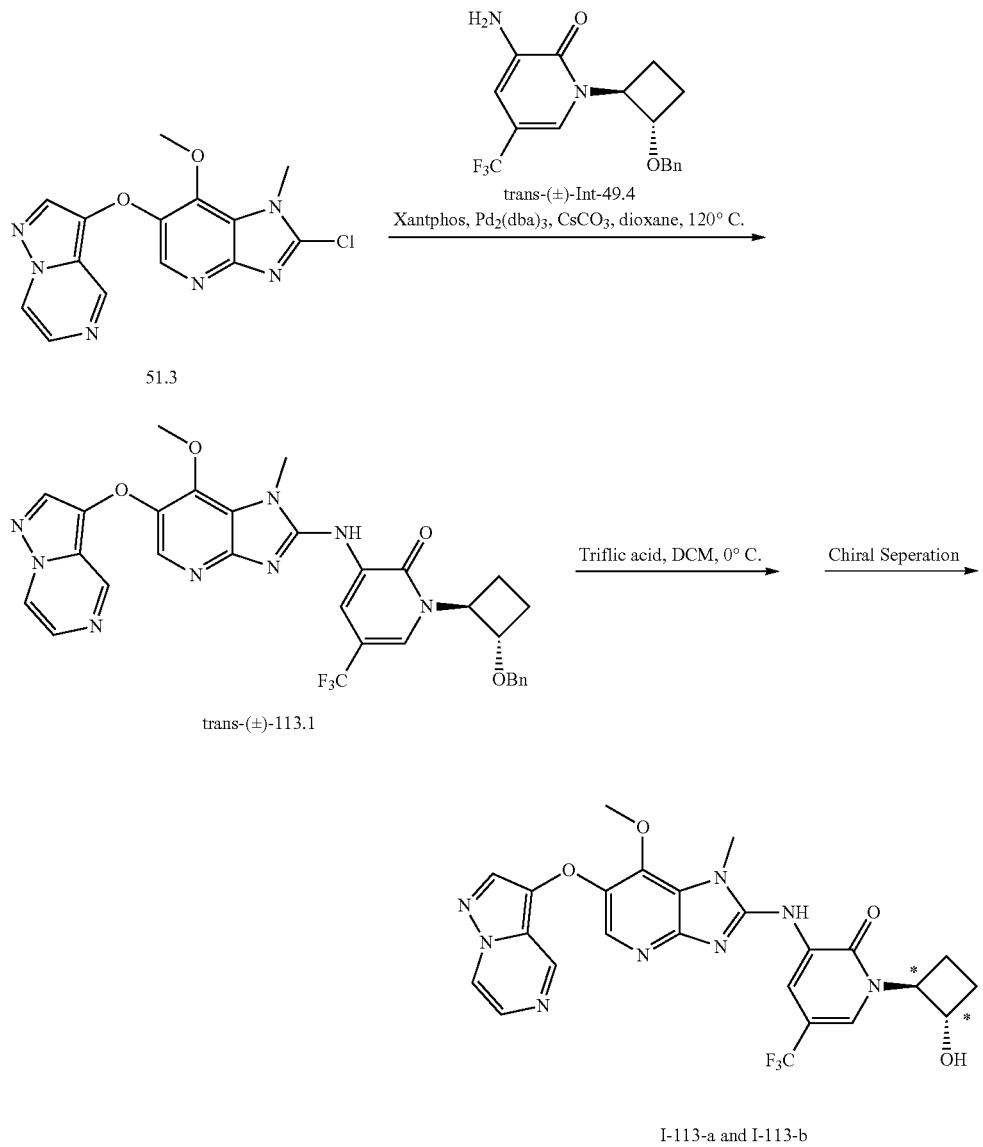

Synthesis of compound trans-(±)-113.1. Compound trans-(±)-113.1 was prepared from 51.3 and trans-(±)-Int-49.4, following the procedure described in the synthesis of I-53. The product was purified by flash column chromatography on silica gel (CombiFlash®, 2.1% methanol in DCM). MS (ES): m/z: 633.5 [M+H]$^+$.

Synthesis of I-113-a and I-113-b. Racemate I-113 was prepared from trans-(±)-113.1, following the procedure described in the synthesis of I-23. The product was purified by flash column chromatography on silica gel (Combi-Flash®, 4.8% methanol in DCM). It was subjected to HPLC (s, 1H), 7.86-7.84 (d, J=4.8 Hz, 1H), 7.27 (s, 1H), 5.72-5.70 (m, 1H), 4.95-4.89 (m, 1H), 4.53-4.49 (m, 1H), 4.12 (s, 3H), 3.93 (s, 3H), 2.19-2.13 (m, 2H), 1.79-1.72 (m, 1H), 1.69-1.62 (m, 1H).

I-113-b: MS (ES): m/z: 543.3 [M+H]$^+$, $^1$H NMR (DMSO-d$_6$, 400 MHz): δ 9.01 (s, 1H), 8.68-8.67 (d, J=4.0 Hz, 2H), 8.64-8.63 (d, J=2.0 Hz, 1H), 8.16 (s, 1H), 8.00 (s, 1H), 7.99 (s, 1H), 7.86-7.84 (d, J=4.8 Hz, 1H), 7.27 (s, 1H), 5.72-5.70 (m, 1H), 4.95-4.89 (m, 1H), 4.53-4.49 (m, 1H), 4.12 (s, 3H), 3.93 (s, 3H), 2.19-2.13 (m, 2H), 1.79-1.72 (m, 1H), 1.69-1.62 (m, 1H).

Example 114: 3-((7-chloro-1-methyl-6-(pyrazolo[1,5-a]pyridin-3-yloxy)-1H-imidazo[4,5-b]pyridin-2-yl)amino)-5-cyclopropyl-1-((1R,2S)-2-hydroxycyclobutyl)pyridin-2(1H)-one and 3-((7-chloro-1-methyl-6-(pyrazolo[1,5-a]pyridin-3-yloxy)-1H-imidazo[4,5-b]pyridin-2-yl)amino)-5-cyclopropyl-1-((1S,2R)-2-hydroxycyclobutyl)pyridin-2(1H)-one

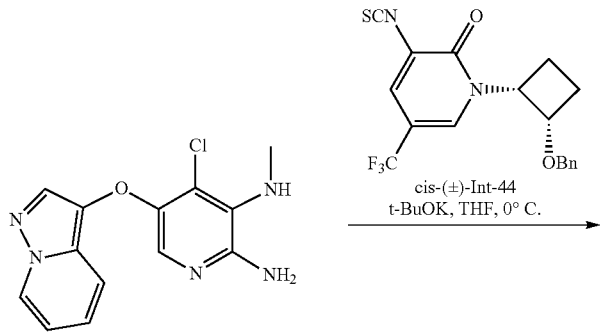

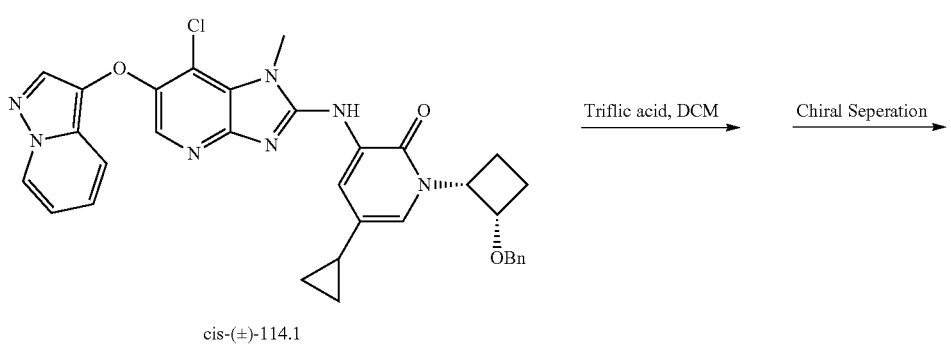

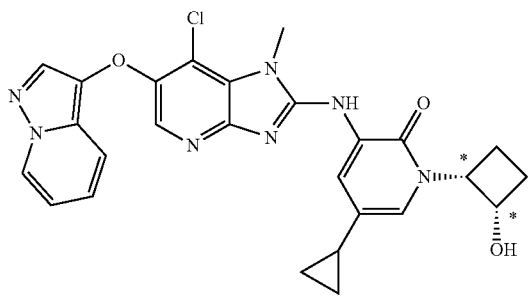

I-114-a and I-114-b

Synthesis of compound cis-(+)114.1. Compound cis-(±)-114.1 was prepared from 78.5 and cis-(±)-Int-58, following the procedure described in the synthesis of I-13. The product was purified by flash column chromatography on silica gel (CombiFlash®, 2.0% methanol in DCM). MS (ES): m/z: 609.1 [M+H]$^+$.

Synthesis of compound I-114-a and I-114-b. Racemate I-114 was prepared from cis-(±)-114.1, following the procedure described in the synthesis of I-23. The product was purified by flash column chromatography on silica gel (CombiFlash®, 3.0% methanol in DCM). MS (ES): m/z 518.2 [M+H]$^+$. It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-114-a) and second eluting fraction (I-114-b). (*Absolute stereochemistry not determined.)

I-114-a: MS (ES): m/z: 518.2 [M+H]$^+$, $^1$H NMR (DMSO-$d_6$, 400 MHz): δ 8.64-8.63 (d, J=6.8 Hz, 1H), 8.52 (s, 1H), 8.23-8.22 (d, J=1.6 Hz, 1H), 8.03-8.01 (d, J=5.6 Hz, 2H), 7.53-7.50 (d, J=9.2 Hz, 1H), 7.29 (s, 1H), 7.21-7.17 (m, 1H), 6.92-6.89 (m, 1H), 5.63-5.61 (d, J=6.8 Hz, 1H), 4.93-4.91 (m, 1H), 4.46-4.40 (m, 1H), 4.00 (s, 3H), 2.17-2.10 (m, 2H), 1.90-1.86 (m, 1H), 1.69-1.62 (m, 2H), 0.90-0.85 (m, 2H), 0.63-0.62 (m, 2H).

I-114-b: MS (ES): m/z: 518.1 [M+H]$^+$, $^1$H NMR (DMSO-$d_6$, 400 MHz): δ 8.63-8.61 (d, J=7.2 Hz, 1H), 8.51 (s, 1H), 8.22 (bs, 1H), 8.01-8.00 (d, J=5.6 Hz, 2H), 7.51-7.49 (d, J=9.2 Hz, 1H), 7.28 (s, 1H), 7.20-7.16 (m, 1H), 6.91-6.88 (m, 1H), 5.62-5.60 (d, J=6.4 Hz, 1H), 4.97-4.87 (m, 1H), 4.48-4.38 (m, 1H), 3.99 (s, 3H), 2.18-2.09 (m, 2H), 1.91-1.85 (m, 1H), 1.68-1.61 (m, 2H), 0.88-0.85 (m, 2H), 0.62-0.61 (m, 2H).

Example 115: 3-((7-chloro-1-methyl-6-(pyrazolo[1,5-a]pyridin-3-yloxy)-1H-imidazo[4,5-b]pyridin-2-yl)amino)-5-cyclopropyl-1-(1-methyl-1H-pyrazol-4-yl)pyridin-2(1H)-one

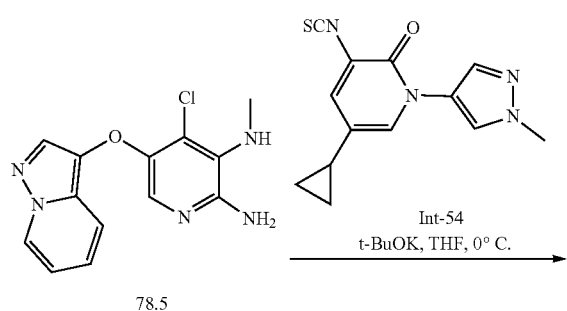

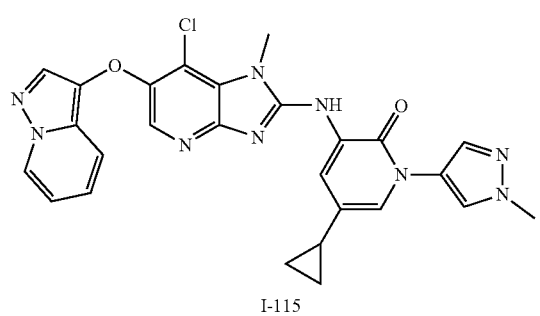

I-115

Synthesis of I-115. Compound I-115 was prepared from 78.5 and Int-54, following the procedure described in the synthesis of I-13. The product was purified by flash column chromatography on silica gel (CombiFlash®, 3.8% methanol in DCM). MS (ES): m/z: 528.2 [M+H]+, 1H NMR (DMSO-d6, 400 MHz): δ 8.64 (s, 1H), 8.62 (s, 1H), 8.37 (s, 1H), 8.28-8.27 (d, J=1.6 Hz, 1H), 8.04-8.03 (d, J=4.0 Hz, 2H), 7.97 (s, 1H), 7.53-7.51 (d, J=8.8 Hz, 1H), 7.35 (s, 1H), 7.22-7.18 (m, 1H), 6.93-6.89 (m, 1H), 4.01 (s, 3H), 3.92 (s, 3H), 1.89 (bs, 1H), 0.91-0.89 (m, 2H), 0.67-0.66 (m, 2H).

Example 116: 4-((7-chloro-1-methyl-6-(pyrazolo[1,5-a]pyridin-3-yloxy)-1H-imidazo[4,5-b]pyridin-2-yl)amino)-6-cyclopropyl-2-methylpyridazin-3(2H)-one

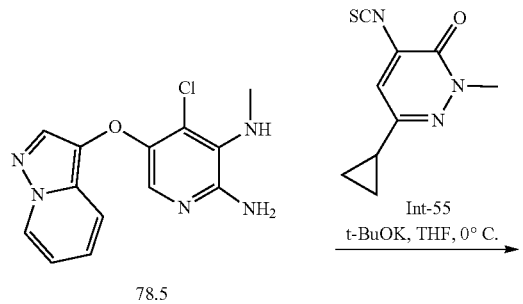

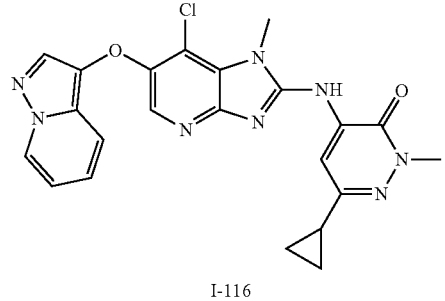

I-116

Synthesis of I-116. Compound I-116 was prepared from 78.5 and Int-55, following the procedure described in the synthesis of I-13. The product was purified by flash column chromatography on silica gel (CombiFlash®, 2.2% methanol in DCM). MS (ES): m/z: 463.3 [M+H]+, 1H NMR (DMSO-d6, 400 MHz): δ 9.19 (s, 1H), 8.65-8.63 (d, J=6.8 Hz, 1H), 8.10 (s, 1H), 8.06 (s, 1H), 7.97 (s, 1H), 7.54-7.52 (d, J=9.2 Hz, 1H), 7.22-7.19 (m, 1H), 6.93-6.90 (m, 1H), 4.03 (s, 3H), 3.71 (s, 3H), 2.00-1.99 (m, 1H), 0.97-0.93 (m, 2H), 0.82-0.79 (m, 2H).

Example 117: 3-((7-chloro-1-methyl-6-(pyrazolo[1,5-a]pyrazin-3-yloxy)-1H-imidazo[4,5-b]pyridin-2-yl)amino)-5-cyclopropyl-1-(3-(3,3-difluoropyrrolidin-1-yl)propyl)pyridin-2(1H)-one

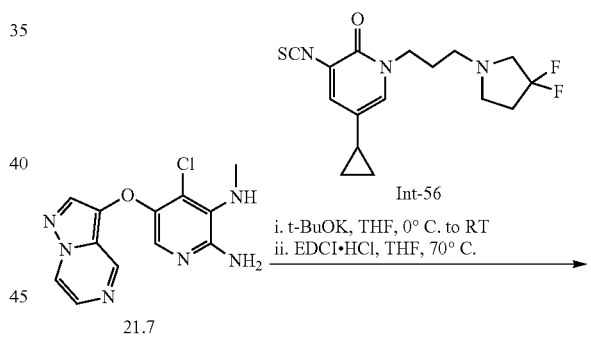

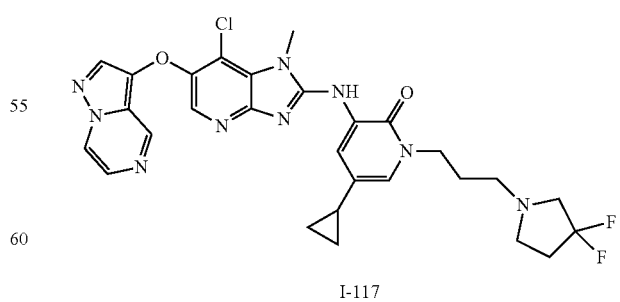

I-117

Synthesis of I-117. Compound I-117 was prepared from 21.7 and Int-56, following the procedure described in the synthesis of I-51. The product was purified by flash column chromatography on silica gel (CombiFlash®, 3.0% methanol in DCM). MS (ES): m/z 596.5 [M+H]⁺, ¹H NMR (DMSO-d$_6$, 400 MHz): δ 9.05-9.04 (d, J=1.6 Hz, 1H), 8.71-8.69 (m, 1H), 8.55 (s, 1H), 8.30-8.29 (d, J=2.4 Hz, 1H), 8.22 (s, 1H), 8.06 (s, 1H), 7.89-7.87 (d, J=5.2 Hz, 1H), 7.24-7.23 (d, J=2.0 Hz, 1H), 4.05-4.01 (m, 2H), 4.00 (s, 3H), 2.94-2.88 (m, 2H), 2.71-2.65 (m, 2H), 2.47 (bs, 2H), 2.30-2.20 (m, 2H), 1.91-1.80 (m, 3H), 0.91-0.86 (m, 2H), 0.62-0.58 (m, 2H).

Example 118: 3-((7-chloro-1-methyl-6-(pyrazolo[1,5-a]pyrazin-3-yloxy)-1H-imidazo[4,5-b]pyridin-2-yl)amino)-1-(3-(3,3-difluoropyrrolidin-1-yl)propyl)-5-(trifluoromethyl)pyridin-2(1H)-one

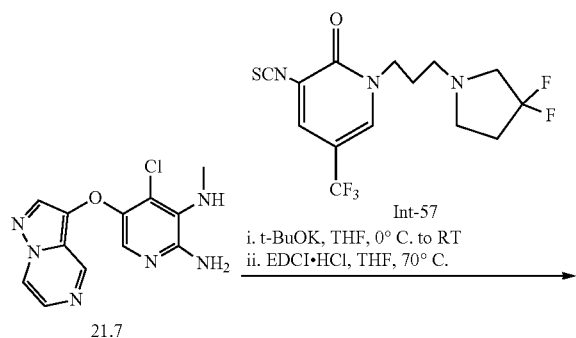

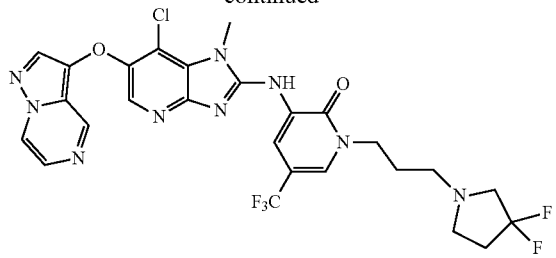

I-118

Synthesis of I-118. Compound I-118 was prepared from 21.7 and Int-57, following the procedure described in the synthesis of I-51. The product was purified by flash column chromatography on silica gel (CombiFlash®, 2.5% methanol in DCM). MS (ES): m/z 624.3 [M+H]⁺, ¹H NMR (DMSO-d$_6$, 400 MHz): δ 9.05-9.04 (d, J=1.6 Hz, 1H), 8.86 (bs, 1H), 8.71 (s, 1H), 8.63 (s, 1H), 8.26-8.25 (d, J=3.6 Hz, 1H), 8.12 (s, 1H), 8.07-8.06 (d, J=3.6 Hz, 1H), 7.88 (s, 1H), 4.17 (bs, 2H), 4.02 (s, 3H), 2.89 (bs, 2H), 2.69 (bs, 2H), 2.25 (bs, 2H), 1.93 (bs, 2H), 1.25 (bs, 2H).

Example 119: 3-((7-chloro-1-methyl-6-(pyrazolo[1,5-a]pyrazin-3-yloxy)-1H-imidazo[4,5-b]pyridin-2-yl)amino)-1-((1R,2S)-2-hydroxycyclobutyl)-5-(trifluoromethyl)pyridin-2(1H)-one and 3-((7-chloro-1-methyl-6-(pyrazolo[1,5-a]pyrazin-3-yloxy)-1H-imidazo[4,5-b]pyridin-2-yl)amino)-1-((1S,2R)-2-hydroxycyclobutyl)-5-(trifluoromethyl)pyridin-2(1H)-one

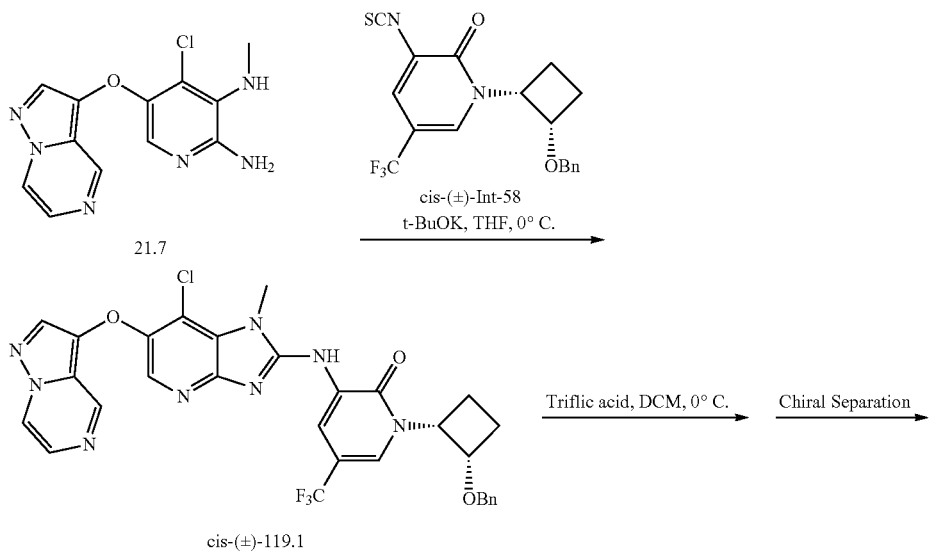

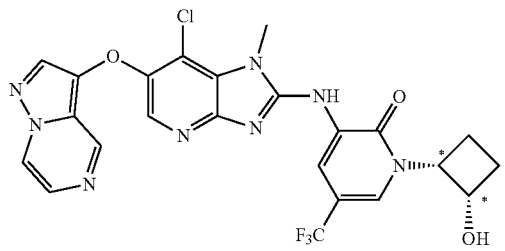

I-119-a and I-119-b

Synthesis of compound cis-(±)-119.1. Compound cis-(±)-119.1 was prepared from 21.7 and cis-(±)-Int-58, following the procedure described in the synthesis of I-13. The product was purified by flash column chromatography on silica gel (CombiFlash®, 1.6% methanol in DCM). MS (ES): m/z: 638.0 [M+H]+.

Synthesis of compound I-119-a and I-119-b. Racemate I-119 was prepared from cis-(±)-119.1, following the procedure described in the synthesis of I-23. The product was purified by flash column chromatography on silica gel (CombiFlash®, 2.4% methanol in DCM). MS (ES): m/z 547.9 [M+H]+. It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-119-a) and second eluting fraction (I-119-b). (*Absolute stereochemistry not determined.)

I-119-a: MS (ES): m/z: 547.4 [M+H]+, 1H NMR (DMSO-d6, 400 MHz): δ 9.05 (s, 1H), 8.87 (s, 1H), 8.71-8.70 (m, 1H), 8.63-8.62 (d, J=2.0 Hz, 1H), 8.26 (s, 1H), 8.06 (s, 1H), 8.04 (s, 1H), 7.89-7.88 (d, J=4.8 Hz, 1H), 5.73-5.71 (m, 1H), 4.94-4.92 (m, 1H), 4.52-4.50 (m, 1H), 4.02 (s, 3H), 2.18-2.16 (m, 2H), 1.77-1.65 (m, 2H).

I-119-b: MS (ES): m/z: 547.3 [M+H]+, 1H NMR (DMSO-d6, 400 MHz): δ 9.05 (s, 1H), 8.87 (s, 1H), 8.71-8.70 (m, 1H), 8.63-8.62 (d, J=2.0 Hz, 1H), 8.26 (s, 1H), 8.06 (s, 1H), 8.04 (s, 1H), 7.89-7.88 (d, J=4.8 Hz, 1H), 5.73-5.71 (m, 1H), 4.94-4.92 (m, 1H), 4.52-4.50 (m, 1H), 4.02 (s, 3H), 2.18-2.16 (m, 2H), 1.77-1.65 (m, 2H).

Example 120: 7-chloro-1-methyl-N-(4-((4-methylpiperazin-1-yl)methyl)-3-(trifluoromethyl)phenyl)-6-(pyrazolo[1,5-a]pyrazin-3-yloxy)-1H-imidazo[4,5-b]pyridin-2-amine

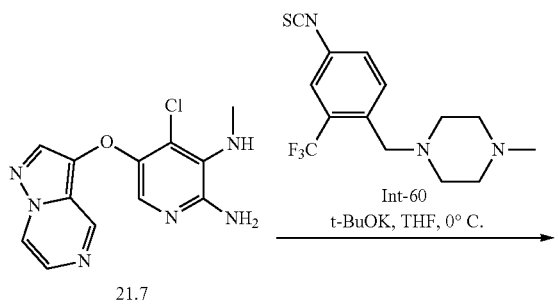

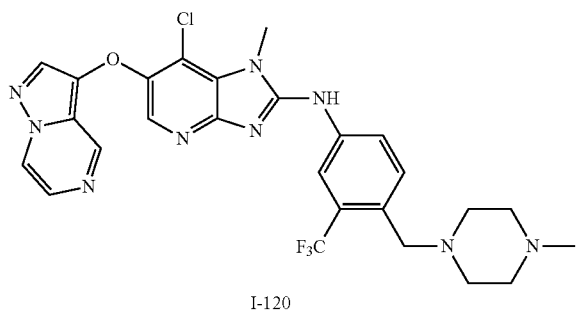

I-120

Synthesis of I-120. Compound I-120 was prepared from 21.7 and Int-60, following the procedure described in the synthesis of I-13. The product was purified by preparative HPLC. MS (ES): m/z: 572.2 [M+H]+, 1H NMR (DMSO-d6, 400 MHz): δ 9.65 (s, 1H), 9.03 (s, 1H), 8.70-8.69 (d, J=4.8 Hz 1H), 8.30 (s, 1H), 8.21 (s, 1H), 8.16 (s, 1H), 8.04 (s, 1H), 7.88-7.87 (d, J=4.8 Hz 1H), 7.73-7.71 (d, J=8.8 Hz 1H), 4.03 (s, 3H), 3.60 (s, 3H), 2.68 (s, 4H), 2.34 (s, 4H), 2.29 (bs, 2H).

Example 121: (S)-3-(5-cyclopropyl-3-((7-methoxy-1-methyl-6-(pyrazolo[1,5-a]pyrazin-3-yloxy)-1H-imidazo[4,5-b]pyridin-2-yl)amino)-2-oxopyridin-1(2H)-yl)butanenitrile and (R)-3-(5-cyclopropyl-3-((7-methoxy-1-methyl-6-(pyrazolo[1,5-a]pyrazin-3-yloxy)-1H-imidazo[4,5-b]pyridin-2-yl)amino)-2-oxopyridin-1(2H)-yl)butanenitrile

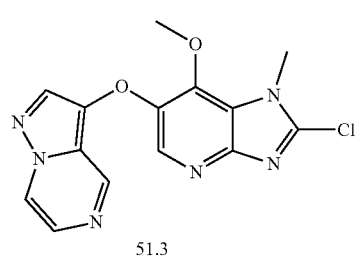

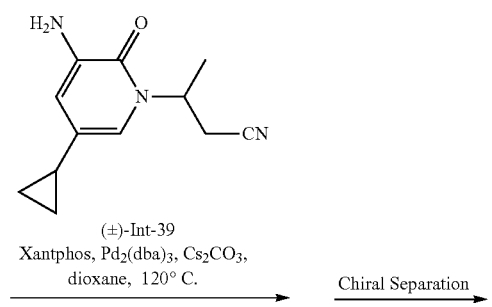

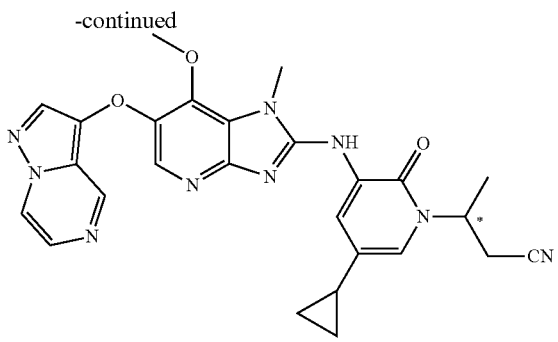

I-121-a and I-121-b

Synthesis of compound I-121-a and I-121-b. Racemate I-121 was prepared from 51.3 and (±)-Int-39, following the procedure described in the synthesis of I-53. The product was purified by flash column chromatography on silica gel (CombiFlash®, 2.2% methanol in DCM). It was subjected to HPLC separation (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-121-a) and second eluting fraction (I-121-b). (*Absolute stereochemistry not determined.)

I-121-a: MS (ES): m/z: 512.3 [M+H]+, 1H NMR (MeOD, 400 MHz): δ 8.99 (s, 1H), 8.50-8.49 (m, 1H), 8.43-8.42 (d, J=2.0 Hz, 1H), 8.10 (s, 1H), 7.85 (s, 1H), 7.82-7.81 (d, J=5.2 Hz, 1H), 7.22 (s, 1H), 5.35-5.34 (m, 1H), 4.23 (s, 3H), 4.01 (s, 3H), 3.23-3.16 (m, 1H), 3.11-3.05 (m, 1H), 1.92-1.88 (m, 1H), 1.64-1.62 (d, 3H), 0.96-0.91 (m, 2H), 0.76-0.72 (m, 2H).

I-121-b: MS (ES): m/z: 512.4 [M+H]+, 1H NMR (MeOD, 400 MHz): δ 9.00 (s, 1H), 8.52-8.50 (d, J=5.2 Hz, 1H), 8.45-8.44 (d, J=1.6 Hz, 1H), 8.12 (s, 1H), 7.86 (s, 1H), 7.82-7.81 (d, J=5.2 Hz, 1H), 7.23 (s, 1H), 5.35-5.34 (m, 1H), 4.31 (s, 3H), 4.02 (s, 3H), 3.20-3.18 (m, 1H), 3.12-3.11 (m, 1H), 1.94-1.91 (m, 1H), 1.65-1.64 (d, 3H), 0.97-0.92 (m, 2H), 0.76-0.75 (m, 2H).

Example 122: 5-cyclopropyl-1-((1R,2R)-2-hydroxycyclobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one and 5-cyclopropyl-1-((1S,2S)-2-hydroxycyclobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one

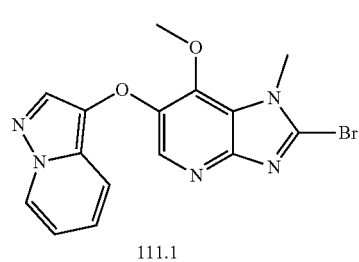

111.1

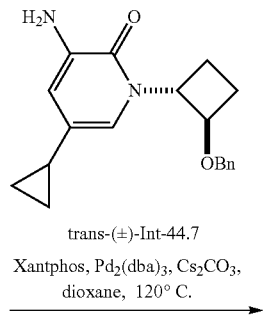

trans-(±)-Int-44.7

Xantphos, Pd2(dba)3, Cs2CO3, dioxane, 120° C.

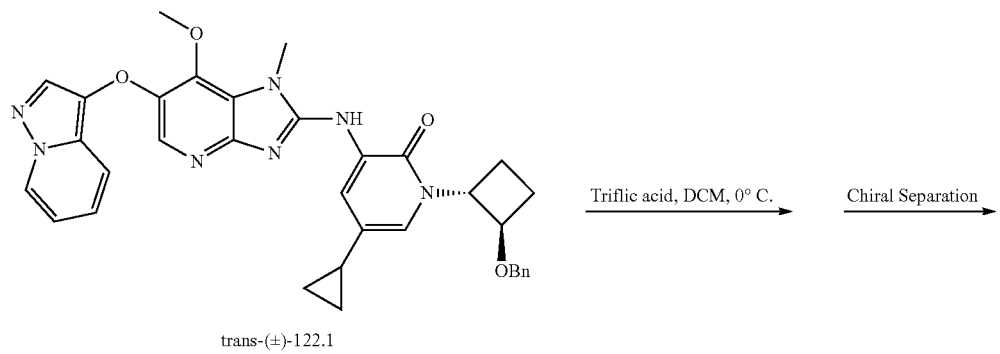

trans-(±)-122.1

Triflic acid, DCM, 0° C. → Chiral Separation →

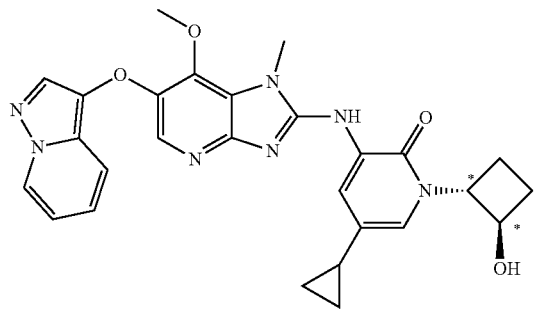

I-122-a and I-122-b

Synthesis of compound trans-(±)-122.1. Compound trans-(±)-122.1 was prepared from 111.1 and trans-(±)-122.1, following the procedure described in the synthesis of I-53. was purified by flash column chromatography on silica gel (CombiFlash®, 2.0% methanol in DCM). MS (ES): m/z: 604.5 [M+H]+.

Synthesis of I-122-a and I-122-b. Racemate I-122 was prepared from trans-(±)-122.1, following the procedure described in the synthesis of I-23. The product was purified by flash column chromatography on silica gel (CombiFlash®, 4.0% methanol in DCM). It was subjected to HPLC separation: (column: CHIRALPAK IB-N (250 mm×21 mm, 5 μm); mobile phase: (A) 0.1% DEA in hexane, (B) 0.1% DEA in isopropanol:acetonitrile (70:30); flow rate: 20 mL/min) to afford first eluting fraction (I-122-a) and second eluting fraction (I-122-b). (*Absolute stereochemistry not determined.)

I-122-a: MS (ES): m/z: 514.5 [M+H]+, 1H NMR (DMSO-d6, 400 MHz): δ 8.61-8.59 (d, J=7.2 Hz, 1H), 8.35 (s, 1H), 8.24 (bs, 1H), 7.96-7.94 (d, J=7.2 Hz, 2H), 7.53-7.51 (d, J=8.8 Hz, 1H), 7.26 (s, 1H), 7.18-7.14 (m, 1H), 6.90-6.86 (m, 1H), 5.63-5.61 (m, 1H), 4.95-4.88 (m, 1H), 4.45-4.42 (m, 1H), 4.14 (s, 3H), 3.90 (s, 3H), 2.17-2.07 (m, 2H), 1.92-1.84 (m, 1H), 1.72-1.59 (m, 2H), 0.91-0.87 (m, 2H), 0.63-0.62 (m, 2H).

I-122-b: MS (ES): m/z: 514.5 [M+H]+, 1H NMR (DMSO-d6, 400 MHz): δ 8.61-8.59 (d, J=7.2 Hz, 1H), 8.34 (s, 1H), 8.24 (bs, 1H), 7.96-7.94 (d, J=7.2 Hz, 2H), 7.53-7.51 (d, J=8.8 Hz, 1H), 7.26 (s, 1H), 7.18-7.14 (m, 1H), 6.90-6.86 (m, 1H), 5.63-5.61 (m, 1H), 4.95-4.88 (m, 1H), 4.47-4.42 (m, 1H), 4.14 (s, 3H), 3.90 (s, 3H), 2.17-2.07 (m, 2H), 1.92-1.84 (m, 1H), 1.72-1.59 (m, 2H), 0.91-0.87 (m, 2H), 0.63-0.62 (m, 2H).

Example 123: 5-cyclopropyl-1-(3-(3,3-difluoropyrrolidin-1-yl)propyl)-3-((7-methoxy-1-methyl-6-(pyrazolo[1,5-a]pyridin-3-yloxy)-1H-imidazo[4,5-b]pyridin-2-yl)amino)pyridin-2(1H)-one

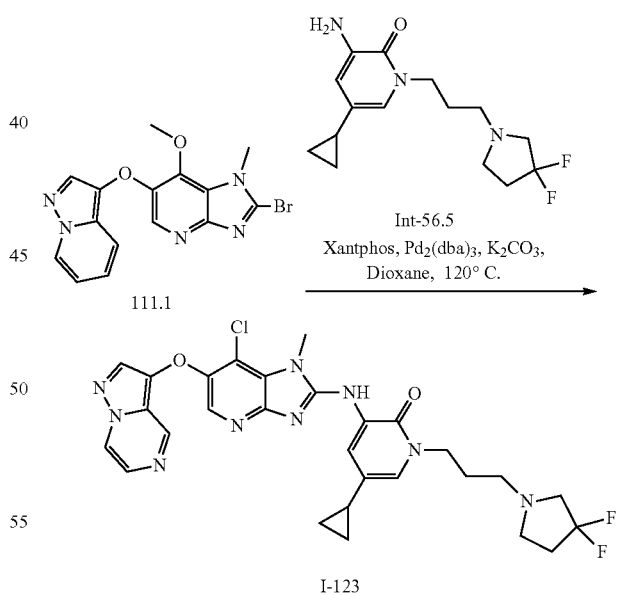

Synthesis of I-123. Compound I-123 was prepared from 111.1 and Int-56.5, following the procedure described in the synthesis of I-53. The product purified by flash column chromatography on silica gel (CombiFlash®, 2.8% methanol in DCM) to afford the title compound. MS (ES): m/z 591.3 [M+H]+, 1H NMR (DMSO-d6, 400 MHz): δ 8.60-8.58 (d, J=7.2 Hz, 1H), 8.33 (s, 1H), 8.28-8.27 (d, J=2.4 Hz, 1H), 7.94-7.93 (d, J=4.0 Hz, 2H), 7.53-7.50 (d, J=9.2 Hz, 1H), 7.17-7.13 (m, 2H), 6.89-6.85 (m, 1H), 4.13 (s, 3H), 4.03-3.99 (m, 2H), 3.89 (s, 3H), 2.93-2.86 (m, 2H), 2.71-2.68 (m, 2H), 2.47-2.44 (m, 2H), 2.30-2.19 (m, 2H), 1.89-1.79 (m, 3H), 0.88-0.83 (m, 2H), 0.59-0.55 (m, 2H).

Example 124: 2-((3-((7-chloro-2-((4,4-dimethyl-4,5,6,7-tetrahydropyrazolo[1,5-a]pyridin-2-yl)amino)-1-methyl-1H-imidazo[4,5-b]pyridin-6-yl)oxy)pyrazolo[1,5-a]pyrazin-4-yl)oxy)ethan-1-ol

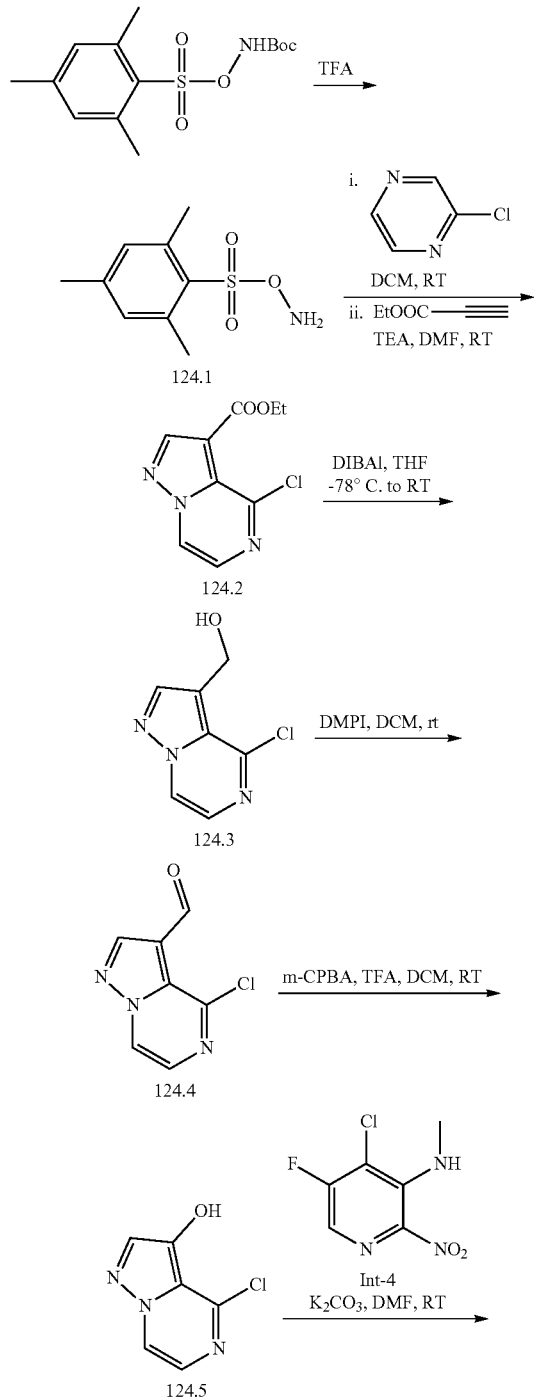

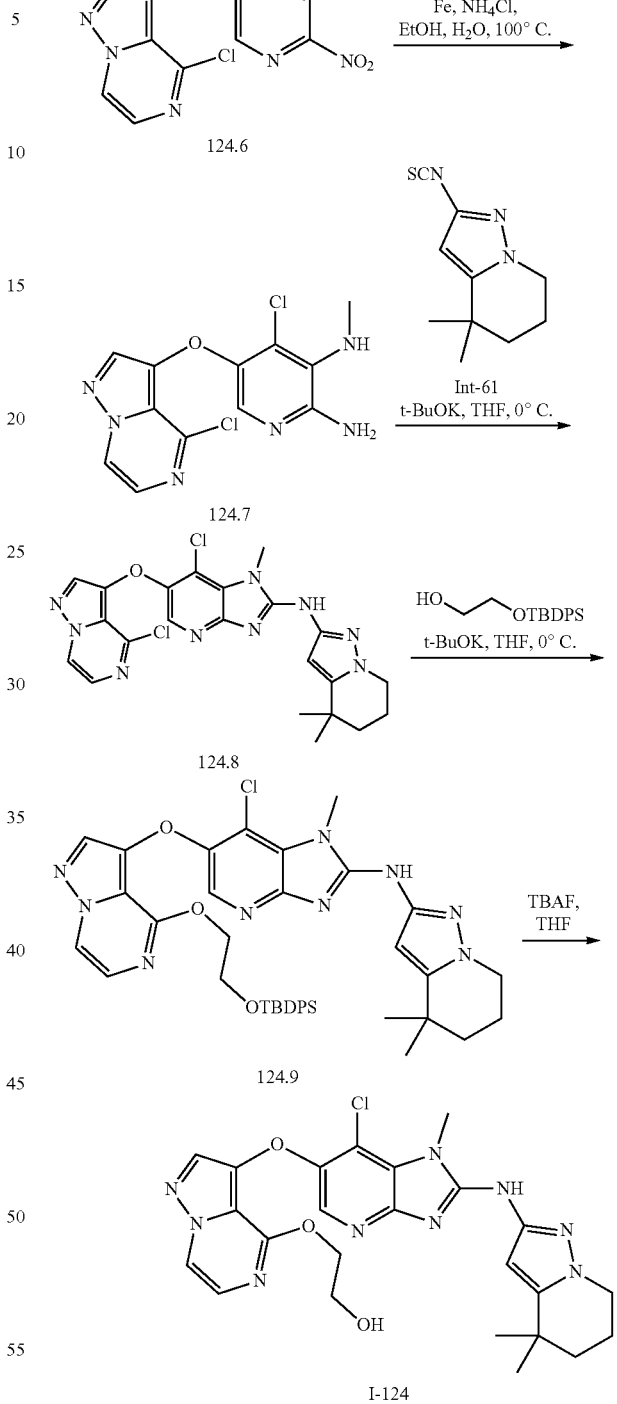

Synthesis of compound 124.1. A solution of tert-butyl ((mesitylsulfonyl)oxy)carbamate (335 g, 1060 mmol, 1.0 equiv) in trifluoroacetic acid (770 mL, 2.3 vol) was stirred at 0° C. for 1 h. The reaction mixture was poured over ice-water and stirred. The precipitated solids were collected by filtration, rained with water and air-dried. This crude product was dissolved in DCM, dried over anhydrous sodium sulfate, filtered and concentrated under reduced pressure to afford 124.1. MS (ES): m/z 216.6 [M+H]+.

Synthesis of compound 124.2. To a solution of 2-chloropyrazine (100.0 g, 873.12 mmol, 1.0 equiv) in DCM (750 mL) was added 124.1 (225.2 g, 1047 mmol, 1.2 equiv) at 0° C. The reaction mixture was stirred at room temperature for 2 h. It was poured over diethyl ether and stirred. The solids were collected by filtration and dissolved in DMF (1250 mL). To the solution was added trimethylamine (279.6 g, 2769 mmol, 2.0 equiv), followed by ethyl propiolate (271.3 g, 2769 mmol, 2.0 equiv) dropwise at 0° C. The reaction mixture was stirred at room temperature for 48 h. It was poured over brine and extracted with ethyl acetate. The combined organic layers were washed with brine, dried over anhydrous sodium sulfate, filtered and concentrated under reduced pressure. The residue was purified by flash column chromatography on silica gel (6.0% ethyl acetate in hexane) to afford 124.2. MS (ES): m/z 226.5 [M+H]$^+$.

Synthesis of compound 124.3. To a solution of 124.2 (34.8 g, 154.23 mmol, 1.0 equiv) in THF (700 mL) was added diisobutylaluminiumhydride (1 M solution in DCM, 771 mL, 771.15 mmol, 5.0 equiv) dropwise at −78° C. The reaction mixture was stirred at room temperature for 1 h. It was carefully poured over 1 N aqueous hydrochloric acid solution and extracted with ethyl acetate. The combined organic layers were washed with brine, dried over anhydrous sodium sulfate, filtered and concentrated under reduced pressure to afford 124.3. MS (ES): m/z 184.2 [M+H]$^+$.

Synthesis of compound 124.4. To a solution of 124.3 (18.5 g, 100.77 mmol, 1 equiv) in DCM was added Dess-Martin periodinane (106.8 g, 251.92 mmol, 2.5 equiv). The reaction mixture was stirred at 0° C. for 1 h. The reaction mixture was transferred into an aqueous solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 45% ethyl acetate in hexane) to afford 124.4. MS (ES): m/z 182 [M+H]$^+$.

Synthesis of compound 124.5. To a solution of 124.4 (11 g, 60.58 mmol, 1 equiv) in DCM (400 mL) was added m-chloroperbenzoic acid (15.5 g, 90.87, 1.5 equiv) and trifluoroacetic acid (0.690 g, 6.05 mmol, 0.1 equiv) dropwise at 0° C. The reaction mixture was stirred at room temperature for 7 h. It was poured over an aqueous solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 26% ethyl acetate in hexane) to afford 124.5. MS (ES): m/z 170.5 [M+H]$^+$.

Synthesis of compound 124.6. Compound 124.6 was prepared from 124.5 and Int-4, following the procedure described in the synthesis of 19.1. The product was used in the next step without purification. MS (ES): m/z 356.1 [M+H]$^+$.

Synthesis of compound 124.7. Compound 124.7 was prepared from 124.6, following the procedure described in the synthesis of 5.4. The product was purified by flash column chromatography on silica gel (CombiFlash®, 2% methanol in DCM) to afford 124.7. MS (ES): m/z 326.1 [M+H]$^+$.

Synthesis of compound 124.8. Compound 124.8 was prepared from 124.7 and Int-61, following the procedure described in the synthesis of I-13. The product was purified by flash column chromatography on silica gel (CombiFlash®, 2.6% methanol in DCM) to afford 124.8. MS (ES): m/z 499.1 [M+H]$^+$.

Synthesis of compound 124.9. To a solution of 124.8 (0.050 g, 0.100 mmol, 1.0 equiv) in THF (3 mL) was added 2-((tert-butyldiphenylsilyl)oxy)ethan-1-ol (0.045 g, 0.150 mmol, 1.5 equiv) followed by addition of potassium tert-butoxide (1 M in THF, 0.25 mL, 0.25 mmol, 2.5 equiv) at 0° C. The reaction mixture was stirred at room temperature for 12 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in DCM) to afford 124.9. MS (ES): m/z 763.3 [M+H]$^+$.

Synthesis of I-124. To a solution of 124.9 (0.035 g, 0.059 mmol, 1.0 equiv) in THF (2 mL) was added TBAF (1 M solution in THF, 0.17 mL, 0.177 mmol, 3.0 equiv) at 0° C. The reaction mixture was stirred at room temperature for 30 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in DCM) to afford I-124. MS (ES): m/z 524.5 [M+H]$^+$. $^1$H NMR (DMSO-d$_6$, 400 MHz): δ 9.96 (s, 1H), 8.28-8.27 (d, J=5.2 Hz, 1H), 7.91 (bs, 2H), 7.37-7.35 (d, J=5.2 Hz, 1H), 6.58 (s, 1H), 4.74-4.73 (m, 1H), 4.38-4.36 (m, 2H), 3.95 (bs, 5H), 3.59-3.57 (m, 2H), 2.03 (bs, 2H), 1.68 (bs, 2H), 1.31 (s, 6H).

Example 125: 7-chloro-N-(4,4-dimethyl-4,5,6,7-tetrahydropyrazolo[1,5-a]pyridin-2-yl)-1-methyl-6-((4-(methylamino)pyrazolo[1,5-a]pyrazin-3-yl)oxy)-1H-imidazo[4,5-b]pyridin-2-amine

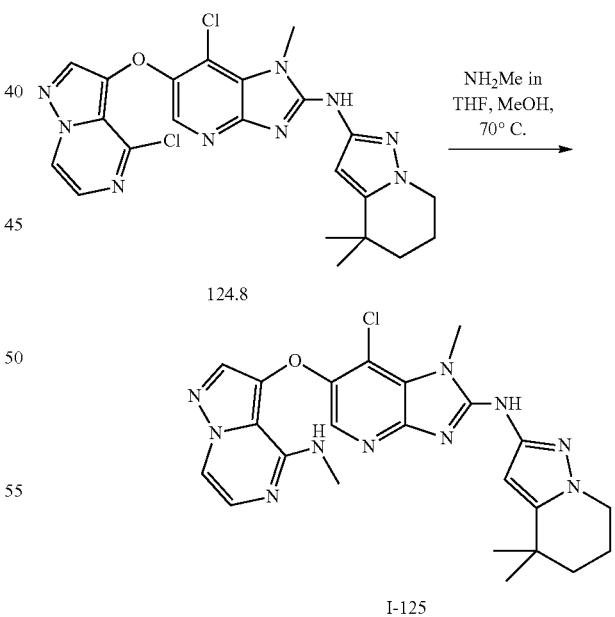

Synthesis of I-125. To a solution of 124.8 (0.030 g, 0.024 mmol, 1.0 equiv) in methanol (1 mL) was added methylamine (2 M in THF) (0.3 mL) at room temperature and stirred at 70° C. for 12 h. It was concentrated under reduced pressure. The residue was purified by trituration with methanol to afford I-125. MS (ES): m/z 493.5 [M+H]$^+$, $^1$H NMR (DMSO-d$_6$, 400 MHz): δ 8.11 (s, 1H), 7.78-7.77 (d, J=4.4 Hz, 1H), 7.72 (bs, 1H), 7.47 (s, 1H), 7.26-7.24 (d, J=4.4 Hz, 1H), 6.81 (bs, 1H), 6.59 (s, 1H), 3.95 (bs, 3H), 3.00-2.99 (d, 3H), 2.37 (bs, 2H), 2.04 (bs, 2H), 1.69 (bs, 2H), 1.32 (s, 6H).

Example 126: 4-((7-chloro-1-methyl-6-(pyrazolo[1,5-a]pyridin-3-yloxy)-1H-imidazo[4,5-b]pyridin-2-yl)amino)-6-cyclopropyl-2-(2-hydroxyethyl)pyridazin-3(2H)-one

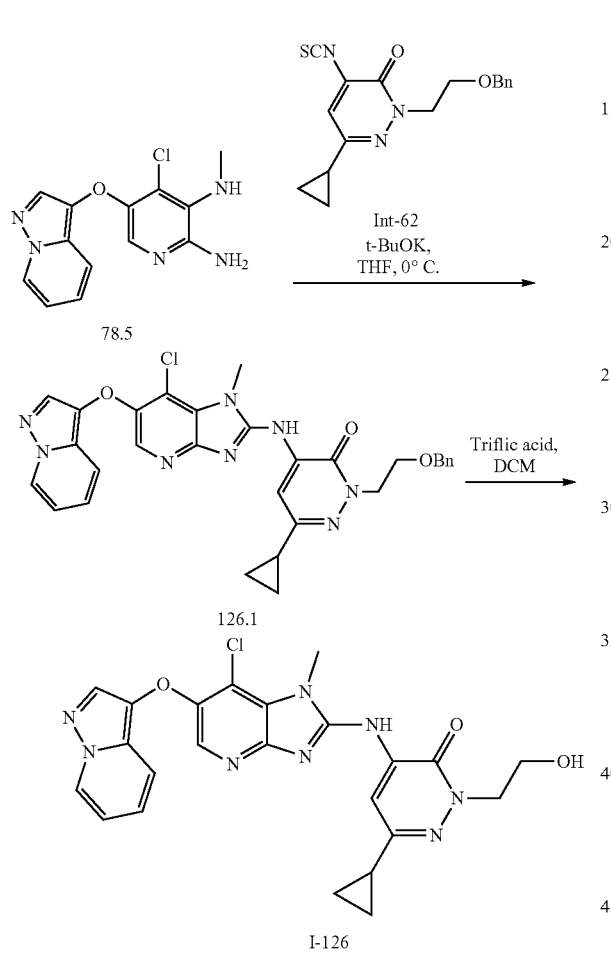

I-126

Example 127: 3-((7-chloro-1-methyl-6-((4-(2-morpholinoethoxy)pyrazolo[1,5-a]pyrazin-3-yl)oxy)-1H-imidazo[4,5-b]pyridin-2-yl)amino)-1-methyl-5-(trifluoromethyl)pyridin-2(1H)-one

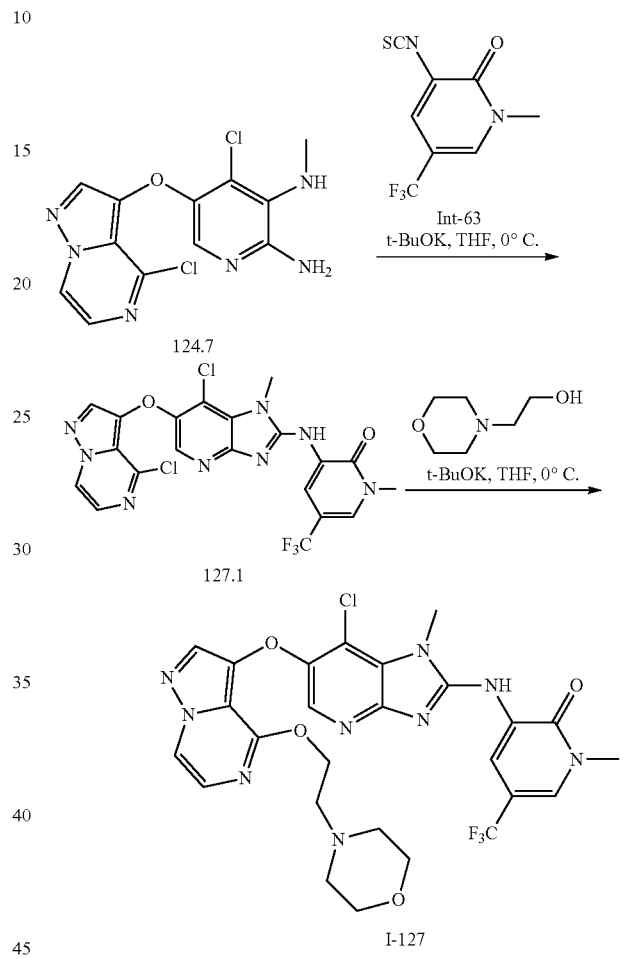

I-127

Synthesis of compound 126.1. Compound 126.1 was prepared from 78.5 and Int-62, following the procedure described in the synthesis of I-13. The product was purified by flash column chromatography on silica gel (CombiFlash®, 1.5% methanol in DCM). MS (ES): m/z 584 [M+H]$^+$.

Synthesis of I-126. To a solution of 126.1 (0.075 g, 0.128 mmol, 1.0 equiv) in DCM (5 mL) was added triflic acid (0.25 mL) at 0° C. and stirred for 5 min. It was poured over a mixture of ice and saturated sodium bicarbonate solution and extracted with DCM. The combined organic layers were washed with brine, dried over anhydrous sodium sulfate, filtered and concentrated under reduced pressure. The residue was purified by flash column chromatography on silica gel (CombiFlash®, 3.0% methanol in DCM) to afford I-126. MS (ES): m/z 493.4 [M+H]$^+$. $^1$H NMR (DMSO-d$_6$, 400 MHz): δ 9.18 (s, 1H), 8.65-8.63 (d, J=6.8 Hz, 1H), 8.09 (s, 1H), 8.05 (s, 1H), 7.96 (s, 1H), 7.54-7.52 (d, J=8.8 Hz, 1H), 7.22-7.18 (m, 1H), 6.93-6.90 (m, 1H), 4.86 (bs, 1H), 4.19-4.16 (m, 2H), 4.03 (s, 3H), 3.76 (bs, 2H), 2.01-1.99 (m, 1H), 0.97-0.95 (m, 2H), 0.82-0.81 (m, 2H).

Synthesis of compound 127.1. Compound 127.1 was prepared from 124.7 and Int-63, following the procedure described in the synthesis of I-13. The product was purified by flash column chromatography on silica gel (CombiFlash®, 2% methanol in DCM) to afford 127.1. MS (ES): m/z 526.2 [M+H]$^+$.

Synthesis of I-127. To a solution of 127.1 (0.030 g, 0.057 mmol, 1.0 equiv) in THF (2 mL) was added 2-morpholinoethan-1-ol (0.008 g, 0.062 mmol, 1.1 equiv) followed by addition of potassium tert-butoxide (1 M in THF, 0.11 mL, 0.114 mmol, 2.0 equiv) at 0° C. The reaction mixture was stirred at 0° C. for 15 min. The reaction mixture was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.3% methanol in DCM) to afford I-127. MS (ES): m/z 620.20 [M+H]$^+$, $^1$H NMR (DMSO-d$_6$, 400 MHz): δ 8.84 (s, 1H), 8.59 (s, 1H), 8.32-8.30 (d, J=4.4 Hz, 1H), 8.13 (s, 1H), 8.03 (s, 1H), 7.96

(s, 1H), 7.39-7.38 (d, J=4.8 Hz, 1H), 4.45-4.42 (m, 2H), 4.03 (s, 3H), 3.67 (s, 3H), 3.39-3.37 (m, 4H), 3.19-3.17 (m, 2H), 2.27 (bs, 4H).

Example 128: 3-((7-chloro-1-methyl-6-((4-(methyl-amino)pyrazolo[1,5-a]pyrazin-3-yl)oxy)-1H-imidazo[4,5-b]pyridin-2-yl)amino)-1-methyl-5-(trifluoromethyl)pyridin-2(1H)-one

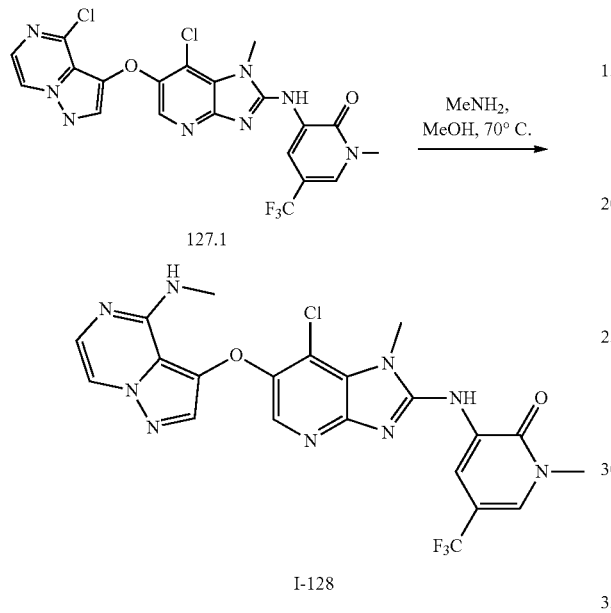

Synthesis of I-128. To a solution of 127.1 (0.030 g, 0.057 mmol, 1.0 equiv) and methylamine solution (2 M in THF, 0.3 mL) in methanol (1 mL) was stirred at 70° C. for 12 h. The reaction mixture was concentrated under reduced pressure. The residue was purified by trituration with methanol to afford I-128. MS (ES): m/z 520.4 [M+H]$^+$, $^1$H NMR (DMSO-d$_6$, 400 MHz): δ 8.84 (s, 1H), 8.62 (s, 1H), 8.24-8.23 (d, J=3.2 Hz, 1H), 8.14 (s, 1H), 7.78 (s, 1H), 7.50-7.49 (d, J=3.2 Hz, 1H), 7.25 (s, 1H), 6.83 (s, 1H), 4.01 (bs, 3H), 3.66 (s, 3H), 2.98 (s, 3H).

Example 129: 3-((7-chloro-1-methyl-6-(pyrazolo[1,5-a]pyrazin-3-yloxy)-1H-imidazo[4,5-b]pyridin-2-yl)amino)-5-cyclopropyl-1-(3-(3,3-difluoropiperidin-1-yl)propyl)pyridin-2(1H)-one

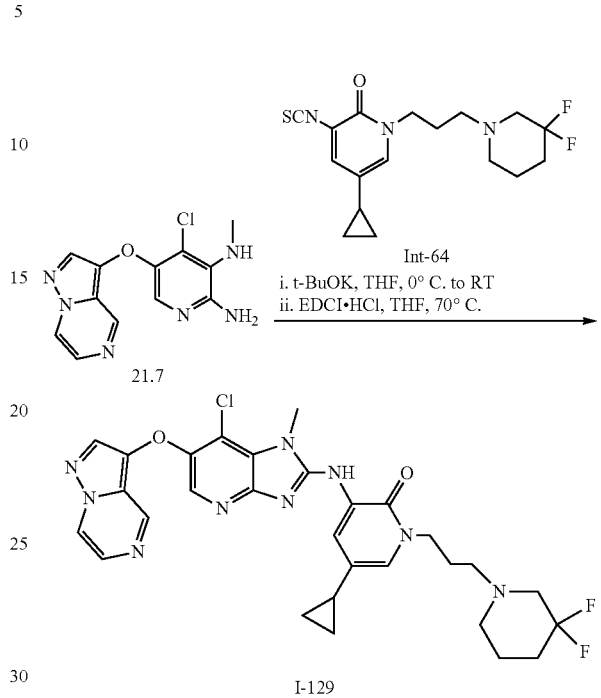

Synthesis of I-129. Compound I-129 was prepared from 21.7 and Int-64, following the procedure described in the synthesis of I-51. The product was purified by flash column chromatography on silica gel (CombiFlash®, 3.0% methanol in DCM. MS (ES): m/z 610.4 [M+H]$^+$, $^1$H NMR (DMSO-d$_6$, 400 MHz): δ 9.03 (s, 1H), 8.69-8.68 (d, J=4.0 Hz, 1H), 8.54 (s, 1H), 8.28 (s, 1H), 8.20 (s, 1H), 8.04 (s, 1H), 7.87-7.86 (d, J=4.4 Hz, 1H), 7.19 (s, 1H), 3.98 (bs, 5H), 2.67-2.61 (m, 4H), 2.39-2.33 (m, 4H), 1.88-1.81 (m, 5H), 0.87-0.85 (m, 2H), 0.58-0.57 (m, 2H).

Example 130: (1r,3r)-3-(5-(tert-butyl)-3-((6-((6-cyclopropylimidazo[1,5-a]pyrimidin-3-yl)oxy)-7-methoxy-1-methyl-1H-imidazo[4,5-b]pyridin-2-yl)amino)-1H-pyrazol-1-yl)cyclobutan-1-ol

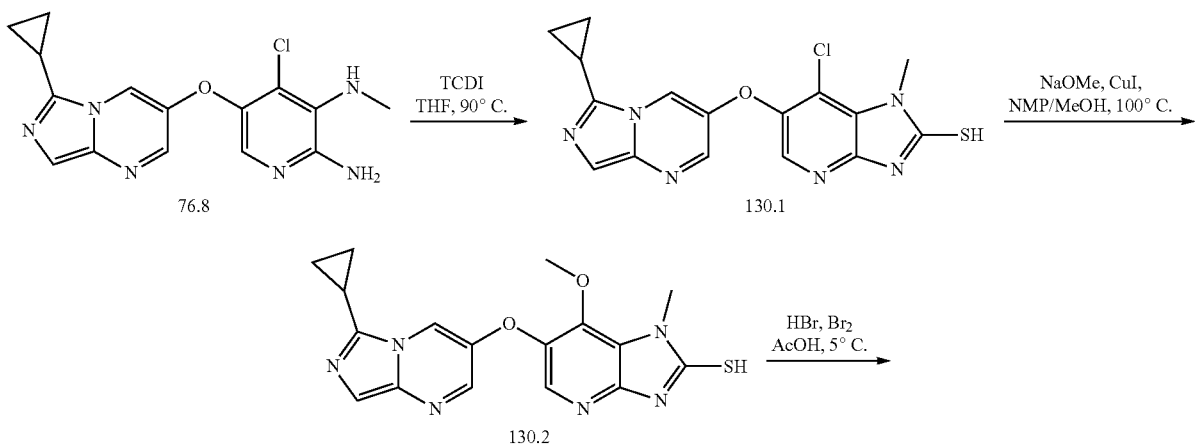

-continued

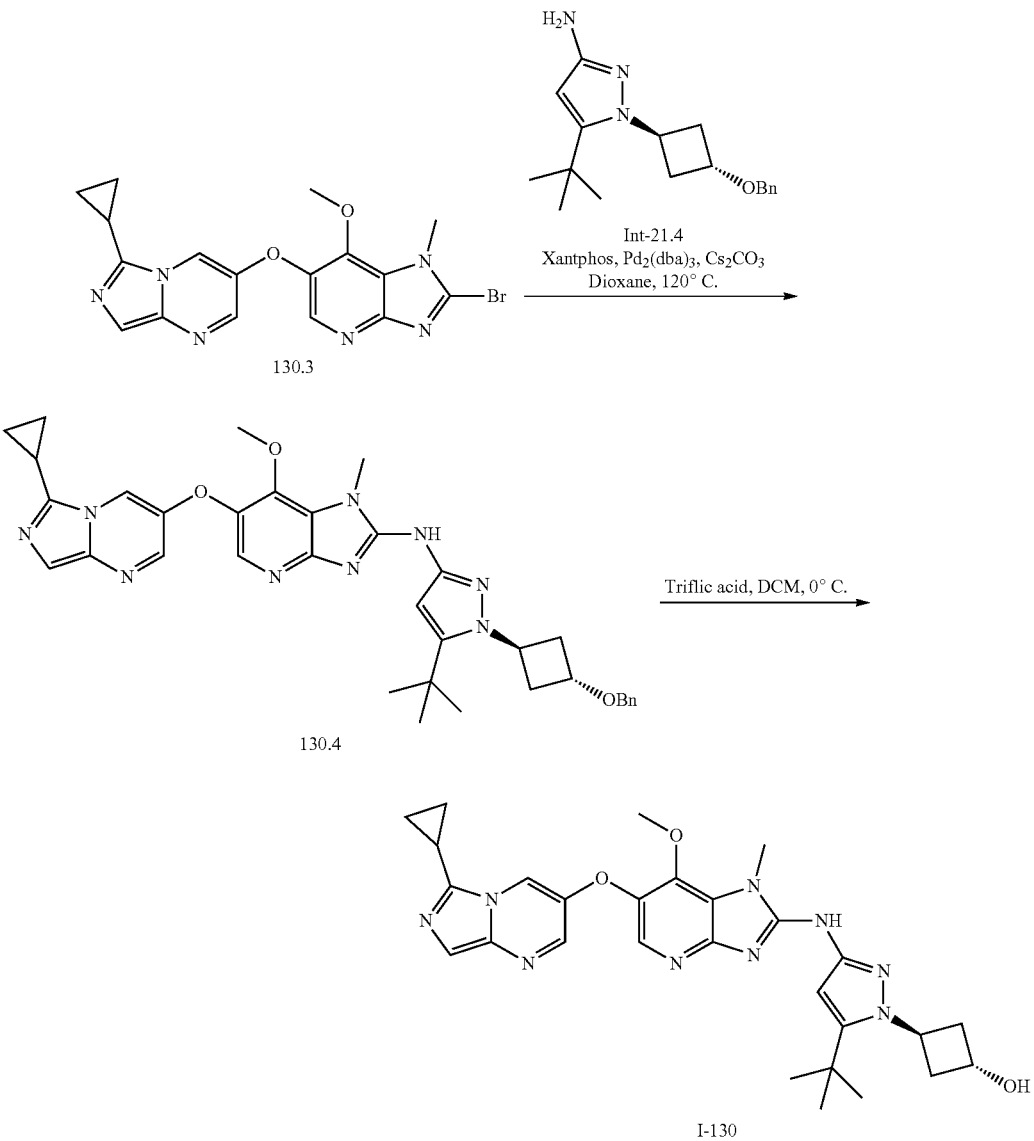

Synthesis of compound 130.1. To a solution of 76.8 (0.8 g, 2.42 mmol, 1.0 equiv) in THF (8 mL) was added 1,1'-thiocarbonyldiimidazole (2.15 g, 12.1 mmol, 5.0 equiv). The reaction mixture was stirred at 90° C. for 3 h. It was cooled to room temperature and transferred into ice-water. The precipitated solids were collected by filtration and triturated with hexane to afford 130.1. MS (ES): m/z 373.5 [M+H]$^+$.

Synthesis of compound 130.2. Compound 130.2 was prepared from 130.1, following the procedure described in the synthesis of 100.2. The product was purified by flash column chromatography on silica gel (CombiFlash®, 2.0% methanol in DCM) to afford 130.2. MS (ES): m/z 369.3 [M+H]$^+$.

Synthesis of compound 130.3. To 130.2 (0.150 g, 0.407 mmol, 1.0 equiv) was added hydrobromic acid in acetic acid (3 mL) at 0° C. followed by bromine (0.325 g, 2.305 mmol, 5.0 equiv). The reaction mixture was stirred for 10 min. It was poured over saturated sodium bicarbonate solution, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.2% methanol in DCM) to afford 130.3. MS (ES): m/z 416.2 [M+H]$^+$.

Synthesis of compound 130.4. Compound 130.4 was prepared from 130.3, following the procedure described in the synthesis of I-53. The product was purified by flash column chromatography on silica gel (CombiFlash®, 3.6% methanol in DCM). MS (ES): m/z 634.5 [M+H]$^+$.

Synthesis of I-130. Compound I-130 was prepared from 130.4, following the procedure described in the synthesis of I-23. The product was purified by flash column chromatography on silica gel (CombiFlash®, 3.1% methanol in DCM). MS (ES): m/z 544.5 [M+H]$^+$, $^1$H NMR (MeOD, 400 MHz): δ 8.28 (s, 1H), 8.11 (s, 1H), 8.03 (bs, 1H), 7.43 (s, 1H), 6.55 (bs, 1H), 5.33-5.29 (m, 1H), 4.66 (bs, 1H), 4.17 (s, 3H), 3.93 (s, 3H), 2.89 (bs, 2H), 2.45 (bs, 2H), 2.14 (bs, 1H), 1.42 (s, 9H), 1.32 (bs, 1H), 1.04-1.02 (m, 2H), 0.96-0.95 (m, 2H).

Example 131: 5-cyclopropyl-1-((1R,2S)-2-hydroxy-cyclobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one and 5-cyclopropyl-1-((1S,2R)-2-hydroxycyclobutyl)-3-((7-methoxy-1-methyl-6-(pyrazolo[1,5-a]pyridin-3-yloxy)-1H-imidazo[4,5-b]pyridin-2-yl)amino)pyridin-2(1H)-one

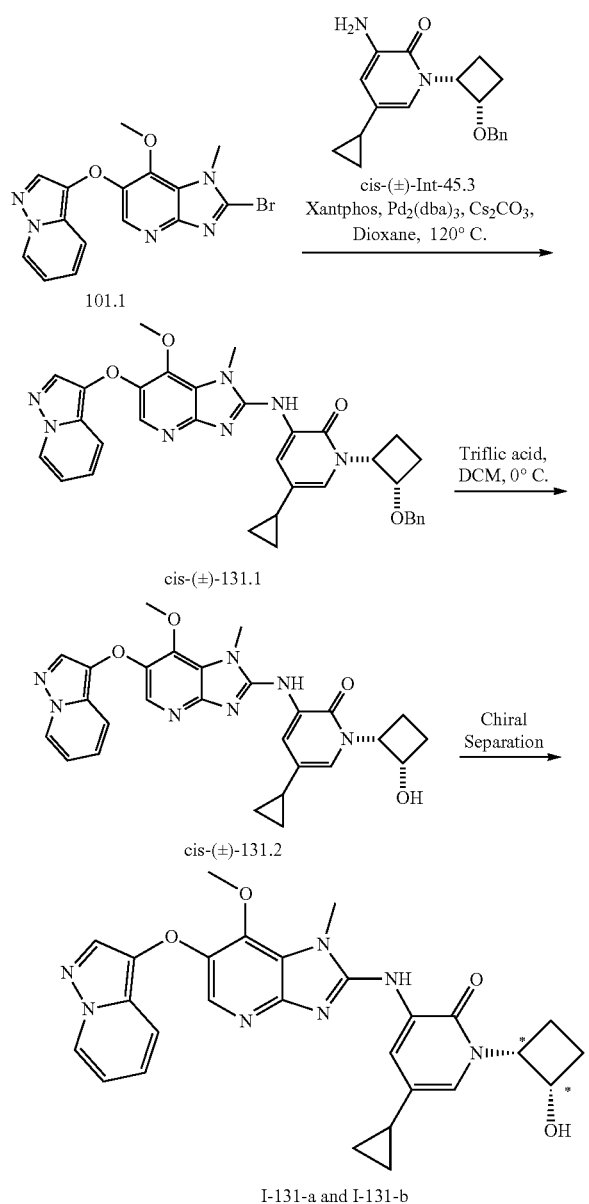

Synthesis of compound cis-(±)-131.1. Compound cis-(±)-131.1 was prepared from 101.1 and cis-(±)-Int-45.3, following the procedure described in the synthesis of I-53. The product was purified by flash column chromatography on silica gel (CombiFlash®, 2.0% methanol in DCM). MS (ES): m/z 604.5 [M+H]$^+$.

Synthesis of compound cis-(±)-131.2. Compound cis-(±)-131.2 was prepared from cis-(±)-131.1, following the procedure described in the synthesis of I-23. The product was purified by flash column chromatography on silica gel (CombiFlash®, 4.0% methanol in DCM). MS (ES): m/z 514.5 [M+H]$^+$.

Separation of I-131-a and I-131-b. cis-(±)-131.2 was separated using HPLC (column CHIRALPAK IB-N (250 mm*21 mm, 5 µm); mobile phases: (A) 0.1% DEA in n-hexane, (B) 0.1% DEA in isopropanol:acetonitrile (70:30); flow rate=20 mL/min) to afford first eluting fraction (I-131-a) and second eluting fraction (I-131-b). (*Absolute stereochemistry not determined.)

I-131-a. MS (ES): m/z 514.5 [M+H]$^+$, LCMS purity: 100%, $^1$H NMR (DMSO-d$_6$, 400 MHz): δ 8.61-8.59 (d, J=7.2 Hz, 1H), 8.34 (s, 1H), 8.24 (bs, 1H), 7.96-7.94 (d, J=7.2 Hz, 2H), 7.53-7.51 (d, J=8.8 Hz, 1H), 7.25 (s, 1H), 7.18-7.15 (m, 1H), 6.90-6.86 (m, 1H), 5.62-5.60 (m, 1H), 4.92-4.90 (m, 1H), 4.45-4.42 (m, 1H), 4.14 (s, 3H), 3.90 (s, 3H), 2.15-2.10 (m, 2H), 1.92-1.88 (m, 1H), 1.72-1.59 (m, 2H), 0.89-0.88 (m, 2H), 0.63-0.62 (m, 2H).

I-131-b. MS (ES): m/z 514.5 [M+H]$^+$, $^1$H NMR (DMSO-d$_6$, 400 MHz): δ 8.60-8.58 (d, J=7.2 Hz, 1H), 8.34 (s, 1H), 8.23 (bs, 1H), 7.95-7.93 (d, J=7.2 Hz, 2H), 7.52-7.50 (d, J=8.8 Hz, 1H), 7.25 (s, 1H), 7.17-7.13 (m, 1H), 6.89-6.85 (m, 1H), 5.63-5.61 (m, 1H), 4.94-4.88 (m, 1H), 4.44-4.41 (m, 1H), 4.12 (s, 3H), 3.89 (s, 3H), 2.18-2.08 (m, 2H), 1.91-1.83 (m, 1H), 1.70-1.56 (m, 2H), 0.90-0.88 (m, 2H), 0.63-0.59 (m, 2H).

Example 132: 2-(3-((7-chloro-1-methyl-6-(pyrazolo[1,5-a]pyrazin-3-yloxy)-1H-imidazo[4,5-b]pyridin-2-yl)amino)-5-cyclopropyl-2-oxopyridin-1(2H)-yl)acetonitrile

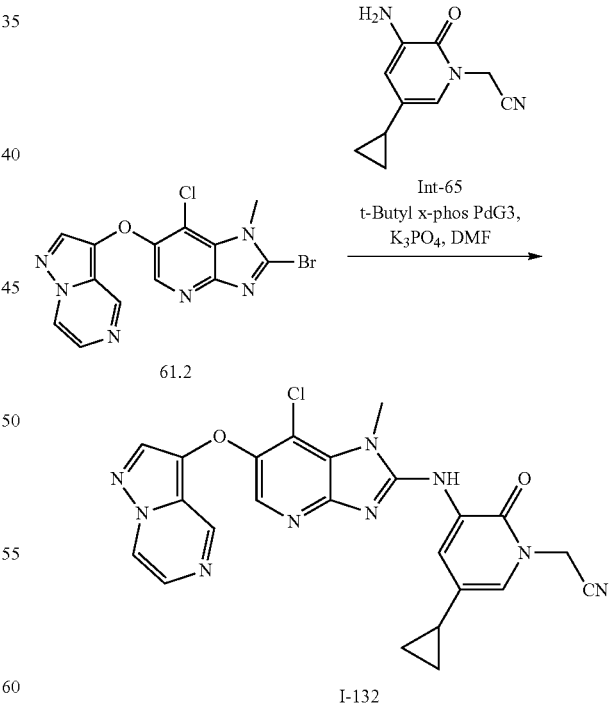

Synthesis of I-132. A mixture of 61.2 (0.090 g, 0.237 mmol, 1.0 equiv), Int-65 (0.054 g, 0.284 mmol, 1.2 equiv) and tripotassium phosphate (0.150 g, 0.711 mmol, 3.0 equiv) in DMF (4 mL) was degassed by bubbling through a stream of argon for 10 min. Under argon atmosphere was added

[(2-di-tert-butylphosphino-2',4',6'-triisopropyl-1,1'-biphenyl)-2-(2'-amino-1,1'-biphenyl)] palladium(II) methanesulfonate (0.056 g, 0.0711 mmol, 0.3 equiv), again degassed for 5 min. The reaction mixture was stirred at 70° C. for 4 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.2% methanol in DCM) to afford I-132. MS (ES): m/z 488.5 [M+H]$^+$, $^1$H NMR (DMSO-d$_6$, 400 MHz): δ 9.04 (s, 1H), 8.70-8.69 (d, J=4.8 Hz, 1H), 8.66 (s, 1H), 8.37-8.36 (d, J=2.0 Hz, 1H), 8.23 (s, 1H), 8.06 (s, 1H), 7.89-7.87 (d, J=5.2 Hz, 1H), 7.35-7.34 (d, J=1.6 Hz, 1H), 5.11 (s, 2H), 4.01 (s, 3H), 1.86-1.82 (m, 1H), 0.92-0.88 (m, 2H), 0.62-0.58 (m, 2H).

Example 133: 3-((7-chloro-6-((4-((1R,2R)-2-hydroxycyclobutoxy)pyrazolo[1,5-a]pyrazin-3-yl)oxy)-1-methyl-1H-imidazo[4,5-b]pyridin-2-yl)amino)-5-cyclopropyl-1-methylpyridin-2(1H)-one and 3-((7-chloro-6-((4-((1S,2S)-2-hydroxycyclobutoxy)pyrazolo[1,5-a]pyrazin-3-yl)oxy)-1-methyl-1H-imidazo[4,5-b]pyridin-2-yl)amino)-5-cyclopropyl-1-methylpyridin-2(1H)-one

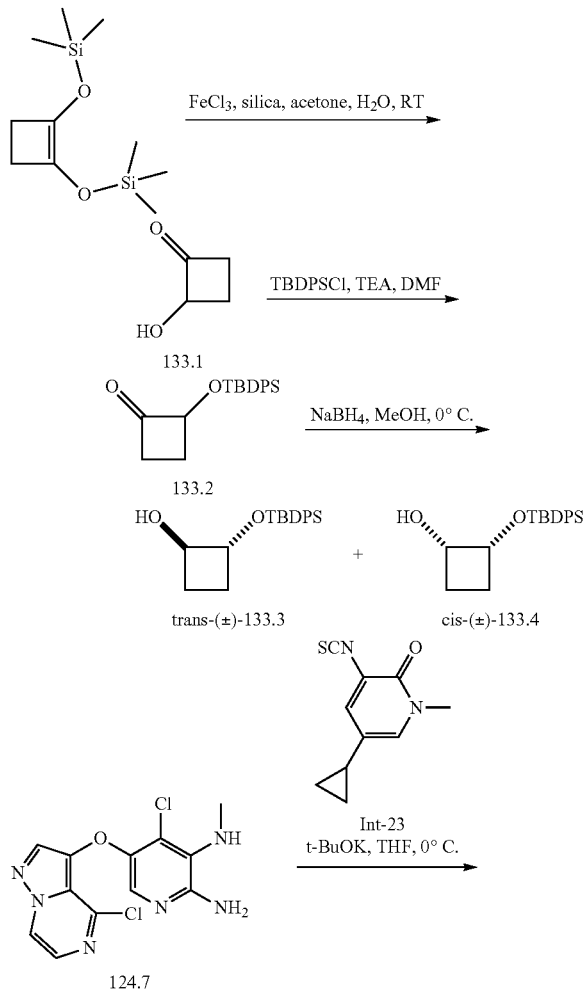

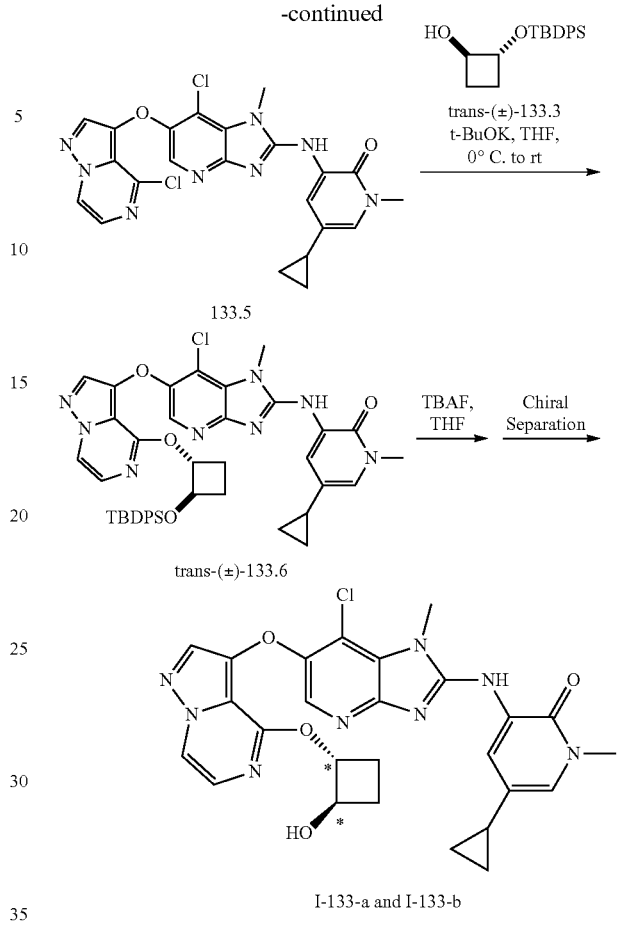

Synthesis of compound 133.1 To a solution of 1,2-bis((trimethylsilyl)oxy)cyclobut-1-ene (10 g, 43.39 mmol, 1.0 equiv) in acetone:water (20:1, 50 mL) was added ferric chloride in silica (0.050 g, 0.5% w/w). The reaction mixture was stirred at room temperature for 1.5 h. It was concentrated under reduced pressure. The residue was purified by flash column chromatography on silica gel (CombiFlash®, 11% ethyl acetate in hexane) to afford 133.1. $^1$H NMR (CDCl$_3$, 400 MHz): δ 5.02-5.00 (m, 1H), 2.88-2.78 (m, 2H), 2.49-2.43 (m, 1H), 1.93-1.88 (m, 1H).

Synthesis of compound 133.2. In compound 133.1 (2.2 g, 25.55 mmol, 1.0 equiv) was added triethylamine (5.16 g, 51.1 mmol, 2.0 equiv) and stirred at room temperature for 10 min followed by addition of tert-butyldiphenylchlorosilane (14.05 g, 51.1 mmol, 2.0 equiv). The reaction mixture was stirred at room temperature for 12 h. The reaction mixture was poured over brine and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% ethyl acetate in hexane) to afford 133.2. MS (ES): m/z 325.6 [M+H]$^+$.

Synthesis of compound trans-(±)-133.3 and cis-(±)-133.4. To a solution of 133.2 (2.2 g, 6.78 mmol, 1.0 equiv) in methanol (15 mL) was added sodium borohydride (0.501 g, 13.56 mmol, 2.0 equiv) in portions at 0° C. The reaction mixture was stirred at 0° C. for 30 min. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 8-10% ethyl acetate in hexane and 12-15% ethyl acetate in hexane) to afford trans-(±)-133.3, MS (ES): m/z 327.3 [M+H]⁺, and cis-(±)-133.3, MS (ES): m/z 327.2 [M+H]⁺, respectively.

Synthesis of compound 133.5. Compound 133.5 was prepared from 124.7 and Int-23, following the procedure described in the synthesis of I-13. The product was purified by flash column chromatography on silica gel (Combi-Flash®, 2.5% methanol in DCM). MS (ES): m/z 498.3 [M+H]⁺.

Synthesis of compound trans-(±)-133.6. Compound trans-(±)-133.6 was prepared from 133.5 and trans-(±)-133.3, following the procedure described in the synthesis of I-127. The product was purified by flash column chromatography on silica gel (CombiFlash®, 2.0% methanol in DCM) to afford trans-(±)-133.6. MS (ES): m/z 788.2 [M+H]⁺.

Synthesis of compound I-133-a and I-133-b. To a solution of trans-(±)-133.6 (0.080 g, 0.101 mmol, 1.0 equiv) in THF (2 mL) was added TBAF (1 M in THF, 0.5 mL, 0.505, 5.0 equiv) at 0° C. The reaction mixture was stirred at room temperature for 1.5 h. It was transferred into ice-water and the precipitated solids were collected by filtration and trituration with methanol to afford the racemate. The enantiomers were separated by HPLC (column: CHIRALPAK IB-N (250 mm*21 mm, 5 µm); mobile phase: (A) 0.1% DEA in n-hexane, (B) 0.1% DEA in isopropanol:acetonitrile (70:30); flow rate=20 mL/min) to afford first eluting fraction (I-133-a) and second eluting fraction (I-133-b). (*Absolute stereochemistry not determined.)

I-133-a: MS (ES): m/z 549.3 [M+H]⁺, ¹H NMR (DMSO-d₆, 400 MHz): δ 8.50 (s, 1H), 8.30-8.29 (d, J=4.4 Hz, 2H), 8.02 (s, 1H), 7.96 (s, 1H), 7.37-7.36 (d, J=4.8 Hz, 1H), 7.23 (s, 1H), 5.39-5.37 (m, 1H), 5.00-4.99 (m, 1H), 4.01 (s, 3H), 3.56 (s, 3H), 2.08-1.94 (m, 2H), 1.81 (bs, 1H), 1.37 (bs, 1H), 1.17-1.12 (m, 2H), 0.87-0.86 (m, 2H), 0.59-0.58 (m, 2H).

I-133-b: MS (ES): m/z 549.3 [M+H]⁺, ¹H NMR (DMSO-d₆, 400 MHz): δ 8.50 (s, 1H), 8.29-8.28 (d, J=4.4 Hz, 2H), 8.01 (s, 1H), 7.94 (s, 1H), 7.36-7.35 (d, J=4.8 Hz, 1H), 7.23 (s, 1H), 5.38-5.36 (m, 1H), 5.01-4.95 (m, 1H), 4.00 (s, 3H), 3.55 (s, 3H), 2.09-1.93 (m, 2H), 1.80-1.79 (m, 1H), 1.38-1.33 (m, 1H), 1.17-1.11 (m, 2H), 0.86-0.84 (m, 2H), 0.58-0.57 (m, 2H).

Example 134: 3-((7-chloro-1-methyl-6-((4-(methylamino)pyrazolo[1,5-a]pyrazin-3-yl)oxy)-1H-imidazo[4,5-b]pyridin-2-yl)amino)-5-cyclopropyl-1-methylpyridin-2(1H)-one

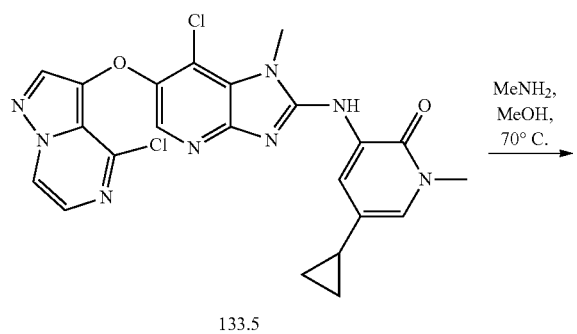

133.5

MeNH₂, MeOH, 70° C.

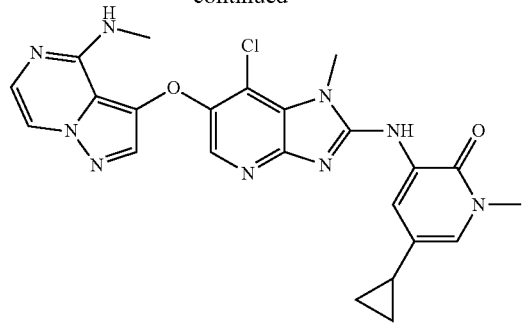

I-134

Synthesis of I-134. Compound I-134 was prepared from 133.5, following the procedure described in the synthesis of I-128. The product was purified by trituration with methanol. MS (ES): m/z 492.4 [M+H]⁺, ¹H NMR (DMSO-d₆, 400 MHz): δ 8.54 (s, 1H), 8.30 (s, 1H), 8.20 (s, 1H), 7.79-7.78 (d, J=4.8 Hz, 1H), 7.49 (s, 1H), 7.26 (s, 1H), 7.25 (s, 1H), 6.84-6.83 (d, J=4.4 Hz, 1H), 3.99 (s, 3H), 3.56 (s, 3H), 3.00-2.99 (d, J=4.4 Hz, 3H), 1.82 (bs, 1H), 0.88-0.87 (m, 2H), 0.60-0.59 (m, 2H).

Example 135: 3-((7-chloro-6-((4-(2-methoxyethoxy)pyrazolo[1,5-a]pyrazin-3-yl)oxy)-1-methyl-1H-imidazo[4,5-b]pyridin-2-yl)amino)-5-cyclopropyl-1-methylpyridin-2(1H)-one

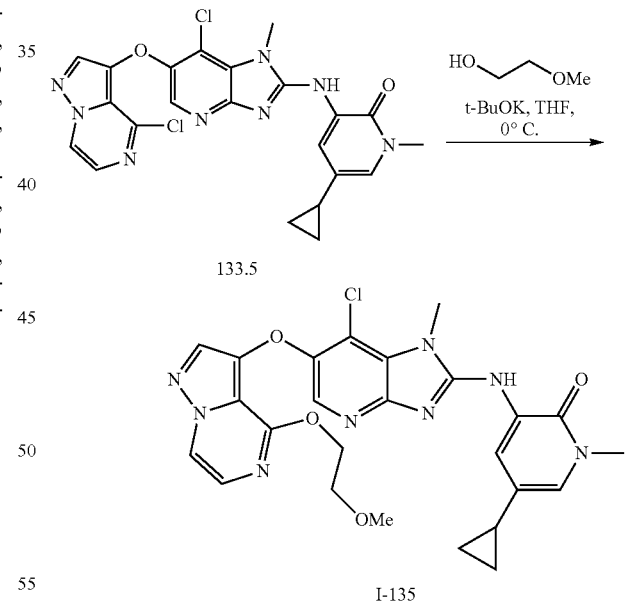

Synthesis of I-135. Compound I-135 was prepared from 133.5 and 2-methoxyethan-1-ol, following the procedure described in the synthesis of I-127. The product was purified by flash column chromatography on silica gel (CombiFlash®, 2.8% methanol in DCM) to afford I-135. MS (ES): m/z 537.3 [M+H]⁺, ¹H NMR (DMSO-d₆, 400 MHz): δ 8.51 (s, 1H), 8.32-8.29 (m, 2H), 8.03 (s, 1H), 7.93 (s, 1H), 7.39-7.38 (d, J=4.8 Hz, 1H), 7.23 (s, 1H), 4.45-4.44 (m, 2H), 4.01 (s, 3H), 3.56 (s, 3H), 3.48-3.47 (m, 2H), 3.11 (s, 3H), 1.82 (bs, 1H), 0.88-0.86 (m, 2H), 0.59-0.58 (m, 2H).

Example 136: 3-((7-chloro-1-methyl-6-((4-(2-mor-pholinoethoxy)pyrazolo[1,5-a]pyrazin-3-yl)oxy)-1H-imidazo[4,5-b]pyridin-2-yl)amino)-5-cyclopropyl-1-methylpyridin-2(1H)-one

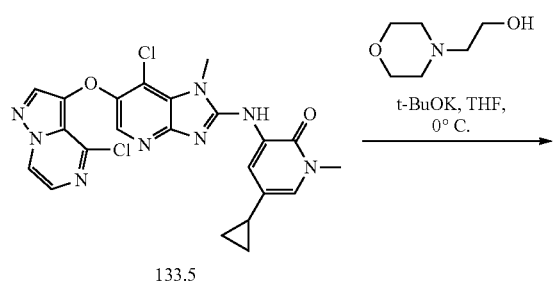

133.5

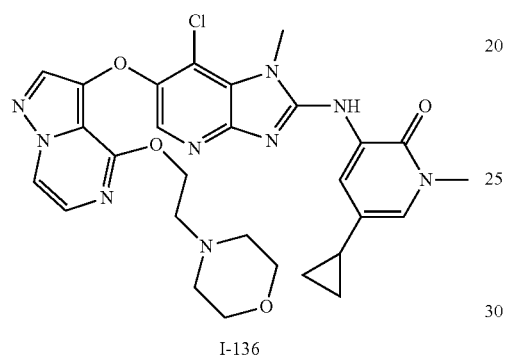

I-136

Synthesis of I-136. Compound I-136 was prepared from 133.5 and 2-morpholinoethan-1-ol, following the procedure described in the synthesis of I-127. The product was purified by flash column chromatography on silica gel (Combi-Flash®, 4.0% methanol in DCM). MS (ES): m/z 592.6 [M+H]⁺, ¹H NMR (DMSO-$d_6$, 400 MHz): δ 8.53 (s, 1H), 8.32-8.30 (d, J=5.2 Hz, 1H), 8.29-8.28 (d, J=2.4 Hz, 1H), 8.02 (s, 1H), 7.92 (s, 1H), 7.39-7.38 (d, J=4.8 Hz, 1H), 7.24-7.23 (d, J=1.6 Hz, 1H), 4.46-4.43 (m, 2H), 4.01 (s, 3H), 3.56 (s, 3H), 3.40-3.38 (m, 4H), 2.48-2.47 (m, 2H), 2.28 (bs, 4H), 1.83-1.79 (m, 1H), 0.89-0.84 (m, 2H), 0.60-0.56 (m, 2H).

Example 137: (S)-2-((5-(tert-butyl)-1-(tetrahydro-furan-3-yl)-1H-pyrazol-3-yl)amino)-1-methyl-6-(pyrazolo[1,5-a]pyrazin-3-yloxy)-1H-imidazo[4,5-b]pyridine-7-carbonitrile

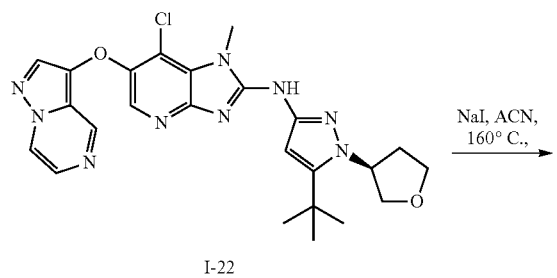

I-22

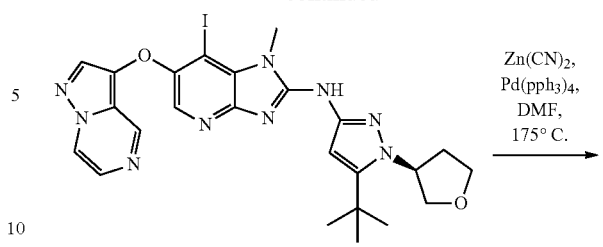

137.1

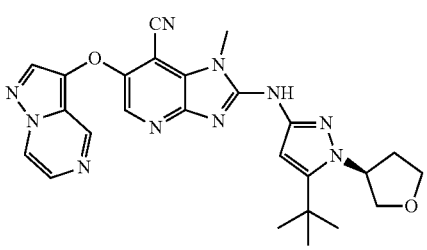

I-137

Synthesis of compound 137.1. A mixture of I-22 (0.110 g, 0.216 mmol, 1.0 equiv) and sodium iodide (0.323 g, 2.16 mmol, 10 equiv) in acetonitrile (2 mL) was stirred at 160° C. for 16 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.5% methanol in DCM) to afford 137.1. MS (ES): m/z 600.1 [M]⁺.

Synthesis of I-137. A mixture of 137.1 (0.075 g, 0.125 mmol, 1.0 equiv) and zinc cyanide (0.016 g, 0.137 mmol, 1.1 equiv) in DMF (2 mL) was degassed by bubbling argon through for 10 min. Under argon atmosphere tetrakis(triphenylphosphine)palladium(0) (0.014 g, 0.012 mmol, 0.1 equiv) was added, and degassed for another 5 min. The reaction mixture was stirred at 170° C. in a microwave reactor for 30 min. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.2% methanol in DCM) to afford I-137. MS (ES): m/z 499.4 [M]⁺, ¹H NMR (DMSO-$d_6$, 400 MHz): δ 10.29 (s, 1H), 9.08 (s, 1H), 8.75-8.74 (d, J=3.6 Hz, 1H), 8.22 (s, 1H), 8.04 (s, 1H), 7.93-7.91 (d, J=4.8 Hz, 1H), 6.56 (s, 1H), 5.28 (bs, 1H), 4.12-4.10 (m, 2H), 3.95 (s, 3H), 3.87-3.83 (m, 1H), 2.24 (bs, 1H), 1.57 (bs, 2H), 1.40 (s, 9H).

Example 138: 3-((7-chloro-1-methyl-6-(pyrazolo[1,5-a]pyrazin-3-yloxy)-1H-imidazo[4,5-b]pyridin-2-yl)amino)-1-(3-(3,3-difluoropiperidin-1-yl)propyl)-5-(trifluoromethyl)pyridin-2(1H)-one

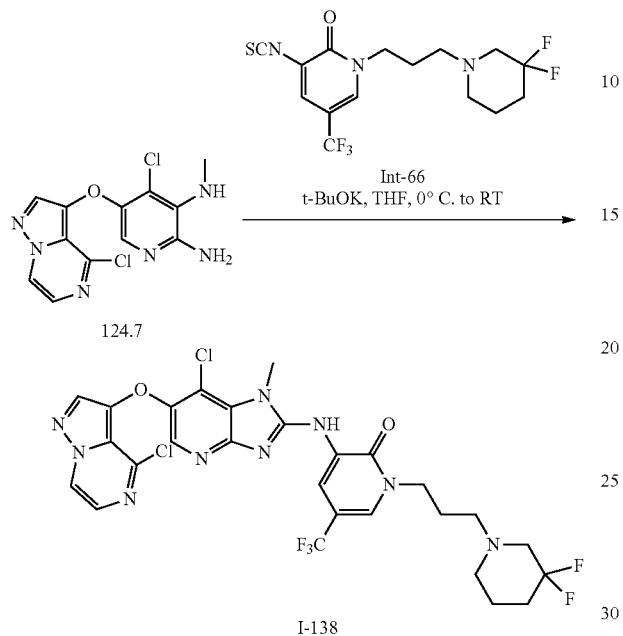

Synthesis of I-138. Compound I-138 was prepared from 124.7 and Int-66, following the procedure described in the synthesis of I-13. The product was purified by flash column chromatography on silica gel (CombiFlash®, 3.0% methanol in DCM). MS (ES): m/z 639.1 [M+H]+; ¹H NMR (DMSO-d₆, 400 MHz): δ 9.04 (s, 1H), 8.86 (s, 1H), 8.70-8.69 (m, 1H), 8.62-8.61 (d, J=2.0 Hz, 1H), 8.24 (s, 1H), 8.06 (s, 1H), 8.04 (s, 1H), 7.88-7.86 (d, J=5.2 Hz, 1H), 4.13-4.10 (m, 2H), 4.01 (s, 3H), 2.67-2.62 (m, 2H), 2.42-2.39 (m, 4H), 1.99-1.85 (m, 4H), 1.64 (bs, 2H).

Example 139: 3-((7-chloro-6-((4-((1R,2R)-2-hydroxycyclobutoxy)pyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one and 3-((7-chloro-6-((4-((1S,2S)-2-hydroxycyclobutoxy)pyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

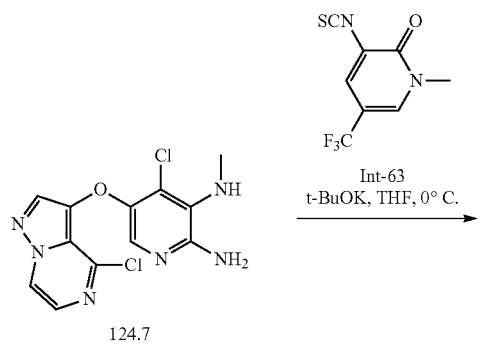

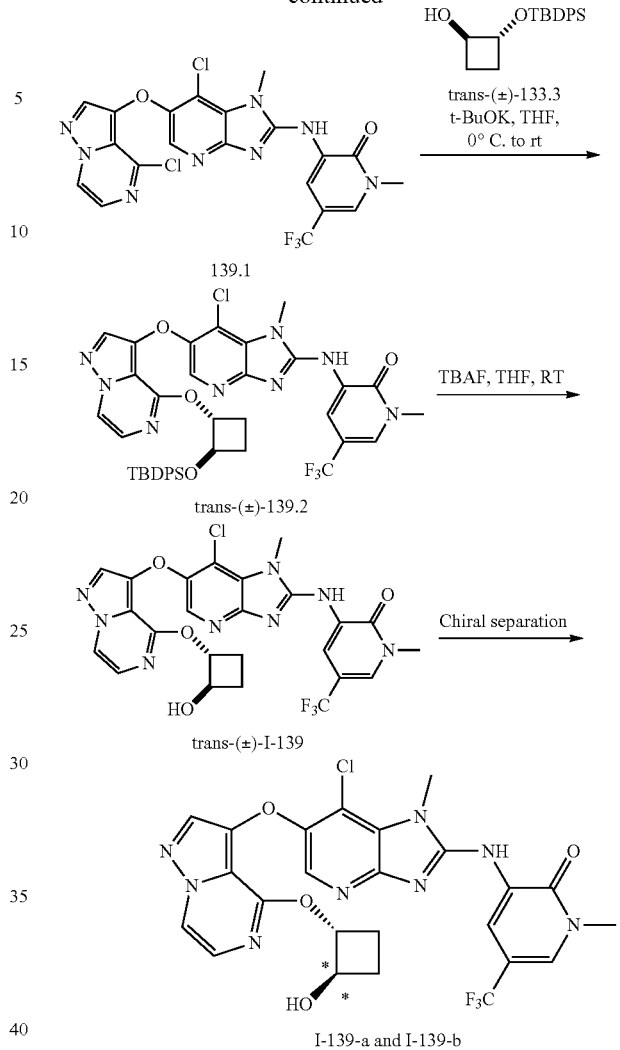

Synthesis of compound 139.1. Compound 139.1 was prepared from 124.7 and Int-63, following the procedure described in the synthesis of I-13. The product was purified by flash column chromatography on silica gel (CombiFlash®, 2.5% methanol in DCM). MS (ES): m/z 526.2 [M+H]⁺.

Synthesis of compound trans-(±)-139.2. Compound trans-(±)-139.2 was prepared from 139.1 and trans-(±)-133.3, following the procedure described in the synthesis of I-127. The product was purified by flash column chromatography on silica gel (CombiFlash®, 2.0% methanol in DCM). MS (ES): m/z 816.2 [M+H]⁺.

Synthesis of compound trans-(±)-I-139. Compound trans-(±)-I-139 was prepared from trans-(±)-139.2, following the procedure described in the synthesis of I-133. The product was purified by trituration with methanol. MS (ES): m/z 577.5 [M+H]⁺.

I-139-a and I-139-b. trans-(±)-139 was separated by HPLC (column: CHIRALPAK IB-N (250 mm*21 mm, 5 μm); mobile phase: (A) 0.1% DEA in n-hexane, (B) 0.1% DEA in isopropanol:methanol (50:50); flow rate=20 mL/min) to afford first eluting fraction (I-139-a) and second eluting fraction (I-139-b). (*Absolute stereochemistry not determined.)

I-139-a: MS (ES): m/z 577.5 [M+H]⁺, ¹H NMR (DMSO-d₆, 400 MHz): δ 8.84 (s, 1H), 8.52 (s, 1H), 8.26-8.24 (d, J=4.8 Hz, 1H), 7.88 (s, 1H), 7.71 (bs, 2H), 7.33-7.32 (d, J=4.8 Hz, 1H), 5.44 (bs, 1H), 5.04-5.02 (m, 1H), 3.89 (bs, 4H), 3.53 (s, 3H), 2.09-2.07 (m, 1H), 1.98-1.95 (m, 1H), 1.38-1.33 (m, 1H), 1.23-1.19 (m, 1H).

I-139-b: MS (ES): m/z 577.5 [M+H]⁺, ¹H NMR (DMSO-d₆, 400 MHz): δ 8.84 (s, 1H), 8.56 (s, 1H), 8.28-8.27 (d, J=4.8 Hz, 1H), 7.97 (bs, 2H), 7.87 (s, 1H), 7.35-7.34 (d, J=4.8 Hz, 1H), 5.40-5.38 (m, 1H), 5.02-4.97 (m, 1H), 3.97 (s, 1H), 3.84 (bs, 1H), 3.60 (s, 3H), 2.10-2.05 (m, 1H), 1.98-1.91 (m, 1H), 1.39-1.31 (m, 1H), 1.17-1.10 (m, 1H).

Example 140: 3-((7-chloro-1-methyl-6-((4-morpholinopyrazolo[1,5-a]pyrazin-3-yl)oxy)-1H-imidazo[4,5-b]pyridin-2-yl)amino)-1-(2-hydroxyethyl)-5-(trifluoromethyl)pyridin-2(1H)-one Synthesis of compound 140.1. Compound 140.1 was prepared from 124.7 and Int-48, following the procedure described in the synthesis of I-13. The product was purified by flash column chromatography on silica gel (CombiFlash®, 2% methanol in DCM). MS (ES): m/z 646.3 [M+H]⁺.

Synthesis of compound 140.2. A solution of 140.1 (0.150 g, 0.232 mmol, 1.0 equiv) in morpholine (3 mL) was stirred at 100° C. for 1 h. It was cooled to room temperature and transferred into ice-water. The precipitated solids were collected by filtration and dried under vacuum to afford 140.2. MS (ES): m/z 696.8 [M+H]⁺.

Synthesis of compound I-140. Compound I-140 was prepared from 100.1, following the procedure described in the synthesis of I-23. The product was purified by trituration with diethyl ether. MS (ES): m/z 607.0 [M+H]⁺. ¹H NMR (DMSO-d₆, 400 MHz): δ 8.84 (s, 1H), 8.64 (s, 1H), 8.17-8.15 (d, J=4.8 Hz, 1H), 8.09 (s, 1H), 7.98 (s, 1H), 7.81 (s, 1H), 7.43-7.41 (d, J=5.2 Hz, 1H), 5.01-4.99 (m, 1H), 4.2 (bs, 2H), 4.03 (s, 3H), 3.75-3.74 (m, 2H), 3.67 (s, 4H), 3.51 (s, 4H).

Example 141: 3-((7-chloro-6-((4-fluoropyrazolo[1,5-a]pyridin-3-yl)oxy)-1-methyl-1H-imidazo[4,5-b]pyridin-2-yl)amino)-5-cyclopropyl-1-(2-hydroxyethyl)pyridin-2(1H)-one

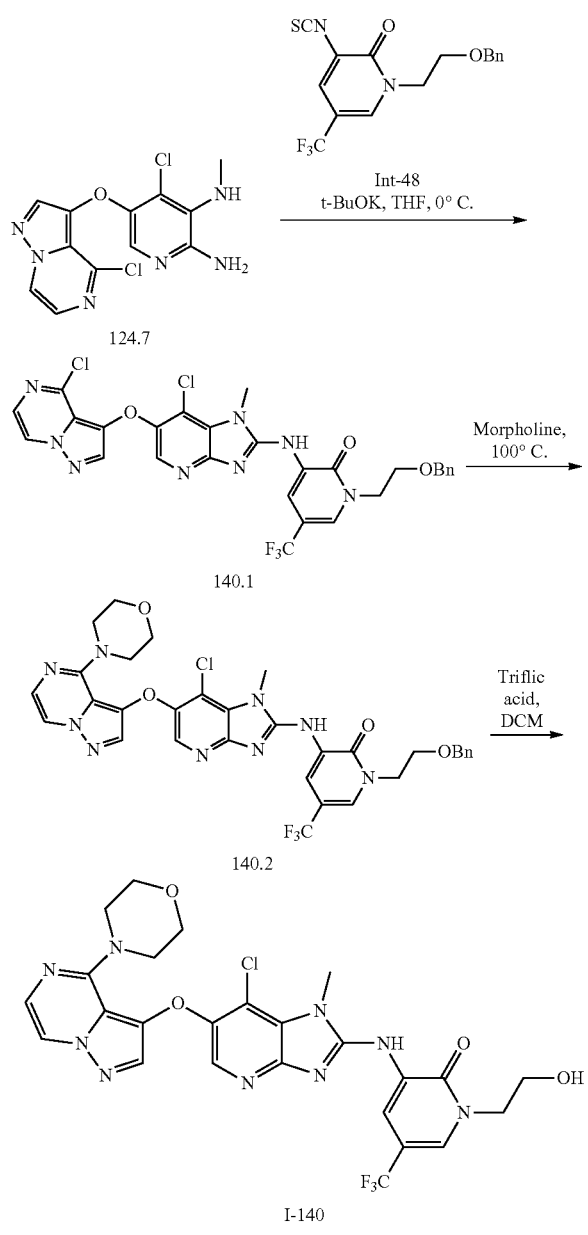

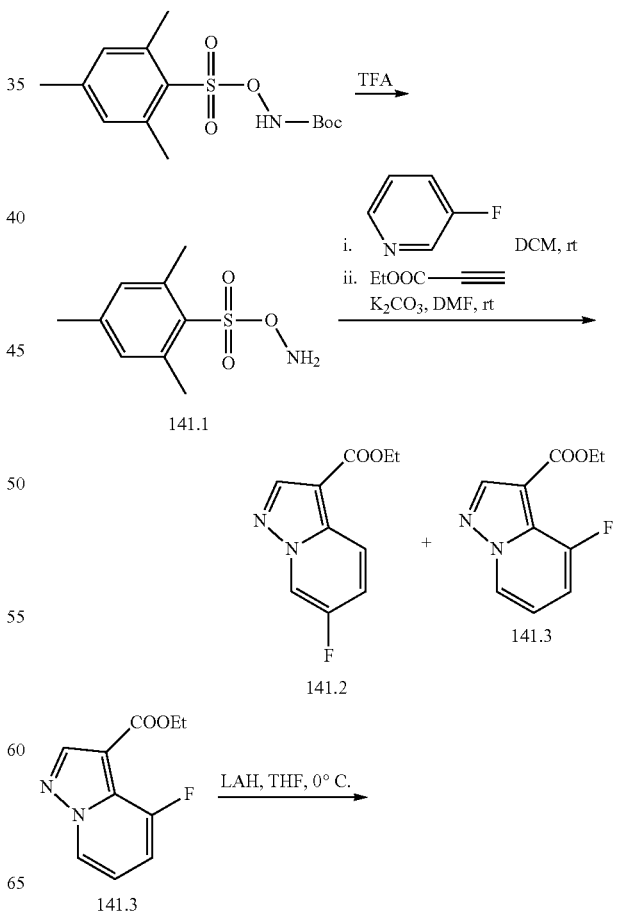

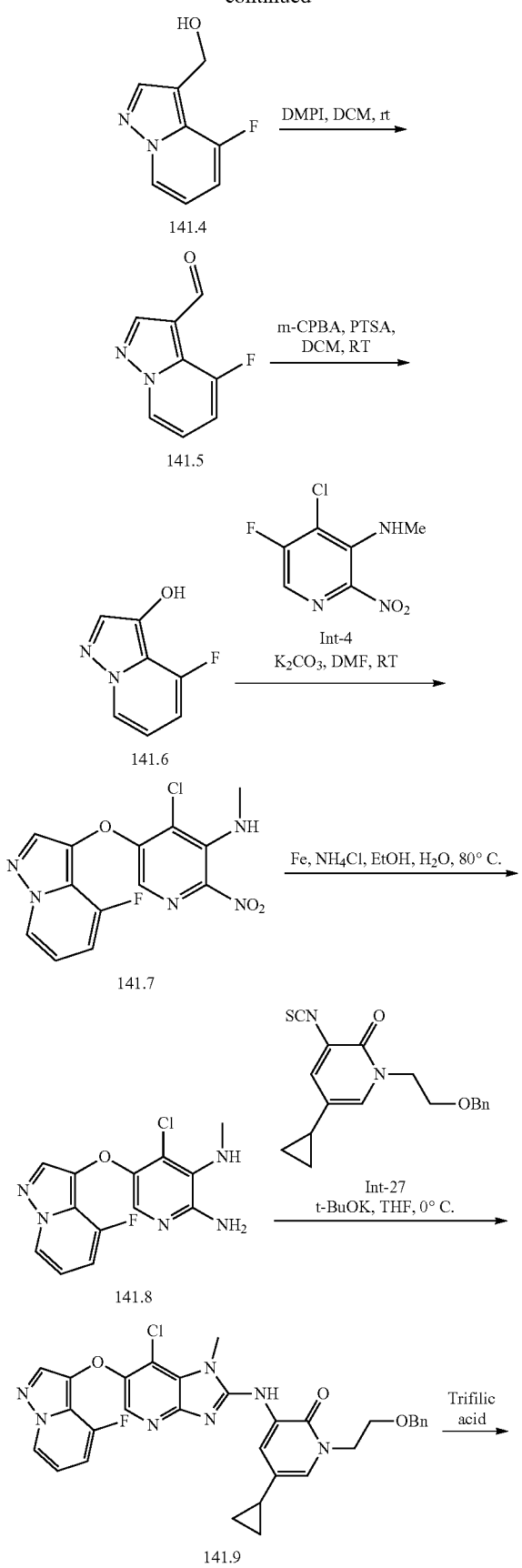
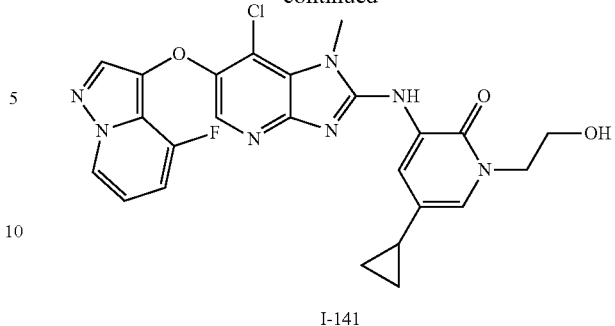

I-141

Synthesis of compound 141.1. tert-Butyl ((mesitylsulfonyl)oxy)carbamate (335 g, 1060 mmol, 1.0 equiv) was dissolved in trifluoroacetic acid (770 mL, 2.3 vol) at −10° C. and stirred at 0° C. for 1 h. It was poured over ice-water and stirred. The precipitated solids were collected by filtration, rinsed with water and dried under vacuum. The product was dissolved in DCM, dried over anhydrous sodium sulfate, filtered and concentrated under reduced pressure to afford 141.1. MS (ES): m/z 216.6 [M+H]$^+$.

Synthesis of compound 141.2 and 141.3. To a solution of 141.1 (25.0 g, 257.7 mmol, 1.0 equiv) in DCM (250 mL) was added 3-fluoropyridine (55.4 g, 257.7 mmol, 1.0 equiv) at 0° C. The reaction mixture was stirred at room temperature for 90 min. It was poured over diethyl ether and stirred. The solids were collected by filtration and air-dried. The product was dissolved in DMF (500 mL) and added trimethylamine (98.3 g, 973.4 mmol, 2.0 equiv) followed by ethyl propiolate (95.39 g, 973.4 mmol, 2.0 equiv) at 0° C. The reaction mixture was stirred at room temperature for 72 h. It was poured over brine and extracted with ethyl acetate. The combined organic layers were washed with brine, dried over anhydrous sodium sulfate, filtered and concentrated under reduced pressure. The residue was purified by flash column chromatography on silica gel (4% ethyl acetate in hexane) to afford 141.2, MS (ES): m/z 209.1 [M] and 141.3, MS (ES): m/z 209.1 [M]$^+$.

Synthesis of compound 141.4. To a solution of 141.3 (1.5 g, 7.20 mmol, 1.0 equiv) in THF (30 mL) was added lithium aluminum hydride (1 M in THF, 14.4 mL, 14.4 mmol, 2.0 equiv) at 0° C. The reaction mixture was refluxed for 30 min. It was cooled to room temperature, transferred into ice, stirred and extracted with ethyl acetate. The combined organic layers were washed with brine, dried over anhydrous sodium sulfate, filtered and concentrated under reduced pressure to afford 141.4. MS (ES): m/z 167.1 [M+H]$^+$.

Synthesis of compound 141.5. To a solution of 141.4 (1.0 g, 6.02 mmol, 1 equiv) in DCM was added Dess-Martin periodinane (6.38 g, 15.05 mmol, 2.5 equiv). The reaction mixture was stirred at room temperature for 10 min. The reaction mixture was transferred into an aqueous solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 26% ethyl acetate in hexane) to afford 141.5. MS (ES): m/z 165.0 [M+H]$^+$.

Synthesis of compound 141.6. To a solution 141.5 (0.400 g, 7.43 mmol, 1.0 equiv) in DCM (10 mL) was added m-chloroperbenzoic acid (0.800 g, 11.14 mmol, 1.5 equiv) and trifluoroacetic acid (0.1 mL, 0.74 mmol, 0.1 equiv) 0° C. The reaction mixture was stirred at room temperature for 12 h. The reaction mixture transferred into an aqueous solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, using 30% ethyl acetate in hexane) to afford 141.6. MS (ES): m/z 153.1 [M+H]+.

Synthesis of compound 141.7. Compound 141.7 was prepared from 141.6 and Int-4, following the procedure described in the synthesis of 19.1. The product was used in the next step without purification. MS (ES): m/z 337.5 [M+H]+.

Synthesis of compound 141.8. Compound 141.8 was prepared from 141.7, following the procedure described in the synthesis of 3.7. The product was purified by flash column chromatography on silica gel (CombiFlash®, 4% methanol in DCM). MS (ES): m/z 308.4 [M+H]+.

Synthesis of compound 141.9. Compound 141.9 was prepared from 141.8 and Int-27, following the procedure described in the synthesis of I-13. The product was purified by flash column chromatography on silica gel (CombiFlash®, 2.8% methanol in DCM). MS (ES): m/z 600.7 [M+H]+.

Synthesis of I-141. Compound I-141 was prepared from 141.9, following the procedure described in the synthesis of I-23. The product was purified by flash column chromatography on silica gel (CombiFlash®, 3.2% methanol in DCM). MS (ES): m/z 511 [M+H]+. $^1$H NMR (DMSO-$d_6$, 400 MHz): δ 8.55 (s, 1H), 8.53-8.51 (d, J=6.4 Hz, 1H), 8.28-8.27 (d, J=2.0 Hz, 1H), 8.05 (s, 1H), 7.96 (s, 1H), 7.17 (bs, 1H), 7.10-7.08 (m, 1H), 6.90-6.85 (m, 1H), 4.96-4.93 (m, 1H), 4.07-4.04 (m, 2H), 4.00 (s, 3H), 3.72-3.70 (m, 2H), 1.85-1.81 (m, 1H), 0.89-0.85 (m, 2H), 0.59-0.55 (m, 2H).

Example 142: (R)-4-((7-chloro-1-methyl-6-(pyrazolo[1,5-a]pyridin-3-yloxy)-1H-imidazo[4,5-b]pyridin-2-yl)amino)-6-cyclopropyl-2-(tetrahydrofuran-3-yl)pyridazin-3(2H)-one

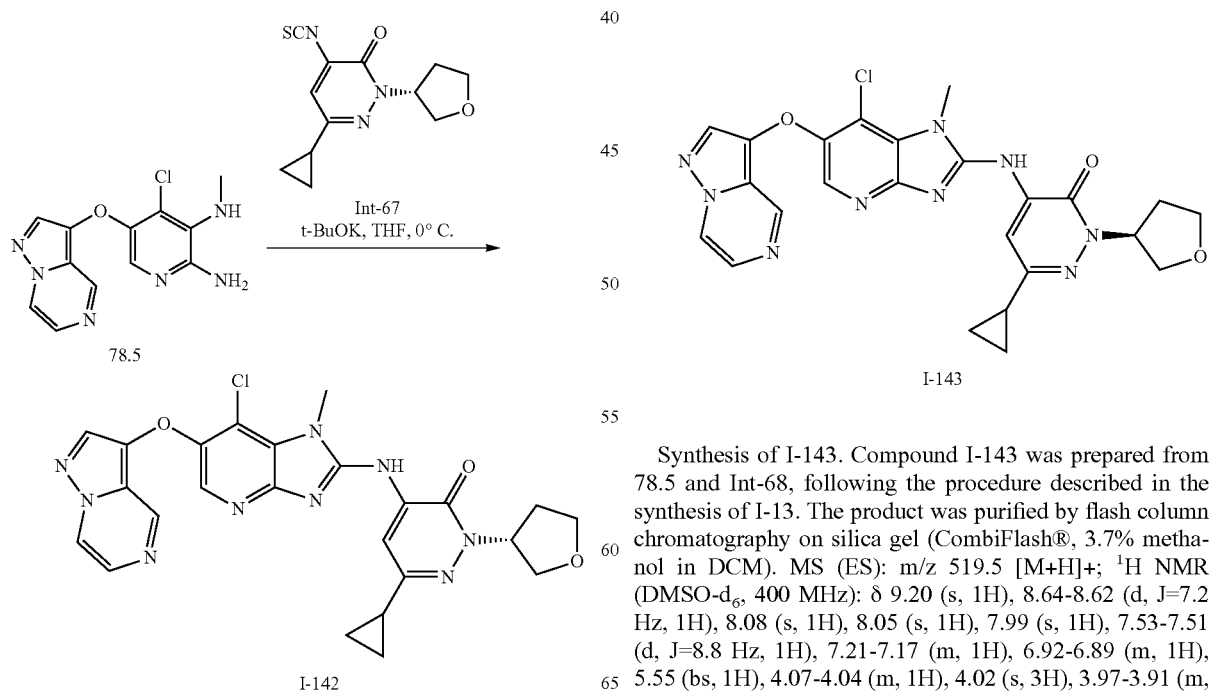

I-142

Synthesis of I-142. Compound I-142 was prepared from 78.5 and Int-67, following the procedure described in the synthesis of I-13. The product was purified by flash column chromatography on silica gel (CombiFlash®, 3.7% methanol in DCM). MS (ES): m/z 519.5 [M+H]+; $^1$H NMR (DMSO-$d_6$, 400 MHz): δ 9.20 (s, 1H), 8.64-8.62 (d, J=7.2 Hz, 1H), 8.08 (s, 1H), 8.05 (s, 1H), 7.99 (s, 1H), 7.53-7.51 (d, J=8.8 Hz, 1H), 7.21-7.17 (m, 1H), 6.92-6.89 (m, 1H), 5.55 (bs, 1H), 4.07-4.04 (m, 1H), 4.02 (s, 3H), 3.97-3.91 (m, 1H), 3.89-3.86 (m, 1H), 3.78-3.75 (m, 1H), 2.28-2.25 (m, 2H), 2.01-1.98 (m, 1H), 0.96-0.94 (m, 2H), 0.81 (bs, 2H).

Example 143: (S)-4-((7-chloro-1-methyl-6-(pyrazolo[1,5-a]pyridin-3-yloxy)-1H-imidazo[4,5-b]pyridin-2-yl)amino)-6-cyclopropyl-2-(tetrahydrofuran-3-yl)pyridazin-3(2H)-one

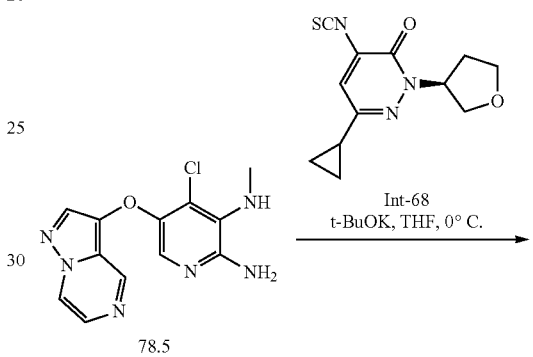

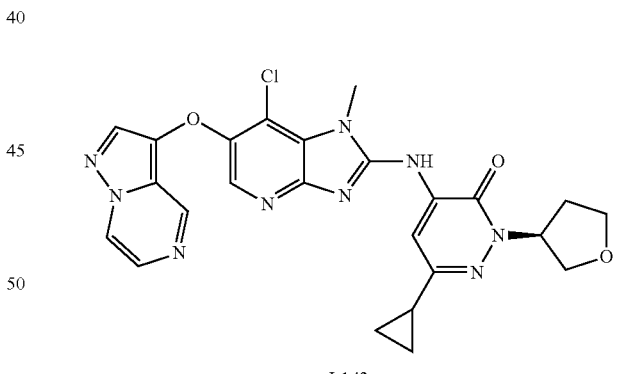

I-143

Synthesis of I-143. Compound I-143 was prepared from 78.5 and Int-68, following the procedure described in the synthesis of I-13. The product was purified by flash column chromatography on silica gel (CombiFlash®, 3.7% methanol in DCM). MS (ES): m/z 519.5 [M+H]+; $^1$H NMR (DMSO-$d_6$, 400 MHz): δ 9.20 (s, 1H), 8.64-8.62 (d, J=7.2 Hz, 1H), 8.08 (s, 1H), 8.05 (s, 1H), 7.99 (s, 1H), 7.53-7.51 (d, J=8.8 Hz, 1H), 7.21-7.17 (m, 1H), 6.92-6.89 (m, 1H), 5.55 (bs, 1H), 4.07-4.04 (m, 1H), 4.02 (s, 3H), 3.97-3.91 (m, 1H), 3.89-3.86 (m, 1H), 3.78-3.75 (m, 1H), 2.28-2.25 (m, 2H), 2.01-1.99 (m, 1H), 0.96-0.94 (m, 2H), 0.81 (bs, 2H).

Example 144: 3-((7-chloro-1-methyl-6-(pyrazolo[1,5-a]pyrazin-3-yloxy)-1H-imidazo[4,5-b]pyridin-2-yl)amino)-1-methyl-5-(perfluoroethyl)pyridin-2(1H)-one Example 145: 3-((7-chloro-1-methyl-6-(pyrazolo[1,5-a]pyridin-3-yloxy)-1H-imidazo[4,5-b]pyridin-2-yl)amino)-N-(2-morpholinoethyl)-5-(trifluoromethyl)benzamide

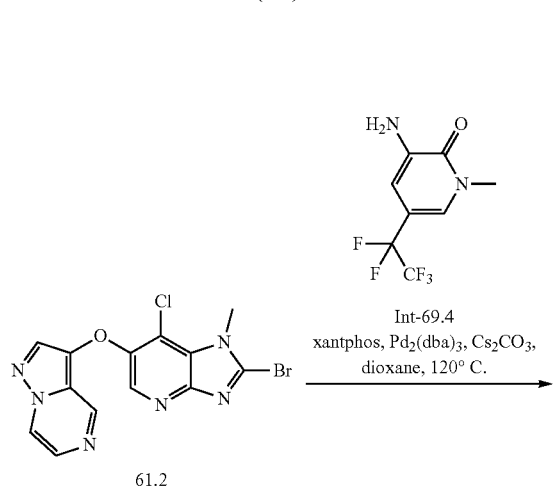

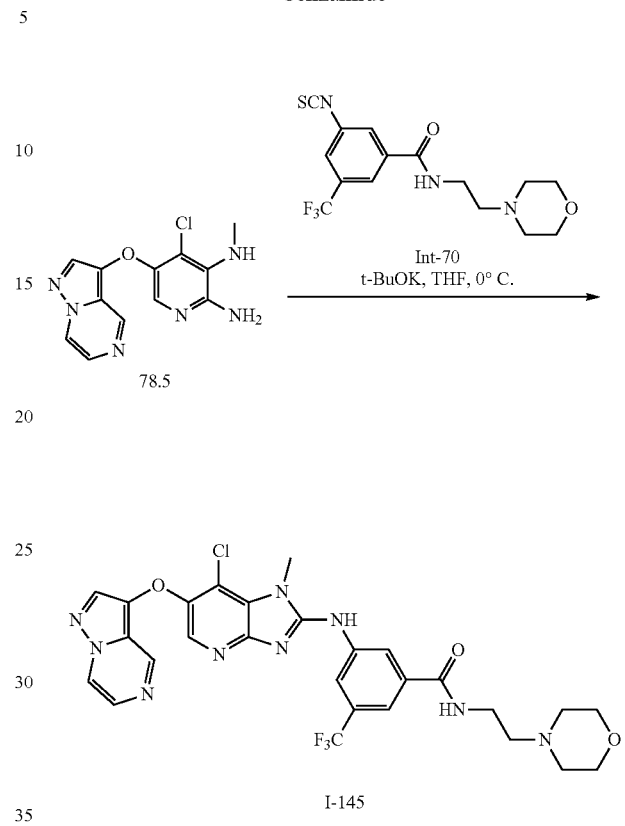

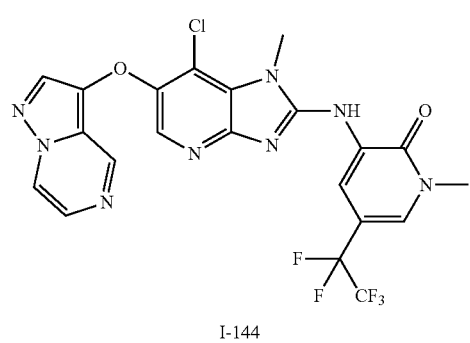

Synthesis of I-144. Compound I-144 was prepared from 61.2 and Int-69.4, following the procedure described in the synthesis of I-53. The product was purified by flash column chromatography on silica gel (CombiFlash®, 2.7% methanol in DCM). MS (ES): m/z 541.2 [M+H]⁺, ¹H NMR (DMSO-d₆, 400 MHz): δ 9.05-9.04 (d, J=0.8 Hz, 1H), 8.84 (s, 1H), 8.71-8.70 (d, J=3.6 Hz, 1H), 8.62 (s, 1H), 8.25 (s, 1H), 8.12 (s, 1H), 8.06 (s, 1H), 7.89-7.87 (d, J=4.8 Hz, 1H), 4.02 (s, 3H), 3.69 (s, 3H).

Synthesis of I-145. Compound I-145 was prepared from 78.5 and Int-70, following the procedure described in the synthesis of I-13. The product was purified by preparative HPLC. MS (ES): m/z 616.2 [M+H]⁺, ¹H NMR (DMSO-d₆, 400 MHz): δ 9.91 (s, 1H), 9.03 (s, 1H), 8.68 (s, 1H), 8.64-8.62 (d, J=6.8 Hz, 1H), 8.56 (s, 1H), 8.02 (bs, 2H), 7.86 (s, 1H), 7.52-7.50 (d, J=8.8 Hz, 1H), 7.19-7.17 (d, J=8.4 Hz, 1H), 6.90 (s, 1H), 4.05 (bs, 4H), 3.67 (s, 3H), 3.56 (s, 4H), 3.16 (s, 4H).

Example 146: 7-chloro-N-(4-((4-ethylpiperazin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

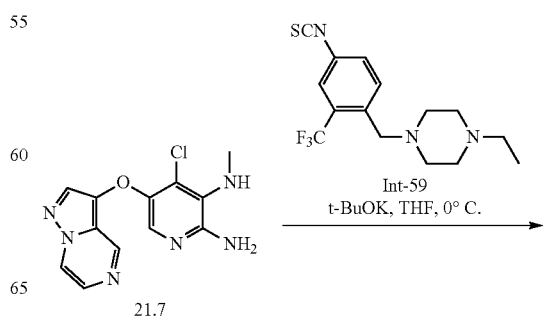

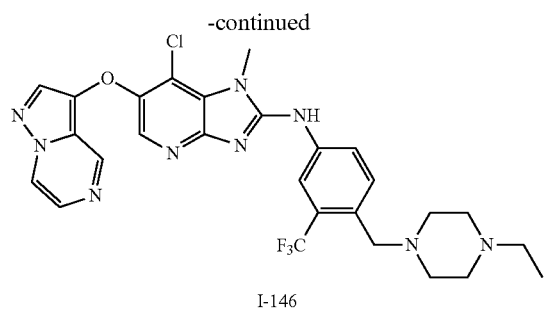

I-146

Synthesis of I-146. Compound I-146 was prepared from 21.7 and Int-59, following the procedure described in the synthesis of I-13. The product was purified by flash column chromatography on silica gel (CombiFlash®, 4.2% methanol in DCM). MS (ES): m/z 586.4 [M+H]+, ¹H NMR (DMSO-d₆, 400 MHz): δ 9.65 (s, 1H), 9.03 (s, 1H), 8.70-8.69 (d, J=4.8 Hz 1H), 8.29 (s, 1H), 8.20 (s, 1H), 8.18-8.17 (d, J=5.2 Hz 1H), 8.04 (s, 1H), 7.88-7.87 (d, J=4.8 Hz 1H), 7.74-7.72 (d, J=8.4 Hz 1H), 4.03 (s, 3H), 3.58 (s, 2H), 2.47 (bs, 4H), 2.40-2.34 (m, 6H), 1.03-0.99 (t, 3H).

Example 147: (1R,2S)-2-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)cyclobutan-1-ol and (1S,2R)-2-(5-(tert-butyl)-3-((7-chloro-1-methyl-6-(pyrazolo[1,5-a]pyrazin-3-yloxy)-1H-imidazo[4,5-b]pyridin-2-yl)amino)-1H-pyrazol-1-yl)cyclobutan-1-ol Synthesis of compound I-147-a and I-147-b. The racemate cis-(±)-I-147 was prepared from 61.2 and cis-(±)-Int-71, following the procedure described in the synthesis of Int-45. The product was purified by flash column chromatography on silica gel (CombiFlash®, 4.0% methanol in DCM). It was separated by HPLC (column: CHIRALPAK IB-N (250 mm*21 mm, 5 μm); mobile phase: (A) 0.1% DEA in hexane, (B) 0.1% DEA in isopropanol:acetonitrile (70:30); flow rate=20 mL/min) to afford first eluting fraction (I-147-a) and second eluting fraction (I-147-b). (*Absolute stereochemistry not determined.)

I-147-a: MS (ES): m/z 508.6 [M+H]+, ¹H NMR (DMSO-d₆, 400 MHz): δ 9.96 (s, 1H), 9.02 (s, 1H), 8.70-8.68 (d, J=4.8 Hz, 1H), 8.13 (s, 1H), 8.03 (s, 1H), 7.87-7.86 (d, J=4.8 Hz, 1H), 6.60 (s, 1H), 5.14-5.12 (m, 2H), 4.51 (bs, 1H), 3.98 (s, 3H), 2.24-2.19 (m, 4H), 1.36 (s, 9H).

I-147-b: MS (ES): m/z 508.7 [M+H]+, ¹H NMR (DMSO-d₆, 400 MHz): δ 9.97 (s, 1H), 9.02 (s, 1H), 8.70-8.68 (d, J=4.8 Hz, 1H), 8.13 (s, 1H), 8.03 (s, 1H), 7.88-7.86 (d, J=4.8 Hz, 1H), 6.60 (s, 1H), 5.14-5.12 (m, 2H), 4.51 (bs, 1H), 3.98 (s, 3H), 2.24-2.19 (m, 4H), 1.36 (s, 9H).

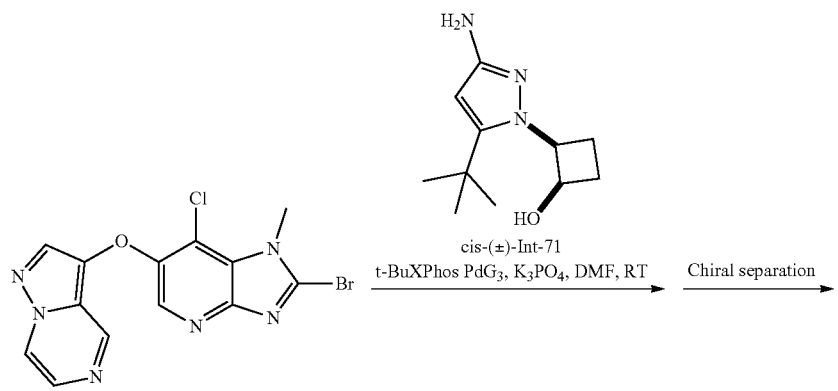

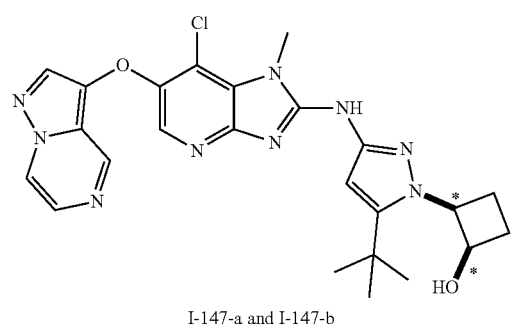

I-147-a and I-147-b

Example 148: (R)-4-((7-chloro-1-methyl-6-(pyrazolo[1,5-a]pyridin-3-yloxy)-1H-imidazo[4,5-b]pyridin-2-yl)amino)-6-cyclopropyl-2-(tetrahydro-2H-pyran-3-yl)pyridazin-3(2H)-one and (S)-4-((7-chloro-1-methyl-6-(pyrazolo[1,5-a]pyridin-3-yloxy)-1H-imidazo[4,5-b]pyridin-2-yl)amino)-6-cyclopropyl-2-(tetrahydro-2H-pyran-3-yl)pyridazin-3(2H)-one

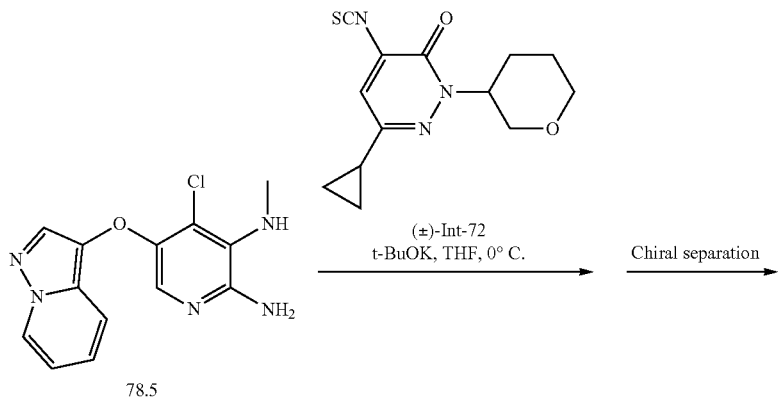

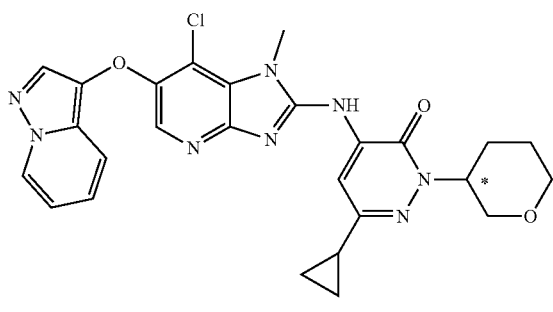

I-148-a and I-148-b

Synthesis of compound I-148-a and I-148-b. The racemate I-148 was prepared from 78.5 and (±)-Int-72, following the procedure described in the synthesis of I-13. The product was purified by flash column chromatography on silica gel (CombiFlash®, 2.4% methanol in DCM). MS (ES): m/z 533.4 [M+H]$^+$. The enantiomers were separated by HPLC (column: CHIRALPAK IB-N (250 mm*21 mm, 5 μm); mobile phase: (A) 0.1% DEA in n-hexane (B) 0.1% DEA in isopropanol:acetonitrile (70:30); flow rate=20 mL/min) to afford first eluting fraction (I-148-a) and second eluting fraction (I-148-b). (*Absolute stereochemistry not determined.)

I-148-a: MS (ES): m/z 533.3 [M+H]$^+$, $^1$H NMR (DMSO-d$_6$, 400 MHz): δ 8.65-8.63 (d, J=6.4 Hz, 1H), 8.01 (s, 1H), 7.98 (s, 1H), 7.91 (s, 1H), 7.52-7.50 (d, J=8.8 Hz, 1H), 7.20-7.16 (m, 1H), 7.08-7.06 (d, J=7.6 Hz, 1H), 6.89 (bs, 1H), 4.87 (bs, 1H), 3.97 (s, 3H), 3.84 (bs, 1H), 3.51-3.46 (m, 2H), 2.05-2.03 (m, 1H), 1.93-1.89 (m, 2H), 1.80-1.70 (m, 2H), 0.92 (bs, 2H), 0.78 (bs, 2H).

I-148-b: MS (ES): m/z 533.3 [M+H]$^+$, $^1$H NMR (DMSO-d$_6$, 400 MHz): δ 8.64-8.62 (d, J=6.8 Hz, 1H), 8.05 (s, 1H), 8.03 (s, 1H), 7.93 (s, 1H), 7.52-7.50 (d, J=8.8 Hz, 1H), 7.21-7.17 (m, 1H), 7.08-7.06 (d, J=8.0 Hz, 1H), 6.92-6.88 (m, 1H), 4.90-4.85 (m, 1H), 4.00 (s, 3H), 3.87-3.85 (m, 2H), 3.52-3.46 (m, 2H), 2.05-2.03 (m, 1H), 1.95-1.90 (m, 2H), 1.77-1.70 (m, 2H), 0.95-0.93 (m, 2H), 0.80 (bs, 2H).

Example 149: 7-chloro-1-methyl-N-(4-(morpholinomethyl)-3-(trifluoromethyl)phenyl)-6-(pyrazolo[1,5-a]pyrazin-3-yloxy)-1H-imidazo[4,5-b]pyridin-2-amine

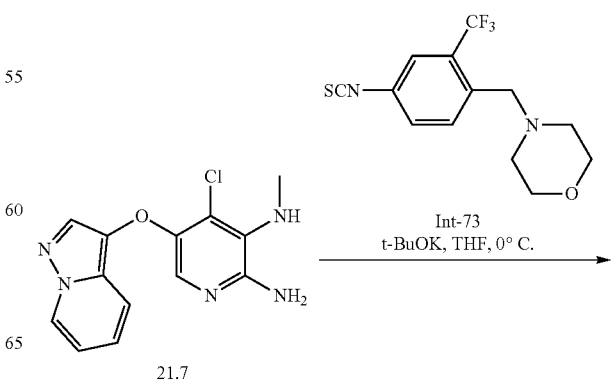

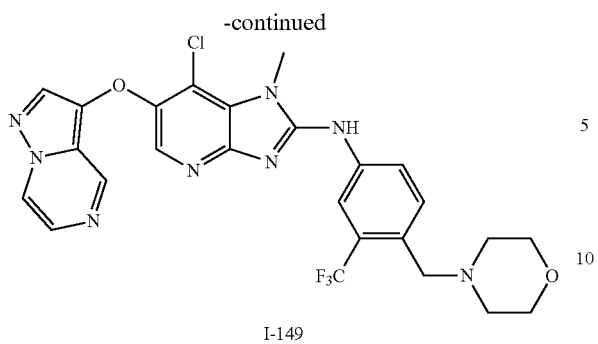

I-149

Synthesis of I-149. Compound I-149 was prepared from 21.7 and Int-73, following the procedure described in the synthesis of I-13. The product was purified by flash column chromatography on silica gel (CombiFlash®, 5.0% methanol in DCM). MS (ES): m/z 559.3 [M+H]+, 1H NMR (DMSO-d6, 400 MHz): δ 9.66 (s, 1H), 9.03 (s, 1H), 8.71-8.70 (d, J=4.4 Hz 1H), 8.30 (s, 1H), 8.21 (s, 1H), 8.18-8.16 (d, J=8.8 Hz 1H), 8.04 (s, 1H), 7.88-7.87 (d, J=4.8 Hz 1H), 7.76-7.74 (d, J=8.8 Hz 1H), 4.03 (s, 3H), 3.61-3.59 (m, 6H), 2.41 (s, 4H).

Example 150: 2-((5-(tert-butyl)-1-((3S,4R)-4-hydroxytetrahydrofuran-3-yl)-1H-pyrazol-3-yl)amino)-1-methyl-6-(pyrazolo[1,5-a]pyrazin-3-yloxy)-1H-imidazo[4,5-b]pyridine-7-carbonitrile and 2-((5-(tert-butyl)-1-((3R,4S)-4-hydroxytetrahydrofuran-3-yl)-1H-pyrazol-3-yl)amino)-1-methyl-6-(pyrazolo[1,5-a]pyrazin-3-yloxy)-1H-imidazo[4,5-b]pyridine-7-carbonitrile

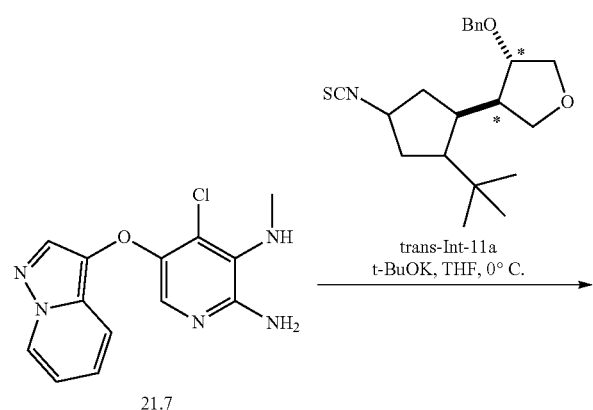

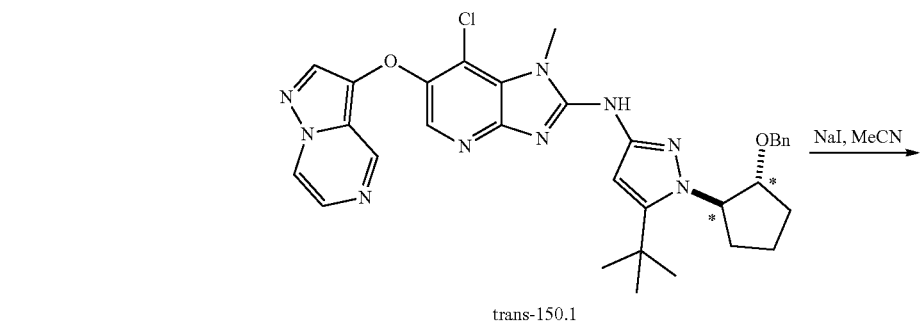

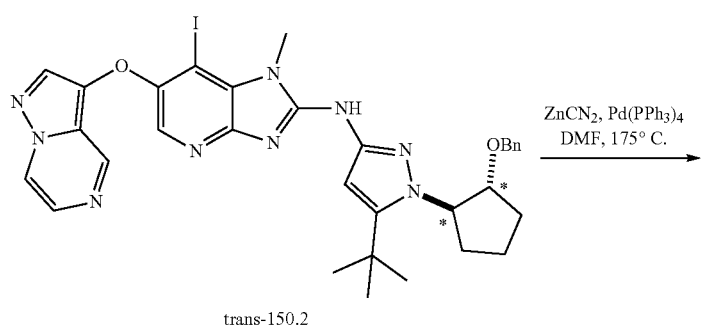

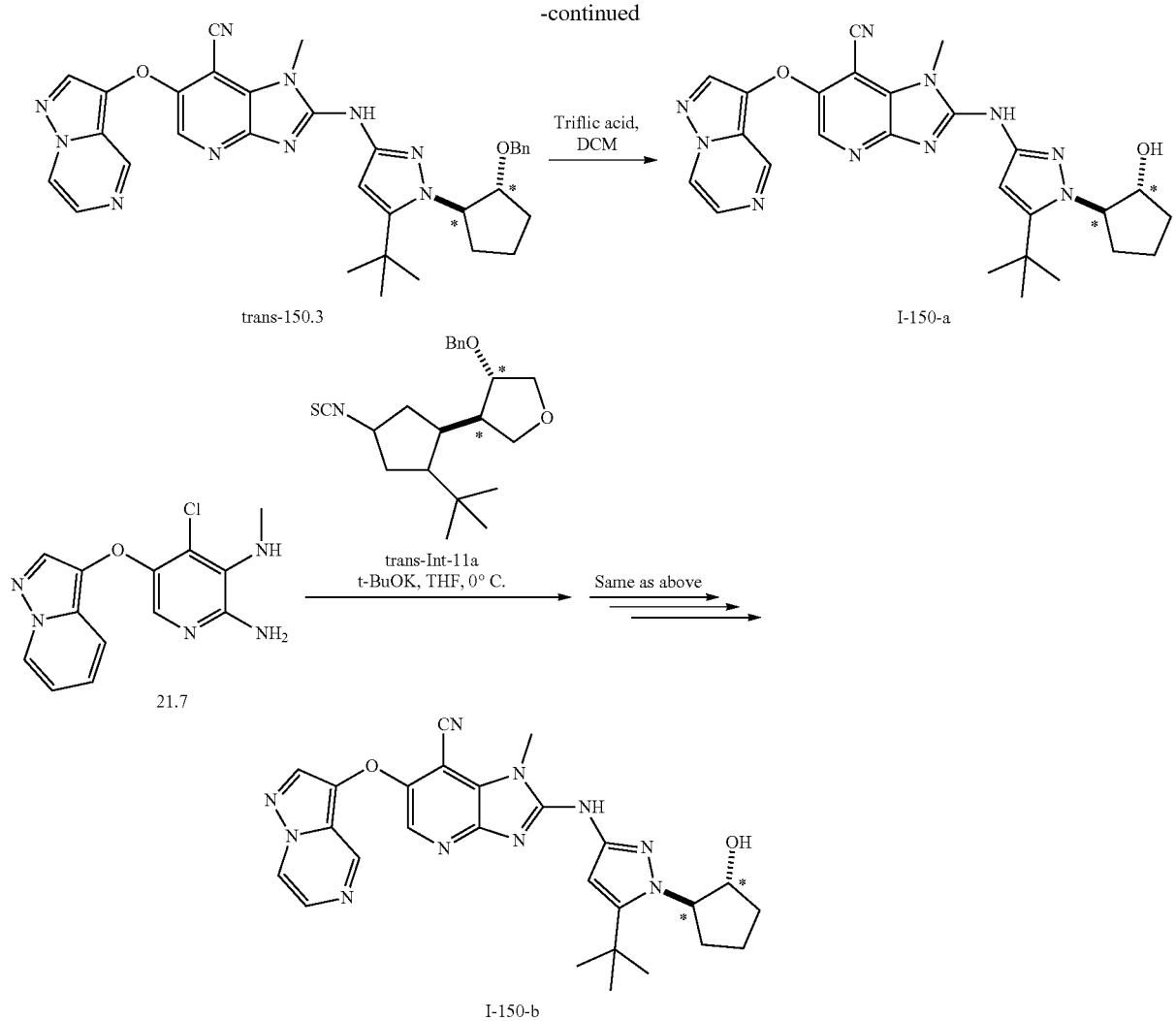

Synthesis of compound trans-150.1. Compound trans-150.1 was prepared from 21.7 and trans-Int-11a, following the procedure described in the synthesis of I-13. The product was purified by flash column chromatography on silica gel (CombiFlash®, 2.1% methanol in DCM) to afford trans-150.1. MS (ES): m/z 615.1 [M+H]$^+$.

Synthesis of compound trans-150.2. To a solution of trans-150.1 (0.160 g, 0.260 mmol, 1.0 equiv) in acetonitrile (2 mL) was added sodium iodide (0.389 g, 2.6 mmol, 10 equiv) and reaction mixture was stirred at 160° C. for 16 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.2% methanol in DCM) to afford trans-150.2. MS (ES): m/z 706.4 [M]$^+$.

Synthesis of compound trans-150.3. A mixture of trans-150.2 (0.070 g, 0.099 mmol, 1.0 equiv) and zinc cyanide (0.119 g, 0.108 mmol, 1.1 equiv) in DMF (2 mL) was degassed by bubbling argon through for 10 min. Under argon atmosphere tetrakis (triphenylphosphine)palladium(0) (0.011 g, 0.009 mmol, 0.1 equiv) was added, again degassed for 5 min. The reaction mixture was stirred at 170° C. in a microwave reactor for 30 min. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.4% methanol in DCM) to afford trans-150.3. MS (ES): m/z 605.5 [M]$^+$.

Synthesis of I-150-a. Compound I-150-a was prepared from trans-150.3, following the procedure described in the synthesis of I-23. The product was purified by flash column chromatography on silica gel (CombiFlash®, 5.0% methanol in DCM). MS (ES): m/z 515.0 [M+H]$^+$, $^1$H NMR (DMSO-d$_6$, 400 MHz): δ 10.32 (s, 1H), 9.09 (s, 1H), 8.76 (s, 1H), 8.23 (s, 1H), 8.04 (s, 1H), 7.92 (s, 1H), 6.59 (s, 1H), 5.58-5.57 (m, 1H), 4.93 (bs, 1H), 4.55 (bs, 1H), 4.29 (bs, 1H), 4.13-4.12 (m, 1H), 3.95 (s, 3H), 3.82-3.79 (m, 1H), 3.70-3.69 (m, 1H), 1.41 (s, 9H). (*Absolute stereochemistry not determined.)

Synthesis of I-150-b. Compound I-150-b was prepared from trans-Int-11b, following the procedures described in the synthesis of I-150-a. The product was purified by flash column chromatography on silica gel. MS (ES): m/z 515.0 [M+H]$^+$, $^1$H NMR (DMSO-d$_6$, 400 MHz): δ 10.32 (s, 1H), 9.09 (s, 1H), 8.76 (s, 1H), 8.23 (s, 1H), 8.04 (s, 1H), 7.92 (s, 1H), 6.59 (s, 1H), 5.58-5.57 (m, 1H), 4.93 (bs, 1H), 4.55 (bs, 1H), 4.29 (bs, 1H), 4.13-4.12 (m, 1H), 3.95 (s, 3H), 3.82-3.79 (m, 1H), 3.70-3.69 (m, 1H), 1.41 (s, 9H). (*Absolute stereochemistry not determined.)

Example 151: cis-3-((7-chloro-6-((6-fluoropyrazolo[1,5-a]pyridin-3-yl)oxy)-1-methyl-1H-imidazo[4,5-b]pyridin-2-yl)amino)-5-cyclopropyl-1-(3-hydroxy-cyclobutyl)pyridin-2(1H)-one

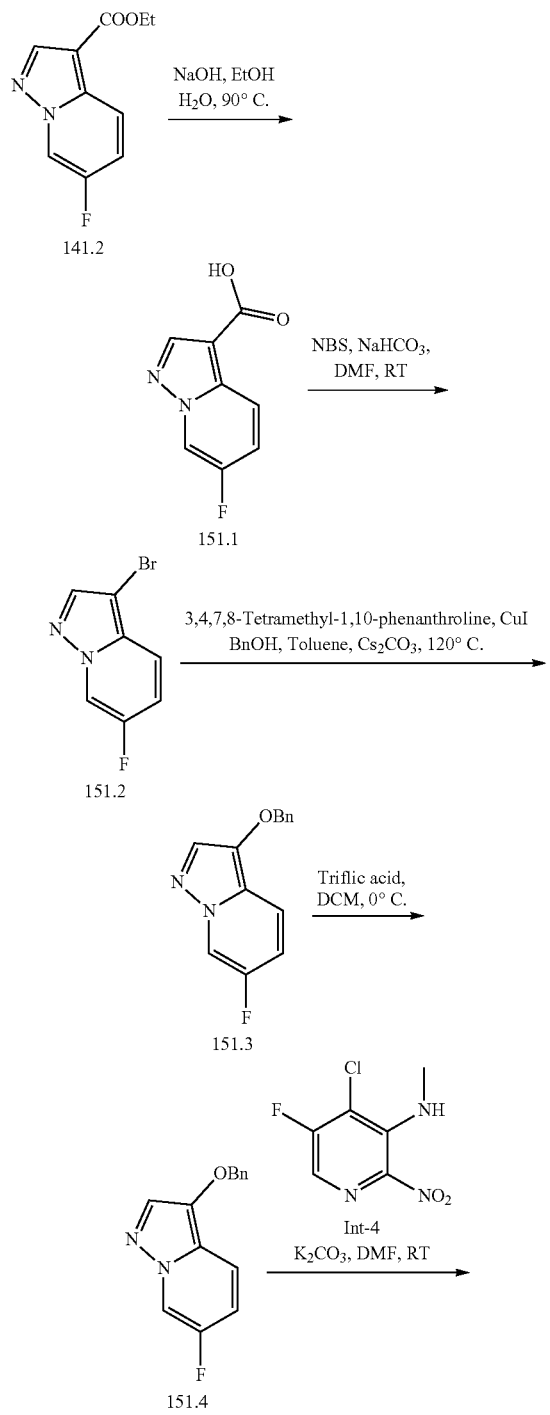

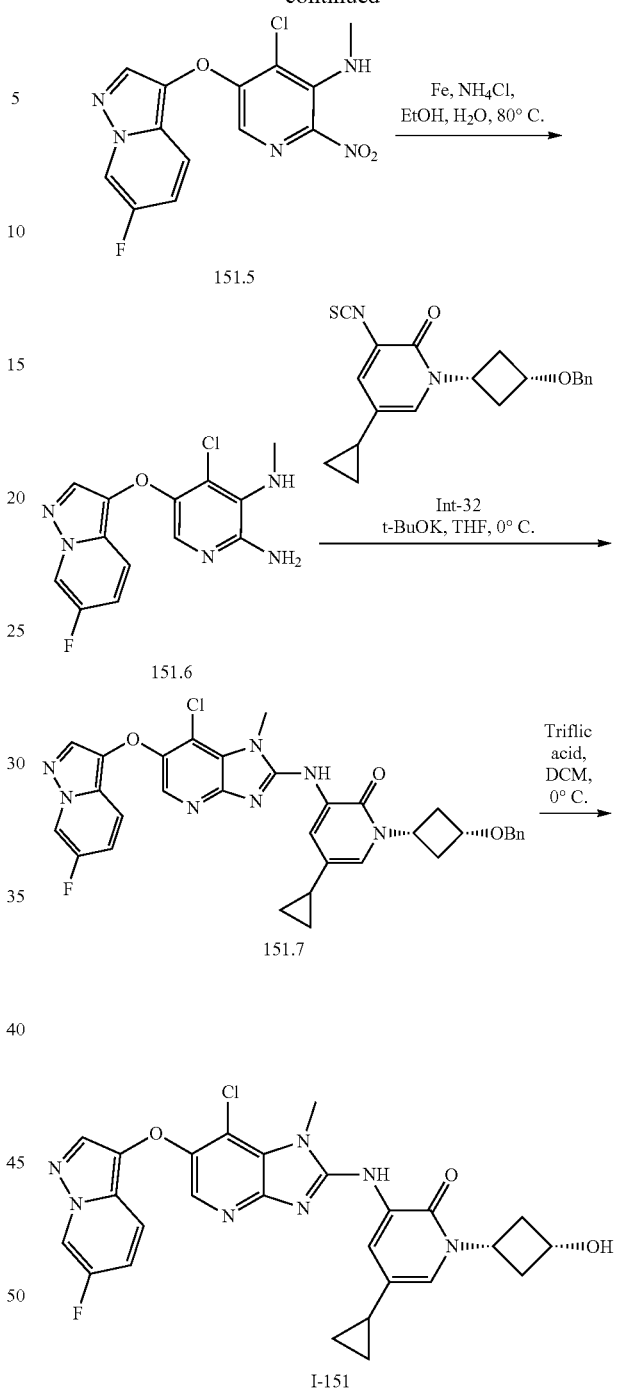

Synthesis of compound 151.1. To a solution of 141.2 (6 g, 28.82 mmol, 1.0 equiv) in ethanol (100 mL) and water (20 mL) was added sodium hydroxide (5.7 g, 144.23 mmol, 5.0 equiv) at room temperature. The reaction mixture was stirred at 90° C. for 1 h. It was concentrated under reduced pressure. The residue was neutralized by dilute hydrochloric acid and the precipitated solids were collected by filtration and dried under vacuum to afford 151.1. MS (ES): m/z 181.2 [M+H]$^+$.

Synthesis of compound 151.2. To a solution of 151.1 (3.5 g, 19.43 mmol, 1.0 equiv) in DMF (20 mL) was added sodium bicarbonate (4.8 g, 58.33 mmol, 3.0 equiv) followed by N-bromosuccinimide (3.45 g, 19.43 mmol, 1.0 equiv) and stirred at room temperature for 6 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 151.2. MS (ES): m/z 216.1 [M+H]$^+$.

Synthesis of compound 151.3 To a solution of 151.2 (3 g, 13.95 mmol, 1.0 equiv) in toluene was added benzyl alcohol (1.51 g, 14.01 mmol, 2.5 equiv), followed by cesium carbonate (9.11 g, 28.03 mmol, 2.0 equiv). The reaction mixture was degassed by bubbling argon through for 15 min. Copper iodide (0.133 g, 0.70 mmol, 0.05 equiv) and 3,4,7,8-tetramethyl-1,10-phenanthroline (0.330 g, 1.39 mmol, 0.1 equiv) were added. The reaction mixture was stirred at room temperature for 20 min and at 120° C. for 24 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 24% ethyl acetate in hexane) to afford 151.3. MS (ES): m/z 243.2 [M+H]$^+$.

Synthesis of compound 151.4. To a solution 151.3 (1.8 g, 7.43 mmol, 1.0 equiv) in DCM (20 mL) was added triflic acid (1.8 mL, 1 vol.) dropwise at 0° C. The reaction mixture was stirred for 15 min. The reaction mixture was transferred into aqueous solution of sodium bicarbonate and extracted with DCM. The combined organic layers were washed with brine, dried over anhydrous sodium sulfate, filtered and concentrated under reduced pressure. The residue was purified by flash column chromatography on silica gel (CombiFlash®, 28% ethyl acetate in hexane) to afford 151.4. MS (ES): m/z 153.1 [M+H]$^+$.

Synthesis of compound 151.5. Compound 151.5 was prepared from 151.4 and Int-4, following the procedure described in the synthesis of 19.1. The product was purified by flash column chromatography on silica gel (CombiFlash®, 25% ethyl acetate in hexane). MS (ES): m/z 338.5 [M+H]$^+$.

Synthesis of compound 151.6. Compound 151.6 was prepared from 151.5, following the procedure described in the synthesis of 3.7. The product was purified by flash column chromatography on silica gel (CombiFlash®, 1.7% methanol in DCM). MS (ES): m/z 308.7 [M+H]$^+$.

Synthesis of compound 151.7. Compound 151.7 was prepared from 151.6 and Int-32, following the procedure described in the synthesis of I-13. The product was purified by flash column chromatography on silica gel (CombiFlash®, 1.8% methanol in DCM). MS (ES): m/z 626.7 [M+H]$^+$.

Synthesis of compound I-151. Compound I-151 was prepared from 151.7, following the procedure described in the synthesis of I-23. The product was purified by flash column chromatography on silica gel (CombiFlash®, 3.8% methanol in DCM). MS (ES): m/z 536.7 [M+H]$^+$, $^1$H NMR (DMSO-d$_6$, 400 MHz): δ 8.98 (s, 1H), 8.52 (s, 1H), 8.20 (s, 1H), 8.04 (s, 1H), 8.01 (s, 1H), 7.64-7.60 (m, 1H), 7.34-7.28 (m, 2H), 5.43-5.39 (m, 1H), 5.256-5.25 (m, 1H), 4.39 (bs, 1H), 3.99 (s, 3H), 2.68-2.60 (m, 2H), 2.33 (bs, 2H), 1.90 (bs, 1H), 0.89-0.87 (m, 2H), 0.62 (bs, 2H).

Example 152: trans-3-((7-chloro-6-((6-fluoropyrazolo[1,5-a]pyridin-3-yl)oxy)-1-methyl-1H-imidazo[4,5-b]pyridin-2-yl)amino)-5-cyclopropyl-1-(3-hydroxycyclobutyl)pyridin-2(1H)-one

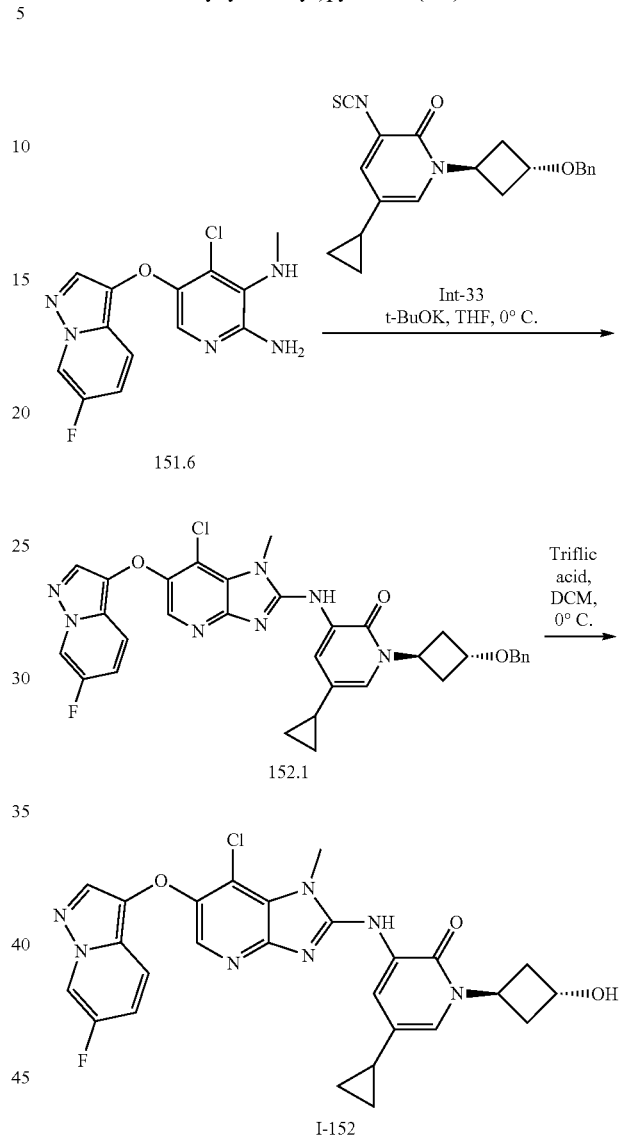

Synthesis of compound 152.1. Compound 152.1 was prepared from 151.6 and Int-33, following the procedure described in the synthesis of I-13. The product was purified by flash column chromatography on silica gel (CombiFlash®, 2.4% methanol in DCM). MS (ES): m/z 626.2 [M+H]$^+$.

Synthesis of compound I-152. Compound I-152 was prepared from 152.1, following the procedure described in the synthesis of I-23. The product was purified by flash column chromatography on silica gel (CombiFlash®, 3.0% methanol in DCM). MS (ES): m/z 536.65 [M+H]$^+$. $^1$H NMR (DMSO-d$_6$, 400 MHz): δ 8.98-8.97 (d, J=3.6 Hz, 1H), 8.52 (s, 1H), 8.21-8.20 (d, J=1.6 Hz, 1H), 8.04 (s, 1H), 8.01 (s, 1H), 7.64-7.60 (m, 1H), 7.34-7.28 (m, 2H), 5.43-5.39 (m, 1H), 5.26-5.25 (m, 1H), 4.38 (bs, 1H), 3.99 (s, 3H), 2.65-2.60 (m, 2H), 2.35-2.30 (m, 2H), 1.93-1.88 (m, 1H), 0.91-0.87 (m, 2H), 0.62-0.60 (m, 2H).

Example 153: 4-((7-chloro-6-((6-(2-methoxyethoxy)pyrazolo[1,5-a]pyridin-3-yl)oxy)-1-methyl-1H-imidazo[4,5-b]pyridin-2-yl)amino)-6-cyclopropyl-2-(2-hydroxyethyl)pyridazin-3(2H)-one
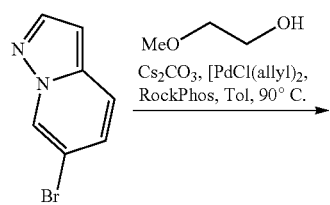
Cs₂CO₃, [PdCl(allyl)]₂, RockPhos, Tol, 90° C.
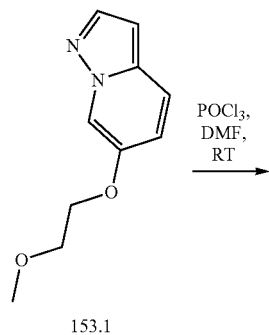
153.1
POCl₃, DMF, RT
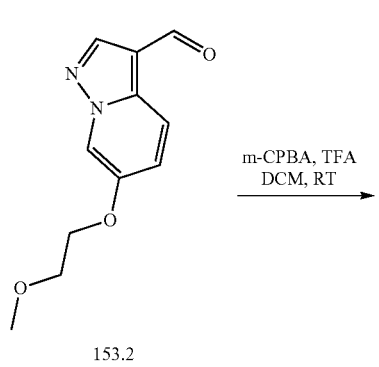
153.2
m-CPBA, TFA DCM, RT
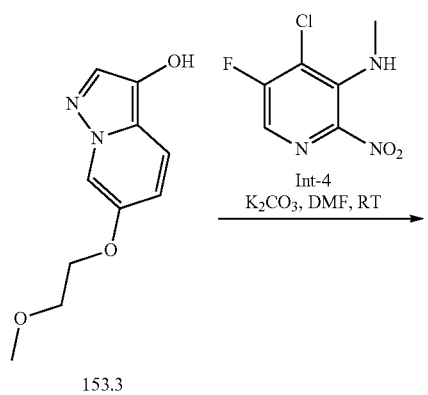
153.3
Int-4
K₂CO₃, DMF, RT
-continued
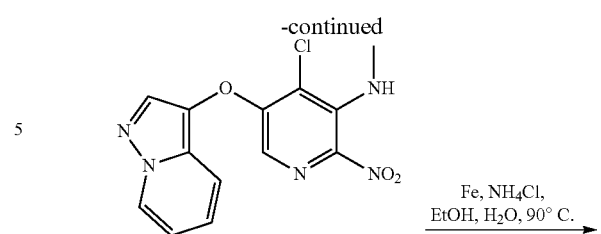
153.4
Fe, NH₄Cl, EtOH, H₂O, 90° C.
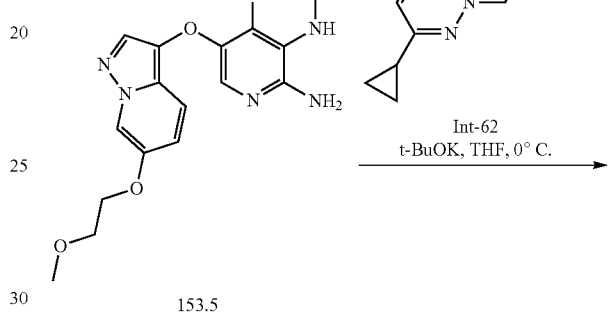
153.5
Int-62
t-BuOK, THF, 0° C.
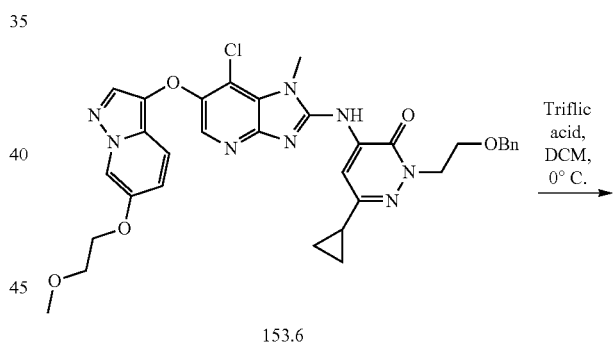
153.6
Triflic acid, DCM, 0° C.
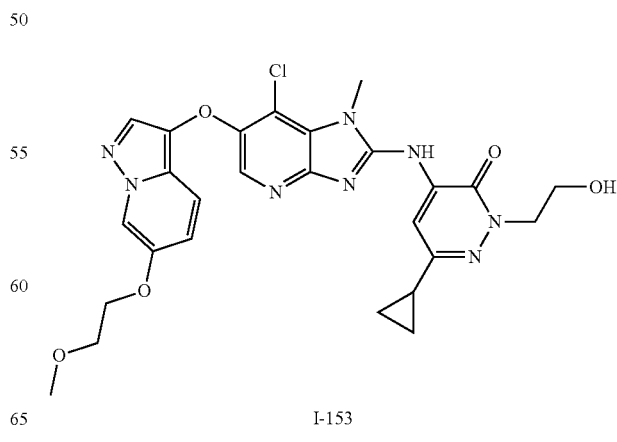
I-153

Synthesis of compound 153.1. A mixture of 6-bromopyrazolo[1,5-a]pyridine (1 g, 5.08 mmol, 1.0 equiv), 2-methoxyethan-1-ol (0.772 g, 10.15 mmol, 2.0 equiv) and cesium carbonate (4.95 g, 15.24 mmol, 3.0 equiv) in toluene (30 mL) was degassed by bubbling argon through for 10 min. Under argon atmosphere, di-tert-butyl(2',4',6'-triisopropyl-3-methoxy-6-methyl-[1,1'-biphenyl]-2-yl)phosphine (0.357 g, 0.762 mmol, 0.15 equiv) and allyl palladium(II) chloride dimer (0.092 g, 0.254 mmol, 0.05 equiv) were added and degassed for another 5 min. The reaction mixture was stirred at 90° C. for 2 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5.3% methanol in DCM) to afford 153.1. MS (ES): m/z 193.2 [M+H]$^+$.

Synthesis of compound 153.2. To a solution of 153.1 (0.610 g, 3.17 mmol, 1.0 equiv) in DMF (8 mL) was added phosphoryl chloride (1.45 g, 9.51 mmol, 3.0 equiv) and the reaction mixture was stirred at room temperature for 1 h. It was concentrated under reduced pressure. The residue was dissolved in DCM and washed with 2N sodium hydroxide. Organic layers combined, washed with brine, dried over anhydrous sodium sulfate, filtered and concentrated under reduced pressure to afford pressure. The residue was purified by flash column chromatography on silica gel (CombiFlash®, 10% methanol in DCM) to afford 153.2. MS (ES): m/z 221.0 [M+H]$^+$.

Synthesis of compound 153.3. To a solution of 153.2 (0.450 g, 2.04 mmol, 1.0 equiv) in DCM (10 mL) was added trifluoroacetic acid (1 mL) at 0° C. followed by addition of m-chloroperoxybenzoic acid (0.351 g, 2.04 mmol, 1.0 equiv). The reaction mixture was stirred at room temperature for 2 h. It was cooled to 0° C. and added saturated sodium bicarbonate solution. The mixture was stirred for 30 min and extracted with ethyl acetate. The organic layer was separated, washed with aq. sodium bisulphite, dried over anhydrous sodium sulfate, filtered and concentrated under reduced pressure. The residue was purified by flash column chromatography on silica gel (CombiFlash®, 5% methanol in DCM) to afford 153.3. MS (ES): m/z 209.1 [M+H]$^+$.

Synthesis of compound 153.4. Compound 153.4 was prepared from 153.3 and Int-4, following the procedure described in the synthesis of 19.1. The product was purified by flash column chromatography on silica gel (CombiFlash®, 2.5% methanol in DCM). MS (ES): m/z 394.5 [M+H]$^+$.

Synthesis of compound 153.5. Compound 153.5 was prepared from 153.4, following the procedure described in the synthesis of 3.7. The product was purified by flash column chromatography on silica gel (CombiFlash®, 2.8% methanol in DCM). MS (ES): m/z 364.4 [M+H]$^+$.

Synthesis of Compound 153.6. Compound 153.6 was prepared from 153.5 and Int-62, following the procedure described in the synthesis of I-13. The product was purified by flash column chromatography on silica gel (CombiFlash®, 4% methanol in DCM). MS (ES): m/z 657.9 [M+H]$^+$.

Synthesis of I-153. Compound I-153 was prepared from 153.6, following the procedure described in the synthesis of I-23. The product was by flash column chromatography on silica gel (CombiFlash®, 4.5% methanol in DCM). MS (ES): m/z 567.3 [M+H]$^+$, $^1$H NMR (DMSO-d$_6$, 400 MHz): δ 9.19 (s, 1H), 8.37 (s, 1H), 8.09 (s, 1H), 7.96 (s, 1H), 7.90 (s, 1H), 7.45-7.43 (d, J=9.6 Hz, 1H), 7.04-7.02 (d, J=9.2 Hz, 1H), 4.88-4.85 (m, 1H), 4.17-4.16 (m, 4H), 4.03 (s, 3H), 3.76-3.69 (m, 4H), 3.33 (s, 3H), 1.56 (bs, 1H), 0.97-0.95 (m, 2H), 0.81 (bs, 2H).

Example 154: 6-((7-chloro-1-methyl-6-(pyrazolo[1,5-a]pyrazin-3-yloxy)-1H-imidazo[4,5-b]pyridin-2-yl)amino)-2,3,3-trimethyl-4-(trifluoromethyl)isoindolin-1-one

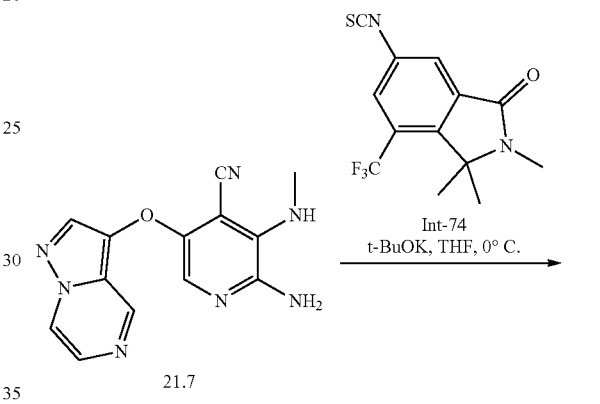

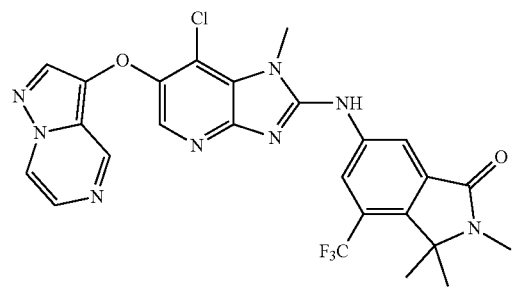

Synthesis of compound I-154. Compound I-154 was prepared from 21.7 and Int-74, following the procedure described in the synthesis of I-13. The product was purified by flash column chromatography on silica gel (CombiFlash®, 2.7% methanol in DCM). MS (ES): m/z 556.7 [M]$^+$, $^1$H NMR (DMSO-d$_6$, 400 MHz): δ 9.90 (s, 1H), 9.03 (s, 1H), 8.72-8.68 (m, 2H), 8.46-8.45 (d, J=1.6 Hz 1H), 8.23 (s, 1H), 8.04 (s, 1H), 7.87-7.86 (d, J=5.2 Hz 1H), 4.04 (s, 3H), 2.99 (s, 3H), 1.52 (s, 6H).

Example 155: 3-((7-chloro-6-((6-(2-methoxyethoxy)pyrazolo[1,5-a]pyridin-3-yl)oxy)-1-methyl-1H-imidazo[4,5-b]pyridin-2-yl)amino)-5-cyclopropyl-1-(2-hydroxyethyl)pyridin-2(1H)-one Synthesis of I-155. Compound I-155 was prepared from 155.1, following the procedure described in the synthesis of I-23. The product was by flash column chromatography on silica gel (CombiFlash®, 4.5% methanol in DCM). MS (ES): m/z 567.3 [M+H, $^1$H NMR (DMSO-d$_6$, 400 MHz): δ

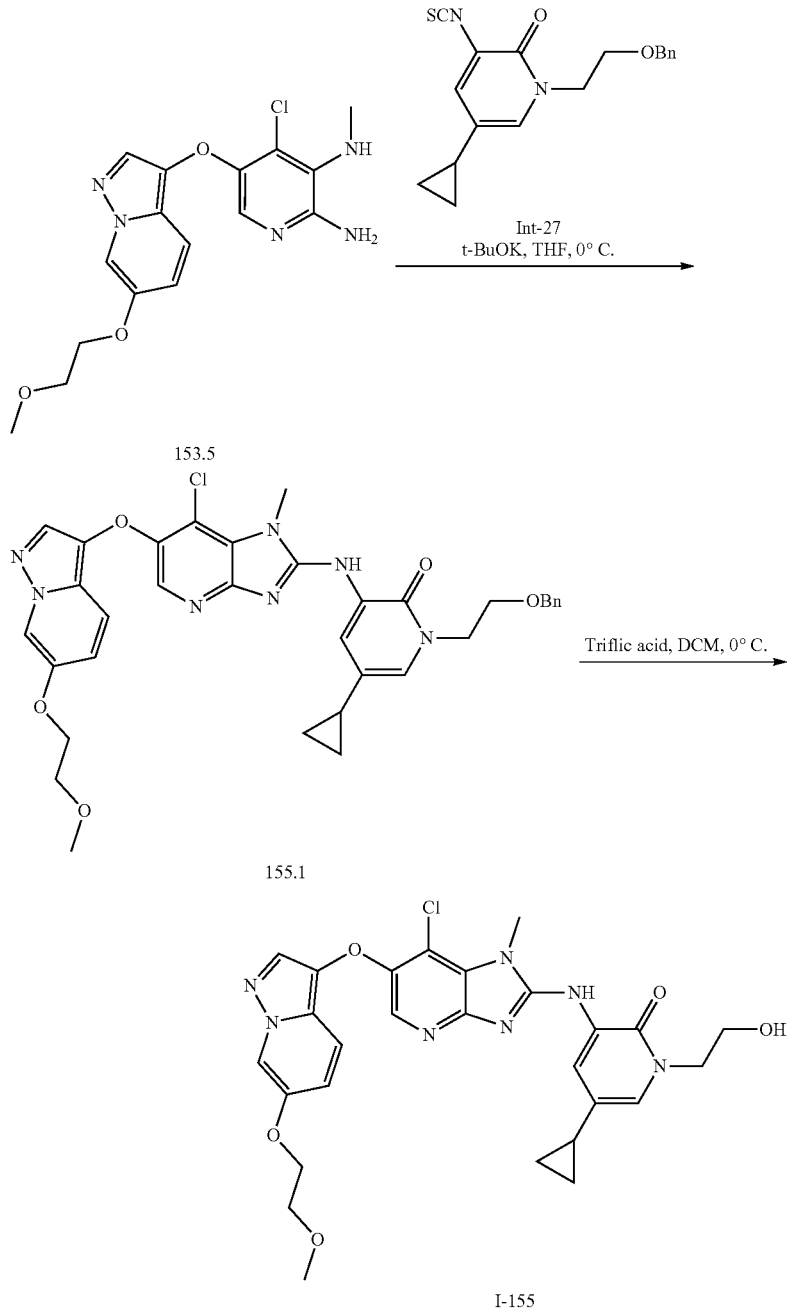

Synthesis of compound 155.1. Compound 155.1 was prepared from 153.5 and Int-27, following the procedure described in the synthesis of I-13. The product was purified by flash column chromatography on silica gel (CombiFlash®, 5% methanol in DCM) to afford I-155. MS (ES): m/z 657.1 [M+H]$^+$.

8.51 (s, 1H), 8.36 (s, 1H), 8.27 (s, 1H), 8.01 (s, 1H), 7.88 (s, 1H), 7.44-7.42 (d, J=9.6 Hz, 1H), 7.17 (s, 1H), 7.03-7.01 (d, J=9.6 Hz, 1H), 4.95-4.94 (m, 1H), 4.16 (bs, 2H), 4.06 (s, 3H), 4.00 (s, 3H), 3.70 (bs, 4H), 3.40 (bs, 2H), 1.83 (bs, 1H), 0.88-0.86 (m, 2H), 0.58-0.57 (m, 2H).

Example 156: 1-(6-(3-((7-chloro-1-methyl-6-(pyrazolo[1,5-a]pyrazin-3-yloxy)-1H-imidazo[4,5-b]pyridin-2-yl)amino)-5-(trifluoromethyl)-1H-pyrazol-1-yl)-2-azaspiro[3.3]heptan-2-yl)ethan-1-one

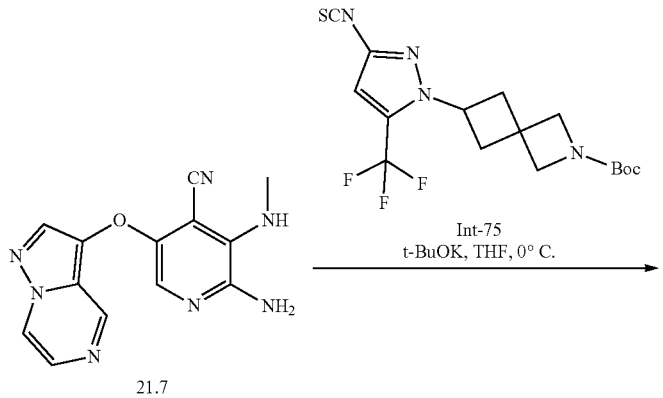

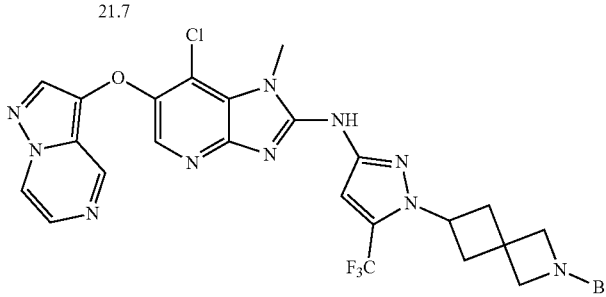

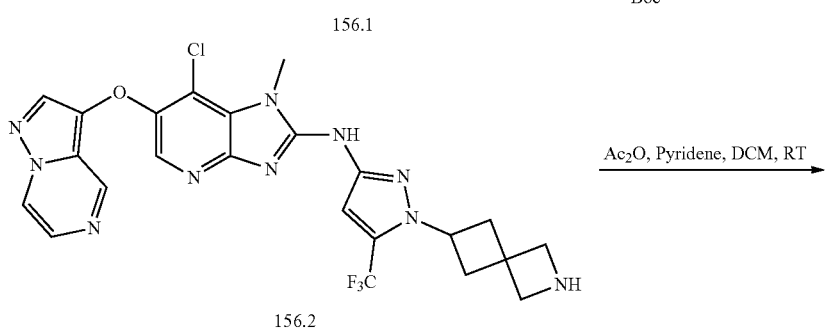

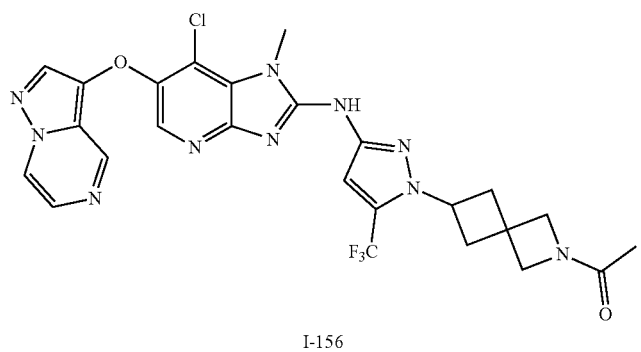

Synthesis of compound 156.1. Compound 156.1 was prepared from 21.7 and Int-75, following the procedure described in the synthesis of I-13. The product was purified by flash column chromatography on silica gel (CombiFlash®, 2.5% methanol in DCM). MS (ES): m/z 645.8 [M+H]⁺.

Synthesis of compound 156.2. To a solution of 156.1 (0.080 g, 0.124 mmol, 1.0 equiv) in DCM (5 mL) was added trifluoroacetic acid (0.42 g, 3.72 mmol, 30 equiv) at 0° C. The reaction mixture was stirred at room temperature for 2 h. It was poured over ice-cold saturated sodium bicarbonate solution and extracted with DCM. The combined organic layers were washed with brine, dried over anhydrous sodium sulfate, filtered and concentrated under reduced pressure to afford 156.2. MS (ES): m/z 545.5 [M+H]⁺.

Synthesis of I-156. To a solution of 156.2 (0.050 g, 0.091 mmol, 1.0 equiv) and triethylamine (0.013 g, 0.136 mmol, 1.5 equiv) in DCM (2 mL) at 0° C. was added acetic anhydride (0.009 g, 0.091 mmol, 1.0 equiv) dropwise. The reaction mixture was stirred at 0° C. for 1 h. It was poured over ice-water, stirred and extracted with DCM. This was purified by flash column chromatography on silica gel (CombiFlash®, 4.6% methanol in DCM) to afford I-156. MS (ES): m/z 587.3 [M+H]+, 1H NMR (DMSO-$d_6$, 400 MHz): δ 10.57-10.56 (d, J=2.8 Hz, 1H), 9.02 (s, 1H), 8.70-8.69 (d, J=4.8 Hz, 1H), 8.18 (s, 1H), 8.04 (s, 1H), 7.88-7.87 (d, J=4.4 Hz, 1H), 7.32 (s, 1H), 4.93-4.87 (m, 1H), 4.27 (s, 1H), 4.15 (s, 1H), 4.00 (bs, 4H), 3.88 (s, 1H), 2.01 (s, 3H), 1.76 (bs, 2H), 1.57 (bs, 2H).

Example 157: 1-methyl-2-((2-oxo-5-(trifluoromethyl)-2H-[1,3'-bipyridin]-3-yl)amino)-6-(pyrazolo[1,5-a]pyridin-3-yloxy)-1H-imidazo[4,5-b]pyridine-7-carbonitrile

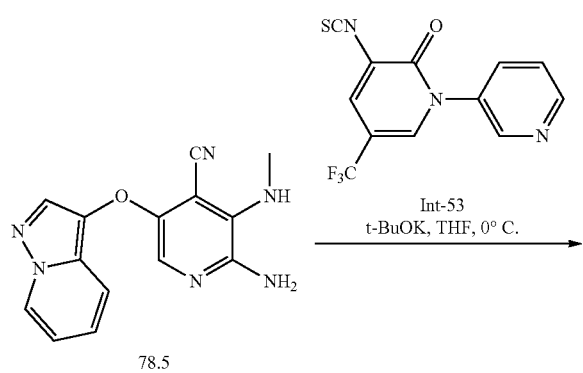

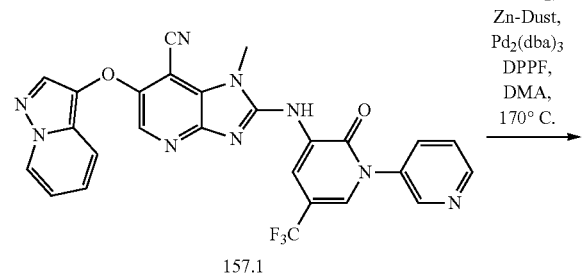

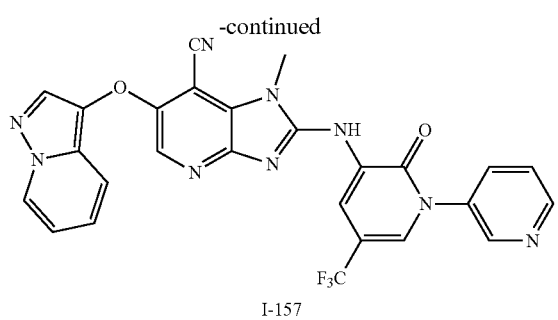

I-157

Synthesis of compound 157.1. Compound 157.1 was prepared from 78.5 and Int-53, following the procedure described in the synthesis of I-13. The product was purified by flash column chromatography on silica gel (CombiFlash®, 2.2% methanol in DCM). MS (ES): m/z 553.6 [M+H]+.

Synthesis of I-157. A mixture of 157.1 (0.100 g, 0.180 mmol, 1.0 equiv), zinc dust (0.002 g, 0.036 mmol, 0.2 equiv) and zinc cyanide (0.105 g, 0.9 mmol, 5.0 equiv) in DMA (4 mL) was degassed by bubbling argon through for 10 min. Under argon atmosphere tris(dibenzylideneacetone)dipalladium(0) (0.024 g, 0.027 mmol, 0.15 equiv) and 1,1'-bis(diphenylphosphino)ferrocene (0.029 g, 0.054 mmol, 0.3 equiv) were added, and degassed for another 5 min. The reaction mixture was stirred at 170° C. in a microwave reactor for 3 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.9% methanol in DCM) to afford I-157. MS (ES): m/z 543.4 [M]+, 1H NMR (DMSO-$d_6$, 400 MHz): δ 9.12 (s, 1H), 8.81 (s, 1H), 8.71-8.68 (m, 3H), 8.19 (s, 1H), 8.16 (s, 1H), 8.09-8.07 (d, J=8.0 Hz, 1H), 7.97 (s, 1H), 7.65 (bs, 1H), 7.56-7.54 (d, J=8.4 Hz, 1H), 7.26-7.22 (m, 1H), 6.96-6.95 (m, 1H), 3.98 (s, 3H).

Example 158: trans-2-((5-(tert-butyl)-1-(3-hydroxycyclobutyl)-1H-pyrazol-3-yl)amino)-1-methyl-6-(pyrazolo[1,5-a]pyrazin-3-yloxy)-1H-imidazo[4,5-b]pyridine-7-carbonitrile

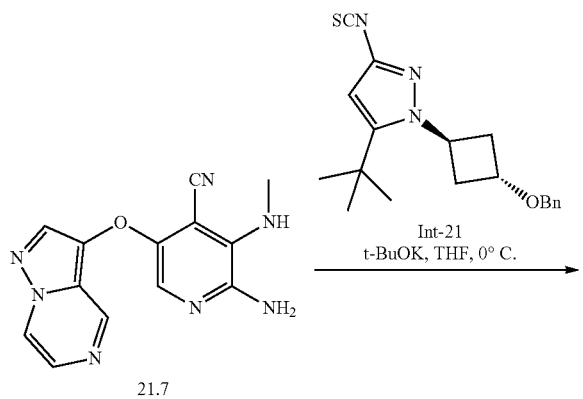

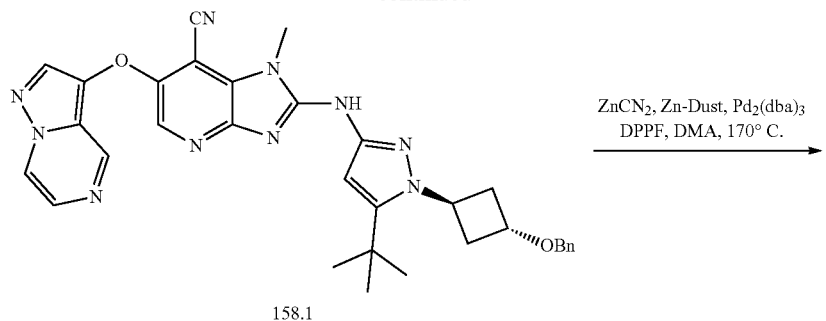

158.1

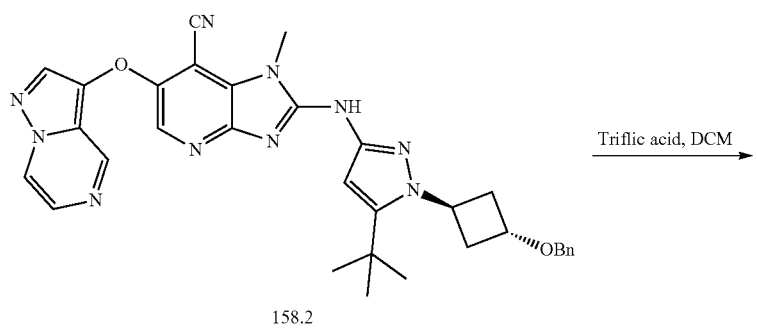

158.2

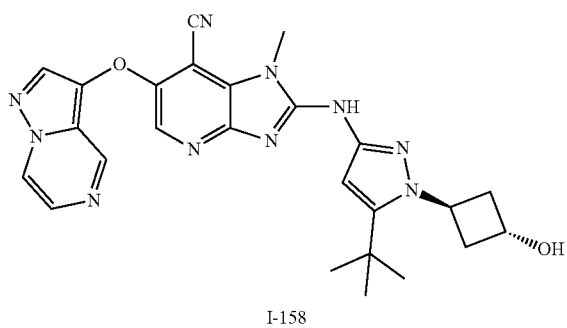

I-158

Synthesis of compound 158.1. Compound 158.1 was prepared from 21.7 and Int-21, following the procedure described in the synthesis of I-13. The product was purified by flash column chromatography on silica gel (CombiFlash®, 3% methanol in DCM). MS (ES): m/z 598.2 [M]⁺.

Synthesis of compound 158.2. Compound 158.2 was prepared from 158.1, following the procedure described in the synthesis of I-157. The product was purified by flash column chromatography on silica gel (CombiFlash®, 2.8% methanol in DCM). MS (ES): m/z 589.3 [M+H]⁺.

Synthesis of I-158. Compound I-158 was prepared from 158.2, following the procedure described in the synthesis of I-23. The product was purified by flash column chromatography on silica gel (CombiFlash®, 3.5% methanol in DCM). MS (ES): m/z 499.7 [M+H]⁺, $^1$H NMR (DMSO-$d_6$, 400 MHz): δ 10.27 (s, 1H), 9.07 (s, 1H), 8.74-8.73 (d, J=4.4 Hz, 1H), 8.21 (s, 1H), 8.02 (s, 1H), 7.91-7.90 (d, J=3.6 Hz, 1H), 6.54 (s, 1H), 5.23-5.20 (m, 2H), 4.47 (bs, 1H), 3.94 (s, 3H), 2.73-2.70 (m, 2H), 2.33 (bs, 2H), 1.34 (s, 9H).

Example 159: 1-methyl-2-((1-(3-morpholinopropyl)-2-oxo-5-(trifluoromethyl)-1,2-dihydropyridin-3-yl)amino)-6-(pyrazolo[1,5-a]pyridin-3-yloxy)-1H-imidazo[4,5-b]pyridine-7-carbonitrile Synthesis of I-159. Compound I-159 was prepared from 159.1, following the procedure described in the synthesis of I-157. The product was purified by preparative HPLC. MS (ES): m/z 594.3 [M+H]$^+$, $^1$H NMR (DMSO-d$_6$, 400 MHz):

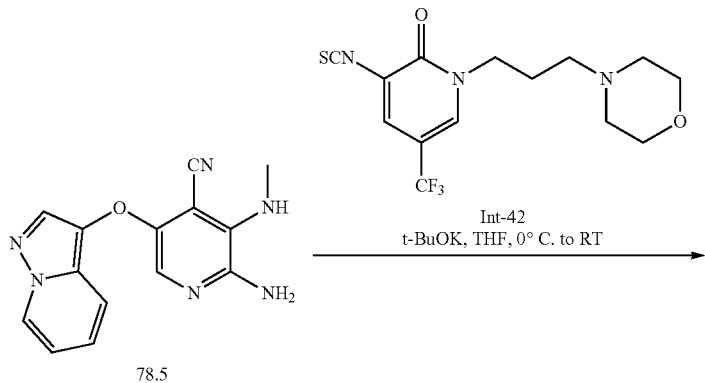

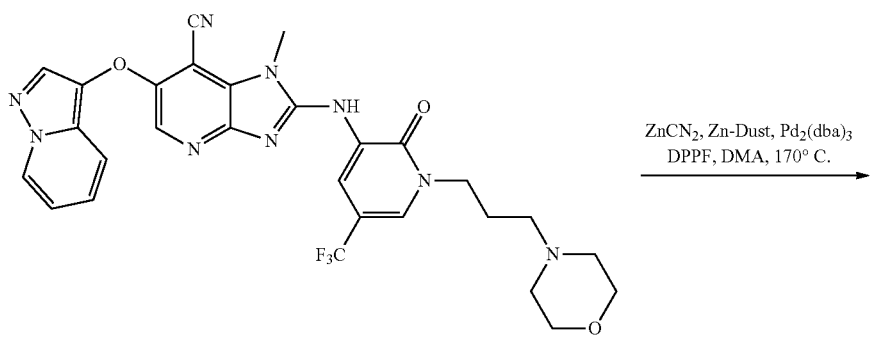

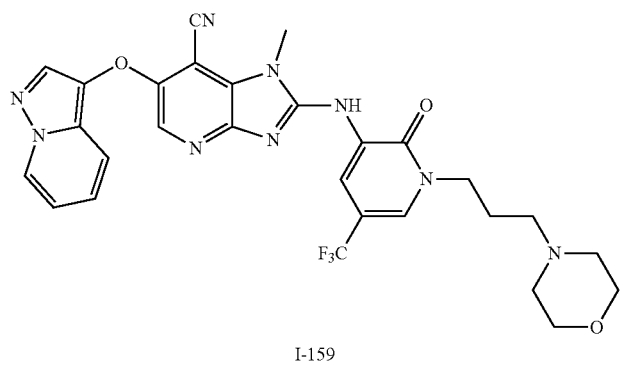

Synthesis of compound 159.1. Compound 159.1 was prepared from 78.5 and Int-42, following the procedure described in the synthesis of I-13. The product was purified by flash column chromatography on silica gel (Combi-Flash®, 3.0% methanol in DCM). MS (ES): m/z 603.2 [M]$^+$.

δ 8.69-8.68 (d, J=6.8 z, 1H), 8.61 (s, 1H), 8.36 (s, 1H), 8.19 (s, 1H), 8.13 (s, 1H), 7.95 (s, 1H), 7.56-7.54 (d, J=4.8 Hz, 1H), 7.26-7.22 (m, 1H), 6.97-6.93 (m, 1H), 4.15 (bs, 2H), 3.99 (s, 3H), 3.55 (bs, 4H), 2.33 (bs, 6H), 1.92 (bs, 2H).

Example 160: 2-((1-(2-hydroxyethyl)-2-oxo-5-(trifluoromethyl)-1,2-dihydropyridin-3-yl)amino)-1-methyl-6-(pyrazolo[1,5-a]pyridin-3-yloxy)-1H-imidazo[4,5-b]pyridine-7-carbonitrile the synthesis of I-157. The product was purified by flash column chromatography on silica gel (CombiFlash®, 1.8% methanol in DCM). MS (ES): m/z 601.2 [M+H]+.

Synthesis of I-160. Compound I-160 was prepared from 160.2, following the procedure described in the synthesis of

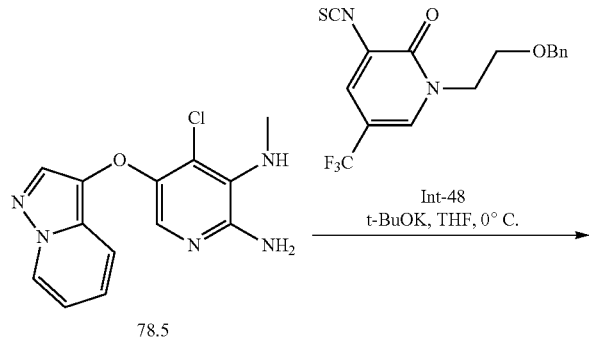

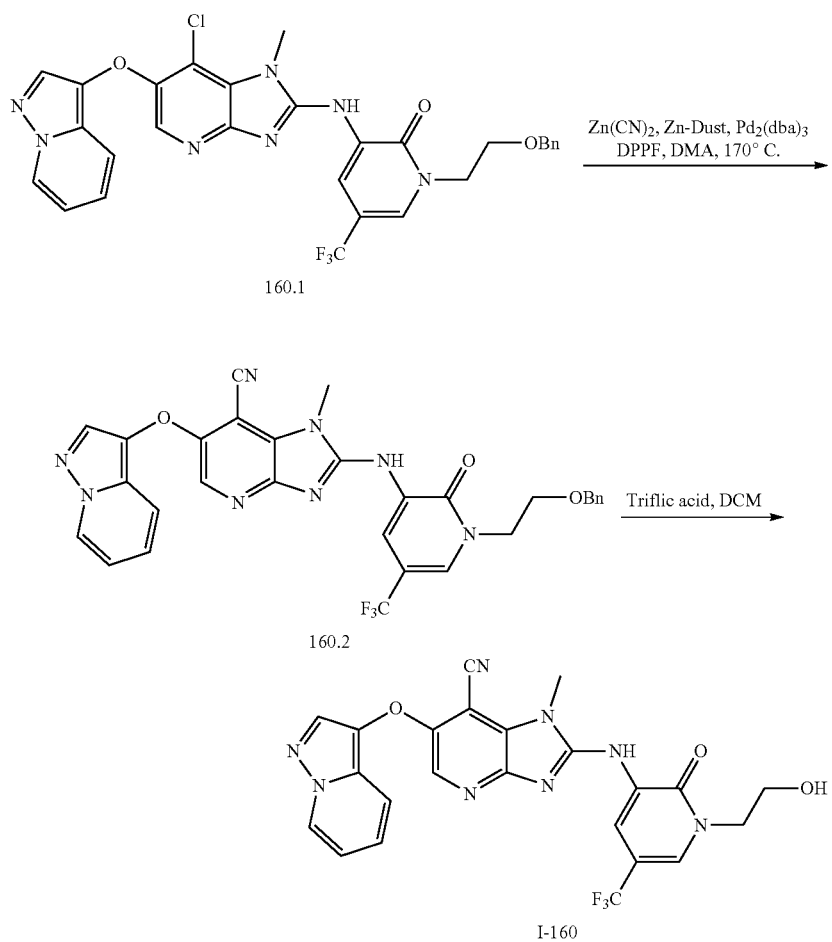

Synthesis of compound 160.1. Compound 160.1 was prepared from 78.5 and Int-48, following the procedure described in the synthesis of I-13. The product was purified by flash column chromatography on silica gel (CombiFlash®, 1.9% methanol in DCM. MS (ES): m/z 610.0 [M]+.

Synthesis of compound 160.2. Compound 160.2 was prepared from 160.1, following the procedure described in I-23. The product was purified by flash column chromatography on silica gel (CombiFlash®, 3.5% methanol in DCM). MS (ES): m/z 511.6 [M+H]+, $^1$H NMR (DMSO-$d_6$, 400 MHz): δ 8.99 (s, 1H), 8.70-8.68 (d, J=6.8 Hz, 1H), 8.63 (s, 1H), 8.19 (s, 1H), 8.00 (s, 1H), 7.97 (s, 1H), 7.56-7.54 (d, J=8.8 Hz, 1H), 7.26-7.23 (m, 1H), 6.97-6.94 (m, 1H), 5.00 (bs, 1H), 4.19 (bs, 2H), 4.00 (s, 3H), 3.75 (bs, 2H).

Example 161: 3-((7-chloro-6-((6-fluoropyrazolo[1,5-a]pyridin-3-yl)oxy)-1-methyl-1H-imidazo[4,5-b]pyridin-2-yl)amino)-1-(1-methyl-1H-pyrazol-4-yl)-5-(trifluoromethyl)pyridin-2(1H)-one

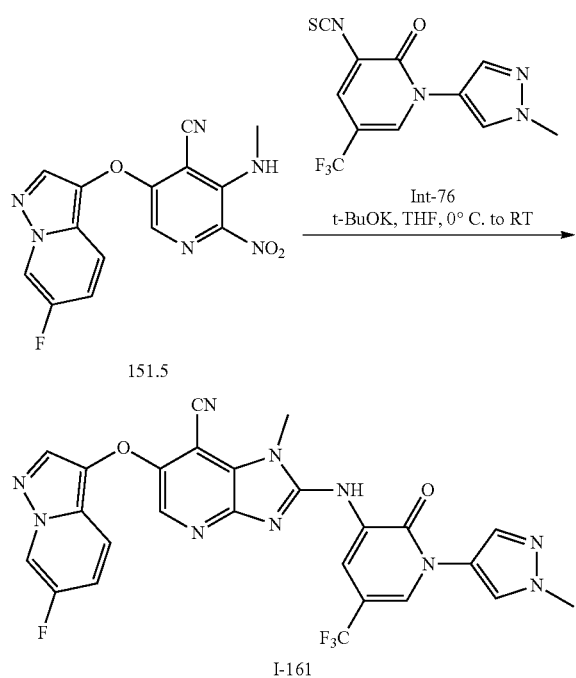

Synthesis of compound I-161. Compound 160.1 was prepared from 151.5 and Int-76, following the procedure described in the synthesis of I-13. The product was purified by flash column chromatography on silica gel (Combi-Flash®, 3.0% methanol in DCM). MS (ES): m/z 574.3 [M+H]$^+$. $^1$H NMR (DMSO-d$_6$, 400 MHz): δ 8.98 (s, 1H), 8.95 (s, 1H), 8.63 (s, 1H), 8.37 (s, 1H), 8.10-8.09 (d, J=6.0 Hz, 2H), 8.03 (s, 1H), 7.98 (s, 1H), 7.65-7.61 (m, 1H), 7.35-7.30 (m, 1H), 4.03 (s, 3H), 3.94 (s, 3H).

Example 162: cis-3-((7-chloro-6-((6-fluoropyrazolo[1,5-a]pyridin-3-yl)oxy)-1-methyl-1H-imidazo[4,5-b]pyridin-2-yl)amino)-1-(3-hydroxycyclobutyl)-5-(trifluoromethyl)pyridin-2(1H)-one

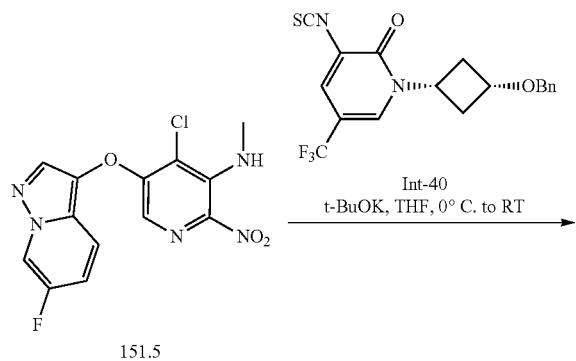

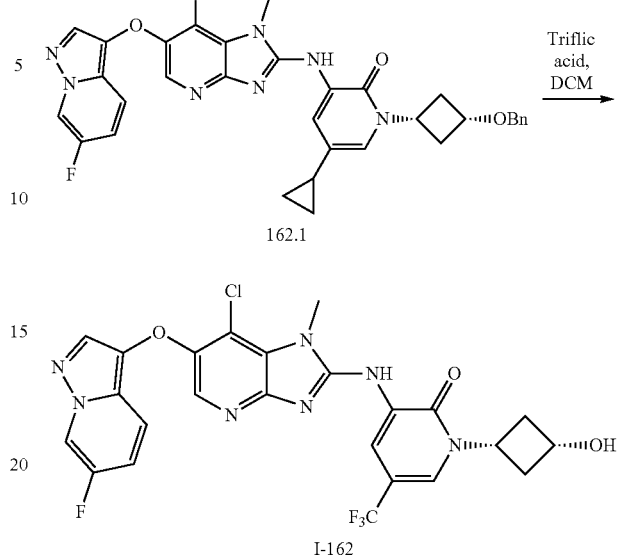

Synthesis of compound 162.1. Compound 162.1 was prepared from 151.5 and Int-40, following the procedure described in the synthesis of I-13. The product was purified by flash column chromatography on silica gel (Combi-Flash®, 2.0% methanol in DCM). MS (ES): m/z 654 [M+H]$^+$.

Synthesis of I-162. Compound I-162 was prepared from 162.1, following the procedure described in the synthesis of I-23. The product was purified by flash column chromatography on silica gel (CombiFlash®, 3.0% methanol in DCM). MS (ES): m/z 563.8 [M]$^+$, $^1$H NMR (DMSO-d$_6$, 400 MHz): δ 8.99-8.98 (d, J=7.2 Hz, 1H), 8.91 (bs, 1H), 8.59 (s, 1H), 8.09 (s, 1H), 8.02 (s, 1H), 7.92 (s, 1H), 7.64-7.61 (m, 1H), 7.35-7.30 (m, 1H), 4.66-4.62 (m, 1H), 4.02 (s, 3H), 3.42-3.36 (m, 1H), 2.84-2.82 (m, 2H), 2.41-2.34 (m, 1H), 2.21-2.19 (m, 2H).

Example 163: 3-((7-chloro-6-((6-fluoropyrazolo[1,5-a]pyridin-3-yl)oxy)-1-methyl-1H-imidazo[4,5-b]pyridin-2-yl)amino)-1-(2-hydroxyethyl)-5-(trifluoromethyl)pyridin-2(1H)-one

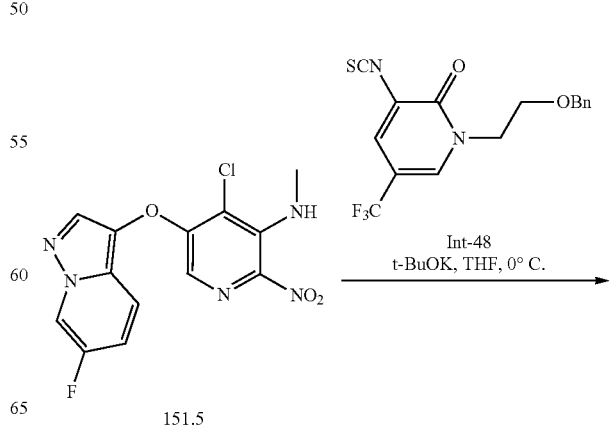

797
-continued

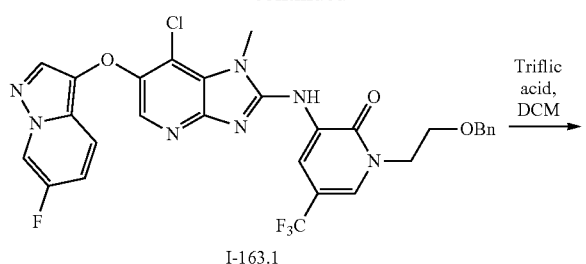
I-163.1

Triflic acid, DCM →

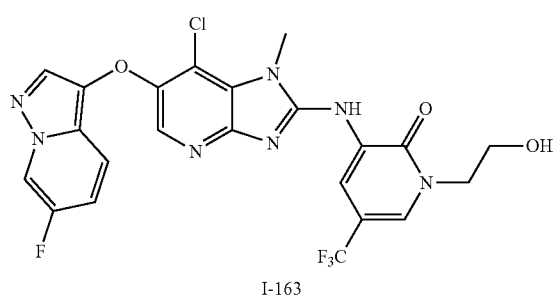
I-163

Synthesis of compound 163.1. Compound 163.1 was prepared from 151.5 and Int-48, following the procedure described in the synthesis of I-13. The product was purified by flash column chromatography on silica gel (CombiFlash®, 2.4% methanol in DCM). MS (ES): m/z 628.8 [M+H]+.

Synthesis of compound I-163. Compound I-163 was prepared from 163.1, following the procedure described in the synthesis of I-23. The product was purified by flash column chromatography on silica gel (CombiFlash®, 3.6% methanol in DCM). MS (ES): m/z 538.3 [M+H]+. 1H NMR (DMSO-d6, 400 MHz): δ 8.97 (bs, 1H), 8.82 (bs, 1H), 8.62 (s, 1H), 8.08 (s, 1H), 8.02 (s, 1H), 7.97 (s, 1H), 7.64-7.61 (m, 1H), 7.34-7.30 (m, 1H), 4.19 (bs, 2H), 4.02 (s, 3H), 3.74 (bs, 2H), 3.18 (bs, 1H).

Example 164: 2-(tert-butyl)-5-((7-chloro-1-methyl-6-(pyrazolo[1,5-a]pyrazin-3-yloxy)-1H-imidazo[4,5-b]pyridin-2-yl)amino)-3-ethylpyrimidin-4(3H)-one

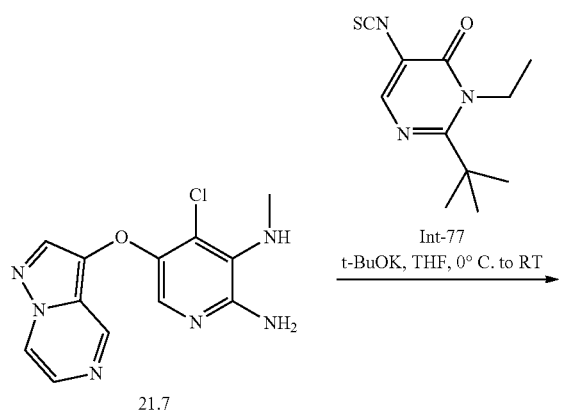
21.7

Int-77
t-BuOK, THF, 0° C. to RT →

798
-continued

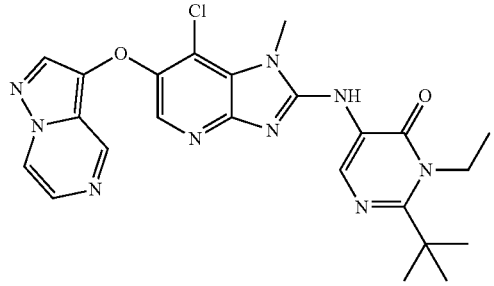
I-164

Synthesis of I-164. Compound I-164 was prepared from 21.7 and Int-77, following the procedure described in the synthesis of I-13. The product was purified by flash column chromatography on silica gel (CombiFlash®, 3.8% methanol in DCM). MS (ES): m/z 494.2 [M+H]+. 1H NMR (DMSO-d6, 400 MHz): δ 9.02 (s, 1H), 8.88 (s, 1H), 8.80 (s, 1H), 8.69-8.68 (d, J=4.4 Hz, 1H), 8.16 (s, 1H), 8.03 (s, 1H), 7.87-7.86 (d, J=4.8 Hz, 1H), 4.55 (m, 2H), 3.99 (s, 3H), 1.38 (s, 9H), 1.34 (bs, 3H).

Example 165: 5-((7-chloro-1-methyl-6-(pyrazolo[1,5-a]pyrazin-3-yloxy)-1H-imidazo[4,5-b]pyridin-2-yl)amino)-1-cyclopropyl-3-methylpyrimidine-2,4(1H,3H)-dione

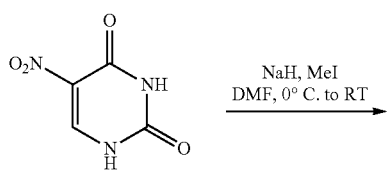

NaH, MeI
DMF, 0° C. to RT →

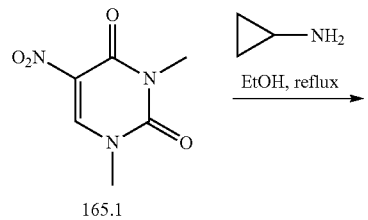
165.1

EtOH, reflux →

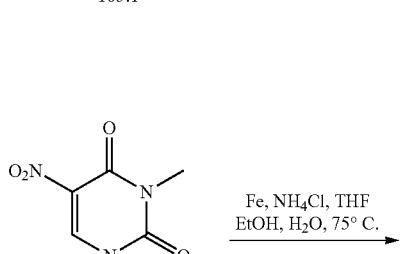
165.2

Fe, NH4Cl, THF
EtOH, H2O, 75° C.

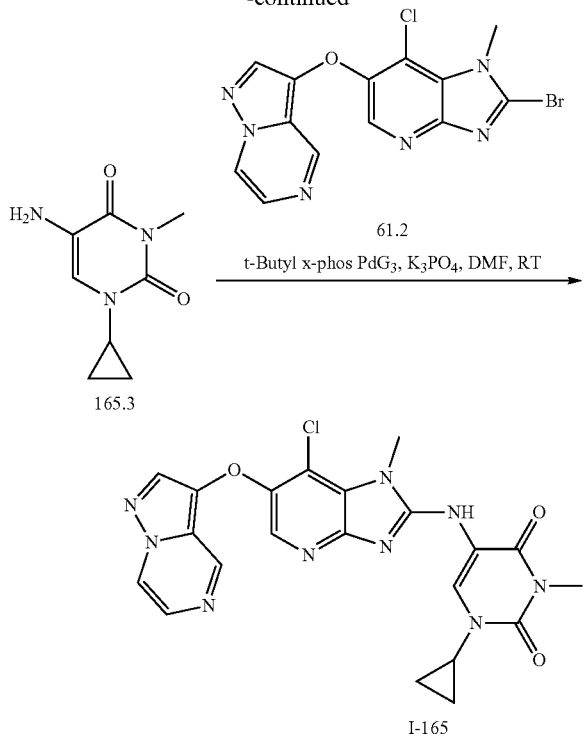

1H), 8.32 (s, 1H), 8.15 (s, 1H), 8.01 (s, 1H), 7.87-7.86 (d, J=4.8 Hz, 1H), 3.96 (s, 3H), 3.24 (s, 3H), 1.35 (bs, 1H), 1.02-1.01 (m, 2H), 0.88-0.85 (m, 2H).

Example 166: 3-((7-chloro-1-methyl-6-((5-morpholinopyrazolo[1,5-a]pyridin-3-yl)oxy)-1H-imidazo[4,5-b]pyridin-2-yl)amino)-1-methyl-5-(trifluoromethyl)pyridin-2(1H)-one

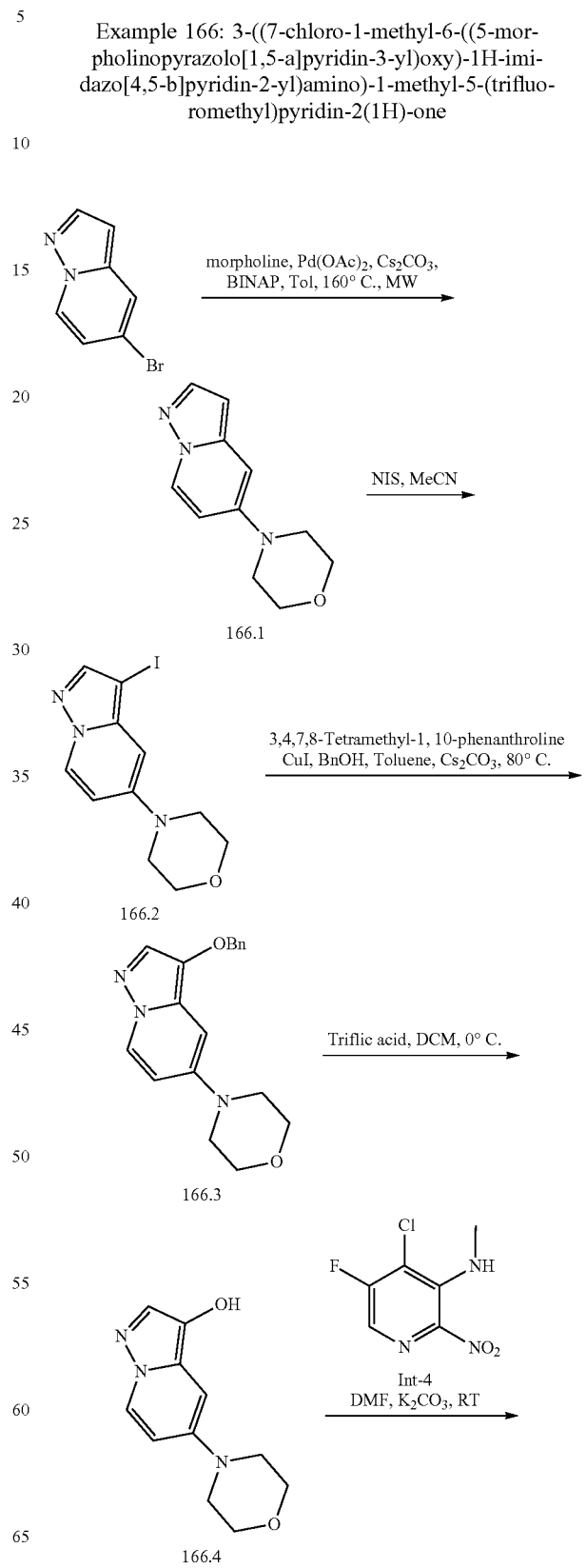

Synthesis of compound 165.1. To a solution of 5-nitropyrimidine-2,4(1H,3H)-dione (10 g, 63.66 mmol, 1.0 equiv) in DMF (20 mL) was added sodium hydride (6.36 g, 159.15 mmol, 2.5 equiv) at 0° C. The reaction mixture was stirred for 2 h. Iodomethane (26.9 g, 190.98 mmol, 3.0 equiv) was added and stirred at room temperature for 16 h. It was poured over ice-water and extracted with ethyl acetate. The combined organic layers were, dried over anhydrous sodium sulfate, filtered and concentrated under reduced pressure. The residue was purified by flash column chromatography on silica gel (CombiFlash®, 1.5% methanol in DCM) to afford 165.1. MS (ES): m/z 186.0 [M+H]$^+$.

Synthesis of compound 165.2. To a solution of 165.1 (5.0 g, 27.01 mmol, 1.0 equiv) and cyclopropanamine (23.9 g, 418.6 mmol, 15.5 equiv) in ethanol (50 mL) was heated to reflux for 48 h. It was concentrated under reduced pressure. The residue was purified by flash column chromatography on silica gel (CombiFlash®, 1.7% methanol in DCM) to afford 165.2. MS (ES): m/z 212.0 [M+H]$^+$.

Synthesis of compound 165.3. A mixture of 165.2 (0.500 g, 2.37 mmol, 1.0 equiv), iron powder (0.663 g, 11.85 mmol, 5.0 equiv) and ammonium chloride (0.063 g, 1.185 mmol, 0.5 equiv) in ethanol (4 mL), THF (4 mL) and water (3 mL) was stirred at 75° C. for 1 h. It was filtered and the filtrate was transferred into water and extracted with ethyl acetate. The combined organic layers were, dried over anhydrous sodium sulfate, filtered and concentrated under reduced pressure. The residue was purified by flash column chromatography on silica gel (CombiFlash®, 50% ethyl in hexane) to afford 165.3. MS (ES): m/z 182.1 [M+H]$^+$.

Synthesis of I-165. Compound I-165 was prepared from 165.3 and 61.2, following the procedure described in the synthesis of Int-45. was purified by flash column chromatography on silica gel (CombiFlash®, 2.8% methanol in DCM). MS (ES): m/z 479.8 [M]$^+$, $^1$H NMR (DMSO-d$_6$, 400 MHz): δ 9.01 (s, 1H), 8.69-8.68 (d, J=3.6 Hz, 1H), 8.53 (s, -continued

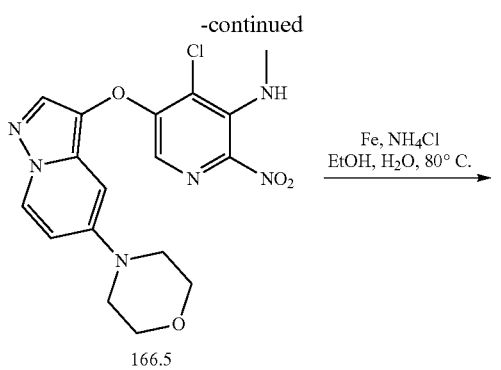

166.5

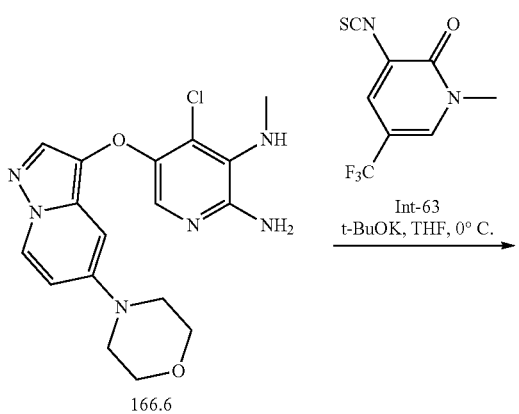

166.6

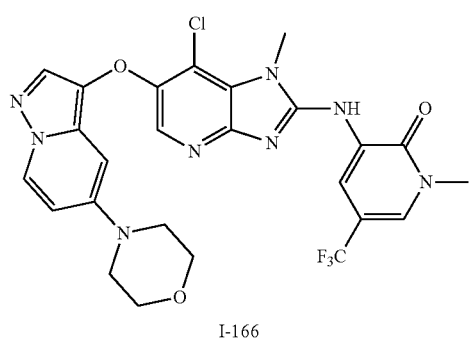

I-166

Synthesis of compound 166.1. A mixture of 5-bromopyrazolo[1,5-a]pyridine (1.5 g, 7.61 mmol, 1.0 equiv), palladium acetate (0.102 g, 0.456 mmol, 0.06 equiv), 2,2'-bis(diphenylphosphino)-1,1'-binaphthyl (0.473 g, 0.761 mmol, 0.1 equiv), cesium carbonate (3.70 g, 11.41 mmol, 1.5 equiv) in toluene (15 mL) was degassed by bubbling through a stream of argon for 5 min. Morpholine (1.32 g, 15.22 mmol, 2.0 equiv) was added and degassed for another 5 min. The reaction mixture was stirred at 160° C. for 30 min in a microwave reactor. It was poured over water and extracted with ethyl acetate. The combined organic layers were, dried over anhydrous sodium sulfate, filtered and concentrated under reduced pressure. The residue was purified by flash column chromatography on silica gel (CombiFlash®, 1% methanol in DCM) to afford 166.1. MS (ES): m/z 204.2 $[M]^+$.

Synthesis of compound 166.2. To a solution of 166.1 (1.2 g, 5.90 mmol, 1.0 equiv) in acetonitrile (30 mL) was added N-iodosuccinimide (1.50 g, 5.90 mmol, 1.0 equiv) at 0° C. and stirred for 5 min. It was poured over sodium thiosulphate solution and extracted with ethyl acetate. The combined organic layers were washed with brine, dried over anhydrous sodium sulfate, filtered and concentrated under reduced pressure. The residue was purified by flash column chromatography on silica gel (CombiFlash®, 0.8% methanol in DCM) to afford 166.2. MS (ES): m/z 330.1 $[M+H]^+$.

Synthesis of compound 166.3. A mixture of 166.2 (0.800 g, 2.43 mmol, 1.0 equiv), benzyl alcohol (0.656 g, 6.07 mmol, 2.5 equiv) and cesium carbonate (1.57 g, 4.86 mmol, 2.0 equiv) in toluene (20 mL) was degassed by bubbling through a stream of argon for 15 min. Copper iodide (0.023 g, 0.121 mmol, 0.05 equiv) and 3,4,7,8-tetramethyl-1,10-phenanthroline (0.057 g, 0.243 mmol, 0.1 equiv) were added. The reaction mixture was stirred at room temperature for 20 min and heated to 110° C. for 16 h. It was cooled to room temperature, poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.2% methanol in DCM) to afford 166.3. MS (ES): m/z 310.2 $[M+H]^+$.

Synthesis of compound 166.4. Compound 166.4 was prepared from 166.3, following the procedure described in the synthesis of I-23. The product was purified by flash column chromatography on silica gel (CombiFlash®, 1.8% methanol in DCM). MS (ES): m/z 220.2 $[M+H]^+$.

Synthesis of compound 166.5. Compound 166.5 was prepared from 166.4 and Int-4, following the procedure described in the synthesis of 19.1. The product was purified by flash column chromatography on silica gel (CombiFlash®, 1.5% methanol in DCM). MS (ES): m/z 405.5 $[M+H]^+$.

Synthesis of compound 166.6. Compound 166.6 was prepared from 166.5, following the procedure described in the synthesis of 5.4. The product was purified by flash column chromatography on silica gel (CombiFlash®, 2.5% methanol in DCM). MS (ES): m/z 375.5 $[M+H]^+$.

Synthesis of I-166. Compound I-166 was prepared from 166.6 and Int-63, following the procedure described in the synthesis of I-13. The product was purified by flash column chromatography on silica gel (CombiFlash®, 2.3% methanol in DCM). MS (ES): m/z 575.3 $[M+H]^+$, $^1$H NMR (DMSO-$d_6$, 400 MHz): δ 8.78 (s, 1H), 8.60-8.59 (d, J=2.0 Hz, 1H), 8.45-8.43 (d, J=8.0 Hz, 1H), 8.13 (bs, 1H), 7.93 (s, 1H), 7.90 (s, 1H), 6.87-6.84 (m, 1H), 6.54-6.53 (d, J=2.0 Hz, 1H), 4.02 (s, 3H), 3.74-3.72 (m, 4H), 3.66 (s, 3H), 3.19-3.18 (m, 4H).

Example 167: cis-2-((1-(3-hydroxycyclobutyl)-2-oxo-5-(trifluoromethyl)-1,2-dihydropyridin-3-yl)amino)-1-methyl-6-(pyrazolo[1,5-a]pyridin-3-yloxy)-1H-imidazo[4,5-b]pyridine-7-carbonitrile

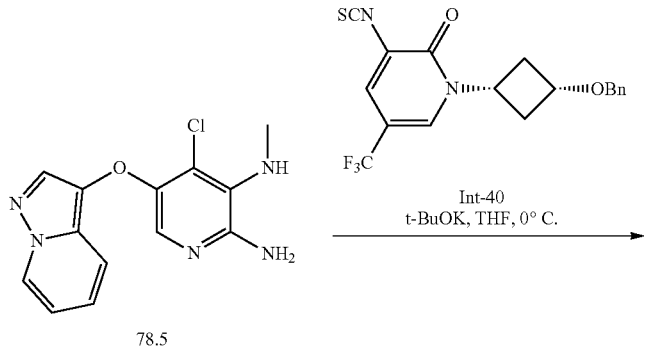

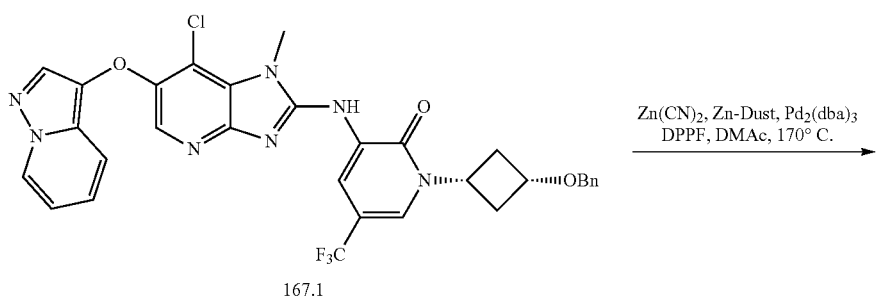

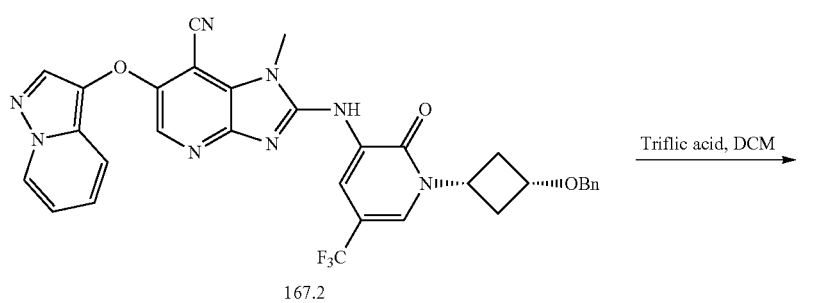

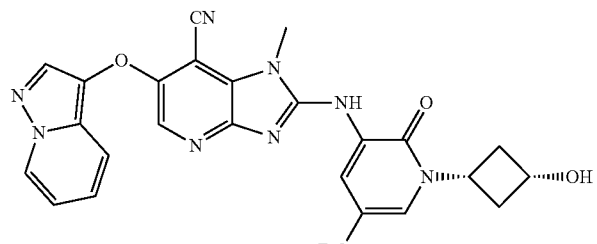

Synthesis of compound 167.1. Compound 167.1 was prepared from 78.5 and Int-40, following the procedure described in the synthesis of I-13. The product was purified by flash column chromatography on silica gel (CombiFlash®, 2.0% methanol in DCM). MS (ES): m/z 637.3 [M+H]⁺.

Synthesis of compound 167.2. Compound 167.2 was prepared from 167.1, following the procedure described in the synthesis of I-157. The product was purified by flash column chromatography on silica gel (CombiFlash®, 1.9% methanol in DCM). MS (ES): m/z 627.4 [M+H]⁺.

Synthesis of I-167. Compound I-167 was prepared from 167.2, following the procedure described in the synthesis of I-23. The product was purified by flash column chromatography on silica gel (CombiFlash®, 3.5% methanol in DCM). MS (ES): m/z 537.1 [M+H]⁺, ¹H NMR (DMSO-$d_6$, 400 MHz): δ 8.97 (s, 1H), 8.69-8.67 (d, J=6.8 Hz, 1H), 8.61 (s, 1H), 8.18 (s, 1H), 7.96 (s, 1H), 7.92 (s, 1H), 7.55-7.53 (d, J=8.8 Hz, 1H), 7.25-7.21 (m, 1H), 6.96-6.92 (m, 1H), 5.30-5.28 (m, 1H), 4.62-4.60 (m, 1H), 4.03 (bs, 1H), 3.99 (s, 3H), 2.83-2.82 (m, 2H), 2.20-2.18 (m, 2H).

Example 168: 2-((5-(tert-butyl)-1-(oxetan-3-yl)-1H-pyrazol-3-yl)amino)-1-methyl-6-(pyrazolo[1,5-a]pyrazin-3-yloxy)-1H-imidazo[4,5-b]pyridine-7-carbonitrile

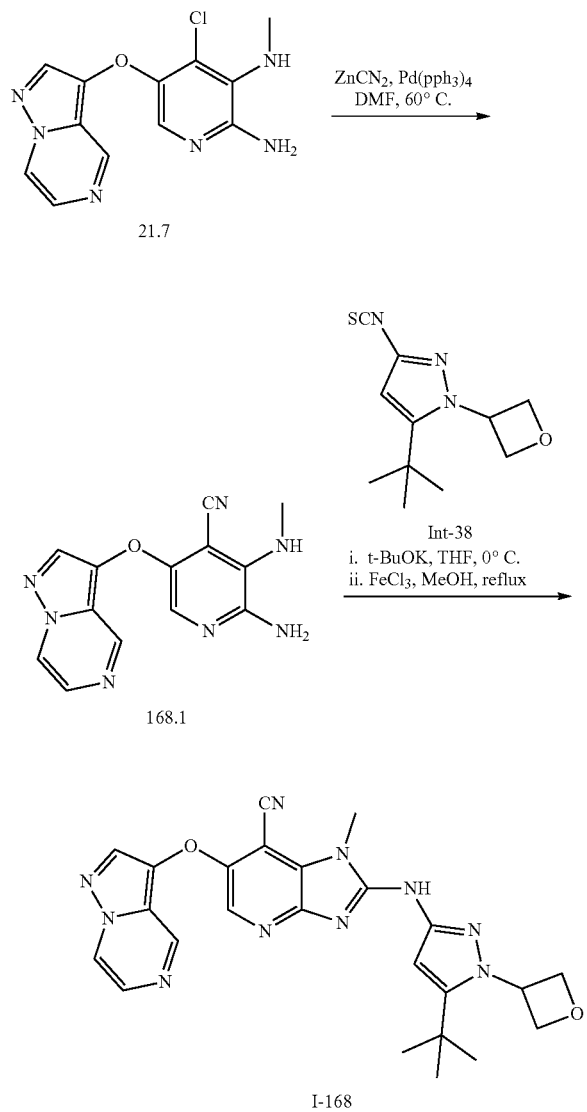

Synthesis of I-168. To a solution of 168.1 (0.070 g, 0.248 mmol, 1.0 equiv) and Int-38 (0.071 g, 0.298 mmol, 1.2 equiv) in THF (5 mL) was added potassium tert-butoxide (1 M in THF, 0.74 mL, 0.744 mmol, 3.0 equiv) at 0° C. The reaction mixture was stirred at room temperature for 2 h. It was concentrated under reduced pressure. The residue was dissolved in methanol (10 mL), and ferric chloride (0.120 g, 0.744 mmol, 3.0 equiv) was added. The reaction mixture was refluxed for 10 min. The reaction mixture was poured over ice-water and extracted with ethyl acetate. The combined organic layers were washed with brine, dried over anhydrous sodium sulfate, filtered and concentrated under reduced pressure. The residue was purified by preparative HPLC to afford I-168. MS (ES): m/z 484.9 [M+H]$^+$, $^1$H NMR (DMSO-d$_6$, 400 MHz): δ 9.05 (s, 1H), 8.72-8.71 (d, J=4.4 Hz, 1H), 8.16 (s, 1H), 7.89-7.88 (d, J=4.8 Hz, 1H), 7.84 (s, 1H), 7.60 (bs, 1H), 6.60 (s, 1H), 5.78-5.75 (m, 1H), 5.01-4.99 (m, 2H), 4.92-4.89 (m, 2H), 3.84 (s, 3H), 1.31 (s, 9H).

Example 169: (S)—N-(5-(tert-butyl)-1-(1-methylpyrrolidin-3-yl)-1H-pyrazol-3-yl)-7-chloro-6-((6-fluoropyrazolo[1,5-a]pyridin-3-yl)oxy)-1-methyl-1H-imidazo[4,5-b]pyridin-2-amine

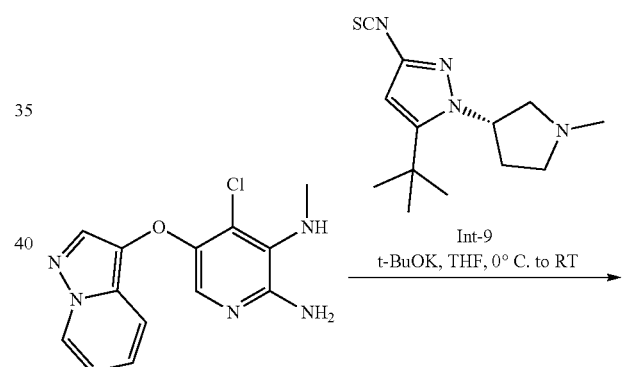

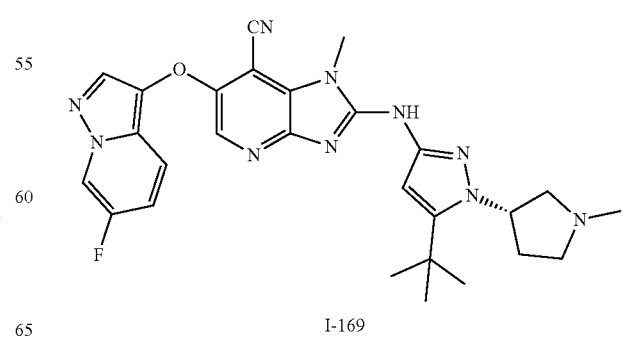

Synthesis of compound 168.1. A mixture of 21.7 (0.500 g, 1.72 mmol, 1.0 equiv) and zinc cyanide (0.402 g, 3.44 mmol, 2.0 equiv) in DMF (15 mL) was degassed by bubbling argon through for 10 min. Under argon atmosphere tetrakis(triphenylphosphine)palladium(0) (0.198 g, 0.172 mmol, 0.1 equiv) was added and degassed for another 5 min. The reaction mixture was stirred at 160° C. for 4 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.0% methanol in DCM) to afford 168.1. MS (ES): m/z 282.2 [M+H]$^+$.

Synthesis of I-169. Compound I-169 was prepared from 151.6 and Int-9, following the procedure described in the synthesis of I-13. The product was purified by flash column chromatography on silica gel (CombiFlash®, 2.6% methanol in DCM): m/z 538.3 [M+H]$^+$, $^1$H NMR (MeOD, 400 MHz): δ 8.58 (s, 1H), 7.93 (s, 1H), 7.82 (s, 1H), 7.62-7.58 (m, 1H), 7.25-7.21 (m, 1H), 6.42 (s, 1H), 5.38 (s, 1H), 4.05 (s, 3H), 3.43-3.39 (m, 3H), 3.12-3.10 (m, 1H), 2.81 (s, 3H), 2.58 (bs, 1H), 2.35-2.34 (m, 1H), 1.45 (s, 9H).

Example 170: ((R)—N-(5-(tert-butyl)-1-(1-methylpyrrolidin-3-yl)-1H-pyrazol-3-yl)-7-chloro-6-((6-fluoropyrazolo[1,5-a]pyridin-3-yl)oxy)-1-methyl-1H-imidazo[4,5-b]pyridin-2-amine

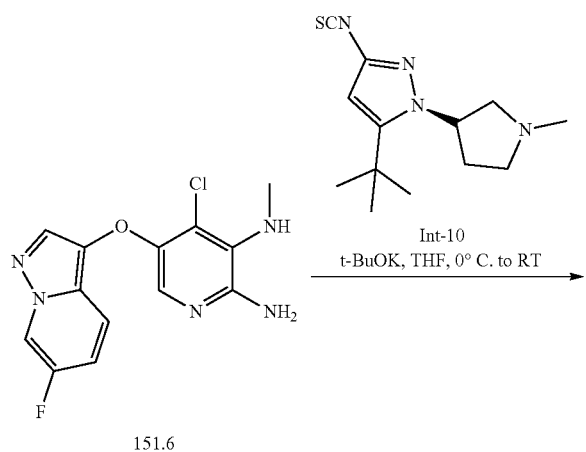

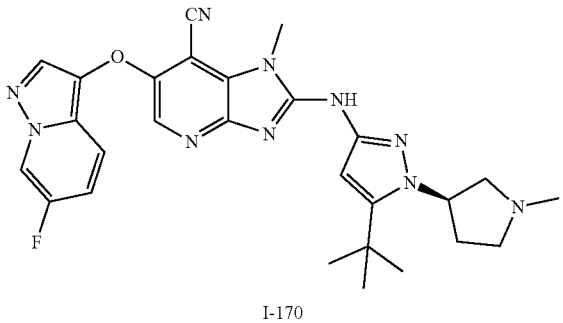

Synthesis of I-170. Compound I-170 was prepared from 151.6 and Int-10, following the procedure described in the synthesis of I-13. The product was purified by flash column chromatography on silica gel (CombiFlash®, 2.6% methanol in DCM) to afford I-170. MS (ES): m/z 538.3 [M+H]$^+$. $^1$H NMR (DMSO-d$_6$, 400 MHz): δ 9.97 (s, 1H), 8.97 (s, 1H), 7.98 (s, 1H), 7.97 (s, 1H), 7.62 (bs, 1H), 7.33-7.31 (m, 1H), 6.51 (s, 1H), 5.17 (s, 1H), 4.03 (bs, 4H), 3.17 (bs, 1H), 2.89 (bs, 3H), 2.35 (bs, 2H), 2.20 (bs, 1H), 2.01 (bs, 1H), 1.39 (s, 9H).

Example 171: 3-((7-chloro-1-methyl-6-((4-(methylamino)pyrazolo[1,5-a]pyrazin-3-yl)oxy)-1H-imidazo[4,5-b]pyridin-2-yl)amino)-1-(1-methyl-1H-pyrazol-4-yl)-5-(trifluoromethyl)pyridin-2(1H)-one

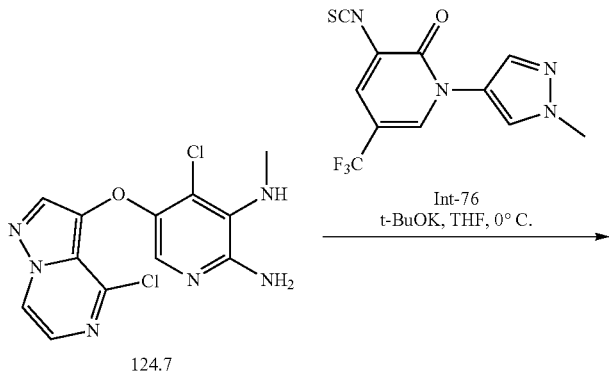

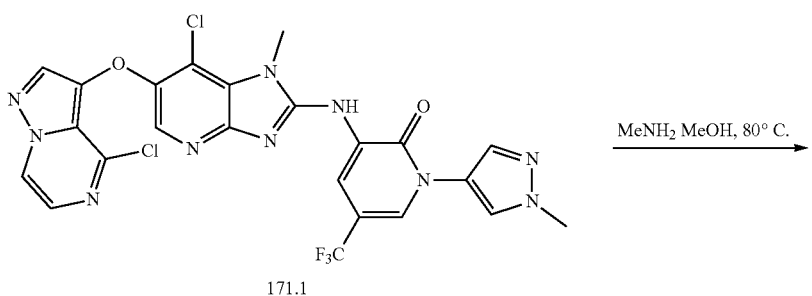

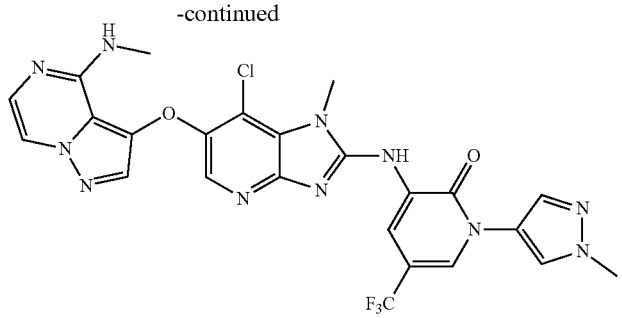

I-171

Synthesis of compound 171.1. Compound 171.1 was prepared from 124.7 and Int-76, following the procedure described in the synthesis of I-13. The product was purified by flash column chromatography on silica gel (CombiFlash®, 2.1% methanol in DCM). MS (ES): m/z 592.1 [M+H]+.

Synthesis of I-171. To a solution of 171.1 (0.045 g, 0.076 mmol, 1.0 equiv) in methanol (2.0 mL) was added methyl amine solution (2 M in THF, 0.4 mL) at room temperature and stirred at 80° C. for 12 h. It was concentrated under reduced pressure. The residue was purified by trituration with methanol to afford I-171. MS (ES): m/z 586.3 [M+H]+, $^1$H NMR (DMSO-$d_6$+TFA, 400 MHz): δ 9.24 (s, 1H), 8.53 (s, 1H), 8.41 (bs, 1H), 8.34 (bs, 1H), 8.15 (bs, 1H), 8.10 (s, 1H), 7.95 (s, 1H), 7.82 (s, 1H), 7.25 (s, 1H), 4.04 (s, 3H), 3.92 (s, 3H), 3.17 (s, 3H).

Example 172: 7-chloro-1-methyl-N-(3-(4-methylpiperazin-1-yl)-5-(trifluoromethyl)phenyl)-6-(pyrazolo[1,5-a]pyrazin-3-yloxy)-1H-imidazo[4,5-b]pyridin-2-amine

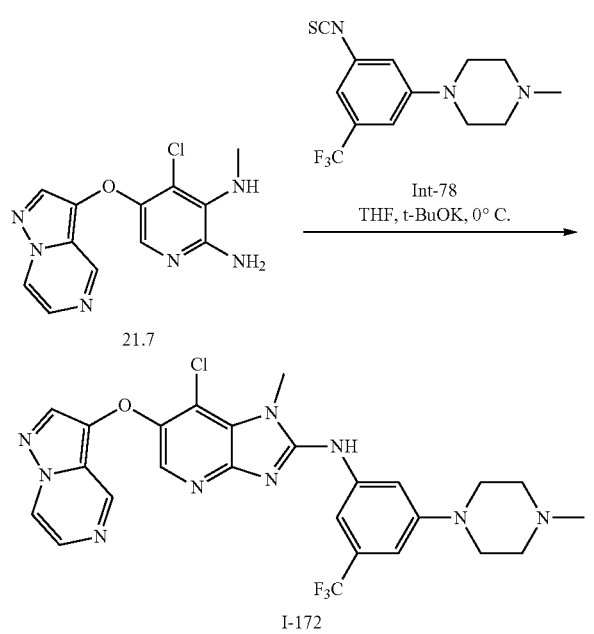

Synthesis of I-172. Compound I-172 was prepared from 21.7 and Int-78, following the procedure described in the synthesis of I-13. The product was purified by flash column chromatography on silica gel (CombiFlash®, 12% methanol in DCM). $^1$H NMR (DMSO-$d_6$, 400 MHz): δ 9.47 (s, 1H), 9.02 (s, 1H), 8.70-8.69 (d, J=3.6 Hz, 1H), 8.20 (s, 1H), 8.04 (s, 1H), 7.88-7.87 (d, J=4.8 Hz, 1H), 7.81 (s, 1H), 7.73 (bs, 1H), 6.90 (s, 1H), 4.02 (s, 3H), 3.25 (s, 4H), 2.26 (s. 3H), 1.24 (s, 4H).

Example 173: 7-chloro-N-(4-((4,4-difluoropiperidin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

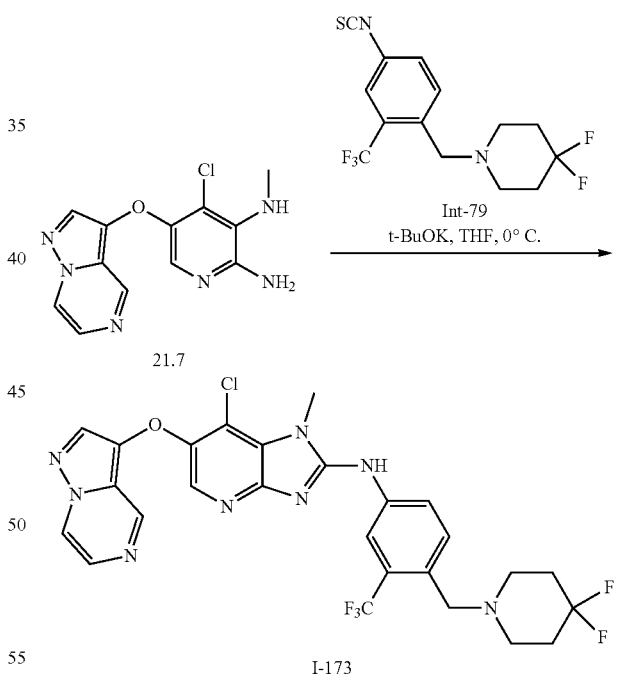

Synthesis of I-173. Compound I-173 was prepared from 21.7 and Int-79, following the procedure described in the synthesis of I-13. The product was purified by flash column chromatography on silica gel (CombiFlash®, 2.6% methanol in DCM). MS (ES): m/z 593.1 [M]+, $^1$H NMR (DMSO-$d_6$, 400 MHz): δ 9.66 (s, 1H), 9.03 (s, 1H), 8.71-8.69 (d, J=4.8 Hz, 1H), 8.30 (s, 1H), 8.21 (s, 1H), 8.18 (s, 1H), 8.04 (s, 1H), 7.88-7.87 (d, J=4.8 Hz, 1H), 7.78-7.76 (d, J=8.4 Hz, 1H), 4.03 (s, 3H), 3.67 (s, 2H), 2.45 (bs, 4H), 2.03-1.96 (m, 4H).

Example 174: 7-chloro-N-(4-((3,3-difluoropiperidin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

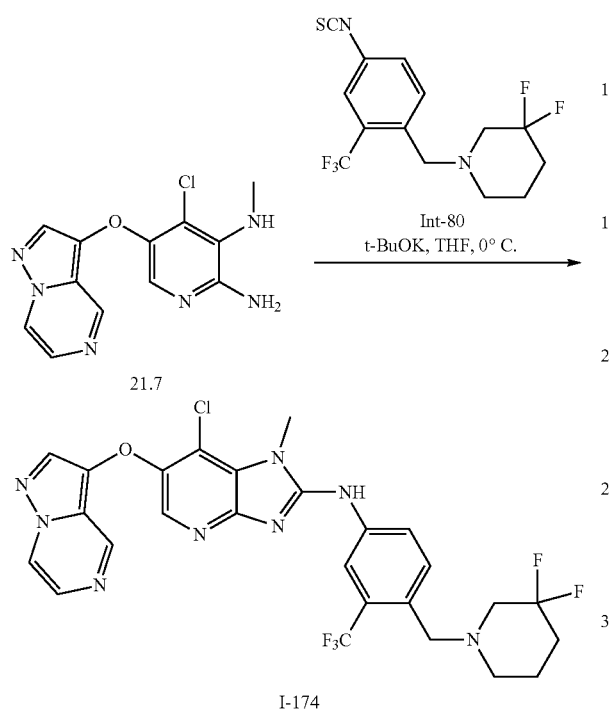

Synthesis of I-174. Compound I-174 was prepared from 21.7 and Int-80, following the procedure described in the synthesis of I-13. The product was purified by flash column chromatography on silica gel (CombiFlash®, 2.6% methanol in DCM). MS (ES): m/z 592.9 [M]+, ¹H NMR (DMSO-d₆, 400 MHz): δ 9.67 (s, 1H), 9.03 (s, 1H), 8.71-8.69 (d, J=4.8 Hz, 1H), 8.32 (s, 1H), 8.21 (s, 1H), 8.18-8.16 (d, J=8.4 Hz, 1H), 8.05 (s, 1H), 7.88-7.87 (d, J=4.8 Hz, 1H), 7.74-7.71 (d, J=8.8 Hz, 1H), 4.03 (s, 3H), 3.69 (s, 2H), 2.72-2.66 (m, 2H), 2.46-2.45 (m, 2H), 1.94-1.89 (m, 2H), 1.69 (bs, 2H).

Example 175: (S)-7-chloro-N-(4-((3-methoxypyrrolidin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

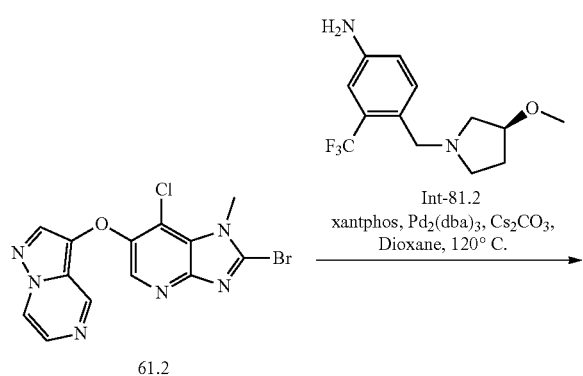

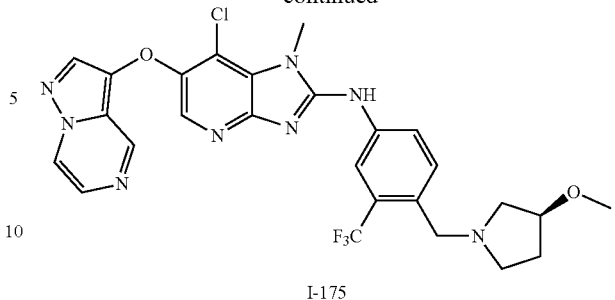

Synthesis of I-175. Compound I-175 was prepared from 61.2 and Int-81.2, following the procedure described in the synthesis of I-53. The product was purified by flash column chromatography on silica gel (CombiFlash®, 5.4% methanol in DCM). MS (ES): m/z 573.1 [M+H]+, ¹H NMR (DMSO-d₆, 400 MHz): δ 9.65 (s, 1H), 9.03 (s, 1H), 8.70-8.69 (d, J=4.0 Hz, 1H), 8.30 (s, 1H), 8.20 (s, 1H), 8.04 (s, 1H), 7.88-7.87 (d, J 4.8 Hz, 1H), 7.74-7.72 (d, J 7.6 Hz, 1H), 7.40 (s, 1H), 4.03 (s, 3H), 3.92 (bs, 1H), 3.71 (bs, 2H), 3.18 (s, 3H), 2.00 (bs, 2H), 1.71-1.66 (m, 2H), 1.12-1.08 (m, 2H).

Example 176: (R)-7-chloro-N-(4-((3-methoxypyrrolidin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

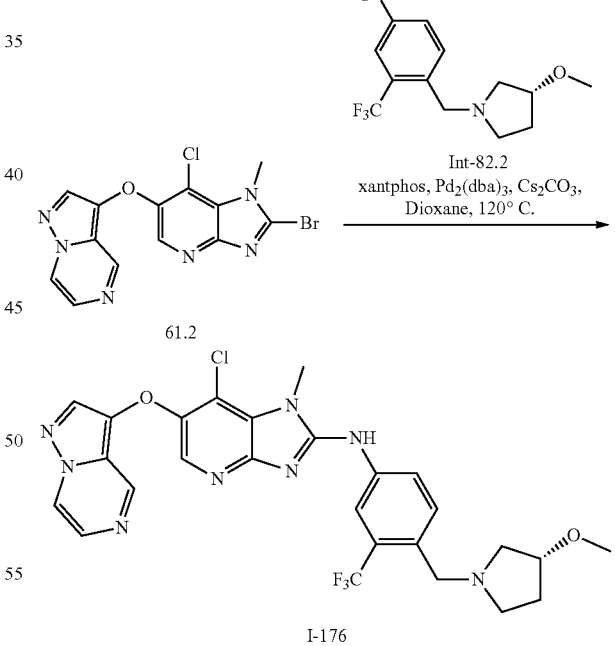

Synthesis of I-176. Compound I-176 was prepared from 61.2 and Int-82.2, following the procedure described in the synthesis of I-53. The product was purified by flash column chromatography on silica gel (CombiFlash®, 5.3% methanol in DCM). MS (ES): m/z 573.3 [M+H]+, ¹H NMR (DMSO-d₆, 400 MHz): δ 9.64 (s, 1H), 9.03 (s, 1H), 8.70-8.69 (d, J=4.0 Hz, 1H), 8.30 (s, 1H), 8.20 (s, 1H), 8.04 (s, 1H), 7.88-7.87 (d, J 4.8 Hz, 1H), 7.74-7.72 (d, J 7.6 Hz, 1H), 7.39 (s, 1H), 4.03 (s, 3H), 3.92 (bs, 1H), 3.71 (bs, 2H), 3.18 (s, 3H), 2.00 (bs, 2H), 1.71-1.66 (m, 2H), 1.12-1.08 (m, 2H).

Example 177: 3-((7-chloro-1-methyl-6-(pyrazolo[1,5-a]pyrazin-3-yloxy)-1H-imidazo[4,5-b]pyridin-2-yl)amino)-1-methyl-5-(trifluoromethyl)pyridin-2(1H)-one

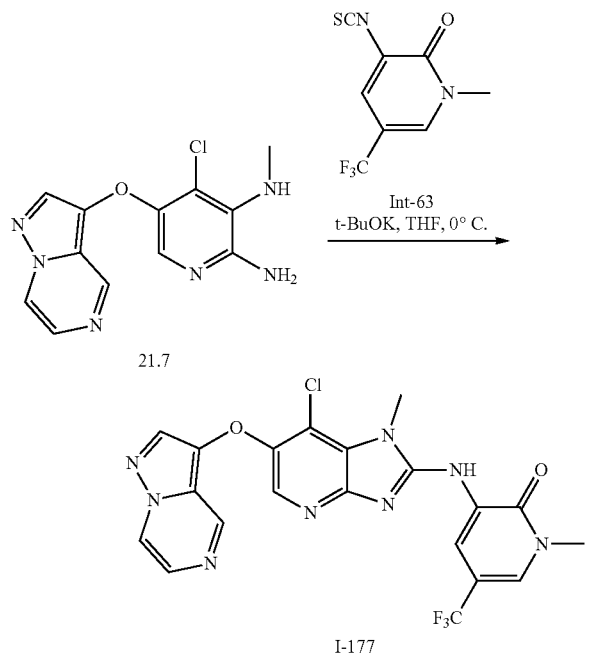

Synthesis of I-177. Compound I-177 was prepared from 21.7 and Int-63, following the procedure described in the synthesis of I-13. The product was purified by flash column chromatography on silica gel (CombiFlash®, 2.2% methanol in DCM). MS (ES): m/z 490.7 [M]$^+$, $^1$H NMR (DMSO-d$_6$, 400 MHz): δ 9.05 (s, 1H), 8.85 (s, 1H), 8.71-8.70 (d, J=4.8 Hz, 1H), 8.62-8.61 (d, J=2.0 Hz, 1H), 8.25 (s, 1H), 8.15 (s, 1H), 8.06 (s, 1H), 7.89-7.87 (d, J=4.8 Hz, 1H), 4.02 (s, 3H), 3.66 (s, 3H).

Example 178. 3-((7-chloro-1-methyl-6-((4-(methylamino)pyrazolo[1,5-a]pyrazin-3-yl)oxy)-1H-imidazo[4,5-b]pyridin-2-yl)amino)-1-cyclopropyl-5-(trifluoromethyl)pyridin-2(1H)-one

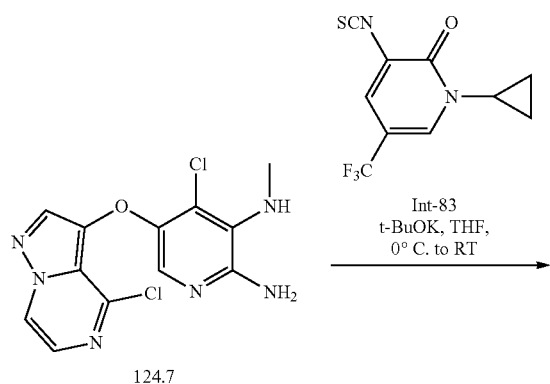

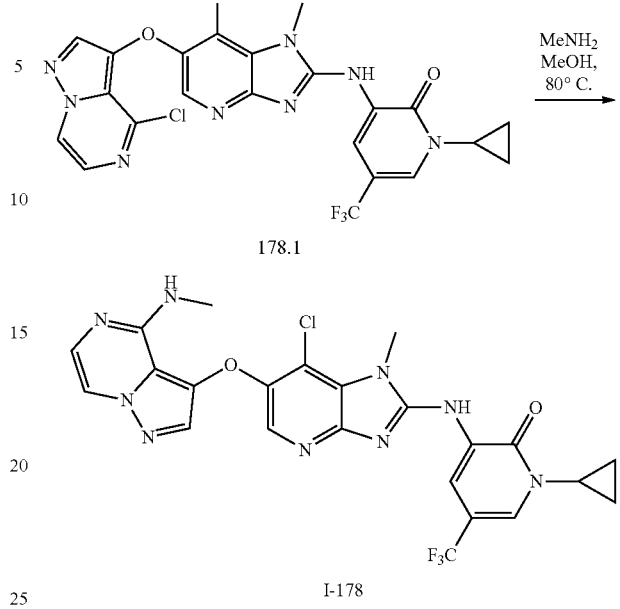

Synthesis of compound 178.1. Compound 178.1 was prepared from 124.7 and Int-83, following the procedure described in the synthesis of I-13. The product was purified by flash column chromatography on silica gel (CombiFlash®, 2.6% methanol in DCM). MS (ES): m/z 552.1 [M+H]$^+$.

Synthesis of I-178. Compound I-178 was prepared from 178.1, following the procedure described in the synthesis of I-171. The product was purified by flash column chromatography on silica gel (CombiFlash®, 3.9% methanol in DCM). MS (ES): m/z 546.1 [M+H]$^+$, $^1$H NMR (DMSO-d$_6$, 400 MHz): δ 8.90 (s, 1H), 8.67-8.66 (d, J=4.0 Hz, 1H), 8.25 (s, 1H), 8.10 (s, 1H), 7.80-7.78 (d, J=8.0 Hz, 1H), 7.51 (s, 1H), 7.27-7.26 (d, J=8.0 Hz, 1H), 6.86-6.84 (m, 1H), 4.02 (s, 3H), 3.00-2.99 (d, 3H), 2.57 (bs, 1H), 1.25 (bs, 4H).

Example 179: 3-((7-chloro-1-methyl-6-((4-(methylamino)pyrazolo[1,5-a]pyrazin-3-yl)oxy)-1H-imidazo[4,5-b]pyridin-2-yl)amino)-5-(trifluoromethyl)-2H-[1,3'-bipyridin]-2-one

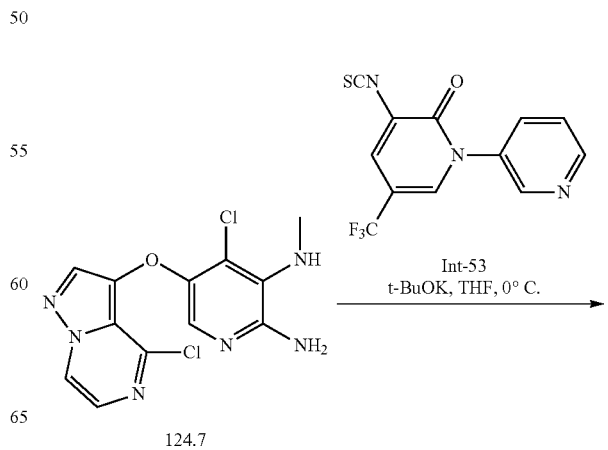

815

-continued

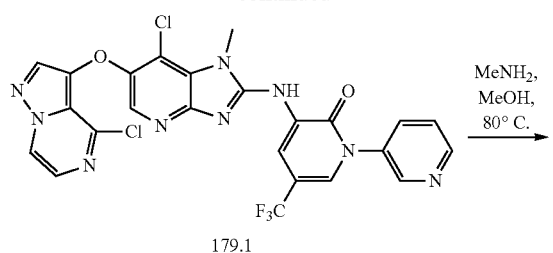

179.1

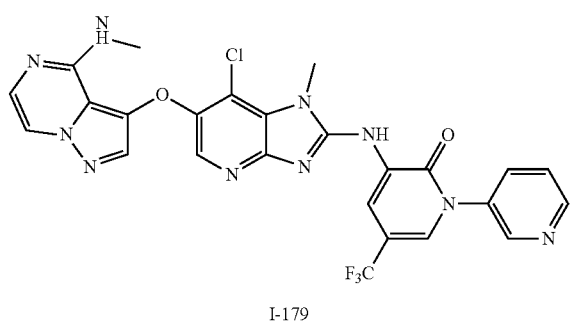

I-179

Synthesis of compound 179.1. Compound 179.1 was prepared from 124.7 and Int-53, following the procedure described in the synthesis of I-13. The product was purified by flash column chromatography on silica gel (CombiFlash®, 2.3% methanol in DCM). MS (ES): m/z 589.3 [M+H]⁺.

Synthesis of I-179. Compound I-179 was prepared from 179.1, following the procedure described in the synthesis of I-171. The product was purified by flash column chromatography on silica gel (CombiFlash®, 3.5% methanol in DCM). MS (ES): m/z 583.4 [M+H]⁺, ¹H NMR (DMSO-d₆, 400 MHz): δ 9.01 (s, 1H), 8.81 (s, 1H), 8.72 (s, 1H), 8.26-8.25 (d, J=6.0 Hz, 1H), 8.15 (s, 1H), 8.08 (s, 1H), 7.79-7.78 (d, J=4.8 Hz, 1H), 7.66-7.64 (d, J=7.6 Hz, 1H), 7.51-7.50 (d, J=5.6 Hz, 1H), 7.26-7.25 (d, J=5.2 Hz, 1H), 6.85 (s, 1H), 5.77-5.75 (m, 1H), 4.01-3.99 (s, 3H), 2.99-2.98 (d, 3H).

Example 180: 7-chloro-1-methyl-N-(3-(4-methyl-1H-imidazol-1-yl)-5-(trifluoromethyl)phenyl)-6-(pyrazolo[1,5-a]pyrazin-3-yloxy)-1H-imidazo[4,5-b]pyridin-2-amine

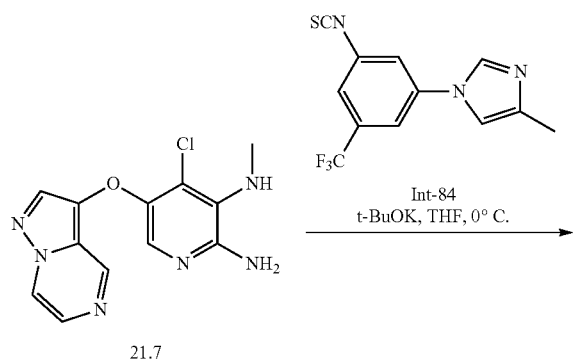

21.7

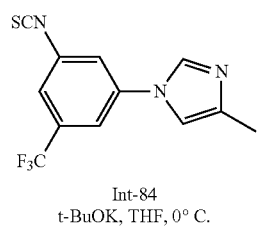

Int-84
t-BuOK, THF, 0° C.

816

-continued

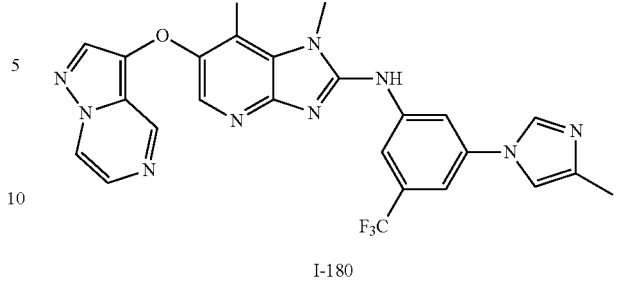

I-180

Synthesis of I-180. Compound I-180 was prepared from 21.7 and Int-84, following the procedure described in the synthesis of I-13. The product was purified by flash column chromatography on silica gel (CombiFlash®, 4% methanol in DCM). MS (ES): m/z 539.9 [M]⁺, ¹H NMR (DMSO-d₆, 400 MHz): δ 9.03 (s, 1H), 8.71-8.70 (d, J=3.6 Hz, 1H), 8.39 (s, 1H), 8.30 (s, 1H), 8.27-8.22 (m, 3H), 8.05 (s, 1H), 7.89-7.88 (d, J=4.8 Hz, 1H), 7.65 (s, 1H), 7.49 (s, 1H), 4.06 (s, 3H), 2.21 (s, 3H).

Example 181: (S)-7-chloro-N-(3-((3-methoxypyrrolidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

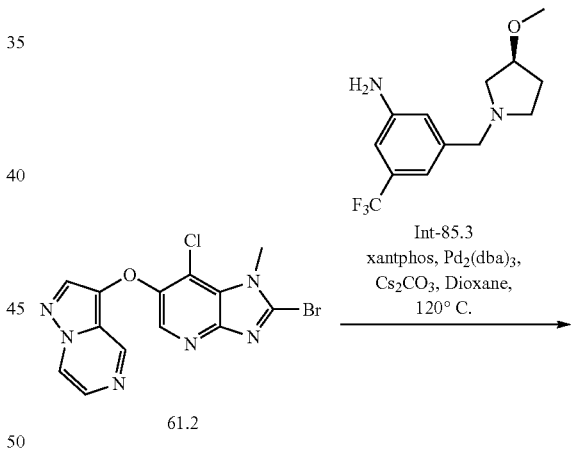

61.2

Int-85.3
xantphos, Pd₂(dba)₃, Cs₂CO₃, Dioxane, 120° C.

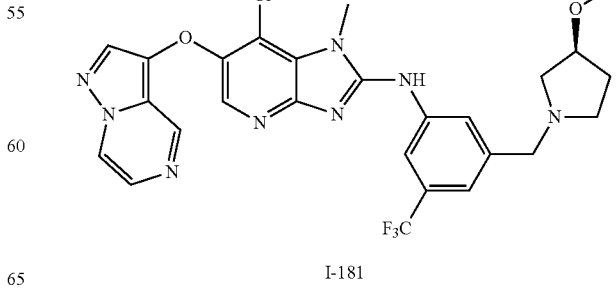

I-181

Synthesis of I-181. Compound I-181 was prepared from 61.2 and Int-85.3, following the procedure described in the synthesis of I-53. The product was purified by flash column chromatography on silica gel (CombiFlash®, 4.5% methanol in DCM. MS (ES): m/z 573.7 [M+H]⁺. ¹H NMR (DMSO-d₆, 400 MHz): δ 9.69 (s, 1H), 9.03-9.02 (d, J=6.8 Hz, 1H), 8.70 (s, 1H), 8.35 (s, 1H), 8.21-8.20 (d, J=7.2 Hz, 1H), 8.05-8.03 (d, J=7.2 Hz, 2H), 7.88-7.86 (m, 1H), 7.30 (s, 1H), 4.02 (s, 3H), 3.91 (bs, 1H), 3.68 (bs, 2H), 3.16 (s, 3H), 2.68 (bs, 2H), 2.34 (bs, 2H), 2.00 (bs, 1H), 1.69 (bs, 1H).

Example 182: (R)-7-chloro-N-(3-((3-methoxypyrrolidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

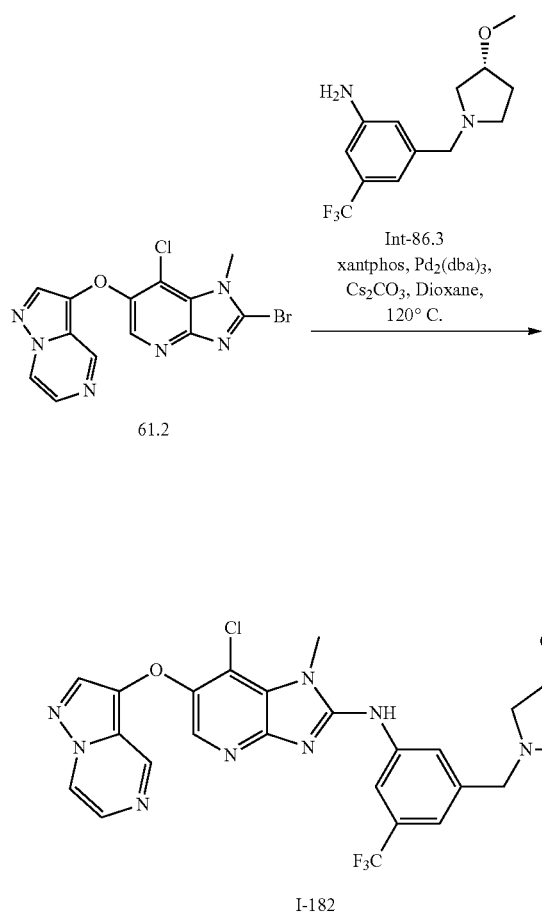

Synthesis of compound I-182. Compound I-182 was prepared from 61.2 and Int-86.3, following the procedure described in the synthesis of I-53. The product was purified by flash column chromatography on silica gel (CombiFlash®, 4.5% methanol in DCM. MS (ES): m/z 573.1 [M+H]⁺, ¹H NMR (DMSO-d₆, 400 MHz): δ 9.68 (s, 1H), 9.02 (bs, 1H), 8.70-8.68 (d, J=4.8 Hz, 1H), 8.34 (s, 1H), 8.20 (s, 1H), 8.05-8.04 (d, J=7.6 Hz, 2H), 7.87-7.86 (d, J=4.8 Hz, 1H), 7.28 (s, 1H), 4.02 (s, 3H), 3.91 (bs, 1H), 3.67 (bs, 2H), 3.16 (s, 3H), 2.67 (bs, 2H), 2.33 (bs, 2H), 2.00 (bs, 1H), 1.69 (bs, 1H).

Example 183: 3-((7-chloro-1-methyl-6-((5-morpholinopyrazolo[1,5-a]pyridin-3-yl)oxy)-1H-imidazo[4,5-b]pyridin-2-yl)amino)-1-(2-hydroxyethyl)-5-(trifluoromethyl)pyridin-2(1H)-one

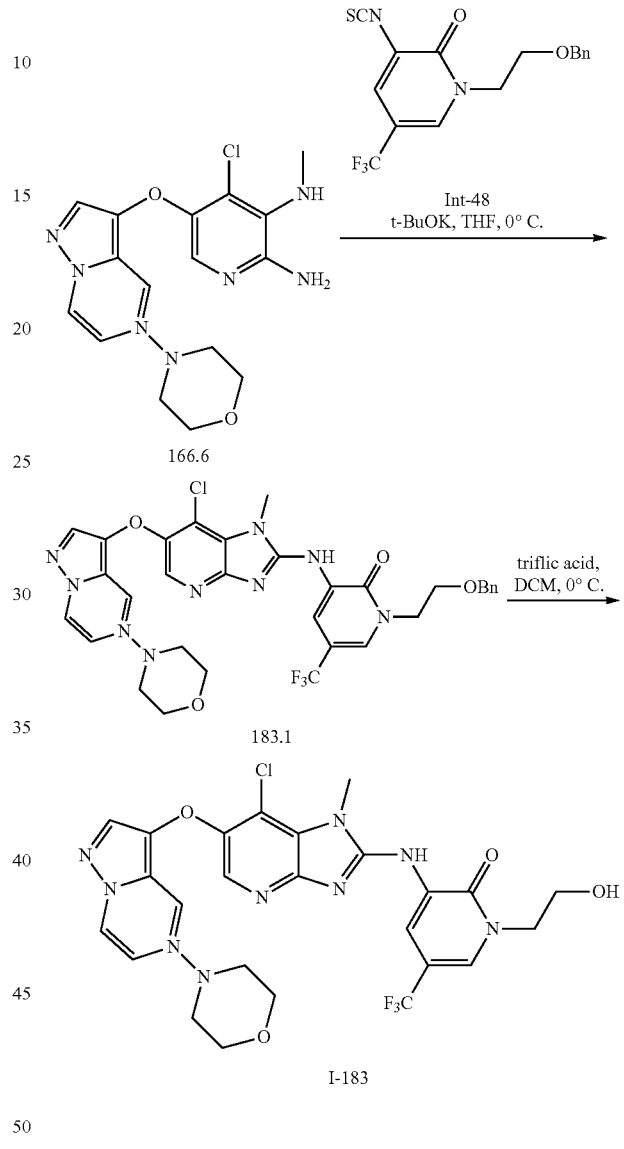

Synthesis of compound 183.1. Compound 183.1 was prepared from 166.6 and Int-48, following the procedure described in the synthesis of I-13. The product was purified by flash column chromatography on silica gel (CombiFlash®, 2.4% methanol in DCM). MS (ES): m/z 695.8 [M+H]⁺.

Synthesis of I-183. Compound I-183 was prepared from 183.1, following the procedure described in the synthesis of I-23. The product was purified by flash column chromatography on silica gel (CombiFlash®, 4.4% methanol in DCM). MS (ES): m/z 605.1 [M+H]⁺, ¹H NMR (DMSO-d₆, 400 MHz): δ 8.54 (s, 1H), 8.37-8.35 (d, J=7.6 Hz, 1H), 7.98 (s, 1H), 7.93 (s, 1H), 7.83 (s, 1H), 6.80-6.78 (d, J=5.6 Hz, 1H), 6.53 (s, 1H), 4.20-4.18 (m, 2H), 4.04 (s, 3H), 3.78-3.74 (m, 6H), 3.43-3.38 (m, 2H), 3.19 (bs, 4H).

Example 184: 7-chloro-6-((4-chloropyrazolo[1,5-a]pyrazin-3-yl)oxy)-N-(4-((3,3-difluoropyrrolidin-1-yl)methyl)-3-(trifluoromethyl)phenyl)-1-methyl-1H-imidazo[4,5-b]pyridin-2-amine

Example 185: (S)-1-(4-((7-chloro-1-methyl-6-(pyrazolo[1,5-a]pyrazin-3-yloxy)-1H-imidazo[4,5-b]pyridin-2-yl)amino)-2-(trifluoromethyl)benzyl)pyrrolidin-3-ol

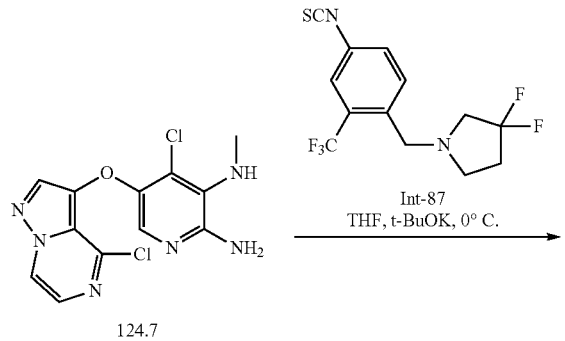

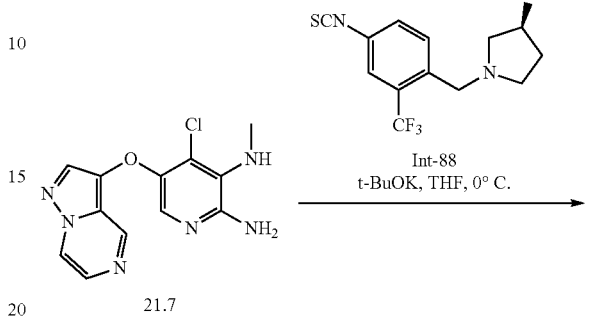

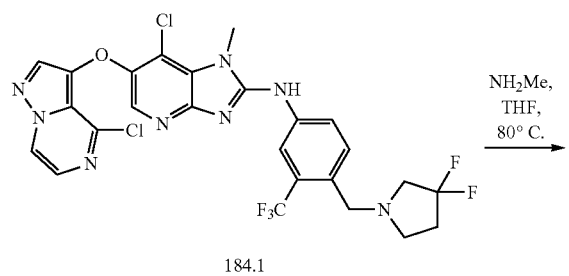

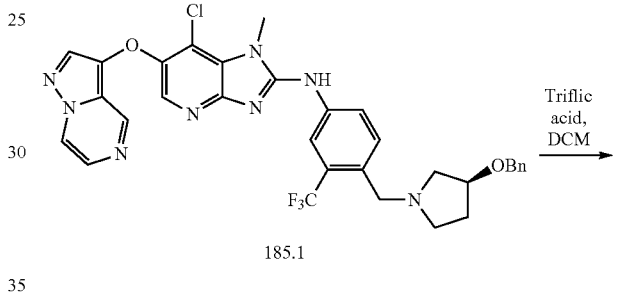

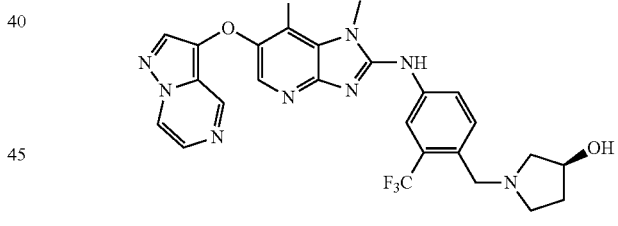

Synthesis of compound 184.1. Compound 184.1 was prepared from 124.7 and Int-87, following the procedure described in the synthesis of I-13. The product was purified by flash column chromatography on silica gel (CombiFlash®, 2.6% methanol in DCM). MS (ES): m/z 614.2 [M+H]+.

Synthesis of I-184. Compound I-184 was prepared from 184.1, following the procedure described in the synthesis of I-171. The product was purified by flash column chromatography on silica gel (CombiFlash®, 3.9% methanol in DCM). MS (ES): m/z 608.3 [M+H]+, $^1$H NMR (DMSO-d$_6$, 400 MHz): δ 9.73 (s, 1H), 8.32 (s, 1H), 8.18-8.17 (d, J=4.8 Hz, 2H), 7.77 (s, 1H), 7.70 (s, 1H), 7.47-7.45 (d, J=4.8 Hz, 1H), 7.25-7.23 (m, 1H), 6.82 (bs, 1H), 4.02-4.01 (bs, 3H), 3.75 (s, 2H), 2.98 (s, 3H), 2.93-2.89 (m, 2H), 2.75-2.74 (m, 2H), 2.32-2.27 (m, 2H).

Synthesis of compound 185.1. Compound 185.1 was prepared from 21.7 and Int-88, following the procedure described in the synthesis of I-13. The product was purified by flash column chromatography on silica gel (CombiFlash®, 4.4% methanol in DCM). MS (ES): m/z 649.8 [M+H]+.

Synthesis of I-185. Compound I-185 was prepared from 185.1, following the procedure described in the synthesis of I-23. The product was purified by flash column chromatography on silica gel (CombiFlash®, 9.0% methanol in DCM). MS (ES): m/z 559.2 [M+H]+, $^1$H NMR (DMSO-d$_6$, 400 MHz): δ 9.64 (s, 1H), 9.01 (s, 1H), 8.68-8.67 (d, J=4.4 Hz, 1H), 8.29 (s, 1H), 8.19 (bs, 2H), 8.02 (s, 1H), 7.86-7.85 (d, J=4.8 Hz, 1H), 7.76 (s, 1H), 4.74 (bs, 1H), 4.24 (bs, 1H), 4.01 (s, 3H), 3.70 (bs, 2H), 2.33 (bs, 2H), 2.19 (bs, 2H), 1.60 (bs, 2H).

Example 186: (R)-1-(4-((7-chloro-1-methyl-6-(pyrazolo[1,5-a]pyrazin-3-yloxy)-1H-imidazo[4,5-b]pyridin-2-yl)amino)-2-(trifluoromethyl)benzyl)pyrrolidin-3-ol Example 187: 2-((5-(tert-butyl)-1-(2-oxaspiro[3.3]heptan-6-yl)-1H-pyrazol-3-yl)amino)-1-methyl-6-(pyrazolo[1,5-a]pyrazin-3-yloxy)-1H-imidazo[4,5-b]pyridine-7-carbonitrile

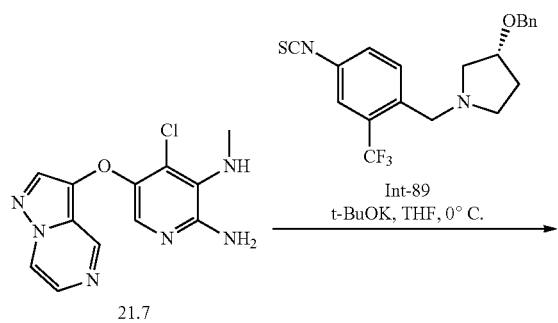

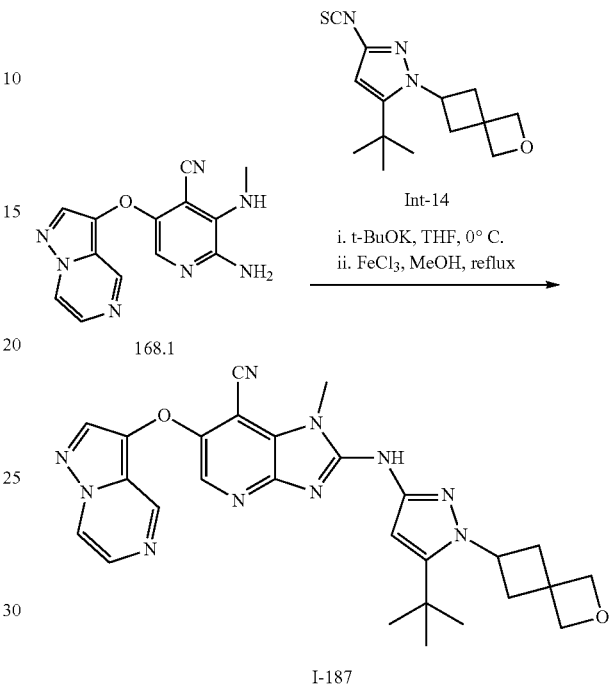

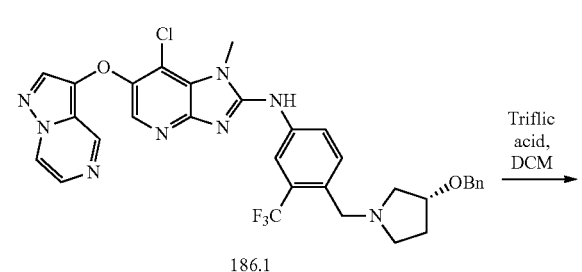

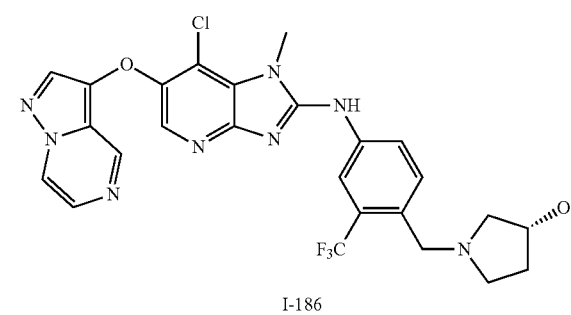

Synthesis of compound 186.1. Compound 186.1 was prepared from 21.7 and Int-89, following the procedure described in the synthesis of I-13. The product was purified by flash column chromatography on silica gel (CombiFlash®, 4.4% methanol in DCM). MS (ES): m/z 649.5 [M+H]⁺.

Synthesis of I-186. Compound I-186 was prepared from 186.1, following the procedure described in the synthesis of I-23. The product was purified by flash column chromatography on silica gel (CombiFlash®, 9.0% methanol in DCM). MS (ES): m/z 559.2 [M+H]⁺, ¹H NMR (DMSO-d₆, 400 MHz): δ 9.65 (s, 1H), 9.03 (s, 1H), 8.70-8.69 (d, J=4.0 Hz, 1H), 8.31 (s, 1H), 8.21 (bs, 2H), 8.04 (s, 1H), 7.88-7.87 (d, J=4.0 Hz, 1H), 7.78 (bs, 1H), 4.75 (bs, 1H), 4.25 (bs, 1H), 4.03 (s, 3H), 3.71 (bs, 2H), 2.33 (bs, 2H), 2.04 (bs, 2H), 1.60 (bs, 2H).

Synthesis of I-187. Compound I-187 was prepared from 168.1 and Int-14, following the procedure described in the synthesis of I-168. The product was purified by flash column chromatography on silica gel (CombiFlash®, 3.2% methanol in DCM). MS (ES): m/z 524.5 [M]⁺, ¹H NMR (DMSO-d₆, 400 MHz): δ 9.08 (s, 1H), 8.73-8.72 (d, J=3.6 Hz, 1H), 8.18 (s, 1H), 7.90-7.89 (d, J=4.0 Hz, 1H), 7.82 (s, 1H), 6.75 (s, 1H), 5.23 (s, 1H), 5.05 (s, 1H), 4.25 (s, 2H), 3.80 (s, 3H), 3.56 (bs, 2H), 1.81-1.79 (d, J=6.8 Hz 2H), 1.37 (s, 9H), 1.24 (bs, 2H).

Example 188: Azetidin-1-yl(4-((7-chloro-1-methyl-6-(pyrazolo[1,5-a]pyrazin-3-yloxy)-1H-imidazo[4,5-b]pyridin-2-yl)amino)-6-ethylpyridin-2-yl)methanone

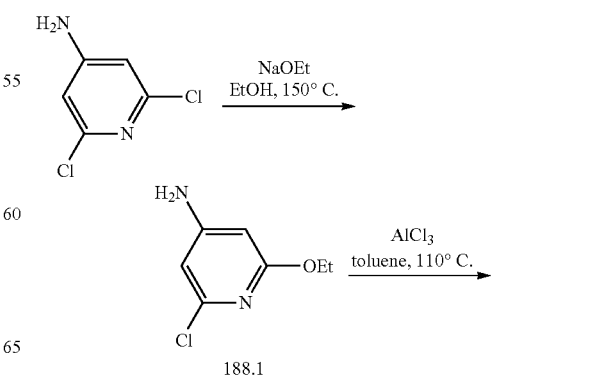

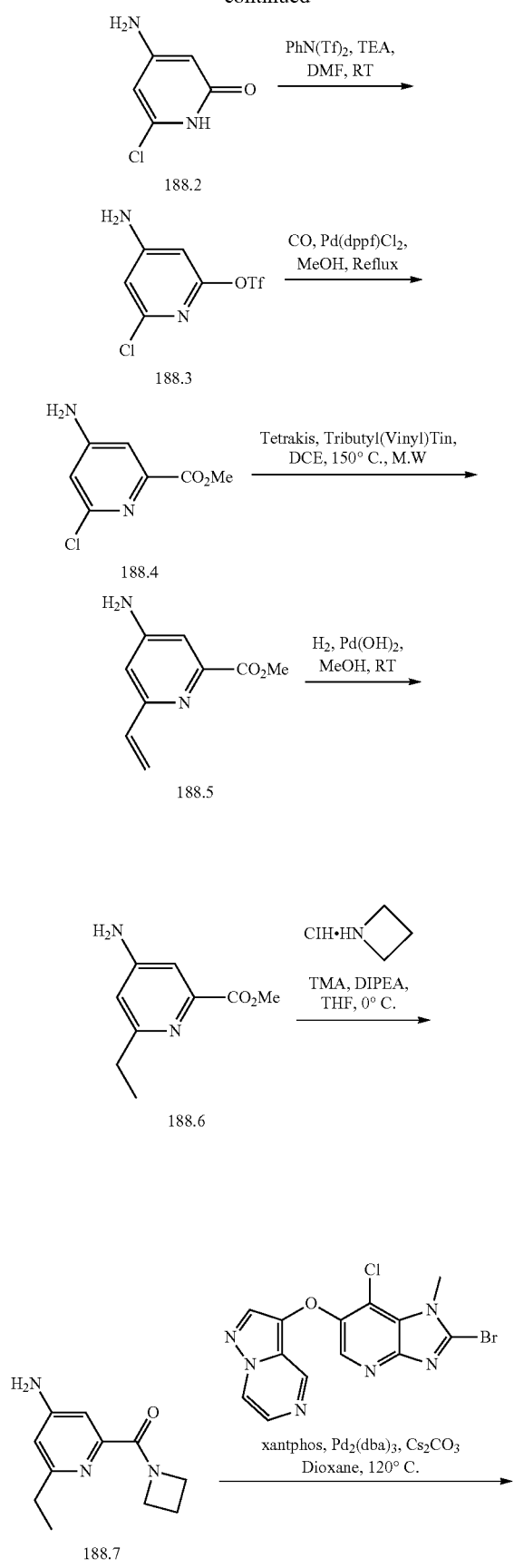

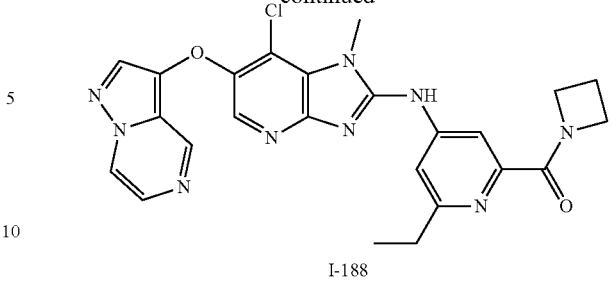

I-188

Synthesis of compound 188.1. To solution of 2,6-dichloropyridin-4-amine (10 g, 61.35 mmol, 1.0 equiv) in ethanol (20 mL) was added 21% sodium ethoxide (20 mL, 61.35 mmol, 1.0 equiv) and stirred at 150° C. for 10 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 15% ethyl acetate in hexane) to afford 188.1. MS (ES): m/z 173.2 [M+H]$^+$.

Synthesis of compound 188.2. To a solution of 188.1 (4.6 g, 26.65 mmol, 1.0 equiv) in toluene (150 mL) was added aluminum chloride (8.86 g, 66.62 mmol, 2.5 equiv). The reaction mixture stirred at 110° C. for 2 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% methanol in DCM) to afford 188.2. MS (ES): m/z 145.4 [M+H]$^+$.

Synthesis of compound 188.3. To a solution of 188.2 (2.2 g, 15.22 mmol, 1.0 equiv) and phenyl-bis(trifluoromethanesulfonimide) (5.43 g, 15.22 mmol, 1.0 equiv) in DMF (20 mL) was added triethylamine (5.3 mL, 38.05 mmol, 2.5 equiv). The reaction mixture was stirred at room temperature for 16 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% methanol in DCM) to afford 188.3. MS (ES): m/z 277.5 [M+H]$^+$.

Synthesis of compound 188.4. A solution of 188.3 (1.97 g, 7.12 mmol, 1.0 equiv) in methanol (50 mL) was degassed by bubbling a stream of argon for 10 min. 1,1-Bis(diphenylphosphino)ferrocene-palladium(II) dichloride-DCM complex (1.16 g, 1.42 mmol, 0.2 equiv) was added followed by triethylamine (1.98 mL, 14.24 mmol, 2.0 equiv). The reaction mixture stirred for 3-4 h at 70-80° C. under carbon monoxide atmosphere. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 40% ethyl acetate in hexane) to afford 188.4. MS (ES): m/z 187.5 [M+H]$^+$.

Synthesis of compound 188.5. To a solution of 188.4 (0.800 g, 4.29 mmol, 1.0 equiv), tetrakis(triphenylphosphine)palladium(0) (0.495 g, 0.429 mmol, 0.1 equiv) and tributylvinyltin (6.79 g, 21.45 mmol, 5.0 equiv) in 1,2-dichloroethane (20 mL) was stirred at 150° C. in a microwave reactor for 4 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% methanol in DCM) to afford 188.5. MS (ES): m/z 178.9 [M+H]⁺.

Synthesis of compound 188.6. A mixture of compound 188.5 (0.312 g, 1.75 mmol, 1.0 equiv) and 20% palladium hydroxide (0.150 g) in methanol (10 mL) was stirred under hydrogen was purged through the reaction mixture for 2 h. The reaction mixture was filtered through a pad of Celite® and washed with methanol. The filtrate was concentrated under reduced pressure to afford 188.6. MS (ES): m/z 181.1 [M+H]⁺.

Synthesis of compound 188.7. To a solution of 188.6 (0.180 g, 0.998 mmol, 1.0 equiv) and azetidine hydrochloride (0.280 g, 3.00 mmol, 3.0 equiv) in THF (5 mL) was added N,N-diisopropylethylamine (0.64 g, 4.99 mmol, 5.0 equiv) at 0° C. followed by addition of trimethylaluminum solution (2.0 M in toluene, 2.0 mL, 3.99 mmol, 4.0 equiv). The reaction mixture was stirred at 90° C. for 10 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 5% methanol in DCM) to afford 188.7. MS (ES): m/z 206.1 [M+H]⁺.

Synthesis of I-188. Compound I-188 was prepared from 61.2 and 188.7, following the procedure described in the synthesis of I-53. The product was purified by flash column chromatography on silica gel (CombiFlash®, 10% methanol in DCM) to afford I-188. MS (ES): m/z 504.2 [M+H]⁺. ¹H NMR (DMSO-d₆, 400 MHz): δ 9.90 (s, 1H), 9.05 (s, 1H), 8.71 (s, 1H), 8.26 (bs, 2H), 8.07-8.06 (d, J=4.0 Hz, 1H), 7.97 (s, 1H), 7.88 (s, 1H), 4.67 (bs, 2H), 4.09-4.04 (m, 6H), 1.29 (bs, 6H).

Example 189: 7-chloro-N-(4-((3-fluoroazetidin-1-yl)methyl)-3-(trifluoromethyl)phenyl)-1-methyl-6-((4-(methylamino)pyrazolo[1,5-a]pyrazin-3-yl)oxy)-1H-imidazo[4,5-b]pyridin-2-amine

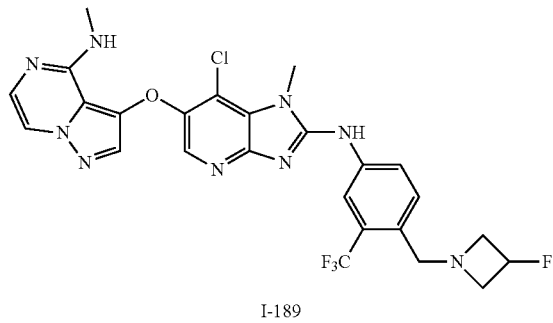

I-189

Synthesis of compound 189.1. Compound 189.1 was prepared from 124.7 and Int-90, following the procedure described in the synthesis of I-13. The product was purified by flash column chromatography on silica gel (CombiFlash®, 2.5% methanol in DCM). MS (ES): m/z 582.2 [M+H]⁺.

Synthesis of compound I-189. Compound I-189 was prepared from 189.1, following the procedure described in the synthesis of I-171. The product was purified by flash column chromatography on silica gel (CombiFlash®, 4.0% methanol in DCM). MS (ES): m/z 576.6 [M+H]⁺, ¹H NMR (DMSO-d₆, 400 MHz): δ 9.63 (s, 1H), 8.29 (s, 1H), 8.18 (s, 1H), 8.16 (s, 1H), 7.78-7.77 (d, J=2.8 Hz, 1H), 7.66-7.64 (d, J=8.0 Hz, 1H), 7.46 (s, 1H), 7.26-7.25 (d, J=2.8 Hz, 1H), 6.81 (s, 1H), 5.29-5.15 (m, 1H), 4.02 (s, 3H), 3.77 (s, 3H), 3.64-3.60 (m, 2H), 3.25-3.18 (m, 2H), 2.99 (s, 2H).

Example 190: 7-chloro-N-(4-((3-methoxyazetidin-1-yl)methyl)-3-(trifluoromethyl)phenyl)-1-methyl-6-((4-(methylamino)pyrazolo[1,5-a]pyrazin-3-yl)oxy)-1H-imidazo[4,5-b]pyridin-2-amine

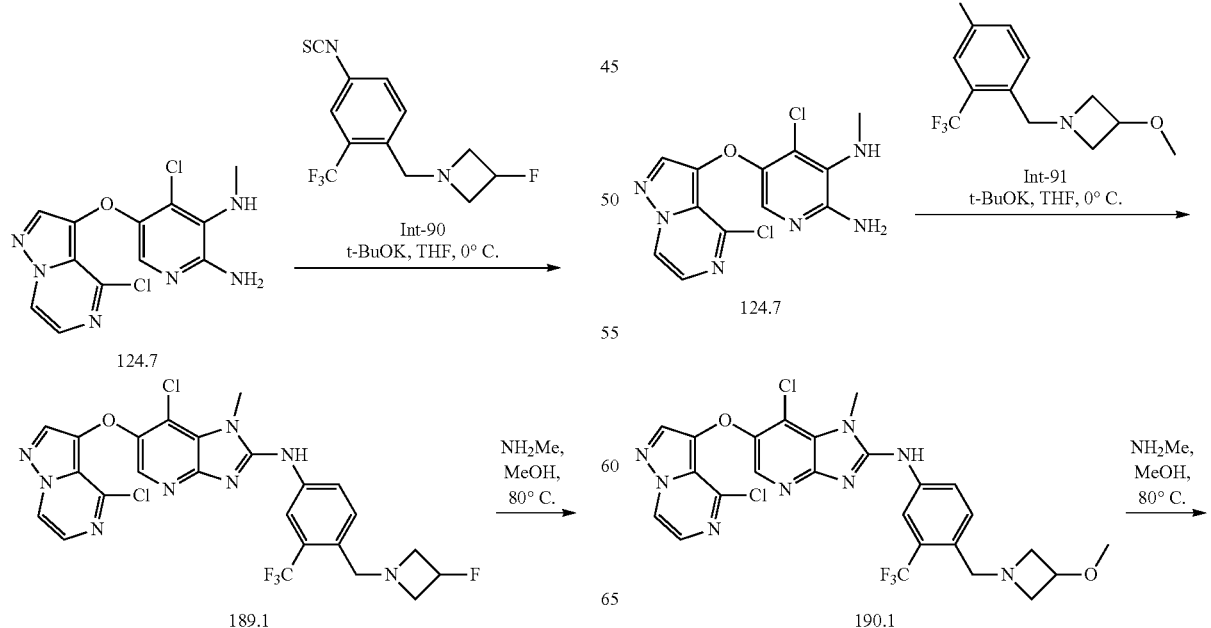

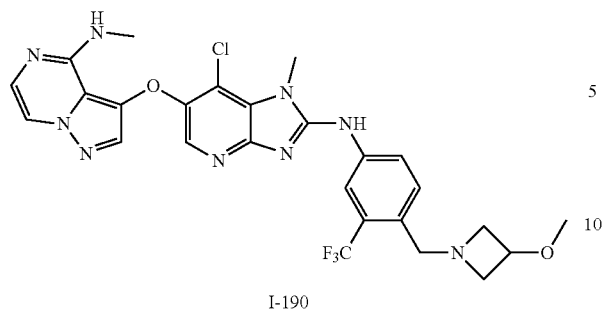

I-190

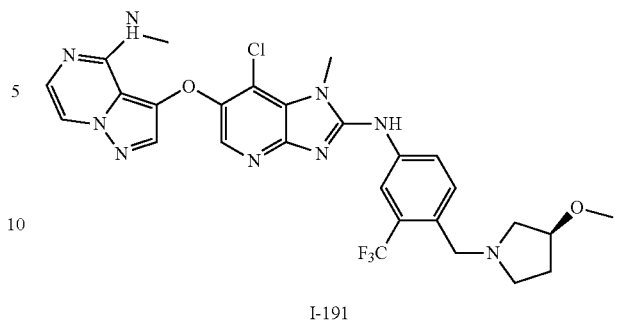

I-191

Synthesis of compound 190.1. Compound 190.1 was prepared from 124.7 and Int-91, following the procedure described in the synthesis of I-13. The product was purified by flash column chromatography on silica gel (Combi-Flash®, 8% methanol in DCM). MS (ES): m/z 594.0 [M+H]$^+$.

Synthesis of I-190. Compound I-190 was prepared from 190.1, following the procedure described in the synthesis of I-171. The product was purified by flash column chromatography on silica gel (CombiFlash®, 10% methanol in DCM). MS (ES): m/z 588.2 [M+H]$^+$, $^1$H NMR (DMSO-d$_6$, 400 MHz): δ 9.66 (s, 1H), 8.29 (s, 1H), 8.18 (bs, 2H), 7.77-7.76 (d, J=4.0 Hz, 1H), 7.67-7.65 (d, J=8.8 Hz, 1H), 7.46 (s, 1H), 7.25-7.24 (d, J=4.0 Hz, 1H), 6.83 (s, 1H), 4.01 (s, 3H), 3.81 (bs, 2H), 3.64 (bs, 2H), 3.17 (s, 3H), 2.99 (bs, 4H), 2.57 (bs, 2H).

Synthesis of compound 191.1. Compound 191.1 was prepared from 124.7 and Int-91, following the procedure described in the synthesis of I-13. The product was purified by flash column chromatography on silica gel (Combi-Flash®, 7.0% methanol in DCM). MS (ES): m/z 608.1 [M+H]$^+$.

Synthesis of I-191. Compound I-191 was prepared from 191.1, following the procedure described in the synthesis of I-171. The product was purified by flash column chromatography on silica gel (CombiFlash®, 5.0% methanol in DCM). MS (ES): m/z 602.2 [M]$^+$, $^1$H NMR (DMSO-d$_6$, 400 MHz): δ 9.65 (s, 1H), 8.31 (s, 1H), 8.20-8.16 (m, 2H), 7.79-7.78 (d, J=4.0 Hz, 1H), 7.75-7.73 (d, J=8.0 Hz, 1H), 7.48 (s, 1H), 7.27-7.26 (d, J=4.0 Hz, 1H), 6.83 (s, 1H), 4.03 (s, 3H), 3.93 (bs, 1H), 3.71 (bs, 2H), 3.19 (s, 3H), 3.01-3.00 (d, 3H), 2.73 (bs, 2H), 2.02 (bs, 2H), 1.71 (bs, 2H).

Example 191: (S)-7-chloro-N-(4-((3-methoxypyrrolidin-1-yl)methyl)-3-(trifluoromethyl)phenyl)-1-methyl-6-((4-(methylamino)pyrazolo[1,5-a]pyrazin-3-yl)oxy)-1H-imidazo[4,5-b]pyridin-2-amine Example 192: (R)-7-chloro-6-((4-chloropyrazolo[1,5-a]pyrazin-3-yl)oxy)-N-(4-((3-methoxypyrrolidin-1-yl)methyl)-3-(trifluoromethyl)phenyl)-1-methyl-1H-imidazo[4,5-b]pyridin-2-amine

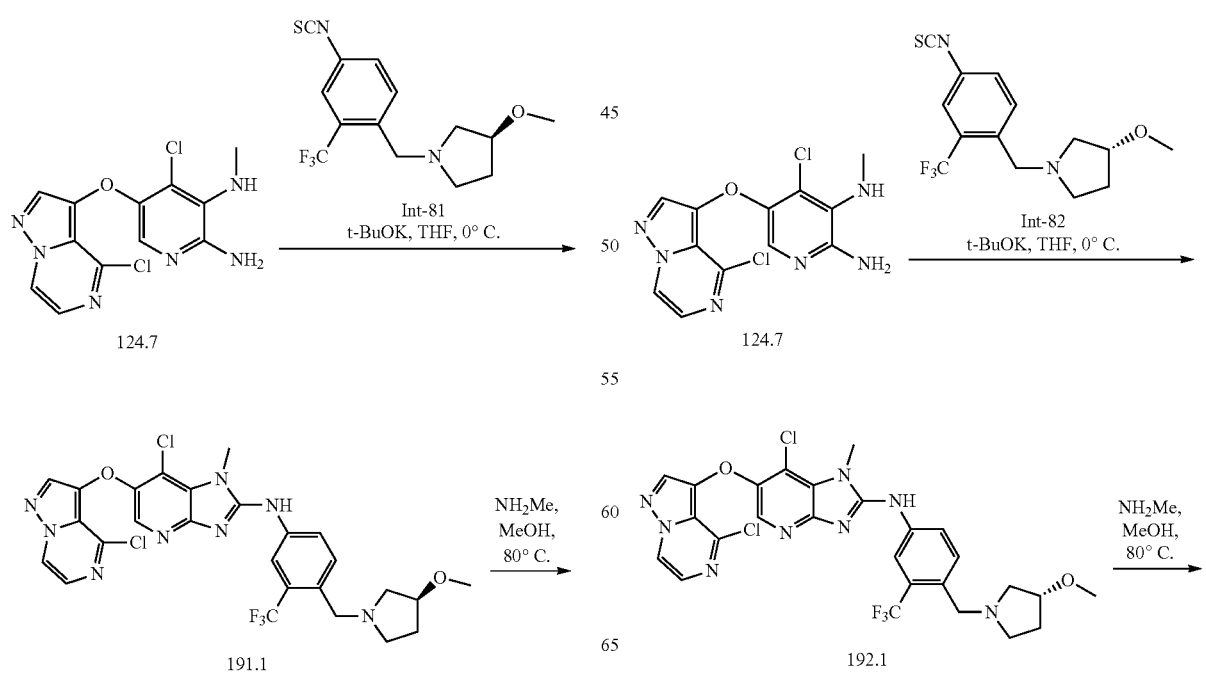

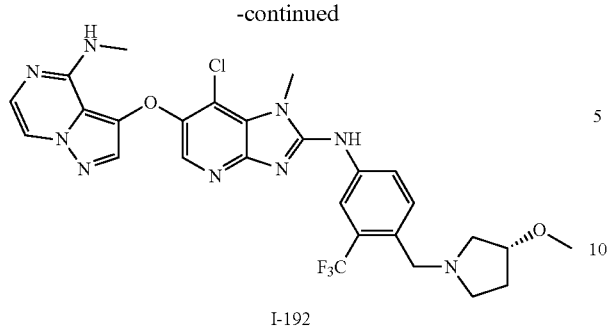

I-192

Synthesis of compound 192.1. Compound 192.1 was prepared from 124.7 and Int-82, following the procedure described in the synthesis of I-13. The product was purified by flash column chromatography on silica gel (CombiFlash®, 7.0% methanol in DCM). MS (ES): m/z 608.2 [M+H]⁺.

Synthesis of I-192. Compound I-192 was prepared from 192.1, following the procedure described in the synthesis of I-171. The product was purified by flash column chromatography on silica gel (CombiFlash®, 5.0% methanol in DCM). MS (ES): m/z 602.2 [M]⁺, H NMR (DMSO-$d_6$, 400 MHz): δ 9.65 (s, 1H), 8.31 (s, 1H), 8.20-8.16 (m, 2H), 7.79-7.78 (d, J=4.0 Hz, 1H), 7.75-7.73 (d, J=8.0 Hz, 1H), 7.48 (s, 1H), 7.27-7.26 (d, J=4.0 Hz, 1H), 6.83 (s, 1H), 4.03 (s, 3H), 3.93 (bs, 1H), 3.71 (bs, 2H), 3.19 (s, 3H), 3.01-3.00 (d, 3H), 2.73 (bs, 2H), 2.02 (bs, 2H), 1.71 (bs, 2H).

Example 193: 1-methyl-2-((1-methyl-2-oxo-5-(trifluoromethyl)-1,2-dihydropyridin-3-yl)amino)-6-((4-(methylamino)pyrazolo[1,5-a]pyrazin-3-yl)oxy)-1H-imidazo[4,5-b]pyridine-7-carbonitrile

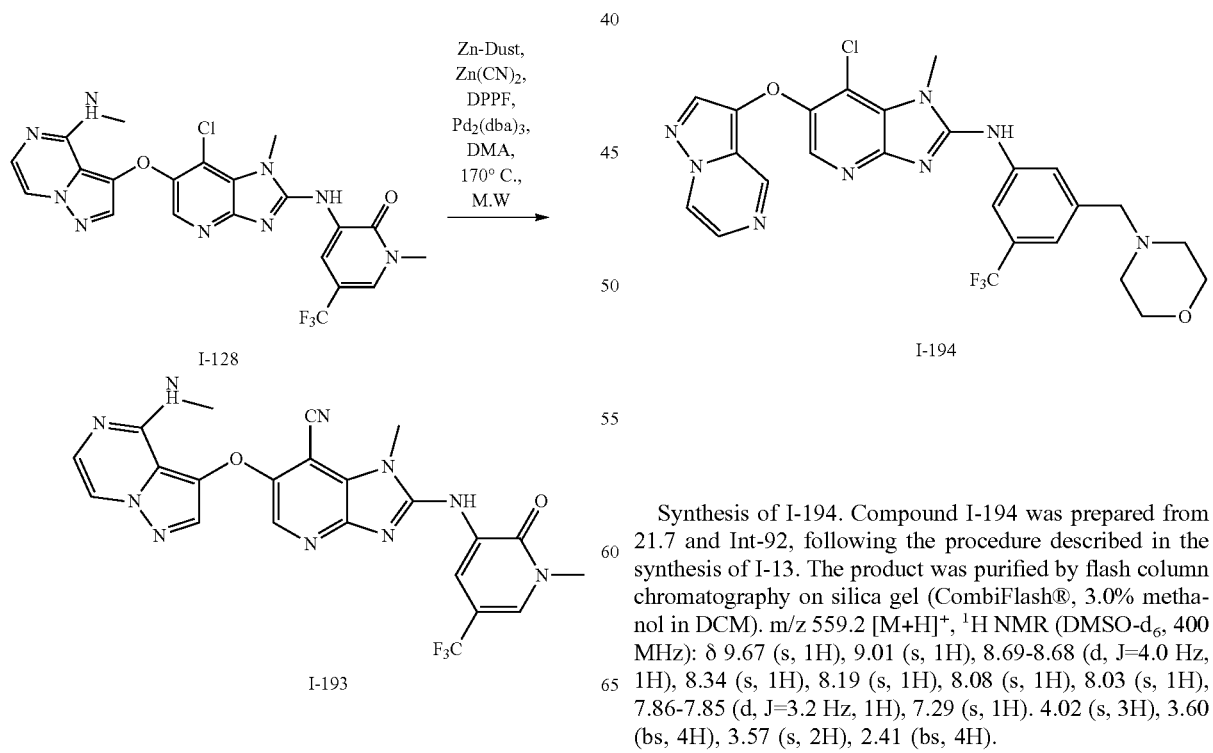

Synthesis of I-193. Compound I-193 was prepared from I-128, following the procedure described in the synthesis of I-157. The product was purified by flash column chromatography on silica gel (CombiFlash®, 2.0% methanol in DCM). MS (ES): m/z 511.5 [M+H]⁺, ¹H NMR (DMSO-$d_6$, 400 MHz): δ 9.00 (s, 1H), 8.62 (s, 1H), 8.17 (s, 1H), 8.14 (s, 1H), 7.85-7.84 (d, J=4.8 Hz, 1H), 7.79 (s, 1H), 7.30-7.29 (d, J=4.8 Hz, 1H), 6.83 (s, 1H), 3.99 (s, 3H), 3.66 (bs, 3H), 2.95-2.94 (d, 3H).

Example 194: 7-chloro-1-methyl-N-(3-(morpholinomethyl)-5-(trifluoromethyl)phenyl)-6-(pyrazolo[1,5-a]pyrazin-3-yloxy)-1H-imidazo[4,5-b]pyridin-2-amine

Synthesis of I-194. Compound I-194 was prepared from 21.7 and Int-92, following the procedure described in the synthesis of I-13. The product was purified by flash column chromatography on silica gel (CombiFlash®, 3.0% methanol in DCM). m/z 559.2 [M+H]⁺, ¹H NMR (DMSO-$d_6$, 400 MHz): δ 9.67 (s, 1H), 9.01 (s, 1H), 8.69-8.68 (d, J=4.0 Hz, 1H), 8.34 (s, 1H), 8.19 (s, 1H), 8.08 (s, 1H), 8.03 (s, 1H), 7.86-7.85 (d, J=3.2 Hz, 1H), 7.29 (s, 1H). 4.02 (s, 3H), 3.60 (bs, 4H), 3.57 (s, 2H), 2.41 (bs, 4H).

Example 195: 7-chloro-N-(3-((3-fluoroazetidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

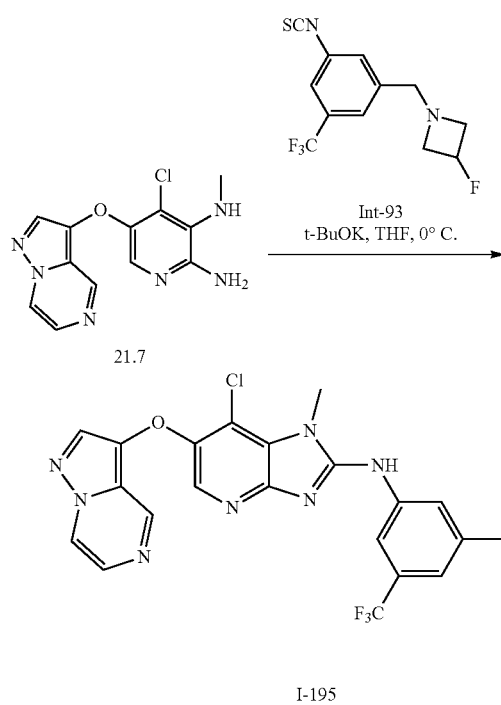

Synthesis of I-195. Compound I-195 was prepared from 21.7 and Int-93, following the procedure described in the synthesis of I-13. The product was purified by flash column chromatography on silica gel (CombiFlash®, 3.5% methanol in DCM). m/z 547.11 [M+H]$^+$, $^1$H NMR (DMSO-d$_6$, 400 MHz): δ 9.68 (s, 1H), 9.04 (s, 1H), 8.71-8.70 (d, J=4 Hz, 1H), 8.32 (s, 1H), 8.22 (s, 1H), 8.08 (s, 1H), 8.05 (s, 1H), 7.89-7.88 (d, J=4 Hz, 1H), 7.28 (s, 1H), 5.32-5.15 (m, 1H), 4.04 (s, 3H), 3.77 (s, 2H), 3.65-3.61 (m, 2H), 3.27-3.21 (m, 2H).

Example 196: 7-chloro-N-(3-((3-methoxyazetidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

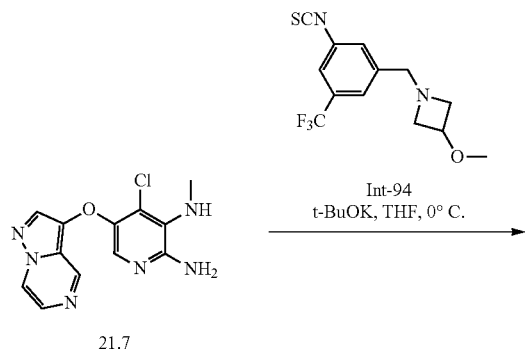

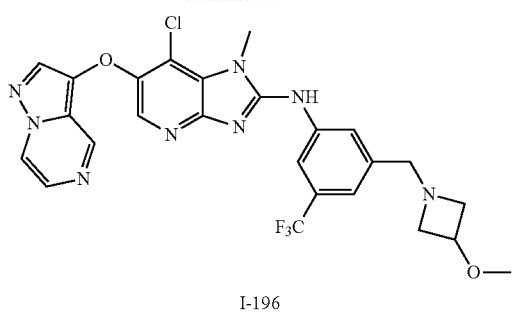

Synthesis of I-196. Compound I-196 was prepared from 21.7 and Int-94, following the procedure described in the synthesis of I-13. The product was purified by flash column chromatography on silica gel (CombiFlash®, 3.5% methanol in DCM). MS (ES): m/z 559.30 [M+H]$^+$, $^1$H NMR (DMSO-d$_6$, 400 MHz): δ 9.66 (s, 1H), 9.02 (s, 1H), 8.70-8.69 (d, J=4 Hz, 1H), 8.31 (s, 1H), 8.20 (s, 1H), 8.06-8.04 (d, J=8 Hz, 2H), 7.87-7.86 (d, J=4 Hz, 1H), 7.26 (s, 1H), 4.03 (s, 4H), 3.71 (bs, 2H), 3.56 (bs, 2H), 3.16 (s, 3H), 2.94 (bs, 2H).

Example 197: 7-chloro-N-(3-((3,3-difluoropyrrolidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

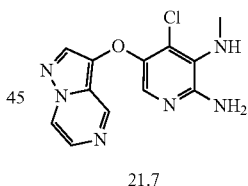
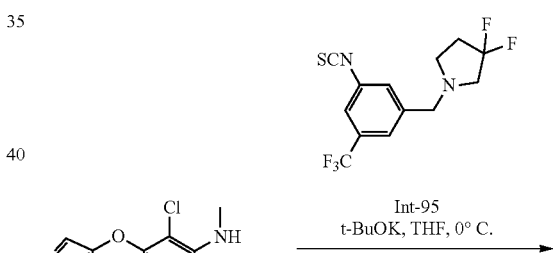

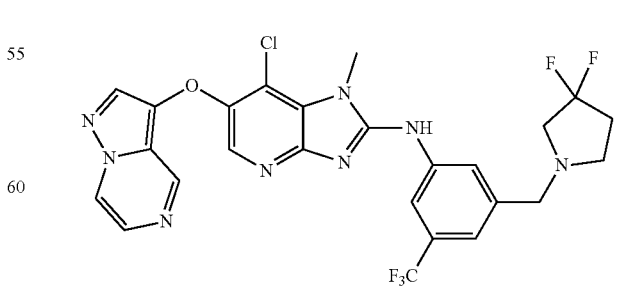

Synthesis of I-197. Compound I-197 was prepared from 21.7 and Int-95, following the procedure described in the synthesis of I-13. The product was purified by flash column chromatography on silica gel (CombiFlash®, 2.4% methanol in DCM) t. MS (ES): m/z 578.9 [M]+. 1H NMR (DMSO-d6, 400 MHz): δ 9.69 (s, 1H), 9.02 (s, 1H), 8.69-8.68 (d, J=4.8 Hz, 1H), 8.36 (s, 1H), 8.20 (s, 1H), 8.07 (s, 1H), 8.03 (s, 1H), 7.87-7.86 (d, J=4 Hz, 1H), 7.30 (s, 1H), 4.02 (s, 3H), 3.74 (bs, 2H), 2.96-2.90 (m, 2H), 2.76-2.73 (m, 2H), 2.33-2.25 (m, 2H).

Example 198: 7-chloro-N-(3-((4-methoxypiperidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

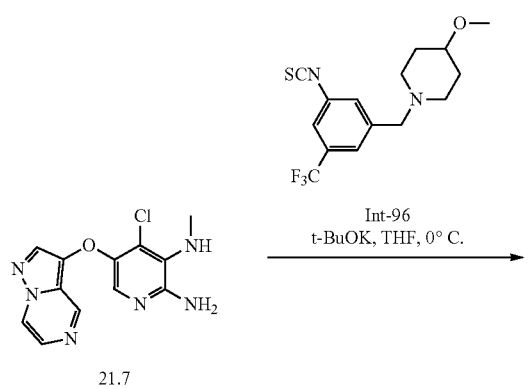

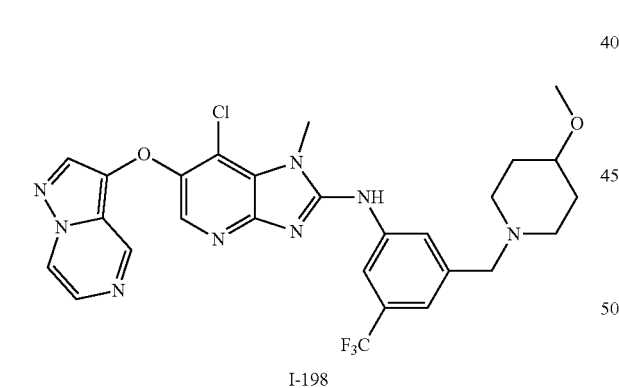

I-198

Synthesis of I-198. Compound I-198 was prepared from 21.7 and Int-96, following the procedure described in the synthesis of I-13. The product was purified by flash column chromatography on silica gel (CombiFlash®, 3.5% methanol in DCM). MS (ES): m/z 587.8 [M+H]+, 1H NMR (DMSO-d6, 400 MHz): δ 9.68 (s, 1H), 9.02 (s, 1H), 8.69 (bs, 1H), 8.36 (s, 1H), 8.20 (s, 1H), 8.04 (s, 1H), 8.03 (s, 1H), 7.87-7.86 (d, J=4.4 Hz, 1H), 7.28 (s, 1H), 4.03 (s, 3H), 3.55-3.50 (m, 3H), 3.22 (s, 3H), 2.68 (bs, 2H), 2.14 (bs, 2H), 1.84 (bs, 2H), 1.46 (bs, 2H).

Example 199: 4-((7-chloro-1-methyl-6-((4-(methylamino)pyrazolo[1,5-a]pyrazin-3-yl)oxy)-1H-imidazo[4,5-b]pyridin-2-yl)amino)-6-cyclopropyl-2-methylpyridazin-3(2H)-one

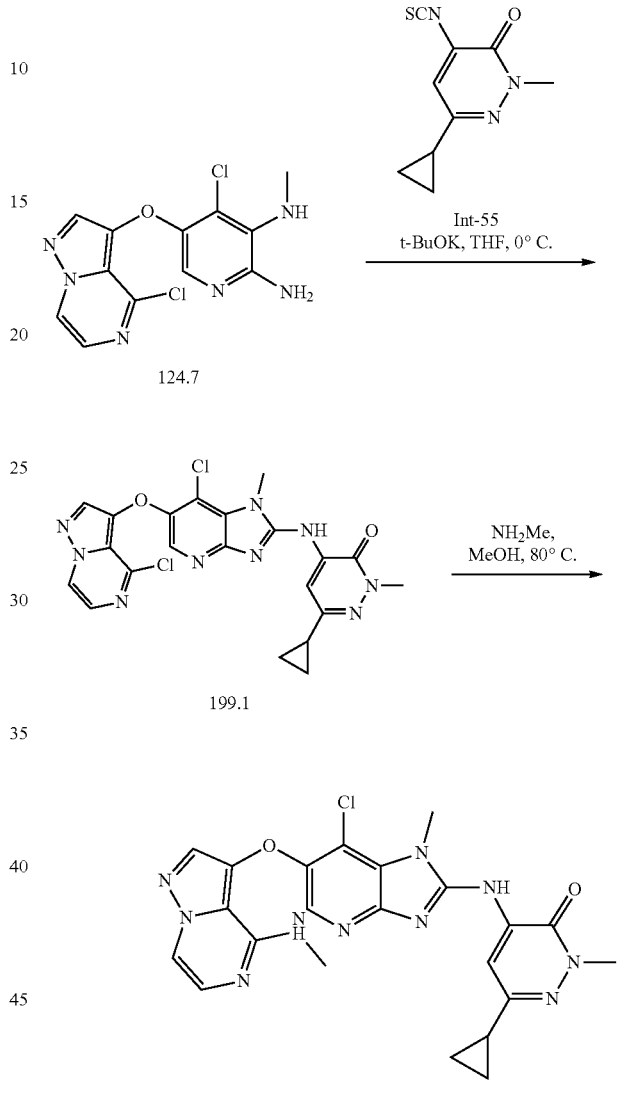

Synthesis of compound 199.1. Compound 199.1 was prepared from 21.7 and Int-55, following the procedure described in the synthesis of I-13. The product was purified by flash column chromatography on silica gel (CombiFlash®, 2.6% methanol in DCM). MS (ES): m/z 499.1 [M+H]+.

Synthesis of I-199. Compound I-199 was prepared from 199.1, following the procedure described in the synthesis of I-171. The product was purified by flash column chromatography on silica gel (CombiFlash®, 4.6% methanol in DCM). MS (ES): m/z 493.2 [M+H]+, 1H NMR (DMSO-d6, 400 MHz): δ 9.23 (s, 1H), 8.28 (s, 1H), 7.99 (s, 1H), 7.78 (bs, 1H), 7.51 (s, 1H), 7.26 (s, 1H), 6.84 (bs, 1H), 4.01 (s, 3H), 3.70 (s, 3H), 2.98 (s, 3H), 1.23 (bs, 1H), 0.96-0.95 (m, 2H), 0.81 (bs, 2H).

835

Example 200: 5-((7-chloro-1-methyl-6-(pyrazolo[1,5-a]pyrazin-3-yloxy)-1H-imidazo[4,5-b]pyridin-2-yl)amino)-1-methyl-6-oxo-3-(trifluoromethyl)-1,6-dihydropyridine-2-carbonitrile

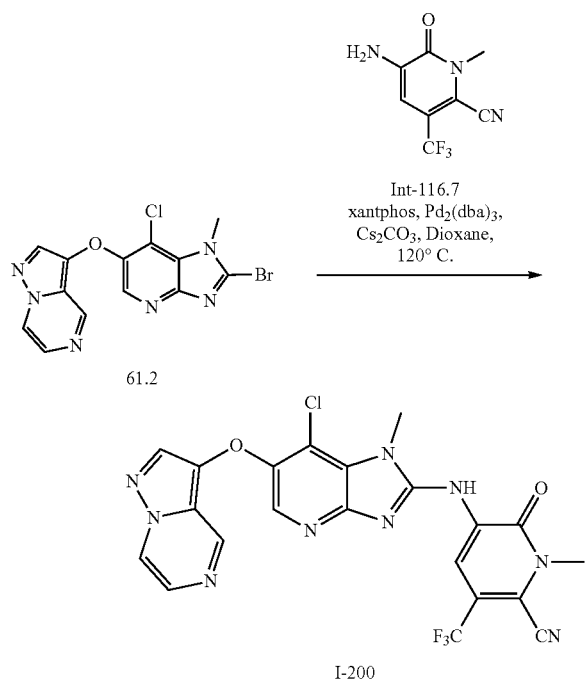

Synthesis of I-200. Compound I-200 was prepared from 61.2 and Int-116.7, following the procedure described in the synthesis of I-53. The product was purified by flash column chromatography on silica gel (CombiFlash®, 3.2% methanol in DCM). MS (ES): m/z 516.1 [M+H]$^+$, $^1$H NMR (DMSO-d$_6$, 400 MHz): δ 9.64 (s, 1H), 9.07 (bs, 1H), 9.05 (bs, 1H), 8.71-8.70 (d, J=4.0 Hz, 1H), 8.32 (s, 1H), 8.08 (s, 1H), 7.89-7.88 (d, J=4.8 Hz, 1H), 4.17 (s, 3H), 4.02 (s, 3H).

Example 201: 3-((7-chloro-1-methyl-6-((4-(methylamino)pyrazolo[1,5-a]pyrazin-3-yl)oxy)-1H-imidazo[4,5-b]pyridin-2-yl)amino)-1-methyl-5-(perfluoroethyl)pyridin-2(1H)-one

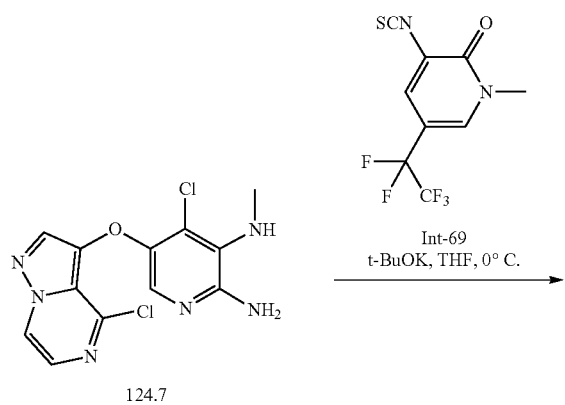

836

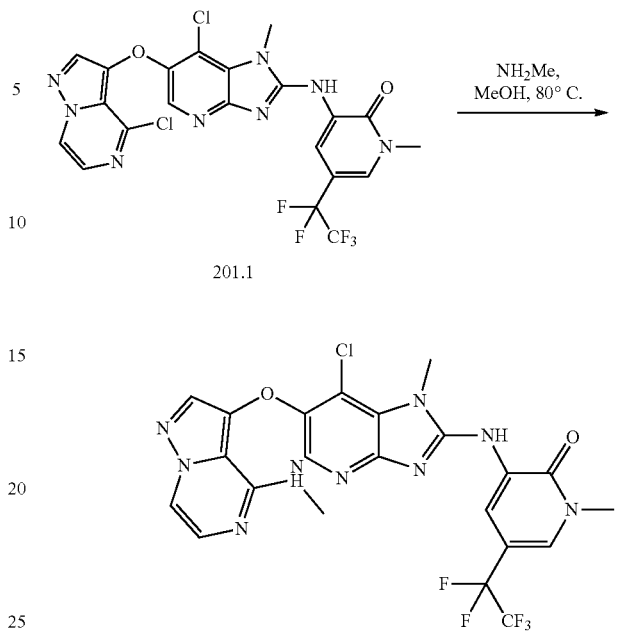

Synthesis of compound 201.1. Compound 201.1 was prepared from 124.7 and Int-69, following the procedure described in the synthesis of I-13. The product was purified by flash column chromatography on silica gel (CombiFlash®, 1.2% methanol in DCM). MS (ES): m/z 576.2 [M]$^+$.

Synthesis of I-201. Compound I-201 was prepared from 201.1, following the procedure described in the synthesis of I-171. The product was purified by flash column chromatography on silica gel (CombiFlash®, 3.5% methanol in DCM). MS (ES): m/z 569.9 [M]$^+$, $^1$H NMR (DMSO-d$_6$, 400 MHz): δ 8.84 (s, 1H), 8.62 (s, 1H), 8.23 (s, 1H), 8.10 (s, 1H), 7.78-7.77 (d, J=2.8 Hz, 1H), 7.48 (s, 1H), 7.25-7.24 (d, J=2.8 Hz, 1H), 6.85 (bs, 1H), 4.00 (s, 3H), 3.68 (s, 3H), 2.99-2.98 (d, 3H).

Example 202: 3-((7-chloro-1-methyl-6-((4-(methylamino)pyrazolo[1,5-a]pyrazin-3-yl)oxy)-1H-imidazo[4,5-b]pyridin-2-yl)amino)-1-isopropyl-5-(trifluoromethyl)pyridin-2(1H)-one

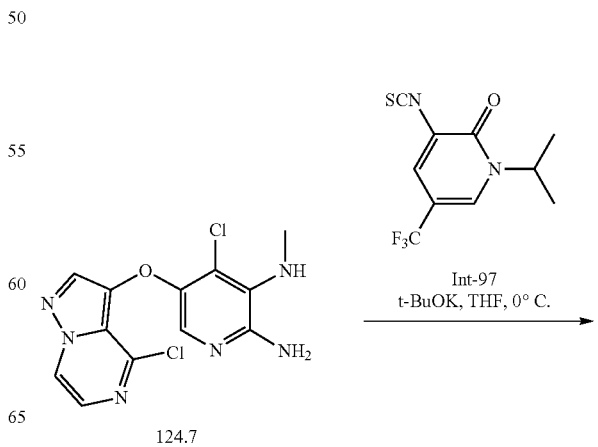

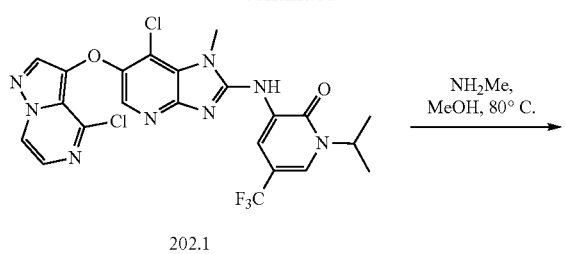

202.1

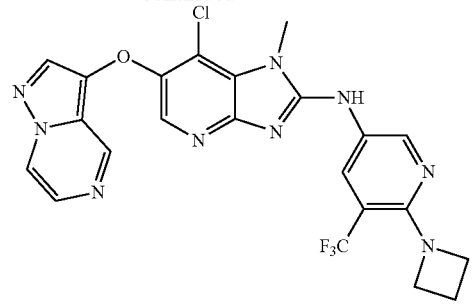

I-203

Synthesis of I-203. Compound I-203 was prepared from 21.7 and Int-98, following the procedure described in the synthesis of I-13. The product was purified by flash column chromatography on silica gel (CombiFlash®, 3.5% methanol in DCM). MS (ES): m/z 516.1 [M+H]⁺, ¹H NMR (DMSO-d₆, 400 MHz): δ 9.01 (bs, 2H), 8.69-8.68 (d, J=4.0 Hz, 1H), 8.37 (s, 1H), 8.13 (s, 1H), 8.01 (s, 1H), 7.88-7.86 (m, 2H), 4.15-4.13 (m, 4H), 3.96 (s, 3H), 2.27-2.23 (m, 2H).

Example 204: (R)-1-(3-((7-chloro-1-methyl-6-(pyrazolo[1,5-a]pyrazin-3-yloxy)-1H-imidazo[4,5-b]pyridin-2-yl)amino)-5-(trifluoromethyl)benzyl)pyrrolidin-3-ol

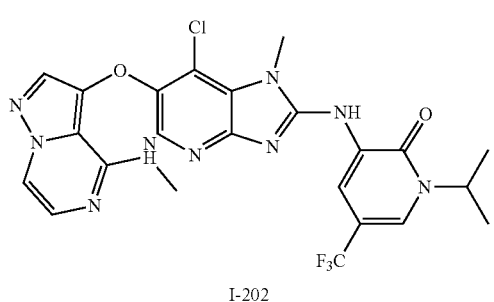

I-202

Synthesis of compound 202.1. Compound 202.1 was prepared from 124.7 and Int-97, following the procedure described in the synthesis of I-13. The product was purified by flash column chromatography on silica gel (CombiFlash®, 2.1% methanol in DCM). MS (ES): m/z 554.2[M+H]⁺.

Synthesis of I-202. Compound I-202 was prepared from 202.1, following the procedure described in the synthesis of I-171. The product was purified by flash column chromatography on silica gel (CombiFlash®, 4.0% methanol in DCM). MS (ES): m/z 548.9 [M+H]⁺, ¹H NMR (DMSO-d₆, 400 MHz): δ 8.86 (s, 1H), 8.61 (s, 1H), 8.23 (s, 1H), 7.99 (s, 1H), 7.78-7.77 (d, J=4.8 Hz, 1H), 7.50 (s, 1H), 7.25-7.24 (d, J=5.2 Hz, 1H), 6.83-6.82 (d, J=4.0 Hz, 1H), 5.18-5.15 (m, 1H), 4.01 (s, 3H), 2.99-2.98 (d, 3H), 1.44-1.43 (d, 6H).

Example 203: N-(6-(azetidin-1-yl)-5-(trifluoromethyl)pyridin-3-yl)-7-chloro-1-methyl-6-(pyrazolo[1,5-a]pyrazin-3-yloxy)-1H-imidazo[4,5-b]pyridin-2-amine

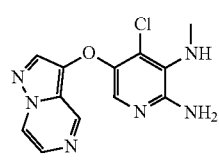

21.7

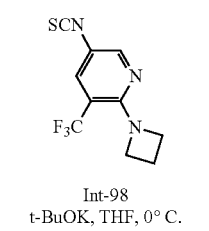

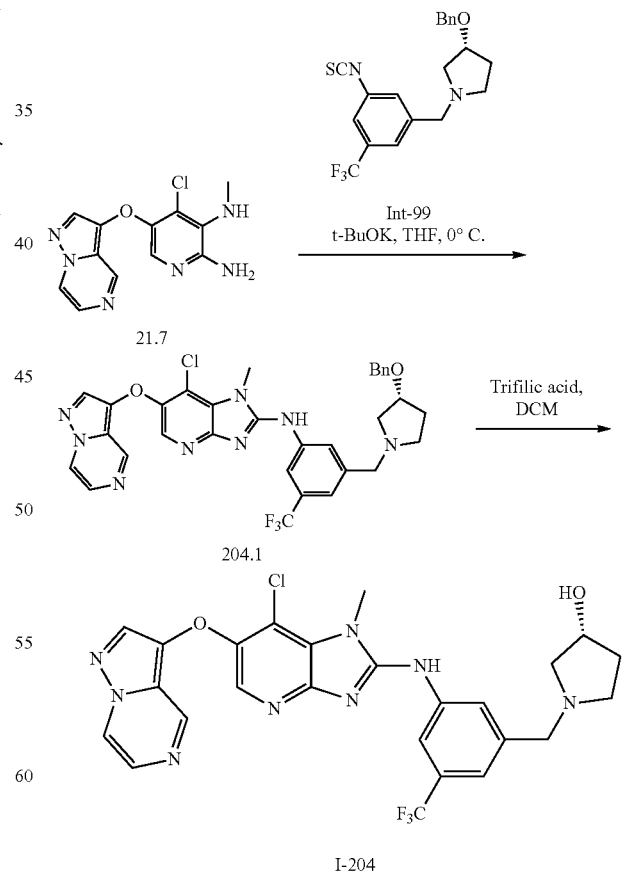

I-204

Synthesis of compound 204.1. Compound 204.1 was prepared from 21.7 and Int-99, following the procedure described in the synthesis of I-13. The product was purified by flash column chromatography on silica gel (Combi-Flash®, 4.4% methanol in DCM). MS (ES): m/z 650.8 [M+H]⁺.

Synthesis of I-204. Compound I-204 was prepared from 204.1, following the procedure described in the synthesis of I-23. The product was purified by flash column chromatography on silica gel (CombiFlash®, 9.0% methanol in DCM). MS (ES): m/z 559.2 [M+H]⁺, $^1$H NMR (DMSO-d$_6$, 400 MHz): δ 9.66 (s, 1H), 9.01 (s, 1H), 8.69-8.68 (d, J=4.0 Hz, 1H), 8.33 (s, 1H), 8.20 (bs, 1H), 8.07 (s, 1H), 8.03 (s, 1H), 7.87-7.86 (d, J=4.0 Hz, 1H), 7.30 (s, 1H), 4.76 (bs, 1H), 4.24 (bs, 1H), 4.02 (s, 3H), 3.71 (bs, 2H), 2.77-2.75 (m, 2H), 2.67 (bs, 2H), 2.04-2.00 (m, 2H).

Example 205: (S)-1-(3-((7-chloro-1-methyl-6-(pyrazolo[1,5-a]pyrazin-3-yloxy)-1H-imidazo[4,5-b]pyridin-2-yl)amino)-5-(trifluoromethyl)benzyl)pyrrolidin-3-ol Synthesis of compound 205.1. Compound 205.1 was prepared from 21.7 and Int-100, following the procedure described in the synthesis of I-13. The product was purified by flash column chromatography on silica gel (CombiFlash®, 4.4% methanol in DCM). MS (ES): m/z 650.1 [M+H]⁺.

Synthesis of compound I-205. Compound I-205 was prepared from 205.1, following the procedure described in the synthesis of I-23. The product was purified by flash column chromatography on silica gel (CombiFlash®, 9.0% methanol in DCM). MS (ES): m/z 559.2 [M+H]⁺, $^1$H NMR (DMSO-d$_6$, 400 MHz): δ 9.68 (s, 1H), 9.03 (s, 1H), 8.71-8.69 (d, J=4.4 Hz, 1H), 8.34 (s, 1H), 8.21 (bs, 1H), 8.09 (s, 1H), 8.05 (s, 1H), 7.88-7.87 (d, J=4.4 Hz, 1H), 7.32 (s, 1H), 4.78 (bs, 1H), 4.25 (bs, 1H), 4.04 (s, 3H), 3.72 (bs, 2H), 2.78-2.77 (m, 2H), 2.68-2.67 (m, 2H), 2.07-2.02 (m, 2H).

Example 206: 7-chloro-1-methyl-N-(3-((1-methylpiperidin-4-yl)oxy)-5-(trifluoromethyl)phenyl)-6-(pyrazolo[1,5-a]pyrazin-3-yloxy)-1H-imidazo[4,5-b]pyridin-2-amine

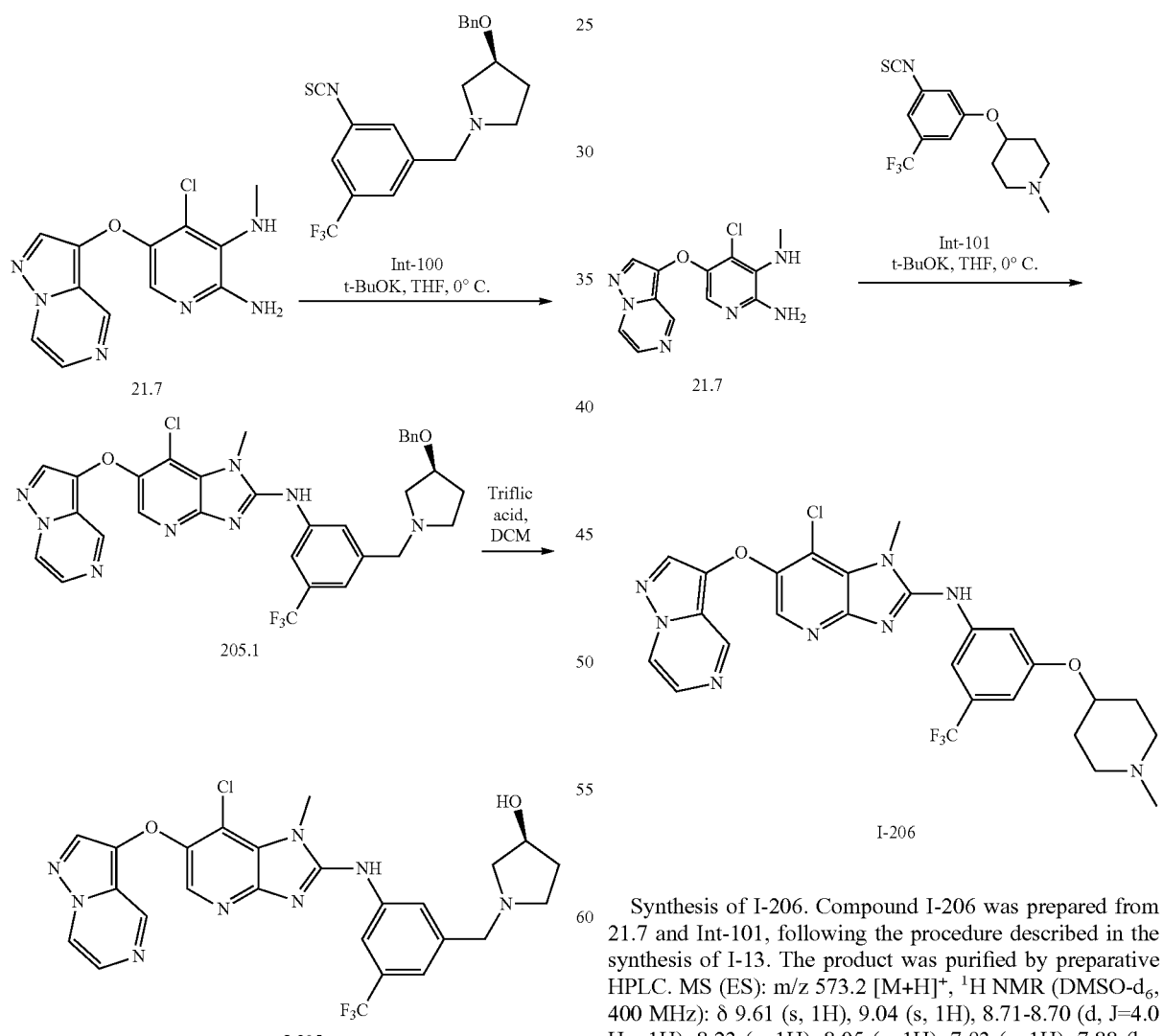

Synthesis of I-206. Compound I-206 was prepared from 21.7 and Int-101, following the procedure described in the synthesis of I-13. The product was purified by preparative HPLC. MS (ES): m/z 573.2 [M+H]⁺, $^1$H NMR (DMSO-d$_6$, 400 MHz): δ 9.61 (s, 1H), 9.04 (s, 1H), 8.71-8.70 (d, J=4.0 Hz, 1H), 8.23 (s, 1H), 8.05 (s, 1H), 7.93 (s, 1H), 7.88 (bs, 2H), 6.94 (s, 1H), 4.49 (bs, 1H), 4.04 (s, 3H), 2.69-2.63 (m, 4H), 2.21 (s, 3H), 1.99 (bs, 2H), 1.72 (bs, 2H).

Example 207: 2-(4-(4-((7-chloro-1-methyl-6-(pyrazolo[1,5-a]pyrazin-3-yloxy)-1H-imidazo[4,5-b]pyridin-2-yl)amino)-2-(trifluoromethyl)benzyl)piperazin-1-yl)ethan-1-ol Synthesis of I-207. Compound I-207 was prepared from 207.1, following the procedure described in the synthesis of I-23. The product was purified by flash column chromatography on silica gel (CombiFlash®, 3.9% methanol in DCM). MS (ES): m/z 602.2 [M+H]+, 1H NMR (DMSO-d6, 400

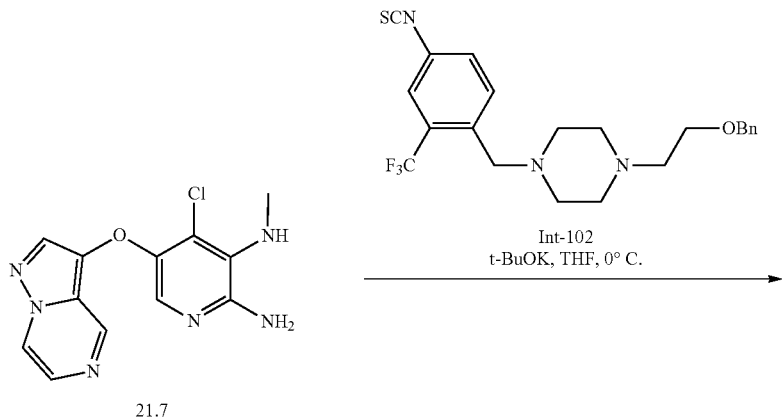

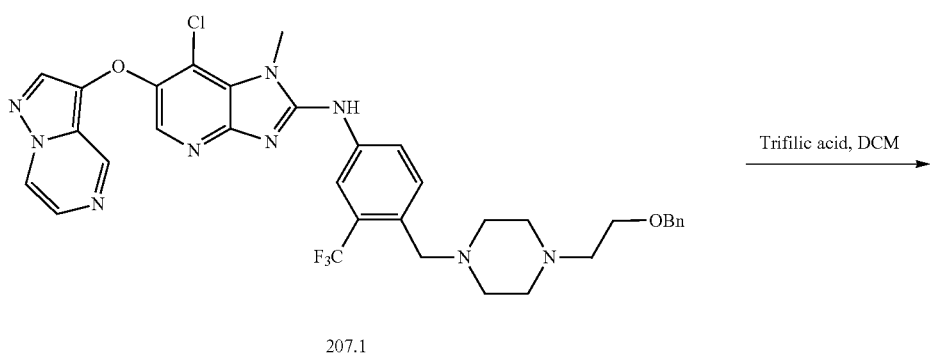

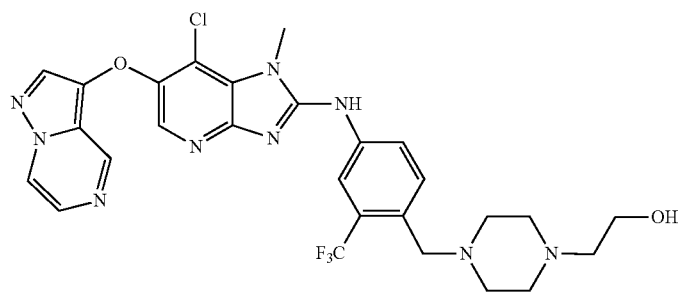

Synthesis of compound 207.1. Compound 207.1 was prepared from 21.7 and Int-102, following the procedure described in the synthesis of I-13. The product was purified by flash column chromatography on silica gel (CombiFlash®, 2.1% methanol in DCM). MS (ES): m/z 693.0 [M+H]+.

MHz): δ 9.67 (s, 1H), 9.02 (s, 1H), 8.69-8.68 (d, J=4.8 Hz, 1H), 8.29 (s, 1H), 8.19 (s, 1H), 8.17-8.14 (d, J=8.8 Hz, 1H), 8.03 (s, 1H), 7.87-7.86 (d, J=4.8 Hz, 1H), 7.73-7.70 (d, J=8.4 Hz, 1H), 4.03 (s, 3H), 3.57-3.51 (m, 5H), 2.67-2.57 (m, 10H).

Example 208. 7-chloro-N-(4-((4-(2,2-difluoroethyl) piperazin-1-yl)methyl)-3-(trifluoromethyl)phenyl)-1-methyl-6-(pyrazolo[1,5-a]pyrazin-3-yloxy)-1H-imidazo[4,5-b]pyridin-2-amine

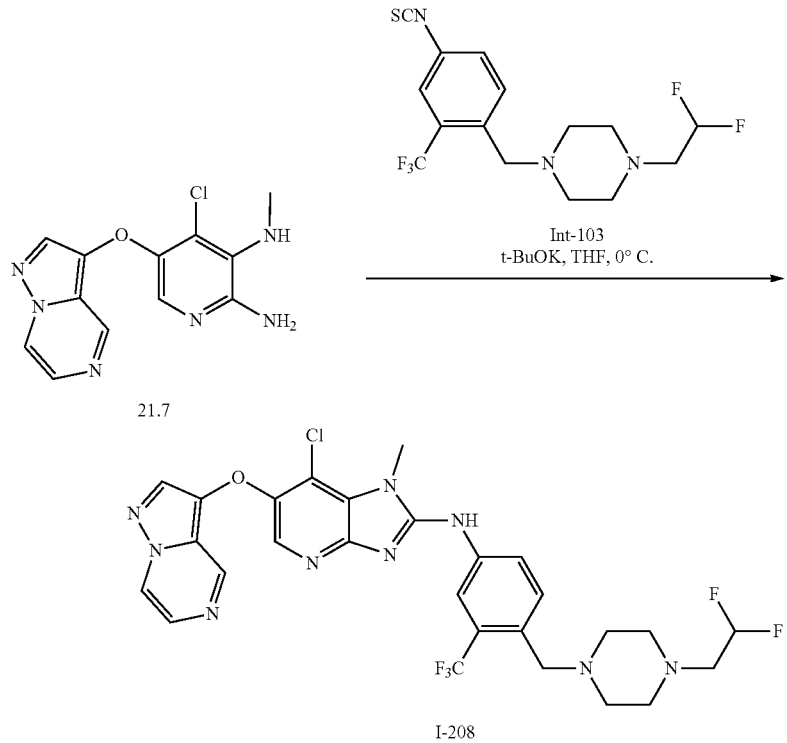

Synthesis of I-208. Compound I-208 was prepared from 21.7 and Int-103, following the procedure described in the synthesis of I-13. The product was purified by flash column chromatography on silica gel (CombiFlash®, 5.1% methanol in DCM). MS (ES): m/z 622.1 [M]+, 1H NMR (DMSO-d6, 400 MHz): δ 9.63 (s, 1H), 9.02 (s, 1H), 8.69 (bs, 1H), 8.28 (s, 1H), 8.19 (s, 1H), 8.16-8.14 (d, J=8.8 Hz, 1H), 8.03 (s, 1H), 7.87-7.86 (d, J=4.4 Hz, 1H), 7.72-7.70 (d, J=8.4 Hz, 1H), 6.25-6.00 (m, 1H), 4.78 (bs, 2H), 4.02 (s, 3H), 3.57 (bs, 2H), 2.67-2.57 (m, 8H).

Example 209: (R)-7-chloro-1-methyl-N-(3-((1-methylpyrrolidin-3-yl)oxy)-5-(trifluoromethyl)phenyl)-6-(pyrazolo[1,5-a]pyrazin-3-yloxy)-1H-imidazo[4,5-b]pyridin-2-amine

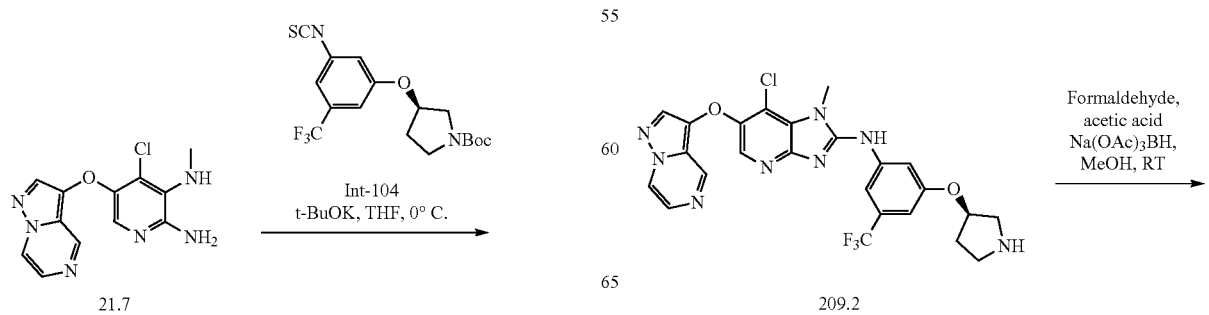

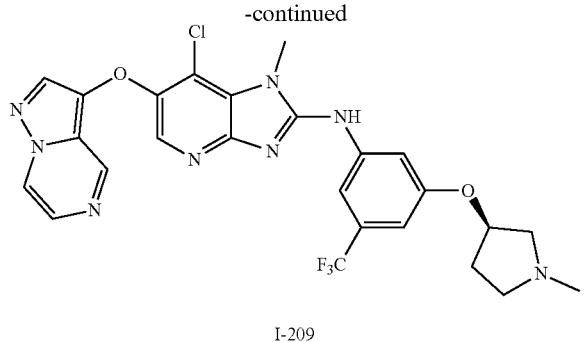

I-209

Synthesis of compound 209.1. Compound 209.1 was prepared from 21.7 and Int-104, following the procedure described in the synthesis of I-13. The product was purified by flash column chromatography on silica gel (CombiFlash®, 4.2% methanol in DCM). MS (ES): m/z 646.0 [M+H]⁺.

Synthesis of compound 209.2. To a solution of 209.1 (0.105 g, 0.162 mmol, 1.0 equiv) in DCM (5 mL) was added hydrogen chloride in dioxane (4.0 M, 2 mL) at 0° C. and stirred at room temperature for 1 h. It was poured over saturated sodium bicarbonate solution and extracted with ethyl acetate. The combined organic layers were washed with brine, dried over anhydrous sodium sulfate, filtered and concentrated under reduced pressure to afford 209.2. MS (ES): m/z 545.8 [M+H]⁺.

Synthesis of I-209. To a solution of 210.2 (0.065 g, 0.119 mmol, 1.0 equiv) in methanol (7.5 mL) was added formaldehyde (0.017 g, 0.595 mmol, 5.0 equiv) and acetic acid (0.017 g, 0.297 mmol, 2.5 equiv) at 0° C. After 10 min, sodium triacetoxyborohydride (0.075 g, 0.357 mmol, 3.0 equiv) was added. The reaction mixture was stirred at room temperature for 30 min. It was poured over ice cold water and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% methanol in DCM) to afford I-209. MS (ES): m/z 559.2 [M+H]⁺, ¹H NMR (DMSO-d₆, 400 MHz): δ 9.92 (s, 1H), 9.03 (bs, 1H), 8.70-8.69 (d, J=3.6 Hz, 1H), 8.21 (s, 1H), 8.05 (bs, 2H), 7.94 (s, 1H), 7.88-7.87 (d, J=4.8 Hz, 1H), 6.89 (s, 1H), 5.11 (bs, 1H), 4.08 (s, 3H), 3.10 (bs, 2H), 2.90-2.68 (m, 6H), 2.02 (bs, 1H).

Example 210: (S)-7-chloro-1-methyl-N-(3-((1-methylpyrrolidin-3-yl)oxy)-5-(trifluoromethyl)phenyl)-6-(pyrazolo[1,5-a]pyrazin-3-yloxy)-1H-imidazo[4,5-b]pyridin-2-amine

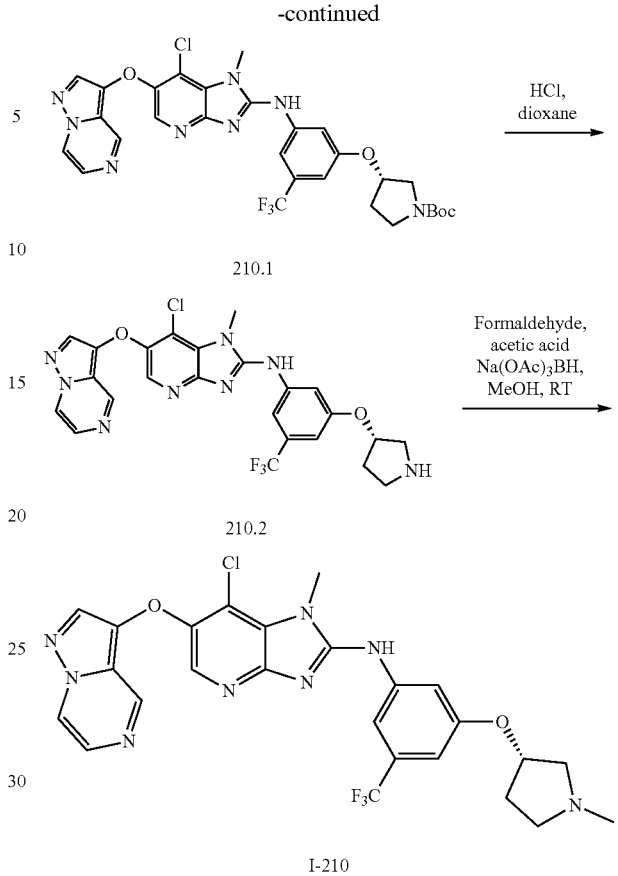

I-210

Synthesis of I-210. Compound I-210 was prepared from 21.7 and Int-105, following the procedures described in the synthesis of I-209. The final product was purified by flash column chromatography on silica gel (CombiFlash®, 12% methanol in DCM). MS (ES): m/z 559.2 [M+H]⁺, LCMS purity: 100%, HPLC purity: 98.46%, Chiral HPLC purity: 99.81%, ¹H NMR (DMSO-d₆, 400 MHz): δ 10.03 (s, 1H), 9.03 (bs, 1H), 8.70-8.69 (d, J=3.6 Hz, 1H), 8.21 (s, 1H), 8.05 (bs, 2H), 7.97 (s, 1H), 7.88-7.87 (d, J=4.8 Hz, 1H), 6.88 (s, 1H), 5.11 (bs, 1H), 4.09 (s, 3H), 3.08 (bs, 2H), 2.87 (bs, 1H), 2.57 (bs, 5H), 2.02 (bs, 1H).

Example 211: 5-cyclopropyl-3-((7-methoxy-6-((4-methoxypyrazolo[1,5-a]pyrazin-3-yl)oxy)-1-methyl-1H-imidazo[4,5-b]pyridin-2-yl)amino)-1-methylpyridin-2(1H)-one

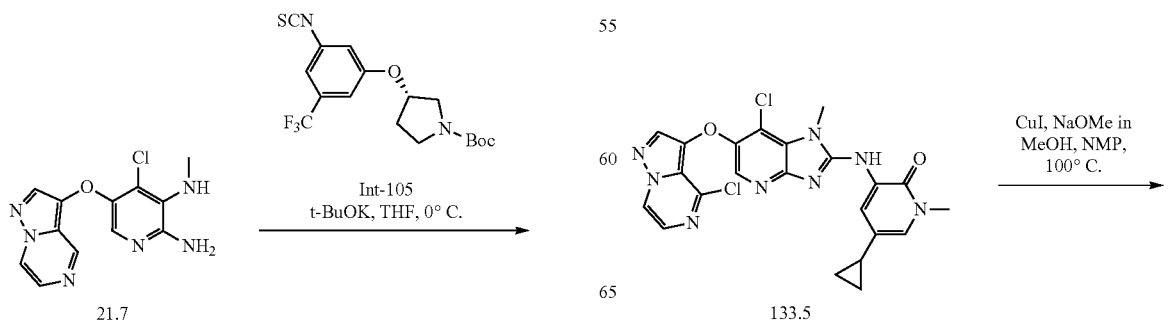

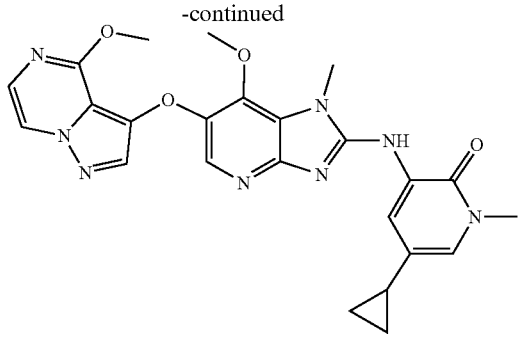

I-211

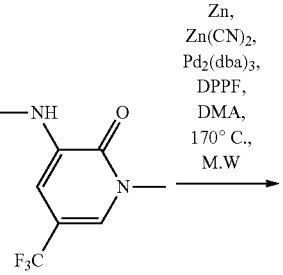

212.1

Synthesis of I-211. To a solution of 133.5 (0.100 g, 0.201 mmol, 1.0 equiv) in N-methyl-2-pyrrolidone (1.0 mL) was added sodium methoxide solution (5 N in methanol, 1.0 mL) followed by copper iodide (0.007 g, 0.040 mmol, 0.2 equiv) at room temperature. The mixture was stirred at 100° C. for 16 h. It was poured over ice-water and extracted with ethyl acetate. The combined organic layers were washed with brine, dried over anhydrous sodium sulfate, filtered and concentrated under reduced pressure. The residue was purified by preparative HPLC to afford I-211. MS (ES): m/z 489.2 [M+H]$^+$, $^1$H NMR (DMSO-d$_6$, 400 MHz): δ 8.34 (s, 1H), 8.30 (s, 1H), 8.28-8.27 (d, J=5.2 Hz, 1H), 7.97 (s, 1H), 7.78 (s, 1H), 7.39-7.38 (d, J=4.8 Hz, 1H), 7.19 (s, 1H), 4.09 (s, 3H), 4.01 (s, 3H), 3.89 (s, 3H), 3.55 (s, 3H), 1.81 (bs, 1H), 0.88-0.86 (m, 2H), 0.59-0.58 (m, 2H).

Example 212: 1-methyl-2-((1-methyl-2-oxo-5-(trifluoromethyl)-1,2-dihydropyridin-3-yl)amino)-6-(pyrazolo[1,5-a]pyridin-3-yloxy)-1H-imidazo[4,5-b]pyridine-7-carbonitrile

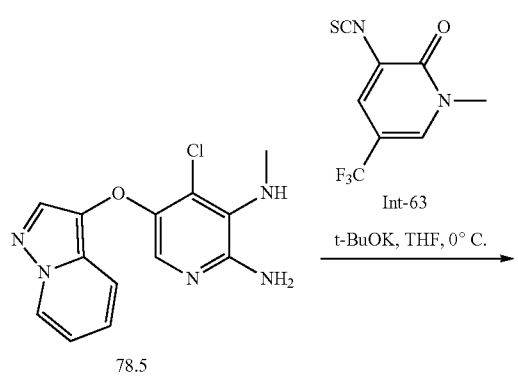

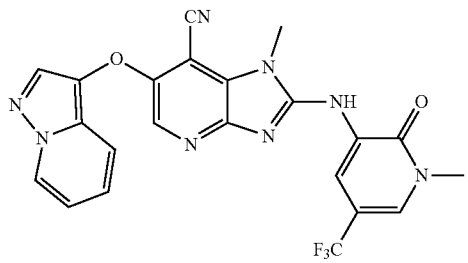

I-212

Synthesis of compound 212.1. Compound 212.1 was prepared from 78.5 and Int-63, following the procedure described in the synthesis of I-13. The product was purified by flash column chromatography on silica gel (CombiFlash®, 3.2% methanol in DCM). MS (ES): m/z 490.5 [M+H]$^+$.

Synthesis of I-212. Compound I-212 was prepared from 212.1, following the procedure described in the synthesis of I-157. The product was purified by flash column chromatography on silica gel (CombiFlash®, 2.8% methanol in DCM). MS (ES): m/z 481.2 [M+H]$^+$, $^1$H NMR (DMSO-d$_6$, 400 MHz): δ 8.95 (s, 1H), 8.68-8.67 (d, J=6.8 Hz, 1H), 8.60 (s, 1H), 8.18 (s, 1H), 8.15 (s, 1H), 7.95 (s, 1H), 7.55-7.53 (d, J=9.2 Hz, 1H), 7.25-7.21 (m, 1H), 6.96-6.92 (m, 1H), 3.98 (s, 3H), 3.65 (s, 3H).

Example 213: cis-3-((7-chloro-6-((5-fluoropyrazolo[1,5-a]pyridin-3-yl)oxy)-1-methyl-1H-imidazo[4,5-b]pyridin-2-yl)amino)-1-(3-hydroxycyclobutyl)-5-(trifluoromethyl)pyridin-2(1H)-one

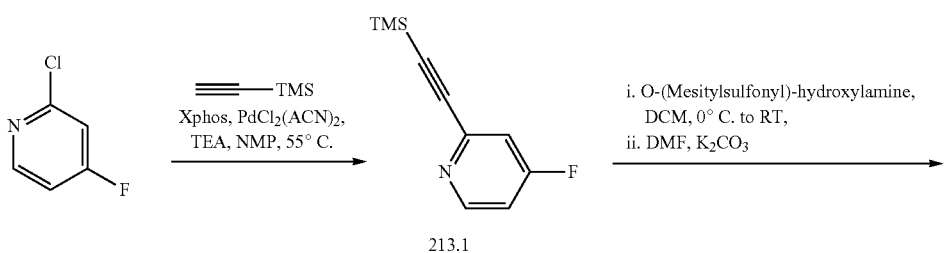

213.1

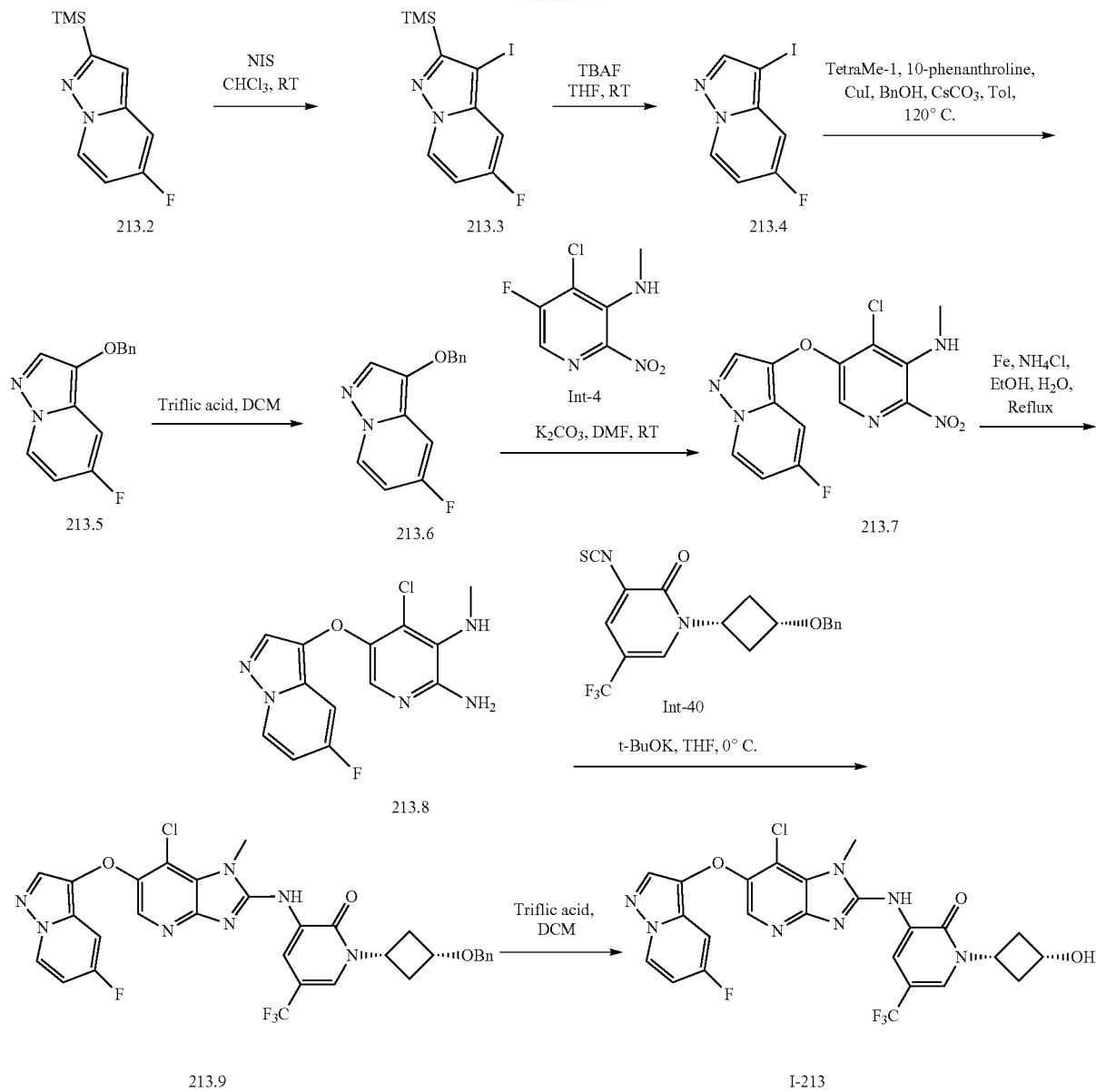

Synthesis of compound 213.1. A mixture of 2-chloro-4-fluoropyridine (20 g, 152.05 mmol, 1.0 equiv), ethynyltrimethylsilane (32.86 g, 334.51 mmol, 2.2 equiv), bis(acetonitrile)dichloropalladium(II) (1.96 g, 7.6 mmol, 0.05 equiv) and 2-dicyclohexylphosphino-2',4',6'-triisopropylbiphenyl (0.723 g, 1.52 mmol, 0.01 equiv) in N-methyl-2-pyrrolidone (140 mL) was degassed for 30 min. Under argon atmosphere was added triethylamine (30.7 g, 304.1 mmol, 2.0 equiv) and degassed for 5 min. The reaction mixture was stirred at 55° C. for 24 h. It was poured over brine and extracted with ethyl acetate. The combined organic layers were washed with brine, dried over anhydrous sodium sulfate, filtered and concentrated under reduced pressure. The residue was purified by flash column chromatography on silica gel (CombiFlash®, 4% ethyl acetate in hexane) to afford 213.1. MS (ES): m/z 194.3 [M+H]⁺.

Synthesis of compound 213.2. To a solution of 213.1 (3.8 g, 19.66 mmol, 1.0 equiv) in DCM (38 mL), was added O-(mesitylsulfonyl)-hydroxylamine (4.2 g, 19.66 mmol, 1.0 equiv) at 0° C. The reaction mixture was stirred at room temperature for 48 h. It was concentrated under reduced pressure and residue was dissolved in DMF (25 mL), followed by the addition of potassium carbonate (8.1 g, 58.98 mmol, 3.0 equiv). The reaction mixture was stirred at room temperature for 24 h. It was poured over brine and extracted with ethyl acetate. The combined organic layers were washed with brine, dried over anhydrous sodium sulfate, filtered and concentrated under reduced pressure. The residue was purified by flash column chromatography on silica gel (CombiFlash®, 12% ethyl acetate in hexane) to afford 213.2. MS (ES): m/z 209.1 [M+H]⁺.

Synthesis of compound 213.3. To a solution of 213.2 (1.2 g, 5.76 mmol, 1.0 equiv) in chloroform (18 mL) was added N-iodosuccinimide (1.42 g, 6.33 mmol, 1.1 equiv) at room temperature. The reaction mixture was stirred at room temperature for 1 h. The reaction mixture was transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 10% ethyl acetate in hexane) to afford 213.3. MS (ES): m/z 335.2 [M+H]⁺.

Synthesis of compound 213.4. To a solution of 213.3 (1.3 g, 3.89 mmol, 1.0 equiv) in THF (2 mL) was added tetra-n-butylammoniumfluoride (1 M in THF, 1.3 mL, 1 volume) at 0° C. The reaction mixture was stirred at room temperature for 4-5 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 16% ethyl acetate in hexane) to afford 213.4. MS (ES): m/z 263.0 [M+H]⁺.

Synthesis of compound 213.5. A mixture of 213.4 (0.400 g, 1.53 mmol, 1 equiv), benzyl alcohol (0.413 g, 3.82 mmol, 2.5 equiv) and cesium carbonate (0.994 g, 3.06 mmol, 2 equiv) in toluene was degassed by bubbling through a stream of argon for 15 min. Copper iodide (0.020 g, 0.107 mmol, 0.07 equiv) and 3,4,7,8-tetramethyl-1,10-phenanthroline (0.036 g, 0.153 mmol, 0.1 equiv) were added. The reaction mixture was stirred at room temperature for 20 min and heated to 120° C. for 24 h. The reaction mixture was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 24% ethyl acetate in hexane) to afford 213.5. MS (ES): m/z 243.1 [M+H]⁺.

Synthesis of compound 213.6. Compound 213.6 was prepared from 213.5, following the procedure described in the synthesis of I-23. The product was purified by flash column chromatography on silica gel (CombiFlash®, 28% ethyl acetate in hexane). MS (ES): m/z 153.1 [M+H]⁺.

Synthesis of compound 213.7. Compound 213.7 was prepared from 213.6 and Int-4, following the procedure described in the synthesis of 19.1. The product was purified by flash column chromatography on silica gel (CombiFlash®, 25% ethyl acetate in hexane). MS (ES): m/z 338.5 [M+H]⁺.

Synthesis of compound 213.8. Compound 213.8 was prepared from 213.7, following the procedure described in the synthesis of 5.4. The product was purified by flash column chromatography on silica gel (CombiFlash®, 1.7% methanol in DCM). MS (ES): m/z 308.6 [M+H]⁺.

Synthesis of compound 213.9. Compound 213.9 was prepared from 213.8 and Int-40, following the procedures described in the synthesis of I-13. The final product was purified by flash column chromatography on silica gel (CombiFlash®, 2.5% methanol in DCM). MS (ES): m/z 655.0 [M+H]⁺.

Synthesis of I-213. Compound I-213 was prepared from 213.9, following the procedure described in the synthesis of I-23. The product was purified by trituration in diethyl ether. MS (ES): m/z 564.2 [M+H]⁺, ¹H NMR (MeOD, 400 MHz): δ 8.66-8.65 (d, J=1.8 Hz, 1H), 8.62-8.59 (m, 1H), 8.08 (s, 1H), 8.04 (s, 1H), 8.02 (s, 1H), 7.33-7.31 (m, 1H), 6.94-6.90 (m, 1H), 4.77-4.75 (m, 1H), 4.23-4.19 (m, 4H), 3.02-3.01 (m, 2H), 2.27-2.25 (m, 2H).

Example 214: 3-((7-chloro-1-methyl-6-((4-(methylamino)pyrazolo[1,5-a]pyrazin-3-yl)oxy)-1H-imidazo[4,5-b]pyridin-2-yl)amino)-1-((1s,3s)-3-hydroxycyclobutyl)-5-(trifluoromethyl)pyridin-2(1H)-one

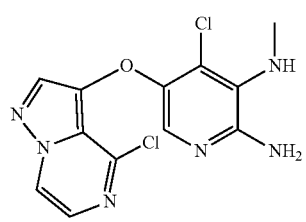

124.7

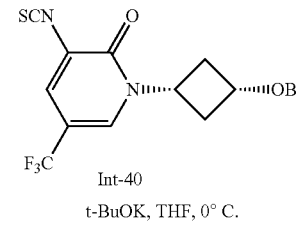

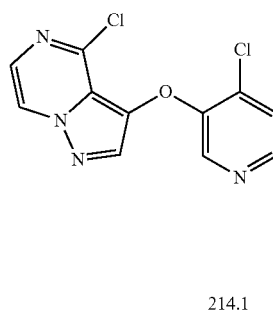

214.1

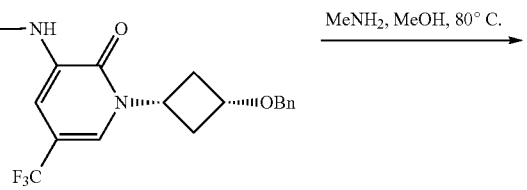

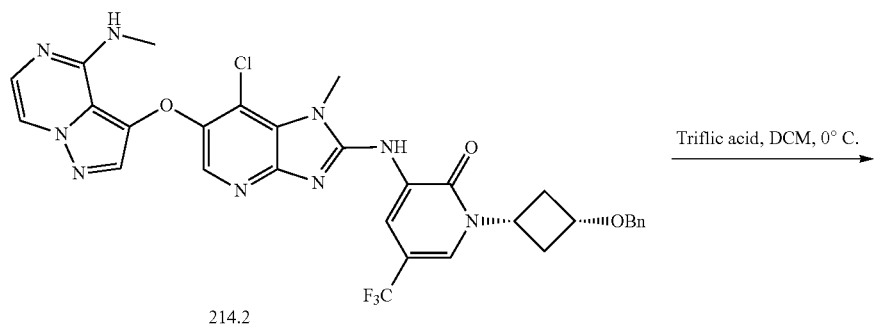

214.2

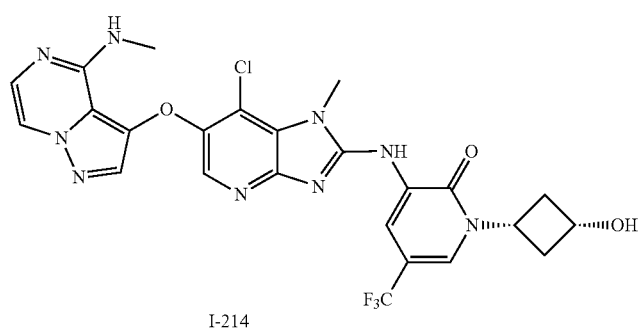

I-214

Synthesis of compound 214.1. Compound 214.1 was prepared from 124.7 and Int-40, following the procedure described in the synthesis of I-13. The product was purified by flash column chromatography on silica gel (CombiFlash®, 1.2% methanol in DCM). MS (ES): m/z 672.2 [M+H]⁺.

Synthesis of compound 214.2. Compound 214.2 was prepared from 214.1, following the procedure described in the synthesis of I-171. The product was purified by flash column chromatography on silica gel (CombiFlash®, 3.5% methanol in DCM). MS (ES): m/z 666.7 [M+H]⁺.

Synthesis of I-214. Compound I-214 was prepared from 214.2, following the procedure described in the synthesis of I-23. The product was purified by flash column chromatography on silica gel (CombiFlash®, 4.7% methanol in DCM). MS (ES): m/z 576.2 [M+H]⁺, ¹H NMR (DMSO-d₆, 400 MHz): δ 8.87 (s, 1H), 865 (s, 1H), 8.25 (s, 1H), 7.92 (s, 1H), 7.79-7.78 (d, J=4.0 Hz, 1H), 7.51 (s, 1H), 7.27-7.26 (d, J=4.0 Hz, 1H), 6.84-6.83 (d, J=4.0 Hz, 1H), 5.31-5.29 (m, 1H), 4.68-4.63 (m, 1H), 4.06-4.02 (m, 4H), 3.01-2.99 (d, 3H), 2.86-2.84 (m, 2H), 2.22-2.20 (m, 2H).

Example 215: 7-chloro-N-(4-((dimethylamino)methyl)-2-fluoro-5-(trifluoromethyl)phenyl)-1-methyl-6-(pyrazolo[1,5-a]pyrazin-3-yloxy)-1H-imidazo[4,5-b]pyridin-2-amine

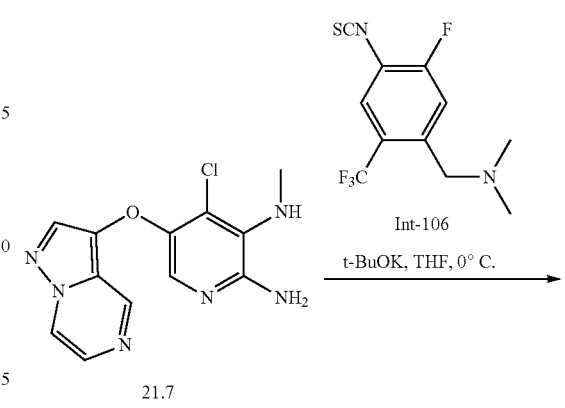

21.7

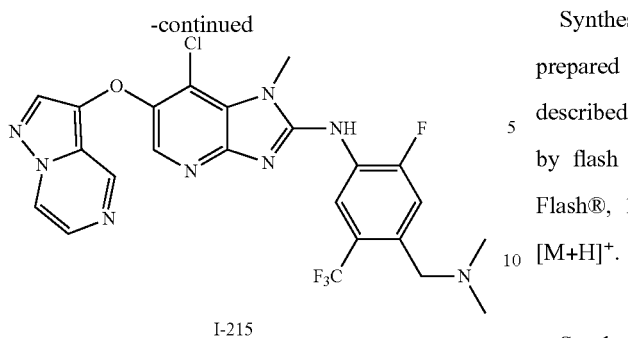

I-215

Synthesis of I-215. Compound I-215 was prepared from 21.7 and Int-106, following the procedure described in the synthesis of I-13. The product was purified by flash column chromatography on silica gel (CombiFlash®, 2.0% methanol in DCM). MS (ES): m/z 536.1 [M+H]+, ¹H NMR (DMSO-d₆, 400 MHz): δ 9.42 (s, 1H), 9.04 (s, 1H), 8.70-8.69 (d, J=4.0 Hz, 1H), 8.36-8.35 (d, J=4.0 Hz, 1H), 8.20 (s, 1H), 8.04 (s, 1H), 7.88-7.87 (d, J=4.0 Hz, 1H), 7.66-7.63 (d, J=8.4 Hz, 1H), 4.01 (s, 3H), 3.55 (s, 2H), 2.24 (s, 6H).

Example 216: 1-(4-((7-chloro-1-methyl-6-((4-(methylamino)pyrazolo[1,5-a]pyrazin-3-yl)oxy)-1H-imidazo[4,5-b]pyridin-2-yl)amino)-2-(trifluoromethyl)benzyl)azetidine-3-carbonitrile Synthesis of compound 216.1. Compound 216.1 was prepared from 124.7 and Int-107, following the procedure described in the synthesis of I-13. The product was purified by flash column chromatography on silica gel (CombiFlash®, 1.9% methanol in DCM). MS (ES): m/z 589.1 [M+H]+.

Synthesis of I-216. Compound I-216 was prepared from 216.1, following the procedure described in the synthesis of I-171. The product was purified by flash column chromatography on silica gel (CombiFlash®, 2.8% methanol in DCM). MS (ES): m/z 583.2 [M+H]+, ¹H NMR (DMSO-d₆, 400 MHz): δ 9.65 (s, 1H), 8.31 (s, 1H), 8.20 (s, 1H), 8.17 (s, 1H), 7.79-7.78 (d, J=4.8 Hz, 1H), 7.67-7.65 (d, J=8.4 Hz, 1H), 7.48 (s, 1H), 7.26-7.25 (d, J=4.8 Hz, 1H), 6.83-6.82 (d, J=4.4 Hz, 1H), 4.03 (s, 3H), 3.74 (s, 2H), 3.38 (bs, 1H), 3.54 (s, 4H), 3.00-2.99 (d, 3H).

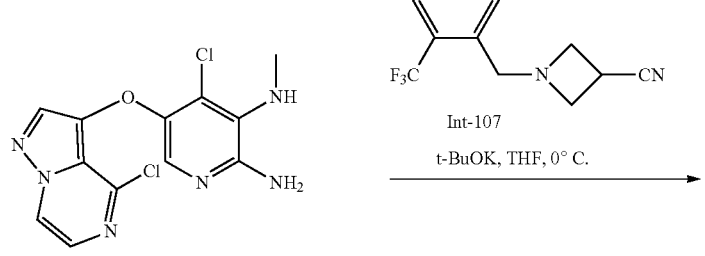

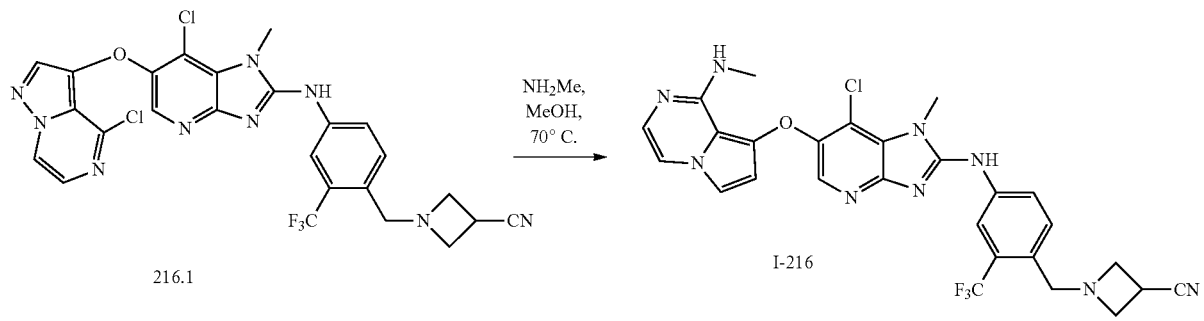

Example 217: 3-((7-chloro-1-methyl-6-((4-(methyl-amino)pyrazolo[1,5-a]pyrazin-3-yl)oxy)-1H-imidazo[4,5-b]pyridin-2-yl)amino)-1-(methyl-d₃)-5-(trifluoromethyl)pyridin-2(1H)-one

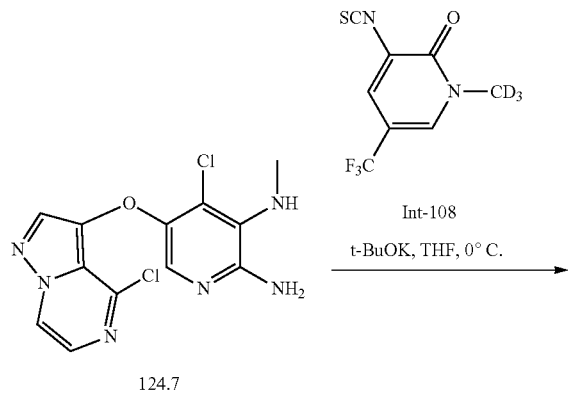

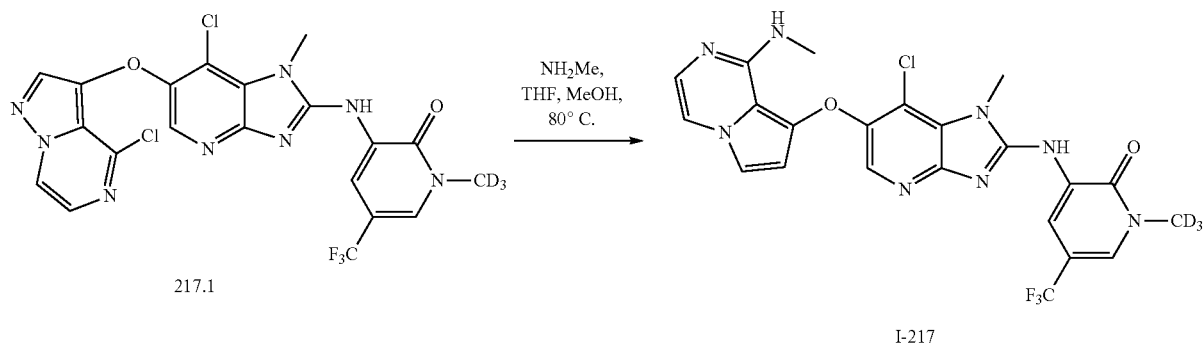

Synthesis of compound 217.1. Compound 217.1 was prepared from 124.7 and Int-108, following the procedure described in the synthesis of I-13. The product was purified by flash column chromatography on silica gel (CombiFlash®, 1.5% methanol in DCM). MS (ES): m/z 529 [M+H]⁺.

Synthesis of I-217. Compound I-217 was prepared from 217.1, following the procedure described in the synthesis of I-171. The product was purified by flash column chromatography on silica gel (CombiFlash®, 3.5% methanol in DCM). MS (ES): m/z 523.2 [M+H]⁺, ¹H NMR (DMSO-d₆, 400 MHz): δ 8.84 (s, 1H), 8.62 (s, 1H), 8.24 (s, 1H), 8.14 (s, 1H), 7.79-7.77 (d, J=4.8 Hz, 1H), 7.50 (s, 1H), 7.26-7.25 (d, J=4.8 Hz, 1H), 6.84 (s, 1H), 4.01 (s, 3H), 3.00-2.99 (d, 3H).

Example 218: 7-chloro-1-methyl-N-(3-((1-methyl-azetidin-3-yl)oxy)-5-(trifluoromethyl)phenyl)-6-(pyrazolo[1,5-a]pyrazin-3-yloxy)-1H-imidazo[4,5-b]pyridin-2-amine

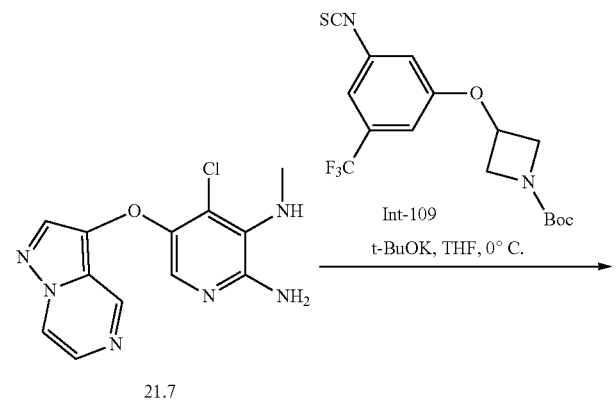

-continued

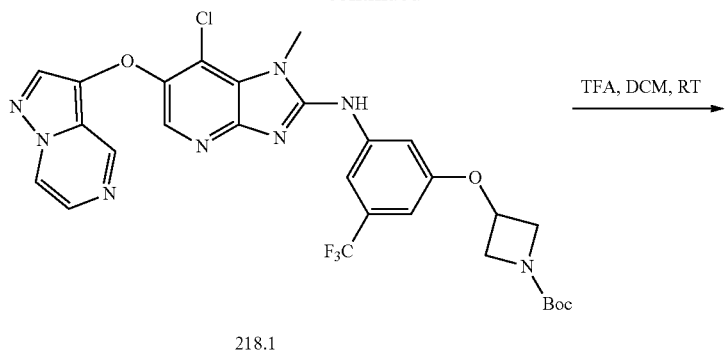

218.1

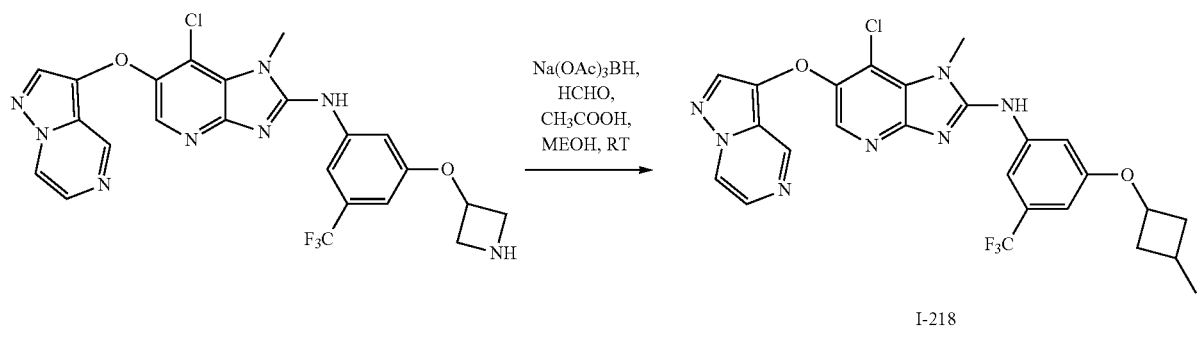

Synthesis of compound 218.1. Compound 218.1 was prepared from 21.7 and Int-109, following the procedure described in the synthesis of I-13. The product was purified by flash column chromatography on silica gel (Combi-Flash®, 1.5% methanol in DCM). MS (ES): m/z 632.0[M+H]+.

Synthesis of compound 218.2. To a solution of 218.1 (0.080 g, 0.126 mmol, 1.0 equiv) in DCM (3 mL) was added trifluoroacetic acid (0.2 mL) dropwise at 0° C. The reaction mixture was stirred at room temperature for 2 h. It was concentrated under reduced pressure to afford residue which was triturated with diethyl ether to afford 218.2. MS (ES): m/z 531.8 [M+H]+.

Synthesis I-218. To a solution of 218.2 (0.050 g, 0.094 mmol, 1.0 equiv) in methanol (2 mL) was added formaldehyde (0.014 g, 0.47 mmol, 5.0 equiv), sodium triacetoxyborohydride (0.039 g, 0.188 mmol, 2.0 equiv) and acetic acid (0.1 mL). The reaction mixture was stirred at room temperature for 30 min. The reaction mixture was poured over ice-water and extracted with ethyl acetate. The combined organic layers were washed with brine, dried over anhydrous sodium sulfate, filtered and concentrated under reduced pressure. The residue was purified by preparative HPLC to afford I-218. MS (ES): m/z 545.2 [M+H]+, 1H NMR (DMSO-d6, 400 MHz): 9.66 (s, 1H), 9.03 (s, 1H), 8.70-8.69 (d, J=4.0 Hz, 1H), 8.23 (s, 1H), 8.20 (s, 1H), 8.04 (s, 1H), 7.91-7.86 (m, 2H), 6.78 (s, 1H), 4.86-4.85 (m, 1H), 4.03 (s, 3H), 3.82 (bs, 2H), 3.05 (bs, 2H), 2.33 (s, 3H).

Example 219: 7-chloro-1-methyl-N-(3-(4-methyl-1H-imidazol-1-yl)-5-(trifluoromethyl)phenyl)-6-((4-(methylamino)pyrazolo[1,5-a]pyrazin-3-yl)oxy)-1H-imidazo[4,5-b]pyridin-2-amine

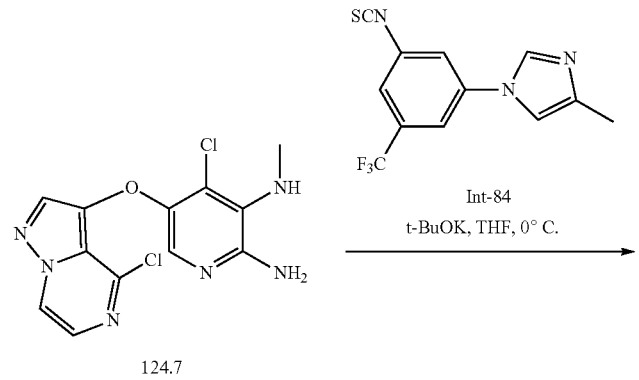

124.7

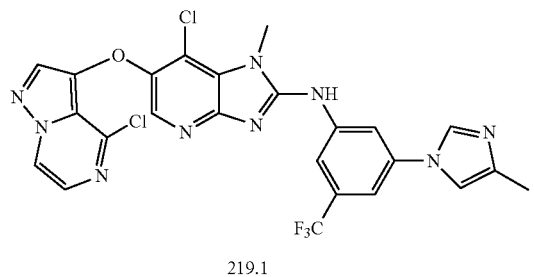

219.1

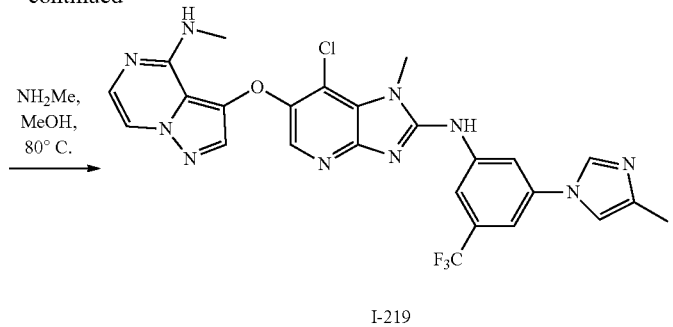

I-219

Synthesis of compound 219.1. Compound 219.1 was prepared from 124.7 and Int-84, following the procedure described in the synthesis of I-13. The product was purified by column using 2.8% methanol in DCM). MS (ES): m/z 575.2 [M+H]$^+$.

Synthesis of I-219. Compound I-219 was prepared from 219.1, following the procedure described in the synthesis of I-171. The product was purified by flash column chromatography on silica gel (CombiFlash®, 4.2% methanol in DCM). MS (ES): m/z 569.1 [M+H]$^+$, $^1$H NMR (DMSO-d$_6$, 400 MHz): δ 9.87 (s, 1H), 8.39 (s, 1H), 8.30 (s, 1H), 8.22-8.21 (d, J=5.6 Hz, 2H), 7.78-7.77 (d, J=4.4 Hz, 1H), 7.65 (s, 1H), 7.47 (bs, 2H), 7.26-7.24 (d, J=4.8 Hz, 1H), 6.83 (s, 1H), 4.05 (s, 3H), 2.99-2.98 (d, 3H), 2.20 (s, 3H).

Example 220: 7-chloro-1-methyl-6-((4-(methylamino)pyrazolo[1,5-a]pyrazin-3-yl)oxy)-N-(3-(4-methylpiperazin-1-yl)-5-(trifluoromethyl)phenyl)-1H-imidazo[4,5-b]pyridin-2-amine Synthesis of compound 220.1 Compound 220.1 was prepared from 124.7 and Int-78, following the procedure described in the synthesis of I-13. The product was purified by flash column chromatography on silica gel (CombiFlash®, 5.2% methanol in DCM). MS (ES): m/z 593.2 [M+H]$^+$.

Synthesis of I-220. Compound I-220 was prepared from 220.1, following the procedure described in the synthesis of I-171. The product was purified by trituration with methanol. MS (ES): m/z 587.2 [M+H]$^+$, $^1$H NMR (DMSO-d$_6$, 400 MHz): δ 9.58 (s, 1H), 8.21 (s, 1H), 7.86 (s, 1H), 7.80-7.79 (m, 2H), 7.48 (s, 1H), 7.28-7.27 (d, J=4.8 Hz, 1H), 6.95 (s, 1H), 6.85-6.84 (d, J=4.4 Hz, 1H), 4.05 (bs, 4H), 3.02-3.01 (d, 4H), 2.70 (s, 3H), 2.39 (bs, 6H).

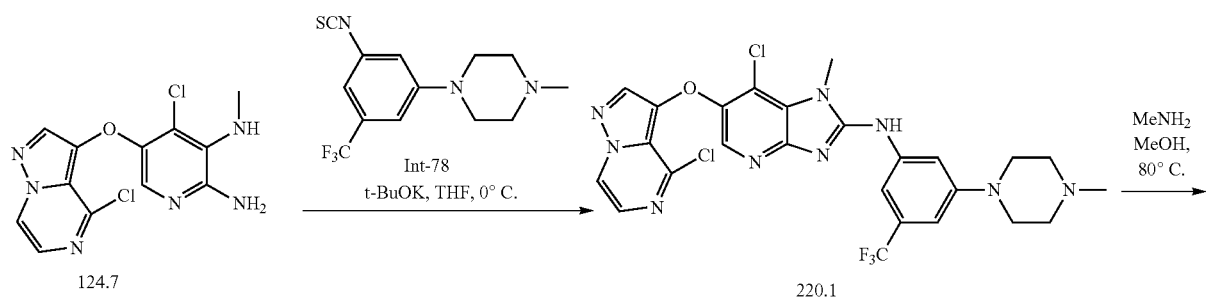

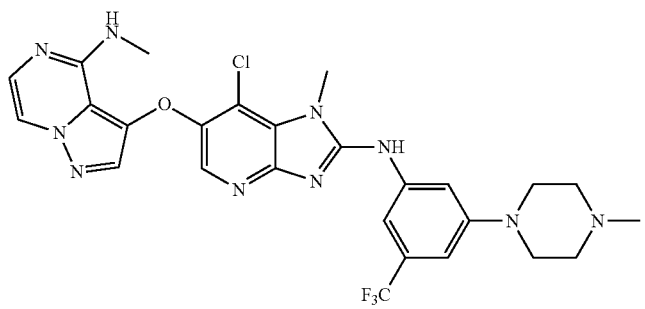

I-220

Example 221: 1-methyl-3-((1-methyl-6-((4-(methyl-amino)pyrazolo[1,5-a]pyrazin-3-yl)oxy)-1H-imidazo[4,5-b]pyridin-2-yl)amino)-5-(trifluoromethyl)pyridin-2(1H)-one Synthesis of I-221. Compound I-221 was prepared from 221.3, following the procedure described in the synthesis of I-171. The product was purified by flash column chromatography on silica gel (CombiFlash®, 5.5% methanol in DCM). MS (ES): m/z 486.43[M+H]$^+$, $^1$H NMR (MeOD,

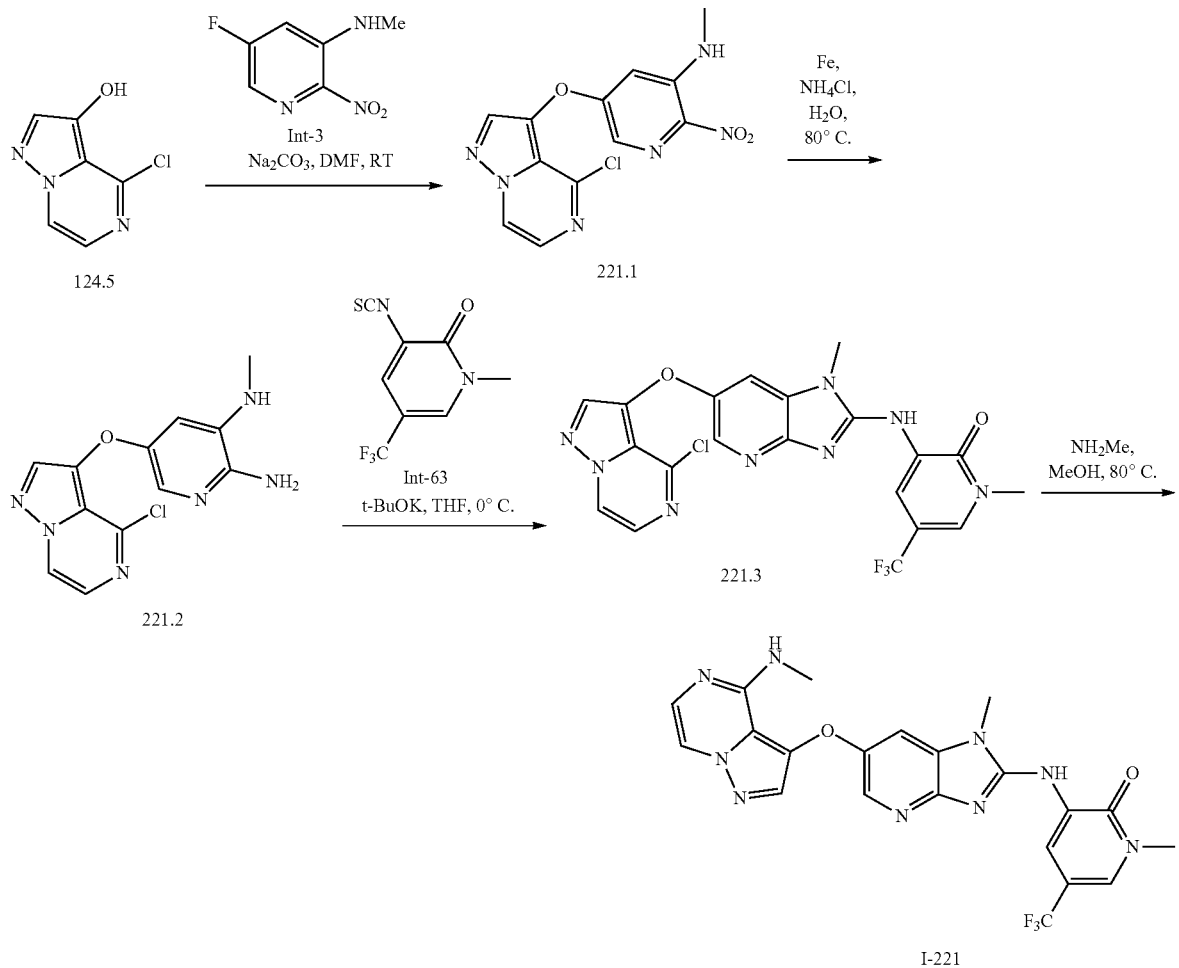

400 MHz): δ 8.89 (s, 1H), 8.52 (bs, 1H), 8.23 (s, 1H), 7.89 (s, 1H), 7.72 (bs, 2H), 7.63 (s, 1H), 7.26 (bs, 1H), 3.79 (s, 3H), 3.76-3.75 (d, 3H), 3.08 (s, 3H).

Synthesis of compound 221.1. To a mixture of Int-3 (0.1 g, 0.584 mmol, 1.0 equiv) and sodium carbonate (0.153 g, 1.46 mmol, 2.5 equiv) in DMF (2 mL) was added 124.5 (0.099 g, 0.584 mmol, 1.0 equiv) and the reaction mixture was stirred at room temperature for 1 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 20% ethyl acetate in hexane) to afford 221.1. MS (ES): m/z 321.5 [M+H]$^+$.

Synthesis of compound 221.2. Compound 221.2 was prepared from 221.1, following the procedure described in the synthesis of 5.4. The product was purified by flash column chromatography on silica gel (CombiFlash®, 30% ethyl acetate in hexane). MS (ES): m/z 291.2 [M+H]$^+$.

Synthesis of compound 221.3 Compound 221.3 was prepared from 221.2 and Int-63, following the procedure described in the synthesis of I-13. The product was purified by flash column chromatography on silica gel (CombiFlash®, 3.2% methanol in DCM). MS (ES): m/z 491.6 [M+H]$^+$.

Example 222: 3-((6-((4-(benzyl(methyl)amino)pyrazolo[1,5-a]pyrazin-3-yl)oxy)-7-chloro-1-methyl-1H-imidazo[4,5-b]pyridin-2-yl)oxy)-5-cyclopropyl-1-isopropylpyridin-2(1H)-one

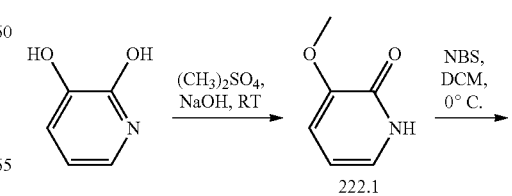

865
-continued
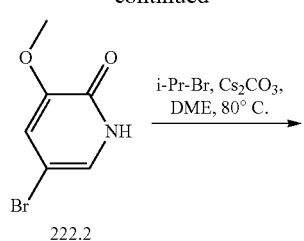
222.2
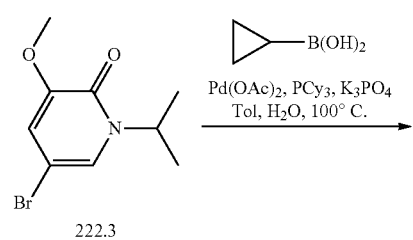
222.3
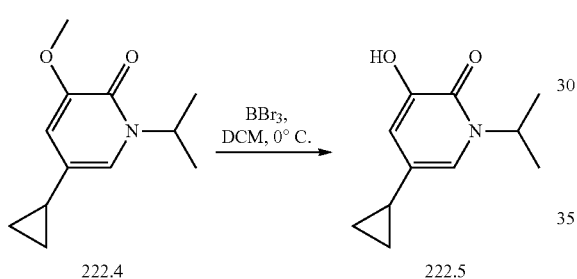
222.4  222.5
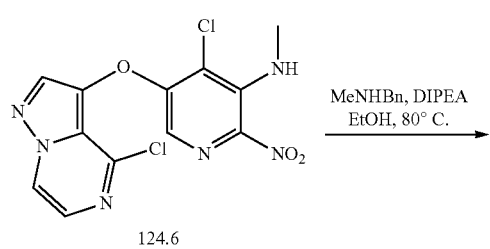
124.6
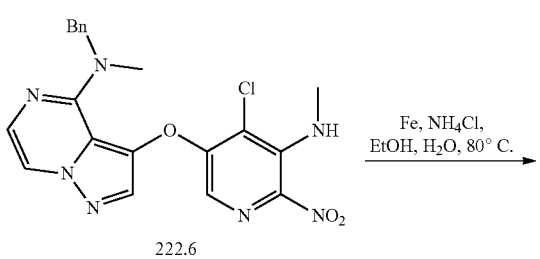
222.6
866
-continued
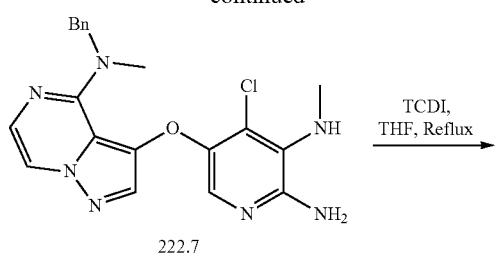
222.7
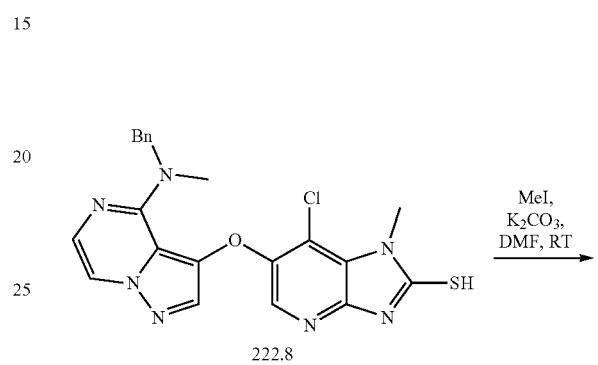
222.8
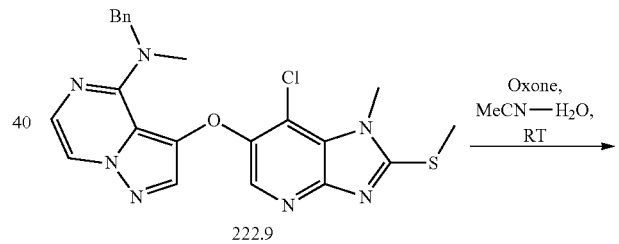
222.9
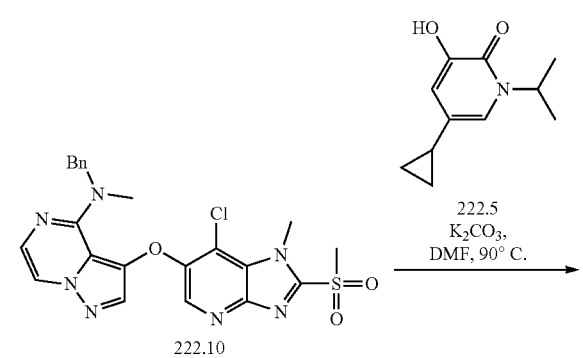
222.10

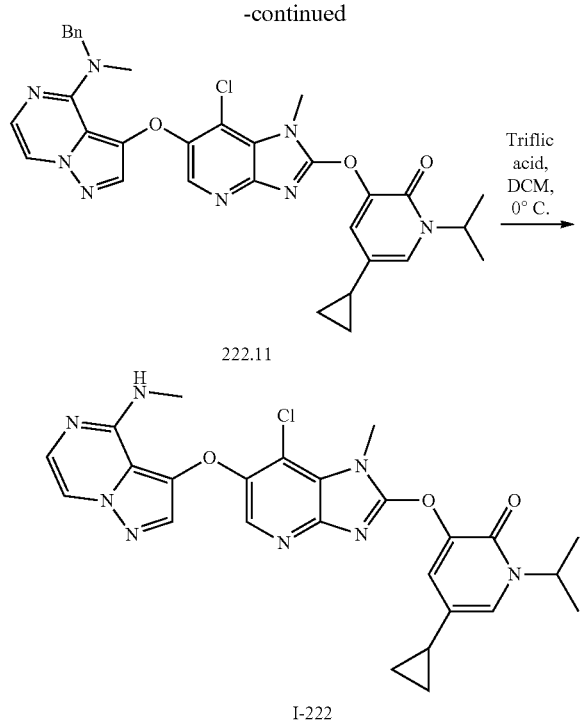

Synthesis of compound 222.1. To a 1 M aqueous solution of sodium hydroxide (51 mL, 135 mmol, 1.0 equiv) at 0° C. was added pyridine-2,3-diol (15 g, 135 mmol, 1.0 equiv). After 15 min, dimethyl sulfate (12.8 mL, 135 mmol, 1.0 equiv) was added at 0° C. The reaction mixture was stirred at room temperature for 3 h. It was neutralized with acetic acid to pH 7 and extracted with dichloromethane. The combined organic layers were washed with brine, dried over anhydrous sodium sulfate, filtered and concentrated under reduced pressure. The residue was purified by flash column chromatography on silica gel (CombiFlash®, 3.2% methanol in dichloromethane) to afford 222.1. MS (ES): m/z 126.2 [M+H]$^+$.

Synthesis of compound 222.2. To a solution of 222.1 (4.0 g, 31.97 mmol, 1.0 equiv) in dichloromethane (40 mL) was added N-bromosuccinimide (6.79 g, 38.36 mmol, 1.2 equiv) at 0° C. The reaction mixture was stirred at room temperature for 30 min. It was poured over ice-water, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 3% methanol in dichloromethane) to afford 222.2. MS (ES): m/z 205.1 [M+H]$^+$.

Synthesis of compound 222.3. To a solution of 222.2 (2.0 g, 9.8 mmol, 1.0 equiv) in dimethoxyethane (20 mL) was added cesium carbonate (7.96 g, 24.5 mmol, 2.5 equiv) and stirred at room temperature for 15 min. To the mixture was added 2-bromopropane (2.41 g, 19.61 mmol, 1.5 equiv). The reaction mixture was stirred at 80° C. for 16 h. It was poured over ice-water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 1.1% methanol in dichloromethane) to afford 222.3. MS (ES): m/z 247.1 [M+H]$^+$.

Synthesis of compound 222.4. Compound 222.4 was prepared from 222.3 following the procedure described in the synthesis of Int-23.2. The product was purified by flash column chromatography on silica gel (CombiFlash®, 2.5% methanol in dichloromethane). MS (ES): m/z 180.2 [M+H]$^+$.

Synthesis of compound 222.5. To a solution of 222.4 (0.950 g, 4.58 mmol, 1.0 equiv) in dichloromethane (10 mL) was added boron tribromide (0.88 mL, 9.16 mmol, 2.0 equiv) at 0° C. The reaction mixture was stirred for 30 min. It was poured over saturated sodium bicarbonate solution, stirred and extracted with dichloromethane. The combined organic layers were washed with brine, dried over anhydrous sodium sulfate, filtered and concentrated under reduced pressure. The residue was purified by flash column chromatography on silica gel (CombiFlash®, 1.5% methanol in dichloromethane as eluant) to afford 222.5. MS (ES): m/z 194.3 [M+H]$^+$.

Synthesis of compound 222.6. To a solution of 124.6 (0.8 g, 2.25 mmol, 1.0 equiv) in ethanol (20 mL) was added N-diisopropylethylamine (0.870 g, 6.75 mmol, 3.0 equiv) followed by N-methylbenzylamine (1.361 g, 11.25 mmol, 5.0 equiv) and the reaction mixture was stirred at 80° C. for 16 h. It was cooled to room temperature, poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 50% ethyl acetate in hexane) to afford 222.6. MS (ES): m/z 440.5 [M+H]$^+$.

Synthesis of compound 222.7. Compound 222.7 was prepared from 222.6, following the procedure described in the synthesis of 5.4. The product was used in the next step without purification. MS (ES): m/z 410.5 [M+H]$^+$.

Synthesis of compound 222.8. To a solution of 222.7 (0.490 g, 1.20 mmol, 1.0 equiv) in THF (5 mL) was added thiocarbonyldiimidazole (1.068 g, 6.0 mmol, 5.0 equiv). The reaction mixture was heated to reflux for 1 h. It was concentrated under reduced pressure to afford residue which was transferred into water and precipitated product was filtered and dried well to afford 222.8. MS (ES): m/z 452.8 [M+H]$^+$.

Synthesis of compound 222.9. To a solution of 222.8 (0.390 g, 0.862 mmol, 1.0 equiv) in DMF (10 mL) was added potassium carbonate (0.237 g, 1.724 mmol, 2.0 equiv) followed by addition of methyl iodide (0.134 g, 0.948 mmol, 1.1 equiv). The reaction mixture was stirred at room temperature for 30 min. It was poured over ice-water and stirred. The precipitated solids were collected by filtration and dried under vacuum to afford 222.9. MS (ES): m/z 466.7 [M+H]$^+$.

Synthesis of compound 222.10. To a solution of 222.9 (0.310 g, 0.665 mmol, 1.0 equiv) in acetonitrile:water (1:1) (10 mL) was added oxone (0.857 g, 1.396 mmol, 2.1 equiv) and the reaction mixture was stirred at room temperature for 30 min. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.1% methanol in DCM) to afford 222.10. MS (ES): m/z 498.6 [M+H]$^+$.

Synthesis of compound 222.11. A mixture of 222.10 (0.180 g, 0.361 mmol, 1.0 equiv), 222.5 (0.069 g, 0.361 mmol, 1.0 equiv) and potassium carbonate (0.149 g, 1.083 mmol, 3.0 equiv) in DMF (5 mL) was stirred at 80° C. for 4 h. It was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 2.6% methanol in DCM) to afford 222.11. MS (ES): m/z 611.9 [M+H]⁺.

Synthesis of I-222. Compound I-222 was prepared from 222.11, following the procedure described in the synthesis of I-23. The product was purified by flash column chromatography on silica gel (CombiFlash®, 3.9% methanol in DCM). MS (ES): m/z 521.2 [M+H]⁺, ¹H NMR (DMSO-d₆, 400 MHz): δ 8.27 (s, 1H), 7.95 (s, 1H), 7.77-7.75 (d, J=8.0 Hz, 1H), 7.52 (s, 1H), 7.25 (s, 1H), 6.81 (s, 1H), 6.37 (bs, 1H), 5.02 (bs, 1H), 4.00 (s, 3H), 2.98 (s, 3H), 1.34-1.33 (d, 6H), 1.25 (bs, 1H), 1.10 (bs, 2H), 0.78 (bs, 2H).

Example 223: 3-((7-chloro-1-methyl-6-((4-(methylamino)pyrazolo[1,5-a]pyrazin-3-yl)oxy)-1H-imidazo[4,5-b]pyridin-2-yl)amino)-5-(trifluoromethyl)pyridin-2(1H)-one

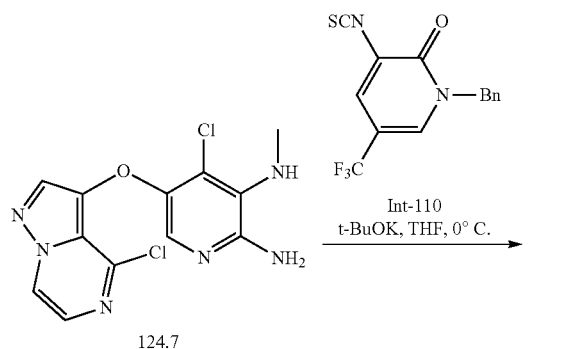

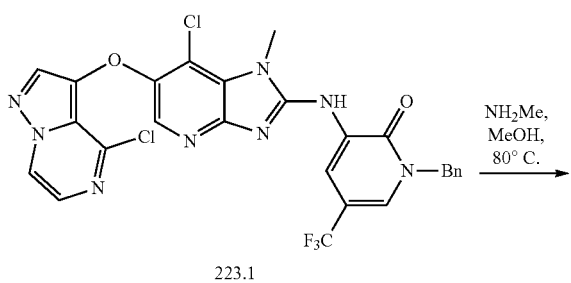

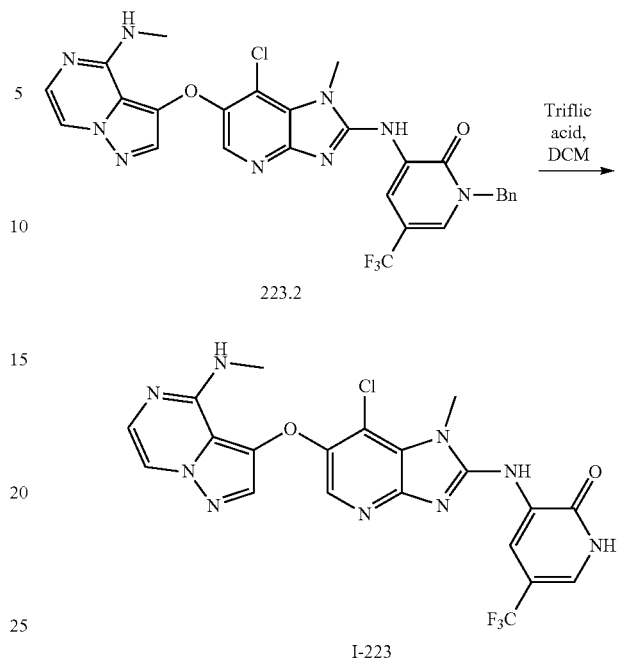

Synthesis of compound 223.1. Compound 223.1 was prepared from 124.7 and Int-110, following the procedure described in the synthesis of I-13. The product was purified by flash column chromatography on silica gel (CombiFlash®, 1.2% methanol in DCM). m/z 602.2 [M+H]⁺.

Synthesis of compound 223.2. Compound 223.2 was prepared from 223.1, following the procedure described in the synthesis of I-171. The product was purified by trituration with methanol. MS (ES): m/z 596.5 [M+H]⁺.

Synthesis of I-223. Compound I-223 was prepared from 223.2, following the procedure described in the synthesis of I-23. The product was purified by trituration with methanol. MS (ES): m/z 506.8 [M+H]⁺, ¹H NMR (DMSO-d₆, 400 MHz): δ 12.72 (s, 1H), 8.79 (s, 1H), 8.64-8.63 (d, J=4.0 Hz, 1H), 8.24 (s, 1H), 7.79-7.78 (d, J=4.0 Hz, 1H), 7.70 (s, 1H), 7.51 (s, 1H), 7.27-7.26 (d, J=4.8 Hz, 1H), 6.84-6.83 (d, J=4.0 Hz, 1H), 4.02 (s, 3H), 3.00-2.99 (d, 3H).

Example 224: 3-((7-chloro-6-((4-methoxypyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

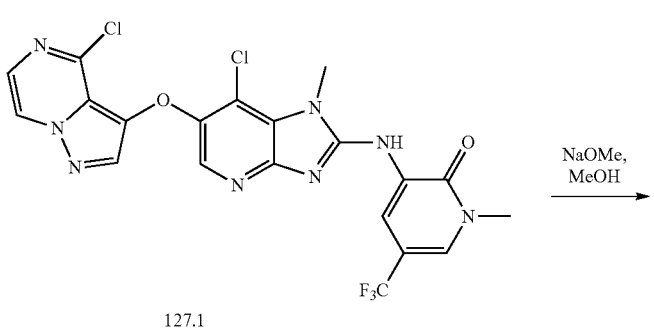

Synthesis of I-224. A solution of 127.1 (0.050 g, 0.095 mmol, 1.0 equiv) in sodium methoxide solution (25% in methanol, 3 mL) stirred at 80° C. for 2 h. It was concentrated under reduced pressure. The residue was purified by trituration with methanol to afford I-224. MS (ES): m/z 521.06 [M+H]$^+$, $^1$H NMR (DMSO-d$_6$, 400 MHz): δ 8.28 (bs, 2H), 8.21-8.19 (m, 3H), 7.94 (s, 1H), 7.36-7.35 (m, 1H), 4.07 (s, 3H), 3.88 (s, 3H), 3.62 (s, 3H).

Example 225: (S)-3-((7-chloro-1-methyl-6-((4-((tetrahydrofuran-3-yl)amino)pyrazolo[1,5-a]pyrazin-3-yl)oxy)-1H-imidazo[4,5-b]pyridin-2-yl)amino)-1-methyl-5-(trifluoromethyl)pyridin-2(1H)-one

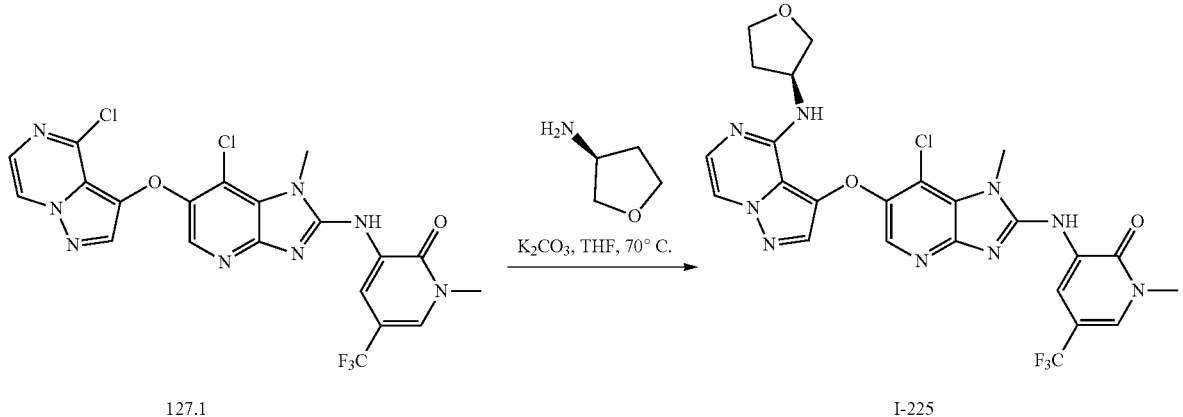

Synthesis of I-225. To a solution of 127.1 (0.050 g, 0.095 mmol, 1.0 equiv) in THF (3 mL) was added (S)-tetrahydrofuran-3-amine (0.082 g, 0.951 mmol, 10.0 equiv) followed by potassium carbonate (0.026 g, 0.190 mmol, 2.0 equiv). The reaction mixture was stirred at 80° C. for 3 days. It was cooled to room temperature, transferred into ice cold water and extracted with DCM. The combined organic layers were washed with brine, dried over anhydrous sodium sulfate, filtered and concentrated under reduced pressure. The residue was purified by trituration with methanol to afford I-225. MS (ES): m/z 576.2 [M+H]$^+$, $^1$H NMR (DMSO-d$_6$, 400 MHz): δ 8.63 (s, 1H), 8.31 (s, 1H), 8.15 (s, 1H), 7.89-7.88 (d, J=4.0 Hz, 1H), 7.68 (s, 1H), 7.30-7.29 (d, J=4.0 Hz, 1H), 6.32-6.31 (d, J=4.0 Hz, 1H), 4.68 (bs, 1H), 4.02 (s, 3H), 3.94-3.90 (m, 1H), 3.86-3.84 (m, 1H), 3.77-3.67 (m, 6H), 2.35-2.25 (m, 2H).

Example 226: 5-((7-chloro-1-methyl-6-((4-(methylamino)pyrazolo[1,5-a]pyrazin-3-yl)oxy)-1H-imidazo[4,5-b]pyridin-2-yl)amino)-2-fluoro-N,N-dimethyl-3-(trifluoromethyl)benzamide

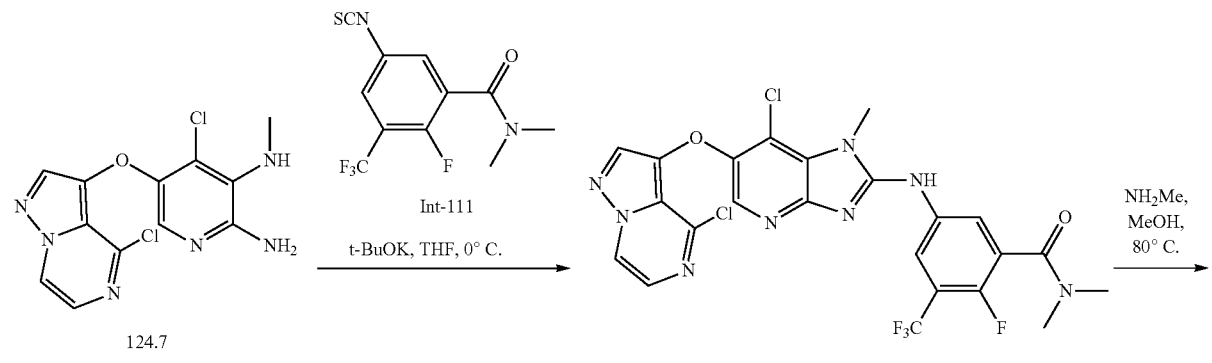

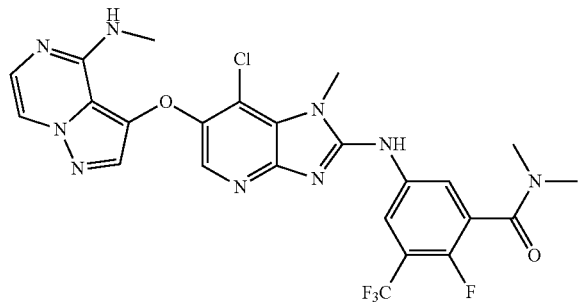

I-226

Synthesis of compound 226.1. Compound 226.1 was prepared from 124.7 and Int-111, following the procedure described in the synthesis of I-13. The product was purified by flash column chromatography on silica gel (Combi-Flash®, 3.0% methanol in DCM). MS (ES): m/z 584.1 [M+H]$^+$.

Synthesis of I-226. Compound I-226 was prepared from 226.1, following the procedure described in the synthesis of I-171. The product was purified by flash column chromatography on silica gel (CombiFlash®, 5.6% methanol in DCM). MS (ES): m/z 577.9 [M]$^+$, H NMR (DMSO-d$_6$, 400 MHz): δ 9.81 (s, 1H), 8.36 (bs, 2H), 8.21 (s, 1H), 7.79-7.78 (d, J=4.0 Hz, 1H), 7.48 (s, 1H), 7.27-7.26 (d, J=4.0 Hz, 1H), 6.82 (s, 1H), 4.04 (s, 3H), 3.08 (s, 3H), 3.01-3.00 (d, 3H), 2.94 (s, 3H).

Example 227: 7-chloro-1-methyl-6-((4-(methylamino)pyrazolo[1,5-a]pyrazin-3-yl)oxy)-N-(3-((1-methylpiperidin-4-yl)oxy)-5-(trifluoromethyl)phenyl)-1H-imidazo[4,5-b]pyridin-2-amine

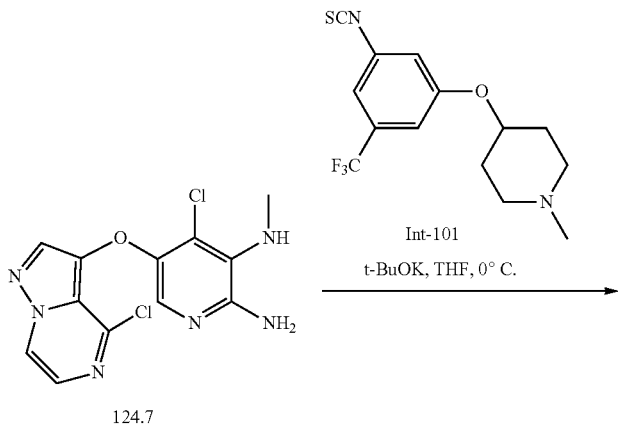

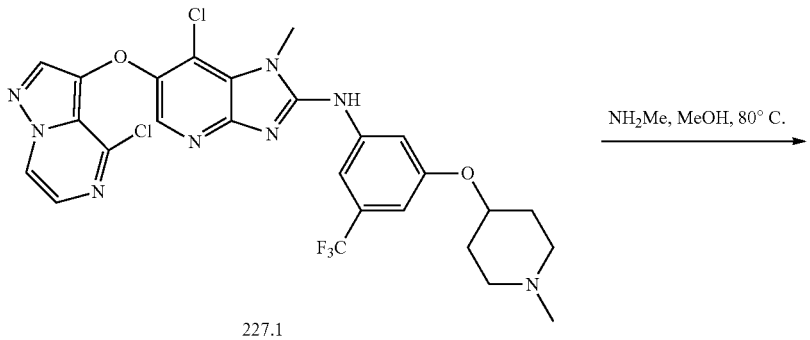

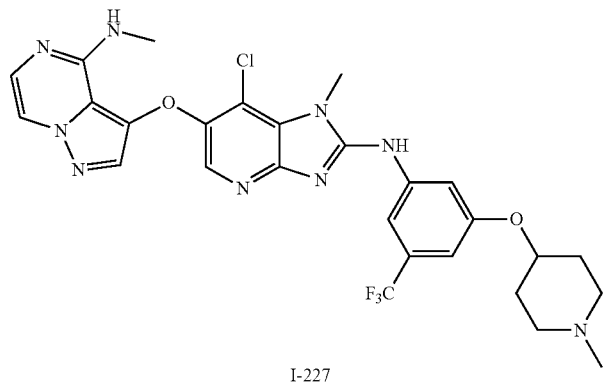

I-227

Synthesis of compound 227.1. Compound 227.1 was prepared from 124.7 and Int-101, following the procedure described in the synthesis of I-13. The product was purified by flash column chromatography on silica gel (Combi-Flash®, 5.0% methanol in DCM). MS (ES): m/z 608.2 [M+H]+.

Synthesis of I-227. Compound I-227 was prepared from 227.1, following the procedure described in the synthesis of I-171. The product was purified by flash column chromatography on silica gel (CombiFlash®, 10% methanol in DCM). MS (ES): m/z 603.2 [M+H]+, $^1$H NMR (DMSO-$d_6$, 400 MHz): δ 9.61 (s, 1H), 8.21 (s, 1H), 7.93 (s, 1H), 7.88 (s, 1H), 7.79-7.78 (d, J=4.8 Hz, 1H), 7.47 (s, 1H), 7.26-7.25 (d, J=4.8 Hz, 1H), 6.94 (s, 1H), 6.84-6.82 (d, J=4.8 Hz, 1H), 4.5 (bs, 1H), 4.03 (s, 3H), 3.00-2.99 (d, 3H), 2.68-2.65 (m, 4H), 2.23 (s, 3H), 1.99 (bs, 2H), 1.73 (bs, 2H).

Example 228: (S)-7-chloro-1-methyl-6-((4-(methylamino)pyrazolo[1,5-a]pyrazin-3-yl)oxy)-N-(3-((1-methylpyrrolidin-3-yl)oxy)-5-(trifluoromethyl)phenyl)-1H-imidazo[4,5-b]pyridin-2-amine

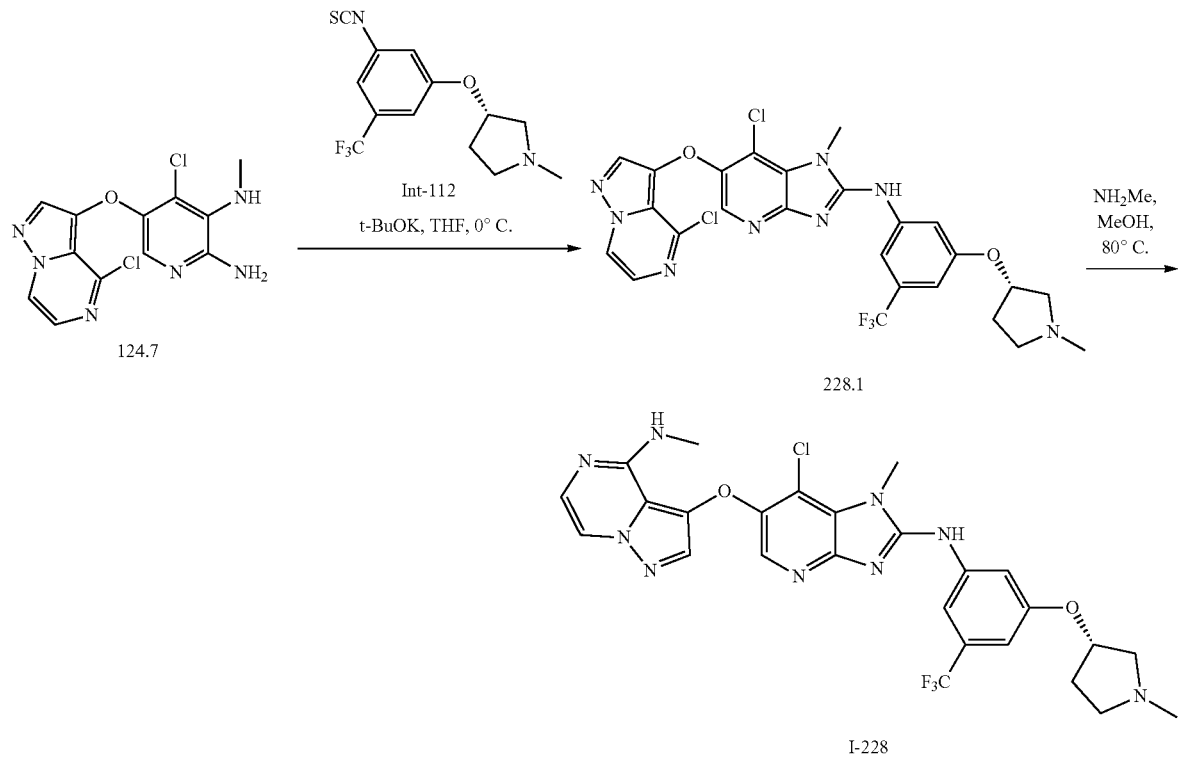

Synthesis of compound 228.1. Compound 228.1 was prepared from 124.7 and Int-112, following the procedure described in the synthesis of I-13. The product was purified by flash column chromatography on silica gel (CombiFlash®, 10% methanol in DCM). MS (ES): m/z 594.3 [M+H]+.

Synthesis of I-228. Compound I-228 was prepared from 228.1, following the procedure described in the synthesis of I-171. The product was purified by flash column chromatography on silica gel (CombiFlash®, 1200 methanol in DCM). MS (ES): m/z 588.3 [M+H]+, 1H NMR (DMSO-d6, 400 MHz): δ 9.81 (s, 1H), 8.22 (s, 1H), 8.00 (s, 1H), 7.92 (s, 1H), 7.80-7.78 (d, J=4.4 Hz, 1H), 7.49 (s, 1H), 7.28-7.26 (d, J=4.4 Hz, 1H), 6.87 (s, 1H), 6.83-6.82 (d, J=4.0 Hz, 1H), 5.04 (bs, 1H), 4.07 (s, 3H), 3.02-3.01 (d, 3H), 2.86 (bs, 2H), 2.41 (s, 3H), 2.30 (bs, 2H), 1.93 (bs, 1H), 1.58 (bs, 1H).

Example 229: (R)-7-chloro-1-methyl-6-((4-(methylamino)pyrazolo[1,5-a]pyrazin-3-yl)oxy)-N-(3-((1-methylpyrrolidin-3-yl)oxy)-5-(trifluoromethyl)phenyl)-1H-imidazo[4,5-b]pyridin-2-amine Synthesis I-229. Compound I-229 was prepared from 229.1, following the procedure described in the synthesis of I-171. The product was purified by flash column chromatography on silica gel (CombiFlash®, 12% methanol in DCM). MS (ES): m/z 588.2 [M+H]+, 1H NMR (DMSO-d6, 400 MHz): δ 9.78 (s, 1H), 8.22 (s, 1H), 7.98 (s, 1H), 7.91 (s, 1H), 7.80-7.79 (d, J=4.0 Hz, 1H), 7.49 (s, 1H), 7.27-7.26 (d, J=4.0 Hz, 1H), 6.86 (bs, 2H), 5.02 (bs, 1H), 4.06 (s, 3H), 3.01-3.00 (d, 3H), 2.81 (bs, 2H), 2.38 (bs, 5H), 1.93-1.90 (m, 1H), 1.58 (bs, 1H).

Example 230: 2-(tert-butyl)-5-((7-chloro-1-methyl-6-((4-(methylamino)pyrazolo[1,5-a]pyrazin-3-yl)oxy)-1H-imidazo[4,5-b]pyridin-2-yl)amino)-3-ethylpyrimidin-4(3H)-one

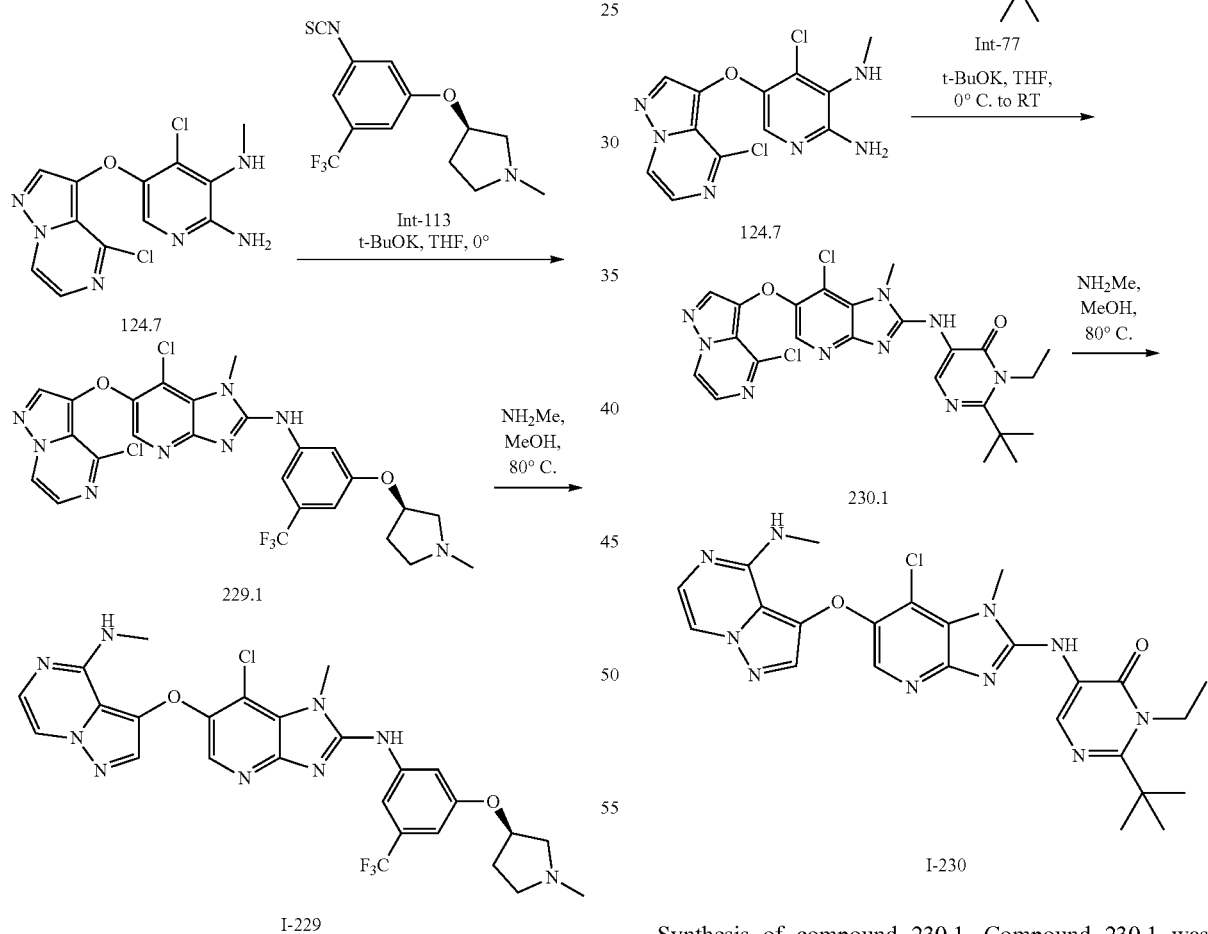

Synthesis of compound 229.1. Compound 229.1 was prepared from 124.7 and Int-113, following the procedure described in the synthesis of I-13. The product was purified by flash column chromatography on silica gel (CombiFlash®, 10% methanol in DCM) to afford 229.1. MS (ES): m/z 594.3 [M+H]+.

Synthesis of compound 230.1. Compound 230.1 was prepared from 124.7 and Int-77, following the procedure described in the synthesis of I-13. The product was purified by flash column chromatography on silica gel (CombiFlash®, 1.8% methanol in DCM). MS (ES): m/z 529.2 [M+H]+.

Synthesis of I-230. Compound I-230 was prepared from 230.1, following the procedure described in the synthesis of I-171. The product was purified by flash column chromatography on silica gel (CombiFlash®, 2.8% methanol in DCM). MS (ES): m/z 523.2 [M+H]$^+$, $^1$H NMR (DMSO-d$_6$, 400 MHz): δ 8.81 (s, 1H), 8.14 (s, 1H), 7.78 (bs, 2H), 7.48 (s, 1H), 7.26 (s, 1H), 6.81 (s, 1H), 4.53-4.52 (m, 2H), 3.99 (s, 3H), 3.00 (s, 3H), 2.38 (s, 3H), 1.39 (s, 9H).

Example 231: 7-chloro-N-(5-cyclopropyl-4,6-dimethylpyrimidin-2-yl)-1-methyl-6-(pyrazolo[1,5-a]pyrazin-3-yloxy)-1H-imidazo[4,5-b]pyridin-2-amine

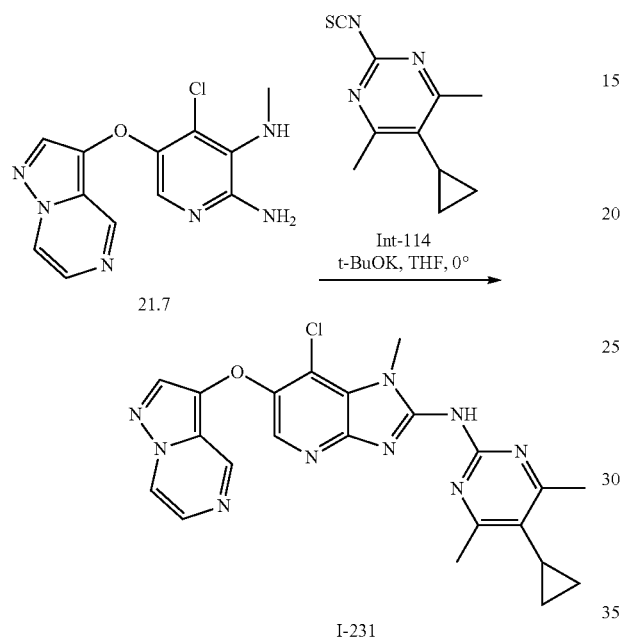

Synthesis of compound I-231. Compound I-231 was prepared from 21.7 and Int-114, following the procedure described in the synthesis of I-13. The product was purified by flash column chromatography on silica gel (CombiFlash®, 2.8% methanol in DCM). MS (ES): m/z 462.1 [M+H]$^+$, $^1$H NMR (DMSO-d$_6$, 400 MHz): δ 10.18 (s, 1H), 9.18 (s, 1H), 8.71-8.70 (d, J=4.0 Hz, 1H), 8.33 (s, 1H), 8.09 (s, 1H), 7.90-7.89 (d, J=4.0 Hz, 1H), 3.84 (s, 3H), 2.46 (s, 6H), 1.71 (bs, 1H), 1.03-1.01 (m, 2H), 0.53-0.52 (m, 2H).

Example 232: N-(7-chloro-1-methyl-6-(pyrazolo[1,5-a]pyrazin-3-yloxy)-1H-imidazo[4,5-b]pyridin-2-yl)-3-fluoro-6,6-dimethyl-6,7-dihydro-4H-pyrazolo[5,1-c][1,4]oxazin-2-amine

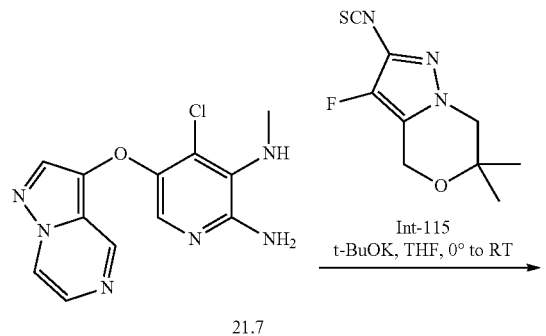

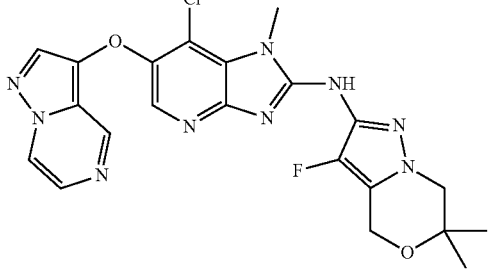

Synthesis of compound I-232. Compound I-232 was prepared from 21.7 and Int-115, following the procedure described in the synthesis of I-13. The product was purified by flash column chromatography on silica gel (CombiFlash®, 2.7% methanol in DCM). MS (ES): m/z 485.1 [M+H]$^+$, $^1$H NMR (DMSO-d$_6$, 400 MHz): δ 9.57 (s, 1H), 9.02 (s, 1H), 8.68 (bs, 1H), 8.12 (s, 1H), 8.01 (s, 1H), 7.86-7.85 (d, J=4.8 Hz, 1H), 4.86 (s, 3H), 3.94 (s, 2H), 3.86 (s, 2H), 1.32 (s, 6H).

Example 233: 5-((7-chloro-1-methyl-6-((4-(methylamino)pyrazolo[1,5-a]pyrazin-3-yl)oxy)-1H-imidazo[4,5-b]pyridin-2-yl)amino)-1-methyl-6-oxo-3-(trifluoromethyl)-1,6-dihydropyridine-2-carbonitrile

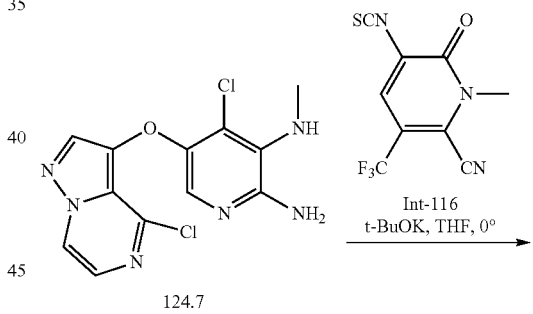

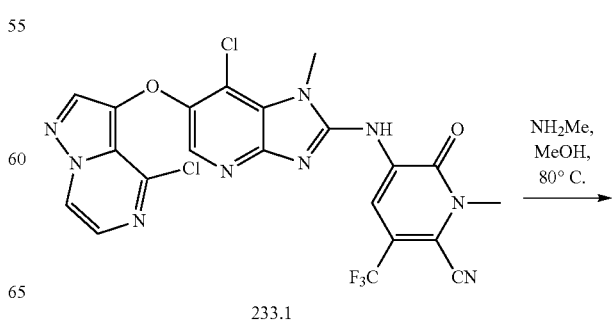

881
-continued

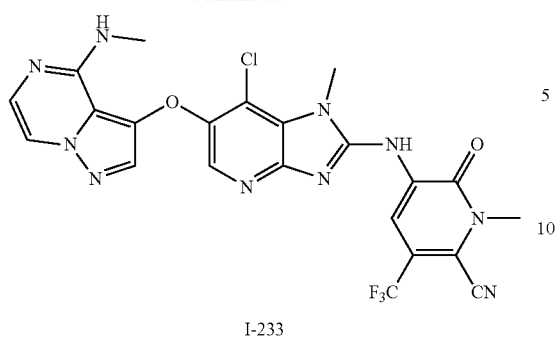

I-233

Synthesis of compound 233.1. Compound 233.1 was prepared from 124.7 and Int-116, following the procedure described in the synthesis of I-13. The product was purified by flash column chromatography on silica gel (Combi-Flash®, 2.2% methanol in DCM). MS (ES): m/z 551.1 [M+H]$^+$.

Synthesis of I-233. Compound I-233 was prepared from 233.1, following the procedure described in the synthesis of I-171. The product was purified by flash column chromatography on silica gel (CombiFlash®, 3.5% methanol in DCM). MS (ES): m/z 546.0 [M+H]$^+$, $^1$H NMR (DMSO-d$_6$, 400 MHz): δ 9.61 (s, 1H), 9.05 (bs, 2H), 8.70 (s, 1H), 8.31 (s, 1H), 8.07 (s, 1H), 7.88-7.87 (m, 1H), 4.16 (s, 3H), 4.01 (s, 3H), 2.69-2.67 (d, 3H).

Example 234: 6-((7-chloro-1-methyl-6-((4-(methylamino)pyrazolo[1,5-a]pyrazin-3-yl)oxy)-1H-imidazo[4,5-b]pyridin-2-yl)amino)-2,3,3-trimethyl-4-(trifluoromethyl)isoindolin-1-one 882
-continued

I-234

Synthesis of compound 234.1. Compound 234.1 was prepared from 124.7 and Int-74, following the procedure described in the synthesis of I-13. The product was purified by flash column chromatography on silica gel (Combi-Flash®, 2.7% methanol in DCM). MS (ES): m/z 592.1 [M+H]$^+$.

Synthesis of I-234. Compound I-234 was prepared from 234.1, following the procedure described in the synthesis of I-171. The product was purified by flash column chromatography on silica gel (CombiFlash®, 3.4% methanol in DCM). MS (ES): m/z 586.6 [M+H]$^+$, $^1$H NMR (DMSO-d$_6$, 400 MHz): δ 9.90 (s, 1H), 8.72 (s, 1H), 8.48 (s, 1H), 8.24 (s, 1H), 7.79-7.78 (d, J=4.8 Hz, 1H), 7.49 (s, 1H), 7.27-7.26 (d, J=4.8 Hz, 1H), 6.83-6.82 (d, J=4.0 Hz, 1H), 4.06 (s, 3H), 3.01 (s, 6H), 1.55 (s, 6H).

Example 235: 7-chloro-N-(4-((dimethylamino)methyl)-2-fluoro-5-(trifluoromethyl)phenyl)-1-methyl-6-((4-(methylamino)pyrazolo[1,5-a]pyrazin-3-yl)oxy)-1H-imidazo[4,5-b]pyridin-2-amine

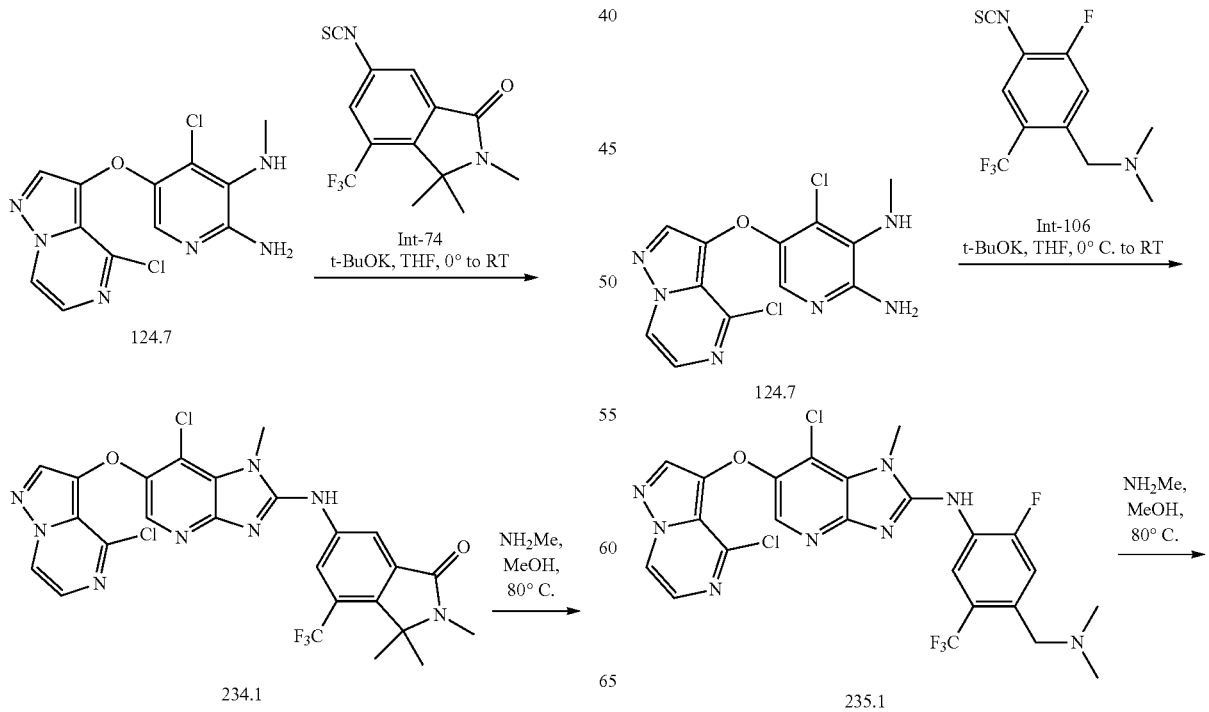

883

-continued

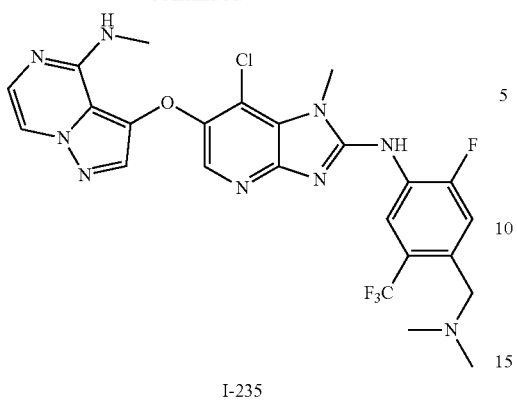

I-235

Synthesis of compound 235.1. Compound 235.1 was prepared from 124.7 and Int-106, following the procedure described in the synthesis of I-13. The product was purified by flash column chromatography on silica gel (Combi-Flash®, 3.0% methanol in DCM). m/z 570.2 [M+H]+.

Synthesis of I-235. Compound I-235 was prepared from 235.1, following the procedure described in the synthesis of I-171. The product was purified by flash column chromatography on silica gel (CombiFlash®, 4.5% methanol in DCM). MS (ES): m/z 563.9 [M]+, $^1$H NMR (DMSO-d$_6$, 400 MHz): δ 9.41 (s, 1H), 8.36-8.35 (d, J=4.0 Hz, 1H), 8.18 (s, 1H), 7.78-7.76 (d, J=8.0 Hz, 1H), 7.66-7.63 (d, J=8.4 Hz, 1H), 7.47 (s, 1H), 7.25-7.24 (d, J=4.0 Hz, 1H), 6.81 (s, 1H), 4.00 (s, 3H), 3.55 (s, 2H), 2.99-2.98 (d, 3H), 2.24 (s 6H).

Example 236: N-(1-(2-oxaspiro[3.3]heptan-6-yl)-5-(trifluoromethyl)-1H-pyrazol-3-yl)-7-chloro-1-methyl-6-((4-(methylamino)pyrazolo[1,5-a]pyrazin-3-yl)oxy)-1H-imidazo[4,5-b]pyridin-2-amine

884

-continued

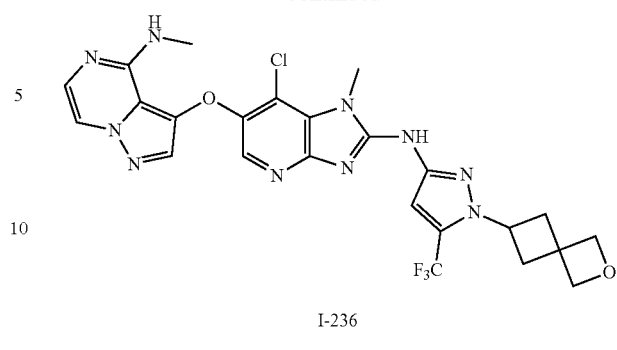

I-236

Synthesis of compound 236.1. Compound 236.1 was prepared from 124.7 and Int-177, following the procedure described in the synthesis of I-13. The product was purified by flash column chromatography on silica gel (Combi-Flash®, 1.4% methanol in DCM). MS (ES): m/z 580.9 [M+H]+.

Synthesis of I-236. Compound I-236 was prepared from 236.1, following the procedure described in the synthesis of I-171. The product was purified by flash column chromatography on silica gel (CombiFlash®, 2.7% methanol in DCM). MS (ES): m/z 575.1 [M]+, $^1$H NMR (DMSO-d$_6$, 400 MHz): δ 10.95 (s, 1H), 8.17 (s, 1H), 7.79-7.77 (d, J=4.8 Hz, 1H), 7.48 (s, 1H), 7.32 (s, 1H), 7.26-7.25 (d, J=4.8 Hz, 1H), 6.82 (s, 1H), 4.85-4.82 (m, 1H), 4.72 (s, 2H), 4.60 (s, 2H), 4.00 (s, 3H), 3.01-3.00 (s, 3H), 2.83-2.81 (m, 4H).

Example 237: 1-(3-((7-chloro-1-methyl-6-(pyrazolo[1,5-a]pyrazin-3-yloxy)-1H-imidazo[4,5-b]pyridin-2-yl)amino)-5-(trifluoromethyl)phenyl)piperidin-4-ol

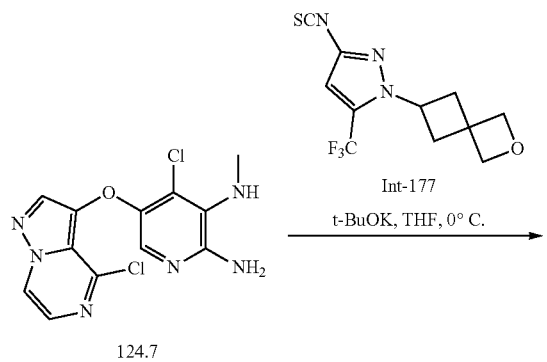

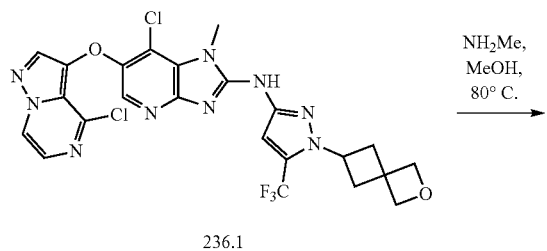

236.1

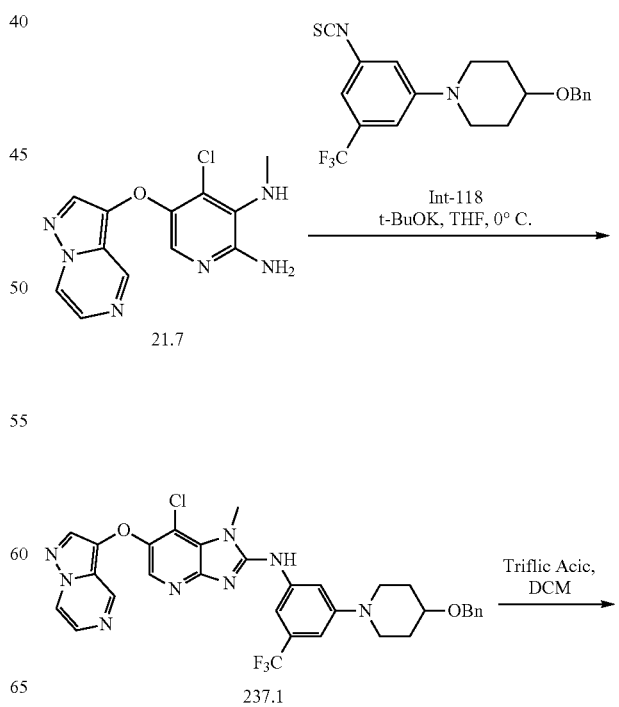

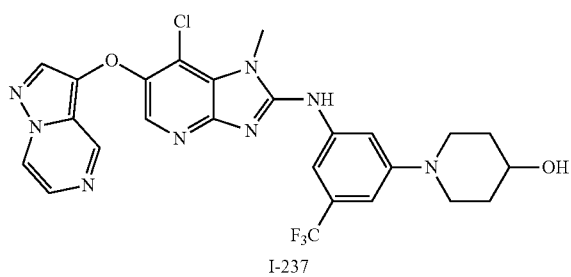
I-237

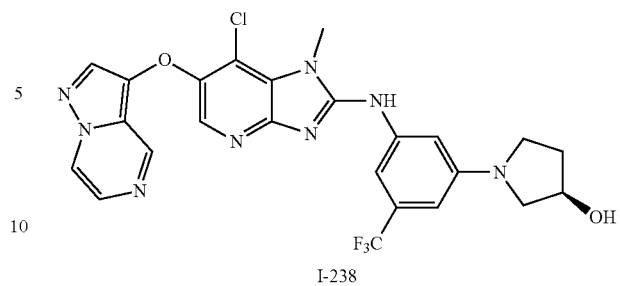
I-238

Synthesis of compound 237.1. Compound 237.1 was prepared from 21.7 and Int-118, following the procedure described in the synthesis of I-13. The product was purified by flash column chromatography on silica gel (Combi-Flash®, 2.8% methanol in DCM). MS (ES): m/z 650.0 [M+H]$^+$.

Synthesis of I-237. Compound I-237 was prepared from 237.1, following the procedure described in the synthesis of I-23. The product was purified by flash column chromatography on silica gel (CombiFlash®, 5.0% methanol in DCM). MS (ES): m/z 559.2 [M+H]$^+$, $^1$H NMR (DMSO-d$_6$, 400 MHz): δ 9.43 (s, 1H), 9.03 (s, 1H), 8.70-8.69 (d, J=4.0 Hz, 1H), 8.21 (s, 1H), 8.05 (s, 1H), 7.89-7.88 (d, J=4.0 Hz, 1H), 7.77-7.75 (d, J=8.0 Hz, 2H), 6.89 (s, 1H), 4.74 (bs, 1H), 4.04 (s, 3H), 3.71 (bs, 1H), 3.63 (bs, 2H), 3.04-3.02 (m, 2H), 1.86 (bs, 2H), 1.53-1.51 (m, 2H).

Example 238: (R)-1-(3-((7-chloro-1-methyl-6-(pyrazolo[1,5-a]pyrazin-3-yloxy)-1H-imidazo[4,5-b]pyridin-2-yl)amino)-5-(trifluoromethyl)phenyl)pyrrolidin-3-ol Synthesis of compound 238.1. Compound 238.1 was prepared from 21.7 and Int-119, following the procedure described in the synthesis of I-13. The product was purified by flash column chromatography on silica gel (Combi-Flash®, 2.4% methanol in DCM). MS (ES): m/z 636.1 [M+H]$^+$.

Synthesis of I-238. Compound I-238 was prepared from 238.1, following the procedure described in the synthesis of I-23. The product was purified by flash column chromatography on silica gel (CombiFlash®, 3.9% methanol in DCM). MS (ES): m/z 545.3 [M+H]$^+$, $^1$H NMR (DMSO-d$_6$, 400 MHz): δ 9.41 (s, 1H), 9.03 (s, 1H), 8.70-8.69 (d, J=4.0 Hz, 1H), 8.19 (s, 1H), 8.04 (s, 1H), 7.88-7.87 (d, J=4.0 Hz, 1H), 7.61 (s, 1H), 7.37 (s, 1H), 6.44 (s, 1H), 5.04-5.03 (d, J=4.0 Hz, 1H), 4.46 (bs, 1H), 4.03 (s, 3H), 3.51-3.48 (m, 1H), 3.43-3.39 (m, 2H), 3.18-3.16 (m, 1H), 2.11-2.07 (m, 1H), 1.97-1.96 (m, 1H).

Example 239: (S)-1-(3-((7-chloro-1-methyl-6-(pyrazolo[1,5-a]pyrazin-3-yloxy)-1H-imidazo[4,5-b]pyridin-2-yl)amino)-5-(trifluoromethyl)phenyl)pyrrolidin-3-ol

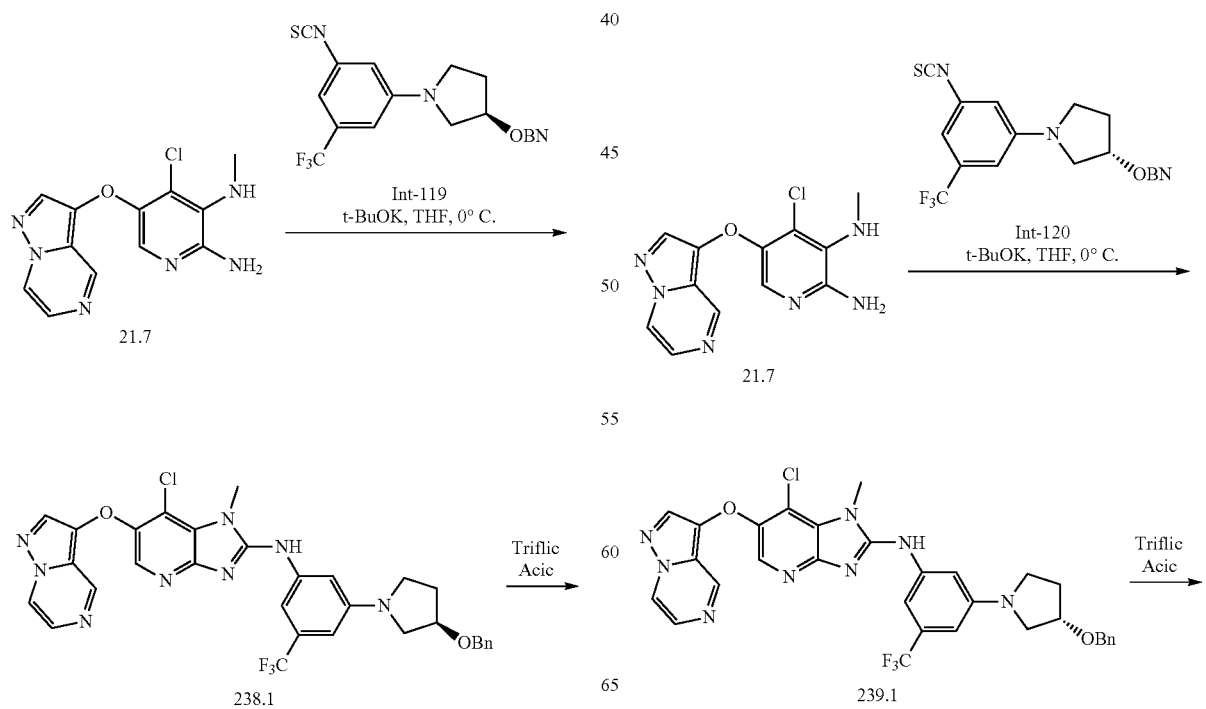

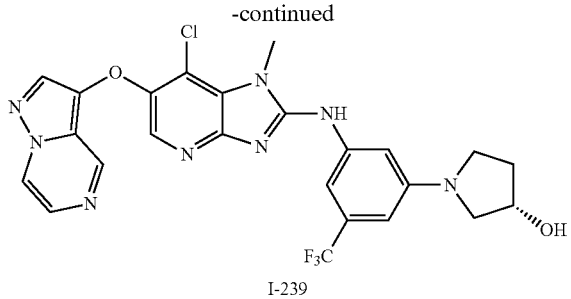

I-239

Synthesis of compound 239.1. Compound 239.1 was prepared from 21.7 and Int-120, following the procedure described in the synthesis of I-13. The product was purified by flash column chromatography on silica gel (Combi-Flash®, 2.4% methanol in DCM). MS (ES): m/z 636.1 [M+H]+.

Synthesis of I-239. Compound I-239 was prepared from 239.1, following the procedure described in the synthesis of I-23. The product was purified by flash column chromatography on silica gel (CombiFlash®, 3.9% methanol in DCM). MS (ES): m/z 545.3 [M+H]+, 1H NMR (DMSO-$d_6$, 400 MHz): δ 9.41 (s, 1H), 9.03 (s, 1H), 8.70-8.69 (d, J=4.0 Hz, 1H), 8.19 (s, 1H), 8.04 (s, 1H), 7.88-7.87 (d, J=4.0 Hz, 1H), 7.61 (s, 1H), 7.36 (s, 1H), 6.44 (s, 1H), 5.04-5.03 (d, J=4.0 Hz, 1H), 4.45 (bs, 1H), 4.03 (s, 3H), 3.51-3.48 (m, 1H), 3.43-3.39 (m, 2H), 3.18-3.16 (m, 1H), 2.11-2.07 (m, 1H), 1.97-1.96 (m, 1H).

Example 240: 1-methyl-6-((4-(methylamino)pyrazolo[1,5-a]pyrazin-3-yl)oxy)-2-((1,1,2-trimethyl-3-oxo-7-(trifluoromethyl)isoindolin-5-yl)amino)-1H-imidazo[4,5-b]pyridine-7-carbonitrile

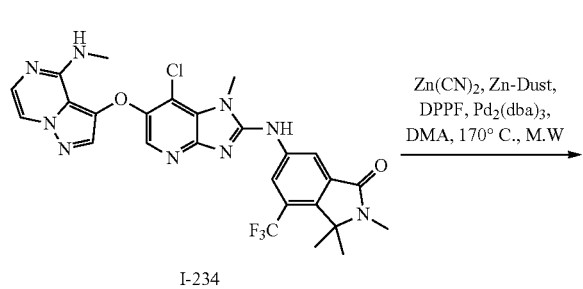

Synthesis of compound I-240. Compound I-240 was prepared from I-234, following the procedure described in the synthesis of I-157. The product was purified by flash column chromatography on silica gel (CombiFlash®, 2.8% methanol in DCM). MS (ES): m/z 577.3 [M+H]+, 1H NMR (DMSO-$d_6$, 400 MHz): δ 10.09 (s, 1H), 8.73 (s, 1H), 8.48 (s, 1H), 8.13 (s, 1H), 7.84-7.83 (d, J=4.8 Hz, 1H), 7.76 (s, 1H), 7.30-7.29 (d, J=4.8 Hz, 1H), 6.81 (bs, 1H), 4.03 (s, 3H), 2.99 (s, 3H), 2.97-2.96 (d, 3H), 1.53 (s, 6H).

Example 241: (S)-7-chloro-1-methyl-6-((4-(methylamino)pyrazolo[1,5-a]pyrazin-3-yl)oxy)-N-(3-((1-methylpyrrolidin-2-yl)methoxy)-5-(trifluoromethyl)phenyl)-1H-imidazo[4,5-b]pyridine-2-amine

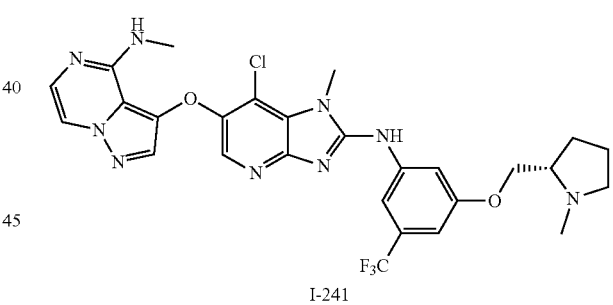

Synthesis of compound 241.1. Compound 241.1 was prepared from 124.7 and Int-121, following the procedure described in the synthesis of I-13. The product was purified by flash column chromatography on silica gel (Combi-Flash®, 2.5% methanol in DCM). MS (ES): m/z 608.2 [M+H]+.

Synthesis of I-241. Compound I-241 was prepared from 241.1, following the procedure described in the synthesis of I-171. The product was purified by flash column chromatography on silica gel (CombiFlash®, 4.0% methanol in DCM). MS (ES): m/z 602.7 [M+H]+, 1H NMR (DMSO-$d_6$, 400 MHz): δ 9.67 (s, 1H), 8.20 (s, 1H), 7.96 (s, 1H), 7.90 (s, 1H), 7.78-7.77 (d, J=4.0 Hz, 1H), 7.47 (s, 1H), 7.26-7.25 (d, J=4.0 Hz, 1H), 6.94 (s, 1H), 6.82-6.81 (d, J=4.0 Hz, 1H), 4.13 (bs, 2H), 4.03 (s, 3H), 3.09 (bs, 1H), 3.00-2.99 (d, 3H), 2.57 (bs, 3H), 2.05 (bs, 2H), 1.80-1.65 (m, 4H).

Example 242: (R)-7-chloro-1-methyl-6-((4-(methyl-amino)pyrazolo[1,5-a]pyrazin-3-yl)oxy)-N-(3-((1-methylpyrrolidin-2-yl)methoxy)-5-(trifluoromethyl)phenyl)-1H-imidazo[4,5-b]pyridin-2-amine Example 243: (S)-7-chloro-1-methyl-N-(3-((1-methylpyrrolidin-2-yl)methoxy)-5-(trifluoromethyl)phenyl)-6-(pyrazolo[1,5-a]pyrazin-3-yloxy)-1H-imidazo[4,5-b]pyridin-2-amine

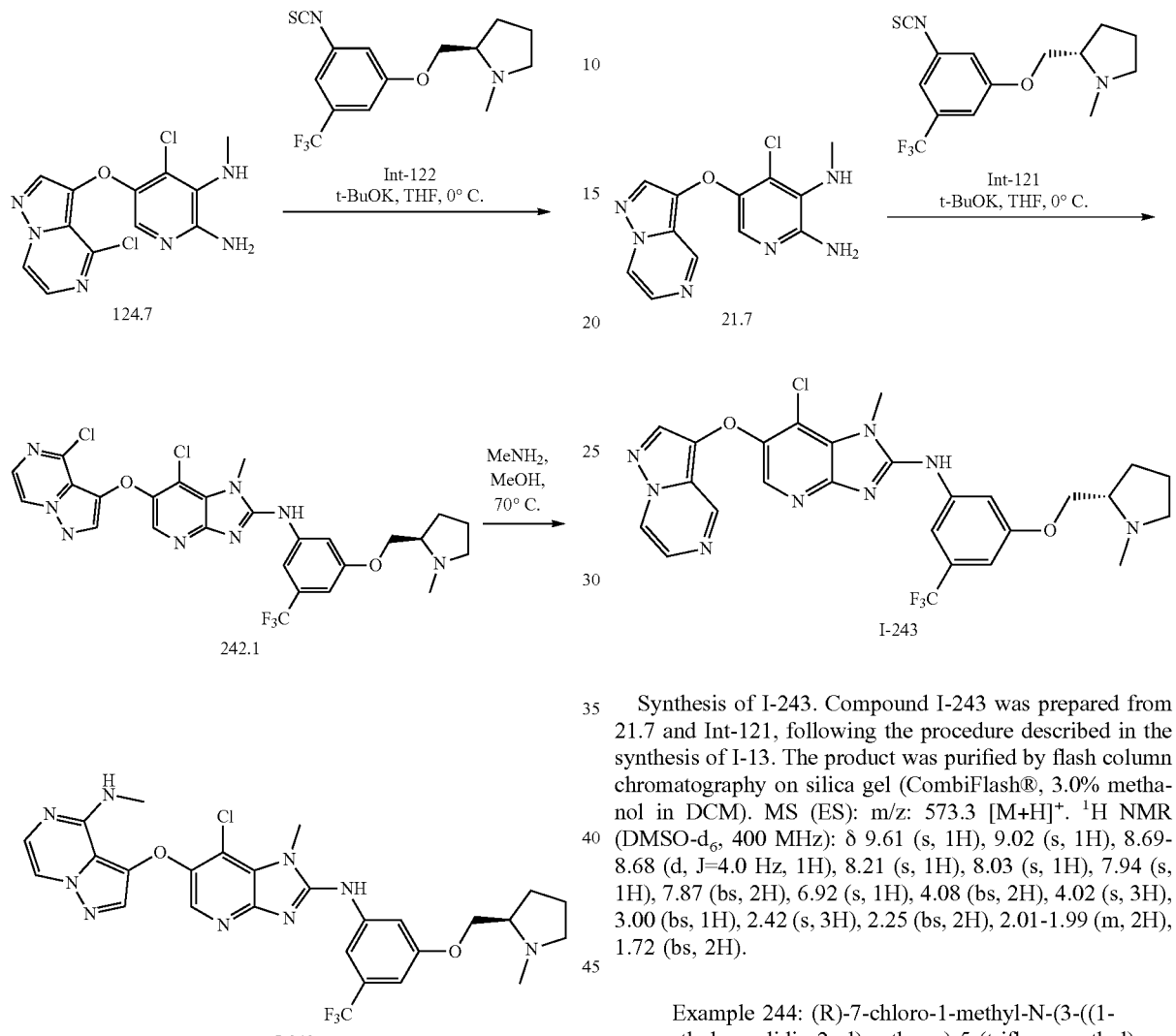

Synthesis of compound 242.1. Compound 242.1 was prepared from 124.7 and Int-122, following the procedure described in the synthesis of I-13. The product was purified by flash column chromatography on silica gel (CombiFlash®, 2.5% methanol in DCM). MS (ES): m/z 608.2 [M+H]⁺.

Synthesis of I-242. Compound I-242 was prepared from 242.1, following the procedure described in the synthesis of I-171. The product was purified by flash column chromatography on silica gel (CombiFlash®, 4.0% methanol in DCM). MS (ES): m/z 603.0 [M+H]⁺, ¹H NMR (DMSO-d₆, 400 MHz): δ 9.71 (s, 1H), 8.20 (s, 1H), 7.98 (s, 1H), 7.92 (s, 1H), 7.79-7.77 (d, J=4.8 Hz, 1H), 7.48 (s, 1H), 7.27-7.25 (d, J=4.8 Hz, 1H), 6.95 (s, 1H), 6.82-6.81 (d, J=4.4 Hz, 1H), 4.14 (bs, 2H), 4.05 (s, 3H), 3.09 (bs, 1H), 3.01-3.00 (d, 3H), 2.57 (bs, 3H), 2.07 (bs, 2H), 1.78-1.70 (m, 4H).

Synthesis of I-243. Compound I-243 was prepared from 21.7 and Int-121, following the procedure described in the synthesis of I-13. The product was purified by flash column chromatography on silica gel (CombiFlash®, 3.0% methanol in DCM). MS (ES): m/z: 573.3 [M+H]⁺. ¹H NMR (DMSO-d₆, 400 MHz): δ 9.61 (s, 1H), 9.02 (s, 1H), 8.69-8.68 (d, J=4.0 Hz, 1H), 8.21 (s, 1H), 8.03 (s, 1H), 7.94 (s, 1H), 7.87 (bs, 2H), 6.92 (s, 1H), 4.08 (bs, 2H), 4.02 (s, 3H), 3.00 (bs, 1H), 2.42 (s, 3H), 2.25 (bs, 2H), 2.01-1.99 (m, 2H), 1.72 (bs, 2H).

Example 244: (R)-7-chloro-1-methyl-N-(3-((1-methylpyrrolidin-2-yl)methoxy)-5-(trifluoromethyl)phenyl)-6-(pyrazolo[1,5-a]pyrazin-3-yloxy)-1H-imidazo[4,5-b]pyridin-2-amine

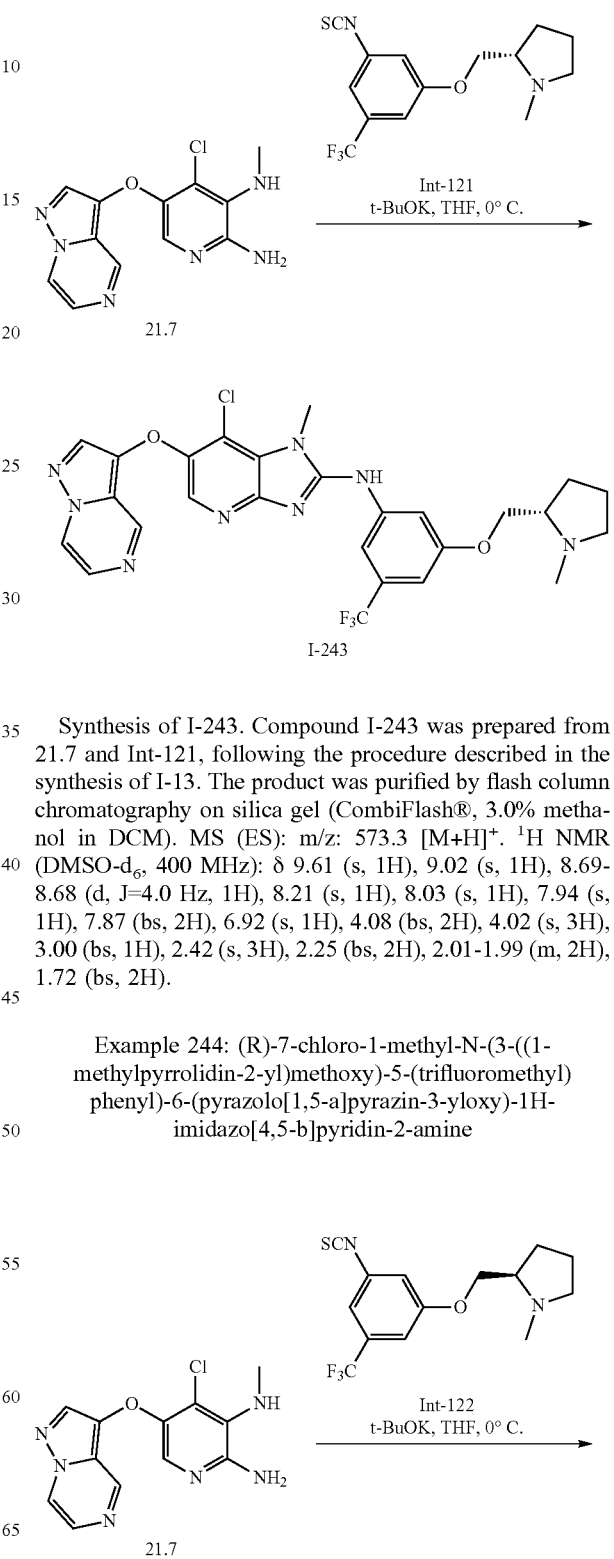

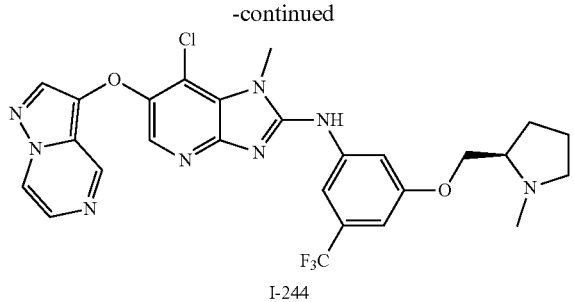

I-244

Synthesis of I-244. Compound I-244 was prepared from 21.7 and Int-122, following the procedure described in the synthesis of I-13. The product was purified by flash column chromatography on silica gel (CombiFlash®, 3.0% methanol in DCM). MS (ES): m/z 573.2 [M+H]+, 1H NMR (DMSO-d$_6$, 400 MHz): δ 9.61 (s, 1H), 9.01 (s, 1H), 8.68 (bs, 1H), 8.20 (s, 1H), 8.03 (s, 1H), 7.94 (s, 1H), 7.87 (bs, 2H), 6.92 (s, 1H), 4.09 (bs, 2H), 4.02 (s, 3H), 3.02 (bs, 1H), 2.43 (s, 3H), 2.25 (bs, 2H), 2.02 (bs, 2H), 1.73 (bs, 2H).

Example 245: (S)-3-((7-chloro-1-methyl-6-((4-(methylamino)pyrazolo[1,5-a]pyrazin-3-yl)oxy)-1H-imidazo[4,5-b]pyridin-2-yl)amino)-1-(tetrahydro-2H-pyran-3-yl)-5-(trifluoromethyl)pyridin-2(1H)-one and (R)-3-((7-chloro-1-methyl-6-((4-(methylamino)pyrazolo[1,5-a]pyrazin-3-yl)oxy)-1H-imidazo[4,5-b]pyridin-2-yl)amino)-1-(tetrahydro-2H-pyran-3-yl)-5-(trifluoromethyl)pyridin-2(1H)-one

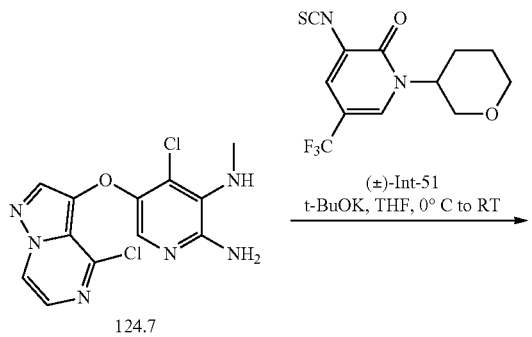

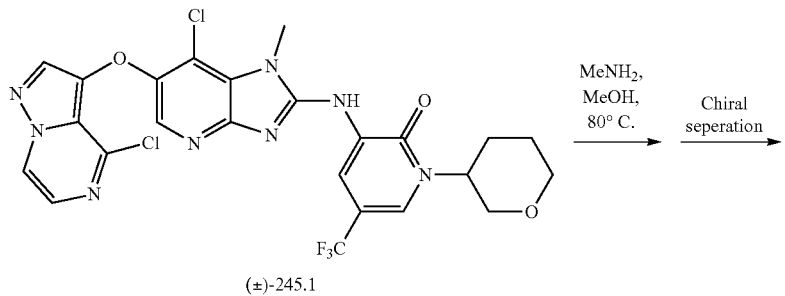

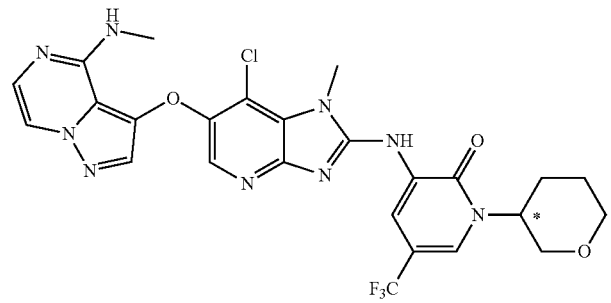

I-245-a and I-245-b

Synthesis of compound (±)-245.1. Compound (±)-245.1 was prepared from 124.7 and (±)-Int-51, following the procedure described in the synthesis of I-13. The product was purified by flash column chromatography on silica gel (CombiFlash®, 2.3% methanol in DCM). m/z 596.36 [M+H]$^+$.

Synthesis of compound I-245-a and I-245-b. The racemate was prepared from (f)-245.1, following the procedure described in the synthesis of I-171. The product was purified by flash column chromatography on silica gel (CombiFlash®, 3.1% methanol in DCM). MS (ES): m/z 590.5 [M+H]$^+$. It was subjected for chiral HPLC separation (column: CHIRALPAK IB-N (250 mm*21 mm, 5 μm); mobile phase: (A) 0.1% DEA in n-hexane; (B) 0.1% DEA in isopropanol:acetonitrile (70:30); flow rate=20 mL/min) to afford first eluting fraction (I-245-a) and second eluting fraction (I-245-b). (*Absolute stereochemistry not determined.)

I-245-a: MS (ES): m/z 590.3 [M+H]$^+$, $^1$H NMR (DMSO-d$_6$, 400 MHz): δ 8.91 (s, 1H), 8.61 (s, 1H), 8.23 (s, 1H), 8.10 (s, 1H), 7.77 (bs, 1H), 7.49 (s, 1H), 7.25 (bs, 1H), 6.83 (s, 1H), 4.88 (bs, 1H), 4.00 (s, 3H), 3.87-3.79 (m, 2H), 3.55-3.53 (m, 1H), 2.98 (s, 3H), 2.21-2.19 (m, 1H), 2.09 (bs, 1H), 2.00 (bs, 1H), 1.75 (bs, 2H).

I-245-b: MS (ES): m/z 590.1 [M+H]$^+$, $^1$H NMR (DMSO-d$_6$, 400 MHz): δ 8.91 (s, 1H), 8.62 (s, 1H), 8.23 (s, 1H), 8.10 (s, 1H), 7.78-7.77 (d, J=4.8 Hz, 1H), 7.49 (s, 1H), 7.25-7.24 (d, J=4.8 Hz, 1H), 6.84 (s, 1H), 4.88 (bs, 1H), 4.00 (s, 3H), 3.87-3.79 (m, 2H), 3.55-3.52 (m, 1H), 2.98 (s, 3H), 2.21-2.19 (m, 1H), 2.09 (bs, 1H), 2.00 (bs, 1H), 1.76 (bs, 2H).

Example 246: 7-chloro-N-(3-((3-fluoroazetidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

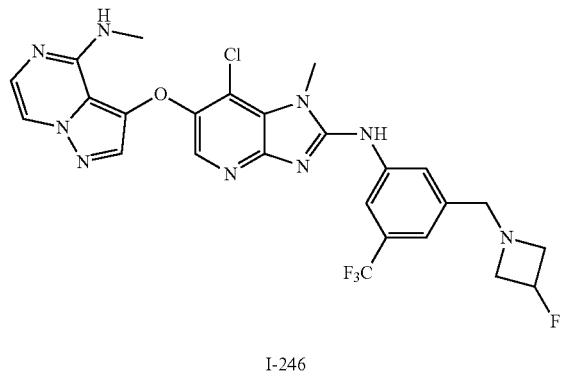

I-246

Synthesis of compound 246.1. Compound 246.1 was prepared from 124.7 and Int-93, following the procedure described in the synthesis of I-13. The product was purified by flash column chromatography on silica gel (CombiFlash®, 3.0% methanol in DCM). MS (ES): m/z 582.1 [M+H]$^+$.

Synthesis of I-246. Compound I-246 was prepared from 246.1, following the procedure described in the synthesis of I-171. The product was purified by flash column chromatography on silica gel (CombiFlash®, 3.5% methanol in DCM). MS (ES): m/z 576.2 [M+H]$^+$, $^1$H NMR (DMSO-d$_6$, 400 MHz): δ 9.66 (s, 1H), 8.31 (s, 1H), 8.20-8.19 (d, J=3.2 Hz, 1H), 8.07 (s, 1H), 7.77-7.76 (d, J=4.2 Hz, 1H), 7.47-7.46 (d, J=3.2 Hz, 1H), 7.26-7.25 (d, J=3.6 Hz, 2H), 6.81 (s, 1H), 5.29-5.15 (m, 1H), 4.03-4.02 (d, 3H), 3.75 (s, 2H), 3.61-3.59 (m, 2H), 3.26-3.19 (m, 2H), 2.99 (s, 3H).

Example 247: 7-chloro-N-(3-((3-methoxyazetidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

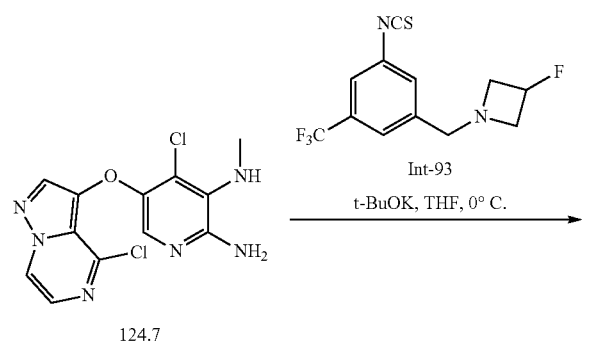

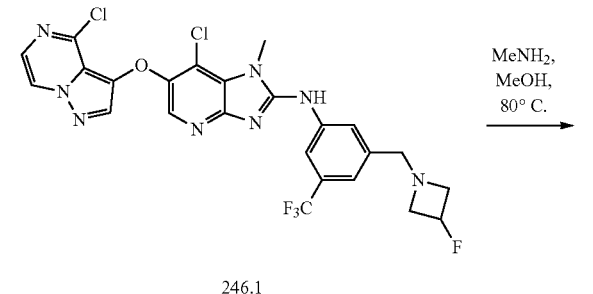

246.1

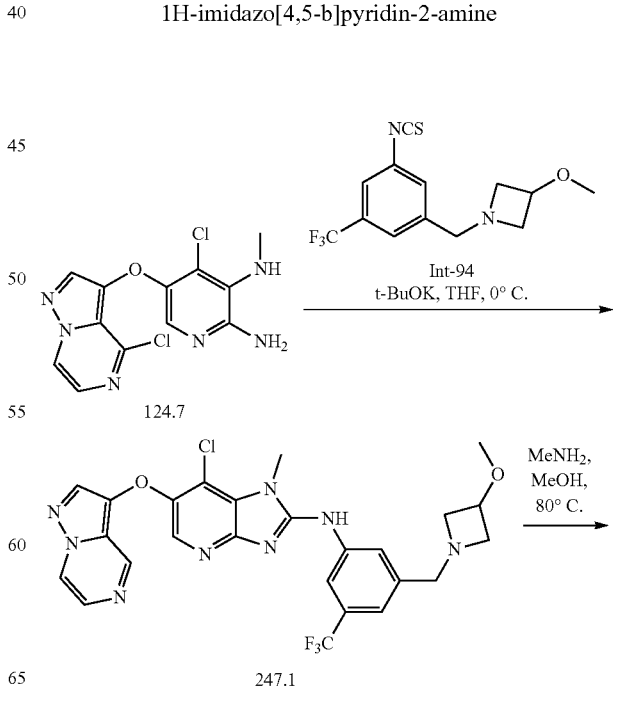

247.1

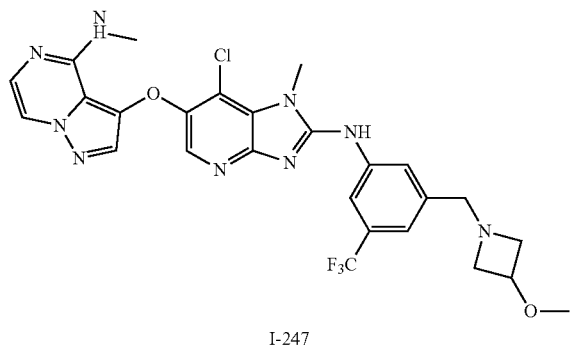

I-247

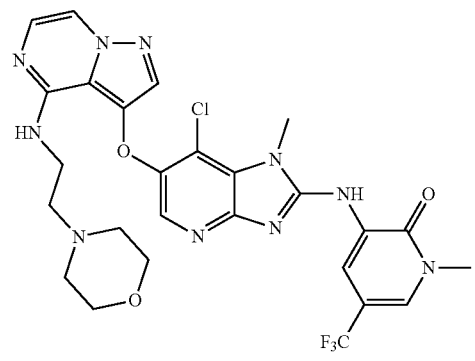

I-248

Synthesis of compound 247.1. Compound 247.1 was prepared from 124.7 and Int-94, following the procedure described in the synthesis of I-13. The product was purified by flash column chromatography on silica gel (Combi-Flash®, 2.2% methanol in DCM). MS (ES): m/z 594.2 [M+H]$^+$.

Synthesis of I-247: Compound I-247 was prepared from 247.1, following the procedure described in the synthesis of I-171. The product was purified by flash column chromatography on silica gel (CombiFlash®, 3.8% methanol in DCM). MS (ES): m/z: 588.2 [M+H]$^+$, $^1$H NMR (DMSO-d$_6$, 400 MHz): δ 9.66 (s, 1H), 8.31 (s, 1H), 8.19-8.17 (d, J=7.6 Hz, 1H), 8.06 (s, 1H), 7.77 (s, 1H), 7.47-7.45 (d, J=7.6 Hz, 1H), 7.26 (bs, 2H), 6.81 (s, 1H), 4.02 (s, 3H), 3.71 (bs, 2H), 3.55 (bs, 2H), 3.34 (bs, 2H), 3.18-3.16 (d, 3H), 2.99-2.94 (m, 4H).

Example 248: 3-((7-chloro-1-methyl-6-((4-((2-morpholinoethyl)amino)pyrazolo[1,5-a]pyrazin-3-yl)oxy)-1H-imidazo[4,5-b]pyridin-2-yl)amino)-1-methyl-5-(trifluoromethyl)pyridin-2(1H)-one Synthesis of compound 248.1. Compound 248.1 was prepared from 124.7 and Int-63, following the procedure described in the synthesis of I-13. The product was purified by flash column chromatography on silica gel (Combi-Flash®, 2.0% methanol in DCM). MS (ES): m/z 526.2 [M+H]$^+$.

Synthesis of I-248. A mixture of 248.1 (0.060 g, 0.114 mmol, 1.0 equiv), potassium carbonate (0.047 g, 0.342 mmol, 3.0 equiv) and 2-morpholinoethan-1-amine (0.16 g, 0.125 mmol, 1.1 equiv) in DMF (2 mL) was stirred at 70° C. for 72 h. It was filtered and filtrate was transferred into water, stirred and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.4% methanol in DCM). MS (ES): m/z 619.2 [M+H]$^+$, $^1$H NMR (DMSO-d$_6$, 400 MHz): δ 8.83 (s, 1H), 8.61 (s, 1H), 8.24 (s, 1H), 8.13 (s, 1H), 7.81-7.80 (d, J=4.8 Hz, 1H), 7.60 (s, 1H), 7.26-7.25 (d, J=4.8 Hz, 1H), 6.72 (s, 1H), 4.01 (bs, 4H), 3.66 (s, 3H), 3.58 (bs, 3H), 3.42 (bs, 4H), 2.38 (bs, 4H).

Example 249: (S)-7-chloro-N-(3-((3-methoxypyrrolidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

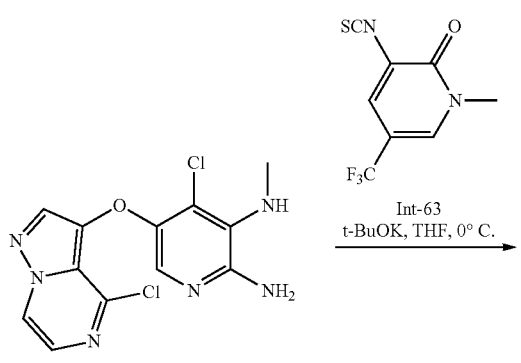

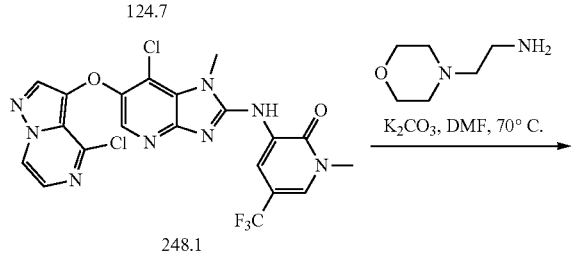

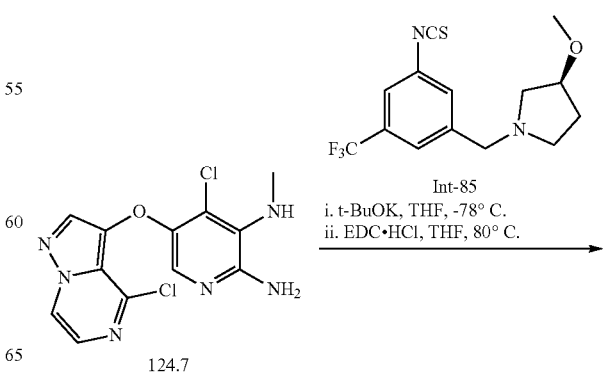

-continued

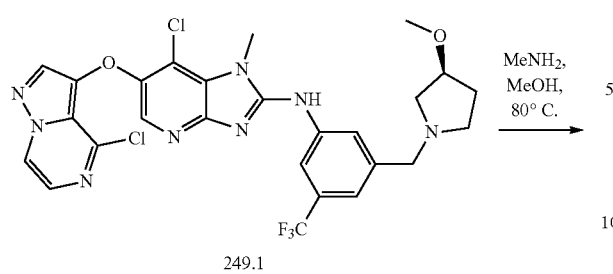

249.1

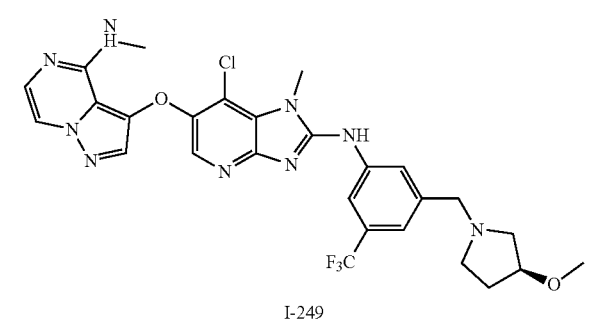

I-249

Synthesis of compound 249.1. To a solution of 124.7 (0.100 g, 0.307 mmol, 1.0 equiv) and Int-85 (0.116 g, 0.369 mmol, 1.2 equiv) in THF (5 mL) was added potassium tert-butoxide (1 M in THF) (0.9 mL, 0.921 mmol, 3.0 equiv) at −78° C. and stirred for 30 min. The reaction mixture was poured over ice-water and extracted with ethyl acetate. The combined organic layers were washed with brine, dried over anhydrous sodium sulfate, filtered and concentrated under reduced pressure. The residue was dissolved in THF (3 mL) and N-(3-dimethylaminopropyl)-N'-ethylcarbodiimide hydrochloride (0.175 g, 0.921 mmol, 3.0 equiv) was added. The reaction mixture was heated at 80° C. for 2 h. It was poured over water and extracted with ethyl acetate. The combined organic layers were washed with brine, dried over anhydrous sodium sulfate, filtered and concentrated under reduced pressure. The residue was purified by flash column chromatography on silica gel (CombiFlash®, 4.8% methanol in DCM). MS (ES): m/z 608.2 [M+H]⁺.

Synthesis of I-249. Compound I-249 was prepared from 249.1, following the procedure described in the synthesis of I-171. The product was purified by flash column chromatography on silica gel (CombiFlash®, 6.8% methanol in DCM). MS (ES): m/z 602.3 [M+H]⁺, 1H NMR (DMSO-$d_6$, 400 MHz): δ 9.70 (s, 1H), 8.38 (s, 1H), 8.22 (s, 1H), 8.10 (s, 1H), 7.81-7.79 (d, J=8.0 Hz, 1H), 7.49 (s, 1H), 7.32 (s, 1H), 7.28-7.27 (d, J=4.0 Hz, 1H), 6.85-6.84 (d, J=4.0 Hz, 1H), 4.05 (s, 3H), 3.94 (bs, 1H), 3.71 (bs, 2H), 3.20 (s, 3H), 3.03-3.01 (d, 3H), 2.75 (bs, 2H), 2.06-2.03 (m, 2H), 1.71 (bs, 2H).

Example 250: (R)-7-chloro-N-(3-((3-methoxypyrrolidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

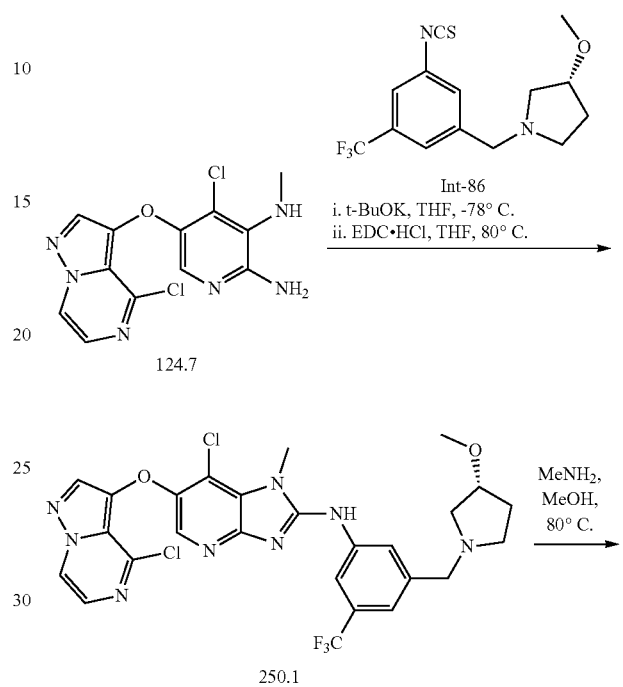

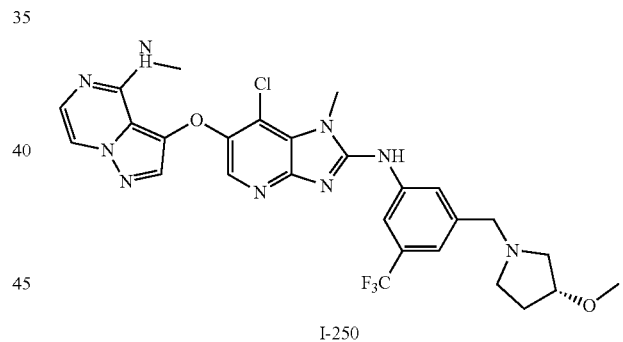

I-250

Synthesis of compound 250.1. Compound 250.1 was prepared from 124.7 and Int-86, following the procedure described in the synthesis of 249.1. The product was purified by flash column chromatography on silica gel (CombiFlash®, 4.8% methanol in DCM). MS (ES): m/z 608.2 [M+H]⁺.

Synthesis of I-250. Compound I-250 was prepared from 250.1, following the procedure described in the synthesis of I-171. The product was purified by flash column chromatography on silica gel (CombiFlash®, 6.8% methanol in DCM). MS (ES): m/z 602.4 [M+H]⁺, 1H NMR (DMSO-$d_6$, 400 MHz): δ 9.69 (s, 1H), 8.37 (s, 1H), 8.21 (s, 1H), 8.09 (s, 1H), 7.80-7.79 (d, J=4.0 Hz, 1H), 7.49 (s, 1H), 7.32 (s, 1H), 7.27-7.26 (d, J=4.0 Hz, 1H), 6.84-6.83 (d, J=4.0 Hz, 1H), 4.05 (s, 3H), 3.94 (bs, 1H), 3.71 (bs, 2H), 3.19 (s, 3H), 3.02-3.00 (d, 3H), 2.75 (bs, 2H), 2.07-2.04 (m, 2H), 1.72 (bs, 2H).

Example 251: (S)—N-(5-(tert-butyl)-1-(1-methylpyrrolidin-3-yl)-1H-pyrazol-3-yl)-7-chloro-1-methyl-6-((4-(methylamino)pyrazolo[1,5-a]pyrazin-3-yl)oxy)-1H-imidazo[4,5-b]pyridin-2-amine

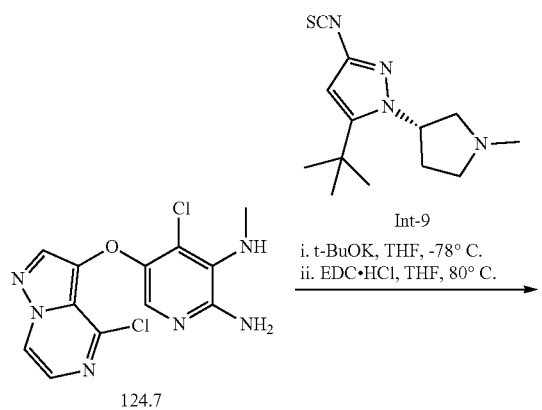

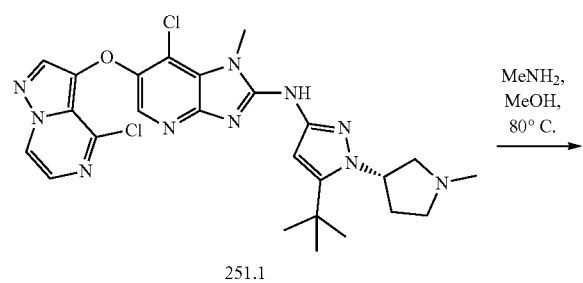

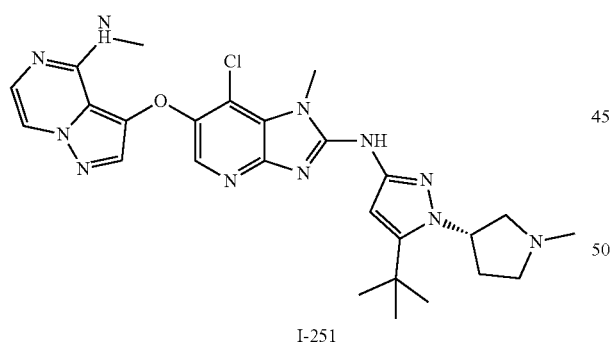

Synthesis of compound 251.1. Compound 251.1 was prepared from 124.7 and Int-9, following the procedure described in the synthesis of 249.1. The product was purified by flash column chromatography on silica gel (Combi-Flash®, 7.5% methanol in DCM). MS (ES): m/z 642.3 [M+H]⁺.

Synthesis of I-251. Compound I-251 was prepared from 251.1, following the procedure described in the synthesis of I-171. The product was purified by preparative HPLC. MS (ES): m/z 550.4 [M+H]⁺, ¹H NMR (DMSO-d₆, 400 MHz): δ 9.97 (s, 1H), 8.10 (s, 1H), 7.77-7.76 (d, J=4.4 Hz, 1H), 7.47 (s, 1H), 7.26-7.25 (d, J=4.4 Hz, 1H), 6.79-6.78 (d, J=4.0 Hz, 1H), 6.52 (s, 1H), 5.08 (bs, 1H), 3.96 (s, 3H), 3.00-2.99 (m, 3H), 2.73-2.62 (m, 3H), 2.34-2.31 (m, 6H), 1.39 (s, 9H).

Example 252: (R)—N-(5-(tert-butyl)-1-(1-methylpyrrolidin-3-yl)-1H-pyrazol-3-yl)-7-chloro-1-methyl-6-((4-(methylamino)pyrazolo[1,5-a]pyrazin-3-yl)oxy)-1H-imidazo[4,5-b]pyridin-2-amine

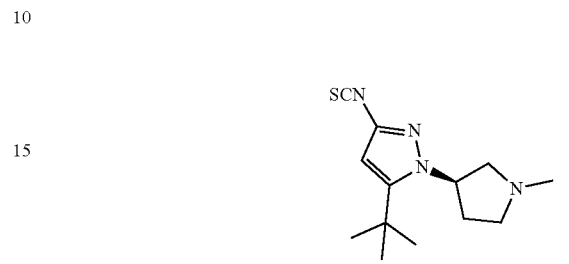

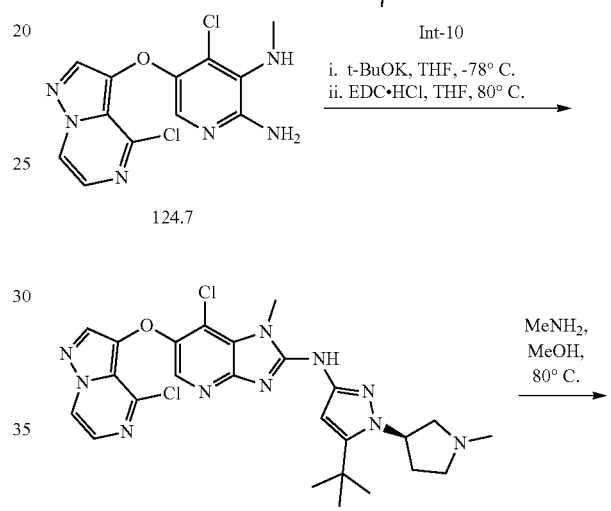

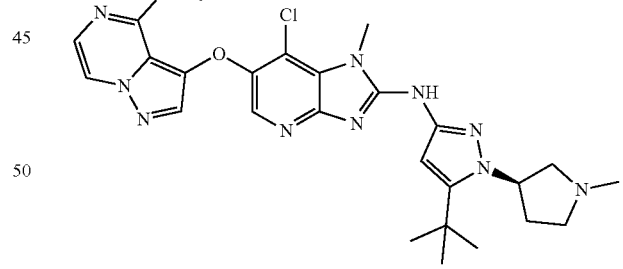

Synthesis of compound 252.1. Compound 252.1 was prepared from 124.7 and Int-10, following the procedure described in the synthesis of 249.1. The product was purified by flash column chromatography on silica gel (Combi-Flash®, 8.0% methanol in DCM). MS (ES): m/z 642.4 [M+H]⁺.

Synthesis of I-252. Compound I-252 was prepared from 252.1, following the procedure described in the synthesis of I-171. The product was purified by preparative HPLC. MS (ES): m/z 551.1 [M+H]$^+$, $^1$H NMR (DMSO-d$_6$, 400 MHz): δ 9.96 (s, 1H), 8.12 (s, 1H), 7.77 (bs, 1H), 7.47 (s, 1H), 7.25 (bs, 1H), 6.79 (bs, 1H), 6.51 (s, 1H), 5.26 (bs, 1H), 3.96 (s, 3H), 3.00 (s, 3H), 2.68-2.63 (m, 3H), 2.34-2.25 (m, 6H), 1.40 (s, 9H).

Example 253: 7-chloro-N-(5-cyclopentyl-4,6-dimethylpyrimidin-2-yl)-1-methyl-6-(pyrazolo[1,5-a]pyrazin-3-yloxy)-1H-imidazo[4,5-b]pyridin-2-amine

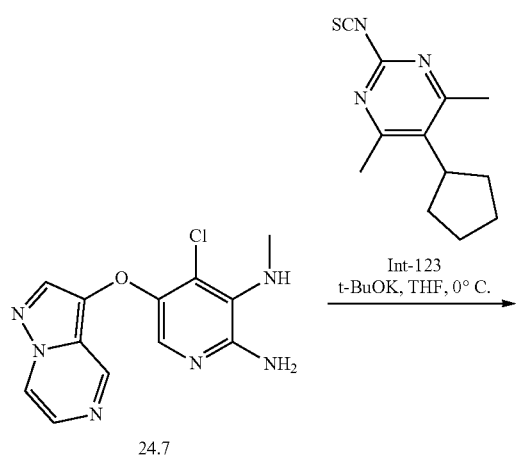

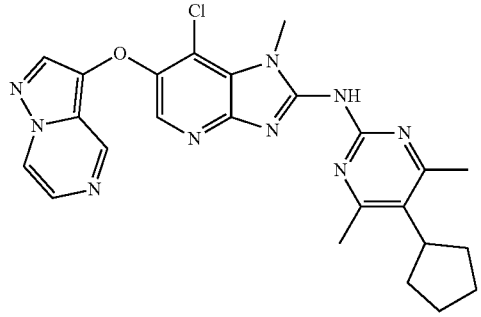

I-253

Synthesis of I-253. Compound I-253 was prepared from 24.7 and Int-123, following the procedure described in the synthesis of I-13. The product was purified by flash column chromatography on silica gel (CombiFlash®, 2.8% methanol in DCM). MS (ES): m/z 490.5 [M+H]$^+$, $^1$H NMR (DMSO-d$_6$, 400 MHz): δ 10.13 (s, 1H), 9.09 (s, 1H), 8.71-8.69 (d, J=4.8 Hz, 1H), 8.32 (s, 1H), 8.08 (s, 1H), 7.89-7.88 (d, J=4.8 Hz, 1H), 3.85 (s, 3H), 2.71 (bs, 1H), 2.42 (s, 6H), 1.94 (bs, 2H), 1.85 (bs, 2H), 1.70 (bs, 4H).

Example 254: 7-chloro-1-methyl-6-((4-(methylamino)pyrazolo[1,5-a]pyrazin-3-yl)oxy)-N-(3-(1-methylpiperidin-4-yl)-5-(trifluoromethyl)phenyl)-1H-imidazo[4,5-b]pyridin-2-amine

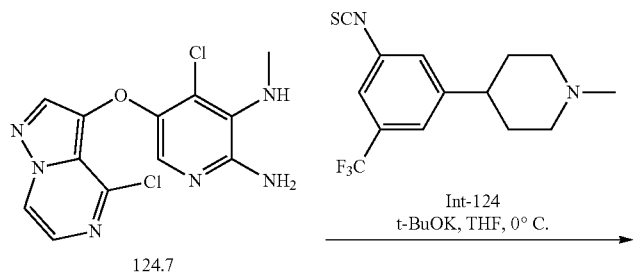

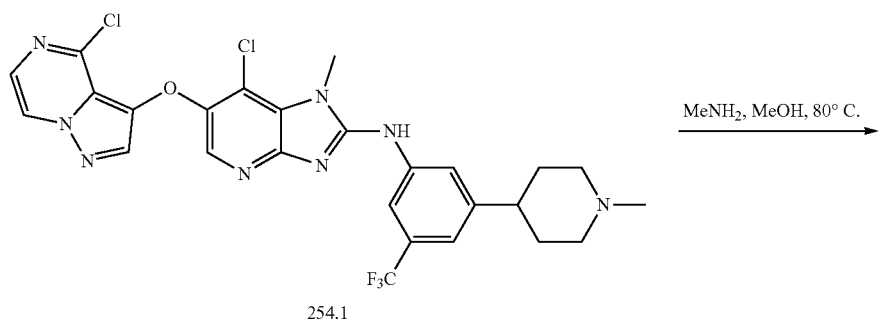

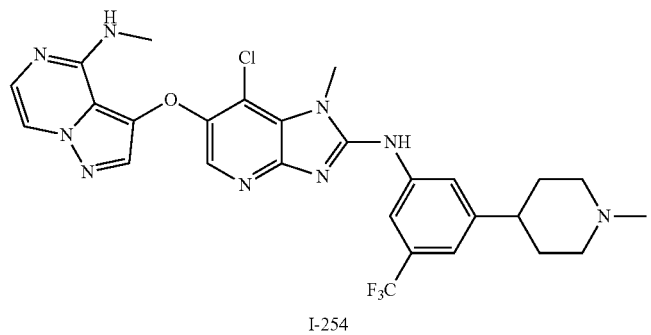

I-254

Synthesis of compound 254.1. Compound 254.1 was prepared from 124.7 and Int-124, following the procedure described in the synthesis of I-13. The product was purified by flash column chromatography on silica gel (CombiFlash®, 5.0% methanol in DCM). m/z 592.2 [M+H]$^+$.

Synthesis of I-254. Compound I-254 was prepared from 254.1, following the procedure described in the synthesis of I-171. The product was purified by flash column chromatography on silica gel (CombiFlash®, 7.0% methanol in DCM). MS (ES): m/z 586.6 [M+H]$^+$, $^1$H NMR (DMSO-d$_6$, 400 MHz): δ 9.84 (s, 1H), 8.29 (s, 1H), 8.18 (s, 1H), 8.11 (s, 1H), 7.76 (s, 1H), 7.47 (s, 1H), 7.25 (bs, 2H), 6.81 (s, 1H), 4.05 (s, 3H), 2.99 (s, 3H), 2.75-2.67 (m, 1H), 2.60 (bs, 4H), 1.97 (bs, 4H), 1.33 (s, 3H).

Example 255: 7-chloro-N-(3-((dimethylamino)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

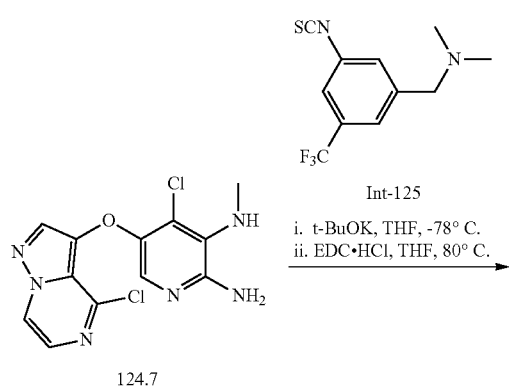

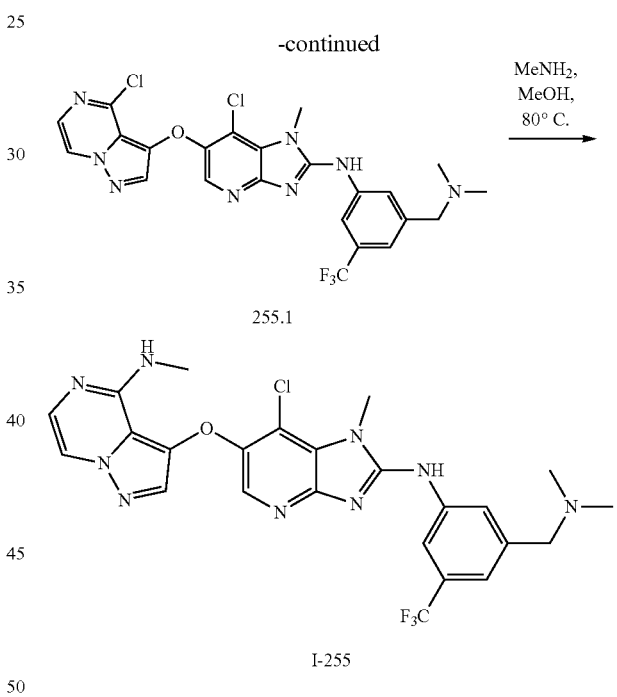

Synthesis of compound 255.1. Compound 255.1 was prepared from 124.7 and Int-125, following the procedure described in the synthesis of 249.1. The product was purified by flash column chromatography on silica gel (CombiFlash®, 2.8% methanol in DCM). MS (ES): m/z 552.1 [M+H]$^+$.

Synthesis of I-255. Compound I-255 was prepared from 255.1, following the procedure described in the synthesis of I-171. The product was purified by flash column chromatography on silica gel (CombiFlash®, 3.5% methanol in DCM). MS (ES): m/z 546.2 [M+H]$^+$, $^1$H NMR (DMSO-d$_6$, 400 MHz): δ 9.69 (s, 1H), 8.35 (s, 1H), 8.20 (s, 1H), 8.11 (s, 1H), 7.79-7.77 (d, J=4.4 Hz, 1H), 7.47 (s, 1H), 7.31 (s, 1H), 7.26-7.25 (d, J=4.4 Hz, 1H), 6.84-6.83 (d, J=4.4 Hz, 1H), 4.03 (s, 3H), 3.56 (bs, 2H), 3.00-2.99 (d, 3H), 2.25 (bs, 6H).

Example 256: N-(3-(azetidin-1-ylmethyl)-5-(trifluoromethyl)phenyl)-7-chloro-1-methyl-6-(pyrazolo[1,5-a]pyrazin-3-yloxy)-1H-imidazo[4,5-b]pyridin-2-amine

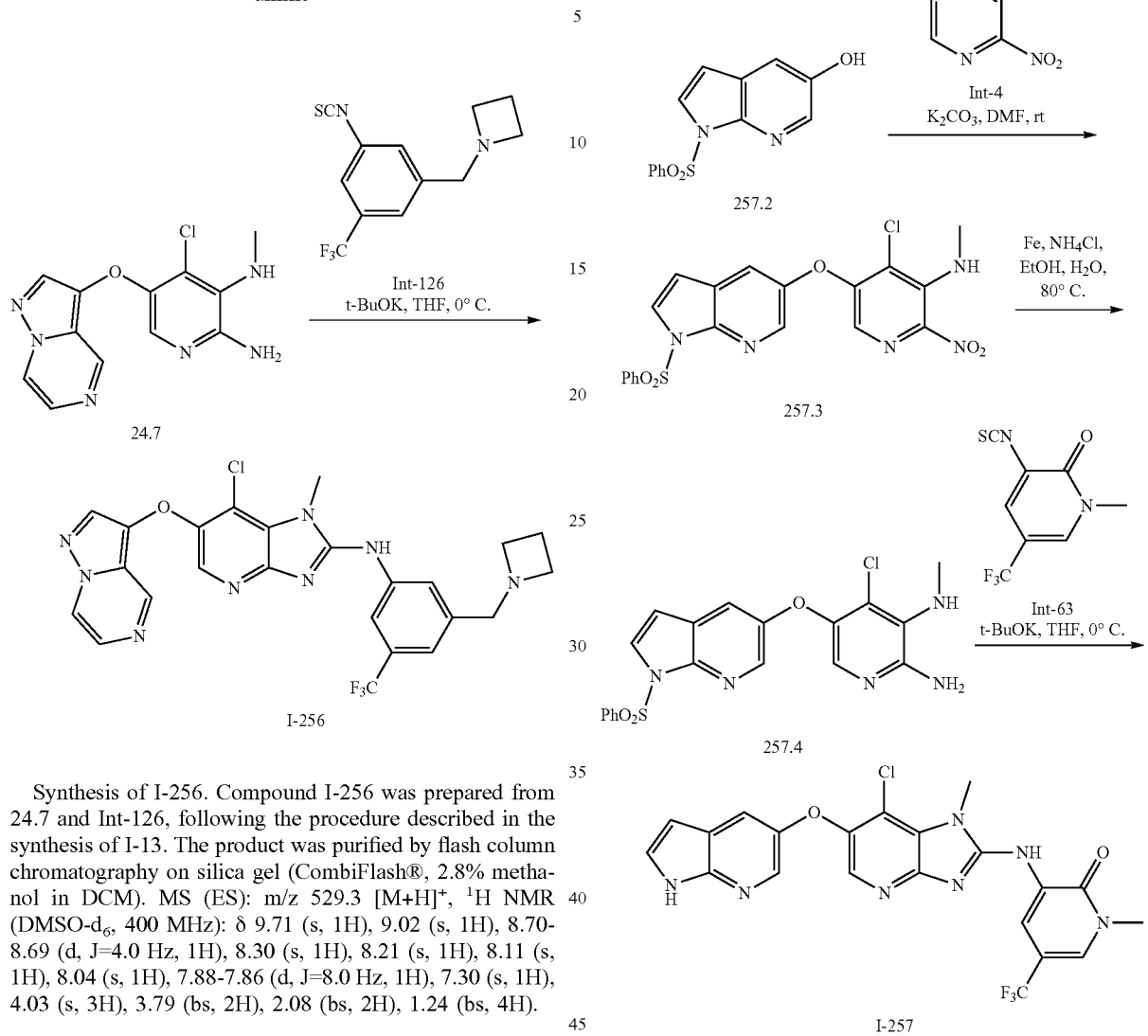

Synthesis of I-256. Compound I-256 was prepared from 24.7 and Int-126, following the procedure described in the synthesis of I-13. The product was purified by flash column chromatography on silica gel (CombiFlash®, 2.8% methanol in DCM). MS (ES): m/z 529.3 [M+H]+, 1H NMR (DMSO-d6, 400 MHz): δ 9.71 (s, 1H), 9.02 (s, 1H), 8.70-8.69 (d, J=4.0 Hz, 1H), 8.30 (s, 1H), 8.21 (s, 1H), 8.11 (s, 1H), 8.04 (s, 1H), 7.88-7.86 (d, J=8.0 Hz, 1H), 7.30 (s, 1H), 4.03 (s, 3H), 3.79 (bs, 2H), 2.08 (bs, 2H), 1.24 (bs, 4H).

Example 257: 1-(3-((7-chloro-1-methyl-6-(pyrazolo[1,5-a]pyrazin-3-yloxy)-1H-imidazo[4,5-b]pyridin-2-yl)amino)-5-(trifluoromethyl)benzyl)azetidin-3-ol

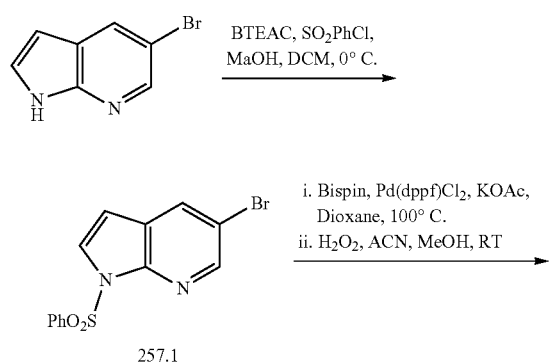

Synthesis of compound 257.1. To a solution of 5-bromo-1H-pyrrolo[2,3-b]pyridine (10.0 g, 50.75 mmol, 1.0 equiv) in DCM (100 mL) was added benzyltriethylammonium chloride (0.230 g, 1.015 mmol, 0.02 equiv), followed by powdered sodium hydroxide (6.33 g, 158.3 mmol, 3.12 equiv) and cooled to 0° C. To the mixture was added benzyl sulphonyl chloride (11.16 g, 63.43 mmol, 1.25 equiv) and the reaction mixture was stirred at 0° C. for 1 h. It was filtered through a pad of Celite® and rinsed with DCM. The filtrate was concentrated under reduced pressure. The residue was purified by flash column chromatography on silica gel (CombiFlash®, DCM) to afford 257.1. MS (ES): m/z 338.1 [M+H]+.

Synthesis of compound 257.2. A solution of 257.1 (2.0 g, 5.93 mmol, 1.0 equiv), bis(pinacolato)diboron (3.02 g, 11.86 mmol, 2.0 equiv) and potassium acetate (1.16 g, 11.86 mmol, 2.0 equiv) in 1,4-dioxane (15 mL) was degassed by bubbling argon through for 5 min. To the mixture was added 1,1-bis(diphenylphosphino)ferrocene-palladium(II) dichloride DCM complex (0.868 g, 1.186 mmol, 0.2 equiv) and degassed for another 5 min. The reaction mixture was heated at 100° C. for 30 min. It was cooled to room temperature and transferred into ice cold water, stirred and extracted with ethyl acetate. The combined organic layers were washed with brine, dried over anhydrous sodium sulfate, filtered and concentrated under reduced pressure. To the residue was added acetonitrile (70 mL), methanol (70 mL) and hydrogen peroxide (20 mL). The reaction mixture was stirred at room temperature for 16 h. It was poured over ice cold water, stirred and extracted with ethyl acetate. The combined organic layers were washed with brine, dried over anhydrous sodium sulfate, filtered and concentrated under reduced pressure to afford 257.2. MS (ES): m/z 275.1 [M+H]$^+$.

Synthesis of compound 257.3. Compound 257.3 was prepared from 257.2 and Int-4, following the procedure described in the synthesis of 19.1. The product was used in the next step without purification. MS (ES): m/z 460.5 [M+H]$^+$.

Synthesis of compound 257.4. Compound 257.4 was prepared from 257.3, following the procedure described in the synthesis of 5.4. The product was purified by flash column chromatography on silica gel (CombiFlash®, 2% methanol in DCM). MS (ES): m/z 430.2 [M+H]$^+$.

Synthesis of I-257. Compound I-257 was prepared from 257.4 and Int-63, following the procedure described in the synthesis of I-13. The product was purified by flash column chromatography on silica gel (CombiFlash®, 4.2% methanol in DCM). MS (ES): m/z 490.2 [M+H]$^+$, $^1$H NMR (DMSO-d$_6$, 400 MHz): δ 11.69 (s, 1H), 8.79 (s, 1H), 8.62-8.61 (d, J=2.0 Hz, 1H), 8.13-8.09 (m, 3H), 7.50-7.48 (m, 2H), 6.37 (s, 1H), 4.00 (s, 3H), 3.66 (s, 3H).

Example 258: 1-(3-((7-chloro-1-methyl-6-(pyrazolo[1,5-a]pyrazin-3-yloxy)-1H-imidazo[4,5-b]pyridin-2-yl)amino)-5-(trifluoromethyl)benzyl)azetidin-3-ol

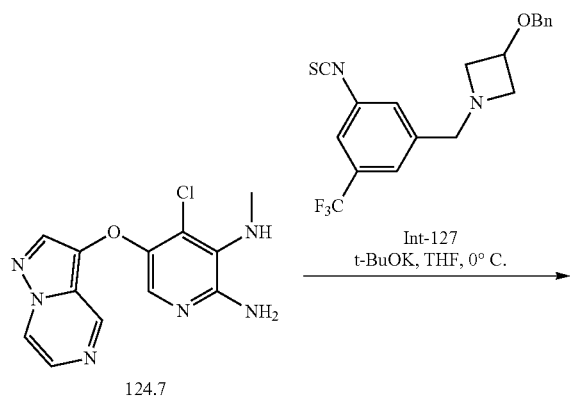

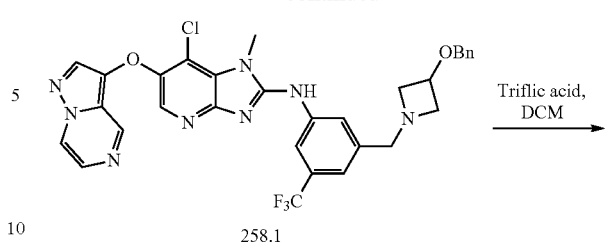

258.1

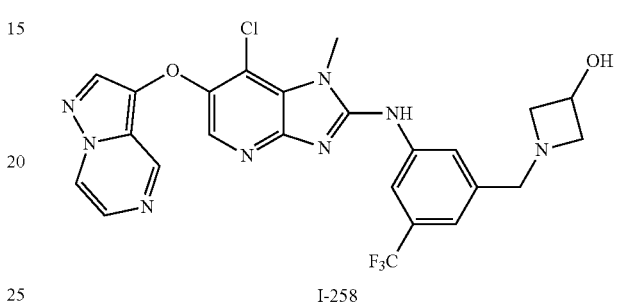

I-258

Synthesis of compound 258.1. Compound 258.1 was prepared from 124.7 and Int-127, following the procedure described in the synthesis of I-13. The product was purified by flash column chromatography on silica gel (CombiFlash®, 3.0% methanol in DCM). MS (ES): m/z 636.0 [M+H]$^+$.

Synthesis of I-258. Compound I-258 was prepared from 258.1, following the procedure described in the synthesis of I-23. The product was purified by flash column chromatography on silica gel (CombiFlash®, 3.7% methanol in DCM). MS (ES): m/z 545.2 [M+H]$^+$, $^1$H NMR (DMSO-d$_6$, 400 MHz): δ 9.75 (s, 1H), 9.02 (s, 1H), 8.70-8.69 (d, J=4.0 Hz, 1H), 8.30 (s, 1H), 8.21 (bs, 2H), 8.04 (s, 1H), 7.88-7.87 (d, J=4.0 Hz, 1H), 7.40 (s, 1H), 5.82 (bs, 1H), 4.40 (bs, 1H), 4.04 (s, 3H), 3.41 (bs, 2H), 2.68 (bs, 4H).

Example 259: 7-chloro-1-methyl-6-((4-(methylamino)pyrazolo[1,5-a]pyrazin-3-yl)oxy)-N-(3-((1-methylazetidin-3-yl)oxy)-5-(trifluoromethyl)phenyl)-1H-imidazo[4,5-b]pyridin-2-amine

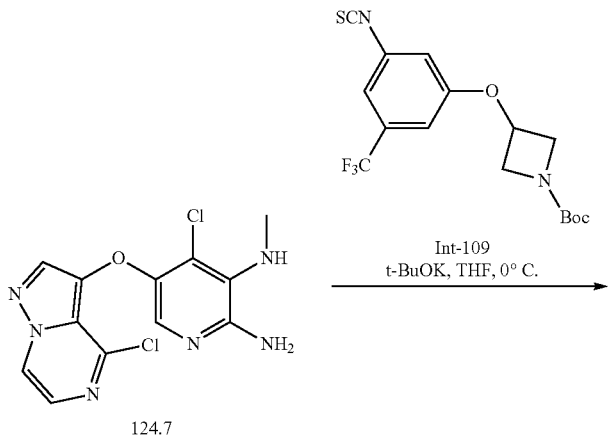

124.7

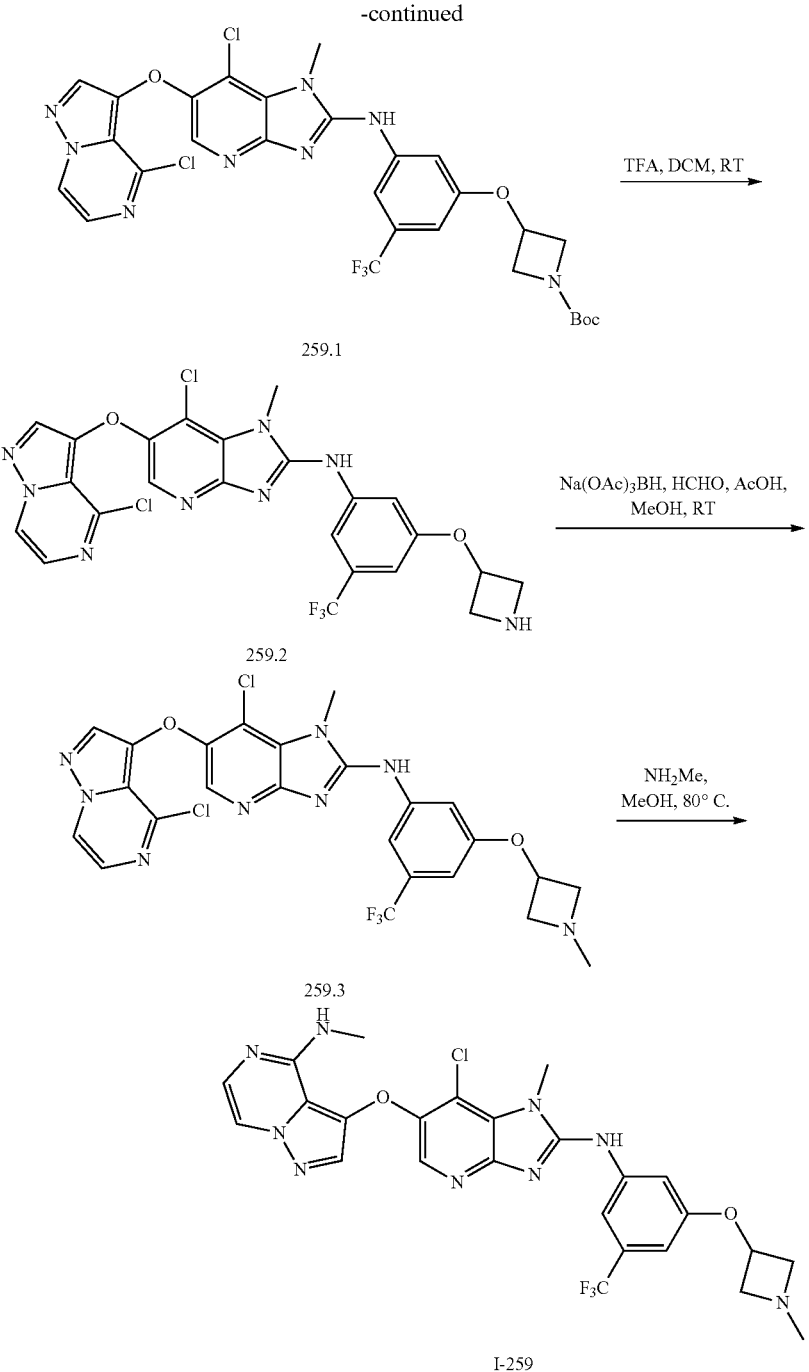

Synthesis of compound 259.1. Compound 259.1 was prepared from 124.7 and Int-109, following the procedure described in the synthesis of I-13. The product was purified by flash column chromatography on silica gel (Combi-Flash®, 2.200 methanol in DCM) to afford 259.1. MS (ES): m/z 666.3 [M+H]⁺.

Synthesis of compound 259.2. To a solution of 259.1 (0.120 g, 0.180 mmol, 1.0 equiv) in DCM (3 mL) was added trifluoroacetic acid (0.2 mL) dropwise at 0° C. The reaction mixture was stirred at room temperature for 2 h. It was concentrated under reduced pressure to afford residue which was triturated with diethyl ether to afford 259.2. MS (ES): m/z 566.2 [M+H]⁺.

Synthesis of compound 259.3. To a solution of 259.2 (0.100 g, 0.176 mmol, 1.0 equiv) in methanol (5 mL) was added formaldehyde (0.026 g, 0.880 mmol, 5.0 equiv), sodium triacetoxyborohydride (0.074 g, 0.352 mmol, 2.0 equiv) and acetic acid (0.1 mL). The reaction mixture was stirred at room temperature for 30 min. The reaction mixture was poured over ice-water and extracted with ethyl acetate. The combined organic layers were washed with brine, dried over anhydrous sodium sulfate, filtered and concentrated under reduced pressure. The residue was purified by flash column chromatography on silica gel (CombiFlash®, 8.0% methanol in DCM) afford 259.3. MS (ES): m/z 579.9 [M+H]⁺.

Synthesis of I-259. Compound I-259 was prepared from 259.3, following the procedure described in the synthesis of I-171. The product was purified by flash column chromatography on silica gel (CombiFlash®, 11% methanol in DCM). MS (ES): m/z 574.2 [M+H]$^+$, $^1$H NMR (DMSO-d$_6$, 400 MHz): δ 9.81 (s, 1H), 8.20 (s, 1H), 7.98 (s, 1H), 7.90 (s, 1H), 7.78-7.77 (d, J=4.8 Hz, 1H), 7.47 (s, 1H), 7.25-7.24 (d, J=4.8 Hz, 1H), 6.80 (bs, 2H), 5.02 (bs, 1H), 4.04 (s, 3H), 4.00-3.96 (m, 2H), 3.61 (bs, 2H), 2.99-2.98 (d, 3H), 2.36 (s, 3H).

Example 260: 6-((1H-pyrazolo[3,4-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

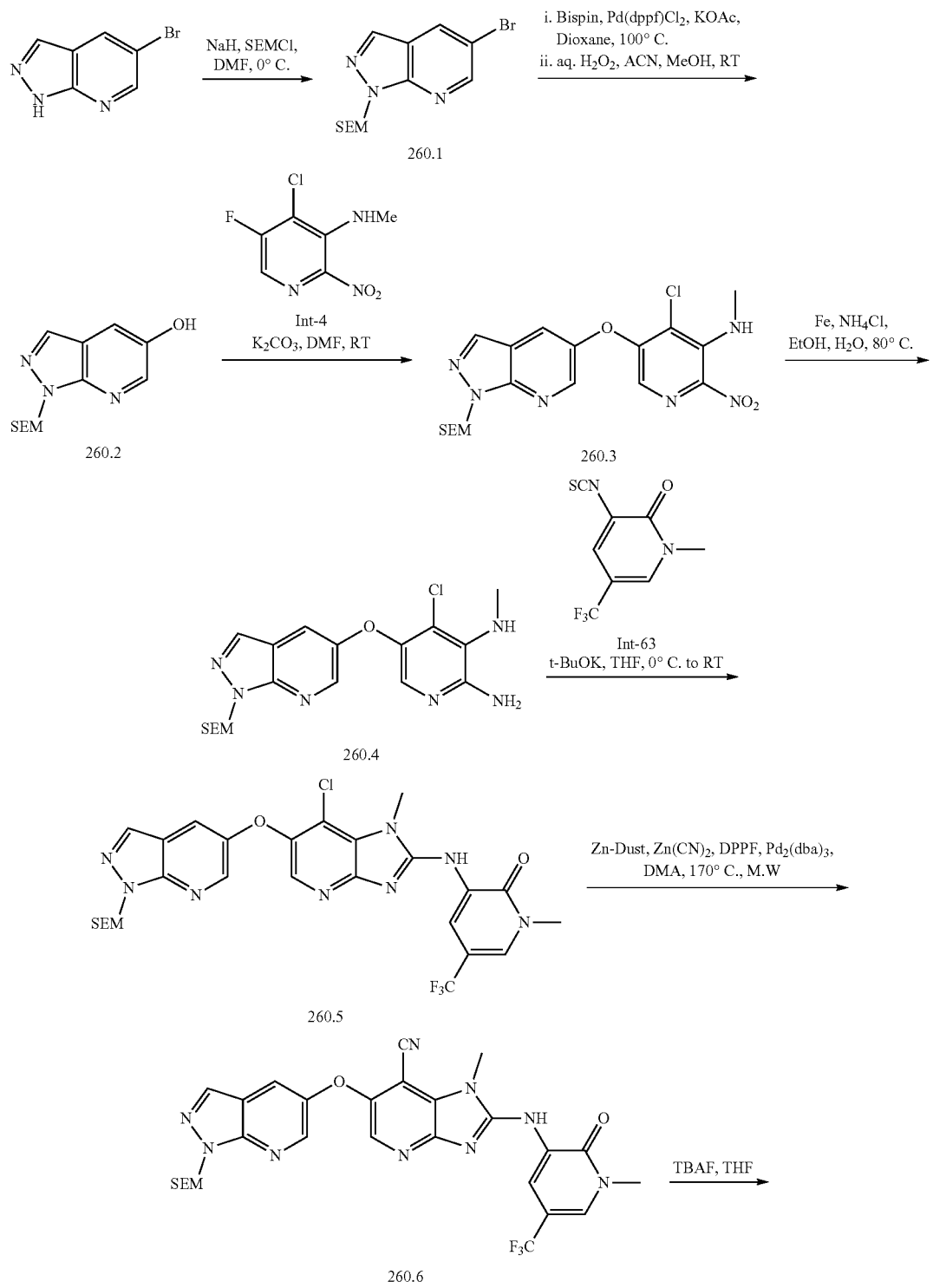

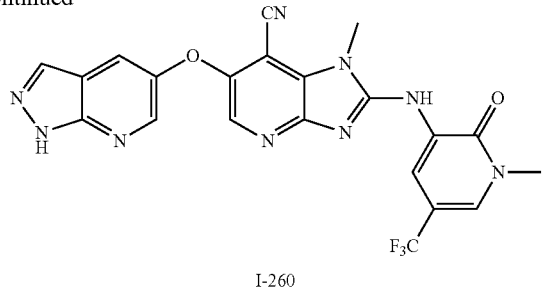

I-260

Synthesis of compound 260.1. To solution of 5-bromo-1H-pyrazolo[3,4-b]pyridine (5.0 g, 25.25 mmol, 1.0 equiv) in DMF (50 mL) was added sodium hydride (1.5 g, 37.87 mmol, 1.5 equiv) at 0° C. portionwise and reaction mixture was stirred for 15 min followed by addition of 2-(trimethylsilyl) ethoxymethyl chloride (6.32 g, 37.87 mmol, 1.5 equiv). The reaction mixture was stirred at room temperature for 3 h. It was poured over water and extracted with ethyl acetate. The combined organic layers were washed with brine, dried over anhydrous sodium sulfate, filtered and concentrated under reduced pressure to afford 260.1. MS (ES): m/z 328.1 [M+H]$^+$.

Synthesis of compound 260.2. A solution of 260.1 (5.2 g, 15.84 mmol, 1.0 equiv), bis(pinacolato)diboron (8.04 g, 31.68 mmol, 2.0 equiv) and potassium acetate (3.10 g, 31.68 mmol, 2.0 equiv) in 1,4-dioxane (50 mL) was degassed by bubbling through a stream of argon for 5 min. To the mixture was added 1,1-bis(diphenylphosphino)ferrocene-palladium (II) dichloride DCM complex (2.31 g, 3.168 mmol, 0.2 equiv) and degassed for another 5 min. It was stirred at 100° C. for 30 min, cooled to room temperature, transferred into ice cold water, stirred and extracted with ethyl acetate. The combined organic layers were washed with brine, dried over anhydrous sodium sulfate, filtered and concentrated under reduced pressure. The residue was added acetonitrile (100 mL), methanol (100 mL) and hydrogen peroxide (30 mL). The mixture was stirred at room temperature for 16 h. It was poured over ice cold water, stirred and extracted with ethyl acetate. The combined organic layers were washed with brine, dried over anhydrous sodium sulfate, filtered and concentrated under reduced pressure to afford 260.2. MS (ES): m/z 266.2 [M+H]$^+$.

Synthesis of compound 260.3. Compound 260.3 was prepared from 260.2 and Int-4, following the procedure described in the synthesis of 19.1. The product was purified by flash column chromatography on silica gel (CombiFlash®, 30% ethyl acetate in hexane). MS (ES): m/z 451.6 [M+H]$^+$.

Synthesis of compound 260.4. Compound 260.4 was prepared from 260.3, following the procedure described in the synthesis of 5.4. The product was purified by flash column chromatography on silica gel (CombiFlash®, 2.0% methanol in DCM). MS (ES): m/z 421.3 [M+H]$^+$.

Synthesis of compound 260.5. Compound 260.5 was prepared from 260.4 and Int-63, following the procedure described in the synthesis of I-13. The product was purified by flash column chromatography on silica gel (CombiFlash®, 2.2% methanol in DCM). MS (ES): m/z 622.8 [M+H]$^+$.

Synthesis of compound 260.6. Compound 260.6 was prepared from 260.5, following the procedure described in the synthesis of I-157. The product was purified by flash column chromatography on silica gel (CombiFlash®, 3.0% methanol in DCM). MS (ES): m/z 612.5 [M+H]$^+$.

Synthesis of I-260. To a solution of 260.6 (0.110 g, 0.179 mmol, 1.0 equiv) in THF (2.0 mL) was added tetra-n-butyl ammonium fluoride (1 M in THF, 4 mL) and stirred at 80° C. for 16 h. The reaction mixture was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in DCM) to afford I-260. MS (ES): m/z 482.2 [M+H]$^+$, $^1$H NMR (DMSO-d$_6$, 400 MHz): δ 13.82 (s, 1H), 9.03 (s, 1H), 8.66-8.65 (d, J=4.0 Hz, 1H), 8.61-8.60 (d, J=4.0 Hz, 1H), 8.20 (s, 1H), 8.13 (bs, 2H), 7.99-7.98 (d, J=4.0 Hz, 1H), 4.01 (s, 3H), 3.69 (s, 3H).

Example 261: 3-((6-((1H-pyrazolo[3,4-b]pyridin-5-yl)oxy)-7-chloro-1-methyl-1H-imidazo[4,5-b]pyridin-2-yl)amino)-1-methyl-5-(trifluoromethyl)pyridin-2(1H)-one

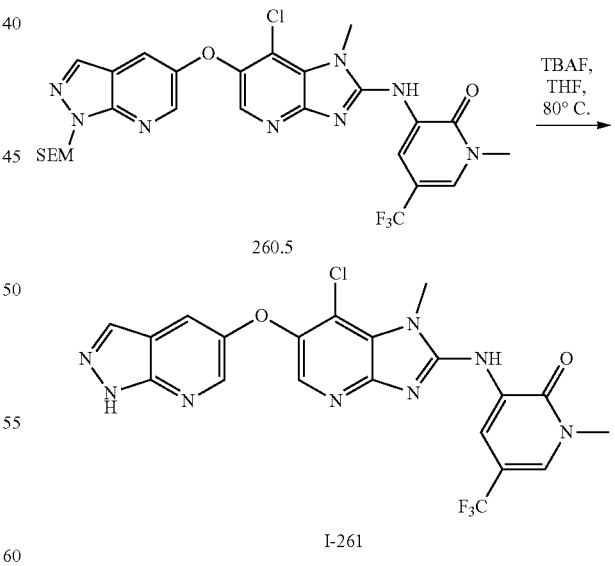

Synthesis of I-261. To a solution of 260.5 (0.160 g, 0.257 mmol, 1.0 equiv) in THF (3.0 mL) was added tetra-n-butyl ammonium fluoride (5 mL). The reaction mixture was stirred at 80° C. for 16 h. It was cooled to room temperature, transferred into water and extracted with ethyl acetate. The combined organic layers were washed with brine, dried over anhydrous sodium sulfate, filtered and concentrated under reduced pressure. The residue was purified by flash column chromatography on silica gel (CombiFlash®, 3.5% methanol in DCM) to afford I-261. MS (ES): m/z 491.2 [M+H]$^+$, $^1$H NMR (DMSO-d$_6$, 400 MHz): δ 13.71 (s, 1H), 8.86 (s, 1H), 8.63-8.62 (d, J=4.0 Hz, 1H), 8.54-8.53 (d, J=4.0 Hz, 1H), 8.19 (s, 1H), 8.15 (bs, 1H), 8.01 (s, 1H), 7.65-7.64 (d, J=4.0 Hz, 1H), 4.00 (s, 3H), 3.66 (s, 3H).

Example 262: (S)-3-((7-chloro-1-methyl-6-((4-(methylamino)pyrazolo[1,5-a]pyrazin-3-yl)oxy)-1H-imidazo[4,5-b]pyridin-2-yl)amino)-1-(tetrahydrofuran-3-yl)-5-(trifluoromethyl)pyridin-2(1H)-one and (R)-3-((7-chloro-1-methyl-6-((4-(methylamino)pyrazolo[1,5-a]pyrazin-3-yl)oxy)-1H-imidazo[4,5-b]pyridin-2-yl)amino)-1-(tetrahydrofuran-3-yl)-5-(trifluoromethyl)pyridin-2(1H)-one Synthesis of compound (±)-262.1. Compound (±)-262.1 was prepared from 124.7 and (±)-Int-128, following the procedure described in the synthesis of I-13. The product was purified by flash column chromatography on silica gel (CombiFlash®, 2.0% methanol in DCM). MS (ES): m/z 582.1 [M+H]$^+$.

Synthesis of compound I-262-a and I-262-b. To a solution (±)-262.1 (0.140 g, 0.240 mmol, 1.0 equiv) in methanol (2 mL) was added methylamine solution (2 M in THF, 1.4 mL) and stirred at 80° C. for 16 h. It was concentrated under reduced pressure. The residue was purified by flash column chromatography on silica gel (CombiFlash®, 5.0% methanol in DCM). The racemate was separated by HPLC (column: CHIRALPAK IB-N (250 mm*21 mm, 5 µm); mobile phase: (A) 0.1% DEA in n-hexane (B) 0.1% DEA in isopropanol:acetonitrile (70:30); flow rate=20 mL/min) to

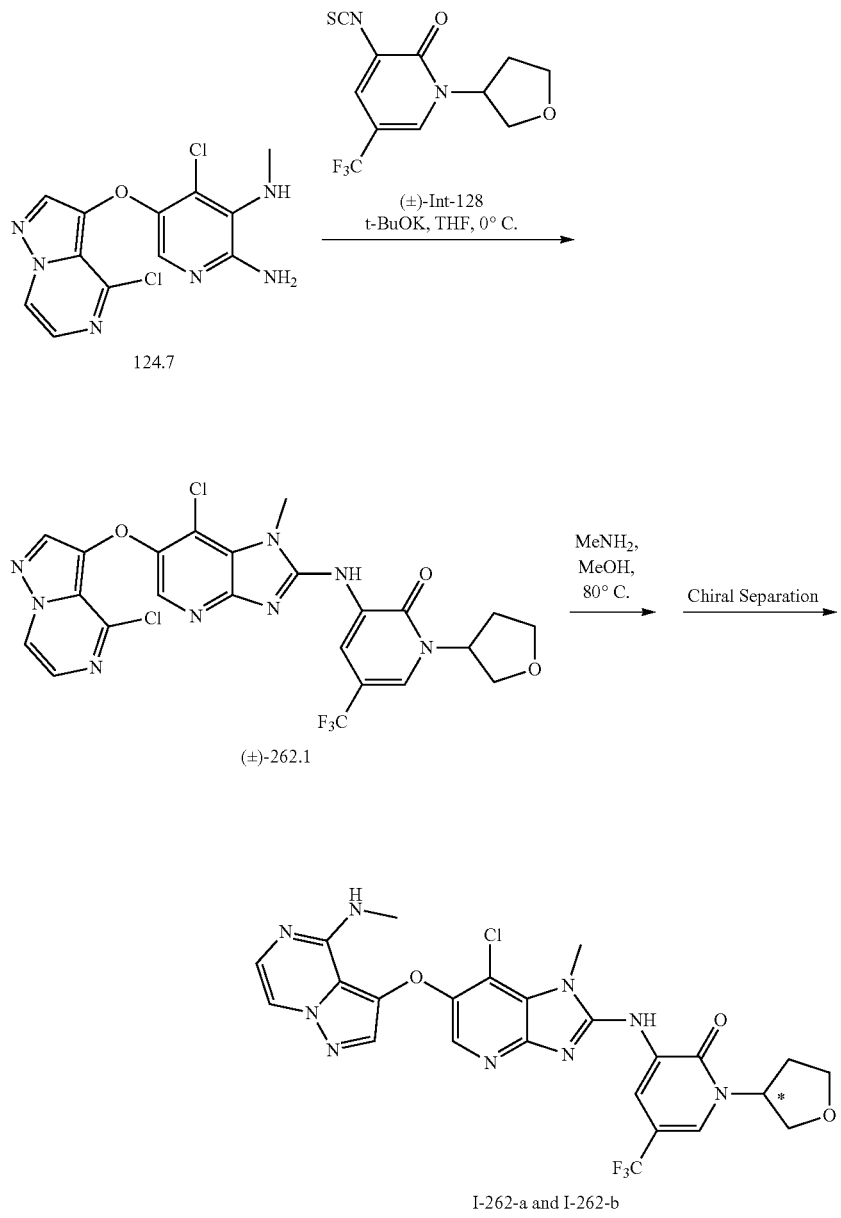

afford first eluting fraction (I-262-a) and second eluting fraction (I-262-b). (*Absolute stereochemistry not determined.)

I-262-a: MS (ES): m/z 576.2 [M+H]$^+$, $^1$H NMR (DMSO-d$_6$, 400 MHz): δ 8.90 (s, 1H), 8.62 (s, 1H), 8.24 (s, 1H), 7.78-7.77 (d, J=4.8 Hz, 1H), 7.74 (s, 1H), 7.50 (s, 1H), 7.26-7.24 (d, J=4.8 Hz, 1H), 6.83-6.82 (d, J=4.4 Hz, 1H), 5.48 (bs, 1H), 4.12-4.06 (m, 2H), 4.01 (s, 3H), 3.92-3.90 (m, 1H), 3.80-3.78 (m, 1H), 2.99-2.98 (d, 3H), 2.14 (bs, 2H).

I-262-b: MS (ES): m/z 576.2 [M+H]$^+$, $^1$H NMR (DMSO-d$_6$, 400 MHz): δ 8.91 (s, 1H), 8.63 (s, 1H), 8.25 (s, 1H), 7.80-7.79 (d, J=4.8 Hz, 1H), 7.75 (s, 1H), 7.51 (s, 1H), 7.27-7.26 (d, J=4.8 Hz, 1H), 6.85 (bs, 1H), 5.49 (bs, 1H), 4.15-4.10 (m, 2H), 4.03 (s, 3H), 3.94-3.90 (m, 1H), 3.81-3.77 (m, 1H), 3.00-2.99 (d, 3H), 2.16 (bs, 2H).

Example 263: N-(3-(azetidin-1-ylmethyl)-5-(trifluoromethyl)phenyl)-7-chloro-1-methyl-6-((4-(methylamino)pyrazolo[1,5-a]pyrazin-3-yl)oxy)-1H-imidazo[4,5-b]pyridin-2-amine

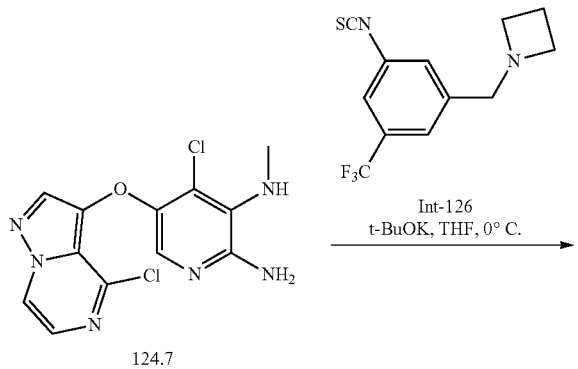

124.7

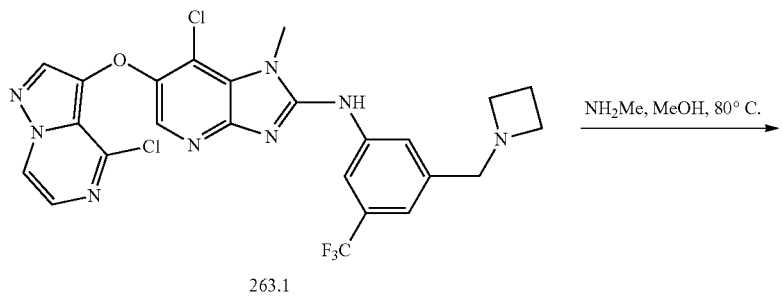

263.1

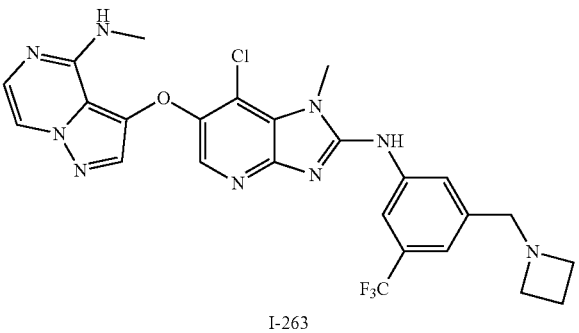

I-263

Synthesis of compound 263.1. Compound 263.1 was prepared from 124.7 and Int-126, following the procedure described in the synthesis of I-13. The product was purified by flash column chromatography on silica gel (Combi-Flash®, 7.0% methanol in DCM) t. m/z 564.3 [M+H]⁺.

Synthesis of I-263. Compound I-263 was prepared from 263.1, following the procedure described in the synthesis of I-171. The product was purified by trituration in diethyl ether. MS (ES): m/z 558.2 [M]⁺, ¹H NMR (DMSO-d₆, 400 MHz): δ 9.81 (s, 1H), 8.33 (s, 1H), 8.21 (s, 1H), 8.17 (s, 1H), 7.79-7.78 (d, J=4.8 Hz, 1H), 7.48 (s, 1H), 7.36 (s, 1H), 7.27-7.26 (d, J=4.8 Hz, 1H), 6.83-6.82 (d, J=4.0 Hz, 1H), 4.05 (s, 3H), 3.91 (bs, 2H), 3.45 (bs, 2H), 3.01-3.00 (d, 3H), 2.38 (s, 2H), 2.14 (s, 2H).

Example 264: 1-(3-((7-chloro-1-methyl-6-((4-(methylamino)pyrazolo[1,5-a]pyrazin-3-yl)oxy)-1H-imidazo[4,5-b]pyridin-2-yl)amino)-5-(trifluoromethyl)benzyl)azetidin-3-ol

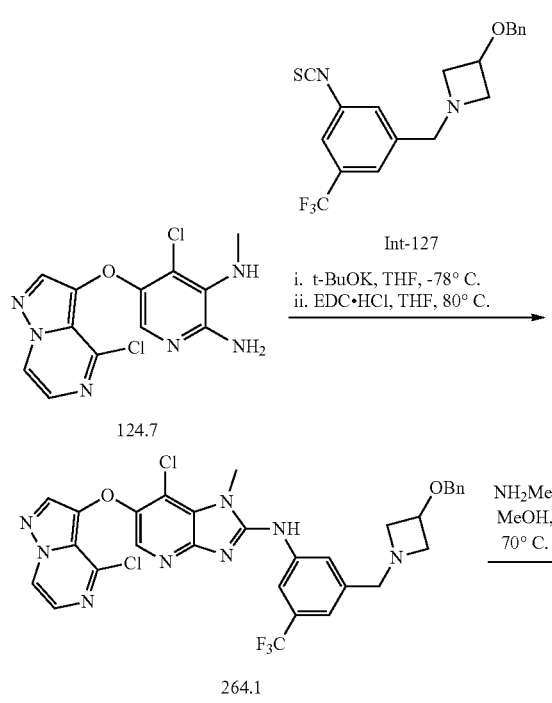

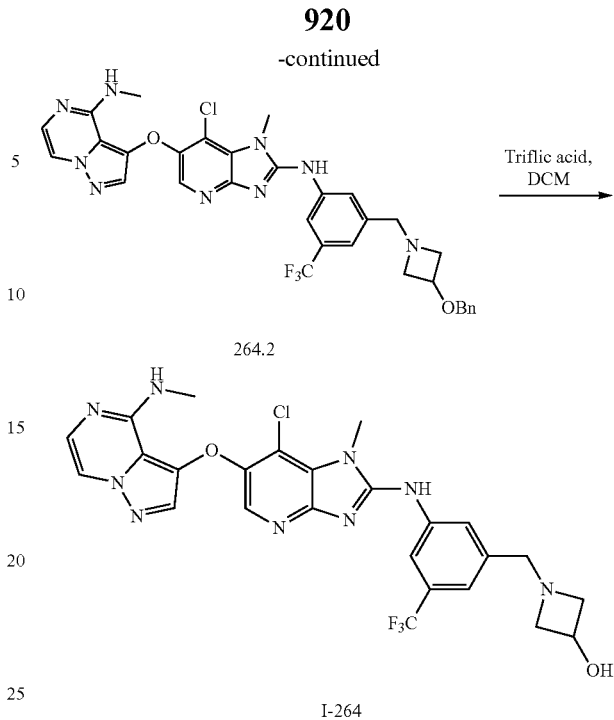

Synthesis of compound 264.1. Compound 264.1 was prepared from 124.7 and Int-127, following the procedure described in the synthesis of 249.1. The product was purified by flash column chromatography on silica gel (CombiFlash®, 2.4% methanol in DCM). MS (ES): m/z 670.3 [M+H]⁺.

Synthesis of compound 264.2. Compound 264.2 was prepared from 264.1, following the procedure described in the synthesis of I-171. The product was purified by trituration in methanol. MS (ES): m/z 664.8 [M+H]⁺.

Synthesis of I-264. Compound I-264 was prepared from 264.2, following the procedure described in the synthesis of I-23. The product was purified by flash column chromatography on silica gel (CombiFlash®, 5.4% methanol in DCM). MS (ES): m/z 574.2 [M+H]⁺, ¹H NMR (DMSO-d₆, 400 MHz): δ 9.71 (s, 1H), 8.31 (s, 1H), 8.21 (s, 1H), 8.14 (s, 1H), 7.79-7.78 (d, J=4.8 Hz, 1H), 7.48 (s, 1H), 7.33 (s, 1H), 7.27-7.26 (s, 1H), 6.83-6.82 (d, J=4.0 Hz, 1H), 5.58 (bs, 1H), 4.32 (bs, 1H), 4.04 (s, 3H), 3.74 (bs, 2H), 3.01-3.00 (d, 3H), 2.62 (bs, 4H).

Example 265: 6-((1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

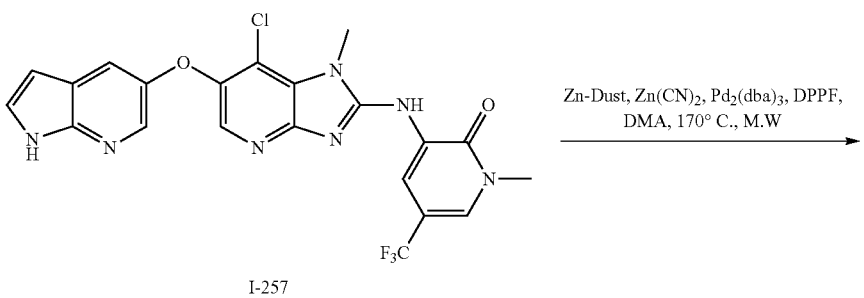

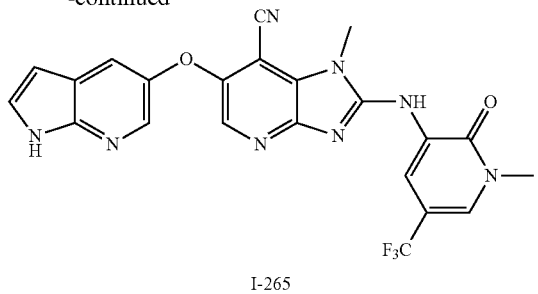

I-265

Synthesis of I-265. Compound I-265 was prepared from I-257, following the procedure described in the synthesis of I-157. The product was purified by flash column chromatography on silica gel (CombiFlash®, 3.5% methanol in DCM). MS (ES): m/z 481.3 [M+H]$^+$, $^1$H NMR (DMSO-d$_6$, 400 MHz): δ 11.82 (s, 1H), 8.97 (s, 1H), 8.63 (s, 1H), 8.22-8.21 (d, J=2.4 Hz, 1H), 8.17 (s, 1H), 7.99 (s, 1H), 7.77 (s, 1H), 7.57 (s, 1H), 6.45 (s, 1H), 3.99 (s, 3H), 3.67 (s, 3H).

Example 266: 3-((7-chloro-1-methyl-6-(pyrazolo[1,5-a]pyrazin-3-yloxy)-1H-imidazo[4,5-b]pyridin-2-yl)amino)-5-cyclopropyl-6-fluoro-1-methylpyridin-2(1H)-one (DMSO-d$_6$, 400 MHz): δ 9.03 (s, 1H), 8.70-8.69 (d, J=4.4 Hz, 1H), 8.47 (s, 1H), 8.23 (s, 1H), 8.20 (s, 1H), 8.04 (s, 1H), 7.88-7.87 (d, J=4.8 Hz, 1H), 3.98 (s, 3H), 3.56 (s, 3H), 1.89 (bs, 1H), 0.96-0.94 (m, 2H), 0.63-0.62 (m, 2H).

Example 267: N-(5-(tert-butyl)-1-((3R,4R)-4-fluoro-1-methylpyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine and N-(5-(tert-butyl)-1-((3S,4S)-4-fluoro-1-methylpyrrolidin-3-yl)-1H-pyrazol-3-yl)-7-chloro-1-methyl-6-(pyrazolo[1,5-a]pyrazin-3-yloxy)-1H-imidazo[4,5-b]pyridin-2-amine

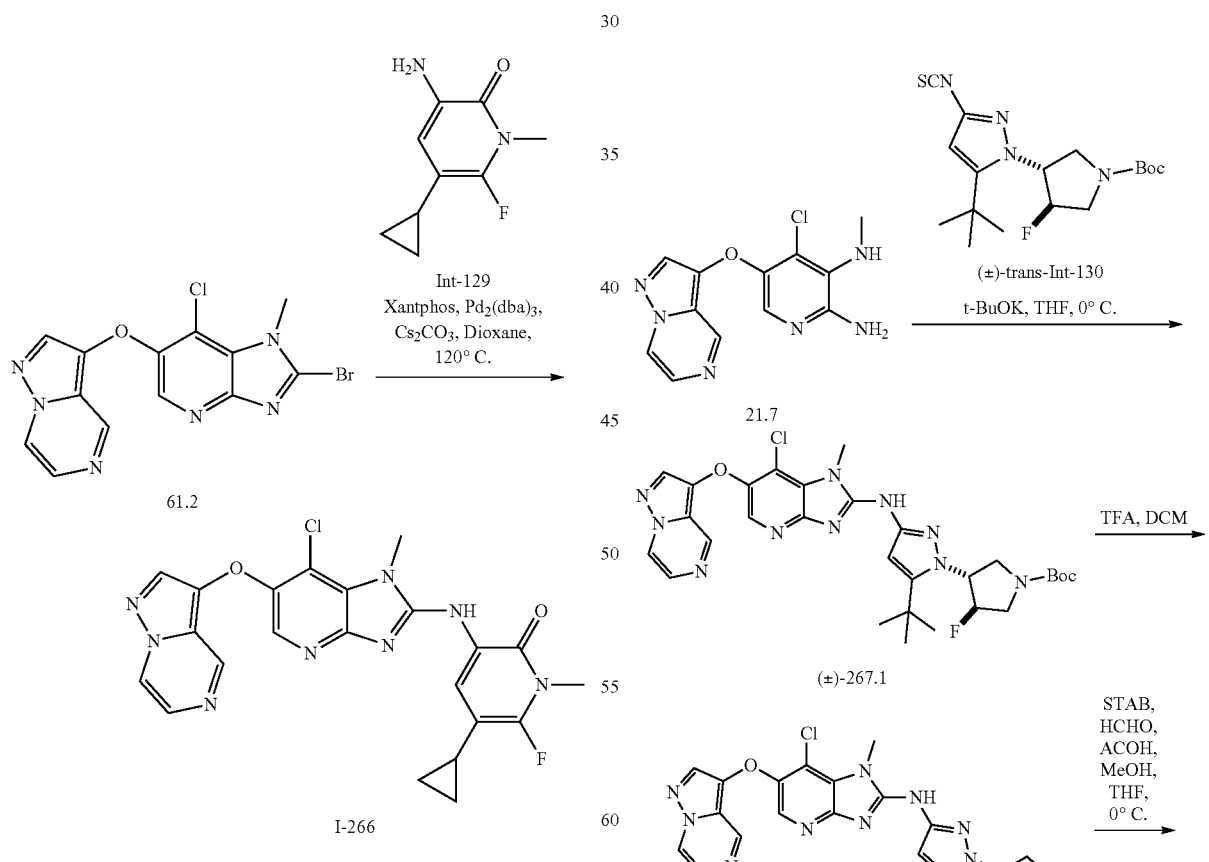

Synthesis of I-266. Compound I-266 was prepared from 61.2 and Int-129, following the procedure described in the synthesis of I-53. The product was purified by flash column chromatography on silica gel (CombiFlash®, 2.4% methanol in DCM). MS (ES): m/z 481.2 [M+H]$^+$. $^1$H NMR

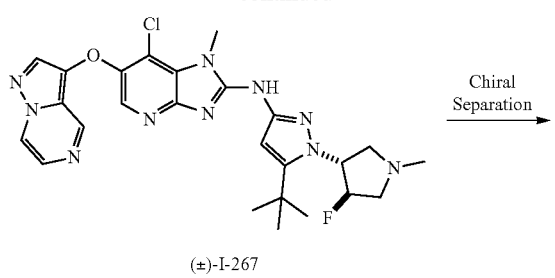

(±)-I-267

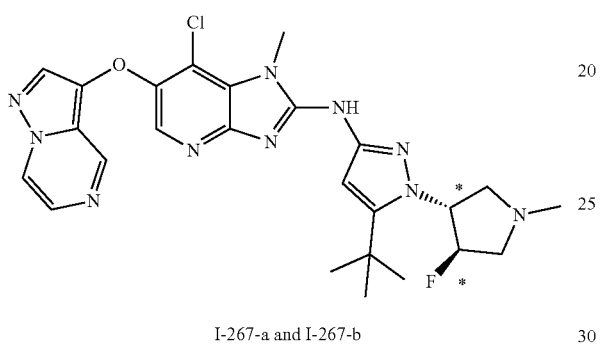

I-267-a and I-267-b

Synthesis of compound (±)-267.1. Compound (±)-267.1 was prepared from 21.7 and (±)-trans-Int-130, following the procedure described in the synthesis of I-13. The product was purified by flash column chromatography on silica gel (CombiFlash®, 2.1% methanol in DCM). MS (ES): m/z 626.1 [M+H]⁺.

Synthesis of compound (±)-267.2. To solution of (±)-267.1 (0.125 g, 0.199 mmol, 1.0 equiv) in DCM (3 mL) was added trifluoroacetic acid (1 mL) at 0° C. and stirred for 30 min. It was transferred into ice-saturated sodium bicarbonate solution and extracted with DCM. The combined organic layers were washed with brine, dried over anhydrous sodium sulfate, filtered, and concentrated under reduced pressure to afford (±)-267.2. MS (ES): m/z 525.5 [M+H]⁺.

Synthesis of compound (±)-I-267. To a solution of (±)-267.2 (0.080 g, 0.152 mmol, 1.0 equiv) and formaldehyde (0.022 g, 0.76 mmol, 5.0 equiv) in methanol (2 mL) and THF (2 mL) was added sodium triacetoxyborohydride (0.096 g, 0.456 mmol, 3.0 equiv) and acetic acid (0.2 mL). The reaction mixture was stirred at room temperature for 30 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford (±)-I-267. MS (ES): m/z 539.3 [M+H]⁺.

I-267-a and I-276-b. (±)-I-267 was submitted to HPLC separation (column: CHIRALPAK IB-N (250 mm*21 mm, 5 μm); mobile phases: (A) 0.1% DEA in hexane, (B) 0.1% DEA in propan-2-ol:acetonitrile (70:30); flow rate: 20 mL/min) to afford first eluting fraction (I-267-a) and second eluting fraction (I-267-b). (*Absolute stereochemistry not determined.)

I-267-a: MS (ES): m/z 539.3 [M+H]⁺, ¹H NMR (DMSO-d₆, 400 MHz): δ 9.05 (s, 1H), 8.71 (s, 1H), 8.11-8.04 (m, 2H), 7.89 (bs, 2H), 6.25 (s, 1H), 5.49 (bs, 1H), 5.35 (bs, 1H), 3.96 (bs, 2H), 3.78 (bs, 2H), 3.46 (s, 3H), 2.34 (s, 3H), 1.27 (s, 9H).

I-267-b: MS (ES): m/z 539.3 [M+H]⁺, ¹H NMR (DMSO-d₆, 400 MHz): δ 9.05 (s, 1H), 8.71 (s, 1H), 8.12-8.05 (m, 2H), 7.89 (bs, 2H), 6.29 (s, 1H), 5.49 (bs, 1H), 5.36 (bs, 1H), 3.97 (bs, 2H), 3.79 (bs, 2H), 3.46 (s, 3H), 2.35 (s, 3H), 1.28 (s, 9H).

Example I-268: N-(5-(azetidin-1-yl)-4,6-dimethylpyrimidin-2-yl)-7-chloro-1-methyl-6-(pyrazolo[1,5-a]pyrazin-3-yloxy)-1H-imidazo[4,5-b]pyridin-2-amine

[Reaction scheme showing 21.7 + Int-131, t-BuOK, THF, 0° C. → I-268]

Synthesis of I-268. Compound I-268 was prepared from 21.7 and Int-131, following the procedure described in the synthesis of I-13. The product was purified by flash column chromatography on silica gel (CombiFlash®, 2.8% methanol in DCM) to afford I-268 (0.040 g, Yield: 20.32%). MS (ES): m/z 477.3 [M+H]⁺, ¹H NMR (DMSO-d₆, 400 MHz): δ 9.95 (s, 1H), 9.07 (s, 1H), 8.69 (bs, 1H), 8.26 (s, 1H), 8.05 (s, 1H), 7.87 (bs, 1H), 4.02-4.01 (m, 4H), 3.83 (s, 3H), 2.33 (s, 6H), 2.19-2.17 (m, 2H).

Example 269: (R)-7-chloro-1-methyl-6-((4-(methylamino)pyrazolo[1,5-a]pyrazin-3-yl)oxy)-N-(3-(1-methylpyrrolidin-2-yl)-5-(trifluoromethyl)phenyl)-1H-imidazo[4,5-b]pyridin-2-amine and (S)-7-chloro-1-methyl-6-((4-(methylamino)pyrazolo[1,5-a]pyrazin-3-yl)oxy)-N-(3-(1-methylpyrrolidin-2-yl)-5-(trifluoromethyl)phenyl)-1H-imidazo[4,5-b]pyridin-2-amine

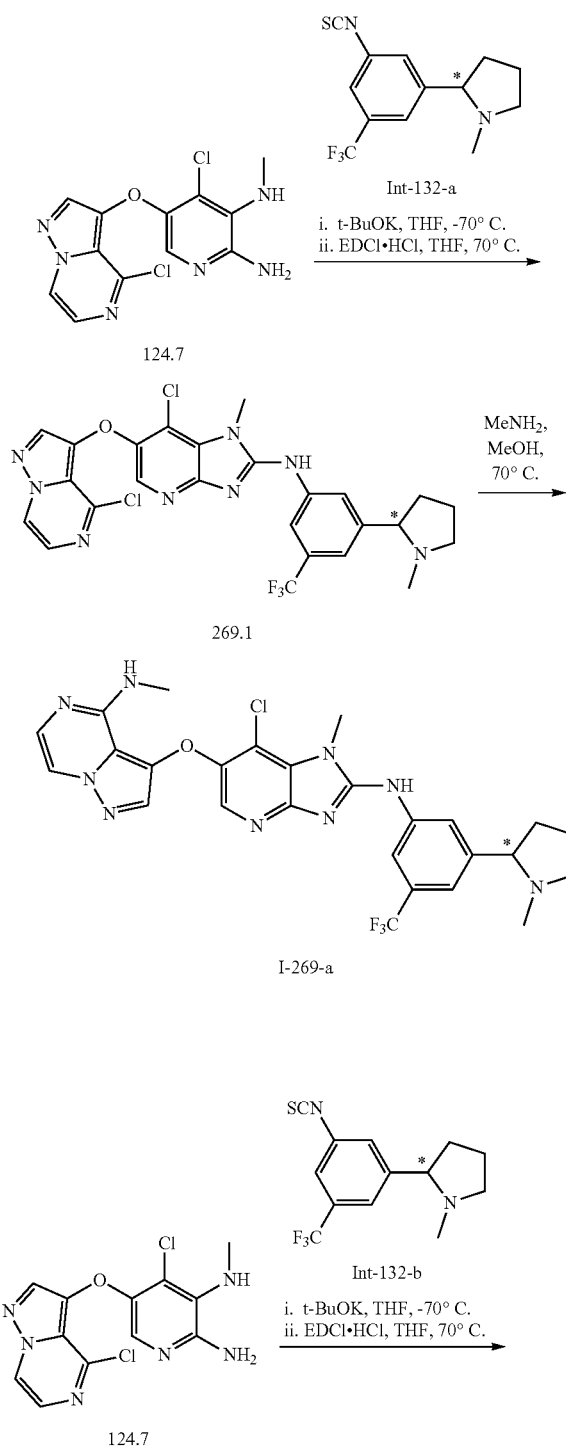

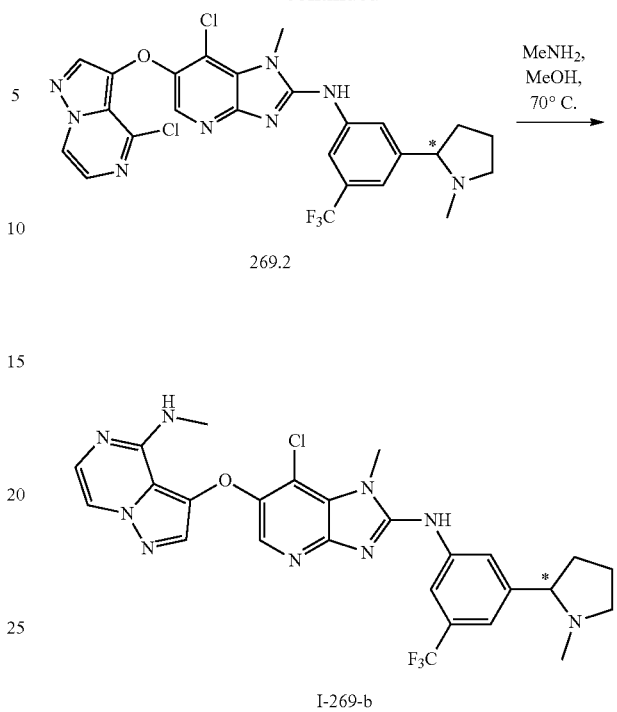

Synthesis of compound 269.1. Compound 269.1 was prepared from 124.7 and Int-132-a, following the procedure described in the synthesis of I-51. The product was purified by flash column chromatography on silica gel (CombiFlash®, 5.0% methanol in DCM). MS (ES): m/z 578.2 [M+H]$^+$.

Synthesis of I-269-a. To a solution of 269.1 (0.061 g, 0.105 mmol, 1.0 equiv) in methanol (2 mL) was added methylamine solution (2 M in THF, 0.6 mL) and stirred at 70° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.2% methanol in DCM) to afford I-269-a. MS (ES): m/z 572.3 [M+H]$^+$, $^1$H NMR (DMSO-d$_6$, 400 MHz): δ 9.68 (s, 1H), 8.39 (s, 1H), 8.20-8.19 (d, J=3.6 Hz, 1H), 8.09 (s, 1H), 7.78-7.77 (d, J=4.8 Hz, 1H), 7.48-7.47 (d, J=4.0 Hz, 1H), 7.32 (s, 1H), 7.26-7.25 (d, J=4.4 Hz, 1H), 6.82 (bs, 1H), 4.04-4.03 (d, 3H), 3.21 (s, 3H), 3.00 (s, 3H), 2.30-2.28 (m, 1H), 2.17 (bs, 2H), 1.83 (bs, 2H), 1.57 (bs, 2H). (*Absolute stereochemistry not determined.)

Synthesis of compound I-269-b. Compound I-269-b was prepared from compound 124.7 and Int-132-b, following the procedures described in the synthesis of I-269-a. The product was purified by flash column chromatography on silica gel (CombiFlash®, 5.4% methanol in DCM). MS (ES): m/z 572.3 [M+H]$^+$, $^1$H NMR (DMSO-d$_6$, 400 MHz): δ 9.68 (s, 1H), 8.38 (s, 1H), 8.19 (s, 1H), 8.08 (s, 1H), 7.78-7.77 (d, J=4.8 Hz, 1H), 7.47 (d, J=4.0 Hz, 1H), 7.31 (s, 1H), 7.25-7.24 (d, J=4.4 Hz, 1H), 6.83-6.82 (d, J=4.4 Hz, 1H), 4.02 (s, 3H), 3.21 (bs, 3H), 2.99 (s, 3H), 2.30-2.28 (m, 1H), 2.16 (bs, 2H), 1.82 (bs, 2H), 1.57 (bs, 2H). (*Absolute stereochemistry not determined.)

Example 270: (R)-7-chloro-1-methyl-N-(3-(1-methylpyrrolidin-2-yl)-5-(trifluoromethyl)phenyl)-6-(pyrazolo[1,5-a]pyrazin-3-yloxy)-1H-imidazo[4,5-b]pyridin-2-amine and (S)-7-chloro-1-methyl-N-(3-(1-methylpyrrolidin-2-yl)-5-(trifluoromethyl)phenyl)-6-(pyrazolo[1,5-a]pyrazin-3-yloxy)-1H-imidazo[4,5-b]pyridin-2-amine

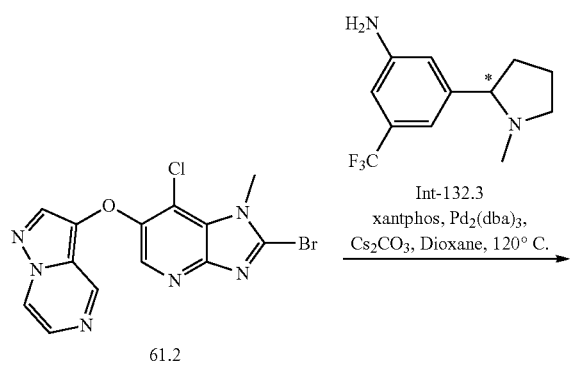

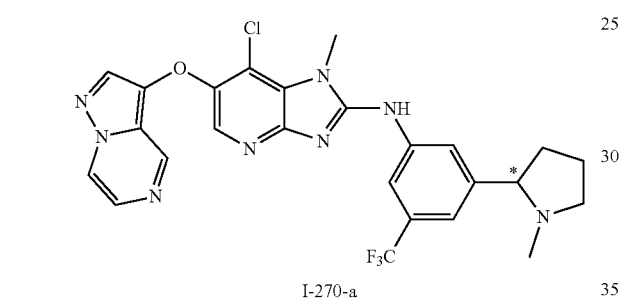

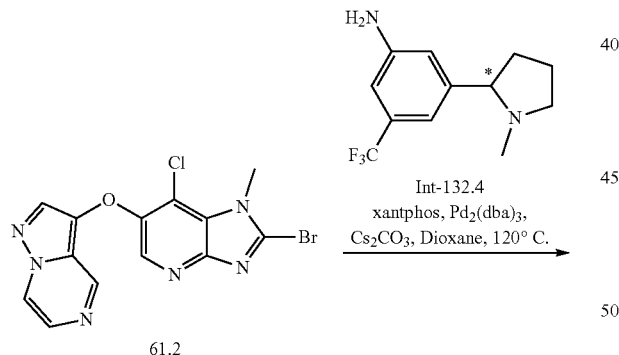

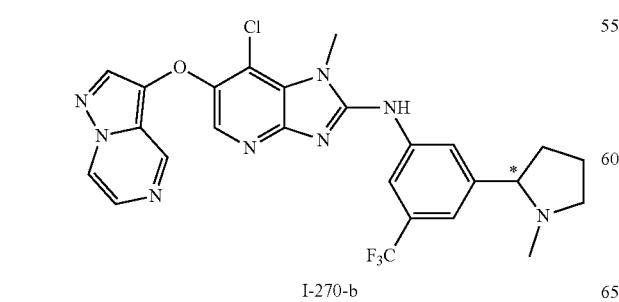

Synthesis of I-270-a. Compound I-270-a was prepared from 61.2 and Int-132.3, following the procedure described in the synthesis of I-53. The product was purified by flash column chromatography on silica gel (CombiFlash®, 3.5% methanol in DCM). MS (ES): m/z 543.2 [M+H]$^+$, $^1$H NMR (DMSO-d$_6$, 400 MHz): δ 9.67 (s, 1H), 9.03 (bs, 1H), 8.70-8.69 (d, J=4.8 Hz, 1H), 8.39 (s, 1H), 8.21 (s, 1H), 8.08 (s, 1H), 8.04 (s, 1H), 7.88-7.87 (d, J=4.8 Hz, 1H), 7.32 (s, 1H), 4.04 (s, 3H), 3.23-3.22 (m, 2H), 2.35 (bs, 1H), 2.16 (bs, 3H), 1.90-1.81 (m, 2H), 1.62 (bs, 2H).

Synthesis of I-270-b. Compound I-270-b was prepared from 61.2 and Int-132.4, following the procedure described in the synthesis of I-53. The product was purified by flash column chromatography on silica gel (CombiFlash®, 3.5% methanol in DCM). MS (ES): m/z 543.2 [M+H]$^+$, $^1$H NMR (DMSO-d$_6$, 400 MHz): δ 9.66 (s, 1H), 9.01 (bs, 1H), 8.69-8.68 (d, J=4.8 Hz, 1H), 8.37 (s, 1H), 8.20 (s, 1H), 8.06 (s, 1H), 8.03 (s, 1H), 7.87-7.86 (d, J=4.8 Hz, 1H), 7.30 (s, 1H), 4.02 (s, 3H), 3.21-3.17 (m, 2H), 2.32 (bs, 1H), 2.15 (bs, 3H), 1.86-1.80 (m, 2H), 1.61 (bs, 2H).

Example 271: (R)-7-chloro-N-(3-((3-(dimethylamino)pyrrolidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

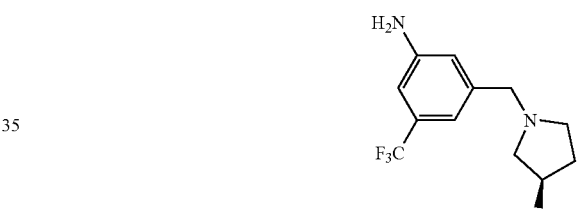

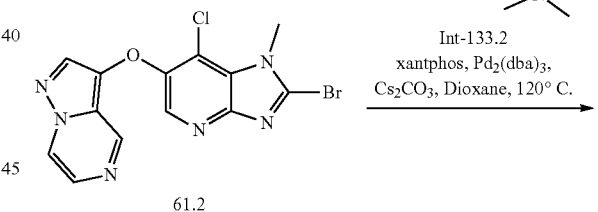

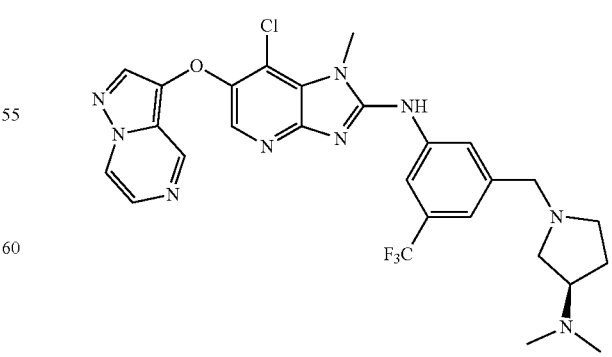

Synthesis of I-271. Compound I-271 was prepared from 61.2 and Int-133.2, following the procedure described in the synthesis of I-53. The product was purified by flash column chromatography on silica gel (CombiFlash®, 10% methanol in DCM). MS (ES): m/z 587.3 [M+H]$^+$, $^1$H NMR (DMSO-$d_6$, 400 MHz): δ 9.66 (s, 1H), 9.01 (s, 1H), 8.69 (bs, 1H), 8.32 (s, 1H), 8.19 (s, 1H), 8.05 (s, 1H), 8.03 (s, 1H), 7.87-7.86 (d, J=3.2 Hz, 1H), 7.27 (s, 1H), 4.02 (s, 3H), 3.74-3.71 (m, 1H), 3.60-3.57 (m, 1H), 2.70 (bs, 2H), 2.63-2.62 (m, 2H), 2.31 (bs, 1H), 2.08 (s, 6H), 1.86 (bs, 1H), 1.64 (bs, 1H).

Example 272: (R)-7-chloro-N-(3-((3-(dimethylamino)pyrrolidin-1-yl)methyl)-5-(trifluoromethyl)phenyl)-1-methyl-6-(pyrazolo[1,5-a]pyrazin-3-yloxy)-1H-imidazo[4,5-b]pyridin-2-amine

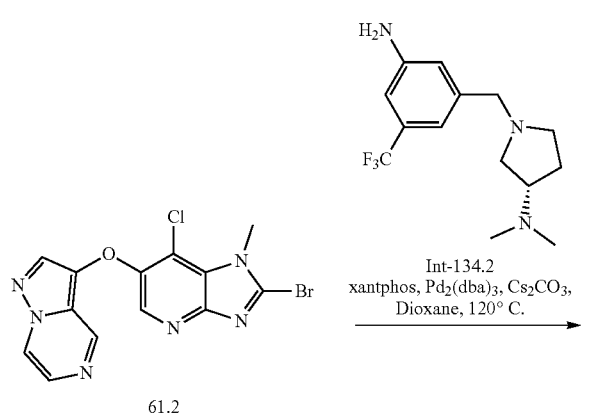

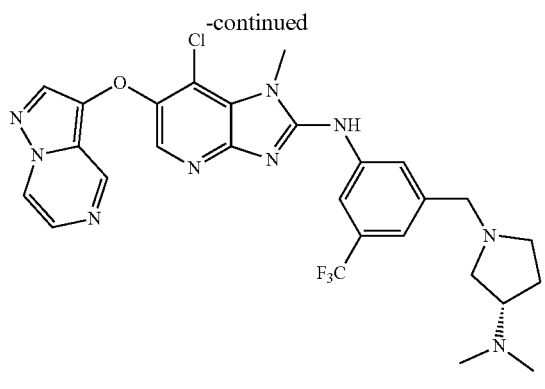

I-272

Synthesis of I-272. Compound I-272 was prepared from 61.2 and Int-134.2, following the procedure described in the synthesis of I-53. The product was purified by flash column chromatography on silica gel (CombiFlash®, 10% methanol in DCM). MS (ES): m/z 587.2 [M+H]$^+$, $^1$H NMR (DMSO-$d_6$, 400 MHz): δ 9.67 (s, 1H), 9.03 (s, 1H), 8.71-8.69 (d, J=4.4 Hz, 1H), 8.33 (s, 1H), 8.21 (s, 1H), 8.08 (s, 1H), 8.05 (s, 1H), 7.88-7.87 (d, J=4.8 Hz, 1H), 7.29 (s, 1H), 4.04 (s, 3H), 3.76-3.72 (m, 1H), 3.62-3.59 (m, 1H), 2.73 (bs, 2H), 2.63-2.61 (m, 2H), 2.33 (bs, 1H), 2.06 (s, 6H), 1.99-1.88 (m, 1H), 1.65-1.64 (m, 1H).

Example 273: N-(1-(2-oxaspiro[3.3]heptan-6-yl)-5-(trifluoromethyl)-1H-pyrazol-3-yl)-7-chloro-6-((4-(2-methoxyethoxy)pyrazolo[1,5-a]pyrazin-3-yl)oxy)-1-methyl-1H-imidazo[4,5-b]pyridin-2-amine

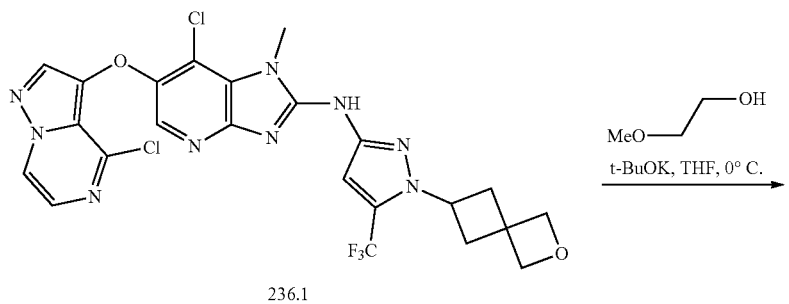

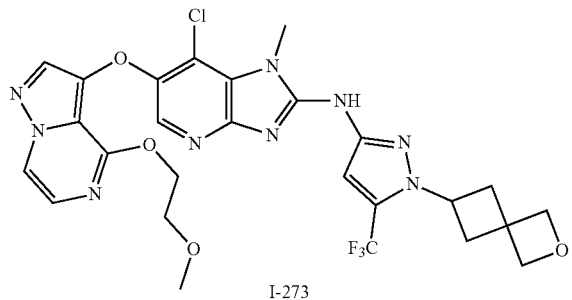

I-273

Synthesis of I-273. To a solution of 236.1 (0.054 g, 0.093 mmol, 1.0 equiv) and 2-methoxyethan-1-ol (0.008 g, 0.111 mmol, 1.2 equiv) in THF (5 mL) was added potassium tert-butoxide (1 M in THF, 0.28 mL, 0.279 mmol, 3.0 equiv) at 0° C. and reaction mixture was stirred at 0° C. for 1 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.1% methanol in DCM) to afford I-273. MS (ES): m/z 620.2 [M]$^+$, $^1$H NMR (DMSO-d$_6$, 400 MHz): δ 10.48 (s, 1H), 8.29-8.28 (d, J=4.8 Hz, 1H), 7.99 (s, 1H), 7.88 (s, 1H), 7.37-7.35 (d, J=4.8 Hz, 1H), 7.28 (s, 1H), 4.84-4.80 (m, 1H), 4.69 (s, 2H), 4.58 (s, 2H), 4.43 (bs, 2H), 3.99 (s, 3H), 3.47-3.46 (m, 2H), 3.10 (s, 3H), 2.80-2.78 (m, 4H).

Example 274: N$^4$-(7-chloro-1-methyl-6-(pyrazolo[1,5-a]pyrazin-3-yloxy)-1H-imidazo[4,5-b]pyridin-2-yl)-N$^2$,N$^2$-dimethyl-6-(trifluoromethyl)pyridine-2,4-diamine

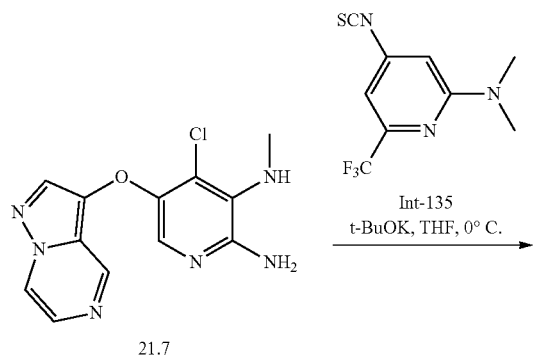

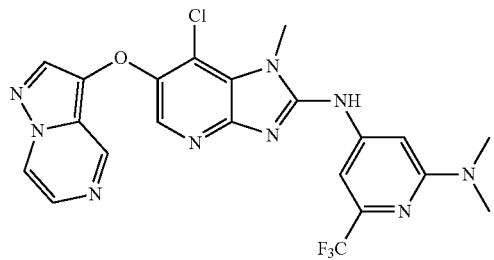

I-274

Synthesis of I-274. Compound I-274 was prepared from 21.7 and Int-135, following the procedure described in the synthesis of I-13. The product was purified by flash column chromatography on silica gel (CombiFlash®, 3.4% methanol in DCM). MS (ES): m/z 504.2 [M+H]$^+$, $^1$H NMR (DMSO-d$_6$, 400 MHz): δ 9.81 (s, 1H), 9.03 (s, 1H), 8.70-8.69 (d, J=4.0 Hz, 1H), 8.25 (s, 1H), 8.05 (s, 1H), 7.89-7.87 (d, J=4.4 Hz, 1H), 7.64 (s, 1H), 7.47 (s, 1H), 4.04 (s, 3H), 3.10 (s, 6H).

Example 275: 7-chloro-1-methyl-6-((4-(methylamino)pyrazolo[1,5-a]pyrazin-3-yl)oxy)-N-(3-((1-methylazetidin-3-yl)methoxy)-5-(trifluoromethyl)phenyl)-1H-imidazo[4,5-b]pyridin-2-amine

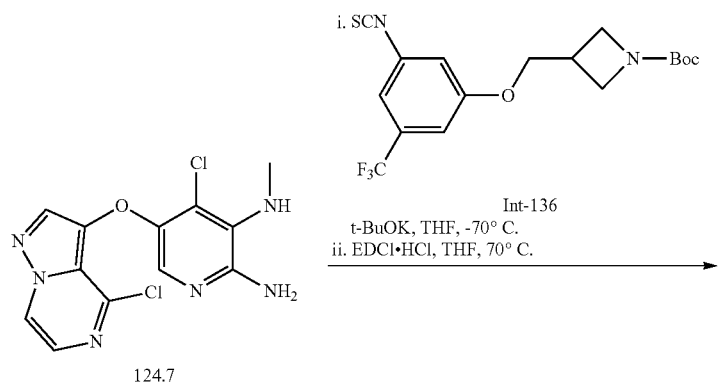

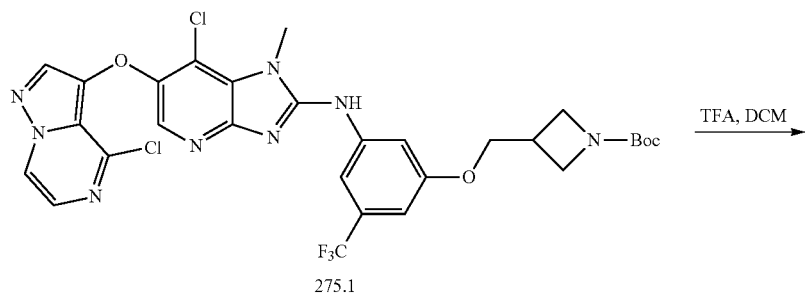

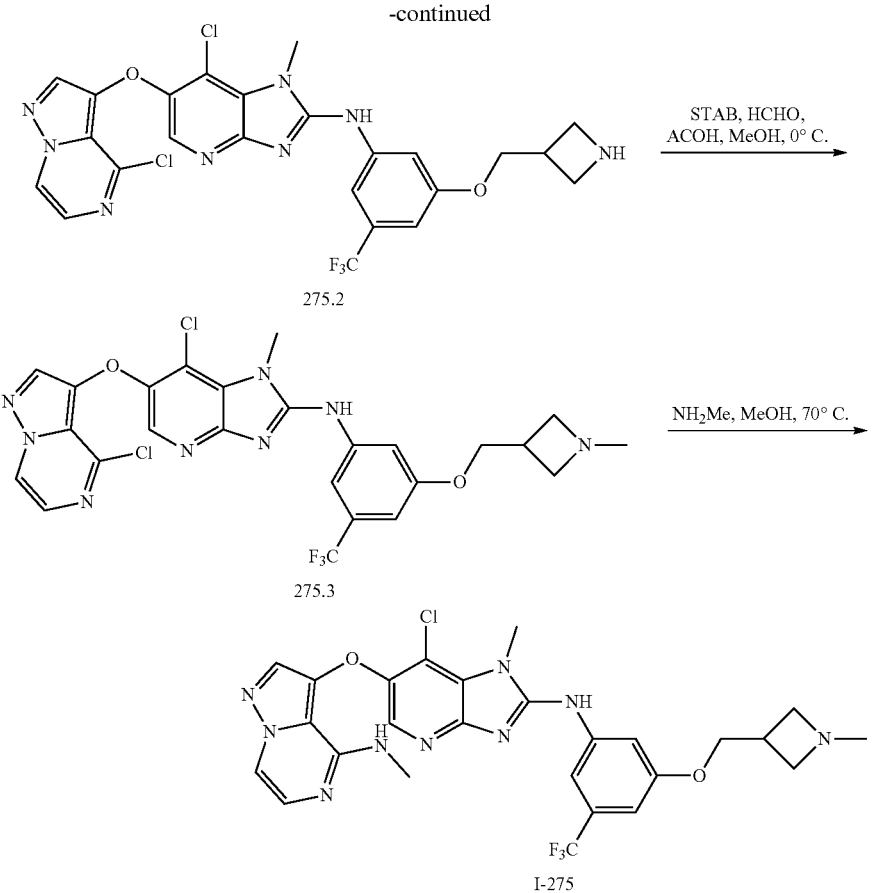

Synthesis of compound 275.1. Compound 275.1 was prepared from 124.7 and Int-136, following the procedure described in the synthesis of I-51. The product was purified by flash column chromatography on silica gel (Combi-Flash®, 3.1% methanol in DCM). MS (ES): m/z 680.1 [M+H]+.

Synthesis of compound 275.2. To solution of 275.1 (0.070 g, 0.103 mmol, 1.0 equiv) in DCM (3 mL) was added trifluoroacetic acid (0.5 mL) at 0° C. and stirred for 30 min. It was transferred into ice-saturated sodium bicarbonate solution and extracted with DCM. The combined organic layers were washed with brine, dried over anhydrous sodium sulfate, filtered, and concentrated under reduced pressure to afford 275.2. MS (ES): m/z 580.3 [M+H]+.

Synthesis of compound 275.3. To a solution of 275.2 (0.059 g, 0.101 mmol, 1.0 equiv), formaldehyde (0.015 g, 0.505 mmol, 5.0 equiv) and acetic acid (0.1 mL) in methanol (3 mL) was added was stirred at 0° C. for 20 min. To the reaction solution was added sodium triacetoxyborohydride (0.064 g, 0.303 mmol, 3.0 equiv) and stirred for 30 min. It was poured into ice-water and extracted with ethyl acetate. The combined organic layers were washed with brine, dried over anhydrous sodium sulfate, filtered, and concentrated under reduced pressure to afford 275.3. MS (ES): m/z 594.1 [M+H]+.

Synthesis of I-275. To a solution of 275.3 (0.060 g, 0.101 mmol, 1.0 equiv) in methanol (3 mL) was added methylamine solution (1 M in THF, 0.6 mL) and stirred at 70° C. for 2 h. The reaction mixture was concentrated under reduced pressure. The residue was purified by preparative HPLC to afford I-275. MS (ES): m/z 588.3 [M+H]+, 1H NMR (DMSO-d6, 400 MHz): δ 8.4 (s, 1H), 8.19 (s, 1H), 7.93 (s, 1H), 7.89 (s, 1H), 7.77-7.76 (d, J=4.4 Hz, 1H), 7.47 (s, 1H), 7.25-7.24 (d, J=4.8 Hz, 1H), 6.91 (s, 1H), 6.81 (s, 1H), 4.20-4.09 (d, J=6.4 Hz, 2H), 4.03 (s, 3H), 3.33 (bs, 3H), 3.01-2.99 (m, 4H), 2.8 (bs, 1H), 2.24 (s, 3H).

Example 276: (R)-7-chloro-1-methyl-6-((4-(methylamino)pyrazolo[1,5-a]pyrazin-3-yl)oxy)-N-(1-(tetrahydrofuran-3-yl)-5-(trifluoromethyl)-1H-pyrazol-3-yl)-1H-imidazo[4,5-b]pyridin-2-amine

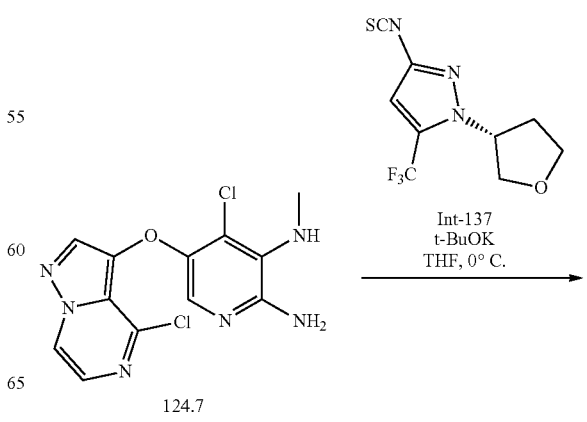

935
-continued

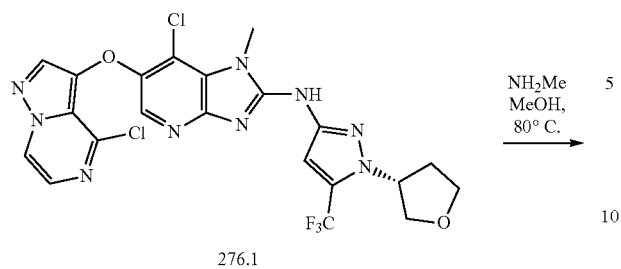

276.1

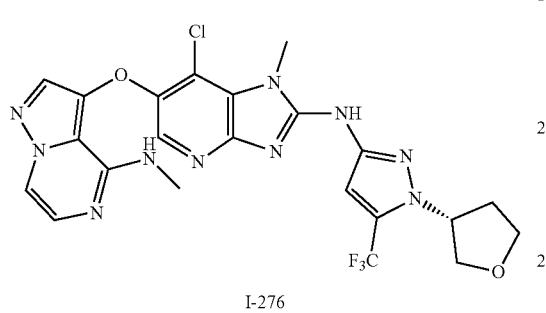

I-276

Synthesis of compound 276.1. Compound 276.1 was prepared from 124.7 and Int-137, following the procedure described in the synthesis of I-13. The product was purified by flash column chromatography on silica gel (Combi-Flash®, 5.7% methanol in DCM). MS (ES): m/z 555.1 [M+H]+.

Synthesis of I-276. To a solution of 276.1 (0.042 g, 0.075 mmol, 1.0 equiv) in methanol (2 mL) was added methylamine solution (1 M in THF, 0.4 mL) and stirred at 80° C. for 2 h. The reaction mixture was concentrated under reduced pressure. The residue was purified by flash column chromatography on silica gel (CombiFlash®, 7.0% methanol in DCM) to afford I-276. MS (ES): m/z 549.2 [M+H]+, $^1$H NMR (DMSO-$d_6$, 400 MHz): δ 10.56 (s, 1H), 8.15 (s, 1H), 7.77-7.76 (d, J=4.4 Hz, 1H), 7.47 (s, 1H), 7.33 (s, 1H), 7.25-7.24 (d, J=4.4 Hz, 1H), 6.81-6.80 (d, J=4.0 Hz, 1H), 5.12 (bs, 1H), 4.09-4.05 (m, 2H), 3.98 (s, 3H), 3.95-3.92 (m, 1H), 3.87-3.82 (m, 1H), 2.98-2.97 (d, 3H), 2.33 (bs, 2H).

936

Example 277: 7-chloro-1-methyl-6-(pyrazolo[1,5-a]pyrazin-3-yloxy)-N-(3-(pyrrolidin-1-ylmethyl)-5-(trifluoromethyl)phenyl)-1H-imidazo[4,5-b]pyridin-2-amine

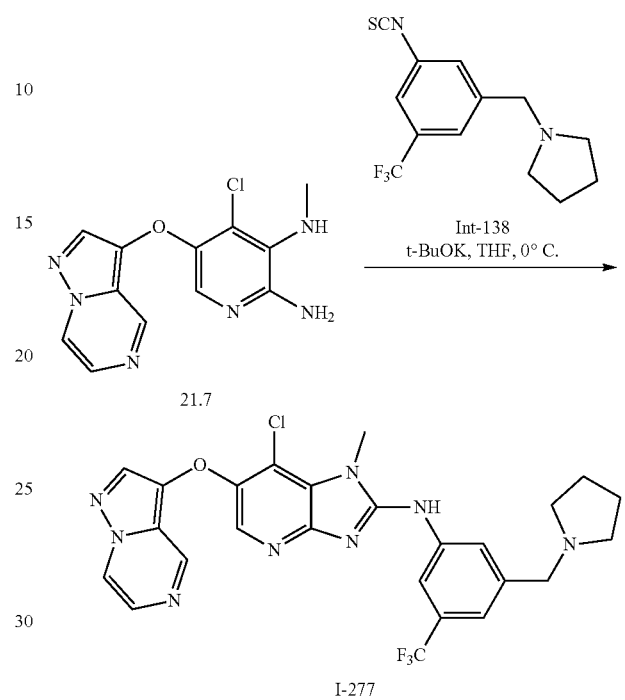

Synthesis of I-277. Compound I-277 was prepared from 21.7 and Int-138, following the procedure described in the synthesis of I-13. The product was purified by flash column chromatography on silica gel (CombiFlash®, 2.5% methanol in DCM). MS (ES): m/z 543.3 [M+H]+, $^1$H NMR (DMSO-$d_6$, 400 MHz): δ 9.64 (s, 1H), 9.03 (s, 1H), 8.70-8.69 (d, J=4.0 Hz, 1H), 8.20 (s, 1H), 8.29 (s, 1H), 8.17 (s, 1H), 8.04 (s, 1H), 7.88-7.87 (d, J=4.8 Hz, 1H), 7.76-7.74 (d, J=8.0 Hz, 1H), 4.03 (s, 3H), 3.72 (s, 2H), 2.34 (bs, 4H), 1.74 (bs, 4H).

Example 278: 1-(6-(3-((7-chloro-1-methyl-6-(pyrazolo[1,5-a]pyridin-3-yloxy)-1H-imidazo[4,5-b]pyridin-2-yl)amino)-5-(trifluoromethyl)-1H-pyrazol-1-yl)-2-azaspiro[3.3]heptan-2-yl)ethan-1-one

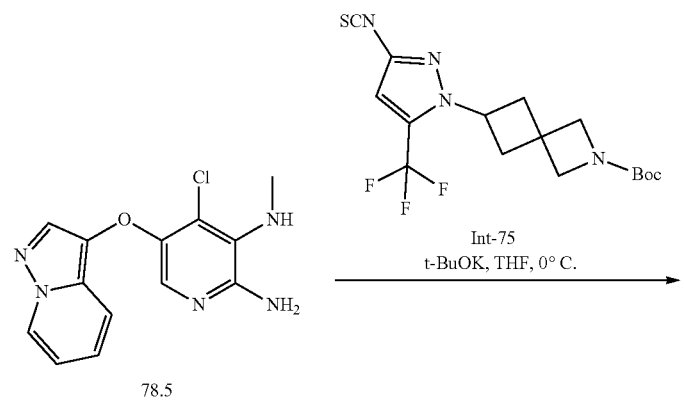

78.5

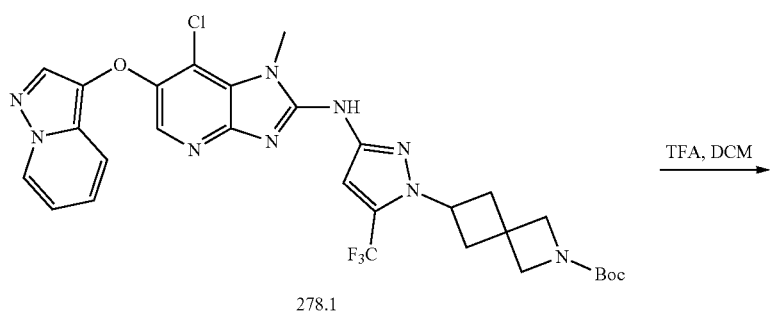

278.1

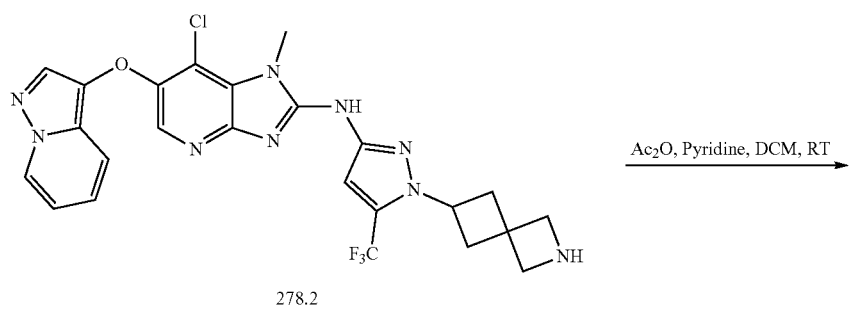

278.2

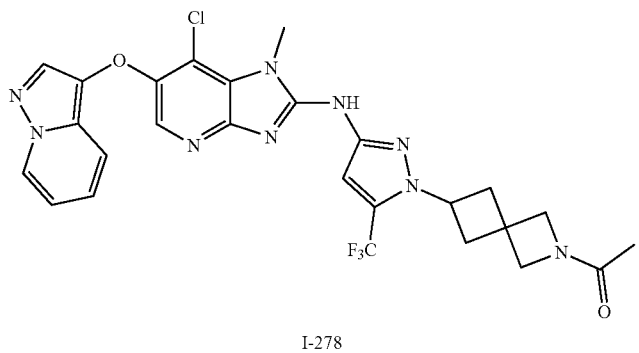

I-278

Synthesis of compound 278.1. Compound 278.1 was prepared from 78.5 and Int-75, following the procedure described in the synthesis of I-13. The product was purified by flash column chromatography on silica gel (Combi-Flash®, 2.3% methanol in DCM. MS (ES): m/z 645.1 [M+H]⁺.

Synthesis of compound 278.2. To a solution of 278.2 (0.120 g, 0.186 mmol, 1.0 equiv) in DCM (5 mL) was added trifluoroacetic acid (0.4 mL, 5.58 mmol, 30 equiv) at 0° C. The reaction mixture was stirred at room temperature for 2 h. It was transferred into ice-saturated sodium bicarbonate solution and extracted with DCM. The combined organic layers were washed with brine, dried over anhydrous sodium sulfate, filtered, and concentrated under reduced pressure to afford 278.2. MS (ES): m/z 544.5 [M+H]⁺.

Synthesis of I-278. To a solution of 278.2 (0.075 g, 0.137 mmol, 1.0 equiv) in DCM (2 mL) was added triethylamine (0.021 g, 0.205 mmol, 1.5 equiv) at 0° C. followed by the addition of acetic anhydride (0.028 g, 0.137 mmol, 1.0 equiv) dropwise. The reaction mixture was stirred at 0° C. for 1 h. It was transferred into ice-water, stirred, and extracted with DCM. The residue was purified by flash column chromatography on silica gel (CombiFlash®, 4.5% methanol in DCM) to afford I-278. MS (ES): m/z 586.5 [M+H]⁺, ¹H NMR (DMSO-d₆, 400 MHz): δ 10.50 (s, 1H), 8.62-8.60 (d, J=6.8 Hz, 1H), 7.99 (s, 1H), 7.96 (s, 1H), 7.51-7.49 (d, J=8.8 Hz, 1H), 7.29 (s, 1H), 7.20-7.16 (m, 1H), 6.90-6.87 (m, 1H), 4.89-4.87 (m, 1H), 4.25 (bs, 1H), 4.14 (bs, 1H), 3.99 (s, 3H), 3.98 (bs, 1H), 3.87 (bs, 1H), 2.78-2.76 (m, 4H), 1.75 (s, 3H).

Example 279: (3R,4S)-4-(3-((7-chloro-1-methyl-6-((4-(methylamino)pyrazolo[1,5-a]pyrazin-3-yl)oxy)-1H-imidazo[4,5-b]pyridin-2-yl)amino)-5-(trifluoromethyl)-1H-pyrazol-1-yl)tetrahydrofuran-3-ol and (3S,4R)-4-(3-((7-chloro-1-methyl-6-((4-(methylamino)pyrazolo[1,5-a]pyrazin-3-yl)oxy)-1H-imidazo[4,5-b]pyridin-2-yl)amino)-5-(trifluoromethyl)-1H-pyrazol-1-yl)tetrahydrofuran-3-ol

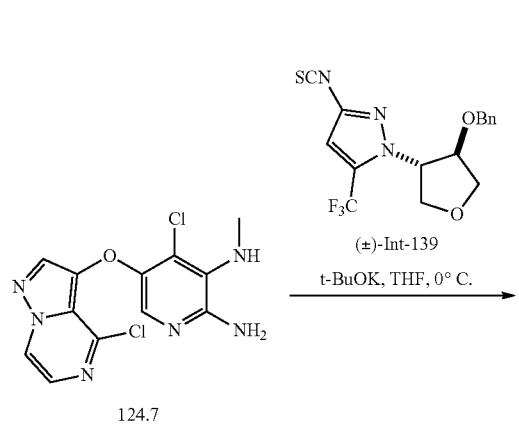

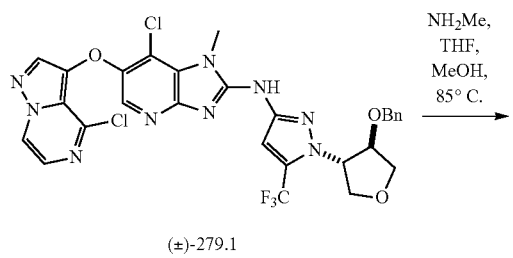

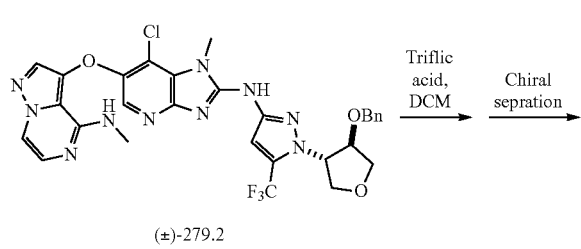

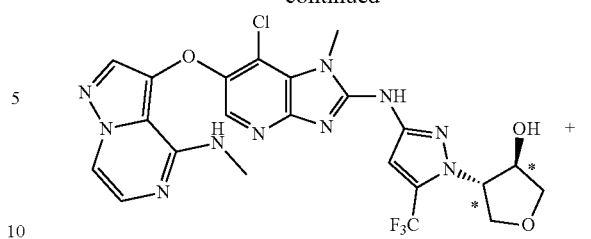

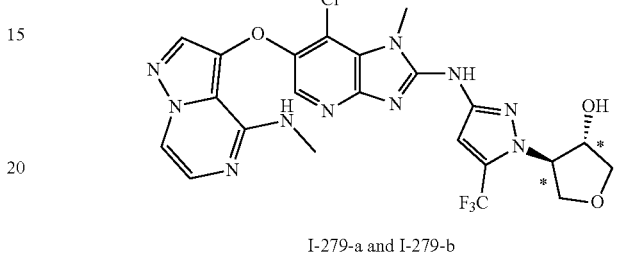

I-279-a and I-279-b

Synthesis of compound (±)-279.1. Compound (±)-279.1 was prepared from 124.7 and (±)-Int-139, following the procedure described in the synthesis of I-13. The product was purified by flash column chromatography on silica gel (CombiFlash®, 1.7% methanol in DCM). MS (ES): m/z 661.7 [M+H]$^+$.

Synthesis of compound (±)-279.2. To a solution of (±)-279.1 (0.030 g, 0.045 mmol, 1.0 equiv) in methanol (10 mL) was added methylamine solution (2 M in THF) (0.4 mL) and stirred at 85° C. for 6 h. The reaction mixture was concentrated under reduced pressure. The residue was purified by trituration using methanol) to afford (±)-279.2. MS (ES): m/z 656.5 [M+H]$^+$.

Synthesis of compound I-279-a and I-279-b. To a solution of (±)-279.2 (0.023 g, 0.035 mmol, 1.0 equiv) in DCM (2 mL) was added triflic acid (0.05 mL) at 0° C. and stirred for 5 min. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 3.5% methanol in DCM). The racemate was separated by HPLC (column CHIRALPAK IB-N (250 mm×4.6 mm, 5 μm); mobile phases: (A) 0.1% DEA in n-hexane, (B) 0.1% DEA in propan-2-ol:acetonitrile (70:30); flow rate: 20 mL/min) to afford first eluting fraction (I-279-a) and second eluting fraction (I-279-b). (*Absolute stereochemistry not determined.)

I-279-a: MS (ES): m/z 565.2 [M+H]$^+$, $^1$H NMR (MeOH-d$_4$, 400 MHz): δ 8.18 (s, 1H), 7.67-7.65 (d, J=4.8 Hz, 1H), 7.39 (bs, 2H), 7.23-7.22 (d, J=4.8 Hz, 1H), 4.68 (bs, 1H), 4.36 (bs, 2H), 4.28 (bs, 2H), 4.03 (s, 3H), 3.85 (bs, 1H), 3.10 (s, 3H).

I-279-b: MS (ES): m/z 565.2 [M+H]$^+$, $^1$H NMR (MeOH-d$_4$, 400 MHz): δ 8.18 (s, 1H), 7.67-7.65 (d, J=4.8 Hz, 1H), 7.39 (bs, 2H), 7.23-7.22 (d, J=4.8 Hz, 1H), 4.68 (bs, 1H), 4.36 (bs, 2H), 4.28 (bs, 2H), 4.03 (s, 3H), 3.85 (bs, 1H), 3.10 (s, 3H).

Example 280: (S)-7-chloro-1-methyl-6-((4-(methyl-amino)pyrazolo[1,5-a]pyrazin-3-yl)oxy)-N-(2-(tetra-hydrofuran-3-yl)-6-(trifluoromethyl)pyridin-4-yl)-1H-imidazo[4,5-b]pyridin-2-amine and (R)-7-chloro-1-methyl-6-((4-(methylamino)pyrazolo[1,5-a]pyrazin-3-yl)oxy)-N-(2-(tetrahydrofuran-3-yl)-6-(trifluoromethyl)pyridin-4-yl)-1H-imidazo[4,5-b]pyridin-2-amine
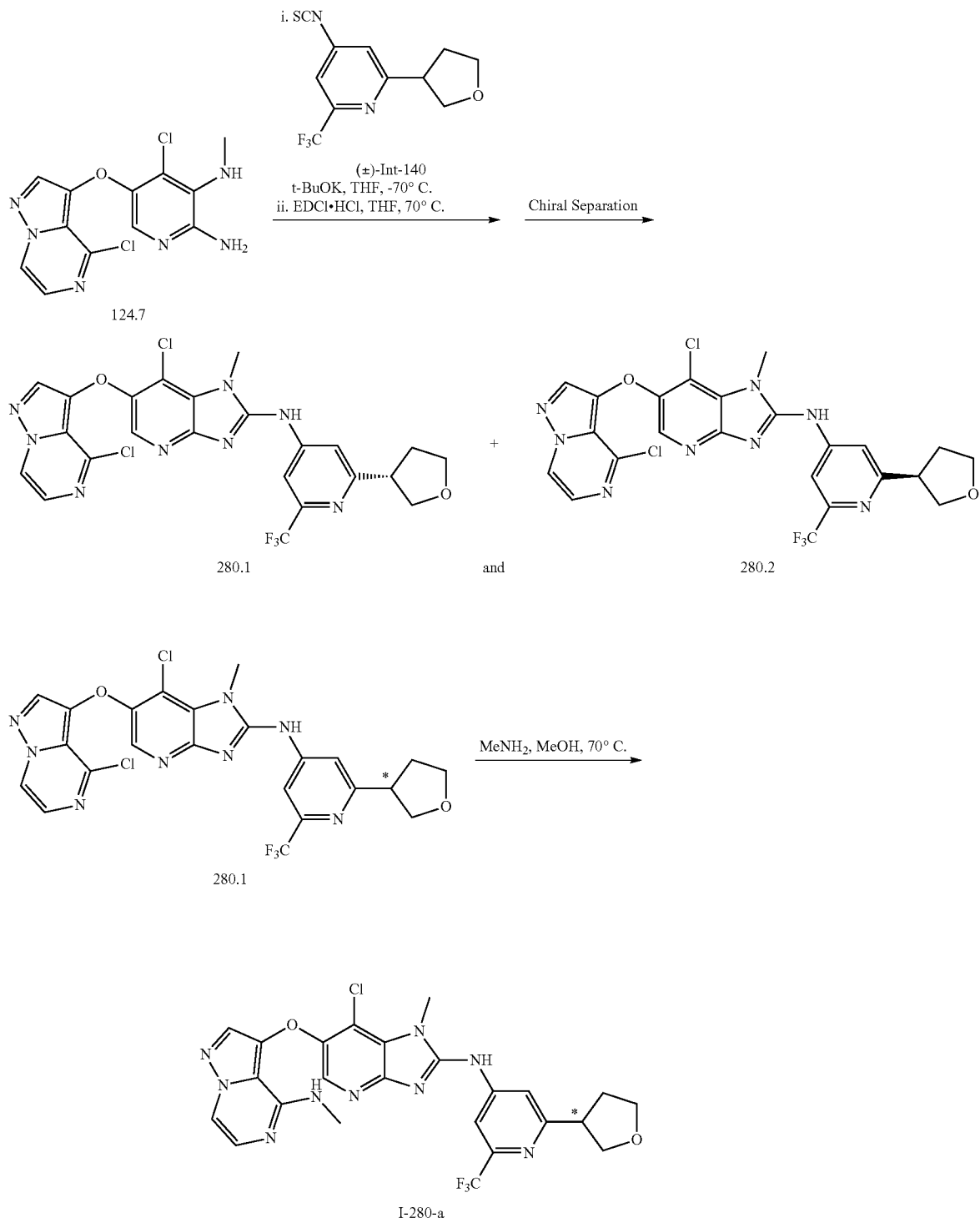

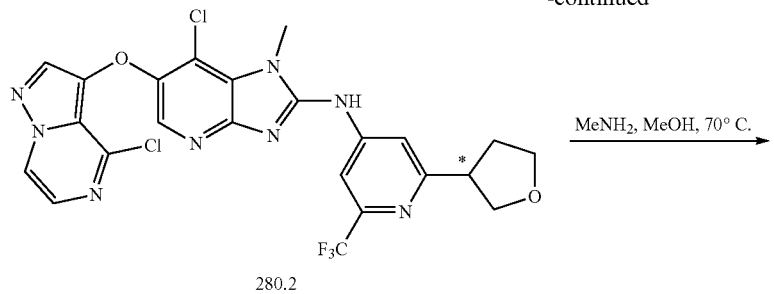

280.2

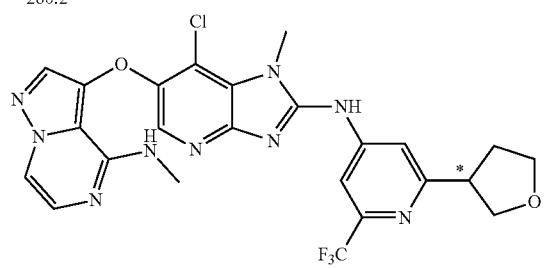

I-280-b

Synthesis of compound 280.1 and 280.2. The racemic mixture of 280.1 and 280.2 was prepared from 124.7 and (±)-Int-140, following the procedure described in the synthesis of I-51. The product was purified by flash column chromatography on silica gel (CombiFlash®, 4.5% methanol in DCM). It was separated by HPLC (column: CHIRALPAK AD-H (250 mm*21 mm, 5 μm); mobile phases: (A) 0.1% DEA in n-hexane, (B) 0.1% DEA in propan-2-ol; flow rate: 20 mL/min) to afford first eluting fraction (280.1) and second eluting fraction (280.2). MS (ES): m/z 566.2 [M+H]$^+$. (*Absolute stereochemistry not determined.)

Synthesis of I-280-a. To a solution of 280.1 (0.031 g, 0.054 mmol, 1.0 equiv) in methanol (2 mL) was added methylamine solution (2 M in THF, 0.5 mL) and stirred at 70° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.4% methanol in DCM) to afford I-280-a. MS (ES): m/z 560.2 [M+H]$^+$, $^1$H NMR (DMSO-d$_6$, 400 MHz): δ 10.18 (s, 1H), 8.37 (s, 1H), 8.27 (s, 1H), 8.02 (s, 1H), 7.78-7.77 (d, J=4.8 Hz, 1H), 7.48 (d, J=4.0 Hz, 1H), 7.26-7.25 (d, J=4.8 Hz, 1H), 6.83-6.82 (d, J=4.4 Hz, 1H), 4.12-4.08 (m, 1H), 4.05 (s, 3H), 3.98-3.94 (m, 1H), 3.86-3.77 (m, 2H), 3.67-3.62 (m, 1H), 2.99 (bs, 3H), 2.40-2.33 (m, 1H), 2.16-2.09 (m, 1H).

Synthesis of I-280-b. To a solution of 280.2 (0.033 g, 0.058 mmol, 1.0 equiv) in methanol (2 mL) was added methylamine solution (2 M in THF, 0.5 mL) and stirred at 70° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.4% methanol in DCM) to afford I-280-b. MS (ES): m/z 560.2 [M+H]$^+$, $^1$H NMR (DMSO-d$_6$, 400 MHz): δ 10.19 (s, 1H), 8.37 (s, 1H), 8.27 (s, 1H), 8.02 (s, 1H), 7.78-7.77 (d, J=4.8 Hz, 1H), 7.48 (d, J=4.0 Hz, 1H), 7.26-7.25 (d, J=4.8 Hz, 1H), 6.83-6.82 (d, J=4.4 Hz, 1H), 4.12-4.08 (m, 1H), 4.05 (s, 3H), 3.98-3.96 (m, 1H), 3.86-3.77 (m, 2H), 3.67-3.62 (m, 1H), 2.99 (bs, 3H), 2.40-2.33 (m, 1H), 2.14-2.09 (m, 1H).

Example 281: 1-methyl-2-((1-methyl-2-oxo-5-(trifluoromethyl)-1,2-dihydropyridin-3-yl)amino)-6-((5-morpholinopyrazolo[1,5-a]pyridin-3-yl)oxy)-1H-imidazo[4,5-b]pyridine-7-carbonitrile

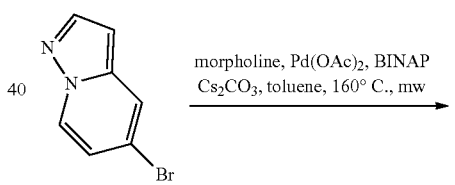

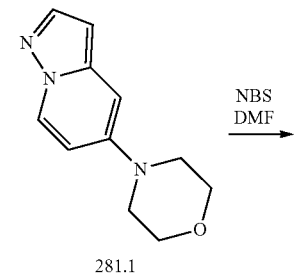

281.1

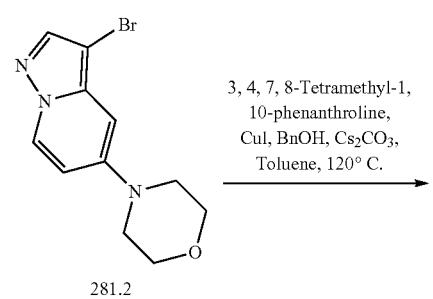

281.2

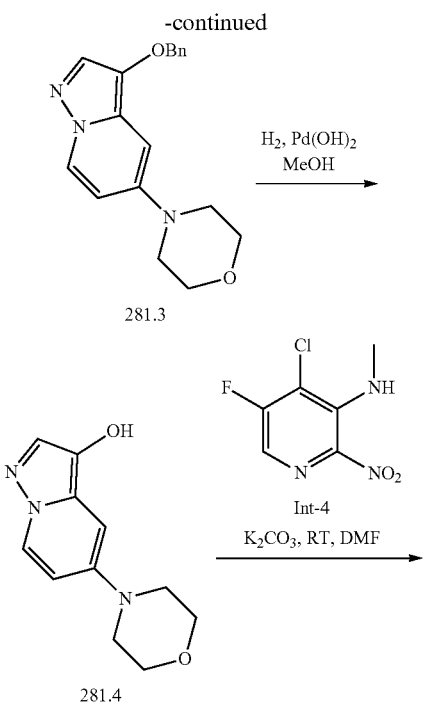

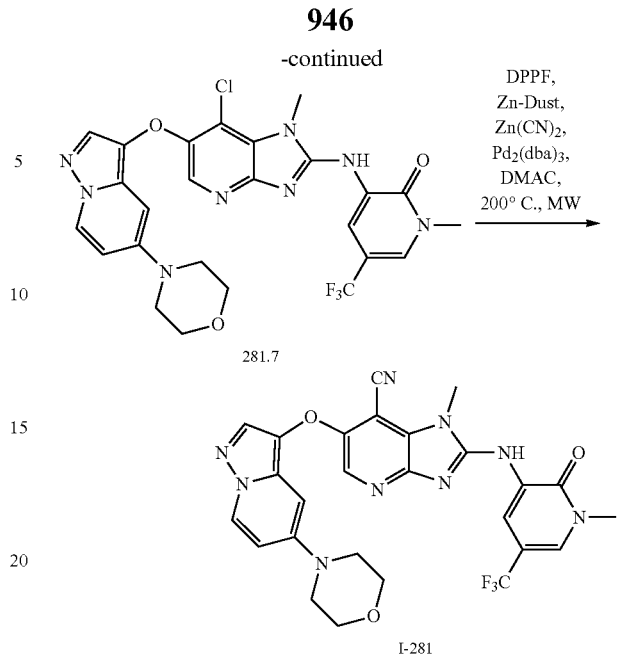

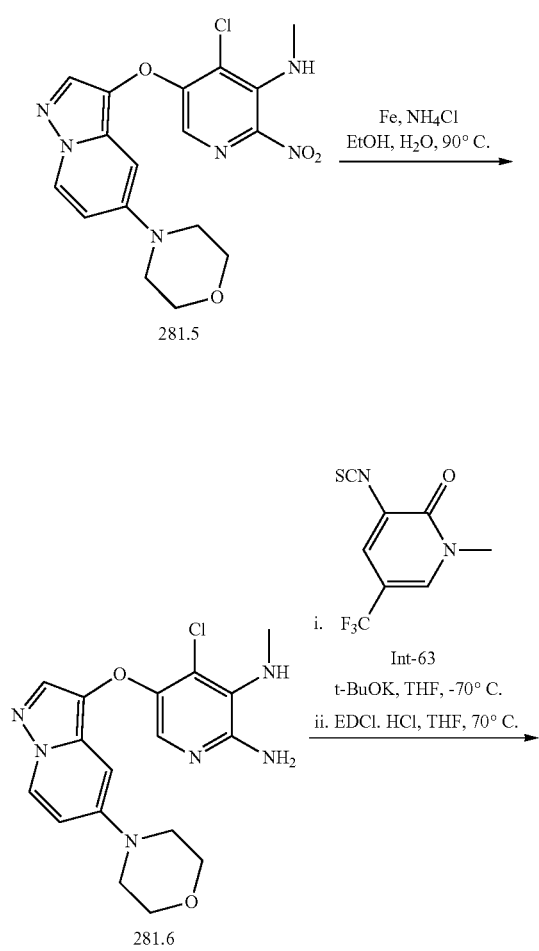

Synthesis of compound 281.1. A mixture of 5-bromopyrazolo[1,5-a]pyridine (2.0 g, 10.15 mmol, 1.0 equiv), cesium carbonate (4.9 g, 15.22 mmol, 1.5 equiv), (2,2'-bis(diphenylphosphino)-1,1'-binaphthyl) (0.631 g, 1.01 mmol, 0.1 equiv) and palladium acetate (0.136 g, 0.609 mmol, 0.06 equiv) in toluene (20 mL) was degassed by bubbling argon through for 15 min. Under argon atmosphere, morpholine (1.76 g, 20.30 mmol, 2.0 equiv) was added dropwise, and degassed for 15 min. The reaction mixture was stirred at 160° C. in microwave for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane) to afford 281.1. MS (ES): m/z 204.2 [M+H]$^+$.

Synthesis of compound 281.2. To a solution of 281.1 (1.5 g, 7.38 mmol, 1.0 equiv) in acetonitrile (10 mL) was added N-bromosuccinimide (1.4 g, 8.11 mmol, 1.1 equiv) in portions at 0° C. The reaction was allowed to warm to room temperature and stirred for 15 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 18% ethyl acetate in hexane) to afford 281.2. MS (ES): m/z 283 [M+H]$^+$.

Synthesis of compound 281.3. A mixture of 281.2 (0.800 g, 2.84 mmol, 1.0 equiv), benzyl alcohol (0.765 g, 7.092 mmol, 2.5 equiv), and cesium carbonate (1.8 g, 5.68 mmol, 2.0 equiv) in toluene (8 mL) was degassed by bubbling argon through for 15 min. Under argon atmosphere, 3,4,7,8-tetramethyl-1,10-phenanthroline (0.100 g, 0.426 mmol, 0.15 equiv) and copper iodide (0.03 g, 0.198 mmol, 0.07 equiv) were added. The reaction mixture was stirred at 120° C. for 16 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 27% ethyl acetate in hexane) to afford 281.3. MS (ES): m/z 310.4 [M+H]$^+$.

Synthesis of compound 281.4. A mixture of compound 281.3 (0.470 g, 1.52 mmol, 1.0 equiv) and palladium on charcoal (0.117 g) in methanol (10 mL) was stirred under hydrogen (1 atm) for 2 h. The reaction mixture was filtered through a pad of Celite® and rinsed with methanol. The filtrate was concentrated under reduced pressure to afford 281.4. MS (ES): m/z 220.2 [M+H]$^+$.

Synthesis of compound 281.5. A solution of 281.4 (0.180 g, 0.821 mmol, 1.0 equiv), Int-4 (0.185 g, 0.903 mmol, 1.1 equiv), and potassium carbonate (0.226 g, 1.642 mmol, 2.0 equiv) in DMF (5 mL) was stirred at room temperature for 35 min. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford 281.5. MS (ES): m/z 405.5 [M+H]$^+$.

Synthesis of compound 281.6. To a solution of 281.5 (0.100 g, 0.247 mmol, 1.0 equiv) in ethanol:water (2:1, 8 mL) was added iron powder (0.069 g, 1.23 mmol, 5.0 equiv) followed by ammonium chloride (0.066 g, 1.23 mmol, 5.0 equiv). The reaction mixture was stirred at 90° C. for 1 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.8% methanol in DCM) to afford 281.6. MS (ES): m/z 375.5 [M+H]$^+$.

Synthesis of compound 281.7. Compound 281.7 was prepared from 281.6 and Int-63, following the procedure described in the synthesis of I-51. The product was purified by flash column chromatography on silica gel (CombiFlash®, 1.6% methanol in DCM. MS (ES): m/z 575.21 [M+H]$^+$.

Synthesis of I-281. A mixture of 281.7 (0.050 g, 0.086 mmol, 1.0 equiv), zinc dust (0.001 g, 0.017 mmol, 0.2 equiv), and zinc cyanide (0.039 g, 0.34 mmol, 5.0 equiv) in N,N-dimethylacetamide (2 mL) was degassed by bubbling argon through for 10 min. Under argon atmosphere, tris(dibenzylideneacetone)dipalladium(0) (0.005 g, 0.005 mmol, 0.07 equiv) and 1,1'-bis(diphenylphosphino)ferrocene (0.007 g, 0.013 mmol, 0.15 equiv) were added, and degassed for 5 min. The reaction mixture was stirred at 200° C. in microwave for 1 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-281. MS (ES): m/z 566.4 [M+H]$^+$, $^1$H NMR (DMSO-d$_6$, 400 MHz): δ 8.91 (s, 1H), 8.60 (s, 1H), 8.48-8.46 (d, J=8.0 Hz, 1H), 8.14 (s, 1H), 8.01 (s, 1H), 7.86 (s, 1H), 6.88-6.86 (d, J=8.0 Hz, 1H), 6.54, (s, 1H), 3.98 (s, 3H), 3.71 (s, 4H), 3.65 (s, 3H), 3.17 (s, 4H).

Example 282: (R)-7-chloro-N-(3-((3-(dimethylamino)pyrrolidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine Synthesis of compound 282.1. Compound 282.1 was prepared from 124.7 and Int-133, following the procedure described in the synthesis of I-13. The product was purified by flash column chromatography on silica gel (CombiFlash®, 7.2% methanol in DCM). m/z 621.2 [M+H]$^+$.

Synthesis of I-282. To a solution of 282.1 (0.040 g, 0.064 mmol, 1.0 equiv) in methanol (2 mL) was added methylamine solution (1 M in THF, 0.4 mL) and stirred at 70° C. for 2 h. The reaction mixture was concentrated under reduced pressure. The residue was purified by flash column chromatography on silica gel (CombiFlash®, 9.0% methanol in DCM) to afford I-282. MS (ES): m/z 616.3 [M+H]$^+$, $^1$H NMR (DMSO-d$_6$, 400 MHz): δ 9.92 (s, 1H), 8.30 (s, 1H), 8.24 (s, 1H), 8.18 (s, 1H), 7.78-7.76 (d, J=4.8 Hz, 1H), 7.47 (s, 1H), 7.29 (s, 1H), 7.25-7.24 (d, J=4.8 Hz, 1H), 6.82-6.81 (d, J=4.8 Hz, 1H), 4.06 (s, 3H), 3.78-3.63 (m, 2H), 2.99-2.98 (d, 3H), 2.71 (bs, 2H), 2.62 (bs, 6H), 2.18-1.94 (m, 4H), 1.55 (bs, 1H).

Example 283: (R)-7-chloro-N-(3-((3-(dimethylamino)pyrrolidin-1-yl)methyl)-2-fluoro-5-(trifluoromethyl)phenyl)-1-methyl-6-(pyrazolo[1,5-a]pyrazin-3-yloxy)-1H-imidazo[4,5-b]pyridin-2-amine

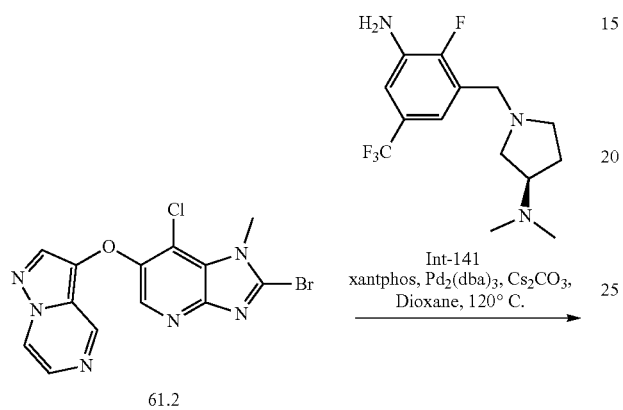

Synthesis of I-283. Compound I-283 was prepared from 61.2 and Int-141, following the procedure described in the synthesis of I-53. The product was purified by flash column chromatography on silica gel (CombiFlash®, 10% methanol in DCM). MS (ES): m/z 604.5 [M+H]⁺, ¹H NMR (DMSO-d₆, 400 MHz): δ 9.40 (bs, 1H), 9.04 (s, 1H), 8.71-8.69 (d, J=4.8 Hz, 1H), 8.32 (bs, 1H), 8.19 (s, 1H), 8.04 (s, 1H), 7.88-7.87 (d, J=5.2 Hz, 1H), 7.52 (s, 1H), 4.00 (s, 3H), 3.81-3.69 (m, 1H), 2.80 (bs, 2H), 2.75-2.71 (m, 2H), 2.34 (bs, 2H), 2.15 (s, 6H), 1.92-1.87 (m, 1H), 1.66-1.64 (m, 1H).

Example 284: 7-chloro-1-methyl-6-((4-(methylamino)pyrazolo[1,5-a]pyrazin-3-yl)oxy)-N-(3-(pyrrolidin-1-ylmethyl)-5-(trifluoromethyl)phenyl)-1H-imidazo[4,5-b]pyridin-2-amine

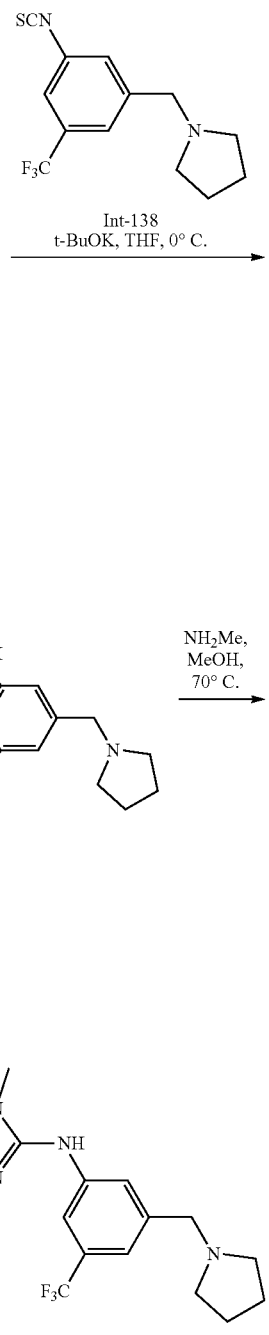

Synthesis of compound 284.1. Compound 284.1 was prepared from 124.7 and Int-138, following the procedure described in the synthesis of I-13. The product was purified by flash column chromatography on silica gel (CombiFlash®, 7.0% methanol in DCM). m/z 578.2 [M+H]⁺.

Synthesis of I-284. To a solution of 284.1 (0.042 g, 0.075 mmol, 1.0 equiv) in methanol (2 mL) was added methylamine solution (1 M in THF, 0.4 mL) and stirred at 80° C. for 2 h. The reaction mixture was concentrated under reduced pressure The residue was purified by flash column chromatography on silica gel (CombiFlash®, 7.0% methanol in DCM) to afford I-284. MS (ES): m/z 572.3 [M+H]+, 1H NMR (DMSO-d6, 400 MHz): δ 10.72 (s, 1H), 10.06 (s, 1H). 8.31 (s, 1H), 8.08 (s, 1H), 7.77-7.76 (d, J=4.4 Hz, 1H), 7.70 (s, 1H), 7.47 (s, 1H), 7.25-7.24 (d, J=4.4 Hz, 1H), 6.83 (bs, 1H), 4.94 (bs, 2H), 4.05 (s, 3H), 2.99 (s, 3H), 2.36 (bs, 4H), 1.91 (bs, 4H).

Example 285: (S)-7-chloro-N-(3-((3-(dimethylamino)pyrrolidin-1-yl)methyl)-2-fluoro-5-(trifluoromethyl)phenyl)-1-methyl-6-(pyrazolo[1,5-a]pyrazin-3-yloxy)-1H-imidazo[4,5-b]pyridin-2-amine

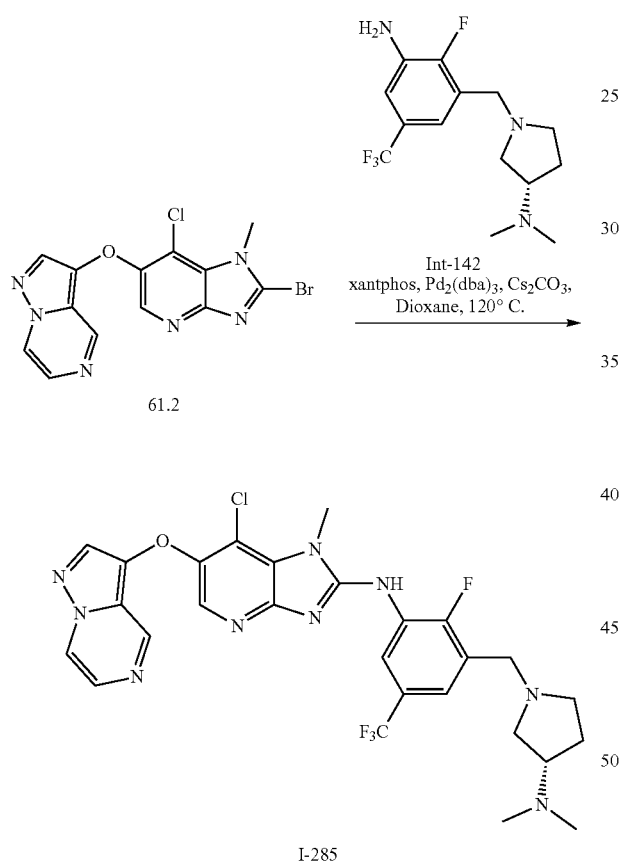

I-285

Synthesis of compound I-285. Compound I-285 was prepared from 61.2 and Int-142, following the procedure described in the synthesis of I-53. The product was purified by flash column chromatography on silica gel (CombiFlash®, 10% methanol in DCM). MS (ES): m/z 604.5 [M+H]+, 1H NMR (DMSO-d6, 400 MHz): δ 9.38 (bs, 1H), 9.0 (s, 1H), 8.69-8.68 (d, J=4.8 Hz, 1H), 8.30 (bs, 1H), 8.18 (s, 1H), 8.03 (s, 1H), 7.87-7.86 (d, J=5.2 Hz, 1H), 7.50 (s, 1H), 3.99 (s, 3H), 3.80-3.68 (m, 1H), 2.80 (bs, 2H), 2.71-2.67 (m, 2H), 2.33 (bs, 2H), 2.14 (s, 6H), 1.88 (bs, 1H), 1.65 (bs, 1H).

Example 286: (S)-7-chloro-N-(3-((3-(dimethylamino)pyrrolidin-1-yl)methyl)-5-(trifluoromethyl)phenyl)-1-methyl-6-((4-(methylamino)pyrazolo[1,5-a]pyrazin-3-yl)oxy)-1H-imidazo[4,5-b]pyridin-2-amine

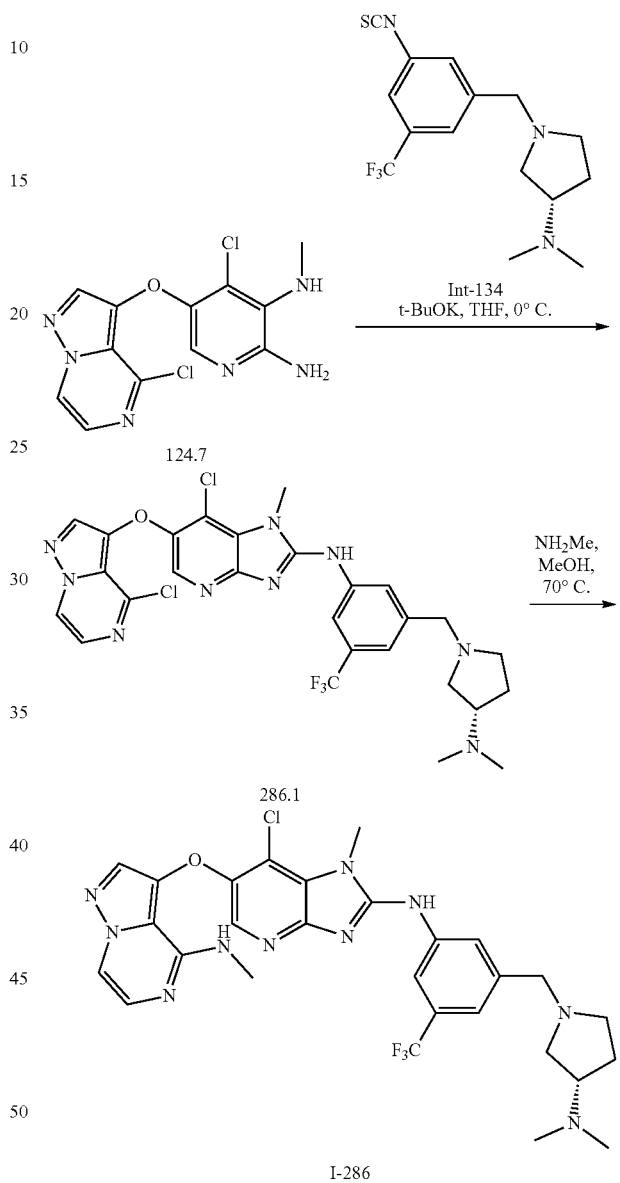

I-286

Synthesis of compound 286.1. Compound 286.1 was prepared from 124.7 and Int-134, following the procedure described in the synthesis of I-13. The product was purified by flash column chromatography on silica gel (CombiFlash®, 7.3% methanol in DCM). MS (ES): m/z 621.3 [M+H]+.

Synthesis of I-286 To a solution of 286.1 (0.050 g, 0.080 mmol, 1.0 equiv) in methanol (2 mL) was added methylamine solution (1 M in THF, 0.5 mL) and stirred at 70° C. for 3 h. The reaction mixture was concentrated under reduced pressure. The residue was purified by flash column chromatography on silica gel (CombiFlash®, 8.8% methanol in DCM) to afford I-286. MS (ES): m/z 616.2 [M+H]+, $^1$H NMR (DMSO-d$_6$, 400 MHz): δ 9.92 (s, 1H), 8.30 (s, 1H), 8.24 (s, 1H), 8.18 (s, 1H), 7.78-7.76 (d, J=4.8 Hz, 1H), 7.47 (s, 1H), 7.29 (s, 1H), 7.25-7.24 (d, J=4.8 Hz, 1H), 6.82-6.81 (d, J=4.8 Hz, 1H), 4.05 (s, 3H), 3.77-3.61 (m, 2H), 2.99-2.98 (d, 3H), 2.71 (bs, 2H), 2.62 (bs, 6H), 2.18-1.94 (m, 4H), 1.55 (bs, 1H).

Example 287: 7-chloro-N-(4,6-dimethyl-5-(pyrrolidin-1-yl)pyrimidin-2-yl)-1-methyl-6-(pyrazolo[1,5-a]pyrazin-3-yloxy)-1H-imidazo[4,5-b]pyridin-2-amine

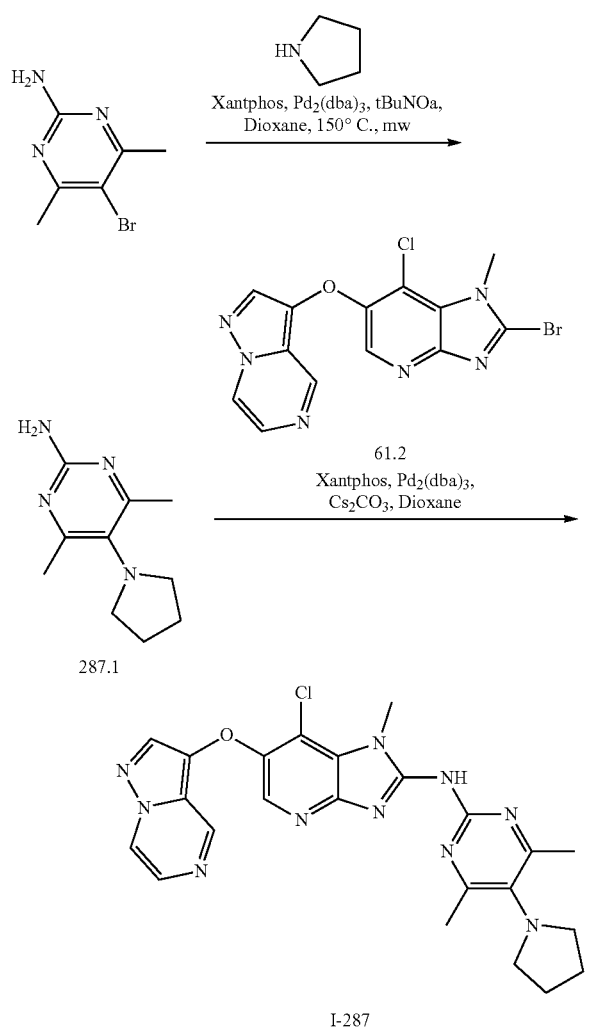

brine, dried over anhydrous sodium sulfate, filtered, and concentrated under reduced pressure. The residue was purified by column chromatography) to afford 287.1. MS (ES): m/z 193.2 [M+H]$^+$.

Synthesis of I-287. Compound I-287 was prepared from 61.2 and 287.1, following the procedure described in the synthesis of I-53. The product was purified by flash column chromatography on silica gel (CombiFlash®, 3.0% methanol in DCM). MS (ES): m/z 491.40 [M+H]$^+$, $^1$H NMR (DMSO-d$_6$, 400 MHz): δ 10.27 (s, 1H), 9.09 (s, 1H), 8.70-8.69 (d, J=4.4 Hz, 1H), 8.29 (s, 1H), 8.08 (s, 1H), 7.88-7.87 (d, J=3.6 Hz, 1H), 3.84 (s, 4H), 3.08 (s, 4H), 2.31 (s, 6H), 1.95 (s, 3H).

Example 288: 3-((7-chloro-6-((3-fluoro-1H-pyrrolo[2,3-b]pyridin-5-yl)oxy)-1-methyl-1H-imidazo[4,5-b]pyridin-2-yl)amino)-1-methyl-5-(trifluoromethyl)pyridin-2(1H)-one

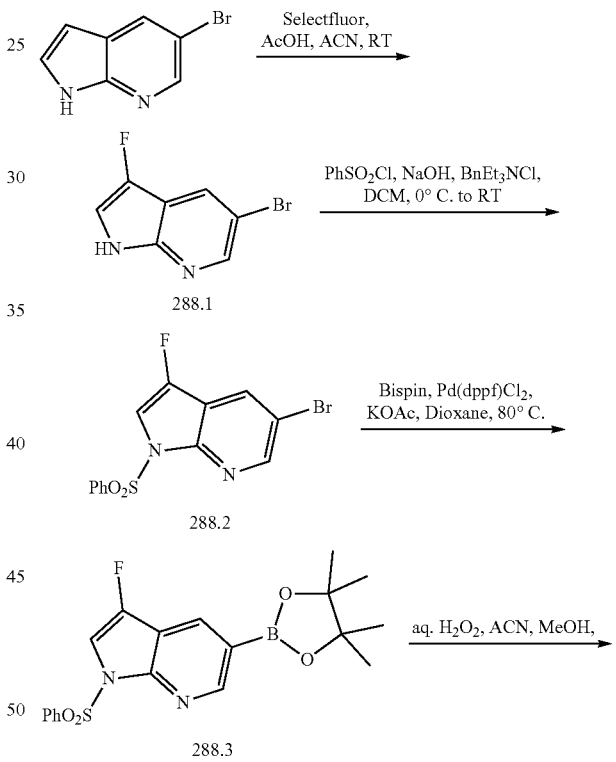

Synthesis of compound 287.1. A mixture of 5-bromo-4,6-dimethylpyrimidin-2-amine (2.0 g, 9.90 mmol, 1.0 equiv), pyrrolidine (1.76 g, 24.75 mmol, 2.5 equiv) and sodium tert-butoxide (2.85 g, 29.70 mmol, 3.0 equiv) in 1,4-dioxane (15 mL) was degassed by bubbling argon through for 10 min. Under argon atmosphere, 4,5-bis(diphenylphosphino)-9,9-dimethylxanthene (0.286 g, 0.495 mmol, 0.05 equiv) and tris(dibenzylideneacetone) dipalladium(0) (0.226 g, 0.247 mmol, 0.025 equiv) were added, and degassed for 5 min. The reaction mixture was stirred in a microwave reactor at 150° C. for 30 min. It was cooled to room temperature, transferred into water, and extracted with ethyl acetate. The combined organic layers were washed with

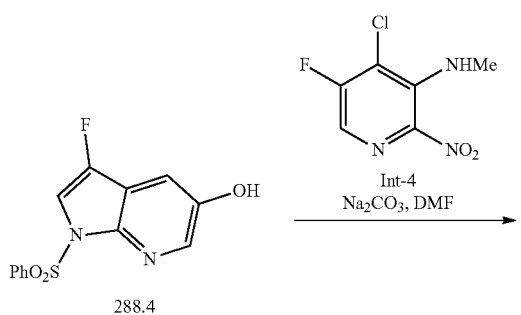

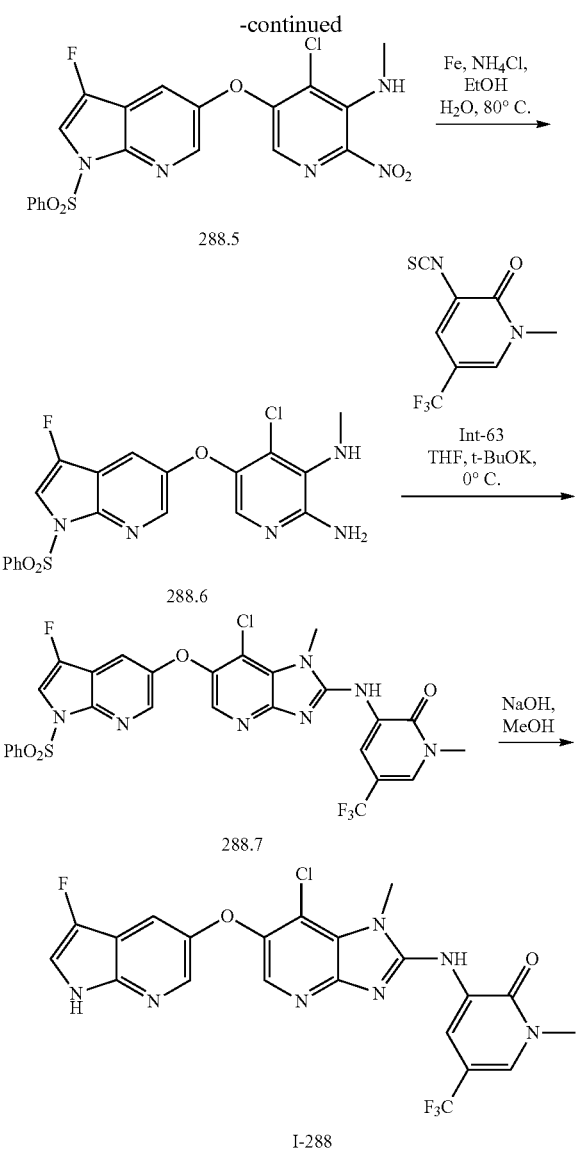

Synthesis of compound 288.1. To a solution of 5-bromo-1H-pyrrolo[2,3-b]pyridine (5.0 g, 25.38 mmol, 1.0 equiv) in acetonitrile (500 mL) was added 1-chloromethyl-4-fluoro-1,4-diazoniabicyclo[2.2.2]octane-bis(tetrafluoroborate) (13 g, 38.07 mmol, 1.5 equiv) followed by acetic acid (125 mL). The reaction mixture was stirred at room temperature for 16 h. It was transferred into water and extracted with ethyl acetate. The combined organic layers were washed with brine, dried over anhydrous sodium sulfate, filtered, and concentrated under reduced pressure to afford crude material. The residue was purified by flash column chromatography on silica gel (CombiFlash®, 25% ethyl acetate in hexane to afford 288.1. MS (ES): m/z 216.03 [M+H]$^+$.

Synthesis of compound 288.2. To a solution of 288.1 (0.623 g, 2.90 mmol, 1.0 equiv) in DCM (6 mL) was added benzyltriethylammonium chloride (0.013 g, 0.072 mmol, 0.025 equiv) followed by the addition of sodium hydroxide powder (0.347 g, 8.70 mmol, 3.0 equiv). It was cooled to 0° C. and benzyl sulfonyl chloride (0.611 g, 3.62 mmol, 1.25 equiv) was added. The reaction mixture was stirred at room temperature for 2 h. It was filtered through a pad of Celite® and rinsed with DCM. The filtrate was concentrated under reduced pressure. The residue was purified by flash column chromatography on silica gel (CombiFlash®, 20% ethyl acetate in hexane) to afford 288.2. MS (ES): m/z 291.31 [M+H]$^+$.

Synthesis of compound 288.3. A solution of 288.2 (0.590 g, 2.03 mmol, 1.0 equiv), bis(pinacolato)diboron (1.03 g, 4.06 mmol, 2.0 equiv) and potassium acetate (0.398 g, 4.06 mmol, 2.0 equiv) in 1,4-dioxane (5 mL) was degassed by bubbling argon through under argon atmosphere for 5 min. To the mixture was added 1,1-bis(diphenylphosphino)ferrocene-palladium(II)dichloride DCM complex (0.297 g, 0.406 mmol, 0.2 equiv) and degassed for 5 min. The reaction mixture was stirred at 80° C. for 30 min. It was cooled to room temperature, transferred into ice-water, stirred, and extracted with ethyl acetate. The combined organic layers were washed with brine, dried over anhydrous sodium sulfate, filtered, and concentrated under reduced pressure to afford 288.3. MS (ES): m/z 403.25 [M+H]$^+$.

Synthesis of compound 288.4. To a solution of 288.3 (0.410 g, 1.02 mmol, 1.0 equiv) in acetonitrile (25 mL) and methanol (25 mL) was added hydrogen peroxide (3 mL). The reaction mixture stirred at room temperature for 16 h. It was transferred into ice-water, stirred, and extracted with ethyl acetate. The combined organic layers were washed with brine, dried over anhydrous sodium sulfate, filtered, and concentrated under reduced pressure to afford 288.4. MS (ES): m/z 293.28 [M+H]$^+$.

Synthesis of compound 288.5. To a mixture of 288.4 (0.205 g, 0.701 mmol, 1.0 equiv), sodium carbonate (0.148 g, 1.40 mmol, 2.0 equiv) and Int-4 (0.087 g, 0.420 mmol, 0.6 equiv) in DMF (5 mL) was stirred at room temperature for 30 min. The reaction mixture was filtered, and the filtrate was transferred into water, stirred, and extracted with ethyl acetate. The combined organic layers were washed with brine, dried over anhydrous sodium sulfate, filtered, and concentrated under reduced pressure to afford 288.5. MS (ES): m/z 478.85 [M+H]$^+$.

Synthesis of compound 288.6. Compound 288.6 was prepared from 288.5 following the procedure described in the synthesis of 5.4. The product was purified by flash column chromatography on silica gel (CombiFlash®, 2% methanol in DCM) to afford 288.6. MS (ES): m/z 448.87 [M+H]$^+$.

Synthesis of compound 288.7. Compound 288.7 was prepared from 288.6 and Int-63, following the procedure described in the synthesis of I-13. The product was purified by flash column chromatography on silica gel (CombiFlash®, 4.2% methanol in DCM). MS (ES): m/z 448.99 [M+H]$^+$.

Synthesis of I-288. To a solution of 288.7 (0.109 g, 0.168 mmol, 1.0 equiv) in methanol (5 mL) was added 40% aq. sodium hydroxide solution (1 mL) and stirred at 80° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.5% methanol in DCM) to afford I-288. MS (ES): m/z 508.1 [M+H]$^+$, $^1$H NMR (DMSO-d$_6$, 400 MHz): δ 11.59 (s, 1H), 8.88 (s, 1H), 8.64 (s, 1H), 8.37 (s, 1H), 8.29 (bs, 2H), 7.54-7.50 (m, 2H), 4.01 (s, 3H), 3.67 (s, 3H).

Example 289: 6-((3-fluoro-1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

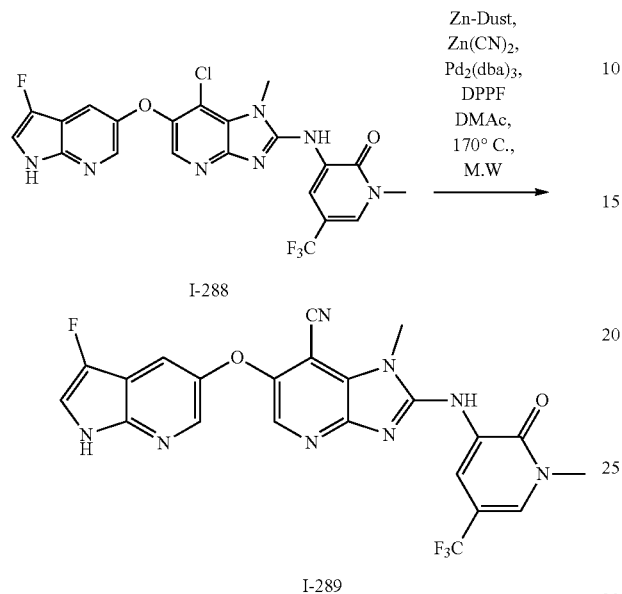

Synthesis of I-289. Compound I-289 was prepared from I-288 following the procedure described in the synthesis of I-157. The product was purified by flash column chromatography on silica gel (CombiFlash®, 4.2% methanol in DCM). MS (ES): m/z 499.2 [M+H]+, 1H NMR (DMSO-d6, 400 MHz): δ 11.68 (s, 1H), 9.01 (s, 1H), 8.64 (bs, 1H), 8.30 (bs, 1H), 8.17 (s, 1H), 8.04 (s, 1H), 7.80 (s, 1H), 7.59 (s, 1H), 3.99 (s, 3H), 3.67 (s, 3H).

Example 290: 1-methyl-6-((2-methyl-1H-pyrrolo[2,3-b]pyridin-5-yl)oxy)-2-((1-methyl-2-oxo-5-(trifluoromethyl)-1,2-dihydropyridin-3-yl)amino)-1H-imidazo[4,5-b]pyridine-7-carbonitrile

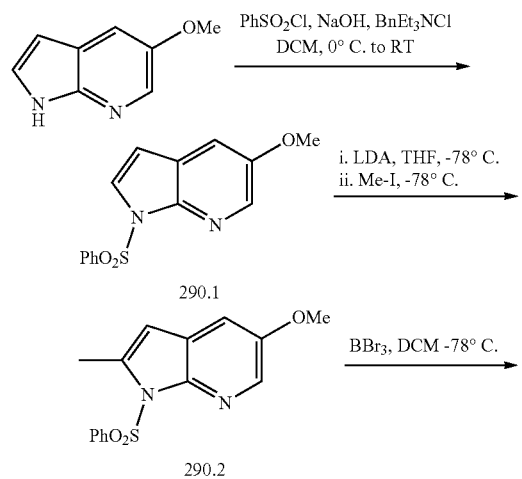

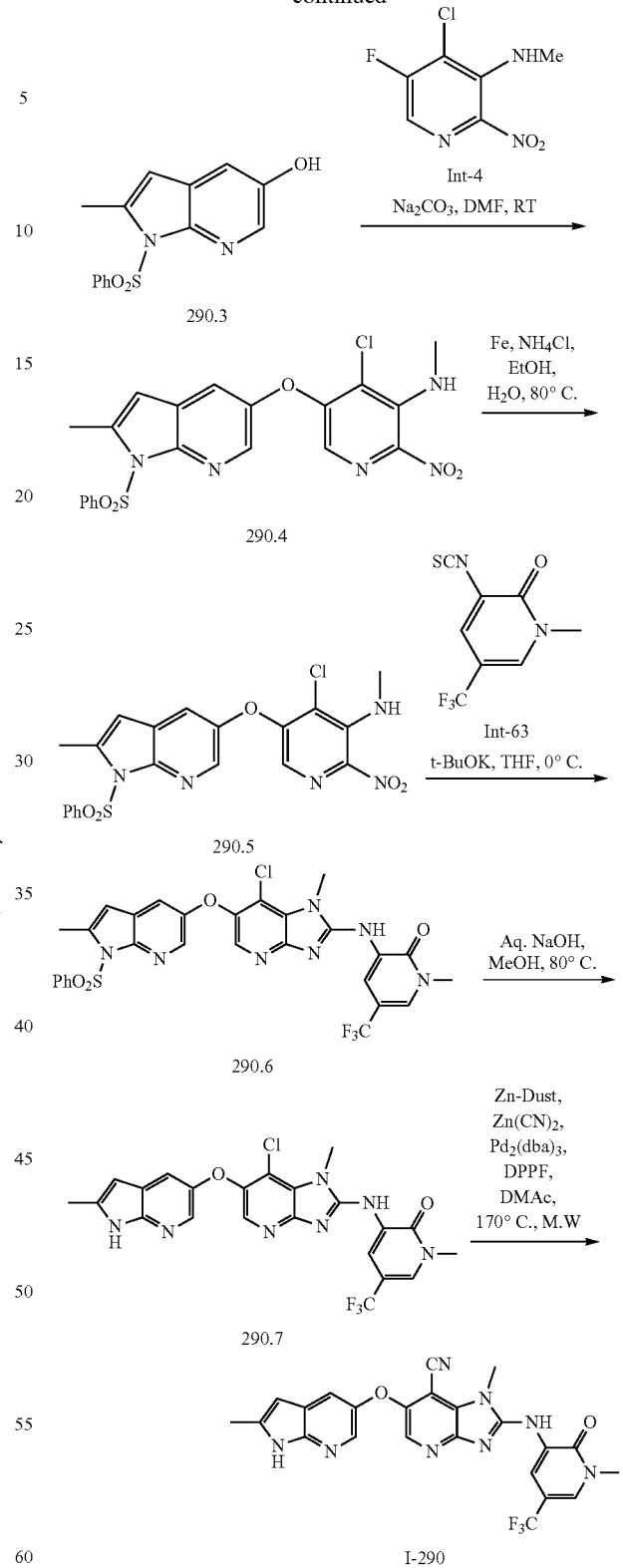

Synthesis of compound 290.1. To a solution of 5-methoxy-1H-pyrrolo[2,3-b]pyridine (7.9 g, 53.32 mmol, 1.0 equiv) in DCM (250 mL) was added benzyltriethylammonium chloride (0.242 g, 1.33 mmol, 0.025 equiv) followed by the addition of sodium hydroxide powder (7.3 g, 159.9 mmol, 3.0 equiv). It was cooled to 0° C., benzyl sulfonyl chloride (11.74 g, 66.65 mmol, 1.25 equiv) was added, and reaction mixture was stirred at room temperature for 2 h. The reaction mixture was filtered through a pad of Celite® and washed with DCM. Filtrate was concentrated under reduced pressure. The residue was purified by flash column chromatography on silica gel (CombiFlash®, 20% ethyl acetate in hexane) to afford 290.1. MS (ES): m/z 289.3 [M+H]$^+$.

Synthesis of compound 290.2. To a solution of 290.1 (5.2 g, 18.04 mmol, 1.0 equiv) in THF (100 mL) was added lithium diisopropylamide solution (2.0 M in THF, 18 mL, 36.8 mmol, 2.0 equiv) at −78° C. and stirred for 30 min followed by the addition of methyl iodide (4.5 mL, 72.16 mmol, 4.0 equiv) and stirred at same temperature for 15 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5% ethyl acetate in hexane) to afford 290.2. MS (ES): m/z 303.1 [M+H]$^+$.

Synthesis of compound 290.3. To a solution of 290.2 (1.7 g, 5.29 mmol, 1.0 equiv) in DCM (34 mL) was added boron tribromide solution (1 M in DCM, 42 mL, 42.16 mmol, 7.5 equiv) at −78° C. and stirred for 3 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 45% ethyl acetate in hexane) to afford 290.3. MS (ES): m/z 289.2 [M+H]$^+$.

Synthesis of compound 290.4. A mixture of 290.3 (1.0 g, 3.47 mmol, 1.0 equiv), sodium carbonate (0.736 g, 6.94 mmol, 2.0 equiv) and Int-4 (0.427 g, 2.08 mmol, 0.6 equiv) in DMF (7 mL) was stirred at room temperature for 30 min. The reaction mixture was filtered, and the filtrate was transferred into water, stirred, and extracted with ethyl acetate. The combined organic layers were washed with brine, dried over anhydrous sodium sulfate, filtered, and concentrated under reduced pressure to afford 290.4. MS (ES): m/z 474.5 [M+H]$^+$.

Synthesis of compound 290.5. Compound 290.5 was prepared from 290.4 following the procedure described in the synthesis of 5.4. The product was purified by flash column chromatography on silica gel (CombiFlash®, 2% methanol in DCM). MS (ES): m/z 448.6 [M+H]$^+$.

Synthesis of compound 290.6. Compound 290.6 was prepared from 290.5 and Int-63, following the procedure described in the synthesis of I-13. The product was purified by flash column chromatography on silica gel (CombiFlash®, 4.2% methanol in DCM). MS (ES): m/z 645.03 [M+H]$^+$.

Synthesis of compound 290.7. To a solution of 290.6 (0.200 g, 0.310 mmol, 1.0 equiv) in methanol (5 mL) was added 40% aq. sodium hydroxide solution (1 mL) and stirred at 80° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.5% methanol in DCM) to afford 290.7. MS (ES): m/z 504.87[M+H]$^+$.

Synthesis of I-290. Compound I-290 was prepared from 290.7 following the procedure described in the synthesis of I-157. The product was purified by flash column chromatography on silica gel (CombiFlash®, 4.1% methanol in DCM). MS (ES): m/z 495.2 [M+H]$^+$, $^1$H NMR (DMSO-d$_6$, 400 MHz): δ 11.53 (s, 1H), 8.82 (s, 1H), 8.61 (bs, 1H), 8.13 (s, 1H), 8.05 (s, 1H), 7.98 (s, 1H), 7.34 (s, 1H), 6.07 (s, 1H), 3.99 (s, 3H), 3.66 (s, 3H), 2.37 (s, 3H).

Example 291: 6-((6-methoxypyrazolo[1,5-a]pyridin-3-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

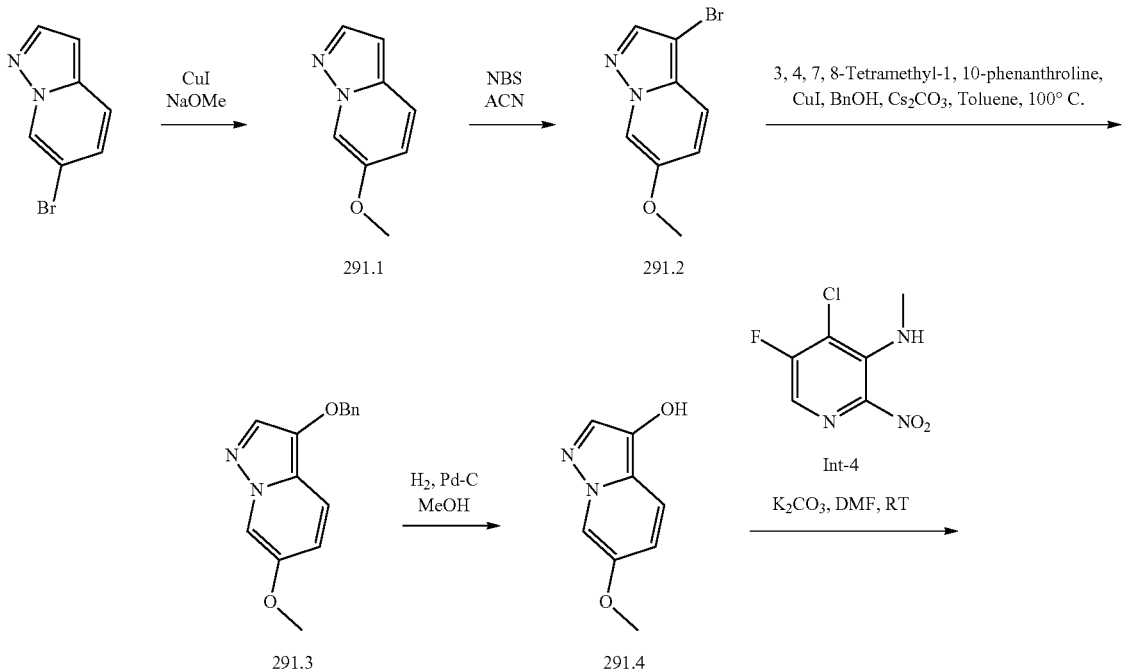

-continued

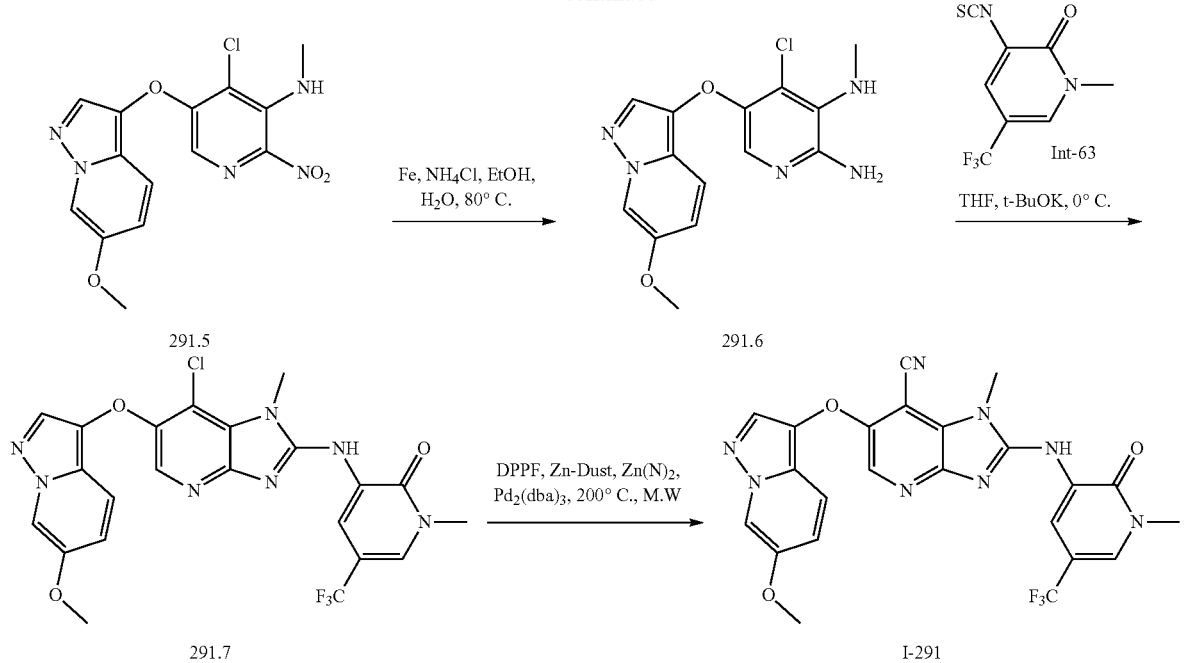

Synthesis of compound 291.1. A solution of 6-bromopyrazolo[1,5-a]pyridine (1.5 g, 7.61 mmol, 1.0 equiv), sodium methoxide in methanol (1 M, 15 mL) and copper iodide (2.9 g, 15.3 mmol, 2.0 equiv) was stirred at 120° C. for 2 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane) to afford 291.1. MS (ES): m/z 149.2 [M+H]$^+$.

Synthesis of compound 291.2. To a solution of 291.1 (0.9 g, 6.07 mmol, 1.0 equiv) in acetonitrile (10 mL) was added N-bromosuccinimide (2.16 g, 12.14 mmol, 2.0 equiv) in portions at 0° C. It was allowed to warm to room temperature and stirred for 15 min. It was transferred into aqueous sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford 291.2. MS (ES): m/z 228.5 [M+H]$^+$.

Synthesis of compound 291.3. To a mixture of 291.2 (0.840 g, 3.7 mmol, 1.0 equiv) in toluene (8 mL) was added benzyl alcohol (0.994 g, 9.25 mmol, 2.5 equiv) followed by cesium carbonate (2.3 g, 7.4 mmol, 2.0 equiv). The reaction mixture was degassed by bubbling argon through for 15 min. Under argon atmosphere, 3,4,7,8-Tetramethyl-1,10-phenanthroline (0.173 g, 0.736 mmol, 0.2 equiv) and copper iodide (0.069 g, 0.37 mmol, 0.1 equiv) was added. The reaction mixture was stirred at 100° C. for 1 h. It was cooled to room temperature was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 11% ethyl acetate in hexane) to afford 291.3 (0.440 g, 46.77%). MS (ES): m/z 255.4 [M+H]$^+$.

Synthesis of compound 291.4. A mixture of compound 291.3 (0.440 g, 1.73 mmol, 1.0 equiv) and palladium on charcoal (0.110 g) in methanol (10 mL) was stirred under hydrogen (1 atm) for 4 h. The reaction mixture was filtered through a pad of Celite® and rinsed with methanol. The filtrate was concentrated under reduced pressure to afford 291.4. MS (ES): m/z 165.2 [M+H]$^+$.

Synthesis of compound 291.5. Compound 291.5 was prepared from 291.4 following the procedure described in the synthesis of 19.1. The product was purified by flash column chromatography on silica gel (CombiFlash®, 35% ethyl acetate in hexane). MS (ES): m/z 350.5 [M+H]$^+$.

Synthesis of compound 291.6. Compound 291.6 was prepared from 291.5 following the procedure described in the synthesis of 5.4. The product was purified by flash column chromatography on silica gel (CombiFlash®, 70% ethyl acetate in hexane) to afford 291.6. MS (ES): m/z 320.5 [M+H]$^+$.

Synthesis of compound 291.7. Compound 291.7 was prepared from 291.6 and Int-63, following the procedure described in the synthesis of I-13. The product was purified by flash column chromatography on silica gel (CombiFlash®, 1.6% methanol in DCM). MS (ES): m/z 520.21 [M+H]$^+$.

Synthesis of I-291. Compound I-291 was prepared from 291.7 following the procedure described in the synthesis of I-281. The product was purified by flash column chromatography on silica gel (CombiFlash®, 4% methanol in DCM). MS (ES): m/z 511.3 [M+H]$^+$, $^1$H NMR (DMSO-d$_6$, 400 MHz): δ 8.96 (s, 1H), 8.62-8.61 (s, J=2.0 Hz, 1H), 8.40 (s, 1H), 8.17 (s, 1H), 8.05 (s, 1H), 7.97 (s, 1H), 7.49-7.47 (d, J=9.6 Hz, 1H), 7.07-7.05 (d, J=9.6 Hz 1H), 4.00 (s, 3H), 3.85 (s, 3H), 3.67 (s, 3H).

Example 292: 3-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)pyrazolo[1,5-a]pyridine-6-carbonitrile

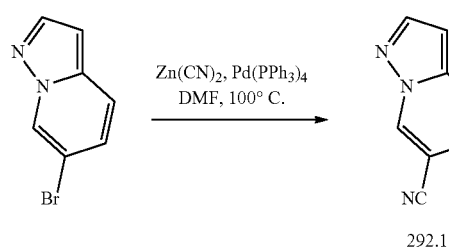
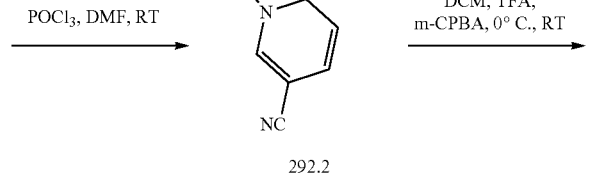

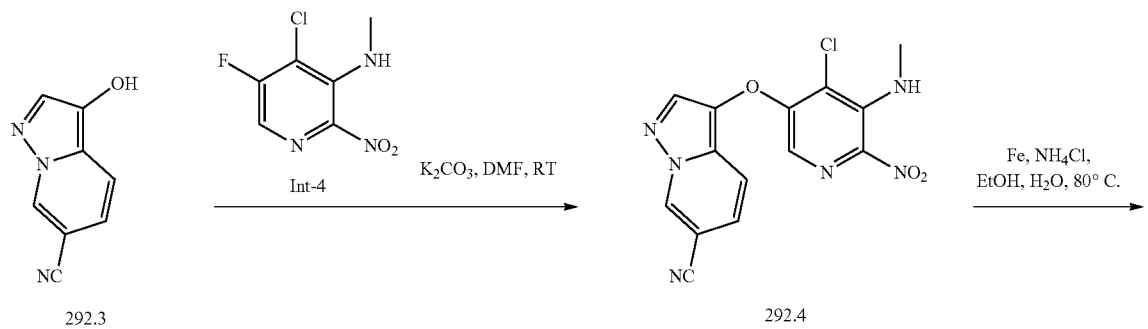
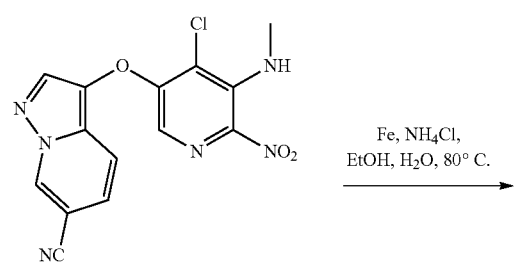

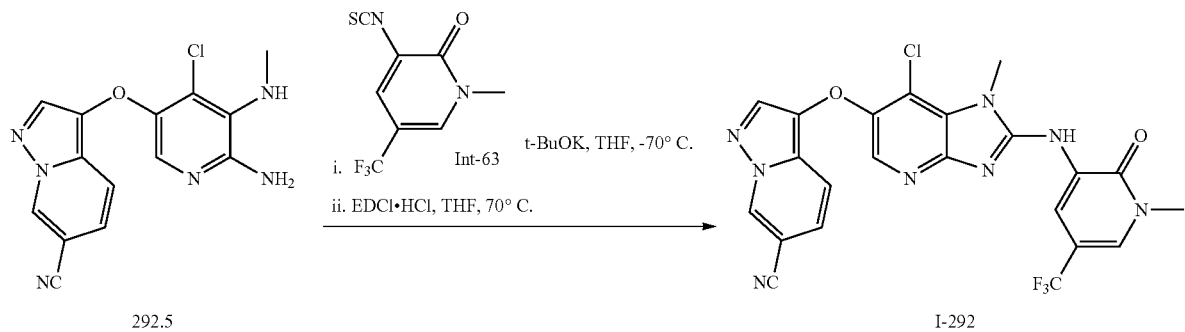

Synthesis of compound 292.1. A mixture of 6-bromopyrazolo[1,5-a]pyridine (4.0 g, 20.3 mmol, 1.0 equiv), tetrakis(triphenylphosphine)palladium(0) (2.3 g, 2.0 mmol, 0.1 equiv) and zinc cyanide (2.37 g, 20.3 mmol, 1.0 equiv) in DMF (25 mL) was stirred at 100° C. for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 16% ethyl acetate in hexane) to afford 292.1. MS (ES): m/z 144.15 [M+H]$^+$.

Synthesis of compound 292.2. To a solution of 292.1 (2.0 g, 13.97 mmol, 1.0 equiv) in DMF (15 mL), was added phosphoryl chloride (6.4 g, 41.9 mmol, 3.0 equiv) and stirred at room temperature for 1 h. The reaction mixture was concentrated under reduced pressure to afford a residue, which was dissolved in DCM and washed with 2 N sodium hydroxide. The combined organic layers were washed with brine, dried over anhydrous sodium sulfate, filtered, and concentrated under reduced pressure to afford pressure. The residue was purified by flash column chromatography on silica gel (CombiFlash®, 30% ethyl acetate in hexane) to afford 292.2. MS (ES): m/z 172.16 [M+H]$^+$.

Synthesis of compound 292.3. To a solution of 292.2 (1.1 g, 6.43 mmol, 1.0 equiv) in DCM (10 mL) was added trifluoroacetic acid (49.1 mL, 0.643 mmol, 0.1 equiv) at 0° C. followed by the addition of m-chloroperoxybenzoic acid (1.65 g, 9.6 mmol, 1.5 equiv). The reaction mixture was stirred at room temperature for 2 h. It was cooled to 0° C. and saturated sodium bicarbonate solution was added, stirred for 30 min and extracted with ethyl acetate. The combined organic layers were washed with aq. sodium bisulfite, dried over anhydrous sodium sulfate, filtered, and concentrated under reduced pressure. The residue was purified by flash column chromatography on silica gel (CombiFlash®, 60% ethyl acetate in hexane) to afford 292.3. MS (ES): m/z 160.15 [M+H]$^+$.

Synthesis of compound 292.4. Compound 292.4 was prepared from 292.3 and Int-4, following the procedure described in the synthesis of 19.1. The reaction mixture was filtered, and the filtrate was concentrated under reduced pressure. The residue was purified by flash column chromatography on silica gel (CombiFlash®, 2.5% methanol in DCM). MS (ES): m/z 345.72 [M+H]⁺.

Synthesis of compound 292.5. Compound 292.5 was prepared from 292.4 following the procedure described in the synthesis of 5.4. The product was purified by flash column chromatography on silica gel (CombiFlash®, 2.8% methanol in DCM). MS (ES): m/z 315.73 [M+H]⁺.

Synthesis of compound I-292. Compound I-292 was prepared from 291.5 and Int-63, following the procedure described in the synthesis of I-51. The product was purified by flash column chromatography on silica gel (Combi-Flash®, 2.8% methanol in DCM). MS (ES): m/z 515.2 [M+H]⁺, ¹H NMR (DMSO-d₆, 400 MHz): δ 9.56 (s, 1H), 8.84 (s, 1H), 8.62 (s, 1H), 8.31 (s, 1H), 8.14 (bs, 2H), 7.70-7.67 (d, J=9.2 Hz, 1H), 7.41-7.38 (d, J=9.2 Hz, 1H), 4.03 (s, 3H), 3.68 (s, 3H).

Example 293: 3-((7-chloro-1-methyl-6-((2-methyl-1H-pyrrolo[2,3-b]pyridin-5-yl)oxy)-1H-imidazo[4,5-b]pyridin-2-yl)amino)-1-methyl-5-(trifluoromethyl)pyridin-2(1H)-one

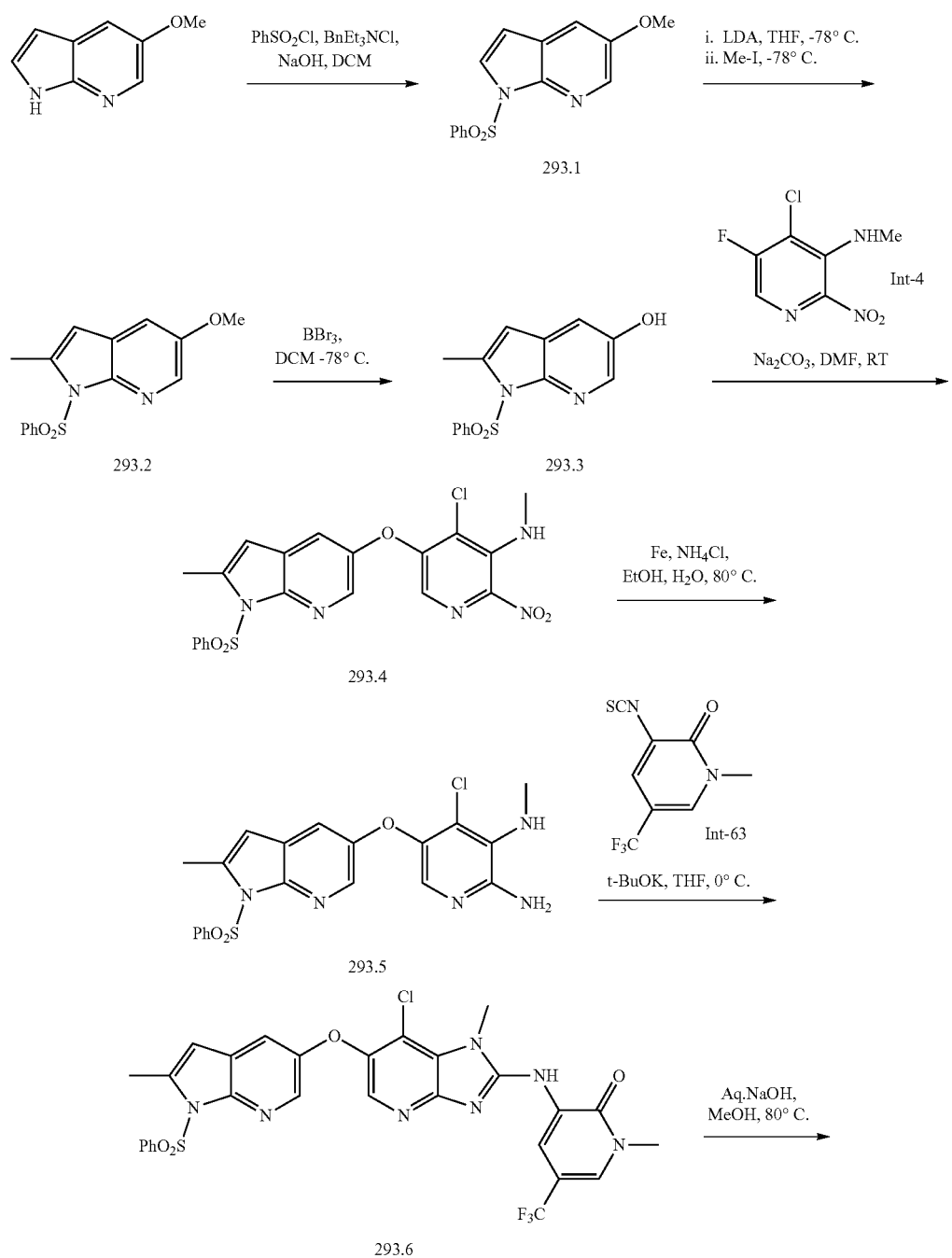

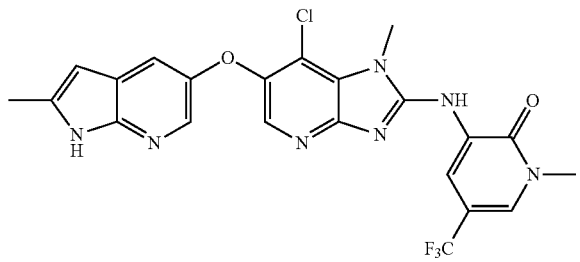

I-293

Synthesis of compound 293.1. To a solution of 5-methoxy-1H-pyrrolo[2,3-b]pyridine (7.9 g, 53.32 mmol, 1.0 equiv) and benzyltriethylammonium chloride (0.242 g, 1.33 mmol, 0.025 equiv) in DCM (250 mL) was added sodium hydroxide powder (7.3 g, 159.9 mmol, 3.0 equiv). To the reaction mixture was added benzyl sulfonyl chloride (11.74 g, 66.65 mmol, 1.25 equiv) at 0° C., and it was allowed to warm to room temperature and stirred for 2 h. It was filtered through a pad of Celite® and rinsed with DCM. The filtrate was concentrated under reduced pressure. The residue was purified by flash column chromatography on silica gel (CombiFlash®, 20% ethyl acetate in hexane) to afford 293.1. MS (ES): m/z 289.3 [M+H]⁺.

Synthesis of compound 293.2. To a solution of 293.1 (5.2 g, 18.04 mmol, 1.0 equiv) in THF (100 mL) was added lithium diisopropylamide solution (2.0 M in THF, 18 mL, 36.8 mmol, 2.0 equiv) at −78° C. and stirred for 30 min before the addition of methyl iodide (4.5 mL, 72.16 mmol, 4.0 equiv). The mixture was allowed to warm to room temperature for 15 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5% ethyl acetate in hexane) to afford 293.2. MS (ES): m/z 303.1 [M+H]⁺.

Synthesis of compound 293.3. To a solution of 293.2 (1.7 g, 5.29 mmol, 1.0 equiv) in DCM (34 mL) was added boron tribromide solution (1 M in DCM) (42 mL, 42.16 mmol, 7.5 equiv) at −78° C. and stirred for 3 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 45% ethyl acetate in hexane) to afford 293.3. MS (ES): m/z 289.2 [M+H]⁺.

Synthesis of compound 293.4. A mixture of 293.3 (1.0 g, 3.47 mmol, 1.0 equiv), sodium carbonate (0.736 g, 6.94 mmol, 2.0 equiv) and Int-4 (0.427 g, 2.08 mmol, 0.6 equiv) in DMF (7 mL) was stirred at room temperature for 30 min. The reaction mixture was filtered, and the filtrate was transferred into water stirred, and extracted with ethyl acetate. The combined organic layers were washed with brine, dried over anhydrous sodium sulfate, filtered, and concentrated under reduced pressure to afford 293.3. MS (ES): m/z 474.5 [M+H]⁺.

Synthesis of compound 293.5. Compound 293.5 was prepared from 293.4 following the procedure described in the synthesis of 5.4. The product was purified by flash column chromatography on silica gel (CombiFlash®, 2% methanol in DCM). MS (ES): m/z 448.6 [M+H]⁺.

Synthesis of compound 293.6. Compound 293.6 was prepared from 293.5 and Int-63, following the procedure described in the synthesis of I-13. The product was purified by flash column chromatography on silica gel (CombiFlash®, 4.2% methanol in DCM). MS (ES): m/z 645.0 [M+H]⁺.

Synthesis of I-293. To a solution of 293.6 (0.200 g, 0.310 mmol, 1.0 equiv) in methanol (5 mL) was added 40% aq. sodium hydroxide solution (1 mL) and stirred at 80° C. for 4 h. It was transferred into ice-saturated sodium bicarbonate solution and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.5% methanol in DCM) to afford I-293. MS (ES): m/z 504.2 [M+H]⁺, ¹H NMR (DMSO-d₆, 400 MHz): δ 11.53 (s, 1H), 8.82 (s, 1H), 8.62 (bs, 1H), 8.14 (s, 1H), 8.06 (s, 1H), 8.00 (bs, 1H), 7.35 (bs, 1H), 6.08 (s, 1H), 4.01 (s, 3H), 3.60 (s, 3H), 2.39 (s, 3H).

Example 294: 3-((7-chloro-6-((2-cyclopropyl-1H-pyrrolo[2,3-b]pyridin-5-yl)oxy)-1-methyl-1H-imidazo[4,5-b]pyridin-2-yl)amino)-1-methyl-5-(trifluoromethyl)pyridin-2(1H)-one

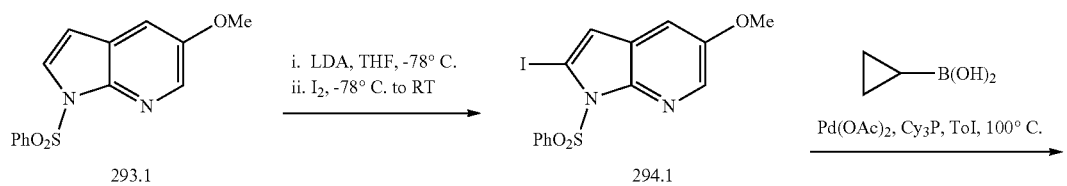

-continued

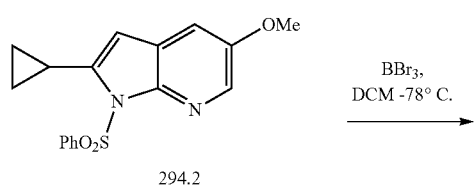 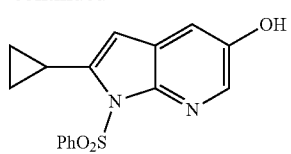 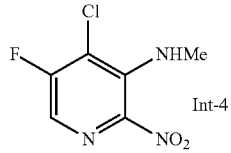

294.2     294.3

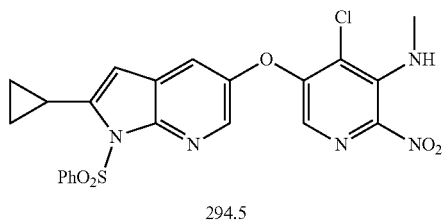

294.5

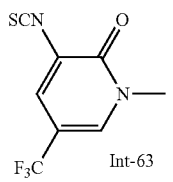

Int-63

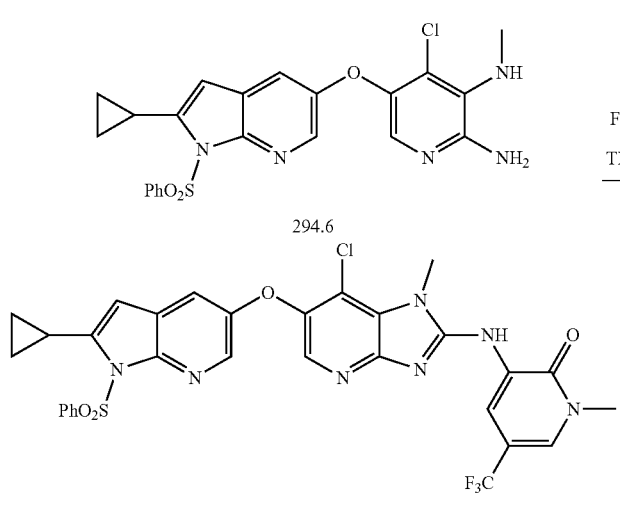

294.6

294.7

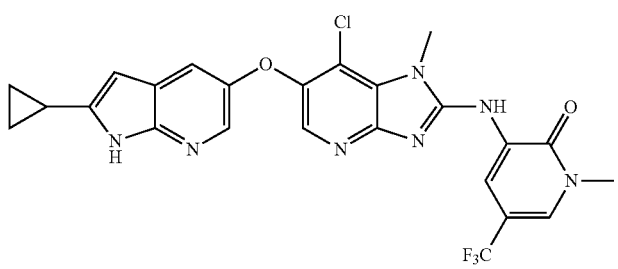

I-294

Synthesis of compound 294.1. To a solution of 293.1 (2.0 g, 6.94 mmol, 1.0 equiv) in THF (40 mL) was added lithium diisopropylamide solution (2.0 M in THF, 14 mL, 13.88 mmol, 2.0 equiv) at −78° C. and stirred for 30 min before the addition of iodine (5.29 g, 20.83 mmol, 3.0 equiv). The reaction mixture was allowed to warm to room temperature and stirred for 15 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4% ethyl acetate in hexane) to afford 294.1. MS (ES): m/z 415.2 [M+H]$^+$.

Synthesis of compound 294.2. A mixture of 294.1 (0.910 g, 2.20 mmol, 1.0 equiv), cyclopropylboronic acid (0.245 g, 2.86 mmol, 1.3 equiv), potassium phosphate (1.67 g, 7.91 mmol, 3.6 equiv) and tricyclohexylphosphine (0.123 g, 0.439 mmol, 0.2 equiv) in toluene (15 mL) and water (2 mL) was degassed by bubbling argon through for 10 min. Under argon atmosphere, palladium(II) acetate (0.049 g, 0.219 mmol, 0.17 equiv) was added, and degassed for 5 min. The reaction mixture was stirred at 100° C. for 4 h. It was cooled to room temperature, filtered through a pad of Celite®. The filtrate was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford 294.2. MS (ES): m/z 329.2 [M+H]$^+$.

Synthesis of compound 294.3. To a solution of compound 294.2 (0.610 g, 1.86 mmol, 1.0 equiv) in DCM (25 mL) was added boron tribromide solution (1 M in DCM, 14 mL, 13.87 mmol, 7.5 equiv) at −78° C. and stirred for 3 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 43% ethyl acetate in hexane) to afford 294.3. MS (ES): m/z 315.3 [M+H]+.

Synthesis of compound 294.5. Compound 294.5 was prepared from 294.3 and Int-4 following the procedure described in the synthesis of 293.4. The crude product was used without purification. MS (ES): m/z 500.8 [M+H]+.

Synthesis of compound 294.6. Compound 294.6 was prepared from 294.5 following the procedure described in the synthesis of 5.4. The product was purified by flash column chromatography on silica gel (CombiFlash®, 2% methanol in DCM) t. MS (ES): m/z 470.7 [M+H]+.

Synthesis of compound 294.7. Compound 294.7 was prepared from 294.6 and Int-63, following the procedure described in the synthesis of I-13. The product was purified by flash column chromatography on silica gel (CombiFlash®, 4.2% methanol in DCM). MS (ES): m/z 671.0 [M+H]+.

Synthesis of I-294. Compound I-294 was prepared from 294.7 following the procedure described in the synthesis of I-293. The product was purified by flash column chromatography on silica gel (CombiFlash®, 5.5% methanol in DCM). MS (ES): m/z 530.4 [M+H]+, 1H NMR (DMSO-d6, 400 MHz): δ 11.52 (s, 1H), 8.83 (s, 1H), 8.63 (bs, 1H), 8.15 (s, 1H), 8.06 (s, 1H), 7.97 (s, 1H), 7.32 (s, 1H), 6.04 (s, 1H), 4.01 (s, 3H), 3.68 (s, 3H), 2.03-2.02 (m, 1H), 1.01-0.99 (m, 2H), 0.85 (bs, 2H).

Example 295: trans-3-((7-chloro-6-((4-fluoropyrazolo[1,5-a]pyridin-3-yl)oxy)-1-methyl-1H-imidazo[4,5-b]pyridin-2-yl)amino)-1-(3-hydroxycyclobutyl)-5-(trifluoromethyl)pyridin-2(1H)-one

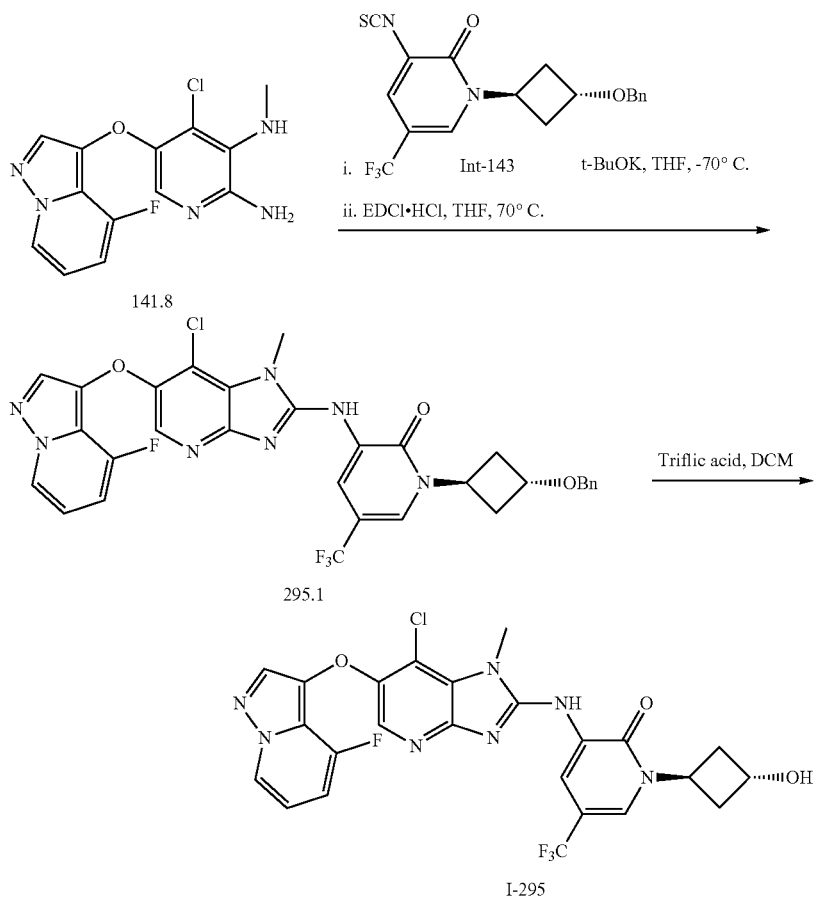

Synthesis of compound 295.1. Compound 295.1 was prepared from 141.8 and Int-143, following the procedure described in the synthesis of I-51. The product was purified by flash column chromatography on silica gel (CombiFlash®, 1.8% methanol in DCM). MS (ES): m/z 655.7 [M+H]+.

Synthesis of I-295. To a solution of 295.1 (0.050 g, 0.076 mmol, 1.0 equiv) in DCM (2 mL) was added triflic acid (0.1 mL) at 0° C. and stirred for 5 min. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-295. MS (ES):

m/z 564.5 [M+H]⁺. ¹H NMR (DMSO-d₆, 400 MHz): δ 8.82 (s, 1H), 8.61 (s, 1H), 8.55-8.53 (d, J=6.8 Hz, 1H), 8.06 (s, 1H), 8.01 (s, 1H), 7.93 (s, 1H), 7.10-7.05 (m, 1H), 6.91-6.87 (m, 1H), 5.39-5.35 (m, 1H), 5.29-5.28 (d, J=4.0 Hz 1H), 4.37 (bs, 1H), 4.03 (s, 3H), 2.68 (bs, 2H), 2.40-2.35 (m, 2H).

Example 296: 6-((2-cyclopropyl-1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

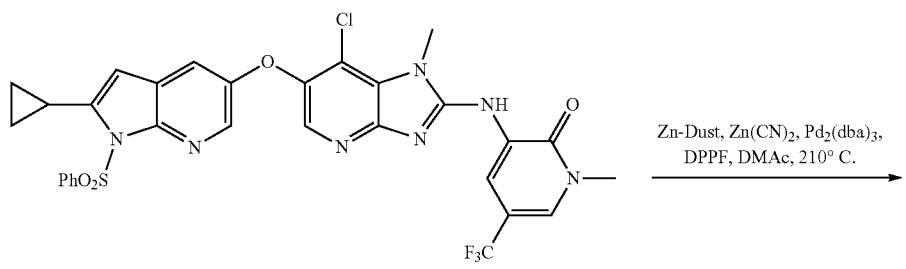

I-294

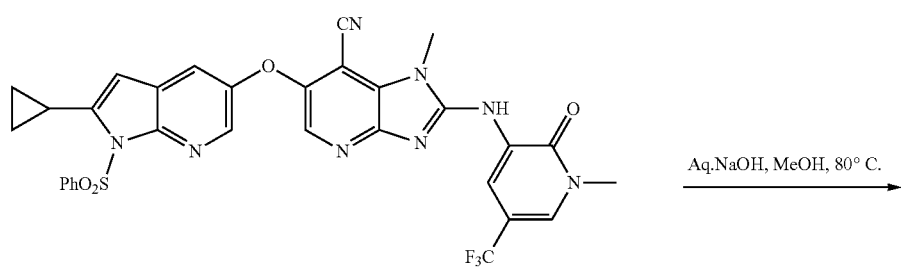

296.1

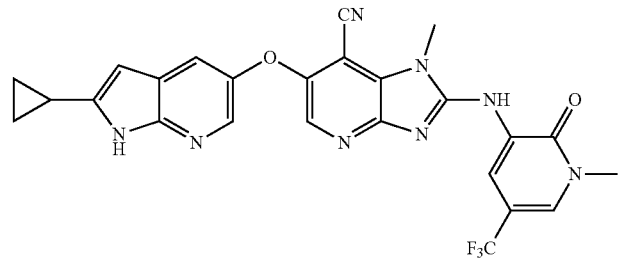

I-296

Synthesis of compound 296.1. A mixture of I-294 (0.139 g, 0.207 mmol, 1.0 equiv), zinc dust (0.007 g, 0.041 mmol, 0.2 equiv) and zinc cyanide (0.012 g, 0.103 mmol, 0.5 equiv) in N,N-dimethylacetamide (11 mL) was degassed by bubbling argon through for 10 min. Under argon atmosphere, tris(dibenzylideneacetone)dipalladium(0) (0.056 g, 0.062 mmol, 0.3 equiv) and 1,1'-bis(diphenylphosphino)ferrocene (0.025 g, 0.031 mmol, 0.15 equiv) were added, and degassed for 5 min. The reaction mixture was stirred at 210° C. for 12 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford 296.1. MS (ES): m/z 661.4 [M+H]⁺.

Synthesis of I-296. Compound I-296 was prepared from 296.1 following the procedure described in the synthesis of I-293. The product was purified by flash column chromatography on silica gel (CombiFlash®, 5.2% methanol in DCM). MS (ES): m/z 521.2 [M+H]⁺, ¹H NMR (DMSO-d₆, 400 MHz): δ 11.62 (s, 1H), 8.97 (s, 1H), 8.63 (bs, 1H), 8.17 (s, 1H), 8.05 (s, 1H), 7.95 (s, 1H), 7.57 (s, 1H), 6.11 (s, 1H), 3.99 (s, 3H), 3.67 (s, 3H), 2.03-2.02 (m, 1H), 1.03 (bs 2H), 0.85 (bs, 2H).

Example 297: trans-6-((4-fluoropyrazolo[1,5-a]pyridin-3-yl)oxy)-2-((1-(3-hydroxycyclobutyl)-2-oxo-5-(trifluoromethyl)-1,2-dihydropyridin-3-yl)amino)-1-methyl-1H-imidazo[4,5-b]pyridine-7-carbonitrile

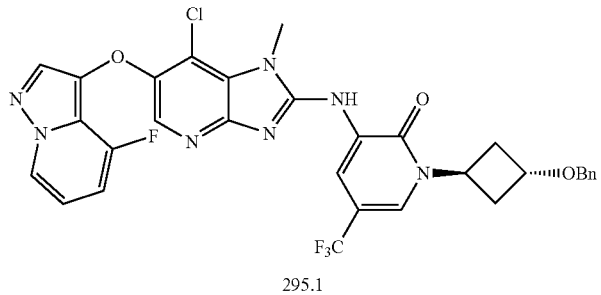

295.1

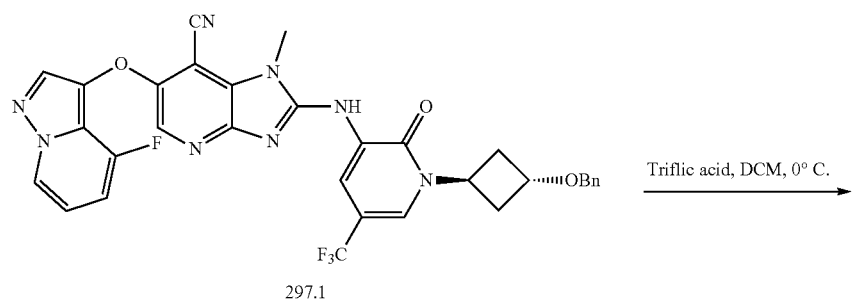

297.1

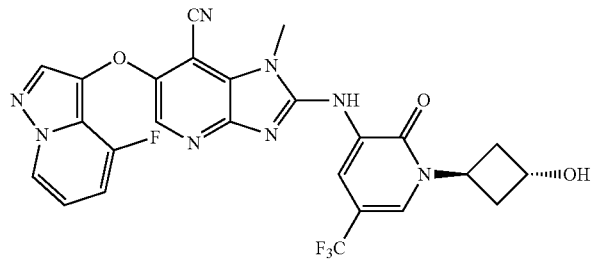

I-297

Synthesis of compound 297.1. Compound 297.1 was prepared from 295.1 following the procedure described in the synthesis of I-157. The product was purified by flash column chromatography on silica gel (CombiFlash®, 4.2% methanol in DCM). MS (ES): m/z 645.4 [M+H]⁺.

Synthesis of I-297. To a solution of 297.1 (0.040 g, 0.062 mmol, 1.0 equiv) in DCM (2 mL) was added triflic acid (0.1 mL) at 0° C. and stirred for 5 min. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-297. MS (ES): m/z 555.21 [M+H]⁺. ¹H NMR (DMSO-d₆, 400 MHz): δ 8.97 (s, 1H), 8.62 (s, 1H), 8.60-8.58 (d, J=7.2 Hz, 1H), 8.25 (s, 1H), 8.00 (s, 1H), 7.95 (s, 1H), 7.15-7.10 (m, 1H), 6.95-6.90 (m, 1H), 5.39-5.35 (m, 1H), 5.29-5.28 (m, 1H), 4.37 (bs, 1H), 4.00 (s, 3H), 2.68 (bs, 2H), 2.40-2.35 (m, 2H).

Example 298: N-(4-((1,4-oxazepan-4-yl)methyl)-3-(trifluoromethyl)phenyl)-7-chloro-1-methyl-6-(pyrazolo[1,5-a]pyrazin-3-yloxy)-1H-imidazo[4,5-b]pyridin-2-amine

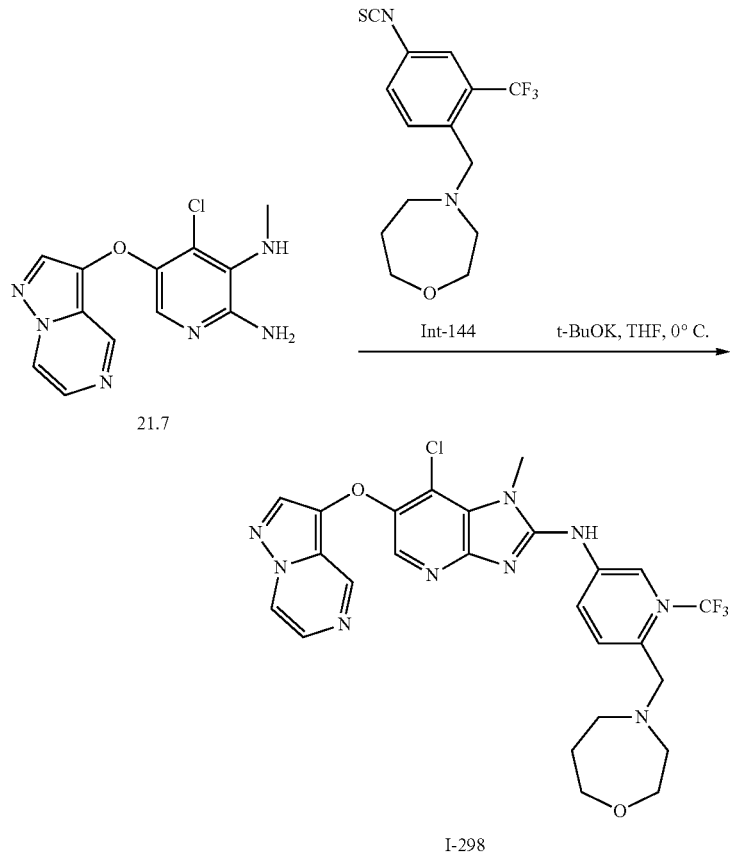

Synthesis of compound I-298. Compound I-298 was prepared from 21.7 and Int-144, following the procedure described in the synthesis of I-13. The product was purified by flash column chromatography on silica gel (CombiFlash®, 2.7% methanol in DCM). MS (ES): m/z 573.3 [M+H]$^+$, $^1$H NMR (DMSO-d$_6$, 400 MHz): δ 9.64 (s, 1H), 9.03 (s, 1H), 8.70-8.69 (d, J=4.4 Hz, 1H), 8.29 (s, 1H), 8.21 (s, 1H), 8.18-8.16 (d, J=8.0 Hz, 1H), 8.04 (s, 1H), 7.88-7.87 (d, J=4.8 Hz, 1H), 7.82-7.79 (d, J=8.8 Hz, 1H), 4.03 (s, 3H), 3.75-3.72 (m, 6H), 3.64 (bs, 2H), 2.66 (bs, 2H), 1.84 (bs, 2H).

Example 299: 6-((3-methoxy-1H-pyrazolo[3,4-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

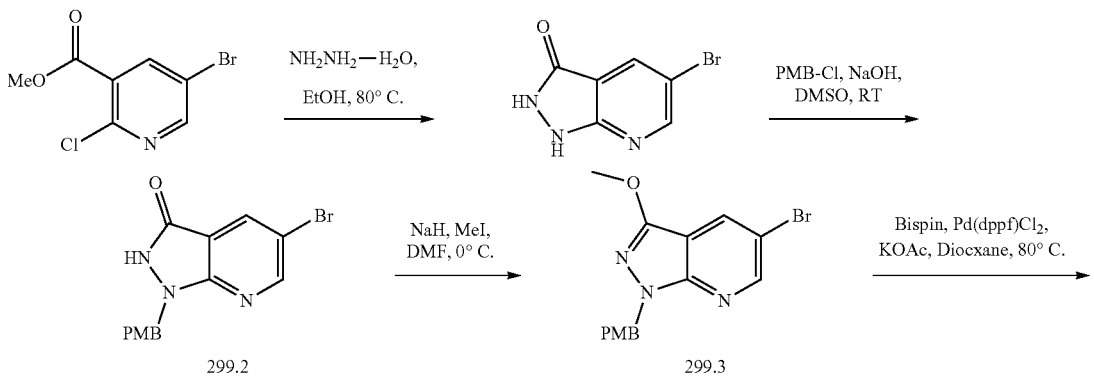

-continued
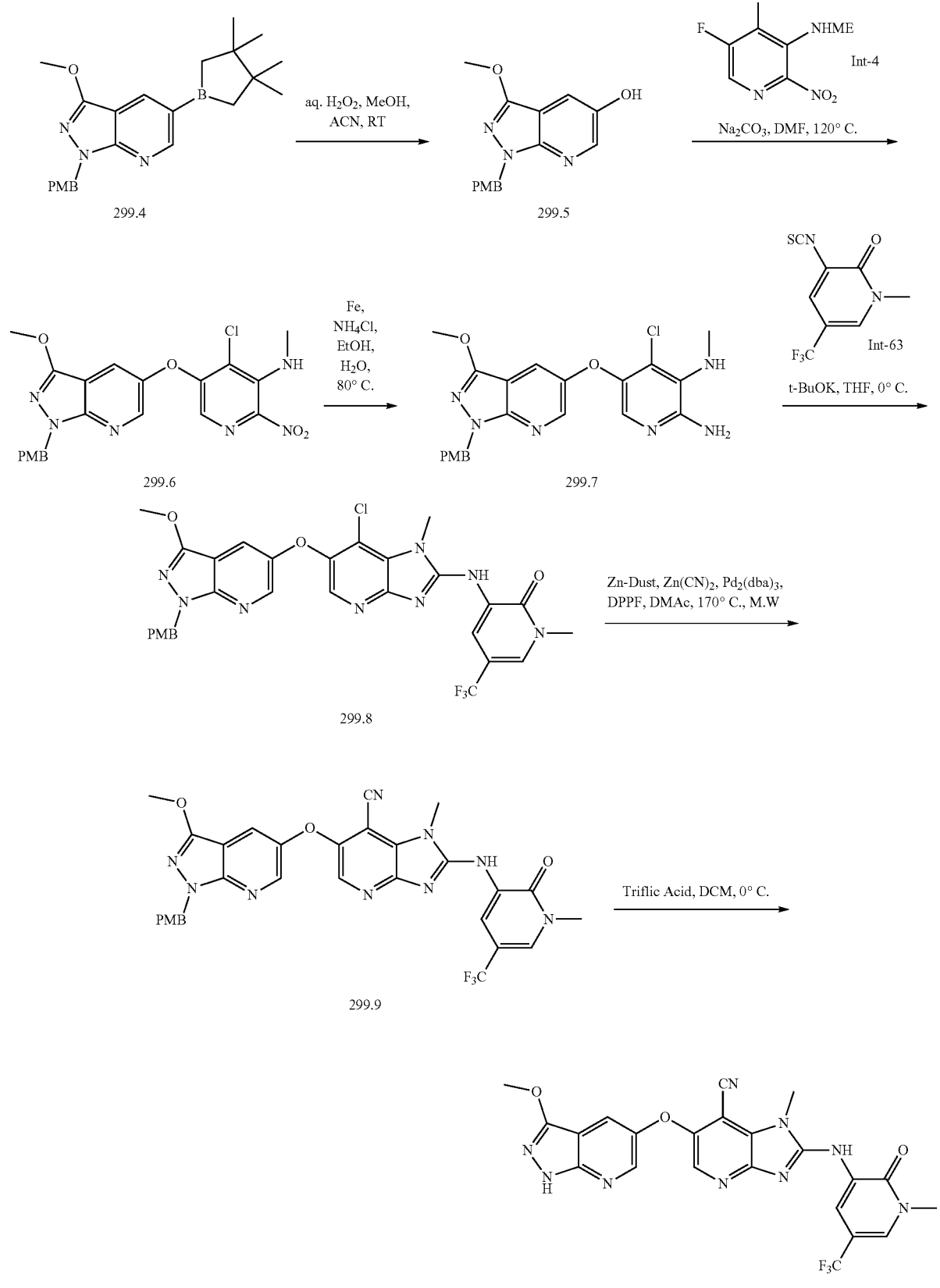

Synthesis of compound 299.1. To a solution of methyl 5-bromo-2-chloronicotinate (2.0 g, 7.98 mmol, 1.0 equiv) and hydrazine hydrate (13 mL) in ethanol (40 mL) was stirred at 80° C. for 16 h. The reaction mixture was concentrated under reduced pressure. The residue was purified by flash column chromatography on silica gel (CombiFlash®, 38% ethyl acetate in hexane) to afford 299.1. MS (ES): m/z 215.0 [M+H]$^+$.

Synthesis of compound 299.2. To a solution of 299.1 (0.903 g, 4.22 mmol, 1.0 equiv) in dimethyl sulfoxide (25 mL) was added sodium hydride (0.253 g, 6.3 mmol, 1.5 equiv) at 0° C. in portions and stirred for 30 min, before the addition of 4-methoxybenzyl chloride (0.986 g, 6.3 mmol, 4.8 equiv). The reaction mixture was stirred at room temperature for 30 min. It was poured into ice-water and stirred. The precipitated solids were collected by filtration and dried under vacuum to afford 299.2. MS (ES): m/z 335.1 [M+H]$^+$.

Synthesis of compound 299.3. To a solution of 299.2 (0.589 g, 1.76 mmol, 1.0 equiv) in DMF (8 mL) was added sodium hydride (0.101 g, 2.1 mmol, 1.2 equiv) at 0° C. and stirred for 30 min. To the mixture was added methyl iodide (0.298 g, 2.1 mmol, 1.2 equiv) and stirred at room temperature for 16 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 22% ethyl acetate in hexane) to afford 299.3. MS (ES): m/z 349.0 [M+H]$^+$.

Synthesis of compound 299.4. A mixture of 299.3 (0.207 g, 5.09 mmol, 1.0 equiv), bis(pinacolato)diboron (0.300 g, 1.1 mmol, 2.0 equiv) and potassium acetate (0.107 g, 1.1 mmol, 2.0 equiv) in 1,4-dioxane (7 mL) and water (3 mL) was degassed by bubbling argon through for 10 min. [1,1'-Bis(diphenylphosphino)ferrocene]dichloropalladium(II), complex with DCM (0.087 g, 0.11 mmol, 0.2 equiv) was added, and degassed for 5 min. The reaction mixture was stirred at 111° C. for 1 h. It was transferred into water and extracted with ethyl acetate. The combined organic layers were washed with brine, dried over anhydrous sodium sulfate, filtered, and concentrated under reduced pressure to afford 299.4. MS (ES): m/z 396.1 [M+H]$^+$.

Synthesis of compound 299.5 To a solution of 299.4 (0.230 g, 0.581 mmol, 1.0 equiv) in methanol (10 mL) was added acetonitrile (10 mL) and hydrogen peroxide (8 mL) at 0° C. and stirred for 5 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 22% ethyl acetate in hexane) to afford 299.5. MS (ES): m/z 286.2 [M+H]$^+$.

Synthesis of compound 299.6. A mixture of 299.5 (0.700 g, 4.33 mmol, 1.0 equiv), potassium carbonate (1.1 g, 7.9 mmol, 3.0 equiv) and Int-4 (0.910 g, 4.33 mmol 1.0 equiv) in DMF (8 mL) was stirred at room temperature for 30 min. The reaction mixture was filtered, and the filtrate was concentrated under reduced pressure. The residue was purified by flash column chromatography on silica gel (CombiFlash®, 42% ethyl acetate in hexane) to afford 299.6. MS (ES): m/z 471.6 [M+H]$^+$.

Synthesis of compound 299.7. Compound 299.7 was prepared from 299.6 following the procedure described in the synthesis of 5.4. The product was purified by flash column chromatography on silica gel (CombiFlash®, 40% ethyl acetate in hexane). MS (ES): m/z 441.7 [M+H]$^+$.

Synthesis of compound 299.8. Compound 299.8 was prepared from 299.7 and Int-63, following the procedure described in the synthesis of I-13. The product was purified by flash column chromatography on silica gel (CombiFlash®, 2.6% methanol in DCM). MS (ES): m/z: 642.01 [M+H]$^+$.

Synthesis of compound 299.9. Compound 299.9 was prepared from 299.8 following the procedure described in the synthesis of I-157. The product was purified by flash column chromatography on silica gel (CombiFlash®, 4.5% methanol in DCM). MS (ES): m/z 632.58.

Synthesis of compound I-299. To a solution of 299.9 (0.069 g, 0.109 mmol, 1.0 equiv) in DCM (4 mL) was added triflic acid (0.3 mL) at 0° C. and stirred for 5 min. It was transferred into ice-saturated sodium bicarbonate solution and extracted with DCM. The combined organic layers were washed with brine, dried over anhydrous sodium sulfate, filtered, and concentrated under reduced pressure The residue was purified by flash column chromatography on silica gel (CombiFlash®, 2.1% methanol in DCM) to afford I-299. MS (ES): m/z 512.2 [M+H]$^+$, $^1$H NMR (DMSO-d$_6$, 400 MHz): δ 12.71 (s, 1H), 9.00 (s, 1H), 8.63 (s, 1H), 8.55-8.54 (d, J=2.8 Hz, 1H), 8.17 (s, 1H), 8.06 (s, 1H), 7.84-7.83 (d, J=2.4 Hz, 1H), 3.97 (bs, 6H), 3.66 (s, 3H).

Example 300: 6-((3-cyano-1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

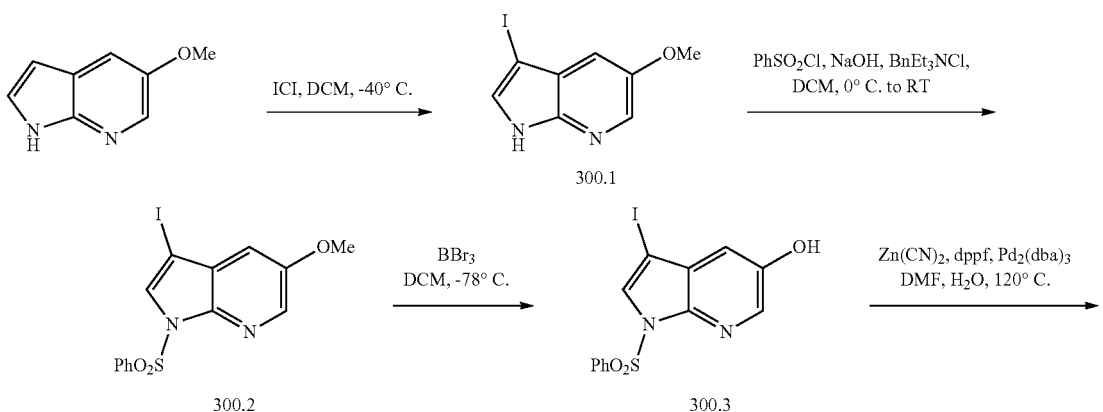

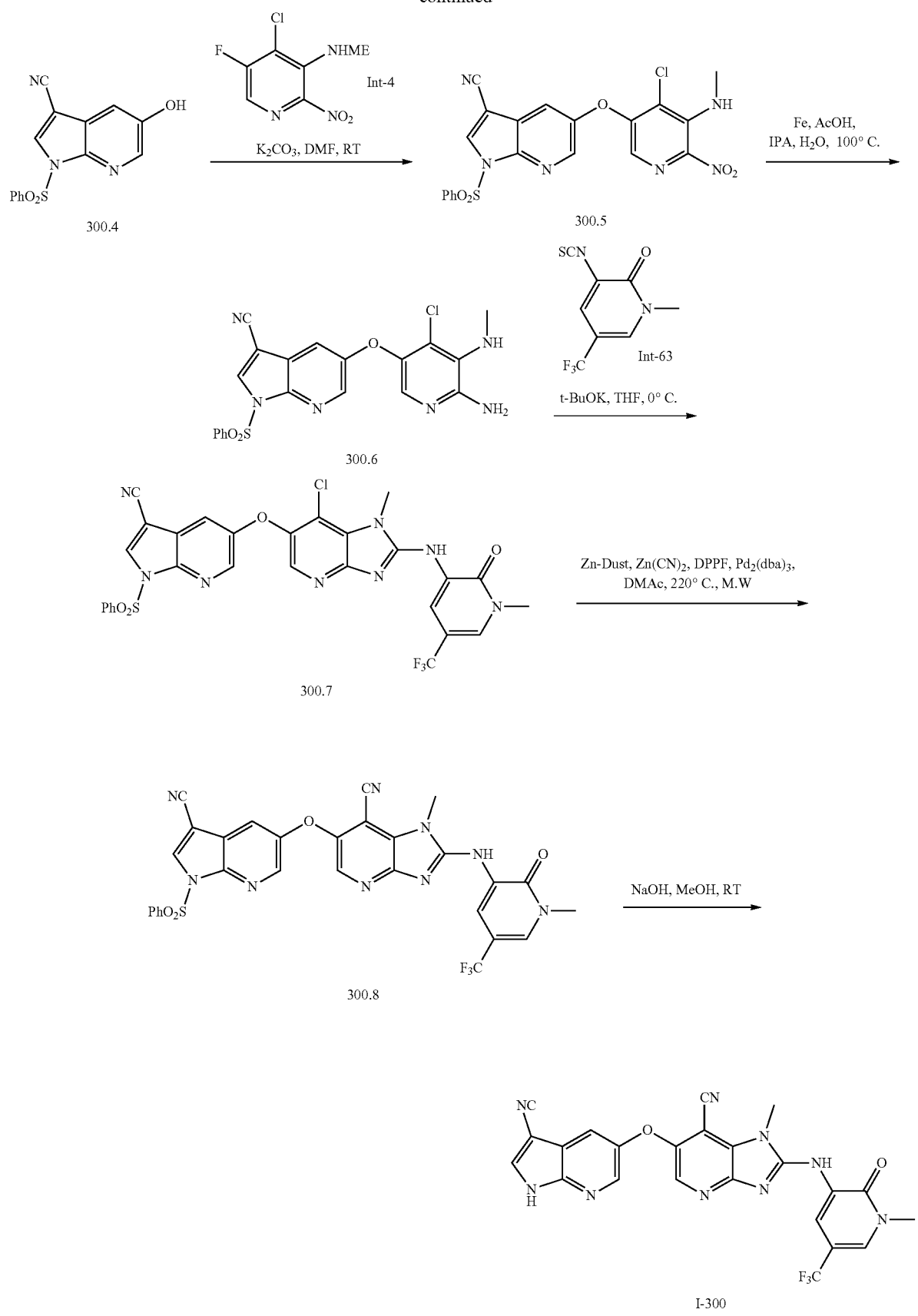

Synthesis of compound 300.1. To a solution of 5-methoxy-1H-pyrrolo[2,3-b]pyridine (1.0 g, 6.75 mmol, 1.0 equiv) in DCM (10 mL) was added iodine monochloride (8 mL, 152 mmol, 22 equiv) at −40° C. and stirred at room temperature for 2 h. It was poured into ice-water and extracted with DCM. The combined organic layers were washed with brine, dried over anhydrous sodium sulfate, filtered, and concentrated under reduced pressure to afford 300.1. MS (ES): m/z 275.1 [M+H]+.

Synthesis of compound 300.2. To a solution of 300.1 (0.9 g, 3.28 mmol, 1.0 equiv) in DCM (10 mL), was added benzyltriethylammonium chloride (0.018 g, 0.082 mmol, 0.025 equiv) followed by the addition of sodium hydroxide powder (0.393 g, 9.84 mmol, 3.0 equiv). It was cooled to 0° C. and added benzyl sulfonyl chloride (0.721 g, 4.1 mmol, 1.25 equiv). The reaction mixture was stirred at room temperature for 2 h. The reaction mixture filtered through a pad of Celite® and rinsed with DCM. The filtrate was concentrated under reduced pressure. The residue was purified by flash column chromatography on silica gel (CombiFlash®, 20% ethyl acetate in hexane) to afford 300.2. MS (ES): m/z 415.1 [M+H]+.

Synthesis of compound 300.3. To a solution of 300.2 (0.850 g, 2.05 mmol, 1.0 equiv) in DCM (10 mL) was added boron tribromide solution (1 M in DCM, 15 mL, 15.37 mmol, 7.5 equiv) at −78° C. and stirred for 3 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 45% ethyl acetate in hexane) to afford 300.3. MS (ES): m/z 401.0 [M+H]+.

Synthesis of compound 300.4. A mixture of 300.3 (0.640 g, 1.6 mmol, 1.0 equiv), zinc cyanide (0.131 g, 1.12 mmol, 0.7 equiv) in DMF (4 mL) and water (4 mL) was degassed by bubbling argon through for 10 min. Under argon atmosphere were added tris(dibenzylideneacetone)dipalladium(0) (0.073 g, 0.08 mmol, 0.05 equiv) and 1,1′-bis(diphenylphosphino)ferrocene (0.088 g, 0.16 mmol, 0.1 equiv), and degassed for 5 min. The reaction mixture was stirred at 120° C. for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 50% ethyl acetate in hexane eluant) to afford 300.4. MS (ES): m/z 300.2 [M+H]+.

Synthesis of compound 300.5. Compound 300.5 was prepared from compound 300.4 and Int-4, following the procedure described in the synthesis of 19.1. The product was used in the next step without purification. MS (ES): m/z 485.5 [M+H]+.

Synthesis of compound 300.6. To a solution of 300.5 (0.470 g, 0.969 mmol, 1.0 equiv) in isopropyl alcohol (5 mL) and water (2 mL) was added iron powder (0.271 g, 4.84 mmol, 5.0 equiv) followed by acetic acid (0.290 g, 4.84 mmol, 5.0 equiv). The reaction mixture was stirred at 100° C. for 1 h. The reaction mixture was concentrated under reduced pressure. This was transferred into saturated sodium bicarbonate and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.2% methanol in DCM) to afford 300.6. MS (ES): m/z 455.5 [M+H]+.

Synthesis of compound 300.7. Compound 300.7 was prepared from 300.6 and Int-63, following the procedure described in the synthesis of I-13. The product was purified by flash column chromatography on silica gel (CombiFlash®, 2.8% methanol in DCM). MS (ES): m/z 656.0 [M+H]+.

Synthesis of compound 300.8. A mixture of 300.7 (0.200 g, 0.305 mmol, 1.0 equiv), zinc dust (0.004 g, 0.061 mmol, 0.2 equiv) and zinc cyanide (0.178 g, 1.525 mmol, 5.0 equiv) in N,N-dimethylacetamide (8 mL) was degassed by bubbling argon through for 10 min. Under argon atmosphere tris(dibenzylideneacetone)dipalladium(0) (0.041 g, 0.045 mmol, 0.15 equiv) and 1,1′-bis(diphenylphosphino)ferrocene (0.050 g, 0.091 mmol, 0.30 equiv) were added, and degassed for 5 min. The reaction mixture was stirred at 220° C. in microwave for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.3% methanol in DCM) to afford 300.8. MS (ES): m/z 646.4 [M+H]+.

Synthesis of I-300. To a solution of 300.8 (0.060 g, 0.070 mmol, 1.0 equiv) in methanol (3 mL) was added 40% aqueous sodium hydroxide (0.5 mL) and stirred at room temperature for 30 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.5% methanol in DCM) to afford I-300. MS (ES): m/z 506.2 [M+H]+, $^1$H NMR (DMSO-$d_6$, 400 MHz): δ 10.09 (s, 1H), 9.12 (s, 1H), 8.75 (s, 1H), 8.67 (s, 1H), 8.54 (s, 1H), 8.23 (s, 1H), 8.06 (s, 1H), 7.52 (s, 1H), 4.00 (s, 3H), 3.67 (s, 3H).

Example 301: 7-chloro-N-(4-((4-ethyl-1,4-diazepan-1-yl)methyl)-3-(trifluoromethyl)phenyl)-1-methyl-6-(pyrazolo[1,5-a]pyrazin-3-yloxy)-1H-imidazo[4,5-b]pyridin-2-amine

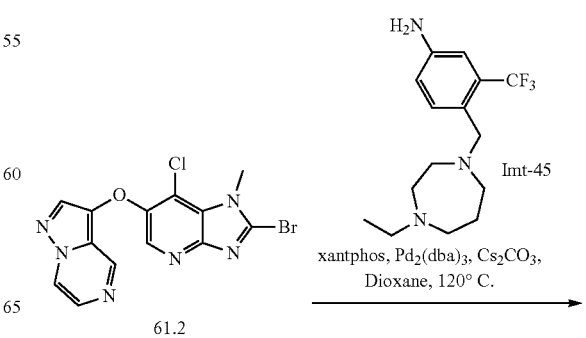

-continued

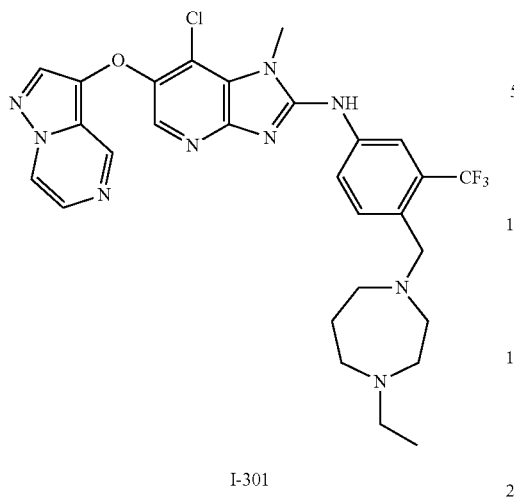

I-301

Synthesis of I-301. Compound I-301 was prepared from 61.2 and Int-145, following the procedure described in the synthesis of I-53. The product was purified by flash column chromatography on silica gel (CombiFlash®, 3.8% methanol in DCM). MS (ES): m/z 600.3 [M+H]$^+$, $^1$H NMR (DMSO-d$_6$, 400 MHz): δ 9.66 (s, 1H), 9.03 (s, 1H), 8.70-8.69 (d, J=4.8 Hz, 1H), 8.27 (s, 1H), 8.20 (s, 1H), 8.17 (s, 1H), 8.04 (s, 1H), 7.88-7.87 (d, J=4.4 Hz, 1H), 7.81-7.78 (d, J=8.4 Hz, 1H), 4.03 (s, 2H), 3.73 (s, 2H), 2.84 (s, 2H), 2.77 (s, 2H), 2.68-2.65 (m, 6H), 1.80 (s, 2H), 1.25 (s, 1H), 1.06-1.03 (m, 3H).

Example 302: 1-methyl-2-((1-methyl-2-oxo-5-(trifluoromethyl)-1,2-dihydropyridin-3-yl)amino)-6-((6-(methylamino)pyrazolo[1,5-a]pyridin-3-yl)oxy)-1H-imidazo[4,5-b]pyridine-7-carbonitrile

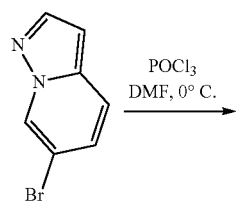

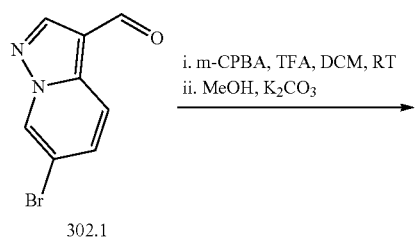
302.1

-continued

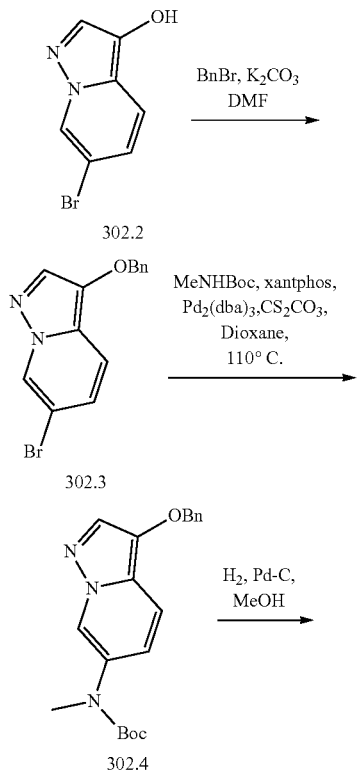

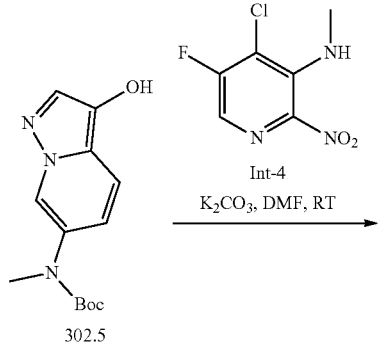

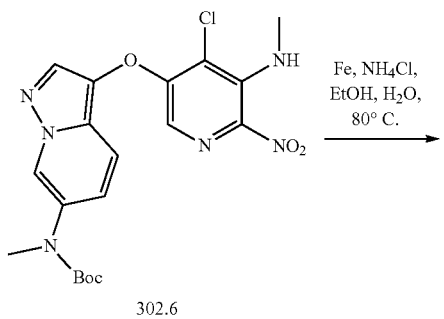
302.6

-continued

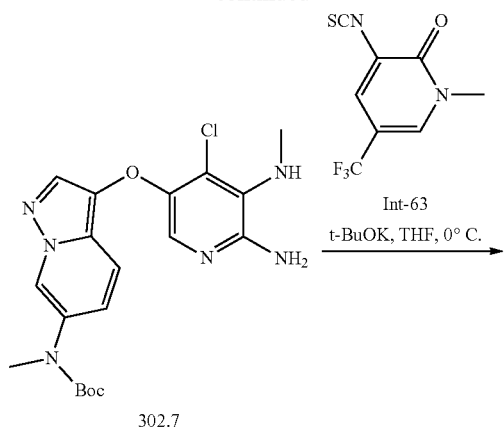

302.7

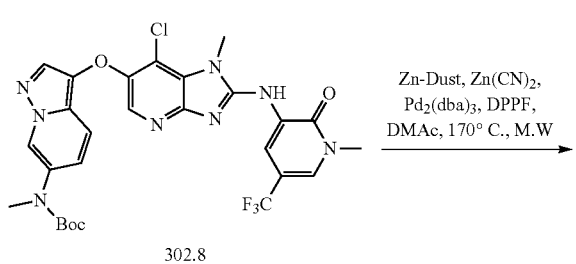

302.8

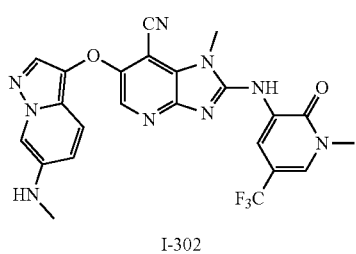

I-302

Synthesis of compound 302.1. To a solution of 6-bromopyrazolo[1,5-a]pyridine (5.0 g, 25.38 mmol, 1.0 equiv) in DMF (25 mL) was added phosphoryl chloride (11.6 g, 76.1 mmol, 3.0 equiv) and stirred at room temperature for 1 h. The reaction mixture was concentrated under reduced pressure. The residue was dissolved in DCM and washed with 2 N sodium hydroxide followed by brine. It was separated, dried over anhydrous sodium sulfate, filtered, and concentrated under reduced pressure. The residue was purified by flash column chromatography on silica gel (CombiFlash®, 15% ethyl acetate in hexane) to afford 302.1. MS (ES): m/z 226.0 $[M+H]^+$.

Synthesis of compound 302.2. To a solution of 302.1 (3.6 g, 16.0 mmol, 1.0 equiv) in DCM (17 mL) was added trifluoroacetic acid (1.2 mL, 1.6 mmol, 0.1 equiv)) at 0° C. followed by the addition of m-chloroperoxybenzoic acid (4.12 g, 24.0 mmol, 1.5 equiv). The reaction mixture was stirred at room temperature for 2 h. It was cooled to 0° C. and adjust pH to neutral by saturated sodium bicarbonate. The mixture was extracted with ethyl acetate. The combined organic layers were washed with aq. sodium bisulfite, dried over anhydrous sodium sulfate, filtered, and concentrated under reduced pressure. The residue was dissolve in methanol then added potassium carbonate (4.41 g, 32.0 mmol, 2.0 equiv). The reaction mixture was stirred at room temperature for 15 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 60% ethyl acetate in hexane) to afford 302.2. MS (ES): m/z 214.0 $[M+H]^+$.

Synthesis of compound 302.3. To a solution of 302.2 (2.3 g, 10.80 mmol, 1.0 equiv) in DMF (30 mL) was added potassium carbonate (4.4 g, 32.39 mmol, 3.0 equiv) stirred for 5 min before the addition of benzyl bromide (1.92 mL, 16.1 mmol, 3.0 equiv). The reaction mixture was stirred at room temperature for 2 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 8.0% ethyl acetate in hexane) to afford 302.3. MS (ES): m/z 304.1 $[M+H]^+$.

Synthesis of compound 302.4. A mixture of 302.3 (2.1 g, 6.93 mmol, 1.0 equiv), tert-butyl methylcarbamate (2.73 g, 20.78 mmol, 3.0 equiv) and cesium carbonate (0.830 g, 2.56 mmol, 3.0 equiv) in 1,4-dioxane (35 mL) was degassed by bubbling argon through for 10 min. Under argon atmosphere, 4,5-bis(diphenylphosphino)-9,9-dimethylxanthene (0.798 g, 1.3 mmol, 0.2 equiv) and tris(dibenzylideneacetone)dipalladium(0) (0.634 g, 0.693 mmol, 0.1 equiv) were added, and degassed for 5 min. The reaction mixture was stirred at 110° C. for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 302.4. MS (ES): m/z 354.2 $[M+H]^+$.

Synthesis of compound 302.5. A mixture of compound 302.4 (1.4 g, 3.96 mmol, 1.0 equiv) and 20% palladium hydroxide (0.800 g) in methanol (20 mL) and THF (20 mL) was stirred under hydrogen for 2 h. The reaction mixture was filtered through a pad of Celite® and rinsed with methanol. The filtrate was concentrated under reduced pressure to afford 302.5. MS (ES): m/z 264.1 $[M+H]^+$.

Synthesis of compound 302.6. Compound 302.6 was prepared from compound 302.5 and Int-4, following the procedure described in the synthesis of 19.1. The product was purified by flash column chromatography on silica gel (CombiFlash®, 40% ethyl acetate in hexane). MS (ES): m/z 449.6$[M+H]^+$.

Synthesis of compound 302.7. Compound 302.7 was prepared from 302.6 following the procedure described in the synthesis of 5.4. The product was purified by flash column chromatography on silica gel (CombiFlash®, 3.4% methanol in DCM). MS (ES): m/z 419.7 $[M+H]^+$.

Synthesis of compound 302.8. Compound 302.8 was prepared from 302.7 and Int-63, following the procedure described in the synthesis of I-13. The product was purified by flash column chromatography on silica gel (CombiFlash®, 3.6% methanol in DCM). MS (ES): m/z: 620.0 $[M+H]^+$.

Synthesis of compound I-302. Compound I-302 was prepared from 302.8 following the procedure described in the synthesis of I-157. The product was purified by flash column chromatography on silica gel (CombiFlash®, 4.5% methanol in DCM). MS (ES): m/z 510.2, $^1$H NMR (DMSO-$d_6$, 400 MHz): δ 8.96 (s, 1H), 8.62 (s, 1H), 8.17 (s, 1H), 7.93 (s, 1H), 7.84 (s, 1H), 7.63 (s, 1H), 7.31-7.28 (d, J=9.6 Hz, 1H), 5.75-5.74 (d, J=4.8 Hz, 1H), 6.87-6.85 (d, J=9.6 Hz, 1H), 3.99 (s, 3H), 3.66 (s, 3H), 2.70-2.69 (d, 3H).

Example 303: 3-((7-chloro-1-methyl-6-((6-(methyl-amino)pyrazolo[1,5-a]pyridin-3-yl)oxy)-1H-imidazo[4,5-b]pyridin-2-yl)amino)-1-methyl-5-(trifluoromethyl)pyridin-2(1H)-one

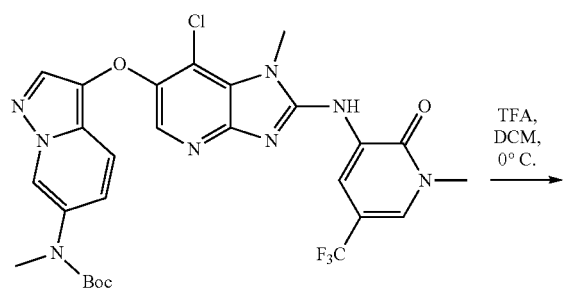

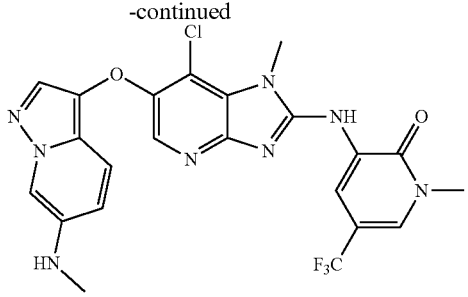

I-303

Synthesis of I-303. To a solution of 302.8 (0.050 g, 0.080 mmol, 1.0 equiv) in DCM (4 mL) was added trifluoracetic acid (0.5 mL) at 0° C. and stirred for 5 min. It was transferred into ice-saturated sodium bicarbonate solution and extracted with DCM. The combined organic layers were washed with brine, dried over anhydrous sodium sulfate, filtered, and concentrated under reduced pressure. The crude product was triturated with diethyl ether to afford I-303. MS (ES): m/z: 519.3 [M+H]$^+$, $^1$H NMR (DMSO-$d_6$, 400 MHz): δ 8.79 (s, 1H), 8.59 (s, 1H), 8.12 (s, 1H), 7.98 (s, 1H), 7.68 (s, 1H), 7.57 (s, 1H), 7.27-7.25 (d, J=9.6 Hz, 1H), 6.82-6.80 (d, J=9.2 Hz, 1H), 5.70-5.69 (d, J=4.8 Hz, 1H), 4.01 (s, 3H), 3.65 (s, 3H), 2.67-2.66 (d, 3H).

Example 304: 3-((7-chloro-1-methyl-6-((6-(methyl-amino)pyrazolo[1,5-a]pyrazin-3-yl)oxy)-1H-imidazo[4,5-b]pyridin-2-yl)amino)-1-methyl-5-(trifluoromethyl)pyridin-2(1H)-one

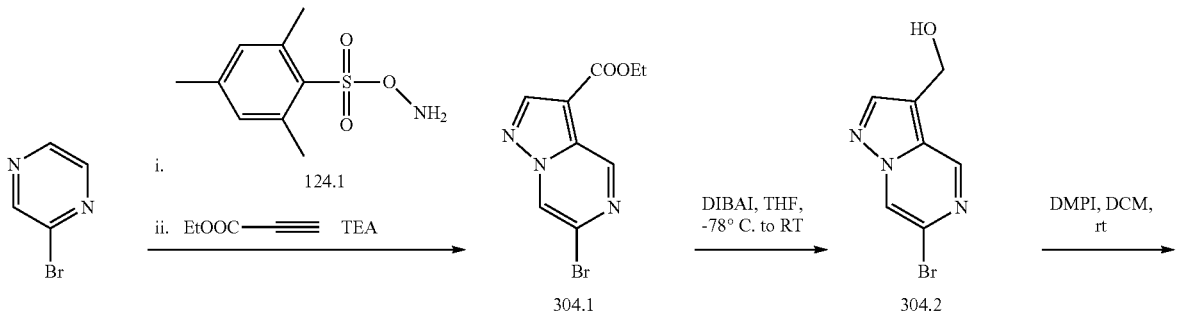

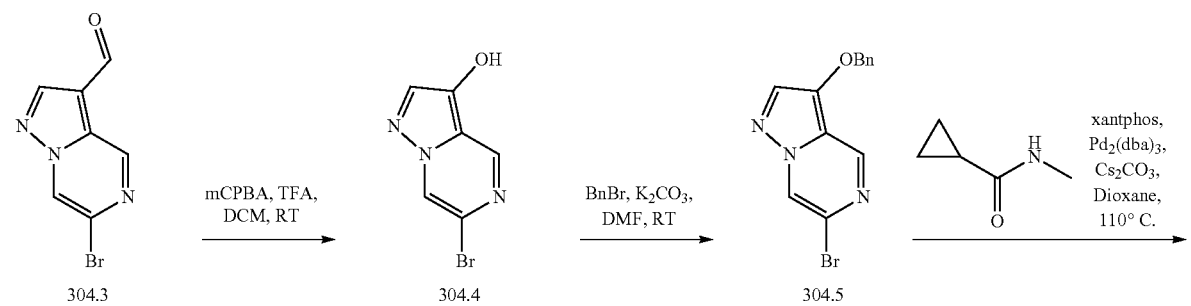

-continued

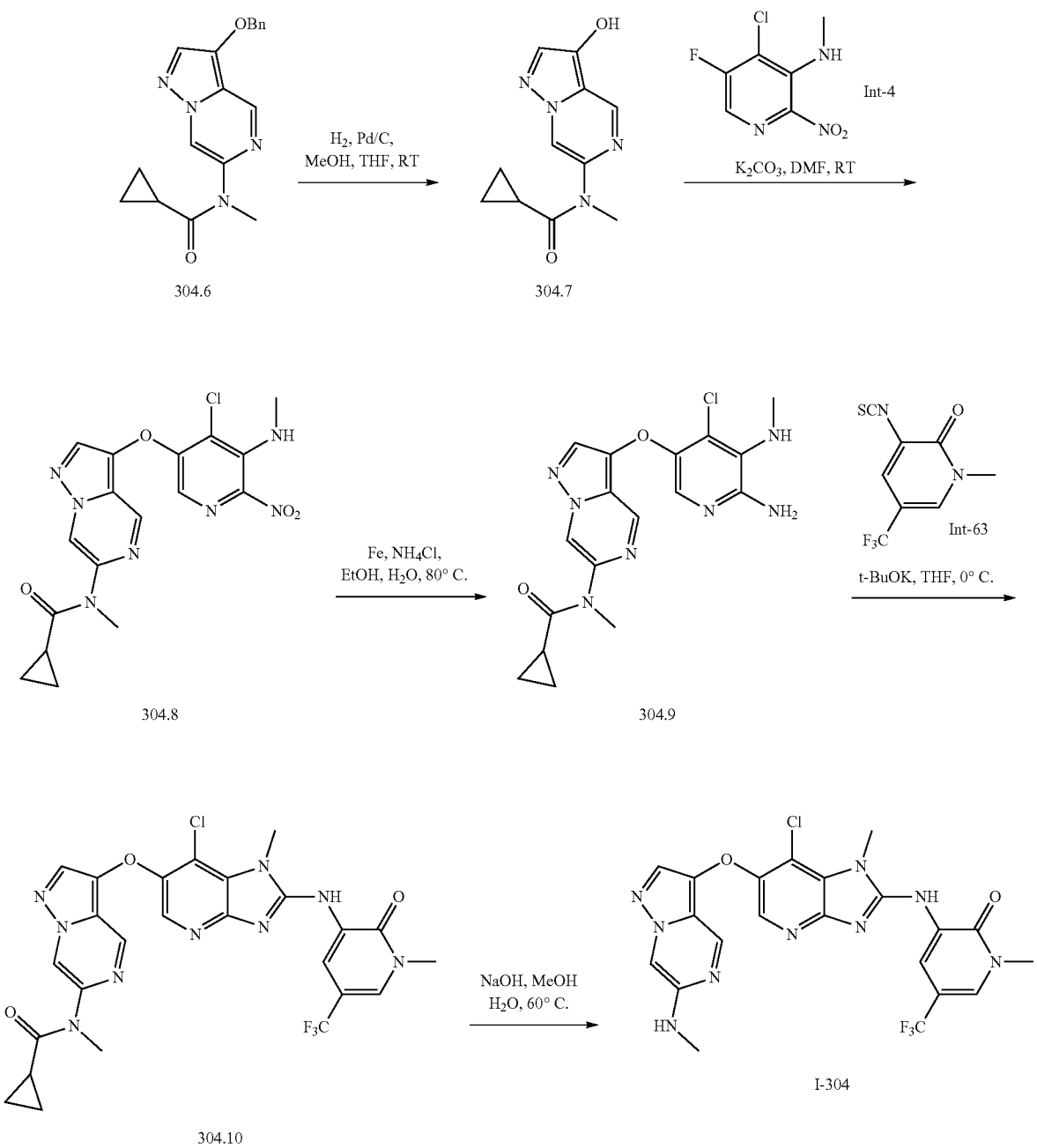

Synthesis of compound 304.1. To a solution of 2-bromopyrazine (432.0 g, 2720 mmol, 1.0 equiv) in DCM (5180 mL) was added 124.1 (701.9 g, 3260 mmol, 1.2 equiv) at 0° C. The reaction mixture was stirred at room temperature for 1 h. It was transferred into diethyl ether, stirred, and the precipitates were collected by filtration (691 g). To the solution of the residue in DMF (2160 mL) was added trimethylamine (372.2 g, 3685 mmol, 2.0 equiv) followed by ethyl propiolate (361.16 g, 3685 mmol, 2.0 equiv) at 0° C. The reaction mixture was stirred at room temperature for 48 h. It was poured into brine and extracted with ethyl acetate. The combined organic layers were washed with brine, dried over anhydrous sodium sulfate, filtered, and concentrated under reduced pressure. The residue was purified by flash column chromatography on silica gel (4% ethyl acetate in hexane) to afford 304.1. MS (ES): m/z 271.1 [M+H]+.

Synthesis of compound 304.2. To a solution of 304.1 (20.0 g, 74.05 mmol, 1.0 equiv) in THF (400 mL) was added diisobutylaluminum hydride (1 M solution in DCM, 222 mL, 222.15 mmol, 3.0 equiv) dropwise at −78° C. The reaction mixture was stirred at room temperature for 1 h. It was transferred into 2 M aqueous hydrochloric acid solution and extracted with ethyl acetate. The combined organic layers were washed with brine, dried over anhydrous sodium sulfate, filtered, and concentrated under reduced pressure to afford 304.2. MS (ES): m/z 229.2 [M+H]+.

Synthesis of compound 304.3. To a solution of 304.2 (12.3 g, 53.94 mmol, 1 equiv) in DCM was added Dess- Martin periodinane (45.84 g, 107.88 mmol, 2 equiv) at 0° C. and stirred for 1 h. The reaction mixture was transferred into aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 47% ethyl acetate in hexane) to afford 304.3. MS (ES): m/z 227 [M+H]$^+$.

Synthesis of compound 304.4. To a solution of 304.3 (7.7 g, 34.11 mmol, 1 equiv) in DCM (154 mL) was added m-chloroperbenzoic acid (60%) (8.7 g, 51.16, 1.5 equiv) and triflouroacetic acid (0.392 g, 3.4 mmol, 0.1 equiv) dropwise at 0° C. The reaction mixture was stirred at room temperature for 18 h. The reaction mixture was poured into aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 27% ethyl acetate in hexane) to afford 304.4. MS (ES): m/z 215.5 [M+H]$^+$.

Synthesis of compound 304.5. To a solution of 304.4 (3.7 g, 17.29 mmol, 1.0 equiv) and potassium carbonate (4.7 g, 34.58 mmol, 2.0 equiv) in DMF (55 mL) was added benzyl bromide (18.5 mL). The reaction mixture was stirred at room temperature for 2 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 8.0% ethyl acetate in hexane) to afford 304.5. MS (ES): m/z 305.3 [M+H]$^+$.

Synthesis of compound 304.6. A mixture of 304.5 (3.2 g, 10.52 mmol, 1.0 equiv), N-methylcyclopropanecarboxamide (2.6 g, 31.56 mmol, 3.0 equiv) and cesium carbonate (10.25 g, 31.56 mmol, 3.0 equiv) in 1,4-dioxane (30 mL) was degassed by bubbling argon through for 10 min. Under argon atmosphere, 4,5-bis(diphenylphosphino)-9,9-dimethylxanthene (1.2 g, 2.1 mmol, 0.2 equiv) and tris(dibenzylideneacetone)dipalladium(0) (0.962 g, 1.052 mmol, 0.1 equiv) were added, and degassed for 5 min. The reaction mixture was stirred at 120° C. for 30 min. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.1% methanol in DCM) to afford 304.6. MS (ES): m/z 323.5 [M+H]$^+$.

Synthesis of compound 304.7. A mixture of compound 304.6 (2.2 g, 6.82 mmol, 1.0 equiv) and 10% palladium on charcoal (1.1 g) in methanol:THF (1:1) (44 mL) was stirred under hydrogen (1 atm) for 4 h. It was filtered through a pad of Celite® and rinsed with methanol. The filtrate was concentrated under reduced pressure to afford 304.7. MS (ES): m/z 233.2 [M+H]$^+$.

Synthesis of compound 304.8. Compound 304.8 was prepared from compound 304.7 and Int-4, following the procedure described in the synthesis of 19.1. The product was purified by flash column chromatography on silica gel (CombiFlash®, 25% ethyl acetate in hexane). MS (ES): m/z 418.5 [M+H]$^+$.

Synthesis of compound 304.9. Compound 304.9 was prepared from 304.8 following the procedure described in the synthesis of 5.4. The product was purified by flash column chromatography on silica gel (CombiFlash®, 2.4% methanol in DCM). MS (ES): m/z 388.5 [M+H]$^+$.

Synthesis of compound 304.10. Compound 304.10 was prepared from 304.9 and Int-63, following the procedure described in the synthesis of I-13. The product was purified by flash column chromatography on silica gel (CombiFlash®, 2.4% methanol in DCM). MS (ES): m/z 588.6 [M+H]$^+$.

Synthesis of I-304. To a solution of 304.10 (0.030 g, 0.051 mmol, 1.0 equiv) in methanol (3 mL) was added a solution of sodium hydroxide (0.020 g, 0.51 mmol, 10 equiv) in water (2 mL) and stirred at room temperature for 30 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford I-304. MS (ES): m/z 520.2 [M+H]$^+$, $^1$H NMR (DMSO-d$_6$, 400 MHz): δ 8.78 (bs, 1H), 8.68 (s, 1H), 8.60 (s, 1H), 8.17 (s, 1H), 8.12 (s, 1H), 7.65 (s, 1H), 7.54 (s, 1H), 6.13 (bs, 1H), 4.00 (s, 3H), 3.65 (s, 3H), 2.71-2.70 (d, J=4.8 Hz, 3H).

Example 305: (S)-3-((7-chloro-1-methyl-6-((6-(methylamino)pyrazolo[1,5-a]pyrazin-3-yl)oxy)-1H-imidazo[4,5-b]pyridin-2-yl)amino)-1-(tetrahydrofuran-3-yl)-5-(trifluoromethyl)pyridin-2(1H)-one and (R)-3-((7-chloro-1-methyl-6-((6-(methylamino) pyrazolo[1,5-a]pyrazin-3-yl)oxy)-1H-imidazo[4,5-b] pyridin-2-yl)amino)-1-(tetrahydrofuran-3-yl)-5-(trifluoromethyl)pyridin-2(1H)-one

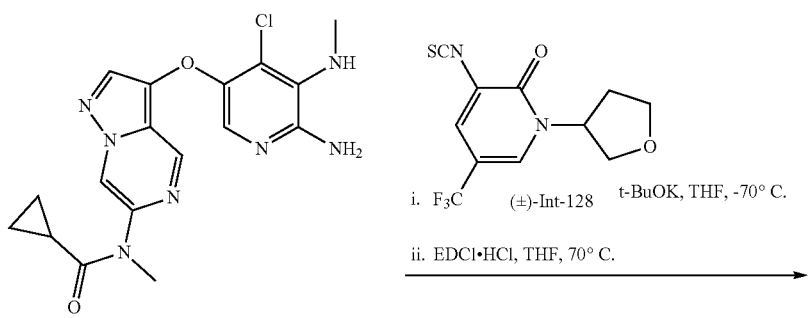

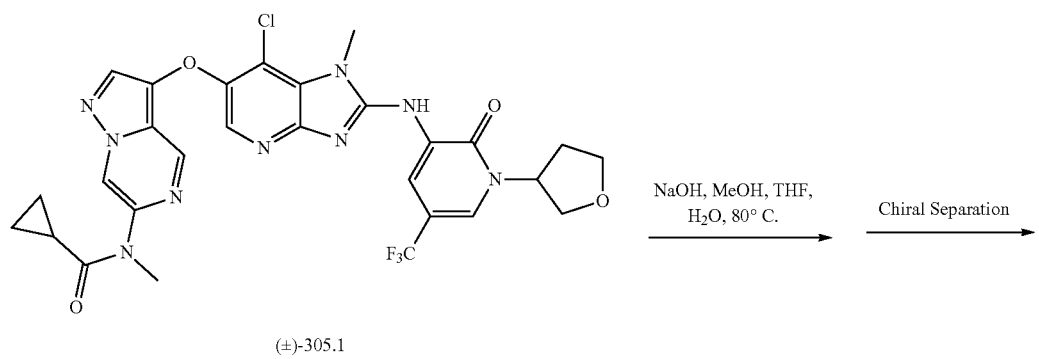

(±)-305.1

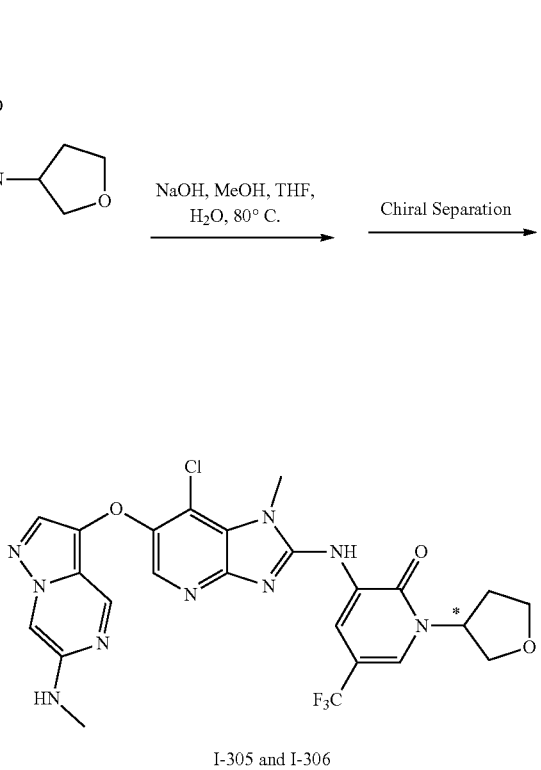

I-305 and I-306

Synthesis of compound (±)-305.1. Compound (±)-305.1 was prepared from 304.9 and (±)-Int-128, following the procedure described in the synthesis of I-51. The product was purified by flash column chromatography on silica gel (CombiFlash®, 4.5% methanol in DCM). MS (ES): m/z 645.0 [M+H]⁺.

Synthesis of compound I-305 and I-306. The racemate was prepared from (±)-305.1 following the procedure described in the synthesis of I-304. The product was purified by flash column chromatography on silica gel (Combi-Flash®, 2.5% methanol in DCM). The enantiomers were separated by HPLC (column: CHIRALPAK IB-N (250 mm*21 mm, 5 μm); mobile phase: (A) 0.1% DEA in n-hexane, (B) 0.1% DEA in propan-2-ol:acetonitrile (70:30); flow rate: 20 mL/min) to afford first eluting fraction (I-305) and second eluting fraction (I-306). (*Absolute stereochemistry not determined.)

I-305: MS (ES): m/z 576.3 [M+H]⁺, ¹H NMR (DMSO-d₆, 400 MHz): δ 8.84 (s, 1H), 8.70 (s, 1H), 8.61 (s, 1H), 8.18 (s, 1H), 7.73 (s, 1H), 7.66 (s, 1H), 7.56 (s, 1H), 6.15-6.14 (d, J=4.8 Hz, 1H), 5.49 (bs, 1H), 4.11-4.06 (m, 2H), 4.01 (s, 3H), 3.92-3.90 (m, 1H), 3.80-3.78 (m, 1H), 2.72-2.71 (d, 3H), 2.14 (bs, 2H).

I-306: MS (ES): m/z 576.2 [M+H]⁺, ¹H NMR (DMSO-d₆, 400 MHz): δ 8.88 (s, 1H), 8.69 (s, 1H), 8.60 (s, 1H), 8.18 (s, 1H), 7.73 (s, 1H), 7.65 (s, 1H), 7.55 (s, 1H), 6.16-6.15 (d, J=4.8 Hz, 1H), 5.47 (bs, 1H), 4.13-4.08 (m, 2H), 4.01 (s, 3H), 3.96-3.88 (m, 1H), 3.81-3.75 (m, 1H), 2.71-2.70 (d, 3H), 2.15 (bs, 2H).

Example 307: (S)-7-chloro-N-(3-((3-methoxypyrrolidin-1-yl)methyl)-5-(trifluoromethyl)phenyl)-1-methyl-6-((6-(methylamino)pyrazolo[1,5-a]pyrazin-3-yl)oxy)-1H-imidazo[4,5-b]pyridin-2-amine

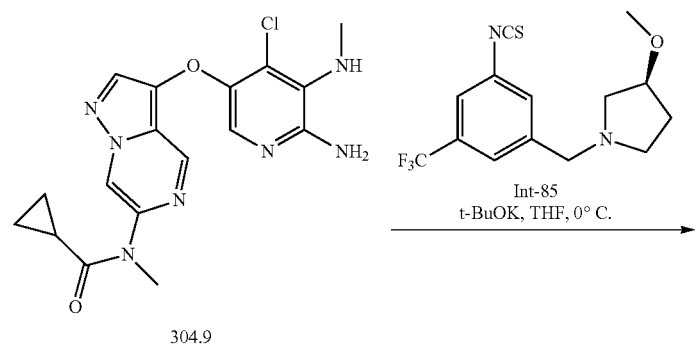

304.9

-continued

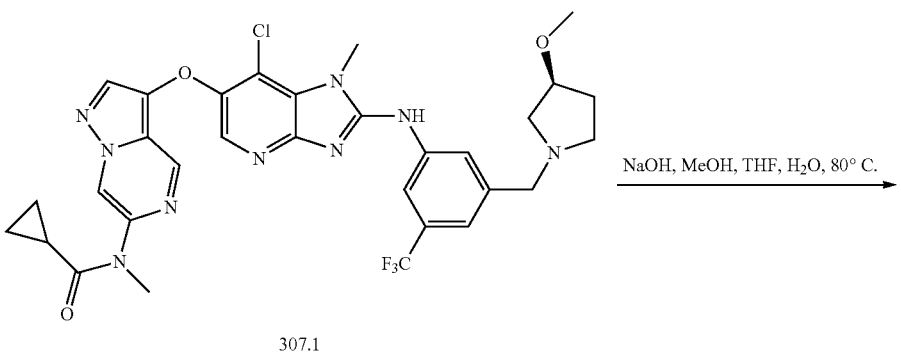

307.1

NaOH, MeOH, THF, H₂O, 80° C.

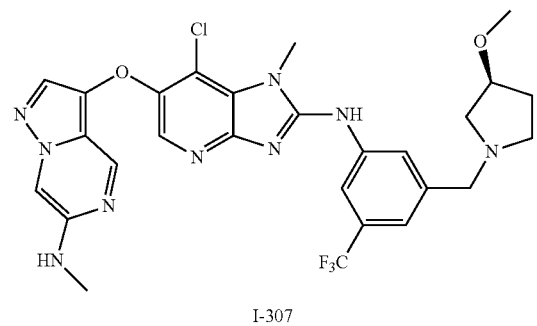

I-307

Synthesis of compound 307.1. Compound 307.1 was prepared from 304.9 and Int-85, following the procedure described in the synthesis of I-13. The product was purified by flash column chromatography on silica gel (Combi-Flash®, 2.5% methanol in DCM). MS (ES): m/z 671.0 [M+H]⁺.

Synthesis of I-307. Compound I-307 was prepared from 307.1 following the procedure described in the synthesis of I-304. The product was purified by flash column chromatography on silica gel (CombiFlash®, 3.9% methanol in DCM). MS (ES): m/z 602.4 [M+H]⁺, ¹H NMR (DMSO-d₆, 400 MHz): δ 9.66 (s, 1H), 8.67 (s, 1H), 8.34 (s, 1H), 8.13 (s, 1H), 8.05 (s, 1H), 7.63 (s, 1H), 7.54 (s, 1H), 7.28 (s, 1H), 6.14-6.13 (d, J=5.2 Hz, 1H), 4.02 (s, 3H), 3.91 (bs, 1H), 3.67 (bs, 2H), 3.16 (s, 3H), 2.71-2.70 (d, 3H), 2.67 (bs, 2H), 2.02-2.01 (m, 2H), 1.60 (bs, 2H).

Example 308: (R)-7-chloro-N-(3-((3-methoxypyrrolidin-1-yl)methyl)-5-(trifluoromethyl)phenyl)-1-methyl-6-((6-(methylamino)pyrazolo[1,5-a]pyrazin-3-yl)oxy)-1H-imidazo[4,5-b]pyridin-2-amine

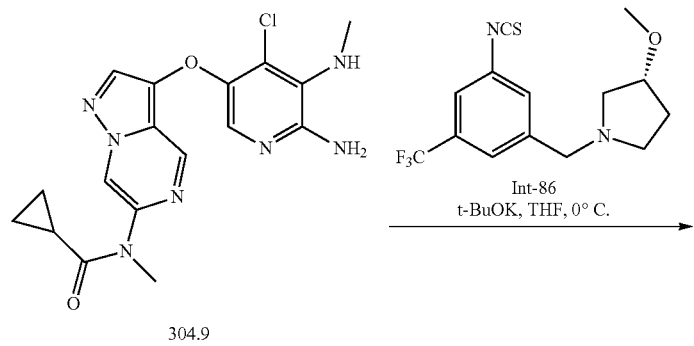

304.9

Int-86
t-BuOK, THF, 0° C.

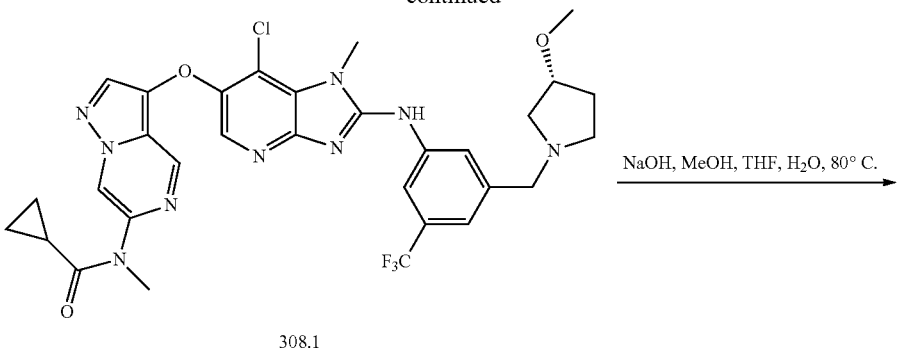

308.1

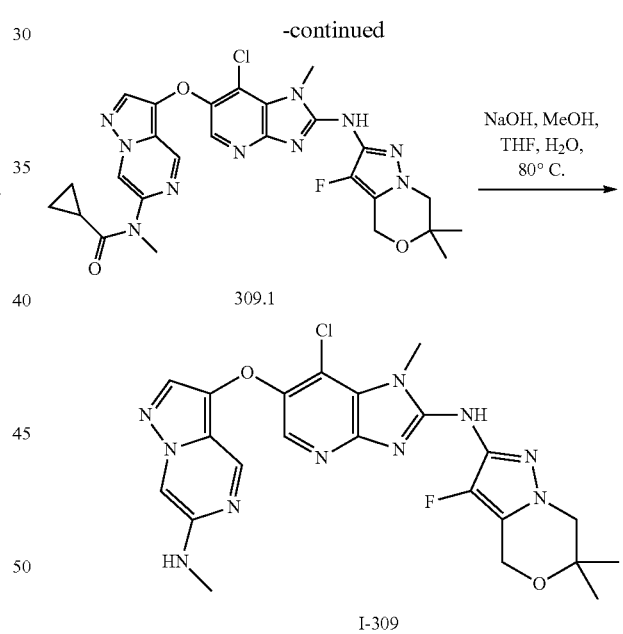

Synthesis of compound 308.1. Compound 308.1 was prepared from 304.9 and Int-86, following the procedure described in the synthesis of I-13. The product was purified by flash column chromatography on silica gel (CombiFlash®, 2.0% methanol in DCM). MS (ES): m/z 671.90 [M+H]$^+$.

Synthesis of I-308. Compound I-308 was prepared from 308.1 following the procedure described in the synthesis of I-304. The product was purified by flash column chromatography on silica gel (CombiFlash®, 3.0% methanol in DCM). MS (ES): m/z 603.4 [M+H]$^+$, $^1$H NMR (DMSO-d$_6$, 400 MHz): δ 9.66 (s, 1H), 8.67 (s, 1H), 8.34 (s, 1H), 8.13 (s, 1H), 8.05 (s, 1H), 7.63 (s, 1H), 7.54 (s, 1H), 7.27 (s, 1H), 6.15-6.13 (d, J=5.2 Hz, 1H), 4.02 (s, 3H), 3.90 (bs, 1H), 3.67 (s, 2H), 3.16 (s, 3H), 2.71-2.70 (d, 3H), 2.0 (bs, 2H), 1.60 (bs, 2H) 1.23 (bs, 2H).

Example 309: N-(7-chloro-1-methyl-6-((6-(methylamino)pyrazolo[1,5-a]pyrazin-3-yl)oxy)-1H-imidazo[4,5-b]pyridin-2-yl)-3-fluoro-6,6-dimethyl-6,7-dihydro-4H-pyrazolo[5,1-c][1,4]oxazin-2-amine

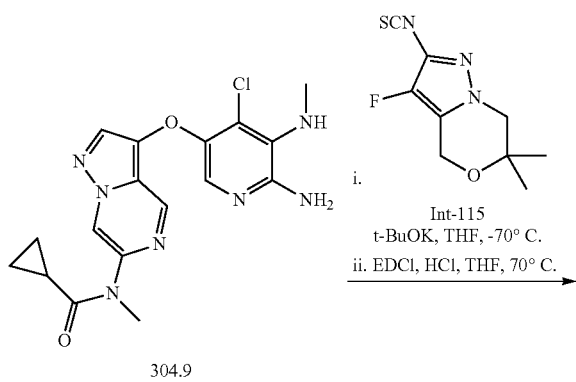

Synthesis of compound 309.1. Compound 309.1 was prepared from 304.9 and Int-115, following the procedure described in the synthesis of I-51. The product was purified by flash column chromatography on silica gel (CombiFlash®, 2.1% methanol in DCM). MS (ES): m/z 581.9 [M+H]$^+$.

Synthesis of I-309. Compound I-309 was prepared from 309.1 following the procedure described in the synthesis of I-304. The product was purified by flash column chromatography on silica gel (CombiFlash®, 2.5% methanol in DCM). MS (ES): m/z 513.2 [M+H]$^+$, $^1$H NMR (DMSO-d$_6$, 400 MHz): δ 9.56 (s, 1H), 8.69 (s, 1H), 8.08 (s, 1H), 7.54 (s, 1H), 7.08 (s, 1H), 6.14 (bs, 1H), 4.88 (s, 2H), 3.96 (s, 3H), 3.88 (s, 2H), 2.72-2.71 (d, 3H), 1.34 (s, 6H).

Example 310: N-(1-(2-oxaspiro[3.3]heptan-6-yl)-5-(trifluoromethyl)-1H-pyrazol-3-yl)-7-chloro-1-methyl-6-((6-(methylamino)pyrazolo[1,5-a]pyrazin-3-yl)oxy)-1H-imidazo[4,5-b]pyridin-2-amine

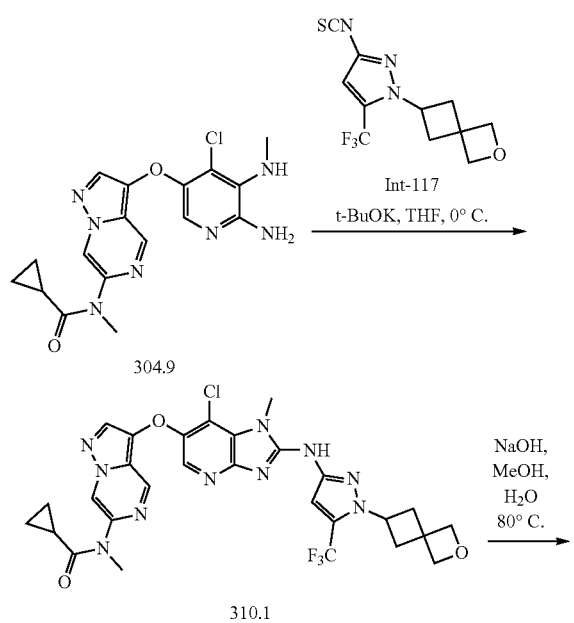

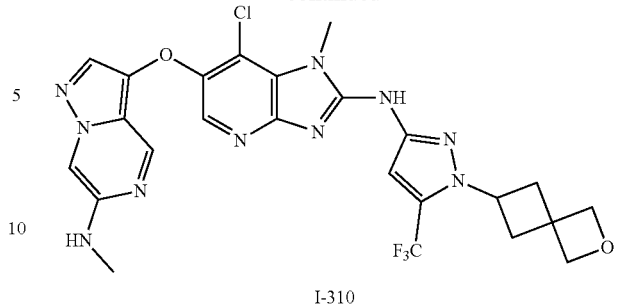

Synthesis of compound 310.1. Compound 310.1 was prepared from 304.9 and Int-117, following the procedure described in the synthesis of I-13. The product was purified by flash column chromatography on silica gel (CombiFlash®, 2.0% methanol in dichloromethane) to afford 310.1. MS (ES): m/z 644.03 [M+H]$^+$.

Synthesis of I-310. Compound I-310 was prepared from 310.1 following the procedure described in the synthesis of I-304. The product was purified by flash column chromatography on silica gel (CombiFlash®, 3.8% methanol in DCM) to afford I-310. MS (ES): m/z 575.6 [M+H]$^+$, $^1$H NMR (DMSO-d$_6$, 400 MHz): δ 11.97 (s, 1H), 8.69 (s, 1H), 7.88 (s, 1H), 7.69 (s, 1H), 7.56 (s, 1H), 6.59 (bs, 1H), 6.16-6.15 (d, J=4.8 Hz, 1H), 5.01 (bs, 1H), 4.70 (s, 2H), 4.59 (s, 2H), 3.80 (s, 3H), 2.72-2.71 (d, 3H), 2.34 (bs, 2H), 1.25 (bs, 2H).

Example 311: 6-((7-chloro-1-methyl-6-((6-(methylamino)pyrazolo[1,5-a]pyrazin-3-yl)oxy)-1H-imidazo[4,5-b]pyridin-2-yl)amino)-2,3,3-trimethyl-4-(trifluoromethyl)isoindolin-1-one

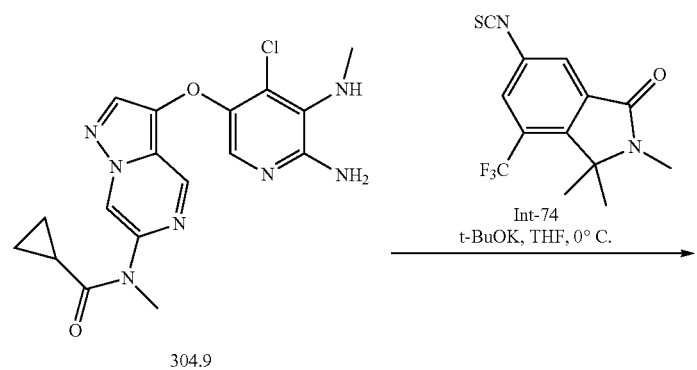

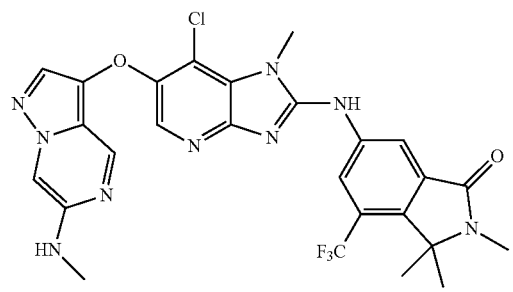

I-311

Synthesis of compound 311.1. Compound 311.1 was prepared from 304.9 and Int-74, following the procedure described in the synthesis of I-13. The product was purified by flash column chromatography on silica gel (Combi-Flash®, 3.1% methanol in DCM). MS (ES): m/z 655.0 [M+H]⁺.

Synthesis of I-311. Compound I-311 was prepared from 311.1 following the procedure described in the synthesis of I-304. The product was purified by flash column chromatography on silica gel (CombiFlash®, 6.8% methanol in DCM). MS (ES): m/z 586.3 [M+H]⁺, ¹H NMR (DMSO-d₆, 400 MHz): δ 9.89 (s, 1H), 8.72 (s, 1H), 8.70-8.69 (d, J=1.2 Hz, 1H), 8.47 (s, 1H), 8.25-8.10 (m, 1H), 7.65 (s, 1H), 7.56-7.55 (d, J=1.2 Hz, 1H), 6.15-6.13 (d, J=5.2 Hz, 1H), 4.06 (s, 3H), 3.00 (s, 3H), 2.73-2.71 (d, 3H), 1.54 (s, 6H).

Example 312: 3-((7-chloro-1-methyl-6-((6-(methyl-amino)pyrazolo[1,5-a]pyrazin-3-yl)oxy)-1H-imidazo[4,5-b]pyridin-2-yl)amino)-5-cyclopropyl-1-methylpyridin-2(1H)-one

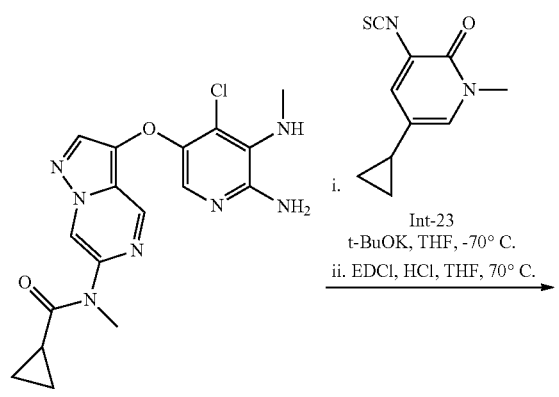

304.9

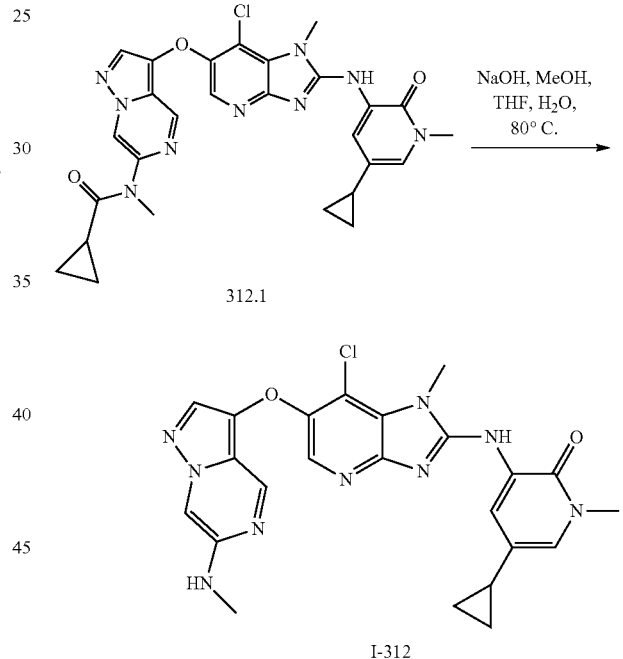

312.1

I-312

Synthesis of compound 312.1. Compound 312.1 was prepared from 304.9 and Int-23, following the procedure described in the synthesis of I-51. The product was purified by flash column chromatography on silica gel (Combi-Flash®, 2.7% methanol in DCM). MS (ES): m/z 561.2 [M+H]⁺.

Synthesis of I-312. Compound I-312 was prepared from 312.1 following the procedure described in the synthesis of I-304. The product was purified by flash column chromatography on silica gel (CombiFlash®, 2.0% methanol in DCM). MS (ES): m/z 493.1 [M+H]⁺, ¹H NMR (DMSO-d₆, 400 MHz): δ 8.68 (s, 1H), 8.50 (s, 1H), 8.28 (s, 1H), 8.14 (s, 1H), 7.64 (s, 1H), 7.54 (s, 1H), 7.23 (s, 1H), 6.15-6.14 (d, J=5.2 Hz, 1H), 3.98 (s, 3H), 3.55 (s, 3H), 2.71-2.70 (d, 3H), 1.23 (bs, 1H), 0.87-0.85 (m, 2H), 0.58-0.57 (m, 2H).

Example 313: 3-((7-chloro-1-methyl-6-((6-(methyl-amino)pyrazolo[1,5-a]pyrazin-3-yl)oxy)-1H-imidazo[4,5-b]pyridin-2-yl)amino)-1-isopropyl-5-(trifluoromethyl)pyridin-2(1H)-one

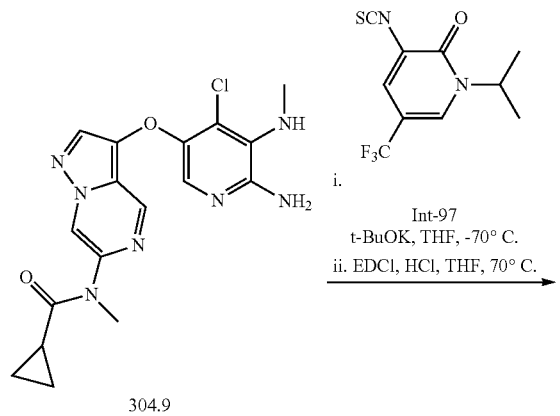

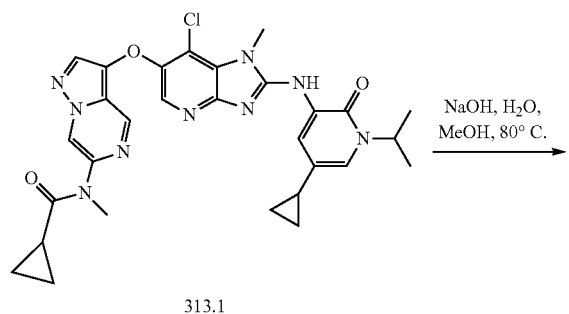

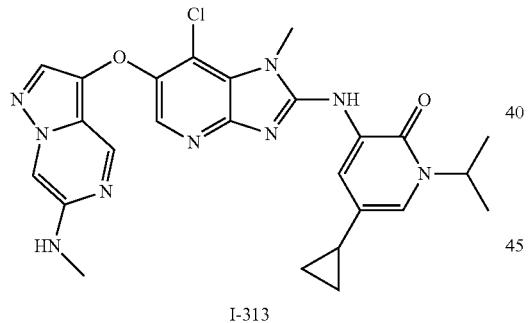

Example 314: (S)-7-chloro-1-methyl-6-((6-(methyl-amino)pyrazolo[1,5-a]pyrazin-3-yl)oxy)-N-(3-((1-methylpyrrolidin-3-yl)oxy)-5-(trifluoromethyl)phenyl)-1H-imidazo[4,5-b]pyridin-2-amine

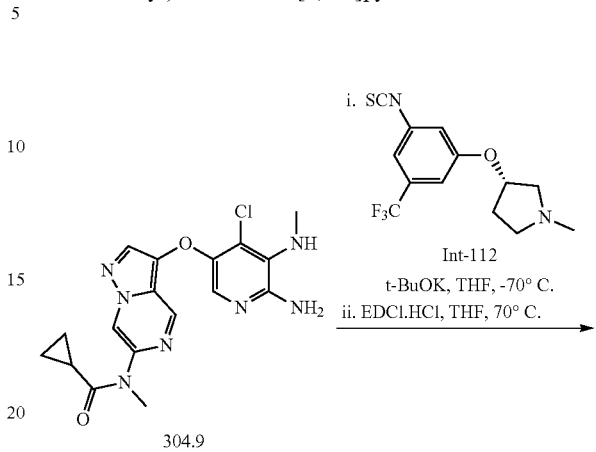

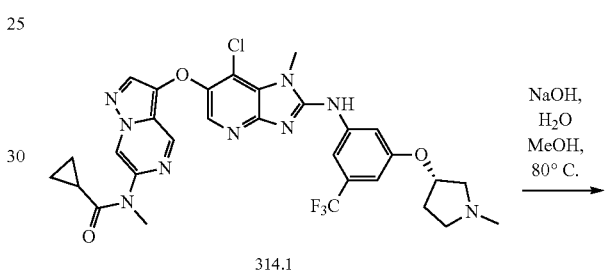

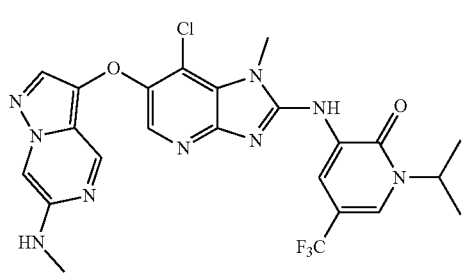

Synthesis of compound 313.1. Compound 313.1 was prepared from 304.9 and Int-97, following the procedure described in the synthesis of I-51. The product was purified by flash column chromatography on silica gel (CombiFlash®, 2.7% methanol in DCM). MS (ES): m/z 617.0 [M+H]+.

Synthesis of I-313. Compound I-313 was prepared from 313.1 following the procedure described in the synthesis of I-304. The product was purified by flash column chromatography on silica gel (CombiFlash®, 4.0% methanol in DCM). MS (ES): m/z 548.2 [M+H]+, $^1$H NMR (DMSO-$d_6$, 400 MHz): δ 8.85 (s, 1H), 8.71 (s, 1H), 8.62-8.61 (d, J=2.0 Hz, 1H), 8.19 (s, 1H), 8.00 (s, 1H), 7.67 (s, 1H), 7.56 (s, 1H), 6.17-6.15 (d, J=4.8 Hz, 1H), 5.20-5.17 (m, 1H), 4.03 (s, 3H), 2.73-2.72 (d, 3H), 1.46-1.44 (d, 6H).

Synthesis of compound 314.1. Compound 314.1 was prepared from 304.9 and Int-112, following the procedure described in the synthesis of I-51. The product was purified by flash column chromatography on silica gel (CombiFlash®, 13.0% methanol in DCM) to afford 1.2 (0.062 g, Yield: 91.63%). MS (ES): m/z 657.1 [M+H]+.

Synthesis of I-314. Compound I-314 was prepared from 314.1 following the procedure described in the synthesis of I-304. The product was purified by flash column chromatography on silica gel (CombiFlash®, 14% methanol in DCM). MS (ES): m/z 588.3 [M+H]+, $^1$H NMR (DMSO-$d_6$, 400 MHz): 9.64 (s, 1H), 8.67 (s, 1H), 8.14 (s, 1H), 7.94 (s, 1H), 7.84 (s, 1H), 7.63 (s, 1H), 7.54 (s, 1H), 6.84 (s, 1H), 6.14 (s, 1H), 4.99 (b s, 1H), 4.02 (s, 3H), 2.91 (bs, 2H), 2.78 (bs, 2H), 2.71-2.70 (d, 3H), 2.35 (s, 3H), 1.91-1.88 (m, 2H).

Example 315: (R)-7-chloro-1-methyl-6-((6-(methyl-amino)pyrazolo[1,5-a]pyrazin-3-yl)oxy)-N-(3-((1-methylpyrrolidin-3-yl)oxy)-5-(trifluoromethyl)phenyl)-1H-imidazo[4,5-b]pyridin-2-amine Synthesis of I-315. Compound I-315 was prepared from 315.1 following the procedure described in the synthesis of I-304. The product was purified by flash column chromatography on silica gel (CombiFlash®, 14% methanol in DCM). MS (ES): m/z 588.3 [M+H]+, 1H NMR (DMSO-d6,

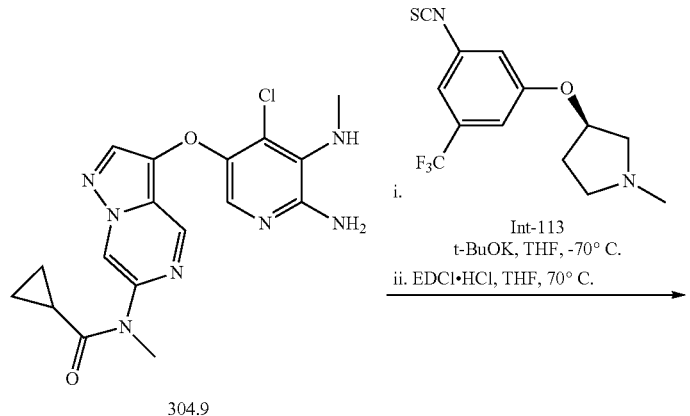

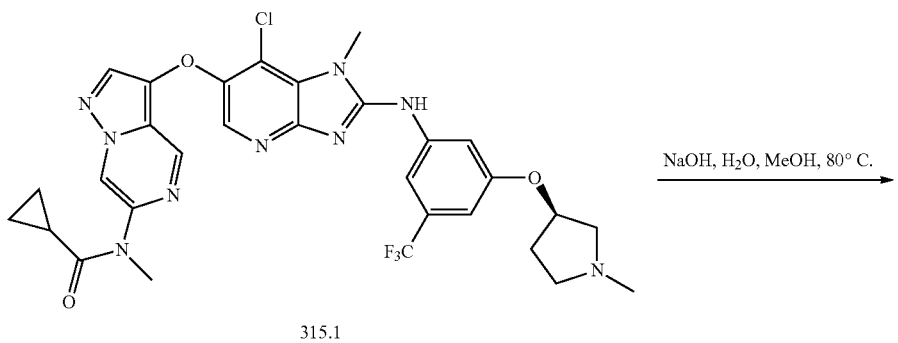

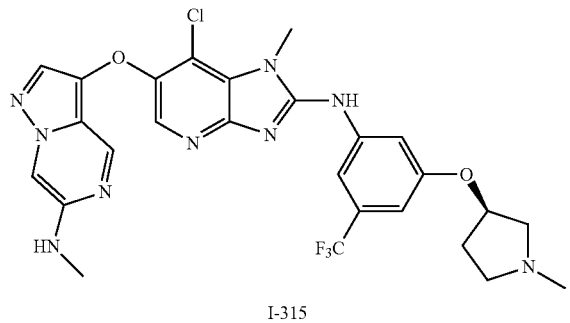

Synthesis of compound 315.1. Compound 315.1 was prepared from 304.9 and Int-113, following the procedure described in the synthesis of I-51. The product was purified by flash column chromatography on silica gel (CombiFlash®, 13.0% methanol in DCM. MS (ES): m/z 657.3 [M+H]+.

400 MHz): 9.63 (s, 1H), 8.69 (s, 1H), 8.16 (s, 1H), 7.94 (s, 1H), 7.86 (s, 1H), 7.64 (s, 1H), 7.56 (s, 1H), 6.84 (s, 1H), 6.15-6.14 (d, J=4.8 Hz, 1H), 4.98 (bs, 1H), 4.04 (s, 3H), 2.91 (bs, 2H), 2.78 (bs, 2H), 2.73-2.72 (d, 3H), 2.32 (s, 3H), 1.92-1.87 (m, 2H).

Example 316: 7-chloro-1-methyl-6-((6-(methyl-amino)pyrazolo[1,5-a]pyrazin-3-yl)oxy)-N-(3-(pyrrolidin-1-ylmethyl)-5-(trifluoromethyl)phenyl)-1H-imidazo[4,5-b]pyridin-2-amine Synthesis of I-316. Compound I-316 was prepared from 316.1 following the procedure described in the synthesis of I-304. The product was purified by flash column chromatography on silica gel (CombiFlash®, 8% methanol in

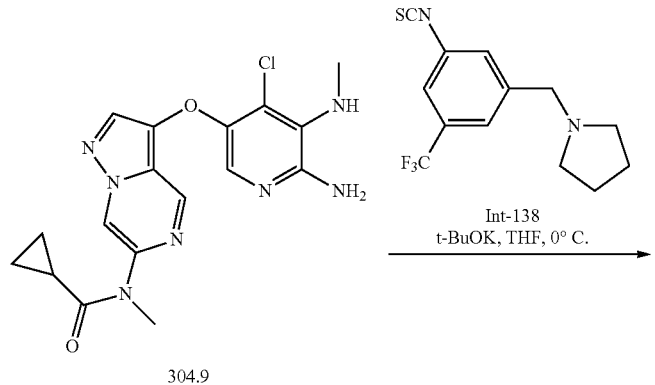

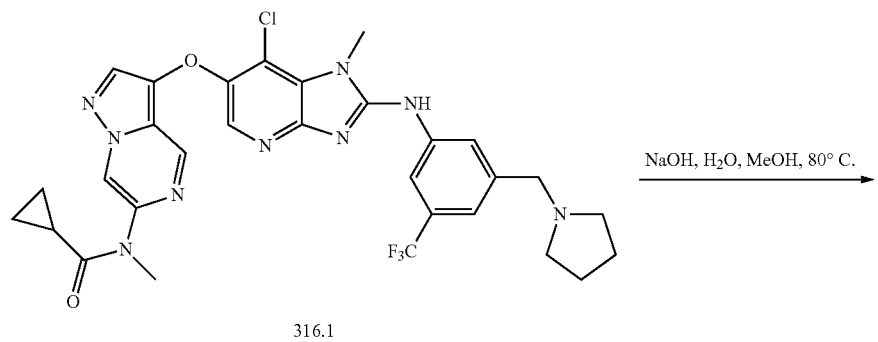

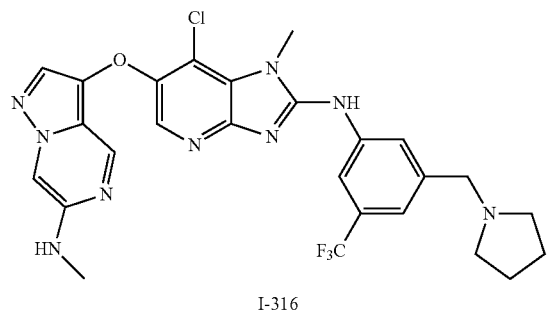

Synthesis of compound 316.1. Compound 316.1 was prepared from 304.9 and Int-138, following the procedure described in the synthesis of I-13. The product was purified by flash column chromatography on silica gel (CombiFlash®, 3.8% methanol in DCM). MS (ES): m/z 641.1 [M+H]$^+$.

DCM). MS (ES): m/z 572.3 [M+H]$^+$, $^1$H NMR (DMSO-d$_6$, 400 MHz): 9.61 (s, 1H), 8.67 (s, 1H), 8.28 (s, 1H), 8.13 (bs, 2H), 7.74 (s, 1H), 7.62 (s, 1H), 7.54 (s, 1H), 6.14 (s, 1H), 4.01 (s, 3H), 3.70 (bs, 2H), 2.71-2.70 (d, J=4.4 Hz, 3H), 1.73 (bs, 4H), 1.33-1.23 (m, 4H).

1013

Example 317: 4-((7-chloro-1-methyl-6-((6-(methyl-amino)pyrazolo[1,5-a]pyrazin-3-yl)oxy)-1H-imidazo[4,5-b]pyridin-2-yl)amino)-6-cyclopropyl-2-methylpyridazin-3(2H)-one

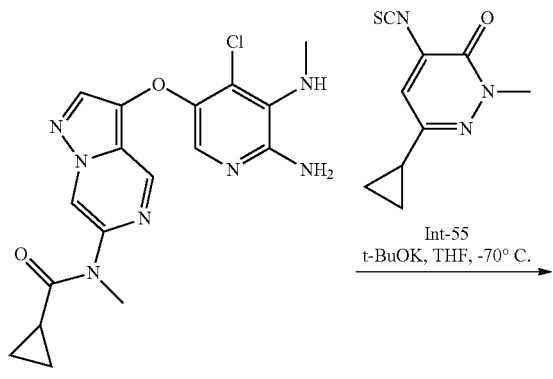

304.9

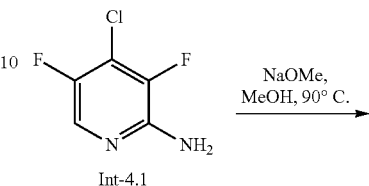

Int-55
t-BuOK, THF, -70° C.

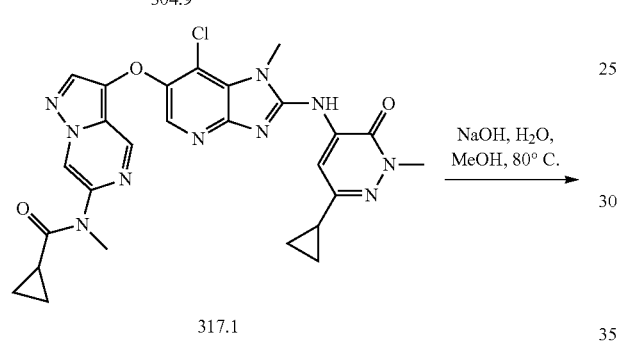

317.1

NaOH, H₂O, MeOH, 80° C.

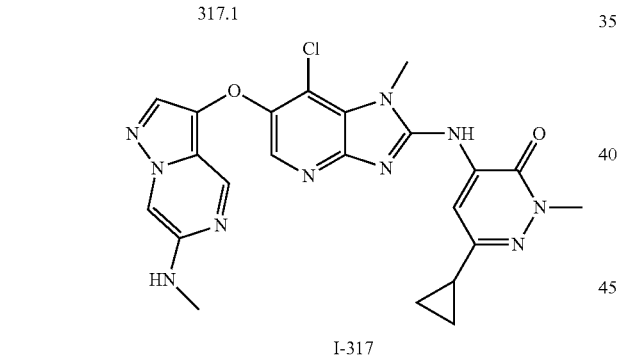

I-317

Synthesis of compound 317.1. Compound 317.1 was prepared from 304.9 and Int-55, following the procedure described in the synthesis of I-13. The product was purified by flash column chromatography on silica gel (Combi-Flash®, 2.6% methanol in DCM). MS (ES): m/z 562.1 [M+H]⁺.

Synthesis of I-317. Compound I-317 was prepared from 317.1 following the procedure described in the synthesis of I-304. The product was purified by flash column chromatography on silica gel (CombiFlash®, 4.1% methanol in DCM). MS (ES): m/z 493.2 [M+H]⁺, ¹H NMR (DMSO-d₆, 400 MHz): 9.21 (s, 1H), 8.70 (s, 1H), 8.22 (s, 1H), 7.97 (s, 1H), 7.67 (s, 1H), 7.55 (s, 1H), 6.16 (s, 1H), 4.01 (s, 3H), 3.70 (s, 3H), 2.71-2.70 (d, 3H), 1.99 (bs, 1H), 0.96-0.94 (m, 2H), 0.80 (bs, 2H).

1014

Example 318: 3-((7-methoxy-1-methyl-6-((6-(methylamino)pyrazolo[1,5-a]pyrazin-3-yl)oxy)-1H-imidazo[4,5-b]pyridin-2-yl)amino)-1-methyl-5-(trifluoromethyl)pyridin-2(1H)-one

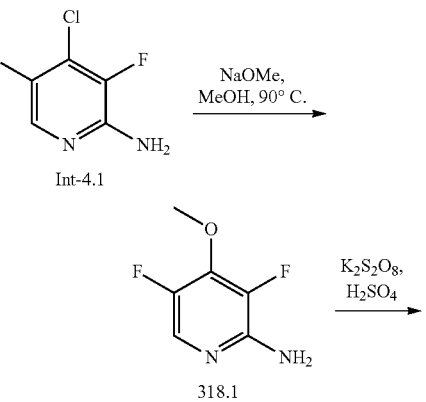

Int-4.1

NaOMe, MeOH, 90° C.

318.1

K₂S₂O₈, H₂SO₄

318.2 aq. MeNH₂, ACN, RT

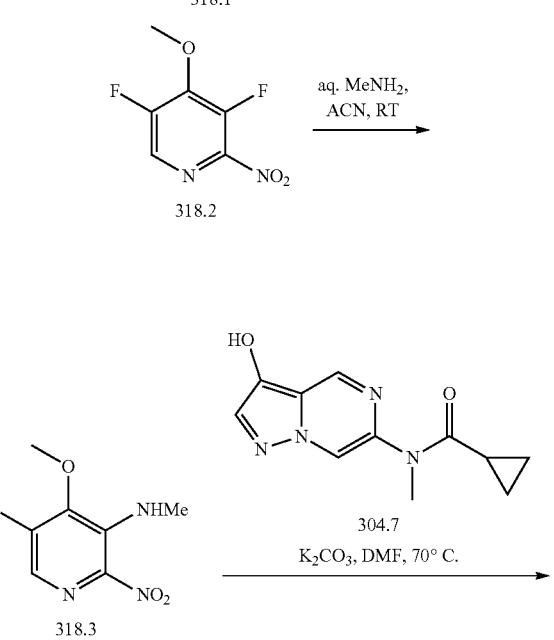

318.3

K₂CO₃, DMF, 70° C.

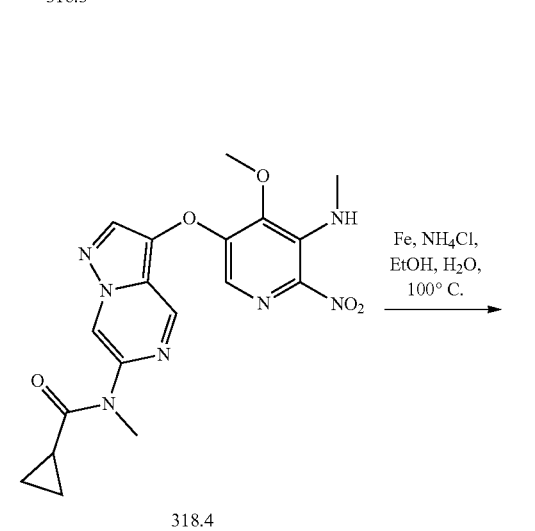

318.4

Fe, NH₄Cl, EtOH, H₂O, 100° C.

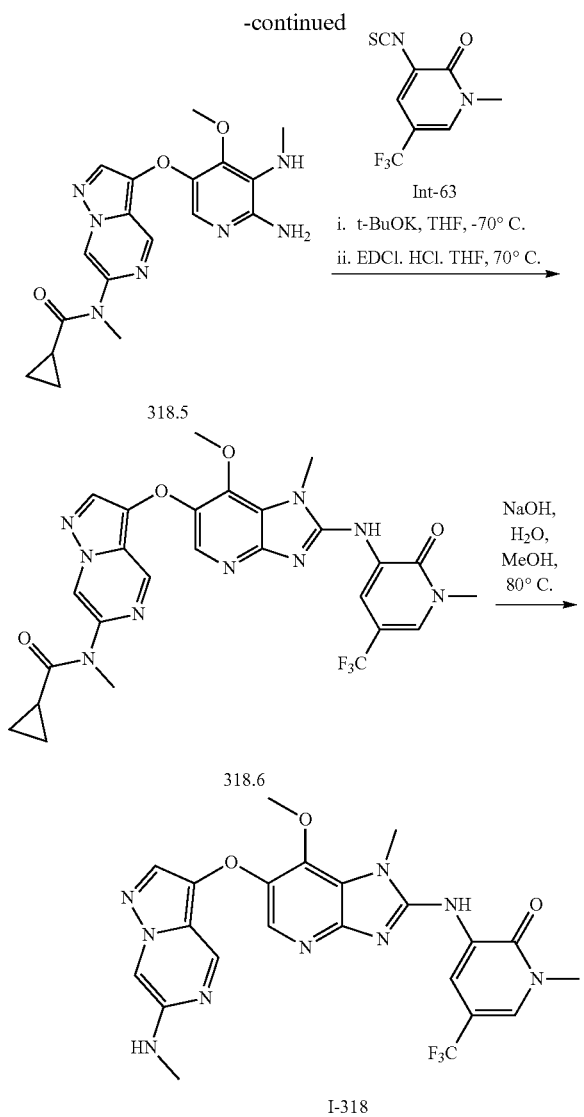

Synthesis of compound 318.1. To a solution of Int-4.1 (0.500 g, 0.164 mmol, 1.0 eq) in methanol (3 mL) was added sodium methoxide solution (0.5 M in methanol, 9.1 mL). The reaction mixture was stirred at 90° C. for 16 h. It was concentrated under reduced pressure. The residue was purified by flash column chromatography on silica gel (CombiFlash®, 25% ethyl acetate in hexane) to afford 318.1. MS (ES): m/z 161.5 [M+H]$^+$.

Synthesis of compound 318.2. Concentrated sulfuric acid (5.2 mL) was added dropwise to potassium persulfate (1.77 g, 6.56 mmol, 2.0 equiv) at 0° C. and stirred for 15 min. To the mixture was added 318.1 (0.525 g, 3.28 mmol, 1.0 equiv) in portions while maintaining the reaction temperature at 30-40° C. It was stirred at room temperature for 18 h, transferred into crushed ice, stirred, and basified with saturated sodium bicarbonate and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 318.2. MS (ES): m/z 161.5 [M+H]$^+$.

Synthesis of compound 318.3. To a solution of 318.2 (0.385 g, 2.03 mmol, 1.0 equiv) in acetonitrile (10 mL) was added aqueous methylamine solution (40 wt %, 0.094 g, 3.04 mmol, 1.5 equiv) dropwise. The reaction mixture was stirred at room temperature for 20 min. It was poured into ice-water and extracted with ethyl acetate. The combined organic layers were washed with brine, dried over anhydrous sodium sulfate, filtered, and concentrated under reduced pressure to afford 318.3. MS (ES): m/z 202.5 [M+H]$^+$.

Synthesis of compound 318.4. A mixture of 318.3 (0.230 g, 1.14 mmol, 1.0 equiv), 304.7 (0.318 g, 1.37 mmol, 1.2 equiv) and potassium carbonate (0.471 g, 3.4 mmol, 3.0 equiv) in DMF (7 mL) was stirred at 70° C. for 2 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.4% methanol in DCM) to afford 318.4. MS (ES): m/z 414.5 [M+H]$^+$.

Synthesis of compound 318.5. A solution of 318.4 (0.180 g, 0.435 mmol, 1.0 equiv), iron powder (0.146 g, 2.61 mmol, 6.0 equiv), and ammonium chloride (0.140 g, 2.61 mmol, 6.0 equiv) in ethanol:water (3:1, 8 mL) was stirred at 100° C. for 10 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3% methanol in DCM) to afford 318.5. MS (ES): m/z 384.5 [M+H]$^+$.

Synthesis of compound 318.6. Compound 318.6 was prepared from 318.5 and Int-63, following the procedure described in the synthesis of I-51. The product was purified by flash column chromatography on silica gel (CombiFlash®, 2.5% methanol in DCM). MS (ES): m/z 584.3 [M+H]$^+$.

Synthesis of I-318. Compound I-318 was prepared from 318.6 following the procedure described in the synthesis of I-304. The product was purified by flash column chromatography on silica gel (CombiFlash®, 3.5% methanol in DCM). MS (ES): m/z 516.4 [M+H]$^+$, $^1$H NMR (DMSO-d$_6$, 400 MHz): 8.66 (s, 1H), 8.61-8.60 (d, J=3.6 Hz, 2H), 8.10 (bs, 2H), 7.56 (s, 1H), 7.52 (s, 1H), 6.11-6.10 (d, J=4.4 Hz, 1H), 4.11 (s, 3H), 3.91 (s, 3H), 3.65 (s, 3H), 2.71-2.70 (d, J=4 Hz, 3H).

Example 319: 6-((3-(methoxymethyl)-1H-pyrazolo[3,4-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

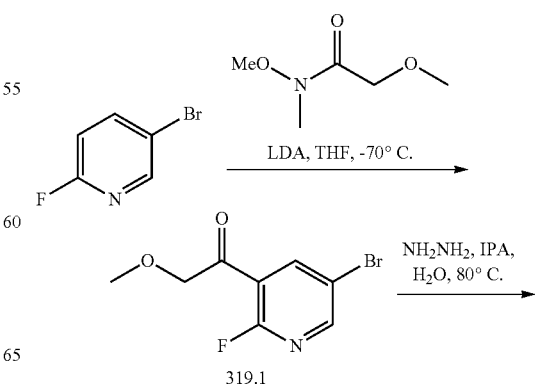

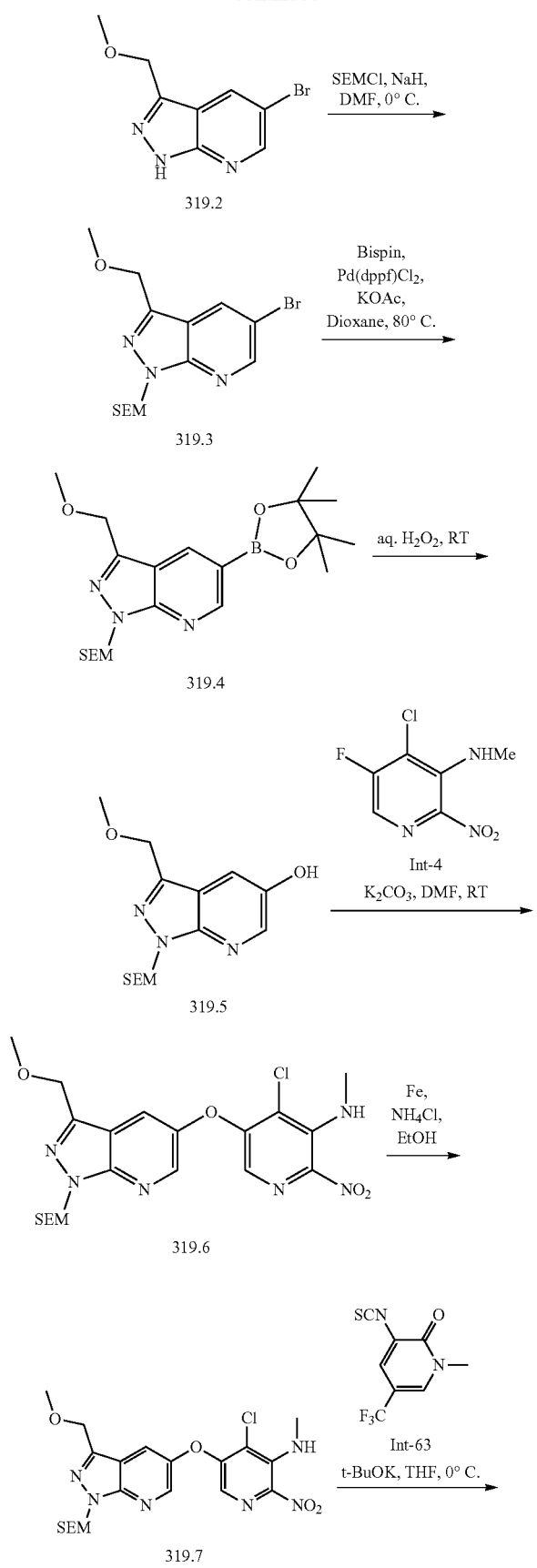
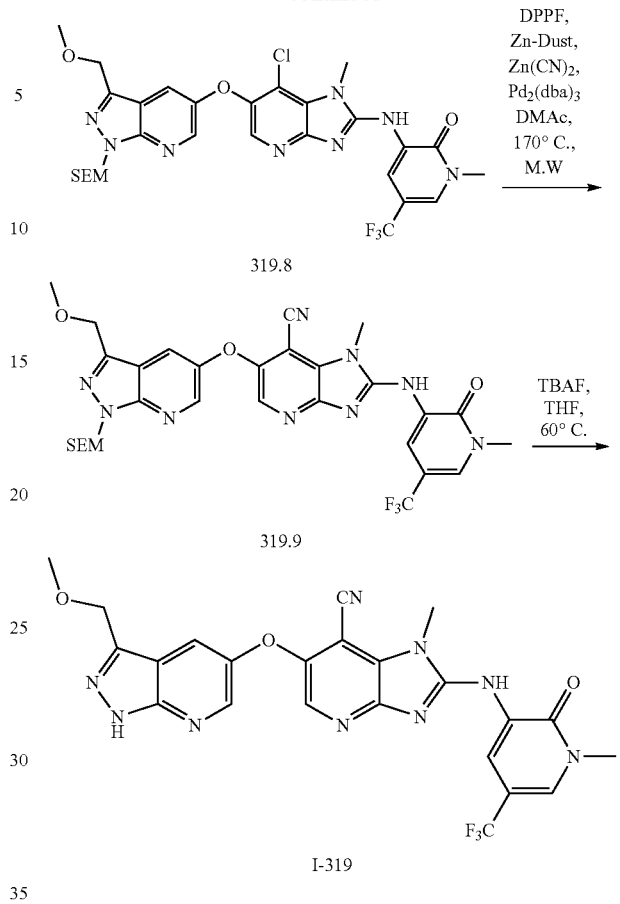

Synthesis of compound 319.1. To a solution of lithium diisopropylamide (2 M in THF, 14.65 mL, 29.31 mmol, 1.3 equiv) was added 5-bromo-2-fluoropyridine (5.16 g, 29.32 mmol, 1.3 equiv) in THF (40 mL) at −78° C. and stirred for 30 min. To the mixture was added N,2-dimethoxy-N-methylacetamide (3.0 g, 22.55 mmol, 1.0 equiv) and stirred for 45 min. It was transferred into aqueous ammonium chloride solution and extracted with ethyl acetate. The combined organic layers were washed with brine, dried over anhydrous sodium sulfate, filtered, and concentrated under reduced pressure to afford 319.1. MS (ES): m/z 249.1 [M+H]$^+$.

Synthesis of compound 319.2. To a solution of 319.2 (1.4 g, 5.64 mmol, 1.0 equiv) in isopropyl alcohol (30 mL) was added hydrazine hydrate (1.4 g, 28.2 mmol, 5.0 equiv) at room temperature. The reaction mixture was stirred at 80° C. for 16 h. It was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford 319.2. MS (ES): m/z 243.1 [M+H]$^+$.

Synthesis of compound 319.3. To a suspension of sodium hydride (0.074 g, 3.1 mmol, 1.5 equiv) in DMF (5 mL) was added a solution of 319.2 (0.500 g, 2.07 mmol, 1.0 equiv) in DMF (5 mL) at 0° C. and stirred for 30 min. To the mixture was added (2-chloromethoxyethyl)trimethylsilane (0.412 g, 2.48 mmol, 1.2 equiv) and stirred at room temperature for 30 min. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 18% ethyl acetate in hexane) to afford 319.3. MS (ES): m/z 373.2 [M+H]$^+$.

Synthesis of compound 319.4. A mixture of 319.3 (0.450 g, 1.21 mmol, 1.0 equiv), bis(pinacolato)diboron (0.778 g, 3.02 mmol, 2.5 equiv) and potassium acetate (0.355 g, 3.63 mmol, 3 equiv) in 1,4-dioxane (9 mL) was degassed by bubbling argon through for 30 min. Under argon atmosphere, 1,1-bis(diphenylphosphino)ferrocene-palladium(II) dichloride DCM complex (0.088 g, 0.121 mmol, 0.1 equiv) was added. The reaction mixture was stirred at 80° C. for 6 h. It was poured into ice-water and extracted with ethyl acetate. The combined organic layers were washed with brine, dried over anhydrous sodium sulfate, filtered, and concentrated under reduced pressure to afford 319.4. MS (ES): m/z 420.1 [M+H]$^+$.

Synthesis of compound 319.5. To a solution 319.4 (0.450 g, 1.07 mmol, 1.0 equiv) in acetonitrile:methanol (1:1, 10 mL) was added aqueous hydrogen peroxide solution (9 mL). The reaction mixture was stirred at room temperature for 16 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford 319.5. MS (ES): m/z 310.2 [M+H]$^+$.

Synthesis of compound 319.6. Compound 319.6 was prepared from compound 319.5 and Int-4, following the procedure described in the synthesis of 19.1. The product was purified by flash column chromatography on silica gel (CombiFlash®, 35% ethyl acetate in hexane. MS (ES): m/z 496.5 [M+H]$^+$.

Synthesis of compound 319.7. Compound 319.7 was prepared from 319.6 following the procedure described in the synthesis of 5.4. The product was purified by flash column chromatography on silica gel (CombiFlash®, 1.8% methanol in DCM). MS (ES): m/z 466.5 [M+H]$^+$.

Synthesis of compound 319.8. Compound 319.8 was prepared from 319.7 and Int-63, following the procedure described in the synthesis of I-13. The product was purified by flash column chromatography on silica gel (CombiFlash®, 1.8% methanol in DCM). MS (ES): m/z 666.7 [M+H]$^+$.

Synthesis of compound 319.9. Compound 319.9 was prepared from 319.8 following the procedure described in the synthesis of I-157. The product was purified by flash column chromatography on silica gel (CombiFlash®, 4.1% methanol in DCM). MS (ES): m/z 656 [M+H]$^+$.

Synthesis of I-319. To a solution of 319.9 (0.095 g, 0.144 mmol, 1.0 equiv) in DCM (2 mL) was added a solution of tetra-n-butylammonium fluoride (1 M in THF, 1 mL) and stirred at 80° C. for 12 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-319. MS (ES): m/z 526.3 [M+H]$^+$. $^1$H NMR (DMSO-d$_6$, 400 MHz): δ 13.74 (s, 1H), 9.03 (s, 1H), 8.66-8.65 (d, J=2.0 Hz, 1H), 8.61-8.60 (d, J=2.8 Hz, 1H), 8.19 (s, 1H), 8.12 (s, 1H), 7.98-7.97 (d, J=2.0 Hz, 1H), 4.68 (s, 2H), 4.00 (s, 3H), 3.68 (s, 3H), 3.27 (s, 3H).

Example 320: 1-methyl-3-((1-methyl-6-((6-(methylamino)pyrazolo[1,5-a]pyridin-3-yl)oxy)-1H-imidazo[4,5-b]pyridin-2-yl)amino)-5-(trifluoromethyl)pyridin-2(1H)-one

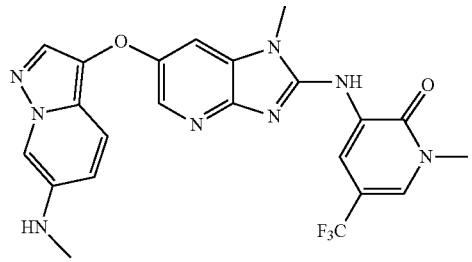

I-320

Compound I-320 was isolated as a side product in the synthesis of I-302. MS (ES): m/z 485.3, $^1$H NMR (DMSO-d$_6$, 400 MHz): δ 8.67 (s, 1H), 8.59 (s, 1H), 8.10 (bs, 2H), 7.73 (s, 1H), 7.59 (s, 1H), 7.57 (s, 1H), 7.25-7.22 (d, J=9.6 Hz, 1H), 6.81-6.78 (d, J=9.2 Hz, 1H), 5.68 (bs, 1H), 3.70 (s, 3H), 3.65 (s, 3H), 2.68 (s, 3H).

Example 321: 3-((7-chloro-1-methyl-6-((6-(methylamino)pyrazolo[1,5-a]pyrazin-3-yl)oxy)-1H-imidazo[4,5-b]pyridin-2-yl)amino)-1-cyclopropyl-5-(trifluoromethyl)pyridin-2(1H)-one

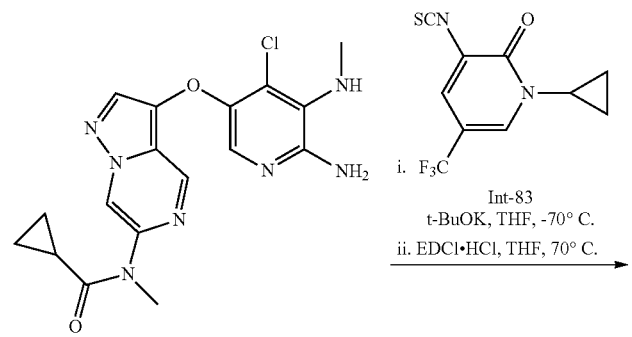

304.9

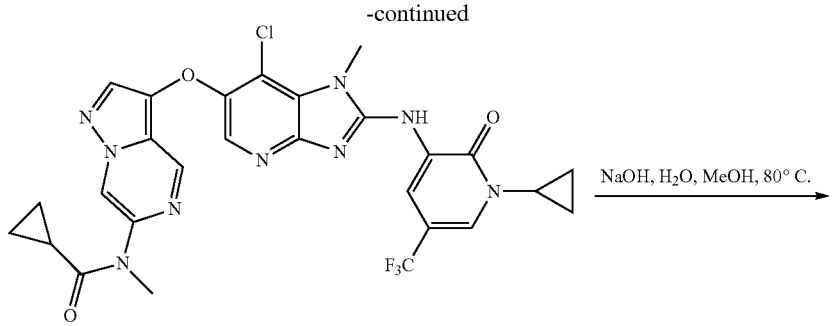

321.1

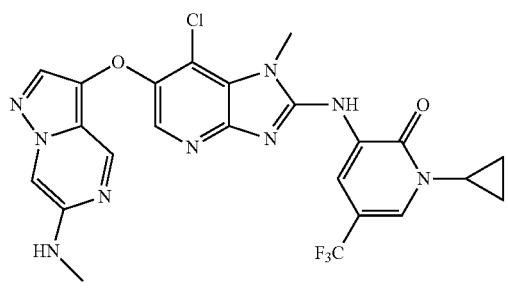

I-321

Synthesis of compound 321.1. Compound 321.1 was prepared from 304.9 and Int-83, following the procedure described in the synthesis of I-51. The product was purified by flash column chromatography on silica gel (CombiFlash®, 3.3% methanol in DCM). MS (ES): m/z 614.1 [M+H]⁺.

Synthesis of I-321. Compound I-321 was prepared from 321.1 following the procedure described in the synthesis of I-304. The product was purified by flash column chromatography on silica gel (CombiFlash®, 2.5% methanol in DCM). MS (ES): m/z 546.3 [M+H]⁺, ¹H NMR (DMSO-d₆, 400 MHz): 8.87 (s, 1H), 8.70 (s, 1H), 8.65 (s, 1H), 8.19 (s, 1H), 8.09 (s, 1H), 7.67 (s, 1H), 7.56 (s, 1H), 6.16-6.15 (d, J=5.2 Hz, 1H), 4.02 (s, 3H), 2.73-2.72 (d, 3H), 2.57 (bs, 1H), 1.25 (bs, 4H).

Example 322: 6-((1H-pyrrolo[2,3-b]pyridin-5-yl)oxy)-2-((1-(2-oxaspiro[3.3]heptan-6-yl)-5-(trifluoromethyl)-1H-pyrazol-3-yl)amino)-1-methyl-1H-imidazo[4,5-b]pyridine-7-carbonitrile

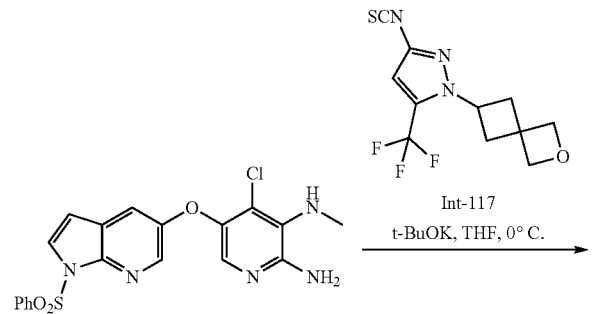

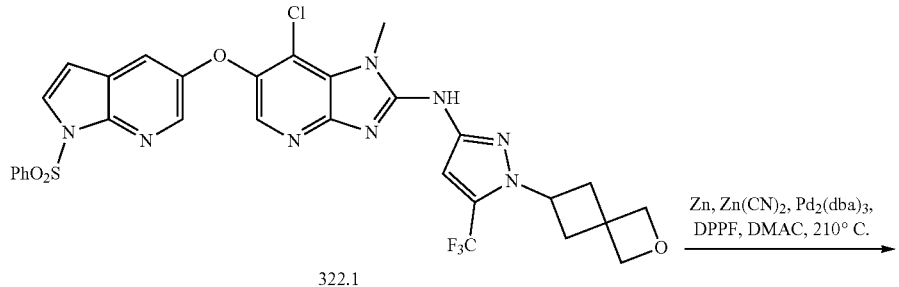

322.1

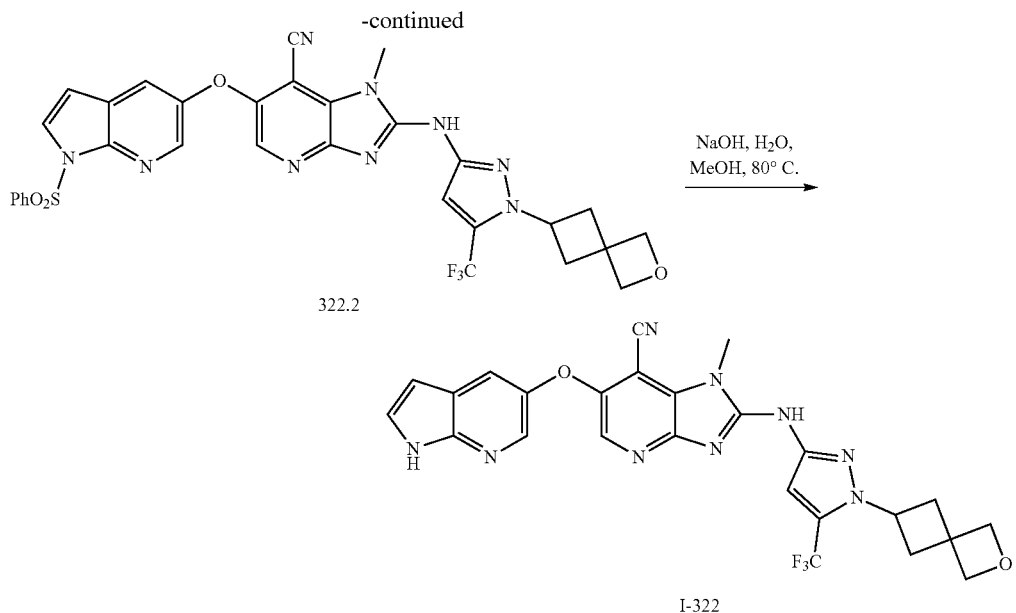

Synthesis of compound 322.1. Compound 322.1 was prepared from 257.4 and Int-117, following the procedure described in the synthesis of I-13. The product was purified by flash column chromatography on silica gel (CombiFlash®, 4.1% methanol in DCM). MS (ES): m/z 686.0 [M+H]⁺.

Synthesis of compound 322.2. Compound 322.2 was prepared from 322.1 following the procedure described in the synthesis of 296.1. The product was purified by flash column chromatography on silica gel (CombiFlash®, 3.8% methanol in DCM). MS (ES): m/z 676.4 [M+H]⁺.

Synthesis of I-322. Compound I-322 was prepared from 322.2 following the procedure described in the synthesis of I-304. The product was purified by flash column chromatography on silica gel (CombiFlash®, 5.2% methanol in DCM). MS (ES): m/z 536.3 [M+H]⁺, ¹H NMR (DMSO-d₆, 400 MHz): δ 11.81 (s, 1H), 10.78 (s, 1H), 8.20-8.19 (d, J=2.4 Hz, 1H), 7.92 (s, 1H), 7.73 (s, 1H), 7.57 (s, 1H), 7.32 (s, 1H), 6.44 (s, 1H), 4.88-4.84 (m, 1H), 4.71 (s, 2H), 4.60 (s, 2H), 3.97 (s, 3H), 1.25 (bs, 4H).

Example 323: 3-((7-chloro-1-methyl-2-((1-methyl-2-oxo-5-(trifluoromethyl)-1,2-dihydropyridin-3-yl)amino)-1H-imidazo[4,5-b]pyridin-6-yl)oxy)-5-methylpyrazolo[1,5-a]pyrazin-4(5H)-one

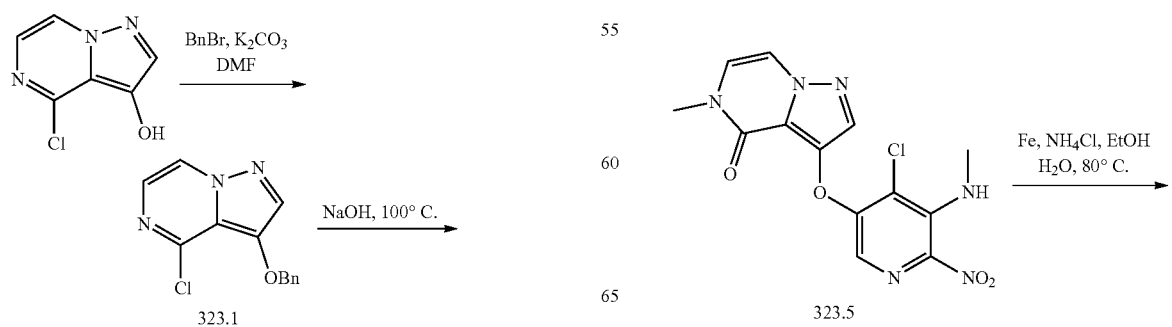

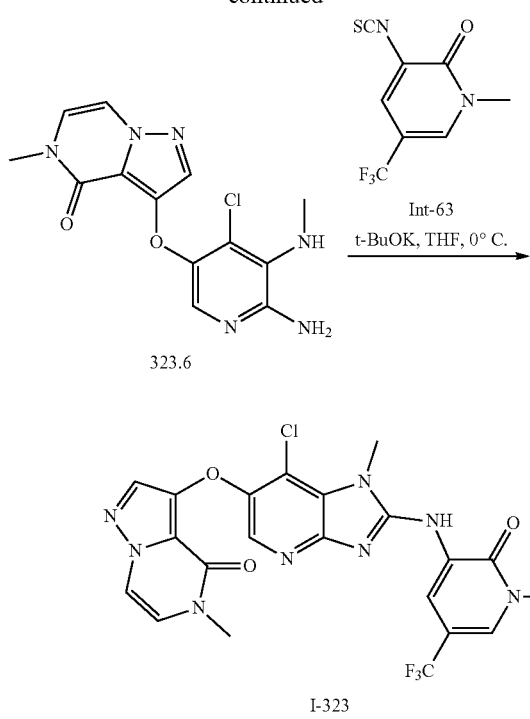

323.6

I-323

Synthesis of compound 323.1. To a solution of 4-chloro-pyrazolo[1,5-a]pyrazin-3-ol (1.0 g, 5.90 mmol, 1.0 equiv) in DMF (22 mL) was added potassium carbonate (1.63 g, 11.83 mmol, 2.0 equiv) and stirred for 5 min followed by the addition of benzyl bromide (1.11 g, 6.50 mmol, 1.1 equiv). The reaction mixture was stirred at room temperature for 2 h. It was cooled to room temperature, poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 8.0% ethyl acetate in hexane) to afford 323.1. MS (ES): m/z 260.5 [M+H]$^+$.

Synthesis of compound 323.2. A solution of 323.1 (0.910 g, 231 mmol 1.0 equiv) in 20% aq. sodium hydroxide solution (10 mL) was heated to 100° C. for 2 h. The reaction mixture was diluted with water and neutralized with citric acid. The precipitated solids were collected by filtration and dried under vacuum to afford 323.2. MS (ES): m/z 242.1 [M+H]$^+$.

Synthesis of compound 323.3. To a solution of 323.2 (0.510 g, 2.11 mmol, 1.0 equiv) in THF (20 mL) was added sodium hydride (0.071 g, 2.96 mmol, 1.4 equiv) at room temperature and stirred for 30 min followed by the addition of methyl iodide (0.330 g, 2.32 mmol, 1.1 equiv). The reaction mixture was stirred at room temperature for 12 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford 323.3. MS (ES): m/z 256.2 [M+H]$^+$.

Synthesis of compound 323.4. A mixture of 323.3 (0.280 g, 1.10 mmol, 1.0 equiv) and 10% palladium on carbon (0.140 g) in methanol (3 mL) was stirred under hydrogen (1 atm) for 2 h. The reaction mixture was filtered through a pad of Celite® and rinsed with methanol. The filtrate was concentrated under reduced pressure to afford 323.4. MS (ES): m/z 166.15 [M+H]$^+$.

Synthesis of compound 323.5. Compound 323.5 was prepared from compound 323.4 and Int-4, following the procedure described in the synthesis of 19.1. The product was purified by flash column chromatography on silica gel (CombiFlash®, 30% ethyl acetate in hexane). MS (ES): m/z 351.72 [M+H]$^+$.

Synthesis of compound 323.6. Compound 323.6 was prepared from 323.5 following the procedure described in the synthesis of 5.4. The product was purified by flash column chromatography on silica gel (CombiFlash®, 2.5% methanol in DCM). MS (ES): m/z 321.74 [M+H]$^+$.

Synthesis of I-323. Compound I-323 was prepared from 323.6 and Int-63, following the procedure described in the synthesis of I-13. The product was purified by flash column chromatography on silica gel (CombiFlash®, 2.4% methanol in DCM). MS (ES): m/z 521.1 [M+H]$^+$, $^1$H NMR (DMSO-d$_6$, 400 MHz): δ 8.80 (s, 1H), 8.59 (s, 1H), 8.12 (s, 1H), 8.01 (s, 1H), 7.75 (s, 1H), 7.69-7.68 (d, J=5.6 Hz, 1H), 7.10-7.09 (d, J=5.6 Hz, 1H), 4.01 (s, 3H), 3.65 (s, 3H), 2.50 (s, 3H).

Example 324: 3-((7-chloro-1-methyl-6-((6-(methyl-amino)pyrazolo[1,5-a]pyrazin-3-yl)oxy)-1H-imidazo[4,5-b]pyridin-2-yl)amino)-5-(trifluoromethyl)-2H-[1,3'-bipyridin]-2-one

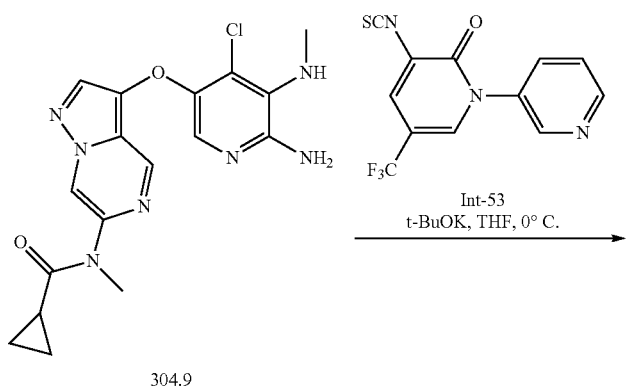

304.9

-continued

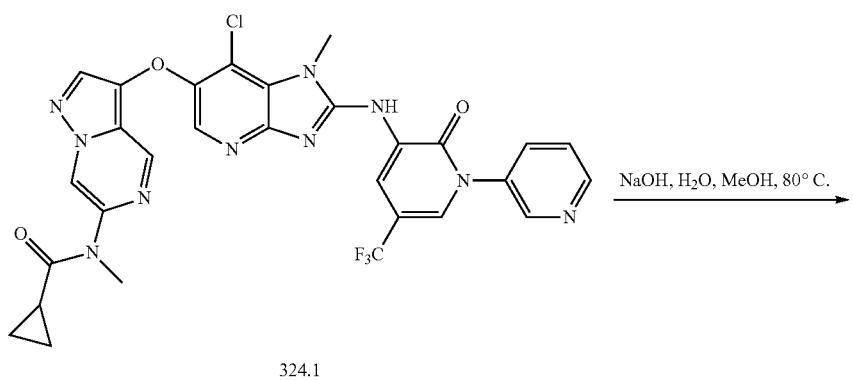

324.1

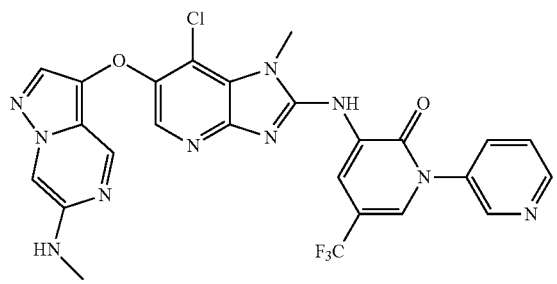

I-324

Synthesis of compound 324.1. Compound 324.1 was prepared from 304.9 and Int-53, following the procedure described in the synthesis of I-13. The product was purified by flash column chromatography on silica gel (Combi-Flash®, 3.8% methanol in DCM). MS (ES): m/z 652.0 [M+H]$^+$.

Synthesis of I-324. Compound I-324 was prepared from 324.1 following the procedure described in the synthesis of I-304. The product was purified by flash column chromatography on silica gel (CombiFlash®, 2.5% methanol in DCM). MS (ES): m/z 583.1[M+H]$^+$, $^1$H NMR (DMSO-d$_6$, 400 MHz): δ 8.99 (s, 1H), 8.82 (s, 1H), 8.74-8.72 (m, 3H), 8.21 (bs, 1H), 8.15 (bs, 1H), 8.11-8.09 (d, J=7.2 Hz, 1H), 7.68 (bs, 2H), 7.57 (s, 1H), 6.17-6.15 (d, J=4.8 Hz, 1H), 4.02 (s, 3H), 2.73-2.72 (d, 3H).

Example 325: 3-((7-chloro-1-methyl-6-((6-(methyl-amino)pyrazolo[1,5-a]pyrazin-3-yl)oxy)-1H-imidazo[4,5-b]pyridin-2-yl)amino)-1-(methyl-d$_3$)-5-(trifluoromethyl)pyridin-2(1H)-one

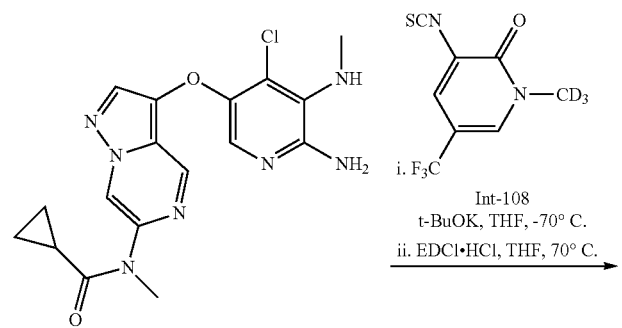

304.9

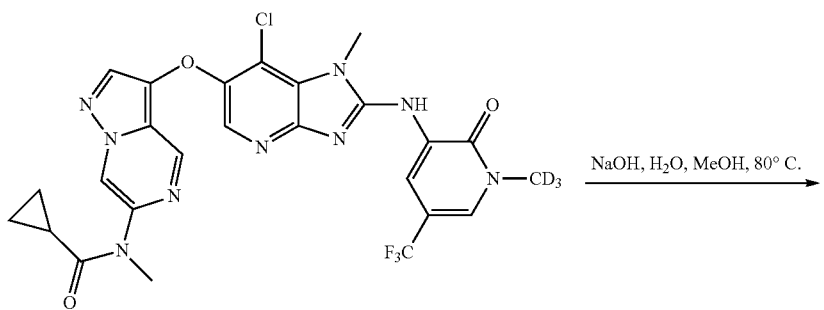

325.1

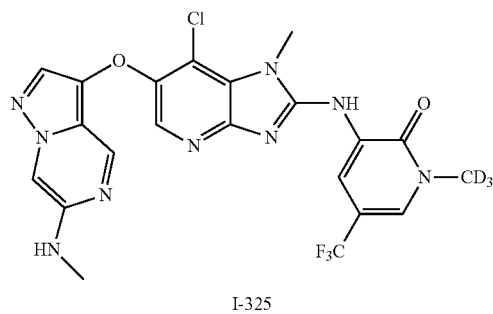

I-325

Synthesis of compound 325.1. Compound 325.1 was prepared from 304.9 and Int-108, following the procedure described in the synthesis of I-51. The product was purified by flash column chromatography on silica gel (CombiFlash®, 2.0% methanol in DCM). MS (ES): m/z 591.97 [M+H]⁺.

Synthesis of I-325. Compound I-325 was prepared from 325.1 following the procedure described in the synthesis of I-304. The product was purified by flash column chromatography on silica gel (CombiFlash®, 10% methanol in DCM). MS (ES): m/z 523.7 [M+H]⁺, ¹H NMR (DMSO-$d_6$, 400 MHz): δ 8.82 (s, 1H), 8.70 (s, 1H), 8.62 (s, 1H), 8.19 (s, 1H), 8.14 (s, 1H), 7.66 (s, 1H), 7.56 (s, 1H), 6.16-6.15 (d, J=4.8 Hz, 1H), 4.02 (s, 3H), 2.73-2.71 (d, 3H).

Example 326: 7-chloro-N-(4-((3,3-difluoropyrrolidin-1-yl)methyl)-3-(trifluoromethyl)phenyl)-1-methyl-6-((6-(methylamino)pyrazolo[1,5-a]pyrazin-3-yl)oxy)-1H-imidazo[4,5-b]pyridin-2-amine

304.9

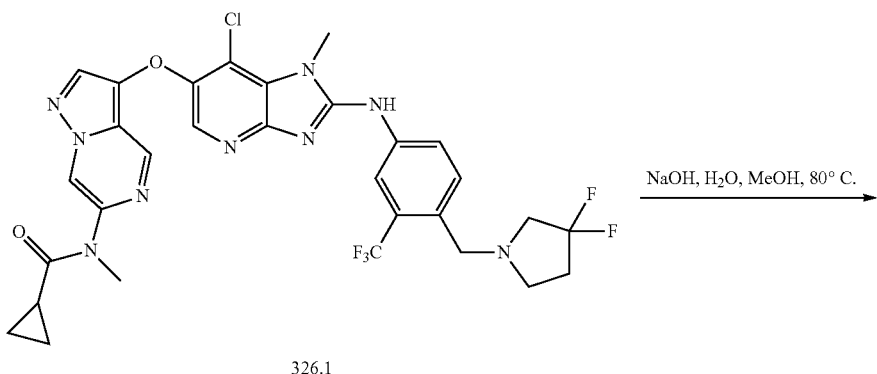

326.1

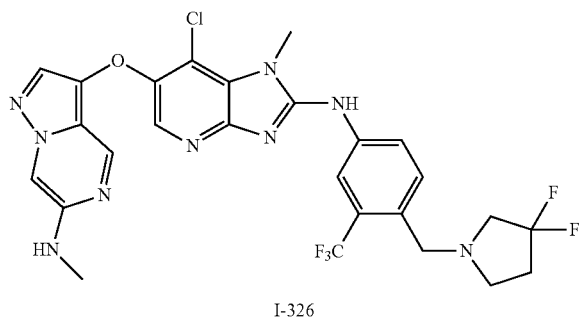

I-326

Synthesis of compound 326.1. Compound 326.1 was prepared from 304.9 and Int-87, following the procedure described in the synthesis of I-51. The product was purified by flash column chromatography on silica gel (Combi-Flash®, 3.3% methanol in DCM). MS (ES): m/z 677.05 [M+H]⁺.

Synthesis of I-326. Compound I-326 was prepared from 326.1 following the procedure described in the synthesis of I-304. The product was purified by flash column chromatography on silica gel (CombiFlash®, 2.5% methanol in DCM). MS (ES): m/z 609.0 [M+H]⁺, $^1$H NMR (DMSO-d$_6$, 400 MHz): δ 9.65 (s, 1H), 8.68 (s, 1H), 8.32 (s, 1H), 8.17 (s, 1H), 8.13 (s, 1H), 8.09 (s, 1H), 7.72-7.70 (d, J=8.8 Hz, 1H), 7.64 (s, 1H), 7.55 (s, 1H), 4.03 (s, 3H), 3.77 (s, 2H), 2.97-2.91 (m, 2H), 2.78-2.75 (m, 2H), 2.73-2.71 (d, 3H), 2.31-2.28 (m, 2H).

Example 327: 7-chloro-N-(3-((dimethylamino)methyl)-5-(trifluoromethyl)phenyl)-1-methyl-6-((6-(methylamino)pyrazolo[1,5-a]pyrazin-3-yl)oxy)-1H-imidazo[4,5-b]pyridin-2-amine

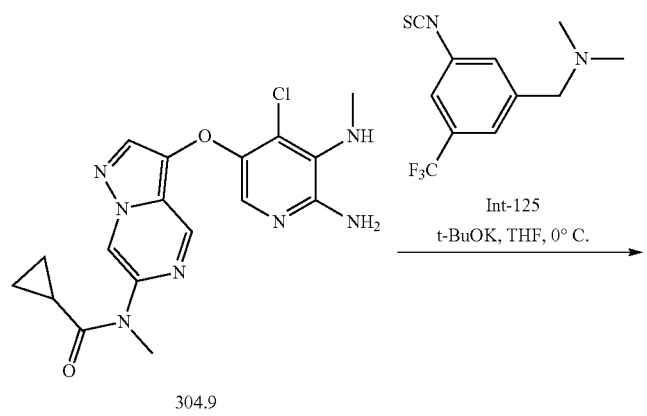

304.9

-continued

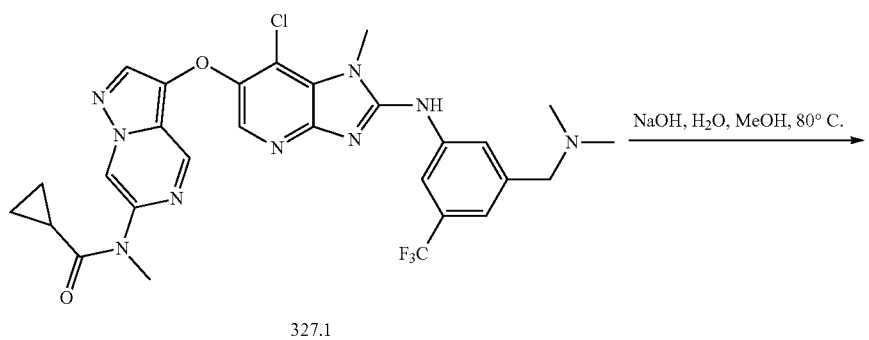

327.1

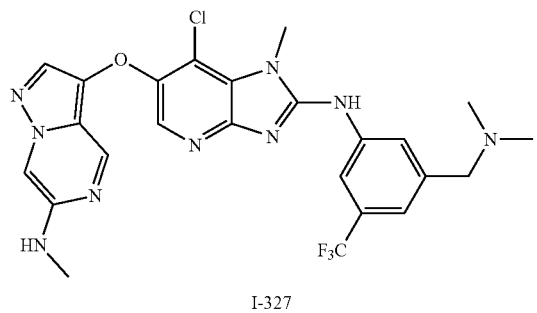

I-327

Synthesis of compound 327.1. Compound 327.1 was prepared from 304.9 and Int-125, following the procedure described in the synthesis of I-13. The product was purified by flash column chromatography on silica gel (CombiFlash®, 3.2% methanol in DCM). MS (ES): m/z 615.0 [M+H]⁺.

Synthesis of I-327. Compound I-327 was prepared from 327.1 following the procedure described in the synthesis of I-304. The product was purified by flash column chromatography on silica gel (CombiFlash®, 7.0% methanol in DCM). MS (ES): m/z 546.4 [M+H]⁺, $^1$H NMR (DMSO-d$_6$, 400 MHz): δ 9.79 (s, 1H), 8.68 (s, 1H), 8.35 (s, 1H), 8.21 (s, 1H), 8.09 (s, 1H), 7.64 (s, 1H), 7.55 (s, 1H), 7.46 (s, 1H), 6.14-6.12 (d, J=4.8 Hz, 1H), 4.05 (s, 3H), 3.87 (bs, 2H), 2.73-2.72 (d, 3H), 2.68 (s, 6H).

Example 328: 3-((7-chloro-1-methyl-6-(((6-(methylamino)pyrazolo[1,5-a]pyrazin-3-yl)oxy)-1H-imidazo[4,5-b]pyridin-2-yl)amino)-1-(1-methyl-1H-pyrazol-4-yl)-5-(trifluoromethyl)pyridin-2(1H)-one

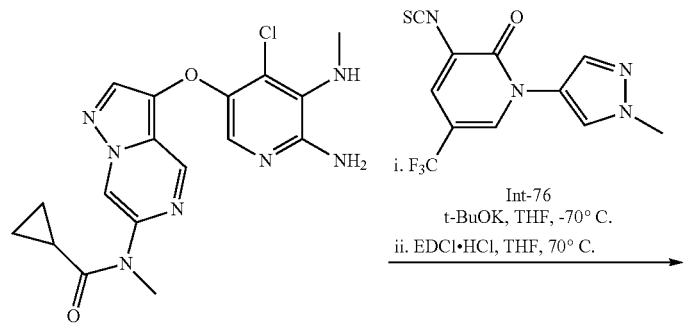

304.9

-continued

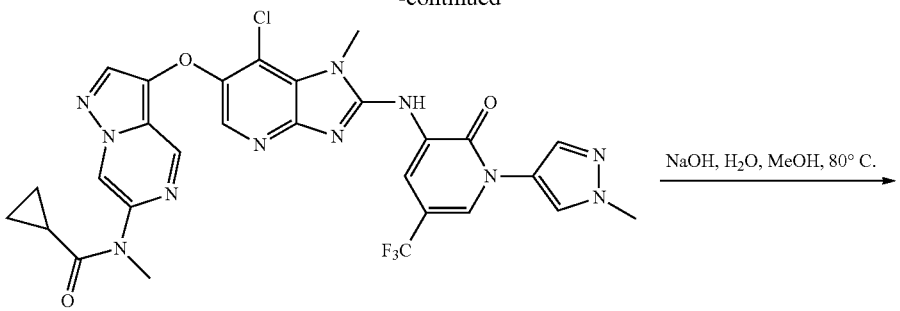

328.1

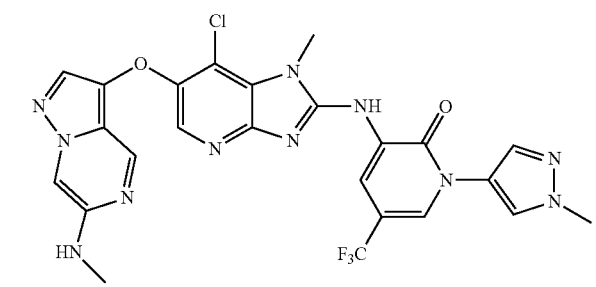

I-328

Synthesis of compound 328.1. Compound 328.1 was prepared from 304.9 and Int-76, following the procedure described in the synthesis of I-51. The product was purified by flash column chromatography on silica gel (Combi-Flash®, 1.8% methanol in DCM). MS (ES): m/z 655.3 [M+H]+.

Synthesis of I-328. Compound I-328 was prepared from 328.1 following the procedure described in the synthesis of I-304. The product was purified by trituration by methanol). MS (ES): m/z 586.3 [M+H]+, $^1$H NMR (DMSO-d$_6$, 400 MHz): 8.94 (s, 1H), 8.69 (s, 1H), 8.63 (s, 1H), 8.36 (s, 1H), 8.19 (s, 1H), 8.07 (s, 1H), 7.97 (s, 1H), 7.66 (s, 1H), 7.55 (s, 1H), 6.15-6.14 (d, J=4.8.4 Hz, 1H), 4.01 (s, 3H), 3.92 (s, 3H), 3.17-3.16 (d, J=4.8 Hz, 3H).

Example 329: 1-methyl-6-((3-methyl-1H-pyrrolo[2,3-b]pyridin-5-yl)oxy)-2-((1-methyl-2-oxo-5-(trifluoromethyl)-1,2-dihydropyridin-3-yl)amino)-1H-imidazo[4,5-b]pyridine-7-carbonitrile

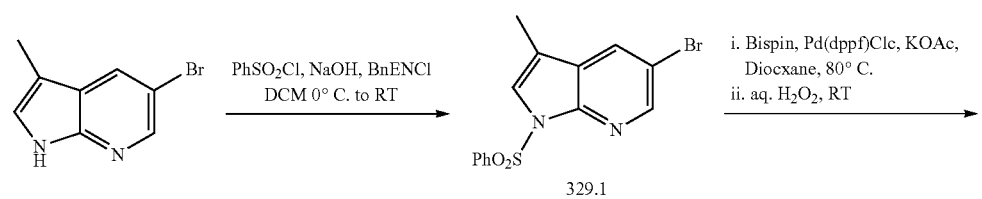

329.1

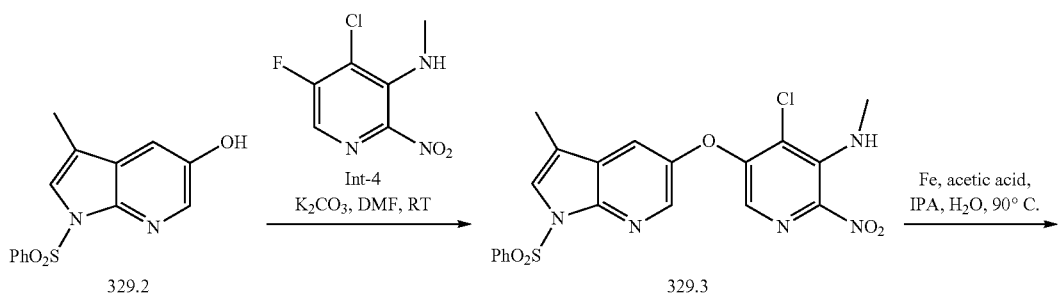

329.2    329.3

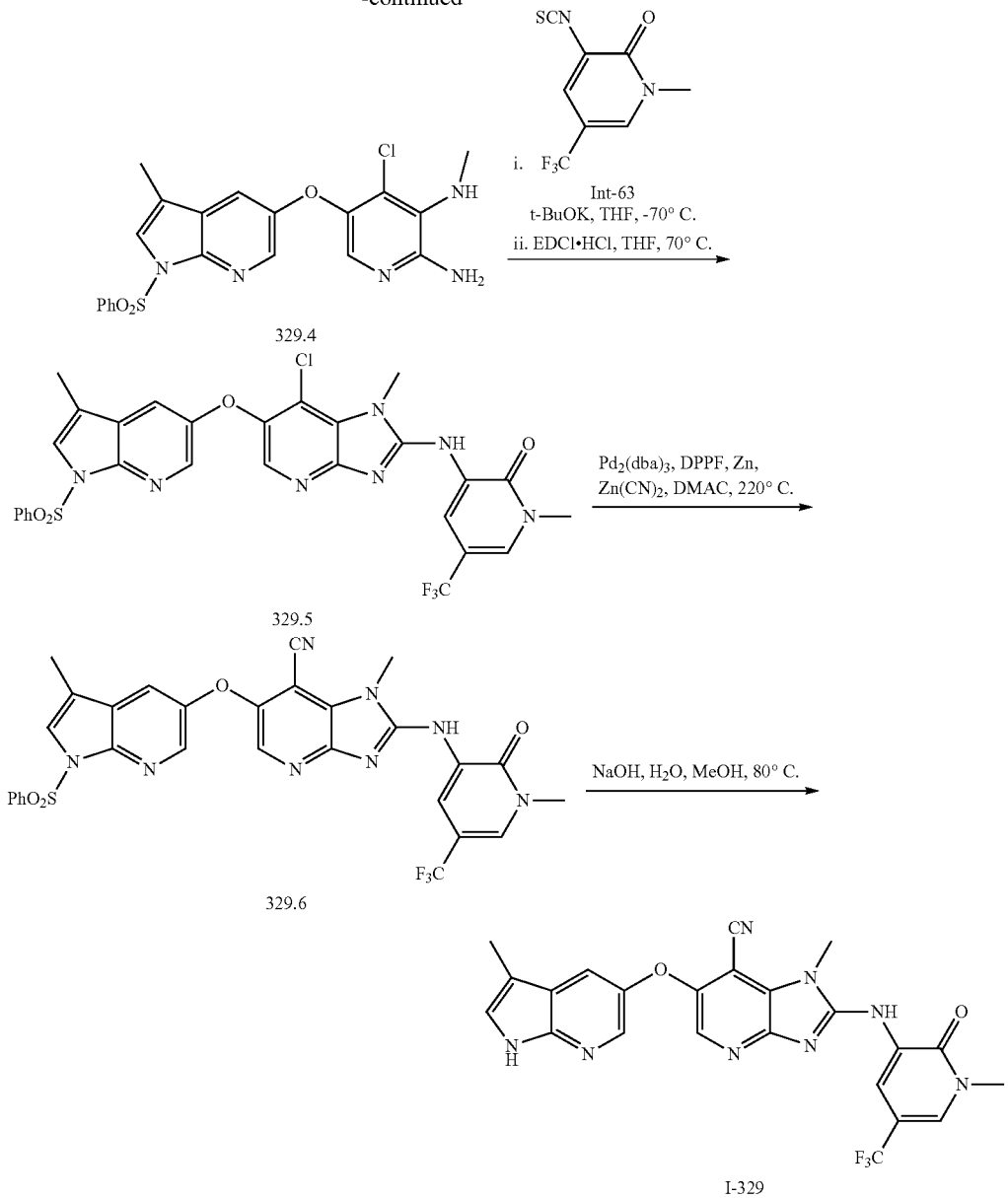

Synthesis of compound 329.1. To a solution of 5-bromo-3-methyl-1H-pyrrolo[2,3-b]pyridine (2.0 g, 9.48 mmol, 1.0 equiv) and benzyltriethylammonium chloride (0.043 g, 0.189 mmol, 0.02 equiv) in DCM (20 mL) was added sodium hydroxide powder (1.13 g, 28.44 mmol, 3.0 equiv) at 0° C. To the mixture was added benzyl sulfonyl chloride (2.08 g, 11.85 mmol, 1.25 equiv) and stirred at room temperature for 2 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford 329.1. MS (ES): m/z 352.1 [M+H]$^+$.

Synthesis of compound 329.2. A solution of 329.1 (1.5 g, 4.27 mmol, 1.0 equiv), bis(pinacolato)diboron (2.16 g, 8.54 mmol, 2.0 equiv) and potassium acetate (0.836 g, 8.54 mmol, 2.0 equiv) in 1,4-dioxane (15 mL) was degassed by bubbling argon through for 5 min. Under argon atmosphere, 1,1-bis(diphenylphosphino)ferrocene-palladium(II) dichloride DCM complex (0.062 g, 0.085 mmol, 0.02 equiv) was added and degassed for 5 min. The reaction mixture was stirred at 90° C. for 2 h. It was cooled to room temperature, transferred into ice-water, stirred, and extracted with ethyl acetate. The combined organic layers were washed with brine, dried over anhydrous sodium sulfate, filtered, and concentrated under reduced pressure. The residue was dissolved in acetonitrile (10 mL) and methanol (10 mL) and treated with hydrogen peroxide (10 mL) at room temperature for 16 h. It was transferred into ice-water, stirred, and extracted with ethyl acetate. The combined organic layers were washed with brine, dried over anhydrous sodium sulfate, filtered, and concentrated under reduced pressure to afford 329.2. MS (ES): m/z 289.1 [M+H]$^+$.

Synthesis of compound 329.3. Compound 329.3 was prepared from compound 329.2 and Int-4, following the procedure described in the synthesis of 19.1. The product was used in the next step without purification. MS (ES): m/z 474.5 [M+H]$^+$.

Synthesis of compound 329.4. To a solution of 329.3 (0.390 g, 0.822 mmol, 1.0 equiv) in isopropyl alcohol:water (1:1, 10 mL) was added iron powder (0.230 g, 4.11 mmol, 5.0 equiv) followed by acetic acid (0.221 g, 4.11 mmol, 5.0 equiv). The reaction mixture was stirred at 90° C. for 1 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 1.4% methanol in DCM) to afford 329.4. MS (ES): m/z 444.5 [M+H]$^+$.

Synthesis of compound 329.5. Compound 329.5 was prepared from 329.4 and Int-63, following the procedure described in the synthesis of I-51. The product was purified by flash column chromatography on silica gel (CombiFlash®, 40% ethyl acetate in hexane). MS (ES): m/z 645.3 [M+H]$^+$.

Synthesis of compound 329.6. Compound 329.6 was prepared from 329.5 following the procedure described in the synthesis of 300.8. The product was purified by flash column chromatography on silica gel (CombiFlash®, 1.8% methanol in DCM). MS (ES): m/z: 635.4 [M]$^+$.

Synthesis of I-329. Compound I-329 was prepared from 329.6 following the procedure described in the synthesis of I-304. The product was purified by flash column chromatography on silica gel (CombiFlash®, 4% methanol in DCM). MS (ES): m/z 495.2 [M+H]$^+$, $^1$H NMR (DMSO-d$_6$, 400 MHz): 11.47 (s, 1H), 8.97 (s, 1H), 8.62 (s, 1H), 8.17 (bs, 2H), 7.96 (s, 1H), 7.73 (s, 1H), 7.33 (s, 1H), 3.98 (s, 3H), 3.66 (s, 3H), 2.21 (s, 3H).

Example 330: 6-((1H-pyrazolo[3,4-b]pyridin-5-yl)oxy)-2-((1-(2-oxaspiro[3.3]heptan-6-yl)-5-(trifluoromethyl)-1H-pyrazol-3-yl)amino)-1-methyl-1H-imidazo[4,5-b]pyridine-7-carbonitrile

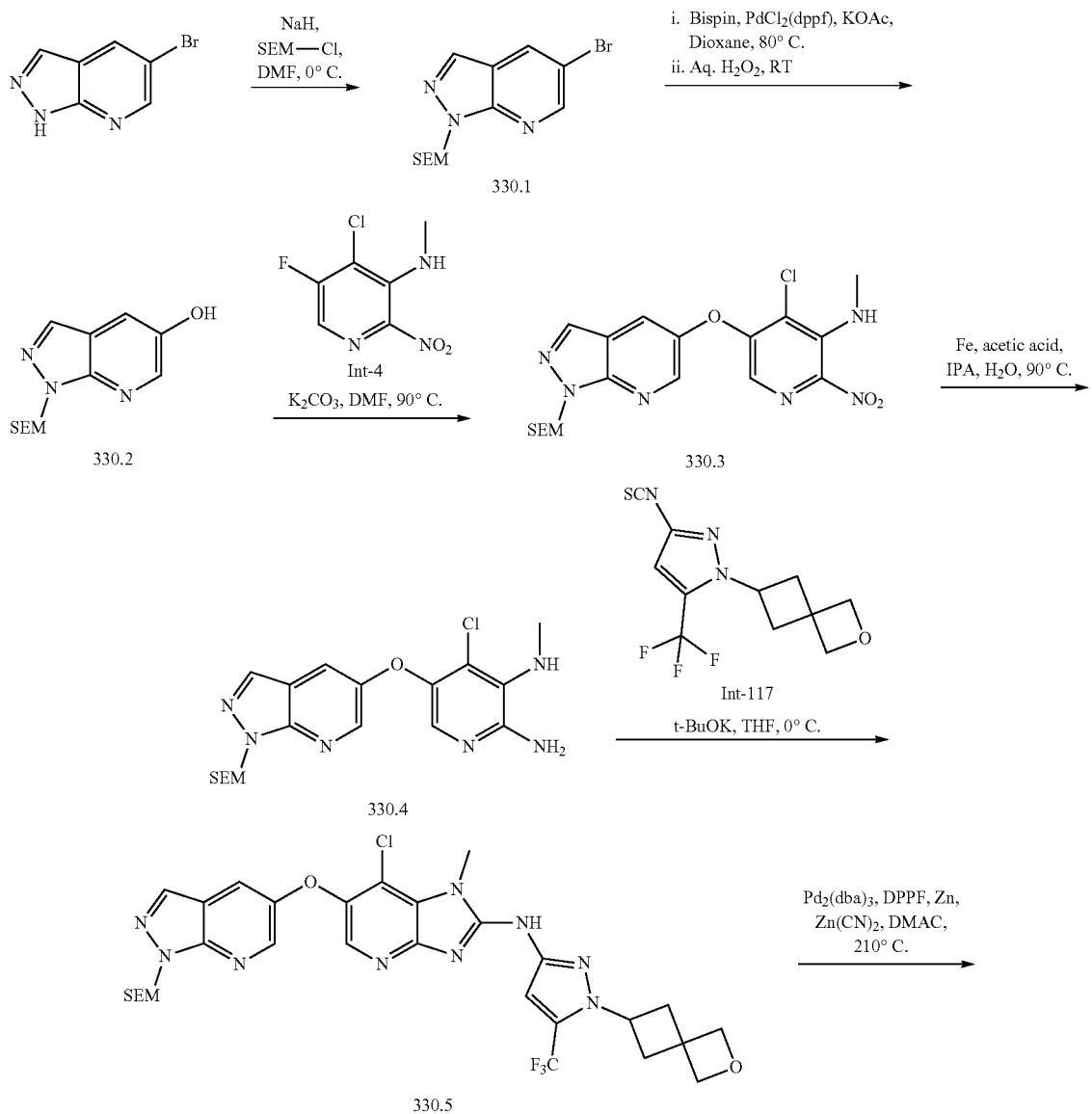

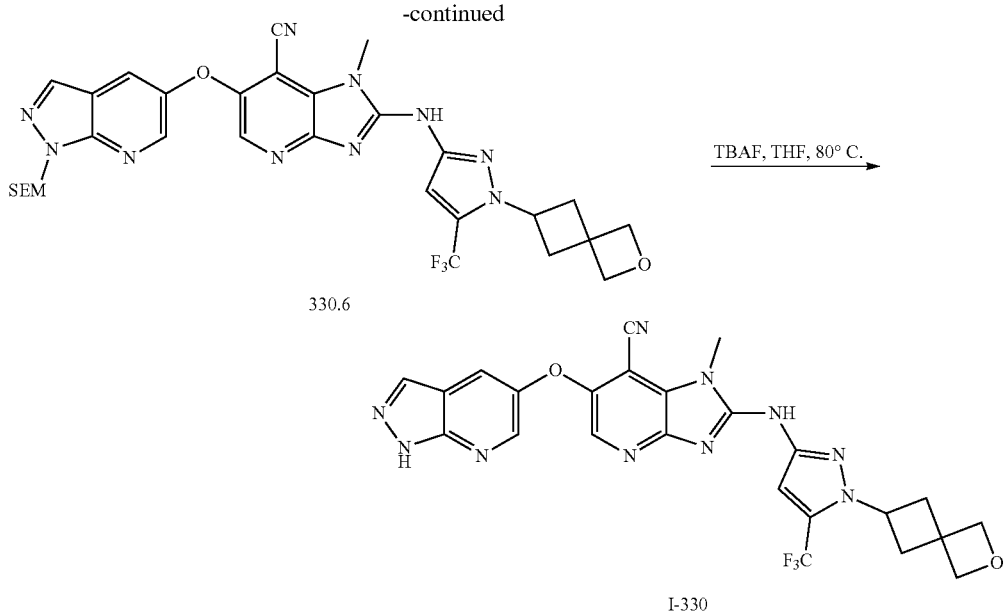

330.6

I-330

Synthesis of compound 330.1. To a suspension of sodium hydride (60%, 1.6 g, 40.40 mmol, 1.5 equiv) in DMF (30 mL) was added a solution of 5-bromo-1H-pyrazolo[3,4-b]pyridine (4 g, 20.20 mmol, 1.0 equiv) in DMF (10 mL) at 0° C. and stirred for 15 min. To the mixture was added (2-chloromethoxyethyl)trimethylsilane (4.048 g, 24.24 mmol, 1.2 equiv) and stirred at room temperature for 3 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 330.1. MS (ES): m/z 329.2 [M+H]+.

Synthesis of compound 330.2. A mixture of 330.1 (3.5 g, 10.66 mmol, 1.0 equiv), bis(pinacolato)diboron (4.9 g, 19.40 mmol, 1.82 equiv) and potassium acetate (1.9 g, 19.40 mmol, 1.82 equiv) in 1,4 dioxane (25 mL) was degassed by bubbling argon through for 10 min. Under argon atmosphere, 1,1-bis(diphenylphosphino)ferrocene-palladium(II) dichloride DCM complex (0.155 g, 0.213 mmol, 0.02 equiv) was added. The reaction mixture was stirred at 80° C. for 18 h. It was poured into ice-water and extracted with ethyl acetate. The combined organic layers were washed with brine, dried over anhydrous sodium sulfate, filtered, and concentrated under reduced pressure. To the residue was added aqueous hydrogen peroxide solution (18 mL) and stirred at room temperature for 5 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 45% ethyl acetate in hexane) to afford 330.2. MS (ES): m/z 266.2 [M+H]+.

Synthesis of compound 330.3. A mixture of 330.2 (1.5 g, 5.65 mmol, 1.3 equiv), Int-4 (0.893 g, 4.35 mmol, 1.0 equiv) and potassium carbonate (1.8 g, 1.938 mmol, 3.0 equiv) in DMF (15 mL) was stirred at 90° C. for 3 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2% methanol in DCM) to afford 330.3. MS (ES): m/z 451.5 [M+H]+.

Synthesis of compound 330.4. To a solution of 330.4 (1.2 g, 2.66 mmol, 1.0 equiv) in isopropyl alcohol:water (2:1, 18 mL) was added iron powder (0.582 g, 10.4 mmol, 4.0 equiv) followed by acetic acid (0.798 g, 13.3 mmol, 5.0 equiv). The reaction mixture was stirred at 90° C. for 3 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 10% methanol in DCM) to afford 330.4. MS (ES): m/z 421.5 [M+H]+.

Synthesis of compound 330.5. Compound 330.5 was prepared from 330.4 and Int-117, following the procedure described in the synthesis of I-13. The product was purified by flash column chromatography on silica gel (CombiFlash®, 2.5% methanol in DCM). MS (ES): m/z 677.7 [M+H]+.

Synthesis of compound 330.6. A mixture of 330.5 (0.065 g, 0.096 mmol, 1.0 equiv), zinc dust (0.001 g, 0.019 mmol, 0.2 equiv) and zinc cyanide (0.005 g, 0.048 mmol, 0.5 equiv) in N,N-dimethylacetamide (7 mL) was degassed by bubbling argon through for 10 min. Under argon atmosphere tris(dibenzylideneacetone)dipalladium(0) (0.013 g, 0.014 mmol, 0.15 equiv) and 1,1'-bis(diphenylphosphino)ferrocene (0.015 g, 0.028 mmol, 0.3 equiv) were added, and degassed for 5 min. The reaction mixture was stirred at 210° C. in microwave for 2 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 3.1% methanol in DCM) to afford 330.6. MS (ES): m/z 656 [M+H]+.

Synthesis of I-330. To a solution of 330.6 (0.029 g, 0.043 mmol, 1.0 equiv) in DCM (2 mL) was added a solution of tetra-n-butylammonium fluoride (1 M in THF, 1 mL) and stirred at 80° C. for 6 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-330. MS (ES): m/z 537.3 [M+H]$^+$. $^1$H NMR (DMSO-d$_6$, 400 MHz): δ 13.79 (s, 1H), 10.81 (s, 1H), 8.56 (s, 1H), 8.08 (s, 1H), 8.02 (s, 1H), 7.90 (s, 1H), 7.31 (s, 1H), 4.86-4.83 (m, 1H), 4.70 (s, 2H), 4.58 (s, 2H), 3.95 (s, 3H), 1.60 (bs, 2H), 1.32 (bs, 2H).

Example 331: (S)-7-chloro-1-methyl-6-((6-(methyl-amino)pyrazolo[1,5-a]pyrazin-3-yl)oxy)-N-(3-((1-methylpyrrolidin-2-yl)methoxy)-5-(trifluoromethyl)phenyl)-1H-imidazo[4,5-b]pyridin-2-amine Synthesis of compound 331.1. To a solution of 304.9 (0.040 g, 0.126 mmol, 1.5 equiv) and Int-121 (0.032 g, 0.084 mmol, 1.0 equiv) in THF (2 mL) was added potassium tert-butoxide (1 M in THF, 0.25 mL, 0.252 mmol, 3.0 equiv) at 0° C. The reaction mixture was stirred at room temperature for 15 min. It was poured into ice-water and extracted with ethyl acetate. The combined organic layers were washed with brine, dried over anhydrous sodium sulfate, filtered, and concentrated under reduced pressure. To the residue was added THF (5 mL) and N-(3-dimethylaminopropyl)-N'-ethylcarbodiimide hydrochloride (0.144 g, 0.252 mmol, 3.0 equiv). The reaction mixture was stirred at 80° C. for 30 min. It was cooled to room temperature, poured into ice-water, and extracted with ethyl acetate. The combined organic layers were washed with brine, dried over anhydrous sodium sulfate, filtered, and concentrated under reduced

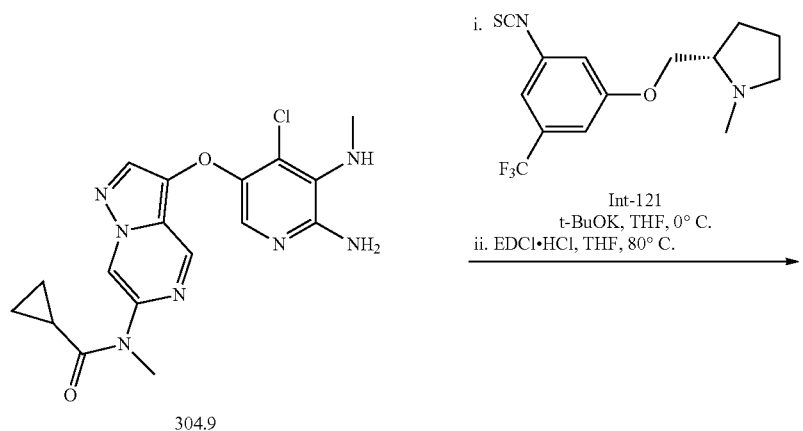

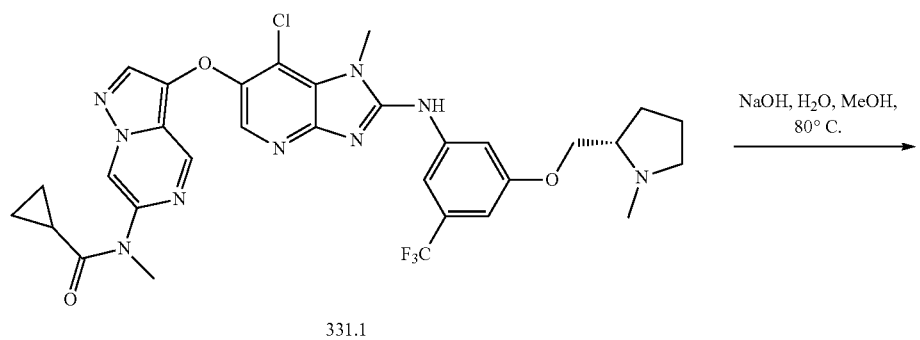

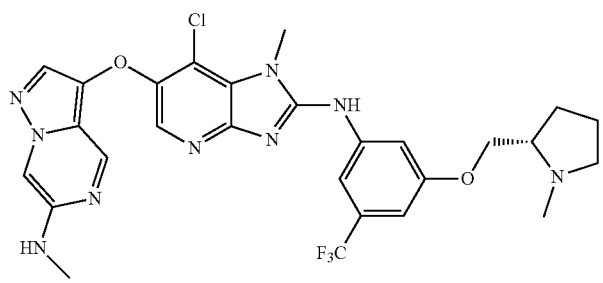

pressure. The residue was purified by flash column chromatography on silica gel (CombiFlash®, 2.8% methanol in DCM) to afford 331.1. MS (ES): m/z 671.0 [M+H]⁺.

Synthesis of I-331. Compound I-331 was prepared from 331.1 following the procedure described in the synthesis of I-304. The product was purified by flash column chromatography on silica gel (CombiFlash®, 2.6% methanol in DCM). MS (ES): m/z 602.3 [M+H]⁺, $^1$H NMR (MeOH-d$_4$, 400 MHz): δ 8.66 (s, 1H), 8.10 (s, 1H), 7.89 (s, 1H), 7.75 (s, 1H), 7.53 (s, 1H), 7.50 (s, 1H), 6.95 (s, 1H), 4.19 (s, 2H), 4.09 (s, 3H), 3.08 (bs, 1H), 2.85 (s, 3H), 2.66 (s, 3H), 2.61-2.58 (m, 2H), 2.21 (bs, 2H), 1.94 (bs, 2H).

Example 332: (R)-7-chloro-1-methyl-6-((6-(methylamino)pyrazolo[1,5-a]pyrazin-3-yl)oxy)-N-(3-((1-methylpyrrolidin-2-yl)methoxy)-5-(trifluoromethyl)phenyl)-1H-imidazo[4,5-b]pyridin-2-amine Synthesis of compound 332.1. Compound 332.1 was prepared from 304.9 and Int-122, following the procedure described in the synthesis of 331.1. The product was purified by flash column chromatography on silica gel (CombiFlash®, 2.8% methanol in DCM). MS (ES): m/z 671.2 [M+H]⁺.

Synthesis of I-332. Compound I-332 was prepared from 332.1 following the procedure described in the synthesis of I-304. The product was purified by flash column chromatography on silica gel (CombiFlash®, 2.6% methanol in DCM). MS (ES): m/z 602.4 [M+H]⁺, $^1$H NMR (DMSO-d$_6$, 400 MHz): δ 9.63 (s, 1H), 8.69 (s, 1H), 8.16 (s, 1H), 7.97 (s, 1H), 7.88 (s, 1H), 7.64 (s, 1H), 7.56 (s, 2H), 6.95 (s, 1H), 6.16-6.14 (d, J=5.2 HZ, 1H), 4.12 (bs, 2H), 4.03 (s, 3H), 3.30 (s, 1H), 2.73-2.71 (d, 3H), 2.47 (bs, 3H), 2.44 (bs, 2H), 2.05 (bs, 2H), 1.75 (bs, 2H).

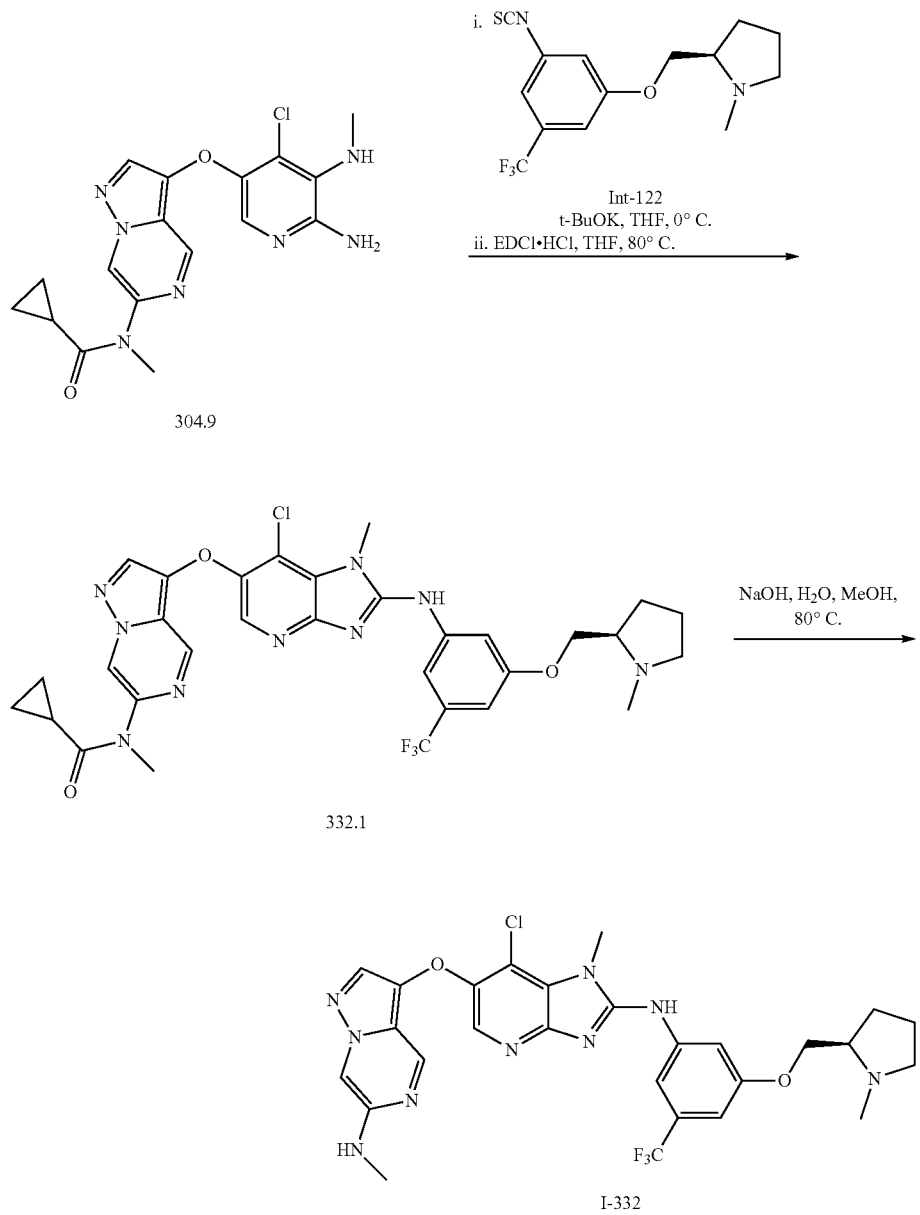

Example 333: 1-methyl-2-((1-methyl-2-oxo-5-(trifluoromethyl)-1,2-dihydropyridin-3-yl)amino)-6-((3-(trifluoromethyl)-1H-pyrazolo[3,4-b]pyridin-5-yl)oxy)-1H-imidazo[4,5-b]pyridine-7-carbonitrile

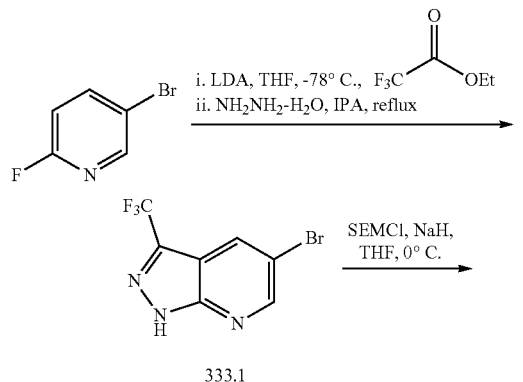
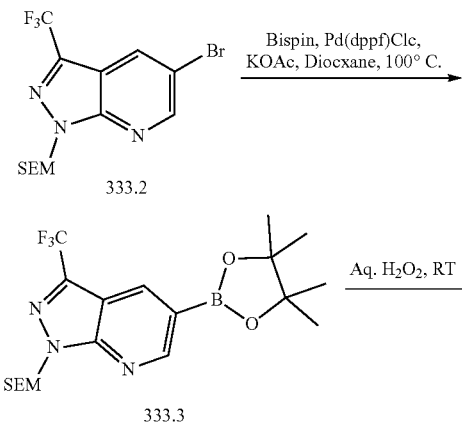
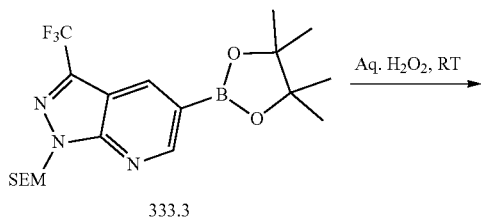
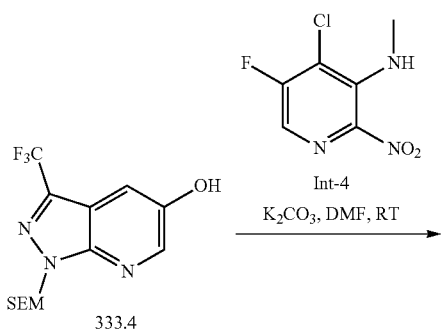
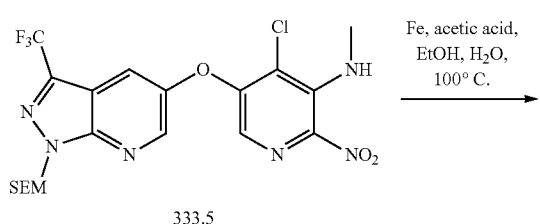
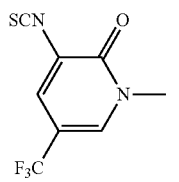
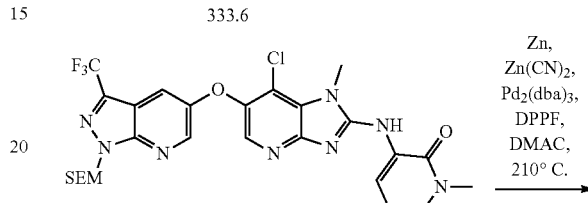
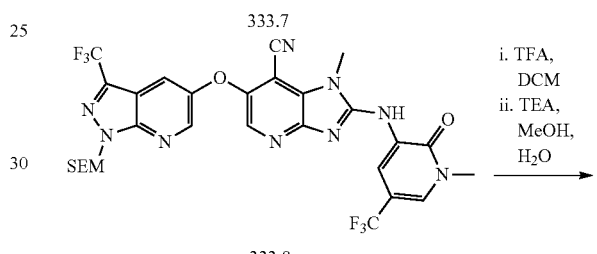
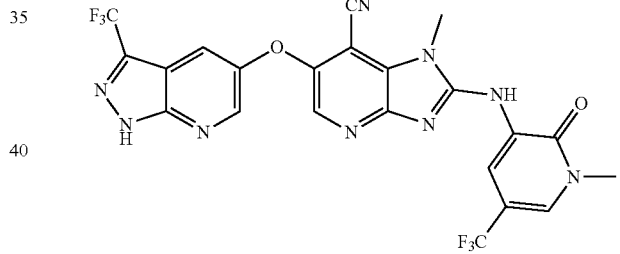
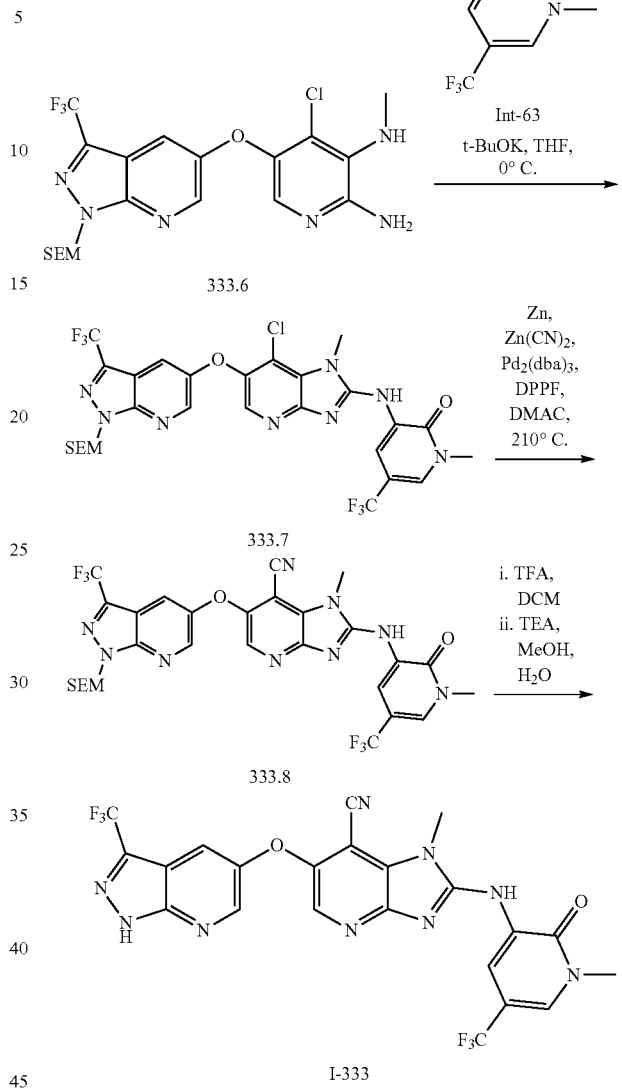

Synthesis of compound 333.1. To solution of lithium diisopropylamide (2 M in THF, (14.2 mL, 28.41 mmol, 1.0 equiv) at −78° C. in THF (60 mL) was added 5-bromo-2-fluoropyridine (5.0 g, 28.41 mmol, 1.0 equiv) and stirred at −78° C. for 30 min. To the mixture was added ethyl 2,2,2-trifluoroacetate (4.43 g, 31.25 mmol, 1.1 equiv) at −78° C. and stirred for 30 min. It was transferred into aqueous ammonium chloride solution and extracted with ethyl acetate. The combined organic layers were washed with brine, dried over anhydrous sodium sulfate, filtered, and concentrated under reduced pressure. To the residence was added isopropyl alcohol (50 mL) and hydrazine hydrate (2.96 g, 59.25 mmol, 5.0 equiv) at room temperature. The reaction mixture was stirred at 80° C. for 18 h. It was cooled to room temperature, transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford 333.1. MS (ES): m/z 267.1 [M+H]+.

Synthesis of compound 333.2. To a suspension of sodium hydride (0.523 g, 21.8 mmol, 2.0 equiv) in DMF (10 mL) was added a solution of 333.1 (2.9 g, 10.90 mmol, 1.0 equiv) in DMF (5 mL) at 0° C. and stirred for 5 min. To the mixture was added (2-chloromethoxyethyl)trimethylsilane (2.36 g, 14.17 mmol, 1.3 equiv) and stirred at room temperature for 30 min. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7% ethyl acetate in hexane) to afford 333.2. MS (ES): m/z 397.2 [M+H]+.

Synthesis of compound 333.3. A mixture of 333.2 (1.8 g, 4.54 mmol, 1.0 equiv), bis(pinacolato)diboron (2.3 g, 9.08 mmol, 2.0 equiv) and potassium acetate (0.889 g, 9.08 mmol, 2.0 equiv) in 1,4-dioxane (15 mL) was degassed by bubbling argon through for 5 min. Under argon atmosphere 1,1-bis(diphenylphosphino)ferrocene-palladium(II) dichloride DCM complex (0.066 g, 0.0908 mmol, 0.02 equiv) was added. The reaction mixture was stirred at 100° C. for 18 h. It was poured into ice-water and extracted with ethyl acetate. The combined organic layers were washed with brine, dried over anhydrous sodium sulfate, filtered, and concentrated under reduced pressure to afford 333.3. MS (ES): m/z 444.1 [M+H]+.

Synthesis of compound 333.4. A mixture of compound 333.3 (1.5 g, 3.38 mmol, 1.0 equiv) and hydrogen peroxide solution (20 mL) was stirred at room temperature for 8 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford 333.4. MS (ES): m/z 334.2 [M+H]+.

Synthesis of compound 333.5. Compound 333.5 was prepared from compound 333.4 and Int-4, following the procedure described in the synthesis of 19.1. The product was purified by flash column chromatography on silica gel (CombiFlash®, 35% ethyl acetate in hexane). MS (ES): m/z 519.5 [M+H]+.

Synthesis of compound 333.6. To a solution of 333.5 (0.850 g, 1.64 mmol, 1.0 equiv) in ethanol:water (2:1, 8 mL) was added iron powder (0.459 g, 8.2 mmol, 5.0 equiv) followed by acetic acid (0.492 g, 8.2 mmol, 5.0 equiv). The reaction mixture was stirred at 100° C. for 1 h. It was transferred into ice-water, filtered, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford 333.6. MS (ES): m/z 489.5 [M+H]+.

Synthesis of compound 333.7. Compound 333.7 was prepared from 333.6 and Int-63, following the procedure described in the synthesis of I-13. The product was purified by flash column chromatography on silica gel (CombiFlash®, 1.0% methanol in DCM). MS (ES): m/z 690.7 [M+H]+.

Synthesis of compound 333.8. Compound 333.8 was prepared from 333.7 following the procedure described in the synthesis of 330.6. The product was purified by flash column chromatography on silica gel (CombiFlash®, 1.5% methanol in DCM). MS (ES): m/z 680.4 [M+H]+.

Synthesis of I-333. To a solution of 333.8 (0.075 g, 0.110 mmol, 1.0 equiv) in DCM (4 mL) was added trifluoroacetic acid (1 mL) and stirred at room temperature for 24 h. The reaction mixture was concentrated under reduced pressure. To a solution of crude material in methanol (3 mL) was added water (1 mL), trimethylamine (1 mL) and stirred at room temperature for 18 h. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford I-333. MS (ES): m/z 550.5 [M+H]+, 1H NMR (DMSO-d6, 400 MHz): δ 14.74 (s, 1H), 8.79-8.78 (d, J=2.4 Hz, 1H), 8.65 (s, 1H), 8.18 (s, 2H), 8.00 (s, 1H), 4.00 (s, 3H), 3.67 (s, 3H).

Example 334: 1-methyl-6-((4-methyl-1H-pyrrolo[2,3-b]pyridin-5-yl)oxy)-2-((1-methyl-2-oxo-5-(trifluoromethyl)-1,2-dihydropyridin-3-yl)amino)-1H-imidazo[4,5-b]pyridine-7-carbonitrile

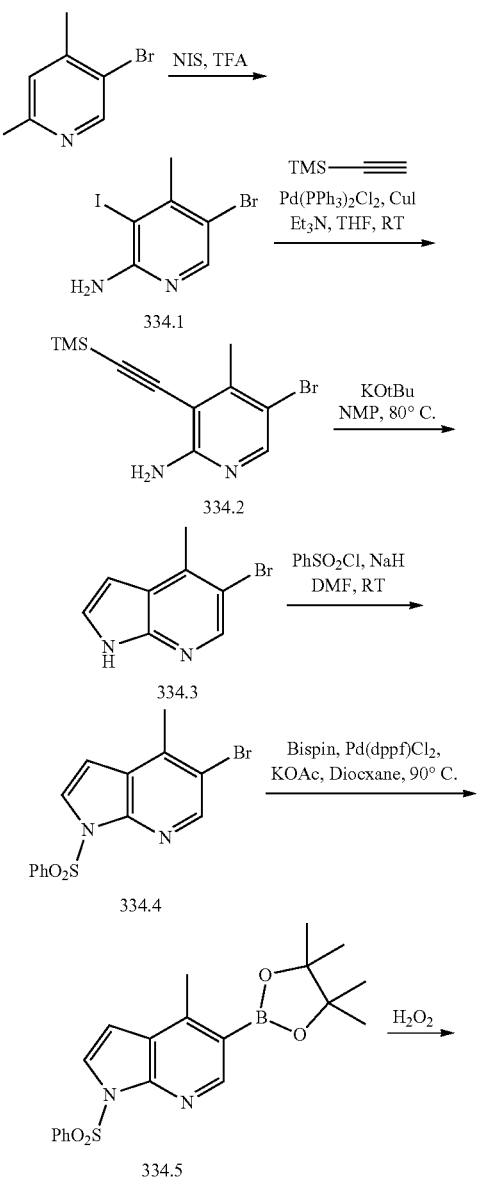

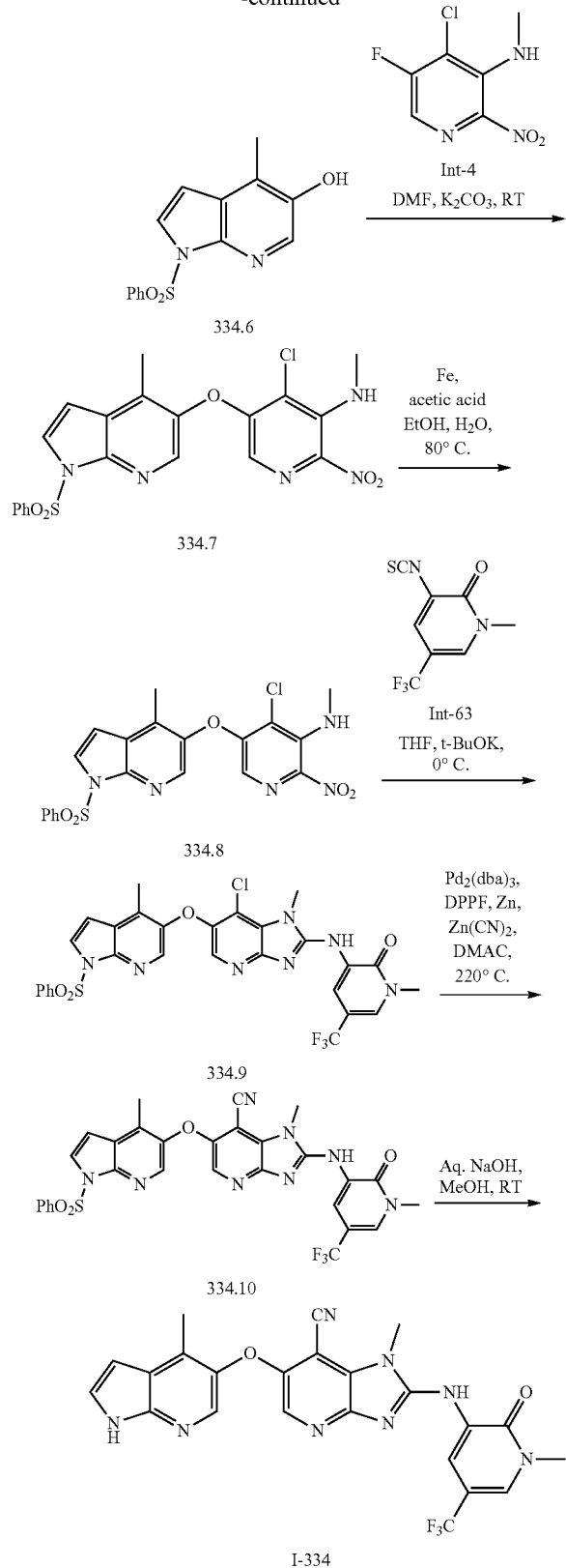

Synthesis of compound 334.1. To a solution of 5-bromo-4-methylpyridin-2-amine (9.0 g, 48.12 mmol, 1.0 equiv) in DMF (180 mL) was added trifluoroacetic acid (6.5 gm, 57.74 mmol, 1.2 equiv) at 0° C. followed by the addition of N-iodosuccinimide (16.16 g, 72.18 mmol, 1.5 equiv). The reaction mixture was stirred at 55° C. for 2 h. It was transferred into aqueous solution of sodium thiosulphate, saturated sodium bicarbonate solution was added, and stirred. The brown solids were collected by filtration and purified by flash column chromatography on silica gel (CombiFlash®, 1% methanol in DCM) to afford 334.1. MS (ES): m/z 313.1 [M+H]$^+$.

Synthesis of compound 334.2. A mixture of 334.1 (10 g, 31.96 mmol, 1.0 equiv), ethynyltrimethylsilane (4.08 g, 41.5 mmol, 1.3 equiv) and triethylamine (21.8 mL, 159.8 mmol, 5.0 equiv) in DMF (10 mL) was degassed by bubbling argon through for 10 min. Under argon atmosphere, bis(triphenylphosphine)palladium(II) dichloride (0.336 g, 0.479 mmol, 0.015 equiv) and copper iodide (0.122 g, 0.639 mmol, 0.02 equiv) were added, and degassed for 5 min. The reaction mixture was stirred at room temperature for 16 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2% ethyl acetate in hexane) to afford 334.2. MS (ES): m/z 284.1 [M+H]$^+$.

Synthesis of compound 334.3. To a solution of 334.2 (8 g, 28.24 mmol, 1.0 equiv) in N-methyl-2-pyrrolidone (80 mL) was added potassium tert-butoxide (1 M in THF, 56.48 mL, 56.48 mmol, 2.0 equiv). The reaction mixture was stirred at 80° C. for 30 min. It was cooled to room temperature, poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2% methanol in DCM) to afford 334.3. MS (ES): m/z 212.3 [M+H]$^+$.

Synthesis of compound 334.4. To a solution of 334.3 (3.0 g, 14.21 mmol, 1.0 equiv) in DMF (30 mL) was added sodium hydride (0.511 g, 21.31 mmol, 1.5 equiv) at 0° C. and stirred for 30 min. To the mixture was added benzyl sulphonyl chloride (3.2 g, 18.47 mmol, 1.3 equiv) and stirred at room temperature for 2 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 1.5% methanol in DCM) to afford 334.4. MS (ES): m/z 352.1 [M+H]$^+$.

Synthesis of compound 334.5. A mixture of 333.4 (1.7 g, 4.84 mmol, 1.0 equiv), bis(pinacolato)diboron (1.59 g, 6.29 mmol, 1.3 equiv) and potassium acetate (1.4 g, 14.52 mmol, 3 equiv) in 1,4-dioxane (17 mL) was degassed by bubbling argon through for 30 min. Under argon atmosphere, 1,1-bis(diphenylphosphino)ferrocene-palladium(II) dichloride DCM complex (0.176 g, 0.242 mmol, 0.05 equiv) was added. The reaction mixture was stirred at 90° C. for 5 h. The reaction mixture was poured into ice-water and extracted with ethyl acetate. The combined organic layers were washed with brine, dried over anhydrous sodium sulfate, filtered, and concentrated under reduced pressure to afford 334.5. MS (ES): m/z 399.1 [M+H]$^+$.

Synthesis of compound 334.6. To a solution of 334.5 (1.7 g, 4.27 mmol, 1.0 equiv) in acetonitrile:methanol (1:1, 17 mL) was added aqueous hydrogen peroxide solution (8.5 mL). The reaction mixture was stirred at room temperature for 12 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 45% ethyl acetate in hexane) to afford 334.6. MS (ES): m/z 289.2 [M+H]$^+$.

Synthesis of compound 334.7. Compound 334.7 was prepared from compound 334.6 and Int-4, following the procedure described in the synthesis of 19.1. The product was purified by flash column chromatography on silica gel (CombiFlash®, 25% ethyl acetate in hexane). MS (ES): m/z 474.5 [M+H]$^+$.

Synthesis of compound 334.8. Compound 334.8 was prepared from 334.7 following the procedure described in the synthesis of 5.4. The product was purified by flash column chromatography on silica gel (CombiFlash®, 30% ethyl acetate in hexane). MS (ES): m/z 444.5 [M+H]$^+$.

Synthesis of compound 334.9. Compound 334.9 was prepared from 334.8 and Int-63, following the procedure described in the synthesis of I-13. The product was purified by flash column chromatography on silica gel (CombiFlash®, 50% ethyl acetate in hexane). MS (ES): m/z 645.7 [M+H]$^+$.

Synthesis of compound 334.10. Compound 334.10 was prepared from 334.9 following the procedure described in the synthesis of 300.8. The product was purified by flash column chromatography on silica gel (CombiFlash®, 30% ethyl acetate in hexane) to afford 334.10. MS (ES): m/z 635.3 [M+H]$^+$.

Synthesis of I-334. To a solution of 334.10 (0.070 g, 0.110 mmol, 1.0 equiv) in methanol:THF (4:1, 2 mL) was added a solution of sodium hydroxide (0.044 g, 1.1 mmol, 40 equiv) in water (1 mL). The reaction mixture was stirred at 80° C. for 30 min. It was cooled to room temperature and concentrated under reduced pressure. The residue was transferred into water and extracted with DCM. The combined organic layers were washed with brine, dried over anhydrous sodium sulfate, filtered, and concentrated under reduced pressure. The residue was purified by trituration by methanol) to afford I-334. MS (ES): m/z 495.2 [M+H]$^+$, $^1$H NMR (DMSO-d$_6$, 400 MHz): δ 11.80 (s, 1H), 8.95 (s, 1H), 8.61 (s, 1H), 8.16 (s, 1H), 8.08 (s, 1H), 7.66 (s, 1H), 7.56 (s, 1H), 6.61 (s, 1H), 4.00 (s, 3H), 3.67 (s, 3H), 2.52 (s, 3H).

Example 335: 6-((4-fluoro-1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

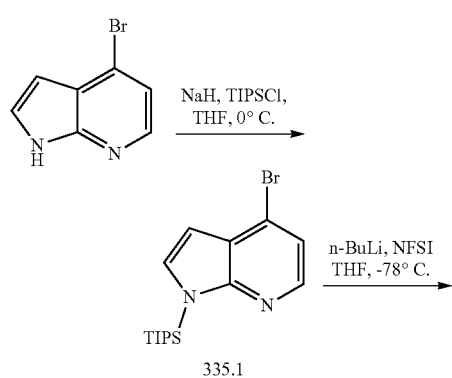

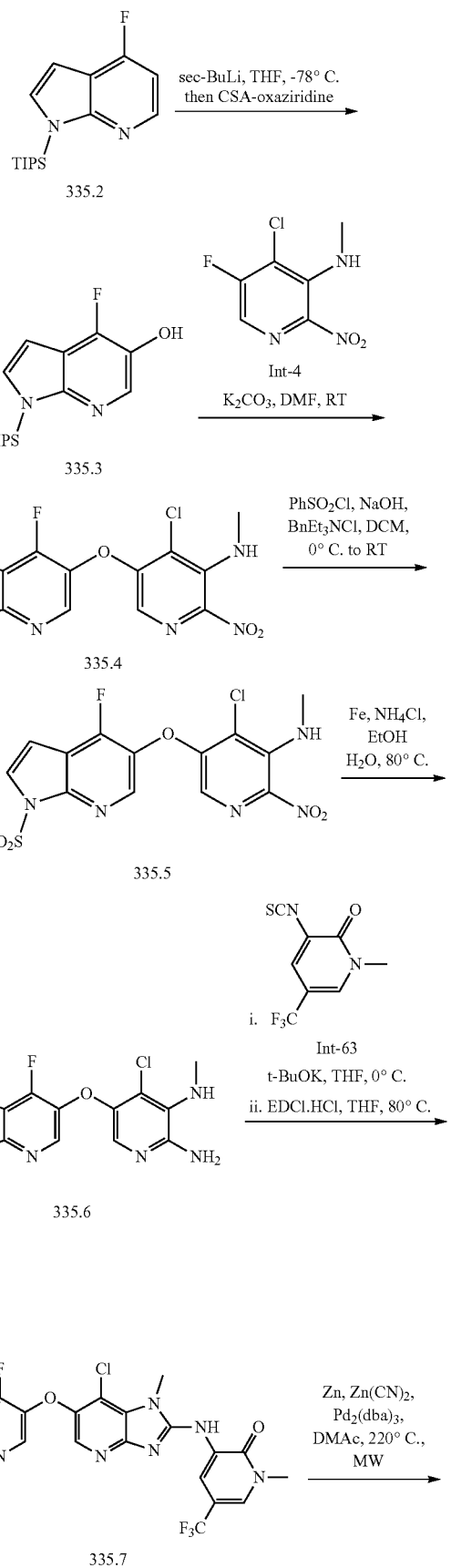

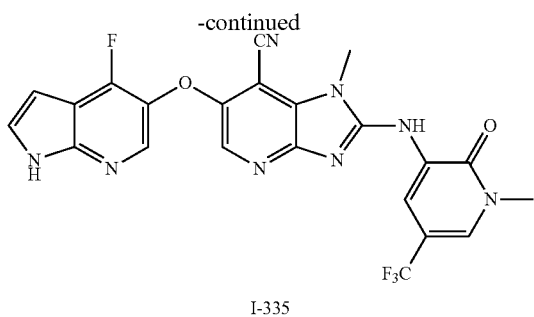

I-335

Synthesis of compound 335.1 TO a solution of 4-bromo-1H-pyrrolo[2,3-b]pyridine (10.0 g, 50.75 mmol, 1.0 equiv) in THF (200 mL) was added sodium hydride (1.46 g, 60.9 mmol, 1.2 equiv) at 0° C. and stirred for 10 min. To the mixture was added triisopropylsilyl chloride (20.462 g, 106.57 mmol, 2.1 equiv) and stirred at 0° C. for 1 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, hexane) to afford 335.1. MS (ES): m/z 354.1 [M+H]+.

Synthesis of compound 335.2. To a solution of 335.1 (4.0 g, 11.32 mmol, 1.0 equiv) in THF (40 mL) was added n-butyl lithium (2.5 M in THF) (6.79 mL, 16.98 mmol, 1.5 equiv) at −78° C. and stirred for 15 min followed by a solution of N-fluorobenzenesulfonimide (4.27 g, 13.58 mmol, 1.2 equiv) in THF (10 mL) and stirred at −78° C. for 15 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5% ethyl acetate in hexane) to afford 335.2. MS (ES): m/z 293.1 [M+H]+.

Synthesis of compound 335.3. To a solution of 335.2 (1.4 g, 4.79 mmol, 1.0 equiv) in THE (30 mL) was added sec-butyl lithium (1.3 M in THF, 8.1 mL, 10.53 mmol, 2.2 equiv) at −78° C. and stirred for 1 h. To the solution was added (1R)-(−)-(10-camphorsulfonyl)oxaziridine (2.74 g, 11.97 mmol, 2.5 equiv) in THE (20 mL) and stirred at for 1 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7% ethyl acetate in hexane) to afford 335.3. MS (ES): m/z 309.1 [M+H]+.

Synthesis of compound 335.4. Compound 335.4 was prepared from 335.3 and Int-4, following the procedure described in the synthesis of 19.1. The product was purified by flash column chromatography on silica gel (CombiFlash®, 30% ethyl acetate in hexane). MS (ES): m/z 338.5 [M+H]+.

Synthesis of compound 335.5. To a solution of 335.4 (0.300 g, 0.888 mmol, 1.0 equiv) and benzyltriethylammonium chloride (0.004 g, 0.0177 mmol, 0.02 equiv) in DCM (7 mL) was added powdered sodium hydroxide (0.110 g, 2.77 mmol, 3.12 equiv) at 0° C. To the mixture was added benzyl sulphonyl chloride (0.155 g, 0.888 mmol, 1.0 equiv) and stirred at 0° C. for 30 min. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford 335.5. MS (ES): m/z 478.1 [M+H]+.

Synthesis of compound 335.6. Compound 335.6 was prepared from 335.5 following the procedure described in the synthesis of 5.4. The product was purified by flash column chromatography on silica gel (CombiFlash®, 18% ethyl acetate in hexane). MS (ES): m/z 448.5 [M+H]+.

Synthesis of compound 335.7. Compound 335.7 was prepared from 335.6 and Int-63, following the procedure described in the synthesis of 331.1. The product was purified by flash column chromatography on silica gel (CombiFlash®, 2.5% methanol in DCM). MS (ES): m/z 508.7 [M+H]+.

Synthesis of I-335. Compound I-335 was prepared from 335.7 following the procedure described in the synthesis of 300.8. The product was purified by flash column chromatography on silica gel (CombiFlash®, 3.0% methanol in DCM). MS (ES): m/z 499.3 [M+H]+, 1H NMR (DMSO-$d_6$, 400 MHz): δ 12.20 (s, 1H), 8.96 (s, 1H), 8.61 (s, 1H), 8.33-8.30 (d, J=9.6, 1H), 8.16 (s, 1H), 7.90 (s, 1H), 7.64 (s, 1H), 6.63 (s, 1H), 3.99 (s, 3H), 3.66 (s, 3H).

Example 336: 1 1-methyl-2-((1-methyl-2-oxo-5-(trifluoromethyl)-1,2-dihydropyridin-3-yl)amino)-6-((6-(2-morpholinoethoxy)pyrazolo[1,5-a]pyridin-3-yl)oxy)-1H-imidazo[4,5-b]pyridine-7-carbonitrile

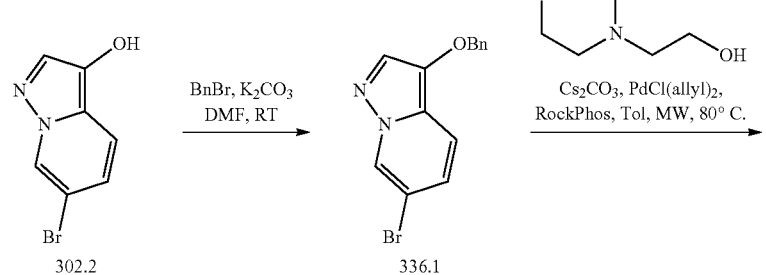

302.2    336.1

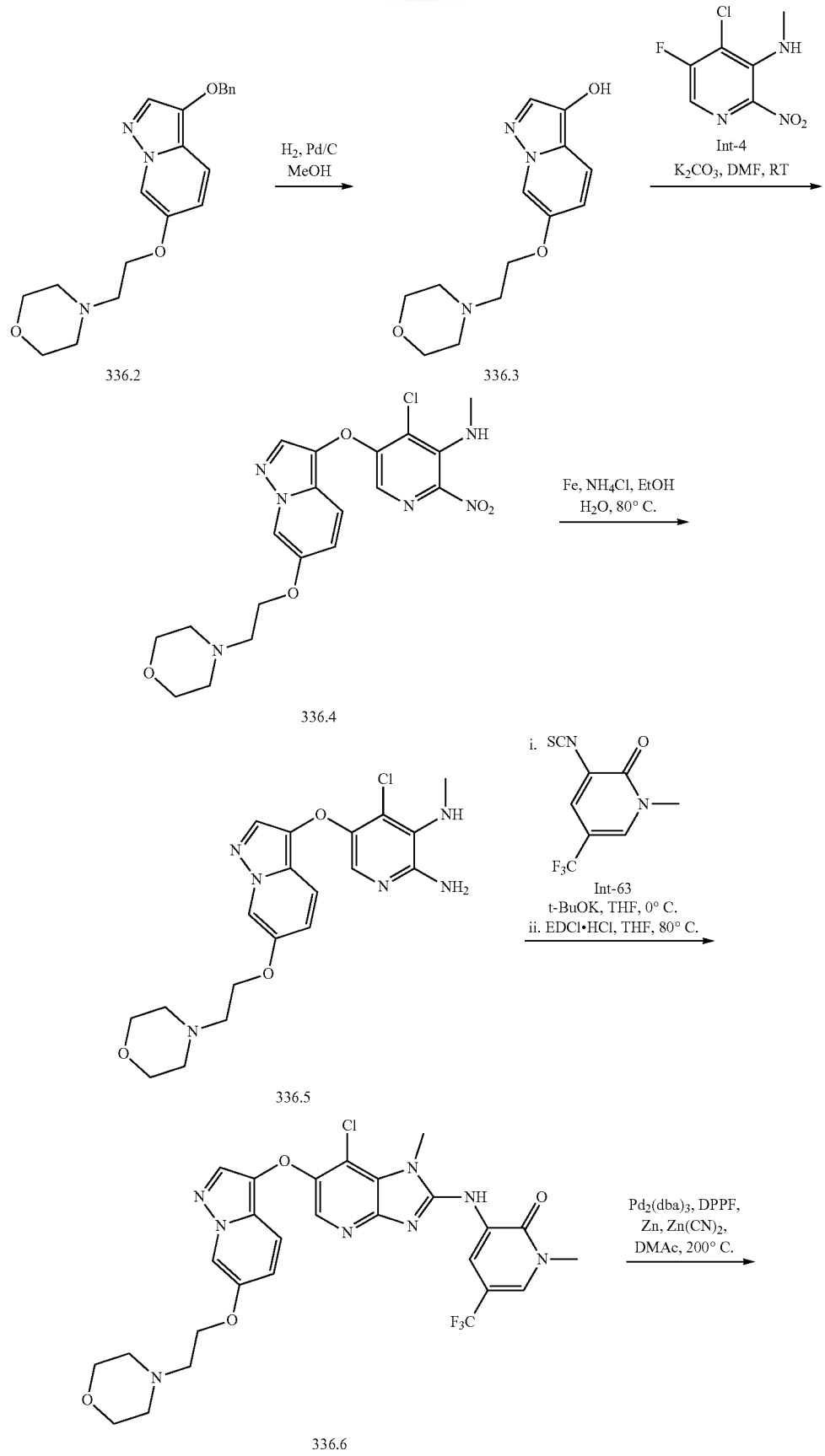

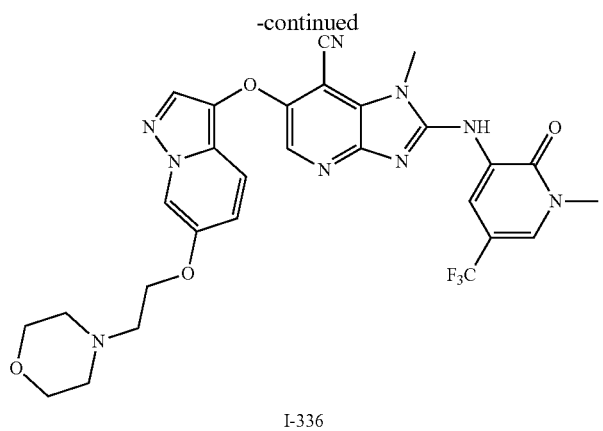

I-336

Synthesis of compound 336.1. To a mixture of 302.2 (1.0 g, 4.69 mmol, 1.0 equiv) and potassium carbonate (1.6 g, 11.72 mmol, 2.5 equiv) in DMF (20 mL) was added benzyl bromide (1.25 g, 7.035 mmol, 1.5 equiv) at 0° C. The reaction mixture was stirred at room temperature for 2 h. It was cooled to room temperature, poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 18% ethyl acetate in hexane) to afford 336.1. MS (ES): m/z 304.3 [M+H]$^+$.

Synthesis of compound 336.2. A suspension of 2-di(tert-butyl)phosphino-2',4',6'-triisopropyl-3-methoxy-6-methyl-biphenyl (0.162 g, 0.346 mmol, 0.15 equiv), allylpalladium (II) chloride dimer (0.042 g, 0.115 mmol, 0.05 equiv) and cesium carbonate (1.12 g, 3.46 mmol, 1.5 equiv) in toluene (10 mL) was degassed by bubbling argon through for 10 min. Under argon atmosphere, 336.1 (0.700 g, 2.31 mmol, 1.0 equiv) and 2-morpholinoethan-1-ol (0.605 g, 4.62 mmol, 2.0 equiv) were added, and degassed for 5 min. The reaction mixture was stirred at 80° C. in a microwave reactor for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford 336.2. MS (ES): m/z 354.5 [M+H]$^+$.

Synthesis of compound 336.3. A mixture of compound 336.2 (0.350 g, 0.990 mmol, 1.0 equiv) and 10% palladium on charcoal (0.115 g) in methanol (10 mL) was stirred under hydrogen (1 atm) for 4 h. The reaction mixture was filtered through a pad of Celite® and rinsed with methanol. The filtrate was concentrated under reduced pressure to afford 336.3. MS (ES): m/z 264.2 [M+H]$^+$.

Synthesis of compound 336.4. Compound 336.4 was prepared from 336.3 and Int-4, following the procedure described in the synthesis of 19.1. The product was purified by flash column chromatography on silica gel (Combi-Flash®, 2% methanol in DCM). MS (ES): m/z 449.5 [M+H]$^+$.

Synthesis of compound 336.5. Compound 336.5 was prepared from 336.4 following the procedure described in the synthesis of 5.4. The product was purified by flash column chromatography on silica gel (CombiFlash®, 3% methanol in DCM). MS (ES): m/z 419.5 [M+H]$^+$.

Synthesis of compound 336.6. Compound 336.6 was prepared from 336.5 and Int-63, following the procedure described in the synthesis of 331.1. The product was purified by flash column chromatography on silica gel (Combi-Flash®, 2.1% methanol in DCM). MS (ES): m/z 620.3 [M+H]$^+$.

Synthesis of I-336. A mixture of 336.6 (0.070 g, 0.113 mmol, 1.0 equiv), zinc dust (0.001 g, 0.002 mmol, 0.02 equiv) and zinc cyanide (0.065 g, 0.565 mmol, 5 equiv) in N,N-dimethylacetamide (2 mL) was degassed by bubbling argon through for 10 min. Under argon atmosphere, tris(dibenzylideneacetone)dipalladium(0) (0.007 g, 0.008 mmol, 0.07 equiv) and 1,1'-bis(diphenylphosphino)ferrocene (0.009 g, 0.016 mmol, 0.15 equiv) were added, and degassed for 5 min. The reaction mixture was stirred at 200° C. for 1 h. It was cooled to room temperature, transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.2% methanol in DCM) to afford I-336. MS (ES): m/z 610.4 [M+H]$^+$, $^1$H NMR (DMSO-d$_6$, 400 MHz): δ 8.97 (s, 1H), 8.62 (s, 1H), 8.44 (s, 1H), 8.17 (s, 1H), 8.05 (s, 1H), 7.96 (s, 1H), 7.47-7.45 (d, J=8.0 Hz, 1H), 7.08 (bs, 1H), 4.16 (s, 2H), 4.00 (s, 3H), 3.67 (bs, 4H), 3.60 (bs, 4H), 2.73 (bs, 5H).

Example 337: 6-((3-cyclopropyl-1H-pyrazolo[3,4-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

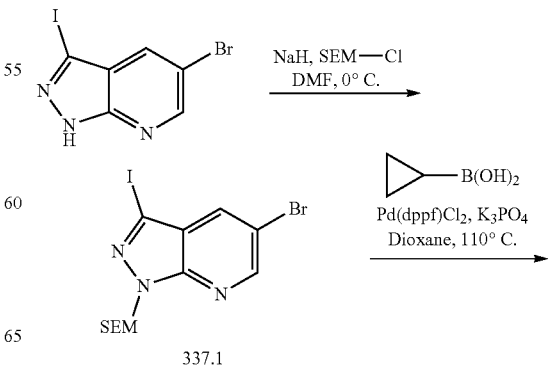

337.1

-continued

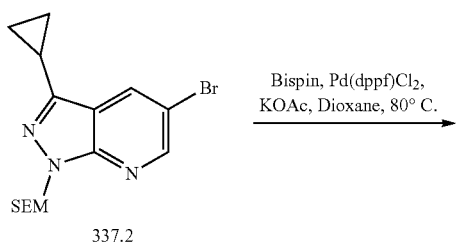
337.2

Bispin, Pd(dppf)Cl₂,
KOAc, Dioxane, 80° C.

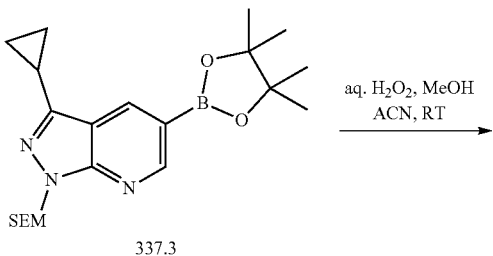
337.3 aq. H₂O₂, MeOH
ACN, RT

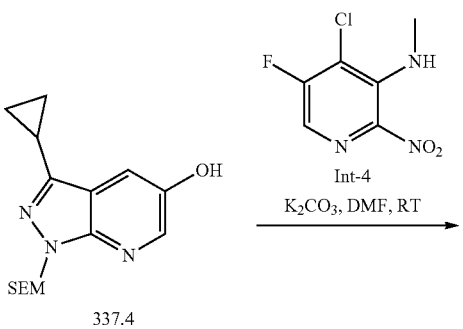
337.4

Int-4
K₂CO₃, DMF, RT

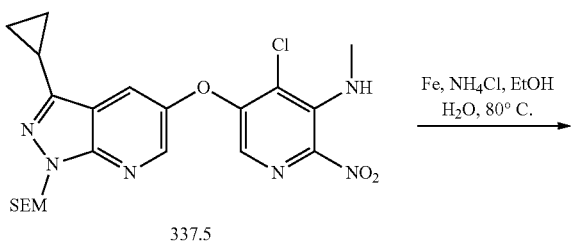
337.5

Fe, NH₄Cl, EtOH
H₂O, 80° C.

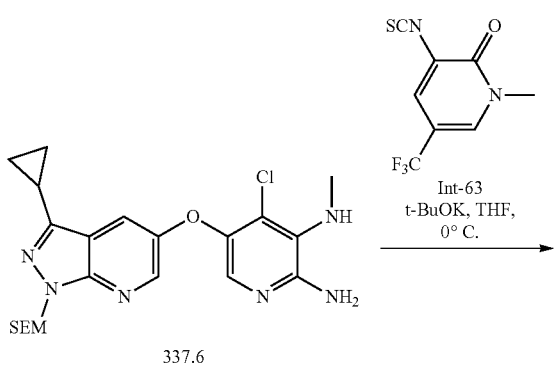
337.6

Int-63
t-BuOK, THF,
0° C.

-continued

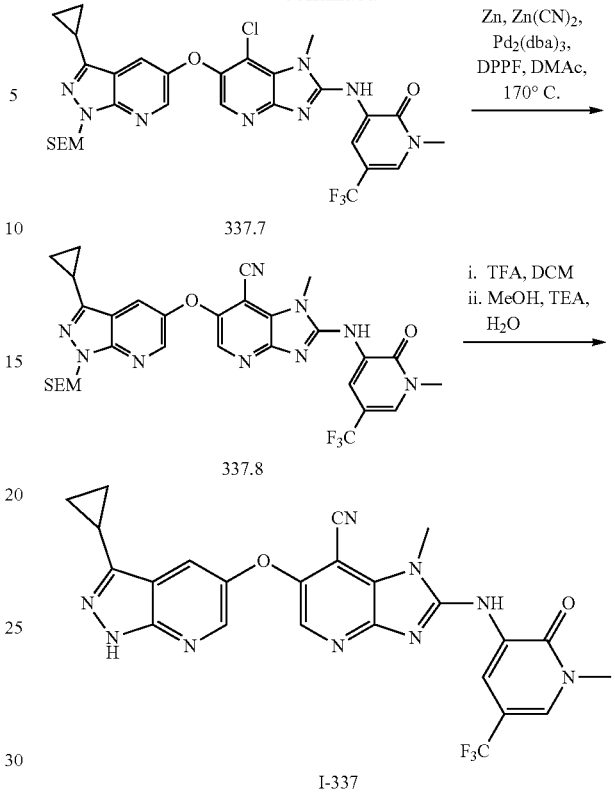
337.7

Zn, Zn(CN)₂,
Pd₂(dba)₃,
DPPF, DMAc,
170° C.

337.8 i. TFA, DCM
ii. MeOH, TEA, H₂O

I-337

Synthesis of compound 337.1. To a suspension of sodium hydride (2.4 g, 102.0 mmol, 2.0 equiv) in DMF (50 mL) was added a solution of 5-bromo-3-iodo-1H-pyrazolo[3,4-b]pyridine (20 g, 61.74 mmol, 1.0 equiv) in DMF (110 mL) at 0° C. and stirred for 15 min. To the mixture was added (2-chloromethoxyethyl)trimethylsilane (14.36 g, 86.5 mmol, 1.7 equiv) and stirred at room temperature for 2 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 337.1. MS (ES): m/z 455.1 [M+H]⁺.

Synthesis of compound 337.2. A mixture of 337.1 (2.0 g, 4.40 mmol, 1.0 equiv), cyclopropylboronic acid (1.51 g, 17.6 mmol, 4.0 equiv) and potassium phosphate (0.107 g, 1.1 mmol, 2.0 equiv) in 1,4-dioxane (20 mL) was degassed by bubbling argon through for 10 min. [1,1'-Bis(diphenylphosphino)ferrocene]dichloropalladium(II) complex with DCM (0.018 g, 0.022 mmol, 0.05 equiv) was added, and degassed for 5 min. The reaction mixture was stirred at 110° C. for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 9.0% ethyl acetate in hexane) to afford 337.2. MS (ES): m/z 369.2 [M+H]⁺.

Synthesis of compound 337.3. A mixture of 337.2 (0.700 g, 1.9 mmol, 1.0 equiv), bis(pinacolato)diboron (0.578 g, 2.2 mmol, 2.0 equiv) and potassium acetate (0.371 g, 3.7 mmol, 2.0 equiv) in 1,4-dioxane (15 mL) was degassed by bubbling argon through for 10 min. To the mixture was added

[1,1′-bis(diphenylphosphino)ferrocene]dichloropalladium (II) complex with DCM (0.067 g, 0.09 mmol, 0.02 equiv), and degassed for 5 min. The reaction mixture was stirred at 111° C. for 1 h. It was transferred into water and extracted with ethyl acetate. The combined organic layers were washed with brine, dried over anhydrous sodium sulfate, filtered, and concentrated under reduced pressure to afford 337.3. MS (ES): m/z 416.1 [M+H]$^+$.

Synthesis of compound 337.4. To a solution of 337.3 (0.550 g, 1.32 mmol, 1.0 equiv) in methanol (10 mL) and acetonitrile (10 mL) was added hydrogen peroxide (8 mL) at 0° C. and stirred for 6 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane) to afford 337.4. MS (ES): m/z 306.1 [M+H]$^+$.

Synthesis of compound 337.5. Compound 337.5 was prepared from 337.4 and Int-4, following the procedure described in the synthesis of 19.1. The product residue was purified by flash column chromatography on silica gel (CombiFlash®, 42% ethyl acetate in hexane). MS (ES): m/z 492.0[M+H]$^+$.

Synthesis of compound 337.6. Compound 337.6 was prepared from 337.5 following the procedure described in the synthesis of 5.4. The product was purified by flash column chromatography on silica gel (CombiFlash®, 25% ethyl acetate in hexane). MS (ES): m/z 462.0 [M+H]$^+$.

Synthesis of compound 337.7. Compound 337.7 was prepared from 337.6 and Int-63, following the procedure described in the synthesis of I-13. The product was purified by flash column chromatography on silica gel (CombiFlash®, 2.6% methanol in DCM. MS (ES): m/z: 662.1 [M+H]$^+$.

Synthesis of compound 337.8. Compound 337.8 was prepared from 337.7 following the procedure described in the synthesis of I-157. The product was purified by flash column chromatography on silica gel (CombiFlash®, 1.5% methanol in DCM). MS (ES): m/z 652.0 [M+H]$^+$.

Synthesis of I-337. To a solution of 337.8 (0.090 g, 0.138 mmol, 1.0 equiv) in DCM (4 mL) was added trifluoracetic acid (1.0 mL) at 0° C. and stirred for 2 h. It was transferred into ice-saturated sodium bicarbonate solution and extracted with DCM. The combined organic layers were washed with brine, dried over anhydrous sodium sulfate, filtered, and concentrated under reduced pressure. To the residue in a mixture of methanol-water was added triethylamine (1.5 mL). The reaction mixture was stirred at 80° C. for 2 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 2.5% methanol in DCM) to afford I-337. MS (ES): m/z: 522.3 [M+H]$^+$, $^1$H NMR (DMSO-d$_6$, 400 MHz): δ 13.31 (s, 1H), 9.02 (s, 1H), 8.65 (s, 1H), 8.55-8.54 (d, J=2.4 Hz, 1H), 8.18 (s, 1H), 8.10 (s, 1H), 8.05 (s, 1H), 4.00 (s, 3H), 3.67 (s, 3H), 2.31-2.26 (m, 1H), 0.96 (bs, 4H).

Example 338: 7-chloro-N-(4,4-dimethyl-4,5,6,7-tetrahydropyrazolo[1,5-a]pyridin-2-yl)-1-methyl-6-((6-(methylamino)pyrazolo[1,5-a]pyrazin-3-yl)oxy)-1H-imidazo[4,5-b]pyridin-2-amine

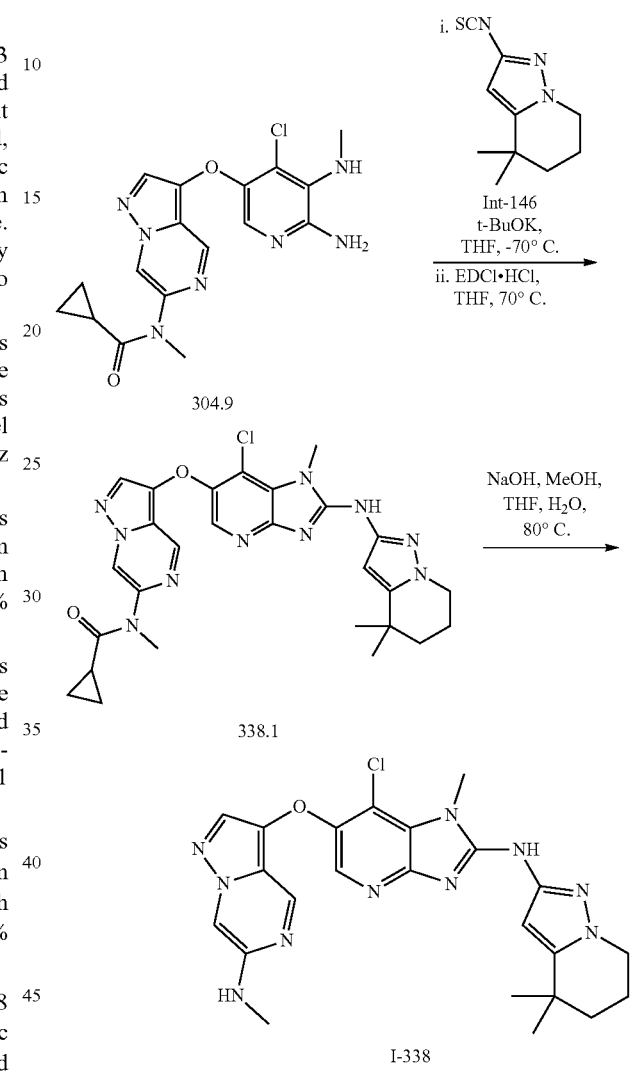

Synthesis of compound 338.1. Compound 338.1 was prepared from 304.9 and Int-146, following the procedure described in the synthesis of I-51. The product was purified by flash column chromatography on silica gel (CombiFlash®, 2.5% methanol in DCM). MS (ES): m/z 562.05 [M+H]$^+$.

Synthesis of I-338. Compound I-338 was prepared from 338.1 following the procedure described in the synthesis of I-304. The product was purified by flash column chromatography on silica gel (CombiFlash®, 3.5% methanol in DCM). MS (ES): m/z 493.3 [M+H]$^+$, $^1$H NMR (DMSO-d$_6$, 400 MHz): δ 9.97 (s, 1H), 8.66 (s, 1H), 8.05 (s, 1H), 7.61 (s, 1H), 7.53 (s, 1H), 6.57 (s, 1H), 6.13-6.12 (d, J=5.2 Hz, 1H), 3.93 (s, 3H), 2.71-2.69 (d, 3H), 2.02-1.99 (m, 2H), 1.68-1.67 (m, 2H), 1.30 (s, 6H), 1.23 (bs, 2H).

Example 339: 7-chloro-1-methyl-N-(3-(4-methyl-1H-imidazol-1-yl)-5-(trifluoromethyl)phenyl)-6-((6-(methylamino)pyrazolo[1,5-a]pyrazin-3-yl)oxy)-1H-imidazo[4,5-b]pyridin-2-amine Synthesis of I-339. Compound I-339 was prepared from 339.1 following the procedure described in the synthesis of I-304. The product was purified by flash column chromatography on silica gel (CombiFlash®, 3.9% methanol in

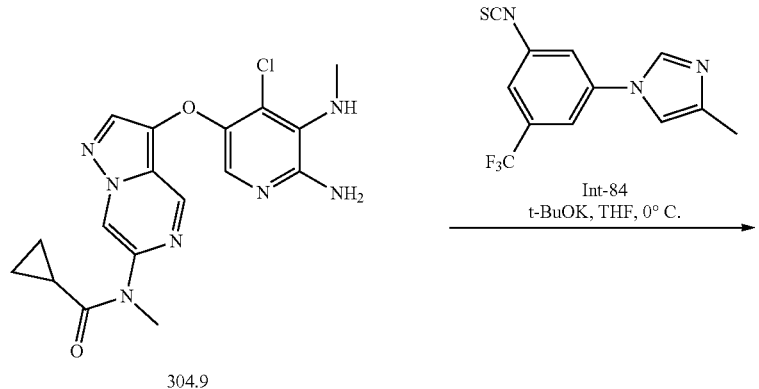

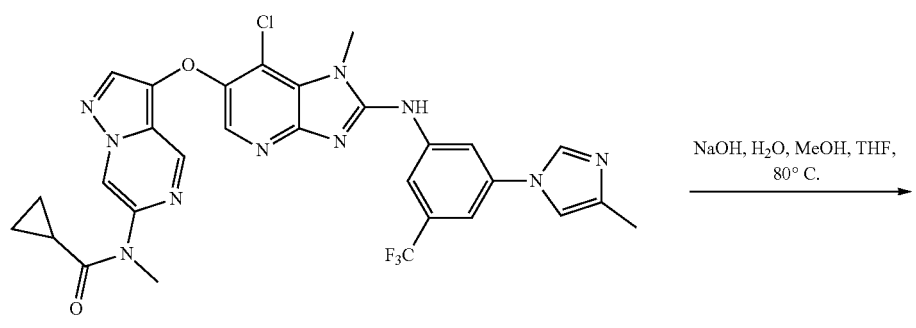

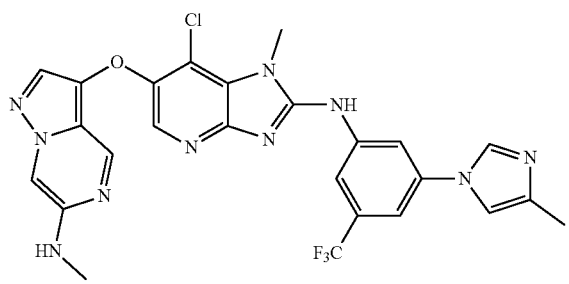

Synthesis of compound 339.1. Compound 339.1 was prepared from 304.9 and Int-84, following the procedure described in the synthesis of I-13. The product was purified by flash column chromatography on silica gel (CombiFlash®, 3.0% methanol in DCM). MS (ES): m/z 638.02 [M+H]⁺.

DCM). MS (ES): m/z 569.2 [M+H]⁺, ¹H NMR (DMSO-$d_6$, 400 MHz): δ 9.87 (s, 1H), 8.69 (s, 1H), 8.39 (s, 1H), 8.30 (s, 1H), 8.22 (s, 1H), 8.18 (s, 1H), 7.65 (bs, 2H), 7.56 (s, 1H), 7.48 (s, 1H), 6.16-6.15 (d, J=4.0 Hz, 1H), 4.06 (s, 3H), 2.73-2.72 (d, 3H), 2.21 (s, 3H).

Example 340: (R)-7-chloro-1-methyl-6-((6-(methyl-amino)pyrazolo[1,5-a]pyrazin-3-yl)oxy)-N-(1-(tetrahydrofuran-3-yl)-5-(trifluoromethyl)-1H-pyrazol-3-yl)-1H-imidazo[4,5-b]pyridin-2-amine

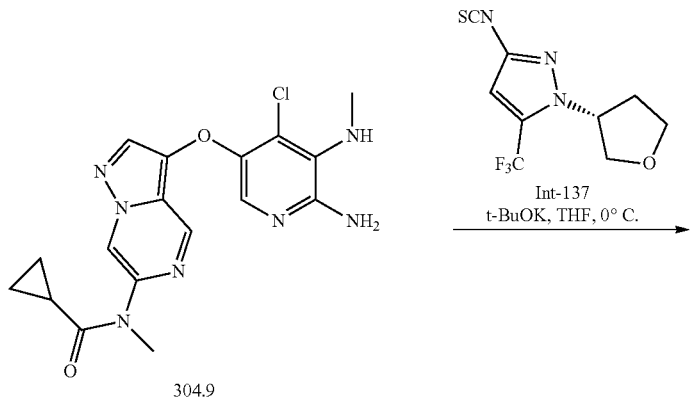

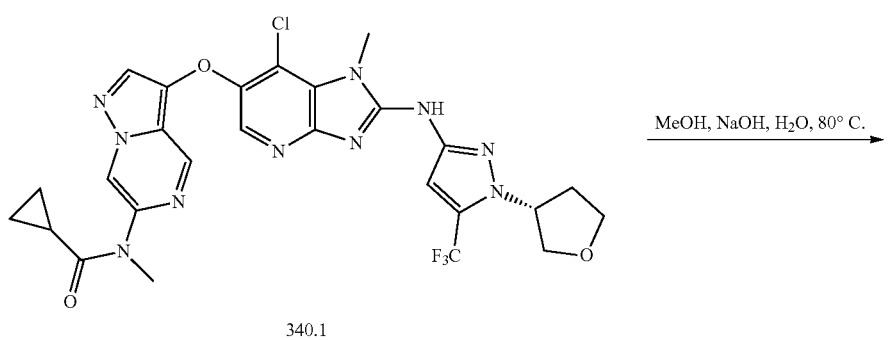

Synthesis of compound 340.1. Compound 340.1 was prepared from 304.9 and Int-137, following the procedure described in the synthesis of I-13. The product was purified by flash column chromatography on silica gel (CombiFlash®, 2.1% methanol in DCM). MS (ES): m/z 617.99 [M+H]+.

Synthesis of I-340. Compound I-340 was prepared from 340.1 following the procedure described in the synthesis of I-304. The product was purified by flash column chromatography on silica gel (CombiFlash®, 3.1% methanol in DCM). MS (ES): m/z 549.4 [M+H]+, 1H NMR (DMSO-d6, 400 MHz): δ 8.93 (s, 1H), 8.66 (s, 1H), 8.06 (s, 1H), 7.61 (s, 1H), 7.53 (s, 1H), 7.31 (s, 1H), 6.13-6.12 (d, J=4.8 Hz, 1H), 5.10 (bs, 1H), 4.08 (s, 3H), 4.06-4.04 (m, 2H), 3.71 (bs, 2H), 2.71-2.69 (d, 3H), 2.67 (bs, 2H).

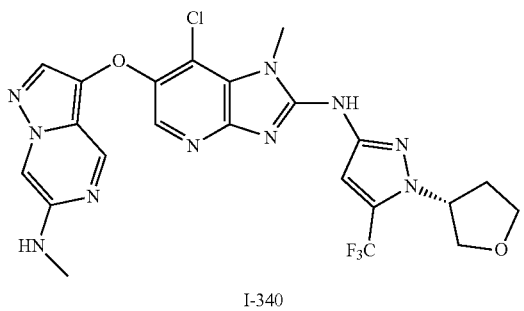

Example 341: 1-methyl-6-((3-methyl-1H-pyrazolo[3,4-b]pyridin-5-yl)oxy)-2-((1-methyl-2-oxo-5-(trifluoromethyl)-1,2-dihydropyridin-3-yl)amino)-1H-imidazo[4,5-b]pyridine-7-carbonitrile

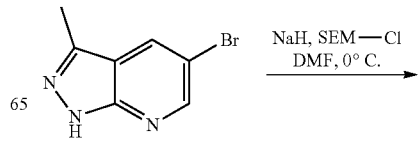

1069
-continued

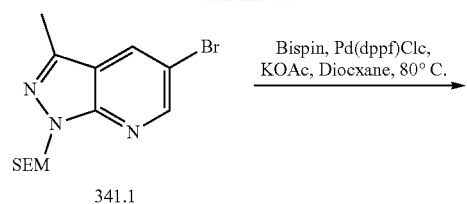
341.1

Bispin, Pd(dppf)Cl₂,
KOAc, Dioxane, 80° C.
→

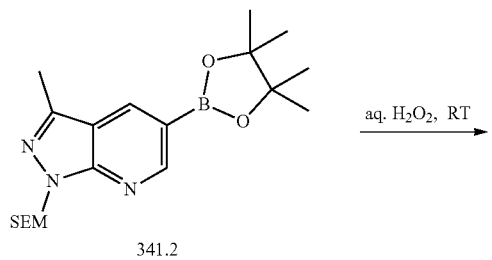
341.2 aq. H₂O₂, RT
→

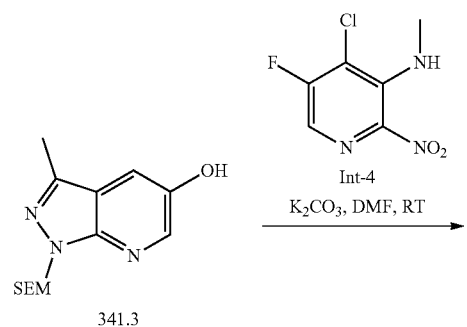
341.3

Int-4
K₂CO₃, DMF, RT
→

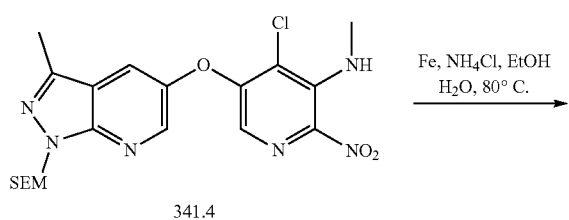
341.4

Fe, NH₄Cl, EtOH
H₂O, 80° C.
→

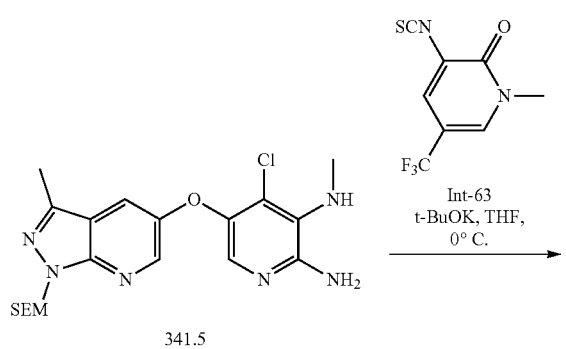
341.5

Int-63
t-BuOK, THF,
0° C.
→

1070
-continued

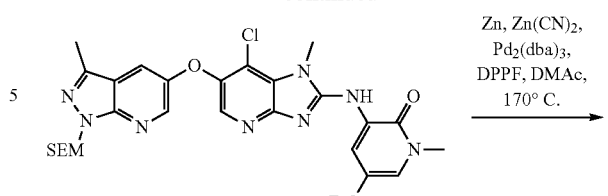
341.6

Zn, Zn(CN)₂,
Pd₂(dba)₃,
DPPF, DMAc,
170° C.
→

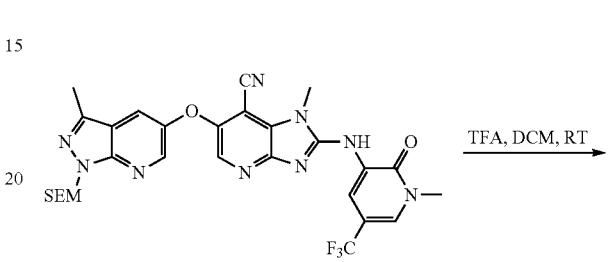
341.7

TFA, DCM, RT
→

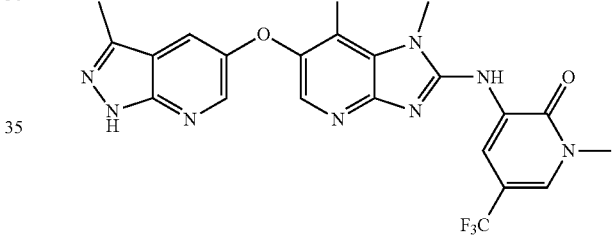
I-341

Synthesis of compound 341.1. To a suspension of sodium hydride (0.750 g, 18.0 mmol, 2.0 equiv) in DMF (5 mL) was added a solution of 5-bromo-3-methyl-1H-pyrazolo[3,4-b]pyridine (2 g, 9.43 mmol, 1.0 equiv) in DMF (15 mL) at 0° C. and stirred for 15 min. To the mixture was added (2-chloromethoxyethyl)trimethylsilane (2.6 g, 16.0 mmol, 1.7 equiv) and stirred at room temperature for 2 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford 341.1. MS (ES): m/z 343.1 [M+H]⁺.

Synthesis of compound 341.2. A mixture of 341.1 (2.7 g, 7.89 mmol, 1.0 equiv), bis(pinacolato)diboron (4.0 g, 15.7 mmol, 2.0 equiv) and potassium acetate (1.5 g, 15.7 mmol, 2.0 equiv) in 1,4-dioxane (25 mL) and water (5 mL) was degassed by bubbling argon through for 10 min. [1,1'-Bis(diphenylphosphino)ferrocene]dichloropalladium(II) complex with DCM (0.115 g, 0.15 mmol, 0.02 equiv) was added, and degassed for 5 min. The reaction mixture was stirred at 80° C. for 8 h. It was transferred into water and extracted with ethyl acetate. The combined organic layers were washed with brine, dried over anhydrous sodium sulfate, filtered, and concentrated under reduced pressure to afford 341.2. MS (ES): m/z 390.3 [M+H]⁺.

Synthesis of compound 341.3. To a solution of 341.2 (2.20 g, 5.65 mmol, 1.0 equiv) in methanol (10 mL) and acetonitrile (10 mL) was added hydrogen peroxide (20 mL) at 0° C. and stirred for 8 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane to afford pure) to afford 341.3. MS (ES): m/z 280.2 [M+H]⁺.

Synthesis of compound 341.4. Compound 341.4 was prepared from 341.3 and Int-4, following the procedure described in the synthesis of 19.1. The product was purified by flash column chromatography on silica gel (CombiFlash®, 20% ethyl acetate in hexane). MS (ES): m/z 468.6 [M+H]⁺.

Synthesis of compound 341.5. Compound 341.5 was prepared from 341.4 following the procedure described in the synthesis of 5.4. The product was purified by flash column chromatography on silica gel (CombiFlash®, 40% ethyl acetate in hexane). MS (ES): m/z 436.0 [M+H]⁺.

Synthesis of compound 341.6. Compound 341.6 was prepared from 341.5 and Int-63, following the procedure described in the synthesis of I-13. The product was purified by flash column chromatography on silica gel (CombiFlash®, 50% ethyl acetate in hexane). MS (ES): m/z: 636.1 [M+H]⁺.

Synthesis of compound 341.7. Compound 341.7 was prepared from 341.6 following the procedure described in the synthesis of I-157. The product was purified by flash column chromatography on silica gel (CombiFlash®, 61.0% methanol in DCM). MS (ES): m/z 626.5 [M+H]⁺.

Synthesis of I-341. To a solution of 341.7 (0.090 g, 0.143 mmol, 1.0 equiv) in DCM (5 mL) was added trifluoroacetic acid (1.5 mL) at 0° C. and stirred for 2 h. It was transferred into ice-saturated sodium bicarbonate solution and extracted with DCM. The combined organic layers were washed with brine, dried over anhydrous sodium sulfate, filtered, and concentrated under reduced pressure. To the residue was added methanol (4 mL), water (2 mL) and triethylamine (1.5 mL) and stirred at room temperature for 3 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 3.8% methanol in DCM) to afford I-341. MS (ES): m/z: 496.2 [M+H]⁺, ¹H NMR (DMSO-d₆, 400 MHz): δ 13.35 (s, 1H), 9.01 (s, 1H), 8.63 (s, 1H), 8.53 (s, 1H), 8.17 (s, 1H), 8.08 (s, 1H), 7.96 (s, 1H), 3.98 (s, 3H), 3.66 (s, 3H), 2.44 (s, 3H).

Example 342: 1-methyl-6-(pyrazolo[1,5-a]pyrazin-3-yloxy)-2-((4-(pyrrolidin-1-ylmethyl)-3-(trifluoromethyl)phenyl)amino)-1H-imidazo[4,5-b]pyridine-7-carbonitrile Synthesis of compound I-342. To a solution of 168.1 (0.050 g, 0.177 mmol, 1.0 equiv) and Int-147 (0.081 g, 0.284 mmol, 1.6 equiv) in THF (5 mL) was added potassium tert-butoxide (1 M in THF, (0.53 mL, 0.531 mmol, 3.0 equiv) at 0° C. The reaction mixture was stirred at room temperature for 15 min. It was poured into ice-water and extracted with ethyl acetate. The combined organic layers were washed with brine, dried over anhydrous sodium sulfate, filtered, and concentrated under reduced pressure. The residue was added methanol (5 mL) and ferric chloride (0.086 g, 0.531 mmol, 3.0 equiv). The reaction mixture was stirred at 80° C. for 30 min. It was cooled to room temperature, poured into ice-water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.8% methanol in DCM) to afford I-342. MS (ES): m/z 534.3 [M+H]⁺, ¹H NMR (DMSO-d₆, 400 MHz): δ 9.86 (s, 1H), 9.09 (s, 1H), 8.77-8.76 (d, J=4.4 Hz, 1H), 8.32 (s, 1H), 8.25 (s, 1H), 8.20 (s, 1H), 8.13 (s, 1H), 7.94-7.93 (d, J=4.8, 1H), 7.78 (s, 1H), 4.01 (s, 3H), 3.72 (s, 2H), 1.75 (s, 6H), 1.25 (s, 2H).

1073

Example 343: (S)-7-chloro-1-methyl-N-(4-(1-methylpyrrolidin-2-yl)-3-(trifluoromethyl)phenyl)-6-(pyrazolo[1,5-a]pyrazin-3-yloxy)-1H-imidazo[4,5-b]pyridin-2-amine and (R)-7-chloro-1-methyl-N-(4-(1-methylpyrrolidin-2-yl)-3-(trifluoromethyl)phenyl)-6-(pyrazolo[1,5-a]pyrazin-3-yloxy)-1H-imidazo[4,5-b]pyridin-2-amine

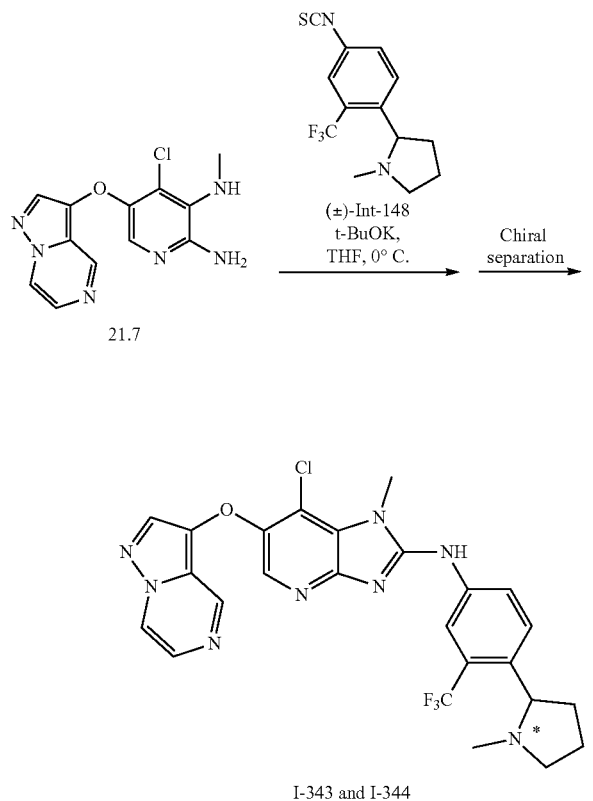

Synthesis of I-343 and I-344. The racemate was prepared from 21.7 and (±)-Int-148, following the procedure described in the synthesis of I-13. The product was purified by flash column chromatography on silica gel (CombiFlash®, 2.2% methanol in DCM). The enantiomers were separated by SFC (column: CHIRALPAK AD-H (250 mm*21 mm, 5 µm); mobile phases: (A) liquid $CO_2$ (B) 0.1% diethylamine in propan-2-ol:acetonitrile (50:50); flow rate: 80 mL/min) to afford first eluting fraction (I-343) and second eluting fraction (I-344). (*Absolute stereochemistry not determined.)

I-343: MS (ES): m/z 543.4 [M+H]$^+$, $^1$H NMR (DMSO-d$_6$, 400 MHz): δ 9.62 (s, 1H), 9.02 (s, 1H), 8.69-8.68 (d, J=4.4 Hz, 1H), 8.25 (s, 1H), 8.18 (s, 1H), 8.16-8.14 (d, J=8.0 Hz, 1H), 8.03 (s, 1H), 7.86 (bs, 2H), 4.01 (s, 3H), 3.19-3.17 (m, 1H), 2.29-2.25 (m, 1H), 2.17 (bs, 1H), 2.08 (s, 3H), 1.89 (bs, 1H), 1.75 (bs, 2H), 1.54 (bs, 1H).

I-343: MS (ES): m/z 543.4 [M+H]$^+$, $^1$H NMR (DMSO-d$_6$, 400 MHz): δ 9.63 (s, 1H), 9.03 (s, 1H), 8.70-8.69 (d, J=4.4 Hz, 1H), 8.26 (s, 1H), 8.17 (s, 1H), 8.17-8.15 (d, J=8.0 Hz, 1H), 8.04 (s, 1H), 7.88 (bs, 2H), 4.02 (s, 3H), 3.20-3.18 (m, 1H), 2.29-2.25 (m, 1H), 2.19 (bs, 1H), 2.09 (s, 3H), 1.90 (bs, 1H), 1.79 (bs, 2H), 1.56 (bs, 1H).

1074

Example 345: 2-(tert-butyl)-5-((7-chloro-1-methyl-6-((6-(methylamino)pyrazolo[1,5-a]pyrazin-3-yl)oxy)-1H-imidazo[4,5-b]pyridin-2-yl)amino)-3-ethylpyrimidin-4(3H)-one

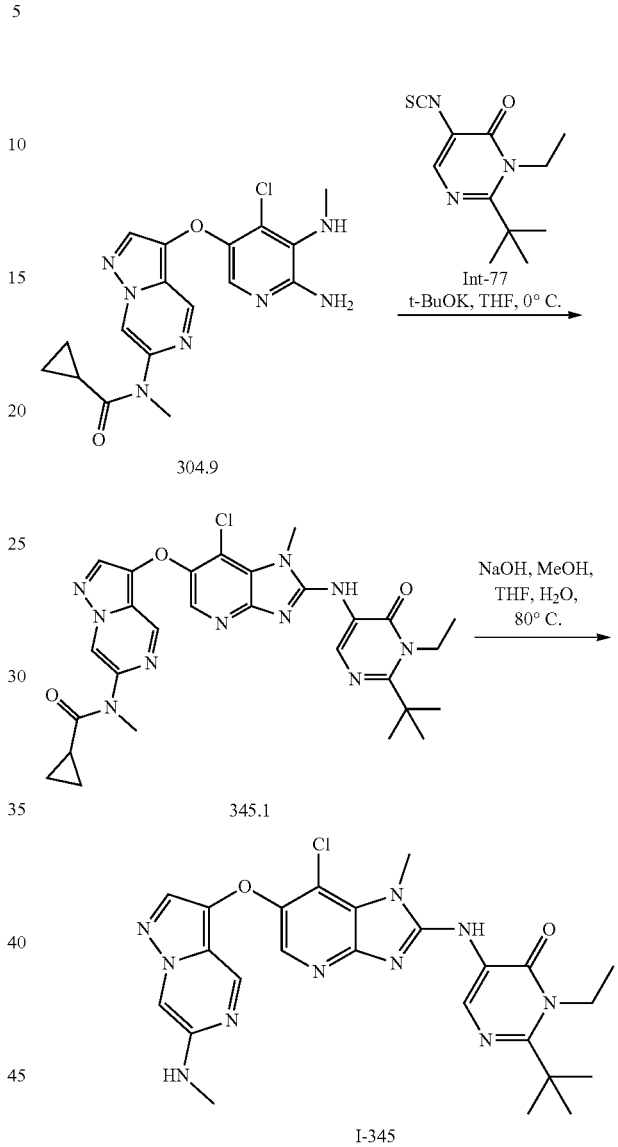

Synthesis of compound 345.1. Compound 345.1 was prepared from 304.9 and Int-77, following the procedure described in the synthesis of I-13. The product was purified by flash column chromatography on silica gel (CombiFlash®, 3.5% methanol in DCM). MS (ES): m/z 592.0 [M+H]$^+$.

Synthesis of I-345. Compound I-345 was prepared from 345.1 following the procedure described in the synthesis of I-304. The product was purified by flash column chromatography on silica gel (CombiFlash®, 4.0% methanol in DCM). MS (ES): m/z 523.3 [M+H]$^+$, $^1$H NMR (DMSO-d$_6$, 400 MHz): δ 8.85 (s, 1H), 8.80 (s, 1H), 8.68 (s, 1H), 8.10 (s, 1H), 7.62 (s, 1H), 7.54 (s, 1H), 6.14 (s, 1H), 4.52-4.51 (m, 2H), 3.99 (s, 3H), 2.72-2.71 (d, 3H), 1.38 (s, 9H), 1.24 (bs, 3H).

Example 346: (S)—N-(5-(tert-butyl)-1-(1-methylpyrrolidin-3-yl)-1H-pyrazol-3-yl)-7-chloro-1-methyl-6-((6-(methylamino)pyrazolo[1,5-a]pyrazin-3-yl)oxy)-1H-imidazo[4,5-b]pyridin-2-amine Synthesis of I-346. Compound I-346 was prepared from 346.1 following the procedure described in the synthesis of I-304. The product was purified by flash column chromatography on silica gel (CombiFlash®, 2.5% methanol in

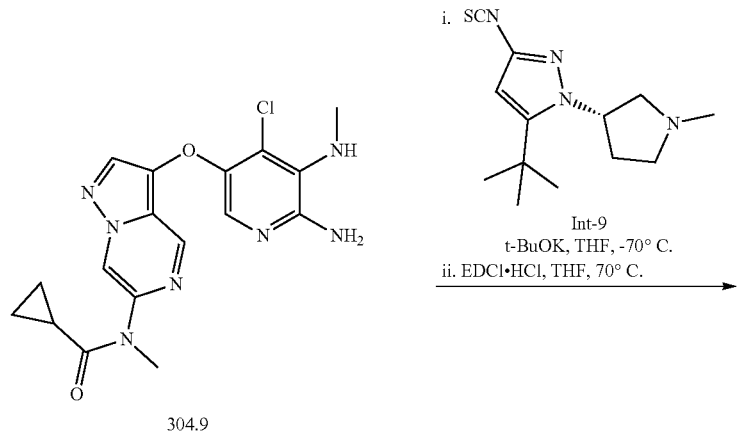

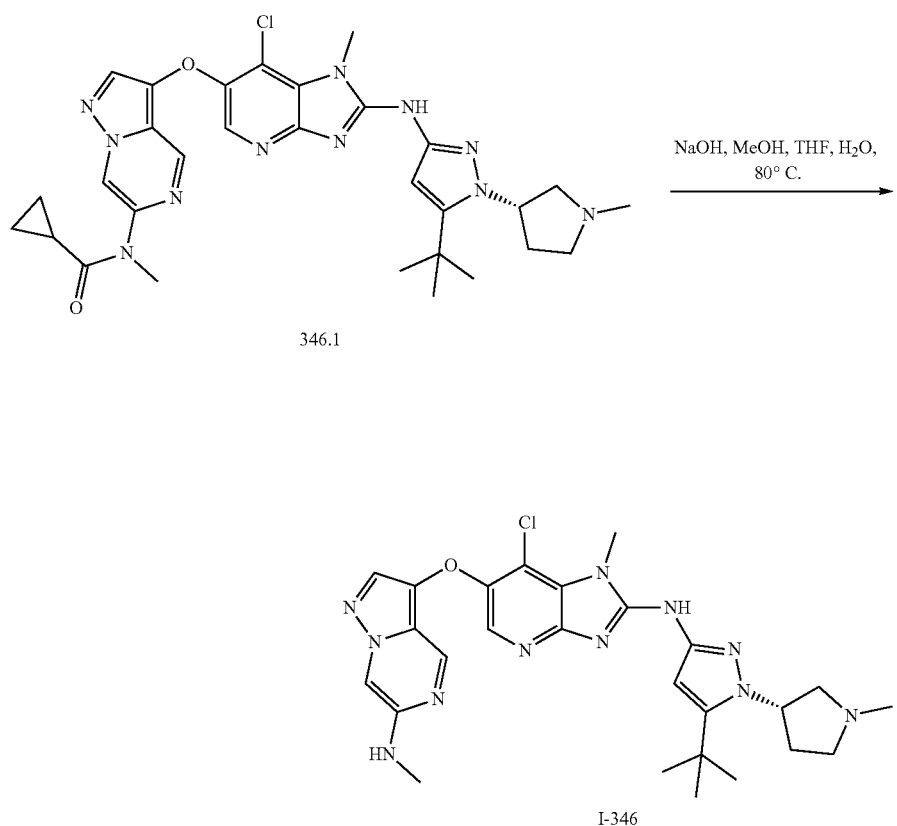

Synthesis of compound 346.1. Compound 346.1 was prepared from 304.9 and Int-9, following the procedure described in the synthesis of I-51. The product was purified by flash column chromatography on silica gel (CombiFlash®, 3.0% methanol in DCM). MS (ES): m/z 619.1 [M+H]⁺.

DCM). MS (ES): m/z 550.4 [M+H]⁺, ¹H NMR (DMSO-$d_6$, 400 MHz): δ 9.95 (s, 1H), 8.67 (s, 1H), 8.06 (s, 1H), 7.62 (s, 1H), 7.54 (s, 1H), 6.51 (s, 1H), 6.14 (bs, 1H), 5.10 (bs, 1H), 3.96 (s, 3H), 2.72-2.71 (d, 3H), 2.68 (bs, 7H), 1.39 (s, 9H), 1.24 (bs, 2H).

Example 347: (R)—N-(5-(tert-butyl)-1-(1-methylpyrrolidin-3-yl)-1H-pyrazol-3-yl)-7-chloro-1-methyl-6-((6-(methylamino)pyrazolo[1,5-a]pyrazin-3-yl)oxy)-1H-imidazo[4,5-b]pyridin-2-amine Synthesis of I-347. Compound I-347 was prepared from 347.1 following the procedure described in the synthesis of I-304. The product was purified by flash column chromatography on silica gel (CombiFlash®, 2.5% methanol in

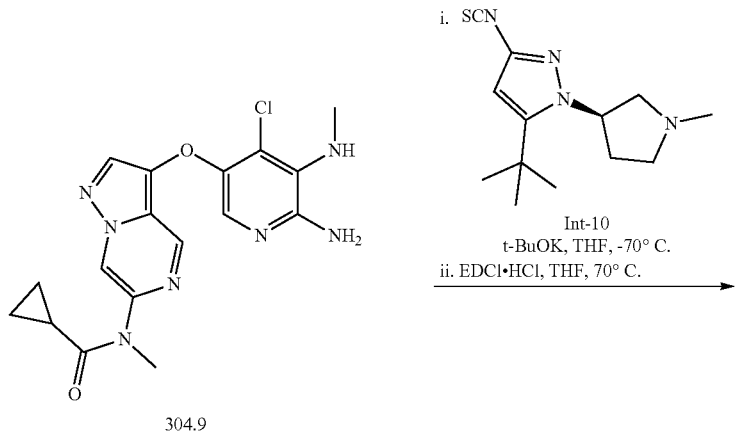

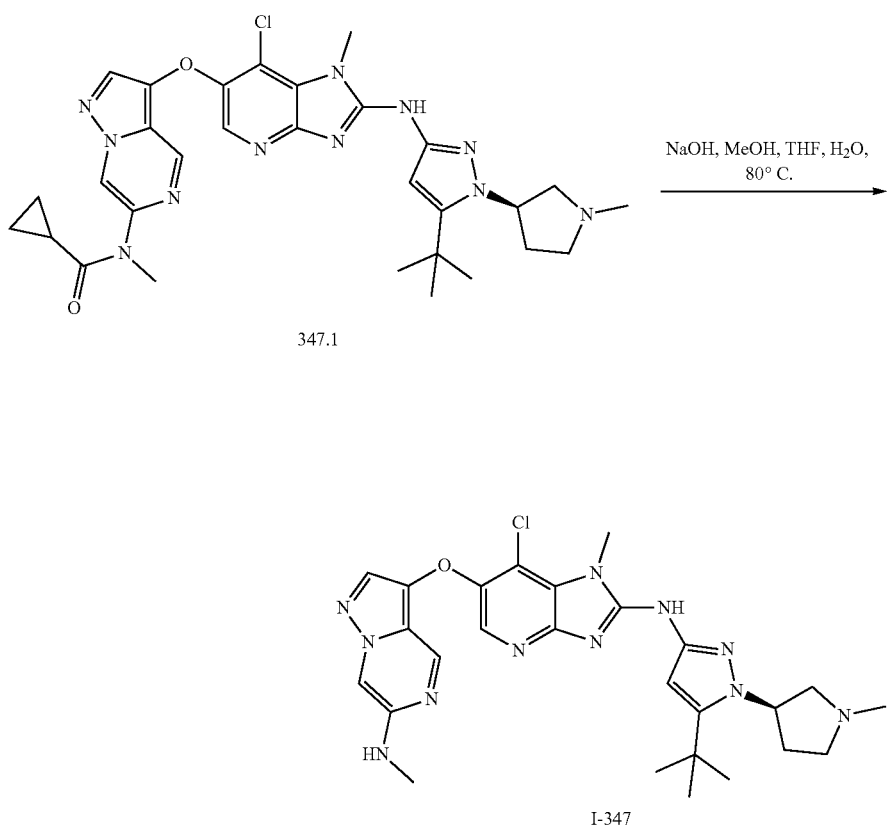

Synthesis of compound 347.1. Compound 347.1 was prepared from 304.9 and Int-10, following the procedure described in the synthesis of I-51. The product was purified by flash column chromatography on silica gel (CombiFlash®, 3.0% methanol in DCM). MS (ES): m/z 619.1 [M+H]$^+$.

DCM. MS (ES): m/z 550.3 [M+H]$^+$, $^1$H NMR (DMSO-d$_6$, 400 MHz): δ 9.97 (s, 1H), 8.66 (s, 1H), 8.05 (s, 1H), 7.61 (s, 1H), 7.53 (s, 1H), 6.50 (s, 1H), 6.14 (bs, 1H), 5.15 (bs, 1H), 3.96 (s, 3H), 2.71-2.69 (d, 3H), 2.68 (bs, 7H), 1.39 (s, 9H), 1.23 (bs, 2H).

Example 348: 5-((7-chloro-1-methyl-6-((6-(methyl-amino)pyrazolo[1,5-a]pyrazin-3-yl)oxy)-1H-imidazo[4,5-b]pyridin-2-yl)amino)-2-fluoro-N,N-dimethyl-3-(trifluoromethyl)benzamide

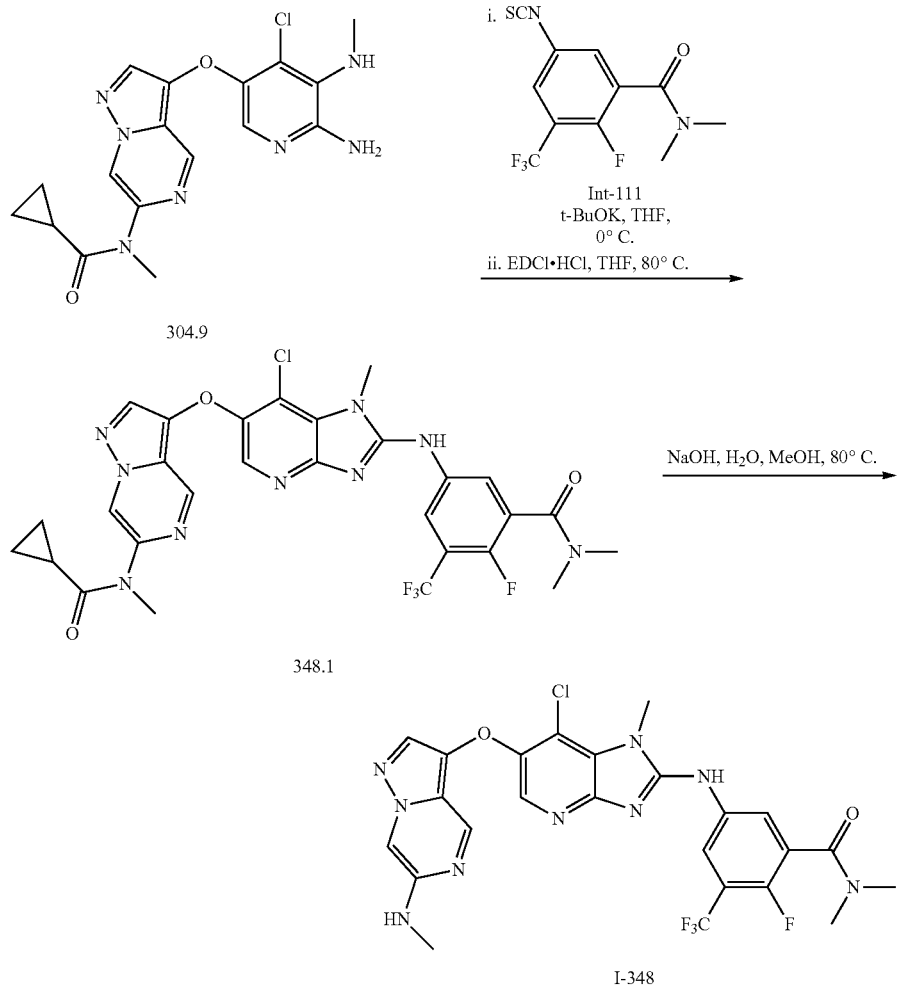

Synthesis of compound 348.1. Compound 348.1 was prepared from 304.9 and Int-111, following the procedure described in the synthesis of 331.1. The product was purified by flash column chromatography on silica gel (CombiFlash®, 3.0% methanol in DCM). MS (ES): m/z 647.1 [M+H]$^+$.

Synthesis of I-348. Compound I-348 was prepared from 348.1 following the procedure described in the synthesis of I-304. The product was purified by flash column chromatography on silica gel (CombiFlash®, 2.8% methanol in DCM). MS (ES): m/z 578.3 [M+H]$^+$, $^1$H NMR (DMSO-d$_6$, 400 MHz): 9.79 (s, 1H), 8.68 (s, 1H), 8.35-8.34 (d, J=5.2 Hz, 2H), 8.16 (s, 1H), 7.65 (s, 1H), 7.56 (s, 1H), 6.15-6.14 (d, J=5.2 Hz, 1H), 4.03 (s, 3H), 3.07 (s, 3H), 2.93 (s, 3H), 2.72-2.71 (d, 3H).

Example 349: 6-((3-methoxy-1H-pyrrolo[2,3-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

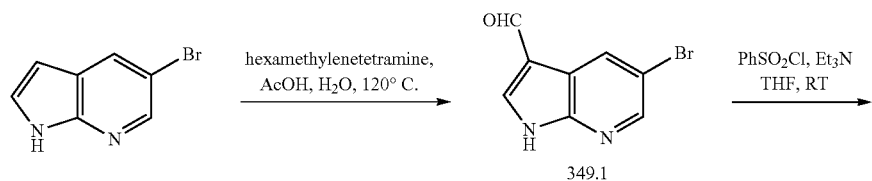

-continued
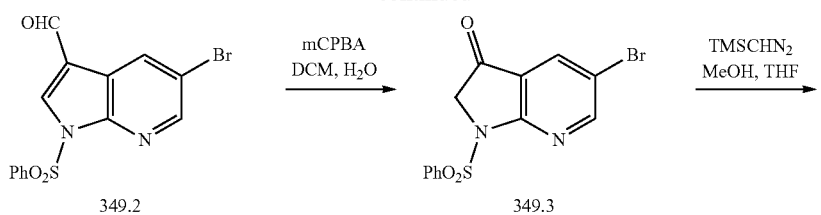
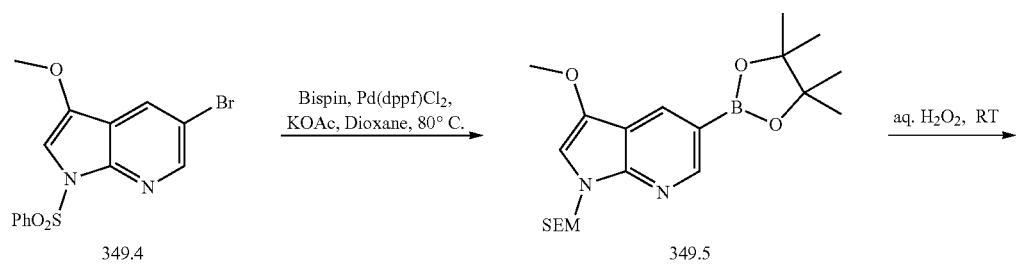
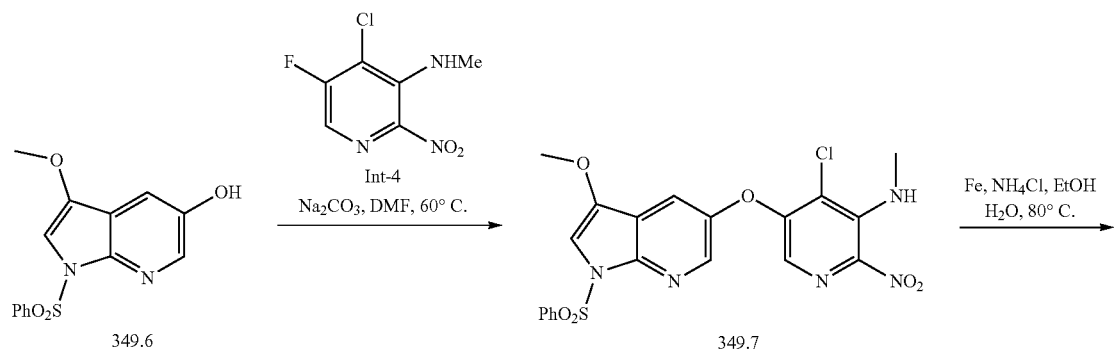
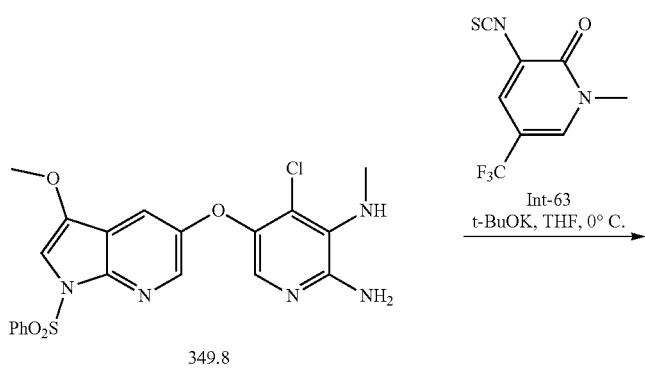

-continued

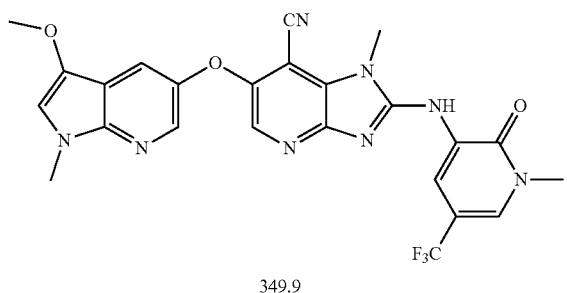

349.9

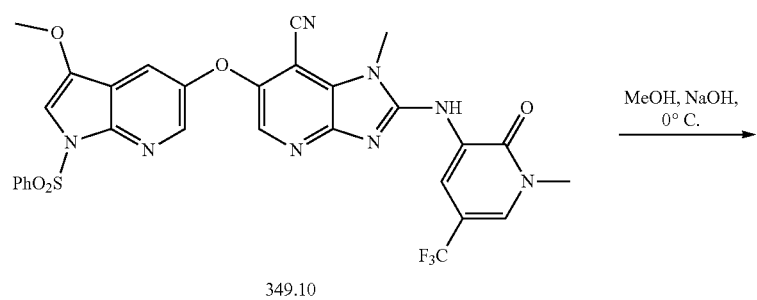

349.10

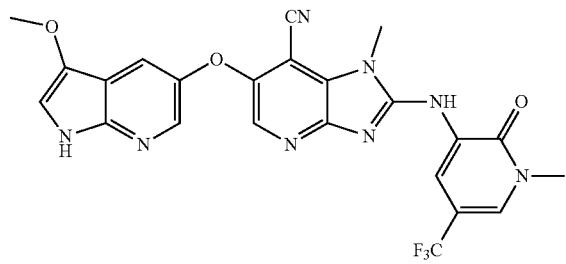

I-349

Synthesis of compound 349.1. To a solution of 5-bromo-1H-pyrrolo[2,3-b]pyridine (40.0 g, 203.01 mmol, 1.0 equiv) in acetic acid (92 mL) was added water (184 mL) followed by hexamethylenetetramine (39.8 g, 284.34 mmol, 1.4 equiv). The reaction mixture was stirred at 120° C. for 16 h. It was transferred into ice-water, stirred, and precipitated solid was filtered, dried under vacuum to afford 349.1. MS (ES): m/z 226.1 [M+H]$^+$.

Synthesis of compound 349.2. To a solution of 349.1 (30.0 g, 133.31 mmol, 1.0 equiv) and triethylamine (22.74 mL, 166.63 mmol, 1.25 equiv) in THF (750 mL) was added benzylsulfonyl chloride (21.65 mL, 159.97 mmol, 1.2 equiv) and stirred at room temperature for 16 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 12% ethyl acetate in hexane) to afford 349.2. MS (ES): m/z 366.1 [M+H]$^+$.

Synthesis of compound 349.3. To a solution of 349.2 (5.0 g, 13.69 mmol, 1 equiv) in DCM (100 mL) was added m-chloroperbenzoic acid (3.53 g, 20.53, 1.5 equiv) at 0° C. The reaction mixture was stirred at room temperature for 8 h. The reaction mixture was transferred into aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford 349.3. MS (ES): m/z 354.5 [M+H]$^+$.

Synthesis of compound 349.4. To a solution of 349.3 (2.0 g, 5.66 mmol, 1.0 equiv) in methanol:THF (1:1, 80 mL) was added trimethylsilyl diazomethane solution (1 M in THF, 15 mL). The reaction mixture was stirred at room temperature for 16 h. A few drops of acetic acid was added to quench the reaction and the reaction mixture was concentrated under reduced pressure. The residue was purified by flash column chromatography on silica gel (CombiFlash®, 10% ethyl acetate in hexane) to afford 349.4. MS (ES): m/z 368.1 [M+H]+.

Synthesis of compound 349.5. A mixture of 349.4 (1.2 g, 3.27 mmol, 1.0 equiv), bis(pinacolato)diboron (1.65 g, 6.54 mmol, 2.0 equiv) and potassium acetate (0.640 g, 6.54 mmol, 2 equiv) in 1,4 dioxane (12 mL) was degassed by bubbling argon through for 30 min. Under argon atmosphere, 1,1-bis(diphenylphosphino)ferrocene-palladium(II) dichloride DCM complex (0.047 g, 0.065 mmol, 0.02 equiv) was added. The reaction mixture was stirred at 80° C. for 6 h. It was poured into ice-water and extracted with ethyl acetate. The combined organic layers were washed with brine, dried over anhydrous sodium sulfate, filtered, and concentrated under reduced pressure to afford 349.5. MS (ES): m/z 415.1 [M+H]+.

Synthesis of compound 349.6. Compound 349.5 (1.2 g, 2.90 mmol, 1.0 equiv) was stirred with aqueous hydrogen peroxide solution (6 mL) at room temperature for 16 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 35% ethyl acetate in hexane) to afford 349.6. MS (ES): m/z 305.2 [M+H]+.

Synthesis of compound 349.7. To a solution of 349.6 (0.600 g, 1.97 mmol, 1.0 equiv) and Int-4 (0.323 g, 1.576 mmol, 0.8 equiv) in DMF (10 mL) was added potassium carbonate (0.815 g, 5.91 mmol, 3.0 equiv). The reaction mixture was stirred at 60° C. for 1 h. It was transferred into water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane) to afford 349.7. MS (ES): m/z 490.5 [M+H]+.

Synthesis of compound 349.8. Compound 349.8 was prepared from 349.7 following the procedure described in the synthesis of 5.4. The product was purified by flash column chromatography on silica gel (CombiFlash®, 40% ethyl acetate in hexane). MS (ES): m/z 460.5 [M+H]+.

Synthesis of compound 349.9. Compound 349.9 was prepared from 349.8 and Int-63, following the procedure described in the synthesis of I-13. The product was purified by flash column chromatography on silica gel (CombiFlash®, 75% ethyl acetate in hexane). MS (ES): m/z 661.7 [M+H]+.

Synthesis of compound 349.10. Compound 349.10 was prepared from 349.9 following the procedure described in the synthesis of I-157. The product was purified by flash column chromatography on silica gel (CombiFlash®, 70% ethyl acetate in hexane). MS (ES): m/z 651.3 [M+H]+.

Synthesis of I-349. To a solution of 349.10 (0.070 g, 0.106 mmol, 1.0 equiv) in methanol:THF (1:1, 4 mL) was added a solution of sodium hydroxide (0.042 g, 1.06 mmol, 10 equiv) in water (2 mL). The reaction mixture was stirred at 60° C. for 30 min. The reaction mixture concentrated under reduced pressure to afford residue. Residue was transferred into cold water and extracted with DCM. The combined organic layers were washed with brine, dried over anhydrous sodium sulfate, filtered, and concentrated under reduced pressure. The residue was purified by trituration by methanol) to afford I-349. MS (ES): m/z 511.3 [M+H]+, 1H NMR (DMSO-d6, 400 MHz): δ 11.21 (s, 1H), 8.62 (s, 1H), 8.21 (s, 1H), 8.14 (s, 2H), 7.97 (s, 1H), 7.62 (s, 1H), 7.15 (s, 1H), 3.96 (s, 3H), 3.78 (s, 3H), 3.65 (s, 3H).

Example 350: (S)-7-chloro-1-methyl-N-(3-((1-methylpiperidin-2-yl)methoxy)-5-(trifluoromethyl)phenyl)-6-(pyrazolo[1,5-a]pyrazin-3-yloxy)-1H-imidazo[4,5-b]pyridin-2-amine and (R)-7-chloro-1-methyl-N-(3-((1-methylpiperidin-2-yl)methoxy)-5-(trifluoromethyl)phenyl)-6-(pyrazolo[1,5-a]pyrazin-3-yloxy)-1H-imidazo[4,5-b]pyridin-2-amine

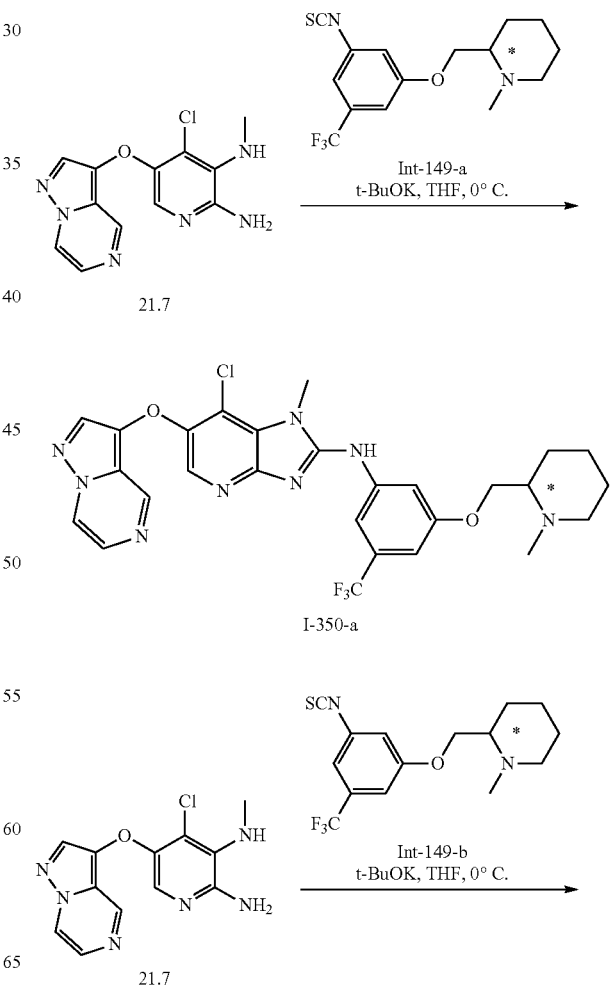

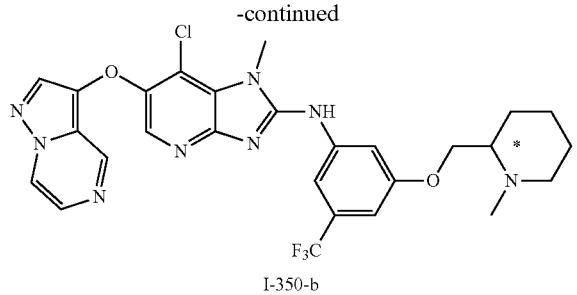

I-350-b

Synthesis of I-350-a. Compound I-350-a was prepared from 21.7 and Int-149-a, following the procedure described in the synthesis of I-13. The product was purified by flash column chromatography on silica gel (CombiFlash®, 2.2% methanol in DCM). MS (ES): m/z 587.4 [M+H]$^+$, $^1$H NMR (DMSO-d$_6$, 400 MHz): δ 9.66 (s, 1H), 9.02 (s, 1H), 8.69-8.68 (d, J=4.4 Hz, 1H), 8.20 (s, 1H), 8.04 (s, 1H), 7.98 (s, 1H), 7.87 (s, 1H), 7.86 (s, 1H), 6.94 (s, 1H), 4.17 (bs, 2H), 4.02 (bs, 4H), 2.45 (s, 3H), 2.33 (bs, 2H), 1.80-1.72 (m, 4H), 1.57 (bs, 2H).

Synthesis of I-350-b. Compound I-350-b was prepared from 21.7 and Int-149-b, following the procedure described in the synthesis of I-13. The product was purified by flash column chromatography on silica gel (CombiFlash®, 2.2% methanol in DCM). MS (ES): m/z 587.3 [M+H]$^+$, $^1$H NMR (DMSO-d$_6$, 400 MHz): δ 9.73 (s, 1H), 9.03 (s, 1H), 8.71-8.70 (d, J=4.4 Hz, 1H), 8.22 (s, 1H), 8.05 (s, 1H), 8.03 (s, 1H), 7.87 (bs, 2H), 6.97 (s, 1H), 4.22 (bs, 2H), 4.02 (bs, 4H), 2.45 (s, 3H), 2.33 (bs, 2H), 1.80-1.74 (m, 4H), 1.56 (bs, 2H).

Example 351: 7-chloro-1-methyl-6-((6-(methylamino)pyrazolo[1,5-a]pyrazin-3-yl)oxy)-N-(3-(4-methylpiperazin-1-yl)-5-(trifluoromethyl)phenyl)-1H-imidazo[4,5-b]pyridin-2-amine

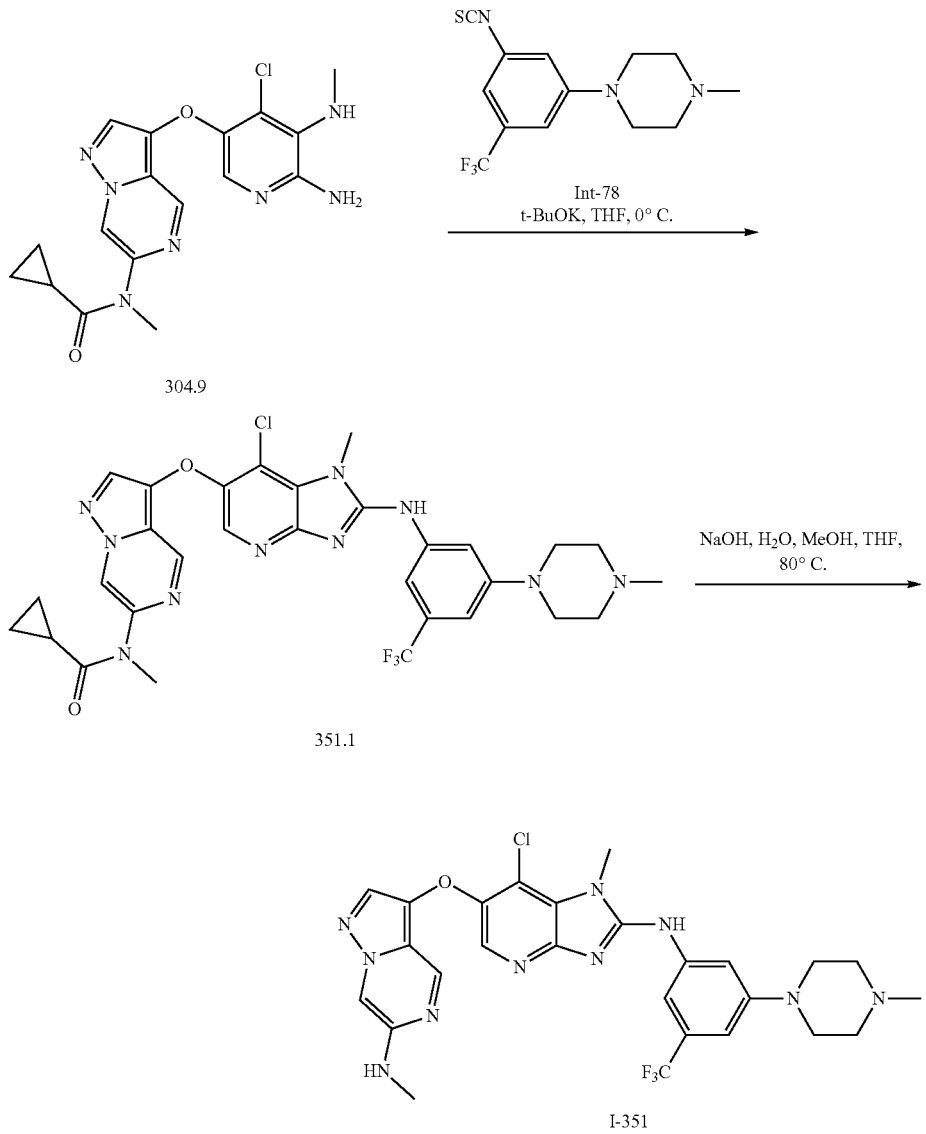

Synthesis of compound 351.1. Compound 351.1 was prepared from 304.9 and Int-78, following the procedure described in the synthesis of I-13. The product was purified by flash column chromatography on silica gel (Combi-Flash®, 3.8% methanol in DCM). MS (ES): m/z 656.0 [M+H]⁺.

Synthesis of I-351. Compound I-351 was prepared from 351.1 following the procedure described in the synthesis of I-304. The product was purified by flash column chromatography on silica gel (CombiFlash®, 8% methanol in DCM). MS (ES): m/z 587.3 [M+H]⁺, ¹H NMR (DMSO-d₆, 400 MHz): δ 9.44 (s, 1H), 8.66 (s, 1H), 8.12 (s, 1H), 7.79 (s, 1H), 7.72 (s, 1H), 7.62 (s, 1H), 7.54 (s, 1H), 6.88 (s, 1H), 6.13 (s, 1H), 4.01 (s, 3H), 3.23 (s, 4H), 2.71-2.70 (d, 3H), 2.33 (s, 3H), 2.24 (s, 4H).

Example 352: (S)-3-((7-chloro-1-methyl-6-((6-(methylamino)pyrazolo[1,5-a]pyrazin-3-yl)oxy)-1H-imidazo[4,5-b]pyridin-2-yl)amino)-1-(tetrahydro-2H-pyran-3-yl)-5-(trifluoromethyl)pyridin-2(1H)-one and (R)-3-((7-chloro-1-methyl-6-((6-(methylamino)pyrazolo[1,5-a]pyrazin-3-yl)oxy)-1H-imidazo[4,5-b]pyridin-2-yl)amino)-1-(tetrahydro-2H-pyran-3-yl)-5-(trifluoromethyl)pyridin-2(1H)-one

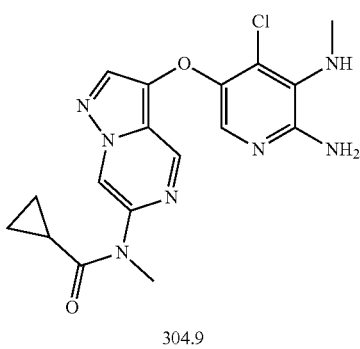

304.9

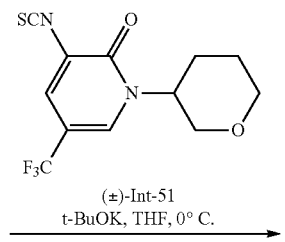

(±)-Int-51
t-BuOK, THF, 0° C.

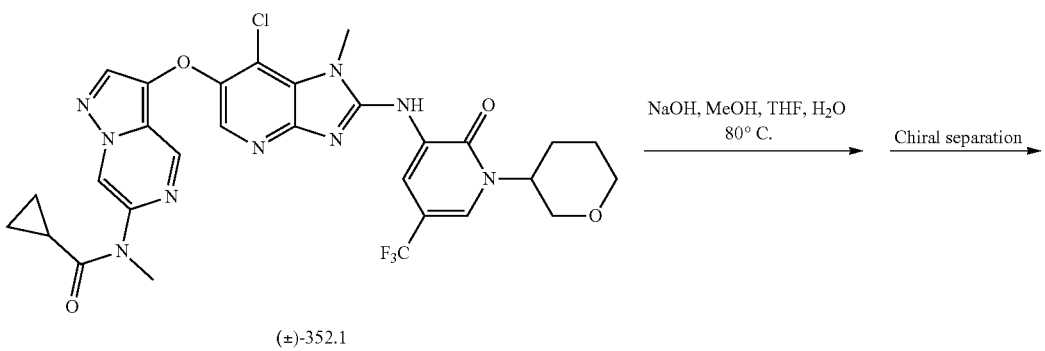

(±)-352.1

NaOH, MeOH, THF, H₂O
80° C. ⟶ Chiral separation

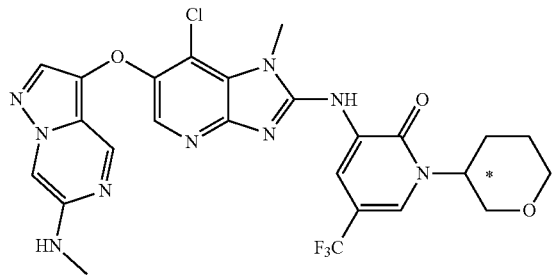

I-352-a and I-352-b

Synthesis of compound (±)-352.1. Compound (±)-352.1 was prepared from 304.9 and (±)-Int-51, following the procedure described in the synthesis of I-13. The product was purified by flash column chromatography on silica gel (CombiFlash®, 3.5% methanol in DCM. MS (ES): m/z 659.0 [M+H]$^+$.

Synthesis of compound I-352-a and I-352-b. The racemate was prepared from (f)-352.1 following the procedure described in the synthesis of I-304. The product was purified by flash column chromatography on silica gel (CombiFlash®, 2.6% methanol in DCM). The enantiomers were separated by HPLC (column: CHIRALPAK IB-N (250 mm×4.6 mm, 5 μm), mobile phase: (A) 0.1% DEA in n-hexane, (B) 0.1% DEA in propan-2-ol:acetonitrile (70: 30); flow rate: 20 mL/min) to afford first eluting fraction (I-352-a) and second eluting fraction (I-352-b).

I-352-a: MS (ES): m/z 590.3 [M+H]$^+$, $^1$H NMR (DMSO-d$_6$, 400 MHz): δ 8.80 (s, 1H), 8.69 (s, 1H), 8.60 (s, 1H), 8.18 (s, 1H), 8.10 (s, 1H), 7.65 (s, 1H), 7.54 (s, 1H), 6.12-6.11 (d, J=4.8 Hz, 1H), 4.87 (bs, 1H), 4.01 (s, 3H), 3.89-3.88 (m, 2H), 3.81-3.79 (m, 2H), 2.72-2.70 (d, 3H), 2.21-2.16 (m, 2H), 2.00 (bs, 2H).

I-352-b: MS (ES): m/z 590.2 [M+H]$^+$, $^1$H NMR (DMSO-d$_6$, 400 MHz): δ 8.80 (s, 1H), 8.68 (s, 1H), 8.60 (s, 1H), 8.18 (s, 1H), 8.09 (s, 1H), 7.65 (s, 1H), 7.54 (s, 1H), 6.10 (bs, 1H), 4.87 (bs, 1H), 4.01 (s, 3H), 3.88-3.87 (m, 2H), 3.82-3.80 (m, 2H), 2.72-2.70 (d, 3H), 2.21-2.16 (m, 2H), 2.01 (bs, 2H).

Example 353: 7-chloro-1-methyl-6-((6-(methylamino)pyrazolo[1,5-a]pyrazin-3-yl)oxy)-N-(3-(1-methylpiperidin-4-yl)-5-(trifluoromethyl)phenyl)-1H-imidazo[4,5-b]pyridin-2-amine

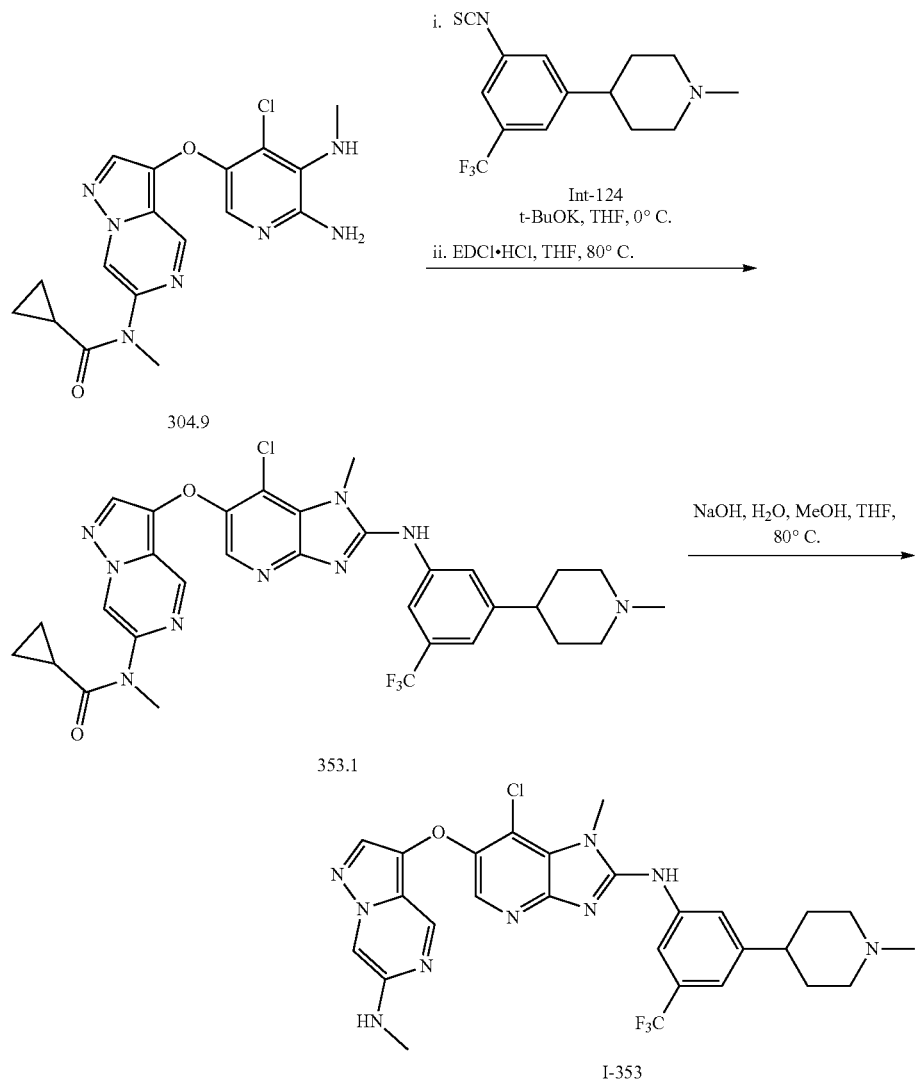

Synthesis of compound 353.1. Compound 353.1 was prepared from 304.9 and Int-124, following the procedure described in the synthesis of 331.1. The product was purified by flash column chromatography on silica gel (CombiFlash®, 7.8% methanol in DCM). MS (ES): m/z 655.10 [M+H]$^+$.

Synthesis of I-353. Compound I-353 was prepared from 353.1 following the procedure described in the synthesis of I-304. The product was purified by flash column chromatography on silica gel (CombiFlash®, 10.0% methanol in DCM). MS (ES): m/z 586.3 [M+H]+, $^1$H NMR (DMSO-$d_6$, 400 MHz): 9.72 (s, 1H), 8.67 (s, 1H), 8.25 (s, 1H), 8.13 (s, 1H), 8.10 (s, 1H), 7.63 (s, 1H), 7.54 (s, 1H), 7.24 (s, 1H), 6.15-6.14 (d, J=4.4 Hz, 1H), 4.03 (s, 3H), 2.71-2.70 (d, 3H), 2.67 (bs, 1H), 2.49 (s, 3H), 1.91 (bs, 2H), 1.85 (bs, 2H), 1.23 (bs, 4H).
Example 354: 3-((7-chloro-6-((4-fluoro-6-(methylamino)pyrazolo[1,5-a]pyridin-3-yl)oxy)-1-methyl-1H-imidazo[4,5-b]pyridin-2-yl)amino)-1-methyl-5-(trifluoromethyl)pyridin-2(1H)-one
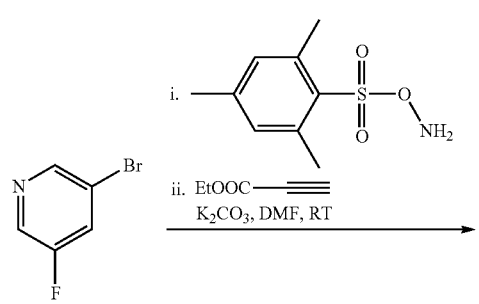
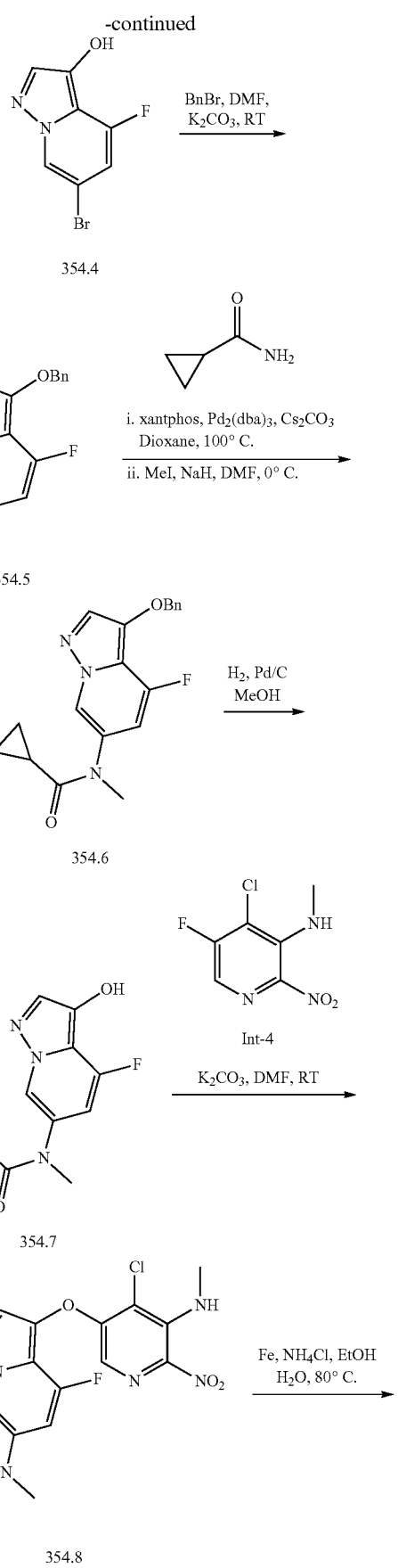

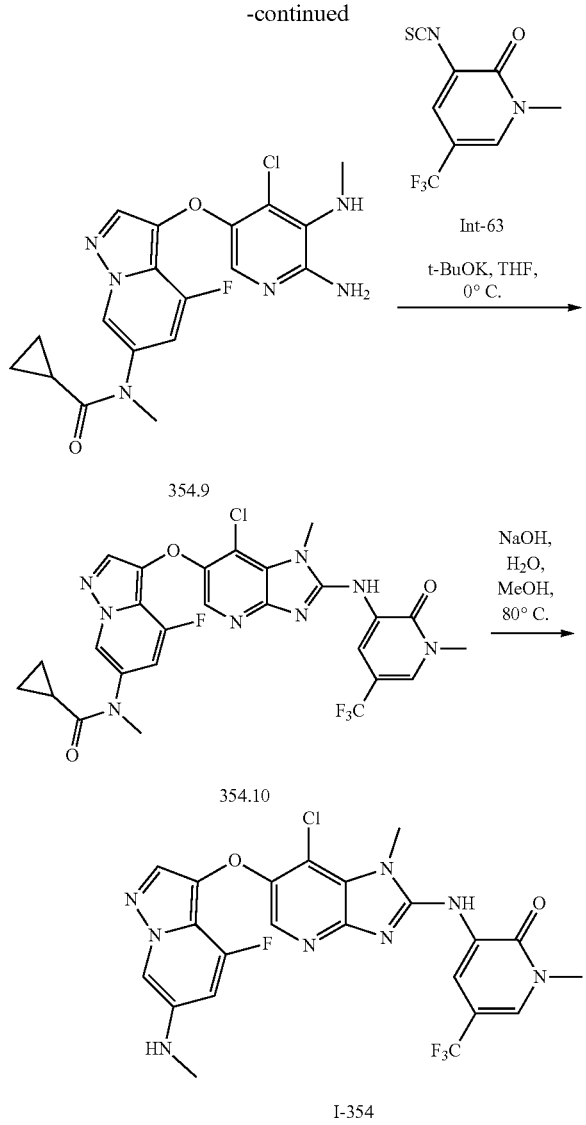

extracted with ethyl acetate. The combined organic layers were washed with brine, dried over anhydrous sodium sulfate, filtered, and concentrated under reduced pressure to afford 354.2. MS (ES): m/z 246.1 [M+H]⁺.

Synthesis of compound 354.3. To a solution of 354.2 (3.1 g, 12.65 mmol, 1.0 equiv) in DCM (60 mL) was added Dess-Martin periodinane (4.44 g, 25.3 mmol, 2.0 equiv). The reaction mixture was stirred at 0° C. for 1 h. It was transferred into aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford 354.3. MS (ES): m/z 243.8 [M+H]⁺.

Synthesis of compound 354.4. To a solution of 354.3 (2.3 g, 9.46 mmol, 1 equiv) in DCM (154 mL) was added m-chloroperbenzoic acid (60%, 3.2 g, 18.9 mmol, 2.0 equiv) and trifluoroacetic acid (0.1 g, 0.946 mmol, 0.1 equiv) at 0° C. The reaction mixture was stirred at room temperature for 18 h. The reaction mixture was transferred into aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 25% ethyl acetate in hexane) to afford 354.4. MS (ES): m/z 232.1 [M+H]⁺.

Synthesis of compound 354.5. To a mixture of 354.4 (0.900 g, 3.9 mmol, 1.0 equiv) and potassium carbonate (1.07 g, 7.7 mmol, 2.0 equiv) in DMF (7 mL) was added benzyl bromide (0.9 mL) and stirred at room temperature for 30 min. It was poured into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 7.0% ethyl acetate in hexane) to afford 354.5. MS (ES): m/z 322.0 [M+H]⁺.

Synthesis of compound 354.6. A mixture of 354.5 (0.550 g, 1.71 mmol, 1.0 equiv), cyclopropyl carboxamide (2.6 g, 31.56 mmol, 3.0 equiv) and cesium carbonate (10.25 g, 31.56 mmol, 3.0 equiv) in 1,4-dioxane (3 mL) was degassed by bubbling argon through for 10 min. Under argon atmosphere, 4,5-bis(diphenylphosphino)-9,9-dimethylxanthene (1.2 g, 2.1 mmol, 0.2 equiv) and tris(dibenzylideneacetone) dipalladium(0) (0.962 g, 1.052 mmol, 0.1 equiv) were added, and degassed for 5 min. The reaction mixture was stirred at 100° C. for 1 h. It was cooled to room temperature, transferred into water, and extracted with ethyl acetate. The combined organic layers were washed with brine, dried over anhydrous sodium sulfate, filtered, and concentrated under reduced pressure. The residue was dissolved in DMF and treated with NaH followed by methyl iodide at 0° C. The product was purified by flash column chromatography on silica gel (CombiFlash®, 15% ethyl acetate in hexane) to afford 354.6. MS (ES): m/z 340.2 [M+H]⁺.

Synthesis of compound 354.7. A mixture of compound 354.6 (0.385 g, 1.13 mmol, 1.0 equiv) and 10% palladium on charcoal (0.200 g) in methanol:THF (1:1, 30 mL) was stirred under hydrogen for 4 h. It was filtered through a pad of Celite® and rinsed with methanol. The filtrate was concentrated under reduced pressure to afford 354.7. MS (ES): m/z 250.1 [M+H]⁺.

Synthesis of compound 354.8. Compound 354.8 was prepared from 354.7 and Int-4, following the procedure described in the synthesis of 19.1. The product was purified Synthesis of compound 354.1. To a solution of 3-bromo-5-fluoropyridine (50.0 g, 284.0 mmol, 1.0 equiv) in DCM (2180 mL) was added O-(mesitylsulfonyl)hydroxylamine (78.77 g, 365.9 mmol, 1.2 equiv) at 0° C. The reaction mixture was stirred at room temperature for 1 h. It was transferred into diethyl ether and the solids were collected by filtration. The solids were added DMF (175 mL) and trimethylamine (76.0 mL, 571.0 mmol, 2.0 equiv), followed by ethyl propiolate ((55.7 g, 568.0 mmol, 2.0 equiv)) at 0° C. The reaction mixture was stirred at room temperature for 48 h. It was transferred into brine and extracted with ethyl acetate. The combined organic layers were washed with brine, dried over anhydrous sodium sulfate, filtered, and concentrated under reduced pressure. The residue was purified by flash column chromatography on silica gel (4% ethyl acetate in hexane) to afford 354.1. MS (ES): m/z 288.0 [M+H]⁺.

Synthesis of compound 354.2. To a solution of 354.1 (4.1 g, 14.28 mmol, 1.0 equiv) in THF (70 mL) was added diisobutylaluminum hydride (1 M solution in DCM, 42 mL, 42.0 mmol, 3.0 equiv) dropwise at −78° C. The reaction mixture was stirred at room temperature for 1 h. It was transferred into 2 M aqueous hydrochloric acid solution and by flash column chromatography on silica gel (Combi-Flash®, 22% ethyl acetate in hexane). MS (ES): m/z 435.6 [M+H]+.

Synthesis of compound 354.9. Compound 354.9 was prepared from 354.8 following the procedure described in the synthesis of 5.4. The product was purified by flash column chromatography on silica gel (CombiFlash®, 2.1% methanol in DCM). MS (ES): m/z 405.5 [M+H]+.

Synthesis of compound 354.10. Compound 354.10 was prepared from 354.9 and Int-63, following the procedure described in the synthesis of I-13. The product was purified by flash column chromatography on silica gel (Combi-Flash®, 2.8% methanol in DCM). MS (ES): m/z 605.8 [M+H]+.

Synthesis of I-354. Compound I-354 was prepared from 354.10 following the procedure described in the synthesis of I-304. MS (ES): m/z 537.2 [M+H]+, $^1$H NMR (CDCl$_3$, 400 MHz): 8.88 (bs, 1H), 8.17 (s, 1H), 8.06 (s, 1H), 7.60 (s, 1H), 7.49 (s, 1H), 7.42 (s, 1H), 7.28 (s, 1H), 6.38 (bs, 1H), 4.10 (s, 3H), 3.74 (s, 3H), 2.86 (s, 3H).

Example 355: 3-((7-chloro-6-((6-(2-methoxyethoxy)pyrazolo[1,5-a]pyridin-3-yl)oxy)-1-methyl-1H-imidazo[4,5-b]pyridin-2-yl)amino)-1-methyl-5-(trifluoromethyl)pyridin-2(1H)-one

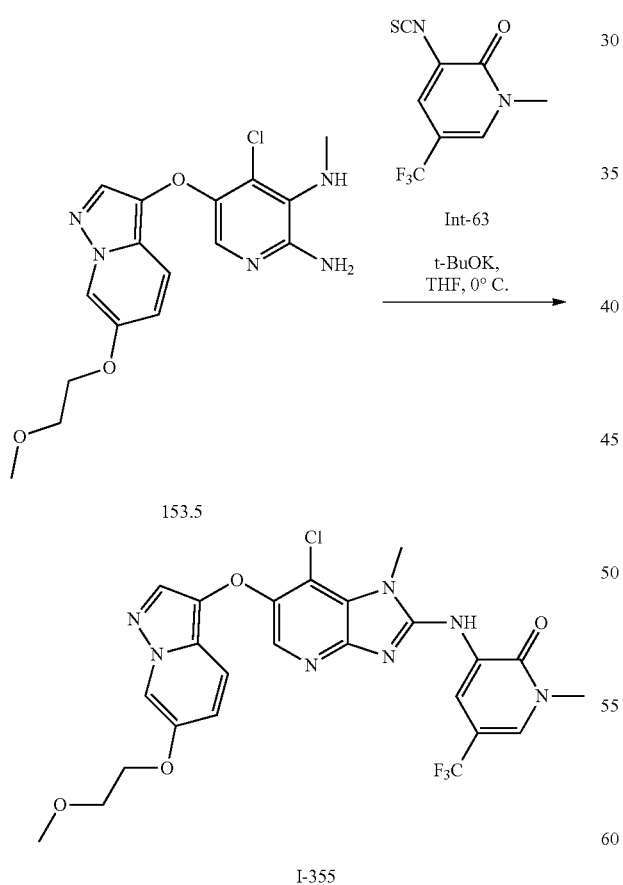

Synthesis of I-355. Compound I-355 was prepared from 153.5 and Int-63, following the procedure described in the synthesis of I-13. The product was purified by flash column chromatography on silica gel (CombiFlash®, 3.6% methanol in DCM). MS (ES): m/z 564.2 [M+H]+, $^1$H NMR (DMSO-d$_6$, 400 MHz): δ 8.79 (s, 1H), 8.60 (s, 1H), 8.36 (s, 1H), 8.13 (s, 1H), 8.04 (s, 1H), 7.88 (s, 1H), 7.44-7.42 (d, J=9.6 Hz, 1H), 7.03-7.01 (d, J=9.6 Hz, 1H), 4.15 (bs, 2H), 4.02 (s, 3H), 3.69 (bs, 2H), 3.66 (s, 3H), 3.33 (s, 3H).

Example 356: N-(3-((2-oxa-6-azaspiro[3.3]heptan-6-yl)methyl)-5-(trifluoromethyl)phenyl)-7-chloro-1-methyl-6-((6-(methylamino)pyrazolo[1,5-a]pyrazin-3-yl)oxy)-1H-imidazo[4,5-b]pyridin-2-amine

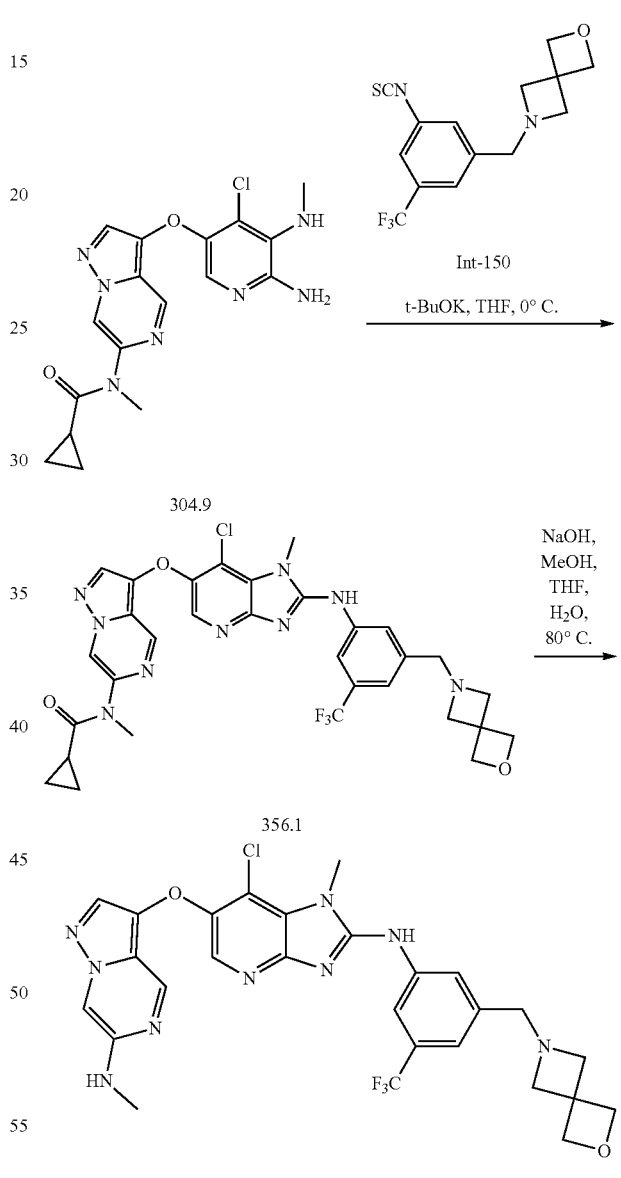

Synthesis of compound 356.1. Compound 356.1 was prepared from 304.9 and Int-150, following the procedure described in the synthesis of I-13. The product was purified by flash column chromatography on silica gel (Combi-Flash®, 5.0% methanol in DCM). MS (ES): m/z 669.08 [M+H]+.

Synthesis of I-356. Compound I-356 was prepared from 356.1 following the procedure described in the synthesis of I-304. The product was purified by flash column chromatography on silica gel (CombiFlash®, 7.0% methanol in DCM). MS (ES): m/z 600.3 [M+H]+, 1H NMR (DMSO-d6, 400 MHz): δ 9.65 (s, 1H), 8.67 (s, 1H), 8.29 (s, 1H), 8.14 (s, 1H), 8.05 (s, 1H), 7.63 (s, 1H), 7.54 (s, 1H), 7.22 (s, 1H), 6.14 (bs, 1H), 4.63 (bs, 4H), 4.02 (s, 3H), 3.62 (bs, 2H), 3.20 (bs, 4H), 2.71 (bs, 3H).

Example 357: N-(3-(azetidin-1-ylmethyl)-5-(trifluoromethyl)phenyl)-7-chloro-1-methyl-6-((6-(methylamino)pyrazolo[1,5-a]pyrazin-3-yl)oxy)-1H-imidazo[4,5-b]pyridin-2-amine DCM). MS (ES): m/z 558.3 [M+H]+, 1H NMR (DMSO-d6, 400 MHz): δ 9.96 (s, 1H), 8.67 (s, 1H), 8.35 (s, 1H), 8.22 (s, 1H), 8.14 (s, 1H), 7.63 (s, 1H), 7.55 (s, 1H), 7.44 (s, 1H), 6.16-6.14 (d, J=5.2 Hz, 1H), 4.02 (s, 3H), 3.68 (s, 2H), 2.71-2.70 (d, 3H), 2.21 (bs, 4H), 1.23 (bs, 2H).

Example 358: 7-chloro-N-(3-((3-fluoroazetidin-1-yl)methyl)-5-(trifluoromethyl)phenyl)-1-methyl-6-((6-(methylamino)pyrazolo[1,5-a]pyrazin-3-yl)oxy)-1H-imidazo[4,5-b]pyridin-2-amine

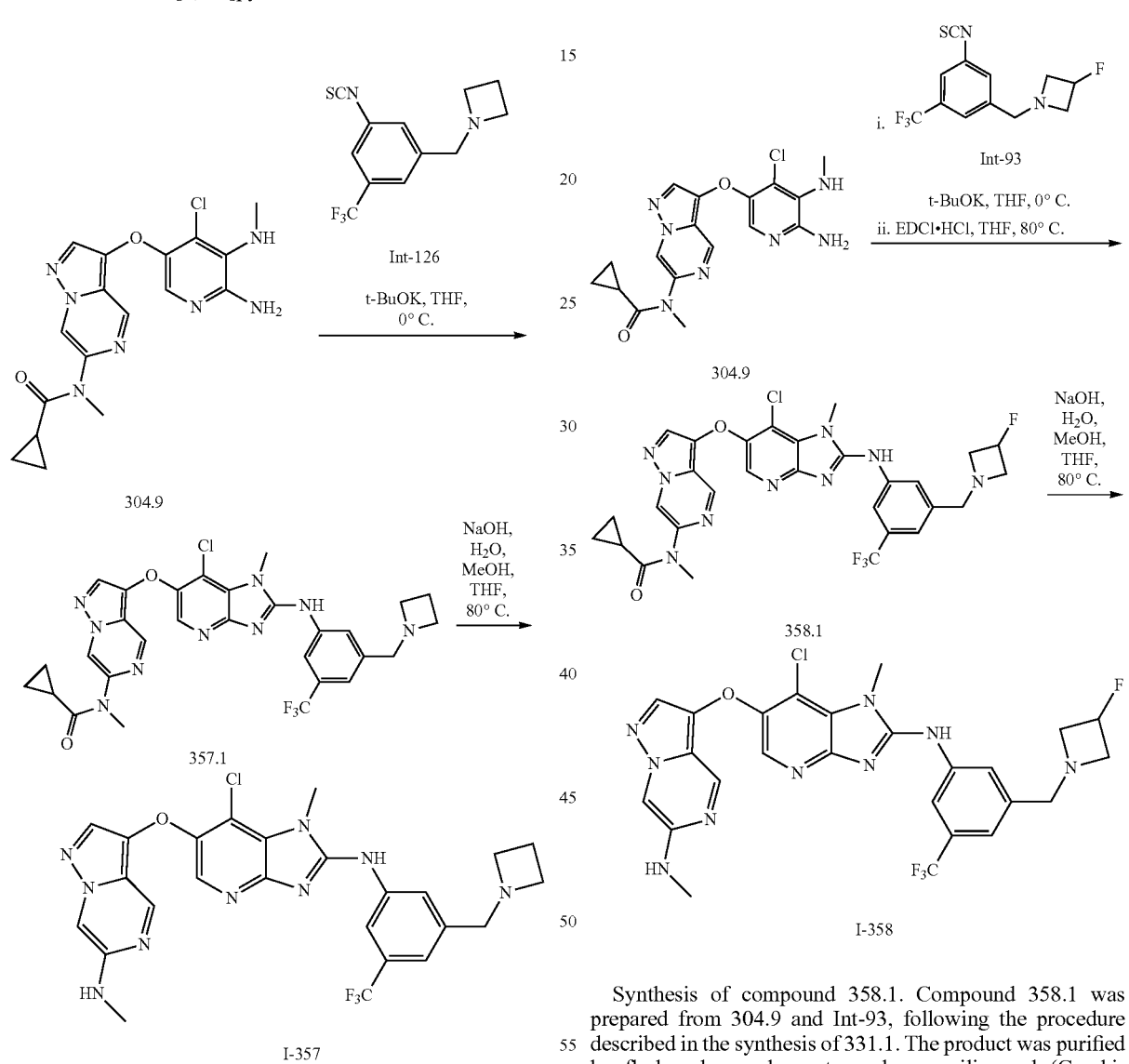

Synthesis of compound 357.1. Compound 357.1 was prepared from 304.9 and Int-126, following the procedure described in the synthesis of I-13. The product was purified by flash column chromatography on silica gel (CombiFlash®, 9.8% methanol in DCM). MS (ES): m/z 627.0 [M+H]+.

Synthesis of I-357. Compound I-357 was prepared from 357.1 following the procedure described in the synthesis of I-304. The product was purified by flash column chromatography on silica gel (CombiFlash®, 15% methanol in Synthesis of compound 358.1. Compound 358.1 was prepared from 304.9 and Int-93, following the procedure described in the synthesis of 331.1. The product was purified by flash column chromatography on silica gel (CombiFlash®, 4.0% methanol in DCM). MS (ES): m/z 645.0 [M+H]+.

Synthesis of I-358. Compound I-358 was prepared from 358.1 following the procedure described in the synthesis of I-304. The product was purified by flash column chromatography on silica gel (CombiFlash®, 4.5% methanol in DCM). MS (ES): m/z 576.3 [M+H]+, 1H NMR (DMSO-d6, 400 MHz): δ 9.65 (s, 1H), 8.67 (s, 1H), 8.30 (s, 1H), 8.14 (s, 1H), 8.06 (s, 1H), 7.63 (s, 1H), 7.54 (bs, 2H), 7.26 (s, 1H), 4.02 (s, 3H), 3.75 (s, 2H), 3.63-3.58 (m, 4H), 3.17 (bs, 1H), 2.71-2.70 (d, 3H).

Example 359: (R)-7-chloro-1-methyl-6-((6-(methylamino)pyrazolo[1,5-a]pyrazin-3-yl)oxy)-N-(3-(1-methylpyrrolidin-2-yl)-5-(trifluoromethyl)phenyl)-1H-imidazo[4,5-b]pyridin-2-amine and (S)-7-chloro-1-methyl-6-((6-(methylamino)pyrazolo[1,5-a]pyrazin-3-yl)oxy)-N-(3-(1-methylpyrrolidin-2-yl)-5-(trifluoromethyl)phenyl)-1H-imidazo[4,5-b]pyridin-2-amine

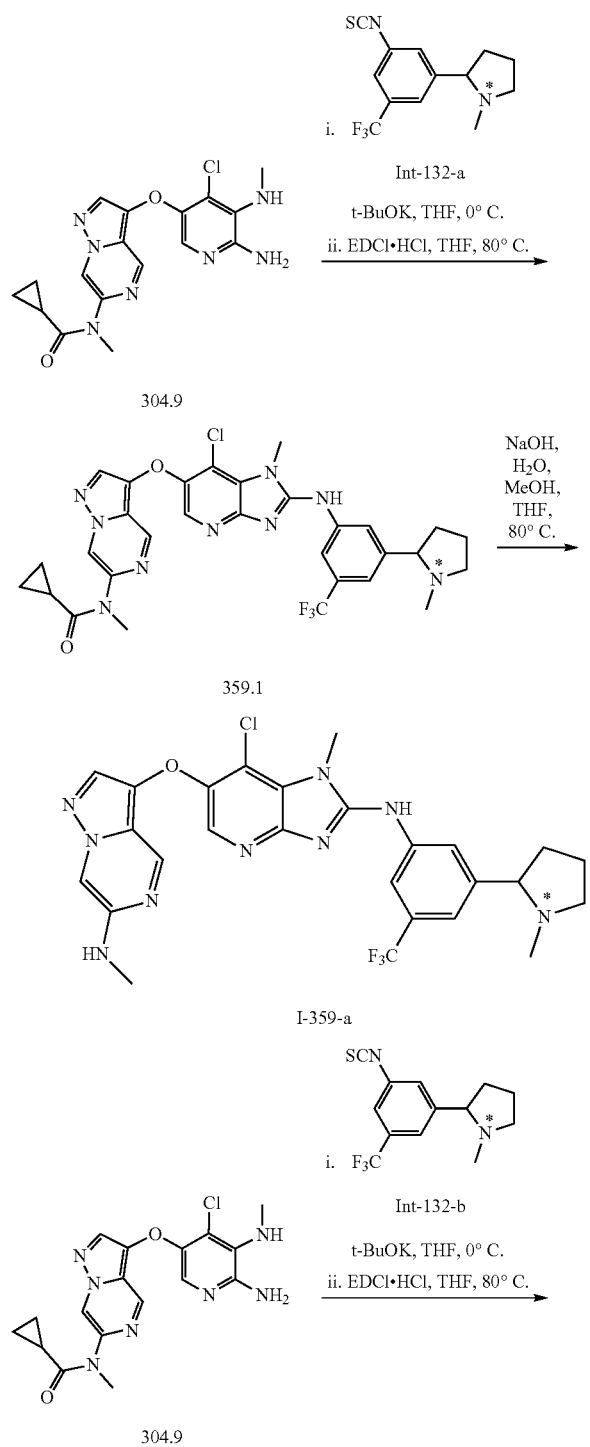

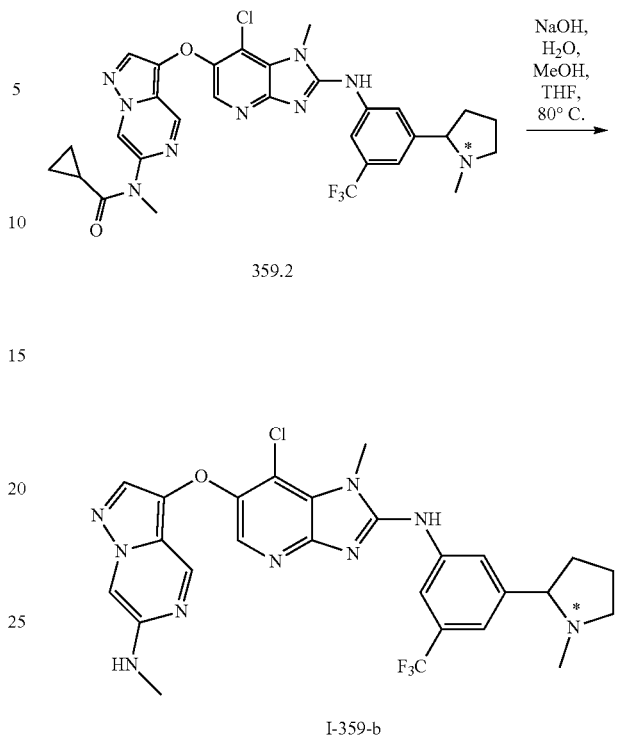

Synthesis of compound 359.1. Compound 359.1 was prepared from 304.9 and Int-132-a, following the procedure described in the synthesis of 331.1. The product was purified by flash column chromatography on silica gel (CombiFlash®, 7.20 methanol in DCM). MS (ES): m/z 641.0 [M+H]$^+$.

Synthesis of I-359-a. Compound I-359-a was prepared from 359.1 following the procedure described in the synthesis of I-304. The product was purified by flash column chromatography on silica gel (CombiFlash®, 10.00% methanol in DCM). MS (ES): m/z 573.0 [M+H]$^+$, $^1$H NMR (DMSO-d$_6$, 400 MHz): δ 9.67 (s, 1H), 8.67 (s, 1H), 8.38 (s, 1H), 8.14 (s, 1H), 8.10 (s, 1H), 7.63 (s, 1H), 7.54 (s, 1H), 7.30 (bs, 1H), 6.14 (bs, 1H), 4.02 (s, 3H), 2.71-2.70 (d, 3H), 2.33 (bs, 3H), 2.15 (bs, 1H), 1.23 (bs, 4H). (*Absolute stereochemistry not determined.)

Synthesis of compound 359.2. Compound 359.2 was prepared from 304.9 and Int-132-b, following the procedure described in the synthesis of 331.1. The product was purified by flash column chromatography on silica gel (CombiFlash®, 7.1% methanol in DCM). MS (ES): m/z 641.0 [M+H]$^+$.

Synthesis of I-359-b. Compound I-359-b was prepared from 359.2 following the procedure described in the synthesis of I-304. The product was purified by flash column chromatography on silica gel (CombiFlash®, 10.0% methanol in DCM). MS (ES): m/z 573.0 [M+H]$^+$, $^1$H NMR (DMSO-d$_6$, 400 MHz): δ 9.65 (s, 1H), 8.67 (s, 1H), 8.38 (s, 1H), 8.13 (s, 1H), 8.06 (s, 1H), 7.63 (s, 1H), 7.54 (s, 1H), 7.30 (bs, 1H), 6.14 (bs, 1H), 4.02 (s, 3H), 3.20 (bs, 3H), 2.71-2.70 (d, 3H), 2.14 (bs, 3H), 1.60 (bs, 2H), 1.23 (bs, 2H). (*Absolute stereochemistry not determined.)

Example 360: (S)-7-chloro-N-(4-((3-methoxypyrrolidin-1-yl)methyl)-3-(trifluoromethyl)phenyl)-1-methyl-6-((6-(methylamino)pyrazolo[1,5-a]pyrazin-3-yl)oxy)-1H-imidazo[4,5-b]pyridin-2-amine

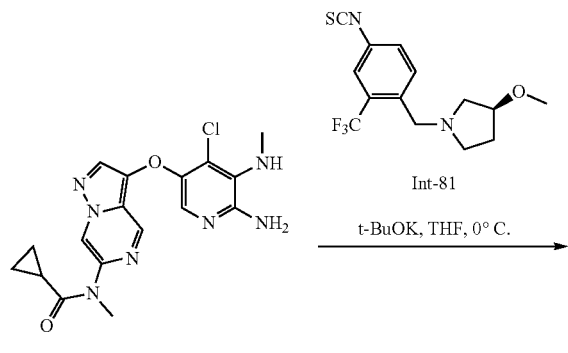

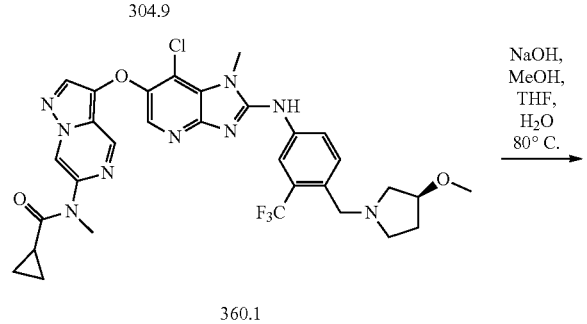

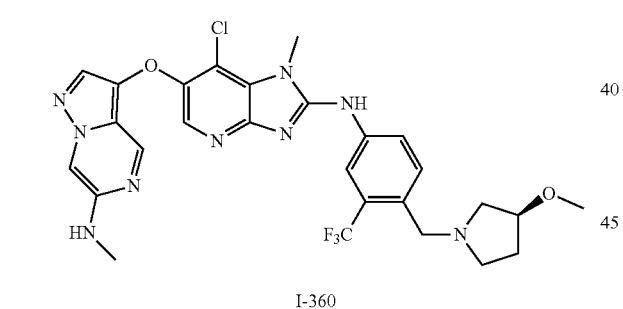

Example 361: (R)-7-chloro-N-(4-((3-methoxypyrrolidin-1-yl)methyl)-3-(trifluoromethyl)phenyl)-1-methyl-6-((6-(methylamino)pyrazolo[1,5-a]pyrazin-3-yl)oxy)-1H-imidazo[4,5-b]pyridin-2-amine

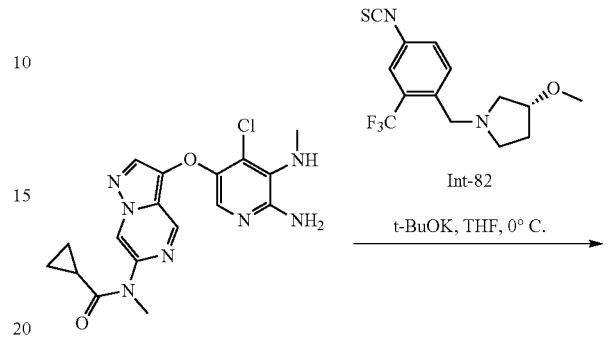

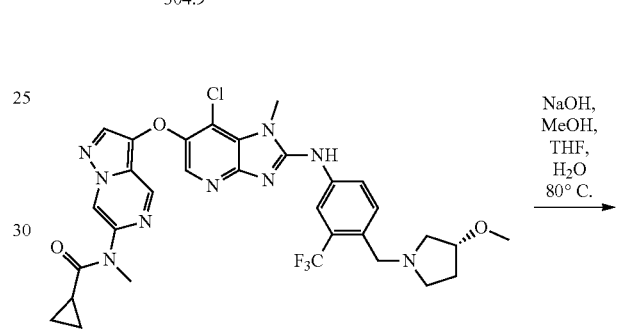

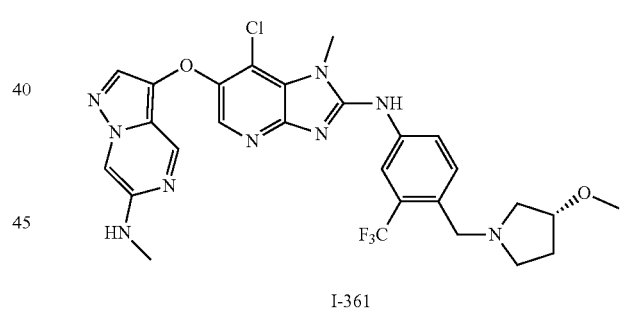

Synthesis of compound 360.1. Compound 360.1 was prepared from 304.9 and Int-81, following the procedure described in the synthesis of I-13. The product was purified by flash column chromatography on silica gel (CombiFlash®, 3.9% methanol in DCM). MS (ES): m/z 671.0 [M+H]+.

Synthesis of I-360. Compound I-360 was prepared from 360.1 following the procedure described in the synthesis of I-304. The product was purified by flash column chromatography on silica gel (CombiFlash®, 4.2% methanol in DCM). MS (ES): m/z 602.4 [M+H]+, $^1$H NMR (DMSO-$d_6$, 400 MHz): δ 9.61 (s, 1H), 8.67 (s, 1H), 8.28 (s, 1H), 8.13 (s, 1H), 7.72-7.70 (d, J 8.4 Hz, 1H), 7.62 (s, 1H), 7.54 (s, 1H), 6.14-6.13 (m, 1H), 4.01 (s, 1H), 3.90 (bs, 1H), 3.69 (s, 2H), 3.17 (s, 3H), 2.71-2.70 (d, 3H), 2.60 (bs, 2H), 2.04-1.99 (m, 1H), 1.69 (bs, 2H).

Synthesis of compound 361.1. Compound 361.1 was prepared from 304.9 and Int-82, following the procedure described in the synthesis of I-13. The product was purified by flash column chromatography on silica gel (CombiFlash®, 4.0% methanol in DCM). MS (ES): m/z 671.0 [M+H]+.

Synthesis of I-361. Compound I-361 was prepared from 361.1 following the procedure described in the synthesis of I-304. The product was purified by flash column chromatography on silica gel (CombiFlash®, 4.5% methanol in DCM). MS (ES): m/z 602.3 [M+H]+, $^1$H NMR (DMSO-$d_6$, 400 MHz): δ 9.61 (s, 1H), 8.68 (s, 1H), 8.29 (s, 1H), 8.13 (s, 1H), 7.73-7.71 (d, J 7.6 Hz, 1H), 7.63 (s, 1H), 7.55 (s, 1H), 6.13 (s, 1H), 4.02 (s, 1H), 3.91 (bs, 1H), 3.70 (s, 2H), 3.17 (s, 3H), 2.71-2.70 (d, 3H), 2.60 (bs, 2H), 2.03-2.01 (m, 1H), 1.69 (bs, 2H).

Example 362: 2-((4,4-difluoro-4,5,6,7-tetrahydropyrazolo[1,5-a]pyridin-2-yl)amino)-1-methyl-6-(pyrazolo[1,5-a]pyrazin-3-yloxy)-1H-imidazo[4,5-b]pyridine-7-carbonitrile

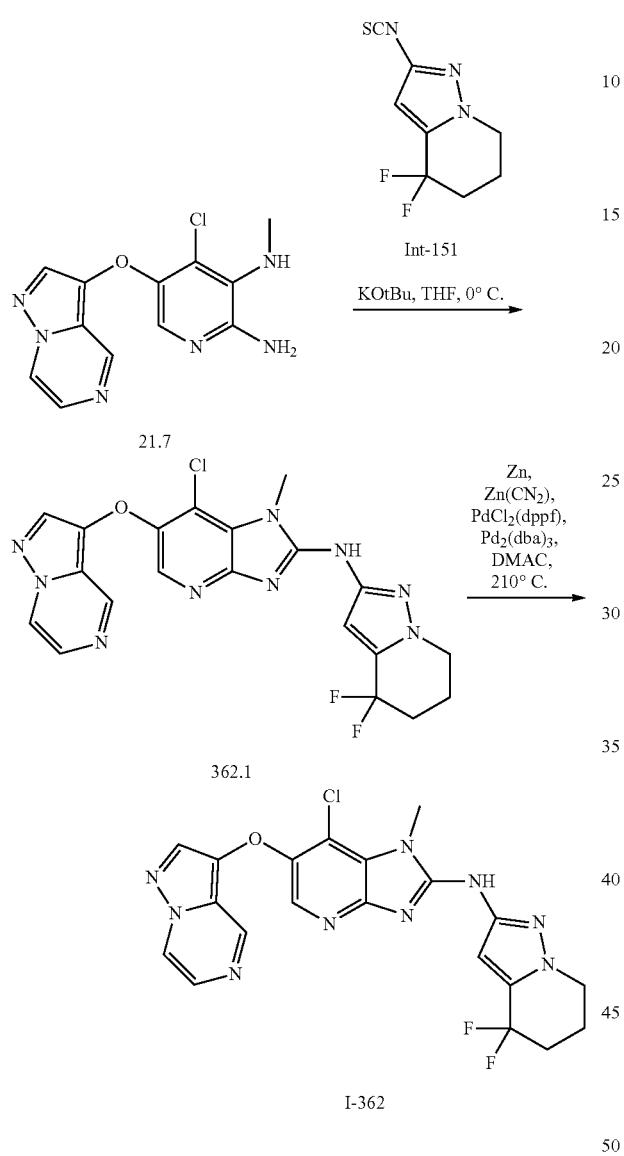

Synthesis of compound 362.1. Compound 362.1 was prepared from 21.7 and Int-151, following the procedure described in the synthesis of I-13. The product was purified by flash column chromatography on silica gel (CombiFlash®, 3.0% methanol in DCM). MS (ES): m/z 471.6 [M+H]+.

Synthesis of I-362. A mixture of 362.1 (0.050 g, 0.106 mmol, 1.0 equiv), zinc dust (0.001 g, 0.021 mmol, 0.2 equiv) and zinc cyanide (0.024 g, 0.212 mmol, 2.0 equiv) in N,N-dimethylacetamide (4 mL) was degassed by bubbling argon through for 10 min. Under argon atmosphere, tris(dibenzylideneacetone)dipalladium(0) (0.009 g, 0.010 mmol, 0.1 equiv) and 1,1'-bis(diphenylphosphino)ferrocene (0.005 g, 0.010 mmol, 0.1 equiv) were added, and degassed for 5 min. The reaction mixture was stirred at 170° C. in a microwave reactor for 3 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford I-362. MS (ES): m/z 463.1, $^1$H NMR (DMSO-$d_6$, 400 MHz): δ 10.62 (s, 1H), 9.08 (s, 1H), 8.75 (s, 1H), 8.22 (s, 1H), 8.09 (s, 1H), 7.92-7.91 (d, J=4.4 Hz, 1H), 7.08 (s, 1H), 4.15 (bs, 2H), 3.96 (s, 3H), 2.19 (bs, 2H), 1.24 (bs, 2H).

Example 363: 3-((7-chloro-6-((6-methoxypyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

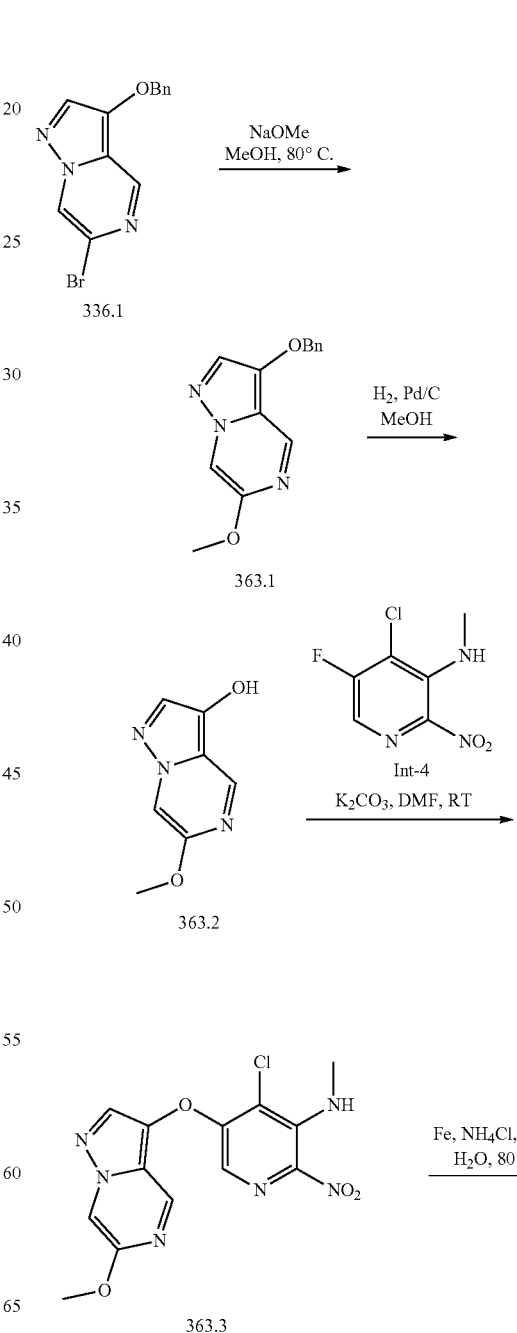

1107

-continued

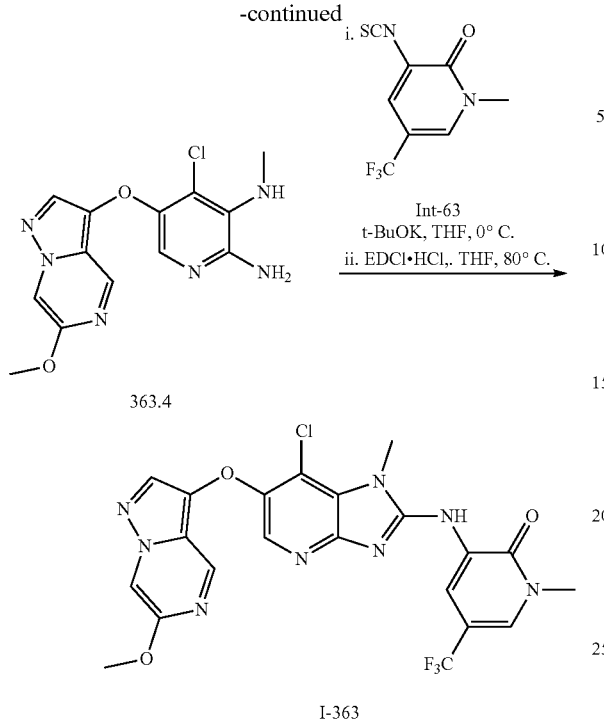

363.4 i. SCN, t-BuOK, THF, 0° C.
ii. EDCl·HCl,. THF, 80° C.

I-363

Synthesis of compound 363.1. A solution of 336.1 (1.0 g, 3.29 mmol, 1.0 equiv) and sodium methoxide solution (25% in methanol, 15 mL) was stirred at 80° C. for 1 h. The reaction mixture was concentrated under reduced pressure. The residue was transferred into ice-water and extracted with ethyl acetate. The combined organic layers were washed with brine, dried over sodium sulfate and concentrated under reduced pressure to afford 363.1. MS (ES): m/z 256.1 [M+H]$^+$.

Synthesis of compound 363.2. A mixture of compound 363.1 (0.500 g, 1.96 mmol, 1.0 equiv) and 10% palladium on carbon (0.500 g) in methanol (10 mL) and THF (1 mL) was stirred under hydrogen (1 atm) for 1 h. The reaction mixture filtered through a pad of Celite® and rinsed with methanol. The filtrate was concentrated under reduced pressure to obtain 363.2. MS (ES): m/z 166.2 [M+H]$^+$.

Synthesis of compound 363.3. Compound 363.3 was prepared from 363.2 and Int-4, following the procedure described in the synthesis of 19.1. The product was purified by flash column chromatography on silica gel (CombiFlash®, 40% ethyl acetate in hexane). MS (ES): m/z 351.5 [M+H]$^+$.

Synthesis of compound 363.4. Compound 363.4 was prepared from 363.3 following the procedure described in the synthesis of 5.4. The product was purified by flash column chromatography on silica gel (CombiFlash®, 3.0% methanol in DCM) to afford 363.4. MS (ES): m/z 321.6 [M+H]$^+$.

Synthesis of I-363. Compound I-363 was prepared from 363.4 and Int-63, following the procedure described in the synthesis of 331.1. The product was purified by flash column chromatography on silica gel (CombiFlash®, 2.2% methanol in DCM). MS (ES): m/z 521.3 [M+H]$^+$, $^1$H NMR (DMSO-d$_6$, 400 MHz): δ 8.83 (bs, 2H), 8.61 (s, 1H), 8.35 (s, 1H), 8.23 (s, 1H), 8.14 (s, 1H), 7.89 (s, 1H), 4.02 (s, 3H), 3.90 (s, 3H), 3.67 (s, 3H).

1108

Example 364: 6-((6-methoxypyrazolo[1,5-a]pyrazin-3-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

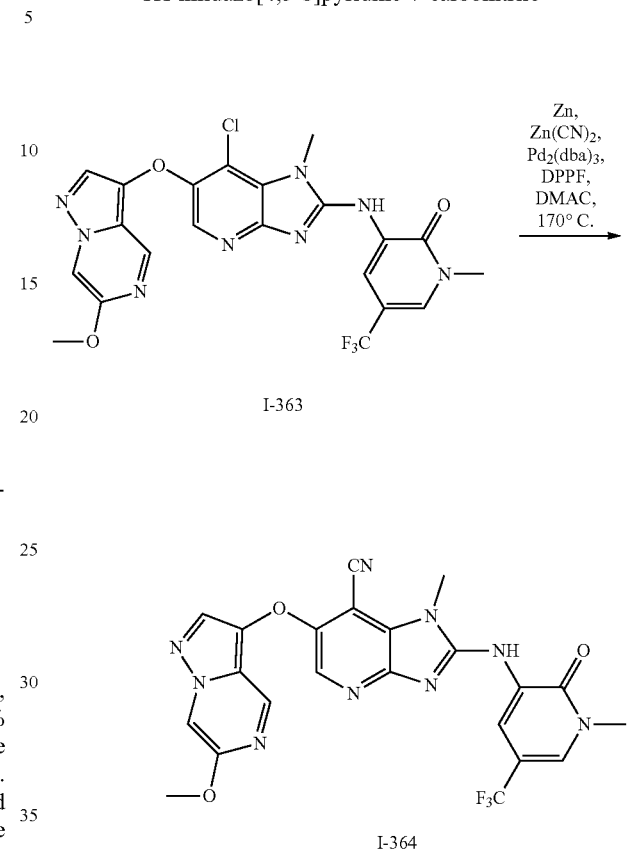

I-363

Zn, Zn(CN)$_2$, Pd$_2$(dba)$_3$, DPPF, DMAC, 170° C.

I-364

Synthesis of I-364. Compound I-364 was prepared from I-363 following the procedure described in the synthesis of I-157. The product was purified by flash column chromatography on silica gel (CombiFlash®, 5.0% methanol in DCM). MS (ES): m/z 512.0 [M+H]$^+$, $^1$H NMR (DMSO-d$_6$, 400 MHz): δ 9.00 (s, 1H), 8.89 (s, 1H), 8.62 (s, 1H), 8.42 (s, 1H), 8.17 (s, 1H), 8.14 (s, 1H), 8.10 (s, 1H), 4.00 (s, 3H), 3.91 (s, 3H), 3.66 (s, 3H).

Example 365: 3-((7-chloro-6-((6-(2-methoxyethoxy)pyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

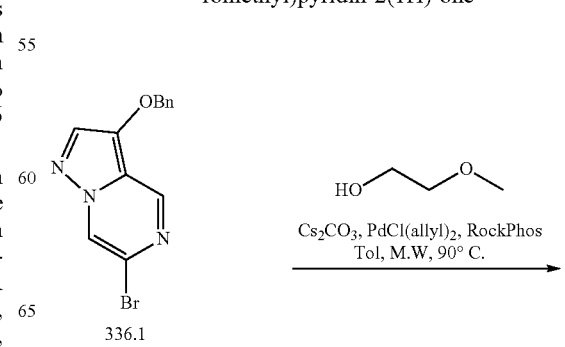

336.1

Cs$_2$CO$_3$, PdCl(allyl)$_2$, RockPhos
Tol, M.W, 90° C.

1109
-continued

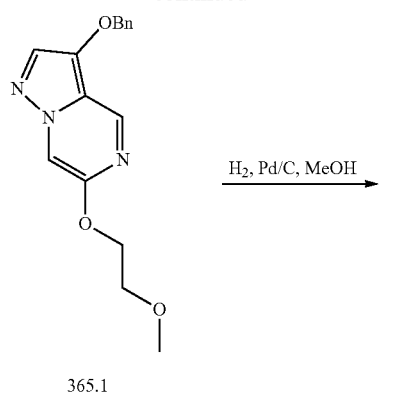

365.1

H₂, Pd/C, MeOH

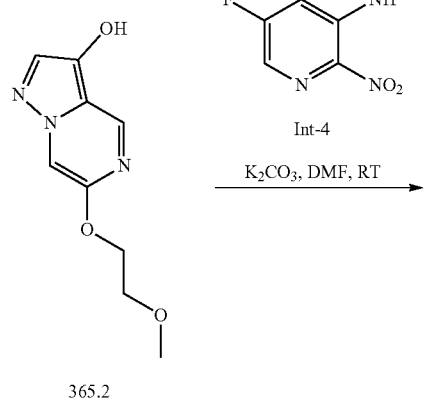

365.2

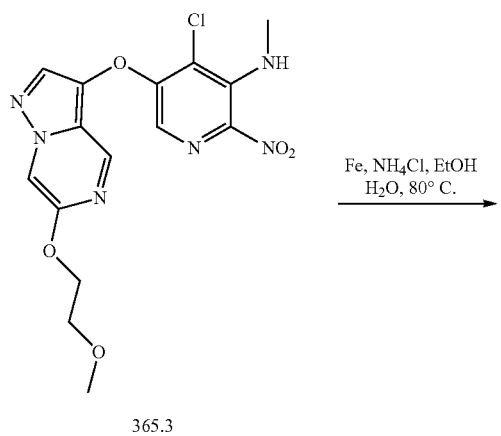

365.3

1110
-continued

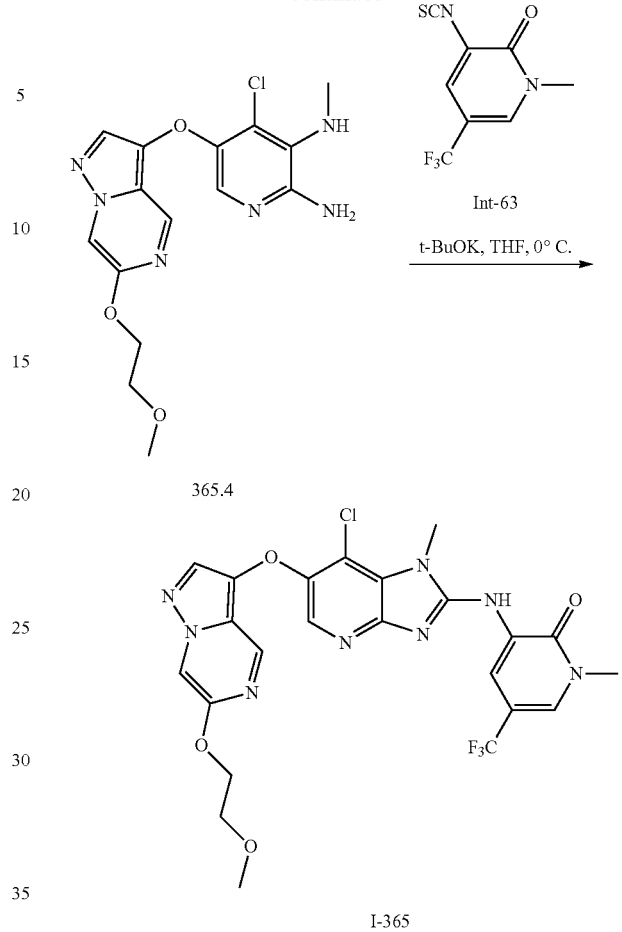

Synthesis of compound 365.1. A mixture of 336.1 (1 g, 5.08 mmol, 1.0 equiv), 2-methoxyethan-1-ol (0.772 g, 10.15 mmol, 2.0 equiv) and cesium carbonate (4.95 g, 15.24 mmol, 3.0 equiv) in toluene (30 mL) was degassed by bubbling argon through for 10 min. Under argon atmosphere, di-tert-butyl(2',4',6'-triisopropyl-3-methoxy-6-methyl-[1,1'-biphenyl]-2-yl)phosphine (0.357 g, 0.762 mmol, 0.15 equiv) and allyl palladium(II) chloride dimer (0.092 g, 0.254 mmol, 0.05 equiv) were added, and degassed for 5 min. The reaction mixture was stirred at 90° C. for 2 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 5.3% methanol in DCM) to afford 365.1). MS (ES): m/z 300.1 [M+H]⁺.

Synthesis of compound 365.2. A mixture of compound 365.1 (0.580 g, 2.83 mmol, 1.0 equiv) and 10% palladium on carbon (0.250 g) in methanol (10 mL) was stirred under hydrogen (1 atm) for 4 h. The reaction mixture was filtered through a pad of Celite® and rinsed with methanol. The filtrate was concentrated under reduced pressure. The residue was purified by flash column chromatography on silica gel (CombiFlash®, 5.0% Methanol in DCM) to afford 365.2. MS (ES): m/z 210.2 [M+H]⁺.

Synthesis of compound 365.3. Compound 365.3 was prepared from 365.2 and Int-4, following the procedure described in the synthesis of 19.1. The product was purified by flash column chromatography on silica gel (Combi-Flash®, 2.8% methanol in DCM). MS (ES): m/z 395.5 [M+H]⁺.

Synthesis of compound 365.4. Compound 365.4 was prepared from 365.3 following the procedure described in the synthesis of 5.4. The product was purified by flash column chromatography on silica gel (CombiFlash®, 3.0% methanol in DCM). MS (ES): m/z 365.6 [M+H]⁺.

Synthesis of I-365. Compound I-365 was prepared from 365.4 and Int-63, following the procedure described in the synthesis of I-13. The product was purified by flash column chromatography on silica gel (CombiFlash®, 3.8% methanol in DCM. MS (ES): m/z 565.2 [M+H]⁺, ¹H NMR (DMSO-d₆, 400 MHz): δ 8.85 (s, 1H), 8.82 (s, 1H), 8.61 (s, 1H), 8.36 (s, 1H), 8.23 (s, 1H), 8.14 (s, 1H), 7.89 (s, 1H), 4.34 (s, 3H), 4.02 (s, 3H), 3.69-3.67 (m, 7H).

Example 366: 2-((4,4-difluoro-4,5,6,7-tetrahydropyrazolo[1,5-a]pyridin-2-yl)amino)-1-methyl-6-(pyrazolo[1,5-a]pyridin-3-yloxy)-1H-imidazo[4,5-b]pyridine-7-carbonitrile Synthesis of compound 366.1. Compound 366.1 was prepared from 78.5 and Int-151, following the procedure described in the synthesis of I-13. The product was purified by flash column chromatography on silica gel (CombiFlash®, 2.8% methanol in DCM). MS (ES): m/z 471.6 [M+H]⁺.

Synthesis of I-366. Compound I-366 was prepared from 366.1 following the procedure described in the synthesis of I-157. The product was purified by flash column chromatography on silica gel (CombiFlash®, 4.2% methanol in DCM). MS (ES): m/z 462.2, ¹H NMR (DMSO-d₆, 400 MHz): δ 8.39 (s, 1H), 8.00 (s, 1H), 7.88 (s, 1H), 7.60 (s, 1H), 7.48-7.43 (m, 2H), 7.06 (s, 1H), 6.83 (s, 1H), 3.95 (s, 3H), 3.68 (bs, 2H), 2.19 (bs, 2H), 1.55 (bs, 2H).

Example 367: 6-((6-(2-methoxyethoxy)pyrazolo[1,5-a]pyrazin-3-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

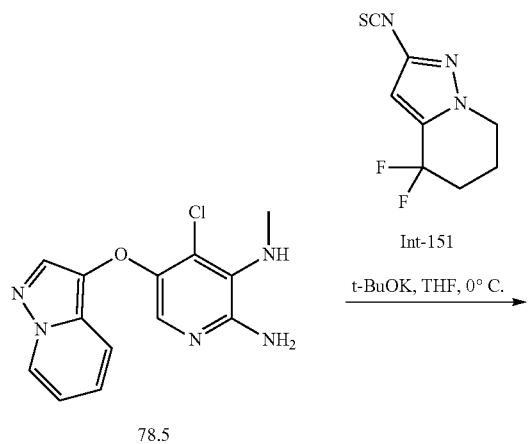
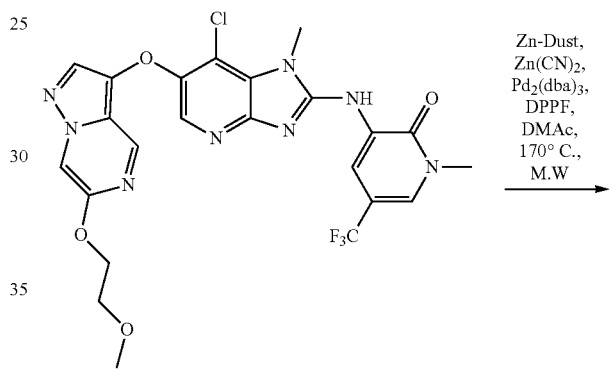
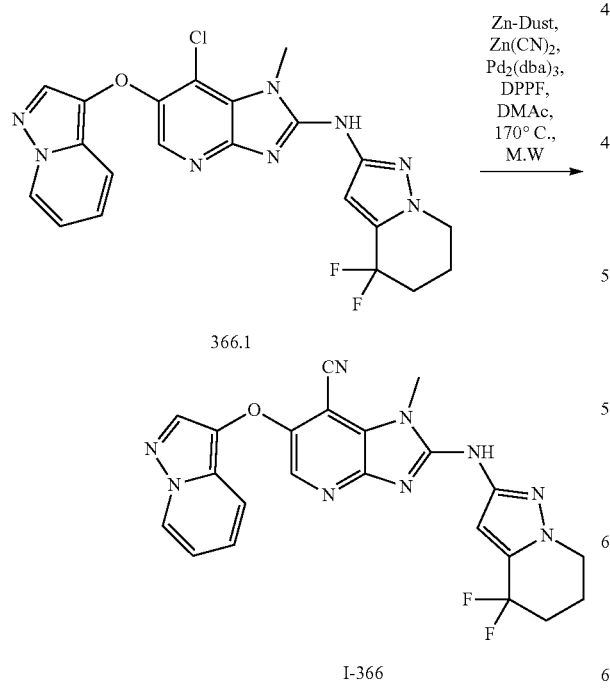
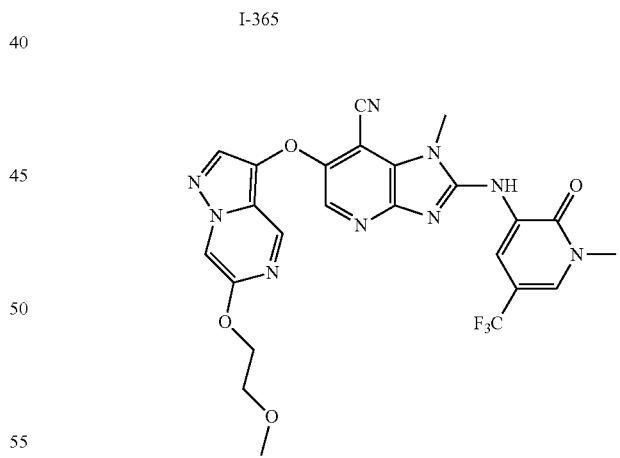

Synthesis of I-367. Compound I-367 was prepared from I-365 following the procedure described in the synthesis of I-157. The product was purified by flash column chromatography on silica gel (CombiFlash®, 5.0% methanol in DCM). MS (ES): m/z 556.3, ¹H NMR (DMSO-d₆, 400 MHz): δ 9.00 (s, 1H), 8.88 (s, 1H), 8.61 (s, 1H), 8.43 (s, 1H), 8.15 (s, 1H), 8.12 (s, 1H), 8.09 (s, 1H), 4.35-4.33 (t, 2H), 3.98 (s, 3H), 3.70-3.68 (t, 2H), 3.65 (s, 3H), 3.31 (s, 3H).

Example 368: 6-((3-(dimethylamino)-1H-pyrazolo[3,4-b]pyridin-5-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile
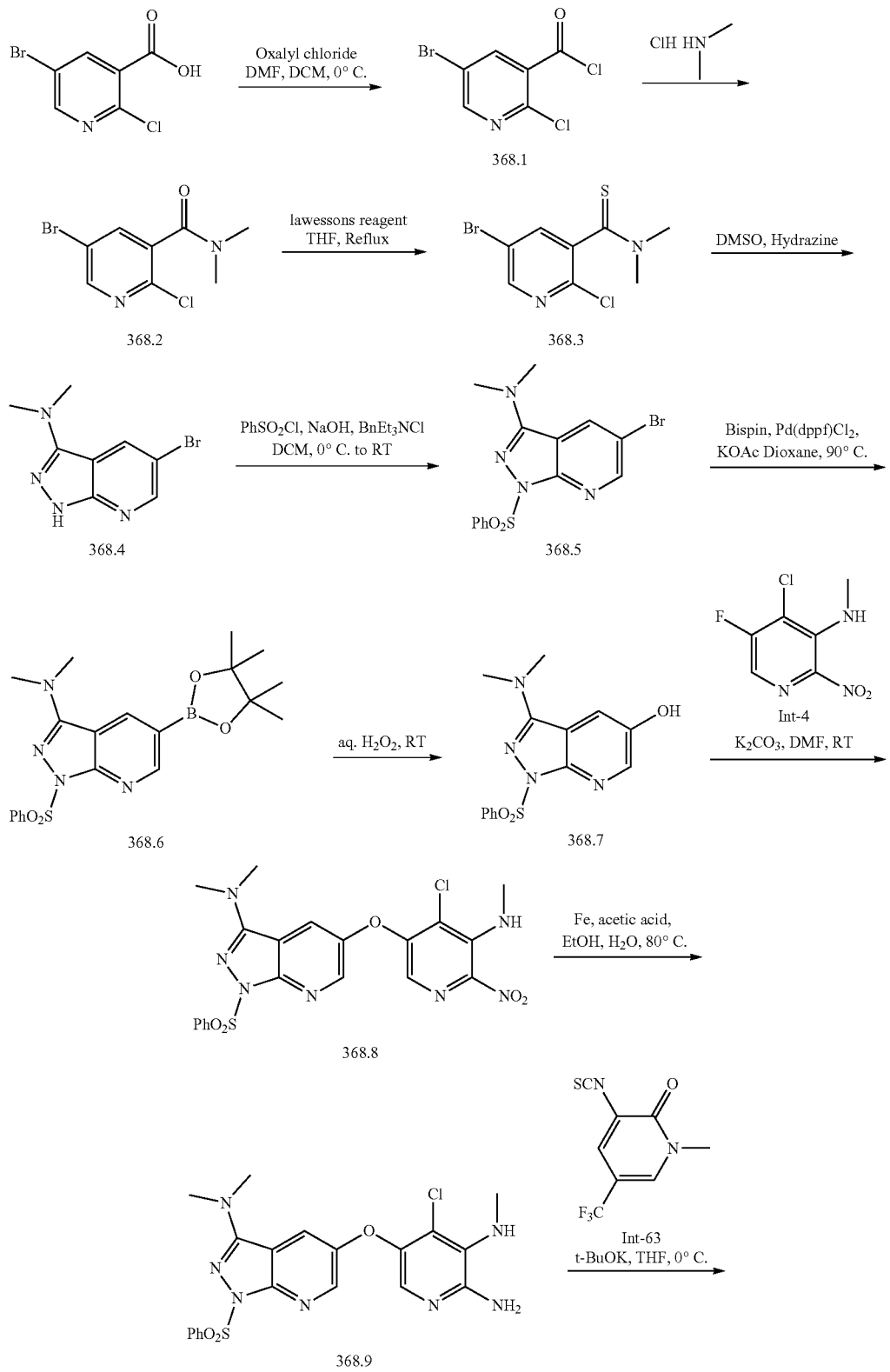

-continued

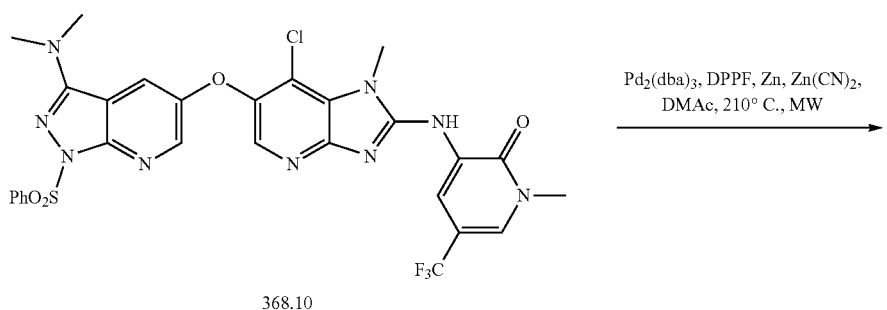
368.10

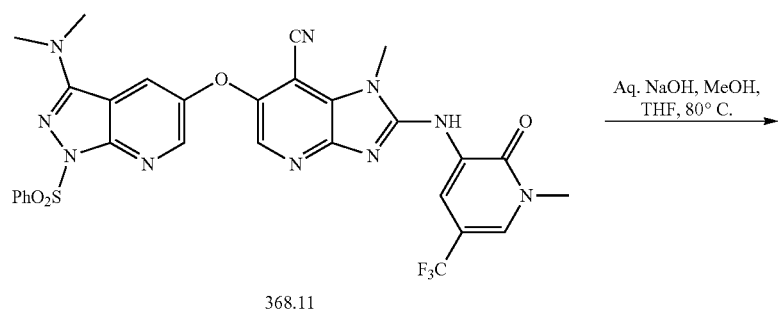
368.11

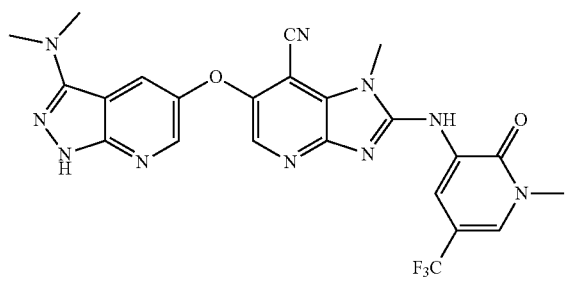
I-368

Synthesis of compound 368.1. To a solution of 5-bromo-2-chloronicotinic acid (10 g, 42.29 mmol, 1.0 equiv) and DMF (1 mL) in DCM (100 mL) was added oxalyl chloride (7.99 g, 63.43 mmol, 1.5 equiv) at 0° C. and stirred for 2 h. The reaction mixture was concentrated under reduced pressure to afford 368.1. MS (ES): m/z 255.1 [M+H]$^+$.

Synthesis of compound 368.2 To a solution of 368.1 (10 g, 39.23 mmol, 1.0 equiv) in DCM (100 mL) was added dimethylamine hydrochloride (7.3 g, 90.22 mmol, 2.3 equiv) and stirred at room temperature for 16 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 60% ethyl acetate in hexane) to afford 368.2. MS (ES): m/z 264.1 [M+H]$^+$.

Synthesis of compound 368.3 To a solution of 368.2 (3.6 g, 13.66 mmol, 1.0 equiv) in THF (36 mL) was added Lawesson's reagent (11.03 g, 27.32 mmol, 2.0 equiv). The solution was heated to reflux for 15 min. It was cooled to room temperature and concentrated under reduced pressure. The residue was purified by flash column chromatography on silica gel (CombiFlash®, 11% ethyl acetate in hexane) to afford 368.3. MS (ES): m/z 280.1 [M+H]$^+$.

Synthesis of compound 368.4 To a solution of 368.3 (3.0 g, 10.73 mmol, 1.0 equiv) in dimethyl sulfoxide (30 mL) was added hydrazine hydrate (5.36 g, 107.3 mmol, 10 equiv) and stirred at 120° C. for 5 h. It was transferred into ice-water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 26% ethyl acetate in hexane) to afford 368.4. MS (ES): m/z 242.1 [M+H]$^+$.

Synthesis of compound 368.5. To a solution of 368.4 (1.3 g, 5.39 mmol, 1.0 equiv), benzyltriethylammonium chloride (0.024 g, 0.107 mmol, 0.02 equiv) and sodium hydroxide (0.646 g, 16.17 mmol, 3.0 equiv) in DCM (20 mL) was added benzyl sulphonyl chloride (1.18 g, 6.73 mmol, 1.25 equiv) at 0° C. The reaction mixture was allowed to warm to room temperature and stirred for 2 h. It was transferred into ice-water, stirred, and extracted with DCM. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford 368.5. MS (ES): m/z 382.1 [M+H]$^+$.

Synthesis of compound 368.6. A mixture of 368.5 (0.910 g, 2.39 mmol, 1.0 equiv), bis(pinacolato)diboron (1.21 g, 3.02 mmol, 2.0 equiv) and potassium acetate (0.295 g, 3.02 mmol, 2.0 equiv) in DMF (18 mL) was degassed by bubbling argon through for 30 min. Under argon atmosphere, 1,1-bis(diphenylphosphino)ferrocene-palladium(II) dichloride DCM complex (0.034 g, 0.047 mmol, 0.02 equiv) was added. The reaction mixture was stirred at 90° C. for 2 h. It was poured into ice-water and extracted with ethyl acetate. The combined organic layers were washed with brine, dried over anhydrous sodium sulfate, filtered, and concentrated under reduced pressure to afford 368.6. MS (ES): m/z 429.1 [M+H]$^+$.

Synthesis of compound 368.7. To a solution 368.6 (0.900 g, 2.10 mmol, 1.0 equiv) in acetonitrile:methanol (1:1, 27 mL) was added aqueous hydrogen peroxide solution (18 mL). The reaction mixture was stirred at room temperature for 16 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2% methanol in DCM) to afford 368.7. MS (ES): m/z 318.2 [M+H]$^+$.

Synthesis of compound 368.8. Compound 368.8 was prepared from 368.7 and Int-4, following the procedure described in the synthesis of 19.1. The product was used in the next step without purification. MS (ES): m/z 504.5 [M+H]$^+$.

Synthesis of compound 368.9. Compound 368.9 was prepared from 368.8 following the procedure described in the synthesis of 5.4. The product was purified by flash column chromatography on silica gel (CombiFlash®, 0.5% methanol in DCM). MS (ES): m/z 474.5 [M+H]$^+$.

Synthesis of compound 368.10. Compound 368.10 was prepared from 368.9 and Int-63, following the procedure described in the synthesis of I-13. The product was purified by flash column chromatography on silica gel (CombiFlash®, 2% methanol in DCM). MS (ES): m/z 675.7 [M+H]$^+$.

Synthesis of compound 368.11. Compound 368.11 was prepared from 368.10 following the procedure described in the synthesis of 330.6. The product was purified by flash column chromatography on silica gel (CombiFlash®, 3% methanol in DCM). MS (ES): m/z 665.3 [M+H]$^+$.

Synthesis of I-368. Compound I-368 was prepared from 368.11 following the procedure described in the synthesis of I-304. The product was purified by flash column chromatography on silica gel (CombiFlash®, 3% methanol in DCM). MS (ES): m/z 525.2 [M+H]$^+$, $^1$H NMR (DMSO-d$_6$, 400 MHz): δ 8.99 (s, 1H), 8.63 (s, 1H), 8.44 (s, 1H), 8.17 (s, 1H), 7.98 (s, 1H), 7.08 (s, 1H), 6.84 (s, 1H), 3.99 (s, 3H), 3.67 (s, 3H), 2.97 (s, 6H).

Example 369: 2-((4,4-difluoro-4,5,6,7-tetrahydropyrazolo[1,5-a]pyridin-2-yl)amino)-6-((6-(2-methoxyethoxy)pyrazolo[1,5-a]pyridin-3-yl)oxy)-1-methyl-1H-imidazo[4,5-b]pyridine-7-carbonitrile

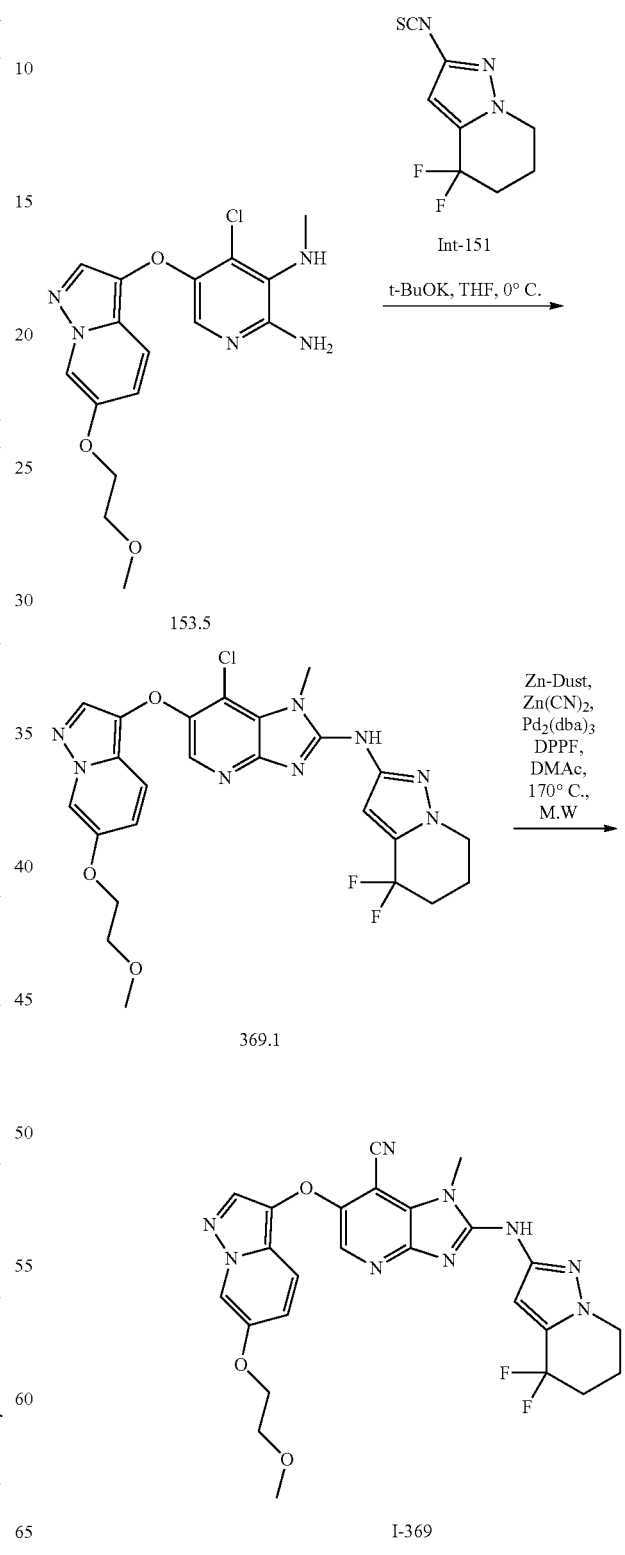

Synthesis of compound 369.1. Compound 369.1 was prepared from 153.5 and Int-151, following the procedure described in the synthesis of I-13. The product was purified by flash column chromatography on silica gel (CombiFlash®, 2.5% methanol in DCM). MS (ES): m/z 545.5 [M+H]$^+$.

Synthesis of I-369. Compound I-369 was prepared from 369.1 following the procedure described in the synthesis of I-157. The product was purified by flash column chromatography on silica gel (CombiFlash®, 4.2% methanol in DCM). MS (ES): m/z 536.52, [M+H]$^+$, $^1$H NMR (DMSO-d$_6$, 400 MHz): δ 8.39 (s, 1H), 8.00 (s, 1H), 7.88 (s, 1H), 7.60 (s, 1H), 7.48-7.43 (m, 2H), 7.06 (s, 1H), 4.16 (bs, 5H), 3.95 (s, 3H), 3.74-3.68 (m, 4H), 2.19 (bs, 2H), 1.55 (bs, 2H).

Example 370: 6-((1H-pyrazolo[3,4-b]pyridin-5-yl)oxy)-2-((4,4-difluoro-4,5,6,7-tetrahydropyrazolo[1,5-a]pyridin-2-yl)amino)-1-methyl-1H-imidazo[4,5-b]pyridine-7-carbonitrile

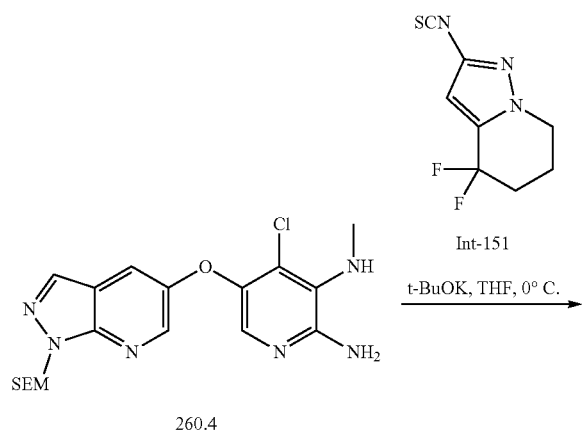

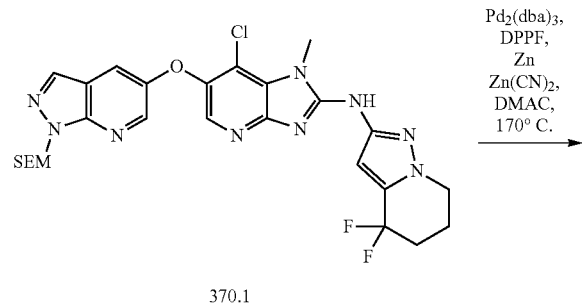

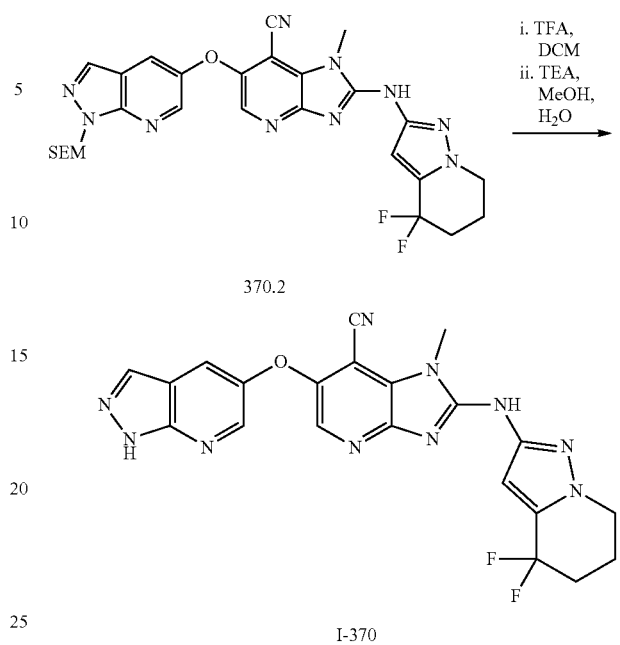

Synthesis of compound 370.1. Compound 370.1 was prepared from 260.4 and Int-151, following the procedure described in the synthesis of I-13. The product was purified by flash column chromatography on silica gel (CombiFlash®, 2.5% methanol in DCM). MS (ES): m/z 603.1 [M+H]$^+$.

Synthesis of compound 370.2. Compound 370.2 was prepared from 370.1 following the procedure described in the synthesis of I-157. The product was purified by flash column chromatography on silica gel (CombiFlash®, 3.1% methanol in DCM). MS (ES): m/z 593.5 [M+H]$^+$.

Synthesis of I-370. To a solution of 370.2 (0.070 g, 0.138 mmol, 1.0 equiv) in DCM (4 mL) was added trifluoroacetic acid (1.0 mL) at 0° C. and stirred for 2 h. It was transferred into ice-saturated sodium bicarbonate solution and extracted with DCM. The combined organic layers were washed with brine, dried over anhydrous sodium sulfate, filtered, and concentrated under reduced pressure. The residue was diluted with methanol (2 mL) and water (2 mL) followed by the addition of triethylamine (1.5 mL). The reaction mixture was stirred at room temperature for 12 h. It was transferred into ice-saturated sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 4.3% methanol in DCM) to afford I-370. MS (ES): m/z 463.2 [M+H]$^+$, $^1$H NMR (DMSO-d$_6$, 400 MHz): δ 13.79 (s, 1H), 10.63 (s, 1H), 8.58-8.57 (d, J=2.4 Hz, 1H), 8.10 (s, 1H), 8.04 (s, 1H), 7.91 (s, 1H), 7.09 (s, 1H), 4.17 (bs, 2H), 3.95 (s, 3H), 2.47 (bs, 2H), 2.20 (bs, 2H).

Example 371: 7-chloro-1-methyl-6-((6-(methyl-amino)pyrazolo[1,5-a]pyrazin-3-yl)oxy)-N-(3-((1-methylpiperidin-4-yl)oxy)-5-(trifluoromethyl)phenyl)-1H-imidazo[4,5-b]pyridin-2-amine

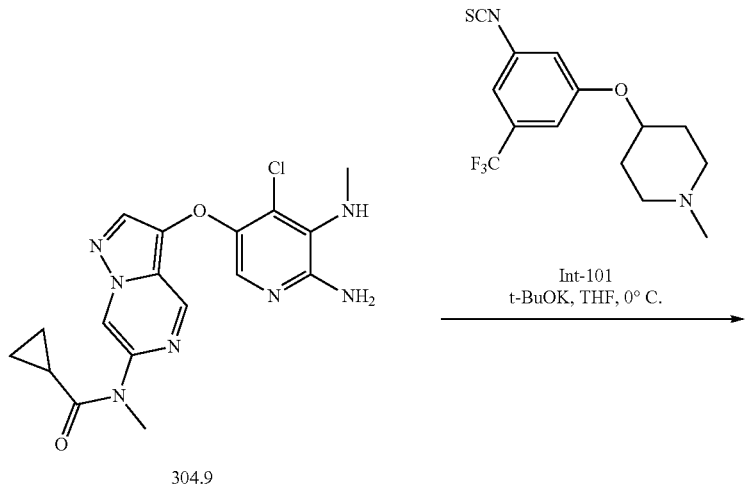

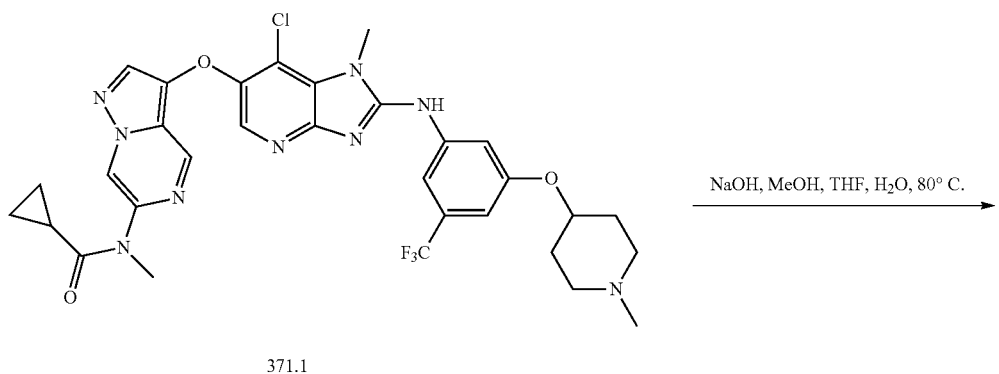

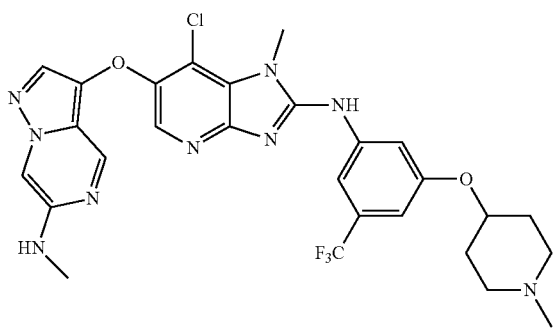

Synthesis of compound 371.1. Compound 371.1 was prepared from 304.9 and Int-101, following the procedure described in the synthesis of I-13. The product was purified by flash column chromatography on silica gel (CombiFlash®, 5.5% methanol in DCM). MS (ES): m/z 671.1 [M+H]$^+$.

Synthesis of I-371. Compound I-371 was prepared from 371.1 following the procedure described in the synthesis of I-304. The product was purified by flash column chromatography on silica gel (CombiFlash®, 4.2% methanol in DCM). MS (ES): m/z 601.3 [M−H]$^+$.

Example 372: 7-chloro-N-(4-((3-methoxyazetidin-1-yl)methyl)-3-(trifluoromethyl)phenyl)-1-methyl-6-((6-(methylamino)pyrazolo[1,5-a]pyrazin-3-yl)oxy)-1H-imidazo[4,5-b]pyridin-2-amine

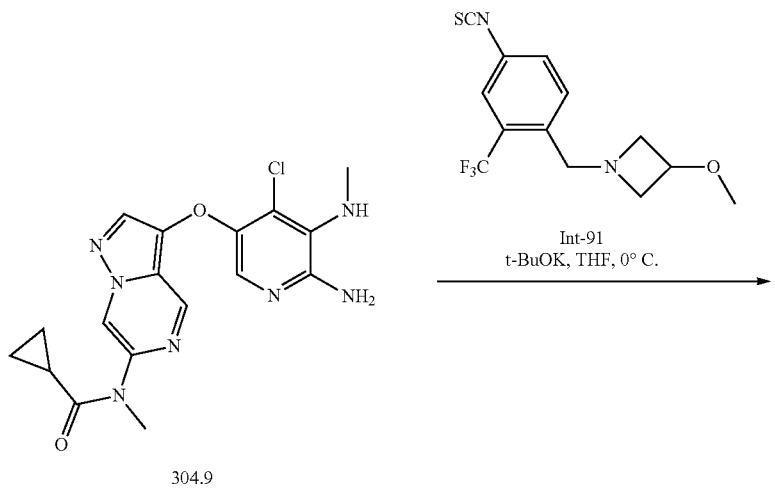

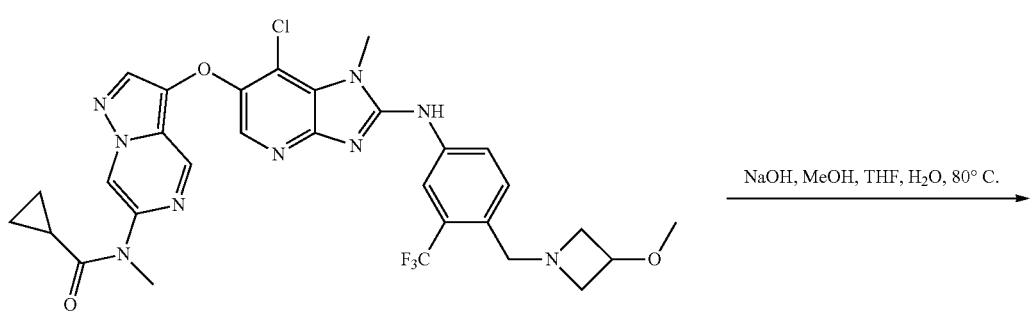

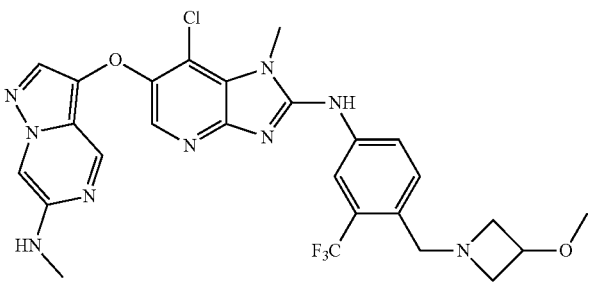

Synthesis of compound 372.1. Compound 372.1 was prepared from 304.9 and Int-91, following the procedure described in the synthesis of I-13. The product was purified by flash column chromatography on silica gel (CombiFlash®, 4.5% methanol in DCM). MS (ES): m/z 657.0 [M+H]$^+$.

Synthesis of I-372. Compound I-372 was prepared from 372.1 following the procedure described in the synthesis of I-304. The product was purified by flash column chromatography on silica gel (CombiFlash®, 4.0% methanol in DCM). MS (ES): m/z 588.2 [M+H]$^+$.

Example 373: 2-((4,4-difluoro-4,5,6,7-tetrahydropyrazolo[1,5-a]pyridin-2-yl)amino)-1-methyl-6-((4-(methylamino)pyrazolo[1,5-a]pyrazin-3-yl)oxy)-1H-imidazo[4,5-b]pyridine-7-carbonitrile

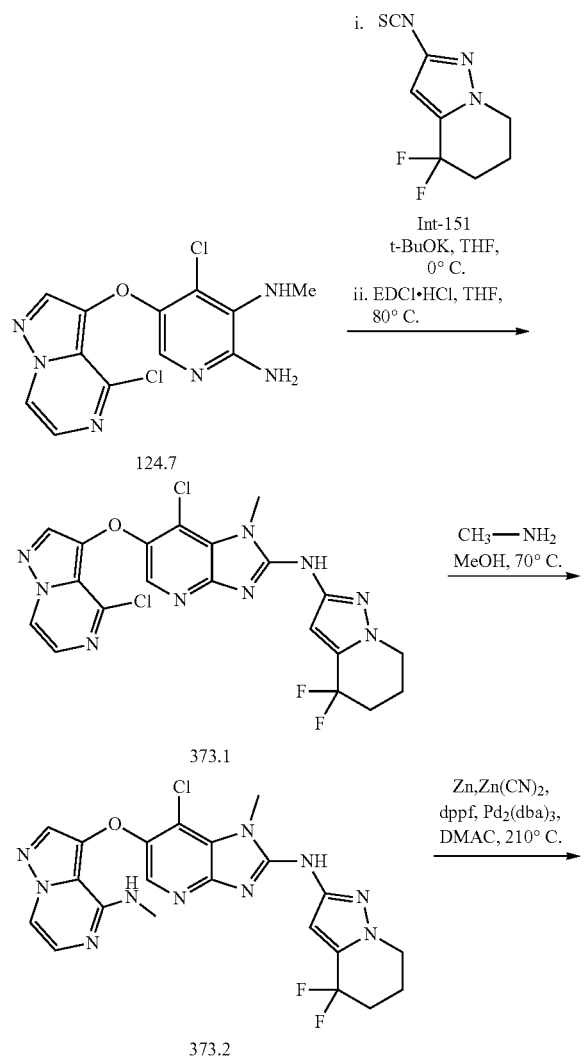

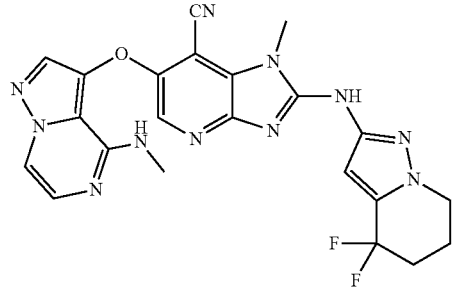

I-373

Synthesis of compound 373.1. Compound 373.1 was prepared from 124.7 and Int-151, following the procedure described in the synthesis of 331.1. The product was purified by flash column chromatography on silica gel (CombiFlash®, 3.0% methanol in DCM). MS (ES): m/z 507.1 [M+H]⁺.

Synthesis of compound 373.2. To a solution of 373.1 (0.060 g, 0.118 mmol, 1.0 equiv) in methanol (3 mL) was added methylamine solution (2 M in THF, 0.6 mL) and reaction mixture was stirred at 70° C. for 6 h. The reaction mixture was concentrated under reduced pressure. The residue was purified by trituration in methanol to afford 373.2. MS (ES): m/z 501.6 [M+H]⁺.

Synthesis of I-373. Compound I-373 was prepared from 373.2 following the procedure described in the synthesis of 330.6. The product was purified by flash column chromatography on silica gel (CombiFlash®, 3.5% methanol in DCM). MS (ES): m/z 492.7 [M+H]⁺, ¹H NMR (DMSO-$d_6$, 400 MHz): δ 10.64 (s, 1H), 8.04 (s, 1H), 7.83-7.82 (d, J=4.8 Hz, 1H), 7.73 (s, 1H), 7.29-7.28 (d, J=4.8 Hz, 1H), 7.06 (s, 1H), 6.80-6.79 (d, J=4.4 Hz, 1H), 4.14 (bs, 2H), 3.94 (s, 3H), 2.96-2.95 (d, 3H), 2.45 (bs, 2H), 2.18 (bs, 2H).

Example 374: 2-((4,4-difluoro-4,5,6,7-tetrahydropyrazolo[1,5-a]pyridin-2-yl)amino)-6-((6-methoxypyrazolo[1,5-a]pyridin-3-yl)oxy)-1-methyl-1H-imidazo[4,5-b]pyridine-7-carbonitrile

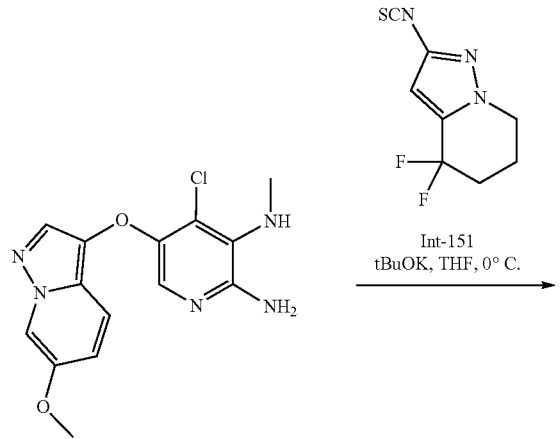

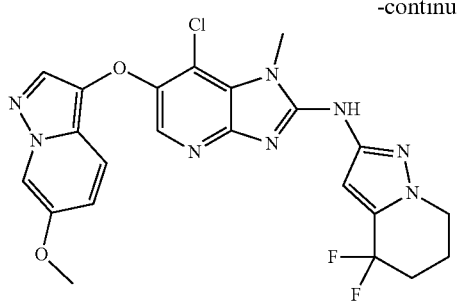

374.1

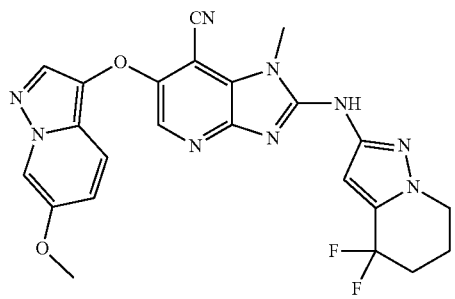

I-374

Synthesis of compound 374.1. Compound 374.1 was prepared from 291.6 and Int-151, following the procedure described in the synthesis of I-13. The product was purified by flash column chromatography on silica gel (CombiFlash®, 2.6% methanol in DCM). MS (ES): m/z 501.7 [M+H]⁺.

Synthesis of I-374. Compound I-374 was prepared from 374.1 following the procedure described in the synthesis of I-157. The product was purified by flash column chromatography on silica gel (CombiFlash®, 5.2% methanol in DCM). MS (ES): m/z 492.1 [M+H]⁺, $^1$H NMR (DMSO-d$_6$, 400 MHz): δ 10.57 (s, 1H), 8.38 (s, 1H), 8.01 (s, 1H), 7.88 (s, 1H), 7.48-7.46 (d, J=9.2 Hz, 1H), 7.06 (s, 1H), 7.04 (s, 1H), 3.96 (s, 3H), 3.85 (bs, 2H), 3.33 (s, 3H), 2.46 (bs, 2H), 2.20 (bs, 2H).

Example 375: 3-((7-chloro-6-((6-(2-methoxyethoxy)pyrazolo[1,5-a]pyrazin-3-yl)oxy)-1-methyl-1H-imidazo[4,5-b]pyridin-2-yl)amino)-5-cyclopropyl-1-methylpyridin-2(1H)-one

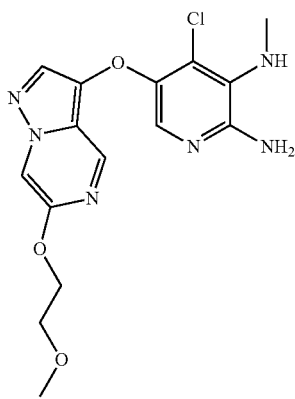

365.4

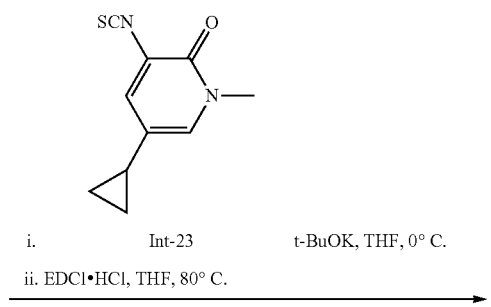

i. Int-23        t-BuOK, THF, 0° C.
ii. EDCl•HCl, THF, 80° C.

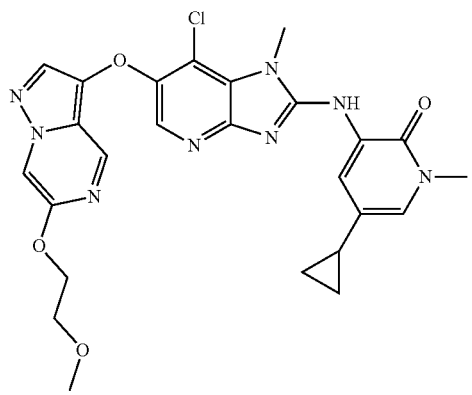

I-375

Synthesis of I-375. Compound I-375 was prepared from 365.4 and Int-23, following the procedure described in the synthesis of 331.1. The product was purified by flash column chromatography on silica gel (CombiFlash®, 4.0% methanol in DCM). MS (ES): m/z 537.4 [M+H]$^+$, $^1$H NMR (DMSO-d$_6$, 400 MHz): δ 8.83 (s, 1H), 8.51 (s, 1H), 8.35 (s, 1H), 8.28 (s, 1H), 8.18 (s, 1H), 7.87 (s, 1H), 7.23 (s, 1H), 4.33 (bs, 2H), 3.98 (s, 3H), 3.68 (bs, 2H), 3.55 (s, 3H), 3.31 (s, 3H), 1.56 (bs, 1H), 0.87-0.85 (m, 2H), 0.58-0.57 (m, 2H).

Example 376: 3-((7-chloro-1-methyl-6-((6-(2-morpholinoethoxy)pyrazolo[1,5-a]pyrazin-3-yl)oxy)-1H-imidazo[4,5-b]pyridin-2-yl)amino)-1-methyl-5-(trifluoromethyl)pyridin-2(1H)-one

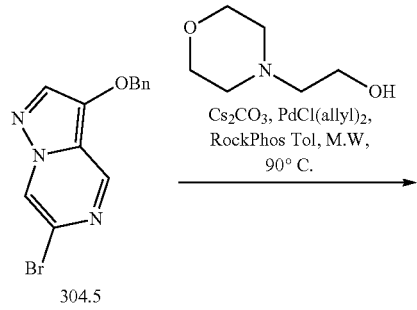

304.5

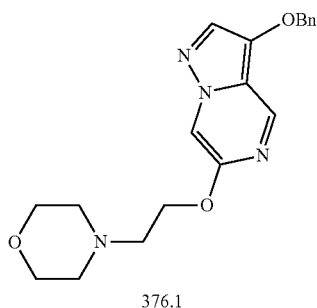

376.1

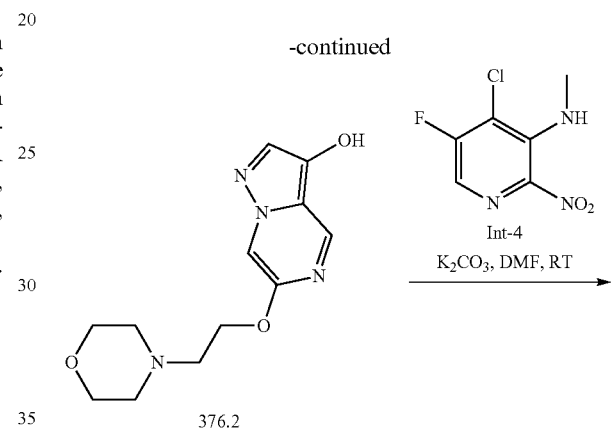

376.2

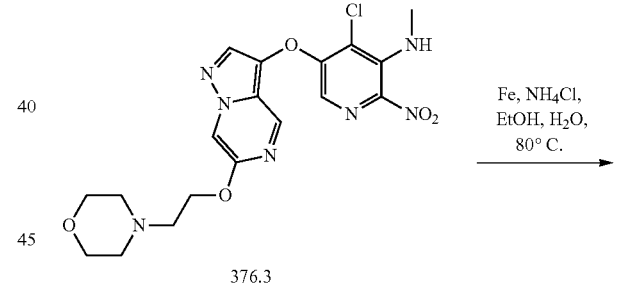

376.3

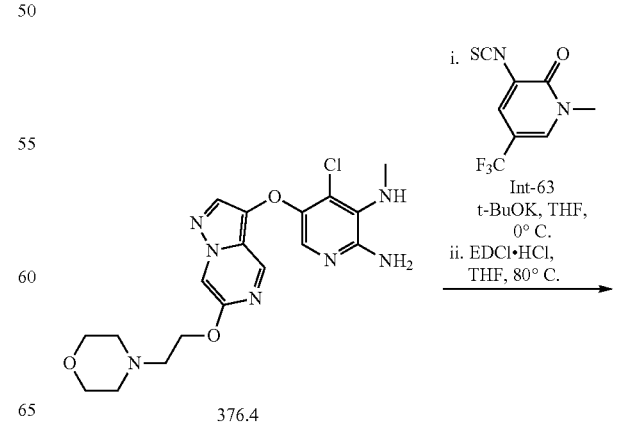

376.4

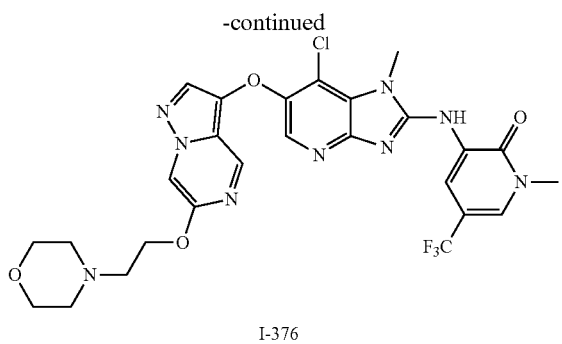

I-376

Synthesis of compound 376.1. A suspension of di-tert-butyl(2',4',6'-triisopropyl-3-methoxy-6-methyl-[1,1'-biphenyl]-2-yl)phosphine (0.154 g, 0.329 mmol, 0.1 equiv), allylpalladium(II) chloride dimer (0.060 g, 0.164 mmol, 0.05 equiv), and cesium carbonate (1.60 g, 4.93 mmol, 1.5 equiv) in toluene (10 mL) was degassed by bubbling argon through for 10 min. Under argon atmosphere, 304.5 (1.0 g, 3.29 mmol, 1.0 equiv) and 2-morpholinoethan-1-ol (0.862 g, 6.58 mmol, 2.0 equiv) were added, and degassed for 5 min. The reaction mixture was stirred at 90° C. for 5 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.6% methanol in DCM) to afford 376.1. MS (ES): m/z 355.5 [M+H]$^+$.

Synthesis of compound 376.2. A mixture of compound 376.1 (0.500 g, 1.41 mmol, 1.0 equiv) and 10% palladium on charcoal (0.500 g) in methanol (10 mL) was stirred under hydrogen (1 atm) for 30 min. The reaction mixture was filtered through a pad of Celite® and rinsed with methanol. The filtrate was concentrated under reduced pressure to afford 376.2. MS (ES): m/z 265.2 [M+H]$^+$.

Synthesis of compound 376.3. Compound 376.3 was prepared from 376.2 and Int-4, following the procedure described in the synthesis of 19.1. The product was purified by flash column chromatography on silica gel (CombiFlash®, 40% ethyl acetate in hexane). MS (ES): m/z 450.5 [M+H]$^+$.

Synthesis of compound 376.4. Compound 376.4 was prepared from 376.3 following the procedure described in the synthesis of 5.4. The product was purified by flash column chromatography on silica gel (CombiFlash®, 3.4% methanol in DCM). MS (ES): m/z 420.5 [M+H]$^+$.

Synthesis of I-376. Compound I-376 was prepared from 376.4 and Int-63, following the procedure described in the synthesis of 331.1. The product was purified by flash column chromatography on silica gel (CombiFlash®, 4% methanol in DCM). MS (ES): m/z 620.3 [M+H]$^+$, $^1$H NMR (DMSO-d$_6$, 400 MHz): δ 8.83 (s, 2H), 8.61 (s, 1H), 8.36 (s, 1H), 8.21 (s, 1H), 8.14 (s, 1H), 7.88 (s, 1H), 4.31 (bs, 2H), 4.01 (s, 3H), 3.66 (s, 3H), 3.57 (s, 4H), 2.71 (bs, 2H), 2.68 (bs, 4H).

Example 377: 1-methyl-2-((1-methyl-2-oxo-5-(trifluoromethyl)-1,2-dihydropyridin-3-yl)amino)-6-((6-(2-morpholinoethoxy)pyrazolo[1,5-a]pyrazin-3-yl)oxy)-1H-imidazo[4,5-b]pyridine-7-carbonitrile

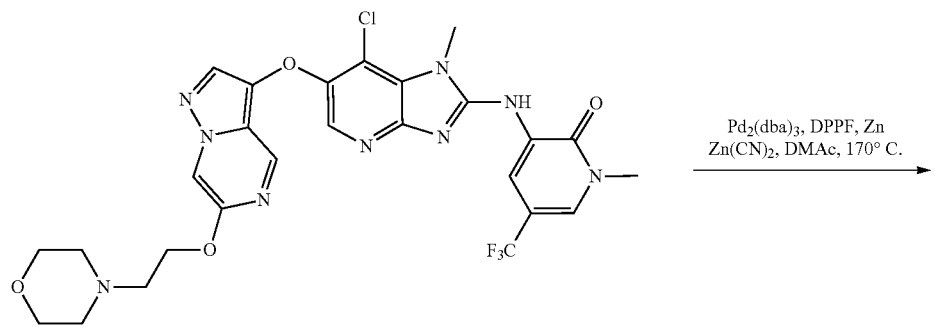

I-376

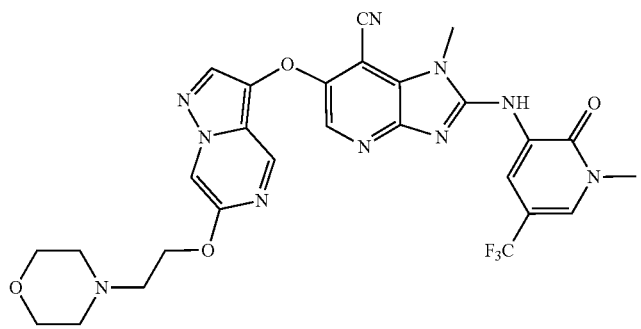

I-377

Synthesis of I-377. Compound I-377 was prepared from I-376 following the procedure described in the synthesis of I-157. The product was purified by flash column chromatography on silica gel (CombiFlash®, 5% methanol in DCM). MS (ES): m/z 610.4 [M+H]+, ¹H NMR (DMSO-d₆, 400 MHz): δ 9.00 (s, 1H), 8.88 (s, 1H), 8.62 (s, 1H), 8.43 (s, 1H), 8.17 (s, 1H), 8.13 (s, 1H), 8.10 (s, 1H), 4.32 (bs, 2H), 3.99 (s, 3H), 3.66 (s, 3H), 3.57 (s, 4H), 3.51 (s, 2H), 2.72 (s, 4H).

Example 378: 2-((4,4-difluoro-4,5,6,7-tetrahydropyrazolo[1,5-a]pyridin-2-yl)amino)-6-((3-methoxy-1H-pyrazolo[3,4-b]pyridin-5-yl)oxy)-1-methyl-1H-imidazo[4,5-b]pyridine-7-carbonitrile

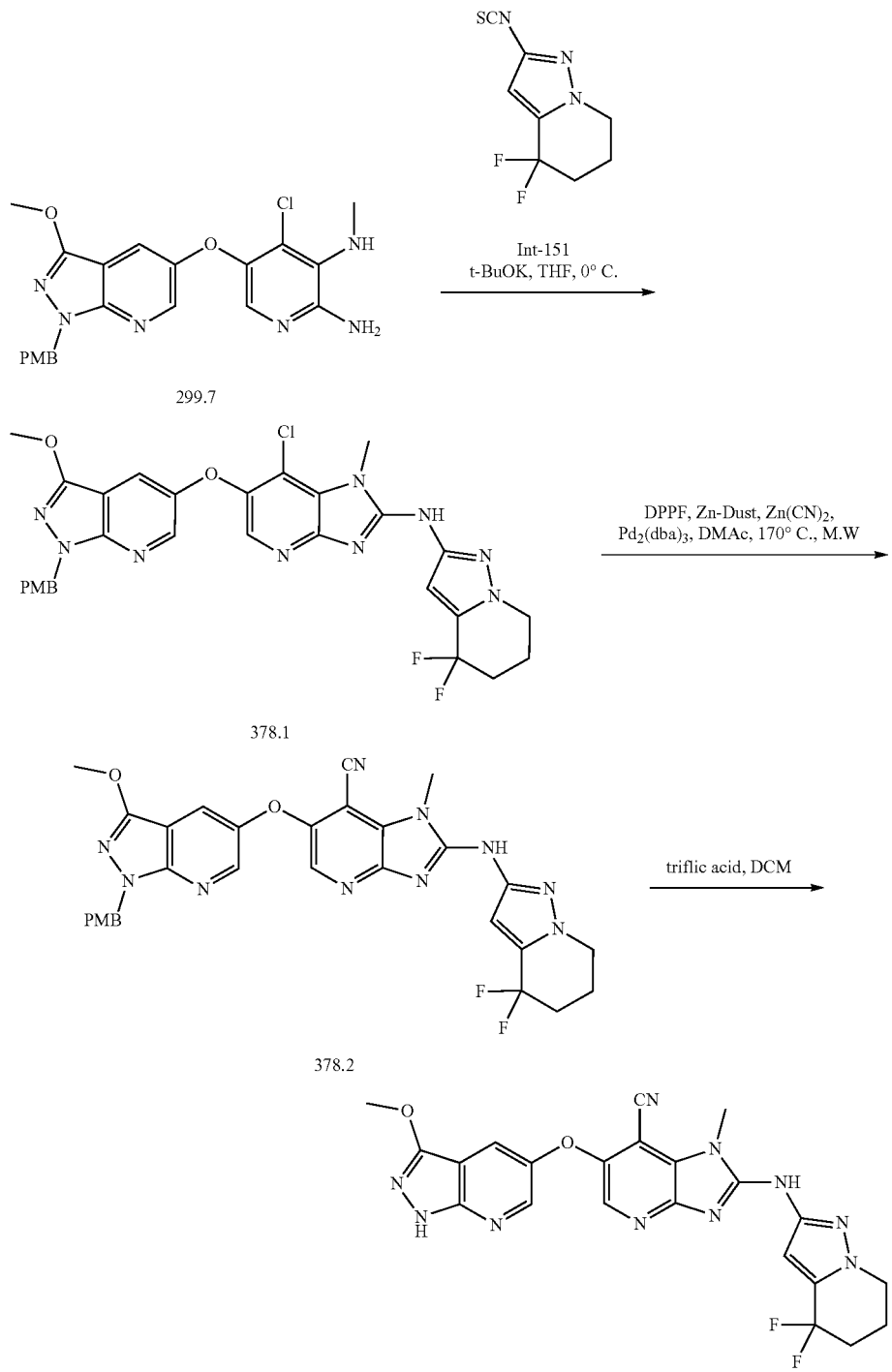

Synthesis of compound 378.1. Compound 378.1 was prepared from 299.7 and Int-151, following the procedure described in the synthesis of I-13. The product was purified by flash column chromatography on silica gel (Combi-Flash®, 3.8% methanol in DCM). MS (ES): m/z 623.7 [M+H]+.

Synthesis of compound 378.2. Compound 378.2 was prepared from 378.1 following the procedure described in the synthesis of I-157. The product was purified by flash column chromatography on silica gel (CombiFlash®, 4% methanol in DCM). MS (ES): m/z 613.3 [M+H]+.

Synthesis of I-378. To a solution of 378.2 (0.050 g, 0.081 mmol, 1.0 equiv) in DCM (4 mL) was added triflic acid (0.5 mL) at 0° C. The reaction mixture was stirred at room temperature for 35 min. It was concentrated under reduced pressure. The residue was transferred into an aqueous sodium bicarbonate solution and extracted with DCM. The combined organic layers were washed with brine, dried over anhydrous sodium sulfate, filtered, and concentrated under reduced pressure. The residue was purified by flash column chromatography on silica gel (CombiFlash®, 4.5% methanol in DCM) to afford I-378. MS (ES): m/z 493.3 [M+H]+. $^1$H NMR (DMSO-$d_6$, 400 MHz): δ 10.60 (s, 1H), 8.53 (s, 1H), 8.00 (s, 1H), 7.76 (s, 1H), 7.09 (s, 1H), 6.84-6.82 (d, J=6.4 Hz, 1H), 4.16 (s, 3H), 3.98 (s, 3H), 3.94 (s, 2H), 2.20 (bs, 2H), 1.56 (bs, 2H).

Example 395: 6-((4-fluoro-6-(methylamino)pyrazolo[1,5-a]pyridin-3-yl)oxy)-1-methyl-2-((1-methyl-2-oxo-5-(trifluoromethyl)-1,2-dihydropyridin-3-yl)amino)-1H-imidazo[4,5-b]pyridine-7-carbonitrile

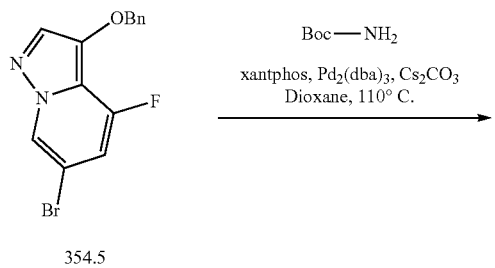

354.5

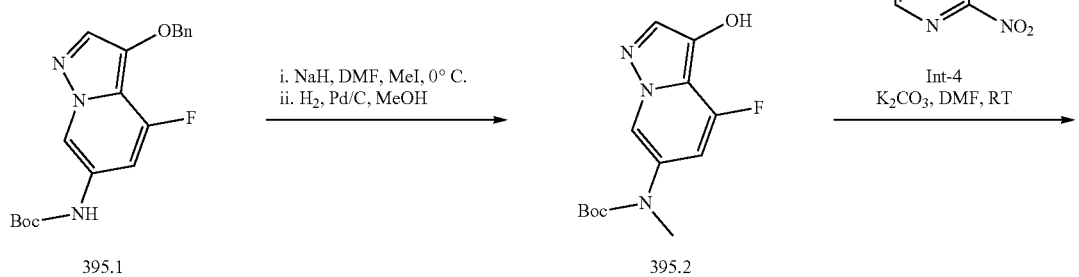

395.1 → 395.2

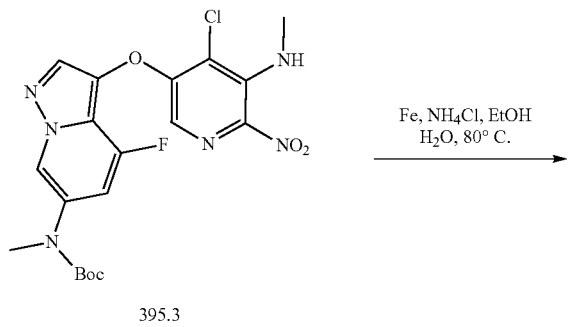

395.3

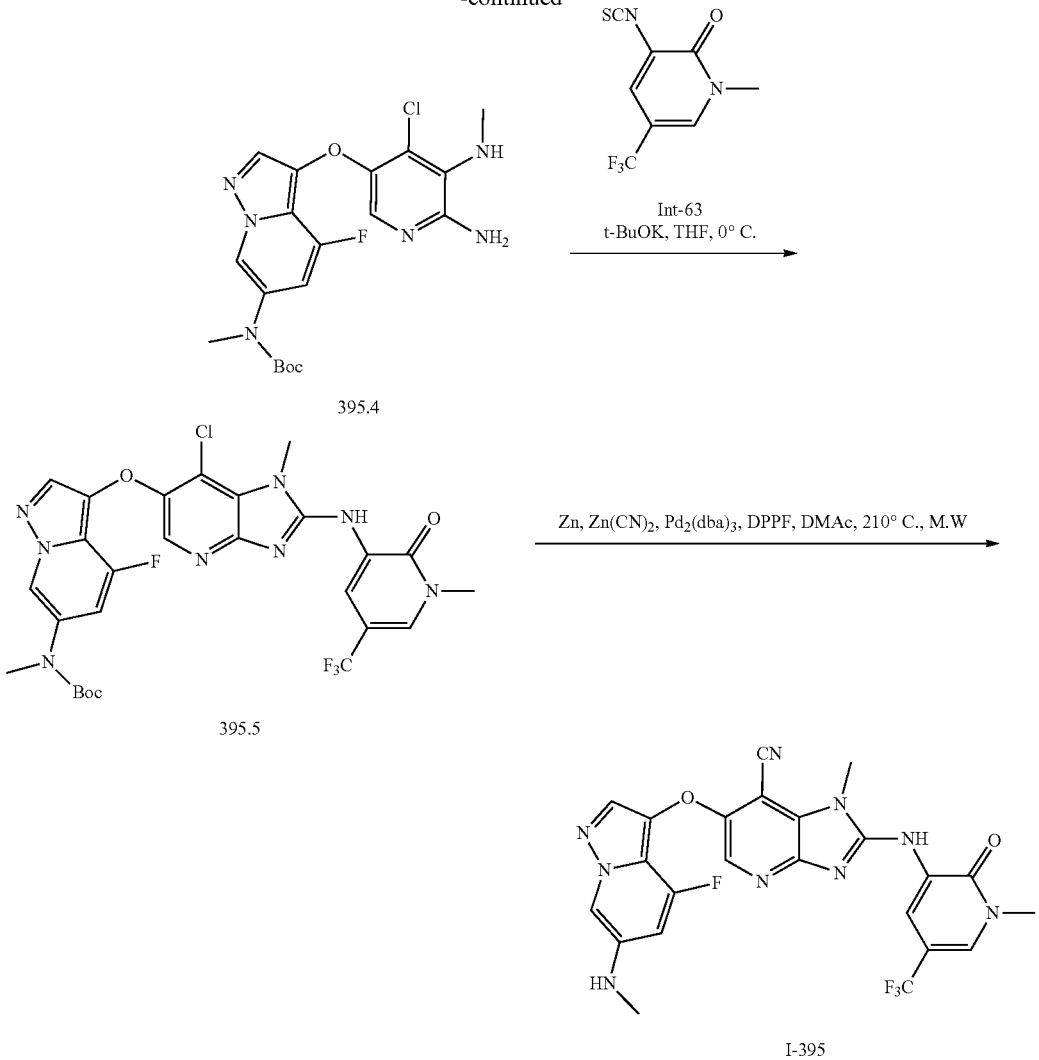

Synthesis of compound 395.1. A mixture of 354.5 (1.3 g, 4.05 mmol, 1.0 equiv), tert-butyl carbamate (1.42 g, 12.14 mmol, 3.0 equiv) and cesium carbonate (3.9 g, 12.14 mmol, 3.0 equiv) in 1,4-dioxane (3 mL) was degassed by bubbling argon through for 10 min. Under argon atmosphere, 4,5-bis(diphenylphosphino)-9,9-dimethylxanthene (0.234 g, 0.404 mmol, 0.1 equiv) and tris(dibenzylideneacetone)dipalladium(0) (0.185 g, 0.202 mmol, 0.05 equiv) were added, and degassed for 5 min. The reaction mixture was stirred at 110° C. for 6 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 15% ethyl acetate in hexane) to afford 379.1. MS (ES): m/z 358.2 [M+H]$^+$.

Synthesis of compound 395.2. To a solution of 395.1 (1.0 g, 2.8 mmol, 1.0 equiv) in DMF (20 mL) was added sodium hydride (0.134 g, 5.6 mmol, 2.0 equiv) at 0° C. and stirred for 30 min. To the mixture was added methyl iodide (0.477 g, 3.3 mmol, 1.3 equiv) and stirred at room temperature for 2 h. It was transferred into ice, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 17% ethyl acetate in hexane). To the residue was added methanol:THF (1:1, 30 mL) and 10% palladium on charcoal (0.500 g). The mixture was stirred under hydrogen (1 atm) for 4 h. It was filtered through a pad of Celite® and rinsed with methanol. The filtrate was concentrated under reduced pressure to afford 395.2. MS (ES): m/z 282.1 [M+H]$^+$.

Synthesis of compound 395.3. Compound 395.3 was prepared from 395.2 and Int-4, following the procedure described in the synthesis of 19.1. The product was purified by flash column chromatography on silica gel (CombiFlash®, 20% ethyl acetate in hexane). MS (ES): m/z 467.7 [M+H]$^+$.

Synthesis of compound 395.4. Compound 395.4 was prepared from 395.3 following the procedure described in the synthesis of 5.4. The product was purified by flash column chromatography on silica gel (CombiFlash®, 1.8% methanol in DCM). MS (ES): m/z 437.5 [M+H]$^+$.

Synthesis of compound 395.5. Compound 395.5 was prepared from 395.4 and Int-63, following the procedure described in the synthesis of I-13. The product was purified by flash column chromatography on silica gel (CombiFlash®, 2.8% methanol in DCM). MS (ES): m/z 637.6 [M+H]+.

Synthesis of I-395. Compound I-395 was prepared from 395.5 following the procedure described in the synthesis of 330.6. The product was purified by flash column chromatography on silica gel (CombiFlash®, 3.7% methanol in DCM). MS (ES): m/z 528.1, $^1$H NMR (DMSO-$d_6$, 400 MHz): δ 8.94 (s, 1H), 8.62-8.61 (d, J=2.0 Hz, 1H), 8.17 (s, 1H), 7.96 (s, 1H), 7.90 (s, 1H), 7.57 (s, 1H), 6.74 (bs, 1H), 5.84-5.82 (d, J=5.2 Hz, 1H), 3.99 (s, 3H), 3.67 (s, 3H), 2.71-2.70 (d, 3H).

Example 396: 1-methyl-2-((1-methyl-2-oxo-5-(trifluoromethyl)-1,2-dihydropyridin-3-yl)amino)-6-((4-methyl-6-(methylamino)pyrazolo[1,5-a]pyrazin-3-yl)oxy)-1H-imidazo[4,5-b]pyridine-7-carbonitrile

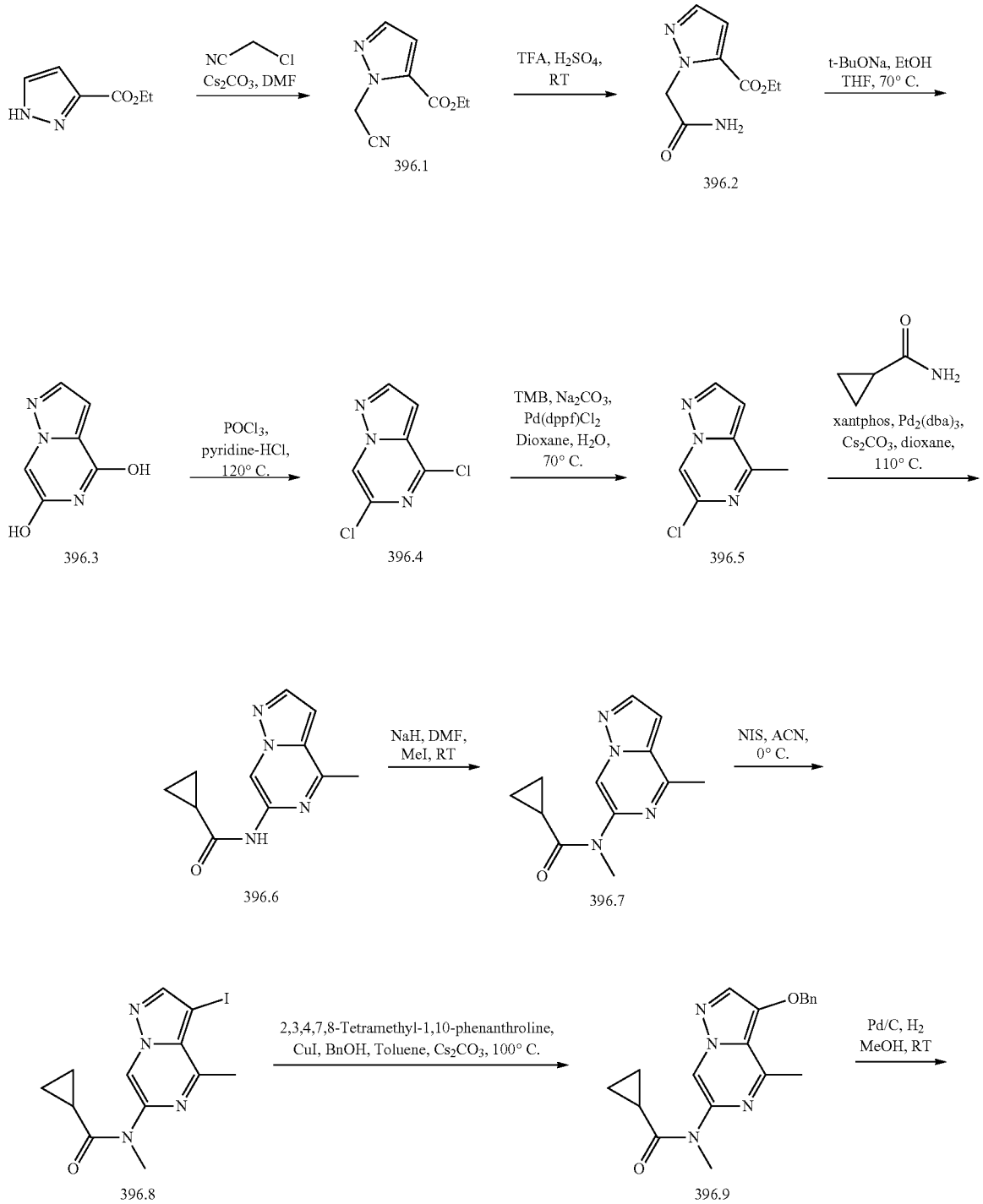

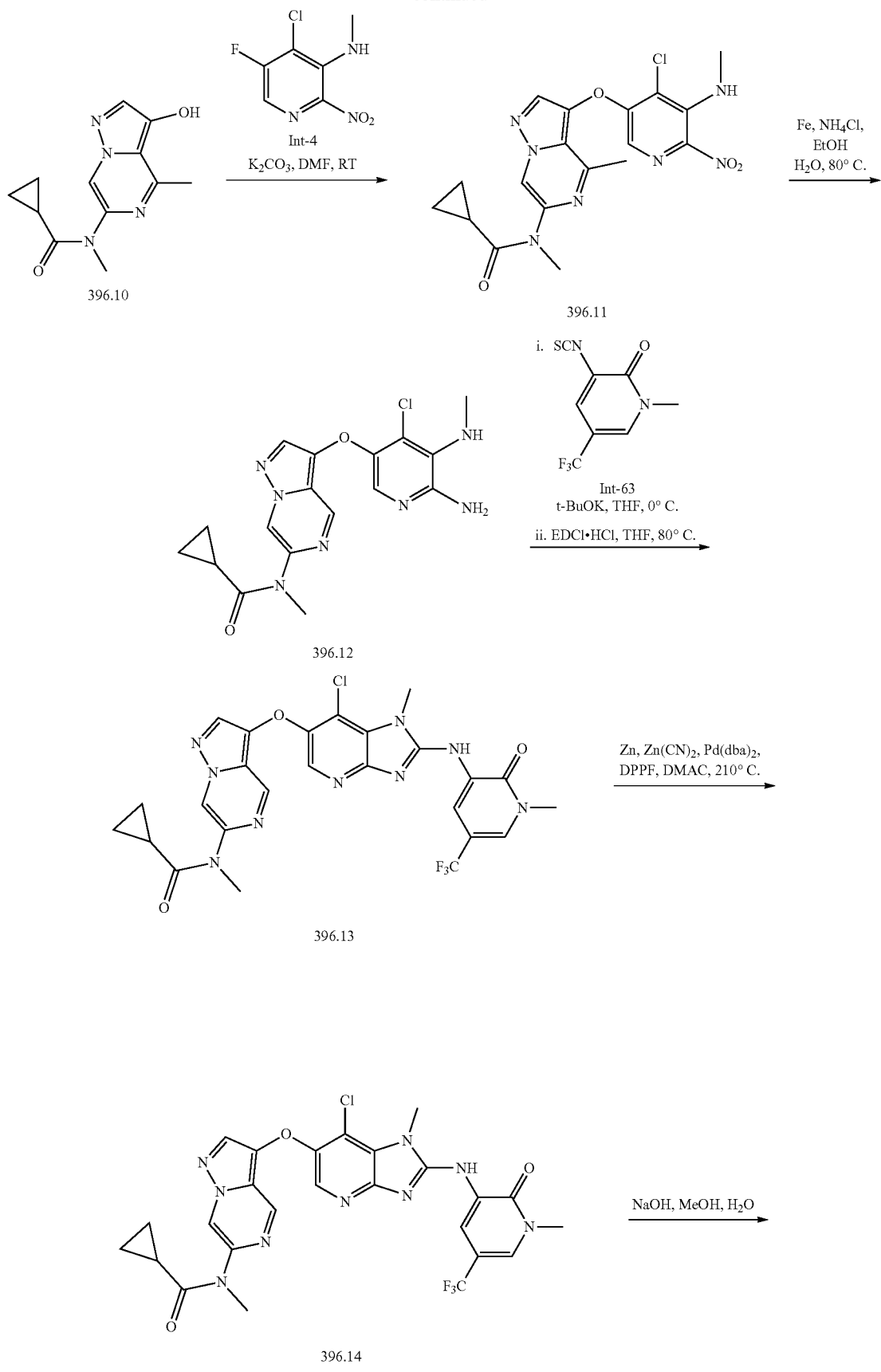

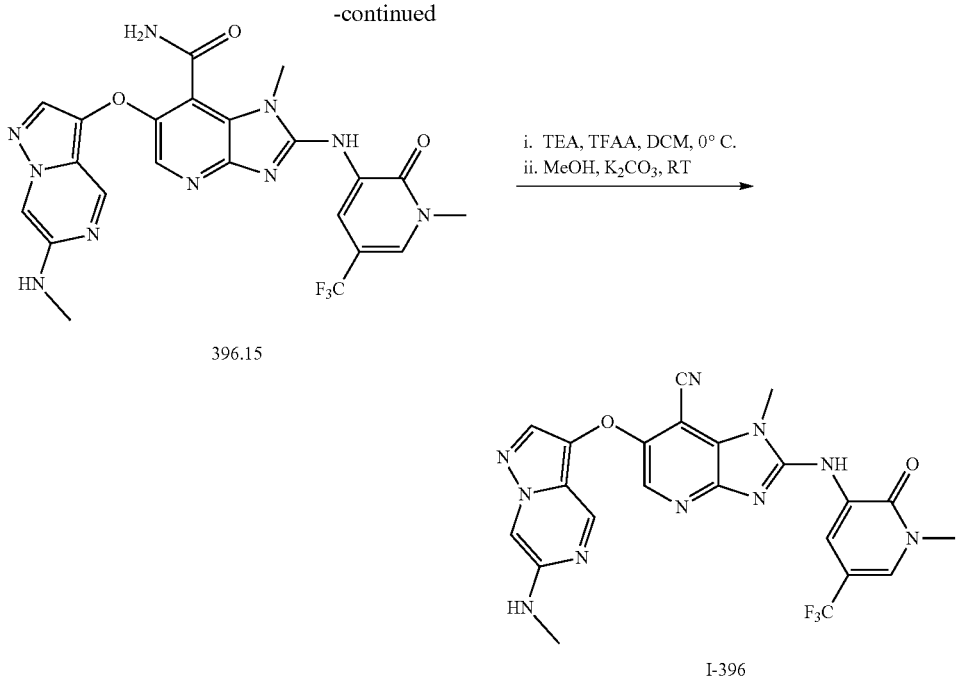

396.15

I-396

Synthesis of compound 396.1. To a mixture of ethyl 1H-pyrazole-3-carboxylate (100 g, 713.56 mmol, 1.0 equiv) and cesium carbonate (417 g, 1284.4 mmol, 1.8 equiv) in DMF (1000 mL) was added 2-chloroacetonitrile (64.6 g, 856.27 mmol, 1.2 equiv) and stirred at room temperature for 16 h. It was transferred into ice-water and extracted with ethyl acetate. The combined organic layers were washed with brine, dried over anhydrous sodium sulfate, and concentrated under reduced pressure. The residue was purified by flash column chromatography on silica gel (Combi-Flash®, 25% ethyl acetate in hexane) to afford 396.1. MS (ES): m/z 180.1 [M+H]$^+$.

Synthesis of compound 396.2. To a solution of 396.1 (38 g, 212.08 mmol, 1.0 equiv) in trifluoroacetic acid (230 mL) was added concentrated sulfuric acid (110.7 g, 1130.38 mmol, 5.33 equiv). The reaction mixture was stirred at room temperature for 16 h. It was concentrated under reduced pressure. To the residue was added ice-water and extracted with ethyl acetate. The combined organic layers were washed with saturated sodium bicarbonate followed by brine, dried over anhydrous sodium sulfate, and concentrated under reduced pressure to afford 396.2. MS (ES): m/z 198.0 [M+H]$^+$.

Synthesis of compound 396.3. To a solution of 396.2 (40 g, 202.85 mmol, 1.0 equiv) in ethanol:THF (8:2, 400 mL) was added sodium tert-butoxide (46.7 g, 486.84 mmol, 2.4 equiv) and stirred at 70° C. for 16 h. It was concentrated under reduced pressure to afford 396.3. It was used for the next step without further purification.

Synthesis of compound 396.4. To a suspension of 396.3 (55 g, 363 mmol, 1.0 equiv) and phosphorous oxychloride (550 mL) was added pyridine hydrochloride (41.74 g, 363 mmol, 1.0 equiv). The reaction mixture was stirred at 120° C. for 12 h. It was concentrated under reduced pressure. The residue was transferred into ice-water, neutralized with saturated sodium bicarbonate, and extracted with ethyl acetate. The combined organic layers were washed with saturated sodium bicarbonate followed by brine, dried over anhydrous sodium sulfate, and concentrated under reduced pressure to afford 396.4. MS (ES): m/z 189.0 [M+H]$^+$.

Synthesis of compound 396.5. To a solution of 396.4 (8.7 g, 46.27 mmol, 1.0 equiv) in 1,4-dioxane:water (1:1, 90 mL) was added trimethyl boroxine (50% in THF, 23 mL, 92.54 mmol, 2.0 equiv) and sodium carbonate (7.35 g, 69.40 mmol, 1.5 equiv). The reaction mixture was degassed for 30 min. Under argon atmosphere, 1,1-bis(diphenylphosphino)ferrocene-palladium(II) dichloride DCM complex (3.38 g, 4.627 mmol, 0.1 equiv) was added. The reaction mixture was stirred at 70° C. for 4 h. It was transferred into ice-water and extracted with ethyl acetate. The combined organic layers were washed with brine, dried over anhydrous sodium sulfate, and concentrated under reduced pressure. The residue was purified by flash column chromatography on silica gel (CombiFlash®, 25% ethyl acetate in hexane) to afford 396.5. MS (ES): m/z 168.5 [M+H]$^+$.

Synthesis of compound 396.6. A mixture of 396.5 (6.5 g, 38.78 mmol, 1.0 equiv), cyclopropyl carboxamide (16.48 g, 193.9 mmol, 5.0 equiv) and cesium carbonate (31.51 g, 96.95 mmol, 2.5 equiv) in 1,4-dioxane (100 mL) was degassed for 10 min. Under argon atmosphere, 4,5-bis(diphenylphosphino)-9,9-dimethylxanthene (4.48 g, 7.756 mmol, 0.2 equiv) and tris(dibenzylideneacetone)dipalladium(0) (3.56 g, 3.878 mmol, 0.1 equiv) were added, and degassed for 5 min. The reaction mixture was stirred at 110° C. for 12 h. It was cooled to room temperature, transferred into water, and extracted with ethyl acetate. The combined organic layers were washed with brine, dried over anhydrous sodium sulfate, and concentrated under reduced pressure. The residue was purified by flash column chromatography on silica gel (CombiFlash®, 35% ethyl acetate in hexane) to afford 396.6. MS (ES): m/z 217.1 [M+H]$^+$.

Synthesis of compound 396.7. To a solution of 396.6 (3.2 g, 14.80 mmol, 1.0 equiv) in DMF (30 mL) was added sodium hydride (0.888 g, 22.2 mmol, 1.5 equiv) at 0° C. and stirred for 30 min. To the mixture was added methyl iodide (2.62 g, 18.5 mmol, 1.25 equiv) and stirred at room temperature for 12 h. It was transferred into ice, stirred, and extracted with ethyl acetate. The combined organic layers were washed with brine, dried over anhydrous sodium sulfate, and concentrated under reduced pressure. The residue was purified by flash column chromatography on silica gel (CombiFlash®, 30% ethyl acetate in hexane) to afford 396.7. MS (ES): m/z 231.2 [M+H]⁺.

Synthesis of compound 396.8. To a solution of 396.7 (1.9 g, 8.25 mmol, 1.0 equiv) in acetonitrile (20 mL) was added N-iodosuccinimide (2.78 g, 12.37 mmol, 1.5 equiv) at 0° C. and stirred for 30 min. It was transferred into saturated sodium bicarbonate solution, stirred, and extracted with ethyl acetate. The combined organic layers were washed with brine, dried over anhydrous sodium sulfate, and concentrated under reduced pressure. The residue was purified by flash column chromatography on silica gel (CombiFlash®, 20% ethyl acetate in hexane) to afford 396.8. MS (ES): m/z 357.1 [M+H]⁺

Synthesis of compound 396.9. A mixture of 396.8 (1.5 g, 4.21 mmol, 1.0 equiv), benzyl alcohol (1.36 g, 12.63 mmol, 3.0 equiv), and cesium carbonate (3.42 g, 10.52 mmol, 2.5 equiv) in toluene (20 mL) was degassed for 10 min. Under argon atmosphere, 3,4,7,8-tetramethyl-1,10-phenanthroline (0.149 g, 0.631 mmol, 0.15 equiv) and copper iodide (0.056 g, 0.294 mmol, 0.07 equiv) were added, and degassed for 5 min. The reaction mixture was stirred at 100° C. for 12 h. It was cooled to room temperature, transferred into water, and extracted with ethyl acetate. The combined organic layers were washed with brine, dried over anhydrous sodium sulfate, and concentrated under reduced pressure. The residue was purified by flash column chromatography on silica gel (CombiFlash®, 25% ethyl acetate in hexane) to afford 396.9. MS (ES): m/z 337.1 [M+H]⁺.

Synthesis of compound 396.10. A mixture of compound 396.9 (0.270 g, 0.802 mmol, 1.0 equiv) and 10% palladium on charcoal (0.125 g) in methanol (5 mL) was stirred under hydrogen (1 atm) for 4 h. It was filtered through a pad of Celite® and rinsed with methanol. The filtrate was concentrated under reduced pressure to afford 396.10. MS (ES): m/z 247.2 [M+H]⁺.

Synthesis of compound 396.11. Compound 396.11 was prepared from 396.10 and Int-4, following the procedure described in the synthesis of 19.1. The product was purified by flash column chromatography on silica gel (Combi-Flash®, 30% ethyl acetate in hexane). MS (ES): m/z 432.5 [M+H]⁺.

Synthesis of compound 396.12. Compound 396.12 was prepared from 396.11 following the procedure described in the synthesis of 5.4. The product was purified by flash column chromatography on silica gel (CombiFlash®, 2.0% methanol in DCM. MS (ES): m/z 402.5 [M+H]⁺.

Synthesis of compound 396.13. Compound 396.13 was prepared from 396.12 and Int-63, following the procedure described in the synthesis of 331.1. The product was purified by column chromatography on silica gel (CombiFlash®, 2.2% methanol in DCM). MS (ES): m/z 602.7 [M+H]⁺.

Synthesis of compound 396.14. Compound 396.14 was prepared from 396.13 following the procedure described in the synthesis of 330.6. The product was purified by flash column chromatography on silica gel (CombiFlash®, 2.5% methanol in DCM). MS (ES): m/z 593.3 [M+H]⁺.

Synthesis of compound 396.15. Compound 396.15 was prepared from 396.14 following the procedure described in the synthesis of I-304. The product was used in the next step without purification. MS (ES): m/z 543.2 [M+H]⁺.

Synthesis of I-396. To a solution of 396.15 (0.010 g, 0.018 mmol, 1.0 equiv) in DCM (1 mL) was added trifluoroacetic anhydride (0.1 mL) followed by triethylamine (0.1 mL) at 0° C. and stirred for 2 h. It was transferred into ice-cold saturated sodium bicarbonate solution and extracted with DCM. The combined organic layers were washed with brine, dried over anhydrous sodium sulfate, and concentrated under reduced pressure. The residue was treated with methanol (1 mL) and potassium carbonate (0.010 g) at room temperature for 30 min. It was filtered and the filtrate was concentrated under reduced pressure. The residue was purified by column chromatography on silica gel (Combi-Flash®, 2.7% methanol in DCM) to afford I-396. MS (ES): m/z 525.3 [M+H]⁺, ¹H NMR (MeOD, 400 MHz): δ 8.87 (s, 1H), 8.04 (s, 1H), 7.91 (s, 1H), 7.52 (s, 1H), 7.35 (s, 1H), 3.89 (s, 3H), 3.75 (s, 3H), 2.85 (s, 3H), 2.71 (s, 3H).

Example 397: 3-((7-chloro-6-((6-(2-hydroxyethoxy) pyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

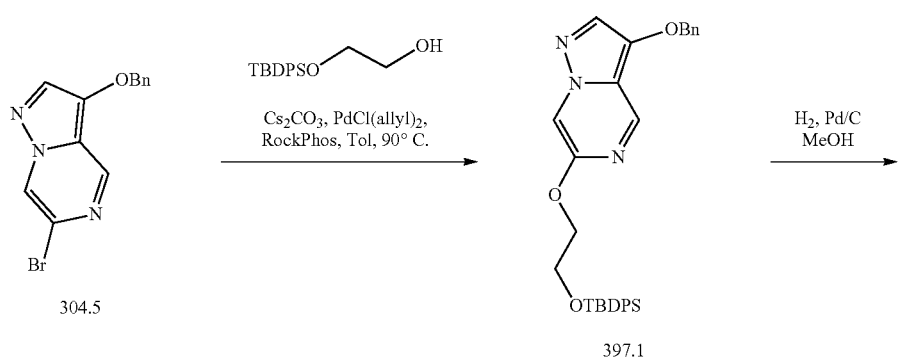

397.1

-continued
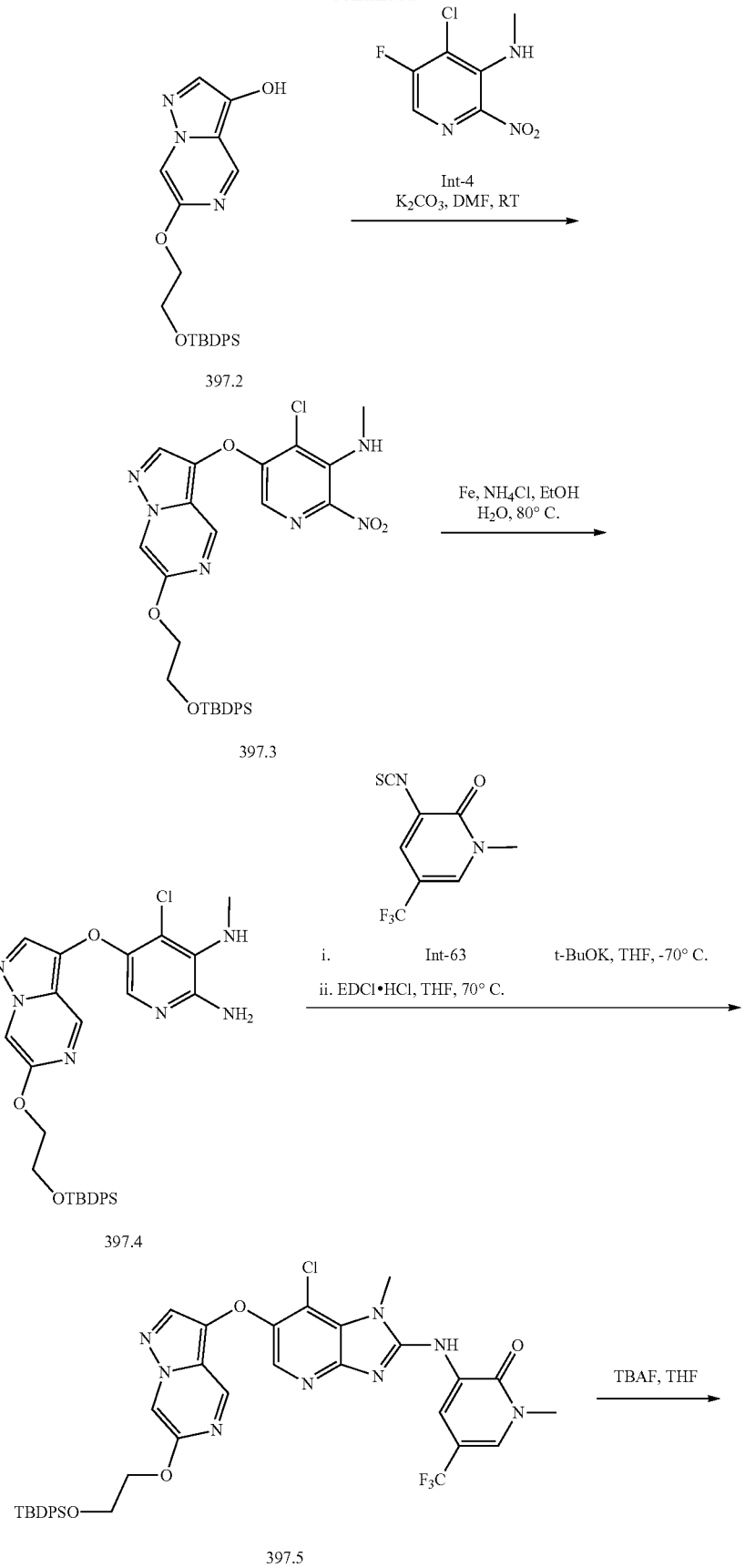
397.2
397.3
397.4
397.5

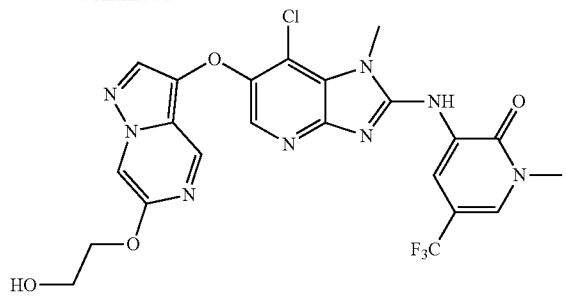

I-397

Synthesis of compound 397.1. A suspension of di-tert-butyl(2',4',6'-triisopropyl-3-methoxy-6-methyl-[1,1'-biphenyl]-2-yl)phosphine (0.154 g, 0.329 mmol, 0.1 equiv), allylpalladium(II) chloride dimer (0.060 g, 0.164 mmol, 0.05 equiv), and cesium carbonate (1.60 g, 4.93 mmol, 1.5 equiv) in toluene (10 mL) was degassed for 10 min. Under argon atmosphere, 304.5 (1.0 g, 3.29 mmol, 1.0 equiv) and 2-((tert-butyldiphenylsilyl)oxy)ethan-1-ol (1.98 g, 6.58 mmol, 2.0 equiv) were added, and degassed for 5 min. The reaction mixture was stirred at 90° C. for 5 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 2.6% methanol in DCM) to afford 397.1. MS (ES): m/z 524.5 [M+H]+.

Synthesis of compound 397.2. A mixture of compound 397.1 (0.510 g, 0.973 mmol, 1.0 equiv) and 10% palladium on charcoal (0.500 g) in methanol (10 mL) was stirred under hydrogen for 30 min. It was filtered through a pad of Celite® and washed with methanol. The filtrate was concentrated under reduced pressure to afford 397.2. MS (ES): m/z 434.4 [M+H]+.

Synthesis of compound 397.3. Compound 397.3 was prepared from 397.2 and Int-4, following the procedure described in the synthesis of 19.1. The product was purified by flash column chromatography on silica gel (CombiFlash®, 40% ethyl acetate in hexane). MS (ES): m/z 620.1 [M+H]+.

Synthesis of compound 397.4. Compound 397.4 was prepared from 397.3 following the procedure described in the synthesis of 5.4. The product was purified by flash column chromatography on silica gel (CombiFlash®, 3.4% methanol in DCM) to afford 397.4. MS (ES): m/z 590.1 [M+H]+.

Synthesis of compound 397.5. Compound 397.5 was prepared from 397.4 and Int-63, following the procedure described in the synthesis of I-51. The product was purified by flash column chromatography on silica gel (CombiFlash®, 4.0% methanol in DCM). MS (ES): m/z 790.1 [M+H]+.

Synthesis of I-397. To a solution of 397.5 (0.035 g, 0.044 mmol, 1.0 equiv) in DCM (2 mL) was added tetra-butylammonium fluoride solution (1 M in THF, 0.5 mL) at 0° C. and stirred for 30 min. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.2% methanol in DCM) to afford I-397. MS (ES): m/z 551.2 [M+H]+, 1H NMR (DMSO-d6, 400 MHz): δ 8.84-8.83 (d, J=6.0 Hz, 2H), 8.61-8.60 (d, J=1.6 Hz, 1H), 8.33 (s, 1H), 8.21 (s, 1H), 8.14 (s, 1H), 7.88 (s, 1H), 4.95-4.92 (m, 1H), 4.22-4.20 (m, 2H), 4.05 (s, 3H), 3.75-3.71 (m, 2H), 3.65 (s, 3H).

Example 398: 2-((3-((7-chloro-2-((4,4-dimethyl-4,5,6,7-tetrahydropyrazolo[1,5-a]pyridin-2-yl)amino)-1-methyl-1H-imidazo[4,5-b]pyridin-6-yl)oxy)pyrazolo[1,5-a]pyrazin-6-yl)oxy)ethan-1-ol

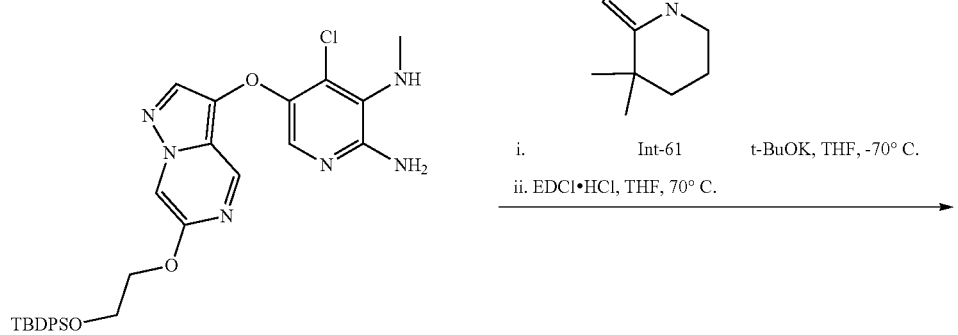

-continued

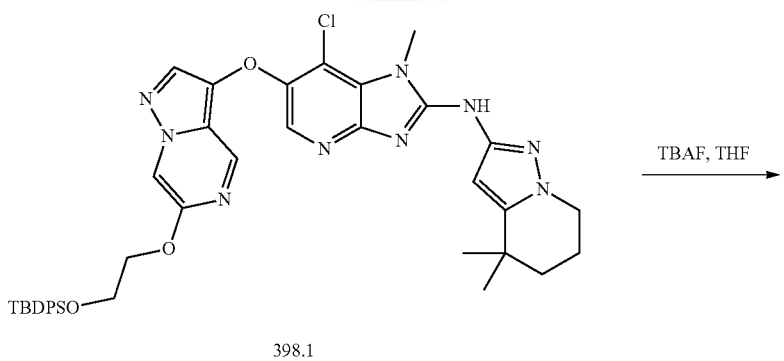

398.1

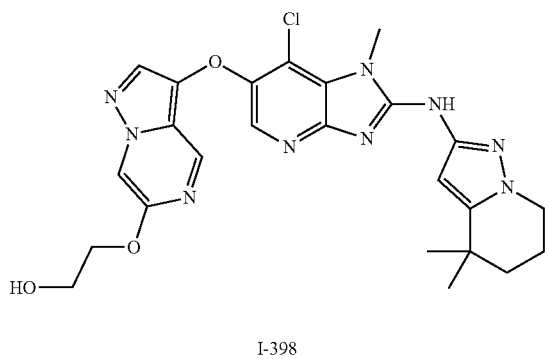

I-398

Synthesis of compound 398.1. Compound 398.1 was prepared from 397.4 and Int-61, following the procedure described in the synthesis of I-51. The product was purified by flash column chromatography on silica gel (CombiFlash®, 3.8% methanol in DCM). MS (ES): m/z 763.1 [M+H]+.

Synthesis of I-398. To a solution of 398.1 (0.038 g, 0.049 mmol, 1.0 equiv) in DCM (2 mL) was added tetra-butyl ammonium fluoride solution (1 M in THF, 0.5 mL) at 0° C. and stirred for 30 min. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 4.0% methanol in DCM) to afford I-398. MS (ES): m/z 524.3 [M+H]+, $^1$H NMR (DMSO-$d_6$, 400 M Hz): δ 9.99 (s, 1H), 8.81 (s, 1H), 8.31 (s, 1H), 8.09 (s, 1H), 7.84 (s, 1H), 6.57 (s, 1H), 4.95-4.92 (m, 1H), 4.21-4.19 (m, 2H), 4.02-3.93 (m, 5H), 3.73-3.72 (m, 2H), 2.02-1.99 (m, 2H), 1.68 (bs, 2H), 1.30 (s, 6H).

Example 399: 2-((4,4-difluoro-4,5,6,7-tetrahydropyrazolo[1,5-a]pyridin-2-yl)amino)-6-((3-(methoxymethyl)-1H-pyrazolo[3,4-b]pyridin-5-yl)oxy)-1-methyl-1H-imidazo[4,5-b]pyridine-7-carbonitrile

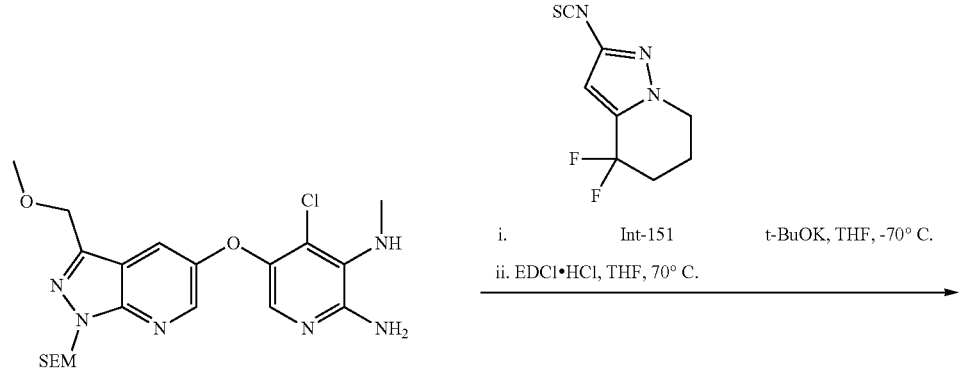

-continued

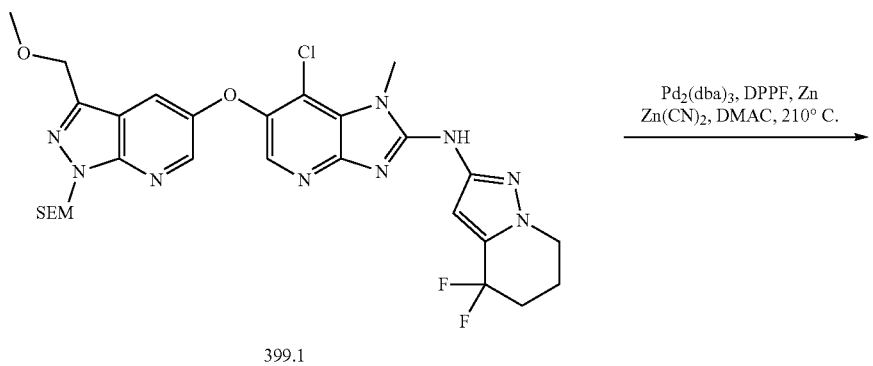
399.1

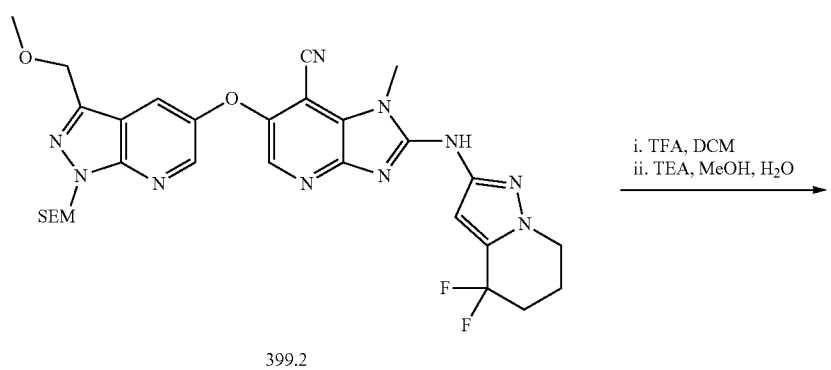
399.2

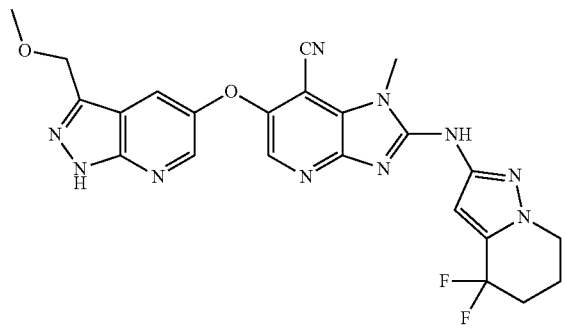
I-399

Synthesis of compound 399.1. Compound 399.1 was prepared from 319.7 and Int-151, following the procedure described in the synthesis of I-51. The product was purified by column chromatography on silica gel (CombiFlash®, 1.8% methanol in DCM). MS (ES): m/z 647.0 [M+H]$^+$.

Synthesis of compound 399.2. Compound 399.2 was prepared from 399.1 following the procedure described in the synthesis of 330.6. The product was purified by flash column chromatography on silica gel (CombiFlash®, 1.8% methanol in DCM). MS (ES): m/z 637.5 [M+H]$^+$.

Synthesis of I-399. To a solution of 399.2 (0.080 g, 0.125 mmol, 1.0 equiv) in DCM (10 mL) was added trifluoroacetic acid (1.0 mL) at 0° C. and stirred for 2 h. It was transferred into ice-cold saturated sodium bicarbonate solution and extracted with DCM. The combined organic layers were washed with brine, dried over anhydrous sodium sulfate, filtered, and concentrated under reduced pressure. The residue was diluted with methanol (5 mL) and water (2 mL) followed by addition of triethylamine (2 mL). The reaction mixture was stirred at room temperature for 8 h. It was transferred into ice-cold saturated sodium bicarbonate solution and extracted with DCM. The combined organic layers were washed with brine, dried over anhydrous sodium sulfate, filtered, and concentrated under reduced pressure. The residue was purified by column chromatography on silica gel (CombiFlash®, 2.2% methanol in DCM) to afford I-399. MS (ES): m/z 507.3 [M+H]$^+$, $^1$H NMR (DMSO-$d_6$, 400 M Hz): δ 13.71 (s, 1H), 10.63 (s, 1H), 8.58-8.57 (d, J=2.8 Hz, 1H), 8.02 (s, 1H), 7.89-7.88 (d, J=2.0 Hz, 1H), 7.08 (s, 1H), 4.66 (s, 2H), 4.15-4.11 (m, 2H), 3.94 (s, 3H), 3.27-3.25 (s, 3H), 2.46 (bs, 2H), 2.19 (bs, 2H).

Example 400: 6-((1H-pyrazolo[3,4-b]pyridin-5-yl)oxy)-2-((1-(7-oxaspiro[3.5]nonan-2-yl)-5-(trifluoromethyl)-1H-pyrazol-3-yl)amino)-1-methyl-1H-imidazo[4,5-b]pyridine-7-carbonitrile Synthesis of compound 400.2. Compound 400.2 was prepared from 400.1 following the procedure described in the synthesis of 330.6. The product was purified by flash column chromatography on silica gel (CombiFlash®, 2.0% methanol in DCM). MS (ES): m/z 695.5 [M+H]+.

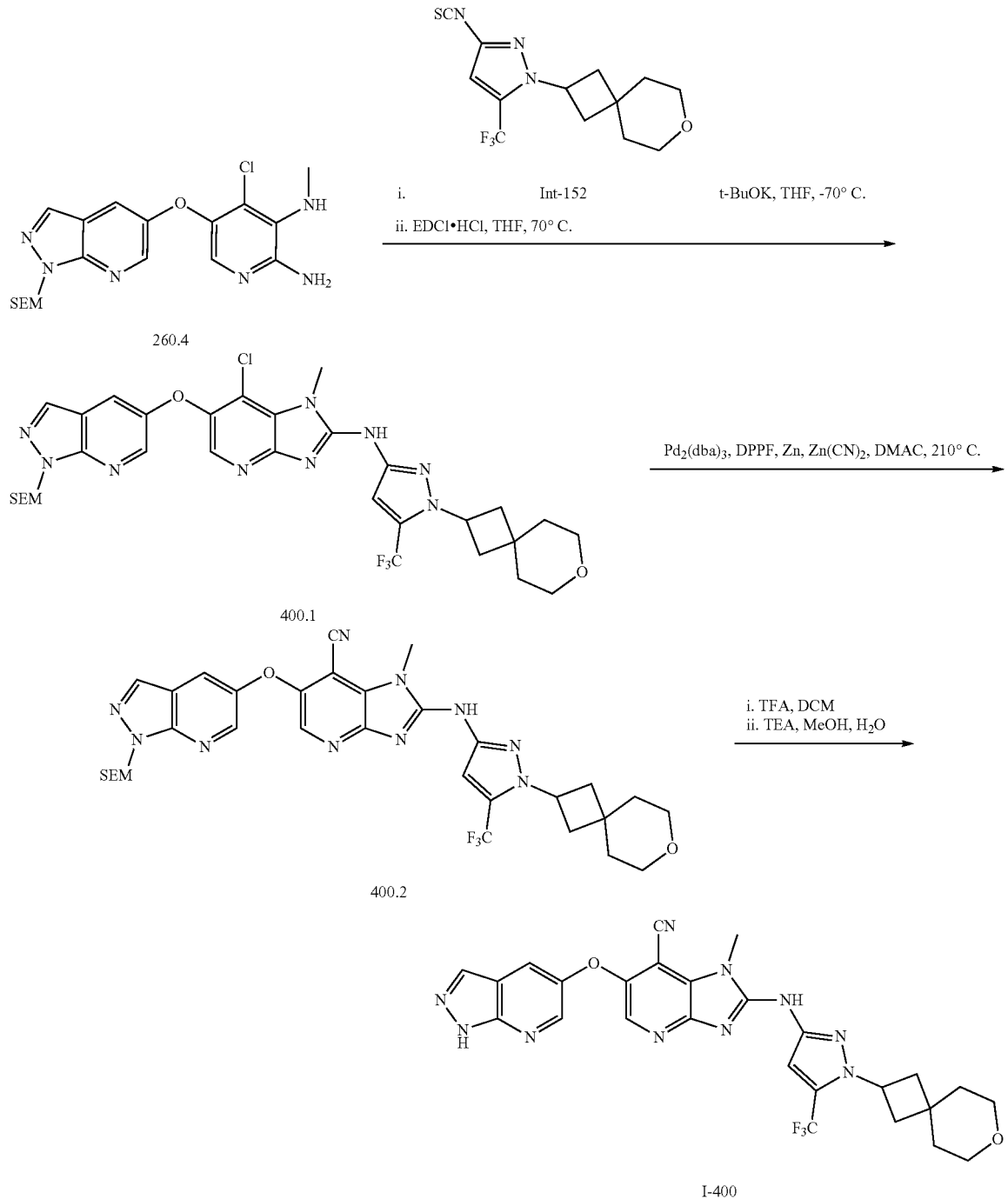

Synthesis of compound 400.1. Compound 400.1 was prepared from 260.4 and Int-152, following the procedure described in the synthesis of I-51. The product was purified by flash column chromatography on silica gel (CombiFlash®, 2.0% methanol in DCM). MS (ES): m/z 705.0 [M+H]+.

Synthesis of I-400. Compound I-400 was prepared from 400.2 following the procedure described in the synthesis of I-333. The product was purified by flash column chromatography on silica gel (CombiFlash®, 2.2% methanol in DCM). MS (ES): m/z 565.4 [M+H]+, 1H NMR (DMSO-d6, 400 MHz): δ 13.79 (s, 1H), 10.77 (s, 1H), 8.57 (s, 1H), 8.09

(s, 1H), 8.03 (d, J=2.0 Hz, 1H), 7.91 (s, 1H), 7.31 (s, 1H), 4.91-4.91 (m, 1H), 3.96 (s, 3H), 3.57 (bs, 2H), 3.50 (bs, 2H), 2.45 (bs, 4H), 1.70 (bs, 2H), 1.62 (bs, 2H).

Example 401: 6-((1H-pyrrolo[2,3-b]pyridin-5-yl)oxy)-2-((1-(7-oxaspiro[3.5]nonan-2-yl)-5-(trifluoromethyl)-1H-pyrazol-3-yl)amino)-1-methyl-1H-imidazo[4,5-b]pyridine-7-carbonitrile Synthesis of compound 401.1. Compound 401.1 was prepared from 257.4 and Int-152, following the procedure described in the synthesis of I-51. The product was purified by column chromatography on silica gel (CombiFlash®, 50% ethyl acetate in hexane). MS (ES): m/z 714.1 [M+H]⁺.

Synthesis of compound 401.2. Compound 401.2 was prepared from 401.1 following the procedure described in the synthesis of 330.6. The product was purified by flash

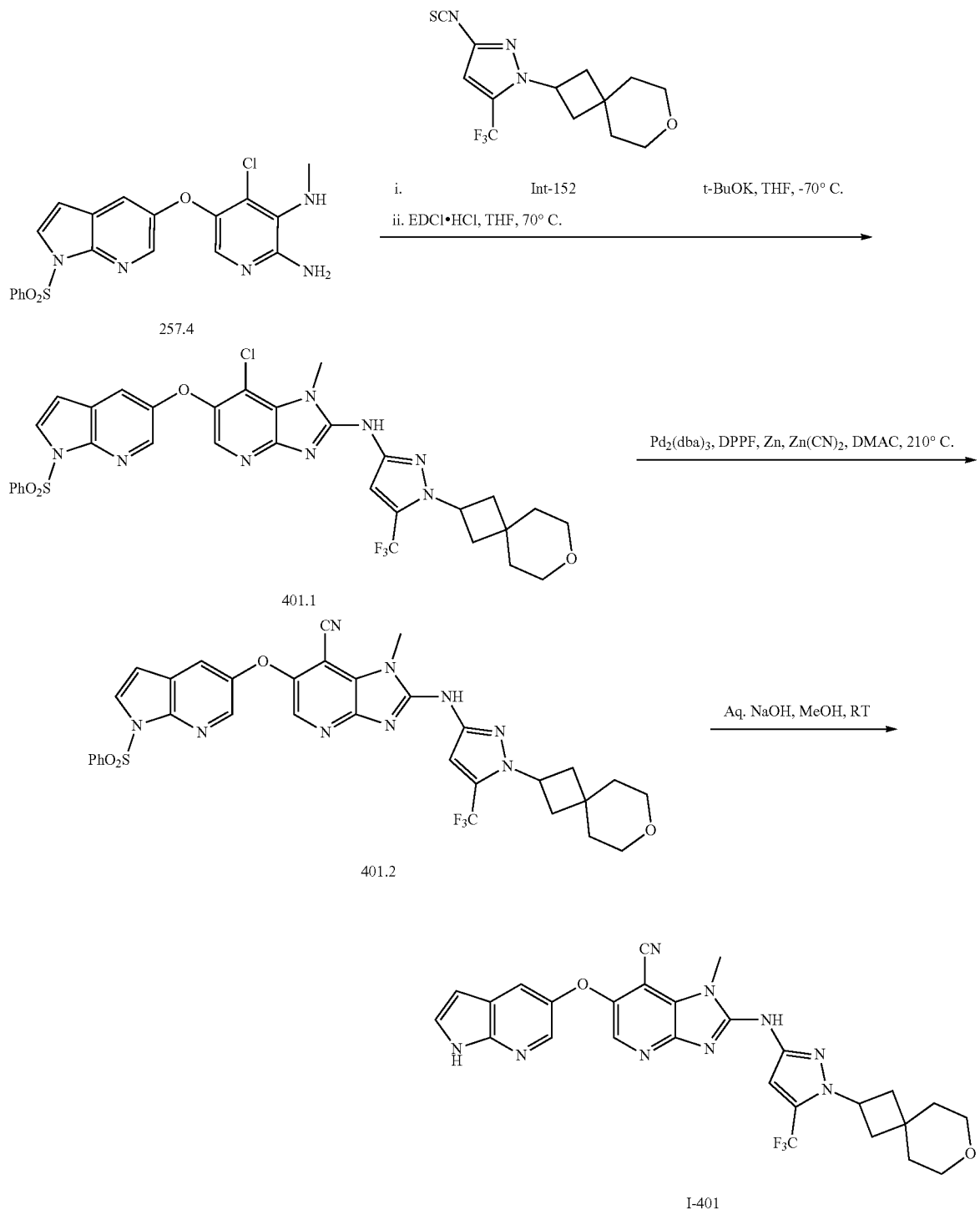

column chromatography on silica gel (CombiFlash®, 60% ethyl acetate in hexane). MS (ES): m/z 704.5 [M+H]⁺.

Synthesis of I-401. To a solution of 401.2 (0.080 g, 0.113 mmol, 1.0 equiv) in methanol (5 mL) was added solution of sodium hydroxide (0.180 g, 4.52 mmol, 40 equiv) in water (2 mL). The reaction mixture was stirred at room temperature for 1 h. It was concentrated under reduced pressure. The residue was transferred into water and extracted with DCM. The combined organic layers were washed with brine, dried over anhydrous sodium sulfate, filtered, and concentrated under reduced pressure. The residue was purified by flash column chromatography on silica gel (CombiFlash®, 3.0% methanol in DCM) to afford I-401. MS (ES): m/z 564.4 [M+H]⁺. ¹H NMR (DMSO-d₆, 400 MHz): δ 11.80 (s, 1H), 10.73 (s, 1H), 8.19-8.18 (d, J=4.0 Hz, 1H), 7.91 (s, 1H), 7.72 (s, 1H), 7.56 (s, 1H), 7.32 (s, 1H), 6.43 (s, 1H), 4.95-4.91 (m, 1H), 3.96 (s, 3H), 3.57 (bs, 2H), 3.50 (bs, 2H), 2.45 (bs, 4H), 1.70 (bs, 2H), 1.62 (bs, 2H).

Example 402: (R)-3-((7-chloro-1-methyl-6-((4-((tetrahydrofuran-3-yl)amino)pyrazolo[1,5-a]pyrazin-3-yl)oxy)-1H-imidazo[4,5-b]pyridin-2-yl)amino)-1-methyl-5-(trifluoromethyl)pyridin-2(1H)-one

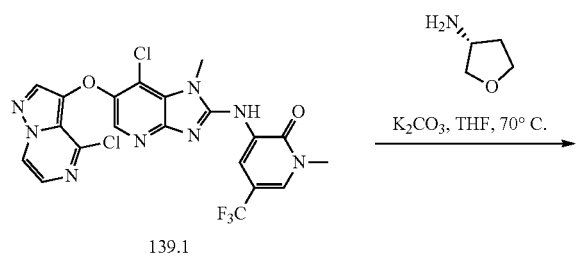

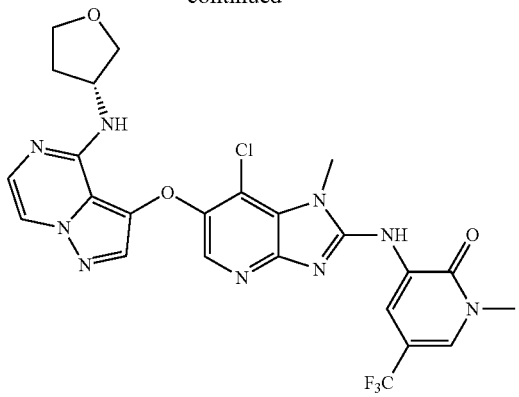

I-402

Synthesis of I-402. A mixture of 139.1 (0.050 g, 0.095 mmol, 1.0 equiv), (R)-tetrahydrofuran-3-amine (0.082 g, 0.951 mmol, 10.0 equiv) and potassium carbonate (0.026 g, 0.190 mmol, 2.0 equiv) in THF (3 mL) was stirred at 70° C. for 3 days. It was cooled to room temperature, transferred into ice cold water and extracted with DCM. The combined organic layers were washed with brine, dried over anhydrous sodium sulfate, filtered, and concentrated under reduced pressure. The residue was purified by preparative HPLC to afford I-142. MS (ES): m/z 576.2 [M+H]⁺, ¹H NMR (DMSO-d₆, 400 M Hz): δ 8.63 (s, 1H), 8.31 (s, 1H), 8.15 (s, 1H), 7.88-7.87 (d, J=4.0 Hz, 1H), 7.68 (s, 1H), 7.30-7.28 (d, J=4.0 Hz, 1H), 6.32-6.31 (d, J=4.0 Hz, 1H), 4.68 (bs, 1H), 4.01 (s, 3H), 3.93-3.90 (m, 1H), 3.86-3.82 (m, 1H), 3.76-3.67 (m, 6H), 2.34-2.23 (m, 2H).

Example 403: 3-((7-chloro-6-((6-((2-(3,3-difluoropyrrolidin-1-yl)ethyl)amino)pyrazolo[1,5-a]pyrazin-3-yl)oxy)-1-methyl-1H-imidazo[4,5-b]pyridin-2-yl)amino)-1-methyl-5-(trifluoromethyl)pyridin-2(1H)-one

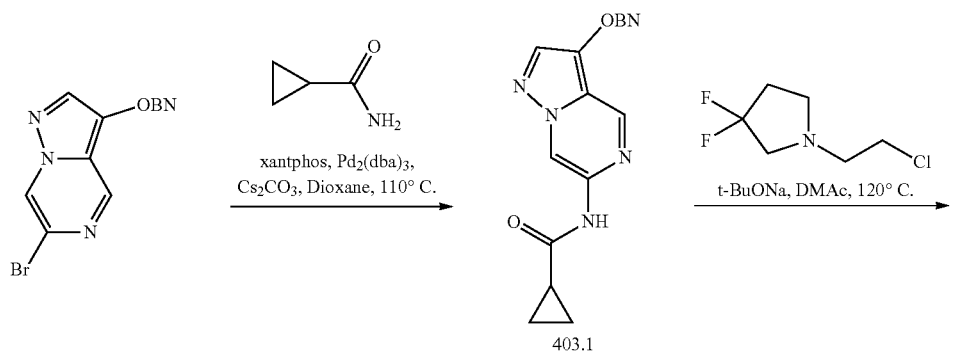

-continued
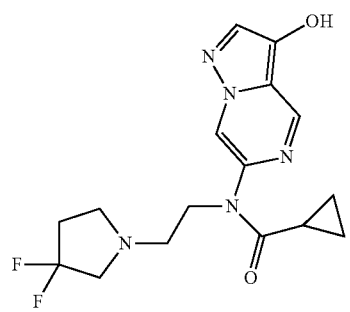
403.2
H₂, Pd/C
MeOH
→
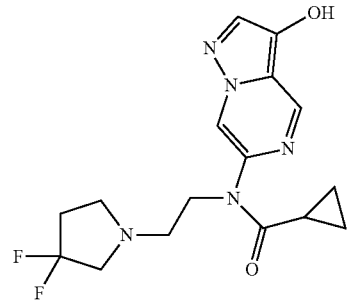
403.3
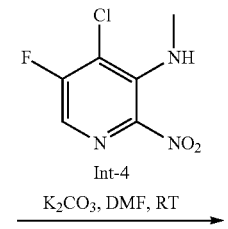
Int-4
K₂CO₃, DMF, RT
→
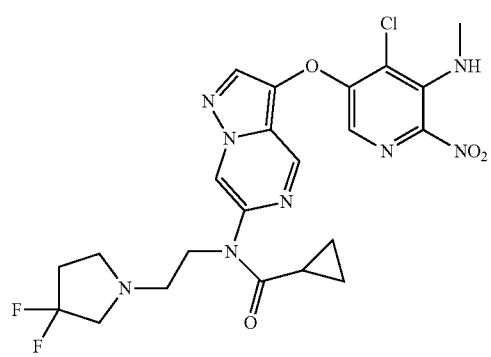
403.4
Fe, NH₄Cl,
EtOH, H₂O,
80° C.
→
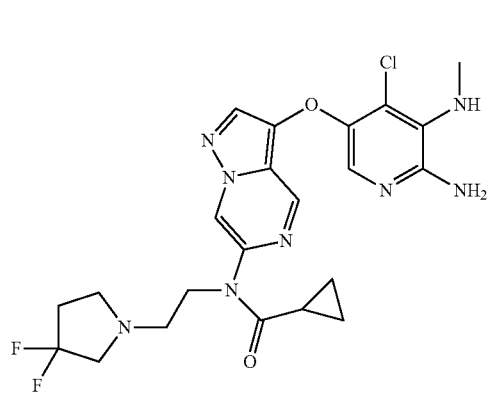
403.5
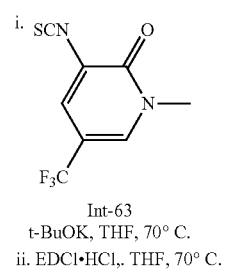
Int-63
i. t-BuOK, THF, 70° C.
ii. EDCl·HCl, THF, 70° C.
→

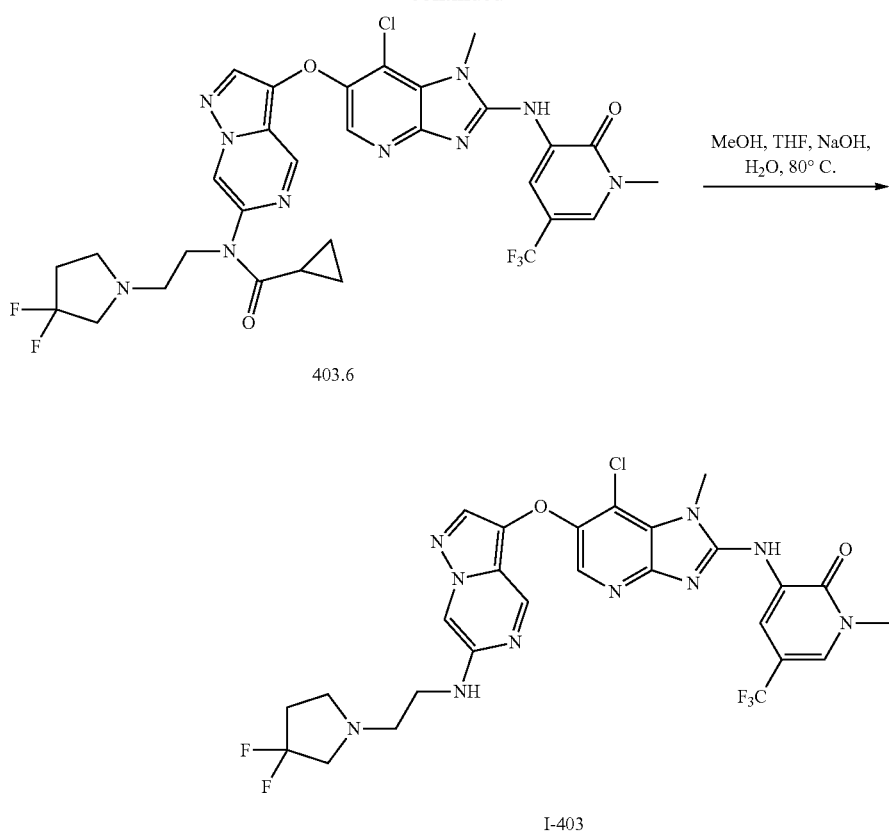 [SMILES: Cn1cc(C(F)(F)F)cc(Nc2nc3ncc(Oc4cnn5cc(N(CCN6CCC(F)(F)C6)C(=O)C6CC6)ncc45)c(Cl)c3n2C)c1=O ; Cn1cc(C(F)(F)F)cc(Nc2nc3ncc(Oc4cnn5cc(NCCN6CCC(F)(F)C6)ncc45)c(Cl)c3n2C)c1=O]

Synthesis of compound 403.1. A mixture of 304.5 (1.0 g, 3.29 mmol, 1.0 equiv), cyclopropyl carboxamide (0.839 g, 9.86 mmol, 3.0 equiv) and cesium carbonate (3.2 g, 9.86 mmol, 3.0 equiv) in 1,4-dioxane (10 mL) was degassed for 10 min. Under argon atmosphere, 4,5-bis(diphenylphosphino)-9,9-dimethylxanthene (0.380 g, 0.658 mmol, 0.2 equiv) and tris(dibenzylideneacetone)dipalladium(0) (0.301 g, 0.329 mmol, 0.1 equiv) were added, and degassed for 5 min. The reaction mixture was stirred at 110° C. for 5 h. It was cooled to room temperature, transferred into water, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 20% ethyl acetate in hexane) to afford 403.1. MS (ES): m/z 309.2 [M+H]+.

Synthesis of compound 403.2. To a solution of 403.1 (0.9 g, 2.92 mmol, 1.0 equiv) and 1-(2-chloroethyl)-3,3-difluoropyrrolidine (0.594 g, 3.50 mmol, 1.2 equiv) in N,N-dimethylacetamide (10 mL) was added sodium tert-butoxide (0.840 g, 8.76 mmol, 3.0 equiv) and stirred at 120° C. for 30 min. It was transferred into water, stirred, and extracted with ethyl acetate. The combined organic layers were washed with brine, dried over anhydrous sodium sulfate, filtered, and concentrated under reduced pressure. The residue was purified by flash column chromatography on silica gel (CombiFlash®, 30% ethyl acetate in hexane as eluant to afford 403.2. MS (ES): m/z 442.3 [M+H]+.

Synthesis of compound 403.3. A mixture of 403.2 (0.200 g, 0.453 mmol, 1.0 equiv) and 10% palladium on carbon (0.100 g) in methanol (10 mL) was stirred under hydrogen (1 atm) for 30 min. It was filtered through a pad of Celite® and rinsed with methanol. The filtrate was concentrated under reduced pressure to afford 403.3. MS (ES): m/z 352.1 [M+H]+.

Synthesis of compound 403.4. Compound 403.4 was prepared from 403.3 and Int-4, following the procedure described in the synthesis of 19.1. The product was purified by flash column chromatography on silica gel (CombiFlash®, 100% ethyl acetate). MS (ES): m/z 537.6 [M+H]+.

Synthesis of compound 403.5. Compound 403.5 was prepared from 403.4 following the procedure described in the synthesis of 5.4. The product was purified by flash column chromatography on silica gel (CombiFlash®, 2.0% methanol in DCM). MS (ES): m/z 507.5 [M+H]+.

Synthesis of compound 403.6. Compound 403.6 was prepared from 403.5 and Int-63, following the procedure described in the synthesis of I-51. The product was purified by column chromatography on silica gel (CombiFlash®, 3.9% methanol in DCM). MS (ES): m/z 707.9 [M+H]+.

Synthesis of I-403. Compound I-403 was prepared from 403.6 following the procedure described in the synthesis of I-304. The product was purified by column chromatography on silica gel (CombiFlash®, 4.8% methanol in DCM). MS (ES): m/z 639.3 [M+H]+, $^1$H NMR (DMSO-$d_6$, 400 M Hz): δ 8.81 (s, 1H), 8.70 (s, 1H), 8.60 (s, 1H), 8.18 (s, 1H), 8.13 (s, 1H), 7.71 (s, 1H), 7.66 (s, 1H), 5.96 (bs, 1H), 4.01 (s, 3H), 3.66 (s, 3H), 3.23-3.21 (m, 2H), 2.99-2.92 (m, 2H), 2.78-2.74 (m, 2H), 2.68 (bs, 2H), 2.28-2.20 (m, 2H).

Example 404: 1-methyl-3-((1-methyl-6-((6-(methylamino)pyrazolo[1,5-a]pyrazin-3-yl)oxy)-1H-imidazo[4,5-b]pyridin-2-yl)amino)-5-(trifluoromethyl)pyridin-2(1H)-one
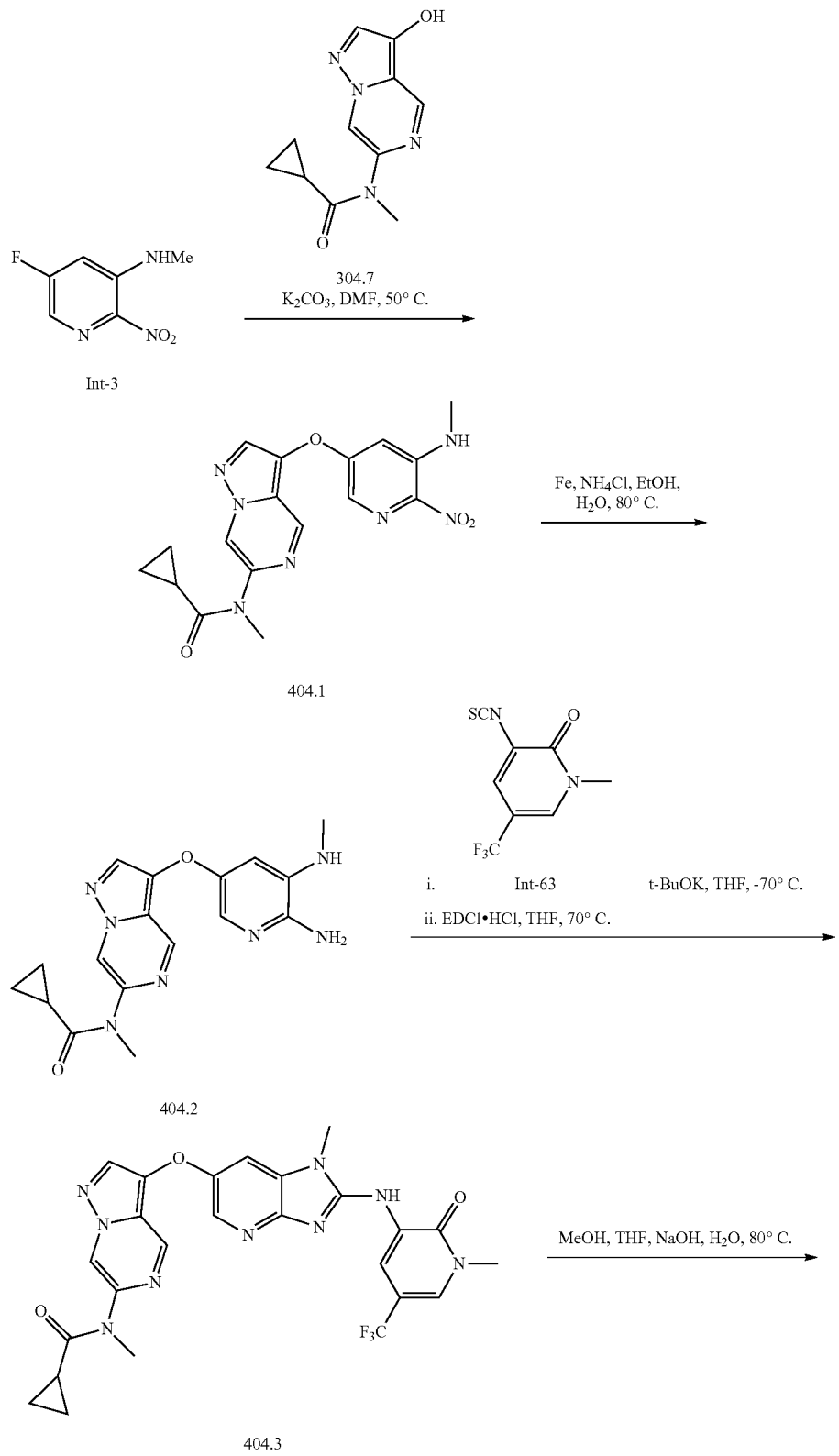

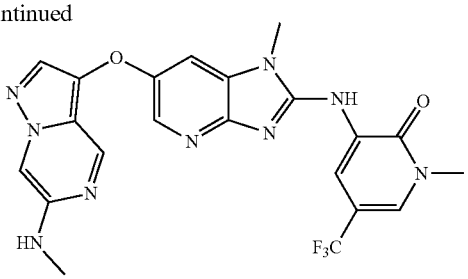

I-404

Synthesis of compound 404.1. To a mixture of Int-3 (0.3 g, 1.75 mmol, 1.0 equiv), potassium carbonate (0.483 g, 3.5 mmol, 2.0 equiv) and 304.7 (0.407 g, 1.75 mmol, 1.0 equiv) in DMF (6 mL) was stirred at room temperature for 1 h. It was transferred into ice-water and extracted with ethyl acetate. The combined organic layers were washed with brine, dried over anhydrous sodium sulfate, filtered, and concentrated under reduced pressure. The residue was purified by flash column chromatography on silica gel (CombiFlash®, 40% ethyl acetate in hexane) to afford 404.1. MS (ES): m/z 384.1 [M+H]$^+$.

Synthesis of compound 404.2. Compound 404.2 was prepared from 404.1 following the procedure described in the synthesis of 5.4. The product was purified by flash column chromatography on silica gel (CombiFlash®, 3.0% methanol in DCM). MS (ES): m/z 354.0 [M+H]$^+$.

Synthesis of compound 404.3. Compound 404.3 was prepared from 404.2 and Int-63, following the procedure described in the synthesis of I-51. The product was purified by column chromatography on silica gel (CombiFlash®, 3.9% methanol in DCM). MS (ES): m/z 554.3 [M+H]$^+$.

Synthesis of I-404. Compound I-404 was prepared from 404.3 following the procedure described in the synthesis of I-304. The product was purified by column chromatography on silica gel (CombiFlash®, 4.5% methanol in DCM). MS (ES): m/z 486.1 [M+H]$^+$, $^1$H NMR (DMSO-d$_6$, 400 MHz): δ 8.69 (s, 1H), 8.66 (s, 1H), 8.61 (s, 1H), 8.19 (s, 1H), 8.11 (s, 1H), 7.77 (s, 1H), 7.72 (s, 1H), 7.59 (s, 1H), 6.14-6.13 (d, J=4.4 Hz, 1H), 3.73 (s, 3H), 3.67 (s, 3H), 2.74-2.73 (d, 3H).

JAK2 Binding Assay

JAK2 (JH1domain-catalytic, Y1007F,Y1008F) kinase was expressed as N-terminal fusion to the DNA binding domain of NFkB in transiently transfected HEK293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mmol/L DTT) to remove unbound ligand and to reduce nonspecific phage binding. Binding reactions were assembled by combining kinases, liganded affinity beads, and test compounds in 1× binding buffer (1×PBS, 0.05% Tween 20, 0.1% BSA, 1 mmol/L DTT). Test compound was prepared as 111× stocks in 100% DMSO and directly diluted into the assay wells. All reactions were performed in polypropylene 384-well plates in a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µmol/L non-biotinylated affinity ligand) and incubated at room temperature with shaking for 30 minutes. The kinase concentration in the eluate was measured by qPCR.

Results of the JAK2 JH1 Domain Binding Assay described above are presented in Table 2. Compounds denoted as "A" had a K$_d$<10 nM; compounds denoted as "B" had a K$_d$≥10 nM and <50 nM; compounds denoted as "C" had a K$_d$≥50 nM and <1 µM; compounds denoted as "D" had a K$_d$≥1 µM and <5 µM.

TABLE 2

| Compound | JAK2 K$_d$ |
| --- | --- |
| I-1 | B |
| I-2 | B |
| I-3 | A |
| I-4 | A |
| I-5 | B |
| I-6 | B |
| I-7 | B |
| I-8 | B |
| I-9 | C |
| I-10 | D |
| I-11 | A |
| I-12 | A |
| I-13 | B |
| I-14 | B |
| I-15 | C |
| I-16 | B |
| I-17 | B |
| I-18 | B |
| I-19 | B |
| I-20 | C |
| I-21 | A |
| I-22 | A |
| I-23 | B |
| I-24 | C |
| I-25 | B |
| I-26 | C |
| I-27 | B |
| I-28 | B |
| I-29 | A |
| I-30 | A |
| I-31 | A |
| I-32 | A |
| I-33 | B |
| I-34 | A |
| I-35 | B |
| I-36 | C |
| I-37 | A |
| I-38 | A |
| I-39 | B |
| I-40 | B |
| I-41-a | A |
| I-41-b | A |
| I-42 | B |
| I-43 | B |
| I-44 | C |
| I-45 | B |
| I-46 | C |

TABLE 2-continued

| Compound | JAK2 $K_d$ |
|---|---|
| I-47 | A |
| I-48 | A |
| I-49 | A |
| I-50 | B |
| I-51 | B |
| I-52 | B |
| I-53 | A |
| I-54 | B |
| I-55 | A |
| I-56-a | B |
| I-56-b | B |
| I-57 | A |
| I-58 | A |
| I-59 | A |
| I-60-a | B |
| I-60-b | A |
| I-61 | A |
| I-62 | B |
| I-63 | B |
| I-64 | A |
| I-65 | A |
| I-66 | A |
| I-67 | A |
| I-68 | A |
| I-69-a | C |
| I-69-b | B |
| I-70 | A |
| I-71-a | C |
| I-71-b | B |
| I-72-a | A |
| I-72-b | A |
| I-73-a | A |
| I-73-b | A |
| I-74 | A |
| I-75 | A |
| I-76-a | B |
| I-76-b | B |
| I-77 | A |
| I-78 | A |
| I-79 | A |
| I-80 | A |
| I-81-a | A |
| I-81-b | A |
| I-82 | B |
| I-83 | B |
| I-84 | A |
| I-85 | A |
| I-86 | A |
| I-87 | B |
| I-88 | B |
| I-89 | A |
| I-90 | A |
| I-91 | A |
| I-92 | A |
| I-93-a | B |
| I-93-b | C |
| I-94 | A |
| I-95-a | A |
| I-95-b | A |
| I-96 | B |
| I-97 | A |
| I-98-a | A |
| I-98-b | A |
| I-99-a | A |
| I-99-b | A |
| I-100 | B |
| I-101-a | A |
| I-101-b | A |
| I-102 | A |
| I-103 | A |
| I-104-a | A |
| I-104-b | A |
| I-105-a | A |
| I-105-b | A |
| I-106 | B |
| I-107-a | A |
| I-107-b | A |
| I-108 | A |
| I-109 | A |
| I-110-a | A |
| I-110-b | B |
| I-111 | A |
| I-112 | A |
| I-113-a | B |
| I-113-b | B |
| I-114-a | A |
| I-114-b | A |
| I-115 | A |
| I-116 | A |
| I-117 | A |
| I-118 | B |
| I-119-a | A |
| I-119-b | A |
| I-120 | A |
| I-121-a | A |
| I-121-b | A |
| I-122-a | A |
| I-122-b | A |
| I-123 | B |
| I-124 | A |
| I-125 | B |
| I-126 | A |
| I-127 | B |
| I-128 | A |
| I-129 | B |
| I-130 | B |
| I-131-a | A |
| I-131-b | B |
| I-132 | A |
| I-133-a | A |
| I-133-b | A |
| I-134 | A |
| I-135 | A |
| I-136 | B |
| I-137 | B |
| I-138 | B |
| I-139-a | A |
| I-139-b | A |
| I-140 | B |
| I-141 | A |
| I-142 | A |
| I-143 | A |
| I-144 | A |
| I-145 | B |
| I-146 | A |
| I-147-a | A |
| I-147-b | A |
| I-148-a | A |
| I-148-b | B |
| I-149 | A |
| I-150-a | B |
| I-150-b | B |
| I-151 | A |
| I-152 | A |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | A |
| I-164 | B |
| I-165 | D |
| I-166 | A |
| I-167 | A |
| I-168 | B |
| I-169 | A |
| I-170 | B |
| I-171 | A |
| I-172 | A |
| I-173 | B |
| I-174 | B |

TABLE 2-continued

| Compound | JAK2 $K_d$ |
|---|---|
| I-175 | B |
| I-176 | A |
| I-177 | A |
| I-178 | A |
| I-179 | A |
| I-180 | A |
| I-181 | A |
| I-182 | A |
| I-183 | A |
| I-184 | C |
| I-185 | A |
| I-186 | A |
| I-187 | B |
| I-188 | A |
| I-189 | B |
| I-190 | B |
| I-191 | B |
| I-192 | B |
| I-193 | A |
| I-194 | A |
| I-195 | A |
| I-196 | A |
| I-197 | A |
| I-198 | A |
| I-199 | A |
| I-200 | B |
| I-201 | A |
| I-202 | A |
| I-203 | B |
| I-204 | A |
| I-205 | A |
| I-206 | A |
| I-207 | A |
| I-208 | C |
| I-209 | B |
| I-210 | A |
| I-211 | A |
| I-212 | A |
| I-213 | B |
| I-214 | A |
| I-215 | A |
| I-216 | B |
| I-217 | A |
| I-218 | A |
| I-219 | B |
| I-220 | B |
| I-221 | B |
| I-222 | B |
| I-223 | A |
| I-224 | A |
| I-225 | A |
| I-226 | B |
| I-227 | B |
| I-228 | B |
| I-229 | B |
| I-230 | C |
| I-231 | A |
| I-232 | A |
| I-233 | C |
| I-234 | B |
| I-235 | B |
| I-236 | A |
| I-237 | B |
| I-238 | A |
| I-239 | A |
| I-240 | C |
| I-241 | A |
| I-242 | A |
| I-243 | A |
| I-244 | A |
| I-245-a | A |
| I-245-b | B |
| I-246 | B |
| I-247 | B |
| I-248 | A |
| I-249 | B |
| I-250 | B |
| I-251 | A |
| I-252 | B |
| I-253 | A |
| I-254 | A |
| I-255 | A |
| I-256 | A |
| I-257 | A |
| I-258 | A |
| I-259 | B |
| I-260 | A |
| I-261 | A |
| I-262-a | A |
| I-262-b | A |
| I-263 | A |
| I-264 | B |
| I-265 | A |
| I-266 | A |
| I-267-a | B |
| I-267-b | C |
| I-268 | C |
| I-269-a | B |
| I-269-b | B |
| I-270-a | A |
| I-270-b | A |
| I-271 | A |
| I-272 | A |
| I-273 | B |
| I-274 | B |
| I-275 | B |
| I-276 | B |
| I-277 | A |
| I-278 | A |
| I-279-a | A |
| I-279-b | A |
| I-280-a | B |
| I-280-b | B |
| I-281 | A |
| I-282 | B |
| I-283 | B |
| I-284 | B |
| I-285 | B |
| I-286 | B |
| I-287 | B |
| I-288 | B |
| I-289 | B |
| I-290 | B |
| I-291 | A |
| I-292 | A |
| I-293 | B |
| I-294 | B |
| I-295 | B |
| I-296 | B |
| I-297 | A |
| I-298 | A |
| I-299 | A |
| I-300 | C |
| I-301 | A |
| I-302 | B |
| I-303 | A |
| I-304 | A |
| I-305 | A |
| I-306 | B |
| I-307 | C |
| I-308 | B |
| I-309 | A |
| I-310 | C |
| I-311 | B |
| I-312 | A |
| I-313 | A |
| I-314 | A |
| I-315 | A |
| I-316 | B |
| I-317 | B |
| I-318 | B |
| I-319 | A |
| I-320 | B |
| I-321 | A |
| I-322 | B |
| I-323 | B |

TABLE 2-continued

| Compound | JAK2 $K_d$ |
| --- | --- |
| I-324 | C |
| I-325 | B |
| I-326 | C |
| I-327 | B |
| I-328 | B |
| I-329 | A |
| I-330 | A |
| I-331 | A |
| I-332 | A |
| I-333 | B |
| I-334 | B |
| I-335 | A |
| I-336 | A |
| I-337 | A |
| I-338 | A |
| I-339 | A |
| I-340 | A |
| I-341 | A |
| I-342 | B |
| I-343 | A |
| I-344 | A |
| I-345 | B |
| I-346 | B |
| I-347 | C |
| I-348 | B |
| I-349 | A |
| I-350-a | A |
| I-350-b | A |
| I-351 | B |
| I-352-a | B |
| I-352-b | B |
| I-353 | A |
| I-354 | A |
| I-355 | A |
| I-356 | B |
| I-357 | C |
| I-358 | C |
| I-359-a | C |
| I-359-b | C |
| I-360 | C |
| I-361 | C |
| I-362 | B |
| I-363 | B |
| I-364 | B |
| I-365 | A |
| I-366 | A |
| I-367 | A |
| I-368 | A |
| I-369 | A |
| I-370 | A |
| I-373 | A |
| I-374 | A |
| I-375 | A |
| I-376 | A |
| I-377 | A |
| I-378 | A |
| I-395 | A |
| I-396 | B |
| I-397 | A |
| I-398 | A |
| I-399 | A |
| I-400 | A |
| I-401 | B |
| I-402 | A |
| I-403 | A |
| I-404 | B |

JAK Family Selectivity Assays

Provided compounds are evaluated for selectivity by comparing their JAK2 binding affinity ($K_d$) in the above JAK2 Binding Assay with their binding affinity ($K_d$) for one or more other kinases. Binding affinity for other kinases is determined as follows: Kinase-tagged T7 phage strains are prepared in an *E. coli* host derived from the BL21 strain. *E. coli* are grown to log-phase and infected with T7 phage and incubated with shaking at 32° C. until lysis. The lysates are centrifuged and filtered to remove cell debris. The remaining kinases are produced in HEK-293 cells and subsequently tagged with DNA for qPCR detection. Streptavidin-coated magnetic beads are treated with biotinylated small molecule ligands for 30 minutes at room temperature to generate affinity resins for kinase assays. The liganded beads are blocked with excess biotin and washed with blocking buffer (SeaBlock (Pierce), 1% BSA, 0.05% Tween 20, 1 mM DTT) to remove unbound ligand and to reduce non-specific binding. Binding reactions are assembled by combining kinases, liganded affinity beads, and test compounds in 1× binding buffer (20% SeaBlock, 0.17×PBS, 0.05% Tween 20, 6 mM DTT). Test compounds are prepared as 111× stocks in 100% DMSO. Kds are determined using an 11-point 3-fold compound dilution series with three DMSO control points. All compounds for Kd measurements are distributed by acoustic transfer (non-contact dispensing) in 100% DMSO. The compounds are then diluted directly into the assays such that the final concentration of DMSO is 0.9%. All reactions are performed in polypropylene 384-well plate. Each has a final volume of 0.02 ml. The assay plates are incubated at room temperature with shaking for 1 hour and the affinity beads are washed with wash buffer (1×PBS, 0.05% Tween 20). The beads are then re-suspended in elution buffer (1×PBS, 0.05% Tween 20, 0.5 µM non-biotinylated affinity ligand) and incubated at room temperature with shaking for 30 minutes. The kinase concentration in the eluates is measured by qPCR. Compounds that exhibit a better binding affinity for JAK2 compared to one or more other kinases are considered to be JAK2-selective compounds. In some embodiments, provided compounds may be JAK2-selective over one or more of the following kinases: JAK1, JAK3, and Tyk2.

SET2-pSTAT5 Cellular Assay

This assay measures inhibition of JAK2-mediated pSTAT5 signaling in constitutively active essential thrombocytopenia cells carrying the V617F mutation. Cells are harvested from a flask into cell culture medium, and the number of cells is counted. The cells are diluted with culture medium and 100 µL of cell suspension (50000/well) is added into each well of a 96-well cell culture plate. A solution of test compound is added to the assay plate. The plates are covered with a lid and placed in a 37° C. 5% $CO_2$ incubator for 4 hours. After 4 hours, the cells are spun, and the cell pellets are re-suspended with 100 µL cold PBS. Then, the cells are spun again at 4° C. and 4000 rpm for 5 min. PBS is aspirated, and 25 µL lysis buffer (with protease and phosphatase inhibitor cocktail) is added to each cell pellet. The cell lysate is shaken at 4° C. for 20 min to fully lyse the cells. The cell lysate is spun at 4° C. and 4000 rpm for 15 min, and then the supernatant is transferred into a new plate and stored at –80° C. Meso-scale discovery (MSD) is used to analyze plates as follows: a standard MSD plate is coated with capture antibody in PBS (40 µL/well) and is incubated at 4° C. overnight with shaking. The MSD plate is washed three times with 150 µL/well of 1×MSD Wash Buffer (Tris-buffered saline with 0.1% Tween® 20 detergent, TBST). The MSD plates are then blocked with 150 µL of blocking buffer (5% BSA in TBST) and shaken for 1 h at room temperature and 600 rpm. The MSD plate is washed three times with 150 µL/well of 1×MSD Wash Buffer (TBST). Sample lysates are then added to MSD plates (25 µL/well) and shaken for 1 h at room temperature and 600 rpm. The MSD plate is washed three times with 150 µL/well of 1×MSD Wash Buffer (TBST). Detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). A secondary detection antibody (prepared in Antibody Detection buffer, 1% BSA in 1×TBST) is then added to the MSD plates, and they are shaken for 1 h at room temperature and 600 rpm. The MSD plate is washed three times with 150 μL/well of 1×MSD Wash Buffer (TBST). MSD reading buffer (1×) is added to the plates (150 μL/well), and they are diluted from 4× with water. The plates are imaged using an MSD imaging instrument according to the manufacturer's instructions.

Caco2 Permeability Assay

Preparation of Caco-2 Cells: 50 μL and 25 mL of cell culture medium are added to each well of a Transwell® insert and reservoir, respectively. Then, the HTS Transwell® plates are incubated at 37° C., 5% $CO_2$ for 1 hour before cell seeding. Caco-2 cell cells are diluted to 6.86×105 cells/mL with culture medium, and 50 μL of cell suspension are dispensed into the filter well of the 96-well HTS Transwell® plate. Cells are cultivated for 14-18 days in a cell culture incubator at 37° C., 5% $CO_2$, 95% relative humidity. Cell culture medium is replaced every other day, beginning no later than 24 hours after initial plating.

Preparation of Stock Solutions: 10 mM stock solutions of test compounds are prepared in DMSO. The stock solutions of positive controls are prepared in DMSO at the concentration of 10 mM. Digoxin and propranolol are used as control compounds in this assay.

Assessment of Cell Monolayer Integrity: Medium is removed from the reservoir and each Transwell® insert and is replaced with prewarmed fresh culture medium. Transepithelial electrical resistance (TEER) across the monolayer is measured using Millicell Epithelial Volt-Ohm measuring system (Millipore, USA). The Plate is returned to the incubator once the measurement is done. The TEER value is calculated according to the following equation: TEER measurement (ohms)×Area of membrane ($cm^2$)=TEER value (ohm·$cm^2$). A TEER value greater than 230 ohm·$cm^2$ indicates a well-qualified Caco-2 monolayer.

Assay Procedure: The Caco-2 plate is removed from the incubator and washed twice with pre-warmed HBSS (10 mM HEPES, pH 7.4), and then incubated at 37° C. for 30 minutes. The stock solutions of control compounds are diluted in DMSO to get 1 mM solutions and then diluted with HBSS (10 mM HEPES, pH 7.4) to get 5 μM working solutions. The stock solutions of the test compounds are diluted in DMSO to get 1 mM solutions and then diluted with HBSS (10 mM HEPES and 4% BSA, pH 7.4) to get 5 μM working solutions. The final concentration of DMSO in the incubation system is 0.5%. To determine the rate of drug transport in the apical to basolateral direction. 75 μL of 5 μM working solutions of test compounds are added to the Transwell® insert (apical compartment) and the wells in the receiver plate (basolateral compartment) are filled with 235 μL of HBSS (10 mM HEPES and 4% BSA, pH 7.4). To determine the rate of drug transport in the basolateral to apical direction, 235 μL of 5 μM working solutions of test compounds are added to the receiver plate wells (basolateral compartment) and then the Transwell® inserts (apical compartment) are filled with 75 μL of HBSS (10 mM HEPES and 4% BSA, pH 7.4). Time 0 samples are prepared by transferring 50 L of 5 μM working solution to wells of the 96-deepwell plate, followed by the addition of 200 L cold methanol containing appropriate internal standards (IS). The plates are incubated at 37° C. for 2 hours. At the end of the incubation, 50 μL samples from donor sides (apical compartment for Ap→Bl flux, and basolateral compartment for Bl→Ap) and receiver sides (basolateral compartment for Ap→Bl flux, and apical compartment for Bl→Ap) are transferred to wells of a new 96-well plate, followed by the addition of 4 volume of cold acetonitrile or methanol containing appropriate internal standards (IS). Samples are vortexed for 5 minutes and then centrifuged at 3,220 g for 40 minutes. An aliquot of 100 μL of the supernatant is mixed with an appropriate volume of ultra-pure water before LC-MS/MS analysis. To determine the Lucifer Yellow leakage after 2 hour transport period, stock solution of Lucifer yellow is prepared in ultra-pure water and diluted with HBSS (10 mM HEPES, pH 7.4) to reach the final concentration of 100 μM. 100 μL of the Lucifer yellow solution is added to each Transwell® insert (apical compartment), followed by filling the wells in the receiver plate (basolateral compartment) with 300 μL of HBSS (10 mM HEPES, pH 7.4). The plates are incubated at 37° C. for 30 minutes. 80 L samples are removed directly from the apical and basolateral wells (using the basolateral access holes) and transferred to wells of new 96 wells plates. The Lucifer Yellow fluorescence (to monitor monolayer integrity) signal is measured in a fluorescence plate reader at 485 nM excitation and 530 nM emission.

Cytotoxicity Assay

HEK293T cells are harvested from flask into cell culture medium, and then the cells are counted. The cells are diluted with culture medium to the desired density, and 40 μL of cell suspension is added into each well of a 384-well cell culture plate. The plates are covered with a lid and spun at room temperature at 1,000 RPM for 1 minute and then transferred into 37° C. 5% $CO_2$ incubator overnight. Test compounds are dissolved at 10 mM DMSO stock solution. 45 μL of stock solution is then transferred to a 384 PP-plate. A 3-fold, 10-point dilution is performed via transferring 15 μL compound into 30 μL DMSO by using TECAN (EVO200) liquid handler. The plates are spun at room temperature at 1,000 RPM for 1 minute and shaken on a plate shaker for 2 minutes. 40 nL of diluted compound is transferred from compound source plate into the cell plate by using liquid handler Echo550. After compound treatment for 48 hours, CTG detection is performed for compound treatment plates: the plates are removed from incubators and equilibrated at room temperature for 15 minutes. 30 μL of CellTiter-Glo reagent is added into each well to be detected. The plates are then placed at room temperature for 30 min followed by reading on EnVision. Inhibition activity is calculated with the following formula: % Inhibition=100×(LumHC−LumSample)/(LumHC−LumLC), wherein HC is reading obtained from cells treated with 0.1% DMSO only and LC is reading from cells treated with 10 L staurosporine. $IC_{50}$ values are calculated using XLFit (equation 201).

Hepatocyte Stability Assay 10 mM stock solutions of test compound and positive control are prepared in DMSO. Stock solutions are diluted to 100 μM by combining 198 μL of 50% acetonitrile/50% water and 2 μL of 10 mM stock solution. Verapamil is used as positive control in the assay. Vials of cryopreserved hepatocytes are thawed in a 37° C. water bath with gently shaking. The contents are poured into the 50 mL thawing medium conical tube. Vials are centrifuged at 100 g for 10 minutes at room temperature. Thawing medium is aspirated and hepatocytes are re-suspended with serum-free incubation medium to yield ~1.5×106 cells/mL. Cell viability and density are counted using a Trypan Blue exclusion, and then cells are diluted with serum-free incubation medium to a working cell density of 0.5×106 viable cells/mL. A portion of the hepatocytes at 0.5×106 viable cells/mL are boiled for 5 min prior to adding to the plate as negative control to eliminate the enzymatic activity so that little or no substrate turnover should be observed. Aliquots of 198 µL hepatocytes are dispensed into each well of a 96-well non-coated plate. The plate is placed in the incubator for approximately 10 minutes. Aliquots of 2 µL of the 100 µM test compound and 2 µL positive control are added into respective wells of a non-coated 96-well plate to start the reaction. The final concentration of test compound is 1 µM. This assay is performed in duplicate. The plate is incubated in the incubator for the designed time points. 25 L of contents are transferred and mixed with 6 volumes (150 µL) of cold acetonitrile with internal standard (100 nM alprazolam, 200 nM labetalol, 200 nM caffeine and 200 nM diclofenac) to terminate the reaction at time points of 0, 15, 30, 60, 90 and 120 minutes. Samples are centrifuged for 25 minutes at 3,220 g and aliquots of 150 µL of the supernatants are used for LC-MS/MS analysis.

Kinetic Solubility Assay

Stock solutions of test compounds are prepared in DMSO at the concentration of 10 mM, and a stock solution of control compound is prepared in DMSO at the concentration of 30 mM. Diclofenac is used as positive control in the assay. 30 µL stock solution of each compound is placed into their a 96-well rack, followed by adding 970 µL of PBS at pH 4.0 and pH 7.4 into each vial of the cap-less solubility sample plate. This study is performed in duplicate. One stir stick is added to each vial and then vials are sealed using a molded PTDE/SIL 96-Well Plate Cover. The solubility sample plate is transferred to the Thermomixer comfort plate shaker and incubated at RT for 2 hours with shaking at 1100 rpm. After 2 hours incubation, stir sticks are removed using a big magnet and all samples from the solubility sample plate are transferred into the filter plate. All the samples are filtered by vacuum manifold. The filtered samples are diluted with methanol. Samples are analyzed by LC-MS/MS and quantified against a standard of known concentration in DMSO using LC coupled with Mass spectral peak identification and quantitation. The solubility values of the test compounds are calculated as follows, wherein INJ VOL is injection volume, DF is dilution factor, and STD is standard:

$$[\text{Sample}] = \frac{AREA_{Sample} \times INJVOL_{Std} \times DF_{Sample} \times [STD]}{AREA_{Std} \times INJVOL_{Sample}}$$

Plasma Protein Binding Assay

Working solutions of test compounds and control compound are prepared in DMSO at the concentration of 200 µM, and then the working solutions are spiked into plasma. The final concentration of compound is 1 µM. The final concentration of DMSO is 0.5%. Ketoconazole is used as positive control in the assay. Dialysis membranes are soaked in ultrapure water for 60 minutes to separate strips, then in 20% ethanol for 20 minutes, finally in dialysis buffer for 20 minutes. The dialysis set up is assembled according to the manufacturer's instruction. Each Cell is with 150 µL of plasma sample and dialyzed against equal volume of dialysis buffer (PBS). The assay is performed in duplicate. The dialysis plate is sealed and incubated in an incubator at 37° C. with 5% $CO_2$ at 100 rpm for 6 hours. At the end of incubation, 50 µL of samples from both buffer and plasma chambers are transferred to wells of a 96-well plate. 50 µL of plasma is added to each buffer samples and an equal volume of PBS is supplemented to the collected plasma sample. 400 µL of precipitation buffer acetonitrile containing internal standards (IS, 100 nM alprazolam, 200 nM labetalol, 200 nM imipramine and 2 µM ketoplofen) is added to precipitate protein and release compounds. Samples are vortexed for 2 minutes and centrifuged for 30 minutes at 3,220 g. Aliquot of 50 µL of the supernatant is diluted by 150 µL acetonitrile containing internal standards:ultra-pure $H_2O$=1:1, and the mixture is used for LC-MS/MS analysis. While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A compound of Formula I-D:

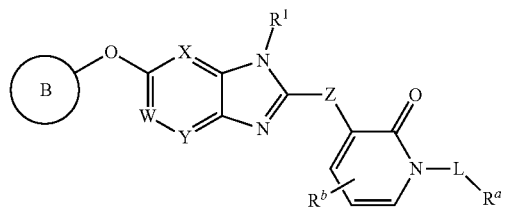

I-D or a pharmaceutically acceptable salt thereof, wherein
W is $CR^w$ or N;
X is $CR^x$ or N;
Y is $CR^y$ or N;
Z is —O— or $—NR^z—$;
$R^w$, $R^x$ and $R^y$ are each independently hydrogen, halogen, $—OR^2$, $—N(R^2)_2$, $—SR^2$, optionally substituted $C_{1-6}$ aliphatic, or —CN;
$R^z$ is hydrogen or optionally substituted $C_{1-6}$ aliphatic;
$R^1$ is optionally substituted $C_{1-6}$ aliphatic;
each $R^2$ is independently hydrogen or optionally substituted $C_{1-6}$ aliphatic;
Ring B is optionally substituted 9- to 16-membered bicyclic or tricyclic aryl, optionally substituted 8- to 10-membered bicyclic heteroaryl having 1-4 heteroatoms independently selected from nitrogen, oxygen, and sulfur, optionally substituted 10- to 16-membered polycyclic heteroaryl having 1-5 heteroatoms independently selected from nitrogen, oxygen, and sulfur, optionally substituted 7- to 10-membered bicyclic heterocyclyl having 1-4 heteroatoms independently selected from nitrogen, oxygen, and sulfur, or optionally substituted 10- to 16-membered polycyclic heterocyclyl having 1-5 heteroatoms independently selected from nitrogen, oxygen, and sulfur;
L is a covalent bond or a bivalent $C_{1-3}$ straight or branched hydrocarbon chain; and
$R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, or sulfur, or optionally substituted 7- to 10-membered saturated or partially unsaturated bicyclic heterocyclyl having 1-4 heteroatoms independently selected from nitrogen, oxygen, and sulfur.

2. A compound of Formula I-E:

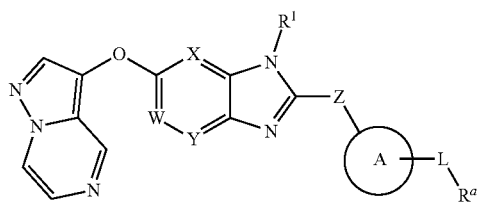

I-E or a pharmaceutically acceptable salt thereof; wherein

W is $CR^w$ or N;

X is $CR^x$ or N;

Y is $CR^y$ or N;

Z is —O— or —$NR^z$—;

$R^w$, $R^x$ and $R^y$ are each independently hydrogen, halogen, —$OR^2$, —$N(R^2)_2$, —$SR^2$, optionally substituted $C_{1-6}$ aliphatic, or —CN;

$R^z$ is hydrogen or optionally substituted $C_{1-6}$ aliphatic;

$R^1$ is optionally substituted $C_{1-6}$ aliphatic;

each $R^2$ is independently hydrogen or optionally substituted $C_{1-6}$ aliphatic;

Ring A is optionally substituted phenyl, optionally substituted 5- to 6-membered monocyclic heteroaryl having 1-4 heteroatoms independently selected from nitrogen, oxygen, and sulfur, optionally substituted 8- to 10-membered bicyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur;

L is a covalent bond or a bivalent $C_{1-3}$ straight or branched hydrocarbon chain; and $R^a$ is hydrogen, halogen, optionally substituted $C_{1-6}$ aliphatic, optionally substituted phenyl, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

3. A compound selected from:

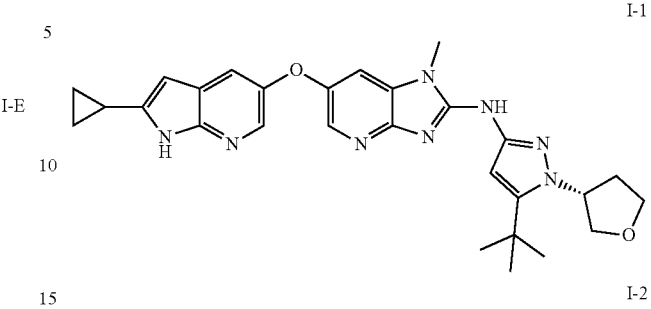

I-1

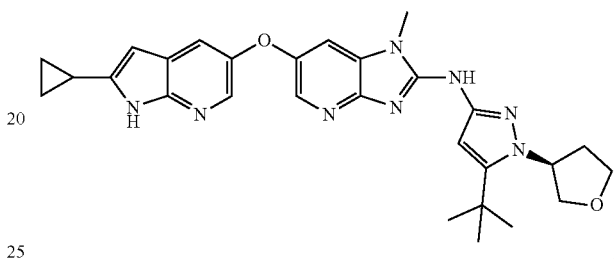

I-2

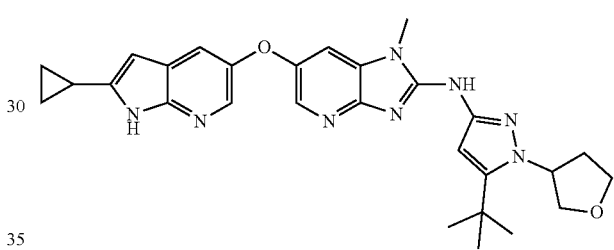

I-1'

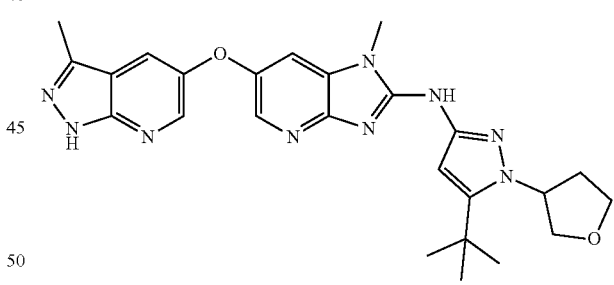

I-3'

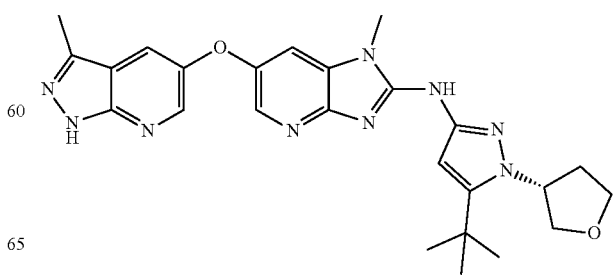

I-3

I-4
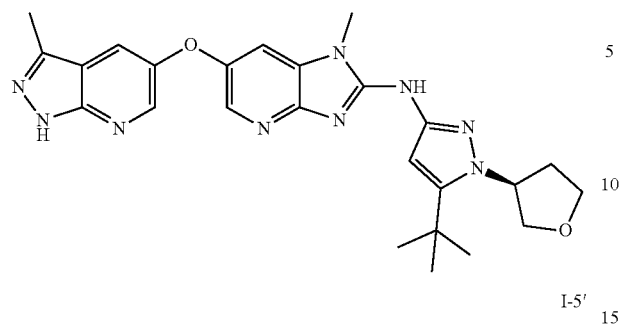
I-5'
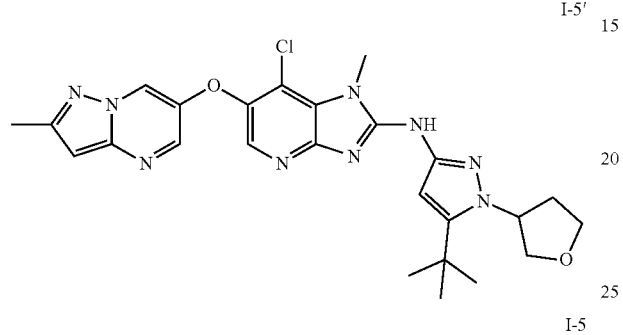
I-5
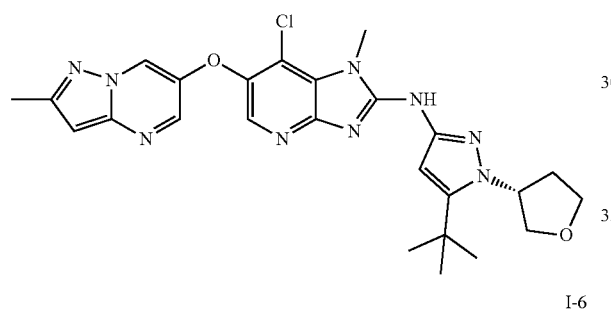
I-6
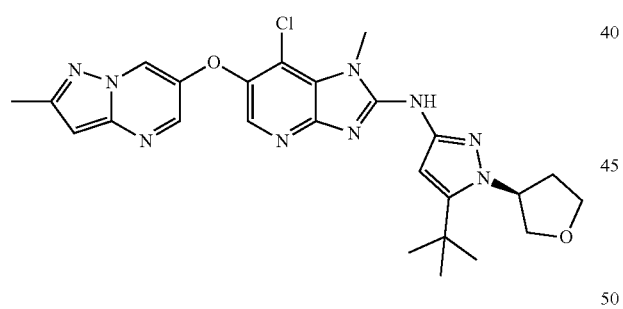
I-7'
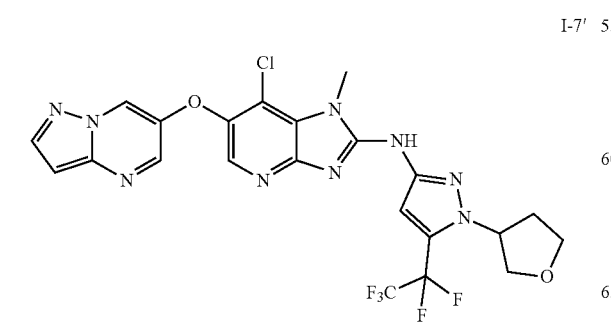
I-7
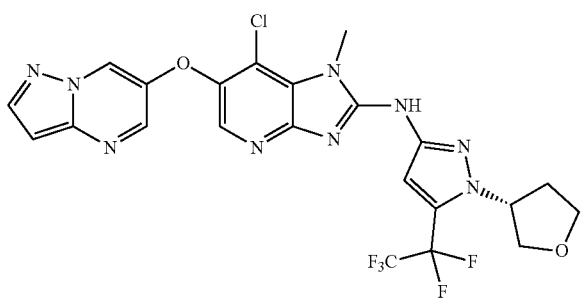
I-8
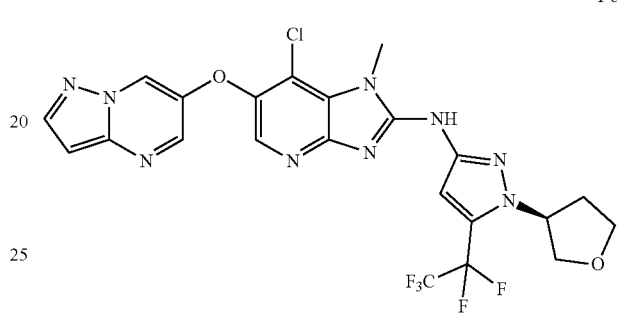
I-9'
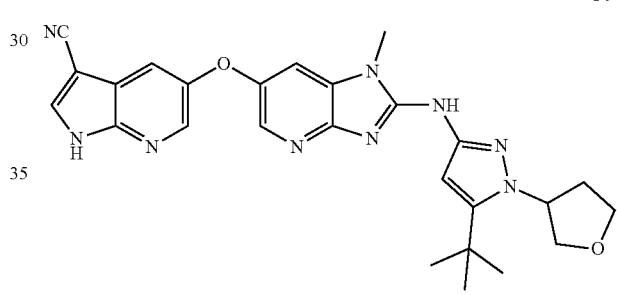
I-9
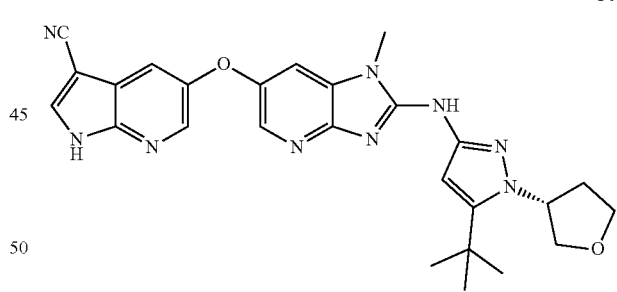
I-10
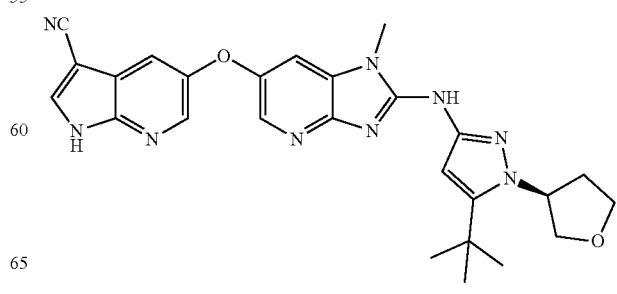

I-11'
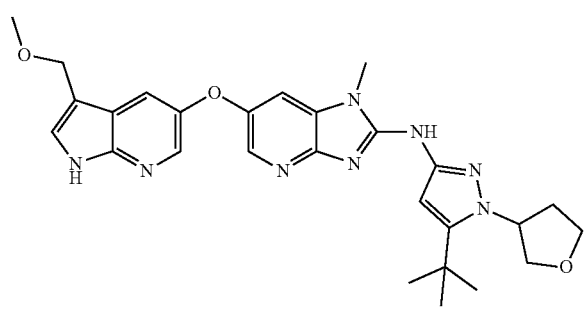
I-11
I-12
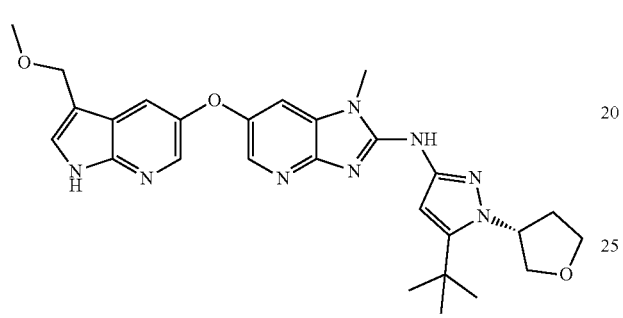
I-13'
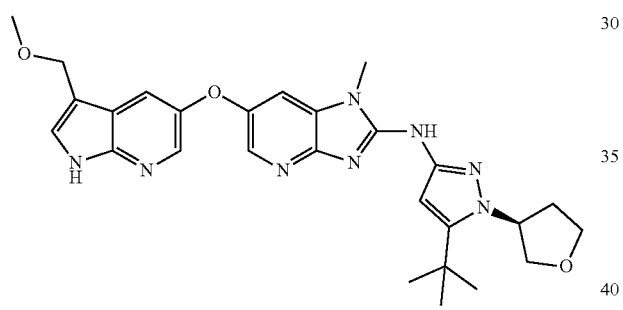
I-13
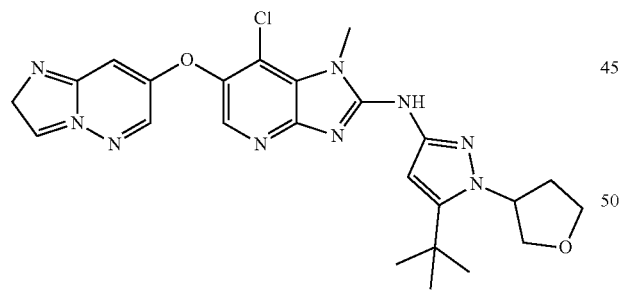
I-14
I-15'
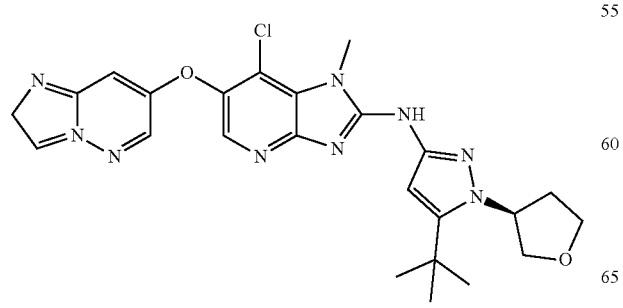
I-15
I-16
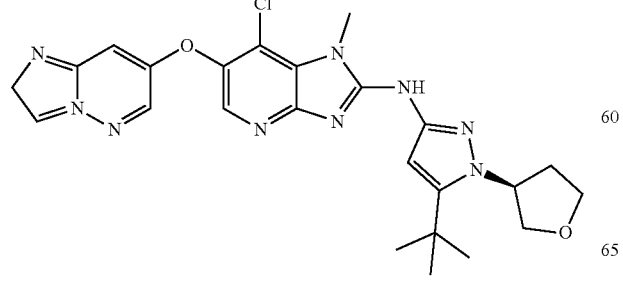
I-17'
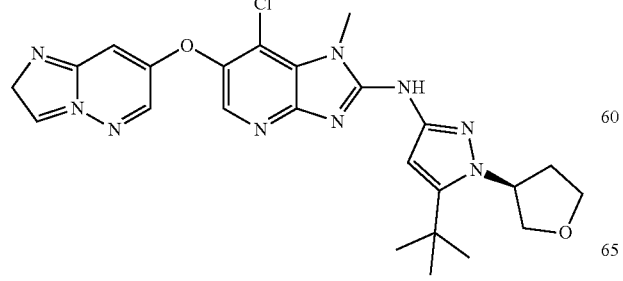

I-17
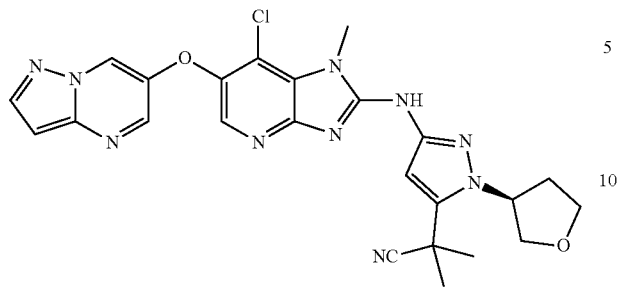
I-21'
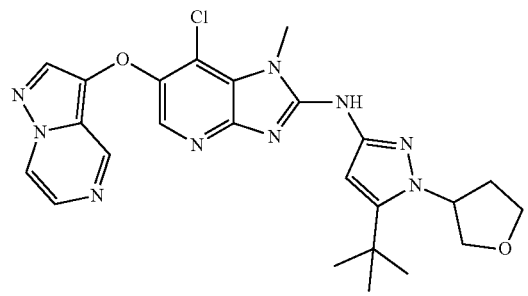
I-18
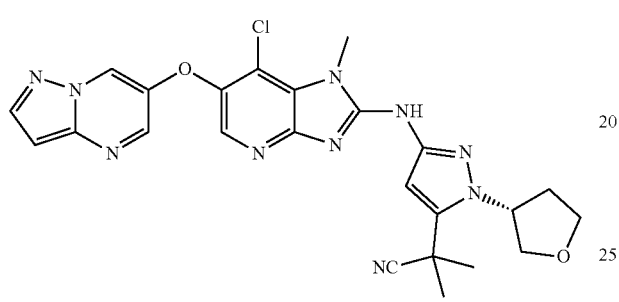
I-21
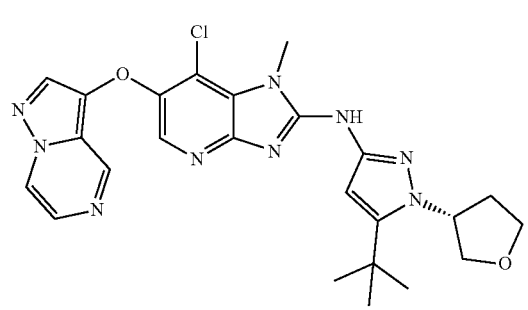
I-19'
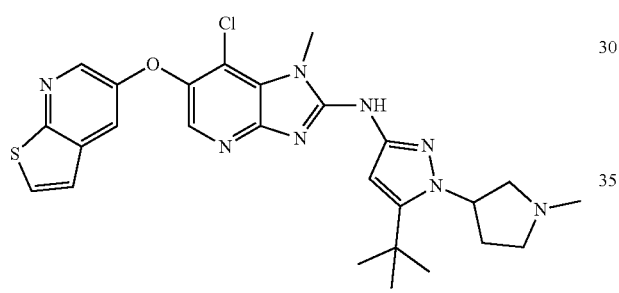
I-22
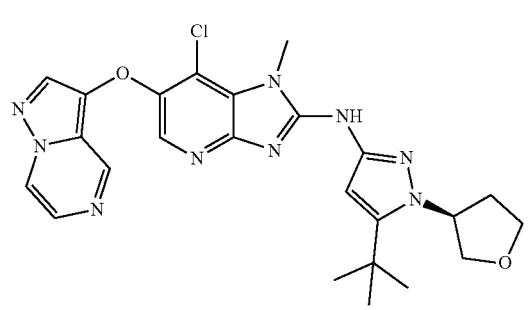
I-19
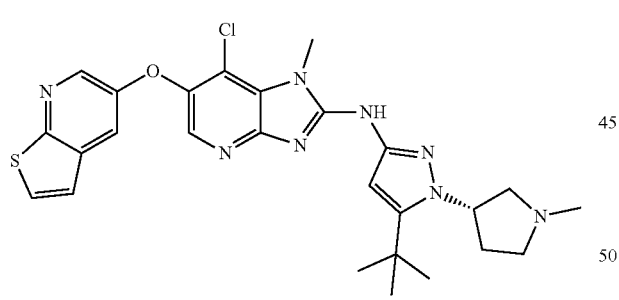
I-23'
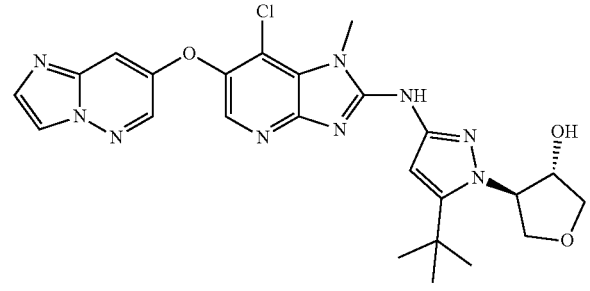
I-20
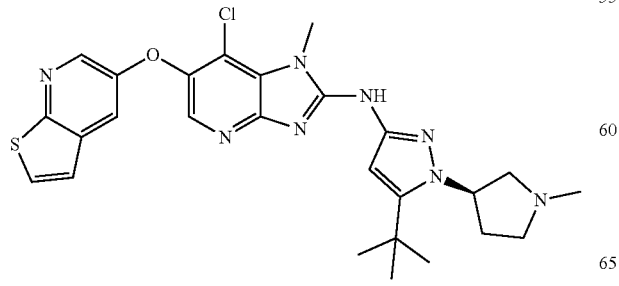
I-23-i I-23-ii
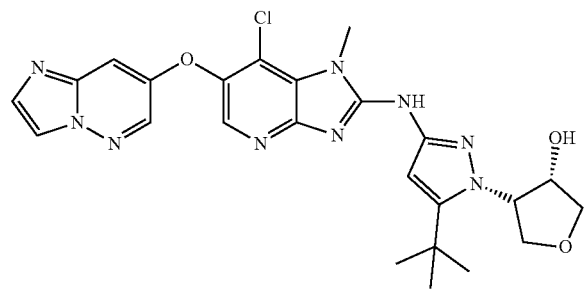
I-23-iii
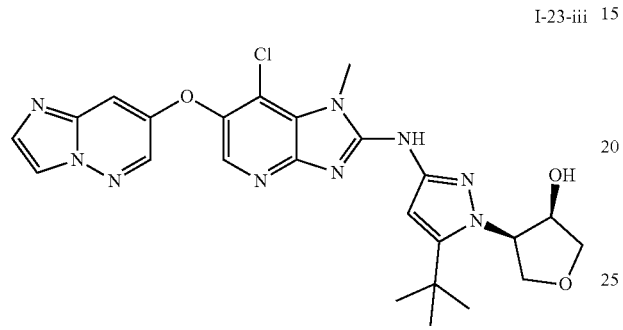
I-23-iv
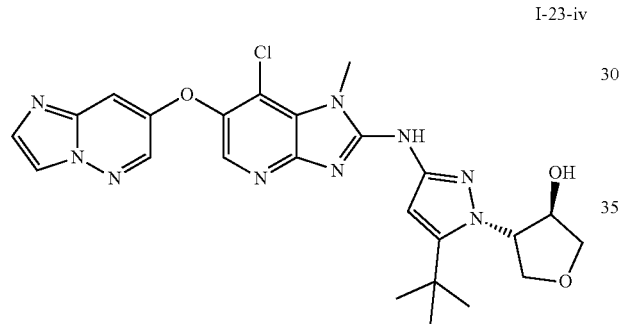
I-25'
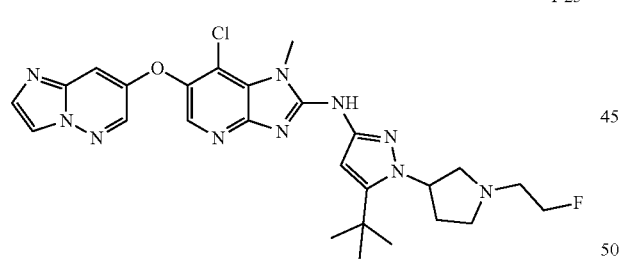
I-25
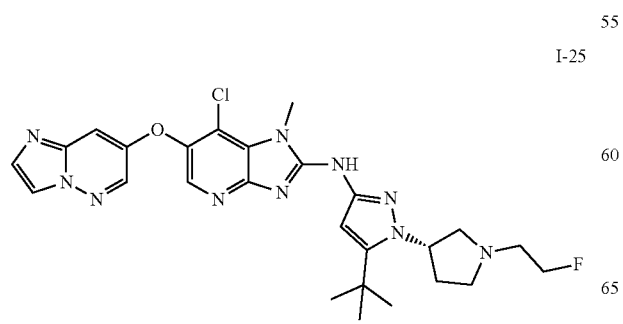
I-26
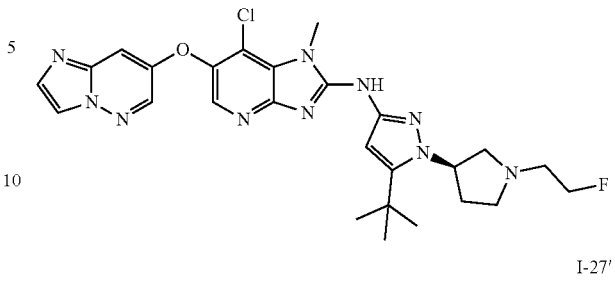
I-27'
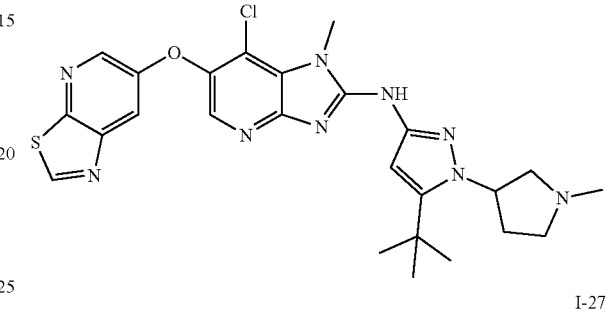
I-27
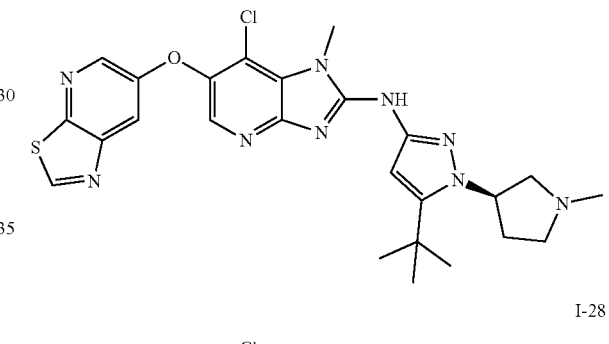
I-28
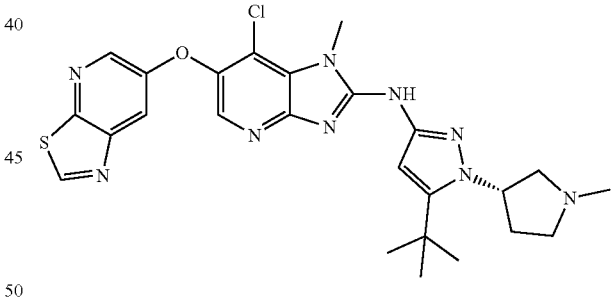
I-29'

I-29
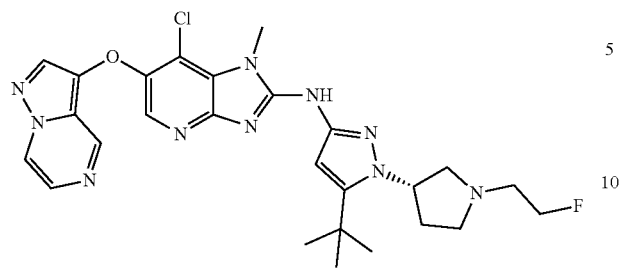
I-30
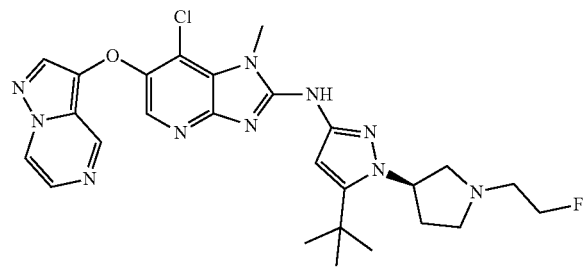
I-31'
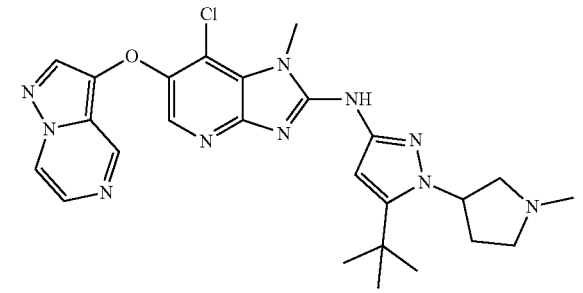
I-31
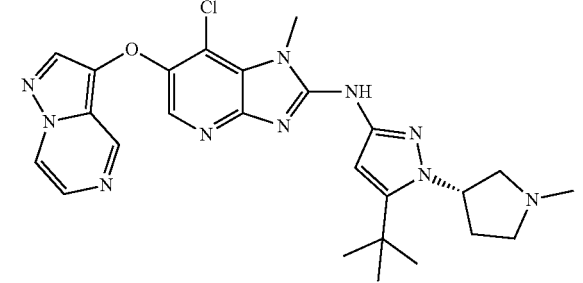
I-32
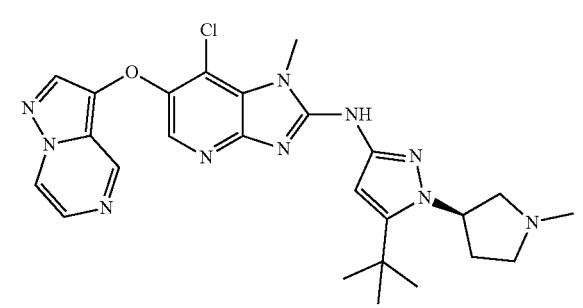
I-33
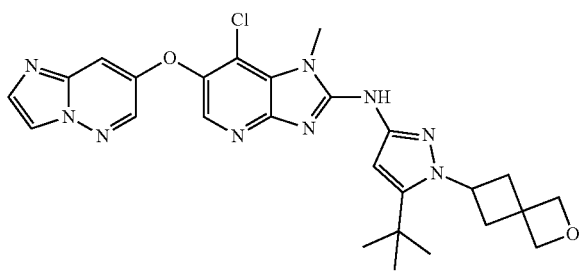
I-34
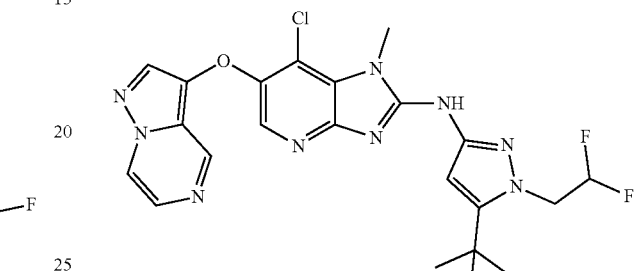
I-35'
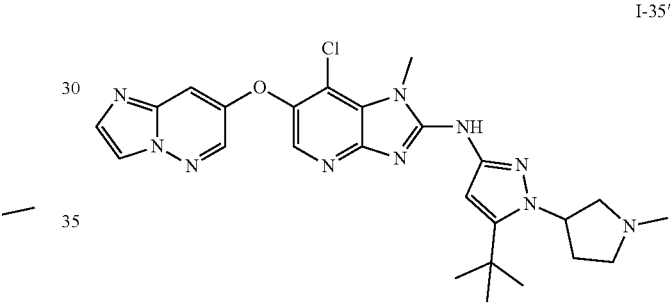
I-35
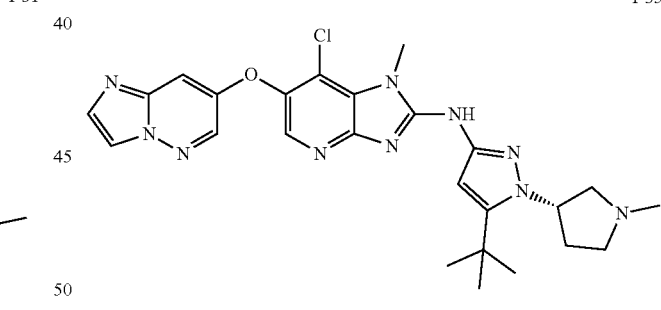
I-36

I-37
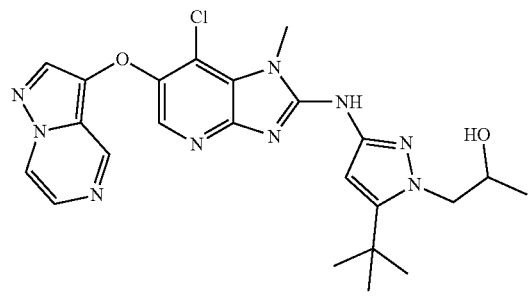
I-40
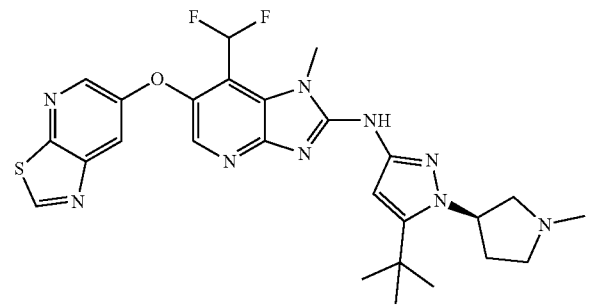
I-37-i
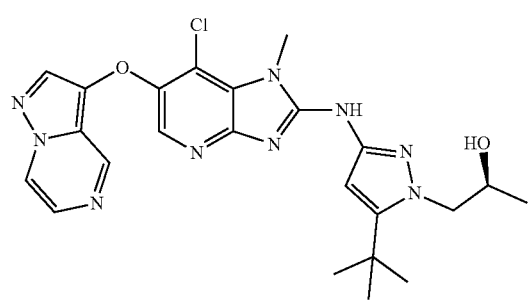
I-41
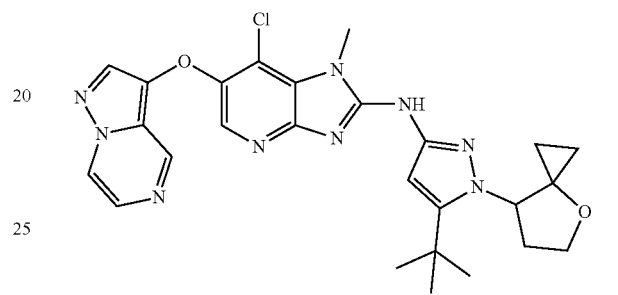
I-37-ii
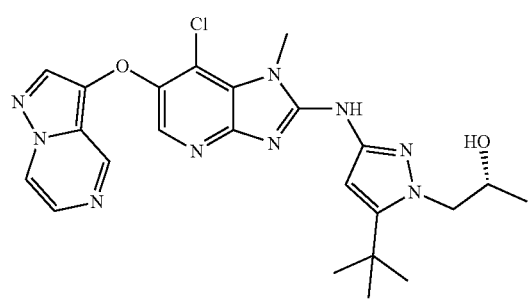
I-41-i
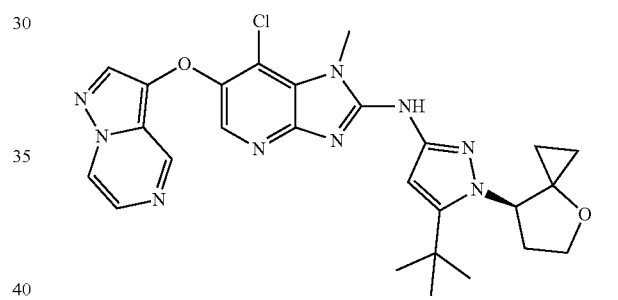
I-39'
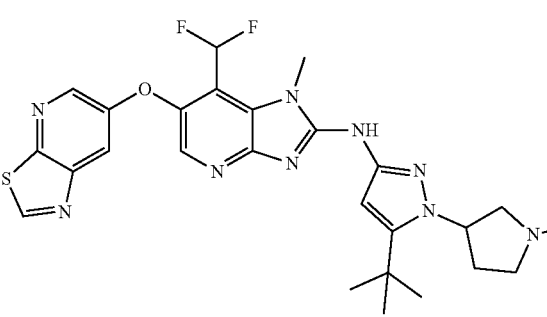
I-41-ii
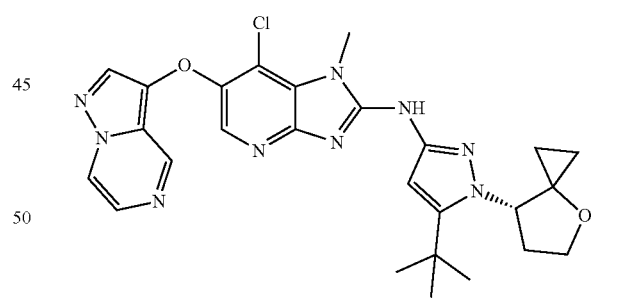
I-39
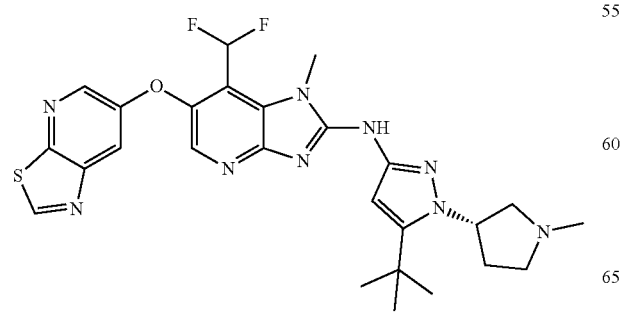
I-42
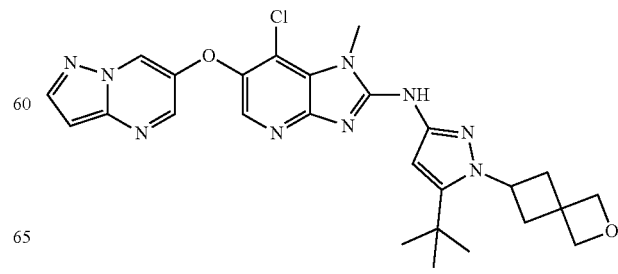

I-43'
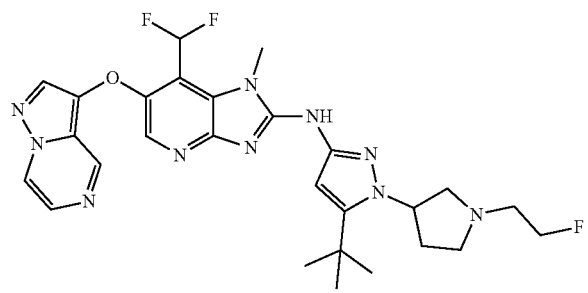
I-43
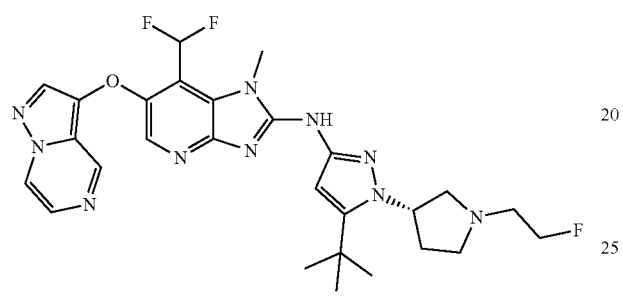
I-44
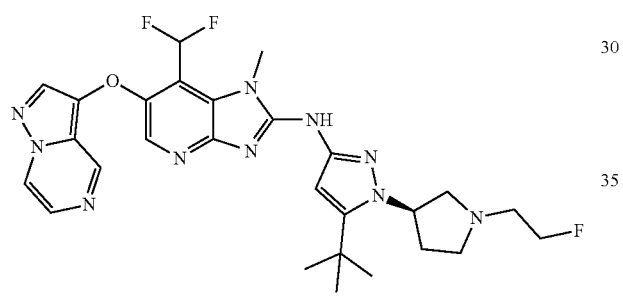
I-45'
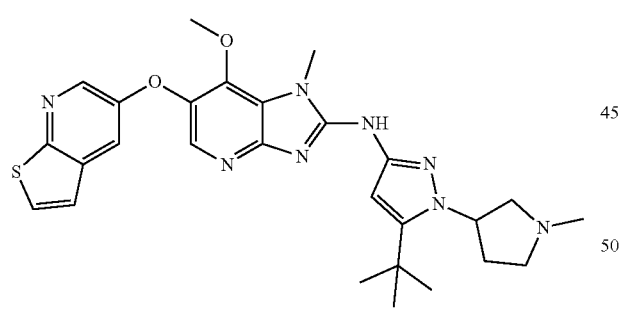
I-45
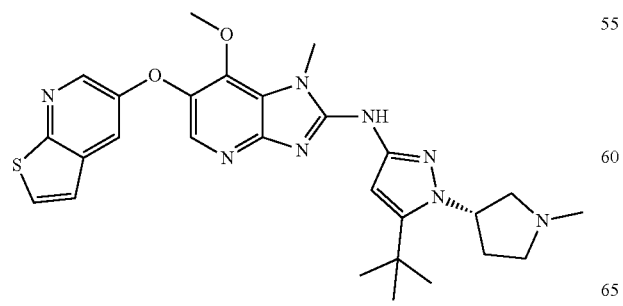
I-46
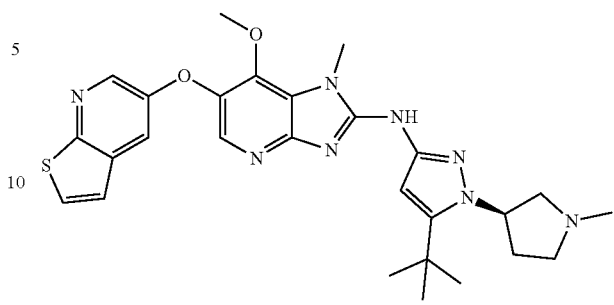
I-47
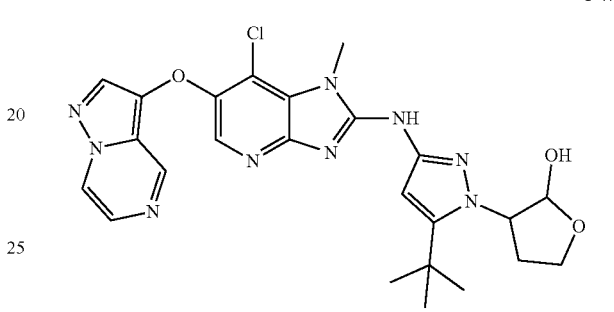
I-47-i
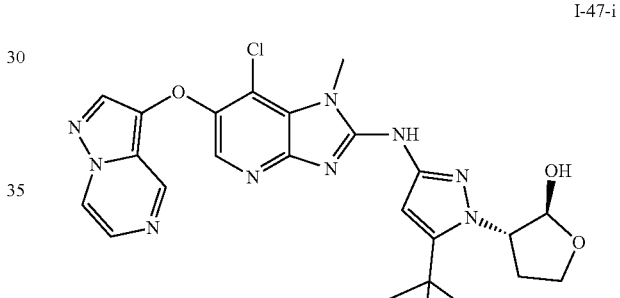
I-47-ii
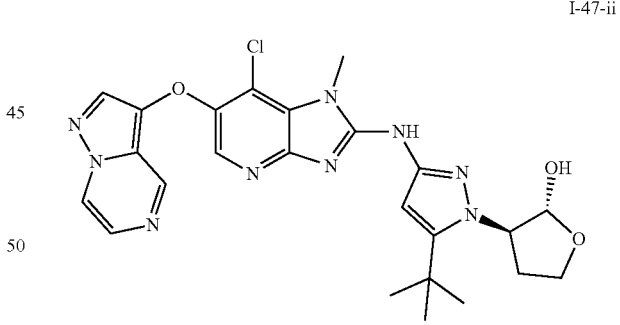
I-47-iii
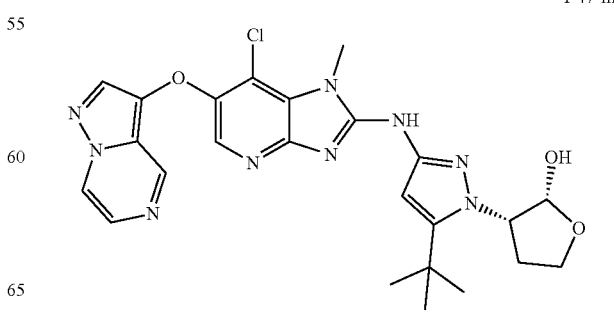

1195
-continued
I-47-iv
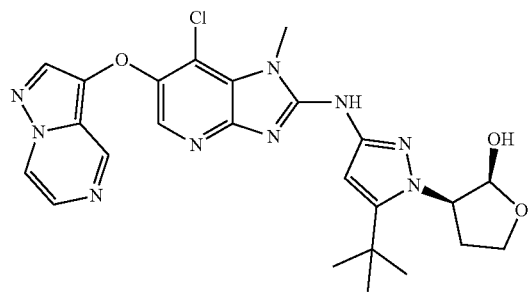
I-49
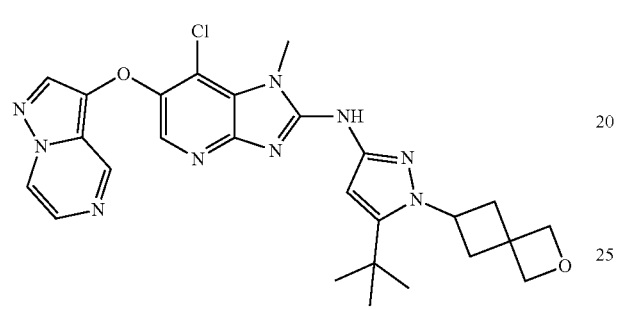
I-50'
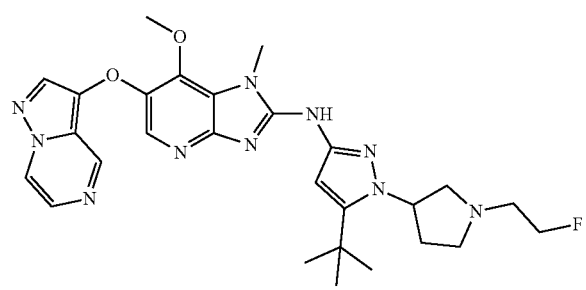
I-50
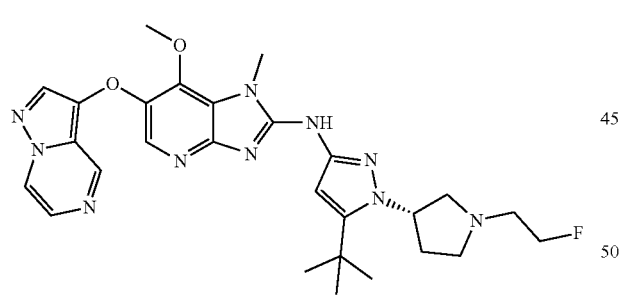
I-50-ii
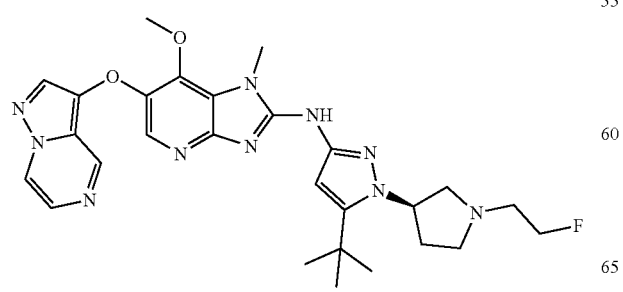
1196
-continued
I-51'
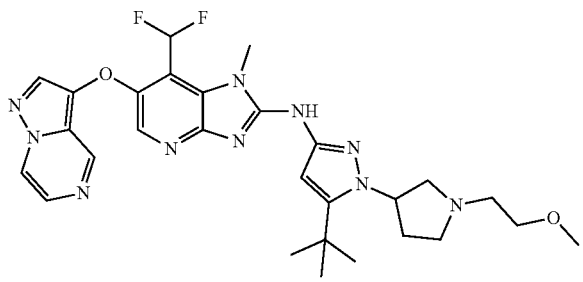
I-51
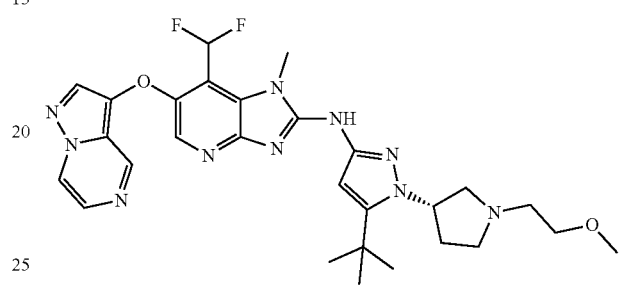
I-52
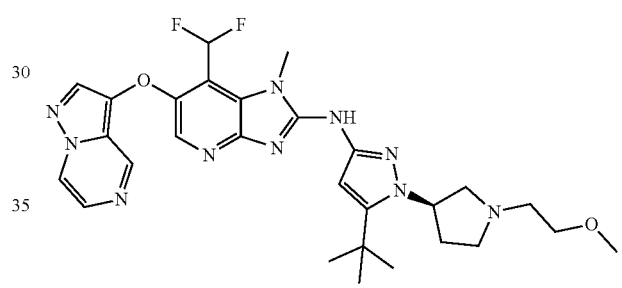
I-53
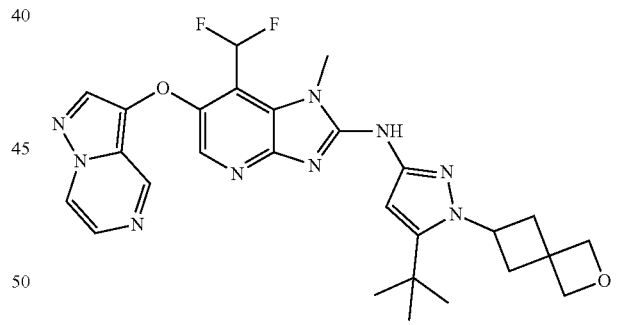
I-54
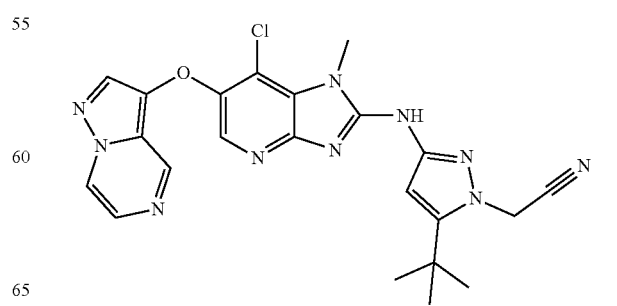

1197
-continued
I-55'
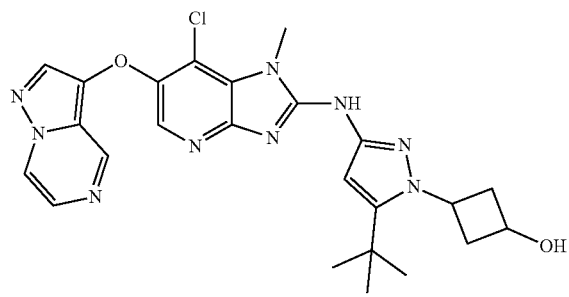
I-55
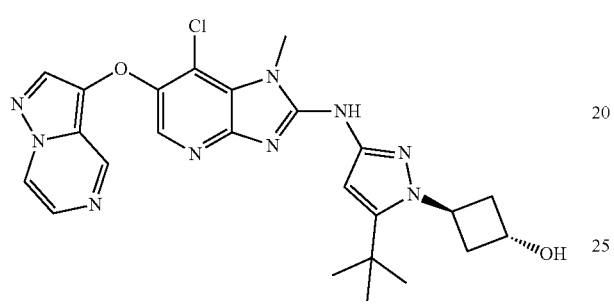
I-55-ii
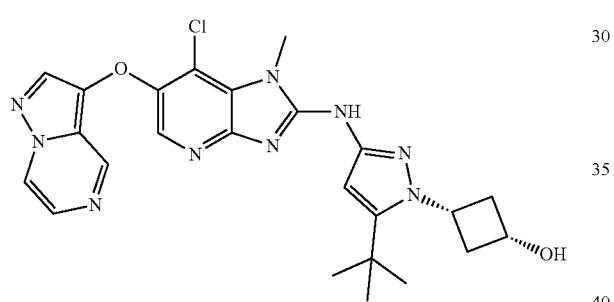
I-56
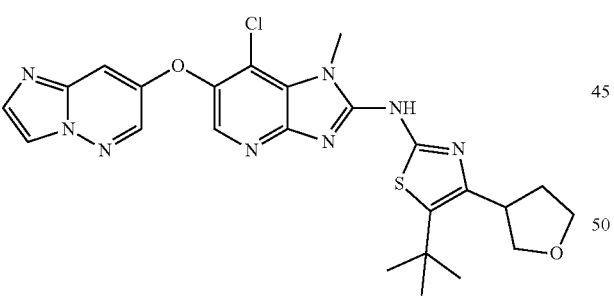
I-56-i
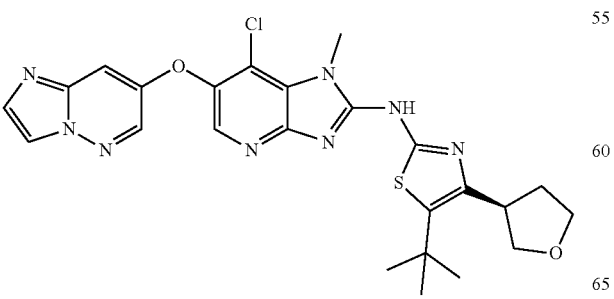
1198
-continued
I-56-ii
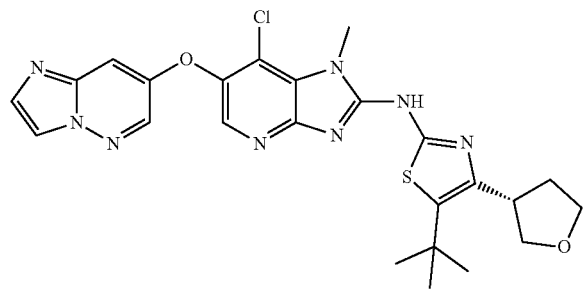
I-57
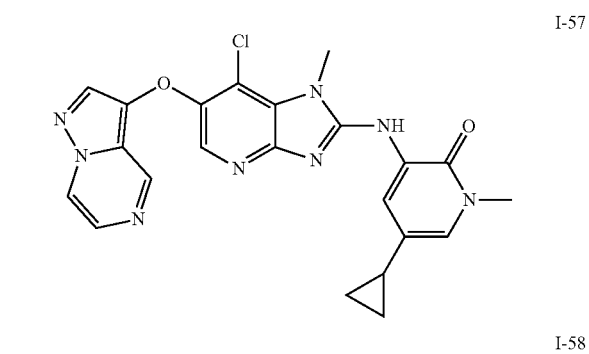
I-58
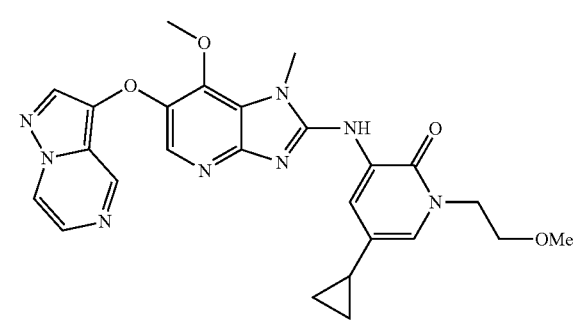
I-59
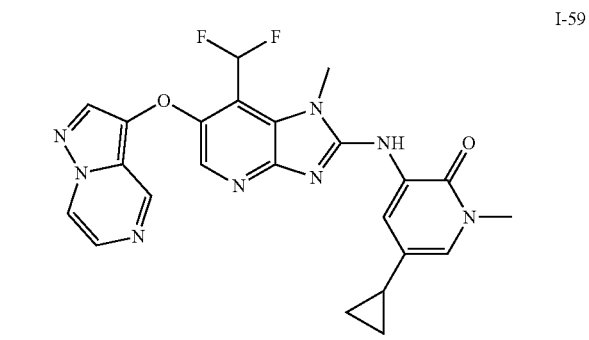
I-60
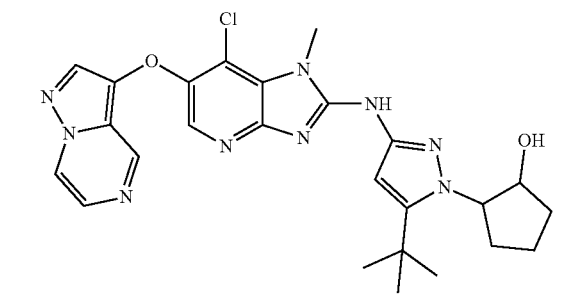

I-60-i
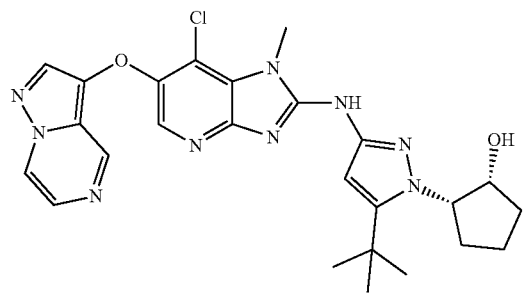
I-62
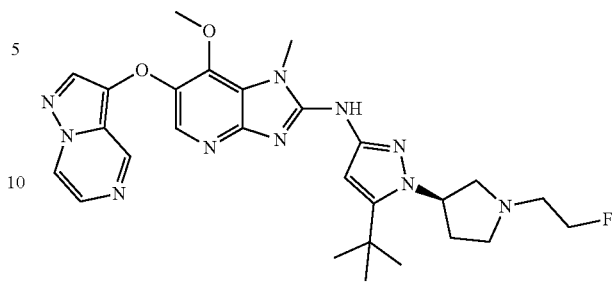
I-60-ii
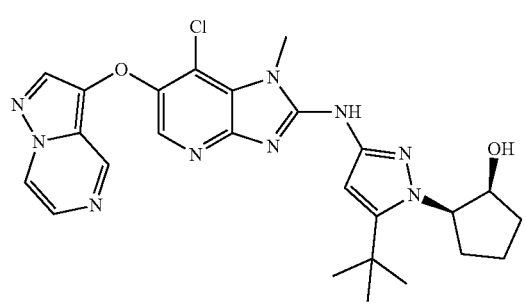
I-63
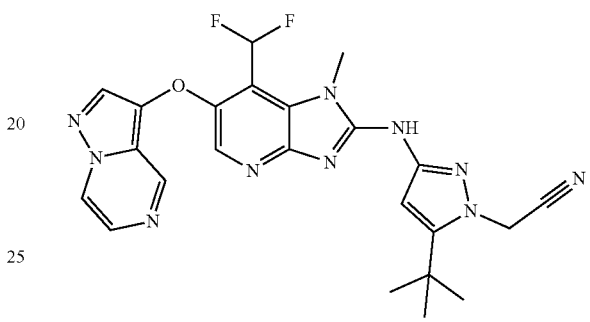
I-60-iii
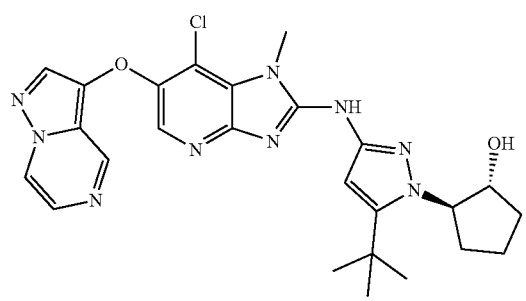
I-64
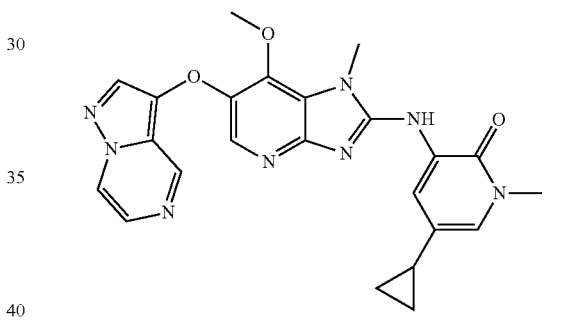
I-60-iv
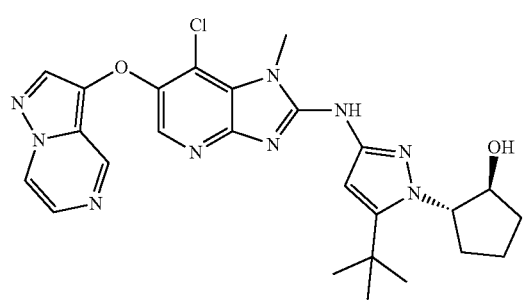
I-65
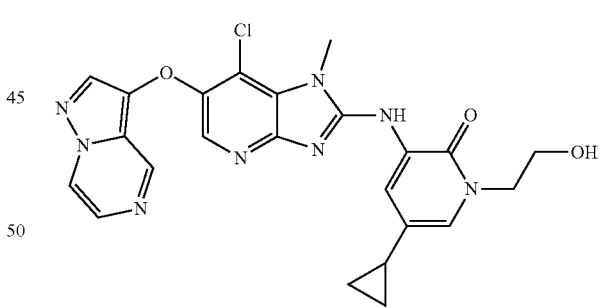
I-61
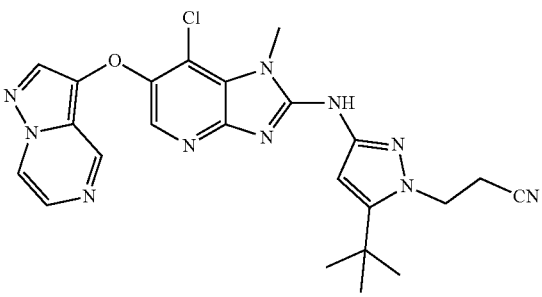
I-66'
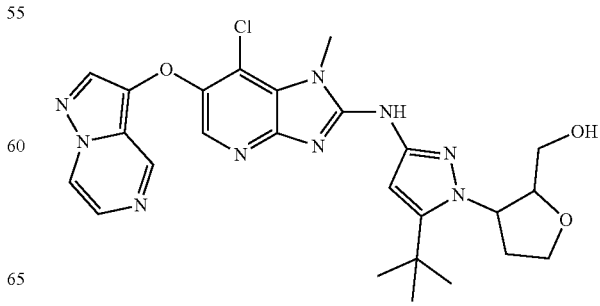

I-66
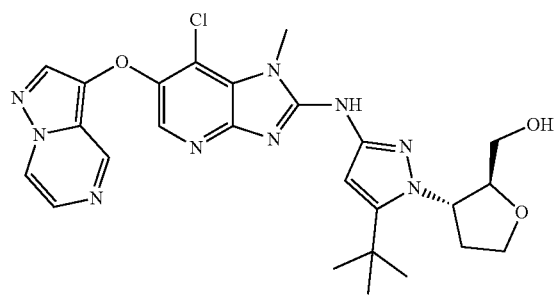
I-66-ii
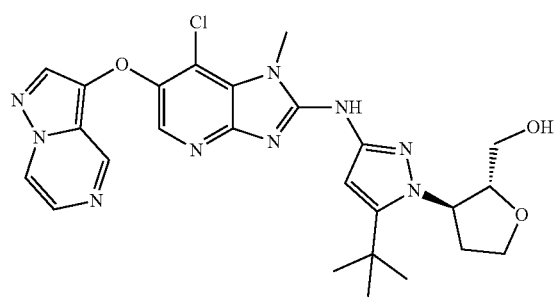
I-66-iii
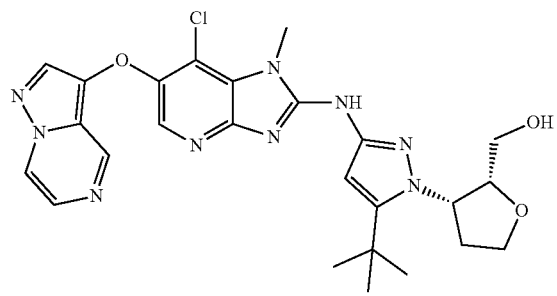
I-66-iv
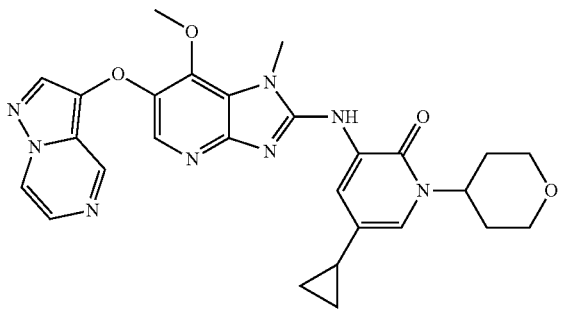
I-67
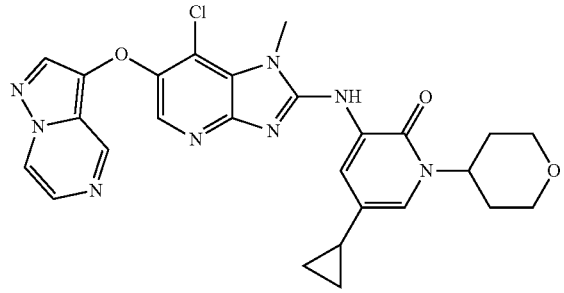
I-68
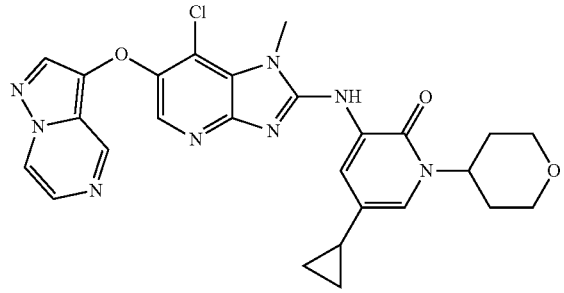
I-69
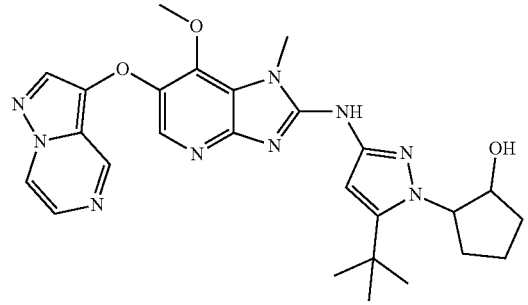
I-69-i
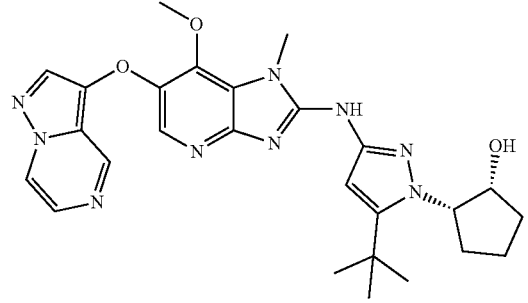
I-69-ii
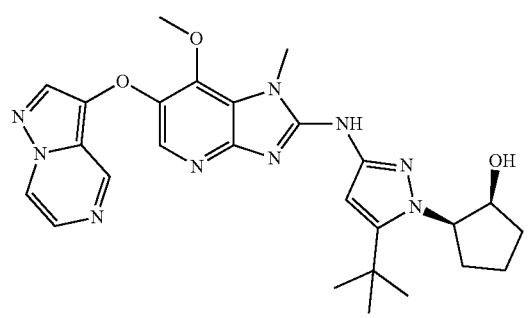
I-69-iii
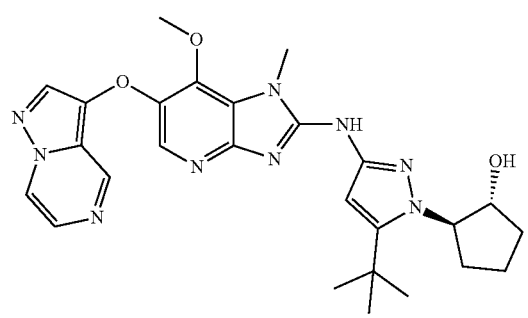

1203
-continued
I-69-iv
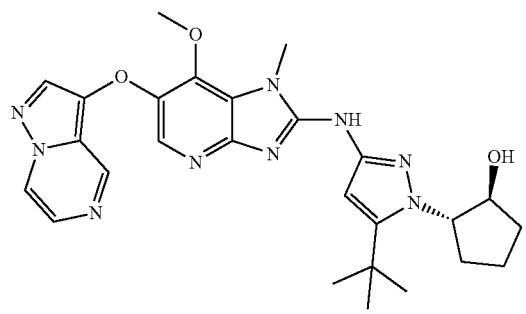
I-70'
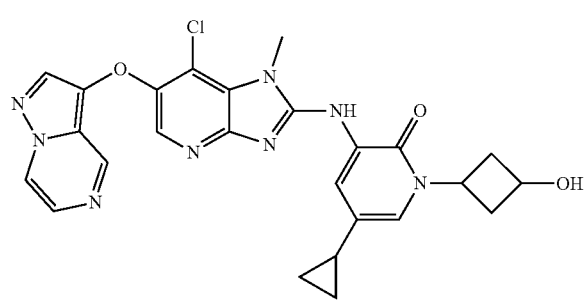
I-70
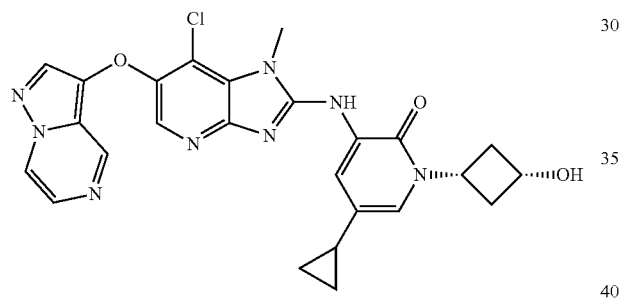
I-70-ii
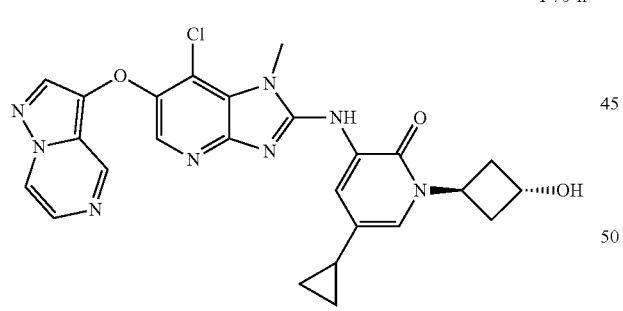
I-71
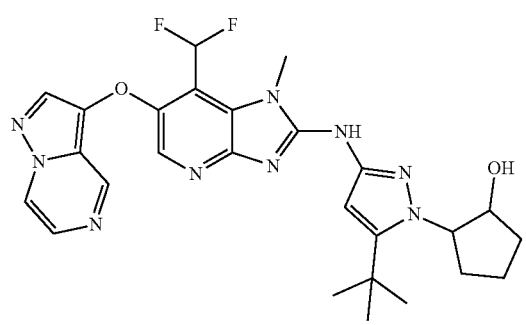
1204
-continued
I-71-i
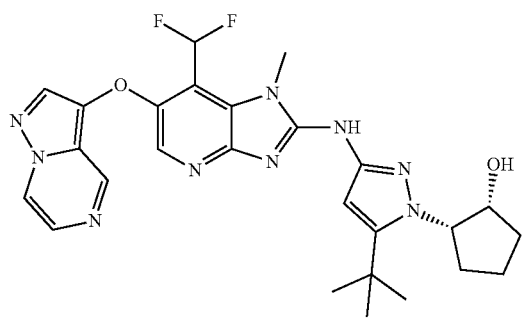
I-71-ii
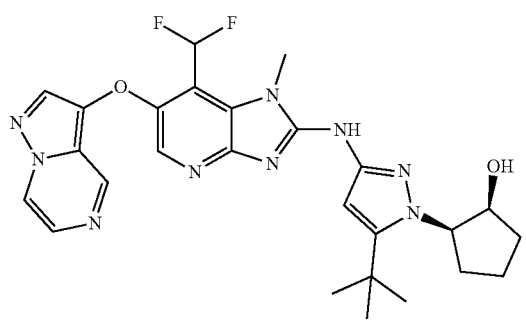
I-71-iii
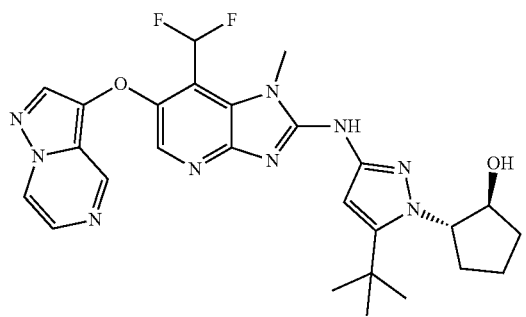
I-71-iv I-72
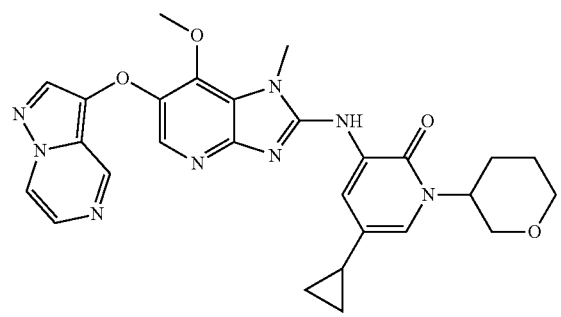
I-72-i
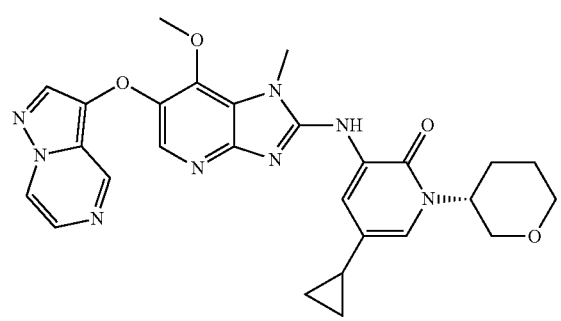
I-72-ii
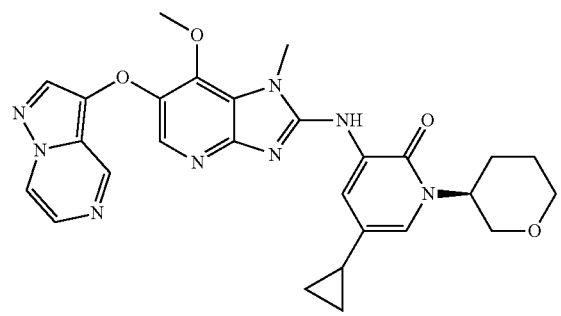
I-73
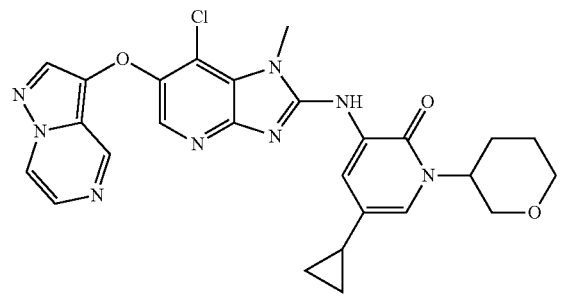
I-73-i
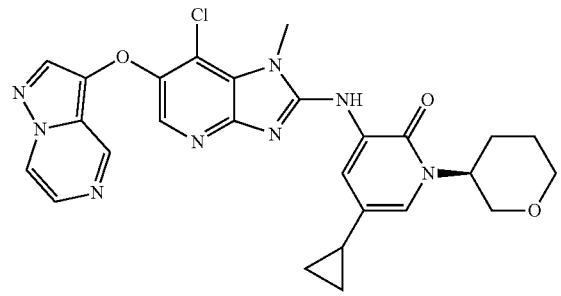
I-73-ii
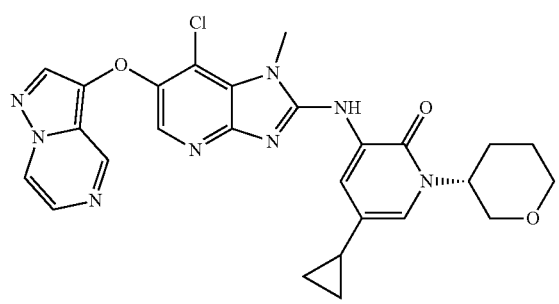
I-74'
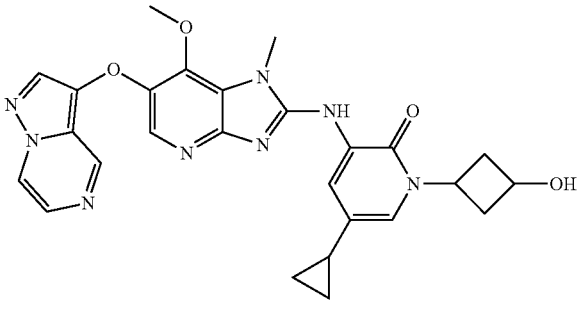
I-74
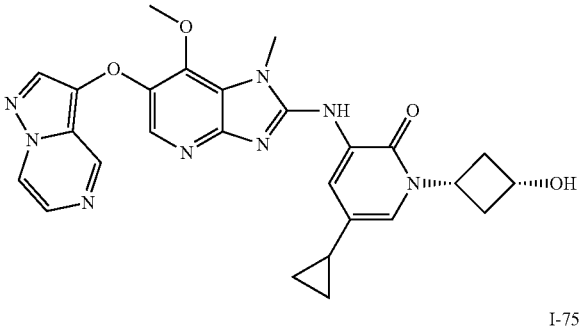
I-75
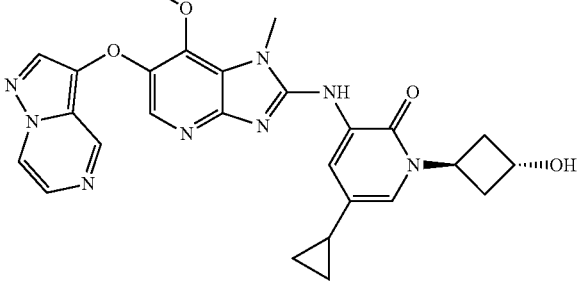
I-76
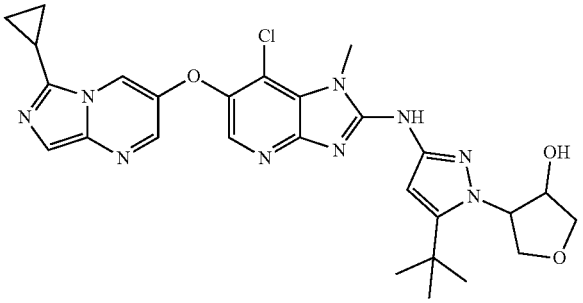

1207
-continued
I-76-i
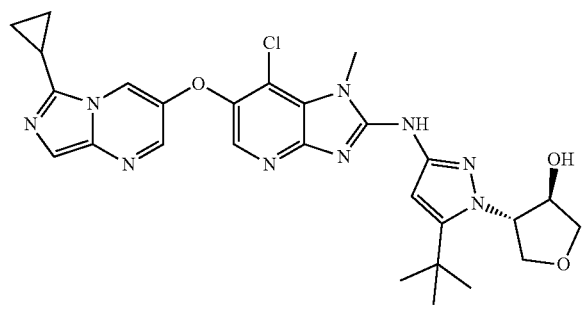
I-76-ii
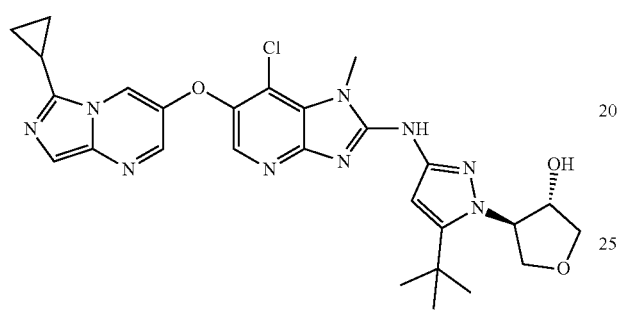
I-76-iii
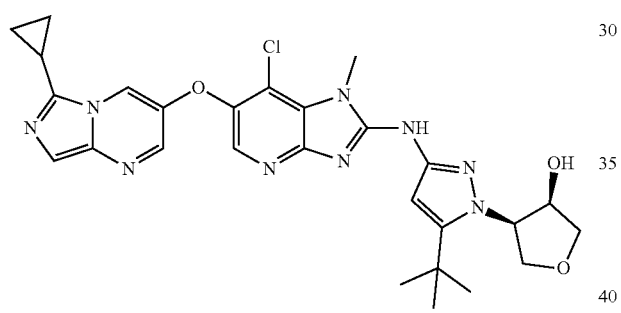
I-76-iv
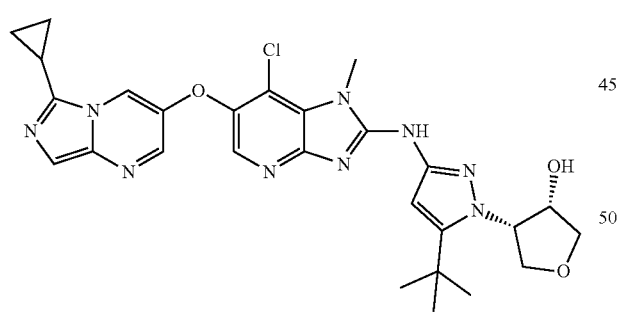
I-77'
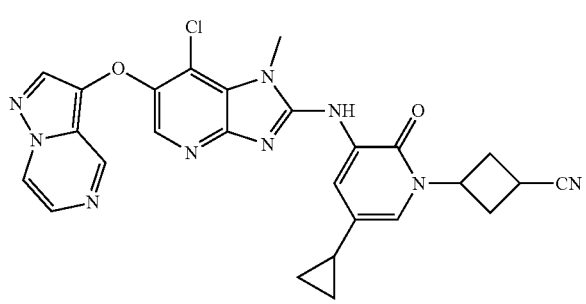
1208
-continued
I-77
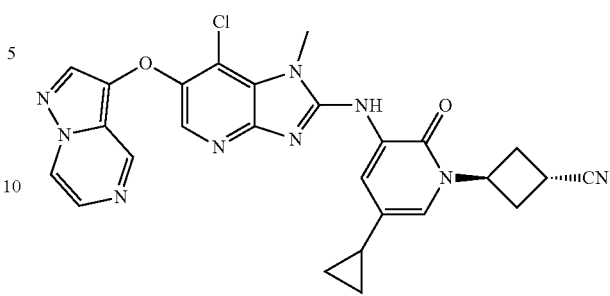
I-78
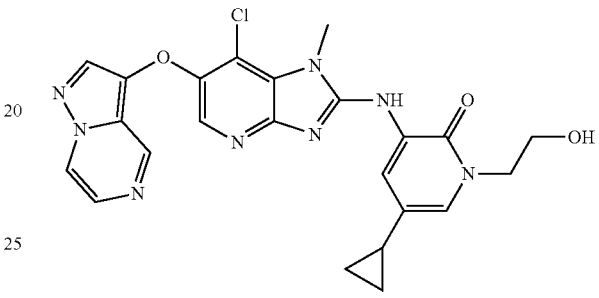
I-79'
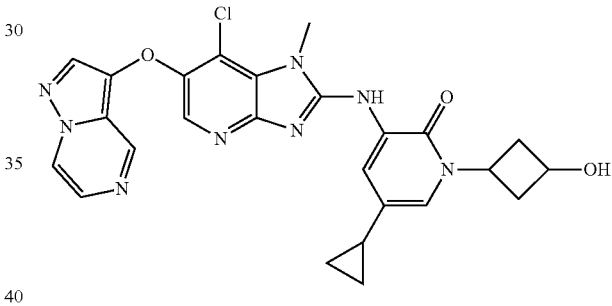
I-79
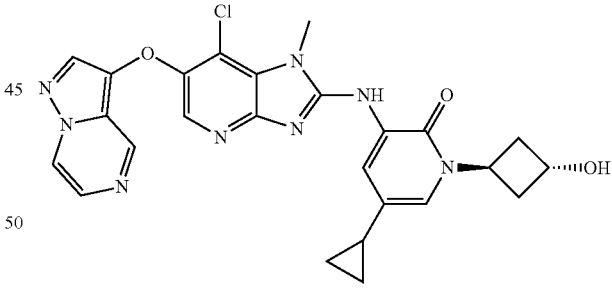
I-79-ii
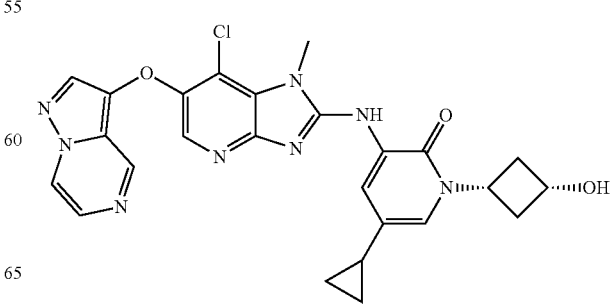

I-80
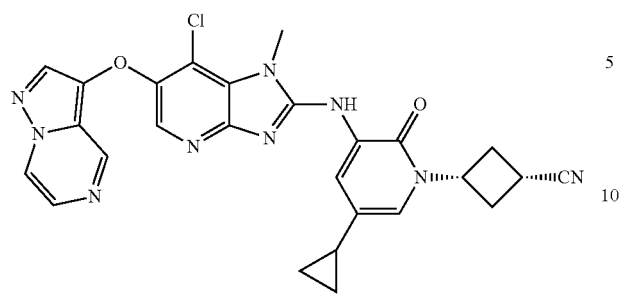
I-81
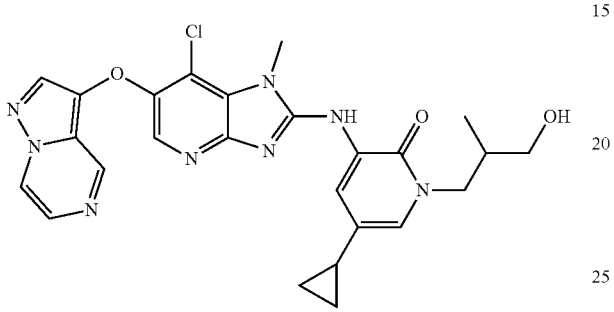
I-81-i
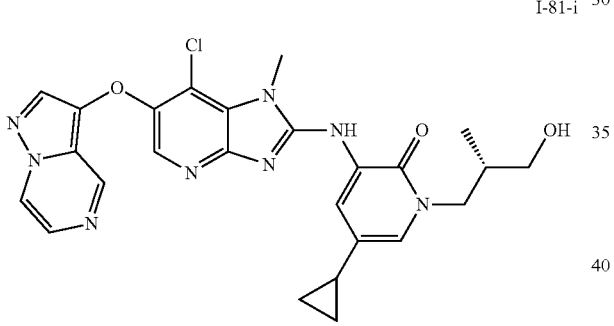
I-81-ii
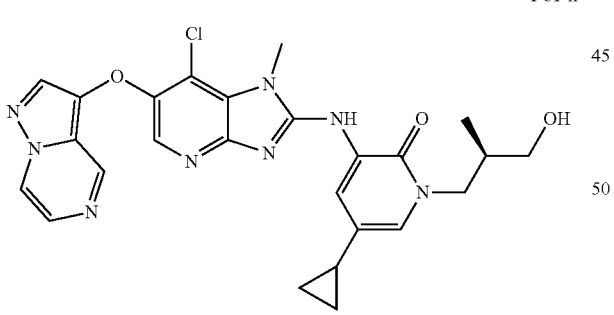
I-82
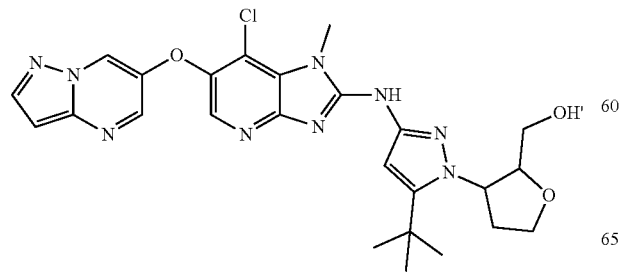
I-82
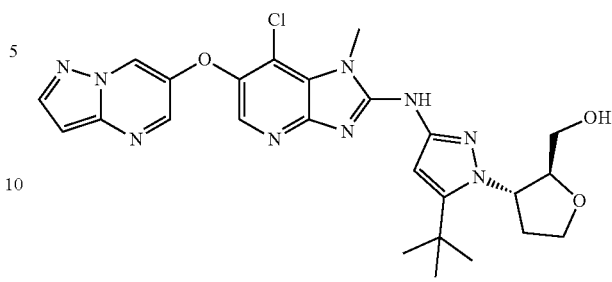
I-82-ii
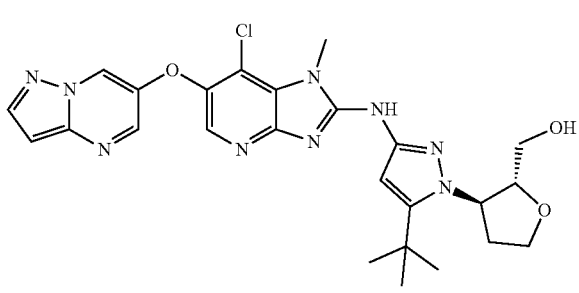
I-82-iii
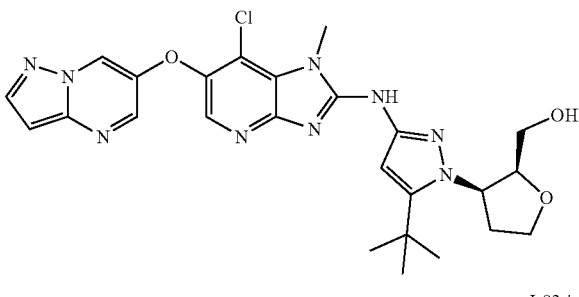
I-82-iv
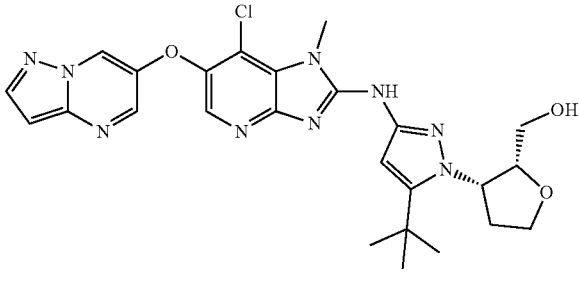
I-83
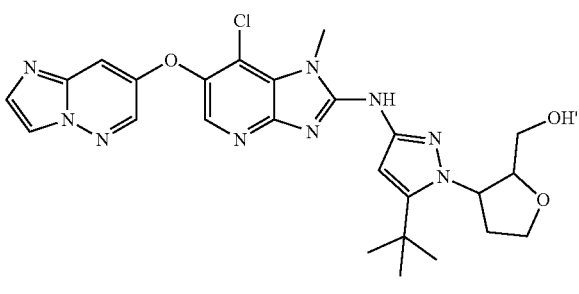

I-83
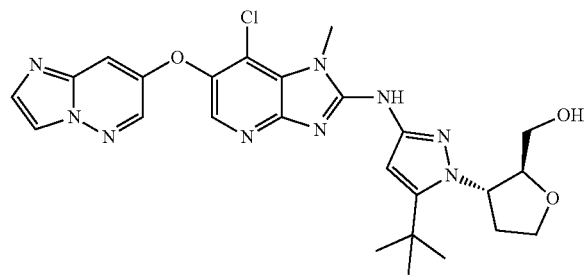
I-83-ii
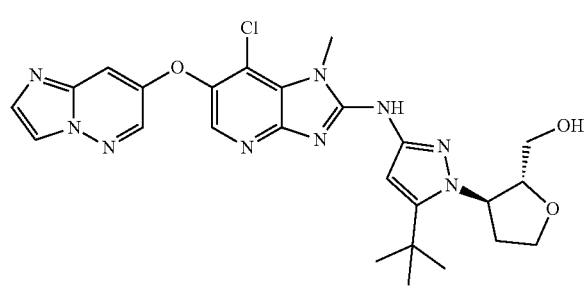
I-83-iii
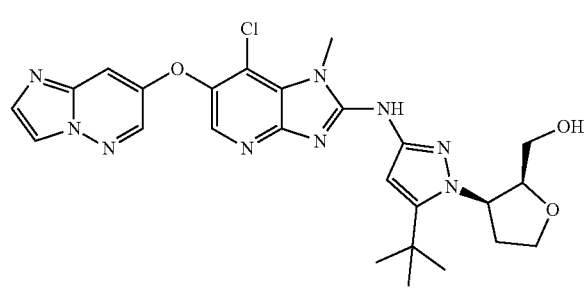
I-83-iv
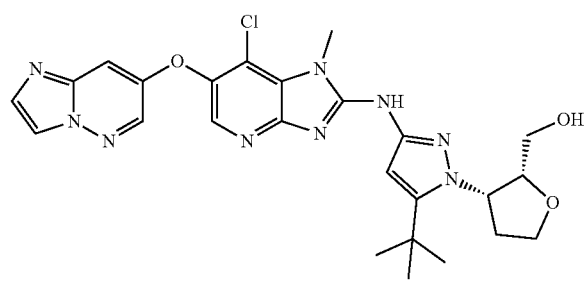
I-84
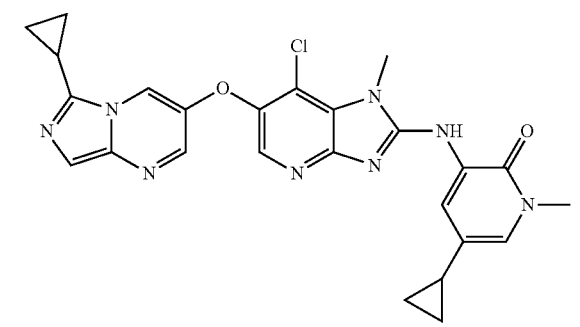
I-85
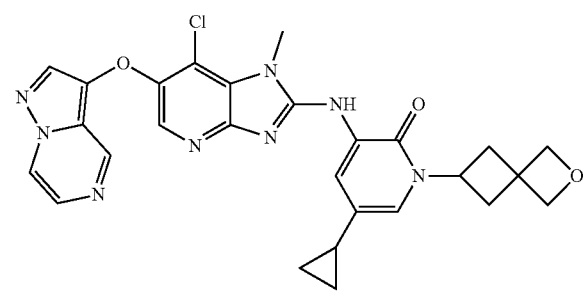
I-86
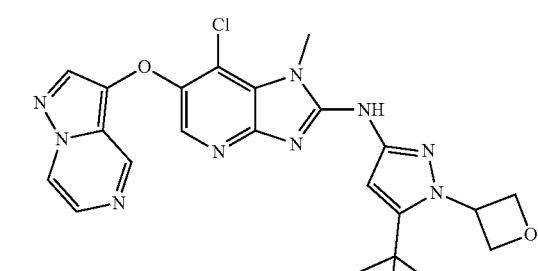
I-87'
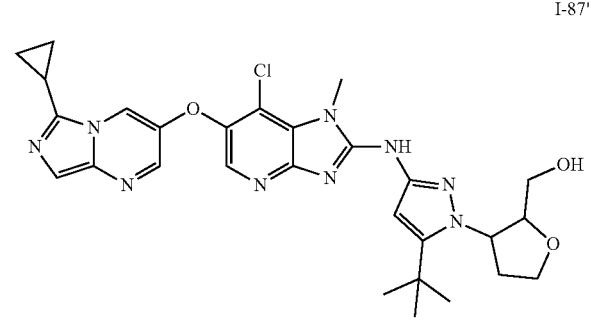
I-87
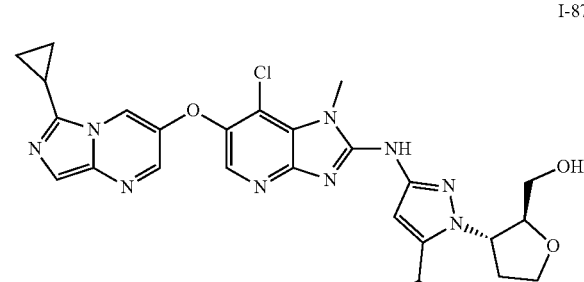
I-87-ii
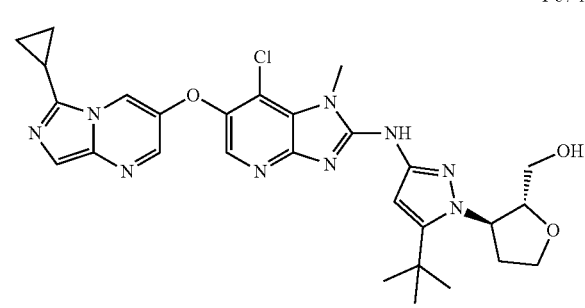

I-87-iii
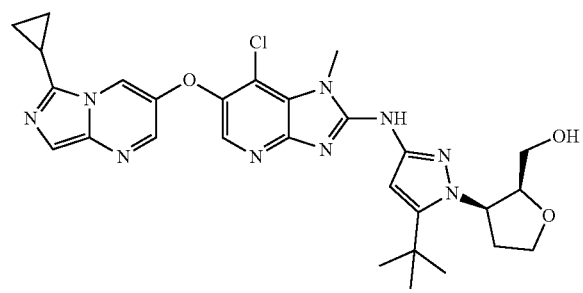
I-89
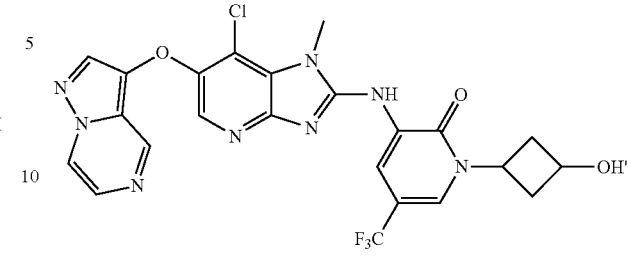
I-87-iv
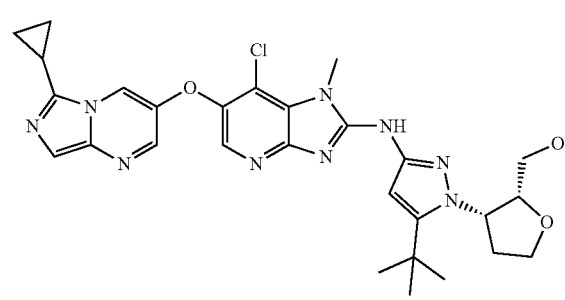
I-89
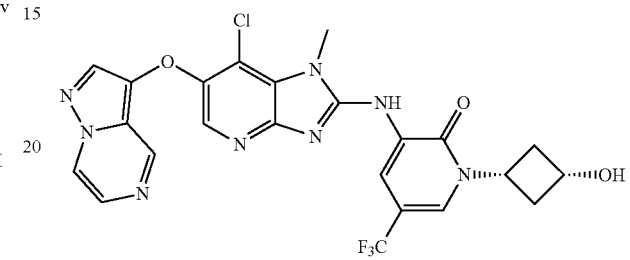
I-88'
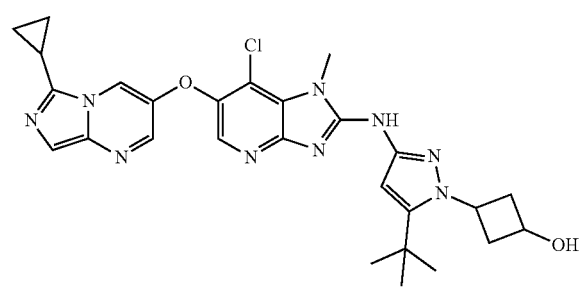
I-89-ii
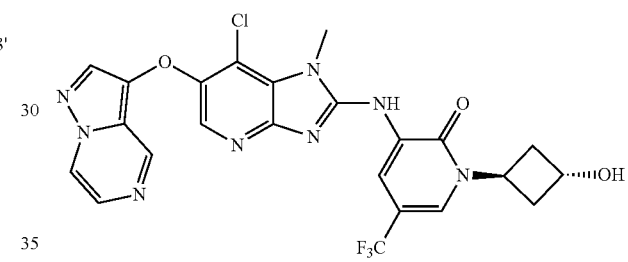
I-88
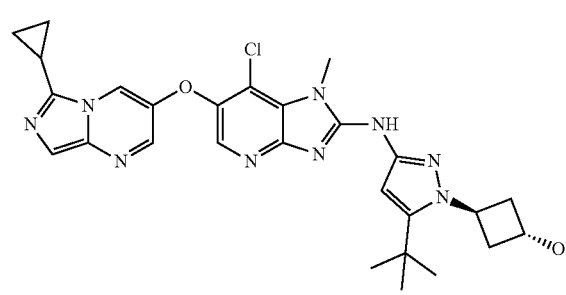
I-90
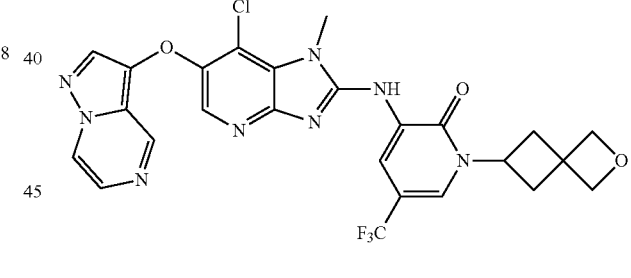
I-88-ii
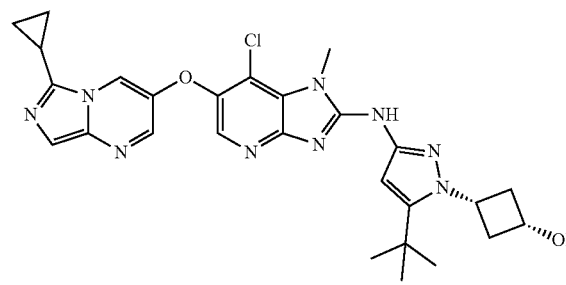
I-91
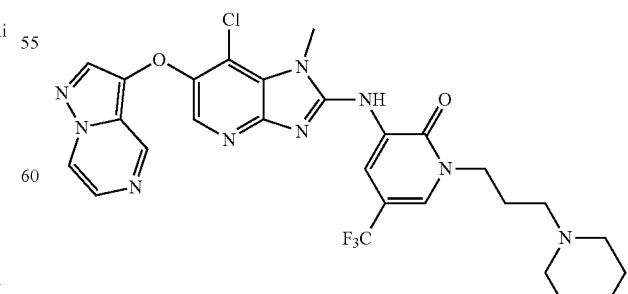

I-92
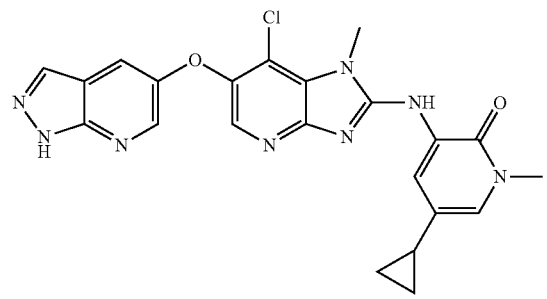
I-93
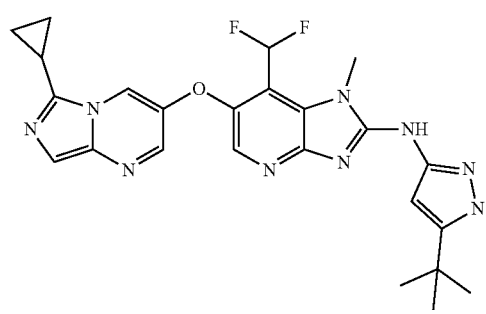
I-93-i
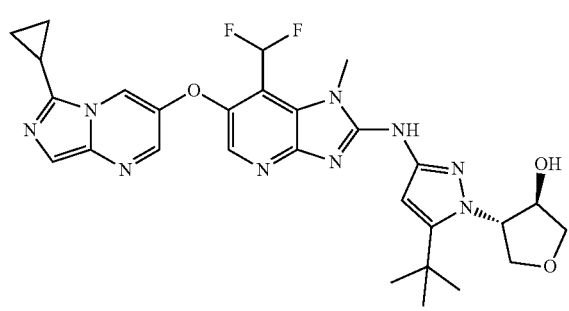
I-93-ii
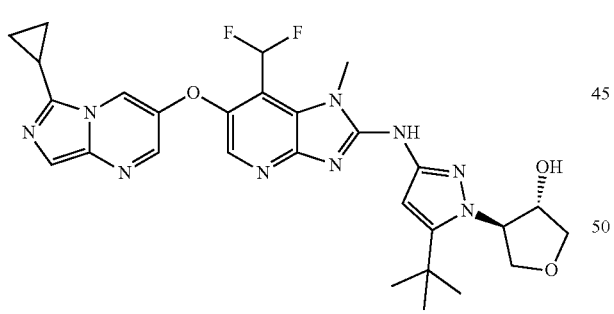
I-93-iii
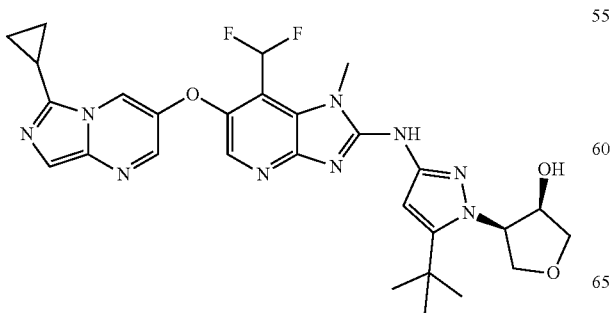
I-93-iv
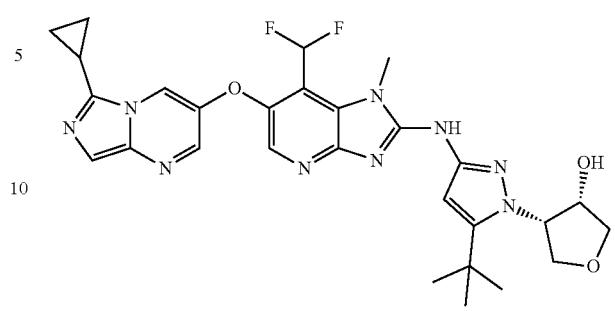
I-94
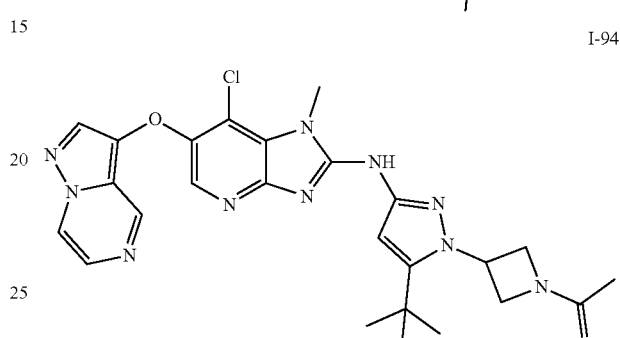
I-95
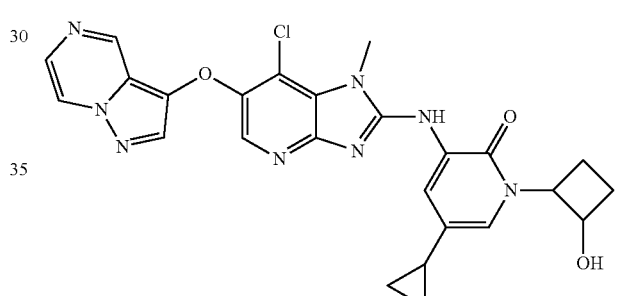
I-95-i
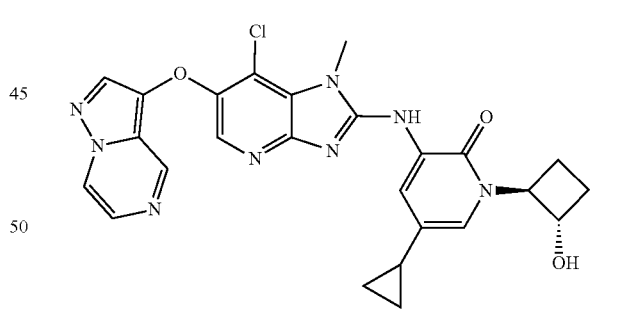
I-95-ii
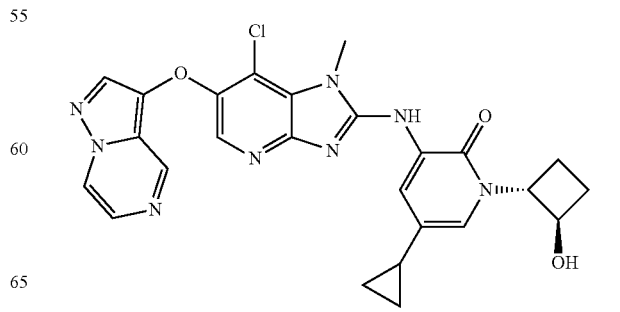

I-96'
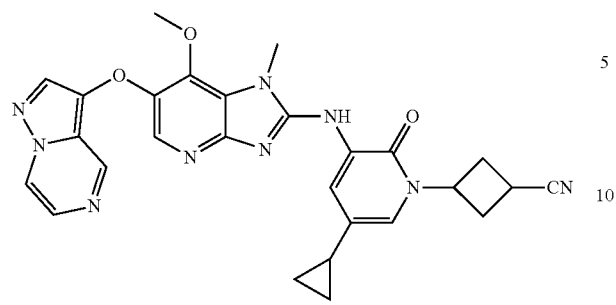
I-96
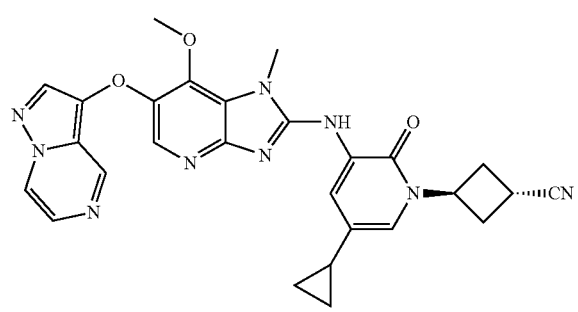
I-96-ii
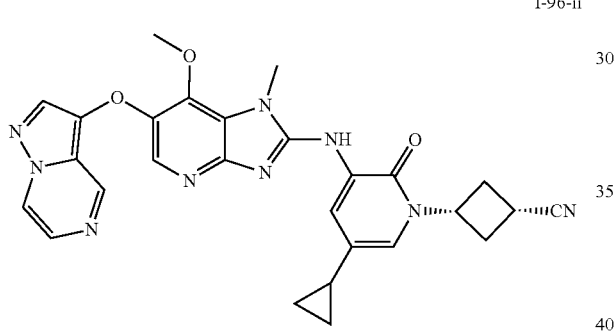
I-97
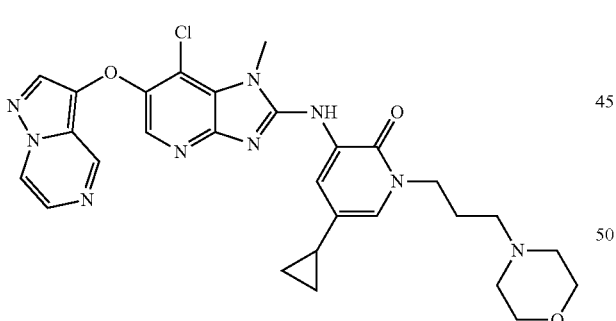
I-98-i
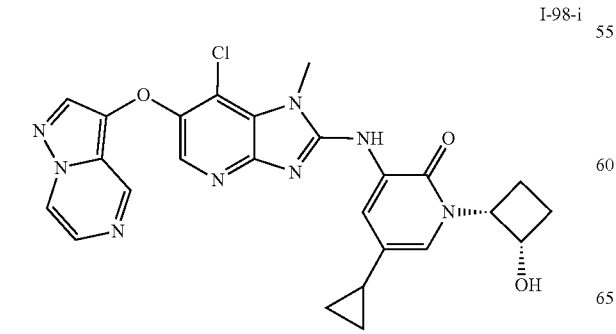
I-98-ii
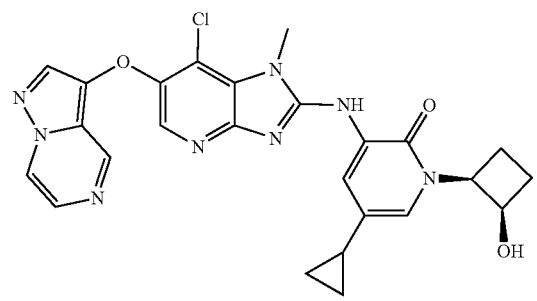
I-99
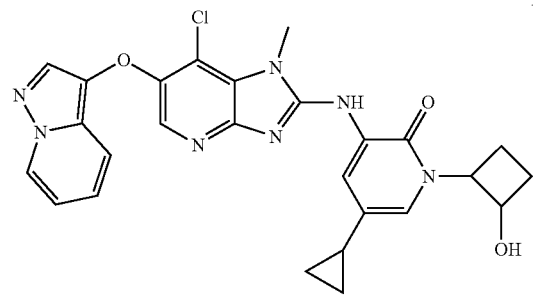
I-99-i
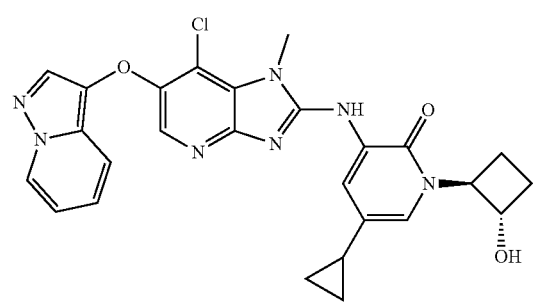
I-99-ii
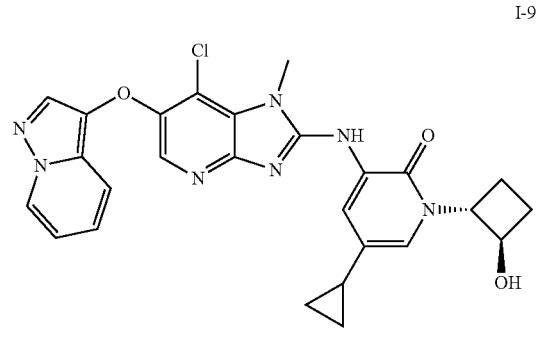
I-100
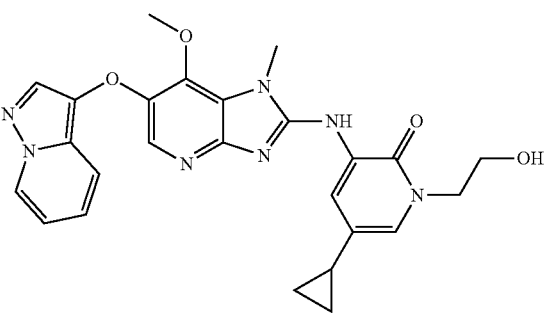

I-101
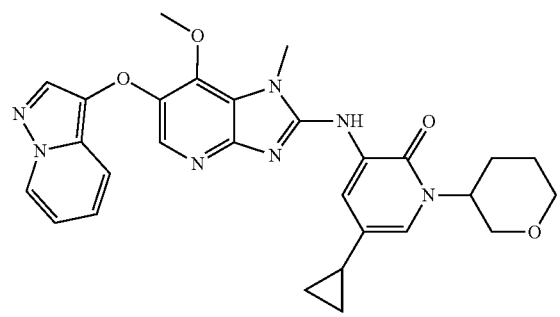
I-101-i
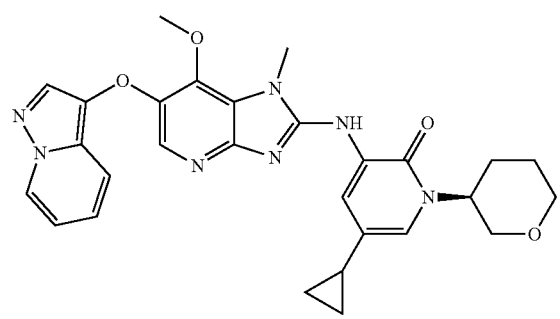
I-101-ii
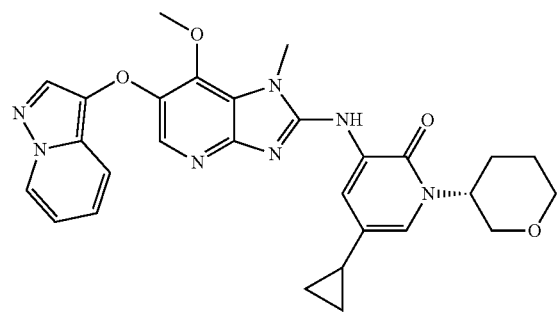
I-102
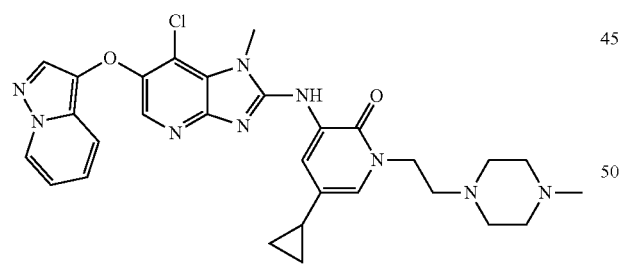
I-103
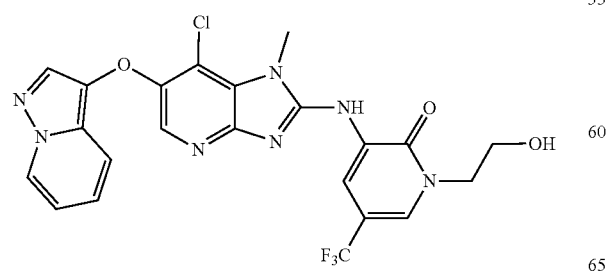
I-104
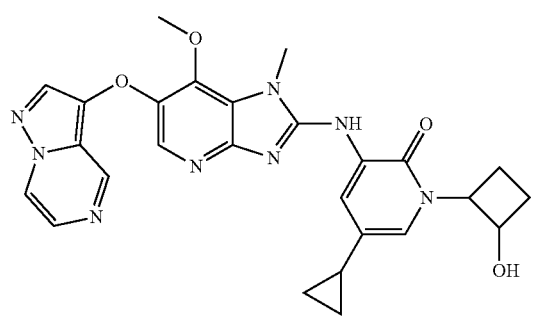
I-104-i
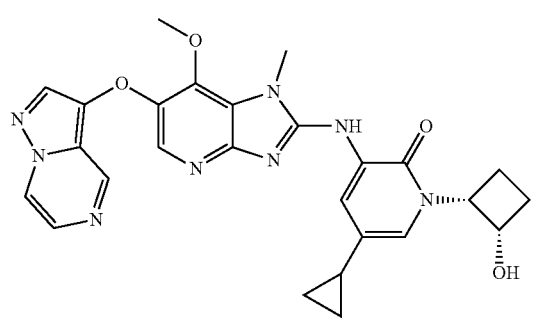
I-104-ii
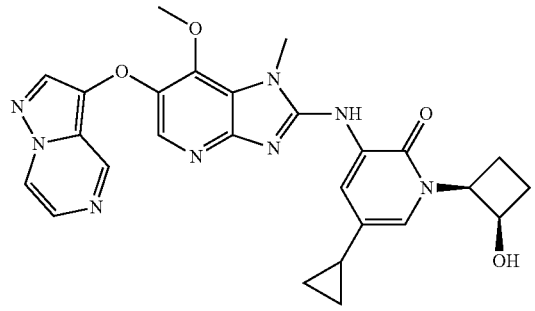
I-105
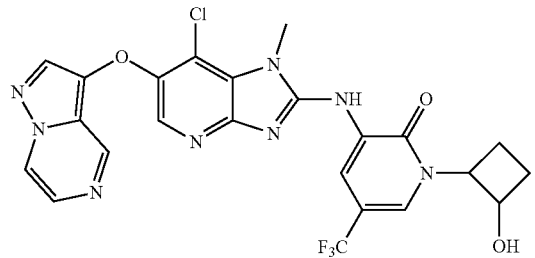
I-105-i
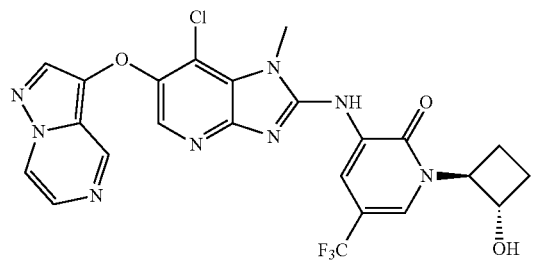

1221
-continued
I-105-ii
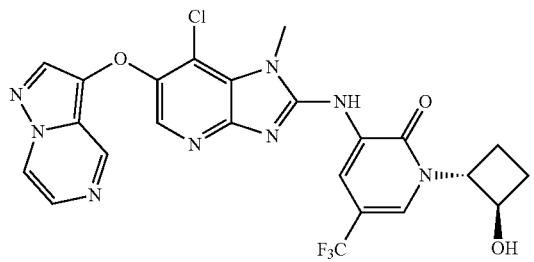
I-106
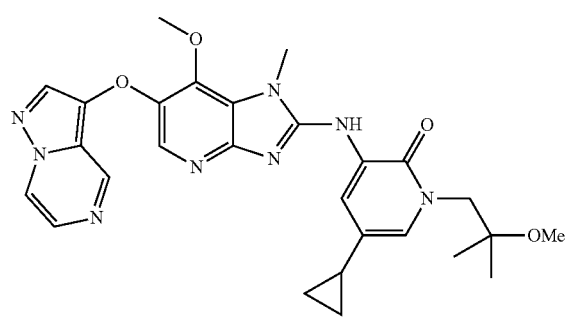
I-107
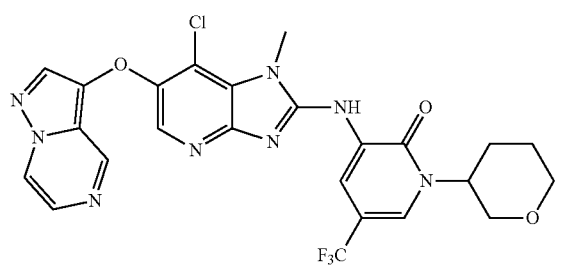
I-107-i
I-107-ii
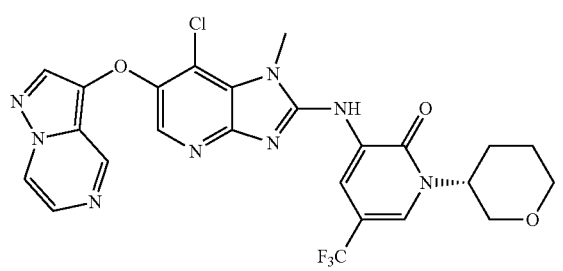
1222
-continued
I-108
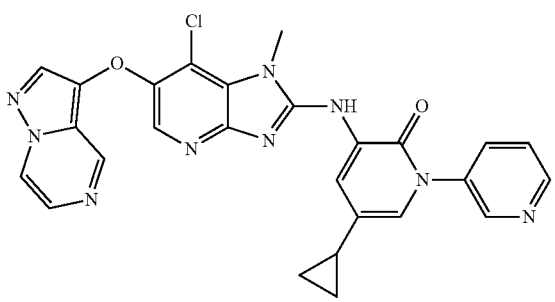
I-109
I-110-i
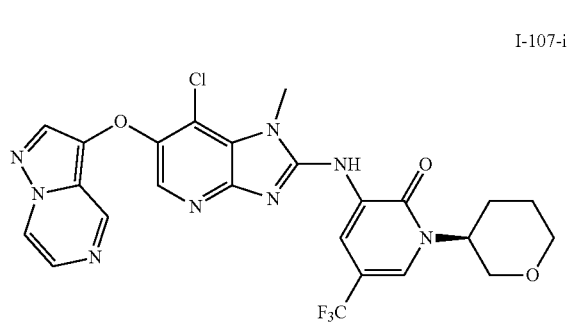
I-110-ii
I-111
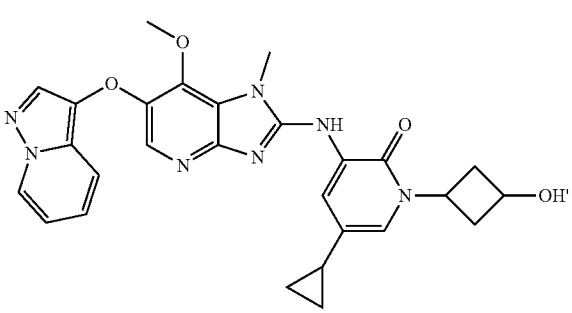

I-111
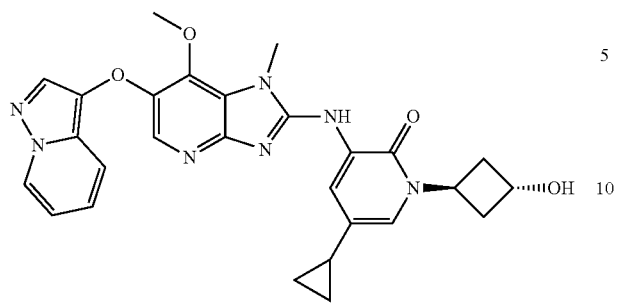
I-112
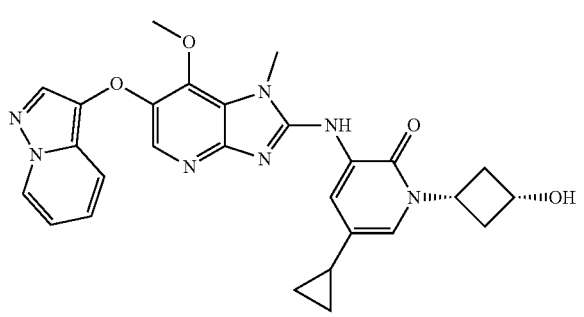
I-113
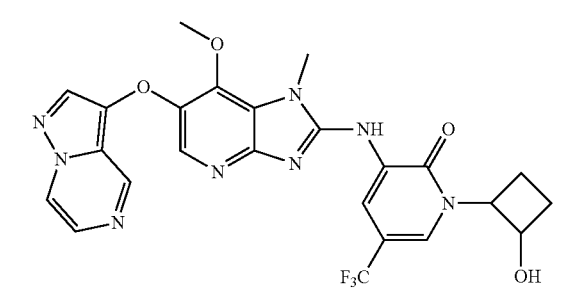
I-113-i
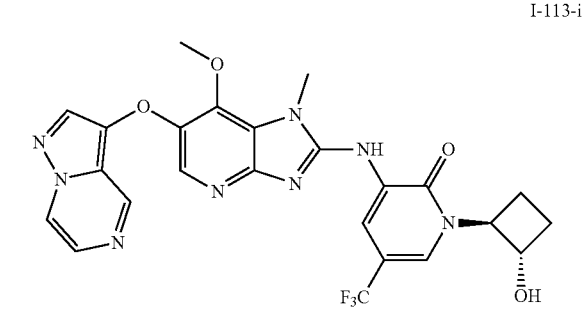
I-113-ii
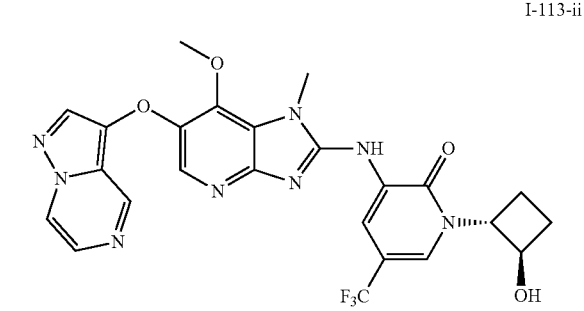
I-113-iii
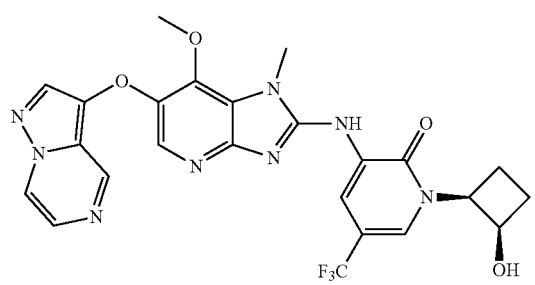
I-113-iv
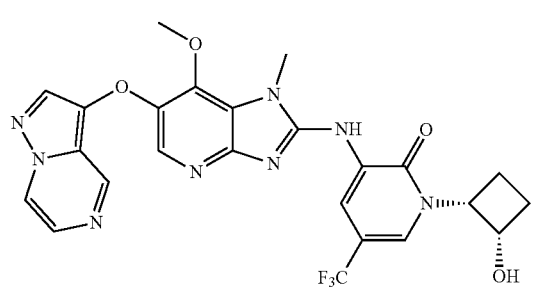
I-114-i
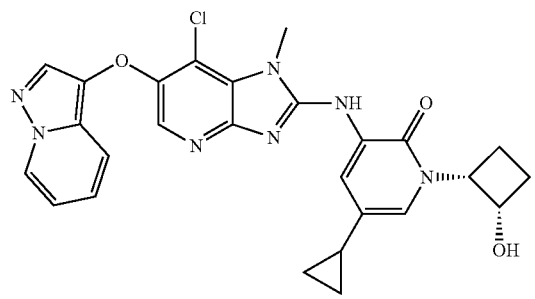
I-114-ii
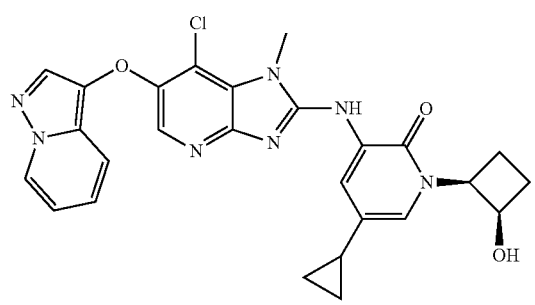
I-115

I-116
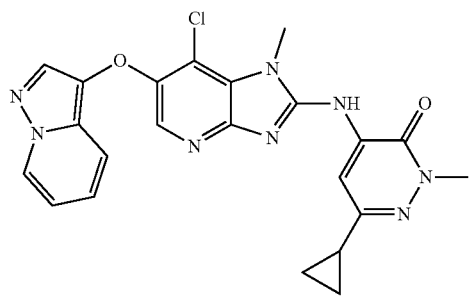
I-120
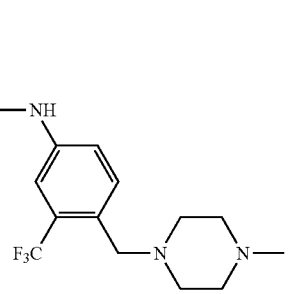
I-117
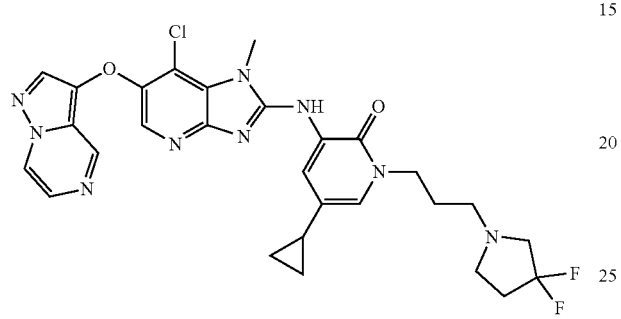
I-121
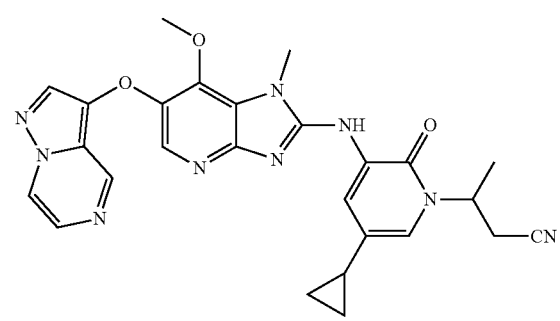
I-118
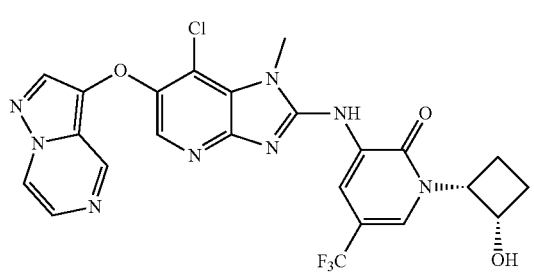
I-121-i
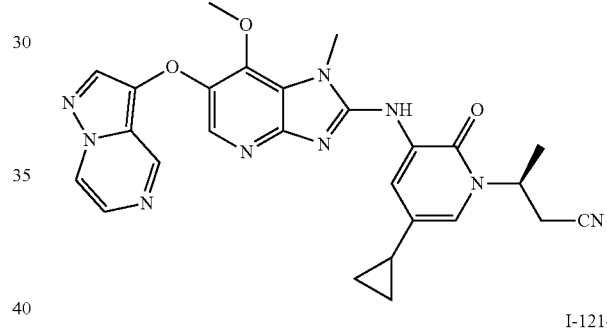
I-119-i
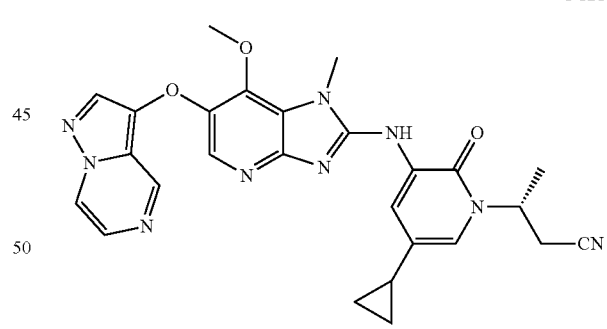
I-121-ii
I-119-ii
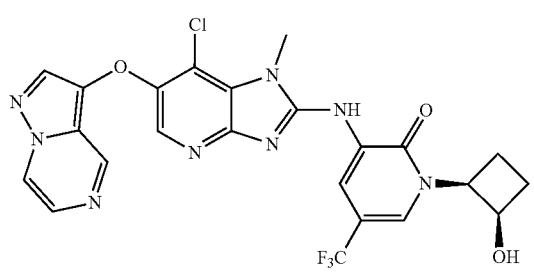
I-122
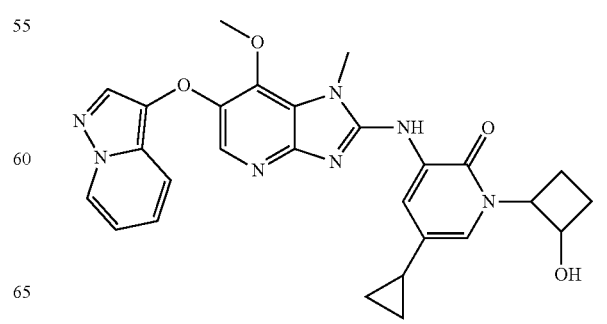

I-122-i
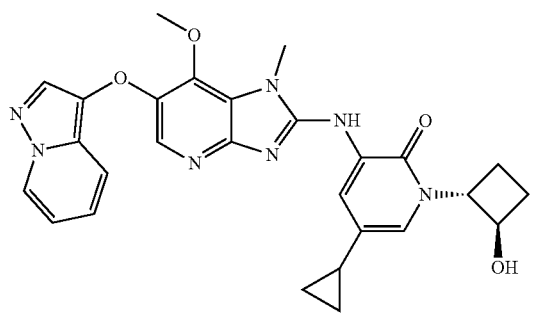
I-125
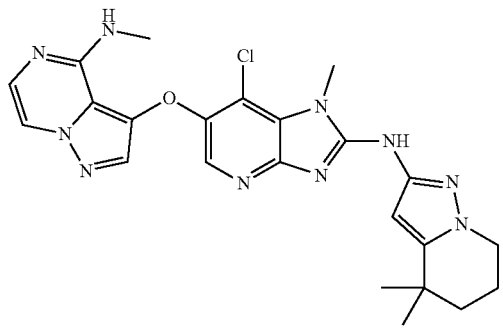
I-122-ii
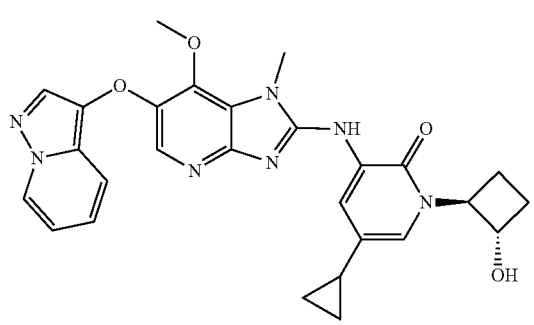
I-126
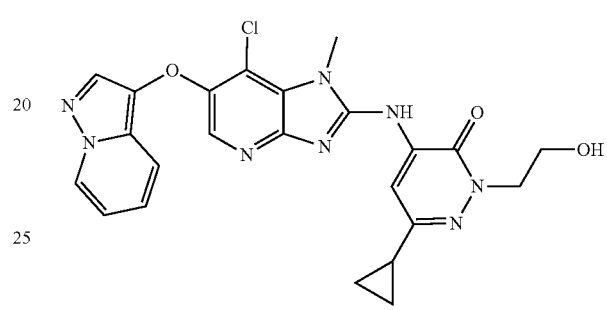
I-123
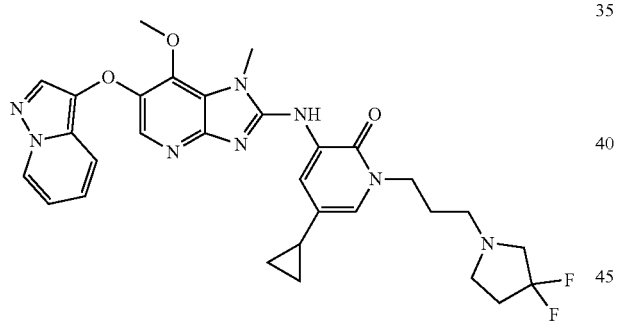
I-127
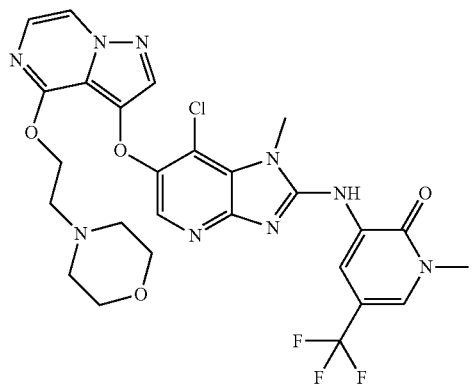
I-124
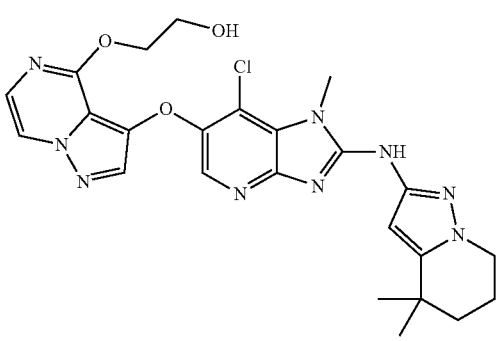
I-128
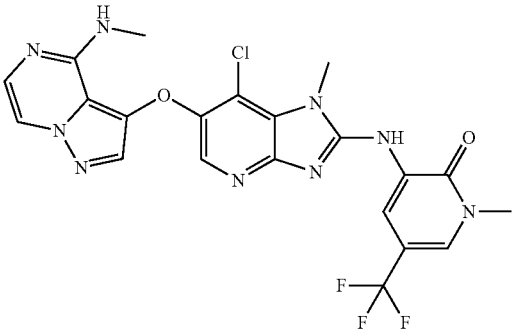

I-129
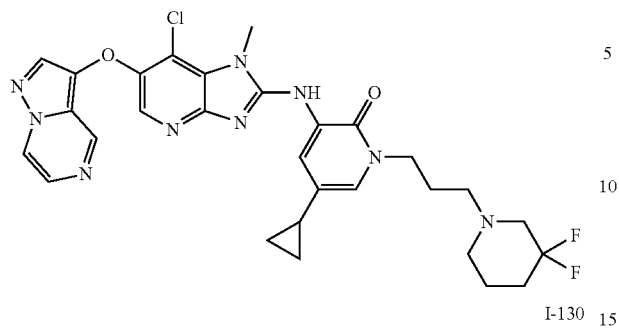
I-130
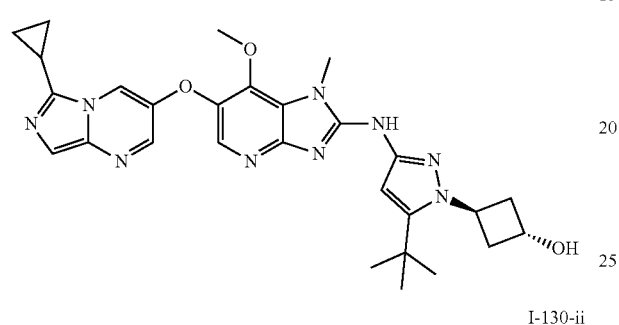
I-130-ii
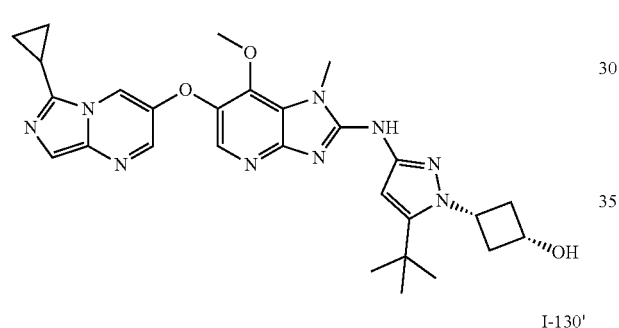
I-130'
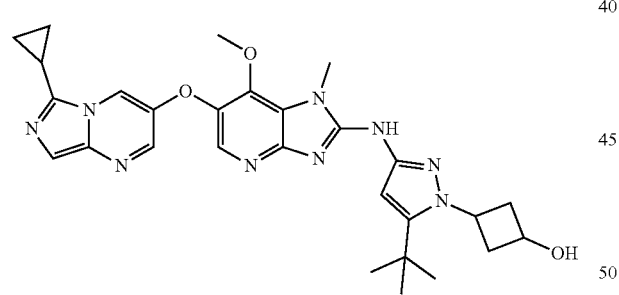
I-131-i
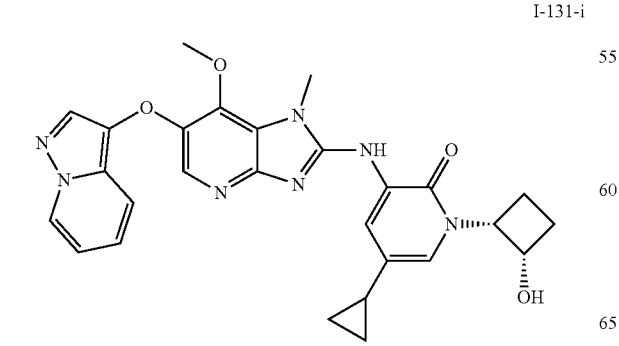
I-131-ii
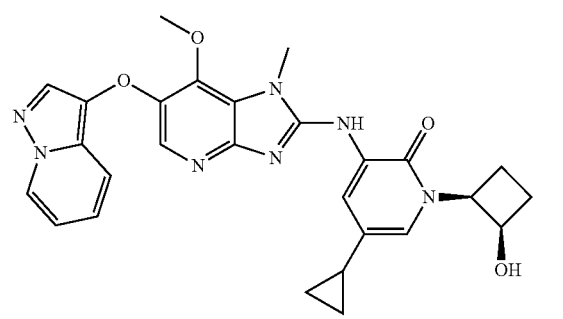
I-132
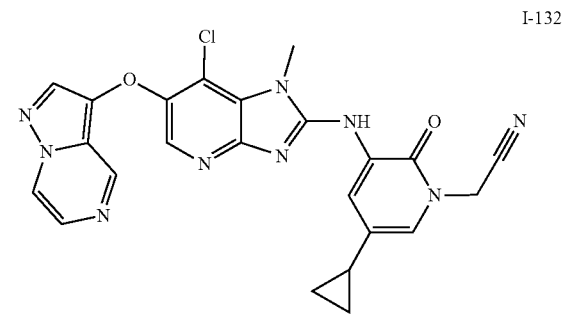
I-133-i
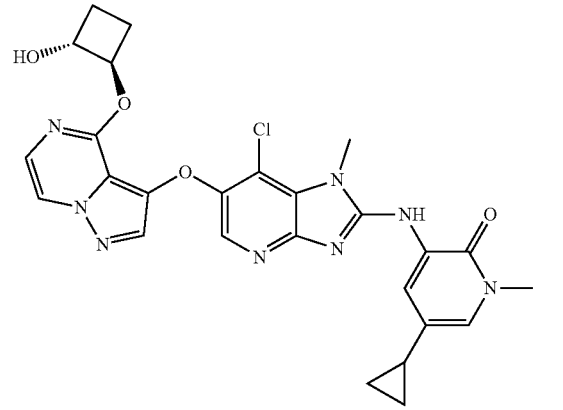
I-133-ii
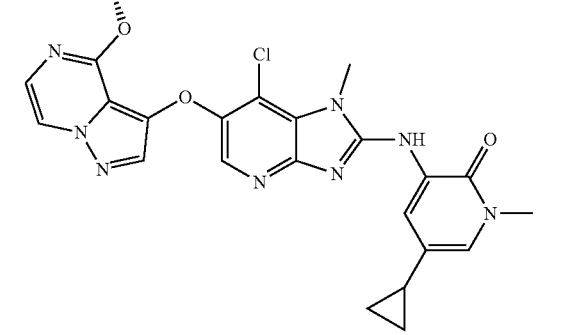

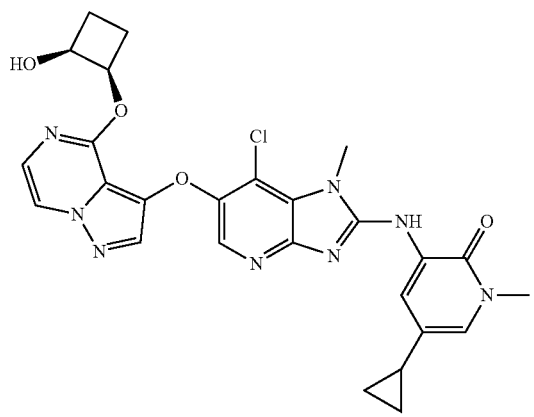
I-133-iii
I-133-iv
I-133
I-134
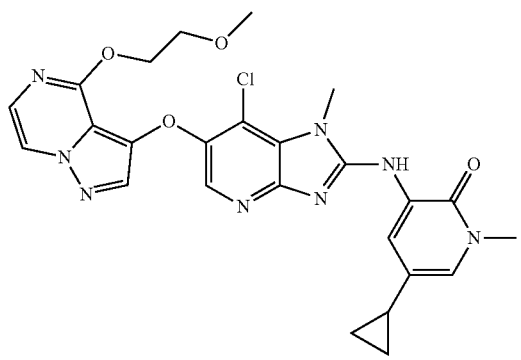
I-135
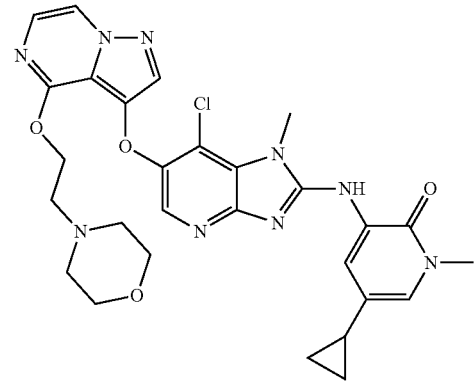
I-136
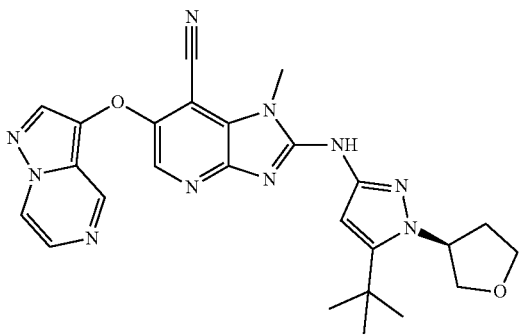
I-137
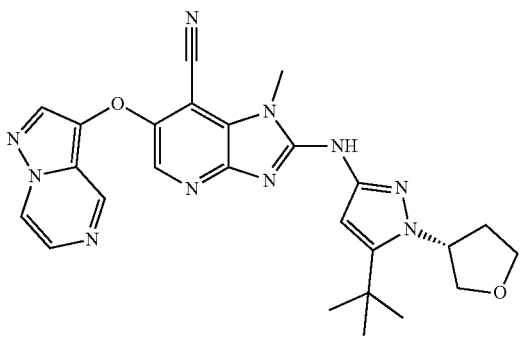
I-137-ii 1233
-continued
I-137'
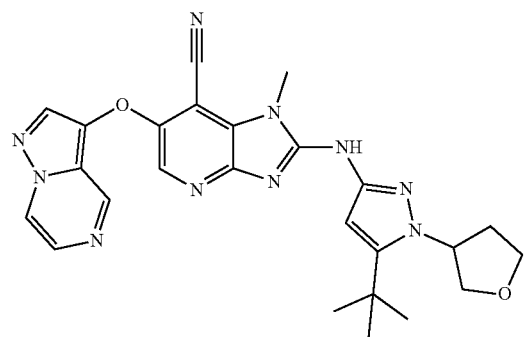
I-138
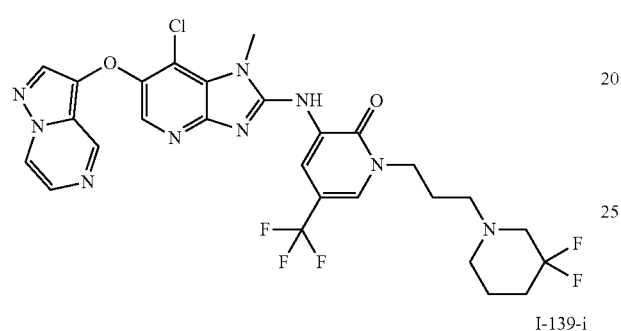
I-139-i
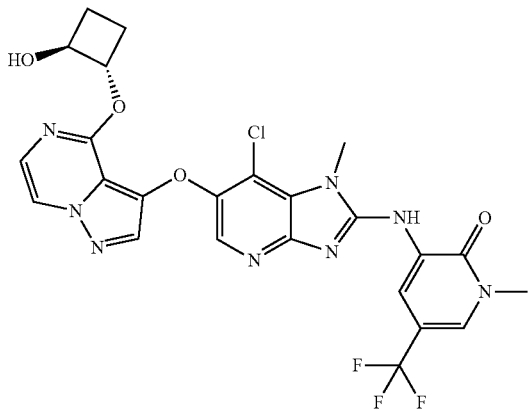
I-139-ii
1234
-continued
I-139-iii
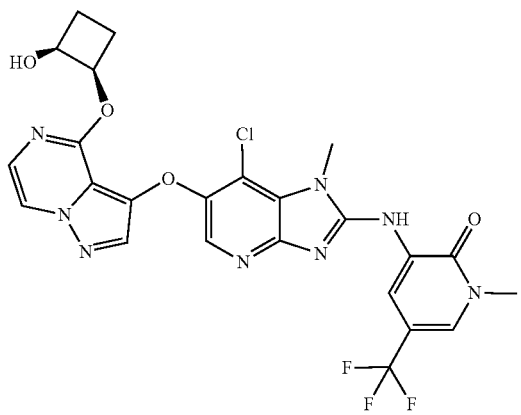
I-139-iv
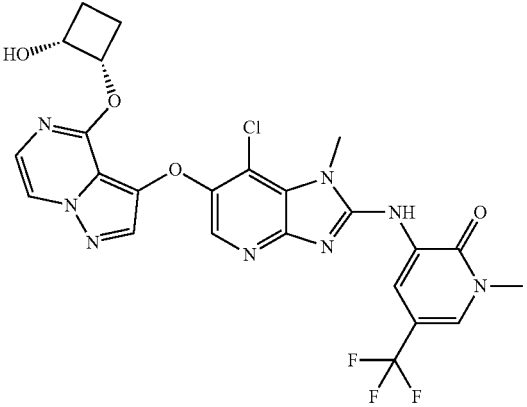
I-139
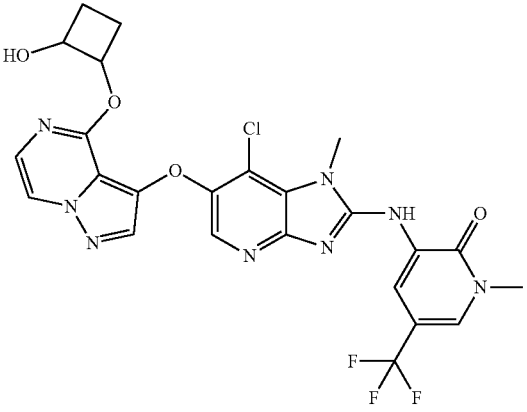

I-140
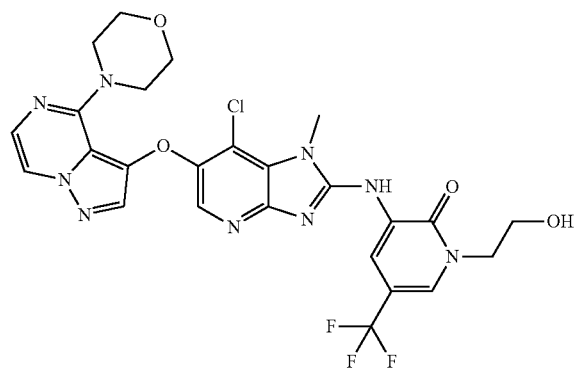
I-141
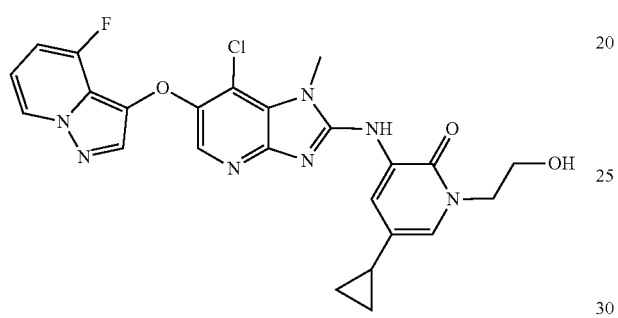
I-142
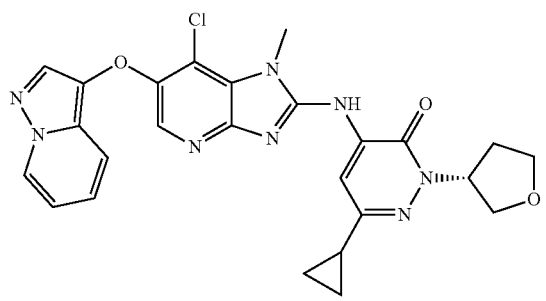
I-143
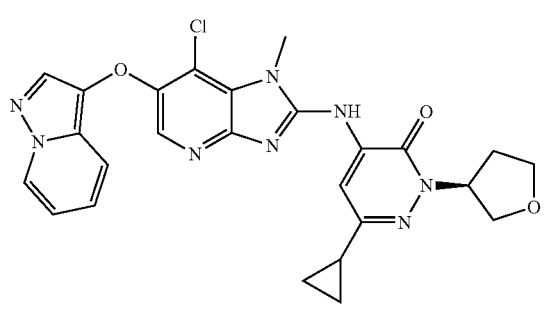
I-142'
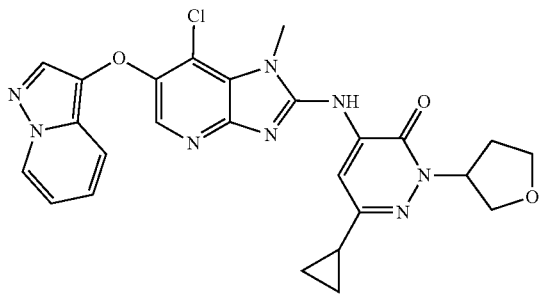
I-144
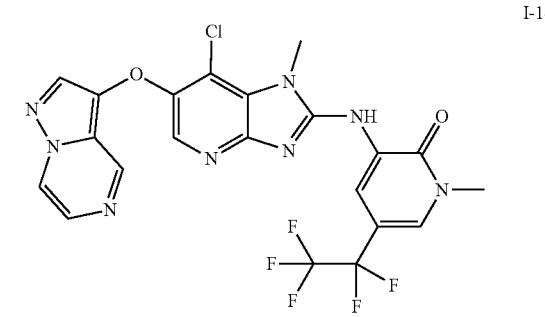
I-145
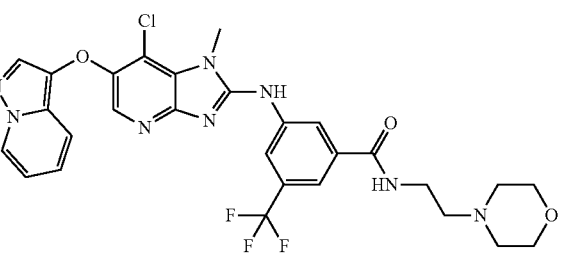
I-146
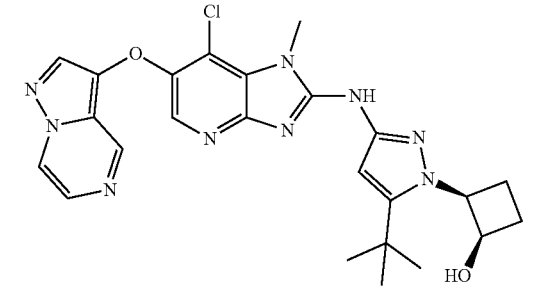
I-147-i I-147-ii
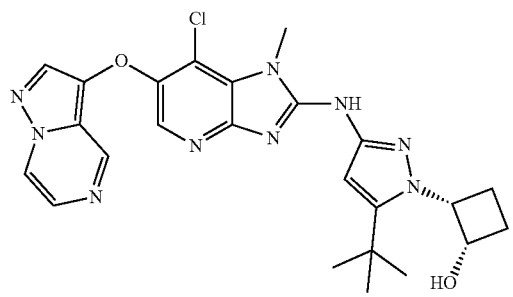
I-147-iii
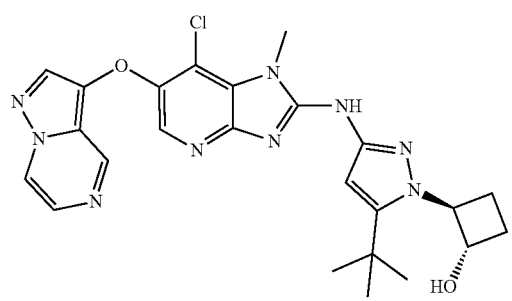
I-147-iv
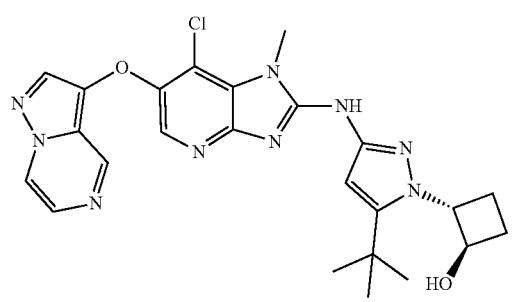
I-147
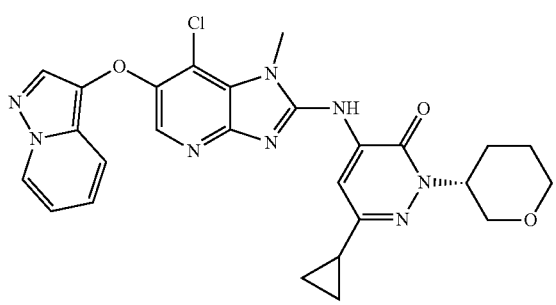
I-148-i
I-148-ii
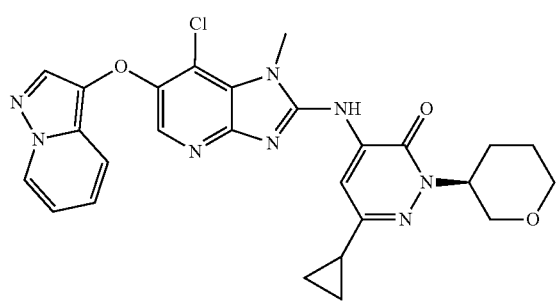
I-148
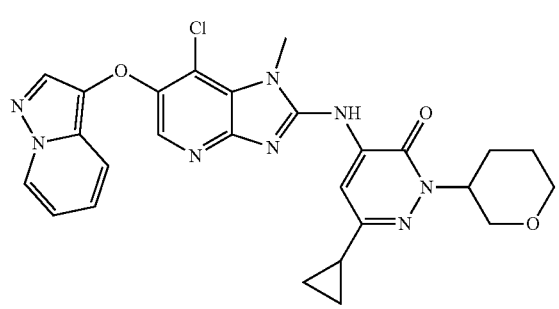
I-149
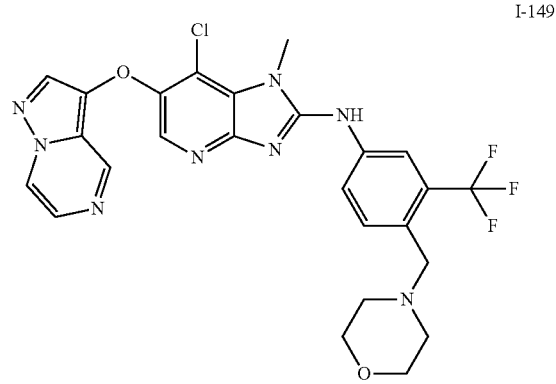
I-150-i
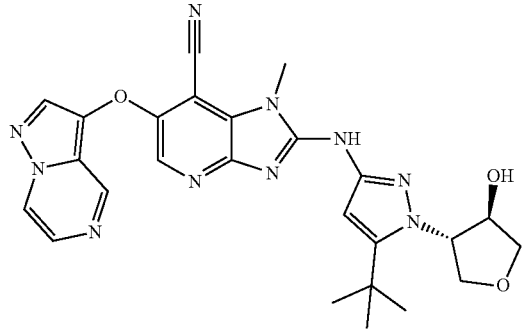

I-150-ii
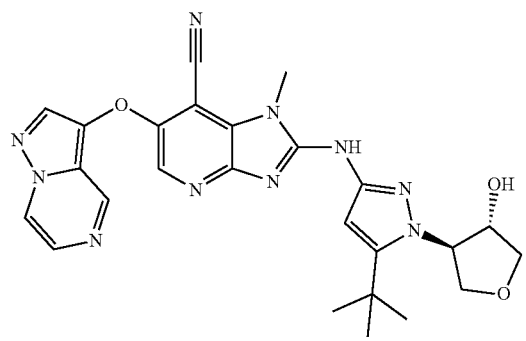
I-151
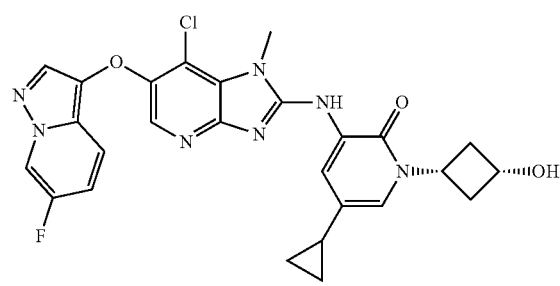
I-150-iii
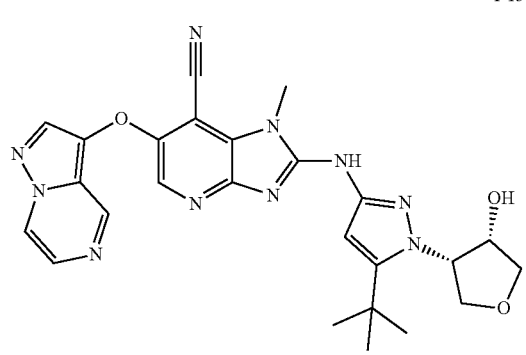
I-152
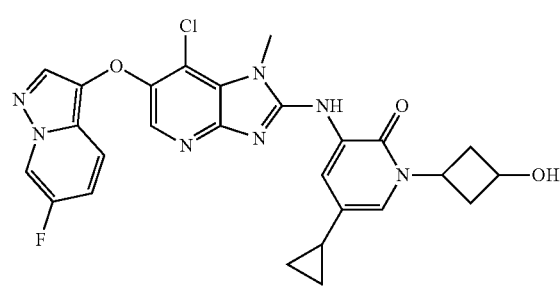
I-150-iv
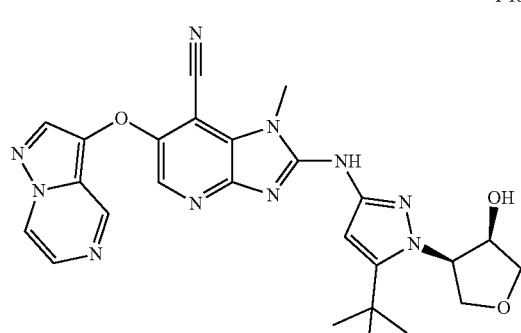
I-151'
I-153
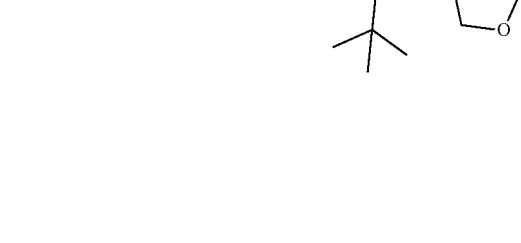
I-150
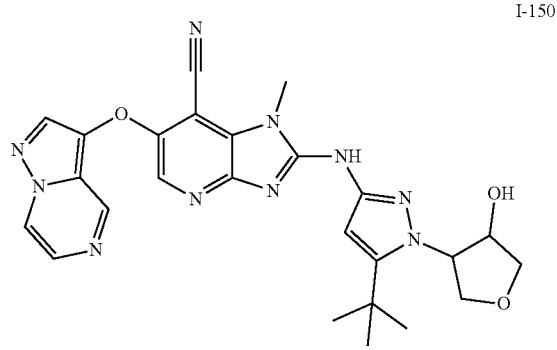
I-154
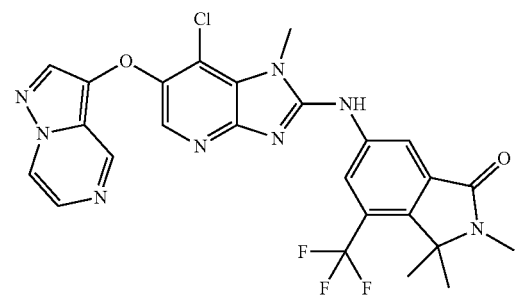

-continued
I-155
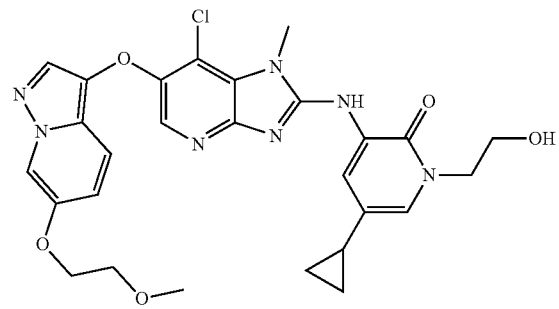
I-156
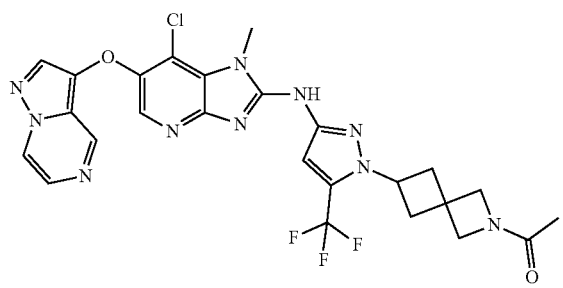
I-157
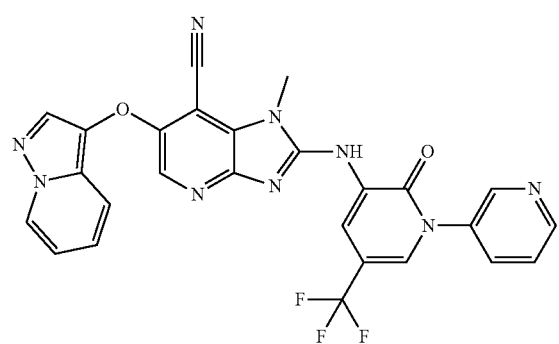
I-158
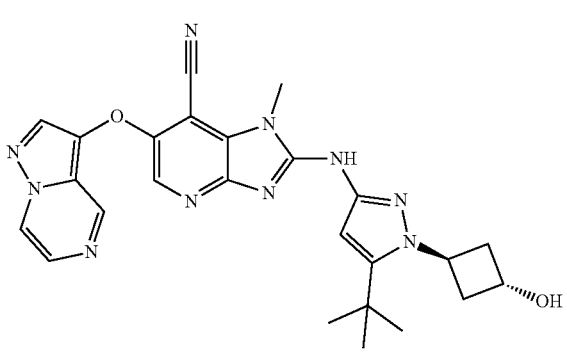
-continued
I-158-ii
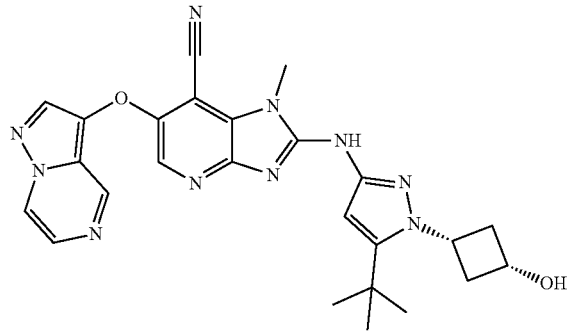
I-158'
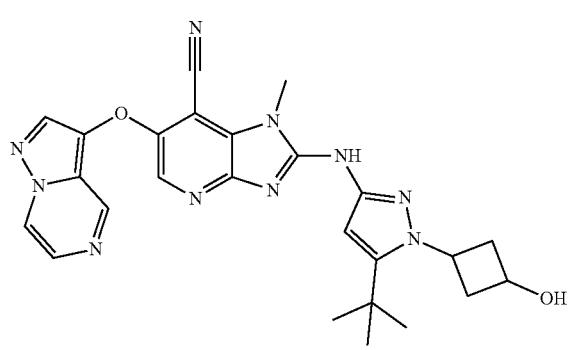
I-159
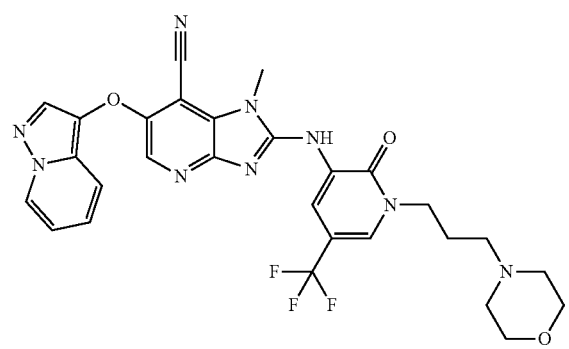
I-160
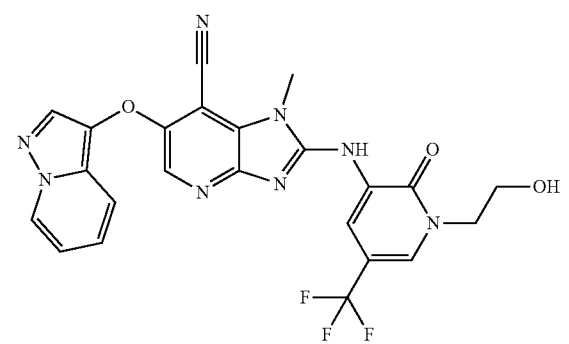

1243
-continued
I-161
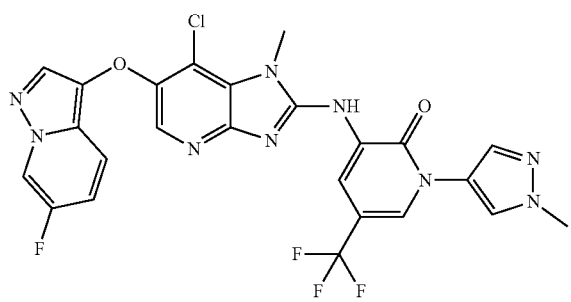
I-162
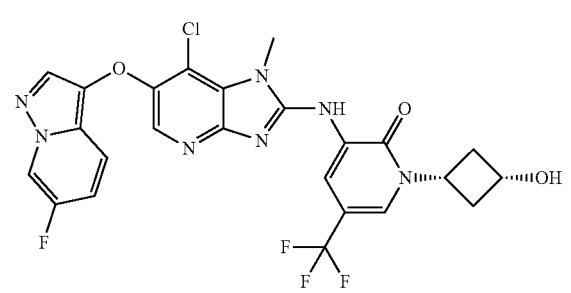
I-162-ii
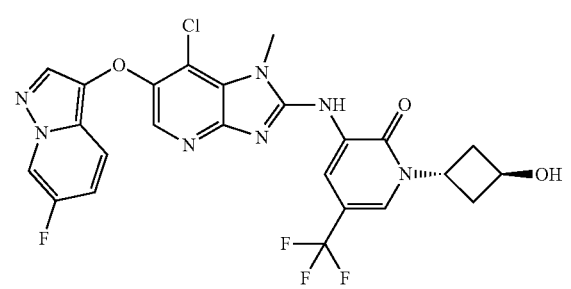
I-162'
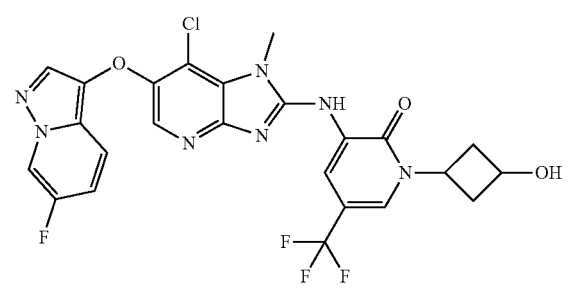
I-163
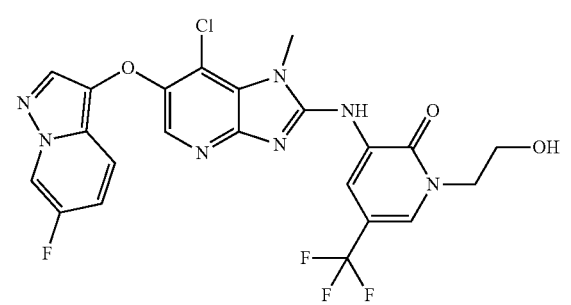
1244
-continued
I-164
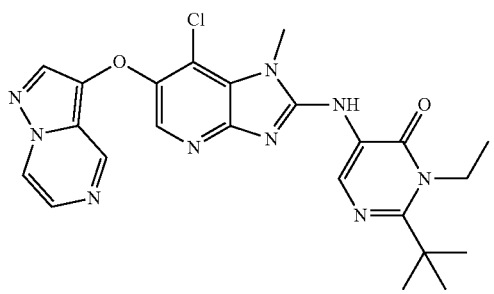
I-165
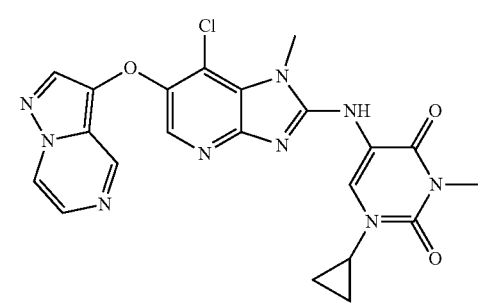
I-166
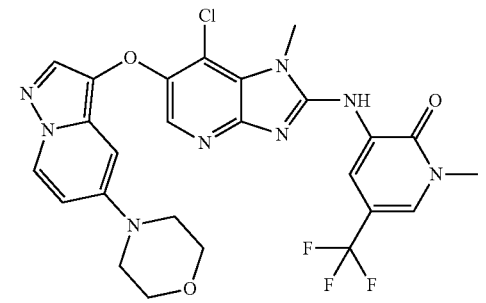
I-167
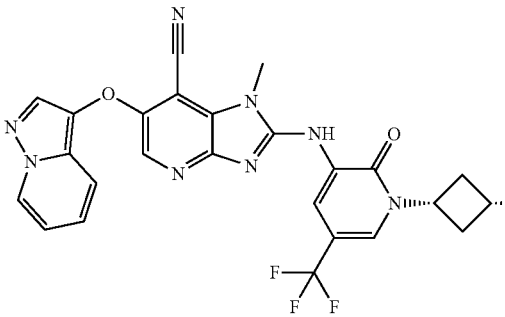
I-167'
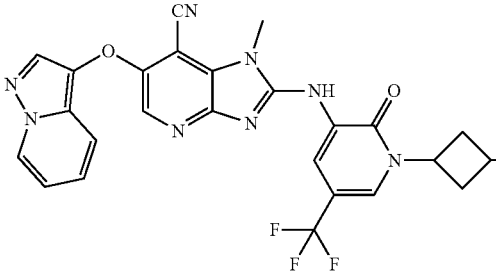

I-167-ii
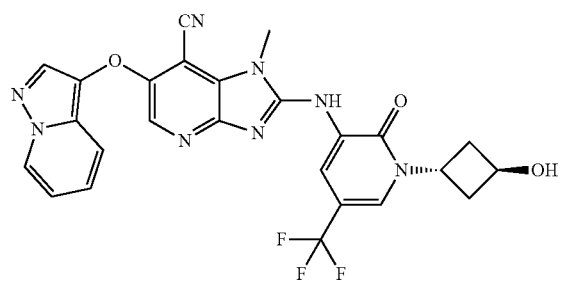
I-168
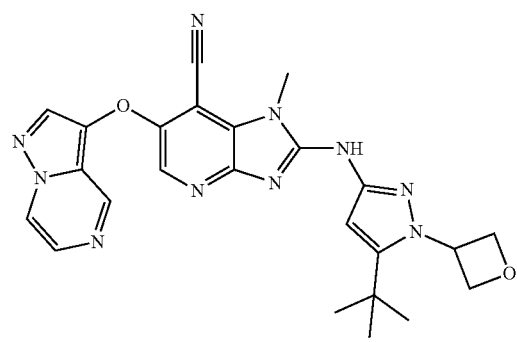
I-169
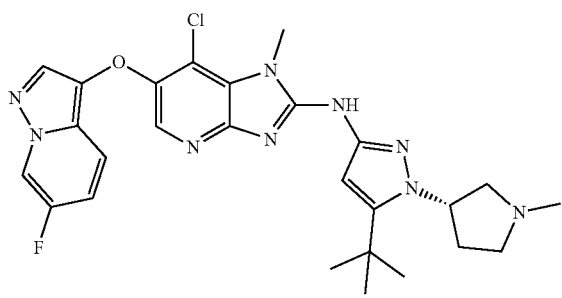
I-169'
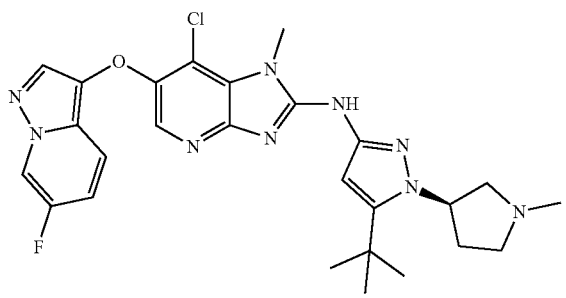
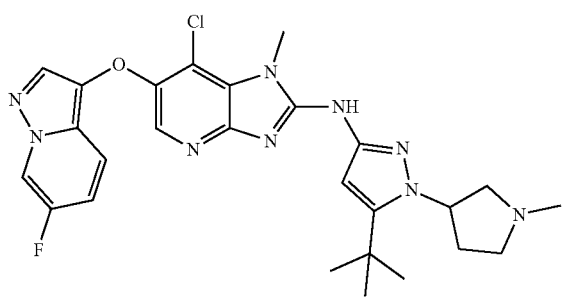
I-171
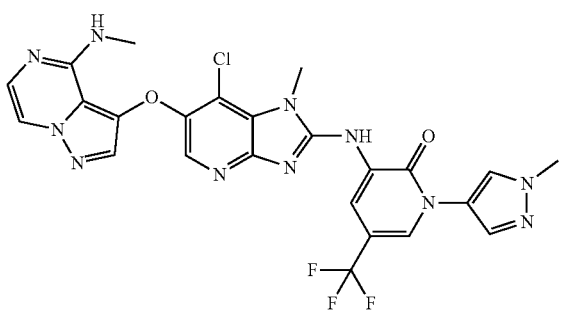
I-172
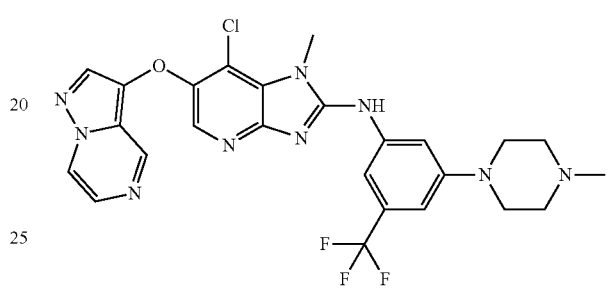
I-173
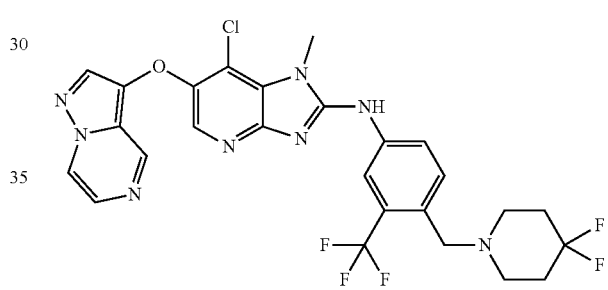
I-174
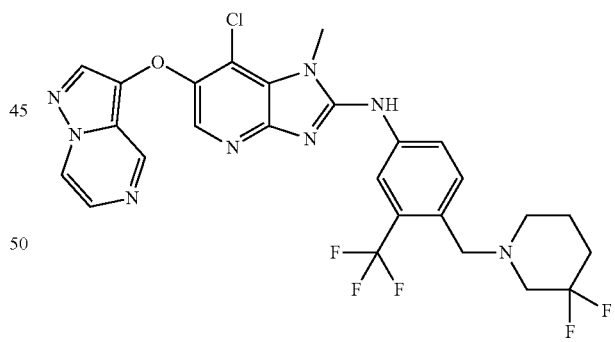
I-175
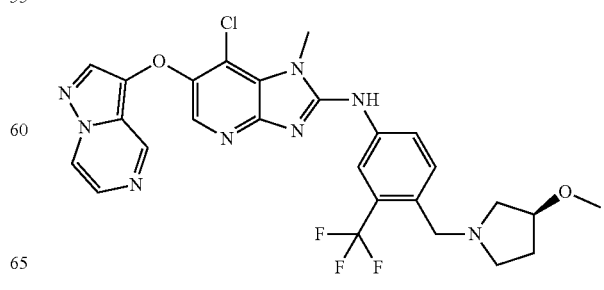

I-176
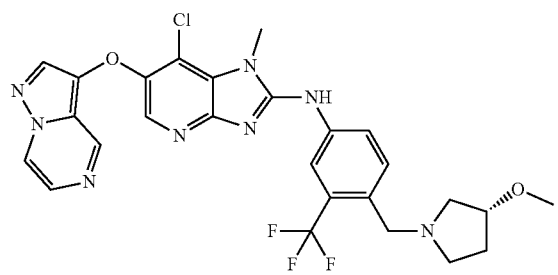
I-175'
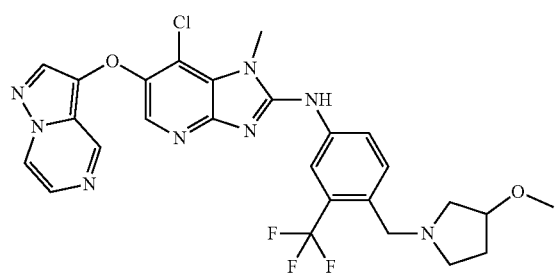
I-177
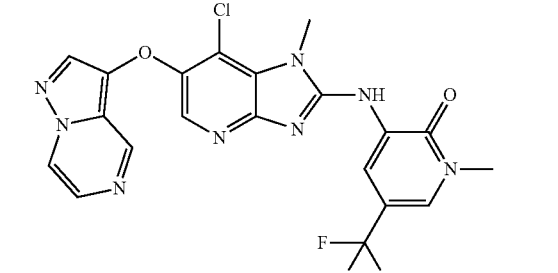
I-178
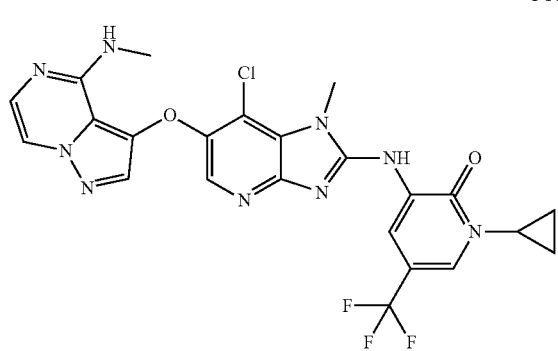
I-179
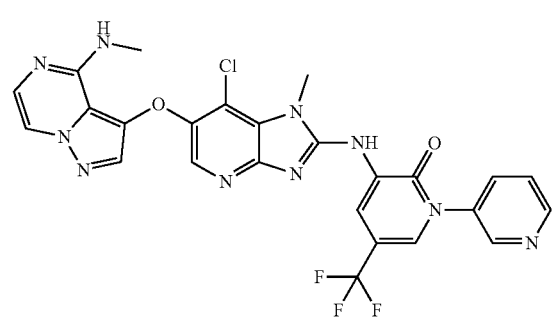
I-180
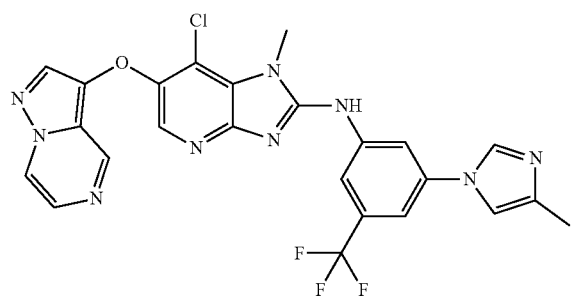
I-181
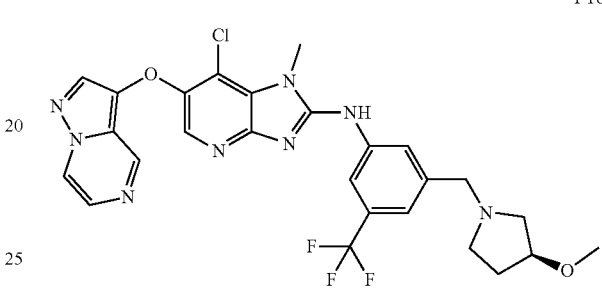
I-182
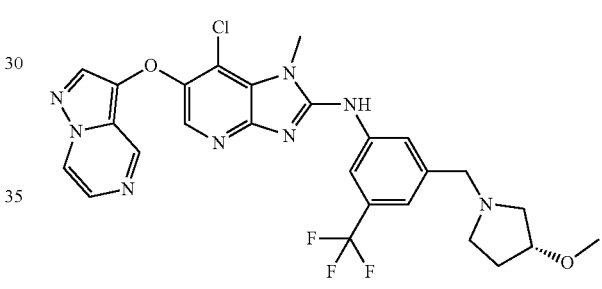
I-181'
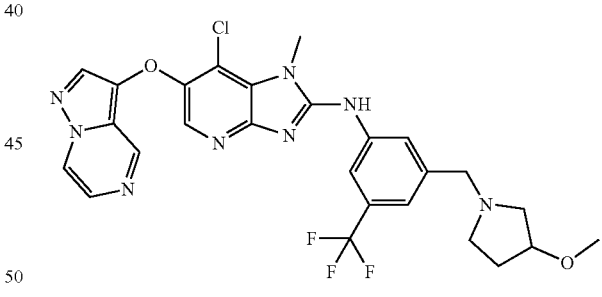
I-183
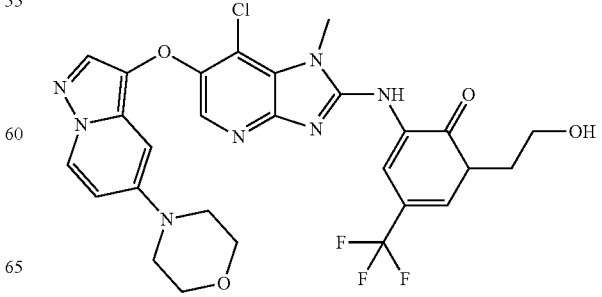

I-184
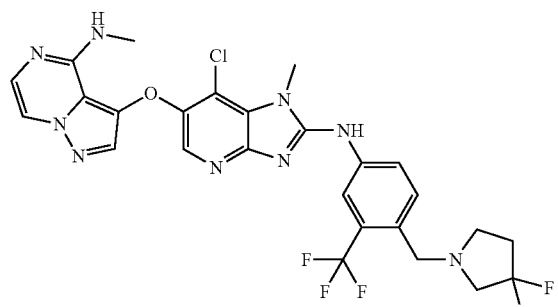
I-185
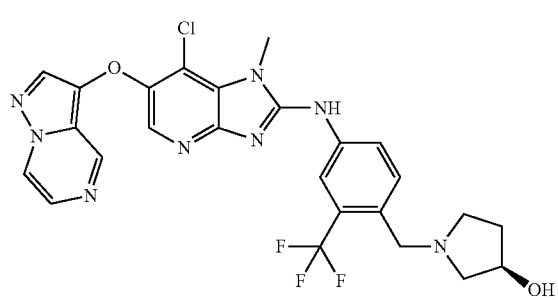
I-185'
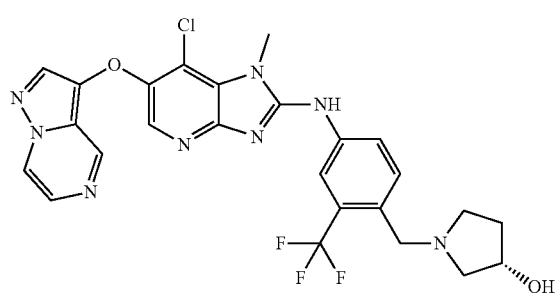
I-186
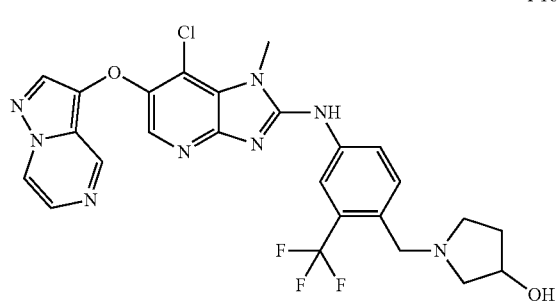
I-187
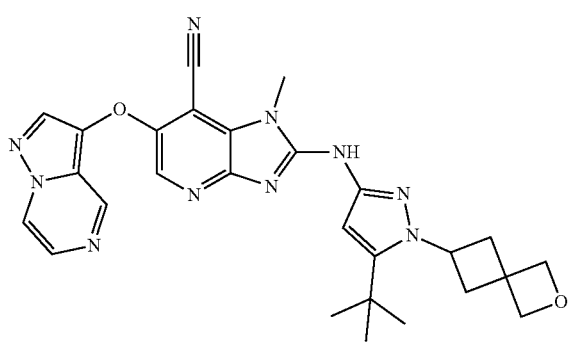
I-188
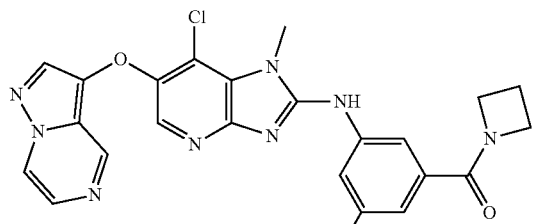
I-189
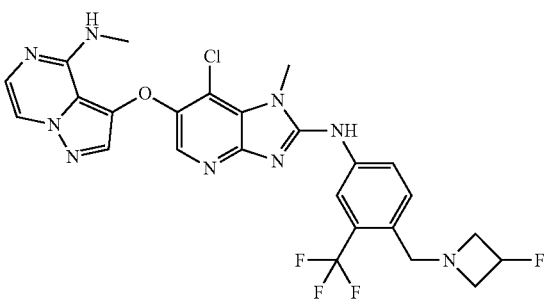
I-190
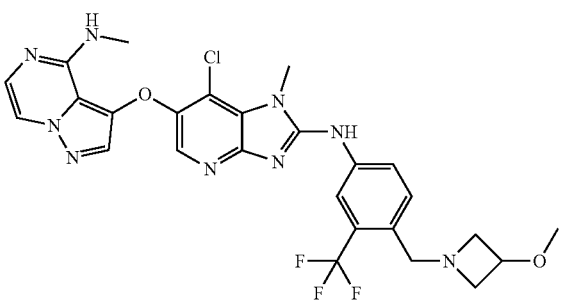
I-191
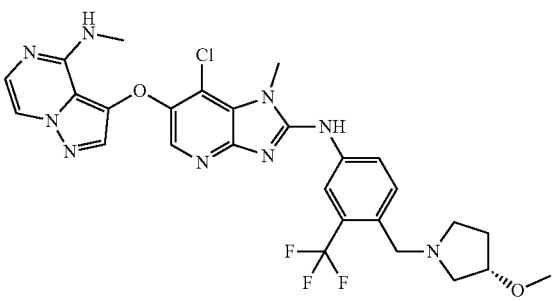
I-192

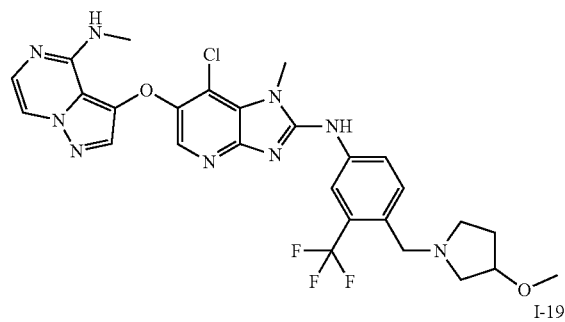
I-192'
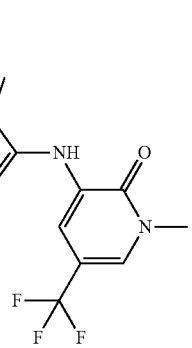
I-193
I-194
I-195
I-196
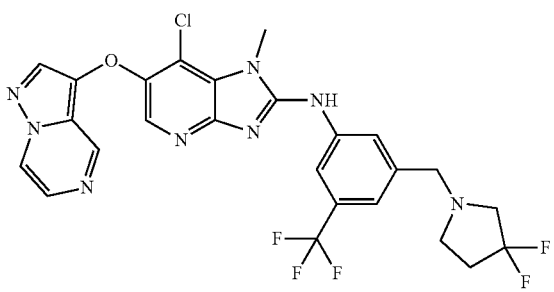
I-197
I-198
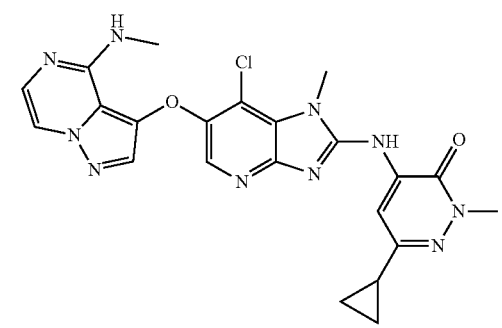
I-199
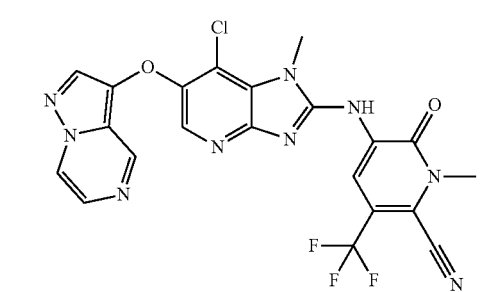
I-200
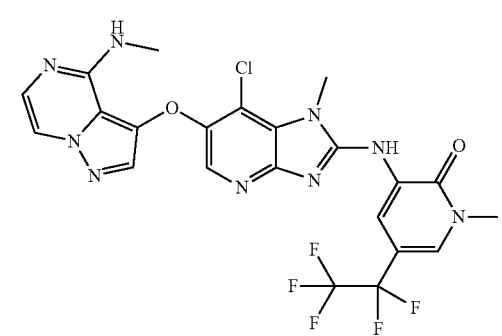
I-201

1253
-continued
I-202
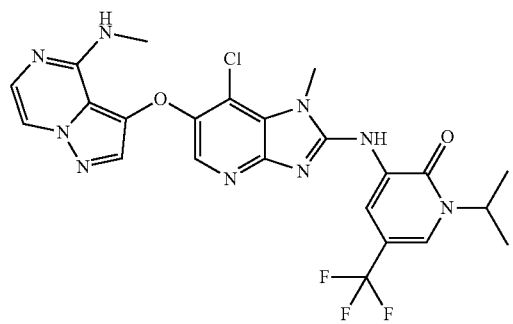
I-203
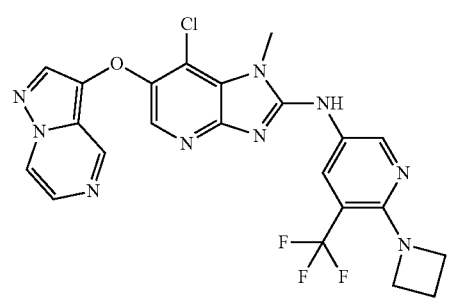
I-204
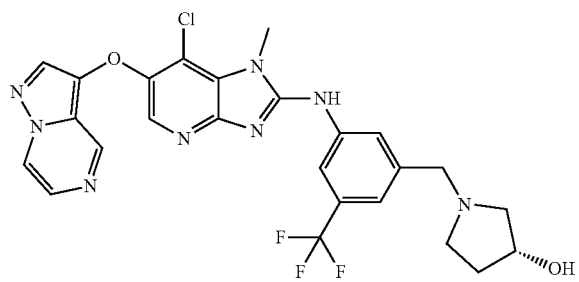
I-204'
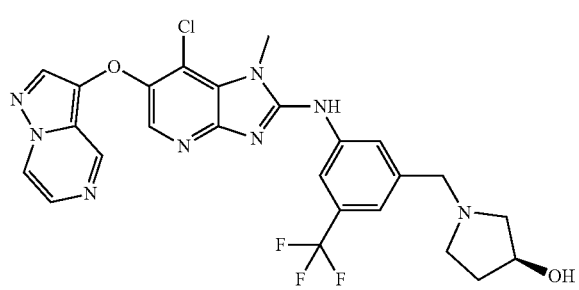
I-204''
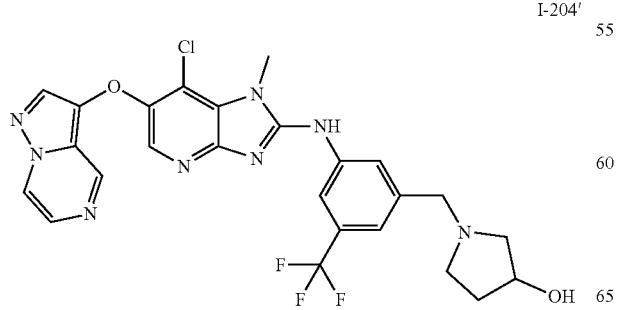
1254
-continued
I-206
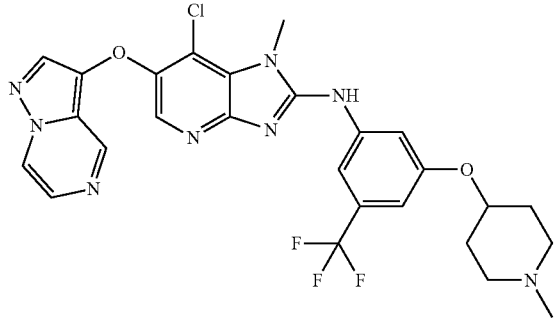
I-207
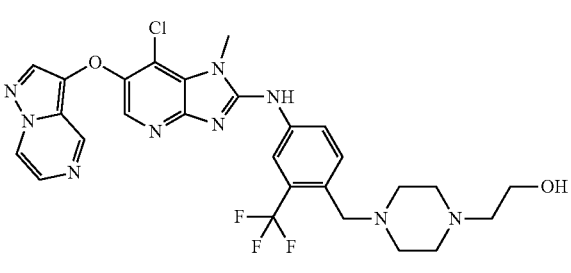
I-208
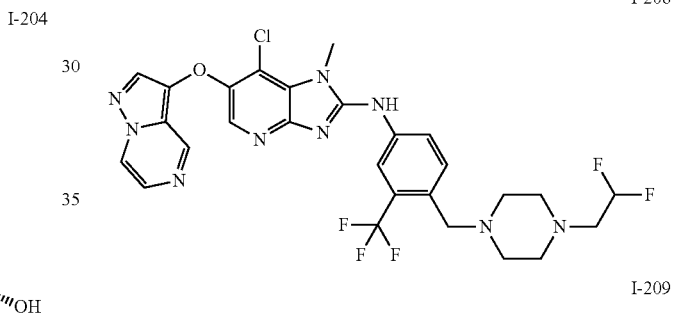
I-209
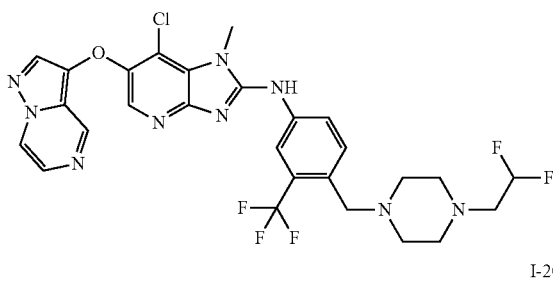
I-210
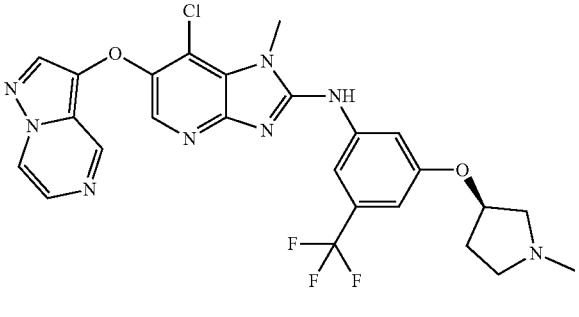

I-209'
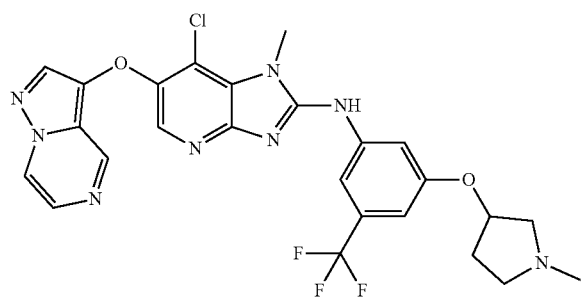
I-211
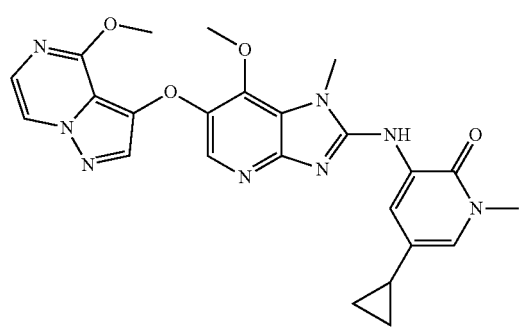
I-212
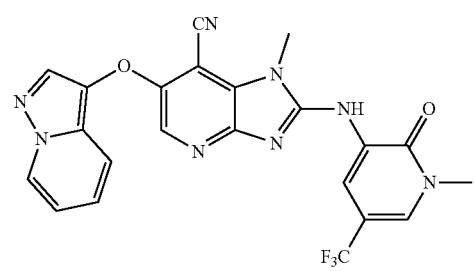
I-213
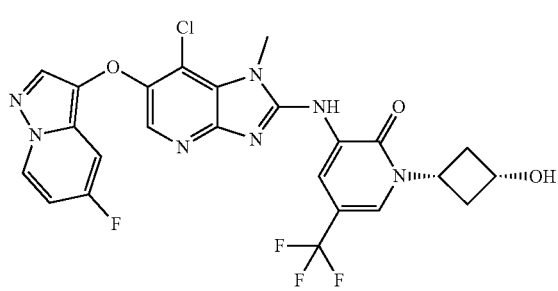
I-213-ii
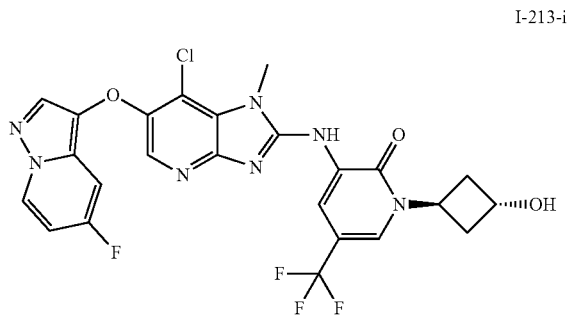
I-213'
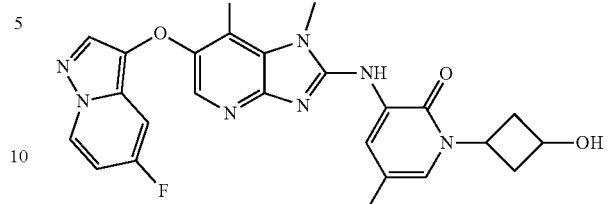
I-214
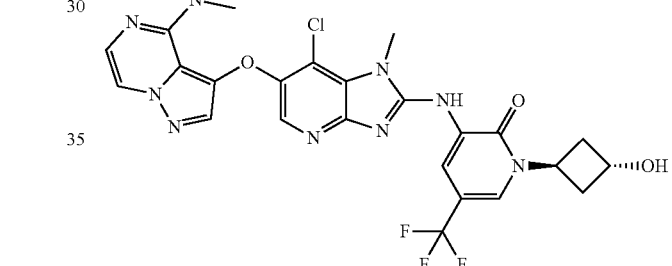
I-214-ii
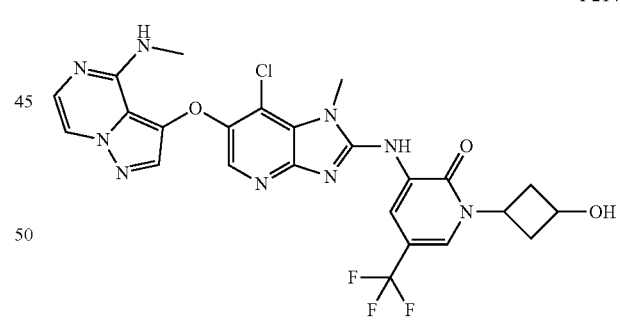
I-214'
I-215
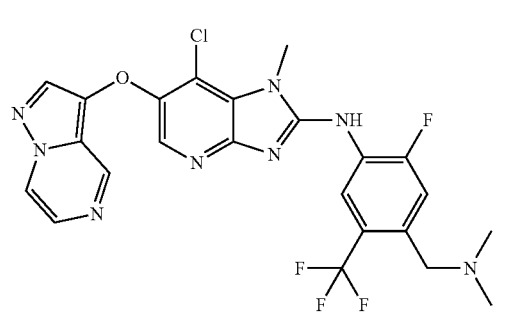

1257
-continued
I-216
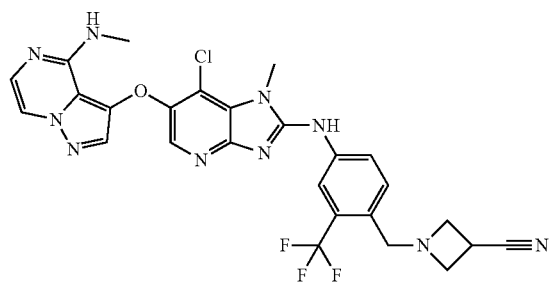
I-217
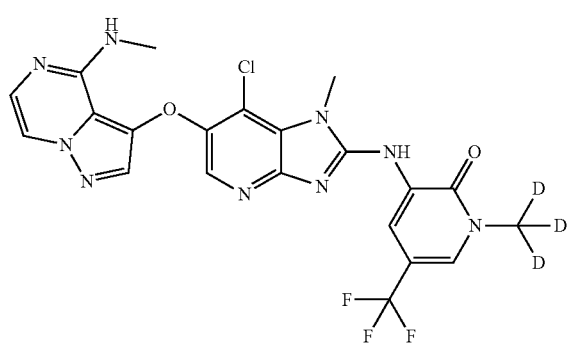
I-218
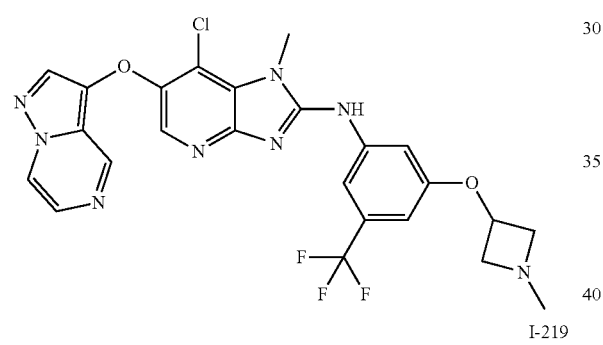
I-219
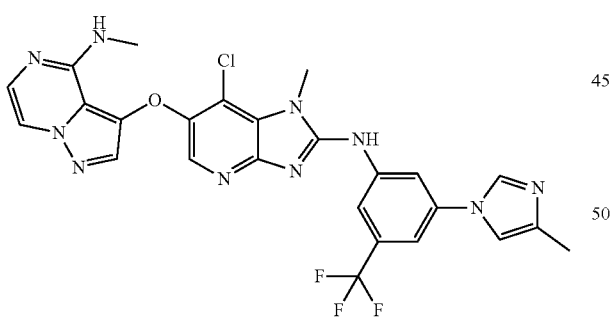
I-220
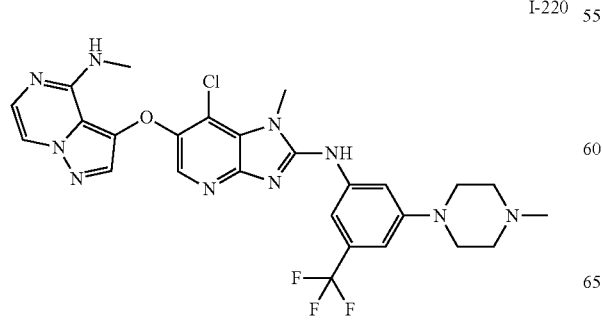
1258
-continued
I-221
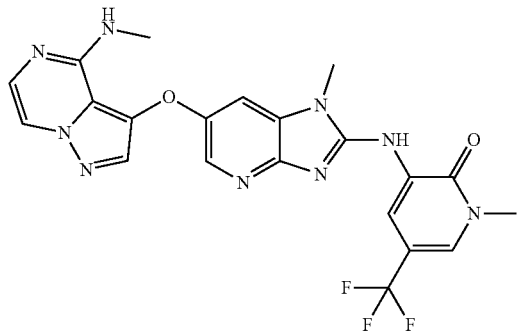
I-222
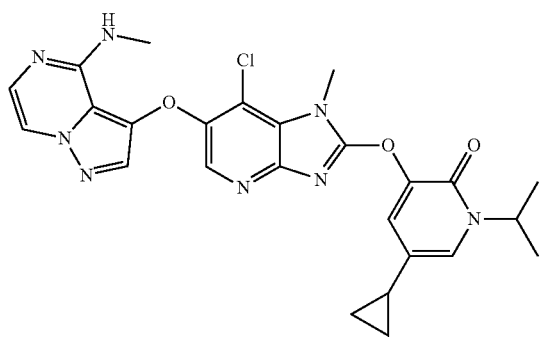
I-223
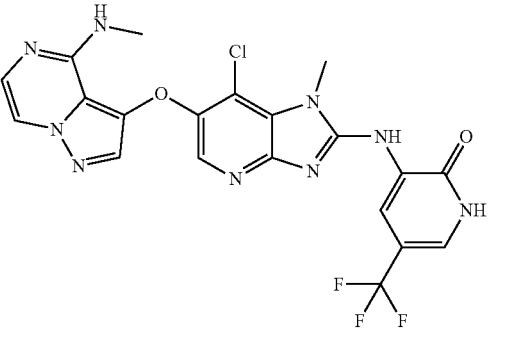
I-224
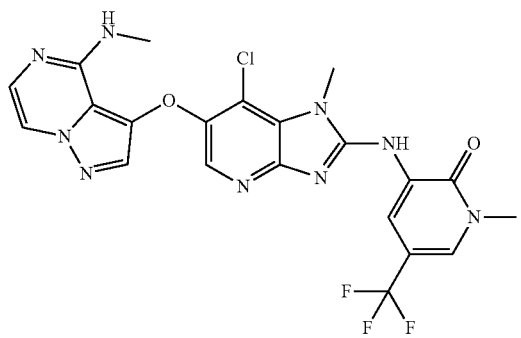

I-225
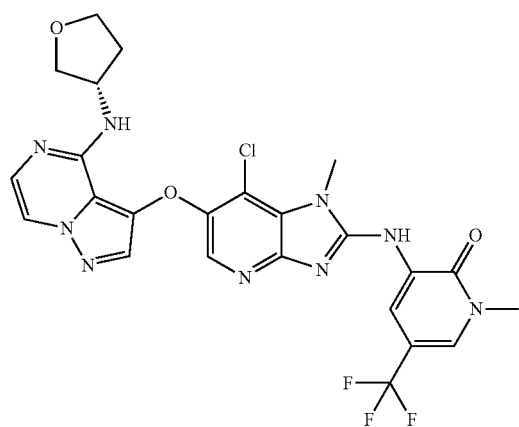
I-226
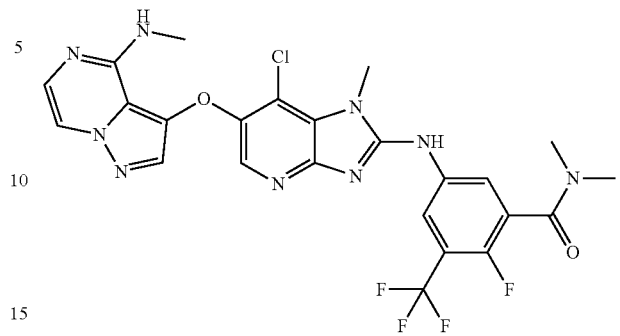
I-225-ii
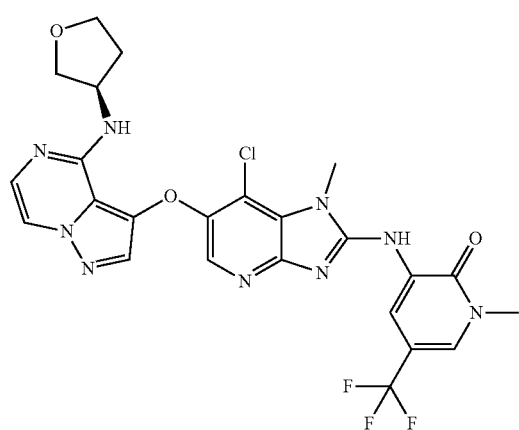
I-227
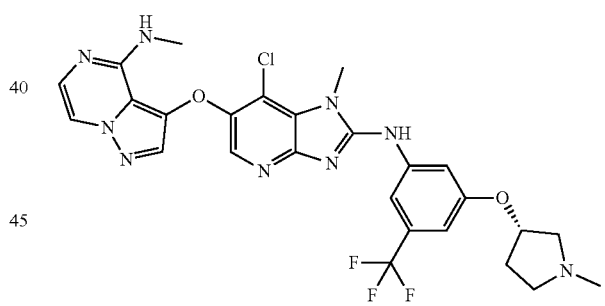
I-228
I-225'
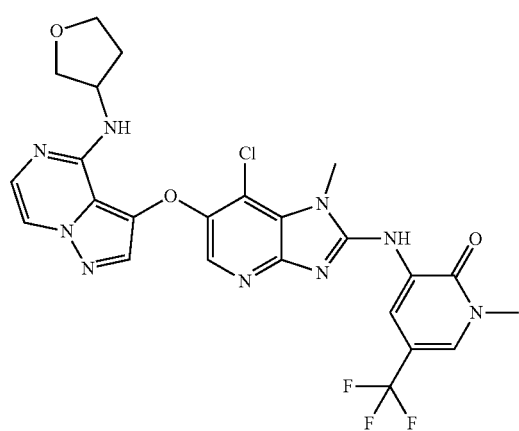
I-229
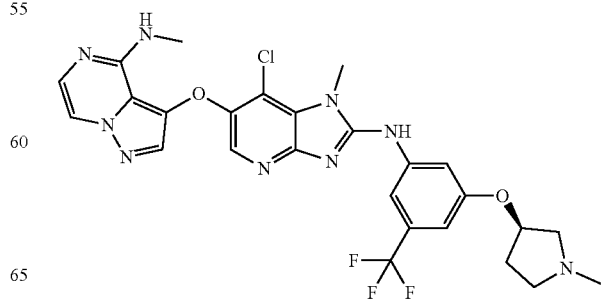

-continued
I-228'
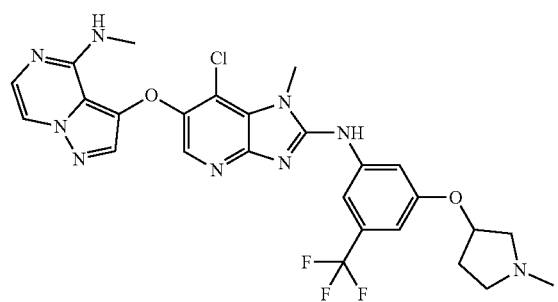
I-230
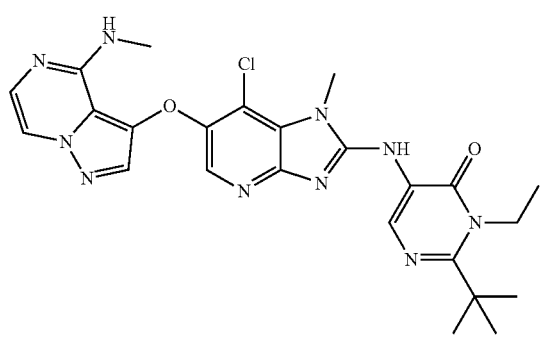
I-231
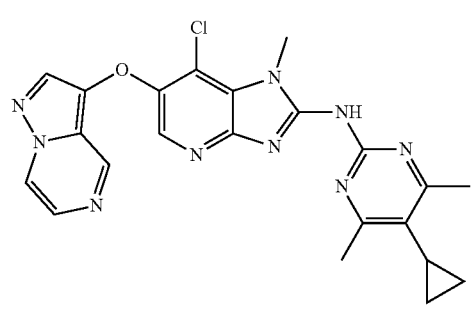
I-232
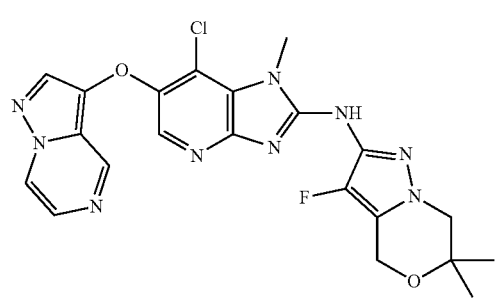
I-233
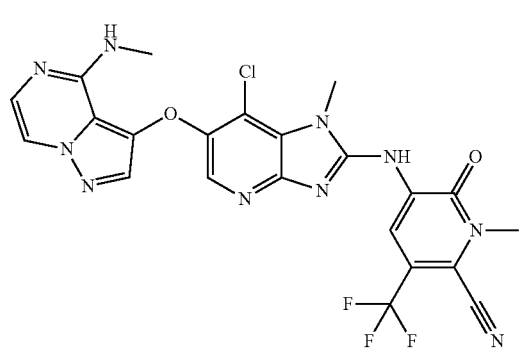
-continued
I-234
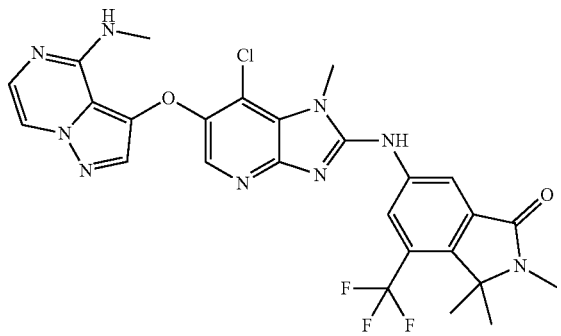
I-235
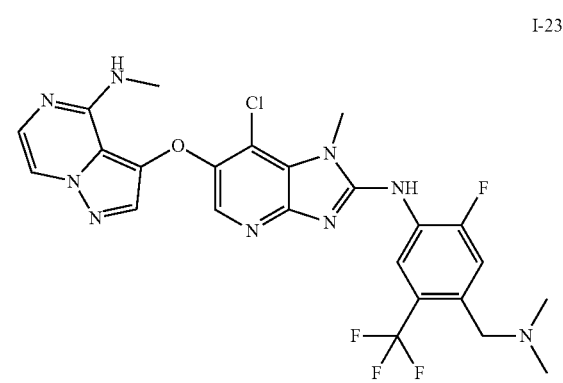
I-236
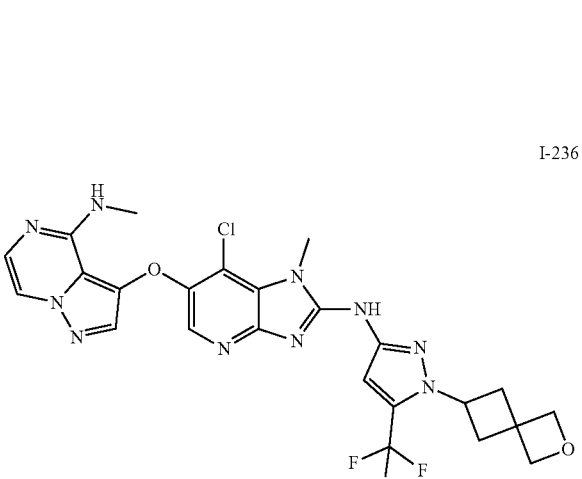
I-237
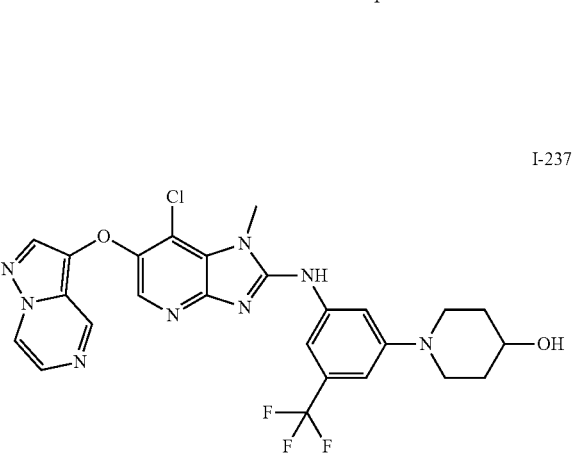

1263
-continued
I-238
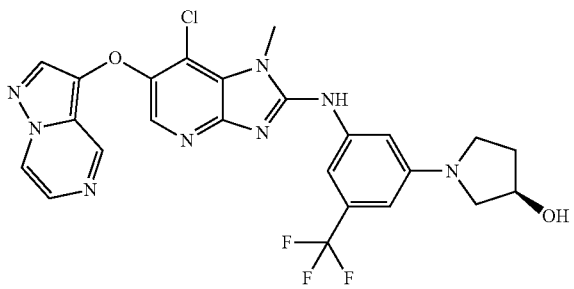
I-239
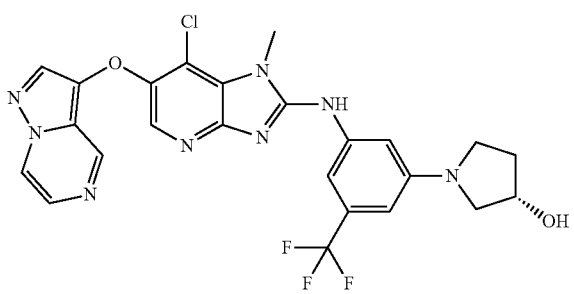
I-238'
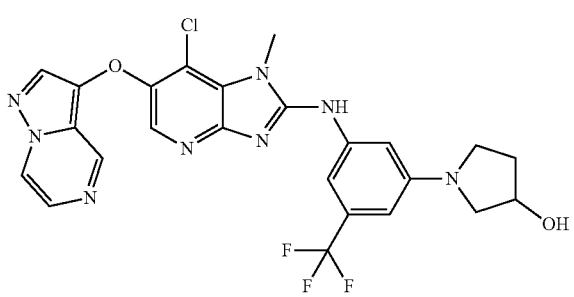
I-240
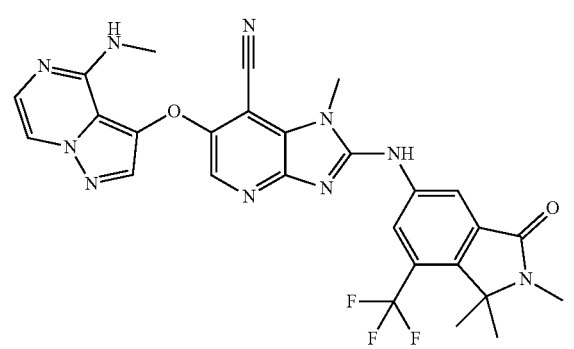
I-241
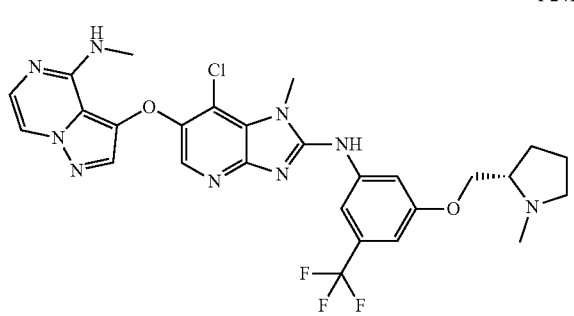
1264
-continued
I-242
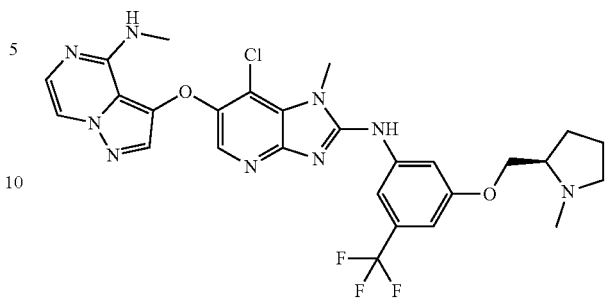
I-241'
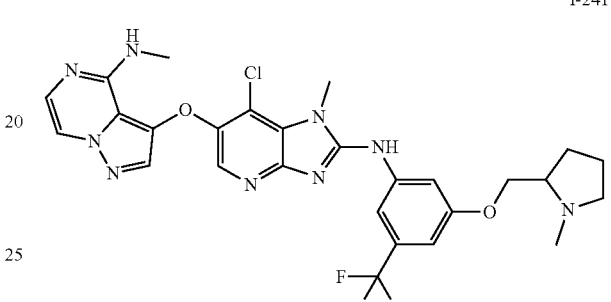
I-243
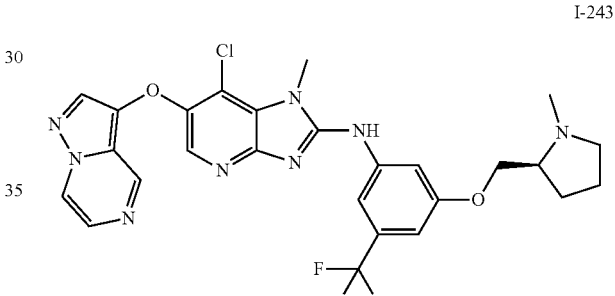
I-244
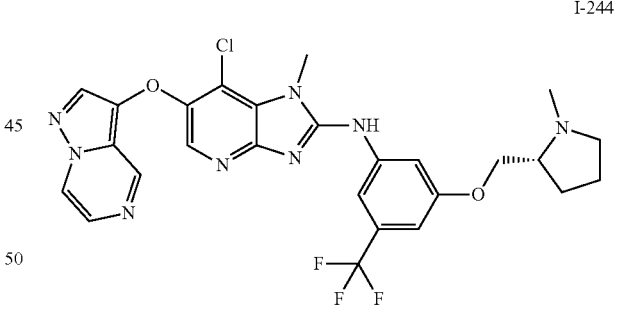
I-243'
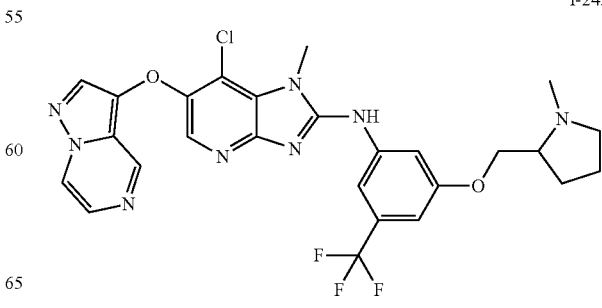

I-245-i
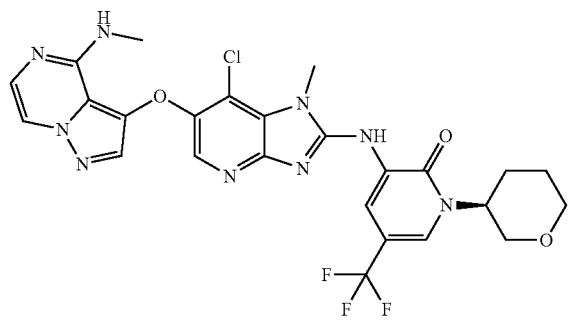
I-245-ii
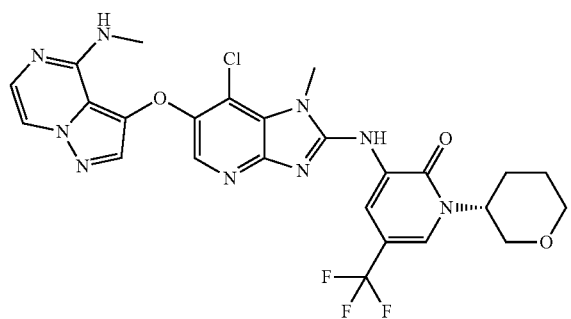
I-245
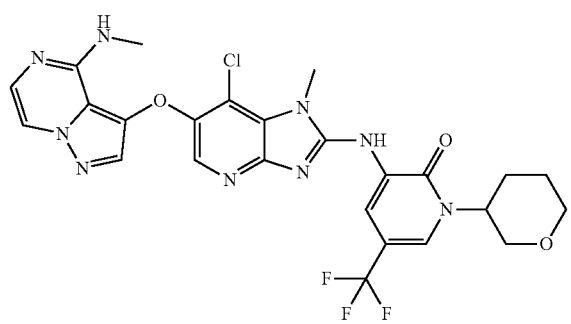
I-246
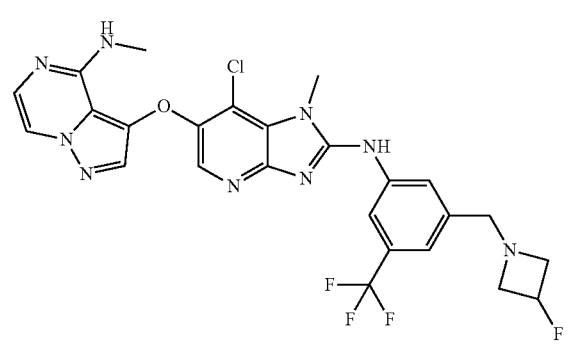
I-247
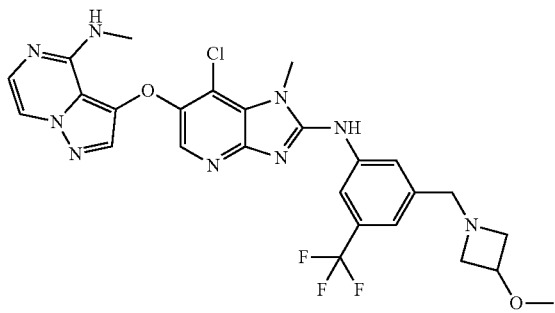
I-248
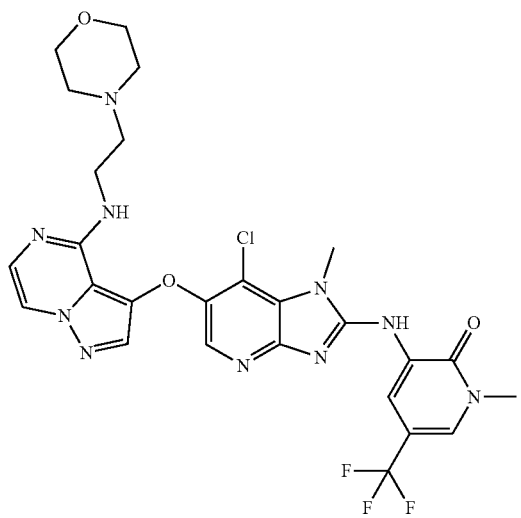
I-249
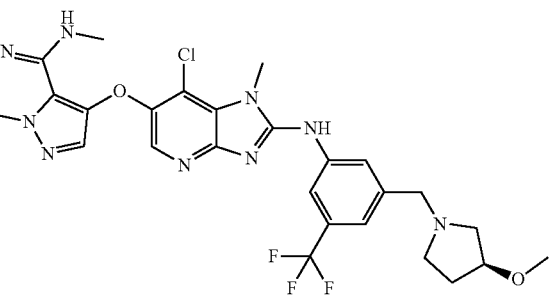
I-250
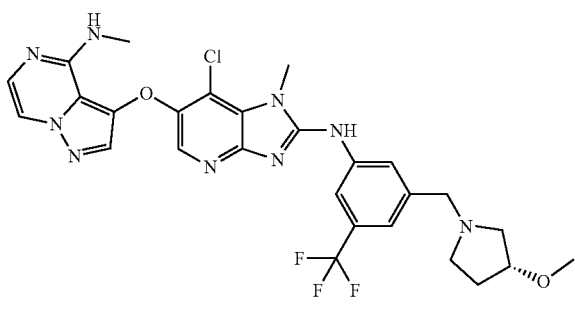

1267 -continued
I-249'
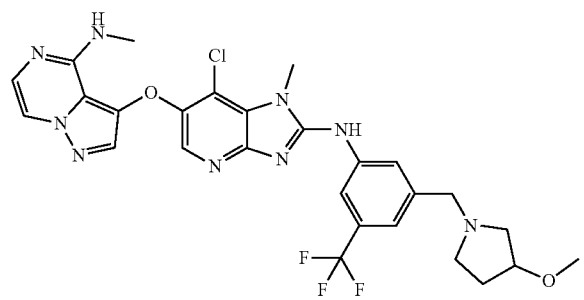
I-251
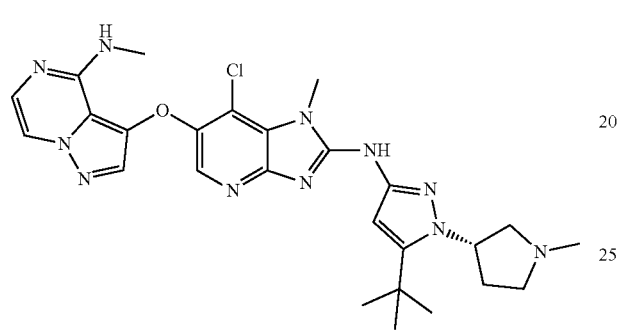
I-252
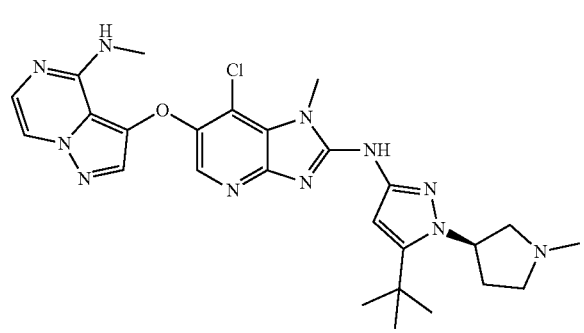
I-251'
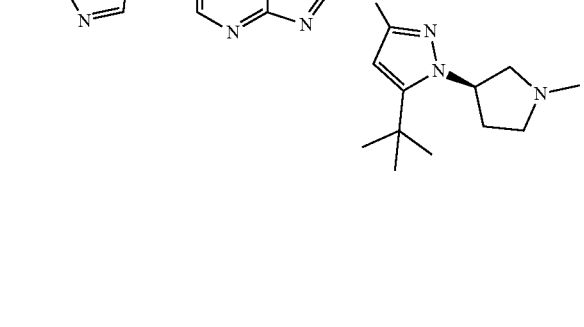
1268 -continued
I-253
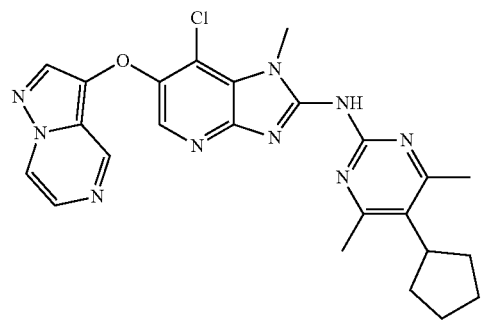
I-254
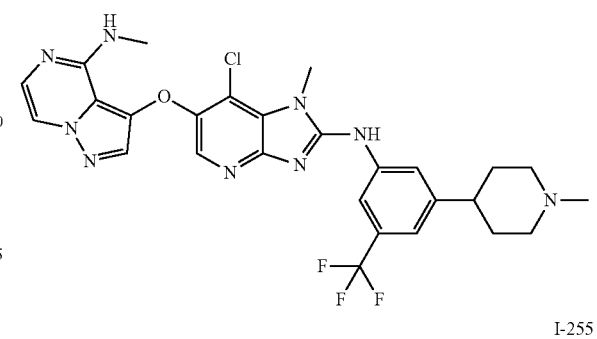
I-255
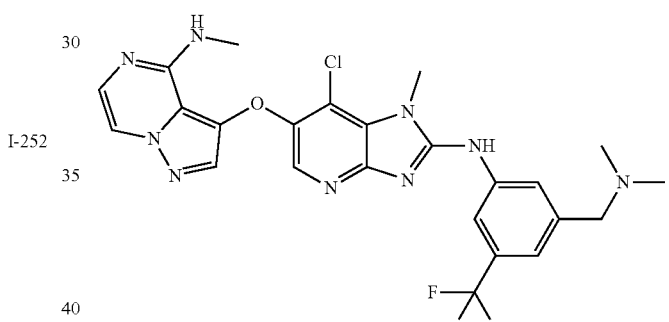
I-256
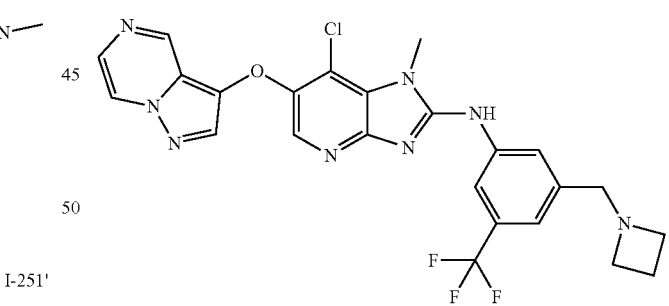
I-257
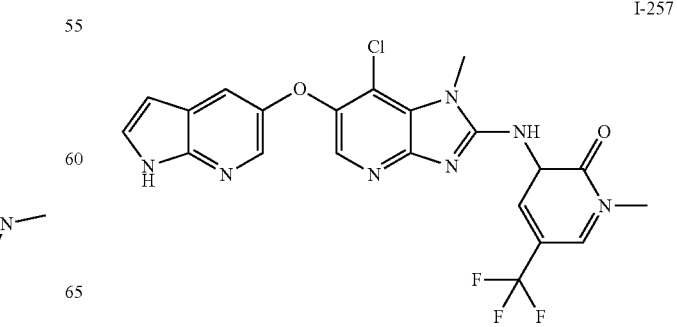

I-258
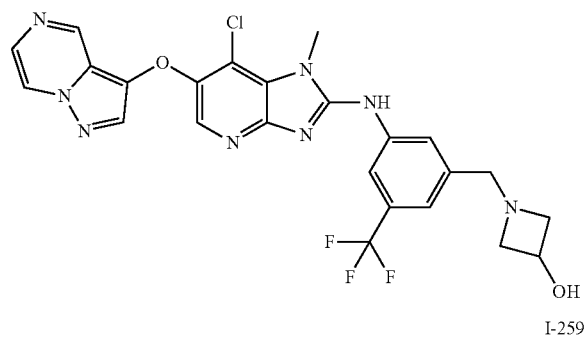
I-262-i
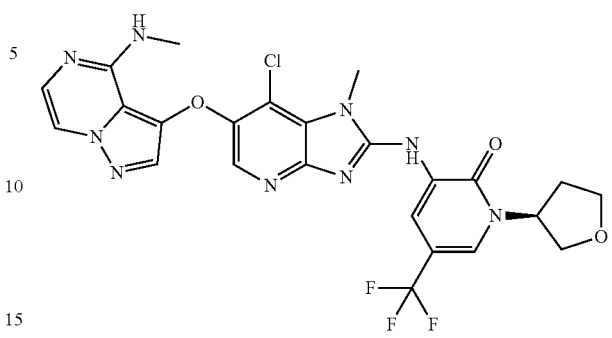
I-259
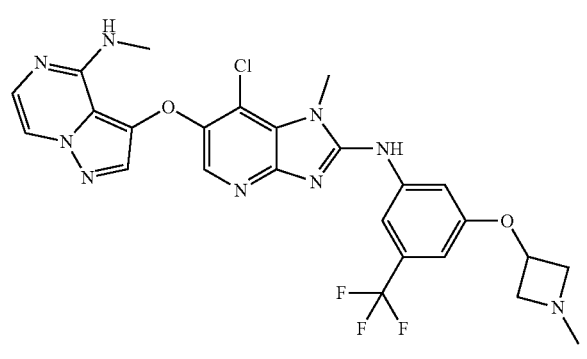
I-262-ii
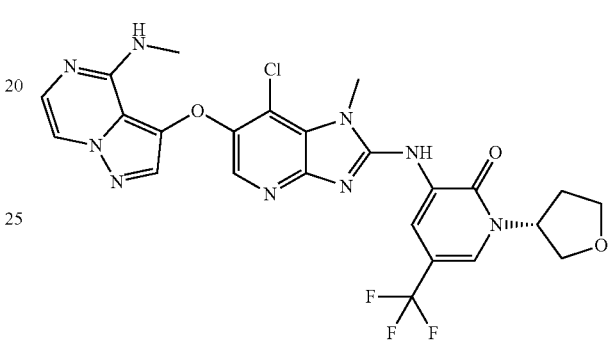
I-260
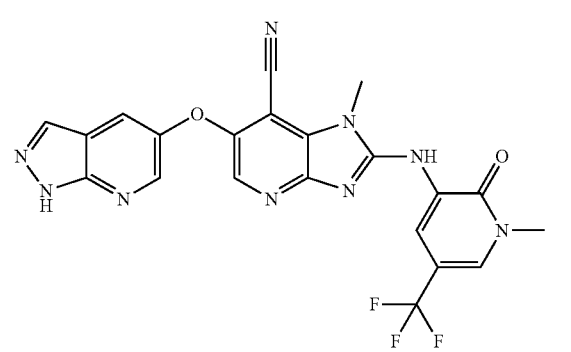
I-262
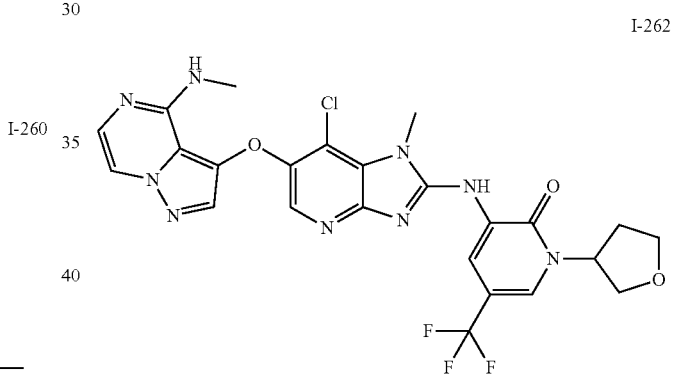
I-261
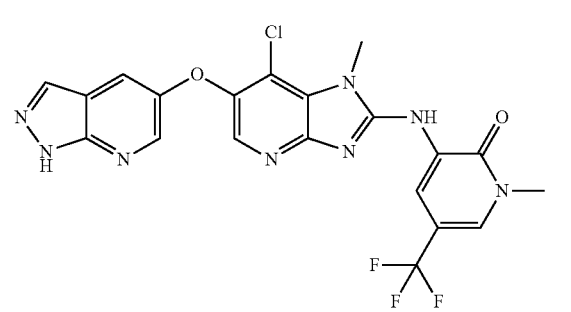
I-263
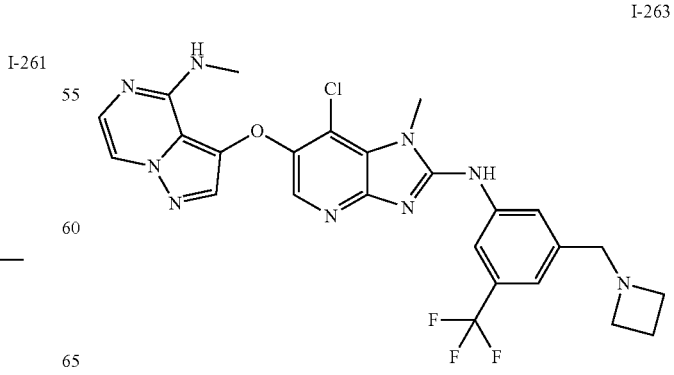

I-264
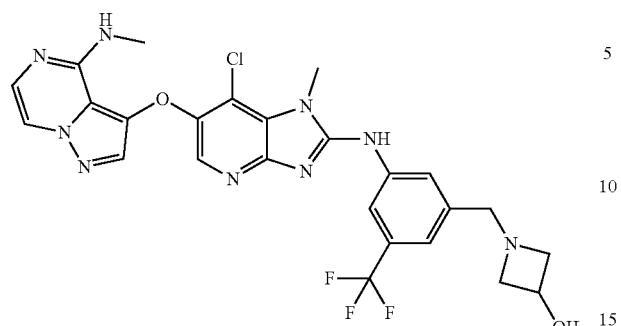
I-267-ii
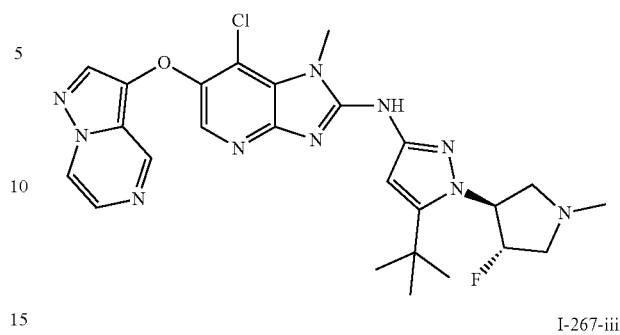
I-265
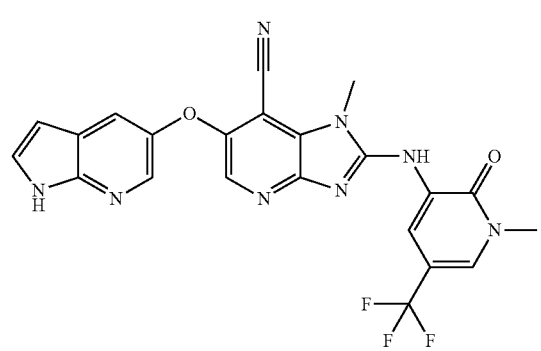
I-267-iii
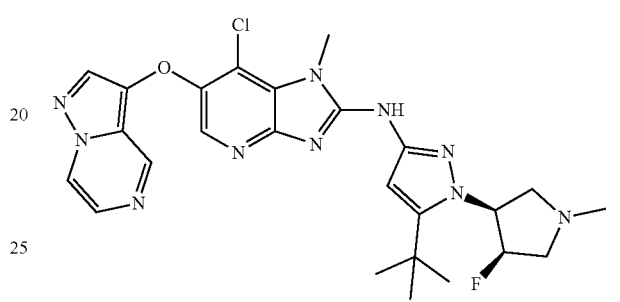
I-266
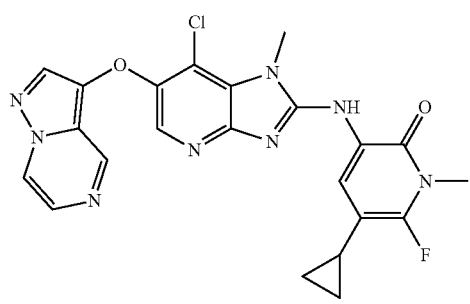
I-267-iv
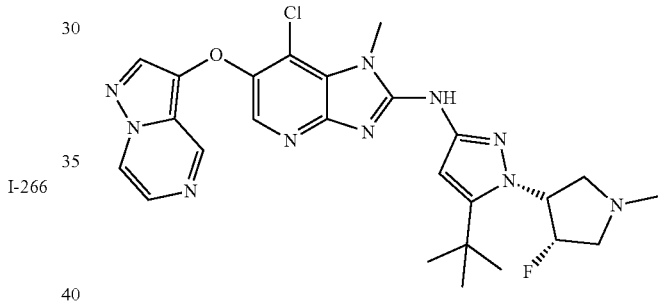
I-267-i
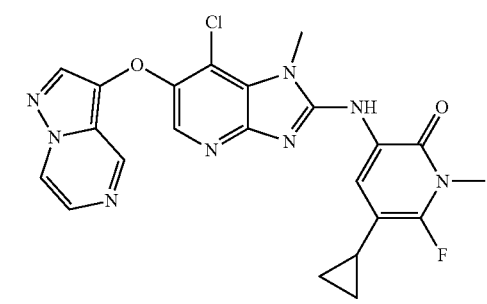
I-267
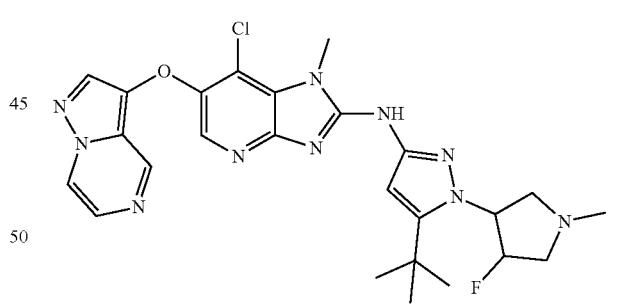
I-268
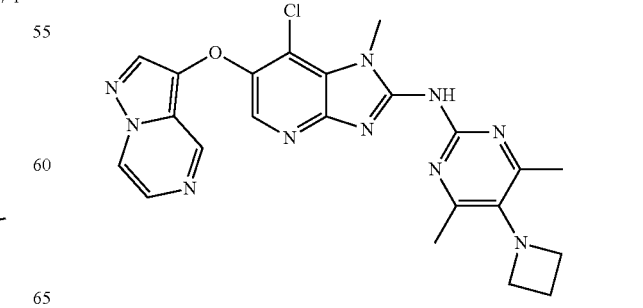

-continued
I-269-i
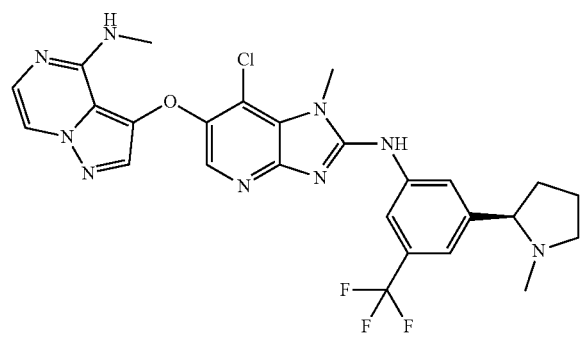
I-269-ii
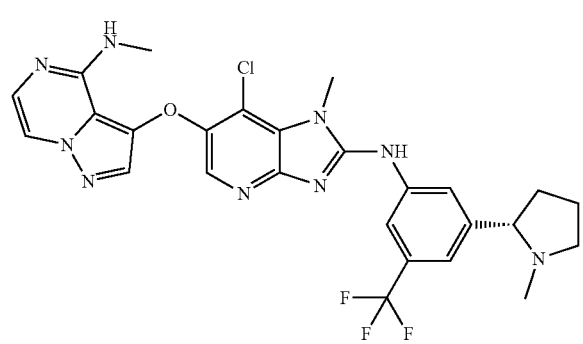
I-269
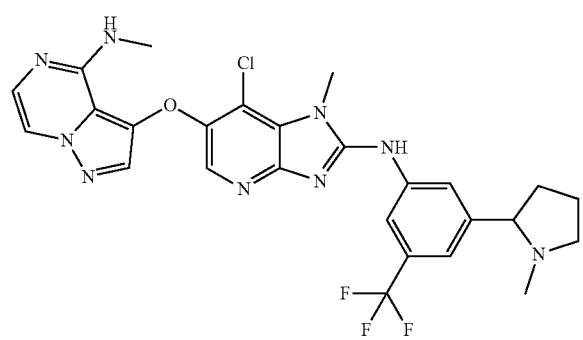
I-270-i
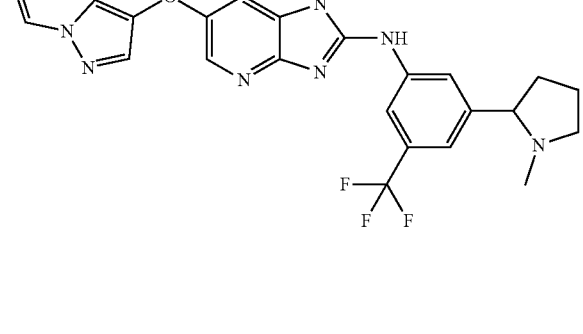
-continued
I-270-ii
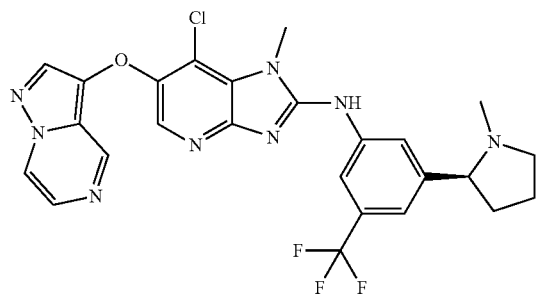
I-270
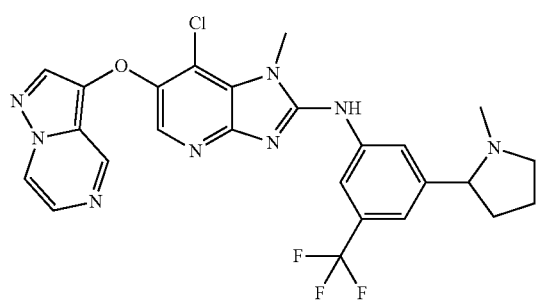
I-271
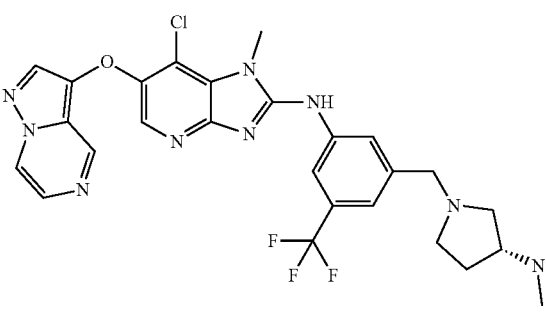
I-272
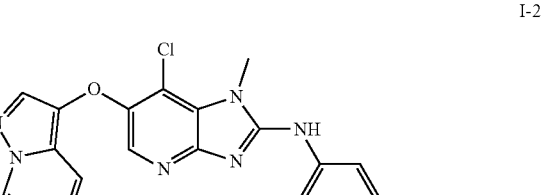
I-271'
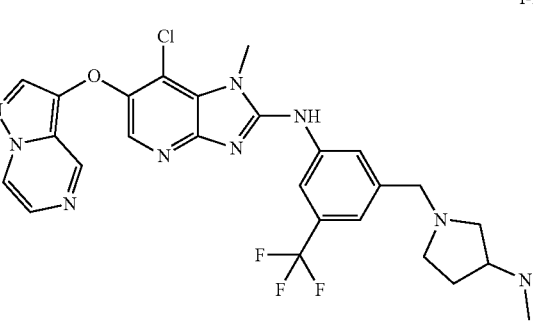

1275 -continued
I-273
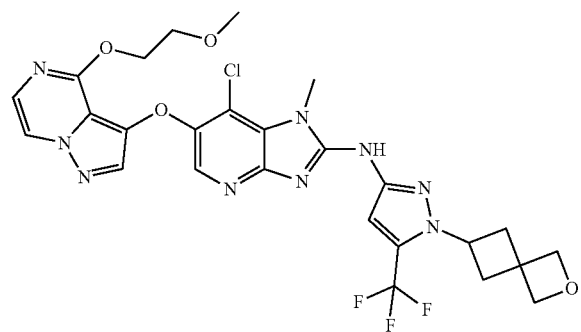
I-274
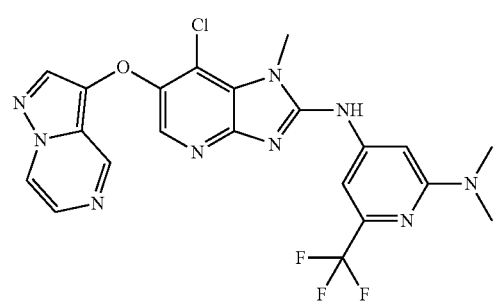
I-275
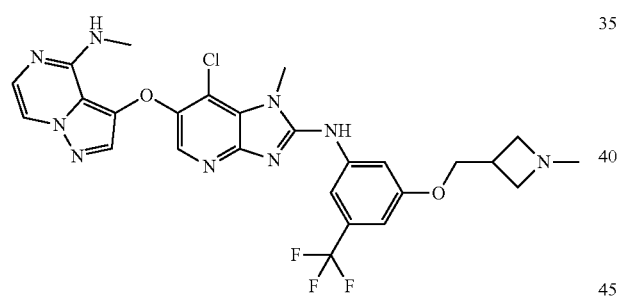
I-276
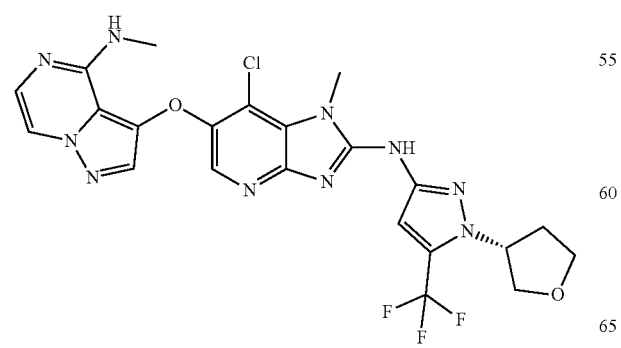
1276 -continued
I-276-ii
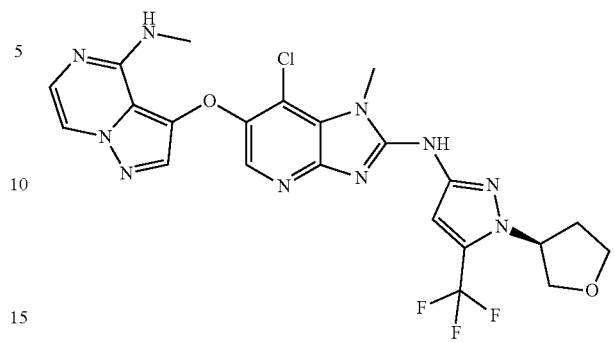
I-276'
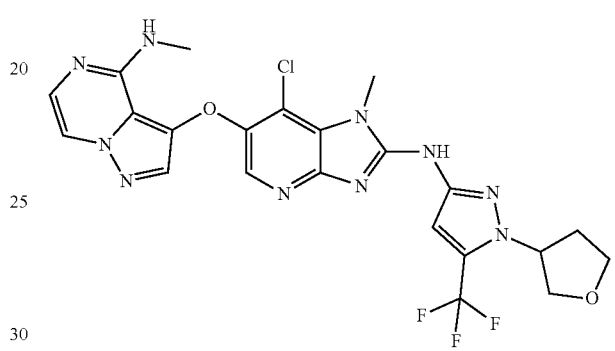
I-277
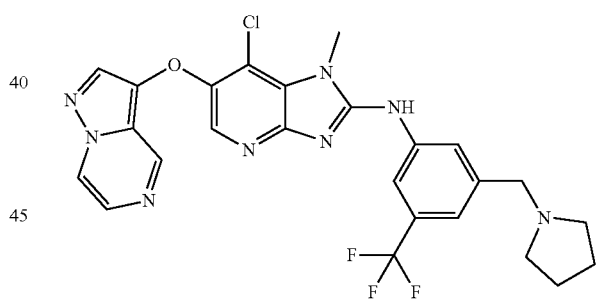
I-278
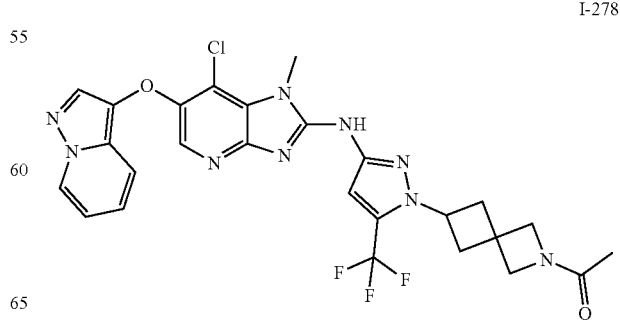

I-279-i
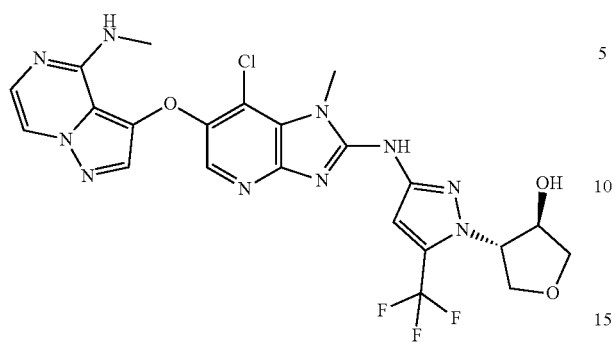
I-279-ii
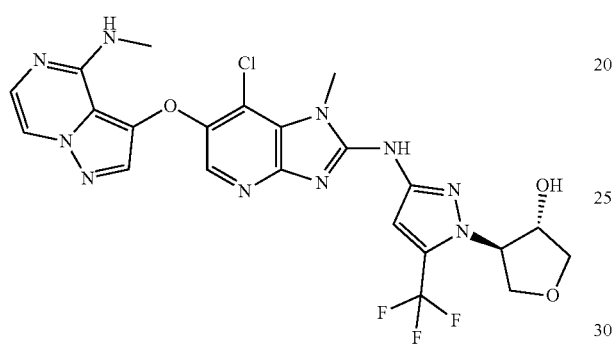
I-279-iii
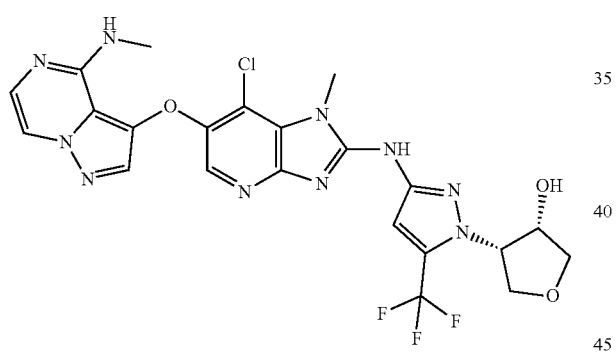
I-279-iv
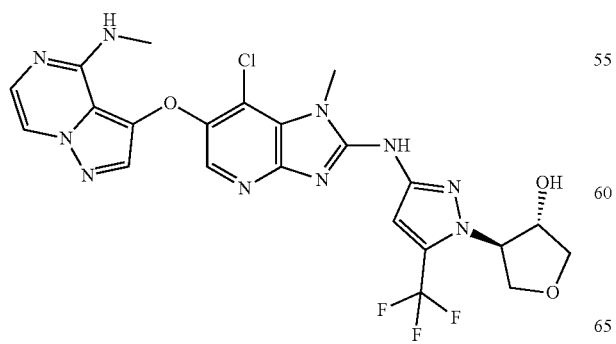
I-279
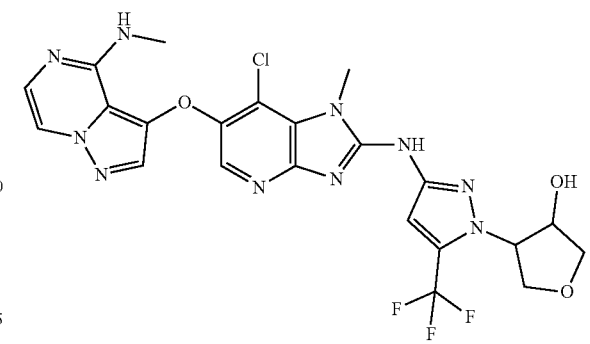
I-280-i
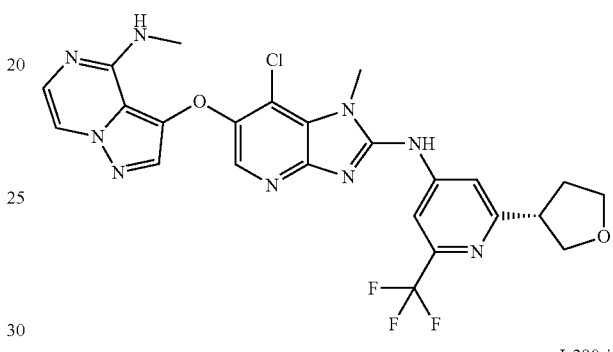
I-280-ii
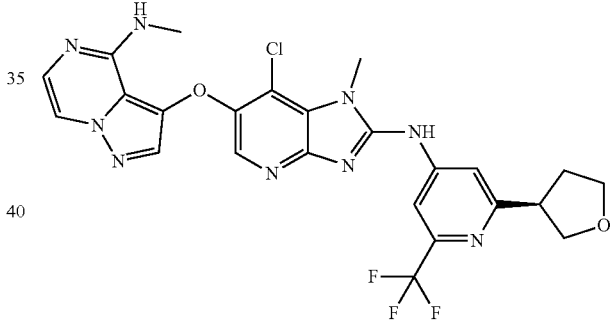
I-280
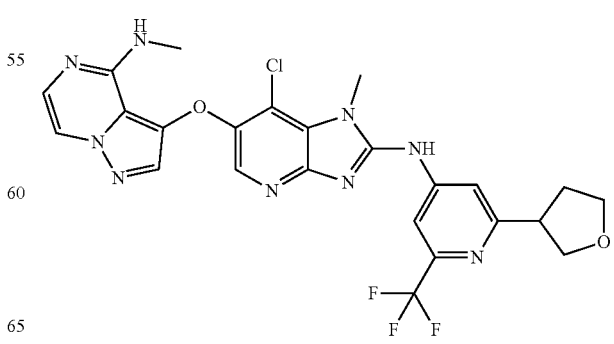

I-281
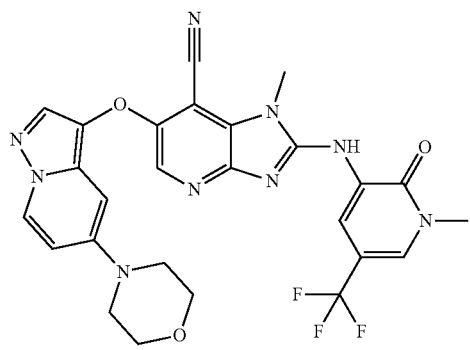
I-282
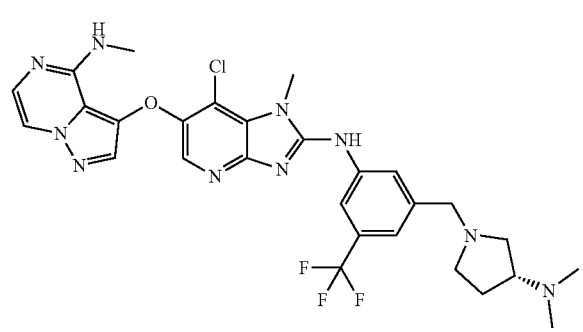
I-283
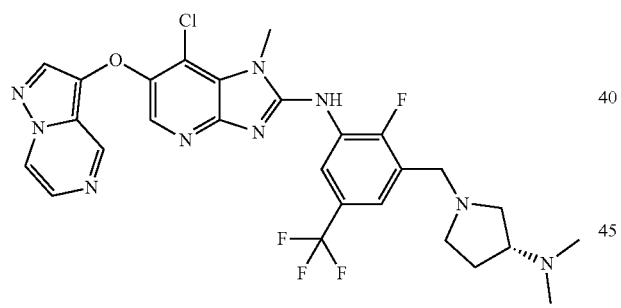
I282'
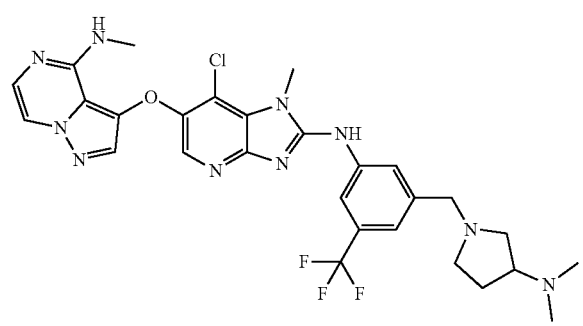
I-284
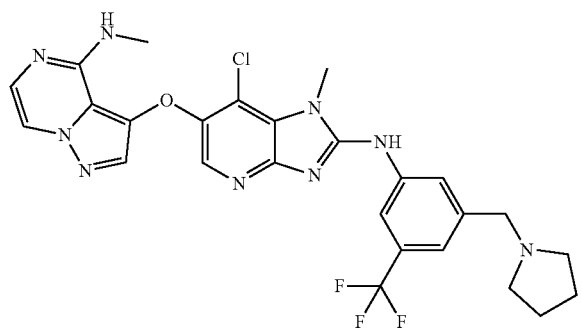
I-285
I-286
I-285'
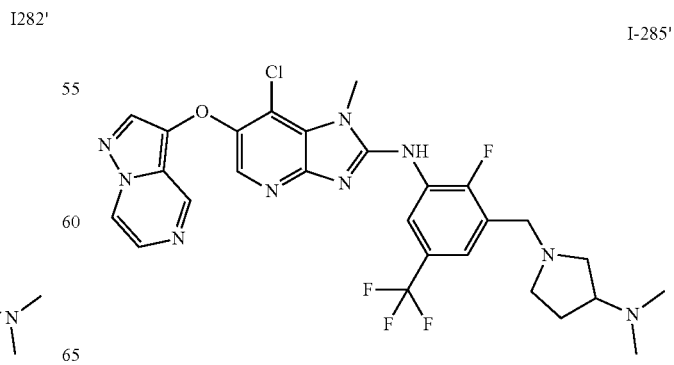

1281
-continued
I-287
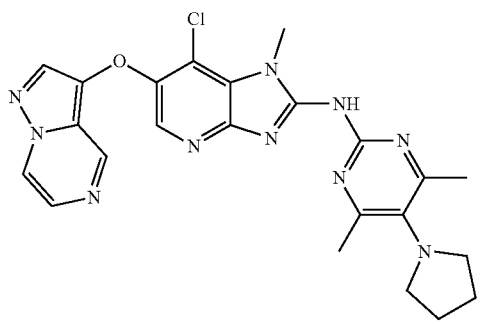
I-288
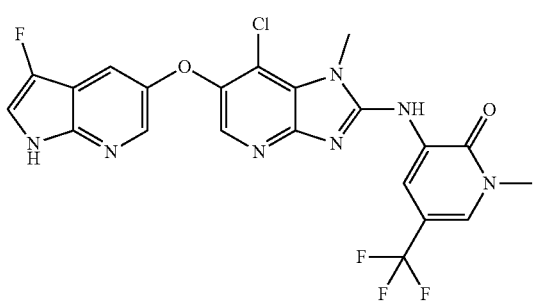
I-289
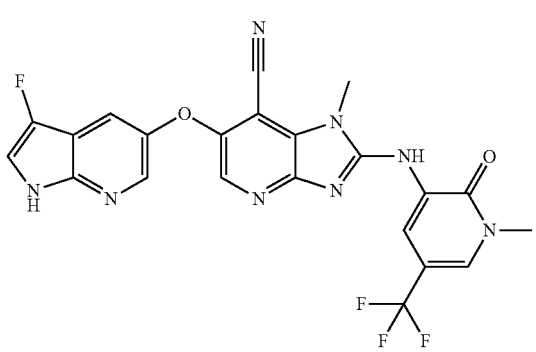
I-290
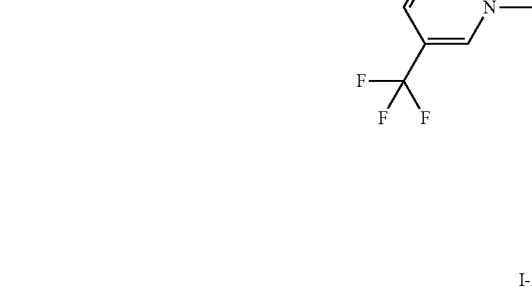
1282
-continued
I-291
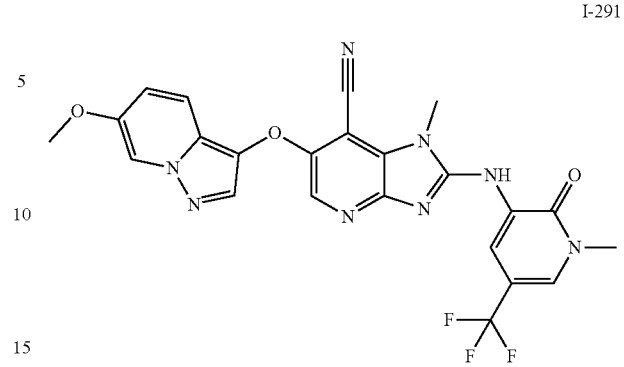
I-292
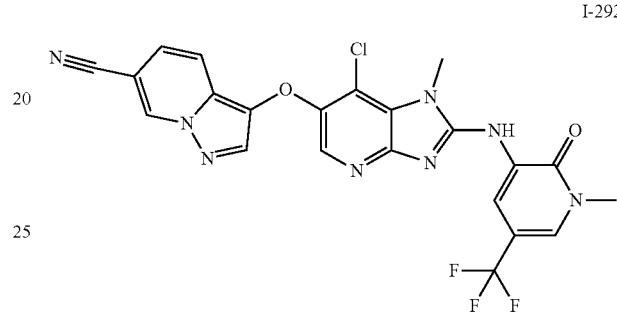
I-293
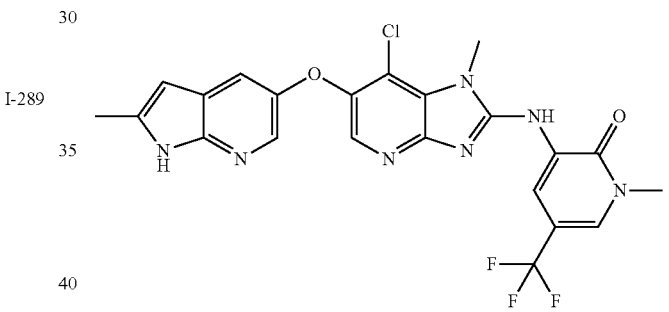
I-294
I-295
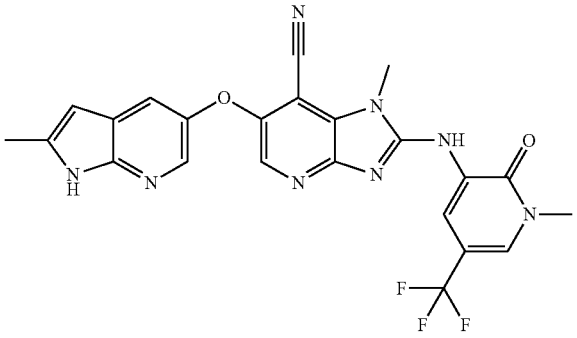

1283
-continued
I-295-ii
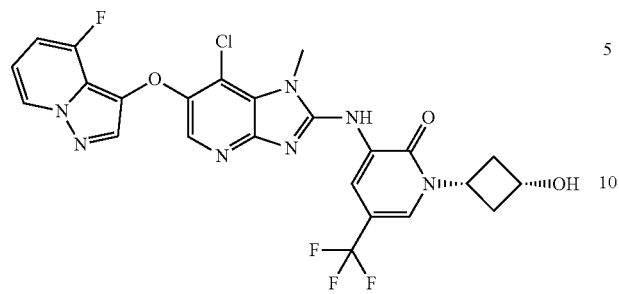
I-295'
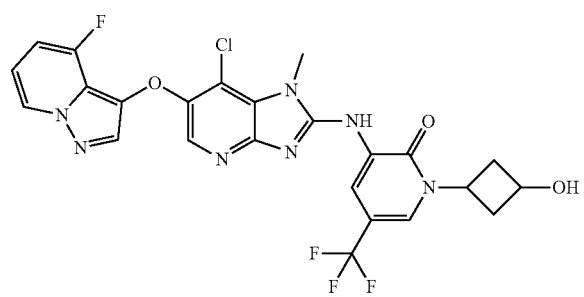
I-296
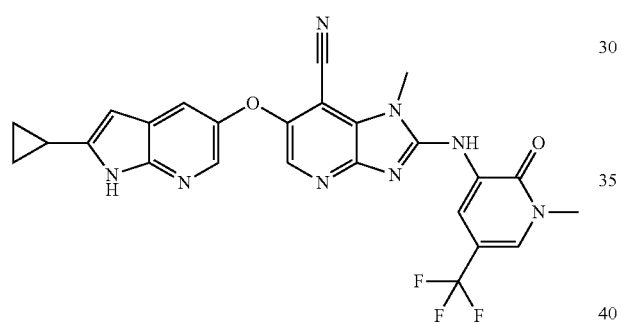
I-297
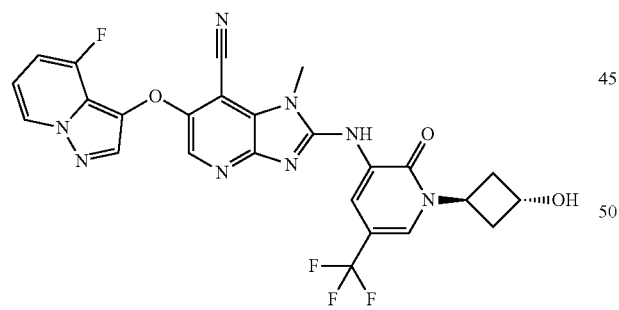
I-297-ii
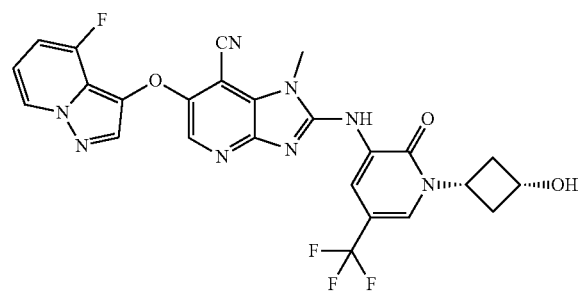
1284
-continued
I-297'
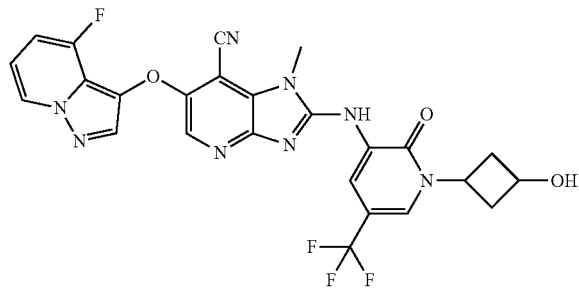
I-298
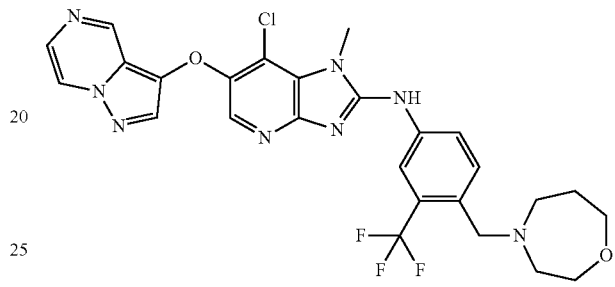
I-299
I-300
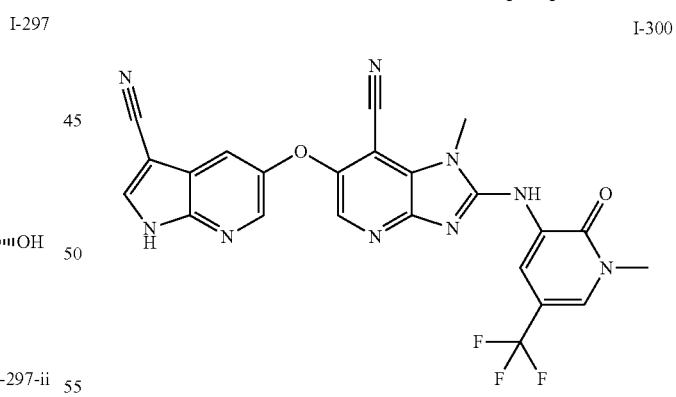
I-301
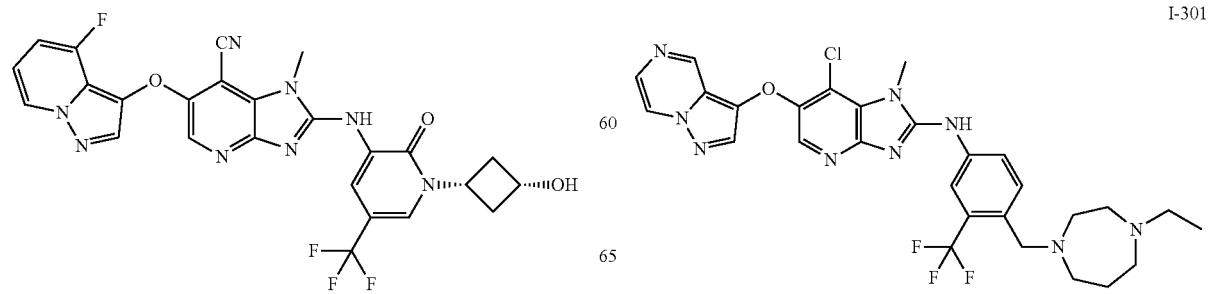

I-302
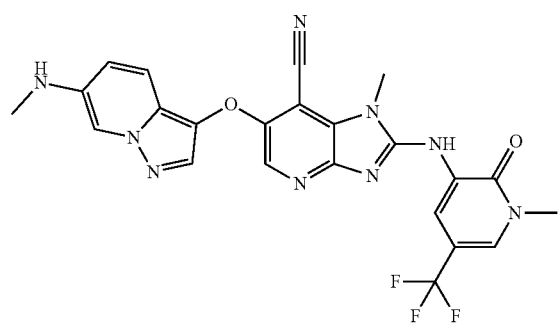
I-303
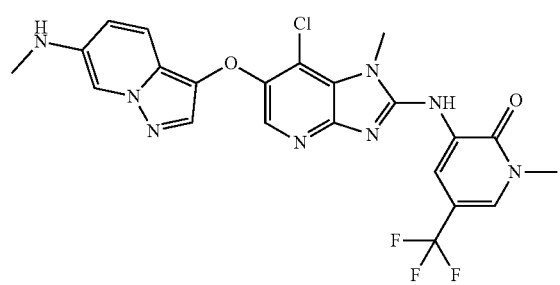
I-304
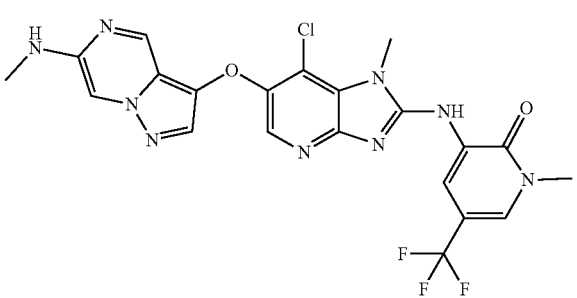
I-305
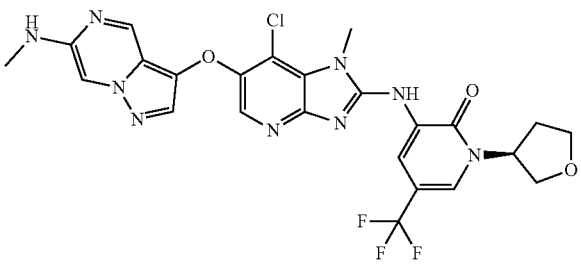
I-306
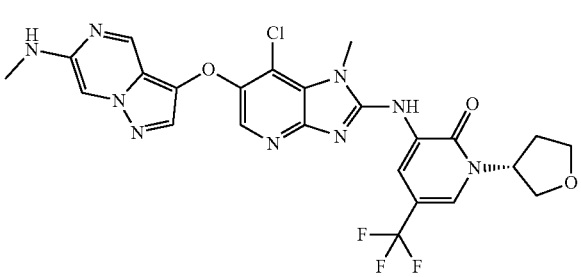
I-305'
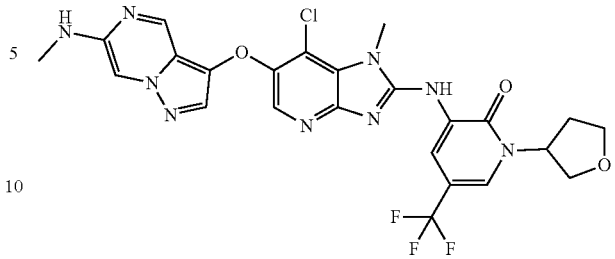
I-307
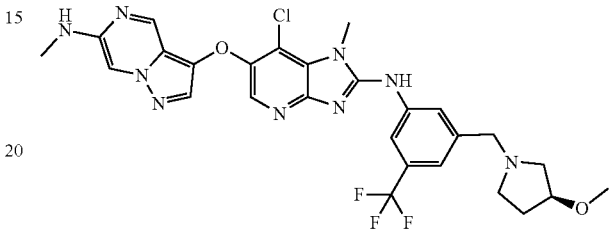
I-307'
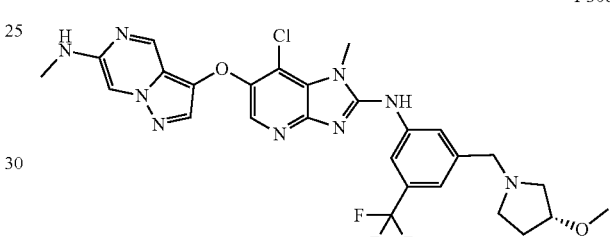
I-308
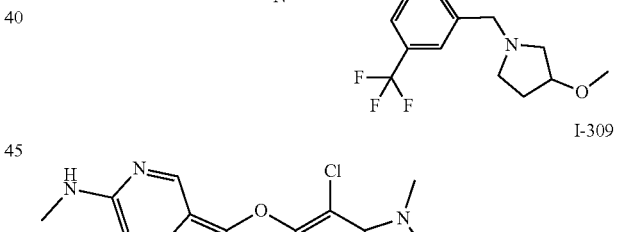
I-309
I-310
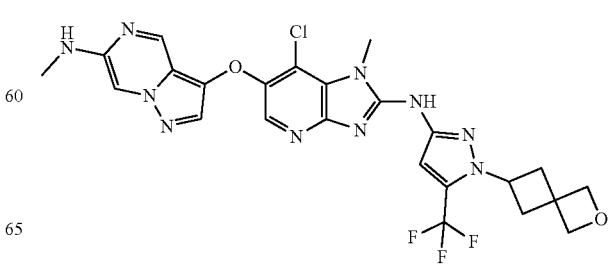

1287
-continued
I-311
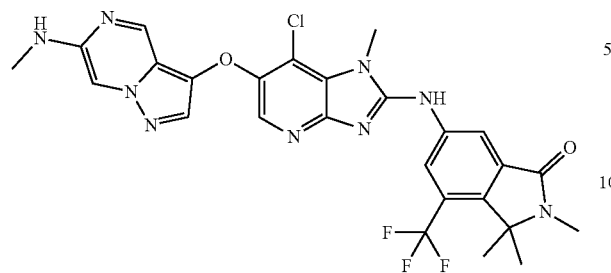
I-312
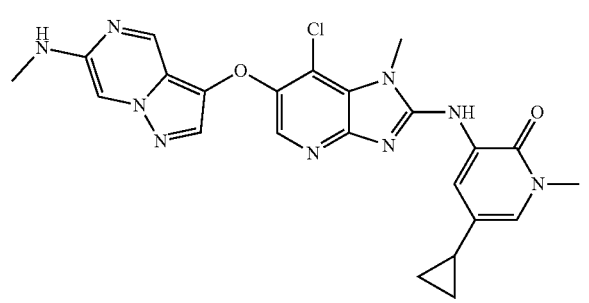
I-313
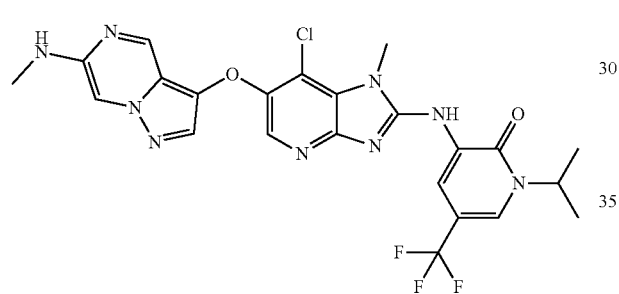
I-314
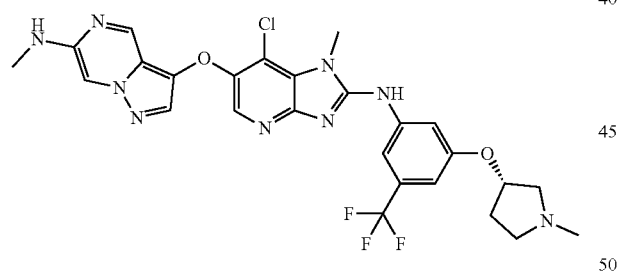
I-315
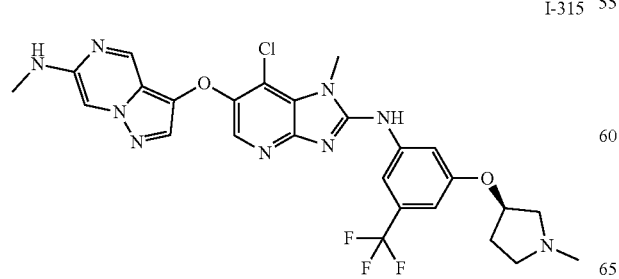
1288
-continued
I-314'
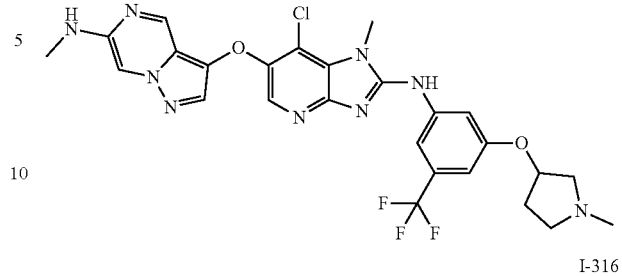
I-316
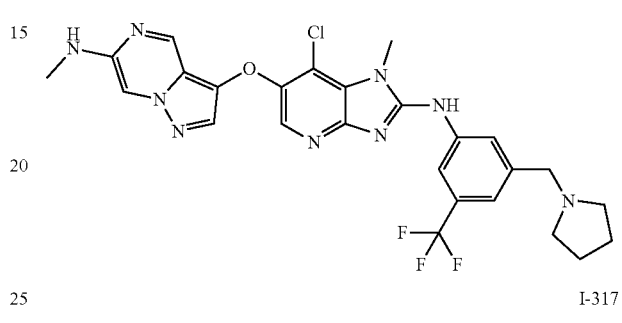
I-317
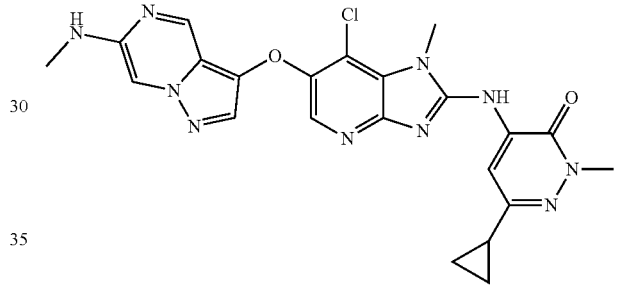
I-318
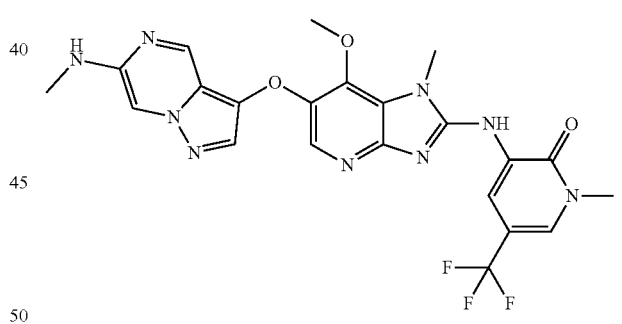
I-319
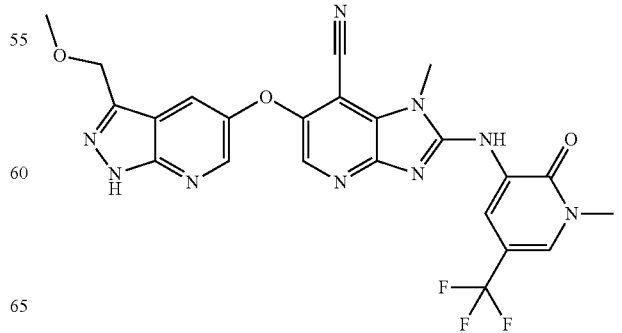

I-320
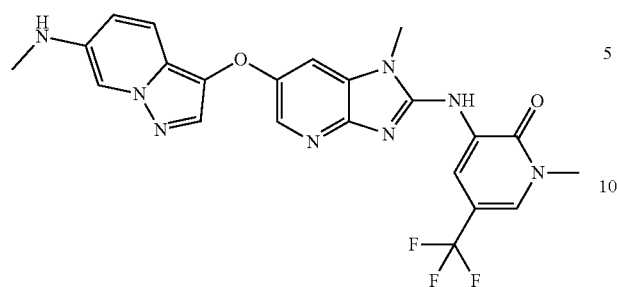
I-321
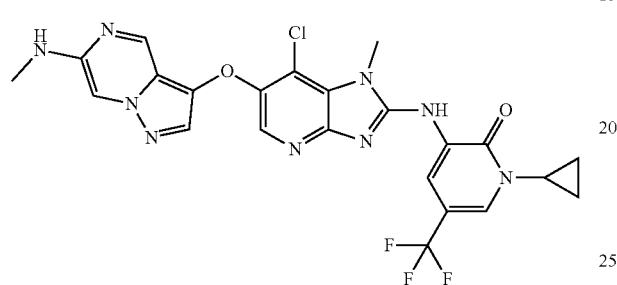
I-322
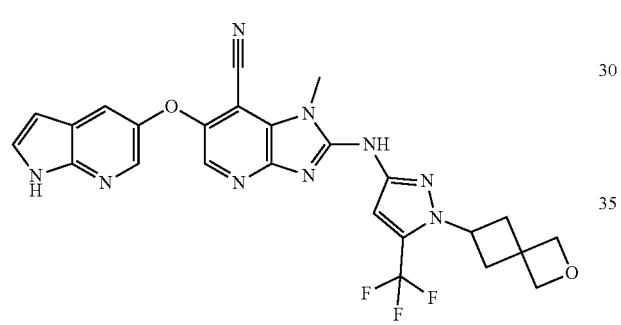
I-323
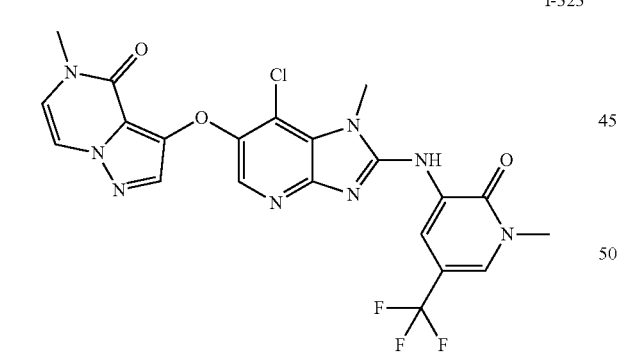
I-324
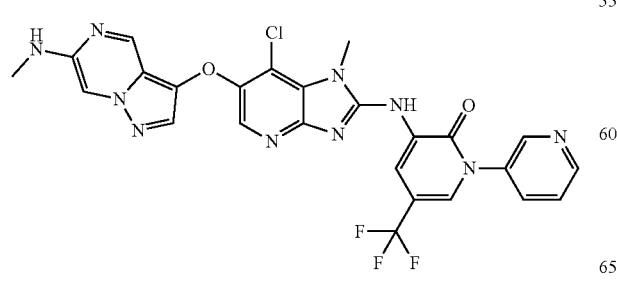
I-325
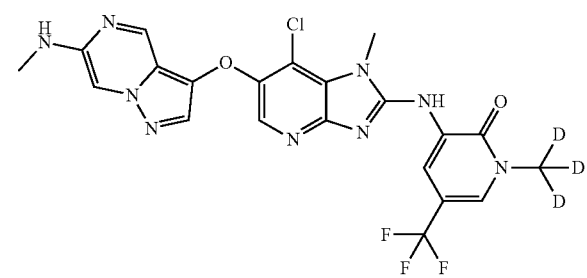
I-326
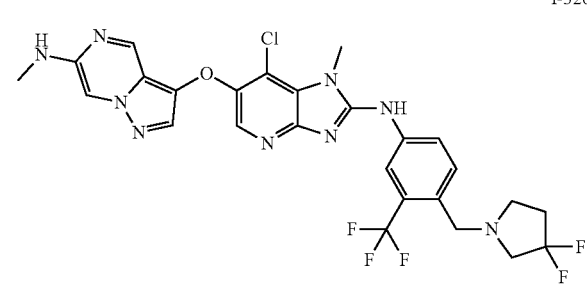
I-327
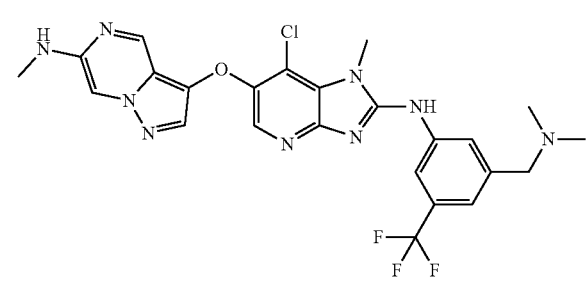
I-328
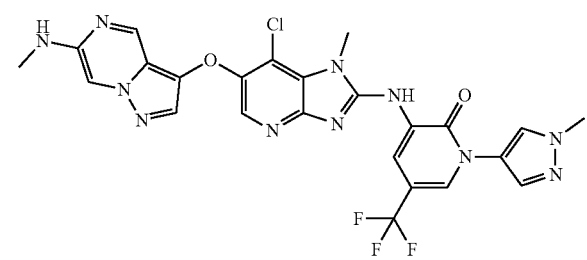
I-329
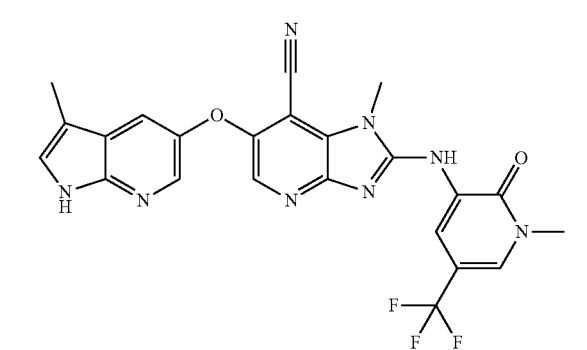

I-330
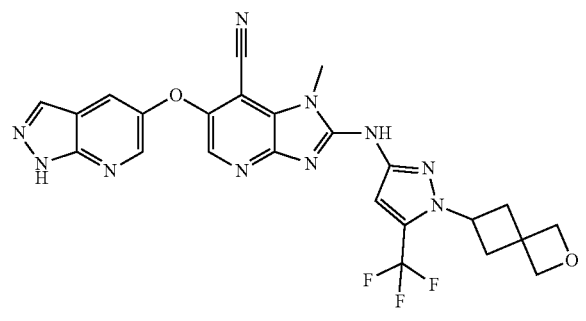
I-331
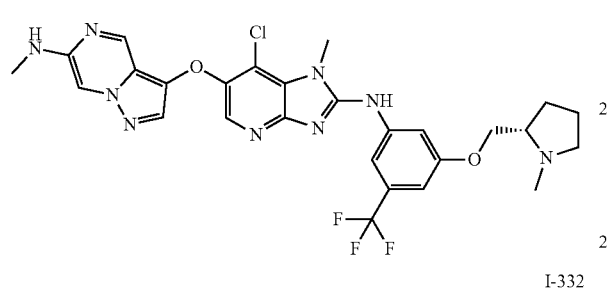
I-332
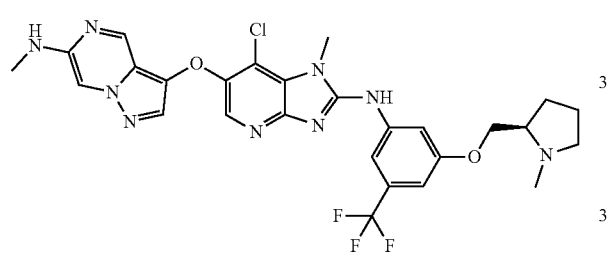
I-331'
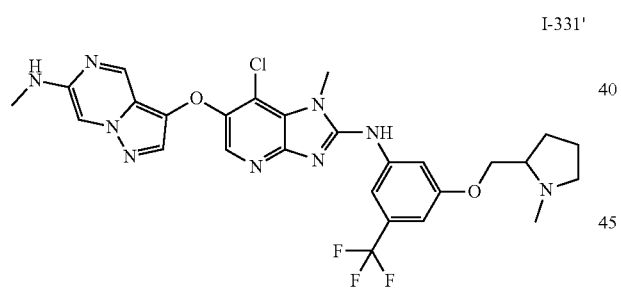
I-333
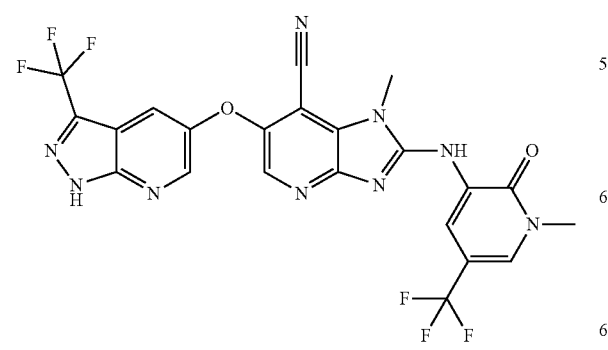
I-334
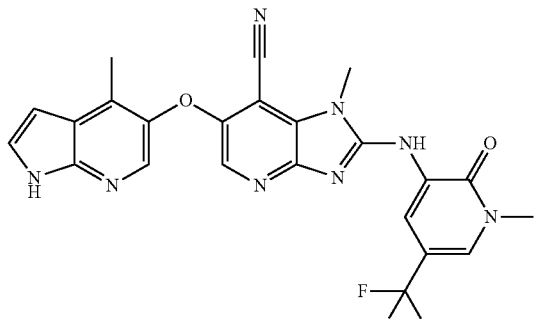
I-335
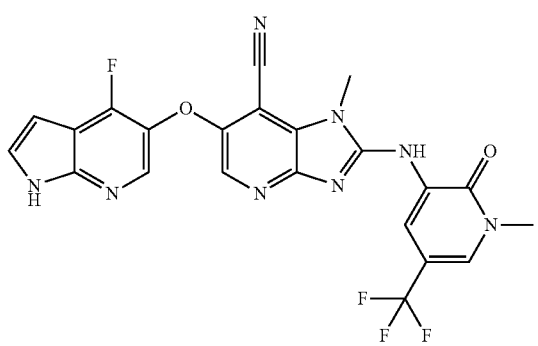
I-336
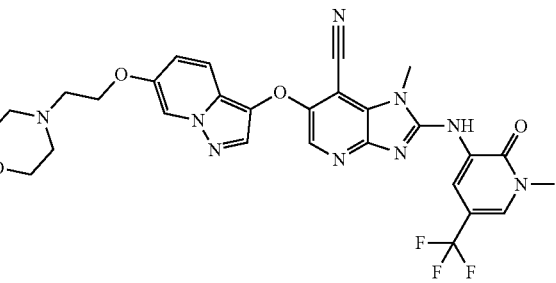
I-337
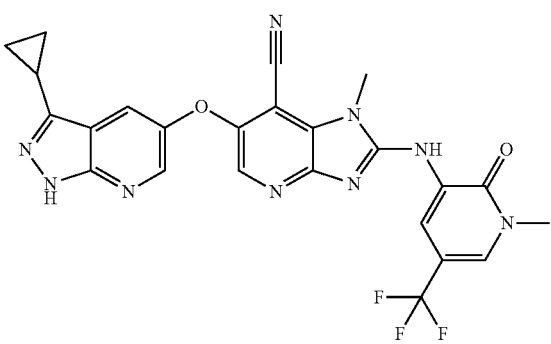

I-338
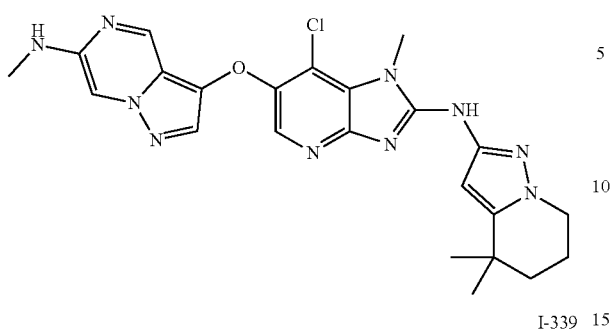
I-341
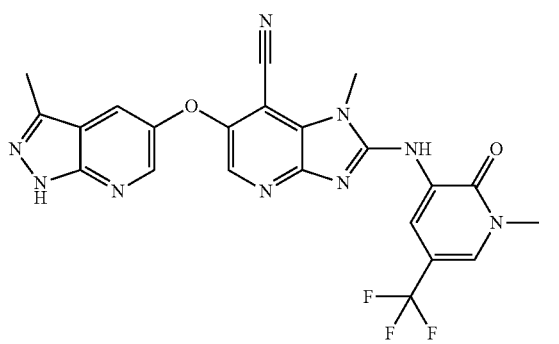
I-339
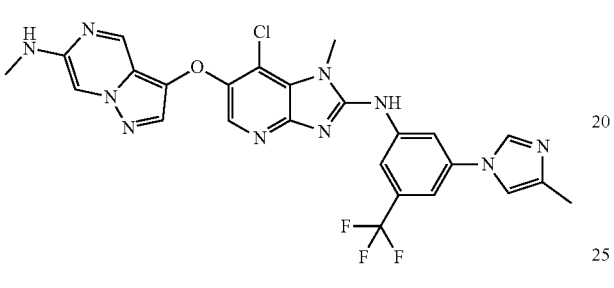
I-342
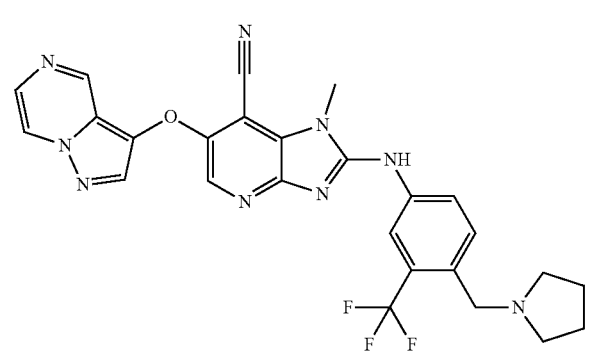
I-340
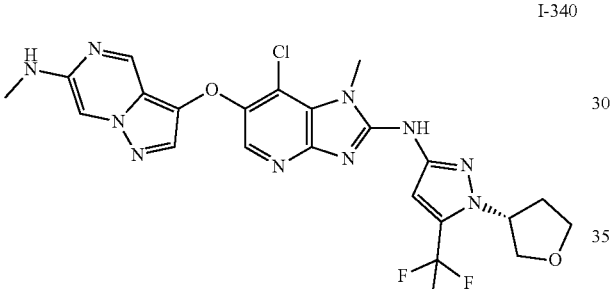
I-343'
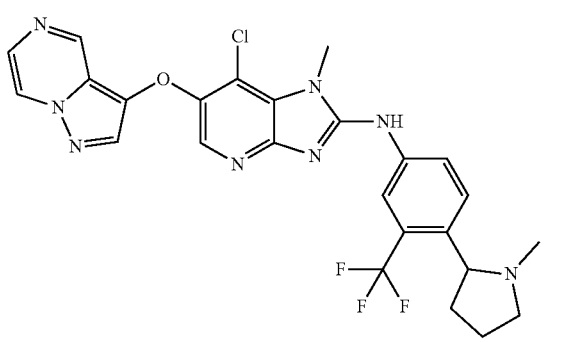
I-340'
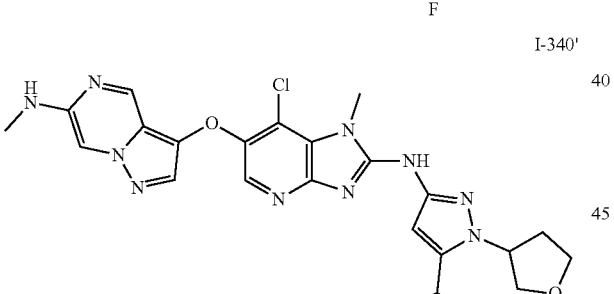
I-340-ii
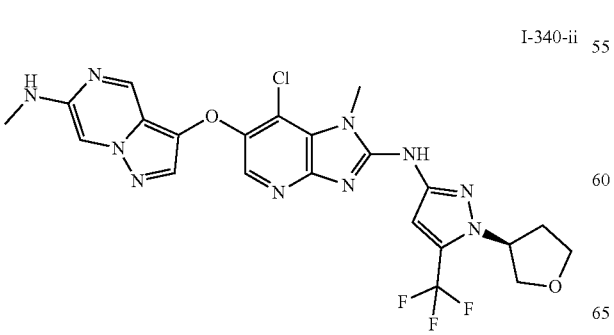
I-343
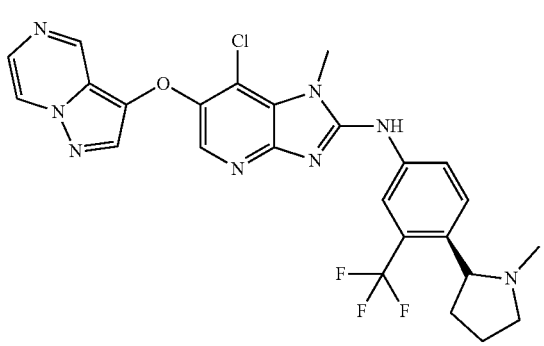

I-344
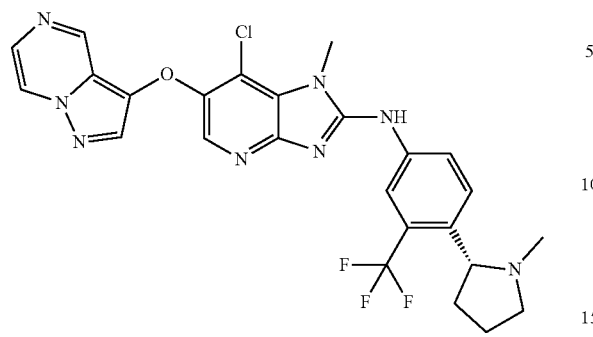
I-345
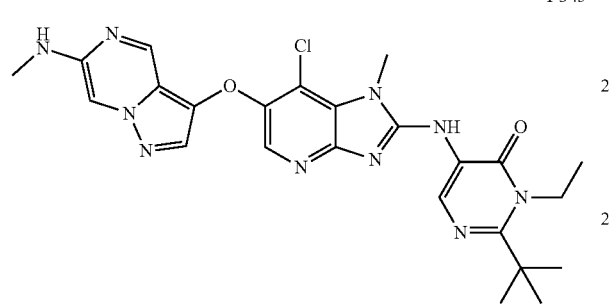
I-346
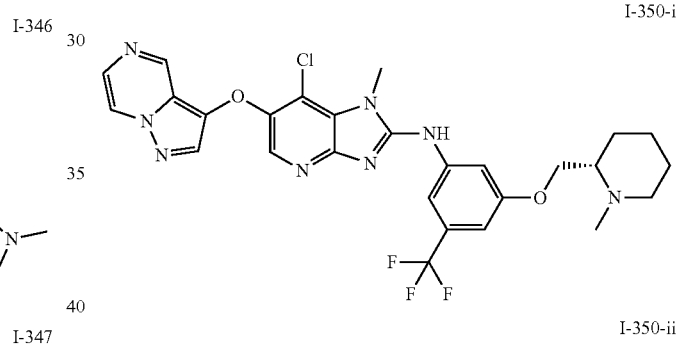
I-347
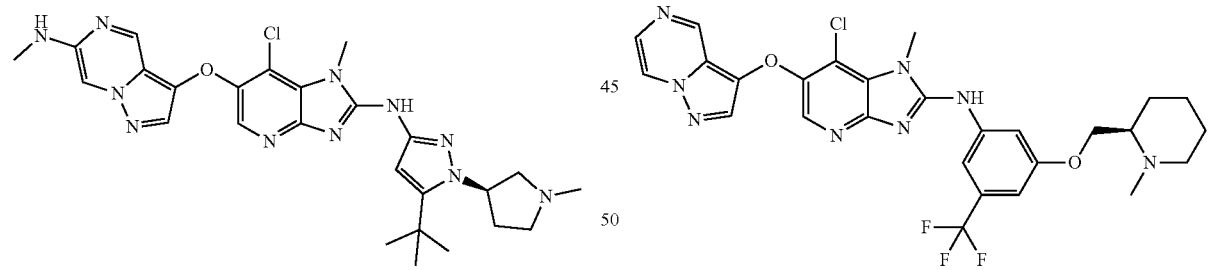
I-346'
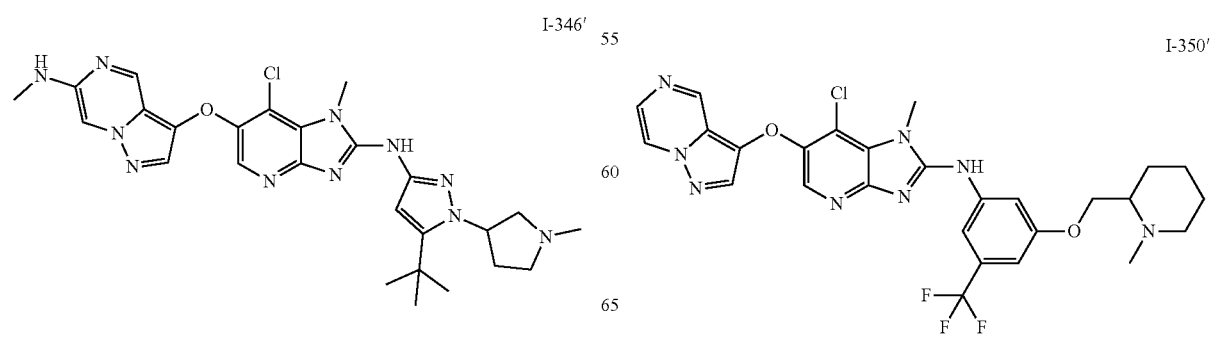
I-348
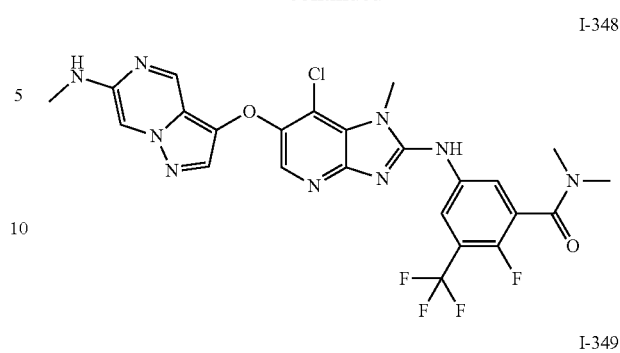
I-349
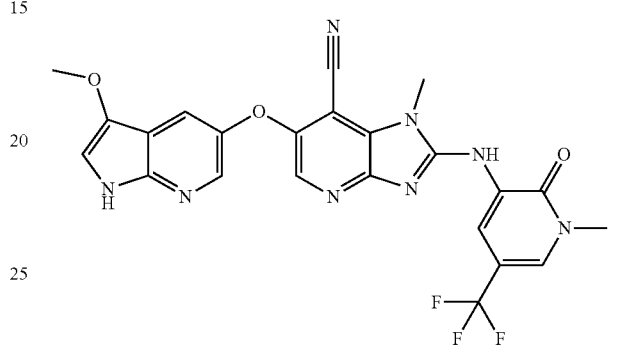
I-350-i
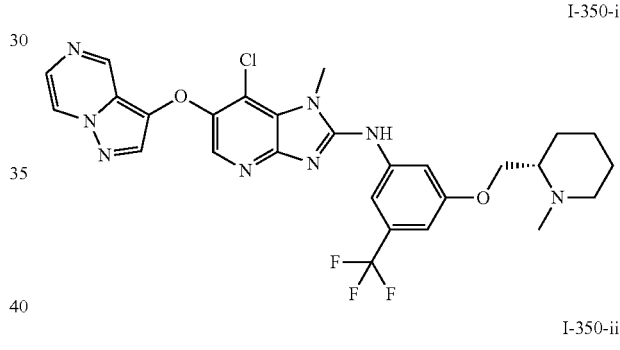
I-350-ii
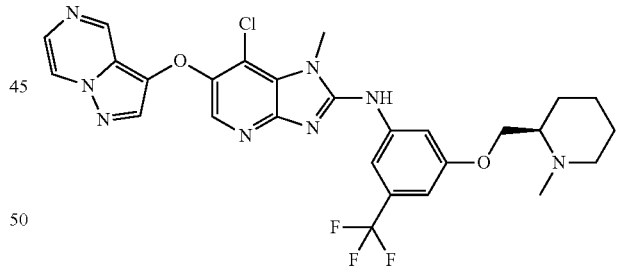
I-350'

I-351
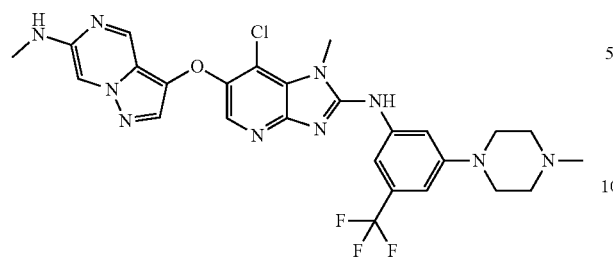
I-352-i
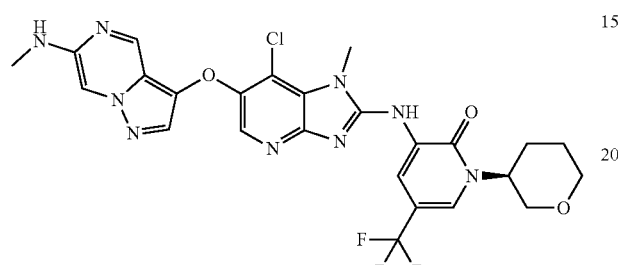
I-352-ii
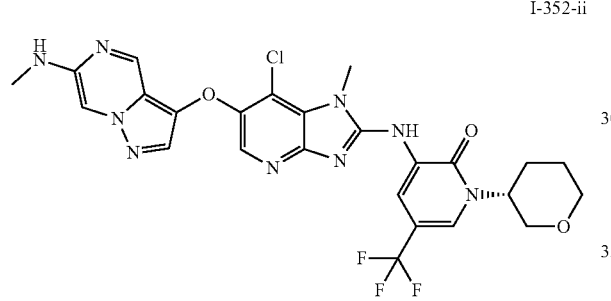
I-352'
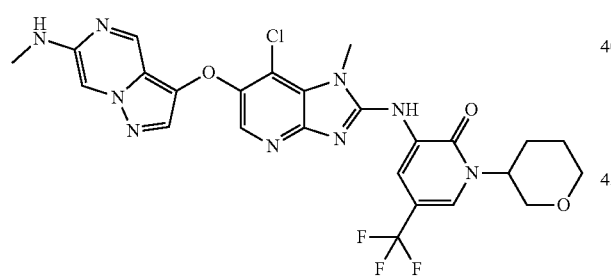
I-353
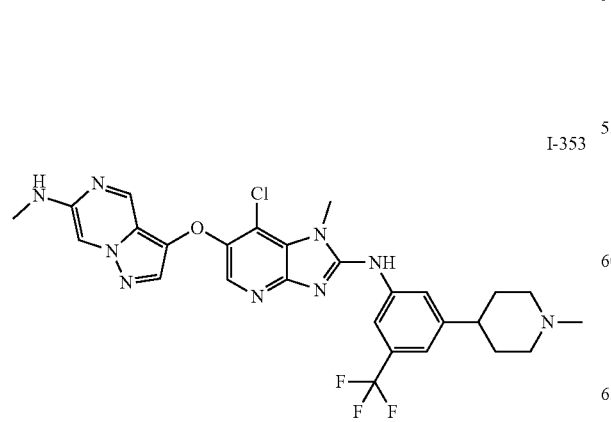
I-354
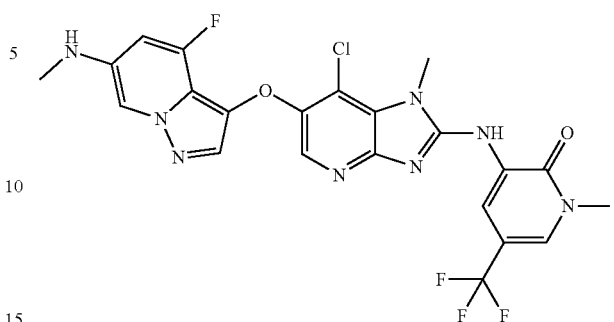
I-355
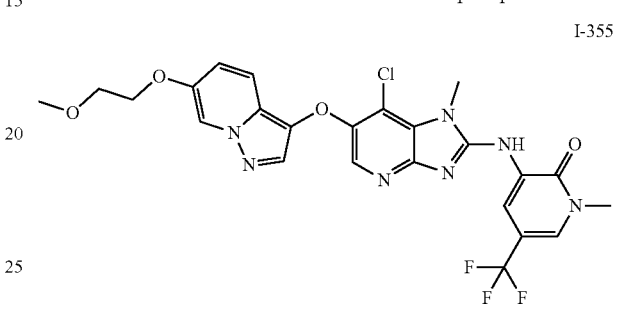
I-356
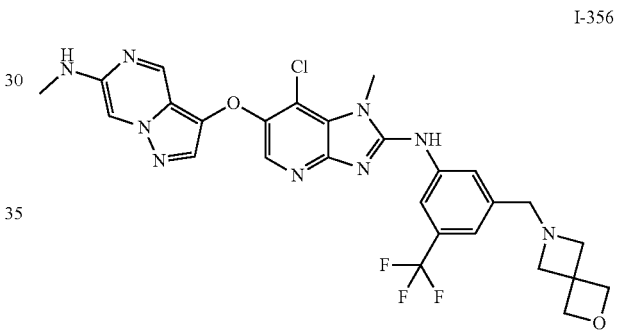
I-357
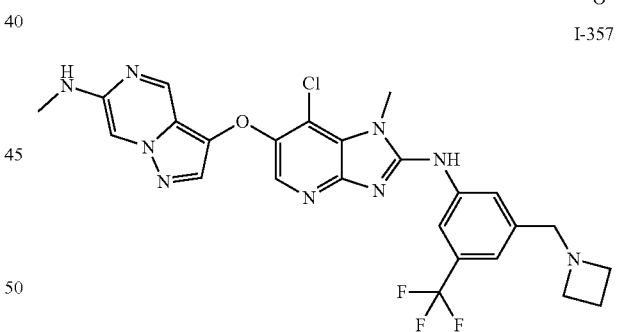
I-358
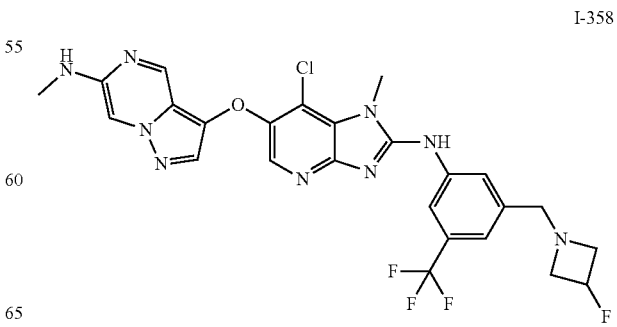

I-359-i
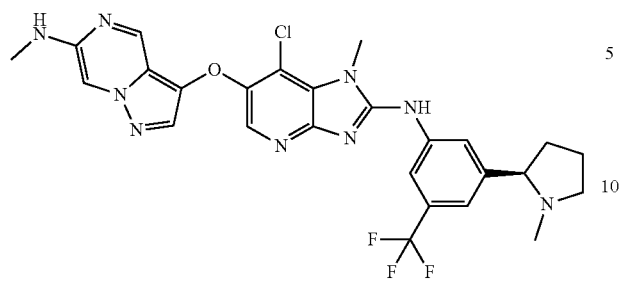
I-359-ii
I-359'
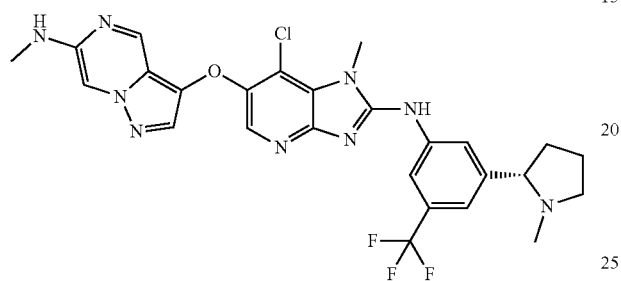
I-360
I-361
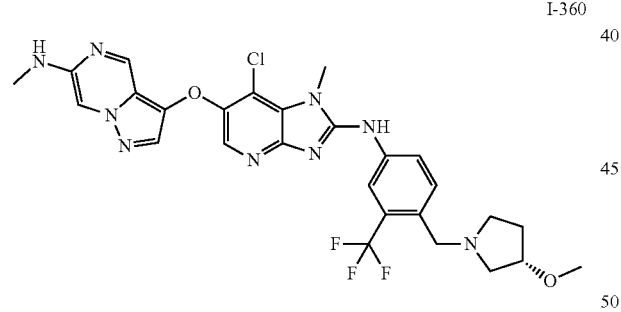
I-360'
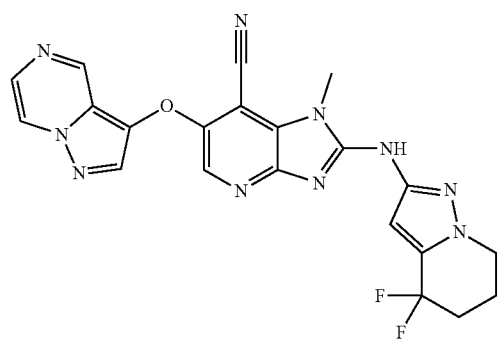
I-362
I-363
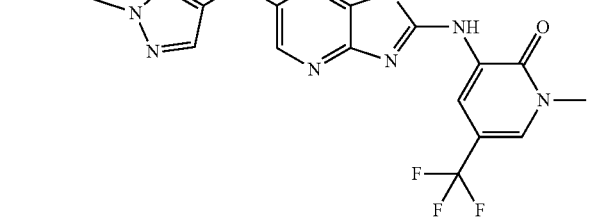
I-364
I-365
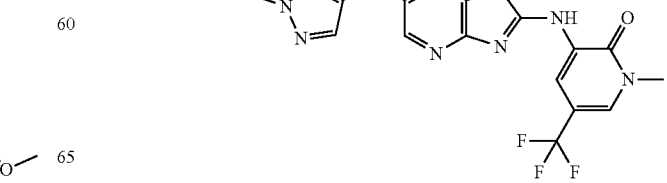

I-366
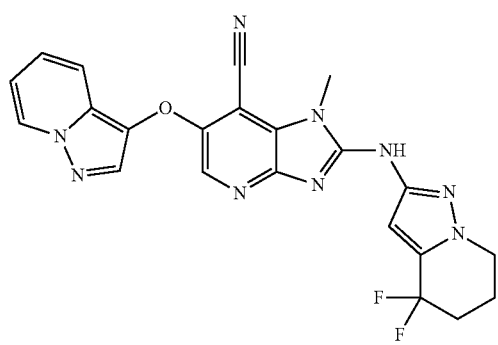
I-367
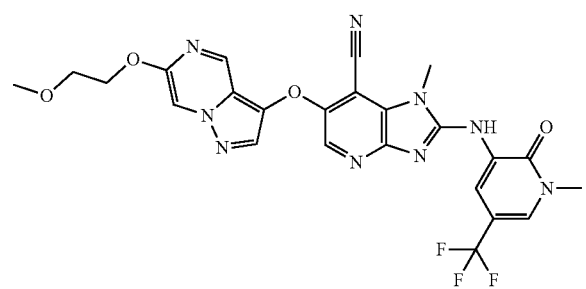
I-368
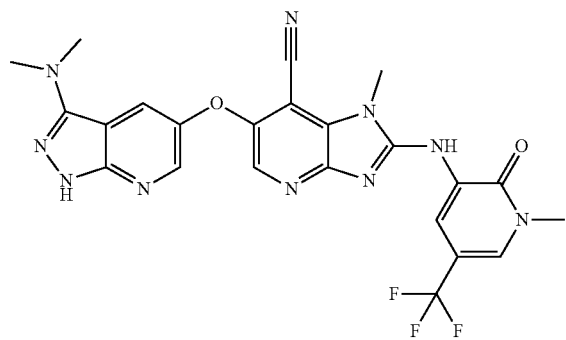
I-369
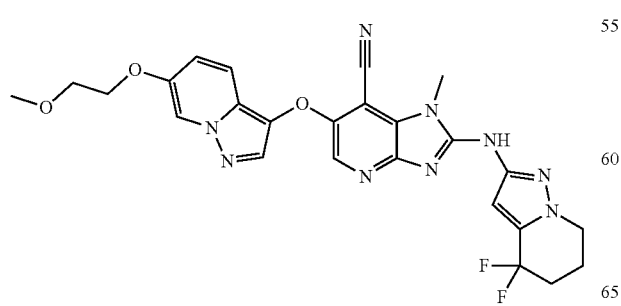
I-370
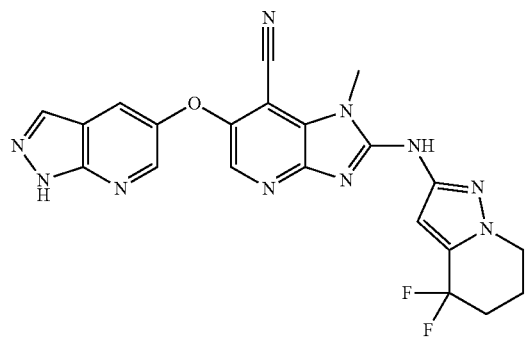
I-371
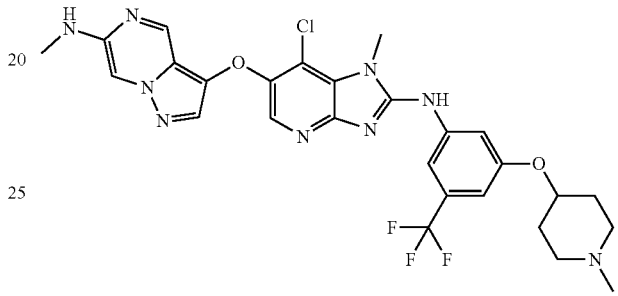
I-372
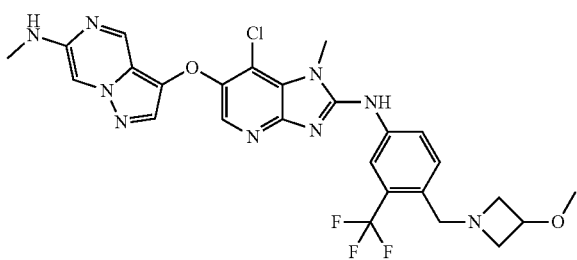
I-373
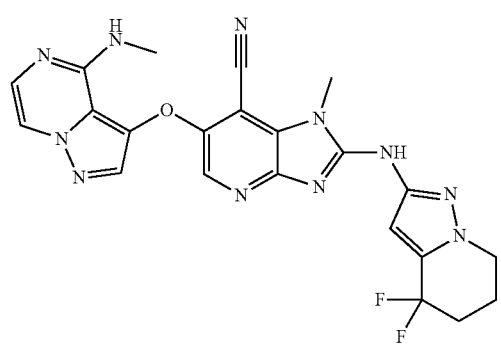

1303
-continued
I-374
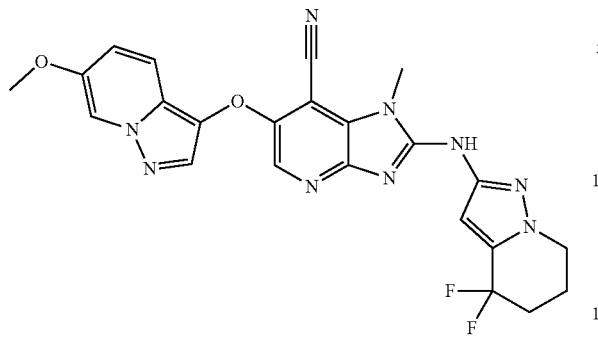
I-375
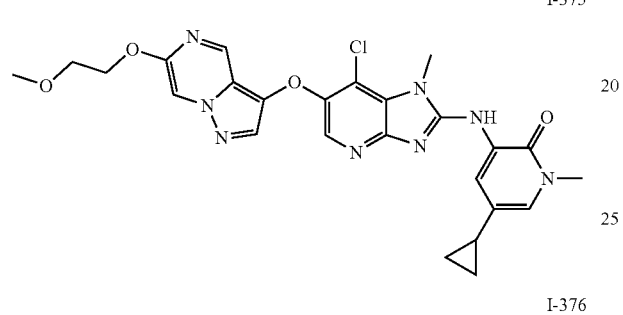
I-376
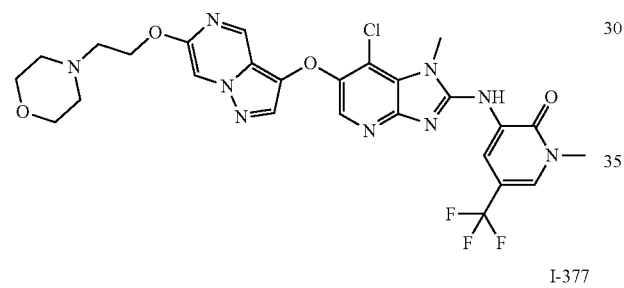
I-377
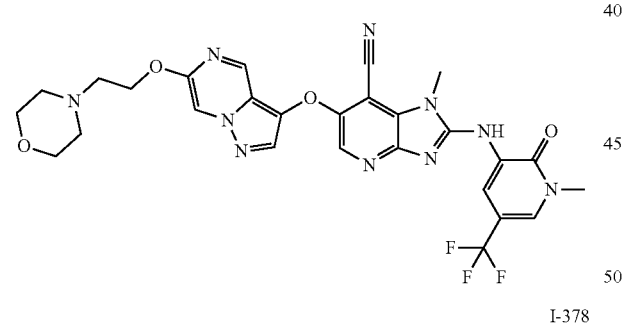
I-378
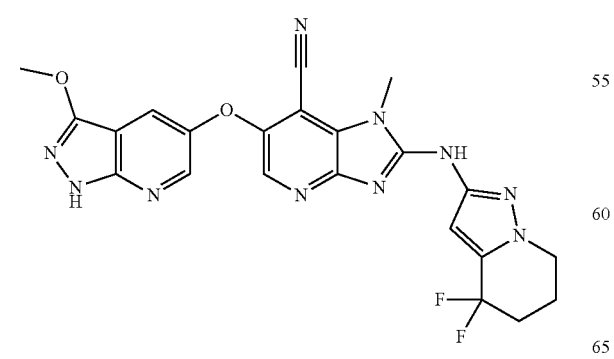
1304
-continued
I-379
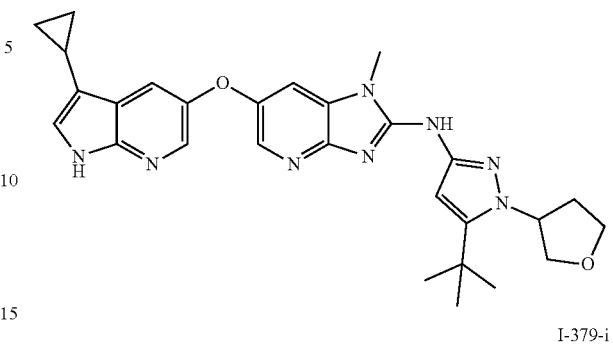
I-379-i
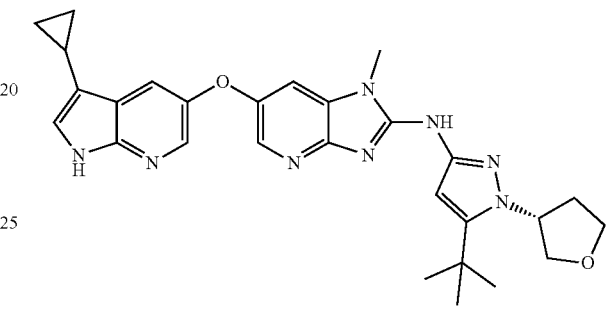
I-379-ii
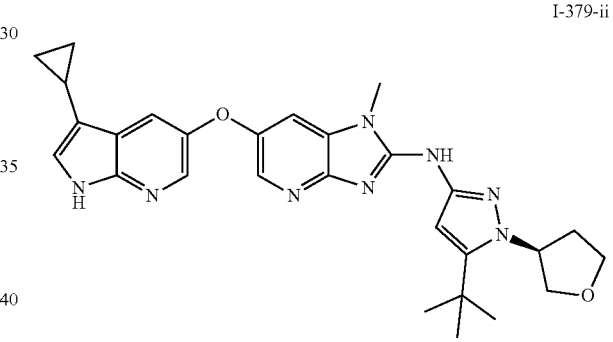
I-380
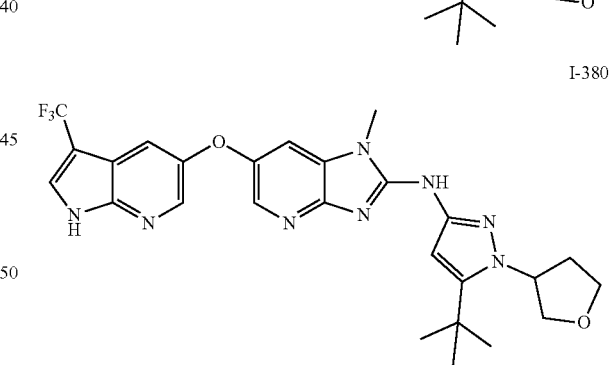
I-380-i
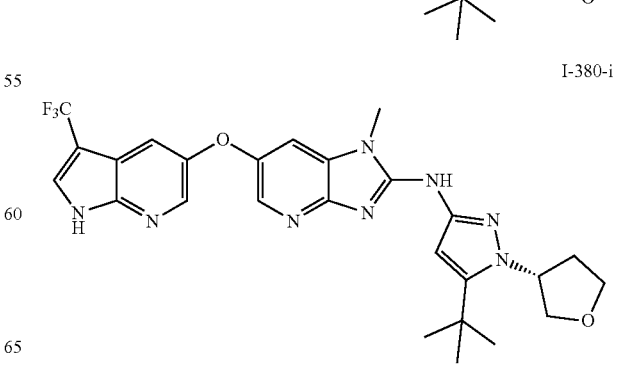

I-380-ii
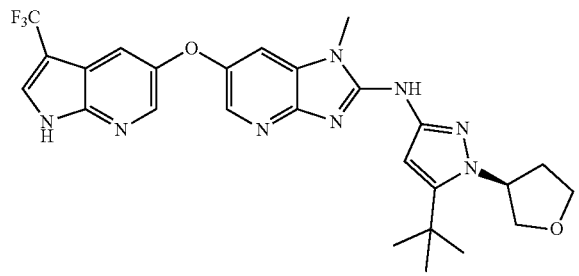
I-381
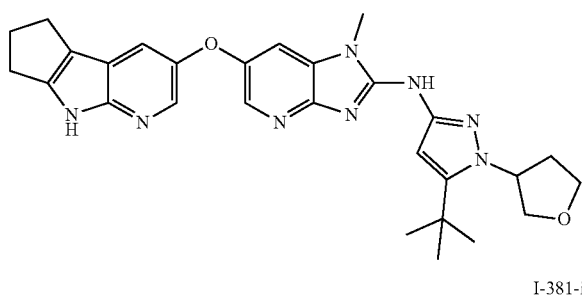
I-381-i
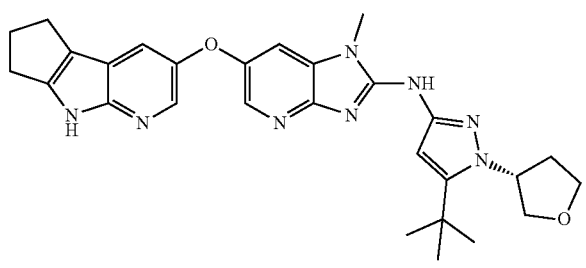
I-381-ii
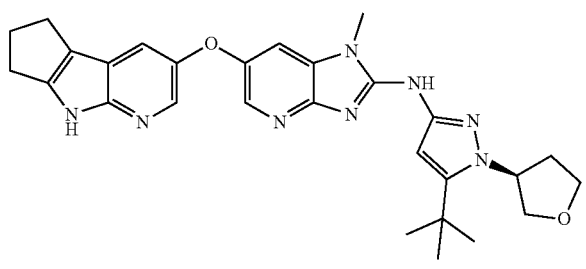
I-382
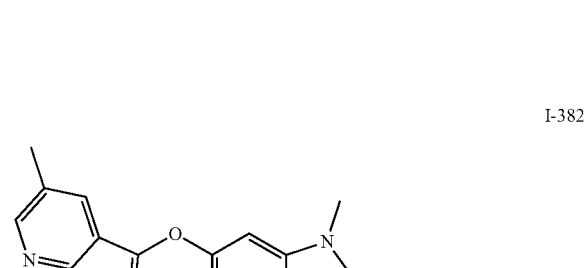
I-382-i
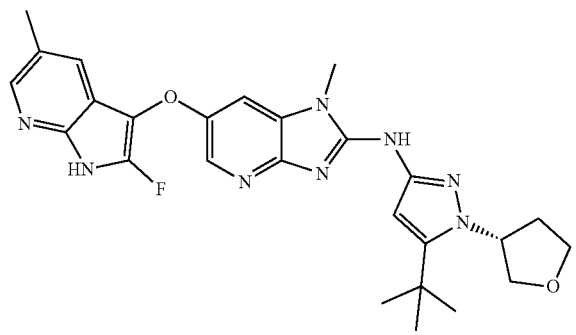
I-382-ii
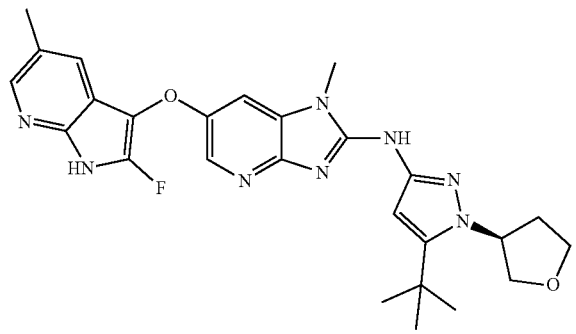
I-383
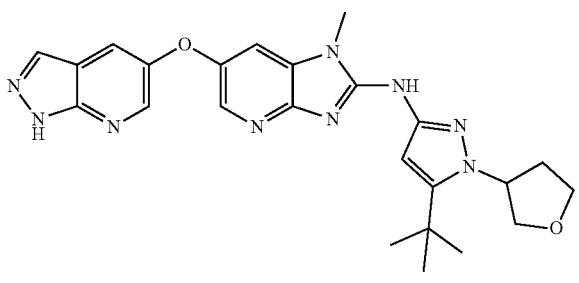
I-383-i
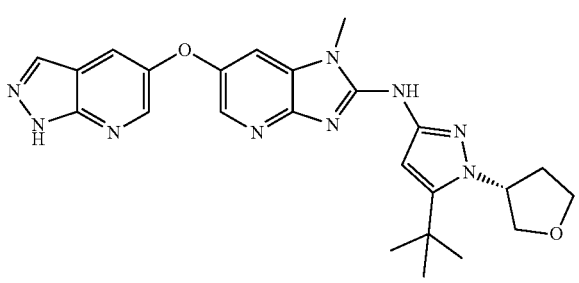
I-383-ii
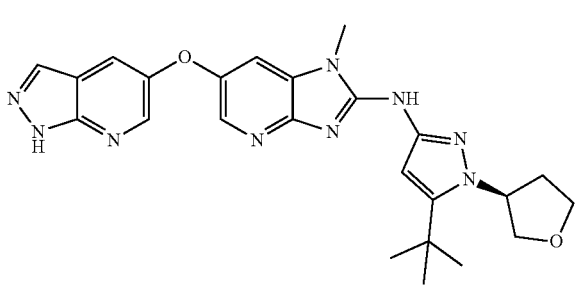

I-384
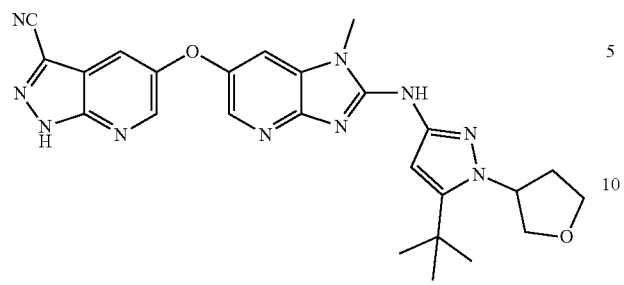
I-384-i
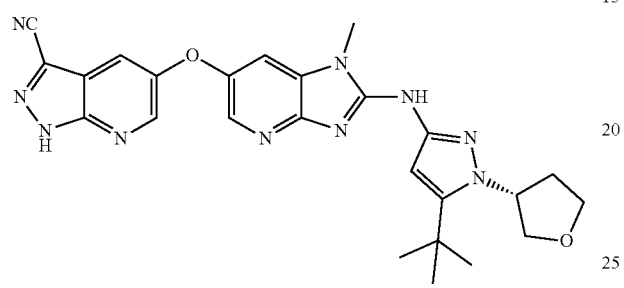
I-384-ii
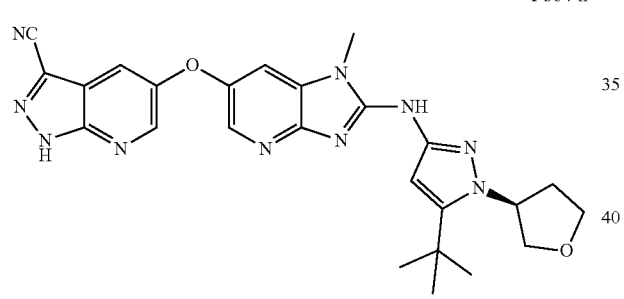
I-385
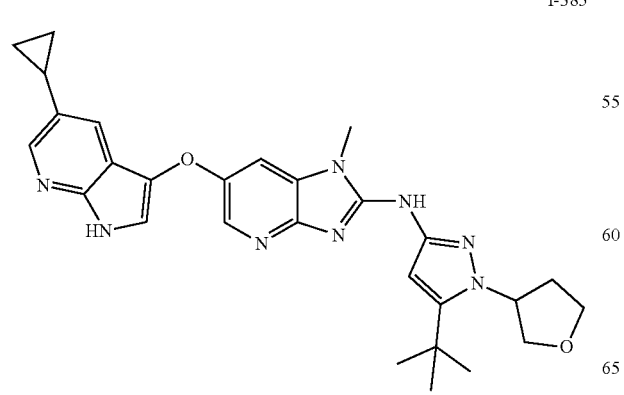
I-385-i
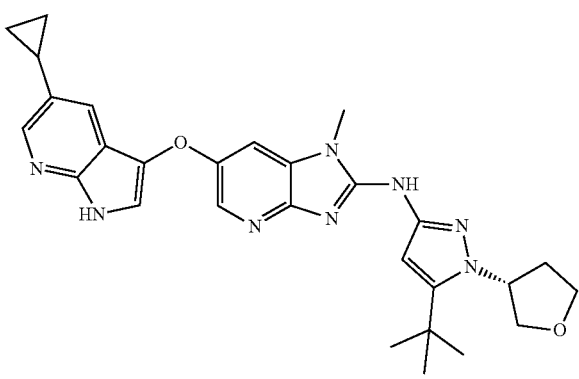
I-385-ii
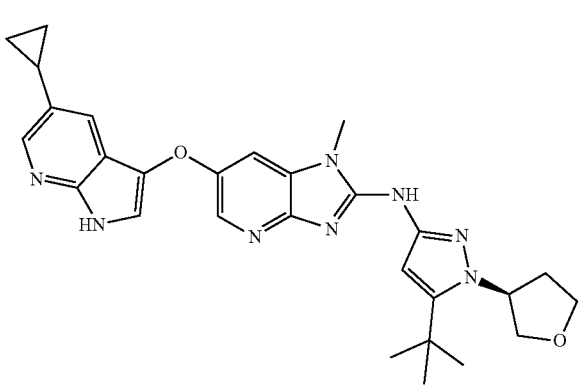
I-386
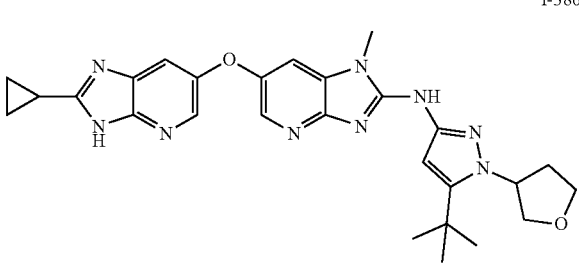
I-386-i
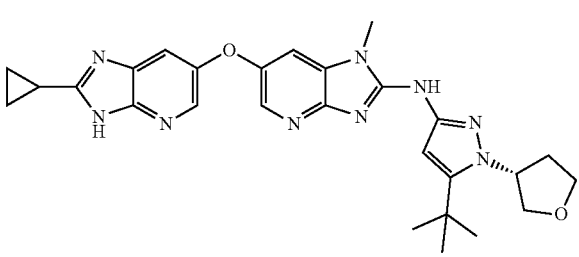
I-386-ii
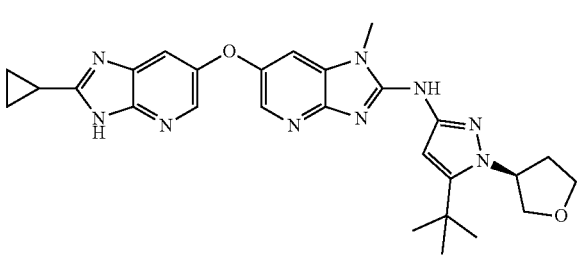

I-387
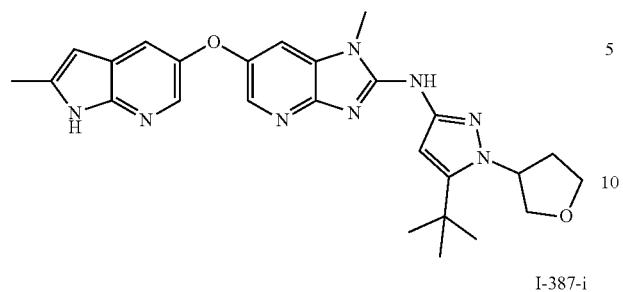
I-389
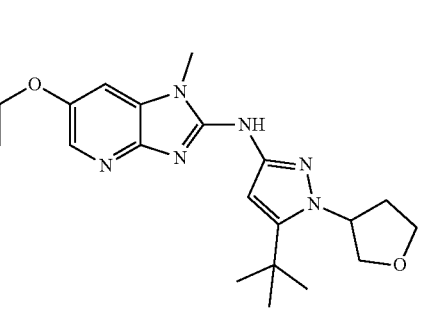
I-387-i
I-389-i
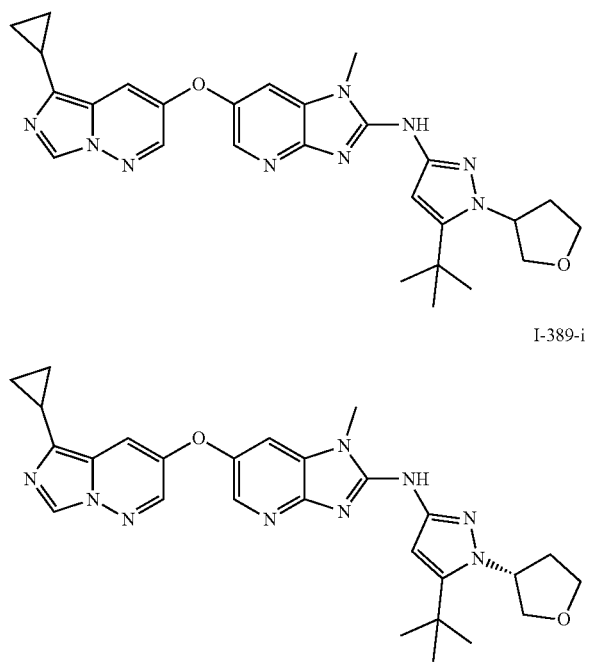
I-387-ii
I-388
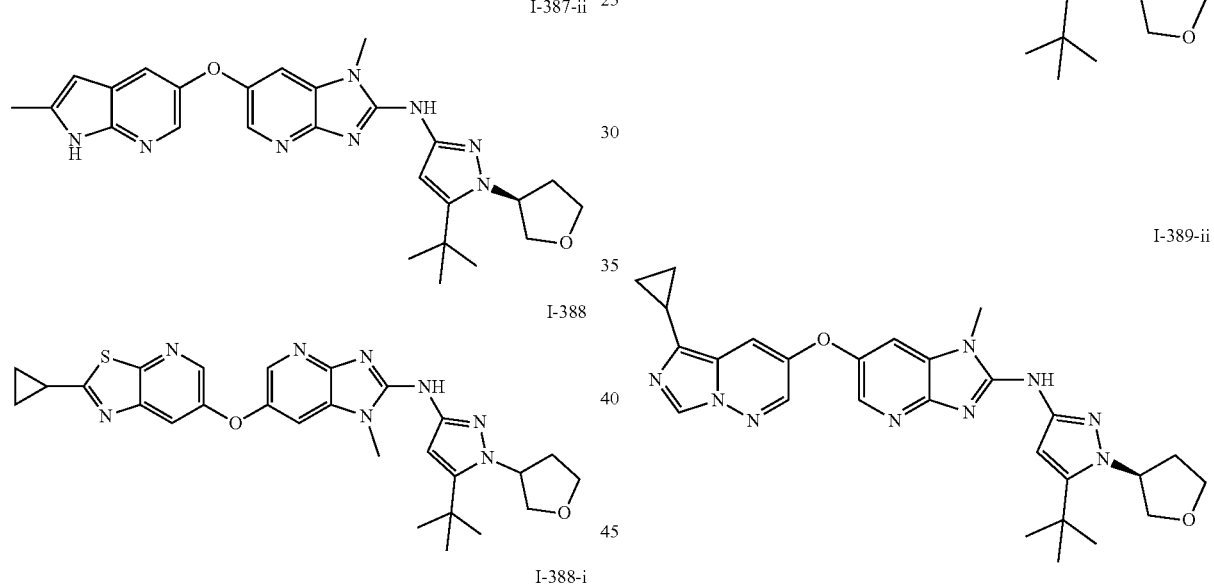
I-389-ii
I-388-i
I-388-ii
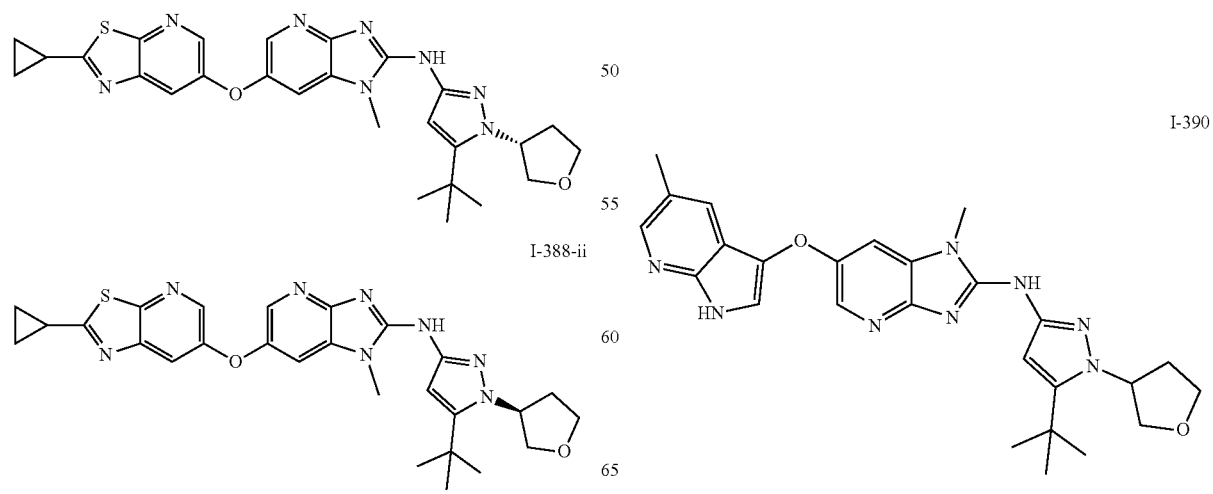
I-390

1311
-continued
I-390-i
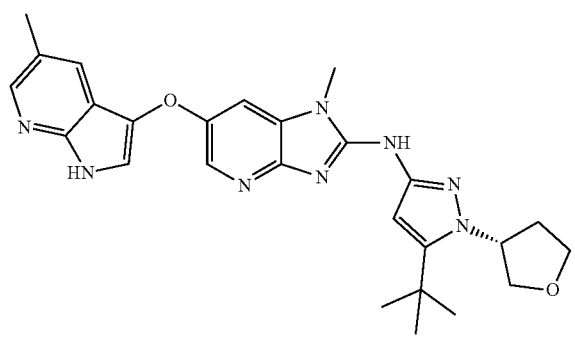
I-390-ii
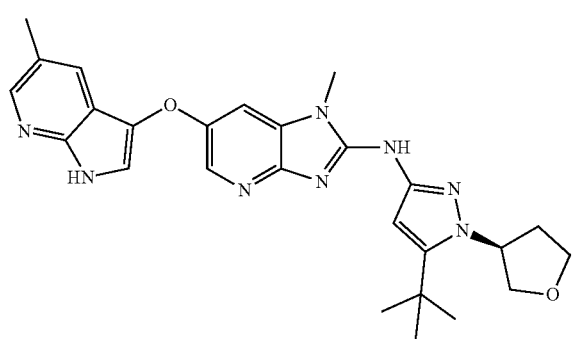
I-391
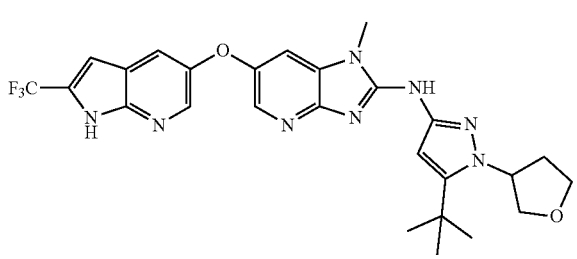
I-391-i
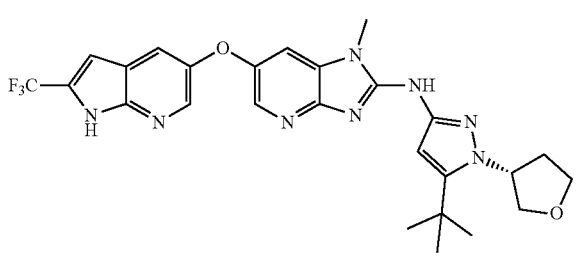
I-391-ii
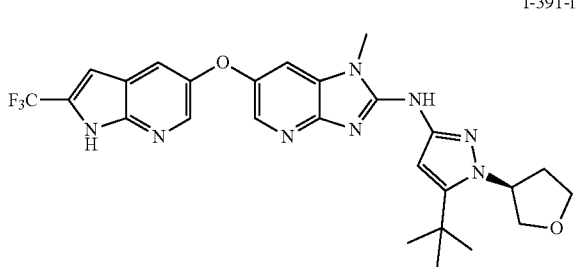
1312
-continued
I-392
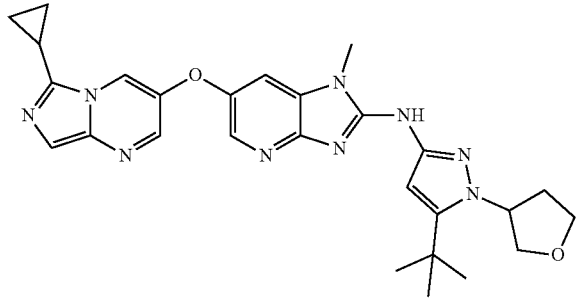
I-392-i
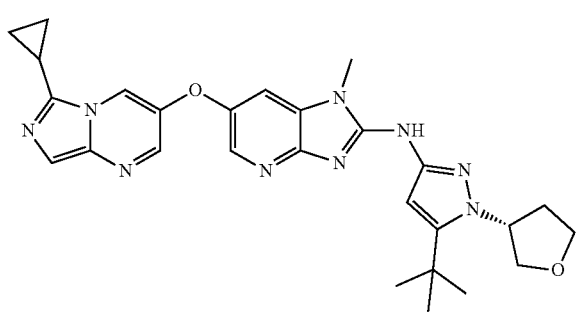
I-392-ii
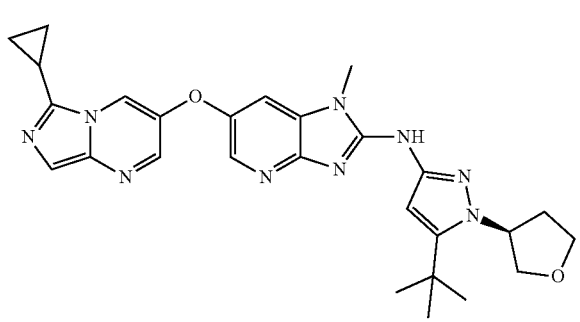
I-393
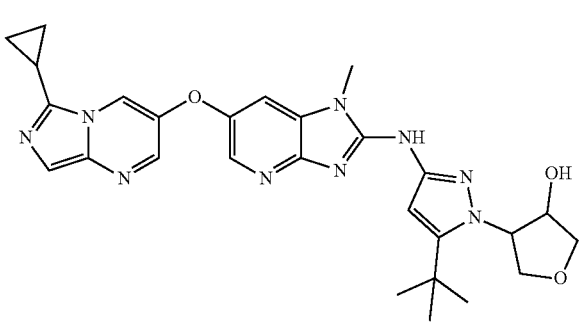
I-393-i
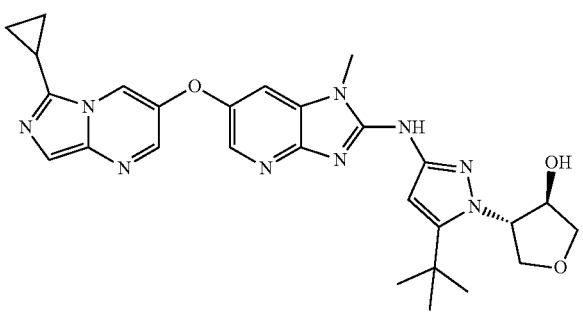

I-393-ii
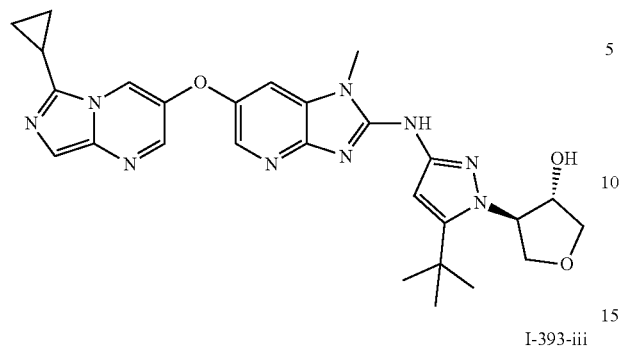
I-393-iii
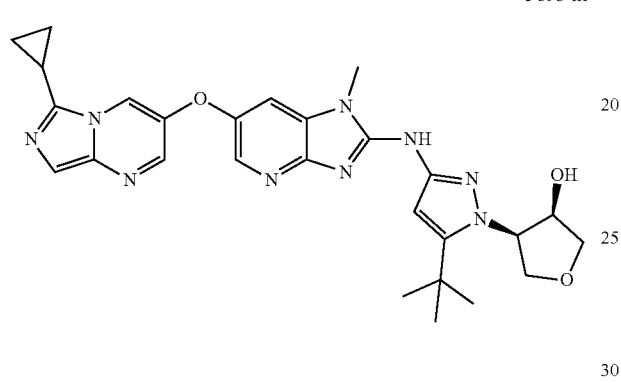
I-393-iv
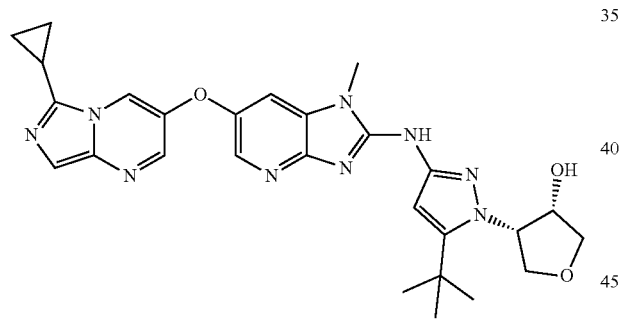
I-394
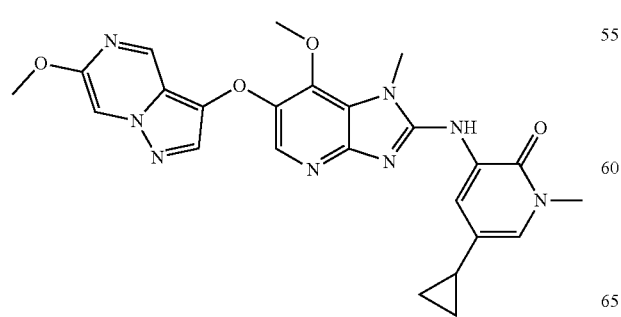
I-395
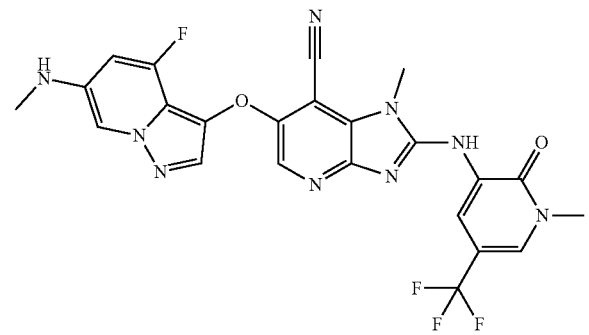
I-396
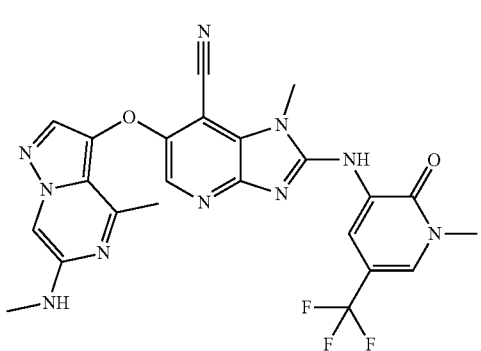
I-397
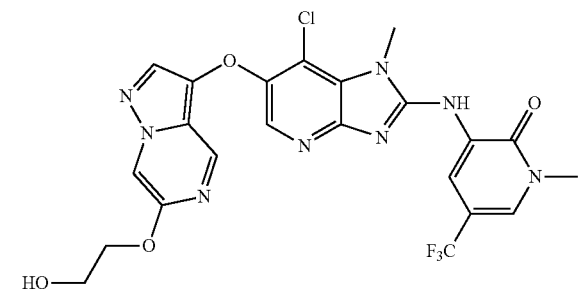
I-398
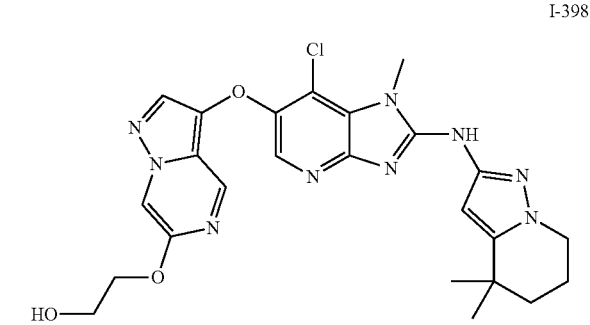

I-399

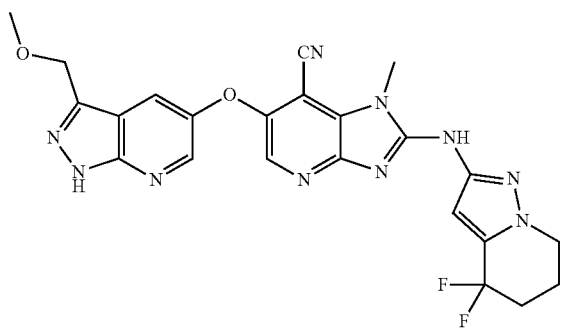

I-400

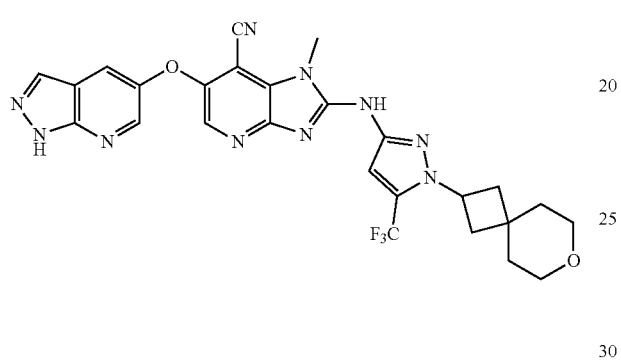

I-401

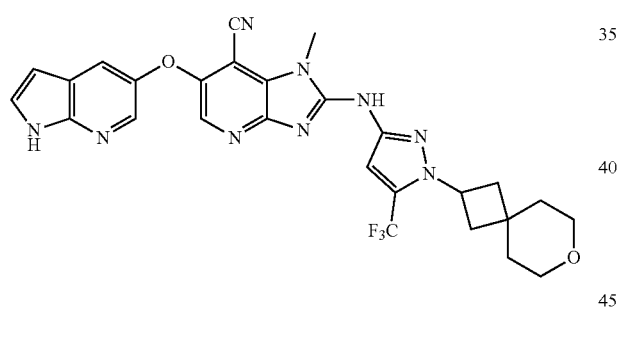

I-402'

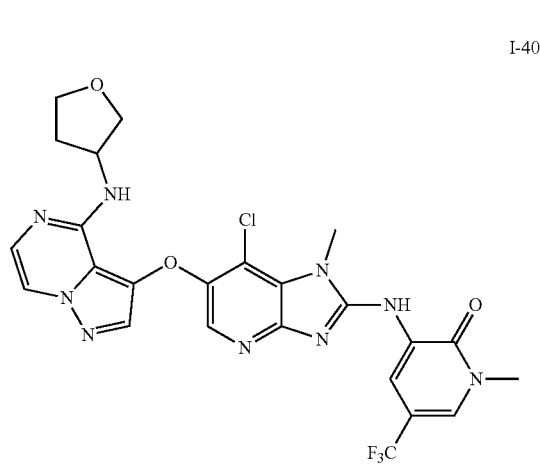

I-402

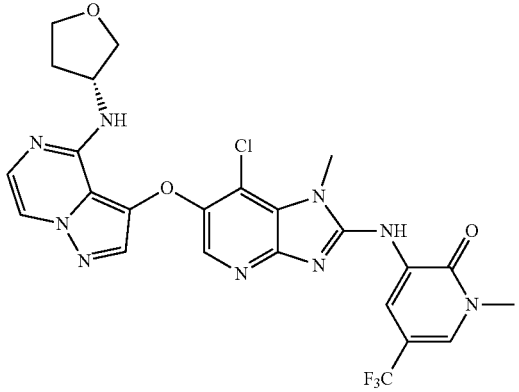

I-402-ii

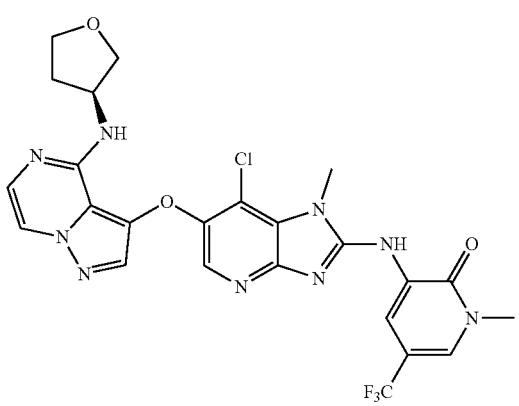

I-403

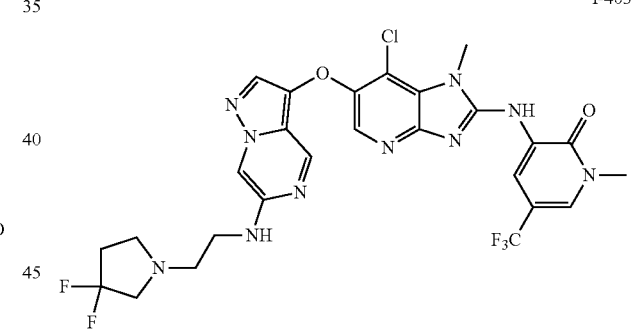

I-404

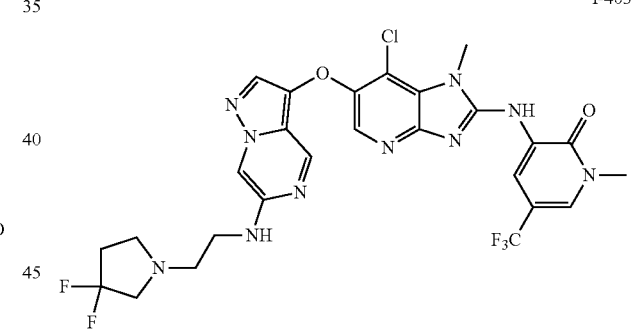

or a pharmaceutically acceptable salt thereof.

4. A pharmaceutical composition comprising the compound of claim 1, or a pharmaceutically acceptable salt thereof, and a pharmaceutically acceptable carrier.

5. A pharmaceutical composition comprising the compound of claim 2, or a pharmaceutically acceptable salt thereof, and a pharmaceutically acceptable carrier.

6. A pharmaceutical composition comprising the compound of claim 3, or a pharmaceutically acceptable salt thereof, and a pharmaceutically acceptable carrier.

7. The compound of claim 1, wherein $R^a$ is hydrogen, halogen, optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

8. The compound of claim 1, wherein $R^a$ is optionally substituted 3- to 7-membered saturated or partially unsaturated monocyclic heterocyclyl having 1-3 heteroatoms independently selected from nitrogen, oxygen, and sulfur.

9. The compound of claim 1, wherein $R^a$ is optionally substituted 7- to 10-membered saturated or partially unsaturated bicyclic heterocyclyl having 1-4 heteroatoms independently selected from nitrogen, oxygen, and sulfur.

10. The compound of claim 1, wherein $R^b$ is optionally substituted $C_{1-4}$ alkyl or optionally substituted $C_3$-$C_4$ cycloalkyl.

11. The compound of claim 1, wherein L is a covalent bond.

12. The compound of claim 1, wherein L is —$CH_2$—.

13. The compound of claim 1, wherein Ring B is optionally substituted 8- to 10-membered bicyclic heteroaryl having 1-4 heteroatoms independently selected from nitrogen, oxygen, and sulfur or optionally substituted 10- to 16-membered polycyclic heteroaryl having 1-5 heteroatoms independently selected from nitrogen, oxygen, and sulfur.

14. The compound of claim 1, wherein:
Ring B is

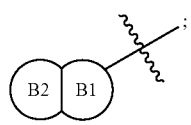

Ring B1 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur; wherein Ring B1 is fused to Ring B2;

Ring B2 is an optionally substituted ring selected from phenyl, 5- to 6-membered monocyclic heteroaryl having 1-3 heteroatoms independently selected from nitrogen, oxygen, and sulfur, 5- to 6-membered saturated or partially unsaturated monocyclic carbocyclyl, and 5- to 6-membered saturated or partially unsaturated monocyclic heterocyclyl having 1-3 heteroatoms independently selected from nitrogen, oxygen, and sulfur; wherein Ring B2 is optionally (i) further fused to Ring B3, or (ii) Ring B2 and Ring B3 combine to form a spirocycle; and Ring B3, when present, is an optionally substituted ring selected from phenyl, 5- to 6-membered monocyclic heteroaryl having 1-3 heteroatoms independently selected from nitrogen, oxygen, and sulfur, 3- to 7-membered saturated or partially unsaturated monocyclic carbocyclyl, and 3- to 7-membered saturated or partially unsaturated monocyclic heterocyclyl having 1-3 heteroatoms independently selected from nitrogen, oxygen, and sulfur.

15. The compound of claim 1, wherein Ring B is selected from the group consisting of:

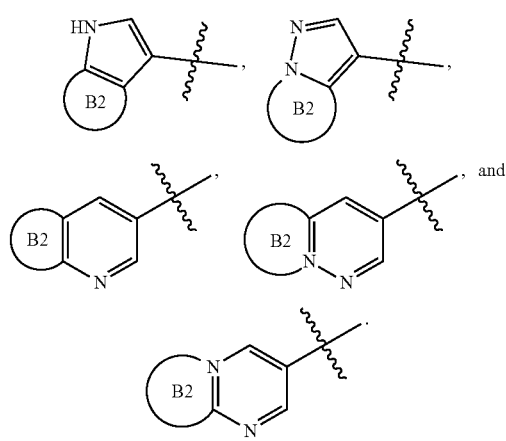

16. The compound of claim 1, wherein Ring B is selected from the group consisting of:

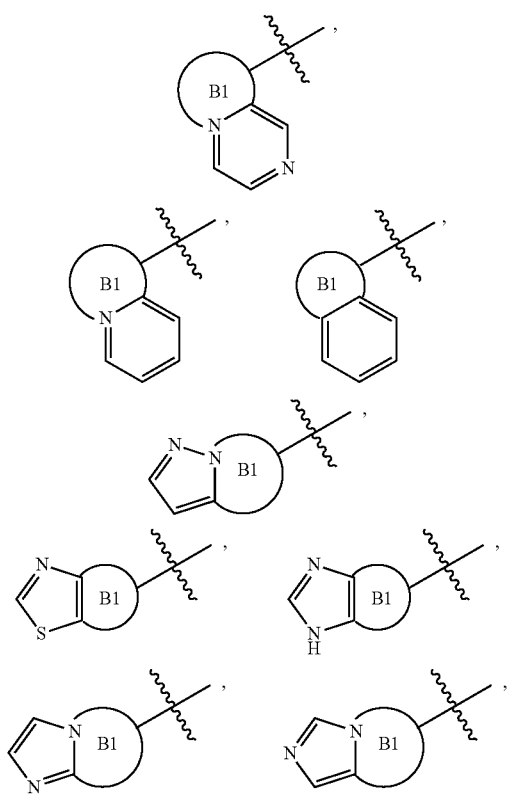

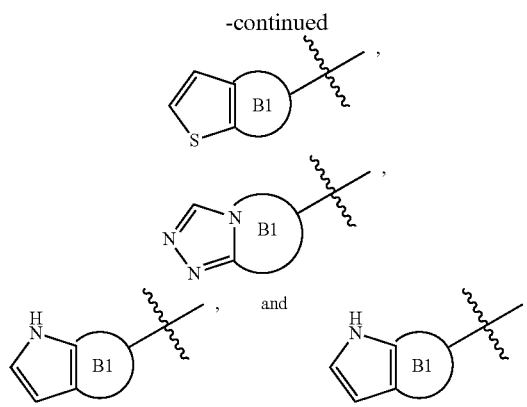

17. The compound of claim 1, wherein $R^1$ is $C_{1-4}$ alkyl.

18. The compound of claim 1, wherein W is CH and Y is N.

19. The compound of claim 1, wherein X is $CR^x$ and $R^x$ is hydrogen, halogen, —CN, —$OR^2$, or optionally substituted $C_{1-6}$ aliphatic.

20. The compound of claim 1, wherein Z is —NH—.

21. The compound of claim 2, wherein Ring A is optionally substituted 8- to 10-membered bicyclic heteroaryl having 1-4 heteroatoms independently selected from nitrogen, oxygen, and sulfur.

22. The compound of claim 2, wherein Ring A is optionally substituted 5- to 6-membered monocyclic heteroaryl having 1-4 heteroatoms independently selected from nitrogen, oxygen, and sulfur.

23. The compound of claim 2, wherein Ring A is optionally substituted phenyl.

24. The compound of claim 2, wherein $R^a$ is hydrogen, halogen, optionally substituted $C_{1-6}$ aliphatic, optionally substituted 5- to 6-membered monocyclic heteroaryl having 1-4 heteroatoms independently selected from nitrogen, oxygen, and sulfur, optionally substituted 3- to 7-membered saturated or partially unsaturated monocyclic carbocyclyl, optionally substituted 3- to 7-membered saturated or partially unsaturated monocyclic heterocyclyl having 1-3 heteroatoms independently selected from nitrogen, oxygen, and sulfur, or optionally substituted 7- to 10-membered saturated or partially unsaturated bicyclic heterocyclyl having 1-4 heteroatoms independently selected from nitrogen, oxygen, and sulfur.

25. The compound of claim 2, wherein $R^a$ is optionally substituted 3- to 7-membered saturated or partially unsaturated monocyclic heterocyclyl having 1-3 heteroatoms independently selected from nitrogen, oxygen, and sulfur.

26. The compound of claim 2, wherein $R^a$ is optionally substituted 7- to 10-membered saturated or partially unsaturated bicyclic heterocyclyl having 1-4 heteroatoms independently selected from nitrogen, oxygen, and sulfur.

27. The compound of claim 2, wherein:

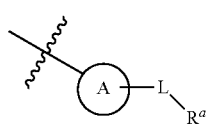

is substituted with 1-5 $R^b$, as valency allows; and
each $R^b$ is independently hydrogen, halogen, —CN, —OR, —O(CH$_2$)$_n$R, —SR, —N(R)$_2$, —NO$_2$, —C(O)R', —C(O)OR, —C(O)N(R)$_2$, —OC(O)R', —OC(O)N(R)$_2$, —OC(O)OR, —OSO$_2$R, —OSO$_2$N(R)$_2$, —N(R)C(O)R', —N(R)SO$_2$R', —SO$_2$R', —SO$_2$N(R)$_2$, —SO$_3$R', optionally substituted $C_{1-6}$ aliphatic, optionally substituted 3- to 6-membered saturated or partially unsaturated monocyclic carbocyclyl, optionally substituted 3- to 6-membered saturated or partially unsaturated monocyclic heterocyclyl having 1-3 heteroatoms independently selected from nitrogen, oxygen, and sulfur, or optionally substituted 5- to 6-membered monocyclic heteroaryl having 1-4 heteroatoms independently selected from nitrogen, oxygen, and sulfur;
each R is independently hydrogen, optionally substituted $C_{1-6}$ aliphatic, optionally substituted phenyl, optionally substituted 5- to 6-membered monocyclic heteroaryl having 1-3 heteroatoms independently selected from nitrogen, oxygen, and sulfur, optionally substituted 3- to 7-membered saturated or partially unsaturated carbocyclyl, or optionally substituted 3- to 7-membered saturated or partially unsaturated monocyclic heterocyclyl having 1-3 heteroatoms independently selected from nitrogen, oxygen, and sulfur, or two R when attached to the same nitrogen atom are taken together form an optionally substituted 3- to 7-membered saturated or partially unsaturated monocyclic heterocyclyl having 0-2 additional heteroatoms independently selected from nitrogen, oxygen, and sulfur;
each R' is independently optionally substituted $C_{1-6}$ aliphatic or optionally substituted 3- to 7-membered saturated or partially unsaturated carbocyclyl; and
n is 1, 2, or 3.

28. The compound of claim 2, wherein $R^b$ is optionally substituted $C_{1-4}$ alkyl or optionally substituted $C_3$-$C_4$ cycloalkyl.

29. The compound of claim 2, wherein

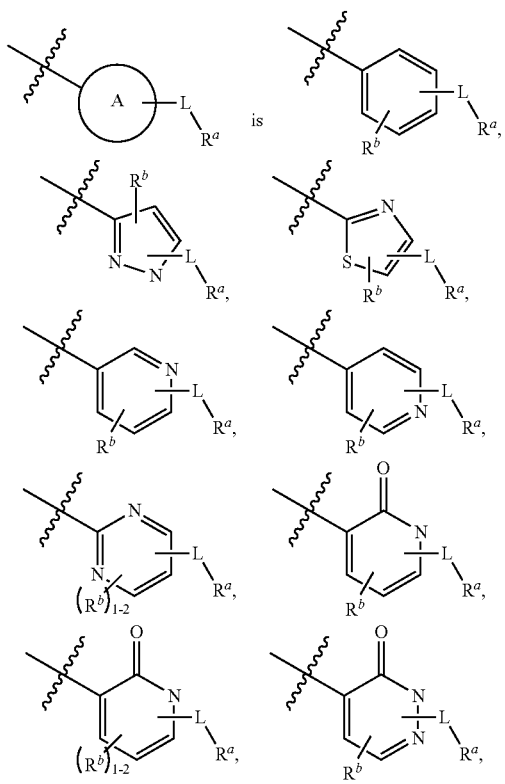

-continued
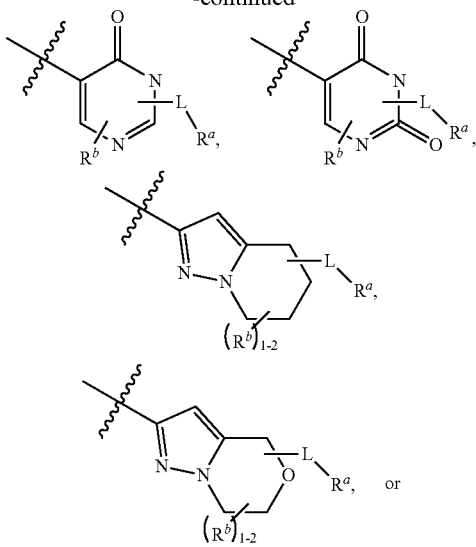
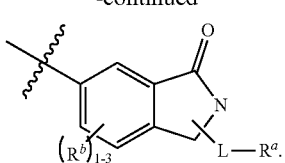
30. The compound of claim 2, wherein L is a covalent bond.
31. The compound of claim 2, wherein L is —CH$_2$—.
32. The compound of claim 2, wherein R$^1$ is C$_{1-4}$ alkyl.
33. The compound of claim 2, wherein W is CH and Y is N.
34. The compound of claim 2, wherein X is CR$^x$ and R$^x$ is hydrogen, halogen, —CN, —OR$^2$, or optionally substituted C$_{1-6}$ aliphatic.
35. The compound of claim 2, wherein Z is —NH—.
* * * * *